United States Patent
Bartberger et al.

(10) Patent No.: US 12,209,087 B2
(45) Date of Patent: *Jan. 28, 2025

(54) AKT1 MODULATORS

(71) Applicant: Alterome Therapeutics, Inc., San Diego, CA (US)

(72) Inventors: Michael David Bartberger, Sherman Oaks, CA (US); Elena V. Dneprovskaia, San Diego, CA (US); Yi Fan, San Diego, CA (US); Eric Anthony Murphy, San Marcos, CA (US); Xuefeng Zhu, San Diego, CA (US)

(73) Assignee: ALTEROME THERAPEUTICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/590,187

(22) Filed: Feb. 28, 2024

(65) Prior Publication Data

US 2024/0239797 A1 Jul. 18, 2024

Related U.S. Application Data

(63) Continuation of application No. 18/474,848, filed on Sep. 26, 2023, now Pat. No. 11,999,730, which is a continuation-in-part of application No. PCT/US2023/075058, filed on Sep. 25, 2023.

(60) Provisional application No. 63/582,697, filed on Sep. 14, 2023, provisional application No. 63/580,327, filed on Sep. 1, 2023, provisional application No. 63/508,418, filed on Jun. 15, 2023, provisional application No. 63/498,770, filed on Apr. 27, 2023, provisional application No. 63/377,183, filed on Sep. 26, 2022.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01); *C07B 2200/05* (2013.01)

(58) Field of Classification Search
CPC .............................. C07D 471/04; C07D 519/00
See application file for complete search history.

(56) References Cited

U.S. PATENT DOCUMENTS

| | | | |
|---|---|---|---|
| 5,846,514 A | 12/1998 | Foster et al. | |
| 6,334,997 B1 | 1/2002 | Foster et al. | |
| 8,501,770 B2 * | 8/2013 | Ashwell | A61P 19/08 546/118 |
| 11,542,248 B2 | 1/2023 | Li et al. | |
| 11,673,898 B2 | 6/2023 | Wu et al. | |
| 11,999,730 B1 * | 6/2024 | Bartberger | C07D 471/04 |
| 2022/0380378 A1 | 12/2022 | Zhou et al. | |

FOREIGN PATENT DOCUMENTS

| | | |
|---|---|---|
| WO | WO-2011082098 A1 | 7/2011 |
| WO | WO-2011082270 A2 | 7/2011 |
| WO | WO-2014165815 A2 | 10/2014 |
| WO | WO-2020172324 A1 | 8/2020 |
| WO | WO-2023168291 A1 | 9/2023 |
| WO | WO-2024073371 A1 | 4/2024 |

OTHER PUBLICATIONS

Alwhaibi et al., The unconventional role of Akt1 in the advanced. Pharmacol Res., 145:104270 (2019).
Berge et al. Pharmaceutical Salts. Journal of Pharmaceutical Sciences 66(1):1-19 (Jan. 1977).
CAS Registry No. 1062165-32-5; STN Entry Date: Oct. 16, 2008.
CAS Registry No. 1320500-69-3; STN Entry Date: Aug. 21, 2011.
CAS Registry No. 1386122-43-5; STN Entry Date: Aug. 3, 2012.
CAS Registry No. 1388210-12-5; STN Entry Date: Aug. 8, 2012.
CAS Registry No. 1390506-66-7; STN Entry Date: Aug. 13, 2012.
CAS Registry No. 1626477-46-0; STN Entry Date: Sep. 25, 2014.
CAS Registry No. 1648195-01-0; STN Entry Date: Feb. 16, 2015.
CAS Registry No. 1648461-12-4; STN Entry Date: Feb. 16, 2015.
CAS Registry No. 2181042-80-6; STN Entry Date: Feb. 28, 2018.
CAS Registry No. 2335252-73-6; STN Entry Date: Jun. 16, 2019.
CAS Registry No. 2335252-79-2; STN Entry Date: Jun. 16, 2019.
CAS Registry No. 2335567-88-7; STN Entry Date: Jun. 16, 2019.
Chemical Structure Search Report on Specifically Substituted N-Phenyl Benzimidazole-Like Structures. CAS Sep. 27, 2023.
Chen et al., Effect of AKT1 (p. E17K) Hotspot Mutation on Malignant Tumorigenesis and Prognosis. Front Cell Dev Biol., 8:573599 (2020).
Co-pending U.S. Appl. No. 18/474,848, inventors Bartberger; Michael David et al., filed Sep. 26, 2023.
Dean. Recent Advances in the Synthesis and Applications of Radiolabeled Compounds for Drug Discovery and Development. Current Pharmaceutical Design 6(10):110 (02 Pages) (Jul. 5, 2000) (Preface only).
Evans. Synthesis of Radiolabelled Compounds. Journal of Radioanalytical Chemistry 64(1-2):9-32 (1981).
Kabalka et al., The synthesis of radiolabeled compounds via organometallic intermediates. Tetrahedron 45(21):6601-6621 (1989).
Nitulescu et al., The Akt pathway in oncology therapy and beyond (Review). Int J Oncol., 53(6):2319-2331 (2018).
PCT/US2023/075058 International Search Report and Written Opinion dated Nov. 30, 2023.
U.S. Appl. No. 18/474,848 Office Action dated Jan. 19, 2024.

* cited by examiner

*Primary Examiner* — Valerie Rodriguez-Garcia
(74) *Attorney, Agent, or Firm* — WILSON SONSINI GOODRICH & ROSATI

(57) ABSTRACT

Provided herein are inhibitors of AKT1, pharmaceutical compositions comprising the inhibitory compounds, and methods for using the AKT1 inhibitory compounds for the treatment of disease.

20 Claims, No Drawings
Specification includes a Sequence Listing.

AKT1 MODULATORS

CROSS-REFERENCE TO RELATED APPLICATIONS

This application is a continuation of U.S. application Ser. No. 18/474,848, filed Sep. 26, 2023, which claims the benefit of U.S. Provisional Application No. 63/377,183, filed on Sep. 26, 2022; U.S. Provisional Application No. 63/498,770, filed on Apr. 27, 2023; U.S. Provisional Application No. 63/508,418, filed on Jun. 15, 2023; U.S. Provisional Application No. 63/580,327, filed on Sep. 1, 2023; and U.S. Provisional Application No. 63/582,697, filed on Sep. 14, 2023; and U.S. application Ser. No. 18/474,848 is a continuation in part of International Patent Application No. PCT/US2023/075058, filed on Sep. 25, 2023; which claims the benefit of U.S. Provisional Application No. 63/377,183, filed on Sep. 26, 2022; U.S. Provisional Application No. 63/498,770, filed on Apr. 27, 2023, U.S. Provisional Application No. 63/508,418, filed on Jun. 15, 2023; U.S. Provisional Application No. 63/580,327, filed on Sep. 1, 2023; and U.S. Provisional Application No. 63/582,697, filed on Sep. 14, 2023, all of which patent applications are hereby incorporated by reference in their entirety.

SEQUENCE LISTING

The instant application contains a Sequence Listing which has been submitted electronically in XML format and is hereby incorporated by reference in its entirety. Said XML copy, created on Sep. 26, 2023, is named 62619-712_301_SL.xml and is 2,421 bytes in size.

BACKGROUND

AKT is a protein kinase and mediates cell survival and proliferation by inhibiting pathways which promotes apoptosis. AKT signaling cascade dysfunction is observed in several cancer types and may be associated with tumor aggressiveness. Additionally, malfunction of AKT typically lead to enhanced proliferation, growth, survival, and resistance to apoptosis. Pharmaceutical agents with the ability to modulate AKT1 activity would be useful in the treatment of disease, such as cancer.

BRIEF SUMMARY OF THE INVENTION

Provided herein are inhibitors of AKT1, pharmaceutical compositions comprising said inhibitory compounds, and methods for using said inhibitory compounds for the treatment of disease.

One embodiment provides a compound having the structure of Formula (I), or a pharmaceutically acceptable salt or solvate thereof:

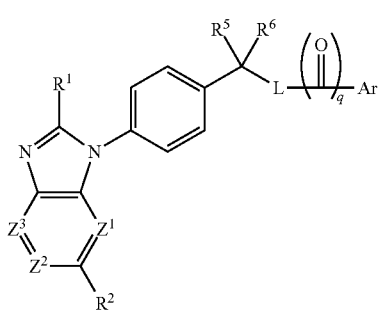

(I)

wherein:
$Z^1$ is N, C—H, or C—$R^3$;
$Z^2$ is N, C—H, or C—$R^4$;
$Z^3$ is N, C—OH, or C—$R^9$;
Ar is selected from:

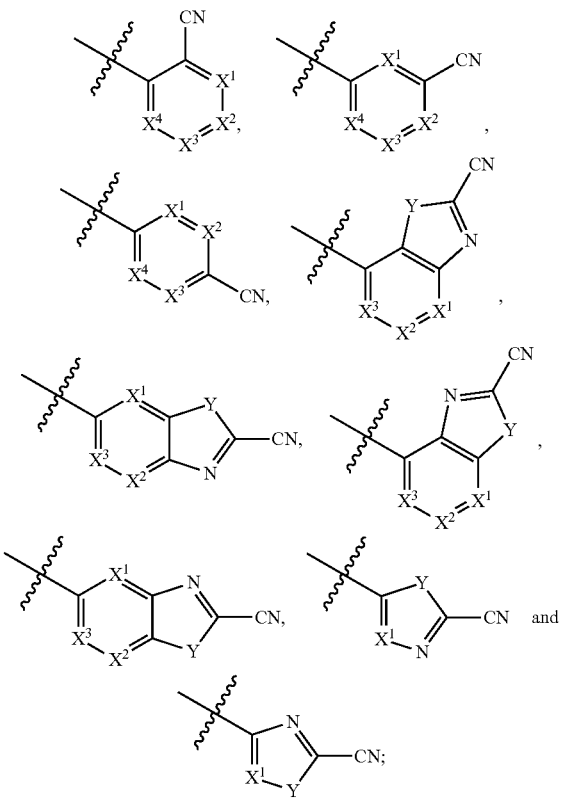

$X^1$ is N or C—$R^7$;
$X^2$ is N or C—$R^7$;
$X^3$ is N or C—$R^7$;
$X^4$ is N or C—$R^7$;
Y is O, S, or N—$R^9$;
$R^1$ is selected from hydrogen, optionally substituted C1-C6 alkyl, optionally substituted aryl, or optionally substituted heteroaryl;
$R^2$ is selected from hydrogen, halogen, —OH, —CN, —N(R))$_2$, —O$R^9$, —S$R^9$, —SO$_2R^9$, —CO$_2R^9$, —CON($R^9$)$_2$, —S$R^9$, —S(O)$R^9$, —S(O)$_2R^9$, optionally substituted C1-C6 alkyl, optionally substituted C1-C6 alkoxy, optionally substituted C2-C6 alkenyl, optionally substituted C2-C6 alkynyl, optionally substituted C3-C7 carbocyclyl, optionally substituted 4-membered to 6-membered heterocyclyl, optionally substituted aryl, aryl substituted with an optionally substituted 4-membered to 6-membered heterocyclyl, optionally substituted heteroaryl or heteroaryl substituted with an optionally substituted 3-membered to 6-membered carbocyclyl;
$R^3$ is selected from optionally substituted C1-C6 alkyl, or optionally substituted aryl;
$R^4$ is selected from halogen, —CN, optionally substituted C1-C6 alkyl, or optionally substituted aryl;
$R^5$ and $R^6$ are each independently hydrogen, deuterium, halogen, —OH, or optionally substituted C1-C6 alkyl; or $R^5$ and $R^6$ together form an oxo; or $R^5$ and $R^6$ join together to form a carbocycle or heterocycle;

each $R^7$ is independently selected from hydrogen, deuterium, halogen, —OH, —SH, optionally substituted C1-C6 alkoxy, —S-(optionally substituted C1-C6 alkyl), —CN, optionally substituted C1-C6 alkyl, and optionally substituted aryl;
L is selected from —N($R^8$)—, or a divalent radical selected from:
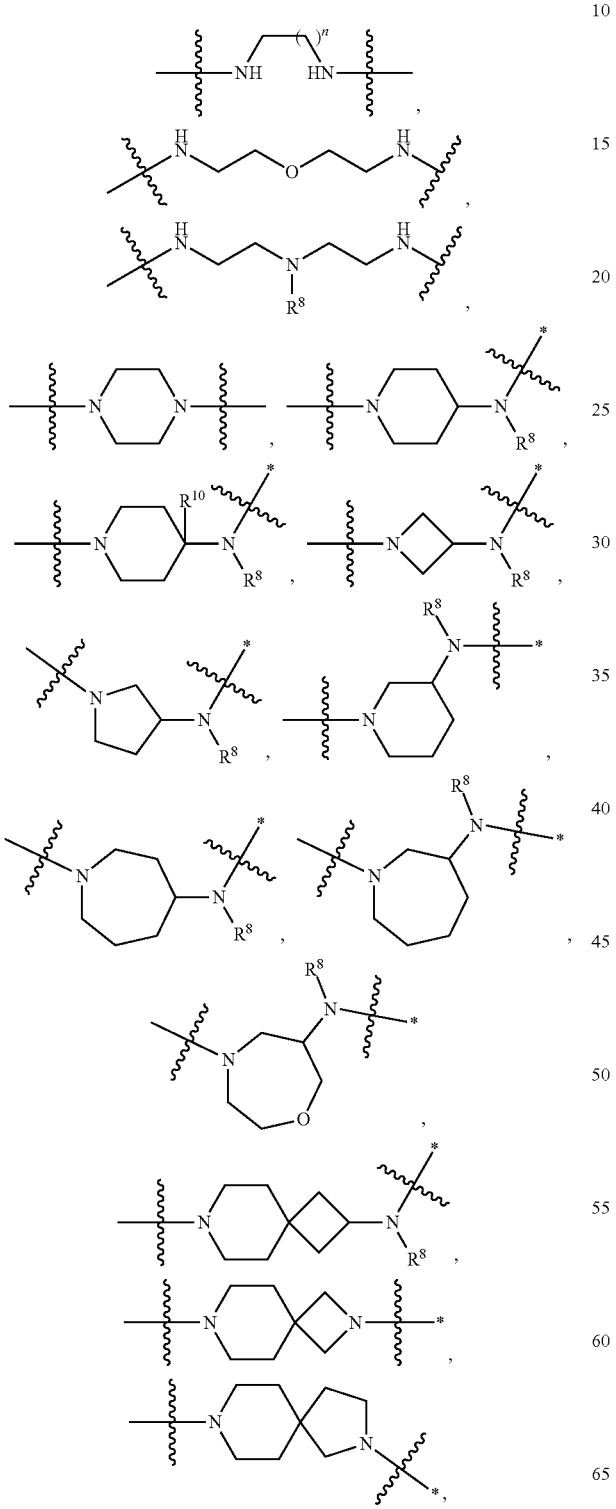
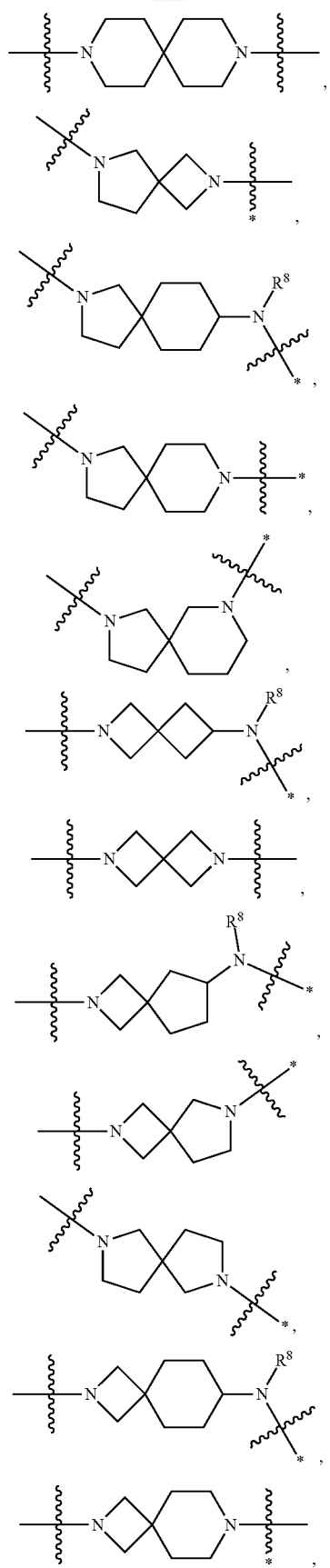

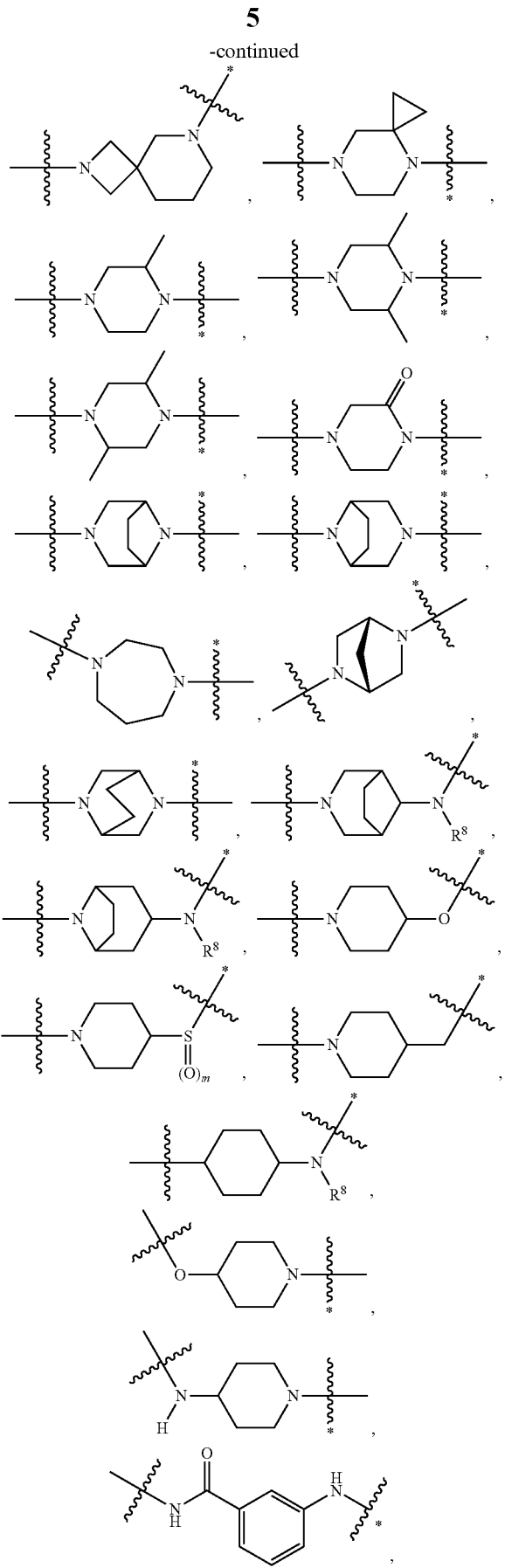

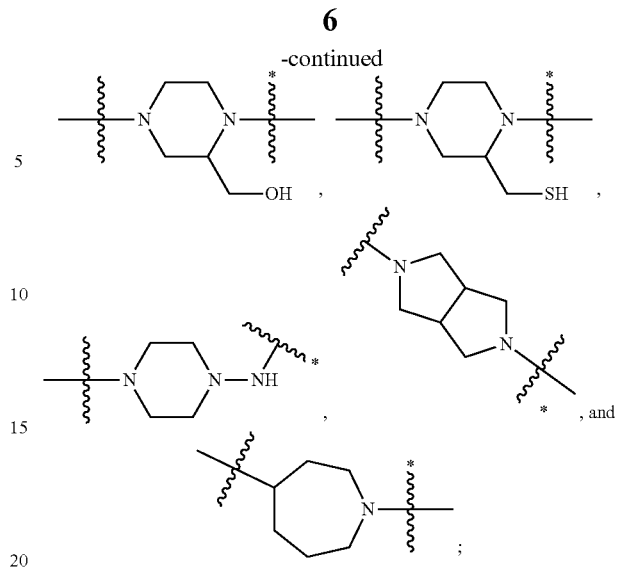

wherein the asterisk (*) indicates the bond to the —CO-Ar group;

$R^8$ is hydrogen, optionally substituted C1-C6 alkyl, optionally substituted C3-C7 cycloalkyl, or optionally substituted heterocyclyl;

each $R^9$ is hydrogen, or optionally substituted C1-C6 alkyl;

$R^{10}$ is optionally substituted C1-C6 alkyl;

m is 0, 1, or 2;

n is 1, 2, or 3, and q is 0 or 1.

One embodiment provides a pharmaceutical composition comprising a compound of Formula (I), or pharmaceutically acceptable salt or solvate thereof, and at least one pharmaceutically acceptable excipient.

One embodiment provides a method of treating a disease or disorder in a patient in need thereof comprising administering to the patient a compound of Formula (I), or pharmaceutically acceptable salt or solvate thereof. Another embodiment provides the method wherein the disease or disorder is cancer.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-C5 alkyl). In other embodiments, an alkyl comprises one to four carbon atoms (e.g., $C_1$-C4 alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_2$-$C_5$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$(where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl). In certain embodiments, an optionally substituted alkyl is a haloalkyl. In other embodiments, an optionally substituted alkyl is a fluoroalkyl. In other embodiments, an optionally substituted alkyl is a —CF, group.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$NOR$^a$(where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^s$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from optionally substituted alkyl, optionally substituted alkenyl, optionally substituted alkynyl, halo, cyano, nitro, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^1$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from optionally substituted alkyl, optionally substituted alkenyl, optionally substituted alkynyl, halo, oxo, thioxo, cyano, nitro, —$R^b$—$OR^a$, —$R^b$—OC(O)—$R^a$, —$R^b$—OC(O)—$OR^a$, —$R^b$—OC(O)—$N(R)_2$, —$R^b$—$N(R^2)_2$, —$R^b$—$C(O)R^a$, —$R^b$—$C(O)OR^a$, —$R^b$—$C(O)N(R^3)_2$, —$R^b$—O—$R^c$—$C(O)N(R^3)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Carbocyclylalkynyl" refers to a radical of the formula —R$^c$-carbocyclyl where R$^c$ is an alkynylene chain as defined above. The alkynylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic, or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from optionally substituted alkyl, optionally substituted alkenyl, optionally substituted alkynyl, halo, fluoroalkyl, oxo, thioxo, cyano, nitro, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the R$^a$, R$^b$, or R$^c$ substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals.

Examples of such N-heterocyclyl radicals include, but are not limited to, 1-morpholinyl, 1-piperidinyl, 1-piperazinyl, 1-pyrrolidinyl, pyrazolidinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —R$^c$-heterocyclyl where R is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen, and sulfur. As used herein, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h] quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo [3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d] pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno [2,3-d]pyrimidinyl, 6,7,8,9-tetrahydro-5H-cyclohepta[4,5] thieno[2,3-d]pyrimidinyl, 5,6,7,8-tetrahydropyrido[4,5-c] pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from optionally substituted alkyl, optionally substituted cycloalkylalkyl, optionally substituted heterocyclylalkyl, optionally substituted alkenyl, optionally substituted alkynyl, halo, optionally substituted fluoroalkyl, optionally substituted haloalkenyl, optionally substituted haloalkynyl, oxo, thioxo, cyano, nitro, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N(R)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

As used herein, "carboxylic acid bioisostere" refers to a functional group or moiety that exhibits similar physical, biological and/or chemical properties as a carboxylic acid moiety.

Examples of carboxylic acid bioisosteres include, but are not limited to,

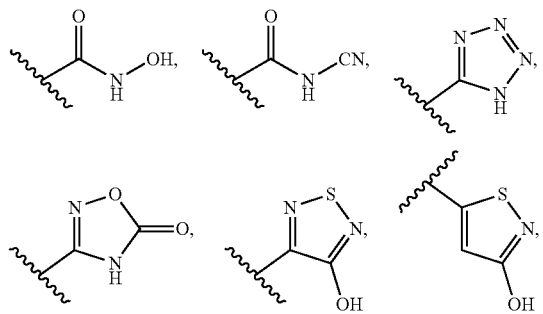

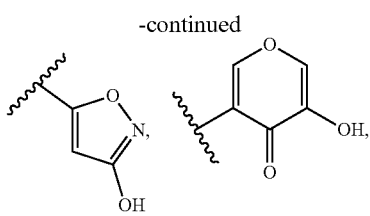

and the like.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

$^{14}$C, $^{15}$C, $^{12}$N, $^{3}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated.

In some embodiments, isotopic substitution with $^{18}$F is contemplated. All isotopic variations of the compounds of the present invention, whether radioactive or not, are encompassed within the scope of the present invention.

In certain embodiments, the compounds disclosed herein have some or all of the $^{1}$H atoms replaced with $^{2}$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetra-

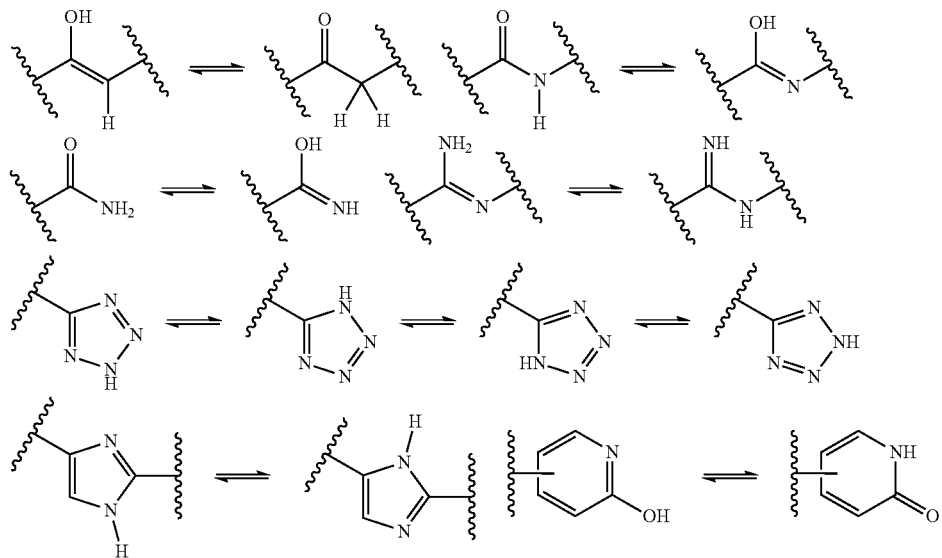

The compounds disclosed herein, in some embodiments, are used in different enriched isotopic forms, e.g., enriched in the content of $^{2}$H, $^{3}$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^{2}$H), tritium ($^{3}$H), iodine-125 ($^{125}$I) or carbon-14 ($^{14}$C). Isotopic substitution with $^{2}$H, $^{11}$C, $^{13}$C, hedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-d$_{3}$ (CD$_{3}$I), are readily available and may be employed to transfer a deuterium-substituted carbon atom under nucleophilic substitution reaction conditions to the reaction substrate. The use of CD$_{3}$I is illustrated, by way of example only, in the reaction schemes below.

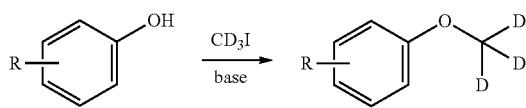

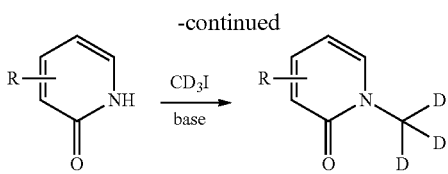

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

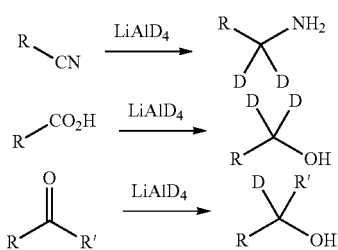

Deuterium gas and palladium catalyst are employed to reduce unsaturated carbon-carbon linkages and to perform a reductive substitution of aryl carbon-halogen bonds as illustrated, by way of example only, in the reaction schemes below.

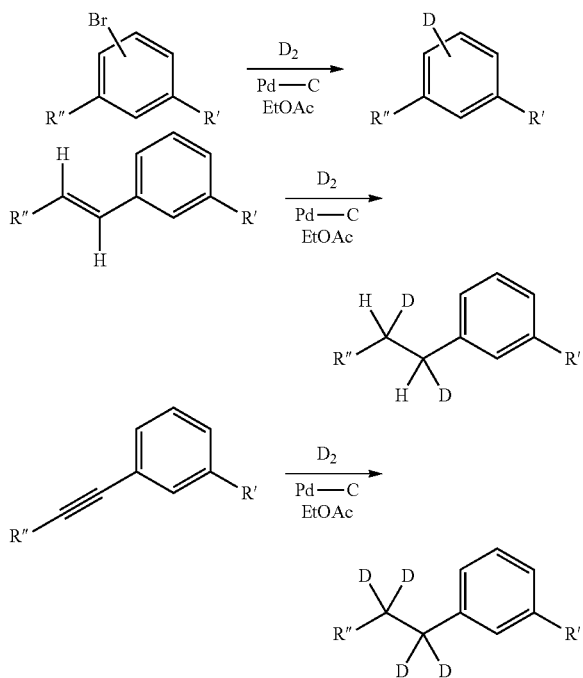

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the AKT1 inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S M et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein exist in either unsolvated or solvated forms.

The term "subject" or "patient" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

AKT1 Protein and Function

AKT, also known as protein kinase B (PKB), is a serine/threonine protein kinase with three isoforms, AKT1, AKT2, and AKT3. While the isoforms are encoded by different genes, they are highly homologous at the protein level and share a conserved domain structure comprising an N-terminal pleckstrin homology (PH) domain, a kinase domain, and a C-terminal regulatory domain comprising a hydrophobic moiety, which includes the regulatory serine residue (Nitulescu, G. M. et al., Int J Oncol., 2018; 53(6): 2319-2331).

AKT proteins play a crucial role in major cellular functions including cell cycle progression, cell size, regulation of glucose metabolism, transcription, protein synthesis, genome stability, and neovascularization. AKT proteins can block apoptosis by inactivation of pro-apoptotic proteins, and mediate cellular growth factors, promoting cell survival. AKT is a major downstream effector of nuclear factor-kappaB (NfκB), which may link AKT signaling to the nucleus of a cell.

AKT1 is ubiquitously expressed, whereas AKT2 is primarily expressed in insulin-responsive tissues, and AKT3 is primarily expressed in brain and testes. A shared phosphorylation site of AKT in the catalytic domain corresponds to a threonine residue; specifically, Thr308 in AKT1, Thr309 in AKT2, and Thr305 in AKT3. A shared phosphorylation site in the C-terminus of the protein cis a serine residue; specifically, Ser473 in AKT1, Ser474 in AKT2, and Ser472 in AKT3.

AKT is a key downstream mediator of the phosphoinositide-3-kinase (PI3K) signaling pathway. PI3Ks are activated by different compounds. For example, PI3Kα, PI3Kβ, and PI3Kδ, are activated by extracellular ligands binding to a transmembrane glycoprotein with enzymatic activity, receptor tyrosine kinases (RTKs). In contrast, PI3Kγ is activated by G-protein-compound receptors (GPCRs) and by RAS family of GTPases.

The AKT cascade can be activated by RTKs and G-protein-compound receptors (GPCRs), along with other signals including integrins, B cell receptors, T cell receptors, and cytokine receptors.

AKT1 Mechanism

AKT is activated by a second phosphorylation at the regulatory serine residue, Ser473. Known phosphorylating agents of AKT at Ser473 include, but are not limited to PDK-1, integrin-linked kinase (ILK), members of the PI3K-related kinase (PIKK) family, and mammalian target of rapamycin (mTOR) (Nitulescu, G. M. et al., Int J Oncol., 2018; 53(6): 2319-2331).

mTOR is a key component in the AKT signaling pathway, which is a downstream member of AKT and important regulator for cell metabolism and growth. mTOR is also an activator which can directly phosphorylate AKT's regulatory serine residue, Ser473. mTOR forms a complex with rapamycin-insensitive companion of mTOR (RICTOR) (and other proteins) to form mTOR complex 2 (mTORC2), which can directly phosphorylate AKT Ser473. AKT can affect cell survival and growth because it can influence the tuberous sclerosis complex (TSC) 1/2 along the mTORC signaling pathway and inhibit pro-apoptotic proteins or signals.

AKT is known as a survival kinase and mediates cell survival and proliferation by inhibiting pathways including, but not limited to Bcl2 and MDM2, which promotes apoptosis. Studies have shown that the AKT signaling cascade have frequent malfunctions in various cancers, and may be associated with tumor aggressiveness (Nitulescu, G. M. et al., Int J Oncol., 2018; 53(6): 2319-2331). Malfunctions of AKT typically lead to enhanced proliferation, growth, survival, and resistance to apoptosis (Alwhaibi, A. et al., Pharmacol Res., 2019, 145: 104270). Malfunction and misregulation of AKT may lead to cancers such as but not limited to breast cancer, gastric carcinoma, glioblastoma, gliosarcomas, head and neck squamous cell carcinoma, ovarian cancer, pancreatic cancer, and prostate cancer.

Additionally, AKT1 has been found to be involved in invasion and migration of cancerous cells (Alwhaibi, A. et al., Pharmacol Res., 2019, 145: 104270). Researchers found that silencing the AKT1 isoform can abrogate specific types of cancer cell migration. However, there have been other studies which have demonstrated that activated AKT1 resulted in less metastatic propensity for lung metastatic lesion cells and breast cancer cells. AKT1 has also been identified as a key protein involved in angiogenesis, lung cancer, and tumorigenesis.

Furthermore, overexpression of AKT has been correlated to resistance to chemotherapeutic agents such as cisplatin, methotrexate, and paclitaxel. Thus, there remains a need to find AKT inhibitors given its role in cell survival and cancer proliferation.

Recently, it has been found that the AKT1 gene mutation E17K can affect cell growth, proliferation, survival, and migration of breast cancer cells, colorectal cancer cells, and ovarian cancer cells (Chen, Y. et al., Front Cell Dev Biol., 2020; 8: 573599). These mutations in the PH structural domain increase the binding of AKT1 to Phosphatidylinositol-3,4,5-triphosphate (PIP3) lipid ligand, which accelerates transfer of AKT from the cytoplasm to the cell membrane through formation of hydrogen bonds. Transfer of AKT into the cell membrane allows it to be further phosphorylated. Once fully activated, AKT can return to the cytoplasm, or go to the nucleus or other intracellular sites, and phosphorylate other substrate proteins to regulate cell function.

The E17K mutation enhances migration of breast cancer cells, and also enhances resistance to chemotherapeutic drugs. However, the E17K mutation can also selectively destroy chemo-resistant tumor-promoting AKT1 quiescent cancer cells, suggesting that the AKT1(E17K) mutation is crucial in the oncogenic/anti-tumor mechanism.

A major pathway that activates PI3K-AKT signaling pathway is somatic cell mutations, with the E17K mutation being the highest frequency of AKT1 mutations. It is nearly exclusively present in AKT1. The AKT1(E17K) is a recurrent somatic cell mutation predominantly in breast cancer, ovarian cancer, meningioma, and Proteus syndrome.

AKT1(E17K) mutations mediate the PI3K-AKT signaling cascade by expanding PIP lipid specificity, which causes conformational changes. This also enhances subcellular localization to accelerate localization of the PH structural domain to the plasma membrane. The E17K mutation increases PIP3 binding specificity by 7-fold and phosphatidylinositol-(4,5)-bisphosphate (PIP2) by 100-fold.

The AKT1(E17K) mutation also causes rapid conformational changes in the AKT1 PH structural domain. The conformational changes to this domain result in a 4.5-fold increase in its membrane localization, which can result in excessive phosphorylation. The AKT1(E17K) mutation can also result in enhanced subcellular localization by increasing the transient expression.

Given the conformational and signaling effects of the AKT1(E17K) mutation, this target may be useful for targeted treatment of cancers.

Prior Art AKT1 Inhibitors

Most AKT inhibitors targeting the ATP binding site are non-selective against the three isoforms, as well as having poor to no selectivity against other structurally similar kinases. Thus, there remains a need to develop new and novel AKT inhibitors. These ATP targeting inhibitors are classified as aminofurazans, azepane derivatives, isoquinoline-5-sulfonamides, phenylpyrazole derivatives, thiophene carboxamide derivatives, and thiazole carboxamide derivatives.

There are also ATP non-competitive AKT inhibitors which are allosteric modulators which has greater specificity than the ATP targeting inhibitors. Many of these allosteric modulator inhibitors are classified as purine derivatives, thiourea derivatives, alkylphospholipids, sulfonamides, 2,3-diphenylquinoxaline analogs, and indole-3-carbinol derivatives.

Novel AKT1 Inhibitory Compounds

In one aspect, provided herein is a AKT1 inhibitory compound.

One embodiment provides a compound having the structure of Formula (I), or a pharmaceutically acceptable salt or solvate thereof.

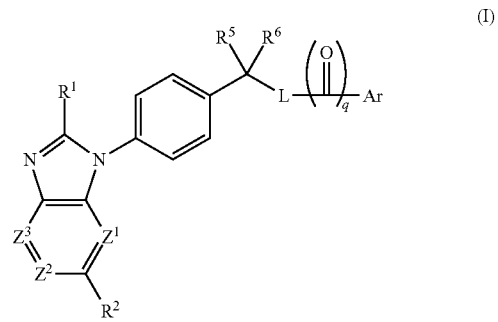

(I)

wherein:
$Z^1$ is N, C—H, or C—$R^3$;
$Z^2$ is N, C—H, or C—$R^4$;
$Z^3$ is N, C—OH, or C—$R^9$;
Ar is selected from:

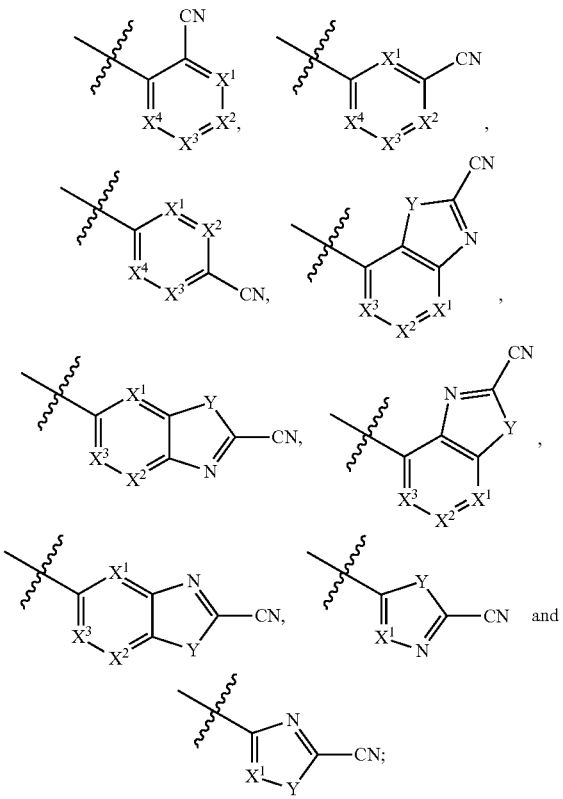

$X^1$ is N or C—$R^7$;
$X^2$ is N or C—$R^7$;
$X^3$ is N or C—$R^7$;
$X^4$ is N or C—$R^7$;
Y is O, S, or N—$R^9$;
$R^1$ is selected from hydrogen, optionally substituted C1-C6 alkyl, optionally substituted aryl, or optionally substituted heteroaryl;
$R^2$ is selected from hydrogen, halogen, —OH, —CN, —N($R^9$)$_2$, —O$R^9$, —S$R^9$, —SO$_2R^9$, —CO$_2R^9$, —CON($R^9$)$_2$, —S$R^9$, —S(O)$R^9$, —S(O)$_2R^9$, optionally substituted C1-C6 alkyl, optionally substituted C1-C6 alkoxy, optionally substituted C2-C6 alkenyl, optionally substituted C2-C6 alkynyl, optionally substituted C3-C7 carbocyclyl, optionally substituted 4-membered to 6-membered heterocyclyl, optionally substituted aryl, aryl substituted with an optionally substituted 4-membered to 6-membered heterocyclyl, optionally substituted heteroaryl or heteroaryl substituted with an optionally substituted 3-membered to 6-membered carbocyclyl;

$R^3$ is selected from optionally substituted C1-C6 alkyl, or optionally substituted aryl;

$R^4$ is selected from halogen, —CN, optionally substituted C1-C6 alkyl, or optionally substituted aryl;

$R^5$ and $R^6$ are each independently hydrogen, deuterium, halogen, —OH, or optionally substituted C1-C6 alkyl; or R and $R^6$ together form an oxo; or $R^5$ and $R^6$ join together to form a carbocycle or heterocycle;

each $R^7$ is independently selected from hydrogen, deuterium, halogen, —OH, —SH, optionally substituted C1-C6 alkoxy, —S-(optionally substituted C1-C6 alkyl), —CN, optionally substituted C1-C6 alkyl, and optionally substituted aryl;

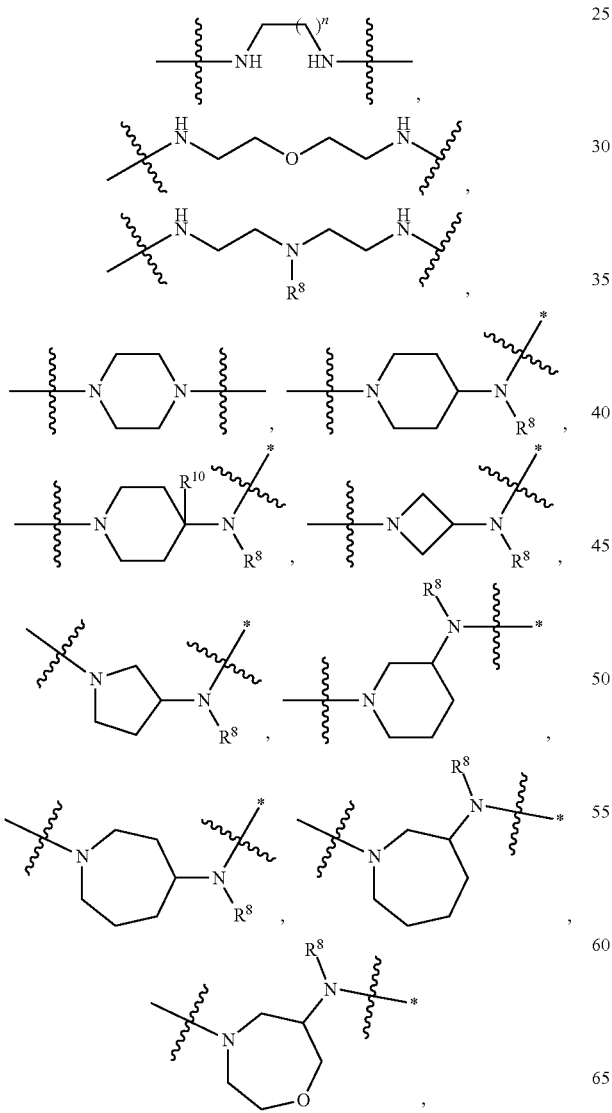

-continued

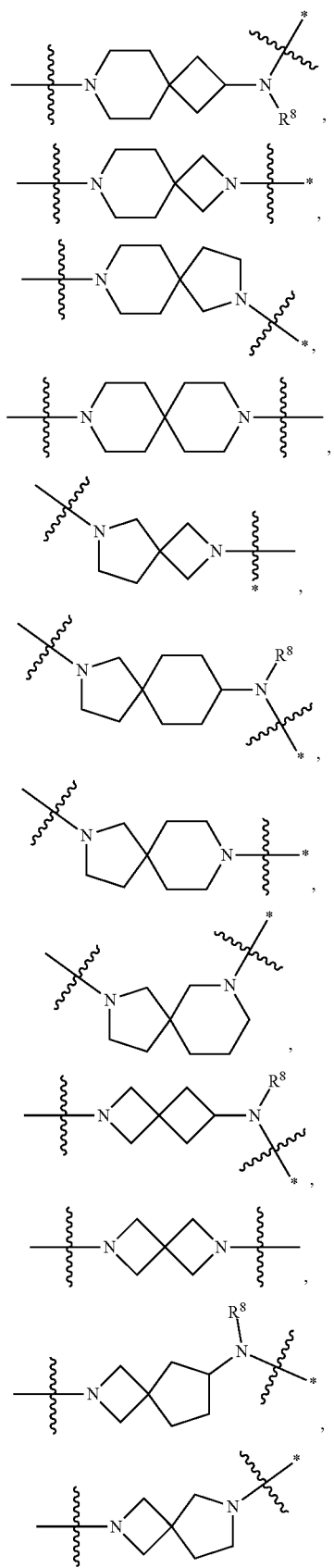

-continued

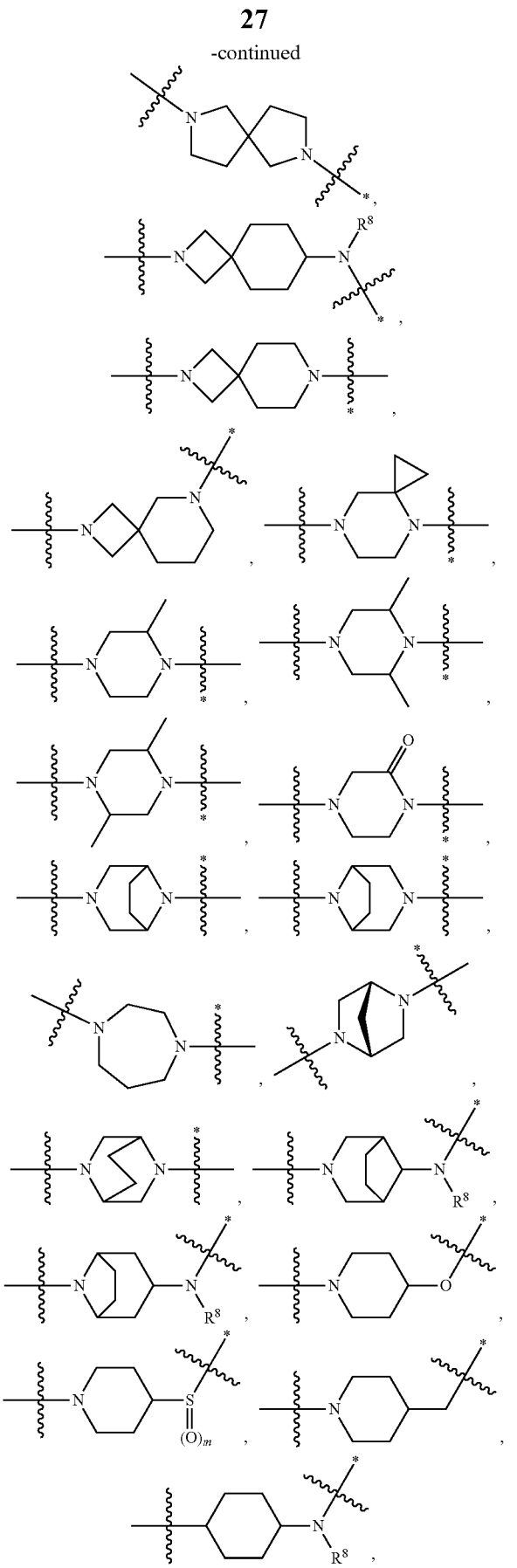

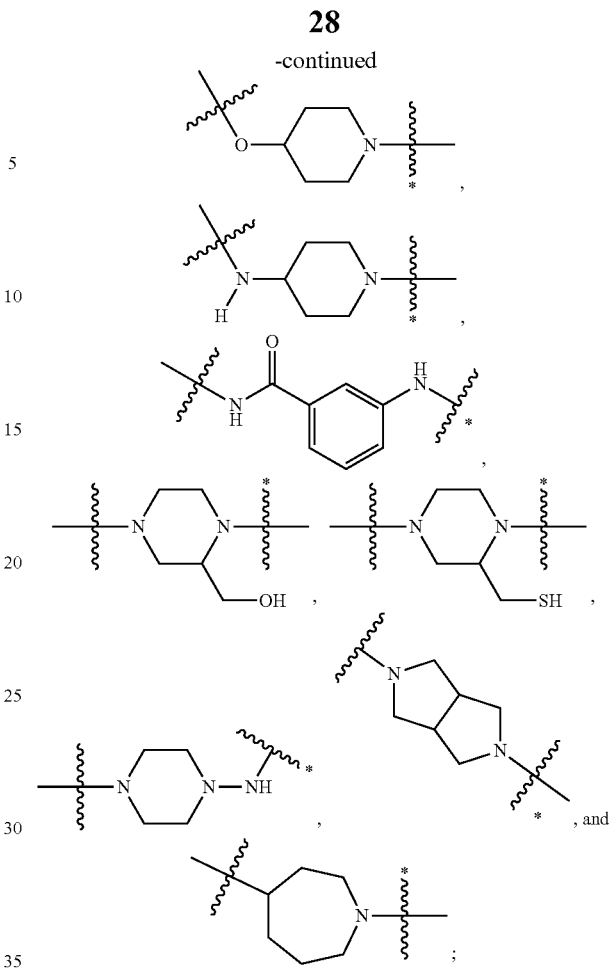

wherein the asterisk (*) indicates the bond to the —CO-Ar group;

$R^8$ is hydrogen, optionally substituted C1-C6 alkyl, optionally substituted C3-C7 cycloalkyl, or optionally substituted heterocyclyl;

each $R^9$ is hydrogen, or optionally substituted C1-C6 alkyl;

$R^{10}$ is optionally substituted C1-C6 alkyl;

m is 0, 1, or 2;

n is 1, 2, or 3; and q is 0 or 1.

One embodiment provides a compound having the structure of Formula (Ia), or a pharmaceutically acceptable salt or solvate thereof:

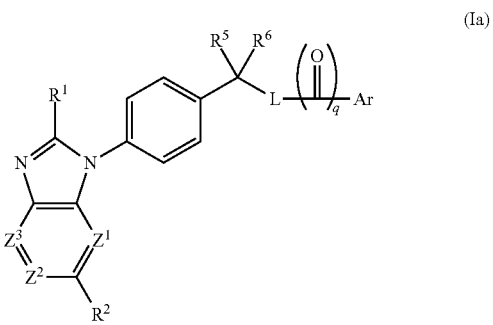

(Ia)

wherein:
Z¹ is N, C—H, or C—R³;
Z² is N, C—H, or C—R⁴;
Z³ is N, C—H;
Ar is selected from

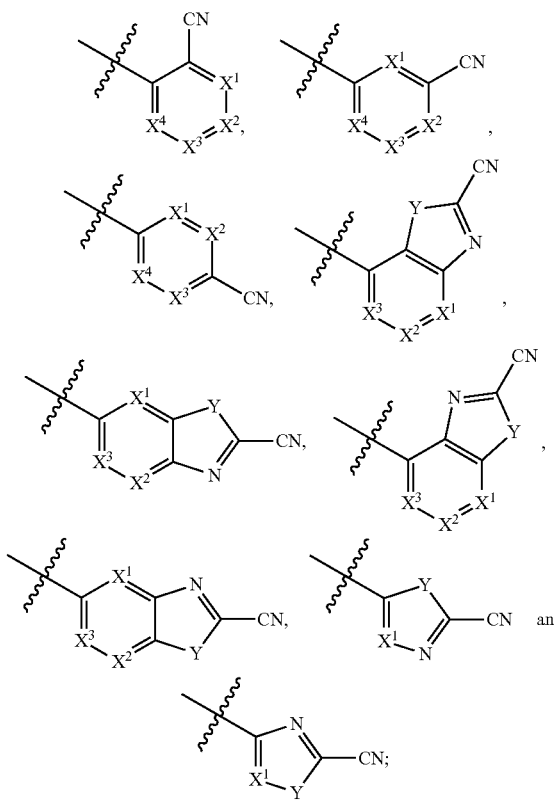

X¹ is N or C—R⁷;
X² is N or C—R⁷;
X¹ is N or C—R⁷;
X² is N or C—R⁷;
Y is O, S, or N—R⁹;
R¹ is selected from hydrogen, optionally substituted C1-C6 alkyl, optionally substituted aryl, or optionally substituted heteroaryl;
R² is selected from hydrogen, halogen, —OH, —CN, —N(R⁹)₂, —OR⁹, —SR⁹, —SO₂R⁹, —CO₂R⁹, —CON(R⁹)₂, optionally substituted C1-C6 alkyl, optionally substituted C3-C7 carbocyclyl, optionally substituted 4-membered to 6-membered heterocyclyl optionally substituted aryl, or optionally substituted heteroaryl;
R³ is selected from optionally substituted C1-C6 alkyl, or optionally substituted aryl;
R⁴ is selected from halogen, —CN, optionally substituted C1-C6 alkyl, or optionally substituted aryl;
R⁵ and R⁶ are each independently hydrogen, deuterium, halogen, —OH, or optionally substituted C1-C6 alkyl; or R⁵ and R⁶ together form an oxo; or R⁵ and R⁶ join together to form a carbocycle or heterocycle;
each R⁷ is independently selected from hydrogen, deuterium, halogen, —OH, —SH, optionally substituted C1-C6 alkoxy, —S-(optionally substituted C1-C6 alkyl), —CN, optionally substituted C1-C6 alkyl, and optionally substituted aryl;
L is selected from —N(R⁸)—, or a divalent radical selected from:

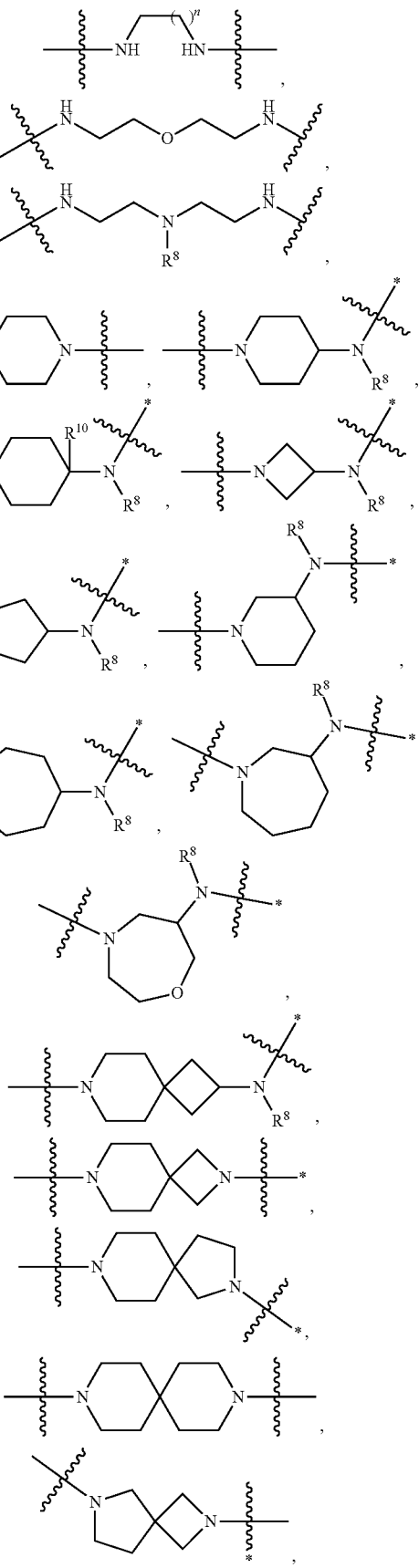

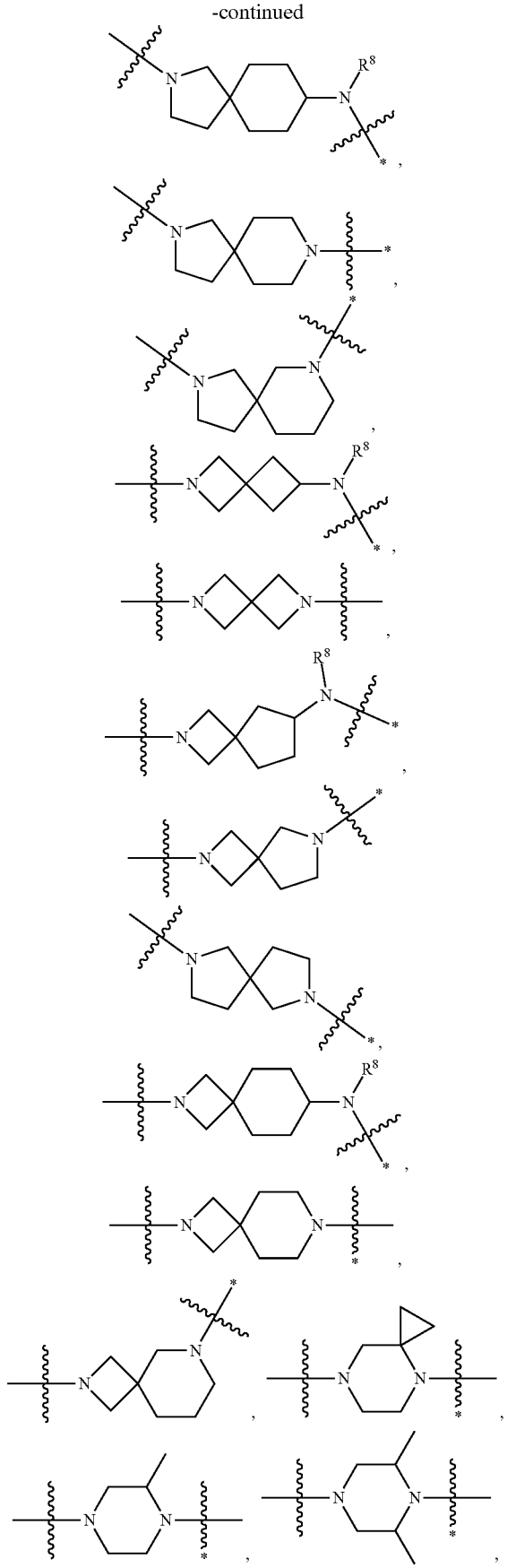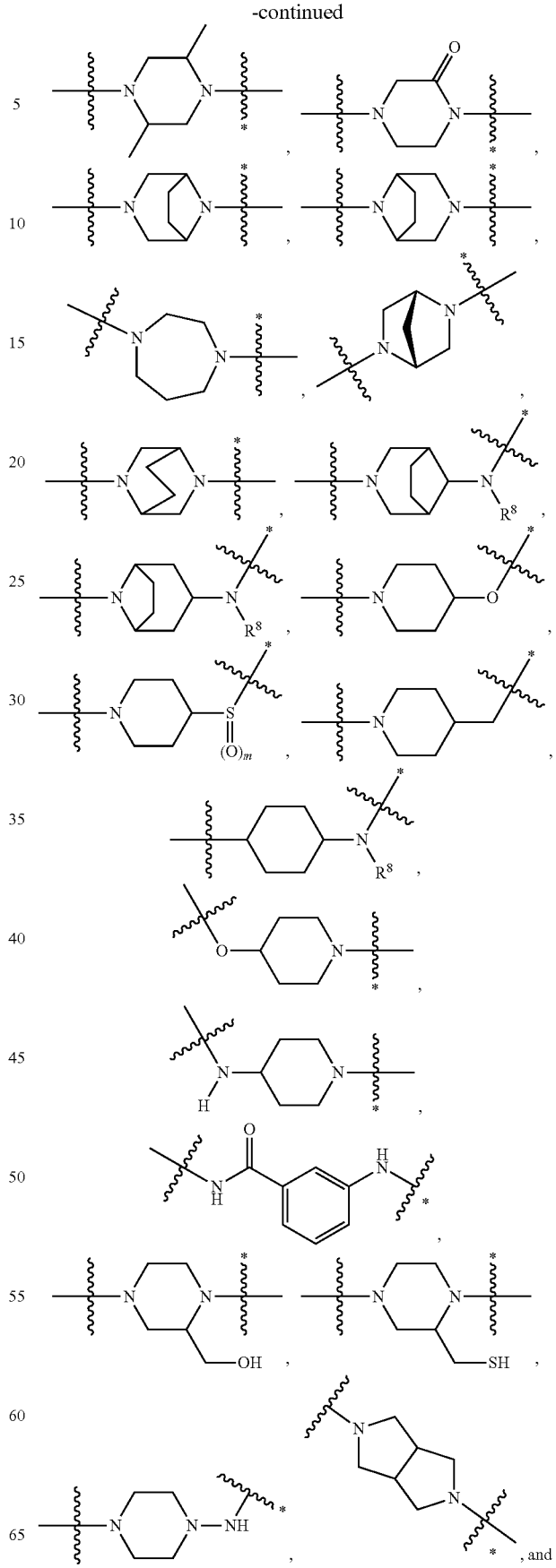

-continued

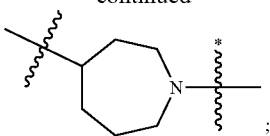

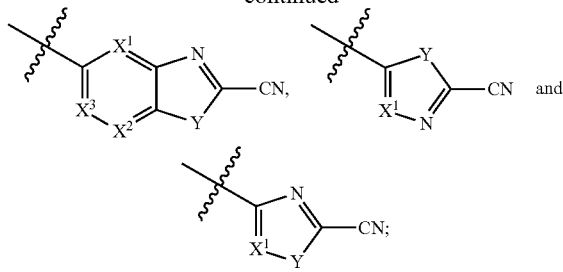

wherein the asterisk (*) indicates the bond to the —CO-Ar group;

$R^8$ is hydrogen, optionally substituted C1-C6 alkyl, optionally substituted C3-C7 cycloalkyl, or optionally substituted heterocyclyl;

each $R^9$ is hydrogen, or optionally substituted C1-C6 alkyl;

$R^{10}$ is optionally substituted C1-C6 alkyl;

m is 0, 1, or 2;

n is 1, 2, or 3; and q is 0 or 1.

One embodiment provides a compound having the structure of Formula (Ib), or a pharmaceutically acceptable salt or solvate thereof:

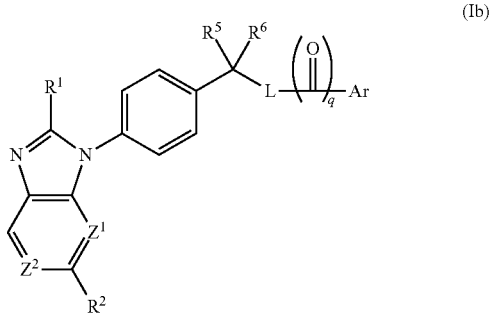

(Ib)

wherein:

$Z^1$ is N, C—H, or C—$R^3$;

$Z^2$ is N, C—H, or C—$R^4$;

Ar is selected from:

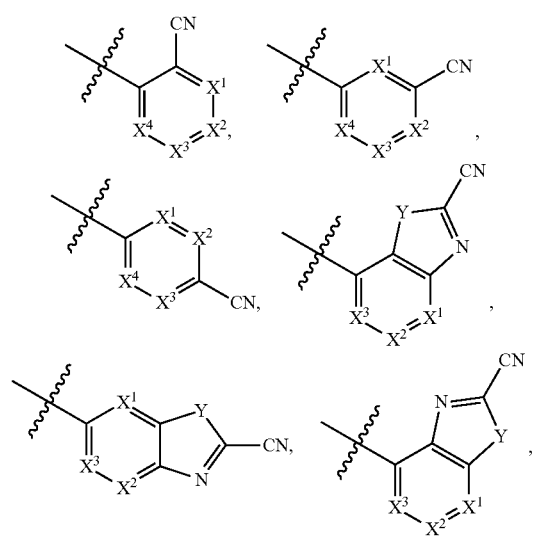

$X^1$ is N or C—$R^7$;

$X^2$ is N or C—$R^7$;

$X^3$ is N or C—$R^7$;

$X^4$ is N or C—$R^7$;

Y is O, S, or N—$R^9$;

$R^1$ is selected from hydrogen, optionally substituted C1-C6 alkyl, optionally substituted aryl, or optionally substituted heteroaryl;

$R^2$ is selected from hydrogen, optionally substituted C1-C6 alkyl, optionally substituted aryl, or optionally substituted heteroaryl;

$R^3$ is selected from optionally substituted C1-C6 alkyl, or optionally substituted aryl;

$R^4$ is selected from optionally substituted C1-C6 alkyl, or optionally substituted aryl;

$R^5$ and $R^6$ are each independently hydrogen, deuterium, halogen, —OH, or optionally substituted C1-C6 alkyl; or $R^5$ and $R^6$ together form an oxo; or $R^5$ and $R^6$ join together to form a carbocycle or heterocycle;

each $R^7$ is independently selected from hydrogen, deuterium, halogen, —OH, —SH, optionally substituted C1-C6 alkoxy, —S-(optionally substituted C1-C6 alkyl), —CN, optionally substituted C1-C6 alkyl, and optionally substituted aryl;

L is selected from —N($R^8$)—, or a divalent radical selected from:

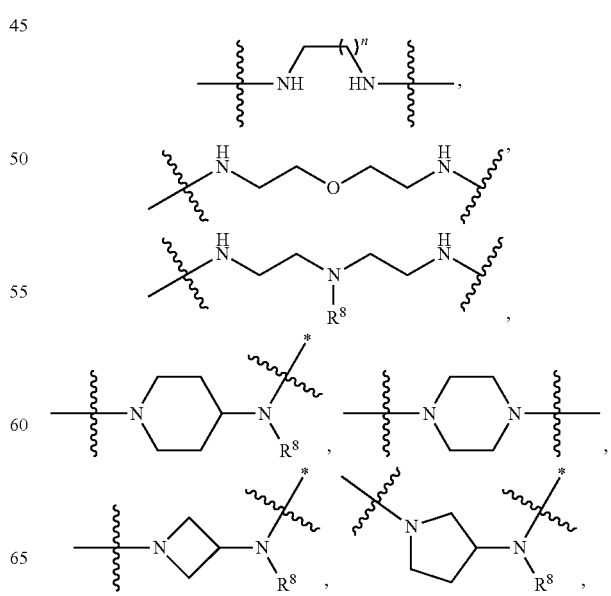

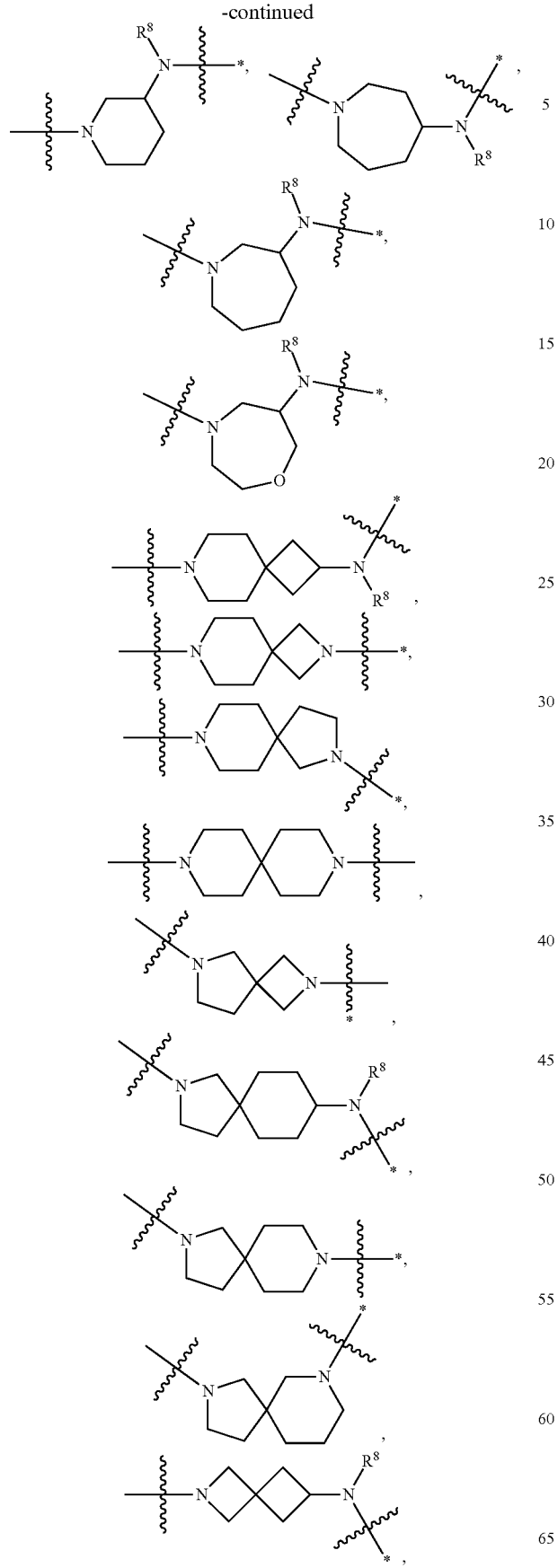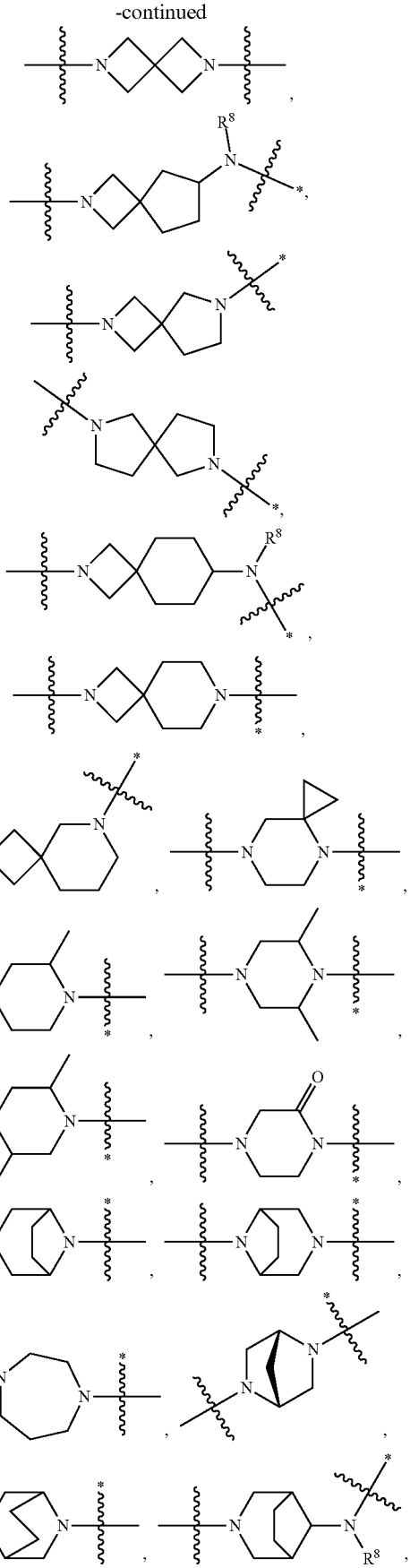

-continued

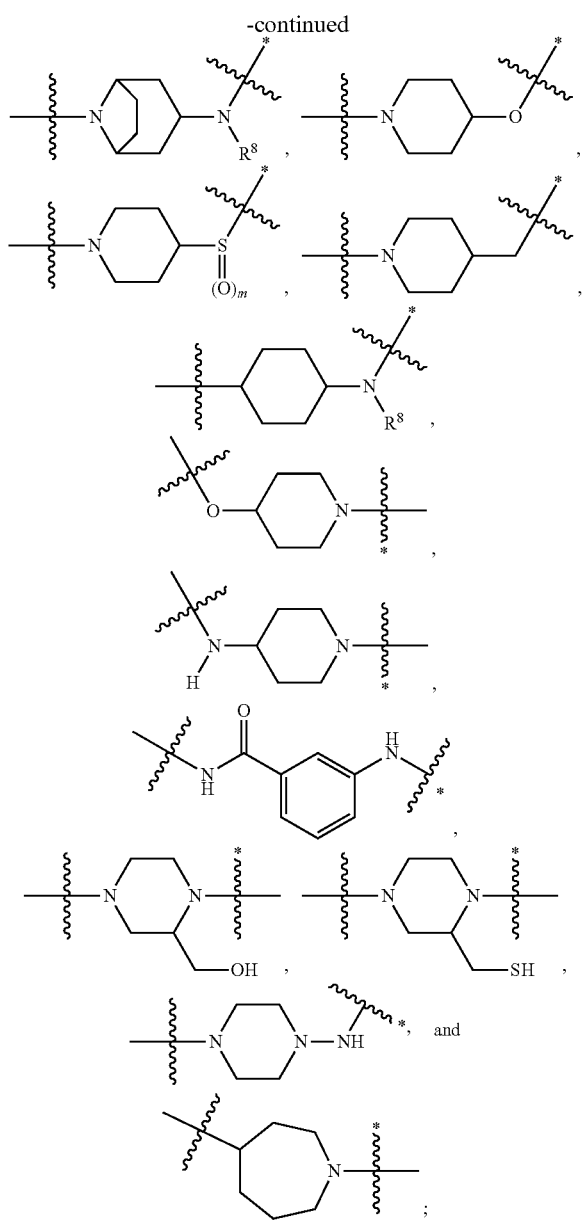

wherein the asterisk (*) indicates the bond to the —CO-Ar group;
R⁸ is hydrogen, optionally substituted C1-C6 alkyl, optionally substituted C3-C7 cycloalkyl, or optionally substituted heterocyclyl;
R⁹ is hydrogen, or optionally substituted C1-C6 alkyl;
m is 0, 1, or 2;
n is 1, 2, or 3; and
q is 0 or 1.

Another embodiment provides the compound of Formula (I), (Ia) or (Ib), or pharmaceutically acceptable salt or solvate thereof, wherein $Z^1$ is N.

Another embodiment provides the compound of Formula (I), (Ia) or (Ib), or pharmaceutically acceptable salt or solvate thereof, wherein $Z^2$ is C—H.

Another embodiment provides the compound of Formula (I), (Ia) or (Ib), or pharmaceutically acceptable salt or solvate thereof, wherein $Z^2$ is C—$R^4$.

Another embodiment provides the compound of Formula (I), (Ta) or (Ib), or pharmaceutically acceptable salt or solvate thereof, wherein $R^1$ is optionally substituted heteroaryl. Another embodiment provides the compound of Formula (I), (Ia) or (Ib), or pharmaceutically acceptable salt or solvate thereof, wherein the optionally substituted heteroaryl is an optionally substituted pyridyl.

Another embodiment provides the compound of Formula (I), (Ia) or (Ib), or pharmaceutically acceptable salt or solvate thereof, wherein $R^2$ is optionally substituted aryl. Another embodiment provides the compound of Formula (I), (Ia) or (Ib), or pharmaceutically acceptable salt or solvate thereof, wherein the optionally substituted aryl is an optionally substituted phenyl.

Another embodiment provides the compound of Formula (I), (Ia) or (Ib), or pharmaceutically acceptable salt or solvate thereof, wherein $R^2$ is optionally substituted heteroaryl. Another embodiment provides the compound of Formula (I), (Ia) or (Ib), or pharmaceutically acceptable salt or solvate thereof, wherein the optionally substituted heteroaryl is an optionally substituted pyridyl.

Another embodiment provides the compound of Formula (I), (Ia) or (Ib), or pharmaceutically acceptable salt or solvate thereof, wherein $R^5$ is hydrogen. Another embodiment provides the compound of Formula (I), (Ia) or (Ib), or pharmaceutically acceptable salt or solvate thereof, wherein $R^6$ is hydrogen. Another embodiment provides the compound of Formula (I), (Ia) or (Ib), or pharmaceutically acceptable salt or solvate thereof, wherein $R^5$ and $R^6$ together form an oxo. Another embodiment provides the compound of Formula (I), (Ia) or (Ib), or pharmaceutically acceptable salt or solvate thereof, wherein $R^6$ is optionally substituted C1-C6 alkyl. Another embodiment provides the compound of Formula (I), (Ia) or (Ib), or pharmaceutically acceptable salt or solvate thereof, wherein $R^5$ and $R^6$ join together to form a carbocycle or heterocycle.

Another embodiment provides the compound of Formula (I), (Ia) or (Ib), or pharmaceutically acceptable salt or solvate thereof, wherein L is —N($R^8$)—.

Another embodiment provides the compound of Formula (I), (Ta) or (Ib), or pharmaceutically acceptable salt or solvate thereof, wherein L is selected from a divalent radical selected from:

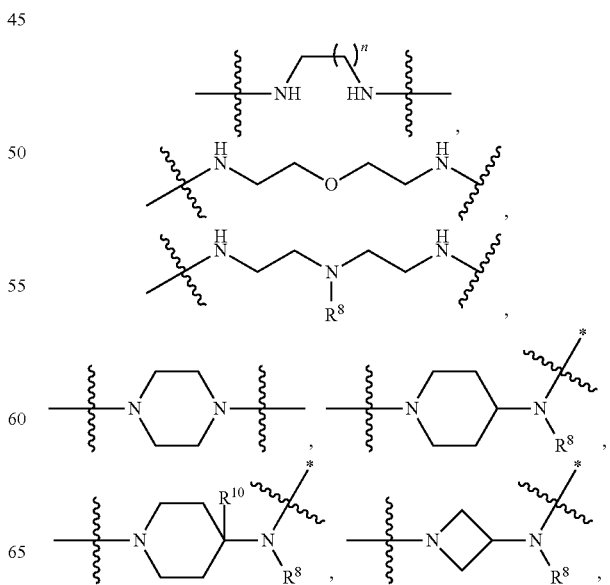

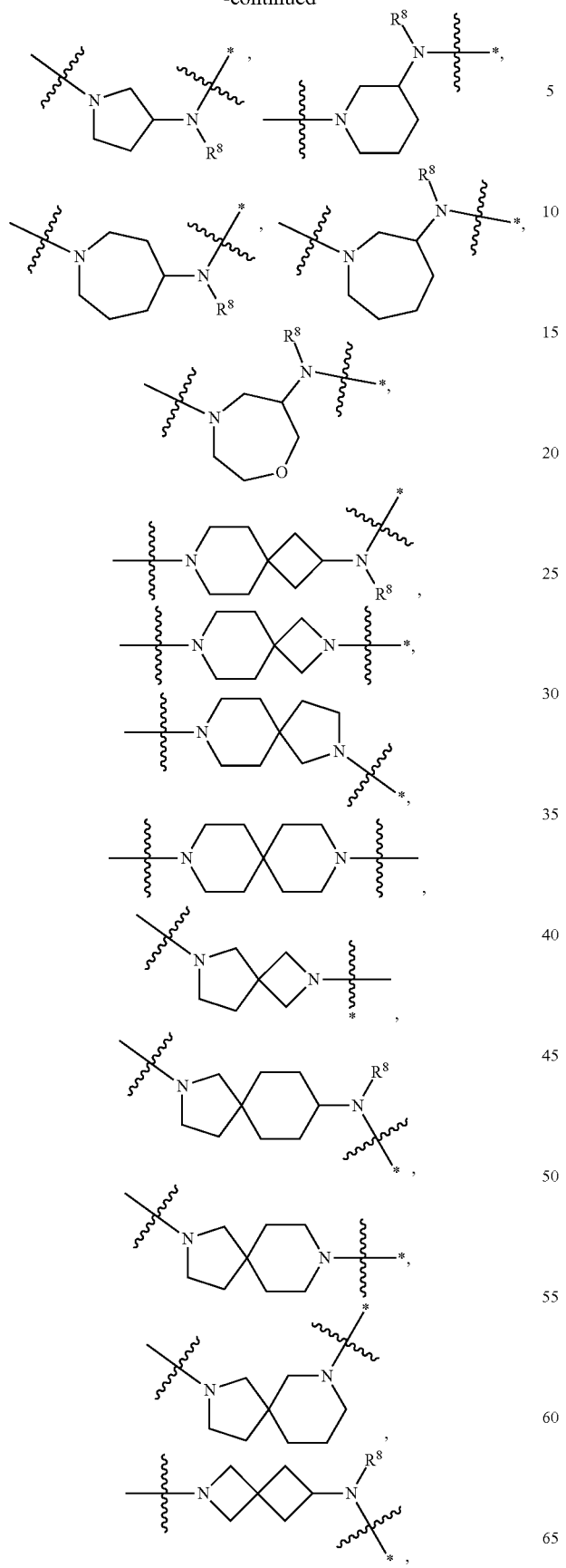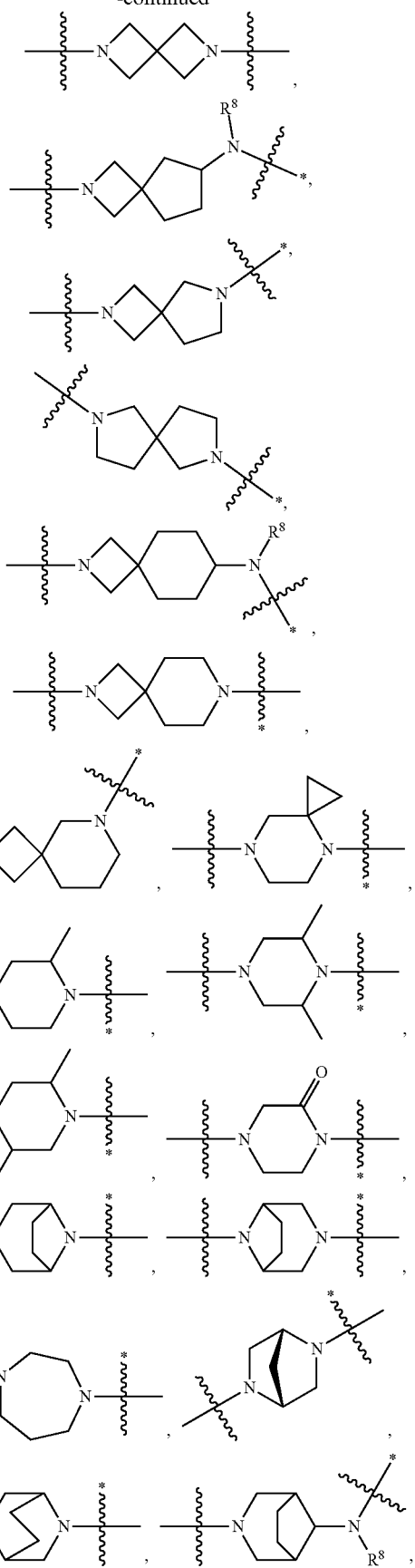

-continued

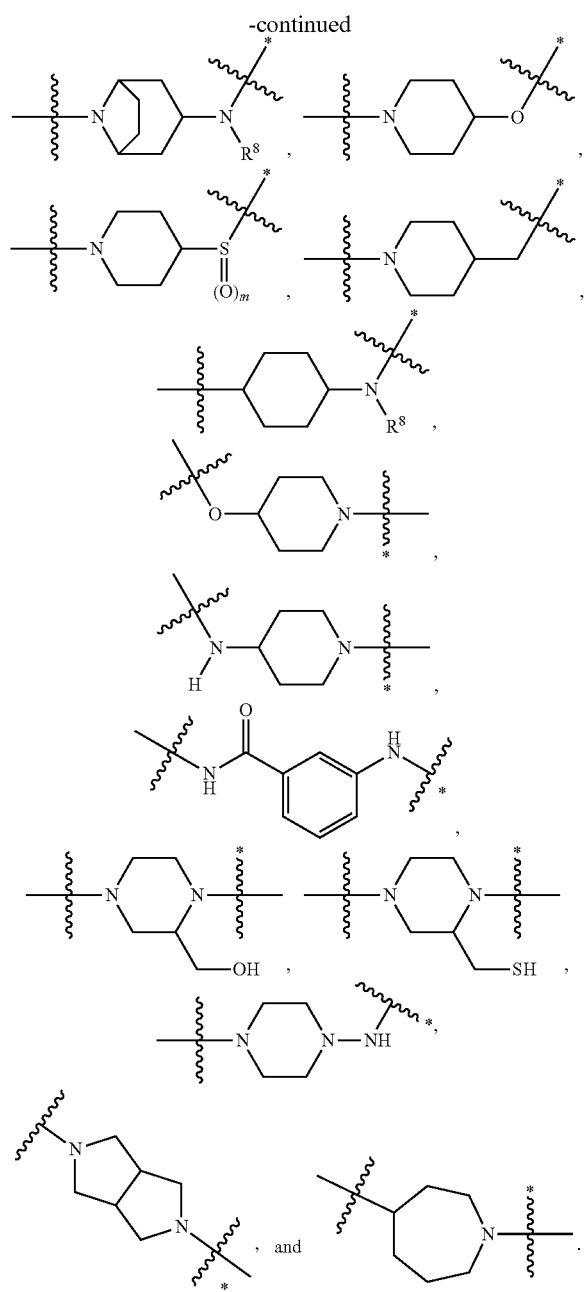

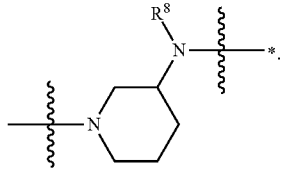

Another embodiment provides the compound of Formula (I), (Ia) or (Ib), or pharmaceutically acceptable salt or solvate thereof, wherein L is selected from:

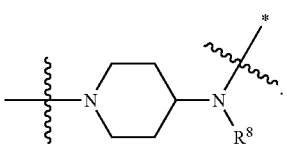

Another embodiment provides the compound of Formula (I), (Ia) or (Ib), or pharmaceutically acceptable salt or solvate thereof, wherein L is selected from:

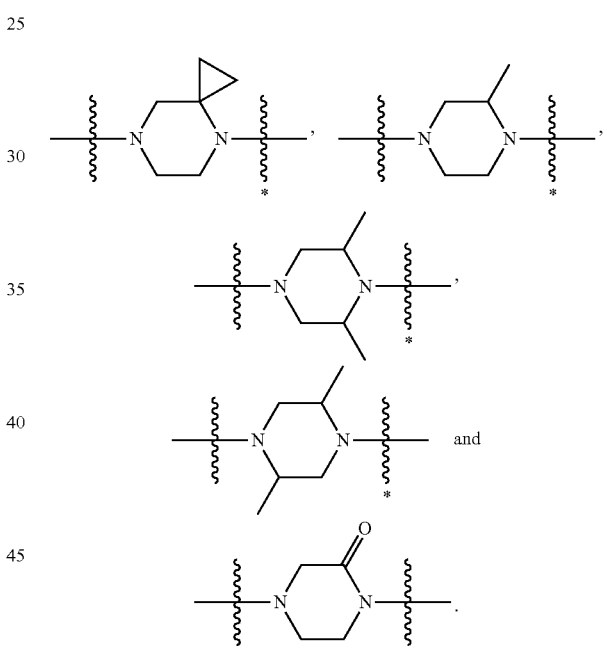

Another embodiment provides the compound of Formula (I), (Ia) or (Ib), or pharmaceutically acceptable salt or solvate thereof, wherein L is selected from:

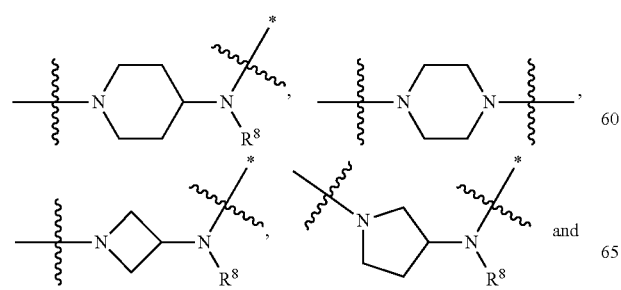

Another embodiment provides the compound of Formula (I), (Ia) or (Ib), or pharmaceutically acceptable salt or solvate thereof, wherein L is selected from:

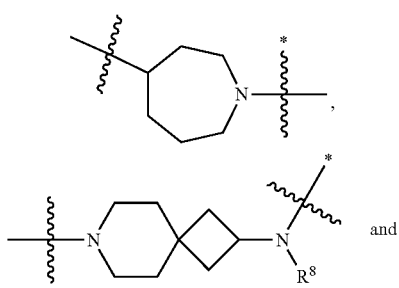

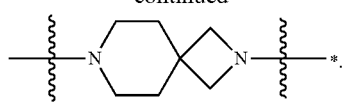

Another embodiment provides the compound of Formula (I), (Ia) or (Ib), or pharmaceutically acceptable salt or solvate thereof, wherein L is selected from:

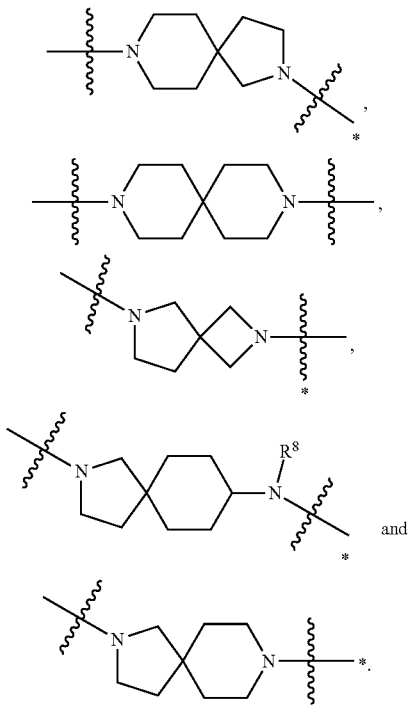

Another embodiment provides the compound of Formula (I), (Ia) or (Ib), or pharmaceutically acceptable salt or solvate thereof, wherein L is selected from:

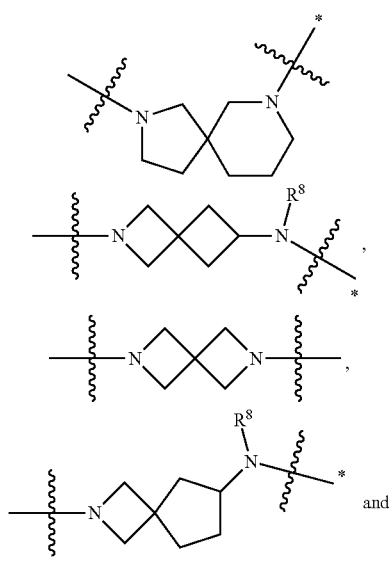

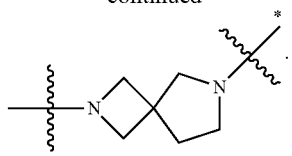

Another embodiment provides the compound of Formula (I), (Ia) or (Ib), or pharmaceutically acceptable salt or solvate thereof, wherein L is selected from:

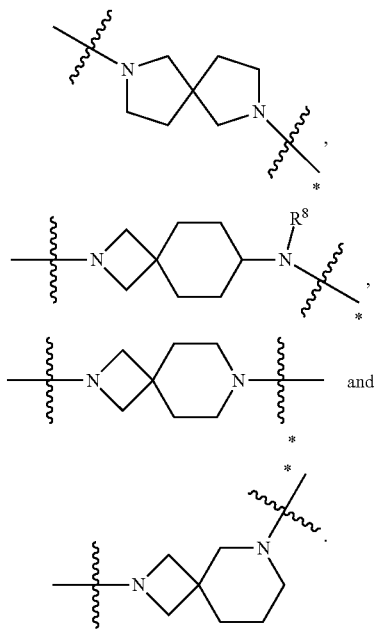

Another embodiment provides the compound of Formula (I), (Ia) or (Ib), or pharmaceutically acceptable salt or solvate thereof, wherein $R^8$ is hydrogen. Another embodiment provides the compound of Formula (I), (Ia) or (Ib), or pharmaceutically acceptable salt or solvate thereof, wherein $R^8$ is optionally substituted $C_1$-$C_6$ alkyl.

Another embodiment provides the compound of Formula (I), (Ia) or (Ib), or pharmaceutically acceptable salt or solvate thereof, wherein q is 0.

Another embodiment provides the compound of Formula (I), (Ia) or (Ib), or pharmaceutically acceptable salt or solvate thereof, wherein q is 1.

Another embodiment provides the compound of Formula (I), (Ia) or (Ib), or pharmaceutically acceptable salt or solvate thereof, wherein Ar is

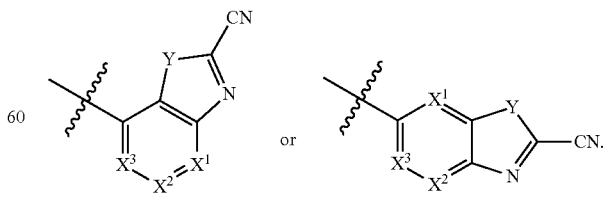

Another embodiment provides the compound of Formula (I), (Ia) or (Ib), or pharmaceutically acceptable salt or solvate thereof, wherein Ar is

[Structures: Ar groups with CN substituents on fused bicyclic heteroaromatic systems]

Another embodiment provides the compound of Formula (I), (Ia) or (Ib), or pharmaceutically acceptable salt or solvate thereof, wherein Ar is

[Structures: two monocyclic heteroaromatic Ar groups with CN]

Another embodiment provides the compound of Formula (I), (Ia) or (Ib), or pharmaceutically acceptable salt or solvate thereof, wherein $X^1$, $X^2$, and $X^3$ are C—H. Another embodiment provides the compound of Formula (I), (Ia) or (Ib), or pharmaceutically acceptable salt or solvate thereof, wherein $X^1$ is N; and $X^2$, and $X^3$ are C—H. Another embodiment provides the compound of Formula (I), (Ia) or (Ib), or pharmaceutically acceptable salt or solvate thereof, wherein $X^2$ is N; and $X^1$, and $X^3$ are C—H. Another embodiment provides the compound of Formula (I), (Ia) or (Ib), or pharmaceutically acceptable salt or solvate thereof, wherein $X^3$ is N; and $X^1$, and $X^2$ are C—H. Another embodiment provides the compound of Formula (I), (Ia) or (Ib), or pharmaceutically acceptable salt or solvate thereof, wherein $X^1$ is N; and $X^2$, and $X^3$ are C—H.

Another embodiment provides the compound of Formula (I), (Ia) or (Ib), or pharmaceutically acceptable salt or solvate thereof, wherein Y is O. Another embodiment provides the compound of Formula (I), (Ia) or (Ib), or pharmaceutically acceptable salt or solvate thereof, wherein Y is S. Another embodiment provides the compound of Formula (I), (Ia) or (Ib), or pharmaceutically acceptable salt or solvate thereof, wherein Y is N—$R^9$. Another embodiment provides the compound of Formula (I), (Ia) or (Ib), or pharmaceutically acceptable salt or solvate thereof, wherein $R^9$ is hydrogen. Another embodiment provides the compound of Formula (I), (Ia) or (Ib), or pharmaceutically acceptable salt or solvate thereof, wherein $R^9$ is optionally substituted $C_1$-$C_6$ alkyl.

Another embodiment provides the compound of Formula (I), (Ia) or (Ib), or pharmaceutically acceptable salt or solvate thereof, wherein Ar is

[Structures: three six-membered heteroaryl Ar groups with CN]

Another embodiment provides the compound of Formula (I), (Ia) or (Ib), or pharmaceutically acceptable salt or solvate thereof, wherein $X^1$ is N. Another embodiment provides the compound of Formula (I), (Ia) or (Ib), or pharmaceutically acceptable salt or solvate thereof, wherein $X^2$ is N. Another embodiment provides the compound of Formula (I), (Ia) or (Ib), or pharmaceutically acceptable salt or solvate thereof, wherein $X^3$ is N. Another embodiment provides the compound of Formula (I), (Ia) or (Ib), or pharmaceutically acceptable salt or solvate thereof, wherein $X^4$ is N. Another embodiment provides the compound of Formula (I), (Ia) or (Ib), or pharmaceutically acceptable salt or solvate thereof, wherein $X^1$ is C—H. Another embodiment provides the compound of Formula (I), (Ia) or (Ib), or pharmaceutically acceptable salt or solvate thereof, wherein $X^2$ is C—H. Another embodiment provides the compound of Formula (I), (Ia) or (Ib), or pharmaceutically acceptable salt or solvate thereof, wherein $X^3$ is C—H. Another embodiment provides the compound of Formula (I), (Ia) or (Ib), or pharmaceutically acceptable salt or solvate thereof, wherein $X^4$ is C—H.

Another embodiment provides the compound of Formula (I), (Ia) or (Ib), or pharmaceutically acceptable salt or solvate thereof, wherein Ar is

[Structure: six-membered heteroaryl with CN and $X^1$-$X^4$]

Another embodiment provides the compound of Formula (I), (Ia) or (Ib), or pharmaceutically acceptable salt or solvate thereof, wherein $X^1$ is N. Another embodiment provides the compound of Formula (I), (Ia) or (Ib), or pharmaceutically acceptable salt or solvate thereof, wherein $X^2$ is N. Another embodiment provides the compound of Formula (I), (Ia) or (Ib), or pharmaceutically acceptable salt or solvate thereof, wherein $X^3$ is N. Another embodiment provides the compound of Formula (I), (Ia) or (Ib), or pharmaceutically acceptable salt or solvate thereof, wherein $X^4$ is N. Another embodiment provides the compound of Formula (I), (Ta) or (Ib), or pharmaceutically acceptable salt or solvate thereof, wherein $X^1$ is C—H. Another embodiment provides the compound of Formula (I), (Ia) or (Ib), or pharmaceutically acceptable salt or solvate thereof, wherein $X^2$ is C—H. Another embodiment provides the compound of Formula (I), (Ia) or (Ib), or pharmaceutically acceptable salt or solvate thereof, wherein $X^3$ is C—H. Another embodiment provides the compound of Formula (I), (Ia) or (Ib), or pharmaceutically acceptable salt or solvate thereof, wherein $X^4$ is C—H.

Another embodiment provides the compound of Formula (I), (Ia) or (Ib), or pharmaceutically acceptable salt or solvate thereof, wherein $R^3$ is optionally substituted $C_1$-$C_6$ alkyl. Another embodiment provides the compound of Formula (I), (Ia) or (Ib), or pharmaceutically acceptable salt or solvate thereof, wherein $R^3$ is optionally substituted aryl. Another embodiment provides the compound of Formula (I), (Ia) or (Ib), or pharmaceutically acceptable salt or solvate thereof, wherein $R^4$ is optionally substituted $C_1$-$C_6$ alkyl. Another embodiment provides the compound of Formula (I), (Ta) or (Ib), or pharmaceutically acceptable salt or solvate thereof, wherein $R^4$ is optionally substituted aryl.

One embodiment provides an AKT1 inhibitory compound, or a pharmaceutically acceptable salt or solvate thereof, having a structure resented in Table 1.

TABLE 1

| Example | Compound Structure | Compound Name |
|---|---|---|
| 1 | 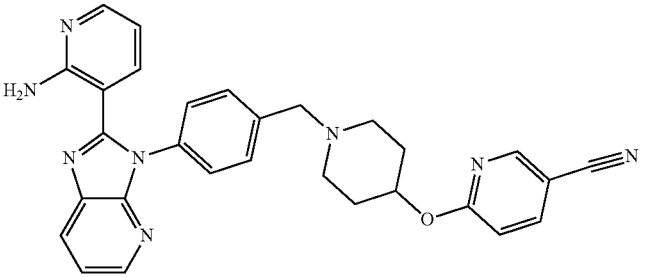 [SMILES: N#Cc1ccc(OC2CCN(Cc3ccc(-n4c(-c5cccnc5N)nc5cccnc54)cc3)CC2)nc1] | 6-((1-(4-(2-(2-aminopyridin-3-yl)-3H-imidazo[4,5-b]pyridin-3-yl)benzyl)piperidin-4-yl)oxy)nicotinonitrile |
| 2 | 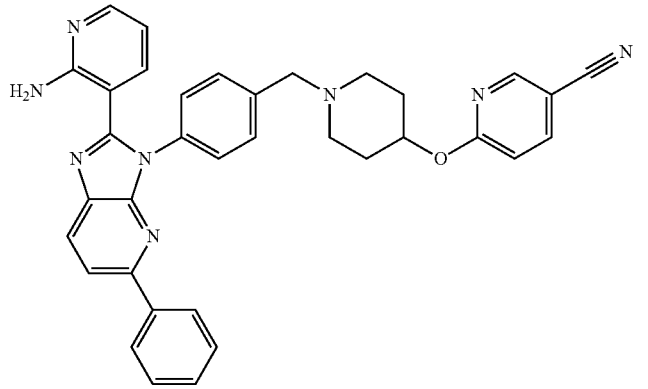 [SMILES: N#Cc1ccc(OC2CCN(Cc3ccc(-n4c(-c5cccnc5N)nc5ccc(-c6ccccc6)nc54)cc3)CC2)nc1] | 6-((1-(4-(2-(2-aminopyridin-3-yl)-5-phenyl-3H-imidazo[4,5-b]pyridin-3-yl)benzyl)piperidin-4-yl)oxy)nicotinonitrile |
| 3 | 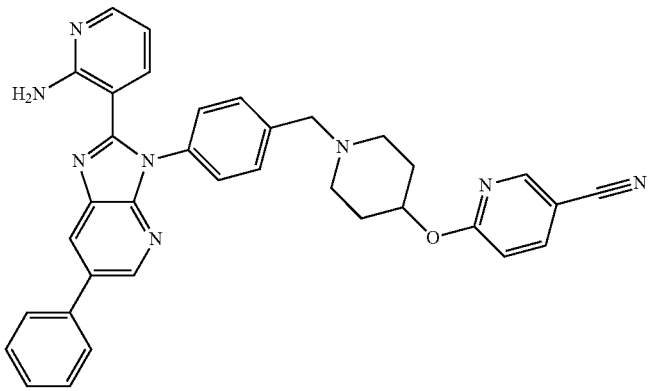 [SMILES: N#Cc1ccc(OC2CCN(Cc3ccc(-n4c(-c5cccnc5N)nc5cc(-c6ccccc6)cnc54)cc3)CC2)nc1] | 6-((1-(4-(2-(2-aminopyridin-3-yl)-6-phenyl-3H-imidazo[4,5-b]pyridin-3-yl)benzyl)piperidin-4-yl)oxy)nicotinonitrile |
| 4 | 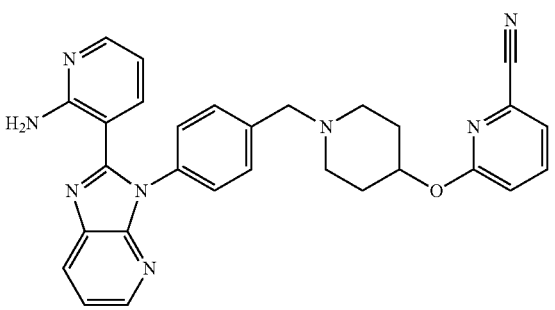 [SMILES: N#Cc1cccc(OC2CCN(Cc3ccc(-n4c(-c5cccnc5N)nc5cccnc54)cc3)CC2)n1] | 6-((1-(4-(2-(2-aminopyridin-3-yl)-3H-imidazo[4,5-b]pyridin-3-yl)benzyl)piperidin-4-yl)oxy)picolinonitrile |

TABLE 1-continued

| Example | Compound Structure | Compound Name |
|---|---|---|
| 5 | 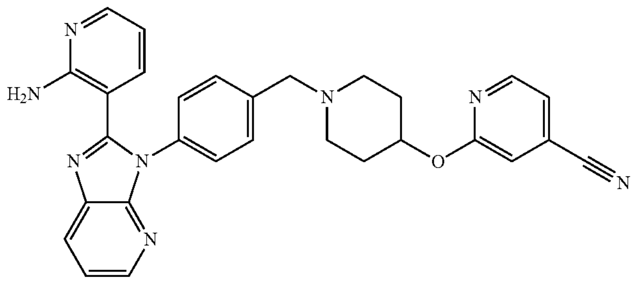 [SMILES: N#Cc1ccnc(OC2CCN(Cc3ccc(-n4c(-c5cccnc5N)nc5cccnc54)cc3)CC2)c1] | 2-((1-(4-(2-(2-aminopyridin-3-yl)-3H-imidazo[4,5-b]pyridin-3-yl)benzyl)piperidin-4-yl)oxy)isonicotinonitrile |
| 6 | 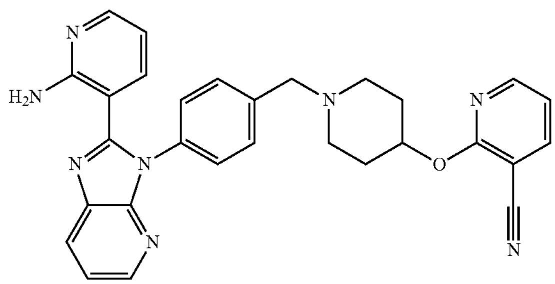 [SMILES: N#Cc1cccnc1OC1CCN(Cc2ccc(-n3c(-c4cccnc4N)nc4cccnc43)cc2)CC1] | 2-((1-(4-(2-(2-aminopyridin-3-yl)-3H-imidazo[4,5-b]pyridin-3-yl)benzyl)piperidin-4-yl)oxy)nicotinonitrile |
| 7 | 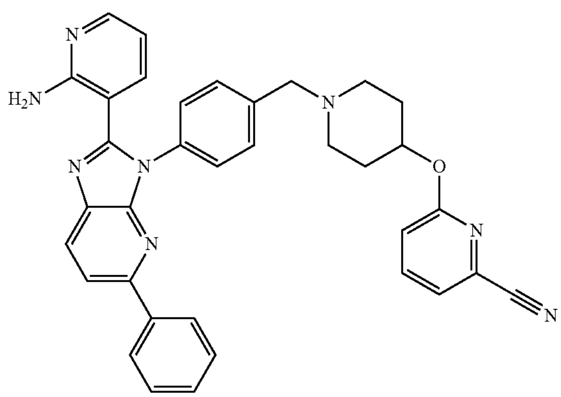 [SMILES: N#Cc1cccc(OC2CCN(Cc3ccc(-n4c(-c5cccnc5N)nc5ccc(-c6ccccc6)nc54)cc3)CC2)n1] | 6-((1-(4-(2-(2-aminopyridin-3-yl)-5-phenyl-3H-imidazo[4,5-b]pyridin-3-yl)benzyl)piperidin-4-yl)oxy)picolinonitrile |
| 8 | 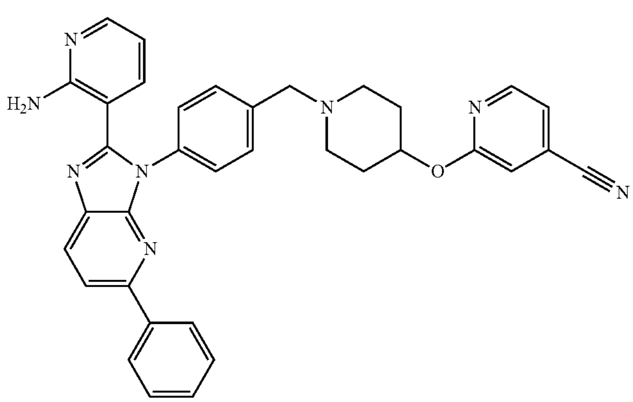 [SMILES: N#Cc1ccnc(OC2CCN(Cc3ccc(-n4c(-c5cccnc5N)nc5ccc(-c6ccccc6)nc54)cc3)CC2)c1] | 2-((1-(4-(2-(2-aminopyridin-3-yl)-5-phenyl-3H-imidazo[4,5-b]pyridin-3-yl)benzyl)piperidin-4-yl)oxy)isonicotinonitrile |

TABLE 1-continued

| Example | Compound Structure | Compound Name |
|---|---|---|
| 9 | 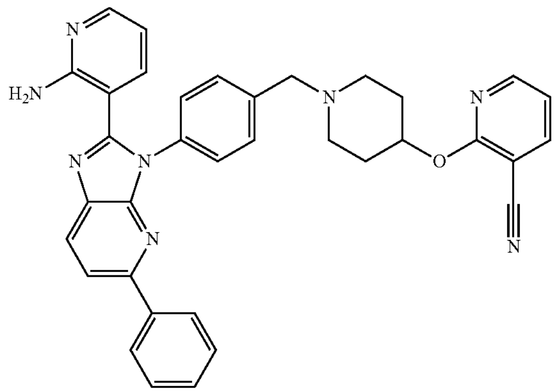 [SMILES: N#Cc1cccnc1OC1CCN(Cc2ccc(-n3c(-c4cccnc4N)nc4ccc(-c5ccccc5)nc43)cc2)CC1] | 2-((1-(4-(2-(2-aminopyridin-3-yl)-5-phenyl-3H-imidazo[4,5-b]pyridin-3-yl)benzyl)piperidin-4-yl)oxy)nicotinonitrile |
| 10 | 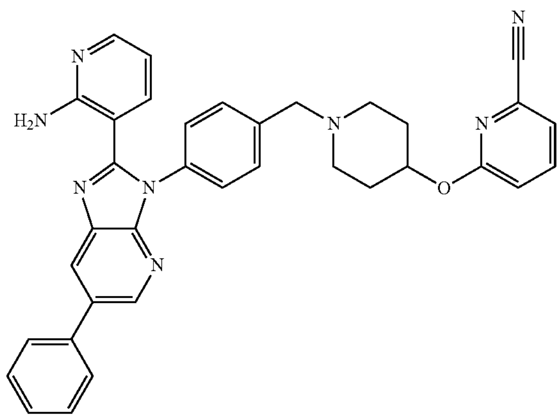 [SMILES: N#Cc1cccc(OC2CCN(Cc3ccc(-n4c(-c5cccnc5N)nc5cc(-c6ccccc6)cnc54)cc3)CC2)n1] | 6-((1-(4-(2-(2-aminopyridin-3-yl)-6-phenyl-3H-imidazo[4,5-b]pyridin-3-yl)benzyl)piperidin-4-yl)oxy)picolinonitrile |
| 11 | 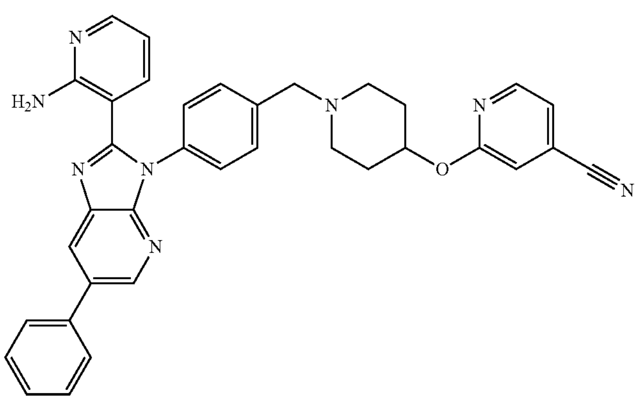 [SMILES: N#Cc1ccnc(OC2CCN(Cc3ccc(-n4c(-c5cccnc5N)nc5cc(-c6ccccc6)cnc54)cc3)CC2)c1] | 2-((1-(4-(2-(2-aminopyridin-3-yl)-6-phenyl-3H-imidazo[4,5-b]pyridin-3-yl)benzyl)piperidin-4-yl)oxy)isonicotinonitrile |
| 12 | 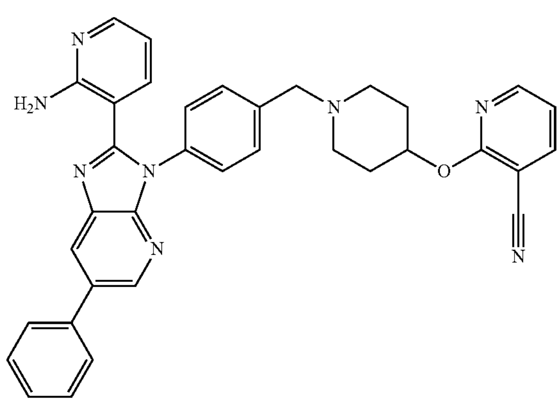 [SMILES: N#Cc1cccnc1OC1CCN(Cc2ccc(-n3c(-c4cccnc4N)nc4cc(-c5ccccc5)cnc43)cc2)CC1] | 2-((1-(4-(2-(2-aminopyridin-3-yl)-6-phenyl-3H-imidazo[4,5-b]pyridin-3-yl)benzyl)piperidin-4-yl)oxy)nicotinonitrile |

TABLE 1-continued

| Example | Compound Structure | Compound Name |
|---|---|---|
| 13 | 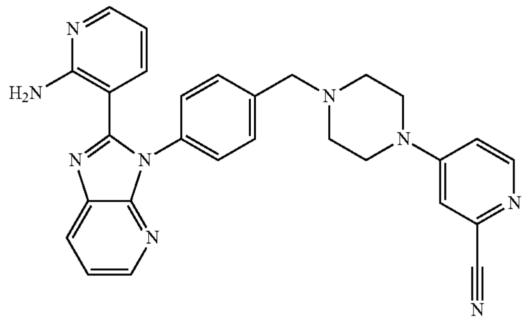 [SMILES: N#Cc1cc(N2CCN(Cc3ccc(-n4c(-c5cccnc5N)nc5cccnc54)cc3)CC2)ccn1] | 4-(4-(4-(2-(2-aminopyridin-3-yl)-3H-imidazo[4,5-b]pyridin-3-yl)benzyl)piperazin-1-yl)picolinonitrile |
| 14 | 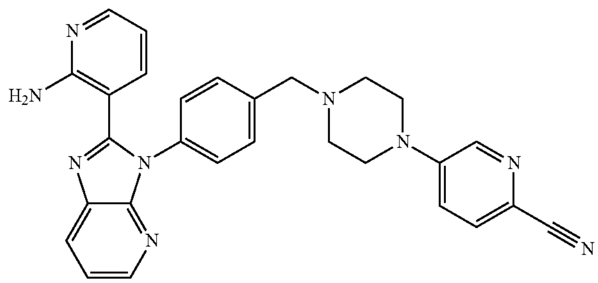 [SMILES: N#Cc1ccc(N2CCN(Cc3ccc(-n4c(-c5cccnc5N)nc5cccnc54)cc3)CC2)cn1] | 5-(4-(4-(2-(2-aminopyridin-3-yl)-3H-imidazo[4,5-b]pyridin-3-yl)benzyl)piperazin-1-yl)picolinonitrile |
| 15 | 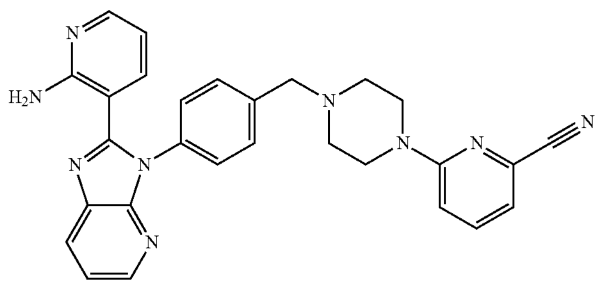 | 6-(4-(4-(2-(2-aminopyridin-3-yl)-3H-imidazo[4,5-b]pyridin-3-yl)benzyl)piperazin-1-yl)picolinonitrile |
| 16 | 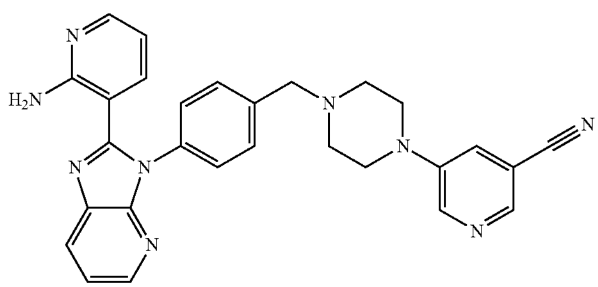 [SMILES: N#Cc1cncc(N2CCN(Cc3ccc(-n4c(-c5cccnc5N)nc5cccnc54)cc3)CC2)c1] | 5-(4-(4-(2-(2-aminopyridin-3-yl)-3H-imidazo[4,5-b]pyridin-3-yl)benzyl)piperazin-1-yl)nicotinonitrile |
| 17 | 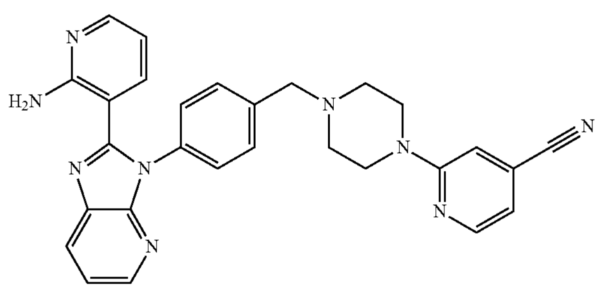 [SMILES: N#Cc1ccnc(N2CCN(Cc3ccc(-n4c(-c5cccnc5N)nc5cccnc54)cc3)CC2)c1] | 2-(4-(4-(2-(2-aminopyridin-3-yl)-3H-imidazo[4,5-b]pyridin-3-yl)benzyl)piperazin-1-yl)isonicotinonitrile |

TABLE 1-continued

| Example | Compound Structure | Compound Name |
|---|---|---|
| 18 | 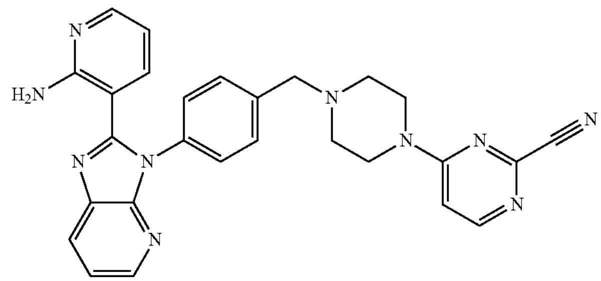 | 4-(4-(4-(2-(2-aminopyridin-3-yl)-3H-imidazo[4,5-b]pyridin-3-yl)benzyl)piperazin-1-yl)pyrimidine-2-carbonitrile |
| 19 | 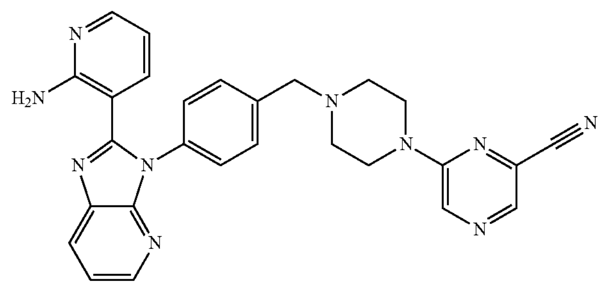 [SMILES: N#Cc1cncc(N2CCN(Cc3ccc(-n4c(-c5cccnc5N)nc5cccnc54)cc3)CC2)n1] | 6-(4-(4-(2-(2-aminopyridin-3-yl)-3H-imidazo[4,5-b]pyridin-3-yl)benzyl)piperazin-1-yl)pyrazine-2-carbonitrile |
| 20 | 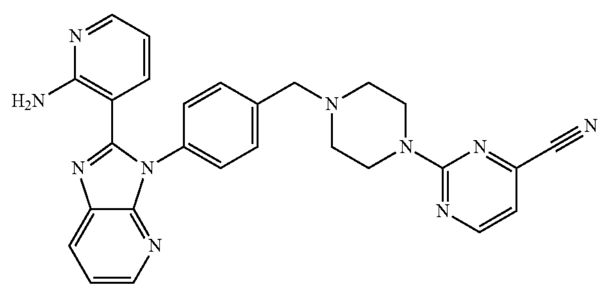 [SMILES: N#Cc1ccnc(N2CCN(Cc3ccc(-n4c(-c5cccnc5N)nc5cccnc54)cc3)CC2)n1] | 2-(4-(4-(2-(2-aminopyridin-3-yl)-3H-imidazo[4,5-b]pyridin-3-yl)benzyl)piperazin-1-yl)pyrimidine-4-carbonitrile |
| 21 | 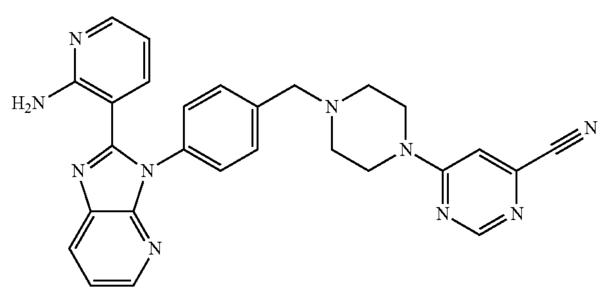 [SMILES: N#Cc1cc(N2CCN(Cc3ccc(-n4c(-c5cccnc5N)nc5cccnc54)cc3)CC2)ncn1] | 6-(4-(4-(2-(2-aminopyridin-3-yl)-3H-imidazo[4,5-b]pyridin-3-yl)benzyl)piperazin-1-yl)pyrimidine-4-carbonitrile |
| 22 | 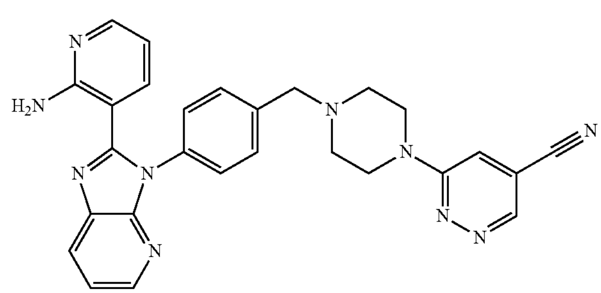 [SMILES: N#Cc1cnnc(N2CCN(Cc3ccc(-n4c(-c5cccnc5N)nc5cccnc54)cc3)CC2)c1] | 6-(4-(4-(2-(2-aminopyridin-3-yl)-3H-imidazo[4,5-b]pyridin-3-yl)benzyl)piperazin-1-yl)pyridazine-4-carbonitrile |

TABLE 1-continued

| Example | Compound Structure | Compound Name |
|---|---|---|
| 23 | 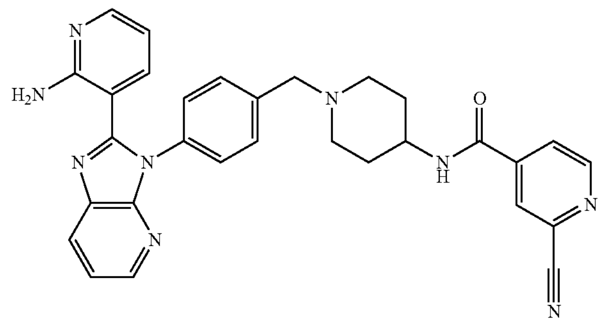 [SMILES: N#Cc1cc(C(=O)NC2CCN(Cc3ccc(-n4c(-c5cccnc5N)nc5cccnc54)cc3)CC2)ccn1] | N-(1-(4-(2-(2-aminopyridin-3-yl)-3H-imidazo[4,5-b]pyridin-3-yl)benzyl)piperidin-4-yl)-2-cyanoisonicotinamide |
| 24 | 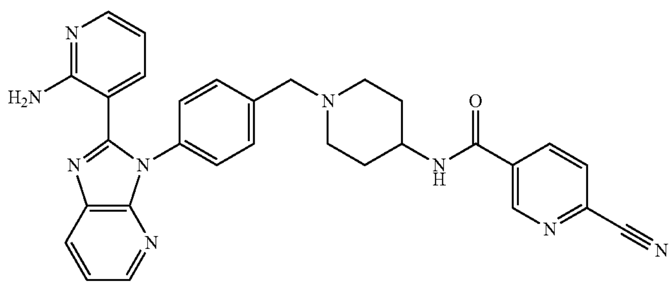 [SMILES: N#Cc1ccc(C(=O)NC2CCN(Cc3ccc(-n4c(-c5cccnc5N)nc5cccnc54)cc3)CC2)cn1] | N-(1-(4-(2-(2-aminopyridin-3-yl)-3H-imidazo[4,5-b]pyridin-3-yl)benzyl)piperidin-4-yl)-6-cyanonicotinamide |
| 25 | 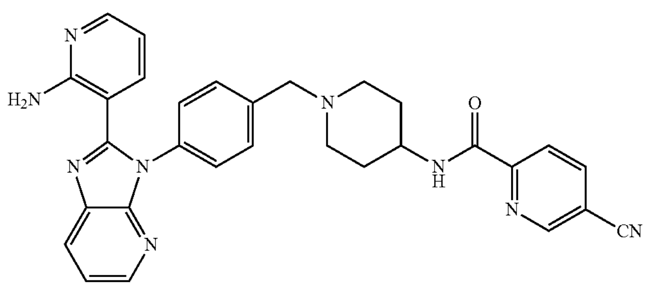 [SMILES: N#Cc1ccc(C(=O)NC2CCN(Cc3ccc(-n4c(-c5cccnc5N)nc5cccnc54)cc3)CC2)nc1] | N-(1-(4-(2-(2-aminopyridin-3-yl)-3H-imidazo[4,5-b]pyridin-3-yl)benzyl)piperidin-4-yl)-5-cyanopicolinamide |
| 26 | 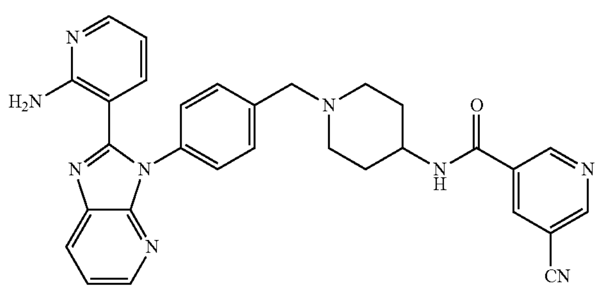 [SMILES: N#Cc1cncc(C(=O)NC2CCN(Cc3ccc(-n4c(-c5cccnc5N)nc5cccnc54)cc3)CC2)c1] | N-(1-(4-(2-(2-aminopyridin-3-yl)-3H-imidazo[4,5-b]pyridin-3-yl)benzyl)piperidin-4-yl)-5-cyanonicotinamide |
| 27 | 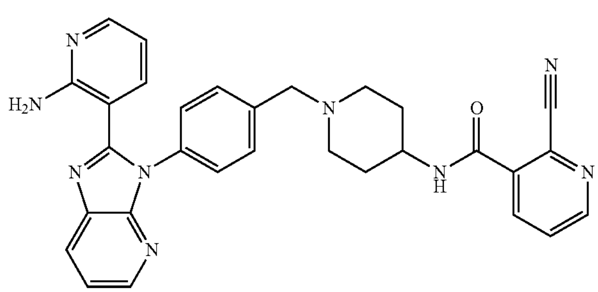 [SMILES: N#Cc1ncccc1C(=O)NC1CCN(Cc2ccc(-n3c(-c4cccnc4N)nc4cccnc43)cc2)CC1] | N-(1-(4-(2-(2-aminopyridin-3-yl)-3H-imidazo[4,5-b]pyridin-3-yl)benzyl)piperidin-4-yl)-2-cyanonicotinamide |

TABLE 1-continued

| Example | Compound Structure | Compound Name |
|---|---|---|
| 28 | 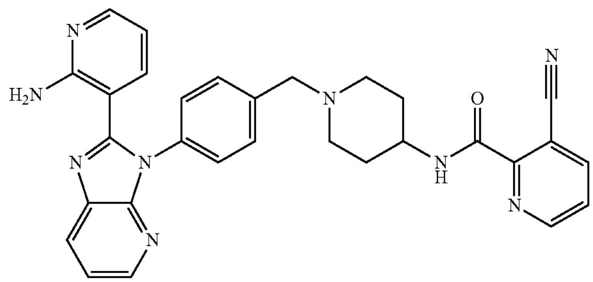 [SMILES: N#Cc1cccnc1C(=O)NC1CCN(Cc2ccc(-n3c(-c4cccnc4N)nc4cccnc43)cc2)CC1] | N-(1-(4-(2-(2-aminopyridin-3-yl)-3H-imidazo[4,5-b]pyridin-3-yl)benzyl)piperidin-4-yl)-3-cyanopicolinamide |
| 29 | 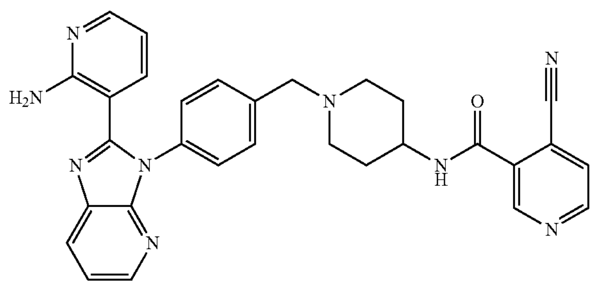 [SMILES: N#Cc1ccncc1C(=O)NC1CCN(Cc2ccc(-n3c(-c4cccnc4N)nc4cccnc43)cc2)CC1] | N-(1-(4-(2-(2-aminopyridin-3-yl)-3H-imidazo[4,5-b]pyridin-3-yl)benzyl)piperidin-4-yl)-4-cyanonicotinamide |
| 30 | 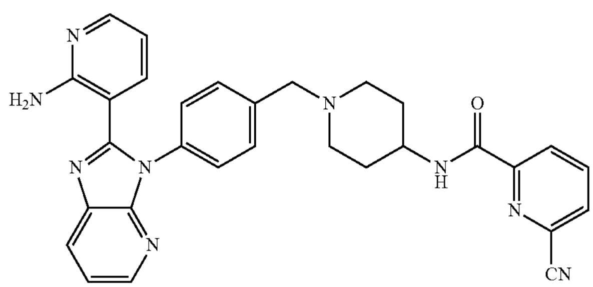 [SMILES: N#Cc1cccc(C(=O)NC2CCN(Cc3ccc(-n4c(-c5cccnc5N)nc5cccnc54)cc3)CC2)n1] | N-(1-(4-(2-(2-aminopyridin-3-yl)-3H-imidazo[4,5-b]pyridin-3-yl)benzyl)piperidin-4-yl)-6-cyanopicolinamide |
| 31 | 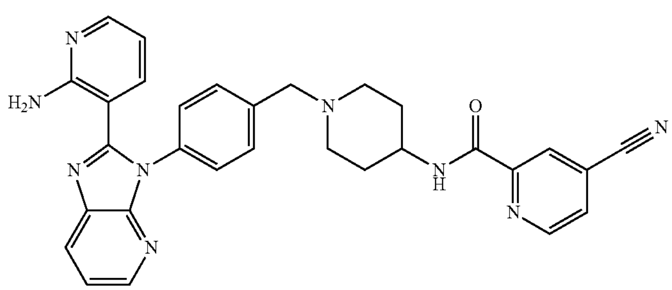 [SMILES: N#Cc1ccnc(C(=O)NC2CCN(Cc3ccc(-n4c(-c5cccnc5N)nc5cccnc54)cc3)CC2)c1] | N-(1-(4-(2-(2-aminopyridin-3-yl)-3H-imidazo[4,5-b]pyridin-3-yl)benzyl)piperidin-4-yl)-4-cyanopicolinamide |
| 32 | 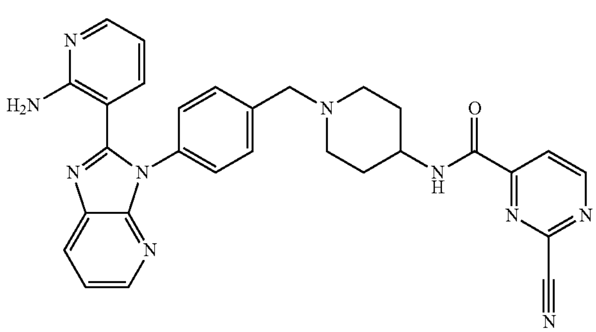 [SMILES: N#Cc1nccc(C(=O)NC2CCN(Cc3ccc(-n4c(-c5cccnc5N)nc5cccnc54)cc3)CC2)n1] | N-(1-(4-(2-(2-aminopyridin-3-yl)-3H-imidazo[4,5-b]pyridin-3-yl)benzyl)piperidin-4-yl)-2-cyanopyrimidine-4-carboxamide |

TABLE 1-continued

| Example | Compound Structure | Compound Name |
|---|---|---|
| 33 | 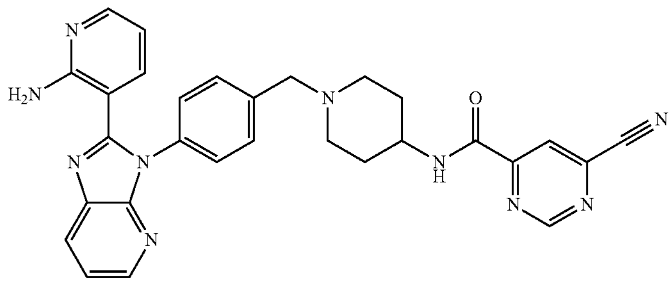 [SMILES: N#Cc1cc(C(=O)NC2CCN(Cc3ccc(-n4c(-c5cccnc5N)nc5cccnc54)cc3)CC2)ncn1] | N-(1-(4-(2-(2-aminopyridin-3-yl)-3H-imidazo[4,5-b]pyridin-3-yl)benzyl)piperidin-4-yl)-6-cyanopyrimidine-4-carboxamide |
| 34 | 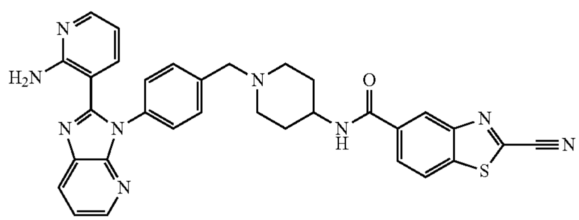 [SMILES: N#Cc1nc2cc(C(=O)NC3CCN(Cc4ccc(-n5c(-c6cccnc6N)nc6cccnc65)cc4)CC3)ccc2s1] | N-(1-(4-(2-(2-aminopyridin-3-yl)-3H-imidazo[4,5-b]pyridin-3-yl)benzyl)piperidin-4-yl)-2-cyanobenzo[d]thiazole-5-carboxamide |
| 35 | 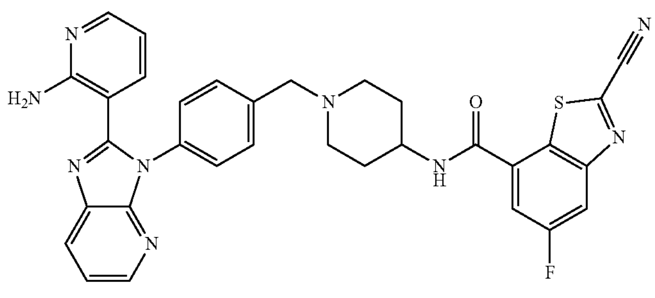 [SMILES: N#Cc1nc2cc(F)cc(C(=O)NC3CCN(Cc4ccc(-n5c(-c6cccnc6N)nc6cccnc65)cc4)CC3)c2s1] | N-(1-(4-(2-(2-aminopyridin-3-yl)-3H-imidazo[4,5-b]pyridin-3-yl)benzyl)piperidin-4-yl)-2-cyano-5-fluorobenzo[d]thiazole-7-carboxamide |
| 36 | 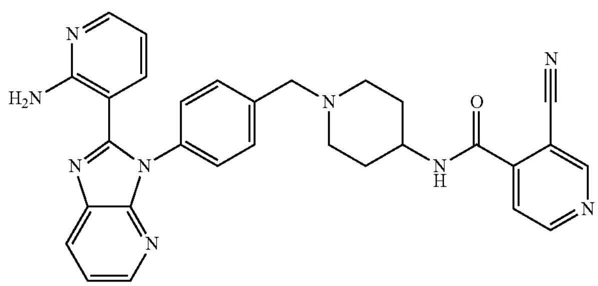 | N-(1-(4-(2-(2-aminopyridin-3-yl)-3H-imidazo[4,5-b]pyridin-3-yl)benzyl)piperidin-4-yl)-3-cyanoisonicotinamide |

TABLE 1-continued

| Example | Compound Structure | Compound Name |
|---|---|---|
| 37 | 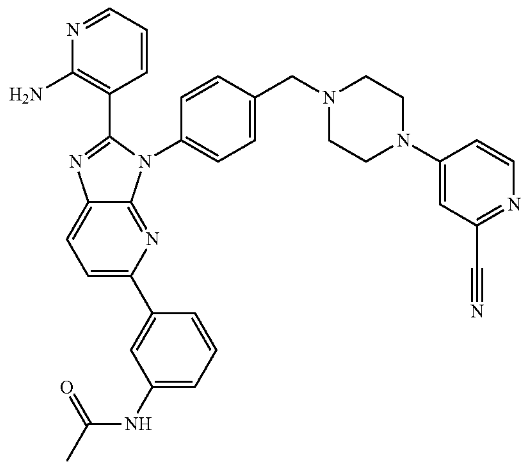 [SMILES: CC(=O)Nc1cccc(-c2ccc3nc(-c4cccnc4N)n(-c4ccc(CN5CCN(c6ccnc(C#N)c6)CC5)cc4)c3n2)c1] | N-(3-(2-(2-aminopyridin-3-yl)-3-(4-((4-(2-cyanopyridin-4-yl)piperazin-1-yl)methyl)phenyl)-3H-imidazo[4,5-b]pyridin-5-yl)phenyl)acetamide |
| 38 | 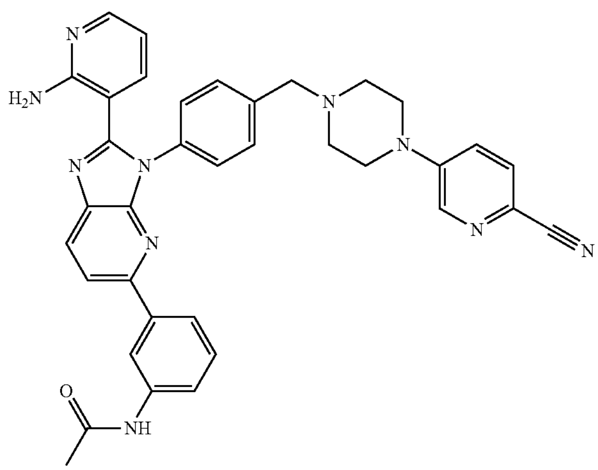 [SMILES: CC(=O)Nc1cccc(-c2ccc3nc(-c4cccnc4N)n(-c4ccc(CN5CCN(c6ccc(C#N)nc6)CC5)cc4)c3n2)c1] | N-(3-(2-(2-aminopyridin-3-yl)-3-(4-((4-(6-cyanopyridin-3-yl)piperazin-1-yl)methyl)phenyl)-3H-imidazo[4,5-b]pyridin-5-yl)phenyl)acetamide |
| 39 | 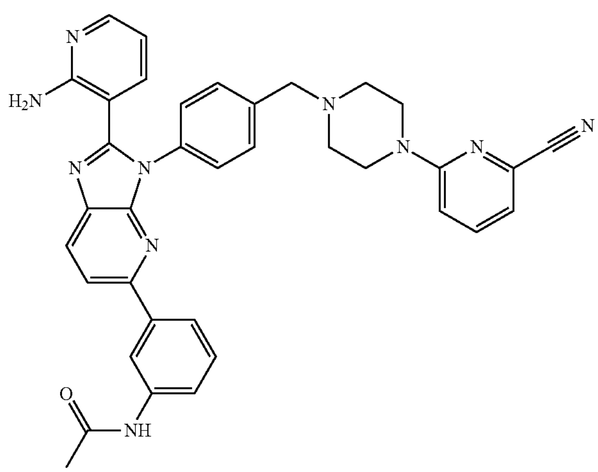 [SMILES: CC(=O)Nc1cccc(-c2ccc3nc(-c4cccnc4N)n(-c4ccc(CN5CCN(c6cccc(C#N)n6)CC5)cc4)c3n2)c1] | N-(3-(2-(2-aminopyridin-3-yl)-3-(4-((4-(6-cyanopyridin-2-yl)piperazin-1-yl)methyl)phenyl)-3H-imidazo[4,5-b]pyridin-5-yl)phenyl)acetamide |

TABLE 1-continued

| Example | Compound Structure | Compound Name |
|---|---|---|
| 40 | 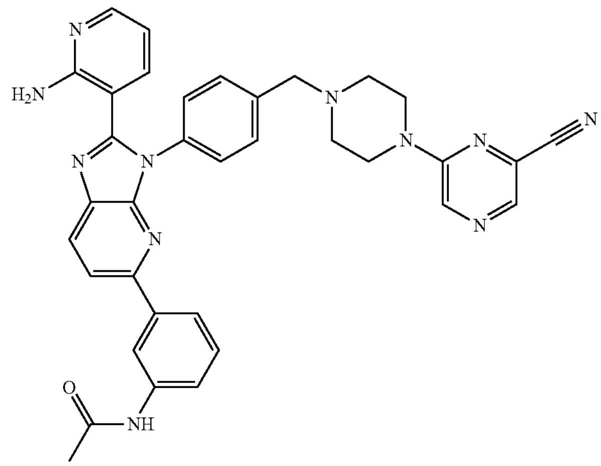 [SMILES: CC(=O)Nc1cccc(-c2ccc3nc(-c4cccnc4N)n(-c4ccc(CN5CCN(c6cncc(C#N)n6)CC5)cc4)c3n2)c1] | N-(3-(2-(2-aminopyridin-3-yl)-3-(4-((4-(6-cyanopyrazin-2-yl)piperazin-1-yl)methyl)phenyl)-3H-imidazo[4,5-b]pyridin-5-yl)phenyl)acetamide |
| 41 | 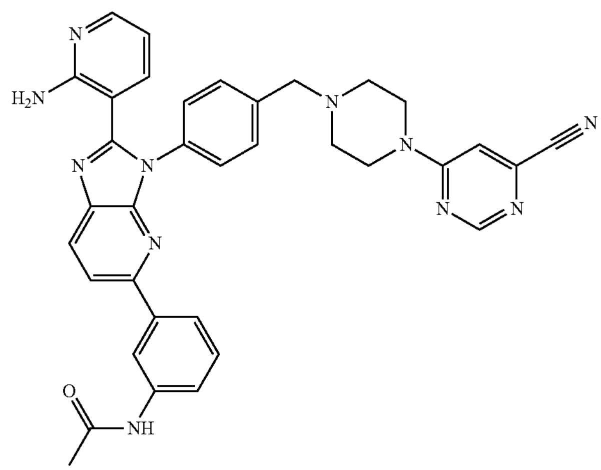 [SMILES: CC(=O)Nc1cccc(-c2ccc3nc(-c4cccnc4N)n(-c4ccc(CN5CCN(c6cc(C#N)ncn6)CC5)cc4)c3n2)c1] | N-(3-(2-(2-aminopyridin-3-yl)-3-(4-((4-(6-cyanopyrimidin-4-yl)piperazin-1-yl)methyl)phenyl)-3H-imidazo[4,5-b]pyridin-5-yl)phenyl)acetamide |
| 42 | 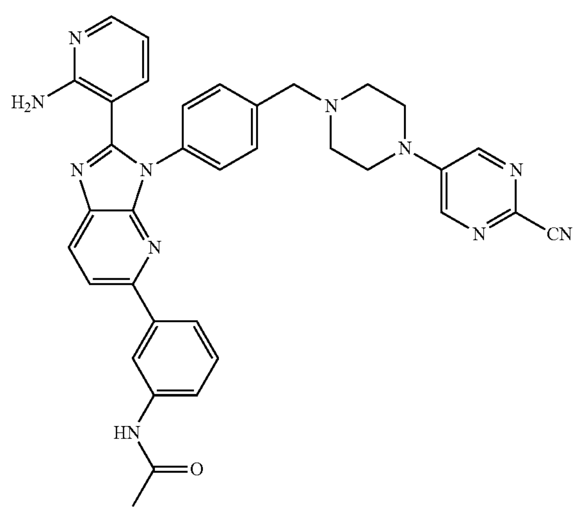 [SMILES: CC(=O)Nc1cccc(-c2ccc3nc(-c4cccnc4N)n(-c4ccc(CN5CCN(c6cnc(C#N)nc6)CC5)cc4)c3n2)c1] | N-(3-(2-(2-aminopyridin-3-yl)-3-(4-((4-(2-cyanopyrimidin-5-yl)piperazin-1-yl)methyl)phenyl)-3H-imidazo[4,5-b]pyridin-5-yl)phenyl)acetamide |

TABLE 1-continued

| Example | Compound Structure | Compound Name |
|---|---|---|
| 43 | 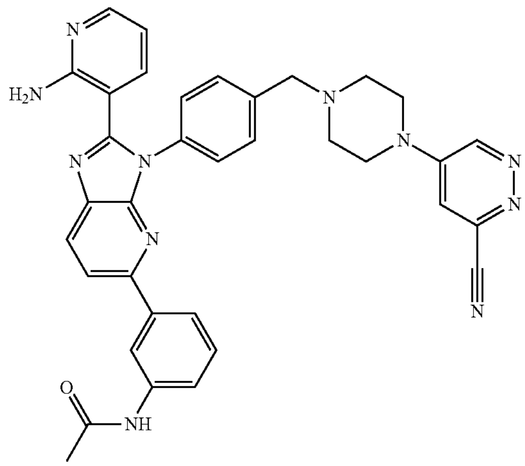 [SMILES: CC(=O)Nc1cccc(-c2ccc3nc(-c4cccnc4N)n(-c4ccc(CN5CCN(c6cnnc(C#N)c6)CC5)cc4)c3n2)c1] | N-(3-(2-(2-aminopyridin-3-yl)-3-(4-((4-(6-cyanopyridazin-4-yl)piperazin-1-yl)methyl)phenyl)-3H-imidazo[4,5-b]pyridin-5-yl)phenyl)acetamide |
| 44 | 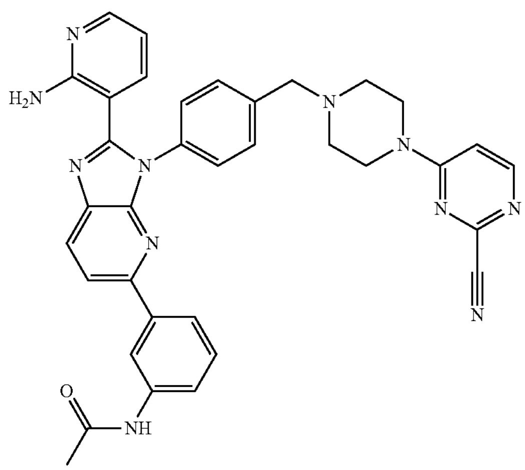 [SMILES: CC(=O)Nc1cccc(-c2ccc3nc(-c4cccnc4N)n(-c4ccc(CN5CCN(c6ccnc(C#N)n6)CC5)cc4)c3n2)c1] | N-(3-(2-(2-aminopyridin-3-yl)-3-(4-((4-(2-cyanopyrimidin-4-yl)piperazin-1-yl)methyl)phenyl)-3H-imidazo[4,5-b]pyridin-5-yl)phenyl)acetamide |
| 45 | 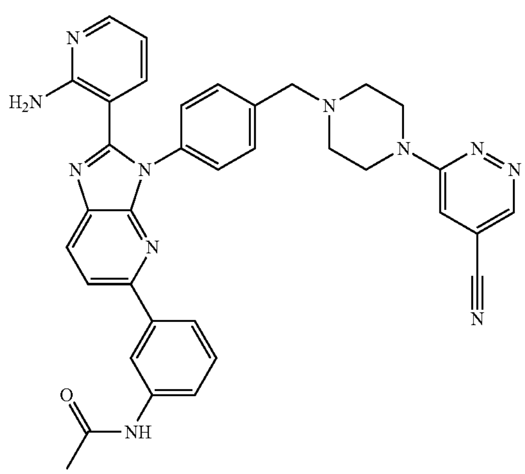 [SMILES: CC(=O)Nc1cccc(-c2ccc3nc(-c4cccnc4N)n(-c4ccc(CN5CCN(c6cc(C#N)cnn6)CC5)cc4)c3n2)c1] | N-(3-(2-(2-aminopyridin-3-yl)-3-(4-((4-(5-cyanopyridazin-3-yl)piperazin-1-yl)methyl)phenyl)-3H-imidazo[4,5-b]pyridin-5-yl)phenyl)acetamide |

TABLE 1-continued

| Example | Compound Structure | Compound Name |
|---|---|---|
| 46 | 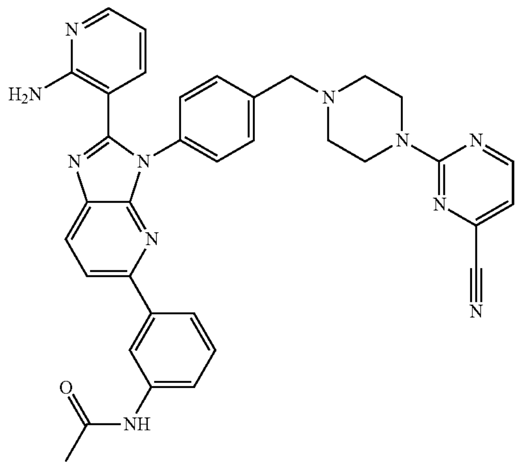 [SMILES: CC(=O)Nc1cccc(-c2ccc3nc(-c4cccnc4N)n(-c4ccc(CN5CCN(c6nccc(C#N)n6)CC5)cc4)c3n2)c1] | N-(3-(2-(2-aminopyridin-3-yl)-3-(4-((4-(4-cyanopyrimidin-2-yl)piperazin-1-yl)methyl)phenyl)-3H-imidazo[4,5-b]pyridin-5-yl)phenyl)acetamide |
| 47 | 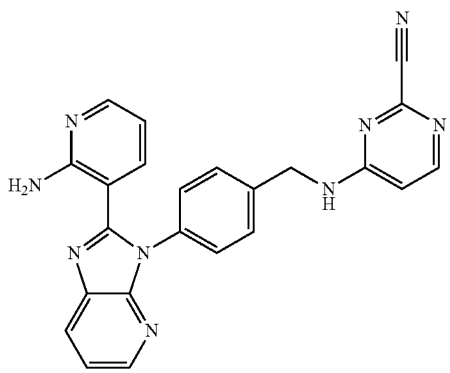 [SMILES: N#Cc1nccc(NCc2ccc(-n3c(-c4cccnc4N)nc4cccnc43)cc2)n1] | 4-((4-(2-(2-aminopyridin-3-yl)-3H-imidazo[4,5-b]pyridin-3-yl)benzyl)amino)pyrimidine-2-carbonitrile |
| 48 | 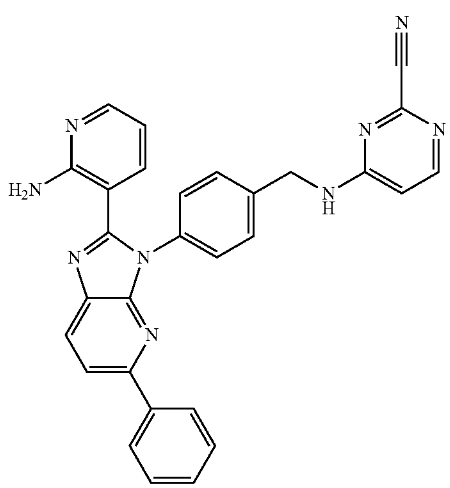 [SMILES: N#Cc1nccc(NCc2ccc(-n3c(-c4cccnc4N)nc4ccc(-c5ccccc5)nc43)cc2)n1] | 4-((4-(2-(2-aminopyridin-3-yl)-5-phenyl-3H-imidazo[4,5-b]pyridin-3-yl)benzyl)amino)pyrimidine-2-carbonitrile |

TABLE 1-continued

| Example | Compound Structure | Compound Name |
|---|---|---|
| 49 | 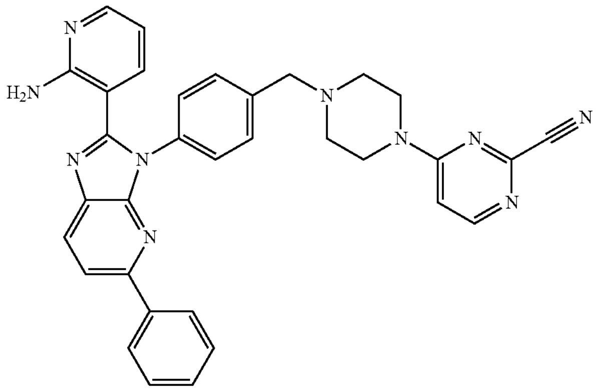 [SMILES: N#Cc1nccc(N2CCN(Cc3ccc(-n4c(-c5cccnc5N)nc5ccc(-c6ccccc6)nc54)cc3)CC2)n1] | 4-(4-(4-(2-(2-aminopyridin-3-yl)-5-phenyl-3H-imidazo[4,5-b]pyridin-3-yl)benzyl)piperazin-1-yl)pyrimidine-2-carbonitrile |
| 50 | 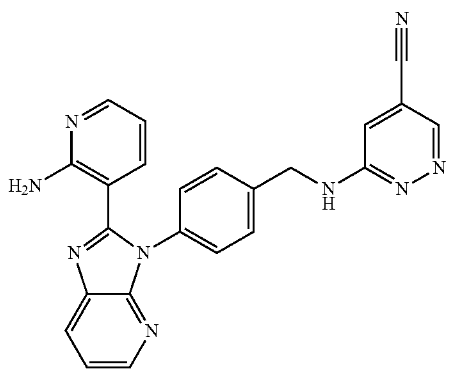 [SMILES: N#Cc1cnnc(NCc2ccc(-n3c(-c4cccnc4N)nc4cccnc43)cc2)c1] | 6-((4-(2-(2-aminopyridin-3-yl)-3H-imidazo[4,5-b]pyridin-3-yl)benzyl)amino)pyridazine-4-carbonitrile |
| 51 | 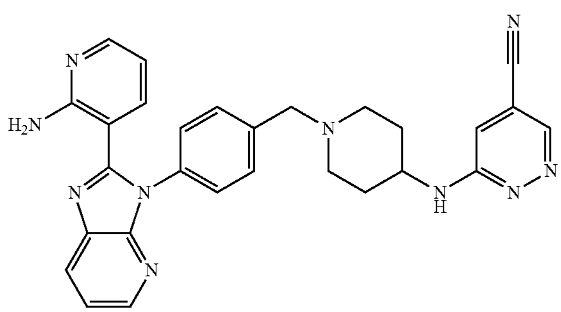 | 6-((1-(4-(2-(2-aminopyridin-3-yl)-3H-imidazo[4,5-b]pyridin-3-yl)benzyl)piperidin-4-yl)amino)pyridazine-4-carbonitrile |
| 52 | 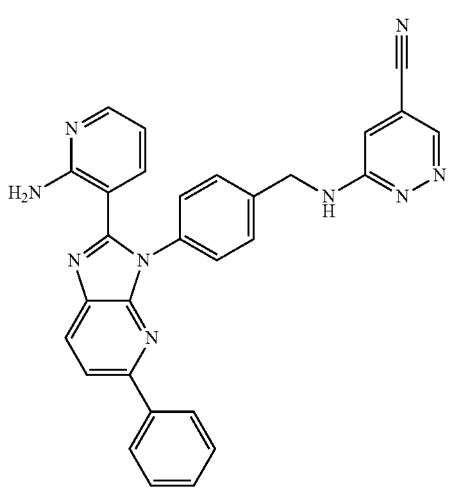 [SMILES: N#Cc1cnnc(NCc2ccc(-n3c(-c4cccnc4N)nc4ccc(-c5ccccc5)nc43)cc2)c1] | 6-((4-(2-(2-aminopyridin-3-yl)-5-phenyl-3H-imidazo[4,5-b]pyridin-3-yl)benzyl)amino)pyridazine-4-carbonitrile |

TABLE 1-continued

| Example | Compound Structure | Compound Name |
|---|---|---|
| 53 | 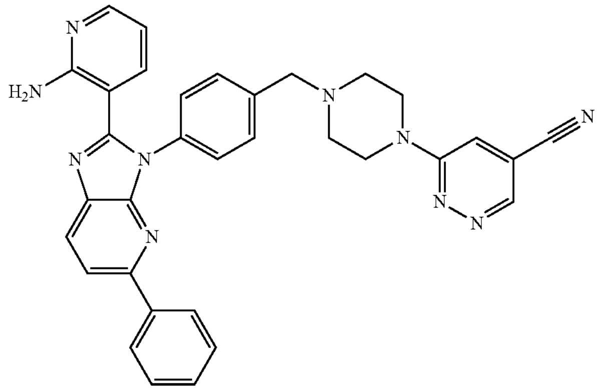 [SMILES: N#Cc1cnnc(N2CCN(Cc3ccc(-n4c(-c5cccnc5N)nc5ccc(-c6ccccc6)nc54)cc3)CC2)c1] | 6-(4-(4-(2-(2-aminopyridin-3-yl)-5-phenyl-3H-imidazo[4,5-b]pyridin-3-yl)benzyl)piperazin-1-yl)pyridazine-4-carbonitrile |
| 54 | 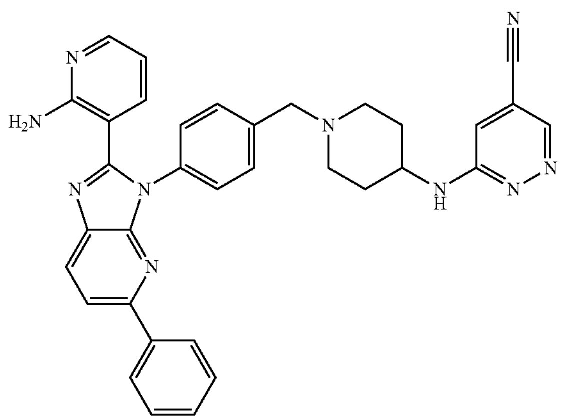 [SMILES: N#Cc1cnnc(NC2CCN(Cc3ccc(-n4c(-c5cccnc5N)nc5ccc(-c6ccccc6)nc54)cc3)CC2)c1] | 6-((1-(4-(2-(2-aminopyridin-3-yl)-5-phenyl-3H-imidazo[4,5-b]pyridin-3-yl)benzyl)piperidin-4-yl)amino)pyridazine-4-carbonitrile |
| 55 | 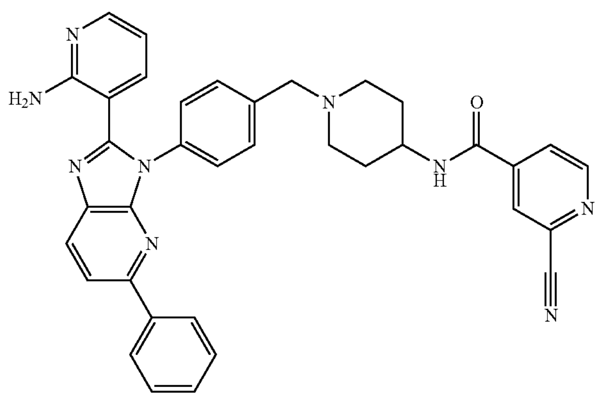 [SMILES: N#Cc1cc(C(=O)NC2CCN(Cc3ccc(-n4c(-c5cccnc5N)nc5ccc(-c6ccccc6)nc54)cc3)CC2)ccn1] | N-(1-(4-(2-(2-aminopyridin-3-yl)-5-phenyl-3H-imidazo[4,5-b]pyridin-3-yl)benzyl)piperidin-4-yl)-2-cyanoisonicotinamide |
| 56 | 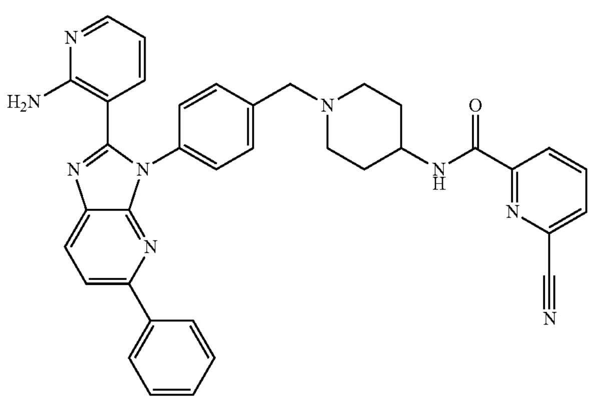 [SMILES: N#Cc1cccc(C(=O)NC2CCN(Cc3ccc(-n4c(-c5cccnc5N)nc5ccc(-c6ccccc6)nc54)cc3)CC2)n1] | N-(1-(4-(2-(2-aminopyridin-3-yl)-5-phenyl-3H-imidazo[4,5-b]pyridin-3-yl)benzyl)piperidin-4-yl)-6-cyanopicolinamide |

TABLE 1-continued

| Example | Compound Structure | Compound Name |
|---|---|---|
| 57 | 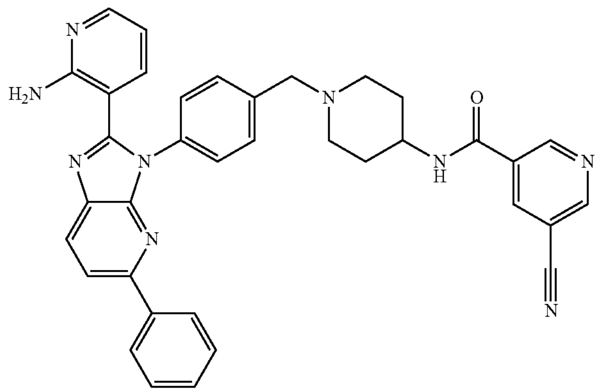 [SMILES: N#Cc1cncc(C(=O)NC2CCN(Cc3ccc(-n4c(-c5cccnc5N)nc5ccc(-c6ccccc6)nc54)cc3)CC2)c1] | N-(1-(4-(2-(2-aminopyridin-3-yl)-5-phenyl-3H-imidazo[4,5-b]pyridin-3-yl)benzyl)piperidin-4-yl)-5-cyanonicotinamide |
| 58 | 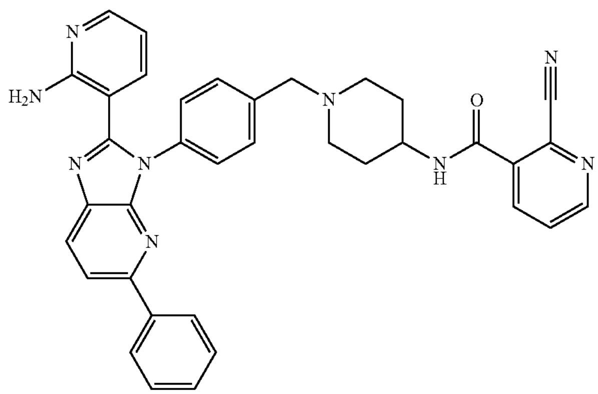 [SMILES: N#Cc1ncccc1C(=O)NC1CCN(Cc2ccc(-n3c(-c4cccnc4N)nc4ccc(-c5ccccc5)nc43)cc2)CC1] | N-(1-(4-(2-(2-aminopyridin-3-yl)-5-phenyl-3H-imidazo[4,5-b]pyridin-3-yl)benzyl)piperidin-4-yl)-2-cyanonicotinamide |
| 59 | 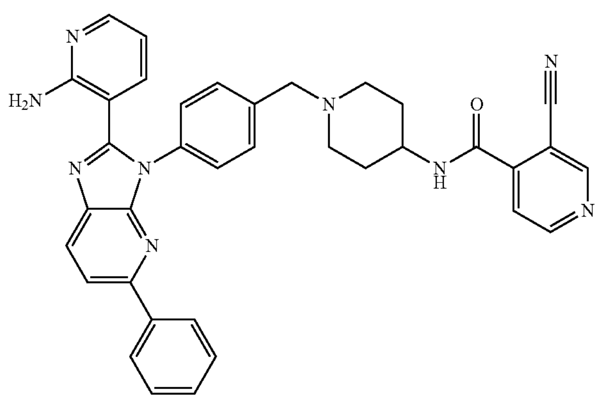 | N-(1-(4-(2-(2-aminopyridin-3-yl)-5-phenyl-3H-imidazo[4,5-b]pyridin-3-yl)benzyl)piperidin-4-yl)-3-cyanoisonicotinamide |
| 60 | 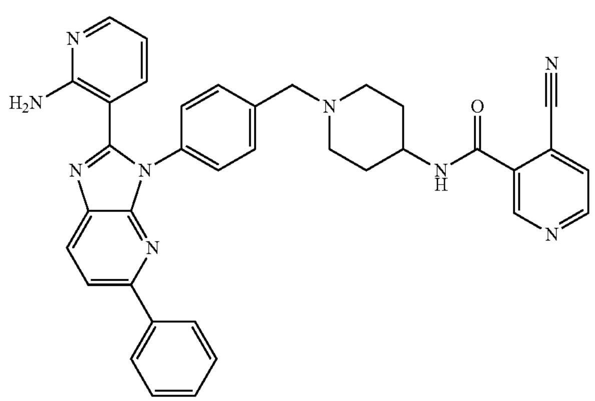 [SMILES: N#Cc1ccncc1C(=O)NC1CCN(Cc2ccc(-n3c(-c4cccnc4N)nc4ccc(-c5ccccc5)nc43)cc2)CC1] | N-(1-(4-(2-(2-aminopyridin-3-yl)-5-phenyl-3H-imidazo[4,5-b]pyridin-3-yl)benzyl)piperidin-4-yl)-4-cyanonicotinamide |

TABLE 1-continued

| Example | Compound Structure | Compound Name |
|---|---|---|
| 61 | 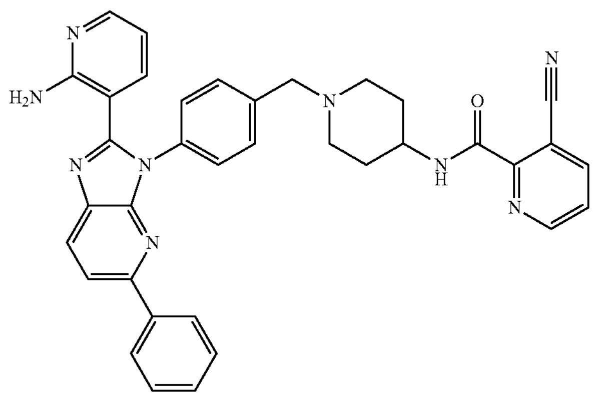 [SMILES: N#Cc1cccnc1C(=O)NC1CCN(Cc2ccc(-n3c(-c4cccnc4N)nc4ccc(-c5ccccc5)nc43)cc2)CC1] | N-(1-(4-(2-(2-aminopyridin-3-yl)-5-phenyl-3H-imidazo[4,5-b]pyridin-3-yl)benzyl)piperidin-4-yl)-3-cyanopicolinamide |
| 62 | 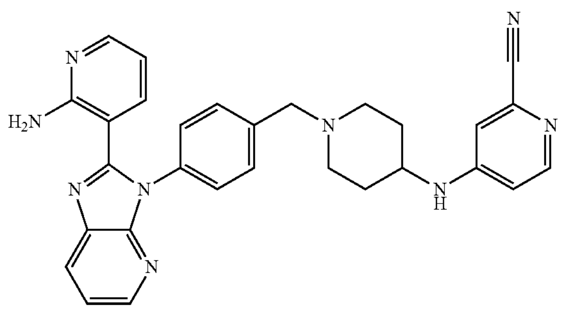 [SMILES: N#Cc1cc(NC2CCN(Cc3ccc(-n4c(-c5cccnc5N)nc5cccnc54)cc3)CC2)ccn1] | 4-((1-(4-(2-(2-aminopyridin-3-yl)-3H-imidazo[4,5-b]pyridin-3-yl)benzyl)piperidin-4-yl)amino)picolinonitrile |
| 63 | 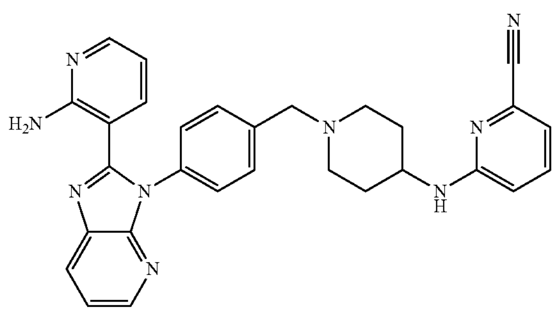 [SMILES: N#Cc1cccc(NC2CCN(Cc3ccc(-n4c(-c5cccnc5N)nc5cccnc54)cc3)CC2)n1] | 6-((1-(4-(2-(2-aminopyridin-3-yl)-3H-imidazo[4,5-b]pyridin-3-yl)benzyl)piperidin-4-yl)amino)picolinonitrile |
| 64 | 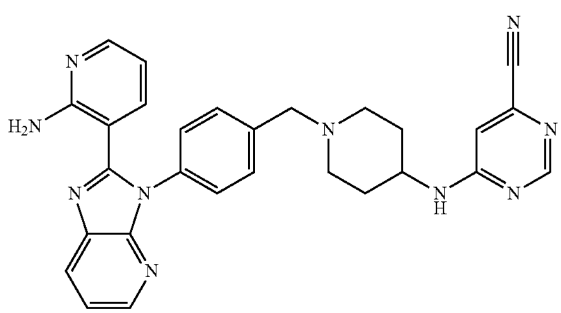 [SMILES: N#Cc1cc(NC2CCN(Cc3ccc(-n4c(-c5cccnc5N)nc5cccnc54)cc3)CC2)ncn1] | 6-((1-(4-(2-(2-aminopyridin-3-yl)-3H-imidazo[4,5-b]pyridin-3-yl)benzyl)piperidin-4-yl)amino)pyrimidine-4-carbonitrile |

TABLE 1-continued

| Example | Compound Structure | Compound Name |
|---|---|---|
| 65 | 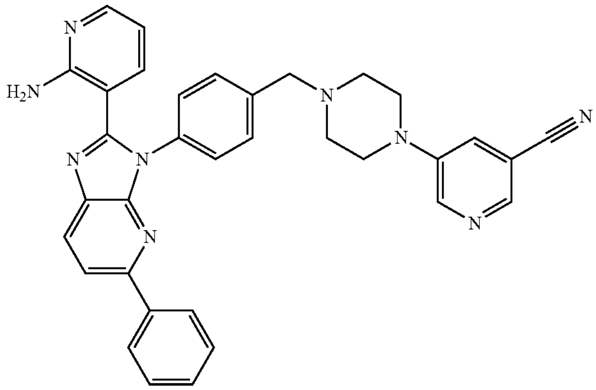 [SMILES: N#Cc1cncc(N2CCN(Cc3ccc(-n4c(-c5cccnc5N)nc5ccc(-c6ccccc6)nc54)cc3)CC2)c1] | 5-(4-(4-(2-(2-aminopyridin-3-yl)-5-phenyl-3H-imidazo[4,5-b]pyridin-3-yl)benzyl)piperazin-1-yl)nicotinonitrile |
| 66 | 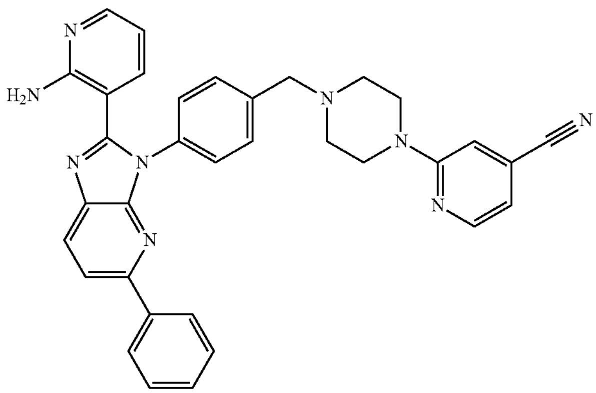 [SMILES: N#Cc1ccnc(N2CCN(Cc3ccc(-n4c(-c5cccnc5N)nc5ccc(-c6ccccc6)nc54)cc3)CC2)c1] | 2-(4-(4-(2-(2-aminopyridin-3-yl)-5-phenyl-3H-imidazo[4,5-b]pyridin-3-yl)benzyl)piperazin-1-yl)isonicotinonitrile |
| 67 | 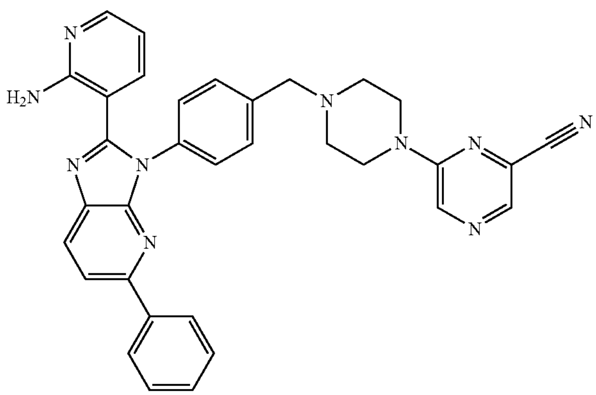 [SMILES: N#Cc1cncc(N2CCN(Cc3ccc(-n4c(-c5cccnc5N)nc5ccc(-c6ccccc6)nc54)cc3)CC2)n1] | 6-(4-(4-(2-(2-aminopyridin-3-yl)-5-phenyl-3H-imidazo[4,5-b]pyridin-3-yl)benzyl)piperazin-1-yl)pyrazine-2-carbonitrile |
| 68 | 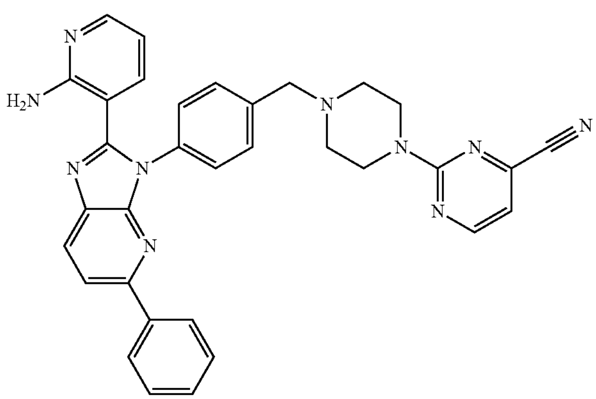 [SMILES: N#Cc1ccnc(N2CCN(Cc3ccc(-n4c(-c5cccnc5N)nc5ccc(-c6ccccc6)nc54)cc3)CC2)n1] | 2-(4-(4-(2-(2-aminopyridin-3-yl)-5-phenyl-3H-imidazo[4,5-b]pyridin-3-yl)benzyl)piperazin-1-yl)pyrimidine-4-carbonitrile |

TABLE 1-continued

| Example | Compound Structure | Compound Name |
|---|---|---|
| 69 | 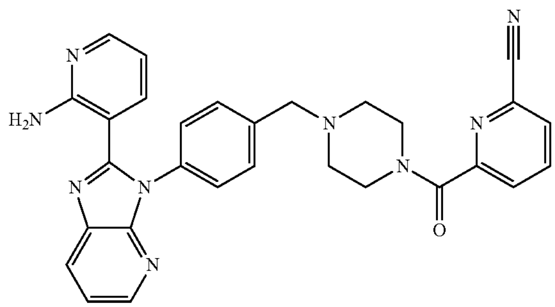 [SMILES: N#Cc1cccc(C(=O)N2CCN(Cc3ccc(-n4c(-c5cccnc5N)nc5cccnc54)cc3)CC2)n1] | 6-(4-(4-(2-(2-aminopyridin-3-yl)-3H-imidazo[4,5-b]pyridin-3-yl)benzyl)piperazine-1-carbonyl)picolinonitrile |
| 70 | 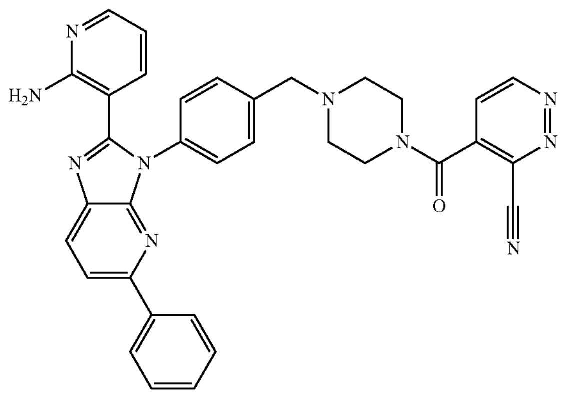 [SMILES: N#Cc1nnccc1C(=O)N1CCN(Cc2ccc(-n3c(-c4cccnc4N)nc4ccc(-c5ccccc5)nc43)cc2)CC1] | 4-(4-(4-(2-(2-aminopyridin-3-yl)-5-phenyl-3H-imidazo[4,5-b]pyridin-3-yl)benzyl)piperazine-1-carbonyl)pyridazine-3-carbonitrile |
| 71 | 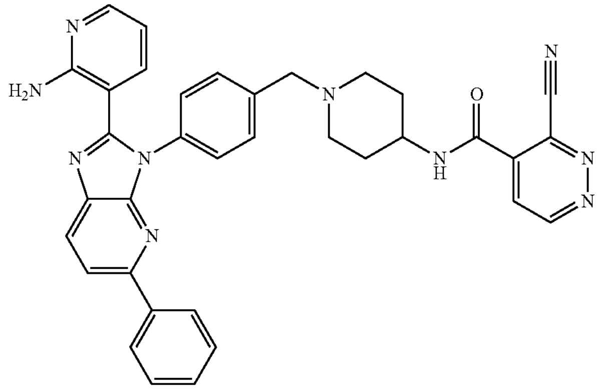 [SMILES: N#Cc1nnccc1C(=O)NC1CCN(Cc2ccc(-n3c(-c4cccnc4N)nc4ccc(-c5ccccc5)nc43)cc2)CC1] | N-(1-(4-(2-(2-aminopyridin-3-yl)-5-phenyl-3H-imidazo[4,5-b]pyridin-3-yl)benzyl)piperidin-4-yl)-3-cyanopyridazine-4-carboxamide |
| 72 | 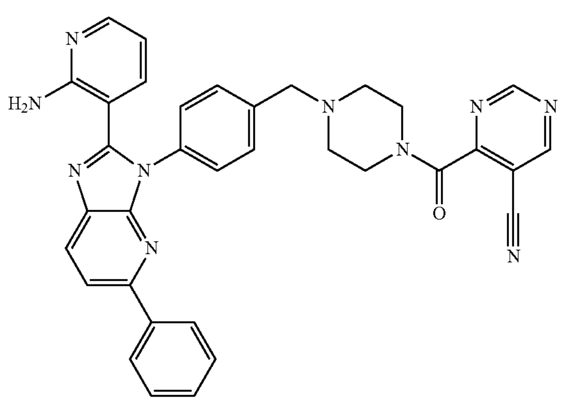 [SMILES: N#Cc1cncnc1C(=O)N1CCN(Cc2ccc(-n3c(-c4cccnc4N)nc4ccc(-c5ccccc5)nc43)cc2)CC1] | 4-(4-(4-(2-(2-aminopyridin-3-yl)-5-phenyl-3H-imidazo[4,5-b]pyridin-3-yl)benzyl)piperazine-1-carbonyl)pyrimidine-5-carbonitrile |

TABLE 1-continued

| Example | Compound Structure | Compound Name |
|---|---|---|
| 73 | 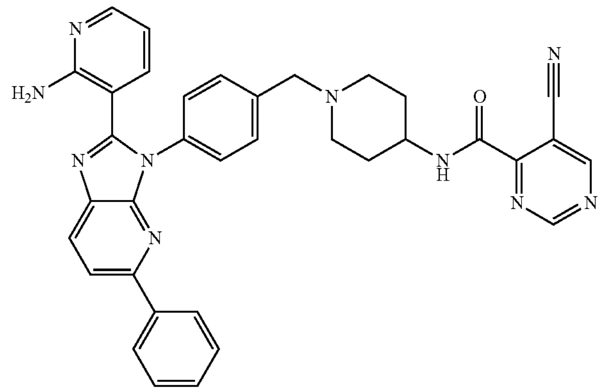 | N-(1-(4-(2-(2-aminopyridin-3-yl)-5-phenyl-3H-imidazo[4,5-b]pyridin-3-yl)benzyl)piperidin-4-yl)-5-cyanopyrimidine-4-carboxamide |
| 74 | 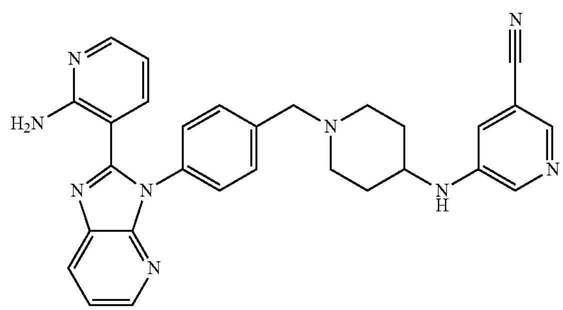 [SMILES: N#Cc1cncc(NC2CCN(Cc3ccc(-n4c(-c5cccnc5N)nc5cccnc54)cc3)CC2)c1] | 5-((1-(4-(2-(2-aminopyridin-3-yl)-3H-imidazo[4,5-b]pyridin-3-yl)benzyl)piperidin-4-yl)amino)nicotinonitrile |
| 75 | 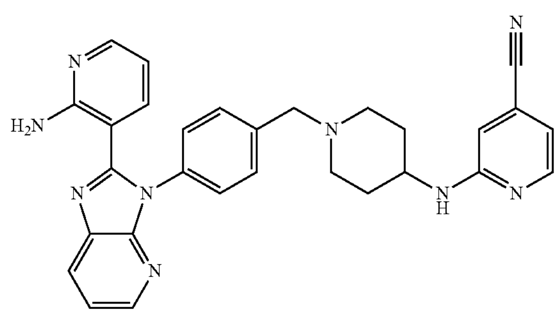 [SMILES: N#Cc1ccnc(NC2CCN(Cc3ccc(-n4c(-c5cccnc5N)nc5cccnc54)cc3)CC2)c1] | 2-((1-(4-(2-(2-aminopyridin-3-yl)-3H-imidazo[4,5-b]pyridin-3-yl)benzyl)piperidin-4-yl)amino)isonicotinonitrile |
| 76 | 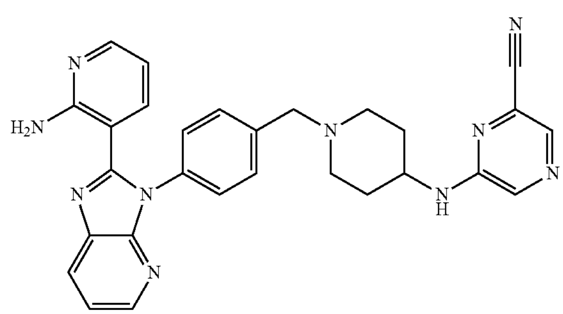 [SMILES: N#Cc1cncc(NC2CCN(Cc3ccc(-n4c(-c5cccnc5N)nc5cccnc54)cc3)CC2)n1] | 6-((1-(4-(2-(2-aminopyridin-3-yl)-3H-imidazo[4,5-b]pyridin-3-yl)benzyl)piperidin-4-yl)amino)pyrazine-2-carbonitrile |

TABLE 1-continued

| Example | Compound Structure | Compound Name |
|---|---|---|
| 77 | 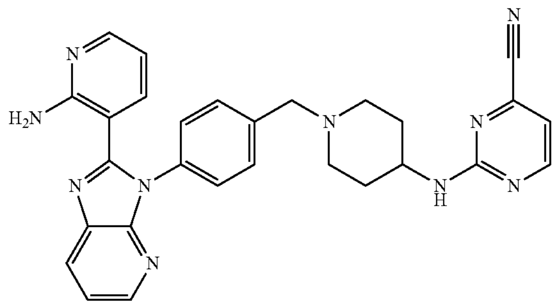 [SMILES: N#Cc1ccnc(NC2CCN(Cc3ccc(-n4c(-c5cccnc5N)nc5cccnc54)cc3)CC2)n1] | 2-((1-(4-(2-(2-aminopyridin-3-yl)-3H-imidazo[4,5-b]pyridin-3-yl)benzyl)piperidin-4-yl)amino)pyrimidine-4-carbonitrile |
| 78 | 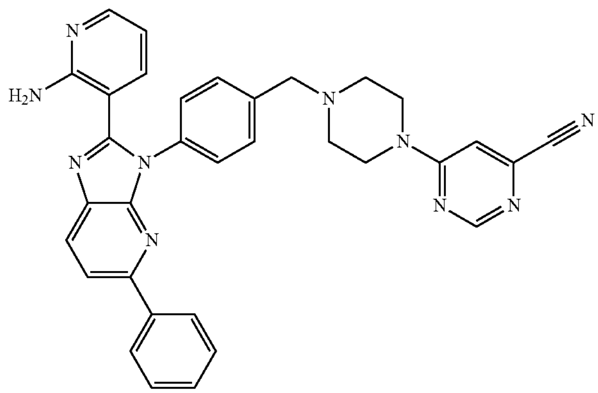 [SMILES: N#Cc1cc(N2CCN(Cc3ccc(-n4c(-c5cccnc5N)nc5ccc(-c6ccccc6)nc54)cc3)CC2)ncn1] | 6-(4-(4-(2-(2-aminopyridin-3-yl)-5-phenyl-3H-imidazo[4,5-b]pyridin-3-yl)benzyl)piperazin-1-yl)pyrimidine-4-carbonitrile |
| 79 | 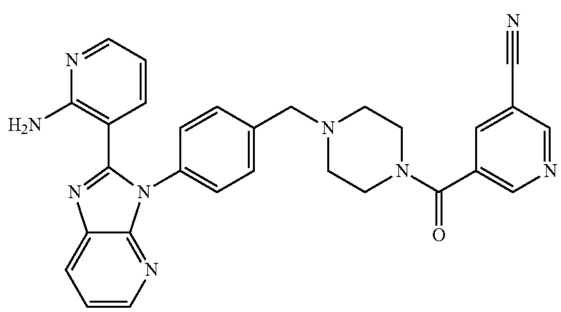 [SMILES: N#Cc1cncc(C(=O)N2CCN(Cc3ccc(-n4c(-c5cccnc5N)nc5cccnc54)cc3)CC2)c1] | 5-(4-(4-(2-(2-aminopyridin-3-yl)-3H-imidazo[4,5-b]pyridin-3-yl)benzyl)piperazine-1-carbonyl)nicotinonitrile |
| 80 | 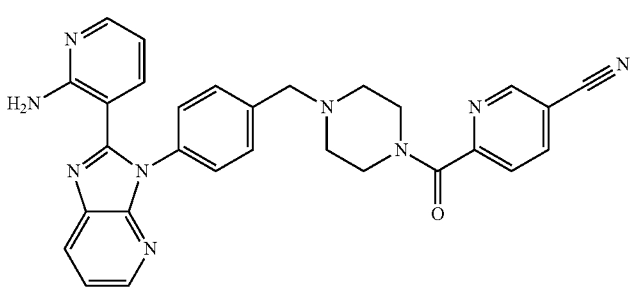 [SMILES: N#Cc1ccc(C(=O)N2CCN(Cc3ccc(-n4c(-c5cccnc5N)nc5cccnc54)cc3)CC2)nc1] | 6-(4-(4-(2-(2-aminopyridin-3-yl)-3H-imidazo[4,5-b]pyridin-3-yl)benzyl)piperazine-1-carbonyl)nicotinonitrile |

TABLE 1-continued

| Example | Compound Structure | Compound Name |
|---|---|---|
| 81 | 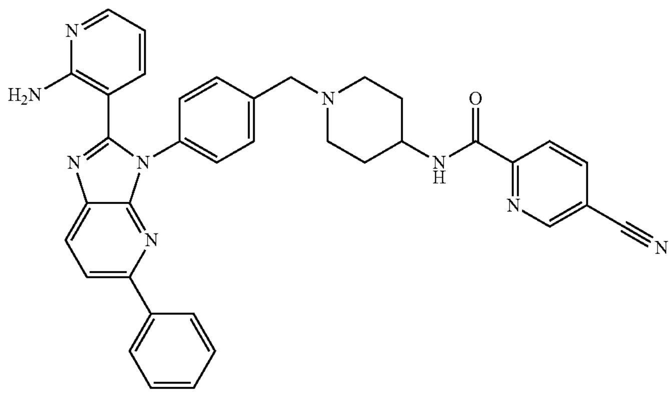 [SMILES: N#Cc1ccc(C(=O)NC2CCN(Cc3ccc(-n4c(-c5cccnc5N)nc5ccc(-c6ccccc6)nc54)cc3)CC2)nc1] | N-(1-(4-(2-(2-aminopyridin-3-yl)-5-phenyl-3H-imidazo[4,5-b]pyridin-3-yl)benzyl)piperidin-4-yl)-5-cyanopicolinamide |
| 82 | 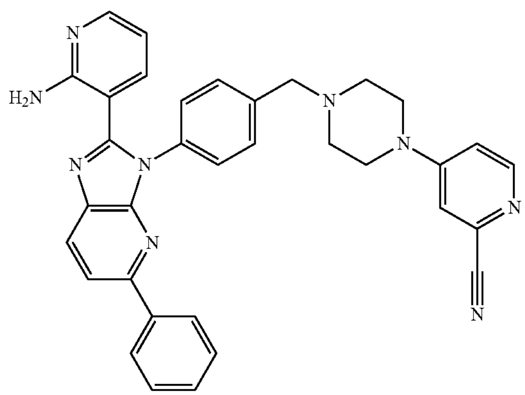 [SMILES: N#Cc1cc(N2CCN(Cc3ccc(-n4c(-c5cccnc5N)nc5ccc(-c6ccccc6)nc54)cc3)CC2)ccn1] | 4-(4-(4-(2-(2-aminopyridin-3-yl)-5-phenyl-3H-imidazo[4,5-b]pyridin-3-yl)benzyl)piperazin-1-yl)picolinonitrile |
| 83 | 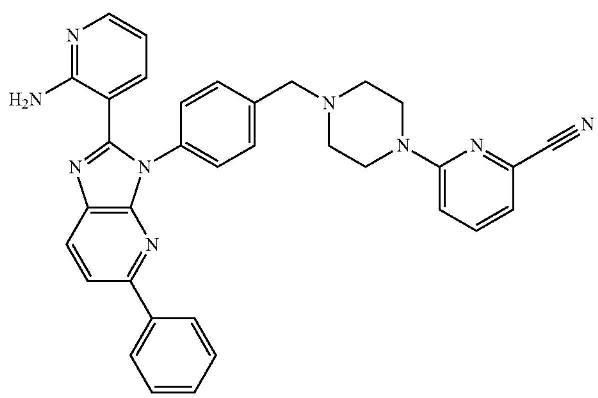 [SMILES: N#Cc1cccc(N2CCN(Cc3ccc(-n4c(-c5cccnc5N)nc5ccc(-c6ccccc6)nc54)cc3)CC2)n1] | 6-(4-(4-(2-(2-aminopyridin-3-yl)-5-phenyl-3H-imidazo[4,5-b]pyridin-3-yl)benzyl)piperazin-1-yl)picolinonitrile |
| 84 | 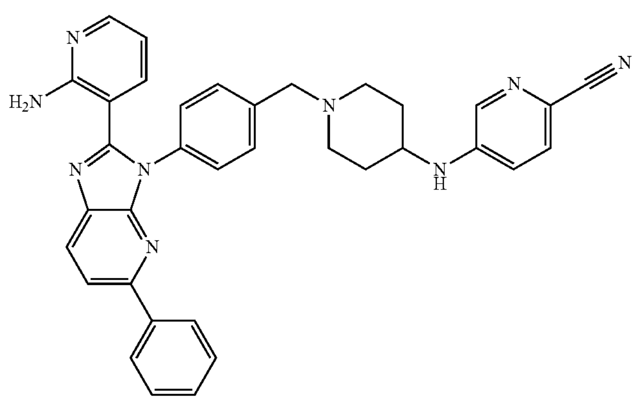 [SMILES: N#Cc1ccc(NC2CCN(Cc3ccc(-n4c(-c5cccnc5N)nc5ccc(-c6ccccc6)nc54)cc3)CC2)cn1] | 5-((1-(4-(2-(2-aminopyridin-3-yl)-5-phenyl-3H-imidazo[4,5-b]pyridin-3-yl)benzyl)piperidin-4-yl)amino)picolinonitrile |

TABLE 1-continued

| Example | Compound Structure | Compound Name |
|---|---|---|
| 85 | 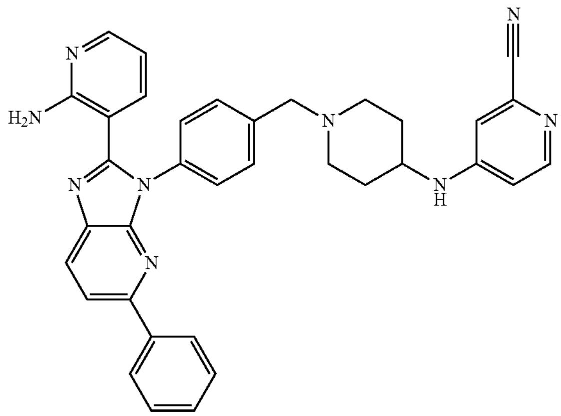 [SMILES: N#Cc1cc(NC2CCN(Cc3ccc(-n4c(-c5cccnc5N)nc5ccc(-c6ccccc6)nc54)cc3)CC2)ccn1] | 4-((1-(4-(2-(2-aminopyridin-3-yl)-5-phenyl-3H-imidazo[4,5-b]pyridin-3-yl)benzyl)piperidin-4-yl)amino)picolinonitrile |
| 86 | 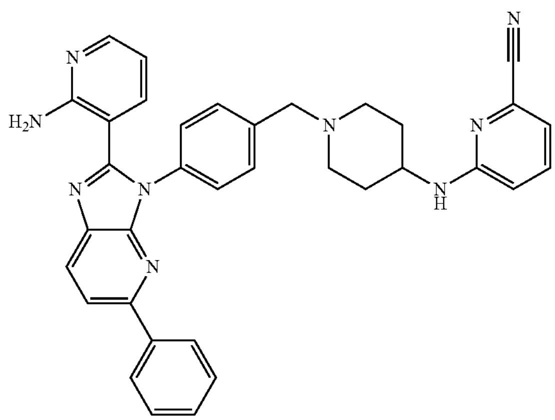 [SMILES: N#Cc1cccc(NC2CCN(Cc3ccc(-n4c(-c5cccnc5N)nc5ccc(-c6ccccc6)nc54)cc3)CC2)n1] | 6-((1-(4-(2-(2-aminopyridin-3-yl)-5-phenyl-3H-imidazo[4,5-b]pyridin-3-yl)benzyl)piperidin-4-yl)amino)picolinonitrile |
| 87 | 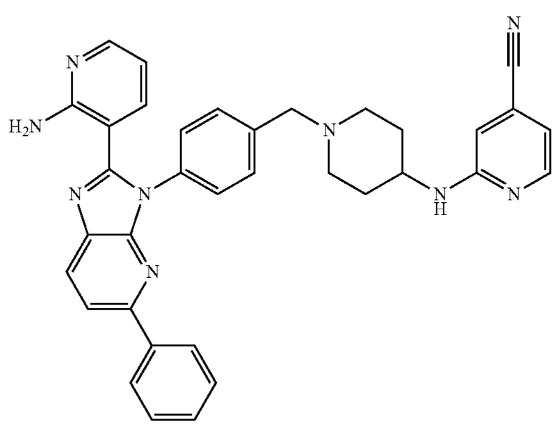 [SMILES: N#Cc1ccnc(NC2CCN(Cc3ccc(-n4c(-c5cccnc5N)nc5ccc(-c6ccccc6)nc54)cc3)CC2)c1] | 2-((1-(4-(2-(2-aminopyridin-3-yl)-5-phenyl-3H-imidazo[4,5-b]pyridin-3-yl)benzyl)piperidin-4-yl)amino)isonicotinonitrile |

TABLE 1-continued
| Example | Compound Structure | Compound Name |
|---|---|---|
| 88 | 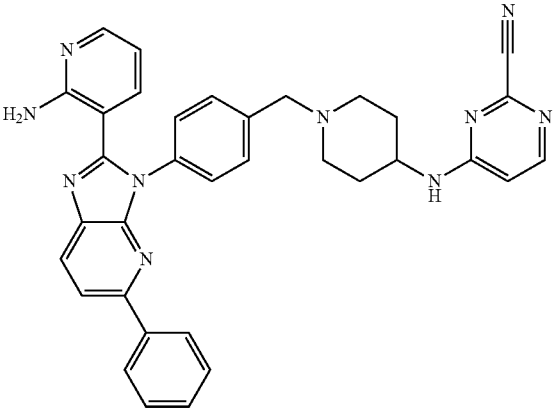 [SMILES: N#Cc1nccc(NC2CCN(Cc3ccc(-n4c(-c5cccnc5N)nc5ccc(-c6ccccc6)nc54)cc3)CC2)n1] | 4-((1-(4-(2-(2-aminopyridin-3-yl)-5-phenyl-3H-imidazo[4,5-b]pyridin-3-yl)benzyl)piperidin-4-yl)amino)pyrimidine-2-carbonitrile |
| 89 | 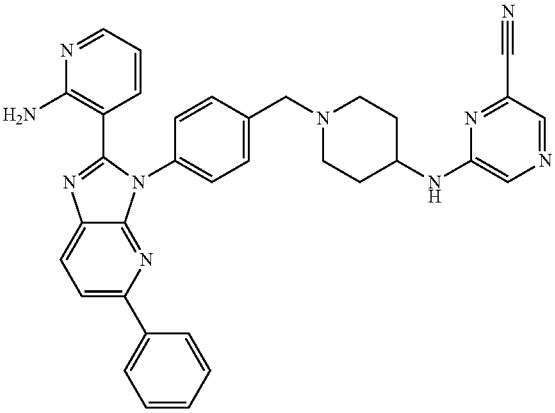 [SMILES: N#Cc1cncc(NC2CCN(Cc3ccc(-n4c(-c5cccnc5N)nc5ccc(-c6ccccc6)nc54)cc3)CC2)n1] | 6-((1-(4-(2-(2-aminopyridin-3-yl)-5-phenyl-3H-imidazo[4,5-b]pyridin-3-yl)benzyl)piperidin-4-yl)amino)pyrazine-2-carbonitrile |
| 90 | 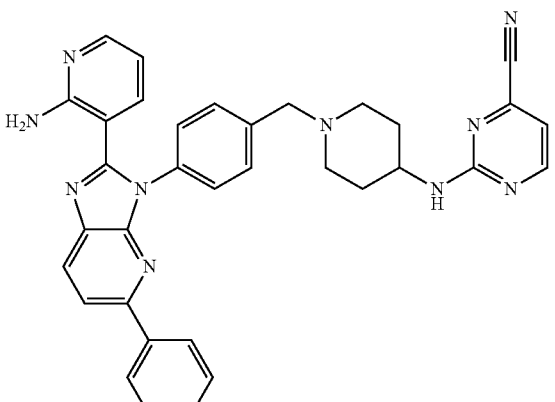 | 2-((1-(4-(2-(2-aminopyridin-3-yl)-5-phenyl-3H-imidazo[4,5-b]pyridin-3-yl)benzyl)piperidin-4-yl)amino)pyrimidine-4-carbonitrile |

TABLE 1-continued

| Example | Compound Structure | Compound Name |
|---|---|---|
| 91 | 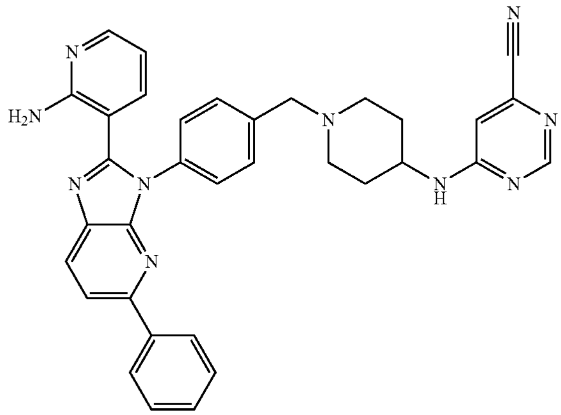 [SMILES: N#Cc1cc(NC2CCN(Cc3ccc(-n4c(-c5cccnc5N)nc5ccc(-c6ccccc6)nc54)cc3)CC2)ncn1] | 6-((1-(4-(2-(2-aminopyridin-3-yl)-5-phenyl-3H-imidazo[4,5-b]pyridin-3-yl)benzyl)piperidin-4-yl)amino)pyrimidine-4-carbonitrile |
| 92 | 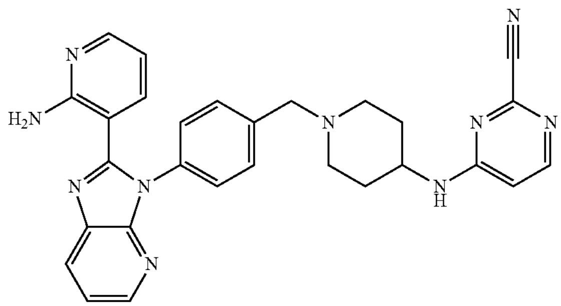 [SMILES: N#Cc1nccc(NC2CCN(Cc3ccc(-n4c(-c5cccnc5N)nc5cccnc54)cc3)CC2)n1] | 4-((1-(4-(2-(2-aminopyridin-3-yl)-3H-imidazo[4,5-b]pyridin-3-yl)benzyl)piperidin-4-yl)amino)pyrimidine-2-carbonitrile |
| 93 | 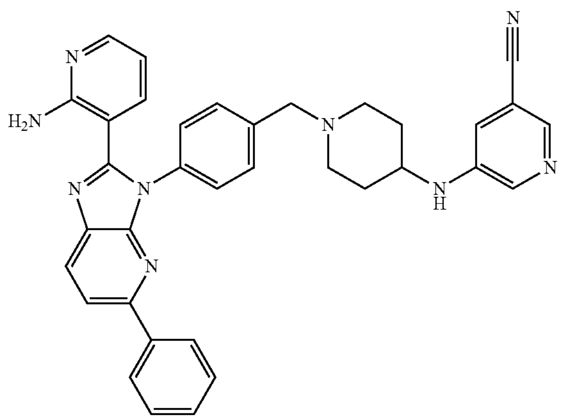 [SMILES: N#Cc1cncc(NC2CCN(Cc3ccc(-n4c(-c5cccnc5N)nc5ccc(-c6ccccc6)nc54)cc3)CC2)c1] | 5-((1-(4-(2-(2-aminopyridin-3-yl)-5-phenyl-3H-imidazo[4,5-b]pyridin-3-yl)benzyl)piperidin-4-yl)amino)nicotinonitrile |
| 94 | 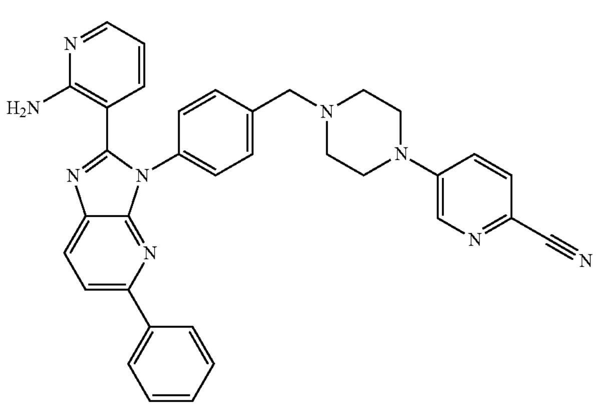 [SMILES: N#Cc1ccc(N2CCN(Cc3ccc(-n4c(-c5cccnc5N)nc5ccc(-c6ccccc6)nc54)cc3)CC2)cn1] | 5-(4-(4-(2-(2-aminopyridin-3-yl)-5-phenyl-3H-imidazo[4,5-b]pyridin-3-yl)benzyl)piperazin-1-yl)picolinonitrile |

TABLE 1-continued

| Example | Compound Structure | Compound Name |
|---|---|---|
| 95 | 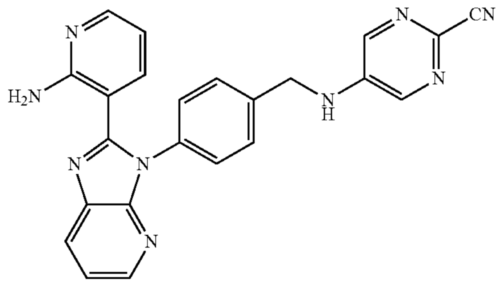 [SMILES: N#Cc1ncc(NCc2ccc(-n3c(-c4cccnc4N)nc4cccnc43)cc2)cn1] | 5-((4-(2-(2-aminopyridin-3-yl)-3H-imidazo[4,5-b]pyridin-3-yl)benzyl)amino)pyrimidine-2-carbonitrile |
| 96 | 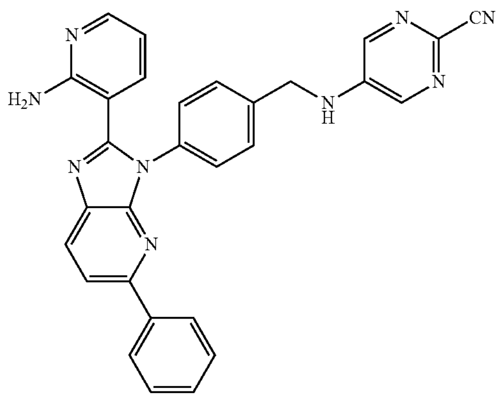 [SMILES: N#Cc1ncc(NCc2ccc(-n3c(-c4cccnc4N)nc4ccc(-c5ccccc5)nc43)cc2)cn1] | 5-((4-(2-(2-aminopyridin-3-yl)-5-phenyl-3H-imidazo[4,5-b]pyridin-3-yl)benzyl)amino)pyrimidine-2-carbonitrile |
| 97 | 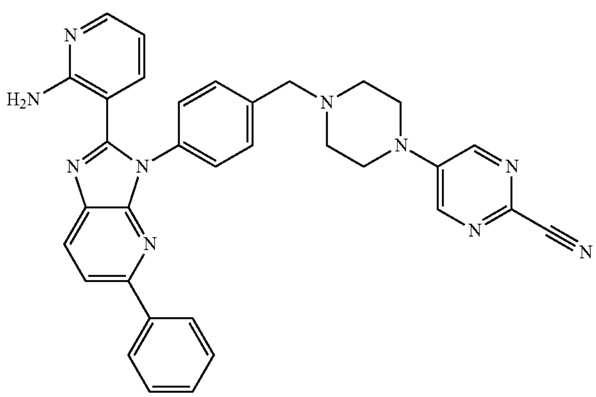 | 5-(4-(4-(2-(2-aminopyridin-3-yl)-5-phenyl-3H-imidazo[4,5-b]pyridin-3-yl)benzyl)piperazin-1-yl)pyrimidine-2-carbonitrile |
| 98 | 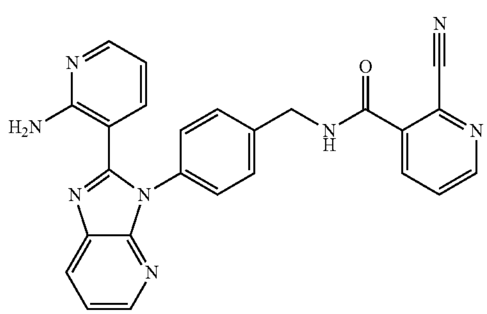 [SMILES: N#Cc1ncccc1C(=O)NCc1ccc(-n2c(-c3cccnc3N)nc3cccnc32)cc1] | N-(4-(2-(2-aminopyridin-3-yl)-3H-imidazo[4,5-b]pyridin-3-yl)benzyl)-2-cyanonicotinamide |

TABLE 1-continued

| Example | Compound Structure | Compound Name |
|---|---|---|
| 99 | 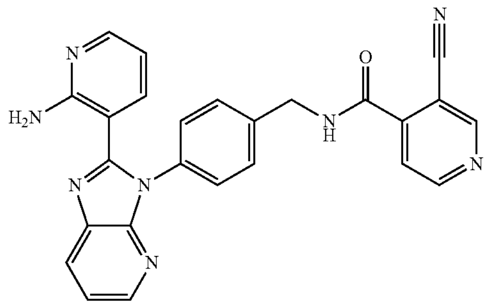 [SMILES: N#Cc1cnccc1C(=O)NCc1ccc(-n2c(-c3cccnc3N)nc3cccnc32)cc1] | N-(4-(2-(2-aminopyridin-3-yl)-3H-imidazo[4,5-b]pyridin-3-yl)benzyl)-3-cyanoisonicotinamide |
| 100 | 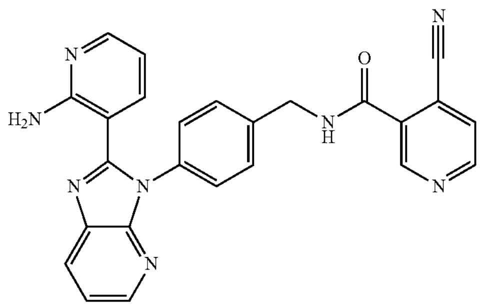 [SMILES: N#Cc1ccncc1C(=O)NCc1ccc(-n2c(-c3cccnc3N)nc3cccnc32)cc1] | N-(4-(2-(2-aminopyridin-3-yl)-3H-imidazo[4,5-b]pyridin-3-yl)benzyl)-4-cyanonicotinamide |
| 101 | 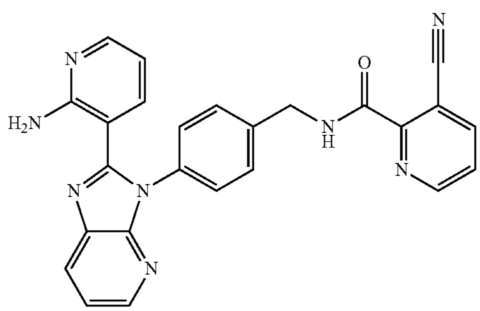 [SMILES: N#Cc1cccnc1C(=O)NCc1ccc(-n2c(-c3cccnc3N)nc3cccnc32)cc1] | N-(4-(2-(2-aminopyridin-3-yl)-3H-imidazo[4,5-b]pyridin-3-yl)benzyl)-3-cyanopicolinamide |
| 102 | 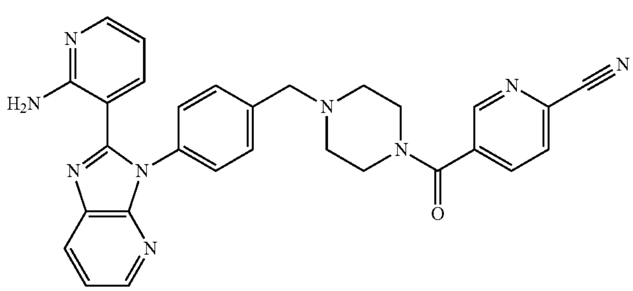 [SMILES: N#Cc1ccc(C(=O)N2CCN(Cc3ccc(-n4c(-c5cccnc5N)nc5cccnc54)cc3)CC2)cn1] | 5-(4-(4-(2-(2-aminopyridin-3-yl)-3H-imidazo[4,5-b]pyridin-3-yl)benzyl)piperazine-1-carbonyl)picolinonitrile |

TABLE 1-continued
| Example | Compound Structure | Compound Name |
|---|---|---|
| 103 | 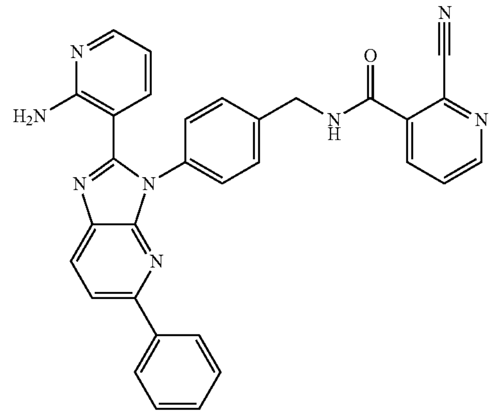 [SMILES: N#Cc1ncccc1C(=O)NCc1ccc(-n2c(-c3cccnc3N)nc3ccc(-c4ccccc4)nc32)cc1] | N-(4-(2-(2-aminopyridin-3-yl)-5-phenyl-3H-imidazo[4,5-b]pyridin-3-yl)benzyl)-2-cyanonicotinamide |
| 104 | 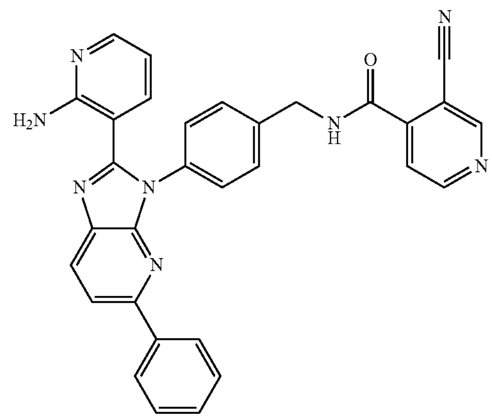 [SMILES: N#Cc1cnccc1C(=O)NCc1ccc(-n2c(-c3cccnc3N)nc3ccc(-c4ccccc4)nc32)cc1] | N-(4-(2-(2-aminopyridin-3-yl)-5-phenyl-3H-imidazo[4,5-b]pyridin-3-yl)benzyl)-3-cyanoisonicotinamide |
| 105 | 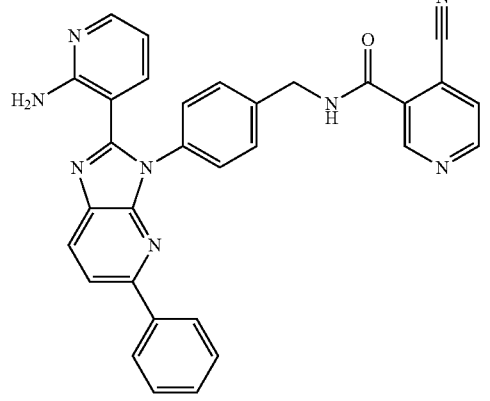 | N-(4-(2-(2-aminopyridin-3-yl)-5-phenyl-3H-imidazo[4,5-b]pyridin-3-yl)benzyl)-4-cyanonicotinamide |

TABLE 1-continued

| Example | Compound Structure | Compound Name |
|---|---|---|
| 106 | 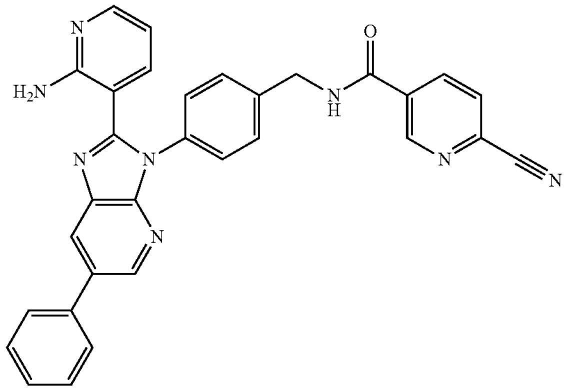 [SMILES: N#Cc1ccc(C(=O)NCc2ccc(-n3c(-c4cccnc4N)nc4cc(-c5ccccc5)cnc43)cc2)cn1] | N-(4-(2-(2-aminopyridin-3-yl)-6-phenyl-3H-imidazo[4,5-b]pyridin-3-yl)benzyl)-6-cyanonicotinamide |
| 107 | 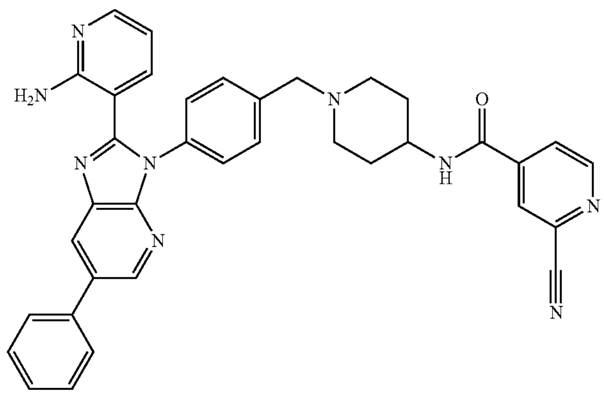 [SMILES: N#Cc1cc(C(=O)NC2CCN(Cc3ccc(-n4c(-c5cccnc5N)nc5cc(-c6ccccc6)cnc54)cc3)CC2)ccn1] | N-(1-(4-(2-(2-aminopyridin-3-yl)-6-phenyl-3H-imidazo[4,5-b]pyridin-3-yl)benzyl)piperidin-4-yl)-2-cyanoisonicotinamide |
| 108 | 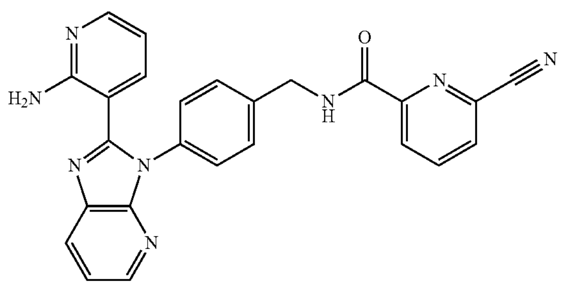 [SMILES: N#Cc1cccc(C(=O)NCc2ccc(-n3c(-c4cccnc4N)nc4cccnc43)cc2)n1] | N-(4-(2-(2-aminopyridin-3-yl)-3H-imidazo[4,5-b]pyridin-3-yl)benzyl)-6-cyanopicolinamide |
| 109 | 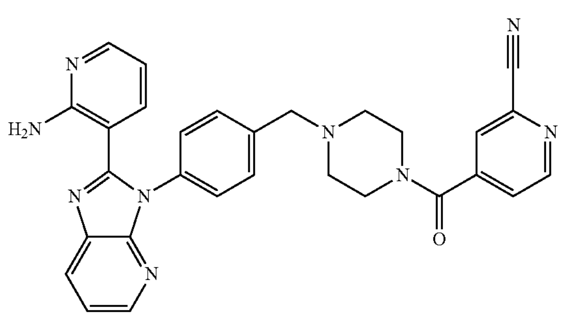 [SMILES: N#Cc1cc(C(=O)N2CCN(Cc3ccc(-n4c(-c5cccnc5N)nc5cccnc54)cc3)CC2)ccn1] | 4-(4-(4-(2-(2-aminopyridin-3-yl)-3H-imidazo[4,5-b]pyridin-3-yl)benzyl)piperazine-1-carbonyl)picolinonitrile |

TABLE 1-continued

| Example | Compound Structure | Compound Name |
|---|---|---|
| 110 | 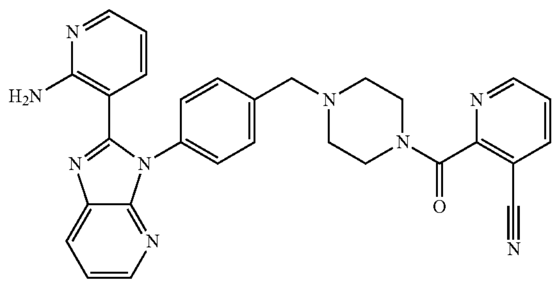 [SMILES: N#Cc1cccnc1C(=O)N1CCN(Cc2ccc(-n3c(-c4cccnc4N)nc4cccnc43)cc2)CC1] | 2-(4-(4-(2-(2-aminopyridin-3-yl)-3H-imidazo[4,5-b]pyridin-3-yl)benzyl)piperazine-1-carbonyl)nicotinonitrile |
| 111 | 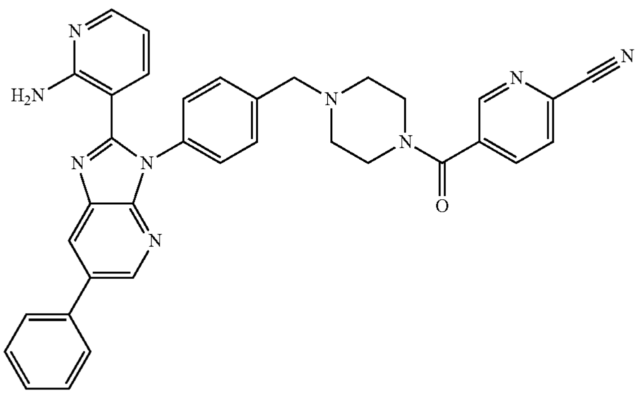 [SMILES: N#Cc1ccc(C(=O)N2CCN(Cc3ccc(-n4c(-c5cccnc5N)nc5cc(-c6ccccc6)cnc54)cc3)CC2)cn1] | 5-(4-(4-(2-(2-aminopyridin-3-yl)-6-phenyl-3H-imidazo[4,5-b]pyridin-3-yl)benzyl)piperazine-1-carbonyl)picolinonitrile |
| 112 | 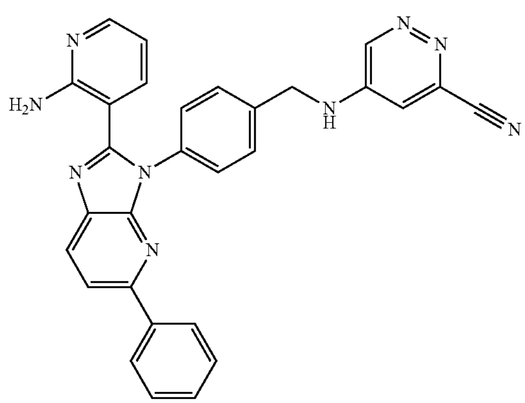 | 5-((4-(2-(2-aminopyridin-3-yl)-5-phenyl-3H-imidazo[4,5-b]pyridin-3-yl)benzyl)amino)pyridazine-3-carbonitrile |
| 113 | 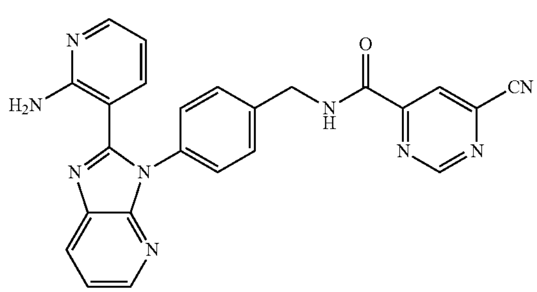 [SMILES: N#Cc1cc(C(=O)NCc2ccc(-n3c(-c4cccnc4N)nc4cccnc43)cc2)ncn1] | N-(4-(2-(2-aminopyridin-3-yl)-3H-imidazo[4,5-b]pyridin-3-yl)benzyl)-6-cyanopyrimidine-4-carboxamide |

TABLE 1-continued

| Example | Compound Structure | Compound Name |
|---|---|---|
| 114 | 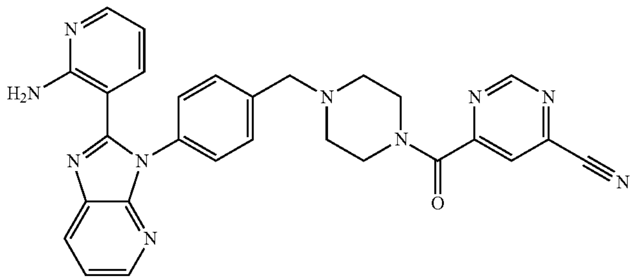 [SMILES: N#Cc1cc(C(=O)N2CCN(Cc3ccc(-n4c(-c5cccnc5N)nc5cccnc54)cc3)CC2)ncn1] | 6-(4-(4-(2-(2-aminopyridin-3-yl)-3H-imidazo[4,5-b]pyridin-3-yl)benzyl)piperazine-1-carbonyl)pyrimidine-4-carbonitrile |
| 115 | 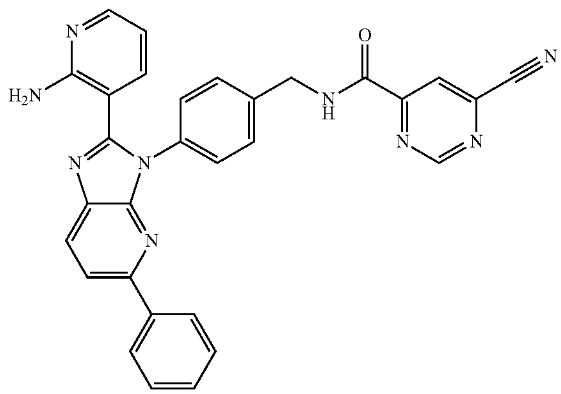 [SMILES: N#Cc1cc(C(=O)NCc2ccc(-n3c(-c4cccnc4N)nc4ccc(-c5ccccc5)nc43)cc2)ncn1] | N-(4-(2-(2-aminopyridin-3-yl)-5-phenyl-3H-imidazo[4,5-b]pyridin-3-yl)benzyl)-6-cyanopyrimidine-4-carboxamide |
| 116 | 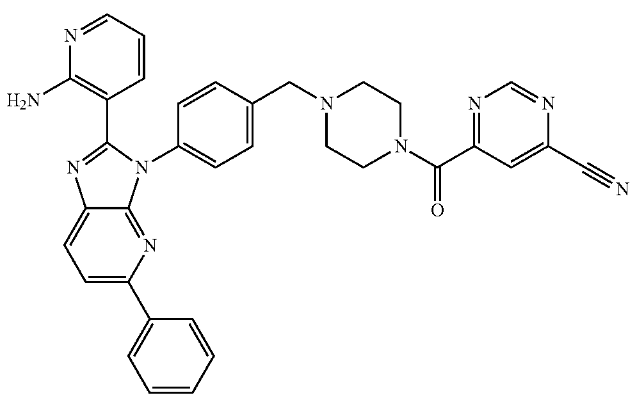 | 6-(4-(4-(2-(2-aminopyridin-3-yl)-5-phenyl-3H-imidazo[4,5-b]pyridin-3-yl)benzyl)piperazine-1-carbonyl)pyrimidine-4-carbonitrile |
| 117 | 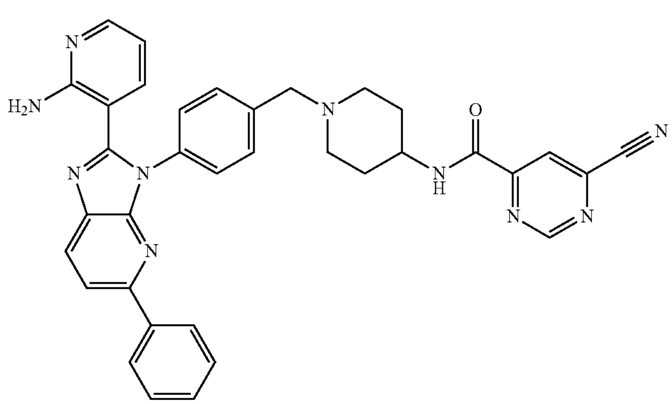 | N-(1-(4-(2-(2-aminopyridin-3-yl)-5-phenyl-3H-imidazo[4,5-b]pyridin-3-yl)benzyl)piperidin-4-yl)-6-cyanopyrimidine-4-carboxamide |

TABLE 1-continued

| Example | Compound Structure | Compound Name |
|---|---|---|
| 118 | 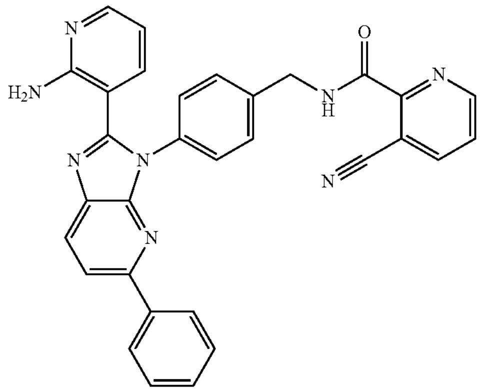 [SMILES: N#Cc1cccnc1C(=O)NCc1ccc(-n2c(-c3cccnc3N)nc3ccc(-c4ccccc4)nc32)cc1] | N-(4-(2-(2-aminopyridin-3-yl)-5-phenyl-3H-imidazo[4,5-b]pyridin-3-yl)benzyl)-3-cyanopicolinamide |
| 119 | 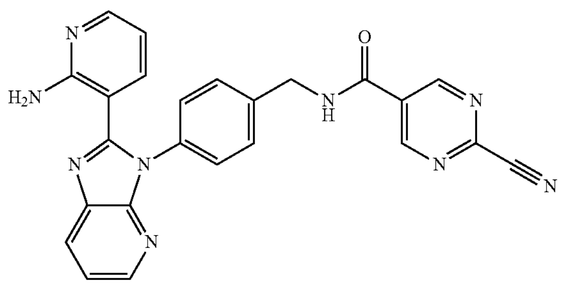 [SMILES: N#Cc1ncc(C(=O)NCc2ccc(-n3c(-c4cccnc4N)nc4cccnc43)cc2)cn1] | N-(4-(2-(2-aminopyridin-3-yl)-3H-imidazo[4,5-b]pyridin-3-yl)benzyl)-2-cyanopyrimidine-5-carboxamide |
| 120 | 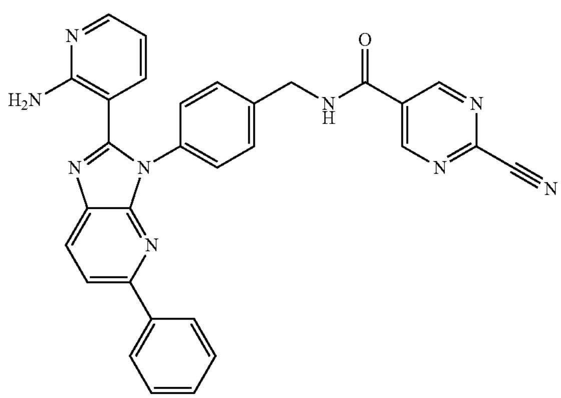 [SMILES: N#Cc1ncc(C(=O)NCc2ccc(-n3c(-c4cccnc4N)nc4ccc(-c5ccccc5)nc43)cc2)cn1] | N-(4-(2-(2-aminopyridin-3-yl)-5-phenyl-3H-imidazo[4,5-b]pyridin-3-yl)benzyl)-2-cyanopyrimidine-5-carboxamide |
| 121 | 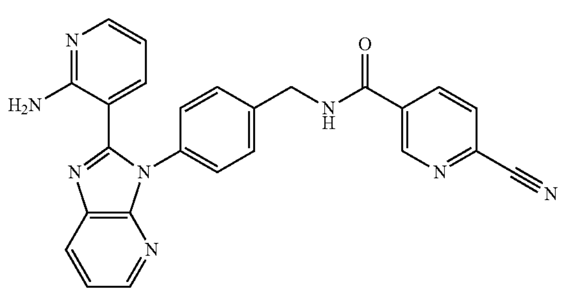 [SMILES: N#Cc1ccc(C(=O)NCc2ccc(-n3c(-c4cccnc4N)nc4cccnc43)cc2)cn1] | N-(4-(2-(2-aminopyridin-3-yl)-3H-imidazo[4,5-b]pyridin-3-yl)benzyl)-6-cyanonicotinamide |

TABLE 1-continued
| Example | Compound Structure | Compound Name |
|---|---|---|
| 122 | 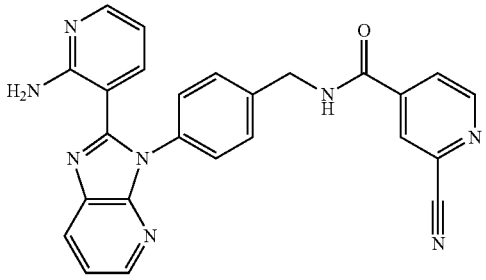 [SMILES: N#Cc1cc(C(=O)NCc2ccc(-n3c(-c4cccnc4N)nc4cccnc43)cc2)ccn1] | N-(4-(2-(2-aminopyridin-3-yl)-3H-imidazo[4,5-b]pyridin-3-yl)benzyl)-2-cyanoisonicotinamide |
| 123 | 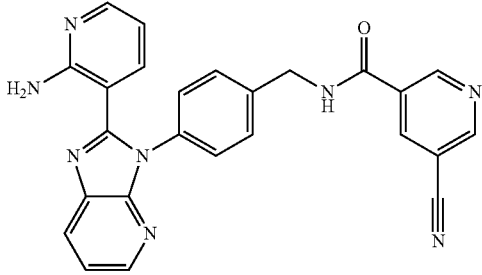 [SMILES: N#Cc1cncc(C(=O)NCc2ccc(-n3c(-c4cccnc4N)nc4cccnc43)cc2)c1] | N-(4-(2-(2-aminopyridin-3-yl)-3H-imidazo[4,5-b]pyridin-3-yl)benzyl)-5-cyanonicotinamide |
| 124 | 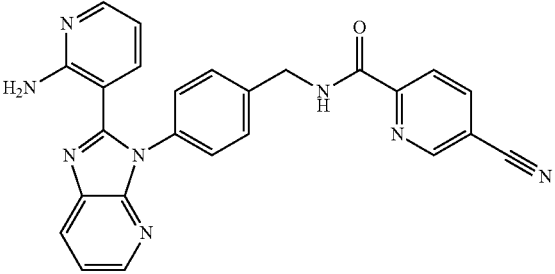 [SMILES: N#Cc1ccc(C(=O)NCc2ccc(-n3c(-c4cccnc4N)nc4cccnc43)cc2)nc1] | N-(4-(2-(2-aminopyridin-3-yl)-3H-imidazo[4,5-b]pyridin-3-yl)benzyl)-5-cyanopicolinamide |
| 125 | 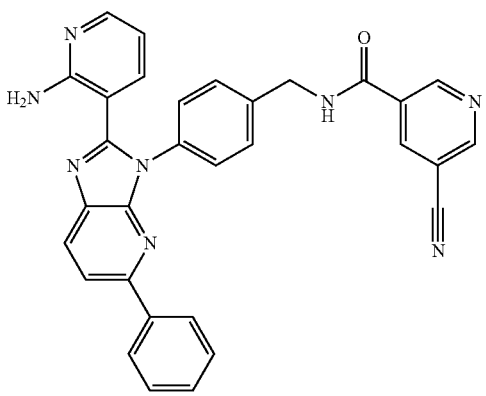 [SMILES: N#Cc1cncc(C(=O)NCc2ccc(-n3c(-c4cccnc4N)nc4ccc(-c5ccccc5)nc43)cc2)c1] | N-(4-(2-(2-aminopyridin-3-yl)-5-phenyl-3H-imidazo[4,5-b]pyridin-3-yl)benzyl)-5-cyanonicotinamide |

TABLE 1-continued

| Example | Compound Structure | Compound Name |
|---|---|---|
| 126 | 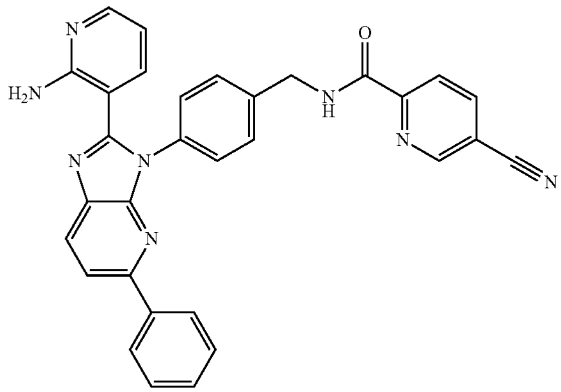 [SMILES: N#Cc1ccc(C(=O)NCc2ccc(-n3c(-c4cccnc4N)nc4ccc(-c5ccccc5)nc43)cc2)nc1] | N-(4-(2-(2-aminopyridin-3-yl)-5-phenyl-3H-imidazo[4,5-b]pyridin-3-yl)benzyl)-5-cyanopicolinamide |
| 127 | 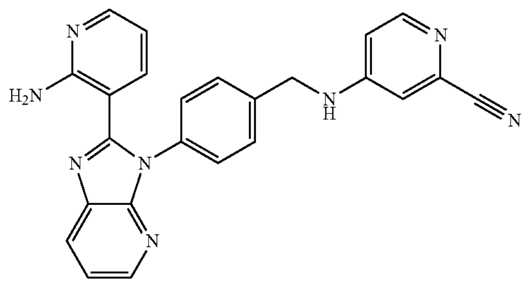 [SMILES: N#Cc1cc(NCc2ccc(-n3c(-c4cccnc4N)nc4cccnc43)cc2)ccn1] | 4-((4-(2-(2-aminopyridin-3-yl)-3H-imidazo[4,5-b]pyridin-3-yl)benzyl)amino)picolinonitrile |
| 128 | 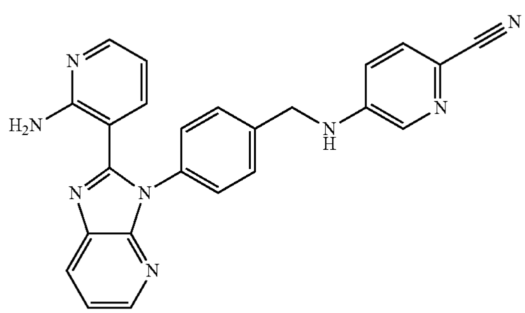 [SMILES: N#Cc1ccc(NCc2ccc(-n3c(-c4cccnc4N)nc4cccnc43)cc2)cn1] | 5-((4-(2-(2-aminopyridin-3-yl)-3H-imidazo[4,5-b]pyridin-3-yl)benzyl)amino)picolinonitrile |
| 129 | 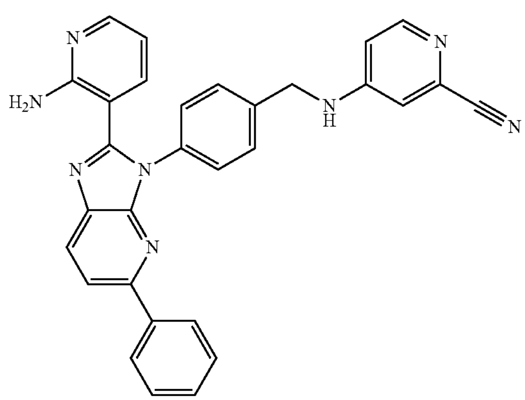 | 4-((4-(2-(2-aminopyridin-3-yl)-5-phenyl-3H-imidazo[4,5-b]pyridin-3-yl)benzyl)amino)picolinonitrile |

TABLE 1-continued

| Example | Compound Structure | Compound Name |
|---|---|---|
| 130 | 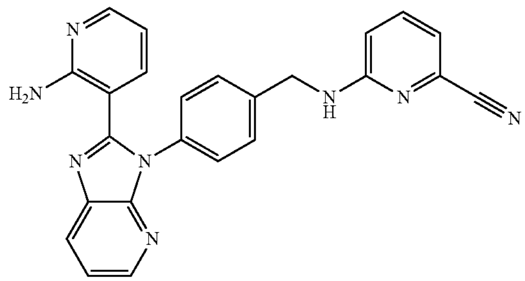 [SMILES: N#Cc1cccc(NCc2ccc(-n3c(-c4cccnc4N)nc4cccnc43)cc2)n1] | 6-((4-(2-(2-aminopyridin-3-yl)-3H-imidazo[4,5-b]pyridin-3-yl)benzyl)amino)picolinonitrile |
| 131 | 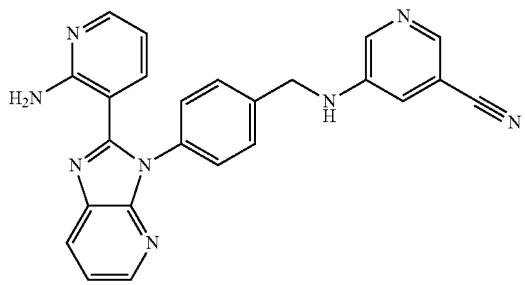 [SMILES: N#Cc1cncc(NCc2ccc(-n3c(-c4cccnc4N)nc4cccnc43)cc2)c1] | 5-((4-(2-(2-aminopyridin-3-yl)-3H-imidazo[4,5-b]pyridin-3-yl)benzyl)amino)nicotinonitrile |
| 132 | 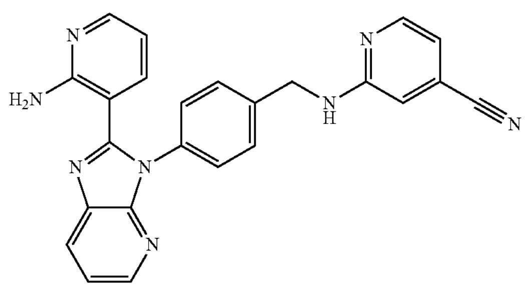 [SMILES: N#Cc1ccnc(NCc2ccc(-n3c(-c4cccnc4N)nc4cccnc43)cc2)c1] | 2-((4-(2-(2-aminopyridin-3-yl)-3H-imidazo[4,5-b]pyridin-3-yl)benzyl)amino)isonicotinonitrile |
| 133 | 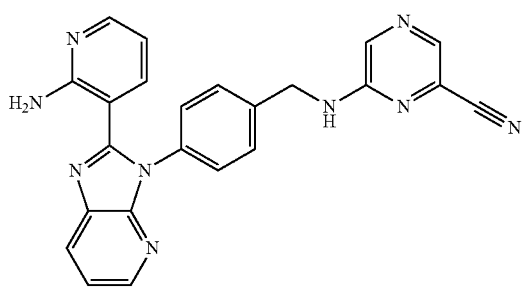 [SMILES: N#Cc1cncc(NCc2ccc(-n3c(-c4cccnc4N)nc4cccnc43)cc2)n1] | 6-((4-(2-(2-aminopyridin-3-yl)-3H-imidazo[4,5-b]pyridin-3-yl)benzyl)amino)pyrazine-2-carbonitrile |
| 134 | 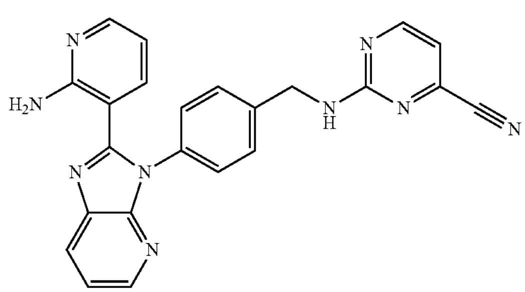 [SMILES: N#Cc1ccnc(NCc2ccc(-n3c(-c4cccnc4N)nc4cccnc43)cc2)n1] | 2-((4-(2-(2-aminopyridin-3-yl)-3H-imidazo[4,5-b]pyridin-3-yl)benzyl)amino)pyrimidine-4-carbonitrile |

TABLE 1-continued

| Example | Compound Structure | Compound Name |
|---|---|---|
| 135 | 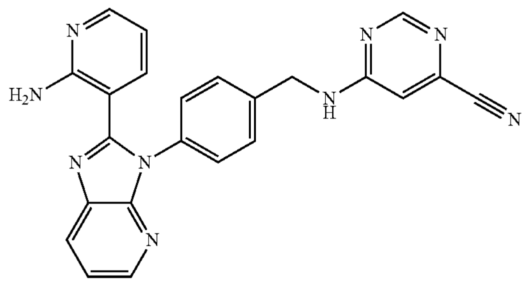 [SMILES: N#Cc1cc(NCc2ccc(-n3c(-c4cccnc4N)nc4cccnc43)cc2)ncn1] | 6-((4-(2-(2-aminopyridin-3-yl)-3H-imidazo[4,5-b]pyridin-3-yl)benzyl)amino)pyrimidine-4-carbonitrile |
| 136 | 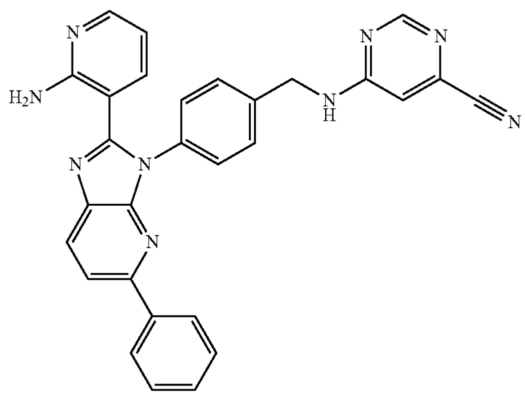 | 6-((4-(2-(2-aminopyridin-3-yl)-5-phenyl-3H-imidazo[4,5-b]pyridin-3-yl)benzyl)amino)pyrimidine-4-carbonitrile |
| 137 | 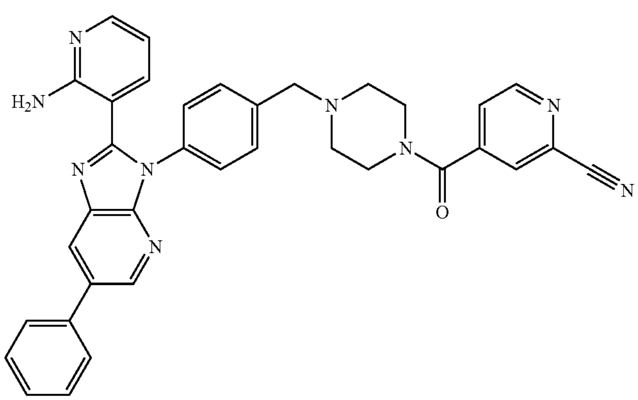 [SMILES: N#Cc1cc(C(=O)N2CCN(Cc3ccc(-n4c(-c5cccnc5N)nc5cc(-c6ccccc6)cnc54)cc3)CC2)ccn1] | 4-(4-(4-(2-(2-aminopyridin-3-yl)-6-phenyl-3H-imidazo[4,5-b]pyridin-3-yl)benzyl)piperazine-1-carbonyl)picolinonitrile |
| 138 | 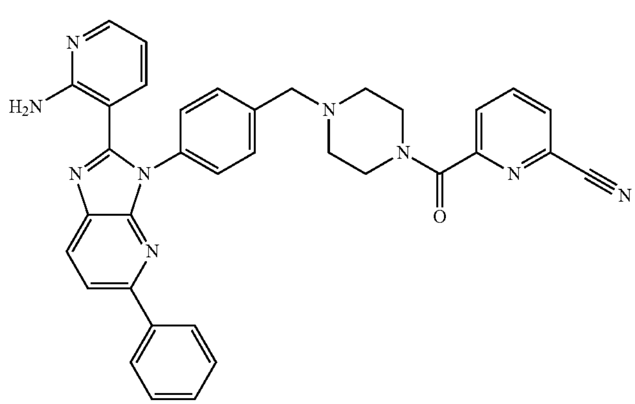 [SMILES: N#Cc1cccc(C(=O)N2CCN(Cc3ccc(-n4c(-c5cccnc5N)nc5ccc(-c6ccccc6)nc54)cc3)CC2)n1] | 6-(4-(4-(2-(2-aminopyridin-3-yl)-5-phenyl-3H-imidazo[4,5-b]pyridin-3-yl)benzyl)piperazine-1-carbonyl)picolinonitrile |

TABLE 1-continued

| Example | Compound Structure | Compound Name |
|---|---|---|
| 139 | 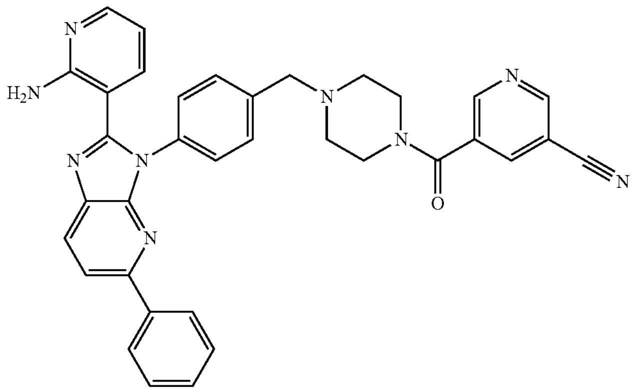 [SMILES: N#Cc1cncc(C(=O)N2CCN(Cc3ccc(-n4c(-c5cccnc5N)nc5ccc(-c6ccccc6)nc54)cc3)CC2)c1] | 5-(4-(4-(2-(2-aminopyridin-3-yl)-5-phenyl-3H-imidazo[4,5-b]pyridin-3-yl)benzyl)piperazine-1-carbonyl)nicotinonitrile |
| 140 | 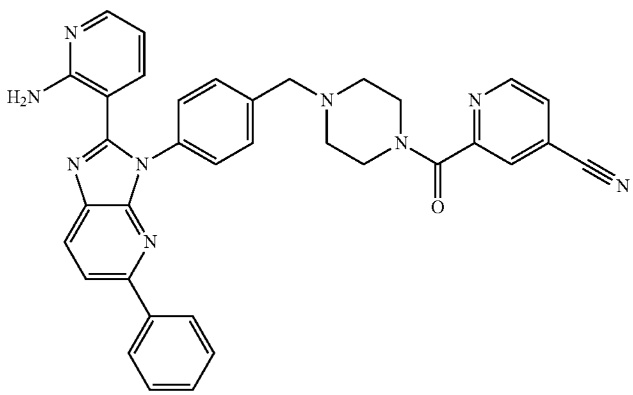 [SMILES: N#Cc1ccnc(C(=O)N2CCN(Cc3ccc(-n4c(-c5cccnc5N)nc5ccc(-c6ccccc6)nc54)cc3)CC2)c1] | 2-(4-(4-(2-(2-aminopyridin-3-yl)-5-phenyl-3H-imidazo[4,5-b]pyridin-3-yl)benzyl)piperazine-1-carbonyl)isonicotinonitrile |
| 141 | 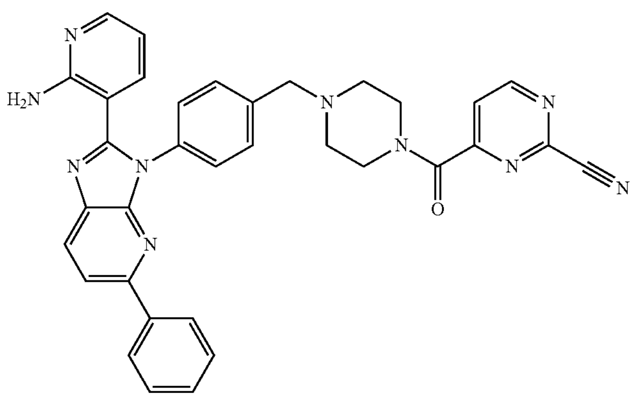 [SMILES: N#Cc1nccc(C(=O)N2CCN(Cc3ccc(-n4c(-c5cccnc5N)nc5ccc(-c6ccccc6)nc54)cc3)CC2)n1] | 4-(4-(4-(2-(2-aminopyridin-3-yl)-5-phenyl-3H-imidazo[4,5-b]pyridin-3-yl)benzyl)piperazine-1-carbonyl)pyrimidine-2-carbonitrile |
| 142 | 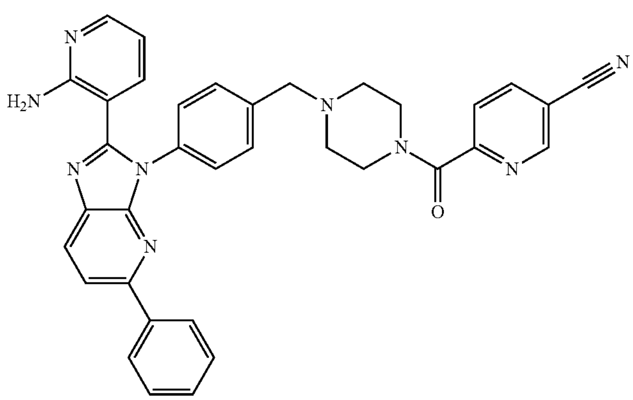 [SMILES: N#Cc1ccc(C(=O)N2CCN(Cc3ccc(-n4c(-c5cccnc5N)nc5ccc(-c6ccccc6)nc54)cc3)CC2)nc1] | 6-(4-(4-(2-(2-aminopyridin-3-yl)-5-phenyl-3H-imidazo[4,5-b]pyridin-3-yl)benzyl)piperazine-1-carbonyl)nicotinonitrile |

TABLE 1-continued

| Example | Compound Structure | Compound Name |
|---|---|---|
| 143 | 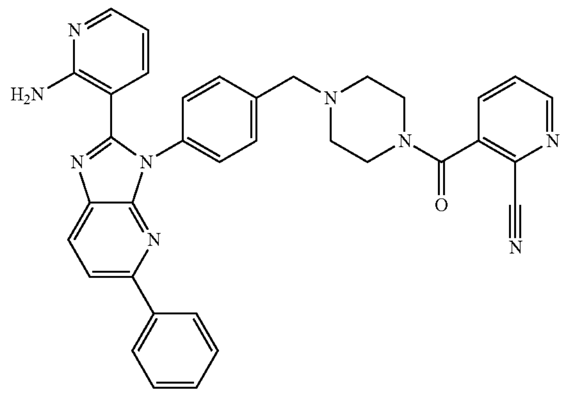 [SMILES: N#Cc1ncccc1C(=O)N1CCN(Cc2ccc(-n3c(-c4cccnc4N)nc4ccc(-c5ccccc5)nc43)cc2)CC1] | 3-(4-(4-(2-(2-aminopyridin-3-yl)-5-phenyl-3H-imidazo[4,5-b]pyridin-3-yl)benzyl)piperazine-1-carbonyl)picolinonitrile |
| 144 | 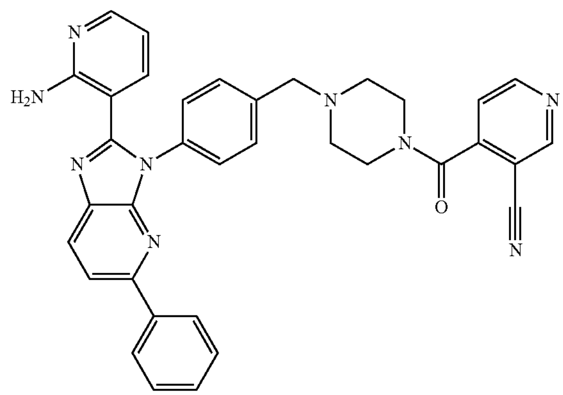 [SMILES: N#Cc1cnccc1C(=O)N1CCN(Cc2ccc(-n3c(-c4cccnc4N)nc4ccc(-c5ccccc5)nc43)cc2)CC1] | 4-(4-(4-(2-(2-aminopyridin-3-yl)-5-phenyl-3H-imidazo[4,5-b]pyridin-3-yl)benzyl)piperazine-1-carbonyl)nicotinonitrile |
| 145 | 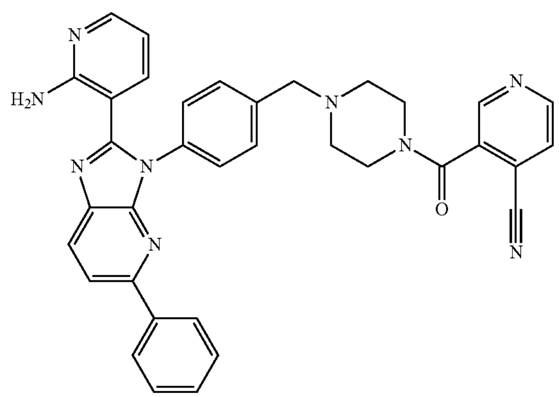 [SMILES: N#Cc1ccncc1C(=O)N1CCN(Cc2ccc(-n3c(-c4cccnc4N)nc4ccc(-c5ccccc5)nc43)cc2)CC1] | 3-(4-(4-(2-(2-aminopyridin-3-yl)-5-phenyl-3H-imidazo[4,5-b]pyridin-3-yl)benzyl)piperazine-1-carbonyl)isonicotinonitrile |
| 146 | 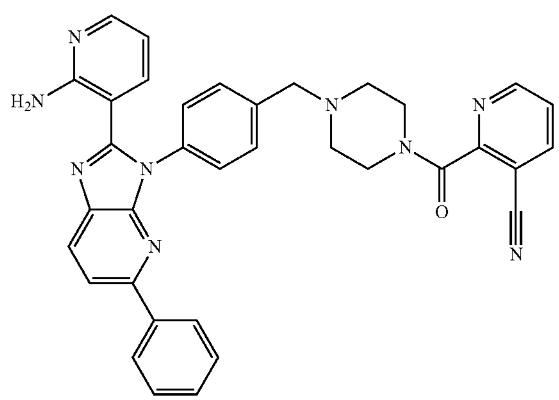 [SMILES: N#Cc1cccnc1C(=O)N1CCN(Cc2ccc(-n3c(-c4cccnc4N)nc4ccc(-c5ccccc5)nc43)cc2)CC1] | 2-(4-(4-(2-(2-aminopyridin-3-yl)-5-phenyl-3H-imidazo[4,5-b]pyridin-3-yl)benzyl)piperazine-1-carbonyl)nicotinonitrile |

TABLE 1-continued

| Example | Compound Structure | Compound Name |
|---|---|---|
| 147 | 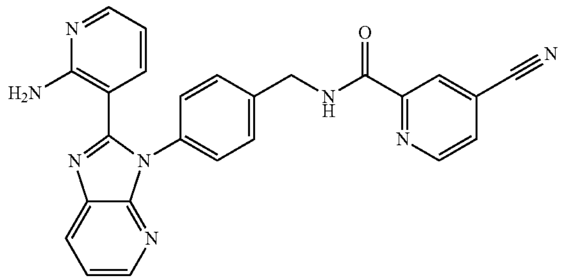 [SMILES: N#Cc1ccnc(C(=O)NCc2ccc(-n3c(-c4cccnc4N)nc4cccnc43)cc2)c1] | N-(4-(2-(2-aminopyridin-3-yl)-3H-imidazo[4,5-b]pyridin-3-yl)benzyl)-4-cyanopicolinamide |
| 148 | 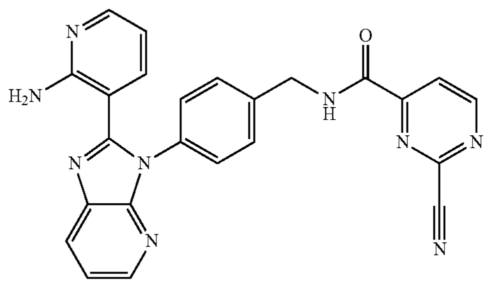 [SMILES: N#Cc1nccc(C(=O)NCc2ccc(-n3c(-c4cccnc4N)nc4cccnc43)cc2)n1] | N-(4-(2-(2-aminopyridin-3-yl)-3H-imidazo[4,5-b]pyridin-3-yl)benzyl)-2-cyanopyrimidine-4-carboxamide |
| 149 | 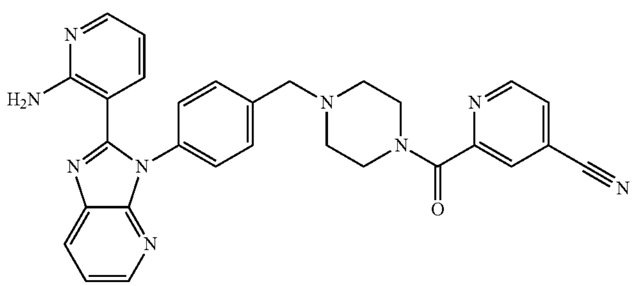 [SMILES: N#Cc1ccnc(C(=O)N2CCN(Cc3ccc(-n4c(-c5cccnc5N)nc5cccnc54)cc3)CC2)c1] | 2-(4-(4-(2-(2-aminopyridin-3-yl)-3H-imidazo[4,5-b]pyridin-3-yl)benzyl)piperazine-1-carbonyl)isonicotinonitrile |
| 150 | 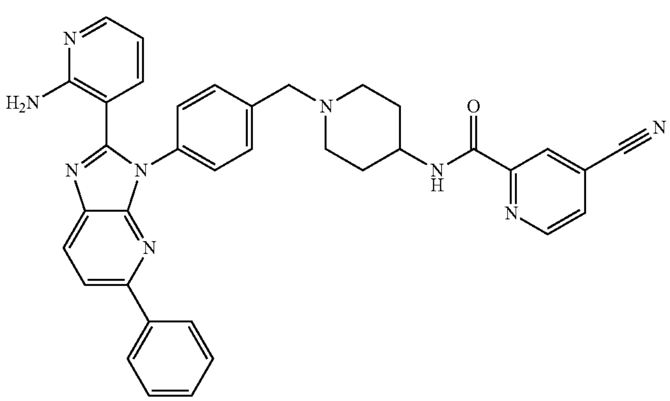 [SMILES: N#Cc1ccnc(C(=O)NC2CCN(Cc3ccc(-n4c(-c5cccnc5N)nc5ccc(-c6ccccc6)nc54)cc3)CC2)c1] | N-(1-(4-(2-(2-aminopyridin-3-yl)-5-phenyl-3H-imidazo[4,5-b]pyridin-3-yl)benzyl)piperidin-4-yl)-4-cyanopicolinamide |

TABLE 1-continued

| Example | Compound Structure | Compound Name |
|---|---|---|
| 151 | 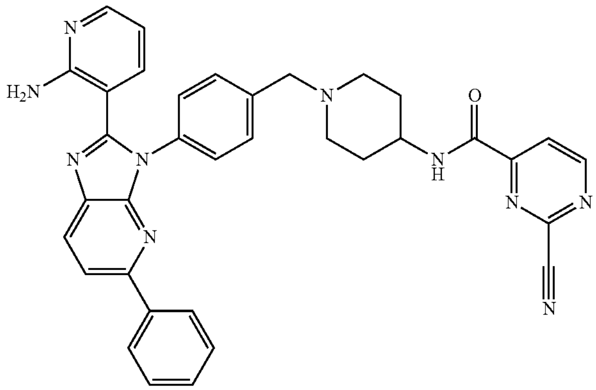 [SMILES: N#Cc1nccc(C(=O)NC2CCN(Cc3ccc(-n4c(-c5cccnc5N)nc5ccc(-c6ccccc6)nc54)cc3)CC2)n1] | N-(1-(4-(2-(2-aminopyridin-3-yl)-5-phenyl-3H-imidazo[4,5-b]pyridin-3-yl)benzyl)piperidin-4-yl)-2-cyanopyrimidine-4-carboxamide |
| 152 | 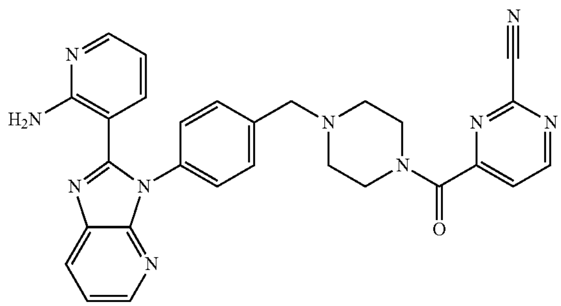 [SMILES: N#Cc1nccc(C(=O)N2CCN(Cc3ccc(-n4c(-c5cccnc5N)nc5cccnc54)cc3)CC2)n1] | 4-(4-(4-(2-(2-aminopyridin-3-yl)-3H-imidazo[4,5-b]pyridin-3-yl)benzyl)piperazine-1-carbonyl)pyrimidine-2-carbonitrile |
| 153 | 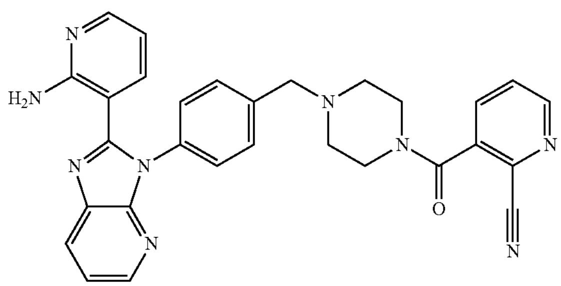 [SMILES: N#Cc1ncccc1C(=O)N1CCN(Cc2ccc(-n3c(-c4cccnc4N)nc4cccnc43)cc2)CC1] | 3-(4-(4-(2-(2-aminopyridin-3-yl)-3H-imidazo[4,5-b]pyridin-3-yl)benzyl)piperazine-1-carbonyl)picolinonitrile |
| 154 | 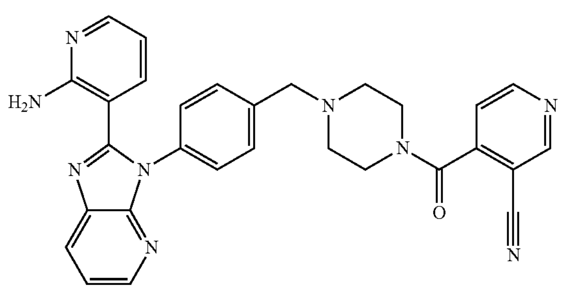 [SMILES: N#Cc1cnccc1C(=O)N1CCN(Cc2ccc(-n3c(-c4cccnc4N)nc4cccnc43)cc2)CC1] | 4-(4-(4-(2-(2-aminopyridin-3-yl)-3H-imidazo[4,5-b]pyridin-3-yl)benzyl)piperazine-1-carbonyl)nicotinonitrile |
| 155 | 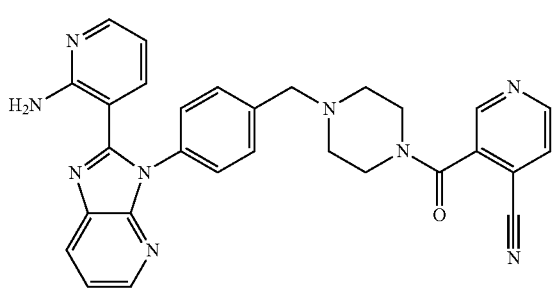 [SMILES: N#Cc1ccncc1C(=O)N1CCN(Cc2ccc(-n3c(-c4cccnc4N)nc4cccnc43)cc2)CC1] | 3-(4-(4-(2-(2-aminopyridin-3-yl)-3H-imidazo[4,5-b]pyridin-3-yl)benzyl)piperazine-1-carbonyl)isonicotinonitrile |

TABLE 1-continued

| Example | Compound Structure | Compound Name |
|---|---|---|
| 156 | 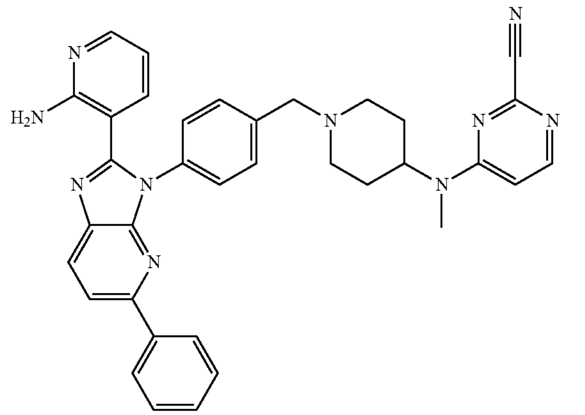 [SMILES: CN(c1ccnc(C#N)n1)C1CCN(Cc2ccc(-n3c(-c4cccnc4N)nc4ccc(-c5ccccc5)nc43)cc2)CC1] | 4-((1-(4-(2-(2-aminopyridin-3-yl)-5-phenyl-3H-imidazo[4,5-b]pyridin-3-yl)benzyl)piperidin-4-yl)(methyl)amino)pyrimidine-2-carbonitrile |
| 157 | 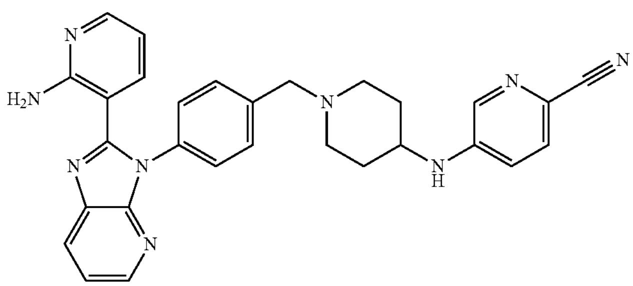 [SMILES: N#Cc1ccc(NC2CCN(Cc3ccc(-n4c(-c5cccnc5N)nc5cccnc54)cc3)CC2)cn1] | 5-((1-(4-(2-(2-aminopyridin-3-yl)-3H-imidazo[4,5-b]pyridin-3-yl)benzyl)piperidin-4-yl)amino)picolinonitrile |
| 158 | 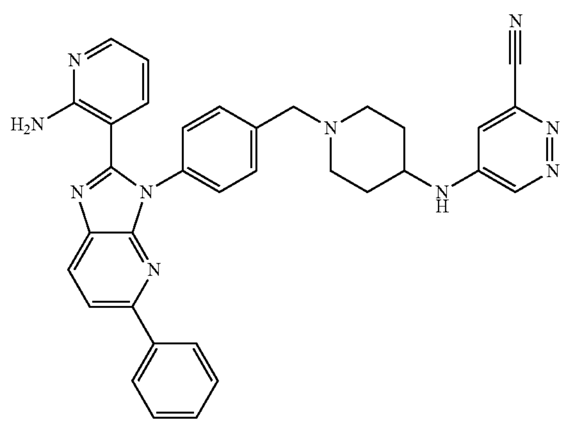 [SMILES: N#Cc1cc(NC2CCN(Cc3ccc(-n4c(-c5cccnc5N)nc5ccc(-c6ccccc6)nc54)cc3)CC2)cnn1] | 5-((1-(4-(2-(2-aminopyridin-3-yl)-5-phenyl-3H-imidazo[4,5-b]pyridin-3-yl)benzyl)piperidin-4-yl)amino)pyridazine-3-carbonitrile |
| 159 | 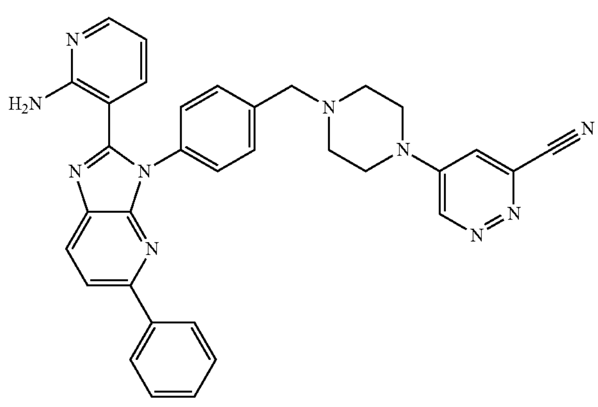 [SMILES: N#Cc1cc(N2CCN(Cc3ccc(-n4c(-c5cccnc5N)nc5ccc(-c6ccccc6)nc54)cc3)CC2)cnn1] | 5-(4-(4-(2-(2-aminopyridin-3-yl)-5-phenyl-3H-imidazo[4,5-b]pyridin-3-yl)benzyl)piperazin-1-yl)pyridazine-3-carbonitrile |

TABLE 1-continued

| Example | Compound Structure | Compound Name |
| --- | --- | --- |
| 160 | 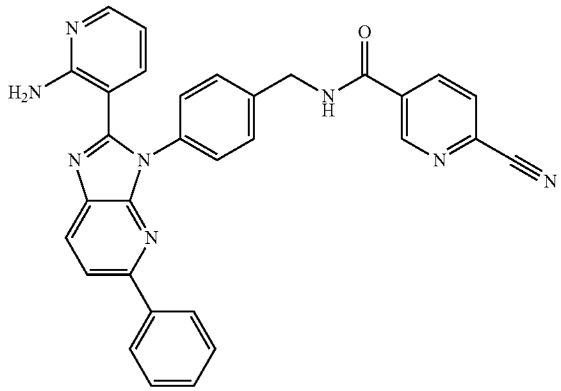 [SMILES: N#Cc1ccc(C(=O)NCc2ccc(-n3c(-c4cccnc4N)nc4ccc(-c5ccccc5)nc43)cc2)cn1] | N-(4-(2-(2-aminopyridin-3-yl)-5-phenyl-3H-imidazo[4,5-b]pyridin-3-yl)benzyl)-6-cyanonicotinamide |
| 161 | 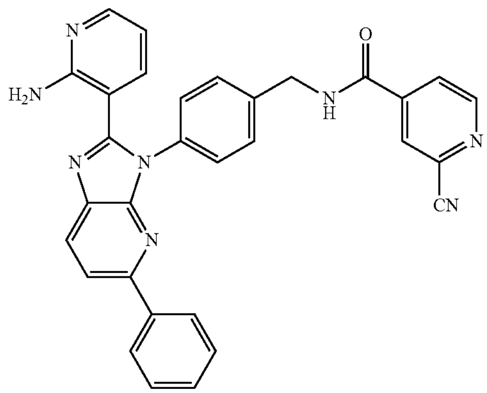 [SMILES: N#Cc1cc(C(=O)NCc2ccc(-n3c(-c4cccnc4N)nc4ccc(-c5ccccc5)nc43)cc2)ccn1] | N-(4-(2-(2-aminopyridin-3-yl)-5-phenyl-3H-imidazo[4,5-b]pyridin-3-yl)benzyl)-2-cyanoisonicotinamide |
| 162 | 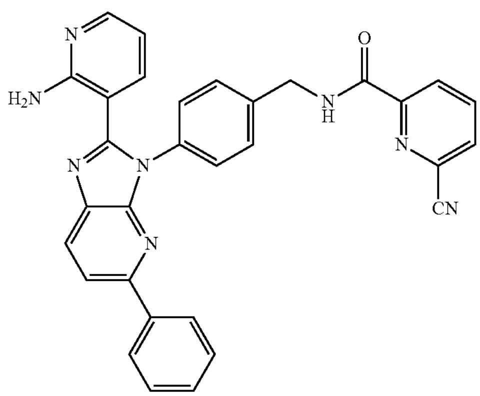 [SMILES: N#Cc1cccc(C(=O)NCc2ccc(-n3c(-c4cccnc4N)nc4ccc(-c5ccccc5)nc43)cc2)n1] | N-(4-(2-(2-aminopyridin-3-yl)-5-phenyl-3H-imidazo[4,5-b]pyridin-3-yl)benzyl)-6-cyanopicolinamide |
| 163 | 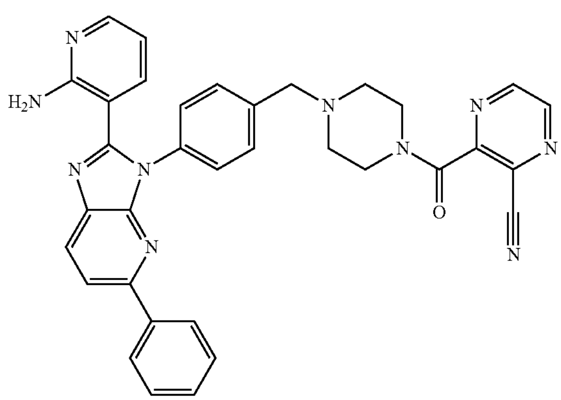 [SMILES: N#Cc1nccnc1C(=O)N1CCN(Cc2ccc(-n3c(-c4cccnc4N)nc4ccc(-c5ccccc5)nc43)cc2)CC1] | 3-(4-(4-(2-(2-aminopyridin-3-yl)-5-phenyl-3H-imidazo[4,5-b]pyridin-3-yl)benzyl)piperazine-1-carbonyl)pyrazine-2-carbonitrile |

TABLE 1-continued

| Example | Compound Structure | Compound Name |
|---|---|---|
| 164 | 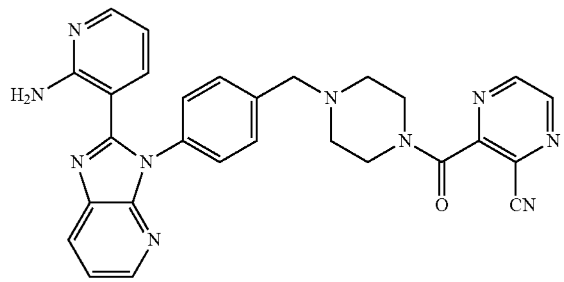 [SMILES: N#Cc1nccnc1C(=O)N1CCN(Cc2ccc(-n3c(-c4cccnc4N)nc4cccnc43)cc2)CC1] | 3-(4-(4-(2-(2-aminopyridin-3-yl)-3H-imidazo[4,5-b]pyridin-3-yl)benzyl)piperazine-1-carbonyl)pyrazine-2-carbonitrile |
| 165 | 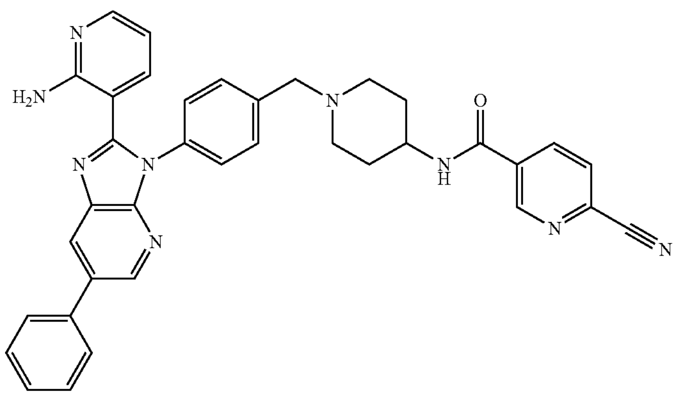 [SMILES: N#Cc1ccc(C(=O)NC2CCN(Cc3ccc(-n4c(-c5cccnc5N)nc5cc(-c6ccccc6)cnc54)cc3)CC2)cn1] | N-(1-(4-(2-(2-aminopyridin-3-yl)-6-phenyl-3H-imidazo[4,5-b]pyridin-3-yl)benzyl)piperidin-4-yl)-6-cyanonicotinamide |
| 166 | 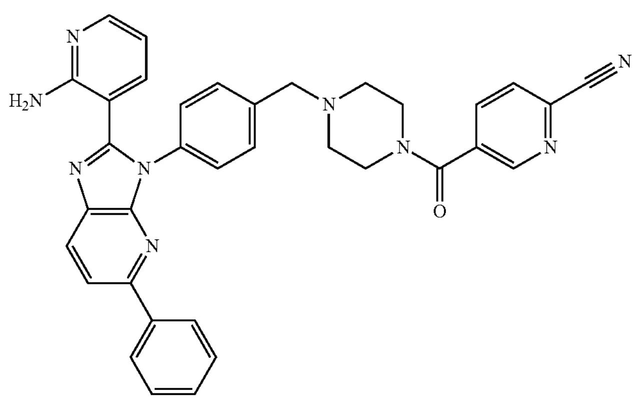 [SMILES: N#Cc1ccc(C(=O)N2CCN(Cc3ccc(-n4c(-c5cccnc5N)nc5ccc(-c6ccccc6)nc54)cc3)CC2)cn1] | 5-(4-(4-(2-(2-aminopyridin-3-yl)-5-phenyl-3H-imidazo[4,5-b]pyridin-3-yl)benzyl)piperazine-1-carbonyl)picolinonitrile |
| 167 | 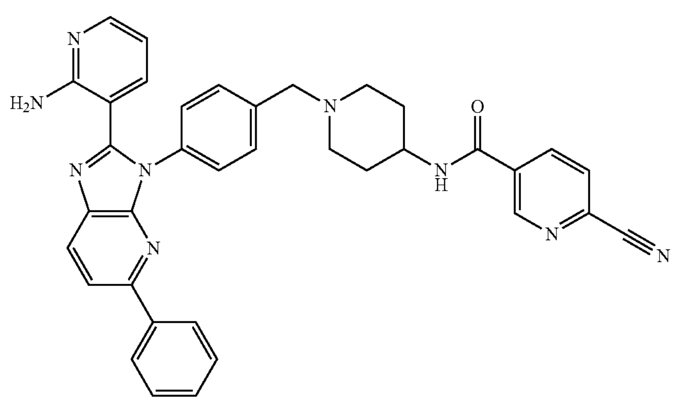 [SMILES: N#Cc1ccc(C(=O)NC2CCN(Cc3ccc(-n4c(-c5cccnc5N)nc5ccc(-c6ccccc6)nc54)cc3)CC2)cn1] | N-(1-(4-(2-(2-aminopyridin-3-yl)-5-phenyl-3H-imidazo[4,5-b]pyridin-3-yl)benzyl)piperidin-4-yl)-6-cyanonicotinamide |

TABLE 1-continued

| Example | Compound Structure | Compound Name |
| --- | --- | --- |
| 168 | 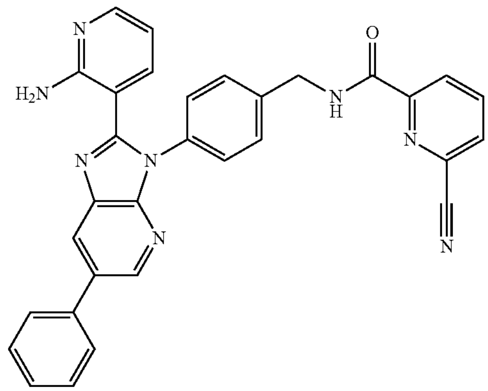 [SMILES: N#Cc1cccc(C(=O)NCc2ccc(-n3c(-c4cccnc4N)nc4cc(-c5ccccc5)cnc43)cc2)n1] | N-(4-(2-(2-aminopyridin-3-yl)-6-phenyl-3H-imidazo[4,5-b]pyridin-3-yl)benzyl)-6-cyanopicolinamide |
| 169 | 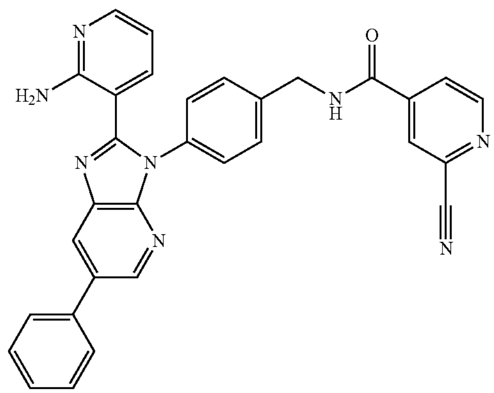 [SMILES: N#Cc1cc(C(=O)NCc2ccc(-n3c(-c4cccnc4N)nc4cc(-c5ccccc5)cnc43)cc2)ccn1] | N-(4-(2-(2-aminopyridin-3-yl)-6-phenyl-3H-imidazo[4,5-b]pyridin-3-yl)benzyl)-2-cyanoisonicotinamide |
| 170 | 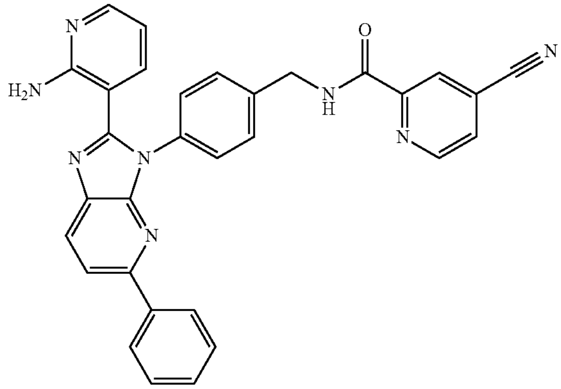 [SMILES: N#Cc1ccnc(C(=O)NCc2ccc(-n3c(-c4cccnc4N)nc4ccc(-c5ccccc5)nc43)cc2)c1] | N-(4-(2-(2-aminopyridin-3-yl)-5-phenyl-3H-imidazo[4,5-b]pyridin-3-yl)benzyl)-4-cyanopicolinamide |
| 171 | 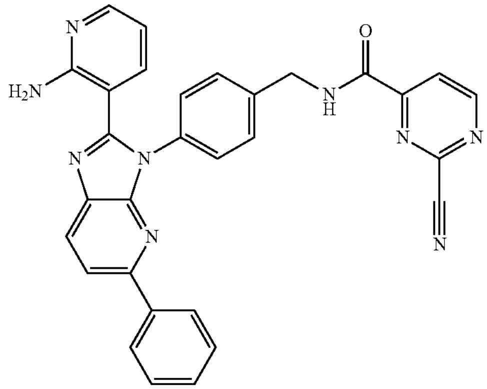 [SMILES: N#Cc1nccc(C(=O)NCc2ccc(-n3c(-c4cccnc4N)nc4ccc(-c5ccccc5)nc43)cc2)n1] | N-(4-(2-(2-aminopyridin-3-yl)-5-phenyl-3H-imidazo[4,5-b]pyridin-3-yl)benzyl)-2-cyanopyrimidine-4-carboxamide |

TABLE 1-continued

| Example | Compound Structure | Compound Name |
|---|---|---|
| 172 | 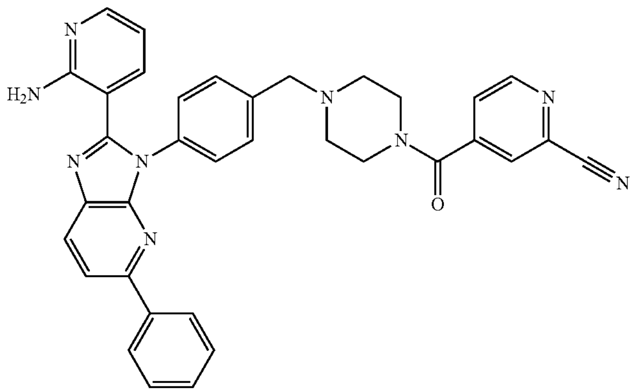 [SMILES: N#Cc1cc(C(=O)N2CCN(Cc3ccc(-n4c(-c5cccnc5N)nc5ccc(-c6ccccc6)nc54)cc3)CC2)ccn1] | 4-(4-(4-(2-(2-aminopyridin-3-yl)-5-phenyl-3H-imidazo[4,5-b]pyridin-3-yl)benzyl)piperazine-1-carbonyl)picolinonitrile |
| 173 | 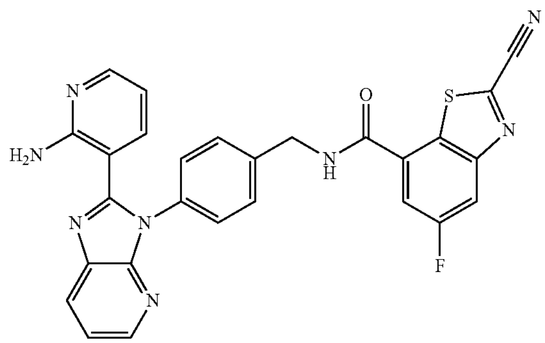 [SMILES: N#Cc1nc2cc(F)cc(C(=O)NCc3ccc(-n4c(-c5cccnc5N)nc5cccnc54)cc3)c2s1] | N-(4-(2-(2-aminopyridin-3-yl)-3H-imidazo[4,5-b]pyridin-3-yl)benzyl)-2-cyano-5-fluorobenzo[d]thiazole-7-carboxamide |
| 174 | 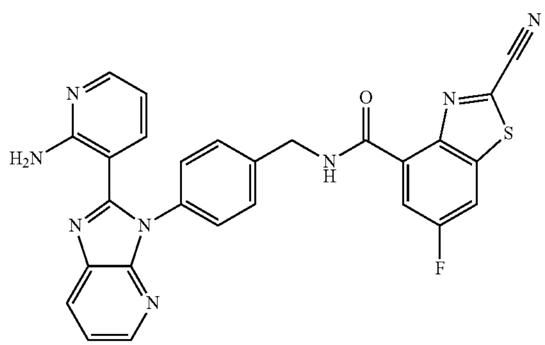 [SMILES: N#Cc1nc2c(C(=O)NCc3ccc(-n4c(-c5cccnc5N)nc5cccnc54)cc3)cc(F)cc2s1] | N-(4-(2-(2-aminopyridin-3-yl)-3H-imidazo[4,5-b]pyridin-3-yl)benzyl)-2-cyano-6-fluorobenzo[d]thiazole-4-carboxamide |
| 175 | 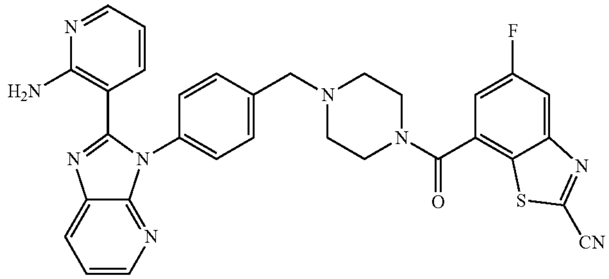 [SMILES: N#Cc1nc2cc(F)cc(C(=O)N3CCN(Cc4ccc(-n5c(-c6cccnc6N)nc6cccnc65)cc4)CC3)c2s1] | 7-(4-(4-(2-(2-aminopyridin-3-yl)-3H-imidazo[4,5-b]pyridin-3-yl)benzyl)piperazine-1-carbonyl)-5-fluorobenzo[d]thiazole-2-carbonitrile |

TABLE 1-continued

| Example | Compound Structure | Compound Name |
| --- | --- | --- |
| 176 | 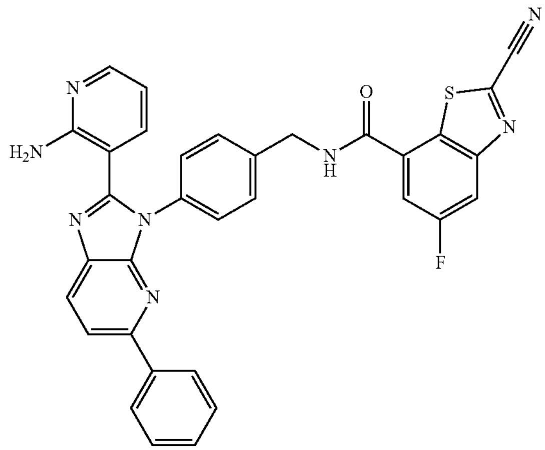 [SMILES: N#Cc1nc2cc(F)cc(C(=O)NCc3ccc(-n4c(-c5cccnc5N)nc5ccc(-c6ccccc6)nc54)cc3)c2s1] | N-(4-(2-(2-aminopyridin-3-yl)-5-phenyl-3H-imidazo[4,5-b]pyridin-3-yl)benzyl)-2-cyano-5-fluorobenzo[d]thiazole-7-carboxamide |
| 177 | 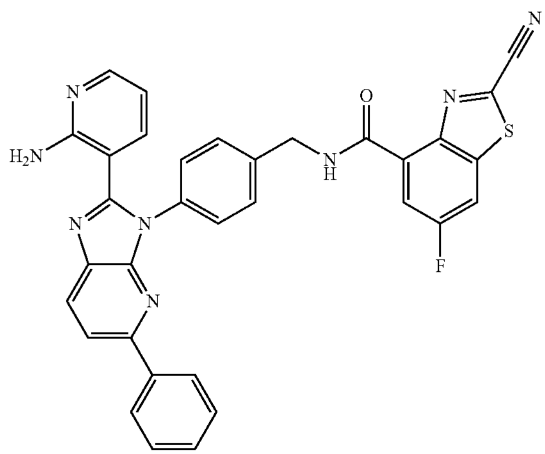 [SMILES: N#Cc1nc2c(C(=O)NCc3ccc(-n4c(-c5cccnc5N)nc5ccc(-c6ccccc6)nc54)cc3)cc(F)cc2s1] | N-(4-(2-(2-aminopyridin-3-yl)-5-phenyl-3H-imidazo[4,5-b]pyridin-3-yl)benzyl)-2-cyano-6-fluorobenzo[d]thiazole-4-carboxamide |
| 178 | 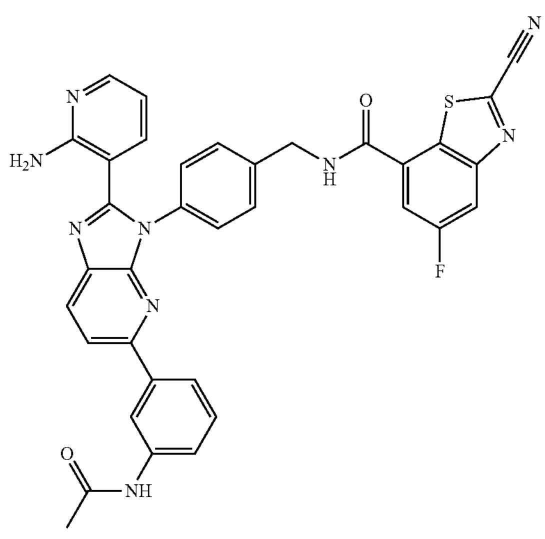 [SMILES: CC(=O)Nc1cccc(-c2ccc3nc(-c4cccnc4N)n(-c4ccc(CNC(=O)c5cc(F)cc6nc(C#N)sc56)cc4)c3n2)c1] | N-(4-(5-(3-acetamidophenyl)-2-(2-aminopyridin-3-yl)-3H-imidazo[4,5-b]pyridin-3-yl)benzyl)-2-cyano-5-fluorobenzo[d]thiazole-7-carboxamide |

TABLE 1-continued

| Example | Compound Structure | Compound Name |
|---|---|---|
| 179 | 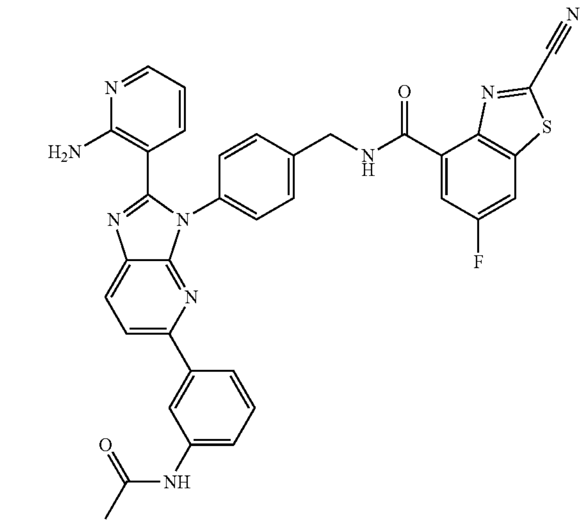 [SMILES: CC(=O)Nc1cccc(-c2ccc3nc(-c4cccnc4N)n(-c4ccc(CNC(=O)c5cc(F)cc6sc(C#N)nc56)cc4)c3n2)c1] | N-(4-(5-(3-acetamidophenyl)-2-(2-aminopyridin-3-yl)-3H-imidazo[4,5-b]pyridin-3-yl)benzyl)-2-cyano-6-fluorobenzo[d]thiazole-4-carboxamide |
| 180 | 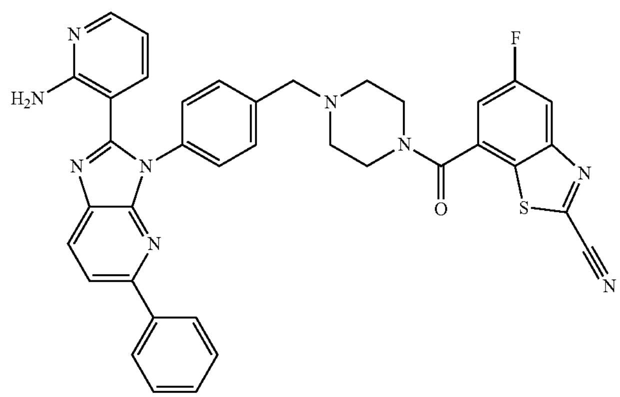 [SMILES: N#Cc1nc2cc(F)cc(C(=O)N3CCN(Cc4ccc(-n5c(-c6cccnc6N)nc6ccc(-c7ccccc7)nc65)cc4)CC3)c2s1] | 7-(4-(4-(2-(2-aminopyridin-3-yl)-5-phenyl-3H-imidazo[4,5-b]pyridin-3-yl)benzyl)piperazine-1-carbonyl)-5-fluorobenzo[d]thiazole-2-carbonitrile |
| 181 | 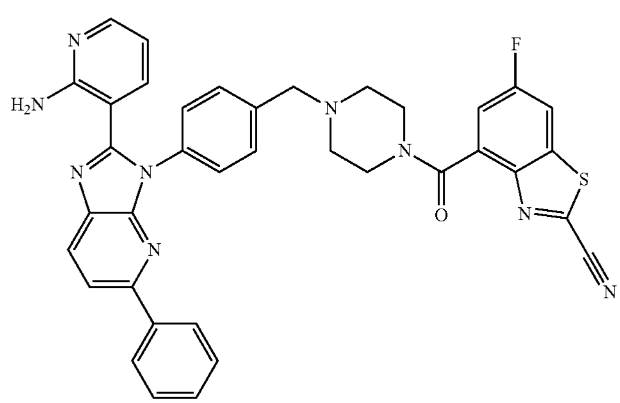 [SMILES: N#Cc1nc2c(C(=O)N3CCN(Cc4ccc(-n5c(-c6cccnc6N)nc6ccc(-c7ccccc7)nc65)cc4)CC3)cc(F)cc2s1] | 4-(4-(4-(2-(2-aminopyridin-3-yl)-5-phenyl-3H-imidazo[4,5-b]pyridin-3-yl)benzyl)piperazine-1-carbonyl)-6-fluorobenzo[d]thiazole-2-carbonitrile |

TABLE 1-continued

| Example | Compound Structure | Compound Name |
|---|---|---|
| 182 | 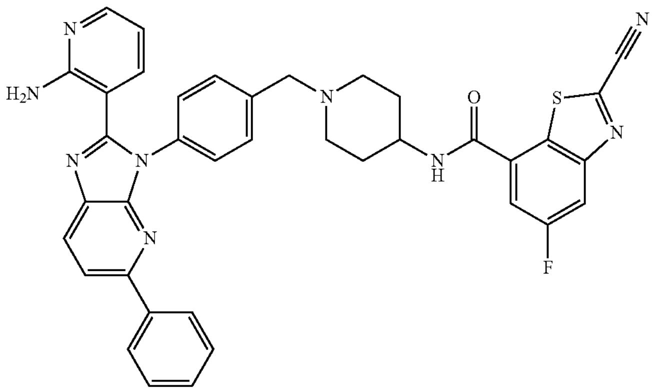 [SMILES: N#Cc1nc2cc(F)cc(C(=O)NC3CCN(Cc4ccc(-n5c(-c6cccnc6N)nc6ccc(-c7ccccc7)nc65)cc4)CC3)c2s1] | N-(1-(4-(2-(2-aminopyridin-3-yl)-5-phenyl-3H-imidazo[4,5-b]pyridin-3-yl)benzyl)piperidin-4-yl)-2-cyano-5-fluorobenzo[d]thiazole-7-carboxamide |
| 183 | 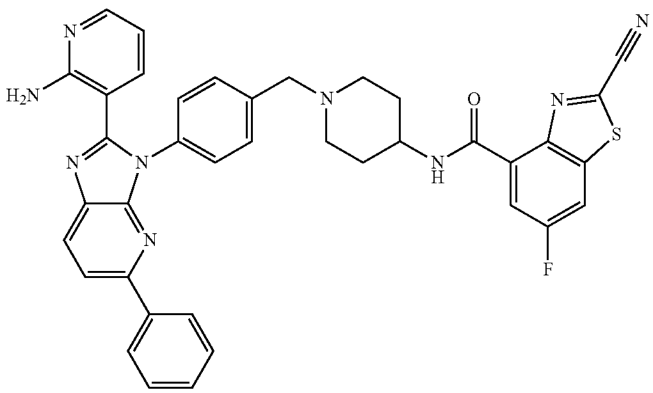 [SMILES: N#Cc1nc2c(C(=O)NC3CCN(Cc4ccc(-n5c(-c6cccnc6N)nc6ccc(-c7ccccc7)nc65)cc4)CC3)cc(F)cc2s1] | N-(1-(4-(2-(2-aminopyridin-3-yl)-5-phenyl-3H-imidazo[4,5-b]pyridin-3-yl)benzyl)piperidin-4-yl)-2-cyano-6-fluorobenzo[d]thiazole-4-carboxamide |
| 184 | 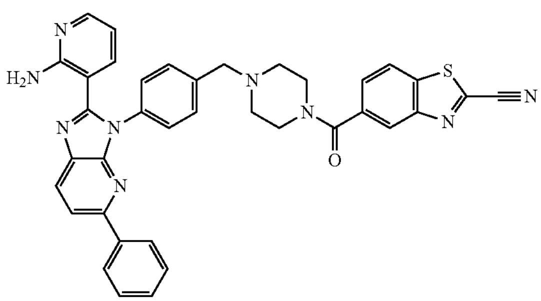 [SMILES: N#Cc1nc2cc(C(=O)N3CCN(Cc4ccc(-n5c(-c6cccnc6N)nc6ccc(-c7ccccc7)nc65)cc4)CC3)ccc2s1] | 5-(4-(4-(2-(2-aminopyridin-3-yl)-5-phenyl-3H-imidazo[4,5-b]pyridin-3-yl)benzyl)piperazine-1-carbonyl)benzo[d]thiazole-2-carbonitrile |
| 185 | 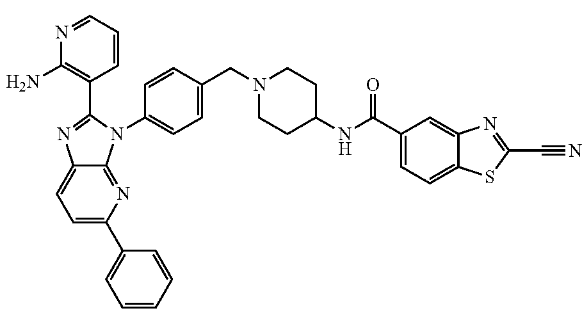 [SMILES: N#Cc1nc2cc(C(=O)NC3CCN(Cc4ccc(-n5c(-c6cccnc6N)nc6ccc(-c7ccccc7)nc65)cc4)CC3)ccc2s1] | N-(1-(4-(2-(2-aminopyridin-3-yl)-5-phenyl-3H-imidazo[4,5-b]pyridin-3-yl)benzyl)piperidin-4-yl)-2-cyanobenzo[d]thiazole-5-carboxamide |

TABLE 1-continued

| Example | Compound Structure | Compound Name |
|---|---|---|
| 186 | 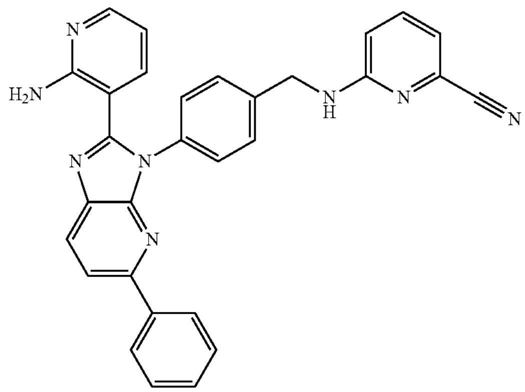 [SMILES: N#Cc1cccc(NCc2ccc(-n3c(-c4cccnc4N)nc4ccc(-c5ccccc5)nc43)cc2)n1] | 6-((4-(2-(2-aminopyridin-3-yl)-5-phenyl-3H-imidazo[4,5-b]pyridin-3-yl)benzyl)amino)picolinonitrile |
| 187 | 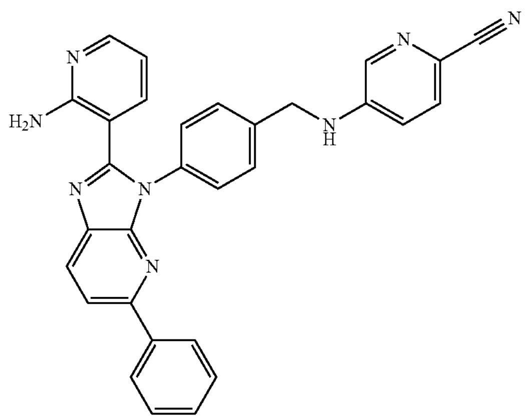 [SMILES: N#Cc1ccc(NCc2ccc(-n3c(-c4cccnc4N)nc4ccc(-c5ccccc5)nc43)cc2)cn1] | 5-((4-(2-(2-aminopyridin-3-yl)-5-phenyl-3H-imidazo[4,5-b]pyridin-3-yl)benzyl)amino)picolinonitrile |
| 188 | 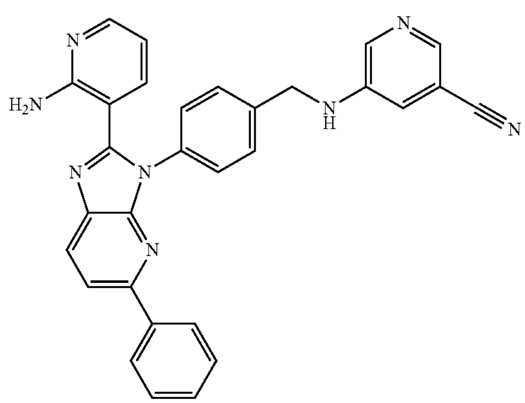 [SMILES: N#Cc1cncc(NCc2ccc(-n3c(-c4cccnc4N)nc4ccc(-c5ccccc5)nc43)cc2)c1] | 5-((4-(2-(2-aminopyridin-3-yl)-5-phenyl-3H-imidazo[4,5-b]pyridin-3-yl)benzyl)amino)nicotinonitrile |
| 189 | 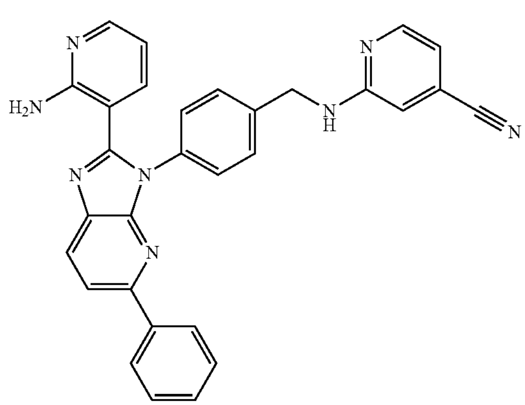 [SMILES: N#Cc1ccnc(NCc2ccc(-n3c(-c4cccnc4N)nc4ccc(-c5ccccc5)nc43)cc2)c1] | 2-((4-(2-(2-aminopyridin-3-yl)-5-phenyl-3H-imidazo[4,5-b]pyridin-3-yl)benzyl)amino)isonicotinonitrile |

TABLE 1-continued

| Example | Compound Structure | Compound Name |
|---|---|---|
| 190 | 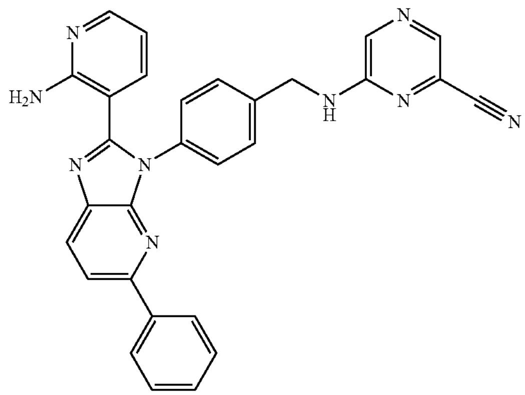 [SMILES: N#Cc1cncc(NCc2ccc(-n3c(-c4cccnc4N)nc4ccc(-c5ccccc5)nc43)cc2)n1] | 6-((4-(2-(2-aminopyridin-3-yl)-5-phenyl-3H-imidazo[4,5-b]pyridin-3-yl)benzyl)amino)pyrazine-2-carbonitrile |
| 191 | 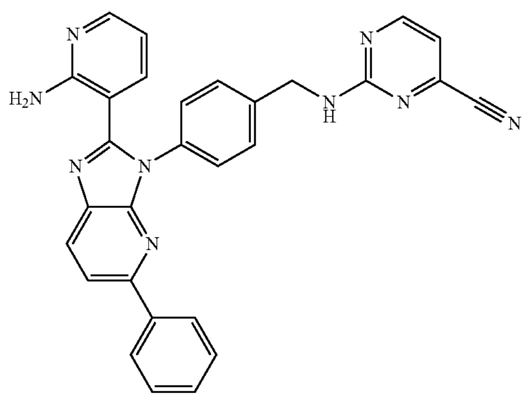 [SMILES: N#Cc1ccnc(NCc2ccc(-n3c(-c4cccnc4N)nc4ccc(-c5ccccc5)nc43)cc2)n1] | 2-((4-(2-(2-aminopyridin-3-yl)-5-phenyl-3H-imidazo[4,5-b]pyridin-3-yl)benzyl)amino)pyrimidine-4-carbonitrile |
| 192 | 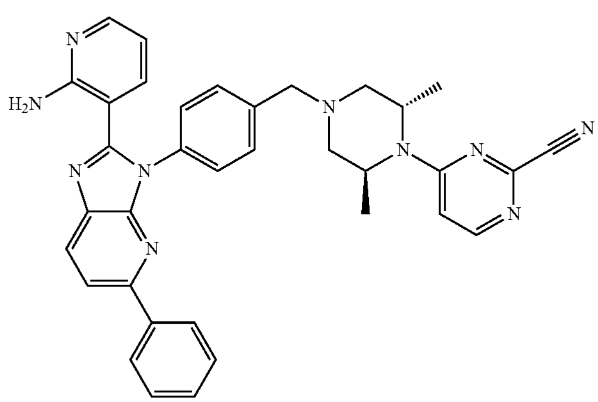 [SMILES: C[C@H]1CN(Cc2ccc(-n3c(-c4cccnc4N)nc4ccc(-c5ccccc5)nc43)cc2)C[C@H](C)N1c1ccnc(C#N)n1] | 4-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile |
| 193 | 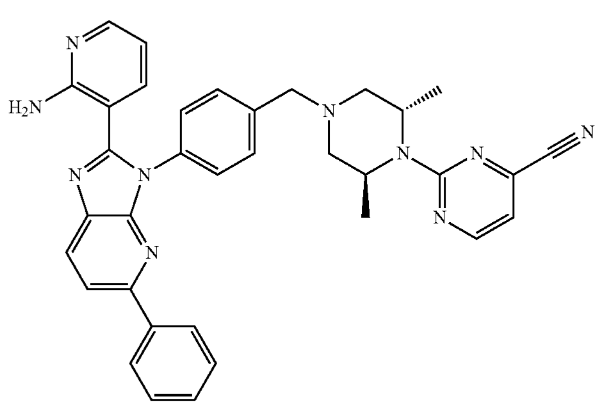 [SMILES: C[C@H]1CN(Cc2ccc(-n3c(-c4cccnc4N)nc4ccc(-c5ccccc5)nc43)cc2)C[C@H](C)N1c1nccc(C#N)n1] | 2-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile |

TABLE 1-continued

| Example | Compound Structure | Compound Name |
|---|---|---|
| 194 | 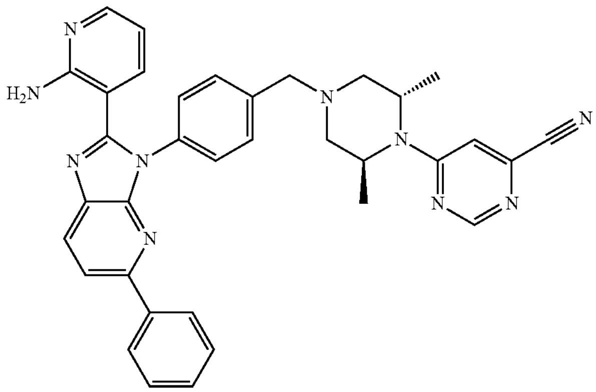 [SMILES: C[C@H]1CN(Cc2ccc(-n3c(-c4cccnc4N)nc4ccc(-c5ccccc5)nc43)cc2)C[C@H](C)N1c1cc(C#N)ncn1] | 6-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile |
| 195 | 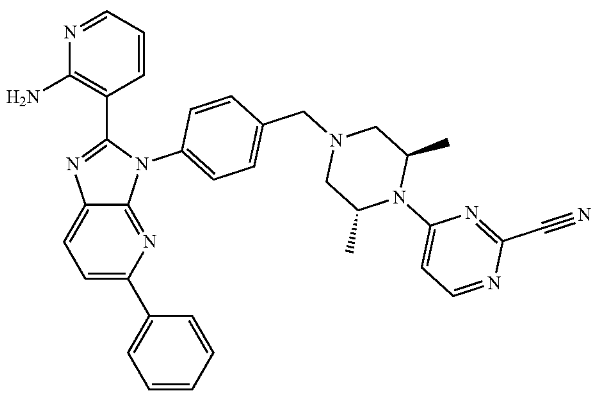 [SMILES: C[C@@H]1CN(Cc2ccc(-n3c(-c4cccnc4N)nc4ccc(-c5ccccc5)nc43)cc2)C[C@@H](C)N1c1ccnc(C#N)n1] | 4-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile |
| 196 | 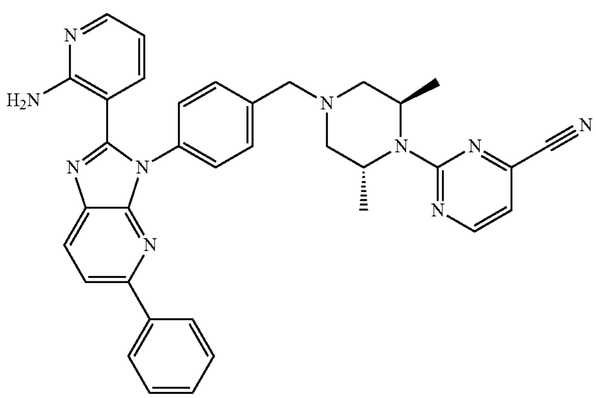 [SMILES: C[C@@H]1CN(Cc2ccc(-n3c(-c4cccnc4N)nc4ccc(-c5ccccc5)nc43)cc2)C[C@@H](C)N1c1nccc(C#N)n1] | 2-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile |
| 197 | 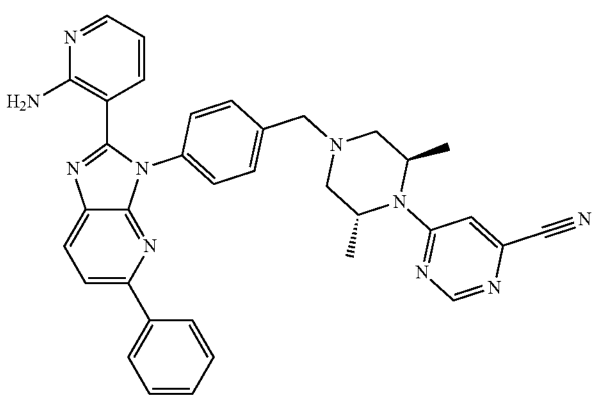 [SMILES: C[C@@H]1CN(Cc2ccc(-n3c(-c4cccnc4N)nc4ccc(-c5ccccc5)nc43)cc2)C[C@@H](C)N1c1cc(C#N)ncn1] | 6-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile |

TABLE 1-continued
| Example | Compound Structure | Compound Name |
|---|---|---|
| 198 | 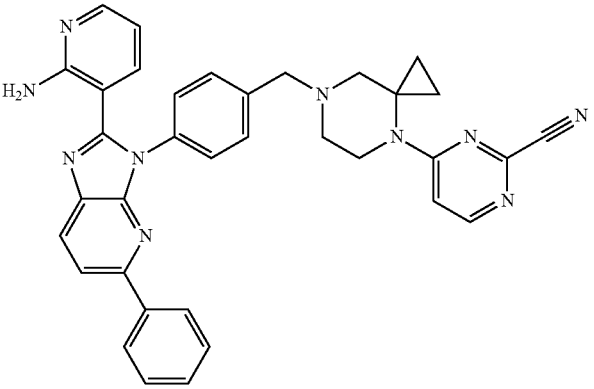 [SMILES: N#Cc1nccc(N2CCN(Cc3ccc(-n4c(-c5cccnc5N)nc5ccc(-c6ccccc6)nc54)cc3)CC23CC3)n1] | 4-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-2-carbonitrile |
| 199 | 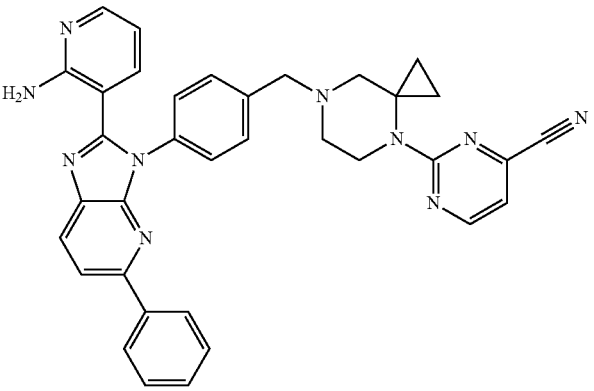 [SMILES: N#Cc1ccnc(N2CCN(Cc3ccc(-n4c(-c5cccnc5N)nc5ccc(-c6ccccc6)nc54)cc3)CC23CC3)n1] | 2-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-4-carbonitrile |
| 200 | 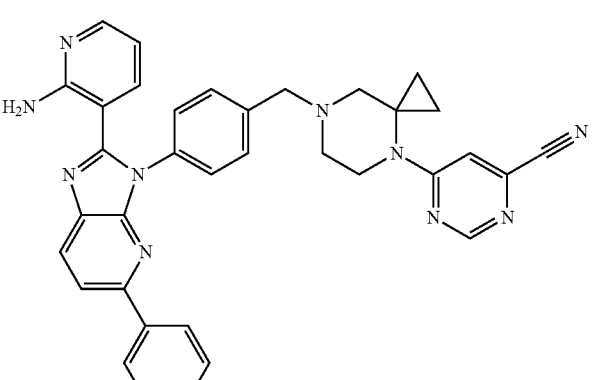 | 6-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-4-carbonitrile |

TABLE 1-continued

| Example | Compound Structure | Compound Name |
|---|---|---|
| 201 | 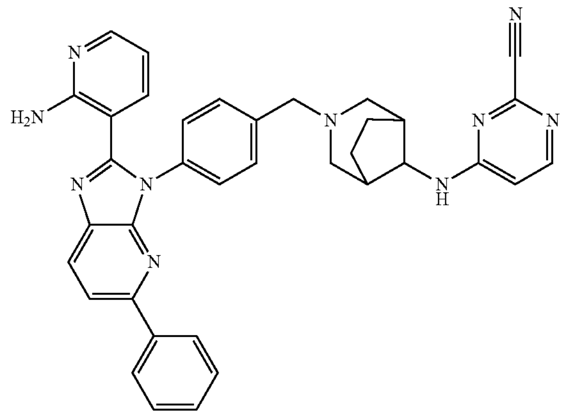 [SMILES: N#Cc1nccc(NC2C3CCC2CN(Cc2ccc(-n4c(-c5cccnc5N)nc5ccc(-c6ccccc6)nc54)cc2)C3)n1] | 4-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-2-carbonitrile |
| 202 | 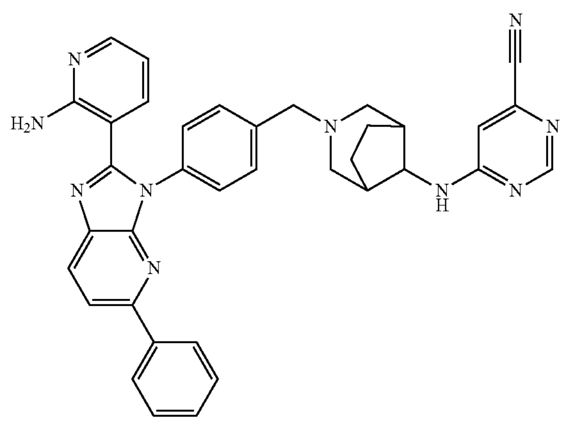 [SMILES: N#Cc1cc(NC2C3CCC2CN(Cc2ccc(-n4c(-c5cccnc5N)nc5ccc(-c6ccccc6)nc54)cc2)C3)ncn1] | 6-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-4-carbonitrile |
| 203 | 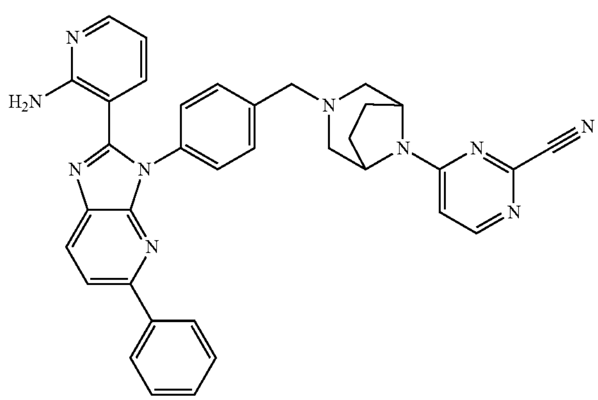 [SMILES: N#Cc1nccc(N2C3CCC2CN(Cc2ccc(-n4c(-c5cccnc5N)nc5ccc(-c6ccccc6)nc54)cc2)C3)n1] | 4-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-2-carbonitrile |

TABLE 1-continued

| Example | Compound Structure | Compound Name |
|---|---|---|
| 204 | 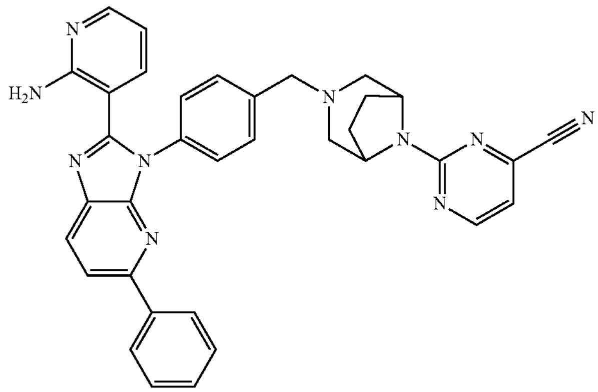 [SMILES: N#Cc1ccnc(N2C3CCC2CN(Cc2ccc(-n4c(-c5cccnc5N)nc5ccc(-c6ccccc6)nc54)cc2)C3)n1] | 2-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-4-carbonitrile |
| 205 | 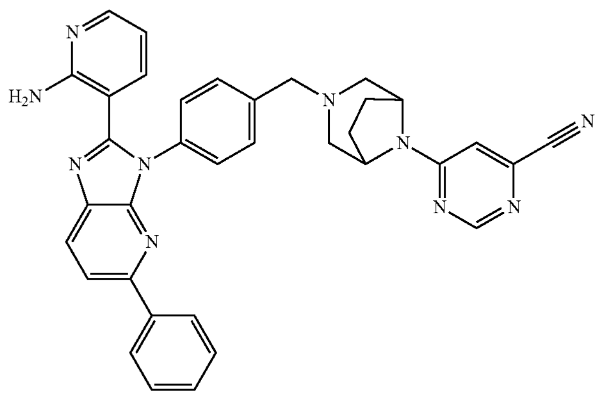 [SMILES: N#Cc1cc(N2C3CCC2CN(Cc2ccc(-n4c(-c5cccnc5N)nc5ccc(-c6ccccc6)nc54)cc2)C3)ncn1] | 6-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-4-carbonitrile |
| 206 | 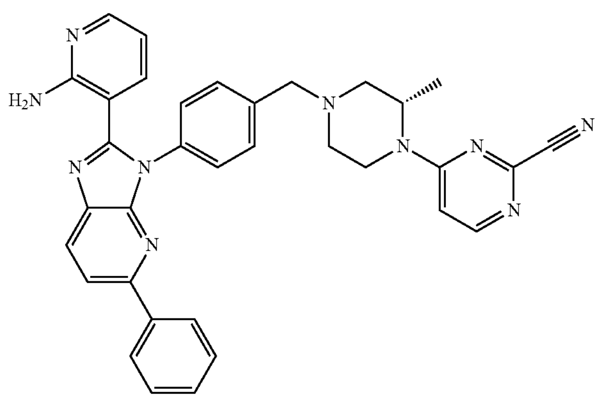 [SMILES: C[C@H]1CN(Cc2ccc(-n3c(-c4cccnc4N)nc4ccc(-c5ccccc5)nc43)cc2)CCN1c1ccnc(C#N)n1] | (S)-4-(4-(4-(2-(2-aminopyridin-3-yl)-5-phenyl-3H-imidazo[4,5-b]pyridin-3-yl)benzyl)-2-methylpiperazin-1-yl)pyrimidine-2-carbonitrile |
| 207 | 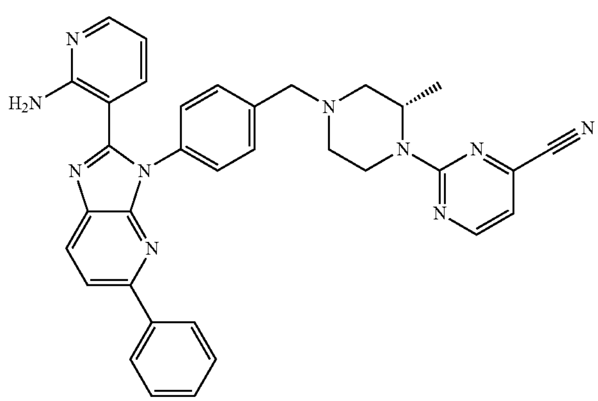 [SMILES: C[C@H]1CN(Cc2ccc(-n3c(-c4cccnc4N)nc4ccc(-c5ccccc5)nc43)cc2)CCN1c1nccc(C#N)n1] | (S)-2-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile |

TABLE 1-continued

| Example | Compound Structure | Compound Name |
|---|---|---|
| 208 | 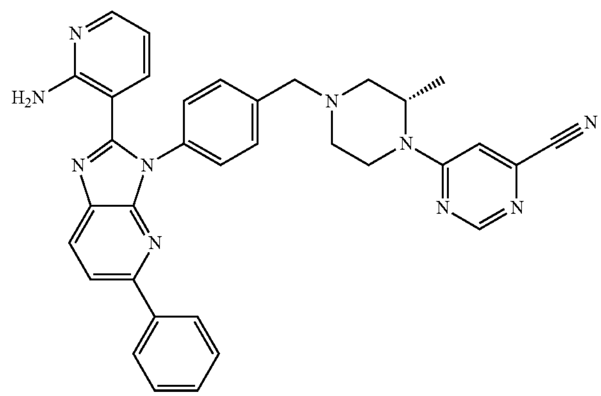 [SMILES: C[C@H]1CN(Cc2ccc(-n3c(-c4cccnc4N)nc4ccc(-c5ccccc5)nc43)cc2)CCN1c1cc(C#N)ncn1] | (S)-6-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile |
| 209 | 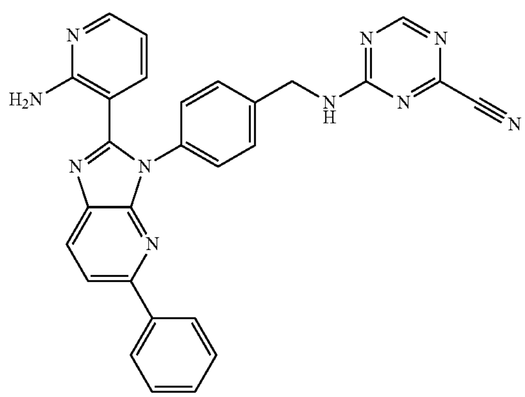 | 4-((4-(2-(2-aminopyridin-3-yl)-5-phenyl-3H-imidazo[4,5-b]pyridin-3-yl)benzyl)amino)-1,3,5-triazine-2-carbonitrile |
| 210 | 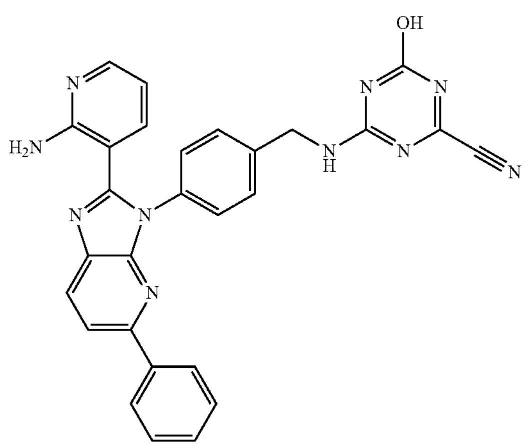 [SMILES: N#Cc1nc(O)nc(NCc2ccc(-n3c(-c4cccnc4N)nc4ccc(-c5ccccc5)nc43)cc2)n1] | 4-((4-(2-(2-aminopyridin-3-yl)-5-phenyl-3H-imidazo[4,5-b]pyridin-3-yl)benzyl)amino)-6-hydroxy-1,3,5-triazine-2-carbonitrile |

TABLE 1-continued

| Example | Compound Structure | Compound Name |
|---|---|---|
| 211 | 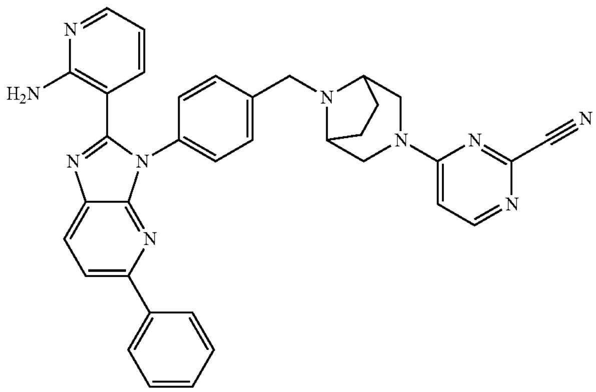 [SMILES: N#Cc1nccc(N2CC3CCC(C2)N3Cc2ccc(-n3c(-c4cccnc4N)nc4ccc(-c5ccccc5)nc43)cc2)n1] | 4-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-2-carbonitrile |
| 212 | 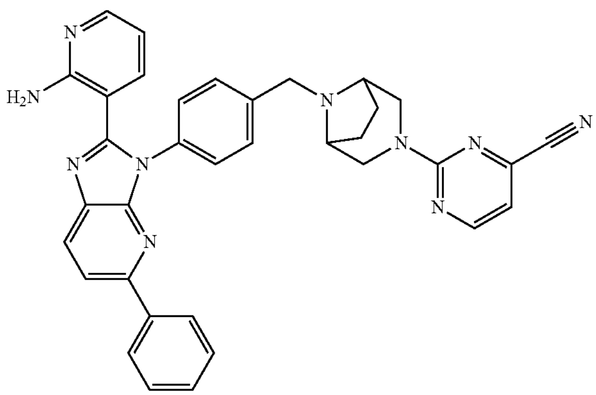 [SMILES: N#Cc1ccnc(N2CC3CCC(C2)N3Cc2ccc(-n3c(-c4cccnc4N)nc4ccc(-c5ccccc5)nc43)cc2)n1] | 2-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-4-carbonitrile |
| 213 | 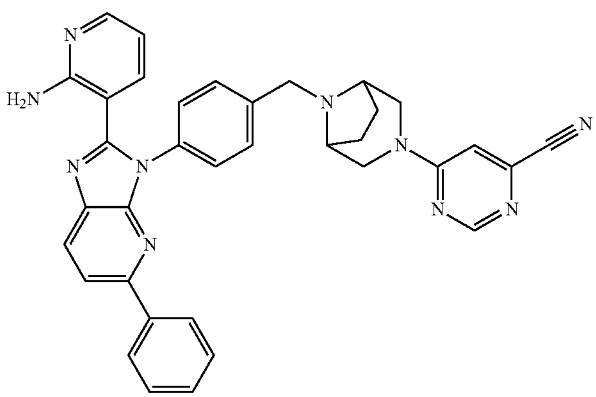 [SMILES: N#Cc1cc(N2CC3CCC(C2)N3Cc2ccc(-n3c(-c4cccnc4N)nc4ccc(-c5ccccc5)nc43)cc2)ncn1] | 6-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-4-carbonitrile |
| 214 | 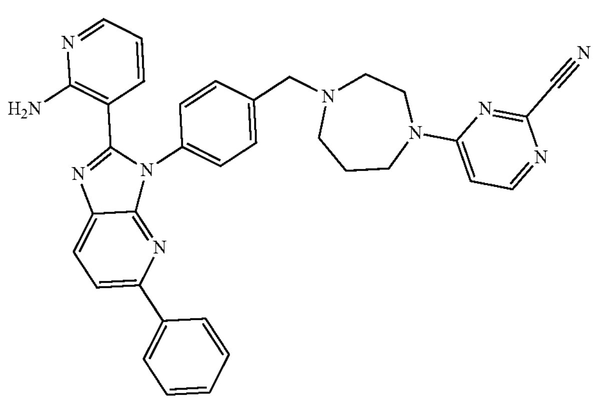 [SMILES: N#Cc1nccc(N2CCCN(Cc3ccc(-n4c(-c5cccnc5N)nc5ccc(-c6ccccc6)nc54)cc3)CC2)n1] | 4-(4-(4-(2-(2-aminopyridin-3-yl)-5-phenyl-3H-imidazo[4,5-b]pyridin-3-yl)benzyl)-1,4-diazepan-1-yl)pyrimidine-2-carbonitrile |

TABLE 1-continued

| Example | Compound Structure | Compound Name |
|---|---|---|
| 215 | 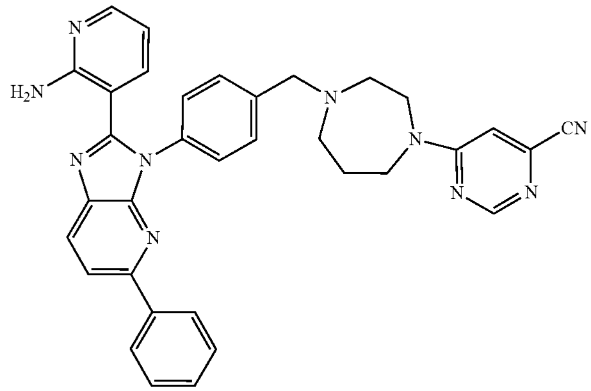 [SMILES: N#Cc1cc(N2CCCN(Cc3ccc(-n4c(-c5cccnc5N)nc5ccc(-c6ccccc6)nc54)cc3)CC2)ncn1] | 6-(4-(4-(2-(2-aminopyridin-3-yl)-5-phenyl-3H-imidazo[4,5-b]pyridin-3-yl)benzyl)-1,4-diazepan-1-yl)pyrimidine-4-carbonitrile |
| 216 | 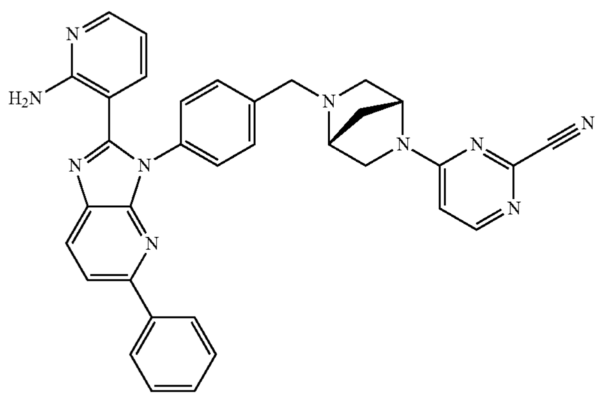 | 4-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-2-carbonitrile |
| 217 | 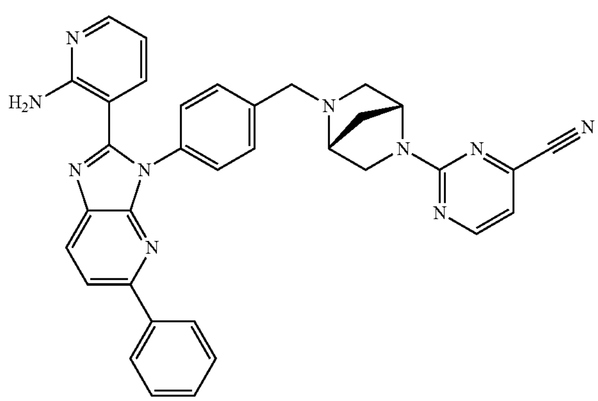 [SMILES: N#Cc1ccnc(N2C[C@H]3C[C@@H]2CN3Cc2ccc(-n3c(-c4cccnc4N)nc4ccc(-c5ccccc5)nc43)cc2)n1] | 2-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile |
| 218 | 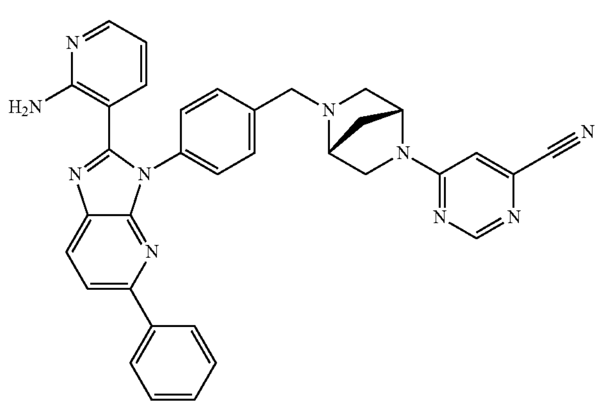 [SMILES: N#Cc1cc(N2C[C@H]3C[C@@H]2CN3Cc2ccc(-n3c(-c4cccnc4N)nc4ccc(-c5ccccc5)nc43)cc2)ncn1] | 6-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile |

TABLE 1-continued

| Example | Compound Structure | Compound Name |
|---|---|---|
| 219 | 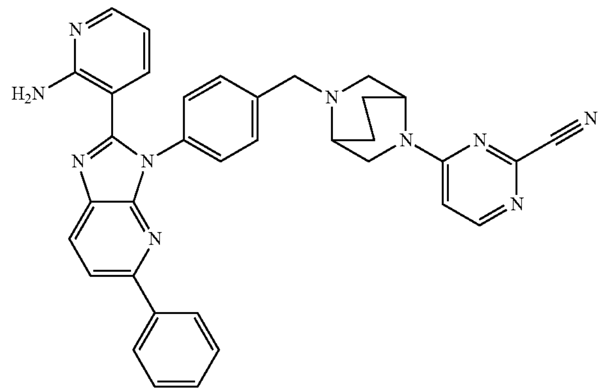 | 4-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-2-carbonitrile |
| 220 | 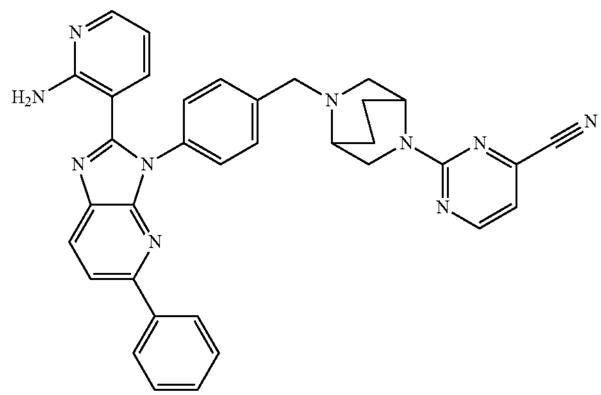 [SMILES: N#Cc1ccnc(N2CC3CCC2CN3Cc2ccc(-n3c(-c4cccnc4N)nc4ccc(-c5ccccc5)nc43)cc2)n1] | 2-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-4-carbonitrile |
| 221 | 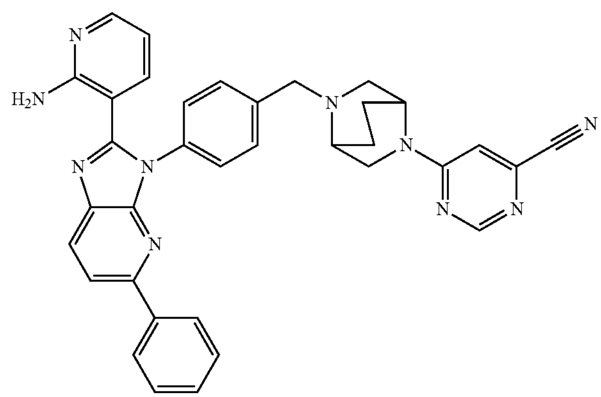 [SMILES: N#Cc1cc(N2CC3CCC2CN3Cc2ccc(-n3c(-c4cccnc4N)nc4ccc(-c5ccccc5)nc43)cc2)ncn1] | 6-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-4-carbonitrile |
| 222 | 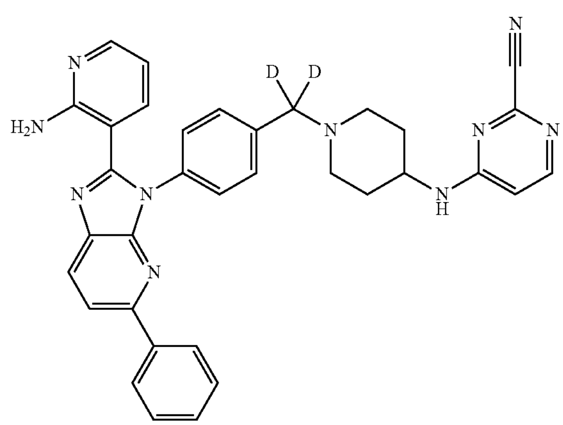 [SMILES: [2H]C([2H])(c1ccc(-n2c(-c3cccnc3N)nc3ccc(-c4ccccc4)nc32)cc1)N1CCC(Nc2ccnc(C#N)n2)CC1] | 4-((1-((4-(2-(2-aminopyridin-3-yl)-5-phenyl-3H-imidazo[4,5-b]pyridin-3-yl)phenyl)methyl-d2)piperidin-4-yl)amino)pyrimidine-2-carbonitrile |

TABLE 1-continued

| Example | Compound Structure | Compound Name |
|---|---|---|
| 223 | 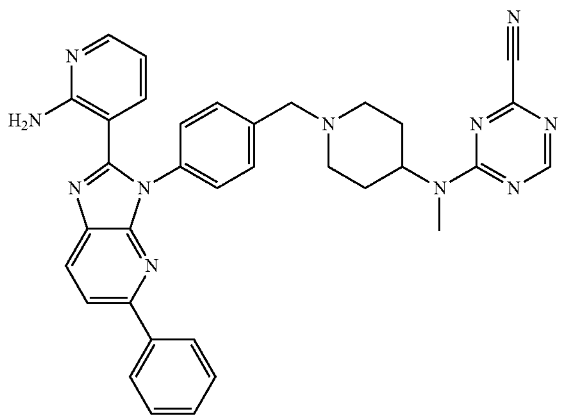 [SMILES: CN(c1ncnc(C#N)n1)C1CCN(Cc2ccc(-n3c(-c4cccnc4N)nc4ccc(-c5ccccc5)nc43)cc2)CC1] | 4-((1-(4-(2-(2-aminopyridin-3-yl)-5-phenyl-3H-imidazo[4,5-b]pyridin-3-yl)benzyl)piperidin-4-yl)(methyl)amino)-1,3,5-triazine-2-carbonitrile |
| 224 | 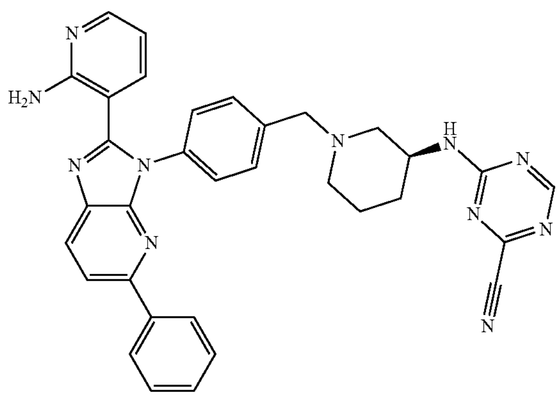 [SMILES: N#Cc1ncnc(N[C@H]2CCCN(Cc3ccc(-n4c(-c5cccnc5N)nc5ccc(-c6ccccc6)nc54)cc3)C2)n1] | (S)-4-((1-(4-(2-(2-aminopyridin-3-yl)-5-phenyl-3H-imidazo[4,5-b]pyridin-3-yl)benzyl)piperidin-3-yl)amino)-1,3,5-triazine-2-carbonitrile |
| 225 | 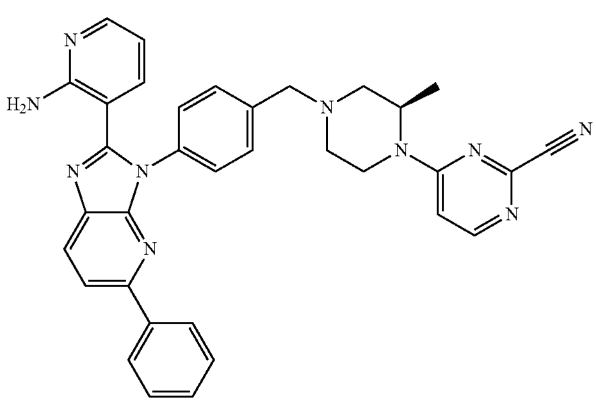 [SMILES: C[C@@H]1CN(Cc2ccc(-n3c(-c4cccnc4N)nc4ccc(-c5ccccc5)nc43)cc2)CCN1c1ccnc(C#N)n1] | (R)-4-(4-(4-(2-(2-aminopyridin-3-yl)-5-phenyl-3H-imidazo[4,5-b]pyridin-3-yl)benzyl)-2-methylpiperazin-1-yl)pyrimidine-2-carbonitrile |

TABLE 1-continued

| Example | Compound Structure | Compound Name |
|---|---|---|
| 226 | 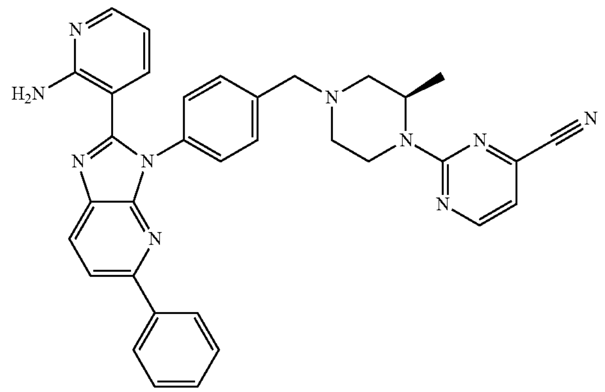 | (R)-2-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile |
| 227 | 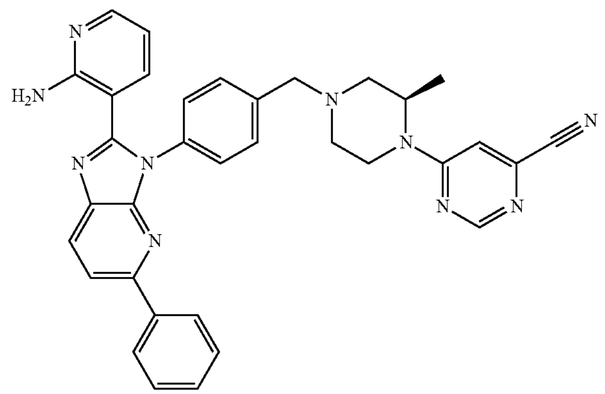 | (R)-6-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile |
| 228 | 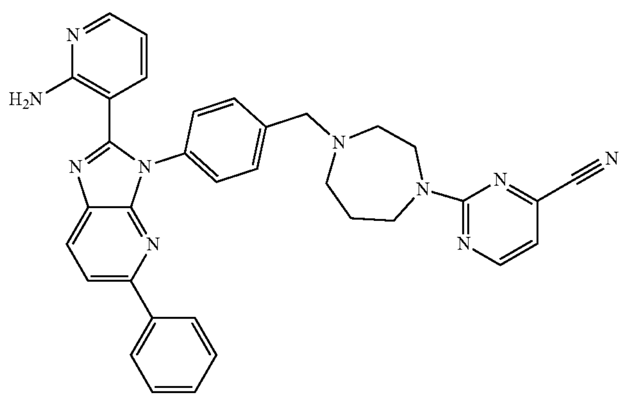 [SMILES: N#Cc1ccnc(N2CCCN(Cc3ccc(-n4c(-c5cccnc5N)nc5ccc(-c6ccccc6)nc54)cc3)CC2)n1] | 2-(4-(4-(2-(2-aminopyridin-3-yl)-5-phenyl-3H-imidazo[4,5-b]pyridin-3-yl)benzyl)-1,4-diazepan-1-yl)pyrimidine-4-carbonitrile |
| 229 | 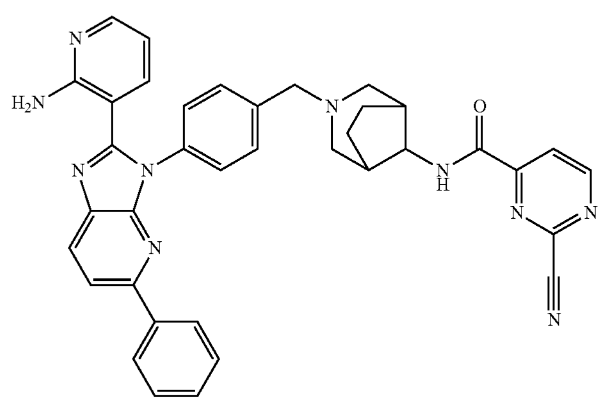 [SMILES: N#Cc1nccc(C(=O)NC2C3CCC2CN(Cc2ccc(-n4c(-c5cccnc5N)nc5ccc(-c6ccccc6)nc54)cc2)C3)n1] | N-(3-(4-(2-(2-aminopyridin-3-yl)-5-phenyl-3H-imidazo[4,5-b]pyridin-3-yl)benzyl)-3-azabicyclo[3.2.1]octan-8-yl)-2-cyanopyrimidine-4-carboxamide |

TABLE 1-continued

| Example | Compound Structure | Compound Name |
|---|---|---|
| 230 | 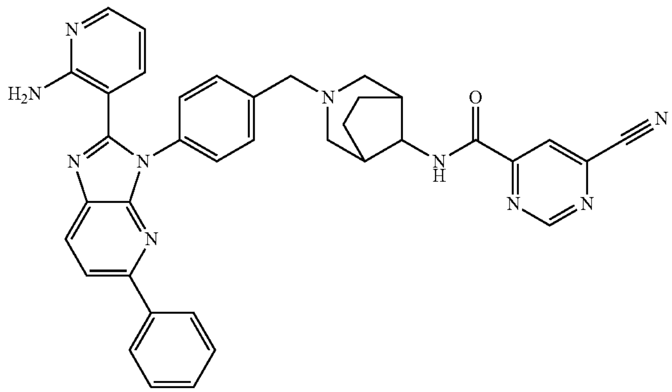 [SMILES: N#Cc1cc(C(=O)NC2C3CCC2CN(Cc2ccc(-n4c(-c5cccnc5N)nc5ccc(-c6ccccc6)nc54)cc2)C3)ncn1] | N-(3-(4-(2-(2-aminopyridin-3-yl)-5-phenyl-3H-imidazo[4,5-b]pyridin-3-yl)benzyl)-3-azabicyclo[3.2.1]octan-8-yl)-6-cyanopyrimidine-4-carboxamide |
| 231 | 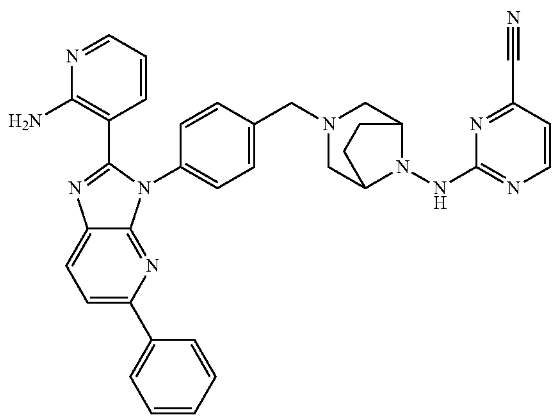 [SMILES: N#Cc1ccnc(NN2C3CCC2CN(Cc2ccc(-n4c(-c5cccnc5N)nc5ccc(-c6ccccc6)nc54)cc2)C3)n1] | 2-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-4-carbonitrile |
| 232 | 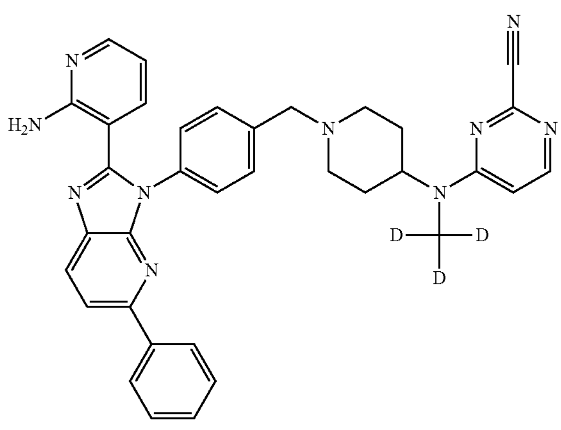 [SMILES: [2H]C([2H])([2H])N(c1ccnc(C#N)n1)C1CCN(Cc2ccc(-n3c(-c4cccnc4N)nc4ccc(-c5ccccc5)nc43)cc2)CC1] | 4-((1-(4-(2-(2-aminopyridin-3-yl)-5-phenyl-3H-imidazo[4,5-b]pyridin-3-yl)benzyl)piperidin-4-yl)(methyl-d3)amino)pyrimidine-2-carbonitrile |

TABLE 1-continued

| Example | Compound Structure | Compound Name |
|---|---|---|
| 233 | 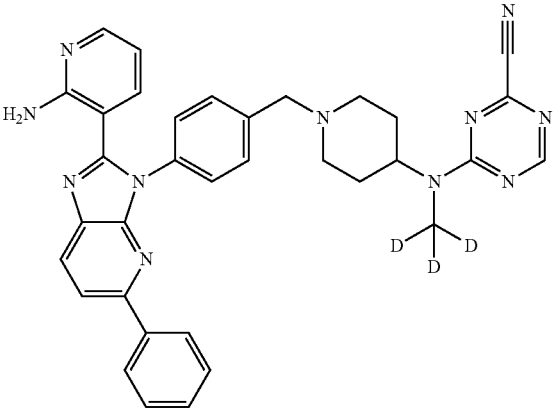 [SMILES: [2H]C([2H])([2H])N(c1ncnc(C#N)n1)C1CCN(Cc2ccc(-n3c(-c4cccnc4N)nc4ccc(-c5ccccc5)nc43)cc2)CC1] | 4-((1-(4-(2-(2-aminopyridin-3-yl)-5-phenyl-3H-imidazo[4,5-b]pyridin-3-yl)benzyl)piperidin-4-yl)(methyl-d3)amino)-1,3,5-triazine-2-carbonitrile |
| 234 | 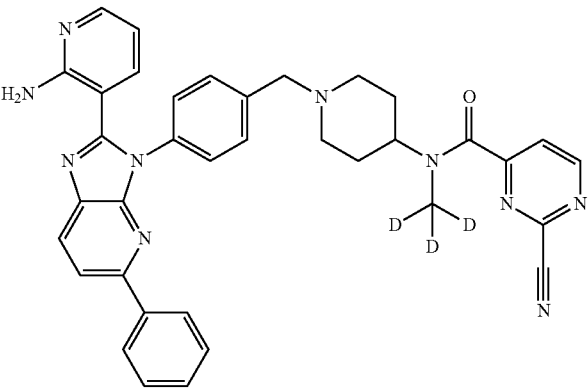 [SMILES: [2H]C([2H])([2H])N(C(=O)c1ccnc(C#N)n1)C1CCN(Cc2ccc(-n3c(-c4cccnc4N)nc4ccc(-c5ccccc5)nc43)cc2)CC1] | N-(1-(4-(2-(2-aminopyridin-3-yl)-5-phenyl-3H-imidazo[4,5-b]pyridin-3-yl)benzyl)piperidin-4-yl)-2-cyano-N-(methyl-d3)pyrimidine-4-carboxamide |
| 235 | 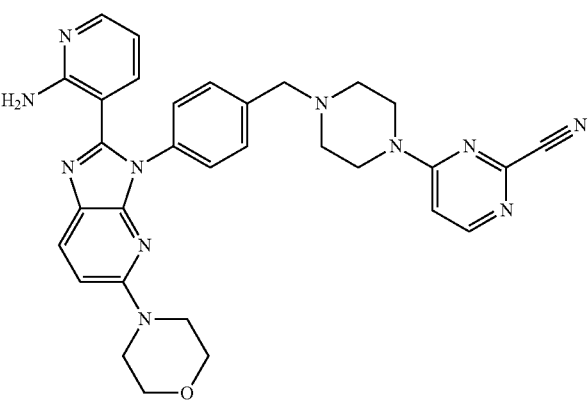 | 4-(4-(4-(2-(2-aminopyridin-3-yl)-5-morpholino-3H-imidazo[4,5-b]pyridin-3-yl)benzyl)piperazin-1-yl)pyrimidine-2-carbonitrile |

TABLE 1-continued

| Example | Compound Structure | Compound Name |
|---|---|---|
| 236 | 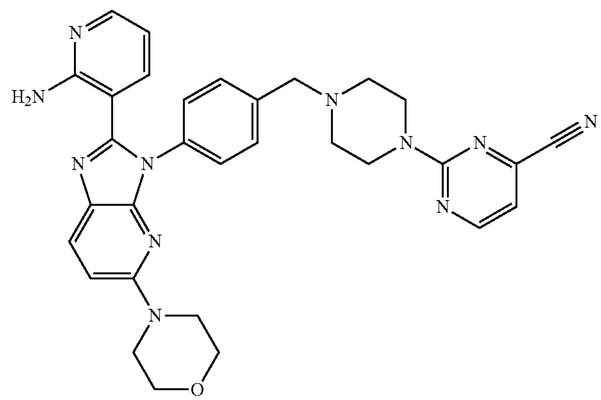 [SMILES: N#Cc1ccnc(N2CCN(Cc3ccc(-n4c(-c5cccnc5N)nc5ccc(N6CCOCC6)nc54)cc3)CC2)n1] | 2-(4-(4-(2-(2-aminopyridin-3-yl)-5-morpholino-3H-imidazo[4,5-b]pyridin-3-yl)benzyl)piperazin-1-yl)pyrimidine-4-carbonitrile |
| 237 | 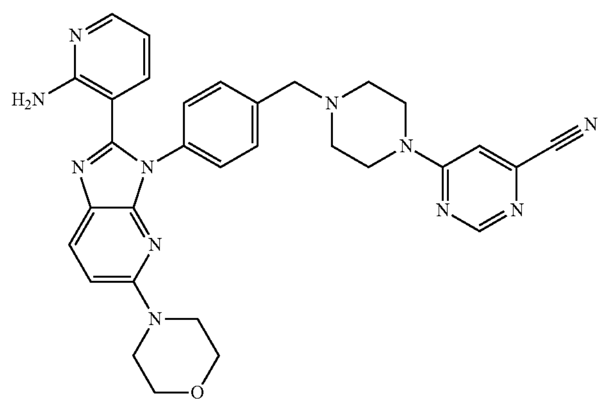 [SMILES: N#Cc1cc(N2CCN(Cc3ccc(-n4c(-c5cccnc5N)nc5ccc(N6CCOCC6)nc54)cc3)CC2)ncn1] | 6-(4-(4-(2-(2-aminopyridin-3-yl)-5-morpholino-3H-imidazo[4,5-b]pyridin-3-yl)benzyl)piperazin-1-yl)pyrimidine-4-carbonitrile |
| 238 | 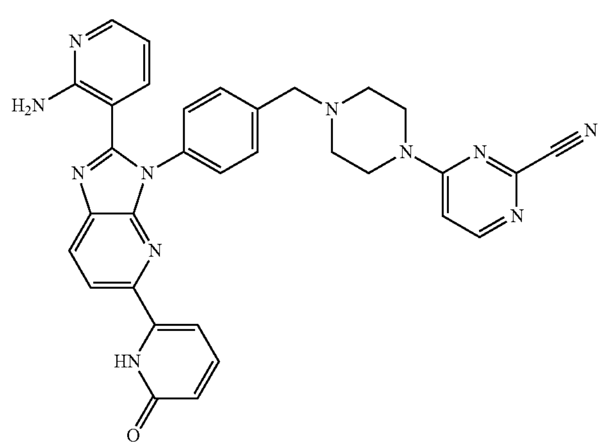 | 4-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-2-carbonitrile |

TABLE 1-continued

| Example | Compound Structure | Compound Name |
|---|---|---|
| 239 | 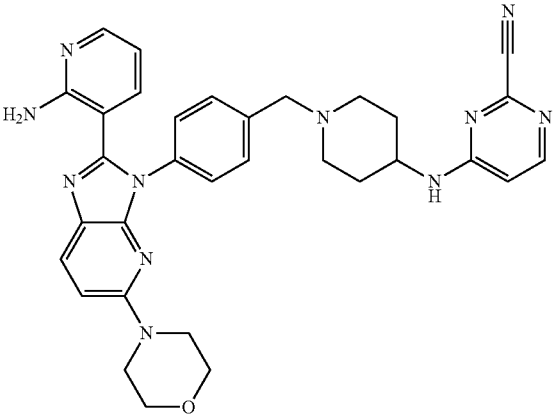 [SMILES: N#Cc1nccc(NC2CCN(Cc3ccc(-n4c(-c5cccnc5N)nc5ccc(N6CCOCC6)nc54)cc3)CC2)n1] | 4-((1-(4-(2-(2-aminopyridin-3-yl)-5-morpholino-3H-imidazo[4,5-b]pyridin-3-yl)benzyl)piperidin-4-yl)amino)pyrimidine-2-carbonitrile |
| 240 | 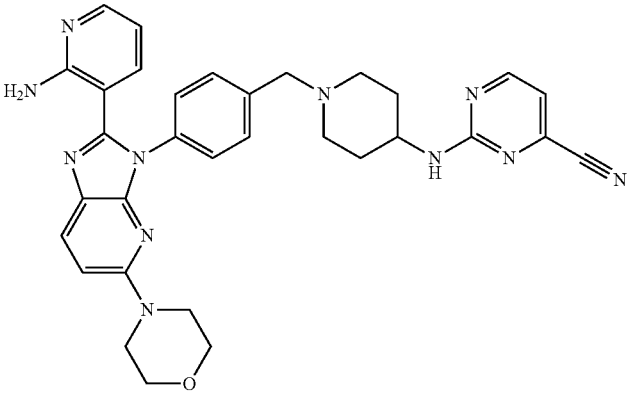 [SMILES: N#Cc1ccnc(NC2CCN(Cc3ccc(-n4c(-c5cccnc5N)nc5ccc(N6CCOCC6)nc54)cc3)CC2)n1] | 2-((1-(4-(2-(2-aminopyridin-3-yl)-5-morpholino-3H-imidazo[4,5-b]pyridin-3-yl)benzyl)piperidin-4-yl)amino)pyrimidine-4-carbonitrile |
| 241 | 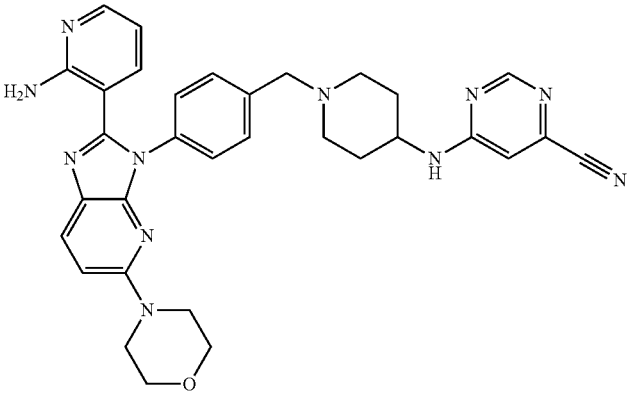 [SMILES: N#Cc1cc(NC2CCN(Cc3ccc(-n4c(-c5cccnc5N)nc5ccc(N6CCOCC6)nc54)cc3)CC2)ncn1] | 6-((1-(4-(2-(2-aminopyridin-3-yl)-5-morpholino-3H-imidazo[4,5-b]pyridin-3-yl)benzyl)piperidin-4-yl)amino)pyrimidine-4-carbonitrile |

TABLE 1-continued

| Example | Compound Structure | Compound Name |
|---|---|---|
| 242 | 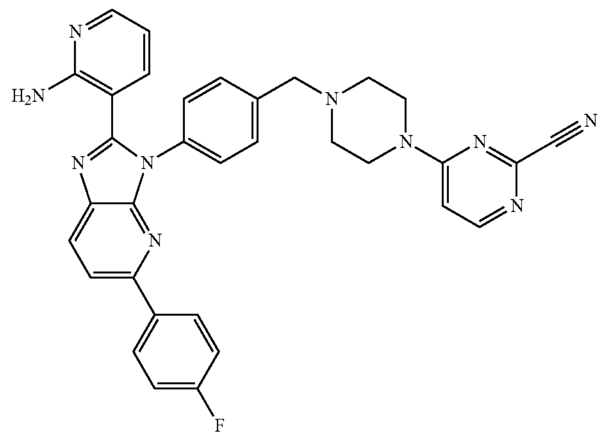 [SMILES: N#Cc1nccc(N2CCN(Cc3ccc(-n4c(-c5cccnc5N)nc5ccc(-c6ccc(F)cc6)nc54)cc3)CC2)n1] | 4-(4-(4-(2-(2-aminopyridin-3-yl)-5-(4-fluorophenyl)-3H-imidazo[4,5-b]pyridin-3-yl)benzyl)piperazin-1-yl)pyrimidine-2-carbonitrile |
| 243 | 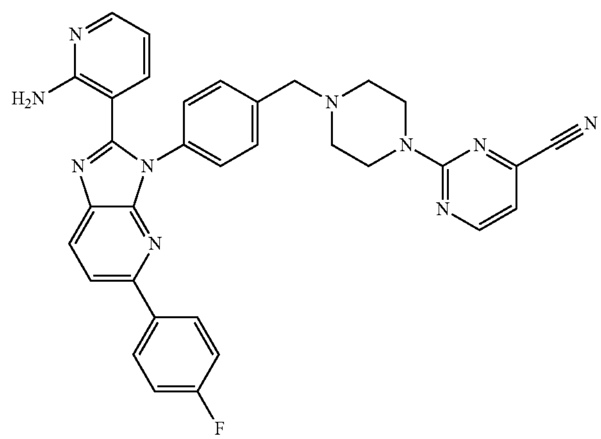 [SMILES: N#Cc1ccnc(N2CCN(Cc3ccc(-n4c(-c5cccnc5N)nc5ccc(-c6ccc(F)cc6)nc54)cc3)CC2)n1] | 2-(4-(4-(2-(2-aminopyridin-3-yl)-5-(4-fluorophenyl)-3H-imidazo[4,5-b]pyridin-3-yl)benzyl)piperazin-1-yl)pyrimidine-4-carbonitrile |
| 244 | 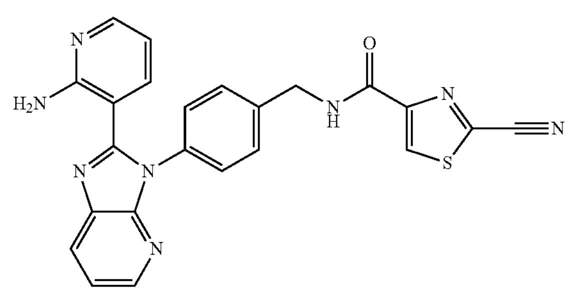 [SMILES: N#Cc1nc(C(=O)NCc2ccc(-n3c(-c4cccnc4N)nc4cccnc43)cc2)cs1] | N-(4-(2-(2-aminopyridin-3-yl)-3H-imidazo[4,5-b]pyridin-3-yl)benzyl)-2-cyanothiazole-4-carboxamide |
| 245 | 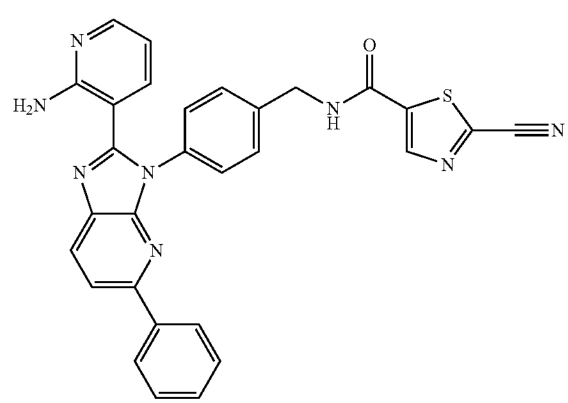 [SMILES: N#Cc1ncc(C(=O)NCc2ccc(-n3c(-c4cccnc4N)nc4ccc(-c5ccccc5)nc43)cc2)s1] | N-(4-(2-(2-aminopyridin-3-yl)-5-phenyl-3H-imidazo[4,5-b]pyridin-3-yl)benzyl)-2-cyanothiazole-5-carboxamide |

TABLE 1-continued

| Example | Compound Structure | Compound Name |
|---|---|---|
| 246 | 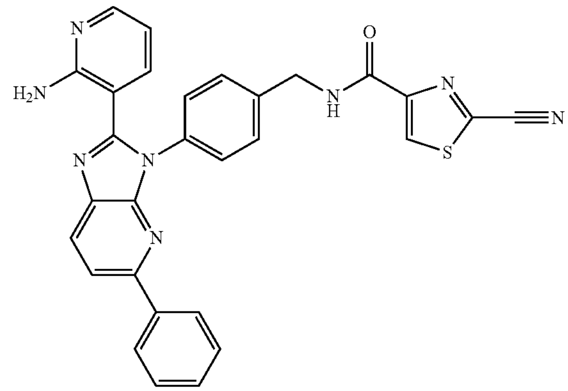 [SMILES: N#Cc1nc(C(=O)NCc2ccc(-n3c(-c4cccnc4N)nc4ccc(-c5ccccc5)nc43)cc2)cs1] | N-(4-(2-(2-aminopyridin-3-yl)-5-phenyl-3H-imidazo[4,5-b]pyridin-3-yl)benzyl)-2-cyanothiazole-4-carboxamide |
| 247 | 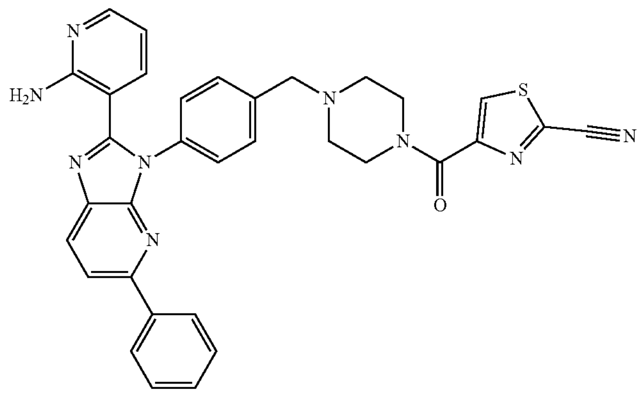 [SMILES: N#Cc1nc(C(=O)N2CCN(Cc3ccc(-n4c(-c5cccnc5N)nc5ccc(-c6ccccc6)nc54)cc3)CC2)cs1] | 4-(4-(4-(2-(2-aminopyridin-3-yl)-5-phenyl-3H-imidazo[4,5-b]pyridin-3-yl)benzyl)piperazine-1-carbonyl)thiazole-2-carbonitrile |
| 248 | 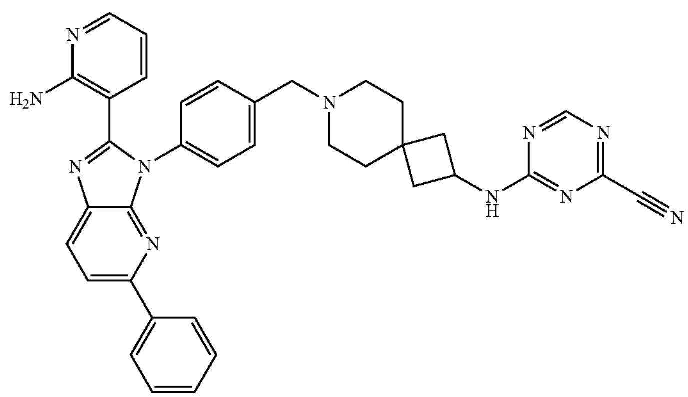 [SMILES: N#Cc1ncnc(NC2CC3(CCN(Cc4ccc(-n5c(-c6cccnc6N)nc6ccc(-c7ccccc7)nc65)cc4)CC3)C2)n1] | 4-((7-(4-(2-(2-aminopyridin-3-yl)-5-phenyl-3H-imidazo[4,5-b]pyridin-3-yl)benzyl)-7-azaspiro[3.5]nonan-2-yl)amino)-1,3,5-triazine-2-carbonitrile |
| 249 | 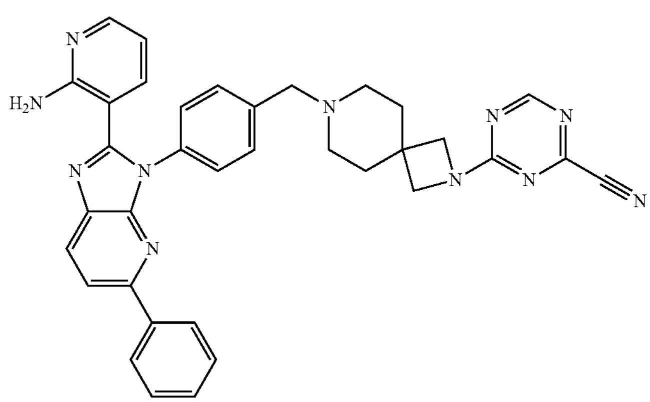 [SMILES: N#Cc1ncnc(N2CC3(CCN(Cc4ccc(-n5c(-c6cccnc6N)nc6ccc(-c7ccccc7)nc65)cc4)CC3)C2)n1] | 4-(7-(4-(2-(2-aminopyridin-3-yl)-5-phenyl-3H-imidazo[4,5-b]pyridin-3-yl)benzyl)-2,7-diazaspiro[3.5]nonan-2-yl)-1,3,5-triazine-2-carbonitrile |

TABLE 1-continued

| Example | Compound Structure | Compound Name |
|---|---|---|
| 250 | 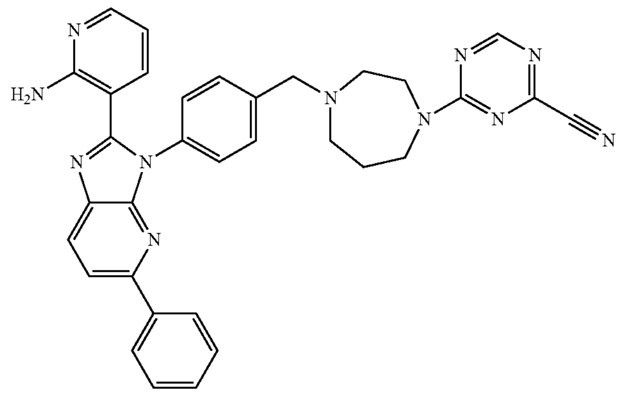 [SMILES: N#Cc1ncnc(N2CCCN(Cc3ccc(-n4c(-c5cccnc5N)nc5ccc(-c6ccccc6)nc54)cc3)CC2)n1] | 4-(4-(4-(2-(2-aminopyridin-3-yl)-5-phenyl-3H-imidazo[4,5-b]pyridin-3-yl)benzyl)-1,4-diazepan-1-yl)-1,3,5-triazine-2-carbonitrile |
| 251 | 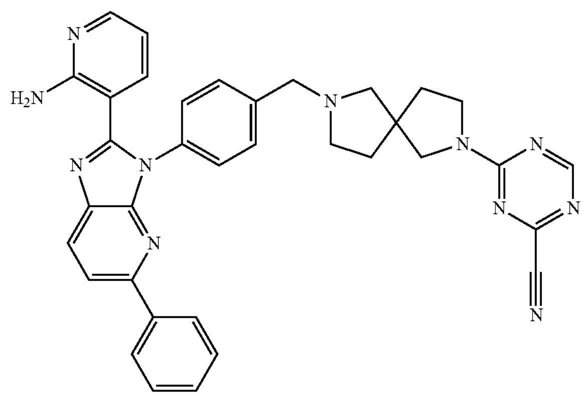 [SMILES: N#Cc1ncnc(N2CCC3(CCN(Cc4ccc(-n5c(-c6cccnc6N)nc6ccc(-c7ccccc7)nc65)cc4)C3)C2)n1] | 4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile |
| 252 | 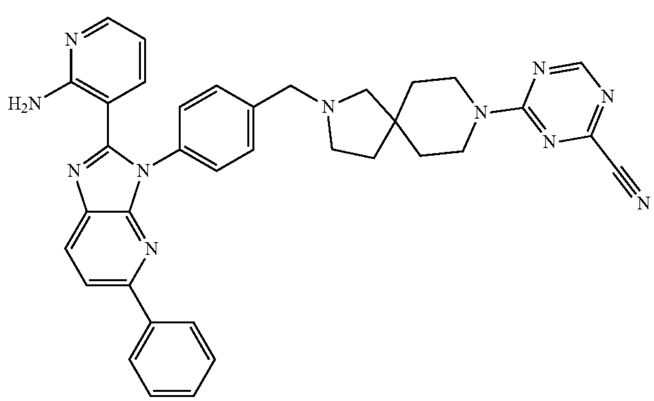 [SMILES: N#Cc1ncnc(N2CCC3(CCN(Cc4ccc(-n5c(-c6cccnc6N)nc6ccc(-c7ccccc7)nc65)cc4)C3)CC2)n1] | 4-(2-(4-(2-(2-aminopyridin-3-yl)-5-phenyl-3H-imidazo[4,5-b]pyridin-3-yl)benzyl)-2,8-diazaspiro[4.5]decan-8-yl)-1,3,5-triazine-2-carbonitrile |

TABLE 1-continued

| Example | Compound Structure | Compound Name |
|---|---|---|
| 253 | 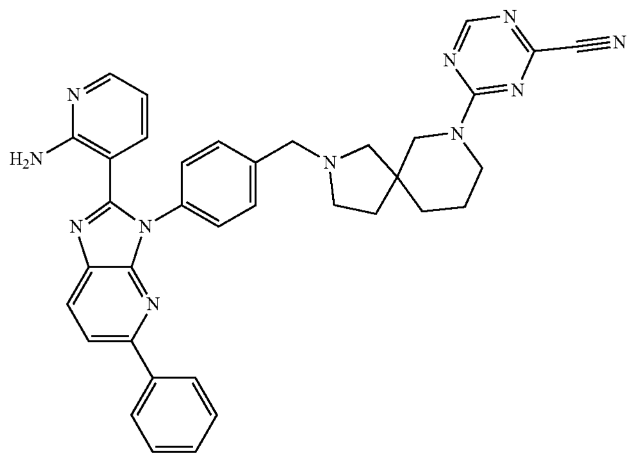 [SMILES: N#Cc1ncnc(N2CCCC3(CCN(Cc4ccc(-n5c(-c6cccnc6N)nc6ccc(-c7ccccc7)nc65)cc4)C3)C2)n1] | 4-(2-(4-(2-(2-aminopyridin-3-yl)-5-phenyl-3H-imidazo[4,5-b]pyridin-3-yl)benzyl)-2,7-diazaspiro[4.5]decan-7-yl)-1,3,5-triazine-2-carbonitrile |
| 254 | 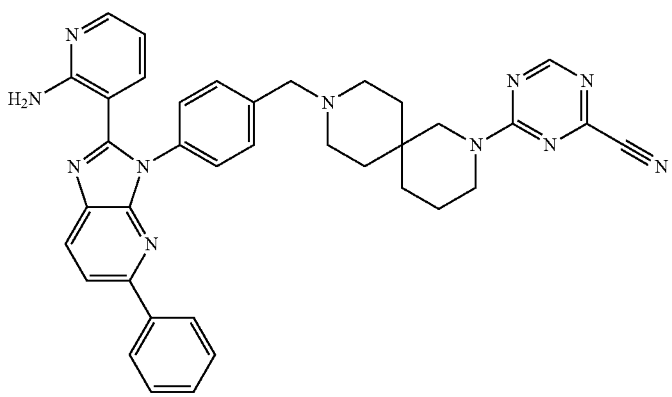 [SMILES: N#Cc1ncnc(N2CCCC3(CCN(Cc4ccc(-n5c(-c6cccnc6N)nc6ccc(-c7ccccc7)nc65)cc4)CC3)C2)n1] | 4-(9-(4-(2-(2-aminopyridin-3-yl)-5-phenyl-3H-imidazo[4,5-b]pyridin-3-yl)benzyl)-2,9-diazaspiro[5.5]undecan-2-yl)-1,3,5-triazine-2-carbonitrile |
| 255 | 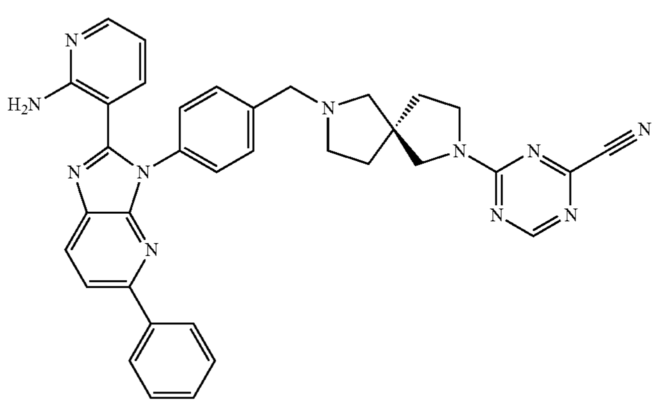 [SMILES: N#Cc1ncnc(N2CC[C@@]3(CCN(Cc4ccc(-n5c(-c6cccnc6N)nc6ccc(-c7ccccc7)nc65)cc4)C3)C2)n1] | (R)-4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile |

TABLE 1-continued

| Example | Compound Structure | Compound Name |
|---|---|---|
| 256 | 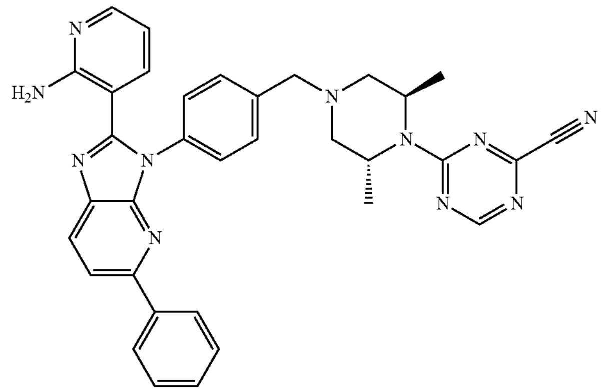 | 4-((2R,6R)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile |
| 257 | 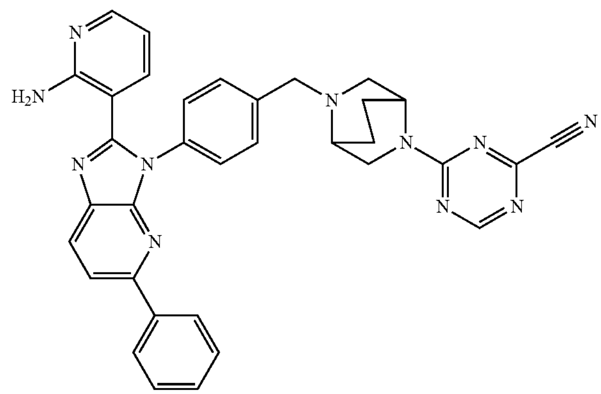 [SMILES: N#Cc1ncnc(N2CC3CCC2CN3Cc2ccc(-n3c(-c4cccnc4N)nc4ccc(-c5ccccc5)nc43)cc2)n1] | 4-(5-(4-(2-(2-aminopyridin-3-yl)-5-phenyl-3H-imidazo[4,5-b]pyridin-3-yl)benzyl)-2,5-diazabicyclo[2.2.2]octan-2-yl)-1,3,5-triazine-2-carbonitrile |
| 258 | 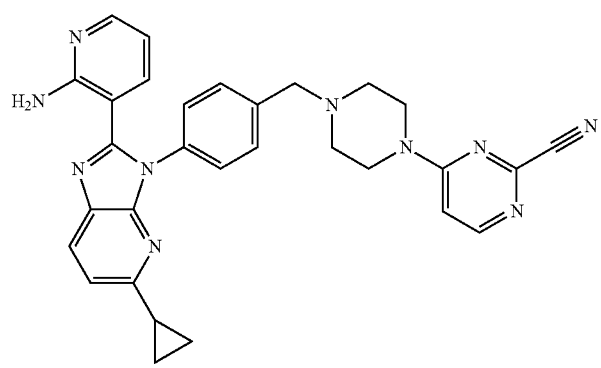 [SMILES: N#Cc1nccc(N2CCN(Cc3ccc(-n4c(-c5cccnc5N)nc5ccc(C6CC6)nc54)cc3)CC2)n1] | 4-(4-(4-(2-(2-aminopyridin-3-yl)-5-cyclopropyl-3H-imidazo[4,5-b]pyridin-3-yl)benzyl)piperazin-1-yl)pyrimidine-2-carbonitrile |
| 259 | 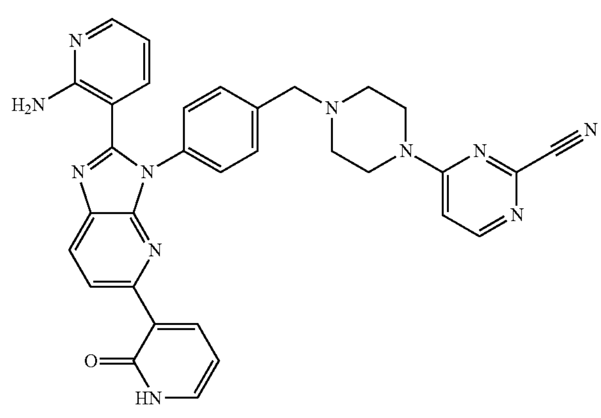 [SMILES: N#Cc1nccc(N2CCN(Cc3ccc(-n4c(-c5cccnc5N)nc5ccc(-c6ccc[nH]c6=O)nc54)cc3)CC2)n1] | 4-(4-(4-(2-(2-aminopyridin-3-yl)-5-(2-oxo-1,2-dihydropyridin-3-yl)-3H-imidazo[4,5-b]pyridin-3-yl)benzyl)piperazin-1-yl)pyrimidine-2-carbonitrile |

TABLE 1-continued

| Example | Compound Structure | Compound Name |
|---|---|---|
| 260 | 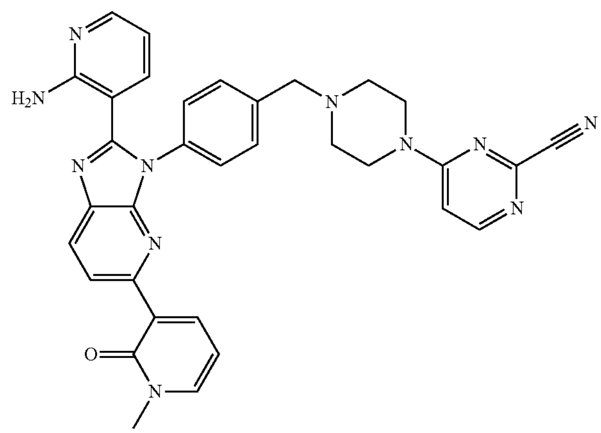 [SMILES: Cn1cccc(-c2ccc3nc(-c4cccnc4N)n(-c4ccc(CN5CCN(c6ccnc(C#N)n6)CC5)cc4)c3n2)c1=O] | 4-(4-(4-(2-(2-aminopyridin-3-yl)-5-(1-methyl-2-oxo-1,2-dihydropyridin-3-yl)-3H-imidazo[4,5-b]pyridin-3-yl)benzyl)piperazin-1-yl)pyrimidine-2-carbonitrile |
| 261 | 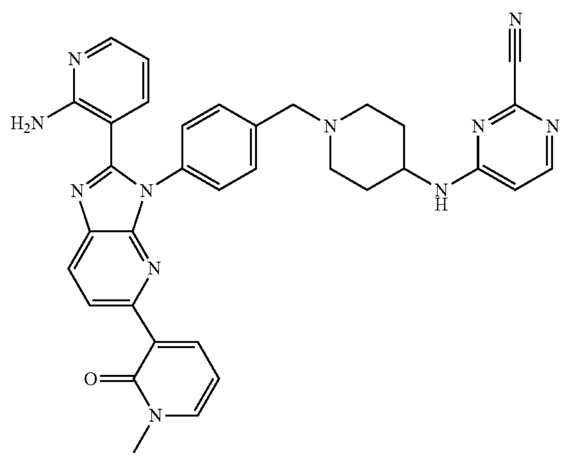 [SMILES: Cn1cccc(-c2ccc3nc(-c4cccnc4N)n(-c4ccc(CN5CCC(Nc6ccnc(C#N)n6)CC5)cc4)c3n2)c1=O] | 4-((1-(4-(2-(2-aminopyridin-3-yl)-5-(1-methyl-2-oxo-1,2-dihydropyridin-3-yl)-3H-imidazo[4,5-b]pyridin-3-yl)benzyl)piperidin-4-yl)amino)pyrimidine-2-carbonitrile |
| 262 | 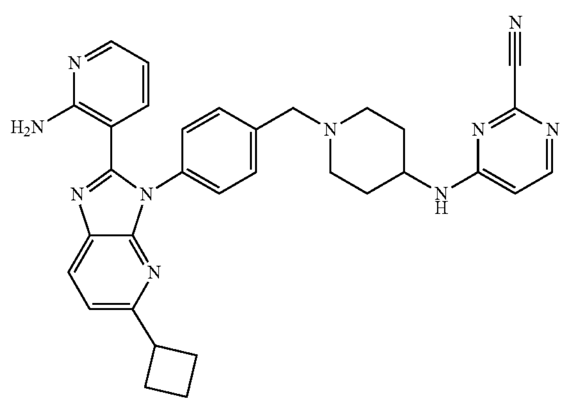 [SMILES: N#Cc1nccc(NC2CCN(Cc3ccc(-n4c(-c5cccnc5N)nc5ccc(C6CCC6)nc54)cc3)CC2)n1] | 4-((1-(4-(2-(2-aminopyridin-3-yl)-5-cyclobutyl-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 263 | 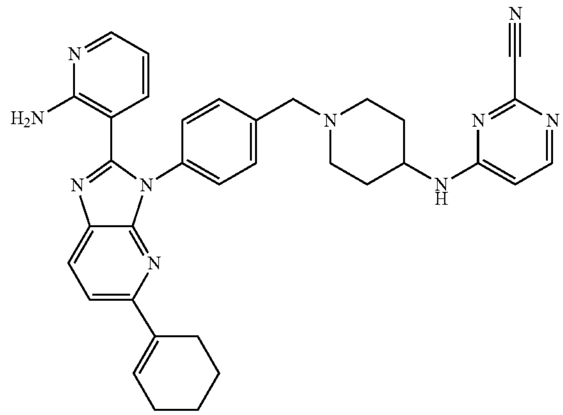 [SMILES: N#Cc1nccc(NC2CCN(Cc3ccc(-n4c(-c5cccnc5N)nc5ccc(C6=CCCCC6)nc54)cc3)CC2)n1] | 4-((1-(4-(2-(2-aminopyridin-3-yl)-5-(cyclohex-1-en-1-yl])-3H-imidazo[4,5-b]pyridin-3-yl)benzyl)piperidin-4-yl)amino)pyrimidine-2-carbonitrile |
| 264 | 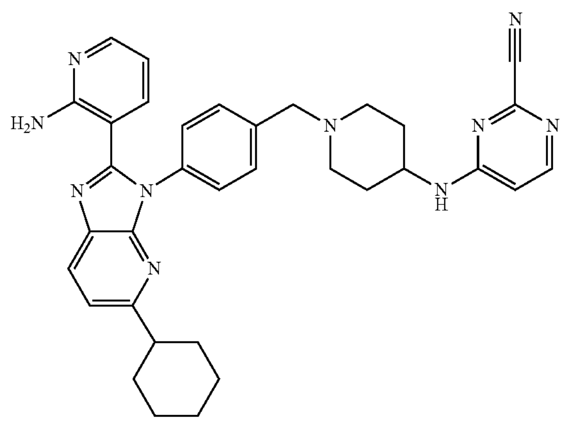 [SMILES: N#Cc1nccc(NC2CCN(Cc3ccc(-n4c(-c5cccnc5N)nc5ccc(C6CCCCC6)nc54)cc3)CC2)n1] | 4-((1-(4-(2-(2-aminopyridin-3-yl)-5-cyclohexyl-3H-imidazo[4,5-b]pyridin-3-yl)benzyl)piperidin-4-yl)amino)pyrimidine-2-carbonitrile |
| 265 | 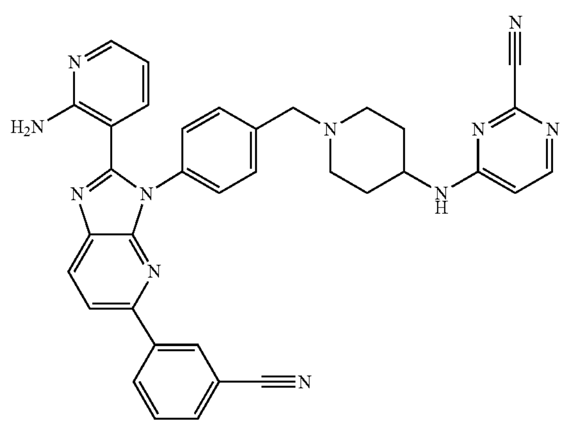 [SMILES: N#Cc1cccc(-c2ccc3nc(-c4cccnc4N)n(-c4ccc(CN5CCC(Nc6ccnc(C#N)n6)CC5)cc4)c3n2)c1] | 4-((1-(4-(2-(2-aminopyridin-3-yl)-5-(3-cyanophenyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 266 | 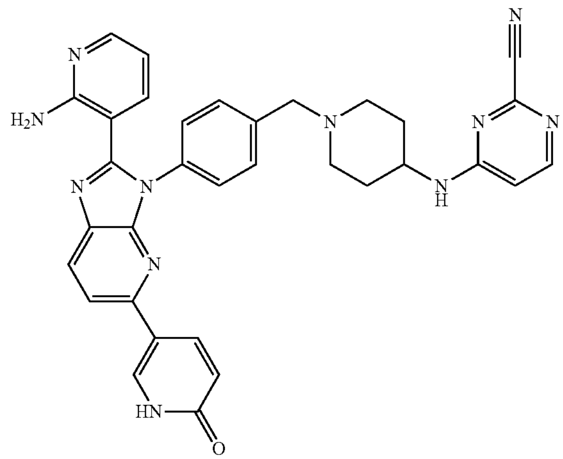 [SMILES: N#Cc1nccc(NC2CCN(Cc3ccc(-n4c(-c5cccnc5N)nc5ccc(-c6ccc(=O)[nH]c6)nc54)cc3)CC2)n1] | 4-((1-(4-(2-(2-aminopyridin-3-yl)-5-(6-oxo-1,6-dihydropyridin-3-yl)-3H-imidazo[4,5-b]pyridin-3-yl)benzyl)piperidin-4-yl)amino)pyrimidine-2-carbonitrile |
| 267 | 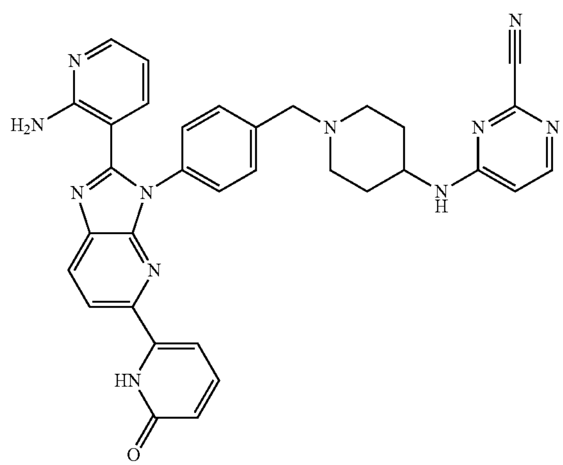 [SMILES: N#Cc1nccc(NC2CCN(Cc3ccc(-n4c(-c5cccnc5N)nc5ccc(-c6cccc(=O)[nH]6)nc54)cc3)CC2)n1] | 4-((1-(4-(2-(2-aminopyridin-3-yl)-5-(6-oxo-1,6-dihydropyridin-2-yl)-3H-imidazo[4,5-b]pyridin-3-yl)benzyl)piperidin-4-yl)amino)pyrimidine-2-carbonitrile |
| 268 | 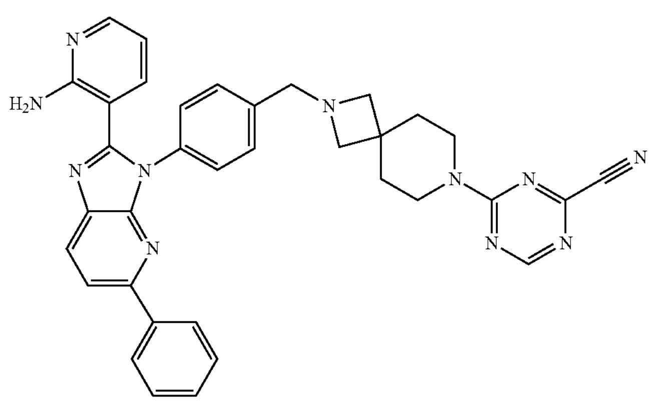 [SMILES: N#Cc1ncnc(N2CCC3(CC2)CN(Cc2ccc(-n4c(-c5cccnc5N)nc5ccc(-c6ccccc6)nc54)cc2)C3)n1] | 4-(2-(4-(2-(2-aminopyridin-3-yl)-5-phenyl-3H-imidazo[4,5-b]pyridin-3-yl)benzyl)-2,7-diazaspiro[3.5]nonan-7-yl)-1,3,5-triazine-2-carbonitrile |

TABLE 1-continued

| Example | Compound Structure | Compound Name |
|---|---|---|
| 269 | 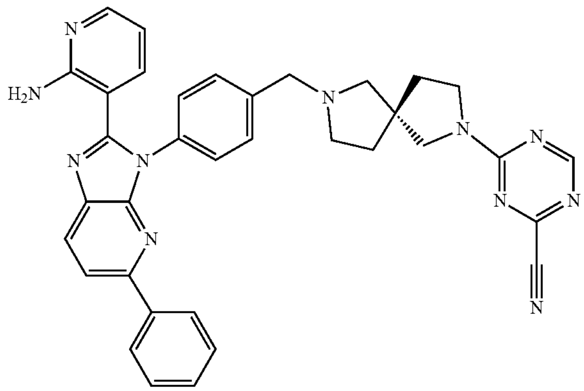 [SMILES: N#Cc1ncnc(N2CC[C@]3(CCN(Cc4ccc(-n5c(-c6cccnc6N)nc6ccc(-c7ccccc7)nc65)cc4)C3)C2)n1] | (S)-4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile |
| 270 | 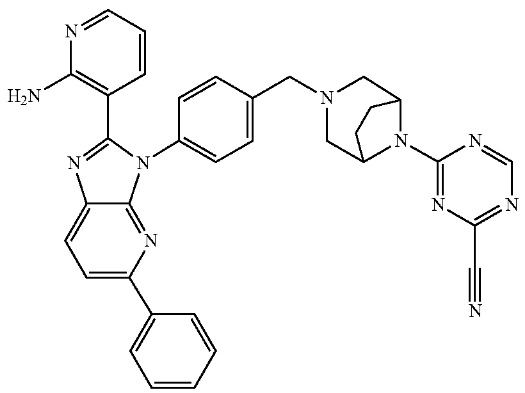 [SMILES: N#Cc1ncnc(N2C3CCC2CN(Cc2ccc(-n4c(-c5cccnc5N)nc5ccc(-c6ccccc6)nc54)cc2)C3)n1] | 4-(3-(4-(2-(2-aminopyridin-3-yl)-5-phenyl-3H-imidazo[4,5-b]pyridin-3-yl)benzyl)-3,8-diazabicyclo[3.2.1]octan-8-yl)-1,3,5-triazine-2-carbonitrile |
| 271 | 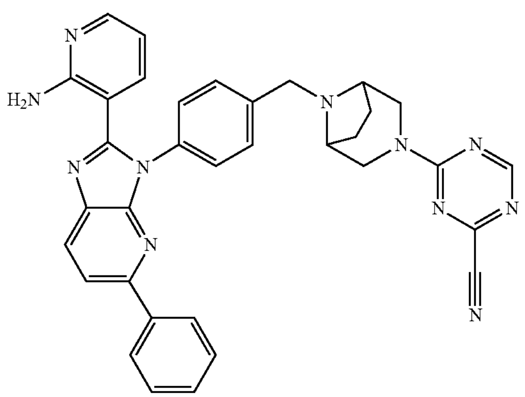 [SMILES: N#Cc1ncnc(N2CC3CCC(C2)N3Cc2ccc(-n3c(-c4cccnc4N)nc4ccc(-c5ccccc5)nc43)cc2)n1] | 4-(8-(4-(2-(2-aminopyridin-3-yl)-5-phenyl-3H-imidazo[4,5-b]pyridin-3-yl)benzyl)-3,8-diazabicyclo[3.2.1]octan-3-yl)-1,3,5-triazine-2-carbonitrile |
| 272 | 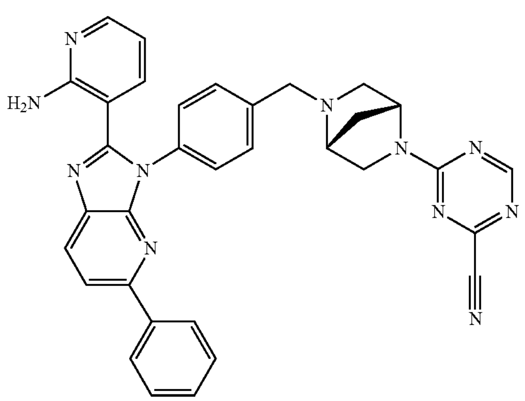 [SMILES: N#Cc1ncnc(N2C[C@H]3C[C@@H]2CN3Cc2ccc(-n3c(-c4cccnc4N)nc4ccc(-c5ccccc5)nc43)cc2)n1] | 4-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile |

TABLE 1-continued

| Example | Compound Structure | Compound Name |
|---|---|---|
| 273 | 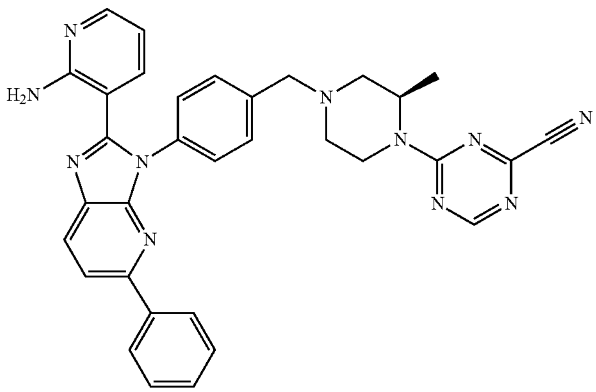 [SMILES: C[C@@H]1CN(Cc2ccc(-n3c(-c4cccnc4N)nc4ccc(-c5ccccc5)nc43)cc2)CCN1c1ncnc(C#N)n1] | (R)-4-(4-(4-(2-(2-aminopyridin-3-yl)-5-phenyl-3H-imidazo[4,5-b]pyridin-3-yl)benzyl)-2-methylpiperazin-1-yl)-1,3,5-triazine-2-carbonitrile |
| 274 | 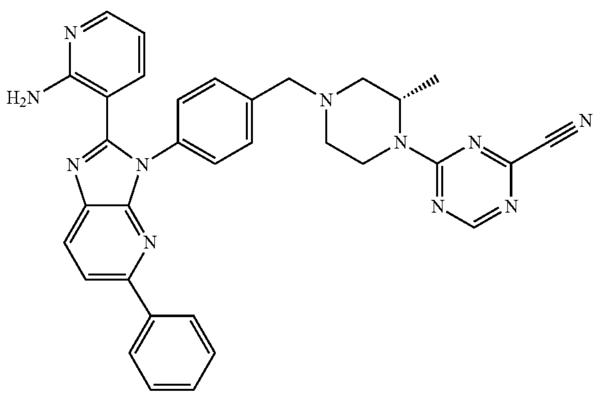 [SMILES: C[C@H]1CN(Cc2ccc(-n3c(-c4cccnc4N)nc4ccc(-c5ccccc5)nc43)cc2)CCN1c1ncnc(C#N)n1] | (S)-4-(4-(4-(2-(2-aminopyridin-3-yl)-5-phenyl-3H-imidazo[4,5-b]pyridin-3-yl)benzyl)-2-methylpiperazin-1-yl)-1,3,5-triazine-2-carbonitrile |
| 275 | 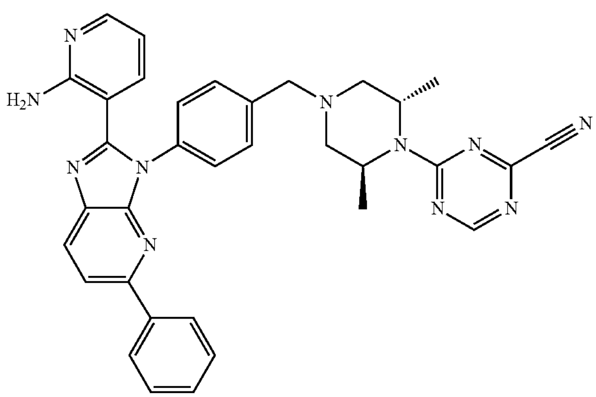 [SMILES: C[C@H]1CN(Cc2ccc(-n3c(-c4cccnc4N)nc4ccc(-c5ccccc5)nc43)cc2)C[C@H](C)N1c1ncnc(C#N)n1] | 4-((2S,6S)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile |
| 276 | 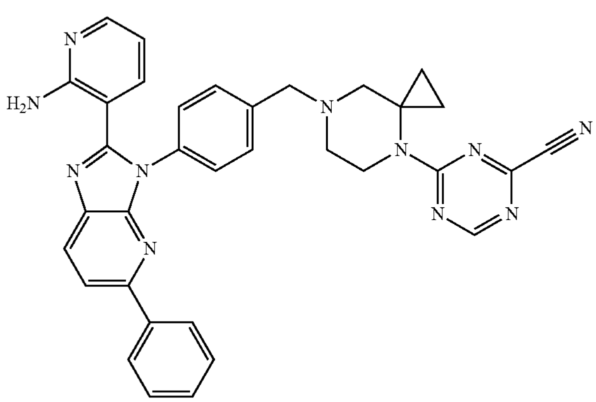 [SMILES: N#Cc1ncnc(N2CCN(Cc3ccc(-n4c(-c5cccnc5N)nc5ccc(-c6ccccc6)nc54)cc3)CC23CC3)n1] | 4-(7-(4-(2-(2-aminopyridin-3-yl)-5-phenyl-3H-imidazo[4,5-b]pyridin-3-yl)benzyl)-4,7-diazaspiro[2.5]octan-4-yl)-1,3,5-triazine-2-carbonitrile |

TABLE 1-continued

| Example | Compound Structure | Compound Name |
|---|---|---|
| 277 | 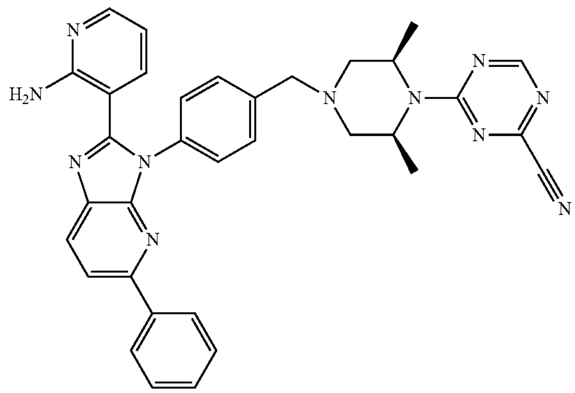 [SMILES: C[C@@H]1CN(Cc2ccc(-n3c(-c4cccnc4N)nc4ccc(-c5ccccc5)nc43)cc2)C[C@H](C)N1c1ncnc(C#N)n1] | 4-((2R,6S)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile |
| 278 | 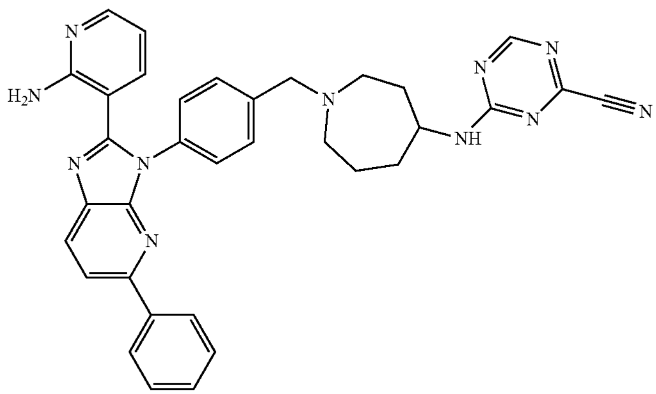 [SMILES: N#Cc1ncnc(NC2CCCN(Cc3ccc(-n4c(-c5cccnc5N)nc5ccc(-c6ccccc6)nc54)cc3)CC2)n1] | 4-((1-(4-(2-(2-aminopyridin-3-yl)-5-phenyl-3H-imidazo[4,5-b]pyridin-3-yl)benzyl)azepan-4-yl)amino)-1,3,5-triazine-2-carbonitrile |
| 279 | 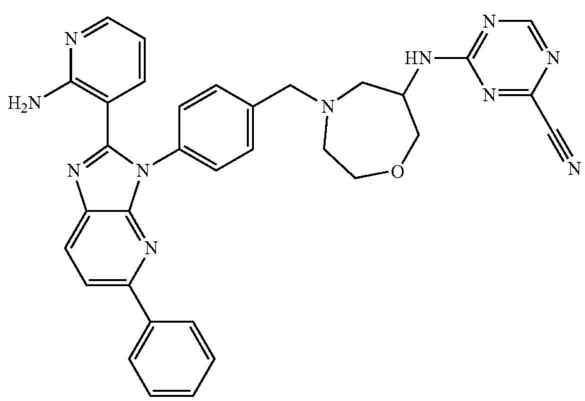 [SMILES: N#Cc1ncnc(NC2COCCN(Cc3ccc(-n4c(-c5cccnc5N)nc5ccc(-c6ccccc6)nc54)cc3)C2)n1] | 4-((4-(4-(2-(2-aminopyridin-3-yl)-5-phenyl-3H-imidazo[4,5-b]pyridin-3-yl)benzyl)-1,4-oxazepan-6-yl)amino)-1,3,5-triazine-2-carbonitrile |
| 280 | 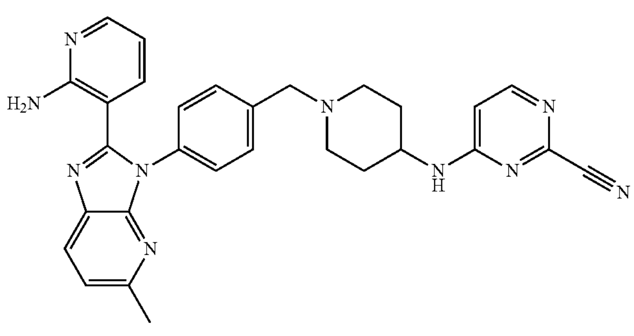 [SMILES: Cc1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-methyl-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 281 | 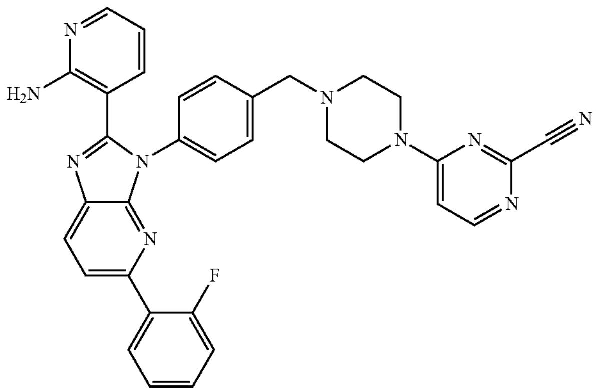 [SMILES: N#Cc1nccc(N2CCN(Cc3ccc(-n4c(-c5cccnc5N)nc5ccc(-c6ccccc6F)nc54)cc3)CC2)n1] | 4-(4-(4-(2-(2-aminopyridin-3-yl)-5-(2-fluorophenyl)-3H-imidazo[4,5-b]pyridin-3-yl)benzyl)piperazin-1-yl)pyrimidine-2-carbonitrile |
| 282 | 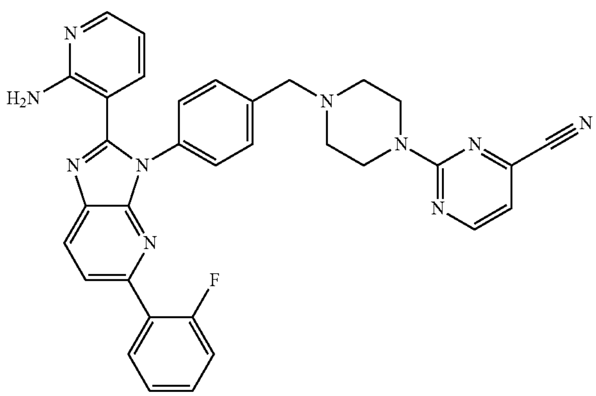 [SMILES: N#Cc1ccnc(N2CCN(Cc3ccc(-n4c(-c5cccnc5N)nc5ccc(-c6ccccc6F)nc54)cc3)CC2)n1] | 2-(4-(4-(2-(2-aminopyridin-3-yl)-5-(2-fluorophenyl)-3H-imidazo[4,5-b]pyridin-3-yl)benzyl)piperazin-1-yl)pyrimidine-4-carbonitrile |
| 283 | 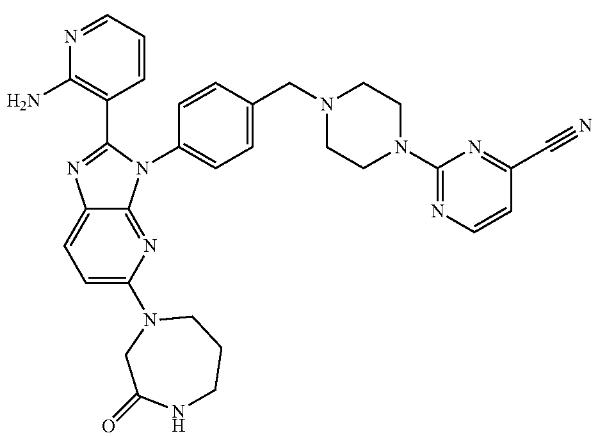 [SMILES: N#Cc1ccnc(N2CCN(Cc3ccc(-n4c(-c5cccnc5N)nc5ccc(N6CCCNC(=O)C6)nc54)cc3)CC2)n1] | 2-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-4-carbonitrile |

TABLE 1-continued

| Example | Compound Structure | Compound Name |
|---|---|---|
| 284 | 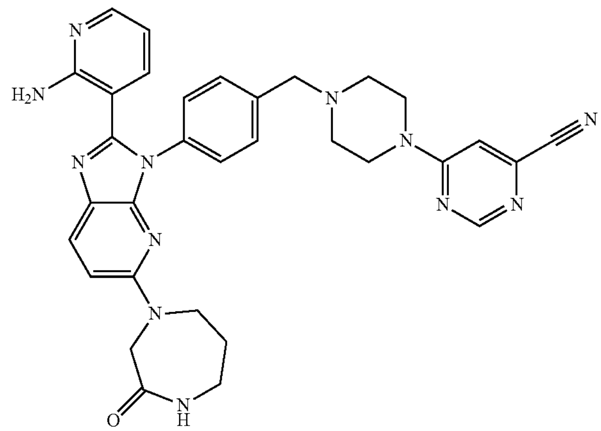 [SMILES: N#Cc1cc(N2CCN(Cc3ccc(-n4c(-c5cccnc5N)nc5ccc(N6CCCNC(=O)C6)nc54)cc3)CC2)ncn1] | 6-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-4-carbonitrile |
| 285 | 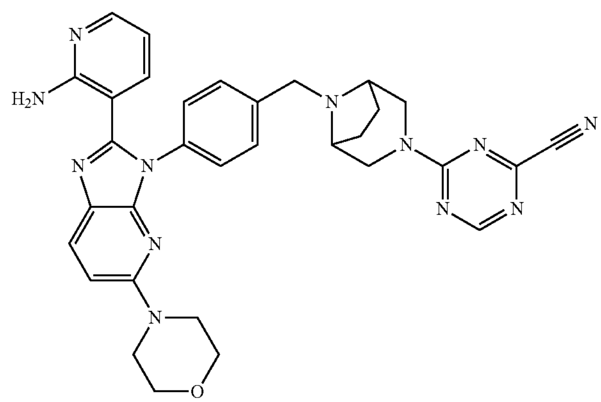 [SMILES: N#Cc1ncnc(N2CC3CCC(C2)N3Cc2ccc(-n3c(-c4cccnc4N)nc4ccc(N5CCOCC5)nc43)cc2)n1] | 4-(8-(4-(2-(2-aminopyridin-3-yl)-5-morpholino-3H-imidazo[4,5-b]pyridin-3-yl)benzyl)-3,8-diazabicyclo[3.2.1]octan-3-yl)-1,3,5-triazine-2-carbonitrile |
| 286 | 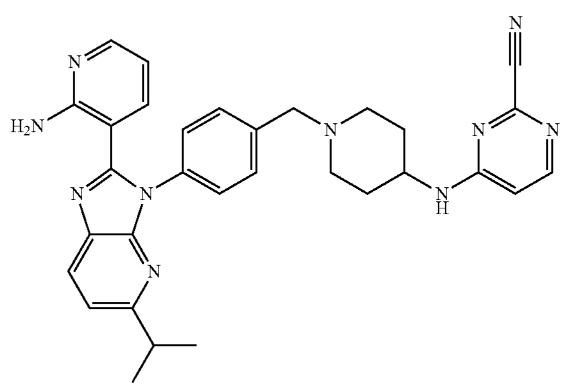 | 4-((1-(4-(2-(2-aminopyridin-3-yl)-5-isopropyl-3H-imidazo[4,5-b]pyridin-3-yl)benzyl)piperidin-4-yl)amino)pyrimidine-2-carbonitrile |
| 287 | 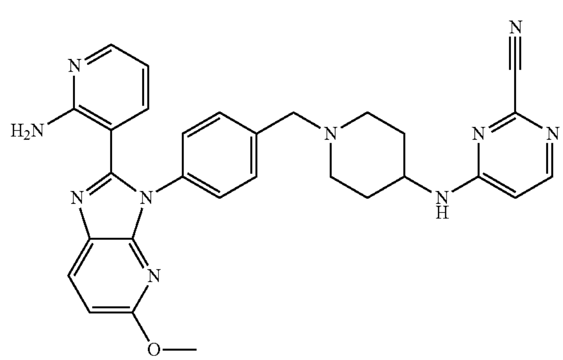 [SMILES: COc1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-methoxy-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 288 | 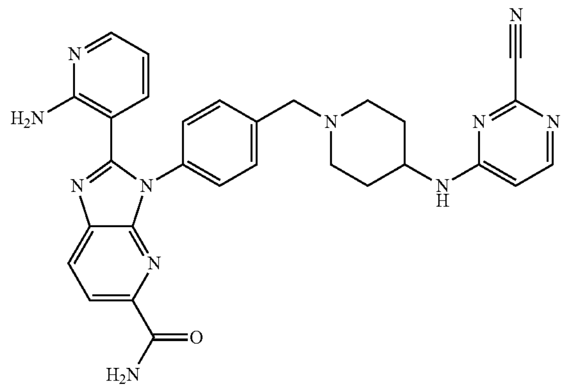 [SMILES: N#Cc1nccc(NC2CCN(Cc3ccc(-n4c(-c5cccnc5N)nc5ccc(C(N)=O)nc54)cc3)CC2)n1] | 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxamide |
| 289 | 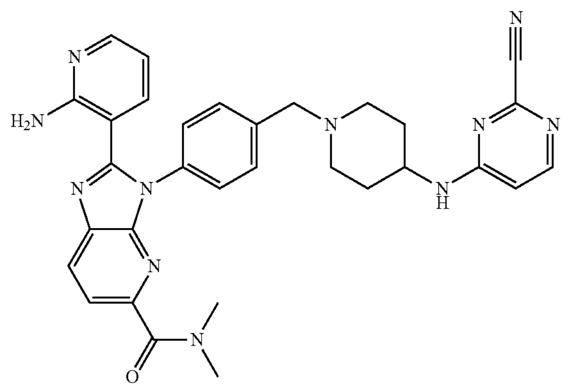 [SMILES: CN(C)C(=O)c1ccc2nc(-c3cccnc3N)n(-c3ccc(CN4CCC(Nc5ccnc(C#N)n5)CC4)cc3)c2n1] | 2-(2-aminopyridin-3-yl)-3-(4-((4-((2-cyanopyrimidin-4-yl)amino)piperidin-1-yl)methyl)phenyl)-N,N-dimethyl-3H-imidazo[4,5-b]pyridine-5-carboxamide |
| 290 | 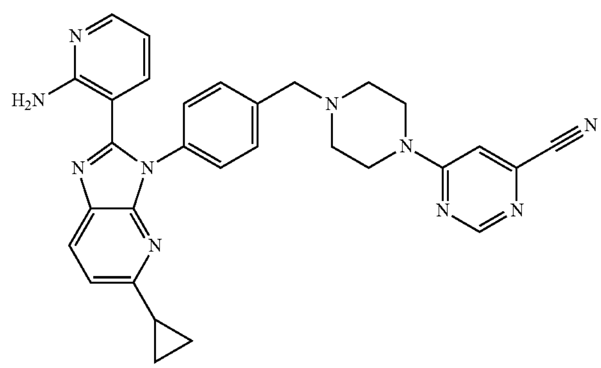 | 6-(4-(4-(2-(2-aminopyridin-3-yl)-5-cyclopropyl-3H-imidazo[4,5-b]pyridin-3-yl)benzyl)piperazin-1-yl)pyrimidine-4-carbonitrile |
| 291 | 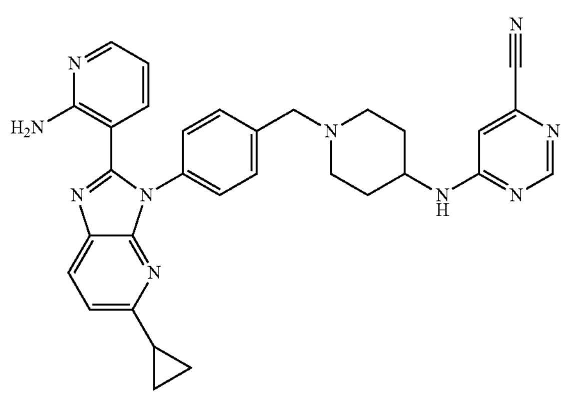 [SMILES: N#Cc1cc(NC2CCN(Cc3ccc(-n4c(-c5cccnc5N)nc5ccc(C6CC6)nc54)cc3)CC2)ncn1] | 6-((1-(4-(2-(2-aminopyridin-3-yl)-5-cyclopropyl-3H-imidazo[4,5-b]pyridin-3-yl)benzyl)piperidin-4-yl)amino)pyrimidine-4-carbonitrile |

TABLE 1-continued

| Example | Compound Structure | Compound Name |
|---|---|---|
| 292 | 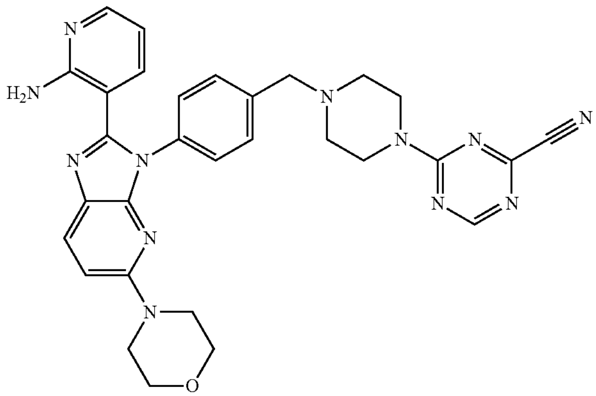 [SMILES: N#Cc1ncnc(N2CCN(Cc3ccc(-n4c(-c5cccnc5N)nc5ccc(N6CCOCC6)nc54)cc3)CC2)n1] | 4-(4-(4-(2-(2-aminopyridin-3-yl)-5-morpholino-3H-imidazo[4,5-b]pyridin-3-yl)benzyl)piperazin-1-yl)-1,3,5-triazine-2-carbonitrile |
| 293 | 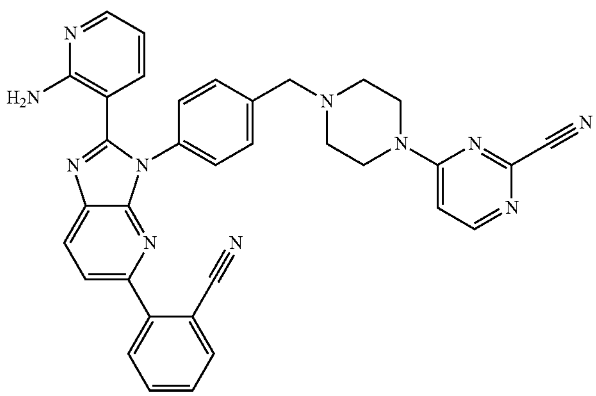 [SMILES: N#Cc1nccc(N2CCN(Cc3ccc(-n4c(-c5cccnc5N)nc5ccc(-c6ccccc6C#N)nc54)cc3)CC2)n1] | 4-(4-(4-(2-(2-aminopyridin-3-yl)-5-(2-cyanophenyl)-3H-imidazo[4,5-b]pyridin-3-yl)benzyl)piperazin-1-yl)pyrimidine-2-carbonitrile |
| 294 | 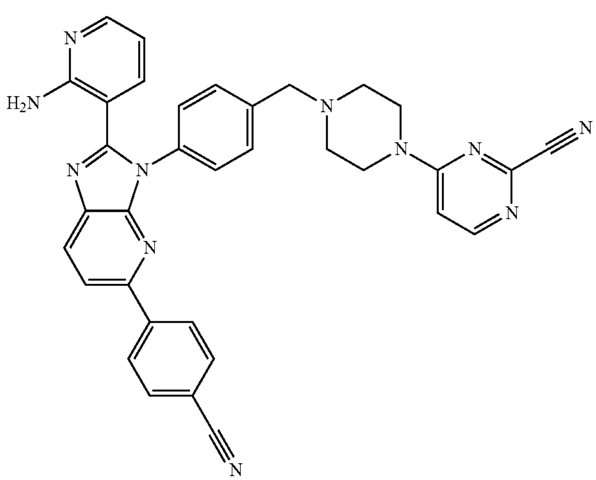 [SMILES: N#Cc1ccc(-c2ccc3nc(-c4cccnc4N)n(-c4ccc(CN5CCN(c6ccnc(C#N)n6)CC5)cc4)c3n2)cc1] | 4-(4-(4-(2-(2-aminopyridin-3-yl)-5-(4-cyanophenyl)-3H-imidazo[4,5-b]pyridin-3-yl)benzyl)piperazin-1-yl)pyrimidine-2-carbonitrile |

TABLE 1-continued

| Example | Compound Structure | Compound Name |
|---|---|---|
| 295 | 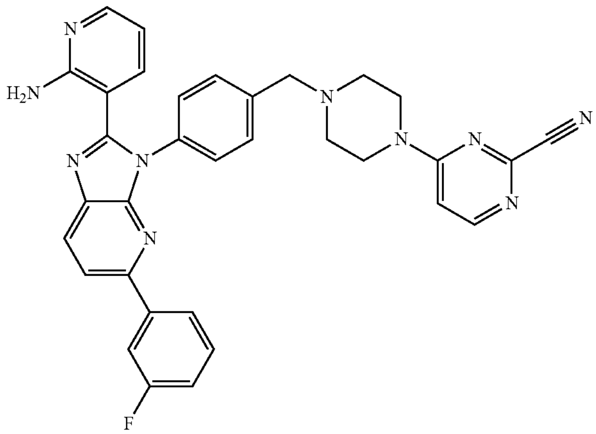 [SMILES: N#Cc1nccc(N2CCN(Cc3ccc(-n4c(-c5cccnc5N)nc5ccc(-c6cccc(F)c6)nc54)cc3)CC2)n1] | 4-(4-(4-(2-(2-aminopyridin-3-yl)-5-(3-fluorophenyl)-3H-imidazo[4,5-b]pyridin-3-yl)benzyl)piperazin-1-yl)pyrimidine-2-carbonitrile |
| 296 | 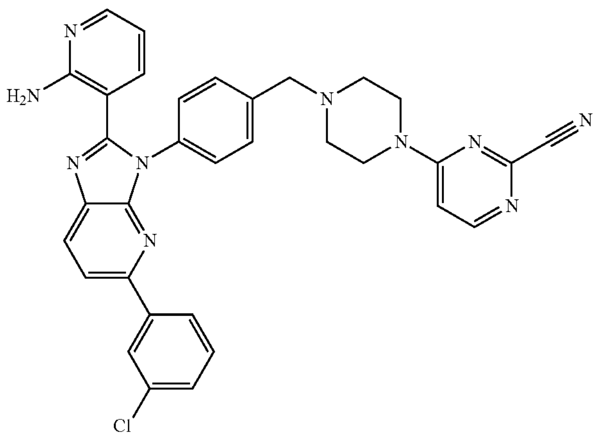 [SMILES: N#Cc1nccc(N2CCN(Cc3ccc(-n4c(-c5cccnc5N)nc5ccc(-c6cccc(Cl)c6)nc54)cc3)CC2)n1] | 4-(4-(4-(2-(2-aminopyridin-3-yl)-5-(3-chlorophenyl)-3H-imidazo[4,5-b]pyridin-3-yl)benzyl)piperazin-1-yl)pyrimidine-2-carbonitrile |
| 297 | 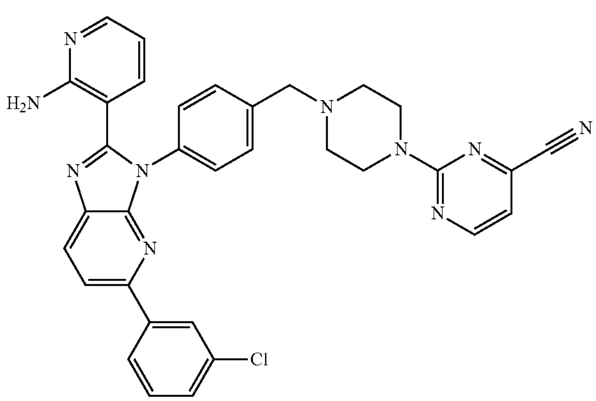 [SMILES: N#Cc1ccnc(N2CCN(Cc3ccc(-n4c(-c5cccnc5N)nc5ccc(-c6cccc(Cl)c6)nc54)cc3)CC2)n1] | 2-(4-(4-(2-(2-aminopyridin-3-yl)-5-(3-chlorophenyl)-3H-imidazo[4,5-b]pyridin-3-yl)benzyl)piperazin-1-yl)pyrimidine-4-carbonitrile |

TABLE 1-continued

| Example | Compound Structure | Compound Name |
|---|---|---|
| 298 | 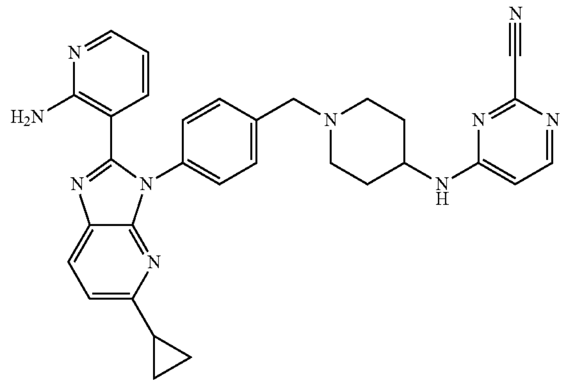 [SMILES: N#Cc1nccc(NC2CCN(Cc3ccc(-n4c(-c5cccnc5N)nc5ccc(C6CC6)nc54)cc3)CC2)n1] | 4-((1-(4-(2-(2-aminopyridin-3-yl)-5-cyclopropyl-3H-imidazo[4,5-b]pyridin-3-yl)benzyl)piperidin-4-yl)amino)pyrimidine-2-carbonitrile |
| 299 | 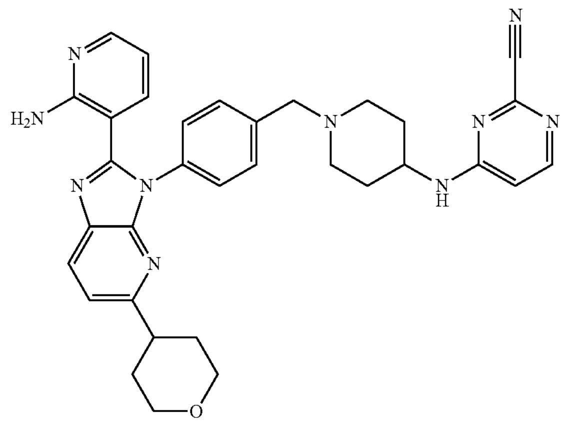 | 4-((1-(4-(2-(2-aminopyridin-3-yl)-5-(tetrahydro-2H-pyran-4-yl)-3H-imidazo[4,5-b]pyridin-3-yl)benzyl)piperidin-4-yl)amino)pyrimidine-2-carbonitrile |
| 300 | 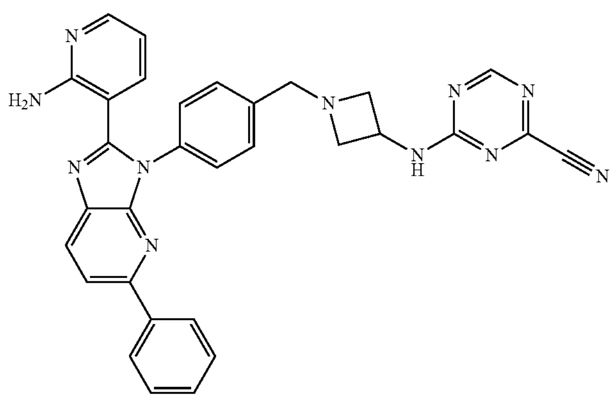 [SMILES: N#Cc1ncnc(NC2CN(Cc3ccc(-n4c(-c5cccnc5N)nc5ccc(-c6ccccc6)nc54)cc3)C2)n1] | 4-((1-(4-(2-(2-aminopyridin-3-yl)-5-phenyl-3H-imidazo[4,5-b]pyridin-3-yl)benzyl)azetidin-3-yl)amino)-1,3,5-triazine-2-carbonitrile |
| 301 | 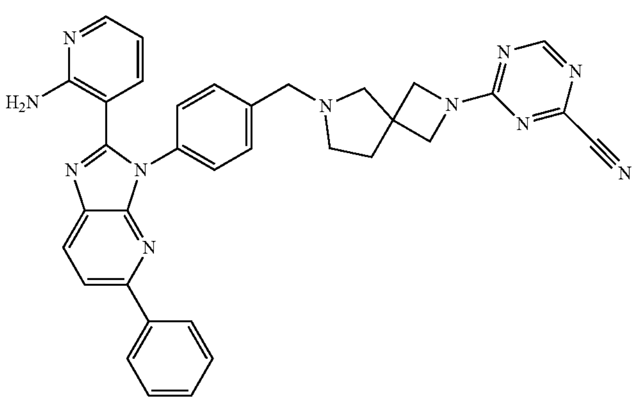 [SMILES: N#Cc1ncnc(N2CC3(CCN(Cc4ccc(-n5c(-c6cccnc6N)nc6ccc(-c7ccccc7)nc65)cc4)C3)C2)n1] | 4-(6-(4-(2-(2-aminopyridin-3-yl)-5-phenyl-3H-imidazo[4,5-b]pyridin-3-yl)benzyl)-2,6-diazaspiro[3.4]octan-2-yl)-1,3,5-triazine-2-carbonitrile |

TABLE 1-continued

| Example | Compound Structure | Compound Name |
|---|---|---|
| 302 | 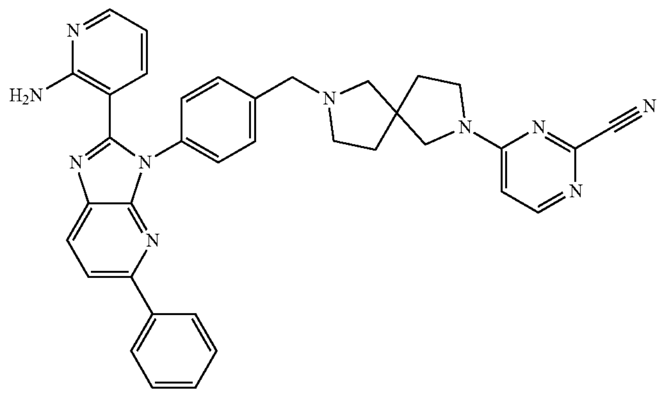 [SMILES: N#Cc1nccc(N2CCC3(CCN(Cc4ccc(-n5c(-c6cccnc6N)nc6ccc(-c7ccccc7)nc65)cc4)C3)C2)n1] | 4-(7-(4-(2-(2-aminopyridin-3-yl)-5-phenyl-3H-imidazo[4,5-b]pyridin-3-yl)benzyl)-2,7-diazaspiro[4.4]nonan-2-yl)pyrimidine-2-carbonitrile |
| 303 | 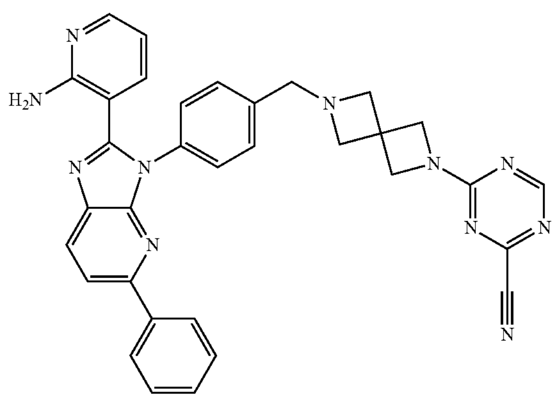 [SMILES: N#Cc1ncnc(N2CC3(CN(Cc4ccc(-n5c(-c6cccnc6N)nc6ccc(-c7ccccc7)nc65)cc4)C3)C2)n1] | 4-(6-(4-(2-(2-aminopyridin-3-yl)-5-phenyl-3H-imidazo[4,5-b]pyridin-3-yl)benzyl)-2,6-diazaspiro[3.3]heptan-2-yl)-1,3,5-triazine-2-carbonitrile |
| 304 | 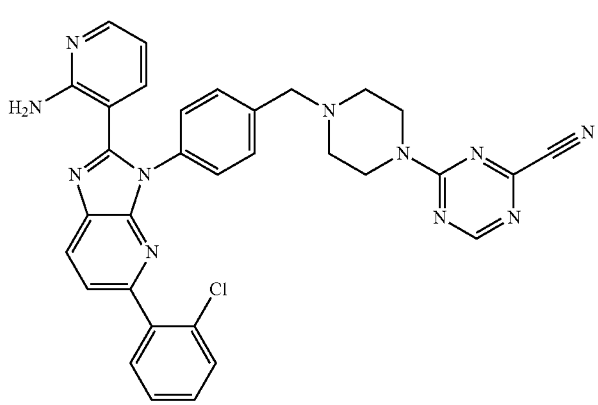 | 4-(4-(4-(2-(2-aminopyridin-3-yl)-5-(2-chlorophenyl)-3H-imidazo[4,5-b]pyridin-3-yl)benzyl)piperazin-1-yl)-1,3,5-triazine-2-carbonitrile |

TABLE 1-continued

| Example | Compound Structure | Compound Name |
|---|---|---|
| 305 | 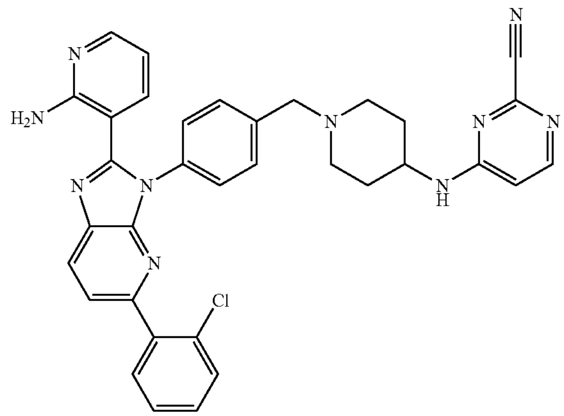 | 4-((1-(4-(2-(2-aminopyridin-3-yl)-5-(2-chlorophenyl)-3H-imidazo[4,5-b]pyridin-3-yl)benzyl)piperidin-4-yl)amino)pyrimidine-2-carbonitrile |
| 306 | 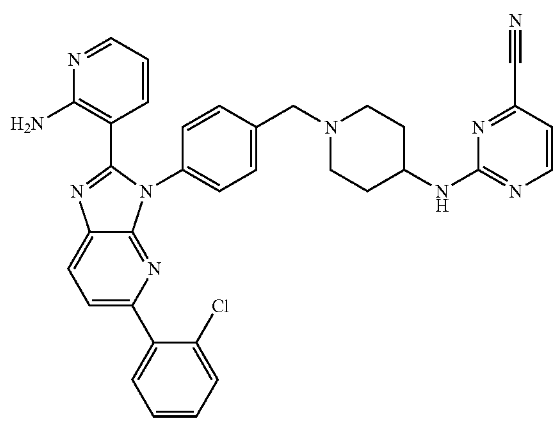 | 2-((1-(4-(2-(2-aminopyridin-3-yl)-5-(2-chlorophenyl)-3H-imidazo[4,5-b]pyridin-3-yl)benzyl)piperidin-4-yl)amino)pyrimidine-4-carbonitrile |
| 307 | 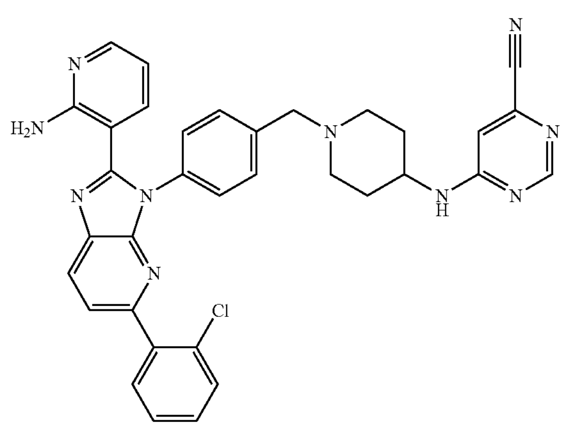 | 6-((1-(4-(2-(2-aminopyridin-3-yl)-5-(2-chlorophenyl)-3H-imidazo[4,5-b]pyridin-3-yl)benzyl)piperidin-4-yl)amino)pyrimidine-4-carbonitrile |

TABLE 1-continued

| Example | Compound Structure | Compound Name |
|---|---|---|
| 308 | 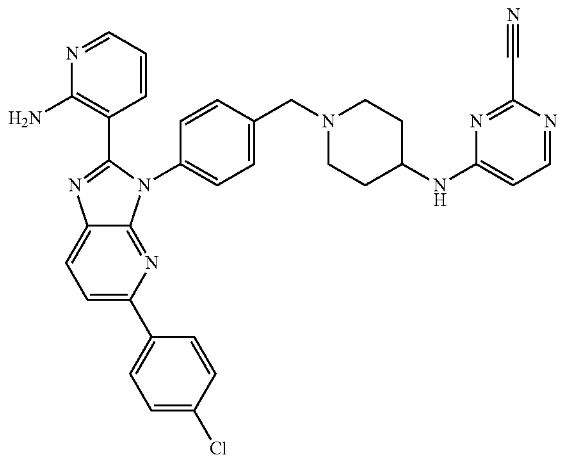 [SMILES: N#Cc1nccc(NC2CCN(Cc3ccc(-n4c(-c5cccnc5N)nc5ccc(-c6ccc(Cl)cc6)nc54)cc3)CC2)n1] | 4-((1-(4-(2-(2-aminopyridin-3-yl)-5-(4-chlorophenyl)-3H-imidazo[4,5-b]pyridin-3-yl)benzyl)piperidin-4-yl)amino)pyrimidine-2-carbonitrile |
| 309 | 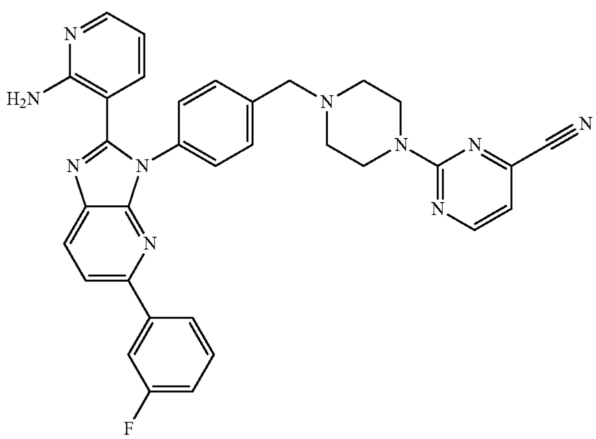 [SMILES: N#Cc1ccnc(N2CCN(Cc3ccc(-n4c(-c5cccnc5N)nc5ccc(-c6cccc(F)c6)nc54)cc3)CC2)n1] | 2-(4-(4-(2-(2-aminopyridin-3-yl)-5-(3-fluorophenyl)-3H-imidazo[4,5-b]pyridin-3-yl)benzyl)piperazin-1-yl)pyrimidine-4-carbonitrile |
| 310 | 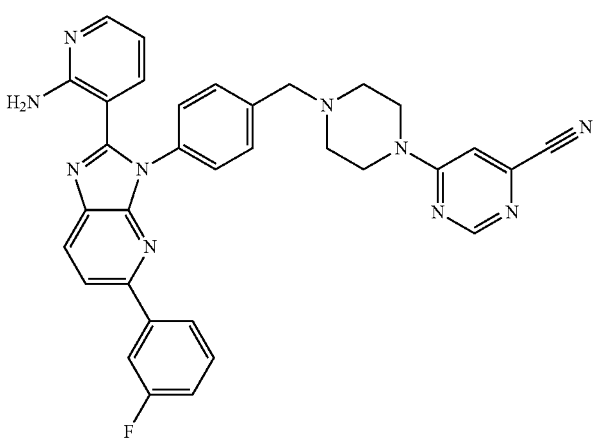 [SMILES: N#Cc1cc(N2CCN(Cc3ccc(-n4c(-c5cccnc5N)nc5ccc(-c6cccc(F)c6)nc54)cc3)CC2)ncn1] | 6-(4-(4-(2-(2-aminopyridin-3-yl)-5-(3-fluorophenyl)-3H-imidazo[4,5-b]pyridin-3-yl)benzyl)piperazin-1-yl)pyrimidine-4-carbonitrile |

TABLE 1-continued

| Example | Compound Structure | Compound Name |
|---|---|---|
| 311 | 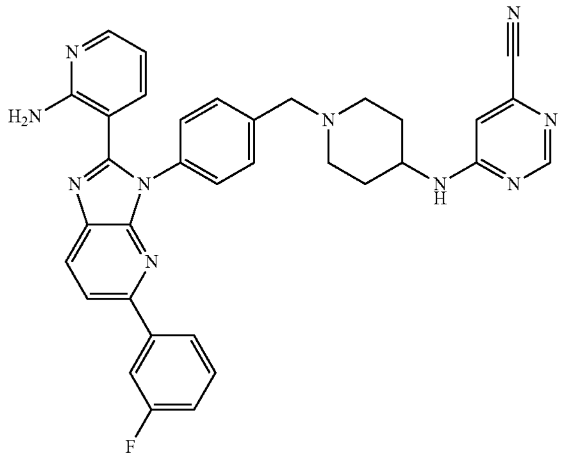 [SMILES: N#Cc1cc(NC2CCN(Cc3ccc(-n4c(-c5cccnc5N)nc5ccc(-c6cccc(F)c6)nc54)cc3)CC2)ncn1] | 6-((1-(4-(2-(2-aminopyridin-3-yl)-5-(3-fluorophenyl)-3H-imidazo[4,5-b]pyridin-3-yl)benzyl)piperidin-4-yl)amino)pyrimidine-4-carbonitrile |
| 312 | 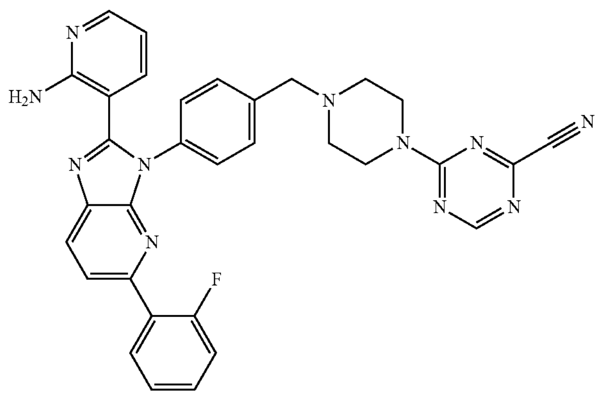 | 4-(4-(4-(2-(2-aminopyridin-3-yl)-5-(2-fluorophenyl)-3H-imidazo[4,5-b]pyridin-3-yl)benzyl)piperazin-1-yl)-1,3,5-triazine-2-carbonitrile |
| 313 | 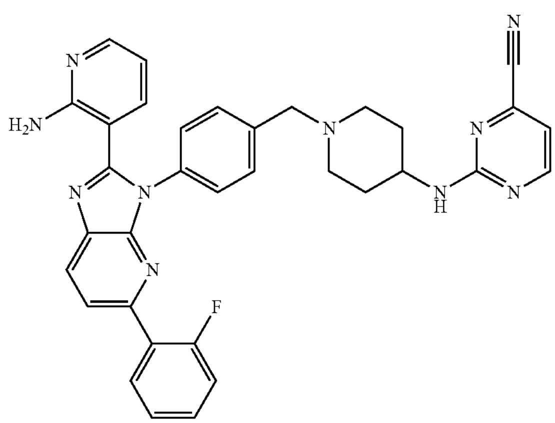 [SMILES: N#Cc1ccnc(NC2CCN(Cc3ccc(-n4c(-c5cccnc5N)nc5ccc(-c6ccccc6F)nc54)cc3)CC2)n1] | 2-((1-(4-(2-(2-aminopyridin-3-yl)-5-(2-fluorophenyl)-3H-imidazo[4,5-b]pyridin-3-yl)benzyl)piperidin-4-yl)amino)pyrimidine-4-carbonitrile |

TABLE 1-continued

| Example | Compound Structure | Compound Name |
|---|---|---|
| 314 | 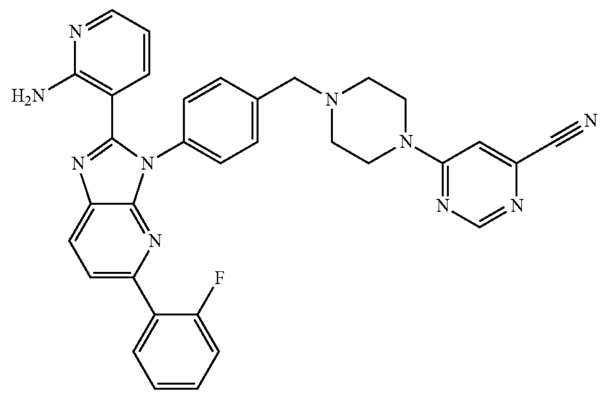 [SMILES: N#Cc1cc(N2CCN(Cc3ccc(-n4c(-c5cccnc5N)nc5ccc(-c6ccccc6F)nc54)cc3)CC2)ncn1] | 6-(4-(4-(2-(2-aminopyridin-3-yl)-5-(2-fluorophenyl)-3H-imidazo[4,5-b]pyridin-3-yl)benzyl)piperazin-1-yl)pyrimidine-4-carbonitrile |
| 315 | 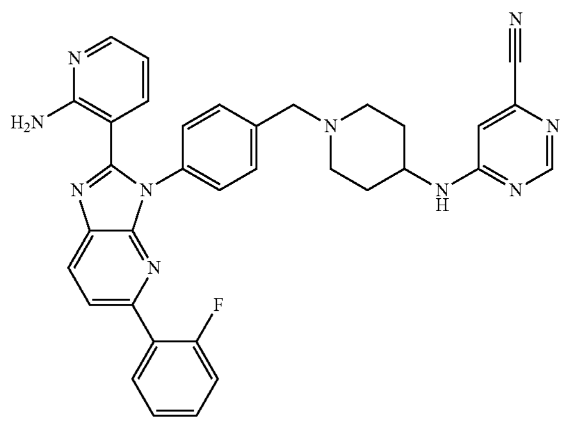 [SMILES: N#Cc1cc(NC2CCN(Cc3ccc(-n4c(-c5cccnc5N)nc5ccc(-c6ccccc6F)nc54)cc3)CC2)ncn1] | 6-((1-(4-(2-(2-aminopyridin-3-yl)-5-(2-fluorophenyl)-3H-imidazo[4,5-b]pyridin-3-yl)benzyl)piperidin-4-yl)amino)pyrimidine-4-carbonitrile |
| 316 | 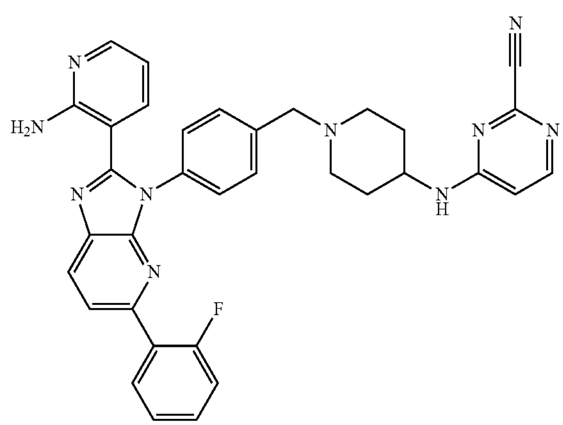 [SMILES: N#Cc1nccc(NC2CCN(Cc3ccc(-n4c(-c5cccnc5N)nc5ccc(-c6ccccc6F)nc54)cc3)CC2)n1] | 4-((1-(4-(2-(2-aminopyridin-3-yl)-5-(2-fluorophenyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 317 | 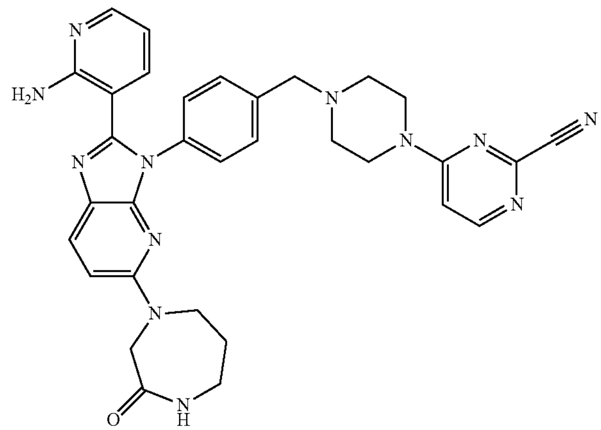 [SMILES: N#Cc1nccc(N2CCN(Cc3ccc(-n4c(-c5cccnc5N)nc5ccc(N6CCCNC(=O)C6)nc54)cc3)CC2)n1] | 4-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-2-carbonitrile |
| 318 | 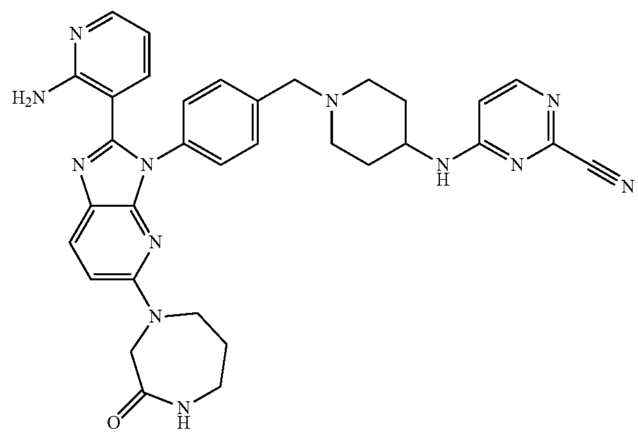 [SMILES: N#Cc1nccc(NC2CCN(Cc3ccc(-n4c(-c5cccnc5N)nc5ccc(N6CCCNC(=O)C6)nc54)cc3)CC2)n1] | 4-((1-(4-(2-(2-aminopyridin-3-yl)-5-(3-oxo-1,4-diazepan-1-yl)-3H-imidazo[4,5-b]pyridin-3-yl)benzyl)piperidin-4-yl)amino)pyrimidine-2-carbonitrile |
| 319 | 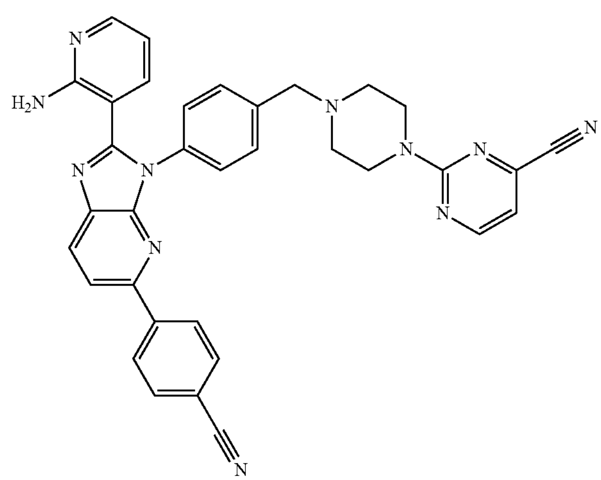 [SMILES: N#Cc1ccc(-c2ccc3nc(-c4cccnc4N)n(-c4ccc(CN5CCN(c6nccc(C#N)n6)CC5)cc4)c3n2)cc1] | 2-(4-(4-(2-(2-aminopyridin-3-yl)-5-(4-cyanophenyl)-3H-imidazo[4,5-b]pyridin-3-yl)benzyl)piperazin-1-yl)pyrimidine-4-carbonitrile |

TABLE 1-continued

| Example | Compound Structure | Compound Name |
|---|---|---|
| 320 | 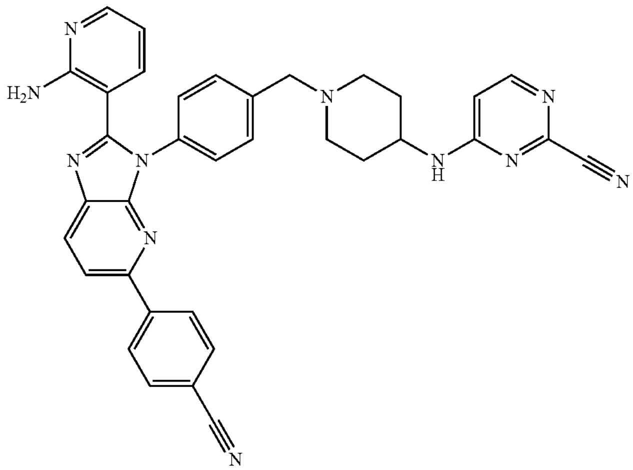 [SMILES: N#Cc1ccc(-c2ccc3nc(-c4cccnc4N)n(-c4ccc(CN5CCC(Nc6ccnc(C#N)n6)CC5)cc4)c3n2)cc1] | 4-((1-(4-(2-(2-aminopyridin-3-yl)-5-(4-cyanophenyl)-3H-imidazo[4,5-b]pyridin-3-yl)benzyl)piperidin-4-yl)amino)pyrimidine-2-carbonitrile |
| 321 | 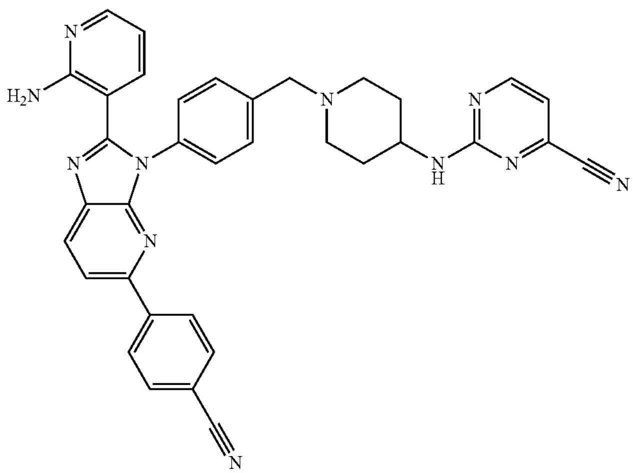 [SMILES: N#Cc1ccc(-c2ccc3nc(-c4cccnc4N)n(-c4ccc(CN5CCC(Nc6nccc(C#N)n6)CC5)cc4)c3n2)cc1] | 2-((1-(4-(2-(2-aminopyridin-3-yl)-5-(4-cyanophenyl)-3H-imidazo[4,5-b]pyridin-3-yl)benzyl)piperidin-4-yl)amino)pyrimidine-4-carbonitrile |
| 322 | 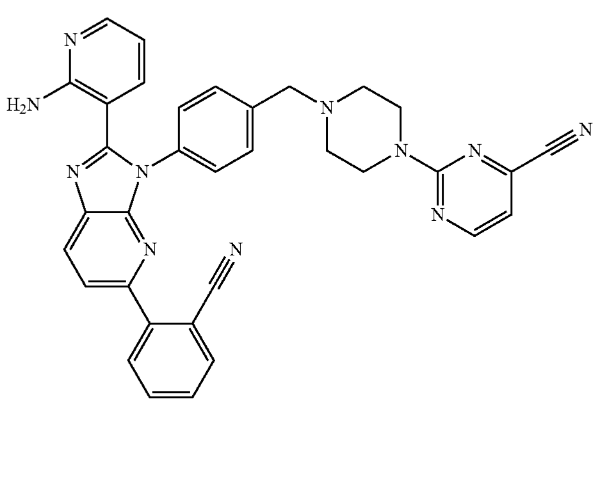 [SMILES: N#Cc1ccnc(N2CCN(Cc3ccc(-n4c(-c5cccnc5N)nc5ccc(-c6ccccc6C#N)nc54)cc3)CC2)n1] | 2-(4-(4-(2-(2-aminopyridin-3-yl)-5-(2-cyanophenyl)-3H-imidazo[4,5-b]pyridin-3-yl)benzyl)piperazin-1-yl)pyrimidine-4-carbonitrile |

TABLE 1-continued

| Example | Compound Structure | Compound Name |
|---|---|---|
| 323 | 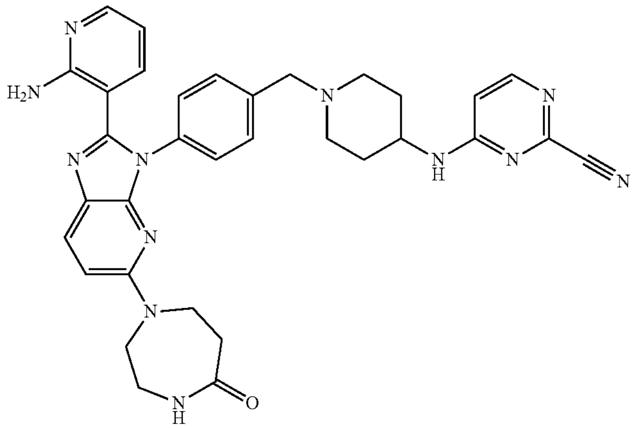 [SMILES: N#Cc1nccc(NC2CCN(Cc3ccc(-n4c(-c5cccnc5N)nc5ccc(N6CCNC(=O)CC6)nc54)cc3)CC2)n1] | 4-((1-(4-(2-(2-aminopyridin-3-yl)-5-(5-oxo-1,4-diazepan-1-yl)-3H-imidazo[4,5-b]pyridin-3-yl)benzyl)piperidin-4-yl)amino)pyrimidine-2-carbonitrile |
| 324 | 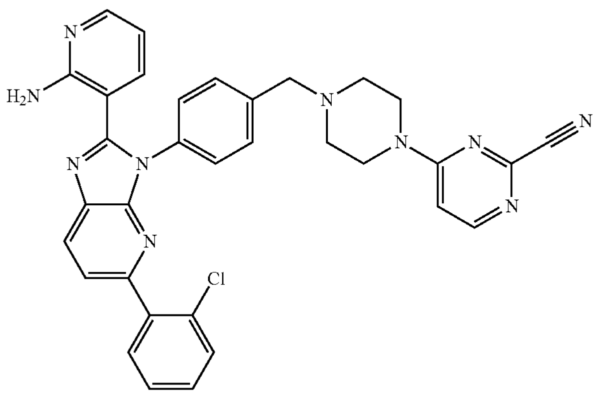 | 4-(4-(4-(2-(2-aminopyridin-3-yl)-5-(2-chlorophenyl)-3H-imidazo[4,5-b]pyridin-3-yl)benzyl)piperazin-1-yl)pyrimidine-2-carbonitrile |
| 325 | 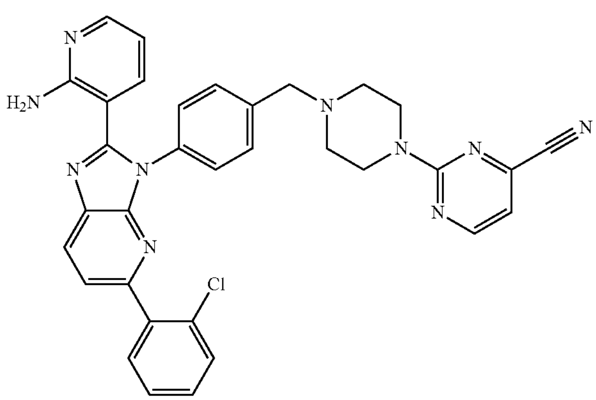 | 2-(4-(4-(2-(2-aminopyridin-3-yl)-5-(2-chlorophenyl)-3H-imidazo[4,5-b]pyridin-3-yl)benzyl)piperazin-1-yl)pyrimidine-4-carbonitrile |

TABLE 1-continued

| Example | Compound Structure | Compound Name |
|---|---|---|
| 326 | 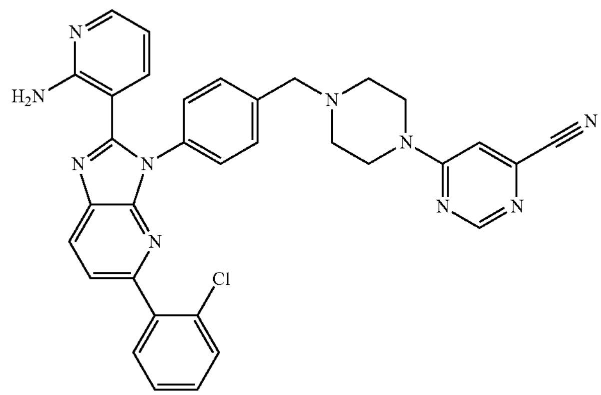 [SMILES: N#Cc1cc(N2CCN(Cc3ccc(-n4c(-c5cccnc5N)nc5ccc(-c6ccccc6Cl)nc54)cc3)CC2)ncn1] | 6-(4-(4-(2-(2-aminopyridin-3-yl)-5-(2-chlorophenyl)-3H-imidazo[4,5-b]pyridin-3-yl)benzyl)piperazin-1-yl)pyrimidine-4-carbonitrile |
| 327 | 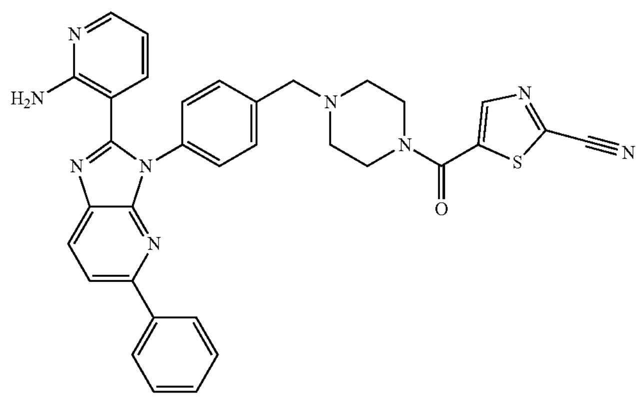 [SMILES: N#Cc1ncc(C(=O)N2CCN(Cc3ccc(-n4c(-c5cccnc5N)nc5ccc(-c6ccccc6)nc54)cc3)CC2)s1] | 5-(4-(4-(2-(2-aminopyridin-3-yl)-5-phenyl-3H-imidazo[4,5-b]pyridin-3-yl)benzyl)piperazine-1-carbonyl)thiazole-2-carbonitrile |
| 328 | 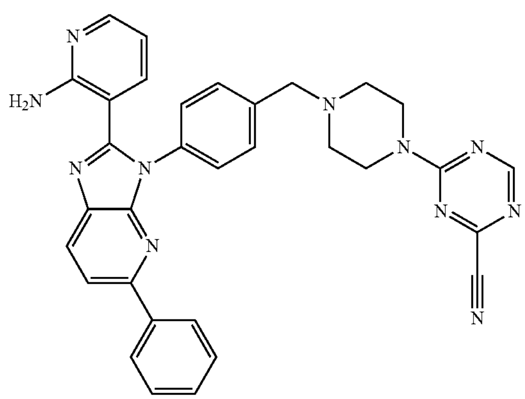 [SMILES: N#Cc1ncnc(N2CCN(Cc3ccc(-n4c(-c5cccnc5N)nc5ccc(-c6ccccc6)nc54)cc3)CC2)n1] | 4-(4-(4-(2-(2-aminopyridin-3-yl)-5-phenyl-3H-imidazo[4,5-b]pyridin-3-yl)benzyl)piperazin-1-yl)-1,3,5-triazine-2-carbonitrile |
| 329 | 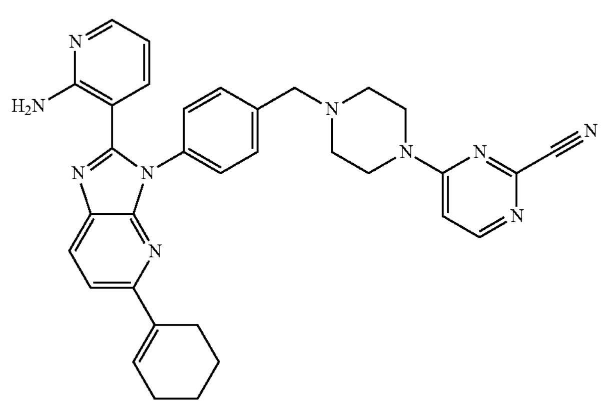 [SMILES: N#Cc1nccc(N2CCN(Cc3ccc(-n4c(-c5cccnc5N)nc5ccc(C6=CCCCC6)nc54)cc3)CC2)n1] | 4-(4-(4-(2-(2-aminopyridin-3-yl)-5-(cyclohex-1-en-1-yl)-3H-imidazo[4,5-b]pyridin-3-yl)benzyl)piperazin-1-yl)pyrimidine-2-carbonitrile |

TABLE 1-continued

| Example | Compound Structure | Compound Name |
|---|---|---|
| 330 | 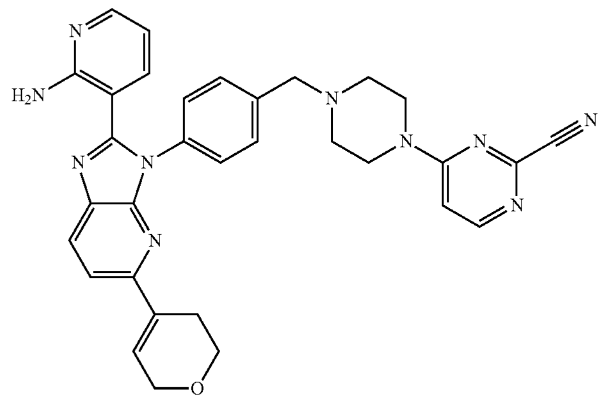 [SMILES: N#Cc1nccc(N2CCN(Cc3ccc(-n4c(-c5cccnc5N)nc5ccc(C6=CCOCC6)nc54)cc3)CC2)n1] | 4-(4-(4-(2-(2-aminopyridin-3-yl)-5-(3,6-dihydro-2H-pyran-4-yl)-3H-imidazo[4,5-b]pyridin-3-yl)benzyl)piperazin-1-yl)pyrimidine-2-carbonitrile |
| 331 | 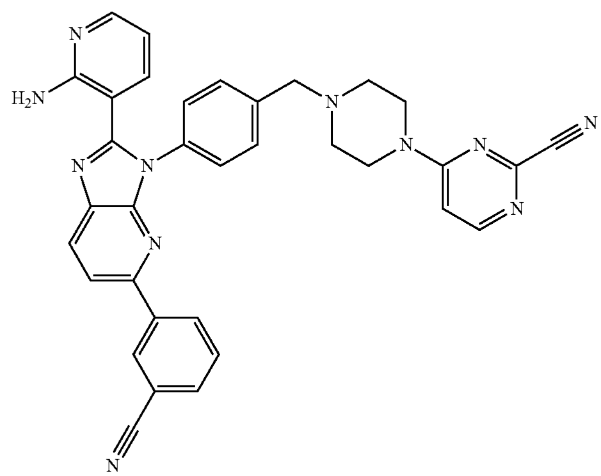 [SMILES: N#Cc1cccc(-c2ccc3nc(-c4cccnc4N)n(-c4ccc(CN5CCN(c6ccnc(C#N)n6)CC5)cc4)c3n2)c1] | 4-(4-(4-(2-(2-aminopyridin-3-yl)-5-(3-cyanophenyl)-3H-imidazo[4,5-b]pyridin-3-yl)benzyl)piperazin-1-yl)pyrimidine-2-carbonitrile |
| 332 | 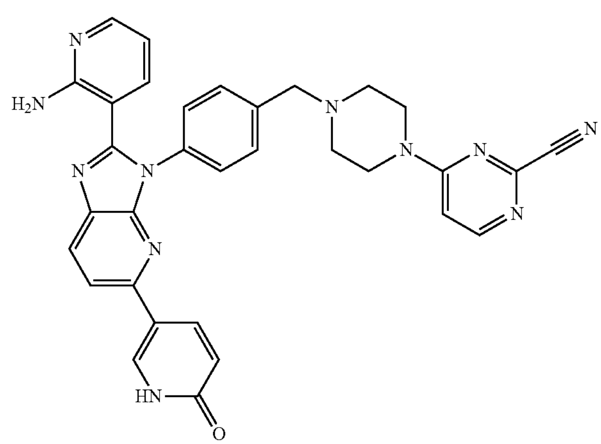 [SMILES: N#Cc1nccc(N2CCN(Cc3ccc(-n4c(-c5cccnc5N)nc5ccc(-c6ccc(=O)[nH]c6)nc54)cc3)CC2)n1] | 4-(4-(4-(2-(2-aminopyridin-3-yl)-5-(6-oxo-1,6-dihydropyridin-3-yl)-3H-imidazo[4,5-b]pyridin-3-yl)benzyl)piperazin-1-yl)pyrimidine-2-carbonitrile |

TABLE 1-continued

| Example | Compound Structure | Compound Name |
|---|---|---|
| 333 | 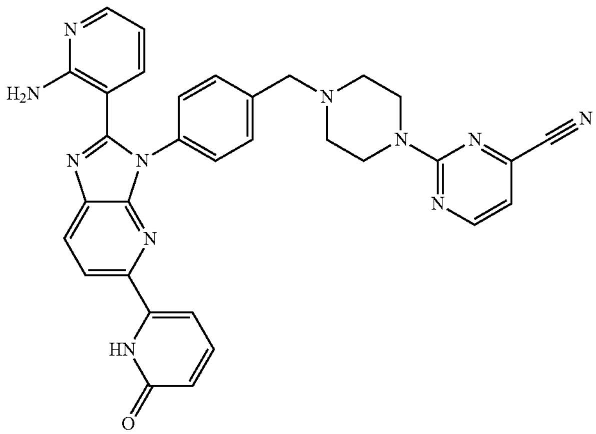 [SMILES: N#Cc1ccnc(N2CCN(Cc3ccc(-n4c(-c5cccnc5N)nc5ccc(-c6cccc(=O)[nH]6)nc54)cc3)CC2)n1] | 2-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-4-carbonitrile |
| 334 | 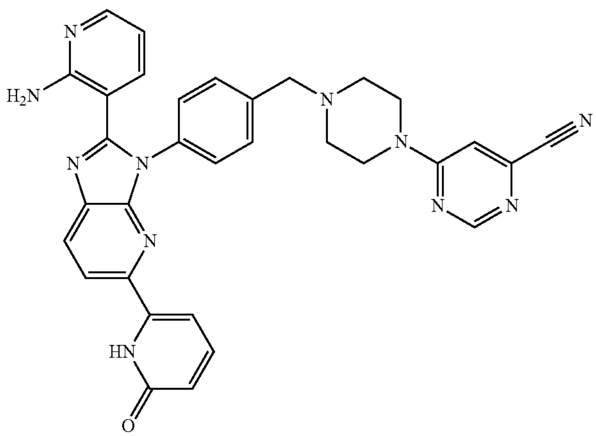 [SMILES: N#Cc1cc(N2CCN(Cc3ccc(-n4c(-c5cccnc5N)nc5ccc(-c6cccc(=O)[nH]6)nc54)cc3)CC2)ncn1] | 6-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-4-carbonitrile |
| 335 | 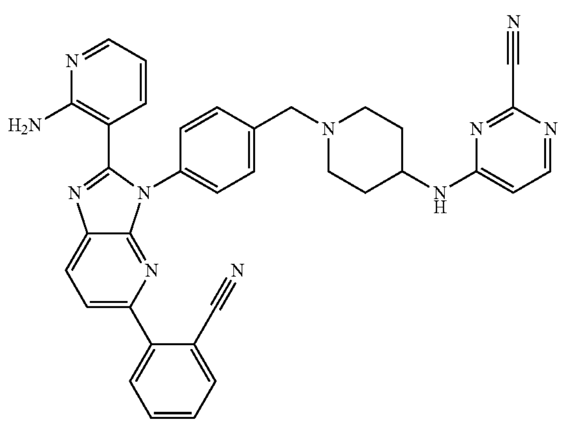 [SMILES: N#Cc1nccc(NC2CCN(Cc3ccc(-n4c(-c5cccnc5N)nc5ccc(-c6ccccc6C#N)nc54)cc3)CC2)n1] | 4-((1-(4-(2-(2-aminopyridin-3-yl)-5-(2-cyanophenyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 336 | 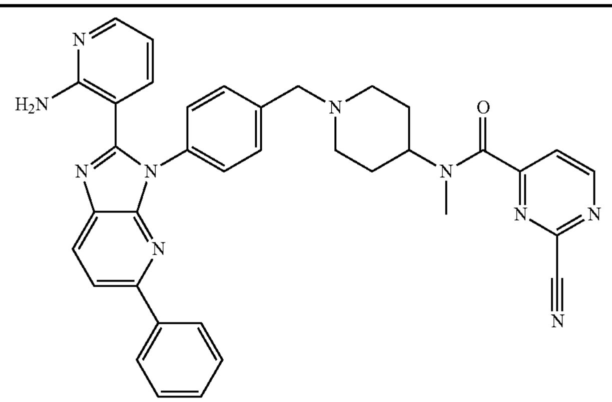 | N-(1-(4-(2-(2-aminopyridin-3-yl)-5-phenyl-3H-imidazo[4,5-b]pyridin-3-yl)benzyl)piperidin-4-yl)-2-cyano-N-methylpyrimidine-4-carboxamide |
| 337 | 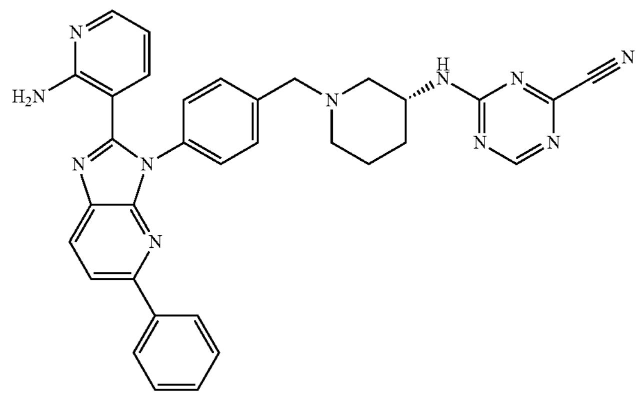 [SMILES: N#Cc1ncnc(N[C@@H]2CCCN(Cc3ccc(-n4c(-c5cccnc5N)nc5ccc(-c6ccccc6)nc54)cc3)C2)n1] | (R)-4-((1-(4-(2-(2-aminopyridin-3-yl)-5-phenyl-3H-imidazo[4,5-b]pyridin-3-yl)benzyl)piperidin-3-yl)amino)-1,3,5-triazine-2-carbonitrile |
| 338 | 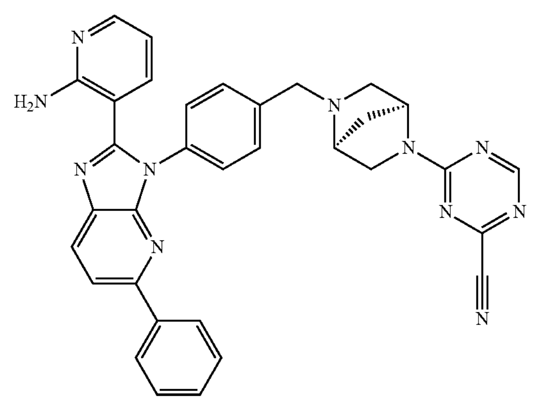 [SMILES: N#Cc1ncnc(N2C[C@@H]3C[C@H]2CN3Cc2ccc(-n3c(-c4cccnc4N)nc4ccc(-c5ccccc5)nc43)cc2)n1] | 4-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile |
| 339 | 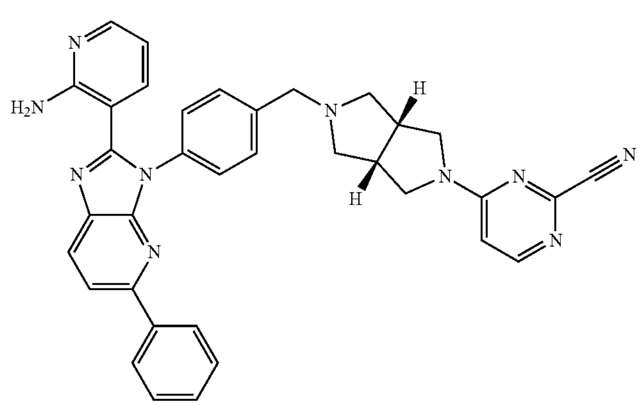 [SMILES: N#Cc1nccc(N2C[C@H]3CN(Cc4ccc(-n5c(-c6cccnc6N)nc6ccc(-c7ccccc7)nc65)cc4)C[C@H]3C2)n1] | 4-((3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile |

TABLE 1-continued

| Example | Compound Structure | Compound Name |
|---|---|---|
| 340 | 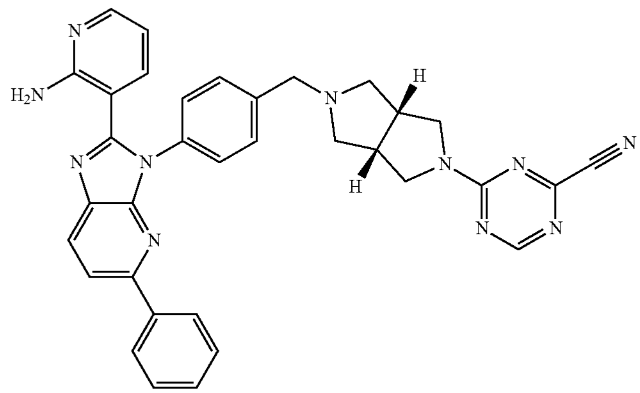 [SMILES: N#Cc1ncnc(N2C[C@H]3CN(Cc4ccc(-n5c(-c6cccnc6N)nc6ccc(-c7ccccc7)nc65)cc4)C[C@H]3C2)n1] | 4-((3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)-1,3,5-triazine-2-carbonitrile |
| 341 | 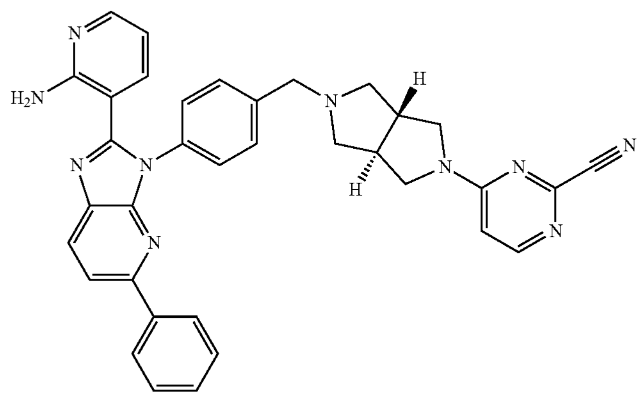 [SMILES: N#Cc1nccc(N2C[C@H]3CN(Cc4ccc(-n5c(-c6cccnc6N)nc6ccc(-c7ccccc7)nc65)cc4)C[C@@H]3C2)n1] | 4-((3aR,6aR)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile |
| 342 | 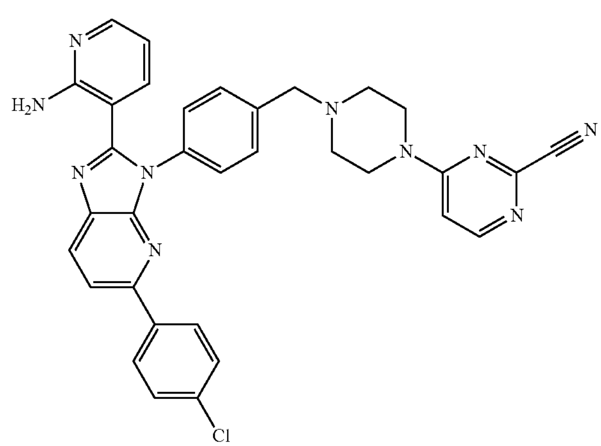 | 4-(4-(4-(2-(2-aminopyridin-3-yl)-5-(4-chlorophenyl)-3H-imidazo[4,5-b]pyridin-3-yl)benzyl)piperazin-1-yl)pyrimidine-2-carbonitrile |

| Example | Compound Structure | Compound Name |
|---|---|---|
| 343 | 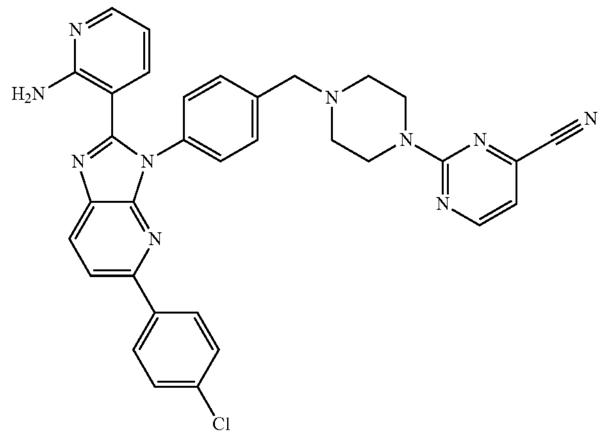 | 2-(4-(4-(2-(2-aminopyridin-3-yl)-5-(4-chlorophenyl)-3H-imidazo[4,5-b]pyridin-3-yl)benzyl)piperazin-1-yl)pyrimidine-4-carbonitrile |
| 344 | 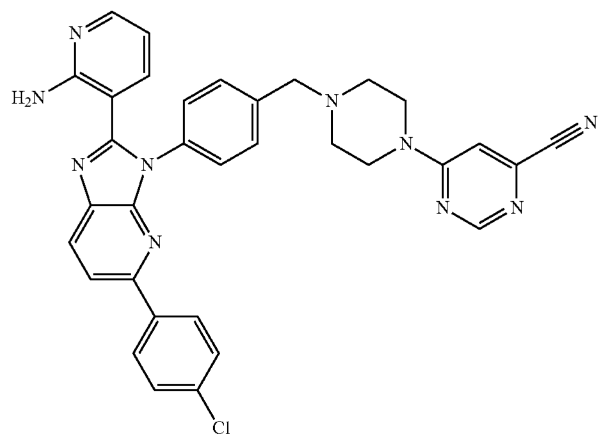 | 6-(4-(4-(2-(2-aminopyridin-3-yl)-5-(4-chlorophenyl)-3H-imidazo[4,5-b]pyridin-3-yl)benzyl)piperazin-1-yl)pyrimidine-4-carbonitrile |
| 345 | 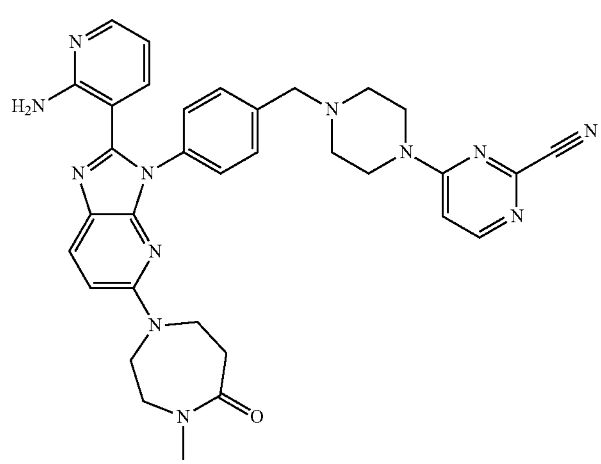 [SMILES: CN1CCN(c2ccc3nc(-c4cccnc4N)n(-c4ccc(CN5CCN(c6ccnc(C#N)n6)CC5)cc4)c3n2)CCC1=O] | 4-(4-(4-(2-(2-aminopyridin-3-yl)-5-(4-methyl-5-oxo-1,4-diazepan-1-yl)-3H-imidazo[4,5-b]pyridin-3-yl)benzyl)piperazin-1-yl)pyrimidine-2-carbonitrile |

TABLE 1-continued

| Example | Compound Structure | Compound Name |
|---|---|---|
| 346 | 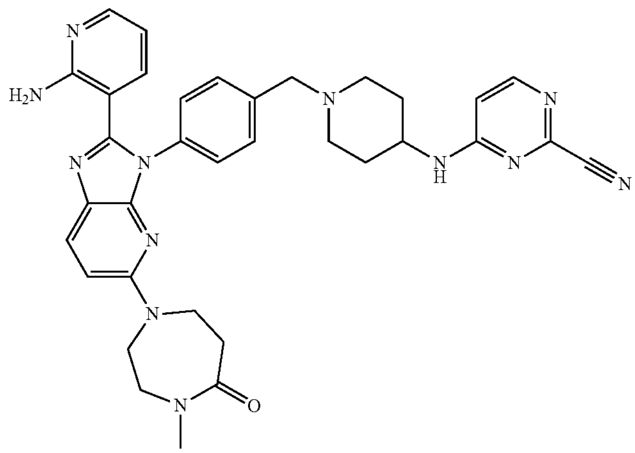 [SMILES: CN1CCN(c2ccc3nc(-c4cccnc4N)n(-c4ccc(CN5CCC(Nc6ccnc(C#N)n6)CC5)cc4)c3n2)CCC1=O] | 4-((1-(4-(2-(2-aminopyridin-3-yl)-5-(4-methyl-5-oxo-1,4-diazepan-1-yl)-3H-imidazo[4,5-b]pyridin-3-yl)benzyl)piperidin-4-yl)amino)pyrimidine-2-carbonitrile |
| 347 | 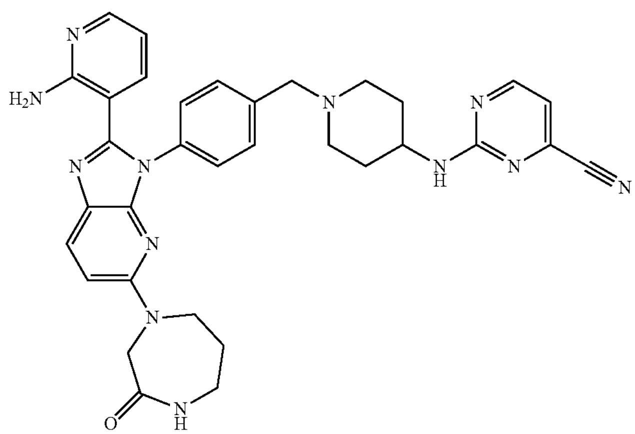 [SMILES: N#Cc1ccnc(NC2CCN(Cc3ccc(-n4c(-c5cccnc5N)nc5ccc(N6CCCNC(=O)C6)nc54)cc3)CC2)n1] | 2-((1-(4-(2-(2-aminopyridin-3-yl)-5-(3-oxo-1,4-diazepan-1-yl)-3H-imidazo[4,5-b]pyridin-3-yl)benzyl)piperidin-4-yl)amino)pyrimidine-4-carbonitrile |
| 348 | 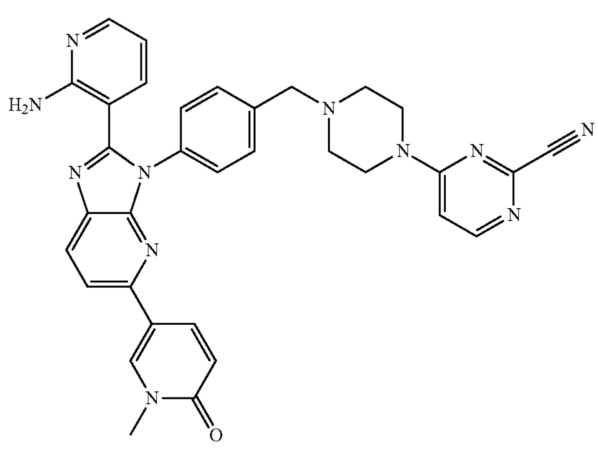 | 4-(4-(4-(2-(2-aminopyridin-3-yl)-5-(1-methyl-6-oxo-1,6-dihydropyridin-3-yl)-3H-imidazo[4,5-b]pyridin-3-yl)benzyl)piperazin-1-yl)pyrimidine-2-carbonitrile |

TABLE 1-continued

| Example | Compound Structure | Compound Name |
|---|---|---|
| 349 | 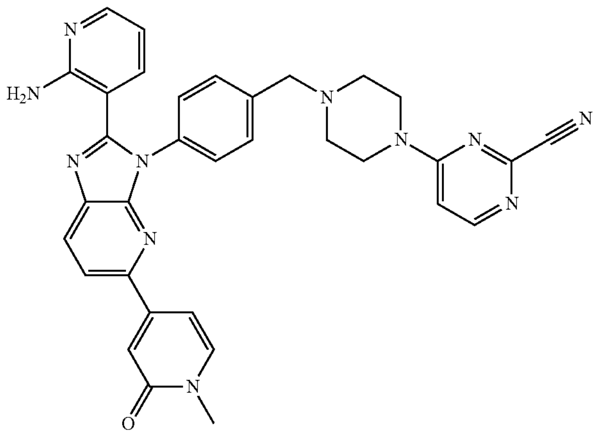 [SMILES: Cn1ccc(-c2ccc3nc(-c4cccnc4N)n(-c4ccc(CN5CCN(c6ccnc(C#N)n6)CC5)cc4)c3n2)cc1=O] | 4-(4-(4-(2-(2-aminopyridin-3-yl)-5-(1-methyl-2-oxo-1,2-dihydropyridin-4-yl)-3H-imidazo[4,5-b]pyridin-3-yl)benzyl)piperazin-1-yl)pyrimidine-2-carbonitrile |
| 350 | 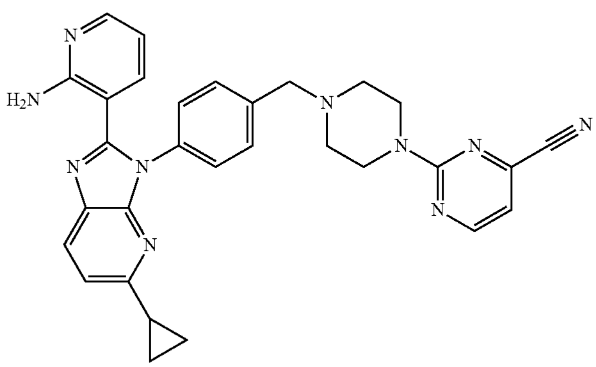 [SMILES: N#Cc1ccnc(N2CCN(Cc3ccc(-n4c(-c5cccnc5N)nc5ccc(C6CC6)nc54)cc3)CC2)n1] | 2-(4-(4-(2-(2-aminopyridin-3-yl)-5-cyclopropyl-3H-imidazo[4,5-b]pyridin-3-yl)benzyl)piperazin-1-yl)pyrimidine-4-carbonitrile |
| 351 | 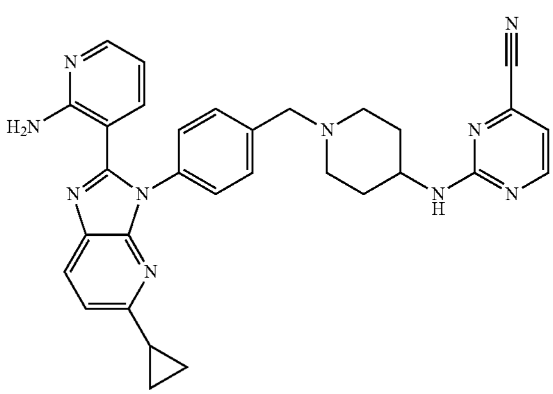 [SMILES: N#Cc1ccnc(NC2CCN(Cc3ccc(-n4c(-c5cccnc5N)nc5ccc(C6CC6)nc54)cc3)CC2)n1] | 2-((1-(4-(2-(2-aminopyridin-3-yl)-5-cyclopropyl-3H-imidazo[4,5-b]pyridin-3-yl)benzyl)piperidin-4-yl)amino)pyrimidine-4-carbonitrile |

TABLE 1-continued

| Example | Compound Structure | Compound Name |
|---|---|---|
| 352 | 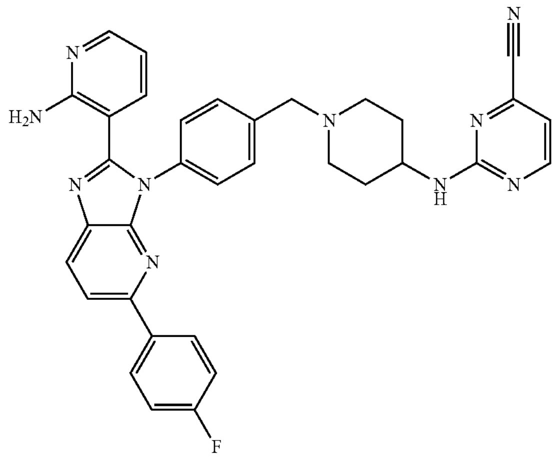 [SMILES: N#Cc1ccnc(NC2CCN(Cc3ccc(-n4c(-c5cccnc5N)nc5ccc(-c6ccc(F)cc6)nc54)cc3)CC2)n1] | 2-((1-(4-(2-(2-aminopyridin-3-yl)-5-(4-fluorophenyl)-3H-imidazo[4,5-b]pyridin-3-yl)benzyl)piperidin-4-yl)amino)pyrimidine-4-carbonitrile |
| 353 | 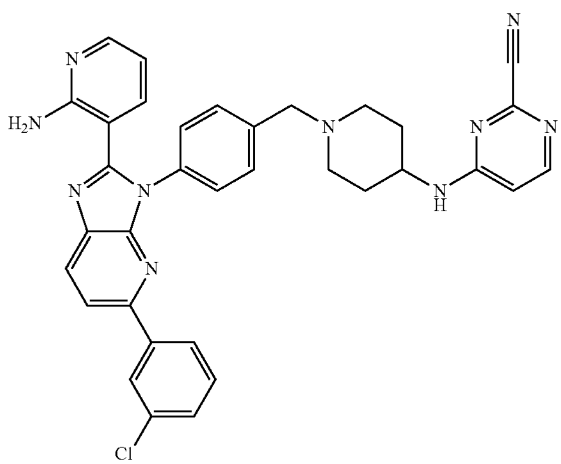 | 4-((1-(4-(2-(2-aminopyridin-3-yl)-5-(3-chlorophenyl)-3H-imidazo[4,5-b]pyridin-3-yl)benzyl)piperidin-4-yl)amino)pyrimidine-2-carbonitrile |
| 354 | 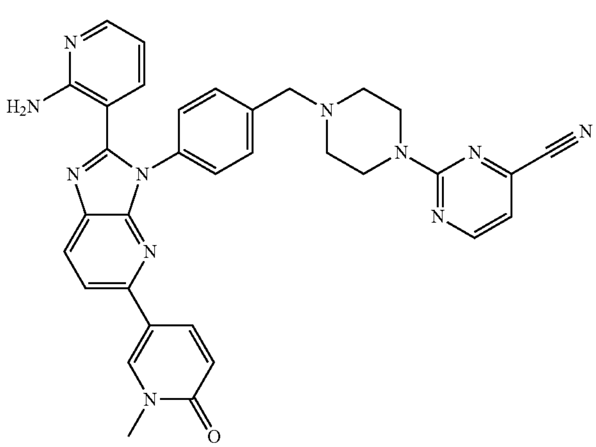 [SMILES: Cn1cc(-c2ccc3nc(-c4cccnc4N)n(-c4ccc(CN5CCN(c6nccc(C#N)n6)CC5)cc4)c3n2)ccc1=O] | 2-(4-(4-(2-(2-aminopyridin-3-yl)-5-(1-methyl-6-oxo-1,6-dihydropyridin-3-yl)-3H-imidazo[4,5-b]pyridin-3-yl)benzyl)piperazin-1-yl)pyrimidine-4-carbonitrile |

TABLE 1-continued

| Example | Compound Structure | Compound Name |
|---|---|---|
| 355 | 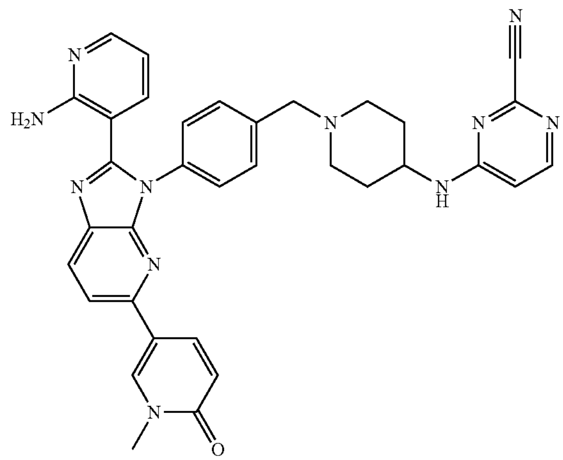 [SMILES: Cn1cc(-c2ccc3nc(-c4cccnc4N)n(-c4ccc(CN5CCC(Nc6ccnc(C#N)n6)CC5)cc4)c3n2)ccc1=O] | 4-((1-(4-(2-(2-aminopyridin-3-yl)-5-(1-methyl-6-oxo-1,6-dihydropyridin-3-yl)-3H-imidazo[4,5-b]pyridin-3-yl)benzyl)piperidin-4-yl)amino)pyrimidine-2-carbonitrile |
| 356 | 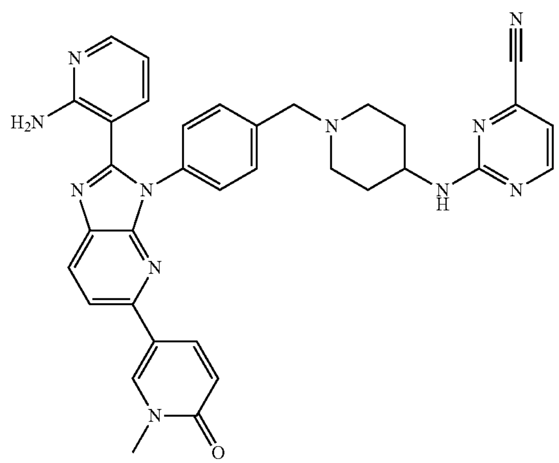 [SMILES: Cn1cc(-c2ccc3nc(-c4cccnc4N)n(-c4ccc(CN5CCC(Nc6nccc(C#N)n6)CC5)cc4)c3n2)ccc1=O] | 2-((1-(4-(2-(2-aminopyridin-3-yl)-5-(1-methyl-6-oxo-1,6-dihydropyridin-3-yl)-3H-imidazo[4,5-b]pyridin-3-yl)benzyl)piperidin-4-yl)amino)pyrimidine-4-carbonitrile |
| 357 | 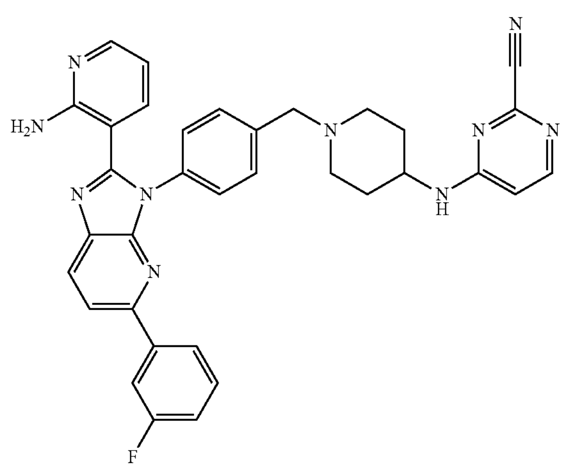 [SMILES: N#Cc1nccc(NC2CCN(Cc3ccc(-n4c(-c5cccnc5N)nc5ccc(-c6cccc(F)c6)nc54)cc3)CC2)n1] | 4-((1-(4-(2-(2-aminopyridin-3-yl)-5-(3-fluorophenyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 358 | 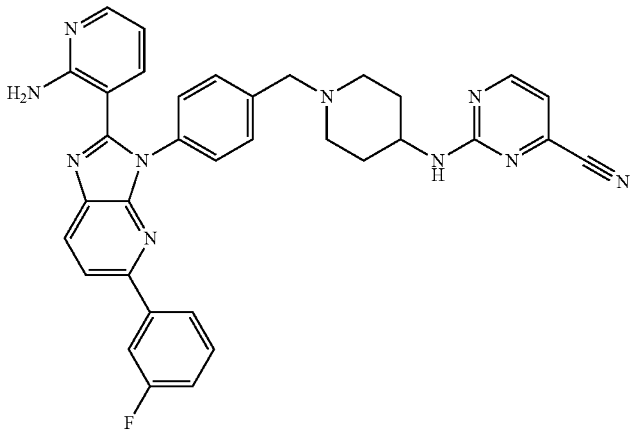 [SMILES: N#Cc1ccnc(NC2CCN(Cc3ccc(-n4c(-c5cccnc5N)nc5ccc(-c6cccc(F)c6)nc54)cc3)CC2)n1] | 2-((1-(4-(2-(2-aminopyridin-3-yl)-5-(3-fluorophenyl)-3H-imidazo[4,5-b]pyridin-3-yl)benzyl)piperidin-4-yl)amino)pyrimidine-4-carbonitrile |
| 359 | 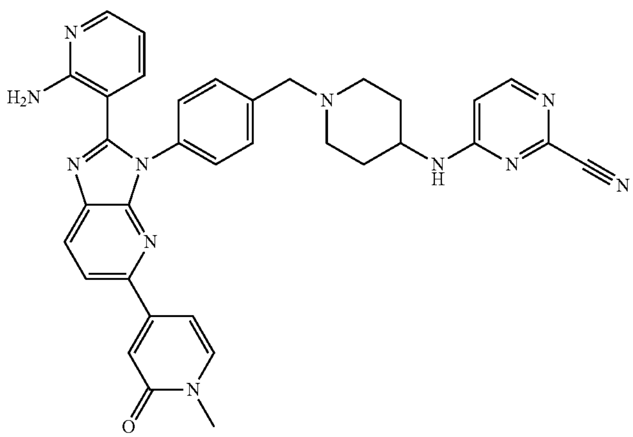 [SMILES: Cn1ccc(-c2ccc3nc(-c4cccnc4N)n(-c4ccc(CN5CCC(Nc6ccnc(C#N)n6)CC5)cc4)c3n2)cc1=O] | 4-((1-(4-(2-(2-aminopyridin-3-yl)-5-(1-methyl-2-oxo-1,2-dihydropyridin-4-yl)-3H-imidazo[4,5-b]pyridin-3-yl)benzyl)piperidin-4-yl)amino)pyrimidine-2-carbonitrile |
| 360 | 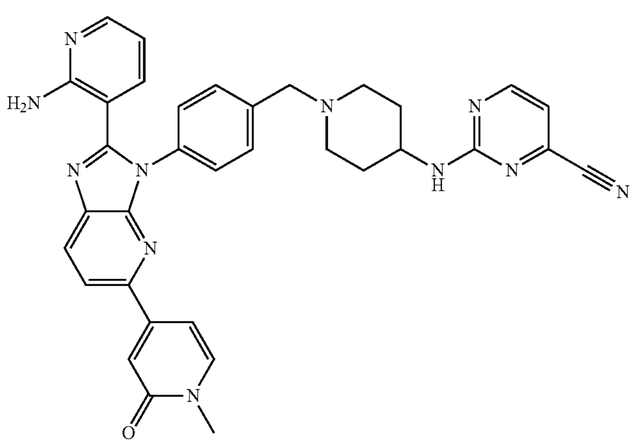 [SMILES: Cn1ccc(-c2ccc3nc(-c4cccnc4N)n(-c4ccc(CN5CCC(Nc6nccc(C#N)n6)CC5)cc4)c3n2)cc1=O] | 2-((1-(4-(2-(2-aminopyridin-3-yl)-5-(1-methyl-2-oxo-1,2-dihydropyridin-4-yl)-3H-imidazo[4,5-b]pyridin-3-yl)benzyl)piperidin-4-yl)amino)pyrimidine-4-carbonitrile |

TABLE 1-continued

| Example | Compound Structure | Compound Name |
|---|---|---|
| 361 | 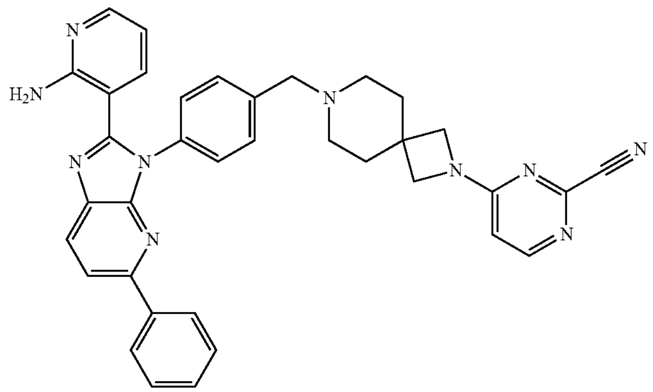 [SMILES: N#Cc1nccc(N2CC3(CCN(Cc4ccc(-n5c(-c6cccnc6N)nc6ccc(-c7ccccc7)nc65)cc4)CC3)C2)n1] | 4-(7-(4-(2-(2-aminopyridin-3-yl)-5-phenyl-3H-imidazo[4,5-b]pyridin-3-yl)benzyl)-2,7-diazaspiro[3.5]nonan-2-yl)pyrimidine-2-carbonitrile |
| 362 | 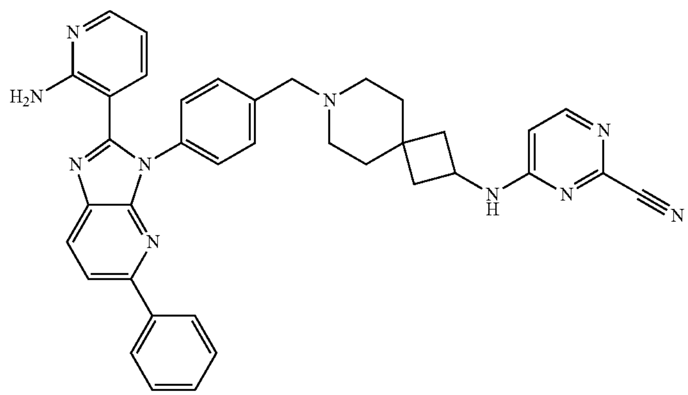 [SMILES: N#Cc1nccc(NC2CC3(CCN(Cc4ccc(-n5c(-c6cccnc6N)nc6ccc(-c7ccccc7)nc65)cc4)CC3)C2)n1] | 4-((7-(4-(2-(2-aminopyridin-3-yl)-5-phenyl-3H-imidazo[4,5-b]pyridin-3-yl)benzyl)-7-azaspiro[3.5]nonan-2-yl)amino)pyrimidine-2-carbonitrile |
| 363 | 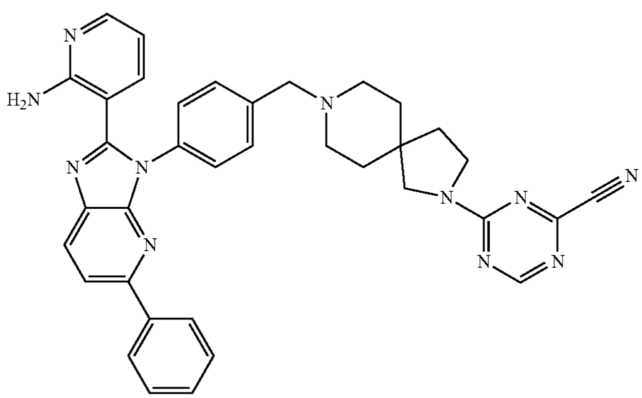 [SMILES: N#Cc1ncnc(N2CCC3(CCN(Cc4ccc(-n5c(-c6cccnc6N)nc6ccc(-c7ccccc7)nc65)cc4)CC3)C2)n1] | 4-(8-(4-(2-(2-aminopyridin-3-yl)-5-phenyl-3H-imidazo[4,5-b]pyridin-3-yl)benzyl)-2,8-diazaspiro[4.5]decan-2-yl)-1,3,5-triazine-2-carbonitrile |
| 364 | 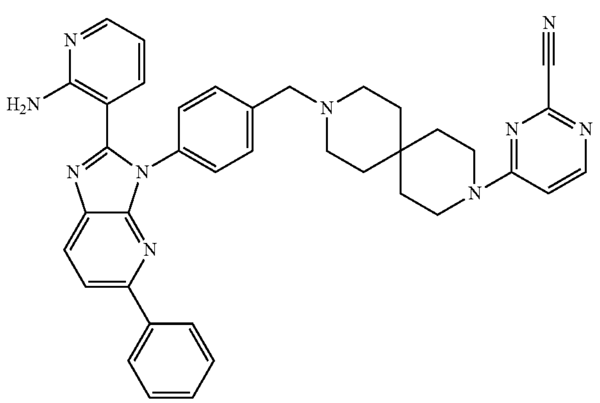 [SMILES: N#Cc1nccc(N2CCC3(CCN(Cc4ccc(-n5c(-c6cccnc6N)nc6ccc(-c7ccccc7)nc65)cc4)CC3)CC2)n1] | 4-(9-(4-(2-(2-aminopyridin-3-yl)-5-phenyl-3H-imidazo[4,5-b]pyridin-3-yl)benzyl)-3,9-diazaspiro[5.5]undecan-3-yl)pyrimidine-2-carbonitrile |

TABLE 1-continued

| Example | Compound Structure | Compound Name |
|---|---|---|
| 365 | 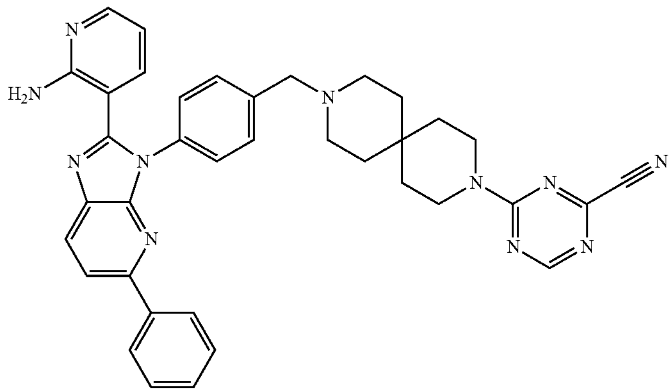 [SMILES: N#Cc1ncnc(N2CCC3(CCN(Cc4ccc(-n5c(-c6cccnc6N)nc6ccc(-c7ccccc7)nc65)cc4)CC3)CC2)n1] | 4-(9-(4-(2-(2-aminopyridin-3-yl)-5-phenyl-3H-imidazo[4,5-b]pyridin-3-yl)benzyl)-3,9-diazaspiro[5.5]undecan-3-yl)-1,3,5-triazine-2-carbonitrile |
| 366 | 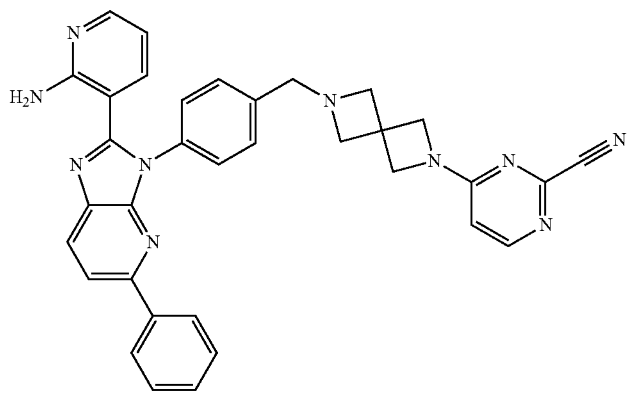 [SMILES: N#Cc1nccc(N2CC3(CN(Cc4ccc(-n5c(-c6cccnc6N)nc6ccc(-c7ccccc7)nc65)cc4)C3)C2)n1] | 4-(6-(4-(2-(2-aminopyridin-3-yl)-5-phenyl-3H-imidazo[4,5-b]pyridin-3-yl)benzyl)-2,6-diazaspiro[3.3]heptan-2-yl)pyrimidine-2-carbonitrile |
| 367 | 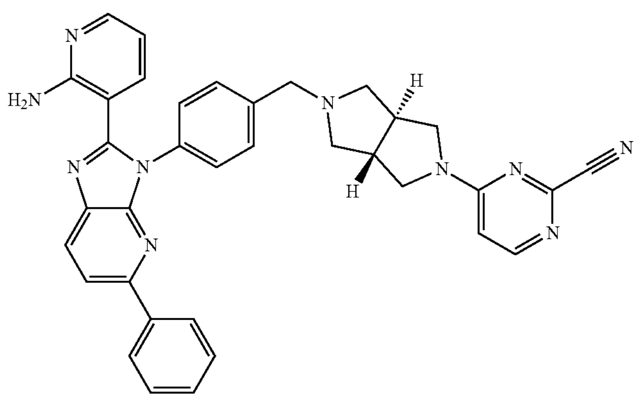 [SMILES: N#Cc1nccc(N2C[C@@H]3CN(Cc4ccc(-n5c(-c6cccnc6N)nc6ccc(-c7ccccc7)nc65)cc4)C[C@H]3C2)n1] | 4-((3aS,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile |

| Example | Compound Structure | Compound Name |
|---|---|---|
| 368 | 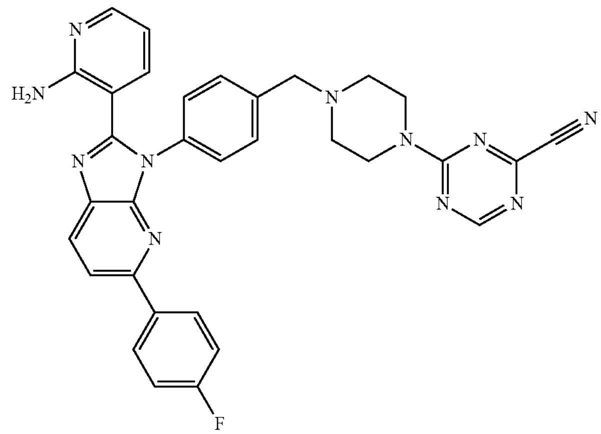 | 4-(4-(4-(2-(2-aminopyridin-3-yl)-5-(4-fluorophenyl)-3H-imidazo[4,5-b]pyridin-3-yl)benzyl)piperazin-1-yl)-1,3,5-triazine-2-carbonitrile |
| 369 | 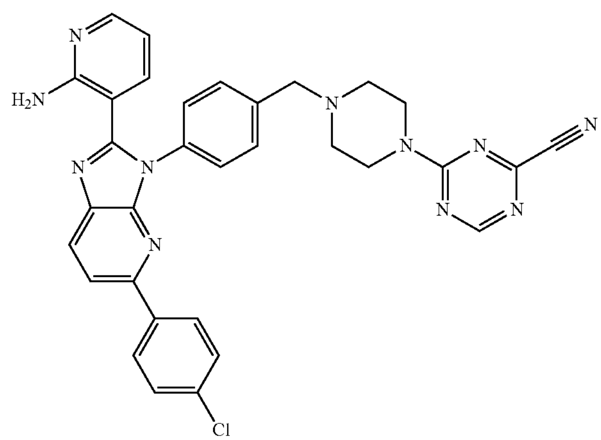 | 4-(4-(4-(2-(2-aminopyridin-3-yl)-5-(4-chlorophenyl)-3H-imidazo[4,5-b]pyridin-3-yl)benzyl)piperazin-1-yl)-1,3,5-triazine-2-carbonitrile |
| 370 | 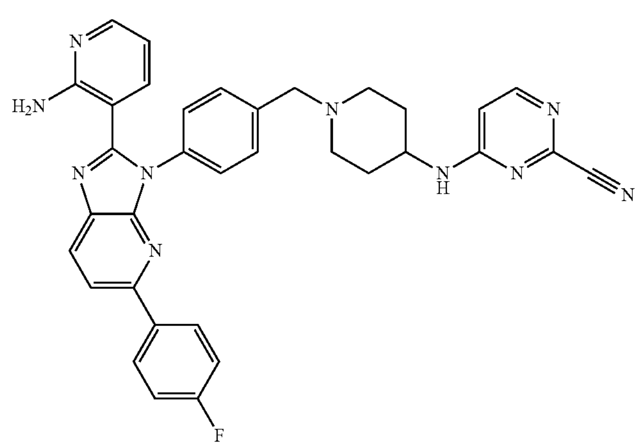 | 4-((1-(4-(2-(2-aminopyridin-3-yl)-5-(4-fluorophenyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 371 | 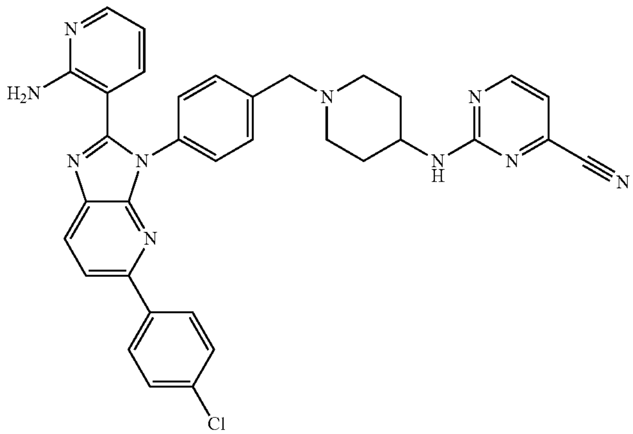 [SMILES: N#Cc1ccnc(NC2CCN(Cc3ccc(-n4c(-c5cccnc5N)nc5ccc(-c6ccc(Cl)cc6)nc54)cc3)CC2)n1] | 2-((1-(4-(2-(2-aminopyridin-3-yl)-5-(4-chlorophenyl)-3H-imidazo[4,5-b]pyridin-3-yl)benzyl)piperidin-4-yl)amino)pyrimidine-4-carbonitrile |
| 372 | 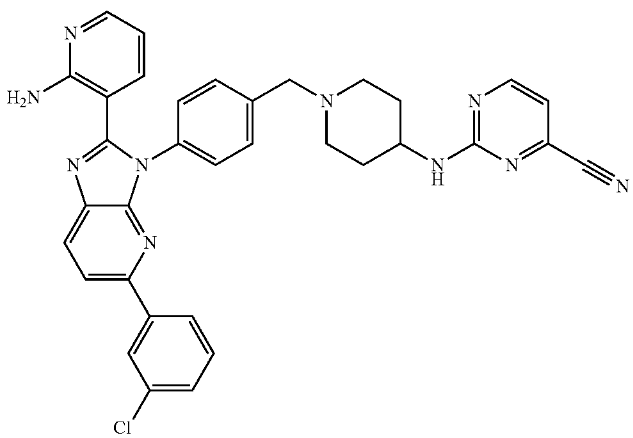 [SMILES: N#Cc1ccnc(NC2CCN(Cc3ccc(-n4c(-c5cccnc5N)nc5ccc(-c6cccc(Cl)c6)nc54)cc3)CC2)n1] | 2-((1-(4-(2-(2-aminopyridin-3-yl)-5-(3-chlorophenyl)-3H-imidazo[4,5-b]pyridin-3-yl)benzyl)piperidin-4-yl)amino)pyrimidine-4-carbonitrile |
| 373 | 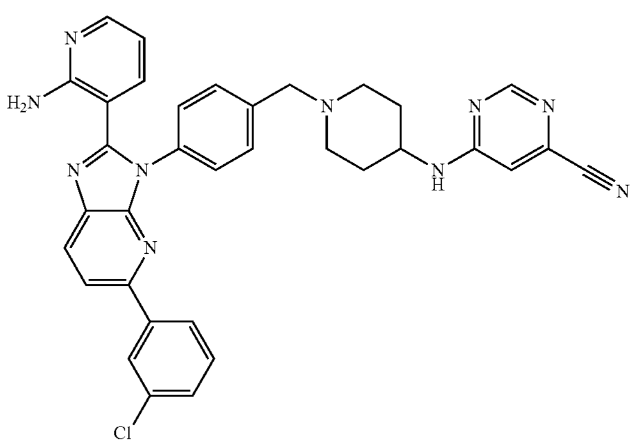 [SMILES: N#Cc1cc(NC2CCN(Cc3ccc(-n4c(-c5cccnc5N)nc5ccc(-c6cccc(Cl)c6)nc54)cc3)CC2)ncn1] | 6-((1-(4-(2-(2-aminopyridin-3-yl)-5-(3-chlorophenyl)-3H-imidazo[4,5-b]pyridin-3-yl)benzyl)piperidin-4-yl)amino)pyrimidine-4-carbonitrile |

TABLE 1-continued

| Example | Compound Structure | Compound Name |
|---|---|---|
| 374 | 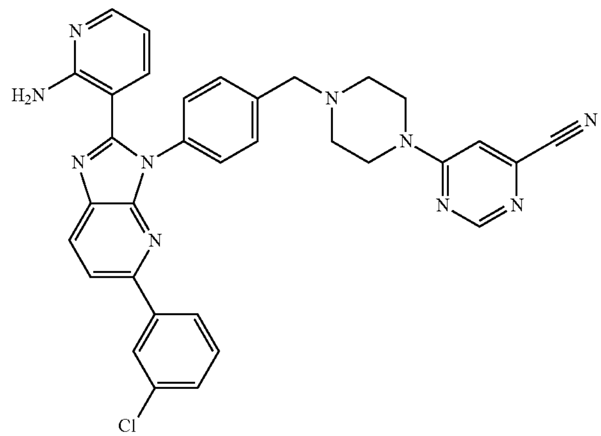 | 6-(4-(4-(2-(2-aminopyridin-3-yl)-5-(3-chlorophenyl)-3H-imidazo[4,5-b]pyridin-3-yl)benzyl)piperazin-1-yl)pyrimidine-4-carbonitrile |
| 375 | 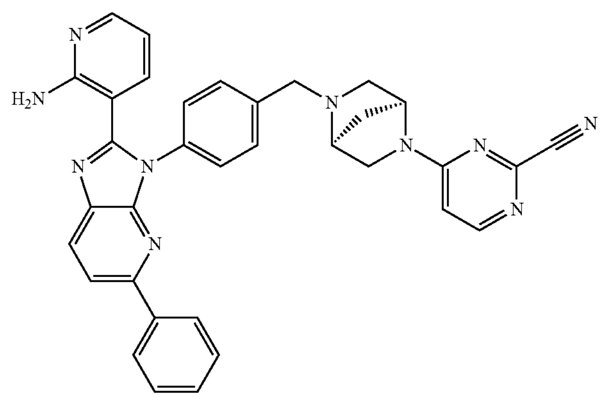 [SMILES: N#Cc1nccc(N2C[C@@H]3C[C@H]2CN3Cc2ccc(-n3c(-c4cccnc4N)nc4ccc(-c5ccccc5)nc43)cc2)n1] | 4-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-2-carbonitrile |
| 376 | 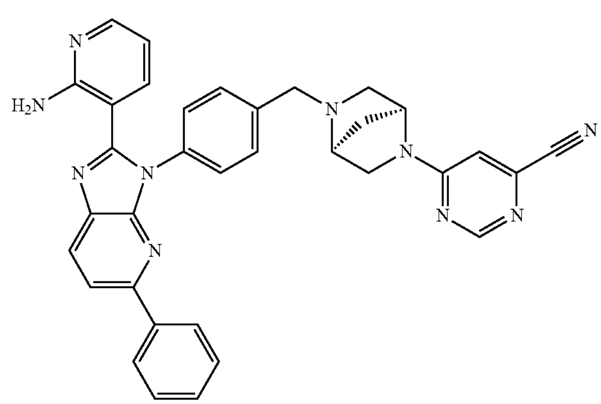 [SMILES: N#Cc1cc(N2C[C@@H]3C[C@H]2CN3Cc2ccc(-n3c(-c4cccnc4N)nc4ccc(-c5ccccc5)nc43)cc2)ncn1] | 6-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile |

TABLE 1-continued

| Example | Compound Structure | Compound Name |
|---|---|---|
| 377 | 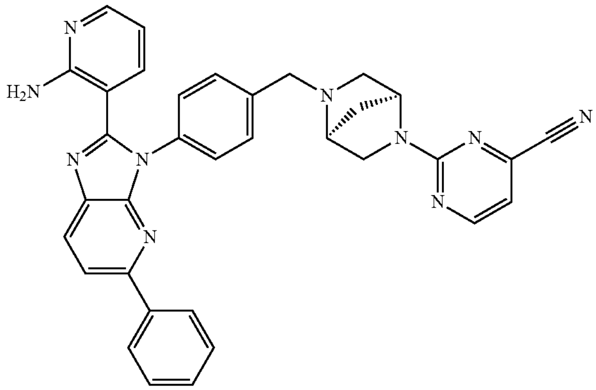 [SMILES: N#Cc1ccnc(N2C[C@@H]3C[C@H]2CN3Cc2ccc(-n3c(-c4cccnc4N)nc4ccc(-c5ccccc5)nc43)cc2)n1] | 2-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile |
| 378 | 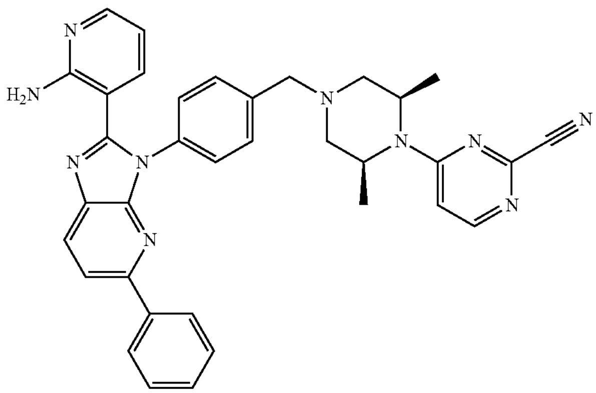 [SMILES: C[C@@H]1CN(Cc2ccc(-n3c(-c4cccnc4N)nc4ccc(-c5ccccc5)nc43)cc2)C[C@H](C)N1c1ccnc(C#N)n1] | 4-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile |
| 379 | 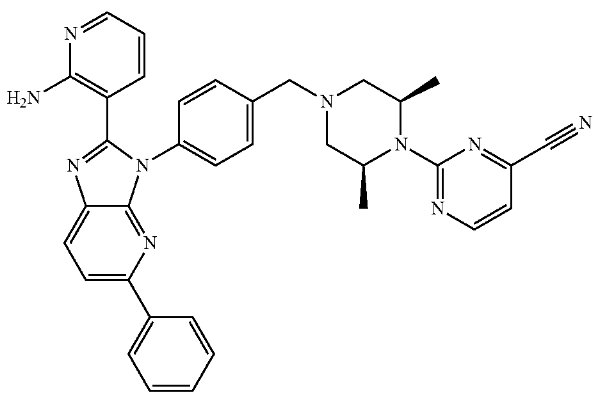 [SMILES: C[C@@H]1CN(Cc2ccc(-n3c(-c4cccnc4N)nc4ccc(-c5ccccc5)nc43)cc2)C[C@H](C)N1c1nccc(C#N)n1] | 2-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile |
| 380 | 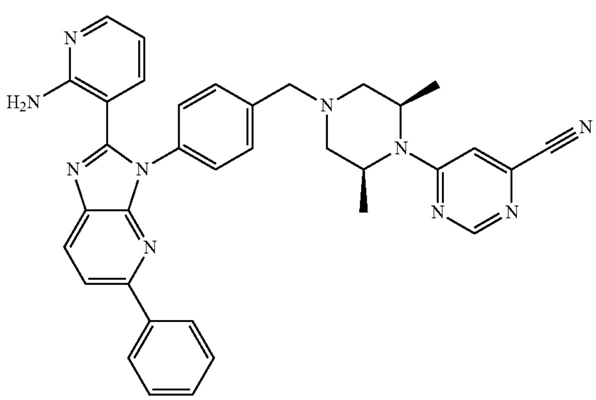 [SMILES: C[C@@H]1CN(Cc2ccc(-n3c(-c4cccnc4N)nc4ccc(-c5ccccc5)nc43)cc2)C[C@H](C)N1c1cc(C#N)ncn1] | 6-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile |

| Example | Compound Structure | Compound Name |
|---|---|---|
| 381 | 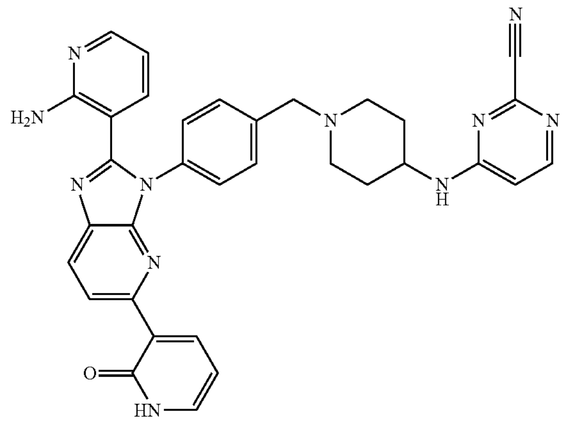 [SMILES: N#Cc1nccc(NC2CCN(Cc3ccc(-n4c(-c5cccnc5N)nc5ccc(-c6ccc[nH]c6=O)nc54)cc3)CC2)n1] | 4-((1-(4-(2-(2-aminopyridin-3-yl)-5-(2-oxo-1,2-dihydropyridin-3-yl)-3H-imidazo[4,5-b]pyridin-3-yl)benzyl)piperidin-4-yl)amino)pyrimidine-2-carbonitrile |
| 382 | 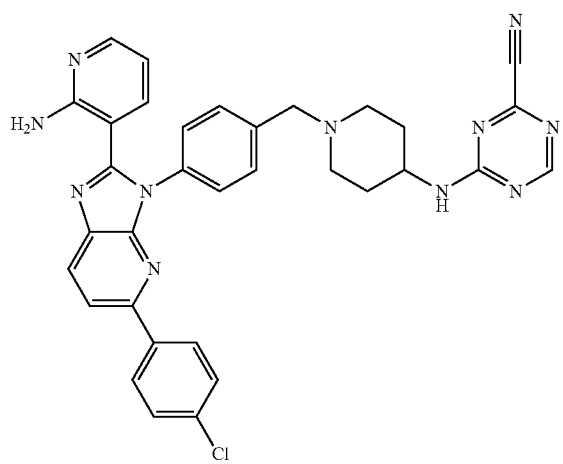 [SMILES: N#Cc1ncnc(NC2CCN(Cc3ccc(-n4c(-c5cccnc5N)nc5ccc(-c6ccc(Cl)cc6)nc54)cc3)CC2)n1] | 4-((1-(4-(2-(2-aminopyridin-3-yl)-5-(4-chlorophenyl)-3H-imidazo[4,5-b]pyridin-3-yl)benzyl)piperidin-4-yl)amino)-1,3,5-triazine-2-carbonitrile |
| 383 | 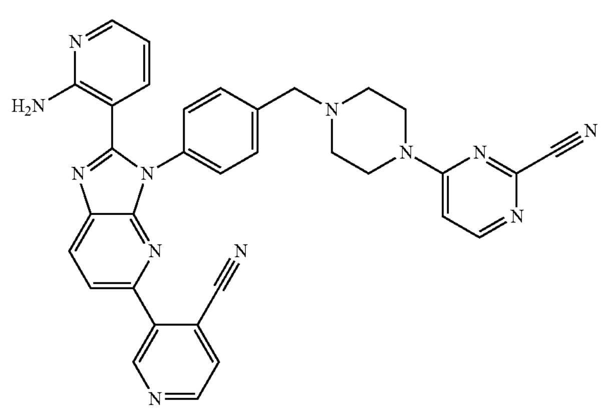 | 4-(4-(4-(2-(2-aminopyridin-3-yl)-5-(4-cyanopyridin-3-yl)-3H-imidazo[4,5-b]pyridin-3-yl)benzyl)piperazin-1-yl)pyrimidine-2-carbonitrile |

TABLE 1-continued

| Example | Compound Structure | Compound Name |
|---|---|---|
| 384 | 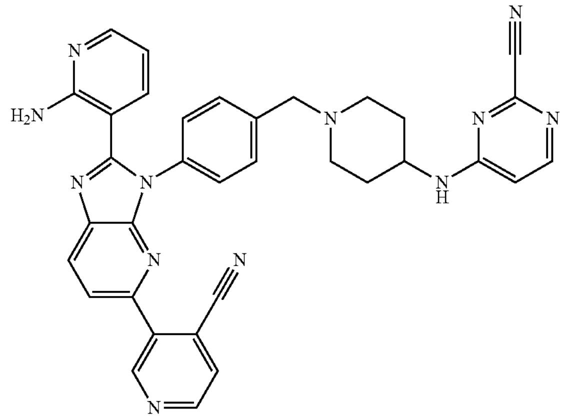 [SMILES: N#Cc1nccc(NC2CCN(Cc3ccc(-n4c(-c5cccnc5N)nc5ccc(-c6cnccc6C#N)nc54)cc3)CC2)n1] | 4-((1-(4-(2-(2-aminopyridin-3-yl)-5-(4-cyanopyridin-3-yl)-3H-imidazo[4,5-b]pyridin-3-yl)benzyl)piperidin-4-yl)amino)pyrimidine-2-carbonitrile |
| 385 | 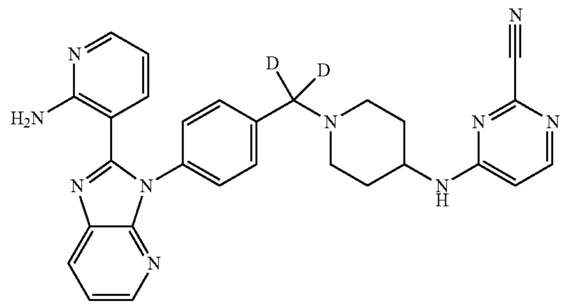 [SMILES: [2H]C([2H])(c1ccc(-n2c(-c3cccnc3N)nc3cccnc32)cc1)N1CCC(Nc2ccnc(C#N)n2)CC1] | 4-((1-((4-(2-(2-aminopyridin-3-yl)-3H-imidazo[4,5-b]pyridin-3-yl)phenyl)methyl-d2)piperidin-4-yl)amino)pyrimidine-2-carbonitrile |
| 386 | 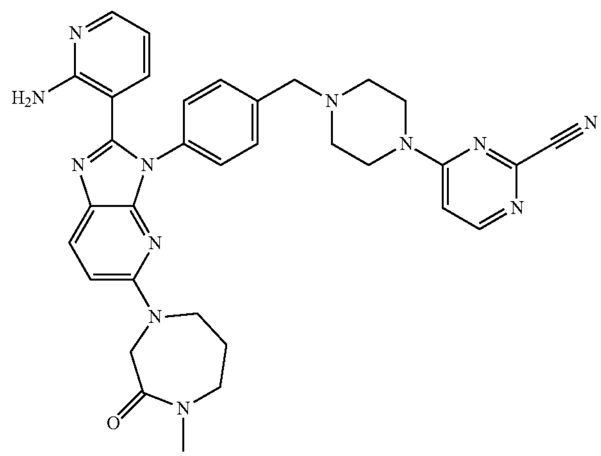 [SMILES: CN1CCCN(c2ccc3nc(-c4cccnc4N)n(-c4ccc(CN5CCN(c6ccnc(C#N)n6)CC5)cc4)c3n2)CC1=O] | 4-(4-(4-(2-(2-aminopyridin-3-yl)-5-(4-methyl-3-oxo-1,4-diazepan-1-yl)-3H-imidazo[4,5-b]pyridin-3-yl)benzyl)piperazin-1-yl)pyrimidine-2-carbonitrile |
| 387 | 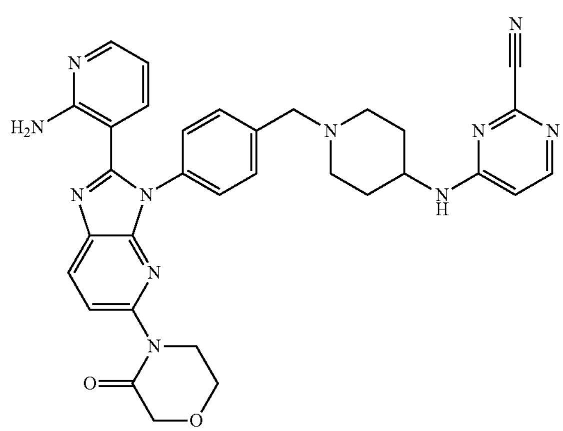 [SMILES: N#Cc1nccc(NC2CCN(Cc3ccc(-n4c(-c5cccnc5N)nc5ccc(N6CCOCC6=O)nc54)cc3)CC2)n1] | 4-((1-(4-(2-(2-aminopyridin-3-yl)-5-(3-oxomorpholino)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 388 | 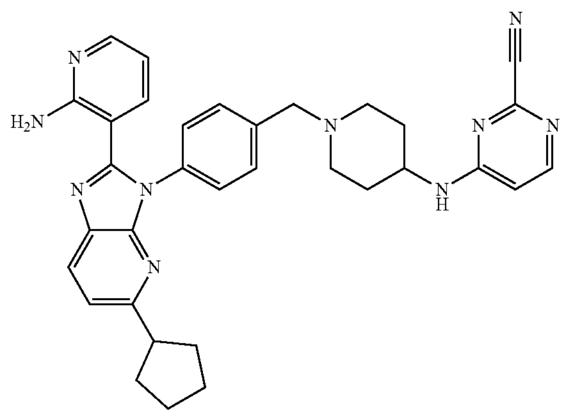 [SMILES: N#Cc1nccc(NC2CCN(Cc3ccc(-n4c(-c5cccnc5N)nc5ccc(C6CCCC6)nc54)cc3)CC2)n1] | 4-((1-(4-(2-(2-aminopyridin-3-yl)-5-cyclopentyl-3H-imidazo[4,5-b]pyridin-3-yl)benzyl)piperidin-4-yl)amino)pyrimidine-2-carbonitrile |
| 389 | 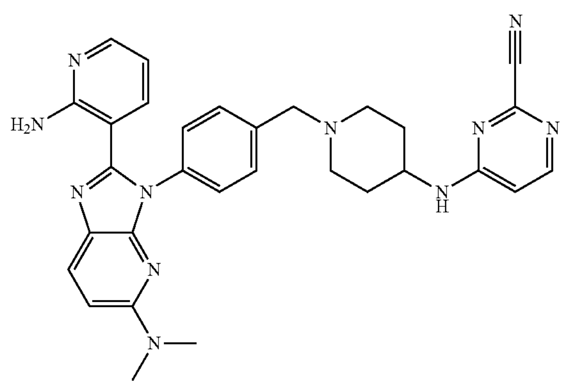 [SMILES: CN(C)c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(dimethylamino)-3H-imidazo[4,5-b]pyridin-3-yl)benzyl)piperidin-4-yl)amino)pyrimidine-2-carbonitrile |
| 390 | 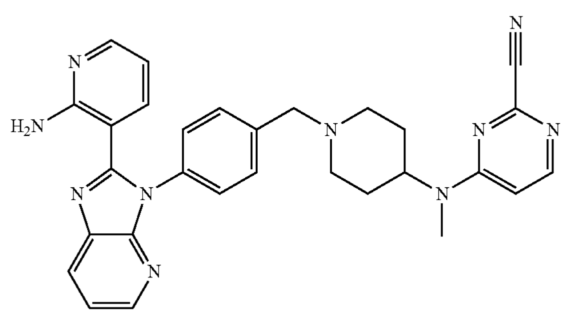 [SMILES: CN(c1ccnc(C#N)n1)C1CCN(Cc2ccc(-n3c(-c4cccnc4N)nc4cccnc43)cc2)CC1] | 4-((1-(4-(2-(2-aminopyridin-3-yl)-3H-imidazo[4,5-b]pyridin-3-yl)benzyl)piperidin-4-yl)(methyl)amino)pyrimidine-2-carbonitrile |
| 391 | 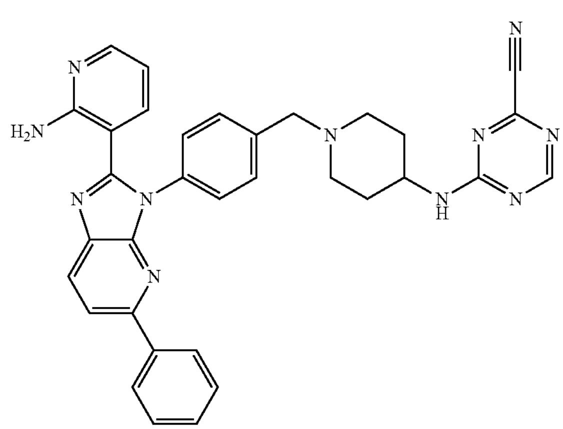 | 4-((1-(4-(2-(2-aminopyridin-3-yl)-5-phenyl-3H-imidazo[4,5-b]pyridin-3-yl)benzyl)piperidin-4-yl)amino)-1,3,5-triazine-2-carbonitrile |

| Example | Compound Structure | Compound Name |
|---|---|---|
| 392 | 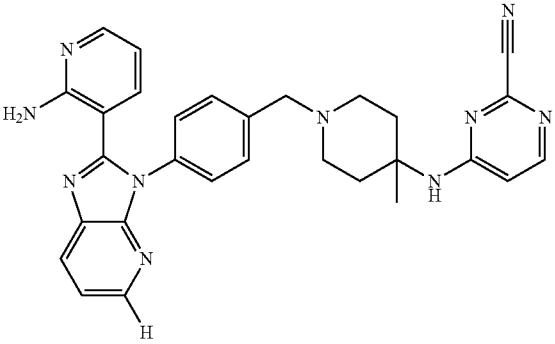 [SMILES: CC1(Nc2ccnc(C#N)n2)CCN(Cc2ccc(-n3c(-c4cccnc4N)nc4cccnc43)cc2)CC1] | 4-((1-(4-(2-(2-aminopyridin-3-yl)-3H-imidazo[4,5-b]pyridin-3-yl)benzyl)-4-methylpiperidin-4-yl)amino)pyrimidine-2-carbonitrile |
| 393 | 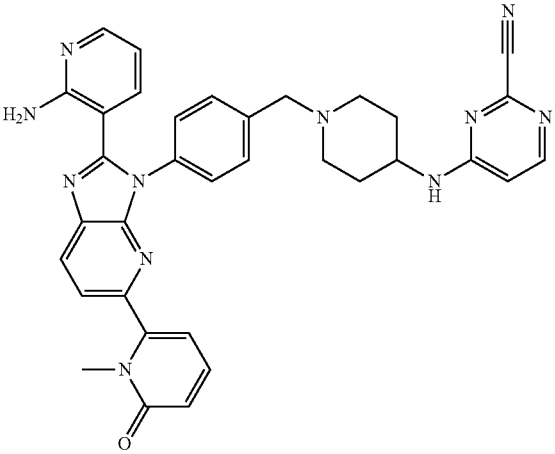 [SMILES: Cn1c(-c2ccc3nc(-c4cccnc4N)n(-c4ccc(CN5CCC(Nc6ccnc(C#N)n6)CC5)cc4)c3n2)cccc1=O] | 4-((1-(4-(2-(2-aminopyridin-3-yl)-5-(1-methyl-6-oxo-1,6-dihydropyridin-2-yl)-3H-imidazo[4,5-b]pyridin-3-yl)benzyl)piperidin-4-yl)amino)pyrimidine-2-carbonitrile |
| 394 | 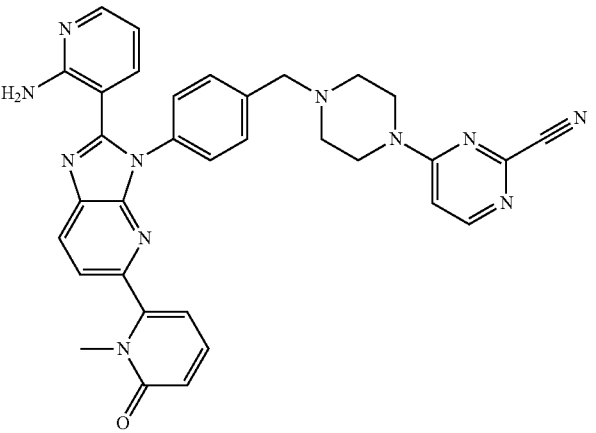 [SMILES: Cn1c(-c2ccc3nc(-c4cccnc4N)n(-c4ccc(CN5CCN(c6ccnc(C#N)n6)CC5)cc4)c3n2)cccc1=O] | 4-(4-(4-(2-(2-aminopyridin-3-yl)-5-(1-methyl-6-oxo-1,6-dihydropyridin-2-yl)-3H-imidazo[4,5-b]pyridin-3-yl)benzyl)piperazin-1-yl)pyrimidine-2-carbonitrile |

TABLE 1-continued

| Example | Compound Structure | Compound Name |
|---|---|---|
| 395 | 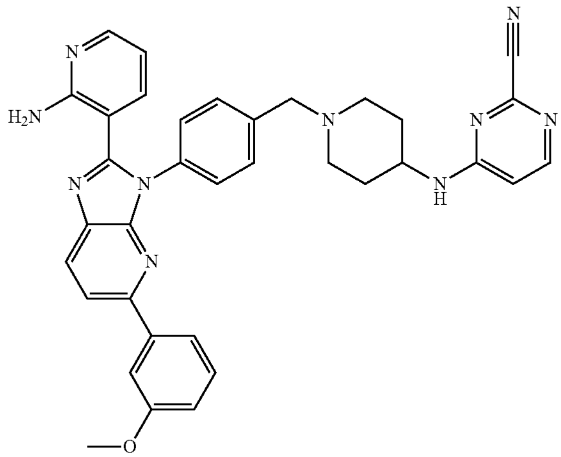 [SMILES: COc1cccc(-c2ccc3nc(-c4cccnc4N)n(-c4ccc(CN5CCC(Nc6ccnc(C#N)n6)CC5)cc4)c3n2)c1] | 4-((1-(4-(2-(2-aminopyridin-3-yl)-5-(3-methoxyphenyl)-3H-imidazo[4,5-b]pyridin-3-yl)benzyl)piperidin-4-yl)amino)pyrimidine-2-carbonitrile |
| 396 | 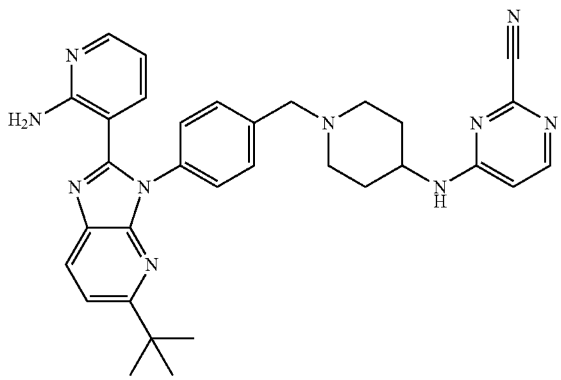 [SMILES: CC(C)(C)c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(tert-butyl)-3H-imidazo[4,5-b]pyridin-3-yl)benzyl)piperidin-4-yl)amino)pyrimidine-2-carbonitrile |
| 397 | 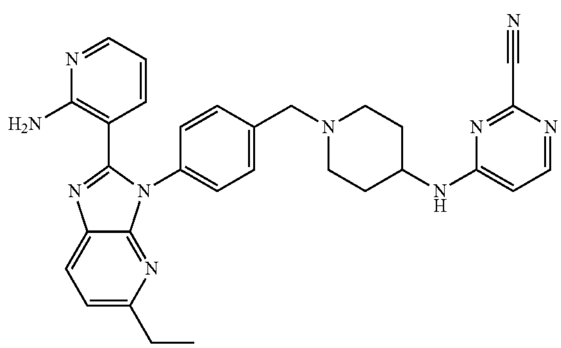 [SMILES: CCc1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-ethyl-3H-imidazo[4,5-b]pyridin-3-yl)benzyl)piperidin-4-yl)amino)pyrimidine-2-carbonitrile |
| 398 | 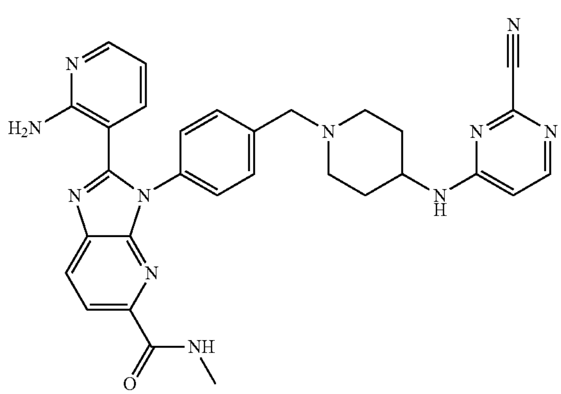 [SMILES: CNC(=O)c1ccc2nc(-c3cccnc3N)n(-c3ccc(CN4CCC(Nc5ccnc(C#N)n5)CC4)cc3)c2n1] | 2-(2-aminopyridin-3-yl)-3-(4-((4-((2-cyanopyrimidin-4-yl)amino)piperidin-1-yl)methyl)phenyl)-N-methyl-3H-imidazo[4,5-b]pyridine-5-carboxamide |

TABLE 1-continued

| Example | Compound Structure | Compound Name |
|---|---|---|
| 399 | 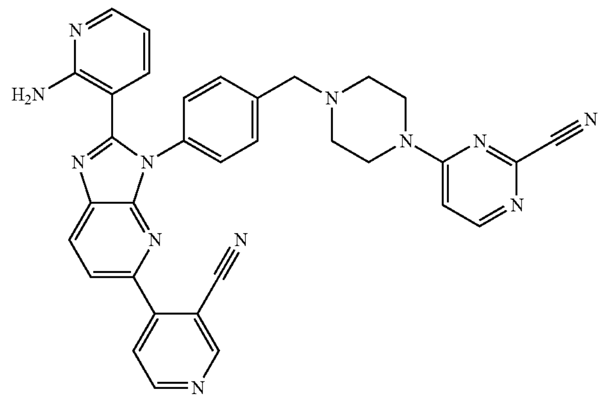 [SMILES: N#Cc1nccc(N2CCN(Cc3ccc(-n4c(-c5cccnc5N)nc5ccc(-c6ccncc6C#N)nc54)cc3)CC2)n1] | 4-(4-(4-(2-(2-aminopyridin-3-yl)-5-(3-cyanopyridin-4-yl)-3H-imidazo[4,5-b]pyridin-3-yl)benzyl)piperazin-1-yl)pyrimidine-2-carbonitrile |
| 400 | 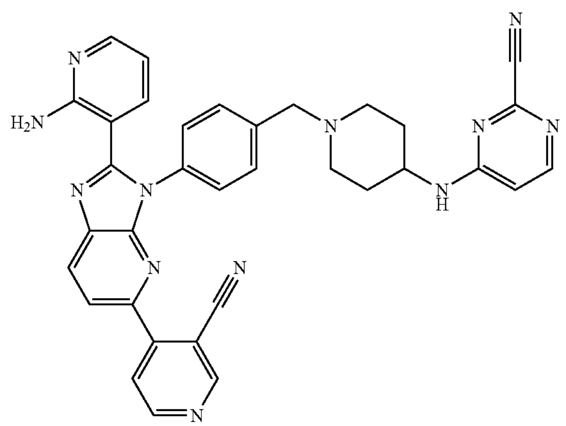 [SMILES: N#Cc1nccc(NC2CCN(Cc3ccc(-n4c(-c5cccnc5N)nc5ccc(-c6ccncc6C#N)nc54)cc3)CC2)n1] | 4-((1-(4-(2-(2-aminopyridin-3-yl)-5-(3-cyanopyridin-4-yl)-3H-imidazo[4,5-b]pyridin-3-yl)benzyl)piperidin-4-yl)amino)pyrimidine-2-carbonitrile |
| 401 | 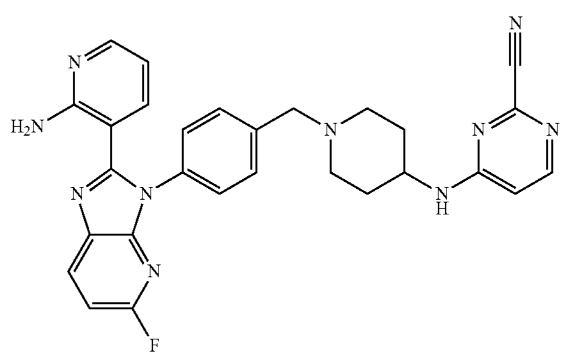 [SMILES: N#Cc1nccc(NC2CCN(Cc3ccc(-n4c(-c5cccnc5N)nc5ccc(F)nc54)cc3)CC2)n1] | 4-((1-(4-(2-(2-aminopyridin-3-yl)-5-fluoro-3H-imidazo[4,5-b]pyridin-3-yl)benzyl)piperidin-4-yl)amino)pyrimidine-2-carbonitrile |
| 402 | 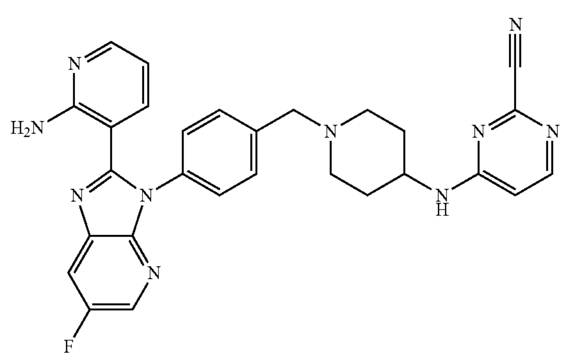 [SMILES: N#Cc1nccc(NC2CCN(Cc3ccc(-n4c(-c5cccnc5N)nc5cc(F)cnc54)cc3)CC2)n1] | 4-((1-(4-(2-(2-aminopyridin-3-yl)-6-fluoro-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 403 | 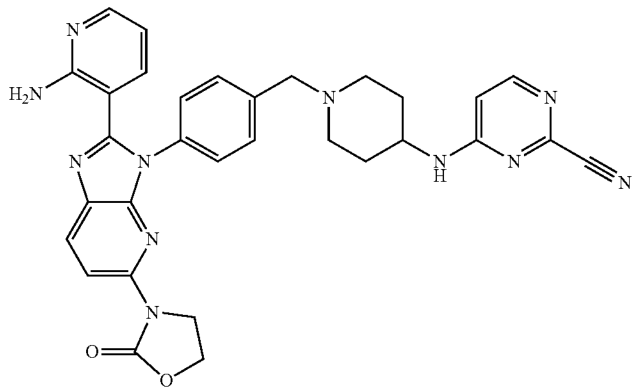 [SMILES: N#Cc1nccc(NC2CCN(Cc3ccc(-n4c(-c5cccnc5N)nc5ccc(N6CCOC6=O)nc54)cc3)CC2)n1] | 4-((1-(4-(2-(2-aminopyridin-3-yl)-5-(2-oxooxazolidin-3-yl)-3H-imidazo[4,5-b]pyridin-3-yl)benzyl)piperidin-4-yl)amino)pyrimidine-2-carbonitrile |
| 404 | 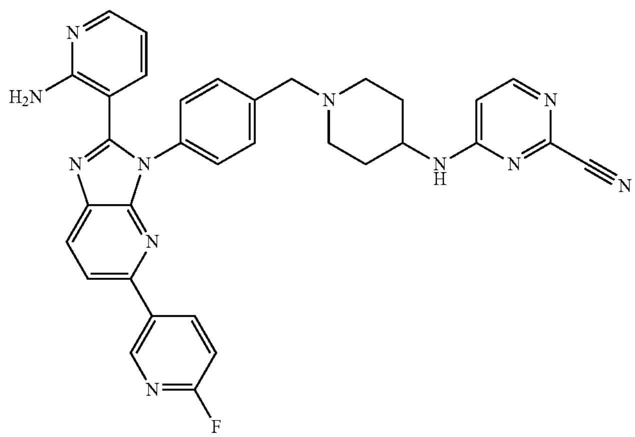 [SMILES: N#Cc1nccc(NC2CCN(Cc3ccc(-n4c(-c5cccnc5N)nc5ccc(-c6ccc(F)nc6)nc54)cc3)CC2)n1] | 4-((1-(4-(2-(2-aminopyridin-3-yl)-5-(6-fluoropyridin-3-yl)-3H-imidazo[4,5-b]pyridin-3-yl)benzyl)piperidin-4-yl)amino)pyrimidine-2-carbonitrile |
| 405 | 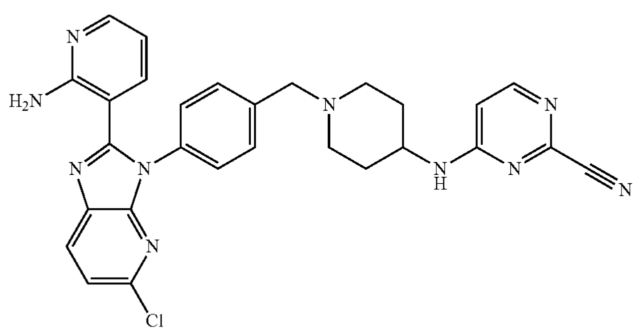 [SMILES: N#Cc1nccc(NC2CCN(Cc3ccc(-n4c(-c5cccnc5N)nc5ccc(Cl)nc54)cc3)CC2)n1] | 4-((1-(4-(2-(2-aminopyridin-3-yl)-5-chloro-3H-imidazo[4,5-b]pyridin-3-yl)benzyl)piperidin-4-yl)amino)pyrimidine-2-carbonitrile |
| 406 | 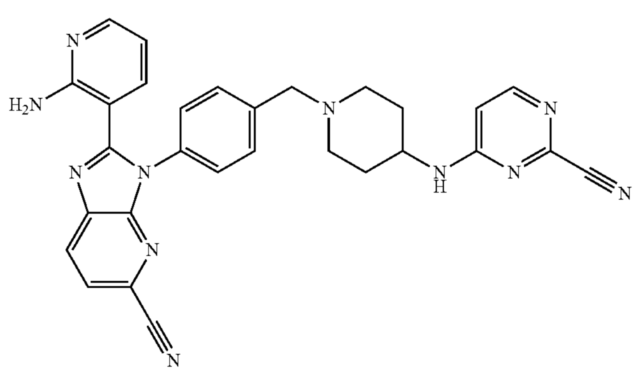 [SMILES: N#Cc1ccc2nc(-c3cccnc3N)n(-c3ccc(CN4CCC(Nc5ccnc(C#N)n5)CC4)cc3)c2n1] | 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carbonitrile |

TABLE 1-continued

| Example | Compound Structure | Compound Name |
|---|---|---|
| 407 | 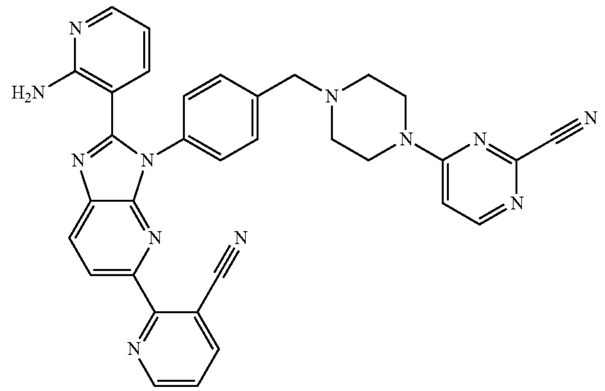 [SMILES: N#Cc1nccc(N2CCN(Cc3ccc(-n4c(-c5cccnc5N)nc5ccc(-c6ncccc6C#N)nc54)cc3)CC2)n1] | 4-(4-(4-(2-(2-aminopyridin-3-yl)-5-(3-cyanopyridin-2-yl)-3H-imidazo[4,5-b]pyridin-3-yl)benzyl)piperazin-1-yl)pyrimidine-2-carbonitrile |
| 408 | 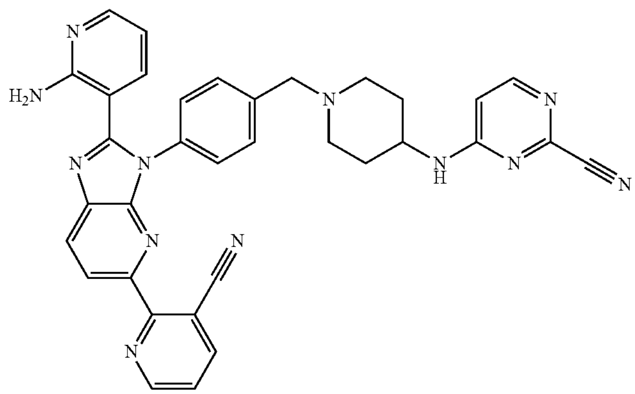 [SMILES: N#Cc1nccc(NC2CCN(Cc3ccc(-n4c(-c5cccnc5N)nc5ccc(-c6ncccc6C#N)nc54)cc3)CC2)n1] | 4-((1-(4-(2-(2-aminopyridin-3-yl)-5-(3-cyanopyridin-2-yl)-3H-imidazo[4,5-b]pyridin-3-yl)benzyl)piperidin-4-yl)amino)pyrimidine-2-carbonitrile |
| 409 | 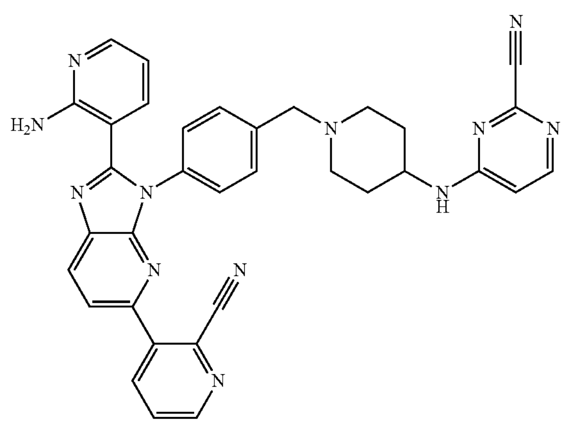 | 4-((1-(4-(2-(2-aminopyridin-3-yl)-5-(2-cyanopyridin-3-yl)-3H-imidazo[4,5-b]pyridin-3-yl)benzyl)piperidin-4-yl)amino)pyrimidine-2-carbonitrile |
| 410 | 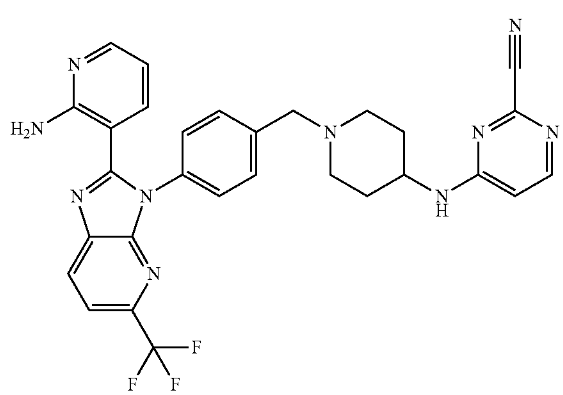 [SMILES: N#Cc1nccc(NC2CCN(Cc3ccc(-n4c(-c5cccnc5N)nc5ccc(C(F)(F)F)nc54)cc3)CC2)n1] | 4-((1-(4-(2-(2-aminopyridin-3-yl)-5-(trifluoromethyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 411 | 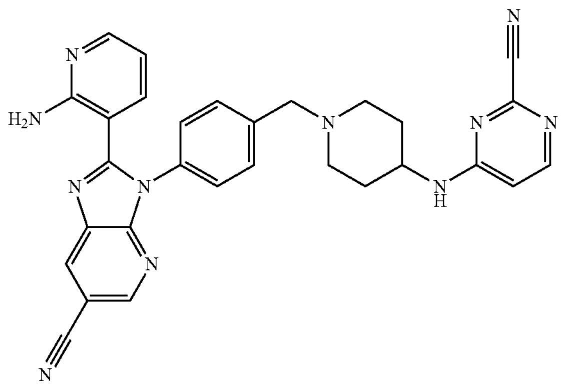 [SMILES: N#Cc1cnc2c(c1)nc(-c1cccnc1N)n2-c1ccc(CN2CCC(Nc3ccnc(C#N)n3)CC2)cc1] | 2-(2-aminopyridin-3-yl)-3-(4-((4-((2-cyanopyrimidin-4-yl)amino)piperidin-1-yl)methyl)phenyl)-3H-imidazo[4,5-b]pyridine-6-carbonitrile |
| 412 | 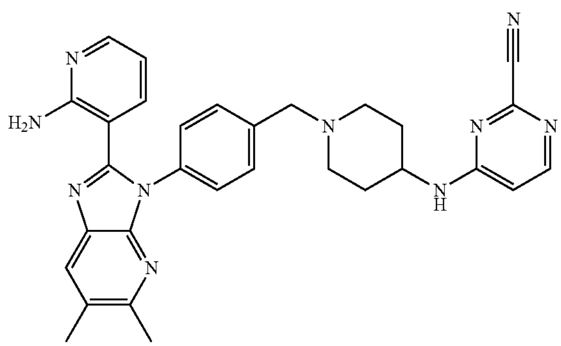 [SMILES: Cc1cc2nc(-c3cccnc3N)n(-c3ccc(CN4CCC(Nc5ccnc(C#N)n5)CC4)cc3)c2nc1C] | 4-((1-(4-(2-(2-aminopyridin-3-yl)-5,6-dimethyl-3H-imidazo[4,5-b]pyridin-3-yl)benzyl)piperidin-4-yl)amino)pyrimidine-2-carbonitrile |
| 413 | 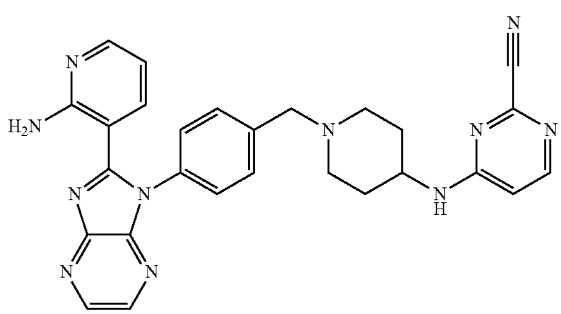 | 4-((1-(4-(2-(2-aminopyridin-3-yl)-1H-imidazo[4,5-b]pyrazin-1-yl)benzyl)piperidin-4-yl)amino)pyrimidine-2-carbonitrile |
| 414 | 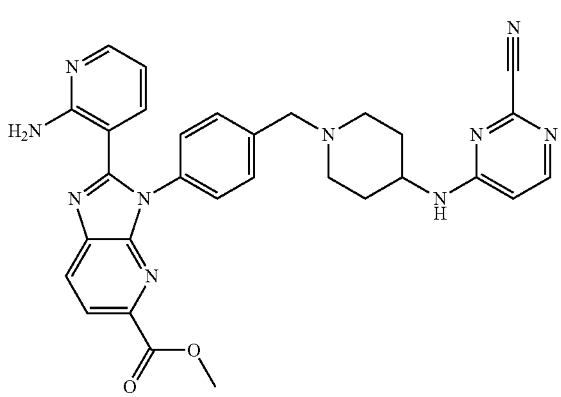 [SMILES: COC(=O)c1ccc2nc(-c3cccnc3N)n(-c3ccc(CN4CCC(Nc5ccnc(C#N)n5)CC4)cc3)c2n1] | methyl 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylate |

TABLE 1-continued

| Example | Compound Structure | Compound Name |
|---|---|---|
| 415 | 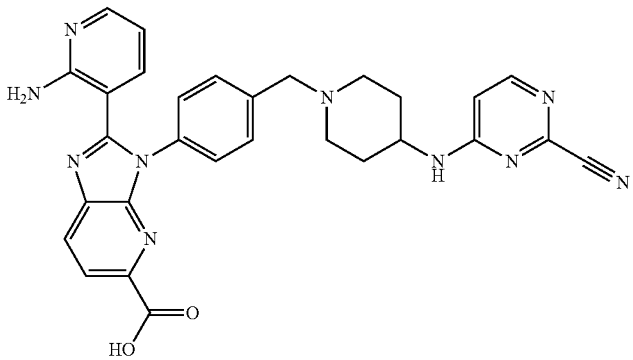 [SMILES: N#Cc1nccc(NC2CCN(Cc3ccc(-n4c(-c5cccnc5N)nc5ccc(C(=O)O)nc54)cc3)CC2)n1] | 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylic acid |
| 416 | 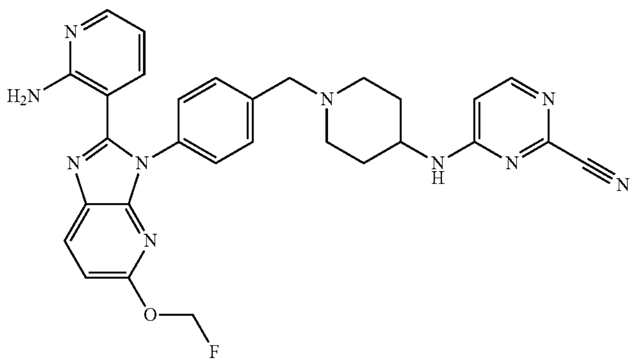 [SMILES: N#Cc1nccc(NC2CCN(Cc3ccc(-n4c(-c5cccnc5N)nc5ccc(OCF)nc54)cc3)CC2)n1] | 4-((1-(4-(2-(2-aminopyridin-3-yl)-5-(fluoromethoxy)-3H-imidazo[4,5-b]pyridin-3-yl)benzyl)piperidin-4-yl)amino)pyrimidine-2-carbonitrile |
| 417 | 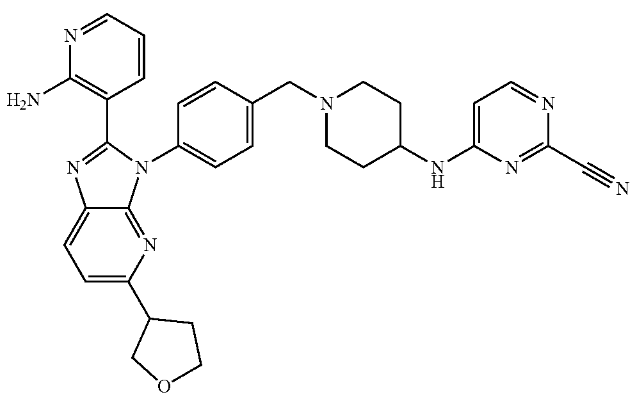 [SMILES: N#Cc1nccc(NC2CCN(Cc3ccc(-n4c(-c5cccnc5N)nc5ccc(C6CCOC6)nc54)cc3)CC2)n1] | 4-((1-(4-(2-(2-aminopyridin-3-yl)-5-(tetrahydrofuran-3-yl)-3H-imidazo[4,5-b]pyridin-3-yl)benzyl)piperidin-4-yl)amino)pyrimidine-2-carbonitrile |
| 418 | 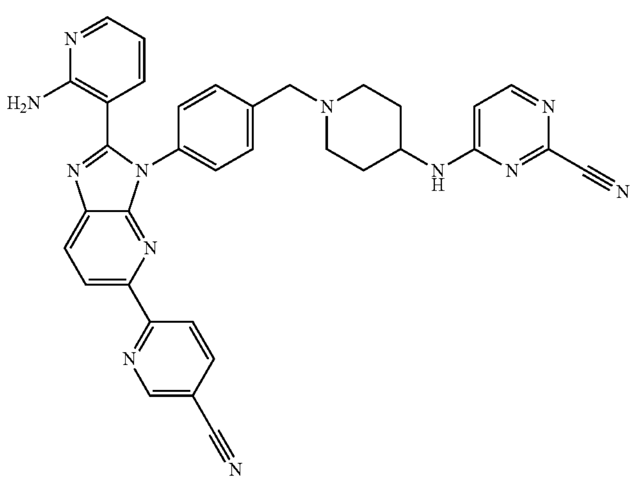 | 4-((1-(4-(2-(2-aminopyridin-3-yl)-5-(5-cyanopyridin-2-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 419 | 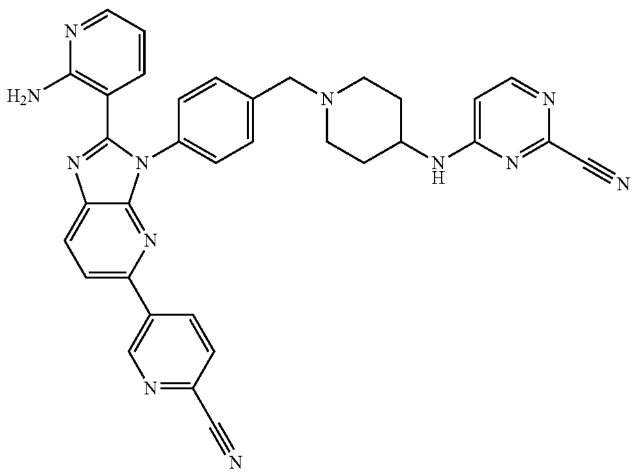 | 4-((1-(4-(2-(2-aminopyridin-3-yl)-5-(6-cyanopyridin-3-yl)-3H-imidazo[4,5-b]pyridin-3-yl)benzyl)piperidin-4-yl)amino)pyrimidine-2-carbonitrile |
| 420 | 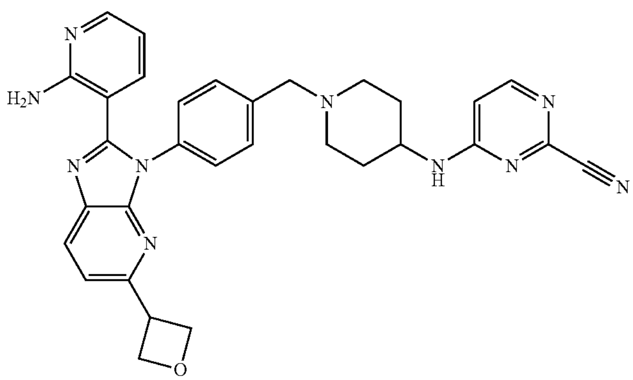 [SMILES: N#Cc1nccc(NC2CCN(Cc3ccc(-n4c(-c5cccnc5N)nc5ccc(C6COC6)nc54)cc3)CC2)n1] | 4-((1-(4-(2-(2-aminopyridin-3-yl)-5-(oxetan-3-yl)-3H-imidazo[4,5-b]pyridin-3-yl)benzyl)piperidin-4-yl)amino)pyrimidine-2-carbonitrile |
| 421 | 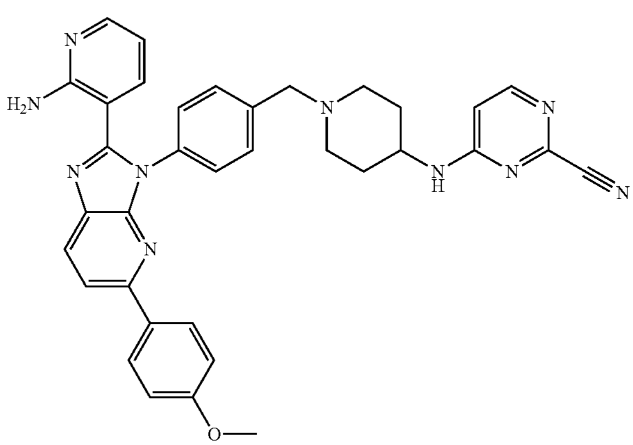 [SMILES: COc1ccc(-c2ccc3nc(-c4cccnc4N)n(-c4ccc(CN5CCC(Nc6ccnc(C#N)n6)CC5)cc4)c3n2)cc1] | 4-((1-(4-(2-(2-aminopyridin-3-yl)-5-(4-methoxyphenyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 422 | 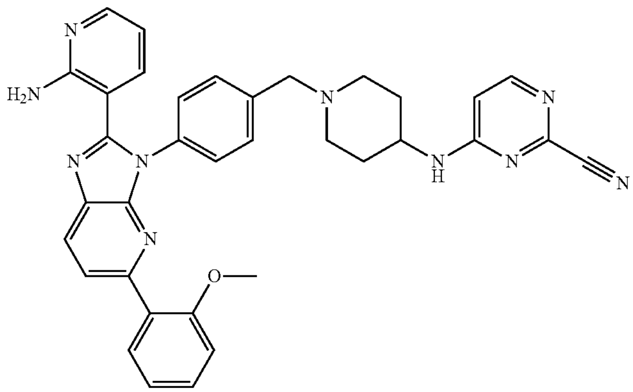 [SMILES: COc1ccccc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(2-methoxyphenyl)-3H-imidazo[4,5-b]pyridin-3-yl)benzyl)piperidin-4-yl)amino)pyrimidine-2-carbonitrile |
| 423 | 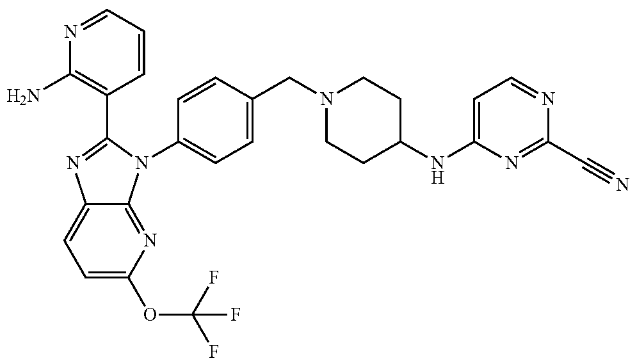 [SMILES: N#Cc1nccc(NC2CCN(Cc3ccc(-n4c(-c5cccnc5N)nc5ccc(OC(F)(F)F)nc54)cc3)CC2)n1] | 4-((1-(4-(2-(2-aminopyridin-3-yl)-5-(trifluoromethoxy)-3H-imidazo[4,5-b]pyridin-3-yl)benzyl)piperidin-4-yl)amino)pyrimidine-2-carbonitrile |
| 424 | 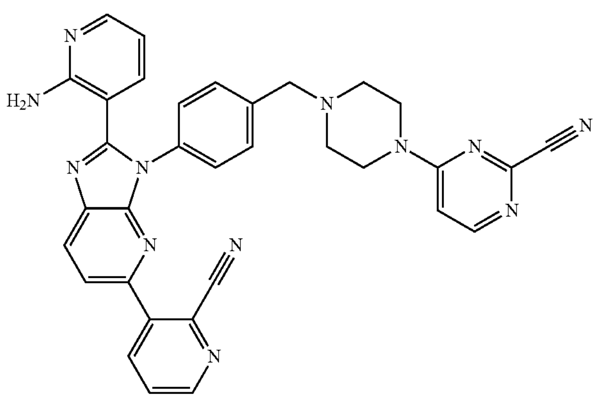 | 4-(4-(4-(2-(2-aminopyridin-3-yl)-5-(2-cyanopyridin-3-yl)-3H-imidazo[4,5-b]pyridin-3-yl)benzyl)piperazin-1-yl)pyrimidine-2-carbonitrile |
| 425 | 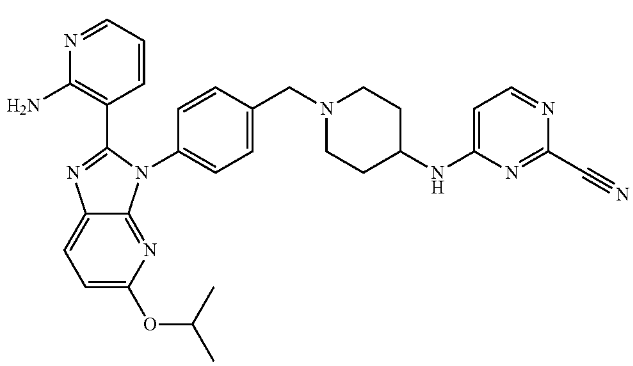 [SMILES: CC(C)Oc1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-isopropoxy-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 426 | 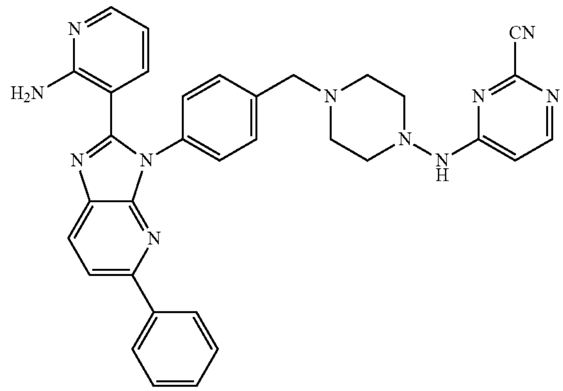 [SMILES: N#Cc1nccc(NN2CCN(Cc3ccc(-n4c(-c5cccnc5N)nc5ccc(-c6ccccc6)nc54)cc3)CC2)n1] | 4-((4-(4-(2-(2-aminopyridin-3-yl)-5-phenyl-3H-imidazo[4,5-b]pyridin-3-yl)benzyl)piperazin-1-yl)amino)pyrimidine-2-carbonitrile |
| 427 | 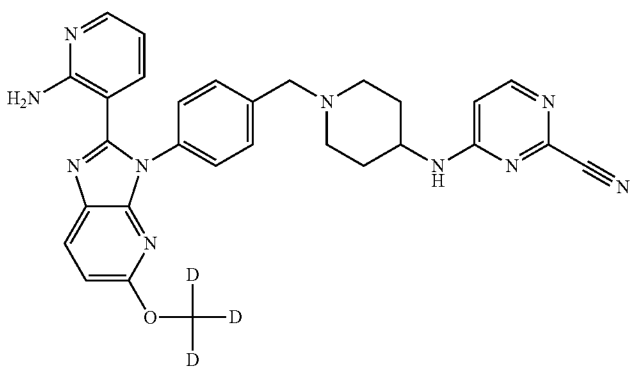 [SMILES: [2H]C([2H])([2H])Oc1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(methoxy-d3)-3H-imidazo[4,5-b]pyridin-3-yl)benzyl)piperidin-4-yl)amino)pyrimidine-2-carbonitrile |
| 428 | 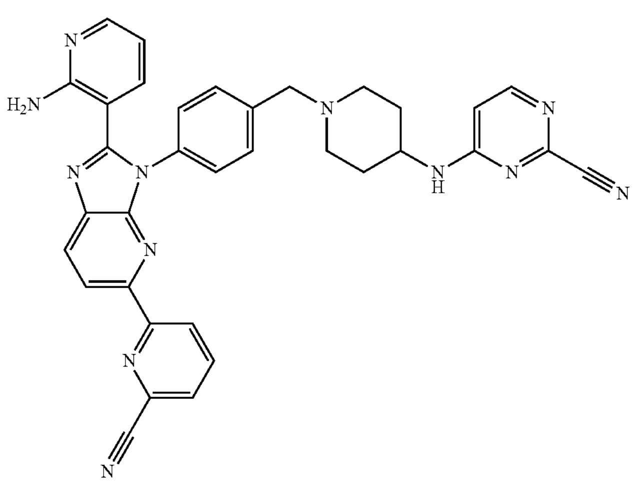 [SMILES: N#Cc1cccc(-c2ccc3nc(-c4cccnc4N)n(-c4ccc(CN5CCC(Nc6ccnc(C#N)n6)CC5)cc4)c3n2)n1] | 4-((1-(4-(2-(2-aminopyridin-3-yl)-5-(6-cyanopyridin-2-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 429 | 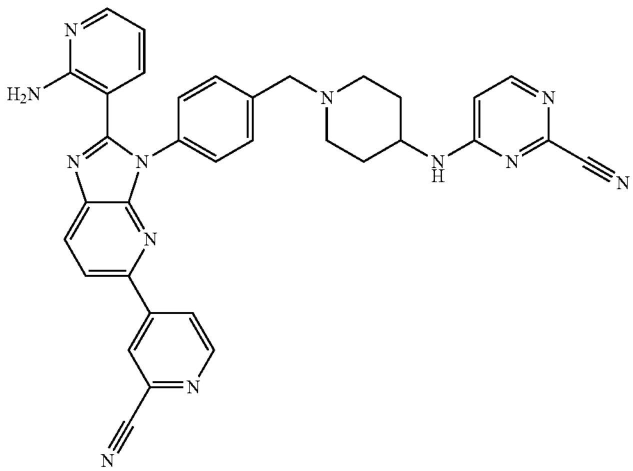 [SMILES: N#Cc1cc(-c2ccc3nc(-c4cccnc4N)n(-c4ccc(CN5CCC(Nc6ccnc(C#N)n6)CC5)cc4)c3n2)ccn1] | 4-((1-(4-(2-(2-aminopyridin-3-yl)-5-(2-cyanopyridin-4-yl)-3H-imidazo[4,5-b]pyridin-3-yl)benzyl)piperidin-4-yl)amino)pyrimidine-2-carbonitrile |
| 430 | 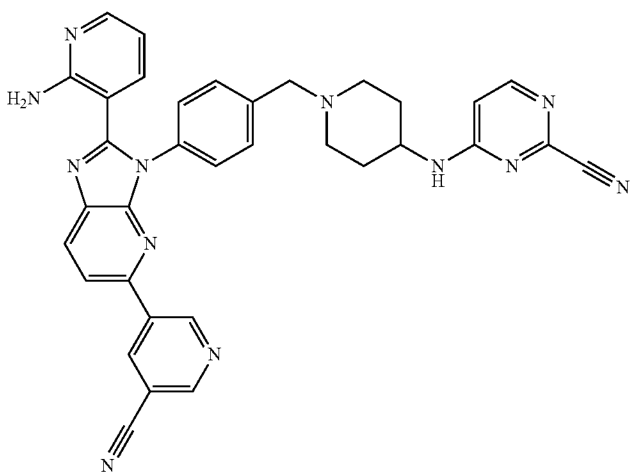 [SMILES: N#Cc1cncc(-c2ccc3nc(-c4cccnc4N)n(-c4ccc(CN5CCC(Nc6ccnc(C#N)n6)CC5)cc4)c3n2)c1] | 4-((1-(4-(2-(2-aminopyridin-3-yl)-5-(5-cyanopyridin-3-yl)-3H-imidazo[4,5-b]pyridin-3-yl)benzyl)piperidin-4-yl)amino)pyrimidine-2-carbonitrile |
| 431 | 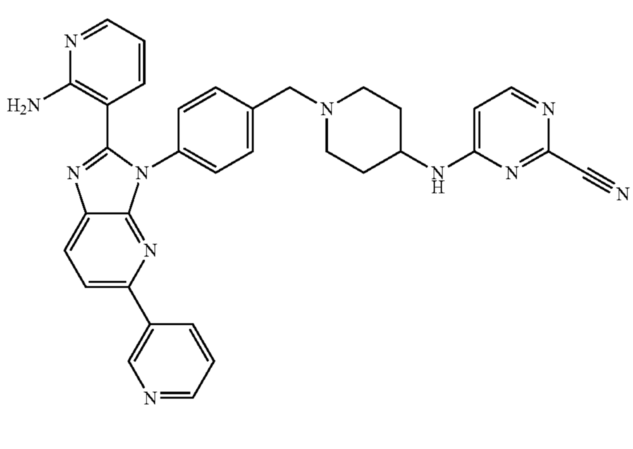 [SMILES: N#Cc1nccc(NC2CCN(Cc3ccc(-n4c(-c5cccnc5N)nc5ccc(-c6cccnc6)nc54)cc3)CC2)n1] | 4-((1-(4-(2-(2-aminopyridin-3-yl)-5-(pyridin-3-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 432 | 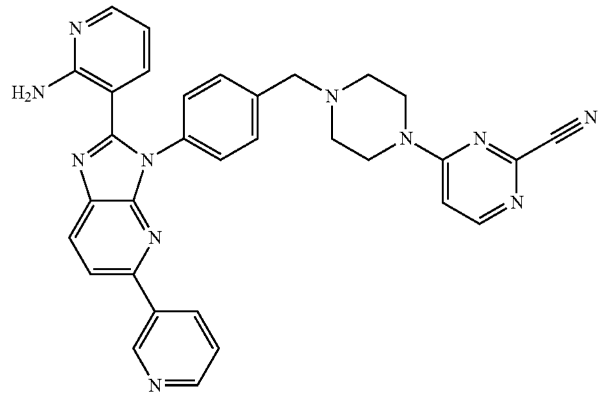 [SMILES: N#Cc1nccc(N2CCN(Cc3ccc(-n4c(-c5cccnc5N)nc5ccc(-c6cccnc6)nc54)cc3)CC2)n1] | 4-(4-(4-(2-(2-aminopyridin-3-yl)-5-(pyridin-3-yl)-3H-imidazo[4,5-b]pyridin-3-yl)benzyl)piperazin-1-yl)pyrimidine-2-carbonitrile |
| 433 | 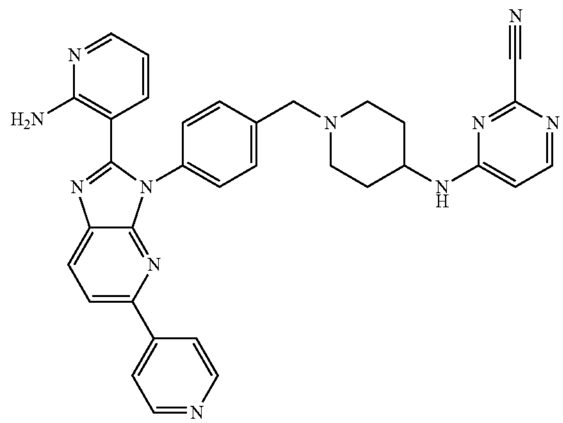 [SMILES: N#Cc1nccc(NC2CCN(Cc3ccc(-n4c(-c5cccnc5N)nc5ccc(-c6ccncc6)nc54)cc3)CC2)n1] | 4-((1-(4-(2-(2-aminopyridin-3-yl)-5-(pyridin-4-yl)-3H-imidazo[4,5-b]pyridin-3-yl)benzyl)piperidin-4-yl)amino)pyrimidine-2-carbonitrile |
| 434 | 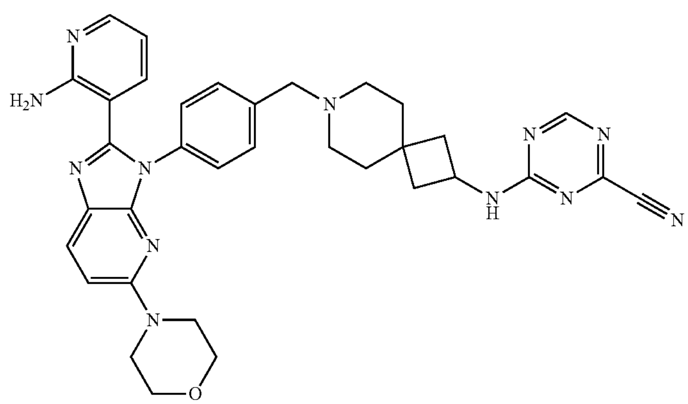 [SMILES: N#Cc1ncnc(NC2CC3(CCN(Cc4ccc(-n5c(-c6cccnc6N)nc6ccc(N7CCOCC7)nc65)cc4)CC3)C2)n1] | 4-((7-(4-(2-(2-aminopyridin-3-yl)-5-morpholino-3H-imidazo[4,5-b]pyridin-3-yl)benzyl)-7-azaspiro[3.5]nonan-2-yl)amino)-1,3,5-triazine-2-carbonitrile |
| 435 | 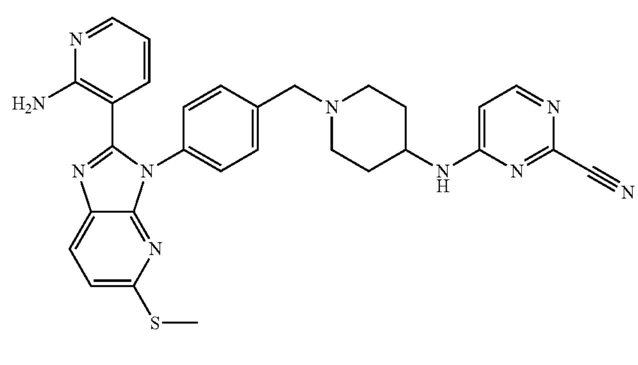 [SMILES: CSc1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(methylthio)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 436 | 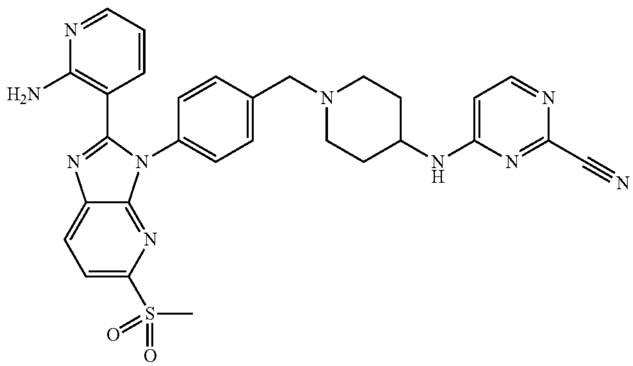 [SMILES: CS(=O)(=O)c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(methylsulfonyl)-3H-imidazo[4,5-b]pyridin-3-yl)benzyl)piperidin-4-yl)amino)pyrimidine-2-carbonitrile |
| 437 | 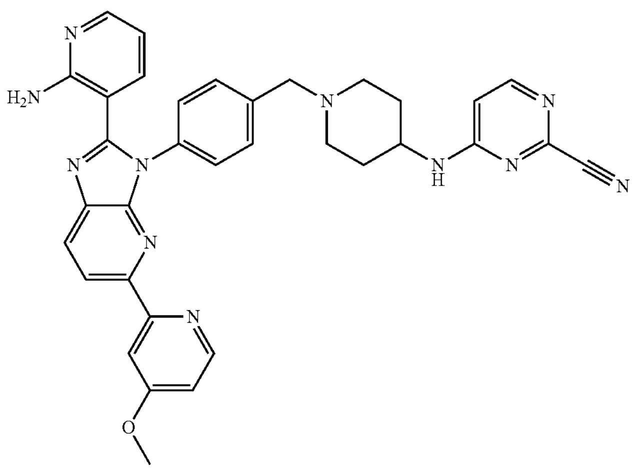 [SMILES: COc1ccnc(-c2ccc3nc(-c4cccnc4N)n(-c4ccc(CN5CCC(Nc6ccnc(C#N)n6)CC5)cc4)c3n2)c1] | 4-((1-(4-(2-(2-aminopyridin-3-yl)-5-(4-methoxypyridin-2-yl)-3H-imidazo[4,5-b]pyridin-3-yl)benzyl)piperidin-4-yl)amino)pyrimidine-2-carbonitrile |
| 438 | 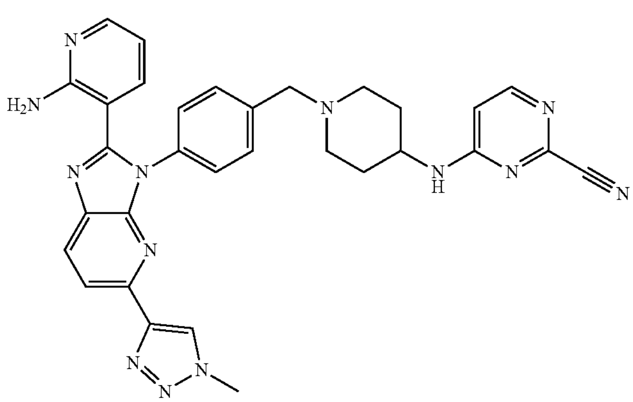 | 4-((1-(4-(2-(2-aminopyridin-3-yl)-5-(1-methyl-1H-1,2,3-triazol-4-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 439 | 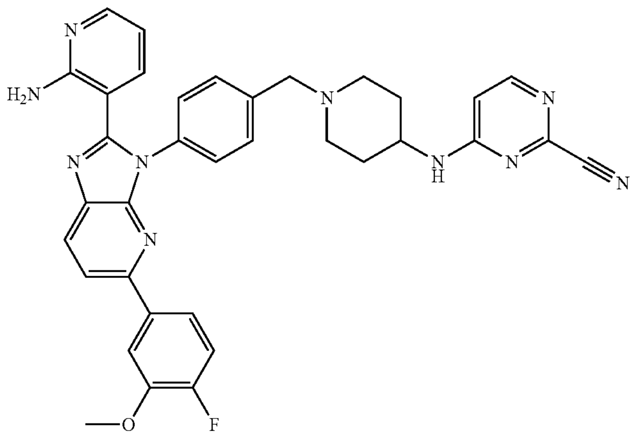 [SMILES: COc1cc(-c2ccc3nc(-c4cccnc4N)n(-c4ccc(CN5CCC(Nc6ccnc(C#N)n6)CC5)cc4)c3n2)ccc1F] | 4-((1-(4-(2-(2-aminopyridin-3-yl)-5-(4-fluoro-3-methoxyphenyl)-3H-imidazo[4,5-b]pyridin-3-yl)benzyl)piperidin-4-yl)amino)pyrimidine-2-carbonitrile |
| 440 | 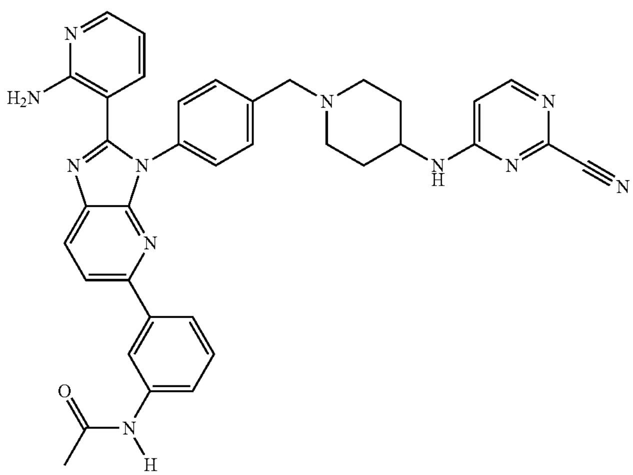 [SMILES: CC(=O)Nc1cccc(-c2ccc3nc(-c4cccnc4N)n(-c4ccc(CN5CCC(Nc6ccnc(C#N)n6)CC5)cc4)c3n2)c1] | N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)acetamide |
| 441 | 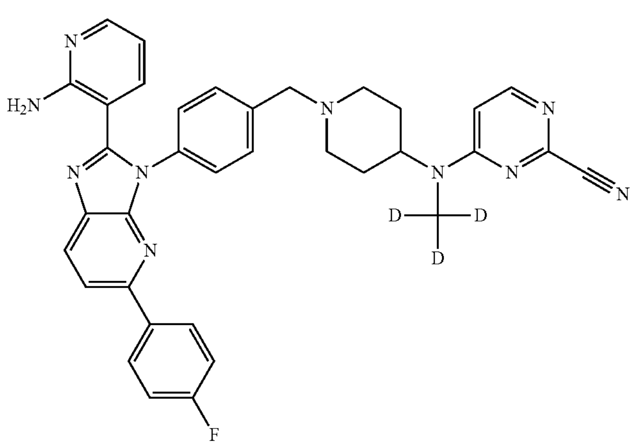 [SMILES: [2H]C([2H])([2H])N(c1ccnc(C#N)n1)C1CCN(Cc2ccc(-n3c(-c4cccnc4N)nc4ccc(-c5ccc(F)cc5)nc43)cc2)CC1] | 4-((1-(4-(2-(2-aminopyridin-3-yl)-5-(4-fluorophenyl)-3H-imidazo[4,5-b]pyridin-3-yl)benzyl)piperidin-4-yl)(methyl-d3)amino)pyrimidine-2-carbonitrile |

TABLE 1-continued

| Example | Compound Structure | Compound Name |
|---|---|---|
| 442 | 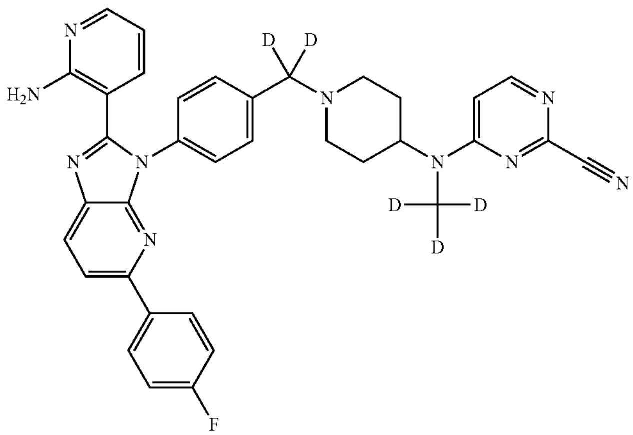 [SMILES: [2H]C([2H])([2H])N(c1ccnc(C#N)n1)C1CCN(C([2H])([2H])c2ccc(-n3c(-c4cccnc4N)nc4ccc(-c5ccc(F)cc5)nc43)cc2)CC1] | 4-((1-((4-(2-(2-aminopyridin-3-yl)-5-(4-fluorophenyl)-3H-imidazo[4,5-b]pyridin-3-yl)phenyl)methyl-d2)piperidin-4-yl)(methyl-d3)amino)pyrimidine-2-carbonitrile |
| 443 | 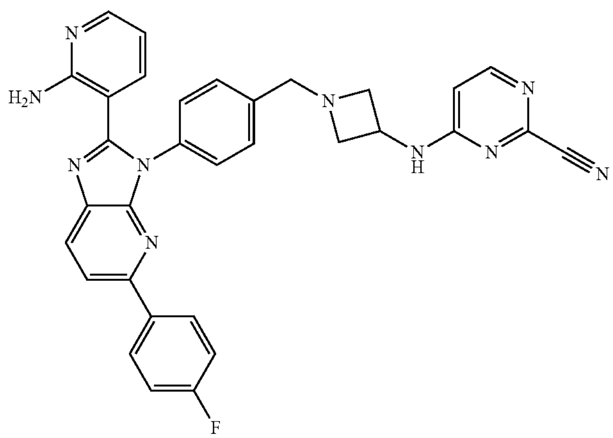 [SMILES: N#Cc1nccc(NC2CN(Cc3ccc(-n4c(-c5cccnc5N)nc5ccc(-c6ccc(F)cc6)nc54)cc3)C2)n1] | 4-((1-(4-(2-(2-aminopyridin-3-yl)-5-(4-fluorophenyl)-3H-imidazo[4,5-b]pyridin-3-yl)benzyl)azetidin-3-yl)amino)pyrimidine-2-carbonitrile |
| 444 | 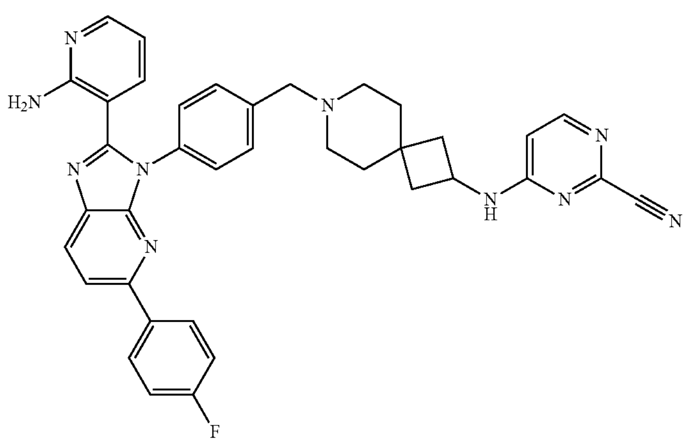 [SMILES: N#Cc1nccc(NC2CC3(CCN(Cc4ccc(-n5c(-c6cccnc6N)nc6ccc(-c7ccc(F)cc7)nc65)cc4)CC3)C2)n1] | 4-((7-(4-(2-(2-aminopyridin-3-yl)-5-(4-fluorophenyl)-3H-imidazo[4,5-b]pyridin-3-yl)benzyl)-7-azaspiro[3.5]nonan-2-yl)amino)pyrimidine-2-carbonitrile |

TABLE 1-continued

| Example | Compound Structure | Compound Name |
|---|---|---|
| 445 | 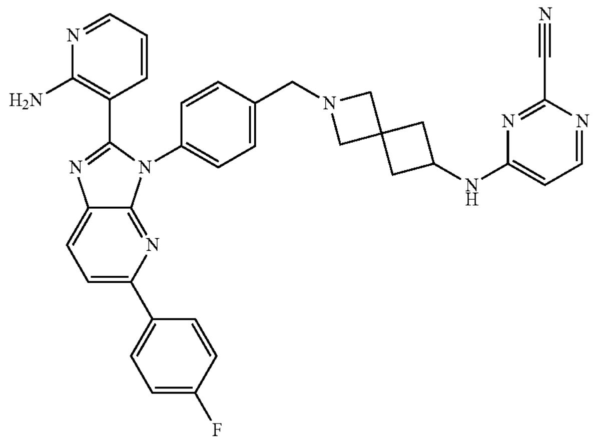 [SMILES: N#Cc1nccc(NC2CC3(C2)CN(Cc2ccc(-n4c(-c5cccnc5N)nc5ccc(-c6ccc(F)cc6)nc54)cc2)C3)n1] | 4-((2-(4-(2-(2-aminopyridin-3-yl)-5-(4-fluorophenyl)-3H-imidazo[4,5-b]pyridin-3-yl)benzyl)-2-azaspiro[3.3]heptan-6-yl)amino)pyrimidine-2-carbonitrile |
| 446 | 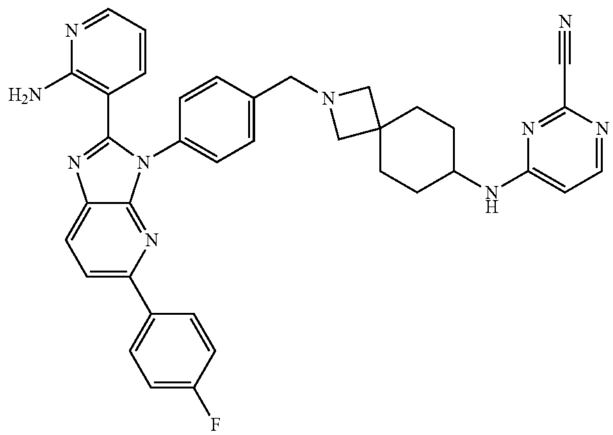 [SMILES: N#Cc1nccc(NC2CCC3(CC2)CN(Cc2ccc(-n4c(-c5cccnc5N)nc5ccc(-c6ccc(F)cc6)nc54)cc2)C3)n1] | 4-((2-(4-(2-(2-aminopyridin-3-yl)-5-(4-fluorophenyl)-3H-imidazo[4,5-b]pyridin-3-yl)benzyl)-2-azaspiro[3.5]nonan-7-yl)amino)pyrimidine-2-carbonitrile |
| 447 | 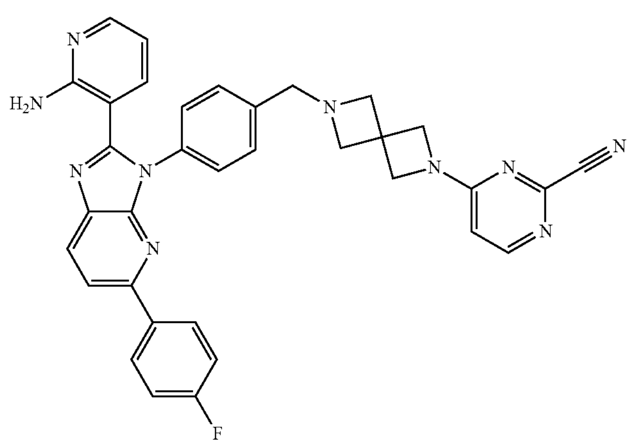 [SMILES: N#Cc1nccc(N2CC3(CN(Cc4ccc(-n5c(-c6cccnc6N)nc6ccc(-c7ccc(F)cc7)nc65)cc4)C3)C2)n1] | 4-(6-(4-(2-(2-aminopyridin-3-yl)-5-(4-fluorophenyl)-3H-imidazo[4,5-b]pyridin-3-yl)benzyl)-2,6-diazaspiro[3.3]heptan-2-yl)pyrimidine-2-carbonitrile |

TABLE 1-continued

| Example | Compound Structure | Compound Name |
|---|---|---|
| 448 | 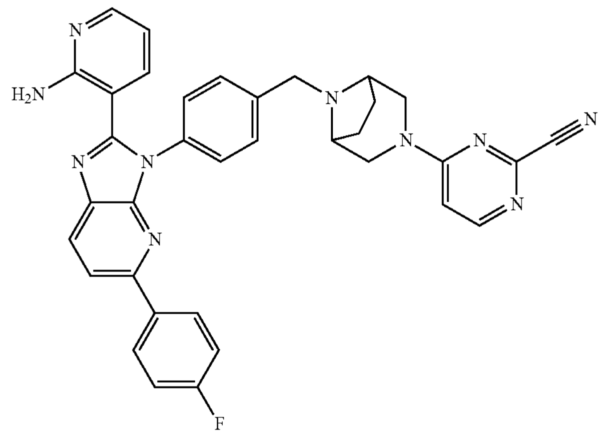 [SMILES: N#Cc1nccc(N2CC3CCC(C2)N3Cc2ccc(-n3c(-c4cccnc4N)nc4ccc(-c5ccc(F)cc5)nc43)cc2)n1] | 4-(8-(4-(2-(2-aminopyridin-3-yl)-5-(4-fluorophenyl)-3H-imidazo[4,5-b]pyridin-3-yl)benzyl)-3,8-diazabicyclo[3.2.1]octan-3-yl)pyrimidine-2-carbonitrile |
| 449 | 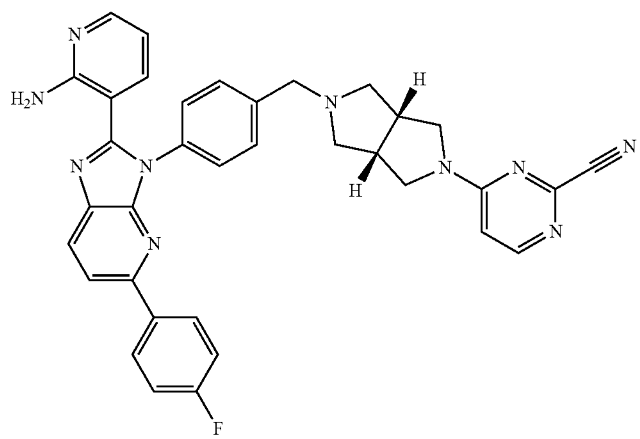 [SMILES: N#Cc1nccc(N2C[C@H]3CN(Cc4ccc(-n5c(-c6cccnc6N)nc6ccc(-c7ccc(F)cc7)nc65)cc4)C[C@H]3C2)n1] | 4-((3aR,6aS)-5-(4-(2-(2-aminopyridin-3-yl)-5-(4-fluorophenyl)-3H-imidazo[4,5-b]pyridin-3-yl)benzyl)hexahydropyrrolo[3,4-c]pyrrol-2(1H)-yl)pyrimidine-2-carbonitrile |
| 450 | 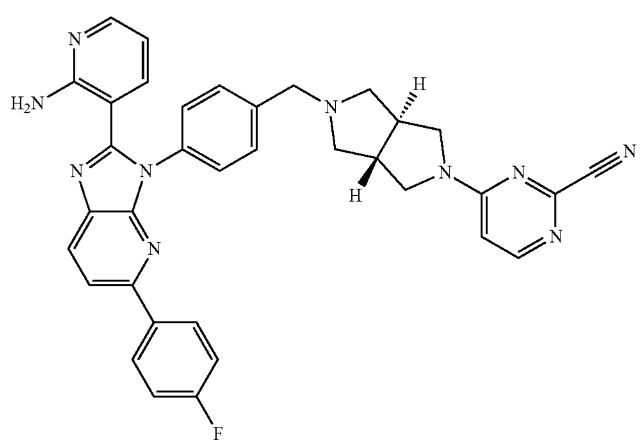 [SMILES: N#Cc1nccc(N2C[C@@H]3CN(Cc4ccc(-n5c(-c6cccnc6N)nc6ccc(-c7ccc(F)cc7)nc65)cc4)C[C@H]3C2)n1] | 4-((3aS,6aS)-5-(4-(2-(2-aminopyridin-3-yl)-5-(4-fluorophenyl)-3H-imidazo[4,5-b]pyridin-3-yl)benzyl)hexahydropyrrolo[3,4-c]pyrrol-2(1H)-yl)pyrimidine-2-carbonitrile |

TABLE 1-continued

| Example | Compound Structure | Compound Name |
|---|---|---|
| 451 | 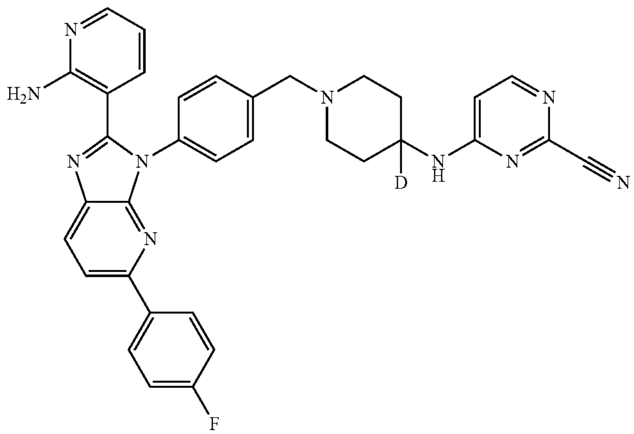 [SMILES: [2H]C1(Nc2ccnc(C#N)n2)CCN(Cc2ccc(-n3c(-c4cccnc4N)nc4ccc(-c5ccc(F)cc5)nc43)cc2)CC1] | 4-((1-(4-(2-(2-aminopyridin-3-yl)-5-(4-fluorophenyl)-3H-imidazo[4,5-b]pyridin-3-yl)benzyl)piperidin-4-yl-4-d)amino)pyrimidine-2-carbonitrile |
| 452 | 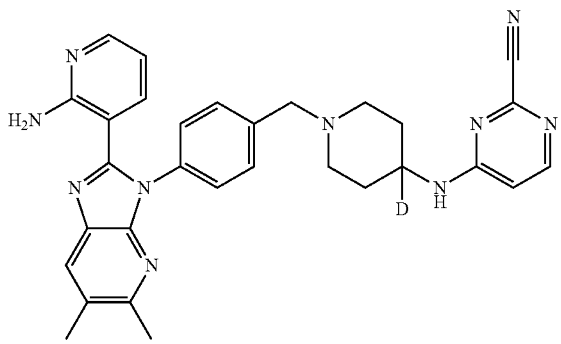 [SMILES: [2H]C1(Nc2ccnc(C#N)n2)CCN(Cc2ccc(-n3c(-c4cccnc4N)nc4cc(C)c(C)nc43)cc2)CC1] | 4-((1-(4-(2-(2-aminopyridin-3-yl)-5,6-dimethyl-3H-imidazo[4,5-b]pyridin-3-yl)benzyl)piperidin-4-yl-4-d)amino)pyrimidine-2-carbonitrile |
| 453 | 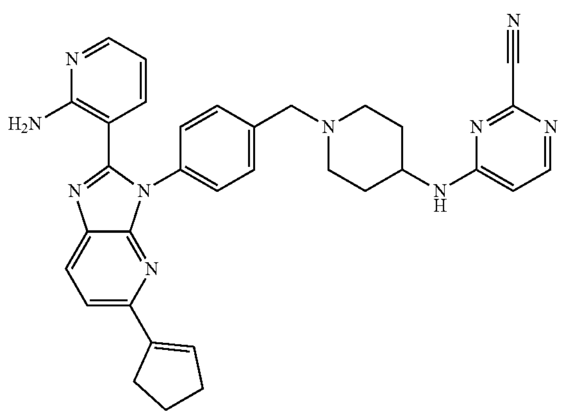 [SMILES: N#Cc1nccc(NC2CCN(Cc3ccc(-n4c(-c5cccnc5N)nc5ccc(C6=CCCC6)nc54)cc3)CC2)n1] | 4-((1-(4-(2-(2-aminopyridin-3-yl)-5-(cyclopent-1-en-1-yl)-3H-imidazo[4,5-b]pyridin-3-yl)benzyl)piperidin-4-yl)amino)pyrimidine-2-carbonitrile |
| 454 | 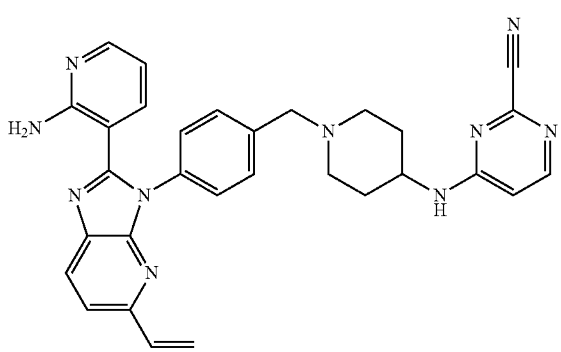 [SMILES: C=Cc1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-vinyl-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 455 | 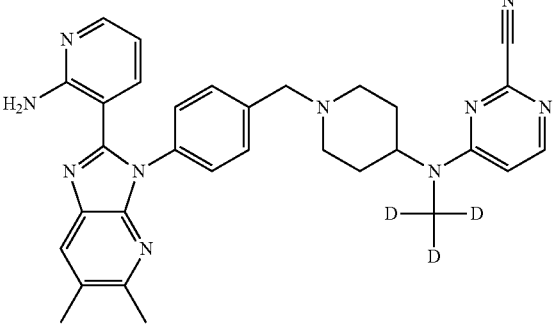 | 4-((1-(4-(2-(2-aminopyridin-3-yl)-5,6-dimethyl-3H-imidazo[4,5-b]pyridin-3-yl)benzyl)piperidin-4-yl)(methyl-d3)amino)pyrimidine-2-carbonitrile |
| 456 | 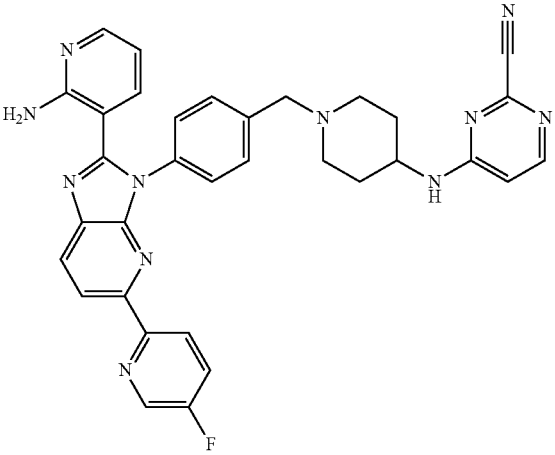 [SMILES: N#Cc1nccc(NC2CCN(Cc3ccc(-n4c(-c5cccnc5N)nc5ccc(-c6ccc(F)cn6)nc54)cc3)CC2)n1] | 4-((1-(4-(2-(2-aminopyridin-3-yl)-5-(5-fluoropyridin-2-yl)-3H-imidazo[4,5-b]pyridin-3-yl)benzyl)piperidin-4-yl)amino)pyrimidine-2-carbonitrile |
| 457 | 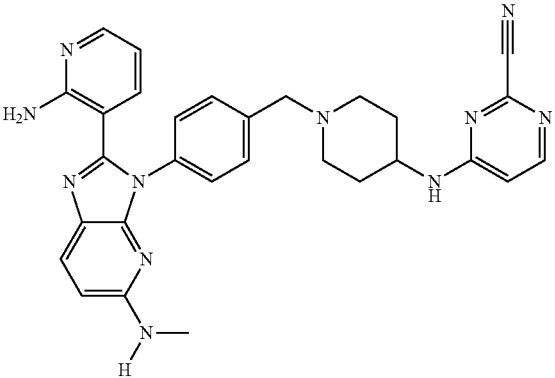 [SMILES: CNc1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(methylamino)-3H-imidazo[4,5-b]pyridin-3-yl)benzyl)piperidin-4-yl)amino)pyrimidine-2-carbonitrile |
| 458 | 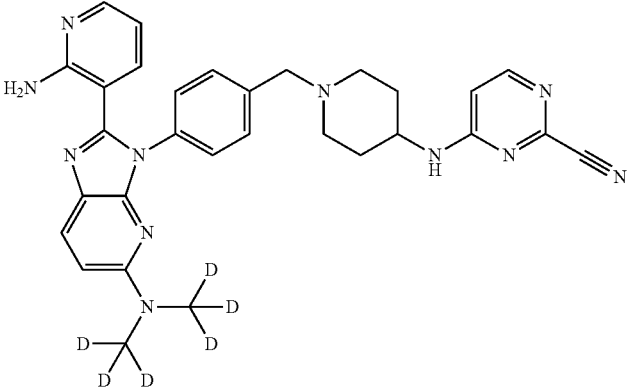 [SMILES: [2H]C([2H])([2H])N(c1ccc2nc(-c3cccnc3N)n(-c3ccc(CN4CCC(Nc5ccnc(C#N)n5)CC4)cc3)c2n1)C([2H])([2H])[2H]] | 4-((1-(4-(2-(2-aminopyridin-3-yl)-5-(bis(methyl-d3)amino)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 459 | 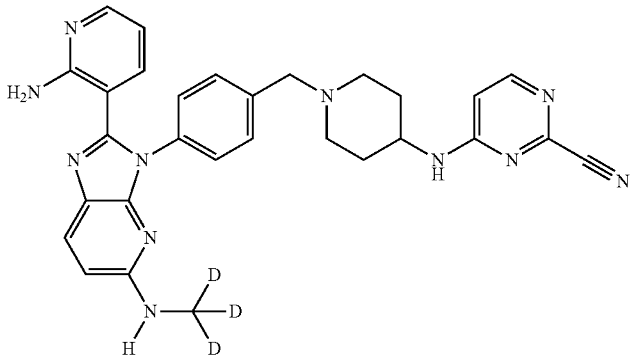 [SMILES: [2H]C([2H])([2H])Nc1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-((methyl-d3)amino)-3H-imidazo[4,5-b]pyridin-3-yl)benzyl)piperidin-4-yl)amino)pyrimidine-2-carbonitrile |
| 460 | 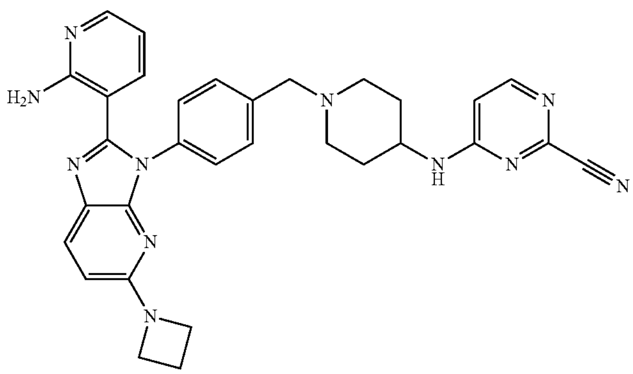 [SMILES: N#Cc1nccc(NC2CCN(Cc3ccc(-n4c(-c5cccnc5N)nc5ccc(N6CCC6)nc54)cc3)CC2)n1] | 4-((1-(4-(2-(2-aminopyridin-3-yl)-5-(azetidin-1-yl)-3H-imidazo[4,5-b]pyridin-3-yl)benzyl)piperidin-4-yl)amino)pyrimidine-2-carbonitrile |
| 461 | 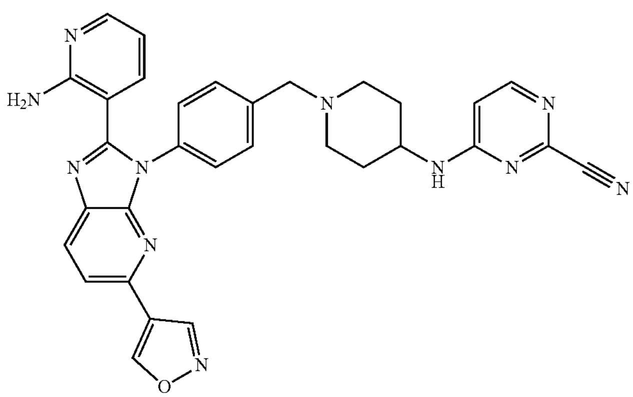 | 4-((1-(4-(2-(2-aminopyridin-3-yl)-5-(isoxazol-4-yl)-3H-imidazo[4,5-b]pyridin-3-yl)benzyl)piperidin-4-yl)amino)pyrimidine-2-carbonitrile |
| 462 | 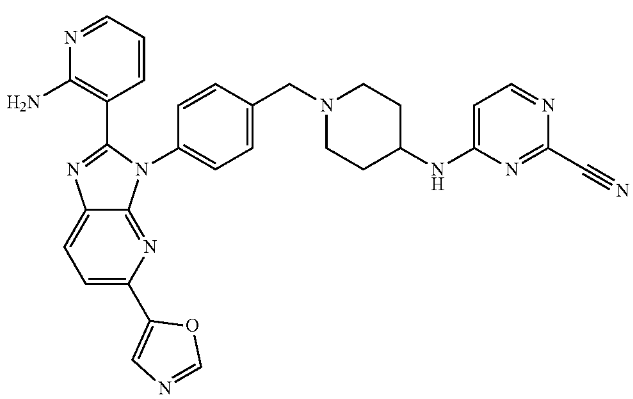 [SMILES: N#Cc1nccc(NC2CCN(Cc3ccc(-n4c(-c5cccnc5N)nc5ccc(-c6cnco6)nc54)cc3)CC2)n1] | 4-((1-(4-(2-(2-aminopyridin-3-yl)-5-(oxazol-5-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 463 | 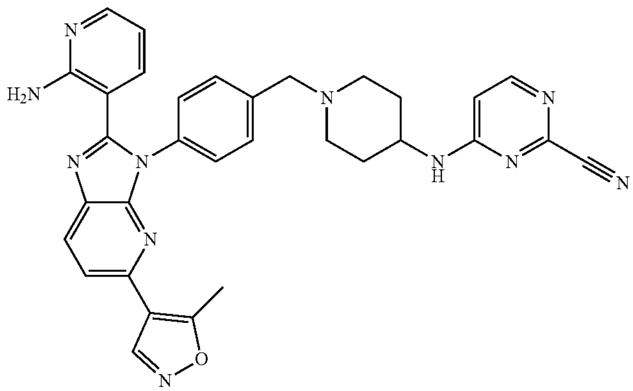 [SMILES: Cc1oncc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(5-methylisoxazol-4-yl)-3H-imidazo[4,5-b]pyridin-3-yl)benzyl)piperidin-4-yl)amino)pyrimidine-2-carbonitrile |
| 464 | 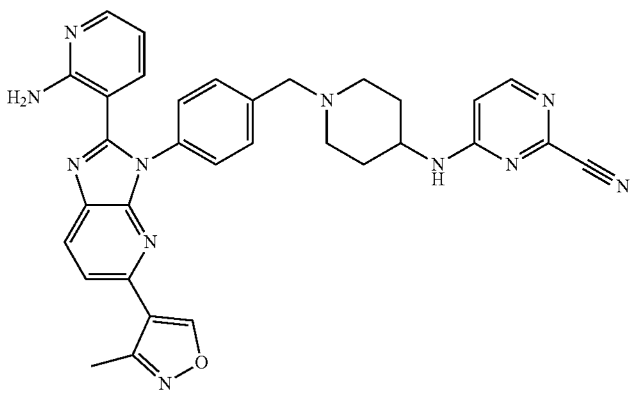 [SMILES: Cc1nocc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(3-methylisoxazol-4-yl)-3H-imidazo[4,5-b]pyridin-3-yl)benzyl)piperidin-4-yl)amino)pyrimidine-2-carbonitrile |
| 465 | 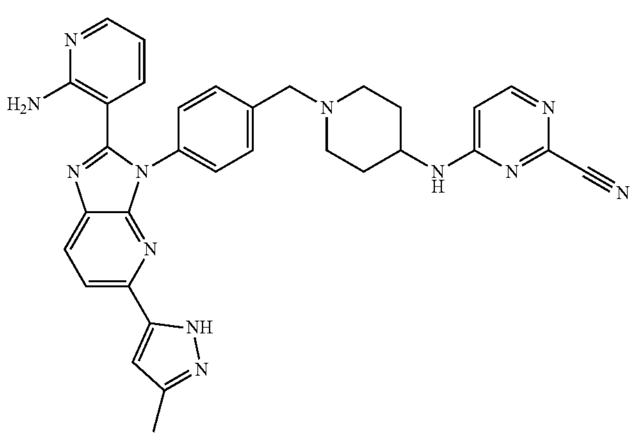 [SMILES: Cc1cc(-c2ccc3nc(-c4cccnc4N)n(-c4ccc(CN5CCC(Nc6ccnc(C#N)n6)CC5)cc4)c3n2)[nH]n1] | 4-((1-(4-(2-(2-aminopyridin-3-yl)-5-(3-methyl-1H-pyrazol-5-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 466 | 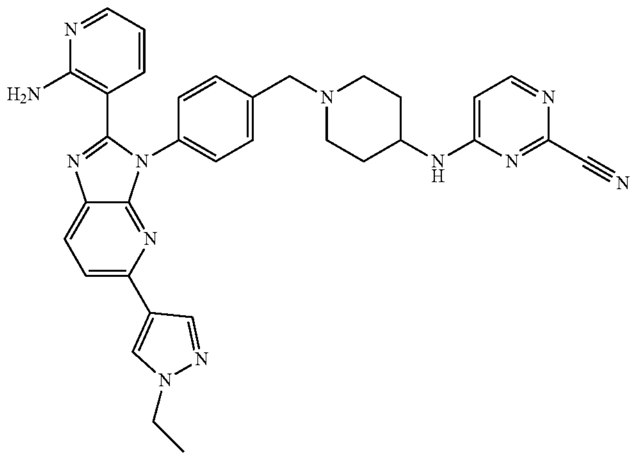 [SMILES: CCn1cc(-c2ccc3nc(-c4cccnc4N)n(-c4ccc(CN5CCC(Nc6ccnc(C#N)n6)CC5)cc4)c3n2)cn1] | 4-((1-(4-(2-(2-aminopyridin-3-yl)-5-(1-ethyl-1H-pyrazol-4-yl)-3H-imidazo[4,5-b]pyridin-3-yl)benzyl)piperidin-4-yl)amino)pyrimidine-2-carbonitrile |
| 467 | 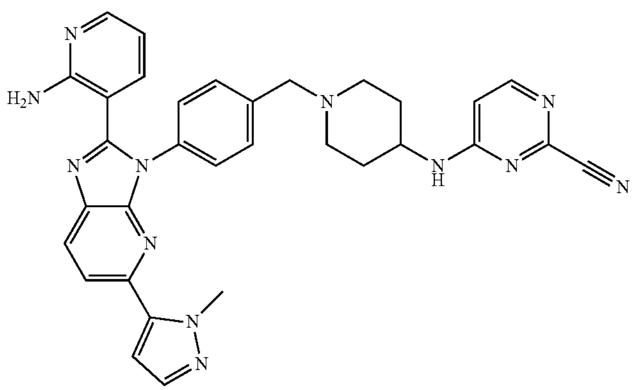 [SMILES: Cn1nccc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(1-methyl-1H-pyrazol-5-yl)-3H-imidazo[4,5-b]pyridin-3-yl)benzyl)piperidin-4-yl)amino)pyrimidine-2-carbonitrile |
| 468 | 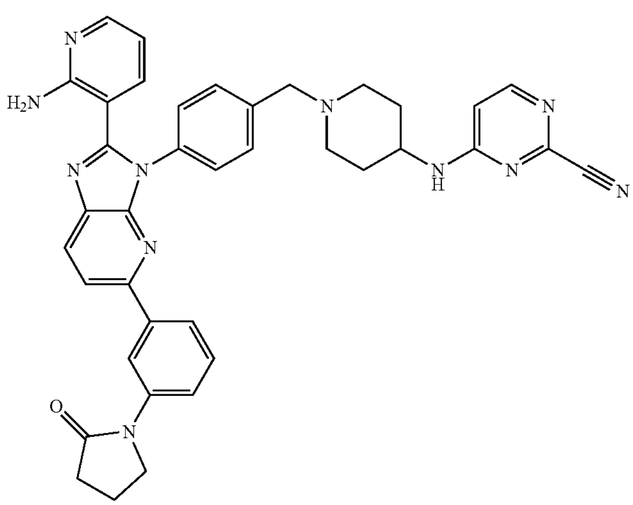 [SMILES: N#Cc1nccc(NC2CCN(Cc3ccc(-n4c(-c5cccnc5N)nc5ccc(-c6cccc(N7CCCC7=O)c6)nc54)cc3)CC2)n1] | 4-((1-(4-(2-(2-aminopyridin-3-yl)-5-(3-(2-oxopyrrolidin-1-yl)phenyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 469 | 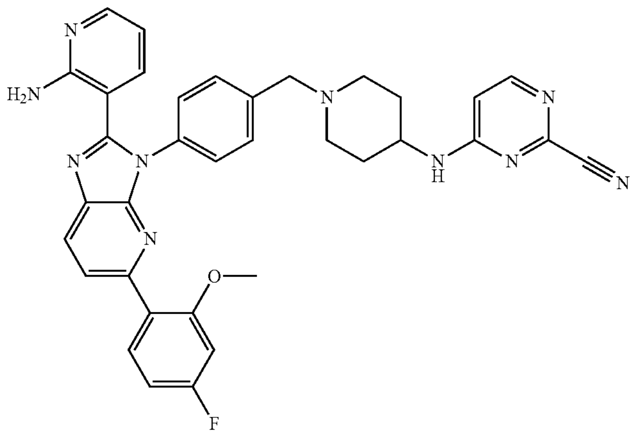 [SMILES: COc1cc(F)ccc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(4-fluoro-2-methoxyphenyl)-3H-imidazo[4,5-b]pyridin-3-yl)benzyl)piperidin-4-yl)amino)pyrimidine-2-carbonitrile |
| 470 | 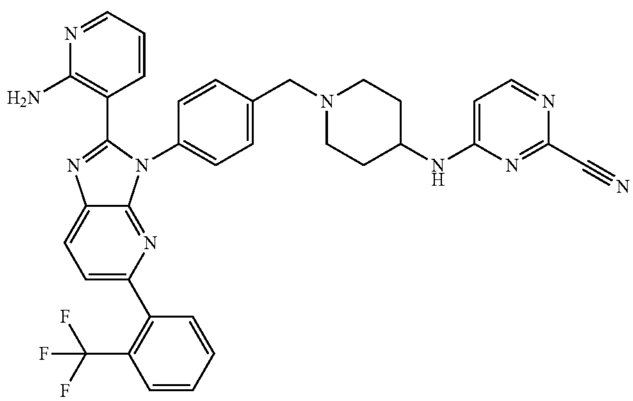 [SMILES: N#Cc1nccc(NC2CCN(Cc3ccc(-n4c(-c5cccnc5N)nc5ccc(-c6ccccc6C(F)(F)F)nc54)cc3)CC2)n1] | 4-((1-(4-(2-(2-aminopyridin-3-yl)-5-(2-(trifluoromethyl)phenyl)-3H-imidazo[4,5-b]pyridin-3-yl)benzyl)piperidin-4-yl)amino)pyrimidine-2-carbonitrile |
| 471 | 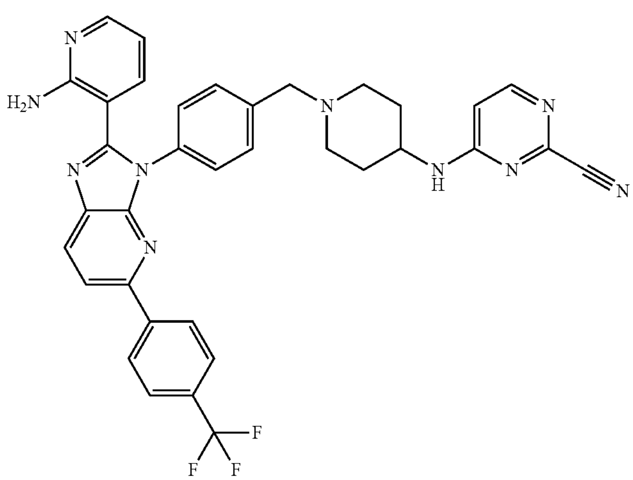 [SMILES: N#Cc1nccc(NC2CCN(Cc3ccc(-n4c(-c5cccnc5N)nc5ccc(-c6ccc(C(F)(F)F)cc6)nc54)cc3)CC2)n1] | 4-((1-(4-(2-(2-aminopyridin-3-yl)-5-(4-(trifluoromethyl)phenyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 472 | 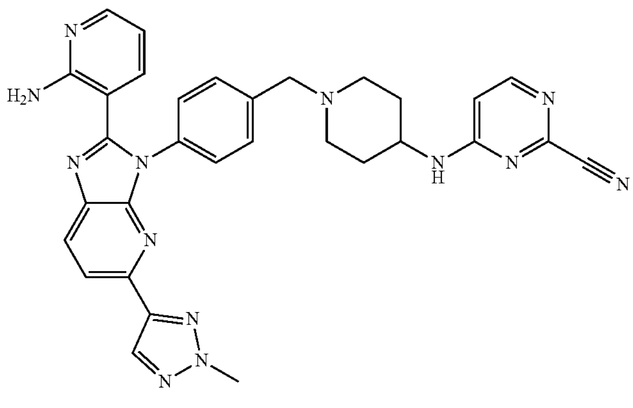 [SMILES: Cn1ncc(-c2ccc3nc(-c4cccnc4N)n(-c4ccc(CN5CCC(Nc6ccnc(C#N)n6)CC5)cc4)c3n2)n1] | 4-((1-(4-(2-(2-aminopyridin-3-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile |
| 473 | 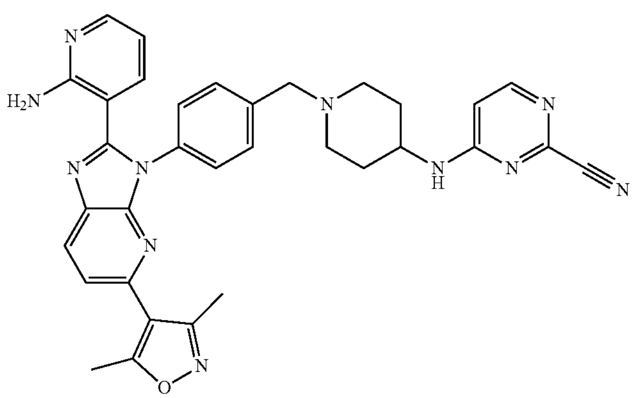 [SMILES: Cc1noc(C)c1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(3,5-dimethylisoxazol-4-yl)-3H-imidazo[4,5-b]pyridin-3-yl)benzyl)piperidin-4-yl)amino)pyrimidine-2-carbonitrile |
| 474 | 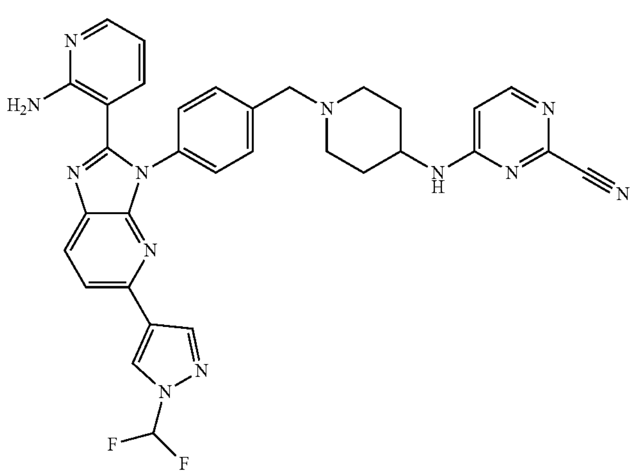 [SMILES: N#Cc1nccc(NC2CCN(Cc3ccc(-n4c(-c5cccnc5N)nc5ccc(-c6cnn(C(F)F)c6)nc54)cc3)CC2)n1] | 4-((1-(4-(2-(2-aminopyridin-3-yl)-5-(1-(difluoromethyl)-1H-pyrazol-4-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 475 | 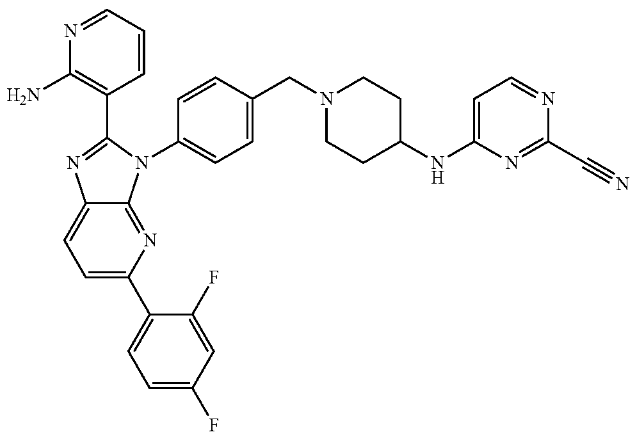 | 4-((1-(4-(2-(2-aminopyridin-3-yl)-5-(2,4-difluorophenyl)-3H-imidazo[4,5-b]pyridin-3-yl)benzyl)piperidin-4-yl)amino)pyrimidine-2-carbonitrile |
| 476 | 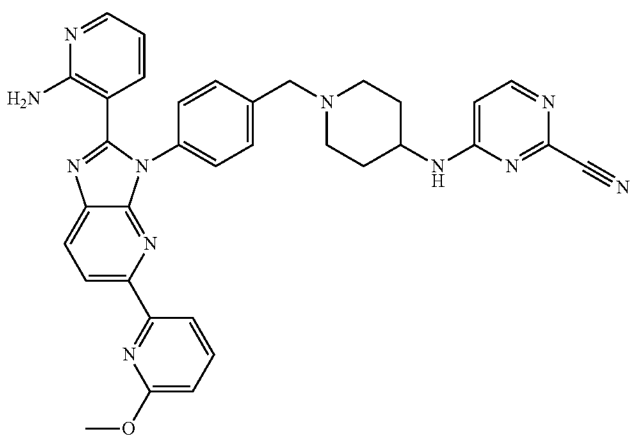 [SMILES: COc1cccc(-c2ccc3nc(-c4cccnc4N)n(-c4ccc(CN5CCC(Nc6ccnc(C#N)n6)CC5)cc4)c3n2)n1] | 4-((1-(4-(2-(2-aminopyridin-3-yl)-5-(6-methoxypyridin-2-yl)-3H-imidazo[4,5-b]pyridin-3-yl)benzyl)piperidin-4-yl)amino)pyrimidine-2-carbonitrile |
| 477 | 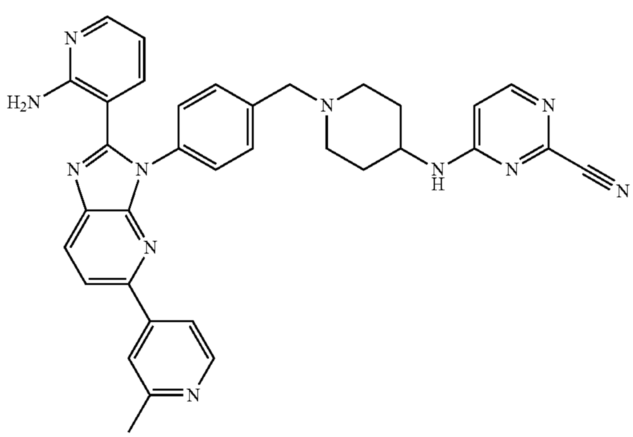 | 4-((1-(4-(2-(2-aminopyridin-3-yl)-5-(2-methylpyridin-4-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 478 | 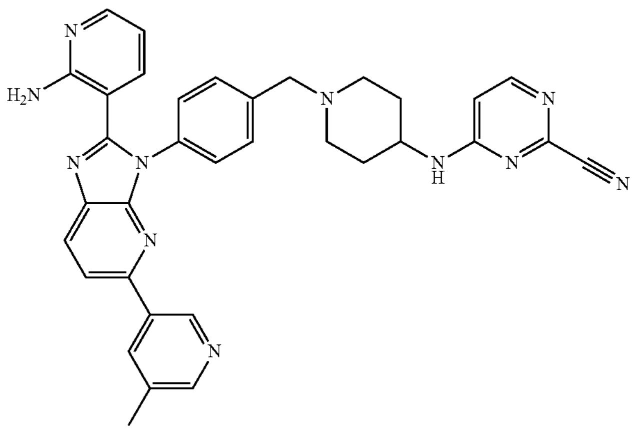 | 4-((1-(4-(2-(2-aminopyridin-3-yl)-5-(5-methylpyridin-3-yl)-3H-imidazo[4,5-b]pyridin-3-yl)benzyl)piperidin-4-yl)amino)pyrimidine-2-carbonitrile |
| 479 | 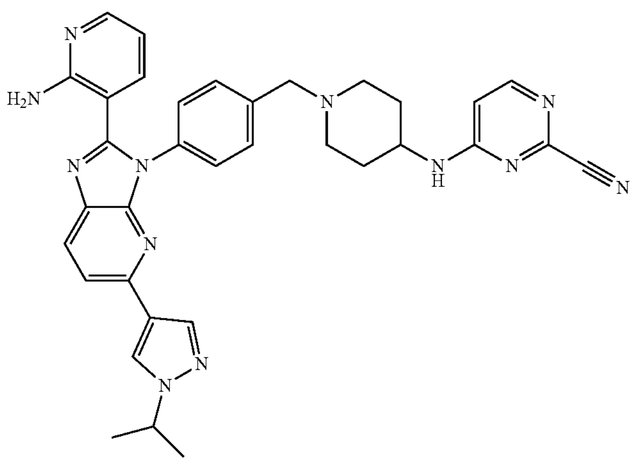 [SMILES: CC(C)n1cc(-c2ccc3nc(-c4cccnc4N)n(-c4ccc(CN5CCC(Nc6ccnc(C#N)n6)CC5)cc4)c3n2)cn1] | 4-((1-(4-(2-(2-aminopyridin-3-yl)-5-(1-isopropyl-1H-pyrazol-4-yl)-3H-imidazo[4,5-b]pyridin-3-yl)benzyl)piperidin-4-yl)amino)pyrimidine-2-carbonitrile |
| 480 | 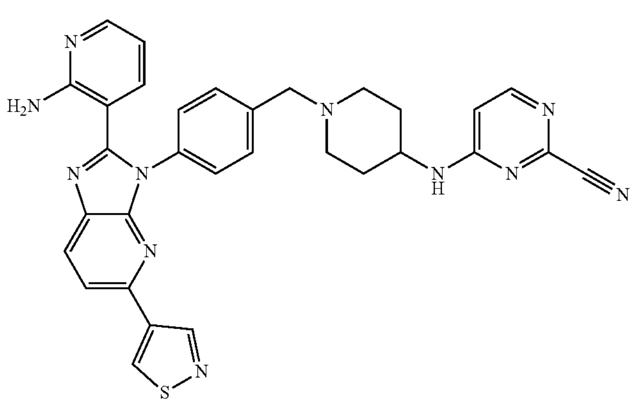 | 4-((1-(4-(2-(2-aminopyridin-3-yl)-5-(isothiazol-4-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 481 | 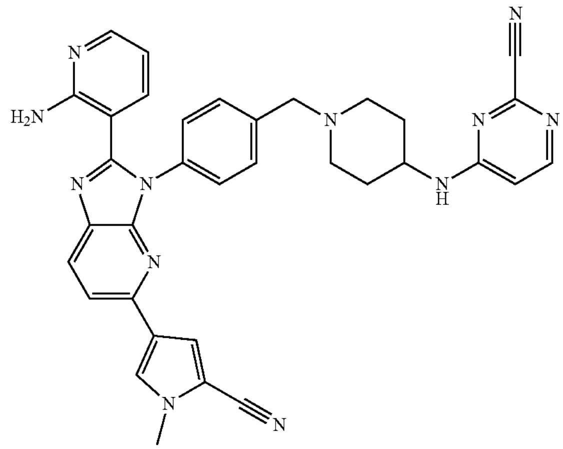 [SMILES: Cn1cc(-c2ccc3nc(-c4cccnc4N)n(-c4ccc(CN5CCC(Nc6ccnc(C#N)n6)CC5)cc4)c3n2)cc1C#N] | 4-((1-(4-(2-(2-aminopyridin-3-yl)-5-(5-cyano-1-methyl-1H-pyrrol-3-yl)-3H-imidazo[4,5-b]pyridin-3-yl)benzyl)piperidin-4-yl)amino)pyrimidine-2-carbonitrile |
| 482 | 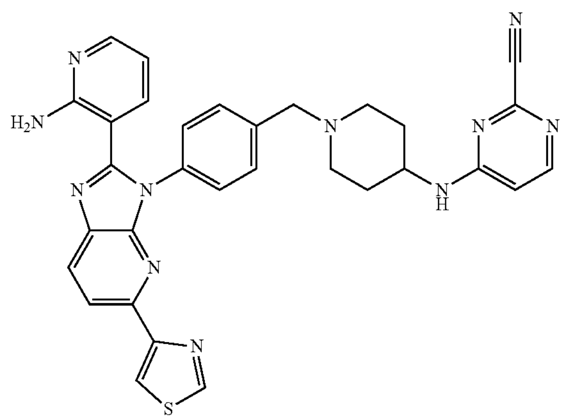 [SMILES: N#Cc1nccc(NC2CCN(Cc3ccc(-n4c(-c5cccnc5N)nc5ccc(-c6cscn6)nc54)cc3)CC2)n1] | 4-((1-(4-(2-(2-aminopyridin-3-yl)-5-(thiazol-4-yl)-3H-imidazo[4,5-b]pyridin-3-yl)benzyl)piperidin-4-yl)amino)pyrimidine-2-carbonitrile |
| 483 | 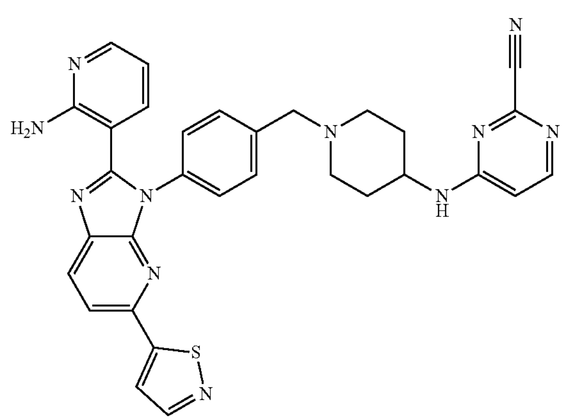 [SMILES: N#Cc1nccc(NC2CCN(Cc3ccc(-n4c(-c5cccnc5N)nc5ccc(-c6ccns6)nc54)cc3)CC2)n1] | 4-((1-(4-(2-(2-aminopyridin-3-yl)-5-(isothiazol-5-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 484 | 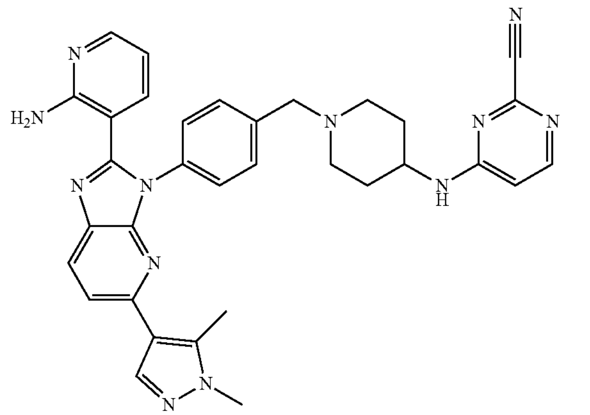 [SMILES: Cc1c(-c2ccc3nc(-c4cccnc4N)n(-c4ccc(CN5CCC(Nc6ccnc(C#N)n6)CC5)cc4)c3n2)cnn1C] | 4-((1-(4-(2-(2-aminopyridin-3-yl)-5-(1,5-dimethyl-1H-pyrazol-4-yl)-3H-imidazo[4,5-b]pyridin-3-yl)benzyl)piperidin-4-yl)amino)pyrimidine-2-carbonitrile |
| 485 | 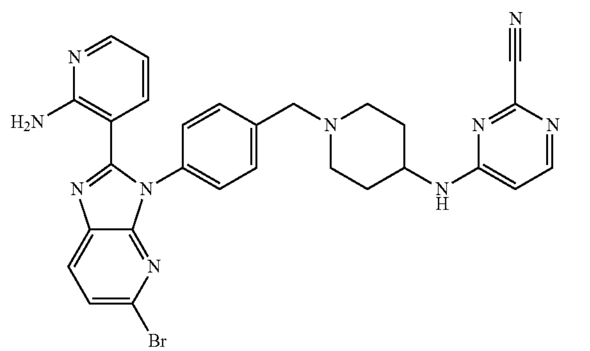 [SMILES: N#Cc1nccc(NC2CCN(Cc3ccc(-n4c(-c5cccnc5N)nc5ccc(Br)nc54)cc3)CC2)n1] | 4-((1-(4-(2-(2-aminopyridin-3-yl)-5-bromo-3H-imidazo[4,5-b]pyridin-3-yl)benzyl)piperidin-4-yl)amino)pyrimidine-2-carbonitrile |
| 486 | 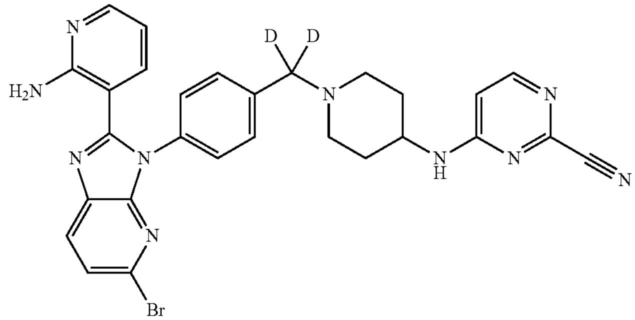 [SMILES: [2H]C([2H])(c1ccc(-n2c(-c3cccnc3N)nc3ccc(Br)nc32)cc1)N1CCC(Nc2ccnc(C#N)n2)CC1] | 4-((1-((4-(2-(2-aminopyridin-3-yl)-5-bromo-3H-imidazo[4,5-b]pyridin-3-yl)phenyl)methyl-d2)piperidin-4-yl)amino)pyrimidine-2-carbonitrile |
| 487 | 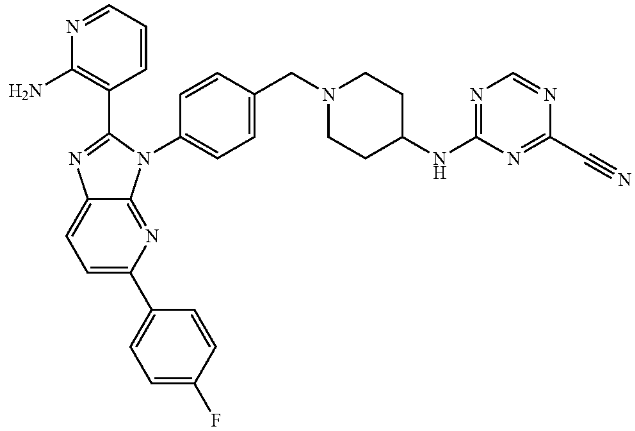 [SMILES: N#Cc1ncnc(NC2CCN(Cc3ccc(-n4c(-c5cccnc5N)nc5ccc(-c6ccc(F)cc6)nc54)cc3)CC2)n1] | 4-((1-(4-(2-(2-aminopyridin-3-yl)-5-(4-fluorophenyl)-3H-imidazo[4,5-b]pyridin-3-yl)benzyl)piperidin-4-yl)amino)-1,3,5-triazine-2-carbonitrile |

TABLE 1-continued

| Example | Compound Structure | Compound Name |
|---|---|---|
| 488 | 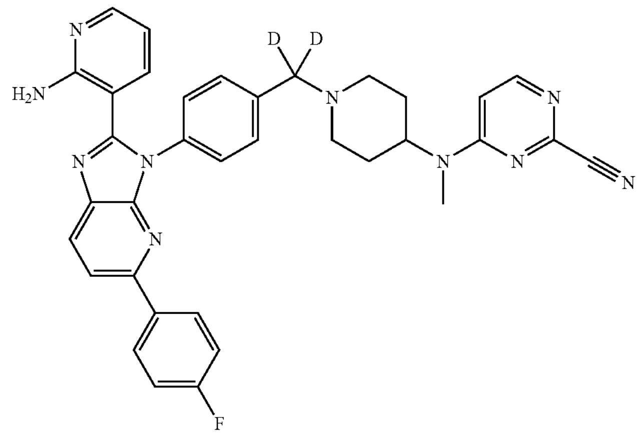 [SMILES: [2H]C([2H])(c1ccc(-n2c(-c3cccnc3N)nc3ccc(-c4ccc(F)cc4)nc32)cc1)N1CCC(N(C)c2ccnc(C#N)n2)CC1] | 4-((1-((4-(2-(2-aminopyridin-3-yl)-5-(4-fluorophenyl)-3H-imidazo[4,5-b]pyridin-3-yl)phenyl)methyl-d2)piperidin-4-yl)(methyl)amino)pyrimidine-2-carbonitrile |
| 489 | 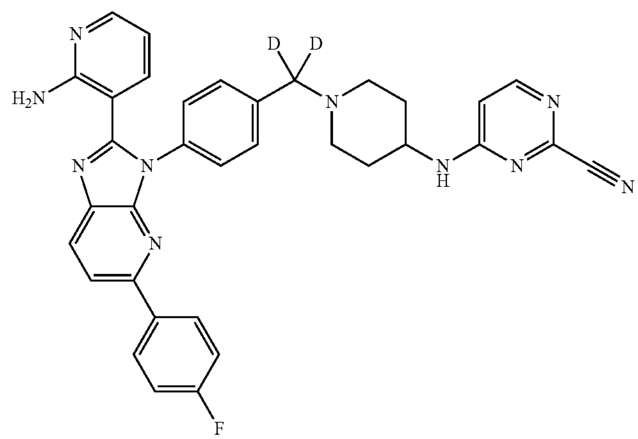 [SMILES: [2H]C([2H])(c1ccc(-n2c(-c3cccnc3N)nc3ccc(-c4ccc(F)cc4)nc32)cc1)N1CCC(Nc2ccnc(C#N)n2)CC1] | 4-((1-((4-(2-(2-aminopyridin-3-yl)-5-(4-fluorophenyl)-3H-imidazo[4,5-b]pyridin-3-yl)phenyl)methyl-d2)piperidin-4-yl)amino)pyrimidine-2-carbonitrile |
| 490 | 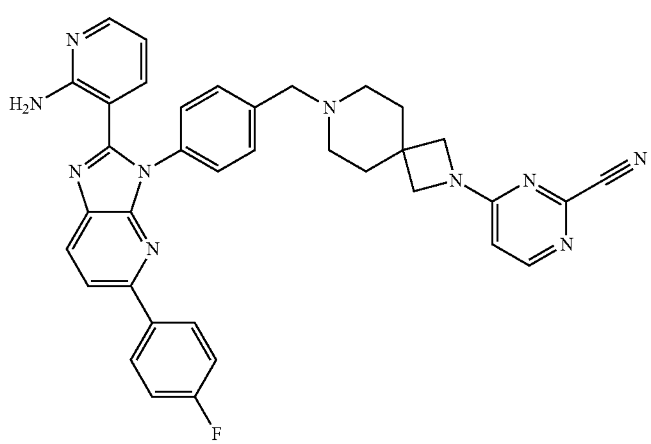 [SMILES: N#Cc1nccc(N2CC3(CCN(Cc4ccc(-n5c(-c6cccnc6N)nc6ccc(-c7ccc(F)cc7)nc65)cc4)CC3)C2)n1] | 4-(7-(4-(2-(2-aminopyridin-3-yl)-5-(4-fluorophenyl)-3H-imidazo[4,5-b]pyridin-3-yl)benzyl)-2,7-diazaspiro[3.5]nonan-2-yl)pyrimidine-2-carbonitrile |

TABLE 1-continued

| Example | Compound Structure | Compound Name |
|---|---|---|
| 491 | 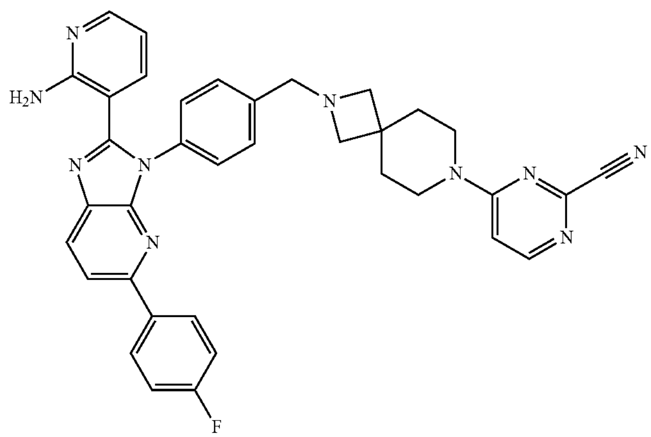 [SMILES: N#Cc1nccc(N2CCC3(CC2)CN(Cc2ccc(-n4c(-c5cccnc5N)nc5ccc(-c6ccc(F)cc6)nc54)cc2)C3)n1] | 4-(2-(4-(2-(2-aminopyridin-3-yl)-5-(4-fluorophenyl)-3H-imidazo[4,5-b]pyridin-3-yl)benzyl)-2,7-diazaspiro[3.5]nonan-7-yl)pyrimidine-2-carbonitrile |
| 492 | 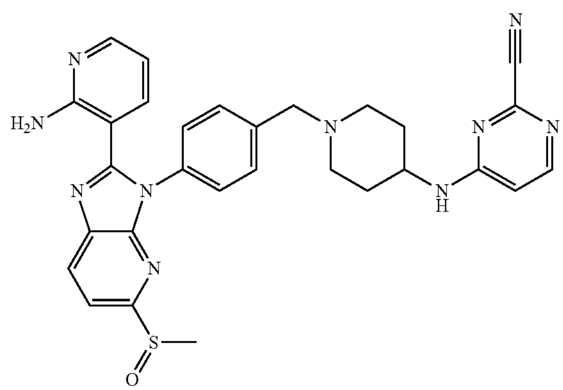 | 4-((1-(4-(2-(2-aminopyridin-3-yl)-5-(methylsulfinyl)-3H-imidazo[4,5-b]pyridin-3-yl)benzyl)piperidin-4-yl)amino)pyrimidine-2-carbonitrile |
| 493 | 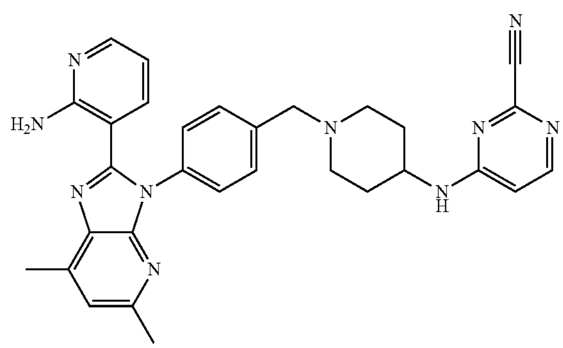 [SMILES: Cc1cc(C)c2nc(-c3cccnc3N)n(-c3ccc(CN4CCC(Nc5ccnc(C#N)n5)CC4)cc3)c2n1] | 4-((1-(4-(2-(2-aminopyridin-3-yl)-5,7-dimethyl-3H-imidazo[4,5-b]pyridin-3-yl)benzyl)piperidin-4-yl)amino)pyrimidine-2-carbonitrile |
| 494 | 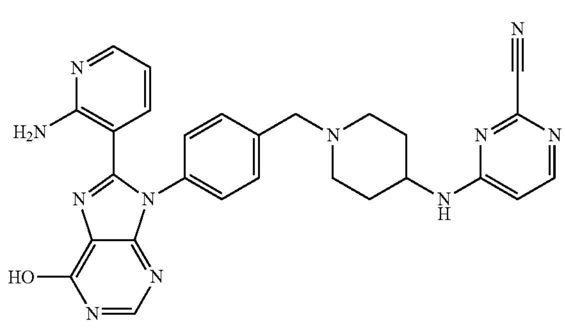 [SMILES: N#Cc1nccc(NC2CCN(Cc3ccc(-n4c(-c5cccnc5N)nc5c(O)ncnc54)cc3)CC2)n1] | 4-((1-(4-(8-(2-aminopyridin-3-yl)-6-hydroxy-9H-purin-9-yl)benzyl)piperidin-4-yl)amino)pyrimidine-2-carbonitrile |

TABLE 1-continued

| Example | Compound Structure | Compound Name |
|---|---|---|
| 495 | 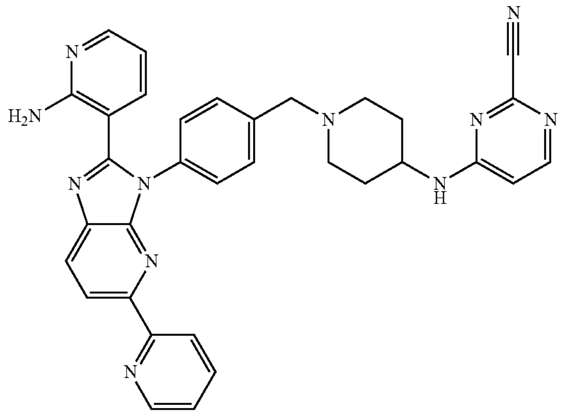 | 4-((1-(4-(2-(2-aminopyridin-3-yl)-5-(pyridin-2-yl)-3H-imidazo[4,5-b]pyridin-3-yl)benzyl)piperidin-4-yl)amino)pyrimidine-2-carbonitrile |
| 496 | 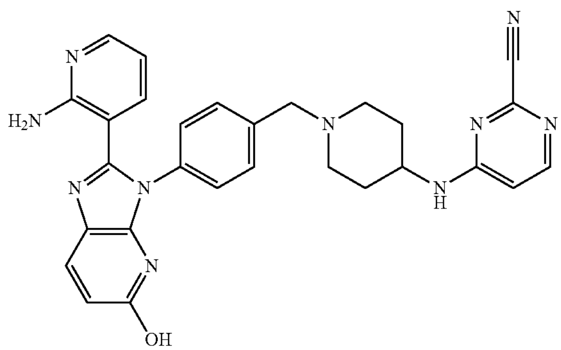 [SMILES: N#Cc1nccc(NC2CCN(Cc3ccc(-n4c(-c5cccnc5N)nc5ccc(O)nc54)cc3)CC2)n1] | 4-((1-(4-(2-(2-aminopyridin-3-yl)-5-hydroxy-3H-imidazo[4,5-b]pyridin-3-yl)benzyl)piperidin-4-yl)amino)pyrimidine-2-carbonitrile |
| 497 | 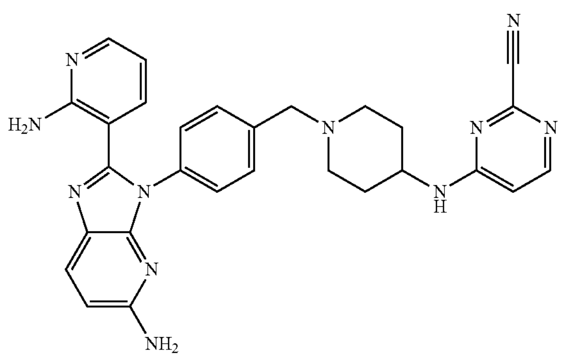 [SMILES: N#Cc1nccc(NC2CCN(Cc3ccc(-n4c(-c5cccnc5N)nc5ccc(N)nc54)cc3)CC2)n1] | 4-((1-(4-(5-amino-2-(2-aminopyridin-3-yl)-3H-imidazo[4,5-b]pyridin-3-yl)benzyl)piperidin-4-yl)amino)pyrimidine-2-carbonitrile |
| 498 | 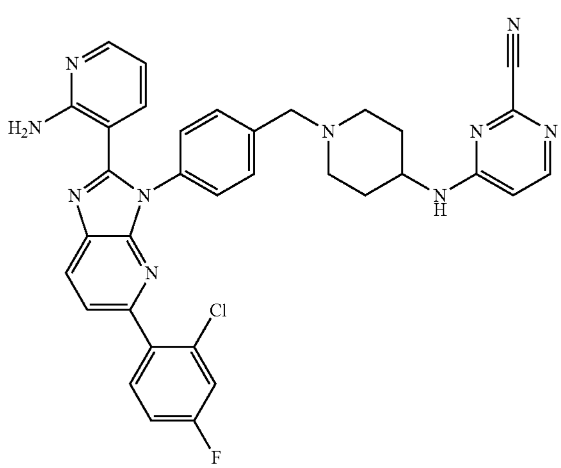 [SMILES: N#Cc1nccc(NC2CCN(Cc3ccc(-n4c(-c5cccnc5N)nc5ccc(-c6ccc(F)cc6Cl)nc54)cc3)CC2)n1] | 4-((1-(4-(2-(2-aminopyridin-3-yl)-5-(2-chloro-4-fluorophenyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 499 | 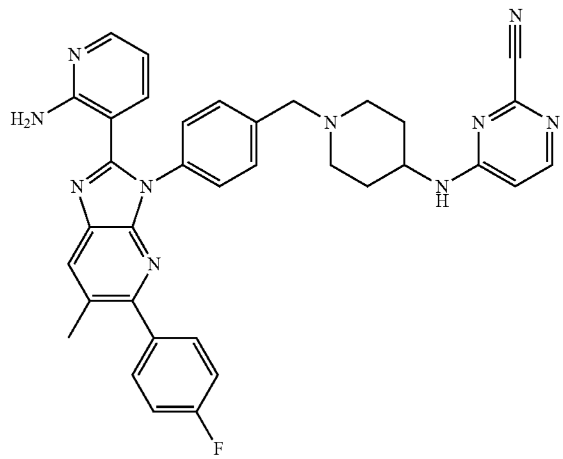 [SMILES: Cc1cc2nc(-c3cccnc3N)n(-c3ccc(CN4CCC(Nc5ccnc(C#N)n5)CC4)cc3)c2nc1-c1ccc(F)cc1] | 4-((1-(4-(2-(2-aminopyridin-3-yl)-5-(4-fluorophenyl)-6-methyl-3H-imidazo[4,5-b]pyridin-3-yl)benzyl)piperidin-4-yl)amino)pyrimidine-2-carbonitrile |
| 500 | 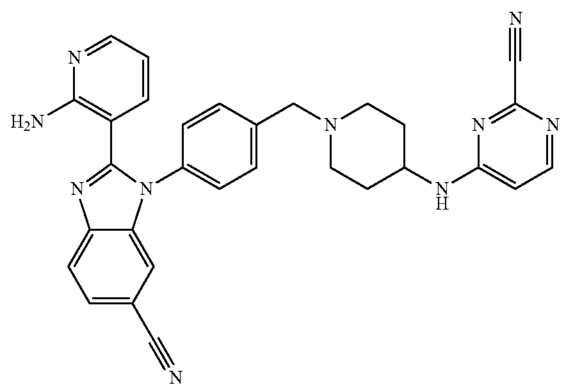 [SMILES: N#Cc1ccc2nc(-c3cccnc3N)n(-c3ccc(CN4CCC(Nc5ccnc(C#N)n5)CC4)cc3)c2c1] | 2-(2-aminopyridin-3-yl)-1-(4-((4-((2-cyanopyrimidin-4-yl)amino)piperidin-1-yl)methyl)phenyl)-1H-benzo[d]imidazole-6-carbonitrile |
| 501 | 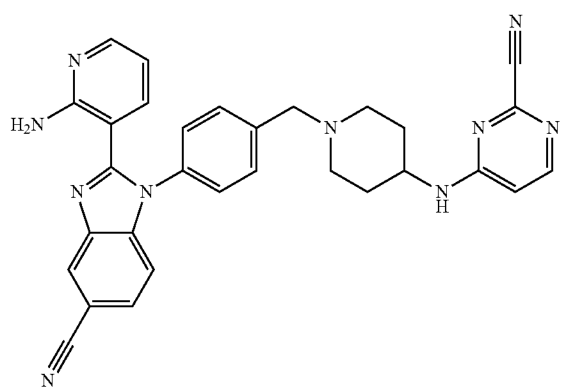 [SMILES: N#Cc1ccc2c(c1)nc(-c1cccnc1N)n2-c1ccc(CN2CCC(Nc3ccnc(C#N)n3)CC2)cc1] | 2-(2-aminopyridin-3-yl)-1-(4-((4-((2-cyanopyrimidin-4-yl)amino)piperidin-1-yl)methyl)phenyl)-1H-benzo[d]imidazole-5-carbonitrile |
| 502 | 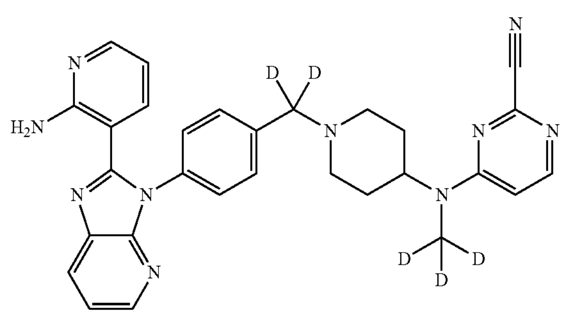 [SMILES: [2H]C([2H])([2H])N(c1ccnc(C#N)n1)C1CCN(C([2H])([2H])c2ccc(-n3c(-c4cccnc4N)nc4cccnc43)cc2)CC1] | 4-((1-((4-(2-(2-aminopyridin-3-yl)-3H-imidazo[4,5-b]pyridin-3-yl)phenyl)methyl-d2)piperidin-4-yl)(methyl-d3)amino)pyrimidine-2-carbonitrile |

TABLE 1-continued

| Example | Compound Structure | Compound Name |
|---|---|---|
| 503 | 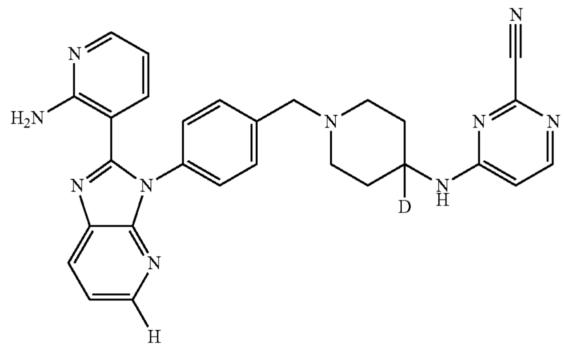 | 4-((1-(4-(2-(2-aminopyridin-3-yl)-3H-imidazo[4,5-b]pyridin-3-yl)benzyl)piperidin-4-yl-4-d)amino)pyrimidine-2-carbonitrile |
| 504 | 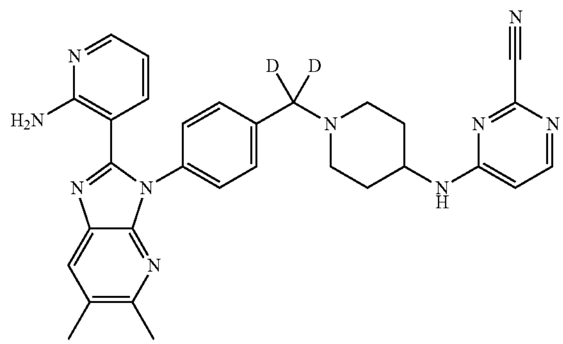 [SMILES: [2H]C([2H])(c1ccc(-n2c(-c3cccnc3N)nc3cc(C)c(C)nc32)cc1)N1CCC(Nc2ccnc(C#N)n2)CC1] | 4-((1-((4-(2-(2-aminopyridin-3-yl)-5,6-dimethyl-3H-imidazo[4,5-b]pyridin-3-yl)phenyl)methyl-d2)piperidin-4-yl)amino)pyrimidine-2-carbonitrile |
| 505 | 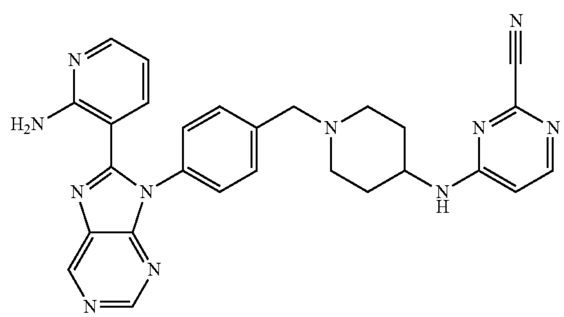 [SMILES: N#Cc1nccc(NC2CCN(Cc3ccc(-n4c(-c5cccnc5N)nc5cncnc54)cc3)CC2)n1] | 4-((1-(4-(8-(2-aminopyridin-3-yl)-9H-purin-9-yl)benzyl)piperidin-4-yl)amino)pyrimidine-2-carbonitrile |
| 506 | 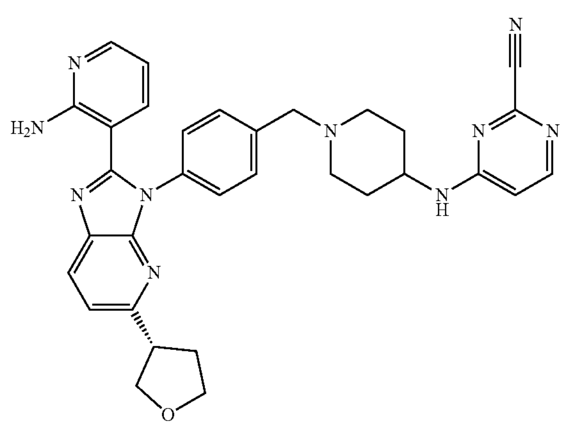 | (S)-4-((1-(4-(2-(2-aminopyridin-3-yl)-5-(tetrahydrofuran-3-yl)-3H-imidazo[4,5-b]pyridin-3-yl)benzyl)piperidin-4-yl)amino)pyrimidine-2-carbonitrile |

Stereochemistry arbitrarily assigned

TABLE 1-continued

| Example | Compound Structure | Compound Name |
|---|---|---|
| 507 | Stereochemistry arbitrarily assigned | (R)-4-((1-(4-(2-(2-aminopyridin-3-yl)-5-(tetrahydrofuran-3-yl)-3H-imidazo[4,5-b]pyridin-3-yl)benzyl)piperidin-4-yl)amino)pyrimidine-2-carbonitrile |
| 508 | 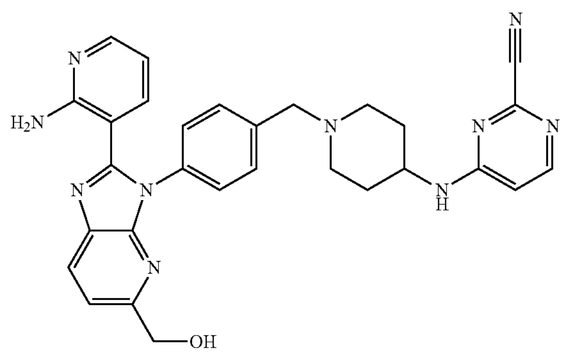 [SMILES: N#Cc1nccc(NC2CCN(Cc3ccc(-n4c(-c5cccnc5N)nc5ccc(CO)nc54)cc3)CC2)n1] | 4-((1-(4-(2-(2-aminopyridin-3-yl)-5-(hydroxymethyl)-3H-imidazo[4,5-b]pyridin-3-yl)benzyl)piperidin-4-yl)amino)pyrimidine-2-carbonitrile |
| 509 | 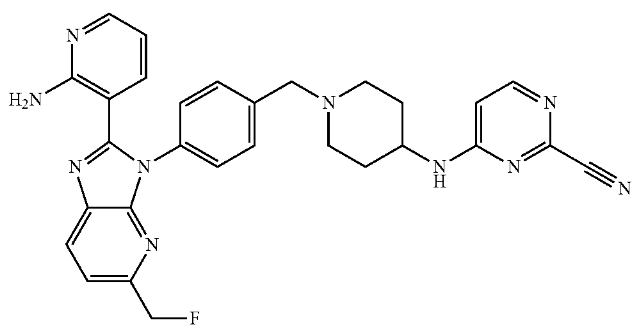 | 4-((1-(4-(2-(2-aminopyridin-3-yl)-5-(fluoromethyl)-3H-imidazo[4,5-b]pyridin-3-yl)benzyl)piperidin-4-yl)amino)pyrimidine-2-carbonitrile |
| 510 | 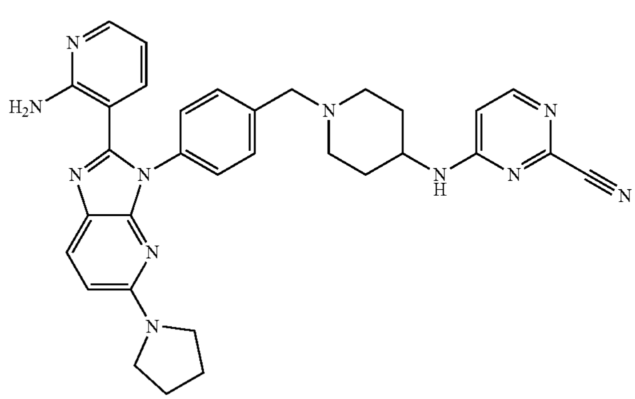 [SMILES: N#Cc1nccc(NC2CCN(Cc3ccc(-n4c(-c5cccnc5N)nc5ccc(N6CCCC6)nc54)cc3)CC2)n1] | 4-((1-(4-(2-(2-aminopyridin-3-yl)-5-(pyrrolidin-1-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 511 | 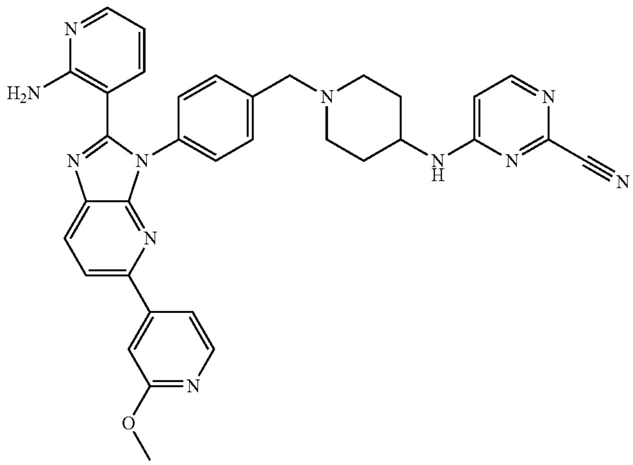 [SMILES: COc1cc(-c2ccc3nc(-c4cccnc4N)n(-c4ccc(CN5CCC(Nc6ccnc(C#N)n6)CC5)cc4)c3n2)ccn1] | 4-((1-(4-(2-(2-aminopyridin-3-yl)-5-(2-methoxypyridin-4-yl)-3H-imidazo[4,5-b]pyridin-3-yl)benzyl)piperidin-4-yl)amino)pyrimidine-2-carbonitrile |
| 512 | 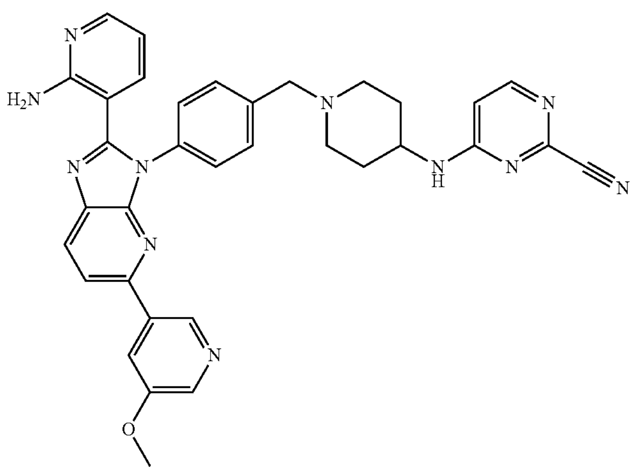 [SMILES: COc1cncc(-c2ccc3nc(-c4cccnc4N)n(-c4ccc(CN5CCC(Nc6ccnc(C#N)n6)CC5)cc4)c3n2)c1] | 4-((1-(4-(2-(2-aminopyridin-3-yl)-5-(5-methoxypyridin-3-yl)-3H-imidazo[4,5-b]pyridin-3-yl)benzyl)piperidin-4-yl)amino)pyrimidine-2-carbonitrile |
| 513 | 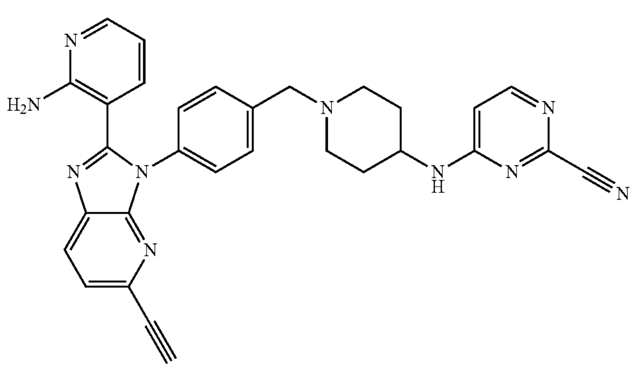 [SMILES: C#Cc1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-ethynyl-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 514 | 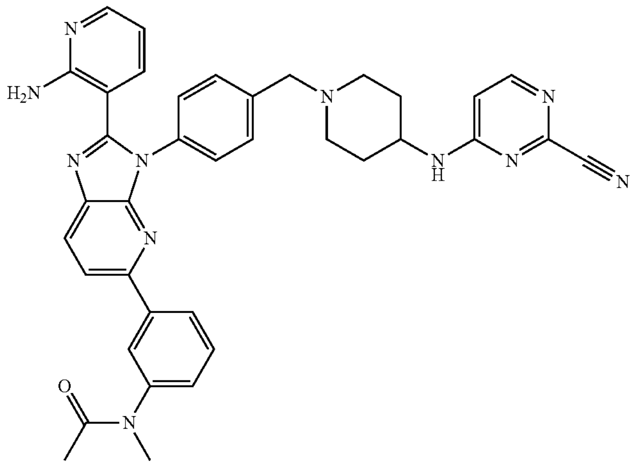 [SMILES: CC(=O)N(C)c1cccc(-c2ccc3nc(-c4cccnc4N)n(-c4ccc(CN5CCC(Nc6ccnc(C#N)n6)CC5)cc4)c3n2)c1] | N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)-N-methylacetamide |
| 515 | 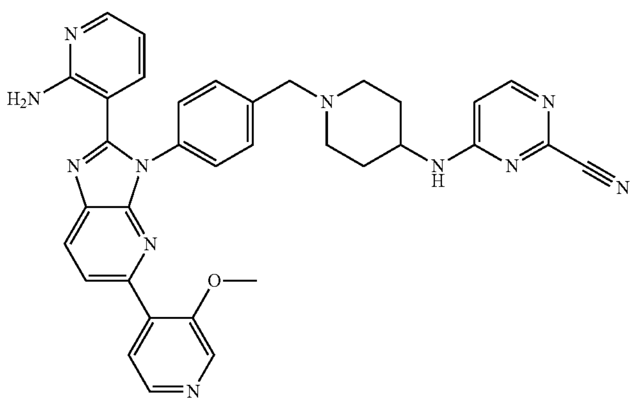 [SMILES: COc1cnccc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(3-methoxypyridin-4-yl)-3H-imidazo[4,5-b]pyridin-3-yl)benzyl)piperidin-4-yl)amino)pyrimidine-2-carbonitrile |
| 516 | 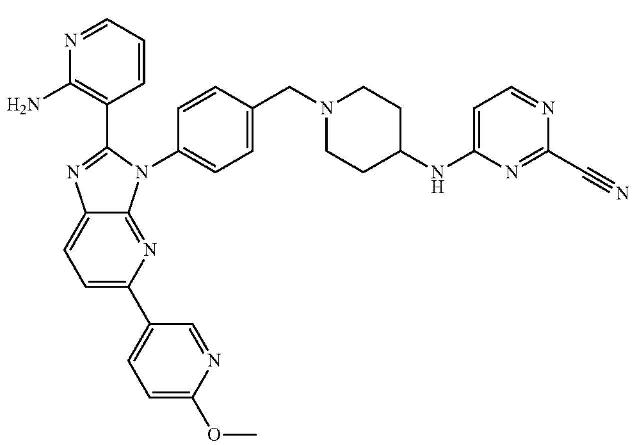 [SMILES: COc1ccc(-c2ccc3nc(-c4cccnc4N)n(-c4ccc(CN5CCC(Nc6ccnc(C#N)n6)CC5)cc4)c3n2)cn1] | 4-((1-(4-(2-(2-aminopyridin-3-yl)-5-(6-methoxypyridin-3-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 517 | 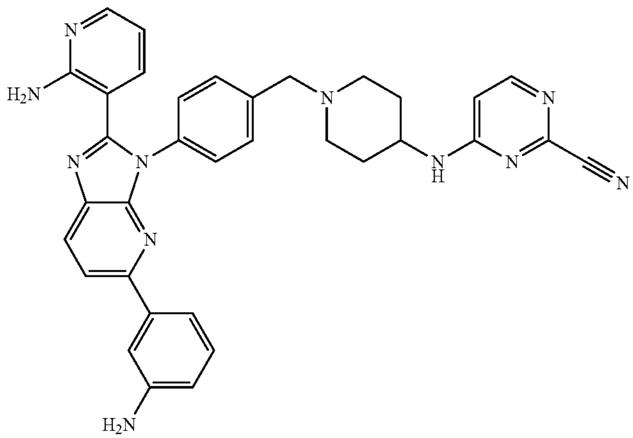 [SMILES: N#Cc1nccc(NC2CCN(Cc3ccc(-n4c(-c5cccnc5N)nc5ccc(-c6cccc(N)c6)nc54)cc3)CC2)n1] | 4-((1-(4-(5-(3-aminophenyl)-2-(2-aminopyridin-3-yl)-3H-imidazo[4,5-b]pyridin-3-yl)benzyl)piperidin-4-yl)amino)pyrimidine-2-carbonitrile |
| 518 | 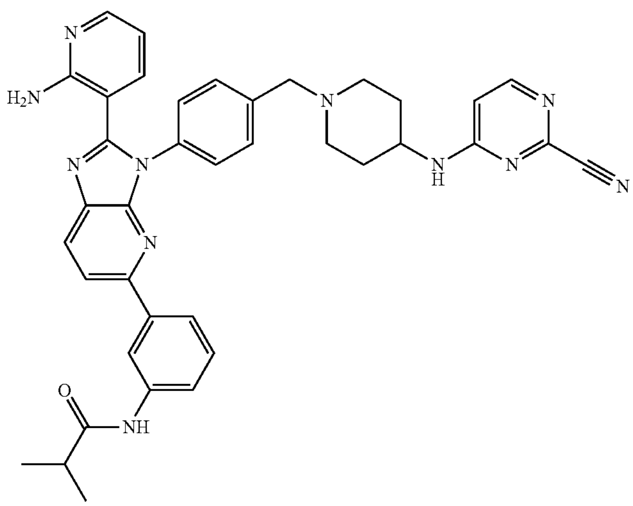 [SMILES: CC(C)C(=O)Nc1cccc(-c2ccc3nc(-c4cccnc4N)n(-c4ccc(CN5CCC(Nc6ccnc(C#N)n6)CC5)cc4)c3n2)c1] | N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)isobutyramide |
| 519 | 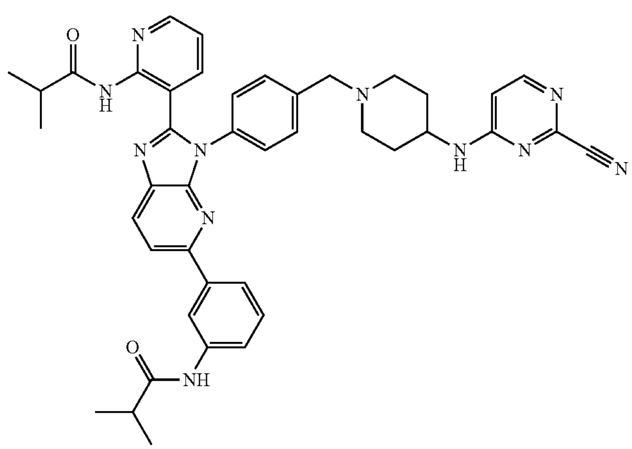 [SMILES: CC(C)C(=O)Nc1cccc(-c2ccc3nc(-c4cccnc4NC(=O)C(C)C)n(-c4ccc(CN5CCC(Nc6ccnc(C#N)n6)CC5)cc4)c3n2)c1] | N-(3-(3-(4-((4-((2-cyanopyrimidin-4-yl)amino)piperidin-1-yl)methyl)phenyl)-2-(2-isobutyramidopyridin-3-yl)-3H-imidazo[4,5-b]pyridin-5-yl)phenyl)isobutyramide |

TABLE 1-continued

| Example | Compound Structure | Compound Name |
|---|---|---|
| 520 | 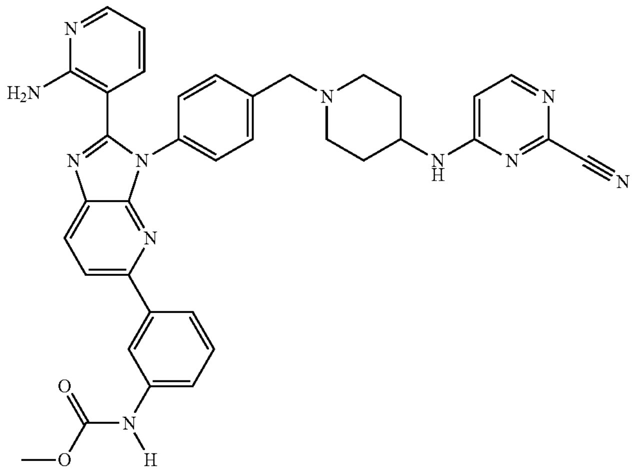 [SMILES: COC(=O)Nc1cccc(-c2ccc3nc(-c4cccnc4N)n(-c4ccc(CN5CCC(Nc6ccnc(C#N)n6)CC5)cc4)c3n2)c1] | methyl (3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)carbamate |
| 521 | 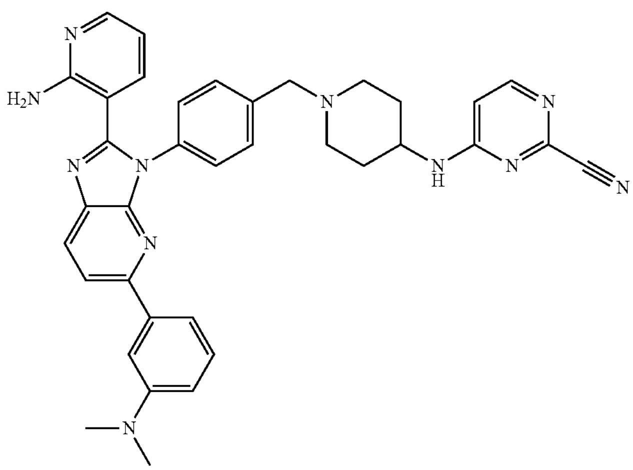 [SMILES: CN(C)c1cccc(-c2ccc3nc(-c4cccnc4N)n(-c4ccc(CN5CCC(Nc6ccnc(C#N)n6)CC5)cc4)c3n2)c1] | 4-((1-(4-(2-(2-aminopyridin-3-yl)-5-(3-(dimethylamino)phenyl)-3H-imidazo[4,5-b]pyridin-3-yl)benzyl)piperidin-4-yl)amino)pyrimidine-2-carbonitrile |
| 522 | 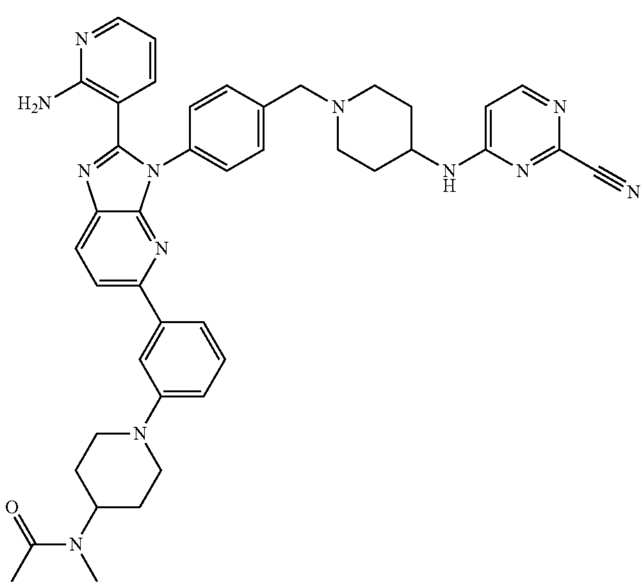 [SMILES: CC(=O)N(C)C1CCN(c2cccc(-c3ccc4nc(-c5cccnc5N)n(-c5ccc(CN6CCC(Nc7ccnc(C#N)n7)CC6)cc5)c4n3)c2)CC1] | N-(1-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)piperidin-4-yl)-N-methylacetamide |

TABLE 1-continued

| Example | Compound Structure | Compound Name |
|---|---|---|
| 523 | 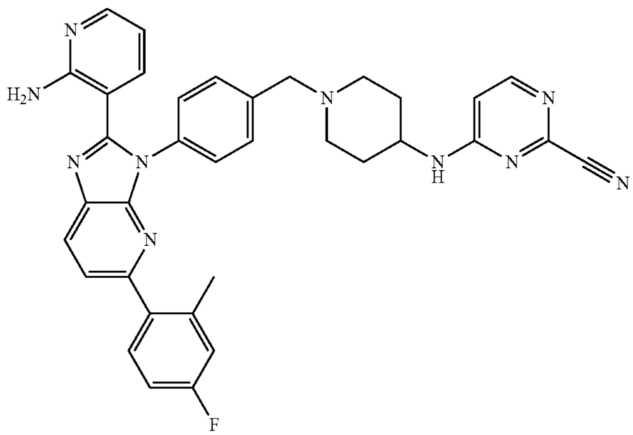 [SMILES: Cc1cc(F)ccc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(4-fluoro-2-methylphenyl)-3H-imidazo[4,5-b]pyridin-3-yl)benzyl)piperidin-4-yl)amino)pyrimidine-2-carbonitrile |
| 524 | 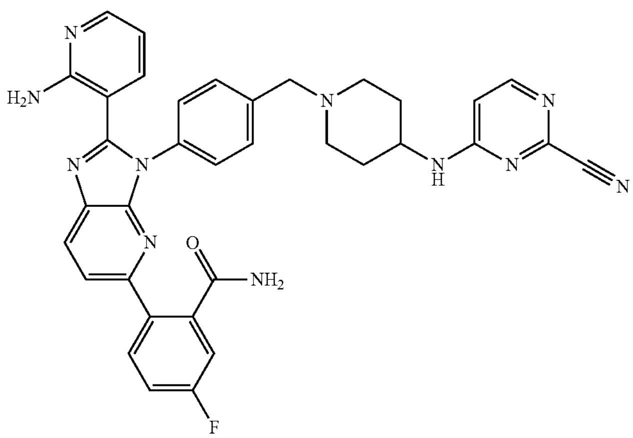 [SMILES: N#Cc1nccc(NC2CCN(Cc3ccc(-n4c(-c5cccnc5N)nc5ccc(-c6ccc(F)cc6C(N)=O)nc54)cc3)CC2)n1] | 2-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)-5-fluorobenzamide |
| 525 | 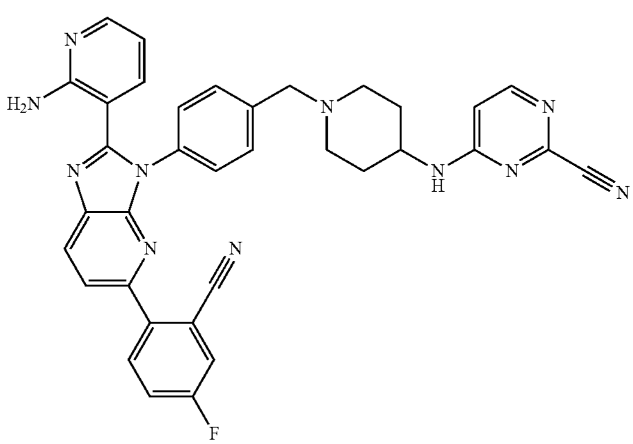 [SMILES: N#Cc1nccc(NC2CCN(Cc3ccc(-n4c(-c5cccnc5N)nc5ccc(-c6ccc(F)cc6C#N)nc54)cc3)CC2)n1] | 4-((1-(4-(2-(2-aminopyridin-3-yl)-5-(2-cyano-4-fluorophenyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 526 | 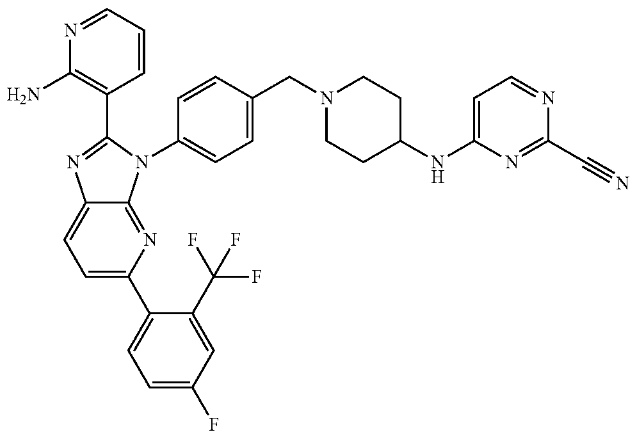 [SMILES: N#Cc1nccc(NC2CCN(Cc3ccc(-n4c(-c5cccnc5N)nc5ccc(-c6ccc(F)cc6C(F)(F)F)nc54)cc3)CC2)n1] | 4-((1-(4-(2-(2-aminopyridin-3-yl)-5-(4-fluoro-2-(trifluoromethyl)phenyl)-3H-imidazo[4,5-b]pyridin-3-yl)benzyl)piperidin-4-yl)amino)pyrimidine-2-carbonitrile |
| 527 | 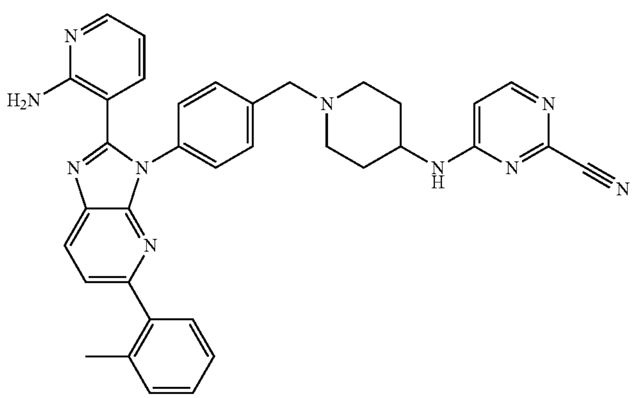 [SMILES: Cc1ccccc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(o-tolyl)-3H-imidazo[4,5-b]pyridin-3-yl)benzyl)piperidin-4-yl)amino)pyrimidine-2-carbonitrile |
| 528 | 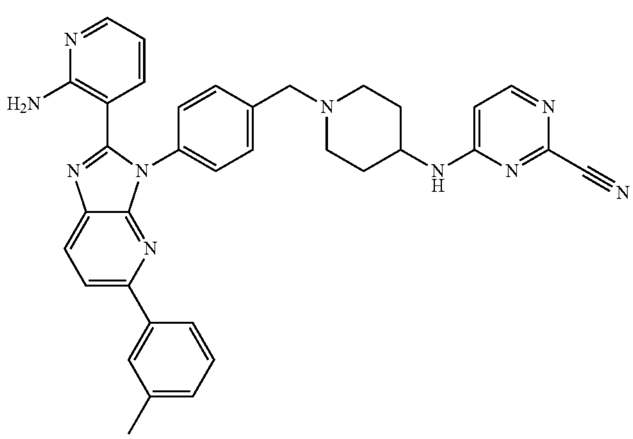 [SMILES: Cc1cccc(-c2ccc3nc(-c4cccnc4N)n(-c4ccc(CN5CCC(Nc6ccnc(C#N)n6)CC5)cc4)c3n2)c1] | 4-((1-(4-(2-(2-aminopyridin-3-yl)-5-(m-tolyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 529 | 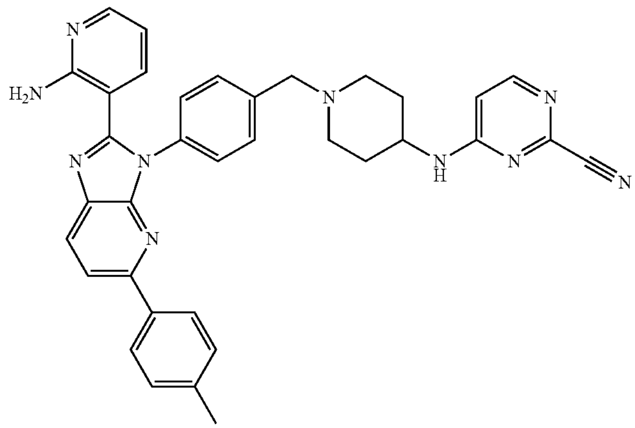 [SMILES: Cc1ccc(-c2ccc3nc(-c4cccnc4N)n(-c4ccc(CN5CCC(Nc6ccnc(C#N)n6)CC5)cc4)c3n2)cc1] | 4-((1-(4-(2-(2-aminopyridin-3-yl)-5-(p-tolyl)-3H-imidazo[4,5-b]pyridin-3-yl)benzyl)piperidin-4-yl)amino)pyrimidine-2-carbonitrile |
| 530 | 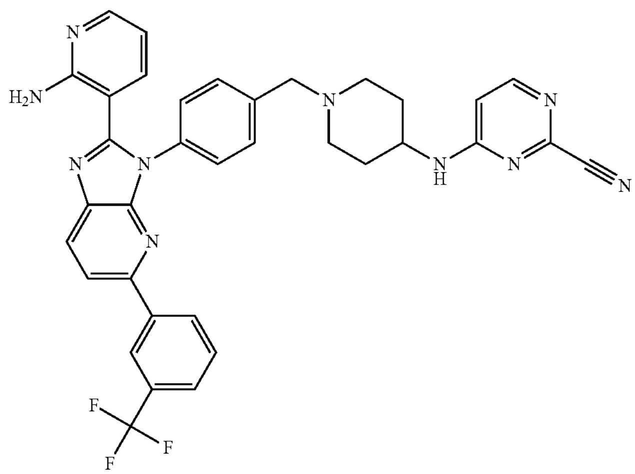 [SMILES: N#Cc1nccc(NC2CCN(Cc3ccc(-n4c(-c5cccnc5N)nc5ccc(-c6cccc(C(F)(F)F)c6)nc54)cc3)CC2)n1] | 4-((1-(4-(2-(2-aminopyridin-3-yl)-5-(3-(trifluoromethyl)phenyl)-3H-imidazo[4,5-b]pyridin-3-yl)benzyl)piperidin-4-yl)amino)pyrimidine-2-carbonitrile |
| 531 | 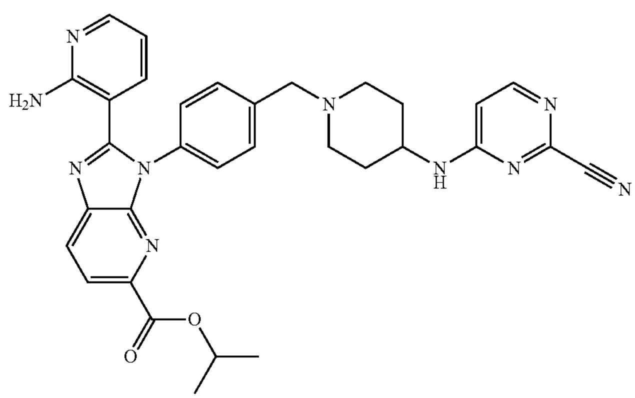 [SMILES: CC(C)OC(=O)c1ccc2nc(-c3cccnc3N)n(-c3ccc(CN4CCC(Nc5ccnc(C#N)n5)CC4)cc3)c2n1] | isopropyl 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylate |
| 532 | 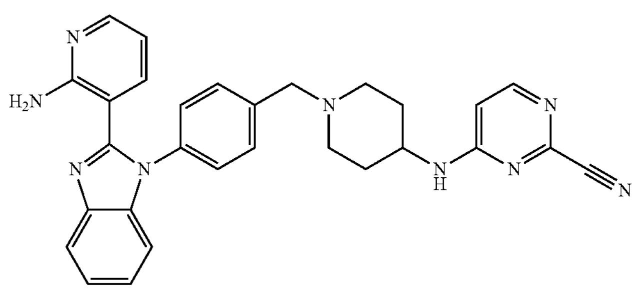 [SMILES: N#Cc1nccc(NC2CCN(Cc3ccc(-n4c(-c5cccnc5N)nc5ccccc54)cc3)CC2)n1] | 4-((1-(4-(2-(2-aminopyridin-3-yl)-1H-benzo[d]imidazol-1-yl)benzyl)piperidin-4-yl)amino)pyrimidine-2-carbonitrile |

TABLE 1-continued

| Example | Compound Structure | Compound Name |
|---|---|---|
| 533 | 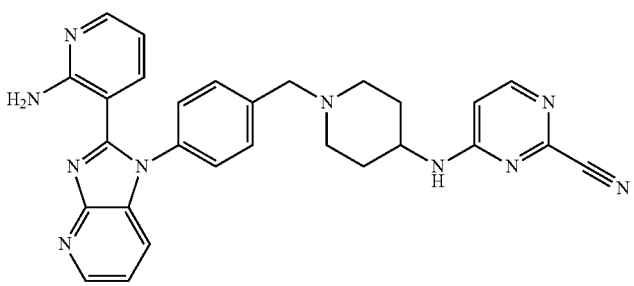 [SMILES: N#Cc1nccc(NC2CCN(Cc3ccc(-n4c(-c5cccnc5N)nc5ncccc54)cc3)CC2)n1] | 4-((1-(4-(2-(2-aminopyridin-3-yl)-1H-imidazo[4,5-b]pyridin-1-yl)benzyl)piperidin-4-yl)amino)pyrimidine-2-carbonitrile |
| 534 | 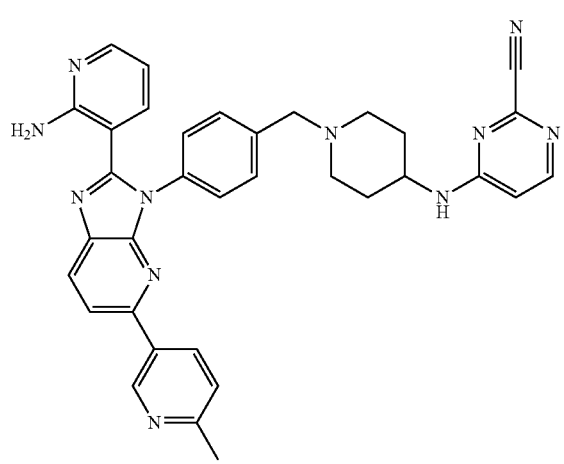 [SMILES: Cc1ccc(-c2ccc3nc(-c4cccnc4N)n(-c4ccc(CN5CCC(Nc6ccnc(C#N)n6)CC5)cc4)c3n2)cn1] | 4-((1-(4-(2-(2-aminopyridin-3-yl)-5-(6-methylpyridin-3-yl)-3H-imidazo[4,5-b]pyridin-3-yl)benzyl)piperidin-4-yl)amino)pyrimidine-2-carbonitrile |
| 535 | 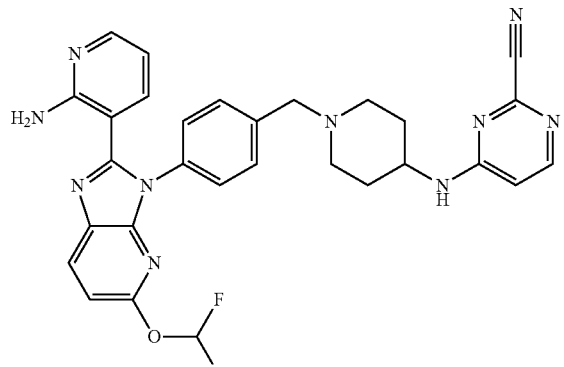 | 4-((1-(4-(2-(2-aminopyridin-3-yl)-5-(difluoromethoxy)-3H-imidazo[4,5-b]pyridin-3-yl)benzyl)piperidin-4-yl)amino)pyrimidine-2-carbonitrile |
| 536 | 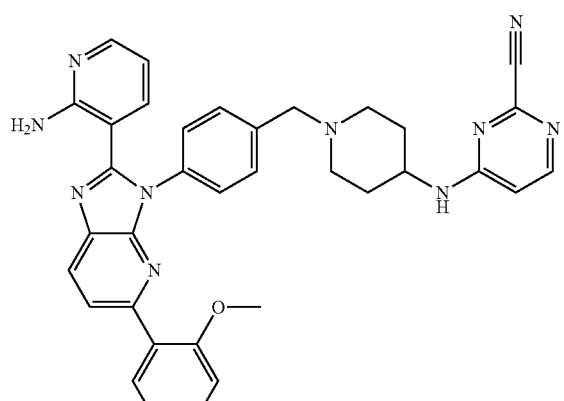 | 4-((1-(4-(2-(2-aminopyridin-3-yl)-5-(4-methoxypyridin-3-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 537 | 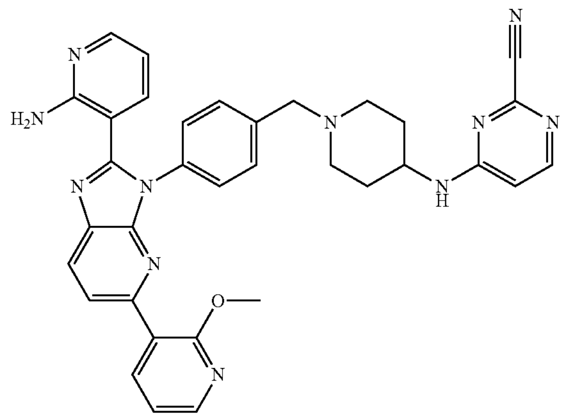 [SMILES: COc1ncccc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(2-methoxypyridin-3-yl)-3H-imidazo[4,5-b]pyridin-3-yl)benzyl)piperidin-4-yl)amino)pyrimidine-2-carbonitrile |
| 538 | 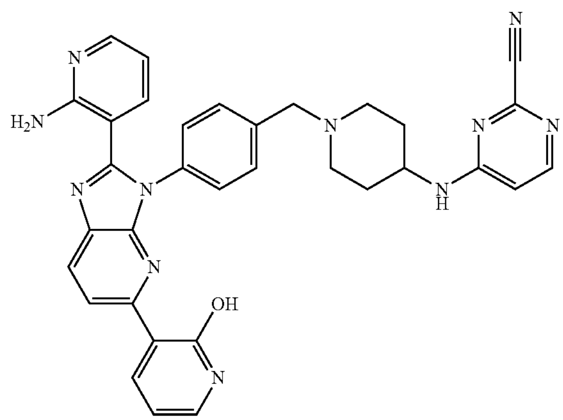 [SMILES: N#Cc1nccc(NC2CCN(Cc3ccc(-n4c(-c5cccnc5N)nc5ccc(-c6cccnc6O)nc54)cc3)CC2)n1] | 4-((1-(4-(2-(2-aminopyridin-3-yl)-5-(2-hydroxypyridin-3-yl)-3H-imidazo[4,5-b]pyridin-3-yl)benzyl)piperidin-4-yl)amino)pyrimidine-2-carbonitrile |
| 539 | 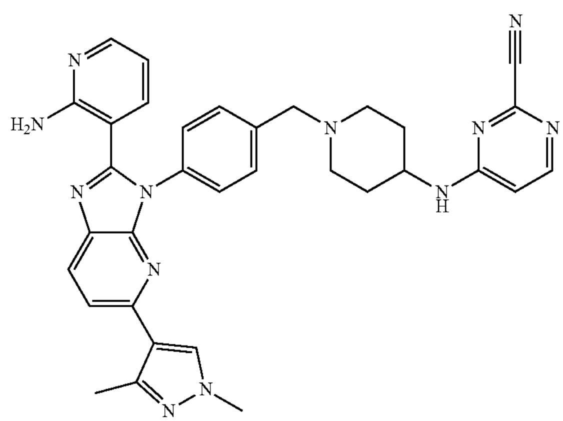 [SMILES: Cc1nn(C)cc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(1,3-dimethyl-1H-pyrazol-4-yl)-3H-imidazo[4,5-b]pyridin-3-yl)benzyl)piperidin-4-yl)amino)pyrimidine-2-carbonitrile |
| 540 | 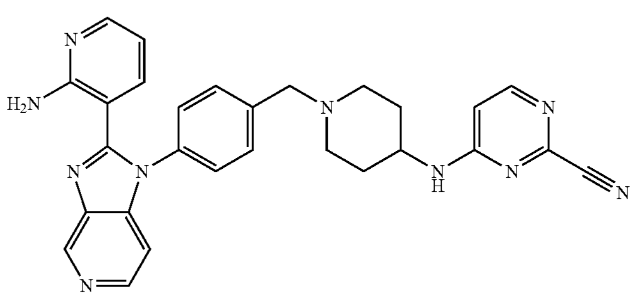 [SMILES: N#Cc1nccc(NC2CCN(Cc3ccc(-n4c(-c5cccnc5N)nc5cnccc54)cc3)CC2)n1] | 4-((1-(4-(2-(2-aminopyridin-3-yl)-1H-imidazo[4,5-c]pyridin-1-yl)benzyl)piperidin-4-yl)amino)pyrimidine-2-carbonitrile |

TABLE 1-continued

| Example | Compound Structure | Compound Name |
|---|---|---|
| 541 | 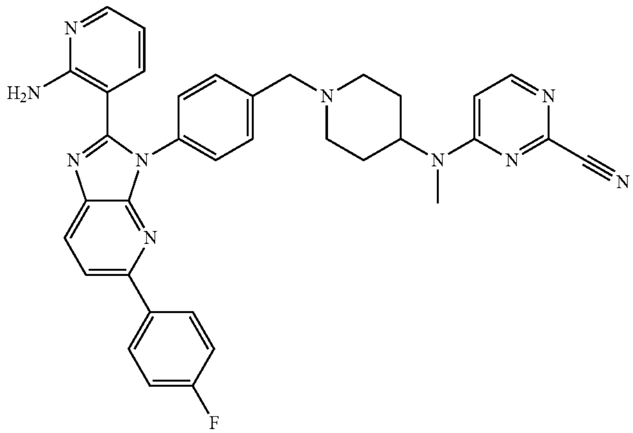 [SMILES: CN(c1ccnc(C#N)n1)C1CCN(Cc2ccc(-n3c(-c4cccnc4N)nc4ccc(-c5ccc(F)cc5)nc43)cc2)CC1] | 4-((1-(4-(2-(2-aminopyridin-3-yl)-5-(4-fluorophenyl)-3H-imidazo[4,5-b]pyridin-3-yl)benzyl)piperidin-4-yl)(methyl)amino)pyrimidine-2-carbonitrile |
| 542 | 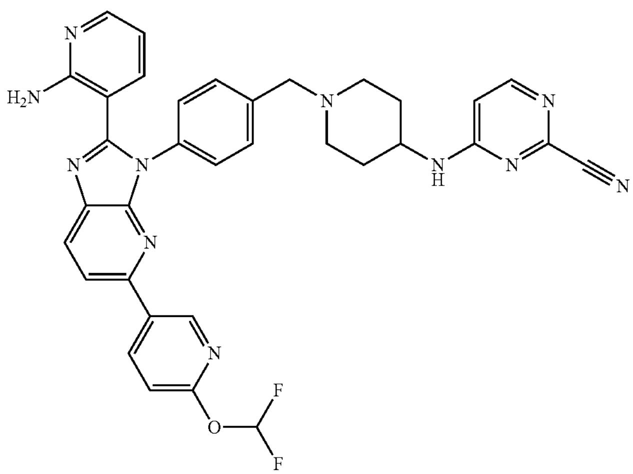 [SMILES: N#Cc1nccc(NC2CCN(Cc3ccc(-n4c(-c5cccnc5N)nc5ccc(-c6ccc(OC(F)F)nc6)nc54)cc3)CC2)n1] | 4-((1-(4-(2-(2-aminopyridin-3-yl)-5-(6-(difluoromethoxy)pyridin-3-yl)-3H-imidazo[4,5-b]pyridin-3-yl)benzyl)piperidin-4-yl)amino)pyrimidine-2-carbonitrile |
| 543 | 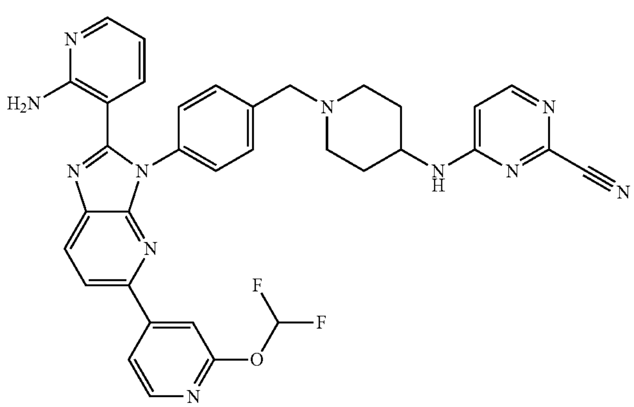 [SMILES: N#Cc1nccc(NC2CCN(Cc3ccc(-n4c(-c5cccnc5N)nc5ccc(-c6ccnc(OC(F)F)c6)nc54)cc3)CC2)n1] | 4-((1-(4-(2-(2-aminopyridin-3-yl)-5-(2-(difluoromethoxy)pyridin-4-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 544 | 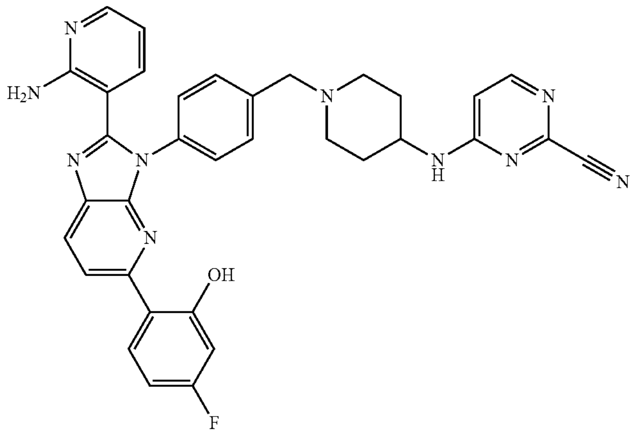 [SMILES: N#Cc1nccc(NC2CCN(Cc3ccc(-n4c(-c5cccnc5N)nc5ccc(-c6ccc(F)cc6O)nc54)cc3)CC2)n1] | 4-((1-(4-(2-(2-aminopyridin-3-yl)-5-(4-fluoro-2-hydroxyphenyl)-3H-imidazo[4,5-b]pyridin-3-yl)benzyl)piperidin-4-yl)amino)pyrimidine-2-carbonitrile |
| 545 | 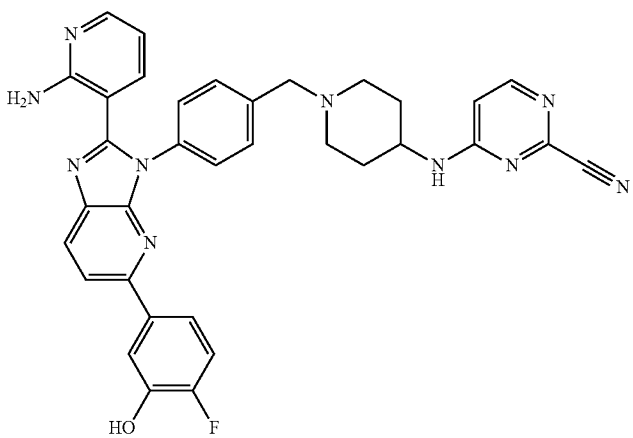 [SMILES: N#Cc1nccc(NC2CCN(Cc3ccc(-n4c(-c5cccnc5N)nc5ccc(-c6ccc(F)c(O)c6)nc54)cc3)CC2)n1] | 4-((1-(4-(2-(2-aminopyridin-3-yl)-5-(4-fluoro-3-hydroxyphenyl)-3H-imidazo[4,5-b]pyridin-3-yl)benzyl)piperidin-4-yl)amino)pyrimidine-2-carbonitrile |
| 546 | 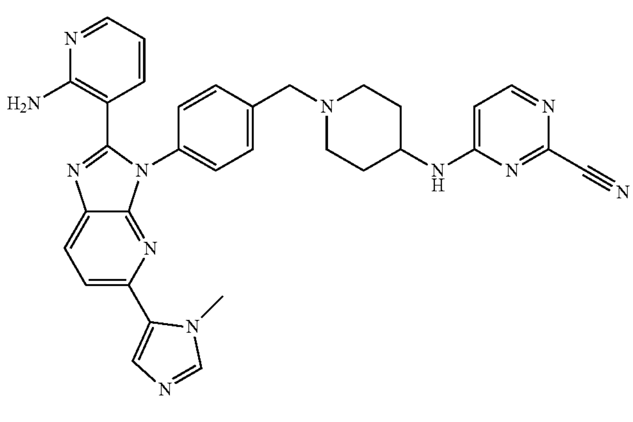 [SMILES: Cn1cncc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(1-methyl-1H-imidazol-5-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 547 | 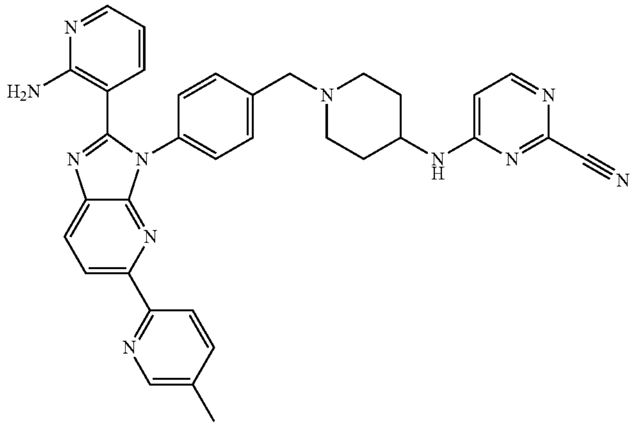 [SMILES: Cc1ccc(-c2ccc3nc(-c4cccnc4N)n(-c4ccc(CN5CCC(Nc6ccnc(C#N)n6)CC5)cc4)c3n2)nc1] | 4-((1-(4-(2-(2-aminopyridin-3-yl)-5-(5-methylpyridin-2-yl)-3H-imidazo[4,5-b]pyridin-3-yl)benzyl)piperidin-4-yl)amino)pyrimidine-2-carbonitrile |
| 548 | 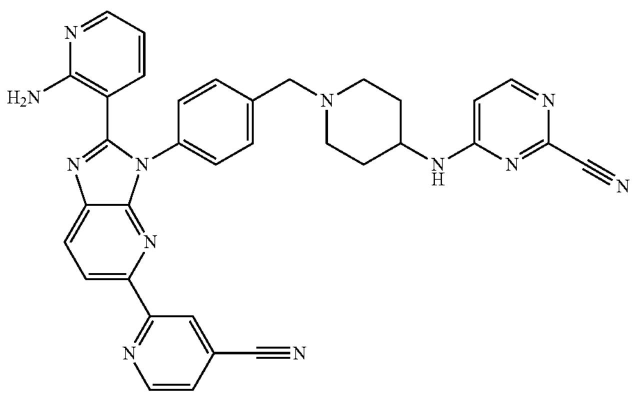 [SMILES: N#Cc1ccnc(-c2ccc3nc(-c4cccnc4N)n(-c4ccc(CN5CCC(Nc6ccnc(C#N)n6)CC5)cc4)c3n2)c1] | 4-((1-(4-(2-(2-aminopyridin-3-yl)-5-(4-cyanopyridin-2-yl)-3H-imidazo[4,5-b]pyridin-3-yl)benzyl)piperidin-4-yl)amino)pyrimidine-2-carbonitrile |
| 549 | 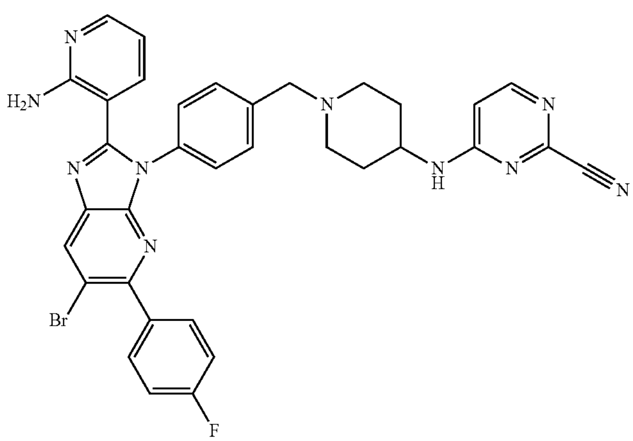 [SMILES: N#Cc1nccc(NC2CCN(Cc3ccc(-n4c(-c5cccnc5N)nc5cc(Br)c(-c6ccc(F)cc6)nc54)cc3)CC2)n1] | 4-((1-(4-(2-(2-aminopyridin-3-yl)-6-bromo-5-(4-fluorophenyl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 550 | 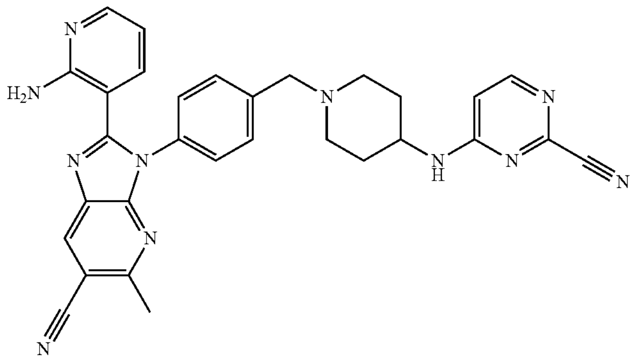 [SMILES: Cc1nc2c(cc1C#N)nc(-c1cccnc1N)n2-c1ccc(CN2CCC(Nc3ccnc(C#N)n3)CC2)cc1] | 2-(2-aminopyridin-3-yl)-3-(4-((4-((2-cyanopyrimidin-4-yl)amino)piperidin-1-yl)methyl)phenyl)-5-methyl-3H-imidazo[4,5-b]pyridine-6-carbonitrile |
| 551 | 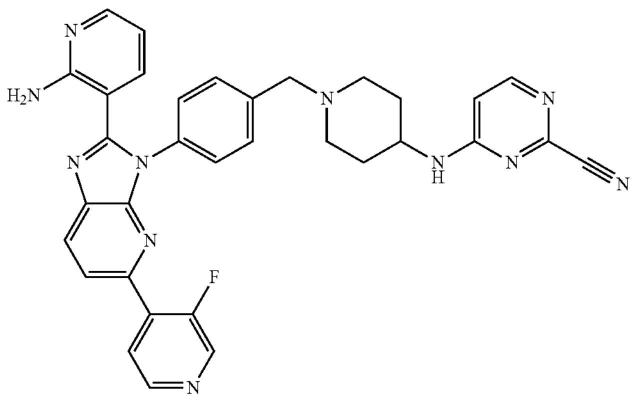 [SMILES: N#Cc1nccc(NC2CCN(Cc3ccc(-n4c(-c5cccnc5N)nc5ccc(-c6ccncc6F)nc54)cc3)CC2)n1] | 4-((1-(4-(2-(2-aminopyridin-3-yl)-5-(3-fluoropyridin-4-yl)-3H-imidazo[4,5-b]pyridin-3-yl)benzyl)piperidin-4-yl)amino)pyrimidine-2-carbonitrile |
| 552 | 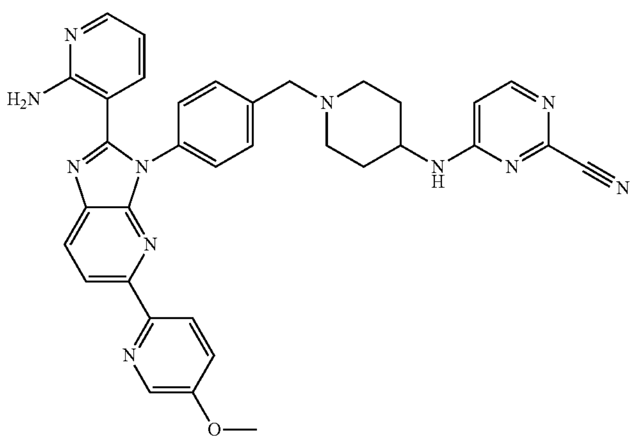 [SMILES: COc1ccc(-c2ccc3nc(-c4cccnc4N)n(-c4ccc(CN5CCC(Nc6ccnc(C#N)n6)CC5)cc4)c3n2)nc1] | 4-((1-(4-(2-(2-aminopyridin-3-yl)-5-(5-methoxypyridin-2-yl)-3H-imidazo[4,5-b]pyridin-3-yl)benzyl)piperidin-4-yl)amino)pyrimidine-2-carbonitrile |
| 553 | 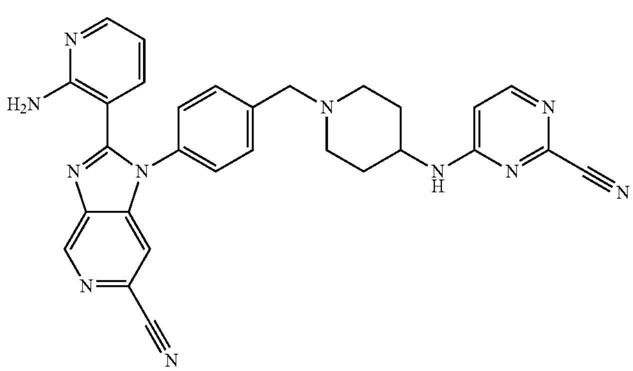 [SMILES: N#Cc1cc2c(cn1)nc(-c1cccnc1N)n2-c1ccc(CN2CCC(Nc3ccnc(C#N)n3)CC2)cc1] | 2-(2-aminopyridin-3-yl)-1-(4-((4-((2-cyanopyrimidin-4-yl)amino)piperidin-1-yl)methyl)phenyl)-1H-imidazo[4,5-c]pyridine-6-carbonitrile |

TABLE 1-continued

| Example | Compound Structure | Compound Name |
|---|---|---|
| 554 | 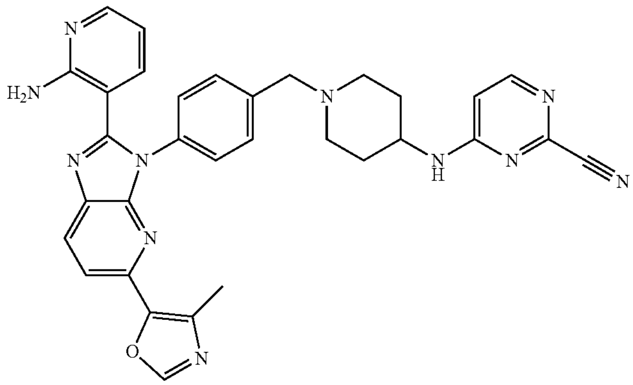 [SMILES: Cc1ncoc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(4-methyloxazol-5-yl)-3H-imidazo[4,5-b]pyridin-3-yl)benzyl)piperidin-4-yl)amino)pyrimidine-2-carbonitrile |
| 555 | 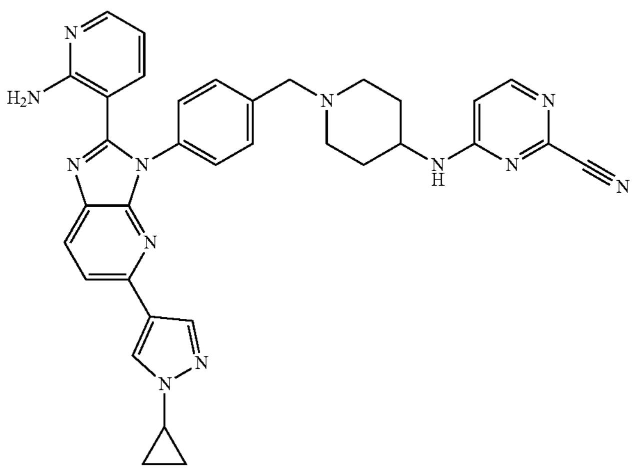 [SMILES: N#Cc1nccc(NC2CCN(Cc3ccc(-n4c(-c5cccnc5N)nc5ccc(-c6cnn(C7CC7)c6)nc54)cc3)CC2)n1] | 4-((1-(4-(2-(2-aminopyridin-3-yl)-5-(1-cyclopropyl-1H-pyrazol-4-yl)-3H-imidazo[4,5-b]pyridin-3-yl)benzyl)piperidin-4-yl)amino)pyrimidine-2-carbonitrile |
| 556 | 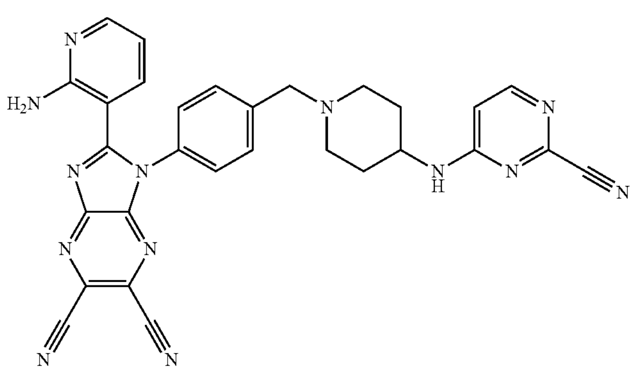 [SMILES: N#Cc1nccc(NC2CCN(Cc3ccc(-n4c(-c5cccnc5N)nc5nc(C#N)c(C#N)nc54)cc3)CC2)n1] | 2-(2-aminopyridin-3-yl)-1-(4-((4-((2-cyanopyrimidin-4-yl)amino)piperidin-1-yl)methyl)phenyl)-1H-imidazo[4,5-b]pyrazine-5,6-dicarbonitrile |

TABLE 1-continued

| Example | Compound Structure | Compound Name |
|---|---|---|
| 557 | 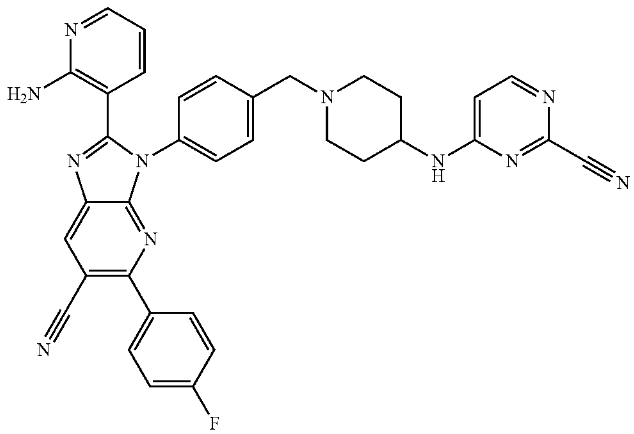 [SMILES: N#Cc1nccc(NC2CCN(Cc3ccc(-n4c(-c5cccnc5N)nc5cc(C#N)c(-c6ccc(F)cc6)nc54)cc3)CC2)n1] | 2-(2-aminopyridin-3-yl)-3-(4-((4-((2-cyanopyrimidin-4-yl)amino)piperidin-1-yl)methyl)phenyl)-5-(4-fluorophenyl)-3H-imidazo[4,5-b]pyridine-6-carbonitrile |
| 558 | 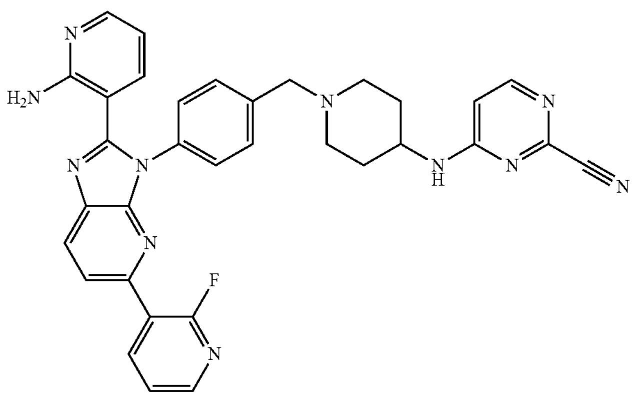 [SMILES: N#Cc1nccc(NC2CCN(Cc3ccc(-n4c(-c5cccnc5N)nc5ccc(-c6cccnc6F)nc54)cc3)CC2)n1] | 4-((1-(4-(2-(2-aminopyridin-3-yl)-5-(2-fluoropyridin-3-yl)-3H-imidazo[4,5-b]pyridin-3-yl)benzyl)piperidin-4-yl)amino)pyrimidine-2-carbonitrile |
| 559 | 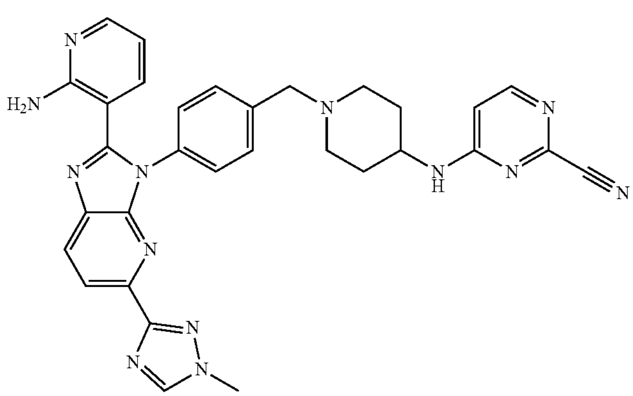 [SMILES: Cn1cnc(-c2ccc3nc(-c4cccnc4N)n(-c4ccc(CN5CCC(Nc6ccnc(C#N)n6)CC5)cc4)c3n2)n1] | 4-((1-(4-(2-(2-aminopyridin-3-yl)-5-(1-methyl-1H-1,2,4-triazol-3-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 560 | 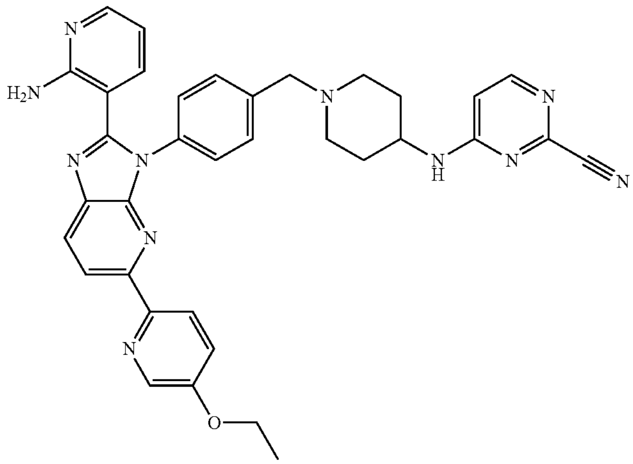 [SMILES: CCOc1ccc(-c2ccc3nc(-c4cccnc4N)n(-c4ccc(CN5CCC(Nc6ccnc(C#N)n6)CC5)cc4)c3n2)nc1] | 4-((1-(4-(2-(2-aminopyridin-3-yl)-5-(5-ethoxypyridin-2-yl)-3H-imidazo[4,5-b]pyridin-3-yl)benzyl)piperidin-4-yl)amino)pyrimidine-2-carbonitrile |
| 561 | 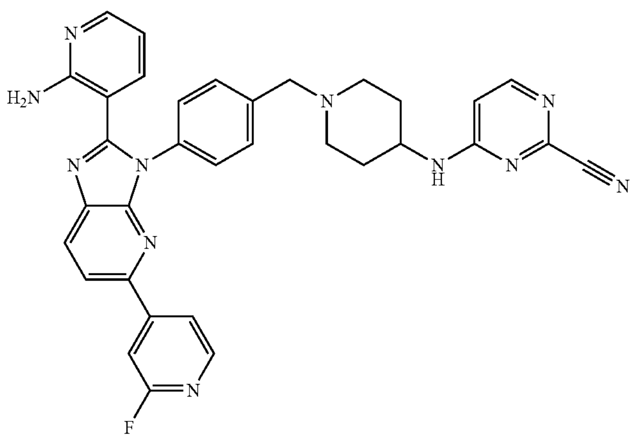 [SMILES: N#Cc1nccc(NC2CCN(Cc3ccc(-n4c(-c5cccnc5N)nc5ccc(-c6ccnc(F)c6)nc54)cc3)CC2)n1] | 4-((1-(4-(2-(2-aminopyridin-3-yl)-5-(2-fluoropyridin-4-yl)-3H-imidazo[4,5-b]pyridin-3-yl)benzyl)piperidin-4-yl)amino)pyrimidine-2-carbonitrile |
| 562 | 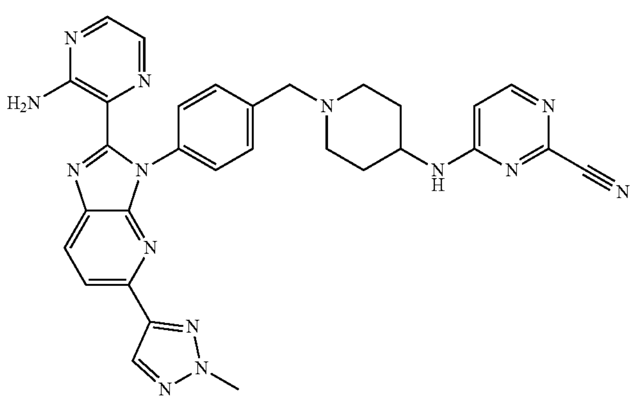 | 4-((1-(4-(2-(3-aminopyrazin-2-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 563 | 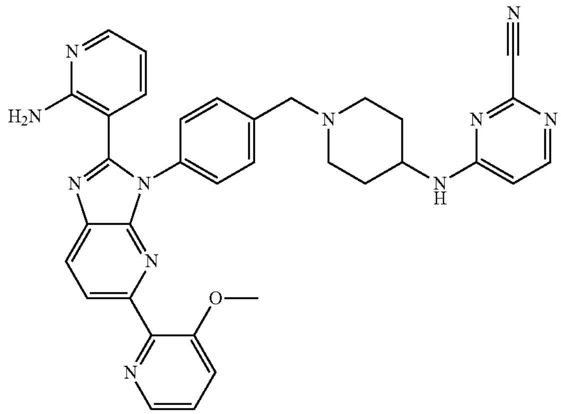 [SMILES: COc1cccnc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(3-methoxypyridin-2-yl)-3H-imidazo[4,5-b]pyridin-3-yl)benzyl)piperidin-4-yl)amino)pyrimidine-2-carbonitrile |
| 564 | 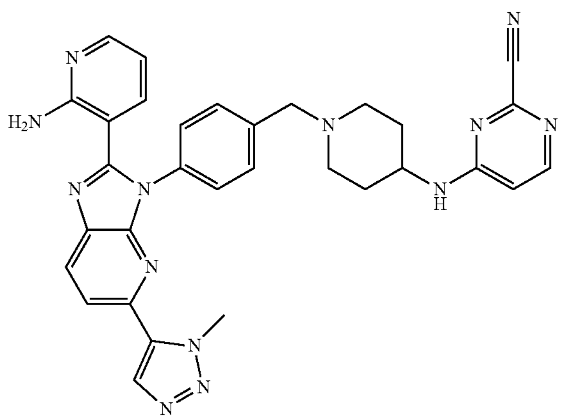 [SMILES: Cn1nncc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(1-methyl-1H-1,2,3-triazol-5-yl)-3H-imidazo[4,5-b]pyridin-3-yl)benzyl)piperidin-4-yl)amino)pyrimidine-2-carbonitrile |
| 565 | 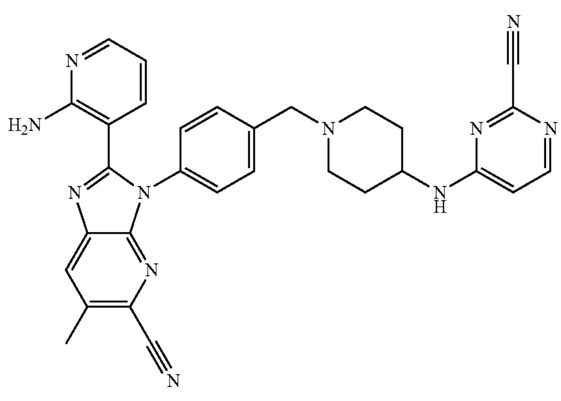 [SMILES: Cc1cc2nc(-c3cccnc3N)n(-c3ccc(CN4CCC(Nc5ccnc(C#N)n5)CC4)cc3)c2nc1C#N] | 2-(2-aminopyridin-3-yl)-3-(4-((4-((2-cyanopyrimidin-4-yl)amino)piperidin-1-yl)methyl)phenyl)-6-methyl-3H-imidazo[4,5-b]pyridine-5-carbonitrile |

TABLE 1-continued

| Example | Compound Structure | Compound Name |
|---|---|---|
| 566 | 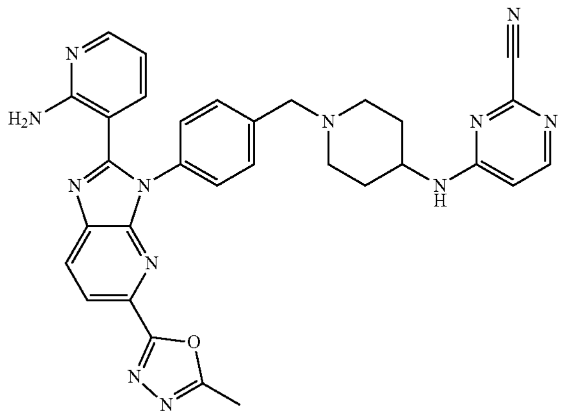 [SMILES: Cc1nnc(-c2ccc3nc(-c4cccnc4N)n(-c4ccc(CN5CCC(Nc6ccnc(C#N)n6)CC5)cc4)c3n2)o1] | 4-((1-(4-(2-(2-aminopyridin-3-yl)-5-(5-methyl-1,3,4-oxadiazol-2-yl)-3H-imidazo[4,5-b]pyridin-3-yl)benzyl)piperidin-4-yl)amino)pyrimidine-2-carbonitrile |
| 567 | 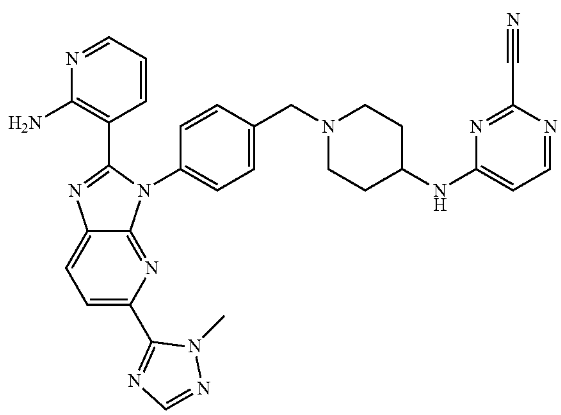 [SMILES: Cn1ncnc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(1-methyl-1H-1,2,4-triazol-5-yl)-3H-imidazo[4,5-b]pyridin-3-yl)benzyl)piperdin-4-yl)amino)pyrimidine-2-carbonitrile |
| 568 | 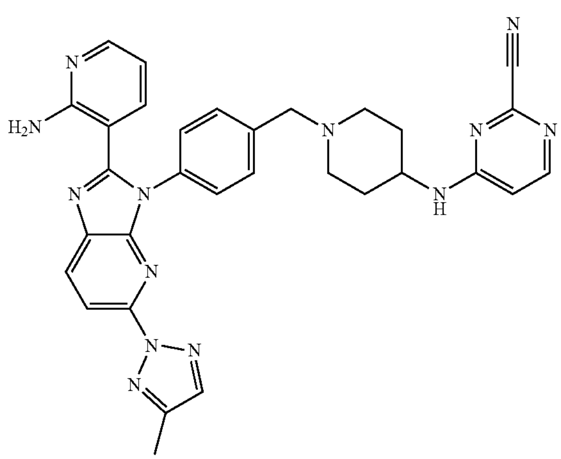 [SMILES: Cc1cnn(-c2ccc3nc(-c4cccnc4N)n(-c4ccc(CN5CCC(Nc6ccnc(C#N)n6)CC5)cc4)c3n2)n1] | 4-((1-(4-(2-(2-aminopyridin-3-yl)-5-(4-methyl-2H-1,2,3-triazol-2-yl)-3H-imidazo[4,5-b]pyridin-3-yl)benzyl)piperidin-4-yl)amino)pyrimidine-2-carbonitrile |

| Example | Compound Structure | Compound Name |
|---|---|---|
| 569 | 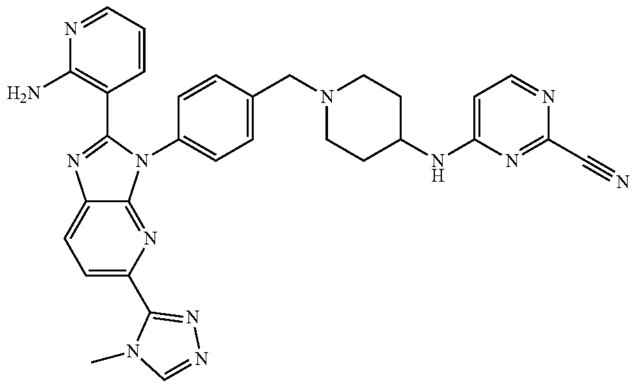 [SMILES: Cn1cnnc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(4-methyl-4H-1,2,4-triazol-3-yl)-3H-imidazo[4,5-b]pyridin-3-yl)benzyl)piperidin-4-yl)amino)pyrimidine-2-carbonitrile |
| 570 | 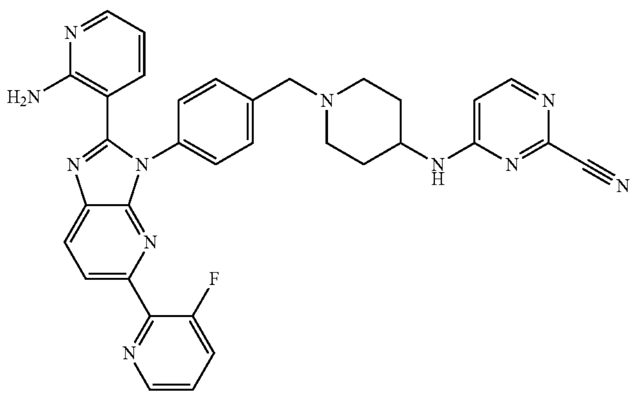 [SMILES: N#Cc1nccc(NC2CCN(Cc3ccc(-n4c(-c5cccnc5N)nc5ccc(-c6ncccc6F)nc54)cc3)CC2)n1] | 4-((1-(4-(2-(2-aminopyridin-3-yl)-5-(3-fluoropyridin-2-yl)-3H-imidazo[4,5-b]pyridin-3-yl)benzyl)piperidin-4-yl)amino)pyrimidine-2-carbonitrile |
| 571 | 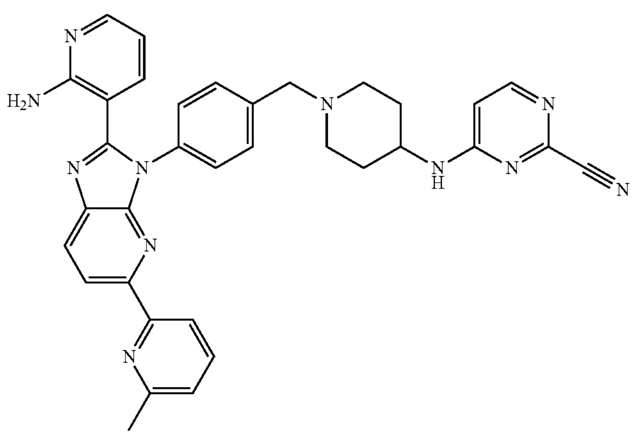 [SMILES: Cc1cccc(-c2ccc3nc(-c4cccnc4N)n(-c4ccc(CN5CCC(Nc6ccnc(C#N)n6)CC5)cc4)c3n2)n1] | 4-((1-(4-(2-(2-aminopyridin-3-yl)-5-(6-methylpyridin-2-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 572 | 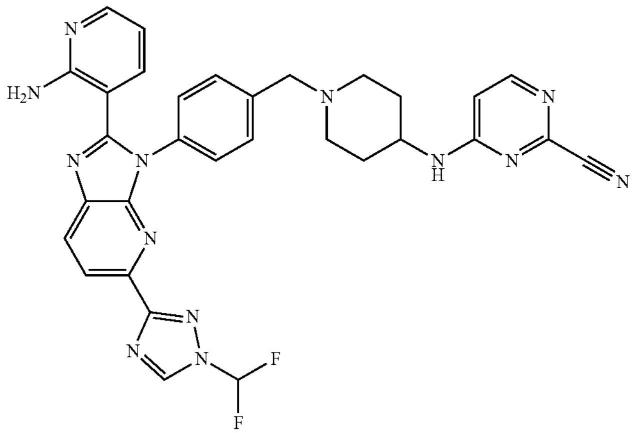 [SMILES: N#Cc1nccc(NC2CCN(Cc3ccc(-n4c(-c5cccnc5N)nc5ccc(-c6ncn(C(F)F)n6)nc54)cc3)CC2)n1] | 4-((1-(4-(2-(2-aminopyridin-3-yl)-5-(1-(difluoromethyl)-1H-1,2,4-triazol-3-yl)-3H-imidazo[4,5-b]pyridin-3-yl)benzyl)piperidin-4-yl)amino)pyrimidine-2-carbonitrile |
| 573 | 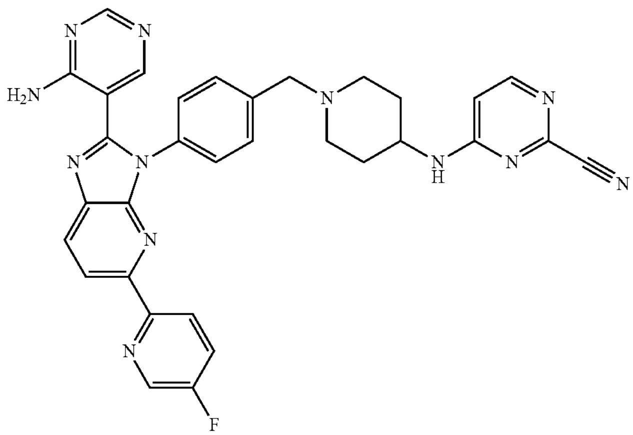 [SMILES: N#Cc1nccc(NC2CCN(Cc3ccc(-n4c(-c5cncnc5N)nc5ccc(-c6ccc(F)cn6)nc54)cc3)CC2)n1] | 4-((1-(4-(2-(4-aminopyrimidin-5-yl)-5-(5-fluoropyridin-2-yl)-3H-imidazo[4,5-b]pyridin-3-yl)benzyl)piperidin-4-yl)amino)pyrimidine-2-carbonitrile |
| 574 | 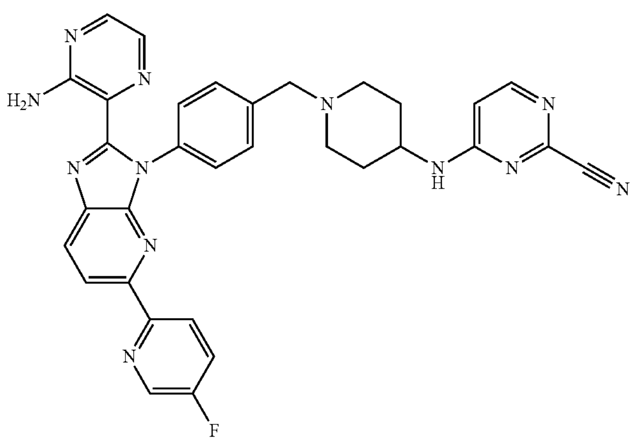 | 4-((1-(4-(2-(3-aminopyrazin-2-yl)-5-(5-fluoropyridin-2-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 575 | 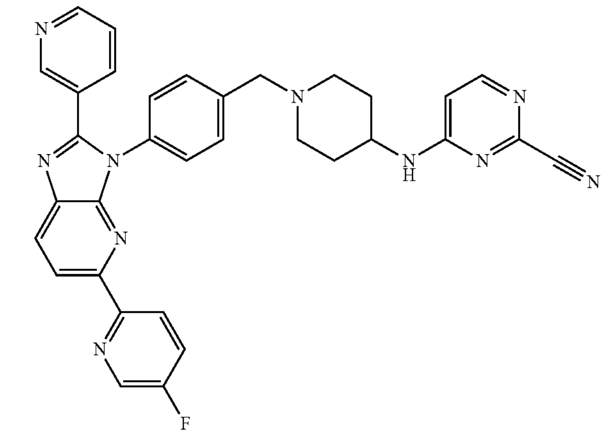 | 4-((1-(4-(5-(5-fluoropyridin-2-yl)-2-(pyridin-3-yl)-3H-imidazo[4,5-b]pyridin-3-yl)benzyl)piperidin-4-yl)amino)pyrimidine-2-carbonitrile |
| 576 | 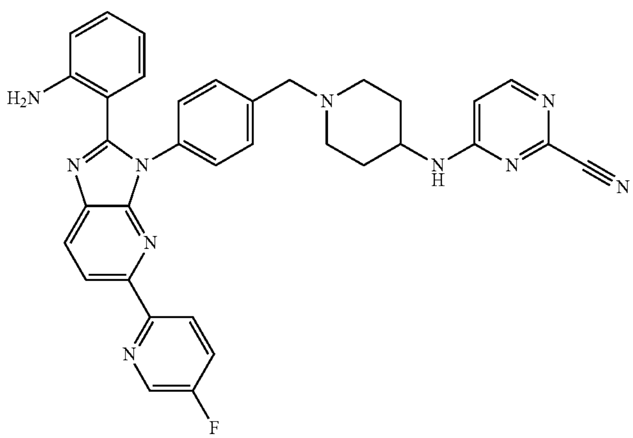 [SMILES: N#Cc1nccc(NC2CCN(Cc3ccc(-n4c(-c5ccccc5N)nc5ccc(-c6ccc(F)cn6)nc54)cc3)CC2)n1] | 4-((1-(4-(2-(2-aminophenyl)-5-(5-fluoropyridin-2-yl)-3H-imidazo[4,5-b]pyridin-3-yl)benzyl)piperidin-4-yl)amino)pyrimidine-2-carbonitrile |
| 577 | 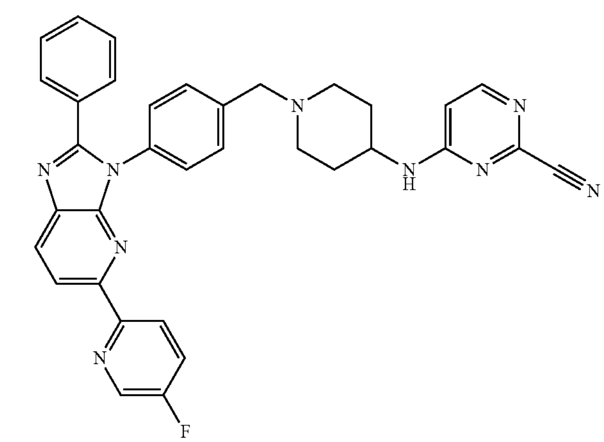 [SMILES: N#Cc1nccc(NC2CCN(Cc3ccc(-n4c(-c5ccccc5)nc5ccc(-c6ccc(F)cn6)nc54)cc3)CC2)n1] | 4-((1-(4-(5-(5-fluoropyridin-2-yl)-2-phenyl-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 578 | 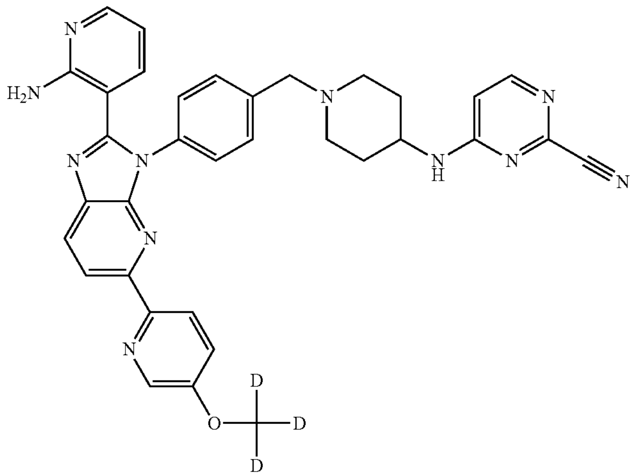 [SMILES: [2H]C([2H])([2H])Oc1ccc(-c2ccc3nc(-c4cccnc4N)n(-c4ccc(CN5CCC(Nc6ccnc(C#N)n6)CC5)cc4)c3n2)nc1] | 4-((1-(4-(2-(2-aminopyridin-3-yl)-5-(5-(methoxy-d3)pyridin-2-yl)-3H-imidazo[4,5-b]pyridin-3-yl)benzyl)piperidin-4-yl)amino)pyrimidine-2-carbonitrile |
| 579 | 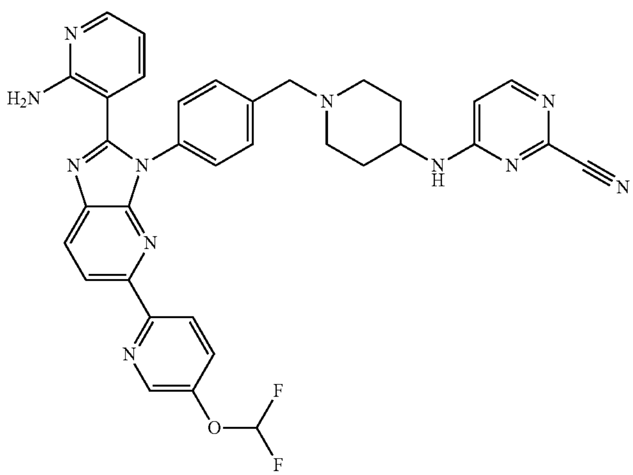 | 4-((1-(4-(2-(2-aminopyridin-3-yl)-5-(5-(difluoromethoxy)pyridin-2-yl)-3H-imidazo[4,5-b]pyridin-3-yl)benzyl)piperidin-4-yl)amino)pyrimidine-2-carbonitrile |
| 580 | 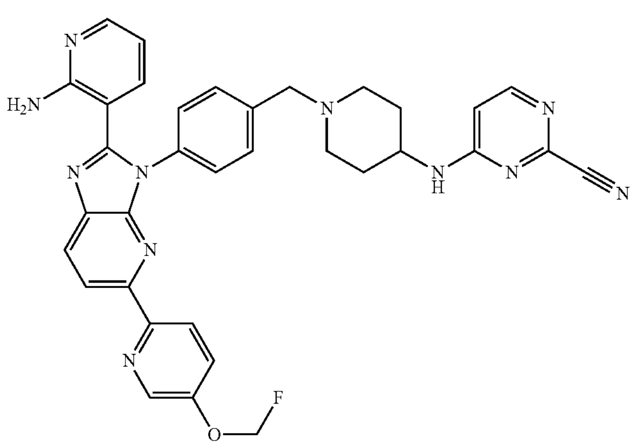 [SMILES: N#Cc1nccc(NC2CCN(Cc3ccc(-n4c(-c5cccnc5N)nc5ccc(-c6ccc(OCF)cn6)nc54)cc3)CC2)n1] | 4-((1-(4-(2-(2-aminopyridin-3-yl)-5-(5-(fluoromethoxy)pyridin-2-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 581 | 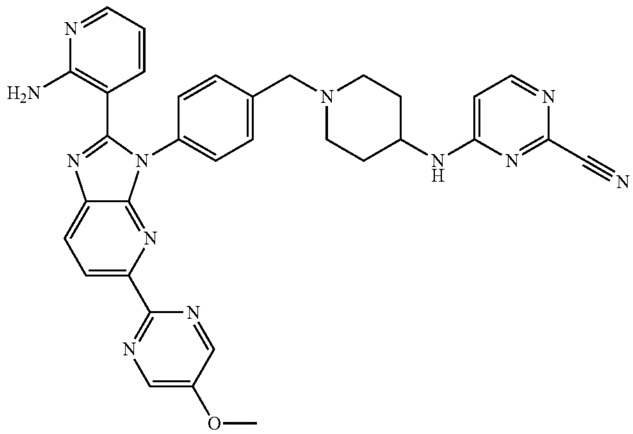 | 4-((1-(4-(2-(2-aminopyridin-3-yl)-5-(5-methoxypyrimidin-2-yl)-3H-imidazo[4,5-b]pyridin-3-yl)benzyl)piperidin-4-yl)amino)pyrimidine-2-carbonitrile |
| 582 | 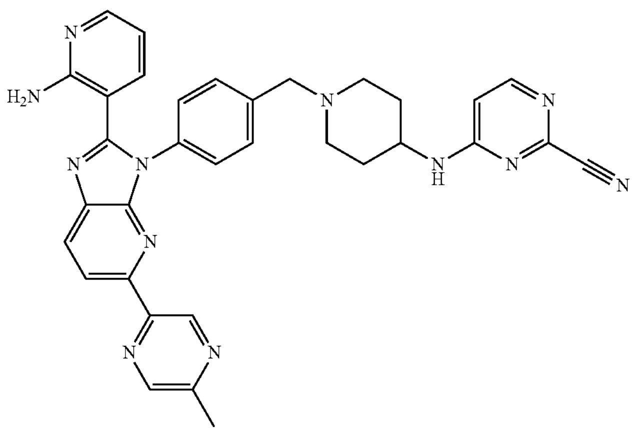 | 4-((1-(4-(2-(2-aminopyridin-3-yl)-5-(5-methylpyrazin-2-yl)-3H-imidazo[4,5-b]pyridin-3-yl)benzyl)piperidin-4-yl)amino)pyrimidine-2-carbonitrile |
| 583 | 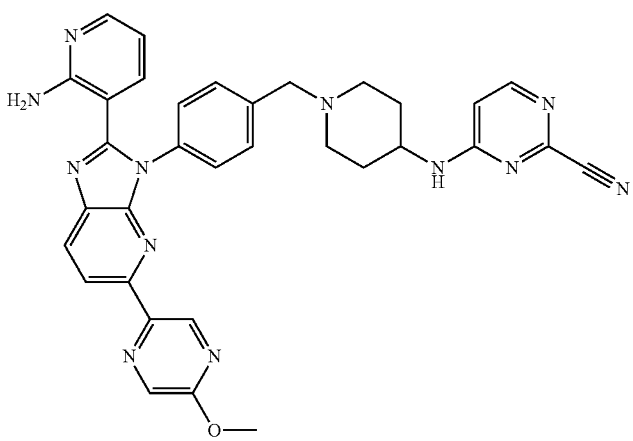 | 4-((1-(4-(2-(2-aminopyridin-3-yl)-5-(5-methoxypyrazin-2-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 584 | 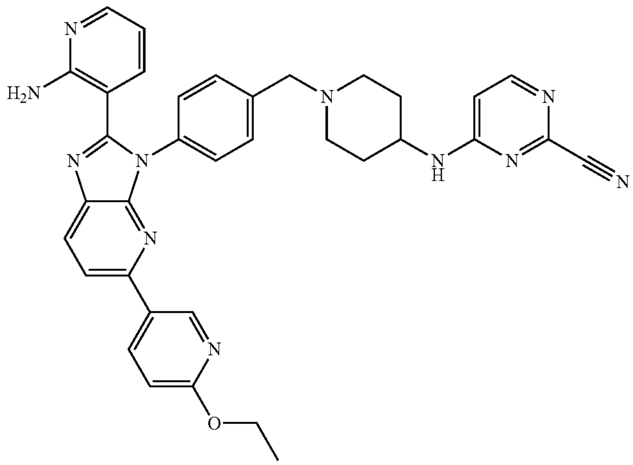 | 4-((1-(4-(2-(2-aminopyridin-3-yl)-5-(6-ethoxypyridin-3-yl)-3H-imidazo[4,5-b]pyridin-3-yl)benzyl)piperidin-4-yl)amino)pyrimidine-2-carbonitrile |
| 585 | 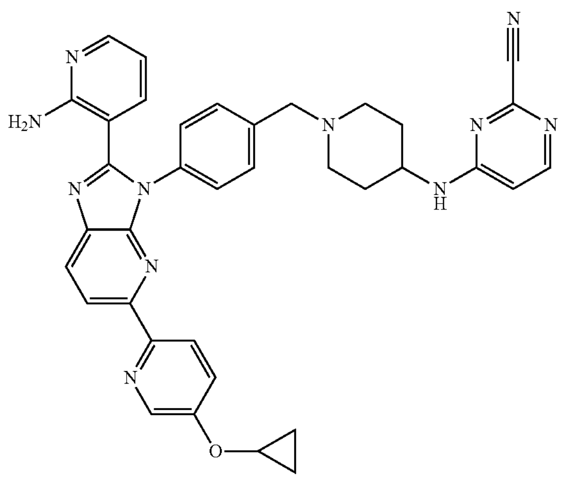 | 4-((1-(4-(2-(2-aminopyridin-3-yl)-5-(5-cyclopropoxypyridin-2-yl)-3H-imidazo[4,5-b]pyridin-3-yl)benzyl)piperidin-4-yl)amino)pyrimidine-2-carbonitrile |
| 586 | 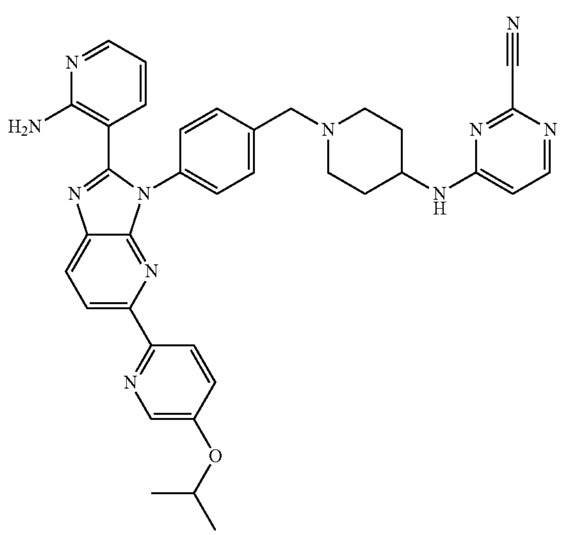 [SMILES: CC(C)Oc1ccc(-c2ccc3nc(-c4cccnc4N)n(-c4ccc(CN5CCC(Nc6ccnc(C#N)n6)CC5)cc4)c3n2)nc1] | 4-((1-(4-(2-(2-aminopyridin-3-yl)-5-(5-isopropoxypyridin-2-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 587 | 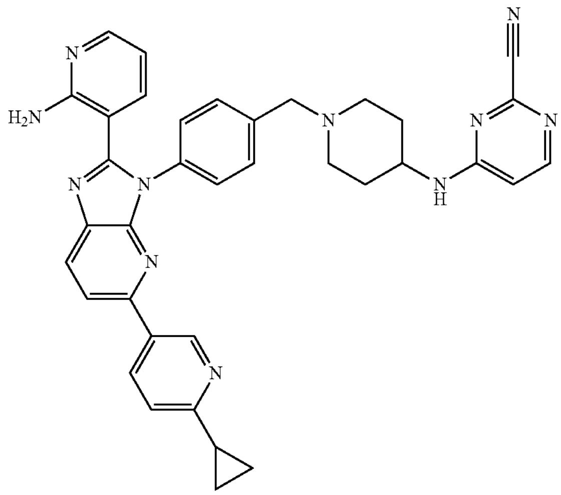 | 4-((1-(4-(2-(2-aminopyridin-3-yl)-5-(6-cyclopropylpyridin-3-yl)-3H-imidazo[4,5-b]pyridin-3-yl)benzyl)piperidin-4-yl)amino)pyrimidine-2-carbonitrile |
| 588 | 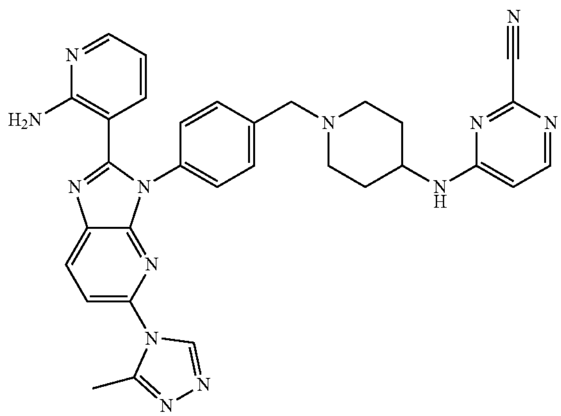 [SMILES: Cc1nncn1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(3-methyl-4H-1,2,4-triazol-4-yl)-3H-imidazo[4,5-b]pyridin-3-yl)benzyl)piperidin-4-yl)amino)pyrimidine-2-carbonitrile |
| 589 | 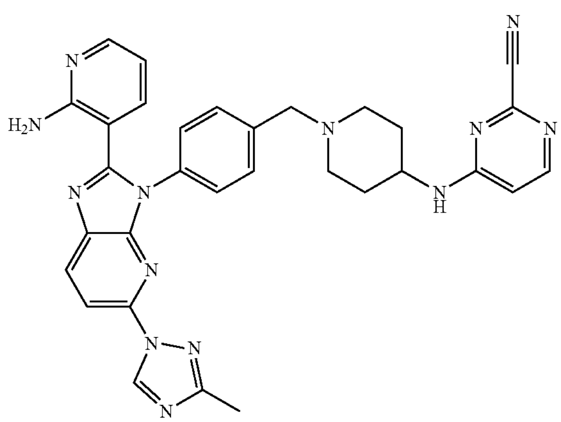 [SMILES: Cc1ncn(-c2ccc3nc(-c4cccnc4N)n(-c4ccc(CN5CCC(Nc6ccnc(C#N)n6)CC5)cc4)c3n2)n1] | 4-((1-(4-(2-(2-aminopyridin-3-yl)-5-(3-methyl-1H-1,2,4-triazol-1-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 590 | 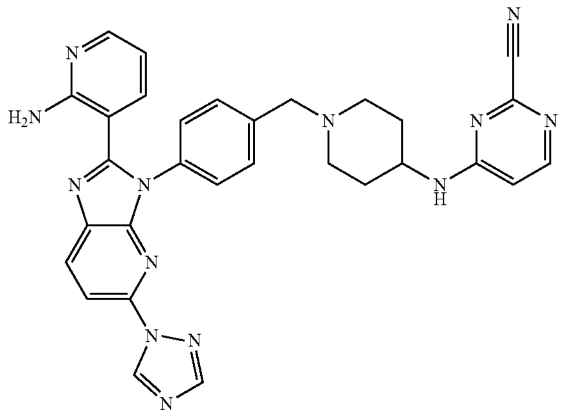 [SMILES: N#Cc1nccc(NC2CCN(Cc3ccc(-n4c(-c5cccnc5N)nc5ccc(-n6cncn6)nc54)cc3)CC2)n1] | 4-((1-(4-(2-(2-aminopyridin-3-yl)-5-(1H-1,2,4-triazol-1-yl)-3H-imidazo[4,5-b]pyridin-3-yl)benzyl)piperidin-4-yl)amino)pyrimidine-2-carbonitrile |
| 591 | 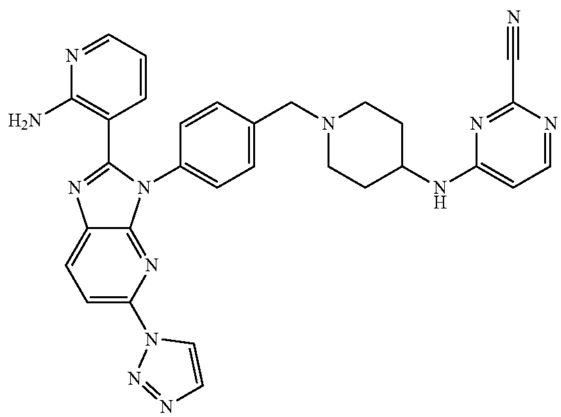 [SMILES: N#Cc1nccc(NC2CCN(Cc3ccc(-n4c(-c5cccnc5N)nc5ccc(-n6ccnn6)nc54)cc3)CC2)n1] | 4-((1-(4-(2-(2-aminopyridin-3-yl)-5-(1H-1,2,3-triazol-1-yl)-3H-imidazo[4,5-b]pyridin-3-yl)benzyl)piperidin-4-yl)amino)pyrimidine-2-carbonitrile |
| 592 | 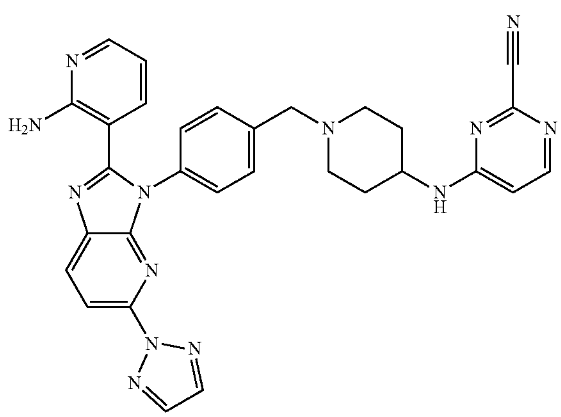 [SMILES: N#Cc1nccc(NC2CCN(Cc3ccc(-n4c(-c5cccnc5N)nc5ccc(-n6nccn6)nc54)cc3)CC2)n1] | 4-((1-(4-(2-(2-aminopyridin-3-yl)-5-(2H-1,2,3-triazol-2-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 593 | 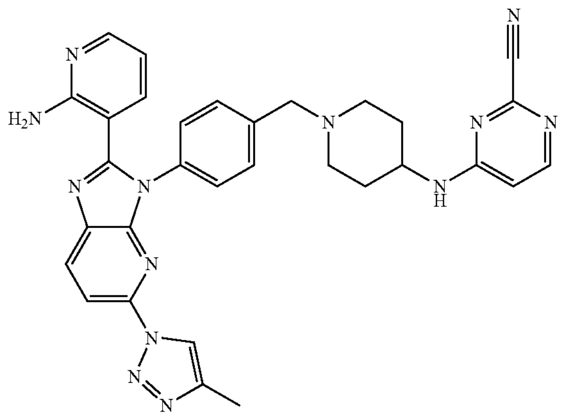 [SMILES: Cc1cn(-c2ccc3nc(-c4cccnc4N)n(-c4ccc(CN5CCC(Nc6ccnc(C#N)n6)CC5)cc4)c3n2)nn1] | 4-((1-(4-(2-(2-aminopyridin-3-yl)-5-(4-methyl-1H-1,2,3-triazol-1-yl)-3H-imidazo[4,5-b]pyridin-3-yl)benzyl)piperidin-4-yl)amino)pyrimidine-2-carbonitrile |
| 594 | 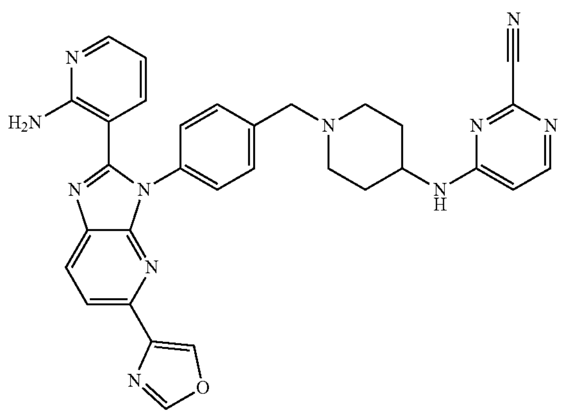 [SMILES: N#Cc1nccc(NC2CCN(Cc3ccc(-n4c(-c5cccnc5N)nc5ccc(-c6cocn6)nc54)cc3)CC2)n1] | 4-((1-(4-(2-(2-aminopyridin-3-yl)-5-(oxazol-4-yl)-3H-imidazo[4,5-b]pyridin-3-yl)benzyl)piperidin-4-yl)amino)pyrimidine-2-carbonitrile |
| 595 | 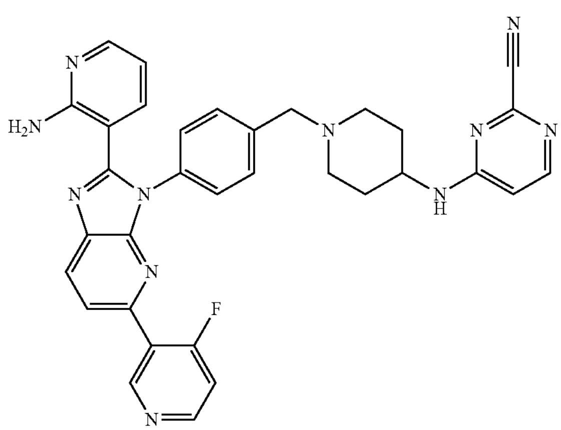 [SMILES: N#Cc1nccc(NC2CCN(Cc3ccc(-n4c(-c5cccnc5N)nc5ccc(-c6cnccc6F)nc54)cc3)CC2)n1] | 4-((1-(4-(2-(2-aminopyridin-3-yl)-5-(4-fluoropyridin-3-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 596 | 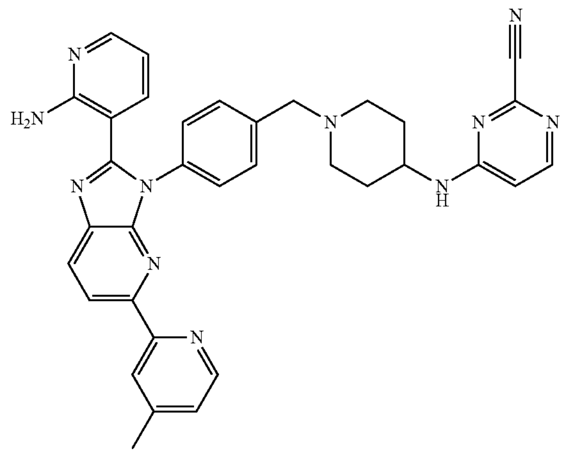 [SMILES: Cc1ccnc(-c2ccc3nc(-c4cccnc4N)n(-c4ccc(CN5CCC(Nc6ccnc(C#N)n6)CC5)cc4)c3n2)c1] | 4-((1-(4-(2-(2-aminopyridin-3-yl)-5-(4-methylpyridin-2-yl)-3H-imidazo[4,5-b]pyridin-3-yl)benzyl)piperidin-4-yl)amino)pyrimidine-2-carbonitrile |
| 597 | 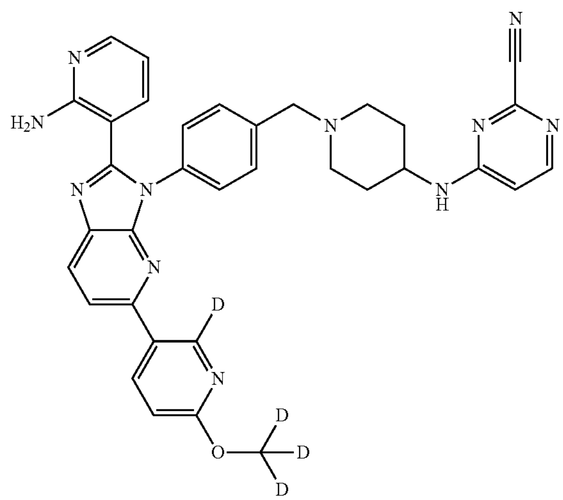 | 4-((1-(4-(2-(2-aminopyridin-3-yl)-5-(6-(methoxy-d3)pyridin-3-yl-2-d)-3H-imidazo[4,5-b]pyridin-3-yl)benzyl)piperidin-4-yl)amino)pyrimidine-2-carbonitrile<br>Mixture of 3D (57.4% and 4D (38.2%)<br>Structure tentatively assigned |
| 598 | 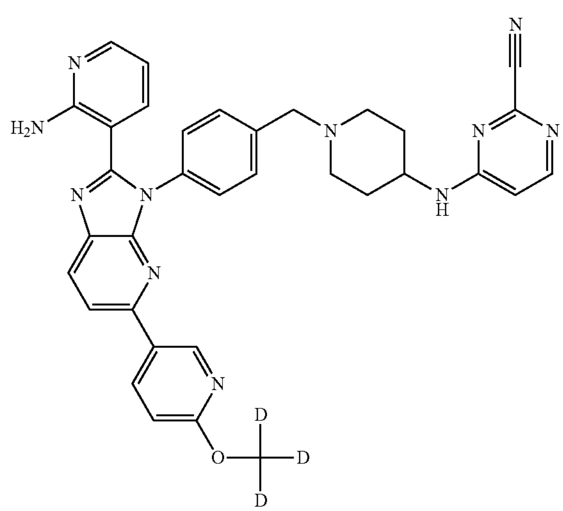 [SMILES: [2H]C([2H])([2H])Oc1ccc(-c2ccc3nc(-c4cccnc4N)n(-c4ccc(CN5CCC(Nc6ccnc(C#N)n6)CC5)cc4)c3n2)cn1] | 4-((1-(4-(2-(2-aminopyridin-3-yl)-5-(6-(methoxy-d3)pyridin-3-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 599 | 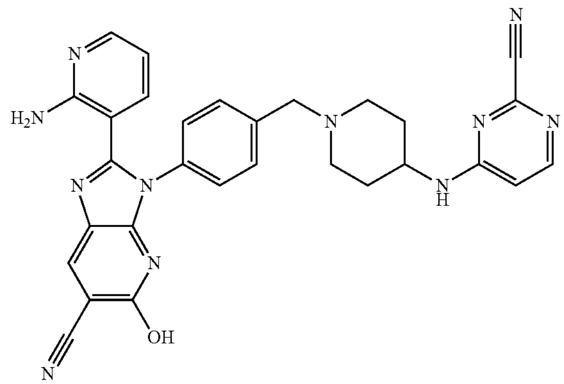 [SMILES: N#Cc1nccc(NC2CCN(Cc3ccc(-n4c(-c5cccnc5N)nc5cc(C#N)c(O)nc54)cc3)CC2)n1] | 2-(2-aminopyridin-3-yl)-3-(4-((4-((2-cyanopyrimidin-4-yl)amino)piperidin-1-yl)methyl)phenyl)-5-hydroxy-3H-imidazo[4,5-b]pyridine-6-carbonitrile |
| 600 | 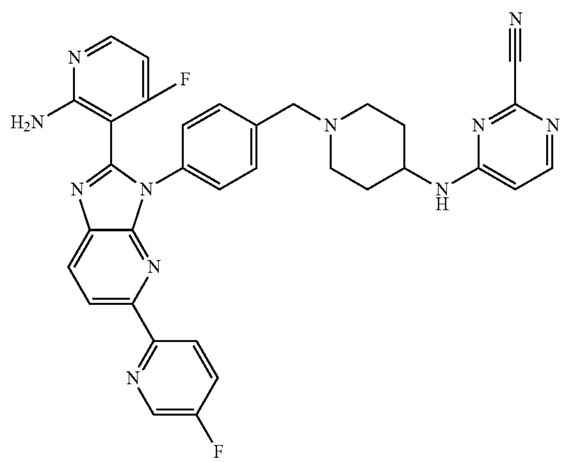 [SMILES: N#Cc1nccc(NC2CCN(Cc3ccc(-n4c(-c5c(F)ccnc5N)nc5ccc(-c6ccc(F)cn6)nc54)cc3)CC2)n1] | 4-((1-(4-(2-(2-amino-4-fluoropyridin-3-yl)-5-(5-fluoropyridin-2-yl)-3H-imidazo[4,5-b]pyridin-3-yl)benzyl)piperidin-4-yl)amino)pyrimidine-2-carbonitrile |
| 601 | 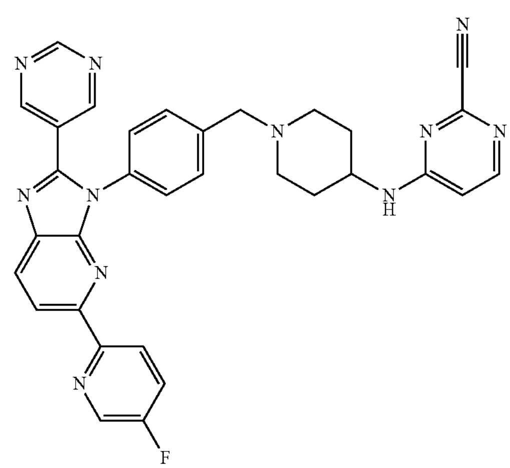 [SMILES: N#Cc1nccc(NC2CCN(Cc3ccc(-n4c(-c5cncnc5)nc5ccc(-c6ccc(F)cn6)nc54)cc3)CC2)n1] | 4-((1-(4-(5-(5-fluoropyridin-2-yl)-2-(pyrimidin-5-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 602 | 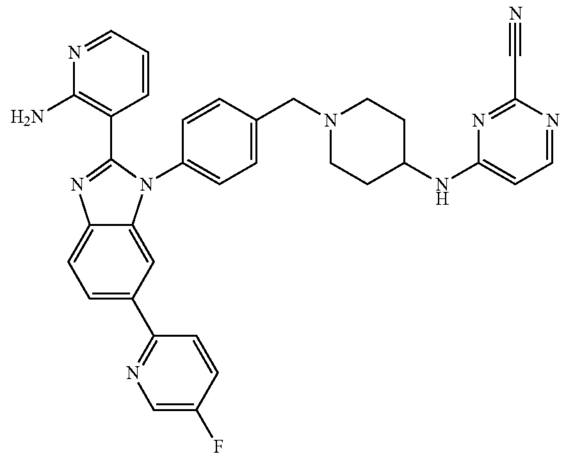 [SMILES: N#Cc1nccc(NC2CCN(Cc3ccc(-n4c(-c5cccnc5N)nc5ccc(-c6ccc(F)cn6)cc54)cc3)CC2)n1] | 4-((1-(4-(2-(2-aminopyridin-3-yl)-6-(5-fluoropyridin-2-yl)-1H-benzo[d]imidazol-1-yl)benzyl)piperidin-4-yl)amino)pyrimidine-2-carbonitrile |
| 603 | 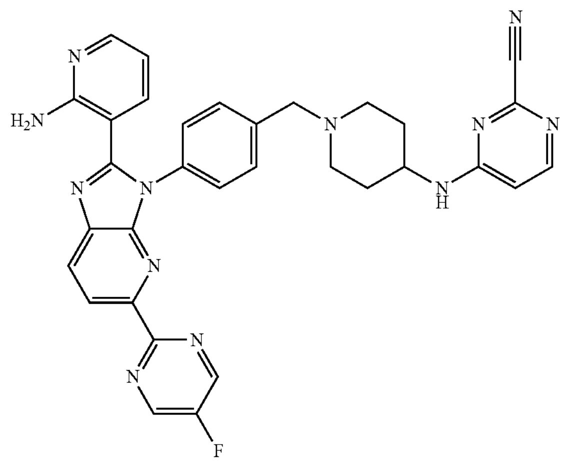 [SMILES: N#Cc1nccc(NC2CCN(Cc3ccc(-n4c(-c5cccnc5N)nc5ccc(-c6ncc(F)cn6)nc54)cc3)CC2)n1] | 4-((1-(4-(2-(2-aminopyridin-3-yl)-5-(5-fluoropyrimidin-2-yl)-3H-imidazo[4,5-b]pyridin-3-yl)benzyl)piperidin-4-yl)amino)pyrimidine-2-carbonitrile |
| 604 | 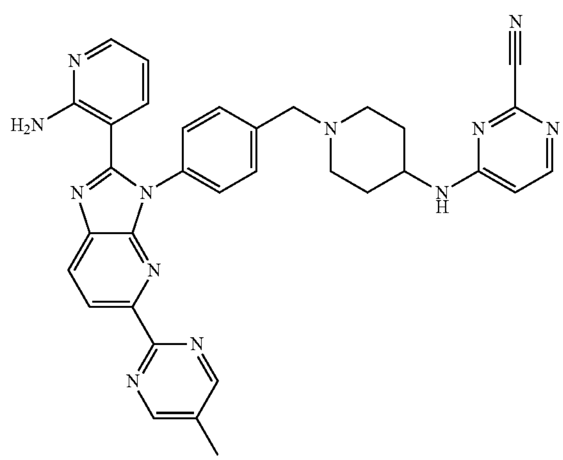 [SMILES: Cc1cnc(-c2ccc3nc(-c4cccnc4N)n(-c4ccc(CN5CCC(Nc6ccnc(C#N)n6)CC5)cc4)c3n2)nc1] | 4-((1-(4-(2-(2-aminopyridin-3-yl)-5-(5-methylpyrimidin-2-yl)-3H-imidazo[4,5-b]pyridin-3-yl)benzyl)piperidin-4-yl)amino)pyrimidine-2-carbonitrile |

TABLE 1-continued

| Example | Compound Name |
|---|---|
| 605 | 4-((1-(4-(2-(2-aminopyridin-3-yl)-5-(5-fluoropyrazin-2-yl)-3H-imidazo[4,5-b]pyridin-3-yl)benzyl)piperidin-4-yl)amino)pyrimidine-2-carbonitrile |
| 606 | 4-((1-(4-(2-(2-aminopyridin-3-yl)-5-(6-(fluoromethoxy)pyridin-3-yl)-3H-imidazo[4,5-b]pyridin-3-yl)benzyl)piperidin-4-yl)amino)pyrimidine-2-carbonitrile |
| 607 | 4-((1-(4-(2-(2-aminopyridin-3-yl)-5-(1-(fluoromethyl)-6-oxo-1,6-dihydropyridin-3-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 608 | 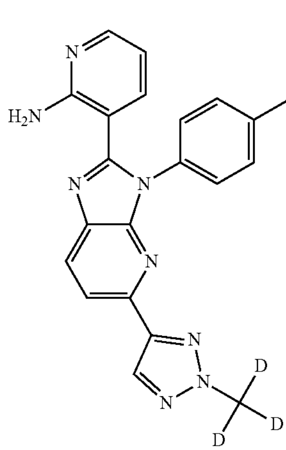 | 4-((1-(4-(2-(2-aminopyridin-3-yl)-5-(2-(methyl-d3)-2H-1,2,3-triazol-4-yl)-3H-imidazo[4,5-b]pyridin-3-yl)benzyl)piperidin-4-yl)amino)pyrimidine-2-carbonitrile |
| 609 | 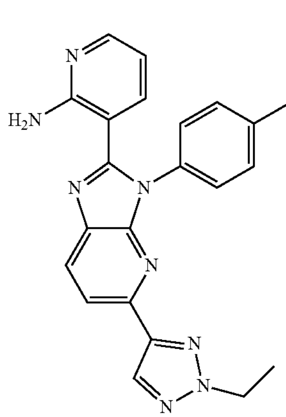 | 4-((1-(4-(2-(2-aminopyridin-3-yl)-5-(2-ethyl-2H-1,2,3-triazol-4-yl)-3H-imidazo[4,5-b]pyridin-3-yl)benzyl)piperidin-4-yl)amino)pyrimidine-2-carbonitrile |
| 610 | 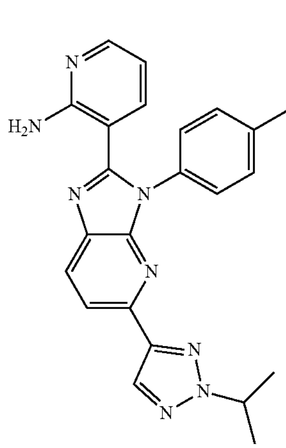 | 4-((1-(4-(2-(2-aminopyridin-3-yl)-5-(2-isopropyl-2H-1,2,3-triazol-4-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 611 | 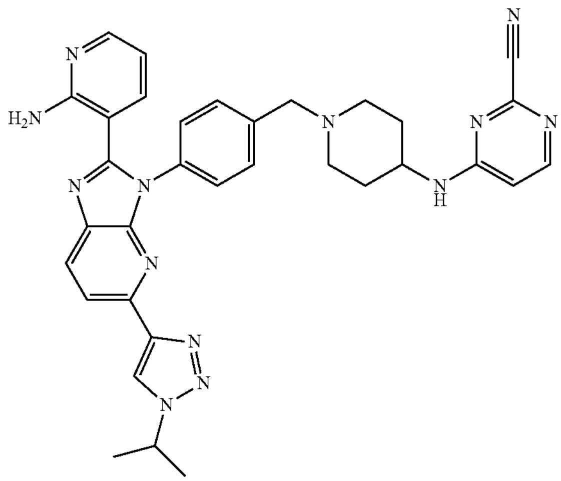 [SMILES: CC(C)n1cc(-c2ccc3nc(-c4cccnc4N)n(-c4ccc(CN5CCC(Nc6ccnc(C#N)n6)CC5)cc4)c3n2)nn1] | 4-((1-(4-(2-(2-aminopyridin-3-yl)-5-(1-isopropyl-1H-1,2,3-triazol-4-yl)-3H-imidazo[4,5-b]pyridin-3-yl)benzyl)piperidin-4-yl)amino)pyrimidine-2-carbonitrile |
| 612 | 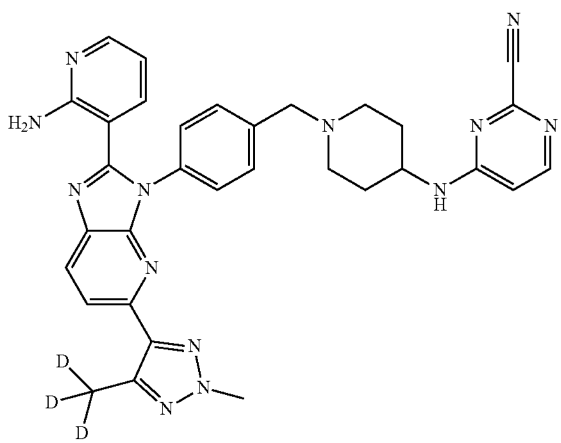 [SMILES: [2H]C([2H])([2H])c1nn(C)nc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(2-methyl-5-(methyl-d3)-2H-1,2,3-triazol-4-yl)-3H-imidazo[4,5-b]pyridin-3-yl)benzyl)piperidin-4-yl)amino)pyrimidine-2-carbonitrile |
| 613 | 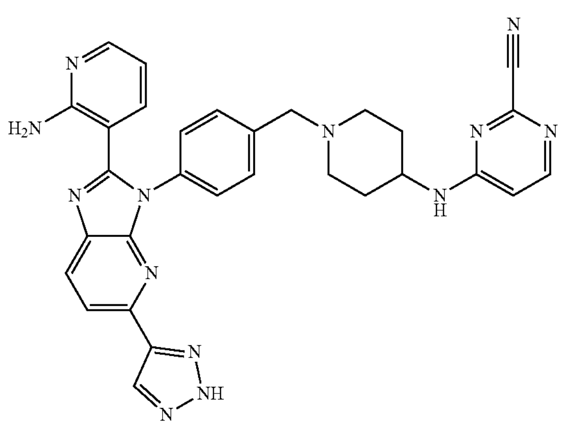 [SMILES: N#Cc1nccc(NC2CCN(Cc3ccc(-n4c(-c5cccnc5N)nc5ccc(-c6cn[nH]n6)nc54)cc3)CC2)n1] | 4-((1-(4-(2-(2-aminopyridin-3-yl)-5-(2H-1,2,3-triazol-4-yl)-3H-imidazo[4,5-b]pyridin-3-yl)benzyl)piperidin-4-yl)amino)pyrimidine-2-carbonitrile |

| Example | Compound Structure | Compound Name |
|---|---|---|
| 614 | 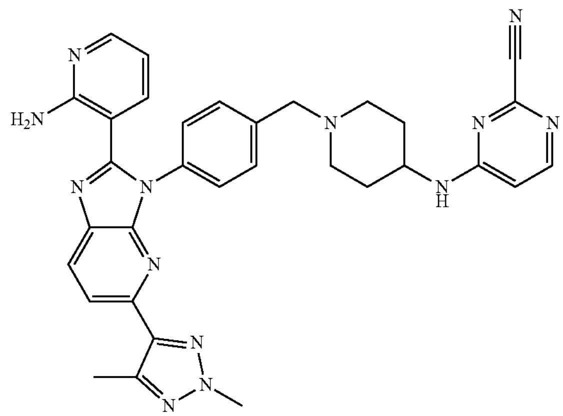 [SMILES: Cc1nn(C)nc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(2,5-dimethyl-2H-1,2,3-triazol-4-yl)-3H-imidazo[4,5-b]pyridin-3-yl)benzyl)piperidin-4-yl)amino)pyrimidine-2-carbonitrile |
| 615 | 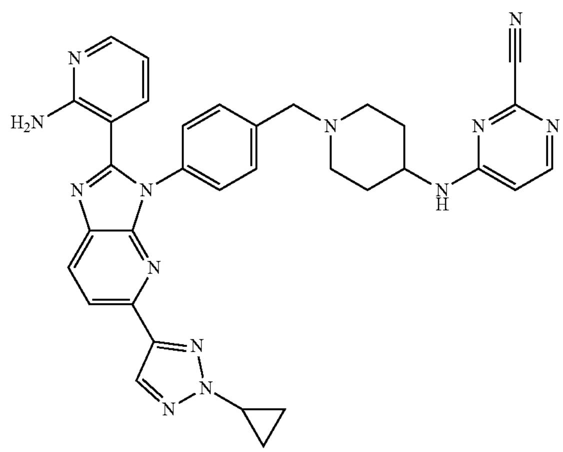 [SMILES: N#Cc1nccc(NC2CCN(Cc3ccc(-n4c(-c5cccnc5N)nc5ccc(-c6cnn(C7CC7)n6)nc54)cc3)CC2)n1] | 4-((1-(4-(2-(2-aminopyridin-3-yl)-5-(2-cyclopropyl-2H-1,2,3-triazol-4-yl)-3H-imidazo[4,5-b]pyridin-3-yl)benzyl)piperidin-4-yl)amino)pyrimidine-2-carbonitrile |
| 616 | 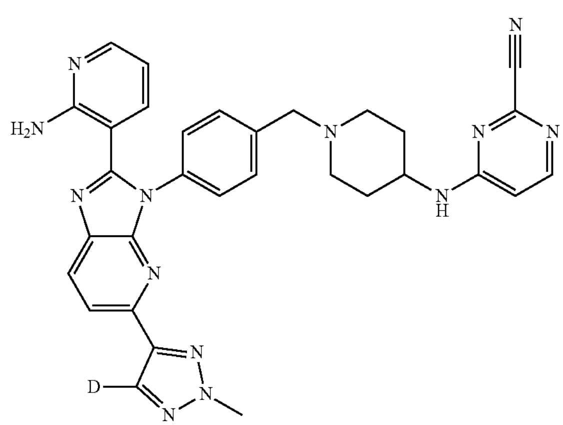 [SMILES: [2H]c1nn(C)nc1-c1ccc2nc(-c3cccnc3N)n(-c3ccc(CN4CCC(Nc5ccnc(C#N)n5)CC4)cc3)c2n1] | 4-((1-(4-(2-(2-aminopyridin-3-yl)-5-(2-methyl-2H-1,2,3-triazol-4-yl-5-d)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 617 | 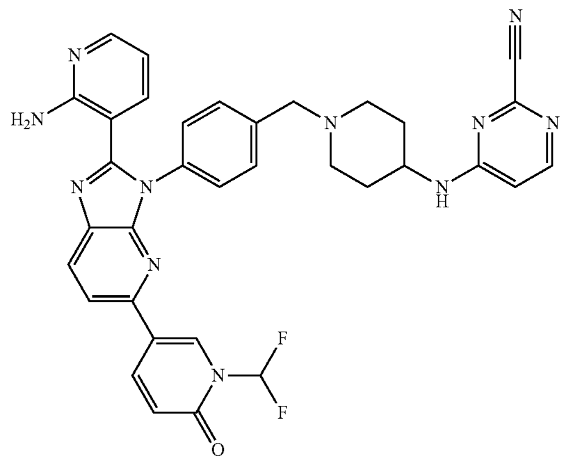 [SMILES: N#Cc1nccc(NC2CCN(Cc3ccc(-n4c(-c5cccnc5N)nc5ccc(-c6ccc(=O)n(C(F)F)c6)nc54)cc3)CC2)n1] | 4-((1-(4-(2-(2-aminopyridin-3-yl)-5-(1-(difluoromethyl)-6-oxo-1,6-dihydropyridin-3-yl)-3H-imidazo[4,5-b]pyridin-3-yl)benzyl)piperidin-4-yl)amino)pyrimidine-2-carbonitrile |
| 618 | 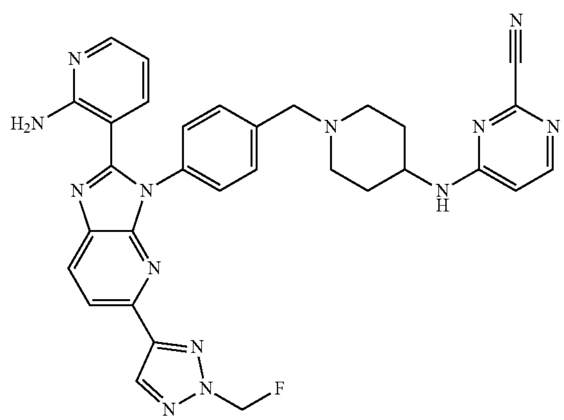 [SMILES: N#Cc1nccc(NC2CCN(Cc3ccc(-n4c(-c5cccnc5N)nc5ccc(-c6cnn(CF)n6)nc54)cc3)CC2)n1] | 4-((1-(4-(2-(2-aminopyridin-3-yl)-5-(2-(fluoromethyl)-2H-1,2,3-triazol-4-yl)-3H-imidazo[4,5-b]pyridin-3-yl)benzyl)piperidin-4-yl)amino)pyrimidine-2-carbonitrile |
| 619 | 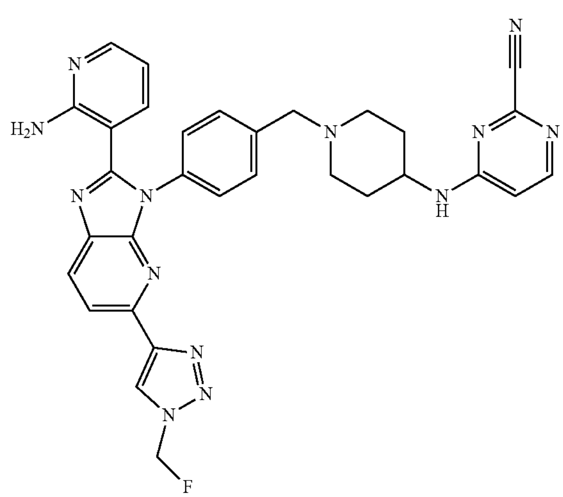 [SMILES: N#Cc1nccc(NC2CCN(Cc3ccc(-n4c(-c5cccnc5N)nc5ccc(-c6cn(CF)nn6)nc54)cc3)CC2)n1] | 4-((1-(4-(2-(2-aminopyridin-3-yl)-5-(1-(fluoromethyl)-1H-1,2,3-triazol-4-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 620 | 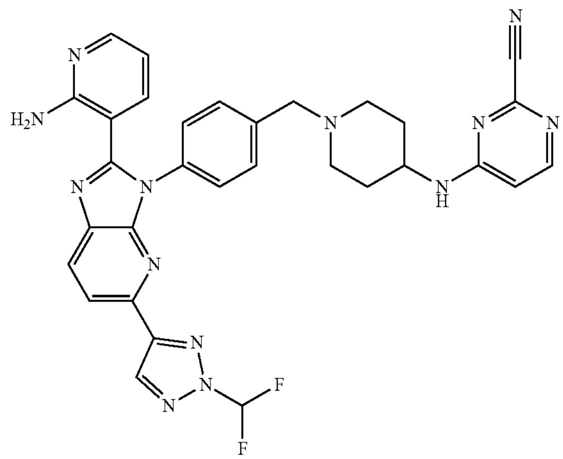 [SMILES: N#Cc1nccc(NC2CCN(Cc3ccc(-n4c(-c5cccnc5N)nc5ccc(-c6cnn(C(F)F)n6)nc54)cc3)CC2)n1] | 4-((1-(4-(2-(2-aminopyridin-3-yl)-5-(2-(difluoromethyl)-2H-1,2,3-triazol-4-yl)-3H-imidazo[4,5-b]pyridin-3-yl)benzyl)piperidin-4-yl)amino)pyrimidine-2-carbonitrile |
| 621 | 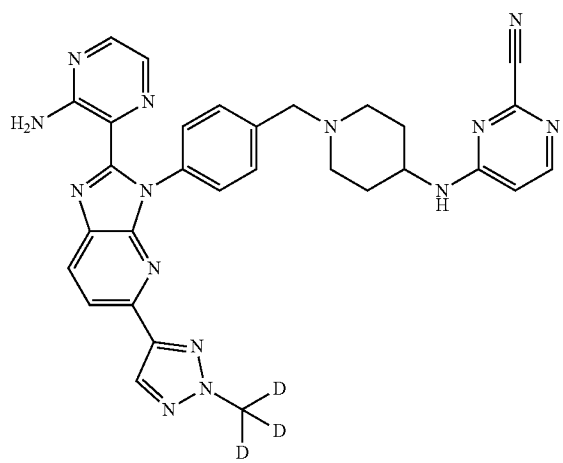 [SMILES: [2H]C([2H])([2H])n1ncc(-c2ccc3nc(-c4nccnc4N)n(-c4ccc(CN5CCC(Nc6ccnc(C#N)n6)CC5)cc4)c3n2)n1] | 4-((1-(4-(2-(3-aminopyrazin-2-yl)-5-(2-(methyl-d3)-2H-1,2,3-triazol-4-yl)-3H-imidazo[4,5-b]pyridin-3-yl)benzyl)piperidin-4-yl)amino)pyrimidine-2-carbonitrile |
| 622 | 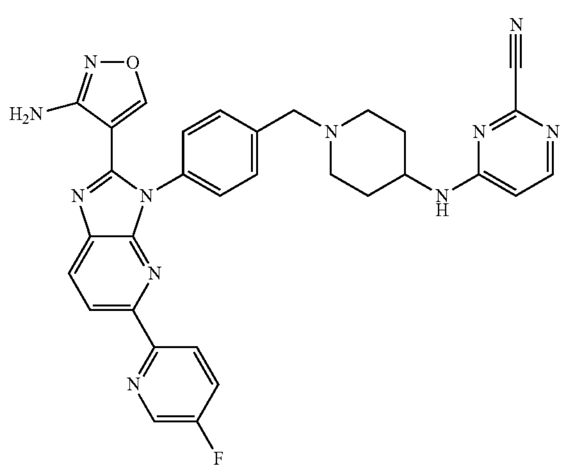 [SMILES: N#Cc1nccc(NC2CCN(Cc3ccc(-n4c(-c5conc5N)nc5ccc(-c6ccc(F)cn6)nc54)cc3)CC2)n1] | 4-((1-(4-(2-(3-aminoisoxazol-4-yl)-5-(5-fluoropyridin-2-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 623 | 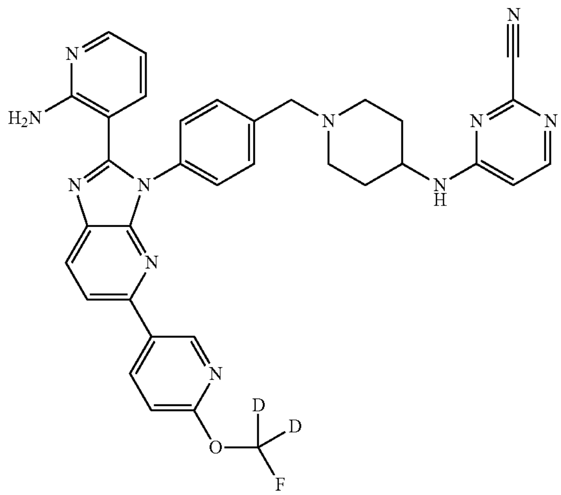 [SMILES: [2H]C([2H])(F)Oc1ccc(-c2ccc3nc(-c4cccnc4N)n(-c4ccc(CN5CCC(Nc6ccnc(C#N)n6)CC5)cc4)c3n2)cn1] | 4-((1-(4-(2-(2-aminopyridin-3-yl)-5-(6-(fluoromethoxy-d2)pyridin-3-yl)-3H-imidazo[4,5-b]pyridin-3-yl)benzyl)piperidin-4-yl)amino)pyrimidine-2-carbonitrile |
| 624 | 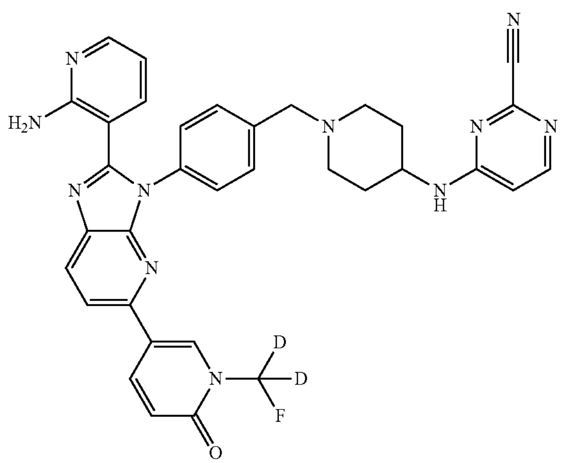 [SMILES: [2H]C([2H])(F)n1cc(-c2ccc3nc(-c4cccnc4N)n(-c4ccc(CN5CCC(Nc6ccnc(C#N)n6)CC5)cc4)c3n2)ccc1=O] | 4-((1-(4-(2-(2-aminopyridin-3-yl)-5-(1-(fluoromethyl-d2)-6-oxo-1,6-dihydropyridin-3-yl)-3H-imidazo[4,5-b]pyridin-3-yl)benzyl)piperidin-4-yl)amino)pyrimidine-2-carbonitrile |
| 625 | 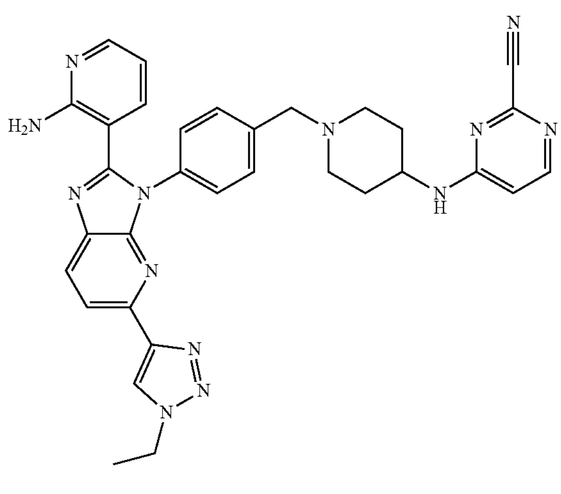 [SMILES: CCn1cc(-c2ccc3nc(-c4cccnc4N)n(-c4ccc(CN5CCC(Nc6ccnc(C#N)n6)CC5)cc4)c3n2)nn1] | 4-((1-(4-(2-(2-aminopyridin-3-yl)-5-(1-ethyl-1H-1,2,3-triazol-4-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 626 | 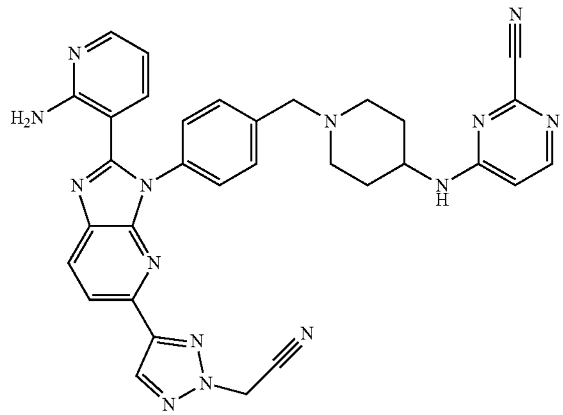 [SMILES: N#CCn1ncc(-c2ccc3nc(-c4cccnc4N)n(-c4ccc(CN5CCC(Nc6ccnc(C#N)n6)CC5)cc4)c3n2)n1] | 4-((1-(4-(2-(2-aminopyridin-3-yl)-5-(2-(cyanomethyl)-2H-1,2,3-triazol-4-yl)-3H-imidazo[4,5-b]pyridin-3-yl)benzyl)piperidin-4-yl)amino)pyrimidine-2-carbonitrile |
| 627 | 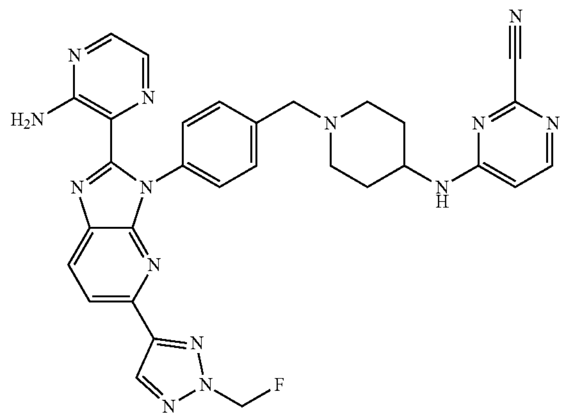 [SMILES: N#Cc1nccc(NC2CCN(Cc3ccc(-n4c(-c5nccnc5N)nc5ccc(-c6cnn(CF)n6)nc54)cc3)CC2)n1] | 4-((1-(4-(2-(3-aminopyrazin-2-yl)-5-(2-(fluoromethyl)-2H-1,2,3-triazol-4-yl)-3H-imidazo[4,5-b]pyridin-3-yl)benzyl)piperidin-4-yl)amino)pyrimidine-2-carbonitrile |
| 628 | 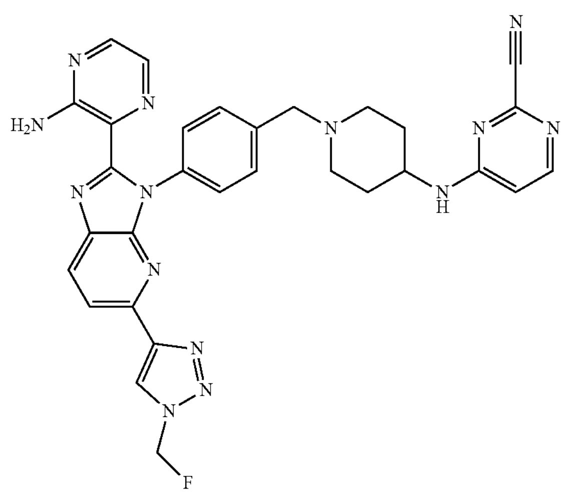 [SMILES: N#Cc1nccc(NC2CCN(Cc3ccc(-n4c(-c5nccnc5N)nc5ccc(-c6cn(CF)nn6)nc54)cc3)CC2)n1] | 4-((1-(4-(2-(3-aminopyrazin-2-yl)-5-(1-(fluoromethyl)-1H-1,2,3-triazol-4-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 629 | 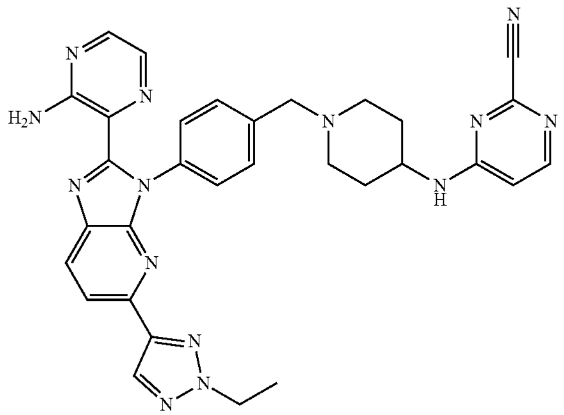 [SMILES: CCn1ncc(-c2ccc3nc(-c4nccnc4N)n(-c4ccc(CN5CCC(Nc6ccnc(C#N)n6)CC5)cc4)c3n2)n1] | 4-((1-(4-(2-(3-aminopyrazin-2-yl)-5-(2-ethyl-2H-1,2,3-triazol-4-yl)-3H-imidazo[4,5-b]pyridin-3-yl)benzyl)piperidin-4-yl)amino)pyrimidine-2-carbonitrile |
| 630 | 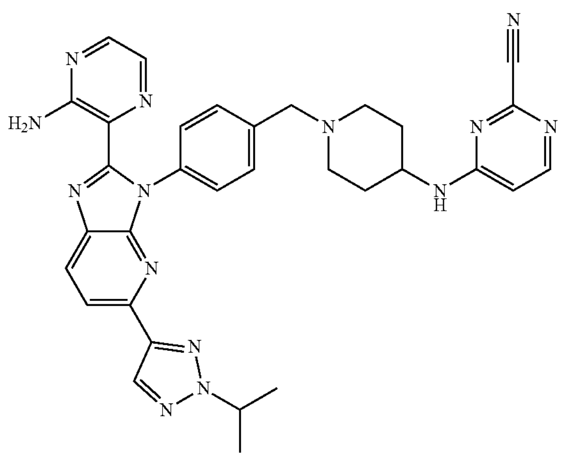 [SMILES: CC(C)n1ncc(-c2ccc3nc(-c4nccnc4N)n(-c4ccc(CN5CCC(Nc6ccnc(C#N)n6)CC5)cc4)c3n2)n1] | 4-((1-(4-(2-(3-aminopyrazin-2-yl)-5-(2-isopropyl-2H-1,2,3-triazol-4-yl)-3H-imidazo[4,5-b]pyridin-3-yl)benzyl)piperidin-4-yl)amino)pyrimidine-2-carbonitrile |
| 631 | 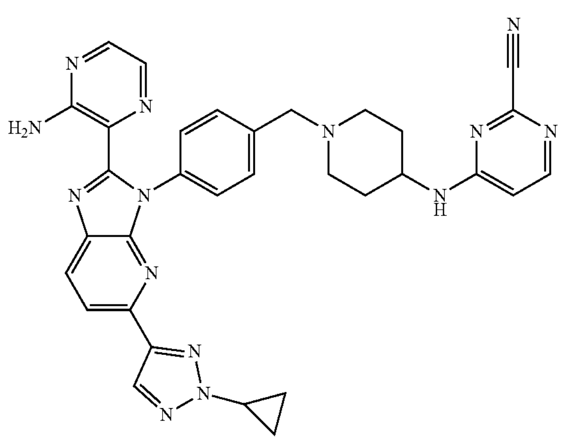 [SMILES: N#Cc1nccc(NC2CCN(Cc3ccc(-n4c(-c5nccnc5N)nc5ccc(-c6cnn(C7CC7)n6)nc54)cc3)CC2)n1] | 4-((1-(4-(2-(3-aminopyrazin-2-yl)-5-(2-cyclopropyl-2H-1,2,3-triazol-4-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 632 | 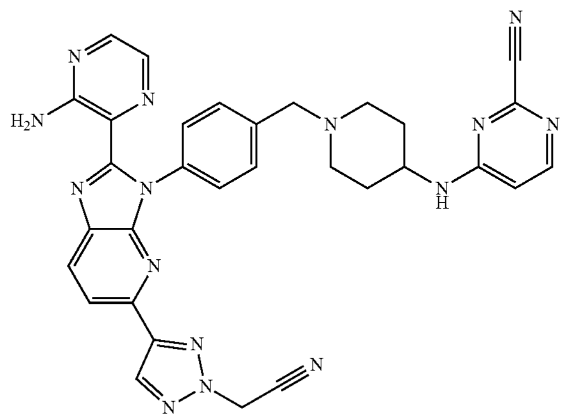 [SMILES: N#CCn1ncc(-c2ccc3nc(-c4nccnc4N)n(-c4ccc(CN5CCC(Nc6ccnc(C#N)n6)CC5)cc4)c3n2)n1] | 4-((1-(4-(2-(3-aminopyrazin-2-yl)-5-(2-(cyanomethyl)-2H-1,2,3-triazol-4-yl)-3H-imidazo[4,5-b]pyridin-3-yl)benzyl)piperidin-4-yl)amino)pyrimidine-2-carbonitrile |
| 633 | 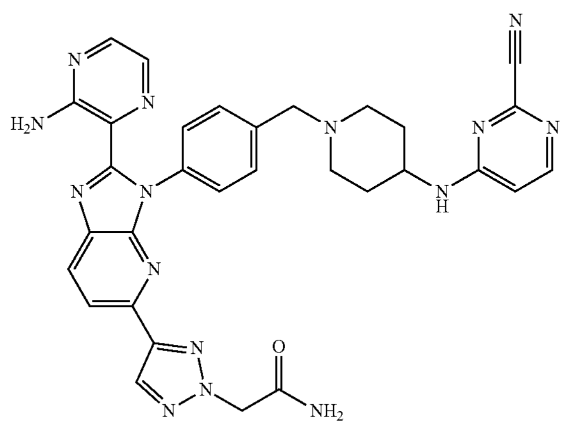 [SMILES: N#Cc1nccc(NC2CCN(Cc3ccc(-n4c(-c5nccnc5N)nc5ccc(-c6cnn(CC(N)=O)n6)nc54)cc3)CC2)n1] | 2-(4-(2-(3-aminopyrazin-2-yl)-3-(4-((4-((2-cyanopyrimidin-4-yl)amino)piperidin-1-yl)methyl)phenyl)-3H-imidazo[4,5-b]pyridin-5-yl)-2H-1,2,3-triazol-2-yl)acetamide |
| 634 | 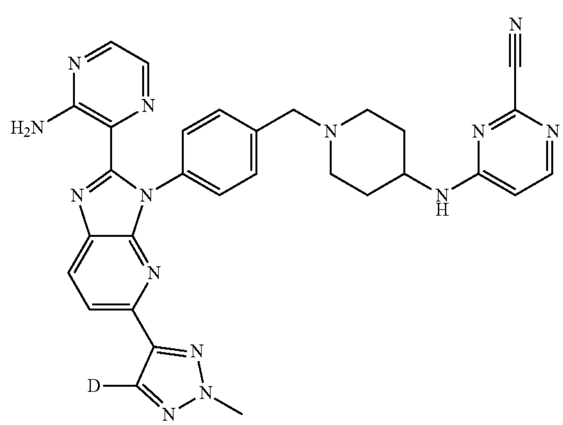 [SMILES: [2H]c1nn(C)nc1-c1ccc2nc(-c3nccnc3N)n(-c3ccc(CN4CCC(Nc5ccnc(C#N)n5)CC4)cc3)c2n1] | 4-((1-(4-(2-(3-aminopyrazin-2-yl)-5-(2-methyl-2H-1,2,3-triazol-4-yl-5-d)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 635 | 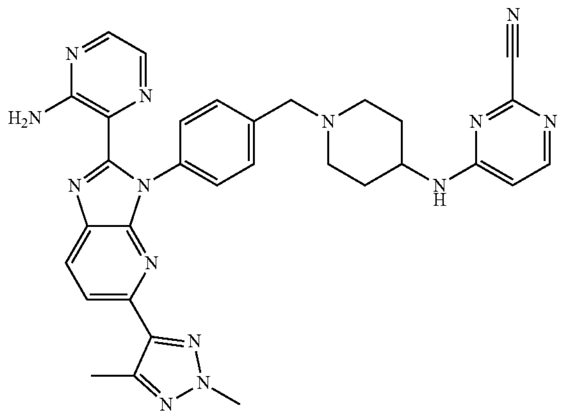 | 4-((1-(4-(2-(3-aminopyrazin-2-yl)-5-(2,5-dimethyl-2H-1,2,3-triazol-4-yl)-3H-imidazo[4,5-b]pyridin-3-yl)benzyl)piperidin-4-yl)amino)pyrimidine-2-carbonitrile |
| 636 | 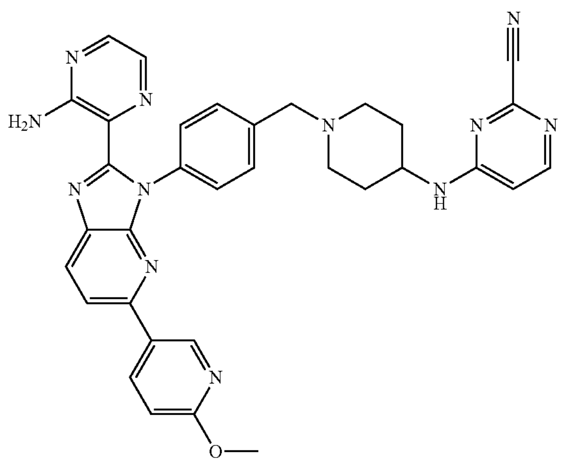 [SMILES: COc1ccc(-c2ccc3nc(-c4nccnc4N)n(-c4ccc(CN5CCC(Nc6ccnc(C#N)n6)CC5)cc4)c3n2)cn1] | 4-((1-(4-(2-(3-aminopyrazin-2-yl)-5-(6-methoxypyridin-3-yl)-3H-imidazo[4,5-b]pyridin-3-yl)benzyl)piperidin-4-yl)amino)pyrimidine-2-carbonitrile |
| 637 | 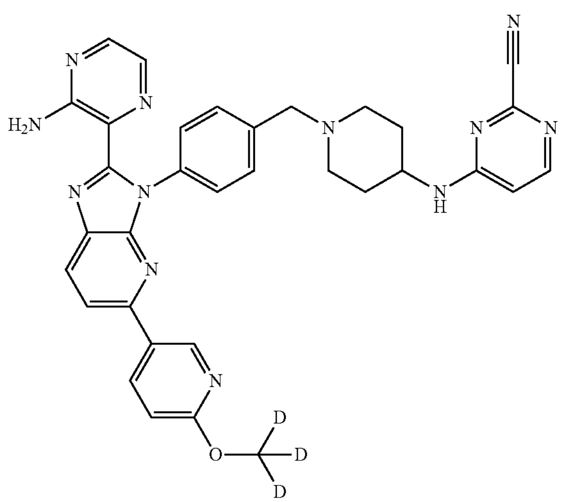 [SMILES: [2H]C([2H])([2H])Oc1ccc(-c2ccc3nc(-c4nccnc4N)n(-c4ccc(CN5CCC(Nc6ccnc(C#N)n6)CC5)cc4)c3n2)cn1] | 4-((1-(4-(2-(3-aminopyrazin-2-yl)-5-(6-(methoxy-d3)pyridin-3-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 638 | 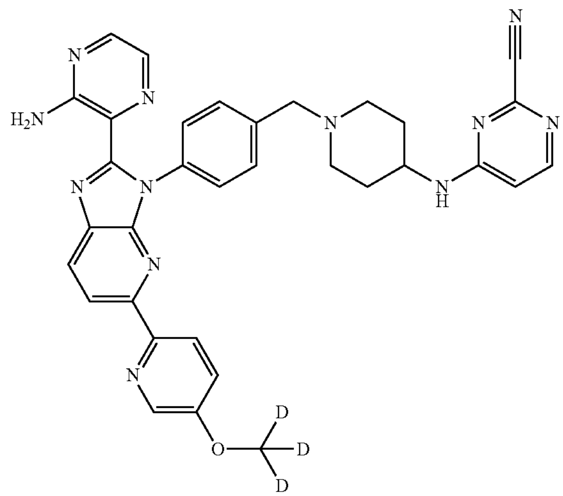 [SMILES: [2H]C([2H])([2H])Oc1ccc(-c2ccc3nc(-c4nccnc4N)n(-c4ccc(CN5CCC(Nc6ccnc(C#N)n6)CC5)cc4)c3n2)nc1] | 4-((1-(4-(2-(3-aminopyrazin-2-yl)-5-(5-(methoxy-d3)pyridin-2-yl)-3H-imidazo[4,5-b]pyridin-3-yl)benzyl)piperidin-4-yl)amino)pyrimidine-2-carbonitrile |
| 639 | 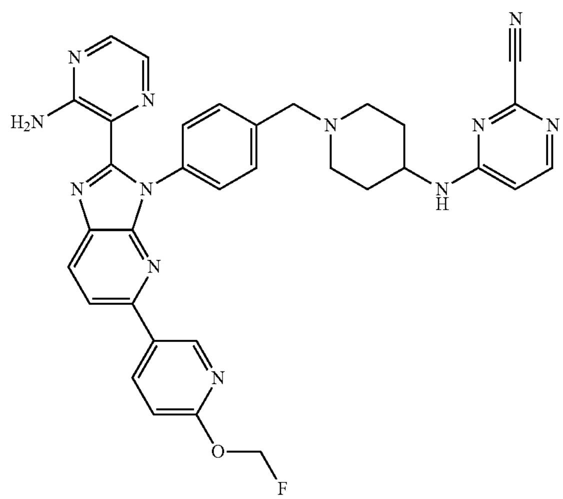 [SMILES: N#Cc1nccc(NC2CCN(Cc3ccc(-n4c(-c5nccnc5N)nc5ccc(-c6ccc(OCF)nc6)nc54)cc3)CC2)n1] | 4-((1-(4-(2-(3-aminopyrazin-2-yl)-5-(6-(fluoromethoxy)pyridin-3-yl)-3H-imidazo[4,5-b]pyridin-3-yl)benzyl)piperidin-4-yl)amino)pyrimidine-2-carbonitrile |
| 640 | 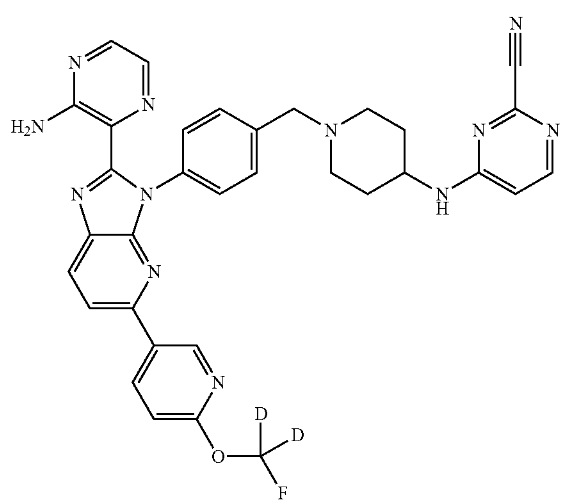 | 4-((1-(4-(2-(3-aminopyrazin-2-yl)-5-(6-(fluoromethoxy-d2)pyridin-3-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 641 | 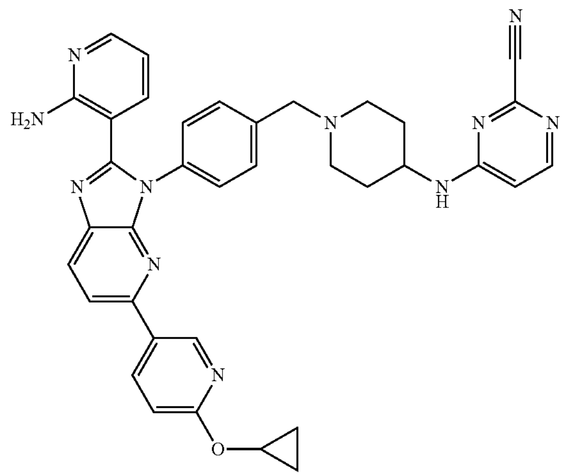 [SMILES: N#Cc1nccc(NC2CCN(Cc3ccc(-n4c(-c5cccnc5N)nc5ccc(-c6ccc(OC7CC7)nc6)nc54)cc3)CC2)n1] | 4-((1-(4-(2-(2-aminopyridin-3-yl)-5-(6-cyclopropoxypyridin-3-yl)-3H-imidazo[4,5-b]pyridin-3-yl)benzyl)piperidin-4-yl)amino)pyrimidine-2-carbonitrile |
| 642 | 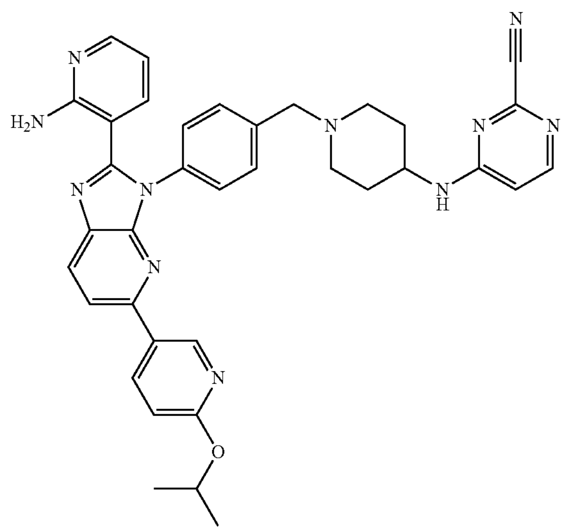 [SMILES: CC(C)Oc1ccc(-c2ccc3nc(-c4cccnc4N)n(-c4ccc(CN5CCC(Nc6ccnc(C#N)n6)CC5)cc4)c3n2)cn1] | 4-((1-(4-(2-(2-aminopyridin-3-yl)-5-(6-isopropoxypyridin-3-yl)-3H-imidazo[4,5-b]pyridin-3-yl)benzyl)piperidin-4-yl)amino)pyrimidine-2-carbonitrile |
| 643 | 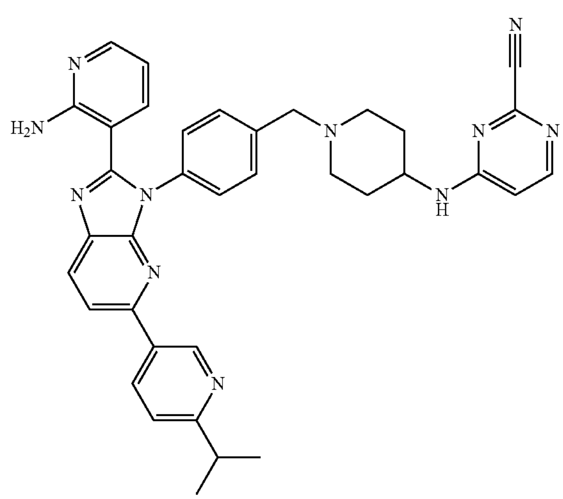 [SMILES: CC(C)c1ccc(-c2ccc3nc(-c4cccnc4N)n(-c4ccc(CN5CCC(Nc6ccnc(C#N)n6)CC5)cc4)c3n2)cn1] | 4-((1-(4-(2-(2-aminopyridin-3-yl)-5-(6-isopropylpyridin-3-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 644 | 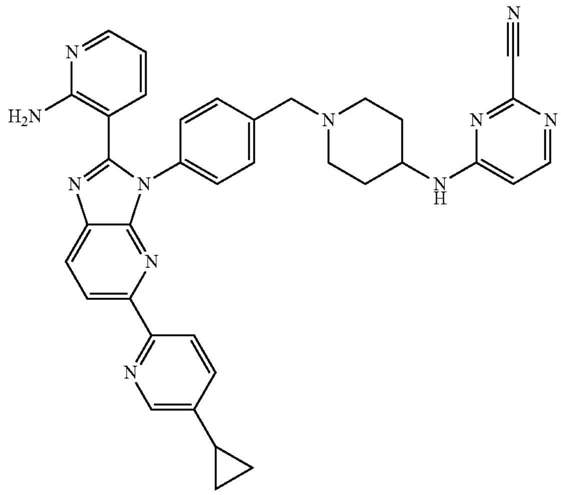 [SMILES: N#Cc1nccc(NC2CCN(Cc3ccc(-n4c(-c5cccnc5N)nc5ccc(-c6ccc(C7CC7)cn6)nc54)cc3)CC2)n1] | 4-((1-(4-(2-(2-aminopyridin-3-yl)-5-(5-cyclopropylpyridin-2-yl)-3H-imidazo[4,5-b]pyridin-3-yl)benzyl)piperidin-4-yl)amino)pyrimidine-2-carbonitrile |
| 645 | 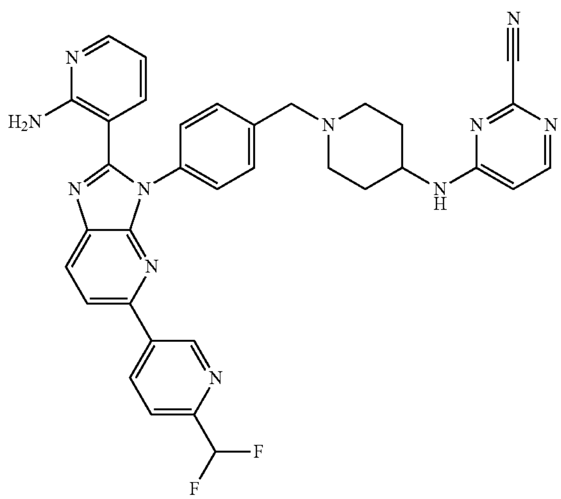 [SMILES: N#Cc1nccc(NC2CCN(Cc3ccc(-n4c(-c5cccnc5N)nc5ccc(-c6ccc(C(F)F)nc6)nc54)cc3)CC2)n1] | 4-((1-(4-(2-(2-aminopyridin-3-yl)-5-(6-(difluoromethyl)pyridin-3-yl)-3H-imidazo[4,5-b]pyridin-3-yl)benzyl)piperidin-4-yl)amino)pyrimidine-2-carbonitrile |
| 646 | 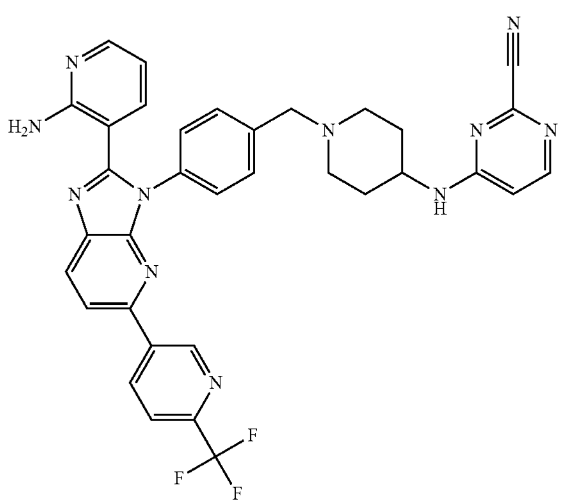 [SMILES: N#Cc1nccc(NC2CCN(Cc3ccc(-n4c(-c5cccnc5N)nc5ccc(-c6ccc(C(F)(F)F)nc6)nc54)cc3)CC2)n1] | 4-((1-(4-(2-(2-aminopyridin-3-yl)-5-(6-(trifluoromethyl)pyridin-3-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 647 | 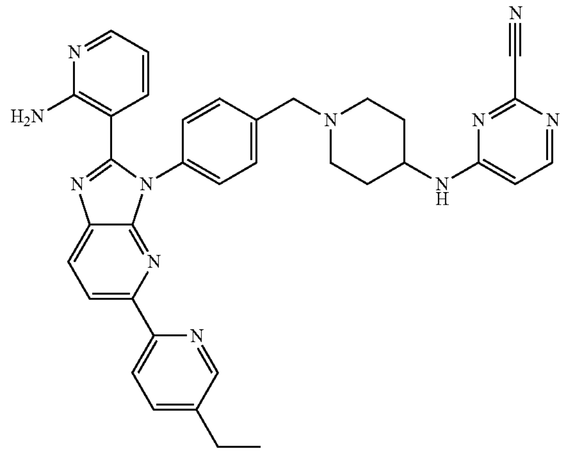 [SMILES: CCc1ccc(-c2ccc3nc(-c4cccnc4N)n(-c4ccc(CN5CCC(Nc6ccnc(C#N)n6)CC5)cc4)c3n2)nc1] | 4-((1-(4-(2-(2-aminopyridin-3-yl)-5-(5-ethylpyridin-2-yl)-3H-imidazo[4,5-b]pyridin-3-yl)benzyl)piperidin-4-yl)amino)pyrimidine-2-carbonitrile |
| 648 | 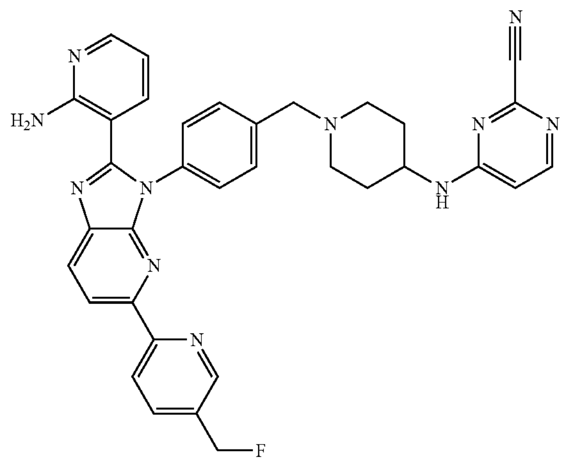 [SMILES: N#Cc1nccc(NC2CCN(Cc3ccc(-n4c(-c5cccnc5N)nc5ccc(-c6ccc(CF)cn6)nc54)cc3)CC2)n1] | 4-((1-(4-(2-(2-aminopyridin-3-yl)-5-(5-(fluoromethyl)pyridin-2-yl)-3H-imidazo[4,5-b]pyridin-3-yl)benzyl)piperidin-4-yl)amino)pyrimidine-2-carbonitrile |
| 649 | 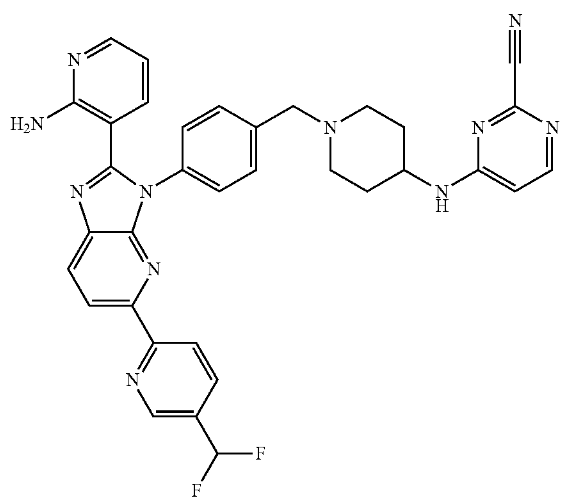 [SMILES: N#Cc1nccc(NC2CCN(Cc3ccc(-n4c(-c5cccnc5N)nc5ccc(-c6ccc(C(F)F)cn6)nc54)cc3)CC2)n1] | 4-((1-(4-(2-(2-aminopyridin-3-yl)-5-(5-(difluoromethyl)pyridin-2-yl)-3H-imidazo[4,5-b]pyridin-3-yl)benzyl)piperidin-4-yl)amino)pyrimidine-2-carbonitrile |

TABLE 1-continued

| Example | Compound Structure | Compound Name |
|---|---|---|
| 650 | 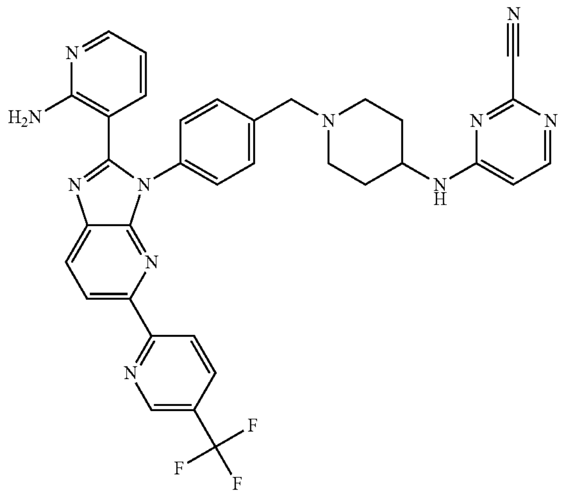 [SMILES: N#Cc1nccc(NC2CCN(Cc3ccc(-n4c(-c5cccnc5N)nc5ccc(-c6ccc(C(F)(F)F)cn6)nc54)cc3)CC2)n1] | 4-((1-(4-(2-(2-aminopyridin-3-yl)-5-(5-(trifluoromethyl)pyridin-2-yl)-3H-imidazo[4,5-b]pyridin-3-yl)benzyl)piperidin-4-yl)amino)pyrimidine-2-carbonitrile |

Another embodiment provides an AKT1 inhibitory compound, or a pharmaceutically acceptable salt or solvate thereof, having a structure presented in Table 2.

TABLE 2

TABLE 2-continued

TABLE 2-continued

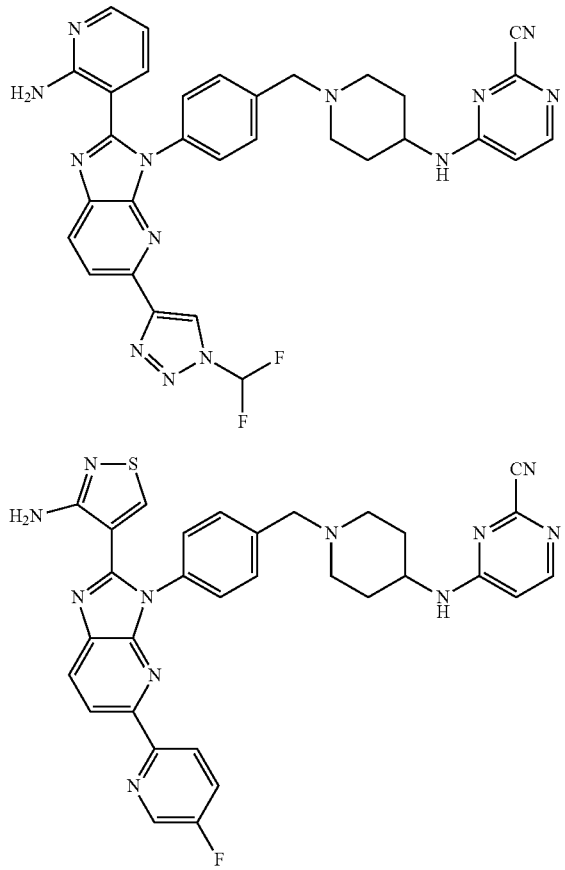

Preparation of Compounds

The compounds used in the synthetic chemistry reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz& Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983: H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the AKT1 inhibitory compound described herein is administered as a pure chemical. In other embodiments, the AKT1 inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, PA (2005)).

Provided herein is a pharmaceutical composition comprising at least one AKT1 inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I), or a pharmaceutically acceptable salt or solvate thereof.

One embodiment provides a method of preparing a pharmaceutical composition comprising mixing a compound of Formula (I), or a pharmaceutically acceptable salt or solvate thereof, and a pharmaceutically acceptable carrier.

In certain embodiments, the AKT1 inhibitory compound as described by Formula (I), or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

One embodiment provides a pharmaceutical composition comprising a pharmaceutically acceptable excipient and a compound of Table 1 or Table 2, or a pharmaceutically acceptable salt or solvate thereof.

One embodiment provides a method of preparing a pharmaceutical composition comprising mixing a compound of Table 1 or Table 2, or a pharmaceutically acceptable salt or solvate thereof, and a pharmaceutically acceptable carrier.

In certain embodiments, the AKT1 inhibitory compound as described by Table 1 or Table 2, or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, PA (2005)).

In some embodiments, the AKT1 inhibitory compound as described by Formula (I) or Table 1 or Table 2, or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one AKT1 inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I), (Ia), or (Ib), or a pharmaceutically acceptable salt or solvate thereof, for use in a method of treatment of the human or animal body.

One embodiment provides a compound of Formula (I), (Ia), or (Ib), or a pharmaceutically acceptable salt or solvate thereof, for use in a method of treatment of cancer or neoplastic disease.

One embodiment provides a pharmaceutical composition comprising a compound of Formula (I), (Ia), or (Ib), or a pharmaceutically acceptable salt or solvate thereof, and a pharmaceutically acceptable excipient for use in a method of treatment of cancer or neoplastic disease.

One embodiment provides a use of a compound of Formula (I), (Ia), or (Ib), or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Formula (I), (Ia), or (Ib), or a pharmaceutically acceptable salt or solvate thereof. In some embodiments is provided a method of treating cancer, in a patient in need thereof, comprising administering to the patient a pharmaceutical composition comprising a compound of Formula (I), (Ia), or (Ib), or a pharmaceutically acceptable salt or solvate thereof, and a pharmaceutically acceptable excipient.

One embodiment provides a compound of Table 1 or Table 2, or a pharmaceutically acceptable salt or solvate thereof, for use in a method of treatment of the human or animal body.

One embodiment provides a compound of Table 1 or Table 2, or a pharmaceutically acceptable salt or solvate thereof, for use in a method of treatment of cancer or neoplastic disease.

One embodiment provides a pharmaceutical composition comprising a compound of Table 1 or Table 2, or a pharmaceutically acceptable salt or solvate thereof, and a pharmaceutically acceptable excipient for use in a method of treatment of cancer or neoplastic disease.

One embodiment provides a use of a compound of Table 1 or Table 2, or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Table 1 or Table 2, or a pharmaceutically acceptable salt or solvate thereof. In some embodiments is provided a method of treating cancer, in a patient in need thereof, comprising administering to the patient a pharmaceutical composition comprising a compound of Table 1 or Table 2, or a pharmaceutically acceptable salt or solvate thereof, and a pharmaceutically acceptable excipient.

Provided herein is the method wherein the pharmaceutical composition is administered orally. Provided herein is the method wherein the pharmaceutical composition is administered by injection.

One embodiment provides a method of inhibiting a AKT1 enzyme comprising contacting the AKT1 enzyme with a compound of Formula (I), (Ia), or (Ib), or Table 1 or Table 2. Another embodiment provides the method of inhibiting a AKT1 enzyme, wherein the AKT1 enzyme is contacted in an in vivo setting. Another embodiment provides the method of inhibiting a AKT1 enzyme, wherein the AKT1 enzyme is contacted in an in vitro setting.

Modification of AKT1

Without wishing to be bound by any theory, the AKT1 inhibitory compounds described herein interact with AKT1 E17K by nucleophilic addition of the lysine of residue 17 to the nitrile group of the compounds of Formula (I), (Ia), or (Ib), or Table 1 or Table 2 as indicated in the scheme below.

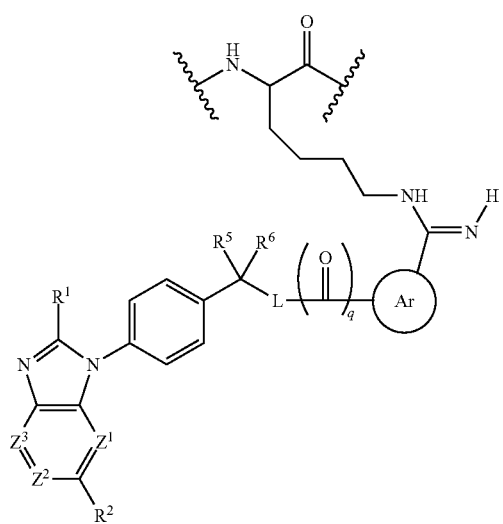

K17

One embodiment provides a modified AKT1 E17K polypeptide wherein the lysine at position 17 of an unmodified AKT1 E17K polypeptide has been modified with a nitrogen substituent having the structure of Formula (X), or a tautomer thereof:

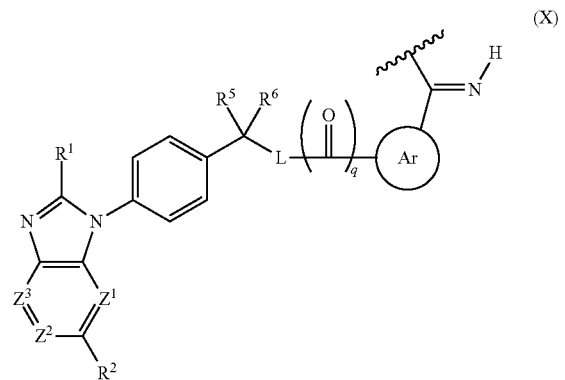

(X)

wherein:
$Z^1$ is N, C—H, or C—$R^3$;
$Z^2$ is N, C—H, or C—$R^4$;
$Z^3$ is N, C—OH, or C—$R^9$;
Ar is selected from:

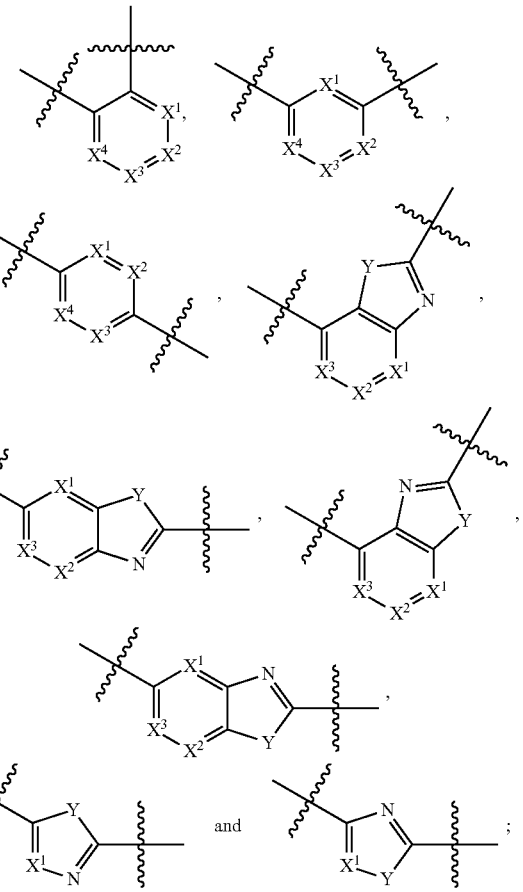

$X^1$ is N or C—$R^7$;
$X^2$ is N or C—$R^7$;
$X^3$ is N or C—$R^7$;
$X^4$ is N or C—$R^7$;
Y is O, S, or N—$R^9$;
$R^1$ is selected from hydrogen, optionally substituted $C_1$-$C_6$ alkyl, optionally substituted aryl, or optionally substituted heteroaryl;
$R^2$ is selected from hydrogen, halogen, —OH, —CN, —N($R^9$)$_2$, —O$R^9$, —S$R^9$, —SO$_2R^9$, —CO$_2R^9$, —CON($R^9$)$_2$, —S$R^9$, —S(O)$R^9$, —S(O)$_2R^9$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, optionally substituted $C_3$-$C_7$ carbocyclyl, optionally substituted 4-membered to 6-membered heterocyclyl, optionally substituted aryl, aryl substituted with an optionally substituted 4-membered to 6-membered heterocyclyl, optionally substituted heteroaryl or heteroaryl substituted with an optionally substituted 3-membered to 6-membered carbocyclyl;
$R^3$ is selected from optionally substituted $C_1$-$C_6$ alkyl, or optionally substituted aryl;
$R^4$ is selected from halogen, —CN, optionally substituted $C_1$-$C_6$ alkyl, or optionally substituted aryl;

429

R⁵ and R⁶ are each independently hydrogen, deuterium, halogen, —OH, or optionally substituted $C_1$-$C_6$ alkyl; or R⁵ and R⁶ together form an oxo; or R⁵ and R⁶ join together to form a carbocycle or heterocycle;

each R⁷ is independently selected from hydrogen, deuterium, halogen, —OH, —SH, optionally substituted $C_1$-$C_6$ alkoxy, —S-(optionally substituted $C_1$-$C_6$ alkyl), —CN, optionally substituted $C_1$-$C_6$ alkyl, and optionally substituted aryl;

L is selected from —N(R⁸)—, or a divalent radical selected from:

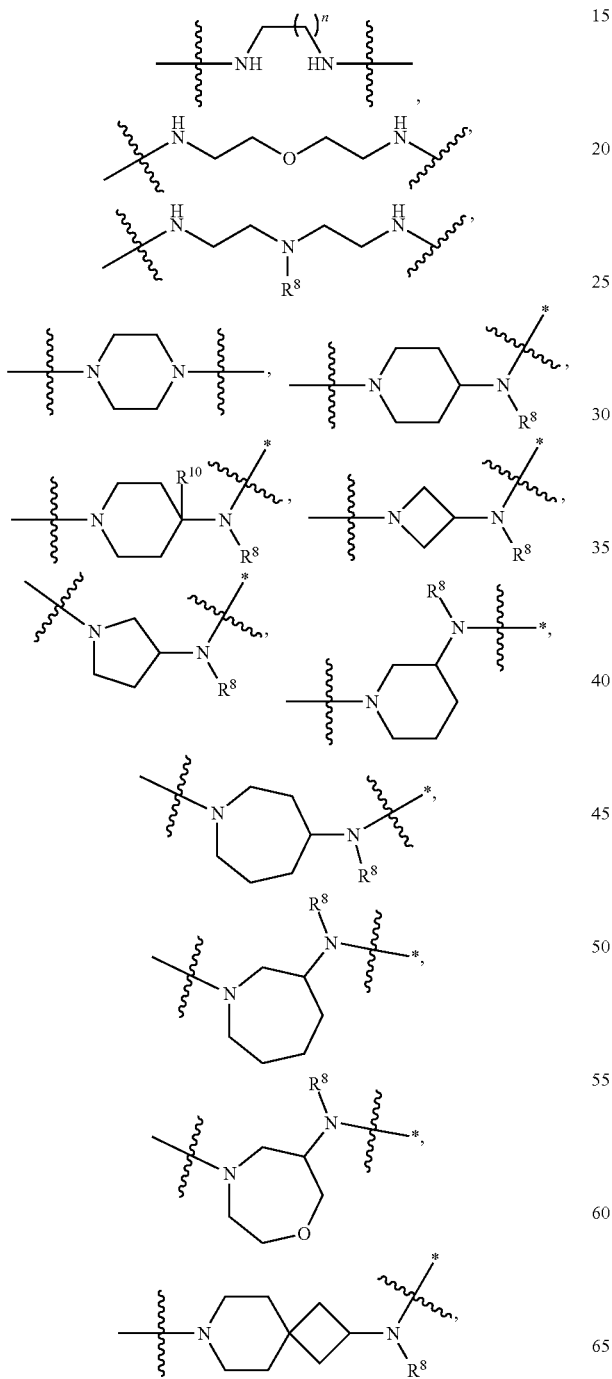

430

-continued

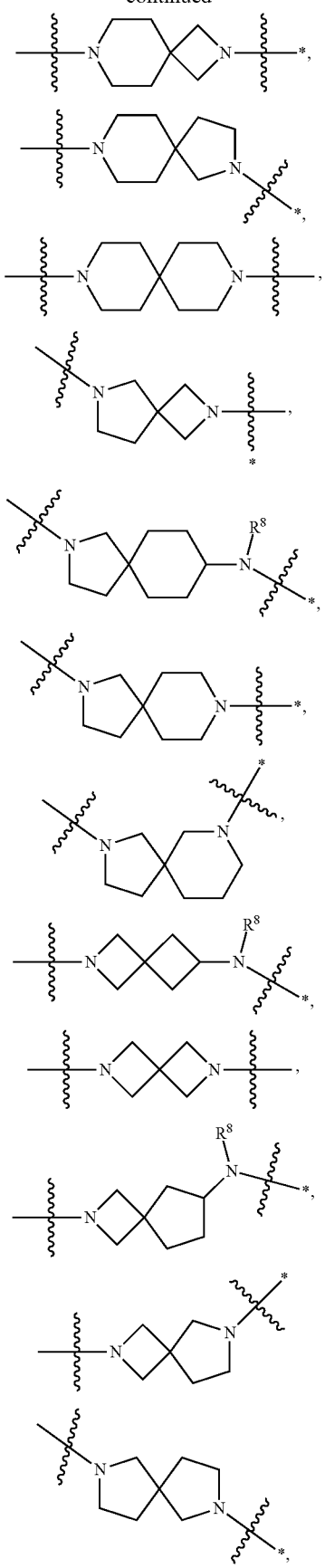

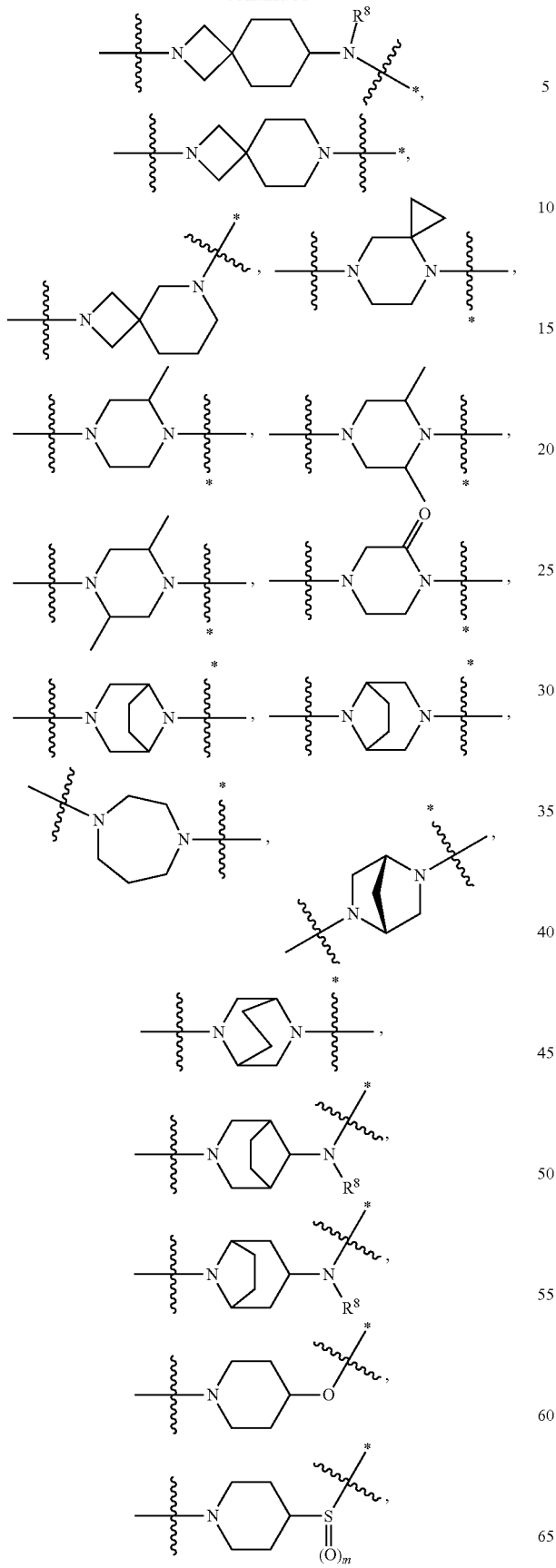
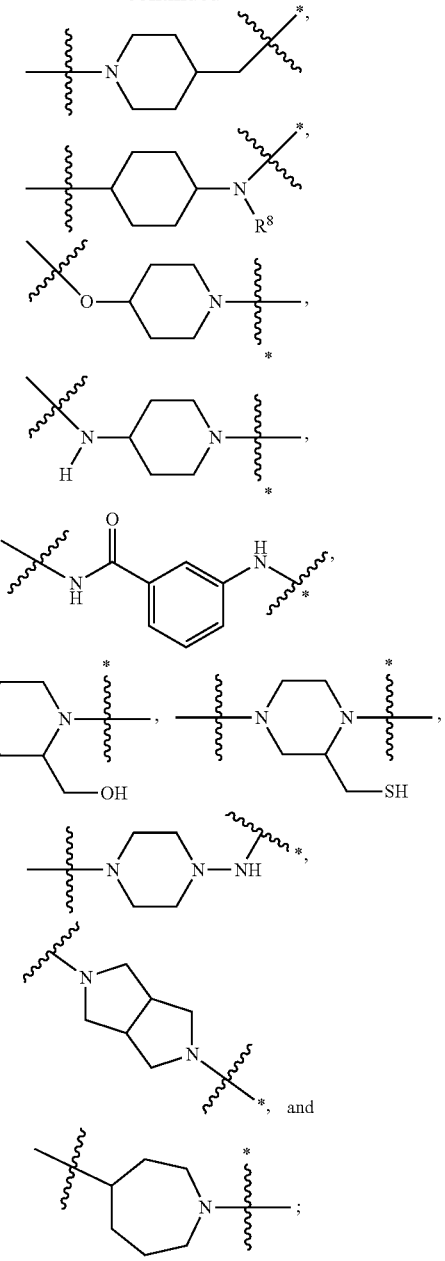

wherein the asterisk (*) indicates the bond to the —CO-Ar group;

$R^8$ is hydrogen, optionally substituted $C_1$-$C_6$ alkyl, optionally substituted $C_3$-$C_7$ cycloalkyl, or optionally substituted heterocyclyl;

each $R^9$ is hydrogen, or optionally substituted $C_1$-$C_6$ alkyl;

$R^{10}$ is optionally substituted $C_1$-$C_6$ alkyl;

m is 0, 1, or 2;

n is 1, 2, or 3; and q is 0 or 1.

Another embodiment provides the modified AKT1 E17K polypeptide of Formula (X), wherein $Z^1$ is N.

Another embodiment provides the modified AKT1 E17K polypeptide of Formula (X), wherein $Z^2$ is C—H.

Another embodiment provides the modified AKT1 E17K polypeptide of Formula (X), wherein $Z^2$ is C—$R^4$.

Another embodiment provides the modified AKT1 E17K polypeptide of Formula (X), wherein $R^1$ is optionally substituted heteroaryl. Another embodiment provides the modified AKT1 E17K polypeptide of Formula (X), wherein the optionally substituted heteroaryl is an optionally substituted pyridyl.

Another embodiment provides the modified AKT1 E17K polypeptide of Formula (X), wherein $R^2$ is optionally substituted aryl. Another embodiment provides the modified AKT1 E17K polypeptide of Formula (X), wherein the optionally substituted aryl is an optionally substituted phenyl.

Another embodiment provides the modified AKT1 E17K polypeptide of Formula (X), wherein $R^2$ is optionally substituted heteroaryl. Another embodiment provides the modified AKT1 E17K polypeptide of Formula (X), wherein the optionally substituted heteroaryl is an optionally substituted pyridyl.

Another embodiment provides the modified AKT1 E17K polypeptide of Formula (X), wherein $R^2$ is hydrogen. Another embodiment provides the modified AKT1 E17K polypeptide of Formula (X), wherein $R^6$ is hydrogen. Another embodiment provides the modified AKT1 E17K polypeptide of Formula (X), wherein $R^5$ and $R^6$ together form an oxo. Another embodiment provides the modified AKT1 E17K polypeptide of Formula (X), wherein $R^6$ is optionally substituted $C_1$-$C_6$ alkyl. Another embodiment provides the modified AKT1 E17K polypeptide of Formula (X), wherein $R^3$ and $R^6$ join together to form a carbocycle or heterocycle.

Another embodiment provides the modified AKT1 E17K polypeptide of Formula (X), wherein L is —N($R^8$)—.

Another embodiment provides the modified AKT1 E17K polypeptide of Formula (X), wherein L is selected from:

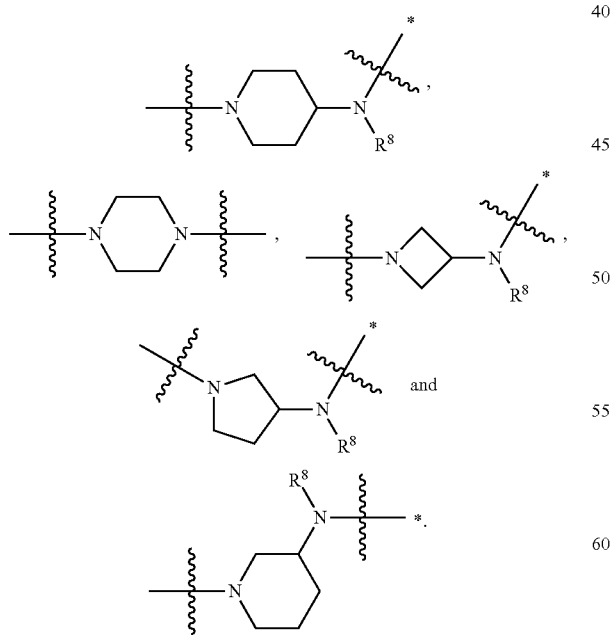

Another embodiment provides the modified AKT1 E17K polypeptide of Formula (X), wherein L is selected from:

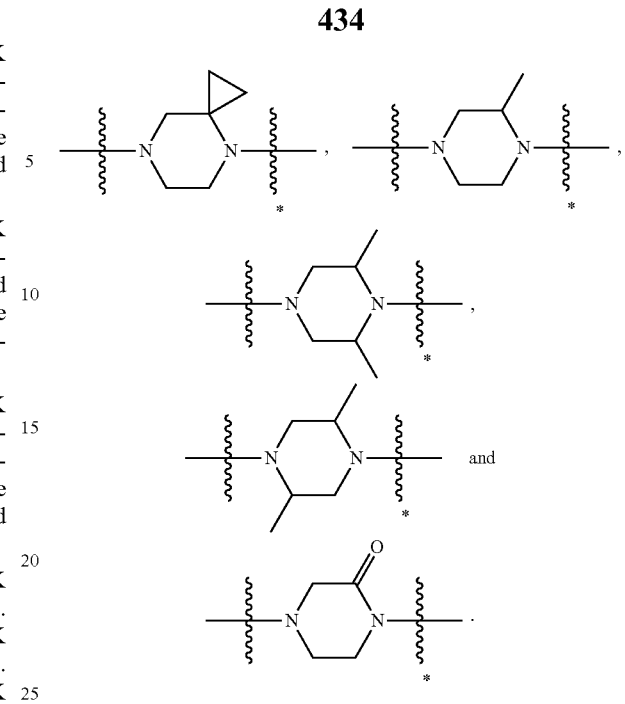

Another embodiment provides the modified AKT1 E17K polypeptide of Formula (X), wherein L is selected from:

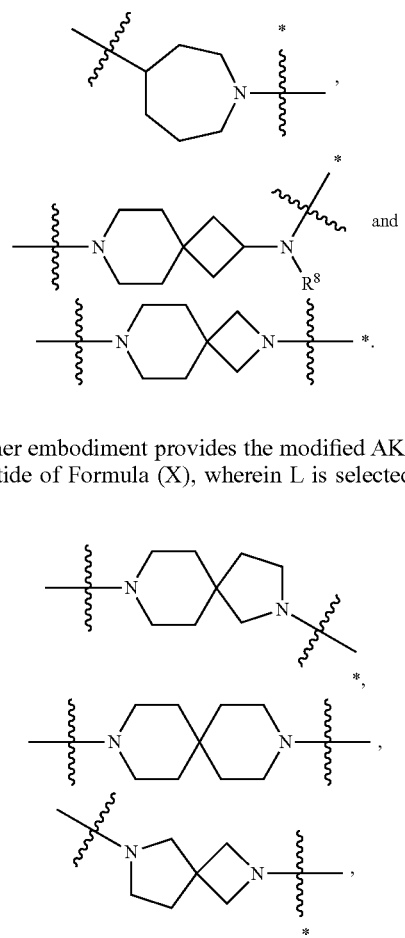

Another embodiment provides the modified AKT1 E17K polypeptide of Formula (X), wherein L is selected from:

435

-continued

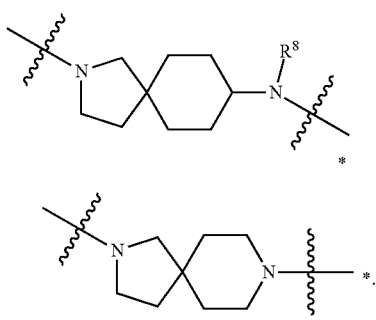
and

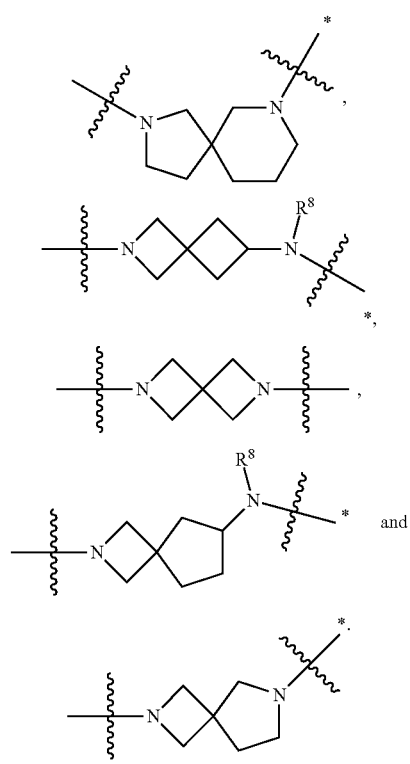

Another embodiment provides the modified AKT1 E17K polypeptide of Formula (X), wherein L is selected from:

436

-continued

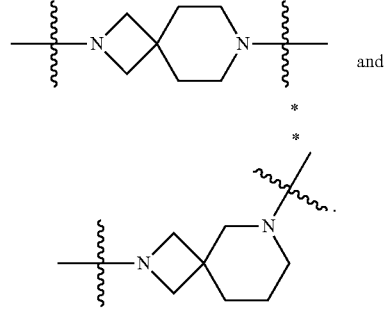
and

Another embodiment provides the modified AKT1 E17K polypeptide of Formula (X), wherein $R^8$ is hydrogen or optionally substituted C1-C6 alkyl.

Another embodiment provides the modified AKT1 E17K polypeptide of Formula (X), wherein q is 0.

Another embodiment provides the modified AKT1 E17K polypeptide of Formula (X), wherein q is 1.

Another embodiment provides the modified AKT1 E17K polypeptide of Formula (X), wherein Ar is

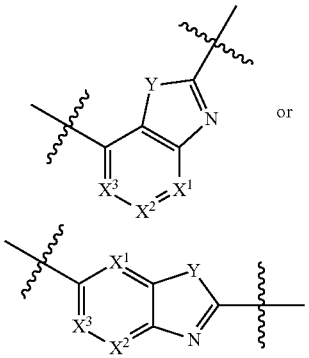
or

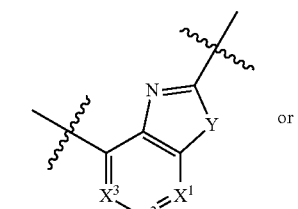

Another embodiment provides the modified AKT1 E17K polypeptide of Formula (X), wherein Ar is

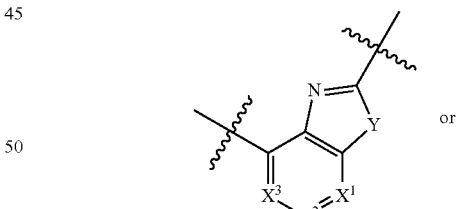
or

Another embodiment provides the modified AKT1 E17K polypeptide of Formula (X), wherein L is selected from:

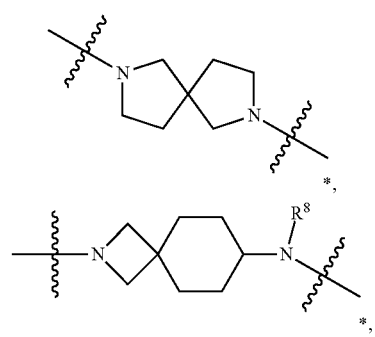

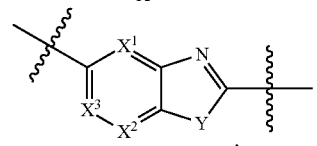
or

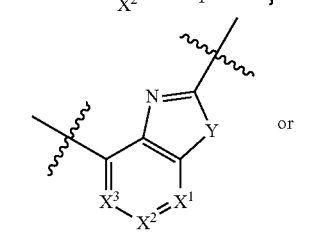

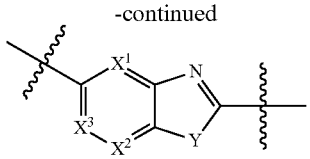

Another embodiment provides the modified AKT1 E17K polypeptide of Formula (X), wherein Ar is

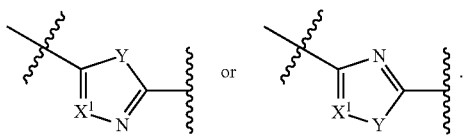

Another embodiment provides the modified AKT1 E17K polypeptide of Formula (X), wherein $X^1$, $X^2$, and $X^3$ are C—H. Another embodiment provides the modified AKT1 E17K polypeptide of Formula (X), wherein $X^1$ is N; and $X^2$, and $X^3$ are C—H. Another embodiment provides the modified AKT1 E17K polypeptide of Formula (X), wherein $X^2$ is N; and $X^1$, and $X^3$ are C—H. Another embodiment provides the modified AKT1 E17K polypeptide of Formula (X), wherein $X^3$ is N; and $X^1$, and $X^2$ are C—H. Another embodiment provides the modified AKT1 E17K polypeptide of Formula (X), wherein $X^1$ is N; and $X^2$, and $X^3$ are C—H.

Another embodiment provides the modified AKT1 E17K polypeptide of Formula (X), wherein Y is O. Another embodiment provides the modified AKT1 E17K polypeptide of Formula (X), wherein Y is S. Another embodiment provides the modified AKT1 E17K polypeptide of Formula (X), wherein Y is N—$R^9$. Another embodiment provides the modified AKT1 E17K polypeptide of Formula (X), wherein $R^9$ is hydrogen. Another embodiment provides the modified AKT1 E17K polypeptide of Formula (X), wherein $R^9$ is optionally substituted C1-C6 alkyl.

Another embodiment provides the modified AKT1 E17K polypeptide of Formula (X), wherein Ar is

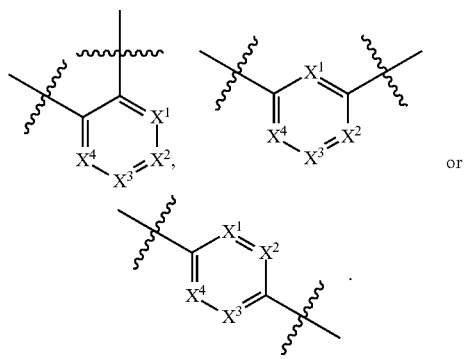

Another embodiment provides the modified AKT1 E17K polypeptide of Formula (X), wherein $X^1$ is N. Another embodiment provides the modified AKT1 E17K polypeptide of Formula (X), wherein $X^2$ is N. Another embodiment provides the modified AKT1 E17K polypeptide of Formula (X), wherein $X^3$ is N. Another embodiment provides the modified AKT1 E17K polypeptide of Formula (X), wherein $X^4$ is N. Another embodiment provides the modified AKT1 E17K polypeptide of Formula (X), $X^1$ is C—H. Another embodiment provides the modified AKT1 E17K polypeptide of Formula (X), $X^2$ is C—H. Another embodiment provides the modified AKT1 E17K polypeptide of Formula (X), $X^3$ is C—H. Another embodiment provides the modified AKT1 E17K polypeptide of Formula (X), wherein $X^4$ is C—H.

Another embodiment provides the modified AKT1 E17K polypeptide of Formula (X), wherein $R^3$ is optionally substituted C1-C6 alkyl. Another embodiment provides the modified AKT1 E17K polypeptide of Formula (X), wherein $R^3$ is optionally substituted aryl. Another embodiment provides the modified AKT1 E17K polypeptide of Formula (X), wherein $R^4$ is optionally substituted C1-C6 alkyl. Another embodiment provides the modified AKT1 E17K polypeptide of Formula (X), wherein $R^4$ is optionally substituted aryl.

Another embodiment provides the modified AKT1 E17K polypeptide of Formula (X), wherein Ar is

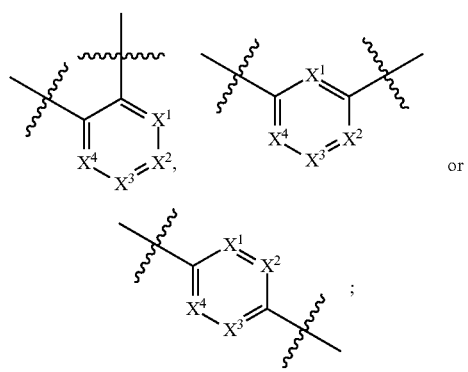

and L is selected from:

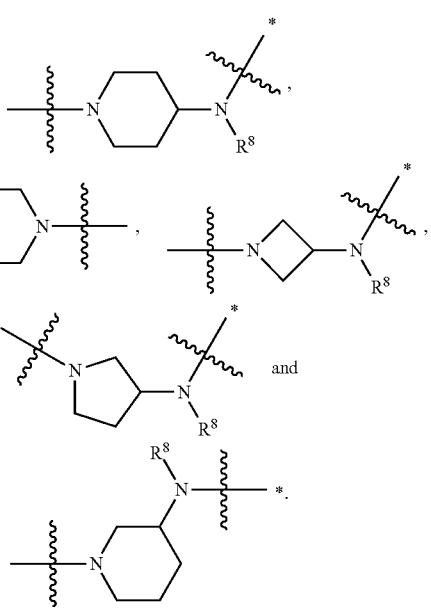

Another embodiment provides the modified AKT1 E17K polypeptide of Formula (X), wherein Ar is

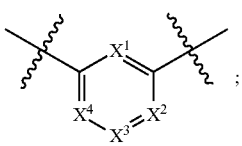

and L is

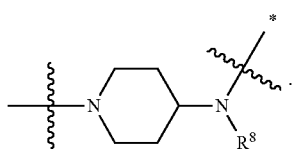

Another embodiment provides the modified AKT1 E17K polypeptide of Formula (X), wherein Ar is

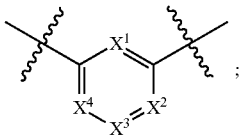

and L is

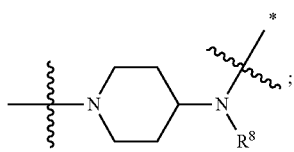

and q is 0.

Another embodiment provides the modified AKT1 E17K polypeptide of Formula (X), wherein Ar is

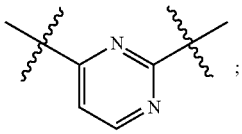 [SMILES: *c1ccnc(*)n1]

and L is selected from:

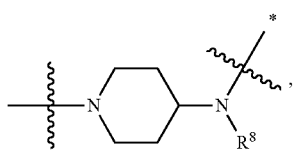

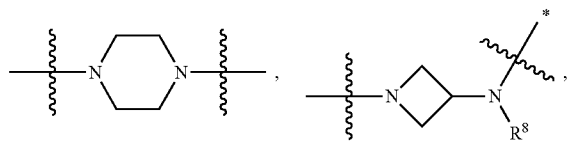

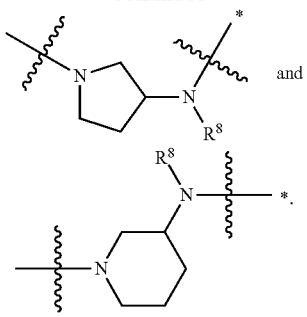

Another embodiment provides the modified AKT1 E17K polypeptide of Formula (X), wherein Ar is

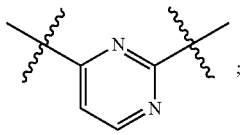 [SMILES: *c1ccnc(*)n1]

and $R^1$ is optionally substituted heteroaryl, and $R^2$ is optionally substituted heteroaryl.

Another embodiment provides the modified AKT1 E17K polypeptide wherein the unmodified AKT1 E17K polypeptide is a SEQID selected from a SEQID provided in Table 3.

TABLE 3

| SEQ ID NO | Amino Acid Sequence |
|---|---|
| 1 | MSDVAIVKEGWLHKRGKYIKTWRPRYFLLKNDGTFIGYKER |
| | PQDVDQREAPLNNFSVAQCOLMKTERPRPNTFIIRCLQWTT |
| | VIERTFHVETPEEREEWTTAIQTVADGLKKQEEEEMDFRSG |
| | SPSDNSGAEEMEVSLAKPKHRVTMNEFEYLKLLGKGTFGKV |
| | ILVKEKATGRYYAMKILKKEVIVAKDEVAHTLTENRVLQNS |
| | RHPFLTALKYSFQTHDRLCFVMEYANGGELFFHLSRERVFS |
| | EDRARFYGAEIVSALDYLHSEKNVVYRDLKLENLMLDKDGH |
| | IKITDFGLCKEGIKDGATMKTFCGTPEYLAPEVLEDNDYGR |
| | AVDWWGLGVVMYEMMCGRLPFYNQDHEKLFELILMEEIRFP |
| | RTLGPEAKSLLSGLLKKDPKQRLGGGSEDAKEIMQHRFFAG |
| | IVWQHVYEKKLSPPFKPQVTSETDTRYFDEEFTAQMITITP |
| | PDQDDSMECVDSERRPHFPQFSYSASGTA |

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the AKT1 inhibitory compounds disclosed herein are synthesized according to the following examples. As used below, and throughout the description of the invention, the following abbreviations, unless otherwise indicated, shall be understood to have the following meanings:

ACN acetonitrile
° C. degrees Celsius
$\delta_H$ chemical shift in parts per million downfield from tetramethylsilane
DCM dichloromethane ($CH_2Cl_2$)
DIAD diisopropyl azodicarboxylate
DIEA diisopropylethylamine
DMF dimethylformamide
DMSO dimethylsulfoxide
EA ethyl acetate
EtOAc ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
μ micro
m multiplet (spectral); meter(s); milli
M molar
$M^+$ parent molecular ion
Me methyl
MsCl methanesulfonyl chloride
MHz megahertz
min minute(s)
mol mole(s); molecular (as in mol wt)
mL milliliter
MS mass spectrometry
nm nanometer(s)
NMR nuclear magnetic resonance
pH potential of hydrogen; a measure of the acidity or basicity of an aqueous solution
PE petroleum ether
RT room temperature
s singlet (spectral)
t triplet (spectral)
SFC Supercritical fluid chromatography
T temperature
TFA trifluoroacetic acid
THF tetrahydrofuran
TPP Triphenylphosphine Experimental Procedures Intermediate 1: 3-(3-(4-(Aminomethyl)phenyl)-3H-imidazo[4,5-b]pyridin-2-yl)pyridin-2-amine

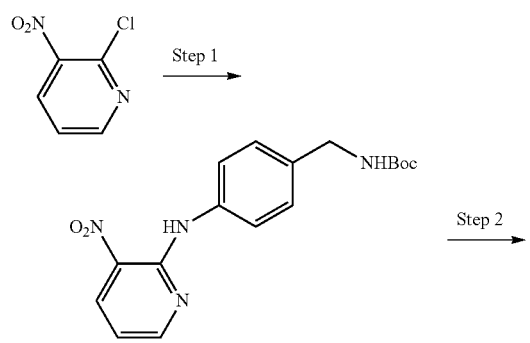

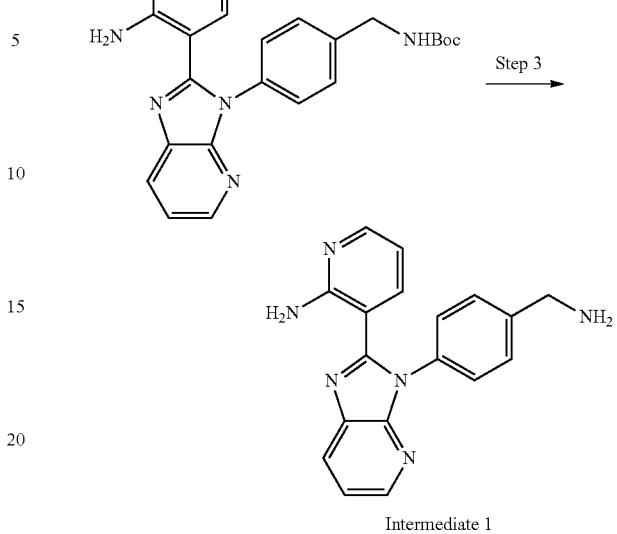

Intermediate 1

Step 1: Tert-butyl 4-((3-nitropyridin-2-yl)amino)benzylcarbamate

To a solution of 2-chloro-3-nitro-pyridine (7.0 g, 44.2 mmol) and tert-butyl N-[(4-aminophenyl)methyl]carbamate (9.8 g, 44.2 mmol) in DMSO (100 mL) was added DIEA (11.4 g, 88.3 mmol). The mixture was stirred at 80° C. for 12 hr. The reaction mixture was diluted with 100 mL $H_2O$ at 25° C. and extracted with EtOAc (100 mL×3). The combined organic layers were washed with brine (150 mL), dried over $Na_2SO_4$, filtered, and concentrated under reduced pressure to give a residue. The residue was purified by triturated (petroleum ether:EtOAc=10:1) to give tert-butyl N-[[4-[(3-nitro-2-pyridyl)amino]phenyl]methyl]carbamate (13.9 g, yield: 91%) as a red solid. MS: m/z=344.8 $[M+H]^+$. $^1$H NMR (400 MHz, Dimethylsulfoxide-$d_6$) δ 9.90 (s, 1H), 8.49 (dd, J=8.4, 1.6 Hz, 1H), 8.45 (dd, J=4.4, 1.6 Hz, 1H), 7.52 (d, J=8.4 Hz, 2H), 7.35 (t, J=6.0 Hz, 1H), 7.19 (d, J=8.4 Hz, 2H), 6.93 (dd, J=8.4, 4.4 Hz, 1H), 4.07 (d, J=6.0 Hz, 2H), 1.36 (s, 9H).

Step 2: Tert-butyl 4-(2-(2-aminopyridin-3-yl)-3H-imidazo[4,5-b]pyridin-3-yl)benzylcarbamate To a solution of tert-butyl N-[[4-[(3-nitro-2-pyridyl)amino]phenyl]methyl]carbamate (10 g, 29.0 mmol) in MeOH (70 mL) and DMSO (140 mL) was added 2-aminopyridine-3-carbaldehyde (3.9 g, 31.9 mmol) and $Na_2S_2O_4$ (10.1 g, 58.1 mmol). The mixture was stirred at 100° C. for 12 hr. After cooling to room temperature, the reaction mixture was diluted with 200 mL of $H_2O$, and extracted with EtOAc (400 mL×2). The combined organic layers were washed with brine (400 mL), dried over $Na_2SO_4$, filtered, and concentrated under reduced pressure to give a residue. The crude product was purified by flash chromatography on silica gel (Eluent of 1~2% MeOH in $CH_2Cl_2$) to give tert-butyl 4-(2-(2-aminopyridin-3-yl)-3H-imidazo[4,5-b]pyridin-3-yl)benzylcarbamate (5.7 g, yield: 44%) as a red solid. MS: m/z=417.4 $[M+H]^+$. $^1$H NMR (400 MHz, Dimethylsulfoxide-$d_6$) δ 8.31 (dd, J=4.8, 1.2 Hz, 1H), 8.20 (dd, J=8.0, 1.2 Hz, 1H), 7.99 (dd, J=4.8, 1.6 Hz, 1H), 7.49 (t, J=6.0 Hz, 1H), 7.41-7.36 (m, 5H), 7.21 (dd, J=7.6, 1.6 Hz, 1H), 6.99 (br s, 2H), 6.39 (dd, J=7.6, 4.8 Hz, 1H), 4.21 (d, J=6.0 Hz, 2H), 1.41 (s, 9H).

Step 3: 3-(3-(4-(Aminomethyl)phenyl)-3H-imidazo[4,5-b]pyridin-2-yl)pyridin-2-amine To a solution of tert-butyl N-[[4-[2-(2-amino-3-pyridyl)imidazo[4,5-b]pyridin-3-yl]phenyl]methyl]carbamate (350 mg, 840 µmol) in 1,4-dioxane (3 mL) was added 4 M HCl in 1,4-dioxane (1 mL) at 20° C. The mixture was stirred at 20° C. for 2 hr. The reaction was concentrated under reduced pressure to give crude product 280 mg (HCl salt, yield: 95%). The crude product was purified by prep-HPLC (Column: Phenomenex luna C18 150×25 mm×10 µm; Condition: water (HCl)-ACN; Begin B: 0; End B: 16; Gradient Time (min): 10; 100% B Hold Time (min): 2; Flow Rate (mL/min): 25) to give product (HCl salt). The product was diluted with 10 mL aqueous NaHCO₃ and extracted with DCM (10 mL×3). The combined organic layers were washed with 20 mL brine, dried over Na₂SO₄, filtered and concentrated under reduced pressure to give 3-(3-(4-(Aminomethyl)phenyl)-3H-imidazo[4,5-b]pyridin-2-yl)pyridin-2-amine (Intermediate 1, 70.0 mg, yield: 95%) was obtained as a light-yellow solid. MS: m/z=317.1 [M+H]⁺. ¹H NMR (400 MHz, Dimethylsulfoxide-d₆) δ 8.31 (dd, J=4.8, 1.2 Hz, 1H), 8.19 (dd, J=8.0, 1.2 Hz, 1H), 7.99 (dd, J=4.8, 1.6 Hz, 1H), 7.47 (d, J=8.4 Hz, 2H), 7.40-7.33 (m, 3H), 7.22 (dd, J=7.6, 2.0 Hz, 1H), 6.98 (br s, 2H), 6.40 (dd, J=7.6, 4.8 Hz, 1H), 3.79 (s, 2H), 1.82 (br s, 2H).

Intermediate 2: 3-(3-(4-(Piperazin-1-ylmethyl)phenyl)-3H-imidazo[4,5-b]pyridin-2-yl)pyridin-2-amine

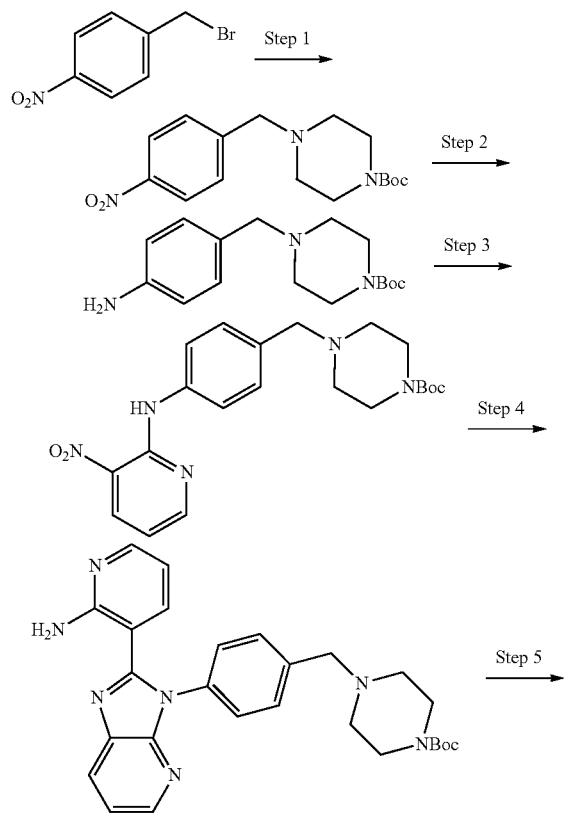

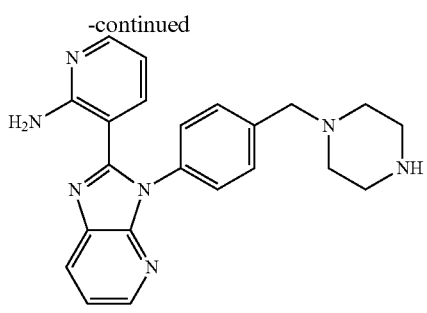

Intermediate 2

Step 1: Tert-butyl 4-(4-nitrobenzyl)piperazine-1-carboxylate

To a solution of 1-(bromomethyl)-4-nitro-benzene (25 g, 116 mmol) in ACN (250 mL) was added tert-butyl piperazine-1-carboxylate (25.8 g, 139 mmol) and K₂CO₃ (31.9 g, 231 mmol) at 20° C. The mixture was stirred at 20° C. for 12 hr. The reaction mixture was filtered. The filter liquor was concentrated to dryness to give a crude tert-butyl 4-(4-nitrobenzyl)piperazine-1-carboxylate (37 g, yield: 99%) as a white solid, which was used in the next step without further purification. MS: m/z=322.2 [M+H]⁺. ¹H NMR (400 MHz, Dimethylsulfoxide-d₆) δ 8.19 (d, J=8.8 Hz, 2H), 7.60 (d, J=8.8 Hz, 2H), 3.62 (s, 2H), 3.32-3.36 (m, 4H), 2.38-2.28 (m, 4H), 1.39 (s, 9H).

Step 2: Tert-butyl 4-(4-aminobenzyl)piperazine-1-carboxylate

To a solution of tert-butyl 4-(4-nitrobenzyl)piperazine-1-carboxylate (20 g, 62.2 mmol) in EtOH (150 mL) and H₂O (50 mL) was added Fe (17.3 g, 311 mmol) and NH₄Cl (13.3 g, 249 mmol) at 25° C., the mixture was stirred at 90° C. for 2 hr. The reaction mixture was filtered and concentrated directly to give a crude product tert-butyl 4-(4-aminobenzyl)piperazine-1-carboxylate (17 g, crude) as a yellow oil, which was used in the next step without further purification. MS: m/z=292.9 [M+H]⁺.

Step 3: Tert-butyl 4-(4-((3-nitropyridin-2-yl)amino)benzyl)piperazine-1-carboxylate To a solution of 2-chloro-3-nitro-pyridine (10 g, 63 mmol) in DMSO (200 mL) was added tert-butyl 4-(4-aminobenzyl)piperazine-1-carboxylate (15.3 g, 52.5 mmol) and DIEA (13.5 g, 105 mmol) at 25° C. The mixture was stirred at 80° C. for 12 hr. The reaction mixture was concentrated to give a residue. The residue was diluted with H₂O (200 mL) and extracted with CH₂Cl₂ (200 mL×2). The combined organic layers were washed with brine (200 mL), dried over Na₂SO₄, filtered, and concentrated under reduced pressure to give a residue. The residue was purified by flash chromatography on silica gel (Eluent of 10~30% EtOAc in petroleum ether) to give tert-butyl 4-(4-((3-nitropyridin-2-yl)amino)benzyl)piperazine-1-carboxylate (11 g, yield: 45%) as a red solid. MS: m/z=413.9 [M+H]⁺. ¹H NMR (400 MHz, Dimethylsulfoxide-d₆) δ 9.95 (s, 1H), 8.48-8.58 (m, 2H), 7.60 (d, J=8.4 Hz, 2H), 7.29 (d, J=8.4 Hz, 2H), 6.98 (dd, J=8.4, 4.8 Hz, 1H), 3.46 (s, 2H), 3.29-3.32 (m, 4H), 2.29-2.35 (m, 4H), 1.39 (s, 9H).

Step 4: Tert-butyl 4-(4-(2-(2-Aminopyridin-3-yl)-3H-imidazo[4,5-b]pyridin-3-yl)benzyl)piperazine-1-carboxylate To a solution of tert-butyl 4-(4-((3-nitropyridin-2-yl)amino)benzyl)piperazine-1-carboxylate (10 g, 24.1 mmol) in DMSO (200 mL), added 2-aminopyridine-3-carbaldehyde (3.54 g, 29.0 mmol) and $Na_2S_2O_4$ (12.6 g, 72.5 mmol) at 25° C. The mixture was stirred at 100° C. for 14 hr. The reaction mixture was poured into 500 mL of $H_2O$. The mixture was extracted with $CH_2Cl_2$ (200 mL×2). The combined organic layers were washed with brine (400 mL), dried over anhydrous $Na_2SO_4$, filtered, and concentrated to dryness. The residue was purified by flash chromatography on silica gel (Eluent of 10~30% MeOH in $CH_2Cl_2$) to give 4-(4-(2-(2-Aminopyridin-3-yl)-3H-imidazo[4,5-b]pyridin-3-yl)benzyl)piperazine-1-carboxyla (4.9 g, yield: 42%) as a red solid. MS: m/z=486.2 [M+H]$^+$. $^1$H NMR (400 MHz, Dimethylsulfoxide-$d_6$) δ 8.33 (dd, J=4.8, 1.2 Hz, 1H), 8.20 (dd, J=8.0, 1.2 Hz, 1H), 7.99 (dd, J=4.8, 2.0 Hz, 1H), 7.43-7.48 (m, 2H), 7.36-7.42 (m, 3H), 7.16 (dd, J=7.6, 1.6 Hz, 1H), 7.00 (br s, 2H), 6.38 (dd, J=7.6, 4.8 Hz, 1H), 3.56 (s, 2H), 3.33-3.37 (m, 4H), 2.32-2.38 (m, 4H), 1.40 (s, 9H).

Step 5: 3-(3-(4-(Piperazin-1-ylmethyl)phenyl)-3H-imidazo[4,5-b]pyridin-2-yl)pyridin-2-amine To a solution of tert-butyl 4-(4-(2-(2-aminopyridin-3-yl)-3H-imidazo[4,5-b]pyridin-3-yl)benzyl)piperazine-1-carboxylate (2 g, 4.12 mmol) in $CH_2Cl_2$ (10 mL) was added dropwise TFA (4.62 g, 40.5 mmol) at 25° C., the mixture was stirred at 25° C. for 3 hr. The reaction mixture was concentrated to a residue. The residue was poured into water (50 mL), then adjusted pH to about 8 by saturated $NaHCO_3$ (aq). The resulting mixture was extracted with $CH_2Cl_2$ (100 mL×3). The combined organic layers were dried over anhydrous $Na_2SO_4$, filtered, and concentrated to give 3-(3-(4-(Piperazin-1-ylmethyl)phenyl)-3H-imidazo[4,5-b]pyridin-2-yl)pyridin-2-amine (1.43 g, yield: 90%) as an off-white solid. 100 mg of solid was triturated with EtOAc (3 mL) at 25° C. for 1 hr and filtered. The filter cake was collected to give 3-(3-(4-(Piperazin-1-ylmethyl)phenyl)-3H-imidazo[4,5-b]pyridin-2-yl)pyridin-2-amine (Intermediate 2, 24.5 mg, yield: 90%). MS: m/z=386.2 [M+H]$^+$. $^1$H NMR (400 MHz, Dimethylsulfoxide-$d_6$) δ 8.33 (d, J=4.0 Hz, 1H), 8.22 (d, J=8.0 Hz, 1H), 8.00 (d, J=3.2 Hz, 1H), 7.35-7.52 (m, 5H), 7.18 (d, J=7.2 Hz, 1H), 7.00 (br s, 2H), 6.40 (dd, d, J=7.8, 4.8 Hz, 1H), 3.63 (s, 2H), 3.16-3.01 (m, 4H), 2.63-2.48 (ms, 4H).

Intermediate 3: 3-(3-(4-((4-aminopiperidin-1-yl)methyl)phenyl)-3H-imidazo[4,5-b]pyridin-2-yl)pyridin-2-amine

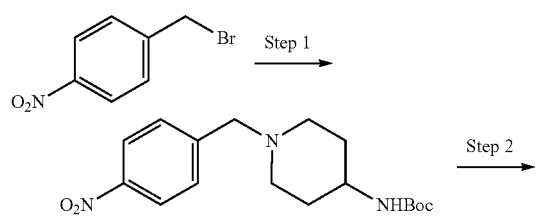

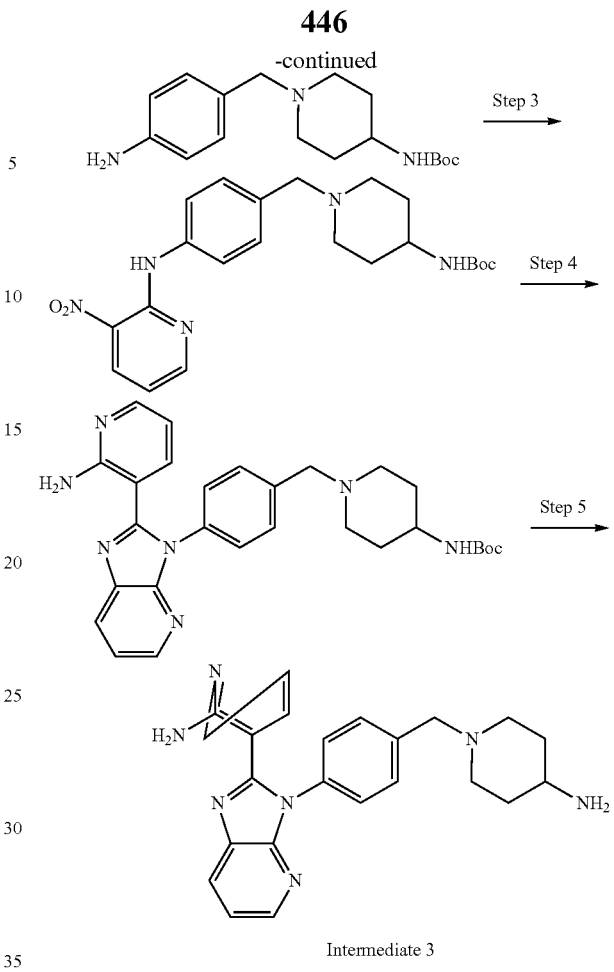

Intermediate 3

Step 1: Tert-butyl (1-(4-nitrobenzyl) piperidin-4-yl) carbamate

To a solution of 1-(bromomethyl)-4-nitro-benzene (108 g, 499 mmol) in ACN (1.5 L) was added $K_2CO_3$ (149 g, 1.1 mol) and tert-butyl N-(4-piperidyl)carbamate (100 g, 499 mmol). The mixture was stirred at 25° C. for 16 hr. The reaction mixture was filtered. The filtrate was concentrated under reduced pressure to give tert-butyl (1-(4-nitrobenzyl) piperidin-4-yl)carbamate (167 g, crude) as a yellow solid, which was used to the next step without further purification. MS: m/z=335.9 [M+H]$^+$. $^1$H NMR (400 MHz, Chloroform-d) δ 8.16 (d, J=8.8 Hz, 2H), 7.49 (d, J=8.8 Hz, 2H), 4.44 (br s, 1H), 3.56 (s, 2H), 3.52-3.42 (m, 1H), 2.77-2.74 (m, 2H), 2.16-2.10 (m, 2H), 1.93-1.90 (m, 2H), 1.43 (s, 9H), 1.42-1.36 (m, 2H).

Step 2: Tert-butyl (1-(4-aminobenzyl) piperidin-4-yl) carbamate

To a solution of tert-butyl (1-(4-nitrobenzyl) piperidin-4-yl)carbamate (109 g, 325 mmol) in EtOH (500 mL) and $H_2O$ (150 mL) was added Fe (91 g, 1.6 mol) and $NH_4Cl$ (174 g, 3.3 mol). The mixture was stirred at 85° C. for 2 hr. The reaction mixture was filtered. The filtrate was concentrated under pressure to remove most of the EtOH. The residue was diluted with 500 mL of $H_2O$ and extracted with $CH_2Cl_2$ (500 mL×2). The combined organic layers were washed with 500 mL of brine, dried over $Na_2SO_4$, filtered, and concentrated under reduced pressure to give tert-butyl (1-(4-aminobenzyl) piperidin-4-yl) carbamate (80 g, crude) as a yellow solid. MS: m/z=306.2 [M+H]+. 1H NMR (400 MHz, Chloroform-d) δ 7.14 (d, J=8.0 Hz, 2H), 6.64 (d, J=8.0 Hz, 2H), 4.51 (br d, J=6.0 Hz, 1H), 3.80-3.59 (m, 2H), 3.55 (s, 2H), 3.51-3.39 (m, 1H), 2.95-2.93 (m, 2H), 2.25-2.20 (m, 2H), 1.96-1.93 (m, 2H), 1.72-1.54 (m, 2H), 1.42 (s, 9H).

Step 3: Tert-butyl (1-(4-((3-nitropyridin-2-yl)amino)benzyl)piperidin-4-yl)carbamate To a solution of tert-butyl (1-(4-aminobenzyl) piperidin-4-yl) carbamate (30 g, 98.2 mmol) in DMSO (500 mL) was added DIEA (38.1 g, 295 mmol) and 2-chloro-3-nitropyridine (18.7 g, 118 mmol). The mixture was stirred at 100° C. for 16 hr. The reaction mixture was quenched with H2O (500 mL) at 20° C. and extracted with EtOAc (300 mL×2). The combined organic layers were washed with 300 mL of brine, dried over Na2SO4, filtered, and concentrated under reduced pressure to give a residue. The crude product was purified by flash chromatography on silica gel (Eluent of 0~10% MeOH in CH2Cl2) to give tert-butyl (1-(4-((3-nitropyridin-2-yl) amino) benzyl) piperidin-4-yl) carbamate (30 g, yield: 71%) as a yellow solid. MS: m/z=428.2 [M+H]+. 1H NMR (400 MHz, Chloroform-d) δ 10.10 (s, 1H), 8.51 (dd, J=8.0, 1.6 Hz, 1H), 8.47 (dd, J=8.4, 1.6 Hz, 1H), 7.58 (d, J=8.4 Hz, 2H), 7.32 (d, J=8.4 Hz, 2H), 6.81 (dd, J=8.4, 4.4 Hz, 1H), 4.44 (br s, 1H), 3.47 (s, 2H), 3.44-3.34 (m, 1H), 2.82-2.79 (m, 2H), 2.13-2.05 (m, 2H), 1.93-1.89 (m, 2H), 1.43 (s, 9H), 1.39-1.37 (m, 2H).

Step 4: Tert-butyl (1-(4-(2-(2-aminopyridin-3-yl)-3H-imidazo[4,5-b]pyridin-3-yl)benzyl)piperidin-4-yl)carbamate To a solution of (12.5 g, 29.2 mmol) in DMSO (500 mL) were added Na2S2O4 (15.3 g, 87.7 mmol) and 2-aminopyridine-3-carbaldehyde (4.3 g, 35.1 mmol). The mixture was stirred at 100° C. for 16 hr. The reaction mixture was quenched with H2O (1000 mL) at 20° C. and extracted with EtOAc (1000 mL×2). The combined organic layers were washed with brine (500 mL), dried over Na2SO4, filtered, and concentrated under reduced pressure to give a residue. The crude product was purified by flash chromatography on silica gel (Eluent of 0~10% MeOH in CH2Cl2) to give tert-butyl (1-(4-(2-(2-aminopyridin-3-yl)-3H-imidazo[4,5-b]pyridin-3-yl)benzyl)piperidin-4-yl)carbamate (5.5 g, yield: 38%) as a yellow solid. MS: m/z=500.2 [M+H]+. 1H NMR (400 MHz, Chloroform-d) δ 8.46-8.37 (m, 1H), 8.12-8.02 (m, 2H), 7.48 (d, J=8.0 Hz, 2H), 7.34-7.28 (m, 3H), 7.07 (dd, J=8.0, 4.0 Hz, 1H), 6.62 (br s, 2H), 6.33 (dd, J=7.6, 4.8 Hz, 1H), 4.46 (br d, J=6.0 Hz, 1H), 3.56 (s, 2H), 3.49-3.47 (m, 1H), 2.84 (br d, J=11.2 Hz, 2H), 2.14 (t, J=12.0 Hz, 2H), 1.93 (br d, J=11.2 Hz, 2H), 1.45 (s, 9H), 1.51-1.38 (m, 2H).

Step 5: 3-(3-(4-((4-Aminopiperidin-1-yl)methyl)phenyl)-3H-imidazo[4,5-b]pyridin-2-yl)pyridin-2-amine A solution of tert-butyl (1-(4-(2-(2-aminopyridin-3-yl)-3H-imidazo[4,5-b]pyridin-3-yl)benzyl)piperidin-4-yl)carbamate (2.0 g, 4.0 mmol) in HCl/1,4-dioxane (4M, 20 mL) was stirred at 25° C. for 1 hr. The reaction mixture was concentrated under reduced pressure to remove solvent. Then residue was quenched with NaHCO3 (30 mL) at 20° C., then MeOH was added, filtered, and the filtrate after freeze-dried to give 3-(3-(4-((4-aminopiperidin-1-yl) methyl)phenyl)-3H-imidazo[4,5-b]pyridin-2-yl)pyridin-2-amine (Intermediate 3, 1.45 g, yield: 91%) as a yellow solid. MS: m/z=400.1 [M+H]+. 1H NMR (400 MHz, Dimethylsulfoxide-d6) δ 8.37-8.28 (m, 1H), 8.19 (dd, J=8.0, 4.0 Hz, 1H), 7.99-7.97 (m, 1H), 7.47-7.32 (m, 5H), 7.15 (dd, J=7.6, 1.6 Hz, 1H), 7.01 (br s, 2H), 6.36 (dd, J=6.8, 4.0 Hz, 1H), 3.50 (s, 2H), 3.27-3.23 (m, 1H), 2.75 (br d, J=10.8 Hz, 2H), 2.00 (t, J=10.8 Hz, 2H), 1.72 (d, J=10.8 Hz, 2H), 1.39-1.31 (m, 2H).

Intermediate 4: 3-(3-(4-(Aminomethyl)phenyl)-5-phenyl-3H-imidazo[4,5-b]pyridin-2-yl)pyridin-2-amine

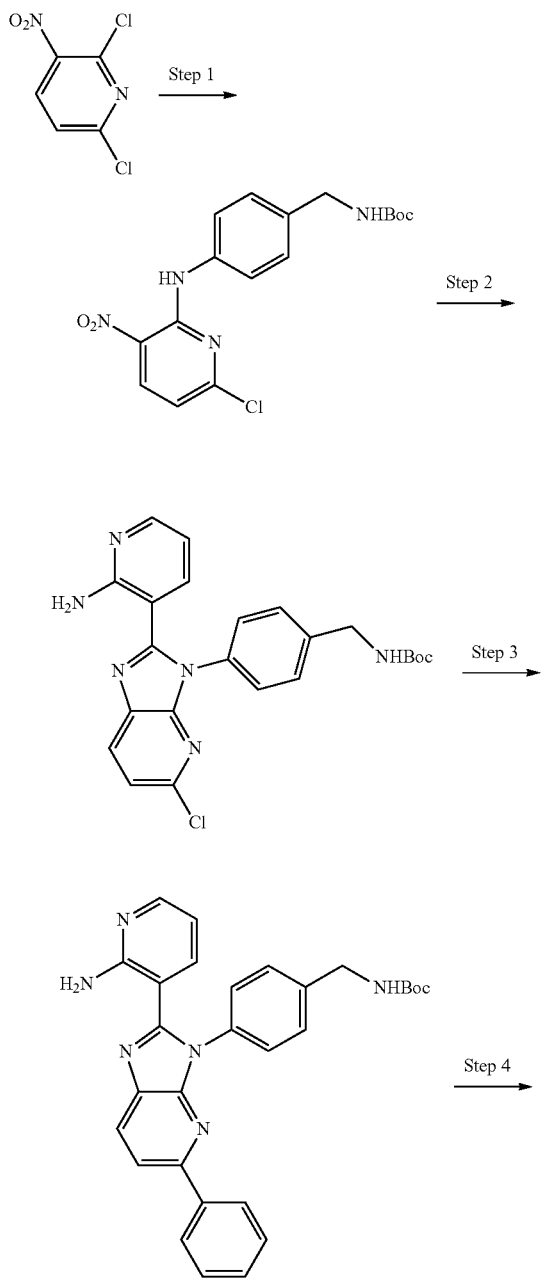

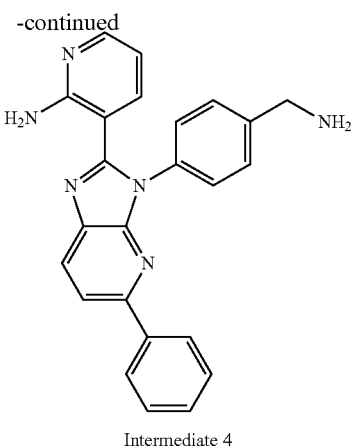

Intermediate 4

Step 1: Tert-butyl 4-((6-chloro-3-nitropyridin-2-yl)amino)benzylcarbamate

To a solution of 2,6-dichloro-3-nitro-pyridine (2.0 g, 10.4 mmol) and tert-butyl N-[(4-aminophenyl)methyl]carbamate (2.3 g, 10.4 mmol) in DMSO (25 mL) was added DIEA (4.0 g, 31.1 mmol). The mixture was stirred at 80° C. for 12 hr. The reaction mixture was quenched with $H_2O$ (50 mL) at 25° C. and extracted with EtOAc (50 mL×3). The combined organic layers were washed with brine (50 mL×2), dried over $Na_2SO_4$, filtered, and concentrated under reduced pressure to give crude product. The crude product was purified by flash chromatography on silica gel (Eluent of 0~10% MeOH in $CH_2Cl_2$) to give tert-butyl N-[[4-[(6-chloro-3-nitro-2-pyridyl)amino]phenyl]methyl]carbamate (2.4 g, yield: 44%) as a red solid. MS: m/z=400.9 [M+Na]$^+$. $^1$H NMR (400 MHz, Dimethylsulfoxide-d$_6$) δ 10.10 (s, 1H), 8.53 (d, J=8.8 Hz, 1H), 7.52 (d, J=8.4 Hz, 2H), 7.40 (t, J=6.0 Hz, 1H), 7.25 (d, J=8.4 Hz, 2H), 6.99 (d, J=8.8 Hz, 1H), 4.13 (d, J=6.0 Hz, 2H), 1.40 (s, 9H).

Step 2: Tert-butyl N-[[4-[2-(2-amino-3-pyridyl)-5-chloro-imidazo[4,5-b]pyridin-3-yl]phenyl]methyl]carbamate To a solution of tert-butyl N-[[4-[(6-chloro-3-nitro-2-pyridyl)amino]phenyl]methyl]carbamate (2.0 g, 5.3 mmol) in DMSO (30 mL) and MeOH (15 mL) was added 2-aminopyridine-3-carbaldehyde (0.7 g, 5.8 mmol) and $Na_2S_2O_4$ (1.8 g, 10.6 mmol). The mixture was stirred at 100° C. for 16 hr. The reaction mixture was quenched with $H_2O$ (50 mL) at 25° C., and extracted with EtOAc (100 mL×3). The combined organic layers were washed with brine (100 mL×2), dried over $Na_2SO_4$, filtered, and concentrated under reduced pressure to give a crude product. The crude product was purified by flash chromatography on silica gel (Eluent of 0~10% MeOH in $CH_2Cl_2$) to give tert-butyl N-[[4-[2-(2-amino-3-pyridyl)-5-chloro-imidazo[4,5-b]pyridin-3-yl]phenyl]methyl]carbamate (1.4 g, yield: 51%) as a yellow solid. MS: m/z=451.0 [M+H]$^+$. $^1$H NMR (400 MHz, Dimethylsulfoxide-d$_6$) δ 8.26 (d, J=8.4 Hz, 1H), 7.99 (dd, J=4.8, 1.6 Hz, 1H), 7.50-7.43 (m, 2H), 7.38 (s, 4H), 7.21 (dd, J=7.6, 1.6 Hz, 1H), 6.91 (br s, 2H), 6.40 (dd, J=7.6, 4.8 Hz, 1H), 4.22 (d, J=6.0 Hz, 2H), 1.41 (s, 9H).

Step 3: Tert-butyl N-[[4-[2-(2-amino-3-pyridyl)-5-phenyl-imidazo[4,5-b]pyridin-3-yl]phenyl]methyl]carbamate To a solution of tert-butyl N-[[4-[2-(2-amino-3-pyridyl)-5-chloro-imidazo[4,5-b]pyridin-3-yl]phenyl]methyl]carbamate (500 mg, 1.1 mmol) and phenylboronic acid (270 mg, 2.2 mmol,) in 1,4-dioxane (5 mL) and $H_2O$ (1 mL) was added Pd(dppf)Cl$_2$ (81.1 mg, 111 μmol) and $Cs_2CO_3$ (1.1 g, 3.3 mmol). The mixture was degassed and purged with $N_2$ three times and then stirred at 80° C. for 16 hr under $N_2$ atmosphere. After cooling to 20° C., the reaction was diluted with 10 mL of EtOAc, and the mixture filtered through celite and extracted with $H_2O$ (10 mL×3), the combined organic layers were washed with brine (15 mL×3), dried over $Na_2SO_4$, filtered and concentrated under reduced pressure to give a residue. The crude product was purified by flash chromatography on silica gel (Eluent of 10~35% EtOAc in petroleum ether) to give tert-butyl N-[[4-[2-(2-amino-3-pyridyl)-5-phenyl-imidazo[4,5-b]pyridin-3-yl]phenyl]methyl]carbamate (126 mg, yield: 21%) as a brown solid. MS: m/z=493.2 [M+H]$^+$.

Step 4: 3-(3-(4-(Aminomethyl)phenyl)-5-phenyl-3H-imidazo[4,5-b]pyridin-2-yl)pyridin-2-amine To a solution of tert-butyl N-[[4-[2-(2-amino-3-pyridyl)-5-phenyl-imidazo[4,5-b]pyridin-3-yl]phenyl]methyl]carbamate (126 mg, 256 μmol) in HCl/1,4-dioxane (4 M, 1 mL). The mixture was stirred at 25° C. for 2 hr. The solvent was removed under reduced pressure to give a crude product (84 mg, yield: 84%). The crude product was purified by prep-HPLC (column: Welch Xtimate C18 150×25 mm×5 μm; mobile phase: [water (HCl)-ACN]; B %: 5%-35%, 8 min) to give the desired product (HCl salt). The product was diluted with aqueous NaHCO$_3$ (10 mL) and extracted with DCM (10 mL×3). The combined organic layers were washed with brine (10 mL), dried over $Na_2SO_4$, filtered, and concentrated under reduced pressure to give 3-(3-(4-(aminomethyl)phenyl)-5-phenyl-3H-imidazo[4,5-b]pyridin-2-yl)pyridin-2-amine (Intermediate 4, 32.2 mg, yield: 84%) as a light-yellow solid. MS: m/z=393.1 [M+H]$^+$. $^1$H NMR (400 MHz, Dimethylsulfoxide-d$_6$) δ 8.26 (d, J=8.4 Hz, 1H), 8.04-7.96 (m, 4H), 7.54-7.49 (m, 2H), 7.49-7.43 (m, 2H), 7.43-7.35 (m, 3H), 7.21 (dd, J=7.6, 1.6 Hz, 1H), 6.98 (br s, 2H), 6.41 (dd, J=7.6, 4.8 Hz, 1H), 3.82 (s, 2H).

Intermediate 5: N-(3-(3-(4-(aminomethyl)phenyl)-2-(2-aminopyridin-3-yl)-3H-imidazo[4,5-b]pyridin-5-yl)phenyl)acetamide

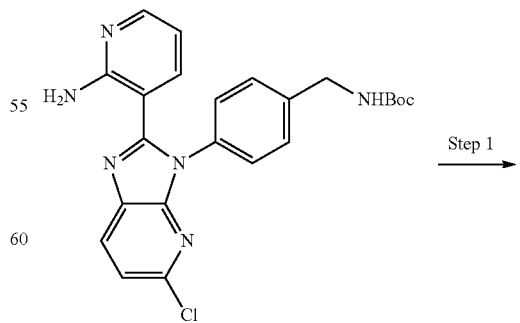

Step 1

-continued

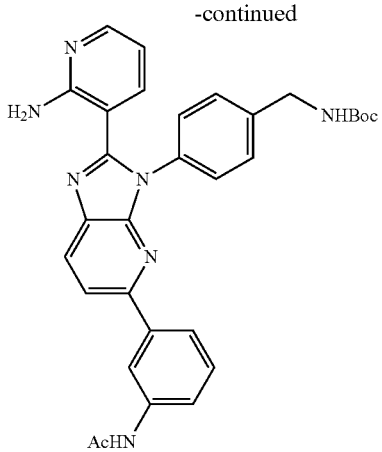

Step 2

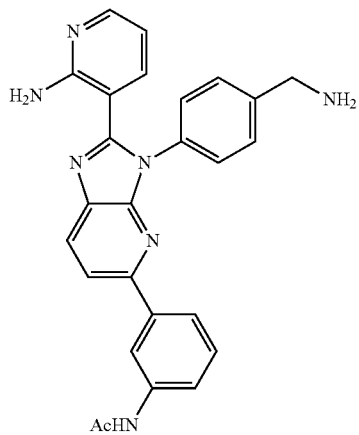

Intermediate 5

Step 1: Tert-butyl 4-(5-(3-acetamidophenyl)-2-(2-aminopyridin-3-yl)-3H-imidazo[4,5-b]pyridin-3-yl)benzylcarbamate To a solution of tert-butyl N-[[4-[2-(2-amino-3-pyridyl)-5-chloro-imidazo[4,5-b]pyridin-3-yl]phenyl]methyl]carbamate (3.5 g, 7.8 mmol) and (3-acetamidophenyl)boronic acid (2.8 g, 15.5 mmol) in 1,4-dioxane (30 mL) and H₂O (6 mL) was added Pd(dppf)Cl₂ (568 mg, 776 μmol) and Cs₂CO₃ (7.6 g, 23.3 mmol). The mixture was degassed and purged with N₂ three times and then stirred at 80° C. for 16 hr under N₂ atmosphere. The reaction mixture was quenched with of H₂O (50 mL) at 25° C. and extracted with EtOAc (50 mL×3). The combined organic layers were washed with brine (50 mL×2), dried over Na₂SO₄, filtered, and concentrated under reduced pressure to give tert-butyl N-[[4-[5-(3-acetamidophenyl)-2-(2-amino-3-pyridyl)imidazo[4,5-b]pyridin-3-yl]phenyl]methyl]carbamate (2.43 g, yield: 57%), which was directly used to the next step without further purification. MS: m/z=550.1 [M+H]⁺.

Step 2: N-(3-(3-(4-(Aminomethyl)phenyl)-2-(2-aminopyridin-3-yl)-3H-imidazo[4,5-b]pyridin-5-yl)phenyl)acetamide To a solution of tert-butyl N-[[4-[5-(3-acetamidophenyl)-2-(2-amino-3-pyridyl)imidazo[4,5-b]pyridin-3-yl]phenyl]methyl]carbamate (8.0 g, 14.6 mmol) in HCV/1,4-dioxane (4 M, 20 mL). The mixture was stirred at 25° C. for 2 hr. Then the solvent was removed under reduced pressure to give a crude product (6.4 g, HCl salt, yield: 90%). 250 mg of the HCl salt was diluted with aqueous NaHCO₃ (10 mL) and extracted with CH₂Cl₂ (10 mL×3). The combined organic layers were washed with brine (10 mL), dried over Na₂SO₄, filtered and concentrated under reduced pressure to give N-(3-(3-(4-(aminomethyl)phenyl)-2-(2-aminopyridin-3-yl)-3H-imidazo[4,5-b]pyridin-5-yl)phenyl)acetamide (Intermediate 5, 86.7 mg, yield: 90%) as a light-yellow solid. MS: m/z=450.0 [M+H]⁺. ¹H NMR (400 MHz, Dimethylsulfoxide-d₆) δ 10.08 (s, 1H), 8.26 (d, J=8.4 Hz, 1H), 8.10 (s, 1H), 8.00 (dd, J=4.8, 1.6 Hz, 1H), 7.84 (d, J=8.4 Hz, 1H), 7.68 (d, J=8.0 Hz, 1H), 7.65 (d, J=8.0 Hz, 1H), 7.53-7.48 (m, 2H), 7.45-7.35 (m, 3H), 7.20 (dd, J=7.6, 1.6 Hz, 1H), 6.94 (br s, 2H), 6.41 (dd, J=7.6, 4.8 Hz, 1H), 3.82 (s, 2H), 2.06 (s, 3H).

Intermediate 6: N-(3-(2-(2-aminopyridin-3-yl)-3-(4-(piperazin-1-ylmethyl)phenyl)-3H-imidazo[4,5-b]pyridin-5-yl)phenyl)acetamide

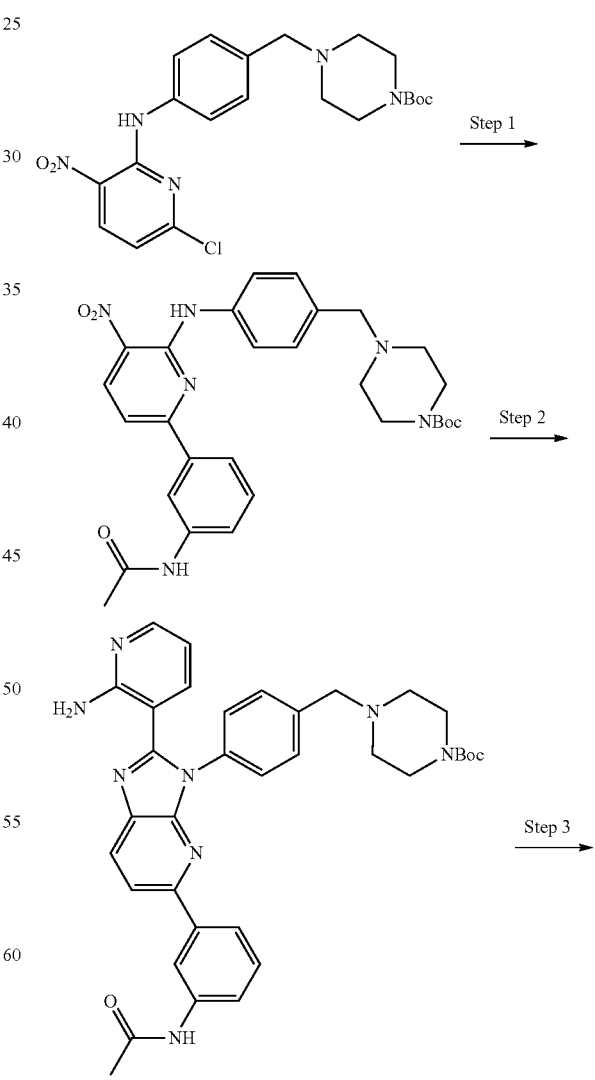

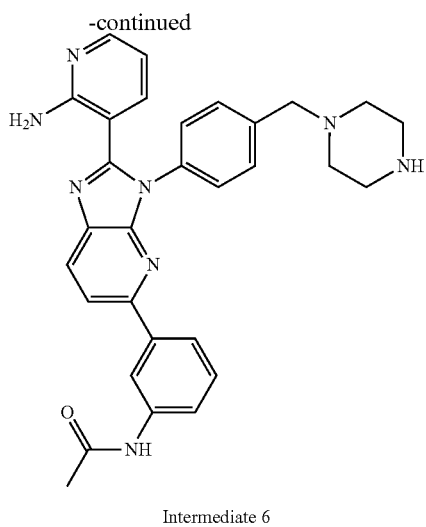

Intermediate 6

Step 1: Tert-butyl 4-(4-((6-(3-Acetamidophenyl)-3-nitropyridin-2-yl)amino)benzyl)piperazine-1-carboxylate To a solution of tert-butyl 4-[[4-[(6-chloro-3-nitro-2-pyridyl)amino]phenyl]methyl]piperazine-1-carboxylate (2.78 g, 5.39 mmol,) and (3-acetamidophenyl)boronic acid (1.93 g, 10.78 mmol) in 1,4-dioxane (30 mL) and H$_2$O (6 mL) was added K$_2$CO$_3$ (2.24 g, 16.2 mmol) and Pd(dppf)Cl$_2$ (789 mg, 1.08 mmol). The mixture was degassed and purged with N$_2$ three times and stirred at 60° C. for 16 hr under N$_2$ atmosphere. The reaction mixture was quenched with H$_2$O (200 mL) at 25° C., and then extracted with CH$_2$Cl$_2$ (60 mL×3). The combined organic layers were washed with brine (100 mL×2), dried over Na$_2$SO$_4$, filtered, and concentrated under reduced pressure to give a residue. The residue was purified by column chromatography (Eluent of 50~100% EtOAc in petroleum ether) to give tert-butyl 4-[[4-[[6-(3-acetamidophenyl)-3-nitro-2-pyridyl]amino]phenyl]methyl]piperazine-1-carboxylate (2.81 g, yield: 83%) as a red solid. MS: m/z=547.1 [M+H]$^+$. $^1$H NMR (400 MHz, Chloroform-d) δ 10.19 (s, 1H), 8.42 (d, J=8.8 Hz, 1H), 8.19 (br s, 1H), 7.68-7.60 (m, 4H), 7.47 (d, J=9.2 Hz, 1H), 7.34-7.27 ((m, 2H), 7.17-7.12 (m, 1H), 3.43 (s, 2H), 3.35 (br t, J=4.8 Hz, 4H), 2.32 (br t, J=4.8 Hz, 4H), 2.11 (s, 3H), 1.36 (s, 9H).

Step 2: Tert-butyl 4-(4-(5-(3-acetamidophenyl)-2-(2-aminopyridin-3-yl)-3H-imidazo[4,5-b]pyridin-3-yl)benzyl)piperazine-1-carboxylate To a solution of 2-aminopyridine-3-carbaldehyde (2.3 g, 18.9 mmol) and tert-butyl 4-[[4-[(6-chloro-3-nitro-2-pyridyl)amino]phenyl]methyl]piperazine-1-carboxylate (9.5 g, 17.2 mmol) in DMSO (100 mL) was added Na$_2$S$_2$O$_4$ (8.97 g, 51.5 mmol). The mixture was degassed and purged with N$_2$ three times and stirred at 60° C. for 16 hr under N$_2$ atmosphere. The reaction mixture was quenched with H$_2$O (400 mL) at 25° C., and then extracted with CH$_2$Cl$_2$ (400 mL×2). The combined organic layers were washed with brine (300 mL×2), dried over Na$_2$SO$_4$, filtered, and concentrated under reduced pressure to give tert-butyl 4-[[4-[5-(3-acetamidophenyl)-2-(2-amino-3-pyridyl)imidazo[4,5-b]pyridin-3-yl]phenyl]methyl]piperazine-1-carboxylate (9.67 g, crude) as a red solid, which was direct used to the next step without further purification. MS: m/z=619.2 [M+H]$^+$.

Step 3: N-(3-(2-(2-aminopyridin-3-yl)-3-(4-(piperazin-1-ylmethyl)phenyl)-3H-imidazo[4,5-b]pyridin-5-yl)phenyl)acetamide To a solution of tert-butyl 4-[[4-[5-(3-acetamidophenyl)-2-(2-amino-3-pyridyl)imidazo[4,5-b]pyridin-3-yl]phenyl]methyl]piperazine-1-carboxylate (0.4 g, 370 μmol, crude) in HCl/1,4-dioxane (4M, 5 mL) and 1,4-dioxane (1 mL). The mixture was degassed and purged with N$_2$ three times and stirred at 25° C. for 4 hr under N$_2$ atmosphere. The reaction mixture was filtered and the filtered cake was washed with 1,4-dioxane (10 mL×2) and then concentrated under reduced pressure to give a residue. The residue was purified by prep-HPLC (column: Phenomenex Luna C18 200*40 mm*10 um; mobile phase: [water (HCl)-ACN]; B %: 1%-30%, 10 min) to give N-(3-(2-(2-aminopyridin-3-yl)-3-(4-(piperazin-1-ylmethyl)phenyl)-3H-imidazo[4,5-b]pyridin-5-yl)phenyl)acetamide (Intermediate 6, 244 mg HCl salt, yield: 68%) as a yellow solid. MS: m/z=519.2 [M+H]$^+$. $^1$H NMR (400 MHz, Dimethylsulfoxide-d$_6$) δ 10.05 (s, 1H), 8.27 (d, J=8.4 Hz, 1H), 8.15 (s, 1H), 7.99 (dd, J=4.8, 1.6 Hz, 1H), 7.86 (d, J=8.4 Hz, 1H), 7.66 (d, J=8.0 Hz, 2H), 7.50-7.33 (m, 5H), 7.14 (dd, J=7.6, 1.2 Hz, 1H), 7.00 (br s, 2H), 6.37 (dd, J=7.6, 4.8 Hz, 1H), 3.52 (s, 2H), 2.77-2.67 (m, 4H), 2.41-2.27 (m, 4H), 2.05 (s, 3H).

Intermediate 7: 3-[3-[4-(aminomethyl)phenyl]-6-phenyl-imidazo[4,5-b]pyridin-2-yl]pyridin-2-amine

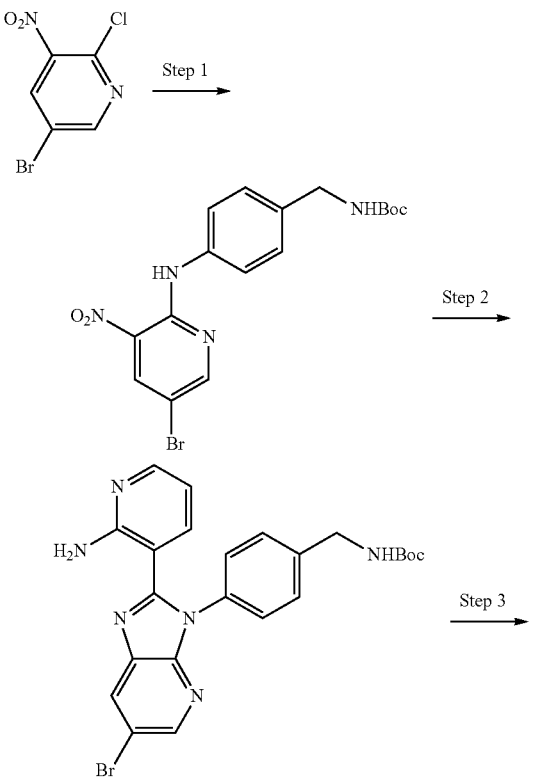

-continued

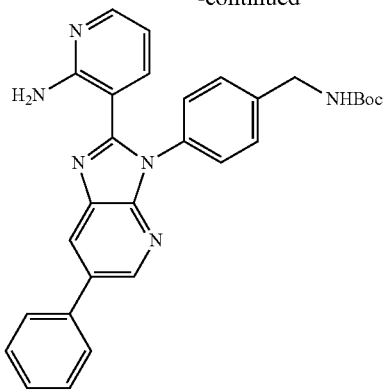

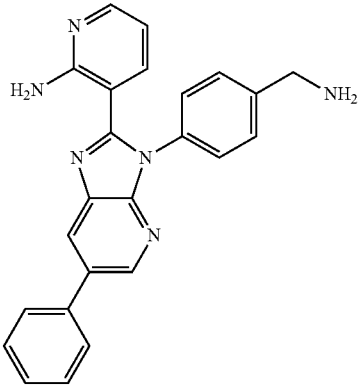

Intermediate 7

Step 1: Tert-butyl N-[[4-[(5-bromo-3-nitro-2-pyridyl)amino]phenyl]methyl]carbamate To a solution of 5-bromo-2-chloro-3-nitro-pyridine (2.1 g, 9.0 mmol) and tert-butyl N-[(4-aminophenyl)methyl]carbamate (2 g, 9.0 mmol) in DMSO (20 mL) was added DIEA (3.5 g, 27.0 mmol). The mixture was stirred at 80° C. for 12 hr. After cooling to 20° C., $H_2O$ (50 mL) was added to the reaction mixture, then extracted with EtOAc (50 mL×2). The combined organic layers were washed with brine (50 mL×2), dried over $Na_2SO_4$, filtered, and concentrated under reduced pressure to give tert-butyl N-[[4-[(5-bromo-3-nitro-2-pyridyl)amino]phenyl]methyl]carbamate (3.5 g crude, yield: 92%) as a red solid. MS: m/z=367.6, 368.6 $[M+H]^+$. $^1$H NMR (400 MHz, Chloroform-d)) δ 10.02 (s, 1H), 8.65 (d, J=2.0 Hz, 1H), 8.49 (d, J=2.0 Hz, 1H), 7.55 (d, J=8.4 Hz, 2H), 7.32 (d, J=8.0 Hz, 2H), 4.84 (br s, 1H), 4.32 (d, J=5.2 Hz, 2H), 1.47 (s, 9H).

Step 2: Tert-butyl N-[[4-[2-(2-amino-3-pyridyl)-6-bromo-imidazo[4,5-b]pyridin-3-yl]phenyl]methyl]carbamate To a solution of tert-butyl N-[[4-[(5-bromo-3-nitro-2-pyridyl)amino]phenyl]methyl]carbamate (3 g, 7.1 mmol) and 2-aminopyridine-3-carbaldehyde (952 mg, 7.8 mmol) in DMSO (30 mL) and MeOH (15 mL) was added $Na_2S_2O_4$ (2.5 g, 14.2 mmol). The mixture was stirred at 100° C. for 12 hr. After cooling to 20° C., $H_2O$ (50 mL) was added to the reaction mixture, then the resulting mixture extracted with EtOAc (50 mL×2). The combined organic layers were washed with brine (50 mL×2), dried over $Na_2SO_4$, filtered and concentrated under reduced pressure to give a residue. The residue was purified by column chromatography (Eluent of 0~1% MeOH in $CH_2Cl_2$) to give tert-butyl-N-[[4-[2-(2-amino-3-pyridyl)-6-bromo-imidazo[4,5-b]pyridin-3-yl]phenyl]methyl]carbamate (1.7 g, yield: 36%) as a yellow solid. MS: m/z=495.9, 496.9 $[M+H]^+$. $^1$H NMR (400 MHz, Chloroform-d)) δ8.40 (d, J=2.0 Hz, 1H), 8.22 (d, J=2.0 Hz, 1H), 8.08 (dd, J=4.8, 2.0 Hz, 1H), 7.46 (d, J=8.4 Hz, 2H), 7.33 (d, J=8.4 Hz, 2H), 7.10 (dd, J=8.0, 2.0 Hz, 1H), 6.63 (br s, 2H), 6.41-6.34 (m, 1H), 4.93 (br s, 1H), 4.42 (d, J=5.6 Hz, 2H), 1.48 (s, 9H).

Step 3: Tert-butyl N-[[4-[2-(2-amino-3-pyridyl)-6-phenyl-imidazo[4,5-b]pyridin-3-yl]phenyl]methyl]carbamate To a solution of tert-butyl N-[[4-[2-(2-amino-3-pyridyl)-6-bromo-imidazo[4,5-b]pyridin-3-yl]phenyl]methyl]carbamate (500 mg, 1.0 mmol) and phenylboronic acid (246 mg, 2.0 mmol) in toluene (5 mL) and EtOH (5 mL) was added $NaHCO_3$ (254 mg, 3.0 mmol) and $Pd(PPh_3)_4$ (233 mg, 202 μmol). The mixture degassed and purged with $N_2$ three times, and then the mixture was stirred at 100° C. for 12 hr under $N_2$ atmosphere. After cooling to 20° C., $H_2O$ (20 mL) was added to the reaction mixture, then extracted with EtOAc (20 mL×2). The combined organic layers were washed with saturated $NaHCO_3$ solution (20 mL×2), dried over $Na_2SO_4$, filtered, and concentrated under reduced pressure to give a residue. The residue was purified by silica gel flash chromatography (Eluent of 0~1% MeOH in $CH_2Cl_2$) to give tert-butyl N-[[4-[2-(2-amino-3-pyridyl)-6-phenyl-imidazo[4,5-b]pyridin-3-yl]phenyl]methyl]carbamate (340 mg, 62% yield) as a brown solid. MS: m/z=493.1 $[M+H]^+$. $^1$H NMR (400 MHz, Dimethylsulfoxide-$d_6$)) δ 8.61 (d, J=2.0 Hz, 1H), 8.45 (d, J=2.0 Hz, 1H), 8.01-7.99 (m, 1H), 7.77 (d, J=7.2 Hz, 2H), 7.63-7.59 (m, 4H), 7.54-7.52 (m, 2H), 7.39 (d, J=5.2 Hz, 2H), 7.23 (dd, J=7.6, 2.0 Hz, 1H), 7.04 (br s, 2H), 6.40 (dd, J=7.6, 5.2 Hz, 1H), 4.21 (d, J=6.0 Hz, 2H), 1.40 (s, 9H).

Step 4: 3-[3-[4-(aminomethyl)phenyl]-6-phenyl-imidazo[4,5-b]pyridin-2-yl]pyridin-2-amine To a solution of tert-butyl N-[[4-[2-(2-amino-3-pyridyl)-6-phenyl-imidazo[4,5-b]pyridin-3-yl]phenyl]methyl]carbamate (340 mg, 690 μmol, 1.0 eq) in 1,4-dioxane (5 mL) was added HCl/dioxane (5 mL). The mixture was stirred at 25° C. for 1 hr. The reaction mixture was concentrated under reduced pressure to give the crude product (297 mg, HCl salt, yield: 96%). The residue was purified by prep-HPLC (column: Welch Xtimate $C_{18}$ 150×25 mm×5 μm; mobile phase: [water (HCl)-ACN]; B %: 3%-33%, 8 min) and dissociated with $NaHCO_3$ to give 3-[3-[4-(aminomethyl)phenyl]-6-phenyl-imidazo[4,5-b]pyridin-2-yl]pyridin-2-amine (Intermediate 7, 83.8 mg, yield: 96%) as an off-white solid. MS: m/z=393.1 $[M+H]^+$. $^1$H NMR (400 MHz, Dimethylsulfoxide-$d_6$)) δ 8.62 (d, J=2.0 Hz, 1H), 8.46 (d, J=2.0 Hz, 1H), 8.00 (dd, J=4.8, 2.0 Hz, 1H), 7.78 (d, J=7.2 Hz, 2H), 7.56-7.46 (m, 5H), 7.45-7.35 (m, 4H), 7.26 (dd, J=8.0, 2.0 Hz, 1H), 7.04 (s, 2H), 6.44-6.39 (m, 1H), 3.80 (s, 2H).

Intermediate 8: 3-(6-Phenyl-3-(4-(piperazin-1-ylmethyl)phenyl)-3H-imidazo[4,5-b]pyridin-2-yl)pyridin-2-amine

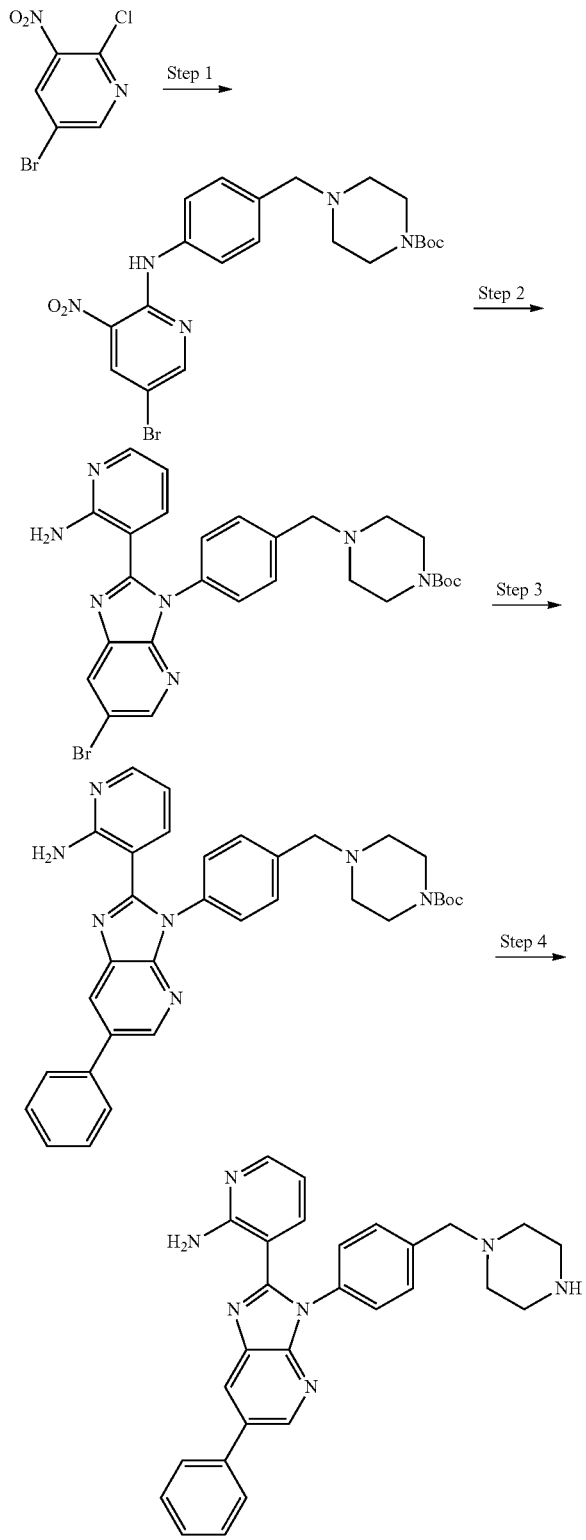

Intermediate 8

Step 1: Tert-butyl 4-(4-((5-bromo-3-nitropyridin-2-yl)amino)benzyl)piperazine-1-carboxylate To a solution of 5-bromo-2-chloro-3-nitro-pyridine (10 g, 42.1 mmol) in DMSO (100 mL) was added tert-butyl 4-[(4-aminophenyl)methyl]piperazine-1-carboxylate (11 g, 30.2 mmol) and DIEA (11.7 g, 94.8 mmol). The mixture was stirred at 80° C. for 12 hr. After cooling to 20° C., the reaction mixture was poured into $H_2O$ (100 mL). The aqueous layer was extracted with EtOAc (200 mL×3). The combined organic layers were washed with brine (200 mL×3). The combined organic layers were dried over anhydrous $Na_2SO_4$, filtered, and concentrated to dryness. The crude product was purified by flash chromatography on silica gel (Elute of 10-50% EtOAc in petroleum ether) to give tert-butyl 4-[[4-[(5-bromo-3-nitro-2-pyridyl)amino]phenyl]methyl]piperazine-1-carboxylate (10.7 g, yield: 43%) as a brown solid. MS: m/z=493.8 [M+H]-$^1$H NMR (400 MHz, Dimethylsulfoxide-$d_6$) δ 9.93 (s, 1H), 8.67 (d, J=2.4 Hz, 1H), 8.60 (d, J=2.4 Hz, 1H), 8.50 (dd, J=10.0, 2.4 Hz, 1H), 7.54 (d, J=8.4 Hz, 2H), 7.29 (d, J=8.0 Hz, 1H), 3.46 (s, 2H), 3.32-3.28 (m, 4H), 2.32-2.30 (m, 4H), 1.39 (s, 9H)

Step 2: Tert-butyl 4-(4-(2-(2-aminopyridin-3-yl)-6-bromo-3H-imidazo[4,5-b]pyridin-3-yl)benzyl)piperazine-1-carboxylate To a solution of tert-butyl 4-[[4-[(5-bromo-3-nitro-2-pyridyl)amino]phenyl]methyl]piperazine-1-carboxylate (10.7 g, 21.6 mmol) in DMSO (60 mL) and methanol (30 mL) was added 2-aminopyridine-3-carbaldehyde (3.2 g, 26 mmol) and $Na_2S_2O_4$ (7.5 g, 43.3 mmol). Then the reaction mixture was stirred at 100° C. for 16 hr. After cooling to 25° C., the reaction mixture was diluted with $H_2O$ (100 mL) and extracted with $CH_2Cl_2$ (100 mL×3) and brine (100 mL×2 times). The organic phase was separated and dried over $Na_2SO_4$, filtered, and concentrated under reduced pressure to give a residue. The crude product tert-butyl 4-[[4-[2-(2-amino-3-pyridyl)-6-bromo-imidazo[4,5-b]pyridin-3-yl]phenyl]methyl]piperazine-1-carboxylate (7.6 g, yield: 62%) was obtained as a red oil. MS: m/z=565.9 [M+H]$^+$.

Step 3: Tert-butyl 4-(4-(2-(2-aminopyridin-3-yl)-6-phenyl-3H-imidazo[4,5-b]pyridin-3-yl)benzyl)piperazine-1-carboxylate To a solution of tert-butyl 4-[[4-[2-(2-amino-3-pyridyl)-6-bromo-imidazo[4,5-b]pyridin-3-yl]phenyl]methyl]piperazine-1-carboxylate (5.8 g, 10.3 mmol) and phenylboronic acid (2.5 g, 20.6 mmol) in 1,4-dioxane (100 mL) and $H_2O$ (10 mL) was added Pd(dppf)$Cl_2$ (752 mg, 1.03 mmol) and $Cs_2CO_3$ (10 g, 30.8 mmol). The mixture was degassed and purged with $N_2$ three times, and then the mixture was stirred at 80° C. for 16 hr under $N_2$ atmosphere. After cooling to 25° C., the reaction mixture was poured into $H_2O$ (100 mL). The aqueous layer was extracted with EtOAc (100 mL×3). The combined organic layers were washed with brine (100 mL×3). The combined organic layers were dried over anhydrous $Na_2SO_4$, filtered, and concentrated to dryness. The crude product tert-butyl 4-[[4-[2-(2-amino-3-pyridyl)-6-phenyl-imidazo[4,5-b]pyridin-3-yl]phenyl]methyl]piperazine-1-carboxylate (2.54 g, yield: 44%) as a brown oil. MS: m/z=562.4 [M+H]$^+$.

Step 4: 3-(6-Phenyl-3-(4-(piperazin-1-ylmethyl)phenyl)-3H-imidazo[4,5-b]pyridin-2-yl)pyridin-2-amine A solution of tert-butyl 4-[[4-[2-(2-amino-3-pyridyl)-6-phenyl-imidazo[4,5-b]pyridin-3-yl]phenyl]methyl]piperazine-1-carboxylate (10 g, 17.80 mmol, 1 eq) in HCl/1,4-dioxane (4M, 100 mL) was stirred at 25° C. for 1 hr. The reaction mixture was filtered and concentrated under reduced pressure to give the crude product. The crude product was triturated with MeOH (30 mL) at 25° C. for 30 min. The suspension was filtered, the filter cake washed with MeOH (20 mL) and concentrated under reduced pressure to give 3-[6-phenyl-3-[4-(piperazin-1-ylmethyl)phenyl]imidazo[4,5-b]pyridin-2-yl]pyridin-2-amine (Intermediate 8, 3.7 g, yield: 42%) as a yellow solid. MS: m/z=462.2 [M+H]$^+$. $^1$H NMR (400 MHz, Dimethylsulfoxide-d$_6$) δ 8.63 (d, J=2.0 Hz, 1H), 8.46 (d, J=2.0 Hz, 1H), 8.00 (dd, J=4.8, 1.6 Hz, 1H), 7.81-7.75 (m, 2H), 7.52 (dd, J=7.6, 7.6 Hz, 2H), 7.47-7.38 (m, 5H), 7.19 (dd, J=7.6, 1.6 Hz, 1H), 7.06 (br s, 2H), 6.39 (dd, J=7.6, 4.8 Hz, 1H), 3.51 (s, 2H), 3.33-3.27 (m, 1H), 2.71 (br t, J=4.4 Hz, 4H), 2.32 (s, 4H).

Intermediate 9: 3-[3-[4-[(4-Amino-1-piperidyl)methyl]phenyl]-6-phenyl-imidazo[4,5-b]pyridin-2-yl]pyridin-2-amine

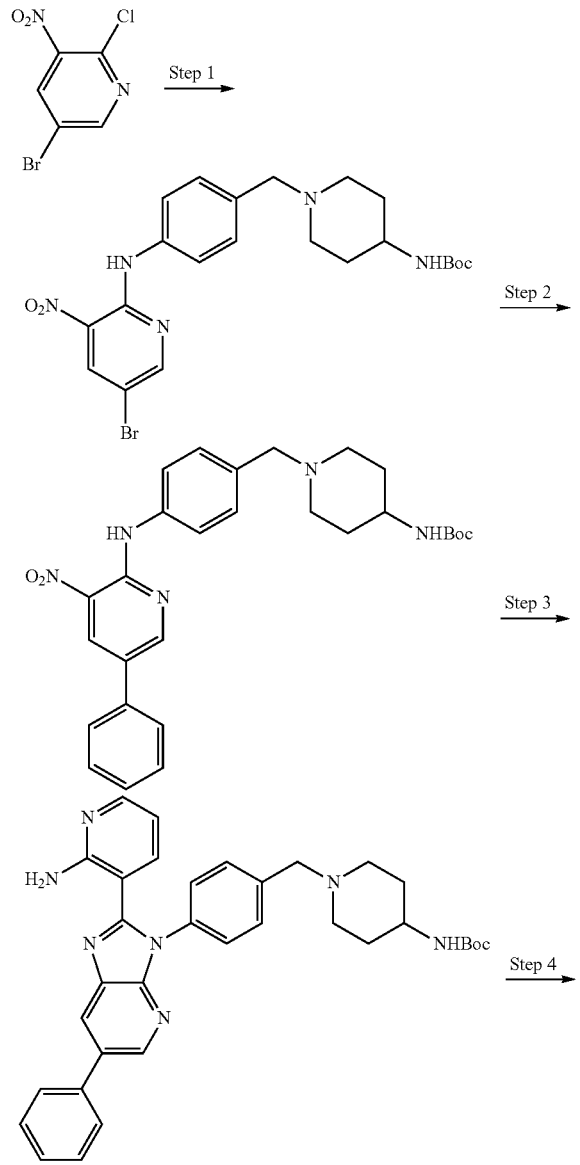

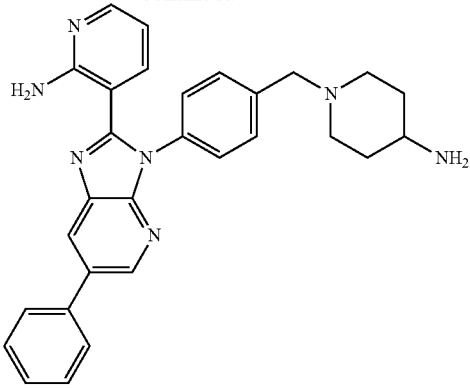

Intermediate 9

Step 1: Tert-butyl N-[1-[[4-[(5-bromo-3-nitro-2-pyridyl)amino]phenyl]methyl]-4-piperidyl]carbamate A mixture of 5-bromo-2-chloro-3-nitro-pyridine (17.1 g, 72 mmol), tert-butyl N-[1-[(4-aminophenyl)methyl]-4-piperidyl]carbamate (22 g, 72 mmol), DIEA (27.9 g, 216 mmol) in DMSO (200 mL) was stirred at 80° C. for 16 hr. After cooling to 25° C., the mixture was extracted with EtOAc (250 mL×3). The combined organic layers were washed with brine (200 mL×2), dried over anhydrous Na$_2$SO$_4$, filtered, and concentrated to give tert-butyl N-[1-[[4-[(5-bromo-3-nitro-2-pyridyl)amino]phenyl]methyl]-4-piperidyl]carbamate crude product as black brown solid (32 g). MS: m/z=506.9, 507.9 [M+H]$^+$. $^1$H NMR (400 MHz, Chloroform-d) δ 10.04 (s, 1H), 8.64 (d, J=2.0 Hz, 1H), 8.49 (d, J=2.4 Hz, 1H), 7.53 (d, J=8.4 Hz, 2H), 7.33 (d, J=8.4 Hz, 2H), 4.34 (d, J=3.2 Hz, 1H), 3.48 (s, 2H), 3.46-3.35 (m, 1H), 2.82 (br d, J=12.0 Hz, 2H), 2.10 (t, J=10.8 Hz, 2H), 1.91 (br d, J=11.2 Hz, 2H), 1.44 (s, 9H).

Step 2: Tert-butyl N-[1-[[4-[(3-nitro-5-phenyl-2-pyridyl)amino]phenyl]methyl]-4-piperidyl]carbamate A mixture of tert-butyl N-[1-[[4-[(5-bromo-3-nitro-2-pyridyl)amino]phenyl]methyl]-4-piperidyl]carbamate (20 g, 39.5 mmol), phenylboronic acid (4.8 g, 39.5 mmol), K$_2$CO$_3$ (16.4 g, 118.5 mmol), Pd(dppf)Cl$_2$ (1.4 g, 2.0 mmol) in 1,4-dioxane (250 mL) and H$_2$O (50 mL) was degassed and purged with N$_2$ three times, and then the mixture was stirred at 80° C. for 16 hr under N$_2$ atmosphere. After cooling to 25° C., the reaction mixture was filtered, then to the liquid added H$_2$O (100 mL) and EtOAc (450 mL). The organic phase was separated, washed with brine (100 mL×3), dried over Na$_2$SO$_4$, filtered, and concentrated under reduced pressure to give the residue. The residue was purified by silica gel flash chromatography (Eluent of 3~4% MeOH in CH$_2$Cl$_2$) to give tert-butyl-[1-[[4-[(3-nitro-5-phenyl-2-pyridyl)amino]phenyl]methyl]-4-piperidyl]carbamate (8.6 g, yield: 43%) as a red brown solid. MS: m/z=504.2 [M+H]$^+$. $^1$H NMR (400 MHz, Chloroform-d) δ 10.14 (s, 1H), 8.75 (dd, J=10.0, 2.0 Hz, 2H), 7.62 (d, J=8.0, Hz, 2H), 7.57 (d, J=7.2, Hz, 2H), 7.49 (dd, J=8.0, 8.0 Hz, 2H), 7.43-7.37 (m, 3H), 4.43 (br s, 1H), 3.50 (br s, 2H), 3.49-3.41 (m, 1H), 2.85-2.81 (m, 2H), 2.15-2.08 (m, 2H), 1.94-1.91 (m, 2H), 1.51-1.45 (m, 2H), 1.44 (s, 9H).

Step 3: Tert-butyl N-[1-[[4-[2-(2-amino-3-pyridyl)-6-phenyl-imidazo[4,5-b]pyridin-3-yl]phenyl]methyl]-4-piperidyl]carbamate A mixture of tert-butyl N-[1-[[4-[(3-nitro-5-phenyl-2-pyridyl)amino]phenyl]methyl]-4-piperidyl]carbamate (2.2 g, 4.4 mmol), 2-aminopyridine-3-carbaldehyde (694 mg, 5.7 mmol), $Na_2S_2O_4$ (1.5 g, 8.7 mmol) in DMSO (100 mL) was degassed and purged with $N_2$ three times, and then the mixture was stirred at 100° C. for 16 hr under $N_2$ atmosphere. After cooling to 25° C., the reaction mixture was filtered, then to the liquid added $H_2O$ (30 mL) and EtOAc (45 mL). The organic phase was separated, washed with brine (10 mL×3), dried over $Na_2SO_4$, filtered and concentrated under reduced pressure to give the residue. The residue was purified by silica gel flash chromatography (Eluent of 5~6% EtOAc in petroleum ether) to give tert-butyl N-[1-[[4-[2-(2-amino-3-pyridyl)-6-phenyl-imidazo[4,5-b]pyridin-3-yl]phenyl]methyl]-4-piperidyl]carbamate (700 mg, yield: 28%) as a black brown solid. MS: m/z=576.2 [M+H]$^+$. $^1$H NMR (400 MHz, Chloroform-d) δ 8.63 (d, J=2.0 Hz, 1H), 8.27 (d, J=2.0 Hz, 1H), 8.07 (dd, J=5.2, 2.0 Hz, 1H), 7.67-7.62 (m, 2H), 7.54-7.47 (m, 4H), 7.44-7.39 (m, 1H), 7.36 (d, J=8.4 Hz, 2H), 7.09 (dd, J=8.0, 2.0 Hz, 1H), 6.65 (br s, 2H), 6.35 (dd, J=8.0, 4.8 Hz, 1H), 4.45 (br s, 1H), 3.58 (s, 2H), 3.55-3.46 (m, 1H), 2.92-2.77 (m, 2H), 2.16 (br t, J=10 Hz, 2H), 1.95 (br d, J=11.2 Hz, 2H), 1.63-1.56 (m, 2H), 1.45 (s, 9H).

Step 4: 3-[3-[4-[(4-Amino-1-piperidyl)methyl]phenyl]-6-phenyl-imidazo[4,5-b]pyridin-2-yl]pyridin-2-amine A mixture of tert-butyl N-[1-[[4-[2-(2-amino-3-pyridyl)-6-phenyl-imidazo[4,5-b]pyridin-3-yl]phenyl]methyl]-4-piperidyl]carbamate (2.4 g, 4.17 mmol) in HCl/1,4-dioxane (4M, 20 mL) and MeOH (4 mL) was stirred at 25° C. for 2 hr. The reaction mixture was filtered to give residue (2 g HCl salt, yield: 94.3%). 100 mg of the residue was purified by prep-HPLC (column: Welch Ultimate C18 150×25 mm×5 um; mobile phase: [water (FA)-ACN]; B %: 0% to 25%, 10 min) to give 3-[3-[4-[(4-amino-1-piperidyl)methyl]phenyl]-6-phenyl-imidazo[4,5-b]pyridin-2-yl]pyridin-2-amine (Intermediate 9, 26.6 mg, 2HCOOH salt, yield: 94%) as a yellow solid. MS: m/z=476.1 [M+H]$^+$. $^1$H NMR (400 MHz, Dimethylsulfoxide-d$_6$) δ 8.63 (d, J=2.0 Hz, 1H), 8.47 (d, J=2.0 Hz, 1H), 8.34 (s, 2H), 8.00 (dd, J=4.8, 1.6 Hz, 1H), 7.78 (d, J=7.6 Hz, 2H), 7.53 (dd, J=7.6, 7.6 Hz, 2H), 7.47-7.39 (m, 5H), 7.20 (dd, J=7.6, 1.6 Hz, 1H), 7.04 (br s, 2H), 6.39 (dd, J=7.6, 4.8 Hz, 1H), 3.55 (s, 2H), 2.98-2.88 (m, 1H), 2.87-2.80 (m, 2H), 2.09-1.97 (m, 2H), 1.90-1.80 (m, 2H), 1.57-1.44 (m, 2H).

Intermediate 10: 3-[5-Phenyl-3-[4-(piperazin-1-ylmethyl)phenyl]imidazo[4,5-b]pyridin-2-yl]pyridin-2-amine

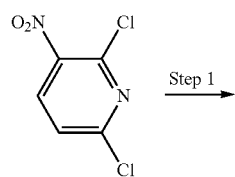

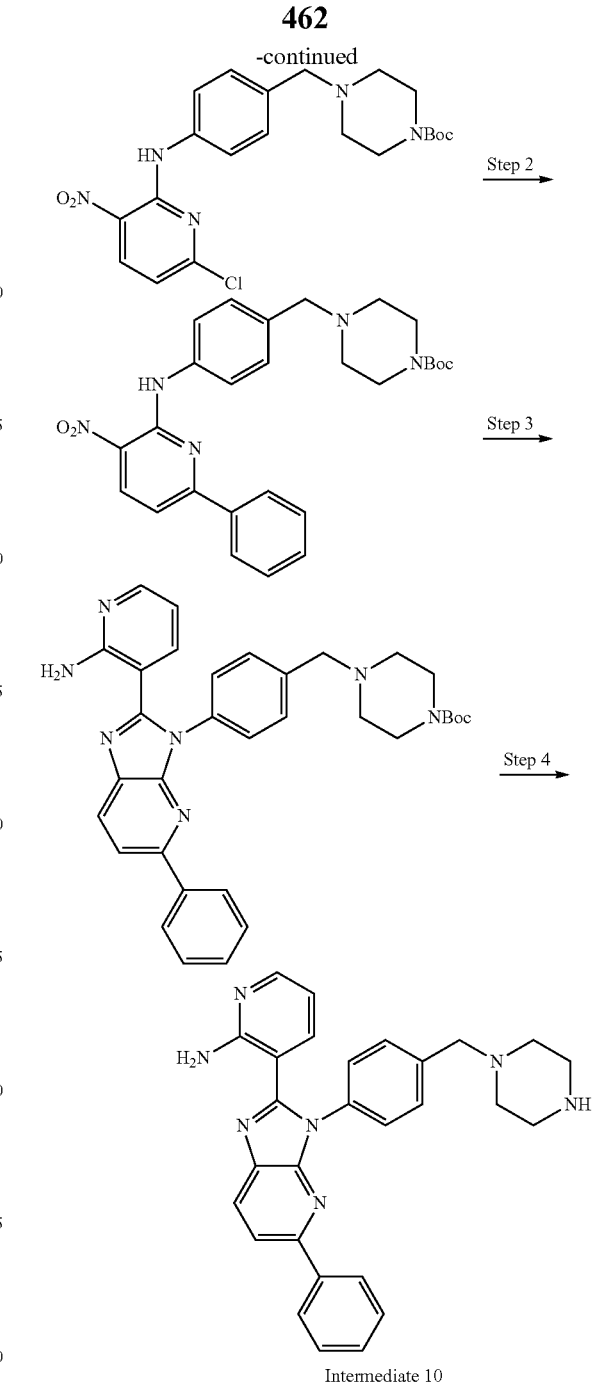

Intermediate 10

Step 1: Tert-butyl 4-[[4-[(6-chloro-3-nitro-2-pyridyl)amino]phenyl]methyl]piperazine-1-carboxylate To a solution of 2,6-dichloro-3-nitro-pyridine (5.0 g, 25.9 mmol) in 1,4-dioxane (50 mL) was added DIEA (6.7 g, 51.8 mmol) and tert-butyl 4-[(4-aminophenyl)methyl]piperazine-1-carboxylate (10.8 g, 25.9 mmol). The mixture was stirred at 60° C. for 12 hr. The reaction mixture was diluted 50 mL of $H_2O$, and the aqueous phase extracted with EtOAc (100 mL×3). The combined organic layers were washed with brine (50 mL×2), dried over $Na_2SO_4$, filtered, and concentrated under reduced pressure to give a residue. The residue was purified by silica gel flash chromatography (Eluent of 0~50% EtOAc in petroleum ether) to give tert-butyl 4-[[4-[(6-chloro-3-nitro-2-pyridyl)amino]phenyl]methyl]piperazine-1-carboxylate (6.1 g, yield: 53%) as a yellow solid. MS: m/z=447.9 [M+H]$^+$. $^1$H NMR (400 MHz, Chloroform-d) δ 10.27 (s, 1H), 8.46 (d, J=8.8 Hz, 1H), 7.61 (d, J=8.4 Hz, 2H), 7.36 (d, J=8.4 Hz, 2H), 6.80 (d, J=8.4 Hz, 1H), 3.52 (s, 2H), 3.48-3.37 (m, 4H), 2.45-2.32 ((m, 4H), 1.46 (s, 9H).

Step 2: Tert-butyl 4-[[4-[(3-nitro-6-phenyl-2-pyridyl)amino]phenyl]methyl]piperazine-1-carboxylate To a solution of tert-butyl 4-[[4-[(6-chloro-3-nitro-2-pyridyl)amino]phenyl]methyl]piperazine-1-carboxylate (1.0 g, 2.23 mmol) and phenylboronic acid (544 mg, 4.47 mmol) in 1,4-dioxane (10 mL) and H$_2$O (2 mL) was added Pd(dppf)Cl$_2$ (327 mg, 0.446 mmol) and K$_2$CO$_3$ (926 mg, 6.7 mmol). The mixture was stirred at 60° C. for 4 hr. The reaction mixture was added with 50 mL of H$_2$O, and the aqueous phase extracted with EtOAc (100 mL×3). The combined organic layers were washed with brine (50 mL×2), dried over Na$_2$SO$_4$, filtered, and concentrated under reduced pressure to give a residue. The residue was purified by silica gel flash chromatography (Eluent of 0~50% EtOAc in petroleum ether) to give tert-butyl 4-[[4-[(3-nitro-6-phenyl-2-pyridyl)amino]phenyl]methyl]piperazine-1-carboxylate (1.0 g, yield: 92%) as a red solid. MS: m/z=490.1 [M+H]$^+$. $^1$H NMR (400 MHz, Chloroform-d) δ 10.31 (s, 1H), 8.59 (d, J=8.8 Hz, 1H), 8.06-8.04 (m, 2H), 7.73 (d, J=8.4 Hz, 2H), 7.52-7.44 (m, 3H), 7.37 (d, J=8.4 Hz, 2H), 7.3 (d, J=8.4 Hz, 1H), 3.54 (s, 2H), 3.52-3.37 (m, 4H), 2.49-2.37 (m, 4H), 1.46 (s, 9H).

Step 3: Tert-butyl 4-[[4-[2-(2-amino-3-pyridyl)-5-phenyl-imidazo[4,5-b]pyridin-3-yl]phenyl]methyl]piperazine-1-carboxylate To a solution of 2-aminopyridine-3-carbaldehyde (269 mg, 2.21 mmol) and tert-butyl 4-[[4-[(3-nitro-6-phenyl-2-pyridyl)amino]phenyl]methyl]piperazine-1-carboxylate (900 mg, 1.84 mmol) in DMSO (10 mL) was added Na$_2$S$_2$O$_4$ (960 mg, 5.52 mmol) at 15° C. The mixture was stirred at 100° C. for 20 hr. The reaction mixture was diluted with H$_2$O (50 mL), and the aqueous phase extracted with DCM (80 mL×3). The combined organic layers were washed with brine (80 mL×3), dried over Na$_2$SO$_4$, filtered, and concentrated under reduced pressure to give a residue. The residue was purified by silica gel flash chromatography (Eluent of 0~10% MeOH in CH$_2$Cl$_2$) to give tert-butyl 4-[[4-[2-(2-amino-3-pyridyl)-5-phenyl-imidazo[4,5-b]pyridin-3-yl]phenyl]methyl]piperazine-1-carboxylate (600 mg, yield: 58%) as a yellow solid. MS: m/z=562.1 [M+H]$^+$. $^1$H NMR (400 MHz, Chloroform-d) δ 8.13 (d, J=8.4 Hz, 1H), 8.06 (dd, J=5.2, 2.0 Hz, 1H), 8.03-8.01 (m, 2H), 7.81 (d, J=8.4 Hz, 1H), 7.51-7.49 (m, 2H), 7.48-7.35 (m, 5H), 7.10 (dd, J=9.6, 2.0 Hz, 1H), 6.66 (br s, 2H), 6.36 (dd, J=8.0, 4.0 Hz, 1H), 3.64 (s, 2H), 3.53-3.42 (m, 4H), 2.55-2.42 (m, 4H), 1.47 (s, 9H).

Step 4: 3-[5-Phenyl-3-[4-(piperazin-1-ylmethyl)phenyl]imidazo[4,5-b]pyridin-2-yl]pyridin-2-amine A solution of tert-butyl 4-[[4-[2-(2-amino-3-pyridyl)-5-phenyl-imidazo[4,5-b]pyridin-3-yl]phenyl]methyl]piperazine-1-carboxylate (400 mg, 712 μmol) in HCl/1,4-dioxane (4M, 8 mL) was stirred at 25° C. for 4 hr. The reaction was filtered and concentrated under reduced pressure to give 3-[5-phenyl-3-[4-(piperazin-1-ylmethyl)phenyl]imidazo[4,5-b]pyridin-2-yl]pyridin-2-amine (450 mg, HCl) as a yellow solid, which was used in the next step without further purification. 200 mg of the residue was purified by prep-HPLC (column: Waters xbridge 150*25 mm 10 um; mobile phase: [water (NH$_4$HCO$_3$)-ACN]; B %: 19/6-49%, 9 min) to give 3-[5-Phenyl-3-[4-(piperazin-1-ylmethyl)phenyl]imidazo[4,5-b]pyridin-2-yl]pyridin-2-amine (Intermediate 10, 49.7 mg) as a yellow solid. MS: m/z=462.2 [M+H]$^+$. $^1$H NMR (400 MHz, Dimethylsulfoxide-d$_6$) δ 8.27 (d, J=8.4 Hz, 1H), 8.04-7.97 (m, 4H), 7.48-7.39 (m, 8H), 7.15 (dd, J=8.0, 2.0 Hz, 1H), 7.03 (br s, 2H), 6.38 (dd, J=7.6, 4.8 Hz, 1H), 3.53 (s, 2H), 2.74-2.66 (m, 4H), 2.38-2.27 (m, 4H).

Intermediate 11: 3-[3-[4-[(4-amino-1-piperidyl)methyl]phenyl]-5-phenyl-imidazo[4,5-b]pyridin-2-yl]pyridin-2-amine

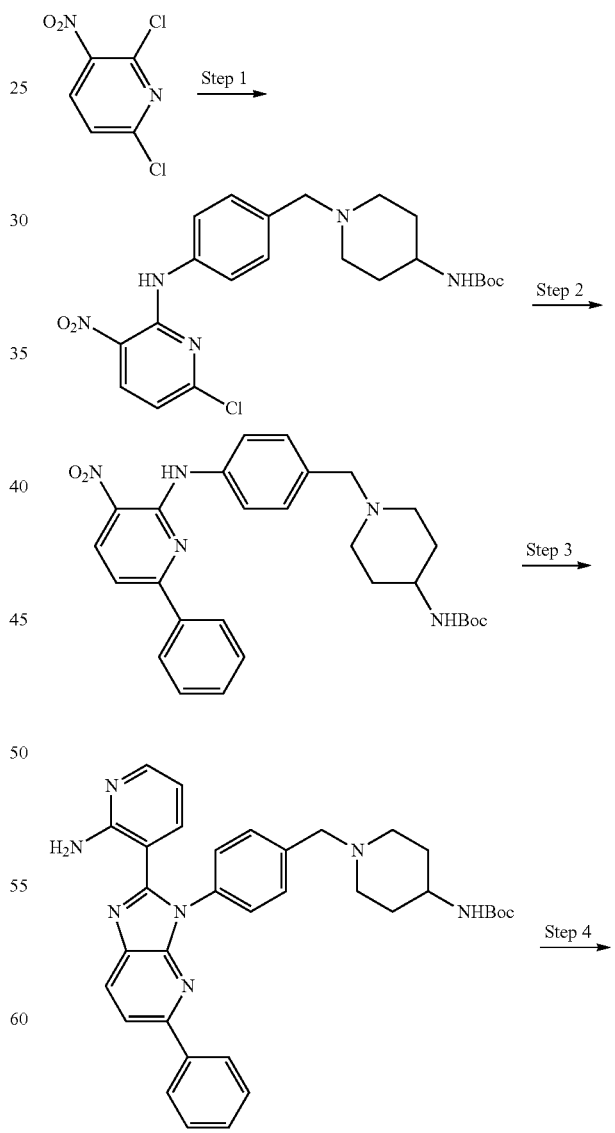

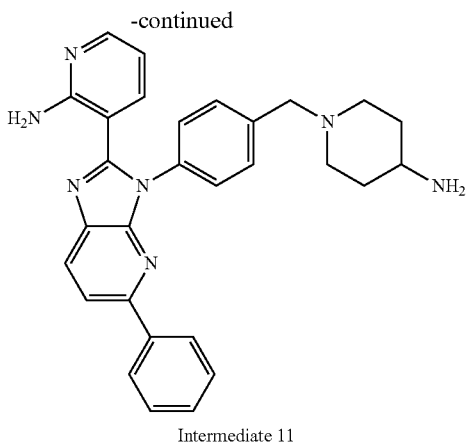

Intermediate 11

Step 1: tert-Butyl (I-(4-((6-chloro-3-nitropyridin-2-yl)amino)benzyl)piperidin-4-yl)carbamate To a solution of 2,6-dichloro-3-nitro-pyridine (3.0 g, 15.5 mmol) and tert-butyl N-[1-[(4-aminophenyl)methyl]-4-piperidyl]carbamate (4.8 g, 15.6 mmol) in 1,4-dioxane (100 mL) was added DIEA (6.0 g, 46.6 mmol). The mixture was stirred at 50° C. for 12 hr. The reaction mixture was diluted with H₂O (50 mL) and extracted with EtOAc (30 mL×2). The combined organic layers were washed with brine (50 mL), dried over Na₂SO₄, filtered, and concentrated under reduced pressure to give a residue. The residue was purified by silica gel flash chromatography (Eluent of 0~5% MeOH in CH₂Cl₂) to give tert-butyl N-[1-[[4-[(6-chloro-3-nitro-2-pyridyl)amino]phenyl]methyl]-4-piperidyl]carbamate (4.6 g, yield: 64%) as an orange solid. MS: m/z=462.1 [M+H]⁺. ¹H NMR (400 MHz, Chloroform-d) δ 10.26 (s, 1H), 8.46 (d, J=8.8 Hz, 1H), 7.60 (d, J=8.8 Hz, 2H), 7.34 (d, J=8.4 Hz, 2H), 6.79 (d, J=8.4 Hz, 1H), 4.42 (br s, 1H), 3.48 (s, 2H), 3.48-3.39 (m, 1H), 2.82 (br d, J=10.8 Hz, 2H), 2.10 (br t, J=10.8 Hz, 2H), 1.92 (br d, J=10.8 Hz, 2H), 1.50-1.40 (m, 2H). 1.44 (s, 9H).

Step 2: tert-Butyl (1-(4-((3-nitro-6-phenylpyridin-2-yl)amino)benzyl)piperidin-4-yl)carbamate A mixture of tert-butyl N-[1-[[4-[(6-chloro-3-nitro-2-pyridyl)amino]phenyl]methyl]-4-piperidyl]carbamate (1.0 g, 2.20 mmol), phenylboronic acid (528 mg, 4.30 mmol), Pd(dppf)Cl₂ (158 mg, 0.216 mmol) and K₂CO₃ (898 mg, 6.50 mmol) in 1,4-dioxane (10 mL) and H₂O (2 mL) was degassed and purged with N₂ three times, and then the mixture was stirred at 100° C. for 12 hr under N₂ atmosphere. After cooling to 25° C., the reaction mixture was diluted with H₂O and extracted with DCM (50 mL×2). The combined organic layers were washed with brine (50 mL), dried over Na₂SO₄, filtered, and concentrated under reduced pressure to give a residue. The residue was purified by silica gel flash chromatography (Eluent of 0~7% MeOH in CH₂Cl₂) to give tert-butyl N-[1-[[4-[(3-nitro-6-phenyl-2-pyridyl)amino]phenyl]methyl]-4-piperidyl]carbamate (1.1 g, yield: 96%) as a yellow solid. MS: m/z=504.1 [M+H]⁺. ¹H NMR (400 MHz, Chloroform-d) δ 10.31 (s, 1H), 8.59 (d, J=8.8 Hz, 1H), 8.09-8.02 (m, 2H), 7.72 (d, J=8.4 Hz, 2H), 7.51-7.47 (m, 3H), 7.36 (d, J=8.8 Hz, 1H), 7.30 (d, J=8.8 Hz, 1H), 4.52-4.37 (m, 1H), 3.52 (s, 2H), 3.51-3.42 (m, 1H), 2.85 (br d, J=11.2 Hz, 2H), 2.12 (br t, J=10.8 Hz, 2H), 1.93 (br d, J=11.0 Hz, 2H), 1.50-1.40 (m, 2H), 1.44 (s, 9H).

Step 3: tert-Butyl N-[1-[[4-[2-(2-amino-3-pyridyl)-5-phenyl-imidazo[4,5-b]pyridin-3-yl]phenyl]methyl]-4-piperidyl]carbamate To a solution of tert-butyl N-[1-[[4-[(3-nitro-6-phenyl-2-pyridyl)amino]phenyl]methyl]-4-piperidyl]carbamate (200 mg, 0.397 mmol), 2-aminopyridine-3-carbaldehyde (53.4 mg, 0.437 mmol) and Na₂S₂O₄ (207 mg, 1.2 mmol) in DMSO (6 mL). The mixture was stirred at 100° C. for 18 hr. After cooling to 25° C., the reaction mixture was diluted with DCM (40 mL). The organic layers were washed with H₂O (20 mL) and brine (20 mL), dried over Na₂SO₄, filtered and concentrated under reduced pressure to give a residue. The residue was purified by silica gel flash chromatography (IEluent of 0~7% MeOH in CH₂Cl₂) to give tert-butyl N-[1-[[4-[2-(2-amino-3-pyridyl)-5-phenyl-imidazo[4,5-b]pyridin-3-yl]phenyl]methyl]-4-piperidyl]carbamate (100 mg, yield: 40%) as a yellow solid. MS: m/z=576.2 [M+H]⁺.

Step 4: 3-(3-(4-((4-Aminopiperidin-1-yl)methyl)phenyl)-5-phenyl-3H-imidazo[4,5-b]pyridin-2-yl)pyridin-2-amine To a solution of tert-butyl (1-(4-(2-(2-aminopyridin-3-yl)-5-phenyl-3H-imidazo[4,5-b]pyridin-3-yl)benzyl)piperidin-4-yl)carbamate (200 mg, 0.347 mmol) in HCl in 1,4-dioxane (4 M, 2 mL). The mixture was stirred at 25° C. for 2 hr. The reaction mixture was concentrated under reduced pressure to give a residue. The residue was purified by prep-HPLC (column: Waters xbridge 150*25 mm 10 um; mobile phase: [water (NH₄HCO₃)-ACN]; B %: 24%-54%, 8 min) to give 3-[3-[4-[(4-amino-1-piperidyl)methyl]phenyl]-5-phenyl-imidazo[4,5-b]pyridin-2-yl]pyridin-2-amine (Intermediate 11, 120 mg, yield: 72%) as a light-yellow solid. MS: m/z=476.2 [M+H]⁺. ¹H NMR (400 MHz, Chloroform-d) δ 8.12 (d, J=8.4 Hz, 1H), 8.05 (dd, J=5.2, 1.6 Hz, 1H), 8.01 (d, J=7.2 Hz, 2H), 7.79 (d, J=8.4 Hz, 1H), 7.50-7.35 (m, 7H), 7.09 (dd, J=7.6, 1.2 Hz, 1H), 6.61 (br s, 2H), 6.35 (dd, J=7.6, 4.8 Hz, 1H), 3.58 (s, 2H), 2.88 (br d, J=11.6 Hz, 2H), 2.75-2.65 (m, 1H), 2.09 (br t, J=11.6 Hz, 2H), 1.83 (br d, J=11.6 Hz, 2H), 1.49-1.38 (m, 2H).

Intermediate 12: N-(3-(3-(4-((4-aminopiperidin-1-yl)methyl)phenyl)-2-(2-aminopyridin-3-yl)-3H-imidazo[4,5-b]pyridin-5-yl)phenyl)acetamide

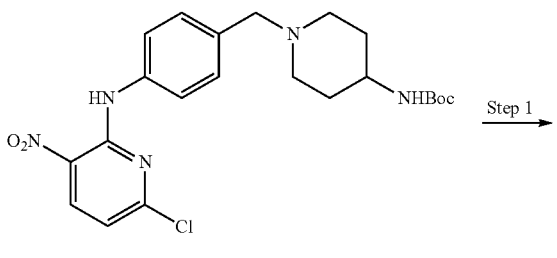

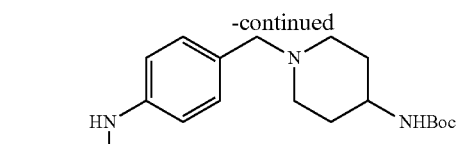

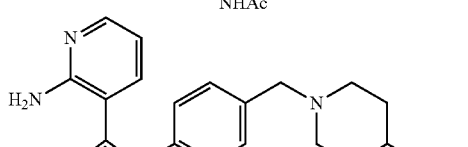

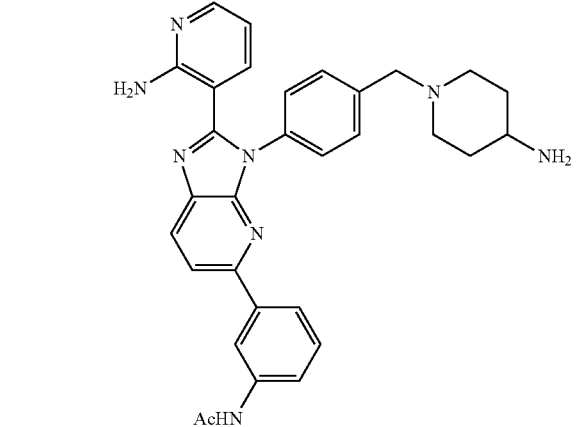

Intermediate 12

Step 1: Pert-butyl (1-(4-(((6-(3-acetamidophenyl)-3-nitropyridin-2-yl)amino)benzyl)piperidin-4-yl)carbamate A mixture of tert-butyl N-[1-[[4-[(6-chloro-3-nitro-2-pyridyl)amino]phenyl]methyl]-4-piperidyl]carbamate (1.0 g, 2.16 mmol), (3-acetamidophenyl)boronic acid (773 mg, 4.32 mmol), Pd(dppf)Cl₂ (158 mg, 0.216 mmol) and K₂CO₃ (895 mg, 6.48 mmol) in H₂O (2 mL) and 1,4-dioxane (10 mL) was degassed and purged with N₂ three times, and then the mixture was stirred at 100° C. for 12 hr under N₂ atmosphere. The reaction mixture was diluted with H₂O (50 mL) and extracted with CH₂Cl₂ (50 mL×2). The combined organic layers were washed with brine (50 mL), dried over Na₂SO₄, filtered, and concentrated under reduced pressure to give a residue. The residue was purified by silica gel flash chromatography (Eluent of 0~5% MeOH in CH₂Cl₂) to give tert-butyl N-[1-[[4-[[6-(3-acetamidophenyl)-3-nitro-2-pyridyl]amino]phenyl]methyl]-4-piperidyl]carbamate (1.04 g, yield: 86%) as an orange solid. MS: m/z=561.1 [M+H]⁺. ¹H NMR (400 MHz, Chloroform-d) δ 10.30 (s, 1H), 8.57 (d, J=8.8 Hz, 1H), 8.26 (br s, 1H), 7.79 (d, J=8.0 Hz, 1H), 7.72 (d, J=8.4 Hz, 2H), 7.63-7.57 (m, 1H), 7.47-7.35 (m, 4H), 7.28 (d, J=8.8 Hz, 1H), 4.44 (br s, 1H), 3.51 (s, 2H), 3.44-3.48 (m, 1H), 2.93-2.78 (m, 2H), 2.23 (s, 3H), 2.13 (br t, J=10.4 Hz, 2H), 1.93 (br d, J=11.2 Hz, 2H), 1.52-1.45 (m, 2H), 1.44 (s, 9H).

Step 2: Tert-butyl (1-(4-((3-nitro-6-phenylpyridin-2-yl)amino)benzyl)piperidin-4-yl)carbamate To a solution of tert-butyl N-[1-[[4-[[6-(3-acetamidophenyl)-3-nitro-2-pyridyl]amino]phenyl]methyl]-4-piperidyl]carbamate (950 mg, 1.69 mmol), 2-aminopyridine-3-carbaldehyde (228 mg, 1.9 mmol) and Na₂SO₄ (590 mg, 3.4 mmol) in DMSO (12 mL). The mixture was stirred at 100° C. for 18 hr. After cooling to 25° C., the reaction mixture was diluted with CH₂Cl₂ (50 mL). The organic layers were washed with H₂O (50 mL) and brine (50 mL), dried over Na₂SO₄, filtered, and concentrated under reduced pressure to give a residue. The residue was purified by silica gel flash chromatography (Eluent of 0~7% MeOH in CH₂Cl₂) to give tert-butyl N-[1-[[4-[5-(3-acetamidophenyl)-2-(2-amino-3-pyridyl)imidazo[4,5-b]pyridin-3-yl]phenyl]methyl]-4-piperidyl]carbamate (536 mg, yield: 50%) as a yellow solid. MS: m/z=633.3 [M+H]⁺. ¹H NMR (400 MHz, Chloroform-d) δ 8.11 (d, J=8.4 Hz, 1H), 8.06 (dd, J=4.8, 2.0 Hz, 1H), 8.00 (br s, 1H), 7.78 (d, J=8.4 Hz, 1H), 7.73 (d, J=8.0 Hz, 1H), 7.66 (d, J=8.0 Hz, 1H), 7.49 (br s, 1H), 7.45 (d, J=8.4 Hz, 2H), 7.40-7.34 (m, 3H), 7.05 (dd, J=8.0, 1.6 Hz, 1H), 6.60 (br s, 2H), 6.33 (dd, J=7.6, 4.8 Hz, 1H), 4.47 (br s, 1H), 3.58 (s, 2H), 3.51-3.48 (m, 1H), 2.85 (br d, J=11.2 Hz, 2H), 2.18-2.16 (m, 2H), 2.14 (s, 3H), 1.94 (br d, J=10.8 Hz, 2H), 1.49-1.47 (m, 2H), 1.45 (s, 9H).

Step 3: N-(3-(3-(4-((4-aminopiperidin-1-yl)methyl)phenyl)-2-(2-aminopyridin-3-yl)-3H-imidazo[4,5-b]pyridin-5-yl)phenyl)acetamide A solution of tert-butyl N-[1-[[4-[5-(3-acetamidophenyl)-2-(2-amino-3-pyridyl)imidazo[4,5-b]pyridin-3-yl]phenyl]methyl]-4-piperidyl]carbamate (300 mg, 474 mmol) in HCl/1,4-dioxane (4 M, 2 mL) was stirred at 25° C. for 2 hr. The reaction mixture was added NaHCO₃ to adjust the pH about 8 and extracted with DCM (15 mL×3). The combined organic layers were washed with brine (10 mL×2), dried by Na₂SO₄, filtered and concentrated under reduced pressure to give N-[3-[3-[4-[(4-amino-1-piperidyl)methyl]phenyl]-2-(2-amino-3-pyridyl)imidazo[4,5-b]pyridin-5-yl]phenyl]acetamide (Intermediate 12, 134 mg, yield: 53%) as a yellow solid. MS: m/z=533.2 [M+H]⁺. ¹H NMR (400 MHz, Chloroform-d) δ 8.13 (d, J=8.4 Hz, 1H), 8.07 (dd, J=4.8, 1.6 Hz, 1H), 8.02 (s, 1H), 7.81 (d, J=8.4 Hz, 1H), 7.76 (d, J=8.0 Hz, 1H), 7.69 (d, J=8.0 Hz, 1H), 7.48 (d, J=8.4 Hz, 2H), 7.42-7.37 (m, 4H), 7.08 (d, J=6.8 Hz, 1H), 6.61 (br s, 2H), 6.36 (dd, J=7.6, 4.8 Hz, 1H), 3.59 (s, 2H), 2.90 (br d, J=11.2 Hz, 2H), 2.77-2.67 (m, 1H), 2.20 (s, 3H), 2.12 (br t, J=11.2 Hz, 2H), 1.85 (br d, J=11.2 Hz, 2H), 1.49-1.41 (m, 2H).

Intermediate 13: Methyl 4-[2-(2-amino-3-pyridyl)-5-phenyl-imidazo[4,5-b]pyridin-3-yl]benzoate

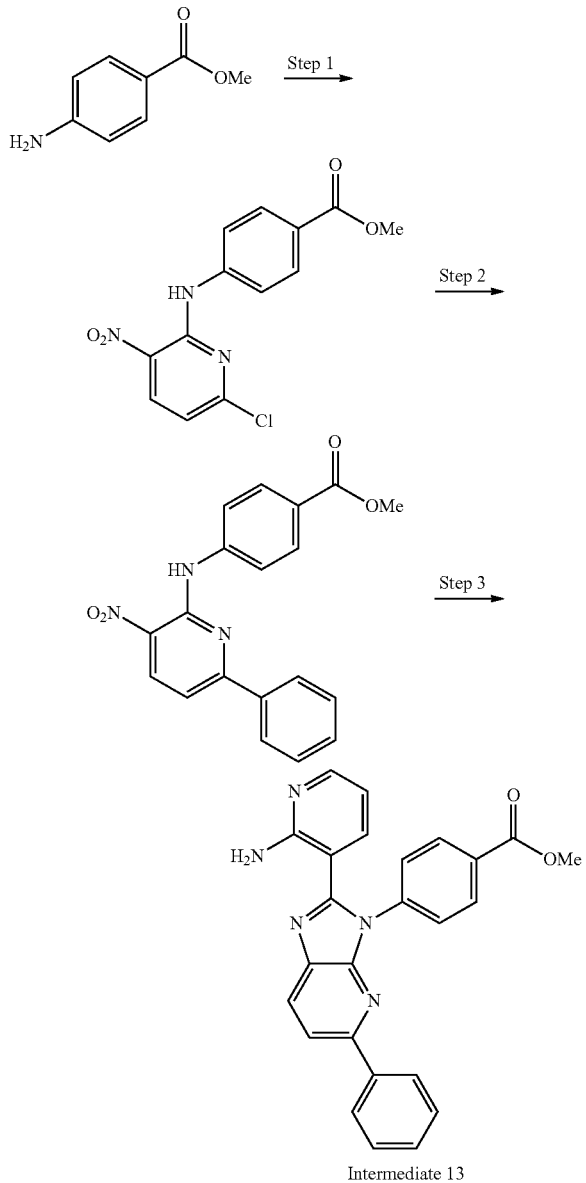

Intermediate 13

Step 1: Methyl 4-((6-chloro-3-nitropyridin-2-yl)amino)benzoate

To a solution of methyl 4-aminobenzoate (5 g, 33.1 mmol) in DMSO (50 mL) was added 2,6-dichloro-3-nitro-pyridine (7.66 g, 39.7 mmol) and DIEA (12.82 g, 99.2 mmol). The mixture was stirred at 80° C. for 16 hr. After cooling to 20° C., the reaction mixture was poured into H$_2$O (100 mL) and extracted with CH$_2$Cl$_2$ (100 mL×3). The combined organic layers were washed with brine (100 mL×2), dried over anhydrous Na$_2$SO$_4$, filtered, and concentrated to dryness. The crude product was triturated with EtOAc at 25° C. for 30 min to give methyl 4-[(6-chloro-3-nitro-2-pyridyl)amino] benzoate (8 g, yield: 51%) as a yellow solid. MS: m z=307.8 [M+H]$^+$. $^1$H NMR (400 MHz, Dimethylsulfoxide-d$_6$) δ 10.25 (s, 1H), 8.57 (d, J=8.4 Hz, 1H), 7.97 (d, J=8.8 Hz, 2H), 7.79 (d, J=8.8 Hz, 2H), 7.12 (d, J=8.4 Hz, 1H), 3.85 (s, 3H).

Step 2: Methyl 4-((3-nitro-6-phenylpyridin-2-yl)amino)benzoate

To a solution of methyl 4-[(6-chloro-3-nitro-2-pyridyl) amino]benzoate (45 g, 146 mmol) and phenylboronic acid (21.4 g, 176 mmol) in 1,4-dioxane (500 mL) and H$_2$O (100 mL) were added Pd(dppf)Cl$_2$ (10.7 g, 14.6 mmol) and Cs$_2$CO$_3$ (143 g, 439 mmol). The mixture was degassed and purged with N$_2$ three times, and then the mixture was stirred at 80° C. for 16 hr under N$_2$ atmosphere. The reaction mixture was poured into H$_2$O (500 mL) and extracted with CH$_2$Cl$_2$ (500 mL×3). The combined organic layers were washed with brine (500 mL×3), dried over anhydrous Na$_2$SO$_4$, filtered, and concentrated to dryness. The crude product was triturated with EtOAc at 25° C. for 30 min to give methyl 4-[(3-nitro-6-phenyl-2-pyridyl)amino]benzoate (35.2 g, yield: 69%) as a red solid. MS: m/z=350.0 [M+H]$^+$. $^1$H NMR (400 MHz, Dimethylsulfoxide-d$_6$) δ 10.25 (s, 1H), 8.62 (d, J=8.8 Hz, 1H), 8.15-8.10 (m, 2H), 8.00 (d, J=8.4 Hz, 2H), 7.92 (d, J=8.4 Hz, 2H), 7.67 (d, J=8.8 Hz, 1H), 7.59-7.54 (m, 3H), 3.86 (s, 3H)

Step 3: Methyl 4-(2-(2-aminopyridin-3-yl)-5-phenyl-3H-imidazo[4,5-b]pyridin-3-yl)benzoate To a solution of methyl 4-[(3-nitro-6-phenyl-2-pyridyl) amino]benzoate (15 g, 42.9 mmol) in DMSO (150 mL) was added 2-aminopyridine-3-carbaldehyde (6.29 g, 51.5 mmol) and Na$_2$S$_2$O$_4$ (15 g, 85.9 mmol). Then the reaction mixture was heated to 100° C. for 16 hr. After cooling to 25° C., the reaction mixture was diluted with H$_2$O (200 mL) and extracted with CH$_2$Cl$_2$ (200 ml×3), the combined organic layers were washed with brine (200 ml×2), dried over Na$_2$SO$_4$, filtered, and concentrated under reduced pressure to give a residue. The crude product was triturated with CH$_2$Cl$_2$ at 25° C. for 30 min to give methyl 4-[2-(2-amino-3-pyridyl)-5-phenyl-imidazo[4,5-b]pyridin-3-yl]benzoate (Intermediate 13, 12 g, yield: 66%) as a yellow solid. MS: m z=422.0 [M+H]$^+$. $^1$H NMR (400 MHz, Dimethylsulfoxide-d$_6$) δ 8.29 (d, J=8.0 Hz, 1H), 8.12 (d, J=8.4 Hz, 2H), 8.07-8.00 (m, 4H), 7.67 (d, J=8.8 Hz, 2H), 7.49-7.44 (m, 2H), 7.42-7.38 (m, 1H), 7.23 (dd, J=7.6, 1.6 Hz, 1H), 6.89 (br s, 2H), 6.46 (dd, J=7.6, 4.8 Hz, 1H), 3.90 (s, 3H).

Intermediate 14: 3-(3-(4-(Chloromethyl)phenyl)-5-phenyl-3H-imidazo[4,5-b]pyridin-2-yl)pyridin-2-amine

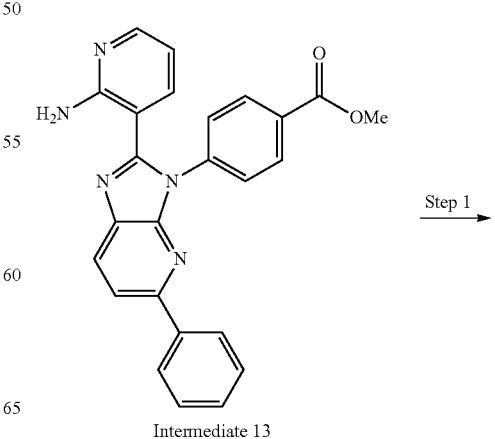

Intermediate 13

-continued

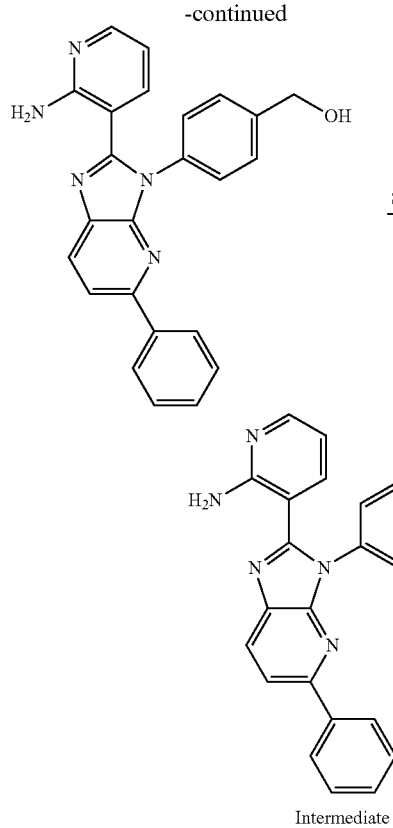

Intermediate 14

Step 1: (4-(2-(2-Aminopyridin-3-yl)-5-phenyl-3H-imidazo[4,5-b]pyridin-3-yl)phenyl)methanol To a solution of Intermediate 13 (2.5 g, 5.9 mmol) in THF (25 mL) was added LiAlH$_4$ (450 mg, 11.9 mmol) at 0° C. After addition, the resulting mixture was stirred at 25° C. for 2 hr. After the reaction mixture was cooled to 0° C., the reaction mixture was quenched with H$_2$O (100 mL), followed by 15% aqueous NaOH (30 mL). Then the reaction mixture was filtered. The filter liquor was concentrated to dryness to give [4-[2-(2-amino-3-pyridyl)-5-phenyl-imidazo[4,5-b]pyridin-3-yl]phenyl]methanol (1.87 g, yield: 80%) as a yellow solid, which was directly used to the next step without further purification. MS: m/z=394.1 [M+H]$^+$.

Step 2: 3-(3-(4-(Chloromethyl)phenyl)-5-phenyl-3H-imidazo[4,5-b]pyridin-2-yl)pyridin-2-amine To a solution of [4-[2-(2-amino-3-pyridyl)-5-phenyl-imidazo[4,5-b]pyridin-3-yl]phenyl]methanol (2.3 g, 5.9 mmol) in CH$_2$Cl$_2$ (25 mL) was added SOCl$_2$ (2.1 g, 17.5 mmol). The mixture was stirred at 40° C. for 1 hr. The reaction mixture was filtered. The filter liquor was concentrated to dryness to give 3-(3-(4-(chloromethyl)phenyl)-5-phenyl-3H-imidazo[4,5-b]pyridin-2-yl)pyridin-2-amine (Intermediate 14, 1.71 g, yield: 71%) as a yellow solid. MS: m/z=412.0 [M+H]$^+$. $^1$H NMR (400 MHz, Dimethylsulfoxide-d$_6$) δ 8.29 (d, J=8.4 Hz, 1H), 8.12 (d, J=8.4 Hz, 2H), 8.07-8.00 (m, 4H), 7.67 (d, J=8.4 Hz, 2H), 7.50-7.44 (m, 2H), 7.42-7.37 (m, 1H), 7.24 (d, J=7.2 Hz, 1H), 6.88 (br s, 2H), 6.46 (dd, J=4.8, 7.6 Hz, 1H), 3.90 (s, 2H).

Intermediate 15: 3-(3-(4-(Chloromethyl)phenyl)-3H-imidazo[4,5-b]pyridin-2-yl)pyridin-2-amine

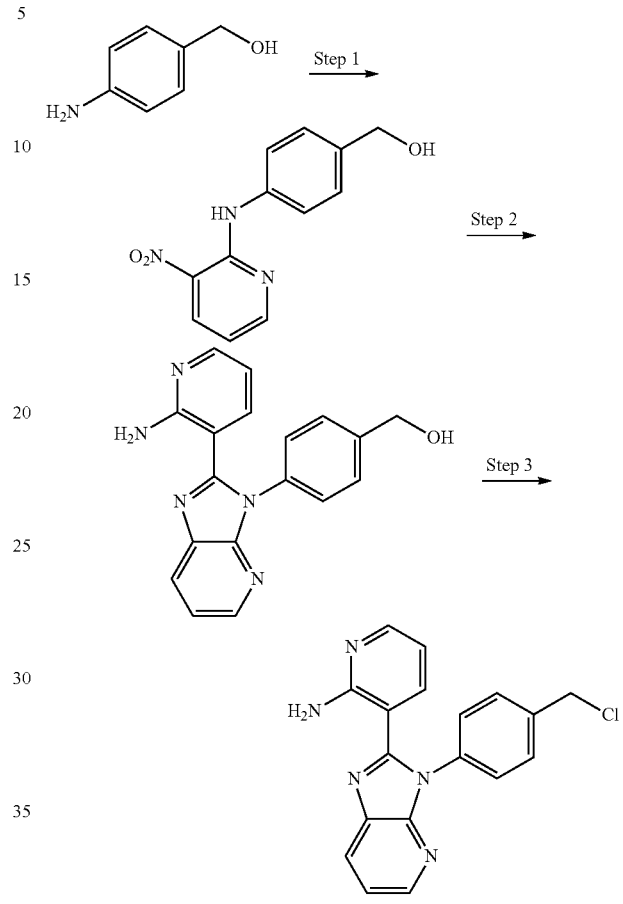

Intermediate 15

Step 1: (4-((3-Nitropyridin-2-yl)amino)phenyl)methanol

To a solution of (4-aminophenyl)methanol (10 g, 81.2 mmol) in 1,4-dioxane (150 mL) was added DIEA (31.5 g, 244 mmol) and 2-chloro-3-nitro-pyridine (15.5 g, 97.4 mmol). The mixture was stirred at 100° C. for 16 hr. The reaction mixture was concentrated under reduced pressure to remove solvent. The residue was diluted with H$_2$O (200 mL) and extracted with EtOAc (200 mL×2). The combined organic layers were washed with brine (500 mL), dried over Na$_2$SO$_4$, filtered and concentrated under reduced pressure to give a residue. The crude product was purified by flash chromatography on silica gel (Eluent of 0~82% EtOAc in petroleum ether) to give (4-((3-nitropyridin-2-yl)amino)phenyl)methanol (15.3 g, yield: 77%) as a yellow solid. MS: m/z=245.8 [M+H]$^+$. $^1$H NMR (400 MHz, Chloroform-d) δ 10.12 (s, 1H), 8.53 (dd, J=8.4, 2.0 Hz, 1H), 8.48 (dd, J=4.4, 1.6 Hz, 1H), 7.64 (d, J=8.0 Hz, 2H), 7.40 (d, J=8.4 Hz, 2H), 6.84 (dd, J=8.4, 4.8 Hz, 1H), 4.70 (s, 2H).

Step 2: (4-(2-(2-Aminopyridin-3-yl)-3H-imidazo[4,5-b]pyridin-3-yl)phenyl)methanol To a solution of 4-((3-nitropyridin-2-yl)amino)phenyl)methanol (10 g, 40.8 mmol) in DMSO (500 mL) was added Na₂S₂O₄ (21.3 g, 122 mmol) and 2-aminopyridine-3-carbaldehyde (5.98 g, 48.9 mmol). The mixture was stirred at 100° C. for 16 hr. The reaction mixture was quenched by H₂O (500 mL) at 20° C. and extracted with EtOAc (500 mL×2). The combined organic layers were washed with brine (500 mL), dried over Na₂SO₄, filtered, and concentrated under reduced pressure to give a residue. The crude product was purified by flash chromatography on silica gel (Eluent of 0~100% EtOAc in petroleum ether) to give (4-(2-(2-aminopyridin-3-yl)-3H-imidazo[4,5-b]pyridin-3-yl)phenyl)methanol (3.1 g, yield: 24%) as a yellow solid. MS: m/z=318.3 [M+H]⁺. ¹H NMR (400 MHz, Chloroform-d) δ 8.39-8.32 (m, 1H), 8.08 (dd, J=8.0, 1.2 Hz, 1H), 8.02 (dd, J=4.8, 1.6 Hz, 1H), 7.52 (d, J=8.4 Hz, 2H), 7.35 (d, J=8.0 Hz, 2H), 7.30-7.27 (m, 1H), 7.12 (dd, J=7.6, 1.6 Hz, 1H), 6.65 (br s, 2H), 6.35 (dd, J=7.6, 4.8 Hz, 1H), 4.76 (s, 2H).

Step 3: 3-(3-(4-(Chloromethyl)phenyl)-3H-imidazo[4,5-b]pyridin-2-yl)pyridin-2-amine To a solution of [4-[2-(2-amino-3-pyridyl)imidazo[4,5-b]pyridin-3-yl]phenyl]methanol (1.0 g, 3.15 mmol) in CH₂Cl₂ (10 mL) was added SOCl₂ (3.3 g, 27.6 mmol). The mixture was stirred at 40° C. for 1 hr. The reaction mixture was concentrated under reduced pressure to remove solvent to give 3-(3-(4-(chloromethyl)phenyl)-3H-imidazo[4,5-b]pyridin-2-yl)pyridin-2-amine (Intermediate 15, 1.2 g HCl salt) as a gray solid, which was used to the next step without further purification. MS: m/z=336.0 [M+H]⁺. ¹H NMR (400 MHz, Chloroform-d) δ 9.35 (brs, 1H), 8.55 (d, J=8.0 Hz, 1H), 8.28 (d, J=7.6 Hz, 1H), 7.91-7.83 (m, 1H), 7.68 (d, J=8.0 Hz, 2H), 7.64-7.59 (m, 1H), 7.54-7.50 (m, 1H), 7.46 (d, J=8.0 Hz, 2H), 7.30-7.27 (m, 2H), 6.70-6.60 (m, 1H), 4.70 (s, 2H).

Intermediate 16: 6-(Piperidin-4-yloxy) nicotinonitrile

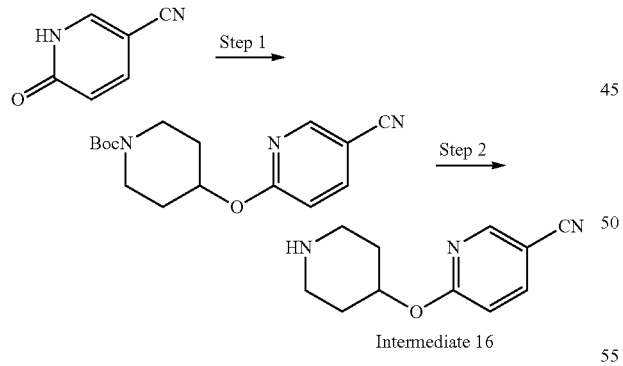

Intermediate 16

Step 1: Tert-butyl 4-((5-cyanopyridin-2-yl)oxy)piperidine-1-carboxylate

To a solution of 6-oxo-1H-pyridine-3-carbonitrile (1.0 g, 8.33 mmol) in THF (30 mL) was added PPh₃ (4.4 g, 16.7 mmol), then the mixture was degassed and purged with N₂ three times, DEAD (2.9 g, 16.7 mmol) and tert-butyl 4-hydroxypiperidine-1-carboxylate (1.8 g, 9.16 mmol) was added dropwise at 0° C. The resulting mixture was stirred at 25° C. for 16 hr. The mixture was 3 diluted with H₂O (50 mL) and extracted with EtOAc (50 mL×2). The combined organic layers were washed with 50 mL brine, dried over Na₂SO₄, filtered and concentrated under reduced pressure to give a residue. The crude product was purified by flash chromatography on silica gel (Eluent of 0~25% EtOAc in petroleum ether) to give tert-butyl 4-((5-cyanopyridin-2-yl)oxy)piperidine-1-carboxylate (2.5 g, yield: 99%) as a pink solid. ¹H NMR (400 MHz, Chloroform-d) δ 8.44 (d, J=2.4 Hz, 1H), 7.77 (dd, J=8.8, 2.4 Hz, 1H), 6.78 (d, J=8.4 Hz, 1H), 5.30-5.26 (m, 1H), 3.79-3.74 (m, 2H), 3.30-3.25 (m, 2H), 1.99-1.95 (m, 2H), 1.74-1.70 (m, 2H), 1.46 (s, 9H).

Step 2: 6-(Piperidin-4-yloxy) nicotinonitrile

To a solution of tert-butyl 4-[(5-cyano-2-pyridyl)oxy]piperidine-1-carboxylate (200 mg, 659 μmol) in HCl in 1,4-dioxane (4M, 2 mL). The mixture was stirred at 25° C. for 1 hr. The reaction mixture was concentrated under reduced pressure to remove solvent to give 6-(piperidin-4-yloxy)nicotinonitrile (Intermediate 16, 150 mg, HCl salt) as a pink solid, which was directly used to the next step without further purification. ¹H NMR (400 MHz, Chloroform-d) δ 9.64 (br s, 2H), 8.45 (d, J=1.6 Hz, 1H), 7.82 (dd, J=8.4, 1.6 Hz, 1H), 6.83 (d, J=8.4 Hz, 1H), 5.43 (br s, 1H), 4.28-4.14 (m, 1H), 3.44-3.24 (m, 4H), 2.40-2.16 (m, 4H).

Intermediate 17: 6-(Piperidin-4-yloxy)picolinonitrile

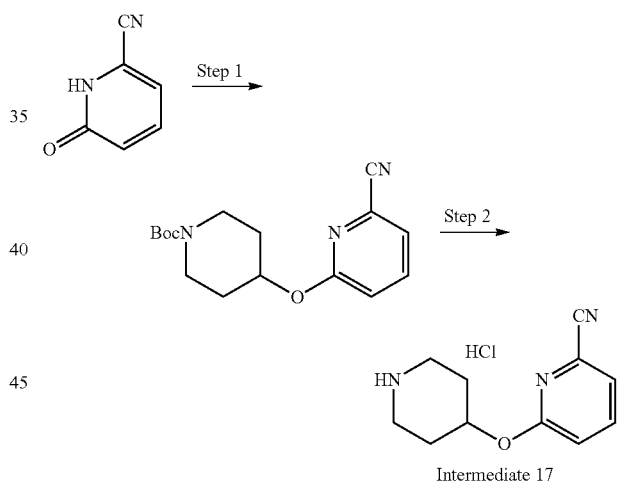

Intermediate 17

Step 1: Tert-butyl 4-((6-cyanopyridin-2-yl)oxy)piperidine-1-carboxylate

To a solution of 6-oxo-1,6-dihydropyridine-2-carbonitrile (500 mg, 4.2 mmol) and tert-butyl 4-hydroxypiperidine-1-carboxylate (922 mg, 4.6 mmol) in THF (15 mL) was added PPh₃ (2.2 g, 8.3 mmol) was degassed and purged with N₂ three times, and then DEAD (1.5 g, 8.3 mmol) was added dropwise at 0° C. The resulting mixture was stirred at 25° C. for 16 hr. The mixture was diluted with H₂O (20 mL) and extracted with EtOAc (30 mL×2). The combined organic layers were washed with 20 mL brine, dried over Na₂SO₄, filtered, and concentrated under reduced pressure to give a residue. The crude product was purified by flash chromatography on silica gel (Eluent of 0~25% EtOAc in petroleum ether), tert-butyl 4-((6-cyanopyridin-2-yl)oxy)piperidine-1- carboxylate (1.2 g, yield: 94%) was obtained as a white solid. $^1$H NMR (400 MHz, Chloroform-d) δ 7.63 (dd, J=8.4, 7.2 Hz, 1H), 7.24 (d, J=8.0 Hz, 1H), 6.90 (d, J=8.4 Hz, 1H), 5.27-5.17 (m, 1H), 3.79-3.70 (m, 2H), 3.30-3.21 (m, 2H), 1.99-1.91 (m, 2H), 1.72-1.65 (m, 2H), 1.44 (s, 9H).

Step 2: 6-(Piperidin-4-yloxy)picolinonitrile

To a solution of tert-butyl 4-((6-cyanopyridin-2-yl)oxy) piperidine-1-carboxylate (500 mg, 1.7 mmol) in HCl in 1,4-dioxane (4M, 5 mL). The mixture was stirred at 25° C. for 1 hr. The reaction mixture was concentrated under reduced pressure to give 6-(piperidin-4-yloxy)picolinonitrile (Intermediate 17,330 mg, HCl salt, yield: 81%) as a white solid, which was used to the next step without further purification.

Intermediate 18: 2-(Piperidin-4-yloxy)isonicotinonitrile

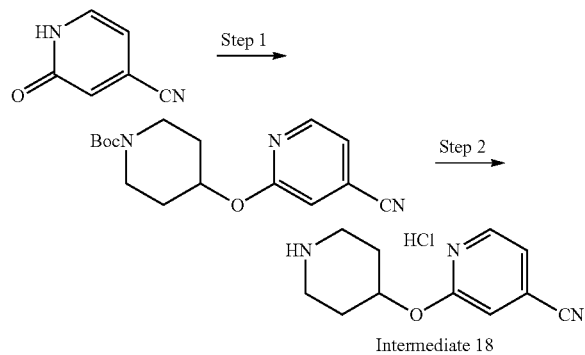

Intermediate 18

Step 1: Tert-butyl 4-((4-cyanopyridin-2-yl)oxy)piperidine-1-carboxylate

Following the general procedure of Intermediate 17, the reaction of 2-oxo-1,2-dihydropyridine-4-carbonitrile (1.0 g, 8.3 mmol) with tert-butyl 4-hydroxypiperidine-1-carboxylate (1.8 g, 9.2 mmol) was carried out. After purified flash chromatography on silica gel (Eluent of 0~20% EtOAc in petroleum ether), tert-butyl 4-((4-cyanopyridin-2-yl)oxy)piperidine-1-carboxylate (2.1 g, yield: 83%) was obtained as a pink solid. $^1$H NMR (400 MHz, Chloroform-d) δ 8.25 (d, J=5.2 Hz, 1H), 7.04 (dd, J=5.2, 1.2 Hz, 1H), 6.96 (s, 1H), 5.26-5.20 (m, 1H), 3.80-3.72 (m, 2H), 3.31-3.24 (m, 2H), 1.99-1.93 (m, 2H), 1.75-1.68 (m, 2H), 1.46 (s, 9H).

Step 2: 2-(Piperidin-4-yloxy)isonicotinonitrile

Following the general procedure of Intermediate 17, the reaction of tert-butyl 4-((4-cyanopyridin-2-yl)oxy)piperidine-1-carboxylate (500 mg, 1.7 mmol) in HCl in 1,4-dioxane (5 mL) was carried out, 2-(piperidin-4-yloxy)isonicotinonitrile (Intermediate 18, 330 mg, HCl salt, yield: 81%) was obtained as a pink solid, which was used to the next step without further purification.

Intermediate 19: 2-(Piperidin-4-yloxy)nicotinonitrile

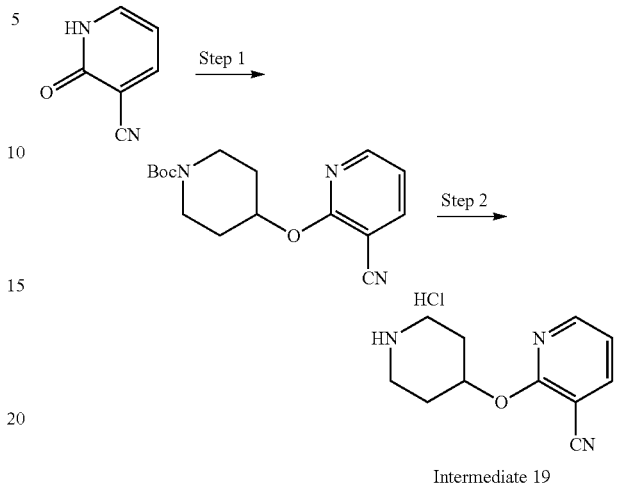

Intermediate 19

Step 1: Tert-butyl 4-((3-cyanopyridin-2-yl)oxy)piperidine-1-carboxylate

Following the general procedure of Intermediate 17, the reaction of 2-oxo-1,2-dihydropyridine-3-carbonitrile (1.0 g, 8.3 mmol) with tert-butyl 4-hydroxypiperidine-1-carboxylate (1.8 g, 9.2 mmol) was carried out. After purified flash chromatography on silica gel (Eluent of 0~20% EtOAc in petroleum ether), tert-butyl 4-((3-cyanopyridin-2-yl)oxy)piperidine-1-carboxylate (2.3 g, yield: 91%) was obtained as a pink solid. $^1$H NMR (400 MHz, Chloroform-d) δ 8.31 (dd, J=5.2, 2.0 Hz, 1H), 7.87 (dd, J=7.6, 2.0 Hz, 1H), 6.95 (dd, J=7.6, 5.2 Hz, 1H), 5.39-5.32 (m, 1H), 3.76-3.69 (m, 2H), 3.42-3.35 m, 2H), 2.00-1.93 (m, 2H), 1.85-1.78 (m, 2H), 1.46 (s, 9H).

Step 2: 2-(Piperidin-4-yloxy)nicotinonitrile

Following the general procedure of Intermediate 17, the reaction of tert-butyl 4-((3-cyanopyridin-2-yl)oxy)piperidine-1-carboxylate (500 mg, 1.7 mmol) in HCl in 1,4-dioxane (4M, 5 mL) was carried out, 2-(piperidin-4-yloxy)nicotinonitrile (Intermediate 19, 330 mg. HCl salt, yield: 81%) was obtained as a pink solid, which was used to the next step without further purification.

Intermediate 20: 3-(3-(4-(Chloromethyl)phenyl)-6-phenyl-3H-imidazo[4,5-b]pyridin-2-yl)pyridin-2-amine

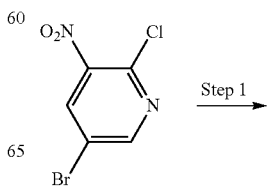

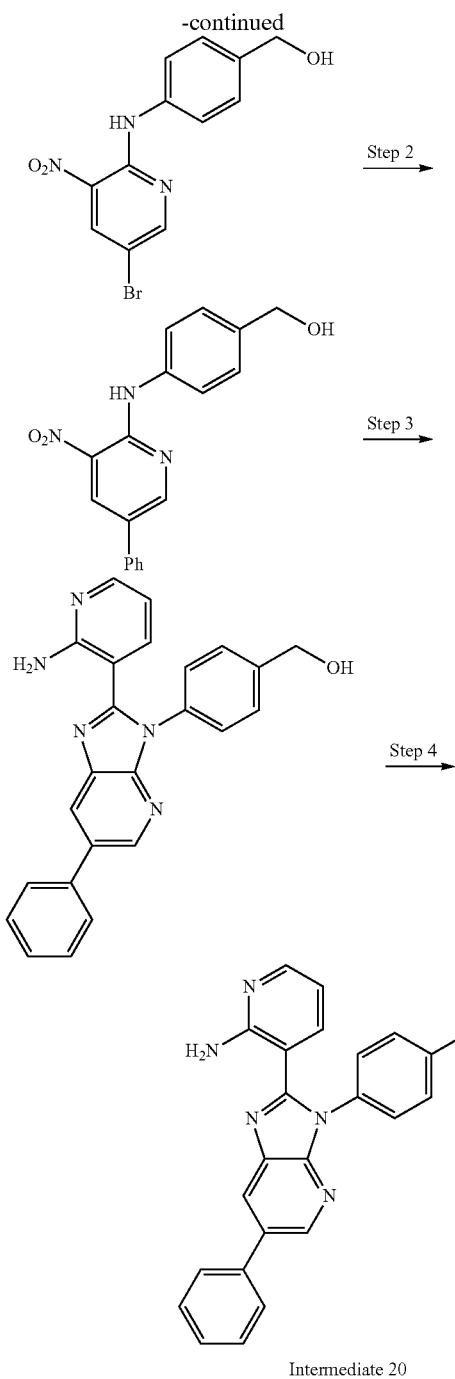

Step 1: (4-((5-Bromo-3-nitropyridin-2-yl)amino)phenyl)methanol

To a solution of 5-bromo-2-chloro-3-nitro-pyridine (10 g, 42 mmol) and (4-aminophenyl)methanol (5.2 g, 42 mmol) in DMSO (100 mL) was added DIEA (16.3 g, 126 mmol). The mixture was stirred at 25° C. for 16 hr. Then the reaction mixture was poured into H$_2$O (200 mL) and extracted with EtOAc (300 mL×2). The combined organic layers were washed with brine (200 mL×2), dried over anhydrous Na$_2$SO$_4$, filtered, and concentrated to dryness. The residue was purified by silica gel flash chromatography (Eluent of 10~50% EtOAc in petroleum ether) to give (4-((5-bromo-3-nitropyridin-2-yl)amino)phenyl)methanol (6.28 g, yield: 46%) as a red solid. MS: m/z=324.0, 325.0 [M+H]$^+$. $^1$H NMR (400 MHz, Chloroform-d-) δ 10.05 (br s, 1H), 8.65 (d, J=2.4 Hz, 1H), 8.50 (d, J=2.4 Hz, 1H), 7.59 (d, J=8.4 Hz, 2H), 7.40 (d, J=8.4 Hz, 2H), 4.71 (s, 2H).

Step 2: (4-((3-Nitro-5-phenylpyridin-2-yl)amino)phenyl)methanol

A mixture of [4-[(5-bromo-3-nitro-2-pyridyl)amino]phenyl]methanol (5.4 g, 16.7 mmol), phenylboronic acid (6.1 g, 50 mmol), K$_2$CO$_3$ (4.62 g, 33.44 mmol), Pd(dppf)Cl$_2$ (1.22 g, 1.67 mmol) in 1,4-dioxane (60 mL) and H$_2$O (12 mL) was degassed and purged with N$_2$ three times, and then the mixture was stirred at 100° C. for 8 hr under N$_2$ atmosphere. The reaction mixture was poured into H$_2$O (100 mL) and extracted with CH$_2$Cl$_2$ (100 mL×3). The combined organic layers were washed with brine (100 mL×2), dried over anhydrous Na$_2$SO$_4$, filtered, and concentrated to dryness. The residue was purified by silica gel flash chromatography (Eluent of 0~50% EtOAc in petroleum ether) to give [4-[(3-nitro-5-phenyl-2-pyridyl)amino]phenyl]methanol (4.6 g, yield: 86%) as a red solid. MS: m/z=322.1 [M+H]$^+$. $^1$H NMR (400 MHz, Chloroform-d) δ 10.15 (s, 1H), 8.78-8.72 (m, 2H), 8.25 (d, J=8.0 Hz 1H), 7.70-7.65 (m, 2H), 7.59-7.56 (m, 2H), 7.51-7.49 (m, 2H), 7.44-7.41 (m, 2H), 4.72 (s, 2H).

Step 3: (4-(2-(2-Aminopyridin-3-yl)-6-phenyl-3H-imidazo[4,5-b]pyridin-3-yl)phenyl)methanol To a solution of [4-[(3-nitro-5-phenyl-2-pyridyl)amino]phenyl]methanol (15 g, 46.7 mmol) in DMSO (600 mL) was added Na$_2$S$_2$O$_4$ (16 g, 93 mmol) and 2-aminopyridine-3-carbaldehyde (6.8 g, 56 mmol). The mixture was stirred at 100° C. for 12 hr. After cooling to 25° C., the reaction mixture was diluted with H$_2$O (200 mL) and extracted with CH$_2$Cl$_2$ (200 ml×3), the combined organic layers were washed with brine (200 ml×2), dried over Na$_2$SO$_4$, filtered, and concentrated under reduced pressure to give a residue. The residue was purified by silica gel flash chromatography (Eluent of 0~100% EtOAc in petroleum ether) to give [4-[2-(2-amino-3-pyridyl)-6-phenyl-imidazo[4,5-b]pyridin-3-yl]phenyl]methanol (5.15 g crude, yield: 28%) as a yellow solid. MS: m/z=394.0 [M+H]$^+$.

Step 4: 3-(3-(4-(Chloromethyl)phenyl)-6-phenyl-3H-imidazo[4,5-b]pyridin-2-yl)pyridin-2-amine To a solution of [4-[2-(2-amino-3-pyridyl)-6-phenyl-imidazo[4,5-b]pyridin-3-yl]phenyl]methanol (500 mg, 1.3 mmol) in CH$_2$Cl$_2$ (10 mL) was added SOCl$_2$ (771 mg, 6.5 mmol). The mixture was stirred at 40° C. for 2 hr. The reaction mixture was concentrated under reduced pressure to give a residue. The residue was purified by silica gel flash chromatography (Eluent of 0~100% EtOAc in petroleum ether) to give 3-[3-[4-(chloromethyl)phenyl]-6-phenyl-imidazo[4,5-b]pyridin-2-yl]pyridin-2-amine (Intermediate 20,267 mg, yield: 51%) as a yellow solid. MS: m/z=411.8 [M+H]$^+$. $^1$H NMR (400 MHz, Dimethylsulfoxide-d$_6$) δ 8.63 (d, J=2.0 Hz, 1H), 8.47 (d, J=2.0 Hz, 1H), 8.01 (dd, J=8.8, 3.2 Hz, 1H), 7.79 (d, J=7.2 Hz, 2H), 7.61 (d, J=8.4 Hz, 2H), 7.55-7.47 (m, 4H), 7.45-7.40 (m, 1H), 7.25 (dd, J=7.6, 1.8 Hz, 1H), 6.96 (br s, 2H), 6.44 (dd, J=7.6, 4.8 Hz, 1H), 4.86 (s, 2H).

Intermediate 21: 6-Chloropyridazine-4-carbonitrile

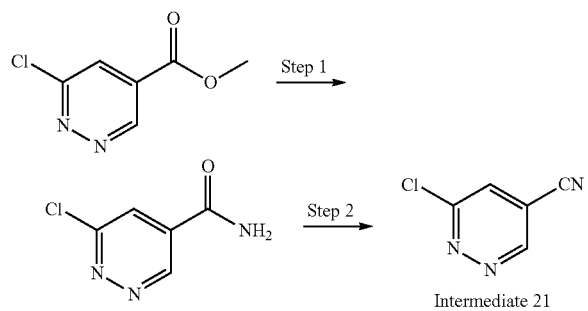

Step 1: 6-Chloropyridazine-4-carboxamide

A solution of methyl 6-chloropyridazine-4-carboxylate (9.0 g, 52 mmol) and ammonia in MeOH (7 M, 90 mL) was stirred at 80° C. for 3 hr. The residue was purified by silica gel flash chromatography (Eluent of 0~98% EtOAc in petroleum ether), 6-chloropyridazine-4-carboxamide (6.4 g, yield: 78%) was obtained as a yellow solid. $^1$H NMR (400 MHz, Dimethylsulfoxide-$d_6$) δ 9.52 (s, 1H), 8.48 (br s, 1H), 8.21 (s, 1H), 8.09 (br s, 1H).

Step 2: 6-Chloropyridazine-4-carbonitrile

To a solution of 6-chloropyridazine-4-carboxamide (3.0 g, 19.0 mmol) in Py (30 mL) was added POCl$_3$ (14.6 g, 95.0 mmol). The mixture was stirred at 25° C. for 12 hr. The residue was purified by column chromatography (0-30% EtOAc in petroleum ether), 6-chloropyridazine-4-carbonitrile (Intermediate 21, 1.48 g, yield: 56%) was obtained as a yellow solid. MS: m/z=140.0 [M+H]$^+$. $^1$H NMR (400 MHz, Dimethylsulfoxide-$d_6$) δ 9.67 (s, 1H), 8.64 (s, 1H).

Intermediate 22: 5-(Piperidin-4-ylamino)nicotinonitrile

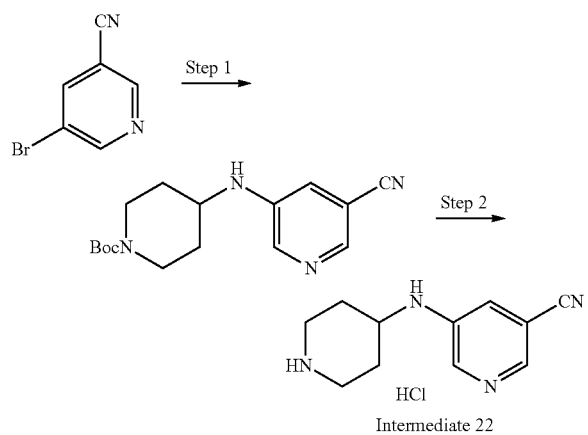

Step 1: Tert-butyl 4-((5-cyanopyridin-3-yl)amino)piperidine-1-carboxylate

A mixture of tert-butyl 4-aminopiperidine-1-carboxylate (1.3 g, 6.6 mmol), 5-bromonicotinonitrile (1.0 g, 5.5 mmol), BINAP (170 mg, 273 μmol), Pd(OAc)$_2$ (25 mg, 109 mmol) and Cs$_2$CO$_3$ (3.56 g, 10.9 mmol) in 1,4-dioxane (20 mL) was degassed and purged with N$_2$ three times, and then the mixture was stirred at 100° C. for 16 hr under N$_2$ atmosphere. The mixture was diluted with H$_2$O (50 mL) and extracted with EtOAc (50 mL×2). The combined organic layers were washed with 50 mL brine, dried over Na$_2$SO$_4$, filtered, and concentrated under reduced pressure to give a residue. The crude product was purified by flash chromatography on silica gel (Eluent of 0~30% EtOAc in petroleum ether), tert-butyl 4-((5-cyanopyridin-3-yl)amino)piperidine-1-carboxylate (1.2 g, yield: 72%) was obtained as a light yellow solid. $^1$H NMR (400 MHz, Chloroform-d) δ 8.16 (s, 2H), 7.06-6.97 (m, 1H), 4.17-3.98 (m, 3H), 3.41 (br s, 1H), 2.99-2.87 (m, 2H), 2.05-1.97 (m, 2H), 1.46 (s, 9H), 1.43-1.32 (m, 2H).

Step 2: 5-(Piperidin-4-ylamino)nicotinonitrile

To a solution of tert-butyl 4-((5-cyanopyridin-3-yl)amino)piperidine-1-carboxylate (150 mg, 496 μmol) in HCl in 1,4-dioxane (4M, 2 mL). The mixture was stirred at 25° C. for 1 hr. The reaction mixture was concentrated under reduced pressure to give 5-(piperidin-4-ylamino)nicotinonitrile (110 mg, HCl salt, yield: 93%) as a light-yellow solid, which was used to the next step without further purification.

Intermediate 23: 3-Cyanopyridazine-4-carboxylic acid

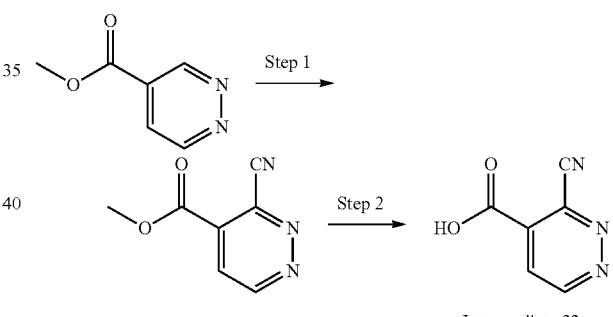

Step 1: Methyl 3-cyanopyridazine-4-carboxylate

To a solution of methyl pyridazine-4-carboxylate (600 mg, 4.34 mmol) in CHCl$_3$ (25 mL) was added Tf$_2$O (1.47 g, 5.21 mmol). The mixture was stirred at 25° C. for 1 hr. And then TMSCN (2.15 g, 21.7 mmol) was added dropwise at 25° C. The reaction mixture was stirred at 60° C. for 3 hr. And then 4-methylmorpholine (571 mg, 5.65 mmol) was added dropwise at 60° C. The mixture was stirred at 60° C. for another 12 hr. The reaction mixture was quenched with NaHCO$_3$ (aq) (10 mL) at 25° C. and extracted with CH$_2$Cl$_2$ (50 mL×2). The combined organic layers were washed with brine (50 mL), dried over Na$_2$SO$_4$, filtered, and concentrated under reduced pressure to give a residue. The residue was purified by silica gel flash chromatography (Eluent of 0~40% EtOAc in petroleum ether), methyl 3-cyanopyridazine-4-carboxylate (400 mg, yield: 56%) was obtained as a brown solid. $^1$H NMR (400 MHz, Dimethylsulfoxide-$d_6$) δ 9.71 (d, J=5.6 Hz, 1H), 8.31 (d, J=5.6 Hz, 1H), 3.98 (s, 3H).

Step 2: 3-Cyanopyridazine-4-carboxylic acid

To a solution of methyl 3-cyanopyridazine-4-carboxylate (400 mg, 2.45 mmol) in THF (5 mL) was added the mixture of LiOH·H$_2$O (205 mg, 4.90 mmol) in H$_2$O (5 mL) at 0° C. The reaction mixture was stirred at 0° C. for 0.5 hr. The reaction mixture was then adjusted to pH=5 by aq. HCl (1 N). The resulting mixture was extracted with CH$_2$Cl$_2$ (20 mL×3). The combined organic layers were dried over anhydrous Na$_2$SO$_4$, filtered, and concentrated to give a residue 3-cyanopyridazine-4-carboxylic acid (Intermediate 23, 350 mg, yield: 96%) as a brown solid. $^1$H NMR (400 MHz, Dimethylsulfoxide-d$_6$) δ 9.68 (d, J=5.6 Hz, 1H), 8.26 (d, J=5.6 Hz, 1H).

Intermediate 24: 5-Cyanopyrimidine-4-carboxylic acid

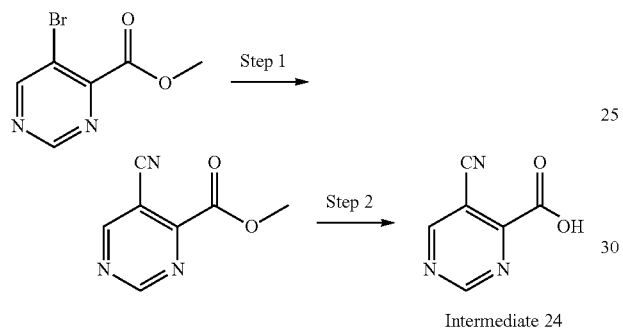

Intermediate 24

Step 1: Methyl 5-cyanopyrimidine-4-carboxylate

To a solution of methyl 5-bromopyrimidine-4-carboxylate (400 mg, 1.84 mmol) and Zn(CN)$_2$ (216 mg, 1.84 mmol) in DMF (10 mL) was added DPPF (102 mg, 184 μmol) and Pd$_2$(dba)$_3$ (84 mg, 92.2 μmol) at 25° C. After addition the reaction mixture was stirred at 90° C. under N$_2$ atmosphere for 12 hr. The reaction mixture was poured into H$_2$O (50 mL). The resulting mixture was extracted with EtOAc (30 mL×2). The combined organic phase was washed with water (50 mL), dried over anhydrous Na$_2$SO$_4$, filtered and concentrated. The residue was purified by silica gel flash chromatography (Eluent of 0~40% EtOAc in petroleum ether), methyl 5-cyanopyrimidine-4-carboxylate (130 mg, yield: 42%) was obtained as a yellow solid. $^1$H NMR (400 MHz, Dimethylsulfoxide-d$_6$) δ 9.58 (s, 1H), 9.54 (s, 1H), 3.98 (s, 3H).

Step 2: 5-Cyanopyrimidine-4-carboxylic acid

To a solution of methyl 5-cyanopyrimidine-4-carboxylate (400 mg, 2.45 mmol) in THF (4 mL) was added the mixture of LiOH·H$_2$O (205 mg, 4.90 mmol) in H$_2$O (4 mL) at 0° C. The reaction mixture was stirred at 0° C. for 0.5 hr. The reaction mixture was then adjusted to pH=5 by aq. HCl (1 N). The resulting mixture was extracted with CH$_2$Cl$_2$ (20 mL×3). The combined organic phase was dried over anhydrous Na$_2$SO$_4$, filtered, and concentrated to give a residue 5-cyanopyrimidine-4-carboxylic acid (Intermediate 24, 350 mg, yield: 96%) as a brown solid. $^1$H NMR (400 MHz, Dimethylsulfoxide-d$_6$) δ 9.22 (s, 1H), 9.08 (s, 1H).

Intermediate 25: 2-Carbamoylbenzo[d]thiazole-5-carboxylic acid

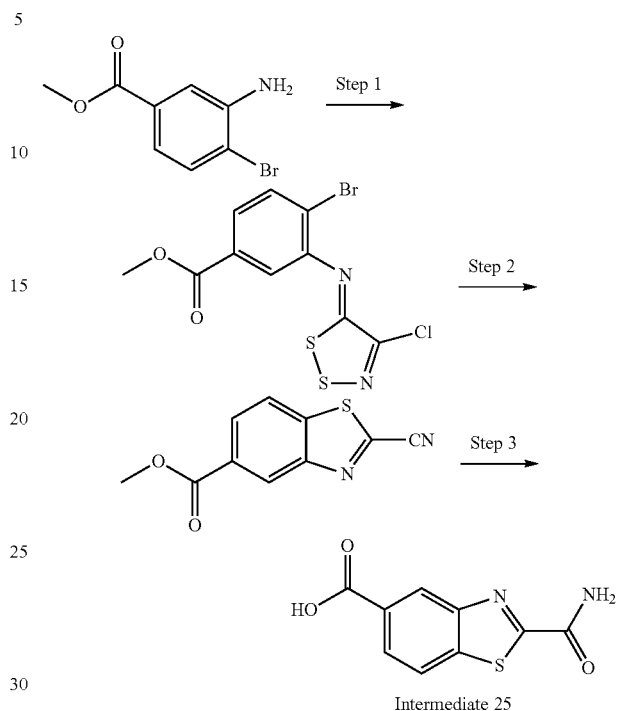

Intermediate 25

Step 1: Methyl (Z)-4-bromo-3-((4-chloro-5H-1,2,3-dithiazol-5-ylidene)amino)benzoate To a solution of methyl 3-amino-4-bromo-benzoate (5.0 g, 22 mmol) in 50 mL DCM was added 4,5-dichlorodithiazol-2-ium; chloride (5.9 g, 28 mmol). The mixture was stirred at 25° C. for 3 hr. Then pyridine (3.4 g, 43 mmol) was added to the mixture, the resulting mixture was stirred at 25° C. for 2 hr. The mixture was concentrated under reduced pressure. The residue was purified by column chromatography (Eluent of 0~10% EtOAc in petroleum ether), methyl methyl (Z)-4-bromo-3-((4-chloro-5H-1,2,3-dithiazol-5-ylidene)amino)benzoate (2.27 g, yield: 27%) was obtained as a yellow solid. MS: m/z=366.6 [M+H]$^+$. $^1$H NMR (400 MHz, Chloroform-d) δ 7.80 (d, J=1.6 Hz, 1H), 7.76 (s, 1H), 7.76 (d, J=2.0 Hz, 1H), 3.92-3.92 (m, 3H).

Step 2: (4-((3-Nitro-5-phenylpyridin-2-yl)amino)phenyl)methanol

Methyl 4-bromo-3-[(Z)-(4-chlorodithiazol-5-ylidene)amino]benzoate (1.13 g, 3.0 mmol) and CuI (588 mg, 3.0 mmol) were taken up into a microwave tube in pyridine (20 mL). The sealed tube was heated at 115° C. for 0.5 hr under microwave. The reaction mixture was diluted with EtOAc (50 mL) and quenched with Na$_2$SO$_3$ (50 mL) at 25° C. The combined organic layers were washed with brine (50 mL), dried over, filtered, and concentrated under reduced pressure to give a residue. The residue was purified by column chromatography (Eluent of 0~5% EtOAc in petroleum ether), (4-((3-nitro-5-phenylpyridin-2-yl)amino)phenyl)methanol (1.0 g, yield: 70%) was obtained as a yellow solid.

MS: m/z=218.9 [M+H]⁺. ¹H NMR (400 MHz, Chloroform-d) δ 8.89 (d, J=2.0 Hz, 1H), 8.33-8.26 (m, 1H), 8.05 (d, J=8.4 Hz, 1H), 4.01 (s, 3H).

Step 3: 2-Carbamoylbenzo[d]thiazole-5-carboxylic acid

To a solution of methyl 2-cyano-1,3-benzothiazole-5-carboxylate (200 mg, 916 μmol) in THF (2 mL) was added LiOH·H₂O in H₂O (1 M, 1.37 mL). The mixture was stirred at 0° C. for 3 hr. The mixture was concentrated under pressure at 20° C., 2-Carbamoylbenzo[d]thiazole-5-carboxylic acid (Intermediate 25, 200 mg, used directly) was obtained as a yellow solid. MS: m/z=223.0 [M+H]⁺.

Intermediate 26: 2-carbamoyl-5-fluorobenzo[d]thiazole-7-carboxylic acid

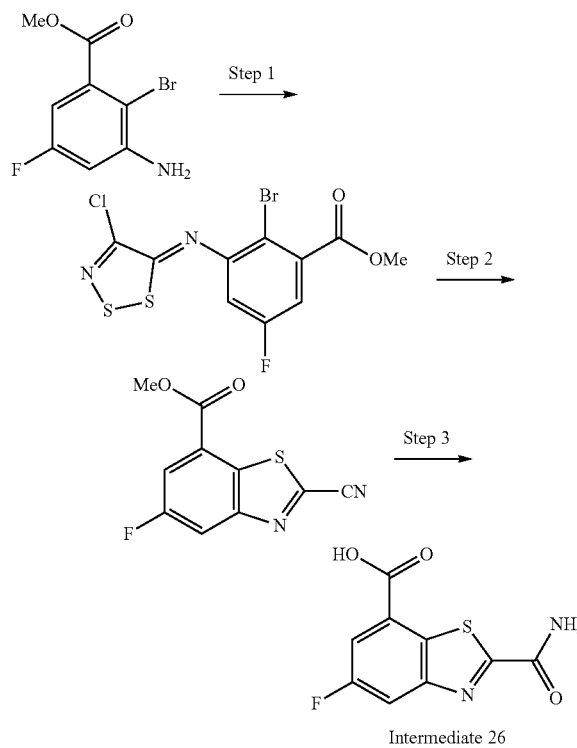

Step 1: Methyl (Z)-2-bromo-3-((4-chloro-5H-1,2,3-dithiazol-5-ylidene)amino)-5-fluorobenzoate A mixture of 4,5-dichlorodithiazol-2-ium; chloride (2.19 g, 10.48 mmol) and methyl 3-amino-2-bromo-5-fluoro-benzoate (2.0 g, 8.06 mmol) in DCM (30 mL) was stirred at 25° C. for 3 hr, and then Py (1.28 g, 16.13 mmol) was added dropwise to the solution, the reaction mixture was stirred for another 2 hr. The reaction mixture was concentrated under reduced pressure to give a residue. Methyl (Z)-2-bromo-3-((4-chloro-5H-1,2,3-dithiazol-5-ylidene)amino)-5-fluorobenzoate (3.0 g, yield: 92%) was obtained as a yellow solid, which was directly used to the next step without further purification. MS: m/z=384.5 [M+H]⁺.

Step 2: Methyl 2-cyano-5-fluorobenzo[d]thiazole-7-carboxylate

To a solution of methyl 2-bromo-3-[(Z)-(4-chlorodithiazol-5-ylidene)amino]-5-fluoro-benzoate (1.0 g, 2.61 mmol) in pyridine (15 mL) was added CuI (496 mg, 2.61 mmol). The mixture was stirred under microwave irradiation (400 W) 115° C. for 0.5 hr. The reaction was diluted with H₂O (40 mL) and extracted with EtOAc (30 mL×3). The combined organic layers were washed with 0.5 M HCl (30 mL×3) and brine (10 mL×5), dried over Na₂SO₄, filtered, and concentrated under reduced pressure to give a residue. The residue was purified by silica gel flash chromatography (Eluent of 2~3% EtOAc in petroleum ether), methyl 2-cyano-5-fluorobenzo[d]thiazole-7-carboxylate (117 mg, yield: 19%) was obtained as white solid, which was directly used to the next step. MS: m/z=236.9 [M+H]⁺. ¹H NMR (400 MHz, Chloroform-d) δ 8.13-8.07 ((m, 1H), 4.07 (s, 3H. ¹F NMR (400 MHz, Chloroform-d) δ −111.7.

Step 3: 2-Carbamoyl-5-fluorobenzo[d]thiazole-7-carboxylic acid

A mixture of methyl 2-cyano-5-fluorobenzo[d]thiazole-7-carboxylate (400 mg, 1.69 mmol), LiOH·H₂O (81.1 mg, 3.39 mmol) in THF (2 mL) and H₂O (2 mL) was stirred at 60° C. for 0.5 hr. The reaction was concentrated under reduced pressure to give a residue, 2-carbamoyl-5-fluorobenzo[d]thiazole-7-carboxylic acid (Intermediate 26, 350 mg, yield: 88%) was obtained as light-yellow solid, which was directly used to the next step without further purification. MS: m/z=240.8 [M+H]⁺. ¹H NMR (400 MHz, Dimethylsulfoxide-d₆) δ 8.30 (s, 1H), 7.91 (s, 1H), 7.83-7.72 (m, 1H), 7.65-7.62 (m, 1H). ¹F NMR (400 MHz, Dimethylsulfoxide-d₆) δ −116.1.

Intermediate 27: 2-Carbamoyl-6-fluorobenzo[d]thiazole-4-carboxylic acid

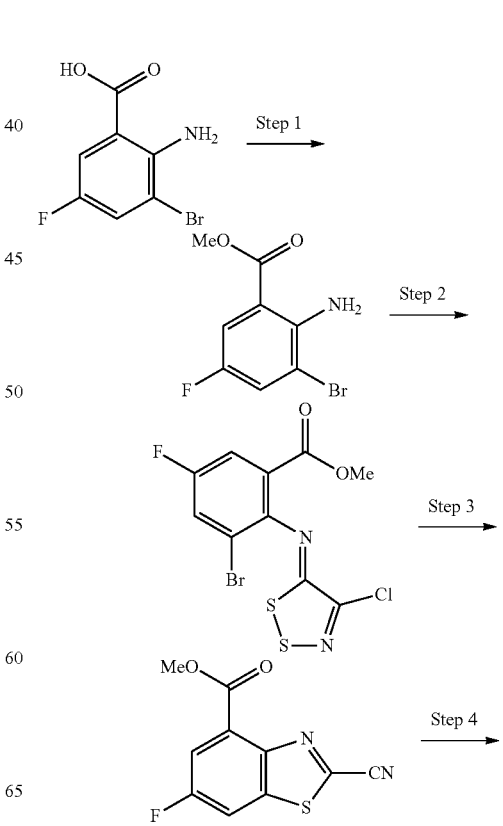

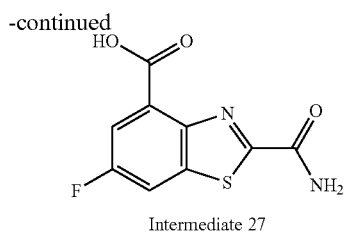

Intermediate 27

Step 1: Methyl 2-amino-3-bromo-5-fluorobenzoate

To a solution of 2-amino-3-bromo-5-fluoro-benzoic acid (2.0 g, 8.55 mmol) in MeOH (50 mL) was added $SOCl_2$ (3.05 g, 25.64 mmol) dropwise. The mixture was stirred at 70° C. for 2 hr. The reaction mixture was concentrated under reduced pressure to give methyl 2-amino-3-bromo-5-fluorobenzoate (2.0 g, yield: 73%) was obtained as a black solid, which was directly used to the next step without further purification. MS: m/z=249.8, 250.8 [M+H]$^+$. $^1$H NMR (400 MHz, Chloroform-d) δ 7.68-7.53 (m, 1H), 7.42-7.40 (m, 1H), 5.34 (br s, 2H), 3.90 (s, 3H). $^1$F NMR (400 MHz, Chloroform-d) δ –127.5.

Step 2: Methyl (Z)-3-bromo-2-((4-chloro-5H-1,2,3-dithiazol-5-ylidene)amino)-5-fluorobenzoate A mixture of 4,5-dichlorodithiazol-2-ium; chloride (168.1 mg, 806 μmol) and methyl 2-amino-3-bromo-5-fluorobenzoate (200 mg, 806 μmol) in DCM (3 mL) was stirred at 25° C. for 3 hr, and then pyridine (128 mg, 1.61 mmol) was added dropwise to the solution, the reaction mixture was stirred for another 2 hr. The reaction mixture was concentrated under reduced pressure to give a residue. Methyl (Z)-3-bromo-2-((4-chloro-5H-1,2,3-dithiazol-5-ylidene)amino)-5-fluorobenzoate (300 mg, yield: 63%) was obtained as light-green oil, which was used directly to the next step without further purification. MS: m/z=384.4 [M+H]$^+$.

Step 3: Methyl 2-cyano-6-fluorobenzo[d]thiazole-4-carboxylate

To a solution of methyl methyl (Z)-3-bromo-2-((4-chloro-5H-1,2,3-dithiazol-5-ylidene)amino)-5-fluorobenzoate (200 mg, 521 μmol) in pyridine (4 mL) was added CuI (99 mg, 521 μmol). The mixture was stirred under microwave irradiation (400 W) 115° C. for 0.5 hr. The reaction was diluted with $H_2O$ (20 mL) and extracted with EtOAc (10 mL×3). The combined organic layers were washed with 0.5 M HCl (5 mL×3) and brine (10 mL×5), dried over $Na_2SO_4$, filtered, and concentrated under reduced pressure to give a residue. The residue was purified by silica gel flash chromatography (Eluent of 6~8% Ethyl acetate in petroleum ether), Methyl 2-cyano-6-fluorobenzo[d]thiazole-4-carboxylate (65 mg, yield: 51%) was obtained as white solid, which was used directly to the next step. MS: m/z=236.7 [M+H]$^+$. $^1$H NMR (400 MHz, Dimethylsulfoxide-d$_6$) δ 8.01 (dd, J=9.2, 2.8 Hz, 1H), 7.87 (dd, J=7.2, 2.8 Hz, 1H), 4.08 (s, 3H). $^1$F NMR (400 MHz, Chloroform-d) δ –108.7.

Step 4: 2-Carbamoyl-6-fluorobenzo[d]thiazole-4-carboxylic acid

A mixture of methyl 2-cyano-6-fluorobenzo[d]thiazole-4-carboxylate (20 mg, 85 μmol), LiOH·$H_2O$ (3 mg, 85 μmol) in THF (1 mL) and $H_2O$ (1 mL) was stirred at 60° C. for 0.5 hr. The reaction was concentrated under reduced pressure to give 2-carbamoyl-6-fluorobenzo[d]thiazole-4-carboxylic acid (Intermediate 27, 15 mg, yield: 68%) was obtained as white solid, which was used directly used to the next step without further purification. MS: m/z=240.6 [M+H]$^+$. 1 H NMR (400 MHz, Dimethylsulfoxide-d$_6$) δ 8.37 (br s, 1H), 8.07 (br s, 1H), 7.90 (dd, J=8.4, 3.2 Hz, 1H), 7.41-7.34 (m, 1H). $^1$F NMR (400 MHz, Chloroform-d) 6-114.2.

Intermediate 28: 3-(3-(4-(((3S,5S)-3,5-Dimethylpiperazin-1-yl)methyl)phenyl)-5-phenyl-3H-imidazo[4,5-b]pyridin-2-yl)pyridin-2-amine

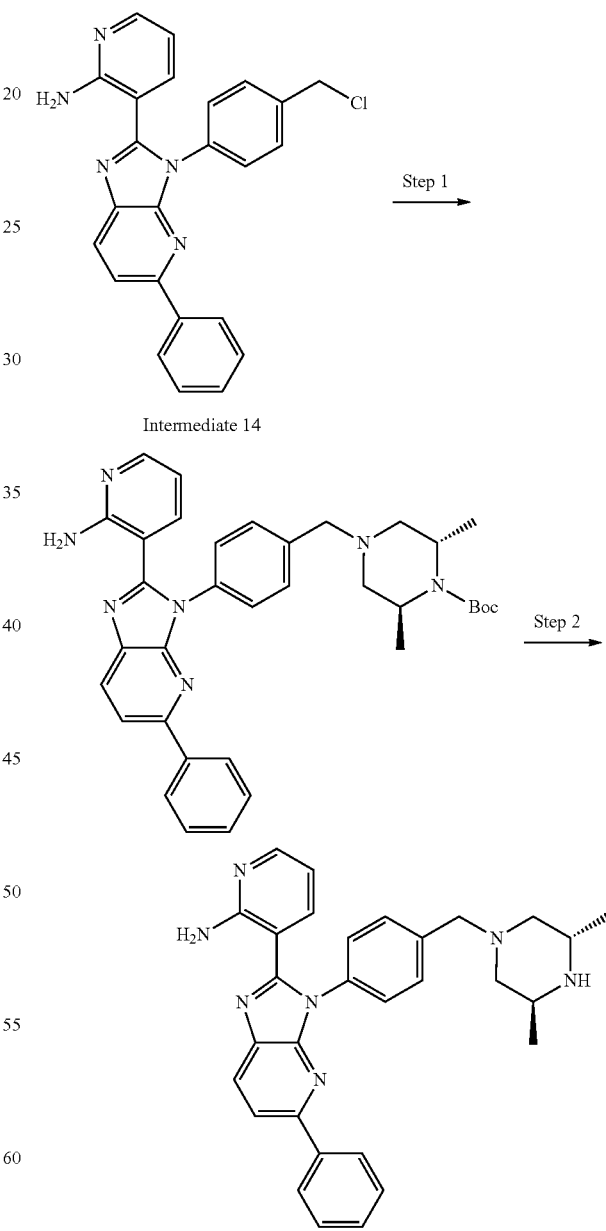

Intermediate 28

Step 1: Tert-butyl (2S,6S)-4-(4-(2-(2-aminopyridin-3-yl)-5-phenyl-3H-imidazo[4,5-b]pyridin-3-yl)benzyl)-2,6-dimethylpiperazine-1-carboxylate To a solution of Intermediate 14 (1.0 g, 2.43 mmol) in DMF (4 mL) were added K₂CO₃ (671 mg, 4.86 mmol) and tert-butyl (2R,6R)-2,6-dimethylpiperazine-1-carboxylate (624 mg, 2.91 mmol). The mixture was stirred at 25° C. for 16 hr. The reaction mixture was quenched with H₂O (10 mL) at 25° C., and then diluted with CH₂Cl₂ (6 mL) and extracted with H₂O (20 mL×3). The combined organic layers were washed with 20 mL brine, dried over Na₂SO₄, filtered, and concentrated under reduced pressure to give a residue. The residue was purified by flash chromatography on silica gel (Eluent of 0~10% MeOH in CH₂Cl₂), tert-butyl (2S,6S)-4-(4-(2-(2-aminopyridin-3-yl)-5-phenyl-3H-imidazo[4,5-b]pyridin-3-yl)benzyl)-2,6-dimethylpiperazine-1-carboxylate (750 mg, yield: 52%) was obtained as a yellow solid. MS: m/z=590.3 [M+H]⁺. ¹H NMR (400 MHz, Dimethylsulfoxide-d₆) δ 8.26 (d, J=8.4 Hz, 1H), 8.04-7.95 (m, 4H), 7.51-7.38 (m, 7H), 7.16 (dd, J=7.6, 1.6 Hz, 1H), 7.04 (br s, 2H), 6.38 (dd, J=8.0, 4.8 Hz, 1H), 3.82-3.75 (m, 2H), 3.64 (d, J=13.6 Hz, J H), 3.47 (d, J=13.6 Hz, 1H), 2.90-2.86 (m, 1H), 2.76-2.70 (m, 1H), 2.26-2.18 (m, 2H), 1.40 (s, 9H), 1.22 (d, J=6.4 Hz, 6H).

Step 2: 3-(3-(4-(((3S,5S)-3,5-Dimethylpiperazin-1-yl)methyl)phenyl)-5-phenyl-3H-imidazo[4,5-b]pyridin-2-yl)pyridin-2-amine A solution of tert-butyl (2S,6S)-4-(4-(2-(2-aminopyridin-3-yl)-5-phenyl-3H-imidazo[4,5-b]pyridin-3-yl)benzyl)-2,6-dimethylpiperazine-1-carboxylate (700 mg, 1.19 mmol) in HCl/1,4-dioxane (10 mL) was stirred at 25° C. for 2 hr. The reaction was filtered and concentrated under reduced pressure to give 3-(3-(4-(((3S,5S)-3,5-dimethylpiperazin-1-yl)methyl)phenyl)-5-phenyl-3H-imidazo[4,5-b]pyridin-2-yl)pyridin-2-amine (Intermediate 28, 540 mg, HCl salt, yield: 86%) as a white solid MS: m/z=490.6 [M+H]⁺. ¹H NMR (400 MHz, Dimethylsulfoxide-d₆) δ 8.27 (d, J=8.4 Hz, 1H), 8.08-7.95 (m, 4H), 7.52-7.35 (m, 7H), 7.15 (dd, J=7.6, 1.6 Hz, 1H), 7.04 (br s, 2H), 6.40-6.34 (m, 1H), 3.54 (d, J=14.0 Hz, 1H), 3.45-3.40 (m, 1H), 3.10-3.04 (m, 2H), 2.41-2.33 (m, 2H), 2.06-2.00 (m, 2H), 1.04 (d, J=6.4 Hz, 6H).

Intermediate 29: 3-(3-(4-(((3R,5R)-3,5-dimethylpiperazin-1-yl)methyl)phenyl)-5-phenyl-3H-imidazo[4,5-b]pyridin-2-yl)pyridin-2-amine

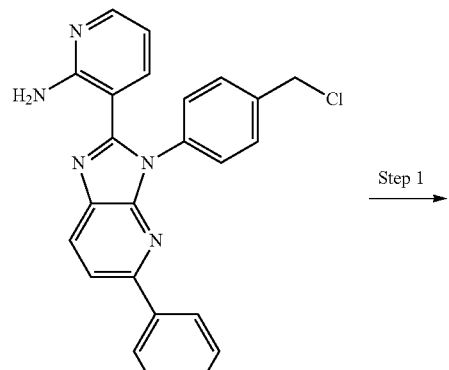

Intermediate 14

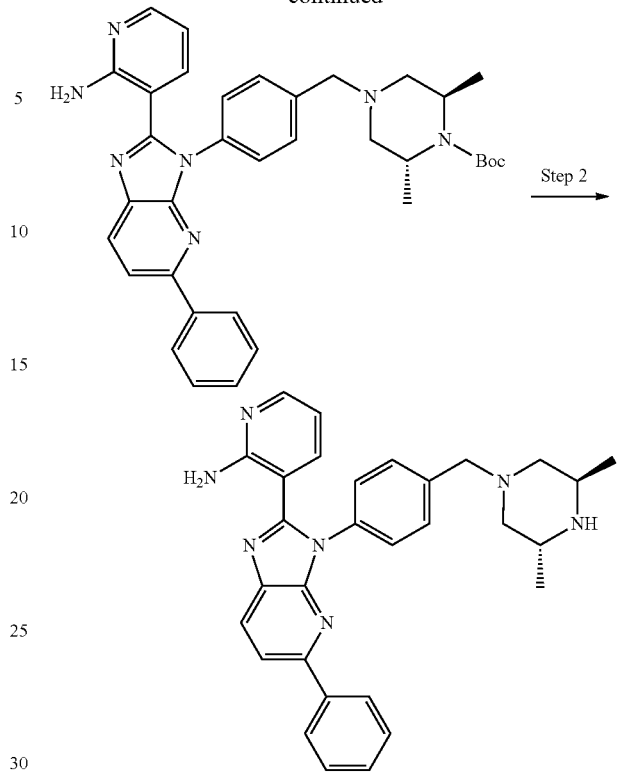

Intermediate 29

Step 1: Tert-butyl (2R,6R)-4-(4-(2-(2-aminopyridin-3-yl)-5-phenyl-3H-imidazo[4,5-b]pyridin-3-yl)benzyl)-2,6-dimethylpiperazine-1-carboxylate To a solution of Intermediate 14 (1.06 g, 2.57 mmol), tert-butyl (2R,6R)-2,6-dimethylpiperazine-1-carboxylate (500 mg, 2.33 mmol) in DMF (10 mL) was added DIEA (905 mg, 7.0 mmol). The mixture was stirred at 80° C. for 16 hr. The mixture was quenched with H₂O (40 mL) and extracted with EtOAc (40 mL×3), the combined organic layers were dried over anhydrous Na₂SO₄, filtered, and concentrated to give a residue. The residue was purified by silica gel flash chromatography (Eluent of 0~9% MeOH in CH₂Cl₂), tert-butyl (2R,6R)-4-(4-(2-(2-aminopyridin-3-yl)-5-phenyl-3H-imidazo[4,5-b]pyridin-3-yl)benzyl)-2,6-dimethylpiperazine-1-carboxylate (Intermediate 29, 1 g, yield: 69.4%) was obtained as a yellow solid. MS: m/z=590.4 [M+H]⁺. ¹H NMR (400 MHz, Dimethylsulfoxide-d₆) δ 8.27 (d, J=8.4 Hz, 1H), 8.05-7.98 (m, 4H), 7.52-7.43 (m, 6H), 7.42-7.36 (m, 1H), 7.16 (dd, J=7.6, 1.6 Hz, 1H), 7.04 (br s, 2H), 6.37 (dd, J=7.6, 4.8 Hz, 1H), 3.83-3.74 (m, 2H), 3.65 (d, J=13.6 Hz, 1H), 3.48 (d, J=13.6 Hz, 1H), 3.35-3.39 (m, 2H), 2.27-2.19 (m, 2H), 1.42-1.41 (m, 1H), 1.40 (s, 9H), 1.23 (d, J=6.4 Hz, 6H).

Step 2: 3-(3-(4-(((3R,5R)-3,5-Dimethylpiperazin-1-yl)methyl)phenyl)-5-phenyl-3H-imidazo[4,5-b]pyridin-2-yl)pyridin-2-amine A solution of tert-butyl (2R,6R)-4-(4-(2-(2-aminopyridin-3-yl)-5-phenyl-3H-imidazo[4,5-b]pyridin-3-yl)benzyl)-2,6-dimethylpiperazine-1-carboxylate (100 mg, 169 μmol) in HCl/1,4-dioxane (4M, 1 mL) was stirred at 25° C. for 0.5 hr.

The mixture was filtered to give 3-(3-(4-(((3R,5R)-3,5-dimethylpiperazin-1-yl)methyl)phenyl)-5-phenyl-3H-imidazo[4,5-b]pyridin-2-yl)pyridin-2-amine (Intermediate 29, 84 mg HCl salt, yield: 95%) as a yellow solid. MS: m/z=490.2 [M+H]$^+$. $^1$H NMR (400 MHz, Dimethylsulfoxide-d$_6$) δ 12.41-11.57 (m, 0.5H), 10.79-10.27 (m, 0.5H), 10.07-9.71 (m, 1H), 8.65-8.51 (m, 1H), 8.38 (d, J=8.4 Hz, 1H), 8.16 (d, J=6.0 Hz, 1H), 8.11-7.95 (m, 4H), 7.93-7.82 (m, 3H), 7.68 (d, J=8.0 Hz, 2H), 7.51-7.42 (m, 3H), 7.04 (t, J=6.8 Hz, 1H), 4.50-4.25 (m, 2H), 3.44-3.32 (m, 2H), 3.20-3.01 (m, 2H), 2.91-2.87 (m, 1H), 2.75-2.71 (m, 1H), 1.60-1.31 (m, 6H).

Intermediate 30: 3-[3-[4-(4,7-Diazaspiro[2.5]octan-7-ylmethyl)phenyl]-5-phenyl-imidazo[4,5-b]pyridin-2-yl]pyridin-2-amine

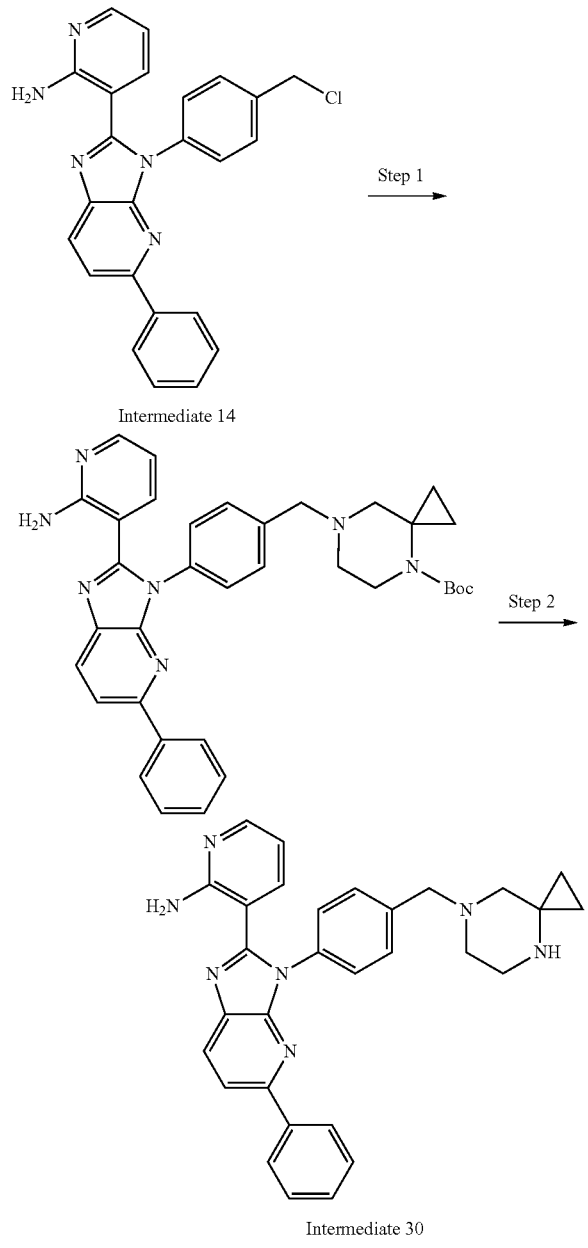

Step 1: Tert-butyl 7-(4-(2-(2-aminopyridin-3-yl)-5-phenyl-3H-imidazo[4,5-b]pyridin-3-yl)benzyl)-4,7-diazaspiro[2.5]octane-4-carboxylate To a solution of Intermediate 14 (1.0 g, 2.43 mmol) and tert-butyl 4,7-diazaspiro[2.5]octane-4-carboxylate (618 mg, 2.91 mmol) in DMF (10 mL) was added K$_2$CO$_3$ (671 mg, 4.86 mmol). The mixture was stirred at 25° C. for 24 hr. The reaction mixture was diluted with H$_2$O (10 mL) at 25° C. and extracted with CH$_2$Cl$_2$ (20 mL×3). The combined organic layers were washed with brine (15 mL), dried over Na$_2$SO$_4$, filtered, and concentrated under reduced pressure to give a residue. The residue was purified by silica gel flash chromatography (Eluent of 0~60% EtOAc in petroleum ether) to give tert-butyl 7-[[4-[2-(2-amino-3-pyridyl)-5-phenyl-imidazo[4,5-b]pyridin-3-yl]phenyl]methyl]-4,7-diazaspiro[2.5]octane-4-carboxylate (610 mg, yield: 38%) as a yellow solid, which was used directly in the next step without further purification. MS: m/z=588.1 [M+H]$^+$.

Step 2: 3-(3-(4-(4,7-Diazaspiro[2.5]octan-7-ylmethyl)phenyl)-5-phenyl-3H-imidazo[4,5-b]pyridin-2-yl)pyridin-2-amine To a solution of tert-butyl 7-[[4-[2-(2-amino-3-pyridyl)-5-phenyl-imidazo[4,5-b]pyridin-3-yl]phenyl]methyl]-4,7-diazaspiro[2.5]octane-4-carboxylate (500 mg, 0.851 mmol) in 1,4-dioxane (3 mL) was added HCl/1,4-dioxane (4M, 5 mL). The mixture was stirred at 25° C. for 1 hr. The reaction mixture was concentrated under reduced pressure to remove 1,4-dioxane.

The crude was dissolved in H$_2$O (5 mL) and extracted with CH$_2$Cl$_2$ (5 mL×3), the aqueous phase was added NaHCO$_3$ and extracted with CH$_2$Cl$_2$ (5 mL×3), filtered and concentrated to give 3-[3-[4-(4,7-diazaspiro[2.5]octan-7-ylmethyl)phenyl]-5-phenyl-imidazo[4,5-b]pyridin-2-yl]pyridin-2-amine (Intermediate 30, 350 mg, yield: 81%) as a yellow solid. MS: m/z=488.3 [M+H]$^+$. $^1$H NMR (400 MHz, Dimethylsulfoxide-d$_6$) δ 8.26 (d, J=8.4 Hz, 1H), 8.09-7.92 (m, 4H), 7.56-7.33 (m, 7H), 7.14 (dd, J=7.8, 1.8 Hz, 11H), 7.05 (br s, 2H), 6.34 (dd, J=7.6, 4.8 Hz, 1H), 3.52 (s, 2H), 2.76 (t, J=4.8 Hz, 2H), 2.44-2.32 (m, 2H), 2.18 (s, 2H), 0.47-0.38 (m, 2H), 0.35-0.25 (m, 2H).

Intermediate 31: 3-(3-(4-((3,8-Diazabicyclo[3.2.1]octan-3-yl)methyl)phenyl)-5-phenyl-3H-imidazo[4,5-b]pyridin-2-yl)pyridin-2-amine

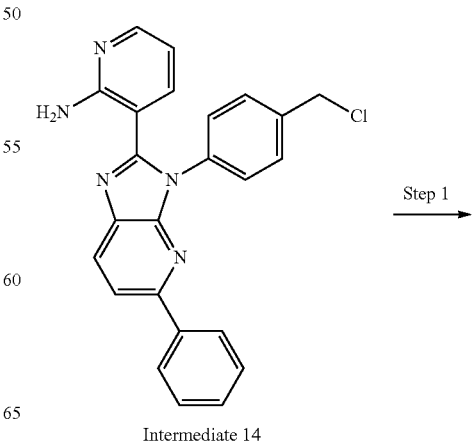

-continued

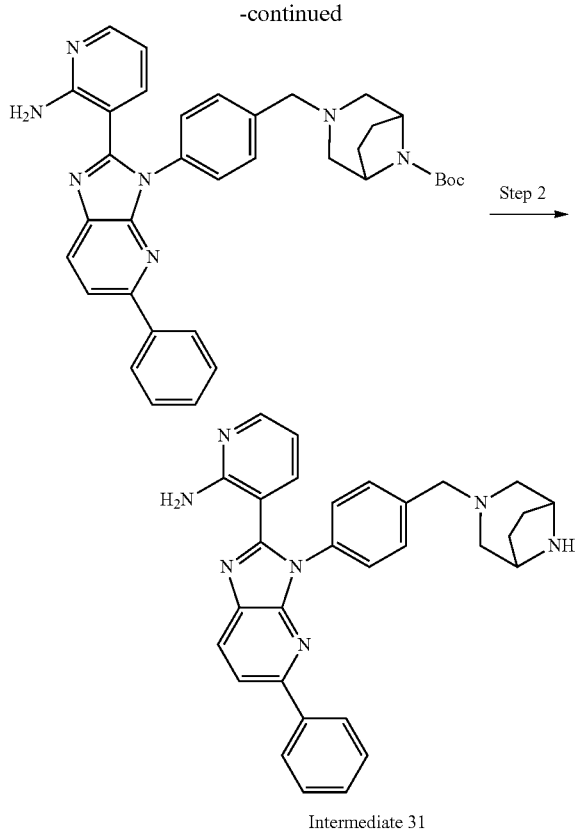

Intermediate 31

Step 1: Tert-butyl 3-(4-(2-(2-aminopyridin-3-yl)-5-phenyl-3H-imidazo[4,5-b]pyridin-3-yl)benzyl)-3,8-diazabicyclo[3.2.1]octane-8-carboxylate To a solution of Intermediate 14 (500 mg, 1.21 mmol) and tert-butyl 3,8-diazabicyclo[3.2.1]octane-8-carboxylate (309 mg, 1.46 mmol) in DMF (8 mL) was added $K_2CO_3$ (336 mg, 2.43 mmol). The mixture was stirred at 25° C. for 8 hr. The reaction mixture was diluted with $H_2O$ (10 mL) at 25° C. and extracted with $CH_2Cl_2$ (20 mL×3). The combined organic layers were washed with brine (30 mL), dried over $Na_2SO_4$, filtered, and concentrated under reduced pressure to give a residue. The residue was purified by flash chromatography on silica gel (Eluent of 0~10% EtOAc in petroleum ether), tert-butyl 3-(4-(2-(2-aminopyridin-3-yl)-5-phenyl-3H-imidazo[4,5-b]pyridin-3-yl)benzyl)-3,8-diazabicyclo[3.2.1]octane-8-carboxylate (450 mg, yield: 63%) as a yellow solid. MS: m/z=588.3 [M+H]$^+$.

Step 2: 3-(3-(4-((3,8-Diazabicyclo[3.2.1]octan-3-yl)methyl)phenyl)-5-phenyl-3H-imidazo[4,5-b]pyridin-2-yl)pyridin-2-amine To a solution of tert-butyl 3-(4-(2-(2-aminopyridin-3-yl)-5-phenyl-3H-imidazo[4,5-b]pyridin-3-yl)benzyl)-3,8-diazabicyclo[3.2.1]octane-8-carboxylate (450 mg, 0.766 mmol) in 1,4-dioxane (5 mL) was added HCl/1,4-dioxane (4M, 5 mL) at 25° C. The mixture was stirred at 25° C. for 6 hr. The reaction was filtered and concentrated under reduced pressure to give 3-(3-(4-((3,8-diazabicyclo[3.2.1]octan-3-yl)methyl)phenyl)-5-phenyl-3H-imidazo[4,5-b]pyridin-2-yl)pyridin-2-amine (Intermediate 31, 240 mg, HCl salt) as a light yellow solid. MS: m/z=488.1 [M+H]$^+$. $^1$H NMR (400 MHz, Methanol-$d_4$) δ8.34-8.28 (m, 1H), 8.05-7.95 (m, 4H), 7.90-7.85 (m, 3H), 7.65 (d, J=8.0 Hz, 2H), 7.48-7.37 (m, 3H), 6.90 (t, J=6.8 Hz, 1H), 4.35-4.25 (m, 4H), 3.50-3.40 (m, 4H), 2.41 (d, J=8.4 Hz, 2H), 2.25-2.16 (m, 2H).

Intermediate 32: 3-(3-(4-((3,8-diazabicyclo[3.2.1]octan-8-yl)methyl)phenyl)-5-phenyl-3H-imidazo[4,5-b]pyridin-2-yl)pyridin-2-amine

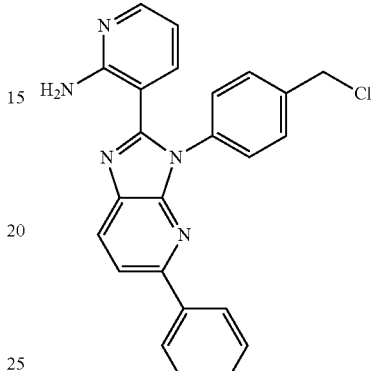

Intermediate 14

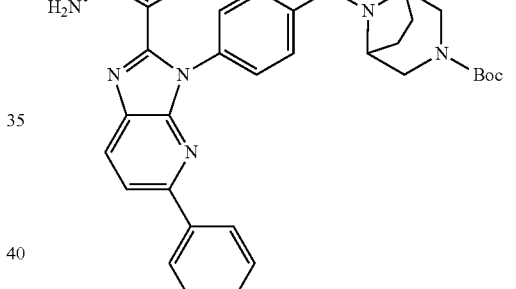

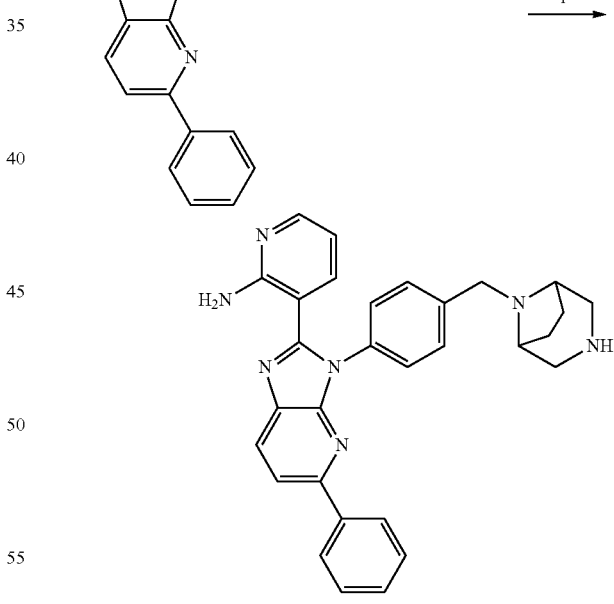

Intermediate 32

Step 1: Tert-butyl 8-(4-(2-(2-aminopyridin-3-yl)-5-phenyl-3H-imidazo[4,5-b]pyridin-3-yl)benzyl)-3,8-diazabicyclo[3.2.1]octane-3-carboxylate To a solution of Intermediate 14 (1.0 g, 2.43 mmol) and tert-butyl 3,8-diazabicyclo[3.2.1]octane-3-carboxylate (618 mg, 2.91 mmol) in DMF (15 mL) was added $K_2CO_3$ (671 mg, 4.86 mmol). The mixture was stirred at 25° C. for 8 hr. The reaction mixture was diluted with H₂O (10 mL) at 25° C. and extracted with CH₂Cl₂ (20 mL×3). The combined organic layers were washed with brine (30 mL), dried over Na₂SO₄, filtered and concentrated under reduced pressure to give a residue. The residue was purified by flash chromatography on silica gel (Eluent of 0~10% EtOAc in petroleum ether), tert-butyl 8-(4-(2-(2-aminopyridin-3-yl)-5-phenyl-3H-imidazo[4,5-b]pyridin-3-yl)benzyl)-3,8-diazabicyclo[3.2.1]octane-3-carboxylate (956 mg, yield: 67%) was obtained as a yellow solid. MS: m/z=588.2 [M+H]⁺. ¹H NMR (400 MHz, Dimethylsulfoxide-d₆) δ 8.26 (d, J=8.4 Hz, 1H), 8.05-7.95 (m, 4H), 7.55 (d, J=8.4 Hz, 2H), 7.48-7.37 (m, 5H), 7.16 (dd, J=7.6, 1.6 Hz, 1H), 7.01 (br s, 2H), 6.38 (dd, J=7.6, 4.8 Hz, 1H), 3.59 (s, 2H), 3.20-2.85 (m, 6H), 2.02-1.92 (m, 2H), 1.54-1.48 (m, 2H), 1.40 (s, 9H).

Step 2: 3-(3-(4-((3,8-Diazabicyclo[3.2.1]octan-8-yl)methyl)phenyl)-5-phenyl-3H-imidazo[4,5-b]pyridin-2-yl)pyridin-2-amine To a solution of tert-butyl 8-(4-(2-(2-aminopyridin-3-yl)-5-phenyl-3H-imidazo[4,5-b]pyridin-3-yl)benzyl)-3,8-diazabicyclo[3.2.1]octane-3-carboxylate (600 mg, 1.02 mmol) in 1,4-dioxane (5 mL) was added HCl/1,4-dioxane (4M, 5 mL) at 25° C. The mixture was stirred at 25° C. for 6 hr. The reaction was filtered and concentrated under reduced pressure to give 3-(3-(4-((3,8-diazabicyclo[3.2.1]octan-8-yl)methyl)phenyl)-5-phenyl-3H-imidazo[4,5-b]pyridin-2-yl)pyridin-2-amine (Intermediate 32, 535 mg, HCl salt) as a light yellow solid. MS: m/z=488.2 [M+H]⁺. ¹H NMR (400 MHz, Dimethylsulfoxide-d₆) δ 12.42 (br s, 1H), 10.4-10.0 (m, 2H), 8.55 (br s, 1H), 8.38 (d, J=8.0 Hz, 1H), 8.13-8.07 (m, 1H), 8.06-8.00 (m, 5H), 7.98-7.94 (m, 1H), 7.69 (d, J=8.0 Hz, 2H), 7.50-7.40 (m, 3H), 6.94 (t, J=7.2 Hz, 1H), 4.39-4.33 (m, 2H), 4.01 (s, 2H), 3.95-3.89 (m, 3H), 3.42-3.39 (m, 3H), 2.47-2.38 (m, 2H).

Intermediate 33: 3-(4-(2-(2-Aminopyridin-3-yl)-5-phenyl-3H-imidazo[4,5-b]pyridin-3-yl)benzyl)-3-azabicyclo[3.2.1]octan-8-amine

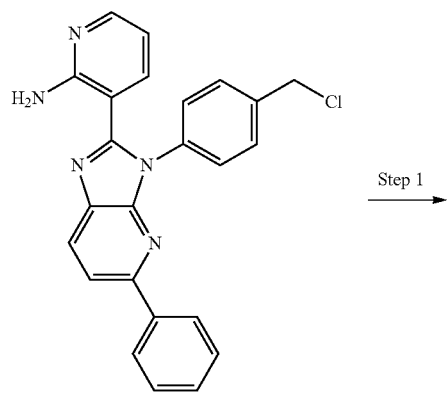

Intermediate 14

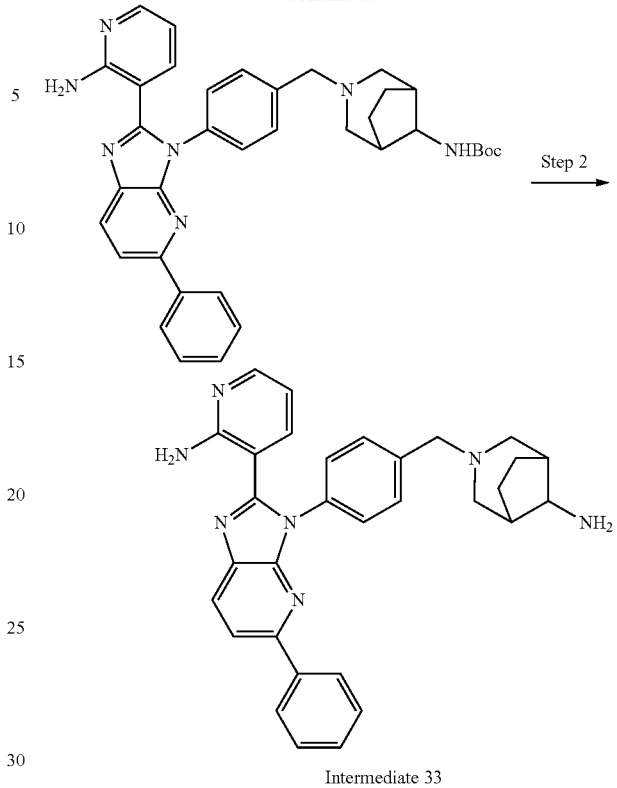

Intermediate 33

Step 1: Tert-butyl (3-(4-(2-(2-aminopyridin-3-yl)-5-phenyl-3H-imidazo[4,5-b]pyridin-3-yl)benzyl)-3-azabicyclo[3.2.1]octan-8-yl)carbamate To a solution of Intermediate 14 and tert-butyl (3-azabicyclo[3.2.1]octan-8-yl)carbamate (549 mg, 2.43 mmol) in DMF (10 mL) were added K₂CO₃ (1.01 g, 7.28 mmol) and NaI (36.4 mg, 243 µmol). The resulting mixture was stirred at 25° C. for 14 hr. Then the reaction mixture was diluted with H₂O (50 mL) and extracted with CH₂Cl₂ (50 mL×2). The combined organic layers were dried over Na₂SO₄, filtered and concentrated under reduced pressure to give a residue. The crude product was purified by column chromatography (Eluent of 30~50% ethyl acetate in petroleum ether), tert-butyl (3-(4-(2-(2-aminopyridin-3-yl)-5-phenyl-3H-imidazo[4,5-b]pyridin-3-yl)benzyl)-3-azabicyclo[3.2.1]octan-8-yl)carbamate (500 mg, yield: 32%) was obtained as a yellow solid. MS: m/z=602.3 [M+H]⁺. ¹H NMR (400 MHz, Dimethylsulfoxide-d₆) δ 8.26 (d, J=8.4 Hz, 1H), 8.04-7.94 (m, 4H), 7.50-7.39 (m, 7H), 7.15 (d, J=7.2 Hz, 1H), 7.05 (br s, 2H), 6.92-6.79 (m, 1H), 6.41-6.32 (m, 1H), 3.60-3.51 (m, 2H), 2.66-2.63 (m, 1H), 2.38-2.33 (dd, J=10.4, 2.8 Hz, 1H), 2.15 (d, J=10.4 Hz, 1H), 2.10-2.02 (m, 2H), 1.74-1.57 (m, 4H), 1.42-1.37 (m, 9H), 1.30-1.18 (m, 2H).

Step 2: 3-(4-(2-(2-Aminopyridin-3-yl)-5-phenyl-3H-imidazo[4,5-b]pyridin-3-yl)benzyl)-3-azabicyclo[3.2.1]octan-8-amine To a solution of tert-butyl (3-(4-(2-(2-aminopyridin-3-yl)-5-phenyl-3H-imidazo[4,5-b]pyridin-3-yl)benzyl)-3-azabicyclo[3.2.1]octan-8-yl)carbamate (500 mg, 831 µmol) in 1,4-dioxane (2 mL) was added HCl/dioxane (2 mL). The mixture was stirred at 25° C. for 0.5 hr. The reaction mixture was diluted with H₂O (10 mL) and extracted with 10 mL EtOAc. The aqueous layer was alkalized with NaHCO₃ to pH around 10, then extracted with EtOAc (20 mL×2). The combined organic layers were dried over Na₂SO₄, filtered and concentrated under reduced pressure to give a residue. The crude product was purified by column chromatography (Eluent of 5~10% MeOH in CH₂Cl₂), 3-(4-(2-(2-aminopyridin-3-yl)-5-phenyl-3H-imidazo[4,5-b]pyridin-3-yl)benzyl)-3-azabicyclo[3.2.1]octan-8-amine (Intermediate 33, 270 mg, yield: 62%) was obtained as a yellow solid. MS: m/z=502.3 [M+H]. ¹H NMR (400 MHz, Methanol-d₄)) δ 8.17 (d, J=8.4 Hz, 1H), 8.02 (d, J=7.2 Hz, 2H), 7.97 (dd, J=5.2, 1.6 Hz, 1H), 7.92 (d, J=8.4 Hz, 1H), 7.51 (d, J=8.4 Hz, 2H), 7.43-7.35 (m, 5H), 7.29 (dd, J=7.6, 1.6 Hz, 1H), 6.44 (dd, J=7.6, 4.8 Hz, 1H), 3.62 (s, 2H), 2.96 (t, J=4.4 Hz, 1H), 2.57-2.49 (m, 4H), 1.93-1.88 (m, 2H), 1.85-1.79 (m, 2H), 1.75-1.68 (m, 2H)

Intermediate 34: (S)-3-(3-(4-((3-methylpiperazin-1-yl)methyl)phenyl)-5-phenyl-3H-imidazo[4,5-b]pyridin-2-yl)pyridin-2-amine

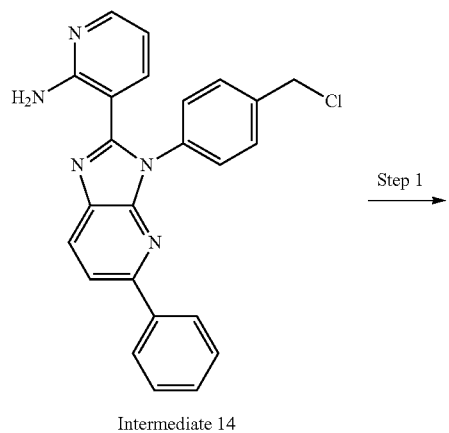

Intermediate 14

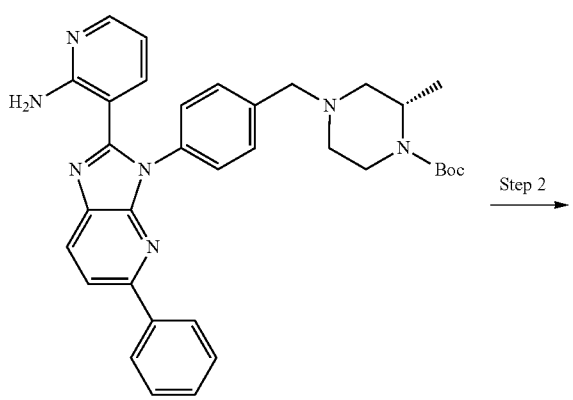

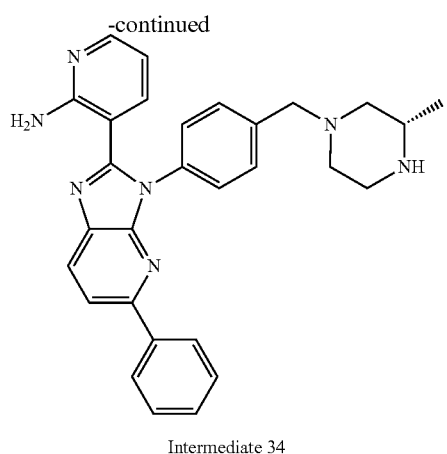

Intermediate 34

Step 1: (S)-Tert-butyl 4-(4-(2-(2-aminopyridin-3-yl)-5-phenyl-3H-imidazo[4,5-b]pyridin-3-yl)benzyl)-2-methylpiperazine-1-carboxylate To a solution of Intermediate 14 (1.0 g, 2.43 mmol) and (S)-tert-butyl 2-methylpiperazine-1-carboxylate (583 mg, 2.91 mmol) in DMF (10 mL) was added K₂CO₃ (671 mg, 4.86 mmol). The mixture was stirred at 25° C. for 24 hr. The reaction mixture was diluted with H₂O (10 mL) at 25° C. and extracted with CH₂Cl₂ (20 mL×3). The combined organic layers were washed with (15 mL), dried over Na₂SO₄, filtered, and concentrated under reduced pressure to give a residue. The residue was purified by silica gel flash chromatography (Eluent of 0~60% EtOAc in petroleum ether) to give tert-butyl tert-butyl (S)-4-(4-(2-(2-aminopyridin-3-yl)-5-phenyl-3H-imidazo[4,5-b]pyridin-3-yl)benzyl)-2-methylpiperazine-1-carboxylate (550 mg, yield: 35%) as a yellow solid, which was used directly in the next step without further purification. MS: m/z=576.1 [M+H]⁺.

Step 2: (S)-3-(3-(4-((3-Methylpiperazin-1-yl)methyl)phenyl)-5-phenyl-3H-imidazo[4,5-b]pyridin-2-yl)pyridin-2-amine To a solution of (S)-4-(4-(2-(2-aminopyridin-3-yl)-5-phenyl-3H-imidazo[4,5-b]pyridin-3-yl)benzyl)-2-methylpiperazine-1-carboxylate (500 mg, 0.869 mmol) in HCl/1,4-dioxane (4M, 5 mL) was added. The mixture was stirred at 25° C. for 1 hr. The reaction mixture was concentrated under reduced pressure to remove 1,4-dioxane. The crude product was triturated with MeOH (2 mL) at 25° C. for 0.5 hr to give (S)-3-(3-(4-((3-methylpiperazin-1-yl)methyl)phenyl)-5-phenyl-3H-imidazo[4,5-b]pyridin-2-yl)pyridin-2-amine (Intermediate 34, 350 mg, yield: 82%) as a yellow solid. MS: m/z=476.2 [M+H]⁺. ¹H NMR (400 MHz, Methanol-d₄) δ 8.32 (d, J=8.4 Hz, 1H), 8.07-7.99 (m, 4H), 7.94-7.84 (m, 3H), 7.73 (d, J=8.4 Hz, 2H), 7.50-7.37 (m, 3H), 6.96-6.88 (m, 1H), 4.57 (s, 1H), 4.60-4.53 (s, 2H), 3.94-3.83 (m, 1H), 3.81-3.69 (m, 3H), 3.68-3.56 (m, 1H), 3.54-3.41 (m, 1H), 3.39-3.31 (m, 1H), 1.45 (d, J=6.8 Hz, 3H).

Intermediate 35: 3-(3-(4-((1,4-Diazepan-1-yl)methyl)phenyl)-5-phenyl-3H-imidazo[4,5-b]pyridin-2-yl)pyridin-2-amine

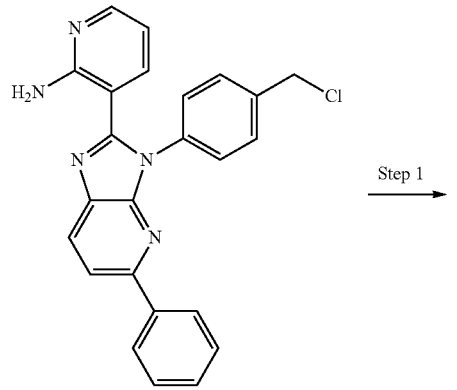

Intermediate 14

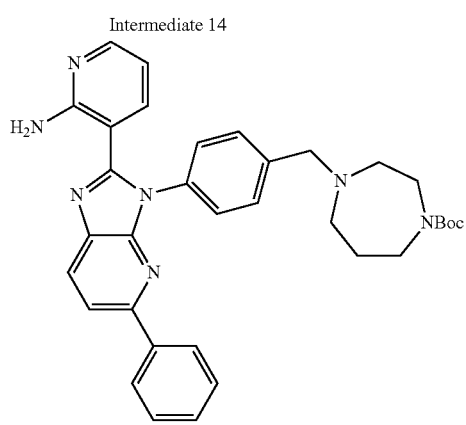

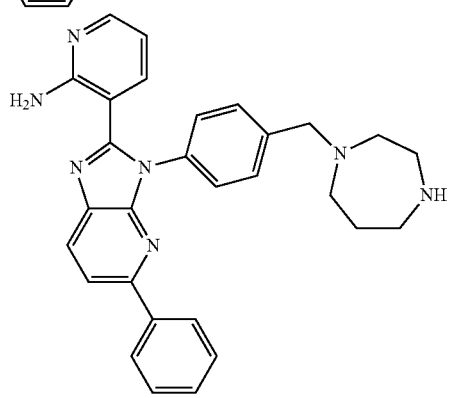

Intermediate 35

Step 1: Tert-butyl 4-(4-(2-(2-aminopyridin-3-yl)-5-phenyl-3H-imidazo[4,5-b]pyridin-3-yl)benzyl)-1,4-diazepane-1-carboxylate To a solution of Intermediate 14 (1 g, 2.43 mmol), tert-butyl 1,4-diazepane-1-carboxylate (584 mg, 2.92 mmol) in ACN (20 mL) was added NaI (36.4 mg, 243 µmol) and $K_2CO_3$ (671 mg, 4.86 mmol). The mixture was stirred at 80° C. for 2 hr. The reaction mixture was concentrated directly. The residue was purified by silica gel flash chromatography (Eluent of 0~10% MeOH in $CH_2Cl_2$) to give tert-butyl 4-[[4-[2-(2-amino-3-pyridyl)-5-phenyl-imidazo[4,5-b]pyridin-3-yl]phenyl]methyl]-1,4-diazepane-1-carboxylate (520 mg, yield: 33%) as a light-yellow solid, which was used directly in the next step without further purification. MS: m/z=576.4 [M+H]+.

Step 2: 3-(3-(4-((1,4-Diazepan-1-yl)methyl)phenyl)-5-phenyl-3H-imidazo[4,5-b]pyridin-2-yl)pyridin-2-amine To a solution of tert-butyl 4-[[4-[2-(2-amino-3-pyridyl)-5-phenyl-imidazo[4,5-b]pyridin-3-yl]phenyl]methyl]-1,4-diazepane-1-carboxylate (520 mg, 0.903 mmol) in HCl/1,4-dioxane (4M, 10 mL). The mixture was stirred at 25 C for 1 hr. The reaction mixture was concentrated directly to give the crude product (310 mg HCl salt, yield: 67%). The 100 mg was purified by prep-HPLC (column: Phenomenex C18 150×25 mm×10 um; mobile phase: [water ($NH_4HCO_3$)-ACN]; B %: 28%-58%, 8 min) to give 3-[3-[4-(1,4-diazepan-1-ylmethyl)phenyl]-5-phenyl-imidazo[4,5-b]pyridin-2-yl]pyridin-2-amine (Intermediate 35, 9 mg) as light-yellow solid. MS: m/z=476.3 [M+H]+. $^1$H NMR (400 MHz, Dimethylsulfoxide-$d_6$) δ 8.4 (d, J=8.4 Hz, 1H), 8.04-7.97 (m, 4H), 7.52-7.39 (m, 7H), 7.14 (dd, J=7.6, 1.8 Hz, 1H), 7.05 (br s, 2H), 6.39-6.34 (m, 1H), 3.72 (s, 2H), 2.82 (t, J=6.4 Hz, 2H), 2.78-2.74 (m, 2H), 2.67 (t, J=6.4 Hz, 2H), 2.66-2.57 (m, 2H), 1.78-1.64 (m, 2H).

Intermediate 36: 3-(3-(4-((4-(Methylamino)piperidin-1-yl)methyl)phenyl)-5-phenyl-3H-imidazo[4,5-b]pyridin-2-yl)pyridin-2-amine

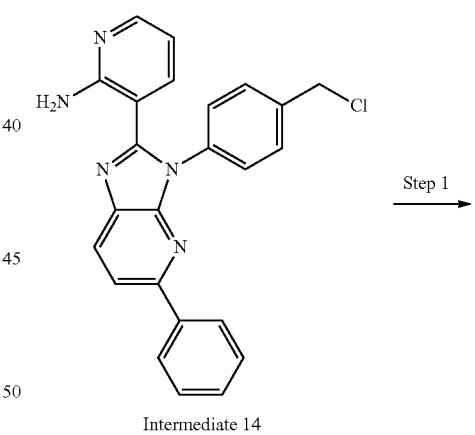

Intermediate 14

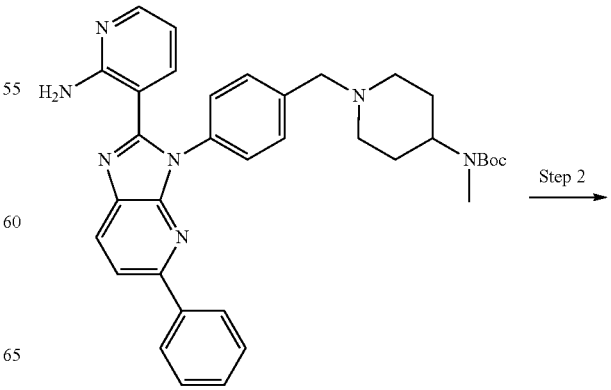

-continued

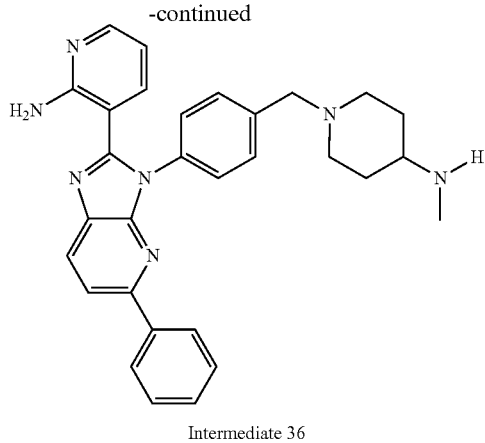

Intermediate 36

Step 1: 3-[3-[4-[[4-(methylamino)-1-piperidyl]methyl]phenyl]-5-phenyl-imidazo[4,5-b]pyridin-2-yl]pyridin-2-amine To a solution of Intermediate 14 (300 mg, 0.73 mmol) and tert-butyl N-methyl-N-(4-piperidyl)carbamate (312 mg, 1.46 mmol) in DMF (2 mL) were added NaI (18.2 mg, 0.073 mmol) and $K_2CO_3$ (336 mg, 2.43 mmol). The mixture was stirred at 80° C. for 2 hr. After cooling to 20° C., the reaction mixture was poured into $H_2O$ (3 mL), extracted with EtOAc (10 mL×3). The combined organic layers were dried over anhydrous $Na_2SO_4$, filtered, and concentrated under reduced pressure to give a residue. The residue was purified by silica gel flash chromatography (Eluent of 0~7% MeOH in $CH_2Cl_2$) to give tert-butyl N-[1-[[4-[2-(2-amino-3-pyridyl)-5-phenyl-imidazo[4,5-b]pyridin-3-yl]phenyl]methyl]-4-piperidyl]-N-methyl-carbamate (220 mg, yield: 51%,) as a yellow solid. MS: m/z=590.3 [M+H]⁺.

Step 2: 3-(3-(4-((4-(Methylamino)piperidin-1-yl)methyl)phenyl)-5-phenyl-3H-imidazo[4,5-b]pyridin-2-yl)pyridin-2-amine To a solution of tert-butyl N-[1-[[4-[2-(2-amino-3-pyridyl)-5-phenyl-imidazo[4,5-b]pyridin-3-yl]phenyl]methyl]-4-piperidyl]-N-methyl-carbamate (200 mg, 0.339 mmol) in $CH_2Cl_2$ (2 mL) was added TFA (38.7 mg, 0.339 mmol). The mixture was stirred at 25° C. for 2 hr. The reaction mixture was concentrated directly to give a residue (185 mg TFA salt, yield: 93%). The 50 mg crude product was diluted with aqueous $NaHCO_3$ (10 mL) and extracted with $CH_2Cl_2$ (10 mL×3). and then purified by prep-TLC ($CH_2Cl_2$: MeOH=10:1) to give 3-[3-[4-[[4-(methylamino)-1-piperidyl]methyl]phenyl]-5-phenyl-imidazo[4,5-b]pyridin-2-yl]pyridin-2-amine (Intermediate 36) as an off-white solid. MS: m/z=490.2 [M+H]⁺. ¹H NMR (400 MHz, Dimethylsulfoxide-d₆) δ 8.27 (d, J=8.4 Hz, 1H), 8.07-7.94 (m, 4H), 7.53-7.43 (m, 6H), 7.41-7.39 (m, 1H), 7.16 (dd, J=7.8, 1.2 Hz, 1H), 7.02 (br s, 2H), 6.37 (dd, J=7.4, 4.8 Hz, 1H), 3.55 (s, 2H), 3.47-3.37 (m, 1H), 2.80 (br d, J=12.0 Hz, 2H), 2.31 (s, 3H), 2.01 (dd, J=11.4, 9.8 Hz, 2H), 1.85-1.77 (m, 2H), 1.36-1.22 (m, 2H).

Intermediate 37: 3-(3-(4-(((1R,4R)-2,5-Diazabicyclo[2.2.1]heptan-2-yl)methyl)phenyl)-5-phenyl-3H-imidazo[4,5-b]pyridin-2-yl)pyridin-2-amine

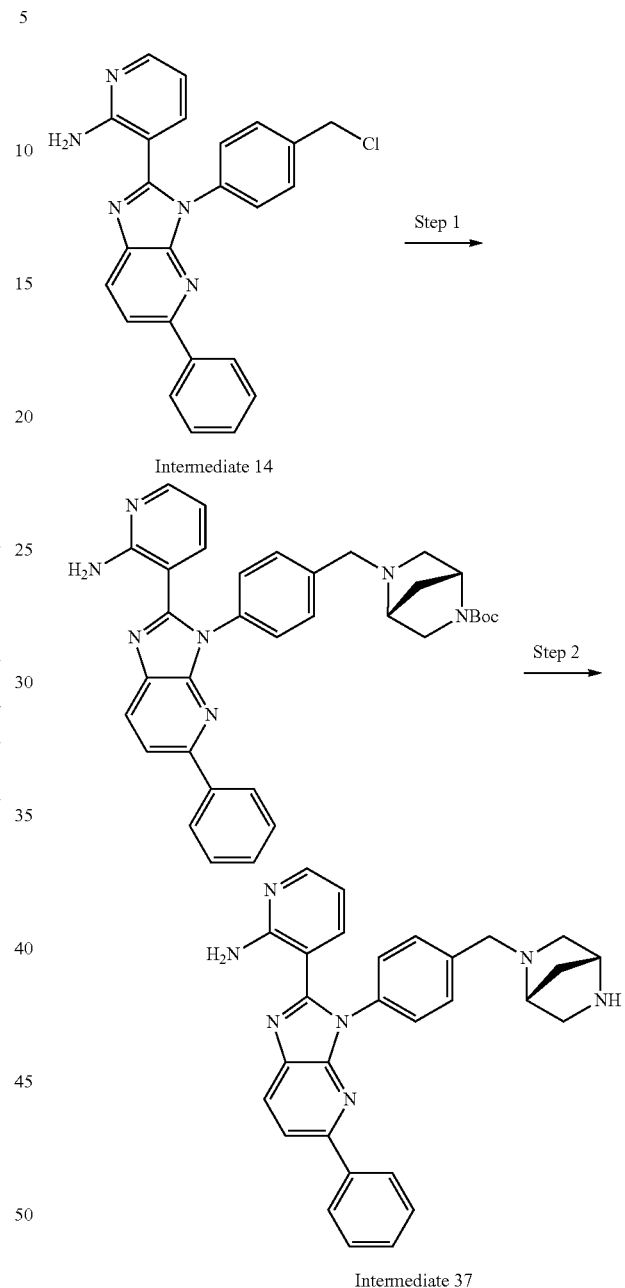

Intermediate 37

Step 1: Tert-butyl (1R,4R)-5-(4-(2-(2-aminopyridin-3-yl)-5-phenyl-3H-imidazo[4,5-b]pyridin-3-yl)benzyl)-2,5-diazabicyclo[2.2.1]heptane-2-carboxylate To a solution of Intermediate 14 (1.0 g, 2.43 mmol) and tert-butyl (1R,4R)-2,5-diazabicyclo[2.2.1]heptane-2-carboxylate (578 mg, 2.91 mmol) in DMF (15 mL) was added $K_2CO_3$ (671 mg, 4.86 mmol). The mixture was stirred at 25° C. for 16 hr. The reaction mixture was quenched with $H_2O$ (10 mL) at 25° C. and extracted with EtOAc (50 mL×3). The combined organic layers were washed with brine (20 mL×3), dried over $Na_2SO_4$, filtered, and concentrated under reduced pressure to give a residue. The residue was purified by silica gel flash chromatography ((Eluent of 0~10% MeOH in CH₂Cl₂), tert-butyl (1R,4R)-5-(4-(2-(2-aminopyridin-3-yl)-5-phenyl-3H-imidazo[4,5-b]pyridin-3-yl)benzyl)-2,5-diazabicyclo[2.2.1]heptane-2-carboxylate (1.0 g, yield: 72%) was obtained as a yellow solid. MS: m/z=574.2 [M+H]⁺.

Step 2: 3-(3-(4-(((1R,4R)-2,5-Diazabicyclo[2.2.1]heptan-2-yl)methyl)phenyl)-5-phenyl-3H-imidazo[4,5-b]pyridin-2-yl)pyridin-2-amine To a solution of tert-butyl (1R,4R)-5-(4-(2-(2-aminopyridin-3-yl)-5-phenyl-3H-imidazo[4,5-b]pyridin-3-yl)benzyl)-2,5-diazabicyclo[2.2.1]heptane-2-carboxylate (1.0 g, 1.74 mmol) in 1,4-dioxane (2 mL) was added HCl/1,4-dioxane (4M, 10 mL). The mixture was stirred at 25° C. for 2 hr. The reaction mixture was concentrated under reduced pressure to remove 1,4-dioxane. 3-(3-(4-(((1R,4R)-2,5-Diazabicyclo[2.2.1]heptan-2-yl)methyl)phenyl)-5-phenyl-3H-imidazo[4,5-b]pyridin-2-yl)pyridin-2-amine (Intermediate 37, 854 mg, 2HCl salt, yield: 90%) was obtained as a yellow solid. MS: m/z=474.2 [M+H]⁺. ¹H NMR (400 MHz, Methanol-d₄)δ 8.33 (d, J=8.4 Hz, 1H), 8.06-8.00 (m, 6H), 7.88 (dd, J=7.6, 1.6 Hz, 1H), 7.73 (d, J=8.4 Hz, 2H), 7.46-7.40 (m, 3H), 6.92 (dd, J=7.6, 6.4 Hz, 1H), 4.84-4.81 (m, 1H), 4.75-4.65 (m, 2H), 4.14 (d, J=12.8 Hz, 1H), 3.96-3.92 (m, 1H), 3.74-3.71 (m, 1H), 3.62-3.60 (m, 1H), 3.38-3.32 (m, 1H), 2.87-2.82 (m, 1H), 2.39-2.36 (m, 1H).

Intermediate 38: 3-(3-(4-((2,5-Diazabicyclo[2.2.2]octan-2-yl)methyl)phenyl)-5-phenyl-3H-imidazo[4,5-b]pyridin-2-yl)pyridin-2-amine

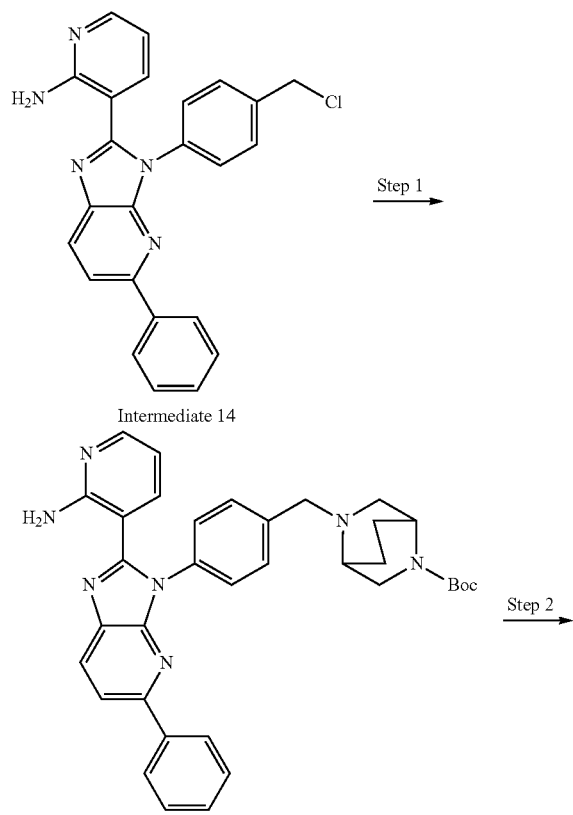

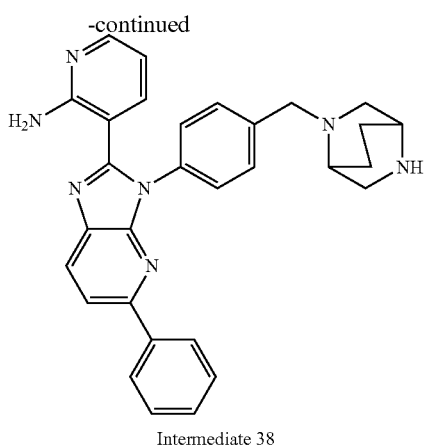

Intermediate 38

Step 1: Tert-butyl 5-(4-(2-(2-aminopyridin-3-yl)-5-phenyl-3H-imidazo[4,5-b]pyridin-3-yl)benzyl)-2,5-diazabicyclo[2.2.2]octane-2-carboxylate To a solution of Intermediate 14 (1.0 g, 2.43 mmol) and tert-butyl 2,5-diazabicyclo[2.2.2]octane-2-carboxylate (567 mg, 2.67 mmol) in MeCN (10 mL) was added K₂CO₃ (1.0 mg, 7.28 mmol,) and NaI (109 mg, 728 μmol). The mixture was stirred at 25° C. for 16 hr. The reaction mixture was diluted with H₂O (10 mL) at 25° C. and extracted with CH₂Cl₂ (10 mL×3). The combined organic layers were washed with brine (30 mL), dried over Na₂SO₄, filtered, and concentrated under reduced pressure to give a residue. The crude product was purified by flash chromatography on silica gel (Eluent of 0~5% MeOH in CH₂Cl₂), tert-butyl 5-(4-(2-(2-aminopyridin-3-yl)-5-phenyl-3H-imidazo[4,5-b]pyridin-3-yl)benzyl)-2,5-diazabicyclo[2.2.2]octane-2-carboxylate (700 mg, yield: 45%) was obtained as a yellow solid. MS: m/z=588.3 [M+H]⁺. ¹H NMR (400 MHz, Dimethylsulfoxide-d₆) δ 8.26 (d, J=8.4 Hz, 1H), 8.06-7.95 (m, 4H), 7.54-7.36 (m, 7H), 7.15 (dd, J=8.0, 1.6 Hz, 1H), 7.02 (s, 2H), 6.38 (dd, J=7.6, 4.8 Hz, 1H), 3.94-3.72 (m, 3H), 3.69-3.54 (m, 1H), 3.27-3.20 (m, 1H), 3.17 (d, J=5.2 Hz, 0.0.5H), 2.90-2.86 (m, 0.5H), 2.84-2.79 (m, 2H), 2.07-1.95 (m, 1H), 1.78-1.69 (m, 2H), 1.63-1.52 (m, 1H), 1.45-1.37 (d, J=9.6 Hz, 9H).

Step 2: 3-(3-(4-((2,5-Diazabicyclo[2.2.2]octan-2-yl)methyl)phenyl)-5-phenyl-3H-imidazo[4,5-b]pyridin-2-yl)pyridin-2-amine To a solution of tert-butyl 5-(4-(2-(2-aminopyridin-3-yl)-5-phenyl-3H-imidazo[4,5-b]pyridin-3-yl)benzyl)-2,5-diazabicyclo[2.2.2]octane-2-carboxylate (50 mg, 85 μmol) in 4 M HCl in 1,4-dioxane (1 mL). The mixture was stirred at 25° C. for 2 hr. The mixture was then filtered, the collected solid residue was washed with 1,4-dioxane (10 mL×2) and dried in vacuo to give 3-(3-(4-((2,5-diazabicyclo[2.2.2]octan-2-yl)methyl)phenyl)-5-phenyl-3H-imidazo[4,5-b]pyridin-2-yl)pyridin-2-amine (Intermediate 38, 44.9 mg, yield: 99%) as a yellow solid. MS: m/z=488.2 [M+H]⁺. ¹H NMR (400 MHz, Dimethylsulfoxide-d₆) δ 12.11-11.44 (m, 1H), 10.27-9.61 (m, 2H), 8.56-8.40 (m, 1H), 8.38 (d, J=8.4 Hz, 1H), 8.15 (dd, J=6.0, 1.2 Hz, 1H), 8.10-7.99 (m, 5H), 7.86 (dd, J=7.2, 1.2 Hz, 1H), 7.68 (d, J=8.4 Hz, 2H), 7.51-7.46 (m, 2H), 7.46-7.40 (m, 1H), 6.91 (dd, J=7.6, 6.4 Hz, 1H), 4.62 (br s, 2H), 4.01-3.79 (m, 4H), 3.76-3.70 (m, 2H), 2.21 (m, 2H), 1.97-1.80 (m, 2H).

Intermediate 39: 2-(4-Piperidylamino)pyridine-4-carbonitrile

Intermediate 40: 3-(3-(4-((4-Aminopiperidin-1-yl)methyl-d2)phenyl)-5-phenyl-3H-imidazo[4,5-b]pyridin-2-yl)pyridin-2-amine hydrochloride

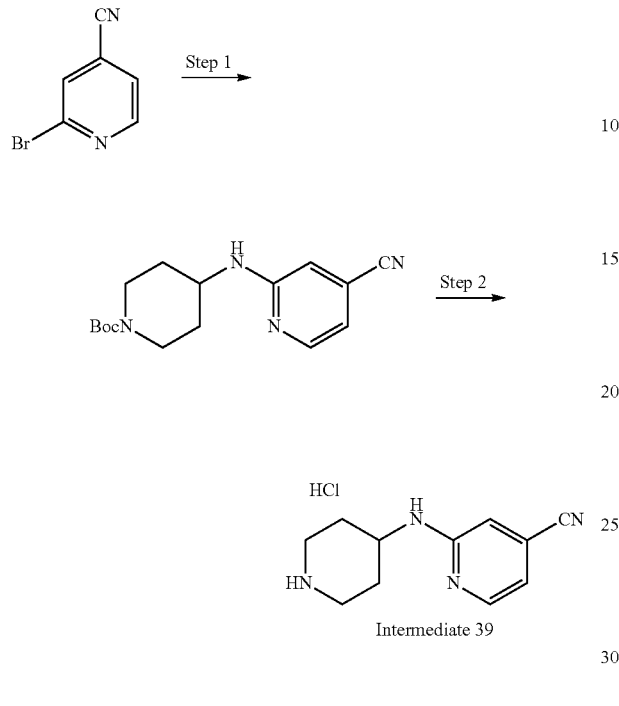

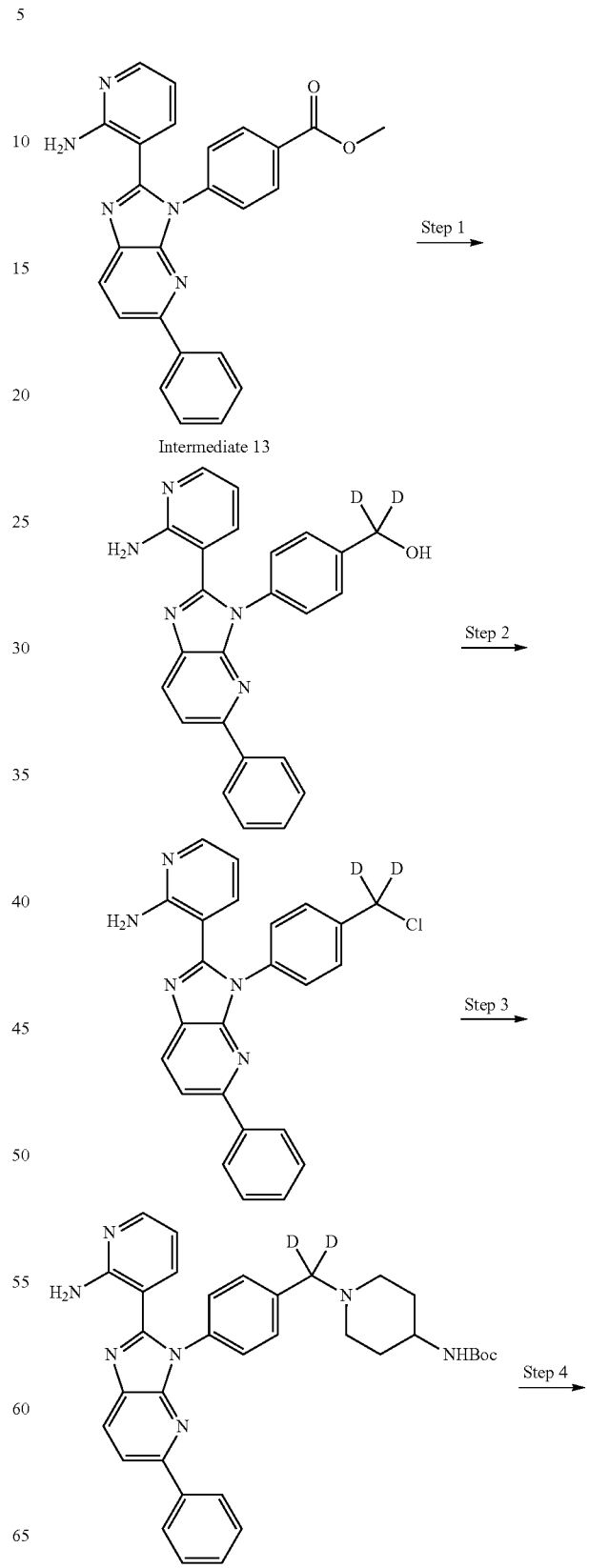

Step 1: Tert-butyl 4-[(4-cyano-2-pyridyl)amino]piperidine-1-carboxylate

A mixture of tert-butyl 4-aminopiperidine-1-carboxylate (1.20 g, 6.01 mmol), 2-bromopyridine-4-carbonitrile (1.0 g, 5.46 mmol), BINAP (136 mg, 219 μmol), $Pd_2(dba)_3$ (100 mg, 109 μmol) and t-BuONa (1.05 g, 10.9 mmol) in toluene (20 mL) was degassed and purged with $N_2$ three times, and then the mixture was stirred at 100° C. for 2 hr under $N_2$ atmosphere. The mixture was diluted with 50 mL $H_2O$ and extracted with EtOAc (50 mL×2). The combined organic layers were washed with 50 mL brine, dried over $Na_2SO_4$, filtered and concentrated under reduced pressure to give a residue. The crude product was purified by flash chromatography on silica gel (Eluent of 0~25% EtOAc in petroleum ether), tert-butyl 4-[(4-cyano-2-pyridyl)amino]piperidine-1-carboxylate (350 mg, yield: 20%) was obtained as a yellow solid. $^1$H NMR (400 MHz, Chloroform-d) δ 8.18 (d, J=5.2 Hz, 1H), 6.71 (dd, J=5.2, 1.2 Hz, 1H), 6.56 (s, 1H), 4.72 (d, J=7.6 Hz, 1H), 4.14-4.00 (m, 2H), 3.90-3.76 (m, 1H), 2.96-2.90 (m, 2H), 2.05-1.99 (m, 2H), 1.46 (s, 9H), 1.43-1.33 (m, 2H).

Step 2: 2-(4-Piperidylamino)pyridine-4-carbonitrile

A solution of tert-butyl 4-[(4-cyano-2-pyridyl)amino]piperidine-1-carboxylate (350 mg, 1.16 mmol) in HCl in 1,4-dioxane (4M, 5 mL). The mixture was stirred at 25° C. for 1 hr. The reaction mixture was concentrated under reduced pressure to give 2-(4-piperidylamino)pyridine-4-carbonitrile (Intermediate 39, 200 mg, HCl salt, yield: 72%) as a yellow solid, which was used to the next step without further purification.

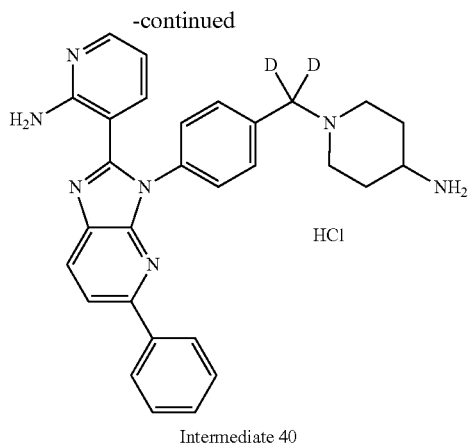

Intermediate 40

Step 1: (4-(2-(2-Aminopyridin-3-yl)-5-phenyl-3H-imidazo[4,5-b]pyridin-3-yl)phenyl)methan-d2-ol To a solution of Intermediate 13 (500 mg, 119 mmol) in THF (50 mL) at 0° C. was added LiAlD$_4$ (99.6 mg, 2.37 mmol) in portions under N$_2$ atmosphere. The mixture was stirred at 0° C. for 1 hr. The reaction mixture was quenched with Na$_2$SO$_4$·10H$_2$O at 0° C., filtered and concentrated under reduced pressure. The residue was purified by silica gel flash chromatography (Eluent of 0~100% EtOAc in petroleum ether) to give (4-(2-(2-aminopyridin-3-yl)-5-phenyl-3H-imidazo[4,5-b]pyridin-3-yl)phenyl)methan-d2-ol (190 mg, yield: 41%) as a yellow solid. MS: m/z=396.1 [M+H]+. $^1$H NMR (400 MHz, Chloroform-d) δ 8.15 (d, J=8.4 Hz, 1H), 8.03-7.97 (m, 3H), 7.83 (d, J=8.4 Hz, 1H), 7.57 (d, J=8.4 Hz, 2H), 7.47-7.37 (m, 6H), 6.44 (dd, J=7.6, 5.2 Hz, 1H).

Step 2: 3-(3-(4-(Chloromethyl-d2)phenyl)-5-phenyl-3H-imidazo[4,5-h]pyridin-2-yl)pyridin-2-amine To a solution of (4-(2-(2-aminopyridin-3-yl)-5-phenyl-3H-imidazo[4,5-b]pyridin-3-yl)phenyl)methan-d2-ol (190 mg, 480 μmol) in CH$_2$Cl$_2$ (5 mL) was added SOCl$_2$ (171 mg, 1.44 mmol) in portions under N$_2$ atmosphere. The mixture was stirred at 40° C. for 1 hr. The reaction mixture was filtered. The filter liquor was concentrated to dryness. The crude was used in the next step without further purification. 3-(3-(4-(chloromethyl-d2)phenyl)-5-phenyl-3H-imidazo[4,5-h]pyridin-2-yl)pyridin-2-amine (198 mg, crude) was obtained as a yellow solid. MS: m/z=414.0 [M+H]t. $^1$H NMR (400 MHz, Dimethylsulfoxide-d$_6$) δ 8.36 (d, J=8.4 Hz, 1H), 8.12 (dd, J=6.4, 1.6 Hz, 1H), 8.09-8.04 (m, 3H), 7.90-7.87 (m, 1H), 7.68-7.56 (m, 4H), 7.51-7.41 (m, 3H), 6.90 (dd, J=7.2, 6.4 Hz, 1H).

Step 3: tert-Butyl(1-((4-(2-(2-aminopyridin-3-yl)-5-phenyl-3H-imidazo[4,5-b]pyridin-3-yl)phenyl)methyl-d2)piperidin-4-yl)carbamate A solution of 3-(3-(4-(chloromethyl-d2)phenyl)-5-phenyl-3H-imidazo[4,5-b]pyridin-2-yl)pyridin-2-amine (248 mg, 599 gmol), tert-butyl N-(4-piperidyl)carbamate (132 mg, 659 mol), K$_2$CO$_3$ (166 mg, 1.20 mmol) and NaI (89.8 mg, 599.2 μmol) in DMF (3 mL) was stirred at 80° C. for 2 h under N$_2$ atmosphere. The water (10 mL) was added to the mixture, and the mixture was extracted with EtOAc (3×5 mL). The combined organic layers were washed with brine (10 mL), dried over Na$_2$SO$_4$, filtered, and concentrated. The residue was purified by silica gel flash chromatography (Eluent of 0~100% EtOAc in petroleum ether) and prep-HPLC (column: Xtimate C18 100*30 mm*3 μm; mobile phase: [water (FA)-ACN]; B %: 20%-60%, 9 min). tert-Butyl(1-((4-(2-(2-aminopyridin-3-yl)-5-phenyl-3H-imidazo[4,5-b]pyridin-3-yl)phenyl)methyl-d2)piperidin-4-yl)carbamate (180 mg, yield: 52%) was obtained as a yellow solid. MS: m/z=578.2 [M+H]+. $^1$H NMR (400 MHz, Chloroform-d) δ 8.13 (d, J=8.4 Hz, 1H), 8.07 (dd, J=4.8, 1.6 Hz, 1H), 8.03-8.00 (m, 2H), 7.81 (d, J=8.4 Hz, 1H), 7.63-7.52 (m, 2H), 7.46-7.42 (m, 4H), 7.40-7.36 (m, 1H), 7.08 (dd, J=7.6, 1.6 Hz, 1H), 6.59 (br s, 2H), 6.36 (dd, J=7.6, 4.8 Hz, 1H), 4.52-4.39 (br s, 1H), 3.57-3.59 (m, 1H), 3.01-2.98 (m, 1H), 2.33-2.28 (m, 2H), 2.00-1.98 (m, 2H), 1.68-1.65 (m, 2H), 1.47-1.46 (m, 1H), 1.44 (s, 9H).

Step 4: 3-(3-(4-((4-Aminopiperidin-1-yl)methyl-d2)phenyl)-5-phenyl-3H-imidazo[4,5-b]pyridin-2-yl)pyridin-2-amine hydrochloride To a solution of tert-butyl (1-((4-(2-(2-aminopyridin-3-yl)-5-phenyl-3H-imidazo[4,5-b]pyridin-3-yl)phenyl)methyl-d2)piperidin-4-yl)carbamate (90.0 mg, 156 μmol) in CH$_2$Cl$_2$ (3 mL) was added HCl in 1,4-dioxane (4 M, 974 μL) under N$_2$ atmosphere. The mixture was stirred at 20° C. for 1 hr. The mixture was filtered, washed with CH$_2$Cl$_2$ (2×10 mL). The filter liquor was concentrated to dryness. Filter cake was dried to remove solvent. The crude product was used in the next step without further purification. 3-(3-(4-((4-Aminopiperidin-1-yl)methyl-d2)phenyl)-5-phenyl-3H-imidazo[4,5-b]pyridin-2-yl)pyridin-2-amine hydrochloride (Intermediate 40, 70 mg, HCl salt, yield: 93%) was obtained as a yellow solid. MS: m/z=478.2 [M+H]+. $^1$H NMR (400 MHz, Methanol-d$_4$) δ 8.33 (d, J=8.4 Hz, 1H), 8.08-8.00 (m, 4H), 7.91 (d, J=8.0 Hz, 3H), 7.73 (d, J=9.2 Hz, 2H), 7.50-7.38 (m, 3H), 6.91 (t, J=6.6 Hz, 1H), 3.70 (d, J=12.0 Hz, 2H), 3.61-3.52 (m, 1H), 3.35-3.29 (m, 1H), 3.28-3.17 (m, 1H), 2.31 (d, J=10.8 Hz, 2H), 2.23-2.04 (m, 2H).

Intermediate 41: 3-(3-(4-((4-((Methyl-d3)amino)piperidin-1-yl)methyl)phenyl)-5-phenyl-3H-imidazo[4,5-b]pyridin-2-yl)pyridin-2-amine

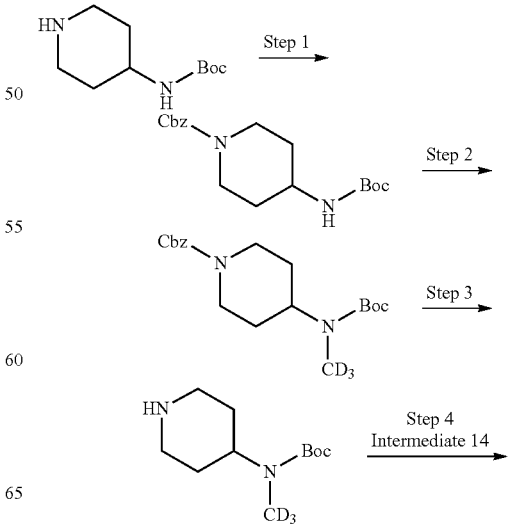

-continued

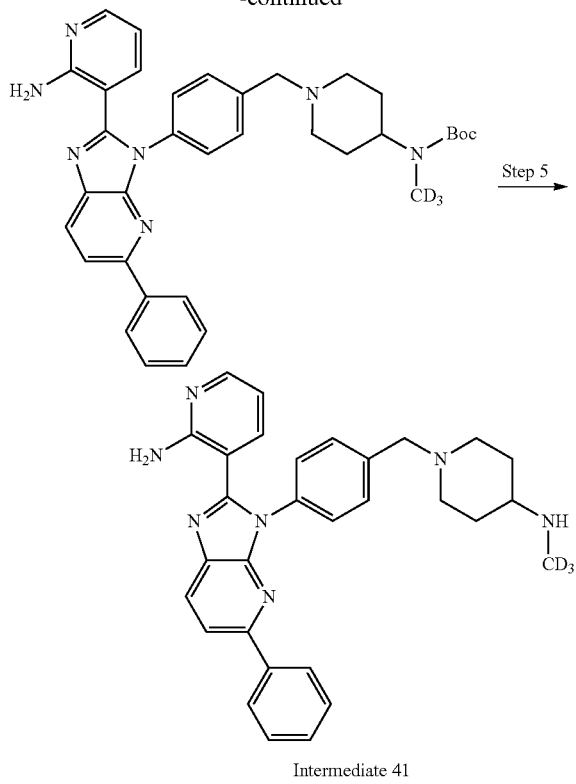

Intermediate 41

Step 1: Benzyl 4-((tert-butoxycarbonyl)amino)piperidine-1-carboxylate

To a solution of tert-butyl N-(4-piperidyl)carbamate (12 g, 59.9 mmol) in CH$_2$Cl$_2$ (100 mL) was added TEA (18.2 g, 179 mmol), and then the CbzCl (11.2 g, 65.9 mmol) was added into the mixture at 0° C. The mixture was stirred at 25° C. for 2 hr. The mixture was concentrated under reduced pressure. The crude was purified by silica gel flash chromatography (Eluent of 10~50% EtOAc in petroleum ether) to give benzyl 4-((tert-butoxycarbonyl)amino)piperidine-1-carboxylate (16 g, yield: 71%) as an off-white solid. $^1$H NMR (400 MHz, Dimethylsulfoxide-d$_6$) δ 7.40-7.28 (m, 5H), 5.06 (s, 2H), 3.90 (d, J=13.6 Hz, 2H), 3.50-3.34 (m, 2H), 2.89 (s, 2H), 1.71 (d, J=10.8 Hz, 2H), 1.37 (s, 9H), 1.30-1.18 (m, 2H).

Step 2: Benzyl 4-((tert-butoxycarbonyl)(methyl-d$_3$)amino)piperidine-1-carboxylate To a solution of benzyl 4-(tert-butoxycarbonylamino)piperidine-1-carboxylate (13 g, 38.9 mmol) in THF (200 mL) was added NaH (4.66 g, 117 mmol) at 0° C. After stirring at 0° C. for 30 min, CD$_3$I (16.5 g, 117 mmol) was added to the mixture. The mixture was stirred at 25° C. for 16 hr. The mixture was quenched with NH$_4$C$_1$ (aq) (100 mL) at 0° C. The mixture was diluted with H$_2$O (100 mL) and extracted with CH$_2$Cl$_2$ (200 mL×2). The combined organic layers were washed with brine (200 mL×2), dried over Na$_2$SO$_4$, filtered and concentrated under reduced pressure. The residue was purified by silica gel flash chromatography (Eluent of 0~20% EtOAc in petroleum ether) to give benzyl 4-((tert-butoxycarbonyl)(methyl-d$_3$)amino)piperidine-1-carboxylate (8.6 g, yield: 56%) as a colorless oil. MS: m/z=252.3 [M+H−100]$^+$. $^1$H NMR (400 MHz, Dimethylsulfoxide-d$_6$) δ 7.42-7.28 (m, 5H), 5.07 (s, 2H), 4.14-3.89 (m, 3H), 2.82 (s, 2H), 1.58-1.48 (m, 4H), 1.39 (s, 9H).

Step 3: tert-Butyl (methyl-d$_3$)(piperidin-4-yl)carbamate

To a solution of benzyl 4-[tert-butoxycarbonyl(trideuteriomethyl)amino]piperidine-1-carboxylate (8.6 g, 24.5 mmol) in MeOH (90 mL) was added Pd/C (900 mg, 24.5 mmol). The mixture was stirred at 25° C. for 16 hr under H$_2$ (15 psi). The mixture was filtered, and the filter cake was washed with MeOH (30 mL). The filtrate was concentrated under reduced pressure to give a tert-butyl (methyl-d$_3$)(piperidin-4-yl)carbamate (5 g, yield: 80%) as a colorless oil. MS: m/z=218.3 [M+H]$^+$. $^1$H NMR (400 MHz, Dimethylsulfoxide-d$_6$) δ 3.93-3.62 (m, 1H), 3.26-3.16 (m, 1H), 2.95 (d, J=12.0 Hz, 2H), 2.47-2.38 (m, 2H), 1.54-1.42 (m, 4H), 1.39 (s, 9H).

Step 4: tert-Butyl (1-(4-(2-(2-aminopyridin-3-yl)-5-phenyl-3H-imidazo[4,5-b]pyridin-3-yl)benzyl)piperidin-4-yl)(methyl-d$_3$)carbamate To a solution of Intermediate 14 (1 g, 2.43 mmol) in DMF (10 mL) were added tert-butyl (methyl-d$_3$)(piperidin-4-yl)carbamate (527 mg, 2.43 mmol), NaI (182 mg, 1.21 mmol) and K$_2$CO$_3$ (1.0 g, 7.28 mmol). The mixture was stirred at 80° C. for 18 hr. The reaction mixture was diluted with H$_2$O (20 mL) and extracted with CH$_2$Cl$_2$ (20 mL×3). The combined organic layers were washed with brine (20 mL×2), dried over Na$_2$SO$_4$, filtered and concentrated under reduced pressure. The residue was purified by silica gel flash chromatography (Eluent of 0~6% MeOH in CH$_2$Cl$_2$) to give tert-butyl (1-(4-(2-(2-aminopyridin-3-yl)-5-phenyl-3H-imidazo[4,5-b]pyridin-3-yl)benzyl)piperidin-4-yl)(methyl-d$_3$) carbamate (750 mg, yield: 49%) as a yellow solid. MS: m/z=593.3 [M+H]$^+$.

Step 5: 3-(3-(4-((4-((Methyl-da)amino)piperidin-1-yl)methyl)phenyl)-5-phenyl-3H-imidazo[4,5-b]pyridin-2-yl)pyridin-2-amine To a solution of tert-butyl (1-(4-(2-(2-aminopyridin-3-yl)-5-phenyl-3H-imidazo[4,5-b]pyridin-3-yl)benzyl)piperidin-4-yl)(methyl-d3)carbamate (430 mg, 725 μmol) in CH$_2$Cl$_2$ (5 mL) was added TFA (165 mg, 1.45 mmol). The mixture was stirred at 25° C. for 1 hr. The mixture was diluted with H$_2$O (10 mL), and pH was adjusted to about 8 by NaHCO$_3$ (aq.). The mixture was extracted with CH$_2$Cl$_2$ (10 mL×2). The combined organic layers were washed with brine (10 mL×2), dried over Na$_2$SO$_4$, filtered and concentrated under reduced pressure. After purified by prep-TLC (CH$_2$Cl$_2$: MeOH=5:1), 3-(3-(4-((4-((methyl-d$_3$)amino)piperidin-1-yl)methyl)phenyl)-5-phenyl-3H-imidazo[4,5-b]pyridin-2-yl) pyridin-2-amine (Intermediate 41, 350 mg crude, yield: 50%) was obtained as a light-yellow solid. MS: m/z=493.3 [M+H]$^+$. $^1$H NMR (400 MHz, Methanol-d$_4$) δ 8.19 (d, J=8.4 Hz, 1H), 8.03 (d, J=7.2 Hz, 2H), 7.98 (dd, J=4.8, 1.6 Hz, J H), 7.93 (d, J=8.4 Hz, 1H), 7.53 (d, J=8.4 Hz, 2H), 7.47-7.35 (m, 5H), 7.32 (dd, J=7.6, 1.6 Hz, 1H), 6.47 (dd, J=7.6, 4.8 Hz, 1H), 3.65 (s. 2H), 3.08-3.03 (m, 2H), 3.02-2.95 (m, 1H), 2.21-2.15 (m, 2H), 2.08-2.05 (m, 2H), 1.67-1.61 (m, 2H).

509

Intermediate 42: tert-Butyl 4-(4-(2-(2-aminopyridin-3-yl)-5-chloro-3H-imidazo[4,5-b]pyridin-3-yl)benzyl)piperazine-1-carboxylate

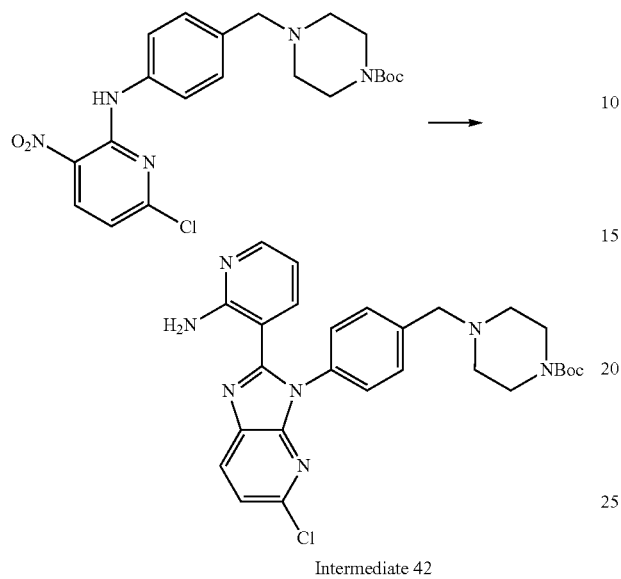

Intermediate 42

To a solution of tert-butyl 4-(4-((6-chloro-3-nitropyridin-2-yl)amino)benzyl)piperazine-1-carboxylate (refer to Intermediate 10 for detail procedures, 21 g, 46.9 mmol) in DMSO (300 mL) were added 2-aminonicotinaldehyde (6.87 g, 56.4 mmol) and $Na_2S_2O_4$ (28.8 g, 141 mmol). The mixture was stirred at 100° C. for 16 hr. The reaction mixture was quenched with $H_2O$ (300 mL) at 25° C., and extracted with $CH_2Cl_2$ (500 mL×2). The combined organic layers were washed with $H_2O$ (1000 mL×3), dried over $Na_2SO_4$, filtered and concentrated under reduced pressure to give a crude product. After purified by silica gel flash chromatography (Eluent of 1~8% MeOH in $CH_2Cl_2$), tert-butyl 4-(4-(2-(2-aminopyridin-3-yl)-5-chloro-3H-imidazo[4,5-b]pyridin-3-yl)benzyl)piperazine-1-carboxylate (Intermediate 42, 6.3 g, yield: 25%) was obtained as a yellow solid. MS: m/z=520.1 [M+H]⁺. ¹H NMR (400 MHz, Chloroform-d) δ 8.05 (dd, J=4.8, 2.0 Hz, 1H), 8.02 (d, J=8.4 Hz, 1H), 7.49 (d, J=8.4 Hz, 2H), 7.31 (dd, J=8.4, 2.8 Hz, 3H), 7.02 (dd, J=8.0, 2.0 Hz, 1H), 6.62 (br s, 2H), 6.33 (dd, J=8.0, 4.8 Hz, 11H), 3.61 (s, 2H), 3.50-3.45 (m, 4H), 2.49-2.43 (m, 4H), 1.47 (s, 9H).

Intermediate 43: 3-(5-(4-Chlorophenyl)-3-(4-(piperazin-1-ylmethyl)phenyl)-3H-imidazo[4,5-b]pyridin-2-yl)pyridin-2-amine hydrochloride

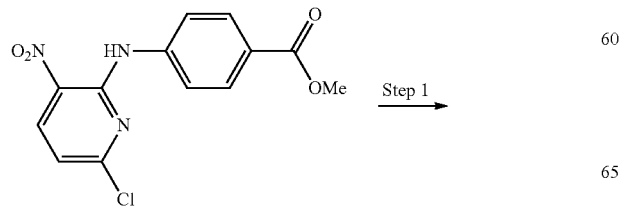

Step 1 →

510

-continued

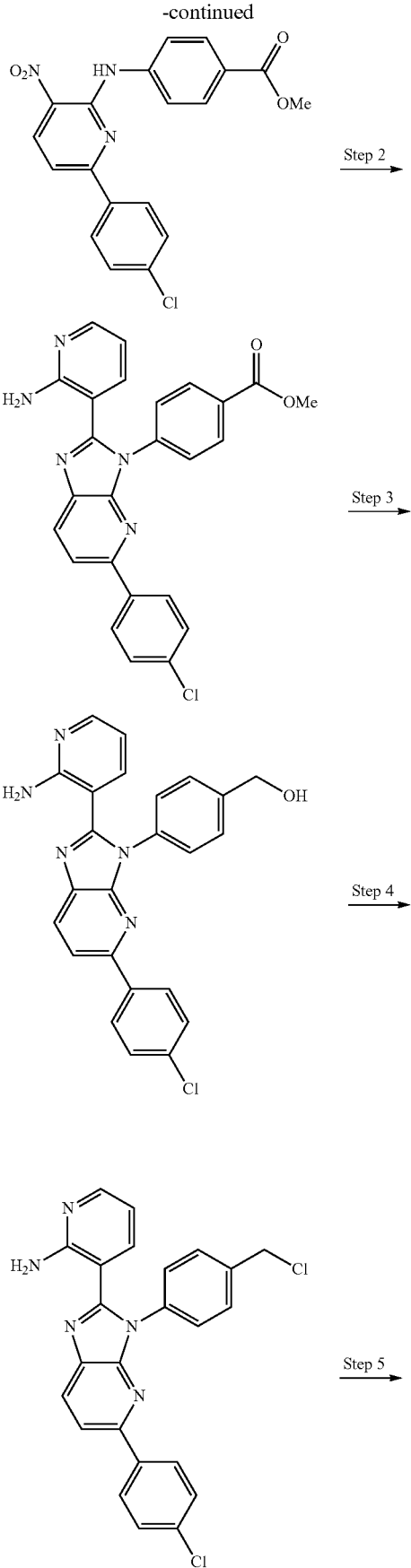

-continued

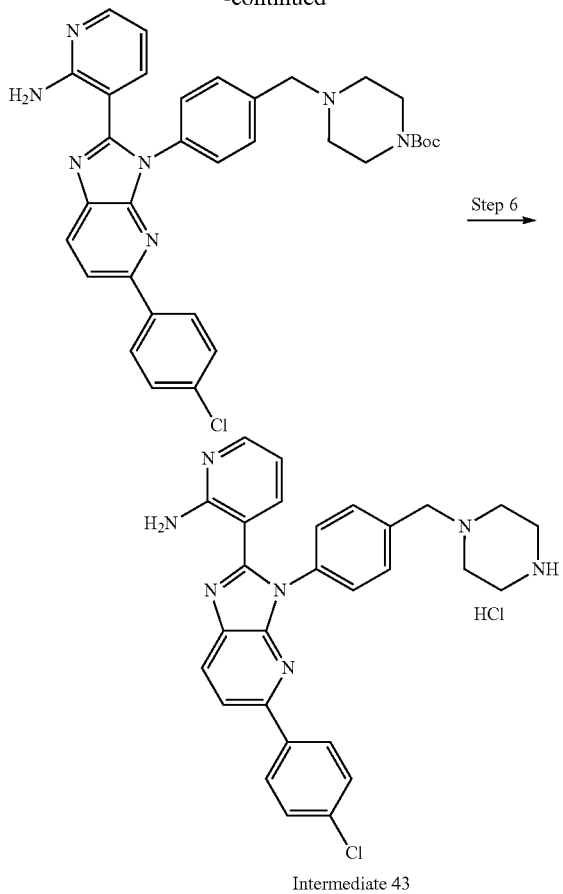

Intermediate 43

Step 1: Methyl 4-((6-(4-chlorophenyl)-3-nitropyridin-2-yl)amino)benzoate

A mixture of methyl 4-((6-chloro-3-nitropyridin-2-yl)amino)benzoate (refer to Intermediate 13 for detail procedures, 5 g, 16.3 mmol), (4-chlorophenyl)boronic acid (2.54 g, 16.3 mmol), Cs$_2$CO$_3$ (15.9 g, 48.8 mmol), and Pd(dppf)Cl$_2$ (2.38 g, 3.25 mmol) in 1,4-dioxane (100 mL) and H$_2$O (20 mL) was degassed and purged with N$_2$ three times, and then the mixture was stirred at 80° C. for 16 hr under N$_2$ atmosphere. The reaction mixture was diluted with H$_2$O (100 mL) and extracted with CH$_2$Cl$_2$ (50 mL×4). The combined organic layers were washed with brine (30 mL×3), dried over Na$_2$SO$_4$, filtered and concentrated under reduced pressure. The residue was purified by silica gel flash chromatography (Eluent of 35~45% EtOAc in petroleum ether) to give methyl 4-((6-(4-chlorophenyl)-3-nitropyridin-2-yl)amino)benzoate (5 g, yield: 80%) as a yellow solid. MS: m/z=383.9 [M+H]$^+$.

Step 2: Methyl 4-(2-(2-aminopyridin-3-yl)-5-(4-chlorophenyl)-3H-imidazo[4,5-b]pyridin-3-yl)benzoate To a solution of methyl 4-((6-(4-chlorophenyl)-3-nitropyridin-2-yl)amino)benzoate (5 g, 13.0 mmol) and 2-aminonicotinaldehyde (1.75 g, 14.3 mmol) in DMSO (150 mL) was added Na$_2$S$_2$O$_4$ (9.07 g, 52.1 mmol). The mixture was stirred at 100° C. for 16 hr. The reaction mixture was diluted with H$_2$O (100 mL) and extracted with CH$_2$Cl$_2$ (500 mL×6). The combined organic layers were washed with brine (250 mL×2), dried over Na$_2$SO$_4$, filtered and concentrated under reduced pressure. The residue was purified by silica gel flash chromatography (Eluent of 25~30% EtOAc in CH$_2$Cl$_2$) to give methyl 4-(2-(2-aminopyridin-3-yl)-5-(4-chlorophenyl)-3H-imidazo[4,5-b]pyridin-3-yl)benzoate (2.3 g, yield: 34%) as a yellow solid. MS: m/z=456.0 [M+H]$^+$.

Step 3: (4-(2-(2-Aminopyridin-3-yl)-5-(4-chlorophenyl)-3H-imidazo[4,5-b]pyridin-3-yl)phenyl)methanol To a solution of 4-(2-(2-aminopyridin-3-yl)-5-(4-chlorophenyl)-3H-imidazo[4,5-b]pyridin-3-yl)benzoate (2.3 g, 5.05 mmol) in THF (30 mL) was added LiAlH$_4$ (2.5 M, 2.42 mL) at 0° C., then the mixture was stirred at 25° C. for 2 hr. The reaction mixture was quenched with Na$_2$SO$_4$—H$_2$O (4 g) at 0° C., and the mixture was filtered, the filter cake was washed by CH$_2$Cl$_2$ (30 mL×3). The filtrate was concentrated under reduced pressure to give (4-(2-(2-aminopyridin-3-yl)-5-(4-chlorophenyl)-3H-imidazo[4,5-b]pyridin-3-yl)phenyl)methanol (2.1 g, yield: 97%) as a yellow solid, which was directly used in the next step without purification. MS: m/z=428.1 [M+H]$^+$.

Step 4: 3-(3-(4-(Chloromethyl)phenyl)-5-(4-chlorophenyl)-3H-imidazo[4,5-b]pyridin-2-yl)pyridin-2-amine To a solution of (4-(2-(2-aminopyridin-3-yl)-5-(4-chlorophenyl)-3H-imidazo[4,5-b]pyridin-3-yl)phenyl)methanol (1.85 g, 4.32 mmol) in CH$_2$Cl$_2$ (40 mL) was added SOCl$_2$ (1.54 g, 13.0 mmol) at 0° C. The mixture was stirred at 40° C. for 3 hr. The reaction mixture was quenched with H$_2$O (5 mL) at 0° C., and then filtered and concentrated under reduced pressure to give 3-(3-(4-(chloromethyl)phenyl)-5-(4-chlorophenyl)-3H-imidazo[4,5-b]pyridin-2-yl)pyridin-2-amine (1.9 g, yield: 98%) as a black brown solid. MS: m/z=455.9, 447.8 [M+H]$^+$.

Step 5: tert-Butyl 4-(4-(2-(2-aminopyridin-3-yl)-5-(4-chlorophenyl)-3H-imidazo[4,5-b]pyridin-3-yl)benzyl)piperazine-1-carboxylate To a solution of 3-(3-(4-(chloromethyl)phenyl)-5-(4-chlorophenyl)-3H-imidazo[4,5-b]pyridin-2-yl)pyridin-2-amine (1 g, 2.24 mmol), tert-butyl piperazine-1-carboxylate (417 mg, 2.24 mmol) in DMF (10 mL) were added NaI (67.2 mg, 448 gmol) and K$_2$CO$_3$ (929 mg, 6.72 mmol). The mixture was stirred at 25° C. for 16 hr. The residue was diluted with H$_2$O (30 mL) and extracted with EtOAc (30 mL×3). The combined organic layers were washed with brine (20 mL×2), dried over Na$_2$SO$_4$, filtered and concentrated under reduced pressure. The residue was purified by silica gel flash chromatography (Eluent of 0~4% MeOH in CH$_2$Cl$_2$) to give tert-butyl 4-(4-(2-(2-aminopyridin-3-yl)-5-(4-chlorophenyl)-3H-imidazo[4,5-b]pyridin-3-yl)benzyl)piperazine-1-carboxylate (550 mg, yield: 40%) as a yellow solid. MS: m/z=596.1 [M+H]$^+$.

Step 6: 3-(5-(4-Chlorophenyl)-3-(4-(piperazin-1-ylmethyl)phenyl)-3H-imidazo[4,5-b]pyridin-2-yl)pyridin-2-amine To a solution of tert-butyl 4-(4-(2-(2-aminopyridin-3-yl)-5-(4-chlorophenyl)-3H-imidazo[4,5-b]pyridin-3-yl)benzyl)piperazine-1-carboxylate (550 mg, 923 μmol) in 1,4-dioxane (5 mL) was added 4.0 M HCl in 1,4-dioxane (3 mL) at 25° C. The mixture was stirred at 25° C. for 1 hr. The reaction was concentrated under reduced pressure to give 3-(5-(4-chlorophenyl)-3-(4-(piperazin-1-ylmethyl)phenyl)-3H-imidazo[4,5-b]pyridin-2-yl)pyridin-2-amine (Intermediate 43, 550 mg, HCl salt, yield: 98%) as a yellow solid. MS: m/z=496.0 [M+H]$^+$. $^1$H NMR (400 MHz, Methanol-d$_4$) δ 8.33 (d, J=8.4 Hz, 1H), 8.08-8.02 (m, 4H), 7.95 (d, J=8.4 Hz, 2H), 7.90 (d, J=7.6 Hz, 1H), 7.74 (d, J=8.0 Hz, 2H), 7.45 (d, J=8.8 Hz, 2H), 6.94 (t, J=7.2 Hz, 1H), 4.67 (s, 2H), 3.80-3.64 (m, 8H).

Intermediate 44: tert-Butyl (I-(4-(2-(2-aminopyridin-3-yl)-5-chloro-3H-imidazo[4,5-b]pyridin-3-yl)benzyl)piperidin-4-yl)carbamate

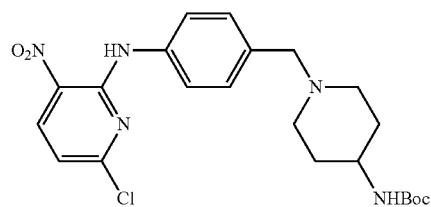

Intermediate 44

A mixture of tert-butyl (1-(4-((6-chloro-3-nitropyridin-2-yl)amino)benzyl)piperidin-4-yl)carbamate (refer to Intermediate 11 for detail procedures, 13.0 g, 28.0 mmol), 2-aminopyridine-3-carbaldehyde (4.12 g, 33.8 mmol), and Na$_2$S$_2$O$_4$ (23.1 g, 112 mmol) in DMSO (500 mL) was degassed and purged with N$_2$ three times, and then the mixture was stirred at 100° C. for 16 hr under N$_2$ atmosphere. The reaction mixture was diluted with water (500 mL) and extracted with EtOAc (500 mL×3). The combined organic layers were dried over Na$_2$SO$_4$, filtered and concentrated under reduced pressure. The residue was purified by silica gel flash chromatography (Eluent of 0~8% MeOH in CH$_2$Cl$_2$) to give tert-butyl (1-(4-(2-(2-aminopyridin-3-yl)-5-chloro-3H-imidazo[4,5-b]pyridin-3-yl)benzyl)piperidin-4-yl)carbamate (Intermediate 44, 4.8 g, yield: 28%) as a yellow solid. MS: m/z=534.3 [M+H]$^+$.

Intermediate 45: 3-(2-(2-Aminopyridin-3-yl)-3-(4-(piperazin-1-ylmethyl)phenyl)-3H-imidazo[4,5-b]pyridin-5-yl)pyridin-2(1H)-one

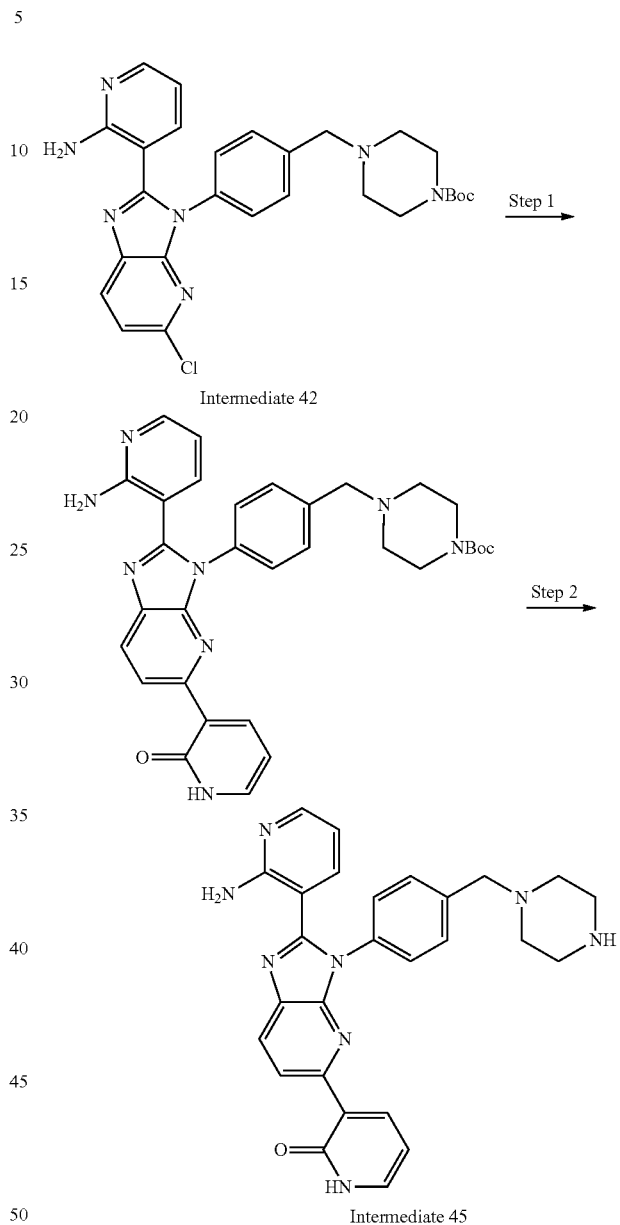

Step 1: tert-Butyl 4-(4-(2-(2-aminopyridin-3-yl)-5-(2-oxo-1,2-dihydropyridin-3-yl)-3H-imidazo[4,5-b]pyridin-3-yl)benzyl)piperazine-1-carboxylate A mixture of Intermediate 42 (250 mg, 481 μmol), (2-oxo-1,2-dihydropyridin-3-yl)boronic acid (80.1 mg, 577 μmol), Cs$_2$CO$_3$ (470 mg, 1.44 mmol), and Pd(dppf)Cl$_2$ (70.4 mg, 96.2 μmol) in 1,4-dioxane (5 mL) and H$_2$O (1 mL) was degassed and purged with N$_2$ three times, and then the mixture was stirred at 80° C. for 16 hr under N$_2$ atmosphere. The reaction mixture was filtered at 25° C., and then diluted with H$_2$O (20 mL) and extracted with EtOAc (20 mL×3). The combined organic layers were washed with brine (30 mL), dried over Na$_2$SO$_4$, filtered, and concentrated under reduced pressure. After purified by silica gel flash chromatography (Eluent of 1~100% EtOAc in petroleum ether and eluent of 1~10% MeOH in CH$_2$Cl$_2$), tert-butyl 4-(4-(2-(2-aminopyridin-3-yl)-5-(2-oxo-1,2-dihydropyridin-3-yl)-3H-imidazo[4,5-b]pyridin-3-yl)benzyl)piperazine-1-carboxylate (200 mg, yield: 58%) was obtained as a brown solid. MS: m/z=579.3 [M+H]$^+$.

Step 2: 3-(2-(2-Aminopyridin-3-yl)-3-(4-(piperazin-1-ylmethyl)phenyl)-3H-imidazo[4,5-b]pyridin-5-yl)pyridin-2(1H)-one To a solution of tert-butyl 4-(4-(2-(2-aminopyridin-3-yl)-5-(2-oxo-1,2-dihydropyridin-3-yl)-3H-imidazo[4,5-b]pyridin-3-yl)benzyl)piperazine-1-carboxylate (200 mg, 346 µmol) in 1,4-dioxane (3 mL) was added 4 M HCl in 1,4-dioxane (3 mL) at 25° C. The mixture was stirred at 25° C. for 16 hr. The pH of the mixture was adjusted to ~8 with NaHCO$_3$. Then the mixture was extracted with CH$_2$Cl$_2$ (20 mL×3). The combined organic layers were washed with brine (20 mL), dried over Na$_2$SO$_4$, filtered and concentrated under reduced pressure to give 3-(2-(2-aminopyridin-3-yl)-3-(4-(piperazin-1-ylmethyl)phenyl)-3H-imidazo[4,5-b]pyridin-5-yl)pyridin-2(1H)-one (Intermediate 45, 200 mg, yield: 85%) as a yellow solid. MS: m/z=479.2 [M+H]$^+$.

Intermediate 46: 3-(5-Morpholino-3-(4-(piperazin-1-ylmethyl)phenyl)-3H-imidazo[4,5-b]pyridin-2-yl)pyridin-2-amine

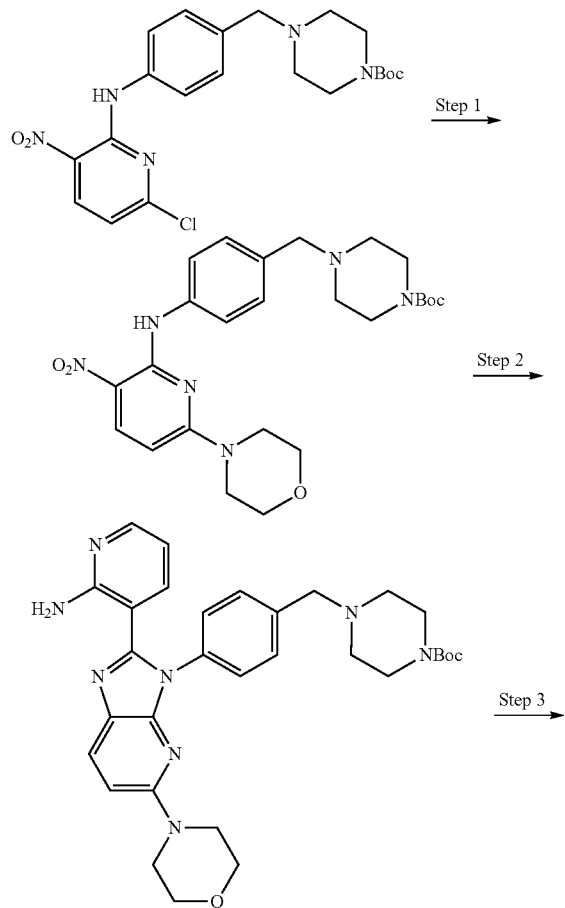

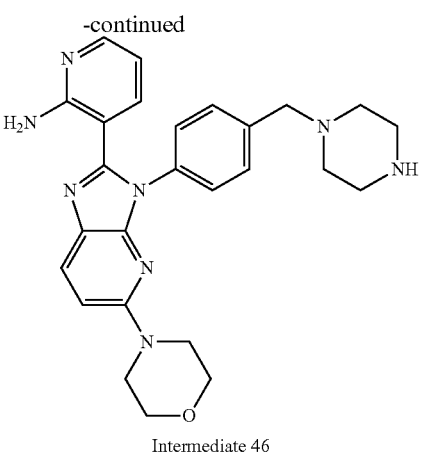

Intermediate 46

Step 1: Tert-butyl 4-(4-((6-morpholino-3-nitropyridin-2-yl)amino)benzyl)piperazine-1-carboxylate To a solution of tert-butyl 4-(4-((6-chloro-3-nitropyridin-2-yl)amino)benzyl)piperazine-1-carboxylate (refer to Intermediate 10 for detail procedures, 300 mg, 670 µmol) and morpholine (117 mg, 1.34 mmol) in CH$_3$CN (4 mL) was added DIEA (173 mg, 1.34 mmol). The mixture was stirred at 90° C. for 2 hr. The reaction mixture was quenched with H$_2$O (10 mL) at 25° C., and then extracted with CH$_2$Cl$_2$ (15 mL×2). The combined organic layers were washed with brine (15 mL), dried over Na$_2$SO$_4$, filtered and concentrated under reduced pressure to give tert-butyl 4-(4-((6-morpholino-3-nitropyridin-2-yl)amino)benzyl)piperazine-1-carboxylate (330 mg, yield: 93%) as a yellow solid. MS: m/z=499.2 [M+H]$^+$. $^1$H NMR (400 MHz, Chloroform-d) δ 10.71 (s, 1H), 8.32 (d, J=9.2 Hz, 1H), 7.53 (d, J=8.0 Hz, 2H), 7.30 (d, J=8.0 Hz, 2H), 6.13 (d, J=9.6 Hz, 1H), 3.79-3.75 (m, 4H), 3.73-3.67 (m, 4H), 3.50 (s, 2H), 3.46-3.40 (m, 4H), 2.44-2.35 (m, 4H), 1.45 (s, 9H).

Step 2: tert-Butyl 4-(4-(2-(2-aminopyridin-3-yl)-5-morpholino-3H-imidazo[4,5-b]pyridin-3-yl)benzyl)piperazine-1-carboxylate To a solution of tert-butyl 4-(4-((6-morpholino-3-nitropyridin-2-yl)amino)benzyl)piperazine-1-carboxylate (330 mg, 662 µmol) in DMSO (10 mL) were added 2-aminonicotinaldehyde (97 mg, 794 µmol) and Na$_2$S$_2$O$_4$ (542 mg, 2.65 mmol). The mixture was stirred at 100° C. for 2 hr. The reaction mixture was quenched with H$_2$O (20 mL) at 25° C., and extracted with CH$_2$Cl$_2$ (50 mL×3). The combined organic layers were washed with brine (50 mL), dried over Na$_2$SO$_4$, filtered and concentrated under reduced pressure to give the crude product. The crude was purified by silica gel flash chromatography (Eluent of 1~5% MeOH in CH$_2$Cl$_2$) to give tert-butyl 4-(4-(2-(2-aminopyridin-3-yl)-5-morpholino-3H-imidazo[4,5-b]pyridin-3-yl)benzyl)piperazine-1-carboxylate (270 mg, yield: 68%) as a yellow solid. MS: m/z=571.2 [M+H]$^+$.

Step 3: 3-(5-Morpholino-3-(4-(piperazin-1-ylmethyl)phenyl)-3H-imidazo[4,5-b]pyridin-2-yl)pyridin-2-amine To a solution of tert-butyl 4-(4-(2-(2-aminopyridin-3-yl)-5-morpholino-3H-imidazo[4,5-b]pyridin-3-yl)benzyl)piperazine-1-carboxylate (270 mg, 473 µmol) in 1,4-dioxane (2 mL) was added 4 M HCl in 1,4-dioxane (2 mL) at 25° C. The mixture was stirred at 25° C. for 16 hr. The reaction was concentrated under reduced pressure to give 3-(5-morpholino-3-(4-(piperazin-1-ylmethyl)phenyl)-3H-imidazo[4,5-b]pyridin-2-yl)pyridin-2-amine (Intermediate 46, 240 mg, HCl salt, yield: 93%) as a yellow solid. MS: m/z=471.2 [M+H]+. 1H NMR (400 MHz, Methanol-d4) δ 8.13-7.99 (m, 2H), 7.96-7.82 (m, 3H), 7.66 (dd, J=8.4, 3.2 Hz, 2H), 7.14-7.02 (m, 1H), 7.01-6.90 (m, 1H), 4.66-4.59 (m, 2H), 3.82-3.77 (m, 4H), 3.73-3.69 (m, 6H), 3.68 (s, 2H), 3.60-3.55 (m, 4H).

Intermediate 47: 6-(2-(2-Aminopyridin-3-yl)-3-(4-(piperazin-1-ylmethyl)phenyl)-3H-imidazo[4,5-b]pyridin-5-yl)pyridin-2(1H)-one

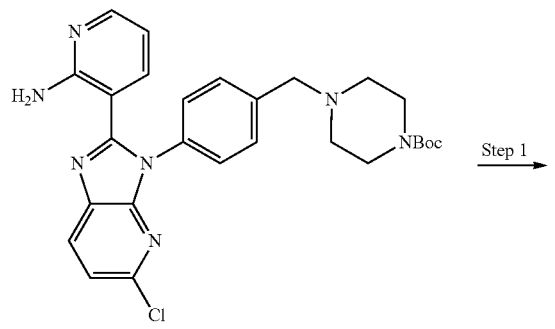

Intermediate 42

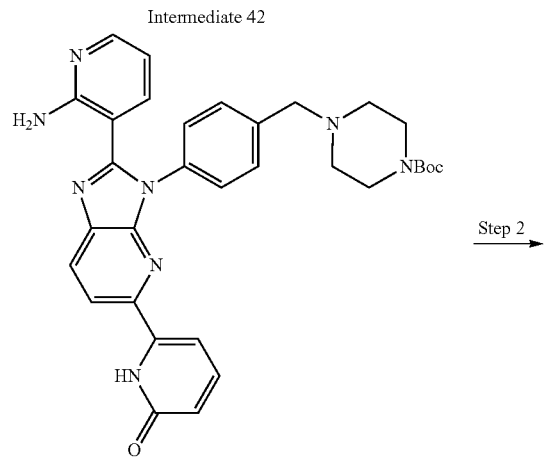

Intermediate 47

Step 1: Tert-butyl 4-(4-(2-(2-aminopyridin-3-yl)-5-(6-oxo-1,6-dihydropyridin-2-yl)-3H-imidazo[4,5-b]pyridin-3-yl)benzyl)piperazine-1-carboxylate A mixture of Intermediate 42 (500 mg, 961 µmol), 6-(4,4,5,5-tetramethyl-1,3,2-dioxaborolan-2-yl)pyridin-2(1H)-one (255 mg, 1.15 mmol), Cs2CO3 (940 mg, 2.88 mmol), and Pd(dppf)Cl2 (141 mg, 192 µmol) in 1,4-dioxane (10 mL) and H2O (2 mL) was degassed and purged with N2 three times, and then the mixture was stirred at 80° C. for 16 hr under N2 atmosphere. The reaction mixture was filtered through Celite at 25° C., and then diluted with H2O (20 mL) and extracted with EtOAc (20 mL×3). The combined organic layers were washed with brine (30 mL), dried over Na2SO4, filtered, and concentrated under reduced pressure. After purified by silica gel flash chromatography (Eluent of 1~6% MeOH in CH2Cl2), tert-butyl 4-(4-(2-(2-aminopyridin-3-yl)-5-(6-oxo-1,6-dihydropyridin-2-yl)-3H-imidazo[4,5-b]pyridin-3-yl)benzyl)piperazine-1-carboxylate (500 mg, yield: 76%) was obtained as a brown solid. MS: m/z=579.2 [M+H]+.

Step 2: 6-(2-(2-Aminopyridin-3-yl)-3-(4-(piperazin-1-ylmethyl)phenyl)-3H-imidazo[4,5-b]pyridin-5-yl)pyridin-2(1H)-one To a solution of tert-butyl 4-(4-(2-(2-aminopyridin-3-yl)-5-(6-oxo-1,6-dihydropyridin-2-yl)-3H-imidazo[4,5-b]pyridin-3-yl)benzyl)piperazine-1-carboxylate (150 mg, 259 µmol) in 1,4-dioxane (2 mL) was added 4 M HCl in 1,4-dioxane (2 mL) at 25° C. The mixture was stirred at 25° C. for 16 hr. The reaction was concentrated under reduced pressure to give the crude (HCl salt). The crude was diluted with aqueous NaHCO3 (10 mL) and extracted with CH2Cl2 (10 mL×5). The combined organic layers were washed with brine (20 mL), dried over Na2SO4, filtered and concentrated under reduced pressure to give 6-(2-(2-aminopyridin-3-yl)-3-(4-(piperazin-1-ylmethyl)phenyl)-3H-imidazo[4,5-b]pyridin-5-yl)pyridin-2(1H)-one (Intermediate 47, 68.2 mg, yield: 52%) as a yellow solid. MS: m/z=479.2 [M+H]+. 1H NMR (400 MHz, Dimethylsulfoxide-d6) δ 8.33 (d, J=8.4 Hz, 1H), 8.16 (d, J=8.4 Hz, 1H), 8.01 (dd, J=4.8, 2.0 Hz, 1H), 7.60 (dd, J=8.8, 6.8 Hz, 1H), 7.52-7.41 (m, 5H), 7.20-7.14 (m, 2H), 7.02 (br s, 2H), 6.46 (d, J=8.8 Hz, 1H), 6.38 (dd, J=7.6, 4.8 Hz, 1H), 3.53 (s, 2H), 2.73-2.69 (m, 4H), 2.36-2.30 (m, 4H).

Intermediate 48: 3-(3-(4-((4-Aminopiperidin-1-yl)methyl)phenyl)-5-morpholino-3H-imidazo[4,5-b]pyridin-2-yl)pyridin-2-amine

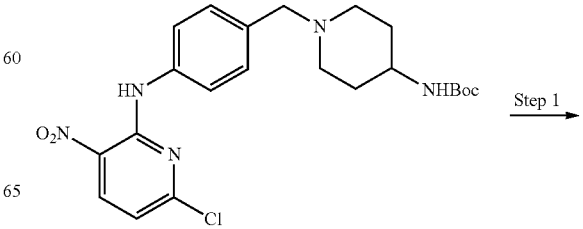

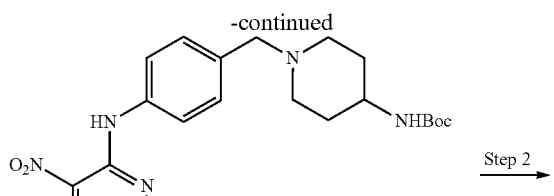

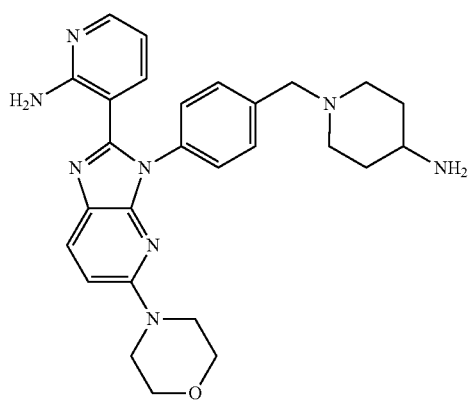

Intermediate 48

Step 1: tert-Butyl (1-(4-((6-morpholino-3-nitropyridin-2-yl)amino)benzyl)piperidin-4-yl)carbamate A mixture of tert-butyl (1-(4-((6-chloro-3-nitropyridin-2-yl)amino)benzyl)piperidin-4-yl)carbamate (refer to Intermediate 11 for detail procedures, 3 g, 6.49 mmol), morpholine (678 mg, 7.79 mmol), DIEA (1.68 g, 12.9 mmol) in MeCN (40 mL) was stirred at 90° C. for 2 hr. The reaction mixture was diluted with $H_2O$ (100 mL) and extracted with $CH_2Cl_2$ (100 mL×3). The combined organic layers were washed with $H_2O$ (50 mL×2), dried over $Na_2SO_4$, filtered and concentrated to give tert-butyl (1-(4-((6-morpholino-3-nitropyridin-2-yl)amino)benzyl)piperidin-4-yl)carbamate (3.24 g, yield: 97%) as a yellow solid, which was directly used in the next step. MS: m/z=513.2 $[M+H]^+$. $^1H$ NMR (400 MHz, Chloroform-d) 10.70 (s, 1H), 8.32 (d, J=9.2 Hz, 1H), 7.52 (d, J=8.4 Hz, 2H), 7.30 (d, J=8.0 Hz, 2H), 6.12 (d, J=9.6 Hz, 1H), 4.53-4.34 (m, 1H), 3.79-3.75 (m, 4H), 3.75-3.55 (m, 4H), 3.48 (s, 3H), 2.90-2.75 (m, 2H), 2.15-2.05 (m, 2H), 1.95-1.75 (m, 2H), 1.76-1.53 (m, 2H), 1.44 (s, 9H).

Step 2: 3-(3-(4-((4-Aminopiperidin-1-yl)methyl)phenyl)-5-morpholino-3H-imidazo[4,5-b]pyridin-2-yl)pyridin-2-amine A mixture of tert-butyl (1-(4-((6-morpholino-3-nitropyridin-2-yl)amino)benzyl)piperidin-4-yl)carbamate (3.24 g, 6.32 mmol), 2-aminopyridine-3-carbaldehyde (926 mg, 7.58 mmol), and $Na_2S_2O_4$ (3.88 g, 18.9 mmol) in DMSO (90 mL) was stirred at 100° C. for 24 hr. The reaction mixture was diluted with $H_2O$ (200 mL) and extracted with $CH_2Cl_2$ (50 mL×3). Then sat. aq. $Na_2CO_3$ (100 mL) was added to aqueous phase to adjust pH about 8-9. The aqueous phase was extracted with EtOAc (50 mL×6), dried over $Na_2SO_4$, filtered and concentrated under reduced pressure. The residue was purified by silica gel flash chromatography (Eluent of 0~7% MeOH in $CH_2Cl_2$) to give 3-(3-(4-((4-aminopiperidin-1-yl)methyl)phenyl)-5-morpholino-3H-imidazo[4,5-b]pyridin-2-yl)pyridin-2-amine (1.2 g, yield: 29%) as a yellow solid. The product (80 mg) was purified by prep-HPLC (column: Phenomenex C18 150*25 mm*10 μm; mobile phase: [water ($NH_4HCO_3$)-ACN]; gradient: 7%-37% B over 10 min) to give 3-(3-(4-((4-aminopiperidin-1-yl)methyl)phenyl)-5-morpholino-3H-imidazo[4,5-b]pyridin-2-yl)pyridin-2-amine (Intermediate 48, 36.5 mg) as a light-yellow powder. MS: m/z=485.3 $[M+H]^+$. $^1H$ NMR (400 MHz, Dimethylsulfoxide-$d_6$) δ 7.98 (d, J=8.8 Hz, 1H), 7.96 (dd, J=4.8, 2.0 Hz, 1H), 7.40 (d, J=8.4 Hz, 2H), 7.29 (d, J=8.4 Hz, 2H), 7.03 (br s, 2H), 6.98 (dd, J=8.0, 1.6 Hz, 1H), 6.89 (d, J=8.8 Hz, 1H), 6.30 (dd, J=8.0, 4.8 Hz, 1H), 3.69-3.65 (m, 4H), 3.50 (s, 2H), 3.41-3.38 (m, 5H), 2.78-2.70 (m, 2H), 2.02-1.92 (m, 2H), 1.70-1.64 (m, 2H), 1.35-1.16 (m, 2H).

Intermediate 49: 3-(5-(4-fluorophenyl)-3-(4-(piperazin-1-ylmethyl)phenyl)-3H-imidazo[4,5-b]pyridin-2-yl)pyridin-2-amine hydrochloride

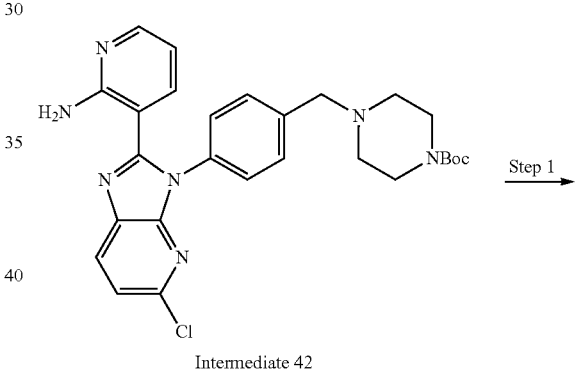

Intermediate 42

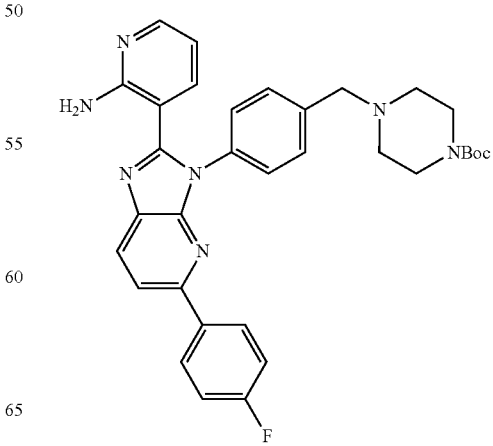

521

-continued

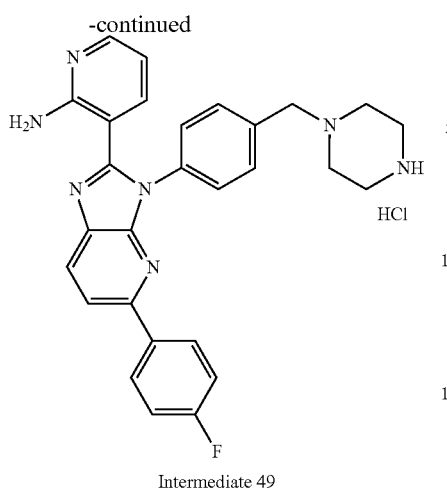

Intermediate 49

Step 1: Tert-butyl 4-(4-(2-(2-aminopyridin-3-yl)-5-(4-fluorophenyl)-3H-imidazo[4,5-b]pyridin-3-yl)benzyl)piperazine-1-carboxylate To a solution of Intermediate 42 (500 mg, 961 μmol) and (4-fluorophenyl)boronic acid (135 mg, 961 μmol) in 1,4-dioxane (10 mL) and $H_2O$ (2 mL) were added $Cs_2CO_3$ (940 mg, 2.88 mmol) and $Pd(dppf)Cl_2$ (70.4 mg, 96.1 μmol). The mixture was degassed and purged with $N_2$ three times, the resulting mixture was stirred at 80° C. for 16 hr under $N_2$ atmosphere. Then the reaction mixture was diluted with $H_2O$ (50 mL) and extracted with $CH_2Cl_2$ (50 mL×2). The combined organic layers were dried over $Na_2SO_4$, filtered and concentrated under reduced pressure. The crude product was purified by silica gel flash chromatography (Eluent of 50~100% EtOAc in petroleum ether) to give tert-butyl 4-(4-(2-(2-aminopyridin-3-yl)-5-(4-fluorophenyl)-3H-imidazo[4,5-b]pyridin-3-yl)benzyl)piperazine-1-carboxylate (500 mg, yield: 86%) as a yellow solid. MS: m/z=580.3 $[M+H]^+$. $^1H$ NMR (400 MHz, Dimethylsulfoxide-$d_6$) δ 8.26 (d, J=8.4 Hz, 1H), 8.13-8.04 (m, 2H), 8.01-7.87 (m, 2H), 7.52-7.41 (m, 4H), 7.29 (t, J=8.8 Hz, 2H), 7.14 (dd, J=7.6, 1.6 Hz, 1H), 7.03 (s, 2H), 6.38 (dd, J=8.0, 4.8 Hz, 1H), 3.59 (s, 2H), 3.37-3.33 (m, 4H), 2.40-2.26 (m, 4H), 1.40 (s, 9H). $^{19}F$ NMR (400 MHz, Dimethylsulfoxide-$d_6$) δ −113.59.

Step 2: 3-(5-(4-fluorophenyl)-3-(4-(piperazin-1-ylmethyl)phenyl)-3H-imidazo[4,5-b]pyridin-2-yl)pyridin-2-amine hydrochloride To a solution of tert-butyl 4-(4-(2-(2-aminopyridin-3-yl)-5-(4-fluorophenyl)-3H-imidazo[4,5-b]pyridin-3-yl)benzyl)piperazine-1-carboxylate (500 mg, 863 μmol) in 1,4-dioxane (5 mL) was added HCl/1,4-dioxane (4 M, 5 mL). The mixture was stirred at 25° C. for 0.5 hr. The reaction mixture was filtered and concentrated under reduced pressure to give 3-(5-(4-fluorophenyl)-3-(4-(piperazin-1-ylmethyl)phenyl)-3H-imidazo[4,5-b]pyridin-2-yl)pyridin-2-amine (Intermediate 49,400 mg HCl salt, yield: 92%) as a yellow solid. MS: m/z=480.2 $[M+H]^+$. $^1H$ NMR (400 MHz, Dimethylsulfoxide-$d_6$) δ 13.00-12.05 (m, 1H), 10.26-9.46 (m, 2H), 8.60-8.48 (m, 1H), 8.38 (d, J=8.4 Hz, 1H), 8.19-8.06 (m, 4H), 7.90-7.82 (m, 3H), 7.68 (d, J=8.4 Hz, 2H), 7.32 (t, J=9.2 Hz, 2H), 7.03-6.93 (m, 1H), 4.51 (br s, 2H), 3.55-3.50 (m, 4H), 2.59-2.51 (m, 4H). $^{19}F$ NMR (400 MHz, Dimethylsulfoxide-$d_6$) δ −113.04.

522

Intermediate 50: 3-(3-(4-(Chloromethyl)phenyl)-5-cyclopropyl-3H-imidazo[4,5-b]pyridin-2-yl)pyridin-2-amine

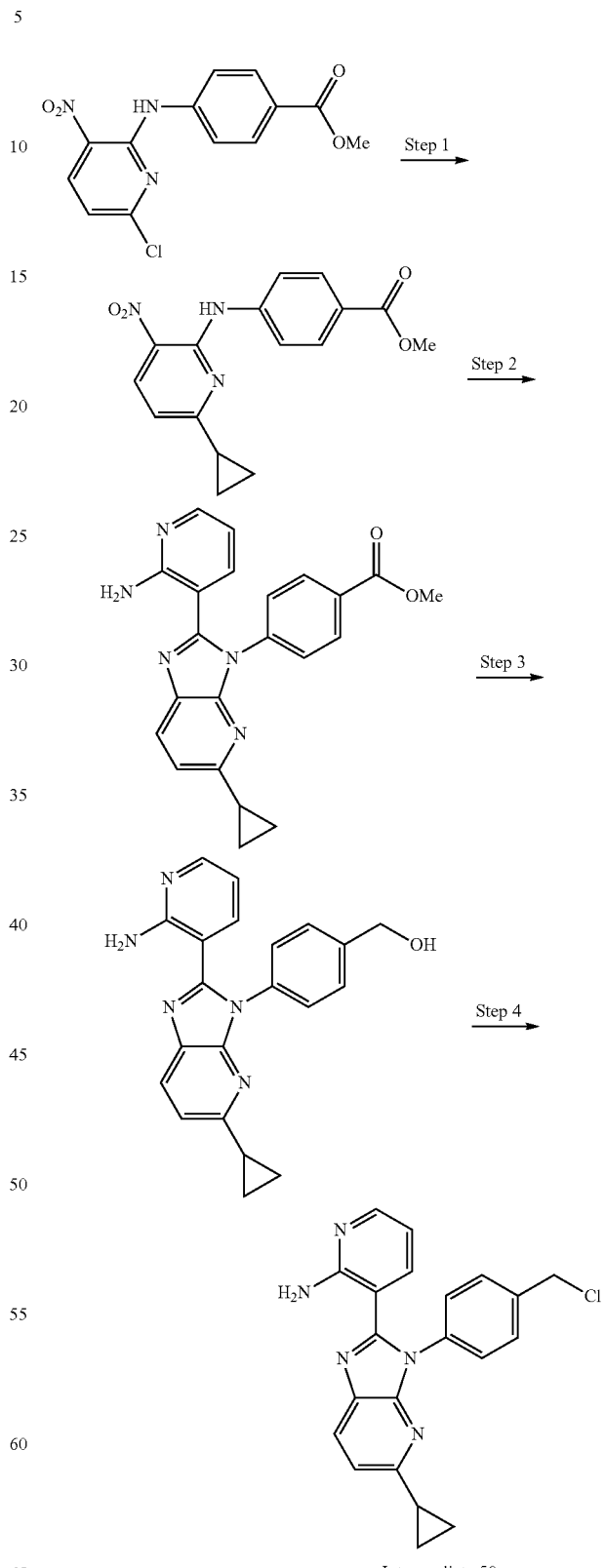

Intermediate 50

Step 1: Methyl 4-((6-cyclopropyl-3-nitropyridin-2-yl)amino)benzoate

To a solution of methyl 4-((6-chloro-3-nitropyridin-2-yl)amino)benzoate (refer to Intermediate 13 for detail procedures. 30 g, 97.5 mmol) in 1,4-dioxane (300 mL) were added cyclopropylboronic acid (12.6 g, 146 mmol), $Cs_2CO_3$ (95.3 g, 292 mmol) and $H_2O$ (50 mL) at 25° C. The mixture was stirred at 100° C. for 12 hr under $N_2$. The reaction mixture was poured into $H_2O$ (500 mL) and extracted with $CH_2Cl_2$ (200 mL×2). The combined organic layers were washed with brine (400 mL), dried over anhydrous $Na_2SO_4$, filtered and concentrated. The residue was purified by silica gel flash chromatography (Eluent of 0~50% EtOAc in petroleum ether, and then use $CH_2C_2$ directly) to give methyl 4-((6-cyclopropyl-3-nitropyridin-2-yl)amino)benzoate (25 g, yield: 74%) as an off-white solid. MS: m/z=314.0 [M+H]$^+$. $^1$H NMR (400 MHz, Dimethylsulfoxide-d$_6$) δ 10.20 (s, 1H), 8.42 (d, J=8.4 Hz, 1H), 7.94 (d, J=8.4 Hz, 2H), 7.80 (d, J=8.8 Hz, 2H), 7.05 (d, J=8.4 Hz, 1H), 3.84 (s, 3H), 2.28-2.18 (m, 1H), 1.15-1.08 (m, 2H), 1.07-1.01 (m, 2H).

Step 2: Methyl 4-(2-(2-aminopyridin-3-yl)-5-cyclopropyl-3H-imidazo[4,5-b]pyridin-3-yl)benzoate To a solution of methyl 4-((6-cyclopropyl-3-nitropyridin-2-yl)amino)benzoate (20 g, 63.8 mmol) in DMSO (500 mL) were added 2-aminopyridine-3-carbaldehyde (9.4 g, 76.6 mmol) and $Na_2S_2O_4$ (44.5 g, 255 mmol) at 25° C. The mixture was stirred at 100° C. for 12 hr. The reaction mixture was poured into $H_2O$ (500 mL) and then extracted with $CH_2Cl_2$ (200 mL×2). The combined organic layers were washed with brine (400 mL), dried over anhydrous $Na_2SO_4$, filtered and concentrated to dryness. The residue was purified by silica gel flash chromatography (Eluent of 1~3% MeOH in $CH_2Cl_2$) to give methyl 4-(2-(2-aminopyridin-3-yl)-5-cyclopropyl-3H-imidazo[4,5-b]pyridin-3-yl)benzoate (10 g. yield: 37%) as a red solid. MS: m/z=386.1 [M+H]$^+$. $^1$H NMR (400 MHz, Dimethylsulfoxide-d$_6$) δ 8.11-8.06 (m, 3H), 8.02 (dd, J=5.6, 1.6 Hz, 1H), 7.57 (d, J=8.4 Hz, 2H), 7.41-7.27 (m, 4H), 6.59 (dd, J=7.6, 5.2 Hz, 1H), 3.89 (s, 3H), 2.24-2.17 (m, 1H), 0.98-0.92 (m, 2H), 0.87-0.82 (m, 2H).

Step 3: (4-(2-(2-Aminopyridin-3-yl)-5-cyclopropyl-3H-imidazo[4,5-b]pyridin-3-yl)phenyl)methanol To a solution of methyl 4-(2-(2-aminopyridin-3-yl)-5-cyclopropyl-3H-imidazo[4,5-b]pyridin-3-yl)benzoate (2 g, 5.2 mmol) in THF (50 mL) was added LiAlH$_4$ (3.1 mL, 2.5M) at 0° C. The mixture was stirred at 0° C. for 1.5 hr, and then was quenched with $Na_2SO_4 \cdot 10H_2O$ (8 g) at 0° C. The mixture was filtered, and the filter cake was washed by $CH_2Cl_2$ (30 mL×2). The filtrate was concentrated under reduced pressure to give (4-(2-(2-aminopyridin-3-yl)-5-cyclopropyl-3H-imidazo[4,5-b]pyridin-3-yl)phenyl)methanol (1.8 g, crude) as a yellow solid, which was used in the next step without further purification. MS: m/z=358.0 [M]$^+$.

Step 4: 3-(3-(4-(Chloromethyl)phenyl)-5-cyclopropyl-3H-imidazo[4,5-b]pyridin-2-yl)pyridin-2-amine To a solution of (4-(2-(2-aminopyridin-3-yl)-5-cyclopropyl-3H-imidazo[4,5-b]pyridin-3-yl)phenyl)methanol (1.4 g, 3.9 mmol) in $CH_2Cl_2$ (20 mL) was added $SOCl_2$ (2.8 g, 23.5 mmol) dropwise at 25° C. The mixture was stirred at 40° C. for 1 hr. The reaction mixture was concentrated to give 3-(3-(4-(chloromethyl)phenyl)-5-cyclopropyl-3H-imidazo[4,5-b]pyridin-2-yl)pyridin-2-amine (Intermediate 50, 1.43 g, yield: 93%) as an off-white solid. MS: m/z=376.0 [M+H]$^+$. $^1$H NMR (400 MHz, Dimethylsulfoxide-d$_6$) δ 8.59-8.24 ((m, 2H), 8.17-8.08 (m, 2H), 7.81 (dd, J=7.2, 1.6 Hz, 1H), 7.60 (d, J=8.0 Hz, 2H), 7.48 (d, J=8.4 Hz, 2H), 7.35 (d, J=8.4 Hz, 1H), 6.87 (dd, J=7.6, 6.0 Hz, 1H), 4.85 (s, 2H), 2.27-2.17 (m, 1H), 1.00-0.92 (m, 2H), 0.88-0.81 (m, 2H).

Intermediate 51: 4-(Piperidin-4-ylamino)pyrimidine-2-carbonitrile

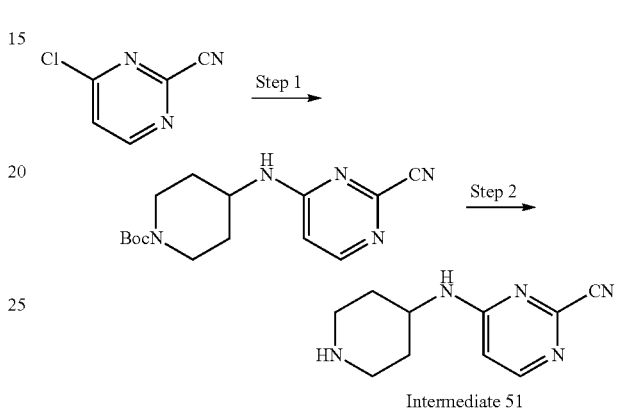

Step 1: tert-Butyl 4-((2-cyanopyrimidin-4-yl)amino)piperidine-1-carboxylate

To a solution of tert-butyl 4-aminopiperidine-1-carboxylate (600 mg, 3.0 mmol) and 2-chloropyrimidine-4-carbonitrile (418 mg, 3.0 mmol) in DMF (5 mL) were added $K_2CO_3$ (1.24 g, 8.99 mmol) and NaI (89.8 mg, 599 μmol). The mixture was stirred at 80° C. for 1 hr. The reaction mixture was diluted with $H_2O$ (20 mL), and then extracted with EtOAc (30 mL×2). The combined organic layers were washed with brine (50 mL), dried over $Na_2SO_4$, filtered, and concentrated under reduced pressure. The residue was purified by silica gel flash chromatography (Eluent of 0~50% EtOAc in petroleum ether) to give tert-butyl 4-[(2-cyanopyrimidin-4-yl)amino]piperidine-1-carboxylate (860 mg, yield: 92%) as a white solid. $^1$H NMR (400 MHz, Dimethylsulfoxide-d$_6$) δ 8.13-8.01 (m, 2H), 6.66 (d, J=5.6 Hz, 1H), 4.05-3.95 (m, 1H), 3.87-3.84 (m, 2H), 2.99-2.86 (m, 2H), 1.86-1.83 (m, 2H), 1.40 (s, 9H), 1.34-1.26 (m, 2H).

Step 2: 4-(Piperidin-4-ylamino)pyrimidine-2-carbonitrile

To a solution of tert-butyl 4-[(2-cyanopyrimidin-4-yl)amino]piperidine-1-carboxylate (110 mg, 362 μmol) in DCM (3 mL) was added TFA (767 mg, 6.73 mmol). The mixture was stirred at 25° C. for 1 hr. The reaction mixture was concentrated under reduced pressure. The crude 4-(piperidin-4-ylamino)pyrimidine-2-carbonitrile (Intermediate 51, 120 mg, yield: 100%, TFA salt) was used in the next step without further purification. MS: m/z=204.0 [M+H]$^+$.

Intermediate 52:
6-(Piperidin-4-ylamino)pyrimidine-4-carbonitrile

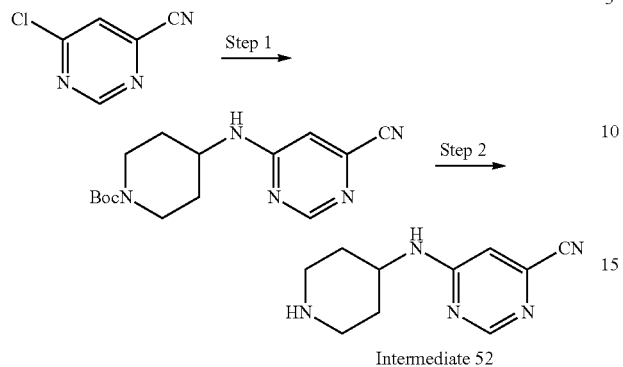

Intermediate 52

Step 1: tert-Butyl 4-((6-cyanopyrimidin-4-yl)amino)piperidine-1-carboxylate

To a solution of tert-butyl 4-aminopiperidine-1-carboxylate (700 mg, 3.50 mmol) and 6-chloropyrimidine-4-carbonitrile (487 mg, 3.50 mmol) in DMF (5 mL) were added $K_2CO_3$ (1.45 g, 10.5 mmol) and NaI (104 mg, 699 μmol). The mixture was stirred at 80° C. for 2 hr. The reaction mixture was diluted with $H_2O$ (20 mL), and then extracted with EtOAc (30 mL×2). The combined organic layers were washed with brine (50 mL), dried over $Na_2SO_4$, filtered and concentrated under reduced pressure. The residue was purified by silica gel flash chromatography (Eluent of 0~45% EtOAc in petroleum ether) to give tert-butyl 4-[(6-cyanopyrimidin-4-yl)amino]piperidine-1-carboxylate (1.0 g, yield: 94%) as a white solid. MS: m/z=304.0 $[M+H]^+$. $^1H$ NMR (400 MHz, Dimethylsulfoxide-$d_6$) δ 8.50 (s, 1H), 8.07 (d, J=7.6 Hz, 1H), 6.92 (s, 1H), 4.08-4.01 (m, 1H), 3.88-3.85 (m, 2H), 2.95-2.75 (m, 2H), 1.86-1.8.3 (m, 2H), 1.40 (s, 9H), 1.34-1.27 (m, 2H).

Step 2: 6-(Piperidin-4-ylamino)pyrimidine-4-carbonitrile

To a solution of tert-butyl 4-[(6-cyanopyrimidin-4-yl)amino]piperidine-1-carboxylate (285 mg, 939 μmol) in $CH_2Cl_2$ (5 mL) was added TFA (535 mg, 4.7 mol). The mixture was stirred at 25° C. for 1 hr. The reaction mixture was concentrated under reduced pressure. The crude product 6-(piperidin-4-ylamino)pyrimidine-4-carbonitrile (Intermediate 52, 298 mg TFA salt, yield: 100%), which was used in the next step without further purification. MS: m/z=204.0 $[M+H]^+$.

Intermediate 53:
4-(Piperazin-1-yl)pyrimidine-2-carbonitrile

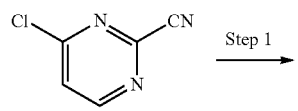

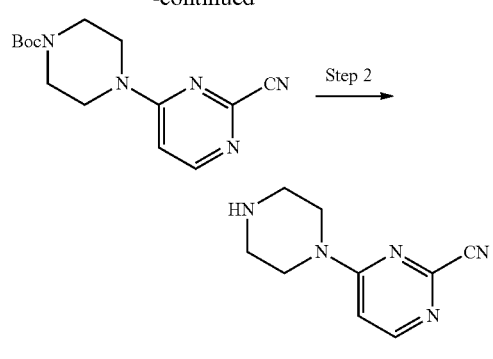

Intermediate 53

Step 1: Tert-butyl 4-(2-cyanopyrimidin-4-yl)piperazine-1-carboxylate

To a solution of tert-butyl piperazine-1-carboxylate (550 mg, 2.95 mmol) and 2-chloropyrimidine-4-carbonitrile (412 mg, 2.95 mmol) in DMF (5 mL) were added $K_2CO_3$ (1.22 g, 8.86 mmol) and NaI (88.5 mg, 590 μmol). The mixture was stirred at 80° C. for 1 hr. The reaction mixture was diluted with $H_2O$ (20 mL), and then extracted with EtOAc (30 mL×2). The combined organic layers were washed with brine (50 mL), dried over $Na_2SO_4$, filtered and concentrated under reduced pressure. The residue was purified by silica gel flash chromatography (Eluent of 0~10% EtOAc in petroleum ether) to give tert-butyl 4-(2-cyanopyrimidin-4-yl)piperazine-1-carboxylate (780 mg, yield: 92%) as a white solid. MS: m/z=290.0 $[M+H]^+$. $^1H$ NMR (400 MHz, Dimethylsulfoxide-$d_6$) δ 8.29 (d, J=6.4 Hz, 1H), 7.10 (d, J=6.4 Hz, 1H), 3.73-3.60 (m, 4H), 3.46-3.41 (m, 4H), 1.42 (s, 9H).

Step 2: 4-(Piperazin-1-yl)pyrimidine-2-carbonitrile

To a solution of tert-butyl 4-(2-cyanopyrimidin-4-yl)piperazine-1-carboxylate (140 mg, 483 μmol) in $CH_2Cl_2$ (3 mL) was added TFA (767 mg, 6.73 mmol). The mixture was stirred at 25° C. for 1 hr. The reaction mixture was concentrated under reduced pressure. The crude 4-(piperazin-1-yl)pyrimidine-2-carbonitrile (Intermediate 53, 146 mg TFA salt, yield: 100%) was used in the next step without further purification. MS: m/z=190.0 $[M+H]^+$.

Intermediate 54:
6-(Piperazin-1-yl)pyrimidine-4-carbonitrile

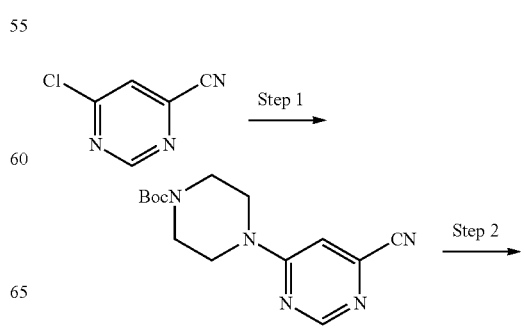

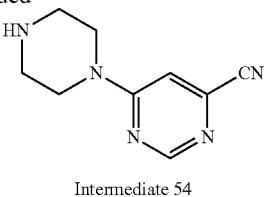

Intermediate 54

Step 1: tert-Butyl 4-(6-cyanopyrimidin-4-yl)piperazine-1-carboxylate

To a solution of tert-butyl piperazine-1-carboxylate (700 mg, 3.7 mmol) and 6-chloropyrimidine-4-carbonitrile (524 mg, 3.7 mmol) in DMF (7 mL) were added K$_2$CO$_3$ (1.56 g, 11.3 mmol) and NaI (112 mg, 751 μmol). The mixture was stirred at 80° C. for 2 hr. The reaction mixture was diluted with H$_2$O (20 mL), and then extracted with EtOAc (30 mL×2). The combined organic layers were washed with brine (50 mL), dried over Na$_2$SO$_4$, filtered and concentrated under reduced pressure. The residue was purified by silica gel flash chromatography (Eluent of 0~10% EtOAc in petroleum ether) to give tert-butyl 4-(6-cyanopyrimidin-4-yl)piperazine-1-carboxylate (890 mg yield: 82%) as a white solid. MS: m/z=290.0 [M+H]$^+$. $^1$H NMR (400 MHz, Dimethylsulfoxide-d$_6$) δ 8.58 (s, 1H), 7.56 (s, 1H), 3.75-3.60 (m, 4H), 3.43-3.40 (m, 4H), 1.42 (s, 9H).

Step 2: 6-(Piperazin-1-yl)pyrimidine-4-carbonitrile

To a solution of tert-butyl 4-(6-cyanopyrimidin-4-yl)piperazine-1-carboxylate (180 mg, 622 μmol) in CH$_2$Cl$_2$ (3 mL) was added TFA (1.54 g, 13.5 mmol). The mixture was stirred at 25° C. for 1 hr. The reaction mixture was concentrated under reduced pressure. The crude 6-(piperazin-1-yl)pyrimidine-4-carbonitrile (Intermediate 54, 188 mg, yield: 100%, TFA) was used in the next step without further purification.

Intermediate 55: 4-(Piperazin-1-yl)-1,3,5-triazine-2-carbonitrile

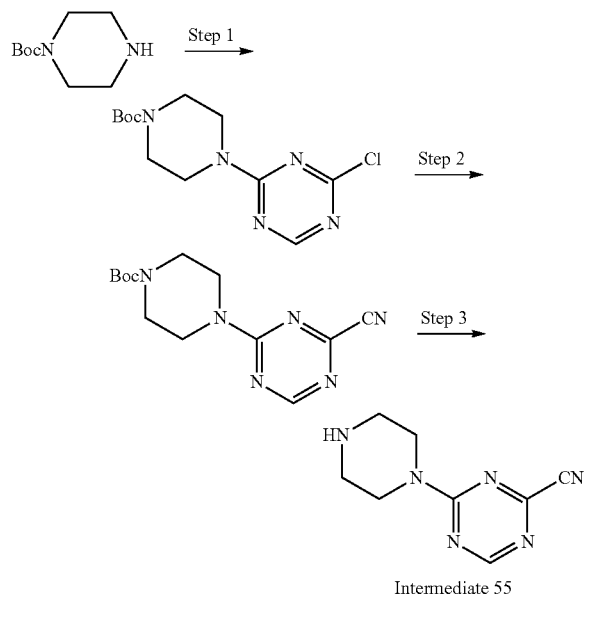

Intermediate 55

Step 1: tert-Butyl 4-(4-chloro-1,3,5-triazin-2-yl)piperazine-1-carboxylate

To a solution of tert-butyl piperazine-1-carboxylate (3 g, 1.11 mmol) in THF (70 mL) was added DIEA (3.12 g, 24.2 mmol). The mixture was stirred at 0° C. for 10 min. Then 2,4-dichloro-1,3,5-triazine (2.42 g, 16.1 mmol) in THF (30 mL) was added to the mixture. The mixture was stirred at 25° C. for 16 hr. The mixture was partitioned between EtOAc (600 mL) and H$_2$O (200 mL). The combined organic layers were washed with H$_2$O (60 mL) and dried over Na$_2$SO$_4$, filtered and concentrated. The residue was purified by silica gel flash chromatography (Eluent of 0~27% EtOAc in petroleum ether) to give tert-butyl 4-(4-chloro-1,3,5-triazin-2-yl)piperazine-1-carboxylate (3.45 g, yield: 70%) as a light-yellow solid. MS: m/z=300.1 [M+H]$^+$. $^1$H NMR (400 MHz, Chloroform-d) δ 8.36 (s, 1H), 3.87-3.83 (m, 4H), 3.51-3.48 (m, 4H), 1.48 (s, 9H).

Step 2: Tert-butyl 4-(4-cyano-1,3,5-triazin-2-yl)piperazine-1-carboxylate

To a solution of tert-butyl 4-(4-chloro-1,3,5-triazin-2-yl)piperazine-1-carboxylate (3.45 g, 11.5 mmol) in DMSO (110 mL) were added KCN (1.64 g, 25.2 mmol) and DABCO (258 mg, 2.30 mmol). The mixture was stirred at 25° C. for 1 hr. The reaction mixture was poured into H$_2$O (1 L). The resulting mixture was extracted with EtOAc (500 mL×2). The combined organic layers were washed with brine (100 mL), dried over Na$_2$SO$_4$, filtered and concentrated under reduced pressure. After purified by silica gel flash chromatography (Eluent of 0~30% EtOAc in petroleum ether), tert-butyl 4-(4-cyano-1,3,5-triazin-2-yl)piperazine-1-carboxylate (1.5 g, yield: 44%) was obtained as a light-yellow solid. MS: m/z=291.1 [M+H]$^+$. $^1$H NMR (400 MHz, Chloroform-d) δ 8.57 (s, 1H), 3.89-3.82 (m, 4H), 3.53-3.50 (m, 4H), 1.48 (s, 9H).

Step 3: 4-(Piperazin-1-yl)-1,3,5-triazine-2-carbonitrile

To a solution of tert-butyl 4-(4-cyano-1,3,5-triazin-2-yl)piperazine-1-carboxylate (200 mg, 689 μmol) in CH$_2$Cl$_2$ (3 mL) was added TFA (1.02 g, 8.07 mmol). The mixture was stirred at 25° C. for 1 hr. The reaction mixture was concentrated under reduced pressure. The crude 4-(piperazin-1-yl)-1,3,5-triazine-2-carbonitrile (Intermediate 55, 209 mg TFA salt, yield: 100%) was used in the next step without further purification.

Intermediate 56: 3-(3-(4-(Chloromethyl)phenyl)-5-morpholino-3H-imidazo[4,5-b]pyridin-2-yl)pyridin-2-amine

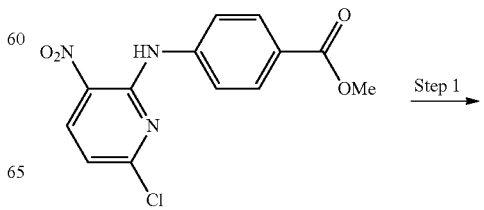

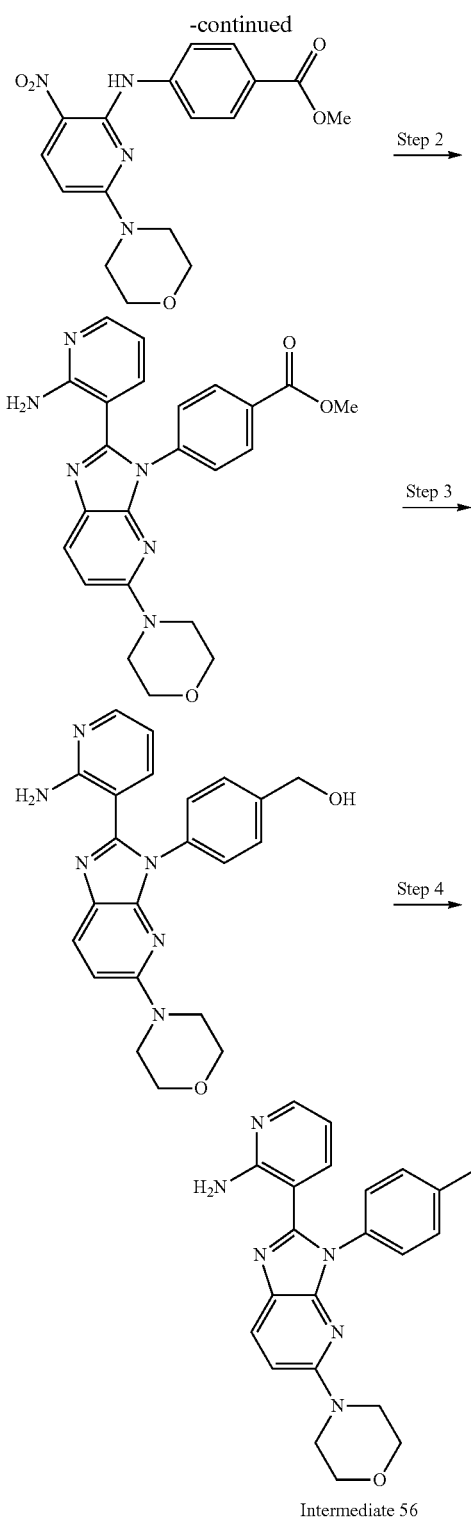

Intermediate 56

Step 1: Methyl 4-((6-morpholino-3-nitropyridin-2-yl)amino)benzoate

A mixture of methyl 4-((6-chloro-3-nitropyridin-2-yl)amino)benzoate (refer to Intermediate 13 for detail procedures, 2.5 g, 8.13 mmol), morpholine (849 mg, 9.75 mmol), DIEA (2.10 g, 16.2 mmol) in CH$_3$CN (30 mL) was stirred at 90° C. for 2 hr. The reaction mixture was filtered and the filter cake was dried under reduced pressure to give methyl 4-((6-morpholino-3-nitropyridin-2-yl)amino)benzoate (2.94 g, yield: 92%) as a yellow solid. MS: m/z=359.0 [M+H]$^+$. $^1$H NMR (400 MHz, Dimethylsulfoxide-d$_6$) 10.74 (s, 1H), 8.27 (d, J=9.6 Hz, 1H), 7.98-7.94 (m, 2H), 7.83-7.79 (m, 2H), 6.58 (d, J=9.6 Hz, 1H), 3.84 (s, 3H), 3.75-3.65 (m, 8H).

Step 2: Methyl 4-(2-(2-aminopyridin-3-yl)-5-morpholino-3H-imidazo[4,5-b]pyridin-3-yl)benzoate A mixture of methyl 4-((6-morpholino-3-nitropyridin-2-yl)amino)benzoate (2.94 g, 8.20 mmol), 2-aminonicotinaldehyde (1.10 g, 9.02 mmol), and Na$_2$S$_2$O$_4$ (5.71 g, 32.8 mmol) in DMSO (30 mL) was stirred at 100° C. for 16 hr. The reaction mixture was cooled to room temperature and the pH was adjusted to about 9 with sat. NaHCO$_3$. Then the mixture was diluted with H$_2$O (100 mL) and extracted with CH$_2$Cl$_2$ (100 mL×3). The combined organic layers were washed with brine (100 mL), dried over Na$_2$SO$_4$, filtered, and concentrated under reduced pressure. The crude was triturated with EtOAc (100 mL) at 20° C. for 30 min to give methyl 4-(2-(2-aminopyridin-3-yl)-5-morpholino-3H-imidazo[4,5-b]pyridin-3-yl)benzoate (3.5 g, yield: 83%) as a green solid. MS: m/z=431.1 [M+H]$^+$. $^1$H NMR (400 MHz, Dimethylsulfoxide-d$_6$) δ 8.07 (d, J=8.4 Hz, 2H), 8.03-7.97 (m, 2H), 7.55 (d, J=8.8 Hz, 2H), 7.32-7.13 (m, 3H), 6.93 (d, J=8.8 Hz, 1H), 6.51-6.44 (m, 1H), 3.88 (s, 3H), 3.70-3.65 (m, 4H), 3.44-3.38 (m, 4H)

Step 3: (4-(2-(2-Aminopyridin-3-yl)-5-morpholino-3H-imidazo[4,5-b]pyridin-3-yl)phenyl)methanol A mixture of methyl 4-(2-(2-aminopyridin-3-yl)-5-morpholino-3H-imidazo[4,5-b]pyridin-3-yl)benzoate (3.5 g, 8.13 mmol) in THF (100 mL) was added LiAlH$_4$ (2.5 M, 3.90 mL) dropwise at 0° C., then the mixture was stirred at 20° C. for 1 hr. The reaction mixture was quenched with Na$_2$SO$_4$·10H$_2$O (5 g) at 0° C., filtered and concentrated under reduced pressure to give (4-(2-(2-aminopyridin-3-yl)-5-morpholino-3H-imidazo[4,5-b]pyridin-3-yl)phenyl)methanol (2.4 g, yield: 63%) as a green solid. MS: m/z=403.1 [M+H]$^+$.

Step 4: 3-(3-(4-(Chloromethyl)phenyl)-5-morpholino-3H-imidazo[4,5-b]pyridin-2-yl)pyridin-2-amine To a mixture of (4-(2-(2-aminopyridin-3-yl)-5-morpholino-3H-imidazo[4,5-b]pyridin-3yl)phenyl)methanol (2.4 g, 5.96 mmol) in CH$_2$Cl$_2$ (16 mL) was added SOCl$_2$ (4.26 g, 35.7 mmol,). The mixture was stirred at 40° C. for 1 hr. The reaction mixture was concentrated under reduced pressure to give 3-(3-(4-(chloromethyl)phenyl)-5-morpholino-3H-imidazo[4,5-b]pyridin-2-yl)pyridin-2-amine (Intermediate 56, 2.6 g, yield: 64%) as a green solid. MS: m/z=421.0 [M+H]$^+$.

Intermediate 57: 3-(2-(2-Aminopyridin-3-yl)-3-(4-(chloromethyl)phenyl)-3H-imidazo[4,5-b]pyridin-5-yl)-1-methylpyridin-2(1H)-one

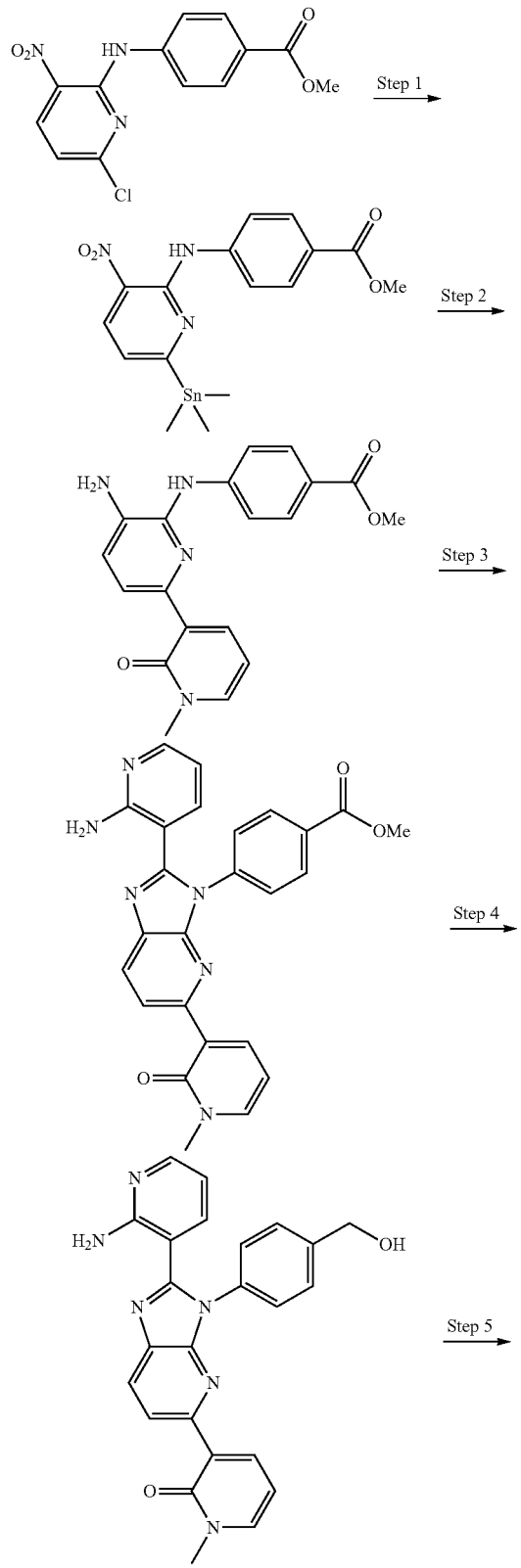

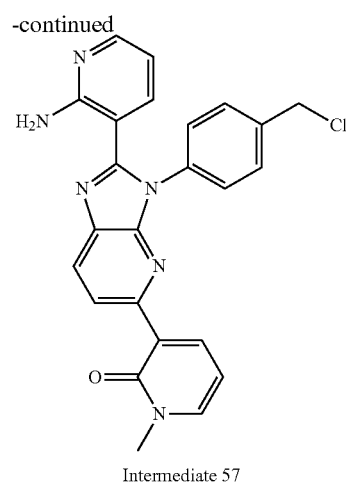

Intermediate 57

Step 1: Methyl 4-((3-nitro-6-(trimethylstannyl)pyridin-2-yl)amino)benzoate

To a solution of methyl 4-((6-chloro-3-nitropyridin-2-yl)amino)benzoate (refer to Intermediate 13 for detail procedure, 5 g, 16.3 mmol), Pd(PPh$_3$)$_4$ (939 mg, 813 µmol) and 1,1,1,2,2,2-hexamethyldistannane (11.1 g, 33.7 mmol) in 1,4-dioxane (100 mL) was degassed and purged with N$_2$ three times. The mixture was stirred at 90° C. for 16 hr under N$_2$ atmosphere. The reaction was concentrated under reduced pressure to give methyl 4-((3-nitro-6-(trimethylstannyl)pyridin-2-yl)amino)benzoate (7.09 g, yield: 34%) as a black solid, which was directly used in the next step.

Step 2: Methyl 4-((1'-methyl-5-nitro-2'-oxo-1',2'-dihydro-[2,3'-bipyridin]-6-yl)amino)benzoate A mixture of methyl 4-((3-nitro-6-(trimethylstannyl)pyridin-2-yl)amino)benzoate (7.09 g, 16.3 mmol), 3-bromo-1-methylpyridin-2(1H)-one (3.06 g, 16.3 mmol), and Pd(PPh$_3$)$_4$ (939 mg, 813 µmol) in 1,4-dioxane (100 mL) was degassed and purged with N$_2$ three times, and then the mixture was stirred at 125° C. for 1 hr under N$_2$ atmosphere. The reaction was concentrated under reduced pressure. After purified by silica gel flash chromatography (Eluent of 1~5% MeOH in CH$_2$Cl$_2$), methyl 4-((1'-methyl-5-nitro-2'-oxo-1',2'-dihydro-[2,3'-bipyridin]-6-yl)amino)benzoate (3.6 g, purity: 58%) was obtained as a black solid. MS: m/z=351.1 [M+H]$^+$.

Step 3: Methyl 4-(2-(2-aminopyridin-3-yl)-5-(1-methyl-2-oxo-1,2-dihydropyridin-3-yl)-3H-imidazo[4,5-b]pyridin-3-yl)benzoate To a solution of methyl 4-((5-amino-1'-methyl-2'-oxo-1',2'-dihydro-[2,3'-bipyridin]-6-yl)amino)benzoate (2.6 g, 7.42 mmol) in DMSO (30 mL) were added Na$_2$S$_2$O$_4$ (5.94 g, 29.7 mmol, 87% purity) and 2-aminonicotinaldehyde (1.09 g, 8.9 mmol). The mixture was stirred at 100° C. for 2 hr. The reaction mixture was quenched with H$_2$O (50 mL) at 25° C., and then diluted with CH$_2$Cl$_2$ (100 mL) and extracted with H$_2$O (100 mL×3). The combined organic layers were washed with brine (100 mL), dried over Na$_2$SO$_4$, filtered, and concentrated under reduced pressure. After purified by silica gel flash chromatography (Eluent of 1~5% MeOH in CH$_2$Cl$_2$), methyl 4-(2-(2-aminopyridin-3-yl)-5-(1-methyl-2- oxo-1,2-dihydropyridin-3-yl)-3H-imidazo[4,5-b]pyridin-3-yl)benzoate (750 mg, yield: 24%) was obtained as a brown solid. MS: m/z=453.1 [M+H]+.

Step 4: 3-(2-(2-Aminopyridin-3-yl)-3-(4-(hydroxymethyl)phenyl)-3H-imidazo[4,5-b]pyridin-5-yl)-1-methylpyridin-2(1H)-one To a solution of methyl 4-(2-(2-aminopyridin-3-yl)-5-(1-methyl-2-oxo-1,2-dihydropyridin-3-yl)-3H-imidazo[4,5-b]pyridin-3-yl)benzoate (1.0 g, 2.21 mmol) in THF (15 mL) was added LiAlH$_4$ (1.33 mL, 2.5 M in THF). The mixture was stirred at 0° C. for 1 hr. The reaction mixture was quenched with Na$_2$SO$_4$·10H$_2$O (2 g) at 0° C., filtered and concentrated under reduced pressure. After purified by silica gel flash chromatography (Eluent of 1~5% MeOH in CH$_2$Cl$_2$), 3-(2-(2-aminopyridin-3-yl)-3-(4-(hydroxymethyl)phenyl)-3H-imidazo[4,5-b]pyridin-5-yl)-1-methylpyridin-2(1H)-one (200 mg, yield: 16%) was obtained as a yellow solid, which was used to the next step directly.

Step 5: 3-(2-(2-Aminopyridin-3-yl)-3-(4-(chloromethyl)phenyl)-3H-imidazo[4,5-b]pyridin-5-yl)-1-methylpyridin-2(1H)-one To a solution of 3-(2-(2-aminopyridin-3-yl)-3-(4-(hydroxymethyl)phenyl)-3H-imidazo[4,5-b]pyridin-5-yl)-1-methylpyridin-2(1H)-one (160 mg, 377 μmol) in CH$_2$Cl$_2$ (20 mL) was added SOCl$_2$ (135 mg, 1.13 mmol) at 0° C. The mixture was stirred at 25° C. for 1 hr. The reaction mixture was quenched with H$_2$O (3 mL) at 0° C., and then filtered and concentrated under reduced pressure to give 3-(2-(2-aminopyridin-3-yl)-3-(4-(chloromethyl)phenyl)-3H-imidazo[4,5-b]pyridin-5-yl)-1-methylpyridin-2(11H)-one (Intermediate 57, 150 mg, yield: 66%) as a yellow solid. MS: m/z=443.0 [M+H]+.

Intermediate 58: 3-(3-(4-(Chloromethyl)phenyl)-5-cyclobutyl-3H-imidazo[4,5-b]pyridin-2-yl)pyridin-2-amine

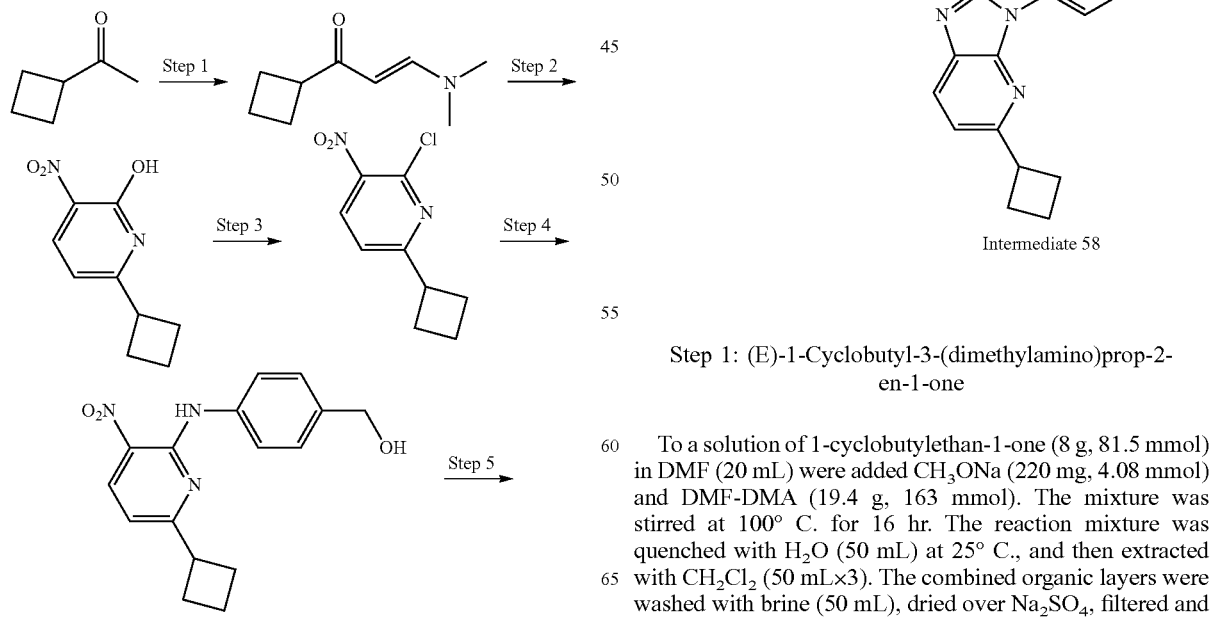

Intermediate 58

Step 1: (E)-1-Cyclobutyl-3-(dimethylamino)prop-2-en-1-one

To a solution of 1-cyclobutylethan-1-one (8 g, 81.5 mmol) in DMF (20 mL) were added CH$_3$ONa (220 mg, 4.08 mmol) and DMF-DMA (19.4 g, 163 mmol). The mixture was stirred at 100° C. for 16 hr. The reaction mixture was quenched with H$_2$O (50 mL) at 25° C., and then extracted with CH$_2$Cl$_2$ (50 mL×3). The combined organic layers were washed with brine (50 mL), dried over Na$_2$SO$_4$, filtered and concentrated under reduced pressure to give (E)-1-cyclobutyl-3-(dimethylamino)prop-2-en-1-one (10 g, yield: 74%) as a yellow oil. MS: m/z=154.2 [M+H]+.

Step 2: 6-Cyclobutyl-3-nitropyridin-2-ol

To a solution of (E)-1-cyclobutyl-3-(dimethylamino)prop-2-en-1-one (10 g, 65.3 mmol) in $H_2O$ (100 mL) were added piperidinium acetate (4.74 g, 32.6 mmol) and 2-nitroacetamide (10.2 g, 97.9 mmol). The mixture was stirred at 25° C. for 16 hr. The reaction mixture was extracted with $CH_2Cl_2$ (150 mL×2). The combined organic layers were washed with brine (150 mL), dried over $Na_2SO_4$, filtered, and concentrated under reduced pressure. The crude was triturated with EtOAc:petroleum ether=1:10 at 25° C. for 10 min to give 6-cyclobutyl-3-nitropyridin-2-ol (6.5 g, yield: 51%) as a yellow solid. MS: m/z=195.1 [M+H]+. 1H NMR (400 MHz, Dimethylsulfoxide-$d_6$) δ 12.85-12.40 (m, 1H), 8.42 (d, J=8.0 Hz, 1H), 6.34 (d, J=8.0 Hz, 1H), 3.55-3.44 (m, 1H), 2.30-2.13 (m, 4H), 2.00-1.94 (m, 1H), 1.86-1.77 (m, 1H).

Step 3: 2-Chloro-6-cyclobutyl-3-nitropyridine

A solution of 6-cyclobutyl-3-nitropyridin-2-ol (6.5 g, 33.5 mmol) in $POCl_3$ (50 mL) was stirred at 100° C. for 1.5 hr. The reaction mixture was filtered and concentrated under reduced pressure. The crude was quenched with aqueous $NaHCO_3$ (50 mL) at 10° C., and then extracted with $CH_2Cl_2$ (50 mL×3). The combined organic layers were washed with brine (100 mL), dried over $Na_2SO_4$, filtered, and concentrated under reduced pressure to give 2-chloro-6-cyclobutyl-3-nitropyridine (5.5 g, yield: 76%) as a black oil. MS: m/z=213.1 [M+H]+. 1H NMR (400 MHz, Dimethylsulfoxide-$d_6$) δ 8.48 (d, J=8.0 Hz, 1H), 7.56 (d, J=8.4 Hz, 1H), 3.83-3.71 (m, 1H), 2.34-2.22 (m, 4H), 2.07-1.96 (m, 1H), 1.92-1.79 (m, 1H).

Step 4: (4-((6-Cyclobutyl-3-nitropyridin-2-yl)amino)phenyl)methanol

To a solution of 2-chloro-6-cyclobutyl-3-nitropyridine (5.5 g, 25.9 mmol) in DMSO (60 mL) were added DIEA (10 g, 77.6 mmol) and (4-aminophenyl)methanol (3.19 g, 25.9 mmol). The mixture was stirred at 100° C. for 16 hr. The reaction mixture was quenched with $H_2O$ (200 mL) at 25° C., and extracted with $CH_2Cl_2$ (500 mL×3). The combined organic layers were washed with brine (500 mL), dried over $Na_2SO_4$, filtered and concentrated under reduced pressure to give (4-((6-cyclobutyl-3-nitropyridin-2-yl)amino)phenyl)methanol (7.74 g, yield: 83%) as a brown solid. MS: m/z=300.1 [M+H]+.

Step 5: 4-((6-Cyclobutyl-3-nitropyridin-2-yl)amino)benzyl acetate

To a solution of (4-((6-cyclobutyl-3-nitropyridin-2-yl)amino)phenyl)methanol (7.7 g, 25.7 mmol) in $CH_2Cl_2$ (100 mL) were added TEA (7.81 g, 77.2 mmol), $Ac_2O$ (3.94 g, 38.6 mmol) and DMAP (314 mg, 2.57 mmol). The mixture was stirred at 25° C. for 1 hr. The reaction mixture was quenched with $H_2O$ (100 mL) at 25° C., and then extracted with $CH_2Cl_2$ (100 mL×3). The combined organic layers were washed with brine (100 mL), dried over $Na_2SO_4$, filtered and concentrated under reduced pressure. After purified by silica gel flash chromatography (Eluent of 1~5% EtOAc in petroleum ether), 4-((6-cyclobutyl-3-nitropyridin-2-yl)amino)benzyl acetate (5.65 g, yield: 64%) was obtained as a yellow oil. MS: m/z=342.0 [M+H]+.

Step 6: 4-(2-(2-Aminopyridin-3-yl)-5-cyclobutyl-3H-imidazo[4,5-b]pyridin-3-yl)benzyl acetate acetate To a solution of 4-((6-cyclobutyl-3-nitropyridin-2-yl)amino)benzyl acetate (5.6 g, 16.4 mmol) in DMSO (60 mL) were added $Na_2S_2O_4$ (13.1 g, 65.6 mmol, 87% purity) and 2-aminonicotinaldehyde (2.4 g, 19.7 mmol). The mixture was stirred at 100° C. for 16 hr. The reaction mixture was quenched with $H_2O$ (100 mL) at 25° C., and then extracted with $CH_2Cl_2$ (150 mL×2). The combined organic layers were washed with brine (150 mL), dried over $Na_2SO_4$, filtered and concentrated under reduced pressure. After purified by silica gel flash chromatography (Eluent of 1~50% $CH_2Cl_2$ in EtOAc), 4-(2-(2-aminopyridin-3-yl)-5-cyclobutyl-3H-imidazo[4,5-b]pyridin-3-yl)benzyl acetate acetate (2.1 g, yield: 31%) was obtained as a yellow solid. MS: m/z=414.1 [M+H]+. 1H NMR (400 MHz, Dimethylsulfoxide-$d_6$) δ 8.10 (d, J=8.4 Hz, 1H), 7.98 (d, J=4.4 Hz, 1H), 7.52 (d, J=8.0 Hz, 2H), 7.43 (d, J=8.0 Hz, 2H), 7.30 (d, J=8.4 Hz, 1H), 7.16 (d, J=7.2 Hz, 1H), 6.85 (br s, 2H), 6.41 (dd, J=7.6, 5.2 Hz, 1H), 5.16 (s, 2H), 3.74-3.64 (m, 1H), 2.27-2.20 (m, 4H), 2.11 (s, 3H), 1.99-1.92 (m, 1H), 1.84-1.75 (m, 1H).

Step 7: (4-(2-(2-Aminopyridin-3-yl)-5-cyclobutyl-3H-imidazo[4,5-b]pyridin-3-yl)phenyl)methanol To a solution of 4-(2-(2-aminopyridin-3-yl)-5-cyclobutyl-3H-imidazo[4,5-b]pyridin-3-yl)benzyl acetate acetate (500 mg, 1.21 mmol) in MeOH (5 mL), THF (5 mL) and $H_2O$ (2 mL) was added $K_2CO_3$ (501 mg, 3.63 mmol). The mixture was stirred at 25° C. for 0.5 hr. The reaction mixture was diluted with $H_2O$ (10 mL) and extracted with $CH_2Cl_2$ (15 mL×2). The combined organic layers were washed with brine (15 mL), dried over $Na_2SO_4$, filtered and concentrated under reduced pressure to give (4-(2-(2-aminopyridin-3-yl)-5-cyclobutyl-3H-imidazo[4,5-b]pyridin-3-yl)phenyl)methanol (450 mg, yield: 86%) as a yellow solid. MS: m/z=372.0 [M+H]+.

Step 8: 3-(3-(4-(Chloromethyl)phenyl)-5-cyclobutyl-3H-imidazo[4,5-b]pyridin-2-yl)pyridin-2-amine To a solution of (4-(2-(2-aminopyridin-3-yl)-5-cyclobutyl-3H-imidazo[4,5-b]pyridin-3-yl)phenyl)methanol (449 mg, 1.21 mmol) in $CH_2Cl_2$ (10 mL) was added $SOCl_2$ (288 mg, 2.42 mmol) at 0° C. The mixture was stirred at 25° C. for 0.3 hr. The reaction was concentrated under reduced pressure to give 3-(3-(4-(chloromethyl)phenyl)-5-cyclobutyl-3H-imidazo[4,5-b]pyridin-2-yl)pyridin-2-amine (Intermediate 58, 560 mg, HCl salt, yield: 90%) as a yellow solid. MS: m/z=390.1[M+H]+.

Intermediate 59: 3-(3-(4-((4-Aminopiperidin-1-yl)methyl)phenyl)-5-(cyclohex-1-en-1-yl)-3H-imidazo[4,5-b]pyridin-2-yl)pyridin-2-amine

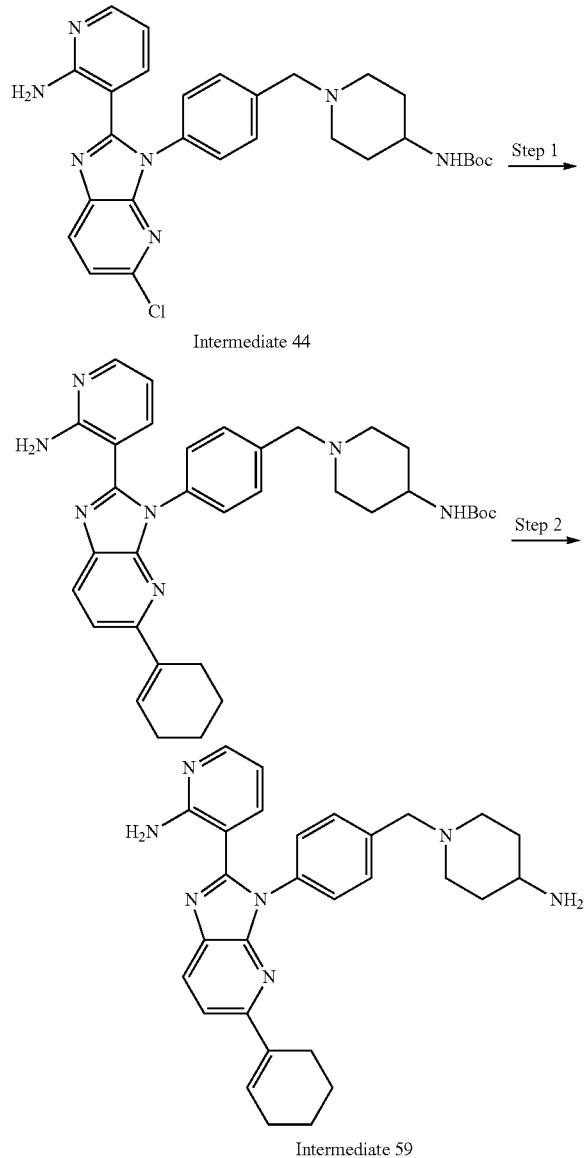

Intermediate 44

Intermediate 59

Step 1: Tert-butyl (1-(4-(2-(2-aminopyridin-3-yl)-5-(cyclohex-1-en-1-yl)-3H-imidazo[4,5-b]pyridin-3-yl)benzyl)piperidin-4-yl)carbamate A mixture of Intermediate 44 (800 mg, 1.5 mmol), cyclohex-1-en-1-ylboronic acid (283 mg, 2.25 mmol), $Cs_2CO_3$ (974 mg, 3.00 mmol), and Pd(dppf)Cl$_2$ (219 mg, 299 μmol) in 1,4-dioxane (2 mL) and H$_2$O (0.5 mL) was degassed and purged with N$_2$ three times, and then the mixture was stirred at 100° C. for 16 hr under N$_2$ atmosphere. The reaction mixture was poured into H$_2$O (10 mL), extracted with EtOAc (15 mL×3). The combined organic layers were dried over anhydrous Na$_2$SO$_4$, filtered and concentrated under reduced pressure. The residue was purified by silica gel flash chromatography (Eluent of 0~7% MeOH in CH$_2$Cl$_2$) to give tert-butyl (1-(4-(2-(2-aminopyridin-3-yl)-5-(cyclohex-1-en-1-yl)-3H-imidazo[4,5-b]pyridin-3-yl)benzyl)piperidin-4-yl)carbamate (702 mg, yield: 81%) as a black brown solid. MS: m/z=580.2 [M+H]$^+$.

Step 2: 3-(3-(4-((4-Aminopiperidin-1-yl)methyl)phenyl)-5-(cyclohex-1-en-1-yl)-3H-imidazo[4,5-b]pyridin-2-yl)pyridin-2-amine To a solution of tert-butyl (1-(4-(2-(2-aminopyridin-3-yl)-5-(cyclohex-1-en-1-yl)-3H-imidazo[4,5-b]pyridin-3-yl)benzyl)piperidin-4-yl)carbamate (200 mg, 345 μmol) in CH$_2$Cl$_2$ (2 mL) was added 4 M HCl in 1,4-dioxane (2.0 mL). After concentrated under reduced pressure, 3-(3-(4-((4-Aminopiperidin-1-yl)methyl)phenyl)-5-(cyclohex-1-en-1-yl)-3H-imidazo[4,5-b]pyridin-2-yl)pyridin-2-amine (Intermediate 59, 160 mg HCl salt, yield: 90%) was obtained as an off-white solid. MS: m/z=480.3 [M+H]$^+$. $^1$H NMR (400 MHz, Dimethylsulfoxide-d$_6$) δ 8.10 (d, J=8.4 Hz, 1H), 7.98 (dd, J=4.8, 1.2 Hz, 1H), 7.53 (d, J=8.0 Hz, 1H), 7.45-7.40 (m, 2H), 7.38-7.32 (m, 2H), 7.14-7.07 (m, 1H), 7.01 (br s, 2H), 6.67-6.60 (m, 1H), 6.34 (dd, J=7.6, 4.8 Hz, 11H), 3.52 (br s, 2H), 3.49-3.48 (m, 1H), 2.76-2.73 (m, 2H), 2.44-2.43 (m, 2H), 2.20-2.19 (m, 2H), 2.02-1.96 (m, 2H), 1.72-1.65 (m, 4H), 1.61-1.54 (m, 2H), 1.27-1.23 (m, 2H).

Intermediate 60: 3-(3-(4-((4-Aminopiperidin-1-yl)methyl)phenyl)-5-cyclohexyl-3H-imidazo[4,5-b]pyridin-2-yl)pyridin-2-amine

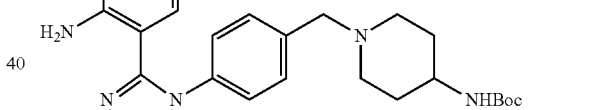

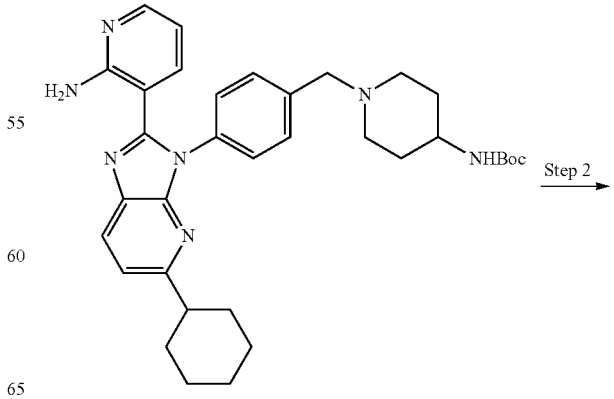

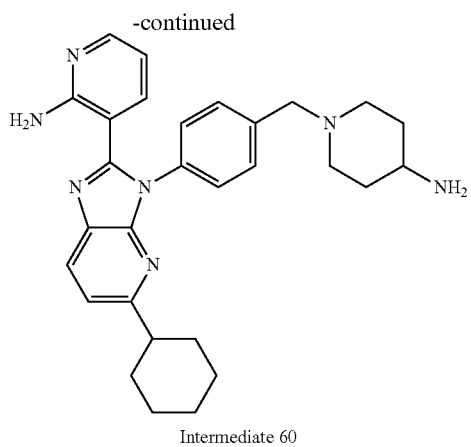

Intermediate 60

Step 1: tert-Butyl (1-(4-(2-(2-aminopyridin-3-yl)-5-cyclohexyl-3H-imidazo[4,5-b]pyridin-3-yl)benzyl) piperidin-4-yl)carbamate To a solution of tert-butyl (1-(4-(2-(2-aminopyridin-3-yl)-5-(cyclohex-1-en-1-yl)-3H-imidazo[4,5-b]pyridin-3-yl)benzyl)piperidin-4-yl)carbamate (refer to Intermediate 59 for detail procedures, 242 mg, 417 μmol) in MeOH (10 mL) was added Pd/C (50 mg, 834 μmol, 10% w/w). The suspension was degassed under reduced pressure and purged with $H_2$ several times. The mixture was stirred under $H_2$ (50 psi) at 50° C. for 24 hr under $H_2$. The reaction mixture was cooled to 25° C., then filtered and concentrated under reduced pressure. The residue was purified by silica gel flash chromatography (Eluent of 0~82% EtOAc in petroleum ether) to give tert-butyl (1-(4-(2-(2-aminopyridin-3-yl)-5-cyclohexyl-3H-imidazo[4,5-b]pyridin-3-yl)benzyl)piperidin-4-yl)carbamate (182 mg, yield: 75%) as a yellow solid. MS: m/z=582.3 [M+H]$^+$.

Step 2: 3-(3-(4-((4-Aminopiperidin-1-yl)methyl) phenyl)-5-cyclohexyl-3H-imidazo[4,5-b]pyridin-2-yl)pyridin-2-amine To a solution of tert-butyl (1-(4-(2-(2-aminopyridin-3-yl)-5-cyclohexyl-3H-imidazo[4,5-b]pyridin-3-yl)benzyl)piperidin-4-yl)carbamate (182 mg, 345 μmol) in 1,4-dioxane (2 mL) was added 4 M HCl in 1,4-dioxane (2.0 mL). The mixture was stirred at 25° C. for 1 hr. The reaction mixture was filtered to give 3-(3-(4-((4-Aminopiperidin-1-yl)methyl)phenyl)-5-cyclohexyl-3H-imidazo[4,5-b]pyridin-2-yl)pyridin-2-amine (Intermediate 60, 162 mg HCl salt, yield: 91%) was obtained as a yellow solid. MS: m/z=482.1 [M+H]$^+$. $^1$H NMR (400 MHz, Methanol-d$_4$) δ 8.25-8.11 (m, 1H), 7.99-7.92 (m, 1H), 7.93-7.77 (m, 3H), 7.65 (d, J=8.0 Hz, 2H), 7.50-7.35 (m, 1H), 6.95-6.73 (m, 1H), 3.70 (d, J=12.0 Hz, 2H), 3.64-3.40 (m, 2H), 3.33-3.31 (m, 3H), 2.88-2.70 (m, 1H), 2.30 (d, J=12.8 Hz, 2H), 2.21-2.02 (m, 2H), 1.95-1.81 (m, 4H), 1.79-1.71 (m, 1H), 1.63-1.49 (m, 2H), 1.39 (m, 2H), 1.35-1.24 (m, 1H).

Intermediate 61: 3-(3-(4-((4-Aminopiperidin-1-yl)methyl)phenyl)-2-(2-aminopyridin-3-yl)-3H-imidazo[4,5-b]pyridin-5-yl)benzonitrile

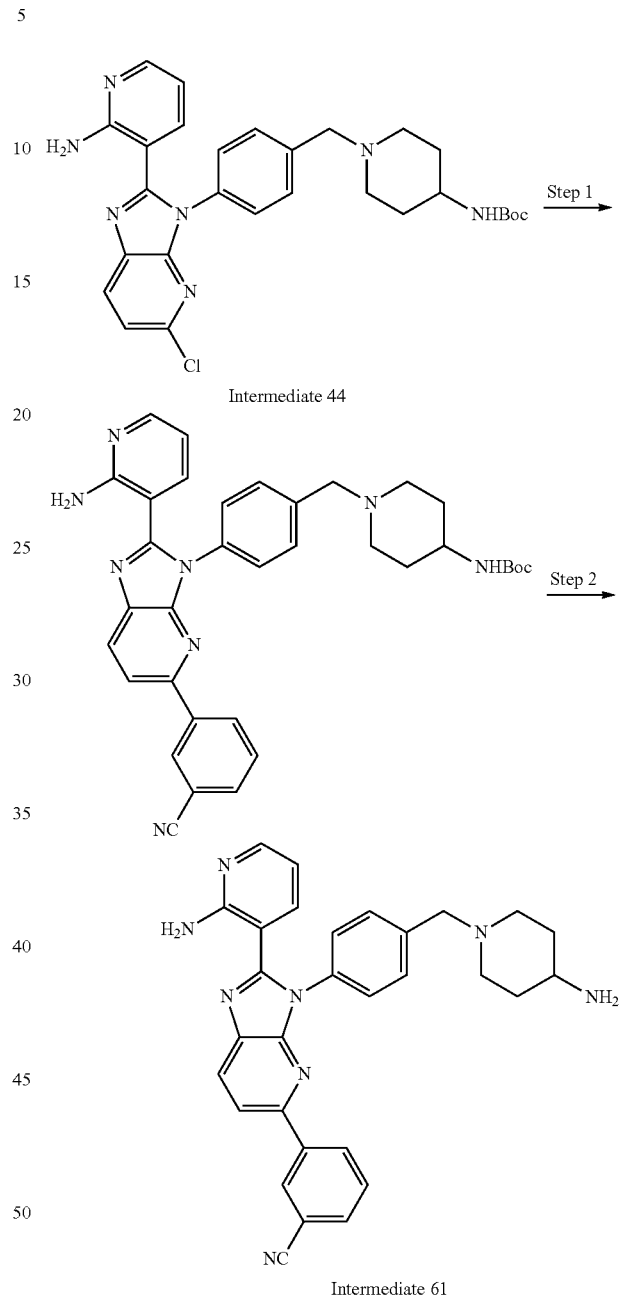

Intermediate 61

Step 1: tert-Butyl (1-(4-(2-(2-aminopyridin-3-yl)-5-(3-cyanophenyl)-3H-imidazo[4,5-b]pyridin-3-yl)benzyl)piperidin-4-yl)carbamate A mixture of Intermediate 44 (350 mg, 655 μmol), (3-cyanophenyl)boronic acid (116 mg, 786 μmol), $K_2CO_3$ (181 mg, 1.31 mmol), and Pd(dppf)Cl$_2$ (24 mg, 33 μmol) in 1,4-dioxane (10 mL) and $H_2O$ (2 mL) was degassed and purged with $N_2$ three times, and then the mixture was stirred at 100° C. for 16 hr under $N_2$ atmosphere. The reaction mixture was poured into $H_2O$ (3 mL) and extracted with EtOAc (15 mL). The combined organic layers were dried over anhydrous Na$_2$SO$_4$, filtered and concentrated under reduced pressure. The residue was purified by silica gel flash chromatography (Eluent of 0~9% MeOH in CH$_2$Cl$_2$) to give tert-butyl (1-(4-(2-(2-aminopyridin-3-yl)-5-(3-cyanophenyl)-3H-imidazo[4,5-b]pyridin-3-yl)benzyl)piperidin-4-yl)carbamate (150 mg, yield: 38%) as a yellow solid. MS: m/z=601.4 [M+H]$^+$.

Step 2: 3-(3-(4-((4-Aminopiperidin-1-yl)methyl)phenyl)-2-(2-aminopyridin-3-yl)-3H-imidazo[4,5-b]pyridin-5-yl)benzonitrile To a solution of tert-butyl (1-(4-(2-(2-aminopyridin-3-yl)-5-(3-cyanophenyl)-3H-imidazo[4,5-b]pyridin-3-yl)benzyl)piperidin-4-yl)carbamate (50 mg, 73 μmol) in 1,4-dioxane (2 mL) was added 4M HCl in 1,4-dioxane (2 mL). The mixture was stirred at 25° C. for 1 hr. The reaction mixture was filtered to give the filter cake. 3-(3-(4-((4-Aminopiperidin-1-yl)methyl)phenyl)-2-(2-aminopyridin-3-yl)-3H-imidazo[4,5-b]pyridin-5-yl)benzonitrile (Intermediate 61, 32 mg HCl salt, yield: 87%) was obtained as a yellow solid. MS: m/z=501.3 [M+H]$^+$. $^1$H NMR (400 MHz, Methanol-d$_4$) δ 8.48-8.32 (m, 3H), 8.14 (d, J=8.8 Hz, 1H), 8.06 (d, J=5.6 Hz, 1H), 7.99-7.87 (m, 3H), 7.83-7.73 (m, 3H), 7.71-7.64 (m, 1H), 6.93-6.89 (m, 1H), 3.79-3.68 (m, 2H), 3.67-3.45 (m, 3H), 3.37 (s, 2H), 2.35-2.33 (m, 2H), 2.23-2.05 (m, 2H).

Intermediate 62: 5-(3-(4-((4-aminopiperidin-1-yl)methyl)phenyl)-2-(2-aminopyridin-3-yl)-3H-imidazo[4,5-b]pyridin-5-yl)pyridin-2(1H)-one

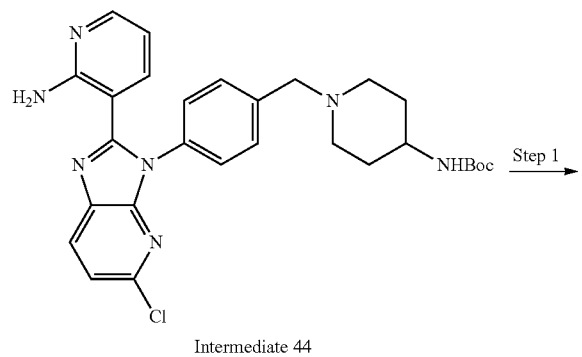

Intermediate 44

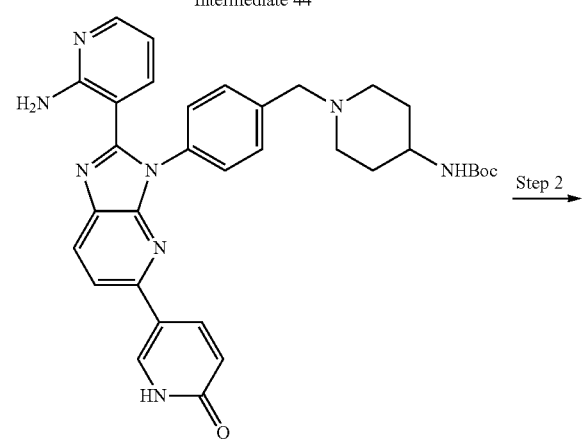

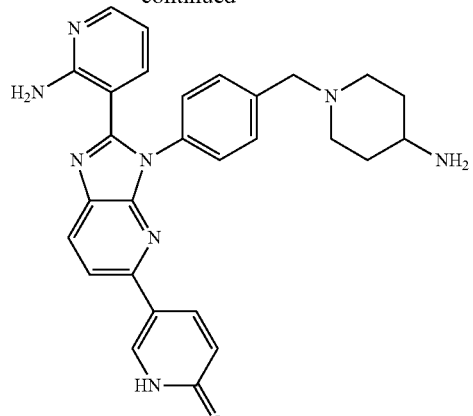

Intermediate 62

Step 1: tert-Butyl (1-(4-(2-(2-aminopyridin-3-yl)-5-(6-oxo-1,6-dihydropyridin-3-yl)-3H-imidazo[4,5-b]pyridin-3-yl)benzyl)piperidin-4-yl)carbamate A mixture of Intermediate 44 (100 mg, 187 μmol), (6-oxo-1,6-dihydropyridin-3-yl)boronic acid (39 mg, 281 μmol), Cs$_2$CO$_3$ (122 mg, 375 μmol), Pd(dppf)Cl$_2$ (14 mg, 19 μmol) in H$_2$O (2 mL) and 1,4-dioxane (8 mL) was degassed and purged with N$_2$ three times, and then the mixture was stirred at 100° C. for 1 hr under N$_2$ atmosphere. The reaction mixture was quenched with H$_2$O (10 mL) at 25° C. and extracted with EtOAc (15 mL×2). The combined organic layers were washed with brine (20 mL), dried over Na$_2$SO$_4$, filtered, and concentrated under reduced pressure. The crude was purified by silica gel flash chromatography (Eluent of 0~10% MeOH in CH$_2$Cl$_2$) to give tert-butyl (1-(4-(2-(2-aminopyridin-3-yl)-5-(6-oxo-1,6-dihydropyridin-3-yl)-3H-imidazo[4,5-b]pyridin-3-yl)benzyl)piperidin-4-yl)carbamate (52 mg, yield: 47%) as a light-yellow solid. MS: m/z=593.3 [M+H]$^+$. $^1$H NMR (400 MHz, Chloroform-d) δ 12.64-12.02 (m, 1H), 8.11-8.03 (m, 4H), 7.54 (d, J=8.4 Hz, 1H), 7.48 (d, J=8.0 Hz, 2H), 7.33 (d, J=7.6 Hz, 2H), 7.06 (d, J=7.6 Hz, 1H), 6.70-6.58 (m, 3H), 6.34 (dd, J=7.6, 4.8 Hz, 1H), 4.53-4.38 (m, 1H), 3.61 (s, 2H), 3.50-3.48 (m, 1H), 2.92-2.80 (m, 2H), 2.22-2.13 (m, 2H), 2.00-1.93 (m, 2H), 1.52-1.48 (m, 2H), 1.45 (s, 9H).

Step 2: 5-(3-(4-((4-Aminopiperidin-1-yl)methyl)phenyl)-2-(2-aminopyridin-3-yl)-3H-imidazo[4,5-b]pyridin-5-yl)pyridin-2(1H)-one To a solution of tert-butyl (1-(4-(2-(2-aminopyridin-3-yl)-5-(6-oxo-1,6-dihydropyridin-3-yl)-3H-imidazo[4,5-b]pyridin-3-yl)benzyl)piperidin-4-yl)carbamate (50 mg, 84 μmol) in HCl in 1,4-dioxane (4 M, 2 mL). The mixture was stirred at 25° C. for 1 hr. Then the mixture was concentrated under reduced pressure to give 5-(3-(4-((4-aminopiperidin-1-yl)methyl)phenyl)-2-(2-aminopyridin-3-yl)-3H-imidazo[4,5-b]pyridin-5-yl)pyridin-2(1H)-one (Intermediate 62, 33.3 mg, yield: 72%) as a light-yellow solid. MS: m/z=493.2 [M+H]$^+$. $^1$H NMR (400 MHz, Methanol-d$_4$) δ 8.59-8.52 (m, 1H), 8.45-8.39 (m, 1H), 8.33 (d, J=8.4 Hz, 1H), 8.05-8.01 (m, 1H), 7.97 (d, J=8.4 Hz, 1H), 7.92-7.86 (m, 3H), 7.73-7.69 (m, 2H), 6.92-6.84 (m, 2H), 3.73-3.67 (m, 2H), 3.67-3.65 (m, 1H), 3.62-3.57 (m, 2H), 3.38-3.34 (m, 2H), 2.35-2.30 (m, 2H), 2.21-2.13 (m, 2H).

Intermediate 63: 6-(3-(4-((4-aminopiperidin-1-yl)methyl)phenyl)-2-(2-aminopyridin-3-yl)-3H-imidazo[4,5-b]pyridin-5-yl)pyridin-2(1H)-one

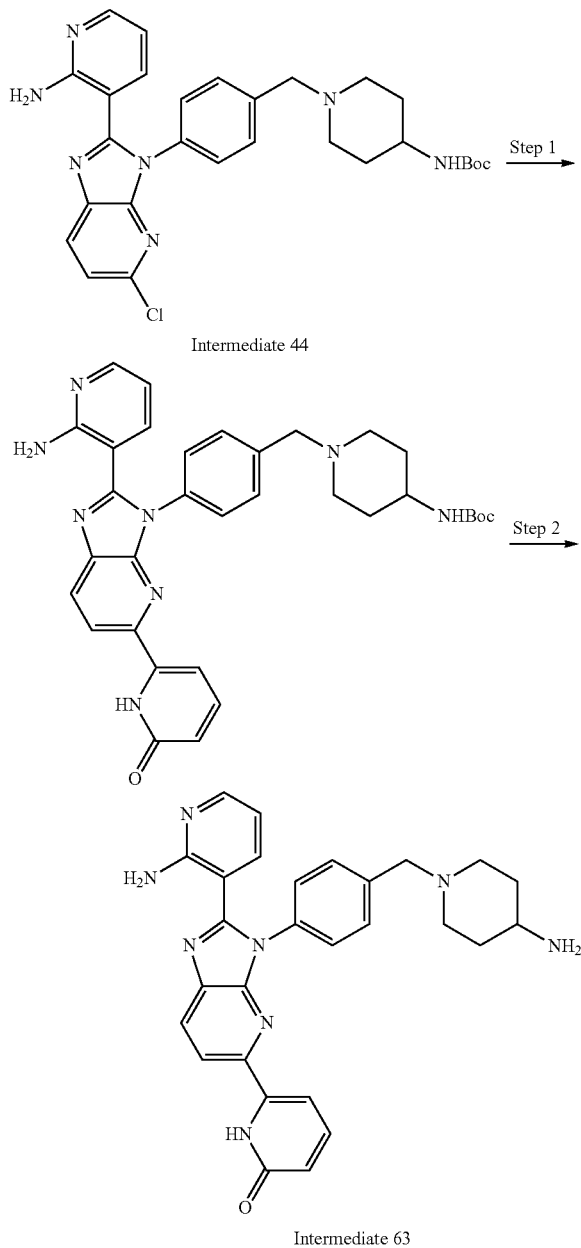

Intermediate 63

Step 1: tert-Butyl (1-(4-(2-(2-aminopyridin-3-yl)-5-(6-oxo-1,6-dihydropyridin-2-yl)-3H-imidazo[4,5-b]pyridin-3-yl)benzyl)piperidin-4-yl)carbamate A mixture of Intermediate 44 (100 mg, 187 μmol), 6-(4,4,5,5-tetramethyl-1,3,2-dioxaborolan-2-yl)pyridin-2(1H)-one (62 mg, 281 μmol), Cs$_2$CO$_3$ (122 mg, 374 μmol), Pd(dppf)Cl$_2$ (14 mg, 19 μmol) in H$_2$O (2 mL) and 1,4-dioxane (8 mL) was degassed and purged with N$_2$ three times, and then the mixture was stirred at 100° C. for 1 hr under N$_2$ atmosphere. The reaction mixture was quenched with H$_2$O (10 mL) at 25° C. and extracted with EtOAc (15 mL×2). The combined organic layers were washed with brine (20 mL), dried over Na$_2$SO$_4$, filtered and concentrated under reduced pressure. The crude was purified by silica gel flash chromatography (Eluent of 0~10% MeOH in CH$_2$Cl$_2$) to give tert-butyl (1-(4-(2-(2-aminopyridin-3-yl)-5-(6-oxo-1,6-dihydropyridin-2-yl)-3H-imidazo[4,5-b]pyridin-3-yl)benzyl)piperidin-4-yl)carbamate (100 mg, yield: 90%) as a light-yellow solid. MS: m/z=593.3 [M+H]$^+$. $^1$H NMR (400 MHz, Chloroform-d) δ 10.25 (br s, 1H), 8.17 (d, J=8.4 Hz, 1H), 8.08 (dd, J=4.8, 2.0 Hz, 1H), 7.86 (d, J=8.8 Hz, 1H), 7.58-7.53 (m, 2H), 7.50-7.46 (m, 1H), 7.31 (d, J=8.0 Hz, 2H), 7.05 (dd, J=7.6, 1.6 Hz, 1H), 6.87 (d, J=6.8 Hz, 1H), 6.65 (br s, 2H), 6.58 (d, J=8.0 Hz, 1H), 6.33 (dd, J=7.6, 4.8 Hz, 1H), 4.54-4.42 (m, 1H), 3.66 (s, 2H), 3.59-3.50 (m, 1H), 2.97-2.86 (m, 2H), 2.30-2.18 (m, 2H), 2.01-1.95 (m, 2H), 1.56-1.50 (m, 2H), 1.45 (s, 9H)

Step 2: 6-(3-(4-((4-Aminopiperidin-1-yl)methyl)phenyl)-2-(2-aminopyridin-3-yl)-3H-imidazo[4,5-b]pyridin-5-yl)pyridin-2(1H)-one To a solution of tert-butyl (1-(4-(2-(2-aminopyridin-3-yl)-5-(6-oxo-1,6-dihydropyridin-2-yl)-3H-imidazo[4,5-b]pyridin-3-yl)benzyl)piperidin-4-yl)carbamate (100.00 mg, 169 μmol) in HCl in 1,4-dioxane (4 M, 3 mL). The mixture was stirred at 25° C. for 1 hr. Then the mixture was concentrated under reduced pressure to give 6-(3-(4-((4-aminopiperidin-1-yl)methyl)phenyl)-2-(2-aminopyridin-3-yl)-3H-imidazo[4,5-b]pyridin-5-yl)pyridin-2(1H)-one (Intermediate 63, 62.6 mg, yield: 67%) as a light-yellow solid. MS: m/z=493.2 [M+H]$^+$. $^1$H NMR (400 MHz, Methanol-d$_4$) δ 8.47 (d, J=8.4 Hz, 1H), 8.25 (d, J=8.0 Hz, 1H), 8.08-7.98 (m, 2H), 7.96-7.89 (m, 3H), 7.78-7.72 (m, 2H), 7.50-7.58 (m, 1H), 6.94-6.82 (m, 2H), 3.76-3.68 (m, 2H), 3.66 (s, 2H), 3.61-3.56 (m, 1H), 3.38-3.32 (m, 2H), 2.36-2.29 (m, 2H), 2.21-2.08 (m, 2H).

Intermediate 64: 4-(2,7-Diazaspiro[3.5]nonan-7-yl)-1,3,5-triazine-2-carbonitrile

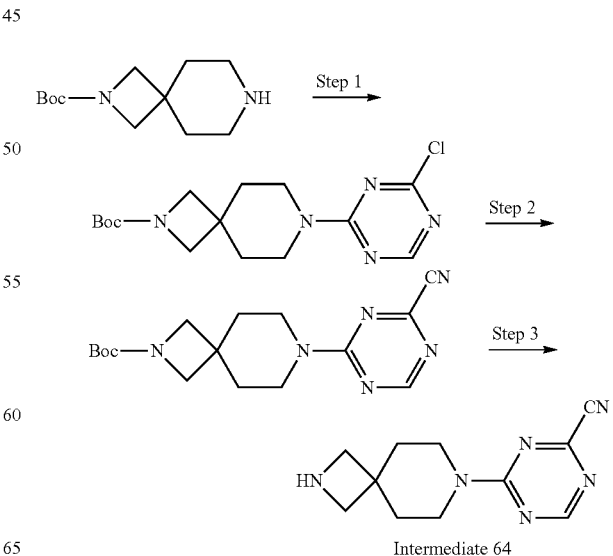

Intermediate 64

Step 1: tert-Butyl 7-(4-chloro-1,3,5-triazin-2-yl)-2,7-diazaspiro[3.5]nonane-2-carboxylate To a solution of tert-butyl 2,7-diazaspiro[3.5]nonane-2-carboxylate (400 mg, 1.77 mmol) and 2,4-dichloro-1,3,5-triazine (265 mg, 1.77 mmol) in THF (10 mL) was added DIEA (685 mg, 5.3 mmol). The resulting mixture was stirred at 0° C. for 1 hr. Then the reaction mixture was diluted with H$_2$O (50 mL) and extracted with CH$_2$Cl$_2$ (50 mL×2). The combined organic layers were dried over Na$_2$SO$_4$, filtered and concentrated under reduced pressure. tert-Butyl 7-(4-chloro-1,3,5-triazin-2-yl)-2,7-diazaspiro[3.5]nonane-2-carboxylate (500 mg, yield: 78%) was obtained as a white solid. MS: m/z=340.0 [M+H]$^+$. $^1$H NMR (400 MHz, Chloroform-d) δ 8.34 (s, 1H), 3.84-3.78 (m, 4H), 3.71 (s, 4H), 1.83-1.79 (m, 4H), 1.46 (s, 9H).

Step 2: tert-Butyl 7-(4-cyano-1,3,5-triazin-2-yl)-2,7-diazaspiro[3.5]nonane-2-carboxylate To a solution of tert-butyl 7-(4-chloro-1,3,5-triazin-2-yl)-2,7-diazaspiro[3.5]nonane-2-carboxylate (500 mg, 1.47 mmol) in DMSO (10 mL) were added KCN (660 mg, 10.1 mmol) and DABCO (33 mg, 294 μmol). The mixture was stirred at 25° C. for 16 hr. The reaction mixture was poured into H$_2$O (50 mL). The resulting mixture was extracted with EtOAc (50 mL×2). The combined organic layers were washed with brine (50 mL), dried over Na$_2$SO$_4$, filtered and concentrated under reduced pressure. After purified by silica gel flash chromatography (Eluent of 20~30% EtOAc in petroleum ether), tert-butyl 7-(4-cyano-1,3,5-triazin-2-yl)-2,7-diazaspiro[3.5]nonane-2-carboxylate (200 mg, yield: 37%) was obtained as a white solid. MS: m/z=275.1 [M+H−56]$^+$.

Step 3: 4-(2,7-Diazaspiro[3.5]nonan-7-yl)-1,3,5-triazine-2-carbonitrile

To a solution of tert-butyl 7-(4-cyano-1,3,5-triazin-2-yl)-2,7-diazaspiro[3.5]nonane-2-carboxylate (200 mg, 605 μmol) in CH$_2$Cl$_2$ (5 mL) was added TFA (207 mg, 1.82 mmol). The mixture was stirred at 25° C. for 0.5 hr. The reaction mixture was filtered and concentrated under reduced pressure to give 4-(2,7-diazaspiro[3.5]nonan-7-yl)-1,3,5-triazine-2-carbonitrile (Intermediate 64, 130 mg TFA salt, yield: 56%) as a yellow oil. MS: m/z=231.1 [M+H]$^+$. $^1$H NMR (400 MHz, Dimethylsulfoxide-d$_6$) δ 8.74-8.68 (m, 3H), 3.82-3.76 (m, 6H), 3.75-3.71 (m, 2H), 1.86-1.80 (m, 4H).

Intermediate 65: 4-(7-Azaspiro[3.5]nonan-2-ylamino)-1,3,5-triazine-2-carbonitrile

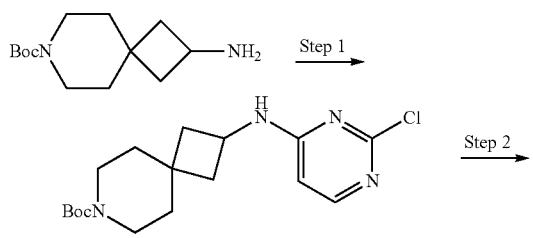

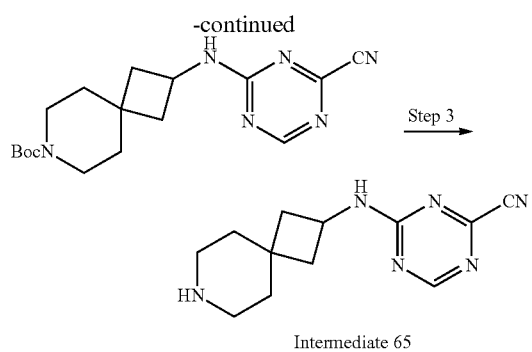

Intermediate 65

Step 1: tert-Butyl 2-((2-chloropyrimidin-4-yl)amino)-7-azaspiro[3.5]nonane-7-carboxylate To a solution of tert-butyl 2-amino-7-azaspiro[3.5]nonane-7-carboxylate (2.0 g, 8.32 mmol) in THF (50 mL) was added DIPEA (1.61 g, 12.5 mmol). The mixture was stirred at 0° C. for 10 min, and then 2,4-dichloro-1,3,5-triazine (1.25 g, 8.32 mmol) in THF (20 mL) was added dropwise at 0° C. The resulting mixture was stirred at 0° C. for 4 hr. The reaction mixture diluted with H$_2$O (100 mL) and extracted with EtOAc (50 mL×2). The combined organic layers were washed with brine (100 mL), dried over Na$_2$SO$_4$, filtered and concentrated under reduced pressure. The residue was purified by silica gel flash chromatography (Eluent of 0~30% EtOAc in petroleum ether) to give tert-butyl 2-[(4-chloro-1,3,5-triazin-2-yl)amino]-7-azaspiro[3.5]nonane-7-carboxylate (1.6 g, yield: 54% yield) was obtained as a white solid. MS: m/z=354.1 [M+H]$^+$. $^1$H NMR (400 MHz, Chloroform-d) δ 8.42-8.30 (m, 1H), 5.81-5.69 (m, 1H), 4.53-4.42 (m, 1H), 3.39-3.36 (m, 2H), 3.32-3.28 (m, 2H), 2.45-2.39 (m, 2H), 1.73-1.67 (m, 2H), 1.64-1.60 (m, 2H), 1.55-1.51 (m, 2H), 1.45 (s, 9H).

Step 2: tert-Butyl 2-((4-cyano-1,3,5-triazin-2-yl)amino)-7-azaspiro[3.5]nonane-7-carboxylate To a solution of tert-butyl 2-[(4-chloro-1,3,5-triazin-2-yl)amino]-7-azaspiro[3.5]nonane-7-carboxylate (1.51 g, 4.27 mmol) and KCN (610 mg, 9.37 mmol) in DMSO (35 mL) was added DABCO (95.7 mg, 853 gmol). The mixture was stirred at 25° C. for 1 hr. The reaction mixture was poured into water (200 mL). The resulting mixture was extracted with EtOAc (100 mL×2). The combined organic layers were washed with brine (100 mL) and dried over anhydrous Na$_2$SO$_4$, filtered and concentrated to dryness. The residue was purified by silica gel flash chromatography (Eluent of 0~30% EtOAc in petroleum ether) to give tert-butyl 2-[(4-cyano-1,3,5-triazin-2-yl)amino]-7-azaspiro[3.5]nonane-7-carboxylate (1.2 g, yield: 82%) as a white solid. MS: m/z=289.1 [M−56+H]$^+$. $^1$H NMR (400 MHz, Chloroform-d) δ 8.63-8.51 (m, 1H), 5.94-5.84 (m, 1H), 4.50-4.43 (m, 1H), 3.41-3.36 (m, 2H), 3.32-3.28 (m, 2H), 2.47-2.40 (m, 2H), 1.76-1.70 (m, 2H), 1.65-1.61 (m, 2H), 1.56-1.52 (m, 2H), 1.45 (s, 9H).

Step 3: 4-(7-Azaspiro[3.5]nonan-2-ylamino)-1,3,5-triazine-2-carbonitrile

To a solution of tert-butyl 2-[(4-cyano-1,3,5-triazin-2-yl)amino]-7-azaspiro[3.5]nonane-7-carboxylate (980 mg, 2.85 mmol) in CH$_2$Cl$_2$ (10 mL) was added TFA (1.95 g, 17.1 mmol). The mixture was stirred at 25° C. for 1 hr. The reaction mixture was concentrated under reduced pressure. The crude 4-(7-azaspiro[3.5]nonan-2-ylamino)-1,3,5-triazine-2-carbonitrile (Intermediate 65, 1.02 g TFA salt, yield: 100%) was used in the next step without further purification. MS: m/z=245.1 [M+H]⁺.

Intermediate 66: Methyl 4-(2-(2-aminopyridin-3-yl)-5-chloro-3H-imidazo[4,5-b]pyridin-3-yl)benzoate

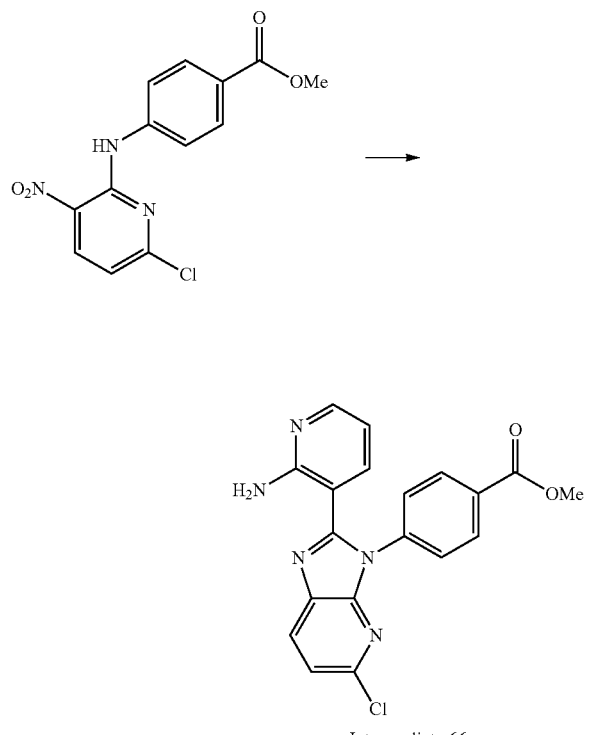

Intermediate 66

Intermediate 67: 3-(3-(4-((4-Aminopiperidin-1-yl)methyl)phenyl)-5-methyl-3H-imidazo[4,5-b]pyridin-2-yl)pyridin-2-amine

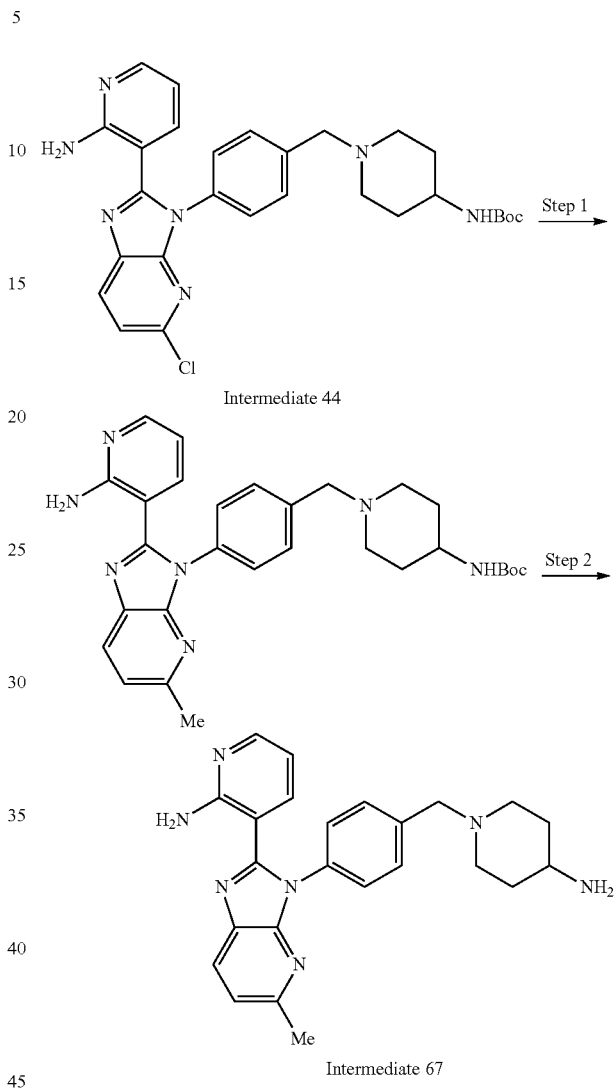

To a solution of methyl 4-((6-chloro-3-nitropyridin-2-yl)amino)benzoate (refer to Intermediate 13 for detail procedures, 5.0 g, 16.3 mmol) and 2-aminonicotinaldehyde (2.18 g, 81.8 mmol) in DMSO (150 mL) was added $Na_2S_2O_4$ (5.66 g, 32.5 mmol). The mixture was stirred at 105° C. for 12 hr. The reaction mixture was diluted with water (300 mL) and extracted with EtOAc (300 mL×3). The combined organic layers were washed with brine (100 mL), dried over $Na_2SO_4$, filtered and concentrated under reduced pressure. The residue was purified by silica gel flash chromatography (Eluent of 0~100% EtOAc in petroleum ether) to give methyl 4-(2-(2-aminopyridin-3-yl)-5-chloro-3H-imidazo[4,5-b]pyridin-3-yl)benzoate (Intermediate 66, 700 mg, yield: 11.3%) as a yellow solid. MS: m/z=380.0 [M+H]⁺. ¹H NMR (400 MHz, Dimethylsulfoxide-d₆) δ 8.28 (d, J=8.4 Hz, 1H), 8.09 (d, J=8.4 Hz, 2H), 8.01 (dd, J=4.4, 1.6 Hz, 1H), 7.60 (d, J=8.4 Hz, 2H), 7.48 (d, J=8.4 Hz, 1H), 7.23 (dd, J=7.6, 1.6 Hz, 1H), 6.78 (br s, 2H), 6.45 (dd, J=7.6, 4.8 Hz, 1H), 3.89 (s, 3H).

Step 1: tert-Butyl (1-(4-(2-(2-aminopyridin-3-yl)-5-methyl-3H-imidazo[4,5-b]pyridin-3-yl)benzyl)piperidin-4-yl)carbamate A mixture of Intermediate 44 (300 mg, 562 μmol), methylboronic acid (47 mg, 786 μmol), $Cs_2CO_3$ (366 mg, 1.12 mmol), and Pd(dppf)Cl₂ (41 mg, 56.2 μmol) in 1,4-dioxane (2 mL) and H₂O (0.5 mL) was degassed and purged with N₂ three times, and then the mixture was stirred at 100° C. for 16 hr under N₂ atmosphere. The reaction mixture was poured into H₂O (10 mL) and extracted with EtOAc (15 mL×2). The combined organic layers were dried over anhydrous $Na_2SO_4$, filtered and concentrated under reduced pressure. The residue was purified by silica gel flash chromatography (Eluent of 0~86% EtOAc in petroleum ether) to give tert-butyl (1-(4-(2-(2-aminopyridin-3-yl)-5-methyl-3H-imidazo[4,5-b]pyridin-3-yl)benzyl)piperidin-4-yl)carbamate (210 mg, yield: 73%) as a yellow solid. MS: m/z=514.2 [M+H]⁺.

Step 2: 3-(3-(4-((4-Aminopiperidin-1-yl)methyl) phenyl)-5-methyl-3H-imidazo[4,5-b]pyridin-2-yl) pyridin-2-amine To a solution of tert-butyl (1-(4-(2-(2-aminopyridin-3-yl)-5-methyl-3H-imidazo[4,5-b]pyridin-3-yl)benzyl)piperidin-4-yl)carbamate (60 mg, 117 μmol) in CH$_2$Cl$_2$ (2 mL) was added 4 M HCl in 1,4-dioxane (1.5 mL). The mixture was stirred at 25° C. for 1 hr. The reaction was concentrated under reduced pressure to give crude product. The crude was triturated with CH$_2$Cl$_2$ (10 mL) at 25° C. for 30 min. 3-(3-(4-((4-Aminopiperidin-1-yl)methyl)phenyl)-5-methyl-3H-imidazo[4,5-b]pyridin-2-yl)pyridin-2-amine (Intermediate 67, 43.6 mg HCl salt, yield: 83%) was obtained as a yellow solid. MS: m/z=414.0 [M+H]$^+$. $^1$H NMR (400 MHz, Methanol-d$_4$) δ 8.17 (d, J=8.4 Hz, 1H), 7.99 (d, J=5.6 Hz, 1H), 7.88 (d, J=7.6 Hz, 2H), 7.81 (d, J=7.2 Hz, 1H), 7.63 (d, J=7.6 Hz, 2H), 7.38 (d, J=8.4 Hz, 1H), 6.88-6.82 (m, 1H), 3.70-3.64 (m, 2H), 3.59-3.54 (m, 1H), 3.29-3.17 (m, 2H), 2.61 (s, 3H), 2.32-2.29 (m, 2H), 2.20-2.06 (m, 2H), 1.33-1.27 (m, 2H).

Intermediate 68: 3-(5-(2-Fluorophenyl)-3-(4-(piperazin-1-ylmethyl)phenyl)-3H-imidazo[4,5-b]pyridin-2-yl)pyridin-2-amine hydrochloride

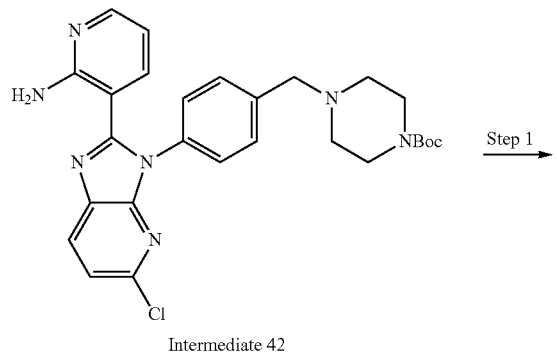

Intermediate 42

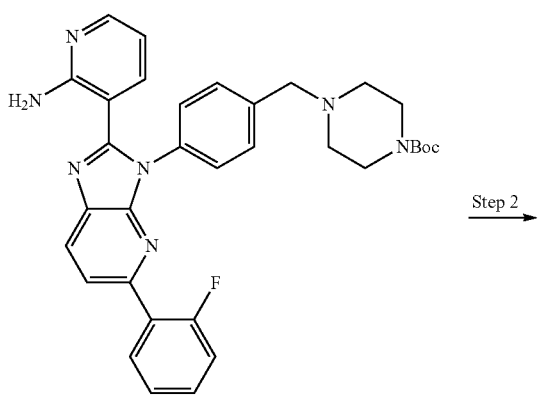

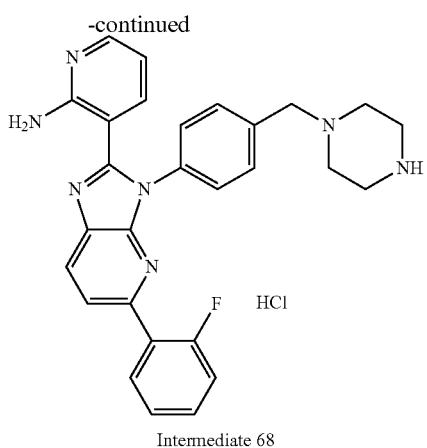

Intermediate 68

Step 1: tert-Butyl 4-(4-(2-(2-aminopyridin-3-yl)-5-(2-fluorophenyl)-3H-imidazo[4,5-b]pyridin-3-yl) benzyl)piperazine-1-carboxylate To a solution of Intermediate 42 (500 mg, 961 μmol) and (2-fluorophenyl)boronic acid (134 mg, 961 μmol) in 1,4-dioxane (10 mL) and H$_2$O (2 mL) was added Cs$_2$CO$_3$ (940 mg, 2.88 mmol) and Pd(dppf)Cl$_2$ (70.4 mg, 96.1 μmol). The mixture was degassed and purged with N$_2$ three times, the resulting mixture was stirred at 80° C. for 16 hr under N$_2$ atmosphere. Then the reaction mixture was diluted with H$_2$O (50 mL) and extracted with CH$_2$Cl$_2$ (50 mL×2). The combined organic layers were dried over Na$_2$SO$_4$, filtered and concentrated under reduced pressure. The crude product was purified by silica gel flash chromatography (Eluent of 30~80% EtOAc in petroleum ether) to give tert-Butyl 4-(4-(2-(2-aminopyridin-3-yl)-5-(2-fluorophenyl)-3H-imidazo[4,5-b]pyridin-3-yl)benzyl)piperazine-1-carboxylate (500 mg, yield: 87%) as a yellow solid. MS: m/z=580.2 [M+H]$^+$. $^1$H NMR (400 MHz, Dimethylsulfoxide-d$_6$) δ 8.30 (d, J=8.4 Hz, 1H), 8.00 (dd, J=4.8, 1.6 Hz, 1H), 7.90-7.70 (m, 2H), 7.56-7.40 (m, 5H), 7.37-7.26 (m, 2H), 7.16 (dd, J=8.0, 2.0 Hz, 1H), 6.99 (br s, 2H), 6.39 (dd, J=7.6, 4.8 Hz, 1H), 3.57 (s, 2H), 3.36-3.33 (m, 4H), 2.42-2.30 (m, 4H), 1.40 (s, 9H).

Step 2: 3-(5-(2-Fluorophenyl)-3-(4-(piperazin-1-ylmethyl)phenyl)-3H-imidazo[4,5-b]pyridin-2-yl) pyridin-2-amine hydrochloride To a solution of tert-butyl 4-(4-(2-(2-aminopyridin-3-yl)-5-(2-fluorophenyl)-3H-imidazo[4,5-b]pyridin-3-yl)benzyl)piperazine-1-carboxylate (500 mg, 863 μmol) in 1,4-dioxane (5 mL) was added HCl/1,4-dioxane (4M, 5 mL). The mixture was stirred at 25° C. for 0.5 hr. The reaction mixture was filtered and concentrated under reduced pressure to give 3-(5-(2-fluorophenyl)-3-(4-(piperazin-1-ylmethyl)phenyl)-3H-imidazo[4,5-b]pyridin-2-yl)pyridin-2-amine (Intermediate 68, 400 mg, yield: 92%, HCl salt) as a yellow solid. MS: m/z=480.2 [M+H]$^+$. $^1$H NMR (400 MHz, Dimethylsulfoxide-d$_6$) δ 12.82-11.99 (m, 1H), 10.20-9.62 (m, 2H), 8.53-8.43 (m, 1H), 8.40 (d, J=8.0 Hz, 1H), 8.15 (dd, J=6.0, 1.6 Hz, 1H), 7.91-7.81 (m, 5H), 7.67 (d, J=8.4 Hz, 2H), 7.52-7.46 (m, 1H), 7.39-7.30 (m, 2H), 6.98 (dd, J=7.6, 6.4 Hz, 1H), 4.48 (s, 2H), 3.53-3.48 (m, 4H), 2.50 (m, 4H). $^{19}$F NMR (400 MHz, Dimethylsulfoxide-d$_6$) δ −117.18.

Intermediate 69: 2-(2-(2-Aminopyridin-3-yl)-3-(4-(piperazin-1-ylmethyl)phenyl)-3H-imidazo[4,5-b]pyridin-5-yl)benzonitrile

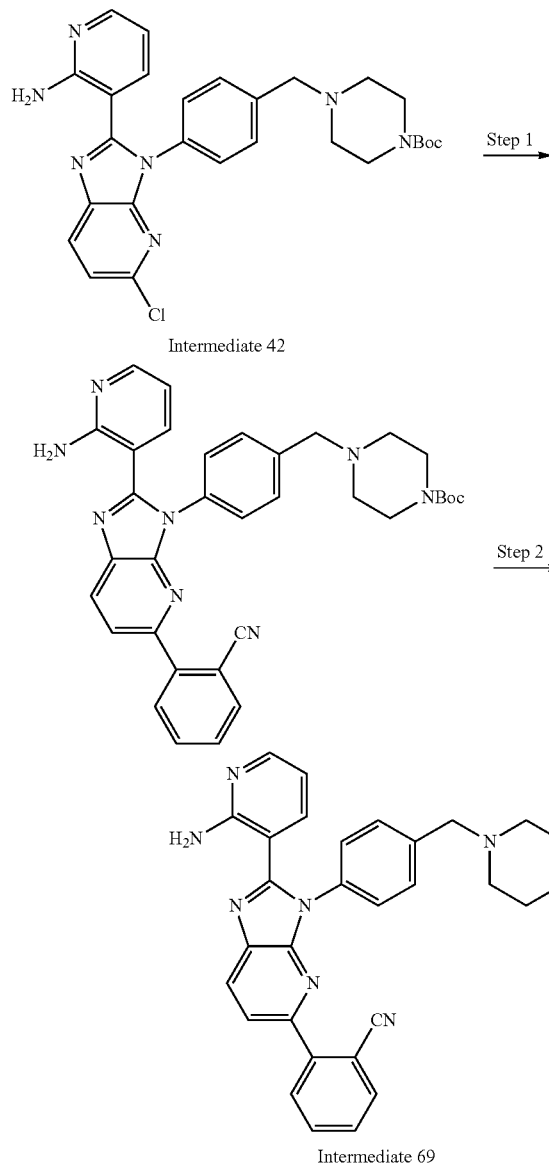

Step 1: tert-Butyl 4-(4-(2-(2-aminopyridin-3-yl)-5-(2-cyanophenyl)-3H-imidazo[4,5-b]pyridin-3-yl)benzyl)piperazine-1-carboxylate A mixture of Intermediate 42 (400 mg, 770 μmol), (2-cyanophenyl)boronic acid (124 mg, 846 gmol), K₃PO₄ (327 mg, 1.54 mmol), cataCXiumAPdG₃ (280 mg, 385 μmol), and tricyclohexylphosphane (22 mg, 76.9 μmol) in DMF (5 mL) was degassed and purged with N₂ three times, and then the mixture was stirred at 120° C. for 16 hr under N₂ atmosphere. The reaction mixture was filtered at 25° C., and then diluted with H₂O (20 mL) and extracted with CH₂Cl₂ (20 mL×3). The combined organic layers were washed with brine (30 mL), dried over Na₂SO₄, filtered and concentrated under reduced pressure. After purified by silica gel flash chromatography (Eluent of 20~80% EtOAc in Petroleum ether), tert-butyl 4-(4-(2-(2-aminopyridin-3-yl)-5-(2-cyanophenyl)-3H-imidazo[4,5-b]pyridin-3-yl)benzyl)piperazine-1-carboxylate (400 mg, yield: 80%) was obtained as a yellow solid. MS: m/z=587.2 [M+H]⁺.

Step 2: 2-(2-(2-Aminopyridin-3-yl)-3-(4-(piperazin-1-ylmethyl)phenyl)-3H-imidazo[4,5-b]pyridin-5-yl)benzonitrile To a solution of tert-butyl 4-(4-(2-(2-aminopyridin-3-yl)-5-(2-cyanophenyl)-3H-imidazo[4,5-b]pyridin-3-yl)benzyl)piperazine-1-carboxylate (400 mg, 682 μmol) in 1,4-dioxane (5 mL) was added 4 M HCl in 1,4-dioxane (3 mL) at 25° C. The mixture was stirred at 25° C. for 16 hr. The reaction mixture was then filtered and the collected solid was washed with 1,4-dioxane (5 mL×2) and dried in vacuo to give 2-(2-(2-aminopyridin-3-yl)-3-(4-(piperazin-1-ylmethyl)phenyl)-3H-imidazo[4,5-b]pyridin-5-yl)benzonitrile (Intermediate 69, 268 mg HCl salt, yield: 75%) as a yellow solid. MS: m/z=487.2 [M+H]⁺. ¹H NMR (400 MHz, Dimethylsulfoxide-d₆) δ 8.38 (d, J=8.0 Hz, 1H), 8.03-7.99 (m, 1H), 7.97-7.92 (m, 1H), 7.90-7.77 (m, 3H), 7.64-7.58 (m, 1H), 7.50-7.37 (m, 5H), 7.19 (dd, J=7.6, 2.0 Hz, 1H), 6.98 (br s, 2H), 6.40 (dd, J=7.6, 4.8 Hz, 1H), 3.50 (s, 2H), 2.80-2.70 (m, 4H), 2.37-2.32 (m, 4H).

Intermediate 70: 4-(2-(2-aminopyridin-3-yl)-3-(4-(piperazin-1-ylmethyl)phenyl)-3H-imidazo[4,5-b]pyridin-5-yl)-1,4-diazepan-2-one

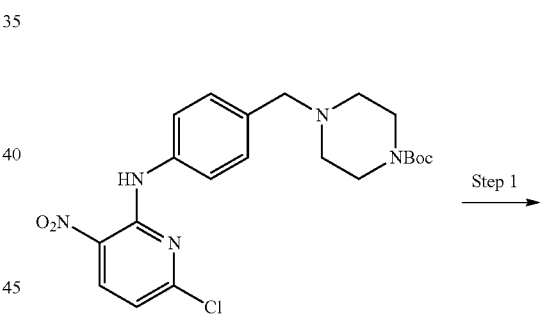

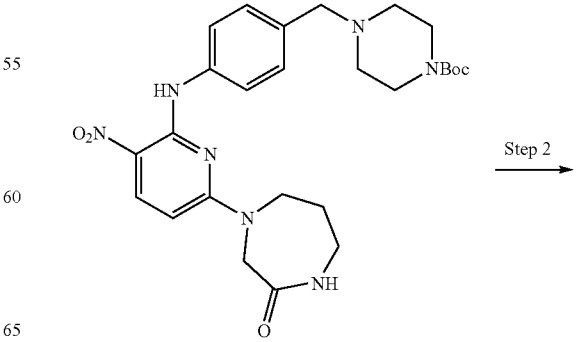

553
-continued

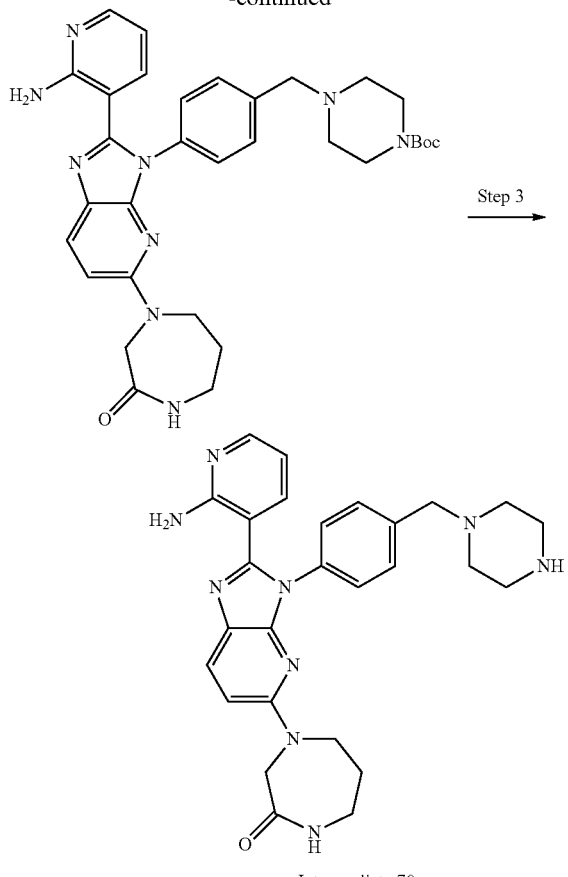

Intermediate 70

Step 1: tert-Butyl 4-(4-((3-nitro-6-(3-oxo-1,4-diazepan-1-yl)pyridin-2-yl)amino)benzyl)piperazine-1-carboxylate To a solution of tert-butyl 4-(4-((6-chloro-3-nitropyridin-2-yl)amino)benzyl)piperazine-1-carboxylate (refer to Intermediate 10 for detail procedures, 1.5 g, 3.35 mmol) and 1,4-diazepan-2-one (382 mg, 3.35 mmol) in ACN (20 mL) was added DIEA (866 mg, 6.7 mmol). The mixture was stirred at 90° C. for 4 hr. The reaction was concentrated under reduced pressure to give tert-butyl 4-(4-((3-nitro-6-(3-oxo-1,4-diazepan-1-yl)pyridin-2-yl)amino)benzyl)piperazine-1-carboxylate (1.8 g, yield: 92%) as a yellow solid. MS: m/z=526.1 [M+H]$^+$.

Step 2: tert-Butyl 4-(4-(2-(2-aminopyridin-3-yl)-5-(3-oxo-1,4-diazepan-1-yl)-3H-imidazo[4,5-b]pyridin-3-yl)benzyl)piperazine-1-carboxylate To a solution of tert-butyl 4-(4-((3-nitro-6-(3-oxo-1,4-diazepan-1-yl)pyridin-2-yl)amino)benzyl)piperazine-1-carboxylate (1.8 g, 3.42 mmol) in DMSO (20 mL) was added 2-aminonicotinaldehyde (502 mg, 4.11 mmol) and $Na_2S_2O_4$ (2.74 g, 13.7 mmol, 87% purity). The mixture was stirred at 100° C. for 8 hr. The reaction mixture was quenched with $H_2O$ (30 mL) at 25° C., and extracted with $CH_2Cl_2$ (50 mL×3). The combined organic layers were washed with brine (50 mL), dried over $Na_2SO_4$, filtered and concentrated under reduced pressure to give tert-butyl 4-(4-(2-(2-aminopyridin-3-yl)-5-(3-oxo-1,4-diazepan-1-yl)-3H-imidazo[4,5-b]pyridin-3-yl)benzyl)piperazine-1-carboxylate (1.3 g, purity: 49%, yield: 30%) as a yellow solid. MS: m/z=598.3 [M+H]$^+$, 498.2 [M–Boc+H]$^+$ Step 3: 4-(2-(2-Aminopyridin-3-yl)-3-(4-(piperazin-1-ylmethyl)phenyl)-3H-imidazo[4,5-b]pyridin-5-yl)-1,4-diazepan-2-one To a solution of tert-butyl 4-(4-(2-(2-aminopyridin-3-yl)-5-(3-oxo-1,4-diazepan-1-yl)-3H-imidazo[4,5-b]pyridin-3-yl)benzyl)piperazine-1-carboxylate (1.2 g, 2.01 mmol) in 4 M HCl in 1,4-dioxane (10 mL) at 25° C. The mixture was stirred at 25° C. for 0.5 hr. The reaction was concentrated under reduced pressure to give crude product (1 g, yield: 54%). The crude (100 mg) was purified by prep-HPLC (column: Phenomenex C18 150*25 mm*10 μm; mobile phase: [water ($NH_4HCO_3$)-ACN]; gradient: B: 9%-39%, 10 min) to give 4-(2-(2-aminopyridin-3-yl)-3-(4-(piperazin-1-ylmethyl)phenyl)-3H-imidazo[4,5-b]pyridin-5-yl)-1,4-diazepan-2-one (Intermediate 70, 25.1 mg) as a yellow solid. MS: m/z=498.3 [M+H]$^+$. $^1$H NMR (400 MHz, Dimethylsulfoxide-$d_6$) δ 8.01-7.89 (m, 2H), 7.52-7.42 (m, 1H), 7.40 (d, J=8.4 Hz, 2H), 7.31 (d, J=8.4 Hz, 2H), 7.00 (dd, J=7.6, 1.6 Hz, 1H), 6.98 (br s, 1H), 6.80 (d, J=8.8 Hz, 1H), 6.32 (dd, J=7.6, 4.8 Hz, 1H), 4.17 (s, 2H), 3.85-3.77 (m, 2H), 3.49 (s, 2H), 3.19-3.15 (m, 2H), 2.70 (t, J=4.8 Hz, 4H), 2.35-2.27 (m, 4H), 1.68-1.61 (m, 2H).

Intermediate 71: 4-(3,8-Diazabicyclo[3.2.1]octan-3-yl)-1,3,5-triazine-2-carbonitrile

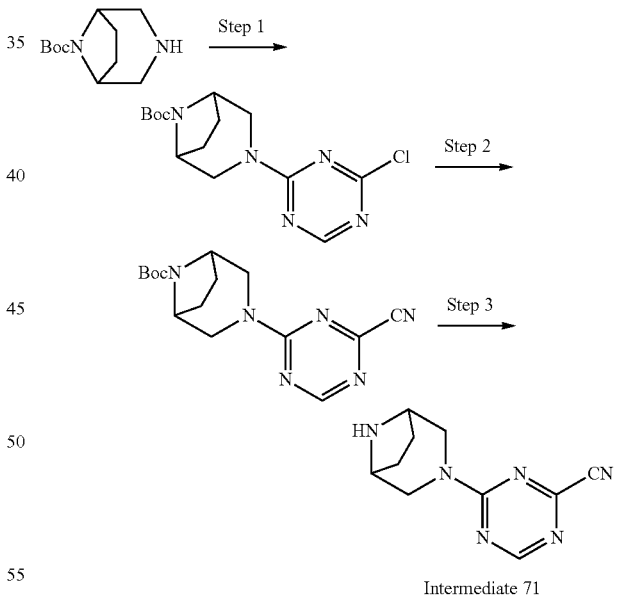

Intermediate 71

Step 1: tert-Butyl 3-(4-chloro-1,3,5-triazin-2-yl)-3,8-diazabicyclo[3.2.1]octane-8-carboxylate To a solution of tert-butyl 3,8-diazabicyclo[3.2.1]octane-8-carboxylate (5 g, 23.6 mmol) and 2,4-dichloro-1,3,5-triazine (3.89 g, 25.9 mmol) in THF (100 mL) was added DIEA (9.13 g, 70.7 mmol). The resulting mixture was stirred at 0° C. for 1 hr. Then the reaction mixture was diluted with $H_2O$ (100 mL) and extracted with $CH_2Cl_2$ (100 mL×2). The combined organic layers were dried over Na₂SO₄, filtered and concentrated under reduced pressure. After purified by silica gel flash chromatography (Eluent of 20~30% EtOAc in petroleum ether), tert-butyl 3-(4-chloro-1,3,5-triazin-2-yl)-3,8-diazabicyclo[3.2.1]octane-8-carboxylate (4 g, yield: 51%) was obtained as a white solid. MS: m/z=326.2 [M+H]⁺. ¹H NMR (400 MHz, Dimethylsulfoxide-d₆) δ 8.50 (s, 1H), 4.42-4.35 (m, 1H), 4.27-4.19 ((m, 3H), 3.14-3.08 (m, 2H), 1.85-1.77 (m, 2H), 1.56-1.50 (m, 2H), 1.43 (s, 9H).

Step 2: tert-Butyl 3-(4-cyano-1,3,5-triazin-2-yl)-3,8-diazabicyclo[3.2.1]octane-8-carboxylate To a solution of tert-butyl 3-(4-chloro-1,3,5-triazin-2-yl)-3,8-diazabicyclo[3.2.1]octane-8-carboxylate (1.9 g, 5.83 mmol) in DMSO (20 mL) were added KCN (790 mg, 12.1 mmol) and DABCO (131 mg, 1.17 mmol). The mixture was stirred at 25° C. for 16 hr. The reaction mixture was poured into H₂O (100 mL). The resulting mixture was extracted with EtOAc (100 mL×2). The combined organic layers were washed with brine (100 mL), dried over Na₂SO₄, filtered and concentrated under reduced pressure. After purified by silica gel flash chromatography (Eluent of 20~30% EtOAc in petroleum ether), tert-butyl 3-(4-cyano-1,3,5-triazin-2-yl)-3,8-diazabicyclo[3.2.1]octane-8-carboxylate (650 mg, yield: 30%) was obtained as a yellow solid. MS: m/z=317.2 [M+H]⁺.

Step 3: 4-(3,8-Diazabicyclo[3.2.1]octan-3-yl)-1,3,5-triazine-2-carbonitrile

To a solution of tert-butyl 3-(4-cyano-1,3,5-triazin-2-yl)-3,8-diazabicyclo[3.2.1]octane-8-carboxylate (630 mg, 1.99 mmol) in CH₂Cl₂ (10 mL) was added TFA (681 mg, 5.97 mmol). The mixture was stirred at 25° C. for 0.5 hr. The reaction mixture was filtered and concentrated under reduced pressure, 4-(3,8-diazabicyclo[3.2.1]octan-3-yl)-1,3,5-triazine-2-carbonitrile (Intermediate 71, 430 mg TFA salt, yield: 52%) was obtained as a yellow oil. MS: m/z=217.1 [M+H]⁺.

Intermediate 72: 3-(3-(4-(Chloromethyl)phenyl)-5-isopropyl-3H-imidazo[4,5-b]pyridin-2-yl)pyridin-2-amine

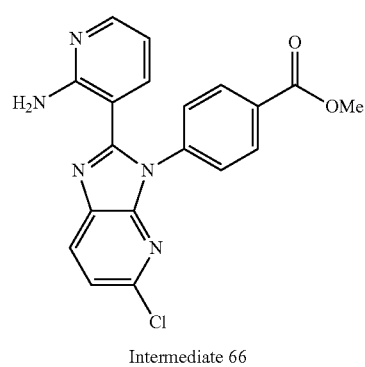

Intermediate 66

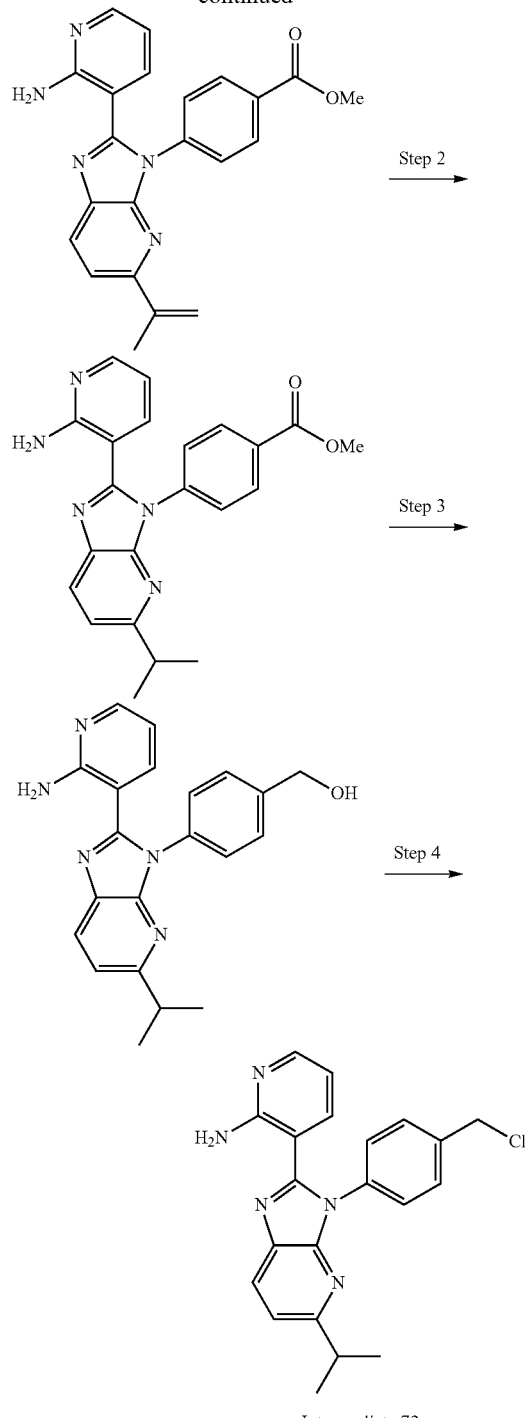

Intermediate 72

Step 1: Methyl 4-(2-(2-aminopyridin-3-yl)-5-(prop-1-en-2-yl)-3H-imidazo[4,5-b]pyridin-3-yl)benzoate A mixture of Intermediate 66 (660 mg, 1.74 mmol), 4,4,5,5-tetramethyl-2-(prop-1-en-2-yl)-1,3,2-dioxaborolane (321 mg, 1.91 mmol), Pd(dppf)Cl₂ (127 mg, 173 μmol) and Cs₂CO₃ (1.13 g, 3.48 mmol) in 1,4-dioxane (10 mL) and H₂O (1 mL) was degassed and purged with N₂ three times. The mixture was stirred at 100° C. for 3 hr. The reaction mixture was diluted with H₂O (50 mL) and extracted with CH₂Cl₂ (50 mL×2). The combined organic layers were dried over Na₂SO₄, filtered and concentrated under reduced pressure. After purified by silica gel flash chromatography (eluent of 50% EtOAc in petroleum ether), methyl 4-(2-(2-aminopyridin-3-yl)-5-(prop-1-en-2-yl)-3H-imidazo[4,5-b]pyridin-3-yl)benzoate (530 mg, yield: 72%) was obtained as a yellow solid. MS: m/z=386.0 [M+H]⁺.

Step 2: Methyl 4-(2-(2-aminopyridin-3-yl)-5-isopropyl-3H-imidazo[4,5-b]pyridin-3-yl)benzoate A mixture of methyl 4-(2-(2-aminopyridin-3-yl)-5-(prop-1-en-2-yl)-3H-imidazo[4,5-b]pyridin-3-yl)benzoate (530 mg, 1.38 mmol) in MeOH (20 mL) was added Pd/C (150 mg, 2.75 mmol, 10% purity), the mixture was stirred at 50° C. and 50 psi under H₂ atmosphere for 24 hr. The reaction mixture was cooled to 25° C., then filtered to get the liquor and concentrated under reduced pressure to give methyl 4-(2-(2-aminopyridin-3-yl)-5-isopropyl-3H-imidazo[4,5-b]pyridin-3-yl)benzoate (500 mg, yield: 94%) as a green solid. MS: m/z=388.1 [M+H]⁺. ¹H NMR (400 MHz, Dimethylsulfoxide-d₆) δ 8.13 (d, J=8.4 Hz, 1H), 8.08 (d, J=8.4 Hz, 2H), 8.00 (dd, J=4.8, 1.6 Hz, 1H), 7.58 (d, J=8.4 Hz, 2H), 7.33 (d, J=8.0 Hz, 1H), 7.17 (dd, J=7.6, 1.6 Hz, 1H), 6.78 (br s, 2H), 6.43 (dd, J=7.6, 4.8 Hz, 1H), 3.88 (s, 3H), 3.12-3.04 (m, 1H), 1.23 (d, J=6.8 Hz, 6H).

Step 3: (4-(2-(2-Aminopyridin-3-yl)-5-isopropyl-3H-imidazo[4,5-b]pyridin-3-yl)phenyl)methanol A mixture of methyl methyl 4-(2-(2-aminopyridin-3-yl)-5-isopropyl-3H-imidazo[4,5-b]pyridin-3-yl)benzoate (500 mg, 1.29 mmol) in THF (20 mL) was added LiAlH₄ (2.5 M, 800 L) at 0° C. dropwise, the mixture was stirred at 25° C. for 1 hr. The reaction mixture was quenched with Na₂SO₄·10H₂O (3 g) at 0° C., and then filtered and concentrated under reduced pressure to give (4-(2-(2-aminopyridin-3-yl)-5-isopropyl-3H-imidazo[4,5-b]pyridin-3-yl)phenyl)methanol (480 mg, crude) as a yellow solid. MS: m/z=360.0 [M+H]⁺.

Step 4: 3-(3-(4-(Chloromethyl)phenyl)-5-isopropyl-3H-imidazo[4,5-b]pyridin-2-yl)pyridin-2-amine A mixture of (4-(2-(2-aminopyridin-3-yl)-5-isopropyl-3H-imidazo[4,5-b]pyridin-3-yl)phenyl)methanol (480 mg, 1.34 mmol) in CH₂Cl₂ (10 mL) was added SOCl₂ (953 mg, 8.0 mmol), the mixture was stirred at 40° C. for 1 hr. The reaction mixture was filtered and the filter cake was washed with CH₂Cl₂ (5 mL) to give 3-(3-(4-(chloromethyl)phenyl)-5-isopropyl-3H-imidazo[4,5-b]pyridin-2-yl)pyridin-2-amine (Intermediate 72, 220 mg, yield: 41%) as a yellow solid. MS: m/z=378.0 [M+H]⁺.

Intermediate 73: 3-(3-(4-(Chloromethyl)phenyl)-5-methoxy-3H-imidazo[4,5-b]pyridin-2-yl)pyridin-2-amine

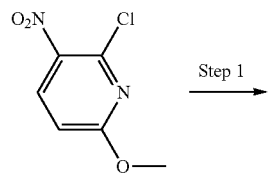

Step 1

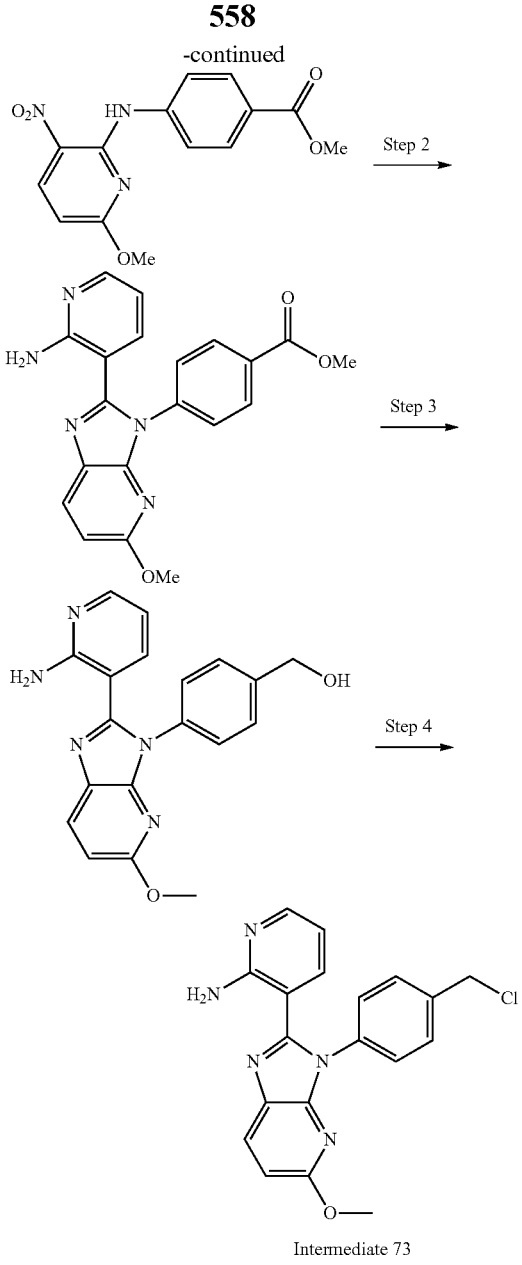

Intermediate 73

Step 1: Methyl 4-((6-methoxy-3-nitropyridin-2-yl)amino)benzoate

To a solution of 2-chloro-6-methoxy-3-nitropyridine (10 g, 53.0 mmol) and methyl 4-aminobenzoate (7.62 g, 50.4 mmol) in DIEA (50 mL). The mixture was stirred at 130° C. for 4 hr. The reaction mixture was diluted with EtOAc (50 mL) and H₂O (30 mL). The separated organic layer was washed with H₂O (60 mL) and dried over Na₂SO₄, filtered and concentrated. After purified by silica gel flash chromatography (Eluent of 0~10% EtOAc in petroleum ether), methyl 4-((6-methoxy-3-nitropyridin-2-yl)amino)benzoate (5.12 g, yield: 26%) was obtained as a light-yellow solid. MS: m/z=304.0 [M+H]⁺. ¹H NMR (400 MHz, Chloroform-d) δ 10.79 (s, 1H), 8.48-8.41 (m, 1H), 8.06 (d, J=8.4 Hz, 2H), 7.78 (d, J=8.0 Hz, 2H), 6.31 (dd, J=9.2, 0.8 Hz, 1H), 4.01 (s, 3H), 3.92 (s, 3H).

Step 2: Methyl 4-(2-(2-aminopyridin-3-yl)-5-methoxy-3H-imidazo[4,5-b]pyridin-3-yl)benzoate To a solution of methyl 4-((6-methoxy-3-nitropyridin-2-yl)amino)benzoate (5.12 g, 16.9 mmol) in DMSO (100 mL) was added Na₂S₂O₄ (13.5 g, 67.5 mmol, 87% purity) and 2-aminonicotinaldehyde (2.47 g, 20.3 mmol). The mixture was stirred at 100° C. for 16 hr. The reaction mixture was quenched with H₂O (25 mL) at 25° C., and then extracted with CH₂Cl₂ (50 mL×3). The combined organic layers were washed with brine (50 mL), dried over Na₂SO₄, filtered and concentrated under reduced pressure. After purified by silica gel flash chromatography (Eluent of 0~35% EtOAc in petroleum ether), methyl 4-(2-(2-aminopyridin-3-yl)-5-methoxy-3H-imidazo[4,5-b]pyridin-3-yl)benzoate (2.0 g, yield: 28%) was obtained as a light-yellow solid. MS: m/z=376.0 [M+H]⁺. ¹H NMR (400 MHz, Chloroform-d) δ 8.16 (d, J=8.4 Hz, 2H), 8.04 (dd, J=5.2, 2.0 Hz, 1H), 7.97 (d, J=8.8 Hz, 1H), 7.47 (d, J=8.8 Hz, 2H), 6.99 (dd, J=7.6, 1.6 Hz, 1H), 6.77 (d, J=8.4 Hz, 1H), 6.55 (br s, 2H), 6.37 (dd, J=8.0, 5.2 Hz, 1H), 3.96 (s, 3H), 3.86 (s, 3H).

Step 3: (4-(2-(2-Aminopyridin-3-yl)-5-methoxy-3H-imidazo[4,5-b]pyridin-3-yl)phenyl)methanol A mixture of methyl 4-(2-(2-aminopyridin-3-yl)-5-methoxy-3H-imidazo[4,5-b]pyridin-3-yl)benzoate (2.0 g, 5.33 mmol) in THF (130 mL) was added LiAlH₄ (2.5 M, 2.77 mL) at 0° C. dropwise, the mixture was stirred at 25° C. for 2 hr. The reaction mixture was quenched with Na₂SO₄·10H₂O (3 g) at 0° C., and then filtered and concentrated under reduced pressure to give (4-(2-(2-aminopyridin-3-yl)-5-methoxy-3H-imidazo[4,5-b]pyridin-3-yl)phenyl)methanol (1.8 g, crude) as a yellow solid. MS: m/z=348.0 [M+H]⁺.

Step 4: 3-(3-(4-(Chloromethyl)phenyl)-5-methoxy-3H-imidazo[4,5-b]pyridin-2-yl)pyridin-2-amine To a solution of (4-(2-(2-aminopyridin-3-yl)-5-methoxy-3H-imidazo[4,5-b]pyridin-3-yl)phenyl)methanol (1.8 g, 5.18 mmol) in CH₂Cl₂ (20 mL) was added SOCl₂ (1.23 g, 10.4 mmol). The mixture was stirred at 40° C. for 2 hr. The residue was poured into water (200 mL). The resulting mixture was washed with CH₂Cl₂ (10 mL×2), then aqueous phase was adjusted pH to around 8 by NaHCO₃. The resulting mixture was extracted with CH₂Cl₂ (100 mL). The combined organic layers were dried over anhydrous Na₂SO₄, filtered and concentrated to dryness. After purified by silica gel flash chromatography (Eluent of 0~35% EtOAc in petroleum ether), 3-(3-(4-(chloromethyl)phenyl)-5-methoxy-3H-imidazo[4,5-b]pyridin-2-yl)pyridin-2-amine (Intermediate 73, 1.3 g, yield: 65%) was obtained as a light-yellow solid. MS: m/z=366.0 [M+H]⁺.

Intermediate 74: 2-(2-Aminopyridin-3-yl)-3-(4-(chloromethyl)phenyl)-3H-imidazo[4,5-b]pyridine-5-carboxamide

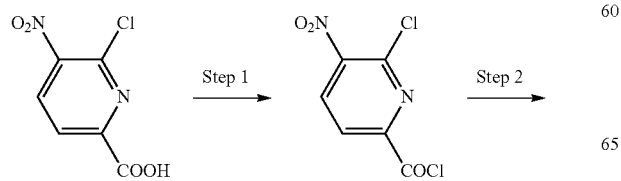

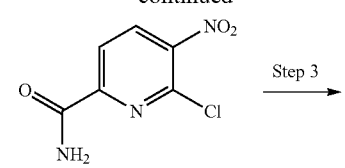

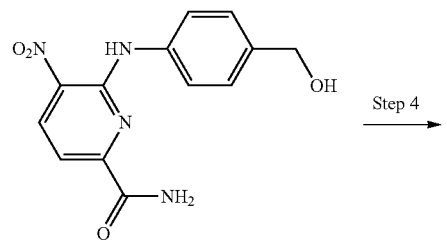

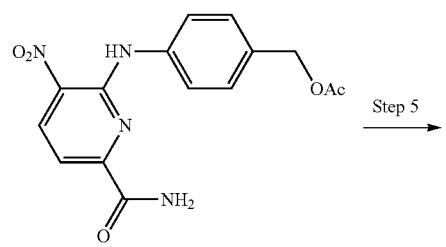

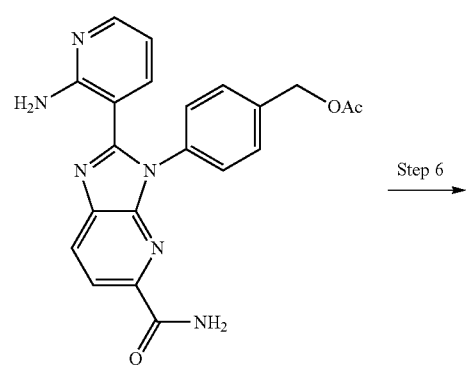

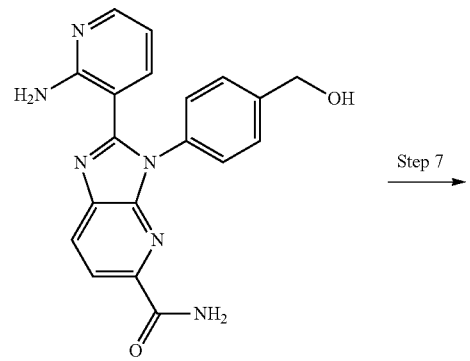

-continued

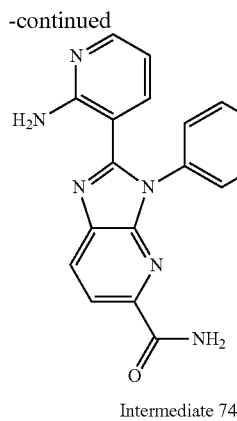

Intermediate 74

Step 1: 6-Chloro-5-nitropicolinoyl chloride

A solution of 6-chloro-5-nitropicolinic acid (5 g, 24.7 mmol) in $SOCl_2$ (20 mL) was stirred at 80° C. for 16 hr. The reaction mixture was filtered and concentrated under reduced pressure to give 6-chloro-5-nitropicolinoyl chloride (5.4 g, yield: 97%) as a yellow solid, which was directly used to the next step.

Step 2: 6-Chloro-5-nitropicolinamide

To a solution of 6-chloro-5-nitropicolinoyl chloride (5 g, 22.6 mmol) in THF (50 mL) was added $NH_3 \cdot H_2O$ (9.51 g, 67.9 mmol) at 0° C. The mixture was stirred at 0° C. for 1 hr. Then the reaction mixture was diluted with $H_2O$ (100 mL) and extracted with EtOAc (100 mL×2). The combined organic layers were dried over $Na_2SO_4$, filtered and concentrated under reduced pressure to give 6-chloro-5-nitropicolinamide (3.3 g, yield: 65%) as a yellow solid. MS: m/z=201.9 $[M+H]^+$.

Step 3: 6-((4-(Hydroxymethyl)phenyl)amino)-5-nitropicolinamide

To a solution of 6-chloro-5-nitropicolinamide (3.3 g, 16.4 mmol) in DMSO (20 mL) were added (4-aminophenyl)methanol (2.02 g, 16.4 mmol) and DIEA (6.35 g, 49.1 mmol). The mixture was stirred at 100° C. for 16 hr. The reaction mixture was diluted with $H_2O$ (100 mL) and extracted with $CH_2Cl_2$ (100 mL×2). The combined organic layers were washed with brine (100 mL×2), dried over $Na_2SO_4$, filtered and concentrated under reduced pressure to give 6-((4-(hydroxymethyl)phenyl)amino)-5-nitropicolinamide (3.2 g, yield: 67%) as a yellow solid. MS: m/z=288.9 $[M+H]^+$. $^1H$ NMR (400 MHz, Dimethylsulfoxide-$d_6$) δ 9.96 (s, 1H), 8.67 (d, J=8.4 Hz, 1H), 7.94 (s, 1H), 7.61-7.55 (m, 2H), 7.47 (d, J=8.0 Hz, 1H), 7.35 (d, J=8.4 Hz, 2H), 7.27 (s, 1H), 5.18 (t, J=5.6 Hz, 1H), 4.50 (d, J=5.6 Hz, 2H).

Step 4: 4-((6-Carbamoyl-3-nitropyridin-2-yl)amino)benzyl acetate

To a solution of 6-((4-(hydroxymethyl)phenyl)amino)-5-nitropicolinamide (2.4 g, 8.33 mmol) in $CH_2Cl_2$ (20 mL) were added TEA (2.53 g, 25 mmol), $Ac_2O$ (1.27 g, 12.5 mmol) and DMAP (101 mg, 823 μmol). The mixture was stirred at 25° C. for 1 hr. The reaction mixture was quenched with $H_2O$ (50 mL) at 25° C., and then extracted with $CH_2Cl_2$ (50 mL×3). The combined organic layers were washed with brine (50 mL), dried over $Na_2SO_4$, filtered and concentrated under reduced pressure to give 4-((6-carbamoyl-3-nitropyridin-2-yl)amino)benzyl acetate (2.5 g, yield: 90%) as a red solid. MS: m/z=353.0 $[M+Na]^+$. $^1H$ NMR (400 MHz, Dimethylsulfoxide-$d_6$) δ 9.98 (s, 1H), 8.67 (d, J=8.4 Hz, 1H), 7.94 (s, 1H), 7.69-7.62 (m, 2H), 7.49 (d, J=8.4 Hz, 1H), 7.40 (d, J=8.4 Hz, 2H), 7.36-7.29 (m, 1H), 5.07 (s, 2H), 2.07 (s, 3H).

Step 5: 4-(2-(2-Aminopyridin-3-yl)-5-carbamoyl-3H-imidazo[4,5-b]pyridin-3-yl)benzyl acetate To a solution of 4-((6-(dimethylcarbamoyl)-3-nitropyridin-2-yl)amino)benzyl acetate (2.2 g, 6.66 mmol) in DMSO (20 mL) were added $Na_2S_2O_4$ (2.32 g, 13.3 mmol) and 2-aminonicotinaldehyde (895 mg, 7.33 mmol). The mixture was stirred at 100° C. for 16 hr. The reaction mixture was quenched with $H_2O$ (50 mL) at 25° C., and then extracted with $CH_2Cl_2$ (50 mL×3). The combined organic layers were washed with brine (50 mL), dried over $Na_2SO_4$, filtered and concentrated under reduced pressure. After purified by silica gel flash chromatography (Eluent of 50~80% EtOAc in petroleum ether), 4-(2-(2-aminopyridin-3-yl)-5-carbamoyl-3H-imidazo[4,5-b]pyridin-3-yl)benzyl acetate (900 mg, yield: 30%) was obtained as a yellow solid. MS: m/z=403.0 $[M+H]^+$.

Step 6: 2-(2-Aminopyridin-3-yl)-3-(4-(hydroxymethyl)phenyl)-3H-imidazo[4,5-b]pyridine-5-carboxamide To a solution of 4-(2-(2-aminopyridin-3-yl)-5-carbamoyl-3H-imidazo[4,5-b]pyridin-3-yl)benzyl acetate (900 mg, 2.24 mmol) in THF (10 mL) and MeOH (10 mL) was added $K_2CO_3$ (927 mg, 6.71 mmol). The mixture was stirred at 25° C. for 0.5 hr. The reaction mixture was diluted with $H_2O$ (20 mL) and extracted with $CH_2Cl_2$ (20 mL×2). The combined organic layers were washed with brine (20 mL), dried over $Na_2SO_4$, filtered and concentrated under reduced pressure to give 2-(2-aminopyridin-3-yl)-3-(4-(hydroxymethyl)phenyl)-3H-imidazo[4,5-b]pyridine-5-carboxamide (700 mg, yield: 46%) as a yellow solid. MS: m/z=361.0 $[M+H]^+$. $^1H$ NMR (400 MHz, Dimethylsulfoxide-$d_6$) δ 8.32 (d, J=8.4 Hz, 1H), 8.07 (d, J=8.4 Hz, 1H), 8.03-8.00 (m, J H), 7.65-7.51 (m, 2H), 7.50-7.43 (m, 4H), 7.25 (dd, J=7.6, 1.6 Hz, 1H), 6.91 (br s, 2H), 6.44 (dd, J=7.6, 4.8 Hz, 1H), 4.59 (s, 2H), 3.32-3.29 (m, 1H).

Step 7: 2-(2-Aminopyridin-3-yl)-3-(4-(chloromethyl)phenyl)-3H-imidazo[4,5-b]pyridine-5-carboxamide To a solution of 2-(2-aminopyridin-3-yl)-3-(4-(hydroxymethyl)phenyl)-3H-imidazo[4,5-b]pyridine-5-carboxamide (400 mg, 1.11 mmol) in $CH_2Cl_2$ (5 mL) was added $SOCl_2$ (396 mg, 3.33 mmol). The mixture was stirred at 40° C. for 0.5 hr. The reaction was concentrated under reduced pressure to give 2-(2-aminopyridin-3-yl)-3-(4-(chloromethyl)phenyl)-3H-imidazo[4,5-b]pyridine-5-carboxamide (Intermediate 74, 400 mg, yield: 81%) was obtained as a brown solid. MS: m/z=378.9 $[M+H]^+$. $^1H$ NMR (400 MHz, Dimethylsulfoxide-$d_6$) δ 8.42 (d, J=8.4 Hz, 1H), 8.18-8.09 (m, 2H), 7.97-7.93 (m, 1H), 7.74-7.34 (m, 6H), 6.99-6.84 (m, 1H), 4.85 (s, 2H).

Intermediate 75: 2-(2-Aminopyridin-3-yl)-3-(4-(chloromethyl)phenyl)-N,N-dimethyl-3H-imidazo[4,5-b]pyridine-5-carboxamide

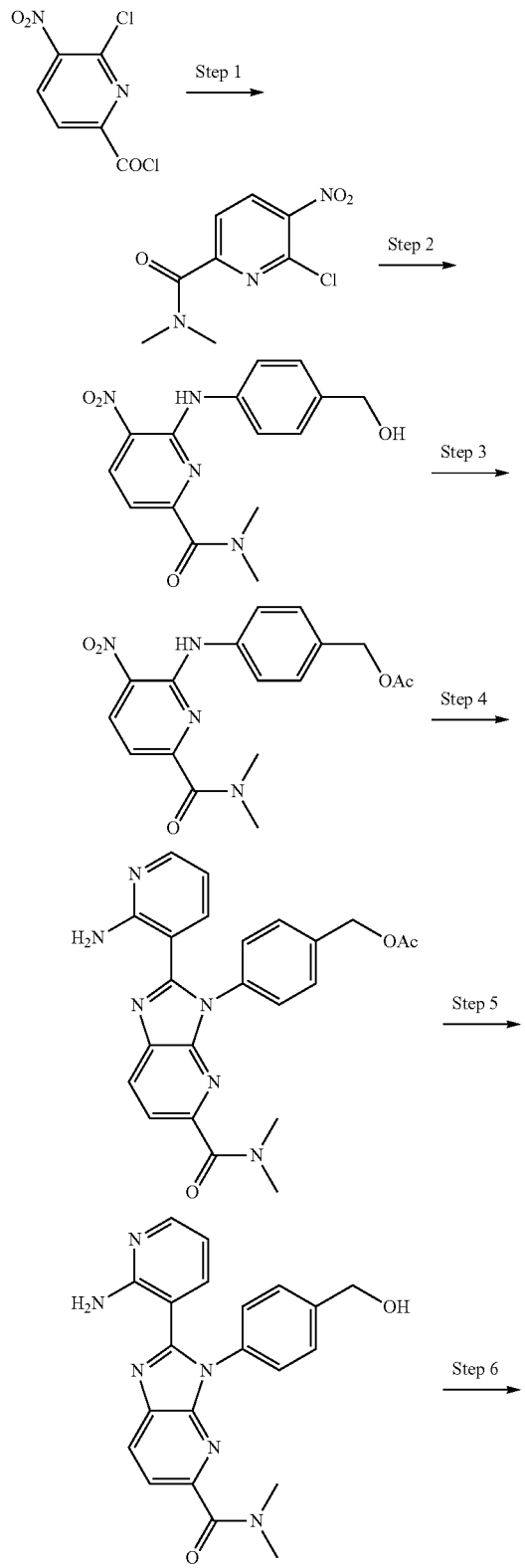

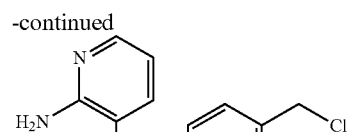

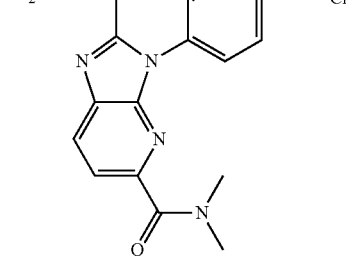

Intermediate 75

Step 1: 6-Chloro-N,N-dimethyl-5-nitropicolinamide

To a solution of 6-chloro-5-nitropicolinoyl chloride (2 g, 9.05 mmol) in $CH_2Cl_2$ (20 mL) were added TEA (2.75 g, 27.2 mmol) and dimethylamine (738 mg, 9.05 mmol, HCl salt). The mixture was stirred at 0° C. for 1 hr. The reaction mixture was quenched with $H_2O$ (20 mL) at 25° C., and then diluted with $CH_2Cl_2$ (30 mL) and extracted with $CH_2Cl_2$ (50 mL×3). The combined organic layers were washed with brine (50 mL), dried over $Na_2SO_4$, filtered and concentrated under reduced pressure to give 6-chloro-N,N-dimethyl-5-nitropicolinamide (1.9 g, yield: 70%) as a yellow solid. MS: m/z=230.0 [M+H]$^+$.

Step 2: 6-((4-(Hydroxymethyl)phenyl)amino)-N,N-dimethyl-5-nitropicolinamide

To a solution of 6-chloro-N,N-dimethyl-5-nitropicolinamide (1.9 g, 8.27 mmol) in DMSO (20 mL) were added (4-aminophenyl)methanol (815 mg, 6.62 mmol) and DIEA (3.21 g, 24.8 mmol). The mixture was stirred at 110° C. for 16 hr. The reaction mixture was quenched with $H_2O$ (20 mL) at 25° C., and extracted with $CH_2Cl_2$ (50 mL×3). The combined organic layers were washed with brine (50 mL), dried over $Na_2SO_4$, filtered and concentrated under reduced pressure to give 6-((4-(hydroxymethyl)phenyl)amino)-N,N-dimethyl-5-nitropicolinamide (2.6 g, yield: 79%) as a red solid. MS: m/z=317.0 [M+H]$^+$.

Step 3: 4-((6-(Dimethylcarbamoyl)-3-nitropyridin-2-yl)amino)benzyl acetate

To a solution of 6-((4-(hydroxymethyl)phenyl)amino)-N,N-dimethyl-5-nitropicolinamide (2.6 g, 8.22 mmol) in $CH_2Cl_2$ (20 mL) were added TEA (2.50 g, 24.7 mmol), $Ac_2O$ (1.26 g, 12.3 mmol) and DMAP (100 mg, 822 µmol). The mixture was stirred at 25° C. for 1 hr. The reaction mixture was quenched with $H_2O$ (50 mL) at 25° C., and extracted with $CH_2Cl_2$ (50 mL×3). The combined organic layers were washed with brine (50 mL), dried over $Na_2SO_4$, filtered and concentrated under reduced pressure. After purified by silica gel flash chromatography (Eluent of 1~30% EtOAc in petroleum ether), 4-((6-(dimethylcarbamoyl)-3-nitropyridin-2-yl)amino)benzyl acetate (1.7 g, yield: 55%) was obtained as a red solid. MS: m/z=380.9 [M+Na]$^+$.

Step 4: 4-(2-(2-Aminopyridin-3-yl)-5-(dimethylcarbamoyl)-3H-imidazo[4,5-b]pyridin-3-yl)benzyl acetate To a solution of 4-((6-(dimethylcarbamoyl)-3-nitropyridin-2-yl)amino)benzyl acetate (1.6 g, 4.46 mmol) in DMSO (20 mL) were added Na₂S₂O₄ (3.57 g, 17.9 mmol) and 2-aminonicotinaldehyde (654 mg, 5.36 mmol). The mixture was stirred at 100° C. for 16 hr. The reaction mixture was quenched with H₂O (25 mL) at 25° C. and extracted with CH₂Cl₂ (50 mL×3). The combined organic layers were washed with brine (50 mL), dried over Na₂SO₄, filtered and concentrated under reduced pressure. After purified by silica gel flash chromatography (Eluent of 50%~100% EtOAc in petroleum ether), 4-(2-(2-aminopyridin-3-yl)-5-(dimethylcarbamoyl)-3H-imidazo[4,5-b]pyridin-3-yl)benzyl acetate (370 mg, yield: 19%) was obtained as a brown solid. MS: m/z=431.1 [M+H]⁺.

Step 5: 2-(2-Aminopyridin-3-yl)-3-(4-(hydroxymethyl)phenyl)-N,N-dimethyl-3H-imidazo[4,5-b]pyridine-5-carboxamide To a solution of 4-(2-(2-aminopyridin-3-yl)-5-(dimethylcarbamoyl)-3H-imidazo[4,5-b]pyridin-3-yl)benzyl acetate (370 mg, 860 μmol) in THF (5 mL) and MeOH (5 mL) was added K₂CO₃ (356 mg, 2.58 mmol). The mixture was stirred at 25° C. for 0.5 hr. The reaction mixture was diluted with H₂O (10 mL) and extracted with CH₂Cl₂ (15 mL×2). The combined organic layers were washed with brine (10 mL), dried over Na₂SO₄, filtered and concentrated under reduced pressure to give 2-(2-aminopyridin-3-yl)-3-(4-(hydroxymethyl)phenyl)-N,N-dimethyl-3H-imidazo[4,5-b]pyridine-5-carboxamide (320 mg, yield: 74%) as a yellow solid. MS: m/z=389.1 [M+H]⁺.

Step 6: 2-(2-Aminopyridin-3-yl)-3-(4-(chloromethyl)phenyl)-N,N-dimethyl-3H-imidazo[4,5-b]pyridine-5-carboxamide To a solution of 2-(2-aminopyridin-3-yl)-3-(4-(hydroxymethyl)phenyl)-N,N-dimethyl-3H-imidazo[4,5-b]pyridine-5-carboxamide (320 mg, 824 μmol) in CH₂Cl₂ (5 mL) was added SOCl₂ (294 mg, 2.47 mmol). The mixture was stirred at 40° C. for 0.4 hr. The reaction was concentrated under reduced pressure to give 2-(2-aminopyridin-3-yl)-3-(4-(chloromethyl)phenyl)-N,N-dimethyl-3H-imidazo[4,5-b]pyridine-5-carboxamide (Intermediate 75, 330 mg, yield: 91%) as a yellow solid. MS: m/z=407.0 [M+H]⁺.

Intermediate 76: 3-(3-(4-(Chloromethyl)phenyl)-5-(2-chlorophenyl)-3H-imidazo[4,5-b]pyridin-2-yl)pyridin-2-amine

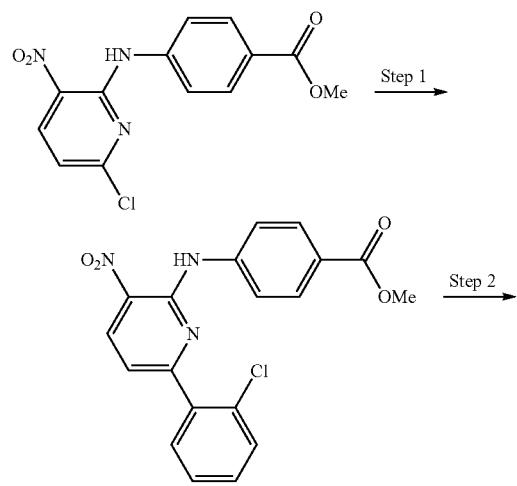

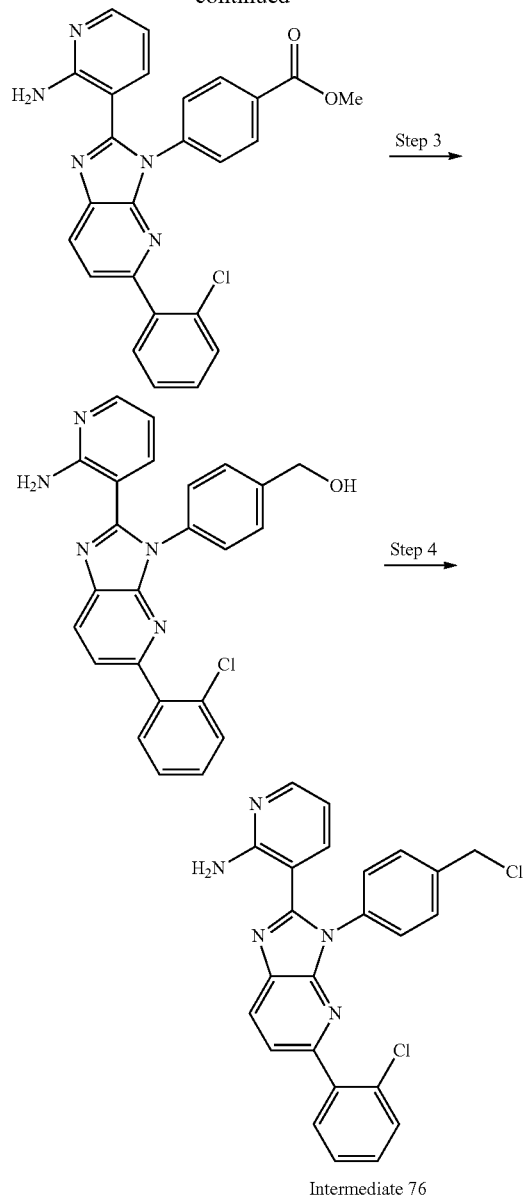

Intermediate 76

Step 1: Methyl 4-((6-(2-chlorophenyl)-3-nitropyridin-2-yl)amino)benzoate

To a mixture of methyl 4-((6-chloro-3-nitropyridin-2-yl)amino)benzoate (refer to Intermediate 13 for detail procedures, 5 g, 16.2 mmol), (2-chlorophenyl)boronic acid (3.3 g, 21.1 mmol), Pd(dppf)Cl₂ (1.19 g, 1.63 mmol), Cs₂CO₃ (15.8 g, 48.7 mmol) in dioxane (50 mL) and H₂O (5 mL) was degassed and purged with N₂ three times, and the mixture was stirred at 100° C. for 12 hr under N₂ atmosphere. The reaction mixture was diluted with water (20 mL) and extracted with CH₂Cl₂ (30 mL×2). The combined organic layers were dried over Na₂SO₄, filtered and concentrated under reduced pressure. The residue was purified by silica gel flash chromatography (Eluent of 0-10% MeOH in CH₂Cl₂) to give methyl 4-((6-(2-chlorophenyl)-3-nitropyridin-2-yl)amino)benzoate (1.5 g, yield: 21%) as a yellow solid. MS: m/z=384.0 [M+H]⁺. ¹H NMR (400 MHz, Chloroform-d) δ 10.49 (br s, 1H), 8.63 (d, J=8.8 Hz, 1H), 8.04 (d, J=6.8 Hz, 2H), 7.90 (d, J=9.2 Hz, 2H), 7.68-7.63 (m, 1H), 7.56-7.52 (m, 1H), 7.46-7.39 (m, 2H), 7.33 (d, J=8.8 Hz, 1H), 3.91 (s, 3H).

Step 2: Methyl 4-(2-(2-aminopyridin-3-yl)-5-(2-chlorophenyl)-3H-imidazo[4,5-b]pyridin-3-yl)benzoate To a solution of methyl 4-((6-(2-chlorophenyl)-3-nitropyridin-2-yl)amino)benzoate (1.5 g, 3.91 mmol) and 2-aminonicotinaldehyde (525 mg, 4.30 mmol) in DMSO (45 mL) was added Na$_2$S$_2$O$_4$ (3.20 g, 15.6 mmol). The mixture was stirred at 100° C. for 12 hr. The reaction mixture was diluted with water (100 mL) and extracted with CH$_2$Cl$_2$ (300 mL×2). The combined organic layers were washed with brine (100 mL), dried over Na$_2$SO$_4$, filtered and concentrated under reduced pressure. The residue was purified by silica gel flash chromatography (Eluent of 0~100% EtOAc in petroleum ether) to give methyl 4-(2-(2-aminopyridin-3-yl)-5-(2-chlorophenyl)-3H-imidazo[4, 5-b]pyridin-3-yl)benzoate (800 mg, yield: 41%) as a yellow solid. MS: m/z=456.0 [M+H]$^+$. $^1$H NMR (400 MHz, Chloroform-d) S 8.23-8.15 (m, 3H), 8.07 (dd, J=4.8, 1.6 Hz, 1H), 7.73 (d, J=8.4 Hz, 1H), 7.60-7.52 (m, 3H), 7.50-7.46 (m, 1H), 7.36-7.31 (m, 2H), 7.10 (dd, J=7.6, 1.6 Hz, 1H), 6.92 (br s, 2H), 6.43 (dd, J=8.0, 5.2 Hz, 1H), 3.96 (s, 3H).

Step 3: (4-(2-(2-Aminopyridin-3-yl)-5-(2-chlorophenyl)-3H-imidazo[4,5-b]pyridin-3-yl)phenyl)methanol To a solution of methyl 4-(2-(2-aminopyridin-3-yl)-5-(2-chlorophenyl)-3H-imidazo[4,5-b]pyridin-3-yl)benzoate (800 mg, 1.75 mmol) in THF (50 mL) was added LiAlH$_4$ (2.5 M, 1.05 mL) at 0° C. The mixture was stirred at 25° C. for 2 hr. The reaction mixture was quenched with Na$_2$SO$_4$·10H$_2$O (120 mg) at 0° C. and filtered. The filtrate was concentrated under reduced pressure to give (4-(2-(2-aminopyridin-3-yl)-5-(2-chlorophenyl)-3H-imidazo[4,5-b]pyridin-3-yl)phenyl)methanol (700 mg, crude as a yellow solid.

Step 4: 3-(3-(4-(Chloromethyl)phenyl)-5-(2-chlorophenyl)-3H-imidazo[4,5-b]pyridin-2-yl)pyridin-2-amine To a solution of (4-(2-(2-aminopyridin-3-yl)-5-(2-chlorophenyl)-3H-imidazo[4,5-b]pyridin-3-yl)phenyl)methanol (700 mg, 1.64 mmol) in CH$_2$Cl$_2$ (10 mL) was added SOCl$_2$ (1.17 g, 9.82 mmol). The mixture was stirred at 40° C. for 2 hr. The mixture was concentrated under reduced pressure. 3-(3-(4-(Chloromethyl)phenyl)-5-(2-chlorophenyl)-3H-imidazo[4,5-b]pyridin-2-yl)pyridin-2-amine (Intermediate 76, 750 mg HCl salt) was obtained as a yellow solid. MS: m/z=446.0 [M+H]$^+$.

Intermediate 77: 3-(5-(2-Chlorophenyl)-3-(4-(piperazin-1-ylmethyl)phenyl)-3H-imidazo[4,5-b]pyridin-2-yl)pyridin-2-amine Step 1: tert-Butyl 4-(4-(2-(2-aminopyridin-3-yl)-5-(2-chlorophenyl)-3H-imidazo[4,5-b]pyridin-3-yl)benzyl)piperazine-1-carboxylate

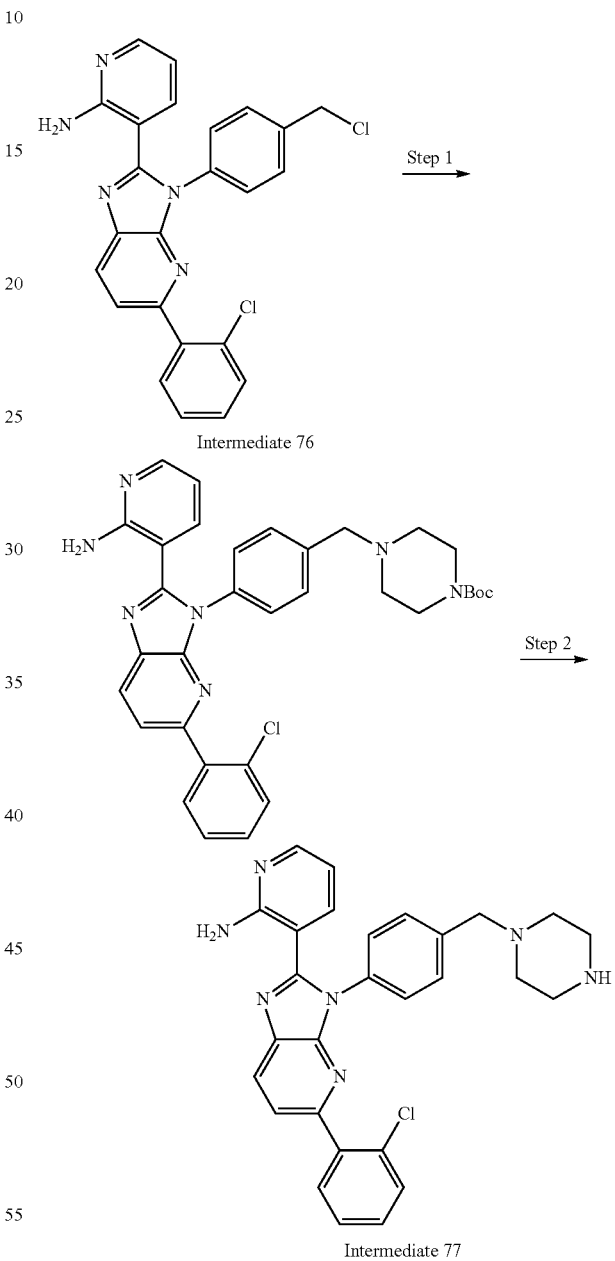

Intermediate 76

Intermediate 77

To a solution of Intermediate 76 (1 g, 2.24 mmol) and tert-butyl piperazine-1-carboxylate (417 mg, 2.24 mmol) in MeCN (10 mL) were added NaI (67.2 mg, 448 μmol) and K$_2$CO$_3$ (929 mg, 6.72 mmol). The mixture was stirred at 25° C. for 16 hr. The residue was diluted with H$_2$O (30 mL) and extracted with EtOAc (30 mL×3). The combined organic layers were washed with brine (20 mL×2), dried over Na$_2$SO$_4$, filtered and concentrated under reduced pressure. The residue was purified by silica gel flash chromatography (Eluent of 0~3% MeOH in CH₂Cl₂) to give tert-butyl 4-(4-(2-(2-aminopyridin-3-yl)-5-(2-chlorophenyl)-3H-imidazo[4,5-b]pyridin-3-yl)benzyl)piperazine-1-carboxylate (600 mg, yield: 45%) as a yellow solid. MS: m/z=596.1 [M+H]⁺.

Step 6: 3-(5-(2-Chlorophenyl)-3-(4-(piperazin-1-ylmethyl)phenyl)-3H-imidazo[4,5-b]pyridin-2-yl)pyridin-2-amine To a solution of tert-butyl 4-(4-(2-(2-aminopyridin-3-yl)-5-(2-chlorophenyl)-3H-imidazo[4,5-b]pyridin-3-yl)benzyl)piperazine-1-carboxylate (600 mg, 1.01 mmol) in MeOH (2 mL) was added HCl in 1,4-dioxane (4 M, 5 mL). The mixture was stirred at 25° C. for 3 hr. The reaction mixture was filtered and concentrated under reduced pressure to give 3-(5-(2-chlorophenyl)-3-(4-(piperazin-1-ylmethyl)phenyl)-3H-imidazo[4,5-b]pyridin-2-yl)pyridin-2-amine (Intermediate 77, HCl salt, 530 mg, yield: 90%). MS: m/z=496.3 [M+H]⁺. ¹H NMR (400 MHz, Methanol-d₄) δ 8.23 (d, J=8.4 Hz, 1H), 8.01-7.96 (m, 1H), 7.66 (d, J=8.0 Hz, 1H), 7.56-7.48 (m, 4H), 7.44-7.32 (m, 5H), 6.48 (dd, J=7.6, 5.6 Hz, 1H), 3.58 (s, 2H), 2.87-2.84 (m, 4H), 2.52-2.44 (m, 4H).

Intermediate 78: 4-(2-(2-Aminopyridin-3-yl)-3-(4-(piperazin-1-ylmethyl)phenyl)-3H-imidazo[4,5-b]pyridin-5-yl)benzonitrile

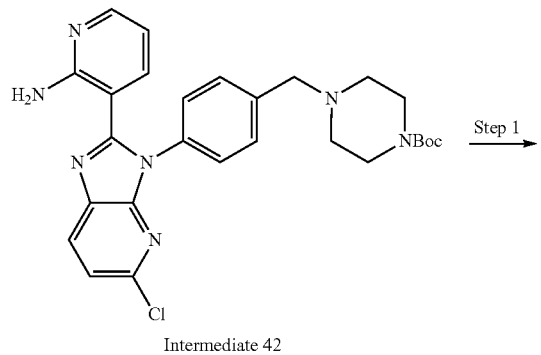

Intermediate 42

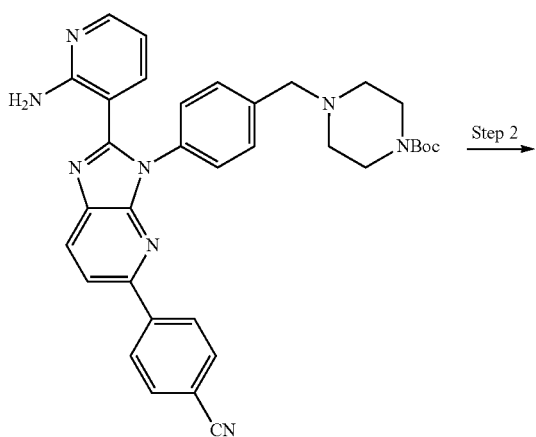

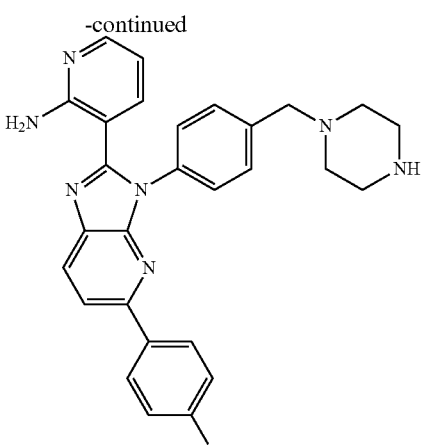

Intermediate 78

Step 1: Tert-butyl 4-(4-(2-(2-aminopyridin-3-yl)-5-(4-cyanophenyl)-3H-imidazo[4,5-b]pyridin-3-yl)benzyl)piperazine-1-carboxylate A mixture of Intermediate 42 (220 mg, 423 μmol), (4-cyanophenyl)boronic acid (68.4 mg, 465 μmol), Cs₂CO₃ (414 mg, 1.27 mmol), Pd(dppf)Cl₂ (155 mg, 212 μmol) in 1,4-dioxane (5 mL) and H₂O (1 mL) was degassed and purged with N₂ three times, and then the mixture was stirred at 100° C. for 16 hr under N₂ atmosphere. The reaction mixture was filtered at 25° C., and then diluted with H₂O (20 mL) and extracted with CH₂Cl₂ (20 mL×3). The combined organic layers were washed with brine (30 mL), dried over Na₂SO₄, filtered and concentrated under reduced pressure. After purified by silica gel flash chromatography (Eluent of 0~30% EtOAc in petroleum ether), tert-butyl 4-(4-(2-(2-aminopyridin-3-yl)-5-(3-cyanophenyl)-3H-imidazo[4,5-b]pyridin-3-yl)benzyl)piperazine-1-carboxylate (220 mg, yield: 89%) was obtained as a brown solid. MS: m/z=587.4 [M+H]⁺.

Step 2: 4-(2-(2-Aminopyridin-3-yl)-3-(4-(piperazin-1-ylmethyl)phenyl)-3H-imidazo[4,5-b]pyridin-5-yl)benzonitrile To a solution of tert-butyl 4-(4-(2-(2-aminopyridin-3-yl)-5-(3-cyanophenyl)-3H-imidazo[4,5-b]pyridin-3-yl)benzyl)piperazine-1-carboxylate (220 mg, 375 μmol) in 1,4-dioxane (3 mL) was added 4 M HCl in 1,4-dioxane (3 mL) at 25° C. The mixture was stirred at 25° C. for 16 hr. The reaction mixture was then filtered. The collected solid was washed with 1,4-dioxane (2 mL×2) and dried in vacuo to give 4-(2-(2-aminopyridin-3-yl)-3-(4-(piperazin-1-ylmethyl)phenyl)-3H-imidazo[4,5-b]pyridin-5-yl)benzonitrile (Intermediate 78, 192 mg HCl solid, yield: 98%) as a yellow solid. MS: m/z=487.2 [M+H]⁺. ¹H NMR (400 MHz, Methanol-d₆) δ 8.38 (d, J=8.4 Hz, 1H), 8.25 (d, J=8.4 Hz, 2H), 8.13 (d, J=8.4 Hz, 1H), 8.04 (d, J=5.6 Hz, 1H), 7.95 (d, J=7.6 Hz, 2H), 7.89 (d, J=7.2 Hz, 1H), 7.81 (d, J=8.4 Hz, 2H), 7.74 (d, J=7.6 Hz, 2H), 6.93 (t, J=6.8 Hz, 1H), 3.71-3.70 (m, 6H), 3.68-3.64 (m, 4H).

Intermediate 79: 3-(5-(3-Fluorophenyl)-3-(4-(piperazin-1-ylmethyl)phenyl)-3H-imidazo[4,5-b]pyridin-2-yl)pyridin-2-amine

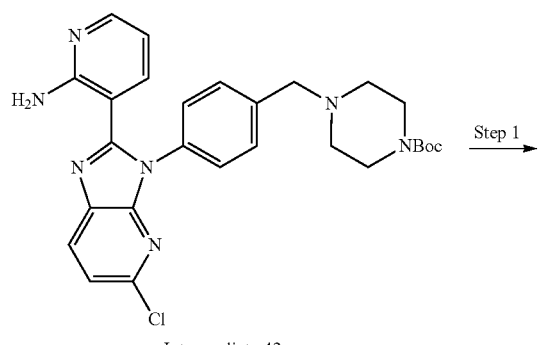

Intermediate 42

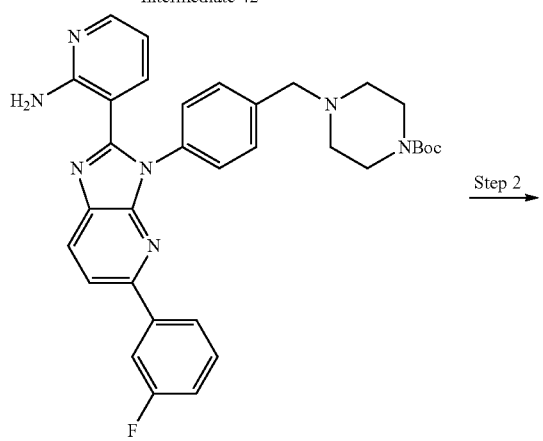

Intermediate 79

Step 1: Tert-butyl 4-(4-(2-(2-aminopyridin-3-yl)-5-(3-fluorophenyl)-3H-imidazo[4,5-b]pyridin-3-yl)benzyl)piperazine-1-carboxylate A mixture of Intermediate 42 (200 mg, 385 μmol), (3-fluorophenyl)boronic acid (59.2 mg, 423 μmol), Cs$_2$CO$_3$ (376 mg, 1.15 mmol), Pd(dppf)Cl$_2$ (141 mg, 192 μmol) in 1,4-dioxane (5 mL) and H$_2$O (1 mL) was degassed and purged with N$_2$ three times, and then the mixture was stirred at 100° C. for 16 hr under N$_2$ atmosphere. The reaction mixture was filtered at 25° C., and then diluted with H$_2$O (20 mL) and extracted with CH$_2$Cl$_2$ (20 mL×3). The combined organic layers were washed with brine (30 mL), dried over Na$_2$SO$_4$, filtered and concentrated under reduced pressure. After purified by silica gel flash chromatography (Eluent of 0~30% EtOAc in petroleum ether), tert-butyl 4-(4-(2-(2-aminopyridin-3-yl)-5-(3-fluorophenyl)-3H-imidazo[4,5-b]pyridin-3-yl)benzyl)piperazine-1-carboxylate (250 mg, yield: 98%) was obtained as a yellow solid. MS: m/z=580.2 [M+H]$^+$.

Step 2: 3-(5-(3-Fluorophenyl)-3-(4-(piperazin-1-ylmethyl)phenyl)-3H-imidazo[4,5-b]pyridin-2-yl)pyridin-2-amine To a solution of tert-butyl 4-(4-(2-(2-aminopyridin-3-yl)-5-(3-fluorophenyl)-3H-imidazo[4,5-b]pyridin-3-yl)benzyl)piperazine-1-carboxylate (200 mg, 345 μmol) in 1,4-dioxane (3 mL) was added 4 M HCl in 1,4-dioxane (3 mL) at 25° C. The mixture was stirred at 25° C. for 16 hr. The reaction mixture was then filtered and the collected solid was washed with 1,4-dioxane (2 mL×2) and dried in vacuo to give 3-(5-(3-fluorophenyl)-3-(4-(piperazin-1-ylmethyl)phenyl)-3H-imidazo[4,5-b]pyridin-2-yl)pyridin-2-amine (Intermediate 79, 174 mg HCl salt, yield: 98%) as a yellow solid. MS: m/z=480.1 [M+H]$^+$. $^1$H NMR (400 MHz, Methanol-d$_4$) δ 8.34 (d, J=8.4 Hz, 1H), 8.08-8.01 (m, 2H), 7.98-7.86 (m, 4H), 7.81-7.71 (m, 3H), 7.52-7.42 (m, 1H), 7.18-7.12 (m, 1H), 6.98-6.85 (m, 1H), 3.69-3.67 (m, 4H), 3.35 (s, 2H), 3.34-3.31 (m, 4H). $^{19}$F NMR (400 MHz, Methanol-d$_4$) δ −115.02.

Intermediate 80: 3-(5-(3-Chlorophenyl)-3-(4-(piperazin-1-ylmethyl)phenyl)-3H-imidazo[4,5-b]pyridin-2-yl)pyridin-2-amine

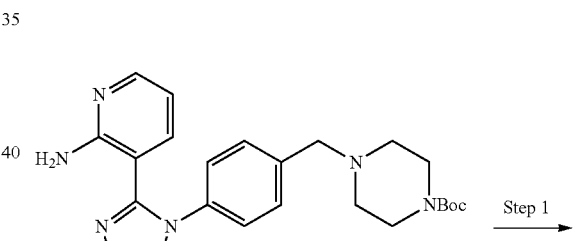

Intermediate 42

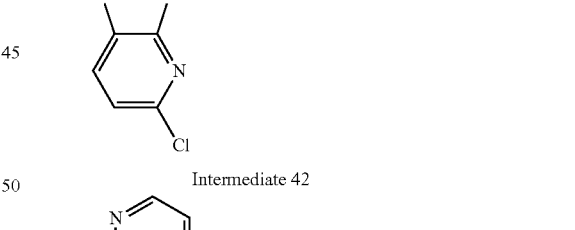

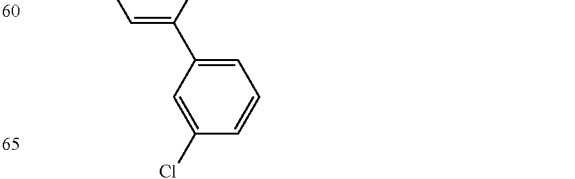

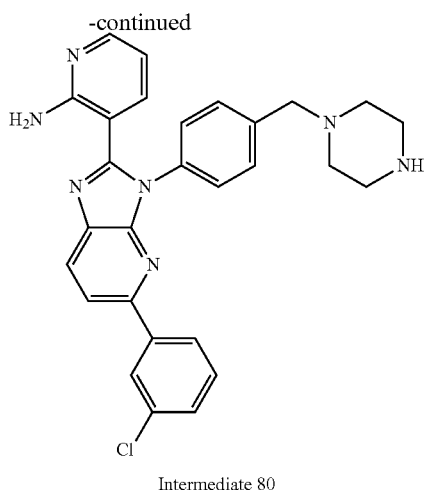

Intermediate 80

Step 1: tert-Butyl 4-(4-(2-(2-aminopyridin-3-yl)-5-(3-chlorophenyl)-3H-imidazo[4,5-b]pyridin-3-yl)benzyl)piperazine-1-carboxylate A mixture of Intermediate 42 (200 mg, 385 μmol), (3-chlorophenyl)boronic acid (66.2 mg, 423 μmol), $Cs_2CO_3$ (376 mg, 1.15 mmol), $Pd(dppf)Cl_2$ (141 mg, 192 μmol) in 1,4-dioxane (5 mL) and $H_2O$ (1 mL) was degassed and purged with $N_2$ three times, and then the mixture was stirred at 100° C. for 16 hr under $N_2$ atmosphere. The reaction mixture was filtered at 25° C., and then diluted with $H_2O$ (20 mL) and extracted with $CH_2Cl_2$ (20 mL×3). The combined organic layers were washed with brine (30 mL), dried over $Na_2SO_4$, filtered and concentrated under reduced pressure. After purified by silica gel flash chromatography (Eluent of 0~30% EtOAc in petroleum ether), tert-butyl 4-(4-(2-(2-aminopyridin-3-yl)-5-(3-chlorophenyl)-3H-imidazo[4,5-b]pyridin-3-yl)benzyl)piperazine-1-carboxylate (200 mg, yield: 77%) was obtained as a yellow solid. MS: m/z=596.3 $[M+H]^+$.

Step 2: 3-(5-(3-Chlorophenyl)-3-(4-(piperazin-1-ylmethyl)phenyl)-3H-imidazo[4,5-b]pyridin-2-yl)pyridin-2-amine To a solution of tert-butyl 4-(4-(2-(2-aminopyridin-3-yl)-5-(3-chlorophenyl)-3H-imidazo[4,5-b]pyridin-3-yl)benzyl)piperazine-1-carboxylate (150 mg, 252 μmol) in 1,4-dioxane (3 mL) was added 4 M HCl in 1,4-dioxane (3 mL) at 25° C. The mixture was stirred at 25° C. for 16 hr. The reaction mixture was then filtered and the collected solid was washed with 1,4-dioxane (2 mL×2) and dried in vacuo to give 3-(5-(3-chlorophenyl)-3-(4-(piperazin-1-ylmethyl)phenyl)-3H-imidazo[4,5-b]pyridin-2-yl)pyridin-2-amine (Intermediate 80, 113 mg, HCl salt, yield: 84%) as a yellow solid. MS: m/z=496.1 $[M+H]^+$. $^1H$ NMR (400 MHz, Methanol-$d_4$) δ 8.21 (d, J=8.4 Hz, 1H), 8.04 (s, 1H), 8.01-7.92 (m, 3H), 7.55 (d, J=8.0 Hz, 2H), 7.45 (d, J=8.4 Hz, 2H), 7.43-7.33 (m, 3H), 6.48 (dd, J=7.6, 5.2 Hz, 1H), 3.64 (s, 2H), 2.92 (t, J=5.2 Hz, 4H), 2.50-2.58 (m, 4H).

Intermediate 81: 3-(3-(4-((4-Aminopiperidin-1-yl)methyl)phenyl)-5-cyclopropyl-3H-imidazo[4,5-b]pyridin-2-yl)pyridin-2-amine

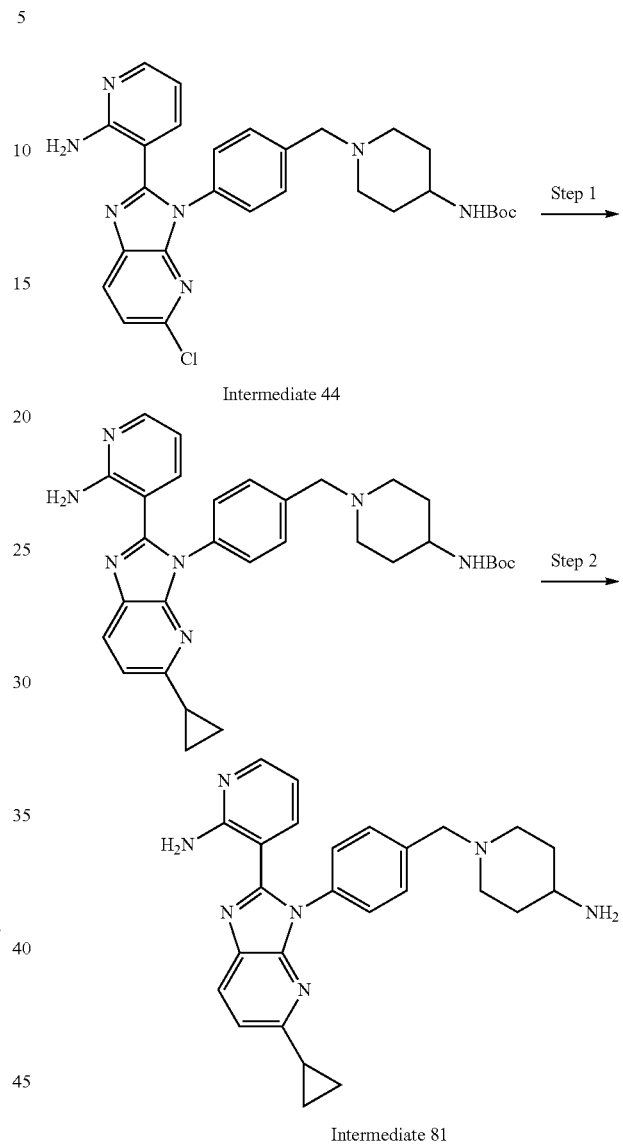

Intermediate 44

Intermediate 81

Step 1: tert-Butyl (1-(4-(2-(2-aminopyridin-3-yl)-5-cyclopropyl-3H-imidazo[4,5-b]pyridin-3-yl)benzyl)piperidin-4-yl)carbamate A mixture of Intermediate 44 (300 mg, 562 μmol), cyclopropylboronic acid (97 mg, 1.1 mmol), t-BuOK (126 mg, 1.1 mmol), cataCXiumAPdG3 (41 mg, 56 μmol) in $H_2O$ (2 mL) and 1,4-dioxane (8 mL) was degassed and purged with $N_2$ three times, and then the mixture was stirred at 100° C. for 16 hr under $N_2$ atmosphere. The reaction mixture was quenched with $H_2O$ (30 mL) at 25° C., and extracted with EtOAc (30 mL×2). The combined organic layers were washed with brine (30 mL), dried over $Na_2SO_4$, filtered, and concentrated under reduced pressure. The crude was purified by silica gel flash chromatography (Eluent of 0~100% EtOAc in petroleum ether) to give tert-butyl (1-(4-(2-(2-aminopyridin-3-yl)-5-cyclopropyl-3H-imidazo[4,5-b]pyridin-3-yl)benzyl)piperidin-4-yl)carbamate (120 mg, yield: 40%) as a yellow solid. MS: m/z=540.3 [M+H]+. 1H NMR (400 MHz, Chloroform-d) δ 8.03 (dd, J=4.8, 1.6 Hz, 1H), 7.92 (d, J=8.4 Hz, 1H), 7.48-7.43 (m, 2H), 7.31-7.28 (m, 2H), 7.12 (d, J=8.4 Hz, 1H), 7.02 (dd, J=7.6, 1.6 Hz, 1H), 6.52 (br s, 2H), 6.33 (dd, J=7.6, 4.8 Hz, 1H), 4.52-4.41 (m, 1H), 3.68-3.51 (m, 3H), 2.98-2.85 (m, 2H), 2.30-2.17 (m, 2H), 2.12-2.11 (m, 1H), 2.01-1.95 (m, 2H), 1.45-1.43 (m, 11H), 0.96-0.92 (m, 4H).

Step 2: 3-(3-(4-((4-Aminopiperidin-1-yl)methyl) phenyl)-5-cyclopropyl-3H-imidazo[4,5-b]pyridin-2-yl)pyridin-2-amine To a solution of tert-butyl (1-(4-(2-(2-aminopyridin-3-yl)-5-cyclopropyl-3H-imidazo[4,5-b]pyridin-3-yl)benzyl)piperidin-4-yl)carbamate (130 mg, 241 μmol) in HCl in 1,4-dioxane (4M, 3 mL). The mixture was stirred at 25° C. for 1 hr. Then the mixture was concentrated under reduced pressure to give 3-(3-(4-((4-aminopiperidin-1-yl)methyl) phenyl)-5-cyclopropyl-3H-imidazo[4,5-b]pyridin-2-yl)pyridin-2-amine (Intermediate 81, 110 mg HCl salt, yield: 96%) was obtained as a light yellow solid. MS: m/z=440.1 [M+H]+. 1H NMR (400 MHz, Methanol-d4) δ8.16-8.06 (m, 1H), 8.05-7.95 (m, 1H), 7.98-7.85 (m, 3H), 7.61 (d, J=7.2 Hz, 2H), 7.41-7.30 (m, 1H), 6.96-6.79 (m, 1H), 4.48 (s, 2H), 3.68 (d, J=11.6 Hz, 2H), 3.60-3.65 (m, 2H), 3.29-3.23 (m, 1H), 2.31 (d, J=12.8 Hz, 2H), 2.26-2.03 (m, 3H), 1.07-0.88 (m, 4H).

Intermediate 82: 3-(3-(4-(Chloromethyl)phenyl)-5-(tetrahydro-2H-pyran-4-yl)-3H-imidazo[4,5-b]pyridin-2-yl)pyridin-2-amine

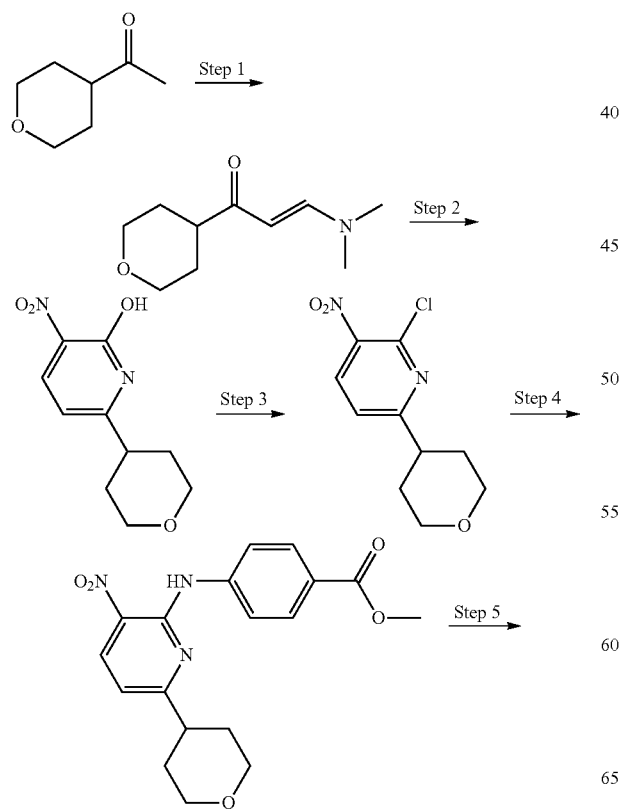

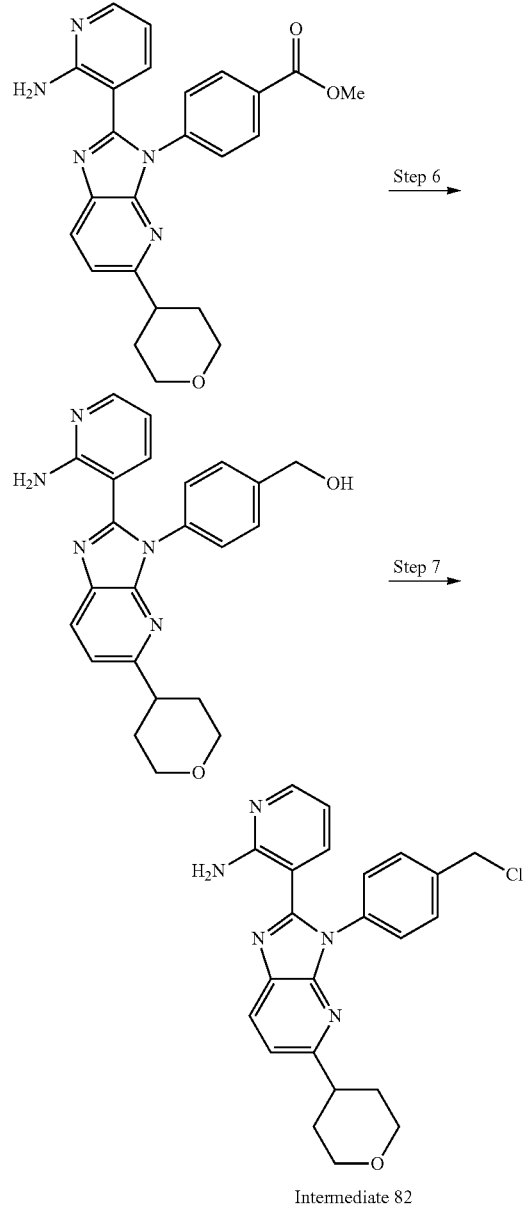

Intermediate 82

Step 1: (E)-3-(dimethylamino)-1-(tetrahydro-2H-pyran-4-yl)prop-2-en-1-one

To a solution of 1-(tetrahydro-2H-pyran-4-yl)ethan-1-one (10 g, 78 mmol) in DMF (100 mL) was added DMF-DMA (18.6 g, 156 mmol) and CH3ONa (422 mg, 7.8 mmol). The mixture was stirred at 100° C. for 16 hr. The reaction mixture was quenched with H2O (500 mL) at 25° C., and extracted with EtOAc (500 mL×2). The combined organic layers were washed with brine (500 mL), dried over Na2SO4, filtered and concentrated under reduced pressure to give a (E)-3-(dimethylamino)-1-(tetrahydro-2H-pyran-4-yl) prop-2-en-1-one (12.56 g, crude) as light yellow oil, which was used to the next step directly. MS: m/z=184.0 [M+H]+.

Step 2: 3-Nitro-6-(tetrahydro-2H-pyran-4-yl) pyridin-2-ol

To a solution of (E)-3-(dimethylamino)-1-(tetrahydro-2H-pyran-4-yl)prop-2-en-1-one (2.3 g, 13 mmol) in H$_2$O (20 mL) were added piperidine acetic acid salt (911 mg, 6.3 mmol) and 2-nitroacetamide (2.0 g, 18.8 mmol). The mixture was stirred at 25° C. for 16 hr. The reaction mixture was filtered, and the filter cake was washed with H$_2$O (20 mL), dried in reduced pressure to give a 3-nitro-6-(tetrahydro-2H-pyran-4-yl) pyridin-2-ol (1.2 g, yield: 41%) as a light yellow solid. MS: m/z=225.0 [M+H]$^+$. $^1$H NMR (400 MHz, Dimethylsulfoxide-d$_6$) δ 12.78 (br s, 1H), 8.41 (d, J=8.0 Hz, 1H), 6.30 (d, J=8.0 Hz, 1H), 3.97-3.89 (m, 2H), 3.39-3.32 (m, 2H), 2.89-2.79 (m, 1H), 1.77-1.61 (m, 4H).

Step 3: 2-Chloro-3-nitro-6-(tetrahydro-2H-pyran-4-yl)pyridine

A solution of 3-nitro-6-(tetrahydro-2H-pyran-4-yl) pyridin-2-ol (4.5 g, 20 mmol) in POCl$_3$ (40 mL) was stirred at 80° C. for 16 hr. The reaction mixture was quenched with H$_2$O (80 mL) at 25° C., and then diluted with Na$_2$CO$_3$ aqueous solution (80 mL) and extracted with EtOAc (100 mL×2). The combined organic layers were washed with brine (100 mL), dried over Na$_2$SO$_4$, filtered and concentrated under reduced pressure to give a 2-chloro-3-nitro-6-(tetrahydro-2H-pyran-4-yl)pyridine (4.1 g, crude) as a brown oil, which was used to the next step directly. MS: m/z=242.9 [M+H]$^+$.

Step 4: Methyl 4-((3-nitro-6-(tetrahydro-2H-pyran-4-yl)pyridin-2-yl)amino)benzoate To a solution of 2-chloro-3-nitro-6-(tetrahydro-2H-pyran-4-yl)pyridine (1.1 g, 4.5 mmol) in DIEA (15 mL) was added methyl 4-aminobenzoate (754 mg, 4.9 mmol). The mixture was stirred at 130° C. for 16 hr. The reaction mixture was poured into H$_2$O (100 mL), extracted with EtOAc (100 mL×2). The organic phase was dried over anhydrous Na$_2$SO$_4$, filtered and concentrated under reduced pressure. The crude product was purified by silica gel flash chromatography (Eluent of 0~18% EtOAc in petroleum ether) to give methyl 4-((3-nitro-6-(tetrahydro-2H-pyran-4-yl) pyridin-2-yl) amino) benzoate (500 mg, yield: 31%) as a yellow solid. MS: m/z=358.0 [M+H]$^+$. $^1$H NMR (400 MHz, Dimethylsulfoxide-d$_6$) δ 10.17 (s, 1H), 8.50 (d, J=8.4 Hz, 1H), 7.95 (d, J=8.8 Hz, 2H), 7.89 (d, J=8.8 Hz, 2H), 7.02 (d, J=8.4 Hz, 1H), 4.01-3.93 (m, 2H), 3.84 (s, 3H), 3.47-3.40 (m, 2H), 3.06-2.95 (m, 1H), 1.83-1.65 (m, 4H).

Step 5: Methyl 4-(2-(2-aminopyridin-3-yl)-5-(tetrahydro-2H-pyran-4-yl)-3H-imidazo[4,5-b]pyridin-3-yl)benzoate To a solution of methyl 4-((3-nitro-6-(tetrahydro-2H-pyran-4-yl) pyridin-2-yl) amino) benzoate (0.5 g, 1.4 mmol) in DMSO (30 mL) were added Na$_2$S$_2$O$_4$ (9741 mg, 5.6 mmol) and 2-aminonicotinaldehyde (205 mg, 1.7 mmol). The mixture was stirred at 100° C. for 16 hr. The reaction mixture was poured into H$_2$O (100 mL), extracted with CH$_2$Cl$_2$ (100 mL×2). The organic phase was dried over anhydrous Na$_2$SO$_4$, filtered and concentrated under reduced pressure. The crude product was purified by silica gel flash chromatography (Eluent of 0~76% EtOAc in petroleum ether) to give methyl 4-(2-(2-aminopyridin-3-yl)-5-(tetrahydro-2H-pyran-4-yl)-3H-imidazo[4,5-b]pyridin-3-yl)benzoate (200 mg, yield: 33%) as a yellow solid. MS: m/z=430.0 [M+H]$^+$. $^1$H NMR (400 MHz, Chloroform-d) δ 8.20-8.17 (m, 2H), 8.06 (dd, J=4.8, 1.6 Hz, 1H), 8.03 (d, J=8.4 Hz, 1H), 7.51-7.47 (m, 2H), 7.22 (d, J=8.4 Hz, 1H), 7.04 (dd, J=7.6, 1.6 Hz, 1H), 6.61 (br s, 2H), 6.39 (dd, J=8.0, 4.8 Hz, 1H), 4.09-4.05 (m, 2H), 3.97 (s, 3H), 3.57-3.51 (m, 2H), 3.05-2.97 (m, 1H), 1.95-1.83 (m, 4H).

Step 6: (4-(2-(2-Aminopyridin-3-yl)-5-(tetrahydro-2H-pyran-4-yl)-3/H-imidazo[4,5-b]pyridin-3-yl) phenyl)methanol To a solution of methyl 4-(2-(2-aminopyridin-3-yl)-5-(tetrahydro-2H-pyran-4-yl)-3H-imidazo[4,5-b]pyridin-3-yl) benzoate (200 mg, 466 µmol) in THF (10 mL) was added dropwise LiAlH$_4$ (2.5 M, 372 µL) at 0° C. The resulting mixture was stirred at 25° C. for 1 hr. After the reaction mixture was cooled to 0° C., the reaction mixture was quenched with H$_2$O (15 mL), followed by 15% aqueous NaOH (10 mL). After being stirred at room temperature for 30 min, the mixture was filtered through celite. The filtrate was concentrated to dryness to give (4-(2-(2-aminopyridin-3-yl)-5-(tetrahydro-2H-pyran-4-yl)-3H-imidazo[4,5-b]pyridin-3-yl)phenyl)methanol (190 mg, crude) as a light yellow solid, which was used to the next step directly. MS: m/z=402.2 [M+H]$^+$

Step 7: 3-(3-(4-(Chloromethyl)phenyl)-5-(tetrahydro-2H-pyran-4-yl)-3H-imidazo[4,5-b]pyridin-2-yl)pyridin-2-amine To a solution of (4-(2-(2-aminopyridin-3-yl)-5-(tetrahydro-2H-pyran-4-yl)-3H-imidazo[4,5-b]pyridin-3-yl)phenyl)methanol (190 mg, 473 µmol) in CH$_2$Cl$_2$ (5 mL) was added SOCl$_2$ (1.6 g, 13.1 mmol). The mixture was stirred at 40° C. for 1 hr. The reaction mixture was concentrated under reduced pressure to give 3-(3-(4-(chloromethyl)phenyl)-5-(tetrahydro-2H-pyran-4-yl)-3H-imidazo[4,5-b]pyridin-2-yl)pyridin-2-amine (Intermediate 82, 200 mg, crude) as a brown solid, which was used to the next step directly. MS: m/z=420.0 [M+H]$^+$

Intermediate 83: 4-(Azetidin-3-ylamino)-1,3,5-triazine-2-carbonitrile

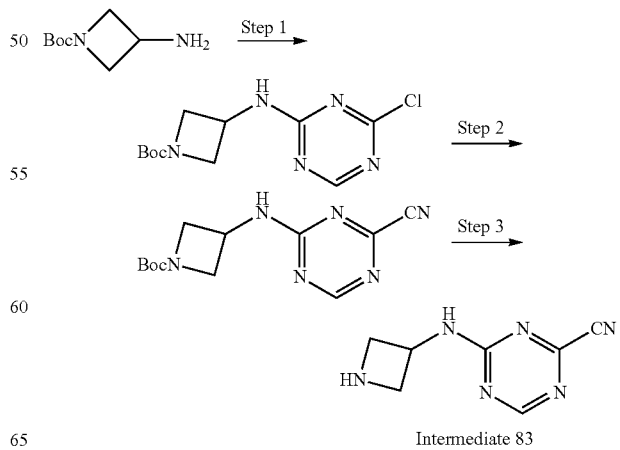

Intermediate 83

Step 1: tert-Butyl 3-((4-chloro-1,3,5-triazin-2-yl) amino)azetidine-1-carboxylate To a solution of tert-butyl 3-aminoazetidine-1-carboxylate (500 mg, 2.50 mmol) in THF (15 mL) was added DIEA (562 mg, 4.35 mmol) at 0° C. A solution of 2,4-dichloro-1,3,5-triazine (435 mg, 2.90 mmol) in THF (5 mL) was added to the mixture 10 minutes later. The mixture was stirred at 0° C. for 4 hr. The reaction mixture was diluted with water (20 mL) and extracted with EtOAc (30 mL×3). The combined organic layers were dried over Na$_2$SO$_4$, filtered and concentrated under reduced pressure. The residue was purified by silica gel flash chromatography (Eluent of 0~30% EtOAc in petroleum ether) to give tert-butyl 3-((4-chloro-1,3,5-triazin-2-yl)amino)azetidine-1-carboxylate (250 mg, yield: 31%) as a colorless oil. MS: m/z=286.1 [M+H]$^+$. $^1$H NMR (400 MHz, Chloroform-d) δ 8.49-8.32 (m, 1H), 6.25-6.00 (m, 1H), 4.85-4.66 (m, 1H), 4.40-4.25 (m, 2H), 3.90-3.75 (m, 2H), 1.45 (s, 9H).

Step 2: tert-Butyl 3-((4-cyano-1,3,5-triazin-2-yl) amino)azetidine-1-carboxylate To a solution of tert-butyl 3-((4-chloro-1,3,5-triazin-2-yl)amino)azetidine-1-carboxylate (350 mg, 1.22 mmol) in DMSO (3 mL) was added KCN (159 mg, 2.45 mmol), the mixture was stirred 0.5 hr at 25° C. Then DABCO (27.5 mg, 244 μmol) was added to the reaction mixture. The reaction mixture was stirred at 25° C. for 1 hr. The reaction mixture was poured into water (20 mL). The resulting mixture was extracted with EtOAc (20 mL×2). The combined organic layers were washed with brine (20 ml) and dried over anhydrous Na$_2$SO$_4$, filtered and concentrated to dryness. The residue was purified by silica gel flash chromatography (Eluent of 0~40% EtOAc in petroleum ether) to give tert-butyl 3-((4-cyano-1,3,5-triazin-2-yl)amino)azetidine-1-carboxylate (140 mg, yield: 33%) as a yellow solid. MS: m/z=299.1 [M+Na]+. $^1$H NMR (400 MHz, Chloroform-d) δ 8.75-8.53 (m, 1H), 6.24-5.96 (m, 1H), 4.81-4.64 (m, 1H), 4.45-4.23 (m, 2H), 3.95-3.75 (m, 2H), 1.45 (s, 9H).

Step 3: 4-(Azetidin-3-ylamino)-1,3,5-triazine-2-carbonitrile

To a solution of tert-butyl 3-((4-cyano-1,3,5-triazin-2-yl)amino)azetidine-1-carboxylate (140 mg, 506 μmol) in CH$_2$Cl$_2$ (2 mL) was added TFA (57.7 mg, 506 μmol). The mixture was stirred at 25° C. for 1 hr. The mixture was concentrated under reduced pressure to give 4-(azetidin-3-ylamino)-1,3,5-triazine-2-carbonitrile (Intermediate 83, 130 mg, TFA salt) as a yellow oil.

Intermediate 84: 4-(2,6-Diazaspiro[3.4]octan-2-yl)-1,3,5-triazine-2-carbonitrile

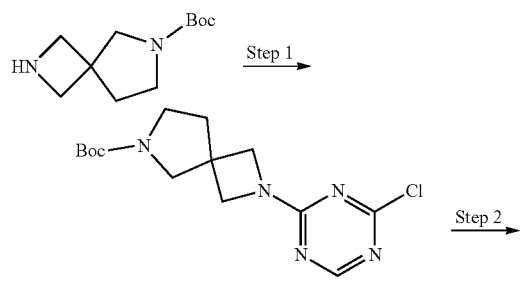

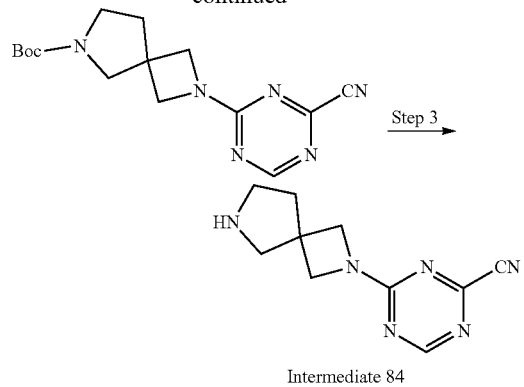

Intermediate 84

Step 1: Tert-butyl 2-(4-chloro-1,3,5-triazin-2-yl)-2,6-diazaspiro[3.4]octane-6-carboxylate To a solution of tert-butyl 2,6-diazaspiro[3.4]octane-6-carboxylate (300 mg, 1.4 mmol) in THF (5 mL) was added DIEA (548 mg, 4.3 mmol) at 25° C., then 2,4-dichloro-1,3,5-triazine (212 mg, 1.4 mmol) in THF (5 mL) was added into the mixture at 0° C. The mixture was stirred at 25° C. for 12 hr under N$_2$. The reaction mixture was poured into H$_2$O (50 mL). The mixture was extracted with CH$_2$Cl$_2$ (20 mL×2). The combined organic layers were washed with brine (40 mL), dried over anhydrous Na$_2$SO$_4$, filtered and concentrated to dryness. The residue was purified by silica gel flash chromatography (Eluent of 0~30% EtOAc in petroleum ether) to give tert-butyl 2-(4-chloro-1,3,5-triazin-2-yl)-2,6-diazaspiro[3.4]octane-6-carboxylate (230 mg, yield: 47%) as a yellow solid. MS: m/z=326.1 [M+H]$^+$. $^1$H NMR (400 MHz, Dimethylsulfoxide-d$_6$) δ 8.44 (s, 1H), 4.16-3.98 (m, 4H), 3.47-3.41 (m, 2H), 3.31-3.25 (m, 2H), 2.11-2.05 (m, 2H), 1.40 (s, 9H).

Step 2: Tert-butyl 2-(4-cyano-1,3,5-triazin-2-yl)-2,6-diazaspiro[3.4]octane-6-carboxylate To a solution of tert-butyl 2-(4-chloro-1,3,5-triazin-2-yl)-2,6-diazaspiro[3.4]octane-6-carboxylate (200 mg, 613 μmol) in DMSO (5 mL) were added KCN (140 mg, 2.2 mmol) and DABCO (14 mg, 123 μmol) at 25° C. The mixture was stirred at 25° C. for 2 hr. The reaction mixture was poured into H$_2$O (20 mL). The mixture was extracted with EtOAc (20 mL×2). The combined organic layers were washed with brine (40 mL), dried over anhydrous Na$_2$SO$_4$, filtered and concentrated to dryness. The residue was purified by silica gel flash chromatography (Eluent of 0~30% EtOAc in petroleum ether) to give tert-butyl 2-(4-cyano-1,3,5-triazin-2-yl)-2,6-diazaspiro[3.4]octane-6-carboxylate (150 mg, yield: 76%) as a yellow solid. MS: m/z=317.0 [M+H]$^+$.

Step 3: 4-(2,6-Diazaspiro[3.4]octan-2-yl)-1,3,5-triazine-2-carbonitrile

To a solution of tert-butyl 2-(4-cyano-1,3,5-triazin-2-yl)-2,6-diazaspiro[3.4]octane-6-carboxylate (150 mg, 474 μmol) in CH$_2$Cl$_2$ (3 mL) was added TFA (1.5 g, 13 mmol) at 25° C. The mixture was stirred at 25° C. for 2 hr. The reaction mixture was concentrated under reduced pressure to give a crude 4-(2,6-diazaspiro[3.4]octan-2-yl)-1,3,5-triazine-2-carbonitrile (Intermediate 84, 130 mg, TFA salt) as a yellow solid, which was used in the next step without further purification.

Intermediate 85: 4-(2,6-Diazaspiro[3.3]heptan-2-yl)-1,3,5-triazine-2-carbonitrile

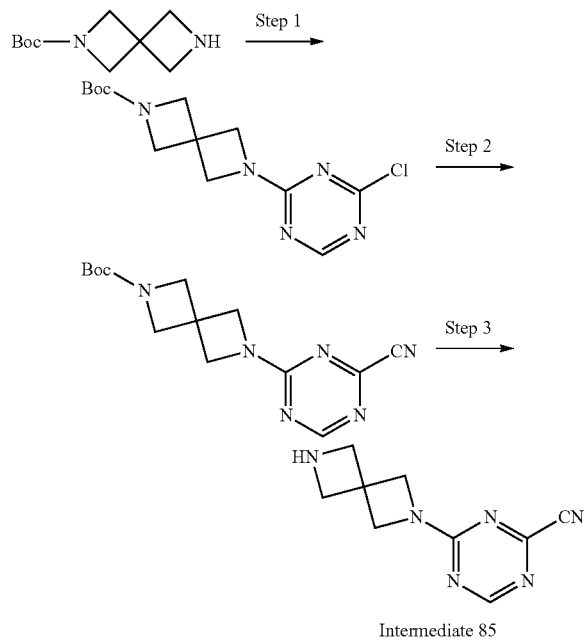

Intermediate 85

Step 1: tert-Butyl 6-(4-chloro-1,3,5-triazin-2-yl)-2,6-diazaspiro[3.3]heptane-2-carboxylate To a solution of tert-butyl 2,6-diazaspiro[3.3]heptane-2-carboxylate (300 mg, 1.5 mmol) in THF (5 mL) was added DIEA (587 mg, 4.5 mmol) at 25° C., then a solution of 2,4-dichloro-1,3,5-triazine (227 mg, 1.5 mmol) in THF (5 mL) was added into the mixture at 0° C. The mixture was stirred at 25° C. for 12 hr under $N_2$. The reaction mixture was poured into $H_2O$ (50 mL). The mixture was extracted with $CH_2Cl_2$ (20 mL×2). The combined organic layers were washed with brine (40 mL), dried over anhydrous $Na_2SO_4$, filtered and concentrated to dryness. The residue was purified by silica gel flash chromatography (Eluent of 0~30% EtOAc in petroleum ether) to give tert-butyl 6-(4-chloro-1,3,5-triazin-2-yl)-2,6-diazaspiro[3.3]heptane-2-carboxylate (200 mg, yield: 42%) as a yellow solid. MS: m/z=312.1 [M+H]$^+$. $^1$H NMR (400 MHz, Dimethylsulfoxide-d$_6$) δ 8.44 (s, 1H), 4.28 (d, J=4.8 Hz, 4H), 4.03 (s, 4H), 1.38 (s, 9H).

Step 2: tert-Butyl 6-(4-cyano-1,3,5-triazin-2-yl)-2,6-diazaspiro[3.3]heptane-2-carboxylate To a solution of tert-butyl 6-(4-chloro-1,3,5-triazin-2-yl)-2,6-diazaspiro[3.3]heptane-2-carboxylate (191 mg, 614 μmol) in DMSO (5 mL) were added KCN (160 mg, 2.5 mmol) and DABCO (14 mg, 123 μmol) at 25° C. The mixture was stirred at 25° C. for 2 hr. The reaction mixture was poured into $H_2O$ (20 mL), and extracted with EtOAc (20 mL×2). The combined organic layers were washed with brine (40 mL), dried over anhydrous $Na_2SO_4$, filtered and concentrated to dryness. The residue was purified by silica gel flash chromatography (Eluent of 0~30% EtOAc in petroleum ether) to give tert-butyl 6-(4-cyano-1,3,5-triazin-2-yl)-2,6-diazaspiro[3.3]heptane-2-carboxylate (150 mg, yield: 70%) was obtained as a yellow solid. MS: m/z=303.0 [M+H]$^+$.

Step 3: 4-(2,6-Diazaspiro[3.3]heptan-2-yl)-1,3,5-triazine-2-carbonitrile

To a solution of tert-butyl 6-(4-cyano-1,3,5-triazin-2-yl)-2,6-diazaspiro[3.3]heptane-2-carboxylate (150 mg, 496 μmol) in $CH_2Cl_2$ (3 mL) was added TFA (1.6 g, 14 mmol) at 25° C., the mixture was stirred at 25° C. for 2 hr. The reaction mixture was concentrated under reduced pressure to give a crude product 4-(2,6-diazaspiro[3.3]heptan-2-yl)-1,3,5-triazine-2-carbonitrile (Intermediate 85, 130 mg, TFA salt) as a yellow solid, which was used in the next step without further purification.

Intermediate 86: 2-(Piperazin-1-yl)pyrimidine-4-carbonitrile

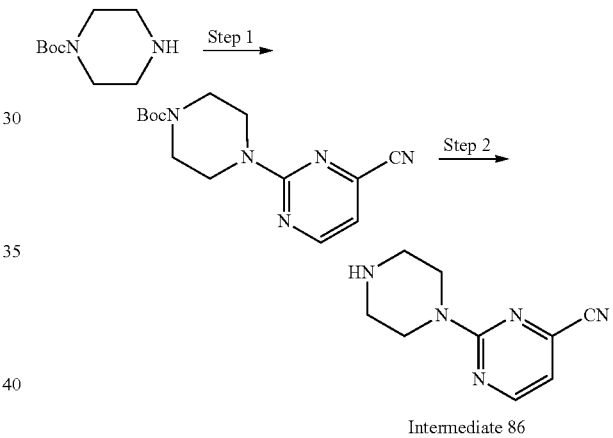

Intermediate 86

Step 1: tert-Butyl 4-(4-cyanopyrimidin-2-yl)piperazine-1-carboxylate

To a solution of 2-chloropyrimidine-4-carbonitrile (2 g, 14.3 mmol) in MeCN (20 mL) were added $K_2CO_3$ (5.94 g, 43 mmol), tert-butyl piperazine-1-carboxylate (2.67 g, 14.3 mmol) and NaI (430 mg, 2.87 mmol). The mixture was stirred at 80° C. for 16 hr. The reaction mixture was diluted with $H_2O$ (50 mL) and EtOAc (50 mL), and then extracted with EtOAc (150 mL×2). The combined organic layers were washed with brine (150 mL), dried over $Na_2SO_4$, filtered and concentrated under reduced pressure to give tert-butyl 4-(4-cyanopyrimidin-2-yl)piperazine-1-carboxylate (4.2 g, yield: 98%) as a yellow solid. MS: m/z=190.1 [M+H−100]$^+$. $^1$H NMR (400 MHz, Dimethylsulfoxide-d$_6$) δ 8.67 (d, J=4.8 Hz, 1H), 7.19 (d, J=4.8 Hz, 1H), 3.77-3.68 (m, 4H), 3.46-3.37 (m, 4H), 1.43 (s, 9H).

Step 2: 2-(Piperazin-1-yl)pyrimidine-4-carbonitrile

To a solution of tert-butyl 4-(2-cyanopyrimidin-4-yl)piperazine-1-carboxylate (130 mg, 449 mol) in $CH_2Cl_2$ (3 mL) was added TFA (717 mg, 6.30 mmol). The mixture was stirred at 25° C. for 1 hr. The reaction mixture was concentrated under reduced pressure. The crude 2-(piperazin-1-yl)pyrimidine-4-carbonitrile (Intermediate 86, 137 mg, TFA salt, yield: 100%) was used in the next step without further purification.

Intermediate 87: 2-(Piperidin-4-ylamino)pyrimidine-4-carbonitrile

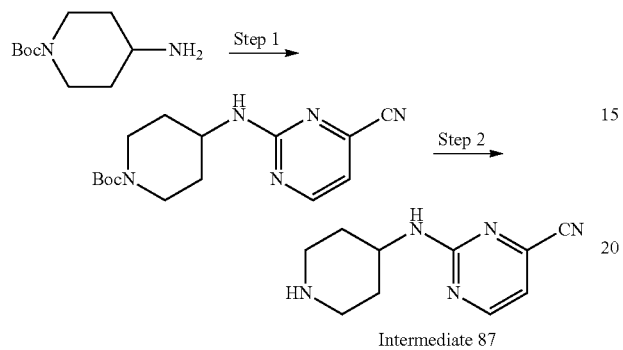

Intermediate 87

Step 1: tert-Butyl 4-((4-cyanopyrimidin-2-yl)amino)piperidine-1-carboxylate To a solution of 2-chloropyrimidine-4-carbonitrile (2 g, 14.3 mmol) in MeCN (20 mL) were added $K_2CO_3$ (5.94 g, 43 mmol), tert-butyl 4-aminopiperidine-1-carboxylate (2.87 g, 14.3 mmol) and NaI (430 mg, 2.87 mmol). The mixture was stirred at 80° C. for 16 hr. The reaction mixture was diluted with $H_2O$ (50 mL) and EtOAc (50 mL), and then extracted with EtOAc (150 mL×2). The combined organic layers were washed with aqueous NaCl (150 mL), dried over $Na_2SO_4$, filtered and concentrated under reduced pressure to give tert-butyl 4-((4-cyanopyrimidin-2-yl)amino)piperidine-1-carboxylate (4.5 g, yield: 98%) as a yellow solid. MS: m/z=248.1 [M+H−56]$^+$. $^1$H NMR (400 MHz, Dimethylsulfoxide-$d_6$) δ 8.61 (d, J=4.4 Hz, 1H), 7.10 (d, J=4.8 Hz, 1H), 6.86 (d, J=7.6 Hz, 1H), 4.50-4.41 (m, 2H), 3.62-3.47 (m, 1H), 3.12-3.03 (m, 2H), 1.84-1.75 (m, 2H), 1.39 (s, 9H), 1.33-1.24 (m, 2H).

Step 2: 2-(Piperidin-4-ylamino)pyrimidine-4-carbonitrile

To a solution of tert-butyl 4-((4-cyanopyrimidin-2-yl)amino)piperidine-1-carboxylate (140 mg, 483 μmol) in $CH_2Cl_2$ (3 mL) was added TFA (767 mg, 6.73 mmol). The mixture was stirred at 25° C. for 1 hr. The reaction mixture was concentrated under reduced pressure. The crude product 2-(piperidin-4-ylamino)pyrimidine-4-carbonitrile (Intermediate 87, 146 mg TFA salt, yield: 100%) was used in the next step without further purification. MS: m/z=204.0 [M+H]$^+$.

Intermediate 88: (R)-4-(Piperidin-3-ylamino)-1,3,5-triazine-2-carbonitrile

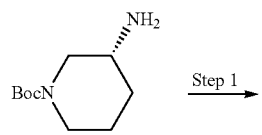

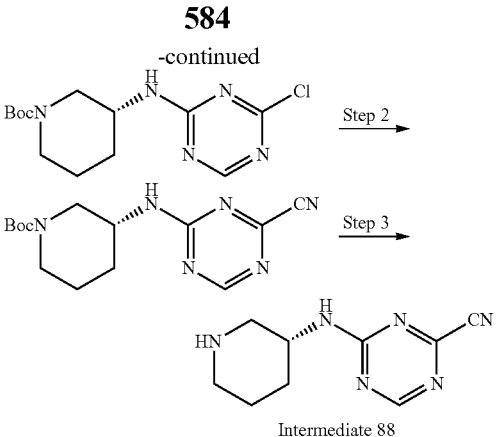

Intermediate 88

Step 1: Tert-butyl (R)-3-((4-chloro-1,3,5-triazin-2-yl)amino)piperidine-1-carboxylate To a solution of tert-butyl (R)-3-aminopiperidine-1-carboxylate (500 mg, 2.50 mmol) in THF (15 mL) was added DIEA (483 mg, 3.74 mmol) at 0° C., the mixture was stirred 10 min followed by addition of a solution of 2,4-dichloro-1,3,5-triazine (374 mg, 2.50 mmol) in THF (5 mL). The mixture was stirred at 0° C. for 4 hr. The reaction mixture was diluted with water (20 mL) and extracted with EtOAc (30 mL×3). The combined organic layers were dried over $Na_2SO_4$, filtered and concentrated under reduced pressure. The residue was purified by silica gel flash chromatography (Eluent of 0~30% EtOAc in petroleum ether) to give tert-butyl (R)-3-((4-chloro-1,3,5-triazin-2-yl)amino)piperidine-1-carboxylate (250 mg, yield: 31%) as a colorless oil. MS: m/z=314.1 [M+H]$^+$. $^1$H NMR (400 MHz, Chloroform-d) δ 8.52-8.25 (m, 1H), 5.88-5.61 (m, 1H), 4.17-3.96 (m, 1H), 3.68-3.28 (m, 4H), 1.98-1.85 (m, 1H), 1.77-1.59 (m, 3H), 1.44 (s, 9H).

Step 2: Tert-butyl (R)-3-((4-cyano-1,3,5-triazin-2-yl)amino)piperidine-1-carboxylate To a solution of tert-butyl (R)-3-((4-chloro-1,3,5-triazin-2-yl)amino)piperidine-1-carboxylate (250 mg, 796 mmol) in DMSO (5 mL) was added KCN (60 mg, 921 mmol), the mixture was stirred 0.5 hr at 25° C. DABCO (17.9 mg, 159 μmol) was added to the reaction mixture. The reaction mixture was stirred at 25° C. for 1 hr. The reaction mixture was poured into water (20 mL). The resulting mixture was extracted with EtOAc (20 mL×2). The combined organic layers were washed with brine (20 mL) and dried over anhydrous $Na_2SO_4$, filtered and concentrated to dryness. The residue was purified by silica gel flash chromatography (Eluent of 0~29% EtOAc in petroleum ether) to give tert-butyl (R)-3-((4-cyano-1,3,5-triazin-2-yl)amino)piperidine-1-carboxylate (135 mg, yield: 51%) was obtained as a yellow solid. MS: m/z=305.1 [M+H]$^+$. $^1$H NMR (400 MHz, Chloroform-d) δ 8.66-8.54 (m, 11H), 6.02-5.75 (m, 1H), 4.10-4.01 (m, 1H), 3.62-3.28 (m, 4H), 1.97-1.85 (m, 1H), 1.83-1.62 (m, 3H), 1.45 (s, 9H).

Step 3: (R)-4-(Piperidin-3-ylamino)-1,3,5-triazine-2-carbonitrile

To a solution of tert-butyl (R)-3-((4-cyano-1,3,5-triazin-2-yl)amino)piperidine-1-carboxylate (135 mg, 443 μmol) in $CH_2Cl_2$ (2 mL) was added TFA (50.5 mg, 443 μmol). The mixture was stirred at 25° C. for 1 hr. The mixture was concentrated under reduced pressure to give (R)-4-(piperidin-3-ylamino)-1,3,5-triazine-2-carbonitrile (Intermediate 88, 130 mg, TFA salt used directly) as a yellow oil.

Intermediate 89: 3-(3-(4-(Chloromethyl)phenyl)-5-(3-fluorophenyl)-3H-imidazo[4,5-b]pyridin-2-yl)pyridin-2-amine

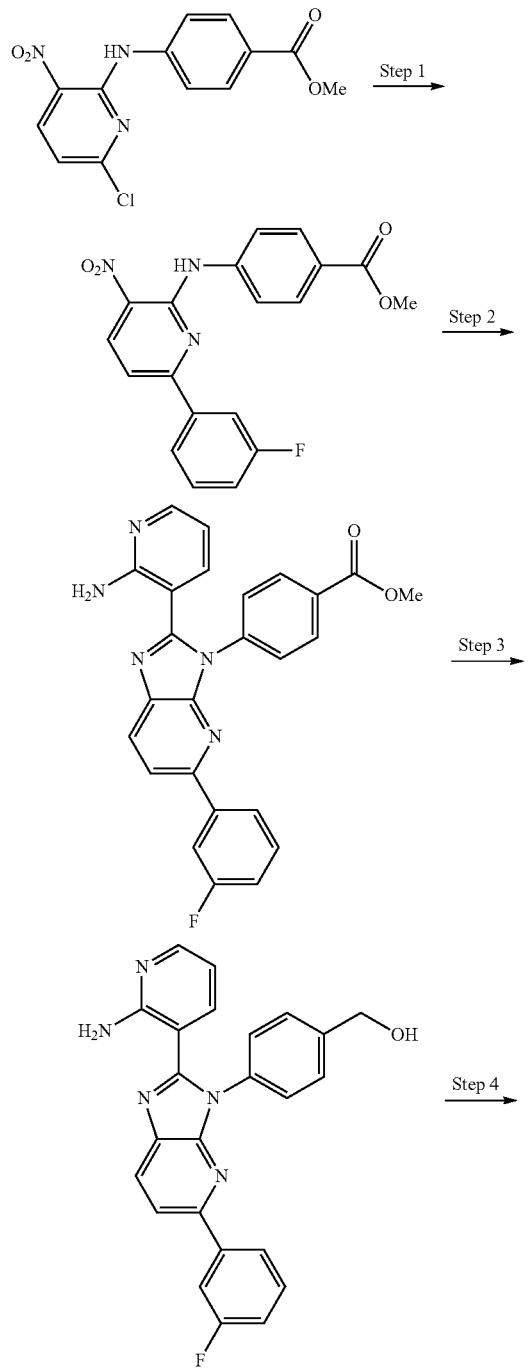

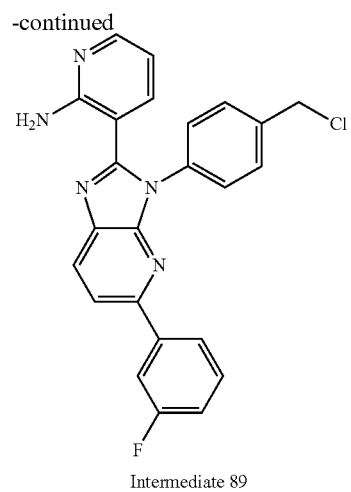

Intermediate 89

Step 1: Methyl 4-((6-(3-fluorophenyl)-3-nitropyridin-2-yl)amino)benzoate

To a mixture of methyl 4-((6-chloro-3-nitropyridin-2-yl)amino)benzoate (refer to Intermediate 13 for detail procedures, 5.0 g, 16.2 mmol), (3-fluorophenyl)boronic acid (2.96 g, 21.1 mmol), Pd(dppf)Cl$_2$ (1.19 g, 1.63 mmol), Cs$_2$CO$_3$ (15.8 g, 48.7 mmol) in 1,4-dioxane (50 mL) and H$_2$O (5 mL) was degassed and purged with N$_2$ three times, and the mixture was stirred at 100° C. for 12 hr under N$_2$ atmosphere. The reaction mixture was diluted with water (20 mL) and extracted with CH$_2$Cl$_2$ (30 mL×3). The combined organic layers were dried over Na$_2$SO$_4$, filtered and concentrated under reduced pressure. The residue was purified by silica gel flash chromatography (Eluent of 0~10% MeOH in CH$_2$Cl$_2$) to give methyl 4-((6-(3-fluorophenyl)-3-nitropyridin-2-yl)amino)benzoate (4.5 g, yield: 67%) as a yellow solid. MS: m/z=367.9 [M+H]$^+$. $^1$H NMR (400 MHz, Chloroform-d) δ 10.44 (br s, 1H), 8.64 (d, J=8.4 Hz, 1H), 8.13 (d, J=8.0 Hz, 2H), 7.92-7.80 (m, 3H), 7.77 (d, J=10.0 Hz, 1H), 7.55-7.46 (m, 1H), 7.37 (d, J=8.8 Hz, 1H), 7.26-7.19 (m, 1H), 3.95 (s, 3H), $^{19}$F NMR (400 MHz, Chloroform-d) δ −111.554.

Step 2: Methyl 4-(2-(2-aminopyridin-3-yl)-5-(3-fluorophenyl)-3H-imidazo[4,5-b]pyridin-3-yl)benzoate To a solution of methyl 4-((6-(3-fluorophenyl)-3-nitropyridin-2-yl)amino)benzoate (4.3 g, 11.7 mmol) and 2-aminonicotinaldehyde (1.57 g, 12.9 mmol) in DMSO (100 mL) was added Na$_2$S$_2$O$_4$ (9.59 g, 46.8 mmol). The mixture was stirred at 100° C. for 12 hr. The reaction mixture was diluted with water (100 mL) and extracted with CH$_2$Cl$_2$ (300 mL×2). The combined organic layers were washed with brine (100 mL), dried over Na$_2$SO$_4$, filtered and concentrated under reduced pressure. The residue was purified by silica gel flash chromatography (Eluent of 0~100% EtOAc in petroleum ether) to give methyl 4-(2-(2-aminopyridin-3-yl)-5-(3-fluorophenyl)-3H-imidazo[4,5-b]pyridin-3-yl)benzoate (3.0 g, yield: 41%) as a yellow solid. MS: m/z=440.1 [M+H]$^+$. $^1$H NMR (400 MHz, Chloroform-d) δ 8.22 (d, J=8.4 Hz, 2H), 8.17-8.06 (m, 2H), 7.83-7.69 (m, 3H), 7.55 (d, J=8.4 Hz, 2H), 7.45-7.35 (m, 1H), 7.11-7.02 (m, 2H), 6.63 (br s, 2H), 6.39 (dd, J=7.6, 5.2 Hz, 1H), 3.98 (s, 3H).

Step 3: (4-(2-(2-Aminopyridin-3-yl)-5-(3-fluorophenyl)-3H-imidazo[4,5-b]pyridin-3-yl)phenyl)methanol To a solution of methyl 4-(2-(2-aminopyridin-3-yl)-5-(3-fluorophenyl)-3H-imidazo[4,5-b]pyridin-3-yl)benzoate (3 g, 6.83 mmol) in THF (125 mL) was added LiAlH$_4$ (2.5 M, 4.10 mL) at 0° C. The mixture was stirred at 25° C. for 2 hr. The reaction mixture was quenched with Na$_2$SO$_4$10H$_2$O (120 mg) at 0° C. and filtered. The filtrate was concentrated under reduced pressure to give (4-(2-(2-aminopyridin-3-yl)-5-(3-fluorophenyl)-3H-imidazo[4,5-b]pyridin-3-yl)phenyl)methanol (3 g, crude) as a yellow solid.

Step 4: 3-(3-(4-(Chloromethyl)phenyl)-5-(3-fluorophenyl)-3H-imidazo[4,5-b]pyridin-2-yl)pyridin-2-amine To a solution of (4-(2-(2-aminopyridin-3-yl)-5-(3-fluorophenyl)-3H-imidazo[4,5-b]pyridin-3-yl)phenyl)methanol (3 g, 7.29 mmol) in CH$_2$Cl$_2$ (20 mL) was added SOCl$_2$ (5.20 g, 43.7 mmol). The mixture was stirred at 40° C. for 2 hr. The mixture was concentrated under reduced pressure to give 3-(3-(4-(chloromethyl)phenyl)-5-(3-fluorophenyl)-3H-imidazo[4,5-b]pyridin-2-yl)pyridin-2-amine (Intermediate 89, 3.4 g, HCl salt) as yellow solid. MS: m/z=430.0 [M+H]$^+$.

Intermediate 90: 3-(3-(4-(Chloromethyl)phenyl)-5-(2-fluorophenyl)-3H-imidazo[4,5-b]pyridin-2-yl)pyridin-2-amine

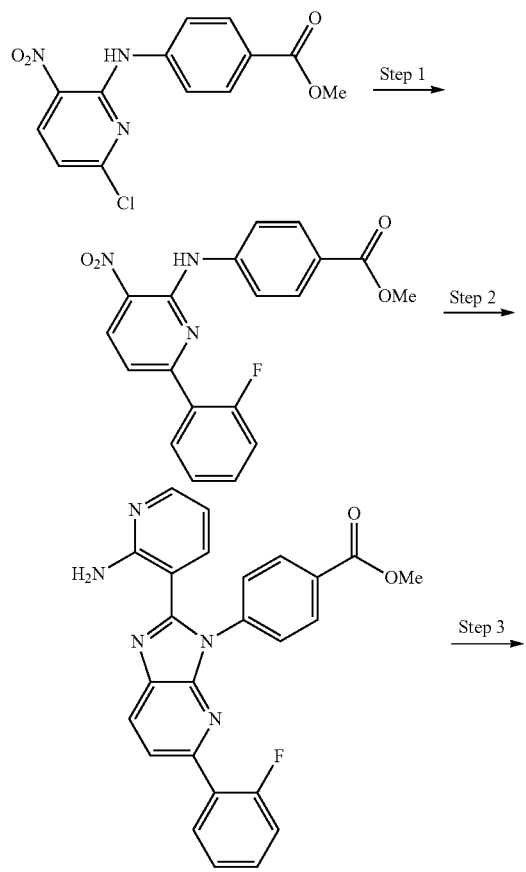

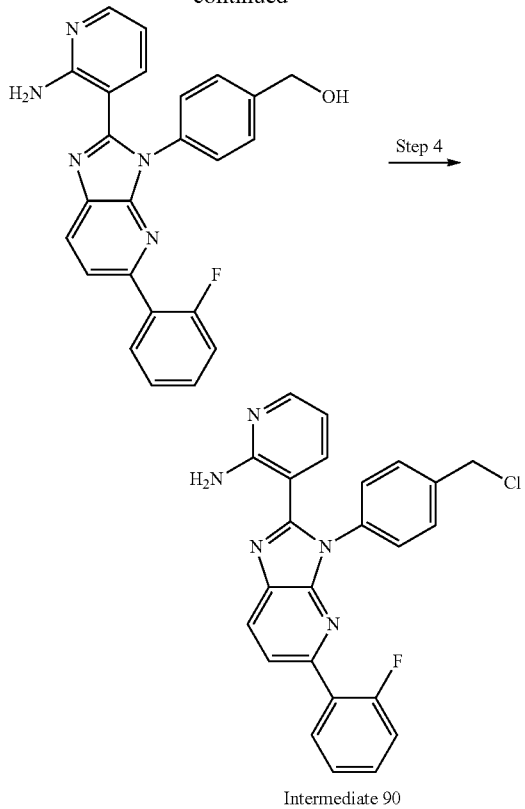

Intermediate 90

Step 1: Methyl 4-((6-(2-fluorophenyl)-3-nitropyridin-2-yl)amino)benzoate

To a mixture of methyl 4-((6-chloro-3-nitropyridin-2-yl)amino)benzoate (refer to Intermediate 13 for detail procedures, 5 g, 16.2 mmol), (2-fluorophenyl)boronic acid (2.9 g, 21.1 mmol), Pd(dppf)Cl$_2$ (1.19 g, 1.63 mmol), Cs$_2$CO$_3$ (15.8 g, 48.7 mmol) in 1,4-dioxane (50 mL) and H$_2$O (5 mL) was degassed and purged with N$_2$ three times, and the mixture was stirred at 100° C. for 12 hr under N$_2$ atmosphere. The reaction mixture was diluted with water (20 mL) and extracted with CH$_2$Cl$_2$ (30 mL×2). The combined organic layers were dried over Na$_2$SO$_4$, filtered and concentrated under reduced pressure. The residue was purified by silica gel flash silica gel flash chromatography (Eluent of 0~10% MeOH in CH$_2$Cl$_2$) to give methyl 4-((6-(2-fluorophenyl)-3-nitropyridin-2-yl)amino)benzoate (4.5 g, yield: 73%) as a yellow solid. MS: m/z=368.0 [M+H]$^+$. $^1$H NMR (400 MHz, Chloroform-d) δ 10.44 (s, 1H), 8.62 (d, J=8.4 Hz, 1H), 8.11-8.07 (m, 2H), 8.07-8.02 (m, 1H), 7.90-7.84 (m, 2H), 7.54-7.46 (m, 2H), 7.34-7.29 (m, 1H), 7.25-7.19 (m, 1H), 3.94 (s, 3H)

Step 2: Methyl 4-(2-(2-aminopyridin-3-yl)-5-(2-fluorophenyl)-3H-imidazo[4,5-b]pyridin-3-yl)benzoate To a solution of methyl 4-((6-(2-fluorophenyl)-3-nitropyridin-2-yl)amino)benzoate (4.5 g, 12.2 mmol) and 2-aminonicotinaldehyde (1.65 g, 13.5 mmol) in DMSO (100 mL) was added Na$_2$S$_2$O$_4$ (10.0 g, 49.0 mmol). The mixture was stirred at 100° C. for 12 hr. The reaction mixture was diluted with water (100 mL) and extracted with CH$_2$Cl$_2$ (300 mL×2). The combined organic layers were washed with brine (100 mL), dried over Na$_2$SO$_4$, filtered and concentrated under reduced pressure. The residue was purified by silica gel flash chromatography (Eluent of 0~100% EtOAc in petroleum ether) to give methyl 4-(2-(2-aminopyridin-3-yl)-5-(2-fluorophenyl)-3H-imidazo[4,5-b]pyridin-3-yl)benzoate (2.5 g, yield: 45%) as a yellow solid. MS: m/z=440.1 [M+H]$^+$. $^1$H NMR (400 MHz, Chloroform-d) δ 8.22 (d, J=8.4 Hz, 2H), 8.17 (d, J=8.4 Hz, 11H), 8.09 (dd, J=5.2, 2.0 Hz, 11H), 7.98-7.90 (m, 2H), 7.56 (d, J=8.4 Hz, 2H), 7.39-7.33 (m, 1H), 7.24-7.09 (m, 3H), 6.80 (br s, 2H), 6.42 (dd, J=7.6, 4.8 Hz, 1H), 3.98 (s, 3H).

Step 3: (4-(2-(2-Aminopyridin-3-yl)-5-(2-fluorophenyl)-3H-imidazo[4,5-b]pyridin-3-yl)phenyl)methanol To a solution of methyl 4-(2-(2-aminopyridin-3-yl)-5-(2-fluorophenyl)-3H-imidazo[4,5-b]pyridin-3-yl)benzoate (2.5 g, 5.69 mmol) in THF (100 mL) was added LiAlH$_4$ (2.5 M, 3.41 mL) at 0° C. The mixture was stirred at 25° C. for 2 hr. The reaction mixture was quenched with Na$_2$SO$_4$·H$_2$O (389 mg) at 0° C. and filtered. The filtrate was concentrated under reduced pressure to give (4-(2-(2-aminopyridin-3-yl)-5-(2-fluorophenyl)-3H-imidazo[4,5-b]pyridin-3-yl)phenyl)methanol (1.5 g, crude) as a yellow solid.

Step 4: 3-(3-(4-(Chloromethyl)phenyl)-5-(2-fluorophenyl)-3H-imidazo[4,5-b]pyridin-2-yl)pyridin-2-amine To a solution of (4-(2-(2-aminopyridin-3-yl)-5-(2-fluorophenyl)-3H-imidazo[4,5-b]pyridin-3-yl)phenyl)methanol (1.5 g, 3.65 mmol) in CH$_2$Cl$_2$ (20 mL) was added SOCl$_2$ (2.60 g, 21.9 mmol). The mixture was stirred at 40° C. for 2 hr. The mixture was concentrated under reduced pressure to give 3-(3-(4-(chloromethyl)phenyl)-5-(2-fluorophenyl)-3H-imidazo[4,5-b]pyridin-2-yl)pyridin-2-amine (Intermediate 90, 1.6 g, HCl salt) was obtained as a yellow solid. MS: m/z=430.1 [M+H]$^+$.

Intermediate 91: 4-(2-(2-Aminopyridin-3-yl)-3-(4-(chloromethyl)phenyl)-3H-imidazo[4,5-b]pyridin-5-yl)-1,4-diazepan-2-one

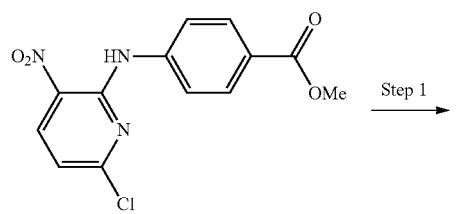

Step 1 →

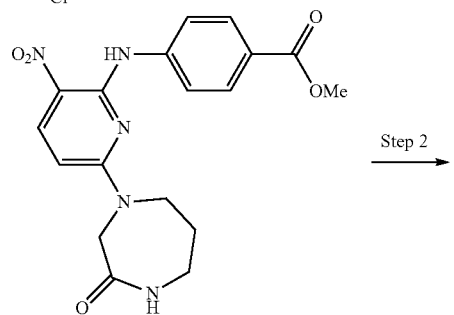

Step 2 →

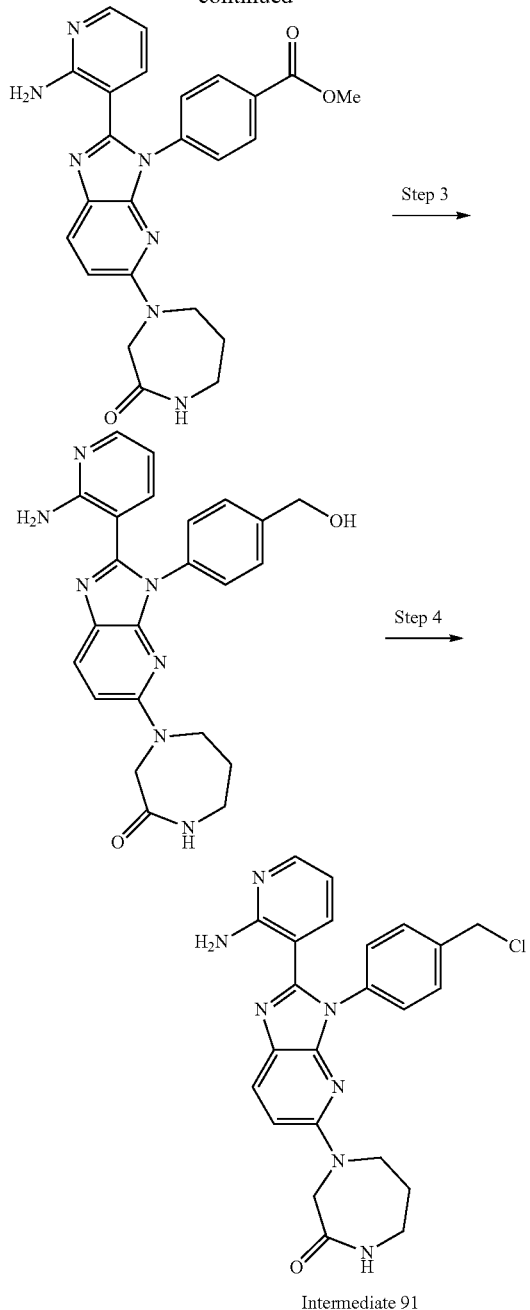

Intermediate 91

Step 1: Methyl 4-((3-nitro-6-(3-oxo-1,4-diazepan-1-yl)pyridin-2-yl)amino)benzoate To a solution of methyl 4-[(6-chloro-3-nitro-2-pyridyl)amino]benzoate (refer to Intermediate 13 for detail procedures, 1 g, 3.25 mmol) in CH$_3$CN (10 mL) were added DIEA (1.26 g, 9.75 mmol, 1.70 mL) and 1,4-diazepan-2-one (556 mg, HCl salt, 3.69 mmol). The mixture was stirred at 90° C. for 12 hr. Water (10 mL) was added to the mixture and the mixture was filtrated and the filter cake was dried under reduced pressure to give methyl 4-((3-nitro-6-(3-oxo-1,4-diazepan-1-yl)pyridin-2-yl)amino)benzoate (900 mg, yield: 72%) as a yellow solid. $^1$H NMR (400 MHz, Dimethylsulfoxide-d$_6$) δ 10.85-10.68 (m, 1H), 8.30 (d, J=8.4 Hz, 1H), 8.31-7.64 (m, 5H), 6.60-6.45 (m, 1H), 4.46-4.27 (m, 2H), 3.99 (s, 2H), 3.84 (s, 3H), 3.31-3.24 (m, 2H), 1.85-1.65 (m, 2H)).

Step 2: Methyl 4-(2-(2-aminopyridin-3-yl)-5-(3-oxo-1,4-diazepan-1-yl)-3H-imidazo[4,5-b]pyridin-3-yl)benzoate To a solution of methyl 4-((3-nitro-6-(3-oxo-1,4-diazepan-1-yl)pyridin-2-yl)amino)benzoate (900 mg, 2.34 mmol) in DMSO (10 mL) were added Na$_2$S$_2$O$_4$ (1.22 g, 7.01 mmol) and 2-aminopyridine-3-carbaldehyde (342 mg, 2.80 mmol). The mixture was stirred at 100° C. for 12 hr. Water (10 mL) was added to the mixture and the mixture was extracted with CH$_2$Cl$_2$ (10 mL×2). The combined organic phases were washed with brine (10 mL), dried over anhydrous Na$_2$SO$_4$, filtered and concentrated to give methyl 4-(2-(2-aminopyridin-3-yl)-5-(3-oxo-1,4-diazepan-1-yl)-3H-imidazo[4,5-b]pyridin-3-yl)benzoate (1 g, yield: 94%) as a yellow solid. MS: m/z=458.2 [M+H]$^+$.

Step 3: 4-(2-(2-Aminopyridin-3-yl)-3-(4-(hydroxymethyl)phenyl)-3H-imidazo[4,5-b]pyridin-5-yl)-1,4-diazepan-2-one To a solution of methyl 4-(2-(2-aminopyridin-3-yl)-5-(3-oxo-1,4-diazepan-1-yl)-3H-imidazo[4,5-b]pyridin-3-yl) benzoate (1 g, 2.19 mmol) in THF (50 mL) was added LiAlH$_4$ (166 mg, 109 μL) at 0° C. under N$_2$. The reaction mixture was stirred at 20° C. for 12 hr. Na$_2$SO$_4$·10H$_2$O was added in portions at 0° C. until no bubbles formed, and the resulting mixture was stirred for 10 min. Then filtered and the filter cake was washed with THF (10 mL×2). The filtrate was concentrated under reduced pressure to give 4-(2-(2-aminopyridin-3-yl)-3-(4-(hydroxymethyl)phenyl)-3H-imidazo[4,5-b]pyridin-5-yl)-1,4-diazepan-2-one (939 mg, yield: 100%) as a brown oil, which was used in the next step directly. MS: m/z=430.0 [M+H]$^+$.

Step 4; 4-(2-(2-Aminopyridin-3-yl)-3-(4-(chloromethyl)phenyl)-3H-imidazo[4,5-b]pyridin-5-yl)-1,4-diazepan-2-one To a solution of 4-(2-(2-aminopyridin-3-yl)-3-(4-(hydroxymethyl)phenyl)-3H-imidazo[4,5-b]pyridin-5-yl)-1,4-diazepan-2-one (939 mg, 2.19 mmol) in CH$_2$Cl$_2$ (20 mL) was added SOCl$_2$ (780 mg, 476 μL) at 20° C. The reaction mixture was stirred at 40° C. for 2 hr. The reaction mixture was concentrated to dryness to give 4-(2-(2-aminopyridin-3-yl)-3-(4-(chloromethyl)phenyl)-3H-imidazo[4,5-b]pyridin-5-yl)-1,4-diazepan-2-one (Intermediate 91, 760 mg, yield: 78%) as a brown solid, which was used in the next step directly. MS: m/z=448.1 [M+H]$^+$.

Intermediate 92: 4-(2-(2-Aminopyridin-3-yl)-3-(4-(chloromethyl)phenyl)-3H-imidazo[4,5-b]pyridin-5-yl)benzonitrile

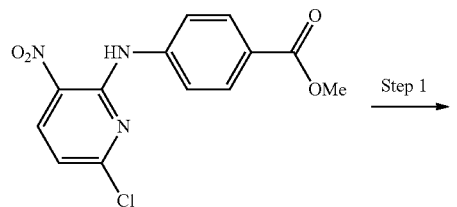

Step 1

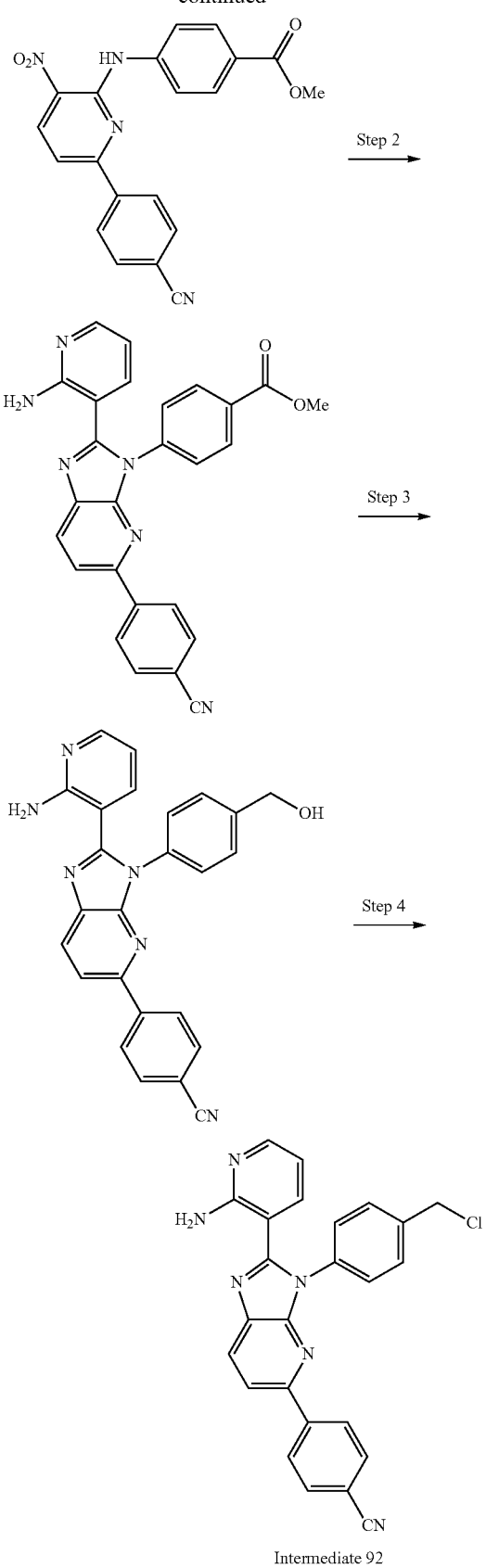

Intermediate 92

Step 1: Methyl 4-((6-(4-cyanophenyl)-3-nitropyridin-2-yl)amino)benzoate

A mixture of methyl 4-((6-chloro-3-nitropyridin-2-yl)amino)benzoate (refer to Intermediate 13 for detail procedures, 5 g, 16.3 mmol), (4-cyanophenyl)boronic acid (2.39 g, 16.3 mmol), Cs$_2$CO$_3$ (15.9 g, 48.8 mmol), Pd(dppf)Cl$_2$ (2.38 g, 3.25 mmol) in 1,4-dioxane (100 mL) and H$_2$O (20 mL) was degassed and purged with N$_2$ three times, and then the mixture was stirred at 80° C. for 16 hr under N$_2$ atmosphere. The reaction mixture was diluted with H$_2$O (100 mL) and extracted with CH$_2$Cl$_2$ (50 mL×4). The combined organic layers were washed with brine (30 mL×3), dried over Na$_2$SO$_4$, filtered and concentrated under reduced pressure. The residue was purified by silica gel flash chromatography (Eluent of 20~30% EtOAc in CH$_2$Cl$_2$), methyl 4-((6-(4-cyanophenyl)-3-nitropyridin-2-yl)amino)benzoate (6 g, yield: 50%) as a yellow solid. MS: m/z=374.9 [M+H]$^+$.

Step 2: Methyl 4-(2-(2-aminopyridin-3-yl)-5-(4-cyanophenyl)-3H-imidazo[4,5-b]pyridin-3-yl)benzoate To a solution of methyl 4-((6-(4-cyanophenyl)-3-nitropyridin-2-yl)amino)benzoate (5 g, 13.4 mmol), 2-aminonicotinaldehyde (1.63 g, 13.4 mmol) in DMSO (150 mL) was added Na$_2$S$_2$O$_4$ (9.3 g, 53.4 mmol). The mixture was stirred at 100° C. for 16 hr. The reaction mixture was diluted with H$_2$O (100 mL) and extracted with CH$_2$Cl$_2$ (500 mL×6). The combined organic layers were washed with brine (250 mL×2), dried over Na$_2$SO$_4$, filtered and concentrated under reduced pressure to give methyl 4-(2-(2-aminopyridin-3-yl)-5-(4-cyanophenyl)-3H-imidazo[4,5-b]pyridin-3-yl)benzoate (4.8 g, yield: 62%) as a black brown solid, which was directly used in the next step without further purification. MS: m/z=446.9 [M+H]$^+$.

Step 3: 4-(2-(2-Aminopyridin-3-yl)-3-(4-(hydroxymethyl)phenyl)-3H-imidazo[4,5-b]pyridin-5-yl)benzonitrile To a solution of methyl 4-(2-(2-aminopyridin-3-yl)-5-(4-cyanophenyl)-3H-imidazo[4,5-b]pyridin-3-yl)benzoate (4.8 g, 10.8 mmol) in THF (50 mL) was added LiAlH$_4$ (2.5 M, 5.16 mL) at 0° C., then the mixture was stirred at 25° C. for 2 hr. The reaction mixture was quenched with Na$_2$SO$_4$·10H$_2$O (8 g) at 0° C., and the mixture was filtered, the filter cake was washed by CH$_2$Cl$_2$ (30 mL×3), and the filtrate was concentrated under reduced pressure to give 4-(2-(2-aminopyridin-3-yl)-3-(4-(hydroxymethyl)phenyl)-3H-imidazo[4,5-b]pyridin-5-yl)benzonitrile (4.2 g, yield: 93%) as a yellow solid, which was used in the next step without purification. MS: m/z=419.1 [M+H]$^+$.

Step 4: 4-(2-(2-Aminopyridin-3-yl)-3-(4-(chloromethyl)phenyl)-3H-imidazo[4,5-b]pyridin-5-yl)benzonitrile To a solution of 4-(2-(2-aminopyridin-3-yl)-3-(4-(hydroxymethyl)phenyl)-3H-imidazo[4,5-b]pyridin-5-yl)benzonitrile (4.2 g, 10.0 mmol) in CH$_2$Cl$_2$ (40 mL) was added SOCl$_2$ (3.58 g, 30.1 mmol) at 0° C. The mixture was stirred at 40° C. for 3 hr. The reaction mixture was quenched with addition NaHCO$_3$ (5 mL) at 0° C., and then filtered and concentrated under reduced pressure. The residue was purified by silica gel flash chromatography (Eluent of 5~8% MeOH in CH$_2$Cl$_2$), 4-(2-(2-aminopyridin-3-yl)-3-(4-(chloromethyl)phenyl)-3H-imidazo[4,5-b]pyridin-5-yl)benzonitrile (Intermediate 92, 320 mg, yield: 12%) as a yellow solid. MS: m/z=437.0 [M+H]$^+$.

Intermediate 93: 2-(2-(2-Aminopyridin-3-yl)-3-(4-(chloromethyl)phenyl)-3H-imidazo[4,5-b]pyridin-5-yl)benzonitrile

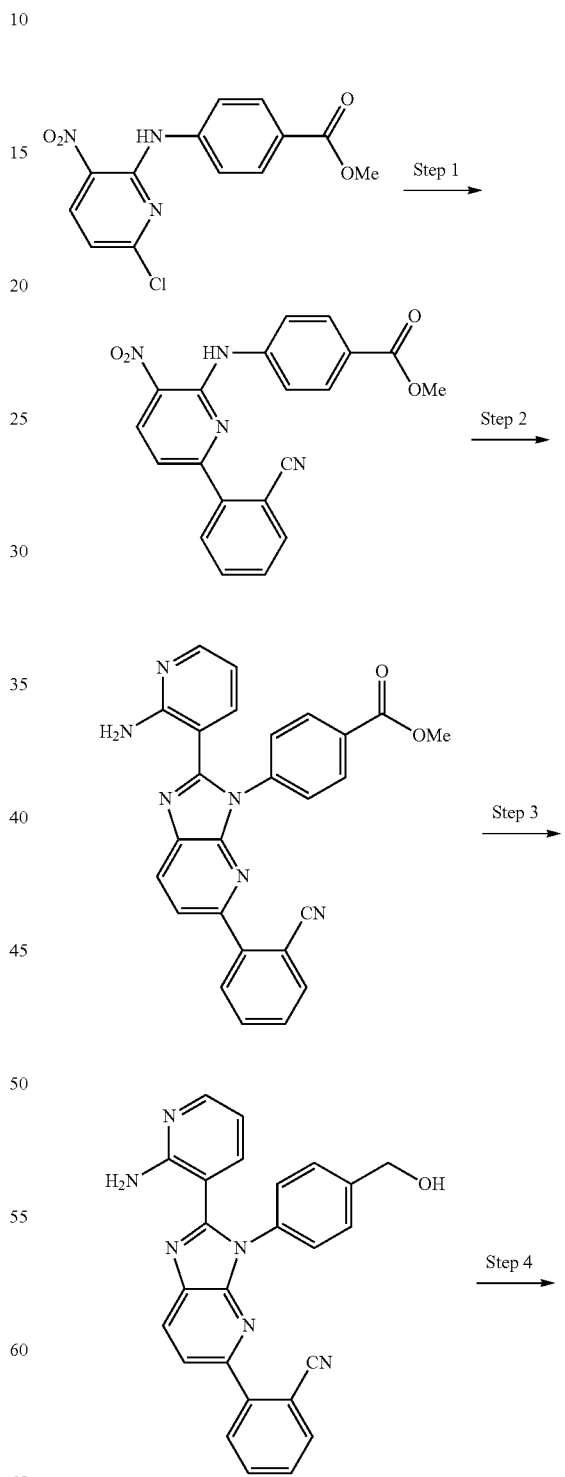

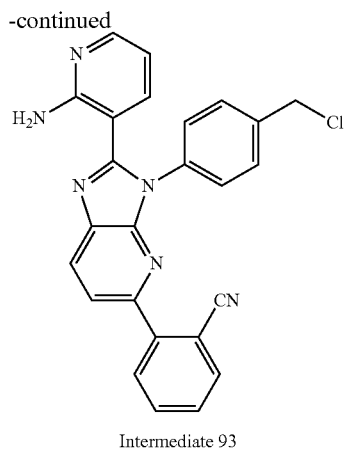

Intermediate 93

Step 1: Methyl 4-((6-(2-cyanophenyl)-3-nitropyridin-2-yl)amino)benzoate

A mixture of methyl 4-((6-chloro-3-nitropyridin-2-yl)amino)benzoate (refer to Intermediate 13 for detail procedures, 5 g, 16.3 mmol), (2-cyanophenyl)boronic acid (2.39 g, 16.3 mmol), $Cs_2CO_3$ (15.9 g, 48.8 mmol), $Pd(dppf)Cl_2$ (2.38 g, 3.25 mmol) in 1,4-dioxane (100 mL) and $H_2O$ (20 mL) was degassed and purged with $N_2$ three times, and then the mixture was stirred at 80° C. for 16 hr under $N_2$ atmosphere. The reaction mixture was diluted with $H_2O$ (100 mL) and extracted with $CH_2Cl_2$ (50 mL×4). The combined organic layers were washed with brine (30 mL×3), dried over $Na_2SO_4$, filtered and concentrated under reduced pressure. The residue was purified by silica gel flash chromatography (Eluent of 20~30% EtOAc in $CH_2Cl_2$) to give methyl 4-((6-(2-cyanophenyl)-3-nitropyridin-2-yl)amino)benzoate (8.5 g, yield: 71%) as a yellow solid. MS: m/z=374.9 $[M+H]^+$.

Step 2: Methyl 4-(2-(2-aminopyridin-3-yl)-5-(2-cyanophenyl)-3H-imidazo[4,5-b]pyridin-3-yl)benzoate To a solution of methyl 4-((6-(2-cyanophenyl)-3-nitropyridin-2-yl)amino)benzoate (8 g, 21.4 mmol), 2-aminonicotinaldehyde (2.61 g, 21.4 mmol) in DMSO (200 mL) was added $Na_2S_2O_4$ (14.9 g, 84.5 mmol). The mixture was stirred at 100° C. for 16 hr. The reaction mixture was diluted with $H_2O$ (100 mL) and extracted with $CH_2Cl_2$ (500 mL×6). The combined organic layers were washed with brine (250 mL×2), dried over $Na_2SO_4$, filtered and concentrated under reduced pressure. The residue was purified by silica gel flash chromatography (Eluent of 20~30% EtOAc in $CH_2Cl_2$) to give methyl 4-(2-(2-aminopyridin-3-yl)-5-(2-cyanophenyl)-3H-imidazo[4,5-b]pyridin-3-yl)benzoate (5.2 g, yield: 51%) as a yellow solid. MS: m/z=446.9 $[M+H]^+$.

Step 3: 2-(2-(2-Aminopyridin-3-yl)-3-(4-(hydroxymethyl)phenyl)-3H-imidazo[4,5-b]pyridin-5-yl)benzonitrile To a solution of methyl 4-(2-(2-aminopyridin-3-yl)-5-(2-cyanophenyl)-3H-imidazo[4,5-b]pyridin-3-yl)benzoate (5 g, 11.2 mmol) in THF (50 mL) was added $LiAlH_4$ (2.5 M, 5.38 mL) at 0° C., then the mixture was stirred at 25° C. for 2 hr. The reaction mixture was quenched with $Na_2SO_4 \cdot 10H_2O$ (10 g) at 0° C. The mixture was filtered and the filter cake was washed by $CH_2Cl_2$ (30 mL×3). The filtrate was concentrated under reduced pressure to give 2-(2-(2-aminopyridin-3-yl)-3-(4-(hydroxymethyl)phenyl)-3H-imidazo[4,5-b]pyridin-5-yl)benzonitrile (4.53 g, yield: 84%) as a yellow solid, which was used to the next step without purification. MS: m/z=421.0 $[M+H]^+$.

Step 4: 2-(2-(2-Aminopyridin-3-yl)-3-(4-(chloromethyl)phenyl)-3H-imidazo[4,5-b]pyridin-5-yl)benzonitrile To a solution of 2-(2-(2-aminopyridin-3-yl)-3-(4-(hydroxymethyl)phenyl)-3H-imidazo[4,5-b]pyridin-5-yl)benzonitrile (4.5 g, 10.8 mmol) in $CH_2Cl_2$ (40 mL) was added $SOCl_2$ (3.84 g, 32.3 mmol) at 0° C. The mixture was stirred at 40° C. for 3 hr. The reaction mixture was concentrated under reduced pressure to give 2-(2-(2-aminopyridin-3-yl)-3-(4-(chloromethyl)phenyl)-3H-imidazo[4,5-b]pyridin-5-yl)benzonitrile (Intermediate 93, 3.5 g, yield: 60%) as a yellow solid. MS: m/z=437.0

Intermediate 94: 1-(2-(2-Aminopyridin-3-yl)-3-(4-(chloromethyl)phenyl)-3H-imidazo[4,5-b]pyridin-5-yl)-1,4-diazepan-5-one

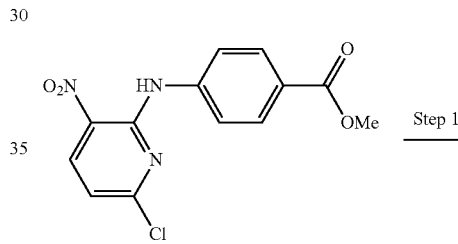

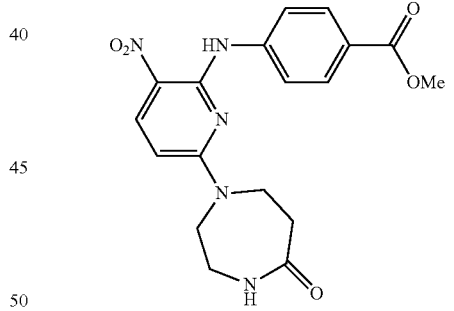

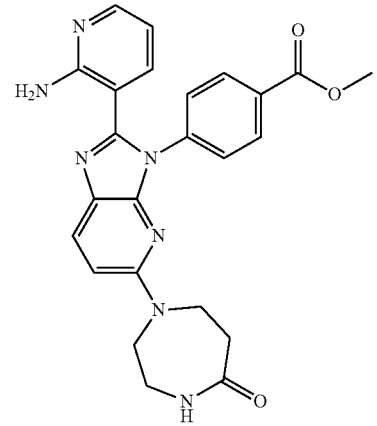

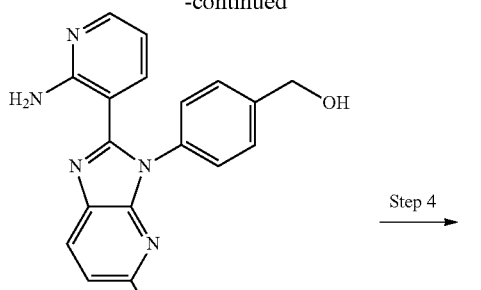

6

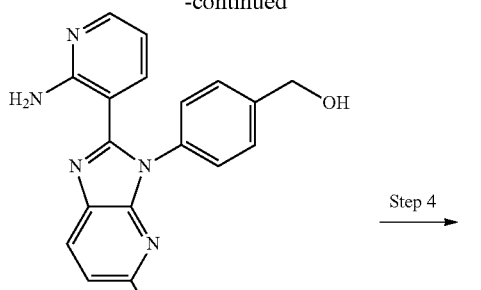

Intermediate 94

Step 1: Methyl 4-((3-nitro-6-(5-oxo-1,4-diazepan-1-yl)pyridin-2-yl)amino)benzoate To a solution of methyl 4-((6-chloro-3-nitropyridin-2-yl)amino)benzoate (refer to Intermediate 13 for detail procedures, 2 g, 6.50 mmol) in CH$_3$CN (50 mL) were added DIEA (2.52 g, 3.40 mL) and 1,4-diazepan-5-one (1.47 g, HCl salt, 9.75 mmol). The mixture was stirred at 90° C. for 12 hr. Water (10 mL) was added to the mixture and the mixture was extracted with EtOAc (20 mL×2). The combined organic layers were washed with brine (10 mL), dried over anhydrous Na$_2$SO$_4$, filtered and concentrated. Methyl 4-((3-nitro-6-(5-oxo-1,4-diazepan-1-yl)pyridin-2-yl)amino)benzoate (2.2 g, yield: 88%) was obtained as a yellow solid, which was used in the next step directly. MS: m/z=386.3 [M+H]$^+$.
$^1$H NMR (400 MHz, Dimethylsulfoxide-d$_6$) 9.29 (br s, 1H), 8.26 (d, J=9.6 Hz, 1H), 7.97 (d, J=8.8 Hz, 2H), 7.78 (d, J=8.4 Hz, 2H), 6.59 (d, J=10.0 Hz, 1H), 3.84 (s, 3H), 3.39-3.18 (m, 4H), 3.16-3.11 (m, 2H), 2.68-2.58 (m, 2H).

Step 2: Methyl 4-(2-(2-aminopyridin-3-yl)-5-(5-oxo-1,4-diazepan-1-yl)-3H-imidazo[4,5-b]pyridin-3-yl)benzoate To a solution of methyl 4-((3-nitro-6-(5-oxo-1,4-diazepan-1-yl)pyridin-2-yl)amino)benzoate (2 g, 5.19 mmol) in DMSO (50 mL) were added 2-aminopyridine-3-carbaldehyde (697 mg, 5.71 mmol) and Na$_2$S$_2$O$_4$ (2.71 g, 15.6 mmol). The mixture was stirred at 100° C. for 12 hr. Water (100 mL) was added to the mixture. The mixture was extracted with CH$_2$Cl$_2$ (50 mL×2). The combined organic layers were washed with brine (10 mL), dried over anhydrous Na$_2$SO$_4$, filtered and concentrated to give methyl 4-(2-(2-aminopyridin-3-yl)-5-(5-oxo-1,4-diazepan-1-yl)-3H-imidazo[4,5-b]pyridin-3-yl)benzoate (2.3 g, yield: 97%) as a yellow solid. MS: m/z=458.2 [M+H]$^+$.

Step 3: 1-(2-(2-Aminopyridin-3-yl)-3-(4-(hydroxymethyl)phenyl)-3H-imidazo[4,5-b]pyridin-5-yl)-1,4-diazepan-5-one Three-necked round 100 mL bottom flask equipped with thermometer was charged with a solution of methyl 4-(2-(2-aminopyridin-3-yl)-5-(5-oxo-1,4-diazepan-1-yl)-3H-imidazo[4,5-b]pyridin-3-yl)benzoate (500 mg, 1.09 mmol) in THF (5 mL). The flask was degassed and purged with N$_2$ three times, then LiAlH$_4$ (133 mg, 3.50 mmol) was added in portions under N$_2$ at 0° C. The mixture was stirred at 0° C. for 0.5 hr, then was warmed to 25° C. After stirring for 2 h under N$_2$, the mixture was quenched with water (10 mL), 15% NaOH (aq. 5 mL) and water (15 ml) at 0° C. The resulting mixture was stirred for 1 hr. The solid was filtered off and the filtrate was concentrated. The crude was purified by silica gel flash silica gel flash chromatography (Eluent of 0~10% MeOH in CH$_2$Cl$_2$) to give 1-(2-(2-aminopyridin-3-yl)-3-(4-(hydroxymethyl)phenyl)-3H-imidazo[4,5-b]pyridin-5-yl)-1,4-diazepan-5-one (50 mg, yield: 11%) as yellow oil. MS: m/z=430.3 [M+H]$^+$.

Step 4: 1-(2-(2-Aminopyridin-3-yl)-3-(4-(chloromethyl)phenyl)-3H-imidazo[4,5-b]pyridin-5-yl)-1,4-diazepan-5-one To a solution of 1-(2-(2-aminopyridin-3-yl)-3-(4-(hydroxymethyl)phenyl)-3H-imidazo[4,5-b]pyridin-5-yl)-1,4-diazepan-5-one (50 mg, 116 μmol) in CH$_2$Cl$_2$ (5 mL) was added SOCl$_2$ (41.6 mg, 25.4 μL). The mixture was stirred at 20° C. for 1 hr. The reaction mixture was concentrated to give 1-(2-(2-aminopyridin-3-yl)-3-(4-(chloromethyl)phenyl)-3H-imidazo[4,5-b]pyridin-5-yl)-1,4-diazepan-5-one (Intermediate 94, 52.2 mg, yield: 100%) as yellow solid. MS: m/z=448.3 [M+H]$^+$.

Intermediate 95: 1-(2-(2-Aminopyridin-3-yl)-3-(4-(chloromethyl)phenyl)-3H-imidazo[4,5-b]pyridin-5-yl)-4-methyl-1,4-diazepan-5-one

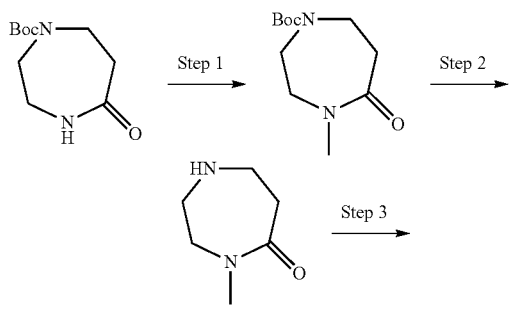

599
-continued

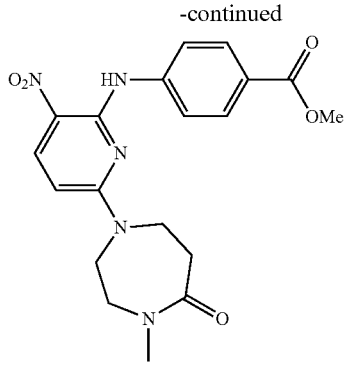

Step 4 →

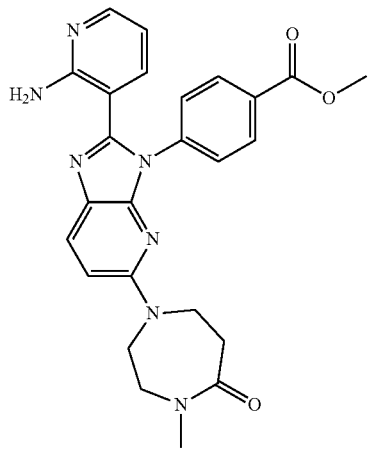

Step 5 →

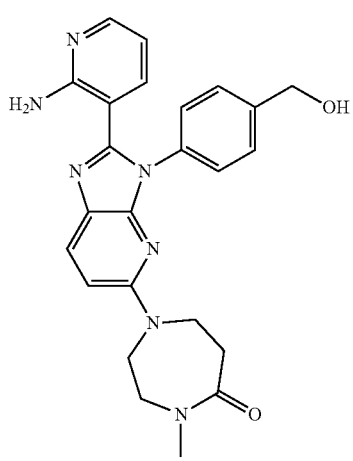

Step 6 →

600
-continued

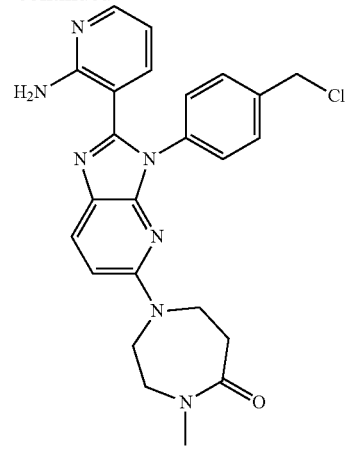

Intermediate 95

Step 1: Tert-butyl 4-methyl-5-oxo-1,4-diazepane-1-carboxylate

To a solution of tert-butyl 5-oxo-1,4-diazepane-1-carboxylate (5 g, 23.3 mmol) in THF (50 mL) were added MeI (4.97 g, 35.0 mmol, 2.18 mL) and NaH (1.87 g, 46.7 mmol, 60% purity) at 0° C. under $N_2$. This mixture was stirred at 25° C. for 3 h. The mixture was quenched with water (10 mL) at 0° C. and then phase was extracted with $CH_2Cl_2$ (20 mL×3). The combined organic phase was washed with brine (30 mL), dried over anhydrous $Na_2SO_4$, filtered and concentrated to give Tert-butyl 4-methyl-5-oxo-1,4-diazepane-1-carboxylate (5.33 g, yield: 100%) as light-yellow oil, which was used next step without purification. $^1H$ NMR (400 MHz, Dimethylsulfoxide-$d_6$) δ 3.51-3.39 (m, 6H), 2.84 (s, 3H), 2.56-2.52 (m, 2H), 1.39 (s,

Step 2: 4-Methyl-1,4-diazepan-5-one

To a solution of tert-butyl 4-methyl-5-oxo-1,4-diazepane-1-carboxylate (5.33 g, 23.4 mmol) in 1,4-dioxane (10 mL) was added HCl/1,4-dioxane (4 M, 40 mL) at 25° C. under $N_2$. This mixture was stirred at 25° C. for 3 hr. The reaction was concentrated. 4-Methyl-1,4-diazepan-5-one (3.84 g, HCl salt, yield: 100%) was obtained as a light-yellow solid, which was used next step without purification. $^1H$ NMR (400 MHz, Dimethylsulfoxide-$d_6$) δ 9.63-9.39 (m, 1H), 3.71-3.63 (m, 2H), 3.22-3.09 (m, 4H), 2.87 (s, 3H), 2.81-2.73 (m, 2H).

Step 3: Methyl 4-((6-(4-methyl-5-oxo-1,4-diazepan-1-yl)-3-nitropyridin-2-yl)amino)benzoate To a solution methyl 4-((6-chloro-3-nitropyridin-2-yl)amino)benzoate (refer to Intermediate 13 for detail procedures, 6.2 g, 20.2 mmol) in DMSO (50 mL) were added DIEA (7.81 g, 10.53 mL) and 4-methyl-1,4-diazepan-5-one (3.65 g, HCl salt, 22.2 mmol). The mixture was stirred at 80° C. for 12 hr. Water (50 mL) was added to the mixture and the mixture was extracted with EtOAc (50 mL×2). The combined organic layers were washed with brine (10 mL), dried over anhydrous $Na_2SO_4$, filtered and concentrated. Methyl 4-((6-(4-methyl-5-oxo-1,4-diazepan-1-yl)-3-nitropyridin-2-yl)amino)benzoate (8.05 g, yield: 100%) was obtained as a light-yellow solid. MS: m/z=400.2 [M+H]$^+$. $^1H$ NMR (400

MHz, Chloroform-d) δ 10.78 (s, 1H), 8.32 (d, J=9.2 Hz, 1H), 8.03 (d, J=8.8 Hz, 2H), 7.62 (d, J=8.4 Hz, 2H), 6.21 (d, J=9.6 Hz, 1H), 3.99-3.94 (m, 2H), 3.92 (s, 3H), 3.88-3.82 (m, 2H), 3.58-3.507 (m, 2H), 3.04 (s, 3H), 2.82-2.76 (m, 2H).

Step 4: Methyl 4-(2-(2-aminopyridin-3-yl)-5-(4-methyl-5-oxo-1,4-diazepan-1-yl)-3H-imidazo[4,5-b]pyridin-3-yl)benzoate To a solution of methyl 4-((6-(4-methyl-5-oxo-1,4-diazepan-1-yl)-3-nitropyridin-2-yl)amino)benzoate (7.99 g, 20 mmol) in DMSO (80 mL) were added Na$_2$S$_2$O$_4$ (10.5 g, 60 mmol) and 2-aminopyridine-3-carbaldehyde (2.44 g, 20 mmol). The mixture was stirred at 100° C. for 12 hr. The reaction was concentrated. Water (100 mL) was added and the aqueous was extracted with CH$_2$Cl$_2$ (200 mL×2). The combined organic layers were dried over anhydrous Na$_2$SO$_4$, filtered and concentrated. Methyl 4-(2-(2-aminopyridin-3-yl)-5-(4-methyl-5-oxo-1,4-diazepan-1-yl)-3H-imidazo[4,5-b]pyridin-3-yl)benzoate (7 g, yield: 74%) was obtained as a yellow solid, which was used in next step without purification. MS: m/z=472.2 [M+H]$^+$. $^1$H NMR (400 MHz, Dimethylsulfoxide-d$_6$) δ 8.09 (d, J=8.8 Hz, 2H), 8.04-7.95 (m, 2H), 7.57 (d, J=8.8 Hz, 2H), 7.30 (d, J=6.8 Hz, 1H), 6.95 (d, J=9.2 Hz, 1H), 6.57 (dd, J=7.6, 5.6 Hz, 1H), 3.89 (s, 3H), 3.80-3.74 (m, 2H), 3.73-3.68 (m, 2H), 3.54-3.44 (m, 2H), 2.82 (s, 3H), 2.64-2.60 (m, 2H).

Step 5: 1-(2-(2-Aminopyridin-3-yl)-3-(4-(hydroxymethyl)phenyl)-3H-imidazo[4,5-b]pyridin-5-yl)-4-methyl-1,4-diazepan-5-one To a solution of methyl methyl 4-(2-(2-aminopyridin-3-yl)-5-(4-methyl-5-oxo-1,4-diazepan-1-yl)-3H-imidazo[4,5-b]pyridin-3-yl)benzoate (100 mg, 212 μmol) in THF (I mL) was added LiAlH$_4$ (24.2 mg, 636 μmol) at 0° C. for 30 min. The mixture was stirred at 0° C. for 1.5 hr. The mixture was diluted with THF (20 mL). Na$_2$SO$_4$ 10H$_2$O was added in portions until no bubbles were formed. The resulting mixture was stirred at 25° C. for 20 min and filtered. The filter cake was washed with THF (20 mL×2), the combined filtrate was concentrated. 1-(2-(2-Aminopyridin-3-yl)-3-(4-(hydroxymethyl)phenyl)-3H-imidazo[4,5-b]pyridin-5-yl)-4-methyl-1,4-diazepan-5-one (82 mg, yield: 87%) was obtained as light-yellow oil, which was used next step without further purification. MS: m/z=444.1 [M+H]$^+$.

Step 6: 1-(2-(2-Aminopyridin-3-yl)-3-(4-(chloromethyl)phenyl)-3H-imidazo[4,5-b]pyridin-5-yl)-4-methyl-1,4-diazepan-5-one To a solution of 1-(2-(2-aminopyridin-3-yl)-3-(4-(hydroxymethyl)phenyl)-3H-imidazo[4,5-b]pyridin-5-yl)-4-methyl-1,4-diazepan-5-one (82 mg, 185 μmol) in CH$_2$Cl$_2$ (1 mL) were added SOCl$_2$ (110 mg, 924 μmol). The mixture was stirred at 25° C. for 12 hr. The reaction was concentrated. 1-(2-(2-Aminopyridin-3-yl)-3-(4-(chloromethyl)phenyl)-3H-imidazo[4,5-b]pyridin-5-yl)-4-methyl-1,4-diazepan-5-one (Intermediate 95, 85.4 mg, yield: 100%) was obtained as a light-yellow solid, which was used for next step without purification. MS: m/z=462.1 [M+H]$^+$.

Intermediate 96: 3-(5-(Cyclohex-1-en-1-yl)-3-(4-(piperazin-1-ylmethyl)phenyl)-3H-imidazo[4,5-b]pyridin-2-yl)pyridin-2-amine

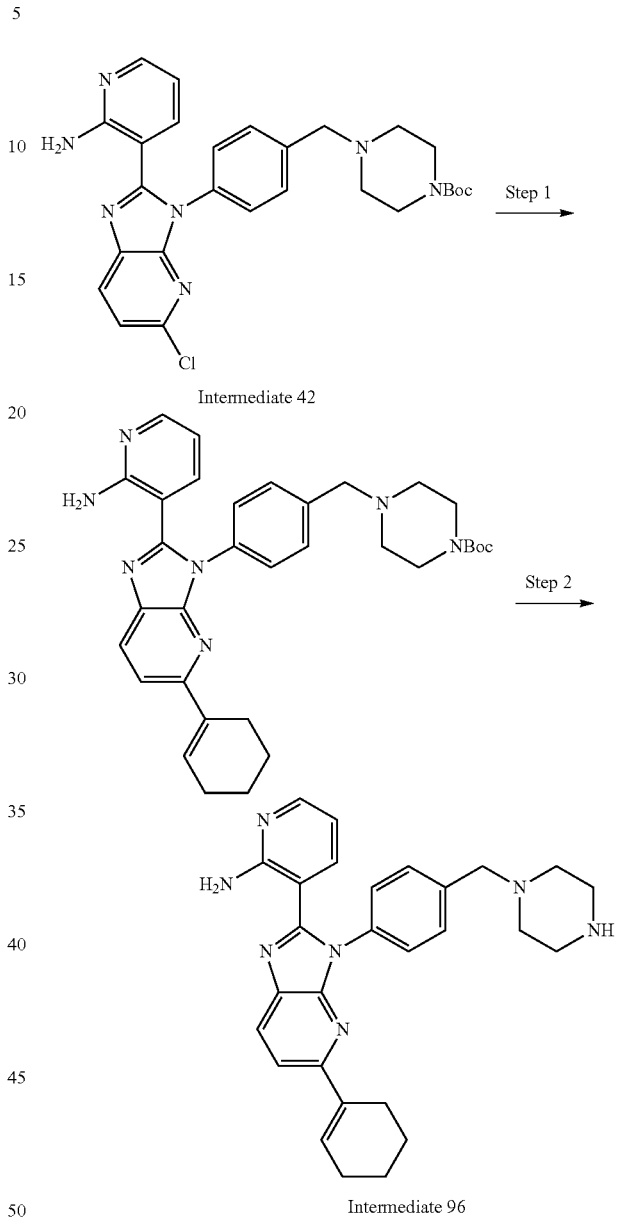

Step 1: Tert-butyl 4-(4-(2-(2-aminopyridin-3-yl)-5-(cyclohex-1-en-1-yl)-3H-imidazo[4,5-b]pyridin-3-yl)benzyl)piperazine-1-carboxylate To a solution of Intermediate 42 (200 mg, 385 μmol) in 1,4-dioxane (5 mL) and H$_2$O (1 mL) were added cyclohex-1-en-1-ylboronic acid (72.7 mg, 577 μmol), K$_2$CO$_3$ (159 mg, 1.15 mmol) and Pd(dppf)Cl$_2$ (28.1 mg, 38.5 μmol) at 25° C. under N$_2$. This mixture was stirred at 100° C. for 5 hr. H$_2$O (5 mL) was added to the mixture. The aqueous phase was extracted with EtOAc (20 mL×3). The combined organic layers were washed with brine (30 mL), dried over anhydrous Na$_2$SO$_4$, filtered and concentrated. The residue was purified by prep-TLC (EtOAc:petroleum ether=2:1) to give tert-butyl 4-(4-(2-(2-aminopyridin-3-yl)-5-(cyclohex-1-en-1-yl)-3H-imidazo[4,5-b]pyridin-3-yl)benzyl)piperazine-1-carboxylate (100 mg, yield: 83%) as a yellow oil. MS: m/z=566.4 [M+H]⁺.

Step 2: 3-(5-(Cyclohex-1-en-1-yl)-3-(4-(piperazin-1-ylmethyl)phenyl)-3H-imidazo[4,5-b]pyridin-2-yl)pyridin-2-amine To a solution of tert-butyl 4-(4-(2-(2-aminopyridin-3-yl)-5-(cyclohex-1-en-1-yl)-3H-imidazo[4,5-b]pyridin-3-yl)benzyl)piperazine-1-carboxylate (79.7 mg, 141 μmol) in 1,4-dioxane (1 mL) was added HCl/1,4-dioxane (4 M, 35.2 L) at 25° C. This mixture was stirred at 25° C. for 3 hr. The mixture was filtrated and concentrated. 3-(5-(Cyclohex-1-en-1-yl)-3-(4-(piperazin-1-ylmethyl)phenyl)-3H-imidazo[4,5-b]pyridin-2-yl)pyridin-2-amine (Intermediate 96, 60 mg, HCl salt, yield: 84%) was obtained as a yellow solid, which was used in the next step directly without purification. MS: m/z=466.2 [M+H]⁺. ¹H NMR (400 MHz, Methanol-d₄) δ 8.16 (d, J=8.4 Hz, 1H), 8.01 (dd, J=6.4, 1.6 Hz, 1H), 7.90 (d, J=8.4 Hz, 2H), 7.85 (dd, J=7.6, 1.4 Hz, 1H), 7.70-7.62 (m, 3H), 6.92 (dd, J=7.6, 6.4 Hz, 1H), 6.75-6.69 (m, 1H), 4.62 (s, 2H), 3.69-3.68 (m, 7H), 3.60-3.59 (m, 1H), 2.56-2.47 (m, 2H), 2.30-2.21 (m, 2H), 1.81-1.64 (m, 4H).

Intermediate 97: 3-(5-(3,6-Dihydro-2H-pyran-4-yl)-3-(4-(piperazin-1-ylmethyl)phenyl)-3H-imidazo[4,5-b]pyridin-2-yl)pyridin-2-amine

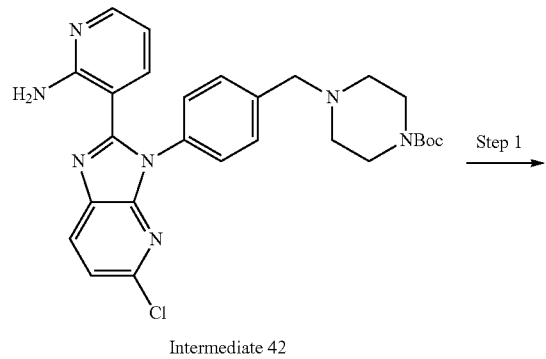

Intermediate 42

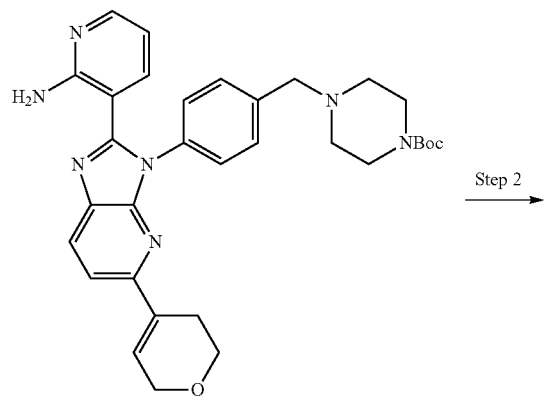

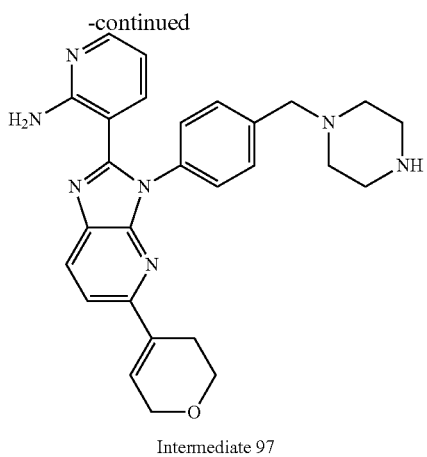

Intermediate 97

Step 1: Tert-butyl 4-(4-(2-(2-aminopyridin-3-yl)-5-(3,6-dihydro-2H-pyran-4-yl)-3H-imidazo[4,5-b]pyridin-3-yl)benzyl)piperazine-1-carboxylate To a solution of Intermediate 42 (200 mg, 385 μmol) in 1,4-dioxane (5 mL) and H₂O (1 mL) were added 2-(3,6-dihydro-2H-pyran-4-yl)-4,4,5,5-tetramethyl-1,3,2-dioxaborolane (121 mg, 577 μmol), K₂CO₃ (159 mg, 1.15 mmol) and Pd(dppf)Cl₂ (28.1 mg, 38.5 μmol) at 25° C. under N₂. This mixture was stirred at 100° C. for 5 hr. The water (5 mL) was added to the mixture. The aqueous phase was extracted with EtOAc (20 mL×3). The combined organic layers were washed with brine (30 mL), dried over anhydrous Na₂SO₄, filtered and concentrated. The residue was purified by prep-TLC (EtOAc:petroleum ether=2:1) to give tert-butyl 4-(4-(2-(2-aminopyridin-3-yl)-5-(3,6-dihydro-2H-pyran-4-yl)-3H-imidazo[4,5-b]pyridin-3-yl)benzyl)piperazine-1-carboxylate (45 mg, yield: 50%) as an off-white solid. MS: m/z=568.3 [M+H]⁺. ¹H NMR (400 MHz, Methanol-d₄) δ 8.08 (d, J=8.4 Hz, 1H), 7.97 (dd, J=4.8, 1.6 Hz, 1H), 7.62 (d, J=8.4 Hz, 1H), 7.51 (d, J=8.0 Hz, 2H), 7.39 (d, J=8.4 Hz, 2H), 7.29 (dd, J=8.0, 2.0 Hz, 1H), 6.72-6.65 (m, 1H), 6.47 (dd, J=8.0, 5.2 Hz, 1H), 4.36-4.28 (m, 2H), 3.90 (t, J=5.6 Hz, 2H), 3.62 (s, 2H), 3.46-3.45 (m, 4H), 2.67-2.60 (m, 2H), 2.46 (t, J=4.8 Hz, 4H), 1.46 (s, 9H).

Step 2: 3-(5-(3,6-Dihydro-2H-pyran-4-yl)-3-(4-(piperazin-1-ylmethyl)phenyl)-3H-imidazo[4,5-b]pyridin-2-yl)pyridin-2-amine To a solution of tert-butyl 4-(4-(2-(2-aminopyridin-3-yl)-5-(3,6-dihydro-2H-pyran-4-yl)-3H-imidazo[4,5-b]pyridin-3-yl)benzyl)piperazine-1-carboxylate (45.0 mg, 79.3 μmol) in 1,4-dioxane (1 mL) was added HC/1,4-dioxane (4 M, 19.8 μL) at 25° C. This mixture was stirred at 25° C. for 3 hr. The mixture was filtrated and concentrated. 3-(5-(3,6-Dihydro-2H-pyran-4-yl)-3-(4-(piperazin-1-ylmethyl)phenyl)-3H-imidazo[4,5-b]pyridin-2-yl)pyridin-2-amine (Intermediate 97, 20.8 mg, HCl salt, yield: 52%) was obtained as a yellow solid, which was used in the next step directly without purification. MS: m/z=468.2 [M+H]⁺. ¹H NMR (400 MHz, Methanol-d₄) δ 8.21 (d, J=8.4 Hz, 1H), 8.01 (dd, J=6.4, 1.2 Hz, 1H), 7.93-7.83 (m, 3H), 7.75-7.62 (m, 3H), 6.96-6.87 (m, 1H), 6.75-6.74 (m, 1H), 4.62 (s, 2H), 4.39-4.29 (m, 2H), 3.90 (t, J=5.2 Hz, 2H), 3.69-3.68 (m, 8H), 2.68-2.57 (m, 2H).

Intermediate 98: 3-(2-(2-Aminopyridin-3-yl)-3-(4-(piperazin-1-ylmethyl)phenyl)-3H-imidazo[4,5-b]pyridin-5-yl)benzonitrile

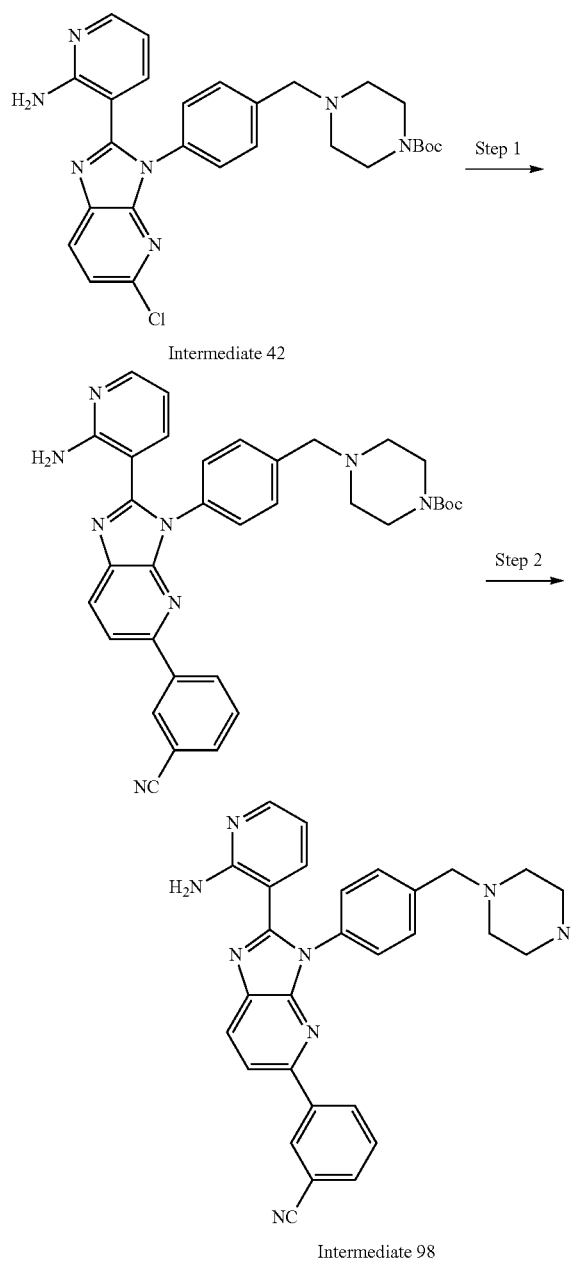

Step 1: Tert-butyl 4-(4-(2-(2-aminopyridin-3-yl)-5-(3-cyanophenyl)-3H-imidazo[4,5-b]pyridin-3-yl)benzyl)piperazine-1-carboxylate A mixture of Intermediate 42 (220 mg, 423 μmol), (3-cyanophenyl)boronic acid (68.4 mg, 465 μmol), Cs₂CO₃ (414 mg, 1.27 mmol), Pd(dppf)Cl₂ (155 mg, 212 μmol) in 1,4-dioxane (5 mL) and H₂O (1 mL) was degassed and purged with N₂ three times, and then the mixture was stirred at 100° C. for 16 hr under N₂ atmosphere. The reaction mixture was filtered at 25° C. Then it was diluted with H₂O (20 mL) and extracted with CH₂Cl₂ (20 mL×3). The combined organic layers were washed with brine (30 mL), dried over Na₂SO₄, filtered and concentrated under reduced pressure. After purified by silica gel flash chromatography (Eluent of 0~30% EtOAc in petroleum ether), tert-butyl 4-(4-(2-(2-aminopyridin-3-yl)-5-(3-cyanophenyl)-3H-imidazo[4,5-b]pyridin-3-yl)benzyl)piperazine-1-carboxylate (240 mg, yield: 97%) was obtained as a brown solid. MS: m/z=587.4 [M+H]⁺.

Step 2: 3-(2-(2-Aminopyridin-3-yl)-3-(4-(piperazin-1-ylmethyl)phenyl)-3H-imidazo[4,5-b]pyridin-5-yl)benzonitrile To a solution of tert-butyl 4-(4-(2-(2-aminopyridin-3-yl)-5-(3-cyanophenyl)-3H-imidazo[4,5-b]pyridin-3-yl)benzyl)piperazine-1-carboxylate (240 mg, 409 μmol) in 1,4-dioxane (3 mL) was added 4 M HCl in 1,4-dioxane (3 mL) at 25° C. The mixture was stirred at 25° C. for 16 hr. The reaction mixture was filtered and the collected solid was washed with 1,4-dioxane (2 mL×2) and dried in vacuo to give 3-(2-(2-aminopyridin-3-yl)-3-(4-(piperazin-1-ylmethyl)phenyl)-3H-imidazo[4,5-b]pyridin-5-yl)benzonitrile (Intermediate 98, 203 mg HCl salt, yield: 95%) as a yellow solid. MS: m/z=487.2 [M+H]⁺. ¹H NMR (400 MHz, Methanol-d₄) δ 8.43-8.34 (m, 3H), 8.11 (d, J=8.4 Hz, 1H), 8.03 (d, J=5.6 Hz, 1H), 7.96 (d, J=8.4 Hz, 2H), 7.90 (d, J=7.6 Hz, 1H), 7.79-7.73 (m, 3H), 7.68-7.63 (m, 1H), 6.96-6.90 (m, 1H), 3.70-3.68 (m, 6H), 3.67-3.65 (m, 4H).

Intermediate 99: 5-(2-(2-aminopyridin-3-yl)-3-(4-(piperazin-1-ylmethyl)phenyl)-3H-imidazo[4,5-b]pyridin-5-yl)pyridin-2(1H)-one

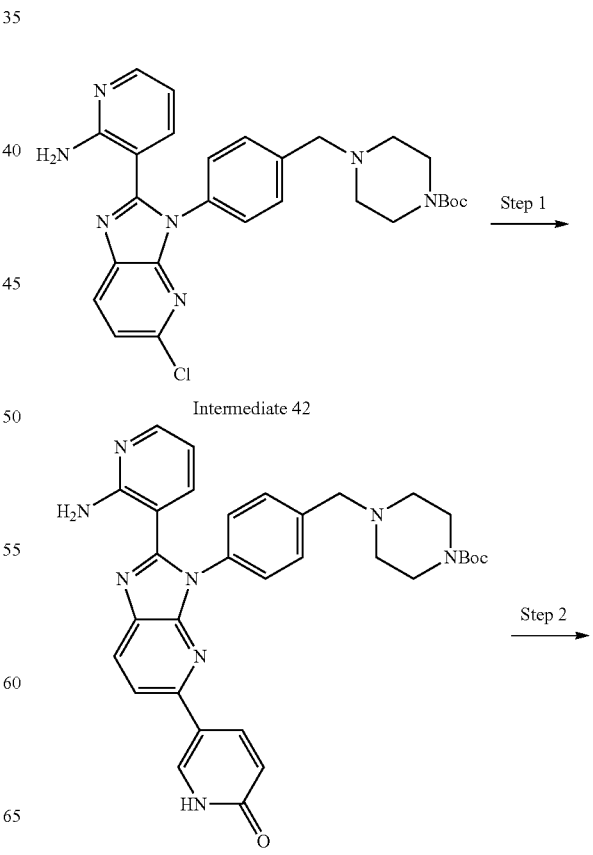

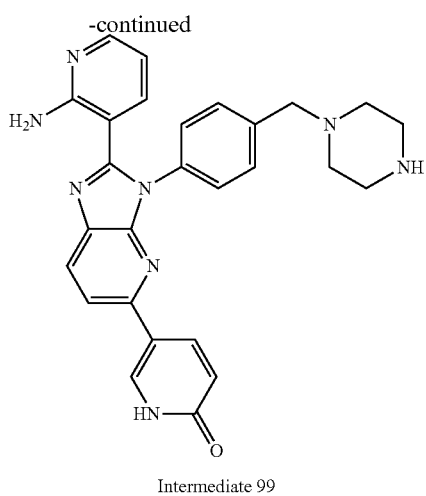

Intermediate 99

Step 1: Tert-butyl 4-(4-(2-(2-aminopyridin-3-yl)-5-(6-oxo-1,6-dihydropyridin-3-yl)-3H-imidazo[4,5-b]pyridin-3-yl)benzyl)piperazine-1-carboxylate A mixture of Intermediate 42 (200 mg, 385 μmol), (6-oxo-1,6-dihydropyridin-3-yl)boronic acid (54 mg, 385 μmol), Cs$_2$CO$_3$ (376 mg, 1.15 mmol), Pd(dppf)Cl$_2$ (31.4 mg, 38.5 μmol) in 1,4-dioxane (2.5 mL) and H$_2$O (0.5 mL) was degassed and purged with N$_2$ three times, and then the mixture was stirred at 100° C. for 16 hr under N$_2$ atmosphere. The reaction mixture was filtered at 25° C., and then diluted with H$_2$O (10 mL) and extracted with CH$_2$Cl$_2$ (10 mL×3). The combined organic layers were washed with brine (30 mL), dried over Na$_2$SO$_4$, filtered and concentrated under reduced pressure. After purified by silica gel flash chromatography (Eluent of 0~10% CH$_2$Cl$_2$ in MeOH), tert-butyl 4-(4-(2-(2-aminopyridin-3-yl)-5-(6-oxo-1,6-dihydropyridin-3-yl)-3H-imidazo[4,5-b]pyridin-3-yl)benzyl)piperazine-1-carboxylate (60 mg, yield: 22%) was obtained as a yellow solid. MS: m/z=579.2 [M+H]$^+$.

Step 2: 5-(2-(2-Aminopyridin-3-yl)-3-(4-(piperazin-1-ylmethyl)phenyl)-3H-imidazo[4,5-b]pyridin-5-yl)pyridin-2(1H)-one To a solution of tert-butyl 4-(4-(2-(2-aminopyridin-3-yl)-5-(6-oxo-1,6-dihydropyridin-3-yl)-3H-imidazo[4,5-b]pyridin-3-yl)benzyl)piperazine-1-carboxylate (60 mg, 104 μmol) in 1,4-dioxane (2 mL) was added 4 M HCl in 1,4-dioxane (1 mL) at 25° C. The mixture was stirred at 25° C. for 16 hr. The reaction mixture was then filtered and the collected solid was washed with 1,4-dioxane (5 mL×2) and dried in vacuo to give 5-(2-(2-aminopyridin-3-yl)-3-(4-(piperazin-1-ylmethyl)phenyl)-3H-imidazo[4,5-b]pyridin-5-yl)pyridin-2(1H)-one (Intermediate 99, 48.6 mg, yield: 89%) as a yellow solid. MS: m/z=479.2 [M+H]$^+$. $^1$H NMR (400 MHz, Methanol-d$_4$) δ 8.76 (d, J=9.2 Hz, 1H), 8.61 (s, 1H), 8.37 (d, J=8.4 Hz, 1H), 8.01-8.07 (m, 2H), 7.95 (d, J=8.0 Hz, 2H), 7.90 (d, J=7.2 Hz, 1H), 7.73 (d, J=7.6 Hz, 2H), 7.08 (d, J=9.2 Hz, 1H), 6.94 (t, J=6.8 Hz, 1H), 4.67 (s, 2H), 3.82-3.64 (m, 8H).

Intermediate 100: 2-(3-(4-((4-Aminopiperidin-1-yl)methyl)phenyl)-2-(2-aminopyridin-3-yl)-3H-imidazo[4,5-b]pyridin-5-yl)benzonitrile

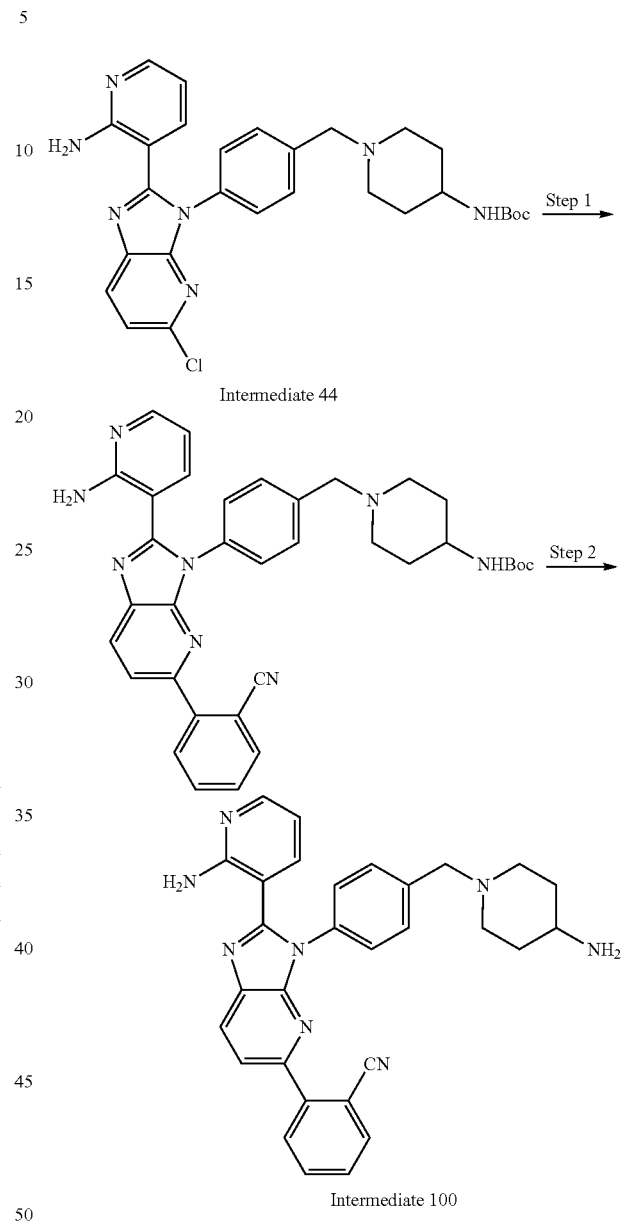

Intermediate 100

Step 1: Tert-butyl (1-(4-(2-(2-aminopyridin-3-yl)-5-(2-cyanophenyl)-3H-imidazo[4,5-b]pyridin-3-yl)benzyl)piperidin-4-yl)carbamate A mixture of Intermediate 44 (100 mg, 187 μmol), (2-cyanophenyl)boronic acid (55 mg, 375 μmol) in DMF (2 mL), cataCXiumAPdG$_3$ (68 mg, 94 μmol), K$_3$PO$_4$ (80 mg, 375 μmol), PCy$_3$ (5 mg, 19 μmol) in 1,4-dioxane (2.5 mL) and H$_2$O (0.5 mL) was degassed and purged with N$_2$ three times, and then the mixture was stirred at 120° C. for 16 hr under N$_2$ atmosphere. The reaction mixture was poured into H$_2$O (15 mL), extracted with EtOAc (60 mL×2). The combined organic layers were dried over anhydrous Na$_2$SO$_4$, filtered and concentrated under reduced pressure. The residue was purified by silica gel flash chromatography (Eluent of 0~6%

MeOH in CH₂Cl₂) to give tert-butyl (1-(4-(2-(2-aminopyridin-3-yl)-5-(2-cyanophenyl)-3H-imidazo[4,5-b]pyridin-3-yl)benzyl)piperidin-4-yl)carbamate (76 mg, yield: 68%) as a yellow solid. MS: m/z=601.2 [M+H]⁺.

Step 2: 2-(3-(4-((4-Aminopiperidin-1-yl)methyl)phenyl)-2-(2-aminopyridin-3-yl)-3H-imidazo[4,5-b]pyridin-5-yl)benzonitrile To a solution of tert-butyl (1-(4-(2-(2-aminopyridin-3-yl)-5-(2-cyanophenyl)-3H-imidazo[4,5-b]pyridin-3-yl)benzyl)piperidin-4-yl)carbamate (152 mg, 253 μmol) in CH₂Cl₂ (2 mL) was added 4 M HCl in 1,4-dioxane (2.0 mL). The mixture was stirred at 25° C. for 1 hr. The reaction mixture was concentrated. The crude was triturated with CH₂Cl₂ at 25° C. for 30 min. 2-(3-(4-((4-Aminopiperidin-1-yl)methyl)phenyl)-2-(2-aminopyridin-3-yl)-3H-imidazo[4,5-b]pyridin-5-yl)benzonitrile (Intermediate 100, 114 mg, HCl salt, yield: 84%) was obtained as a yellow solid. MS: m/z=501.2 [M+H]⁺. ¹H NMR (400 MHz, Methanol-d₄) δ 8.42 (d, J=8.0 Hz, 1H), 8.06-8.01 (m, 1H), 7.96-7.90 (m, 3H), 7.85-7.83 (m, 3H), 7.80-7.75 (m, 3H), 7.62-7.55 (m, 1H), 6.88 (t, J=7.2 Hz, 1H), 3.69-3.65 (m, 2H), 3.62-3.35 (m, 2H), 3.29-3.21 (m, 3H), 2.30-2.26 (m, 2H), 2.12-2.01 (m, 2H).

Intermediate 101: 3-(3-(4-(((3aR,6aS)-hexahydropyrrolo[3,4-c]pyrrol-2(1H)-yl)methyl)phenyl)-5-phenyl-3H-imidazo[4,5-b]pyridin-2-yl)pyridin-2-amine

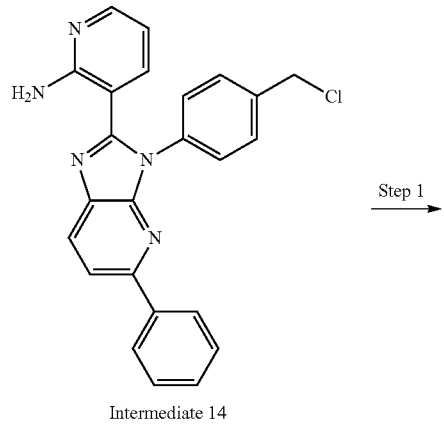

Intermediate 14

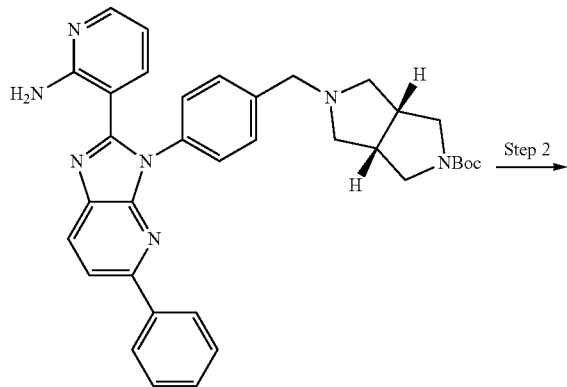

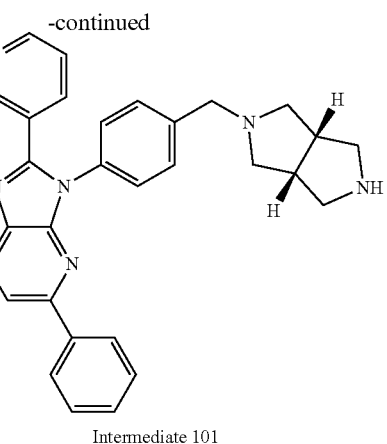

Intermediate 101

Step 1: Tert-butyl (3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrole-2(1H)-carboxylate To a solution of Intermediate 14 (4.6 g, 11.2 mmol) and tert-butyl (3aR,6aS)-2,3,3a,4,6,6a-hexahydro-1H-pyrrolo[3,4-c]pyrrole-5-carboxylate (2.61 g, 12.3 mmol) in DMF (60 mL) were added NaI (502 mg, 3.35 mmol) and K₂CO₃ (3.09 g, 22.3 mmol) in one portion at 25° C. Then the mixture was stirred at 80° C. for 12 hr. The reaction mixture was poured into water (100 mL) at 25° C., then extracted with EtOAc (100 mL×3). The combined organic layers were washed with brine (150 mL), dried over anhydrous Na₂SO₄, filtered and concentrated under reduced pressure. The residue was purified by silica gel flash chromatography (Eluent of 0~6% MeOH in CH₂Cl₂) to give tert-butyl (3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrole-2(1H)-carboxylate (3.6 g, yield: 55%) as a yellow solid. MS: m/z=588.4 [M+H]⁺. ¹H NMR (400 MHz, Dimethylsulfoxide-d₆) δ 8.27 (d, J=8.4 Hz, 1H), 8.06-7.96 (m, 4H), 7.50-7.36 (m, 7H), 7.16 (dd, J=7.6, 1.6 Hz, 1H), 7.03 (br s, 2H), 6.38 (dd, J=7.6, 4.8 Hz, 1H), 3.65 (s, 2H), 3.51-3.41 (m, 2H), 3.17-3.10 (m, 2H), 2.76-2.75 (m, 2H), 2.59-2.53 (m, 2H), 2.45-2.39 (m, 2H), 1.39 (s, 9H).

Step 2: 3-(3-(4-(((3aR,6aS)-hexahydropyrrolo[3,4-c]pyrrol-2(1H)-yl)methyl)phenyl)-5-phenyl-3H-imidazo[4,5-b]pyridin-2-yl)pyridin-2-amine To a solution of tert-butyl (3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrole-2(1H)-carboxylate (50 mg, 85.1 μmol) in 1,4-dioxane (2 mL) was added HCl/1,4-dioxane (4 M, 212 μL). The reaction mixture was stirred at 20° C. for 12 hr. The mixture was quenched with sat. NaHCO₃ (10 mL) and extracted with CH₂Cl₂ (10 mL×2). The combined organic layers were washed with brine (10 mL), dried over anhydrous Na₂SO₄, filtered and concentrated. 3-(3-(4-(((3aR,6aS)-Hexahydropyrrolo[3,4-c]pyrrol-2(1H)-yl)methyl)phenyl)-5-phenyl-3H-imidazo[4,5-b]pyridin-2-yl)pyridin-2-amine (Intermediate 101, 35.4 mg, yield: 85%) was obtained as an off-white solid. MS: m/z=488.2 [M+H]⁺. ¹H NMR (400 MHz, Dimethylsulfoxide-d₆) δ 27 (d, J=8.0 Hz, 1H), 8.04-7.97 (m, 4H), 7.49-7.44 (m, 5H), 7.43-7.37 (m, 2H), 7.16 (dd, J=7.6, 1.6 Hz, 1H), 7.04 (br s, 2H), 6.38 (dd, J=7.6, 4.8 Hz, 1H), 3.60 (s, 2H), 2.85-2.76 (m, 2H), 2.58-2.51 (m, 7H), 2.31-2.26 (m, 2H).

Intermediate 102: 3-(3-(4-(((3aR,6aR)-hexahydropyrrolo[3,4-c]pyrrol-2(1H)-yl)methyl)phenyl)-5-phenyl-3H-imidazo[4,5-b]pyridin-2-yl)pyridin-2-amine

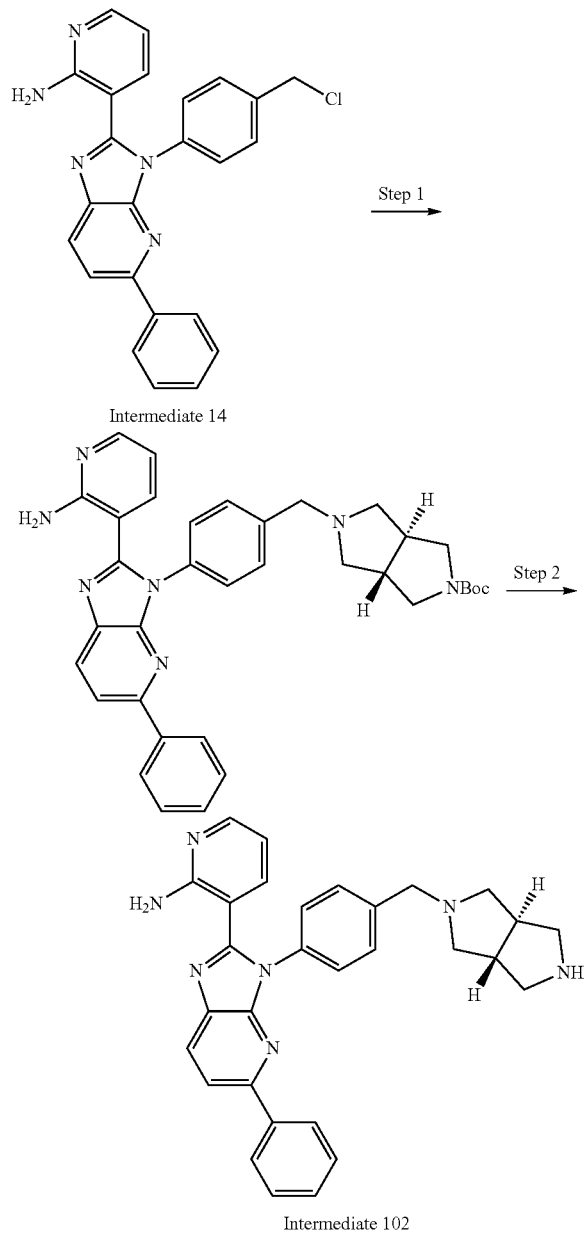

Step 1: Tert-butyl (3aS,6aS)-5-(4-(2-(2-aminopyridin-3-yl)-5-phenyl-3H-imidazo[4,5-b]pyridin-3-yl)benzyl)hexahydropyrrolo[3,4-c]pyrrole-2(1H)-carboxylate To a solution of Intermediate 14 (200 mg, 486 µmol) in DMF (4 mL) were added K₂CO₃ (201 mg, 1.46 mmol), NaI (21.8 mg, 146 µmol) and tert-butyl (3aS,6aS)-hexahydropyrrolo[3,4-c]pyrrole-2(1H)-carboxylate (134 mg, 631 µmol). The mixture was stirred at 25° C. for 16 hr. The reaction mixture was quenched with H₂O (10 mL) at 25° C., and then extracted with EtOAc (20 mL×3). The combined organic layers were washed with brine (20 mL), dried over Na₂SO₄, filtered and concentrated under reduced pressure. After purified by prep-TLC (CH₂Cl₂: MeOH=10:1), tert-butyl (3aS,6aS)-5-(4-(2-(2-aminopyridin-3-yl)-5-phenyl-3H-imidazo[4,5-b]pyridin-3-yl)benzyl)hexahydropyrrolo[3,4-c]pyrrole-2(1H)-carboxylate (100 mg, yield: 32%) was obtained as a yellow solid. MS: m/z=588.3 [M+H]⁺.

Step 2: 3-(3-(4-(((3aR,6aR)-Hexahydropyrrolo[3,4-c]pyrrol-2(1H)-yl)methyl)phenyl)-5-phenyl-3H-imidazo[4,5-b]pyridin-2-yl)pyridin-2-amine To a solution of tert-butyl (3aS,6aS)-5-(4-(2-(2-aminopyridin-3-yl)-5-phenyl-3H-imidazo[4,5-b]pyridin-3-yl)benzyl)hexahydropyrrolo[3,4-c]pyrrole-2(1H)-carboxylate (100 mg, 170 µmol) in 1,4-dioxane (2 mL) was added 4 M HCl in 1,4-dioxane (2 mL). The mixture was stirred at 25° C. for 1 hr. The reaction was concentrated under reduced pressure to give 3-(3-(4-(((3aR,6aR)-hexahydropyrrolo[3,4-c]pyrrol-2(1H)-yl)methyl)phenyl)-5-phenyl-3H-imidazo[4,5-b]pyridin-2-yl)pyridin-2-amine (Intermediate 102, 30 mg, HCl salt, yield: 33%) as a yellow solid. MS: m/z=488.3 [M+H]⁺. ¹H NMR (400 MHz, Dimethylsulfoxide-d₆) δ 12.14-11.98 (m, 1H), 9.92-9.78 (m, 1H), 9.73-9.54 (m, 1H), 8.37 (d, J=8.8 Hz, 1H), 8.33-8.19 (m, 1H), 8.13 (dd, J=6.0, 1.2 Hz, 1H), 8.09-8.04 (m, 3H), 7.86 (d, J=8.4 Hz, 2H), 7.81-7.76 (m, 1H), 7.66 (d, J=8.0 Hz, 2H), 7.51-7.41 (m, 3H), 6.89-6.83 (m, 1H), 4.66-4.51 (m, 2H), 3.72-3.63 (m, 2H), 3.20-3.10 (m, 2H), 3.04-2.93 (m, 2H), 2.85-2.76 (m, 1H), 2.64-2.57 (m, 1H), 2.46-2.33 (m, 2H).

Intermediate 103: 4-((3aR,6aR)-Hexahydropyrrolo[3,4-c]pyrrol-2(1H)-yl)pyrimidine-2-carbonitrile

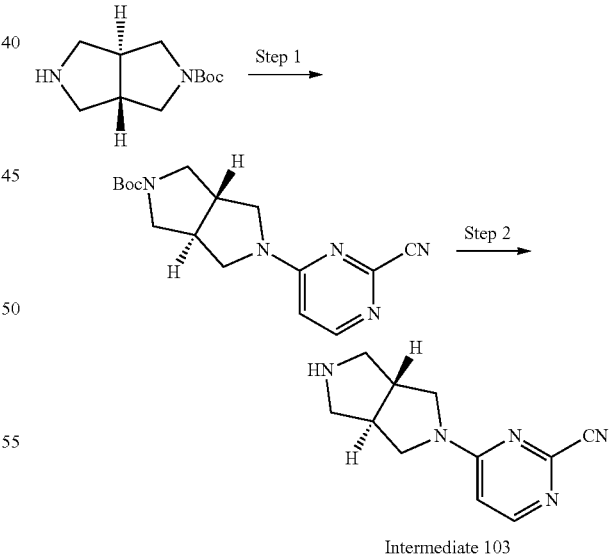

Step 1: Tert-butyl (3aS,6aS)-5-(2-cyanopyrimidin-4-yl)hexahydropyrrolo[3,4-c]pyrrole-2(1H)-carboxylate To a mixture of tert-butyl (3aS,6aS)-hexahydropyrrolo[3,4-c]pyrrole-2(1H)-carboxylate (300 mg, 1.41 mmol) and 4-chloropyrimidine-2-carbonitrile (197 mg, 1.41 mmol) in NMP (4 mL) was added DIEA (547 mg, 4.24 mmol, 738 μL). The mixture was stirred at 60° C. for 1 hr. H₂O (10 mL) was added and the reaction mixture was filtrated. The filtration cake was dried to give tert-butyl (3aS,6aS)-5-(2-cyanopyrimidin-4-yl)hexahydropyrrolo[3,4-c]pyrrole-2(1H)-carboxylate (230 mg, yield: 52%) as a white solid. MS: m/z=316.0 [M+H]⁺. ¹H NMR (400 MHz, Dimethylsulfoxide-d₆) δ 24 (d, J=6.4 Hz, 1H), 6.76 (d, J=6.4 Hz, 1H), 3.91-3.80 (m, 1H), 3.70-3.60 (m, 1H), 3.57-3.49 (m, 2H), 3.18-3.10 (m, 2H), 3.08-2.96 (m, 2H), 2.43-2.22 (m, 2H), 1.41 (s, 9H).

Step 2: 4-((3aR,6aR)-Hexahydropyrrolo[3,4-c]pyrrol-2(1H)-yl)pyrimidine-2-carbonitrile To a mixture of tert-butyl (3aS,6aS)-5-(2-cyanopyrimidin-4-yl)hexahydropyrrolo[3,4-c]pyrrole-2(1H)-carboxylate (100 mg, 317 μmol) in CH₂Cl₂ (3 mL) was added TFA (767 mg, 0.5 mL), the mixture was stirred at 20° C. for 1 hr. The mixture was concentrated to give 4-((3aR,6aR)-hexahydropyrrolo[3,4-c]pyrrol-2(1H)-yl)pyrimidine-2-carbonitrile (Intermediate 103, 104 mg, TFA salt, yield: 100%) as yellow oil. MS: m/z=215.8 [M+H]⁺.

Intermediate 105: 5-(2-(2-Aminopyridin-3-yl)-3-(4-(chloromethyl)phenyl)-3H-imidazo[4,5-b]pyridin-5-yl)-1-methylpyridin-2(1H)-one

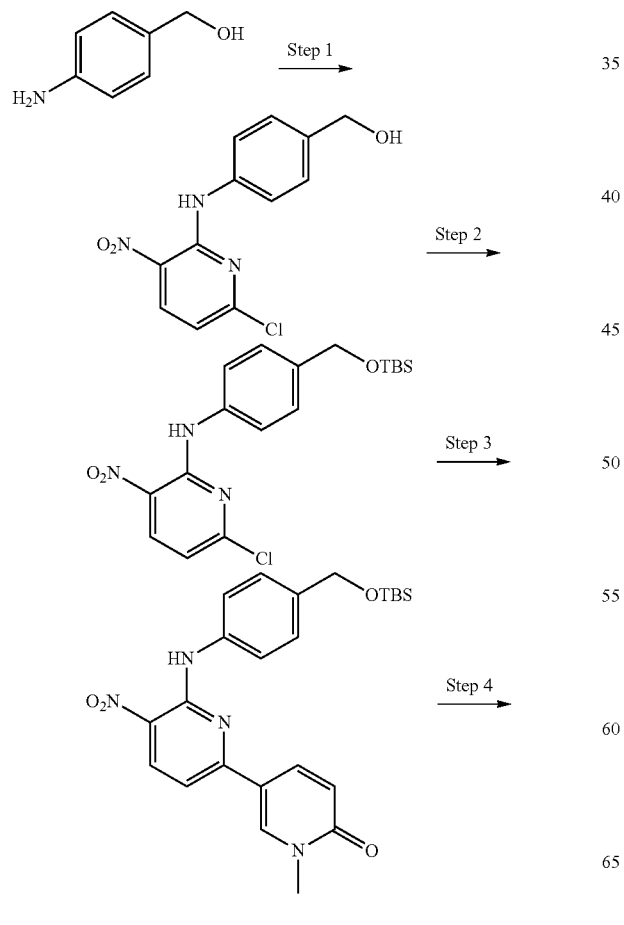

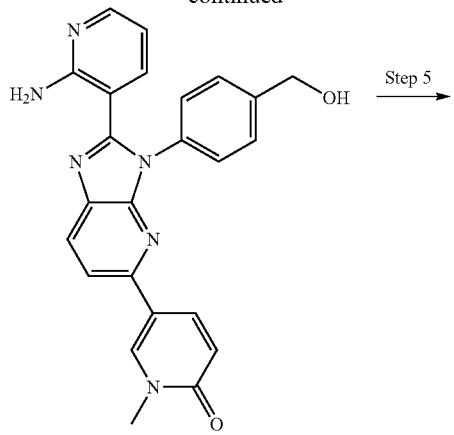

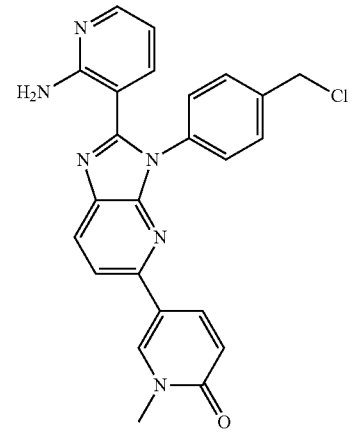

Intermediate 105

Step 1: (4-((6-Chloro-3-nitropyridin-2-yl)amino)phenyl)methanol

To a mixture of (4-aminophenyl)methanol (5 g, 40.6 mmol) and 2,6-dichloro-3-nitro-pyridine (7.84 g, 40.6 mmol) in THF (70 mL) was added DIEA (10.5 g, 81.2 mmol, 14.1 mL). The mixture was stirred at 80° C. for 1 hr. The mixture was concentrated to give (4-((6-chloro-3-nitropyridin-2-yl)amino)phenyl)methanol (11.36 g, yield: 100%) as a yellow oil. MS: m/z=279.8 [M+H]⁺.

Step 2: N-(4-(((tert-butyldimethylsilyl)oxy)methyl)phenyl)-6-chloro-3-nitropyridin-2-amine To a mixture of (4-((6-chloro-3-nitropyridin-2-yl)amino)phenyl)methanol (1 g, 3.58 mmol) in CH₂Cl₂ (10 mL) were added imidazole (365 mg, 5.36 mmol) and TBSCl (701 mg, 4.65 mmol). The mixture was stirred at 20° C. for 1 hr. The mixture was diluted with H₂O (50 mL) and extracted with CH₂Cl₂ (50 mL×2). The combined organic layers were washed with brine (20 mL), dried over Na₂SO₄, filtered and concentrated to give N-(4-(((tert-butyldimethylsilyl)oxy)methyl)phenyl)-6-chloro-3-nitropyridin-2-amine (1.1 g, yield: 78%) as a yellow solid. MS: m/z=394.0 [M+H]⁺. ¹H NMR (400 MHz, Dimethylsulfoxide-d₆) δ 10.12 (s, 1H), 8.54 (d, J=8.8 Hz, 1H), 7.59-7.52 (m, 2H), 7.36-7.30 (m, 2H), 7.00 (d, J=8.4 Hz, 1H), 4.71 (s, 2H), 0.91 (s, 9H), 0.09 (s, 6H).

Step 3: 6-((4-(((Tert-butyldimethylsilyl)oxy)methyl)phenyl)amino)-1'-methyl-5-nitro-[2,3'-bipyridin]-6'(1'H)-one To a mixture of N-(4-(((tert-butyldimethylsilyl)oxy)methyl)phenyl)-6-chloro-3-nitropyridin-2-amine (900 mg, 2.28 mmol) and (1-methyl-6-oxo-1,6-dihydropyridin-3-yl)boronic acid (591 mg, 2.51 mmol) in 1,4-dioxane (10 mL) and H$_2$O (2 mL) were added Cs$_2$CO$_3$ (2.23 g, 6.85 mmol) and Pd(dppf)Cl$_2$ (167 mg, 228 μmol). The mixture was stirred at 100° C. for 12 hr under N$_2$ atmosphere. The mixture was diluted with EtOAc (100 mL) and H$_2$O (100 mL) and filtered. The filtration cake was concentrated to give 6-((4-(((tert-butyldimethylsilyl)oxy)methyl)phenyl)amino)-1'-methyl-5-nitro-[2,3'-bipyridin]-6'(1'H)-one (600 mg, yield: 56%) as a brown solid. MS: m/z=467.1 [M+H]$^+$. $^1$H NMR (400 MHz, Dimethylsulfoxide-d$_6$) δ 10.13 (s, 1H), 8.66 (s, 1H), 8.54 (d, J=8.8 Hz, 1H), 8.06 (d, J=8.4 Hz, 1H), 7.64 (d, J=8.0 Hz, 2H), 7.45-7.32 (m, 3H), 6.47 (d, J=9.6 Hz, 1H), 4.72 (s, 2H), 3.52 (s, 3H), 0.91 (s, 9H), 0.10 (s, 6H).

Step 4: 5-(2-(2-Aminopyridin-3-yl)-3-(4-(hydroxymethyl)phenyl)-3H-imidazo[4,5-b]pyridin-5-yl)-1-methylpyridin-2(1H)-one To a mixture of 6-((4-((tert-butyldimethylsilyl)oxy)methyl)phenyl)amino)-1'-methyl-5-nitro-[2,3'-bipyridin]-6'(1'H)-one (300 mg, 643 μmol) and 2-aminopyridine-3-carbaldehyde (86.4 mg, 707 μmol) in DMSO (3 mL) was added Na$_2$S$_2$O$_4$ (280 mg, 1.61 mmol). The mixture was stirred at 100° C. for 12 hr. The mixture was diluted with H$_2$O (50 mL) and extracted with CH$_2$Cl$_2$/MeOH (10/1) (30 mL×3). The combined organic layers were washed with brine (20 mL×3), dried over Na$_2$SO$_4$, filtered and concentrated. The mixture was purified by silica gel flash chromatography (Eluent of 0~60% EtOAc/EtOH (3/1) in petroleum ether) to give 5-(2-(2-aminopyridin-3-yl)-3-(4-(hydroxymethyl)phenyl)-3H-imidazo[4,5-b]pyridin-5-yl)-1-methylpyridin-2(1H)-one (100 mg, yield: 37%) as a yellow solid. MS: m/z=425.0 [M+H]$^+$. $^1$H NMR (400 MHz, Dimethylsulfoxide-d$_6$) δ 8.49 (d, J=2.4 Hz, 1H), 8.24 (d, J=8.8 Hz, 1H), 8.08 (dd, J=9.6, 2.4 Hz, 1H), 8.00 (dd, J=4.8, 2.0 Hz, 1H), 7.84 (d, J=8.4 Hz, 1H), 7.50-7.42 (m, 4H), 7.19 (dd, J=8.0, 2.0 Hz, 1H), 6.98 (br s, 2H), 6.50 (d, J=9.6 Hz, 1H), 6.44-6.37 (m, 1H), 5.37 (t, J=6.0 Hz, 1H), 4.61 (d, J=6.0 Hz, 2H), 3.53 (s, 3H).

Step 5: 5-(2-(2-Aminopyridin-3-yl)-3-(4-(chloromethyl)phenyl)-3H-imidazo[4,5-b]pyridin-5-yl)-1-methylpyridin-2(1H)-one To a mixture of 5-(2-(2-aminopyridin-3-yl)-3-(4-(hydroxymethyl)phenyl)-3H-imidazo[4,5-b]pyridin-5-yl)-1-methylpyridin-2(1H)-one (100 mg, 236 μmol) in CH$_2$Cl$_2$ (2 mL) was added SOCl$_2$ (84.1 mg, 51.3 μL). The mixture was stirred at 40° C. for 1 hr. The mixture was concentrated to give 5-(2-(2-aminopyridin-3-yl)-3-(4-(chloromethyl)phenyl)-3H-imidazo[4,5-b]pyridin-5-yl)-1-methylpyridin-2(1H)-one (Intermediate 105.80 mg, yield: 77%) as a yellow solid. MS: m/z=443.0 [M+H]$^+$. $^1$H NMR (400 MHz, Dimethylsulfoxide-d$_6$) δ 8.59-8.51 (m, 2H), 8.33 (d, J=8.4 Hz, 1H), 8.17-8.05 (m, 2H), 7.96-7.80 (m, 2H), 7.74-7.48 (m, 3H), 6.94-6.84 (m, 1H), 6.56-6.47 (m, 1H), 4.86 (s, 2H), 3.53 (s, 3H).

Intermediate 106: 4-(2-(2-aminopyridin-3-yl)-3-(4-(chloromethyl)phenyl)-3H-imidazo[4,5-b]pyridin-5-yl)-1-methylpyridin-2(1H)-one

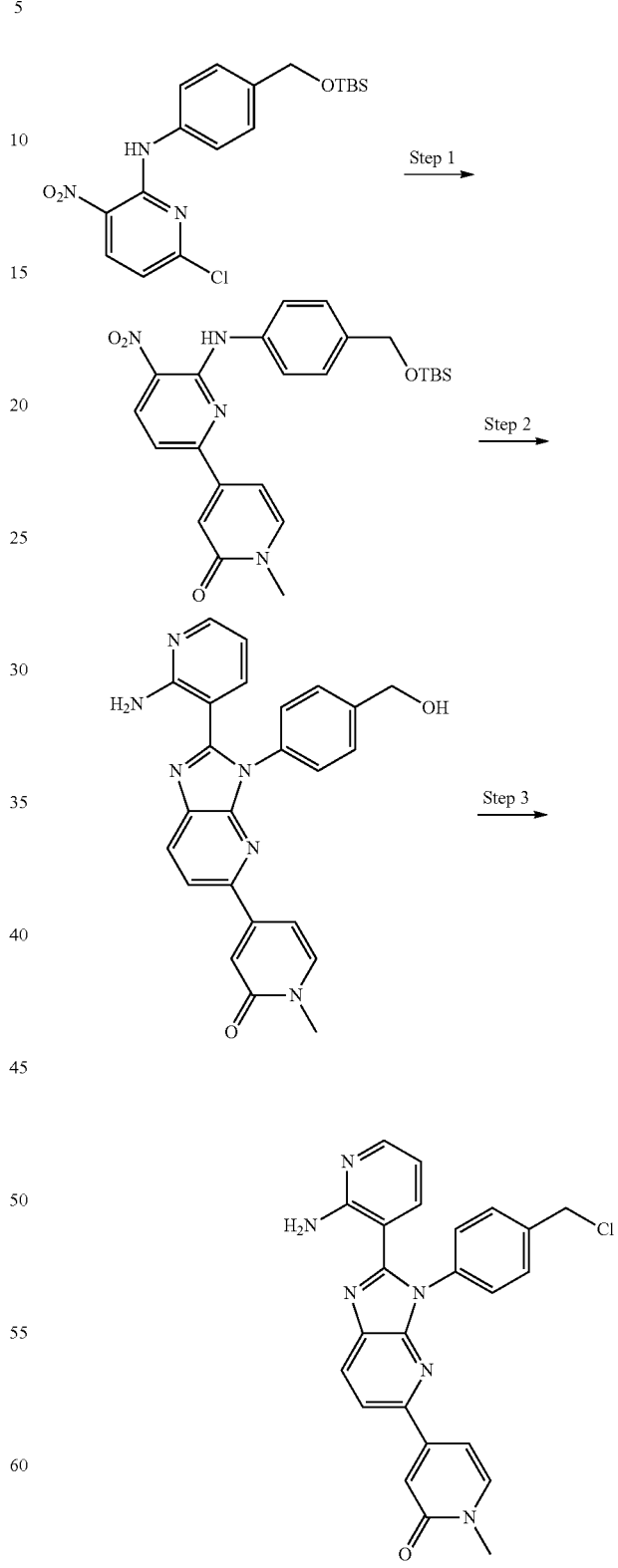

Intermediate 106

Step 1: 6-((4-(((Tert-butyldimethylsilyl)oxy)methyl) phenyl)amino)-1'-methyl-5-nitro-[2,4'-bipyridin]-2' (1'H)-one To a mixture of N-(4-(((tert-butyldimethylsilyl)oxy) methyl)phenyl)-6-chloro-3-nitropyridin-2-amine (refer to Intermediate 105 for detail procedures, 6 g, 15.2 mmol) and (1-methyl-2-oxo-4-pyridyl)boronic acid (2.56 g, 16.8 mmol) in H$_2$O (12 mL) and dioxane (60 mL) were added Pd(dppf) Cl$_2$ (1.11 g, 1.52 mmol) and Cs$_2$CO$_3$ (14.9 g, 45.7 mmol). The mixture was stirred at 100° C. for 2 hr under N$_2$. H$_2$O (200 mL) was added and extracted with EtOAc (300 mL×2). The combined organic layers were washed with brine (200 mL), dried over Na$_2$SO$_4$, filtered and concentrated. The mixture was purified by silica gel flash chromatography (Eluent 0-50% EtOAc in petroleum ether) to give 6-((4-(((tert-butyldimethylsilyl)oxy)methyl)phenyl)amino)-1'-methyl-5-nitro-[2,4'-bipyridin]-2'(1'H)-one (3.2 g, yield: 45%) as a yellow solid. $^1$H NMR (400 MHz, Dimethyl-sulfoxide-d$_6$) δ 10.02 (s, 1H), 8.61 (d, J=8.4 Hz, 1H), 7.81 (d, J=7.2 Hz, 1H), 7.64 (d, J=8.4 Hz, 2H), 7.58 (d, J=8.8 Hz, 1H), 7.34 (d, J=8.4 Hz, 2H), 7.06 (s, 1H), 6.77 (dd, J=6.8, 1.6 Hz, 1H), 4.73 (s, 2H), 3.45 (s, 3H), 0.92 (s, 9H), 0.10 (s, 6H).

Step 2: 4-(2-(2-Aminopyridin-3-yl)-3-(4-(hy-droxymethyl)phenyl)-3H-imidazo[4,5-b]pyridin-5-yl)-1-methylpyridin-2(1H)-one To a mixture of 6-((4-(((tert-butyldimethylsilyl)oxy) methyl)phenyl)amino)-1'-methyl-5-nitro-[2,4'-bipyridin]-2' (1'H)-one (3.1 g, 6.64 mmol) and 2-aminopyridine-3-carb-aldehyde (892 mg, 7.31 mmol) in DMSO (3 mL) was added Na$_2$S$_2$O$_4$ (2.89 g, 16.6 mmol). The mixture was stirred at 100° C. for 12 hr. Sat. NaHCO$_3$ (500 mL) was added and extracted with CH$_2$Cl$_2$/MeOH (10/1) (300 mL×3). The combined organic layers were washed with brine (200 mL×3), dried over Na$_2$SO$_4$, filtered and concentrated. The mixture was purified by silica gel flash chromatography (Eluent of 0~100% EtOAc/EtOH (3/1) in petroleum ether) to give 4-(2-(2-aminopyridin-3-yl)-3-(4-(hydroxymethyl) phenyl)-3H-imidazo[4,5-b]pyridin-5-yl)-1-methylpyridin-2 (1H)-one (1.4 g, yield: 50%) as a yellow solid. MS: m/z=425.1 [M+H]$^+$. $^1$H NMR (400 MHz, Dimethylsulfox-ide-d$_6$) δ 8.28 (d, J=8.0 Hz, 1H), 8.08-7.98 (m, 2H), 7.75 (d, J=7.2 Hz, 1H), 7.54-7.41 (m, 4H), 7.27-7.20 (m, 1H), 7.04 (d, J=1.6 Hz, 1H), 6.97 (d, J=4.4 Hz, 1H), 6.86 (dd, J=7.2, 2.0 Hz, 1H), 6.42 (dd, J=7.6, 4.8 Hz, 1H), 4.64-4.56 (m, 2H), 3.44 (s, 3H).

Step 3: 4-(2-(2-Aminopyridin-3-yl)-3-(4-(chlorom-ethyl)phenyl)-3H-imidazo[4,5-b]pyridin-5-yl)-1-methylpyridin-2(11H)-one To a mixture of 4-(2-(2-aminopyridin-3-yl)-3-(4-(hy-droxymethyl)phenyl)-3H-imidazo[4,5-b]pyridin-5-yl)-1-methylpyridin-2(1H)-one (400 mg, 942 μmol) in CH$_2$Cl$_2$ (5 mL) was added SOCl$_2$ (336 mg, 205 μL), the mixture was stirred at 40° C. for 1 hr. The mixture was concentrated to give 4-(2-(2-aminopyridin-3-yl)-3-(4-(chloromethyl)phe-nyl)-3H-imidazo[4,5-b]pyridin-5-yl)-1-methylpyridin-2 (1H)-one (Intermediate 106, 400 mg, yield: 96%) as a yellow solid. MS: m/z=443.1 [M+H]$^+$. $^1$H NMR (400 MHz, Dimethylsulfoxide-d$_6$) δ 8.50-8.36 (m, 2H), 8.17-8.10 (m, 2H), 7.95 (dd, J=7.6, 1.6 Hz, 1H), 7.81 (d, J=7.2 Hz, 1H), 7.71-7.56 (m, 4H), 7.13-7.07 (m, 1H), 6.97-6.86 (m, 2H), 4.88 (s, 2H), 3.46 (s, 3H).

Intermediate 107: 3-(3-(4-(Chloromethyl)phenyl)-5-(4-fluorophenyl)-3H-imidazo[4,5-b]pyridin-2-yl) pyridin-2-amine

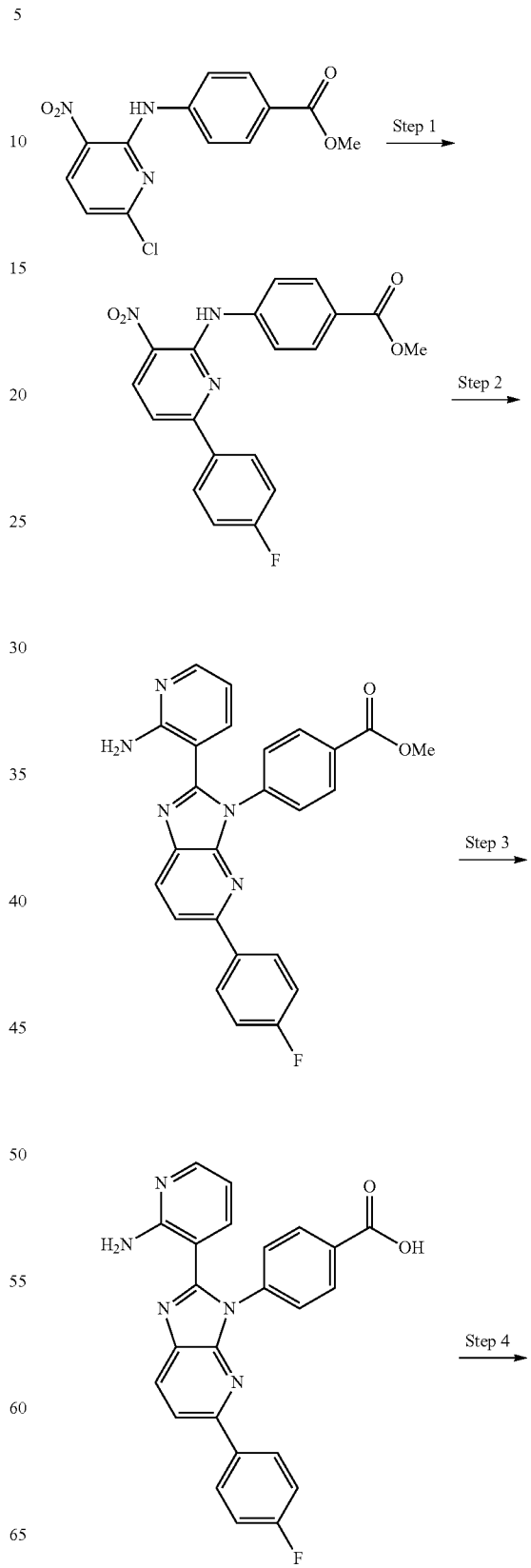

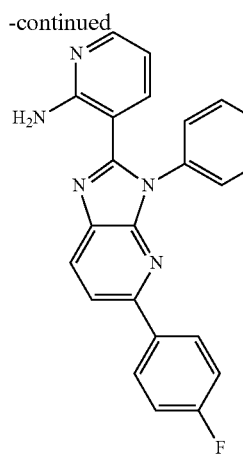

Intermediate 107

Step 1: Methyl 4-((6-(4-fluorophenyl)-3-nitropyridin-2-yl)amino)benzoate

A mixture of methyl 4-((6-chloro-3-nitropyridin-2-yl)amino)benzoate (refer to Intermediate 13 for detail procedures, 5.0 g, 16.3 mmol), (4-fluorophenyl)boronic acid (3.0 g, 21.1 mmol), Pd(dppf)Cl$_2$ (0.2 g, 1.63 mmol), and Cs$_2$CO$_3$ (15.9 g, 48.8 mmol) in 1,4-dioxane (50 mL) and H$_2$O (5 mL) was degassed and purged with N$_2$ three times, and then the mixture was stirred at 100° C. for 16 hr under N$_2$ atmosphere. The reaction mixture was diluted with water (200 mL) and extracted with EtOAc (300 mL×3). The combined organic layers were dried over Na$_2$SO$_4$, filtered and concentrated under reduced pressure. The residue was purified by silica gel flash chromatography (Eluent of 0~10% MeOH in CH$_2$Cl$_2$) to give methyl 4-((6-(4-fluorophenyl)-3-nitropyridin-2-yl)amino)benzoate (2.5 g, yield: 34%) as a yellow solid. MS: m/z=340.3 [M+H]$^+$. $^1$H NMR (400 MHz, Dimethylsulfoxide-d$_6$) δ 10.45 (s, 1H), 8.62 (d, J=8.6 Hz, 1H), 8.15-8.04 (m, 4H), 7.85 (d, J=8.4 Hz, 2H), 7.34 (d, J=8.6 Hz, 1H), 7.24-7.18 (m, 2H), 3.95 (s, 3H).

Step 2: Methyl 4-(2-(2-aminopyridin-3-yl)-5-(4-fluorophenyl)-3H-imidazo[4,5-b]pyridin-3-yl)benzoate To a solution of methyl 4-((6-(4-fluorophenyl)-3-nitropyridin-2-yl)amino)benzoate (2.5 g 6.81 mmol) and 2-aminopyridine-3-carbaldehyde (914 mg, 7.49 mmol) in DMSO (100 mL) was added Na$_2$S$_2$O$_4$ (4.74 g, 7.49 mmol). The mixture was stirred at 100° C. for 12 hr. The reaction mixture was diluted with water (100 mL) and extracted with CH$_2$Cl$_2$ (300 mL×2). The combined organic layers were washed with brine (100 mL), dried over Na$_2$SO$_4$, filtered and concentrated under reduced pressure. The residue was purified by silica gel flash chromatography (Eluent of 0~100% EtOAc in petroleum ether) to give methyl 4-(2-(2-aminopyridin-3-yl)-5-(4-fluorophenyl)-3H-imidazo[4,5-b]pyridin-3-yl)benzoate (1.3 g, yield: 40%) as yellow solid. MS: m/z=440.0 [M+H]$^+$. $^1$H NMR (400 MHz, Chloroform-d) δ 8.26-8.21 (m, 2H), 8.15 (d, J=8.4 Hz, 1H), 8.08 (dd, J=5.2, 1.6 Hz, 1H), 8.03-7.98 (m, 2H), 7.79 (d, J=8.4 Hz, 1H), 7.56 (d, J=8.4 Hz, 2H), 7.17-7.08 (m, 3H), 6.82 (br s, 2H), 6.42 (dd, J=7.6, 4.8 Hz, 1H), 3.99 (s, 3H).

Step 3: (4-(2-(2-Aminopyridin-3-yl)-5-(4-fluorophenyl)-3H-imidazo[4,5-b]pyridin-3-yl)phenyl)methanol To a solution of methyl 4-(2-(2-aminopyridin-3-yl)-5-(4-fluorophenyl)-3H-imidazo[4,5-b]pyridin-3-yl)benzoate (1.3 g, 2.92 mmol) in THF (100 mL) was added LiAlH$_4$ (2.5 M, 4.44 mmol) at 0° C. The mixture was stirred at 0° C. for 2 hr. The reaction mixture was quenched with Na$_2$SO$_4$ 10H$_2$O (203 mg) at 0° C. and filtered. The filtrate was concentrated under reduced pressure. The crude (4-(2-(2-aminopyridin-3-yl)-5-(4-fluorophenyl)-3H-imidazo[4,5-b]pyridin-3-yl)phenyl)methanol (1.2 g) was used in the next step without further purification. MS: m/z=412.0 [M+H]$^+$.

Step 4: 3-(3-(4-(Chloromethyl)phenyl)-5-(4-fluorophenyl)-3H-imidazo[4,5-b]pyridin-2-yl)pyridin-2-amine To a solution of (4-(2-(2-aminopyridin-3-yl)-5-(4-fluorophenyl)-3H-imidazo[4,5-b]pyridin-3-yl)phenyl)methanol (1.2 g, 2.91 mmol) in CH$_2$Cl$_2$ (20 mL) was added SOCl$_2$ (2.1 g, 17.5 mmol). The mixture was stirred at 40° C. for 2 hr. The mixture was concentrated under reduced pressure. 3-(3-(4-(Chloromethyl)phenyl)-5-(4-fluorophenyl)-3H-imidazo[4,5-b]pyridin-2-yl)pyridin-2-amine (Intermediate 107, 1.25 g HCl salt, yield: 89%) was obtained as a yellow solid. MS: m/z=429.9 [M+H]$^+$.

Intermediate 108: 3-(3-(4-(Chloromethyl)phenyl)-5-(3-chlorophenyl)-3H-imidazo[4,5-b]pyridin-2-yl)pyridin-2-amine

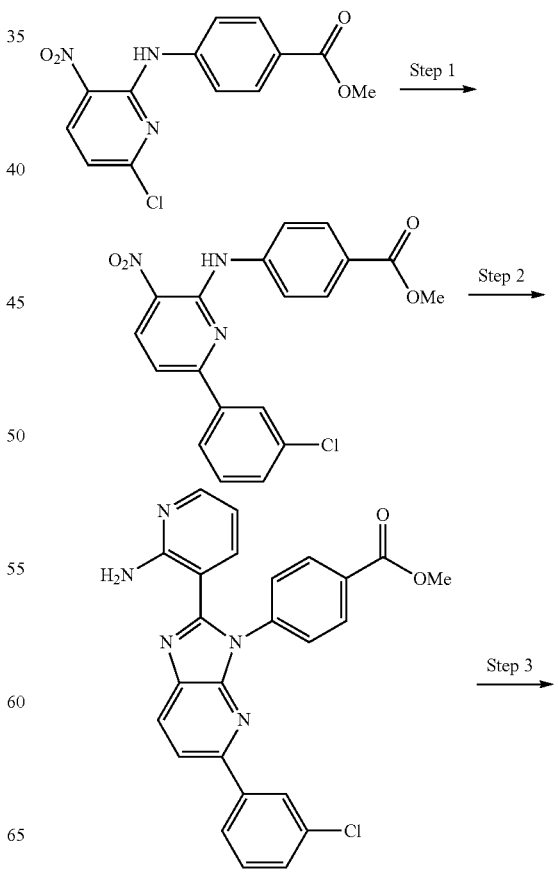

-continued

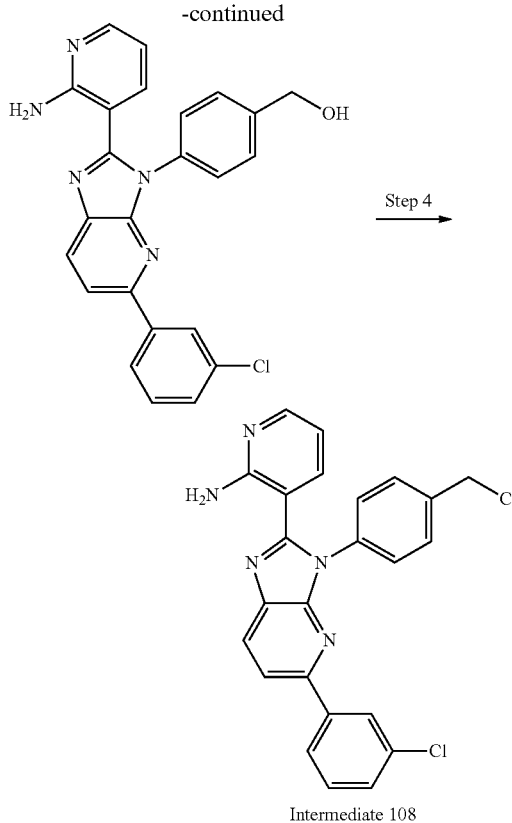

Intermediate 108

Step 1: Methyl 4-((6-(3-chlorophenyl)-3-nitropyridin-2-yl)amino)benzoate

A mixture of methyl 4-((6-chloro-3-nitropyridin-2-yl)amino)benzoate (refer to Intermediate 13 for detail procedures, 5.0 g, 16.2 mmol), (3-chlorophenyl)boronic acid (3.3 g, 21.1 mmol), Pd(dppf)Cl$_2$ (1.2 g, 1.63 mmol), Cs$_2$CO$_3$ (16 g, 48.8 mmol) in 1,4-dioxane (50 mL) and H$_2$O (5 mL) was degassed and purged with N$_2$ three times, and the mixture was stirred at 100° C. for 12 hr under N$_2$ atmosphere. The reaction mixture was diluted with water (20 mL) and extracted with CH$_2$Cl$_2$ (30 mL×2). The combined organic layers were dried over Na$_2$SO$_4$, filtered and concentrated under reduced pressure. The residue was purified by silica gel flash chromatography (Eluent of 0~10% MeOH in CH$_2$Cl$_2$) to give methyl 4-((6-(3-chlorophenyl)-3-nitropyridin-2-yl)amino)benzoate (6 g, yield: 84%) as a yellow solid. MS: m/z=383.9 [M+H]$^+$. $^1$H NMR (400 MHz, Chloroform-d) δ 10.44 (br s, 1H), 8.64 (d, J=8.4 Hz, 1H), 8.12 (d, J=8.4 Hz, 2H), 8.04 (s, 1H), 7.94 (d, J=7.6 Hz, 1H), 7.86 (d, J=8.4 Hz, 2H), 7.53-7.43 (m, 2H), 7.36 (d, J=8.6 Hz, 1H), 3.95 (s, 3H).

Step 2: Methyl 4-(2-(2-aminopyridin-3-yl)-5-(3-chlorophenyl)-3H-imidazo[4,5-b]pyridin-3-yl)benzoate To a solution of methyl 4-((6-(3-chlorophenyl)-3-nitropyridin-2-yl)amino)benzoate (5.5 g, 14.3 mmol) and 2-aminonicotinaldehyde (1.9 g, 15.7 mmol) in DMSO (200 mL) was added Na$_2$S$_2$O$_4$ (10 g, 57.3 mmol). The mixture was stirred at 100° C. for 12 hr. The reaction mixture was diluted with water (100 mL) and extracted with CH$_2$Cl$_2$ (300 mL×2). The combined organic layers were washed with brine (100 mL), dried over Na$_2$SO$_4$, filtered and concentrated under reduced pressure. The residue was purified by silica gel flash chromatography (Eluent of 0~100% EtOAc in petroleum ether) to give methyl 4-(2-(2-aminopyridin-3-yl)-5-(3-chlorophenyl)-3H-imidazo[4,5-b]pyridin-3-yl)benzoate (2.4 g, yield: 52%) as a yellow solid. MS: m/z=456.0 [M+H]$^+$. $^1$H NMR (400 MHz, Chloroform-d) δ 8.22 (d, J=8.4 Hz, 2H), 8.14 (d, J=8.4 Hz, 1H), 8.11-8.08 (m, 1H), 7.98 (s, 1H), 7.89-7.86 (m, 1H), 7.78 (d, J=8.4 Hz, 1H), 7.54 (d, J=8.6 Hz, 2H), 7.38-7.32 (m, 2H), 7.05 (dd, J=7.6, 1.6 Hz, 1H), 6.60 (br s, 2H), 6.39 (dd, J=7.6, 4.8 Hz, 1H), 3.98 (s, 3H).

Step 3: (4-(2-(2-Aminopyridin-3-yl)-5-(3-chlorophenyl)-3H-imidazo[4,5-b]pyridin-3-yl)phenyl)methanol To a solution of methyl 4-(2-(2-aminopyridin-3-yl)-5-(3-chlorophenyl)-3H-imidazo[4,5-b]pyridin-3-yl)benzoate (2.4 g, 5.26 mmol) in THF (100 mL) was added LiAlH$_4$ (2.5 M, 1.05 mL) at 0° C. The mixture was stirred at 0° C. for 2 hr. The reaction mixture was quenched with Na$_2$SO$_4$ 10H$_2$O (300 mg) at 0° C. and filtered. The filtrate was concentrated under reduced pressure to give (4-(2-(2-aminopyridin-3-yl)-5-(3-chlorophenyl)-3H-imidazo[4,5-b]pyridin-3-yl)phenyl)methanol (2.2 g, yield: 85%) as a yellow solid. MS: m/z=430.0 [M+H]$^+$.

Step 4: 3-(3-(4-(Chloromethyl)phenyl)-5-(3-chlorophenyl)-3H-imidazo[4,5-b]pyridin-2-yl)pyridin-2-amine To a solution of (4-(2-(2-aminopyridin-3-yl)-5-(3-chlorophenyl)-3H-imidazo[4,5-b]pyridin-3-yl)phenyl)methanol (2.2 g, 5.14 mmol) in CH$_2$Cl$_2$ (25 mL) was added SOCl$_2$ (3.67 g, 30.9 mmol). The mixture was stirred at 40° C. for 2 hr. The mixture was concentrated under reduced pressure to give 3-(3-(4-(chloromethyl)phenyl)-5-(3-chlorophenyl)-3H-imidazo[4,5-b]pyridin-2-yl)pyridin-2-amine (Intermediate 108, 2.2 g HCl salt, yield: 84%) as a yellow solid. MS: m/z=446.0 [M+H]$^+$.

Intermediate 109: 3-(3-(4-(((1S,4S)-2,5-Diazabicyclo[2.2.1]heptan-2-yl)methyl)phenyl)-5-phenyl-3H-imidazo[4,5-b]pyridin-2-yl)pyridin-2-amine

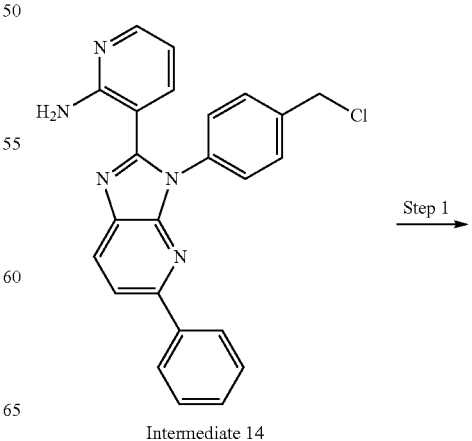

Intermediate 14

-continued

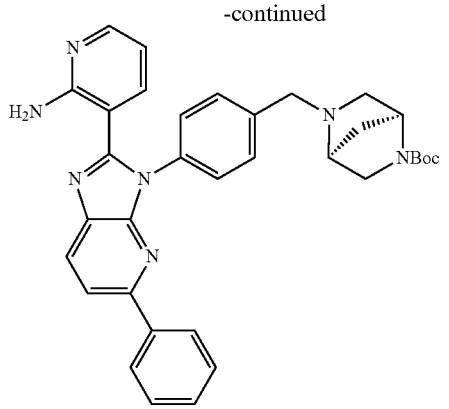

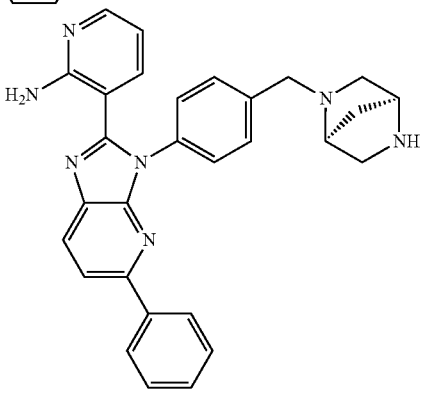

Intermediate 109

Step 1: Tert-butyl (1S,4S)-5-(4-(2-(2-aminopyridin-3-yl)-5-phenyl-3H-imidazo[4,5-b]pyridin-3-yl)benzyl)-2,5-diazabicyclo[2.2.1]heptane-2-carboxylate To a solution of Intermediate 14 (1.0 g, 2.43 mmol) in DMF (10 mL) were added DIEA (1.27 mL, 7.28 mmol) and tert-butyl (1 S,4S)-2,5-diazabicyclo[2.2.1]heptane-2-carboxylate (530 mg, 2.67 mmol). The mixture was degassed and purged with $N_2$ three times and stirred at 80° C. for 16 hr under $N_2$. The reaction mixture was diluted with $CH_2Cl_2$ (80 mL) at 25° C., washed with brine (50 mL×3), dried over $Na_2SO_4$, filtered and concentrated under reduced pressure. The residue was purified by silica gel flash chromatography (Eluent of 1~4% MeOH in $CH_2Cl_2$) to give tert-butyl (1S,4S)-5-(4-(2-(2-aminopyridin-3-yl)-5-phenyl-3H-imidazo[4,5-b]pyridin-3-yl)benzyl)-2,5-diazabicyclo[2.2.1]heptane-2-carboxylate (1.14 g, yield: 75%) as a yellow solid. MS: m/z=574.4 [M+H]$^+$. $^1$H NMR (400 MHz, Chloroform-d) δ 8.12 (d, J=8.4 Hz, 1H), 8.06 (dd, J=4.8, 1.6 Hz, 1H), 8.04-7.98 (m, 2H), 7.80 (d, J=8.4 Hz, 1H), 7.50 (d, J=8.4 Hz, 2H), 7.47-7.33 (m, 5H), 7.10 (d, J=7.6 Hz, 1H), 6.60 (br s, 2H), 6.36 (dd, J=8.0, 4.8 Hz, 1H), 4.47-4.24 (m, 1H), 3.88-3.80 (m, 2H), 3.71-3.49 (m, 2H), 3.28-3.16 (m, 1H), 3.02-2.89 (m, 1H), 2.82-2.57 (m, 1H), 1.96-1.87 (m, 1H), 1.77-1.68 (m, 1H), 1.48 (s, 9H).

Step 2: 3-(3-(4-(((1 S,4S)-2,5-Diazabicyclo[2.2.1]heptan-2-yl)methyl)phenyl)-5-phenyl-3H-imidazo[4,5-b]pyridin-2-yl)pyridin-2-amine To a solution of tert-butyl (1S,4S)-5-(4-(2-(2-aminopyridin-3-yl)-5-phenyl-3H-imidazo[4,5-b]pyridin-3-yl)benzyl)-2,5-diazabicyclo[2.2.1]heptane-2-carboxylate (50 mg, 87.2 μmol) in dioxane (0.5 mL) was added HCl in 1,4-dioxane (4M, 1 mL). The mixture was degassed and purged with $N_2$ three times and stirred at 25° C. for 2 hr under $N_2$. The reaction mixture was concentrated under reduced pressure. The residue was triturated with 1 mL 1,4-dioxane at 25° C. for 10 min. 3-(3-(4-(((1S,4S)-2,5-Diazabicyclo[2.2.1]heptan-2-yl)methyl)phenyl)-5-phenyl-3H-imidazo[4,5-b]pyridin-2-yl)pyridin-2-amine (Intermediate 109, 41 mg, HCl salt, yield: 95%) was obtained as a light-yellow solid. MS: m/z=474.2 [M+H]$^+$. $^1$H NMR (400 MHz, Dimethylsulfoxide-d$_6$) δ 12.43-11.57 (m, 1H), 10.39-9.51 (m, 2H), 8.55-8.39 (m, 1H), 8.38 (d, J=8.4 Hz, 1H), 8.14 (d, J=5.2 Hz, 1H), 8.11-8.01 (m, 3H), 7.94 (d, J=8.0 Hz, 2H), 7.84 (d, J=7.2 Hz, 1H), 7.69 (d, J=8.4 Hz, 2H), 7.54-7.40 (m, 3H), 6.91-6.87 (m, 1H), 4.68-4.40 (m, 4H), 3.99-3.94 (m, 1H), 3.80-3.75 (m, 2H), 3.42-3.40 (m, 1H), 2.60-2.52 (m, 1H), 2.20-2.06 (m, 1H).

Intermediate 110: 3-(3-(4-((4-Aminopiperidin-1-yl)methyl)phenyl)-2-(2-aminopyridin-3-yl)-3H-imidazo[4,5-b]pyridin-5-yl)pyridin-2(1H)-one

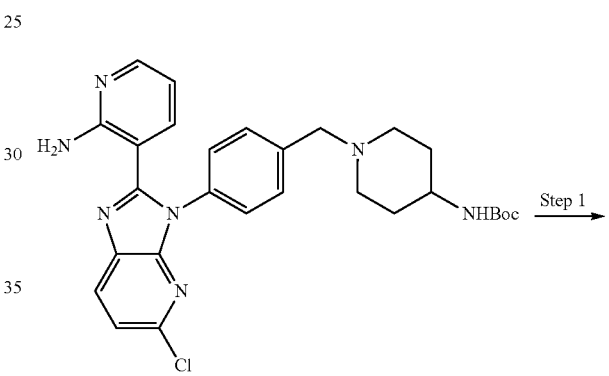

Intermediate 44

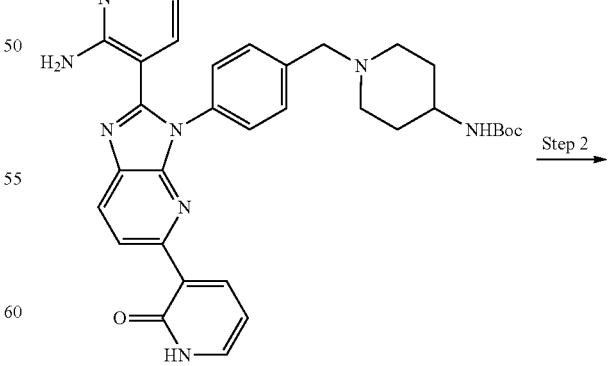

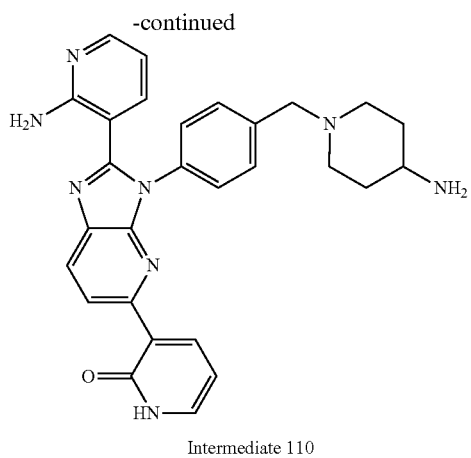

Intermediate 110

Step 1: tert-Butyl (1-(4-(2-(2-aminopyridin-3-yl)-5-(2-oxo-1,2-dihydropyridin-3-yl)-3H-imidazo[4,5-b]pyridin-3-yl)benzyl)piperidin-4-yl)carbamate A mixture of Intermediate 44 (200 mg, 375 µmol), (2-oxo-1,2-dihydropyridin-3-yl)boronic acid (78 mg, 562 µmol), $Cs_2CO_3$ (244 mg, 749 µmol), and $Pd(dppf)Cl_2$ (27 mg, 37 µmol) in 1,4-dioxane (5 mL) and $H_2O$ (1 mL) was degassed and purged with $N_2$ three times, and then the mixture was stirred at 100° C. for 16 hr under $N_2$ atmosphere. The mixture was diluted with $H_2O$ (30 mL) and extracted with EtOAc (30 mL×2). The combined organic layers were washed with brine (30 mL), dried over $Na_2SO_4$, filtered and concentrated under reduced pressure. The crude was purified by silica gel flash chromatography (Eluent of 0-10% MeOH in $CH_2Cl_2$) to give tert-butyl (1-(4-(2-(2-aminopyridin-3-yl)-5-(2-oxo-1,2-dihydropyridin-3-yl)-3H-imidazo[4,5-b]pyridin-3-yl)benzyl)piperidin-4-yl)carbamate (90 mg, yield 41%) as a light-yellow solid. MS: m/z=593.3 [M+H]$^+$. $^1$H NMR (400 MHz, Chloroform-d) δ 12.66 (br s, 1H), 8.65 (d, J=7.6 Hz, 1H), 8.40 (dd, J=7.2, 1.6 Hz, 1H), 8.13 (d, J=8.4 Hz, 1H), 8.06 (dd, J=4.4, 1.2 Hz, 1H), 7.52-7.45 (m, 3H), 7.37 (d, J=8.0 Hz, 2H), 7.08 (dd, J=7.6, 1.2 Hz, 1H), 6.68 (brs, 2H), 6.50-6.45 (m, 1H), 6.34 (dd, J=7.6, 4.8 Hz, 1H), 4.52-4.44 (m, 1H), 3.60 (s, 2H), 3.52-3.47 (m, 1H), 2.91-2.84 (m, 2H), 2.21-2.14 (m, 2H), 1.99-1.93 (m, 2H), 1.55-1.48 (m, 2H), 1.45 (s, 9H).

Step 2: 3-(3-(4-((4-Aminopiperidin-1-yl)methyl)phenyl)-2-(2-aminopyridin-3-yl)-3H-imidazo[4,5-b]pyridin-5-yl)pyridin-2(1H)-one A solution of tert-butyl (1-(4-(2-(2-aminopyridin-3-yl)-5-(2-oxo-1,2-dihydropyridin-3-yl)-3H-imidazo[4,5-b]pyridin-3-yl)benzyl)piperidin-4-yl)carbamate (90 mg, 152 µmol) in HCl in 1,4-dioxane (4 M, 2 mL) was stirred at 25° C. for 1 hr. The mixture was concentrated under reduced pressure to give 3-(3-(4-((4-aminopiperidin-1-yl)methyl)phenyl)-2-(2-aminopyridin-3-yl)-3H-imidazo[4,5-b]pyridin-5-yl)pyridin-2(1H)-one (Intermediate 110, 63.5 mg, yield: 78%) as a yellow solid. MS: m/z=493.2 [M+H]$^+$. $^1$H NMR (400 MHz, Methanol-d$_4$) δ 8.67-8.62 (m, 1H), 8.55 (d, J=8.4 Hz, 1H), 8.43 (d, J=8.0 Hz, 1H), 8.05-8.03 (m, 1H), 7.96-7.88 (m, 3H), 7.80 (d, J=5.2 Hz, 1H), 7.75-7.74 (m, 2H), 6.94-6.84 (m, 2H), 4.52 (s, 2H), 3.78-3.62 (m, 3H), 3.61-3.49 (m, 2H), 2.35-2.28 (m, 2H), 2.20-2.10 (m, 2H).

Intermediate 111: 4-(4-(2-(2-Aminopyridin-3-yl)-5-phenyl-3H-imidazo[4,5-b]pyridin-3-yl)benzyl)piperazin-1-amine hydrochloride

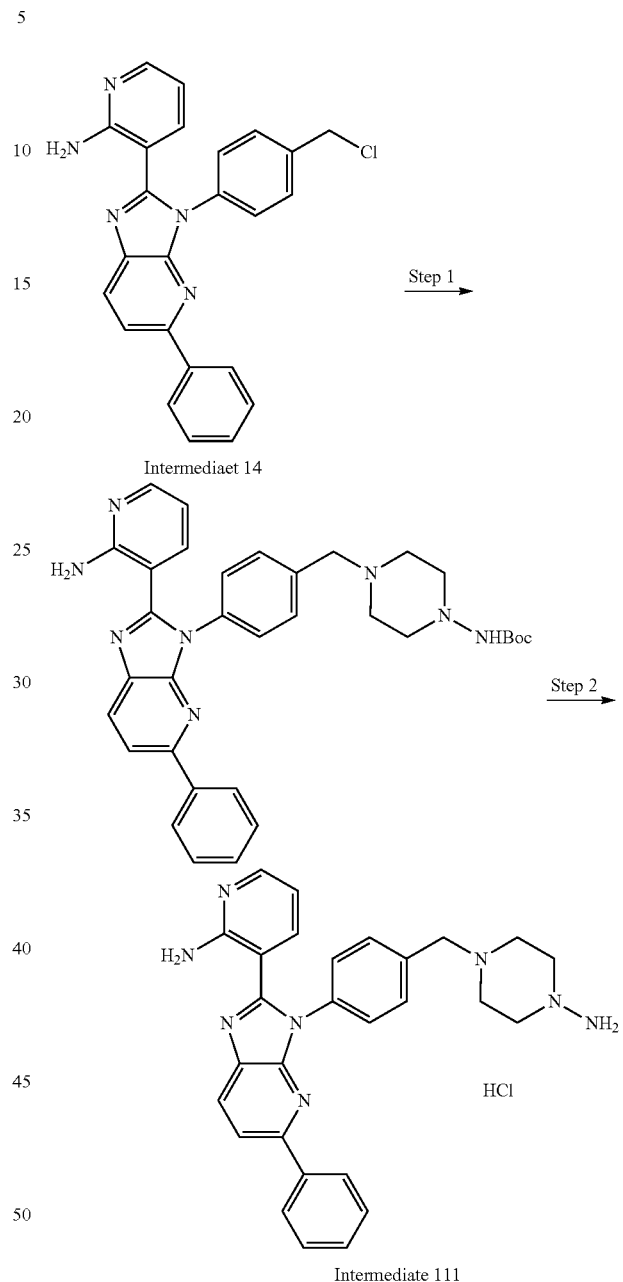

Intermediate 111

Step 1: Tert-butyl (4-(4-(2-(2-aminopyridin-3-yl)-5-phenyl-3H-imidazo[4,5-b]pyridin-3-yl)benzyl)piperazin-1-yl)carbamate To a solution of Intermediate 14 (1.50 g, 3.64 mmol) in DMF (5 mL) were added $K_2CO_3$ (1.01 g, 7.28 mmol), NaI (109 mg, 728 µmol), and tert-butyl piperazin-1-ylcarbamate (806 mg, 4.01 mmol) at 25° C. This mixture was stirred at 60° C. for 5 hr. $H_2O$ (35 mL) was added to the mixture. The aqueous phase was extracted with EtOAc (30 mL×3). The combined organic layers were washed with brine (30 mL), dried over anhydrous $Na_2SO_4$, filtered and concentrated.

The crude was purified by silica gel flash chromatography (Eluent of 0~10% MeOH in CH₂Cl₂) to give tert-butyl(4-(4-(2-(2-aminopyridin-3-yl)-5-phenyl-3H-imidazo[4,5-b]pyridin-3-yl)benzyl)piperazin-1-yl)carbamate (1.65 g, yield: 79%) as yellow oil. MS: m/z=577.3 [M+H]⁺.

Step 2: 4-(4-(2-(2-Aminopyridin-3-yl)-5-phenyl-3H-imidazo[4,5-b]pyridin-3-yl)benzyl)piperazin-1-amine hydrochloride To a solution of tert-butyl(4-(4-(2-(2-aminopyridin-3-yl)-5-phenyl-3H-imidazo[4,5-b]pyridin-3-yl)benzyl)piperazin-1-yl)carbamate (800 mg, 1.39 mmol) in 1,4-dioxane (10 mL) was added HCl/1,4-dioxane (4 M, 347 μL) at 25° C. This mixture was stirred at 25° C. for 12 hr. The mixture was filtered and concentrated to give 4-(4-(2-(2-aminopyridin-3-yl)-5-phenyl-3H-imidazo[4,5-b]pyridin-3-yl)benzyl)piperazin-1-amine hydrochloride (Intermediate 111, 700 mg, HCl salt, yield: 98%) as a yellow solid, which was used in the next step without purification. MS: m/z=477.3 [M+H]⁺.

Intermediate 112: 3-(2-(2-Aminopyridin-3-yl)-3-(4-(chloromethyl)phenyl)-3H-imidazo[4,5-b]pyridin-5-yl)isonicotinonitrile

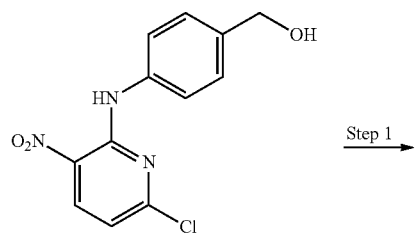

Step 1

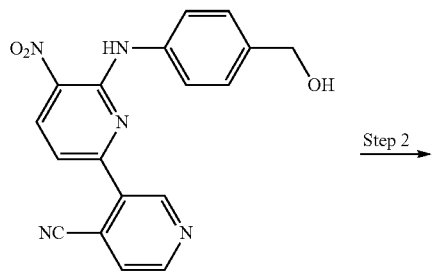

Step 2

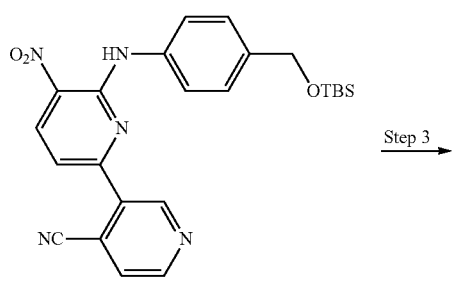

Step 3

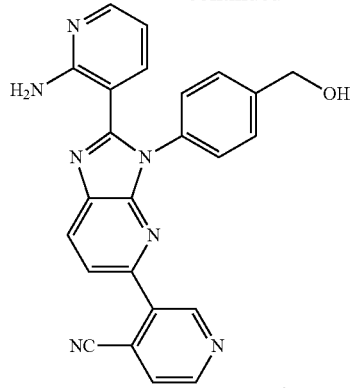

Step 4

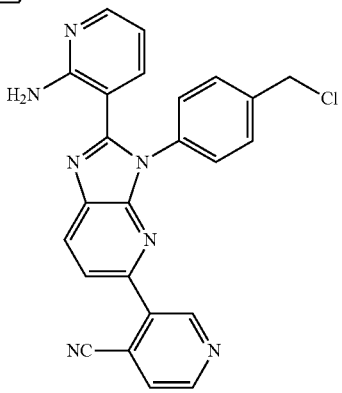

Intermediate 112

Step 1: 6-((4-(Hydroxymethyl)phenyl)amino)-5-nitro-[2,3'-bipyridine]-4'-carbonitrile A mixture of (4-(6-chloro-3-nitropyridin-2-yl)amino)phenyl)methanol (refer to Intermediate 105 for detail procedures, 2.0 g, 7.0 mmol), 3-(4,4,5,5-tetramethyl-1,3,2-dioxaborolan-2-yl)pyridine-4-carbonitrile (1.8 g, 7.9 mmol), cataCXiumAPdG₃ (2.6 g, 3.6 mmol), PCy₃ (200 mg, 715 μmol), and K₃PO₄ (3.0 g, 14.0 mmol) in DMF (20 mL) was degassed and purged with N₂ three times, and then mixture was stirred at 120° C. for 2 hr under N₂ atmosphere. The reaction mixture was diluted with water (100 mL) and extracted with EtOAc (150 mL×2). The combined organic layers were washed with brine (100 mL), dried over Na₂SO₄, filtered and concentrated under reduced pressure. After purified by silica gel flash chromatography (Eluent of 0~26% EtOAc in petroleum ether), 6-((4-(hydroxymethyl)phenyl)amino)-5-nitro-[2,3'-bipyridine]-4'-carbonitrile (1.9 g, yield: 58%) was obtained as an orange solid. MS: m/z=348.0 [M+H]⁺, ¹H NMR (400 MHz, Dimethylsulfoxide-d₆) δ 10.07 (s, 1H), 9.10 (s, 1H), 8.93 (d, J=5.2 Hz, 1H), 8.74 (d, J=8.4 Hz, 1H), 8.04 (d, J=5.2 Hz, 1H), 7.67 (d, J=8.4 Hz, 2H), 7.48 (d, J=8.4 Hz, 1H), 7.29 (d, J=8.4 Hz, 2H), 5.16 (t, J=6.0 Hz, 1H), 4.47 (d, J=6.4 Hz, 2H).

Step 2: 6-((4-(((tert-butyldimethylsilyl)oxy)methyl)phenyl)amino)-5-nitro-[2,3'-bipyridine]-4'-carbonitrile A mixture of 6-((4-(hydroxymethyl)phenyl)amino)-5-nitro-[2,3'-bipyridine]-4'-carbonitrile (1.9 g, 5.5 mmol), TBSCl (1.65 g, 11 mmol) and imidazole (931 mg, 14 mmol) in CH₂Cl₂ (20 mL) was degassed and purged with N₂ three times, and then the mixture was stirred at 25° C. for 2 hr under N$_2$ atmosphere. The reaction mixture was diluted with water (100 mL) and extracted with EtOAc (150 mL×2). The combined organic layers were washed with brine (100 mL), dried over Na$_2$SO$_4$, filtered and concentrated under reduced pressure. After purified by silica gel flash chromatography (Eluent of 0~5% MeOH in CH$_2$Cl$_2$), 6-((4-(((tert-butyldimethylsilyl)oxy)methyl)phenyl)amino)-5-nitro-[2,3'-bipyridine]-4'-carbonitrile (1.2 g, yield: 34%) was obtained as an orange solid. MS: m/z=462.1 [M+H]$^+$, $^1$H NMR (400 MHz, Dimethylsulfoxide-d$_6$) δ 10.08 (s, 1H), 9.11 (s, 1H), 8.93 (d, J=5.2 Hz, 1H), 8.74 (d, J=8.4 Hz, 1H), 8.04 (d, J=5.4 Hz, 1H), 7.68 (d, J=8.4 Hz, 2H), 7.48 (d, J=8.4 Hz, 1H), 7.28 (d, J=8.4 Hz, 2H), 4.69 (s, 2H), 0.89 (s, 9H), 0.07 (s, 6H).

Step 3: 3-(2-(2-Aminopyridin-3-yl)-3-(4-(hydroxymethyl)phenyl)-3H-imidazo[4,5-b]pyridin-5-yl)isonicotinonitrile A mixture of 6-((4-(((tert-butyldimethylsilyl)oxy)methyl)phenyl)amino)-5-nitro-[2,3'-bipyridine]-4'-carbonitrile (1.2 g, 2.6 mmol), 2-aminopyridine-3-carbaldehyde (349 mg, 2.9 mmol), Na$_2$S$_2$O$_4$ (1.8 g, 10 mmol) in DMSO (50 mL) was degassed and purged with N$_2$ three times, and then the mixture was stirred at 100° C. for 16 hr under N$_2$ atmosphere. The reaction mixture was diluted with water (100 mL) and extracted with EtOAc (300 mL×2). The combined organic layers were washed with brine (200 mL), dried over Na$_2$SO$_4$, filtered and concentrated under reduced pressure. After purified by silica gel flash chromatography (Eluent of 0~5% MeOH in CH$_2$Cl$_2$), 3-(2-(2-aminopyridin-3-yl)-3-(4-(hydroxymethyl)phenyl)-3H-imidazo[4,5-b]pyridin-5-yl)isonicotinonitrile (600 mg, yield: 22%) was obtained as a red solid. MS: m/z=420.0 [M+H]$^+$.

Step 4: 3-(2-(2-Aminopyridin-3-yl)-3-(4-(chloromethyl)phenyl)-3H-imidazo[4,5-b]pyridin-5-yl)isonicotinonitrile To a solution of 3-(2-(2-aminopyridin-3-yl)-3-(4-(hydroxymethyl)phenyl)-3H-imidazo[4,5-b]pyridin-5-yl)isonicotinonitrile (600 mg, 715 μmol) in CH$_2$Cl$_2$ (20 mL) was added SOCl$_2$ (511 mg, 4.3 mmol). The mixture was stirred at 40° C. for 2 hr. The reaction mixture was diluted with water (20 mL) and adjusted the pH to about 7-8 by saturated NaHCO$_3$ solution, then extracted with EtOAc (50 mL×2). The combined organic layers were washed with brine (30 mL), dried over Na$_2$SO$_4$, filtered and concentrated under reduced pressure. After purified by silica gel flash chromatography (Eluent of 0~26% EtOAc in petroleum ether), 3-(2-(2-aminopyridin-3-yl)-3-(4-(chloromethyl)phenyl)-3H-imidazo[4,5-b]pyridin-5-yl)isonicotinonitrile (Intermediate 112, 202 mg, yield: 55%) was obtained as a yellow solid. MS: m/z=437.9 [M+H]$^+$.

Intermediate 113: 3-(3-(4-((4-Aminopiperidin-1-yl)methyl)phenyl)-5-(3-chlorophenyl)-3H-imidazo[4,5-b]pyridin-2-yl)pyridin-2-amine

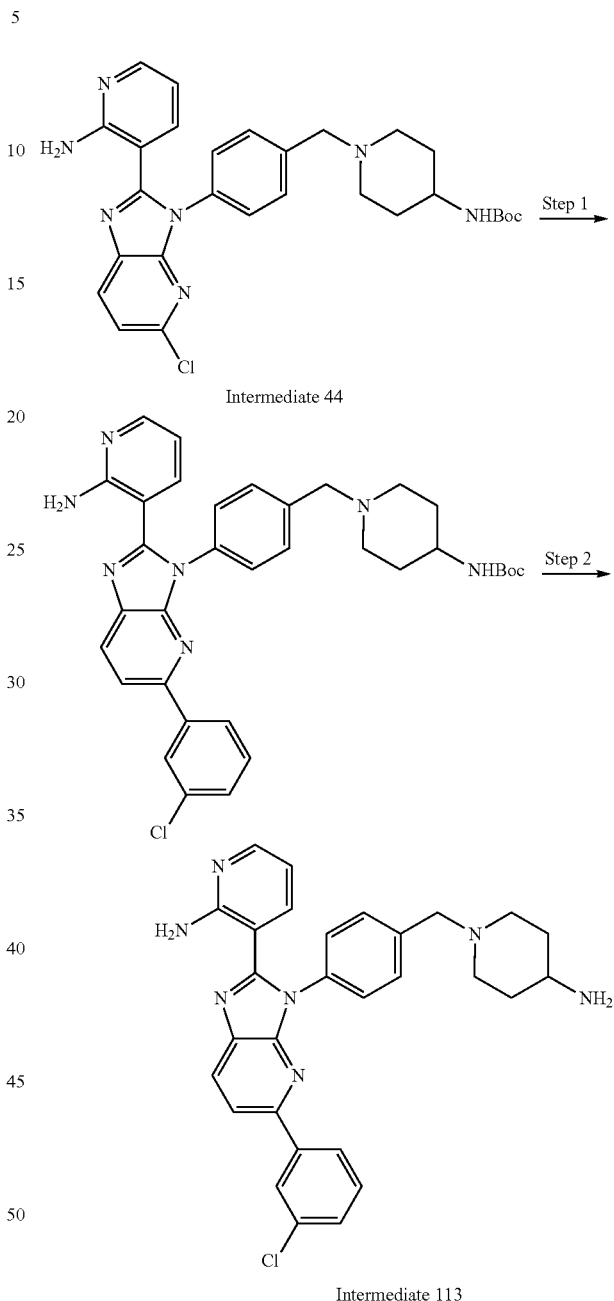

Step 1: tert-Butyl (1-(4-(2-(2-aminopyridin-3-yl)-5-(3-chlorophenyl)-3H-imidazo[4,5-b]pyridin-3-yl)benzyl)piperidin-4-yl)carbamate A mixture of Intermediate 44 (200 mg, 375 μmol), (3-chlorophenyl)boronic acid (88 mg, 562 μmol), Pd(dppf)Cl$_2$ (27 mg, 37 μmol), and Cs$_2$CO$_3$ (244 mg, 749 μmol) in 1,4-dioxane (3 mL) and H$_2$O (0.3 mL) was degassed and purged with N$_2$ three times, and the mixture was stirred at 100° C. for 12 hr under N$_2$ atmosphere. The reaction mixture was diluted with H$_2$O (20 mL) and extracted with CH$_2$Cl$_2$ (10 mL×3). The combined organic layers were dried over Na₂SO₄, filtered and concentrated under reduced pressure. After purified by silica gel flash chromatography (Eluent of 0~6% MeOH in CH₂Cl₂), tert-butyl (1-(4-(2-(2-aminopyridin-3-yl)-5-(3-chlorophenyl)-3H-imidazo[4,5-b]pyridin-3-yl)benzyl)piperidin-4-yl)carbamate (143 mg, yield: 40%) was obtained as brown yellow solid. MS: m/z=610.3 [M+H]⁺.

Step 2: 3-(3-(4-((4-Aminopiperidin-1-yl)methyl)phenyl)-5-(3-chlorophenyl)-3H-imidazo[4,5-b]pyridin-2-yl)pyridin-2-amine To a solution of tert-butyl (4-(4-(2-(2-aminopyridin-3-yl)-5-(3-chlorophenyl)-3H-imidazo[4,5-b]pyridin-3-yl)benzyl)cyclohexyl)carbamate (50 mg, 82 μmol) in CH₂Cl₂ (5 mL) was added HCl in 1,4-dioxane (4 M, 20.5 μL). The mixture was stirred at 25° C. for 1 hr. The mixture was concentrated under reduced pressure, 3-(3-(4-((4-aminopiperidin-1-yl)methyl)phenyl)-5-(3-chlorophenyl)-3H-imidazo[4,5-b]pyridin-2-yl)pyridin-2-amine (Intermediate 113, 10 mg, HCl salt, yield: 23%) was obtained as light-yellow solid. MS: m/z=510.3 [M+H]⁺. ¹H NMR (400 MHz, Methanol-d₄) δ 8.21 (d, J=8.4 Hz, 1H), 8.07-8.03 (m, 1H), 7.99-7.96 (m, 2H), 7.55 (d, J=8.4 Hz, 2H), 7.48-7.31 (m, 6H), 6.47 (dd, J=7.6, 4.8 Hz, 1H), 3.64 (s, 2H), 2.98-2.93 (m, 2H), 2.80-2.72 (m, 1H), 2.18-2.12 (m, 2H), 1.91-1.85 (m, 2H), 1.55-1.48 (m, 2H).

Intermediate 114: 4-(2-(2-Aminopyridin-3-yl)-3-(4-(chloromethyl)phenyl)-3H-imidazo[4,5-b]pyridin-5-yl)-1-methyl-1,4-diazepan-2-one

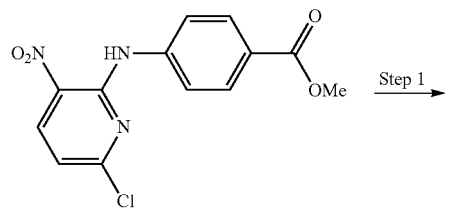

Step 1

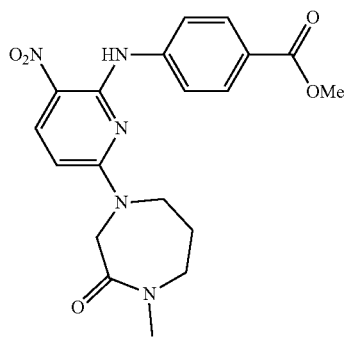

Step 2

-continued

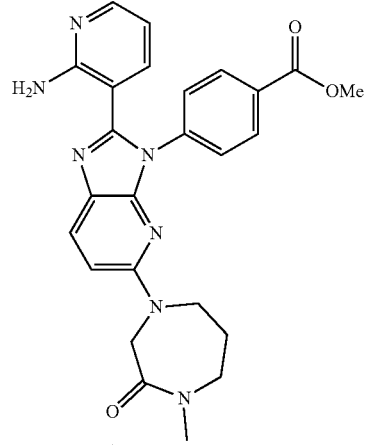

Step 3

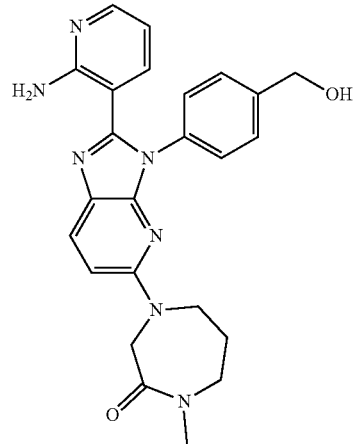

Step 4

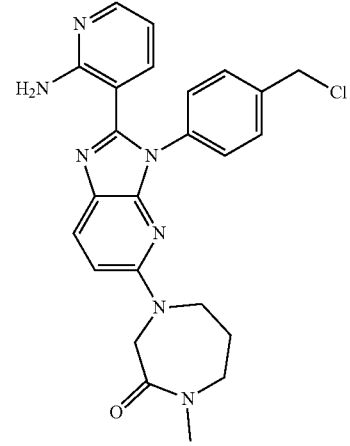

Intermediate 114

Step 1: Methyl 4-((6-(4-methyl-3-oxo-1,4-diazepan-1-yl)-3-nitropyridin-2-yl)amino)benzoate To a solution of methyl 4-((6-chloro-3-nitropyridin-2-yl)amino)benzoate (refer to Intermediate 13 for detail procedures, 5 g, 16.3 mmol), 1-methyl-1,4-diazepan-2-one (4.01 g HCl salt, 24.4 mmol) in ACN (50 mL) was added DIEA (6.30 g, 48.8 mmol). The mixture was stirred at 80° C. for 16 hr under N₂. Water (50 mL) was added, and the mixture was extracted with EtOAc (50 mL×2). The combined organic layers were filtered and concentrated. The filter cake was washed with ACN (10 mL). Methyl 4-((6-(4-methyl-3- oxo-1,4-diazepan-1-yl)-3-nitropyridin-2-yl)amino)benzoate (4.6 g, yield: 71%) was obtained as yellow solid, which was used in the next step without further purification. MS: m/z=400.0 [M+H]$^+$. $^1$H NMR (400 MHz, Dimethylsulfoxide-d$_6$) δ 10.90-10.65 (m, 1H), 8.28 (d, J=8.8 Hz, 1H), 8.12-7.98 (m, 1H), 7.95 (d, J=8.4 Hz, 2H), 7.88-7.75 (m, 1H), 6.65-6.37 (m, 1H), 4.63-4.30 (m, 2H), 3.84 (s, 3H) 3.62-3.47 ((m, 2H), 3.40-3.25 (m, 2H), 2.83 (s, 3H), 1.97-1.793 (m, 2H).

Step 2: Methyl 4-(2-(2-aminopyridin-3-yl)-5-(4-methyl-3-oxo-1,4-diazepan-1-yl)-3H-imidazo[4,5-b]pyridin-3-yl)benzoate To a solution of methyl 4-((6-(4-methyl-3-oxo-1,4-diazepan-1-yl)-3-nitropyridin-2-yl)amino)benzoate (4.60 g, 11.5 mmol) in DMSO (15 mL) and MeOH (1.5 mL) were added 2-aminopyridine-3-carbaldehyde (1.55 g, 12.7 mmol) and Na$_2$S$_2$O$_4$ (6.02 g, 34.6 mmol). The mixture was stirred at 100° C. for 48 hr. Water (300 mL) was added to the mixture and the mixture was extracted with CH$_2$Cl$_2$ (50 mL×2). The combined organic layers were washed with brine (20 mL), dried over Na$_2$SO$_4$, filtered and concentrated. Methyl 4-(2-(2-aminopyridin-3-yl)-5-(4-methyl-3-oxo-1,4-diazepan-1-yl)-3H-imidazo[4,5-b]pyridin-3-yl)benzoate (4.7 g, yield: 87%) was obtained as yellow oil, which was used in next step without further purification. MS: m/z=472.3 [M+H]$^+$. $^1$H NMR (400 MHz, Dimethylsulfoxide-d$_6$) δ 8.06 (d, J=8.4 Hz, 2H), 8.02-7.97 (m, 2H), 7.58 (d, J=8.4 Hz, 2H), 7.45 (br s, 2H), 7.31 (d, J=7.8 Hz, 1H), 6.86 (d, J=8.8 Hz, 1H), 6.57 (dd, J=7.2, 5.6 Hz, 1H), 4.28 (s, 2H), 3.87 (s, 3H), 3.84-3.78 (m, 2H), 3.48-3.44 (m, 2H), 2.76 (s, 3H), 1.76-1.66 (m, 2H).

Step 3: 4-(2-(2-Aminopyridin-3-yl)-3-(4-(hydroxymethyl)phenyl)-3H-imidazo[4,5-b]pyridin-5-yl)-1-methyl-1,4-diazepan-2-one To a solution of methyl 4-(2-(2-aminopyridin-3-yl)-5-(4-methyl-3-oxo-1,4-diazepan-1-yl)-3H-imidazo[4,5-b]pyridin-3-yl)benzoate (1.0 g, 2.12 mmol) in THF (20 mL) was added LiAlH$_4$ (121 mg, 3.18 mmol) in portions under N$_2$ at 0° C. The mixture was stirred at 0° C. for 2 hr under N$_2$. The mixture was diluted with THF (20 mL). Na$_2$SO$_4$·10H$_2$O was added in portions until no bubbles were formed. The resulting mixture was stirred at 25° C. for 20 min and filtered. The filter cake was washed with THF (20 mL×2), the combined filtrate was concentrated. 4-(2-(2-Aminopyridin-3-yl)-3-(4-(hydroxymethyl)phenyl)-3H-imidazo[4,5-b]pyridin-5-yl)-1-methyl-1,4-diazepan-2-one (941 mg) as brown oil, which was used in the next step directly. MS: m/z=444.3 [M+H]$^+$.

Step 4: 4-(2-(2-Aminopyridin-3-yl)-3-(4-(chloromethyl)phenyl)-3H-imidazo[4,5-b]pyridin-5-yl)-1-methyl-1,4-diazepan-2-one To a solution of 4-(2-(2-aminopyridin-3-yl)-3-(4-(hydroxymethyl)phenyl)-3H-imidazo[4,5-b]pyridin-5-yl)-1-methyl-1,4-diazepan-2-one (941 mg, 2.12 mmol) in CH$_2$Cl$_2$ (10 mL) was added SOCl$_2$ (757 mg, 6.36 mmol) at 25° C. The mixture was stirred at 40° C. for 1 hr under N$_2$. The mixture was concentrated. 4-(2-(2-Aminopyridin-3-yl)-3-(4-(chloromethyl)phenyl)-3H-imidazo[4,5-b]pyridin-5-yl)-1-methyl-1,4-diazepan-2-one (Intermediate 114, 980 mg) as brown solid, which was used in the next step directly. MS: m/z=462.2 [M+H]$^+$.

Intermediate 115: 3-(2-(2-Aminopyridin-3-yl)-3-(4-(chloromethyl)phenyl)-3H-imidazo[4,5-b]pyridin-5-yl)benzonitrile

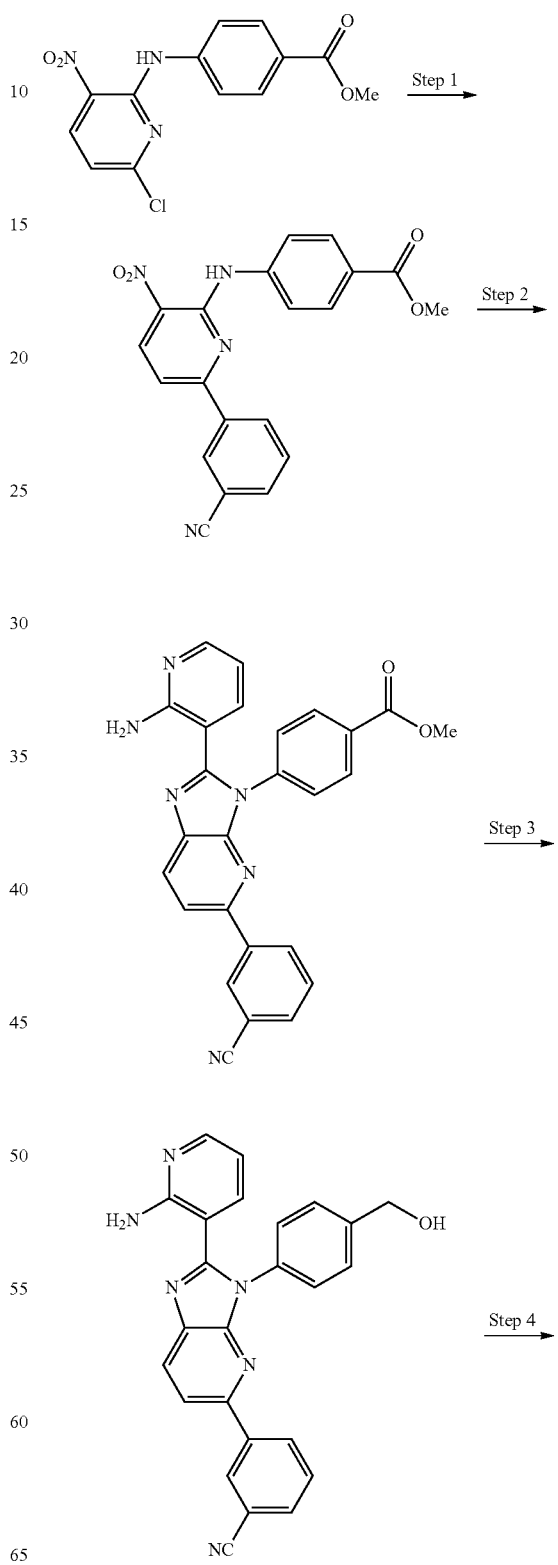

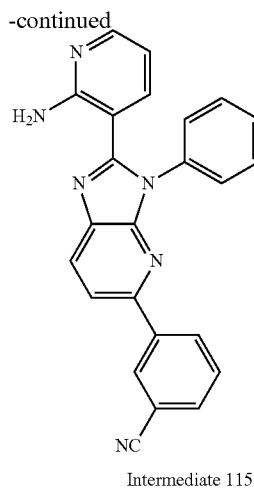

Intermediate 115

Step 1: Methyl 4-((6-(3-cyanophenyl)-3-nitropyridin-2-yl)amino)benzoate

A mixture of methyl 4-((6-chloro-3-nitropyridin-2-yl)amino)benzoate (refer to Intermediate 13 for detail procedures, 25 g, 81.3 mmol), (3-cyanophenyl)boronic acid (13.1 g, 89.4 mmol), $Cs_2CO_3$ (79.4 g, 244 mmol), $Pd(dppf)Cl_2$ (5.95 g, 8.13 mmol) in 1,4-dioxane (250 mL) and $H_2O$ (50 mL) was degassed and purged with $N_2$ three times, and then the mixture was stirred at 100° C. for 16 hr under $N_2$ atmosphere. The reaction mixture was diluted with $H_2O$ (300 mL) and extracted with $CH_2Cl_2$ (200 mL×4). The combined organic layers were washed with brine (300 mL×3), dried over $Na_2SO_4$, filtered and concentrated under reduced pressure. After purified by silica gel flash chromatography (Eluent of 30~100% EtOAc in petroleum ether), methyl 4-((6-(3-cyanophenyl)-3-nitropyridin-2-yl)amino)benzoate (18 g, yield: 60%) was obtained as a yellow solid. MS: m/z=374.9 [M+H]$^+$. $^1$H NMR (400 MHz, Dimethylsulfoxide-d$_6$) δ 10.23 (s, 1H), 8.74 (d, J=8.4 Hz, 1H), 8.04 (dd, J=7.6, 0.8 Hz, 1H), 7.96-7.92 (m, 4H), 7.92-7.85 (m, 2H), 7.73 (dt, J=7.2, 1.2 Hz, 1H), 7.50 (d, J=8.4 Hz, 1H), 3.83 (s, 3H).

Step 2: Methyl 4-(2-(2-aminopyridin-3-yl)-5-(3-cyanophenyl)-3H-imidazo[4,5-b]pyridin-3-yl)benzoate To a solution of methyl 4-((6-(3-cyanophenyl)-3-nitropyridin-2-yl)amino)benzoate (11.6 g, 31 mmol), 2-aminonicotinaldehyde (3.78 g, 31 mmol) in DMSO (120 mL) was added $Na_2S_2O_4$ (21.6 g, 124 mmol). The mixture was stirred at 100° C. for 16 hr. The reaction mixture was diluted with $H_2O$ (300 mL) and extracted with $CH_2Cl_2$ (300 mL×5). The combined organic layers were washed with brine (250 mL×2), dried over $Na_2SO_4$, filtered and concentrated under reduced pressure. After purified by silica gel flash chromatography (Eluent of 30~50% EtOAc in petroleum ether and 50% EtOAc in $CH_2Cl_2$), methyl 4-(2-(2-aminopyridin-3-yl)-5-(3-cyanophenyl)-3H-imidazo[4,5-b]pyridin-3-yl)benzoate (6 g, yield: 43%) was obtained as a black brown solid. MS: m/z=447.0 [M+H]$^+$. $^1$H NMR (400 MHz, Dimethylsulfoxide-d$_6$) δ 8.40 (d, J=8.4 Hz, 1H), 8.08-8.02 (m, 3H), 7.97-7.88 (m, 3H), 7.84-7.78 (m, 1H), 7.72-7.67 (m, 2H), 7.64-7.59 (m, 1H), 7.28 (dd, J=7.6, 1.6 Hz, 1H), 6.86 (br s, 2H), 6.47 (dd, J=8.0, 5.2 Hz, 1H), 3.88 (s, 3H).

Step 3: 3-(2-(2-Aminopyridin-3-yl)-3-(4-(hydroxymethyl)phenyl)-3H-imidazo[4,5-b]pyridin-5-yl)benzonitrile To a solution of methyl 4-(2-(2-aminopyridin-3-yl)-5-(3-cyanophenyl)-3H-imidazo[4,5-b]pyridin-3-yl)benzoate (1.5 g, 3.36 mmol) in THF (50 mL) was added LiAlH$_4$ (2.5 M, 2.69 mL) at 0° C., then the mixture was stirred at 25° C. for 1 hr. The reaction mixture was quenched with $Na_2SO_4$ 10$H_2O$ (2 g) at 0° C., and the mixture was filtered, the filter cake was washed by $CH_2Cl_2$ (30 mL×3), and the filtrate was concentrated under reduced pressure to give 3-(2-(2-aminopyridin-3-yl)-3-(4-(hydroxymethyl)phenyl)-3H-imidazo[4,5-b]pyridin-5-yl)benzonitrile (1.4 g, yield: 86%) as a yellow solid. MS: m/z=419.1 [M+H]$^+$.

Step 4: 3-(2-(2-Aminopyridin-3-yl)-3-(4-(chloromethyl)phenyl)-3H-imidazo[4,5-b]pyridin-5-yl)benzonitrile To a solution of 3-(2-(2-aminopyridin-3-yl)-3-(4-(hydroxymethyl)phenyl)-3H-imidazo[4,5-b]pyridin-5-yl)benzonitrile (1.4 g, 3.35 mmol) in $CH_2Cl_2$ (20 mL) was added SOCl$_2$ (1.19 g, 10.1 mmol) at 25° C. The mixture was stirred at 40° C. for 1 hr. The reaction mixture was quenched with $H_2O$ (20 mL) at 0° C., and the filtrate was concentrated under reduced pressure to give 3-(2-(2-aminopyridin-3-yl)-3-(4-(chloromethyl)phenyl)-3H-imidazo[4,5-b]pyridin-5-yl)benzonitrile (Intermediate 115, 1.6 g, yield: 98%) as a yellow solid. MS: m/z=437.0 [M+H]$^+$.

Intermediate 116: 4-(2-(2-Aminopyridin-3-yl)-3-(4-(chloromethyl)phenyl)-3H-imidazo[4,5-b]pyridin-5-yl)morpholin-3-one hydrochloride

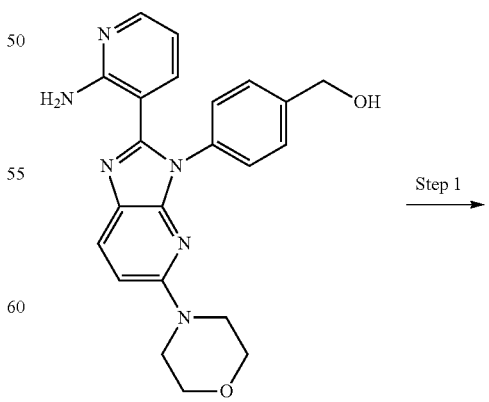

Step 1 →

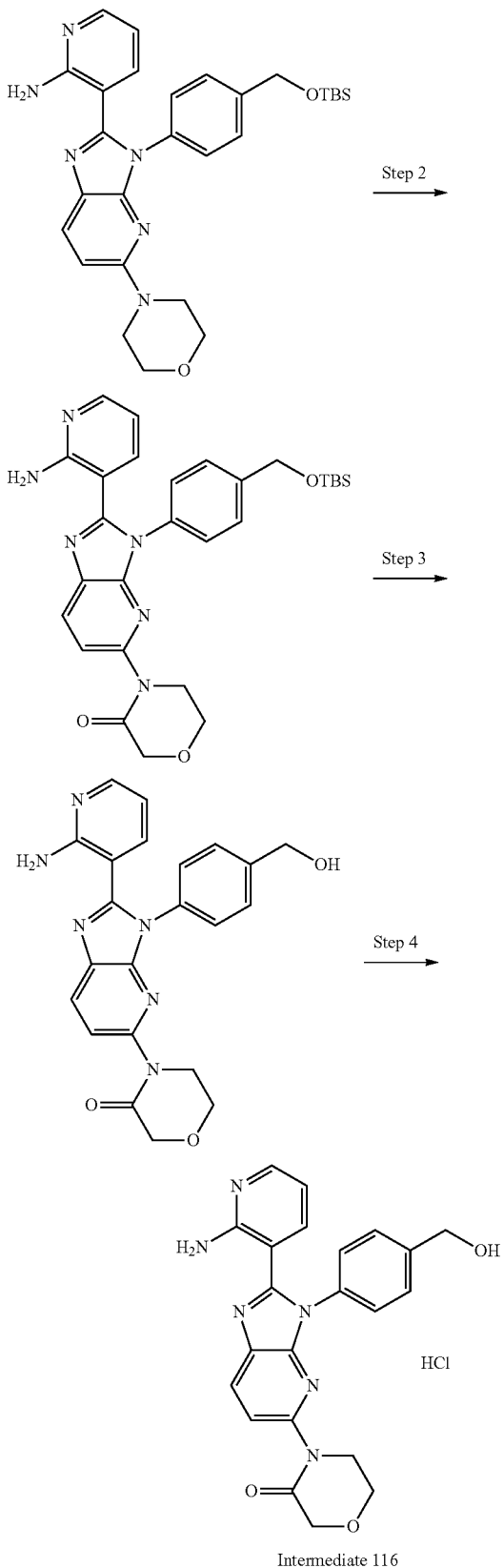

Intermediate 116

Step 1: 3-(3-(4-(((Tert-butyldimethylsilyl)oxy) methyl)phenyl)-5-morpholino-3H-imidazo[4,5-b] pyridin-2-yl)pyridin-2-amine A mixture of (4-(2-(2-aminopyridin-3-yl)-5-morpholino-3H-imidazo[4,5-b]pyridin-3-yl)phenyl)methanol (refer to Intermediate 56 for detail procedures, 5.1 g, 13 mmol), TBSCl (3.8 g, 25 mmol) and imidazole (2.2 g, 32 mmol) in CH$_2$Cl$_2$ (70 mL) was degassed and purged with N$_2$ three times, and then the mixture was stirred at 25° C. for 2 hr under N$_2$ atmosphere. The reaction mixture was diluted with water (40 mL) and extracted with EtOAc (100 mL×2). The combined organic layers were washed with brine (30 mL), dried over Na$_2$SO$_4$, filtered and concentrated under reduced pressure. After purified by silica gel flash chromatography (Eluent of 0~16%, EtOAc in petroleum ether), 3-(3-(4-(((tert-butyldimethylsilyl)oxy)methyl)phenyl)-5-morpholino-3H-imidazo[4,5-b]pyridin-2-yl)pyridin-2-amine (3.5 g, yield: 53%) was obtained as yellow solid. MS: m/z=517.6 [M+H]$^+$. $^1$H NMR (400 MHz, Chloroform-d) δ 8.00 (dd, J=5.2, 1.6 Hz, 1H), 7.90 (d, J=8.8 Hz, 1H), 7.43 (d, J=8.4 Hz, 2H), 7.34-7.28 (m, 2H), 7.04 (dd, J=7.6, 1.6 Hz, 1H), 6.69 (d, J=8.8 Hz, 1H), 6.60 (br s, 2H), 6.34 (dd, J=7.6, 4.8 Hz, 1H), 4.69 (s, 2H), 3.83-3.77 (m, 4H), 3.51-3.43 (m, 4H), 0.96 (s, 9H), 0.13 (s, 6H).

Step 2: 4-(2-(2-Aminopyridin-3-yl)-3-(4-(((tert-butyldimethylsilyl)oxy)methyl)phenyl)-3H-imidazo[4,5-b]pyridin-5-yl)morpholin-3-one To a solution of 3-(3-(4-(((tert-butyldimethylsilyl)oxy)methyl)phenyl)-5-morpholino-3H-imidazo[4,5-b]pyridin-2-yl)pyridin-2-amine (1.0 g, 1.9 mmol) in MeCN (30 mL) was added dropwise NaClO$_2$ (1.4 g, 15 mmol) in H$_2$O (5 mL) at 50° C. over 10 min. The resulting mixture was stirred at 50° C. for 12 hr under CO$_2$ atmosphere. The reaction mixture was concentrated under reduced pressure. After purified by silica gel flash chromatography (Eluent of 0~100% EtOAc in petroleum ether), 4-(2-(2-aminopyridin-3-yl)-3-(4-(((tert-butyldimethylsilyl)oxy)methyl)phenyl)-3H-imidazo[4,5-b]pyridin-5-yl)morpholin-3-one (200 mg, yield: 16%) was obtained as a yellow solid. MS: m/z=531.1 [M+H]-$^1$H NMR (400 MHz, Chloroform-d) δ 8.11-8.02 (m, 3H), 7.48 (d, J=8.4 Hz, 2H), 7.31 (d, J=8.4 Hz, 2H), 7.14-7.11 (m, 1H), 6.99 (br s, 2H), 6.38 (dd, J=7.6, 5.2 Hz, 1H), 4.85 (s, 2H), 4.35 (s, 2H), 3.99 (br s, 4H), 0.97 (s, 9H), 0.14 (s, 6H).

Step 3: 4-(2-(2-Aminopyridin-3-yl)-3-(4-(hydroxymethyl)phenyl)-3H-imidazo[4,5-b]pyridin-5-yl)morpholin-3-one To a solution of 4-(2-(2-aminopyridin-3-yl)-3-(4-(((tert-butyldimethylsilyl)oxy)methyl)phenyl)-3H-imidazo[4,5-b]pyridin-5-yl)morpholin-3-one (200 mg, 377 gmol) in TBAF (1 M, 5 mL). The mixture was stirred at 25° C. for 1 hr. The reaction mixture was diluted with H$_2$O (30 mL) and extracted with EtOAc (30 mL×2). The combined organic layers were washed with brine (30 mL), dried over Na$_2$SO$_4$, filtered and concentrated under reduced pressure. The crude 4-(2-(2-aminopyridin-3-yl)-3-(4-(hydroxymethyl)phenyl)-3H-imidazo[4,5-b]pyridin-5-yl)morpholin-3-one (157 mg, yield: 100%) was used in the next step without further purification. MS: m/z=417.1 [M+H]$^+$.

Step 4: 4-(2-(2-Aminopyridin-3-yl)-3-(4-(chloromethyl)phenyl)-3H-imidazo[4,5-b]pyridin-5-yl)morpholin-3-one hydrochloride To a solution of 4-(2-(2-aminopyridin-3-yl)-3-(4-(hydroxymethyl)phenyl)-3H-imidazo[4,5-b]pyridin-5-yl)morpholin-3-one (150 mg, 360 μmol) in CH$_2$Cl$_2$ (2 mL) was added SOCl$_2$ (129 mg, 1 mmol). The mixture was stirred at 25° C. for 1 hr. The reaction mixture was concentrated under reduced pressure. The crude 4-(2-(2-Aminopyridin-3-yl)-3-(4-(chloromethyl)phenyl)-3H-imidazo[4,5-b]pyridin-5-yl)morpholin-3-one hydrochloride (Intermediate 116, 170 mg HCl salt, yield: 100%) was used in the next step without further purification. MS: m/z=435.2 [M+H]$^+$.

Intermediate 117: 3-(5-Chloro-3-(4-(chloromethyl)phenyl)-3H-imidazo[4,5-b]pyridin-2-yl)pyridin-2-amine

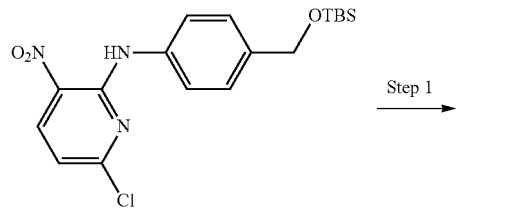

Step 1

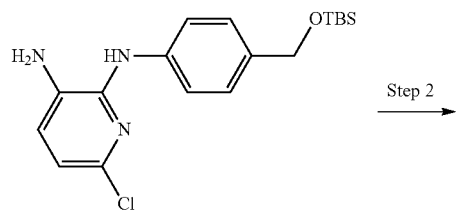

Step 2

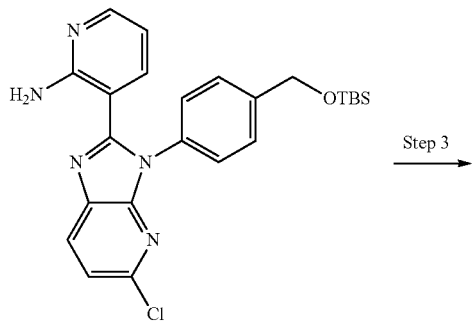

Step 3

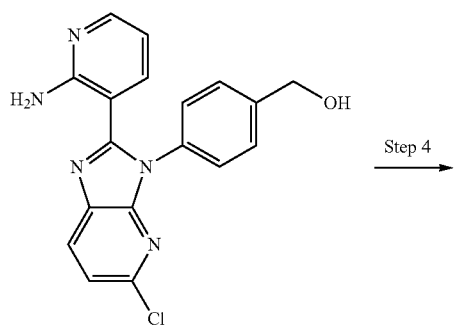

Step 4

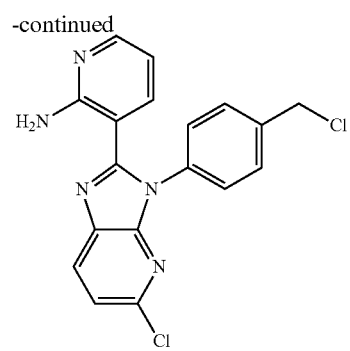

Intermediate 117

Step 1: N$^2$-(4-(((tert-butyldimethylsilyl)oxy)methyl)phenyl)-6-chloropyridine-2,3-diamine To a solution of N-(4-(((tert-butyldimethylsilyl)oxy)methyl)phenyl)-6-chloro-3-nitropyridin-2-amine (refer to Intermediate 105 for detail procedures, 5 g, 12.7 mmol) in EtOH (50 mL) and H$_2$O (10 mL) was added Fe (1.42 g, 25.4 mmol) and NH$_4$Cl (3.39 g, 63.5 mmol). The mixture was degassed and purged with N$_2$ three times and stirred at 80° C. for 2 hr under N$_2$. The reaction mixture was filtered and concentrated under reduced pressure to give N$^2$-(4-(((tert-butyldimethylsilyl)oxy)methyl)phenyl)-6-chloropyridine-2,3-diamine (4.62 g, crude) as a black solid, which was used in the next step directly. MS: m/z=364.2 [M+H]$^+$.

Step 2: 3-(3-(4-(((tert-butyldimethylsilyl)oxy)methyl)phenyl)-5-chloro-3H-imidazo[4,5-b]pyridin-2-yl)pyridin-2-amine To a solution of N$^2$-(4-(((tert-butyldimethylsilyl)oxy)methyl)phenyl)-6-chloropyridine-2,3-diamine (13.9 g, 38.1 mmol), 2-aminonicotinaldehyde (4.65 g, 38.1 mmol) in EtOH (150 mL) was added InCl$_3$ (842 mg, 3.81 mmol). The mixture was degassed and purged with N$_2$ three times and stirred at 80° C. for 2 hr under N$_2$. Then MnO$_2$ (19.9 g, 228 mmol) was added. The mixture was degassed and purged with N$_2$ three times and stirred at 80° C. for 2 hr under N$_2$. The reaction mixture was filtered and concentrated under reduced pressure. After purified by silica gel flash chromatography (Eluent of 1~50% EtOAc in petroleum ether), 3-(3-(4-(((tert-butyldimethylsilyl)oxy)methyl)phenyl)-5-chloro-3H-imidazo[4,5-b]pyridin-2-yl)pyridin-2-amine (6.02 g, 11.8 mmol) was obtained as a gray solid. MS: m/z=466.3 [M+H]$^+$. $^1$H NMR (400 MHz, Chloroform-d) δ 8.06-8.00 (m, 2H), 7.49 (d, J=8.0 Hz, 2H), 7.31 (dd, J=1.8, 8.4 Hz, 3H), 7.09 (dd, J=7.6, 1.2 Hz, 1H), 6.80 (br s, 2H), 6.36 (dd, J=7.6, 5.2 Hz, 1H), 4.83 (s, 2H), 0.97 (s, 9H), 0.14 (s, 6H).

Step 3: (4-(2-(2-Aminopyridin-3-yl)-5-chloro-3H-imidazo[4,5-b]pyridin-3-yl)phenyl)methanol To a solution of 3-(3-(4-(((tert-butyldimethylsilyl)oxy)methyl)phenyl)-5-chloro-3H-imidazo[4,5-b]pyridin-2-yl)pyridin-2-amine (500 mg, 1.07 mmol) in CH$_2$Cl$_2$ (5 mL) was added TBAF (1 M, 1.61 mL). The mixture was degassed and purged with N$_2$ three times and stirred at 25° C. for 2 hr under N$_2$. The reaction mixture was quenched with Sat. NH$_4$Cl (20 mL) at 25° C., and then extracted with CH$_2$Cl$_2$ (10 mL×3). The combined organic layers were washed with brine (20 mL×2), dried over Na$_2$SO$_4$, filtered and concentrated under reduced pressure. (4-(2-(2-aminopyridin-3-yl)-5-chloro-3H-imidazo[4,5-b]pyridin-3-yl)phenyl)methanol (377 mg, crude) was obtained as a yellow solid. MS: m/z=352.2 [M+H]$^+$.

Step 4: 3-(5-Chloro-3-(4-(chloromethyl)phenyl)-3H-imidazo[4,5-b]pyridin-2-yl)pyridin-2-amine To a solution of (4-(2-(2-aminopyridin-3-yl)-5-chloro-3H-imidazo[4,5-b]pyridin-3-yl)phenyl)methanol (377 mg, 1.07 mmol) in CH$_2$Cl$_2$ (5 mL) was added SOCl$_2$ (1.28 g, 10.7 mmol). The mixture was degassed and purged with N$_2$ three times and stirred at 25° C. for 4 hr under N$_2$. The reaction mixture was concentrated under reduced pressure to give 3-(5-chloro-3-(4-(chloromethyl)phenyl)-3H-imidazo[4,5-b]pyridin-2-yl)pyridin-2-amine (Intermediate 117, 430 mg, crude) as a gray solid. MS: mm/z=370.1 [M+H]$^+$.

Intermediate 118: 3-(3-(4-(Chloromethyl)phenyl)-5-cyclopentyl-3H-imidazo[4,5-b]pyridin-2-yl)pyridin-2-amine

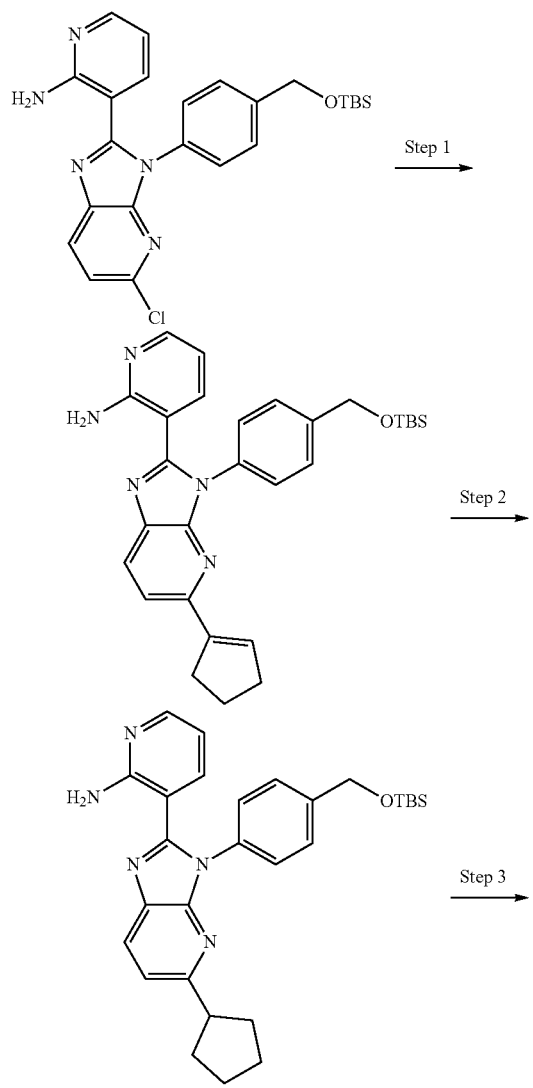

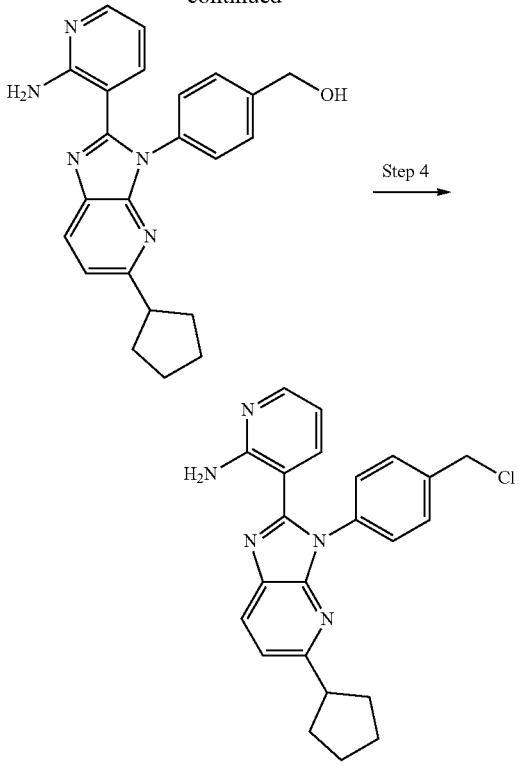

Intermediate 118

Step 1: 3-(3-(4-(((Tert-butyldimethylsilyl)oxy)methyl)phenyl)-5-(cyclopent-1-en-1-yl)-3H-imidazo[4,5-b]pyridin-2-yl)pyridin-2-amine A mixture of 3-(3-(4-(((ter-butyldimethylsilyl)oxy)methyl)phenyl)-5-chloro-3H-imidazo[4,5-b]pyridin-2-yl)pyridin-2-amine (refer to Intermediate 117 for detail procedures, 1 g, 2.15 mmol), cyclopenten-1-ylboronic acid (288 mg, 2.57 mmol), Cs$_2$CO$_3$ (2.1 g, 6.4 mmol), Pd(dppf)Cl$_2$ (157 mg, 215 mol) in 1,4-dioxane (10 mL) and H$_2$O (2 mL) was degassed and purged with N$_2$ three times, then the mixture was stirred at 100° C. for 16 hr under N$_2$ atmosphere. The reaction mixture was poured into H$_2$O (15 mL), extracted with EtOAc (15 mL×3). The combined organic layers were dried over anhydrous Na$_2$SO$_4$, filtered and concentrated under reduced pressure. After purified by silica gel flash chromatography (Eluent of 0~35% EtOAc in petroleum ether), 3-(3-(4-(((tert-butyldimethylsilyl)oxy)methyl)phenyl)-5-(cyclopent-1-en-1-yl)-3H-imidazo[4,5-b]pyridin-2-yl)pyridin-2-amine (930 mg, yield: 84%) was obtained as a gray solid. MS: m/z=498.1 [M+H]$^+$. $^1$H NMR (400 MHz, Chloroform-d) δ 8.04 (dd, J=4.8, 1.6 Hz, 1H), 7.98 (d, J=8.4 Hz, 1H), 7.50-7.32 (m, 5H), 7.12 (dd, J=7.6, 1.6 Hz, 1H), 6.67 (br s, 2H), 6.56 (t, J=2.0 Hz, 1H), 6.36 (dd, J=7.6, 5.2 Hz, 1H), 4.84 (s, 2H), 2.88-2.72 (m, 2H), 2.59-2.50 (m, 2H), 2.01 (d, J=7.6 Hz, 1H), 1.86-1.74 (m, 1H), 0.97 (s, 9H), 0.14 (s, 6H)

Step 2: 3-(3-(4-(((Tert-butyldimethylsilyl)oxy)methyl)phenyl)-5-cyclopentyl-3H-imidazo[4,5-b]pyridin-2-yl)pyridin-2-amine To a solution of 3-(3-(4-(((tert-butyldimethylsilyl)oxy)methyl)phenyl)-5-(cyclopent-1-en-1-yl)-3H-imidazo[4,5-b]

pyridin-2-yl)pyridin-2-amine (160 mg, 322 μmol) in MeOH (10 mL) was added Pd/C (230 mg, 216 μmol, 10% purity) under $N_2$. The suspension was degassed under reduced pressure and purged with $H_2$ several times. The mixture was stirred under $H_2$ (15 psi) at 25° C. for 4 hr. The reaction mixture was filtered and concentrated under reduced pressure. The crude 3-(3-(4-(((tert-butyldimethylsilyl)oxy)methyl)phenyl)-5-cyclopentyl-3H-imidazo[4,5-b]pyridin-2-yl)pyridin-2-amine (150 mg, yield: 94%) was obtained as a yellow solid. MS: m/z=500.3 [M+H]$^+$. $^1$H NMR (400 MHz, Dimethylsulfoxide-d$_6$) δ 8.07 (d, J=8.0 Hz, 1H), 7.97 (dd, J=4.4, 1.6 Hz, 1H), 7.46-7.43 (m, 2H), 7.40-7.36 (m, 2H), 7.29 (d, J=8.4 Hz, 1H), 7.13 (dd, J=7.2, 1.6 Hz, 1H), 6.93 (br s, 2H), 6.36 (dd, J=7.6, 4.8 Hz, 1H), 4.80 (s, 2H), 4.10-4.08 (m, 1H), 1.98-1.94 (m, 2H), 1.75-1.67 (m, 4H), 1.64-1.58 (m, 2H), 0.92 (s, 9H), 0.10 (s, 6H).

Step 3: (4-(2-(2-Aminopyridin-3-yl)-5-cyclopentyl-3H-imidazo[4,5-b]pyridin-3-yl)phenyl)methanol To a solution of 3-(3-(4-(((tert-butyldimethylsilyl)oxy)methyl)phenyl)-5-cyclopentyl-3H-imidazo[4,5-b]pyridin-2-yl)pyridin-2-amine (150 mg, 300 μmol) in THF (2 mL) was added TBAF (157 mg, 600 μmol). The mixture was stirred at 25° C. for 0.3 hr. The reaction mixture was poured into $H_2O$ (15 mL), extracted with EtOAc (15 mL×3). The combined organic layers were dried over anhydrous $Na_2SO_4$, filtered and concentrated under reduced pressure., (4-(2-(2-aminopyridin-3-yl)-5-cyclopentyl-3H-imidazo[4,5-b]pyridin-3-yl)phenyl)methanol (110 mg, crude) as a yellow oil. MS: m/z=386.1 [M+H]$^+$.

Step 4: 3-(3-(4-(Chloromethyl)phenyl)-5-cyclopentyl-3H-imidazo[4,5-b]pyridin-2-yl)pyridin-2-amine To a solution of (4-(2-(2-aminopyridin-3-yl)-5-cyclopentyl-3H-imidazo[4,5-b]pyridin-3-yl)phenyl)methanol (110 mg, 285 μmol) in $CH_2Cl_2$ (2 mL) was added $SOCl_2$ (68 mg, 571 μmol). The mixture was stirred at 40° C. for 0.5 hr. The mixture was concentrated under reduced pressure to give the crude 3-(3-(4-(chloromethyl)phenyl)-5-cyclopentyl-3H-imidazo[4,5-b]pyridin-2-yl)pyridin-2-amine (Intermediate 118, 100 mg) as a yellow solid. MS: m/z=404.1 [M+H]$^+$.

Intermediate 119: 2-(2-Aminopyridin-3-yl)-3-(4-(chloromethyl)phenyl)-N,N-dimethyl-3H-imidazo[4,5-b]pyridin-5-amine

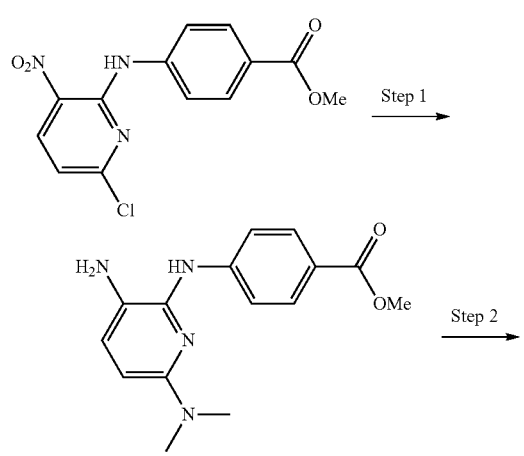

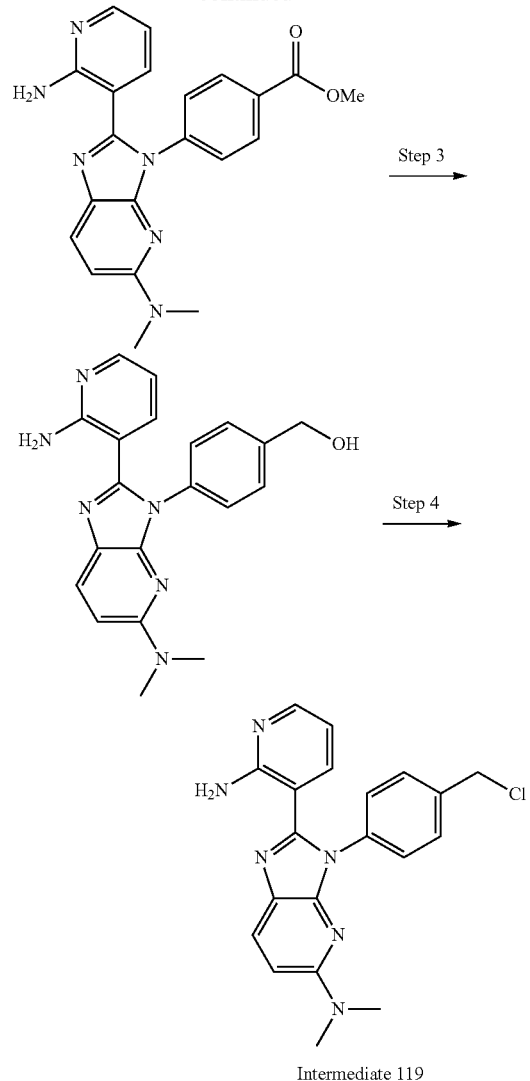

Intermediate 119

Step 1: Methyl 4-((6-(dimethylamino)-3-nitropyridin-2-yl)amino)benzoate

To a solution of methyl 4-((6-chloro-3-nitropyridin-2-yl)amino)benzoate (refer to Intermediate 13 for detail procedures, 5 g, 16.3 mmol) in MeCN (50 mL) were added DIEA (10.5 g, 81.3 mmol) and dimethylamine (1.33 g, 1.49 mmol). The mixture was stirred at 90° C. for 16 hr. The reaction mixture was quenched with $H_2O$ (50 mL) at 25° C., and then extracted with $CH_2Cl_2$ (50 mL×3). The combined organic layers were washed with brine (50 mL), dried over $Na_2SO_4$, filtered and concentrated under reduced pressure. The crude product was triturated with MeCN at 25° C. for 30 min, methyl 4-((6-(dimethylamino)-3-nitropyridin-2-yl)amino)benzoate (4.5 g, yield: 87%) was obtained as a yellow solid. MS: m/z=317.0 [M+H]$^+$. $^1$H NMR (400 MHz, Dimethyl-sulfoxide-d$_6$) δ 10.86 (s, 1H), 8.22 (d, J=9.6 Hz, 1H), 7.95 (d, J=8.8 Hz, 1H), 7.89 (d, J=8.8 Hz, 1H), 6.42 (d, J=9.6 Hz, 1H), 3.83 (s, 3H), 3.19 (s, 6H).

Step 2: Methyl 4-(2-(2-aminopyridin-3-yl)-5-(dimethylamino)-3H-imidazo[4,5-b]pyridin-3-yl)benzoate To a solution of methyl 4-((6-(dimethylamino)-3-nitropyridin-2-yl)amino)benzoate (4.5 g, 14.2 mmol) in DMSO (50 mL) were added $Na_2S_2O_4$ (9.91 g, 56.9 mmol, 87% purity) and 2-aminonicotinaldehyde (1.91 mg, 15.7 mmol). The mixture was stirred at 100° C. for 16 hr. The reaction mixture was quenched with $H_2O$ (100 mL) at 25° C., and then extracted with $CH_2Cl_2$ (100 mL×3). The combined organic layers were washed with brine (50 mL), dried over $Na_2SO_4$, filtered and concentrated under reduced pressure. After triturated with $CH_2Cl_2$:EtOAc (1:10) at 25° C. for 30 min, methyl 4-(2-(2-aminopyridin-3-yl)-5-(dimethylamino)-3H-imidazo[4,5-b]pyridin-3-yl)benzoate (6 g, yield: 95%) was obtained as a brown solid. MS: m/z=389.1 $[M+H]^+$. $^1$H NMR (400 MHz, Dimethylsulfoxide-$d_6$) δ 8.07 (d, J=8.4 Hz, 2H), 7.97 (dd, J=5.2, 1.6 Hz, 1H), 7.94 (d, J=8.8 Hz, 1H), 7.56 (d, J=8.4 Hz, 2H), 7.36 (br s, 2H), 7.19 (d, J=7.6 Hz, 1H), 6.73 (d, J=8.8 Hz, 1H), 6.49 (dd, J=7.6, 5.2 Hz, 1H), 3.88 (s, 3H), 3.01 (s, 3H), 2.54 (s, 3H).

Step 3: (4-(2-(2-Aminopyridin-3-yl)-5-(dimethylamino)-3H-imidazo[4,5-b]pyridin-3-yl)phenyl)methanol To a solution of methyl 4-(2-(2-aminopyridin-3-yl)-5-(dimethylamino)-3H-imidazo[4,5-b]pyridin-3-yl)benzoate (500 mg, 1.29 mmol) in THF (5 mL) was added $LiAlH_4$ (97.7 mg, 2.5 mmol) at 0° C. The resulting mixture was stirred at 25° C. for 1 hr. The reaction mixture was filtered, and concentrated to give (4-(2-(2-aminopyridin-3-yl)-5-(dimethylamino)-3H-imidazo[4,5-b]pyridin-3-yl)phenyl)methanol (350 mg, yield: 75%) as a yellow solid. MS: m/z=361.1 $[M+H]^+$.

Step 4: 2-(2-Aminopyridin-3-yl)-3-(4-(chloromethyl)phenyl)-N,N-dimethyl-3H-imidazo[4,5-b]pyridin-5-amine To a solution of (4-(2-(2-aminopyridin-3-yl)-5-(dimethylamino)-3H-imidazo[4,5-b]pyridin-3-yl)phenyl)methanol (350 mg, 971 μmol) in $CH_2Cl_2$ (5 mL) was added $SOCl_2$ (347 mg, 2.91 mmol). The mixture was stirred at 40° C. for 0.5 hr. The reaction was concentrated under reduced pressure to give 2-(2-aminopyridin-3-yl)-3-(4-(chloromethyl)phenyl)-N,N-dimethyl-3H-imidazo[4,5-b]pyridin-5-amine (Intermediate 119,430 mg, yield: 82%) as a yellow solid. MS: m/z=379.0 $[M+H]^+$.

Intermediate 120: 4-(Methyl(piperidin-4-yl)amino)pyrimidine-2-carbonitrile

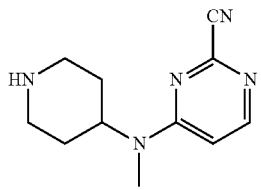

Intermediate 120

Step 1: tert-Butyl 4-((2-cyanopyrimidin-4-yl)(methyl)amino)piperidine-1-carboxylate To a solution of tert-butyl 4-(methylamino)piperidine-1-carboxylate (500 mg, 2.3 mmol) and 4-chloropyrimidine-2-carbonitrile (326 mg, 2.3 mmol) in DMF (5 mL) were added NaI (35 mg, 233 μmol) and $K_2CO_3$ (645 mg, 4.7 mmol). The mixture was stirred at 80° C. for 2 hr. The reaction mixture was quenched with $H_2O$ (10 mL) at 25° C., and extracted with EtOAc (10 mL×2). The combined organic layers were washed with brine (10 mL), dried over $Na_2SO_4$, filtered and concentrated under reduced pressure. After purified by silica gel flash chromatography (Eluent of 0~50%, EtOAc in petroleum ether), tert-butyl 4-((2-cyanopyrimidin-4-yl)(methyl)amino)piperidine-1-carboxylate (700 mg, yield: 95%) was obtained as a light yellow solid. MS: m/z=318.2 $[M+H]^+$. $^1$H NMR (400 MHz, Chloroform-d) S 8.19 (d, J=6.4 Hz, 1H), 6.51 (d, J=6.0 Hz, 1H), 5.29-4.62 (m, 1H), 4.25 (s, 2H), 2.93-2.81 (m, 5H), 1.68-1.62 (m, 4H), 1.47 (s, 9H).

Step 2: 4-(Methyl(piperidin-4-yl)amino)pyrimidine-2-carbonitrile

To a solution of tert-butyl 4-((2-cyanopyrimidin-4-yl)(methyl)amino)piperidine-1-carboxylate (150 mg, 473 μmol) in $CH_2Cl_2$ (3 mL) was added TFA (1.5 g, 13 mmol). The mixture was stirred at 25° C. for 0.5 hr. The reaction mixture was concentrated under reduced pressure to give 4-(methyl(piperidin-4-yl)amino)pyrimidine-2-carbonitrile (Intermediate 120, 156 mg) as a light yellow oil, which was used in the next step without further purification. MS: m/z=218.0 $[M+H]^+$.

Intermediate 121: 4-((4-Methylpiperidin-4-yl)amino)pyrimidine-2-carbonitrile

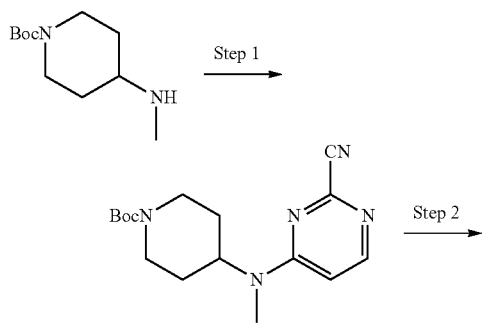

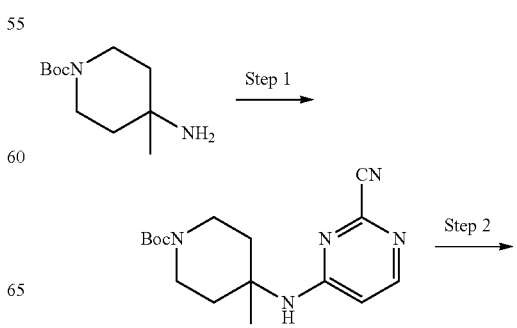

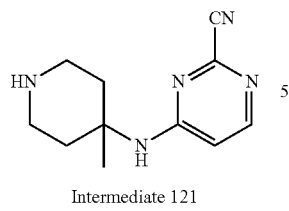

Intermediate 121

Step 1: tert-Butyl 4-((2-cyanopyrimidin-4-yl)amino)-4-methylpiperidine-1-carboxylate To a solution of tert-butyl 4-amino-4-methylpiperidine-1-carboxylate (500 mg, 2.3 mmol) and 4-chloropyrimidine-2-carbonitrile (326 mg, 2.3 mmol) in DMF (5 mL) were added NaI (35 mg 233 μmol) and $K_2CO_3$ (645 mg, 4.7 mmol). The mixture was stirred at 80° C. for 2 hr. The reaction mixture was quenched with $H_2O$ (10 mL) at 25° C., and extracted with EtOAc (10 mL×2). The combined organic layers were washed with brine (10 mL), dried over $Na_2SO_4$, filtered and concentrated under reduced pressure. After purified by silica gel flash chromatography (Eluent of 0~50% EtOAc in petroleum ether), tert-butyl 4-((2-cyanopyrimidin-4-yl)amino)-4-methylpiperidine-1-carboxylate (700 mg, yield: 95%) was obtained as a light-yellow oil. MS: m/z=318.1 [M+H]$^+$. $^1$H NMR (400 MHz, Chloroform-d) δ 8.11 (d, J=6.0 Hz, 1H), 6.47 (d, J=6.0 Hz, 1H), 5.10 (br s, 1H), 3.66-3.59 (m, 2H), 3.26-3.19 (m, 2H), 1.74-1.68 (m, 2H), 1.51 (s, 3H), 1.45 (s, 9H), 1.44-1.43 (m, 2H).

Step 2: 4-((4-Methylpiperidin-4-yl)amino)pyrimidine-2-carbonitrile

To a solution of tert-butyl 4-((2-cyanopyrimidin-4-yl)amino)-4-methylpiperidine-1-carboxylate (150 mg, 473 μmol) in $CH_2Cl_2$ (5 mL) was added TFA (1.5 g, 13 mmol). The mixture was stirred at 25° C. for 0.5 hr. The reaction mixture was concentrated under reduced pressure to give 4-((4-methylpiperidin-4-yl)amino)pyrimidine-2-carbonitrile (Intermediate 121, 100 mg) as a light-yellow oil, which was used directly in the next step. MS: m/z=218.0 [M+H]$^+$.

Intermediate 122: 3-(3-(4-(Chloromethyl)phenyl)-5-(3-methoxyphenyl)-3H-imidazo[4,5-b]pyridin-2-yl)pyridin-2-amine

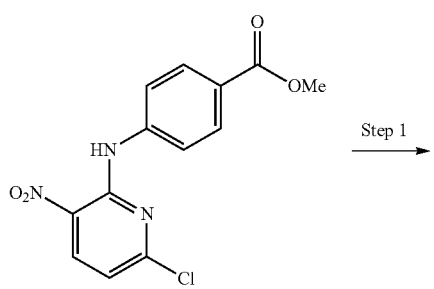

Step 1

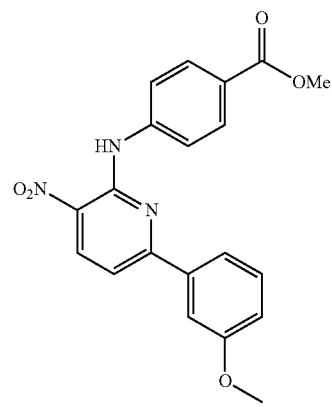

Step 2

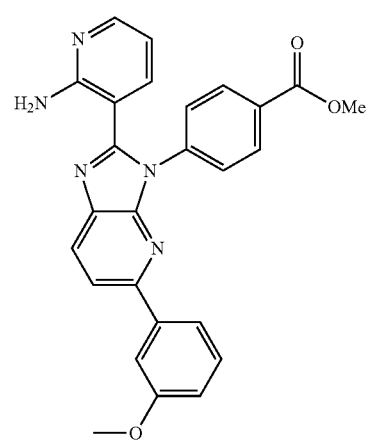

Step 3

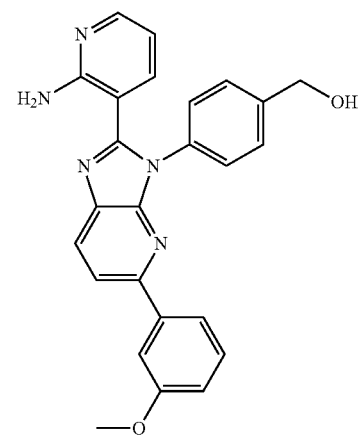

Step 4

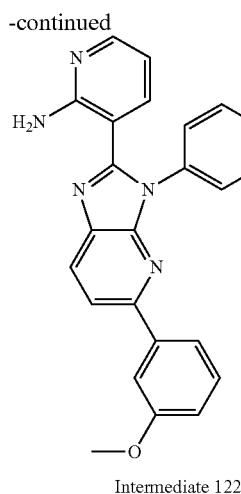

Intermediate 122

Step 1: Methyl 4-((6-(3-methoxyphenyl)-3-nitropyridin-2-yl)amino)benzoate

To a solution of methyl 4-((6-chloro-3-nitropyridin-2-yl)amino)benzoate (refer to Intermediate 13 for detail procedures, 5 g, 16 mmol) and 2-(3-methoxyphenyl)-4,4,5,5-tetramethyl-1,3,2-dioxaborolane (3.8 g, 16 mmol) in 1,4-dioxane (50 mL) and H$_2$O (5 m L) were added Cs$_2$CO$_3$ (16 g, 49 mmol) and Pd(dppf)Cl$_2$ (1.2 g, 1.6 mmol) at 25° C. The mixture was stirred at 80° C. for 12 hr. The reaction mixture was poured into water (900 mL), extracted with EtOAc (900 mL×2). The combined organic layers were washed with brine (500 ml) and dried over anhydrous Na$_2$SO$_4$, filtered and concentrated to dryness. After purified by silica gel flash chromatography (Eluent of 0~100% EtOAc in petroleum ether), methyl 4-((6-(3-methoxyphenyl)-3-nitropyridin-2-yl)amino)benzoate (4.93 g, yield: 80%) was obtained as a yellow solid. MS: m/z=380.0 [M+H]$^+$.

Step 2: Methyl 4-(2-(2-aminopyridin-3-yl)-5-(3-methoxyphenyl)-3H-imidazo[4,5-b]pyridin-3-yl)benzoate A mixture of methyl 4-((6-(3-methoxyphenyl)-3-nitropyridin-2-yl)amino)benzoate (6.2 g, 16 mmol) and Na$_2$S$_2$O$_4$ (2.8 g, 16 mmol) in DMSO (60 mL) was degassed and purged with N$_2$ three times, and then the mixture was stirred at 100° C. for 16 hr under N$_2$ atmosphere. The reaction mixture was diluted with H$_2$O (600 mL) and extracted with CH$_2$Cl$_2$ (900 mL). The combined organic layers were washed with brine (300 mL), dried over Na$_2$SO$_4$, filtered and concentrated under reduced pressure. After purified by silica gel flash chromatography (Eluent of 0~80%, EtOAc in petroleum ether), methyl 4-(2-(2-aminopyridin-3-yl)-5-(3-methoxyphenyl)-3H-imidazo[4,5-b]pyridin-3-yl)benzoate (2.0 g, yield: 27%) was obtained as a brown solid. MS: m/z=452.1 [M+H]$^+$. $^1$H NMR (400 MHz, Chloroform-d) δ 8.20 (d, J=8.4 Hz, 2H), 8.13 (d, J=8.4 Hz, 1H), 8.08 (dd, J=4.8, 1.6 Hz, 1H), 7.82 (d, J=8.4 Hz, 1H), 7.62-7.53 (m, 4H), 7.39-7.33 (m, 1H), 7.07 (dd, J=8.0, 1.6 Hz, 1H), 6.97-6.90 (m, 1H), 6.68 (br s, 2H), 6.40 (dd, J=7.6, 4.8 Hz, 1H), 3.97 (s, 3H), 3.86 (s, 3H).

Step 3: (4-(2-(2-Aminopyridin-3-yl)-5-(3-methoxyphenyl)-3H-imidazo[4,5-b]pyridin-3-yl)phenyl)methanol To a solution of methyl 4-(2-(2-aminopyridin-3-yl)-5-(3-methoxyphenyl)-3H-imidazo[4,5-b]pyridin-3-yl)benzoate (1.0 g, 2 mmol) in THF (10 mL) was added LiAlH$_4$ (2.5 M, 1.8 mL) at 0° C. The mixture was stirred at 25° C. for 1 hr. The mixture was added Na$_2$SO$_4$·10H$_2$O (1 g) slowly at 0° C., then stirred at 25° C. for 20 min. The mixture was filtered and concentrated under reduced pressure to give (4-(2-(2-aminopyridin-3-yl)-5-(3-methoxyphenyl)-3H-imidazo[4,5-b]pyridin-3-yl)phenyl)methanol (800 mg as a yellow solid.

Step 4: 3-(3-(4-(Chloromethyl)phenyl)-5-(3-methoxyphenyl)-3H-imidazo[4,5-b]pyridin-2-yl)pyridin-2-amine To a solution of (4-(2-(2-aminopyridin-3-yl)-5-(3-methoxyphenyl)-3H-imidazo[4,5-b]pyridin-3-yl)phenyl)methanol (800 mg, 1.9 mmol) in CH$_2$Cl$_2$ (5 mL) was added SOCl$_2$ (450 mg, 3.8 mmol). The mixture was stirred at 40° C. for 1 hr. The mixture was concentrated under reduced pressure, 3-(3-(4-(chloromethyl)phenyl)-5-(3-methoxyphenyl)-3H-imidazo[4,5-b]pyridin-2-yl)pyridin-2-amine (Intermediate 122, 800 mg, crude) was obtained as a yellow solid. MS: m/z=442.1 [M+H]$^+$.

Intermediate 123: 3-(5-(Tert-butyl)-3-(4-(chloromethyl)phenyl)-3H-imidazo[4,5-b]pyridin-2-yl)pyridin-2-amine

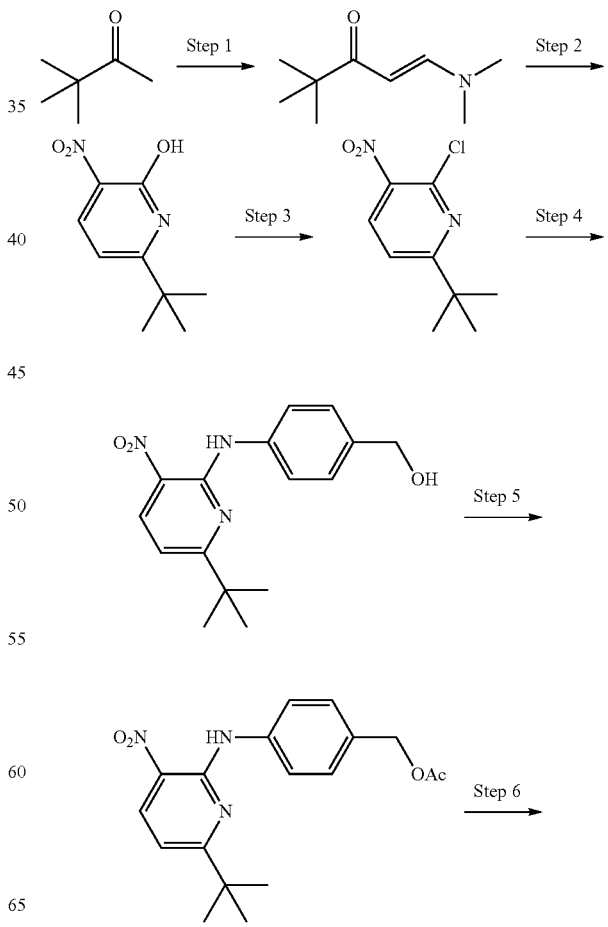

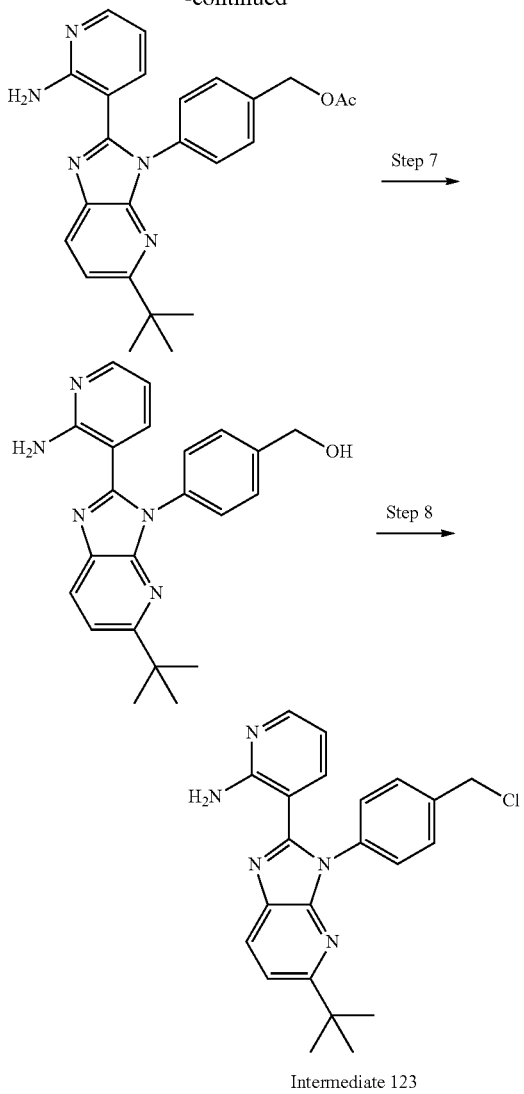

Intermediate 123

Step 1: (E)-1-(dimethylamino)-4,4-dimethylpent-1-en-3-one

To a solution of 3,3-dimethylbutan-2-one (10 g, 100 mmol) in DMF (100 mL) was added DMF-DMA (23.8 g, 200 mmol) and CH$_3$ONa (539 mg, 9.98 mmol). The mixture was stirred at 100° C. for 16 hr. The mixture was diluted with H$_2$O (500 mL) and extracted with CH$_2$Cl$_2$ (500 mL×2). The combined organic layers were washed with brine (500 mL), dried over Na$_2$SO$_4$, filtered and concentrated under reduced pressure to give (E)-1-(dimethylamino)-4,4-dimethylpent-1-en-3-one (10.6 g, yield: 68%) as a brown oil. MS: m/z=156.2 [M+H]$^+$.

Step 2: 6-(Tert-butyl)-3-nitropyridin-2-ol

To a solution of (E)-1-(dimethylamino)-4,4-dimethyl-pent-1-en-3-one (10.6 g, 68.3 mmol) in H$_2$O (100 mL) were added piperidinium acetate (5 g, 34 mmol) and 2-nitroacetamide (10.6 g, 102 mmol). The mixture was stirred at 25° C. for 16 hr. The reaction mixture was filtered and the filter cake was dried to give 6-(tert-butyl)-3-nitropyridin-2-ol (3.1 g, yield: 23%) as a light-yellow solid. MS: m/z=197.1 [M+H]$^+$. $^1$H NMR (400 MHz, Chloroform-d) δ 8.41 (d, J=8.0 Hz, 1H), 6.34 (d, J=7.6 Hz, 1H), 1.44 (s, 9H).

Step 3: 6-(Ter-butyl)-3-nitropyridin-2-ol

A solution of 6-(tert-butyl)-3-nitropyridin-2-ol (3.1 g, 15.8 mmol) in POCl$_1$ (5 mL) was stirred at 100° C. for 16 hr. The reaction mixture was concentrated under reduced pressure to remove POCl$_3$. The reaction mixture was poured into H$_2$O (20 mL), extracted with CH$_2$Cl$_2$ (60 mL). The organic phase was dried over anhydrous Na$_2$SO$_4$, filtered and concentrated under reduced pressure. 6-(tert-Butyl)-3-nitropyridin-2-ol (2.3 g, crude) was obtained as a black brown oil. MS: m/z=214.9 [M+Na]$^+$.

Step 4: (4-((6-(tert-Butyl)-3-nitropyridin-2-yl)amino)phenyl)methanol

To a solution of 6-(tert-butyl)-3-nitropyridin-2-ol (1 g, 4.7 mmol) in DMSO (10 mL) were added DIEA (1.8 g, 14 mmol) and (4-aminophenyl)methanol (574 mg, 4.7 mmol). The mixture was stirred at 100° C. for 16 hr. The reaction mixture was poured into H$_2$O (50 mL) and was extracted with EtOAc (300 mL). The organic phase was dried over anhydrous Na$_2$SO$_4$, filtered and concentrated under reduced pressure. to give (4-((6-(tert-butyl)-3-nitropyridin-2-yl)amino)phenyl)methanol (1.5 g) as a yellow oil. MS: m/z=302.1 [M+H]$^+$.

Step 5: 4-((6-(Tert-butyl)-3-nitropyridin-2-yl)amino) benzyl acetate

To a solution of (4-((6-(tert-butyl)-3-nitropyridin-2-yl)amino)phenyl)methanol (1.5 g, 5 mmol) in CH$_2$Cl$_2$ (20 mL) were added TEA (1.51 g, 14.9 mmol) and DMAP (61 mg, 498 gmol). The mixture was stirred at 0° C. for 5 min, and Ac$_2$O (508 mg, 5 mmol) was added dropwise at 0° C. The mixture was stirred at 0° C. for 1 hr, Na$_2$CO$_3$ (aq. 15 mL) was added to adjust the pH about 8 and extracted with CH$_2$Cl$_2$ (60 mL). The organic layer was dried over Na$_2$SO$_4$, filtered and concentrated under reduced pressure. After purified by silica gel flash chromatography (Eluent of 0~5%, EtOAc in petroleum ether), 4-((6-(tert-butyl)-3-nitropyridin-2-yl)amino)benzyl acetate (877 mg, yield: 52%) was obtained as a yellow solid. MS: m/z=344.0 [M+H]$^+$. $^1$H NMR (400 MHz, Chloroform-d) δ 10.39-10.22 (m, 1H), 8.4 (d, J=8.4 Hz, 1H), 7.77 (d, J=8.0 Hz, 2H), 7.38 (d, J=8.4 Hz, 2H), 6.89 (d, J=8.4 Hz, 1H), 5.11 (s, 2H), 2.12 (s, 3H), 1.36 (s, 9H).

Step 6: 4-(2-(2-Aminopyridin-3-yl)-5-(tert-butyl)-3H-imidazo[4,5-b]pyridin-3-yl)benzyl acetate To a solution of 4-((6-(tert-butyl)-3-nitropyridin-2-yl)amino)benzyl acetate in DMSO (30 mL) were added Na$_2$S$_2$O$_4$ (1.85 g, 9 mmol) and 2-aminopyridine-3-carbaldehyde (311 mg, 2.6 mmol). The mixture was stirred at 100° C. for 16 hr. The reaction mixture was poured into H$_2$O (10 mL), extracted with CH$_2$Cl$_2$ (90 mL). The organic phase was dried over anhydrous Na$_2$SO$_4$, filtered and concentrated under reduced pressure. After purified by silica gel flash chromatography (Eluent of 0~72% EtOAc in petroleum ether), 4-(2-(2-aminopyridin-3-yl)-5-(tert-butyl)-3H-imidazo[4,5-b]pyridin-3-yl)benzyl acetate (285 mg, yield: 30%) was obtained as a yellow solid. MS: m/z=416.1 [M+H]$^+$.

Step 7: (4-(2-(2-Aminopyridin-3-yl)-5-(tert-butyl)-3H-imidazo[4,5-b]pyridin-3-yl)phenyl)methanol To a solution of 4-(2-(2-aminopyridin-3-yl)-5-(tert-butyl)-3H-imidazo[4,5-b]pyridin-3-yl)benzyl acetate (285 mg, 686 mol) in MeOH (2 mL) and THF (2 mL) were added K₂CO₃ (190 mg, 1.4 mmol) in H₂O (1 mL). The mixture was stirred at 25° C. for 0.5 hr. The reaction mixture was concentrated under reduced pressure to remove MeOH. The residue was diluted with H₂O (5 mL) and extracted with EtOAc (30 mL). The organic layer was dried over Na₂SO₄, filtered and concentrated under reduced pressure to give (4-(2-(2-Aminopyridin-3-yl)-5-(tert-butyl)-3H-imidazo[4,5-b]pyridin-3-yl)phenyl)methanol (216 mg, crude) as a yellow solid. MS: m/z=374.1 [M+H]⁺.

Step 8: 3-(5-(Tert-butyl)-3-(4-(chloromethyl)phenyl)-3H-imidazo[4,5-b]pyridin-2-yl)pyridin-2-amine To a solution of (4-(2-(2-aminopyridin-3-yl)-5-(tert-butyl)-3H-imidazo[4,5-b]pyridin-3-yl)phenyl)methanol (216 mg, 578 μmol) in CH₂Cl₂ (5 mL) was added SOCl₂ (206 mg, 1.7 mmol). The mixture was stirred at 40° C. for 0.3 hr. The reaction was concentrated under reduced pressure to give 3-(5-(tert-butyl)-3-(4-(chloromethyl)phenyl)-3H-imidazo[4,5-b]pyridin-2-yl)pyridin-2-amine (Intermediate 123, 200 mg, crude) as a yellow solid. MS: m/z=392.1 [M+H]⁺.

Intermediate 124: 3-(3-(4-(Chloromethyl)phenyl)-5-ethyl-3H-imidazo[4,5-b]pyridin-2-yl)pyridin-2-amine

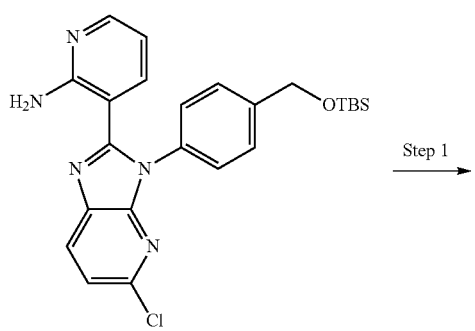

Step 1

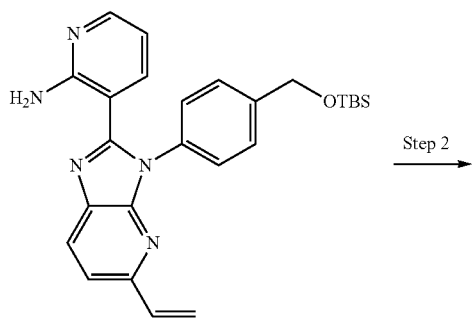

Step 2

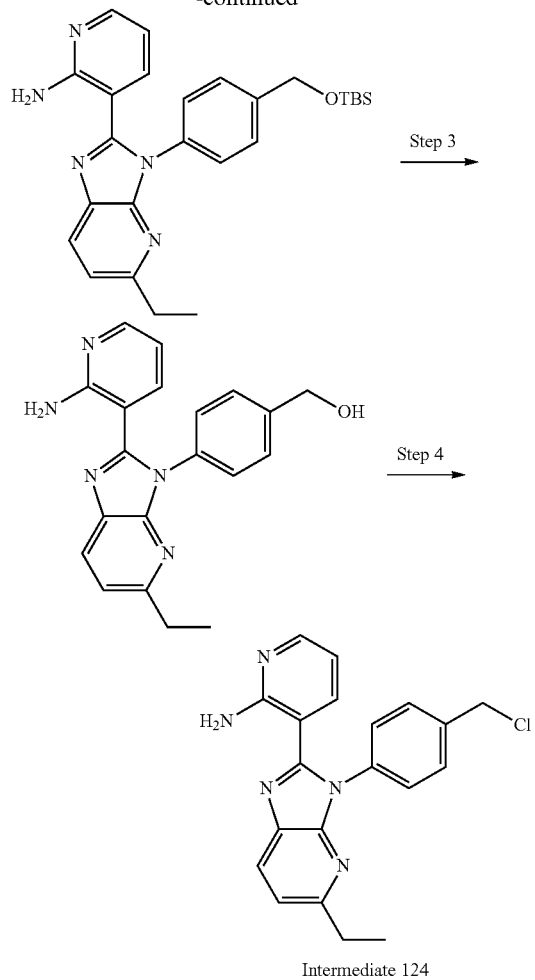

Intermediate 124

Step 1: 3-(3-(4-(((Tert-butyldimethylsilyl)oxy)methyl)phenyl)-5-vinyl-3H-imidazo[4,5-b]pyridin-2-yl)pyridin-2-amine A mixture of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 800 mg, 1.7 mmol), 4,4,5,5-tetramethyl-2-vinyl-1,3,2-dioxaborolane (317 mg, 2 mmol), Cs₂CO₃ (1.7 g, 5 mmol), and Pd(dppf)Cl₂ (126 mg, 172 μmol) in 1,4-dioxane (8 mL) and H₂O (2 mL) was degassed and purged with N₂ three times, then the mixture was stirred at 100° C. for 1.5 hr under N₂ atmosphere. The reaction mixture was diluted with H₂O (30 mL) and extracted with EtOAc (60 mL). The organic layers were washed with brine (30 mL), dried over Na₂SO₄, filtered and concentrated under reduced pressure. After purified by silica gel flash chromatography (Eluent of 0~35% EtOAc in petroleum ether), 3-(3-(4-(((tert-butyldimethylsilyl)oxy)methyl)phenyl)-5-vinyl-3H-imidazo[4,5-b]pyridin-2-yl)pyridin-2-amine (630 mg, yield: 80%) was obtained as a black brown solid. MS: m/z=458.2 [M+H]⁺. ¹H NMR (400 MHz, Chloroform-d) δ 8.04 (dd, J=4.8, 1.6 Hz, 1H), 8.01 (d, J=8.0 Hz, 1H), 7.47 (d, J=8.4 Hz, 2H), 7.40-7.34 (m, 3H), 7.11 (dd, J=7.6, 1.6 Hz, 1H), 6.85 (dd, J=17.2, 10.8 Hz, 1H), 6.69 (br s, 2H), 6.36 (dd, J=7.6, 5.2 Hz, 1H), 6.15 (dd, J=17.2, 1.2 Hz, 1H), 5.40 (dd, J=10.8, 1.2 Hz, 1H), 4.84 (s, 2H), 0.97 (s, 9H), 0.14 (s, 6H).

Step 2: 3-(3-(4-(((Tert-butyldimethylsilyl)oxy) methyl)phenyl)-5-ethyl-3H-imidazo[4,5-b]pyridin-2-yl)pyridin-2-amine A mixture of 3-(3-(4-(((tert-butyldimethylsilyl)oxy)methyl)phenyl)-5-vinyl-3H-imidazo[4,5-b]pyridin-2-yl)pyridin-2-amine (200 mg, 437 gmol) in MeOH (5 mL) was added Pd/C (80.0 mg, 10% purity), then the mixture was degassed and purged with $H_2$ three times The mixture was stirred at 25° C. for 4 hr under $H_2$ atmosphere. The reaction mixture was filtered and the mixture was concentrated under reduced pressure to give 3-(3-(4-(((tert-butyldimethylsilyl)oxy)methyl)phenyl)-5-ethyl-3H-imidazo[4,5-b]pyridin-2-yl)pyridin-2-amine (200 mg, yield: 89%) as yellow oil. MS: m/z=460.2 [M+H]$^+$. $^1$H NMR (400 MHz, Dimethylsulfoxide-d$_6$) δ 8.10 (d, J=8.0 Hz, 1H), 7.97 (dd, J=4.4, 1.6 Hz, 1H), 7.48-7.43 (m, 2H), 7.41-7.35 (m, 2H), 7.27 (d, J=8.4 Hz, 1H), 7.13 (dd, J=8.0, 2.0 Hz, 1H), 6.98 (br s, 2H), 6.35 (dd, J=7.6, 4.8 Hz, 1H), 4.80 (s, 2H), 3.19-3.13 (m, 2H), 1.20 (t, J=7.6 Hz, 3H), 0.92 (s, 9H), 0.11 (s, 6H).

Step 3: (4-(2-(2-Aminopyridin-3-yl)-5-ethyl-3H-imidazo[4,5-b]pyridin-3-yl)phenyl)methanol To a solution of 3-(3-(4-(((tert-butyldimethylsilyl)oxy)methyl)phenyl)-5-ethyl-3H-imidazo[4,5-b]pyridin-2-yl)pyridin-2-amine (200 mg, 435 μmol) in THF (2 mL) was added TBAF (1 M, 1.74 mL). The mixture was stirred at 25° C. for 0.5 hr. The reaction mixture was diluted with water (10 mL) and extracted with EtOAc (2×10 mL). The combined organic layers were dried over $Na_2SO_4$, filtered and concentrated under reduced pressure to give (4-(2-(2-aminopyridin-3-yl)-5-ethyl-3H-imidazo[4,5-b]pyridin-3-yl)phenyl)methanol (150 mg, yield: 99%) as a yellow solid. MS: m/z=346.1 [M+H]$^+$.

Step 4: 3-(3-(4-(Chloromethyl)phenyl)-5-ethyl-3H-imidazo[4,5-b]pyridin-2-yl)pyridin-2-amine To a solution of (4-(2-(2-aminopyridin-3-yl)-5-ethyl-3H-imidazo[4,5-b]pyridin-3-yl)phenyl)methanol (150 mg, 434 μmol) in $CH_2Cl_2$ (2 mL) was added $SOCl_2$ (206 mg, 1.74 mmol). The mixture was stirred at 40° C. for 0.5 hr. The mixture was concentrated under reduced pressure, 3-(3-(4-(chloromethyl)phenyl)-5-ethyl-3H-imidazo[4,5-b]pyridin-2-yl)pyridin-2-amine (Intermediate 124, 170 mg, HCl salt) was obtained as a yellow solid. MS: m/z=364.1 [M+H]$^+$.

Intermediate 125: 2-(2-Aminopyridin-3-yl)-3-(4-(chloromethyl)phenyl)-N-methyl-3H-imidazo[4,5-b]pyridine-5-carboxamide

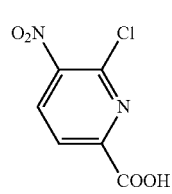

Step 1

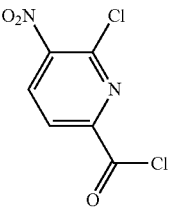

Step 2

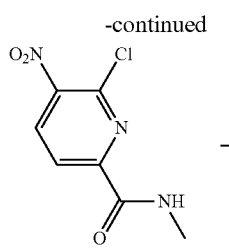

Step 3

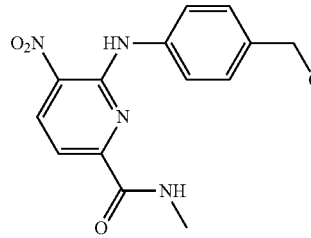

Step 4

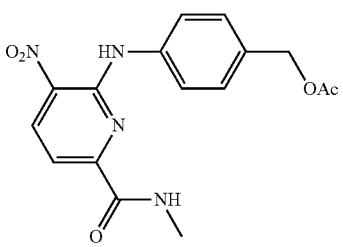

Step 5

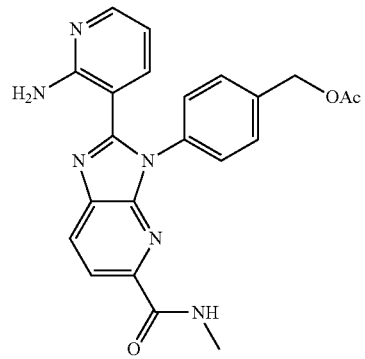

Step 6

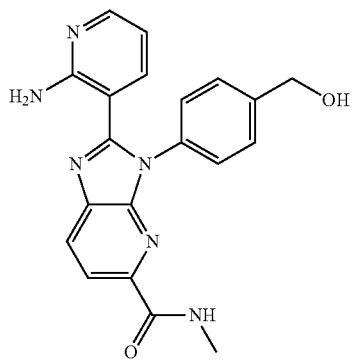

Step 7

-continued

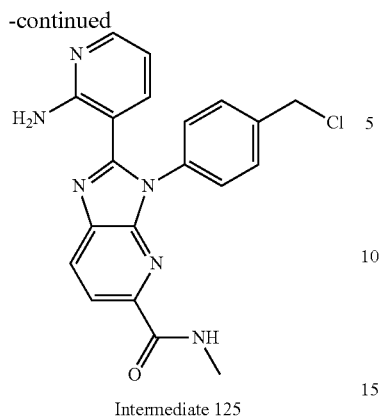

Intermediate 125

Step 1: 6-Chloro-5-nitropicolinoyl chloride

A solution of 6-chloro-5-nitropicolinic acid (10 g, 49 mmol) in SOCl$_2$ (50 mL) was stirred at 80° C. for 16 hr. The reaction mixture was concentrated to give 6-chloro-5-nitropicolinoyl chloride (9.5 g, crude) as a light-green solid.

Step 2: 6-Chloro-N-methyl-5-nitropicolinamide

To a solution of methylamine (183 mg, 2.71 mmol) in CH$_2$Cl$_2$ (5 mL) was added TEA (687 mg, 6.8 mmol) dropwise at 25° C. The mixture was stirred at 25° C. for 5 min, then 6-chloro-5-nitropicolinoyl chloride (500 mg, 2.26 mmol) in CH$_2$Cl$_2$ (5 mL) was added dropwise at 0° C. The resulting mixture was stirred at 0° C. for 1 hr. The residue was purified by silica gel flash chromatography (Eluent of 0~10% EtOAc in petroleum ether) to give 6-chloro-N-methyl-5-nitropicolinamide (308 mg, yield: 63%) as a yellow solid. MS: m/z=215.9 [M+H]$^+$. $^1$H NMR (400 MHz, Chloroform-d) S 8.36-8.30 (m, 2H), 7.76 (br s, 1H), 3.07 (d, J=5.2 Hz 3H).

Step 3: 6-((4-(Hydroxymethyl)phenyl)amino)-N-methyl-5-nitropicolinamide

To a solution of 6-chloro-N-methyl-5-nitropicolinamide (2.3 g, 11 mmol) and (4-aminophenyl)methanol (1.3 g, 11 mmol) in 1,4-dioxane (30 mL) was added DIEA (4.1 g, 32 mmol). The mixture was stirred at 100° C. for 16 hr. The reaction mixture was poured into H$_2$O (30 mL), extracted with EtOAc (100 mL). The organic phase was dried over anhydrous Na$_2$SO$_4$, filtered and concentrated under reduced pressure. The crude 6-((4-(hydroxymethyl)phenyl)amino)-N-methyl-5-nitropicolinamide (3.6 g, crude) was obtained as a red solid. MS: m/z=302.9 [M+H]$^+$.

Step 4: 4-((6-(Methylcarbamoyl)-3-nitropyridin-2-yl)amino)benzyl acetate

To a solution of 6-((4-(hydroxymethyl)phenyl)amino)-N-methyl-5-nitropicolinamide (1.7 g, 5.6 mmol) in CH$_2$Cl$_2$ (10 mL) were added TEA (1.7 g, 17 mmol) and DMAP (69 mg, 562 µmol). The mixture was stirred at 0° C. for 5 min, and then Ac$_2$O (574 mg, 5.6 mmol) was added dropwise at 0° C. The mixture was stirred at 0° C. for 1 hr. Then sat. Na$_2$CO$_3$ (5 mL) was added to adjust pH about 8 and extracted with CH$_2$Cl$_2$ (15 mL). The combined layer was dried over Na$_2$SO$_4$, filtered and concentrated under reduced pressure. After purified by silica gel flash chromatography (Eluent of 0~50% EtOAc in petroleum ether), 4-((6-(methylcarbamoyl)-3-nitropyridin-2-yl)amino)benzyl acetate (1.4 g, yield: 72%) was obtained as an orange solid. MS: m/z=345.0 [M+H]$^+$. $^1$H NMR (400 MHz, Chloroform-d) δ 9.92 (s, 1H), 8.68 (d, J=8.4 Hz, 1H), 7.71 (d, J=8.8 Hz, 1H), 7.54-7.37 (m, 5H), 5.15 (s, 2H), 2.98 (d, J=5.2 Hz, 3H), 2.14 (s, 3H).

Step 5: 4-(2-(2-Aminopyridin-3-yl)-5-(methylcarbamoyl)-3H-imidazo[4,5-b]pyridin-3-yl)benzyl acetate To a solution of 4-((6-(methylcarbamoyl)-3-nitropyridin-2-yl)amino)benzyl acetate (1.4 g, 4 mmol) and 2-aminopyridine-3-carbaldehyde (546 mg, 4.5 mmol) in DMSO (15 mL) was added Na$_2$S$_2$O$_4$ (3.3 g, 16 mmol). The mixture was stirred at 100° C. for 16 hr. The reaction mixture was poured into H$_2$O (30 mL), extracted with CH$_2$Cl$_2$ (150 mL). The organic phase was dried over anhydrous Na$_2$SO$_4$, filtered and concentrated under reduced pressure. After purified by silica gel flash chromatography (Eluent of 0~82% EtOAc in petroleum ether), 4-(2-(2-aminopyridin-3-yl)-5-(methylcarbamoyl)-3H-imidazo[4,5-b]pyridin-3-yl)benzyl acetate (650 mg, yield: 38%) was obtained as a yellow oil. MS: m/z=417.1 [M+H]$^+$.

Step 6: 2-(2-Aminopyridin-3-yl)-3-(4-(hydroxymethyl)phenyl)-N-methyl-3H-imidazo[4,5-b]pyridine-5-carboxamide To a solution of 4-(2-(2-aminopyridin-3-yl)-5-(methylcarbamoyl)-3H-imidazo[4,5-b]pyridin-3-yl)benzyl acetate (420 mg, 1 mmol) in MeOH (8 mL) and THF (8 mL) was added K$_2$CO$_3$ (279 mg, 2 mmol) in H$_2$O (2 mL). The mixture was stirred at 25° C. for 0.5 hr. The reaction mixture was concentrated under reduced pressure to move MeOH. Then the residue was diluted with H$_2$O (20 mL) and extracted with EtOAc (30 mL). The organic layer was dried over Na$_2$SO$_4$, filtered and concentrated under reduced pressure to give 2-(2-aminopyridin-3-yl)-3-(4-(hydroxymethyl)phenyl)-N-methyl-3H-imidazo[4,5-b]pyridine-5-carboxamide (350 mg, crude) as a yellow solid. MS: m/z=375.1 [M+H]$^+$.

Step 7: 2-(2-Aminopyridin-3-yl)-3-(4-(chloromethyl)phenyl)-N-methyl-3H-imidazo[4,5-b]pyridine-5-carboxamide To a solution of 2-(2-aminopyridin-3-yl)-3-(4-(hydroxymethyl)phenyl)-N-methyl-3H-imidazo[4,5-b]pyridine-5-carboxamide (350 mg, 935 µmol) in CH$_2$Cl$_2$ (5 mL) was added SOCl$_2$ (334 mg, 2.8 mmol). The mixture was stirred at 40° C. for 0.3 hr. The reaction was concentrated under reduced pressure to give 2-(2-aminopyridin-3-yl)-3-(4-(chloromethyl)phenyl)-N-methyl-3H-imidazo[4,5-b]pyridine-5-carboxamide (Intermediate 125, 200 mg, HCl salt, crude) as a yellow solid. MS: m/z=393.0 [M+H]$^+$.

Intermediate 126: 4-(2-(2-Aminopyridin-3-yl)-3-(4-(chloromethyl)phenyl)-3H-imidazo[4,5-b]pyridin-5-yl)nicotinonitrile

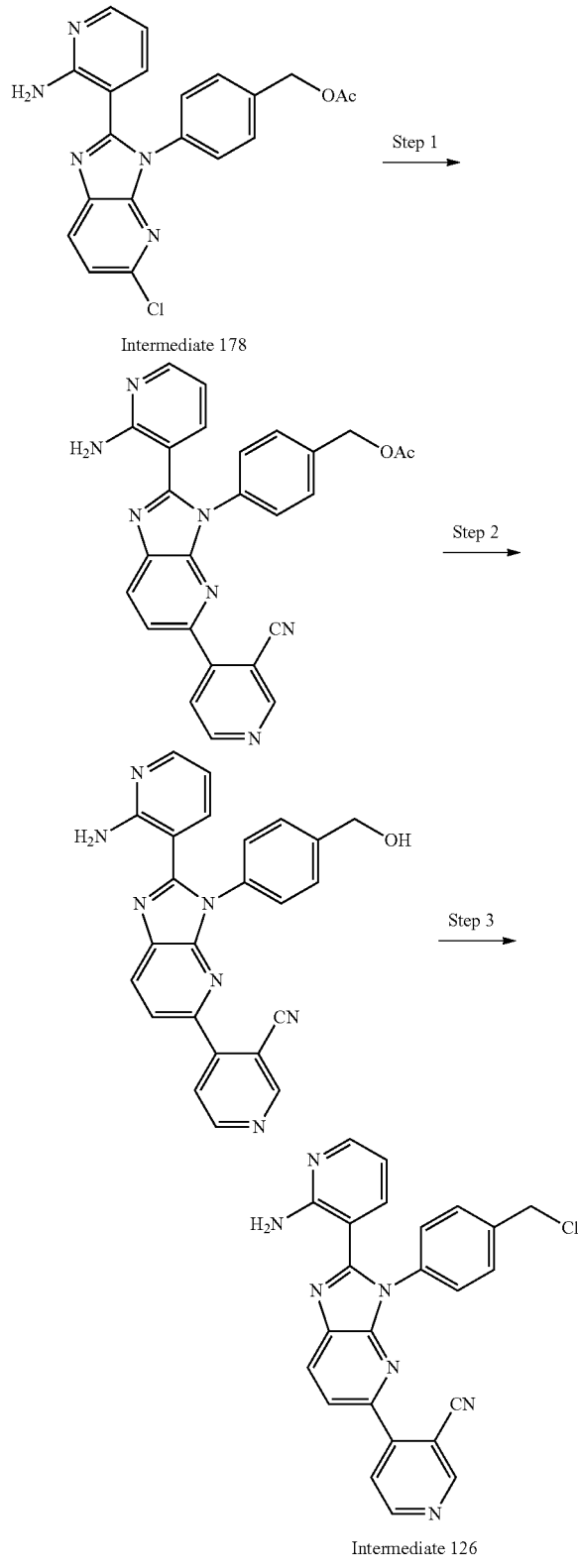

Step 1: 4-(2-(2-Aminopyridin-3-yl)-5-(3-cyanopyridin-4-yl)-3H-imidazo[4,5-b]pyridin-3-yl)benzyl acetate A mixture of Intermediate 178 (400 mg, 1.02 mmol), 4-(4,4,5,5-tetramethyl-1,3,2-dioxaborolan-2-yl)nicotinonitrile (257 mg, 1.12 mmol), cataCXiumAPdG3 (369 mg, 507 μmol), $K_3PO_4$ (431 mg, 2.03 mmol) and $PCy_3$ (28.4 mg, 101 μmol) in DMF (10 mL) was degassed and purged with $N_2$ three times, and then the mixture was stirred at 120° C. for 12 hr under $N_2$ atmosphere. The reaction mixture was diluted with water (20 mL) and extracted with EtOAc (2×30 mL). The combined organic layers were washed with brine (10 mL), dried over $Na_2SO_4$, filtered and concentrated under reduced pressure. After purified by silica gel flash chromatography (Eluent of 0~8% MeOH in $CH_2Cl_2$), 4-(2-(2-aminopyridin-3-yl)-5-(3-cyanopyridin-4-yl)-3H-imidazo[4,5-b]pyridin-3-yl)benzyl acetate (450 mg, yield: 76%) was obtained as a red solid. MS: m/z=462.1 [M+H]+.

Step 2: 4-(2-(2-Aminopyridin-3-yl)-3-(4-(hydroxymethyl)phenyl)-3H-imidazo[4,5-b]pyridin-5-yl)nicotinonitrile To a solution of 4-(2-(2-aminopyridin-3-yl)-5-(3-cyanopyridin-4-yl)-3H-imidazo[4,5-b]pyridin-3-yl)benzyl acetate (450 mg, 975 μmol) in MeOH (3 mL) and THF (3 mL) was added a solution of $K_2CO_3$ (134 mg, 975 μmol) in $H_2O$ (1 mL). The mixture was stirred at 25° C. for 0.5 hr. The reaction mixture was diluted with water (10 mL) and extracted with EtOAc (2×10 mL). The combined organic layers were washed with brine (10 mL), dried over $Na_2SO_4$, filtered, and concentrated under reduced pressure to give 4-(2-(2-aminopyridin-3-yl)-3-(4-(hydroxymethyl)phenyl)-3H-imidazo[4,5-b]pyridin-5-yl)nicotinonitrile (300 mg, yield: 73%) as a yellow solid. MS: m/z=420.1 [M+H]+.

Step 3: 4-(2-(2-Aminopyridin-3-yl)-3-(4-(chloromethyl)phenyl)-3H-imidazo[4,5-b]pyridin-5-yl)nicotinonitrile To a solution of 4-(2-(2-aminopyridin-3-yl)-3-(4-(hydroxymethyl)phenyl)-3H-imidazo[4,5-b]pyridin-5-yl)nicotinonitrile (300 mg, 715 mol) in $CH_2Cl_2$ (5 mL) was added $SOCl_2$ (340 mg, 2.86 mmol). The mixture was stirred at 40° C. for 0.5 hr. The mixture was concentrated under reduced pressure to give 4-(2-(2-aminopyridin-3-yl)-3-(4-(chloromethyl)phenyl)-3H-imidazo[4,5-b]pyridin-5-yl)nicotinonitrile (Intermediate 126, 300 mg, HCl salt) as a yellow solid. MS: m/z=437.9 [M+H]+.

Intermediate 127: 3-(3-(4-(Chloromethyl)phenyl)-5-fluoro-3H-imidazo[4,5-b]pyridin-2-yl)pyridin-2-amine

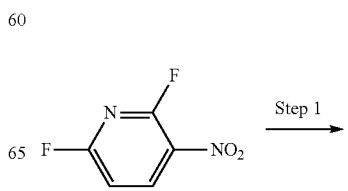

-continued

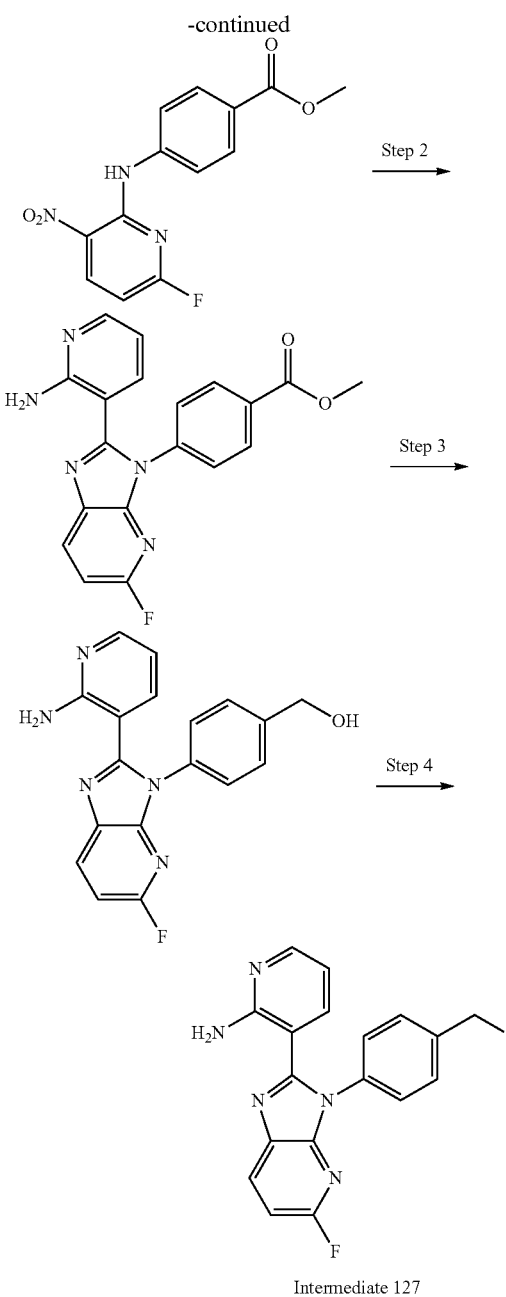

Intermediate 127

Step 1: Methyl 4-((6-fluoro-3-nitropyridin-2-yl)amino)benzoate

To a solution of methyl 4-aminobenzoate (10 g, 66.1 mmol) and 2,6-difluoro-3-nitropyridine (10.5 g, 66 mmol) in dioxane (175 mL) was added DIEA (17.1 g, 132 mmol). The mixture was stirred at 80° C. for 12 hr. The reaction mixture was diluted with water (100 mL) and extracted with EtOAc (2×200 mL). The combined organic layers were dried over $Na_2SO_4$, filtered and concentrated under reduced pressure. After triturated with EtOAc (100 mL) and filtered, methyl 4-((6-fluoro-3-nitropyridin-2-yl)amino)benzoate (13.4 g, yield: 60%) was obtained as a yellow solid. MS: m/z=292.0 $[M+H]^+$. $^1H$ NMR (400 MHz, Chloroform-d) δ 10.53 (br s, 1H), 8.74-8.62 (m, 1H), 8.07 (d, J=8.4 Hz, 2H), 7.76 (d, J=8.8 Hz, 2H), 6.49 (dd, J=8.8, 3.6 Hz, 1H), 3.92 (s, 3H), $^{19}F$ NMR (400 MHz, Chloroform-d) δ −52.533.

Step 2: Methyl 4-(2-(2-aminopyridin-3-yl)-5-fluoro-3H-imidazo[4,5-b]pyridin-3-yl)benzoate To a solution of methyl 4-((6-fluoro-3-nitropyridin-2-yl)amino)benzoate (6.2 g, 21.2 mmol) and 2-aminonicotinaldehyde (2.86 g, 23.4 mmol) in DMSO (186 mL) was added $Na_2S_2O_4$ (17 g, 85.1 mmol, 87% purity). The mixture was stirred at 100° C. for 12 hr. The reaction mixture was diluted with water (50 mL) and extracted with $CH_2Cl_2$ (2×250 mL). The combined organic layers were washed with brine (100 mL), dried over $Na_2SO_4$, filtered and concentrated under reduced pressure. After purified by silica gel flash chromatography (Eluent of 0~00% EtOAc in petroleum ether), methyl 4-(2-(2-aminopyridin-3-yl)-5-fluoro-3H-imidazo[4,5-b]pyridin-3-yl)benzoate (1.5 g, yield: 18%) was obtained as a yellow solid. MS: m/z=364.1 $[M+H]^+$. $^1H$ NMR (400 MHz, Chloroform-d) δ 8.22-8.14 (m, 3H), 8.08 (dd, J=4.8, 1.6 Hz, 1H), 7.48-7.42 (m, 2H), 7.01 (dd, J=8.0, 1.6 Hz, 1H), 6.96 (d, J=8.4 Hz, 1H), 6.56 (br s, 2H), 6.37 (dd, J=8.0, 4.8 Hz, 1H), 3.97 (s, 3H), $^{19}F$ NMR (400 MHz, Chloroform-d) δ −71.619.

Step 3: (4-(2-(2-Aminopyridin-3-yl)-5-fluoro-3H-imidazo[4,5-b]pyridin-3-yl)phenyl)methanol To a solution of methyl 4-(2-(2-aminopyridin-3-yl)-5-fluoro-3H-imidazo[4,5-b]pyridin-3-yl)benzoate (1.5 g, 4.13 mmol) in THF (30 mL) was added $LiAlH_4$ (2.5 M, 2.48 mL). The mixture was stirred at 0° C. for 2 hr. The reaction mixture was quenched with $Na_2SO_4·10H_2O$ (282 mg) at 0° C. and filtered. The filtrate was concentrated under reduced pressure to give (4-(2-(2-aminopyridin-3-yl)-5-fluoro-3H-imidazo[4,5-b]pyridin-3-yl)phenyl)methanol (1.3 g) as a yellow solid.

Step 4: 3-(3-(4-(Chloromethyl)phenyl)-5-fluoro-3H-imidazo[4,5-b]pyridin-2-yl)pyridin-2-amine To a solution of (4-(2-(2-aminopyridin-3-yl)-5-fluoro-3H-imidazo[4,5-b]pyridin-3-yl)phenyl)methanol (1.3 g, 3.88 mmol) in $CH_2Cl_2$ (10 mL) was added $SOCl_2$ (2.77 g, 23.3 mmol). The mixture was stirred at 40° C. for 0.5 hr. The mixture was concentrated under reduced pressure. The residue was purified by silica gel flash chromatography (Eluent of 0-~6% MeOH in $CH_2Cl_2$), 3-(3-(4-(chloromethyl)phenyl)-5-fluoro-3H-imidazo[4,5-b]pyridin-2-yl)pyridin-2-amine (Intermediate 127, 400 mg, yield: 27%) was obtained as a yellow solid. MS: m/z=353.9 $[M+H]^+$.

Intermediate 128: 3-(3-(4-(Chloromethyl)phenyl)-6-fluoro-3H-imidazo[4,5-h]pyridin-2-yl)pyridin-2-amine

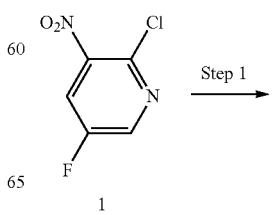

1

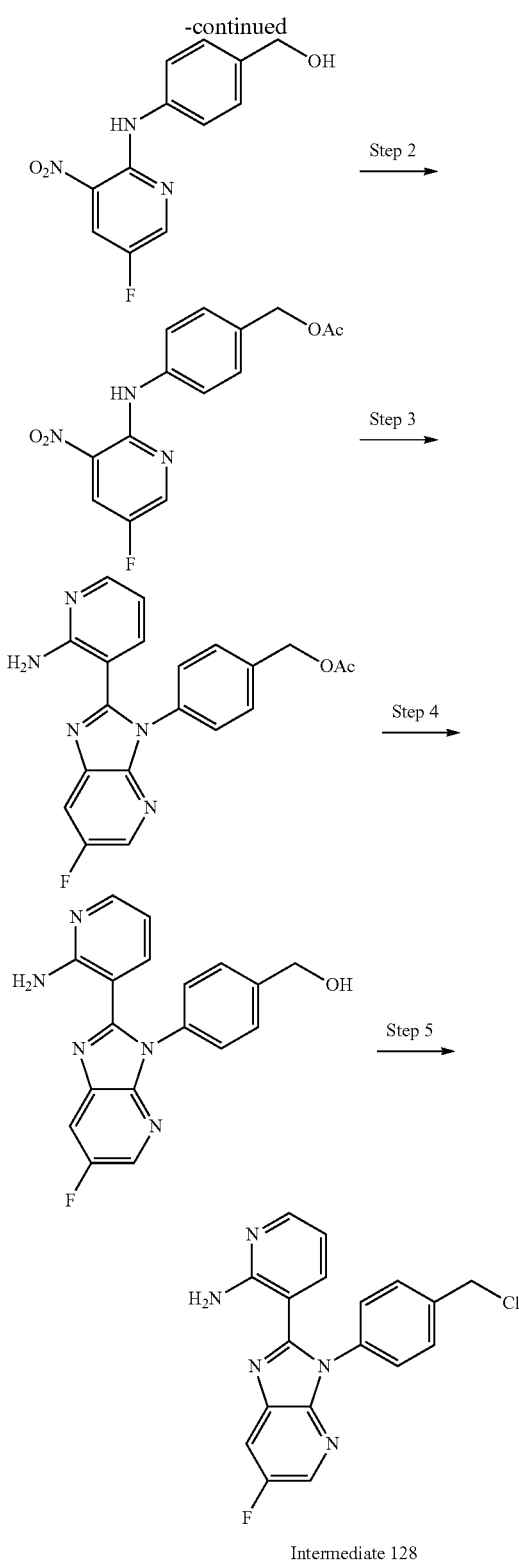

Intermediate 128

Step 1: (4-((5-Fluoro-3-nitropyridin-2-yl)amino)phenyl)methanol

To a solution of 2-chloro-5-fluoro-3-nitro-pyridine (4 g, 23 mmol) in 1,4-dioxane (40 mL) were added DIEA (7.3 g, 57 mmol) and (4-aminophenyl)methanol (2.8 g, 23 mmol). The mixture was stirred at 110° C. for 16 hr. The reaction mixture was diluted with H$_2$O (200 mL) and extracted with EtOAc (400 mL). The organic layer was washed with brine (130 mL), dried over Na$_2$SO$_4$, filtered and concentrated under reduced pressure to give (4-((5-fluoro-3-nitropyridin-2-yl)amino)phenyl)methanol (3.8 g, crude) as a yellow solid. MS: m/z=263.9 [M+H]$^+$.

Step 2: 4-((5-Fluoro-3-nitropyridin-2-yl)amino)benzyl acetate

To a solution of (4-((5-fluoro-3-nitropyridin-2-yl)amino)phenyl)methanol (3.8 g, 14 mmol) and Ac$_2$O (1.5 g, 14 mmol) in CH$_2$Cl$_2$ (38 mL) was added TEA (4.4 g, 43 mmol) and DMAP (176 mg, 1.4 mmol) at 0° C. The mixture was stirred at 0° C. for 1 hr. The reaction mixture was diluted with H$_2$O (150 mL) and extracted with CH$_2$Cl$_2$ (400 mL). The organic layer was washed with brine (150 mL), dried over Na$_2$SO$_4$, filtered and concentrated under reduced pressure. After purified by silica gel flash chromatography (Eluent of 10~30%, EtOAc in petroleum ether), 4-((5-fluoro-3-nitropyridin-2-yl)amino)benzyl acetate (1.4 g, yield: 30%) was obtained as a yellow solid. MS: m/z=305.9 [M+H]$^+$. $^1$H NMR (400 MHz, Chloroform-d) δ 10.02 (br s, 1H), 8.44 (d, J=2.4 Hz, 1H), 8.30 (dd, J=7.6, 2.8 Hz, 1H), 7.61 (d, J=8.4 Hz, 2H), 7.39 (d, J=8.0 Hz, 2H), 5.11 (s, 2H), 2.11 (s, 3H).

Step 3: 4-(2-(2-Aminopyridin-3-yl)-6-fluoro-3H-imidazo[4,5-b]pyridin-3-yl)benzyl acetate A mixture of 4-((5-fluoro-3-nitropyridin-2-yl)amino)benzyl acetate (1.4 g, 4.6 mmol), 2-aminopyridine-3-carbaldehyde (616 mg, 5 mmol), Na$_2$S$_2$O$_4$ (3.2 g, 18 mmol) in DMSO (40 mL) was degassed and purged with N$_2$ three times, and then the mixture was stirred at 100° C. for 16 hr under N$_2$ atmosphere. The reaction mixture was diluted with H$_2$O (200 mL) and extracted with CH$_2$Cl$_2$ (200 mL×3). The combined organic layers were washed with brine (150 mL), dried over Na$_2$SO$_4$, filtered and concentrated under reduced pressure. After purified by silica gel flash chromatography (Eluent of 10~2 0% EtOAc in petroleum ether), 4-(2-(2-aminopyridin-3-yl)-6-fluoro-3H-imidazo[4,5-b]pyridin-3-yl)benzyl acetate (285 mg, yield: 11%) was obtained as a brown solid. MS: m/z=378.0 [M+H]$^+$. $^1$H NMR (400 MHz, Chloroform-d) δ 8.35-8.23 (m, 1H), 8.06 (dd, J=5.2, 1.6 Hz, 1H), 7.82 (dd, J=5.2, 1.6 Hz, 1H), 7.54 (d, J=8.4 Hz, 2H), 7.38 (d, J=8.4 Hz, 2H), 7.13 (dd, J=8.0, 1.6 Hz, 1H), 6.89 (br s, 2H), 6.41 (dd, J=8.0, 5.2 Hz, 1H), 5.20 (s, 2H), 2.15 (s, 3H).

Step 4: (4-(2-(2-Aminopyridin-3-yl)-6-fluoro-3H-imidazo[4,5-b]pyridin-3-yl)phenyl)methanol To a solution of 4-(2-(2-aminopyridin-3-yl)-6-fluoro-3H-imidazo[4,5-b]pyridin-3-yl)benzyl acetate (285 mg, 755 μmol) in THF (2 mL) and MeOH (2 mL) was added K$_2$CO$_3$ (313 mg, 2.3 mmol) in H$_2$O (1 mL). The mixture was stirred at 25° C. for 0.5 hr. The mixture was concentrated under reduced pressure. The residue was diluted with H$_2$O (10 mL) and extracted with CH$_2$Cl$_2$ (20 mL). The organic layer was washed with brine (10 mL), dried over Na$_2$SO$_4$, filtered and concentrated under reduced pressure. (4-(2-(2-Aminopyridin-3-yl)-6-fluoro-3H-imidazo[4,5-b]pyridin-3-yl)phenyl)methanol (230 mg, crude) was obtained as a brown solid. MS: m/z=336.0 [M+H]$^+$.

Step 5: 3-(3-(4-(Chloromethyl)phenyl)-6-fluoro-3H-imidazo[4,5-b]pyridin-2-yl)pyridin-2-amine To a solution of (4-(2-(2-aminopyridin-3-yl)-6-fluoro-3H-imidazo[4,5-b]pyridin-3-yl)phenyl)methanol (230 mg, 686 μmol) in CH₂Cl₂ (5 mL) was added SOCl₂ (163 mg, 1 mmol). The mixture was stirred at 40° C. for 0.5 hr. The mixture was concentrated under reduced pressure. 3-(3-(4-(Chloromethyl)phenyl)-6-fluoro-3H-imidazo[4,5-b]pyridin-2-yl)pyridin-2-amine (Intermediate 128, 284 mg, crude) was obtained as a yellow solid. MS: m/z=353.9 [M+H]I.

Intermediate 129: 3-(5-Bromo-3-(4-(((tert-butyldimethylsilyl)oxy)methyl)phenyl)-3H-imidazo[4,5-b]pyridin-2-yl)pyridin-2-amine

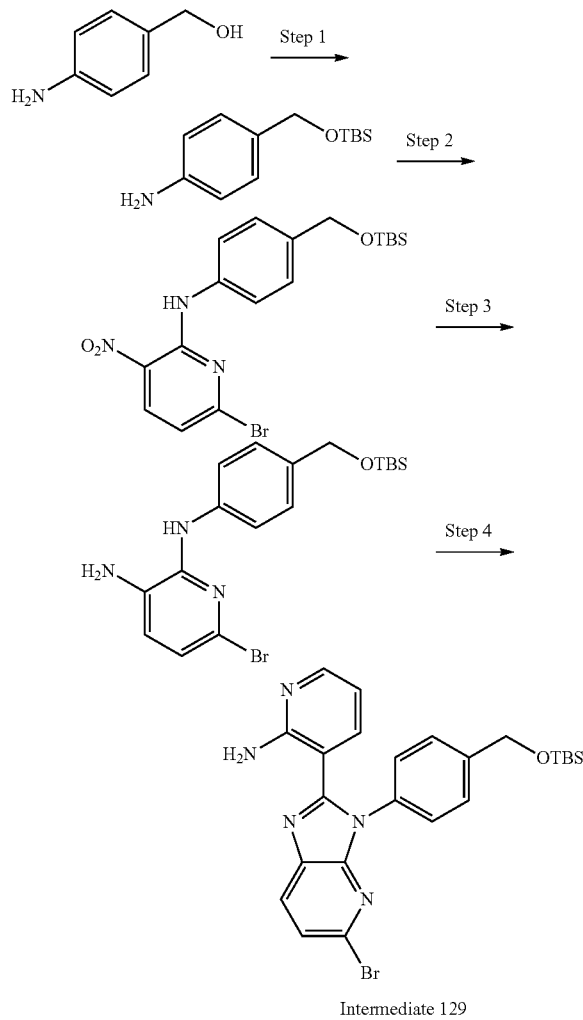

Intermediate 129

Step 1: 4-(((tert-Butyldimethylsilyl)oxy)methyl)aniline

To a solution of (4-aminophenyl)methanol (5 g, 40.6 mmol) in CH₂Cl₂ (50 mL) were added TBSCl (8.34 g, 55.4 mmol), TEA (10.3 mL, 73.8 mmol), and DMAP (225 mg, 1.85 mmol). The mixture was degassed and purged with N₂ three times, and stirred at 25° C. for 2 hr under N₂. The reaction mixture was filtered and concentrated under reduced pressure to give 4-(((tert-butyldimethylsilyl)oxy)methyl) aniline (8.76 g, crude) as a white oil, which was used in the next step without further purification.

Step 2: 6-Bromo-N-(4-(((tert-butyldimethylsilyl)oxy)methyl)phenyl)-3-nitropyridin-2-amine To a solution of 4-[[tert-butyl(dimethyl)silyl]oxymethyl] aniline (8.76 g, 36.9 mmol) in 1,4-dioxane (100 mL) were added DIEA (19.3 mL, 111 mmol) and 2,6-dibromo-3-nitropyridine (10.4 g, 36.9 mmol). The mixture was degassed and purged with N₂ three times and stirred at 45° C. for 16 hr under N₂. The reaction mixture was concentrated under reduced pressure and purified by silica gel flash chromatography (Eluent of 1~10% EtOAc in Petroleum ether) to give 6-bromo-N-(4-(((tert-butyldimethylsilyl)oxy)methyl)phenyl)-3-nitropyridin-2-amine (13.7 g, yield: 72%) as a red solid. MS: m/z=440.2 [M+H]⁺. ¹H NMR (400 MHz, Chloroform-d) δ 10.23 (s, 1H), 8.32 (d, J=8.4 Hz, 1H), 7.61 (d, J=8.4 Hz, 2H), 6.95 (d, J=8.4 Hz, 1H), 4.75 (s, 2H), 0.96 (s, 9H), 0.12 (s, 6H).

Step 3: 6-Bromo-N²-(4-(((tert-butyldimethylsilyl)oxy)methyl)phenyl)pyridine-2,3-diamine To a solution of 6-bromo-N-(4-(((tert-butyldimethylsilyl)oxy)methyl)phenyl)-3-nitropyridin-2-amine (46 g, 105 mmol) in EtOH (500 mL) and H₂O (100 mL) were added Fe (17.6 g, 315 mmol) and NH₄Cl (39.3 g, 735 mmol). The mixture was degassed and purged with N₂ three times and stirred at 80° C. for 2 hr under N₂. The reaction mixture was filtered and concentrated under reduced pressure. 6-Bromo-N²-(4-(((tert-butyldimethylsilyl)oxy)methyl)phenyl)pyridine-2,3-diamine (42.9 g, crude) was obtained as a yellow solid, which was used in the next step without further purification. MS: m/z=408.9, 409.9 [M+H]⁺.

Step 4: 3-(5-Bromo-3-(4-(((tert-butyldimethylsilyl)oxy)methyl)phenyl)-3H-imidazo[4,5-b]pyridin-2-yl)pyridin-2-amine To a solution of 6-bromo-N²-(4-(((tert-butyldimethylsilyl)oxy)methyl)phenyl)pyridine-2,3-diamine (41 g, 100 mmol), 2-aminonicotinaldehyde (9.81 g, 80.3 mmol) in EtOH (500 mL) was added InCl₁ (2.22 g, 10.0 mmol). The mixture was degassed and purged with N₂ three times and stirred at 80° C. for 2 hr under N₂. Then MnO₂ (52.4 g, 602 mmol) was added. The mixture was stirred at 80° C. for 2 hr under N₂. The reaction mixture was filtered and concentrated under reduced pressure. The crude was purified by silica gel flash chromatography (Eluent of 1~50% EtOAc in petroleum ether) to give 3-(5-bromo-3-(4-(((tert-butyldimethylsilyl)oxy)methyl)phenyl)-3H-imidazo[4,5-b]pyridin-2-yl)pyridin-2-amine (Intermediate 129, 19.5 g, yield: 32%) as a brown solid. MS: m/z=509.9, 511.9 [M+H]⁺. ¹H NMR (400 MHz, Chloroform-d) δ 8.10-8.01 (m, 1H), 7.92 (d, J=8.4 Hz, 1H), 7.54-7.40 (m, 3H), 7.31 (d, J=8.0 Hz, 2H), 7.07 (d, J=7.6 Hz, 1H), 6.64 (br s, 2H), 6.41-6.27 (m, 1H), 4.83 (s, 2H), 0.97 (s, 9H), 0.14 (s, 6H).

Intermediate 130: 3-(2-(2-Aminopyridin-3-yl)-3-(4-(chloromethyl)phenyl)-3H-imidazo[4,5-b]pyridin-5-yl)oxazolidin-2-one

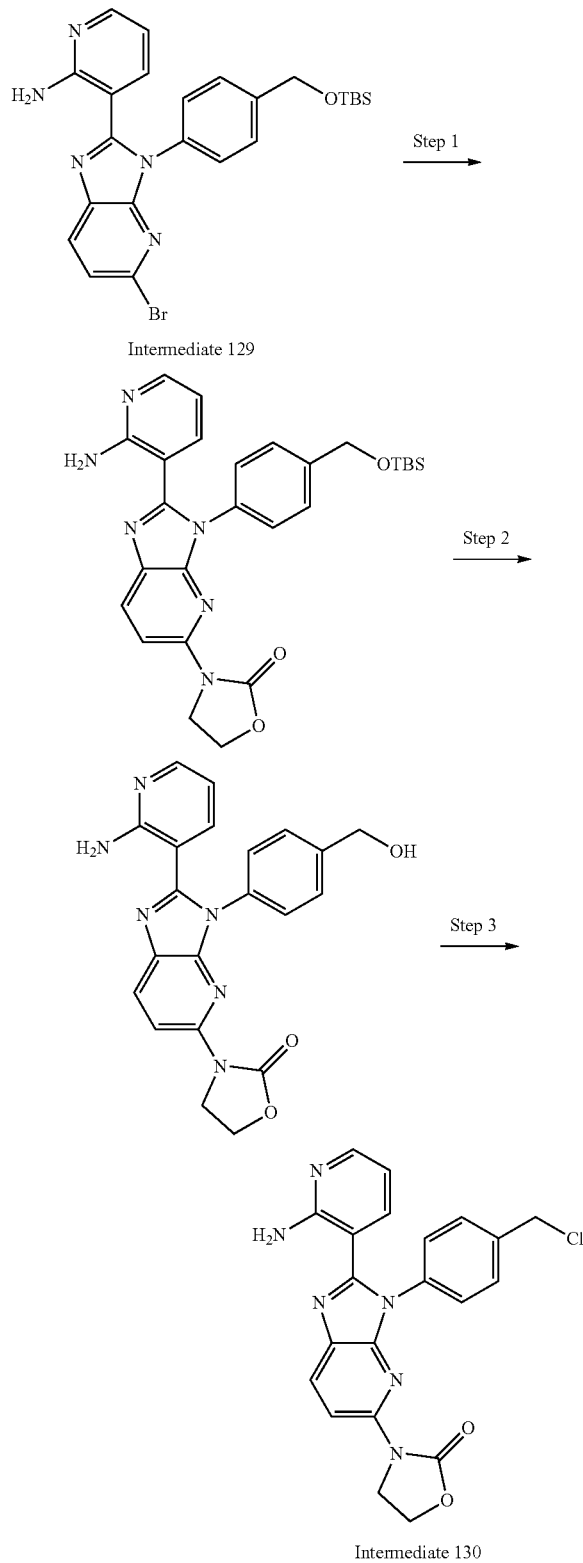

Step 1: 3-(2-(2-Aminopyridin-3-yl)-3-(4-(((tert-butyldimethylsilyl)oxy)methyl)phenyl)-3H-imidazo[4,5-b]pyridin-5-yl)oxazolidin-2-one A mixture of Intermediate 129 (800 mg, 783 μmol), oxazolidin-2-one (82 mg, 940 μmol), CuI (8 mg, 39 μmol), $K_2CO_3$ (216 mg, 1.57 mmol), and dimethylaminoacetic acid (8 mg, 78.3 μmol) in DMF (8 mL) was degassed and purged with $N_2$ three times, and then the mixture was stirred at 120° C. for 16 hr under $N_2$ atmosphere. The reaction mixture was diluted with $H_2O$ (100 mL) and extracted with EtOAc (30 mL×2). The combined organic layers were washed with brine (50 mL), dried over $Na_2SO_4$, filtered and concentrated under reduced pressure. The residue was purified by silica gel flash chromatography (Eluent of 0~7% MeOH in $CH_2Cl_2$) to give 3-(2-(2-aminopyridin-3-yl)-3-(4-(((tert-butyldimethylsilyl)oxy)methyl)phenyl)-3H-imidazo[4,5-b]pyridin-5-yl)oxazolidin-2-one (300 mg, yield: 33%) as a brown solid. MS: m/z=517.1 $[M+H]^+$.

Step 2: 3-(2-(2-Aminopyridin-3-yl)-3-(4-(hydroxymethyl)phenyl)-3H-imidazo[4,5-b]pyridin-5-yl)oxazolidin-2-one A solution of 3-(2-(2-aminopyridin-3-yl)-3-(4-(((tert-butyldimethylsilyl)oxy)methyl)phenyl)-3H-imidazo[4,5-b]pyridin-5-yl)oxazolidin-2-one (300 mg, 580 μmol) in TBAF (1 M, 4.69 mL) was stirred at 25° C. for 1 hr. The reaction mixture was diluted with $H_2O$ (30 mL) and extracted with $CH_2Cl_2$ (30 mL×2). The combined organic layers were washed with brine (30 mL), dried over $Na_2SO_4$, filtered and concentrated under reduced pressure. The residue was purified by silica gel flash chromatography (Eluent of 0~7% MeOH in $CH_2Cl_2$) to give 3-(2-(2-aminopyridin-3-yl)-3-(4-(hydroxymethyl)phenyl)-3H-imidazo[4,5-b]pyridin-5-yl)oxazolidin-2-one (90 mg, yield: 38%) as a yellow solid. MS: m/z=403.1 $[M+H]^+$. $^1$H NMR (400 MHz, Chloroform-d) δ 8.27 (d, J=8.8 Hz, 1H), 8.10 (d, J=8.8 Hz, 1H), 8.05 (dd, J=5.2, 1.6 Hz, 1H), 7.50 (d, J=8.4 Hz, 2H), 7.35 (d, J=8.4 Hz, 2H), 7.07 (dd, J=7.6, 1.6 Hz, 1H), 6.57 (br s, 2H), 6.37 (dd, J=7.6, 5.2 Hz, 1H), 4.82 (s, 2H), 4.48-4.40 (m, 2H), 4.25-4.16 (m, 2H).

Step 3: 3-(2-(2-Aminopyridin-3-yl)-3-(4-(chloromethyl)phenyl)-3H-imidazo[4,5-b]pyridin-5-yl)oxazolidin-2-one To a solution of 3-(2-(2-aminopyridin-3-yl)-3-(4-(hydroxymethyl)phenyl)-3H-imidazo[4,5-b]pyridin-5-yl)oxazolidin-2-one (80 mg, 198 μmol) in $CH_2Cl_2$ (2 mL) was added $SOCl_2$ (142 mg, 1.19 mmol). The mixture was stirred at 40° C. for 1 hr. The reaction mixture was concentrated under reduced pressure. The crude 3-(2-(2-aminopyridin-3-yl)-3-(4-(chloromethyl)phenyl)-3H-imidazo[4,5-b]pyridin-5-yl)oxazolidin-2-one (Intermediate 130, 90 mg, HCl salt, yield: 100%) was used in the next step without further purification. MS: m/z=420.9 $[M+H]^+$.

Intermediate 131: 3-(3-(4-(Chloromethyl)phenyl)-5-(6-fluoropyridin-3-yl)-3H-imidazo[4,5-b]pyridin-2-yl)pyridin-2-amine

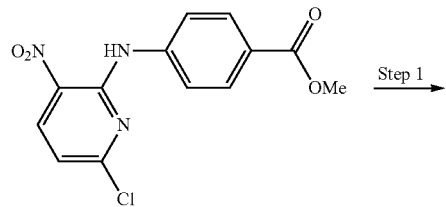

Step 1

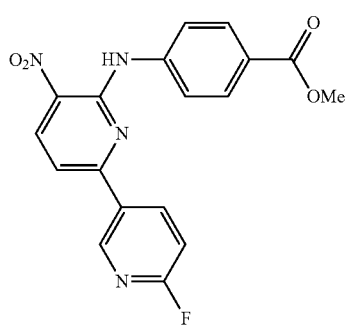

Step 2

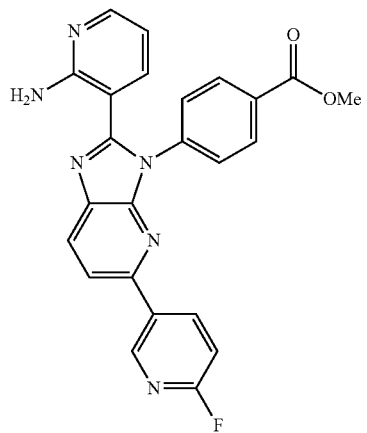

Step 3

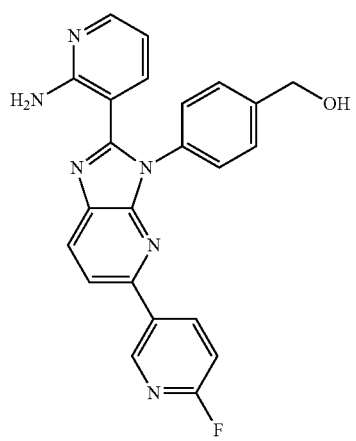

Step 4

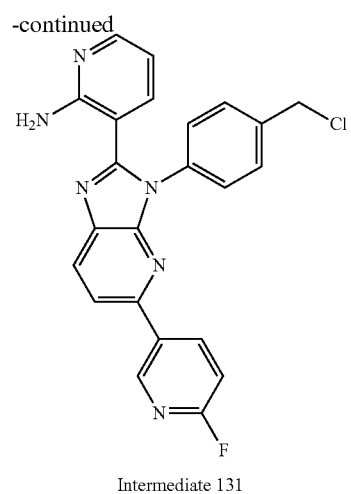

Intermediate 131

Step 1: Methyl 4-((6'-fluoro-5-nitro-[2,3'-bipyridin]-6-yl)amino)benzoate

A mixture of methyl 4-((6-chloro-3-nitropyridin-2-yl)amino)benzoate (refer to Intermediate 13 for detail procedures, 10 g, 33 mmol), (6-fluoro-3-pyridyl)boronic acid (5 g, 36 mmol), Pd(dppf)Cl$_2$ (2.4 g, 3.3 mmol), and Cs$_2$CO$_3$ (31.8 g, 97.5 mmol) in 1,4-dioxane (100 mL) and H$_2$O (10 mL) was degassed and purged with N$_2$ three times, then the mixture was stirred at 100° C. for 16 hr under N$_2$ atmosphere. The reaction mixture was diluted with water (200 mL) and extracted with EtOAc (3×300 mL). The combined organic layers were washed with brine (300 mL), dried over Na$_2$SO$_4$, filtered and concentrated under reduced pressure. After purified by silica gel flash chromatography (Eluent of 0~100% EtOAc in petroleum ether), methyl 4-((6'-fluoro-5-nitro-[2,3'-bipyridin]-6-yl)amino)benzoate (6.6 g, yield: 33%) was obtained as a yellow solid. MS: m/z=369.0 [M+H]$^+$. $^1$H NMR (400 MHz, Chloroform-d) o 10.41 (s, 1H), 8.90 (d, J=2.4 Hz, 1H), 8.67 (d, J=8.4 Hz, 1H), 8.48-8.43 (m, 1H), 8.12 (d, J=8.8 Hz, 2H), 7.80 (d, J=8.8 Hz, 2H), 7.36 (d, J=8.8 Hz, 1H), 7.09 (dd, J=8.4, 2.8 Hz, 1H), 3.94 (s, 3H)

Step 2: Methyl 4-(2-(2-aminopyridin-3-yl)-5-(6-fluoropyridin-3-yl)-3H-imidazo[4,5-b]pyridin-3-yl)benzoate A mixture of methyl 4-((6'-fluoro-5-nitro-[2,3'-bipyridin]-6-yl)amino)benzoate (6.6 g, 18 mmol), 2-aminopyridine-3-carbaldehyde (2.41 g, 19.7 mmol), and Na$_2$S$_2$O$_4$ (12.5 g, 71.7 mmol) in DMSO (180 mL) was degassed and purged with N$_2$ three times. The mixture was stirred at 100° C. for 16 hr under N$_2$ atmosphere. The reaction mixture was diluted with water (200 mL) and extracted with EtOAc (3×300 mL). The combined organic layers were washed with brine (300 mL), dried over Na$_2$SO$_4$, filtered and concentrated under reduced pressure. After purified by silica gel flash chromatography (Eluent of 0~100%, EtOAc in petroleum ether), methyl 4-(2-(2-aminopyridin-3-yl)-5-(6-fluoropyridin-3-yl)-3H-imidazo[4,5-b]pyridin-3-yl)benzoate (5 g, yield: 62%) was obtained as a yellow solid. MS: m/z=441.0 [M+H]$^+$.

Step 3: (4-(2-(2-Aminopyridin-3-yl)-5-(6-fluoropyridin-3-yl)-3H-imidazo[4,5-b]pyridin-3-yl)phenyl) methanol To a mixture of methyl 4-(2-(2-aminopyridin-3-yl)-5-(6-fluoropyridin-3-yl)-3H-imidazo[4,5-b]pyridin-3-yl)benzoate (2.6 g, 5.9 mmol) in THF (100 mL) was added LiAlH$_4$ (2.5 M in THF, 3.54 mL), then the mixture was degassed and purged with N$_2$ three times. The mixture was stirred at 0° C. for 2 hr under N$_2$ atmosphere. The reaction mixture was quenched with Na$_2$SO$_4$·10H$_2$O (600 mg) at 0° C. and filtered. The filtrate was concentrated under reduced pressure to give the crude (4-(2-(2-aminopyridin-3-yl)-5-(6-fluoropyridin-3-yl)-3H-imidazo[4,5-b]pyridin-3-yl)phenyl) methanol 2.3 g, yield: 85%) as a yellow solid. MS: m/z=413.0 [M+H]$^+$.

Step 4: 3-(3-(4-(Chloromethyl)phenyl)-5-(6-fluoropyridin-3-yl)-3H-imidazo[4,5-b]pyridin-2-yl)pyridin-2-amine To a solution of (4-(2-(2-aminopyridin-3-yl)-5-(6-fluoropyridin-3-yl)-3H-imidazo[4,5-b]pyridin-3-yl)phenyl) methanol (2.3 g, 5.58 mmol) in CH$_2$Cl$_2$ (50 mL) was added SOCl$_2$ (3.98 g, 33.5 mmol). The mixture was stirred at 40° C. for 1 hr. The mixture was concentrated under reduced pressure, 3-(3-(4-(chloromethyl)phenyl)-5-(6-fluoropyridin-3-yl)-3H-imidazo[4,5-b]pyridin-2-yl)pyridin-2-amine (Intermediate 131, 2.2 g, yield: 86%) was obtained as a yellow solid. MS: m/z=430.9 [M+H]$^+$.

Intermediate 132: 2-(2-Aminopyridin-3-yl)-3-(4-(chloromethyl)phenyl)-3H-imidazo[4,5-b]pyridine-5-carbonitrile

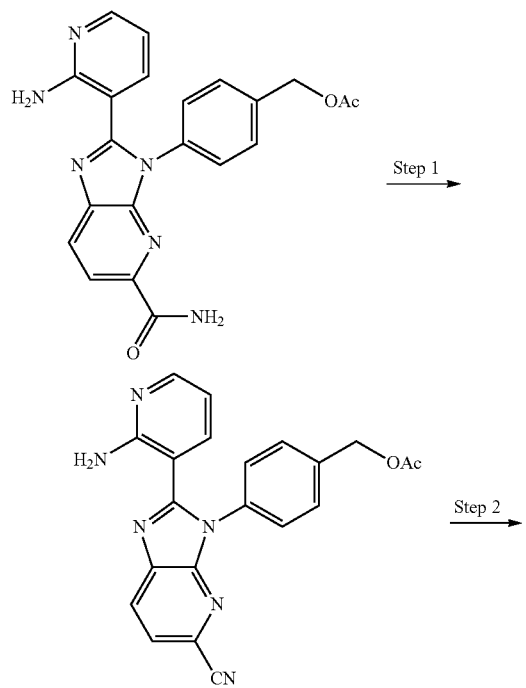

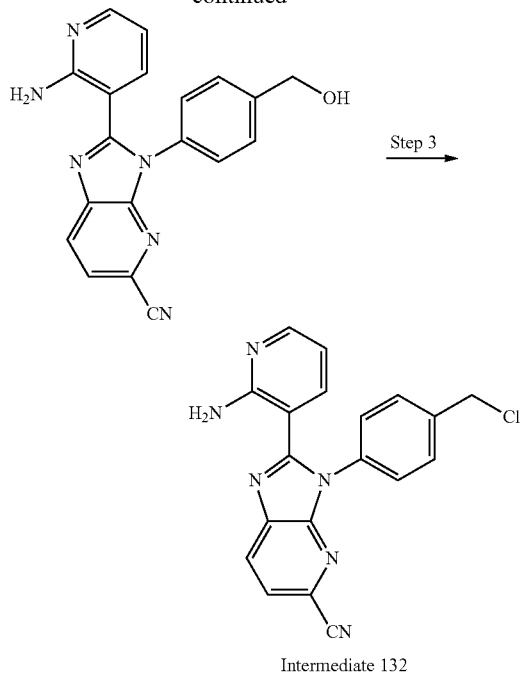

Intermediate 132

Step 1: 4-(2-(2-Aminopyridin-3-yl)-5-cyano-3H-imidazo[4,5-b]pyridin-3-yl)benzyl acetate A solution of 4-(2-(2-aminopyridin-3-yl)-5-carbamoyl-3H-imidazo[4,5-b]pyridin-3-yl)benzyl acetate (refer to Intermediate 74 for detail procedures, 250 mg, 621 μmol) in POCl$_3$ (3 mL) was stirred at 100° C. for 1 hr. The reaction mixture was filtered and concentrated under reduced pressure to give 4-(2-(2-aminopyridin-3-yl)-5-cyano-3H-imidazo[4,5-b]pyridin-3-yl)benzyl acetate (230 mg, yield: 71%) as a brown solid. MS: m/z=385.0 [M+H]$^+$. $^1$H NMR (400 MHz, Dimethylsulfoxide-d$_6$) δ 8.52 (d, J=8.0 Hz, 1H), 8.14-8.07 (m, 2H), 7.95-7.90 (m, 1H), 7.66-7.61 (m, 1H), 7.58-7.44 (m, 5H), 6.91-6.80 (m, 1H), 5.16 (s, 2H), 2.11 (s, 3H).

Step 2: 2-(2-Aminopyridin-3-yl)-3-(4-(hydroxymethyl)phenyl)-3H-imidazo[4,5-b]pyridine-5-carbonitrile To a solution of 4-(2-(2-aminopyridin-3-yl)-5-cyano-3H-imidazo[4,5-b]pyridin-3-yl)benzyl acetate (230 mg, 598 μmol) in THF (5 mL) and MeOH (5 mL) was added K$_2$CO$_3$ (248 mg, 1.8 mmol). The mixture was stirred at 25° C. for 0.5 hr. The reaction mixture was diluted with H$_2$O (20 mL) and extracted with CH$_2$Cl$_2$ (20 mL×2). The combined organic layers were washed with brine (20 mL), dried over Na$_2$SO$_4$, filtered and concentrated under reduced pressure to give 2-(2-aminopyridin-3-yl)-3-(4-(hydroxymethyl)phenyl)-3H-imidazo[4,5-b]pyridine-5-carbonitrile (200 mg, yield: 68%) as a yellow solid. MS: m/z=343.0 [M+H]$^+$. $^1$H NMR (400 MHz, Dimethylsulfoxide-d$_6$) δ 8.41 (d, J=8.4 Hz, 1H), 8.04-7.96 (m, 2H), 7.51-7.41 (m, 4H), 7.29 (dd, J=7.6, 1.6 Hz, 1H), 6.96 (s, 2H), 6.43 (dd, J=7.6, 4.8 Hz, 1H), 4.59 (s, 2H).

Step 3: 2-(2-Aminopyridin-3-yl)-3-(4-(chloromethyl)phenyl)-3H-imidazo[4,5-b]pyridine-5-carbonitrile To a solution of 2-(2-aminopyridin-3-yl)-3-(4-(hydroxymethyl)phenyl)-3H-imidazo[4,5-b]pyridine-5-carbonitrile (230 mg, 672 gmol) in CH₂Cl₂ (5 mL) was added SOCl₂ (240 mg, 2.02 mmol). The mixture was stirred at 40° C. for 0.5 hr. The reaction was concentrated under reduced pressure to give 2-(2-aminopyridin-3-yl)-3-(4-(chloromethyl)phenyl)-3H-imidazo[4,5-b]pyridine-5-carbonitrile (Intermediate 132, 240 mg, yield: 42%) as a brown solid. MS: m/z=360.9 [M+H]⁺.

Intermediate 133: 3-(3-(4-(Chloromethyl)phenyl)-5-(methylthio)-3H-imidazo[4,5-b]pyridin-2-yl)pyridin-2-amine

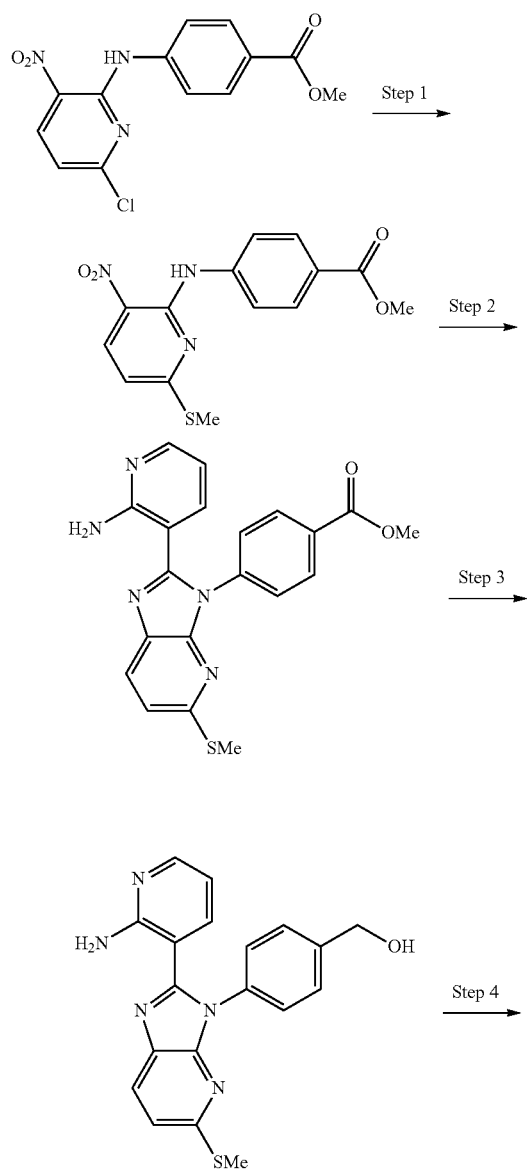

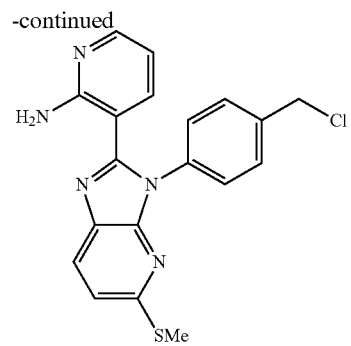

Intermediate 133

Step 1: Methyl 4-((6-(methylthio)-3-nitropyridin-2-yl)amino)benzoate

To a solution of methyl 4-[(6-chloro-3-nitro-2-pyridyl)amino]benzoate (refer to Intermediate 13 for detail procedures, 5 g, 16.3 mmol) in THF (50 mL) was added NaSMe (1.09 g, 15.6 mmol). The mixture was stirred at 25° C. for 2 hr. The mixture was diluted with H₂O (50 mL) and extracted with CH₂Cl₂ (100 mL×3). The combined organic layers were washed with brine (50 mL×2), dried over Na₂SO₄, filtered and concentrated under reduced pressure to give methyl 4-((6-(methylthio)-3-nitropyridin-2-yl)amino)benzoate (5 g, yield: 94%), which was used in the next step without further purification. MS: m/z=320.2 [M+H]⁺. ¹H NMR (400 MHz, Chloroform-d) δ 10.63 (s, 1H), 8.31 (d, J=9.2 Hz, 1H), 8.10-8.04 (m, 2H), 7.81-7.73 (m, 2H), 6.76 (d, J=8.8 Hz, 1H), 3.94 (s, 3H), 2.59 (s, 3H).

Step 2: Methyl 4-(2-(2-aminopyridin-3-yl)-5-(methylthio)-3H-imidazo[4,5-b]pyridin-3-yl)benzoate To a solution of methyl 4-((6-(methylthio)-3-nitropyridin-2-yl)amino)benzoate (5 g, 15.7 mmol), 2-aminonicotinaldehyde (1.51 g, 15.7 mmol) in DMSO (100 mL) was added Na₂S₂O₄ (10.9 g, 62.6 mmol). The mixture was stirred at 100° C. for 16 hr. The reaction mixture was diluted with H₂O (100 mL) and extracted with CH₂Cl₂ (500 mL×6). The combined organic layers were washed with brine (250 mL×2), dried over Na₂SO₄, filtered and concentrated under reduced pressure. After purified by silica gel flash chromatography (Eluent of 20~30% EtOAc in CH₂Cl₂), methyl 4-(2-(2-aminopyridin-3-yl)-5-(methylthio)-3H-imidazo[4,5-b]pyridin-3-yl)benzoate (3 g, yield: 44%) was obtained as an orange solid. MS: m/z=392.2 [M+H]⁺. ¹H NMR (400 MHz, Chloroform-d) δ 8.25-8.20 (m, 2H), 7.94-7.92 (m, 2H), 7.51 (d, J=8.4 Hz, 2H), 7.26-7.23 (m, 1H), 7.21-7.11 (m, 1H), 6.49-6.43 (m, 1H), 4.00 (s, 3H), 2.49 (s, 3H).

Step 3: (4-(2-(2-Aminopyridin-3-yl)-5-(methylthio)-3H-imidazo[4,5-b]pyridin-3-yl)phenyl)methanol To a solution of methyl 4-(2-(2-aminopyridin-3-yl)-5-(methylthio)-3H-imidazo[4,5-b]pyridin-3-yl)benzoate (1.5 g, 3.83 mmol) in THF (30 mL) was added LiAlH₄ (2.5 M, 1.53 mL) at 0° C., then the mixture was stirred at 25° C. for 2 hr. The reaction mixture was quenched with Na₂SO₄—H₂O (about 1 g) at 0° C., and the mixture was filtered, the filter cake was washed by CH₂Cl₂ (10 mL×3). The filtrate was concentrated under reduced pressure to give (4-(2-(2-aminopyridin-3-yl)-5-(methylthio)-3H-imidazo[4,5-b]pyridin-3-yl)phenyl)methanol (1.2 g, yield: 86%) as a yellow solid, which was used in the next step without purification. MS: m/z=364.1 [M+H]+ 0.1H NMR (400 MHz, Methanol-d$_4$) δ 7.86 (dd, J=5.2 Hz, 1.6 Hz, 1H), 7.53-7.49 (m, 3H), 7.30-7.23 (m, 2H), 6.84 (d, J=8.4 Hz, 1.6 Hz, 1H), 6.67-6.65 (m, 1H), 6.64-6.62 (m, 1H), 4.19 (s, 3H), 2.49 (s, 3H).

Step 4: 3-(3-(4-(Chloromethyl)phenyl)-5-(methylthio)-3H-imidazo[4,5-b]pyridin-2-yl)pyridin-2-amine To a solution of (4-(2-(2-aminopyridin-3-yl)-5-(methylthio)-3H-imidazo[4,5-b]pyridin-3-yl)phenyl)methanol (1.2 g, 3.30 mmol) in CH$_2$Cl$_2$ (15 mL) was added SOCl$_2$ (1.18 g, 9.91 mmol) at 0° C. The mixture was stirred at 40° C. for 2 hr. The reaction mixture was quenched with H$_2$O (0.5 mL) at 0° C., filtered and concentrated under reduced pressure to give 3-(3-(4-(chloromethyl)phenyl)-5-(methylthio)-3H-imidazo[4,5-b]pyridin-2-yl)pyridin-2-amine (Intermediate 133, 500 mg, yield: 42%) as a yellow solid. MS: m/z=382.2 [M+H]$^+$.

Intermediate 134: 2-(2-(2-Aminopyridin-3-yl)-3-(4-(chloromethyl)phenyl)-3H-imidazo[4,5-b]pyridin-5-yl)nicotinonitrile

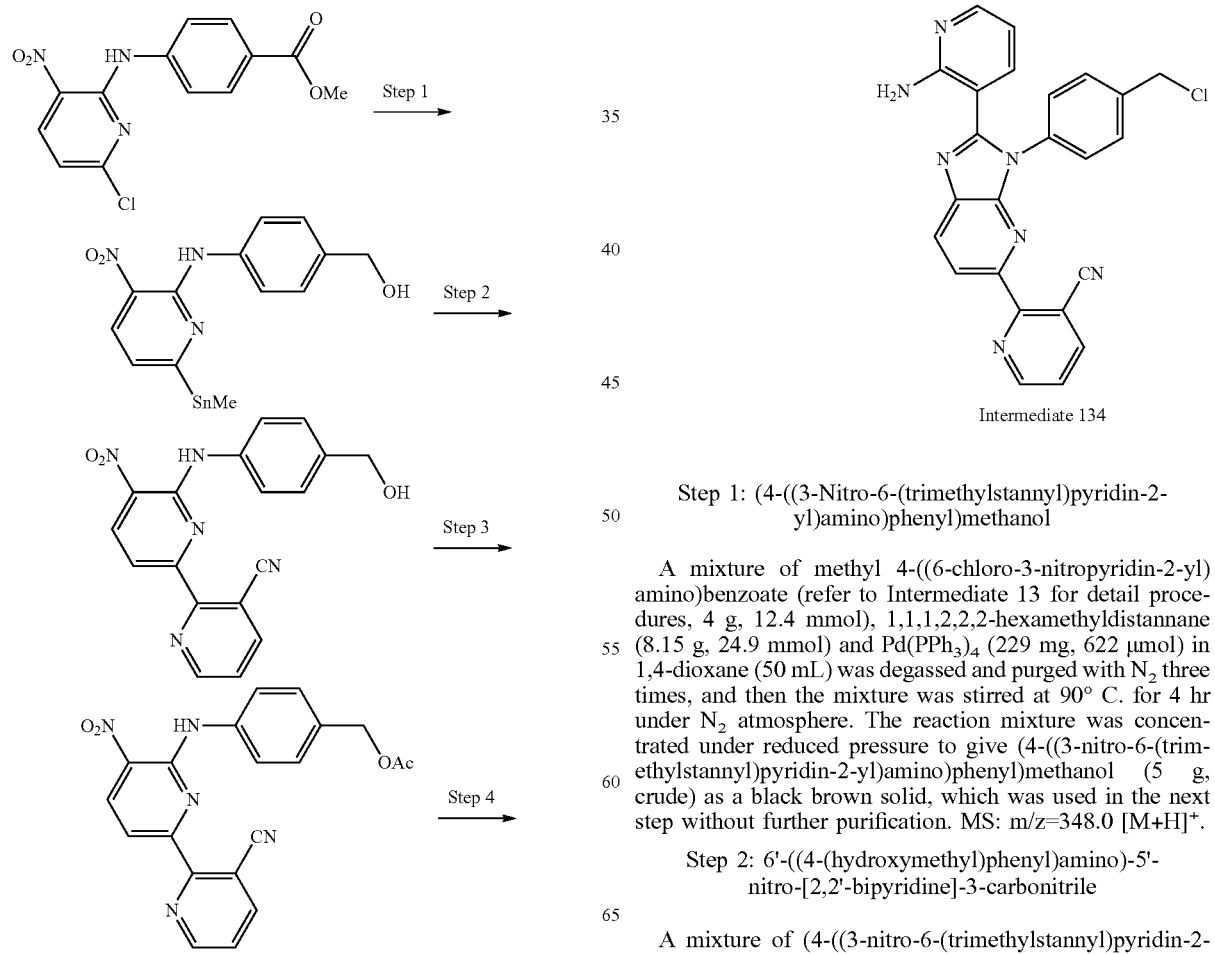

Intermediate 134

Step 1: (4-((3-Nitro-6-(trimethylstannyl)pyridin-2-yl)amino)phenyl)methanol

A mixture of methyl 4-((6-chloro-3-nitropyridin-2-yl)amino)benzoate (refer to Intermediate 13 for detail procedures, 4 g, 12.4 mmol), 1,1,1,2,2,2-hexamethyldistannane (8.15 g, 24.9 mmol) and Pd(PPh$_3$)$_4$ (229 mg, 622 μmol) in 1,4-dioxane (50 mL) was degassed and purged with N$_2$ three times, and then the mixture was stirred at 90° C. for 4 hr under N$_2$ atmosphere. The reaction mixture was concentrated under reduced pressure to give (4-((3-nitro-6-(trimethylstannyl)pyridin-2-yl)amino)phenyl)methanol (5 g, crude) as a black brown solid, which was used in the next step without further purification. MS: m/z=348.0 [M+H]$^+$.

Step 2: 6'-((4-(hydroxymethyl)phenyl)amino)-5'-nitro-[2,2'-bipyridine]-3-carbonitrile A mixture of (4-((3-nitro-6-(trimethylstannyl)pyridin-2-yl)amino)phenyl)methanol (5 g, 12.3 mmol), 2-bromonicotinonitrile (2.24 g, 12.3 mmol), and Pd(PPh₃)₄ (226 mg, 613 µmol) in 1,4-dioxane (60 mL) was degassed and purged with N₂ three times, and then the mixture was stirred at 100° C. for 16 hr under N₂ atmosphere. The residue was diluted with H₂O (50 mL) and extracted with CH₂Cl₂ (40 mL×3). The combined organic layers were washed with brine (30 mL×2), dried over Na₂SO₄, filtered and concentrated under reduced pressure to give 6'-((4-(hydroxymethyl)phenyl)amino)-5'-nitro-[2,2'-bipyridine]-3-carbonitrile (4.6 g, crude) as an orange red solid, which was directly used in the next step without further purification. MS: m/z=348.0 [M+H]⁺.

Step 3: 4-((3'-Cyano-5-nitro-[2,2'-bipyridin]-6-yl)amino)benzyl acetate

To a solution of 2-[6-[4-(hydroxymethyl) anilino]-5-nitro-2-pyridyl]pyridine-3-carbonitrile (4 g, 11.5 mmol) and Ac₂O (1.76 g, 17.3 mmol) in CH₂Cl₂ (60 mL) were added DMAP (141 mg, 1.15 mmol) and TEA (3.50 g, 34.6 mmol). The reaction mixture was diluted with H₂O (50 mL) and extracted with CH₂Cl₂ (50 mL×4). The organic layers were washed with brine (50 mL×2), dried over Na₂SO₄, filtered and concentrated under reduced pressure. After purified by silica gel flash chromatography (Eluent of 0~35% EtOAc in CH₂Cl₂), 4-((3'-cyano-5-nitro-[2,2'-bipyridin]-6-yl)amino)benzyl acetate (1.0 g, yield: 11%) was obtained as a light-yellow solid. MS: m/z=390.0 [M+H]⁺.

Step 4: 4-(2-(2-Aminopyridin-3-yl)-5-(3-cyanopyridin-2-yl)-3H-imidazo[4,5-b]pyridin-3-yl)benzyl acetate To a solution of 4-((3'-cyano-5-nitro-[2,2'-bipyridin]-6-yl)amino)benzyl acetate (500 mg, 1.28 mmol) in DMSO (20 mL) were added Na₂S₂O₄ (894 mg, 5.14 mmol, 87% purity) and 2-aminonicotinaldehyde (188 mg, 1.54 mmol). The mixture was stirred at 100° C. for 16 hr. The reaction mixture was quenched with H₂O (25 mL) at 25° C., and then diluted with H₂O (50 mL) and extracted with CH₂Cl₂ (50 mL×3). The combined organic layers were washed with brine (50 mL), dried over Na₂SO₄, filtered and concentrated under reduced pressure. After purified by silica gel flash chromatography (Eluent of 0~45% EtOAc in petroleum ether), 4-(2-(2-aminopyridin-3-yl)-5-(3-cyanopyridin-2-yl)-3H-imidazo[4,5-b]pyridin-3-yl)benzyl acetate (300 mg, yield: 42%) was obtained as a light-yellow solid. MS: m/z=462.0 [M+H]⁺. ¹H NMR (400 MHz, Chloroform-d) δ 8.82-8.78 (m, 1H), 8.29-8.23 (m, 2H), 8.07-8.04 (m, 2H), 7.60-7.55 (m, 2H), 7.53-7.49 ((m, 2H), 7.40-7.36 (m, 1H), 7.22-7.18 (m, 1H), 6.93 (br s, 2H), 6.48-6.37 (m, 1H), 5.18 (s, 2H), 2.13 (s, 3H).

Step 5: 2-(2-(2-Aminopyridin-3-yl)-3-(4-(hydroxymethyl)phenyl)-3H-imidazo[4,5-b]pyridin-5-yl)nicotinonitrile To a solution of 4-(2-(2-aminopyridin-3-yl)-5-(3-cyano-pyridin-2-yl)-3H-imidazo[4,5-b]pyridin-3-yl)benzyl acetate (300 mg, 650 µmol) in THF (2 mL) and MeOH (2 mL) was added K₂CO₃ (89.9 mg, 650 µmol). The mixture was stirred at 25° C. for 0.5 hr. The reaction mixture was diluted with H₂O (20 mL) and extracted with CH₂Cl₂ (20 mL×2). The combined organic layers were washed with brine (10 mL), dried over Na₂SO₄, filtered and concentrated under reduced pressure to give 2-(2-(2-aminopyridin-3-yl)-3-(4-(hydroxymethyl)phenyl)-3H-imidazo[4,5-b]pyridin-5-yl)nicotinonitrile (280 mg, yield: 82%) as a light-yellow solid. MS: m/z=420.0 [M+H]⁺.

Step 6: 2-(2-(2-Aminopyridin-3-yl)-3-(4-(chloromethyl)phenyl)-3H-imidazo[4,5-b]pyridin-5-yl)nicotinonitrile To a solution of 2-(2-(2-aminopyridin-3-yl)-3-(4-(hydroxymethyl)phenyl)-3H-imidazo[4,5-b]pyridin-5-yl)nicotinonitrile (280 mg, 668 µmol) in CH₂Cl₂ (5 mL) was added SOCl₂ (159 mg, 1.34 mmol). The mixture was stirred at 40° C. for 0.5 hr. The reaction was concentrated under reduced pressure to give 2-(2-(2-aminopyridin-3-yl)-3-(4-(chloromethyl)phenyl)-3H-imidazo[4,5-b]pyridin-5-yl)nicotinonitrile (Intermediate 134, 260 mg, yield: 89%) as a yellow solid. MS: m/z=438.1 [M+H]⁺.

Intermediate 135: 3-(2-(2-Aminopyridin-3-yl)-3-(4-(chloromethyl)phenyl)-3H-imidazo[4,5-b]pyridin-5-yl)picolinonitrile

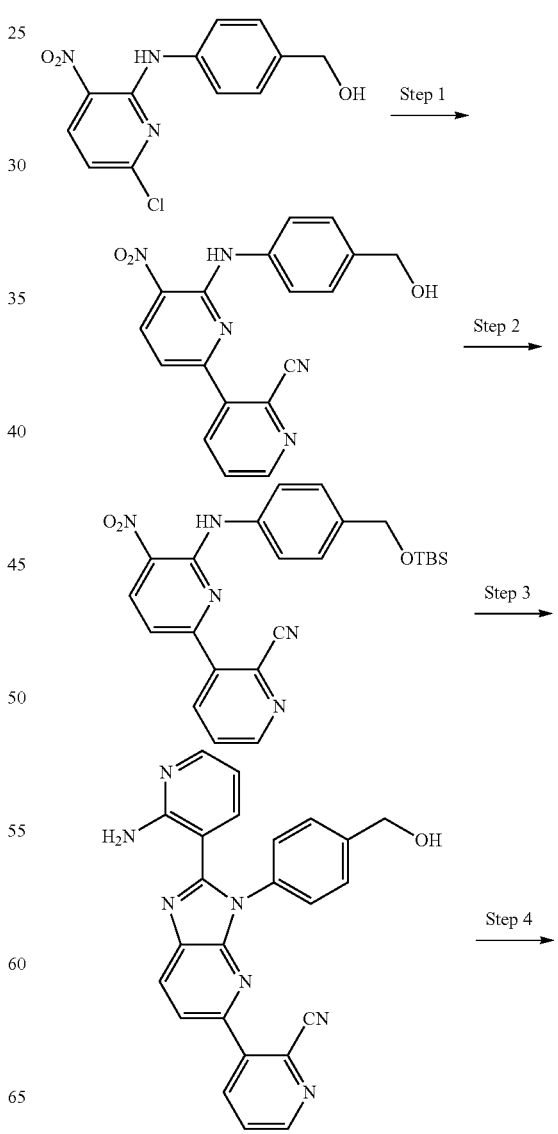

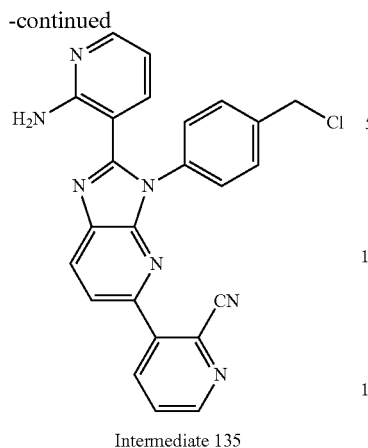

Intermediate 135

Step 1: 6-(4-(Hydroxymethyl)phenyl)amino)-5-nitro-[2,3'-bipyridine]-2'-carbonitrile To a solution of (4-((6-chloro-3-nitropyridin-2-yl)amino)phenyl)methanol (refer to Intermediate 105 for detail procedures, 2.0 g, 7.15 mmol) and (2-cyanopyridin-3-yl)boronic acid (1.16 g, 7.87 mmol) in DMF (20 mL) were added cataCXiumAPdG₃ (2.60 g, 3.58 mmol) and K₃PO₄ (3.04 g, 14.3 mmol) and tricyclohexylphosphane (200 mg, 715 μmol). The mixture was stirred at 120° C. for 3 hr under N₂ atmosphere. The reaction mixture was diluted with H₂O (500 mL) and extracted with EtOAc (250 mL×2). The combined organic layers were washed with brine (500 mL×2), dried over Na₂SO₄, filtered and concentrated under reduced pressure. After purified by silica gel flash chromatography (Eluent of 0~50% EtOAc in petroleum ether), 6-((4-(hydroxymethyl)phenyl)amino)-5-nitro-[2,3'-bipyridine]-2'-carbonitrile (1.64 g, yield: 63%) was obtained as a black brown solid. MS: m/z=347.9 [M+H]⁺. ¹H NMR (400 MHz, Dimethylsulfoxide-d₆) δ 10.07 (s, 1H), 8.86 (dd, J=4.8, 1.2 Hz, 1H), 8.74 (d, J=8.4 Hz, 1H), 8.30 (dd, J=8.0, 1.2 Hz, 1H), 7.89 (dd, J=8.0, 4.8 Hz, 1H), 7.67 (d, J=8.4 Hz, 2H), 7.45 (d, J=8.4 Hz, 1H), 7.29 (d, J=8.4 Hz, 2H), 5.15 (t, J=5.6 Hz, 1H), 4.47 (d, J=6.0 Hz, 2H)

Step 2: 6-((4-(((Tert-butyldimethylsilyl)oxy)methyl)phenyl)amino)-5-nitro-[2,3'-bipyridine]-2'-carbonitrile To a solution of 6-((4-(hydroxymethyl)phenyl)amino)-5-nitro-[2,3'-bipyridine]-2'-carbonitrile (1.6 g, 4.61 mmol) in CH₂Cl₂ (20 mL) were added imidazole (784 mg, 11.5 mmol) and TBSCl (1.39 g, 9.21 mmol) at 0° C. The reaction mixture was stirred at 25° C. for 16 hr. The mixture was concentrated under reduced pressure. After purified by silica gel flash chromatography (Eluent of 0~35% EtOAc in petroleum ether), 6-((4-(((tert-butyldimethylsilyl)oxy)methyl)phenyl)amino)-5-nitro-[2,3'-bipyridine]-2'-carbonitrile was obtained (1.7 g, yield: 79%) as a red solid. MS: m/z=462.1 [M+H]⁺. ¹H NMR (400 MHz, Dimethylsulfoxide-d₆) δ 10.08 (s, 1H), 8.85 (dd, J=4.8, 1.6 Hz, 1H), 8.74 (d, J=8.4 Hz, 1H), 8.30 (dd, J=8.4, 1.6 Hz, 1H), 7.88 (dd, J=8.0, 4.8 Hz, 1H), 7.68 (d, J=8.4 Hz, 2H), 7.45 (d, J=8.0 Hz, 1H), 7.29 (d, J=8.4 Hz, 2H), 4.68 (s, 2H), 0.89 (s, 9H), 0.07 (s, 6H).

Step 3: 3-(2-(2-Aminopyridin-3-yl)-3-(4-(hydroxymethyl)phenyl)-3H-imidazo[4,5-b]pyridin-5-yl)picolinonitrile To a solution of 6-((4-(((tert-butyldimethylsilyl)oxy)methyl)phenyl)amino)-5-nitro-[2,3'-bipyridine]-2'-carbonitrile (1.7 g, 3.68 mmol) and 2-aminonicotinaldehyde (540 mg, 4.42 mmol) in DMSO (50 mL) was added Na₂S₂O₄ (2.56 g, 14.7 mmol). The mixture was stirred at 100° C. for 16 hr. The reaction mixture was diluted with H₂O (300 mL) and extracted with EtOAc (300 mL×2). The combined organic layers were washed with brine (300 mL×2), dried over Na₂SO₄, filtered and concentrated under reduced pressure. After purified by silica gel flash chromatography (Eluent of 0~5% MeOH in CH₂Cl₂), 3-(2-(2-aminopyridin-3-yl)-3-(4-(hydroxymethyl)phenyl)-3H-imidazo[4,5-b]pyridin-5-yl)picolinonitrile (100 mg, yield: 5.7%) was obtained as a yellow solid. MS: m/z=420.0 [M+H]⁺.

Step 4: 3-(2-(2-Aminopyridin-3-yl)-3-(4-(chloromethyl)phenyl)-3H-imidazo[4,5-b]pyridin-5-yl)picolinonitrile To a solution of 3-(2-(2-aminopyridin-3-yl)-3-(4-(hydroxymethyl)phenyl)-3H-imidazo[4,5-b]pyridin-5-yl)picolinonitrile (100 mg, 238 μmol) in CH₂Cl₂ (4 mL) was added SOCl₂ (28.4 mg, 238 μmol). The mixture was stirred at 40° C. for 2 hr. The mixture was concentrated under reduced pressure to give 3-(2-(2-aminopyridin-3-yl)-3-(4-(chloromethyl)phenyl)-3H-imidazo[4,5-b]pyridin-5-yl)picolinonitrile (Intermediate 135, 100 mg, yield: 66%) as a light-yellow solid. MS: m/z=438.0 [M+H]⁺.

Intermediate 136: 3-(3-(4-(Chloromethyl)phenyl)-5-(trifluoromethyl)-3H-imidazo[4,5-b]pyridin-2-yl)pyridin-2-amine

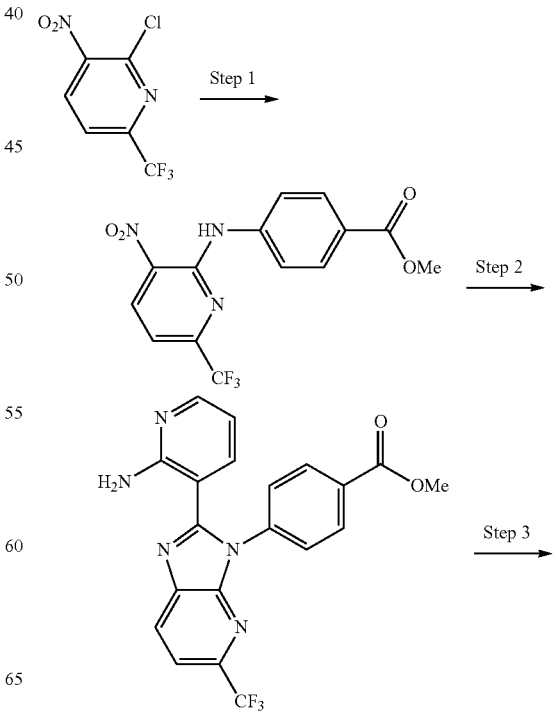

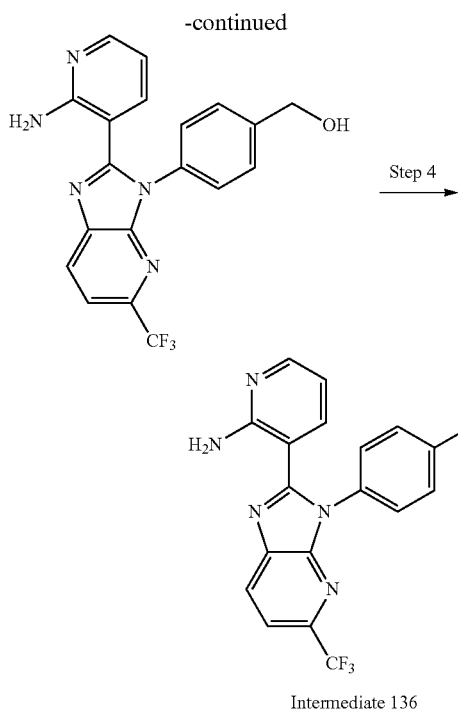

Intermediate 136

Step 1: Methyl 4-((3-nitro-6-(trifluoromethyl)pyridin-2-yl)amino)benzoate

To a solution of methyl 2-chloro-3-nitro-6-(trifluoromethyl)pyridine (5 g, 22.1 mmol) in 1,4-dioxane (50 mL) were added DIEA (8.56 g, 66.2 mmol) and methyl 4-aminobenzoate (3.34 g, 22.1 mmol). The mixture was stirred at 100° C. for 16 hr. The reaction mixture was quenched with $H_2O$ (50 mL) at 25° C., and then diluted with $H_2O$ (500 mL) and extracted EtOAc with (200 mL×3). The combined organic layers were washed with brine (50 mL), dried over $Na_2SO_4$, filtered and concentrated under reduced pressure. The crude product was triturated with EtOAc at 25° C. for 30 min to give methyl 4-((3-nitro-6-(trifluoromethyl)pyridin-2-yl)amino)benzoate (3.7 g, yield: 49%) as a yellow solid. MS: m/z=341.9 [M+H]$^+$. $^1$H NMR (400 MHz, Dimethylsulfoxide-d$_6$) δ 10.17 (s, 1H), 8.78 (d, J=8.4 Hz, 1H), 7.96 (d, J=8.8 Hz, 2H), 7.87-7.80 (m, 2H), 7.51 (d, J=8.4 Hz, 1H), 3.84 (s, 3H). $^{19}$F NMR (400 MHz, Dimethylsulfoxide-d$_6$) δ −67.72.

Step 2: Methyl 4-(2-(2-aminopyridin-3-yl)-5-(trifluoromethyl)-3H-imidazo[4,5-b]pyridin-3-yl)benzoate To a solution of methyl 4-((3-nitro-6-(trifluoromethyl)pyridin-2-yl)amino)benzoate (2.2 g, 6.45 mmol) in DMSO (50 mL) were added $Na_2S_2O_4$ (4.5 g, 25.8 mmol, 87% purity) and 2-aminonicotinaldehyde (866 mg, 7.1 mmol). The mixture was stirred at 100° C. for 16 hr. The reaction mixture was quenched with $H_2O$ (100 mL) at 25° C., and then diluted with $H_2O$ (300 mL) and extracted with $CH_2Cl_2$ (100 mL×4). The combined organic layers were washed with brine (50 mL), dried over $Na_2SO_4$, filtered and concentrated under reduced pressure. The crude was triturated with EtOAc at 25° C. for 30 min to give methyl 4-(2-(2-aminopyridin-3-yl)-5-(trifluoromethyl)-3H-imidazo[4,5-b]pyridin-3-yl)benzoate (1.3 g, yield: 49%) as a yellow solid. MS: m/z=414.0 [M+H]$^+$. $^1$H NMR (400 MHz, Dimethylsulfoxide-d$_6$) δ 8.47 (d, J=8.4 Hz, 1H), 8.11 (d, J=8.4 Hz, 2H), 8.03 (dd, J=4.8, 2.0 Hz, 1H), 7.90 (d, J=8.0 Hz, 1H), 7.63 (d, J=8.4 Hz, 2H), 7.30 (dd, J=7.2, 1.2 Hz, 1H), 6.77 (s, 2H), 6.47 (dd, J=7.6, 4.8 Hz, 1H), 3.89 (s, 3H), 19F NMR (400 MHz, Dimethylsulfoxide-d6) δ −64.28.

Step 3: (4-(2-(2-Aminopyridin-3-yl)-5-(trifluoromethyl)-3H-imidazo[4,5-b]pyridin-3-yl)phenyl)methanol To a solution of methyl 4-(2-(2-aminopyridin-3-yl)-5-(trifluoromethyl)-3H-imidazo[4,5-b]pyridin-3-yl)benzoate (500 mg, 1.21 mmol) in THF (5 mL) was added LiAlH$_4$ (91.8 mg, 2.5 mmol) at 0° C. The resulting mixture was stirred at 25° C. for 1 hr. The reaction mixture was filtered and concentrated to give (4-(2-(2-aminopyridin-3-yl)-5-(trifluoromethyl)-3H-imidazo[4,5-b]pyridin-3-yl)phenyl)methanol (450 mg, yield: 84%) as a brown solid. MS: m/z=388.0 [M+3]+.

Step 4: 3-(3-(4-(Chloromethyl)phenyl)-5-(trifluoromethyl)-3H-imidazo[4,5-b]pyridin-2-yl)pyridin-2-amine To a solution of (4-(2-(2-aminopyridin-3-yl)-5-(trifluoromethyl)-3H-imidazo[4,5-b]pyridin-3-yl)phenyl)methanol (450 mg, 1.17 mmol) in $CH_2Cl_2$ (5 mL) was added $SOCl_2$ (417 mg, 3.5 mmol). The mixture was stirred at 40° C. for 0.5 hr. The reaction was concentrated under reduced pressure to give 3-(3-(4-(chloromethyl)phenyl)-5-(trifluoromethyl)-3H-imidazo[4,5-b]pyridin-2-yl)pyridin-2-amine (Intermediate 136, 450 mg, yield: 68%) was obtained as a brown solid. MS: m/z=404.0 [M+H]$^+$.

Intermediate 137: 2-(2-Aminopyridin-3-yl)-3-(4-(chloromethyl)phenyl)-3H-imidazo[4,5-b]pyridine-6-carboxamide

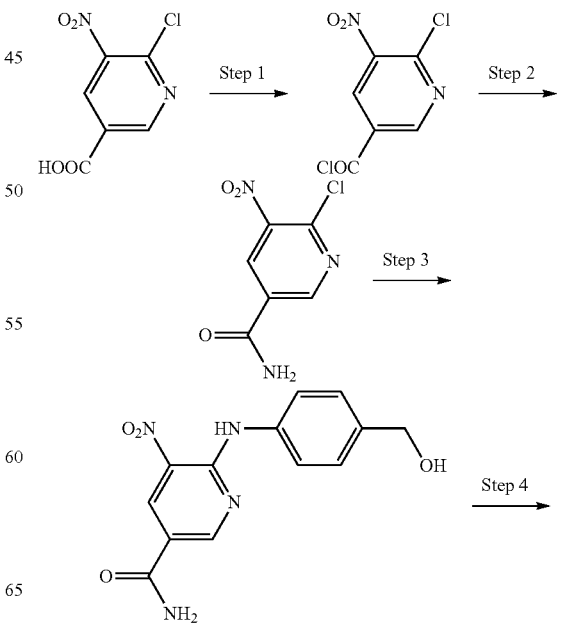

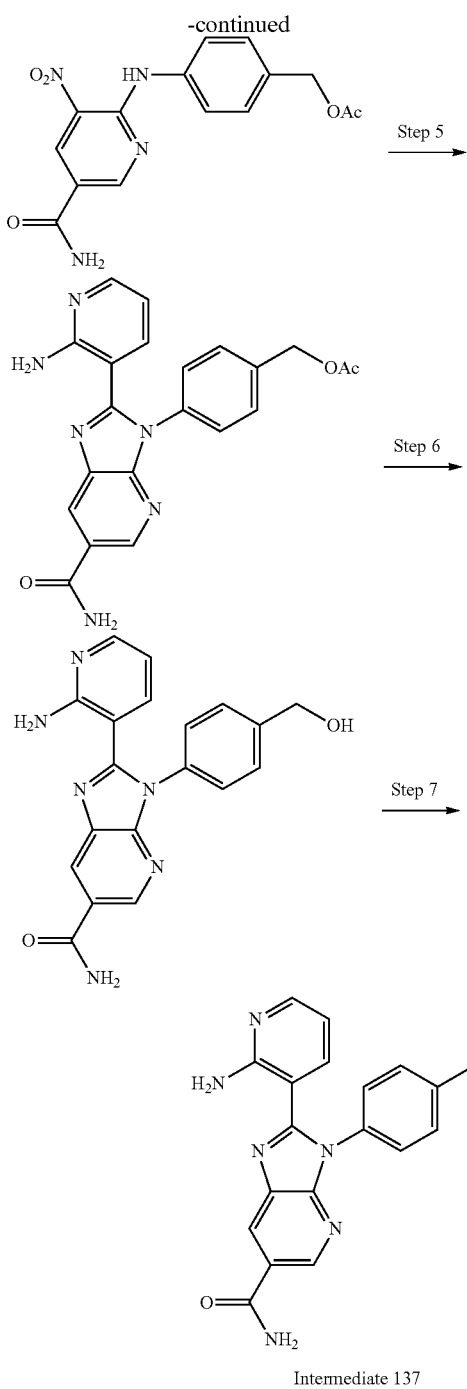

Intermediate 137

Step 1: 6-Chloro-5-nitronicotinoyl chloride

To a solution of 6-chloro-5-nitronicotinic acid (5 g, 24.7 mmol) in SOCl$_2$ (50 mL) was stirred at 80° C. for 16 hr. The reaction mixture was filtered and concentrated under reduced pressure to give 6-chloro-5-nitronicotinoyl chloride (5.4 g, yield: 91%) as a yellow solid. $^1$H NMR (400 MHz, Dimethylsulfoxide-d$_6$) δ 9.12 (s, 1H), 8.87 (s, 1H).

Step 2: 6-Chloro-5-nitronicotinamide

To a solution of 6-chloro-5-nitronicotinoyl chloride (5.4 g, 24.4 mmol) in THF (50 mL) was added NH$_3$·H$_2$O (10.3 g, 73.3 mmol) at 0° C. The mixture was stirred at 0° C. for 1 hr. Then the reaction mixture was diluted with H$_2$O (100 mL) and extracted with EtOAc (100 mL×2). The combined organic layers were dried over Na$_2$SO$_4$, filtered and concentrated under reduced pressure to give 6-chloro-5-nitronicotinamide (2.3 g, yield: 41%) as a yellow solid. MS: m/z=201.9 [M+H]$^+$. $^1$H NMR (400 MHz, Dimethylsulfoxide-d$_6$) δ 9.11 (d, J=2.0 Hz, 1H), 8.92 (d, J=2.0 Hz, 1H), 8.45 (s, 1H), 7.97 (s, 1H).

Step 3: 6-((4-(Hydroxymethyl)phenyl)amino)-5-nitronicotinamide

To a solution of 6-chloro-5-nitronicotinamide (2.3 g, 11.4 mmol) in DMSO (40 mL) were added (4-aminophenyl)methanol (1.41 g, 11.4 mmol) and DIEA (4.42 g, 34.2 mmol). The mixture was stirred at 100° C. for 16 hr. The reaction mixture was diluted with H$_2$O (100 mL) and extracted with CH$_2$Cl$_2$ (100 mL×2). The combined organic layers were washed with brine (100 mL×2), dried over Na$_2$SO$_4$, filtered and concentrated under reduced pressure to give 6-((4-(hydroxymethyl)phenyl)amino)-5-nitronicotinamide (3.2 g, yield: 78%) as a yellow solid. MS: m/z=289.0 [M+H]$^+$. $^1$H NMR (400 MHz, Dimethylsulfoxide-d$_6$) δ 10.17 (s, 1H), 9.63-9.24 (m, 1H), 8.94 (d, J=11.6 Hz, 2H), 8.21 (s, 1H), 7.58-7.55 (m, 2H), 7.33 (d, J=8.0 Hz, 2H), 5.28-5.16 (m, 1H), 4.49 (d, J=4.4 Hz, 2H).

Step 4: 4-((5-Carbamoyl-3-nitropyridin-2-yl)amino)benzyl acetate

To a solution of 6-((4-(hydroxymethyl)phenyl)amino)-5-nitronicotinamide (3.2 g, 11.1 mmol) in CH$_2$Cl$_2$ (20 mL) were added TEA (3.37 g, 33.3 mmol), Ac$_2$O (1.27 g, 12.5 mmol) and DMAP (1.7 g, 16.7 mmol). The mixture was stirred at 25° C. for 1 hr. The reaction mixture was quenched with H$_2$O (50 mL) at 25° C., and then diluted with CH$_2$Cl$_2$ (200 mL) and washed with H$_2$O (200 mL×3). The combined organic layers were washed with brine (200 mL), dried over Na$_2$SO$_4$, filtered and concentrated under reduced pressure to give 4-((5-carbamoyl-3-nitropyridin-2-yl)amino)benzyl acetate (2.5 g, yield: 84%) as a red solid. MS: m/z=331.0 [M+H]$^+$. $^1$H NMR (400 MHz, Dimethylsulfoxide-d$_6$) δ 10.19 (s, 1H), 8.94 (d, J=17.6 Hz, 2H), 8.19 (s, 1H), 7.66-7.53 (m, 3H), 7.39 (d, J=8.0 Hz, 2H), 5.07 (s, 2H), 2.07 (s, 3H).

Step 5: 4-(2-(2-Aminopyridin-3-yl)-6-carbamoyl-3H-imidazo[4,5-b]pyridin-3-yl)benzyl acetate To a solution of 4-((5-carbamoyl-3-nitropyridin-2-yl)amino)benzyl acetate (2 g, 6.06 mmol) in DMSO (10 mL) were added Na$_2$S$_2$O$_4$ (2.11 g, 12.1 mmol, 87% purity) and 2-aminonicotinaldehyde (813 mg, 6.66 mmol). The mixture was stirred at 100° C. for 16 hr. The reaction mixture was quenched with H$_2$O (100 mL) at 25° C., and then diluted with water (200 mL) and extracted with CH$_2$Cl$_2$ (100 mL×3). The combined organic layers were washed with brine (200 mL), dried over Na$_2$SO$_4$, filtered and concentrated under reduced pressure. After purified by silica gel flash chromatography (Eluent of 5%~15% MeOH in CH$_2$Cl$_2$), 4-(2-(2-aminopyridin-3-yl)-6-carbamoyl-3H-imidazo[4,5-b]pyridin-3-yl)benzyl acetate (400 mg, yield: 12%) was obtained as a brown oil. MS: m/z=403.3 [M+H]$^+$. $^1$H NMR (400 MHz, Dimethylsulfoxide-d$_6$) δ 8.86 (d, J=2.0 Hz, 1H), 8.67 (d, J=2.0 Hz, 1H), 8.14 (s, 1H), 8.04-8.01 (m, 1H), 7.59-7.45 (m, 5H), 7.39-7.33 (m, 1H), 7.05 (br s, 2H), 6.51 (dd, J=7.6, 4.8 Hz, 1H), 5.16 (s, 2H), 2.13 (s, 3H).

Step 6: 2-(2-Aminopyridin-3-yl)-3-(4-(hydroxymethyl)phenyl)-3H-imidazo[4,5-b]pyridine-6-carboxamide To a solution of 4-(2-(2-aminopyridin-3-yl)-6-carbamoyl-3H-imidazo[4,5-b]pyridin-3-yl)benzyl acetate (300 mg, 746 μmol) in THF (10 mL) and MeOH (10 mL) was added K$_2$CO$_3$ (309 mg, 2.24 mmol). The mixture was stirred at 25° C. for 0.5 hr. The reaction mixture was diluted with H$_2$O (50 mL) and extracted with CH$_2$Cl$_2$ (50 mL×2). The combined organic layers were washed with brine (50 mL), dried over Na$_2$SO$_4$, filtered and concentrated under reduced pressure to give 2-(2-aminopyridin-3-yl)-3-(4-(hydroxymethyl)phenyl)-3H-imidazo[4,5-b]pyridine-6-carboxamide (260 mg, yield: 83%) as a yellow solid. MS: m/z=361.2 [M+H]$^+$. $^1$H NMR (400 MHz, Dimethylsulfoxide-d$_6$) δ 8.93 (d, J=2.0 Hz, 1H), 8.75 (d, J=2.0 Hz, 1H), 8.58-8.28 (m, 2H), 8.20-8.07 (m, 1H), 7.95 (dd, J=7.6, 1.6 Hz, 1H), 7.60 (s, 1H), 7.47-7.46 (m, 4H), 6.96-6.82 (m, 1H), 4.57 (s, 2H).

Step 7: 2-(2-Aminopyridin-3-yl)-3-(4-(chloromethyl)phenyl)-3H-imidazo[4,5-b]pyridine-6-carboxamide To a solution of 2-(2-aminopyridin-3-yl)-3-(4-(hydroxymethyl)phenyl)-3H-imidazo[4,5-b]pyridine-6-carboxamide (260 mg, 721 μmol) in CH$_2$Cl$_2$ (5 mL) was added SOCl$_2$ (258 mg, 2.16 mmol). The mixture was stirred at 40° C. for 0.5 hr. The reaction mixture was concentrated under reduced pressure to give 2-(2-aminopyridin-3-yl)-3-(4-(chloromethyl)phenyl)-3H-imidazo[4,5-b]pyridine-6-carboxamide (Intermediate 137, 270 mg, yield: 74%) as a yellow solid. MS: m/z=379.2 [M+H]$^+$.

Intermediate 138: 3-(3-(4-(Chloromethyl)phenyl)-5,6-dimethyl-3H-imidazo[4,5-b]pyridin-2-yl)pyridin-2-amine

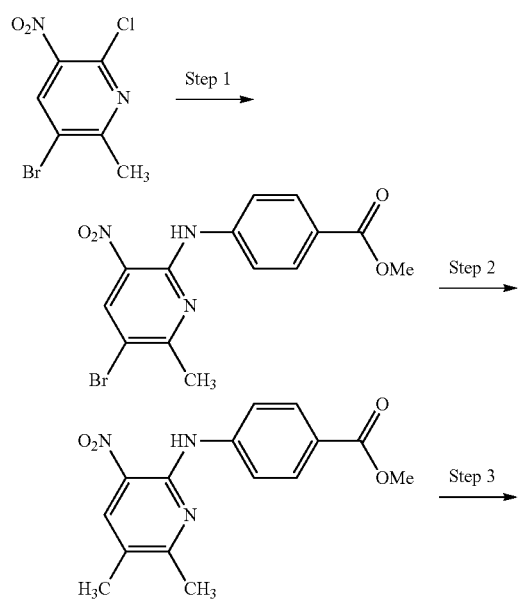

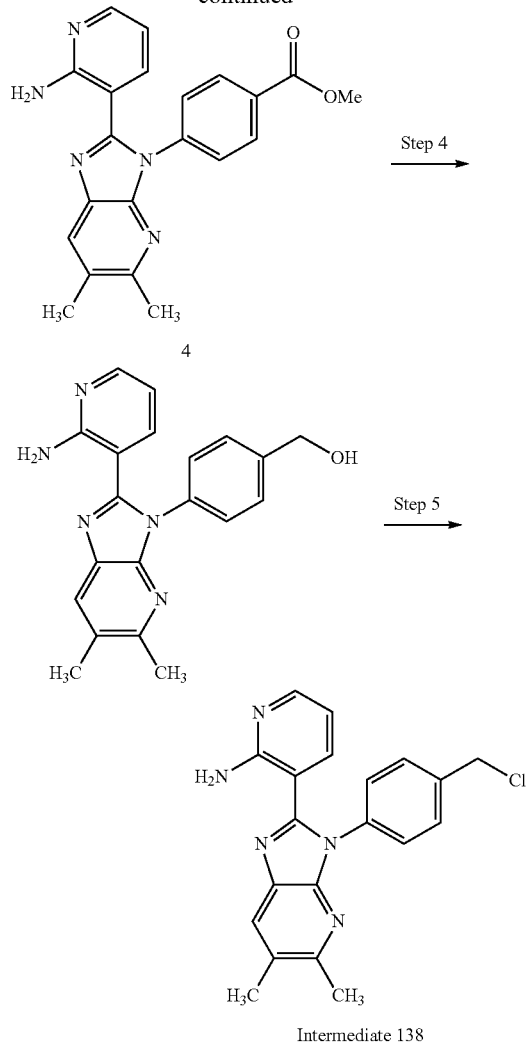

Intermediate 138

Step 1: Methyl 4-((5-bromo-6-methyl-3-nitropyridin-2-yl)amino)benzoate

To a solution of 3-bromo-6-chloro-2-methyl-5-nitropyridine (8 g, 31.8 mmol) and methyl 4-aminobenzoate (5.29 g, 35 mmol) in DMSO (200 mL) was added DIEA (4.93 g, 38.2 mmol). The mixture was stirred at 100° C. for 16 hr. The mixture was added into H$_2$O (500 mL), the mixture was filtered and the filter cake was concentrated under reduced pressure. After purified by silica gel flash chromatography (Eluent of 0~50% EtOAc in petroleum ether (adding 50% CH$_2$Cl$_2$)) and purified again by triturated with EtOAc (20 mL) at 25° C. for 0.5 hr, methyl 4-((5-bromo-6-methyl-3-nitropyridin-2-yl)amino)benzoate (2.2 g, yield: 17%) was obtained as a red solid. MS: m/z=365.8, 367.8 [M+H]$^+$. $^1$H NMR (400 MHz, Dimethylsulfoxide-d$_6$) δ 10.11 (s, 1H), 8.66 (s, 1H), 7.95 (d, J=8.8 Hz, 2H), 7.87 (d, J=8.8 Hz, 2H), 3.84 (s, 3H), 2.59 (s, 3H).

Step 2: Methyl 4-((5,6-dimethyl-3-nitropyridin-2-yl)amino)benzoate

To a solution of methyl 4-((5-bromo-6-methyl-3-nitropyridin-2-yl)amino)benzoate (2.1 g, 5.74 mmol) and methylboronic acid (412 mg, 6.88 mmol) in H₂O (2 mL) and 1,4-dioxane (20 mL) were added Pd(dppf)Cl₂ (41.9 mg, 57.4 µmol) and Cs₂CO₃ (3.74 g, 11.5 mmol). The mixture was stirred at 100° C. for 16 hr under N₂ atmosphere. The mixture was concentrated under reduced pressure. After purified by silica gel flash chromatography (Eluent of 0~10% EtOAc in petroleum ether (adding 20% CH₂Cl₂)), methyl 4-((5,6-dimethyl-3-nitropyridin-2-yl)amino)benzoate (1.6 g, yield: 81%) was obtained as a red solid. MS: m/z=302.0 [M+H]⁺. ¹H NMR (400 MHz, Dimethylsulfoxide-d₆) δ 10.10 (s, 1H), 8.34 (s, 1H), 7.93 (br s, 4H), 3.83 (s, 3H), 2.48 (s, 3H), 2.27 (s, 3H).

Step 3: Methyl 4-(2-(2-aminopyridin-3-yl)-5,6-dimethyl-3H-imidazo[4,5-b]pyridin-3-yl)benzoate To a solution of methyl 4-((5,6-dimethyl-3-nitropyridin-2-yl)amino)benzoate (1.5 g, 4.98 mmol) and 2-aminonicotinaldehyde (669 mg, 5.48 mmol) in DMSO (30 mL) was added Na₂S₂O₄ (3.47 g, 19.9 mmol). The mixture was stirred at 100° C. for 16 hr. H₂O (50 mL) was added to the mixture. The mixture was filtered. The filter cake was dissolved in CH₂Cl₂ (200 mL). The organic layer was washed with brine (100 mL×2), dried over Na₂SO₄, filtered and concentrated under reduced pressure to give a yellow solid. The yellow solid was triturated with EtOAc (10 mL) at 25° C. for 30 min to give methyl 4-(2-(2-aminopyridin-3-yl)-5,6-dimethyl-3H-imidazo[4,5-b]pyridin-3-yl)benzoate (950 mg, yield: 66%) as a light-yellow solid. MS: m/z=374.1 [M+H]⁺. ¹H NMR (400 MHz, Dimethylsulfoxide-d₆) δ 8.08 (d, J=8.4 Hz, 2H), 7.99-7.96 (m, 2H), 7.55 (d, J=8.8 Hz, 2H), 7.12 (dd, J=7.6, 1.6 Hz, 1H), 6.91 (s, 2H), 6.40 (dd, J=7.6, 4.8 Hz, 1H), 3.89 (s, 3H), 2.45 (s, 3H), 2.39 (s, 3H).

Step 4: (4-(2-(2-Aminopyridin-3-yl)-5,6-dimethyl-3H-imidazo[4,5-b]pyridin-3-yl)phenyl)methanol To a solution of methyl 4-(2-(2-aminopyridin-3-yl)-5,6-dimethyl-3H-imidazo[4,5-b]pyridin-3-yl)benzoate (950 mg, 2.54 mmol) in THF (10 mL) was added LiAlH₄ (2.5 M, 2.04 mL) at 0° C. The mixture was stirred at 25° C. for 0.5 hr under N₂ atmosphere. The Na₂SO₄·10H₂O (1 g) was added into the mixture slowly at 0° C. The mixture was stirred at 25° C. for 20 min. The mixture was filtered, concentrated under reduced pressure to give (4-(2-(2-aminopyridin-3-yl)-5,6-dimethyl-3H-imidazo[4,5-b]pyridin-3-yl)phenyl)methanol (870 mg, yield: 55%) as a light-yellow solid. MS: m/z=346.0 [M+H]⁺.

Step 5: 3-(3-(4-(Chloromethyl)phenyl)-5,6-dimethyl-3H-imidazo[4,5-b]pyridin-2-yl)pyridin-2-amine To a solution of (4-(2-(2-aminopyridin-3-yl)-5,6-dimethyl-3H-imidazo[4,5-b]pyridin-3-yl)phenyl)methanol (870 mg, 2.52 mmol) in CH₂Cl₂ (10 mL) was added SOCl₂ (819 mg, 6.88 mmol). The mixture was stirred at 40° C. for 2 hr. The mixture was concentrated under reduced pressure to give 3-(3-(4-(chloromethyl)phenyl)-5,6-dimethyl-3H-imidazo[4,5-b]pyridin-2-yl)pyridin-2-amine (Intermediate 138, 1 g, yield: 87%) as a yellow solid. MS: m/z=364.0 [M+H]⁺.

Intermediate 139: 3-(1-(4-(Chloromethyl)phenyl)-1H-imidazo[4,5-b]pyrazin-2-yl)pyridin-2-amine

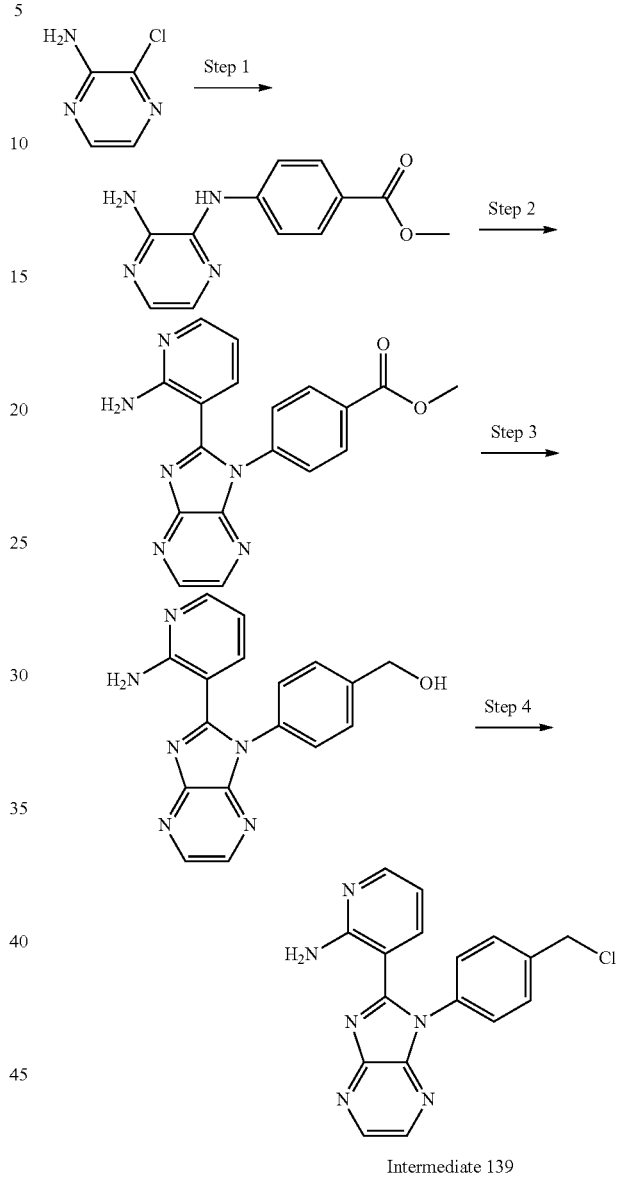

Intermediate 139

Step 1: Methyl 4-((3-aminopyrazin-2-yl)amino)benzoate

To a mixture of 3-chloropyrazin-2-amine (5 g, 38.6 mmol) in H₂O (100 mL) were added TsOH·H₂O (7.34 g, 38.6 mmol) and methyl 4-aminobenzoate (5.83 g, 38.6 mmol). The mixture was stirred at 100° C. for 16 hr. The reaction mixture was filtered and concentrated under reduced pressure. The crude was triturated with EtOAc/MeOH (1:1) (50 mL) to give methyl 4-((3-aminopyrazin-2-yl)amino)benzoate (10 g, yield: 77%) as an off-white solid. MS: m/z=245.1 [M+H]⁺. ¹H NMR (400 MHz, Dimethylsulfoxide-d₆) δ 9.31 (s, 1H), 7.58 (d, J=3.6 Hz, 1H), 7.49 (d, J=8.0 Hz, 2H), 7.44 (d, J=4.0 Hz, 1H), 7.12 (d, J=8.0 Hz, 2H), 3.83 (s, 3H).

Step 2: Methyl 4-(2-(2-aminopyridin-3-yl)-1H-imidazo[4,5-b]pyrazin-1-yl)benzoate A mixture of methyl 4-((3-aminopyrazin-2-yl)amino)benzoate (5 g, 20.4 mmol), 2-aminonicotinaldehyde (2.75 g, 22.5 mmol), and Cu(OAc)$_2$ (743 mg, 4.09 mmol) in AcOH (300 mL) was degassed and purged with N$_2$ three times. The mixture was stirred at 70° C. for 24 hr under N$_2$ atmosphere. The reaction mixture was diluted with H$_2$O (100 mL) and pH was adjusted to about 7 with sat. Na$_2$CO$_3$ (1500 mL). The mixture was extracted with EtOAc (300 mL). The combined organic layers were washed with H$_2$O (100 mL×3), dried over Na$_2$SO$_4$, filtered and concentrated under reduced pressure. After purified by silica gel flash chromatography (Eluent of 0~50% EtOAc in petroleum ether), methyl 4-(2-(2-aminopyridin-3-yl)-1H-imidazo[4,5-b]pyrazin-1-yl)benzoate (1.6 g, yield: 22%) was obtained as a yellow solid. MS: m/z=347.0 [M+H]$^+$. $^1$H NMR (400 MHz, Dimethylsulfoxide-d$_6$) δ 8.61 (d, J=2.8 Hz, 1H), 8.40 (d, J=2.8 Hz, 1H), 8.12-8.07 (m, 2H), 8.05 (dd, J=4.8, 2.0 Hz, 1H), 7.66-7.59 (m, 2H), 7.34 (dd, J=8.0, 2.0 Hz, 1H), 6.80 (s, 2H), 6.48 (dd, J=8.0, 5.2 Hz, 1H), 3.89 (s, 3H).

Step 3: (4-(2-(2-Aminopyridin-3-yl)-1H-imidazo[4,5-b]pyrazin-1-yl)phenyl)methanol A mixture of methyl 4-(2-(2-aminopyridin-3-yl)-1H-imidazo[4,5-b]pyrazin-1-yl)benzoate (1 g, 2.89 mmol) in THF (100 mL) was added LiAlH$_4$ (2.5 M, 1.73 mL) dropwise at 0° C. The mixture was stirred at 25° C. for 1 hr under N$_2$ atmosphere. The reaction mixture was quenched with 1.7 g Na$_2$SO$_4$·10H$_2$O at 0° C., filtered and concentrated under reduced pressure to give (4-(2-(2-aminopyridin-3-yl)-1H-imidazo[4,5-b]pyrazin-1-yl)phenyl)methanol (750 mg, crude) as a yellow solid. MS: m/z=318.9 [M+H]$^+$.

Step 4: 3-(1-(4-(Chloromethyl)phenyl)-1H-imidazo[4,5-b]pyrazin-2-yl)pyridin-2-amine A mixture of (4-(2-(2-aminopyridin-3-yl)-1H-imidazo[4,5-b]pyrazin-1-yl)phenyl)methanol (745 mg, 2.34 mmol) in CH$_2$Cl$_2$ (5 mL) was added SOCl$_2$ (1.67 g, 14.0 mmol), and then the mixture was stirred at 40° C. for 1 hr. The reaction mixture was filtered and concentrated under reduced pressure to give 3-(1-(4-(chloromethyl)phenyl)-1H-imidazo[4,5-b]pyrazin-2-yl)pyridin-2-amine (Intermediate 139, 100 mg, yield: 10% for 2 steps) as a brown solid. MS: m/z=337.0 [M+H]$^+$. $^1$H NMR (400 MHz, Dimethylsulfoxide-d$_6$) δ 8.69 (d, J=2.8 Hz, 1H), 8.50 (d, J=2.8 Hz, 1H), 8.15 (dd, J=6.0, 1.2 Hz, 1H), 7.96 (dd, J=7.6, 1.2 Hz, 1H), 7.62 (d, J=8.4 Hz, 2H), 7.54 (d, J=8.4 Hz, 2H), 6.90 (dd, J=7.2, 6.0 Hz, 1H), 4.84 (s, 2H).

Intermediate 140: Methyl 2-(2-aminopyridin-3-yl)-3-(4-(chloromethyl)phenyl)-3H-imidazo[4,5-b]pyridine-5-carboxylate

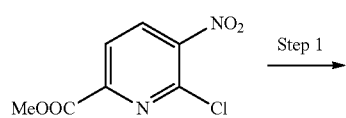

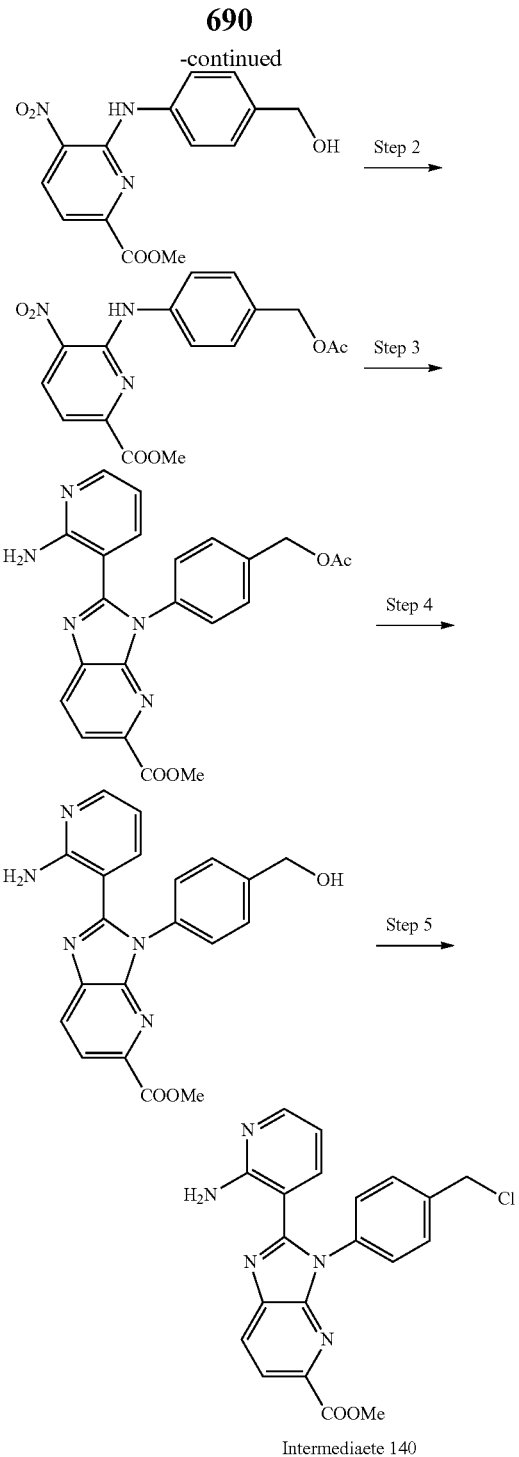

Intermediaete 140

Step 1: Methyl 6-((4-(hydroxymethyl)phenyl)amino)-5-nitropicolinate

To a solution of 6-chloro-5-nitropyridin-2-yl acetate (4.8 g, 22.2 mmol) in DMSO (40 mL) were added (4-aminophenyl)methanol (2.73 g, 22.2 mmol) and DIEA (8.59 g, 66.5 mmol). The mixture was stirred at 100° C. for 1 hr. The reaction mixture was diluted with H$_2$O (200 mL) and extracted with CH$_2$Cl$_2$ (200 mL×2). The combined organic layers were washed with brine (200 mL×2), dried over Na$_2$SO$_4$, filtered and concentrated under reduced pressure to give methyl 6-((4-(hydroxymethyl)phenyl)amino)-5-nitropicolinate (6 g, yield: 74%) as a yellow solid. MS: m/z=304.0 [M+H]⁺. ¹H NMR (400 MHz, Dimethylsulfoxide-d₆) δ 9.95 (s, 1H), 9.32 (brs, 1H), 8.68 (d, J=8.4 Hz, 1H), 7.78 (d, J=8.4 Hz, 2H), 7.52 (d, J=8.4 Hz, 1H), 7.31 (d, J=8.0 Hz, 2H), 5.18 (t, J=5.6 Hz, 2H), 4.49 (d, J=5.2 Hz, 2H), 3.90 (s, 3H).

Step 2: Methyl 6-((4-(acetoxymethyl)phenyl)amino)-5-nitropicolinate

To a solution of methyl 6-((4-(hydroxymethyl)phenyl)amino)-5-nitropicolinate (6 g, 19.8 mmol) in CH₂Cl₂ (20 mL) were added TEA (6.01 g, 59.4 mmol), Ac₂O (3.03 g, 29.7 mmol) and DMAP (242 mg, 1.98 mmol). The mixture was stirred at 25° C. for 1 hr. The reaction mixture was quenched with H₂O (100 mL) at 25° C., diluted with water (200 mL) and extracted with CH₂Cl₂ (200 mL×3). The combined organic layers were washed with brine (200 mL), dried over Na₂SO₄, filtered and concentrated under reduced pressure to give methyl 6-((4-(acetoxymethyl)phenyl)amino)-5-nitropicolinate (6.5 g, yield: 59%) as a red solid. MS: m/z=346.0 [M+H]⁺. ¹H NMR (400 MHz, Dimethylsulfoxide-d₆) δ 9.97 (s, 1H), 8.68 (d, 1=8.4 Hz, 1H), 7.84 (d, J=8.4 Hz, 2H), 7.54 (d, J=8.4 Hz, 1H), 7.37 (d, J=8.4 Hz, 2H), 5.06 (s, 2H), 3.91 (s, 3H), 2.07 (s, 3H).

Step 3: Methyl 3-(4-(acetoxymethyl)phenyl)-2-(2-aminopyridin-3-yl)-3H-imidazo[4,5-b]pyridine-5-carboxylate To a solution of methyl 6-((4-(acetoxymethyl)phenyl)amino)-5-nitropicolinate (4 g, 11.6 mmol) in DMSO (20 mL) were added Na₂S₂O₄ (4.03 g, 23.2 mmol, 87% purity) and 2-aminonicotinaldehyde (1.56 g, 12.7 mmol). The mixture was stirred at 100° C. for 16 hr. The reaction mixture was quenched with H₂O (100 mL) at 25° C., and then diluted with H₂O (200 mL) and extracted with CH₂Cl₂ (100 mL×2). The combined organic layers were washed with brine (200 mL), dried over Na₂SO₄, filtered and concentrated under reduced pressure. After purified by silica gel flash chromatography (Eluent of 30~50%, EtOAc in petroleum ether), methyl 3-(4-(acetoxymethyl)phenyl)-2-(2-aminopyridin-3-yl)-3H-imidazo[4,5-b]pyridine-5-carboxylate (560 mg, yield: 10%) was obtained as a yellow solid. MS: m/z=418.0 [M+H]⁺. ¹H NMR (400 MHz, Dimethylsulfoxide-d₆) δ 8.34 (d, J=8.0 Hz, 1H), 8.12 (d, J=8.0 Hz, 1H), 8.03-7.98 (m, 1H), 7.57-7.44 (m, 4H), 7.25 (dd, J=7.6, 1.6 Hz, 1H), 6.87 (s, 2H), 6.51-6.34 (m, 1H), 5.17 (s, 2H), 3.85 (s, 3H), 2.12 (s, 3H).

Step 4: Methyl 2-(2-aminopyridin-3-yl)-3-(4-(hydroxymethyl)phenyl)-3H-imidazo[4,5-b]pyridine-5-carboxylate To a solution of methyl 3-(4-(acetoxymethyl)phenyl)-2-(2-aminopyridin-3-yl)-3H-imidazo[4,5-b]pyridine-5-carboxylate (560 mg, 1.34 mmol) in THF (10 mL) and MeOH (10 mL) was added K₂CO₃ (556 mg, 4.02 mmol). The mixture was stirred at 25° C. for 0.5 hr. The reaction mixture was diluted with H₂O (100 mL) and extracted with CH₂Cl₂ (100 mL×2). The combined organic layers were washed with brine (100 mL), dried over Na₂SO₄, filtered and concentrated under reduced pressure to give methyl 2-(2-aminopyridin-3-yl)-3-(4-(hydroxymethyl)phenyl)-3H-imidazo[4,5-b]pyridine-5-carboxylate (330 mg, yield: 57%) was obtained as a yellow solid. MS: m/z=376.0 [M+H]⁺. ¹H NMR (400 MHz, Dimethylsulfoxide-d₆) δ 8.33 (d, J=8.0 Hz, 1H), 8.12 (d, J=8.4 Hz, 1H), 8.03-7.98 (m, 1H), 7.51-7.39 (m, 4H), 7.28-7.20 (m, 1H), 6.94 (s, 2H), 6.42 (dd, J=7.2, 4.8 Hz, 1H), 5.46-5.29 (m, 1H), 4.59 (d, J=4.4 Hz, 2H), 3.85 (s, 3H).

Step 5: Methyl 2-(2-aminopyridin-3-yl)-3-(4-(chloromethyl)phenyl)-3H-imidazo[4,5-b]pyridine-5-carboxylate To a solution of methyl 2-(2-aminopyridin-3-yl)-3-(4-(hydroxymethyl)phenyl)-3H-imidazo[4,5-b]pyridine-5-carboxylate (330 mg, 879 μmol) in CH₂Cl₂ (5 mL) was added SOCl₂ (314 mg, 2.64 mmol). The mixture was stirred at 40° C. for 0.5 hr. The reaction was concentrated under reduced pressure to give methyl 2-(2-aminopyridin-3-yl)-3-(4-(chloromethyl)phenyl)-3H-imidazo[4,5-b]pyridine-5-carboxylate (Intermediate 140, 340 mg, yield: 98%) as a yellow solid. MS: m/z=394.1 [M+H]⁺.

Intermediate 141: 3-(3-(4-(Chloromethyl)phenyl)-5-(fluoromethoxy)-3H-imidazo[4,5-b]pyridin-2-yl)pyridin-2-amine

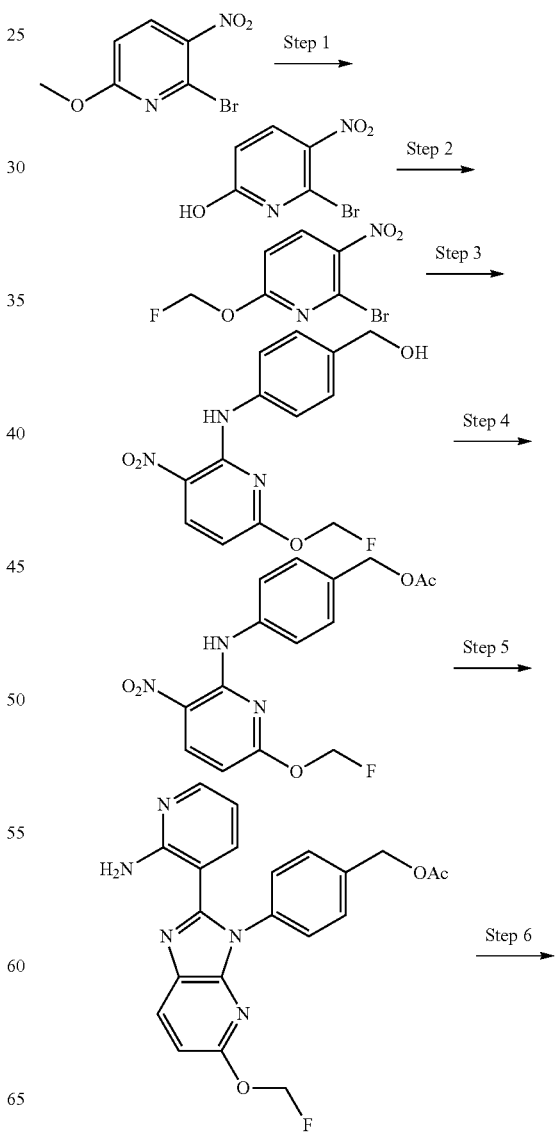

-continued

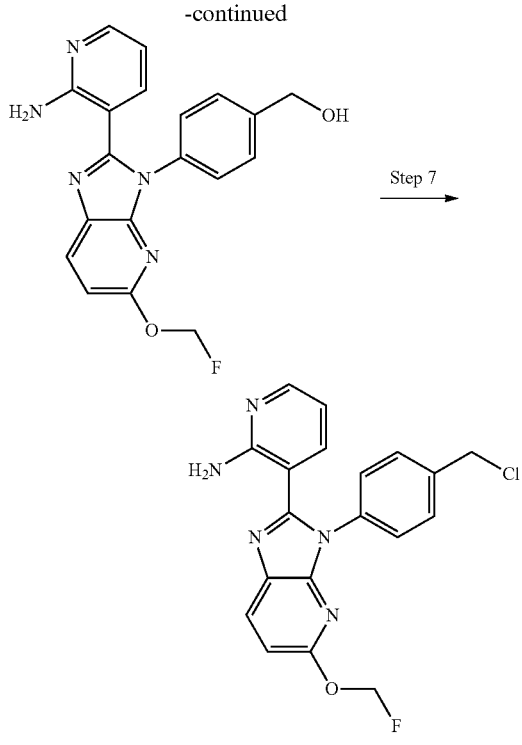

Intermediaete 141

Step 1: 6-Bromo-5-nitropyridin-2-ol

A solution of 2-bromo-6-methoxy-3-nitropyridine (9.9 g, 42.5 mmol) in hydrogen bromide (186 g, 759 mmol, 33% purity) was stirred at 80° C. for 12 hr. The reaction mixture was filtered and washed with petroleum ether. The filter cake was concentrated under reduced pressure to give 6-bromo-5-nitropyridin-2-ol (7.4 g, yield: 71%) as a brown solid. $^1$H NMR (400 MHz, Dimethylsulfoxide-d$_6$) δ 14.90-11.14 (m, 1H), 8.35 (d, J=8.8 Hz, 1H), 6.79 (d, J=8.8 Hz, 1H).

Step 2: 2-Bromo-6-(fluoromethoxy)-3-nitropyridine

To a solution of 6-bromo-5-nitropyridin-2-ol (4 g, 18.3 mmol) in DMF (30 mL) were added K$_2$CO$_3$ (5.05 g, 36.5 mmol) and CH$_2$FI (4.38 g, 27.4 mmol). The mixture was stirred at 20° C. for 2 hr. The reaction mixture was diluted with water (50 mL) and extracted with EtOAc (2×30 mL). The combined organic layers were washed with brine (130 mL), dried over Na$_2$SO$_4$, filtered and concentrated under reduced pressure. 2-bromo-6-(fluoromethoxy)-3-nitropyridine (3.1 g, yield: 64%) was obtained as a yellow solid. $^1$H NMR (400 MHz, Dimethylsulfoxide-d$_6$) δ 8.55 (d, J=8.8 Hz, 1H), 7.28 (d, J=8.8 Hz, 1H), 6.11 (d, J=51.6 Hz, 2H), $^{19}$F NMR (400 MHz, Dimethylsulfoxide-d$_6$) δ -156.386.

Step 3: (4-((6-(Fluoromethoxy)-3-nitropyridin-2-yl)amino)phenyl)methanol

To a solution of 2-bromo-6-(fluoromethoxy)-3-nitropyridine (3.1 g, 12.3 mmol) and (4-aminophenyl)methanol (1.67 g, 13.6 mmol) in DMSO (30 mL) was added DIEA (4.79 g, 37.1 mmol). The mixture was stirred at 100° C. for 2 hr. The reaction mixture was diluted with water (50 mL), filtered and concentrated under reduced pressure to give (4-((6-(fluoromethoxy)-3-nitropyridin-2-yl)amino)phenyl)methanol (3.6 g, crude) as yellow a solid. MS: m/z=294.1 [M+H]$^+$.

Step 4: 4-((6-(Fluoromethoxy)-3-nitropyridin-2-yl)amino)benzyl acetate

To a solution of 4-((6-(fluoromethoxy)-3-nitropyridin-2-yl)amino)benzyl acetate (3.5 g, 11.9 mmol) in CH$_2$Cl$_2$ (30 mL) were added Ac$_2$O (1.22 g, 11.9 mmol), DMAP (145 mg, 1.19 mmol) and TEA (3.62 g, 35.8 mmol). The mixture was stirred at 0° C. for 2 hr. The reaction mixture was diluted with water (20 mL) and extracted with CH$_2$Cl$_2$ (3×30 mL). The combined organic layers were washed with brine (30 mL), dried over Na$_2$SO$_4$, filtered and concentrated under reduced pressure. After purified by silica gel flash chromatography (Eluent of 0~100% EtOAc in petroleum ether), 4-((6-(fluoromethoxy)-3-nitropyridin-2-yl)amino)benzyl acetate (3.2 g, yield: 79%) was obtained as yellow solid. MS: m/z=336.1 [M+H]$^+$. $^1$H NMR (400 MHz, Dimethylsulfoxide-d$_6$) δ 10.35 (s, 1H), 8.58 (d, J=8.8 Hz, 1H), 7.68 (d, J=8.4 Hz, 2H), 7.38 (d, J=8.4 Hz, 2H), 6.53 (d, J=9.2 Hz, 1H), 6.01 (d, J=51.6 Hz, 2H), 5.07 (s, 2H), 2.07 (s, 3H), $^{19}$F NMR (400 MHz, Dimethylsulfoxide-d$_6$) δ -156.402.

Step 5: 4-(2-(2-Aminopyridin-3-yl)-5-(fluoromethoxy)-3H-imidazo[4,5-b]pyridin-3-yl)benzyl acetate To a solution of 4-((6-(fluoromethoxy)-3-nitropyridin-2-yl)amino)benzyl acetate (3.2 g, 9.54 mmol) and 2-aminonicotinaldehyde (1.28 g, 10.5 mmol) in DMSO (100 mL) was added Na$_2$S$_2$O$_4$ (7.64 g, 38.2 mmol, 85% purity). The mixture was stirred at 100° C. for 12 hr. The reaction mixture was diluted with water (100 mL) and extracted with CH$_2$Cl$_2$ (300 mL×2). The combined organic layers were washed with brine (100 mL), dried over Na$_2$SO$_4$, filtered and concentrated under reduced pressure. The residue was purified by silica gel flash chromatography (Eluent of 0~100% EtOAc in petroleum ether) to give 4-(2-(2-aminopyridin-3-yl)-5-(fluoromethoxy)-3H-imidazo[4,5-b]pyridin-3-yl)benzyl acetate (300 mg, yield: 6.8%) as a yellow solid. MS: m/z=408.0 [M+H]$^+$. $^1$H NMR (400 MHz, Dimethylsulfoxide-d$_6$) δ 8.25 (d, J=8.4 Hz, 1H), 7.98 (dd, J=4.8, 1.6 Hz, 1H), 7.53-7.48 (m, 2H), 7.45-7.42 (m, 2H), 7.17 (dd, J=7.6, 2.0 Hz, 1H), 6.98 (d, J=8.4 Hz, 11H), 6.78 (br s, 2H), 6.42 (dd, J=7.6, 4.8 Hz, 1H), 6.10-6.05 (m, 1H), 5.96-5.92 (m, 1H), 5.15 (s, 2H), 2.11 (s, 3H), $^{19}$F NMR (400 MHz, Dimethylsulfoxide-d$_6$) δ -153.980.

Step 6: (4-(2-(2-Aminopyridin-3-yl)-5-(fluoromethoxy)-3H-imidazo[4,5-b]pyridin-3-yl)phenyl)methanol To a solution of 4-(2-(2-aminopyridin-3-yl)-5-(fluoromethoxy)-3H-imidazo[4,5-b]pyridin-3-yl)benzyl acetate (300 mg, 736 µmol) in MeOH (3 mL) and THF (3 mL) was added a solution of K$_2$CO$_3$ (101 mg, 736 µmol) in H$_2$O (1 mL). The mixture was stirred at 25° C. for 0.5 hr. The reaction mixture was diluted with water (10 mL) and extracted with EtOAc (2×10 mL). The combined organic layers were dried over Na$_2$SO$_4$, filtered and concentrated under reduced pressure to give (4-(2-(2-aminopyridin-3-yl)-5-(fluoromethoxy)-3H-imidazo[4,5-b]pyridin-3-yl)phenyl)methanol (260 mg, yield: 83%) as a pink solid. MS: m/z=366.1 [M+H]$^+$.

Step 7: 3-(3-(4-(Chloromethyl)phenyl)-5-(fluoromethoxy)-3H-imidazo[4,5-b]pyridin-2-yl)pyridin-2-amine To a solution of (4-(2-(2-aminopyridin-3-yl)-5-(fluoromethoxy)-3H-imidazo[4,5-b]pyridin-3-yl)phenyl)methanol (260 mg, 711 μmol) in CH$_2$Cl$_2$ (5 mL) was added SOCl$_2$ (338 mg, 2.85 mmol). The mixture was stirred at 40° C. for 0.5 hr. The mixture was concentrated under reduced pressure, 3-(3-(4-(chloromethyl)phenyl)-5-(fluoromethoxy)-3H-imidazo[4,5-b]pyridin-2-yl)pyridin-2-amine (Intermediate 141, 290 mg, yield: 89%, HCl salt) was obtained as green solid. MS: m/z=384.1 [M+H]$^+$.

Intermediate 142: 3-(3-(4-(Chloromethyl)phenyl)-5-(tetrahydrofuran-3-yl)-3H-imidazo[4,5-b]pyridin-2-yl)pyridin-2-amine

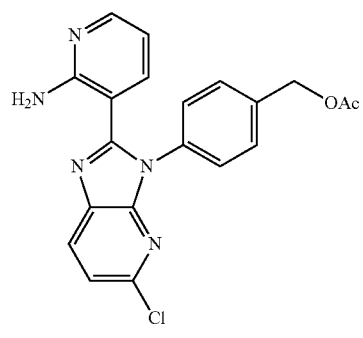

Intermediate 178


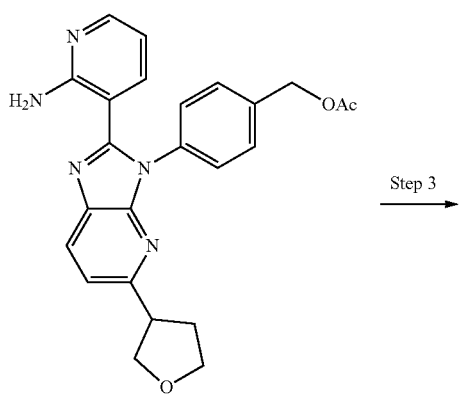

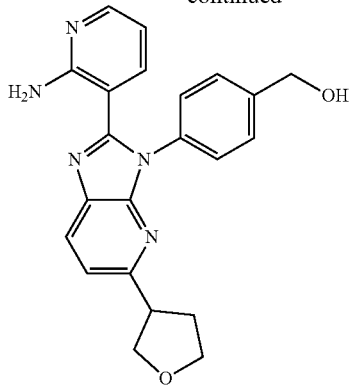

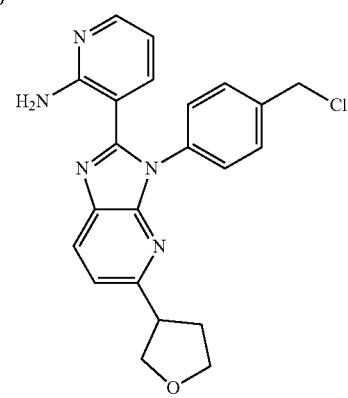

Intermediate 142

Step 1: 4-(2-(2-Aminopyridin-3-yl)-5-(2,5-dihydrofuran-3-yl)-3H-imidazo[4,5-b]pyridin-3-yl)benzyl acetate To a solution of Intermediate 178 (1 g, 2.54 mmol) and 2-(2,5-dihydrofuran-3-yl)-4,4,5,5-tetramethyl-1,3,2-dioxaborolane (547 mg, 2.79 mmol) in DMF (15 mL) were added cataCXiumAPdG3 (71.2 mg, 253 μmol), PCy$_3$ (185 mg, 254 μmol) and K$_3$PO$_4$ (1.08 g, 5.08 mmol). The mixture was stirred at 120° C. for 12 hr. The reaction mixture was diluted with H$_2$O (30 mL) and extracted with EtOAc (2×40 mL). The combined organic layers were washed with brine (10 mL), dried over Na$_2$SO$_4$, filtered and concentrated under reduced pressure. After purified by silica gel flash chromatography (Eluent of 0~70% EtOAc in petroleum ether), 4-(2-(2-aminopyridin-3-yl)-5-(2,5-dihydrofuran-3-yl)-3H-imidazo[4,5-b]pyridin-3-yl)benzyl acetate (900 mg, yield: 77%) was obtained as a yellow solid. MS: m/z=428.1 [M+H]$^+$. $^1$H NMR (400 MHz, Chloroform-d) δ 8.07 (dd, J=4.8, 1.6 Hz, 1H), 8.03 (d, J=8.4 Hz, 1H), 7.48 (d, J=8.4 Hz, 2H), 7.43-7.37 (m, 3H), 7.09 (dd, J=8.0 1.6 Hz, 1H), 6.60 (br s, 2H), 6.53 (t, J=2.0 Hz, 1H), 6.40 (dd, J=8.0, 4.8 Hz, 1H), 5.21 (s, 2H), 5.07-5.03 (m, 2H), 4.90-4.86 (m, 2H), 2.17 (s, 3H).

Step 2: 4-(2-(2-Aminopyridin-3-yl)-5-(tetrahydrofuran-3-yl)-3H-imidazo[4,5-b]pyridin-3-yl)benzyl acetate To a solution of 4-(2-(2-aminopyridin-3-yl)-5-(2,5-dihydrofuran-3-yl)-3H-imidazo[4,5-b]pyridin-3-yl)benzyl acetate (550 mg, 1.29 mmol) in MeOH (10 mL) was added Pd/C (68.4 mg, 64.3 μmol, 10% purity). The mixture was degassed and purged with H₂ three times. The mixture was stirred at 40° C. for 16 hr under H₂. The reaction mixture was filtered and concentrated under reduced pressure to give 4-(2-(2-aminopyridin-3-yl)-5-(tetrahydrofuran-3-yl)-3H-imidazo[4,5-b]pyridin-3-yl)benzyl acetate (240 mg, yield: 35%) as a yellow solid. MS: m/z=430.1 [M+H]⁺.

Step 3: (4-(2-(2-Aminopyridin-3-yl)-5-(tetrahydrofuran-3-yl)-3H-imidazo[4,5-b]pyridin-3-yl)phenyl)methanol To a solution of 4-(2-(2-aminopyridin-3-yl)-5-(tetrahydrofuran-3-yl)-3H-imidazo[4,5-b]pyridin-3-yl)benzyl acetate (240 mg, 558 µmol) in THF (7 mL) and MeOH (7 mL) was added a solution of K₂CO₃ (77.2 mg, 558 µmol) in H₂O (3.5 mL). The mixture was stirred at 25° C. for 0.5 hr. The reaction mixture was diluted with H₂O (20 mL) and extracted with EtOAc (3×30 mL). The combined organic layers were washed with brine (30 mL), dried over Na₂SO₄, filtered and concentrated under reduced pressure, (4-(2-(2-aminopyridin-3-yl)-5-(tetrahydrofuran-3-yl)-3H-imidazo[4,5-b]pyridin-3-yl)phenyl)methanol (220 mg, crude) was obtained as a yellow solid. MS: m/z=388.0 [M+H]⁺.

Step 4: 3-(3-(4-(Chloromethyl)phenyl)-5-(tetrahydrofuran-3-yl)-3H-imidazo[4,5-b]pyridin-2-yl)pyridin-2-amine To a solution of (4-(2-(2-aminopyridin-3-yl)-5-(tetrahydrofuran-3-yl)-3H-imidazo[4,5-b]pyridin-3-yl)phenyl)methanol (220 mg, 567 µmol) in CH₂Cl₂ (10 mL) was added SOCl₂ (405 mg, 3.41 mmol). The mixture was stirred at 40° C. for 0.5 hr. The mixture was concentrated under reduced pressure to give 3-(3-(4-(chloromethyl)phenyl)-5-(tetrahydrofuran-3-yl)-3H-imidazo[4,5-b]pyridin-2-yl)pyridin-2-amine (Intermediate 142, 230 mg, crude) as a yellow solid. MS: m/z=406.0 [M+H]⁺.

Intermediate 143: 6-(2-(2-Aminopyridin-3-yl)-3-(4-(chloromethyl)phenyl)-3H-imidazo[4,5-b]pyridin-5-yl)nicotinonitrile

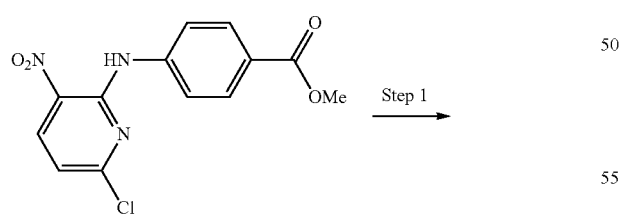

Step 1

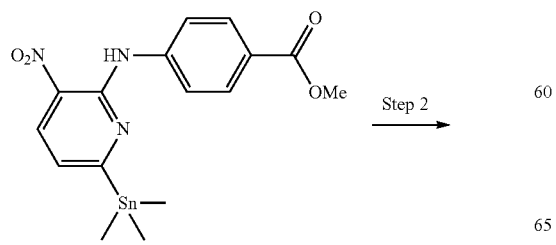

Step 2

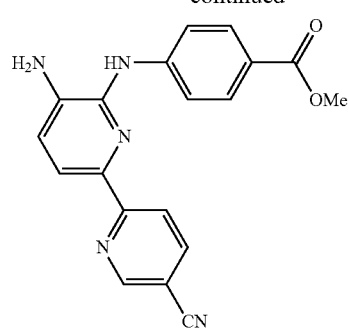

Step 3

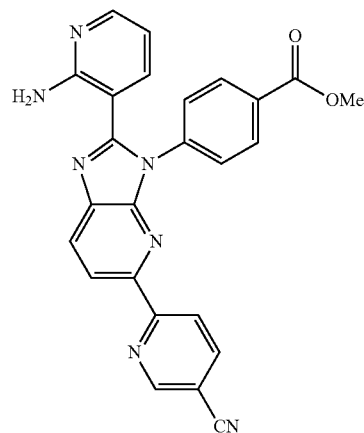

Step 4

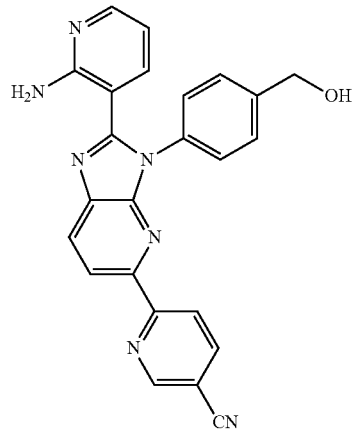

Step 5

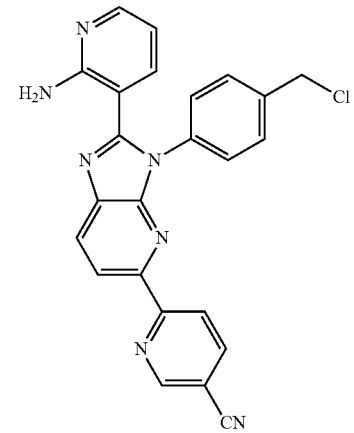

Intermediate 143

Step 1: Methyl 4-((3-nitro-6-(trimethylstannyl)pyridin-2-yl)amino)benzoate

A mixture of 4-((6-chloro-3-nitropyridin-2-yl)amino)benzoate (refer to Intermediate 13 for detail procedures, 2 g, 6.5 mmol), Pd(PPh$_3$)$_4$ (751 mg, 650 gmol), and 1,1,1,2,2,2-hexamethyldistannane (5.06 g, 15.4 mmol) in 1,4-dioxane (20 mL) was degassed and purged with N$_2$ three times, and then the mixture was stirred at 125° C. for 2 hr under N$_2$ atmosphere. The reaction mixture was used for next step directly without work-up and purification. Methyl 4-((3-nitro-6-(trimethylstannyl)pyridin-2-yl)amino)benzoate (2.83 g) was obtained as a black oil. MS: m/z=438.1 [M+H]$^+$.

Step 2: Methyl 4-((5-amino-5'-cyano-[2,2'-bipyridin]-6-yl)amino)benzoate

A mixture of methyl 4-((3-nitro-6-(trimethylstannyl)pyridin-2-yl)amino)benzoate (2.83 g, 6.49 mmol), 6-bromonicotinonitrile (594 mg, 3.25 mmol), and Pd(PPh$_3$)$_4$ (375 mg, 325 μmol) in 1,4-dioxane (30 mL) was degassed and purged with N$_2$ three times, then the mixture was stirred at 100° C. for 2 hr under N$_2$ atmosphere. The reaction was concentrated under reduced pressure. After purified by silica gel flash chromatography (Eluent of 1~33%, EtOAc in petroleum ether), methyl 4-((5-amino-5'-cyano-[2,2'-bipyridin]-6-yl) amino)benzoate (380 mg, yield: 17% for two steps) was obtained as a yellow solid. MS: m/z=346.3 [M+H]$^+$. $^1$H NMR (400 MHz, Dimethylsulfoxide-d$_6$) δ 95 (d, J=1.2 Hz, 1H), 8.51 (s, 1H), 8.29 (dd, 1=8.4, 2.0 Hz, 1H), 8.22-8.19 (m, 1H), 7.95-7.89 (m, 3H), 7.82-7.79 (m, 2H), 7.08 (d, J=8.4 Hz, 1H), 3.82 (s, 3H).

Step 3: Methyl 4-(2-(2-aminopyridin-3-yl)-5-(5-cyanopyridin-2-yl)-3H-imidazo[4,5-b]pyridin-3-yl)benzoate To a solution of methyl 4-((5-amino-5'-cyano-[2,2'-bipyridin]-6-yl)amino)benzoate (160 mg 426 μmol) in DMSO (5 mL) were added Na$_2$S$_2$O$_4$ (349 mg, 1.71 mmol 85% purity) and 2-aminonicotinaldehyde (62.5 mg, 512 μmol). The mixture was stirred at 100° C. for 16 hr. The reaction mixture was quenched with H$_2$O (10 mL) at 25° C., and then diluted with water (30 mL) and extracted with CH$_2$Cl$_2$ (50 mL×3). The combined organic layers were washed with brine (50 mL), dried over Na$_2$SO$_4$, filtered and concentrated under reduced pressure. After purified by silica gel flash chromatography (Eluent of 1~50% EtOAc in petroleum ether), methyl 4-(2-(2-aminopyridin-3-yl)-5-(5-cyanopyridin-2-yl)-3H-imidazo[4,5-b]pyridin-3-yl)benzoate (100 mg, yield: 47%) was obtained as a yellow solid. MS: m/z=448.2 [M+H]$^+$. $^1$H NMR (400 MHz, Chloroform-d) δ 8.93 (s, 1H), 8.73-8.65 (m, 1H), 8.40 (d, J=7.6 Hz, I H), 8.34-8.28 (m, 3H), 8.27-8.09 (m, 2H), 8.00-7.96 (m, 2H), 7.58 (d, J=7.2 Hz, 2H), 7.32 (d, J=7.6 Hz, 1H), 6.56-6.46 (m, 1H), 4.03 (s, 3H).

Step 4: 6-(2-(2-Aminopyridin-3-yl)-3-(4-(hydroxymethyl)phenyl)-3H-imidazo[4,5-b]pyridin-5-yl)nicotinonitrile To a solution of methyl 4-(2-(2-aminopyridin-3-yl)-5-(5-cyanopyridin-2-yl)-3H-imidazo[4,5-b]pyridin-3-yl)benzoate (100 mg, 223 μmol) in THF (2 mL) was added LiAlH$_4$ (12.7 mg, 335 μmol). The mixture was stirred at 0° C. for 1 hr. The reaction mixture was quenched with Na$_2$SO$_4$·10H$_2$O (100 mg) at 0° C., filtered and concentrated under reduced pressure to give 6-(2-(2-aminopyridin-3-yl)-3-(4-(hydroxymethyl)phenyl)-3H-imidazo[4,5-b]pyridin-5-yl)nicotinonitrile (60 mg, yield: 15%) as a yellow solid. MS: m/z=420.2 [M+H]$^+$.

Step 5: 6-(2-(2-Aminopyridin-3-yl)-3-(4-(chloromethyl)phenyl)-3H-imidazo[4,5-b]pyridin-5-yl)nicotinonitrile To a solution of 6-(2-(2-aminopyridin-3-yl)-3-(4-(hydroxymethyl)phenyl)-3H-imidazo[4,5-b]pyridin-5-yl)nicotinonitrile (60 mg, 143 μmol) in CH$_2$Cl$_2$ (5 mL) was added SOCl$_2$ (34 mg, 286 μmol) at 0° C. Then the mixture was stirred at 40° C. for 1 hr. The reaction mixture was concentrated under reduced pressure to give 6-(2-(2-aminopyridin-3-yl)-3-(4-(chloromethyl)phenyl)-3H-imidazo[4,5-b]pyridin-5-yl)nicotinonitrile (Intermediate 143, 70 mg, yield: 45%, HCl salt) as a yellow solid. MS: m/z=438.2 [M+H]$^+$.

Intermediate 144: 5-(2-(2-Aminopyridin-3-yl)-3-(4-(chloromethyl)phenyl)-3H-imidazo[4,5-b]pyridin-5-yl)picolinonitrile

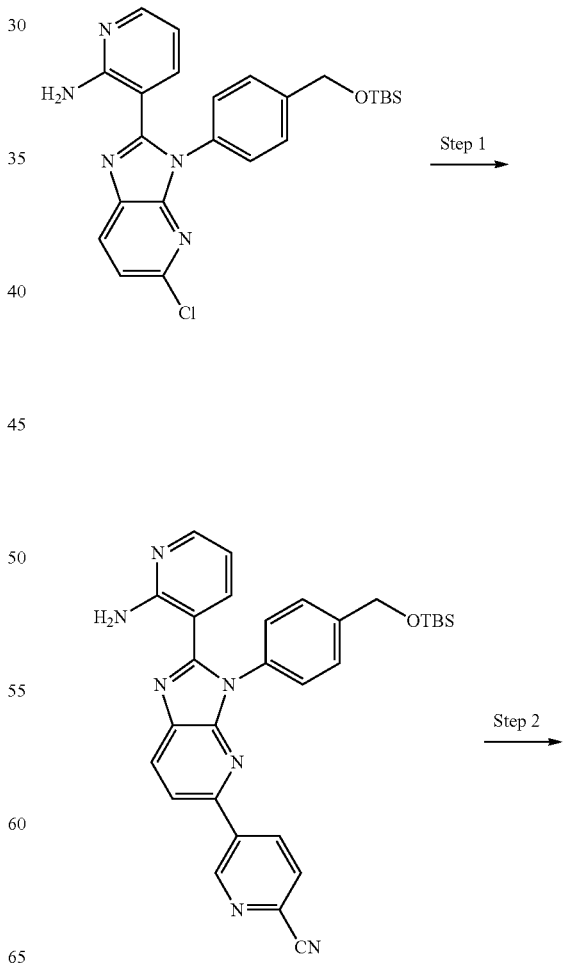

-continued

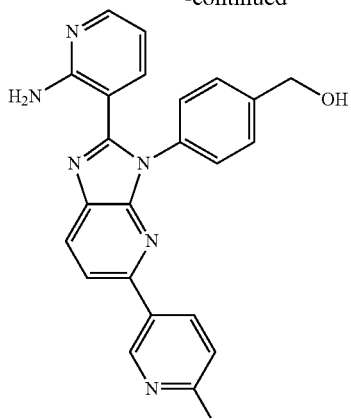

Step 3 →

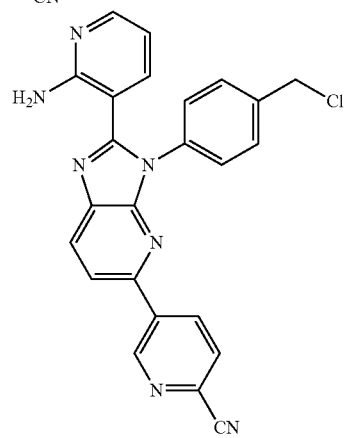

Intermediate 144

Step 1: 5-(2-(2-Aminopyridin-3-yl)-3-(4-(((tert-butyldimethylsilyl)oxy)methyl)phenyl)-3H-imidazo[4,5-b]pyridin-5-yl)picolinonitrile A mixture of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 700 mg, 1.50 mmol), (6-cyanopyridin-3-yl)boronic acid (267 mg, 1.80 mmol), Cs₂CO₃ (1.47 g, 4.51 mmol), and Pd(dppf)Cl₂ (220 mg, 300 µmol) in 1,4-dioxane (10 mL) and H₂O (2 mL) was degassed and purged with N₂ three times. The mixture was stirred at 80° C. for 2 hr under N₂ atmosphere. The reaction mixture was diluted with CH₂Cl₂ (50 mL) and extracted with H₂O (50 mL×3). The combined organic layers were washed with brine (50 mL), dried over Na₂SO₄, filtered and concentrated under reduced pressure. After purified by silica gel flash chromatography (Eluent of 50~100% EtOAc in petroleum ether), 5-(2-(2-aminopyridin-3-yl)-3-(4-(((tert-butyldimethylsilyl)oxy)methyl)phenyl)-3H-imidazo[4,5-b]pyridin-5-yl)picolinonitrile (700 mg, yield: 74%) was obtained as a yellow solid. MS: m/z=534.1 [M+H].

Step 2: 5-(2-(2-Aminopyridin-3-yl)-3-(4-(hydroxymethyl)phenyl)-3H-imidazo[4,5-b]pyridin-5-yl)picolinonitrile To a solution of 5-(2-(2-aminopyridin-3-yl)-3-(4-(((tert-butyldimethylsilyl)oxy)methyl)phenyl)-3H-imidazo[4,5-b]pyridin-5-yl)picolinonitrile (100 mg, 187 µmol) in THF (5 mL) was added TBAF (73.5 mg, 281p mol, 1 M). The mixture was stirred at 25° C. for 0.5 hr. The reaction mixture was quenched with H₂O (20 mL) at 25° C. and extracted with CH₂Cl₂ (50 mL×3). The combined organic layers were washed with brine (50 mL), dried over Na₂SO₄, filtered and concentrated under reduced pressure to give 5-(2-(2-aminopyridin-3-yl)-3-(4-(hydroxymethyl)phenyl)-3H-imidazo[4,5-b]pyridin-5-yl)picolinonitrile (100 mg, yield: 96%) as a yellow solid. MS: m/z=420.0 [M+H]⁺.

Step 3: 5-(2-(2-Aminopyridin-3-yl)-3-(4-(chloromethyl)phenyl)-3H-imidazo[4,5-b]pyridin-5-yl)picolinonitrile To a solution of 5-(2-(2-aminopyridin-3-yl)-3-(4-(hydroxymethyl)phenyl)-3H-imidazo[4,5-b]pyridin-5-yl)picolinonitrile (100 mg, 238 µmol) in CH₂Cl₂ (3 mL) was added SOCl₂ (56.7 mg, 477 µmol) at 0° C. Then the mixture was stirred at 40° C. for 1 hr. The reaction mixture was quenched with H₂O (1 mL) at 25° C., and concentrated under reduced pressure to give 5-(2-(2-aminopyridin-3-yl)-3-(4-(chloromethyl)phenyl)-3H-imidazo[4,5-b]pyridin-5-yl)picolinonitrile (Intermediate 144, 120 mg, HCl salt, yield: 82%) as a yellow solid. MS: m/z=438.2 [M+H]⁺.

Intermediate 145: 4-(2-(2-Aminopyridin-3-yl)-5-(oxetan-3-yl)-3H-imidazo[4,5-b]pyridin-3-yl)benzyl methanesulfonate

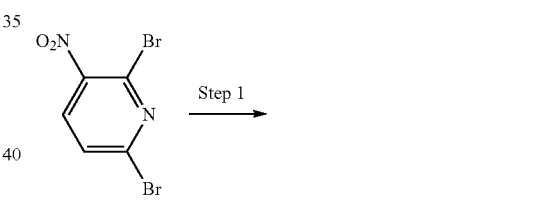

Step 1 →

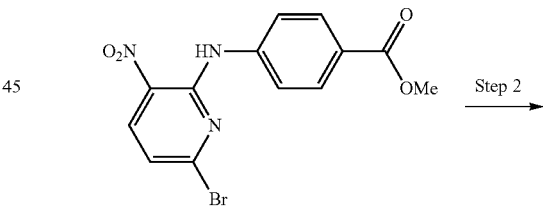

Step 2 →

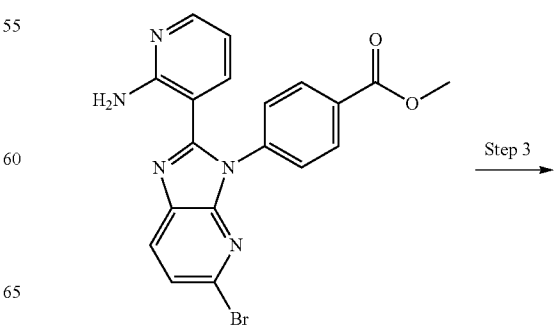

Step 3 →

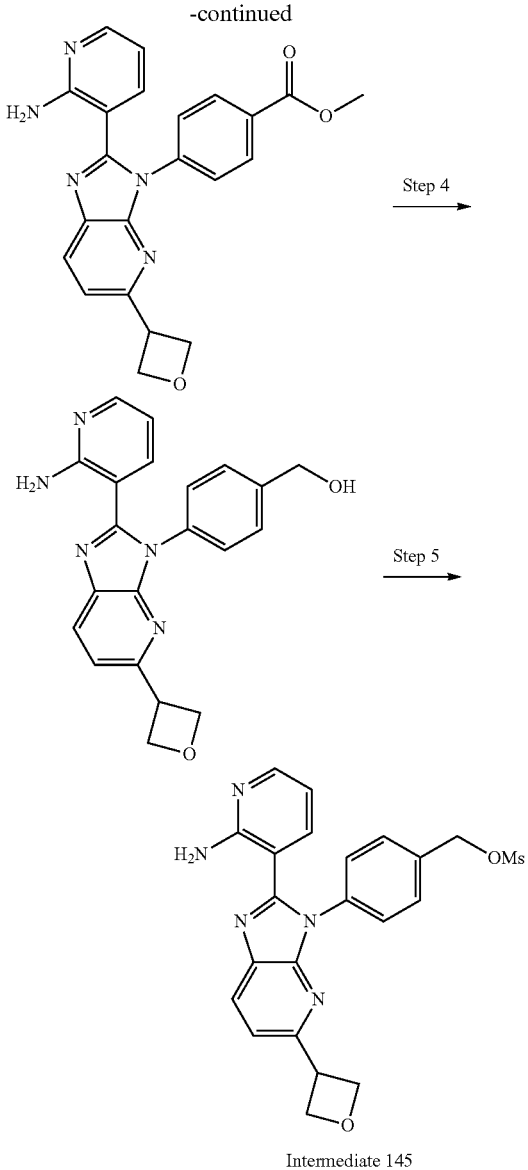

Intermediate 145

Step 1: Methyl 4-((6-bromo-3-nitropyridin-2-yl)amino)benzoate

To a solution of 2,6-dibromo-3-nitropyridine (5 g, 17.7 mmol) and methyl 4-aminobenzoate (2.68 g, 17.7 mmol) in 1,4-dioxane (50 mL) was added DIEA (4.58 g, 35.5 mmol). The mixture was stirred at 50° C. for 12 hr under $N_2$. The mixture was concentrated under reduced pressure. The crude was triturated with EtOAc (100 mL) at 25° C. for 30 min to give methyl 4-((6-bromo-3-nitropyridin-2-yl)amino)benzoate (4.4 g, yield: 70%) as a red solid. MS: m/z=351.9, 353.9 [M+H]$^+$.

Step 2: Methyl 4-(2-(2-aminopyridin-3-yl)-5-bromo-3H-imidazo[4,5-b]pyridin-3-yl)benzoate To a solution of methyl 4-((6-bromo-3-nitropyridin-2-yl)amino)benzoate (2 g, 5.68 mmol) and 2-aminopyridine-3-carbaldehyde (763 mg, 6.25 mmol) in DMSO (20 mL) was added $Na_2S_2O_4$ (2.47 g, 14.2 mmol). The mixture was stirred at 100° C. for 12 hr under $N_2$. Sat. aq. $NaHCO_3$ (50 mL) was added and the mixture was extracted with $CH_2Cl_2$/MeOH (10/1, 50 mL×3). The combined organic layers were washed with brine (50 mL×3), dried over $Na_2SO_4$, filtered and concentrated. After purified by silica gel flash chromatography (Eluent of 0-100% EtOAc in petroleum ether), methyl 4-(2-(2-aminopyridin-3-yl)-5-bromo-3H-imidazo[4,5-b]pyridin-3-yl)benzoate (1.3 g, yield: 54%) was obtained as a black brown solid. MS: m/z=423.9, 425.9 [M+H]$^+$. $^1$H NMR (400 MHz, Chloroform-d) δ 8.25-8.15 (m, 2H), 8.10-8.00 (m, 1H), 7.95 (d, J=8.4 Hz, 1H), 7.55-7.40 (m, 3H), 7.05-7.00 (m, 1H), 6.83 (br s, 2H), 6.45-6.30 (m, 1H), 3.97 (s, 3H).

Step 3: Methyl 4-(2-(2-aminopyridin-3-yl)-5-(oxetan-3-yl)-3H-imidazo[4,5-b]pyridin-3-yl)benzoate To a solution of methyl 4-(2-(2-aminopyridin-3-yl)-5-bromo-3H-imidazo[4,5-b]pyridin-3-yl)benzoate (500 mg, 1.18 mmol) and 3-bromooxetane (242 mg, 1.77 mmol) in DME (8 mL) were added bis(trimethylsilyl)silyl-trimethylsilane (293 mg, 1.18 mmol), $Na_2CO_3$ (250 mg, 2.36 mmol), 4-tert-butyl-2-(4-tert-butyl-2-pyridyl)pyridine (15.8 mg, 59.0 μmol), (Ir[df(CF$_3$)ppy]$_2$(dtbpy))PF$_6$ (13.2 mg, 11.8 μmol), and $NiCl_2$·glyme (12.9 mg, 58.9 μmol). The mixture was stirred at 25° C. for 16 hr under 450 nm blue-light with fan cooling at 5000 rpm. $H_2O$ (50 mL) was added and the mixture was extracted with $CH_2Cl_2$/MeOH (10/1, 30 mL×3). The combined organic layers were washed with brine (50 mL), dried over $Na_2SO_4$, filtered and concentrated. After purified by silica gel flash chromatography (Eluent of 0-100% EtOAc in petroleum ether), methyl 4-(2-(2-aminopyridin-3-yl)-5-(oxetan-3-yl)-3H-imidazo[4,5-b]pyridin-3-yl)benzoate (170 mg, yield: 36%) was obtained as a black brown oil. MS: m/z=402.2 [M+H]$^+$.

Step 4: (4-(2-(2-Aminopyridin-3-yl)-5-(oxetan-3-yl)-3H-imidazo[4,5-b]pyridin-3-yl)phenyl)methanol To a solution of methyl 4-(2-(2-aminopyridin-3-yl)-5-bromo-3H-imidazo[4,5-b]pyridin-3-yl)benzoate (170 mg, 424 μmol) in THF (4 mL) was added LiAlH$_4$ (32.2 mg, 847 μmol) in portions under $N_2$ at 0° C. The mixture was stirred at 0° C. for 1 hr under $N_2$. The mixture was diluted with THF (20 mL). $Na_2SO_4$·10H$_2$O was added in portions until no bubbles were formed. The resulting mixture was stirred at 25° C. for 20 min and filtered. The filter cake was washed with THF (20 mL×2), the combined filtrate was concentrated under reduced pressure. After purified by silica gel flash chromatography (Eluent of 0~100% EtOAc in petroleum ether), (4-(2-(2-aminopyridin-3-yl)-5-(oxetan-3-yl)-3H-imidazo[4,5-b]pyridin-3-yl)phenyl)methanol (50 mg, yield: 32%) was obtained as yellow oil. MS: m/z=374.2 [M+H]$^+$.

Step 5: 4-(2-(2-Aminopyridin-3-yl)-5-(oxetan-3-yl)-3H-imidazo[4,5-b]pyridin-3-yl)benzyl methanesulfonate To a solution of (4-(2-(2-aminopyridin-3-yl)-5-(oxetan-3-yl)-3H-imidazo[4,5-b]pyridin-3-yl)phenyl)methanol (50 mg, 134 μmol) in $CH_2Cl_2$ (1 mL) were added TEA (40.7 mg, 402 μmol) and MsCl (100 mg, 873 μmol) at 0° C. The mixture was stirred at 0° C. for 2 hr under $N_2$. The mixture was added dropwise into $H_2O$ (20 ml) at 0° C. The mixture was extracted with $CH_2Cl_2$ (10 mL×2). The combined organic layers were dried over Na₂SO₄, filtered and concentrated. 4-(2-(2-Aminopyridin-3-yl)-5-(oxetan-3-yl)-3H-imidazo[4,5-b]pyridin-3-yl)benzyl methanesulfonate (Intermediate 145, 60.5 mg) was obtained as yellow oil, which was used in the next step directly. MS: m/z=452.1 [M+H]⁺.

Intermediate 146: 3-(3-(4-(Chloromethyl)phenyl)-5-(4-methoxyphenyl)-3H-imidazo[4,5-b]pyridin-2-yl)pyridin-2-amine

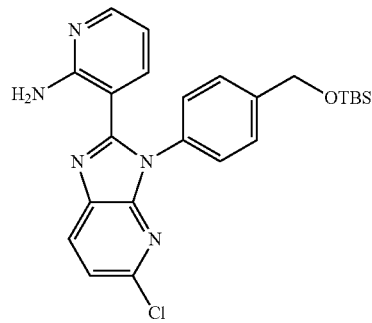

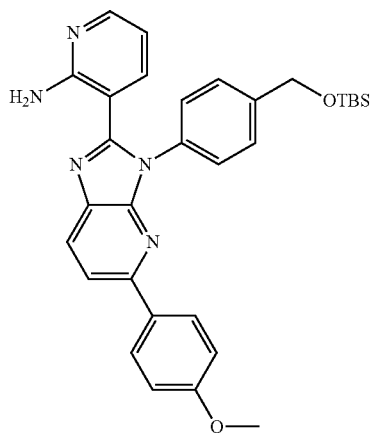

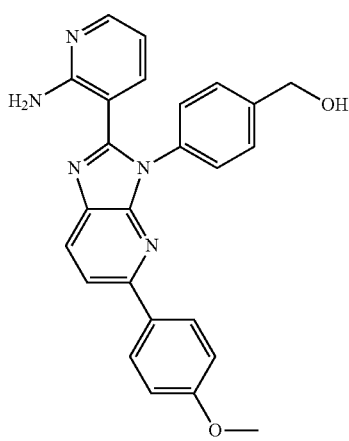

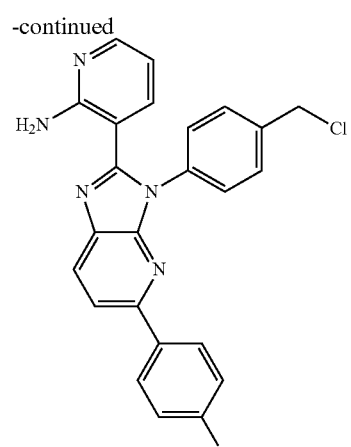

Intermediate 146

Step 1: 3-(3-(4-(((Tert-butyldimethylsilyl)oxy)methyl)phenyl)-5-(4-methoxyphenyl)-3H-imidazo[4,5-b]pyridin-2-yl)pyridin-2-amine To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 350 mg, 751 μmol) and (4-methoxyphenyl)boronic acid (126 mg, 826 μmol) in 1,4-dioxane (4 mL) and H₂O (0.8 mL) were added Pd(dppf)Cl₂ (55.0 mg, 75.1 μmol) and Cs₂CO₃ (734 mg, 2.25 mmol). The mixture was degassed and purged with N₂ three times and then was stirred at 100° C. for 2 hr under N₂. H₂O (50 mL) was added, and the mixture was extracted with EtOAc (30 mL×3). The combined organic layers were washed with brine (50 mL), dried over Na₂SO₄, filtered and concentrated. After purified by silica gel flash chromatography (Eluent of 0~70% EtOAc in petroleum ether), 3-(3-(4-(((tert-butyldimethylsilyl)oxy)methyl)phenyl)-5-(4-methoxyphenyl)-3H-imidazo[4,5-b]pyridin-2-yl)pyridin-2-amine (330 mg, yield: 82%) was obtained as a brown solid. MS: m/z=538.3 [M+H]⁺.

Step 2: (4-(2-(2-Aminopyridin-3-yl)-5-(4-methoxyphenyl)-3H-imidazo[4,5-b]pyridin-3-yl)phenyl)methanol To a solution of 3-(3-(4-(((tert-butyldimethylsilyl)oxy)methyl)phenyl)-5-(4-methoxyphenyl)-3H-imidazo[4,5-b]pyridin-2-yl)pyridin-2-amine (330 mg, 614 μmol) in THF (8 mL) was added TBAF (1 M). The mixture was stirred at 25° C. for 2 hr under N₂. H₂O (30 mL) was added and the mixture was extracted with EtOAc (10 mL×2). The combined organic layers were dried over anhydrous Na₂SO₄, filtered and concentrated. (4-(2-(2-Aminopyridin-3-yl)-5-(4-methoxyphenyl)-3H-imidazo[4,5-b]pyridin-3-yl)phenyl)methanol (250 mg, yield: 96%) was obtained as a black brown solid, which was used in the next step directly. MS: m/z=424.2 [M+H]⁺.

Step 3: 3-(3-(4-(Chloromethyl)phenyl)-5-(4-methoxyphenyl)-3H-imidazo[4,5-b]pyridin-2-yl)pyridin-2-amine To a solution of (4-(2-(2-aminopyridin-3-yl)-5-(4-methoxyphenyl)-3H-imidazo[4,5-b]pyridin-3-yl)phenyl)methanol (250 mg, 590 μmol) in CH₂Cl₂ (3 mL) was added SOCl$_2$ (211 mg, 1.77 mmol). The mixture was stirred at 25° C. for 2 hr under N$_2$. The mixture was concentrated to give 3-(3-(4-(Chloromethyl)phenyl)-5-(4-methoxyphenyl)-3H-imidazo[4,5-b]pyridin-2-yl)pyridin-2-amine (Intermediate 146, 200 mg, yield: 77%) as a black brown solid, which was used in the next step directly. MS: m/z=442.3 [M+H]$^+$.

Intermediate 147: 3-(3-(4-(Chloromethyl)phenyl)-5-(2-methoxyphenyl)-3H-imidazo[4,5-b]pyridin-2-yl)pyridin-2-amine

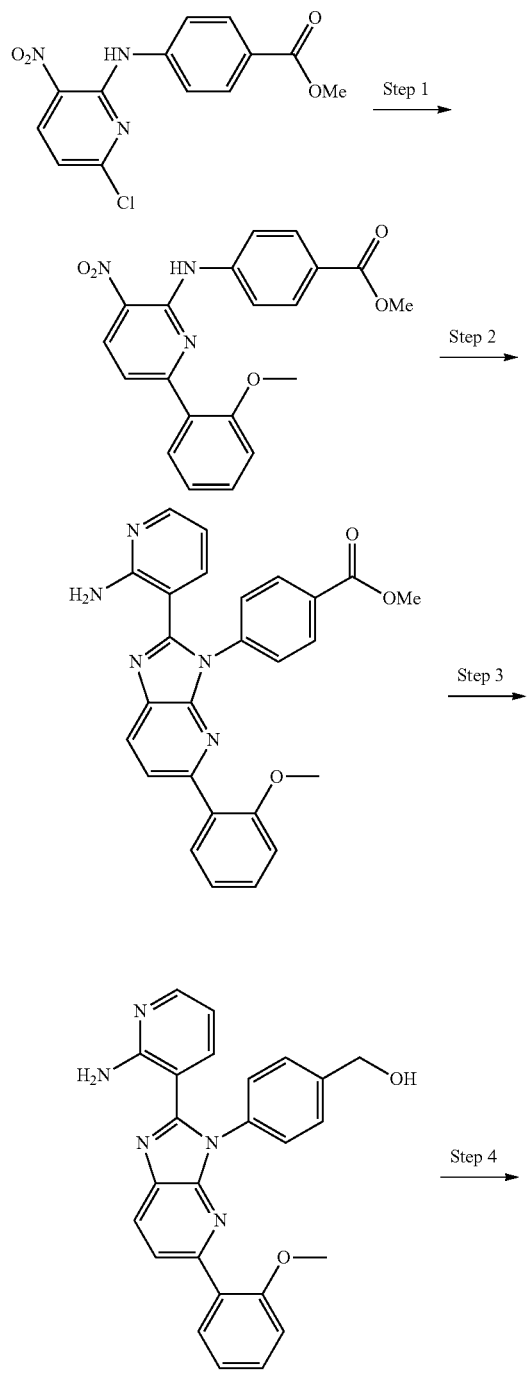

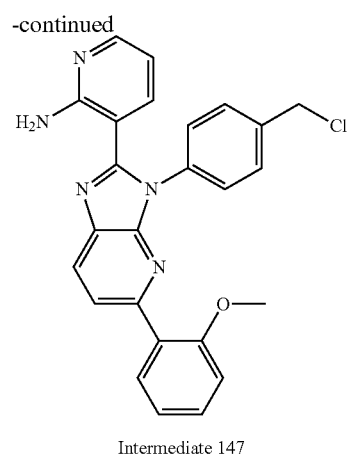

Intermediate 147

Step 1: Methyl 4-((6-(2-methoxyphenyl)-3-nitropyridin-2-yl)amino)benzoate

A mixture of methyl 4-((6-chloro-3-nitropyridin-2-yl)amino)benzoate (refer to Intermediate 13 for detail procedures, 5 g, 16.3 mmol), (2-methoxyphenyl)boronic acid (2.47 g, 16.3 mmol), Cs$_2$CO$_3$ (15.9 g, 48.8 mmol), and Pd(dppf)Cl$_2$ (595 mg, 813 µmol) in 1,4-dioxane (100 mL) and H$_2$O (20 mL) was degassed and purged with N$_2$ three times. The mixture was stirred at 80° C. for 16 hr under N$_2$ atmosphere. The reaction mixture was diluted with H$_2$O (100 mL) and extracted with EtOAc (50 mL×3). The combined organic layers were washed with brine (30 mL×3), dried over Na$_2$SO$_4$, filtered and concentrated under reduced pressure. After purified by silica gel flash chromatography (Eluent of 15~20% EtOAc in CH$_2$Cl$_2$), methyl 4-((6-(2-methoxyphenyl)-3-nitropyridin-2-yl)amino)benzoate (4 g, yield: 59%) was obtained as an orange red solid. MS: m/z=380.1 [M+H]$^+$.

Step 2: Methyl 4-(2-(2-aminopyridin-3-yl)-5-(2-methoxyphenyl)-3H-imidazo[4,5-b]pyridin-3-yl)benzoate To a solution of methyl 4-((6-(2-methoxyphenyl)-3-nitropyridin-2-yl)amino)benzoate (4 g, 10.5 mmol), 2-aminonicotinaldehyde (1.55 g, 12.7 mmol) in DMSO (100 mL) was added Na$_2$S$_2$O$_4$ (7.34 g, 42.2 mmol). The mixture was stirred at 100° C. for 16 hr. The reaction mixture was diluted with water (100 mL) and extracted with CH$_2$Cl$_2$ (100 mL×3). The combined organic layers were washed with brine (250 mL×2), dried over Na$_2$SO$_4$, filtered and concentrated under reduced pressure. After purified by silica gel flash chromatography (Eluent of 25~30% EtOAc in CH$_2$Cl$_2$), methyl 4-(2-(2-aminopyridin-3-yl)-5-(2-methoxyphenyl)-3H-imidazo[4,5-b]pyridin-3-yl)benzoate (3 g, yield: 59%) was obtained as an orange red solid. MS: m/z=452.5 [M+H]$^+$. $^1$H NMR (400 MHz, Chloroform-d) δ 8.19 (d, J=8.4 Hz, 2H), 8.11 (d, J=8.4 Hz, 1H), 8.08 (dd, J=4.8, 1.6 Hz, 1H), 7.98 (d, J=8.4 Hz, 1H), 7.78 (dd, J=7.6, 1.6 Hz, 1H), 7.55 (d, J=8.8 Hz, 2H), 7.39-7.33 (m, 1H), 7.09-7.00 (m, 3H), 6.67 (br s, 2H), 6.41 (dd, J=7.6, 4.8 Hz, 1H), 3.97 (s, 3H), 3.89 (s, 3H).

Step 3: (4-(2-(2-Aminopyridin-3-yl)-5-(2-methoxyphenyl)-3H-imidazo[4,5-b]pyridin-3-yl)phenyl)methanol To a solution of methyl 4-(2-(2-aminopyridin-3-yl)-5-(2-methoxyphenyl)-3H-imidazo[4,5-b]pyridin-3-yl)benzoate (500 mg, 1.11 mmol) in THF (10 mL) was added LiAlH$_4$ (2.5 M, 886 L) at 0° C. The mixture was stirred at 25° C. for 2 hr. The reaction mixture was quenched with Na$_2$SO$_4$·10H$_2$O (1 g) at 0° C. The mixture was filtered, and the filter cake was washed with CH$_2$Cl$_2$ (10 mL×3). The filtrate was concentrated under reduced pressure to give (4-(2-(2-aminopyridin-3-yl)-5-(2-methoxyphenyl)-3H-imidazo[4,5-b]pyridin-3-yl)phenyl)methanol (460 mg, yield: 73%) as a yellow solid, which was used to the next step without purification. MS: m/z=424.0 [M+H]$^+$.

Step 4: 3-(3-(4-(Chloromethyl)phenyl)-5-(2-methoxy phenyl)-3H-imidazo[4,5-b]pyridin-2-yl) pyridin-2-amine To a solution of (4-(2-(2-aminopyridin-3-yl)-5-(2-methoxyphenyl)-3H-imidazo[4,5-b]pyridin-3-yl)phenyl) methanol (460 mg, 1.09 mmol) in CH$_2$Cl$_2$ (5 mL) was added SOCl$_2$ (388 mg 3.26 mmol) at 0° C. The mixture was stirred at 40° C. for 1 hr. The reaction mixture was quenched with H$_2$O (0.5 mL) at 0° C., then filtered and concentrated under reduced pressure to give 3-(3-(4-(chloromethyl)phenyl)-5-(2-methoxyphenyl)-3H-imidazo[4,5-b]pyridin-2-yl)pyridin-2-amine (Intermediate 147, 500 mg, yield: 96%) as a black brown solid. MS: m/z=442.0 [M+H]-$^1$H NMR (400 MHz, Methanol-d$_4$) δ 8.31 (d, J=8.8 Hz, 1H), 8.09 (d, J=4.8 Hz, 1H), 8.05 (dd, J=6.4, 1.2 Hz, 1H), 7.95 (dd, J=7.6, 1.2 Hz, 1H), 7.71-7.65 (m, 3H), 7.60-7.56 (m, 2H), 7.43-7.38 (m, 1H), 7.13 (d, J=8.0 Hz, 1H), 7.04-6.99 (m, 1H), 6.91-6.88 (m, 1H), 4.76 (s, 2H), 3.88 (s, 3H).

Intermediate 148: 3-(3-(4-(Chloromethyl)phenyl)-5-(trifluoromethoxy)-3H-imidazo[4,5-b]pyridin-2-yl) pyridin-2-amine

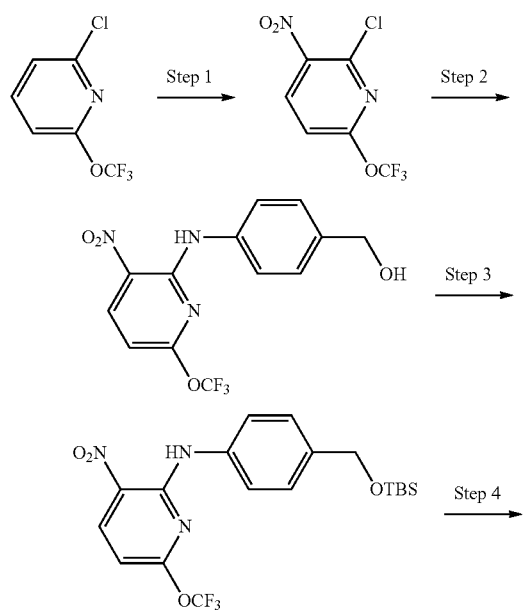

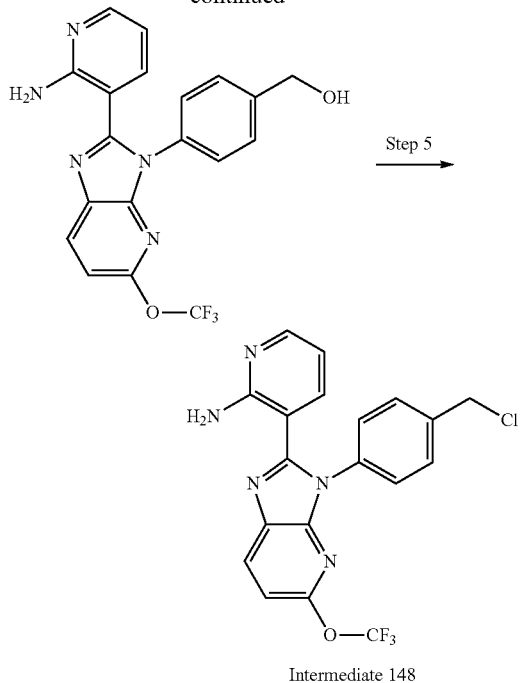

Intermediate 148

Step 1: 2-Chloro-3-nitro-6-(trifluoromethoxy)pyridine

To a solution of 2-chloro-6-(trifluoromethoxy)pyridine (2.0 g, 10.1 mmol) in H$_2$SO$_4$ (25 mL) at 0° C. was added HNO$_3$ (18.9 g, 300 mmol) dropwise and stirred for 1 hr. This mixture was stirred at 40° C. for 12 hr. This mixture was poured into ice water (30 mL) and extracted with CH$_2$Cl$_2$ (50 mL×3). The combined organic layers were washed with brine (50 mL×3), dried over Na$_2$SO$_4$, filtered and concentrated to give 2-chloro-3-nitro-6-(trifluoromethoxy)pyridine (2.40 g, yield: 97%) as yellow oil, which was used in the next step without purification.

Step 2: (4-((3-Nitro-6-(trifluoromethoxy)pyridin-2-yl)amino)phenyl)methanol

To a mixture of 2-chloro-3-nitro-6-(trifluoromethoxy) pyridine (1.80 g, 7.42 mmol) in THF (25 mL) were added DIEA (2.88 g, 22.3 mmol) and (4-aminophenyl)methanol (1.01 g, 8.16 mmol) at 25° C., the mixture was stirred at 80° C. for 1 hr. The mixture was quenched with water (30 mL) and then extracted with EtOAc (30 mL×3). The combined organic layers were filtered and concentrated to give the crude. After purified by silica gel flash chromatography (Eluent of 0~30% EtOAc in petroleum ether), (4-((3-nitro-6-(trifluoromethoxy)pyridin-2-yl)amino)phenyl)methanol (900 mg, yield: 36%) was obtained as a yellow solid. $^1$H NMR (400 MHz, Dimethylsulfoxide-d$_6$) δ 10.26 (s, 1H), 8.70 (d, J=8.8 Hz, 1H), 7.54 (d, J=8.4 Hz, 2H), 7.32 (d, J=8.8 Hz, 2H), 6.70 (d, J=8.8 Hz, 1H), 5.18 (t, J=5.6 Hz, 1H), 4.50 (d, J=5.6 Hz, 2H). $^{19}$F NMR (376.5 MHz, Dimethylsulfoxide-d$_6$) δ −55.544.

Step 3: N-(4-(((Tert-butyldimethylsilyl)oxy)methyl) phenyl)-3-nitro-6-(trifluoromethoxy)pyridin-2-amine To a solution of (4-((3-Nitro-6-(trifluoromethoxy)pyridin-2-yl)amino)phenyl)methanol (900 mg, 2.73 mmol) in CH₂Cl₂ (8 mL) were added imidazole (279 mg, 4.10 mmol) and TBSCl (536 mg, 3.55 mmol) at 25° C. This mixture was stirred at 25° C. for 1 hr. The mixture was filtered and concentrated to give N-(4-(((tert-butyldimethylsilyl)oxy) methyl)phenyl)-3-nitro-6-(trifluoromethoxy)pyridin-2-amine (1.20 g, yield: 99%) as a yellow solid, which was used in the next step without further purification. MS: m/z=444.2 [M+H]⁺. ¹H NMR (400 MHz, Dimethylsulfoxide-d₆) δ 10.25 (s, 1H), 8.69 (d, J=8.8 Hz, 1H), 7.53 (d, J=8.4 Hz, 2H), 7.30 (d, J=8.4 Hz, 2H), 6.69 (d, J=8.8 Hz, 1H), 4.71 (s, 2H), 0.89 (s, 9H), 0.07 (s, 6H). ¹⁹F NMR (400 MHz, Dimethylsulfoxide-d₆) δ −55.611.

Step 4: (4-(2-(2-Aminopyridin-3-yl)-5-(trifluoromethoxy)-3H-imidazo[4,5-b]pyridin-3-yl)phenyl) methanol To a solution of N-(4-(((tert-butyldimethylsilyl)oxy) methyl)phenyl)-3-nitro-6-(trifluoromethoxy)pyridin-2-amine (1.20 g, 2.71 mmol) in DMSO (10 mL) were added Na₂S₂O₄ (1.18 g, 6.76 mmol) and 2-aminopyridine-3-carbaldehyde (363 mg, 2.98 mmol) at 25° C. The mixture was stirred at 100° C. for 12 hr. NaHCO₃ (sat, 50 mL) was added and the mixture was extracted with CH₂Cl₂ (50 mL×3). The combined organic layers were washed with brine (50 mL×3), dried over Na₂SO₄, filtered and concentrated to give the crude. After purified by silica gel flash chromatography (Eluent of 0~100% EtOAc/EtOH (3/1) in petroleum ether), (4-(2-(2-aminopyridin-3-yl)-5-(trifluoromethoxy)-3H-imidazo[4,5-b]pyridin-3-yl)phenyl)methanol (400 mg, yield: 37%) was obtained as a brown oil. MS: m/z=402.0 [M+H]⁺. ¹H NMR (400 MHz, Dimethylsulfoxide-d₆) δ 8.41 (d, J=8.0 Hz, 1H), 7.99 (dd, J=4.8, 1.6 Hz, 1H), 7.45 (d, J=8.4 Hz, 2H), 7.38 (d, J=8.0 Hz, 2H), 7.31-7.21 (m, 2H), 6.79 (s, 2H), 6.43 (dd, J=7.6, 4.8 Hz, 1H), 5.34 (t, J=6.0 Hz, 1H), 4.57 (d, J=5.2 Hz, 2H). ¹⁹F NMR (400 MHz, Dimethylsulfoxide-d₆) δ −55.482.

Step 5: 3-(3-(4-(Chloromethyl)phenyl)-5-(trifluoromethoxy)-3H-imidazo[4,5-b]pyridin-2-yl)pyridin-2-amine To a solution of (4-(2-(2-aminopyridin-3-yl)-5-(trifluoromethoxy)-3H-imidazo[4,5-b]pyridin-3-yl)phenyl)methanol (400 mg, 997 µmol) in CH₂Cl₂ (5 mL) was added SOCl₂ (356 mg, 2.99 mmol) at 25° C. This mixture was stirred at 25° C. for 1 hr. The reaction mixture was concentrated to give 3-(3-(4-(chloromethyl)phenyl)-5-(trifluoromethoxy)-3H-imidazo[4,5-b]pyridin-2-yl)pyridin-2-amine (Intermediate 148, 220 mg) as a brown solid, which was used in the next step without purification. MS: m/z=420.1 [M+H]⁺.

Intermediate 149: 3-(3-(4-(Chloromethyl)phenyl)-5-isopropoxy-3H-imidazo[4,5-b]pyridin-2-yl)pyridin-2-amine

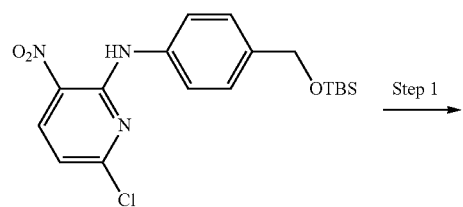

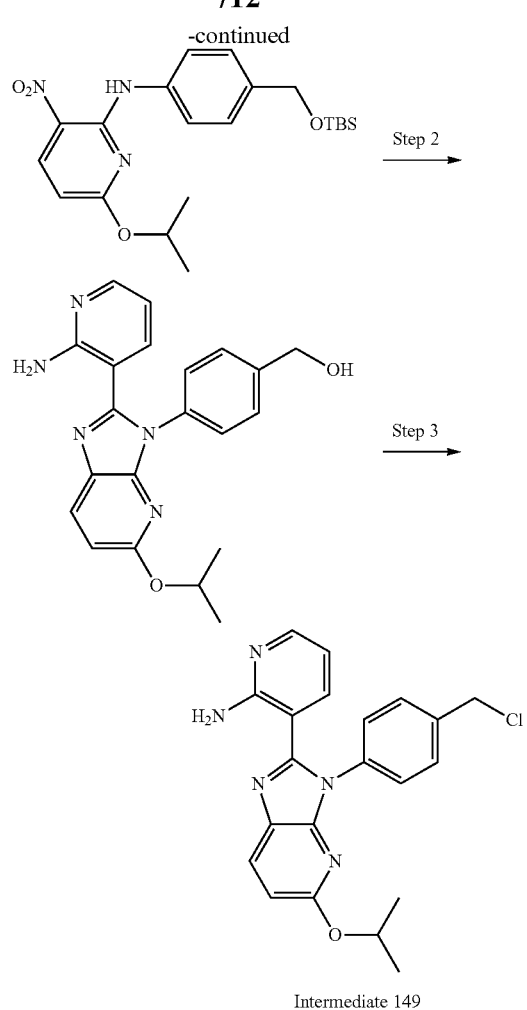

Intermediate 149

Step 1: N-(4-(((tert-butyldimethylsilyl)oxy)methyl) phenyl)-6-isopropoxy-3-nitropyridin-2-amine To a mixture of N-(4-(((tert-butyldimethylsilyl)oxy) methyl)phenyl)-6-chloro-3-nitropyridin-2-amine (refer to Intermediate 105 for detail procedures, 1 g, 2.54 mmol) in i-PrOH (10 mL) was added NaH (203 mg, 5.08 mmol, 60% purity). The mixture was stirred at 20° C. for 12 hr. H₂O (50 mL) was added, and the mixture was extracted with EtOAc (100 mL×2). The combined organic layers were washed with brine (50 mL), dried over Na₂SO₄, filtered and concentrated. After purified by silica gel flash chromatography (Eluent of 0~30% EtOAc in petroleum ether), N-(4-(((tert-butyldimethylsilyl)oxy)methyl)phenyl)-6-isopropoxy-3-nitropyridin-2-amine (710 mg, yield: 67%) was obtained as a yellow solid. MS: m/z=418.1 [M+H]⁺. ¹H NMR (400 MHz, Dimethylsulfoxide-d₆) δ 10.40 (s, 1H), 8.39 (d, J=8.8 Hz, 1H), 7.58 (d, J=8.4 Hz, 2H), 7.32 (d, J=8.4 Hz, 2H), 6.27 (d, J=9.2 Hz, 1H), 5.17-5.00 (m, 1H), 4.71 (s, 2H), 1.25 (d, J=6.2 Hz, 6H), 0.89 (s, 9H), 0.07 (s, 6H).

Step 2: (4-(2-(2-Aminopyridin-3-yl)-5-isopropoxy-3H-imidazo[4,5-b]pyridin-3-yl)phenyl)methanol To a mixture of N-(4-(((tert-butyldimethylsilyl)oxy) methyl)phenyl)-6-isopropoxy-3-nitropyridin-2-amine (700 mg, 1.68 mmol) and 2-aminopyridine-3-carbaldehyde (225 mg, 1.84 mmol) in DMSO (10 mL) was added Na$_2$S$_2$O$_4$ (730 mg, 4.19 mmol). The mixture was stirred at 100° C. for 12 hr. H$_2$O (50 mL) was added. The mixture was filtered and concentrated to give (4-(2-(2-aminopyridin-3-yl)-5-isopropoxy-3H-imidazo[4,5-b]pyridin-3-yl)phenyl)methanol (500 mg, yield: 79%) as a brown solid. MS: m/z=376.0 [M+H]$^+$.

Step 3: 3-(3-(4-(Chloromethyl)phenyl)-5-isopropoxy-3H-imidazo[4,5-b]pyridin-2-yl)pyridin-2-amine To a mixture of (4-(2-(2-aminopyridin-3-yl)-5-isopropoxy-3H-imidazo[4,5-b]pyridin-3-yl)phenyl)methanol (450 mg, 1.20 mmol) in CH$_2$Cl$_2$ (4 mL) was added SOCl$_2$ (174 μL, 2.40 mmol), the mixture was stirred at 40° C. for 1 hr. The mixture was concentrated to give 3-(3-(4-(chloromethyl)phenyl)-5-isopropoxy-3H-imidazo[4,5-b]pyridin-2-yl)pyridin-2-amine (Intermediate 149, 450 mg, yield: 95%) as a yellow solid. MS: m/z=394.0 [M+H]$^+$.

Intermediate 150: 3-(3-(4-(Chloromethyl)phenyl)-5-(methoxy-d$_3$)-3H-imidazo[4,5-b]pyridin-2-yl)pyridin-2-amine

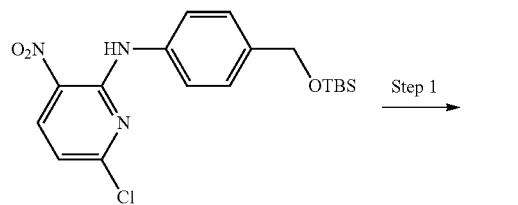

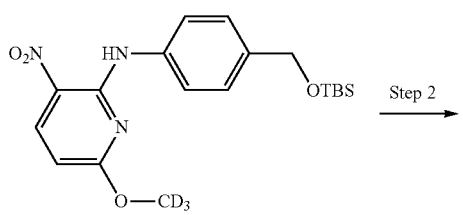

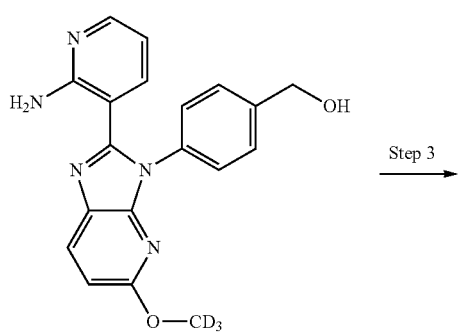

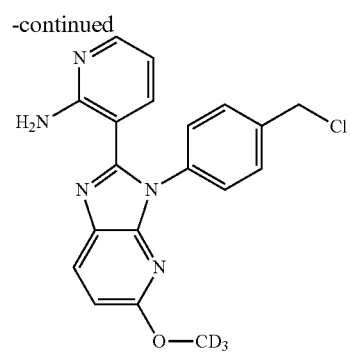

Intermediate 150

Step 1: N-(4-(((tert-butyldimethylsilyl)oxy)methyl)phenyl)-6-(methoxy-d$_3$)-3-nitropyridin-2-amine To a mixture of N-(4-(((tert-butyldimethylsilyl)oxy)methyl)phenyl)-6-chloro-3-nitropyridin-2-amine (refer to Intermediate 105 for detail procedures, 2 g, 5.08 mmol) in CD$_3$OD (30 mL) was added NaH (406 mg, 10.2 mmol, 60% purity) at 0° C. The mixture was stirred at 20° C. for 2 hr. H$_2$O (30 mL) was added slowly, and the mixture was extracted with EtOAc (30 mL×2). The combined organic layers were washed with brine (30 mL), dried over anhydrous Na$_2$SO$_4$, filtered and concentrated. N-(4-(((tert-butyldimethylsilyl)oxy)methyl)phenyl)-6-(methoxy-d$_3$)-3-nitropyridin-2-amine (1.77 g, yield: 89%) was obtained as a brown oil, which was used in the next step directly. MS: m/z=393.1 [M+H]$^+$.

Step 2: (4-(2-(2-Aminopyridin-3-yl)-5-(methoxy-d$_3$)-3H-imidazo[4,5-b]pyridin-3-yl)phenyl)methanol To a solution of N-(4-(((tert-butyldimethylsilyl)oxy)methyl)phenyl)-6-(methoxy-d$_3$)-3-nitropyridin-2-amine (870 mg, 2.22 mmol) in DMSO (15 mL) were added Na$_2$S$_2$O$_4$ (1.16 g, 6.65 mmol) and 2-aminopyridine-3-carbaldehyde (298 mg, 2.44 mmol). The mixture was stirred at 100° C. for 12 hr. Sat. NaHCO$_3$ (50 mL) was added to the mixture and the mixture was extracted with CH$_2$Cl$_2$ (50 mL×2). The combined organic layers were washed with brine (50 mL), dried over anhydrous Na$_2$SO$_4$, filtered and concentrated. After purified by prep-HPLC (column: Xtimate C18 150×40 mm×10 μm; mobile phase: [water (NH$_3$H$_2$O+NH$_4$HCO$_3$)-ACN]; gradient: 26%-56% B over 8 min), (4-(2-(2-aminopyridin-3-yl)-5-(methoxy-d$_3$)-3H-imidazo[4,5-b]pyridin-3-yl)phenyl)methanol (200 mg, yield: 13%) was obtained as a yellow solid. MS: m/z=351.0 [M+H]$^+$. $^1$H NMR (400 MHz, Dimethylsulfoxide-d$_6$) δ 8.11 (d, J=8.8 Hz, 1H), 7.95 (d, J=2.8 Hz, 1H), 7.88 (d, J=4.0 Hz, 1H), 7.47-7.42 (m, 2H), 7.38-7.36 (m, 1H), 7.10 (dd, J=7.6, 2.0 Hz, 1H), 6.90-6.89 (m, 1H), 6.81 (d, J=8.8 Hz, 1H), 6.57 (dd, J=7.2, 4.8 Hz, 1H), 6.38 (dd, J=7.6, 4.8 Hz, 1H), 5.67-5.60 (m, 1H), 5.35 (t, J=5.6 Hz, 1H), 4.58 (d, J=6.0 Hz, 2H).

Step 3: 3-(3-(4-(Chloromethyl)phenyl)-5-(methoxy-d$_3$)-3H-imidazo[4,5-b]pyridin-2-yl)pyridin-2-amine To a solution of (4-(2-(2-aminopyridin-3-yl)-5-(methoxy-d$_3$)-3H-imidazo[4,5-b]pyridin-3-yl)phenyl)methanol (100 mg, 285 μmol) in CH$_2$Cl$_2$ (5 mL) was added SOCl$_2$ (102 mg, 856 mol) at 20° C. The reaction mixture was stirred at 20°

C. for 2 hr. The reaction mixture was concentrated to give 3-(3-(4-(Chloromethyl)phenyl)-5-(methoxy-d₃)-3H-imidazo[4,5-b]pyridin-2-yl)pyridin-2-amine (Intermediate 150, 105 mg, yield: 100%) as a yellow solid, which was used in the next step without further purification. MS: m/z=369.1 [M+H]⁺.

Intermediate 151: 6-(2-(2-Aminopyridin-3-yl)-3-(4-(chloromethyl)phenyl)-3H-imidazo[4,5-b]pyridin-5-yl)picolinonitrile

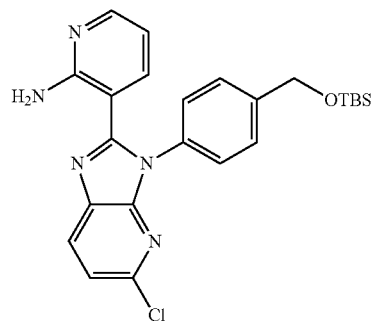

Step 1

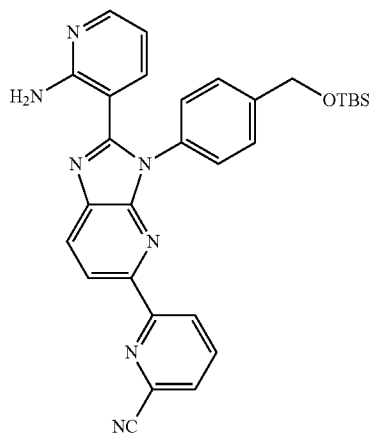

Step 2

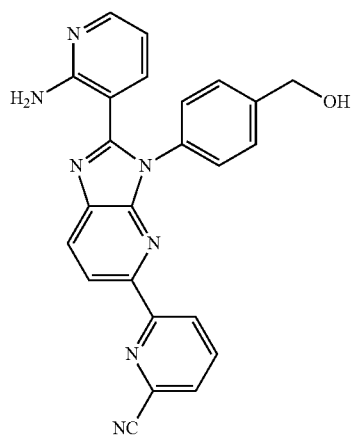

Step 3

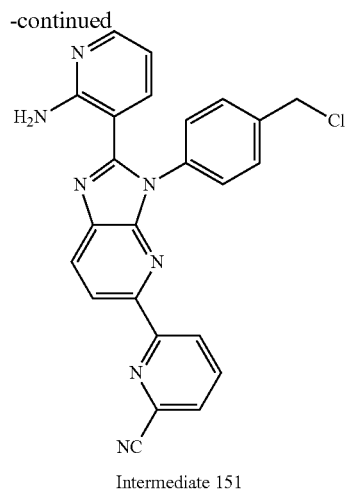

Intermediate 151

Step 1: 6-(2-(2-Aminopyridin-3-yl)-3-(4-(((tert-butyldimethylsilyl)oxy)methyl)phenyl)-3H-imidazo[4,5-b]pyridin-5-yl)picolinonitrile To a mixture of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 600 mg, 1.29 mmol) and 6-(4,4,5,5-Tetramethyl-1,3,2-dioxaborolan-2-yl)picolinonitrile (326 mg, 1.42 mmol) in 1,4-dioxane (10 mL) and H₂O (2 mL) were added Cs₂CO₃ (1.26 g, 3.86 mmol) and Pd(dppf)Cl₂ (94.2 mg, 129 µmol). The mixture was degassed and purged with N₂ three times and stirred at 100° C. for 2 hr. H₂O (100 mL) was added, and the aqueous layer was extracted with EtOAc (200 mL×2). The combined organic layers were washed with brine (200 mL), dried over Na₂SO₄, filtered and concentrated. After purified by silica gel flash chromatography (Eluent of 0~50%, EtOAc in petroleum ether), 6-(2-(2-aminopyridin-3-yl)-3-(4-(((tert-butyldimethylsilyl)oxy)methyl)phenyl)-3H-imidazo[4,5-b]pyridin-5-yl)picolinonitrile (500 mg, yield: 73%) was obtained as a yellow solid. MS: m/z=534.0 [M+H]⁺. ¹H NMR (400 MHz, Dimethylsulfoxide-d₆) δ 8.45-8.41 (m, 2H), 8.38-8.33 (m, 1H), 8.15 (t, J=7.6 Hz, 1H), 8.07-7.99 (m, 2H), 7.54-7.41 (m, 4H), 7.22 (dd, J=7.6, 1.6 Hz, 1H), 7.01 (br s, 2H), 6.40 (dd, J=7.6, 4.8 Hz, 1H), 4.83 (s, 2H), 0.93 (s, 9H), 0.11 (s, 6H).

Step 2: (4-(2-(2-Aminopyridin-3-yl)-5-isopropoxy-3H-imidazo[4,5-b]pyridin-3-yl)phenyl)methanol To a mixture of 6-(2-(2-aminopyridin-3-yl)-3-(4-(((tert-butyldimethylsilyl)oxy)methyl)phenyl)-3H-imidazo[4,5-b]pyridin-5-yl)picolinonitrile (450 mg, 843 µmol) in THF (5 mL) was added TBAF (1 M, 1.26 mL). The mixture was stirred at 20° C. for 1 hr. H₂O (50 mL) was added, and the aqueous layer was extracted with EtOAc (100 mL×2). The combined organic layers were washed with brine (100 mL), dried over Na₂SO₄, filtered and concentrated to give 6-(2-(2-aminopyridin-3-yl)-3-(4-(hydroxymethyl)phenyl)-3H-imidazo[4,5-b]pyridin-5-yl)picolinonitrile (350 mg) as a brown solid. MS: m/z=420.2 [M+H]⁺. ¹H NMR (400 MHz, Dimethylsulfoxide-d₆) δ 8.49-8.40 (m, 2H), 8.38-8.31 (m, 1H), 8.16 (t, J=8.0 Hz, 1H), 8.09-7.98 (m, 2H), 7.53-7.44 (m, 4H), 7.25 (dd, J=7.6, 1.6 Hz, 1H), 6.97 (brs, 2H), 6.43 (dd, J=7.6, 4.8 Hz, 1H), 5.38 (t, J=5.6 Hz, 1H), 4.61 (d, J=5.6 Hz, 2H).

Step 3: 6-(2-(2-Aminopyridin-3-yl)-3-(4-(chloromethyl)phenyl)-3H-imidazo[4,5-b]pyridin-5-yl)picolinonitrile To a mixture of 6-(2-(2-aminopyridin-3-yl)-3-(4-(hydroxymethyl)phenyl)-3H-imidazo[4,5-b]pyridin-5-yl)picolinonitrile (350 mg, 834 μmol) in CH$_2$Cl$_2$ (5 mL) was added SOCl$_2$ (121 L, 1.67 mmol), the mixture was stirred at 40° C. for 1 hr. The mixture was concentrated to give 6-(2-(2-aminopyridin-3-yl)-3-(4-(chloromethyl)phenyl)-3H-imidazo[4,5-b]pyridin-5-yl)picolinonitrile (Intermediate 151, 320 mg) as a yellow solid. MS: m/z=438.0 [M+H]$^+$. $^1$H NMR (400 MHz, Dimethylsulfoxide-d$_6$) δ 8.78-8.25 (m, 5H), 8.25-8.13 (m, 2H), 8.12-8.06 (m, 1H), 7.95 (dd, J=7.6, 1.6 Hz, 1H), 7.68-7.60 (m, 4H), 6.93 (dd, J=7.6, 5.2 Hz, 1H), 4.88 (s, 2H).

Intermediate 152: 4-(2-(2-Aminopyridin-3-yl)-3-(4-(chloromethyl)phenyl)-3H-imidazo[4,5-b]pyridin-5-yl)picolinonitrile

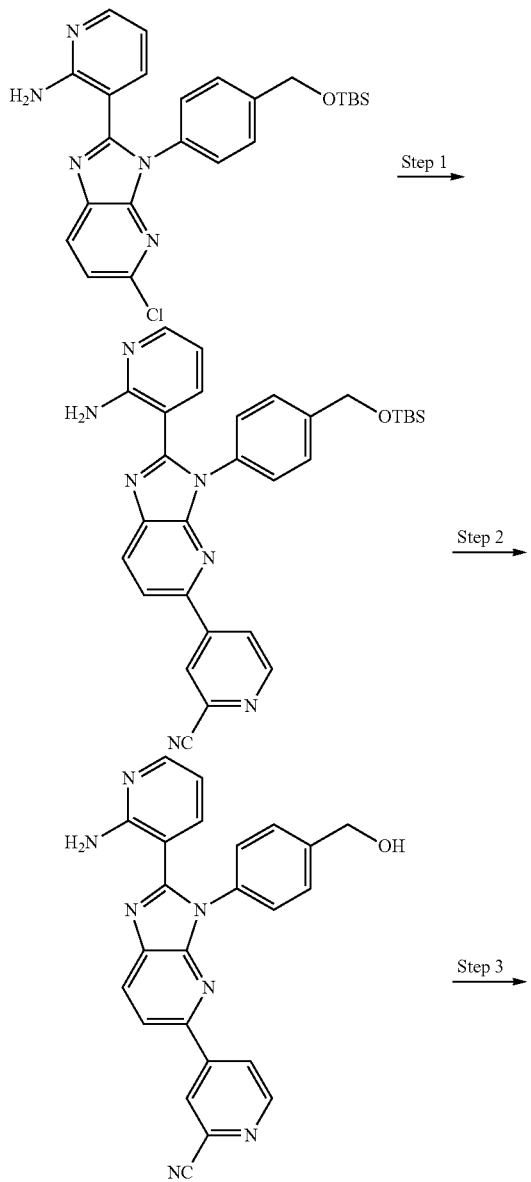

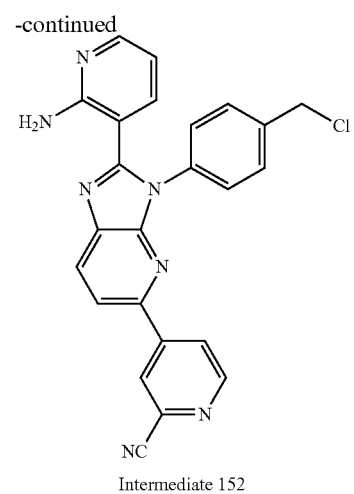

Intermediate 152

Step 1: 4-(2-(2-Aminopyridin-3-yl)-3-(4-(((tert-butyldimethylsilyl)oxy)methyl)phenyl)-3H-imidazo[4,5-b]pyridin-5-yl)picolinonitrile To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 500 mg, 1.07 mmol) and 4-(4,4,5,5-tetramethyl-1,3,2-dioxaborolan-2-yl)pyridine-2-carbonitrile (272 mg, 1.18 mmol) in 1,4-dioxane (30 mL) and H$_2$O (6 mL) were added Pd(dppf)Cl$_2$ (78.5 mg, 107 μmol) and Cs$_2$CO$_3$ (1.05 g, 3.22 mmol) at 25° C. The mixture was degassed and purged with N$_2$ three times and stirred at 100° C. for 2 hr. The mixture was quenched with H$_2$O (50 mL) and the aqueous layer was extracted with EtOAc (50 mL×3). The combined organic layers were washed with brine (50 mL×3), dried over Na$_2$SO$_4$, filtered and concentrated. After purified by silica gel flash chromatography (Eluent of 0~100% EtOAc in petroleum ether), 4-(2-(2-aminopyridin-3-yl)-3-(4-(((tert-butyldimethylsilyl)oxy)methyl)phenyl)-3H-imidazo[4,5-b]pyridin-5-yl)picolinonitrile (550 mg, yield: 96%) was obtained as a brown solid. MS: m/z=534.1 [M+1]$^+$. $^1$H NMR (400 MHz, Dimethylsulfoxide-d$_6$) δ 8.81 (d, J=5.2 Hz, 1H), 8.63-8.56 (m, 1H), 8.39 (d, J=8.4 Hz, 1H), 8.32 (dd, J=5.2, 1.6 Hz, 1H), 8.28 (d, J=8.4 Hz, 1H), 8.01 (dd, J=4.8, 2.0 Hz, 1H), 7.50 (br s, 4H), 7.22 (dd, J=7.6, 2.0 Hz, 1H), 7.12-6.97 (m, 2H), 6.40 (dd, J=7.6, 4.8 Hz, 1H), 4.83 (s, 2H), 0.92 (s, 9H), 0.10 (s, 6H).

Step 2: 4-(2-(2-Aminopyridin-3-yl)-3-(4-(hydroxymethyl)phenyl)-3H-imidazo[4,5-b]pyridin-5-yl)picolinonitrile To a solution of 4-(2-(2-aminopyridin-3-yl)-3-(4-(((tert-butyldimethylsilyl)oxy)methyl)phenyl)-3H-imidazo[4,5-b]pyridin-5-yl)picolinonitrile (500 mg, 937 μmol) in THF (15 mL) was added TBAF (1 M in THF, 1.41 mL) at 25° C. This mixture was stirred at 25° C. for 2 hr. The mixture was quenched with H$_2$O (30 ml) and the aqueous layer was extracted with EtOAc (30 mL×3). The combined organic layers were washed with brine (30 mL×2), dried over Na$_2$SO$_4$, filtered and concentrated to give 4-(2-(2-aminopyridin-3-yl)-3-(4-(hydroxymethyl)phenyl)-3H-imidazo[4,5-b]pyridin-5-yl)picolinonitrile (390 mg, crude) as a brown solid, which was used directly without purification. MS: m/z=420.2 [M+1]$^+$.

Step 3: 4-(2-(2-Aminopyridin-3-yl)-3-(4-(chloromethyl)phenyl)-3H-imidazo[4,5-b]pyridin-5-yl)picolinonitrile To a solution of 4-(2-(2-aminopyridin-3-yl)-3-(4-(hydroxymethyl)phenyl)-3H-imidazo[4,5-b]pyridin-5-yl)picolinonitrile (390 mg, 930 μmol) in CH$_2$Cl$_2$ (5 mL) was added SOCl$_2$ (332 mg, 2.79 mmol) at 25° C. This mixture was stirred at 25° C. for 1 hr. The reaction mixture was concentrated to give 4-(2-(2-aminopyridin-3-yl)-3-(4-(chloromethyl)phenyl)-3H-imidazo[4,5-b]pyridin-5-yl)picolinonitrile (Intermediate 152, 400 mg, crude) as a brown solid, which was used in the next step without purification. MS: m/z=438.2 [M+1]$^+$.

Intermediate 153: 5-(2-(2-Aminopyridin-3-yl)-3-(4-(chloromethyl)phenyl)-3H-imidazo[4,5-b]pyridin-5-yl)nicotinonitrile

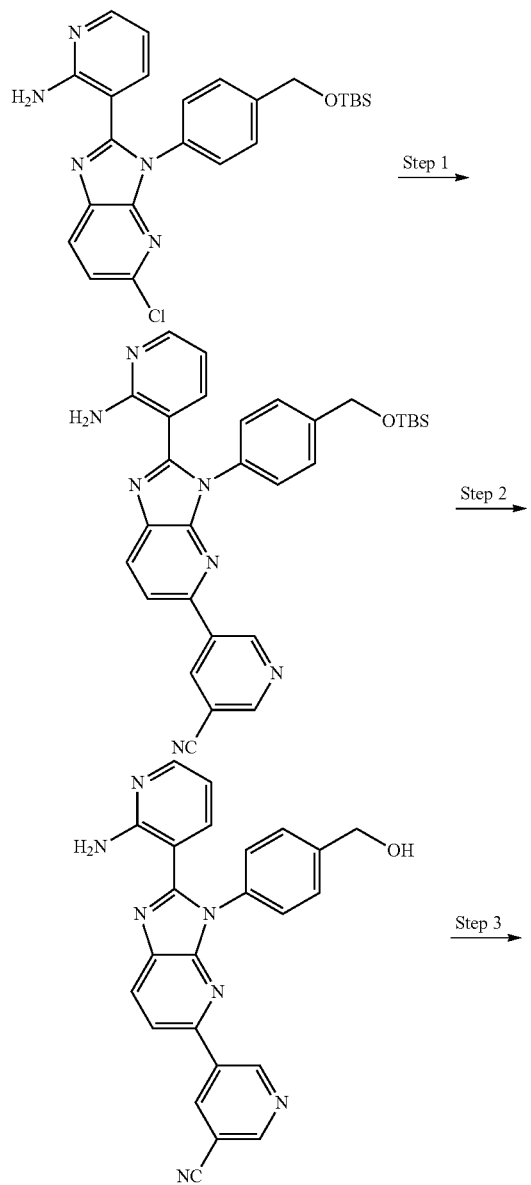

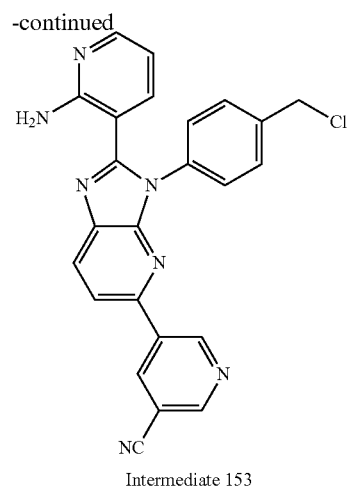

Intermediate 153

Step 1: 5-(2-(2-Aminopyridin-3-yl)-3-(4-(((tert-butyldimethylsilyl)oxy)methyl)phenyl)-3H-imidazo[4,5-b]pyridin-5-yl)nicotinonitrile To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 540 mg, 1.16 mmol) in 1,4-dioxane (30 mL) and H$_2$O (6 mL) were added (5-cyano-3-pyridyl)boronic acid (189 mg, 1.27 mmol), Cs$_2$CO$_3$ (1.13 g, 3.48 mmol) and Pd(dppf)Cl$_2$ (84.8 mg, 116 μmol) at 20° C. The reaction mixture was stirred at 100° C. for 2 hr. The reaction was quenched with H$_2$O (50 mL), and extracted with EtOAc (50 mL×2). The combined organic layers were washed with brine (50 mL), dried over anhydrous Na$_2$SO$_4$, filtered and concentrated. 5-(2-(2-aminopyridin-3-yl)-3-(4-(((tert-butyldimethylsilyl)oxy)methyl)phenyl)-3H-imidazo[4,5-b]pyridin-5-yl)nicotinonitrile (610 mg, crude) was obtained as a purple black oil, which was used in the next step without further purification. MS: m/z=534.1 [M+H]$^+$.

Step 2: 5-(2-(2-Aminopyridin-3-yl)-3-(4-(hydroxymethyl)phenyl)-3H-imidazo[4,5-b]pyridin-5-yl)nicotinonitrile To a solution of 5-(2-(2-aminopyridin-3-yl)-3-(4-(((tert-butyldimethylsilyl)oxy)methyl)phenyl)-3H-imidazo[4,5-b]pyridin-5-yl)nicotinonitrile (310 mg, 581 mol) in THF (12 mL) was added TBAF (1 Min THF) (1 M, 1.00 mL). The reaction mixture was stirred at 20° C. for 2 hr. H$_2$O (20 mL) was added and the mixture was extracted with EtOAc (25 mL×2). The combined organic layers were washed with brine (30 mL), dried over anhydrous Na$_2$SO$_4$, filtered and concentrated. 5-(2-(2-Aminopyridin-3-yl)-3-(4-(hydroxymethyl)phenyl)-3H-imidazo[4,5-b]pyridin-5-yl)nicotinonitrile (240 mg, crude) was obtained as a black solid, which was used in the next step without further purification. MS: m/z=420.2 [M+H]$^+$.

Step 3: 5-(2-(2-Aminopyridin-3-yl)-3-(4-(chloromethyl)phenyl)-3H-imidazo[4,5-b]pyridin-5-yl)nicotinonitrile To a solution of 5-(2-(2-aminopyridin-3-yl)-3-(4-(hydroxymethyl)phenyl)-3H-imidazo[4,5-b]pyridin-5-yl)nicotinonitrile (240 mg, 572 μmol) in CH$_2$Cl$_2$ (8 mL) was added SOCl$_2$ (204 mg, 1.72 mmol) at 20° C. The reaction mixture was stirred at 40° C. for 1 hr. The reaction mixture was concentrated to give 5-(2-(2-aminopyridin-3-yl)-3-(4-(chloromethyl)phenyl)-3H-imidazo[4,5-b]pyridin-5-yl)nicotinonitrile (Intermediate 153, 250 mg, crude) as a brown solid, which was used in the next step directly. MS: m/z=438.1 [M+H]$^+$.

Intermediate 154: 3-(3-(4-(Chloromethyl)phenyl)-5-(pyridin-3-yl)-3H-imidazo[4,5-b]pyridin-2-yl)pyridin-2-amine

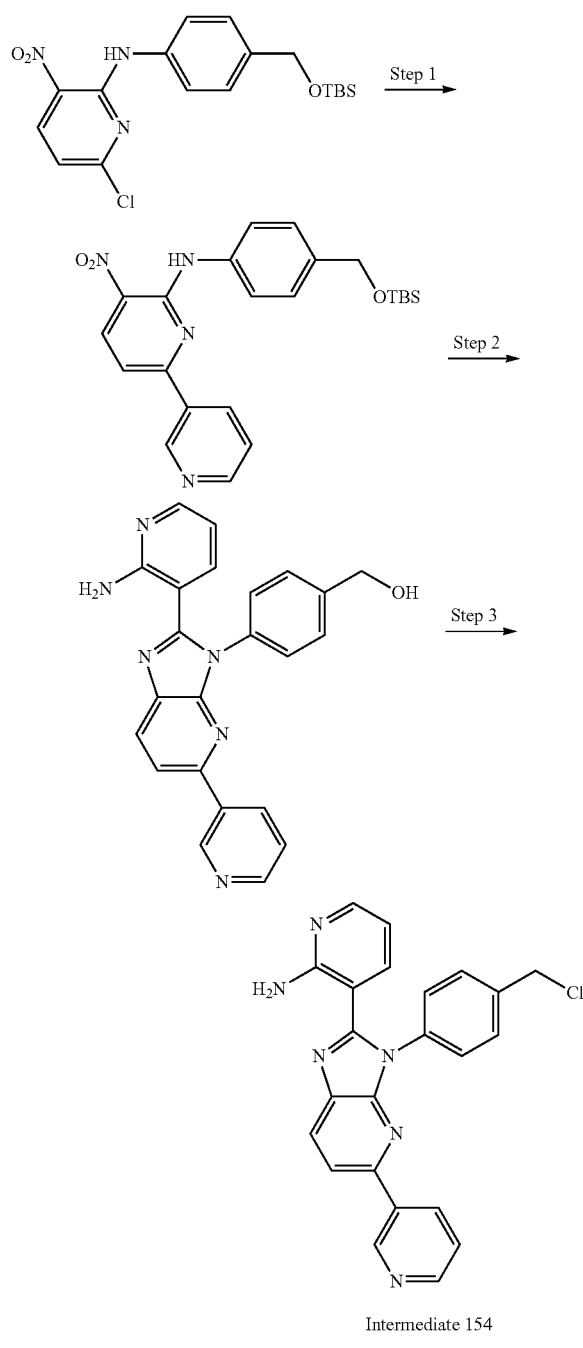

Intermediate 154

Step 1: N-(4-(((tert-butyldimethylsilyl)oxy)methyl)phenyl)-5-nitro-[2,3'-bipyridin]-6-amine To a solution of N-(4-(((tert-butyldimethylsilyl)oxy)methyl)phenyl)-6-chloro-3-nitropyridin-2-amine (refer to Intermediate 105 for detail procedures, 2 g, 5.08 mmol) and 3-pyridylboronic acid (749 mg, 6.09 mmol) in 1,4-dioxane (20 mL) and H$_2$O (4 mL) were added Pd(dppf)Cl$_2$ (371 mg, 508 μmol) and Cs$_2$CO$_3$ (4.96 g, 15.2 mmol). The mixture was degassed and purged with N$_2$ three times, and then was stirred at 100° C. for 12 hr under N$_2$. H$_2$O (50 mL) was added, and the mixture was extracted with EtOAc (30 mL×2). The combined organic layers were dried over anhydrous Na$_2$SO$_4$, filtered and concentrated. N-(4-(((tert-butyldimethylsilyl)oxy)methyl)phenyl)-5-nitro-[2,3'-bipyridin]-6-amine (2.22 g) was obtained as a black brown oil, which was used in the next step directly. MS: m z=437.2 [M+H]$^+$.

Step 2: (4-(2-(2-Aminopyridin-3-yl)-5-(pyridin-3-yl)-3H-imidazo[4,5-b]pyridin-3-yl)phenyl)methanol To a solution of N-(4-(((tert-butyldimethylsilyl)oxy)methyl)phenyl)-5-nitro-[2,3'-bipyridin]-6-amine (2 g, 4.58 mmol) and 2-aminopyridine-3-carbaldehyde (615 mg, 5.04 mmol) in DMSO (20 mL) was added Na$_2$S$_2$O$_4$ (1.99 g, 11.5 mmol). The mixture was stirred at 100° C. for 12 hr under N$_2$. Sat. NaHCO$_3$ (50 mL) was added and the mixture was extracted with CH$_2$Cl$_2$/MeOH (10/1, 50 mL×3). The combined organic layers were washed with brine (50 mL×3), dried over Na$_2$SO$_4$, filtered and concentrated. After purified by silica gel flash chromatography (Eluent of 0~100% EtOAc/EtOH (3/1) in petroleum ether), (4-(2-(2-aminopyridin-3-yl)-5-(pyridin-3-yl)-3H-imidazo[4,5-b]pyridin-3-yl)phenyl)methanol (500 mg, yield: 28% for 2 steps) was obtained as brown oil. MS: m/z=395.2 [M+H]$^+$.

Step 3: 3-(3-(4-(Chloromethyl)phenyl)-5-(pyridin-3-yl)-3H-imidazo[4,5-b]pyridin-2-yl)pyridin-2-amine To a solution of (4-(2-(2-aminopyridin-3-yl)-5-(pyridin-3-yl)-3H-imidazo[4,5-b]pyridin-3-yl)phenyl)methanol (500 mg, 1.27 mmol) in CH$_2$Cl$_2$ (5 mL) was added SOCl$_2$ (452 mg, 3.80 mmol). The mixture was stirred at 40° C. for 1 hr under N$_2$. The solution was concentrated. 3-(3-(4-(Chloromethyl)phenyl)-5-(pyridin-3-yl)-3H-imidazo[4,5-b]pyridin-2-yl)pyridin-2-amine (Intermediate 154, 400 mg, yield: 76%) was obtained as yellow solid, which was used in the next step directly. MS: m/z=413.2 [M+H]$^+$.

Intermediate 155: 3-(3-(4-(Chloromethyl)phenyl)-5-(pyridin-4-yl)-3H-imidazo[4,5-b]pyridin-2-yl)pyridin-2-amine

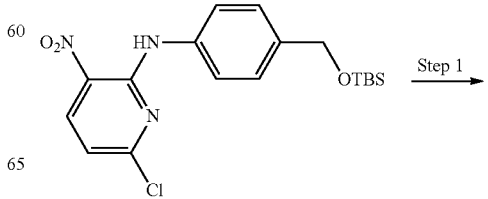

Step 1

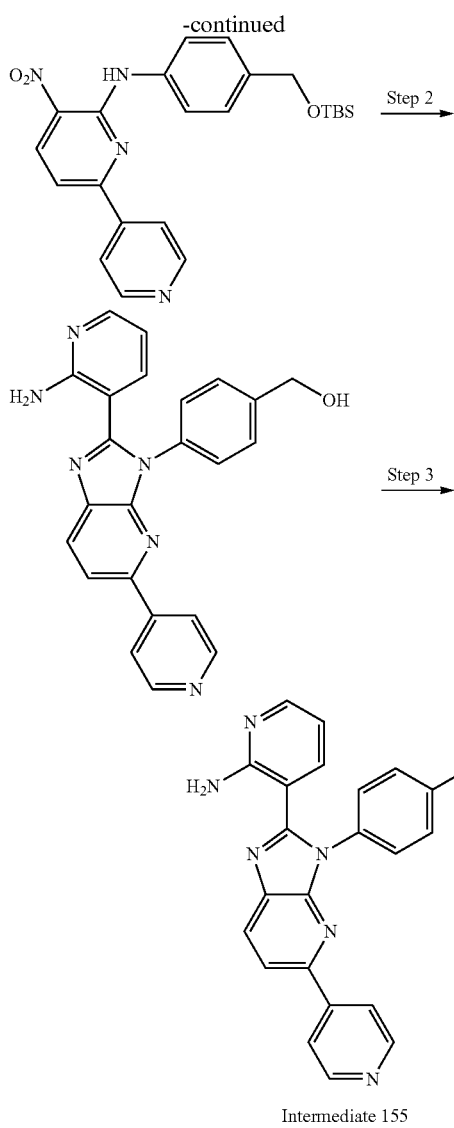

Intermediate 155

Step 1: N-(4-(((tert-Butyldimethylsilyl)oxy)methyl)phenyl)-5-nitro-[2,4'-bipyridin]-6-amine To a solution of N-(4-(((tert-butyldimethylsilyl)oxy)methyl)phenyl)-6-chloro-3-nitropyridin-2-amine (refer to Intermediate 105 for detail procedures, 2 g, 5.08 mmol) in 1,4-dioxane (20 mL) and H₂O (4 mL) were added 4-pyridylboronic acid (686 mg, 5.58 mmol), Pd(dppf)Cl₂ (371 mg, 507 μmol), and Cs₂CO₃ (4.96 g, 15.2 mmol). The mixture was degassed and purged with N₂ three times and was stirred at 100° C. for 2 hr under N₂ atmosphere. The crude was extracted with CH₂Cl₂ (30 mL×3). The combined organic layers were washed with brine (40 mL), dried over Na₂SO₄, filtered and concentrated. N-(4-(((tert-butyldimethylsilyl)oxy)methyl)phenyl)-5-nitro-[2,4'-bipyridin]-6-amine (2.22 g, crude) was obtained as a brown solid, which was used in the next step without further purification. MS: m/z=437.3 [M+H]⁺.

Step 2: (4-(2-(2-Aminopyridin-3-yl)-5-(pyridin-4-yl)-3H-imidazo[4,5-b]pyridin-3-yl)phenyl)methanol To a solution of N-(4-(((tert-butyldimethylsilyl)oxy)methyl)phenyl)-5-nitro-[2,4'-bipyridin]-6-amine (2.12 g, 4.86 mmol), 2-aminopyridine-3-carbaldehyde (711 mg, 5.83 mmol) in DMSO (20 mL) was added Na₂S₂O₄ (2.11 g, 12.1 mmol). The mixture was stirred at 100° C. for 12 hr. Sat. Na₂CO₃ (15 mL) was added to adjust pH about 8 and the mixture was extracted with CH₂Cl₂ (15 mL×3). The combined organic layers were washed with brine (30 mL), dried over Na₂SO₄, filtered and concentrated. After purified by silica gel flash chromatography (Eluent of 0~78% EtOAc/EtOH (3:1) in petroleum ether), (4-(2-(2-aminopyridin-3-yl)-5-(pyridin-4-yl)-3H-imidazo[4,5-b]pyridin-3-yl)phenyl)methanol (100 mg, yield: 5% for 2 steps) was obtained as a yellow solid. MS: m/z=395.3 [M+H]⁺.

Step 3: 3-(3-(4-(Chloromethyl)phenyl)-5-(pyridin-4-yl)-3H-imidazo[4,5-b]pyridin-2-yl)pyridin-2-amine To a solution of (4-(2-(2-aminopyridin-3-yl)-5-(pyridin-4-yl)-3H-imidazo[4,5-b]pyridin-3-yl)phenyl)methanol (100 mg, 253 μmol) in CH₂Cl₂ (2 mL) was added SOCl₂ (60.3 mg, 507 μmol). The mixture was stirred at 25° C. for 2 hr. The residue was concentrated. 3-(3-(4-(Chloromethyl)phenyl)-5-(pyridin-4-yl)-3H-imidazo[4,5-b]pyridin-2-yl)pyridin-2-amine (Intermediate 155, 104 mg, crude) was obtained a brown solid, which was used in the next step without further purification. MS: m/z=413.2 [M+H]⁺.

Intermediate 156: 7-(4-(2-(2-Aminopyridin-3-yl)-5-phenyl-3H-imidazo[4,5-b]pyridin-3-yl)benzyl)-7-azaspiro[3.5]nonan-2-amine

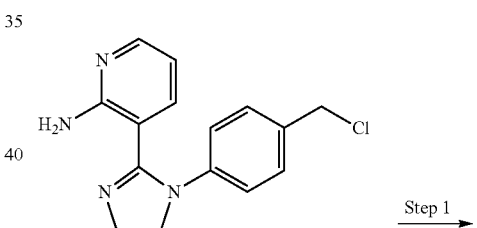

Intermediate 14

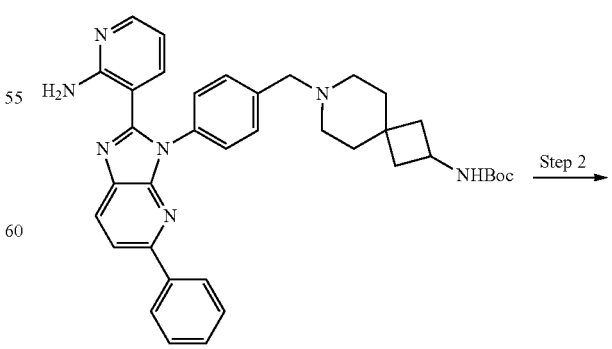

725
-continued

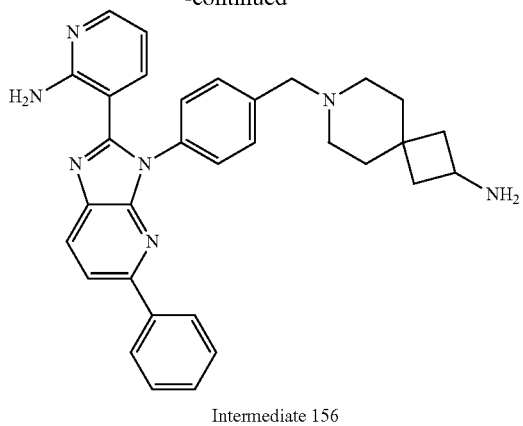

Intermediate 156

Step 1: Tert-butyl (7-(4-(2-(2-aminopyridin-3-yl)-5-phenyl-3H-imidazo[4,5-b]pyridin-3-yl)benzyl)-7-azaspiro[3.5]nonan-2-yl)carbamate To a solution of Intermediate 14 (1 g, 2.43 mmol) and tert-butyl 7-azaspiro[3.5]nonan-2-ylcarbamate (700 mg, 2.92 mmol) in ACN (20 mL) were added NaI (36.4 mg, 243 µmol) and $K_2CO_3$ (671 mg, 4.86 mmol). The mixture was stirred at 80° C. for 2 hr. The reaction mixture was concentrated. The residue was purified by silica gel flash chromatography (Eluent of 0~10% MeOH in $CH_2Cl_2$) to give tert-butyl (7-(4-(2-(2-aminopyridin-3-yl)-5-phenyl-3H-imidazo[4,5-b]pyridin-3-yl)benzyl)-7-azaspiro[3.5]nonan-2-yl)carbamate (480 mg yield: 32%,) as a light-yellow solid, which was used directly to the next step without further purification. MS: m/z=616.1 [M+H]+.

Step 2: 7-(4-(2-(2-Aminopyridin-3-yl)-5-phenyl-3H-imidazo[4,5-b]pyridin-3-yl)benzyl)-7-azaspiro[3.5]nonan-2-amine To a solution of tert-butyl N-[7-[[4-[2-(2-amino-3-pyridyl)-5-phenyl-imidazo[4,5-b]pyridin-3-yl]phenyl]methyl]-7-azaspiro[3.5]nonan-2-yl]carbamate (450 mg, 731 µmol) in HCl/1,4-dioxane (4M, 6 mL). The mixture was stirred at 25° C. for 1 hr. The reaction mixture was concentrated. phase: [water (NH4HCO3)-ACN]; B %: 28%-58%, 8 min) to give 7-[[4-[2-(2-amino-3-pyridyl)-5-phenyl-imidazo[4,5-b]pyridin-3-yl]phenyl]methyl]-7-azaspiro[3.5]nonan-2-amine (Intermediate 156, 370 mg, yield: 91%) as a light-yellow oil. MS: m/z=516.3 [M+H]+. 1H NMR (400 MHz, Dimethylsulfoxide-d6) δ 8.27 (d, J=8.0 Hz, 1H), 8.06-7.95 (m, 4H), 7.55-7.35 (m, 7H), 7.18-7.12 (m, 1H), 7.01 (br s, 2H), 6.36 (dd, J=7.6, 4.8 Hz, 1H), 3.71-3.58 (m, 1H), 3.52 (s, 2H), 3.01-2.98 (m, 4H), 2.41-2.20 (m, 2H), 2.14-2.05 (m, 2H), 1.90-1.80 (m, 2H), 1.67-1.53 (m, 2H).

Intermediate 157: 3-(3-(4-((2,7-Diazaspiro[4.4]nonan-2-yl)methyl)phenyl)-5-phenyl-3H-imidazo[4,5-b]pyridin-2-yl)pyridin-2-amine

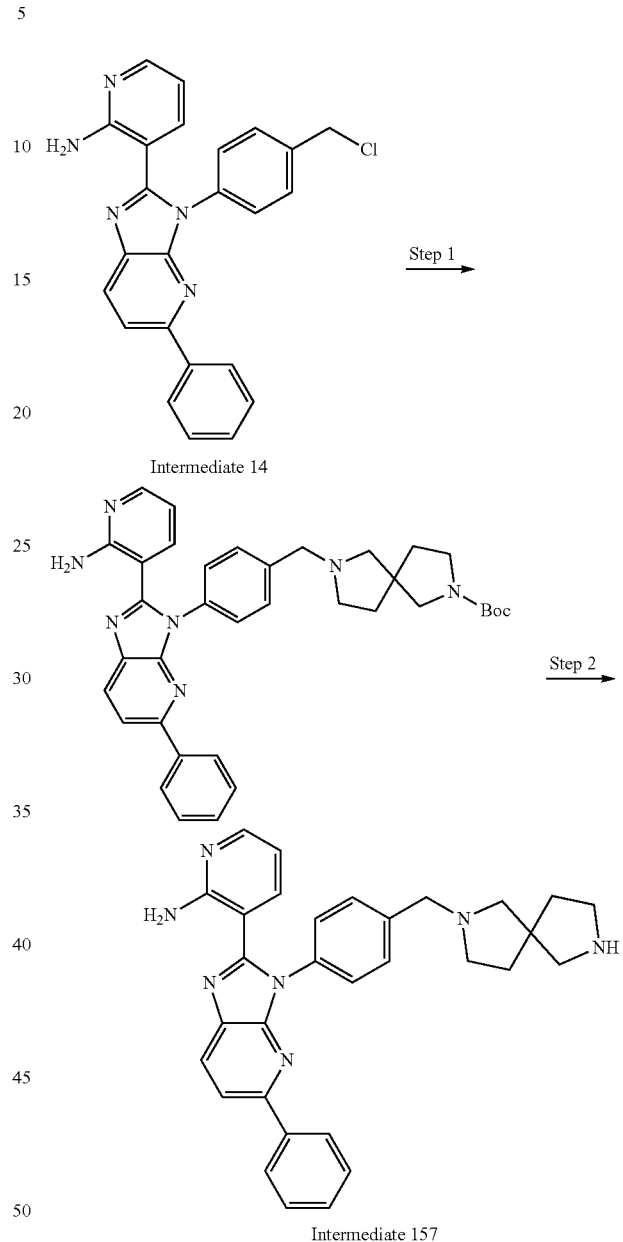

Step 1: Tert-butyl 7-(4-(2-(2-aminopyridin-3-yl)-5-phenyl-3H-imidazo[4,5-b]pyridin-3-yl)benzyl)-2,7-diazaspiro[4.4]nonane-2-carboxylate To a solution of Intermediate 14 (1.5 g, 3.6 mmol) and tert-butyl 2,7-diazaspiro[4.4]nonane-2-carboxylate (988 mg, 4.4 mmol) in DMF (10 mL) was added NaI (273 mg, 1.82 mmol) and $K_2CO_3$ (1.0 g, 7.3 mmol). The mixture was stirred at 80° C. for 1 hr. Then the reaction mixture was poured into $H_2O$ (100 mL) and extracted with EtOAc (50 mL×2). The combined organic layers were washed with brine (50 mL×2), dried over anhydrous $Na_2SO_4$, filtered, and concentrated to dryness. The residue was purified by silica gel flash chromatography (Eluent of 0~98% EtOAc in petroleum ether) to give tert-butyl 7-(4-(2-(2-aminopyridin-3-yl)-5-phenyl-3H-imidazo[4,5-b]pyridin-3-yl)benzyl)-2,7-diazaspiro[4.4]nonane-2-carboxylate (640 mg, yield: 30%) as a yellow solid. MS: m/z=602.4 [M+H]⁺

Step 2: 3-(3-(4-((2,7-Diazaspiro[4.4]nonan-2-yl)methyl)phenyl)-5-phenyl-3H-imidazo[4,5-b]pyridin-2-yl)pyridin-2-amine A solution of tert-butyl 7-(4-(2-(2-aminopyridin-3-yl)-5-phenyl-3H-imidazo[4,5-b]pyridin-3-yl)benzyl)-2,7-diazaspiro[4.4]nonane-2-carboxylate (590 mg, 980 μmol) in HCl in 1,4-dioxane (4 M, 5 mL) was stirred at 25° C. for 0.5 hr. The mixture was concentrated under reduced pressure to give 3-(3-(4-((2,7-diazaspiro[4.4]nonan-2-yl)methyl)phenyl)-5-phenyl-3H-imidazo[4,5-b]pyridin-2-yl)pyridin-2-amine (Intermediate 157, 452 mg, HCl salt, yield: 86%) as a yellow solid. MS: m/z=502.3 [M+H]⁺. ¹H NMR (400 MHz, Dimethylsulfoxide-d₆)-11.93 (br s, 1H), 9.88-9.48 (m, 2H), 8.60-8.35 (m, 2H), 8.38 (d, J=8.4 Hz, 1H), 8.16 (dd, J=6.4, 1.6 Hz, 1H), 8.08-8.05 (m, 3H), 7.98-7.83 (m, 3H), 7.66 (d, J=8.4 Hz, 2H), 7.52-7.40 (m, 3H), 7.02-6.92 (m, 1H), 4.54-4.43 (m, 2H), 3.64-3.47 (m, 2H), 3.43-3.27 (m, 3H), 3.25-3.18 (m, 3H), 2.31-2.14 (m, 2H), 2.11-1.96 (m, 2H).

Intermediate 158: 3-(3-(4-((2,7-Diazaspiro[3.5]nonan-7-yl)methyl)phenyl)-5-phenyl-3H-imidazo[4,5-b]pyridin-2-yl)pyridin-2-amine

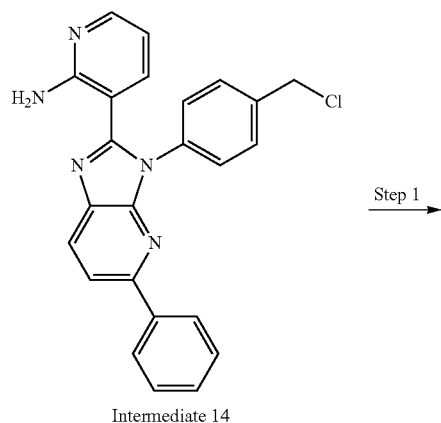

Intermediate 14

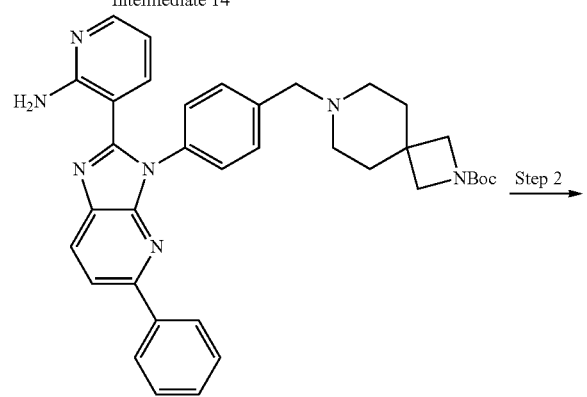

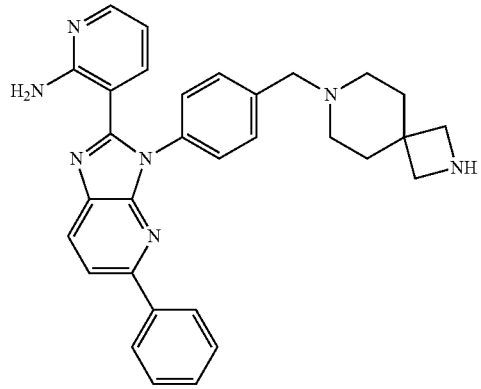

Intermediate 158

Step 1: Tert-butyl 7-(4-(2-(2-aminopyridin-3-yl)-5-phenyl-3H-imidazo[4,5-b]pyridin-3-yl)benzyl)-2,7-diazaspiro[3.5]nonane-2-carboxylate To a solution of Intermediate 14 (1.0 g, 2.43 mmol) and tert-butyl 2,7-diazaspiro[3.5]nonane-2-carboxylate (660 mg, 2.92 mmol) in ACN (20 mL) were added NaI (36.4 mg, 243 μmol) and K₂CO₃ (671 mg, 4.86 mmol). The mixture was stirred at 80° C. for 2 hr. The reaction mixture was concentrated. The residue was purified by silica gel flash chromatography (Eluent of 0~10% MeOH in CH₂Cl₂) to give tert-butyl 7-(4-(2-(2-aminopyridin-3-yl)-5-phenyl-3H-imidazo[4,5-b]pyridin-3-yl)benzyl)-2,7-diazaspiro[3.5]nonane-2-carboxylate (570 mg, yield: 39%) as a light-yellow solid, which was used in the next step without further purification. MS: m/z=602.3 [M+H]⁺.

Step 2: 3-(3-(4-((2,7-Diazaspiro[3.5]nonan-7-yl)methyl)phenyl)-5-phenyl-3H-imidazo[4,5-b]pyridin-2-yl)pyridin-2-amine A solution of tert-butyl 7-(4-(2-(2-aminopyridin-3-yl)-5-phenyl-3H-imidazo[4,5-b]pyridin-3-yl)benzyl)-2,7-diazaspiro[3.5]nonane-2-carboxylate (490 mg, 814 μmol) in HCl in 1,4-dioxane (4M, 9 mL) was stirred at 25° C. for 1 hr. The residue was concentrated and purified by prep-HPLC (column: Waters xbridge 150×25 mm 10 μm; mobile phase: [water (NH₄HCO₃)-ACN]; B %: 32%-62%, 8 min) to give 3-(3-(4-((2,7-diazaspiro[3.5]nonan-7-yl)methyl)phenyl)-5-phenyl-3H-imidazo[4,5-b]pyridin-2-yl)pyridin-2-amine (Intermediate 158, 300 mg, yield: 74%) as a light-yellow oil. MS: m/z=502.3 [M+H]⁺. ¹H NMR (400 MHz, Dimethylsulfoxide-d₆) δ 8.26 (d, J=8.4 Hz, 1H), 8.05-7.97 (m, 4H), 7.49-7.39 (m, 7H), 7.18-7.12 (dd, J=7.6, 1.6 Hz, 1H), 7.02 (br s, 2H), 6.36 (dd, J=7.6, 5.2 Hz, 1H), 3.58-3.41 (m, 6H), 2.38-2.26 (m, 4H), 1.71-1.68 (m, 4H).

Intermediate 159: 3-(3-(4-((2,7-Diazaspiro[4.5]decan-2-yl)methyl)phenyl)-5-phenyl-3H-imidazo[4,5-b]pyridin-2-yl)pyridin-2-amine

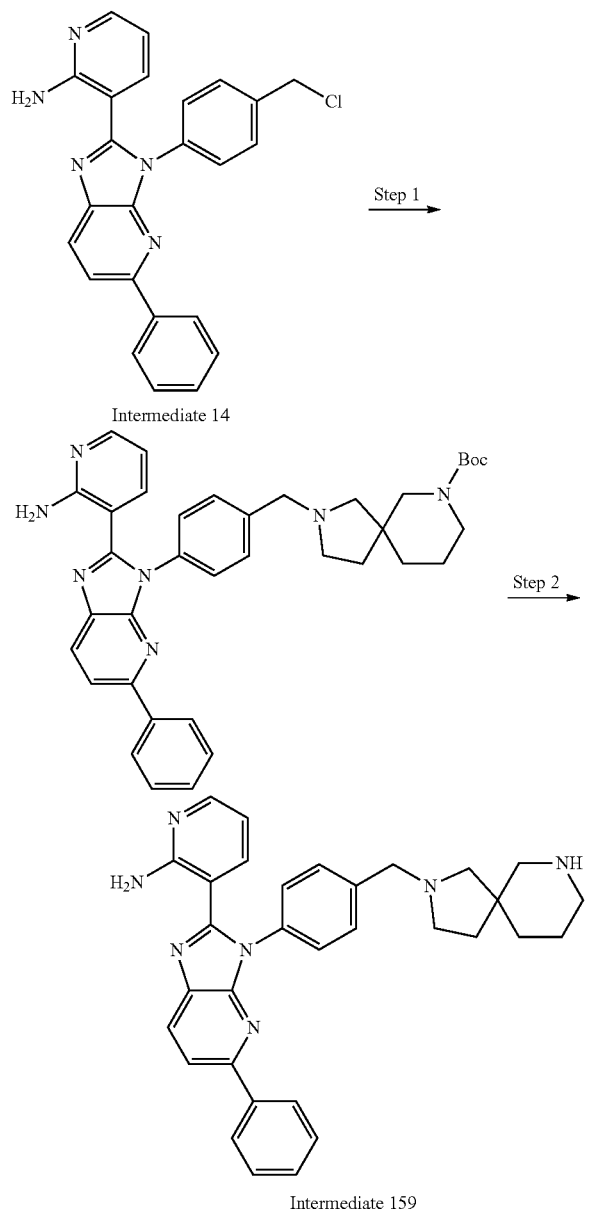

Step 1: Tert-butyl 2-(4-(2-(2-aminopyridin-3-yl)-5-phenyl-3H-imidazo[4,5-b]pyridin-3-yl)benzyl)-2,7-diazaspiro[4.5]decane-7-carboxylate To a solution of Intermediate 14 (1.5 g, 3.6 mmol) and tert-butyl 2,8-diazaspiro[4.5]decane-8-carboxylate (1.0 g, 4.4 mmol) in DMF (10 mL) were added NaI (273 mg, 1.8 mmol) and $K_2CO_3$ (1.5 g, 11 mmol). The mixture was stirred at 80° C. for 1 hr. After cooling to 20° C., the reaction mixture was poured into $H_2O$ (100 mL) and extracted with EtOAc (50 mL×3). The combined organic layers were dried over anhydrous $Na_2SO_4$, filtered, and concentrated under reduced pressure. The residue was purified by silica gel flash chromatography (Eluent of 0~85% EtOAc in petroleum ether) to give tert-butyl 2-(4-(2-(2-aminopyridin-3-yl)-5-phenyl-3H-imidazo[4,5-b]pyridin-3-yl)benzyl)-2,7-diazaspiro[4.5]decane-7-carboxylate (1.2 g, yield: 53%) as a yellow solid. MS: m/z=616.1 [M+H]$^+$.

Step 2: 3-(3-(4-((2,7-Diazaspiro[4.5]decan-2-yl)methyl)phenyl)-5-phenyl-3H-imidazo[4,5-b]pyridin-2-yl)pyridin-2-amine A solution of tert-butyl 2-(4-(2-(2-aminopyridin-3-yl)-5-phenyl-3H-imidazo[4,5-b]pyridin-3-yl)benzyl)-2,7-diazaspiro[4.5]decane-7-carboxylate (240 mg, 390 μmol) in HCl/1,4-dioxane (4 M, 2 mL) was stirred at 25° C. for 0.5 hr. The mixture was concentrated and washed with $CH_2Cl_2$ (3 mL), then concentrated under reduced pressure. 3-(3-(4-((2,7-diazaspiro[4.5]decan-2-yl)methyl)phenyl)-5-phenyl-3H-imidazo[4,5-b]pyridin-2-yl)pyridin-2-amine (Intermediate 159, 188 mg, HCl salt, yield: 88%) was obtained as a yellow solid. MS: m/z=516.4 [M+H]$^+$. $^1$H NMR (400 MHz, Methanol-d$_6$) δ 8.32 (d, J=8.4 Hz, 1H), 8.09-8.00 (m, 4H), 7.93 (d, J=8.4 Hz, 2H), 7.89 (d, J=7.2 Hz, 1H), 7.72 (d, J=8.0 Hz, 2H), 7.49-7.37 (m, 3H), 6.99-6.85 (m, 1H), 4.62 (d, J=11.6 Hz, 2H), 3.78-3.72 (m, 1H), 3.65-3.47 (m, 2H), 3.44-3.38 (m, 1H), 3.35 (s, 2H), 3.18-3.13 (m, 2H), 2.26-2.13 (m, 1H), 2.11-2.01 (m, 1H), 1.95-1.86 (m, 4H).

Intermediate 160: 3-(3-(4-((2,8-diazaspiro[4.5]decan-2-yl)methyl)phenyl)-5-phenyl-3H-imidazo[4,5-b]pyridin-2-yl)pyridin-2-amine

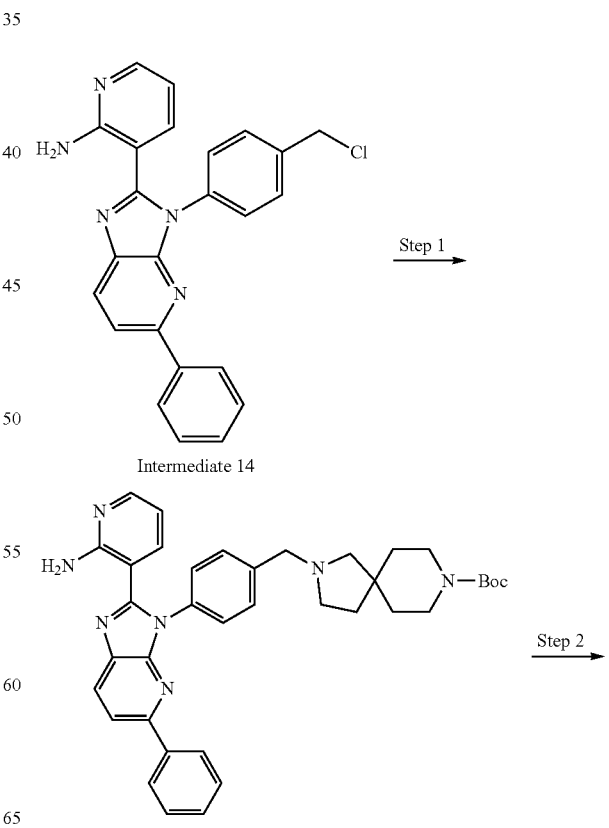

-continued

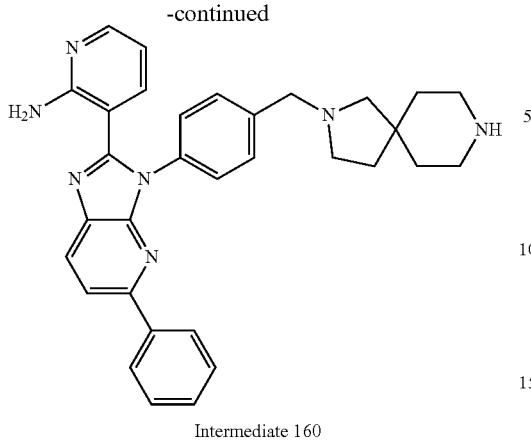

Intermediate 160

Step 1: Tert-butyl 2-(4-(2-(2-aminopyridin-3-yl)-5-phenyl-3H-imidazo[4,5-b]pyridin-3-yl)benzyl)-2,8-diazaspiro[4.5]decane-8-carboxylate To a solution of Intermediate 14 (1.5 g, 3.6 mmol) and tert-butyl 2,8-diazaspiro[4.5]decane-8-carboxylate (1.0 g, 4.4 mmol) in DMF (10 mL) were added NaI (273 mg, 1.8 mmol) and $K_2CO_3$ (1.0 g, 7.0 mmol). The mixture was stirred at 80° C. for 1 hr. After cooling to 20° C., the reaction mixture was poured into $H_2O$ (100 mL), extracted with EtOAc (50 mL×3). The combined organic layers were dried over anhydrous $Na_2SO_4$, filtered, and concentrated under reduced pressure. The residue was purified by silica gel flash chromatography (Eluent of 0~85% EtOAc in petroleum ether) to give tert-butyl 2-(4-(2-(2-aminopyridin-3-yl)-5-phenyl-3H-imidazo[4,5-b]pyridin-3-yl)benzyl)-2,8-diazaspiro[4.5]decane-8-carboxylate (720 mg, yield: 34%) as a yellow solid. MS: m/z=616.4 [M+H]$^+$.

Step 2: 3-(3-(4-(2,8-Diazaspiro[4.5]decan-2-ylmethyl)phenyl)-5-phenyl-3H-imidazo[4,5-b]pyridin-2-yl)pyridin-2-amine A solution of tert-butyl 2-(4-(2-(2-aminopyridin-3-yl)-5-phenyl-3H-imidazo[4,5-b]pyridin-3-yl)benzyl)-2,8-diazaspiro[4.5]decane-8-carboxylate (720 mg, 1.2 mmol) in HCl in 1,4-dioxane (4 M, 5 mL) was stirred at 25° C. for 0.5 hr. The mixture was concentrated and washed with $CH_2Cl_2$ (3 mL), then concentrated under reduced pressure to give 3-(3-(4-((2,8-diazaspiro[4.5]decan-2-yl)methyl)phenyl)-5-phenyl-3H-imidazo[4,5-b]pyridin-2-yl)pyridin-2-amine (Intermediate 160, 600 mg, HCl salt, yield: 91%) as a yellow solid. MS: m/z=516.3 [M+H]$^+$. $^1$H NMR (400 MHz, Methanol-$d_4$) δ 8.33 (d, J=8.8 Hz, 1H), 8.10-8.01 (m, 4H), 7.96-7.87 (m, 3H), 7.72 (d, J=8.0 Hz, 2H), 7.49-7.40 (m, 3H), 6.96-6.87 (m, 1H), 4.67-4.54 (m, 2H), 3.75-3.65 (m, 2H), 3.51 (d, J=10.0 Hz, 1H), 3.35 (s, 2H), 3.32-3.20 (m, 3H), 2.32-2.23 (m, 1H), 2.15-2.05 (m, 2H), 2.04-1.96 (m, 3H).

Intermediate 161: (R)-3-(3-(4-((2,7-Diazaspiro[4.4]nonan-2-yl)methyl)phenyl)-5-phenyl-3H-imidazo[4,5-b]pyridin-2-yl)pyridin-2-amine

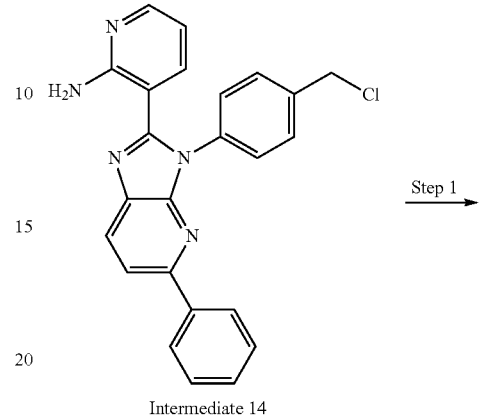

Intermediate 14

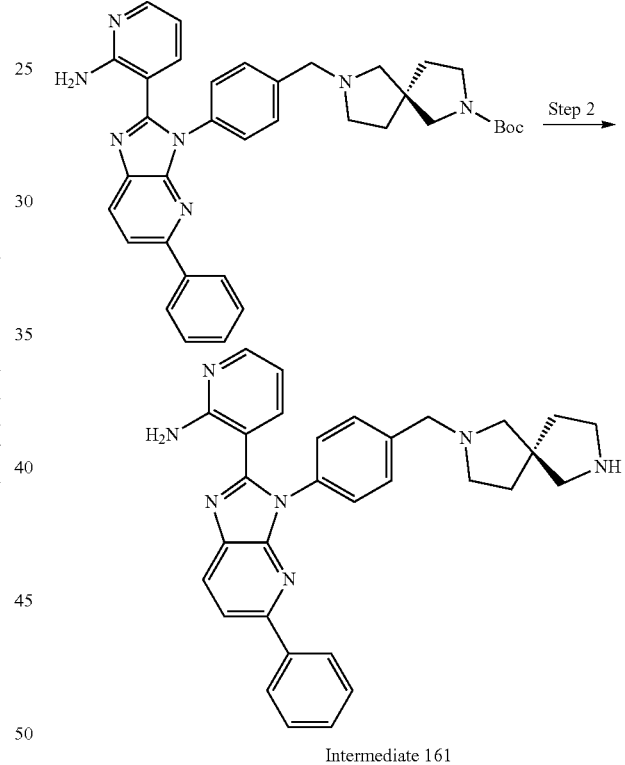

Intermediate 161

Step 1: tert-Butyl (R)-7-(4-(2-(2-aminopyridin-3-yl)-5-phenyl-3H-imidazo[4,5-b]pyridin-3-yl)benzyl)-2,7-diazaspiro[4.4]nonane-2-carboxylate To a solution of Intermediate 14 (1.0 g, 2.43 mmol) in DMF (10 mL) were added $K_2CO_3$ (671 mg, 4.86 mmol) and tert-butyl (R)-2,7-diazaspiro[4.4]nonane-2-carboxylate (604 mg, 2.67 mmol). The mixture was stirred at 25° C. for 16 hr. The reaction mixture was diluted with $H_2O$ (10 mL) at 25° C. and extracted with $CH_2Cl_2$ (20 mL×3). The combined organic layers were washed with brine (30 ml), dried over $Na_2SO_4$, filtered and concentrated under reduced pressure. The crude product was purified by silica gel flash chromatography (Eluent of 1~5% MeOH in CH₂C₂) to give tert-butyl (R)-7-(4-(2-(2-aminopyridin-3-yl)-5-phenyl-3H-imidazo[4,5-b]pyridin-3-yl)benzyl)-2,7-diazaspiro[4.4]nonane-2-carboxylate (920 mg, yield: 63%) as a yellow solid. MS: m/z=602.6 [M+H]⁺.

Step 2: (R)-3-(3-(4-((2,7-Diazaspiro[4.4]nonan-2-yl)methyl)phenyl)-5-phenyl-3H-imidazo[4,5-b]pyridin-2-yl)pyridin-2-amine A solution of tert-butyl (R)-7-(4-(2-(2-aminopyridin-3-yl)-5-phenyl-3H-imidazo[4,5-b]pyridin-3-yl)benzyl)-2,7-diazaspiro[4.4]nonane-2-carboxylate (700 mg, 1.16 mmol) in 4 M HCl/1,4-dioxane (7 mL) was stirred at 25° C. for 2 hr. The reaction was concentrated under reduced pressure to give (R)-3-(3-(4-((2,7-diazaspiro[4.4]nonan-2-yl)methyl)phenyl)-5-phenyl-3H-imidazo[4,5-b]pyridin-2-yl)pyridin-2-amine (Intermediate 161, 600 mg, HCl salt, yield: 96%) as a yellow solid. MS: m/z=502.3 [M+H]⁺. ¹H NMR (400 MHz, Dimethylsulfoxide-d₆) δ 12.00-11.77 (m, 1H), 9.73-9.52 ((m, 2H), 8.58-8.44 (m, 1H), 8.38 (d, J=8.4 Hz, 1H), 8.16 (dd, J=6.0, 1.6 Hz, 1H), 8.04-8.09 (m, 3H), 7.92-7.85 (m, 3H), 7.66 (d, J=8.4 Hz, 2H), 7.52-7.46 (m, 2H), 7.45-7.40 (m, 1H), 7.00-6.92 (m, 1H), 4.57-4.41 (m, 2H), 3.50-3.58 (m, 4H), 3.41-3.33 (m, 2H), 3.25-3.22 (m, 2H), 2.28-2.13 (m, 2H), 2.10-1.97 (m, 2H).

Intermediate 162: 3-(3-(4-(2,9-Diazaspiro[5.5]undecan-9-ylmethyl)phenyl)-5-phenyl-3H-imidazo[4,5-b]pyridin-2-yl)pyridin-2-amine

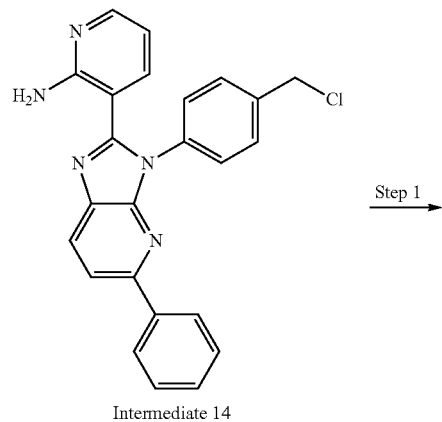

Intermediate 14

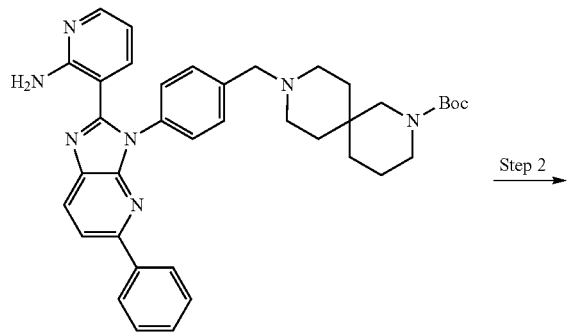

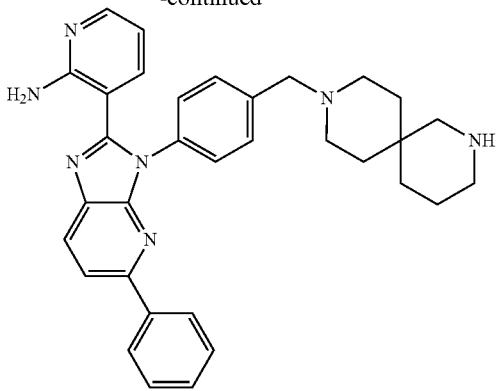

Intermediate 162

Step 1: tert-Butyl 9-(4-(2-(2-aminopyridin-3-yl)-5-phenyl-3H-imidazo[4,5-b]pyridin-3-yl)benzyl)-2,9-diazaspiro[5.5]undecane-2-carboxylate To a solution of Intermediate 14 in DMF (10 mL) were added K₂CO₃ (671 mg, 4.86 mmol) and tert-butyl 2,9-diazaspiro[5.5]undecane-2-carboxylate (679 mg, 2.67 mmol). The mixture was stirred at 25° C. for 48 hr. The reaction mixture was diluted with H₂O (10 ml) at 25° C. and extracted with CH₂Cl₂ (20 mL×3). The combined organic layers were washed with brine (15 mL), dried over Na₂SO₄, filtered and concentrated under reduced pressure. The crude was purified by silica gel flash chromatography (Eluent of 1~4% MeOH in CH₂Cl₂) to give tert-butyl 9-(4-(2-(2-aminopyridin-3-yl)-5-phenyl-3H-imidazo[4,5-b]pyridin-3-yl)benzyl)-2,9-diazaspiro[5.5]undecane-2-carboxylat (612 mg, yield: 40%) as a yellow solid. MS: m/z=630.5 [M+H]⁺. ¹H NMR (400 MHz, Dimethylsulfoxide-d₆) δ 8.26 (d, J=8.4 Hz, 1H), 8.06-7.94 (m, 4H), 7.48-7.33 (m, 7H), 7.14 (dd, J=7.6, 1.6 Hz, 1H), 7.05 (br s, 2H), 6.35 (dd, J=7.2, 5.2 Hz, 1H), 3.62-3.55 (m, 2H), 3.27 (s, 2H), 3.22-3.15 (m, 2H), 2.49-2.44 (m, 2H), 2.35-2.22 (m, 2H), 1.38-1.34 (m, 8H), 1.38 (s, 1H).

Step 2: 3-(3-(4-(2,9-Diazaspiro[5.5]undecan-9-ylmethyl)phenyl)-5-phenyl-3H-imidazo[4,5-b]pyridin-2-yl)pyridin-2-amine A solution of tert-butyl 9-[[4-[2-(2-amino-3-pyridyl)-5-phenyl-imidazo[4,5-b]pyridin-3-yl]phenyl]methyl]-2,9-diazaspiro[5.5]undecane-2-carboxylate (630 mg, 1.0 mmol) in HCl/1,4-dioxane (4M, 6 mL) was stirred at 25° C. for 1 hr. The reaction was concentrated under reduced pressure to give 3-(3-(4-(2,9-diazaspiro[5.5]undecan-9-ylmethyl)phenyl)-5-phenyl-3H-imidazo[4,5-b]pyridin-2-yl)pyridin-2-amine (Intermediate 162, 540 mg, HCl salt, 9.0 mg delivered) as a yellow solid. MS: m/z=530.4 [M+H]⁺. ¹H NMR (400 MHz, Dimethylsulfoxide-d₆) δ 11.24-10.95 (m, 1H), 9.45-8.99 ((m, 2H), 8.52 (br s, 1H), 8.38 (d, J=8.4 Hz, 1H), 8.16 (d, J=6.0 Hz, 1H), 8.12-8.02 (m, 3H), 7.91-7.81 (m, 3H), 7.73-7.62 (m, 2H), 7.52-7.40 (m, 3H), 6.93-6.84 (m, 1H), 4.41 (d, J=5.2 Hz, 2H), 3.21-3.09 (m, 5H), 2.99-2.90 (m, 2H), 2.87-2.75 (m, 1H), 2.13-2.09 (m, 1H), 2.00-1.88 (m, 1H), 1.86-1.73 (m, 2H), 1.72-1.56 (m, 3H), 1.45-1.40 (m, 1H).

Intermediate 163: (S)-3-(3-(4-((2,7-Diazaspiro[4.4]nonan-2-yl)methyl)phenyl)-5-phenyl-3H-imidazo[4,5-b]pyridin-2-yl)pyridin-2-amine

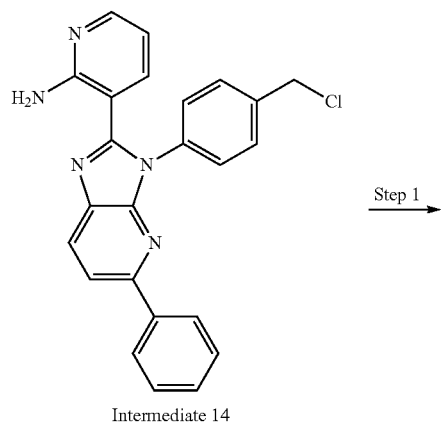

Intermediate 14

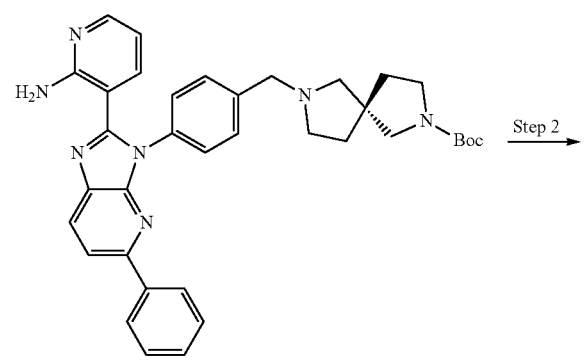

Intermediate 163

Step 1: (S)-3-(3-(4-((2,7-Diazaspiro[4.4]nonan-2-yl)methyl)phenyl)-5-phenyl-3H-imidazo[4,5-b]pyridin-2-yl)pyridin-2-amine To a solution of Intermediate 14 (1.0 g, 2.43 mmol) and tert-butyl (S)-2,7-diazaspiro[4.4]nonane-2-carboxylate (659 mg, 2.91 mmol) in DMF (15 mL) was added K$_2$CO$_3$ (671 mg, 4.86 mmol). The mixture was stirred at 25° C. for 16 hr. The reaction mixture was diluted with H$_2$O (50 mL) at 25° C. and extracted with EtOAc (100 mL×2). The combined organic layers were washed with brine (200 mL), dried over Na$_2$SO$_4$, filtered, and concentrated under reduced pressure. The residue was purified by silica gel flash chromatography (Eluent of 0~5% MeOH in CH$_2$Cl$_2$) to give tert-butyl (S)-7-(4-(2-(2-aminopyridin-3-yl)-5-phenyl-3H-imidazo[4,5-b]pyridin-3-yl)benzyl)-2,7-diazaspiro[4.4]nonane-2-carboxylate (600 mg, yield: 41%) as a brown solid. MS: m/z=602.3 [M+H]$^+$. $^1$H NMR (400 MHz, Chloroform-d) δ 8.13 (d, J=8.4 Hz, 1H), 8.07 (dd, J=4.8, 1.6 Hz, 1H), 8.03-8.01 (m, 2H), 7.8 (d, J=8.4 Hz, 1H), 7.51-7.49 (m, 2H), 7.46-7.35 (m, 5H), 7.09 (dd, J=7.6, 1.6 Hz, 1H), 6.59 (br s, 2H), 6.36 (dd, J=7.6, 4.8 Hz, 1H), 3.80-3.70 (m, 2H), 3.50-3.20 (m, 4H), 2.80-2.50 (m, 4H), 1.95-1.80 (m, 4H), 1.46 (s, 9H).

Step 2: (S)-3-(3-(4-((2,7-Diazaspiro[4.4]nonan-2-yl)methyl)phenyl)-5-phenyl-3H-imidazo[4,5-b]pyridin-2-yl)pyridin-2-amine To a solution of tert-butyl (S)-7-(4-(2-(2-aminopyridin-3-yl)-5-phenyl-3H-imidazo[4,5-b]pyridin-3-yl)benzyl)-2,7-diazaspiro[4.4]nonane-2-carboxylate (580 mg, 964 μmol) in 1,4-dioxane (2 mL) was added HCl/1,4-dioxane (4M, 8 mL). The mixture was stirred at 25° C. for 2 hr. The reaction was filtered and concentrated under reduced pressure. (S)-3-(3-(4-((2,7-Diazaspiro[4.4]nonan-2-yl)methyl)phenyl)-5-phenyl-3H-imidazo[4,5-b]pyridin-2-yl)pyridin-2-amine (Intermediate 163, 500 mg, HCl salt, yield: 96%) was obtained as a yellow solid. MS: m/z=502.3 [M+H]$^+$. $^1$H NMR (400 MHz, Dimethylsulfoxide-d$_6$) δ 11.9 (br s, 1H), 9.80-9.66 (m, 2H), 8.66-8.50 (m, 2H), 8.38 (d, J=8.4 Hz, 1H), 8.17 (dd, J=6.4, 1.6 Hz, 1H), 8.08-8.05 (m, 3H), 7.93-7.86 (M, 3H), 7.66 (d, J=8.4 Hz, 2H), 7.54-7.40 (m, 3H), 7.00-6.95 (m, 1H), 3.55-3.50 (m, 1H), 3.40-3.17 (m, 8H), 2.33-1.95 (m, 5H).

Intermediate 164: (R)-3-(3-(4-((3-Methylpiperazin-1-yl)methyl)phenyl)-5-phenyl-3H-imidazo[4,5-b]pyridin-2-yl)pyridin-2-amine

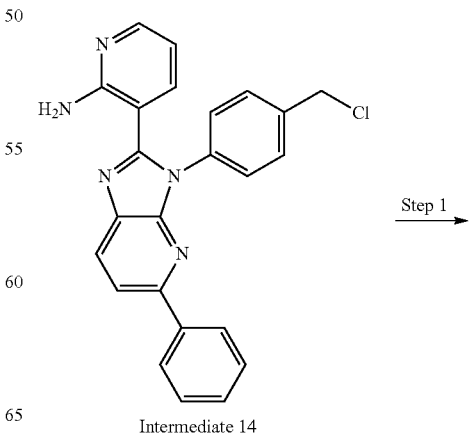

Intermediate 14

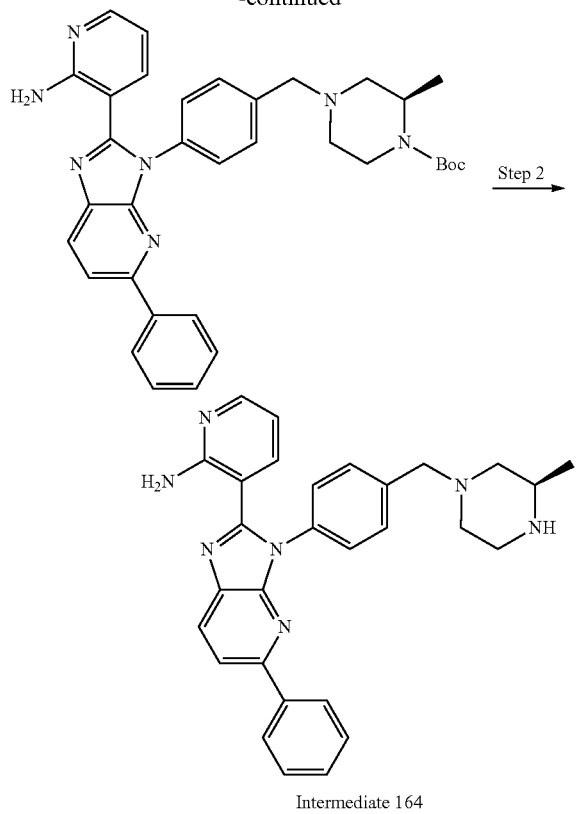

Intermediate 164

Step 1: (R)-Tert-butyl 4-(4-(2-(2-aminopyridin-3-yl)-5-phenyl-3H-imidazo[4,5-b]pyridin-3-yl)benzyl)-2-methylpiperazine-1-carboxylate To a solution of Intermediate 14 (1.0 g, 2.43 mmol) in DMF (5 mL) were added $K_2CO_3$ (671 mg, 4.86 mmol) and (R)-tert-butyl 2-methylpiperazine-1-carboxylate (632 mg, 3.16 mmol). The mixture was stirred at 25° C. for 16 hr. The reaction mixture was diluted with $H_2O$ (10 mL) at 25° C. and extracted with $CH_2Cl_2$ (20 mL×3). The combined organic layers were washed with brine (30 mL), dried over $Na_2SO_4$, filtered, and concentrated under reduced pressure. The crude was purified by silica gel flash chromatography (Eluent of 1~4% MeOH in $CH_2Cl_2$) to give (R)-tert-butyl 4-(4-(2-(2-aminopyridin-3-yl)-5-phenyl-3H-imidazo[4,5-b]pyridin-3-yl)benzyl)-2-methylpiperazine-1-carboxylate (671 mg, yield: 48%) as a yellow solid. MS: m/z=576.3 [M+H]+. $^1$H NMR (400 MHz, Dimethylsulfoxide-d$_6$) δ 8.27 (d, J=8.4 Hz, 1H), 8.04-7.95 (m, 4H), 7.51-7.38 (m, 7H), 7.16 (dd, J=7.6, 1.6 Hz, 1H), 7.04 (br s, 2H), 6.38 (dd, J=8.0, 4.8 Hz, 1H), 4.14-4.07 (m, 1H), 3.72-3.70 (m, 1H), 3.64 (d, J=13.6 Hz, 1H), 3.49 (d, J=13.6 Hz, 1H), 3.09-2.98 (m, 1H), 2.84-2.78 (m, 1H), 2.63-2.57 (m, 1H), 2.08 (dd, J=11.2, 4.0 Hz, 1H), 2.02-1.92 (m, 1H), 1.40 (s, 9H), 1.17 (d, J=6.8 Hz, 3H).

Step 2: (R)-3-(3-(4-((3-Methylpiperazin-1-yl)methyl)phenyl)-5-phenyl-3H-imidazo[4,5-b]pyridin-2-yl)pyridin-2-amine To a solution of (R)-tert-butyl 4-(4-(2-(2-aminopyridin-3-yl)-5-phenyl-3H-imidazo[4,5-b]pyridin-3-yl)benzyl)-2-methylpiperazine-1-carboxylate (700 mg, 1.22 mmol) in 4 M HCl in 1,4-dioxane (5 mL) at 25° C. The mixture was stirred at 25° C. for 2 hr. The reaction was concentrated under reduced pressure to give product (500 mg, HCl salt) as a yellow solid. The product (50 mg, HCl salt) was diluted with aqueous $NaHCO_3$ (10 mL) and extracted with $CH_2Cl_2$ (10 mL×3). The combined organic layers were washed with brine (20 mL), dried over $Na_2SO_4$, filtered and concentrated under reduced pressure. (R)-3-(3-(4-((3-Methylpiperazin-1-yl)methyl)phenyl)-5-phenyl-3H-imidazo[4,5-b]pyridin-2-yl)pyridin-2-amine (Intermediate 164, 22.9 mg, yield: 86%) was obtained as a white solid. MS: m/z=476.2 [M+H]+. $^1$H NMR (400 MHz, Dimethylsulfoxide-d$_6$) δ 8.27 (d, J=8.4 Hz, 1H), 8.08-7.95 (m, 4H), 7.52-7.35 (m, 7H), 7.15 (d, J=6.0 Hz, 1H), 7.04 (br s, 2H), 6.40-6.34 (m, 1H), 3.53 (s, 2H), 2.87-2.77 (m, 1H), 2.75-2.62 (m, 4H), 2.02-1.91 (m, 1H), 1.68-1.58 (m, 1H), 0.92 (d, J=6.0 Hz, 3H).

Intermediate 165: 3-(3-(4-(((3S,5R)-3,5-Dimethylpiperazin-1-yl)methyl)phenyl)-5-phenyl-3H-imidazo[4,5-b]pyridin-2-yl)pyridin-2-amine

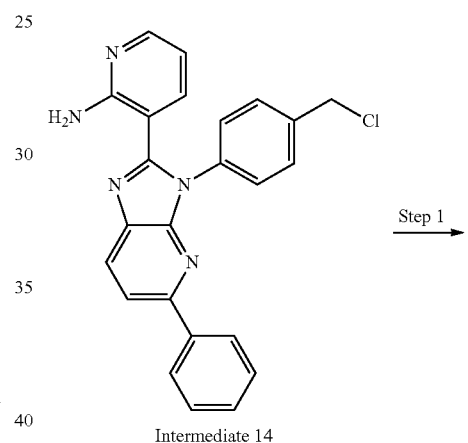

Intermediate 14

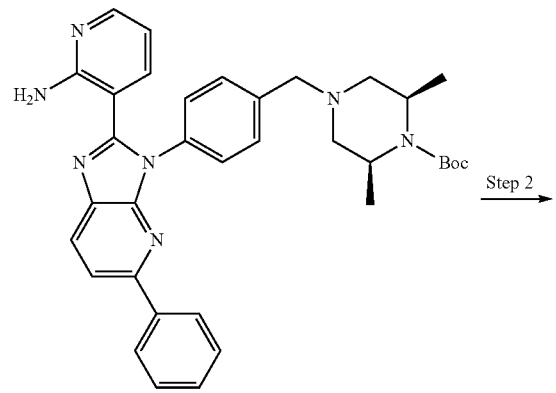

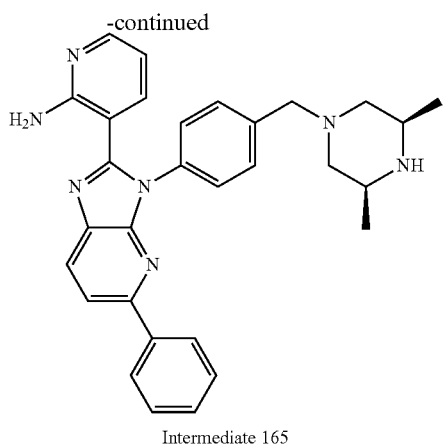

Intermediate 165

Step 1: (2S,6R)-Tert-butyl 4-(4-(2-(2-aminopyridin-3-yl)-5-phenyl-3H-imidazo[4,5-b]pyridin-3-yl)benzyl)-2,6-dimethylpiperazine-1-carboxylate To a solution of Intermediate 14 (1.0 g, 2.43 mmol) and tert-butyl (2S,6R)-2,6-dimethylpiperazine-1-carboxylate (520 mg, 2.43 mmol) in DMF (10 mL) was added $K_2CO_3$ (671 mg, 4.86 mmol). The mixture was stirred at 25° C. for 16 hr. The reaction mixture was diluted with $H_2O$ (10 mL) at 25° C. and extracted with EtOAc (10 mL×3). The combined organic layers were washed with brine (10 mL×3), dried over $Na_2SO_4$, filtered, and concentrated under reduced pressure. The residue was purified by silica gel flash chromatography (Eluent of 1~2% MeOH in $CH_2Cl_2$) to give (2S,6R)-tert-butyl 4-(4-(2-(2-aminopyridin-3-yl)-5-phenyl-3H-imidazo[4,5-b]pyridin-3-yl)benzyl)-2,6-dimethylpiperazine-1-carboxylate (770 mg, yield: 54%) as a yellow solid, which was used directly in the next step. MS: m/z=590.4 [M+H]$^+$.

Step 2: 3-(3-(4-(((3S,5R)-3,5-Dimethylpiperazin-1-yl)methyl)phenyl)-5-phenyl-3H-imidazo[4,5-b]pyridin-2-yl)pyridin-2-amine To a solution of tert-butyl (2S,6R)-4-[[4-[2-(2-amino-3-pyridyl)-5-phenyl-imidazo[4,5-b]pyridin-3-yl]phenyl]methyl]-2,6-dimethyl-piperazine-1-carboxylate (50 mg, 84.9 μmol) in 1,4-dioxane (3 mL) was added HCl/1,4-dioxane (4M, 5 mL). The mixture was stirred at 25° C. for 1 hr. The reaction mixture was concentrated under reduced pressure to remove 1,4-dioxane. The crude was dissolved in $H_2O$ (5 mL) and extracted with $CH_2Cl_2$ (5 mL×3). The aqueous phase was added $NaHCO_3$ and extracted with $CH_2Cl_2$ (5 mL×3), filtered and concentrated to give 3-(3-(4-(((3S,5R)-3,5-dimethylpiperazin-1-yl)methyl)phenyl)-5-phenyl-3H-imidazo[4,5-b]pyridin-2-yl)pyridin-2-amine (Intermediate 165, 34 mg, yield: 82%) as a yellow solid. MS: m/z=490.1 [M+H]$^+$. $^1$H NMR (400 MHz, Dimethylsulfoxide-d$_6$) δ 8.27 (d, J=8.4 Hz, 1H), 7.97-8.04 (m, 4H), 7.42-7.48 (m, 6H), 7.37-7.42 ((m, 1H), 7.15 (dd, J=7.6, 2.0 Hz, 1H), 7.05 (br s, 2H), 6.36 (dd, J=7.6, 4.8 Hz, 1H), 3.52 (s, 2H), 2.73-2.79 (m, 2H), 2.64-2.67 (m, 2H), 1.56-1.50 (m, 2H), 0.91 (d, J=6.0 Hz, 6H).

Intermediate 166: 4-(Azepan-4-ylamino)-1,3,5-triazine-2-carbonitrile

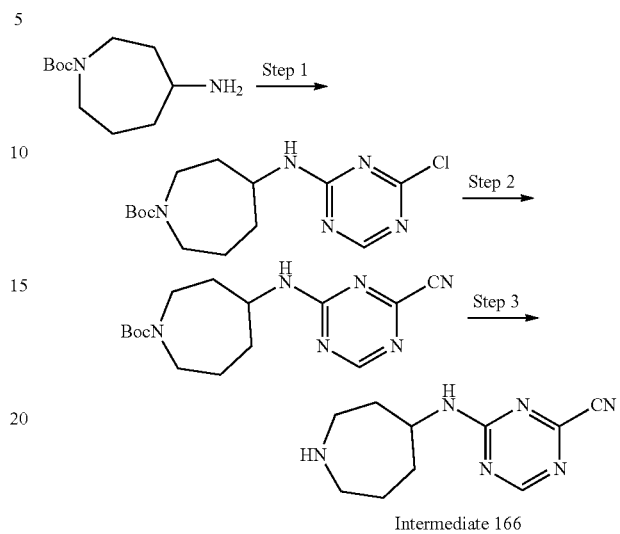

Intermediate 166

Step 1: Tert-butyl 4-((4-chloro-1,3,5-triazin-2-yl)amino)azepane-1-carboxylate To a solution of tert-butyl 4-aminoazepane-1-carboxylate (500 mg, 2.33 mmol) and DIEA (905 mg, 7.00 mmol) in THF (20 mL) was added 2,4-dichloro-1,3,5-triazine (350 mg, 2.33 mmol). The mixture was stirred at 0° C. for 1 hr. The reaction mixture was diluted with $H_2O$ (10 mL) and extracted with $CH_2Cl_2$ (10 mL×3). The combined organic layers were washed with brine (5 mL×2), dried over $Na_2SO_4$, filtered and concentrated under reduced pressure. The residue was purified by silica gel flash chromatography (Eluent of 10~15% EtOAc in petroleum ether) to give tert-butyl 4-((4-chloro-1,3,5-triazin-2-yl)amino)azepane-1-carboxylate (300 mg, yield: 35%) as colorless oil. MS: m/z=328.1 [M+H]$^+$.

Step 2: tert-Butyl 4-((4-cyano-1,3,5-triazin-2-yl)amino)azepane-1-carboxylate To a solution of tert-butyl 4-((4-chloro-1,3,5-triazin-2-yl)amino)azepane-1-carboxylate (300 mg, 915 μmol) in DMSO (10 mL) was added KCN (370 mg, 5.68 mmol). The mixture was stirred at 0° C. for 0.5 hr, then added DABCO (20.5 mg, 183 μmol). The mixture was stirred at 25° C. for 16 hr. The mixture was quenched with water (10 mL) and extracted with EtOAc (10 mL×3). The combined organic layers were dried over anhydrous $Na_2SO_4$, filtered and concentrated. The residue was purified by silica gel flash chromatography (Eluent of 5~8% EtOAc in petroleum ether) to give tert-butyl 4-((4-cyano-1,3,5-triazin-2-yl)amino)azepane-1-carboxylate (240 mg, yield; 81%) as an off-white oil. MS: m/z=319.0 [M+H]$^+$.

Step 3: 4-(Azepan-4-ylamino)-1,3,5-triazine-2-carbonitrile

To a solution of tert-butyl 4-((4-cyano-1,3,5-triazin-2-yl)amino)azepane-1-carboxylate (240 mg, 754 μmol) in $CH_2Cl_2$ (5 mL) was added TFA (172 mg, 1.51 mmol). The mixture was stirred at 25° C. for 1 hr. The reaction mixture was filtered and concentrated under reduced pressure to give 4-(azepan-4-ylamino)-1,3,5-triazine-2-carbonitrile (Intermediate 166, 250 mg yield: 100%) as a pink oil. The crude was directly used to the next step.

Intermediate 167: 4-((1,4-Oxazepan-6-yl)amino)-1,3,5-triazine-2-carbonitrile

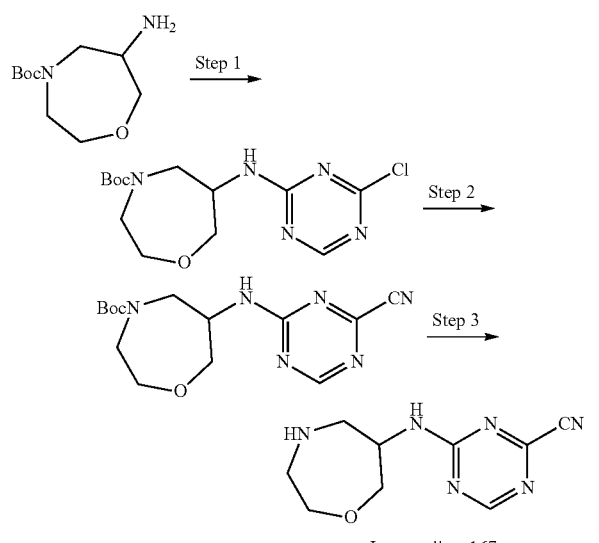

Intermediate 167

Step 1: Tert-butyl 6-((4-chloro-1,3,5-triazin-2-yl)amino)-1,4-oxazepane-4-carboxylate To a solution of tert-butyl 6-amino-1,4-oxazepane-4-carboxylate (600 mg, 2.77 mmol) and 2,4-dichloro-1,3,5-triazine (416 mg, 2.77 mmol) in THF (10 mL) was added DIEA (685 mg, 5.3 mmol). The resulting mixture was stirred at 0° C. for 12 hr. Then the reaction mixture was diluted with H$_2$O (50 mL) and extracted with CH$_2$Cl$_2$ (50 mL×2). The combined organic layers were dried over Na$_2$SO$_4$, filtered and concentrated under reduced pressure. tert-Butyl 6-((4-chloro-1,3,5-triazin-2-yl)amino)-1,4-oxazepane-4-carboxylate (400 mg, yield: 39%) was obtained as a light yellow solid. MS: m/z=330.1 [M+H]$^+$.

Step 2: tert-Butyl 6-((4-cyano-1,3,5-triazin-2-yl)amino)-1,4-oxazepane-4-carboxylate To a solution of tert-butyl 6-((4-chloro-1,3,5-triazin-2-yl)amino)-1,4-oxazepane-4-carboxylate (400 mg, 1.21 mmol) in DMSO (9 mL) were added KCN (260 mg, 3.99 mmol) and then DABCO (27.2 mg, 243 μmol). The mixture was stirred at 25° C. for 1 hr. The reaction mixture was poured into H$_2$O (50 mL). The resulting mixture was extracted with EtOAc (50 mL×2). The combined organic layers were washed with brine (50 mL), dried over Na$_2$SO$_4$, filtered and concentrated under reduced pressure. After purified by flash chromatography on silica gel (Eluent of 20%~30% EtOAc in petroleum ether), tert-butyl 6-((4-cyano-1,3,5-triazin-2-yl)amino)-1,4-oxazepane-4-carboxylate (380 mg, yield: 63%) was obtained as a light yellow solid. MS: m/z=321.0 [M+H]$^+$.

Step 3: 4-((1,4-Oxazepan-6-yl)amino)-1,3,5-triazine-2-carbonitrile

To a solution of tert-butyl 6-((4-cyano-1,3,5-triazin-2-yl)amino)-1,4-oxazepane-4-carboxylate (250 mg, 780 μmol) in CH$_2$Cl$_2$ (3 mL) was added TFA (1.54 g, 13.5 mmol). The mixture was stirred at 25° C. for 0.5 hr. The reaction mixture was filtered and concentrated under reduced pressure to give 4-((1,4-oxazepan-6-yl)amino)-1,3,5-triazine-2-carbonitrile (Intermediate 167, 330 mg, crude) was obtained as a yellow oil, which was used directly in the next step.

Intermediate 168: 3-(3-(4-((2,8-Diazaspiro[4.5]decan-8-yl)methyl)phenyl)-5-phenyl-3H-imidazo[4,5-b]pyridin-2-yl)pyridin-2-amine

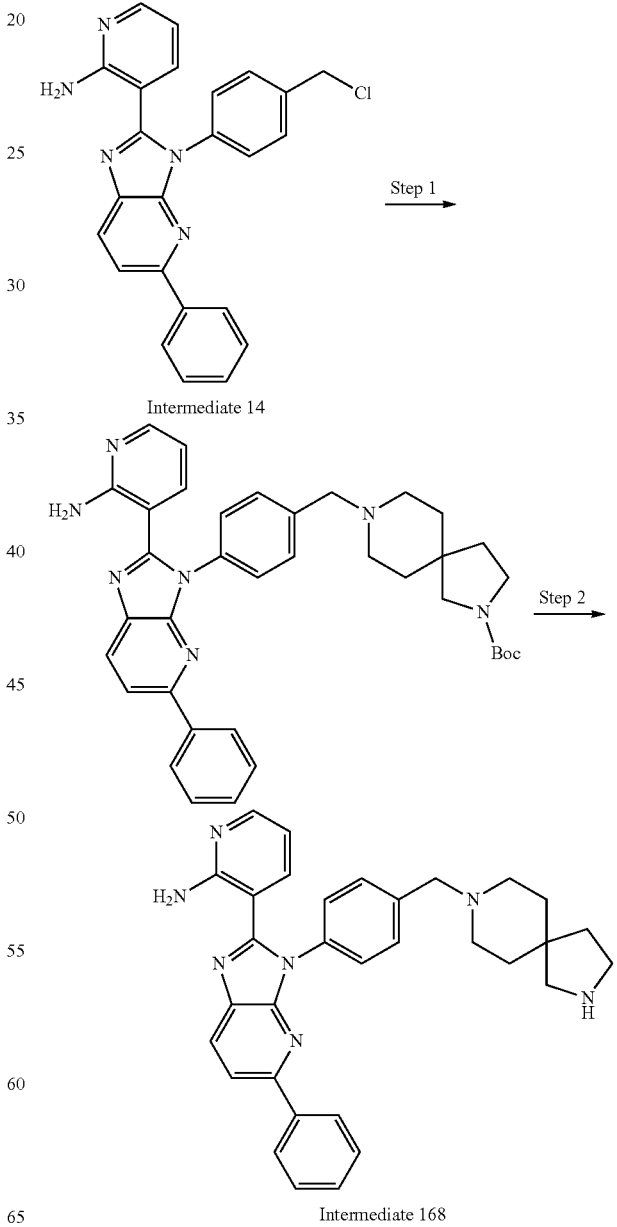

Intermediate 168

Step 1: Tert-butyl 8-(4-(2-(2-aminopyridin-3-yl)-5-phenyl-3H-imidazo[4,5-b]pyridin-3-yl)benzyl)-2,8-diazaspiro[4.5]decane-2-carboxylate To a solution of Intermediate 14 (250 mg, 607 μmol) in DMF (2 mL) were added tert-butyl 2,8-diazaspiro[4.5]decane-2-carboxylate (160 mg, 668 μmol), NaI (9.10 mg, 60.7 μmol) and K₂CO₃ (252 mg, 1.82 mmol). The resulting mixture was stirred at 80° C. for 16 hr. The reaction mixture was poured into H₂O (5 mL) and extracted with EtOAc (10 mL×3). The combined organic layers were dried over anhydrous Na₂SO₄, filtered, and concentrated under reduced pressure. The residue was purified by silica gel flash chromatography (Eluent of 0~65% EtOAc in petroleum ether) to give tert-butyl 8-(4-(2-(2-aminopyridin-3-yl)-5-phenyl-3H-imidazo[4,5-b]pyridin-3-yl)benzyl)-2,8-diazaspiro[4.5]decane-2-carboxylate (200 mg, yield: 53%) as a yellow solid. MS: m/z=616.2 [M+H]⁺.

Step 2: 3-(3-(4-((2,8-Diazaspiro[4.5]decan-8-yl)methyl)phenyl)-5-phenyl-3H-imidazo[4,5-b]pyridin-2-yl)pyridin-2-amine To a solution of tert-butyl 8-(4-(2-(2-aminopyridin-3-yl)-5-phenyl-3H-imidazo[4,5-b]pyridin-3-yl)benzyl)-2,8-diazaspiro[4.5]decane-2-carboxylate (280 mg, 455 μmol) in dioxane (1 mL) was added 4M HCl in 1,4-dioxane (2 mL). The mixture was stirred at 25° C. for 1 hr. The reaction mixture was concentrated under reduced pressure. Saturated NaHCO₃ (5 mL) aqueous solution was added and extracted with CH₂Cl₂ (15 mL). The organic layer was dried over Na₂SO₄, filtered, and concentrated under reduced pressure. (Intermediate 168, 200 mg, yield: 85%). MS: m/z=516.3 [M+H]⁺. ¹H NMR (400 MHz, Methanol-d₄) δ 8.18 (d, J=8.4 Hz, 1H), 8.02 (d, J=7.2 Hz, 2H), 7.97 (dd, J=4.8, 1.6 Hz, 1H), 7.93 (d, J=8.4 Hz, 1H), 7.52 (d, J=8.4 Hz, 2H), 7.45-7.34 (m, 5H), 7.31 (dd, J=6.8, 1.6 Hz, 1H), 6.45 (dd, J=7.6, 4.8 Hz, 1H), 3.62 (s, 2H), 3.10 (t, J=7.2 Hz, 2H), 2.85 (s, 2H), 2.50 (m, 4H), 1.75 (t, J=7.2 Hz, 2H), 1.65 (t, J=5.6 Hz, 4H).

Intermediate 169: 3-(3-(4-(((3,9-diazaspiro[5.5]undecan-3-yl)methyl)phenyl)-5-phenyl-3H-imidazo[4,5-b]pyridin-2-yl)pyridin-2-amine

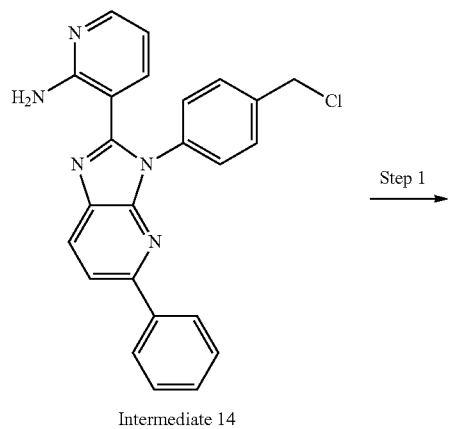

Intermediate 14

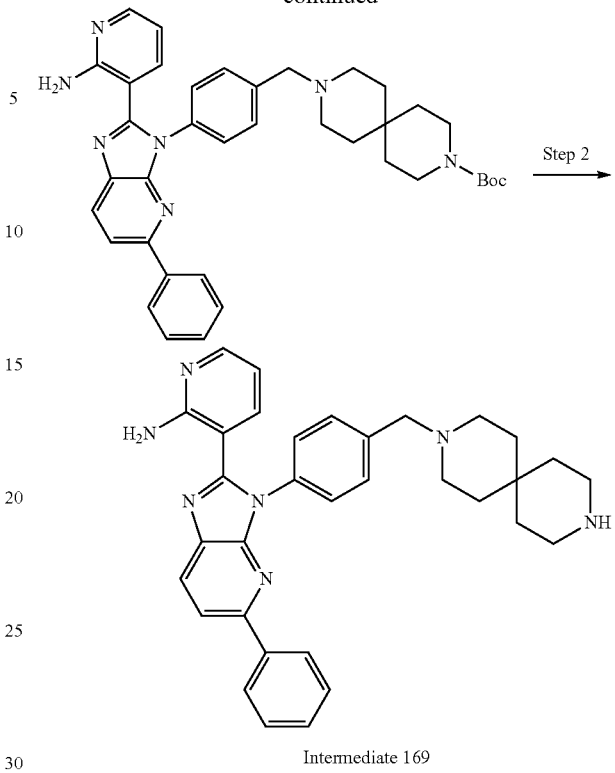

Intermediate 169

Step 1: Tert-butyl 9-(4-(2-(2-aminopyridin-3-yl)-5-phenyl-3H-imidazo[4,5-b]pyridin-3-yl)benzyl)-3,9-diazaspiro[5.5]undecane-3-carboxylate To a solution of Intermediate 14 (600 mg, 1.46 mmol) and tert-butyl 3,9-diazaspiro[5.5]undecane-3-carboxylate (408 mg, 1.60 mmol) in DMF (5 mL) were added NaI (21.9 mg, 146 μmol) and K₂CO₃ (403 mg, 2.91 mmol). The mixture was stirred at 80° C. for 16 hr. The reaction mixture was poured into H₂O (15 mL), extracted with EtOA (20 mL×3). The combined organic layers were dried over anhydrous Na₂SO₄, filtered and concentrated under reduced pressure. The residue was purified by silica gel flash chromatography (Eluent of 0~65% EtOAc in petroleum ether), tert-butyl 9-(4-(2-(2-aminopyridin-3-yl)-5-phenyl-3H-imidazo[4,5-b]pyridin-3-yl)benzyl)-3,9-diazaspiro[5.5]undecane-3-carboxylate (450 mg, yield: 49%) was obtained as a yellow solid. MS: m/z=630.5 [M+H]⁺.

Step 2: 3-(3-(4-((3,9-Diazaspiro[5.5]undecan-3-yl)methyl)phenyl)-5-phenyl-3H-imidazo[4,5-b]pyridin-2-yl)pyridin-2-amine To a solution of 9-(4-(2-(2-aminopyridin-3-yl)-5-phenyl-3H-imidazo[4,5-b]pyridin-3-yl)benzyl)-3,9-diazaspiro[5.5]undecane-3-carboxylate (200 mg, 318 μmol) in 1,4-dioxane (2 mL) was added 4M HCl in 1,4-dioxane (2 mL). The mixture was stirred at 25° C. for 1 hr. The reaction mixture was filtered, and the filter cake was dried. 3-(3-(4-((3,9-Diazaspiro[5.5]undecan-3-yl)methyl)phenyl)-5-phenyl-3H-imidazo[4,5-b]pyridin-2-yl)pyridin-2-amine (Intermediate 169, 121 mg, HCl salt, yield: 67%) was obtained as a yellow solid. MS: m/z=530.3 [M+H]⁺. ¹H NMR (400 MHz, Dimethylsulfoxide-d₆) δ 10.81-10.50 (m, 1H), 8.79-8.66 (m, 2H), 8.38 (dd, J=8.4 Hz, 1H), 8.13-8.11 (m, 1H), 8.08-8.05 (m, 4H), 7.86-7.77 (m, 3H), 7.67 (d, J=8.0 Hz, 2H), 7.51-7.46 (m, 2H), 7.45-7.41 (m, 1H), 6.86-6.78 (m, 1H), 4.41 (d, J=4.4 Hz, 2H), 3.21-3.15 (m, 2H), 3.09-3.01 (m, 6H), 1.91-1.85 (m, 2H), 1.82-1.71 (m, 4H), 1.54-1.53 (m, 2H).

Intermediate 170: 3-(3-(4-((2,6-Diazaspiro[3.3]heptan-2-yl)methyl)phenyl)-5-phenyl-3H-imidazo[4,5-b]pyridin-2-yl)pyridin-2-amine

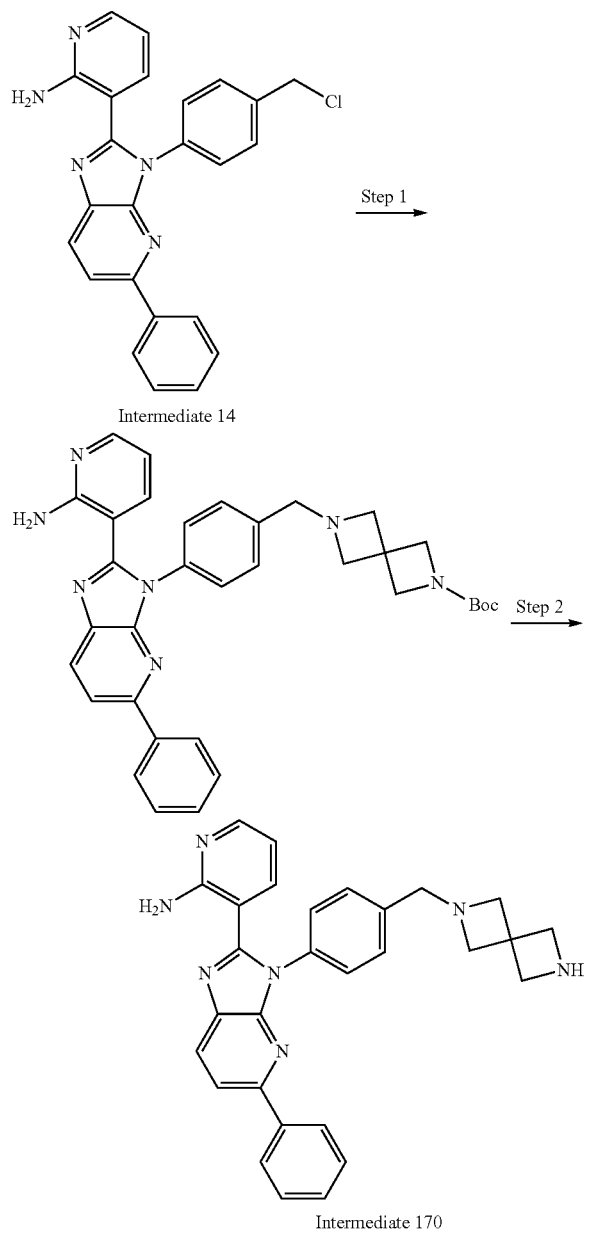

Step 1: tert-Butyl 6-(4-(2-(2-aminopyridin-3-yl)-5-phenyl-3H-imidazo[4,5-b]pyridin-3-yl)benzyl)-2,6-diazaspiro[3.3]heptane-2-carboxylate To a solution of Intermediate 14 (200 mg, 486 μmol) in MeCN (3 mL) were added K$_2$CO$_3$ (268 mg, 1.94 mmol), tert-butyl 2,6-diazaspiro[3.3]heptane-2-carboxylate (106 mg, 534 μmol) and NaI (7.28 mg, 48 μmol) at 25° C. The reaction mixture was stirred at 80° C. for 3 hr. The reaction mixture was filtered and concentrated under reduced pressure. The residue was purified by silica gel flash chromatography (Eluent of 0~7% MeOH in CH$_2$Cl$_2$) to give tert-butyl 6-(4-(2-(2-aminopyridin-3-yl)-5-phenyl-3H-imidazo[4,5-b]pyridin-3-yl)benzyl)-2,6-diazaspiro[3.3]heptane-2-carboxylate (150 mg, yield: 54%) as a yellow solid. MS: m/z=574.6 [M+H]$^+$.

Step 2: 3-(3-(4-((2,6-Diazaspiro[3.3]heptan-2-yl)methyl)phenyl)-5-phenyl-3H-imidazo[4,5-b]pyridin-2-yl)pyridin-2-amine To a solution of tert-butyl 6-(4-(2-(2-aminopyridin-3-yl)-5-phenyl-3H-imidazo[4,5-b]pyridin-3-yl)benzyl)-2,6-diazaspiro[3.3]heptane-2-carboxylate (150 mg, 261 μmol) in CH2Cl2 (3 mL) was added TFA (1.54 g, 13.5 mmol) at 25° C. The reaction mixture was stirred at 25° C. for 2 hr. The reaction mixture was concentrated to dryness to give 3-(3-(4-((2,6-diazaspiro[3.3]heptan-2-yl)methyl)phenyl)-5-phenyl-3H-imidazo[4,5-b]pyridin-2-yl)pyridin-2-amine (Intermediate 170, 120 mg, TFA salt, yield: 81%) as a yellow solid. MS: m/z=474.2 [M+H]$^+$. $^1$H NMR (400 MHz, Dimethylsulfoxide-d$_6$) δ 8.26 (d, J=8.4 Hz, 1H), 8.04-7.97 (m, 4H), 7.49-7.44 (m, 2H), 7.42-7.37 (m, 5H), 7.15 (dd, J=7.6, 1.6 Hz, 1H), 6.99 (br s, 2H), 6.39 (dd, J=8.0, 5.2 Hz, 1H), 3.58 (s, 2H), 3.56 (s, 4H), 3.25 (s, 4H), 1.23 (s, 1H).

Intermediate 171: 2-(4-(2-(2-Aminopyridin-3-yl)-5-phenyl-3H-imidazo[4,5-b]pyridin-3-yl)benzyl)-2-azaspiro[3.3]heptan-6-amine

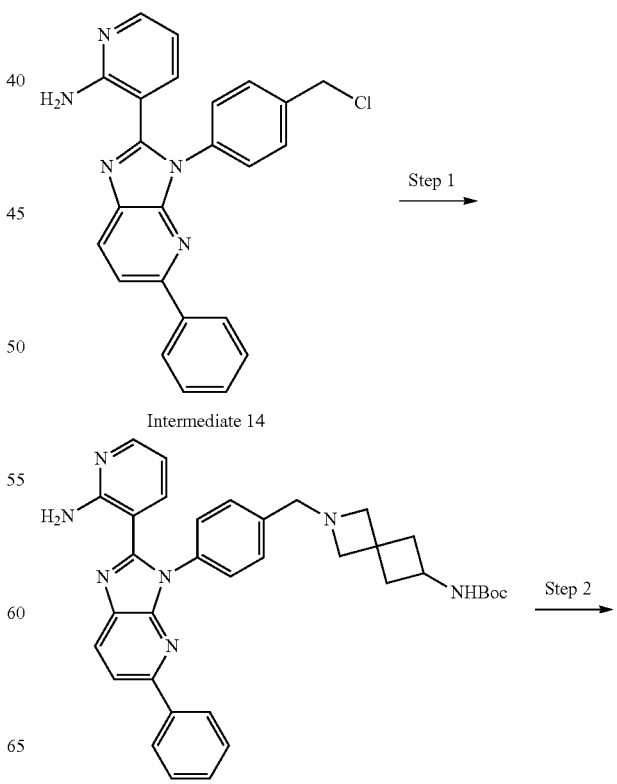

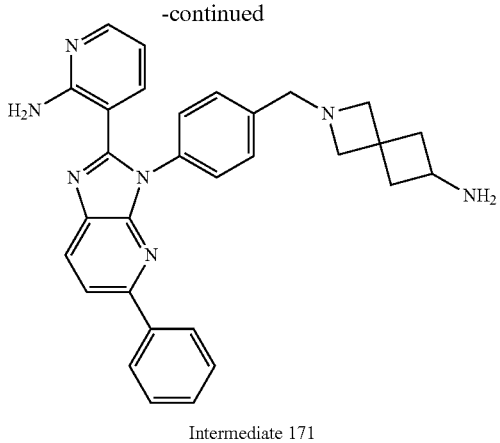

Intermediate 171

Step 1: Tert-butyl (2-(4-(2-(2-aminopyridin-3-yl)-5-phenyl-3H-imidazo[4,5-b]pyridin-3-yl)benzyl)-2-azaspiro[3.3]heptan-6-yl)carbamate To a solution of Intermediate 14 (500 mg, 1.21 mmol) in DMF (8 mL) were added tert-butyl (2-azaspiro[3.3]heptan-6-yl)carbamate (258 mg, 1.21 mmol), NaI (18.2 mg, 121 μmol) and $K_2CO_3$ (671 mg, 4.86 mmol). The mixture was stirred at 80° C. for 1 hr. The mixture was diluted with $H_2O$ (10 mL) and extracted with $CH_2Cl_2$ (20 mL×2). The combined organic layers were washed with brine (10 mL×2), dried over $Na_2SO_4$, filtered, and concentrated under reduced pressure. The residue was purified by silica gel flash chromatography (Eluent of 0~100% EtOAc in petroleum ether) to give tert-butyl (2-(4-(2-(2-aminopyridin-3-yl)-5-phenyl-3H-imidazo[4,5-b]pyridin-3-yl)benzyl)-2-azaspiro[3.3]heptan-6-yl)carbamate (150 mg, yield: 21%) as a yellow solid. MS: m/z=588.3 [M+H]$^+$.

Step 2: 2-(4-(2-(2-Aminopyridin-3-yl)-5-phenyl-3H-imidazo[4,5-b]pyridin-3-yl)benzyl)-2-azaspiro[3.3]heptan-6-amine To a solution of tert-butyl (2-(4-(2-(2-aminopyridin-3-yl)-5-phenyl-3H-imidazo[4,5-b]pyridin-3-yl)benzyl)-2-azaspiro[3.3]heptan-6-yl)carbamate (150 mg, 255 μmol) in $CH_2Cl_2$ (5 mL) was added TFA (87.3 mg, 765 μmol). The mixture was stirred at 25° C. for 0.5 hr. The mixture was diluted with $H_2O$ (10 mL) and pH was adjusted to about 8 with $NaHCO_3$ (aq). The mixture was extracted with $CH_2Cl_2$ (10 mL×2). The combined organic layers were washed with brine (10 mL×2), dried over $Na_2SO_4$, filtered and concentrated under reduced pressure. The residue was purified by prep-TLC ($CH_2Cl_2$:MeOH=10:1) to give 2-(4-(2-(2-aminopyridin-3-yl)-5-phenyl-3H-imidazo[4,5-b]pyridin-3-yl)benzyl)-2-azaspiro[3.3]heptan-6-amine (Intermediate 171, 123 mg, yield: 83%) as a light-yellow solid. MS: m/z=488.3 [M+H]$^+$. $^1$H NMR (400 MHz, Methanol-$d_4$) δ8.20 (d, J=8.8 Hz, 1H), 8.05-8.01 (m, 2H), 7.99 (dd, J=5.2, 1.6 Hz, 1H), 7.95 (d, J=8.4 Hz, 1H), 7.58-7.50 (m, 2H), 7.43-7.39 (m, 2H), 7.34 (dd, J=7.6, 2.0 Hz, 1H), 6.49 (dd, J=7.6, 4.8 Hz, 1H), 6.21-6.17 (m, 2H), 5.65 (dd, J=7.6, 4.4 Hz, 1H), 4.26-4.18 (m, 1H), 4.00 (s, 2H), 3.77 (s, 2H), 3.66 (s, 2H), 2.65-2.60 (m, 2H), 2.22-2.17 (m, 2H).

Intermediate 172: 3-(3-(4-((4-Aminopiperidin-1-yl)methyl)phenyl)-5-(3-fluorophenyl)-3H-imidazo[4,5-b]pyridin-2-yl)pyridin-2-amine

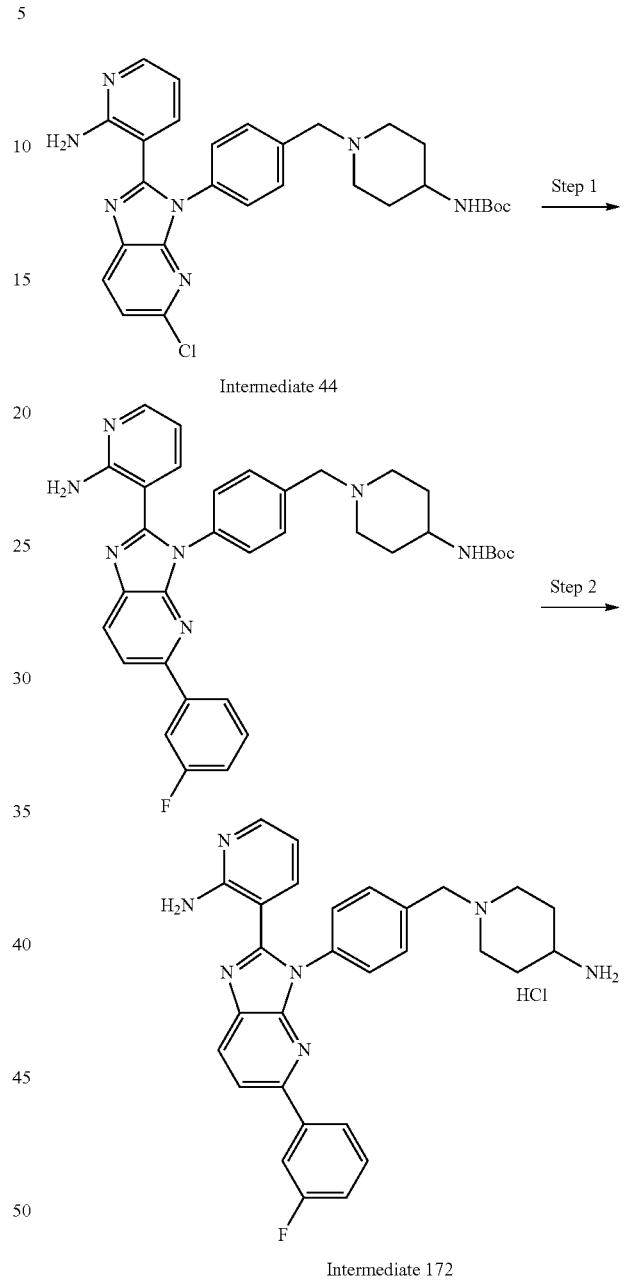

Intermediate 172

Step 1: tert-Butyl (1-(4-(2-(2-aminopyridin-3-yl)-5-(3-fluorophenyl)-3H-imidazo[4,5-b]pyridin-3-yl)benzyl)piperidin-4-yl)carbamate A mixture of Intermediate 44 (200 mg, 375 μmol), (3-fluorophenyl)boronic acid (79 mg, 562 μmol), Pd(dppf)Cl$_2$ (27 mg, 37 μmol), Cs$_2$CO$_3$ (244 mg, 749 μmol) in 1,4-dioxane (3 mL) and H$_2$O (0.3 mL) was degassed and purged with N$_2$ three times, then the mixture was stirred at 100° C. for 16 hr under N$_2$ atmosphere. The reaction mixture was diluted with H$_2$O (20 mL) and extracted with CH$_2$Cl$_2$ (30 mL×2). The combined organic layers were dried over Na₂SO₄, filtered and concentrated under reduced pressure. After purified by silica gel flash chromatography (Eluent of 0~7% MeOH in CH₂Cl₂), tert-butyl (1-(4-(2-(2-aminopyridin-3-yl)-5-(3-fluorophenyl)-3H-imidazo[4,5-b]pyridin-3-yl)benzyl)piperidin-4-yl)carbamate (138 mg, yield: 48%) was obtained as a brown solid. MS: m/z=594.3 [M+H]⁺.

Step 2: 3-(3-(4-((4-Aminopiperidin-1-yl)methyl)phenyl)-5-(3-fluorophenyl)-3H-imidazo[4,5-b]pyridin-2-yl)pyridin-2-amine To a solution of tert-butyl (1-(4-(2-(2-aminopyridin-3-yl)-5-(3-fluorophenyl)-3H-imidazo[4,5-b]pyridin-3-yl)benzyl)piperidin-4-yl)carbamate (135 mg, 227 µmol) in CH₂Cl₂ (3 mL) was added HCl in 1,4-dioxane (4 M, 1 mL). The mixture was stirred at 25° C. for 1 hr. The reaction mixture was concentrated under reduced pressure. The crude product was triturated with MeOH (2 mL) at 25° C. for 30 min. The suspension was filtered, the filter cake washed with 0.5 mL MeOH and concentrated under reduced pressure to give 3-(3-(4-((4-aminopiperidin-1-yl)methyl)phenyl)-5-(3-fluorophenyl)-3H-imidazo[4,5-b]pyridin-2-yl)pyridin-2-amine (Intermediate 172, 15 mg 2HCl salt, yield: 11%) as a light-yellow solid. MS: m/z=494.3 [M+H]⁺. ¹H NMR (400 MHz, Dimethylsulfoxide-d₆) δ 11.38-11.04 (m, 1H), 8.45-8.36 (m, 4H), 8.18-8.10 (m, 2H), 7.94 (d, J=8.0 Hz, 1H), 7.91-7.81 (m, 4H), 7.72-7.64 (m, 2H), 7.57-7.51 (m, 1H), 7.31-7.20 (m, 2H), 7.18-7.12 (m, 11H), 6.94-6.85 (m, 1H), 4.37-4.34 (m, 2H), 3.57 (s, 2H), 3.33-3.30 m, 1H), 3.12-3.02 (m, 2H), 2.22-2.14 (m, 2H), 2.09-1.95 (m, 2H). ¹⁹F NMR (400 MHz, Dimethylsulfoxide-d₆) δ −112.71.

Intermediate 173: (S)-3-(3-(4-((3-Aminopiperidin-1-yl)methyl)phenyl)-5-phenyl-3H-imidazo[4,5-b]pyridin-2-yl)pyridin-2-amine

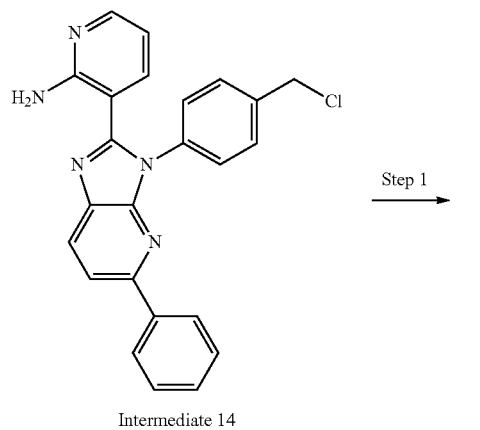

Intermediate 14

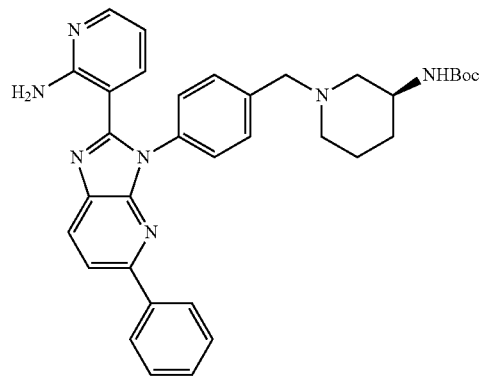

Step 2 →

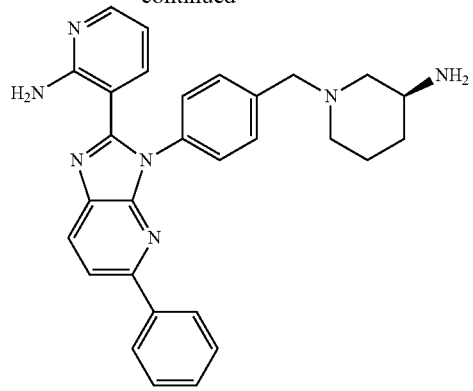

Intermediate 173

Step 1: (S)-Tert-butyl (1-(4-(2-(2-aminopyridin-3-yl)-5-phenyl-3H-imidazo[4,5-b]pyridin-3-yl)benzyl)piperidin-3-yl)carbamate To a solution of Intermediate 14 (800 mg, 1.9 mmol) in ACN (6 mL) were added tert-butyl N-[(3S)-3-piperidyl]carbamate (427 mg, 2.1 mmol), NaI (29.1 mg, 194 µmol) and K₂CO₃ (1.1 g, 7.8 mmol). The mixture was stirred at 80° C. for 2 hr. Then the reaction mixture was concentrated under reduced pressure to give a crude product. The residue was purified by silica gel flash chromatography (Eluent of 0~50% EtOAc in petroleum ether) to give (S)-tert-butyl (1-(4-(2-(2-aminopyridin-3-yl)-5-phenyl-3H-imidazo[4,5-b]pyridin-3-yl)benzyl)piperidin-3-yl)carbamate (400 mg, 29% yield) as a brown solid. MS: m/z=576.2 [M+H]⁺.

Step 2: (S)-3-(3-(4-((3-Aminopiperidin-1-yl)methyl)phenyl)-5-phenyl-3H-imidazo[4,5-b]pyridin-2-yl)pyridin-2-amine To a solution of tert-butyl N-[(3S)-1-[[4-[2-(2-amino-3-pyridyl)-5-phenyl-imidazo[4,5-b]pyridin-3-yl]phenyl]methyl]-3-piperidyl]carbamate (27 mg, 46.9 µmol) in CH₂Cl₂ (1 mL) was added TFA (10.7 mg, 93.8 µmol). The mixture was stirred at 25° C. for 0.5 hr. The mixture was concentrated under reduced pressure to give the crude (26 mg TFA salt, yield: 100%). The crude was purified by prep-HPLC (column: Welch Xtimate C18 150*25 mm 5 µm; mobile phase: [water (HCl)-ACN]; B %: 5%-35%, 8 min) to give (S)-3-(3-(4-((3-aminopiperidin-1-yl)methyl)phenyl)-5-phenyl-3H-imidazo[4,5-b]pyridin-2-yl)pyridin-2-amine (Intermediate 173, 5.3 mg HCl salt) as a light-yellow lyophilized powder. MS: m/z=476.2 [M+H]⁺. ¹H NMR (400 MHz, Methanol-d₄) δ8.32 (d, J=8.4 Hz, 1H), 8.10-7.98 (m, 4H), 7.94 (d, J=8.4 Hz, 2H), 7.89 (dd, J=7.6, 1.2 Hz, 1H), 7.74 (d, J=8.4 Hz, 2H), 7.49-7.34 (m, 3H), 6.93 (dd, J=7.6, 6.4 Hz, 1H), 4.62 (s, 2H), 3.89-3.56 (m, 3H), 3.28-3.12 (m, 2H), 2.26-1.99 (m, 3H), 1.90-1.66 (m, 1H).

Intermediate 174: 6-(2-(2-Aminopyridin-3-yl)-3-(4-(chloromethyl)phenyl)-3H-imidazo[4,5-b]pyridin-5-yl)-1-methylpyridin-2(1H)-one

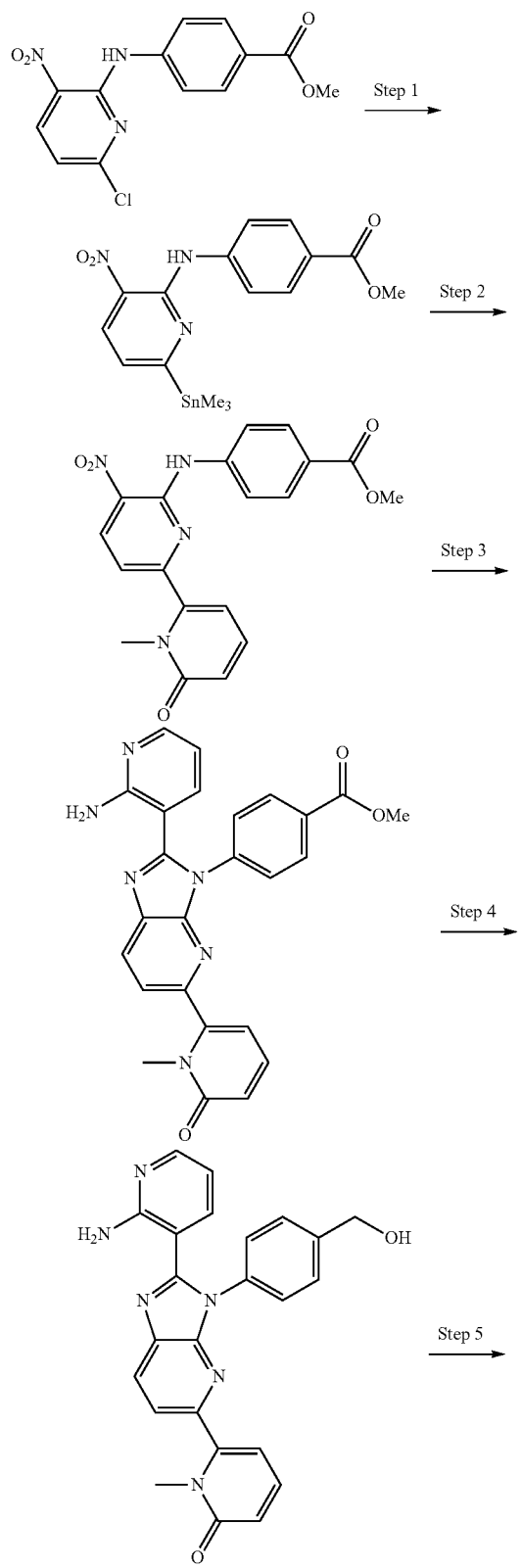

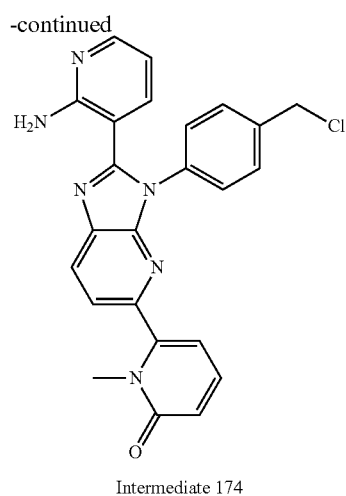

Intermediate 174

Step 1: Methyl 4-((3-nitro-6-(trimethylstannyl)pyridin-2-yl)amino)benzoate

A mixture of methyl 4-((6-chloro-3-nitropyridin-2-yl)amino)benzoate (refer to Intermediate 13 for detail procedures, 5 g, 16.3 mmol), (Me₃Sn)₂ (9.43 g, 28.8 mmol), and Pd(PPh₃)₄ (300 mg, 813 gmol) in 1,4-dioxane (50 mL) was degassed and purged with N₂ three times, and then the mixture was stirred at 90° C. for 4 hr under N₂ atmosphere. The reaction mixture was concentrated under reduced pressure to give methyl 4-((3-nitro-6-(trimethylstannyl)pyridin-2-yl)amino)benzoate (7 g. crude) as a black brown solid, which was directly used in the next step.

Step 2: Methyl 4-((1'-methyl-5-nitro-6'-oxo-1',6'-dihydro-[2,2'-bipyridin]-6-yl)amino)benzoate A mixture of methyl 4-((3-nitro-6-(trimethylstannyl)pyridin-2-yl)amino)benzoate (7 g, 16.1 mmol), 6-bromo-1-methylpyridin-2(1H)-one (3.62 g, 19.3 mmol), and Pd(PPh₃)₄ (296 mg, 803 μmol) in 1,4-dioxane (60 mL) was degassed and purged with N₂ three times, then the mixture was stirred at 100° C. for 16 hr under N₂ atmosphere. The residue was diluted with CH₂Cl₂ (50 mL) and extracted with H₂O (40 mL×3). The combined organic layers were washed with brine (30 mL×2), dried over Na₂SO₄, filtered and concentrated under reduced pressure. After purified by silica gel flash chromatography (Eluent of 20~25% EtOAc in CH₂Cl₂), methyl 4-((1'-methyl-5-nitro-6'-oxo-1',6'-dihydro-[2,2'-bipyridin]-6-yl)amino)benzoate (9.4 g, purity: 29%) was obtained as an orange red solid. MS: m/z=381.0 [M+H]⁺.

Step 3: Methyl 4-(2-(2-aminopyridin-3-yl)-5-(1-methyl-6-oxo-1,6-dihydropyridin-2-yl)-3H-imidazo[4,5-b]pyridin-3-yl)benzoate To a solution of methyl 4-((1'-methyl-5-nitro-6'-oxo-1',6'-dihydro-[2,2'-bipyridin]-6-yl)amino)benzoate (225 mg, 1.84 mmol) in DMSO (15 mL) was added Na₂S₂O₄ (1.28 g, 7.36 mmol). The mixture was stirred at 100° C. for 16 hr. The residue was diluted with H₂O (20 mL) and extracted with CH₂Cl₂ (20 mL×3). The combined organic layers were washed with brine (20 mL×2), dried over Na₂SO₄, filtered and concentrated under reduced pressure. After purified by silica gel flash chromatography (Eluent of 2~3%, MeOH in CH₂Cl₂), methyl 4-(2-(2-aminopyridin-3-yl)-5-(1-methyl-6-oxo-1,6-dihydropyridin-2-yl)-3H-imidazo[4,5-b]pyridin-3-yl)benzoate (300 mg, yield: 31%) was obtained as a black brown solid. MS: m/z=453.0 [M+H]⁺. ¹H NMR (400 MHz, Chloroform-d) δ 8.28-8.23 (m, 3H), 7.94 (dd, J=5.2 Hz, 1.2 Hz, 1H), 7.58 (d, J=8.4 Hz, 1H), 7.50-7.44 (m, 3H), 7.38-7.34 (m, 1H), 7.29 (d, J=7.6 Hz, 1H), 6.67-6.63 (m, 1H), 6.50 (dd, J=7.6, 5.2 Hz, 1H), 6.27 (dd, J=5.6 Hz, 1.2 Hz, 1H), 3.99 (s, 3H), 3.45 (s, 3H).

Step 4: 6-(2-(2-Aminopyridin-3-yl)-3-(4-(hydroxymethyl)phenyl)-3H-imidazo[4,5-b]pyridin-5-yl)-1-methylpyridin-2(1H)-one To a solution of methyl 4-(2-(2-aminopyridin-3-yl)-5-(1-methyl-6-oxo-1,6-dihydropyridin-2-yl)-3H-imidazo[4,5-b]pyridin-3-yl)benzoate (100 mg, 221 μmol) in THF (3 mL) was added LiAlH₄ (2.5 M, 177 μL) at 0° C. The mixture was stirred at 2-5° C. for 2 hr. The reaction mixture was quenched by Na₂SO₄·10H₂O (about 0.5 g) at 0° C., and the mixture was filtered. The filter cake was washed by CH₂Cl₂ (5 mL×3), and the filtrate was concentrated under reduced pressure to give 6-(2-(2-aminopyridin-3-yl)-3-(4-(hydroxymethyl)phenyl)-3H-imidazo[4,5-b]pyridin-5-yl)-1-methylpyridin-2(1H)-one (82 mg, yield: 89%) as a yellow solid. Compound 6 was directly used to the next step without purification. MS: m/z=425.3 [M+H]⁺.

Step 5: 6-(2-(2-Aminopyridin-3-yl)-3-(4-(chloromethyl)phenyl)-3H-imidazo[4,5-b]pyridin-5-yl)-1-methylpyridin-2(1H)-one To a solution of 6-(2-(2-aminopyridin-3-yl)-3-(4-(hydroxymethyl)phenyl)-3H-imidazo[4,5-b]pyridin-5-yl)-1-methylpyridin-2(1H)-one (300 mg, 707 μmol) in CH₂Cl₂ (3 mL) was added SOCl₂ (168 mg, 1.41 mmol) at 0° C. The mixture was stirred at 40° C. for 2 hr. The reaction mixture was quenched with H₂O (0.5 mL) at 0° C., then filtered and concentrated under reduced pressure to give 6-(2-(2-aminopyridin-3-yl)-3-(4-(chloromethyl)phenyl)-3H-imidazo[4,5-b]pyridin-5-yl)-1-methylpyridin-2(1H)-one (Intermediate 174, 300 mg, yield: 89%) as a yellow solid. MS: m/z=443.2 [M+H]⁺. ¹H NMR (400 MHz, Methanol-d₄) δ 8.43 (d, J=8.4 Hz, 1H), 8.05-8.01 (m, 1H), 7.92-7.88 (m, 1H), 7.76 (d, J=8.4 Hz, 1H), 7.70-7.62 (m, 3H), 7.53 (d, J=8.0 Hz, 2H), 6.90-6.85 (m, 1H), 6.71-6.66 (m, 1H), 6.62-6.57 (m, 1H), 4.75 (s, 2H), 3.46 (s, 3H).

Intermediate 175: 4-(Piperidin-4-ylamino)-1,3,5-triazine-2-carbonitrile

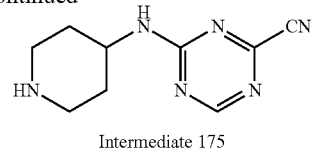

Intermediate 175

Step 1: tert-Butyl 4-((4-chloro-1,3,5-triazin-2-yl)amino)piperidine-1-carboxylate To a solution of tert-butyl piperidin-4-ylcarbamate (6 g, 29.9 mmol) in THF (70 mL) was added DIEA (5.81 g, 44.9 mmol). The mixture was stirred at 0° C. for 10 min. Then 2,4-dichloro-1,3,5-triazine (4.49 g, 29.9 mmol) in THF (30 mL) was added to the mixture. The mixture was stirred at 25° C. for 16 hr. The mixture was partitioned between EtOAc (600 mL) and H₂O (200 mL). The separated organic layer was washed with brine (60 mL) and dried over Na₂SO₄, filtered and concentrated. After purified by silica gel flash chromatography (Eluent of 0~27% EtOAc in petroleum ether), tert-butyl 4-((4-chloro-1,3,5-triazin-2-yl)amino)piperidine-1-carboxylate (5 g, yield: 31%) was obtained as a light-yellow solid. MS: m/z=314.0 [M+H]⁺.

Step 2: tert-Butyl 4-((4-cyano-1,3,5-triazin-2-yl)amino)piperidine-1-carboxylate To a solution of tert-butyl 4-((4-chloro-1,3,5-triazin-2-yl)amino)piperidine-1-carboxylate (5 g, 16 mmol) in DMSO (110 mL) were added KCN (2.01 g, 31 mmol) and DABCO (357 mg, 3.19 mmol). The mixture was stirred at 25° C. for 1 hr. The reaction mixture was poured into H₂O (1 L). The resulting mixture was extracted with EtOAc (500 mL×2). The combined organic layers were washed with brine (100 mL), dried over Na₂SO₄, filtered and concentrated under reduced pressure. After purified by flash chromatography on silica gel (Eluent of 0~30% EtOAc in petroleum ether), tert-butyl 4-((4-cyano-1,3,5-triazin-2-yl)amino)piperidine-1-carboxylate (1.5 g, yield: 28%) was obtained as a off white solid. MS: m/z=305.0 [M+H]⁺. ¹H NMR (400 MHz, Chloroform-d) δ 8.55 (d, J=31.2 HZ, 1H), 5.99-5.89 (m, 1H), 4.15-4.00 (m, 3H), 2.95-2.85 (m, 2H), 2.01-1.98 (m, 2H), 1.45 (s, 1H).

Step 3: 4-(Piperidin-4-ylamino)-1,3,5-triazine-2-carbonitrile

To a solution of tert-butyl 4-((4-cyano-1,3,5-triazin-2-yl)amino)piperidine-1-carboxylate (200 mg, 689 μmol) in CH₂Cl₂ (3 mL) was added TFA (1.02 g, 8.07 mmol). The mixture was stirred at 25° C. for 1 hr. The reaction mixture was concentrated under reduced pressure. The crude 4-(piperidin-4-ylamino)-1,3,5-triazine-2-carbonitrile (Intermediate 175, 209 mg TFA salt, yield: 100%) was used into the next step without further purification.

Intermediate 176: Methyl 4-(2-(2-aminopyridin-3-yl)-3H-imidazo[4,5-b]pyridin-3-yl)benzoate

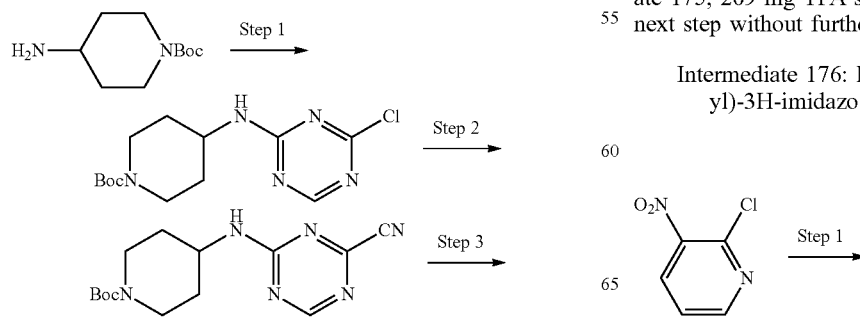

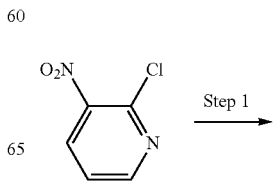

-continued

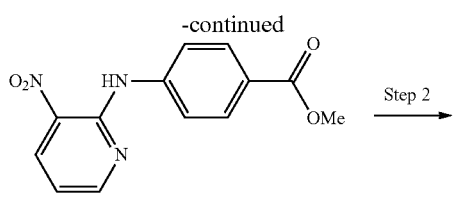

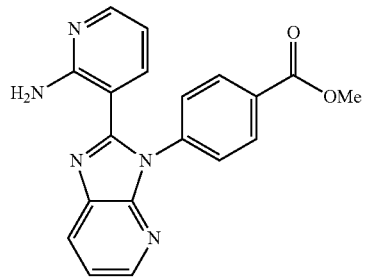

Intermediate 176

Step 1: Methyl 4-((3-nitropyridin-2-yl)amino)benzoate

To a solution of methyl 4-aminobenzoate (10 g, 66 mmol) were added DIEA (111 g, 861 mmol) and 2-chloro-3-nitropyridine (12.6 g, 79 mmol). The mixture was stirred at 130° C. for 16 hr. The mixture was diluted with H$_2$O (500 mL) and extracted with EtOAc (500 mL×2). The combined organic layers were washed with brine (1000 mL), dried over Na$_2$SO$_4$, filtered and concentrated under reduced pressure to give a residue. After purified by column chromatography (Eluent of 0~10% EtOAc in petroleum ether), methyl 4-((3-nitropyridin-2-yl)amino)benzoate (7.2 g, yield: 40%) was obtained as a yellow solid. MS: m/z=274.0 [M+H]$^+$. $^1$H NMR (400 MHz, Chloroform-d) δ 10.32 (br s, 1H), 8.58-8.53 (m, 2H), 8.05 (d, J=8.8 Hz, 2H), 7.81 (d, J=8.8 Hz, 2H), 6.93 (dd, J=8.0, 4.8 Hz, 1H), 3.91 (s, 3H).

Step 2: Methyl 4-(2-(2-aminopyridin-3-yl)-3H-imidazo[4,5-b]pyridin-3-yl)benzoate To a solution of methyl 4-((3-nitropyridin-2-yl)amino) benzoate (7 g, 26 mmol) in DMSO (300 mL) were added Na$_2$S$_2$O$_4$ (18 g, 102 mmol) and 2-aminonicotinaldehyde (3.8 g, 31 mmol). The mixture was stirred at 110° C. for 16 hr. The mixture was diluted with H$_2$O (1000 mL) and extracted with CH$_2$Cl$_2$ (1000 mL×2). The combined organic layers were washed with brine (1000 mL), dried over Na$_2$SO$_4$, filtered and concentrated under reduced pressure. After purified by column chromatography (Eluent of 0~43% EtOAc in petroleum ether), methyl 4-(2-(2-aminopyridin-3-yl)-3H-imidazo[4,5-b]pyridin-3-yl)benzoate (Intermediate 176, 4.1 g, yield: 45%) was obtained as a yellow solid. MS: m/z=346.1 [M+H]$^+$. $^1$H NMR (400 MHz, Chloroform-d) δ 8.43-8.36 (m, 1H), 8.21 (d, J=8.4 Hz, 2H), 8.14-8.06 (m, 2H), 7.49 (d, J=8.4 Hz, 2H), 7.33 (dd, J=8.0, 4.8 Hz, 1H), 7.04 (dd, J=7.6, 1.2 Hz, 1H), 6.59 (br s, 2H), 6.37 (dd, J=8.0, 4.8 Hz, 1H), 3.96 (s, 3H).

Intermediate 177: 3-(3-(4-(Chloromethyl-d$_2$)phenyl)-3H-imidazo[4,5-b]pyridin-2-yl)pyridin-2-amine

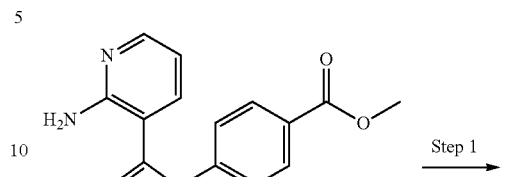

Intermediate 176

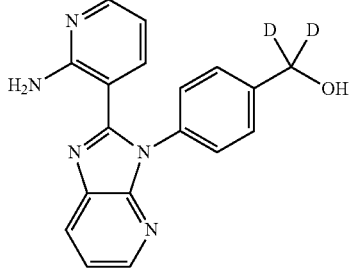

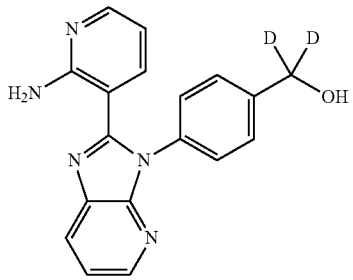

Intermediate 177

Step 1: (4-(2-(2-Aminopyridin-3-yl)-3H-imidazo[4,5-b]pyridin-3-yl)phenyl)methan-d-ol To a solution of Intermediate 176 (400 mg, 1.2 mmol) in THF (10 mL) was added LiAlD$_4$ (88 mg, 2.3 mmol) at 0° C. The resulting mixture was stirred at 25° C. for 1 hr. The reaction mixture was quenched by Na$_2$SO$_4$·10H$_2$O (2 g) at 0° C., filtered and concentrated under reduced pressure to give a (4-(2-(2-Aminopyridin-3-yl)-3H-imidazo[4,5-b]pyridin-3-yl)phenyl)methan-d$_2$-ol (370 mg) as a yellow solid, which was used for next step directly. MS: m/z=320.0 [M+H]$^+$.

Step 2: 3-(3-(4-(Chloromethyl-d$_2$)phenyl)-3H-imidazo[4,5-b]pyridin-2-yl)pyridin-2-amine To a solution of 4-(2-(2-aminopyridin-3-yl)-3H-imidazo [4,5-b]pyridin-3-yl)phenyl)methan-d$_2$-ol (370 mg, 1.2 mmol) in CH$_2$Cl$_2$ (5 mL) was added dropwise SOCl$_2$ (1.6 g, 14 mmol). The resulting mixture was stirred at 40° C. for 1 hr. The reaction mixture was quenched by Na$_2$CO$_3$ (5 mL) at 25° C., diluted with H$_2$O (10 mL) and extracted with EtOAc (10 mL×2). The combined organic layers were washed with brine (10 mL), dried over Na$_2$SO$_4$, filtered and concentrated under reduced pressure. After purified by flash chromatography on silica gel (Eluent of 0~50% EtOAc in petroleum ether), 3-(3-(4-(chloromethyl-d₂)phenyl)-3H-imidazo[4,5-b]pyridin-2-yl)pyridin-2-amine (Intermediate 177, 90 mg, yield: 23% for 2 steps) was obtained as a yellow solid. MS: m/z=337.9 [M+H]⁺.

Intermediate 178: 4-(2-(2-Aminopyridin-3-yl)-5-chloro-3H-imidazo[4,5-b]pyridin-3-yl)benzyl acetate

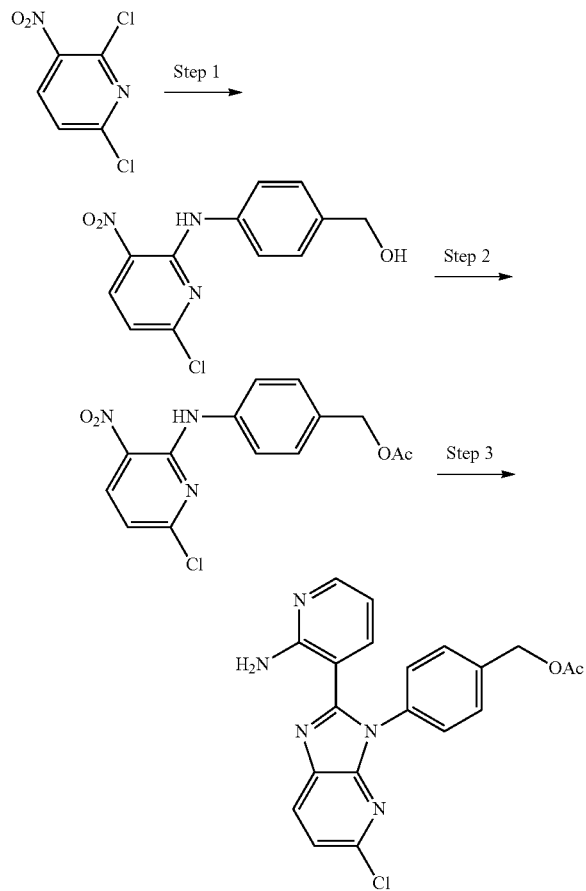

Intermediate 178

Step 1: (4-((6-Chloro-3-nitropyridin-2-yl)amino) phenyl)methanol

To a solution of 2,6-dichloro-3-nitropyridine (50 g, 259 mmol) and (4-aminophenyl)methanol (32 g, 259 mmol) in 1,4-dioxane (500 mL) was added DIEA (100 g, 777 mmol). The mixture was stirred at 70° C. for 1 hr. The reaction mixture was diluted with H₂O (500 mL) and extracted with CH₂Cl₂ (300 mL×2). The combined organic layers were washed with brine (200 mL), dried over Na₂SO₄, filtered and concentrated to give (4-((6-chloro-3-nitropyridin-2-yl) amino)phenyl)methanol (67 g, yield: 92%) as an orange solid, which was used in the next step without purification. ¹H NMR (400 MHz, Dimethylsulfoxide-d₆) δ 10.11 (br s, 1H), 8.53 (d, J=8.4 Hz, 1H), 7.53 (d, J=8.4 Hz, 2H), 7.33 (d, J=8.4 Hz, 2H), 6.98 (d, J=8.8 Hz, 1H), 5.20 (br s, 1H), 4.49 (s, 2H).

Step 2: 4-((6-Chloro-3-nitropyridin-2-yl)amino)benzyl acetate

To a solution of (4-((6-chloro-3-nitropyridin-2-yl)amino) phenyl)methanol (67 g, 239 mmol) in CH₂Cl₂ (600 mL) was added Et₃N (72.7 g, 718 mmol) and DMAP (2.93 g, 23.9 mmol) at 0° C. The mixture was stirred at 0° C. for 10 min, and then Ac₂O (24.5 g, 239 mmol) in CH₂Cl₂ (50 mL) was added dropwise at 0° C. The resulting mixture was stirred at 25° C. for 16 hr. The reaction mixture was diluted with H₂O (500 mL) and extracted with CH₂Cl₂ (500 mL×2). The combined organic layers were washed with brine (500 mL), dried over Na₂SO₄, filtered and concentrated under reduced pressure. After purified by silica gel flash chromatography (Eluent of 0~1% MeOH in CH₂Cl₂), 4-((6-chloro-3-nitropyridin-2-yl)amino)benzyl acetate (36 g, yield: 45%) was obtained as an orange solid. MS: m/z=321.8 [M+H]⁺. ¹H NMR (400 MHz, Dimethylsulfoxide-d₆) δ 10.14 (s, 1H), 8.55 (d, J=8.4 Hz, 1H), 7.61-7.58 (m, 2H), 7.39-7.37 (m, 1H), 7.08-6.97 (m, 2H), 5.07 (s, 2H), 2.07 (s, 3H).

Step 3: 4-(2-(2-Aminopyridin-3-yl)-5-chloro-3H-imidazo[4,5-b]pyridin-3-yl)benzyl acetate To a solution of 4-((6-chloro-3-nitropyridin-2-yl)amino) benzyl acetate (24 g, 74.6 mmol) and 2-aminonicotinaldehyde (10 g, 82 mmol) in DMSO (600 mL) was added Na₂S₂O₄ (52 g, 298 mmol). The mixture was stirred at 100° C. for 16 hr. The reaction mixture was diluted with H₂O (1500 mL) and extracted with CH₂Cl₂ (150 mL×3). The combined organic layers were washed with brine (500 mL), dried over Na₂SO₄, filtered and concentrated under reduced pressure to give a residue. After purified by column chromatography (Eluent of 0~50% EtOAc in petroleum ether), 4-(2-(2-aminopyridin-3-yl)-5-chloro-3H-imidazo[4,5-b] pyridin-3-yl)benzyl acetate (Intermediate 178, 5 g, yield: 14%) was obtained as a black brown solid. MS: m/z=394.0 [M+H]⁺. ¹H NMR (400 MHz, Chloroform-d) δ 8.10-7.99 (m, 2H), 7.52 (d, J=8.0 Hz, 2H), 7.41-7.32 (m, 3H), 7.08 (d, J=7.2 Hz, 1H), 6.80 (br s, 2H), 6.40 (dd, J=7.6, 5.2 Hz, 1H), 5.20 (s, 2H), 2.16 (s, 3H).

Intermediate 179: 4-((7-Azaspiro[3.5]nonan-2-yl) amino)pyrimidine-2-carbonitrile

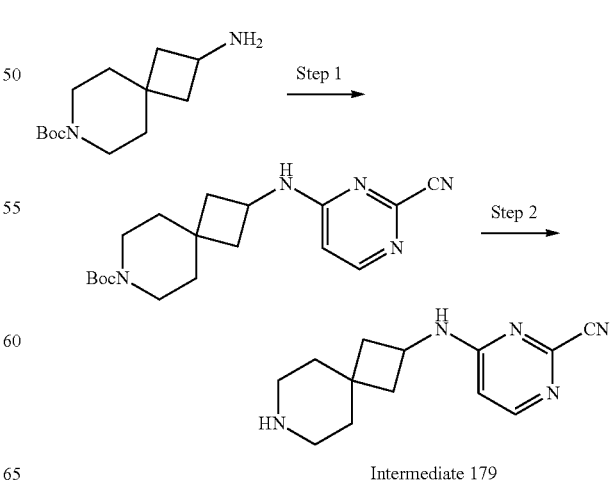

Intermediate 179

Step 1: Tert-butyl 2-((2-cyanopyrimidin-4-yl)amino)-7-azaspiro[3.5]nonane-7-carboxylate To a solution of tert-butyl 2-amino-7-azaspiro[3.5]nonane-7-carboxylate (500 mg, 2.08 mmol) and 4-chloropyrimidine-2-carbonitrile (290 mg, 2.08 mmol) in ACN (5 mL) were added $K_2CO_3$ (864 mg, 6.24 mmol) and NaI (62.4 mg, 416 µmol). The mixture was stirred at 80° C. for 2 hr. The reaction mixture was poured into $H_2O$ (20 mL), extracted with EtOAc (30 mL×3). The organic phase was dried over anhydrous $Na_2SO_4$, filtered, and concentrated under reduced pressure. After purified by silica gel flash chromatography (Eluent of 0%~50% EtOAc in petroleum ether), tert-butyl 2-((2-cyanopyrimidin-4-yl)amino)-7-azaspiro[3.5]nonane-7-carboxylate (505 mg, yield: 70%) was obtained as an off white solid. MS: m/z=344.0 $[M+H]^+$. $^1$H NMR (400 MHz, Dimethylsulfoxide-$d_6$) δ 8.47-8.22 (m, 1H), 8.09 (d, J=6.0 Hz, 1H), 6.65 (d, J=6.0 Hz, 1H), 4.60-4.12 (m, 1H), 3.98-3.86 (m, 2H), 3.83-3.72 (m, 2H), 2.61-2.54 (m, 2H), 2.14-2.04 (m, 2H), 1.39 (s, 9H).

Step 2: 4-((7-Azaspiro[3.5]nonan-2-yl)amino)pyrimidine-2-carbonitrile

To a solution of tert-butyl 2-((2-cyanopyrimidin-4-yl)amino)-7-azaspiro[3.5]nonane-7-carboxylate (240 mg, 699 µmol) in $CH_2Cl_2$ (3 mL) was added TFA (13.5 mmol, 1 mL). The mixture was stirred at 25° C. for 1 hr. The mixture was concentrated under reduced pressure to give 4-((7-azaspiro[3.5]nonan-2-yl)amino)pyrimidine-2-carbonitrile (Intermediate 179, 230 mg, TFA salt, crude) as a yellow oil. MS: m/z=244.0 $[M+H]^+$

Intermediate 180: 4-((2-Azaspiro[3.3]heptan-6-yl)amino)pyrimidine-2-carbonitrile

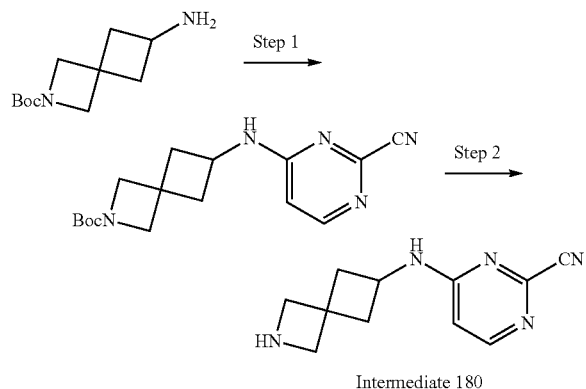

Intermediate 180

Step 1: Tert-butyl 6-((2-cyanopyrimidin-4-yl)amino)-2-azaspiro[3.3]heptane-2-carboxylate To a solution of tert-butyl 6-amino-2-azaspiro[3.3]heptane-2-carboxylate (1 g, 4.71 mmol) and 4-chloropyrimidine-2-carbonitrile (657 mg, 4.71 mmol) in ACN (10 mL) were added $K_2CO_3$ (1.95 g, 14.1 mmol) and NaI (141 mg, 942 µmol). The mixture was stirred at 80° C. for 1 hr. The reaction mixture was poured into $H_2O$ (20 mL), extracted with EtOAc (30 mL×3). The organic phase was dried over anhydrous $Na_2SO_4$, filtered and concentrated under reduced pressure. After purified by silica gel flash chromatography (Eluent of 0%~50% EtOAc in petroleum ether), tert-butyl 6-((2-cyanopyrimidin-4-yl)amino)-2-azaspiro[3.3]heptane-2-carboxylate (1.6 g, yield: 73%) was obtained as a yellow solid. MS: m/z=316.1 $[M+H]^+$. $^1$H NMR (400 MHz, Dimethylsulfoxide-$d_6$) δ 8.43-8.21 (m, 1H), 8.09 (d, J=5.6 Hz, 1H), 6.63 (d, J=5.6 Hz, 1H), 4.33-4.14 (m, 1H), 3.91 (s, 2H), 3.78 (s, 2H), 2.60-2.52 (m, 2H), 2.16-2.03 (m, 2H), 1.36 (s, 9H).

Step 2: 4-((2-Azaspiro[3.3]heptan-6-yl)amino)pyrimidine-2-carbonitrile

To a solution of tert-butyl 6-((2-cyanopyrimidin-4-yl)amino)-2-azaspiro[3.3]heptane-2-carboxylate (200 mg, 634 µmol) in $CH_2Cl_2$ (3 mL) was added TFA (13.5 mmol, 1 mL). The mixture was stirred at 25° C. for 1 hr. The mixture was concentrated under reduced pressure to give 4-((2-azaspiro[3.3]heptan-6-yl)amino)pyrimidine-2-carbonitrile (Intermediate 180, 195 mg, TFA salt, crude) as a yellow oil.

Intermediate 181: 4-(Azetidin-3-ylamino)pyrimidine-2-carbonitrile

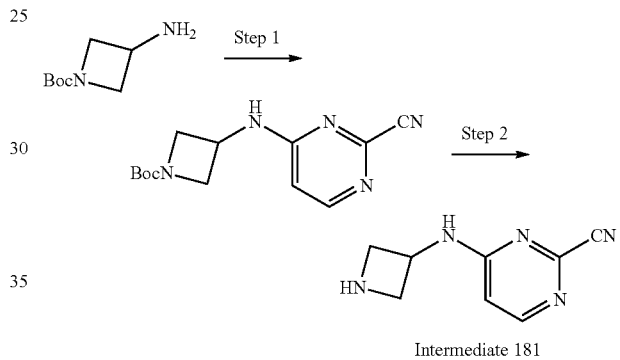

Intermediate 181

Step 1: Tert-butyl 3-((2-cyanopyrimidin-4-yl)amino)azetidine-1-carboxylate

To a solution of tert-butyl 3-aminoazetidine-1-carboxylate (1 g, 5.81 mmol) and 4-chloropyrimidine-2-carbonitrile (810 mg, 5.81 mmol) in ACN (10 mL) were added NaI (174 mg, 1.16 mmol) and $K_2CO_3$ (2.41 g, 17.4 mmol). The mixture was stirred at 80° C. for 2 hr. The reaction mixture was diluted with $H_2O$ (20 mL) and extracted with EtOAc (30 mL×3). The combined organic layers were washed with brine (30 mL), dried over $Na_2SO_4$, filtered and concentrated under reduced pressure. After purified by silica gel flash chromatography (Eluent of 0~50% EtOAc in petroleum ether), tert-butyl 3-((2-cyanopyrimidin-4-yl)amino)azetidine-1-carboxylate (1.4 g, yield: 86%) was obtained as a white solid. MS: m/z=276.0 $[M+H]^+$. $^1$H NMR (400 MHz, Dimethylsulfoxide-$d_6$)S 8.69 (d, J=6.4 Hz, 1H), 8.18 (d, J=5.2 Hz, 1H), 6.73 (d, J=6.0 Hz, 1H), 4.58 (s, 1H), 4.20-4.15 (m, 2H), 3.76-3.69 (m, 2H), 1.39 (s, 9H).

Step 2: 4-(Azetidin-3-ylamino)pyrimidine-2-carbonitrile

To a solution of tert-butyl 3-((2-cyanopyrimidin-4-yl)amino)azetidine-1-carboxylate (200 mg, 726 mol) in $CH_2Cl_2$ (5 mL) was added TFA (13.5 mmol, 1 mL). The mixture was stirred at 25° C. for 1 hr. The mixture was concentrated under reduced pressure to give 4-(azetidin-3-ylamino)pyrimidine-2-carbonitrile (Intermediate 181, 205 mg, TFA salt, crude) as a yellow oil.

Intermediate 182: 4-((2-azaspiro[3.5]nonan-7-yl)amino)pyrimidine-2-carbonitrile

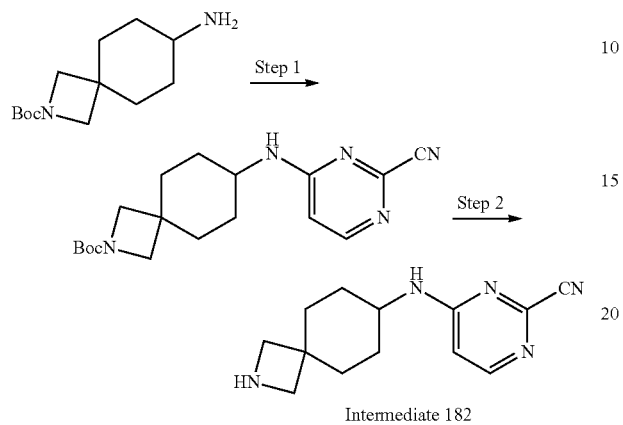

Intermediate 182

Step 1: Tert-butyl 7-((2-cyanopyrimidin-4-yl)amino)-2-azaspiro[3.5]nonane-2-carboxylate To a solution of tert-butyl 7-amino-2-azaspiro[3.5]nonane-2-carboxylate (1 g, 4.16 mmol) and 4-chloropyrimidine-2-carbonitrile (580 mg, 4.16 mmol) in ACN (10 mL) were added NaI (125 mg, 832 μmol) and K₂CO₃ (1.73 g, 12.5 mmol). The mixture was stirred at 80° C. for 2 hr. The reaction mixture was diluted with H₂O (20 mL) and extracted with EtOAc (30 mL×3). The combined organic layers were washed with brine (30 mL), dried over Na₂SO₄, filtered and concentrated under reduced pressure. After purified by silica gel flash chromatography (Eluent of 0~30% EtOAc in petroleum ether), tert-butyl 7-((2-cyanopyrimidin-4-yl)amino)-2-azaspiro[3.5]nonane-2-carboxylate (1.2 g, yield: 76%) was obtained as a white solid. MS: m/z=344.0 [M+H]⁺. ¹H NMR (400 MHz, Chloroform-d) δ 8.1 (s, 1H), 6.41 (d, J=6.0 Hz, 1H), 5.50-4.98 (m, 1H), 3.62 (d, J=8.4 Hz, 4H), 3.48 (s, 2H), 2.01-1.90 (m, 4H), 1.67-1.58 (m, 2H), 1.44 (s, 9H), 1.31-1.22 (m, 2H).

Step 2: 4-((2-Azaspiro[3.5]nonan-7-yl)amino)pyrimidine-2-carbonitrile

To a solution of tert-butyl 7-((2-cyanopyrimidin-4-yl)amino)-2-azaspiro[3.5]nonane-2-carboxylate (200 mg, 582 μmol) in CH₂Cl₂ (10 mL) was added TFA (13.5 mmol, 1 mL). The mixture was stirred at 25° C. for 0.5 hr. The mixture was stirred at 25° C. for 0.5 hr. The mixture was concentrated under reduced pressure to give 4-((2-azaspiro[3.5]nonan-7-yl)amino)pyrimidine-2-carbonitrile (Intermediate 182, 205 mg, TFA salt, crude) as a yellow oil.

Intermediate: 183: 4-(2,6-diazaspiro[3.3]heptan-2-yl)pyrimidine-2-carbonitrile

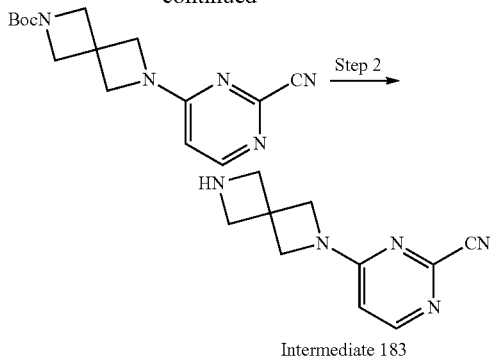

Intermediate 183

Step 1: Tert-butyl 6-(2-cyanopyrimidin-4-yl)-2,6-diazaspiro[3.3]heptane-2-carboxylate To a solution of tert-butyl 2,6-diazaspiro[3.3]heptane-2-carboxylate (180 mg, 908 μmol) and 4-chloropyrimidine-2-carbonitrile (127 mg, 908 μmol) in ACN (10 mL) were added NaI (27.2 mg, 182 μmol) and K₂CO₃ (376 mg, 2.76 mmol). The mixture was stirred at 80° C. for 2 hr. The reaction mixture was diluted with H₂O (20 mL) and extracted with EtOAc (30 mL×3). The combined organic layers were washed with brine (30 mL), dried over Na₂SO₄, filtered and concentrated under reduced pressure. After purified by silica gel flash chromatography (Eluent of 0~48% EtOAc in petroleum ether), tert-butyl 6-(2-cyanopyrimidin-4-yl)-2,6-diazaspiro[3.3]heptane-2-carboxylate (216 mg, yield: 78%) was obtained as an off white solid. MS: m/z=301.9 [M+H]⁺. ¹H NMR (400 MHz, Dimethylsulfoxide-d₆) δ 8.22 (d, J=6.0 Hz, 1H), 6.63 (d, J=6.0 Hz, 1H), 4.23 (s, 3H), 4.03 (s, 3H), 3.31 (s, 2H), 1.37 (s, 9H).

Step 2: 4-(2,6-Diazaspiro[3.3]heptan-2-yl)pyrimidine-2-carbonitrile

To a solution of tert-butyl 6-(2-cyanopyrimidin-4-yl)-2,6-diazaspiro[3.3]heptane-2-carboxylate (180 mg, 597 μmol) in CH₂Cl₂ (5 mL) was added TFA (13.5 mmol, 1 mL). The mixture was stirred at 25° C. for 1 hr. The mixture was concentrated under reduced pressure to give 4-(2,6-diazaspiro[3.3]heptan-2-yl)pyrimidine-2-carbonitrile (Intermediate 183, 201 mg, TFA salt, crude) as a light yellow oil.

Intermediate 184: 4-(3,8-Diazabicyclo[3.2.1]octan-3-yl)pyrimidine-2-carbonitrile

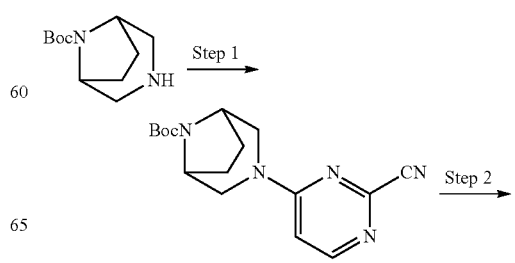

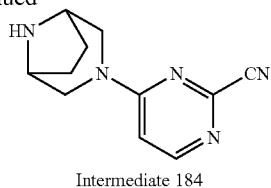

Intermediate 184

Step 1: Tert-butyl 3-(2-cyanopyrimidin-4-yl)-3,8-diazabicyclo[3.2.1]octane-8-carboxylate To a solution of tert-butyl 3,8-diazabicyclo[3.2.1]octane-8-carboxylate (500 mg, 2.36 mmol), 4-chloropyrimidine-2-carbonitrile (329 mg, 2.36 mmol) in ACN (5 mL) were added $K_2CO_3$ (977 mg, 7.07 mmol) and NaI (70.6 mg, 471 µmol). The mixture was stirred at 80° C. for 1 hr. The reaction mixture was poured into $H_2O$ (10 mL), extracted with EtOAc (15 mL×3). After purified by silica gel flash chromatography (Eluent of 0%~50% EtOAc in petroleum ether), tert-buty/3-(2-cyanopyrimidin-4-yl)-3,8-diazabicyclo[3.2.1]octane-8-carboxylate (505 mg, yield: 70%) was obtained as an off white solid. MS: m/z=316.0 [M+H]$^+$. $^1$H NMR (400 MHz, Dimethylsulfoxide-$d_6$) δ 8.30 (d, J=6.4 Hz, 1H), 7.06 (d, J=6.4 Hz, 1H), 4.40-4.15 (m, 3H), 3.98-3.70 (m, 1H), 3.18-2.90 (m, 2H), 1.90-1.75 (m, 2H), 1.61-1.54 (m, 2H), 1.43 (s, 9H).

Step 2: 4-(3,8-Diazabicyclo[3.2.1]octan-3-yl)pyrimidine-2-carbonitrile

To a solution of tert-butyl 3-(2-cyanopyrimidin-4-yl)-3,8-diazabicyclo[3.2.1]octane-8-carboxylate (200 mg, 634 µmol) in $CH_2Cl_2$ (2 mL) was added TFA (13.5 mmol, 1 mL). The mixture was stirred at 25° C. for 1 hr. The mixture was stirred at 25° C. for 1 hr. The mixture was concentrated under reduced pressure to give 4-(3,8-diazabicyclo[3.2.1]octan-3-yl)pyrimidine-2-carbonitrile (Intermediate 184, 210 mg, TFA salt, crude) as a yellow oil. MS: m/z=216.0 [M+H]$^+$.

Intermediate 185: 4-((3aR,6aS)-hexahydropyrrolo[3,4-c]pyrrol-2(1H)-yl)pyrimidine-2-carbonitrile

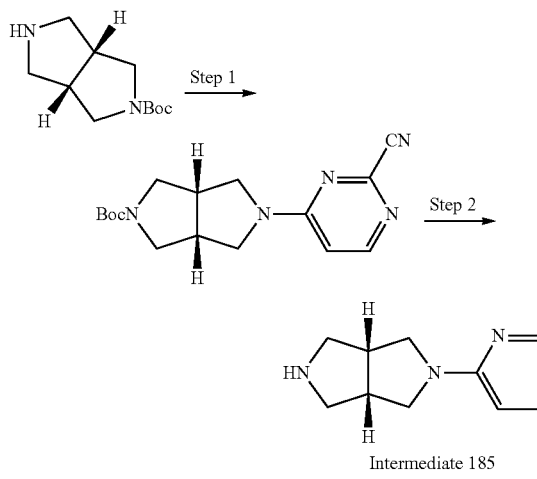

Intermediate 185

Step 1: Tert-butyl (3aR,6aS)-5-(2-cyanopyrimidin-4-yl)hexahydropyrrolo[3,4-c]pyrrole-2(1H)-carboxylate To a solution of tert-butyl (3aR,6aS)-hexahydropyrrolo[3,4-c]pyrrole-2(1H)-carboxylate (500 mg, 2.36 mmol), 4-chloropyrimidine-2-carbonitrile (329 mg, 2.36 mmol) in ACN (5 mL) were added $K_2CO_3$ (977 mg, 7.07 mmol) and NaI (70.6 mg, 471 µmol). The mixture was stirred at 80° C. for 2 hr. The reaction mixture was poured into $H_2O$ (10 mL), extracted with EtOAc (15 mL×3). After purified by silica gel flash chromatography (Eluent of 0%~50% EtOAc in petroleum ether), tert-butyl (3aR,6aS)-5-(2-cyanopyrimidin-4-yl)hexahydropyrrolo[3,4-c]pyrrole-2(1H)-carboxylate (610 mg, yield: 82%) was obtained as an off white solid. MS: m/z=316.1 [M+H]$^+$. $^1$H NMR (400 MHz, Dimethylsulfoxide-$d_6$) δ 8.24 (d, J=6.0 Hz, 1H), 6.74 (d, J=6.4 Hz, 1H), 3.80-3.68 (m, 1H), 3.66-3.58 (m, 1H), 3.56-3.48 (m, 2H), 3.42-3.35 (m, 2H), 3.17 (dd, J=11.2, 4.4 Hz, 2H), 3.08-2.90 (m, 2H), 1.39 (s, 9H).

Step 2: 4-((3aR,6aS)-Hexahydropyrrolo[3,4-c]pyrrol-2(1H)-yl)pyrimidine-2-carbonitrile To a solution of tert-butyl (3aR,6aS)-5-(2-cyanopyrimidin-4-yl)hexahydropyrrolo[3,4-c]pyrrole-2(1H)-carboxylate (200 mg, 634 µmol) in $CH_2Cl_2$ (3 mL) was added TFA (634 µmol, 47 µL). The mixture was stirred at 25° C. for 0.5 hr. The mixture was concentrated under reduced pressure to give 4-((3aR,6aS)-hexahydropyrrolo[3,4-c]pyrrol-2(1H)-yl)pyrimidine-2-carbonitrile (Intermediate 185, 210 mg, TFA salt, crude) as a yellow oil. MS: m/z=216.1 [M+H]$^+$.

Intermediate 186: 4-((Piperidin-4-yl-4-d)amino)pyrimidine-2-carbonitrile

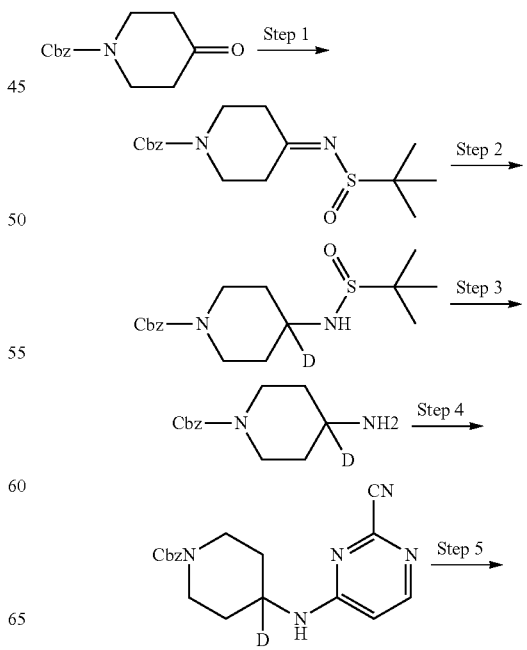

-continued

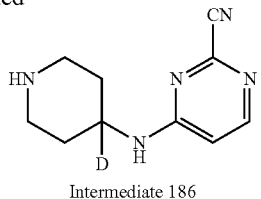

Intermediate 186

Step 1: Benzyl 4-((tert-butylsulfinyl)imino)piperidine-1-carboxylate

A mixture of benzyl 4-oxopiperidine-1-carboxylate (5 g, 21.4 mmol), 2-methylpropane-2-sulfinamide (2.86 g, 23.6 mmol), tetraethoxytitanium (8.31 g, 36.4 mmol) in THF (100 mL) was degassed and purged with $N_2$ three times, and then was stirred at 70° C. for 1 hr under $N_2$ atmosphere. The reaction mixture was concentrated under reduced pressure. After purified by silica gel flash chromatography (Eluent of 0~30% EtOAc in petroleum ether), benzyl 4-((tert-butylsulfinyl)imino)piperidine-1-carboxylate (4.3 g, yield: 60%) was obtained as a light-yellow oil. MS: m/z=337.0 $[M+H]^+$. $^1H$ NMR (400 MHz, Chloroform-d) δ 7.38-7.35 (m, 5H), 5.17 (s, 1H), 5.15 (s, 1H), 3.83-3.73 (m, 4H), 3.16-3.11 (m, 1H), 2.90-2.79 (m, 1H), 2.55-2.51 (m, 1H), 2.46-2.43 (m, 1H), 1.23 (s, 9H).

Step 2: Benzyl 4-((tert-butylsulfinyl)amino)piperidine-1-carboxylate-4-d

To a solution of benzyl 4-((tert-butylsulfinyl)imino)piperidine-1-carboxylate (3 g, 8.92 mmol) in THF (40 mL) was added $LiAlD_4$ (675 mg, 17.8 mmol) at 0° C. The mixture was stirred at 25° C. for 1 hr. The mixture was diluted with $H_2O$ (60 mL) and extracted with EtOAc (40 mL×3). The combined organic layers were washed with brine (30 mL×3), dried over $Na_2SO_4$, filtered, and concentrated under reduced pressure. After purified by silica gel flash chromatography (Eluent of 50~60% EtOAc in $CH_2Cl_2$), benzyl 4-((tert-butylsulfinyl)amino)piperidine-1-carboxylate-4-d (1.4 g, yield: 39%) was obtained as a colorless oil. MS: m/z=340.1 $[M+H]^+$. $^1H$ NMR (400 MHz, Chloroform-d) δ 7.41-7.30 (m, 5H), 5.13 (s, 2H), 4.14-4.06 (m, 2H), 3.05-2.90 (m, 2H), 2.01-1.93 (m, 2H), 1.52-1.40 (m, 2H), 1.21 (s, 9H).

Step 3: Benzyl 4-aminopiperidine-1-carboxylate-4-d

To a solution of benzyl 4-((tert-butylsulfinyl)amino)piperidine-1-carboxylate-4-d (1.31 g, 3.86 mmol) in 1,4-dioxane (10 mL) was added HCl/1,4-dioxane (4 M, 1.93 mL). The mixture was stirred at 25° C. for 1 hr. The reaction mixture was filtered and concentrated under reduced pressure to give benzyl 4-aminopiperidine-1-carboxylate-4-d (900 mg, yield: 99%) as a colorless oil. MS: m/z=236.1 $[M+H]^+$. $^1H$ NMR (400 MHz, Methanol-$d_4$) δ 7.41-7.28 (m, 5H), 5.12 (s, 2H), 4.25-4.21 (m, 2H), 3.37-3.33 (m, 2H), 2.02 (d, J=12.8 Hz, 2H), 1.56-1.45 (m, 2H).

Step 4: Benzyl 4-((2-cyanopyrimidin-4-yl)amino)piperidine-1-carboxylate-4-d

To a solution of benzyl 4-aminopiperidine-1-carboxylate-4-d (500 mg, 2.12 mmol), 4-chloropyrimidine-2-carbonitrile (297 mg, 2.12 mmol) in DMF (10 mL) were added NaI (63.7 mg, 425 μmol) and $K_2CO_3$ (881 mg, 6.37 mmol). The mixture was stirred at 50° C. for 1 hr. The mixture was diluted with $H_2O$ (10 mL) and extracted with $CH_2Cl_2$ (20 mL×3). The combined organic layers were washed with brine (20 mL×3), dried over $Na_2SO_4$, filtered and concentrated under reduced pressure. After purified by silica gel flash chromatography (Eluent of 40~50% EtOAc in petroleum ether), benzyl 4-((2-cyanopyrimidin-4-yl)amino)piperidine-1-carboxylate-4-d (330 mg, yield: 45%) was obtained as a colorless oil. MS: m/z=339.1 $[M+H]^+$. $^1H$ NMR (400 MHz, Chloroform-d) δ 8.26-8.12 (m, 1H), 7.39-7.34 (m, 5H), 6.44 (d, J=5.6 Hz, 1H), 5.15 (s, 2H), 4.30-4.08 (m, 2H), 3.11-2.95 (m, 2H), 2.09-2.00 (m, 2H), 1.66 (br s, 2H).

Step 5: 4-((Piperidin-4-yl-4-d)amino)pyrimidine-2-carbonitrile

To a solution of benzyl 4-((2-cyanopyrimidin-4-yl)amino)piperidine-1-carboxylate-4-d (300 mg, 887 μmol) in $CH_2Cl_2$ (10 mL) was added TMSI (887 mg, 4.43 mmol). The mixture was stirred at 25° C. for 1 hr. The mixture was filtered to give 4-((piperidin-4-yl-4-d)amino)pyrimidine-2-carbonitrile (Intermediate 186, 330 mg, yield: 45%) as a yellow solid. MS: m/z=205.0 $[M+H]^+$. $^1H$ NMR (400 MHz, Dimethylsulfoxide-$d_6$) δ 8.59-8.41 (m, 1H), 8.21-8.09 (m, 2H), 6.77-6.63 (m, 1H), 3.35-3.27 (m, 2H), 3.13-3.03 (m, 2H), 2.08-2.00 (m, 2H), 1.64-1.56 (m, 2H).

Intermediate 187: N-(3-(2-(2-Aminopyridin-3-yl)-3-(4-(chloromethyl)phenyl)-3H-imidazo[4,5-b]pyridin-5-yl)phenyl)acetamide

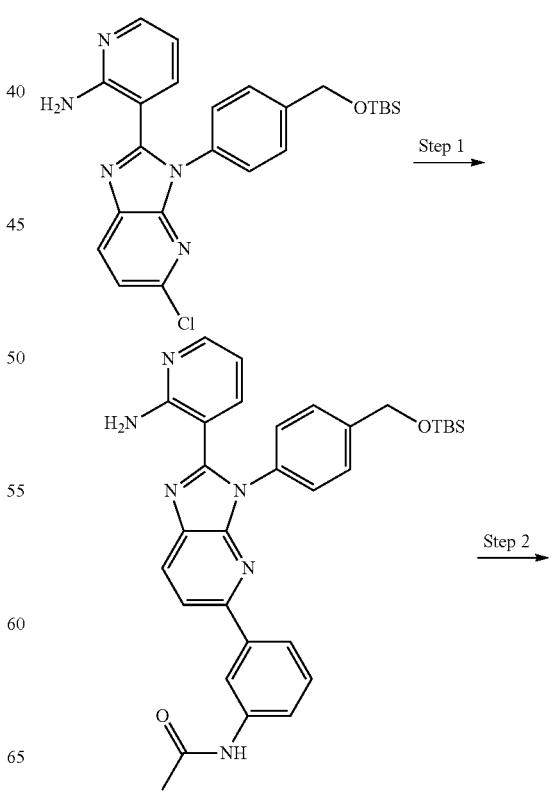

-continued

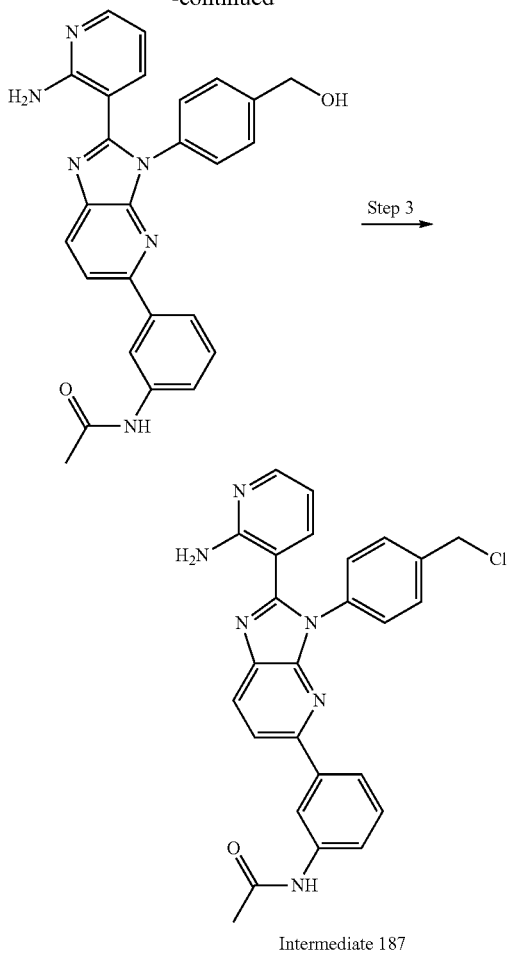

Intermediate 187

Step 1: N-(3-(2-(2-Aminopyridin-3-yl)-3-(4-(((tert-butyldimethylsilyl)oxy)methyl)phenyl)-3H-imidazo[4,5-b]pyridin-5-yl)phenyl)acetamide A mixture of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 500 mg, 1.07 mmol), (3-acetamidophenyl)boronic acid (288 mg, 1.61 mmol), Pd(dppf)Cl$_2$ (78.5 mg, 107 μmol), K$_2$CO$_3$ (444 mg, 3.22 mmol) in 1,4-dioxane (10 mL) and H$_2$O (2 mL) was degassed and purged with N$_2$ three times. The mixture was stirred at 100° C. for 16 hr under N$_2$ atmosphere. The reaction mixture was diluted with H$_2$O (50 mL) and extracted with CH$_2$Cl$_2$ (50 mL×3). The combined organic layers were washed with brine (50 mL), dried over Na$_2$SO$_4$, filtered and concentrated under reduced pressure. After purified by silica gel flash chromatography (eluent of 0-50% EtOAc in petroleum ether), N-(3-(2-(2-aminopyridin-3-yl)-3-(4-(((tert-butyldimethylsilyl)oxy)methyl)phenyl)-3H-imidazo[4,5-b]pyridin-5-yl)phenyl)acetamide (500 mg, yield: 81%) was obtained as a gray solid. MS: m/z=565.2 [M+H]. $^1$H NMR (400 MHz, Dimethylsulfoxide-d$_6$) δ 10.05 (s, 1H), 8.28 (d, J=8.4 Hz, 1H), 8.12 (s, 1H), 8.01 (dd, J=4.8, 1.6 Hz, 1H), 7.86 (d, J=8.4 Hz, 1H), 7.67 (t, J=8.8 Hz, 2H), 7.54-7.42 (m, 4H), 7.37 (t, J=8.0 Hz, 1H), 7.19 (dd, J=7.6, 1.6 Hz, 1H), 6.99 (br s, 2H), 6.39 (dd, J=7.6, 4.8 Hz, 1H), 4.82 (s, 2H), 2.05 (s, 3H), 0.93 (s, 9H), 0.11 (s, 6H).

Step 2: N-(3-(2-(2-Aminopyridin-3-yl)-3-(4-(hydroxymethyl)phenyl)-3H-imidazo[4,5-b]pyridin-5-yl)phenyl)acetamide A mixture of N-(3-(2-(2-aminopyridin-3-yl)-3-(4-(((tert-butyldimethylsilyl)oxy)methyl)phenyl)-3H-imidazo[4,5-b]pyridin-5-yl)phenyl)acetamide (500 mg, 885 μmol) in TBAF (1 M, 5 mL) was stirred at 25° C. for 1 hr. The reaction mixture was diluted with H$_2$O (50 mL) and extracted with EtOAc (50 mL×3). The combined organic layers were washed with brine (50 mL), dried over Na$_2$SO$_4$, filtered, and concentrated under reduced pressure. N-(3-(2-(2-aminopyridin-3-yl)-3-(4-(hydroxymethyl)phenyl)-3H-imidazo[4,5-b]pyridin-5-yl)phenyl)acetamide (400 mg, yield: 89%) was obtained as a gray solid. MS: m/z=451.3 [M+H]$^+$. $^1$H NMR (400 MHz, Dimethylsulfoxide-d$_6$) δ 10.17 (s, 1H), 8.38 (d, J=8.4 Hz, 2H), 8.19 (s, 1H), 8.14 (dd, J=6.0, 1.2 Hz, 2H), 7.96-7.90 (m, 3H), 7.70-7.60 (m, 5H), 7.40 (t, J=7.6 Hz, 2H), 6.91 (d, J=7.6, 6.4 Hz, 1H), 4.87 (s, 2H), 2.06 (s, 3H).

Step 3: N-(3-(2-(2-Aminopyridin-3-yl)-3-(4-(chloromethyl)phenyl)-3H-imidazo[4,5-b]pyridin-5-yl)phenyl)acetamide To a mixture of N-(3-(2-(2-aminopyridin-3-yl)-3-(4-(hydroxymethyl)phenyl)-3H-imidazo[4,5-b]pyridin-5-yl)phenyl)acetamide (200 mg, 443 μmol) in CH$_2$Cl$_2$ (4 mL) was added SOCl$_2$ (3.28 g, 27.5 mmol). The mixture was stirred at 40° C. for 1 hr. The reaction mixture was filtered, and the filter cake was concentrated under reduced pressure. N-(3-(2-(2-Aminopyridin-3-yl)-3-(4-(chloromethyl)phenyl)-3H-imidazo[4,5-b]pyridin-5-yl)phenyl)acetamide (Intermediate 187, 220 mg, yield: 86%) was obtained as a gray solid. MS: m/z=469.0 [M+H]$^+$.

Intermediate 188: 3-(3-(4-(Chloromethyl)phenyl)-5-vinyl-3H-imidazo[4,5-b]pyridin-2-yl)pyridin-2-amine

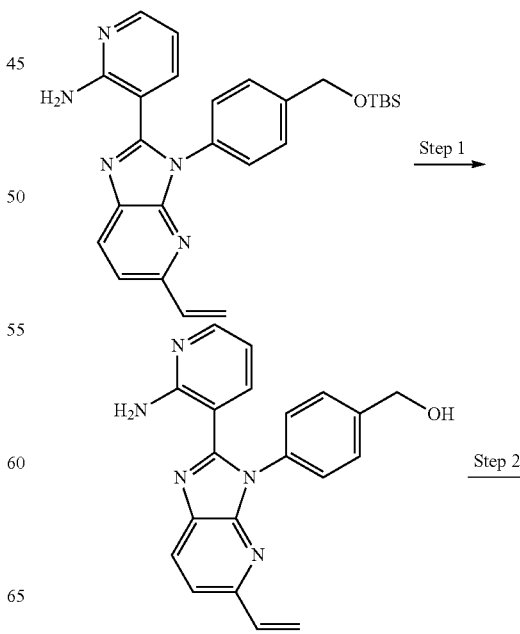

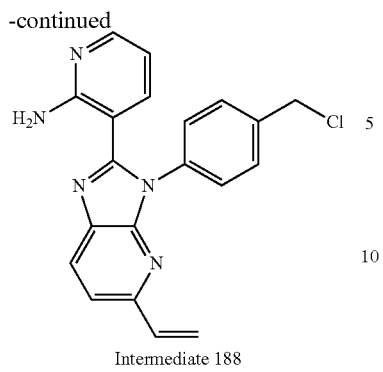

Intermediate 188

Step 1: (4-(2-(2-Aminopyridin-3-yl)-5-vinyl-3H-imidazo[4,5-b]pyridin-3-yl)phenyl)methanol To a solution of 3-(3-(4-(((tert-butyldimethylsilyl)oxy)methyl)phenyl)-5-vinyl-3H-imidazo[4,5-b]pyridin-2-yl)pyridin-2-amine (refer to Intermediate 124 for detail procedures, 320 mg, 699 μmol) in THF (4 mL) was added TBAF (1 M, 2.80 mL). The mixture was stirred at 25° C. for 0.5 hr. The reaction mixture was diluted with water (10 mL) and extracted with EtOAc (2-20 mL). The combined organic layers were dried over $Na_2SO_4$, filtered, and concentrated under reduced pressure. (4-(2-(2-Aminopyridin-3-yl)-5-vinyl-3H-imidazo[4,5-b]pyridin-3-yl)phenyl)methanol (240 mg, crude) was obtained as a brown oil. MS: m/z=344.1 [M+H]$^+$.

Step 2: 3-(3-(4-(Chloromethyl)phenyl)-5-vinyl-3H-imidazo[4,5-b]pyridin-2-yl)pyridin-2-amine To a solution of (4-(2-(2-aminopyridin-3-yl)-5-vinyl-3H-imidazo[4,5-b]pyridin-3-yl)phenyl)methanol (240 mg, 698 μmol) in $CH_2Cl_2$ (2 mL) was added $SOCl_2$ (332 mg, 2.80 mmol). The mixture was stirred at 40° C. for 0.5 hr. The mixture was concentrated under reduced pressure to give 3-(3-(4-(chloromethyl)phenyl)-5-vinyl-3H-imidazo[4,5-b]pyridin-2-yl)pyridin-2-amine (Intermediate 188, 240 mg, yield: 86%, HCl salt) as a yellow solid. MS: m/z=361.9 [M+H]$^+$.

Intermediate 189: 3-(3-(4-(Chloromethyl)phenyl)-5-(5-fluoropyridin-2-yl)-3H-imidazo[4,5-b]pyridin-2-yl)pyridin-2-amine

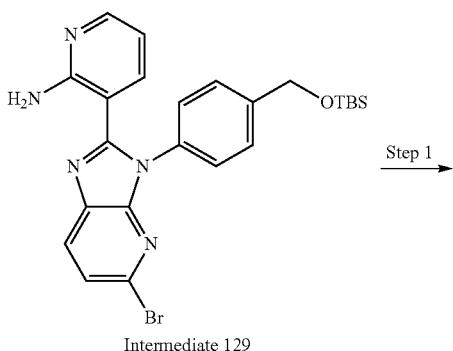

Intermediate 129

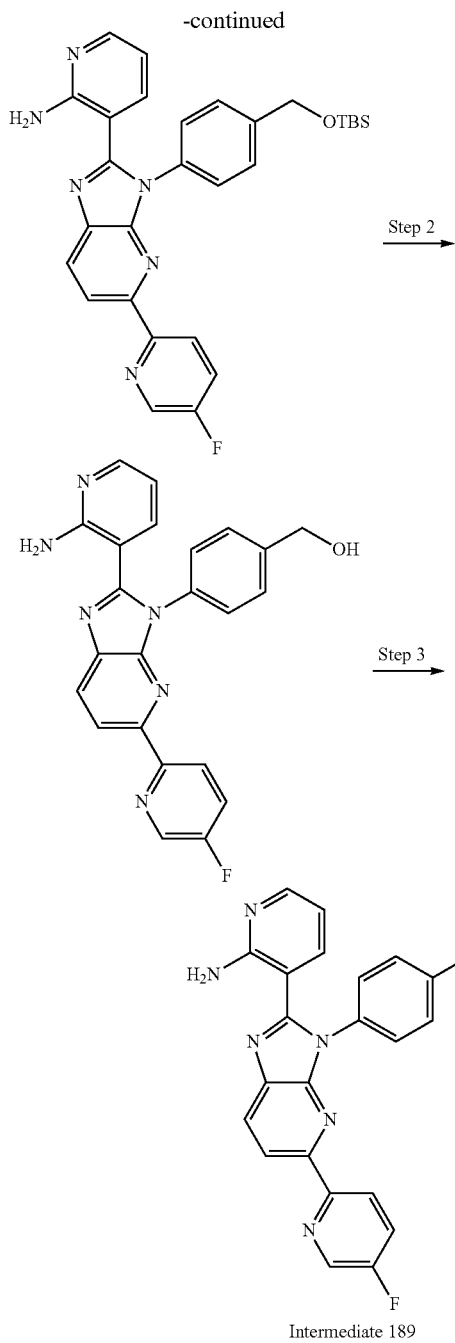

Intermediate 189

Step 1: 3-(3-(4-(((Tert-butyldimethylsilyl)oxy)methyl)phenyl)-5-(5-fluoropyridin-2-yl)-3H-imidazo[4,5-b]pyridin-2-yl)pyridin-2-amine To a solution of Intermediate 129 (500 mg, 979 μmol) in 1,4-dioxane (16.5 mL) were added CuBr (105 mg, 734 μmol), $Cs_2CO_3$ (105 mg, 957 μmol), (5-fluoropyridin-2-yl)boronic acid (690 mg, 957 mmol) and cataCXium A Pd G3 (71 mg, 98 μmol) at 25° C. The reaction mixture was degassed and purged with $N_2$ three times. The mixture was stirred at 100° C. for 4 hr under $N_2$. The reaction mixture was then poured into $H_2O$ (50 mL) and extracted with $CH_2Cl_2$ (20 mL×2). The combined organic layers were washed with brine (40 mL), dried over anhydrous $Na_2SO_4$, filtered and concentrated. After purified by silica gel flash chromatography (Eluent of 0~40% EtOAc in petroleum ether), 3-(3-(4-(((tert-butyldimethylsilyl)oxy)methyl)phenyl)-5-(5-fluoropyridin-2-yl)-3H-imidazo[4,5-b]pyridin-2-yl)pyridin-2-amine (450 mg, yield: 85%) was obtained as a brown solid. MS: m/z=527.2 [M+H]$^+$. $^1$H NMR (400 MHz, Dimethylsulfoxide-d$_6$) δ 8.67 (d, J=3.2 Hz, 1H), 8.40 (d, J=8.4 Hz, 1H), 8.32 (d, J=8.0 Hz, 1H), 8.25-8.17 (m, 1H), 8.04-7.98 (m, 1H), 7.87-7.78 (m, 1H), 7.55-7.45 (m, 4H), 7.25-7.16 (m, 1H), 7.11-6.88 (m, 2H), 6.43-6.35 (m, 1H), 4.83 (s, 2H), 0.95-0.92 (m, 9H), 0.13-0.11 (m, 6H).

Step 2: (4-(2-(2-Aminopyridin-3-yl)-5-(5-fluoropyridin-2-yl)-3H-imidazo[4,5-b]pyridin-3-yl)phenyl)methanol To a solution of 3-(3-(4-(((tert-butyldimethylsilyl)oxy)methyl)phenyl)-5-(5-fluoropyridin-2-yl)-3H-imidazo[4,5-b]pyridin-2-yl)pyridin-2-amine (450 mg, 854 μmol) in THF (5 mL) was added TBAF (670 mg, 2.5 ml, 1 M) at 25° C. The mixture was stirred at 25° C. for 1 hr. The reaction mixture was poured into H$_2$O (20 mL). The mixture was extracted with CH$_2$Cl$_2$ (20 mL×2). The combined organic layers were washed with brine (40 mL), dried over anhydrous Na$_2$SO$_4$, filtered and concentrated. (4-(2-(2-Aminopyridin-3-yl)-5-(5-fluoropyridin-2-yl)-3H-imidazo[4,5-b]pyridin-3-yl)phenyl)methanol (300 mg, crude) was obtained as a yellow solid. MS: m/z=413.1 [M+H]$^+$. $^1$H NMR (400 MHz, Dimethylsulfoxide-d$_6$) δ 8.66 (d, J=2.4 Hz, 1H), 8.40 (d, J=6.4 Hz, 1H), 8.31 (d, J=8.4 Hz, 1H), 8.22 (dd, J=8.8, 4.8 Hz, 1H), 8.01 (dd, J=4.8, 2.0 Hz, 1H), 7.87-7.80 (m, 1H), 7.53-7.44 (m, 4H), 7.23 (dd, J=7.6, 1.6 Hz, 1H), 6.98 (br s, 2H), 6.42 (dd, J=7.6, 4.8 Hz, 1H), 5.36 (br s, 1H), 4.61 (s, 2H).

Step 3: 3-(3-(4-(Chloromethyl)phenyl)-5-(5-fluoropyridin-2-yl)-3H-imidazo[4,5-b]pyridin-2-yl)pyridin-2-amine To a solution of (4-(2-(2-aminopyridin-3-yl)-5-(5-fluoropyridin-2-yl)-3H-imidazo[4,5-b]pyridin-3-yl)phenyl)methanol (300 mg, 727 μmol) in CH$_2$Cl$_2$ (5 mL) was added SOCl$_2$ (433 mg, 3.6 mmol) at 25° C. The mixture was stirred at 40° C. for 0.5 hr. The reaction mixture was concentrated under reduced pressure to give 3-(3-(4-(chloromethyl)phenyl)-5-(5-fluoropyridin-2-yl)-3H-imidazo[4,5-b]pyridin-2-yl)pyridin-2-amine (Intermediate 189, 300 mg, crude) as a yellow solid, which was used in the next step without further purification. MS: m/z=431.0 [M]$^+$. $^1$H NMR (400 MHz, Dimethylsulfoxide-d6) δ 8.67 (d, J=2.8 Hz, 1H), 8.41 (d, J=8.4 Hz, 1H), 8.30 (d, J=8.4 Hz, 1H), 8.24 (dd, J=8.8, 4.8 Hz, 1H), 8.01 (dd, J=4.8, 1.6 Hz, 1H), 7.87-7.82 (m, 1H), 7.63 (d, J=8.4 Hz, 2H), 7.53 (d, J=8.4 Hz, 2H), 7.25-7.21 (m, 1H), 6.90 (br s, 2H), 6.44 (dd, J=7.6, 4.8 Hz, 1H), 4.88 (s, 2H), 19F NMR (400 MHz, Dimethylsulfoxide-d6) δ −127.227

Intermediate 190: 2-(2-Aminopyridin-3-yl)-3-(4-(chloromethyl)phenyl)-N-methyl-3H-imidazo[4,5-h]pyridin-5-amine

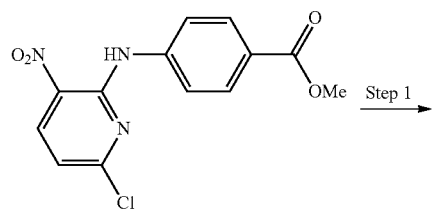

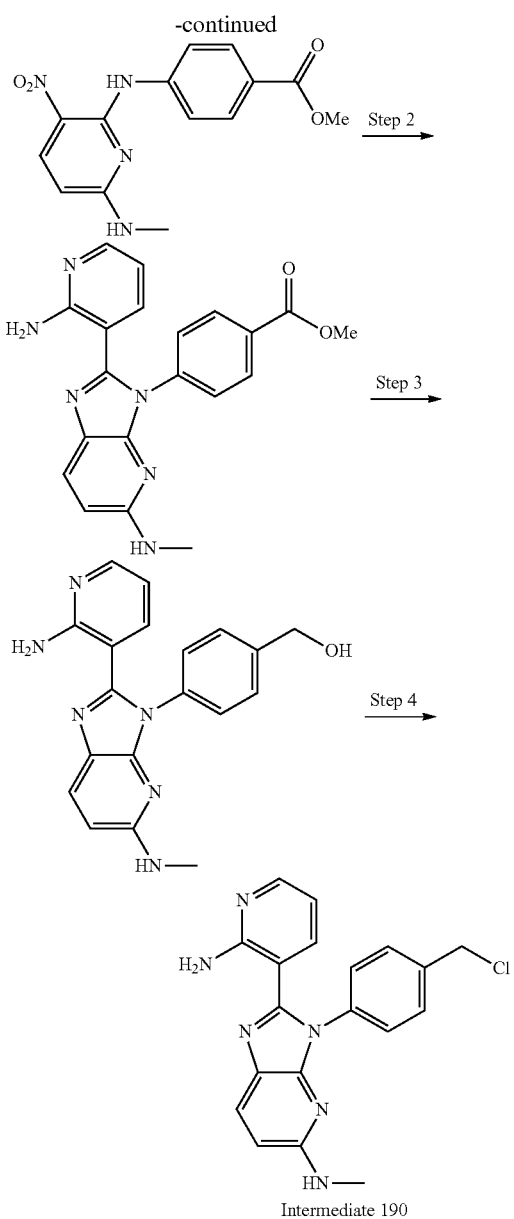

Intermediate 190

Step 1: Methyl 4-((6-(methylamino)-3-nitropyridin-2-yl)amino)benzoate

To a mixture of methyl 4-((6-chloro-3-nitropyridin-2-yl)amino)benzoate (refer to Intermediate 13 for detail procedures, 3 g, 9.75 mmol) in CH$_3$CN (50 mL) were added MeNH$_2$·HCl (790 mg, 11.7 mmol) and DIEA (3.78 g, 29.2 mmol). The mixture was stirred at 90° C. for 1 hr. The reaction mixture was filtered and concentrated under reduced pressure. The crude product was triturated with CH$_3$CN (50 mL) at 25° C. for 5 min to give methyl 4-((6-(methylamino)-3-nitropyridin-2-yl)amino)benzoate (2.6 g, yield: 82%) as a yellow solid. MS: m/z=303.0 [M+H]$^+$. $^1$H NMR (400 MHz, Dimethylsulfoxide-d$_6$) δ 11.06 (s, 1H), 8.39 (d, J=4.4 Hz, 1H), 8.11 (d, J=9.6 Hz, 1H), 8.00-7.93 (m, 4H), 6.18 (d, J=9.2 Hz, 1H), 3.83 (s, 3H), 2.94 (d, J=4.4 Hz, 3H).

Step 2: Methyl 4-(2-(2-aminopyridin-3-yl)-5-(methylamino)-3H-imidazo[4,5-b]pyridin-3-yl)benzoate To a mixture of methyl 4-((6-(methylamino)-3-nitropyridin-2-yl)amino)benzoate (2.6 g, 8.60 mmol) and 2-aminonicotinaldehyde (1.26 g, 10.3 mmol) in DMSO (40 mL) was added Na$_2$S$_2$O$_4$ (5.99 g, 34.4 mmol). The mixture was stirred at 100° C. for 24 hr. The reaction mixture was diluted with H$_2$O (100 mL) and extracted with EtOAc (100 mL×3). The combined organic layers were washed with H$_2$O (100 mL×3), dried over Na$_2$SO$_4$, filtered and concentrated under reduced pressure. After purified by silica gel flash chromatography (eluent of 0~50% Ethyl acetate in petroleum ether), methyl 4-(2-(2-aminopyridin-3-yl)-5-(methylamino)-3H-imidazo[4,5-b]pyridin-3-yl)benzoate (1.5 g, yield: 43%) was obtained as a yellow solid. MS: m/z=375.0 [M+H]$^+$. $^1$H NMR (400 MHz, Dimethylsulfoxide-d$_6$) δ 8.06 (d, J=8.4 Hz, 2H), 7.93 (d, J=3.6 Hz, 1H), 7.81 (d, J=8.8 Hz, 1H), 7.52 (d, J=8.4 Hz, 2H), 7.00 (d, J=7.2 Hz, 1H), 6.91 (br s, 2H), 6.75 (d, J=4.4 Hz, 1H), 6.50 (d, J=9.2 Hz, 1H), 6.36 (dd, J=7.2, 4.8 Hz, 1H), 3.88 (s, 3H), 2.72 (d, J=4.4 Hz, 3H).

Step 3: (4-(2-(2-Aminopyridin-3-yl)-5-((methyl-d$_3$)amino)-3H-imidazo[4,5-b]pyridin-3-yl)phenyl)methanol To a solution of methyl 4-(2-(2-aminopyridin-3-yl)-5-(methylamino)-3H-imidazo[4,5-b]pyridin-3-yl)benzoate (1.5 g, 4.01 mmol) in THF (100 mL) was added LiAlH$_4$ (2.5 M, 2.40 mL) at 0° C. The mixture was stirred at 25° C. for 1 hr. The reaction mixture was quenched with Na$_2$SO$_4$·10H$_2$O (2.5 g) at 0° C., filtered and concentrated under reduced pressure to give (4-(2-(2-aminopyridin-3-yl)-5-(methylamino)-3H-imidazo[4,5-b]pyridin-3-yl)phenyl)methanol (1.2 g, yield: 73%) as a yellow solid. MS: m/z=347.0 [M+H]$^+$. 1H NMR (400 MHz, Dimethylsulfoxide-d$_6$) δ 7.90 (dd, J=4.8, 1.6 Hz, 1H), 7.79 (d, J=8.8 Hz, 1H), 7.43 (d, J=8.4 Hz, 2H), 7.30 (d, J=8.4 Hz, 2H), 7.06-6.95 (m, 3H), 6.72-6.65 (m, 11H), 6.47 (d, J=8.8 Hz, 11H), 6.31 (dd, J=8.0, 4.8 Hz, 11H), 5.33 (t, J=6.0 Hz, 11H), 4.57 (d, J=6.0 Hz, 2H), 2.70 (d, J=4.8 Hz, 3H).

Step 4: 2-(2-Aminopyridin-3-yl)-3-(4-(chloromethyl)phenyl)-N-methyl-3H-imidazo[4,5-b]pyridin-5-amine To a solution of (4-(2-(2-aminopyridin-3-yl)-5-(methylamino)-3H-imidazo[4,5-b]pyridin-3-yl)phenyl)methanol (1.2 g, 3.46 mmol) in CH$_2$Cl$_2$ (8 mL) was added SOCl2 (4.91 g, 41.3 mmol). The mixture was stirred at 40° C. for 1 hr. The reaction mixture was filtered, and the filter cake was concentrated under reduced pressure. 2-(2-Aminopyridin-3-yl)-3-(4-(chloromethyl)phenyl)-N-methyl-3H-imidazo[4,5-b]pyridin-5-amine (Intermediate 190, 1.3 g, yield: 95%) was obtained as a yellow solid. MS: m/z=364.9 [M+H]$^+$.

Intermediate 191: 4-(2,7-Diazaspiro[3.5]nonan-2-yl)pyrimidine-2-carbonitrile

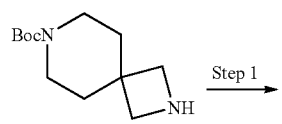

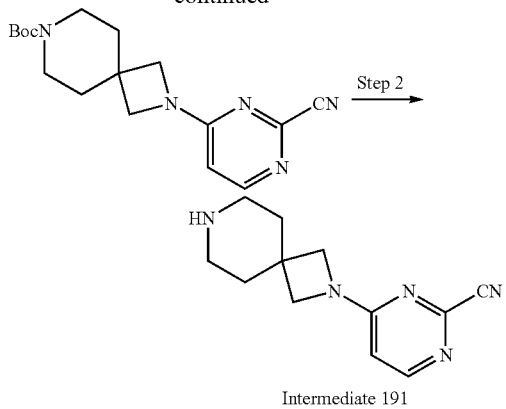

Intermediate 191

Step 1: Tert-butyl 2-(2-cyanopyrimidin-4-yl)-2,7-diazaspiro[3.5]nonane-7-carboxylate To a solution of tert-butyl 2,7-diazaspiro[3.5]nonane-7-carboxylate (180 mg, 908 μmol) and 4-chloropyrimidine-2-carbonitrile (127 mg, 908 μmol) in ACN (10 mL) were added NaI (132 mg, 884 μmol) and K$_2$CO$_3$ (1.83 g, 13.3 mmol). The mixture was stirred at 80° C. for 2 hr. The reaction mixture was diluted with H$_2$O (50 mL) and extracted with EtOAc (50 mL×3). The combined organic layers were washed with brine (50 mL), dried over Na$_2$SO$_4$, filtered, and concentrated under reduced pressure. After purified by silica gel flash chromatography (Eluent of 0~48% EtOAc in petroleum ether), tert-butyl 2-(2-cyanopyrimidin-4-yl)-2,7-diazaspiro[3.5]nonane-7-carboxylate (Intermediate, 1.3 g, yield: 89%) was obtained as a light yellow solid. MS: m/z=330.1 [M+H]$^+$. $^1$H NMR (400 MHz, Chloroform-d) δ 8.15 (d, J=6.0 Hz, 1H), 6.26 (d, J=6.0 Hz, 1H), 3.84 (s, 4H), 3.40 (s, 4H), 1.80-1.75 (m, 4H), 1.46 (s, 9H).

Step 2: 4-(2,7-Diazaspiro[3.5]nonan-2-yl)pyrimidine-2-carbonitrile

To a solution of tert-butyl 2-(2-cyanopyrimidin-4-yl)-2,7-diazaspiro[3.5]nonane-7-carboxylate (120 mg, 364 μmol) in CH$_2$Cl$_2$ (5 mL) was added TFA (13.5 mmol, 1 mL). The mixture was stirred at 25° C. for 1 hr. The mixture was concentrated under reduced pressure to give 4-(2,7-diazaspiro[3.5]nonan-2-yl)pyrimidine-2-carbonitrile (Intermediate 191, 120 mg, TFA salt, crude) as a yellow oil. MS: m/z=230.0 [M+H]$^+$.

Intermediate 192: 4-(2,7-Diazaspiro[3.5]nonan-7-yl)pyrimidine-2-carbonitrile

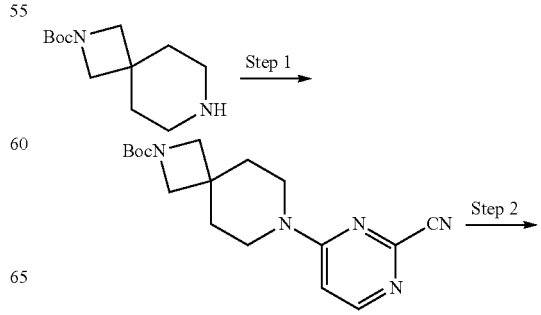

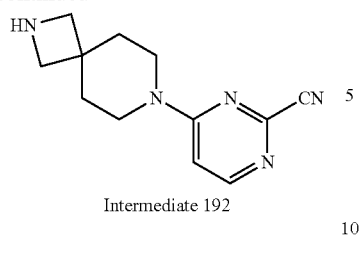

Intermediate 192

Step 1: Tert-butyl 7-(2-cyanopyrimidin-4-yl)-2,7-diazaspiro[3.5]nonane-2-carboxylate To a solution of tert-butyl 2,7-diazaspiro[3.5]nonane-2-carboxylate (500 mg, 2.21 mmol) and 4-chloropyrimidine-2-carbonitrile (308 mg, 2.21 mmol) in ACN (10 mL) were added NaI (33 mg, 221 μmol) and K$_2$CO$_3$ (916 mg, 6.63 mmol). The mixture was stirred at 80° C. for 16 hr. The reaction mixture was diluted with H$_2$O (50 mL) and extracted with EtOAc (50 mL×3). The combined organic layers were washed with brine (50 mL), dried over Na$_2$SO$_4$, filtered and concentrated under reduced pressure, tert-butyl 7-(2-cyanopyrimidin-4-yl)-2,7-diazaspiro[3.5]nonane-2-carboxylate (720 mg, yield: 97%) was obtained as a light yellow solid. MS: m/z=330.2 [M+H]$^+$. $^1$H NMR (400 MHz, Dimethylsulfoxide-d$_6$) δ 0.22 (d, J=6.0 Hz, 1H), 7.13 (d, J=6.8 Hz, 1H), 3.65-3.53 (m, 8H), 1.74-1.69 (m, 4H), 1.38 (s, 9H).

Step 2: 4-(2,7-Diazaspiro[3.5]nonan-7-yl)pyrimidine-2-carbonitrile

To a solution of tert-butyl 7-(2-cyanopyrimidin-4-yl)-2,7-diazaspiro[3.5]nonane-2-carboxylate (110 mg, 334 μmol) in CH$_2$Cl$_2$ (5 mL) was added TFA (13.5 mmol, 1 mL). The mixture was stirred at 25° C. for 1 hr. The mixture was concentrated under reduced pressure to give 4-(2,7-diazaspiro[3.5]nonan-7-yl)pyrimidine-2-carbonitrile (Intermediate 192, 110 mg, TFA salt, crude) as a yellow oil. MS: m/z=230.0 [M+H]$^+$.

Intermediate 193: 3-(5-Bromo-3-(4-(chloromethyl)phenyl)-3H-imidazo[4,5-b]pyridin-2-yl)pyridin-2-amine

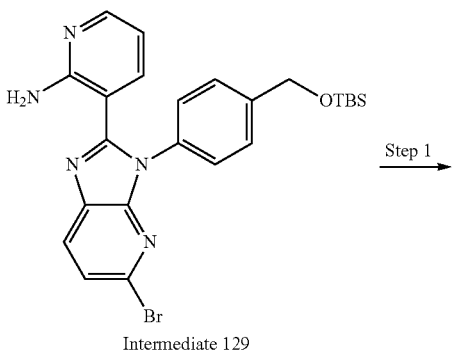

Intermediate 129

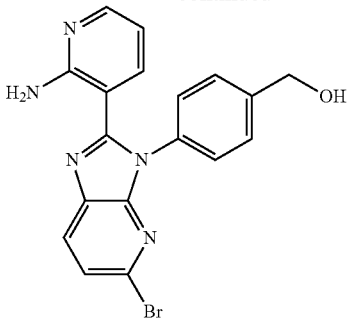

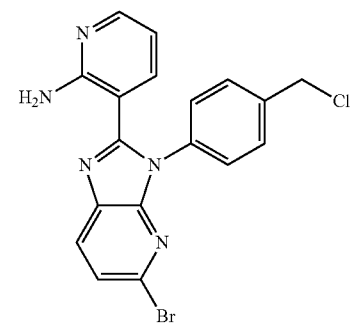

Intermediate 193

Step 1: (4-(2-(2-Aminopyridin-3-yl)-5-bromo-3H-imidazo[4,5-b]pyridin-3-yl)phenyl)methanol To a solution of Intermediate 129 (5 g, 9.79 mmol) in THF (50 mL) was added TBAF (1 M, 14.7 mL). The mixture was degassed and purged with N$_2$ three times and stirred at 25° C. for 2 hr under N$_2$. The reaction mixture was quenched with saturated NH$_4$C$_1$ (100 mL), then extracted with EtOAc (100 mL×2). The combined organic layers were washed with brine (200 mL×3), dried over Na$_2$SO$_4$, filtered and concentrated under reduced pressure, (4-(2-(2-aminopyridin-3-yl)-5-bromo-3H-imidazo[4,5-b]pyridin-3-yl)phenyl)methanol (3.88 g, crude) was obtained as a yellow solid which was used directly into the next step. MS: m/z=395.9, 397.9 [M+H]$^+$.

Step 2: 3-(5-Bromo-3-(4-(chloromethyl)phenyl)-3H-imidazo[4,5-b]pyridin-2-yl)pyridin-2-amine To a solution of (4-(2-(2-aminopyridin-3-yl)-5-bromo-3H-imidazo[4,5-b]pyridin-3-yl)phenyl)methanol (3.88 g, 9.79 mmol) in CH$_2$Cl$_2$ (50 mL) was added SOCl$_2$ (7.11 mL, 97.9 mmol). The mixture was degassed and purged with N$_2$ three times and stirred at 25° C. for 2 hr under N$_2$. The reaction mixture was concentrated under reduced pressure. 3-(5-Bromo-3-(4-(chloromethyl)phenyl)-3H-imidazo[4,5-b]pyridin-2-yl)pyridin-2-amine (Intermediate 193, 4.06 g, crude) was obtained as a gray solid which was used directly into the next step. MS: m/z=414.0, 416.0 [M+H]$^+$.

Intermediate 194: 3-(5-Bromo-3-(4-(chloromethyl-d₂)phenyl)-3H-imidazo[4,5-b]pyridin-2-yl)pyridin-2-amine

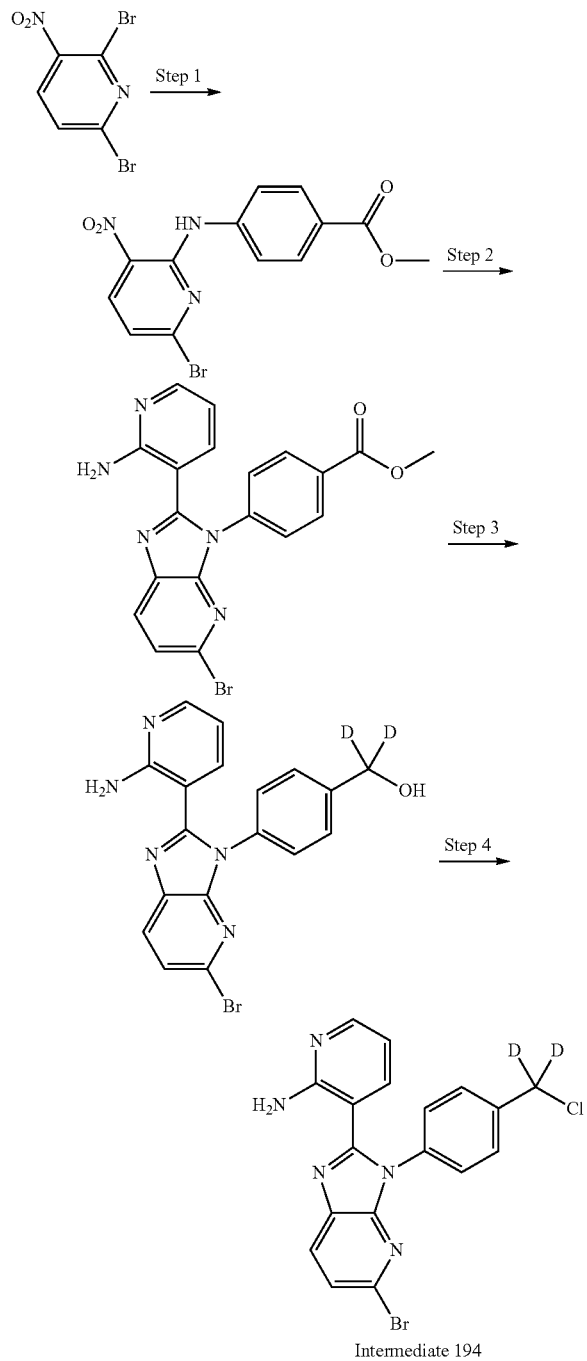

Intermediate 194

Step 1: Methyl 4-((6-bromo-3-nitropyridin-2-yl)amino)benzoate

To a solution of 2,6-dibromo-3-nitropyridine (10 g, 35.5 mmol) and methyl 4-aminobenzoate (5.36 g, 35.5 mmol) in 1,4-dioxane (100 mL) was added DIEA (18.5 mL, 106 mmol). The mixture was degassed and purged with N₂ three times and stirred at 40° C. for 16 hr under N₂. The reaction mixture was concentrated under reduced pressure. The crude product was triturated with EtOAc at 25° C. for 30 mins. Methyl 4-((6-bromo-3-nitropyridin-2-yl)amino)benzoate (9.2 g, yield: 67%) was obtained as a red solid. MS: m/z=351.7, 353.7 [M+H]⁺. ¹H NMR (400 MHz, Chloroform-d) δ 10.38 (s, 1H), 8.35 (d, J=8.8 Hz, 1H), 8.07 (d, J=8.8 Hz, 2H), 7.77 (d, J=8.8 Hz, 2H), 7.05 (d, J=8.8 Hz, 1H), 3.91 (s, 3H).

Step 2: 4-(2-(2-Aminopyridin-3-yl)-5-bromo-3H-imidazo[4,5-b]pyridin-3-yl)benzoate To a solution of methyl 4-((6-bromo-3-nitropyridin-2-yl)amino)benzoate (4.5 g, 12.8 mmol) and 2-aminonicotinaldehyde (1.72 g, 14.1 mmol) in DMSO (50 mL) was added Na₂S₂O₄ (4.45 g, 25.6 mmol). The mixture was degassed and purged with N₂ three times and stirred at 100° C. for 16 hr under N₂. The reaction mixture was quenched with H₂O (200 mL) and then extracted with CH₂Cl₂ (100 mL×3). The combined organic layers were washed with brine (200 mL×2), dried over Na₂SO₄, filtered and concentrated under reduced pressure. After purified by silica gel flash chromatography (EtOAc in petroleum ether=1 to 50%). 4-(2-(2-Aminopyridin-3-yl)-5-bromo-3H-imidazo[4,5-b]pyridin-3-yl)benzoate (2.2 g, yield: 36.5%) was obtained as a yellow solid. MS: m/z=423.8, 425.8 [M+H]⁺. ¹H NMR (400 MHz, Chloroform-d) δ 8.20 (d, J=8.4 Hz, 2H), 8.06 (dd, J=4.4, 1.2 Hz, 1H), 7.95 (d, J=8.4 Hz, 1H), 7.50-7.43 (m, 3H), 7.02 (dd, J=8.0, 1.6 Hz, 1H), 6.69 (br s, 2H), 6.37 (dd, J=7.6, 4.8 Hz, 1H), 3.97 (s, 3H).

Step 3: (4-(2-(2-Aminopyridin-3-yl)-5-bromo-3H-imidazo[4,5-b]pyridin-3-yl)phenyl)methan-d₂-ol To a solution of methyl 4-(2-(2-aminopyridin-3-yl)-5-bromo-3H-imidazo[4,5-b]pyridin-3-yl)benzoate (300 mg, 707 μmol) in THF (30 mL) was added LiAlD₄ (65.1 mg, 1.41 mmol). The mixture was degassed and purged with N₂ three times and stirred at 0° C. for 1 hr under N₂. The reaction mixture was quenched with Na₂SO₄·10H₂O (1 g) at 0° C., and then filtered and concentrated under reduced pressure. (4-(2-(2-Aminopyridin-3-yl)-5-bromo-3H-imidazo[4,5-b]pyridin-3-yl)phenyl)methan-d₂-ol (190 mg, crude) was obtained as a yellow solid which was used directly into the next step. MS: m/z=397.9, 399.9 [M+H]⁺.

Step 4: 3-(5-Bromo-3-(4-(chloromethyl-d₂)phenyl)-3H-imidazo[4,5-b]pyridin-2-yl)pyridin-2-amine To a solution of (4-(2-(2-aminopyridin-3-yl)-5-bromo-3H-imidazo[4,5-b]pyridin-3-yl)phenyl)methan-d₂-ol (190 mg, 477 μmol) in CH₂Cl₂ (2 mL) was added SOCl₂ (347 μL, 4.77 mmol). The mixture was degassed and purged with N₂ three times and stirred at 25° C. for 2 hr under N₂. The reaction mixture was concentrated under reduced pressure. 3-(5-Bromo-3-(4-(chloromethyl-d₂)phenyl)-3H-imidazo[4,5-b]pyridin-2-yl)pyridin-2-amine (Intermediate 194, 199 mg, crude) was obtained as a gray solid, which was used directly into the next step. MS: m/z=416.0, 418.0 [M+H]⁺.

Intermediate 195: 3-(3-(4-(Chloromethyl-d2)phenyl)-5-(4-fluorophenyl)-3H-imidazo[4,5-b]pyridin-2-yl)pyridin-2-amine

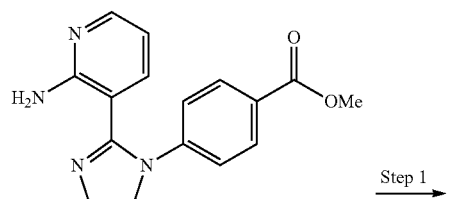

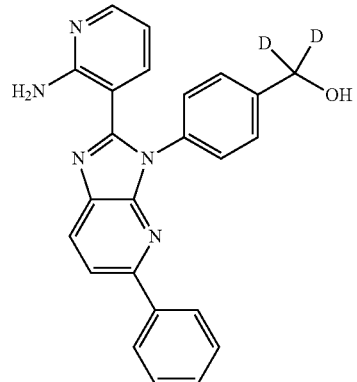

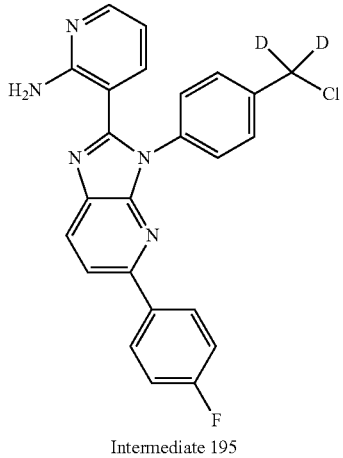

Intermediate 195

Step 1: (4-(2-(2-Aminopyridin-3-yl)-5-(4-fluorophenyl)-3H-imidazo[4,5-b]pyridin-3-yl)phenyl)methan-d2-ol To a solution of methyl 4-(2-(2-aminopyridin-3-yl)-5-(4-fluorophenyl)-3H-imidazo[4,5-b]pyridin-3-yl)benzoate (refer to Intermediate 107 for detail procedures, 900 mg, 2.0 mmol) in THF (3 mL) was added LiAlD$_4$ (155 mg, 4.1 mmol) at 0° C. The reaction mixture was stirred at 25° C. for 1 hr. The reaction mixture was quenched with Na$_2$SO$_4$10H$_2$O (203 mg) at 0° C. and filtered, concentrated under reduced pressure. The crude product (4-(2-(2-aminopyridin-3-yl)-5-(4-fluorophenyl)-3H-imidazo[4,5-b]pyridin-3-yl)phenyl)methan-d2-ol (830 mg) was used into the next step without further purification. MS: m/z=414.1 [M+H]$^+$. $^{19}$F NMR (400 MHz, Dimethylsulfoxide-d$_6$) δ −113.60

Step 2: 3-(3-(4-(Chloromethyl-d2)phenyl)-5-(4-fluorophenyl)-3H-imidazo[4,5-b]pyridin-2-yl)pyridin-2-amine To a solution of (4-(2-(2-aminopyridin-3-yl)-5-(4-fluorophenyl)-3H-imidazo[4,5-b]pyridin-3-yl)phenyl)methan-d2-ol (500 mg, 1.2 mmol) in CH$_2$Cl$_2$ (10 mL) was added SOCl$_2$ (719 mg, 6.0 mmol) at 25° C. The reaction mixture was stirred at 40° C. for 0.5 hr. The reaction mixture was concentrated under reduced pressure. The crude product 3-(3-(4-(chloromethyl-d2)phenyl)-5-(4-fluorophenyl)-3H-imidazo[4,5-b]pyridin-2-yl)pyridin-2-amine (Intermediate 195, 500 mg, yield: 74%) was used into the next step without further purification. MS: m z=432.0 [M+H]$^+$. $^{19}$F NMR (400 MHz, Dimethylsulfoxide-d$_6$) δ −113.05.

Intermediate 196: 3-(3-(4-(Chloromethyl)phenyl)-5,7-dimethyl-3H-imidazo[4,5-b]pyridin-2-yl)pyridin-2-amine

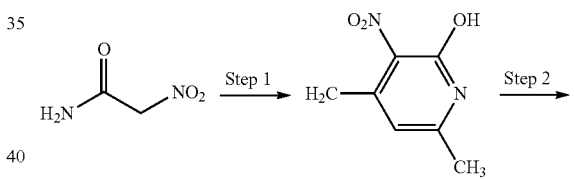

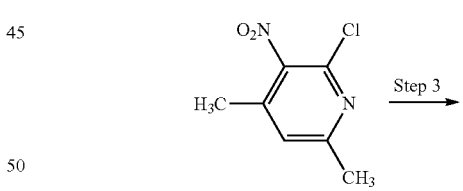

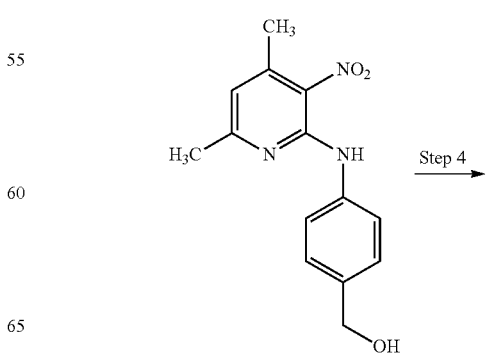

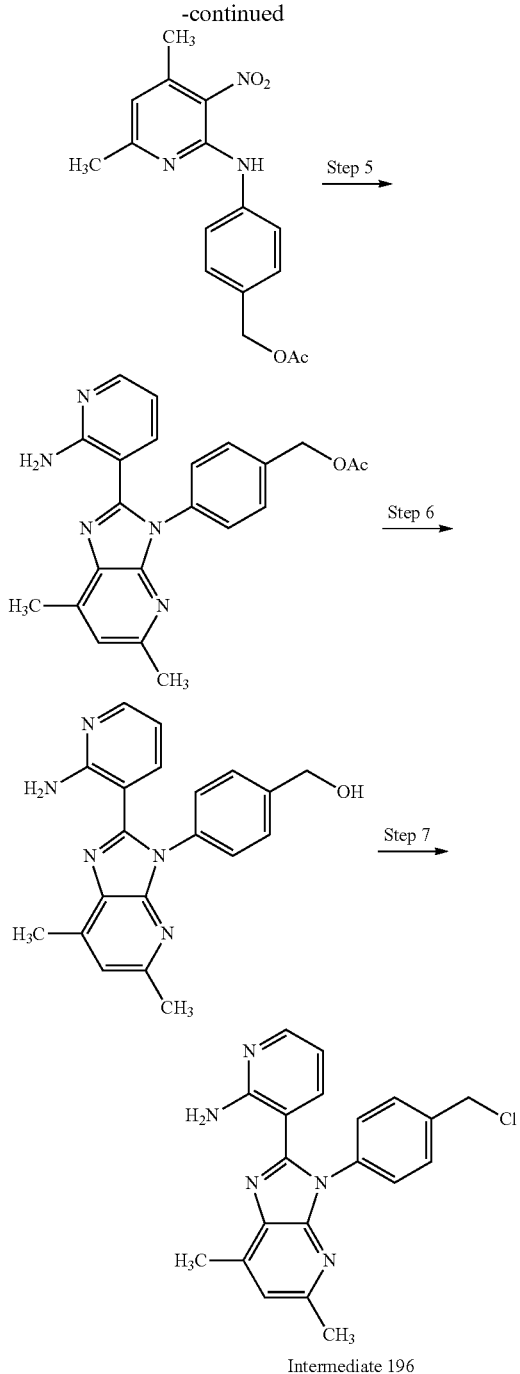

Intermediate 196

Step 1: 4,6-Dimethyl-3-nitropyridin-2-ol

To a solution of 2-nitroacetamide (12.3 g, 118 mmol) in H₂O (120 mL) were added pentane-2,4-dione (14.4 g, 143 mmol), Py (3.09 g, 39.1 mmol), AcOH (2.35 g, 39.2 mmol). The mixture was stirred at 25° C. for 7 days. The mixture was filtered and the filter cake was concentrated under reduced pressure to give 4,6-dimethyl-3-nitropyridin-2-ol (4.5 g, yield: 20%) as a light-yellow solid. $^1$H NMR (400 MHz, Dimethylsulfoxide-d$_6$) δ 12.14 (s, 1H), 6.08 (s, 1H), 2.20 (s, 3H), 2.14 (s, 3H).

Step 2: 2-Chloro-4,6-dimethyl-3-nitropyridine

To a solution of 4,6-dimethyl-3-nitropyridin-2-ol (4 g, 23.8 mmol) in POCl₃ (65.8 g, 429 mmol) was stirred at 100° C. for 2 hr under N₂ atmosphere. The reaction mixture was quenched with H₂O (300 mL) at 25° C., and then extracted with EtOAc (500 mL×2). The combined organic layers were washed with brine (300 mL×2), dried over Na₂SO₄, filtered, and concentrated under reduced pressure. After purified by silica gel flash chromatography (Eluent of 0%~6% EtOAc in petroleum ether), 2-chloro-4,6-dimethyl-3-nitropyridine (3.8 g, yield: 85%) was obtained as a light-yellow solid. MS: m/z=186.9 [M+H]⁺. $^1$H NMR (400 MHz, Dimethylsulfoxide-d$_6$) δ 7.49 (s, 1H), 2.50 (s, 3H), 2.32 (s, 3H).

Step 3: (4-((4,6-Dimethyl-3-nitropyridin-2-yl)amino)phenyl)methanol

To a solution of 2-chloro-4,6-dimethyl-3-nitropyridine (2.4 g, 12.8 mmol) and (4-aminophenyl)methanol (1.74 g, 14.1 mmol) in 1,4-dioxane (30 mL) and was added DIEA (4.99 g, 38.6 mmol). The mixture was stirred at 110° C. for 48 hr. The reaction mixture was diluted H₂O (300 mL) and extracted with EtOAc (500 mL×2). The combined organic layers were washed with brine (300 mL×2), dried over Na₂SO₄, filtered and concentrated under reduced pressure to give (4-((4,6-dimethyl-3-nitropyridin-2-yl)amino)phenyl)methanol (3.3 g, yield: 78%) was obtained as a red solid. MS: m/z=274.0 [M+H]⁺.

Step 4: 4-((4,6-Dimethyl-3-nitropyridin-2-yl)amino)benzyl acetate

To a mixture of (4-((4,6-dimethyl-3-nitropyridin-2-yl)amino)phenyl)methanol (3 g, 10.9 mmol), DMAP (134 mg, 1.10 mmol) and TEA (3.33 g, 32.9 mmol) in CH₂Cl₂ (50 mL) was added acetic anhydride (1.12 g, 10.9 mmol), then degassed and purged with N₂ three times and stirred at 0° C. for 2 hr under N₂ atmosphere. The reaction mixture was diluted with H₂O (200 mL) and extracted with EtOAc (200 mL×3). The combined organic layers were washed with brine (200 mL), dried over Na₂SO₄, filtered and concentrated under reduced pressure. After purified by silica gel flash chromatography (Eluent of 0~50% EtOAc in petroleum ether), 4-((4,6-dimethyl-3-nitropyridin-2-yl)amino) benzyl acetate (970 mg, yield: 28%) was obtained as a yellow solid. MS: m/z=316.0 [M+H]⁺. $^1$H NMR (400 MHz, Chloroform-d) δ 9.59 (s, 1H), 7.64 (d, J=8.4 Hz, 2H), 7.35 (d, J=8.4 Hz, 2H), 6.56 (s, 1H), 5.09 (s, 2H), 2.55 (s, 3H), 2.44 (s, 3H), 2.10 (s, 3H).

Step 5: 4-(2-(2-Aminopyridin-3-yl)-5,7-dimethyl-3H-imidazo[4,5-b]pyridin-3-yl)benzyl acetate A mixture of 4-((4,6-dimethyl-3-nitropyridin-2-yl)amino) benzyl acetate (970 mg, 3.08 mmol), 2-aminonicotinaldehyde (413 mg, 3.38 mmol) and Na₂S₂O₄ (2.14 g, 12.3 mmol) in DMSO (100 mL) was degassed and purged with N₂ three times, and then was stirred at 100° C. for 16 hr under N₂ atmosphere. The reaction mixture was diluted with H₂O (100 mL) and extracted with EtOAc (100 mL×3). The combined organic layers were washed with brine (200 mL), dried over Na₂SO₄, filtered and concentrated under reduced pressure. After purified by silica gel flash chromatography (Eluent of 0~50% EtOAc in petroleum ether), 4-(2-(2-aminopyridin-3-yl)-5,7-dimethyl-3H-imidazo[4,5-b]pyridin-3-yl)benzyl acetate (550 mg, yield: 44%) was obtained as a yellow solid. MS: m/z=388.1 [M+H]+. ¹H NMR (400 MHz, Dimethylsulfoxide-$d_6$) δ 7.97 (dd, J=4.8, 2.0 Hz, 1H), 7.51 (d, J=8.4 Hz, 2H), 7.40 (d, J=8.4 Hz, 2H), 7.17 (dd, J=7.6, 1.6 Hz, 1H), 7.10 (s, 1H), 6.93 (s, 2H), 6.40 (dd, J=7.6, 4.8 Hz, 1H), 5.16 (s, 2H), 2.62 (s, 3H), 2.47 (s, 3H), 2.11 (s, 3H).

Step 6: (4-(2-(2-Aminopyridin-3-yl)-5,7-dimethyl-3H-imidazo[4,5-b]pyridin-3-yl)phenyl)methanol To a mixture of 4-(2-(2-aminopyridin-3-yl)-5,7-dimethyl-3H-imidazo[4,5-b]pyridin-3-yl)benzyl acetate (500 mg, 1.29 mmol) in MeOH (15 mL), THF (15 mL) and H₂O (7 mL) was added K₂CO₃ (178 mg, 1.29 mmol). The mixture was stirred at 25° C. for 0.5 hr. The mixture was filtered, concentrated under reduced pressure, (4-(2-(2-aminopyridin-3-yl)-5,7-dimethyl-3H-imidazo[4,5-b]pyridin-3-yl)phenyl)methanol (400 mg, yield: 80%) was obtained as a yellow solid. MS: m/z=346.1 [M+H]+.

Step 7: 3-(3-(4-(Chloromethyl)phenyl)-5,7-dimethyl-3H-imidazo[4,5-b]pyridin-2-yl)pyridin-2-amine To a solution of (4-(2-(2-aminopyridin-3-yl)-5,7-dimethyl-3H-imidazo[4,5-b]pyridin-3-yl)phenyl)methanol (400 mg, 1.16 mmol) in CH₂Cl₂ (15 mL) was added SOCl₂ (827 mg, 6.95 mmol). The mixture was stirred at 40° C. for 1 hr. The mixture was concentrated to give 3-(3-(4-(chloromethyl)phenyl)-5,7-dimethyl-3H-imidazo[4,5-b]pyridin-2-yl)pyridin-2-amine (Intermediate 196, 350 mg, yield: 88%) as a yellow solid, which was used in the next step without further purification. MS: m/z=364.0 [M+H]+.

Intermediate 197: 3-(3-(4-(chloromethyl)phenyl)-5-(pyridin-2-yl)-3H-imidazo[4,5-b]pyridin-2-yl)pyridin-2-amine

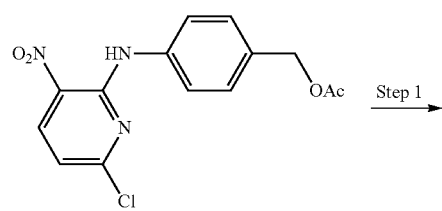

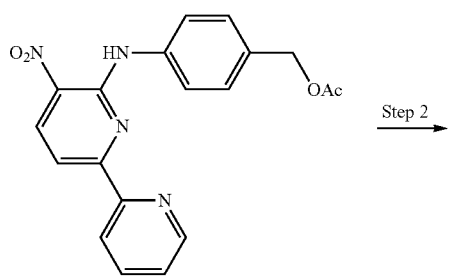

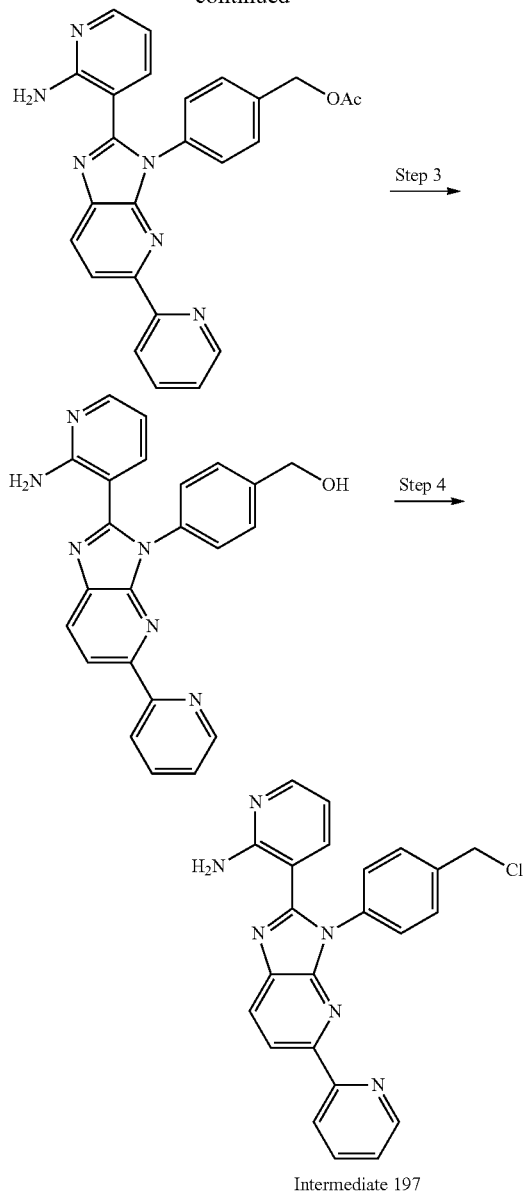

Intermediate 197

Step 1: 4-((5-Nitro-[2,2'-bipyridin]-6-yl)amino)benzyl acetate

To a solution of 4-((6-chloro-3-nitropyridin-2-yl)amino) benzyl acetate (refer to Intermediate 178 for detail procedures, 500 mg, 1.6 mmol) in 1,4-dioxane (10 mL) were added CuBr (167 mg, 1.2 mmol), Cs₂CO₃ (1.5 g, 4.7 μmol), pyridin-2-ylboronic acid (573 mg, 4.7 mmol) and cataCXium A PdG3 (113 mg, 155 μmol) at 25° C., the reaction mixture was degassed and purged with N₂ three times. The mixture was stirred at 100° C. for 4 hr under N₂. The reaction mixture was poured into H₂O (50 mL), then extracted with CH₂Cl₂ (20 mL×2). The combined organic layers were washed with brine (40 mL), dried over anhydrous Na₂SO₄, filtered and concentrated. After purified by silica gel flash chromatography (Eluent of 0~45% EtOAc in petroleum ether), 4-((5-nitro-[2,2'-bipyridin]-6-yl)amino) benzyl acetate (300 mg, yield: 43%) was obtained as a yellow solid. MS: m/z=365.0 [M+H]⁺. ¹H NMR (400 MHz, Dimethylsulfoxide-d₆) δ 10.11 (s, 1H), 8.76 (d, J=4.0 Hz, 1H), 8.70 (d, J=8.8 Hz, 1H), 8.20 (d, J=8.0 Hz, 1H), 8.05-7.95 (m, 2H), 7.81-7.75 (m, 2H), 7.56 (dd, J=7.2, 4.8 Hz, 1H), 7.45 (d, J=8.4 Hz, 2H), 5.10 (s, 2H), 2.09 (s, 3H).

Step 2: 4-(2-(2-Aminopyridin-3-yl)-5-(pyridin-2-yl)-3H-imidazo[4,5-b]pyridin-3-yl)benzyl acetate To a solution of 4-((5-nitro-[2,2'-bipyridin]-6-yl)amino)benzyl acetate (300 mg, 823 μmol) in DMSO (10 mL) were added 2-aminonicotinaldehyde (121 mg, 988 μmol) and Na₂S₂O₄ (573 mg, 3.3 mmol) at 25° C. The mixture was stirred at 100° C. for 12 hr. The reaction mixture was poured into H₂O (100 mL). The mixture was extracted with CH₂Cl₂ (50 mL×2). The combined organic layers were washed with 400 mL brine, dried over anhydrous Na₂SO₄, filtered and concentrated. After purified by silica gel flash chromatography (Eluent of 0~3% MeOH in CH₂Cl₂), 4-(2-(2-aminopyridin-3-yl)-5-(pyridin-2-yl)-3H-imidazo[4,5-b]pyridin-3-yl)benzyl acetate (200 mg, yield: 56%) was obtained as a yellow solid. MS: m/z=437.0 [M+H]⁺. ¹H NMR (400 MHz, Dimethylsulfoxide-d₆) δ 8.67 (d, J=4.0 Hz, 1H), 8.47 (d, J=8.4 Hz, 1H), 8.32 (d, J=8.4 Hz, 1H), 8.19 (d, J=8.0 Hz, 1H), 8.02 (dd, J=4.8, 2.0 Hz, 1H), 7.94-7.87 (m, 1H), 7.59-7.51 (m, 4H), 7.40 (dd, J=7.2, 5.6 Hz, 1H), 7.25 (dd, J=7.6, 2.0 Hz, 1H), 6.90 (s, 2H), 6.44 (dd, J=7.6, 4.8 Hz, 1H), 5.19 (s, 2H), 2.12 (s, 3H).

Step 3: (4-(2-(2-Aminopyridin-3-yl)-5-(pyridin-2-yl)-3H-imidazo[4,5-b]pyridin-3-yl)phenyl)methanol To a solution of 4-(2-(2-aminopyridin-3-yl)-5-(pyridin-2-yl)-3H-imidazo[4,5-b]pyridin-3-yl)benzyl acetate (200 mg, 458 μmol) in H₂O (1 mL) and MeOH (2 mL) THF (2 mL) was added K₂CO₃ (63 mg, 458 μmol) at 25° C. The mixture was stirred at 25° C. for 1 hr. The reaction mixture was poured into H₂O (20 mL). The mixture was extracted with CH₂Cl₂ (20 mL×2). The combined organic layers were washed with brine (40 mL), dried over anhydrous Na₂SO₄, filtered and concentrated, (4-(2-(2-aminopyridin-3-yl)-5-(5-fluoropyridin-2-yl)-3H-imidazo[4,5-b]pyridin-3-yl)phenyl)methanol (300 mg, crude) was obtained as a yellow solid. MS: m/z=395.3 [M+H]⁺. ¹H NMR (400 MHz, Dimethylsulfoxide-d₆) δ 8.64-8.58 (m, 1H), 8.44 (d, J=8.4 Hz, 1H), 8.30-8.20 (m, 2H), 7.99 (dd, J=4.8, 1.6 Hz, 1H), 7.87-7.80 (m, 1H), 7.57 (d, J=8.4 Hz, 2H), 7.47 (d, J=8.4 Hz, 2H), 7.40-7.32 (m, 2H), 6.48 (dd, J=7.6, 5.2 Hz, 1H), 4.72 (s, 2H).

Step 4: 3-(3-(4-(Chloromethyl)phenyl)-5-(pyridin-2-yl)-3H-imidazo[4,5-b]pyridin-2-yl)pyridin-2-amine To a solution of (4-(2-(2-aminopyridin-3-yl)-5-(5-fluoropyridin-2-yl)-3H-imidazo[4,5-b]pyridin-3-yl)phenyl)methanol (180 mg, 456 μmol) in CH₂Cl₂ (5 mL) was added SOCl₂ (271 mg, 2.3 mmol) at 25° C. The mixture was stirred at 40° C. for 0.5 hr. The reaction mixture was concentrated under reduced pressure to give 3-(3-(4-(chloromethyl)phenyl)-5-(pyridin-2-yl)-3H-imidazo[4,5-b]pyridin-2-yl)pyridin-2-amine (Intermediate 197, 188 mg, crude) as a yellow solid, which was used in the next step without further purification. MS: m/z=413.0 [M+H]⁺.

Intermediate 198: 3-(3-(4-(Chloromethyl)phenyl)-5-(pyrrolidin-1-yl)-3H-imidazo[4,5-b]pyridin-2-yl)pyridin-2-amine

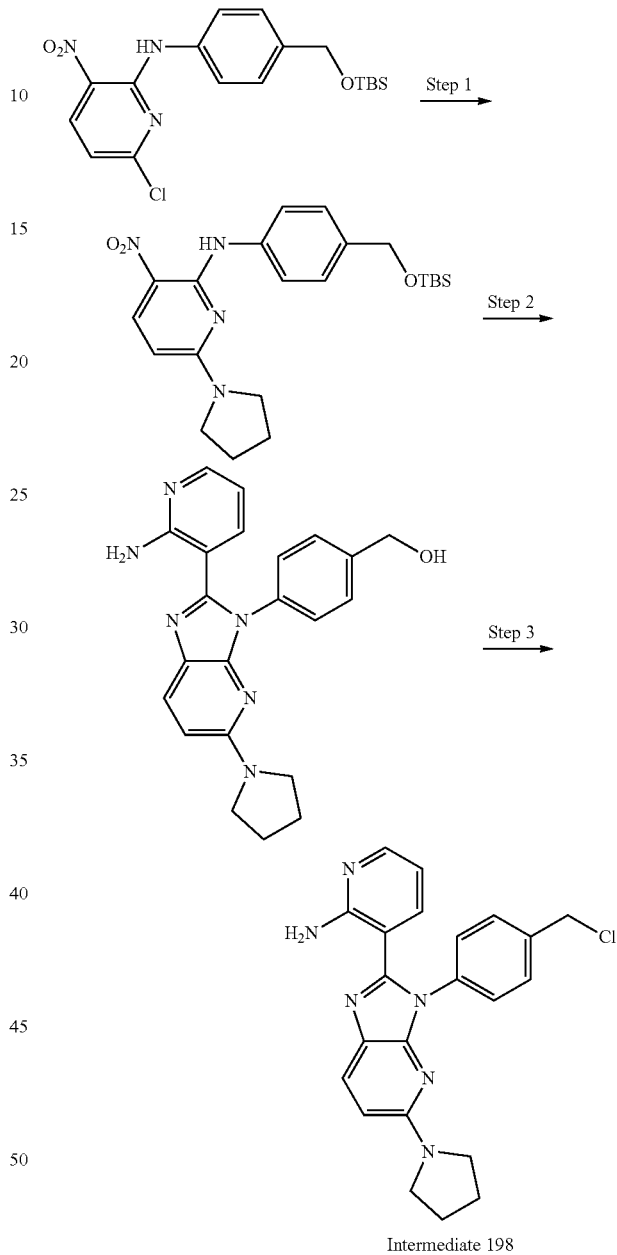

Intermediate 198

Step 1: N-(4-(((Tert-butyldimethylsilyl)oxy)methyl)phenyl)-3-nitro-6-(pyrrolidin-1-yl)pyridin-2-amine To a solution of N-(4-(((tert-butyldimethylsilyl)oxy)methyl)phenyl)-6-chloro-3-nitropyridin-2-amine (refer to Intermediate 105 for detail procedures, 3 g, 7.62 mmol) in MeCN (50 mL) were added DIEA (2.95 g, 22.9 mmol) and pyrrolidine (1.23 g, 11.4 mmol, HCl). The mixture was stirred at 90° C. for 12 hr. The reaction mixture was concentrated. The residue was dissolved in EtOAc (50 mL), washed with brine (50 mL×2), dried over anhydrous Na₂SO₄, filtered and concentrated. N-(4-(((Tert-butyldimethylsilyl)oxy)methyl)phenyl)-3-nitro-6-(pyrrolidin-1-yl)pyridin-2-amine (3 g, yield: 92%) was obtained as a brown solid, which was used directly into the next step. MS: m/z=429.1 [M+H]⁺.

Step 2: (4-(2-(2-Aminopyridin-3-yl)-5-(pyrrolidin-1-yl)-3H-imidazo[4,5-b]pyridin-3-yl)phenyl)methanol To a solution of N-(4-(((tert-butyldimethylsilyl)oxy)methyl)phenyl)-3-nitro-6-(pyrrolidin-1-yl)pyridin-2-amine (1.5 g, 3.50 mmol) in DMSO (30 mL) were added Na₂S₂O₄ (1.83 g, 10.5 mmol) and 2-aminonicotinaldehyde (470 mg, 3.85 mmol). The mixture was stirred at 100° C. for 12 hr. Saturated NaHCO₃ (50 mL) was added to the mixture and the mixture was extracted with CH₂Cl₂ (50 mL×2). The combined organic layers were washed with brine (50 mL), dried over anhydrous Na₂SO₄, filtered and concentrated. After purified by prep-HPLC (column: Xtimate C18 150×40 mm×10 μm; mobile phase: [water (NH₃H₂O+NH₄HCO₃)-ACN]; gradient: 35%-65% B over 8 min), (4-(2-(2-aminopyridin-3-yl)-5-(pyrrolidin-1-yl)-3H-imidazo[4,5-b]pyridin-3-yl)phenyl)methanol (200 mg, yield: 15%) was obtained as a yellow solid. MS: m/z=387.2 [M+H]⁺. ¹H NMR (400 MHz, Dimethylsulfoxide-d₆) δ 7.96-7.86 (m, 2H), 7.43 (d, J=8.0 Hz, 2H), 7.35-7.28 (m, 2H), 7.11-6.98 (m, 3H), 6.49 (d, J=8.8 Hz, 1H), 6.33 (dd, J=7.6, 4.8 Hz, 1H), 5.38-5.30 (m, 1H), 4.57 (d, J=5.6 Hz, 2H), 2.59-2.52 (m, 2H), 2.49-2.47 (m, 2H), 1.96-1.87 (m, 4H).

Step 3: 3-(3-(4-(Chloromethyl)phenyl)-5-(pyrrolidin-1-yl)-3H-imidazo[4,5-b]pyridin-2-yl)pyridin-2-amine To a solution of (4-(2-(2-aminopyridin-3-yl)-5-(pyrrolidin-1-yl)-3H-imidazo[4,5-b]pyridin-3-yl)phenyl)methanol (100 mg, 259 gmol) in CH2Cl₂ (3 mL) was added SOCl2 (92.4 mg, 776 μmol) at 20° C. The mixture was stirred at 20° C. for 2 hr. The reaction mixture was concentrated. 3-(3-(4-(Chloromethyl)phenyl)-5-(pyrrolidin-1-yl)-3H-imidazo[4, 5-b]pyridin-2-yl)pyridin-2-amine (Intermediate 198, 105 mg, yield: 100%) was obtained as a yellow solid, which was used directly into the next step. MS: m/z=405.1 [M+H]⁺.

Intermediate 199: 3-(3-(4-(Chloromethyl)phenyl)-5-(2-methoxypyridin-4-yl)-3H-imidazo[4,5-b]pyridin-2-yl)pyridin-2-amine

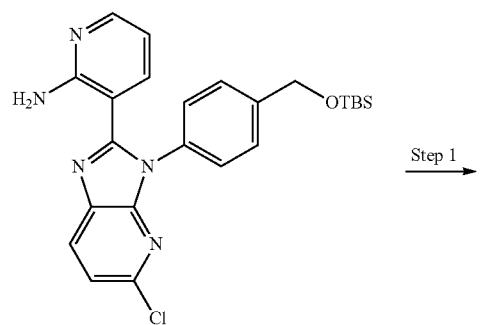

Step 1

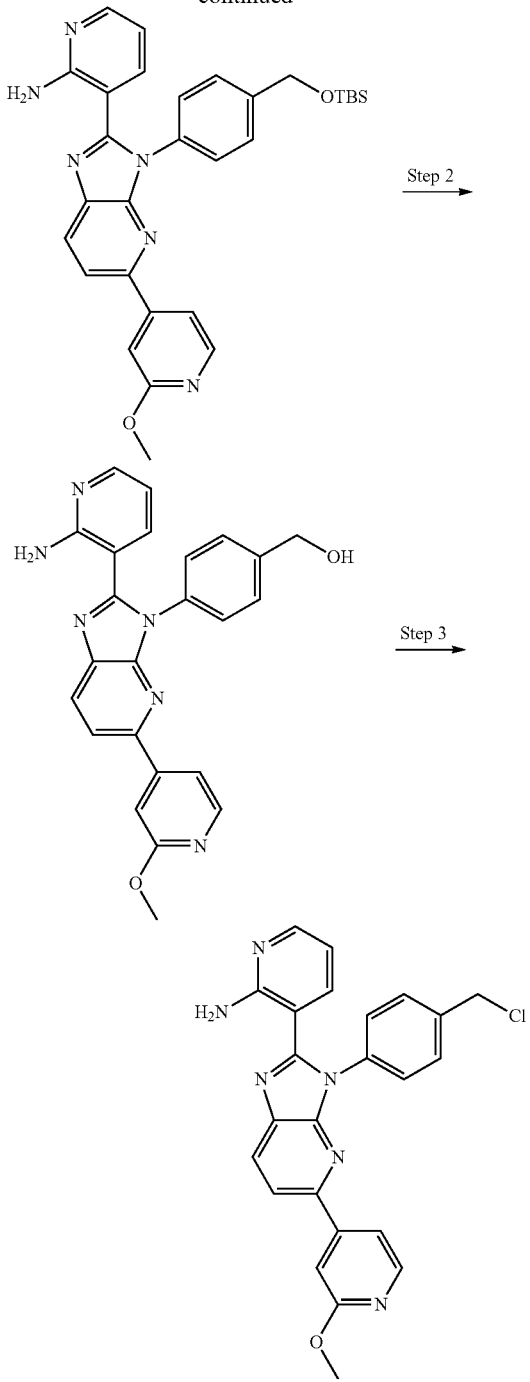

Intermediate 199

Step 1: 3-(3-(4-(((tert-Butyldimethylsilyl)oxy)methyl)phenyl)-5-(2-methoxypyridin-4-yl)-3H-imidazo[4,5-b]pyridin-2-yl)pyridin-2-amine To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 0.5 g, 1.07 mmol) in 1,4-dioxane (5 mL), H₂O (1 mL) were added (2-methoxypyridin-4-yl)boronic acid (230 mg, 1.50 mmol), Pd(dppf)Cl₂ (78.5 mg, 107 μmol), and CS₂CO₃

(445 mg, 1.37 mmol). The mixture was degassed and purged with N$_2$ three times, and stirred at 100° C. for 2 hr under N$_2$ atmosphere. The mixture was quenched with H$_2$O (20 mL) and extracted with EtOAc (8 mL×3). The combined organic layers were washed with brine (20 mL), dried over Na$_2$SO$_4$, filtered and concentrated under reduced pressure. After purified by silica gel flash chromatography (Eluent of 0~62% EtOAc in petroleum ether), 3-(3-(4-(((tert-butyldimethylsilyl)oxy)methyl)phenyl)-5-(2-methoxypyridin-4-yl)-3H-imidazo[4,5-b]pyridin-2-yl)pyridin-2-amine (323 mg, yield: 88%) was obtained as a black brown solid. MS: m/z=539.2 [M+H]$^+$.

Step 2: (4-(2-(2-Aminopyridin-3-yl)-5-(2-methoxy-pyridin-4-yl)-3H-imidazo[4,5-b]pyridin-3-yl)phenyl)methanol To a solution of 3-(3-(4-(((tert-butyldimethylsilyl)oxy)methyl)phenyl)-5-(2-methoxypyridin-4-yl)-3H-imidazo[4,5-b]pyridin-2-yl)pyridin-2-amine (323 mg, 600 µmol) in THF (5 mL) was added TBAF (1 M in THF, 959 µL). The mixture was stirred at 25° C. for 1 hr. The reaction was quenched with H$_2$O (10 mL) and extracted with EtOAc (8 mL×2). The combined organic layers were washed with brine, filtered and concentrated. (4-(2-(2-Aminopyridin-3-yl)-5-(2-methoxypyridin-4-yl)-3H-imidazo[4,5-b]pyridin-3-yl)phenyl)methanol (254 mg, yield: 97%) was obtained as a brown solid. MS: m/z=425.1 [M+H]$^+$.

Step 3: 3-(3-(4-(Chloromethyl)phenyl)-5-(2-methoxypyridin-4-yl)-3H-imidazo[4,5-b]pyridin-2-yl)pyridin-2-amine To a solution of (4-(2-(2-aminopyridin-3-yl)-5-(2-methoxypyridin-4-yl)-3H-imidazo[4,5-b]pyridin-3-yl)phenyl)methanol (500 mg, 1.18 mmol) in CH$_2$Cl$_2$ (5 mL) was added SOCl$_2$ (257 µL, 3.53 mmol). The mixture was stirred at 25° C. for 1 hr. The reaction mixture was concentrated. 3-(3-(4-(Chloromethyl)phenyl)-5-(2-methoxypyridin-4-yl)-3H-imidazo[4,5-b]pyridin-2-yl)pyridin-2-amine (Intermediate 199, 500 mg, yield: 94%) was obtained as a black solid, which was used in the next step without further purification. MS: m/z=443.2 [M+H]$^+$.

Intermediate 200: 3-(3-(4-(Chloromethyl)phenyl)-5-(5-methoxypyridin-3-yl)-3H-imidazo[4,5-b]pyridin-2-yl)pyridin-2-amine

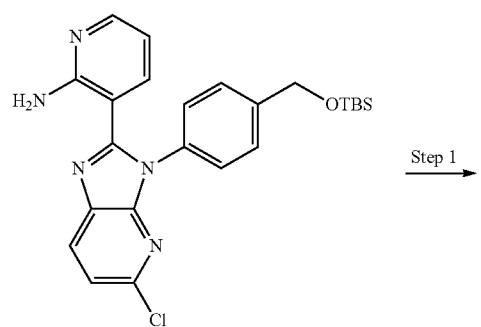

Step 1 →

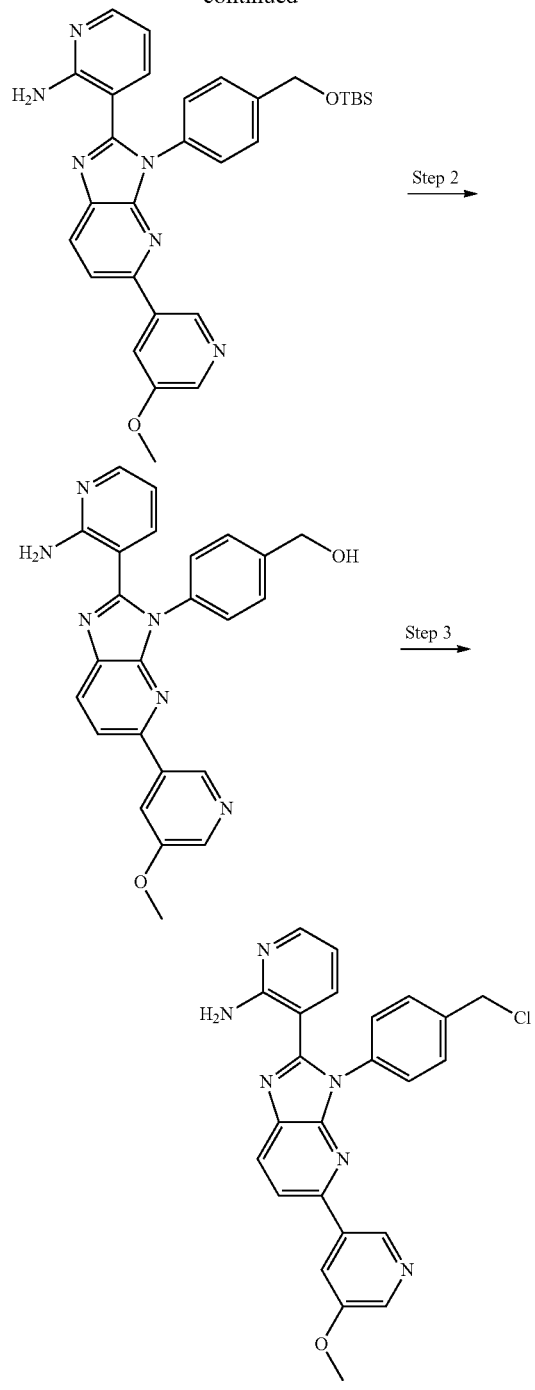

Intermediate 200

Step 1: 3-(3-(4-(((Tert-butyldimethylsilyl)oxy)methyl)phenyl)-5-(5-methoxypyridin-3-yl)-3H-imidazo[4,5-b]pyridin-2-yl)pyridin-2-amine To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 300 mg, 644 µmol) in 1,4-dioxane (3 mL), H$_2$O (0.6 mL) were added (5-methoxy-3-pyridyl)boronic acid (137 mg, 901 µmol), Pd(dppf)Cl$_2$ (47.1 mg, 64.3 µmol,), Cs$_2$CO$_3$ (273 mg, 837 μmol). The mixture was stirred at 100° C. for 2 hr under N$_2$. After purified by silica gel flash chromatography (Eluent of 0%~74% EtOAc in petroleum ether), 3-(3-(4-(((tert-butyldimethylsilyl)oxy)methyl)phenyl)-5-(5-methoxypyridin-3-yl)-3H-imidazo[4,5-b]pyridin-2-yl)pyridin-2-amine (275 mg, yield: 79.3%) was obtained as red solid. MS: m/z=539.3 [M+H]$^+$. 1 H NMR (400 MHz, Chloroform-d) δ 8.70 (d, J=1.6 Hz, 1H), 8.15 (d, J=2.8 Hz, 1H), 8.01 (d, J=8.4 Hz, 1H), 7.91 (dd, J=4.8, 1.6 Hz, 1H), 7.69-7.64 (m, 2H), 7.37-7.32 (m, 2H), 7.24 (s, 1H), 7.11 (s, 1H), 7.01 (dd, J=7.6, 1.6 Hz, 1H), 6.64 (br s, 2H), 6.24 (dd, J=7.6, 5.2 Hz, 1H), 4.71 (s, 2H), 3.76 (s, 3H), 0.84-0.81 (s, 9H), 0.00 (s, 6H).

Step 2: (4-(2-(2-Aminopyridin-3-yl)-5-(5-methoxypyridin-3-yl)-3H-imidazo[4,5-b]pyridin-3-yl)phenyl)methanol To a solution of 3-(3-(4-(((tert-butyldimethylsilyl)oxy)methyl)phenyl)-5-(5-methoxypyridin-3-yl)-3H-imidazo[4,5-b]pyridin-2-yl)pyridin-2-amine (275 mg, 510 μmol) in THF (1 mL) was added TBAF (1 M in THF 817 μL). The mixture was stirred at 25° C. for 1 hr under N$_2$. H$_2$O (30 mL) was add to the reaction mixture. The mixture was extracted with EtOAc (10 mL×3), washed with brine (10 mL), dried over Na$_2$SO$_4$, and concentrated. (4-(2-(2-Aminopyridin-3-yl)-5-(5-methoxypyridin-3-yl)-3H-imidazo[4,5-b]pyridin-3-yl)phenyl)methanol (217 mg, yield: 95%) was obtained as white solid. MS: m/z=425.3 [M+H]$^+$.

Step 3: 3-(3-(4-(Chloromethyl)phenyl)-5-(5-methoxypyridin-3-yl)-3H-imidazo[4,5-b]pyridin-2-yl)pyridin-2-amine To a solution of (4-(2-(2-aminopyridin-3-yl)-5-(5-methoxypyridin-3-yl)-3H-imidazo[4,5-b]pyridin-3-yl)phenyl)methanol (217 mg, 510 μmol) in CH$_2$Cl$_2$ (5 mL) was added SOCl$_2$ (182 mg, 1.53 mmol). The mixture was stirred at 25° C. for 1 hr under N$_2$. The reaction mixture was concentrated to give 3-(3-(4-(chloromethyl)phenyl)-5-(5-methoxypyridin-3-yl)-3H-imidazo[4,5-b]pyridin-2-yl)pyridin-2-amine (Intermediate 200, 226 mg, yield: 97%) as a brown solid. MS: m/z=443.2 [M+H]$^+$.

Intermediate 201: N-Methyl-N-(3-(4,4,5,5-tetramethyl-1,3,2-dioxaborolan-2-yl)phenyl)acetamide Step 1: N-(3-Bromophenyl)-N-methylacetamide To a solution of 3-bromo-N-methyl-aniline (500 mg, 2.69 mmol) in CH$_2$Cl$_2$ (10 mL) were added TEA (816 mg, 8.06 mmol) and AcCl (316 mg, 4.03 mmol) at 25° C. This mixture was stirred at 25° C. for 1 hr. The mixture was quenched with H$_2$O (30 mL) and extracted with EtOAc (20 mL×3). The combined organic layers were washed with brine (50 mL), dried over Na$_2$SO$_4$, filtered and concentrated. N-(3-bromophenyl)-N-methylacetamide (600 mg, yield: 97.9%) was obtained as a yellow oil, which was used directly without purification. $^1$H NMR (400 MHz, Dimethylsulfoxide-d$_6$) δ 7.64 (s, 1H), 7.53 (s, 1H), 7.42-7.32 (m, 2H), 3.40-3.19 (m, 3H), 1.88-1.68 (m, 3H).

Step 2: N-Methyl-N-(3-(4,4,5,5-tetramethyl-1,3,2-dioxaborolan-2-yl)phenyl)acetamide To a solution of N-(3-bromophenyl)-N-methyl-acetamide (500 mg, 2.19 mmol) and 4,4,5,5-tetramethyl-2-(4,4,5,5-tetramethyl-1,3,2-dioxaborolan-2-yl)-1,3,2-dioxaborolane (835 mg, 3.29 mmol) in 1,4-dioxane (20 mL) were added AcOK (861 mg, 8.77 mmol) and Pd(dppf)Cl$_2$ (160 mg, 219 μmol) at 25° C. This mixture was stirred at 100° C. for 12 hr under N$_2$. The mixture was quenched with H$_2$O (30 mL) and extracted with EtOAc (20 mL×3). The combined organic layers were washed with brine (50 mL), dried over Na$_2$SO$_4$, filtered and concentrated. N-methyl-N-(3-(4,4,5,5-tetramethyl-1,3,2-dioxaborolan-2-yl)phenyl)acetamide (Intermediate 201, 600 mg, yield: 99.5%) was obtained as a black solid, which was used directly without purification. MS: m/z=275.8 [M+H]$^+$.

Intermediate 202: 3-(3-(4-(Chloromethyl)phenyl)-5-(3-methoxypyridin-4-yl)-3H-imidazo[4,5-b]pyridin-2-yl)pyridin-2-amine

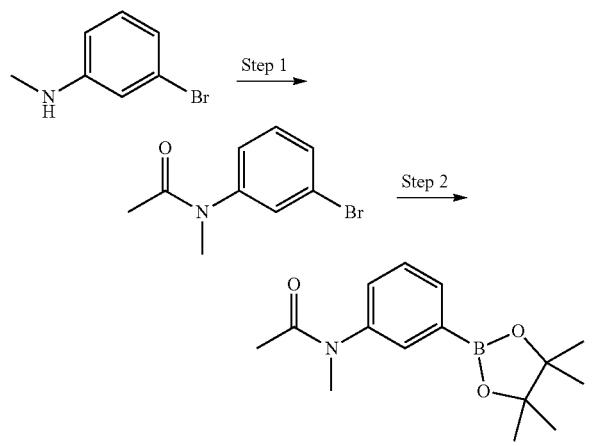

Intermediate 201

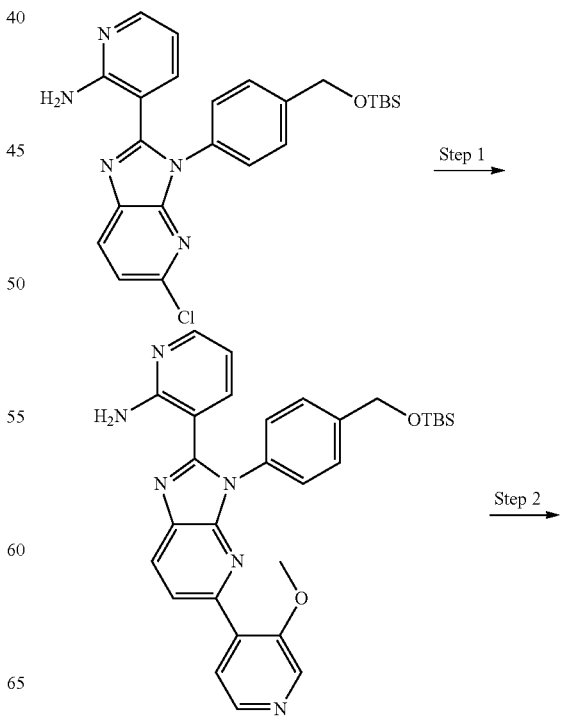

-continued

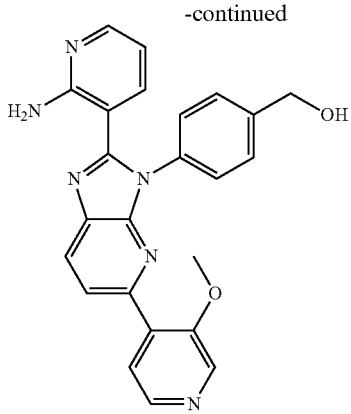

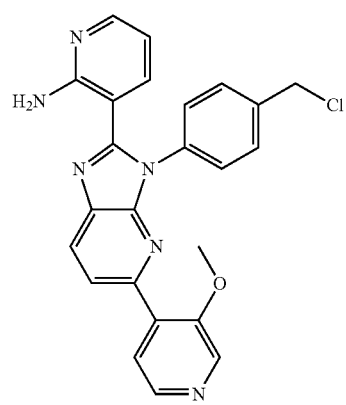

Intermediate 202

Step 1: 3-(3-(4-(((Tert-butyldimethylsilyl)oxy)methyl)phenyl)-5-(3-methoxypyridin-4-yl)-3H-imidazo[4,5-b]pyridin-2-yl)pyridin-2-amine To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 500 mg, 1.07 mmol) in 1,4-dioxane (5 mL) and H$_2$O (1 mL) were added Pd(dppf)Cl$_2$ (78.5 mg, 107 gmol), (3-methoxypyridin-4-yl)boronic acid (213 mg, 1.39 mmol) and Cs$_2$CO$_3$ (1.05 g, 3.22 mmol), then degassed and purged with N$_2$ three times. The mixture was stirred at 100° C. for 12 hr under N$_2$ atmosphere. Water (50 mL) was added, and the mixture was extracted with EtOAc (20 mL×2). The combined organic layers were dried over anhydrous Na$_2$SO$_4$, filtered and concentrated. After purified by silica gel flash chromatography (Eluent of 0~80% EtOAc in petroleum ether), 3-(3-(4-(((tert-butyldimethylsilyl)oxy)methyl)phenyl)-5-(3-methoxypyridin-4-yl)-3H-imidazo[4,5-b]pyridin-2-yl)pyridin-2-amine (350 mg, yield: 61%) was obtained as a black brown solid. MS: m/z=539.2 [M+H]$^+$.

Step 2: (4-(2-(2-Aminopyridin-3-yl)-5-(3-methoxypyridin-4-yl)-3H-imidazo[4,5-b]pyridin-3-yl)phenyl)methanol To a solution of 3-(3-(4-(((tert-butyldimethylsilyl)oxy)methyl)phenyl)-5-(3-methoxypyridin-4-yl)-3H-imidazo[4,5-b]pyridin-2-yl)pyridin-2-amine (350 mg, 650 μmol) in THF (4 mL) was added TBAF (1 M in THF, 1.30 mmol). The mixture was stirred at 20° C. for 2 hr. The mixture was diluted with H$_2$O (50 mL) and extracted with EtOAc (20 mL×2). The combined organic layers were dried over anhydrous Na$_2$SO$_4$, filtered and concentrated, (4-(2-(2-aminopyridin-3-yl)-5-(3-methoxypyridin-4-yl)-3H-imidazo[4,5-b]pyridin-3-yl)phenyl)methanol (250 mg, yield: 91%) was obtained as a black brown solid, which was used in the next step directly. MS: m/z=425.2 [M+H]$^+$.

Step 3: 3-(3-(4-(Chloromethyl)phenyl)-5-(3-methoxypyridin-4-yl)-3H-imidazo[4,5-b]pyridin-2-yl)pyridin-2-amine To a solution of (4-(2-(2-aminopyridin-3-yl)-5-(3-methoxypyridin-4-yl)-3H-imidazo[4,5-b]pyridin-3-yl)phenyl)methanol (250 mg, 589 μmol) in CH$_2$Cl$_2$ (3 mL) was added SOCl$_2$ (210 mg, 1.77 mmol). The mixture was stirred at 25° C. for 2 hr, then concentrated, 3-(3-(4-(chloromethyl)phenyl)-5-(3-methoxypyridin-4-yl)-3H-imidazo[4,5-b]pyridin-2-yl)pyridin-2-amine (Intermediate 202, 160 mg, yield: 61.3%) was obtained as a brown solid, which was used in the next step directly. MS: m/z=443.1 [M+H]$^+$.

Intermediate 203: 3-(3-(4-(Chloromethyl)phenyl)-5-(6-methoxypyridin-3-yl)-3H-imidazo[4,5-b]pyridin-2-yl)pyridin-2-amine

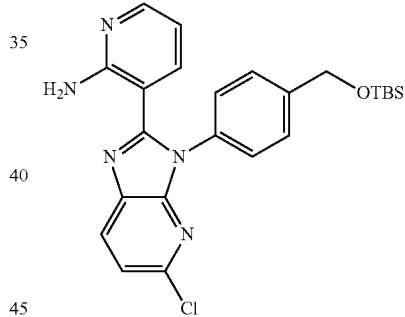

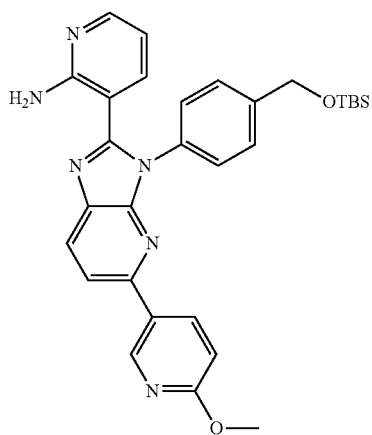

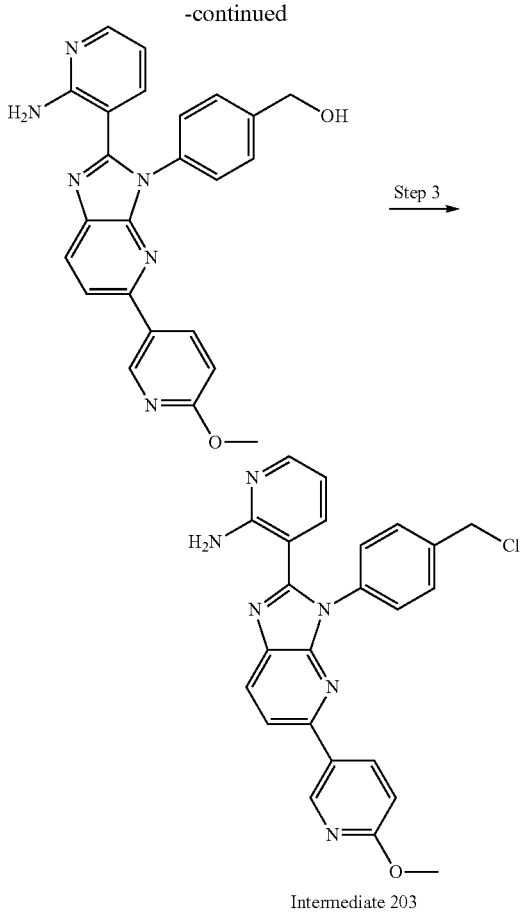

Intermediate 203

Step 1: 3-(3-(4-(((tert-Butyldimethylsilyl)oxy) methyl)phenyl)-5-(6-methoxypyridin-3-yl)-3H-imidazo[4,5-b]pyridin-2-yl)pyridin-2-amine To a solution of 3-(3-(4-(((tert-butyldimethylsilyl)oxy) methyl)phenyl)-5-chloro-3H-imidazo[4,5-b]pyridin-2-yl) pyridin-2-amine (refer to Intermediate 117 for detail procedures, 500 mg, 1.07 mmol) in 1,4-dioxane (5 mL) and $H_2O$ (1 mL) were added Pd(dppf)Cl$_2$ (78.5 mg, 107 μmol), (6-methoxy-3-pyridyl)boronic acid (213 mg, 1.39 mmol) and Cs$_2$CO$_3$ (1.05 g, 3.22 mmol). The mixture was degassed and purged with N$_2$ three times, and stirred at 100° C. for 2 hr under N$_2$ atmosphere. The mixture was diluted with H$_2$O (50 mL) and extracted with EtOAc (30 mL×3). The combined organic layers were washed with brine (50 mL), dried over Na$_2$SO$_4$, filtered and concentrated. After purified by silica gel flash chromatography (Eluent of 0~80% EtOAc in petroleum ether), 3-(3-(4-(((tert-butyldimethylsilyl)oxy) methyl)phenyl)-5-(6-methoxypyridin-3-yl)-3H-imidazo[4, 5-b]pyridin-2-yl)pyridin-2-amine (450 mg, yield: 77.9%) was obtained as a brown solid. MS: m/z=539.2 [M+H]$^+$.

Step 2: (4-(2-(2-Aminopyridin-3-yl)-5-(6-methoxypyridin-3-yl)-3H-imidazo[4,5-b]pyridin-3-yl)phenyl) methanol To a solution of 3-(3-(4-(((tert-butyldimethylsilyl)oxy) methyl)phenyl)-5-(6-methoxypyridin-3-yl)-3H-imidazo[4, 5-b]pyridin-2-yl)pyridin-2-amine (440 mg, 817 μmol) in THF (4 mL) was added TBAF (1 M in THF, 1 mL). The mixture was stirred at 25° C. for 2 hr. The mixture was diluted with H$_2$O (50 mL) and extracted with EtOAc (2×20 mL). The combined organic layers were dried over anhydrous Na$_2$SO$_4$, filtered and concentrated. (4-(2-(2-Aminopyridin-3-yl)-5-(6-methoxypyridin-3-yl)-3H-imidazo[4,5-b]pyridin-3-yl)phenyl)methanol (250 mg, yield: 72.1%) was obtained as a brown solid, which was used in the next step directly. MS: m z=425.2 [M+H]$^+$.

Step 3: 3-(3-(4-(Chloromethyl)phenyl)-5-(6-methoxypyridin-3-yl)-3H-imidazo[4,5-b]pyridin-2-yl)pyridin-2-amine To a solution of (4-(2(2-aminopyridin-3-yl)-5-(6-methoxypyridin-3-yl)-3H-imidazo[4,5-b]pyridin-3-yl)phenyl)methanol (240 mg, 565 μmol) in CH$_2$Cl$_2$ (3 mL) was added SOCl$_2$ (202 mg, 1.70 mmol). The mixture was stirred at 25° C. for 2 hr and then concentrated. 3-(3-(4-(Chloromethyl)phenyl)-5-(6-methoxypyridin-3-yl)-3H-imidazo[4,5-b]pyridin-2-yl)pyridin-2-amine (Intermediate 203, 250 mg, yield: 99.8%) was obtained as a brown solid, which was used in the next step directly. MS: m/z=443.1 [M+H]$^+$.

Intermediate 204: N-Methyl-N-(1-(3-(4,4,5,5-tetramethyl-1,3,2-dioxaborolan-2-yl)phenyl)piperidin-4-yl)acetamide

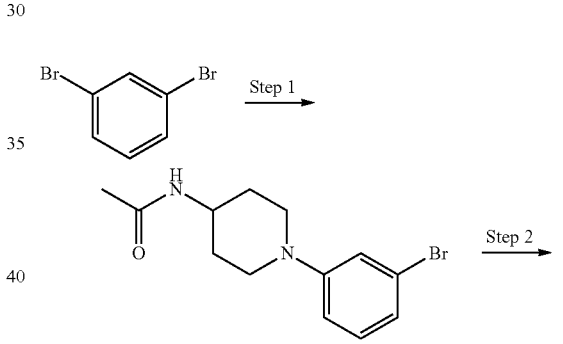

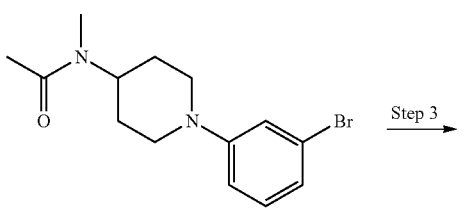

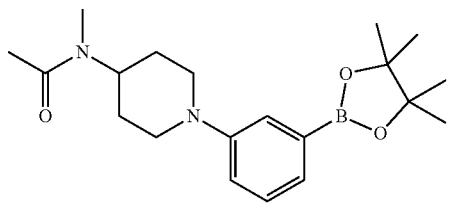

Intermediate 204

Step 1:
N-(1-(3-Bromophenyl)piperidin-4-yl)acetamide

A mixture of 1,3-dibromobenzene (5 g, 21.2 mmol), N-(piperidin-4-yl)acetamide (3.01 g, 21.2 mmol), Pd$_2$(dba)$_3$ (970 mg, 1.06 mmol), BINAP (990 mg, 1.59 mmol) and t-BuONa (2.44 g, 25.4 mmol) in toluene (120 mL) was stirred at 80° C. for 16 hr under N$_2$. After cooling to 25° C., the mixture was diluted with EtOAc (50 mL) and filtered, concentrated.

After purified by silica gel flash chromatography (EtOAc in petroleum ether=50%-100%), N-(1-(3-bromophenyl)piperidin-4-yl)acetamide (4.02 g, yield: 63.8%) was obtained as an off-white solid. MS: m/z=297.0, 299.0 [M+H]$^+$. $^1$H NMR (400 MHz, Dimethylsulfoxide-d$_6$) δ 7.81 (d, J=7.6 Hz, 1H), 7.14-7.09 (m, 1H), 7.07-7.04 (m, 1H), 6.93 (dd, J=8.4, 2.0 Hz, 1H), 6.87 (dd, J=7.6, 0.8 Hz, 1H), 3.78-3.62 (m, 3H), 2.86-2.77 (m, 2H), 1.81-1.73 (m, 5H), 1.46-1.35 (m, 2H).

Step 2: N-(1-(3-Bromophenyl)piperidin-4-yl)-N-methylacetamide

To a solution of N-(1-(3-bromophenyl)piperidin-4-yl)acetamide (2 g, 6.73 mmol) in THF (50 mL) was added NaH (1.08 g, 26.9 mmol, 60% in mineral oil) in portions at 0° C. and stirred at 20° C. for 10 min under N$_2$, then added the MeI (2.87 g, 20.2 mmol) at 0° C. and stirred at 20° C. for 12 hr. The reaction mixture was slowly quenched with water (50 mL) at 0° C. and extracted with EtOAc (50 mL×2). The combined organic layers were washed with brine (50 mL), dried over anhydrous Na$_2$SO$_4$ and filtered, concentrated. After purified by silica gel flash chromatography (EtOAc in petroleum ether=20%-100%), N-(1-(3-bromophenyl)piperidin-4-yl)-N-methylacetamide (1.8 g, yield: 85.9%) was obtained as a brown oil. MS: m/z=310.9, 312.9 [M+H]$^+$. $^1$H NMR (400 MHz, Dimethylsulfoxide-d$_6$) δ 7.16-7.08 (m, 1H), 7.07 (d, J=2.4 Hz, 1H), 6.94 (d, J=8.0 Hz, 1H), 6.88 (d, J=7.6 Hz, 1H), 4.51-4.37 (m, 0.5H), 3.83-3.73 (m, 2.5H), 2.88-2.78 (m, 4H), 2.65 (s, 1H), 2.07 (s, 1H), 1.99 (s, 2H), 1.84-1.62 (m, 3H), 1.53-1.47 (m, 1H).

Step 3: N-Methyl-N-(1-(3-(4,4,5,5-tetramethyl-1,3,2-dioxaborolan-2-yl)phenyl)piperidin-4-yl)acetamide A mixture of N-(1-(3-bromophenyl)piperidin-4-yl)-N-methylacetamide (1.8 g, 5.78 mmol), 4,4,5,5-tetramethyl-2-(4,4,5,5-tetramethyl-1,3,2-dioxaborolan-2-yl)-1,3,2-dioxaborolane (1.76 g, 6.94 mmol), Pd(dppf)Cl$_2$ (212 mg, 289 µmol) and K$_2$CO$_3$ (2.40 g, 17.4 mmol) in 1,4-dioxane (50 mL) was stirred at 80° C. for 12 hr under N$_2$. The mixture was diluted with water (50 mL) at 20° C. and extracted with EtOAc (50 mL×2). The combined organic layers were washed with brine (50 mL), dried over anhydrous Na$_2$SO$_4$, filtered, and concentrated. N-Methyl-N-(1-(3-(4,4,5,5-tetramethyl-1,3,2-dioxaborolan-2-yl)phenyl)piperidin-4-yl) acetamide (Intermediate 204, 2 g, 5.58 mmol, yield: 96.5%) was obtained as a gray solid, which was used directly into the next step. MS: m/z=359.0 [M+H]$^+$. $^1$H NMR (400 MHz, Chloroform-d) δ 7.39 (s, 1H), 7.36-7.26 (m, 2H), 7.05 (d, J=6.4 Hz, 1H), 4.69-4.61 (m, 1H), 3.84-3.74 (m, 2H), 2.90-2.75 (m, 5H), 2.16 (s, 1H), 2.11 (s, 2H), 2.05-2.01 (m, 1H), 1.79-1.68 (m, 3H), 1.34 (s, 12H).

Intermediate 205: 3-(3-(4-(Chloromethyl)phenyl)-5-(4-fluoro-2-(trifluoromethyl)phenyl)-3H-imidazo[4,5-b]pyridin-2-yl)pyridin-2-amine

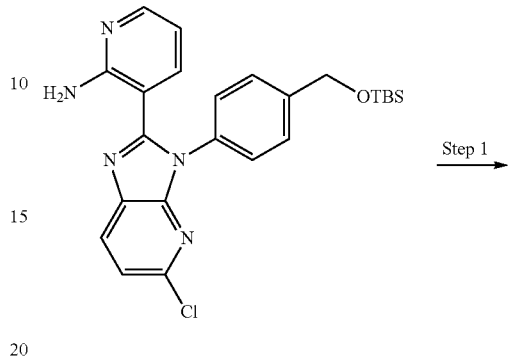

Step 1

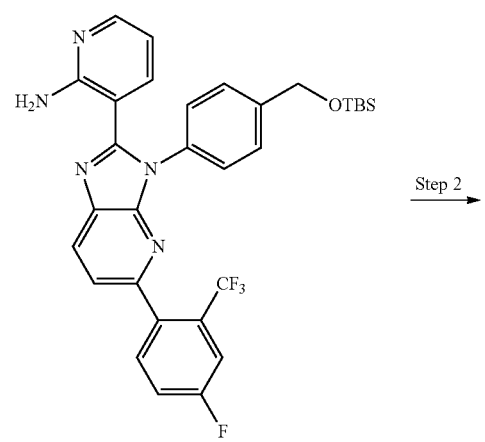

Step 2

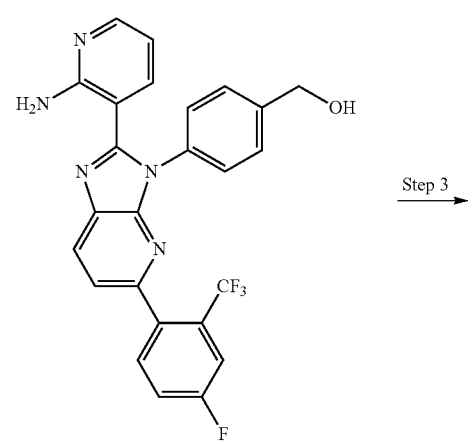

Step 3

799
-continued

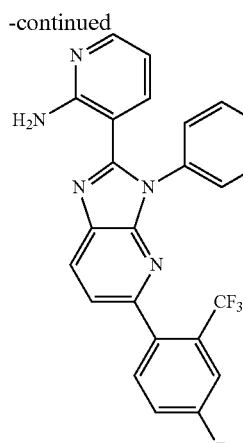

Intermediate 205

Step 1: 3-(3-(4-(((Tert-butyldimethylsilyl)oxy)methyl)phenyl)-5-(4-fluoro-2-(trifluoromethyl)phenyl)-3H-imidazo[4,5-b]pyridin-2-yl)pyridin-2-amine To a mixture of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 400 mg, 858.3 μmol) and (4-fluoro-2-(trifluoromethyl)phenyl)boronic acid (196.3 mg, 944.1 μmol) in 1,4-dioxane (5 mL) and H₂O (1 mL) were added Cs₂CO₃ (838.9 mg, 2.6 mmol) and Pd(dppf)Cl₂ (62.8 mg, 85.8 μmol), the mixture was stirred at 100° C. for 2 hr under N₂. H₂O (50 mL) was added and extracted with EtOAc (100 mL×2). The combined organic layers were washed with brine (100 mL), dried over anhydrous Na₂SO₄, filtered and concentrated. After purified by silica gel flash chromatography ((ethyl acetate/EtOH=3/1) in petroleum ether=0 to 80%), 3-(3-(4-(((tert-butyldimethylsilyl)oxy)methyl)phenyl)-5-(4-fluoro-2-(trifluoromethyl)phenyl)-3H-imidazo[4,5-b]pyridin-2-yl)pyridin-2-amine (400 mg, 673.8 μmol, yield: 78.5%) was obtained as a brown solid. MS: m/z=594.3 [M+H]⁺. ¹H NMR (400 MHz, Dimethylsulfoxide-d₆) δ 8.30 (d, J=8.0 Hz, 1H), 8.03-7.96 (m, 1H), 7.74 (d, J=9.2 Hz, 1H), 7.62 (d, J=7.2 Hz, 2H), 7.51 (d, J=8.0 Hz, 1H), 7.46-7.34 (m, 4H), 7.20 (dd, J=7.6, 1.6 Hz, 1H), 7.07-6.96 (m, 2H), 6.38 (dd, J=7.6, 4.8 Hz, 1H), 4.77 (s, 2H), 0.90 (s, 9H), 0.08 (s, 6H).

Step 2: (4-(2-(2-Aminopyridin-3-yl)-5-(4-fluoro-2-(trifluoromethyl)phenyl)-3H-imidazo[4,5-b]pyridin-3-yl)phenyl)methanol To a mixture of 3-(3-(4-(((tert-butyldimethylsilyl)oxy)methyl)phenyl)-5-(4-fluoro-2-(trifluoromethyl)phenyl)-3H-imidazo[4,5-b]pyridin-2-yl)pyridin-2-amine (350.0 mg, 589.5 μmol) in THF (2 mL) was added TBAF (1 M in THF, 884.3 μL). The mixture was stirred at 20° C. for 1 hr. The mixture was diluted with H₂O (50 mL) and extracted with EtOAc (50 mL×2). The combined organic layers were washed with brine (50 mL), dried over anhydrous Na₂SO₄, filtered and concentrated. (4-(2-(2-Aminopyridin-3-yl)-5-(4-fluoro-2-(trifluoromethyl)phenyl)-3H-imidazo[4,5-b]pyridin-3-yl)phenyl)methanol (280 mg, 584.0 μmol, yield: 99.1%) was obtained as a brown solid. MS: m/z=480.2 [M+H]⁺.

800
Step 3: 3-(3-(4-(Chloromethyl)phenyl)-5-(4-fluoro-2-(trifluoromethyl)phenyl)-3H-imidazo[4,5-b]pyridin-2-yl)pyridin-2-amine To a mixture of (4-(2-(2-aminopyridin-3-yl)-5-(4-fluoro-2-(trifluoromethyl)phenyl)-3H-imidazo[4,5-b]pyridin-3-yl)phenyl)methanol (270.0 mg, 563.2 μmol) in CH₂Cl₂ (2 mL) was added SOCl₂ (201.0 mg, 1.69 mmol). The mixture was stirred at 40° C. for 1 hr and then concentrated under reduced pressure. 3-(3-(4-(Chloromethyl)phenyl)-5-(4-fluoro-2-(trifluoromethyl)phenyl)-3H-imidazo[4,5-b]pyridin-2-yl)pyridin-2-amine (Intermediate 205, 280 mg, 562.4 μmol, yield: 99.9%) was obtained as a yellow solid. MS: m/z=498.1 [M+H]⁺.

Intermediate 206: 3-(3-(4-(Chloromethyl)phenyl)-5-(p-tolyl)-3H-imidazo[4,5-b]pyridin-2-yl)pyridin-2-amine

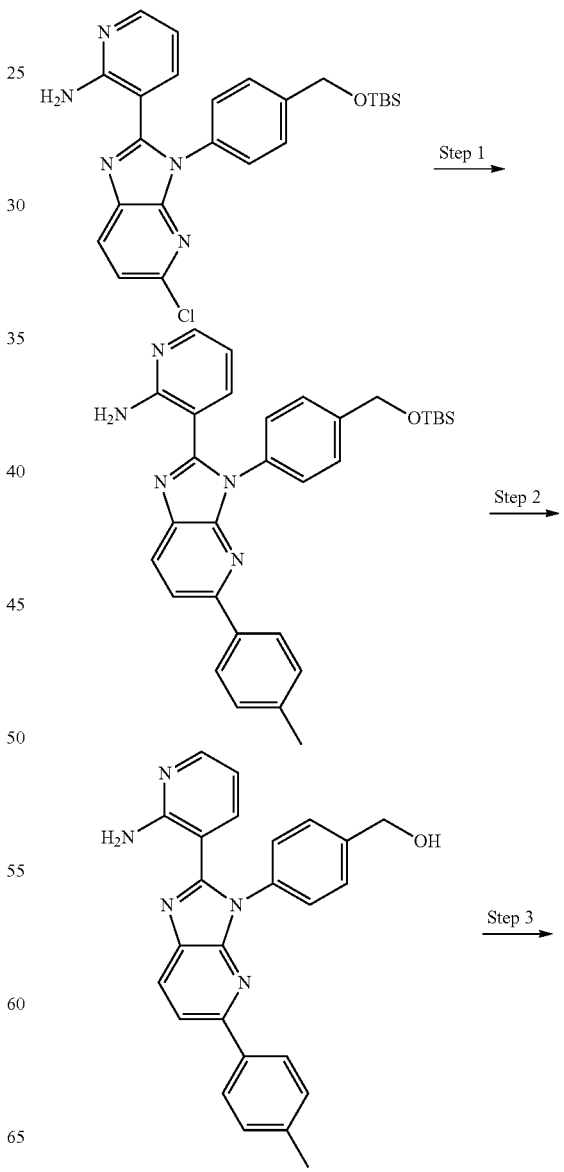

-continued

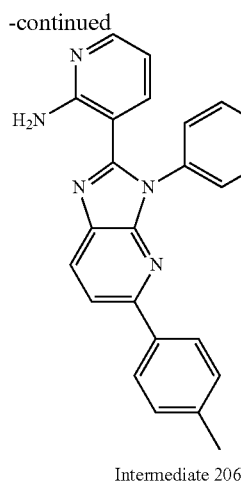

Intermediate 206

Step 1: 3-(3-(4-(((tert-butyldimethylsilyl)oxy)methyl)phenyl)-5-(p-tolyl)-3H-imidazo[4,5-b]pyridin-2-yl)pyridin-2-amine To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 400 mg, 858 μmol) in 1,4-dioxane (5 mL) and H$_2$O (1 mL) were added p-tolylboronic acid (163 mg, 1.2 mmol), Pd(dppf)Cl$_2$ (62.8 mg, 85.8 μmol), Cs$_2$CO$_3$ (839 mg, 2.6 mmol). Water (30 mL) was added and extracted with EtOAc (50 mL×3), the combined organic layers were washed with brine (50 mL×2), dried over anhydrous Na2SO4, filtered and concentrated under reduced pressure. The mixture was stirred at 100° C. for 1 hr under N$_2$. After purified by silica gel flash chromatography (Eluent of 0%~36% EtOAc in petroleum ether), 3-(3-(4-(((tert-butyldimethylsilyl)oxy)methyl)phenyl)-5-(p-tolyl)-3H-imidazo[4,5-b]pyridin-2-yl)pyridin-2-amine (258 mg, yield: 58%) was obtained as a red solid. $^1$H NMR (400 MHz, Chloroform-d) δ 8.12 (d, J=8.4 Hz, 1H), 8.08 (d, J=4.4 Hz, 1H), 7.94 (d, J=8.0 Hz, 2H), 7.80 (d, J=8.4 Hz, 1H), 7.55-7.48 (m, 2H), 7.46-7.40 (m, 2H), 7.31-7.21 (m, 3H), 7.16 (d, J=7.6 Hz, 1H), 6.70 (br s, 2H), 6.40 (dd, J=7.2, 4.4 Hz, 1H), 4.88 (s, 2H), 2.41 (s, 3H), 1.00 (s, 9H), 0.18 (s, 6H).

Step 2: (4-(2-(2-Aminopyridin-3-yl)-5-(p-tolyl)-3H-imidazo[4,5-b]pyridin-3-yl)phenyl)methanol To a solution of 3-(3-(4-(((tert-butyldimethylsilyl)oxy)methyl)phenyl)-5-(p-tolyl)-3H-imidazo[4,5-b]pyridin-2-yl)pyridin-2-amine (258 mg, 494.5 μmol) in THF (4 mL) was added TBAF (1 M in THF, 791 μL). The mixture was stirred at 25° C. for 1 hr. The reaction mixture was quenched with H$_2$O (10 mL) and extracted with EtOAc (10 mL×2). The organic layers were washed with brine (15 mL), dried over Na$_2$SO$_4$, filtered and concentrated under reduced pressure. (4-(2-(2-Aminopyridin-3-yl)-5-(p-tolyl)-3H-imidazo[4,5-b]pyridin-3-yl)phenyl)methanol (120 mg, yield: 60%) was obtained as a red solid, which was used in the next step without further purification. MS: m z=408.3 [M+H]$^+$. $^1$H NMR (400 MHz, Chloroform-d) δ 8.00 (d, J=8.8 Hz, 1H), 7.96 (dd, J=4.8, 1.6 Hz, 1H), 7.81 (d, J=8.0 Hz, 2H), 7.67 (d, J=8.4 Hz, 1H), 7.46-7.41 (m, 2H), 7.37-7.32 (m, 2H), 7.13 (d, J=8.0 Hz, 2H), 7.02 (dd, J=7.6, 1.6 Hz, 1H), 6.49 (br s, 2H), 6.29 (dd, J=8, 4.8 Hz, 1H), 4.73 (s, 2H), 3.28-3.18 (m, 1H), 2.28 (s, 3H).

Step 3: 3-(3-(4-(Chloromethyl)phenyl)-5-(p-tolyl)-3H-imidazo[4,5-b]pyridin-2-yl)pyridin-2-amine To a solution of (4-(2-(2-aminopyridin-3-yl)-5-(p-tolyl)-3H-imidazo[4,5-b]pyridin-3-yl)phenyl)methanol (120 mg, 294.5 μmol) in CH$_2$Cl$_2$ (2 mL) was added SOCl$_2$ (21.4 μL, 295 μmol). The mixture was stirred at 25° C. for 1 hr. The reaction was concentrated under reduced pressure to give 3-(3-(4-(chloromethyl)phenyl)-5-(p-tolyl)-3H-imidazo[4,5-b]pyridin-2-yl)pyridin-2-amine (Intermediate 206, 125 mg, yield: 100%) as a brown solid, which was used in the next step without further purification. MS: m/z=426.3 [M+H]$^+$

Intermediate 207: 3-(3-(4-(Chloromethyl)phenyl)-5-(3-(trifluoromethyl)phenyl)-3H-imidazo[4,5-b]pyridin-2-yl)pyridin-2-amine

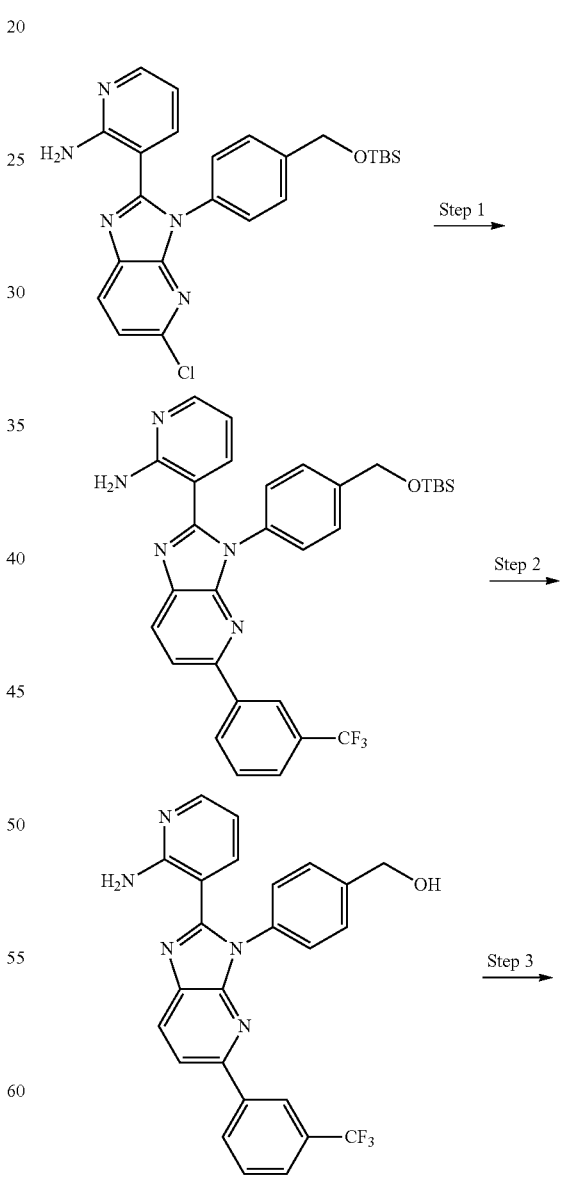

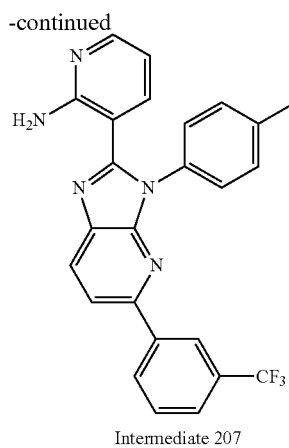

Intermediate 207

Step 1: 3-(3-(4-(((Tert-butyldimethylsilyl)oxy) methyl)phenyl)-5-(3-(trifluoromethyl)phenyl)-3H-imidazo[4,5-b]pyridin-2-yl)pyridin-2-amine To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 400 mg, 858.3 μmol) in 1,4-dioxane (5 mL), H₂O (1 mL) were added (3-(trifluoromethyl)phenyl)boronic acid (228.2 mg, 1.2 mmol), Pd(dppf)Cl₂ (62.8 mg, 85.8 μmol), and Cs₂CO₃ (838.9 mg, 2.6 mmol). The mixture was stirred at 100° C. for 1 hr under N₂. Water (30 mL) was added and extracted with EtOAc (50 mL×3), the combined organic layers were washed with brine (50 mL×2), dried over anhydrous Na2SO4, filtered, and concentrated under reduced pressure. After purified by silica gel flash chromatography (ethyl acetate in petroleum ether=0-36%), 3-(3-(4-(((tert-butyldimethylsilyl)oxy)methyl)phenyl)-5-(3-(trifluoromethyl)phenyl)-3H-imidazo[4,5-b]pyridin-2-yl)pyridin-2-amine (333 mg, yield: 67.4%) was obtained as a red solid. MS: m/z=576.3 [M+H]+ ¹H NMR (400 MHz, Chloroform-d) δ 8.10 (s, 1H), 8.05 (d, J=7.8 Hz, 1H), 8.00 (d, J=8.4 Hz, 1H), 7.91 (dd, J=4.8, 1.6 Hz, 1H), 7.67 (d, J=8.4 Hz, 1H), 7.43-7.48 (m, 1H), 7.40 (d, J=7.6 Hz, 1H), 7.35 (d, J=8.4 Hz, 2H), 7.24-7.22 (m, 1H), 7.10 (s, 1H), 7.00 (dd, J=8.0, 1.6 Hz, 1H), 6.59 (br s, 2H), 6.23 (dd, J=7.6, 4.8 Hz, 1H), 4.71 (s, 2H), 0.82 (s, 9H), 0.11 (s, 6H). ¹⁹F NMR (400 MHz, Chloroform-d₆) δ -62.639.

Step 2: (4-(2-(2-Aminopyridin-3-yl)-5-(3-(trifluoromethyl)phenyl)-3H-imidazo[4,5-b]pyridin-3-yl)phenyl)methanol To a solution of 3-(3-(4-(((tert-butyldimethylsilyl)oxy)methyl)phenyl)-5-(3-(trifluoromethyl)phenyl)-3H-imidazo[4,5-b]pyridin-2-yl)pyridin-2-amine (333 mg, 578.4 μmol) in THF (4 mL) was added TBAF (1 M in THF, 925.5 μL). The mixture was stirred at 25° C. for 1 hr under N₂. The mixture was quenched with H₂O (20 mL) and extracted with EtOAc (10 mL×2). The organic layer were washed with brine (15 mL), dried over Na₂SO₄, then concentrated. (4-(2-(2-Aminopyridin-3-yl)-5-(3-(trifluoromethyl)phenyl)-3H-imidazo[4,5-b]pyridin-3-yl)phenyl)methanol (266.9 mg, yield: 100%) was obtained as a red solid, which was used in the next step without further purification. MS: m/z=462.2 [M+H]+. ¹H NMR (400 MHz, Chloroform-d) δ 8.14 (s, 1H), 8.10 (d, J=8 Hz, 1H), 8.05 (d, J=8.4 Hz, 1H), 7.97 (dd, J=4.8, 1.6 Hz, 1H), 7.72 (d, J=8.0 Hz, 1H), 7.53-7.49 (m, 4H), 7.32 (d, J=8.0 Hz, 2H), 7.03 (dd, J=8.0, 2.0 Hz, J H), 6.53 (br s, 2H), 6.29 (dd, J=7.6, 4.8 Hz, 1H), 4.75 (s, 2H), 2.27-2.47 (m, 1H). ¹⁹F NMR (400 MHz, Chloroform-d₆) δ -62.599.

Step 3: 3-(3-(4-(Chloromethyl)phenyl)-5-(3-(trifluoromethyl)phenyl)-3H-imidazo[4,5-b]pyridin-2-yl)pyridin-2-amine To a solution of (4-(2-(2-aminopyridin-3-yl)-5-(3-(trifluoromethyl)phenyl)-3H-imidazo[4,5-b]pyridin-3-yl)phenyl)methanol (266.9 mg, 578.4 μmol) in CH₂Cl₂ (3.5 mL) was added SOCl₂ (206.5 mg, 1.7 mmol). The mixture was stirred at 25° C. for 1 hr under N₂. The reaction mixture was concentrated. 3-(3-(4-(Chloromethyl)phenyl)-5-(3-(trifluoromethyl)phenyl)-3H-imidazo[4,5-b]pyridin-2-yl)pyridin-2-amine (Intermediate 207, 277.6 mg, yield: 100%) was obtained as a brown solid, which was used in the next step without further purification. MS: m/z=480.2 [M+H]+. ¹H NMR (400 MHz, Dimethylsulfoxide-d₆) δ 8.52 (br s, 1H), 8.42 (d, J=8.4 Hz, 1H), 8.34-8.40 (m, 2H), 8.22 (d, J=8.4 Hz, 1H), 8.17 (dd, J=6.0, 1.6 Hz, 1H), 7.93 (dd, J=7.6, 1.6 Hz, 1H), 7.71-7.81 (m, 2H), 7.64-7.60 (m, 4H), 6.92 (t, J=7.2 Hz, 1H), 4.88 (s, 2H). ¹⁹F NMR (400 MHz, Dimethylsulfoxide-d₆) δ -61.094.

Intermediate 208: 3-(1-(4-(Chloromethyl)phenyl)-1H-benzo[d]imidazol-2-yl)pyridin-2-amine

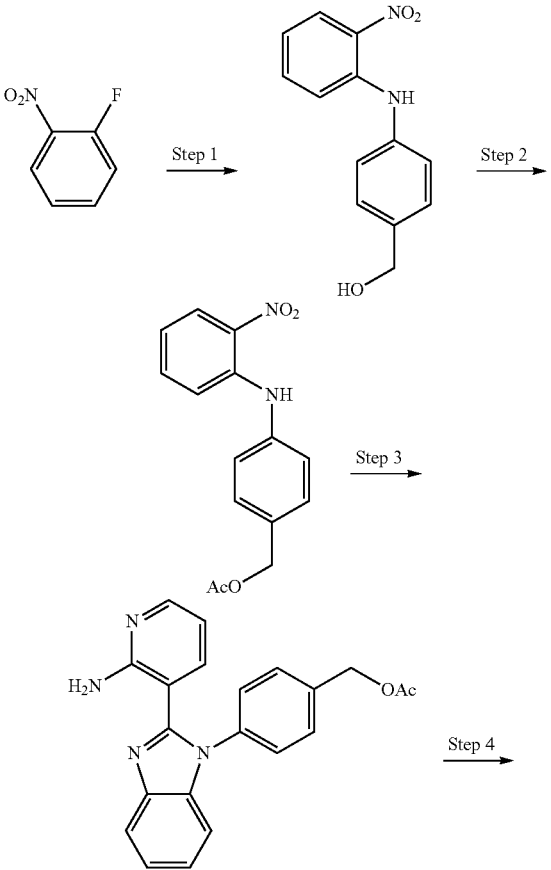

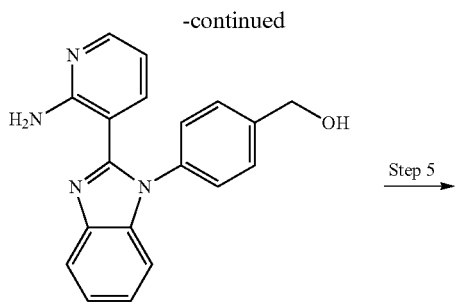

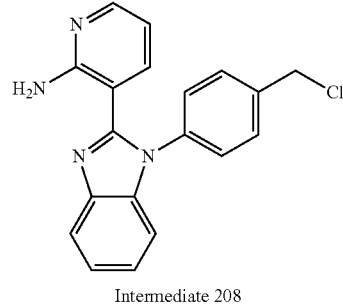

Intermediate 208

Step 1: (4-((2-Nitrophenyl)amino)phenyl)methanol

To a solution of 1-fluoro-2-nitrobenzene (5 g, 35.4 mmol) and (4-aminophenyl)methanol (4.36 g, 35.4 mmol) in DMSO (50 mL) was added DIPEA (13.7 g, 106 mmol) at 20° C. The reaction mixture was stirred at 100° C. for 12 hr. The mixture was diluted with $H_2O$ (100 mL) and the mixture was extracted with EtOAc (100 mL×3). The combined organic layers were washed with brine (100 mL×2), dried over anhydrous Na2SO4, filtered and concentrated under reduced pressure. (4-((2-Nitrophenyl)amino)phenyl)methanol (8.66 g, crude) was obtained as brown oil, which was used directly into the next step.

Step 2: 4-((2-Nitrophenyl)amino)benzyl acetate

To a solution of (4-((2-nitrophenyl)amino)phenyl)methanol (2.8 g, 11.5 mmol) in $CH_2Cl_2$ (30 mL) were added DMAP (140 mg, 1.15 mmol), TEA (3.48 g, 34.4 mmol) and $Ac_2O$ (1.76 g, 17.2 mmol). The mixture was stirred at 20° C. for 1 hr. $H_2O$ (30 mL) was added and the mixture was extracted with $CH_2Cl_2$ (30 mL×3). The combined organic layers were washed with brine (30 mL×2), dried over anhydrous $Na_2SO_4$, filtered and concentrated under reduced pressure. After purified by silica gel flash chromatography (EtOAc in petroleum ether=0~20%), 4-((2-nitrophenyl)amino)benzyl acetate (1.97 g, yield: 60%) was obtained as a brown oil. $^1$H NMR (400 MHz, Dimethylsulfoxide-$d_6$) δ 9.34 (s, 1H), 8.11 (dd, J=8.4, 1.6 Hz, 1H), 7.54-7.48 (m, 1H), 7.42-7.38 (m, 2H), 7.33-7.29 (m, 2H), 7.23 (d, J=8.0 Hz, 1H), 6.92-6.87 (m, 1H), 5.06 (s, 2H), 2.07 (s, 3H).

Step 3: 4-(2-(2-Aminopyridin-3-yl)-1H-benzo[d]imidazol-1-yl)benzyl acetate

To a solution of 4-((2-nitrophenyl)amino)benzyl acetate (950 mg, 3.32 mmol) in DMSO (30 mL) were added $Na_2S_2O_4$ (1.73 g, 9.96 mmol) and 2-aminopyridine-3-carbaldehyde (446 mg, 3.65 mmol). The mixture was stirred at 100° C. for 12 hr. Brine (30 mL) was added to the mixture, and it was extracted with $CH_2Cl_2$ (30 mL×2). The combined organic phase was washed with brine (30 mL), dried over anhydrous $Na_2SO_4$, filtered and concentrated. After purified by silica gel flash chromatography (EtOAc in petroleum ether=55-100%), 4-(2-(2-aminopyridin-3-yl)-1H-benzo[d]imidazol-1-yl)benzyl acetate (230 mg, yield: 19.3%) was obtained as an off-white solid. MS: m/z=359.2 [M+H]$^+$. $^1$H NMR (400 MHz, Dimethylsulfoxide-$d_6$) δ 7.97 (dd, J=4.4, 1.6 Hz, 1H), 7.80 (d, J=7.6 Hz, 1H), 7.56 (d, J=8.4 Hz, 2H), 7.44 (d, J=8.4 Hz, 2H), 7.36-7.26 (m, 2H), 7.19 (d, J=7.6 Hz, 1H), 7.14 (dd, J=1.6, 7.6 Hz, 1H), 6.98 (s, 2H), 6.39 (dd, J=4.8, 7.6 Hz, 1H), 5.17 (s, 2H), 2.11 (s, 3H).

Step 4: (4-(2-(2-Aminopyridin-3-yl)-1H-benzo[d]imidazol-1-yl)phenyl)methanol

To a mixture of 4-(2-(2-aminopyridin-3-yl)-1H-benzo[d]imidazol-1-yl)benzyl acetate (220 mg, 614 μmol) in THF (3 mL), MeOH (3 mL) and $H_2O$ (1 mL) was added $K_2CO_3$ (255 mg, 1.84 mmol) at 20° C. The reaction mixture was stirred at 20° C. for 0.5 hr. Then it was diluted with water (10 mL) and extracted with EtOAc (10 mL×2). The combined organic layers were washed with brine (10 mL×2), dried over anhydrous $Na_2SO_4$, filtered and concentrated. (4-(2-(2-Aminopyridin-3-yl)-1H-benzo[d]imidazol-1-yl)phenyl)methanol (180 mg, yield: 92.7%) was obtained as a yellow solid, which was used directly into the next step. MS: m/z=317.2 [M+H]$^+$.

Step 5: 3-(1-(4-(Chloromethyl)phenyl)-1H-benzo[d]imidazol-2-yl)pyridin-2-amine

To a solution of (4-(2-(2-aminopyridin-3-yl)-1H-benzo[d]imidazol-1-yl)phenyl)methanol (170 mg, 537 μmol) in $CH_2Cl_2$ (5 mL) was added $SOCl_2$ (192 mg, 1.61 mmol). The reaction mixture was stirred at 20° C. for 2 hr. The reaction mixture was concentrated. 3-(1-(4-(Chloromethyl)phenyl)-1H-benzo[d]imidazol-2-yl)pyridin-2-amine (Intermediate 208, 180 mg, crude) was obtained as a yellow solid, which was used directly into the next step. MS: m/z=335.1 [M+H]$^+$.

Intermediate 209: 3-(1-(4-(Chloromethyl)phenyl)-1H-imidazo[4,5-b]pyridin-2-yl)pyridin-2-amine

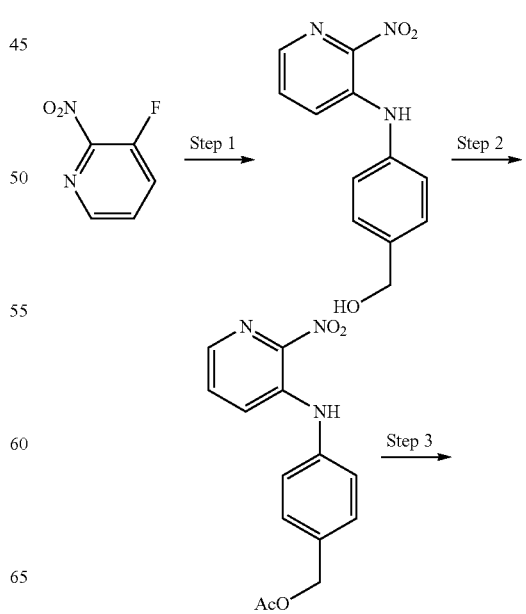

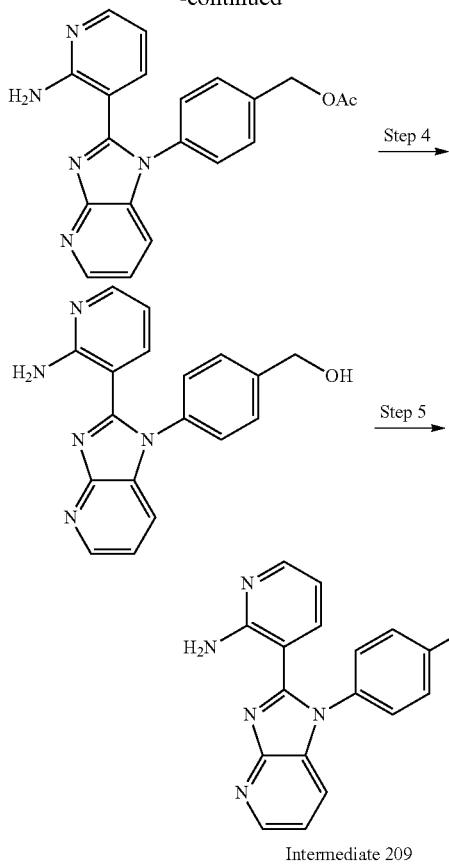

Intermediate 209

Step 1: (4-((2-Nitropyridin-3-yl)amino)phenyl)methanol

To a solution of 3-fluoro-2-nitro-pyridine (5 g, 35.2 mmol) and (4-aminophenyl)methanol (4.33 g, 35.2 mmol) in DMF (50 mL) was added TEA (10.7 g, 106 mmol) at 20° C. The reaction mixture was stirred at 100° C. for 12 hr. $H_2O$ (100 mL) was added, and the mixture was extracted with EtOAc (100 mL×3). The combined organic layers were washed with brine (100 mL×2), dried over anhydrous $Na_2SO_4$, filtered, and concentrated under reduced pressure. (4-((2-Nitropyridin-3-yl)amino)phenyl)methanol (8.63 g, crude) was obtained as brown oil, which was used directly into the next step. MS: m/z=246.0 $[M+H]^+$.

Step 2: 4-((2-Nitropyridin-3-yl)amino)benzyl acetate

To a solution of (4-((2-nitropyridin-3-yl)amino)phenyl) methanol (2.8 g, 11.4 mmol) in $CH_2Cl_2$ (30 mL) were added DMAP (139 mg, 1.14 mmol), TEA (3.47 g, 34.3 mmol), and $Ac_2O$ (1.75 g, 17.1 mmol). The mixture was stirred at 20° C. for 1 hr. $H_2O$ (30 mL) was added, and the resulting mixture was extracted with $CH_2Cl_2$ (30 mL×3). The combined organic layers were washed with brine (30 mL×2), dried over anhydrous $Na_2SO_4$, filtered and concentrated under reduced pressure. After purified by silica gel flash chromatography (EtOAc in petroleum ether=0-50%), 4-((2-nitropyridin-3-yl)amino)benzyl acetate (2.23 g, yield: 68%) was obtained as an orange solid. MS: m/z=288.0 $[M+H]^+$. $^1H$ NMR (400 MHz, Dimethylsulfoxide-$d_6$) δ 9.13 (s, 1H), 7.99 (dd, J=4.0, 1.2 Hz, 1H), 7.77-7.72 ((m, 1H), 7.57 (dd, J=8.4, 4.0 Hz, 1H), 7.40 (d, J=8.4 Hz, 2H), 7.29 (d, J=8.4 Hz, 2H), 5.06 (s, 2H), 2.07 (s, 3H).

Step 3: 4-(2-(2-Aminopyridin-3-yl)-1H-imidazo[4,5-b]pyridin-1-yl)benzyl acetate To a solution of 4-((2-nitropyridin-3-yl)amino)benzyl acetate (1.10 g, 3.84 mmol) in DMSO (30 mL) were added $Na_2S_2O_4$ (2.01 g, 11.5 mmol) and 2-aminopyridine-3-carbaldehyde (516 mg, 4.23 mmol). The mixture was stirred at 100° C. for 12 hr. Brine (30 mL) was added to the mixture and the mixture was extracted with $CH_2Cl_2$ in MeOH (10:1) (30 mL×2). The combined organic layers were washed with brine (30 mL), dried over anhydrous $Na_2SO_4$, filtered and concentrated. After purified by silica gel flash chromatography (MeOH in $CH_2Cl_2$=0-30%), 4-(2-(2-aminopyridin-3-yl)-1H-imidazo[4,5-b]pyridin-1-yl)benzyl acetate (300 mg, yield: 21.7%) was obtained as brown oil. MS: m/z=360.2 $[M+H]^+$.

Step 4: (4-(2-(2-Aminopyridin-3-yl)-1H-imidazo[4,5-b]pyridin-1-yl)phenyl)methanol To a mixture of 4-(2-(2-aminopyridin-3-yl)-1H-imidazo [4,5-b]pyridin-1-yl)benzyl acetate (290 mg 807 μmol) in THF (3 mL), MeOH (3 mL) and $H_2O$ (1 mL) was added $K_2CO_3$ (335 mg, 2.42 mmol) at 20° C. The reaction mixture was stirred at 20° C. for 0.5 hr. The resulting mixture was diluted with brine (10 mL) and extracted with EtOAc (10 mL×2). The combined organic layers were washed with brine (10 mL×2), dried over anhydrous $Na_2SO_4$, filtered and concentrated. (4-(2-(2-Aminopyridin-3-yl)-1H-imidazo[4,5-b]pyridin-1-yl)phenyl)methanol (110 mg, yield: 43%) was obtained as a brown solid, which was used directly into the next step. MS: m/z=318.1 $[M+H]^+$.

Step 5: 3-(1-(4-(Chloromethyl)phenyl)-1H-imidazo[4,5-b]pyridin-2-yl)pyridin-2-amine To a solution of (4-(2-(2-aminopyridin-3-yl)-1H-imidazo [4,5-b]pyridin-1-yl)phenyl)methanol (100 mg, 315 μmol) in $CH_2Cl_2$ (3 mL) was added $SOCl_2$ (112 mg, 945 μmol). The reaction mixture was stirred at 20° C. for 1 hr. The reaction mixture was concentrated. 3-(1-(4-(chloromethyl)phenyl)-1H-imidazo[4,5-b]pyridin-2-yl)pyridin-2-amine (Intermediate 209, 106 mg, crude) was obtained as a yellow solid, which was used directly into the next step. MS: m/z=336.0 $[M+H]^+$.

Intermediate 210: 3-(3-(4-(Chloromethyl)phenyl)-5-(difluoromethoxy)-3H-imidazo[4,5-b]pyridin-2-yl)pyridin-2-amine

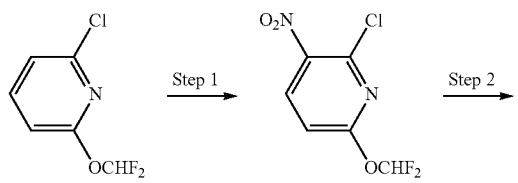

809
-continued

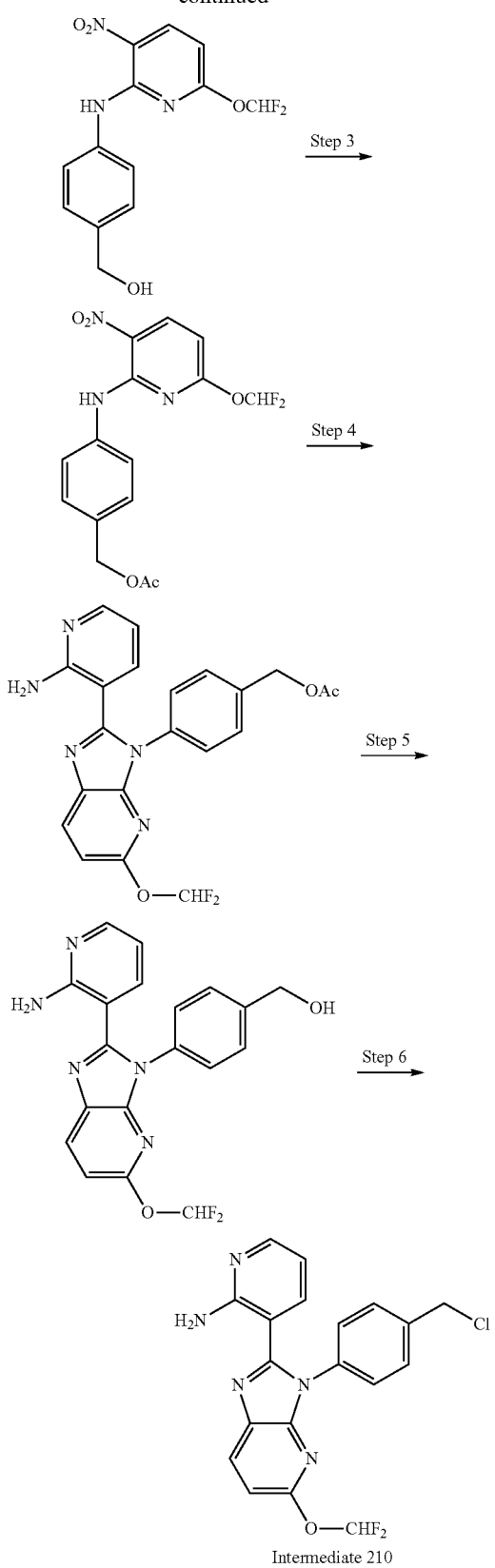

Intermediate 210

810

Step 1:
2-Chloro-6-(difluoromethoxy)-3-nitropyridine

To a solution of 2-chloro-6-(difluoromethoxy)pyridine (1.4 g, 7.80 mmol) in H$_2$SO$_4$ (14 mL) was added dropwise HNO$_3$ (9.80 g, 156 mmol, 7 mL) slowly at 0° C. for 1 hr. The reaction mixture was stirred at 40° C. for 12 hr. The reaction mixture was poured into ice water (60 mL) and extracted with EtOAc (60 mL×3). The combined organic layers were washed with brine (60 mL×3), dried over anhydrous Na$_2$SO$_4$, filtered and concentrated. After purified by silica gel flash chromatography (EtOAc in petroleum ether=0-20%), 2-chloro-6-(difluoromethoxy)-3-nitropyridine (0.9 g, yield: 51%) was obtained as a yellow oil. $^1$H NMR (400 MHz, Chloroform-d) δ 9.11 (s, 1H), 7.55 (t, J=69.6 Hz, 1H). $^{19}$F NMR (400 MHz, Chloroform-d) δ −89.627.

Step 2: (4-((6-(Difluoromethoxy)-3-nitropyridin-2-yl)amino)phenyl)methanol

To a solution of 2-chloro-6-(difluoromethoxy)-3-nitropyridine (0.9 g, 4.01 mmol) in 1,4-dioxane (15 mL) were added (4-aminophenyl)methanol (543 mg, 4.41 mmol) and DIEA (1.55 g, 12.0 mmol) at 20° C. The reaction mixture was stirred at 80° C. for 2 hr. The reaction mixture was concentrated to give (4-((6-(difluoromethoxy)-3-nitropyridin-2-yl)amino)phenyl)methanol (1.25 g, crude) as a brown oil, which was used directly into the next step.

Step 3: 4-((6-(Difluoromethoxy)-3-nitropyridin-2-yl)amino)benzyl acetate

To a solution of (4-((6-(difluoromethoxy)-3-nitropyridin-2-yl)amino)phenyl)methanol (0.65 g, 2.09 mmol) in CH$_2$Cl$_2$ (6 mL) were added Ac$_2$O (320 mg, 3.13 mmol), DMAP (25.5 mg, 209 μmol) and TEA (634 mg, 6.27 mmol). The mixture was stirred at 20° C. for 12 hr. The reaction was diluted with H$_2$O (10 mL) and extracted with CH$_2$Cl$_2$ (10 mL×3). The combined organic layers were washed with brine (10 mL×2), dried over anhydrous Na$_2$SO$_4$, filtered and concentrated under reduced pressure. After purified by silica gel flash chromatography (Eluent of 10~20% EtOAc in petroleum ether), 4-((6-(difluoromethoxy)-3-nitropyridin-2-yl)amino)benzyl acetate (290 mg, yield: 39% for 2 steps) was obtained as an orange solid. $^1$H NMR (400 MHz, Dimethylsulfoxide-d$_6$) δ 10.32 (s, 1H), 8.64 (d, J=9.2 Hz, 1H), 7.74-7.53 (m, 3H), 7.41-7.36 (m, 2H), 6.59 (d, J=8.8 Hz, 1H), 5.07 (s, 2H), 2.07 (s, 3H). $^{19}$F NMR (400 MHz, Dimethylsulfoxide-d$_6$) δ −88.486.

Step 4: 4-(2-(2-Aminopyridin-3-yl)-5-(difluoromethoxy)-3H-imidazo[4,5-b]pyridin-3-yl)benzyl acetate To a solution of 4-((6-(difluoromethoxy)-3-nitropyridin-2-yl)amino)benzyl acetate (290 mg, 821 μmol) in DMSO (10 mL) were added Na$_2$S$_2$O$_4$ (429 mg, 2.46 mmol) and 2-aminonicotinaldehyde (110 mg, 903 μmol). The mixture was stirred at 100° C. for 12 hr. Aqueous NaHCO$_3$ (30 mL) was added and the mixture was extracted with CH$_2$Cl$_2$ (30 mL×2). The combined organic layers were washed with brine (30 mL), dried over anhydrous Na$_2$SO$_4$, filtered and concentrated. After purified by silica gel flash chromatography (EtOAc in petroleum ether=40-100%), 4-(2-(2-aminopyridin-3-yl)-5-(difluoromethoxy)-3H-imidazo[4,5-b]

pyridin-3-yl)benzyl acetate (130 mg, yield: 43%) was obtained as a brown solid. MS: m/z=426.2 [M+H]⁺.

Step 5: (4-(2-(2-Aminopyridin-3-yl)-5-(difluoromethoxy)-3H-imidazo[4,5-b]pyridin-3-yl)phenyl)methanol To a mixture of 4-(2-(2-aminopyridin-3-yl)-5-(difluoromethoxy)-3H-imidazo[4,5-b]pyridin-3-yl)benzyl acetate (130 mg, 306 µmol) in THF (3 mL), MeOH (3 mL), and H₂O (1 mL) was added K₂CO₃ (127 mg, 917 µmol) at 20° C. The reaction mixture was stirred at 20° C. for 0.5 hr. The resulting mixture was quenched with water (10 ml) and extracted with CH₂Cl₂ (10 mL×3). The combined organic layers were washed with brine (10 mL×2), dried over anhydrous Na₂SO₄, filtered and concentrated. (4-(2-(2-Aminopyridin-3-yl)-5-(difluoromethoxy)-3H-imidazo[4,5-b]pyridin-3-yl)phenyl)methanol (117 mg, crude) was obtained as a brown solid, which was used directly into the next step. MS: m/z=384.1 [M+H]⁺.

Step 6: 3-(3-(4-(Chloromethyl)phenyl)-5-(difluoromethoxy)-3H-imidazo[4,5-b]pyridin-2-yl)pyridin-2-amine To a solution of (4-(2-(2-aminopyridin-3-yl)-5-(difluoromethoxy)-3H-imidazo[4,5-b]pyridin-3-yl)phenyl)methanol (117 mg, 306 µmol) in CH₂Cl₂ (5 mL) was added SOCl₂ (109 mg, 917 µmol). The reaction mixture was stirred at 20° C. for 2 hr. The reaction mixture was concentrated to give 3-(3-(4-(chloromethyl)phenyl)-5-(difluoromethoxy)-3H-imidazo[4,5-b]pyridin-2-yl)pyridin-2-amine (Intermediate 210, 123 mg, crude) as a gray solid, which was used directly into the next step. MS: m/z=402.1 [M+H]⁺.

Intermediate 211: 3-(3-(4-(Chloromethyl)phenyl)-5-(4-methoxypyridin-3-yl)-3H-imidazo[4,5-b]pyridin-2-yl)pyridin-2-amine

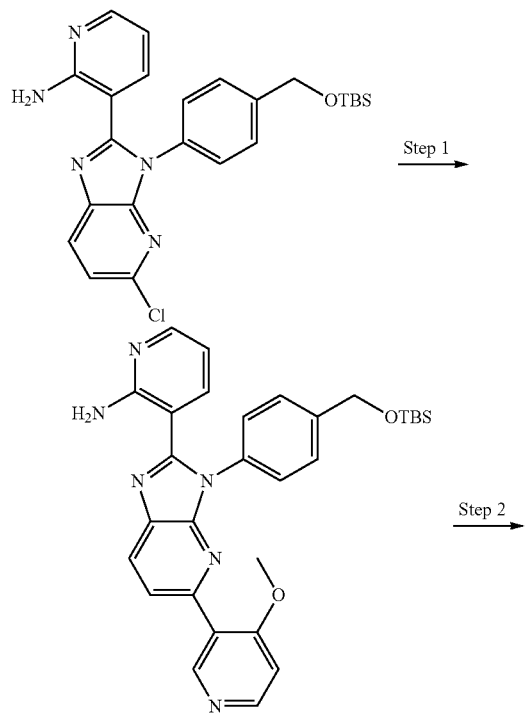

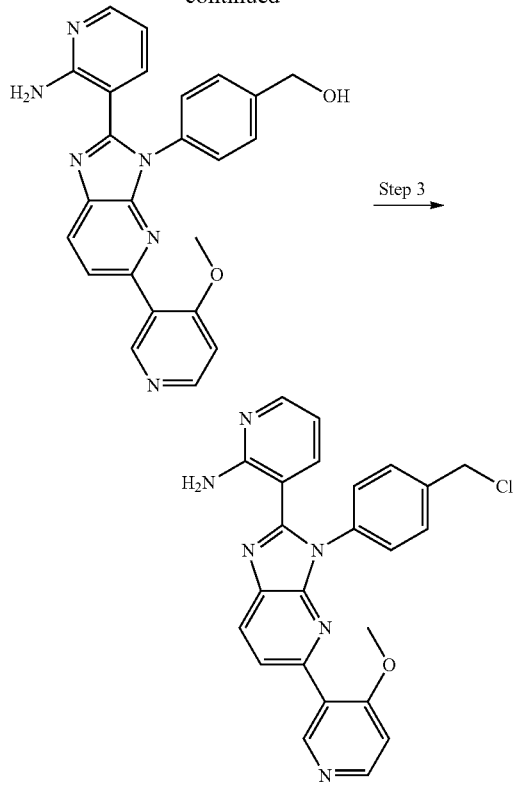

Intermediate 211

Step 1: 3-(3-(4-(((Tert-butyldimethylsilyl)oxy)methyl)phenyl)-5-(4-methoxypyridin-3-yl)-3H-imidazo[4,5-b]pyridin-2-yl)pyridin-2-amine To a mixture of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 400 mg, 858 µmol) and (4-methoxypyridin-3-yl)boronic acid (144 mg, 944 µmol) in 1,4-dioxane (5 mL) and H₂O (1 mL) were added Cs₂CO₃ (839 mg, 2.6 mmol) and Pd(dppf)Cl₂ (62.8 mg, 85.8 µmol), the mixture was stirred at 100° C. for 2 hr under N₂. H₂O (100 mL) was added and extracted with EtOAc (200 mL×2). The combined organic layers were washed with brine (200 mL), dried over anhydrous Na₂SO₄, filtered and concentrated. After purified by silica gel flash chromatography (EtOAc in CH₂Cl₂=0-80%), 3-(3-(4-(((tert-butyldimethylsilyl)oxy)methyl)phenyl)-5-(4-methoxypyridin-3-yl)-3H-imidazo[4,5-b]pyridin-2-yl)pyridin-2-amine (270 mg, yield: 58%) was obtained as a brown solid. MS: m/z=539.2 [M+H]⁺. ¹H NMR (400 MHz, Dimethylsulfoxide-d₆) δ 8.65 (s, 1H) 8.45 (d, J=5.6 Hz, 1H), 8.24 (d, J=8.0 Hz, 1H), 8.00 (dd, J=4.4, 1.6 Hz, 1H), 7.86 (d, J=8.4 Hz, 1H), 7.48-7.44 (m, 4H), 7.22-7.16 (m, 2H), 7.06-7.00 (s, 2H), 6.38 (dd, J=7.6, 4.8 Hz, 1H), 4.80 (s, 2H), 3.92 (s, 3H), 0.90 (s, 9H), 0.09 (s, 6H).

Step 2: (4-(2-(2-Aminopyridin-3-yl)-5-(4-methoxypyridin-3-yl)-3H-imidazo[4,5-b]pyridin-3-yl)phenyl)methanol To a mixture of 3-(3-(4-(((tert-butyldimethylsilyl)oxy)methyl)phenyl)-5-(4-methoxypyridin-3-yl)-3H-imidazo[4,5-b]pyridin-2-yl)pyridin-2-amine (260 mg, 482.6 µmol) in THF (3 mL) was added TBAF (1M in THF, 724 μL), the mixture was stirred at 20° C. for 1 hr. The mixture was diluted with H₂O (50 mL) and extracted with EtOAc (100 mL×2). The combined organic layers were washed with brine (100 mL), dried over anhydrous Na₂SO₄, filtered and concentrated, (4-(2-(2-aminopyridin-3-yl)-5-(4-methoxypyridin-3-yl)-3H-imidazo[4,5-b]pyridin-3-yl)phenyl)methanol (200 mg, yield: 98%) was obtained as a yellow solid. MS: m/z=425.1 [M+H]⁺. ¹H NMR (400 MHz, Dimethylsulfoxide-d₆) δ 8.70 (s, 1H), 8.50 (d, J=6.0 Hz, 1H), 8.29 (d, J=8.4 Hz, 1H), 8.05 (dd, J=4.8, 2.0 Hz, 1H), 7.91 (d, J=8.4 Hz, 1H), 7.54-7.46 (m, 4H), 7.30-7.22 (m, 2H), 7.13-6.99 (m, 2H), 6.46 (dd, J=7.6, 4.8 Hz, 1H), 5.38 (t, J=6.0 Hz, 1H), 4.62 (d, J=6.0 Hz, 2H), 3.97 (s, 3H).

Step 3: 3-(3-(4-(Chloromethyl)phenyl)-5-(4-methoxypyridin-3-yl)-3H-imidazo[4,5-b]pyridin-2-yl)pyridin-2-amine To a solution of (4-(2-(2-aminopyridin-3-yl)-5-(4-methoxypyridin-3-yl)-3H-imidazo[4,5-b]pyridin-3-yl)phenyl)methanol (200 mg, 471 μmol) in CH₂Cl₂ (3 mL) was added SOCl₂ (168 mg, 1.41 mmol). The mixture was stirred at 25° C. for 2 hr. The mixture was concentrated. 3-(3-(4-(Chloromethyl)phenyl)-5-(4-methoxypyridin-3-yl)-3H-imidazo[4,5-b]pyridin-2-yl)pyridin-2-amine (Intermediate 211, 200 mg, yield: 96%) was obtained as a yellow solid, which was used in the next step directly. MS: m/z=443.1 [M+H]⁺.

Intermediate 212: 3-(3-(4-(Chloromethyl)phenyl)-5-(2-methoxypyridin-3-yl)-3H-imidazo[4,5-b]pyridin-2-yl)pyridin-2-amine

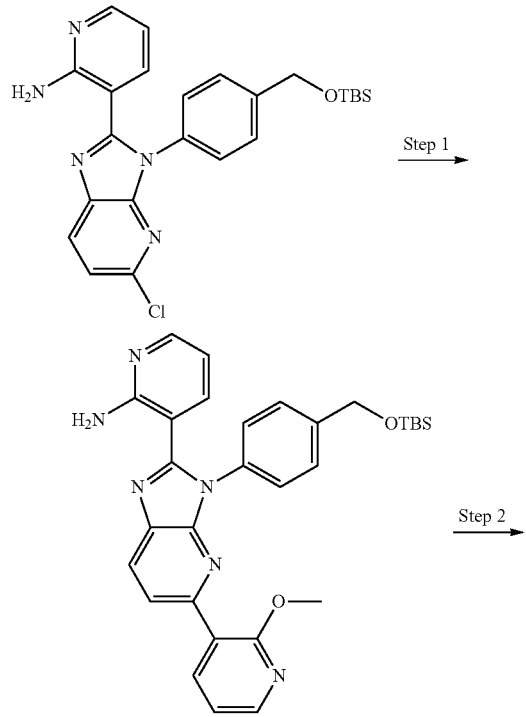

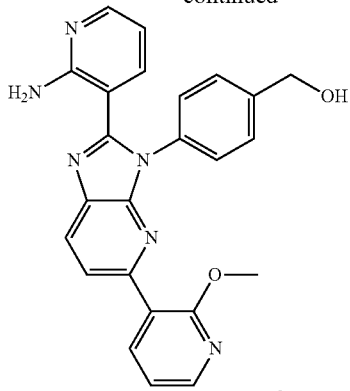

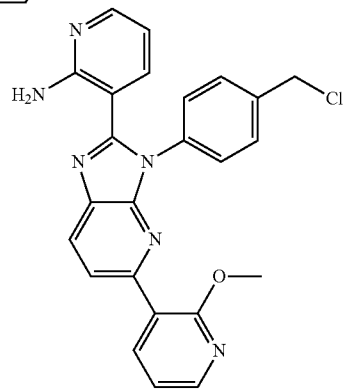

Intermediate 212

Step 1: 3-(3-(4-(((Tert-butyldimethylsilyl)oxy)methyl)phenyl)-5-(2-methoxypyridin-3-yl)-3H-imidazo[4,5-b]pyridin-2-yl)pyridin-2-amine To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 400 mg, 858 μmol) in 1,4-dioxane (25 mL) and H₂O (5 mL) were added (2-methoxypyridin-3-yl)boronic acid (144 mg, 944 μmol), Pd(dppf)Cl₂ (62.8 mg, 85.8 μmol) and Cs₂CO₃ (839 mg, 2.57 mmol) at 20° C. The reaction mixture was stirred at 100° C. for 2 hr. Water (30 mL) was added, and the resulting mixture was extracted with EtOAc (50 mL×3). The combined organic layers were washed with brine (50 mL×2), dried over anhydrous Na₂SO₄, filtered and concentrated under reduced pressure. 3-(3-(4-(((Tert-butyldimethylsilyl)oxy)methyl)phenyl)-5-(2-methoxypyridin-3-yl)-3H-imidazo[4,5-b]pyridin-2-yl)pyridin-2-amine (460 mg, crude) was obtained as a black brown solid, which was used directly into the next step. MS: m/z=539.2 [M+H]⁺. ¹H NMR (400 MHz, Chloroform-d) δ 8.21-8.16 (m, 2H), 8.12 (s, 2H), 8.00 (d, J=4.4 Hz, 1H), 7.62-7.53 (m, 1H), 7.49 (d, J=8.4 Hz, 2H), 7.38 (d, J=8.4 Hz, 2H), 7.20 (d, J=8.0 Hz, 2H), 6.98 (dd, J=7.6, 4.8 Hz, 1H), 6.41 (dd, J=7.6, 4.8 Hz, 1H), 4.85 (s, 2H), 4.05 (s, 3H), 0.97 (s, 9H), 0.14 (s, 6H).

Step 2: (4-(2-(2-Aminopyridin-3-yl)-5-(2-methoxypyridin-3-yl)-3H-imidazo[4,5-b]pyridin-3-yl)phenyl)methanol To a solution of 3-(3-(4-(((tert-butyldimethylsilyl)oxy)methyl)phenyl)-5-(2-methoxypyridin-3-yl)-3H-imidazo[4,5-b]pyridin-2-yl)pyridin-2-amine (450 mg, 835 μmol) in THF (30 mL) was added TBAF (1 M in THF, 1.25 mL). The reaction mixture was stirred at 20° C. for 1 hr. Water (30 mL) was added, and the mixture was extracted with EtOAc (50 mL×3). The combined organic layers were washed with brine (50 mL×2), dried over anhydrous Na₂SO₄, filtered and concentrated under reduced pressure. (4-(2-(2-Aminopyridin-3-yl)-5-(2-methoxypyridin-3-yl)-3H-imidazo[4,5-b]pyridin-3-yl)phenyl)methanol (350 mg, crude) was obtained as a black brown solid, which was used directly into the next step. MS: m/z=425.2 [M+H]⁺.

Step 3: 3-(3-(4-(Chloromethyl)phenyl)-5-(2-methoxypyridin-3-yl)-3H-imidazo[4,5-b]pyridin-2-yl)pyridin-2-amine To a solution of (4-(2-(2-aminopyridin-3-yl)-5-(2-methoxypyridin-3-yl)-3H-imidazo[4,5-b]pyridin-3-yl)phenyl)methanol (350 mg, 825 µmol) in CH₂Cl₂ (15 mL) was added SOCl₂ (294 mg, 2.47 mmol). The reaction mixture was stirred at 20° C. for 2 hr. The reaction mixture was concentrated. 3-(3-(4-(Chloromethyl)phenyl)-5-(2-methoxypyridin-3-yl)-3H-imidazo[4,5-b]pyridin-2-yl)pyridin-2-amine (Intermediate 212, 360 mg, crude) was obtained as a black brown solid, which was used directly into the next step. MS: m/z=443.1 [M+H]⁺.

Intermediate 213: 3-(3-(4-(Chloromethyl)phenyl)-5-(1,3-dimethyl-1H-pyrazol-4-yl)-3H-imidazo[4,5-b]pyridin-2-yl)pyridin-2-amine

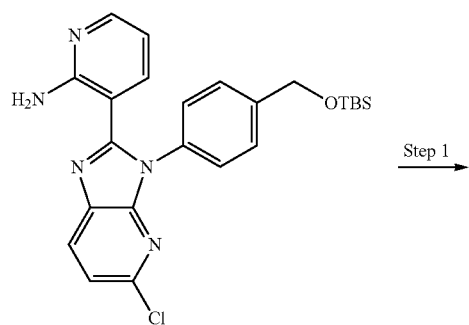

Step 1

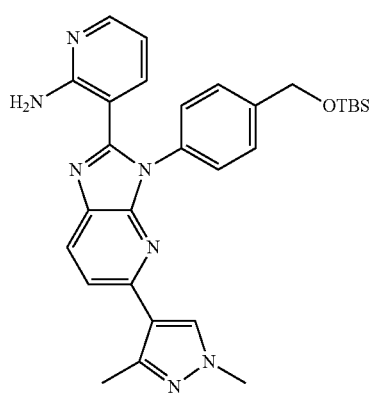

Step 2

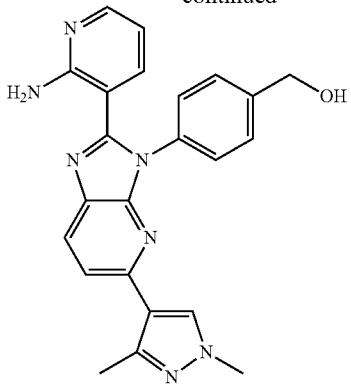

Step 3

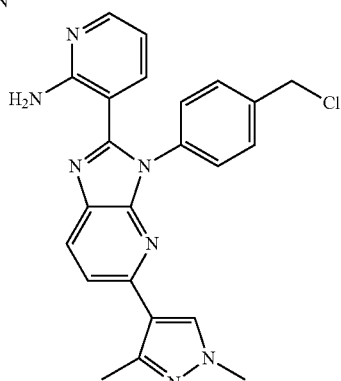

Intermediate 213

Step 1: 3-(3-(4-(((Tert-butyldimethylsilyl)oxy) methyl)phenyl)-5-(1,3-dimethyl-1H-pyrazol-4-yl)-3H-imidazo[4,5-b]pyridin-2-yl)pyridin-2-amine To a solution of 3-(3-(4-(((tert-butyldimethylsilyl)oxy) methyl)phenyl)-5-chloro-3H-imidazo[4,5-b]pyridin-2-yl) pyridin-2-amine (refer to Intermediate 117 for detail procedures, 500 mg, 1.07 mmol) in 1,4-dioxane (30 mL) and H₂O (6 mL) were added (1,3-dimethylpyrazol-4-yl)boronic acid (165 mg, 1.18 mmol), Pd(dppf)Cl₂ (78.5 mg, 107 µmol) and Cs₂CO₃ (1.05 g, 3.22 mmol) at 20° C. The reaction mixture was stirred at 100° C. for 3 hr under N₂. Water (30 mL) was added, and the mixture was extracted with EtOAc (50 mL×3). The combined organic layers were washed with brine (50 mL×2), dried over anhydrous Na₂SO₄, filtered, and concentrated under reduced pressure. 3-(3-(4-(((Tert-butyldimethylsilyl)oxy)methyl)phenyl)-5-(1,3-dimethyl-1H-pyrazol-4-yl)-3H-imidazo[4,5-b]pyridin-2-yl)pyridin-2-amine (560 mg, crude) was obtained as a black brown solid, which was used directly into the next step. MS: m/z=526.3 [M+H]⁺. ¹H NMR (400 MHz, Chloroform-d) δ 8.09-7.99 (m, 2H), 7.72 (s, 1H), 7.48-7.42 (m, 3H), 7.37 (d, J=8.4 Hz, 2H), 7.16-7.09 (m, 1H), 6.69-6.58 (m, 2H), 6.37 (dd, J=7.6, 4.8 Hz, 1H), 4.84 (s, 2H), 3.86 (s, 3H), 2.47 (s, 3H), 0.96 (s, 9H), 0.13 (s, 6H).

Step 2: (4-(2-(2-Aminopyridin-3-yl)-5-(1,3-dimethyl-1H-pyrazol-4-yl)-3H-imidazo[4,5-b]pyridin-3-yl)phenyl)methanol To a solution of 3-(3-(4-(((tert-butyldimethylsilyl)oxy) methyl)phenyl)-5-(1,3-dimethyl-1H-pyrazol-4-yl)-3H-imidazo[4,5-b]pyridin-2-yl)pyridin-2-amine (550 mg, 1.05 mmol) in THF (35 mL) was added TBAF (1 M in THF, 1.57 mL). The reaction mixture was stirred at 20° C. for 1 hr. Water (40 mL) was added, and the mixture was extracted with EtOAc (50 mL×3). The combined organic layers were washed with brine (50 mL×2), dried over anhydrous Na$_2$SO$_4$, filtered, and concentrated under reduced pressure. (4-(2-(2-Aminopyridin-3-yl)-5-(1,3-dimethyl-1H-pyrazol-4-yl)-3H-imidazo[4,5-b]pyridin-3-yl)phenyl)methanol (430 mg, crude) was obtained as a black brown solid, which was used directly into the next step. MS: m/z=412.2 [M+H]$^+$.

Step 3: 3-(3-(4-(Chloromethyl)phenyl)-5-(1,3-dimethyl-1H-pyrazol-4-yl)-3H-imidazo[4,5-b]pyridin-2-yl)pyridin-2-amine To a solution of (4-(2-(2-aminopyridin-3-yl)-5-(1,3-dimethyl-1H-pyrazol-4-yl)-3H-imidazo[4,5-b]pyridin-3-yl)phenyl)methanol (430 mg, 1.05 mmol) in CH$_2$Cl$_2$ (15 mL) was added SOCl$_2$ (373 mg, 3.14 mmol). The reaction mixture was stirred at 20° C. for 2 hr. The reaction mixture was concentrated to give 3-(3-(4-(chloromethyl)phenyl)-5-(1,3-dimethyl-1H-pyrazol-4-yl)-3H-imidazo[4,5-b]pyridin-2-yl)pyridin-2-amine (Intermediate 213, 440 mg, crude) as a black brown solid, which was used directly into the next step. $^1$H NMR (400 MHz, Methanol-d$_4$) δ 8.69 (s, 1H), 8.36 (d, J=7.6 Hz, 1H), 8.06 (d, J=4.4 Hz, 1H), 7.98-7.87 (m, 1H), 7.76-7.58 (m, 5H), 6.90 (s, 11H), 4.78 (s, 2H), 4.11 (s, 3H), 2.61 (s, 3H).

Intermediate 214: 3-(1-(4-(Chloromethyl)phenyl)-1H-imidazo[4,5-c]pyridin-2-yl)pyridin-2-amine

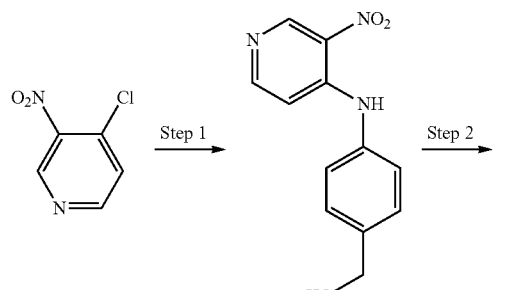

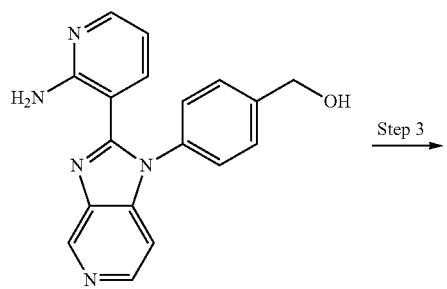

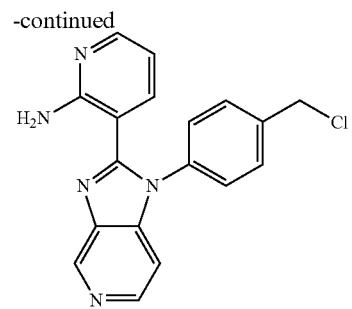

Intermediate 214

Step 1:
(4-((3-Nitropyridin-4-yl)amino)phenyl)methanol

To a mixture of 4-chloro-3-nitropyridine (2 g, 12.6 mmol) and (4-aminophenyl)methanol (1.71 g, 13.9 mmol) in THF (20 mL) was added DIEA (3.3 g, 25.2 mmol). The mixture was stirred at 80° C. for 12 hr. H$_2$O (50 mL) was added and the mixture was extracted with EtOAc (50 mL×2). The combined organic layers were washed with brine (50 mL), dried over anhydrous Na$_2$SO$_4$, filtered and concentrated. (4-((3-nitropyridin-4-yl)amino)phenyl)methanol (3 g, yield: 97%) was obtained as a yellow solid. MS: m/z=246.1 [M+H]$^+$. $^1$H NMR (400 MHz, Dimethylsulfoxide-d$_6$) δ 9.82 (s, 1H), 9.09 (s, 1H), 8.23 (d, J=6.0 Hz, 1H), 7.42 (d, J=8.4 Hz, 2H) 7.31 (d, J=8.0 Hz, 2H), 6.84 (d, J=6.0 Hz, 1H), 5.28 (t, J=6.0 Hz, 1H), 4.53 (d, J=5.4 Hz, 2H).

Step 2: (4-(2-(2-Aminopyridin-3-yl)-1H-imidazo[4,5-c]pyridin-1-yl)phenyl)methanol To a mixture of (4-((3-nitropyridin-4-yl)amino)phenyl)methanol (1.5 g, 6.1 mmol) and 2-aminonicotinaldehyde (821.7 mg, 6.7 mmol) in DMSO (10 mL) was added Na$_2$S$_2$O$_4$ (2.7 g, 15.3 mmol). Then it was stirred at 100° C. for 12 hr. The mixture was quenched with H$_2$O (200 mL) and extracted with CH$_2$Cl$_2$ (200 mL×2). The combined organic layers were washed with brine (100 mL), dried over anhydrous Na$_2$SO$_4$, filtered and concentrated. After purified by silica gel flash chromatography (EtOAc/EtOH (3/1) in petroleum ether=0-80%), (4-(2-(2-aminopyridin-3-yl)-1H-imidazo[4,5-c]pyridin-1-yl)phenyl)methanol (100 mg, yield: 5%) was obtained as a yellow oil. $^1$H NMR (400 MHz, Dimethylsulfoxide-d$_6$) δ 9.09 (s, 1H), 8.37 (d, J=5.6 Hz, 1H), 8.00 (dd, J=4.8, 1.6 Hz, 1H), 7.50 (d, J=8.0 Hz, 2H), 7.44 (d, J=8.0 Hz, 2H), 7.25-7.19 (m, 2H), 6.90 (s, 2H), 6.41 (dd, J=7.6, 4.8 Hz, 1H), 5.38 (t, J=5.6 Hz, 1H), 4.59 (d, J=5.6 Hz, 2H).

Step 3: 3-(1-(4-(Chloromethyl)phenyl)-1H-imidazo[4,5-c]pyridin-2-yl)pyridin-2-amine To a solution of (4-(2-(2-aminopyridin-3-yl)-1H-imidazo[4,5-c]pyridin-1-yl)phenyl)methanol (100 mg, 315 μmol) in CH$_2$Cl$_2$ (5 mL) was added SOCl$_2$ (112 mg, 945 gmol) at 25° C. The mixture was stirred at 25° C. for 2 hr. The reaction mixture was concentrated to give 3-(1-(4-(chloromethyl)phenyl)-1H-imidazo[4,5-c]pyridin-2-yl)pyridin-2-amine (Intermediate 214, 102 mg, yield: 96%) as a yellow solid, which was used directly without purification. MS: m/z=335.9 [M+H]$^+$.

Intermediate 215: 3-(3-(4-(Chloromethyl)phenyl)-5-(3-methoxypyridin-2-yl)-3H-imidazo[4,5-b]pyridin-2-yl)pyridin-2-amine

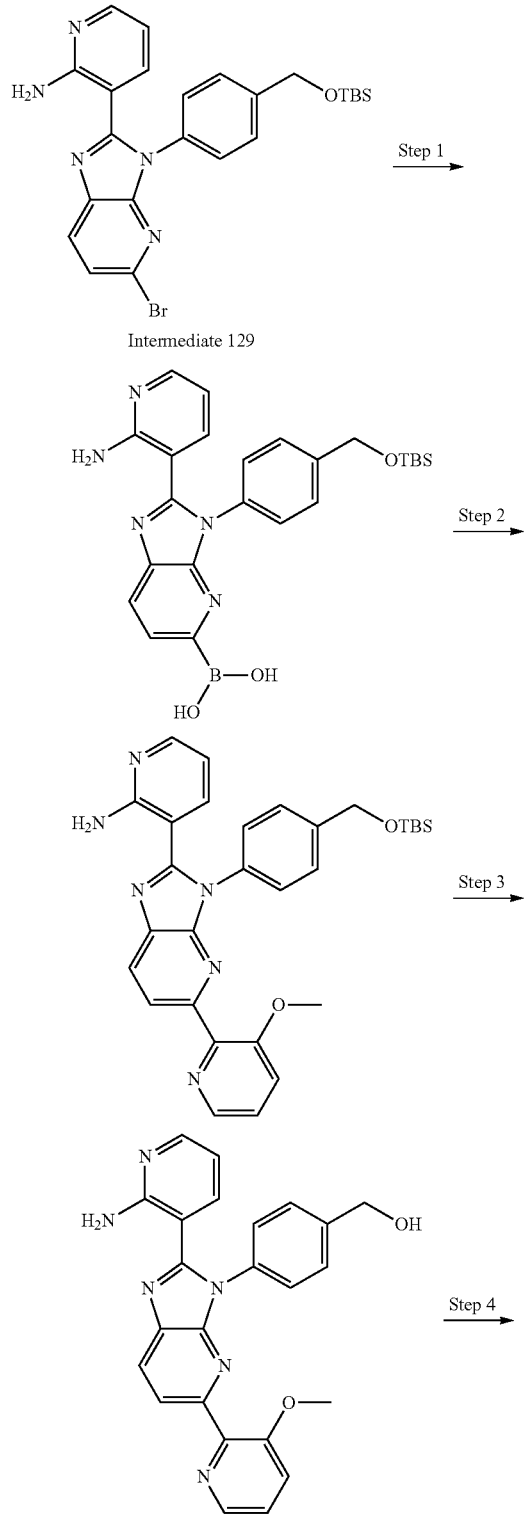

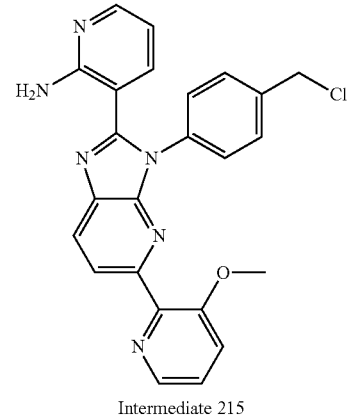 [SMILES: COc1cccnc1-c1ccc2nc(-c3cccnc3N)n(-c3ccc(CCl)cc3)c2n1]

Intermediate 215

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (500 mg 979 μmol), 4,4,4',4',5,5,5',5'-octamethyl-2,2'-bi(1,3,2-dioxaborolane) (497 mg, 1.96 mmol), KOAc (288 mg, 2.94 mmol) and Pd(dppf)Cl$_2$ (71.7 mg, 97.9 gmol) in 1,4-dioxane (2 mL) was degassed and purged with N$_2$ three times. The mixture was stirred at 80° C. for 16 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((tert-Butyldimethylsilyl)oxy)methyl)phenyl)-5-(3-methoxypyridin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (470 mg, 989 μmol), 2-bromo-3-methoxypyridine (186 mg, 989 μmol), Pd(dppf)Cl$_2$ (72.3 mg, 98.9 gmol) and Cs$_2$CO$_3$ (966 mg, 2.97 mmol) in 1,4-dioxane (5 mL) and H$_2$O (1 mL) was degassed and purged with N$_2$ three times. The mixture was stirred at 90° C. for 16 hr under N$_2$ atmosphere. The reaction mixture was quenched with H$_2$O (5 mL), diluted with CH$_2$Cl$_2$ (10 mL), and extracted with CH$_2$Cl$_2$ (15 mL×2). The combined organic layers were washed with brine (30 mL), dried over Na$_2$SO$_4$, filtered, and concentrated under reduced pressure. After purified by silica gel flash chromatography (Eluent of 30%~61% EtOAc in petroleum ether), 3-(3-(4-(((tert-butyldimethylsilyl)oxy)methyl)phenyl)-5-(3-methoxypyridin-2-yl)-3H-imidazo[4,5-b]pyridin-2-yl)pyridin-2-amine (280 mg, yield: 47% for two steps) was obtained as a black solid. MS: m/z=539.2 [M+H]$^+$. $^1$H NMR (400 MHz, Chloroform-d) δ 8.32 (dd, J=4.4, 1.6 Hz, 1H), 8.15 (d, J=8.4 Hz, 1H), 8.04 (dd, J=4.8, 1.6 Hz, 1H), 7.84 (d, J=8.4 Hz, 1H), 7.46-7.40 (m, 4H), 7.34-7.27 (m, 2H), 7.10 (dd, J=7.6, 1.6 Hz, 1H), 6.69 (br s, 2H), 6.36 (dd, J=8.0, 4.8 Hz, 1H), 4.80 (s, 2H), 3.83 (s, 3H), 0.95 (s, 9H), 0.12 (s, 6H).

Step 3: (4-(2-(2-Aminopyridin-3-yl)-5-(3-methoxypyridin-2-yl)-3/H-imidazo[4,5-b]pyridin-3-yl)phenyl)methanol To a solution of 3-(3-(4-(((tert-butyldimethylsilyl)oxy)methyl)phenyl)-5-(3-methoxypyridin-2-yl)-3H-imidazo[4, 5-b]pyridin-2-yl)pyridin-2-amine (250 mg, 464 μmol) in THF (5 mL) was added TBAF (1.4 mL, 1.4 mmol, 1 M in THF). The mixture was stirred at 25° C. for 0.5 hr. The reaction mixture was quenched with H$_2$O (5 mL) at 25° C., diluted with CH$_2$Cl$_2$ (10 mL), and extracted with CH$_2$Cl$_2$ (15 mL×3). The combined organic layers were washed with brine (50 mL×2), dried over Na$_2$SO$_4$, filtered and concentrated under reduced pressure. After triturated with EtOAc: petroleum ether=1:10 (10 mL) at 25° C. for 10 min, (4-(2-(2-aminopyridin-3-yl)-5-(3-methoxypyridin-2-yl)-3H-imidazo[4,5-b]pyridin-3-yl)phenyl)methanol (175 mg, yield: 84%) was obtained as a brown solid. MS: m/z=425.2 [M+H]. $^1$H NMR (400 MHz, Dimethylsulfoxide-d$_6$) δ 8.26-8.20 (m, 2H), 7.99 (dd, J=4.8, 2.0 Hz, 1H), 7.67 (d, J=8.0 Hz, 1H), 7.61-7.53 (m, 1H), 7.46-7.38 (m, 5H), 7.23 (dd, J=7.6, 1.6 Hz, 1H), 6.96 (br s, 2H), 6.42 (dd, J=7.6, 5.2 Hz, 1H), 5.34 (t, J=6.0 Hz, 1H), 4.56 (d, J=6.0 Hz, 2H), 3.77 (s, 3H).

Step 4: 3-(3-(4-(Chloromethyl)phenyl)-5-(3-methoxypyridin-2-yl)-3H-imidazo[4,5-b]pyridin-2-yl)pyridin-2-amine To a solution of (4-(2-(2-aminopyridin-3-yl)-5-(3-methoxypyridin-2-yl)-3H-imidazo[4,5-b]pyridin-3-yl)phenyl)methanol (175 mg, 412 μmol) in CH$_2$Cl$_2$ (5 mL) was added SOCl$_2$ (245 mg, 2.06 mmol). The mixture was stirred at 25° C. for 0.5 hr. The reaction was concentrated under reduced pressure to give 3-(3-(4-(chloromethyl)phenyl)-5-(3-methoxypyridin-2-yl)-3H-imidazo[4,5-b]pyridin-2-yl)pyridin-2-amine (Intermediate 215, 198 mg, HCl salt) as a brown solid. MS: m/z=443.1 [M+H]$^+$. $^1$H NMR (400 MHz, Methanol-d$_4$) δ8.62 (d, J=8.4 Hz, 1H), 8.54-8.45 (m, 3H), 8.09-8.04 (m, 2H), 7.86 (d, J=7.2 Hz, 1H), 7.74-7.69 (m, 2H), 7.66-7.62 (m, 2H), 6.91-6.83 (m, 1H), 4.79 (s, 2H), 4.26 (s, 3H).

Intermediate 216: 3-(3-(4-(Chloromethyl)phenyl)-5-(1-methyl-1H-1,2,3-triazol-5-yl)-3H-imidazo[4,5-b]pyridin-2-yl)pyridin-2-amine

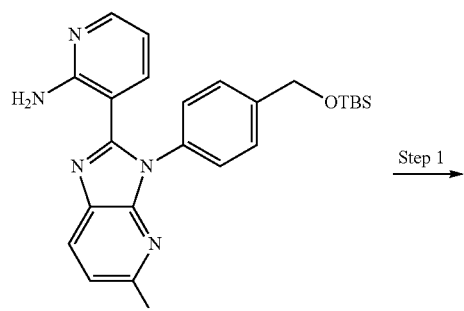

Intermediate 129

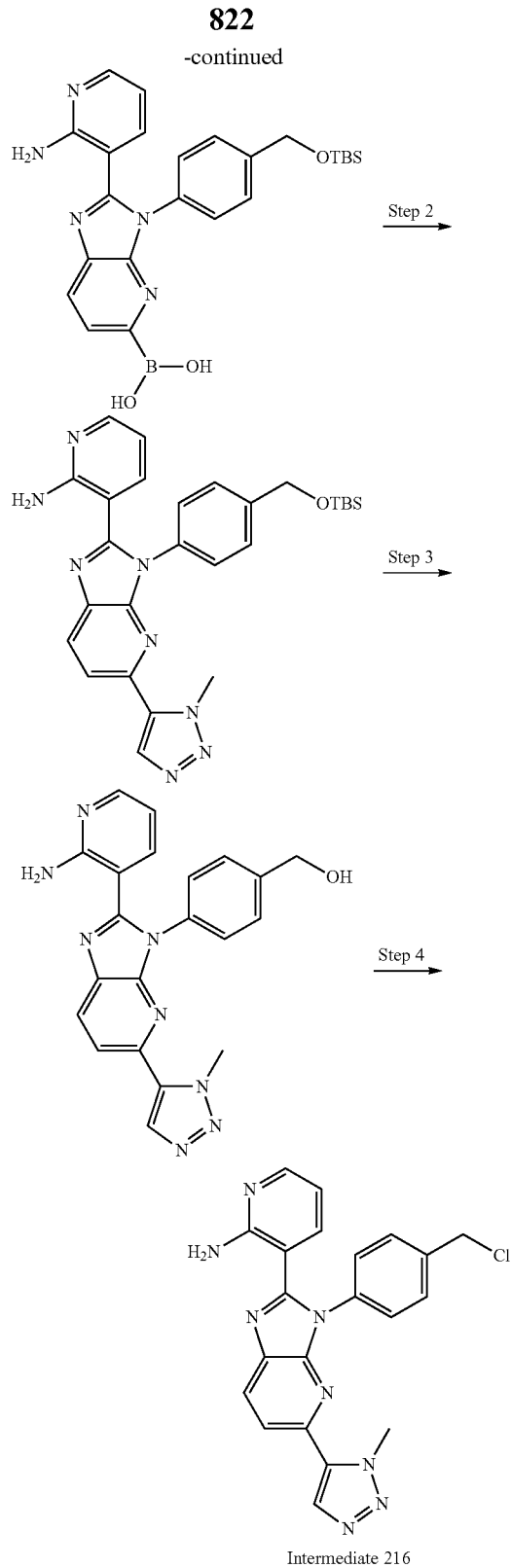

Intermediate 216

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4', 4',5,5,5',5'-octamethyl-2,2'-bi(1,3,2-dioxaborolane) (995 mg, 3.92 mmol), KOAc (577 mg, 5.88 mmol) and Pd(dppf)Cl₂ (143 mg, 196 mmol) in 1,4-dioxane (5 mL) was degassed and purged with N₂ three times. The mixture was stirred at 90° C. for 16 hr under N₂ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid and used in the next step without work-up and purification. MS: m/z=476.2 [M+H]⁺.

Step 2: 3-(3-(4-(((tert-Butyldimethylsilyl)oxy)methyl)phenyl)-5-(1-methyl-1H-1,2,3-triazol-5-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (400 mg, 841 µmol), 5-bromo-1-methyl-1H-1,2,3-triazole (164 mg, 1.01 mmol), Pd(dppf)Cl₂ (61.6 mg, 84.1 µmol) and Cs₂CO₃ (822 mg, 2.52 mmol) in 1,4-dioxane (4 mL) and H₂O (1 mL) was degassed and purged with N₂ three times. The mixture was stirred at 90° C. for 16 hr under N₂ atmosphere. The reaction mixture was poured into H₂O (15 mL) and extracted with EtOAc (15 mL×3). The combined organic layers were dried over anhydrous Na₂SO₄, filtered, and concentrated under reduced pressure. After purified by silica gel flash chromatography (Eluent of 0%~50% EtOAc in petroleum ether), 3-(3-(4-(((tert-butyldimethylsilyl)oxy)methyl)phenyl)-5-(1-methyl-1H-1,2,3-triazol-5-yl)-3H-imidazo[4,5-b]pyridin-2-yl)pyridin-2-amine (210 mg, yield: 49% for two steps) was obtained as a brown solid. MS: m/z=513.2 [M+H]⁺. ¹H NMR (400 MHz, Dimethysulfoxide-d₆) δ 8.36-8.33 (m, 2H), 8.15 (dd, J=5.2, 2.0 Hz, 1H), 7.91 (d, J=8.4 Hz, 1H), 7.53-7.46 (m, 4H), 7.25 (dd, J=7.6, 1.6 Hz, 1H), 7.02 (s, 2H), 6.41 (dd, J=7.6, 4.8 Hz, 1H), 4.80 (s, 2H), 4.16 (s, 3H), 0.91 (s, 9H), 0.09 (s, 6H).

Step 3: (4-(2-(2-Aminopyridin-3-yl)-5-(1-methyl-1H-1,2,3-triazol-5-yl)-3H-imidazo[4,5-b]pyridin-3-yl)phenyl)methanol To a solution of 3-(3-(4-(((tert-butyldimethylsilyl)oxy)methyl)phenyl)-5-(1-methyl-1H-1,2,3-triazol-5-yl)-3H-imidazo[4,5-b]pyridin-2-yl)pyridin-2-amine (210 mg, 410 µmol) in THF (1 mL) was added TBAF (1 mL, 1 M in THF). The mixture was stirred at 25° C. for 1 hr. The reaction mixture was poured into H₂O (15 mL) and extracted with EtOAc (15 mL×3). The combined organic layers were dried over anhydrous Na₂SO₄, filtered, and concentrated under reduced pressure. (4-(2-(2-Aminopyridin-3-yl)-5-(1-methyl-1H-1,2,3-triazol-5-yl)-3H-imidazo[4,5-b]pyridin-3-yl)phenyl)methanol (150 mg, crude) was obtained as a brown solid. MS: m/z=399.1 [M+H]⁺.

Step 4: 3-(3-(4-(Chloromethyl)phenyl)-5-(1-methyl-1H-1,2,3-triazol-5-yl)-3H-imidazo[4,5-b]pyridin-2-yl)pyridin-2-amine To a solution of (4-(2-(2-aminopyridin-3-yl)-5-(1-methyl-1H-1,2,3-triazol-5-yl)-3H-imidazo[4,5-b]pyridin-3-yl)phenyl)methanol (150 mg, 376 µmol) in CH₂Cl₂ (2 mL) was added SOCl₂ (1.09 g, 9.16 mmol). The mixture was stirred at 25° C. for 1 hr. The reaction was concentrated under reduced pressure to give 3-(3-(4-(chloromethyl)phenyl)-5-(1-methyl-1H-1,2,3-triazol-5-yl)-3H-imidazo[4,5-b]pyridin-2-yl)pyridin-2-amine (Intermediate 216, 155 mg, HCl salt) as a brown solid. MS: m/z=417.1 [M+H]⁺.

Intermediate 217: 2-(2-Aminopyridin-3-yl)-3-(4-(chloromethyl)phenyl)-6-methyl-3H-imidazo[4,5-b]pyridine-5-carbonitrile

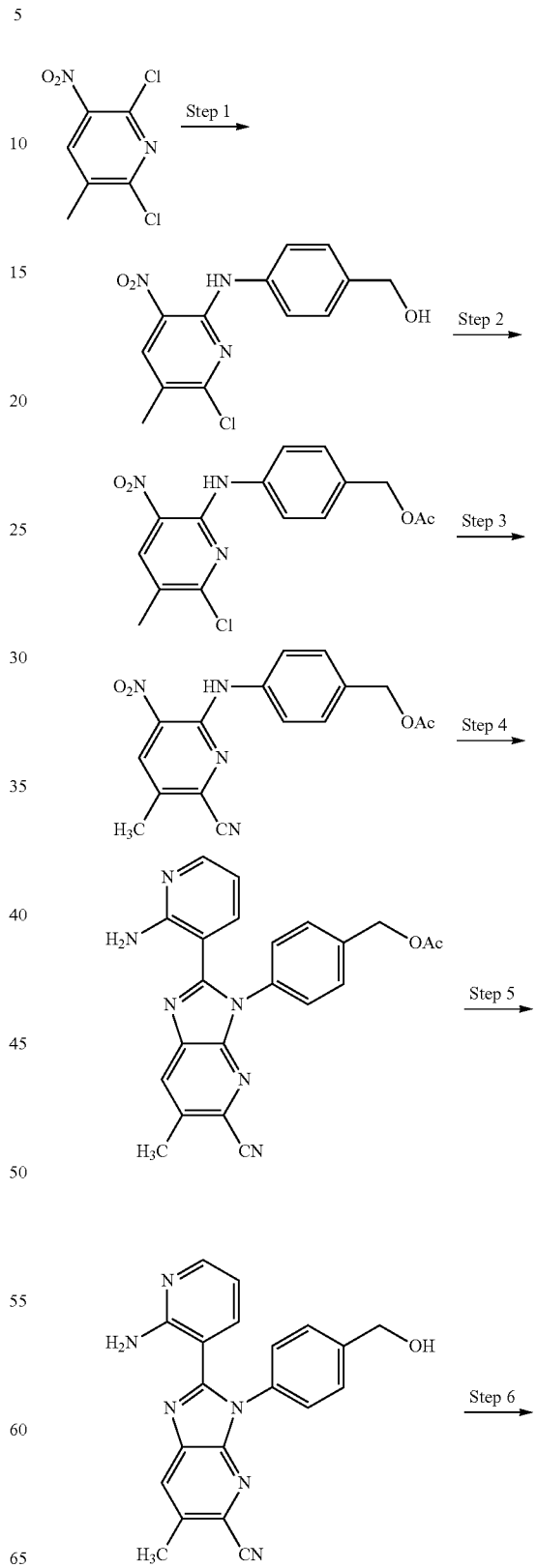

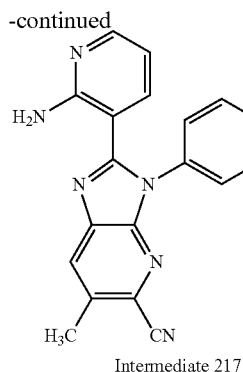

Intermediate 217

Step 1: (4-((6-Chloro-5-methyl-3-nitropyridin-2-yl)amino)phenyl)methanol

To a solution of 2,6-dichloro-3-methyl-5-nitropyridine (10 g, 48.3 mmol) and (4-aminophenyl)methanol (5.35 g, 43.5 mmol) in 1,4-dioxane (100 mL) was added DIEA (12.5 g, 96.6 mmol). The mixture was stirred at 60° C. for 16 hr. The reaction mixture was diluted with $H_2O$ (100 mL) and extracted with $CH_2Cl_2$ (100 mL×3). The combined organic layers were washed with brine (100 mL×4), dried over $Na_2SO_4$, filtered and concentrated under reduced pressure. (4-((6-Chloro-5-methyl-3-nitropyridin-2-yl)amino)phenyl)methanol (14 g, crude) was obtained as a red solid. MS: m/z=294.0 $[M+H]^+$.

Step 2: 4-((6-Chloro-5-methyl-3-nitropyridin-2-yl)amino)benzyl acetate

To a solution of (4-((6-chloro-5-methyl-3-nitropyridin-2-yl)amino)phenyl)methanol (14 g, 47.7 mmol) and TEA (14.5 g, 143 mmol) in $CH_2Cl_2$ (200 mL) were added $Ac_2O$ (7.3 g, 71.5 mmol) and DMAP (582 mg, 4.77 mmol). The mixture was stirred at 25° C. for 1 hr. The reaction mixture was diluted with $H_2O$ (200 mL) and extracted with $CH_2Cl_2$ (200 mL×3). The combined organic layers were washed with brine (300 mL), dried over $Na_2SO_4$, filtered and concentrated under reduced pressure. After purified by silica gel flash chromatography (Eluent of 0~10% EtOAc in petroleum ether), 4-((6-chloro-5-methyl-3-nitropyridin-2-yl)amino)benzyl acetate (7 g, yield: 44% for two steps) was obtained as a red solid. MS: m/z=336.0 $[M+H]^+$. $^1H$ NMR (400 MHz, Dimethylsulfoxide-$d_6$) δ 9.98 (s, 1H), 8.56 (s, 1H), 7.60 (d, J=8.4 Hz, 2H), 7.38 (d, J=8.8 Hz, 2H), 5.06 (s, 2H), 2.29 (s, 3H), 2.07 (s, 3H).

Step 3: 4-((6-Cyano-5-methyl-3-nitropyridin-2-yl)amino)benzyl acetate

To a solution of 4-((6-chloro-5-methyl-3-nitropyridin-2-yl)amino)benzyl acetate (2.4 g, 7.15 mmol) in DMF (30 mL) was added CuCN (3.2 g, 35.7 mmol). The mixture was stirred at 180° C. for 8 hr. The reaction mixture was quenched with $H_2O$ (50 mL) at 25° C. and extracted with $CH_2Cl_2$ (100 mL×3). The combined organic layers were washed with brine (100 mL×5), dried over $Na_2SO_4$, filtered and concentrated under reduced pressure. After purified by silica gel flash chromatography (Eluent of 0~5% EtOAc in petroleum ether), 4-((6-cyano-5-methyl-3-nitropyridin-2-yl)amino)benzyl acetate (150 mg, yield: 6.4%) was obtained as a red solid. MS: m/z=326.9 $[M+H]^+$. $^1H$ NMR (400 MHz, Dimethylsulfoxide-$d_6$) δ 9.80 (s, 1H), 8.66 (s, 1H), 7.57 (d, J=8.4 Hz, 2H), 7.38 (d, J=8.0 Hz, 2H), 5.06 (s, 2H), 2.44 (s, 3H), 2.07 (s, 3H).

Step 4: 4-(2-(2-Aminopyridin-3-yl)-5-cyano-6-methyl-3H-imidazo[4,5-b]pyridin-3-yl)benzyl acetate A mixture of 4-((6-cyano-5-methyl-3-nitropyridin-2-yl)amino)benzyl acetate (140 mg, 429 μmol) and 2-aminonicotinaldehyde (63 mg, 515 μmol) in DMSO (2 mL) was added $Na_2S_2O_4$ (352 mg, 1.72 mmol) at 25° C. The mixture was stirred at 80° C. for 16 hr. The reaction mixture was quenched with $H_2O$ (10 mL) at 25° C., diluted with $CH_2Cl_2$ (10 mL), and extracted with $CH_2Cl_2$ (10 mL×3). The combined organic layers were washed with brine (10 mL×3), dried over $Na_2SO_4$, filtered, and concentrated under reduced pressure. After purified by prep-TLC (100% EtOAc), 4-(2-(2-aminopyridin-3-yl)-5-cyano-6-methyl-3H-imidazo[4,5-b]pyridin-3-yl)benzyl acetate (30 mg, yield: 18%) was obtained as a yellow solid. MS: m/z=399.4 $[M+H]^+$.

Step 5: 2-(2-Aminopyridin-3-yl)-3-(4-(hydroxymethyl)phenyl)-6-methyl-3H-imidazo[4,5-b]pyridine-5-carbonitrile To a solution of 4-(2-(2-aminopyridin-3-yl)-5-cyano-6-methyl-3H-imidazo[4,5-b]pyridin-3-yl)benzyl acetate (30 mg, 75.3 μmol) in THF (1 mL) were added $K_2CO_3$ (31.2 mg, 226 mmol), MeOH (1 mL) and $H_2O$ (1 mL). The mixture was stirred at 25° C. for 0.5 hr. The reaction mixture was diluted with $H_2O$ (20 mL) and extracted with $CH_2Cl_2$ (20 mL×3). The combined organic layers were washed with brine (40 mL), dried over $Na_2SO_4$, filtered and concentrated under reduced pressure to give 2-(2-aminopyridin-3-yl)-3-(4-(hydroxymethyl)phenyl)-6-methyl-3H-imidazo[4,5-b]pyridine-5-carbonitrile (27 mg, crude) as a yellow solid. MS: m/z=357.2 $[M+H]^+$.

Step 6: 2-(2-Aminopyridin-3-yl)-3-(4-(chloromethyl)phenyl)-6-methyl-3H-imidazo[4,5-b]pyridine-5-carbonitrile To a solution of 2-(2-aminopyridin-3-yl)-3-(4-(hydroxymethyl)phenyl)-6-methyl-3H-imidazo[4,5-b]pyridine-5-carbonitrile (27 mg, 75.8 μmol) in $CH_2Cl_2$ (2 mL) was added $SOCl_2$ (0.3 mL). The mixture was stirred at 40° C. for 1 hr. The mixture was concentrated under reduced pressure to give 2-(2-aminopyridin-3-yl)-3-(4-(chloromethyl)phenyl)-6-methyl-3H-imidazo[4,5-b]pyridine-5-carbonitrile (Intermediate 217, 28 mg, crude) was obtained as a yellow solid. MS: m/z=375.0 $[M+H]^+$.

Intermediate 218: 3-(3-(4-(Chloromethyl)phenyl)-5-(5-methyl-1,3,4-oxadiazol-2-yl)-3H-imidazo[4,5-b]pyridin-2-yl)pyridin-2-amine

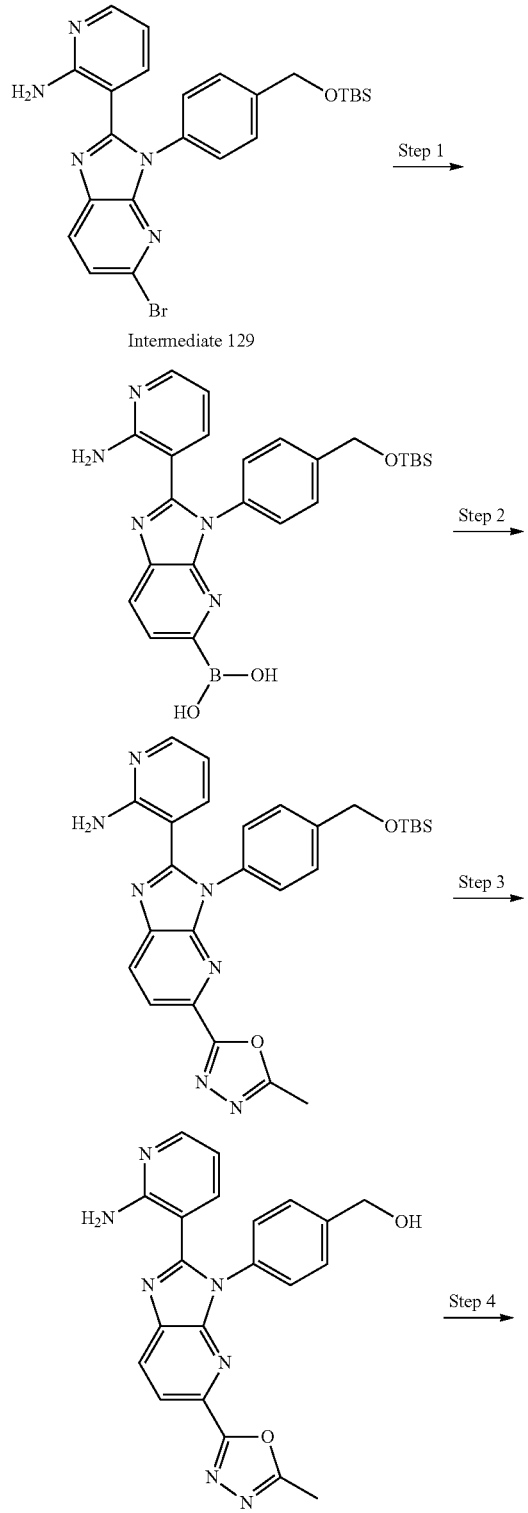

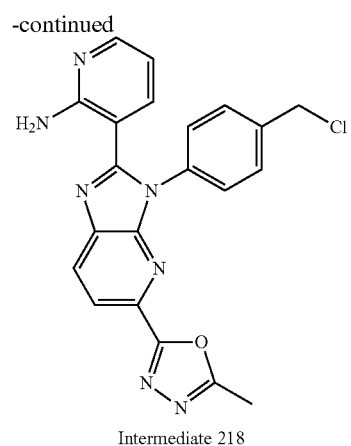

Intermediate 218

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1.5 g, 2.94 mmol), 4,4,5,5-tetramethyl-2-(4,4,5,5-tetramethyl-1,3,2-dioxaborolan-2-yl)-1,3,2-dioxaborolane (1.49 g, 5.88 mmol), KOAc (865 mg, 8.81 mmol) and Pd(dppf)Cl$_2$ (215 mg, 294 μmol) in 1,4-dioxane (5 mL) was degassed and purged with N$_2$ three times, and then the mixture was stirred at 90° C. for 16 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid (1.5 g, crude) was obtained as a black brown solid, which was directly used in the next step without further purification. MS: m/z=476.2 [M+H]$^+$.

Step 2: 3-(3-(4-(((tert-Butyldimethylsilyl)oxy)methyl)phenyl)-5-(5-methyl-1,3,4-oxadiazol-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (475 mg, 999 μmol), 2-bromo-5-methyl-1,3,4-oxadiazole (163 mg, 999 μmol), Cs$_2$CO$_3$ (977 mg, 3.00 mmol) and Pd(dppf)Cl$_2$ (73 mg, 100 μmol) in 1,4-dioxane (4 mL) and H$_2$O (1 mL) was degassed and purged with N$_2$ three times. The mixture was stirred at 90° C. for 16 hr under N$_2$ atmosphere. The reaction mixture was diluted with H$_2$O (30 mL) and extracted with EtOAc (20 mL×3). The combined organic layers were washed with brine (30 mL), dried over Na$_2$SO$_4$, filtered and concentrated under reduced pressure. After purified by silica gel flash chromatography (Eluent of 0~100% EtOAc in petroleum ether), 3-(3-(4-(((tert-butyldimethylsilyl)oxy)methyl)phenyl)-5-(5-methyl-1,3,4-oxadiazol-2-yl)-3H-imidazo[4,5-b]pyridin-2-yl)pyridin-2-amine (150 mg, yield: 23% for two steps) was obtained as a brown solid. MS: m/z=514.1 [M+H]$^+$. $^1$H NMR (400 MHz, Dimethysulfoxide-d) 8.40 (d, J=8.4 Hz, 1H), 8.18 (d, J=8.4 Hz, 1H), 8.01 (dd, J=4.8, 2.0 Hz, 1H), 7.53-7.44 (m, 4H), 7.25-7.18 (m, 1H), 7.04-6.92 (m, 2H), 6.39 (dd, J=7.6, 4.8 Hz, 1H), 4.82 (s, 2H), 2.56 (s, 3H), 0.93 (s, 9H), 0.12 (s, 6H).

Step 3: (4-(2-(2-Aminopyridin-3-yl)-5-(5-methyl-1,3,4-oxadiazol-2-yl)-3H-imidazo[4,5-b]pyridin-3-yl)phenyl)methanol To a solution of 3-(3-(4-(((tert-butyldimethylsilyl)oxy)methyl)phenyl)-5-(5-methyl-1,3,4-oxadiazol-2-yl)-3H-imidazo[4,5-b]pyridin-2-yl)pyridin-2-amine (150 mg, 292 µmol) in THF (3 mL) was added TBAF (0.6 mL, 1 M in THF). The mixture was stirred at 25° C. for 0.5 hr. The reaction mixture was diluted with H₂O (30 mL) and extracted with EtOAc (20 mL×3). The combined organic layers were washed with brine (30 mL), dried over Na₂SO₄, filtered, and concentrated under reduced pressure. The crude product was used in the next step without further purification. (4-(2-(2-Aminopyridin-3-yl)-5-(5-methyl-1,3,4-oxadiazol-2-yl)-3H-imidazo[4,5-b]pyridin-3-yl)phenyl)methanol (100 mg, crude) was obtained as a yellow solid. MS: m/z=400.1 [M+H]⁺.

Step 4: 3-(3-(4-(Chloromethyl)phenyl)-5-(5-methyl-1,3,4-oxadiazol-2-yl)-3H-imidazo[4,5-b]pyridin-2-yl)pyridin-2-amine To a solution of (4-(2-(2-aminopyridin-3-yl)-5-(5-methyl-1,3,4-oxadiazol-2-yl)-3H-imidazo[4,5-b]pyridin-3-yl)phenyl)methanol (100 mg, 250 µmol) in CH₂Cl₂ (2 mL) was added SOCl₂ (60 mg, 501 µmol). The mixture was stirred at 40° C. for 0.5 hr. The mixture was concentrated under reduced pressure. The crude product was used in the next step without further purification. 3-(3-(4-(Chloromethyl)phenyl)-5-(5-methyl-1,3,4-oxadiazol-2-yl)-3H-imidazo[4,5-b]pyridin-2-yl)pyridin-2-amine (Intermediate 218, 100 mg, HCl salt) was obtained as a yellow solid. MS: m/z=418.0 [M+H]⁺.

Intermediate 219: 3-(3-(4-(chloromethyl)phenyl)-5-(1-methyl-1H-1,2,4-triazol-5-yl)-3H-imidazo[4,5-b]pyridin-2-yl)pyridin-2-amine

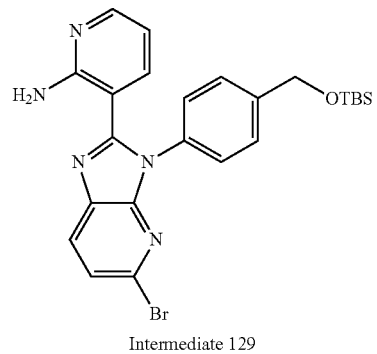

Intermediate 129

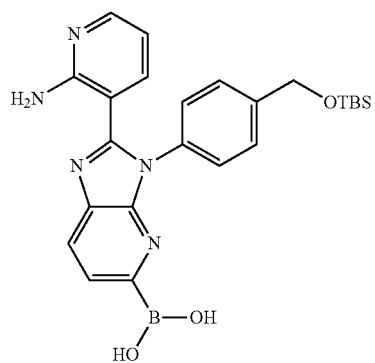

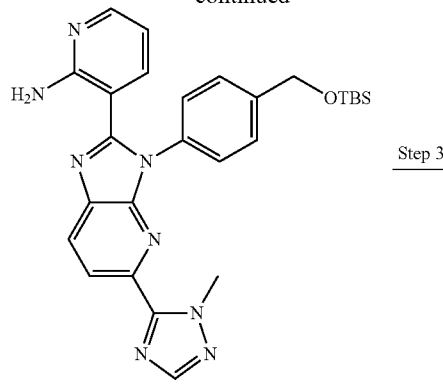

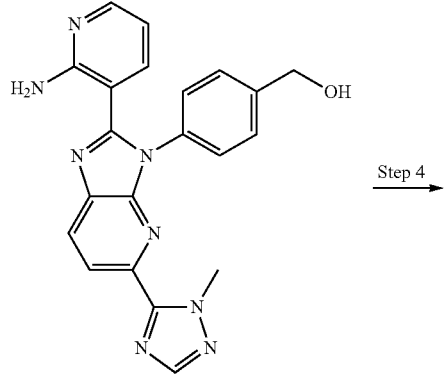

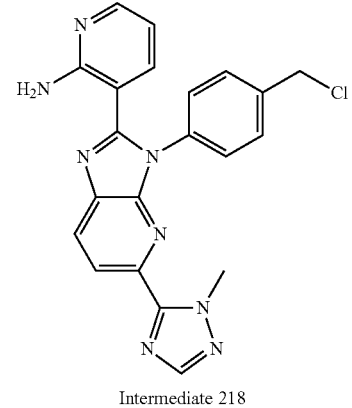 [SMILES: Cn1ncnc1-c1ccc2nc(-c3cccnc3N)n(-c3ccc(CCl)cc3)c2n1]

Intermediate 218

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl₂ (143 mg, 196 mmol) in 1,4-dioxane (5 mL) was degassed and purged with N₂ three times. The mixture was stirred at 90° C. for 16 hr under N₂ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]⁺.

Step 2: 3-(3-(4-(((Tert-butyldimethylsilyl)oxy)methyl)phenyl)-5-(1-methyl-1H-1,2,4-triazol-5-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (470 mg, 988 µmol), 5-bromo-1-methyl-1H-1,2,4-triazole (192 mg, 1.19 mmol), Pd(dppf)Cl$_2$ (72.3 mg, 98.9 µmol) and Cs$_2$CO$_3$ (966 mg, 2.97 mmol) in 1,4-dioxane (4 mL) and H$_2$O (1 mL) was degassed and purged with N$_2$ three times. The mixture was stirred at 90° C. for 16 hr under N$_2$ atmosphere. The reaction mixture was poured into H$_2$O (15 mL) and extracted with EtOAc (15 mL×3). The organic phase was dried over anhydrous Na$_2$SO$_4$, filtered, and concentrated under reduced pressure. After purified by silica gel flash chromatography (Eluent of 0%~50% EtOAc in petroleum ether), 3-(3-(4-(((tert-butyldimethylsilyl)oxy)methyl)phenyl)-5-(1-methyl-1H-1,2,4-triazol-5-yl)-3H-imidazo[4,5-b]pyridin-2-yl)pyridin-2-amine (201 mg, yield: 40% for two steps) was obtained as a brown solid. MS: m/z=513.2 [M+H]$^+$. $^1$H NMR (400 MHz, Dimethysulfoxide-d$_6$) δ 8.37 (d, J=8.4 Hz, 1H), 8.16 (d, J=8.4 Hz, 1H), 8.08-7.92 (m, 2H), 7.53-7.46 (m, 4H), 7.25 (dd, J=7.6, 1.6 Hz, 1H), 7.02 (s, 2H), 6.41 (dd, J=8.0, 4.8 Hz, 1H), 4.80 (s, 2H), 4.08 (s, 3H), 0.91 (s, 9H), 0.07 (s, 6H).

Step 3: (4-(2-(2-Aminopyridin-3-yl)-5-(1-methyl-1H-1,2,4-triazol-5-yl)-3H-imidazo[4,5-b]pyridin-3-yl)phenyl)methanol To a solution of 3-(3-(4-(((tert-butyldimethylsilyl)oxy)methyl)phenyl)-5-(1-methyl-1H-1,2,4-triazol-5-yl)-3H-imidazo[4,5-b]pyridin-2-yl)pyridin-2-amine (201 mg, 392 µmol) in THF (2 mL) was added TBAF (0.4 mL, 392 µmol, 1 M in THF). The mixture was stirred at 25° C. for 1 hr. The reaction mixture was poured into H$_2$O (15 mL), extracted with EtOAc (15 mL×3). The combined organic layers were dried over anhydrous Na$_2$SO$_4$, filtered, and concentrated under reduced pressure to give (4-(2-(2-aminopyridin-3-yl)-5-(1-methyl-1H-1,2,4-triazol-5-yl)-3H-imidazo[4,5-b]pyridin-3-yl)phenyl)methanol (155 mg, crude) as a brown solid. MS: m/z=399.1 [M+H]$^+$.

Step 4: 3-(3-(4-(Chloromethyl)phenyl)-5-(1-methyl-1H-1,2,4-triazol-5-yl)-3H-imidazo[4,5-b]pyridin-2-yl)pyridin-2-amine To a solution of (4-(2-(2-aminopyridin-3-yl)-5-(1-methyl-1H-1,2,4-triazol-5-yl)-3H-imidazo[4,5-b]pyridin-3-yl)phenyl)methanol (i 55 mg, 389 µmol) in CH$_2$Cl$_2$ (2 mL) was added SOCl$_2$ (1 mL). The mixture was stirred at 25° C. for 1 hr. The reaction was concentrated under reduced pressure to give 3-(3-(4-(chloromethyl)phenyl)-5-(1-methyl-1H-1,2,4-triazol-5-yl)-3H-imidazo[4,5-b]pyridin-2-yl)pyridin-2-amine (Intermediate 219, 180 mg HCl salt) as a brown solid. MS: m/z=417.0 [M+H]$^+$.

Intermediate 220: 3-(3-(4-(Chloromethyl)phenyl)-5-(4-methyl-2H-1,2,3-triazol-2-yl)-3H-imidazo[4,5-b]pyridin-2-yl)pyridin-2-amine

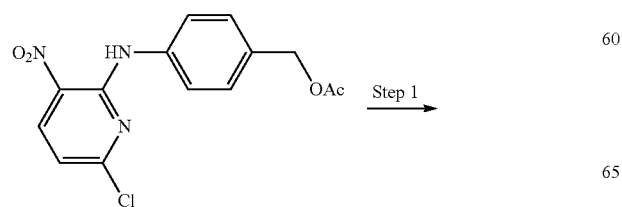

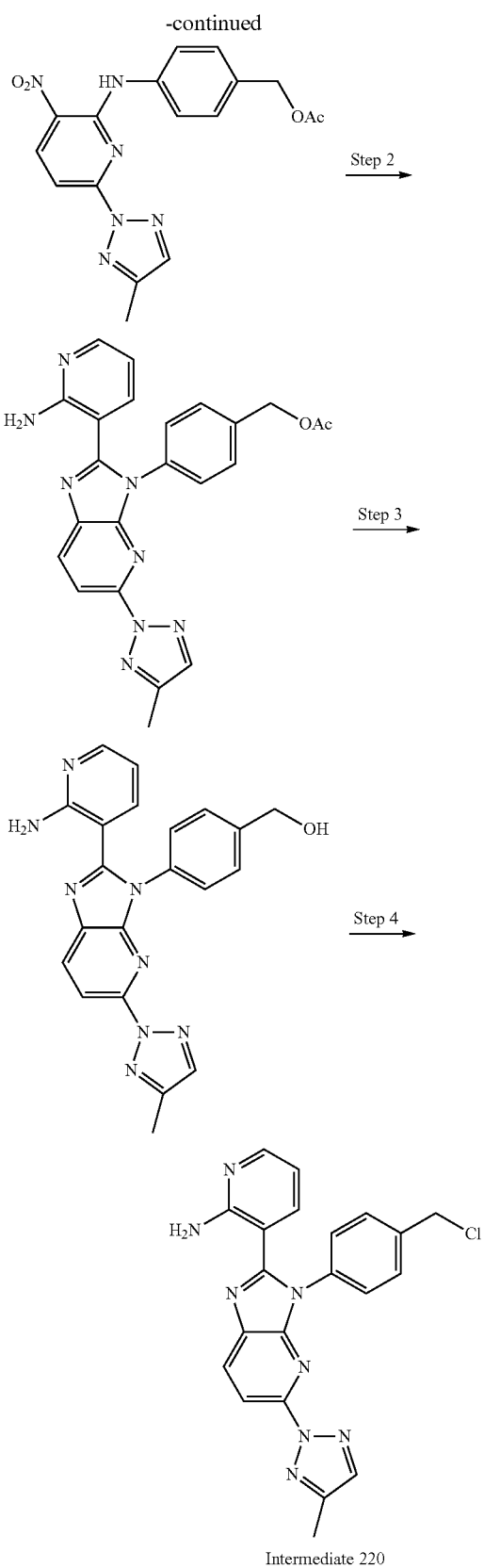

Step 1: 4-((6-(4-Methyl-2H-1,2,3-triazol-2-yl)-3-nitropyridin-2-yl)amino)benzyl acetate To a solution of 4-((6-chloro-3-nitropyridin-2-yl)amino)benzyl acetate (refer to Intermediate 178 for detail procedures, 3 g, 9.33 mmol) and 4-methyl-1H-1,2,3-triazole (775 mg, 9.33 mmol) in DMF (30 mL) were added K$_2$CO$_3$ (6.44 g, 46.6 mmol) and NaI (140 mg, 933 µmol). The mixture was stirred at 80° C. for 1 hr. The reaction mixture was quenched with H$_2$O (100 mL) at 25° C. and extracted with CH$_2$Cl$_2$ (100 mL×2). The combined organic layers were washed with brine (100 mL×3), dried over Na$_2$SO$_4$, filtered, and concentrated under reduced pressure. After purified by silica gel flash chromatography (Eluent of 10%~20% EtOAc in petroleum ether), 4-((6-(4-methyl-2H-1,2,3-triazol-2-yl)-3-nitropyridin-2-yl)amino)benzyl acetate (1.4 g, yield: 40%) was obtained as a red solid. MS: m/z=369.1 [M+H]$^+$. $^1$H NMR (400 MHz, Dimethylsulfoxide-d$_6$) δ 10.33 (s, 1H), 8.76 (d, J=9.2 Hz, 1H), 8.13 (s, 1H), 8.03-7.95 (m, 2H), 7.50 (d, J=9.2 Hz, 1H), 7.41 (d, J=8.4 Hz, 2H), 5.08 (s, 2H), 2.42 (s, 3H), 2.08 (s, 3H).

Step 2: 4-(2-(2-Aminopyridin-3-yl)-5-(4-methyl-2H-1,2,3-triazol-2-yl)-3H-imidazo[4,5-b]pyridin-3-yl)benzyl acetate To a solution of 4-((6-(4-methyl-2H-1,2,3-triazol-2-yl)-3-nitropyridin-2-yl)amino)benzyl acetate (1.4 g, 3.8 mmol) in DMSO (10 mL) were added Na$_2$S$_2$O$_4$ (2.65 g, 15.2 mmol, 87% purity) and 2-aminonicotinaldehyde (511 mg, 4.18 mmol). The mixture was stirred at 100° C. for 4 hr. The reaction mixture was quenched with H$_2$O (100 mL) at 25° C. and extracted with CH$_2$Cl$_2$ (100 mL×2). The combined organic layers were washed with brine (100 mL×2), dried over Na$_2$SO$_4$, filtered, and concentrated under reduced pressure. After purified by silica gel flash chromatography (Eluent of 20%~70% EtOAc in petroleum ether), 4-(2-(2-aminopyridin-3-yl)-5-(4-methyl-2H-1,2,3-triazol-2-yl)-3H-imidazo[4,5-b]pyridin-3-yl)benzyl acetate (240 mg, yield: 14%) was obtained as a red solid. MS: m z=441.1 [M+H]I. $^1$H NMR (400 MHz, Dimethylsulfoxide-d$_6$) δ 8.40 (d, J=8.8 Hz, 1H), 8.03-7.88 (m, 3H), 7.58-7.47 (m, 4H), 7.23 (dd, J=7.6, 1.6 Hz, 1H), 6.84 (s, 2H), 6.43 (dd, J=7.6, 4.8 Hz, 1H), 5.17 (s, 2H), 2.35 (s, 3H), 2.12 (s, 3H).

Step 3: (4-(2-(2-Aminopyridin-3-yl)-5-(4-methyl-2H-1,2,3-triazol-2-yl)-3H-imidazo[4,5-b]pyridin-3-yl)phenyl)methanol To a solution of 4-(2-(2-aminopyridin-3-yl)-5-(4-methyl-2H-1,2,3-triazol-2-yl)-3H-imidazo[4,5-b]pyridin-3-yl)benzyl acetate (240 mg, 545 µmol) in THF (5 mL) and MeOH (5 mL) was added K$_2$CO$_3$ (226 mg, 1.63 mmol). The mixture was stirred at 25° C. for 0.5 hr. The reaction mixture was quenched with H$_2$O (50 mL) at 25° C. and extracted with CH$_2$Cl$_2$ (50 mL×3). The combined organic layers were washed with brine (50 mL×2), dried over Na$_2$SO$_4$, filtered and concentrated under reduced pressure. (4-(2-(2-Aminopyridin-3-yl)-5-(4-methyl-2H-1,2,3-triazol-2-yl)-3H-imidazo[4,5-b]pyridin-3-yl)phenyl)methanol (150 mg, yield: 68%) was obtained as a red solid. MS: m/z=399.2 [M+H]$^+$. $^1$H NMR (400 MHz, Dimethylsulfoxide-d$_6$) δ 8.39 (d, J=8.4 Hz, 1H), 8.02-7.84 (m, 3H), 7.52-7.41 (m, 4H), 7.22 (dd, J=7.6, 2.0 Hz, 1H), 6.91 (s, 2H), 6.44-6.37 (m, 1H), 5.35 (t, J=5.6 Hz, 1H), 4.60 (d, J=6.0 Hz, 2H), 2.35 (s, 3H).

Step 4: 3-(3-(4-(Chloromethyl)phenyl)-5-(4-methyl-2H-1,2,3-triazol-2-yl)-3H-imidazo[4,5-b]pyridin-2-yl)pyridin-2-amine To a solution of (4-(2-(2-aminopyridin-3-yl)-5-(4-methyl-2H-1,2,3-triazol-2-yl)-3H-imidazo[4,5-b]pyridin-3-yl)phenyl)methanol (150 mg, 376 µmol) in CH$_2$Cl$_2$ (5 mL) was added SOCl$_2$ (134 mg, 1.13 mmol). The mixture was stirred at 40° C. for 0.5 hr. The reaction was concentrated under reduced pressure to give 3-(3-(4-(chloromethyl)phenyl)-5-(4-methyl-2H-1,2,3-triazol-2-yl)-3H-imidazo[4,5-b]pyridin-2-yl)pyridin-2-amine (Intermediate 220, 170 mg, HCl salt) as a green solid. MS: m/z=417.1 [M+H]$^+$.

Intermediate 221: 3-(3-(4-(Chloromethyl)phenyl)-5-(4-methyl-4H-1,2,4-triazol-3-yl)-3H-imidazo[4,5-b]pyridin-2-yl)pyridin-2-amine

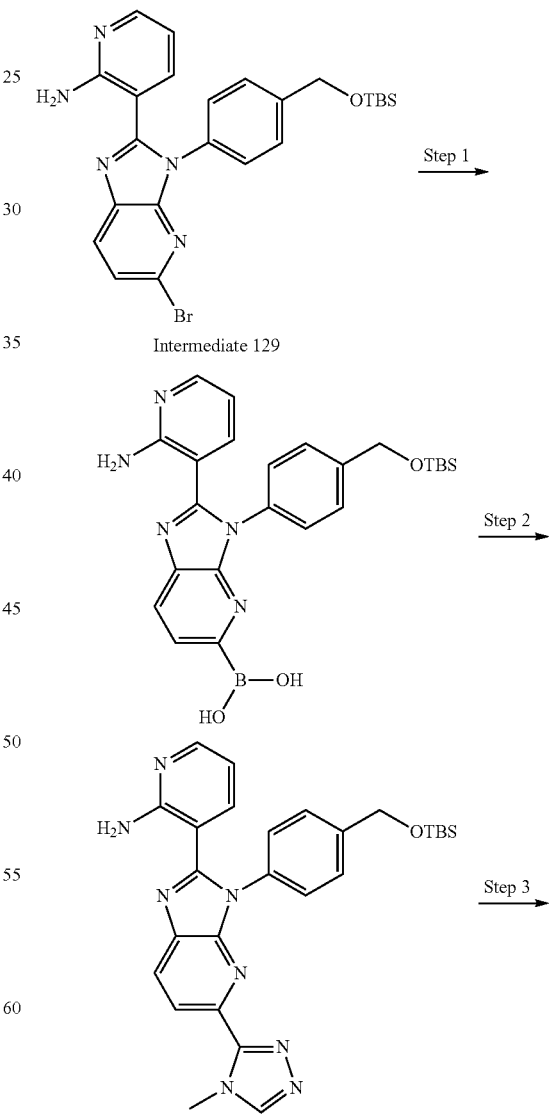

-continued

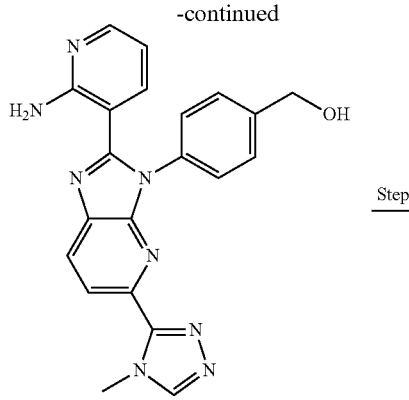

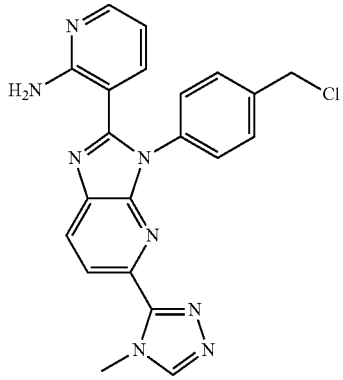

Intermediate 221

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl₂ (143 mg, 196 mmol) in 1,4-dioxane (5 mL) was degassed and purged with N₂ three times. The mixture was stirred at 90° C. for 16 hr under N₂ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid and was used in the next step without work-up and purification. MS: m/z=476.1 [M+H]⁺.

Step 2: 3-(3-(4-(((tert-Butyldimethylsilyl)oxy)methyl)phenyl)-5-(4-methyl-4H-1,2,4-triazol-3-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (470 mg, 989 mol), 3-bromo-4-methyl-4H-1,2,4-triazole (192 mg, 1.19 mmol), Pd(dppf)Cl₂ (72.3 mg, 98.9 μmol) and Cs₂CO₃ (966 mg, 2.97 mmol) in 1,4-dioxane (4 mL) and H₂O (1 mL) was degassed and purged with N₂ three times. The mixture was stirred at 90° C. for 16 hr under N₂ atmosphere. The reaction mixture was poured into H₂O (15 mL) and extracted with EtOAc (15 mL×3). The combined organic phases were dried over anhydrous Na₂SO₄, filtered and concentrated under reduced pressure. After purified by silica gel flash chromatography (Eluent of 0%~50% EtOAc in petroleum ether), 3-(3-(4-(((tert-butyldimethylsilyl)oxy)methyl)phenyl)-5-(4-methyl-4H-1,2,4-triazol-3-yl)-3H-imidazo[4,5-b]pyridin-2-yl)pyridin-2-amine (200 mg, yield: 40% for two steps) was obtained as a brown solid. MS: m/z=513.2 [M+H]⁺. ¹H NMR (400 MHz, Dimethysulfoxide-d₆) δ 8.63 (s, 1H), 8.37 (d, J=8.4 Hz, 1H), 8.16 (d, J=8.4 Hz, 1H), 8.08-7.92 (m, 1H), 7.53-7.46 (m, 4H), 7.25 (dd, J=7.6, 1.6 Hz, 1H), 7.02 (s, 2H), 6.41 (dd, J=7.6, 4.8 Hz, 1H), 4.80 (s, 2H), 4.08 (s, 3H), 0.91 (s, 9H), 0.07 (s, 6H).

Step 3: (4-(2-(2-Aminopyridin-3-yl)-5-(4-methyl-4H-1,2,4-triazol-3-yl)-3H-imidazo[4,5-b]pyridin-3-yl)phenyl)methanol To a solution of 3-(3-(4-(((tert-butyldimethylsilyl)oxy)methyl)phenyl)-5-(4-methyl-4H-1,2,4-triazol-3-yl)-3H-imidazo[4,5-b]pyridin-2-yl)pyridin-2-amine (200 mg, 390 μmol) in THF (2 mL) was added TBAF (1 mL, 1 M in THF). The mixture was stirred at 25° C. for 0.5 hr. The reaction mixture was poured into H₂O (15 mL) and extracted with EtOAc (15 mL×3). The combined organic phases were dried over anhydrous Na₂SO₄, filtered and concentrated under reduced pressure. (4-(2-(2-Aminopyridin-3-yl)-5-(4-methyl-4H-1,2,4-triazol-3-yl)-3H-imidazo[4,5-b]pyridin-3-yl)phenyl)methanol (155 mg, crude) was obtained as a brown solid. MS: m/z=399.1 [M+H]⁺.

Step 4: 3-(3-(4-(Chloromethyl)phenyl)-5-(4-methyl-4H-1,2,4-triazol-3-yl)-3H-imidazo[4,5-b]pyridin-2-yl)pyridin-2-amine To a solution of (4-(2-(2-aminopyridin-3-yl)-5-(4-methyl-4H-1,2,4-triazol-3-yl)-3H-imidazo[4,5-b]pyridin-3-yl)phenyl)methanol (155 mg, 389 μmol) in CH₂Cl₂ (2 mL) was added SOCl₂ (1 mL). The mixture was stirred at 25° C. for 0.5 hr. The reaction was concentrated under reduced pressure, 3-(3-(4-(chloromethyl)phenyl)-5-(4-methyl-4H-1,2,4-triazol-3-yl)-3H-imidazo[4,5-b]pyridin-2-yl)pyridin-2-amine (Intermediate 221, 160 mg, HCl salt) was obtained as a brown solid. MS: m/z=417.1 [M+H]⁺.

Intermediate 222: 3-(3-(4-(Chloromethyl)phenyl)-5-(3-fluoropyridin-2-yl)-3H-imidazo[4,5-b]pyridin-2-yl)pyridin-2-amine

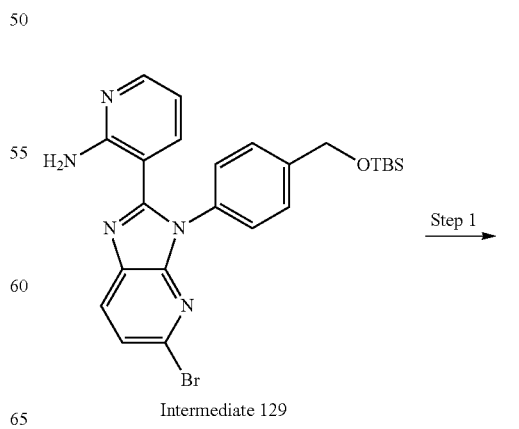

Intermediate 129

-continued

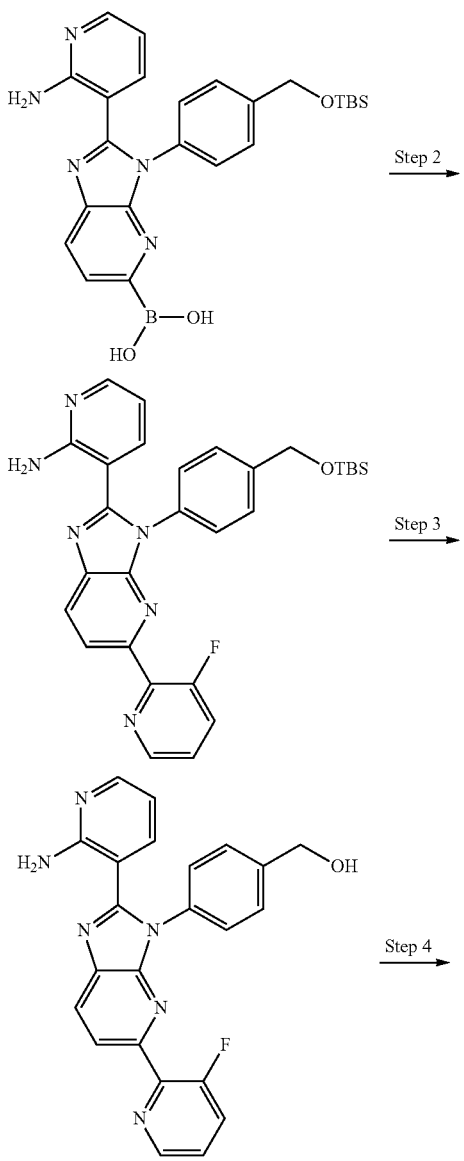

Intermediate 222

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid To a solution of Intermediate 129 (500 mg, 0.98 mmol) and 4,4,5,5-tetramethyl-2-(4,4,5,5-tetramethyl-1,3,2-dioxaborolan-2-yl)-1,3,2-dioxaborolane (497 mg, 1.96 mmol) in 1,4-dioxane (10 mL) were added KOAc (288 mg, 2.94 mmol) and Pd(dppf)Cl$_2$ (71 mg, 98 µmol) at 25° C. This mixture was stirred at 80° C. for 4 hr. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as black liquid, which was used in the next step directly. MS: m/z=476.2 [M+H]$^+$.

Step 2: 3-(3-(4-(((tert-Butyldimethylsilyl)oxy)methyl)phenyl)-5-(3-fluoropyridin-2-yl)-3H-imidazo[4,5-b]pyridin-2-yl)pyridin-2-amine To a mixture of (2-(2-aminopyridin-3-yl)-3-(4-(((tert-butyldimethylsilyl)oxy)methyl)phenyl)-3H-imidazo[4,5-b]pyridin-5-yl)boronic acid (450 mg, 946 µmol) and 2-bromo-3-fluoropyridine (183 mg, 1.04 mmol) in 1,4-dioxane (5 mL) and H$_2$O (1 mL) were added Cs$_2$CO$_3$ (925 mg, 2.84 mmol) and Pd(dppf)Cl$_2$ (69.3 mg, 94.7 µmol). The mixture was stirred at 100° C. for 2 hr under N$_2$. The mixture was diluted with H$_2$O (50 mL) and extracted with EtOAc (50 mL×2). The combined organic layers were washed with brine (50 mL), dried over anhydrous Na$_2$SO$_4$, filtered and concentrated. After purified by silica gel flash chromatography (EtOAc in petroleum ether=0-50%), 3-(3-(4-(((tert-butyldimethylsilyl)oxy)methyl)phenyl)-5-(3-fluoropyridin-2-yl)-3H-imidazo[4,5-b]pyridin-2-yl)pyridin-2-amine (300 mg, yield: 54% for two steps) was obtained as a brown solid. MS: m/z=527.3 [M+H]$^+$. $^1$H NMR (400 MHz, Dimethylsulfoxide-d$_6$) δ 8.57-8.50 (m, 1H), 8.33 (d, J=8.4 Hz, 1H), 8.03-7.98 (m, 2H), 7.86-7.76 (m, 1H), 7.57-7.49 (m, 1H), 7.47-7.41 (m, 4H), 7.21 (dd, J=7.6, 1.6 Hz, 1H), 7.02 (s, 2H), 6.39 (dd, J=7.6, 4.8 Hz, 1H), 4.80 (s, 2H), 0.91 (s, 9H), 0.10 (s, 6H).

Step 3: (4-(2-(2-Aminopyridin-3-yl)-5-(3-fluoropyridin-2-yl)-3H-imidazo[4,5-b]pyridin-3-yl)phenyl)methanol To a mixture of 3-(3-(4-(((tert-butyldimethylsilyl)oxy)methyl)phenyl)-5-(3-fluoropyridin-2-yl)-3H-imidazo[4,5-b]pyridin-2-yl)pyridin-2-amine (250 mg, 475 µmol) in THF (2 mL) was added TBAF (1M in THF, 712 µL). The mixture was stirred at 20° C. for 0.5 hr. The mixture was diluted with H$_2$O (20 mL) and extracted with EtOAc (20 mL×2). The combined organic layers were washed with brine (20 mL), dried over anhydrous Na$_2$SO$_4$, filtered and concentrated. (4-(2-(2-Aminopyridin-3-yl)-5-(3-fluoropyridin-2-yl)-3H-imidazo[4,5-b]pyridin-3-yl)phenyl)methanol (195 mg, yield: 99%) was obtained as a brown solid. MS: m/z=413.2 [M+H]$^+$. $^1$H NMR (400 MHz, Dimethylsulfoxide-d$_6$) δ 8.56-8.50 (m, 1H), 8.33 (d, J=8.0 Hz, 1H), 8.03-7.97 (m, 2H), 7.85-7.76 (m, 1H), 7.56-7.50 (m, 1H), 7.47-7.41 (m, 4H), 7.25 (dd, J=7.6, 1.6 Hz, 1H), 6.94 (s, 2H), 6.43 (dd, J=7.6, 4.8 Hz, 1H), 5.34 (t, J=6.0 Hz, 1H), 4.58 (d, J=5.6 Hz, 2H).

Step 4: 3-(3-(4-(Chloromethyl)phenyl)-5-(3-fluoropyridin-2-yl)-3H-imidazo[4,5-b]pyridin-2-yl)pyridin-2-amine To a mixture of (4-(2-(2-aminopyridin-3-yl)-5-(3-fluoropyridin-2-yl)-3H-imidazo[4,5-b]pyridin-3-yl)phenyl)

methanol (195 mg, 472 µmol) in CH$_2$Cl$_2$ (3 mL) was added SOCl$_2$ (169 mg, 1.42 mmol). The mixture was stirred at 20° C. for 1 hr. The mixture was concentrated to give 3-(3-(4-(chloromethyl)phenyl)-5-(3-fluoropyridin-2-yl)-3H-imidazo[4,5-b]pyridin-2-yl)pyridin-2-amine (Intermediate 222, 203 mg, yield: 99%) as a brown solid. MS: m/z=431.1 [M+H]$^+$.

Intermediate 223: 3-(3-(4-(Chloromethyl)phenyl)-5-(6-methylpyridin-2-yl)-3H-imidazo[4,5-b]pyridin-2-yl)pyridin-2-amine

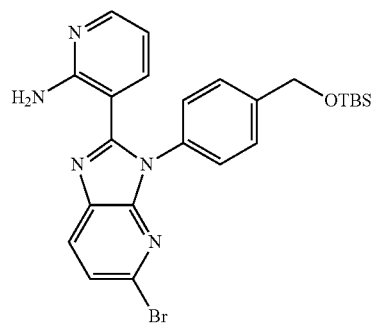

Intermediate 129

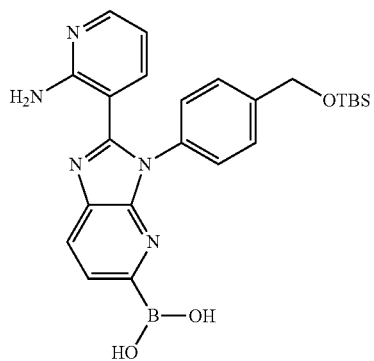

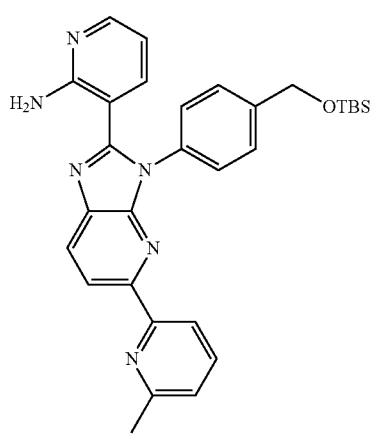

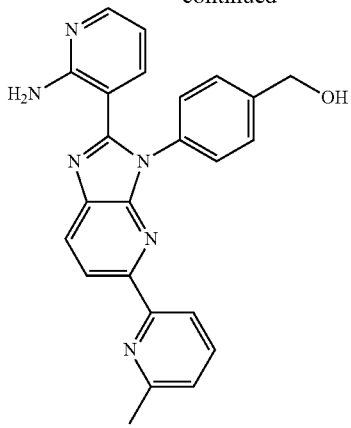

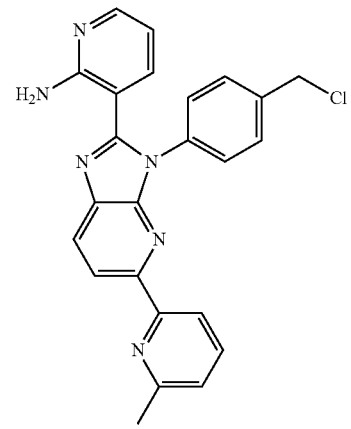

Intermediate 223

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid To a solution of Intermediate 129 (500 mg, 0.98 mmol) and 4,4,5,5-tetramethyl-2-(4,4,5,5-tetramethyl-1,3,2-dioxaborolan-2-yl)-1,3,2-dioxaborolane (497 mg, 1.96 mmol) in 1,4-dioxane (10 mL) were added KOAc (288 mg, 2.94 mmol) and Pd(dppf)Cl$_2$ (71 mg, 98 µmol) at 25° C. This mixture was stirred at 80° C. for 4 hr. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as black liquid, which was used in the next step directly. MS: m/z=476.2 [M+H]$^+$.

Step 2: 3-(3-(4-(((tert-Butyldimethylsilyl)oxy)methyl)phenyl)-5-(6-methylpyridin-2-yl)-3H-imidazo[4,5-b]pyridin-2-yl)pyridin-2-amine To a mixture of (2-(2-aminopyridin-3-yl)-3-(4-(((tert-butyldimethylsilyl)oxy)methyl)phenyl)-3H-imidazo[4,5-b]pyridin-5-yl)boronic acid (450 mg, 947 µmol) and 2-bromo-6-methylpyridine (179 mg, 1.04 mmol) in 1,4-dioxane (5 mL) and H$_2$O (1 mL) were added Cs$_2$CO$_3$ (925 mg, 2.84 mmol) and Pd(dppf)Cl$_2$ (69.3 mg, 94.7 µmol). The mixture was stirred at 100° C. for 2 hr under N$_2$. The mixture was diluted with H$_2$O (50 mL) and extracted with EtOAc (100 mL×2). The combined organic layers were washed with brine (100 mL), dried over anhydrous Na$_2$SO$_4$, filtered and concentrated. After purified by silica gel flash chromatography (EtOAc in petroleum ether=0-50%), 3-(3-(4-(((tert-butyldimethylsilyl)oxy)methyl)phenyl)-5-(6-methylpyridin-2-yl)-3H-imidazo[4,5-b]pyridin-2-yl)pyridin-2-amine (350 mg, yield: 63% for two steps) was obtained as a brown solid. MS: m/z=523.2 [M+H]$^+$. $^1$H NMR (400 MHz, Dimethylsulfoxide-$d_6$) δ 8.47 (d, J=8.4 Hz, 1H), 8.29 (d, J=8.4 Hz, 1H), 8.05-7.96 (m, 2H), 7.75 (t, J=8.0 Hz, 1H), 7.54-7.46 (m, 4H), 7.29-7.18 (m, 2H), 7.02 (s, 2H), 6.39 (dd, J=7.6, 4.8 Hz, 1H), 4.83 (s, 2H), 2.56 (s, 3H), 0.93 (s, 9H), 0.11 (s, 6H).

Step 3: (4-(2-(2-Aminopyridin-3-yl)-5-(6-methylpyridin-2-yl)-3H-imidazo[4,5-b]pyridin-3-yl)phenyl)methanol To a mixture of 3-(3-(4-(((tert-butyldimethylsilyl)oxy)methyl)phenyl)-5-(6-methylpyridin-2-yl)-3H-imidazo[4,5-b]pyridin-2-yl)pyridin-2-amine (300 mg, 574 μmol) in THF (2 mL) was added TBAF (1M in THF, 0.86 mL). The mixture was stirred at 20° C. for 0.5 hr. The mixture was diluted with H$_2$O (20 mL) and extracted with EtOAc (20 mL×2). The combined organic layers were washed with brine (20 mL), dried over anhydrous Na$_2$SO$_4$, filtered and concentrated. (4-(2-(2-Aminopyridin-3-yl)-5-(6-methylpyridin-2-yl)-3H-imidazo[4,5-b]pyridin-3-yl)phenyl)methanol (234 mg, yield: 99%) was obtained as a brown solid. MS: m/z=409.2 [M+H]$^+$. $^1$H NMR (400 MHz, Dimethylsulfoxide-$d_6$) δ 8.48 (d, J=8.4 Hz, 1H), 8.29 (d, J=8.4 Hz, 1H), 8.04-7.94 (m, 2H), 7.77 (t, J=7.6 Hz, 1H), 7.54-7.43 (m, 4H), 7.29-7.22 (m, 2H), 6.96 (s, 2H), 6.43 (dd, J=7.6, 4.8 Hz, 1H), 5.37 (t, J=5.6 Hz, 1H), 4.61 (d, J=5.6 Hz, 2H), 2.57 (s, 3H).

Step 4: 3-(3-(4-(Chloromethyl)phenyl)-5-(6-methylpyridin-2-yl)-3H-imidazo[4,5-b]pyridin-2-yl)pyridin-2-amine To a mixture of (4-(2-(2-aminopyridin-3-yl)-5-(6-methylpyridin-2-yl)-3H-imidazo[4,5-b]pyridin-3-yl)phenyl)methanol (230 mg, 563 μmol) in CH$_2$Cl$_2$ (3 mL) was added SOCl$_2$ (201 mg, 1.69 mmol). The mixture was stirred at 20° C. for 1 hr and concentrated to give 3-(3-(4-(chloromethyl)phenyl)-5-(6-methylpyridin-2-yl)-3H-imidazo[4,5-b]pyridin-2-yl)pyridin-2-amine (Intermediate 223, 240 mg HCl salt, yield: 99%) as a brown solid. MS: m/z=427.2 [M+H]$^+$.

Intermediate 224: 3-(3-(4-(Chloromethyl)phenyl)-5-(1-(difluoromethyl)-1H-1,2,4-triazol-3-yl)-3H-imidazo[4,5-b]pyridin-2-yl)pyridin-2-amine

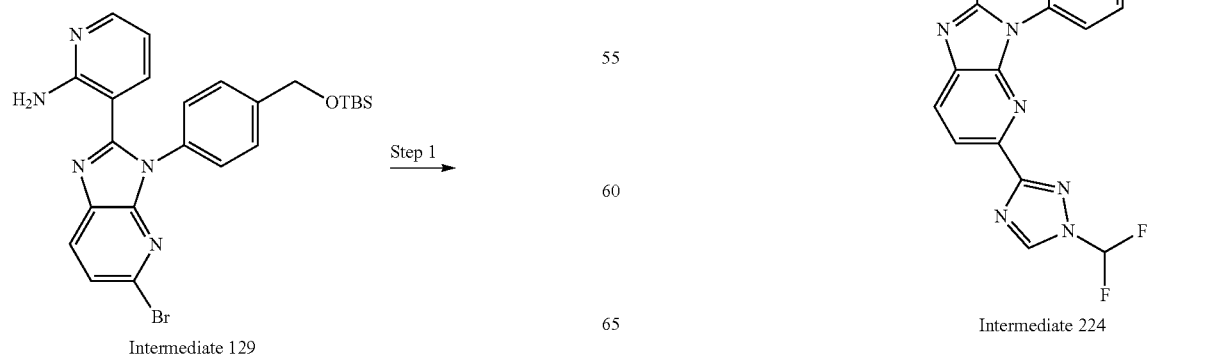

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (400 mg, 784 μmol), 4,4,4',4',5,5,5',5'-octamethyl-2,2'-bi(1,3,2-dioxaborolane) (398 mg, 1.57 mmol), KOAc (231 mg, 2.35 mmol) and Pd(dppf)C$_2$ (57.3 mg, 78.4 μmol) in 1,4-dioxane (5 mL) was degassed and purged with N$_2$ three times. The mixture was stirred at 80° C. for 2 hr under N$_2$ atmosphere. (2-(2-aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]$^+$.

Step 2: 3-(3-(4-(((tert-Butyldimethylsilyl)oxy)methyl)phenyl)-5-(1-(difluoromethyl)-1H-1,2,4-triazol-3-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (372 mg, 782 mol), 3-bromo-1-(difluoromethyl)-H-1,2,4-triazole (186 mg, 939 μmol), Pd(dppf)Cl$_2$ (57.3 mg, 78.3 μmol) and Cs$_2$CO$_3$ (165 mg, 2.35 mmol) in 1,4-dioxane (5 mL) and H$_2$O (I mL) was degassed and purged with N$_2$ three times. The mixture was stirred at 80° C. for 16 hr under N$_2$ atmosphere. The reaction mixture was quenched with H$_2$O (50 mL) and extracted with CH$_2$Cl$_2$ (50 mL×2). The combined organic layers were washed with brine (50 mL), dried over Na$_2$SO$_4$, filtered, and concentrated under reduced pressure. After purified by silica gel flash chromatography (Eluent of 10%~50% EtOAc in petroleum ether), 3-(3-(4-(((tert-butyldimethylsilyl)oxy)methyl)phenyl)-5-(1-(difluoromethyl)-1H-1,2,4-triazol-3-yl)-3H-imidazo[4,5-b]pyridin-2-yl)pyridin-2-amine (220 mg, yield: 37% for two steps) was obtained as a yellow solid. MS: m/z=549.2 [M+H]$^+$. $^1$H NMR (400 MHz, Dimethylsulfoxide-d$_6$) δ 9.18 (s, 1H), 8.36-8.28 (m, 1H), 8.18 (d, J=8.0 Hz, 1H), 8.04-7.82 (m, 2H), 7.50-7.35 (m, 4H), 7.25-7.17 (m, 1H), 7.04-6.89 (m, 2H), 6.46-6.32 (m, 1H), 4.83 (s, 2H), 0.93 (s, 9H), 0.12 (s, 6H).

Step 3: (4-(2-(2-Aminopyridin-3-yl)-5-(1-(difluoromethyl)-1H-1,2,4-triazol-3-yl)-3H-imidazo[4,5-b]pyridin-3-yl)phenyl)methanol To a solution of 3-(3-(4-(((tert-butyldimethylsilyl)oxy)methyl)phenyl)-5-(1-(difluoromethyl)-1H-1,2,4-triazol-3-yl)-3H-imidazo[4,5-b]pyridin-2-yl)pyridin-2-amine (220 mg, 401 μmol) in THF (5 mL) was added TBAF (0.8 mL, 1 M in THF). The mixture was stirred at 25° C. for 0.5 hr. The reaction mixture was quenched with H$_2$O (20 mL) at 25° C. and extracted with CH$_2$Cl$_2$ (20 mL×3). The combined organic layers were washed with brine (20 mL×2), dried over Na$_2$SO$_4$, filtered and concentrated under reduced pressure. After purified by silica gel flash chromatography (Eluent of 50%~100% EtOAc in petroleum ether), (4-(2-(2-aminopyridin-3-yl)-5-(1-(difluoromethyl)-1H-1,2,4-triazol-3-yl)-3H-imidazo[4,5-b]pyridin-3-yl)phenyl)methanol (50 mg, yield: 26%) was obtained as a yellow solid. MS: m/z=435.1 [M+H]$^+$. $^1$H NMR (400 MHz, Dimethylsulfoxide-d$_6$) δ 9.19 (s, 1H), 8.34 (d, J=8.4 Hz, 1H), 8.19 (d, J=8.0 Hz, 1H), 8.07-7.77 (m, 2H), 7.54-7.41 (m, 4H), 7.24 (d, J=7.2 Hz, 1H), 6.97 (s, 2H), 6.46-6.34 (m, 1H), 5.37 (t, J=5.6 Hz, 1H), 4.61 (d, J=5.2 Hz, 2H).

Step 4: 3-(3-(4-(Chloromethyl)phenyl)-5-(1-(difluoromethyl)-1H-1,2,4-triazol-3-yl)-3H-imidazo[4,5-b]pyridin-2-yl)pyridin-2-amine To a solution of (4-(2-(2-aminopyridin-3-yl)-5-(1-(difluoromethyl)-1H-1,2,4-triazol-3-yl)-3H-imidazo[4,5-b]pyridin-3-yl)phenyl)methanol (50 mg, 115 μmol) in CH$_2$Cl$_2$ (5 mL) was added SOCl$_2$ (41.1 mg, 345 μmol). The mixture was stirred at 25° C. for 0.5 hr. The reaction was concentrated under reduced pressure to give 3-(3-(4-(chloromethyl)phenyl)-5-(1-(difluoromethyl)-1H-1,2,4-triazol-3-yl)-3H-imidazo[4,5-b]pyridin-2-yl)pyridin-2-amine (Intermediate 224, 52 mg, HCl slat) as a yellow solid. MS: m/z=453.0 [M+H]$^+$.

Intermediate 225: 4-((5'-Fluoro-5-nitro-[2,2'-bipyridin]-6-yl)amino)benzyl acetate

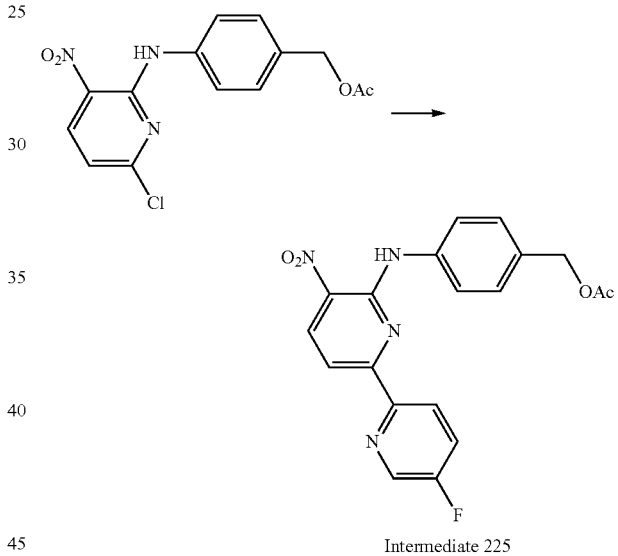

Intermediate 225

A mixture of 4-((6-chloro-3-nitropyridin-2-yl)amino)benzyl acetate (refer to Intermediate 178 for detail procedures, 10 g, 31 mmol), (5-fluoropyridin-2-yl)boronic acid (13 g, 93 mmol), Cata CXium A Pd G3 (2.3 g, 3.1 mmol), CuBr (3.34 g, 23.3 mmol) and Cs$_2$CO$_3$ (30 g, 93 mmol) in 1,4-dioxane (350 mL) was degassed and purged with N$_2$ three times. The mixture was stirred at 125° C. for 2.5 hr under N$_2$ atmosphere. The reaction mixture was poured into H$_2$O (500 mL) and extracted with CH$_2$Cl$_2$ (200 mL×2). The combined organic layers were washed with brine (500 mL), dried over Na$_2$SO$_4$, filtered, and concentrated under reduced pressure. After triturated (10% EtOAc in petroleum ether, 100 mL) at 25° C. for 1 hr, 4-((5'-fluoro-5-nitro-[2,2'-bipyridin]-6-yl)amino)benzyl acetate (Intermediate 225, 10 g, yield: 72%) was obtained as a yellow solid. MS: m/z=383.0 [M+H]$^+$. $^1$H NMR (400 MHz, Dimethylsulfoxide-d$_6$) δ 10.10 (s, 1H), 8.77-8.74 (m, 1H), 8.69 (d, J=8.8 Hz, 1H), 8.25-8.21 (m, 1H), 7.97-7.92 (m, 1H), 7.90 (d, J=8.4 Hz, 1H), 7.75 (d, J=8.4 Hz, 2H), 7.48-7.44 (m, 2H), 5.10 (s, 2H), 2.09 (s, 3H). $^{19}$F NMR (400 MHz, Dimethylsulfoxide-d$_6$) δ −124.159.

Intermediate 226: 5-(3-(4-(Chloromethyl)phenyl)-5-(5-fluoropyridin-2-yl)-3H-imidazo[4,5-b]pyridin-2-yl)pyrimidin-4-amine

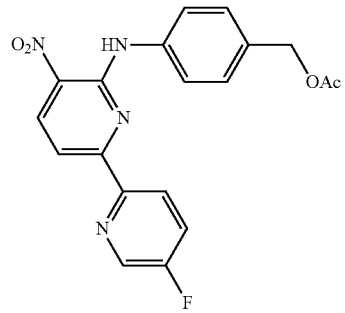

Intermediate 225

Step 1 →

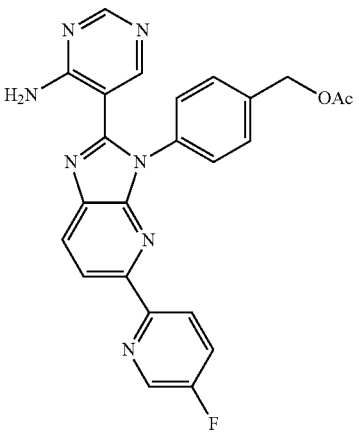

Step 2 →

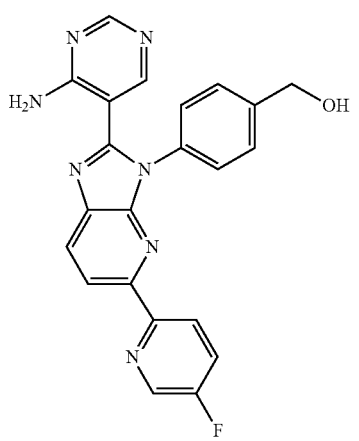

Step 3 →

-continued

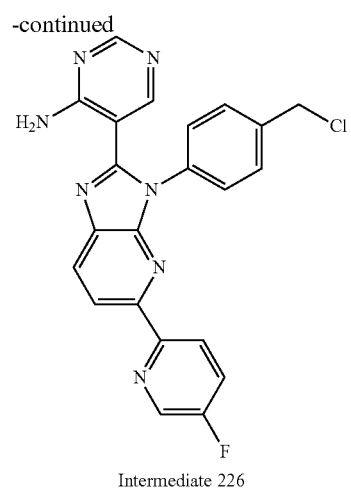

Intermediate 226

Step 1: 4-(2-(4-Aminopyrimidin-5-yl)-5-(5-fluoropyridin-2-yl)-3H-imidazo[4,5-b]pyridin-3-yl)benzyl acetate To a solution of Intermediate 225 (2 g, 5.23 mmol) in DMSO (10 mL) were added $Na_2S_2O_4$ (3.64 g, 20.9 mmol, 87% purity) and 4-aminopyrimidine-5-carbaldehyde (708 mg, 5.75 mmol). The mixture was stirred at 100° C. for 2 hr. The reaction mixture was quenched with $H_2O$ (100 mL) at 25° C. and extracted with $CH_2Cl_2$ (100 mL×2). The combined organic layers were washed with brine (100 mL×2), dried over $Na_2SO_4$, filtered, and concentrated under reduced pressure. After purified by silica gel flash chromatography (Eluent of 20% 70% EtOAc in petroleum ether), 4-(2-(4-aminopyrimidin-5-yl)-5-(5-fluoropyridin-2-yl)-3H-imidazo[4,5-b]pyridin-3-yl)benzyl acetate (500 mg, yield: 21%) was obtained as a yellow solid. MS: m/z=456.1 [M+H]$^+$. $^1$H NMR (400 MHz, Dimethylsulfoxide-d$_6$) δ 8.67 (d, J=2.8 Hz, 1H), 8.46-8.30 (m, 3H), 8.26-8.20 (m, 1H), 8.02 (s, 1H), 7.87-7.80 (m, 1H), 7.69 (s, 2H), 7.59 (s, 4H), 5.20 (s, 2H), 2.13 (s, 3H). $^{19}$F NMR (400 MHz, Dimethylsulfoxide-d$_6$) δ −127.656.

Step 2: (4-(2-(4-Aminopyrimidin-5-yl)-5-(5-fluoropyridin-2-yl)-3H-imidazo[4,5-b]pyridin-3-yl)phenyl)methanol To a solution of 4-(2-(4-aminopyrimidin-5-yl)-5-(5-fluoropyridin-2-yl)-3H-imidazo[4,5-b]pyridin-3-yl)benzyl acetate (500 mg, 1.1 mmol) in THF (5 mL) and MeOH (5 mL) was added $K_2CO_3$ (455 mg, 3.29 mmol). The mixture was stirred at 25° C. for 0.5 hr. The reaction mixture was quenched with $H_2O$ (50 mL) at 25° C. and extracted with $CH_2Cl_2$ (50 mL×3). The combined organic layers were washed with brine (50 mL×2), dried over $Na_2SO_4$, filtered and concentrated under reduced pressure. (4-(2-(4-Aminopyrimidin-5-yl)-5-(5-fluoropyridin-2-yl)-3H-imidazo[4,5-b]pyridin-3-yl)phenyl)methanol (450 mg, yield: 95%) was obtained as a yellow solid. MS: m/z=414.1 [M+H]$^+$.

Step 3: 5-(3-(4-(Chloromethyl)phenyl)-5-(5-fluoropyridin-2-yl)-3H-imidazo[4,5-b]pyridin-2-yl)pyrimidin-4-amine To a solution of (4-(2-(4-aminopyrimidin-5-yl)-5-(5-fluoropyridin-2-yl)-3H-imidazo[4,5-b]pyridin-3-yl)phenyl)

methanol (450 mg, 1.09 mmol) in CH₂Cl₂ (5 mL) was added SOCl₂ (389 mg, 3.27 mmol). The mixture was stirred at 25° C. for 0.5 hr. The reaction was concentrated under reduced pressure to give 5-(3-(4-(chloromethyl)phenyl)-5-(5-fluoropyridin-2-yl)-3H-imidazo[4,5-b]pyridin-2-yl)pyrimidin-4-amine (Intermediate 226, 509 mg, HCl salt) as a yellow solid. MS: m/z=432.0 [M+H]⁺.

Intermediate 227: 3-(3-(4-(Chloromethyl)phenyl)-5-(5-fluoropyridin-2-yl)-3H-imidazo[4,5-b]pyridin-2-yl)pyrazin-2-amine

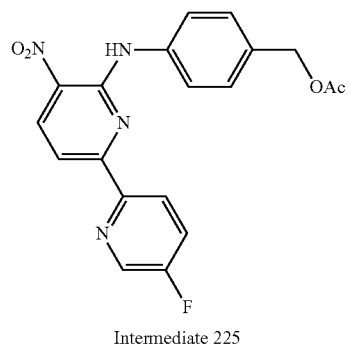

Intermediate 225

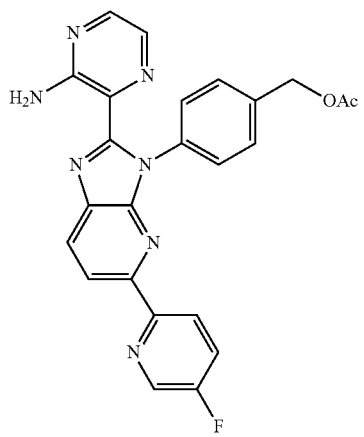

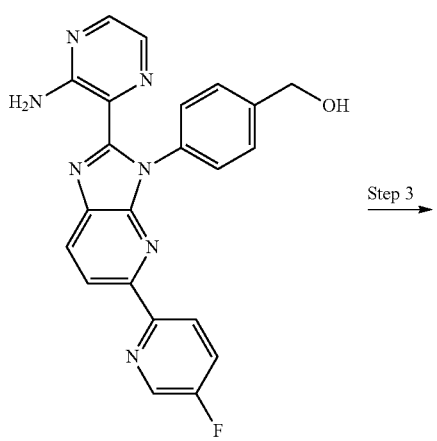

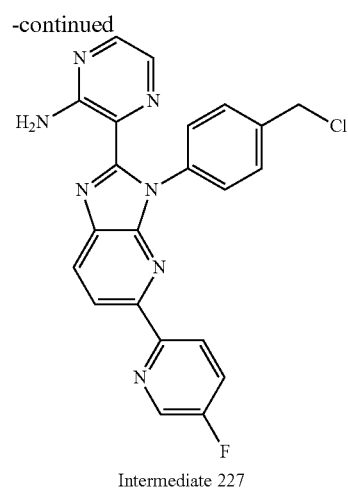

Intermediate 227

Step 1: 4-(2-(3-Aminopyrazin-2-yl)-5-(5-fluoropyridin-2-yl)-3H-imidazo[4,5-b]pyridin-3-yl)benzyl acetate A mixture of Intermediate 225 (1 g, 2.6 mmol) and 3-aminopyrazine-2-carbaldehyde (386 mg, 3.1 mmol) in DMSO (20 mL) was added Na₂S₂O₄ (1.8 g, 10.5 mmol) at 25° C. The mixture was stirred at 100° C. for 12 hr. The reaction mixture was poured into H₂O (50 mL) and extracted with CH₂Cl₂ (20 mL). The combined organic layers were washed with brine (50 mL), dried over Na₂SO₄, filtered, and concentrated under reduced pressure. After purified by silica gel flash chromatography (Eluent of 0%~3% MeOH in CH₂Cl₂), 4-(2-(3-Aminopyrazin-2-yl)-5-(5-fluoropyridin-2-yl)-3H-imidazo[4,5-b]pyridin-3-yl)benzyl acetate (350 mg, yield: 20%) was obtained as a yellow solid. MS: m/z=456.0 [M+H]⁺. ¹H NMR (400 MHz, Dimethylsulfoxide-d₆) δ 8.67 (d, J=2.8 Hz, 1H), 8.45-8.42 (m, 1H), 8.40-8.37 (m, 1H), 8.20 (dd, J=8.8, 4.8 Hz, 1H), 8.03 (d, J=2.4 Hz, 1H), 7.88-7.82 (m, 2H), 7.54 (d, J=2.4 Hz, 1H), 7.52-7.50 (m, 2H), 7.48 (s, 2H), 7.47-7.45 (m, 1H), 5.21 (s, 2H), 2.14 (s, 3H). ¹⁹F NMR (400 MHz, Dimethylsulfoxide-d₆) δ -127.529.

Step 2: (4-(2-(3-Aminopyrazin-2-yl)-5-(5-fluoropyridin-2-yl)-3H-imidazo[4,5-b]pyridin-3-yl)phenyl)methanol To a solution of 4-(2-(3-aminopyrazin-2-yl)-5-(5-fluoropyridin-2-yl)-3H-imidazo[4,5-b]pyridin-3-yl)benzyl acetate (250 mg, 549 μmol) in THF (2 mL) were added K₂CO₃ (228 mg, 1.65 mmol), MeOH (2 mL) and H₂O (2 mL). The mixture was stirred at 25° C. for 1 hr. The reaction mixture was diluted with H₂O (10 mL) and extracted with CH₂Cl₂ (10 mL×3). The combined organic layers were washed with brine (30 mL), dried over Na₂SO₄, filtered and concentrated under reduced pressure. (4-(2-(3-Aminopyrazin-2-yl)-5-(5-fluoropyridin-2-yl)-3H-imidazo[4,5-b]pyridin-3-yl)phenyl)methanol (210 mg, crude) was obtained as a yellow solid. MS: m/z=414.2 [M+H]⁺.

Step 3: 3-(3-(4-(Chloromethyl)phenyl)-5-(5-fluoropyridin-2-yl)-3H-imidazo[4,5-b]pyridin-2-yl)pyrazin-2-amine To a solution of (4-(2-(3-aminopyrazin-2-yl)-5-(5-fluoropyridin-2-yl)-3H-imidazo[4,5-b]pyridin-3-yl)phenyl)

methanol (210 mg, 508 µmol) in CH₂Cl₂ (5 mL) was added SOCl₂ (0.5 mL). The mixture was stirred at 40° C. for 1 hr. The mixture was concentrated under reduced pressure to give 3-(3-(4-(chloromethyl)phenyl)-5-(5-fluoropyridin-2-yl)-3H-imidazo[4,5-b]pyridin-2-yl)pyrazin-2-amine (Intermediate 227, 240 mg, HCl salt, crude) as a yellow solid. MS: m, J=432.0 [M+H]⁺.

Intermediate 228: 3-(4-(Chloromethyl)phenyl)-5-(5-fluoropyridin-2-yl)-2-(pyridin-3-yl)-3H-imidazo[4,5-b]pyridine

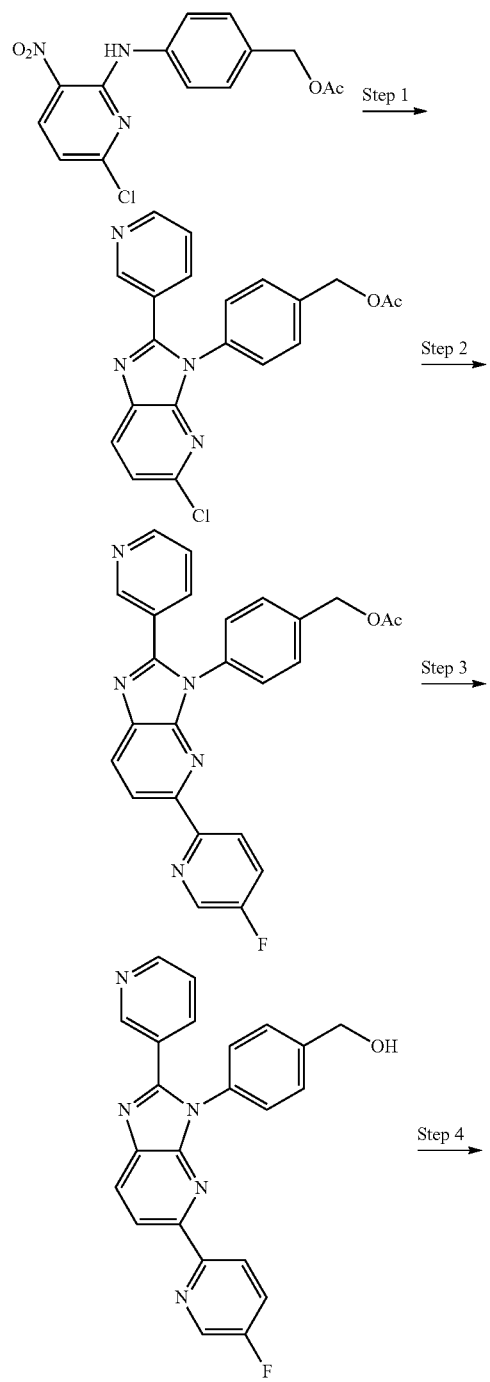

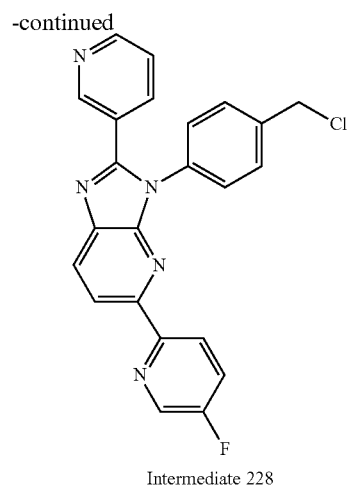

Intermediate 228

Step 1: 4-(5-Chloro-2-(pyridin-3-yl)-3H-imidazo[4,5-b]pyridin-3-yl)benzyl acetate A mixture of 4-((6-chloro-3-nitropyridin-2-yl)amino)benzyl acetate (refer to Intermediate 178 for detail procedures, 2 g, 6.22 mmol) and nicotinaldehyde (799 mg, 7.46 mmol) in DMSO (20 mL) was added Na₂S₂O₄ (5.1 g, 24.9 mmol) at 25° C. The mixture was stirred at 80° C. for 12 hr. The reaction mixture was poured into H₂O (50 mL) and extracted with CH₂Cl₂ (30 mL×3). The combined organic layers were washed with brine (30 mL×3), dried over Na₂SO₄, filtered, and concentrated under reduced pressure. After purified by silica gel flash chromatography (Eluent of 20%~50% EtOAc in petroleum ether), 4-(5-chloro-2-(pyridin-3-yl)-3H-imidazo[4,5-b]pyridin-3-yl)benzyl acetate (1.2 g, yield: 51%) was obtained as a yellow solid. MS: m/z=379.1 [M+H]⁺. ¹H NMR (400 MHz, Dimethylsulfoxide-d₆) δ 8.70 (d, J=1.6 Hz, 1H), 8.63 (d, J=4.8 Hz, 1H), 8.33 (d, J=8.4 Hz, 1H), 7.91 (d, J=8.0 Hz, 1H), 7.59-7.54 (m, 2H), 7.53-7.46 (m, 4H), 5.18 (s, 2H), 2.12 (s, 3H)

Step 2: 4-(5-(5-Fluoropyridin-2-yl)-2-(pyridin-3-yl)-3H-imidazo[4,5-b]pyridin-3-yl)benzyl acetate A mixture of 4-(5-chloro-2-(pyridin-3-yl)-3H-imidazo[4,5-b]pyridin-3-yl)benzyl acetate (640 mg, 1.69 mmol) and (5-fluoropyridin-2-yl)boronic acid (714 mg, 5.07 mmol) in 1,4-dioxane (10 mL) were added cataCXium A Pd G₃ (123 mg, 169 µmol), CuBr (182 mg, 1.27 mmol) and Cs₂CO₃ (1.65 g, 5.07 mmol) was degassed and purged with N₂ three times. The mixture was stirred at 90° C. for 2 hr under N₂ atmosphere. The reaction mixture was poured into H₂O (30 mL) and extracted with CH₂Cl₂ (30 mL×3). The combined organic layers were washed with brine (30 mL×5), dried over Na₂SO₄, filtered, and concentrated under reduced pressure. After triturated with EtOAc (5 mL) at 25° C. for 30 min, 4-(5-(5-fluoropyridin-2-yl)-2-(pyridin-3-yl)-3H-imidazo[4,5-b]pyridin-3-yl)benzyl acetate (700 mg, yield: 94%) was obtained as a yellow solid. MS: m/z=440.1 [M+H]⁺. ¹H NMR (400 MHz, Dimethylsulfoxide-d₆) δ 8.76-8.59 (m, 3H), 8.47-8.33 (m, 2H), 8.24 (dd, J=8.8, 4.4 Hz, 1H), 7.94 (d, J=8.0 Hz, 1H), 7.88-7.80 (m, 1H), 7.59 (br s, 4H), 7.52-7.45 (m, 1H), 5.21 (s, 2H), 2.12 (s, 3H).

Step 3: (4-(5-(5-Fluoropyridin-2-yl)-2-(pyridin-3-yl)-3H-imidazo[4,5-b]pyridin-3-yl)phenyl)methanol To a solution of 4-(5-(5-fluoropyridin-2-yl)-2-(pyridin-3-yl)-3H-imidazo[4,5-b]pyridin-3-yl)benzyl acetate (700 mg, 1.59 mmol) in THF (5 mL) were added K₂CO₃ (661 mg, 4.78 mmol), MeOH (5 mL) and H₂O (5 mL). The mixture was stirred at 25° C. for 1 hr. The reaction mixture was diluted with H₂O (30 mL) and extracted with CH₂Cl₂ (20 mL×3). The combined organic layers were washed with brine (60 mL), dried over Na₂SO₄, filtered and concentrated under reduced pressure. (4-(5-(5-Fluoropyridin-2-yl)-2-(pyridin-3-yl)-3H-imidazo[4,5-b]pyridin-3-yl)phenyl) methanol (360 mg, crude) was obtained as a yellow solid. MS: m/z=398.1 [M+H]⁺.

Step 4: 3-(4-(Chloromethyl)phenyl)-5-(5-fluoropyridin-2-yl)-2-(pyridin-3-yl)-3H-imidazo[4,5-b]pyridine To a solution of (4-(5-(5-fluoropyridin-2-yl)-2-(pyridin-3-yl)-3H-imidazo[4,5-b]pyridin-3-yl)phenyl)methanol (360 mg, 508 µmol) in CH₂Cl₂ (5 mL) was added SOCl₂ (1 mL). The mixture was stirred at 40° C. for 1 hr. The mixture was concentrated under reduced pressure to give 3-(4-(chloromethyl)phenyl)-5-(5-fluoropyridin-2-yl)-2-(pyridin-3-yl)-3H-imidazo[4,5-b]pyridine (Intermediate 228, 410 mg, HCl salt, crude) as a yellow solid. MS: m/z=416.0 [M+H]⁺.

Intermediate 229: 2-(3-(4-(Chloromethyl)phenyl)-5-(5-fluoropyridin-2-yl)-3H-imidazo[4,5-b]pyridin-2-yl) aniline

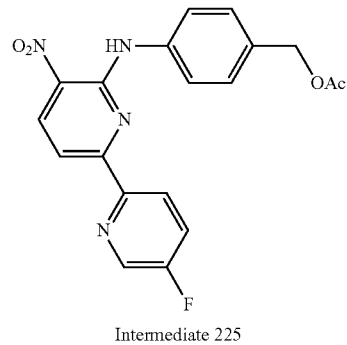

Intermediate 225

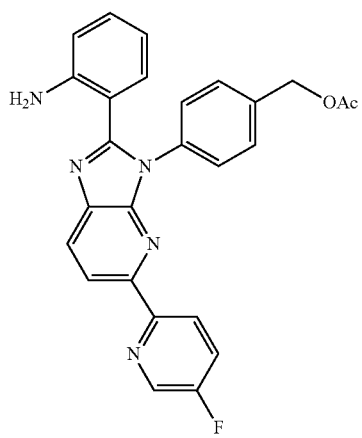

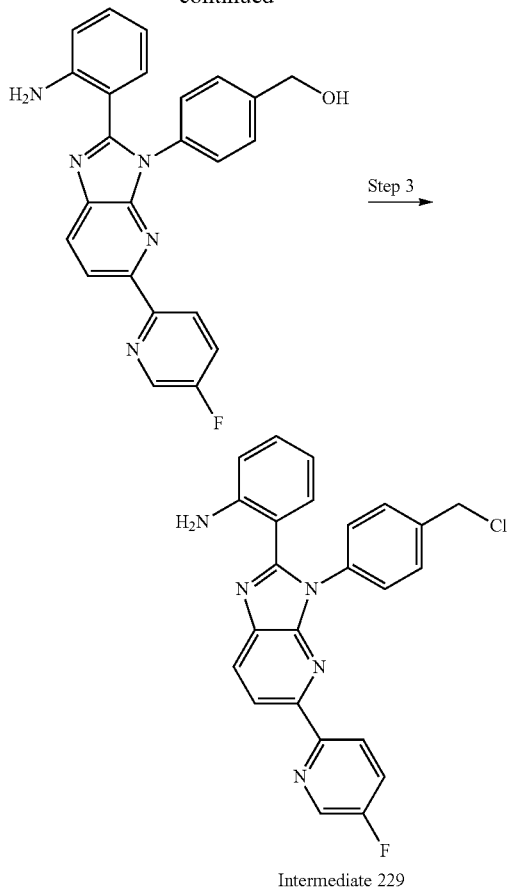

Intermediate 229

Step 1: 4-(2-(2-Aminophenyl)-5-(5-fluoropyridin-2-yl)-3H-imidazo[4,5-b]pyridin-3-yl)benzyl acetate A mixture of Intermediate 225 (1 g, 2.62 mmol), 2-aminobenzaldehyde (348 mg, 2.88 mmol), Na₂S₂O₄ (1.82 g, 10.5 mmol) in DMSO (5 mL) was degassed and purged with N₂ three times. The mixture was stirred at 100° C. for 16 hr under N₂ atmosphere. The reaction mixture was diluted with H₂O (30 mL) and extracted with EtOAc (20 mL×3). The combined organic layers were washed with brine (30 mL), dried over Na₂SO₄, filtered, and concentrated under reduced pressure. After purified by silica gel flash chromatography (Eluent of 0~20% EtOAc in petroleum ether), 4-(2-(2-aminophenyl)-5-(5-fluoropyridin-2-yl)-3H-imidazo[4,5-b]pyridin-3-yl)benzyl acetate (150 mg, yield: 9%) was obtained as a yellow solid. MS: m/z=454.1 [M+H]⁺. ¹H NMR (400 MHz, Dimethysulfoxide-d₆) 8.66 (d, J=2.8 Hz, 1H), 8.39 (d, J=8.4 Hz, 1H), 8.30-8.22 (m, 2H), 7.88-7.79 (m, 1H), 7.55-7.46 (m, 4H), 7.10-7.02 (m, 1H), 6.89-6.77 (m, 2H), 6.41-6.33 (m, 1H), 6.18 (br s, 2H), 5.18 (s, 2H), 2.12 (s, 3H).

Step 2: (4-(2-(2-Aminophenyl)-5-(5-fluoropyridin-2-yl)-3H-imidazo[4,5-b]pyridin-3-yl)phenyl)methanol To a solution of 4-(2-(2-aminophenyl)-5-(5-fluoropyridin-2-yl)-3H-imidazo[4,5-b]pyridin-3-yl)benzyl acetate (150 mg, 331 gmol) in MeOH (2 mL) and THF (2 mL) was added K₂CO₃ (137 mg, 992 µmol) in H₂O (1 mL). The mixture was stirred at 25° C. for 0.5 hr. The reaction mixture was diluted with H₂O (30 mL) and extracted with EtOAc (20 mL×3). The combined organic layers were washed with brine (30 mL), dried over Na₂SO₄, filtered and concentrated under reduced pressure. (4-(2-(2-Aminophenyl)-5-(5-fluoropyridin-2-yl)-3H-imidazo[4,5-b]pyridin-3-yl)phenyl) methanol (155 mg, crude) was obtained as a yellow solid. MS: m z=412.1 [M+H]⁺.

Step 3: 2-(3-(4-(Chloromethyl)phenyl)-5-(5-fluoropyridin-2-yl)-3H-imidazo[4,5-b]pyridin-2-yl) aniline To a solution of 4-(2-(2-aminophenyl)-5-(5-fluoropyridin-2-yl)-3H-imidazo[4,5-b]pyridin-3-yl)phenyl)methanol (155 mg, 377 µmol) in CH₂Cl₂ (2 mL) was added SOCl₂ (90 mg, 753 µmol). The mixture was stirred at 25° C. for 1 hr. The mixture was concentrated under reduced pressure to give 2-(3-(4-(chloromethyl)phenyl)-5-(5-fluoropyridin-2-yl)-3H-imidazo[4,5-b]pyridin-2-yl) aniline (Intermediate 229, 175 mg, HCl salt, crude) as a yellow solid, which was used in the next step without further purification. MS: m/z=430.0 [M+H]⁺.

Intermediate 230: 3-(4-(Chloromethyl)phenyl)-5-(5-fluoropyridin-2-yl)-2-phenyl-3H-imidazo[4,5-b]pyridine

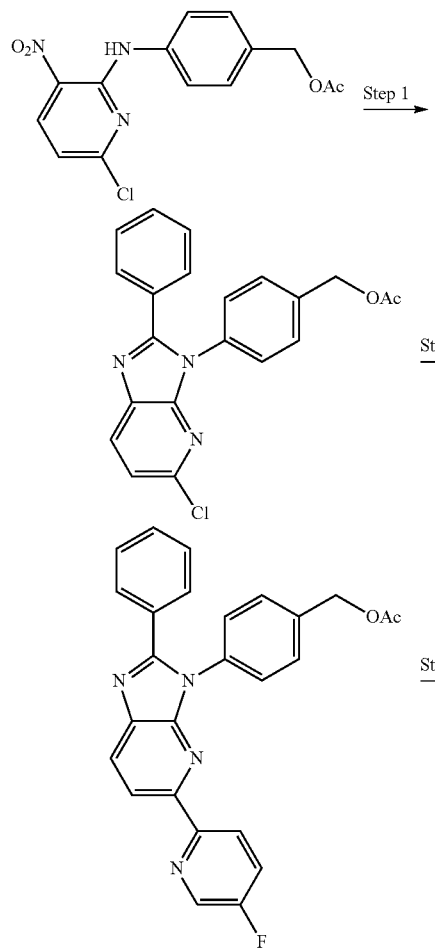

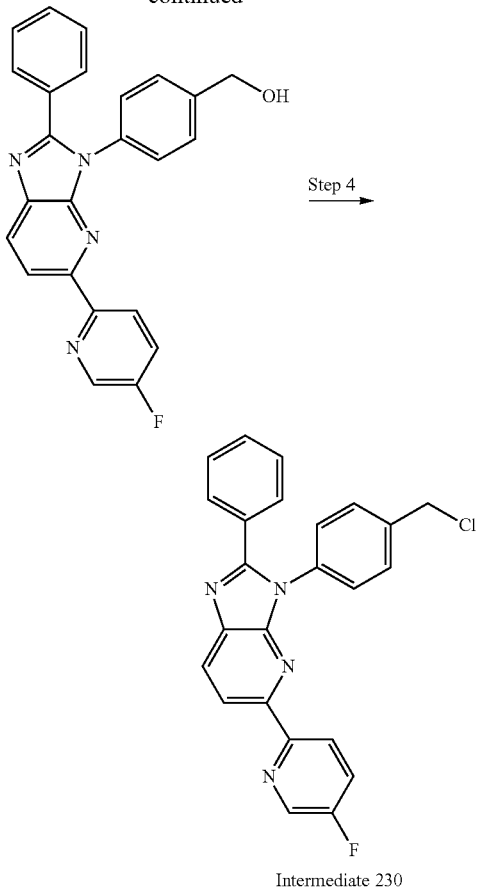

Step 1: 4-(5-Chloro-2-phenyl-3H-imidazo[4,5-b]pyridin-3-yl)benzyl acetate

To a solution of 4-((6-chloro-3-nitropyridin-2-yl)amino) benzyl acetate (refer to Intermediate 178 for detail procedures, 1.4 g, 3.8 mmol) in DMSO (10 mL) were added Na₂S₂O₄ (2 g, 6.22 mmol, 87% purity) and benzaldehyde (792 mg, 7.46 mmol). The mixture was stirred at 100° C. for 16 hr. The reaction mixture was quenched with H₂O (50 mL) and extracted with EtOAc (50 mL×2). The combined organic layers were washed with brine (50 mL×2), dried over Na₂SO₄, filtered, and concentrated under reduced pressure. After purified by silica gel flash chromatography (Eluent of 0%~43% EtOAc in petroleum ether), 4-(5-chloro-2-phenyl-3H-imidazo[4,5-b]pyridin-3-yl)benzyl acetate (440 mg, yield: 18%) was obtained as a light yellow solid. MS: m/z=378.2 [M+H]⁺. ¹H NMR (400 MHz, Chloroform-d) δ 8.09 (d, J=8.4 Hz, 1H), 7.58-7.54 (m, 2H), 7.48 (d, J=8.4 Hz, 2H), 7.41 (d, J=7.2 Hz, 1H), 7.37-7.32 (m, 5H), 5.18 (s, 2H), 2.15 (s, 3H).

Step 2: 4-(5-(5-Fluoropyridin-2-yl)-2-phenyl-3H-imidazo[4,5-b]pyridin-3-yl)benzyl acetate A mixture of 4-(5-chloro-2-phenyl-3H-imidazo[4,5-b]pyridin-3-yl)benzyl acetate (360 mg, 953 µmol), (5-fluoropyridin-2-yl)boronic acid (403 mg, 2.86 mmol), Pd(dppf)Cl₂ (69.7 mg, 95.3 µmol), Cs₂CO₃ (931 mg, 2.86 mmol) and CuBr (54.7 mg, 381 µmol) in 1,4-dioxane (7.5 m L) and H₂O 0.5 mL) was degassed and purged with N₂ three times. The mixture was stirred at 100° C. for 8 hr under N₂ atmosphere. The reaction mixture was quenched with H₂O (100 mL), diluted with CH₂Cl₂ (100 mL), and extracted with CH₂Cl₂ (100 mL×2). The combined organic layers were washed with brine (100 mL), dried over Na₂SO₄, filtered, and concentrated under reduced pressure. After purified by silica gel flash chromatography (Eluent of 0%~35% EtOAc in petroleum ether), 4-(5-(5-fluoropyridin-2-yl)-2-phenyl-3H-imidazo[4,5-b]pyridin-3-yl)benzyl acetate (110 mg, yield: 24%) was obtained as a light yellow solid. MS: m/z=439.1 [M+H]⁺. ¹H NMR (400 MHz, Chloroform-d) δ 8.50 (d, J=2.8 Hz, 1H), 8.47 (d, J=8.4 Hz, 1H), 8.36 (dd, J=8.8, 4.8 Hz, 1H), 8.22 (d, J=8.4 Hz, 1H), 7.62 (d, J=7.6 Hz, 2H), 7.52-7.50 (m, 2H), 7.46-7.43 (m, 4H), 7.38 (d, J=8.0 Hz, 2H), 5.23 (s, 2H), 2.18 (s, 3H).

Step 3: (4-(5-(5-Fluoropyridin-2-yl)-2-phenyl-3H-imidazo[4,5-b]pyridin-3-yl)phenyl)methanol To a solution of 4-(5-(5-fluoropyridin-2-yl)-2-phenyl-3H-imidazo[4,5-b]pyridin-3-yl)benzyl acetate (110 mg, 251 μmol) in THF (2 mL) and MeOH (2 mL) were added K₂CO₃ (104 mg, 753 μmol) and H₂O (1 mL). The mixture was stirred at 25° C. for 1 hr. The reaction mixture was quenched with H₂O (50 mL) at 25° C. and extracted with EtOAc (50 mL×2). The combined organic layers were washed with brine (50 mL×2), dried over Na₂SO₄, filtered and concentrated under reduced pressure. (4-(5-(5-Fluoropyridin-2-yl)-2-phenyl-3H-imidazo[4,5-b]pyridin-3-yl)phenyl)methanol (99 mg, yield: 99%) was obtained as a light yellow solid. MS: m/z=397.1 [M+H]⁺.

Step 4: 3-(4-(Chloromethyl)phenyl)-5-(5-fluoropyridin-2-yl)-2-phenyl-3H-imidazo[4,5-b]pyridine To a solution of (4-(5-(5-fluoropyridin-2-yl)-2-phenyl-3H-imidazo[4,5-b]pyridin-3-yl)phenyl)methanol (99 mg, 250 μmol) in CH₂Cl₂ (2 mL) was added SOCl₂ (89.1 mg, 749 μmol). The mixture was stirred at 40° C. for 0.5 hr. The reaction was concentrated under reduced pressure to give 3-(4-(chloromethyl)phenyl)-5-(5-fluoropyridin-2-yl)-2-phenyl-3H-imidazo[4,5-b]pyridine (Intermediate 230, 103 mg, HCl salt) as a light yellow solid. MS: m/z=415.1 [M+H]⁺.

Intermediate 231: 2-Bromo-5-(methoxy-d₃)pyridine

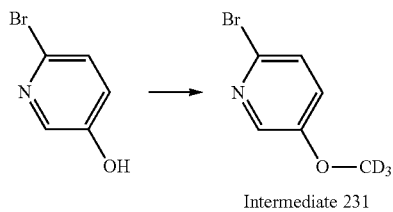 [SMILES: Oc1ccc(Br)nc1 ; [2H]C([2H])([2H])Oc1ccc(Br)nc1]

Intermediate 231

To a solution of 6-bromopyridin-3-ol (1 g, 5.8 mmol), CD₃OD (1.2 g, 34.5 mmol) and PPh₃ (1.7 g, 6.3 mmol) in 1,4-dioxane (10 mL) was added DIAD (1.4 mg, 6.9 mmol) at 0° C. The mixture was stirred at 25° C. for 4 hr. The mixture was quenched with H₂O (50 mL) and extracted with CH₂Cl₂ (20 mL×2). The combined organic layers were washed with brine (50 mL×3), dried over Na₂SO₄, filtered and concentrated. After purified by silica gel flash chromatography (Eluent of 0%/5% EtOAc in petroleum ether), 2-bromo-5-(methoxy-d₃)pyridine (Intermediate 231, 1 g, yield: 84%) was obtained as a light yellow oil. MS: m/z=190.7, 192.7 [M+H]⁺. ¹H NMR (400 MHz, Dimethyl-sulfoxide-d₆) δ 8.12 (d, J=3.2 Hz, 1H), 7.55 (d, J=8.8 Hz, 1H), 7.39 (dd, J=8.8, 3.2 Hz, 1H).

Intermediate 232: 3-(3-(4-(Chloromethyl)phenyl)-5-(5-(methoxy-d₃)pyridin-2-yl)-3H-imidazo[4,5-b]pyridin-2-yl)pyridin-2-amine

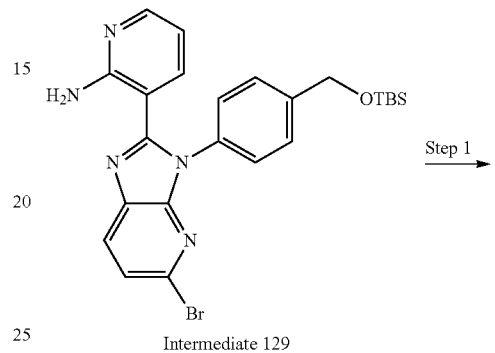

Intermediate 129

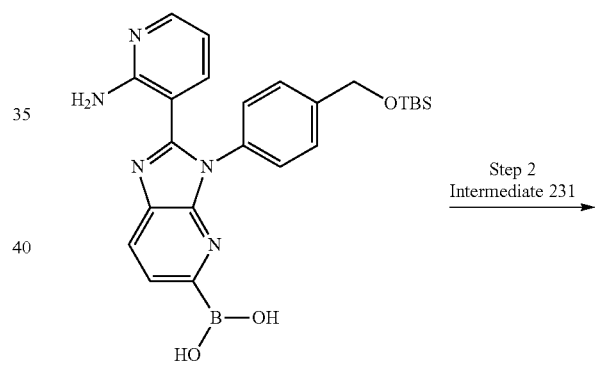

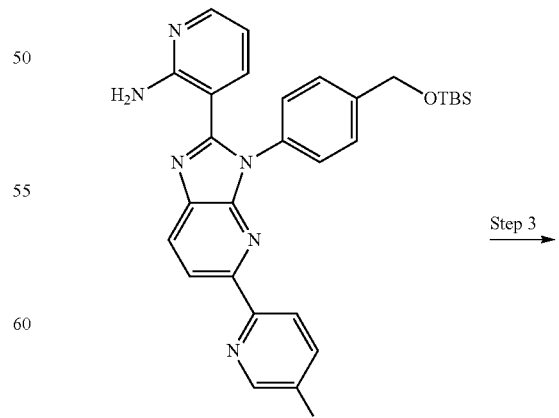

-continued

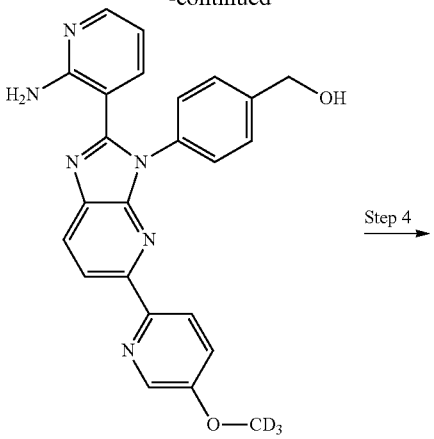

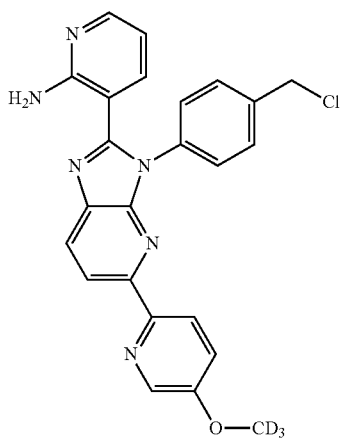

Intermediate 232

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1.5 g, 2.9 mmol), 4,4,4',4',5,5,5',5'-octamethyl-2,2'-bi(1,3,2-dioxaborolane) (1.1 g, 4.4 mmol), KOAc (865 mg, 8.8 mmol) and Pd(dppf)Cl$_2$ (120 mg, 147 μmol) in 1,4-dioxane (15 mL) was degassed and purged with N$_2$ three times. The mixture was stirred at 110° C. for 2 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step directly without work-up and purification. MS: m/z=476.2 [M+H]$^+$.

Step 2: 3-(3-(4-(((tert-Butyldimethylsilyl)oxy)methyl)phenyl)-5-(5-(methoxy-d$_3$)pyridin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (426 mg, 898 μmol), Intermediate 231 (206 mg, 1.0 mmol), Pd(dppf)Cl$_2$ (73 mg, 90 μmol) and Cs$_2$CO$_3$ (877 mg, 2.7 mmol) in 1,4-dioxane (5 mL) and H$_2$O (1 mL) was degassed and purged with N$_2$ three times. The mixture was stirred at 95° C. for 12 hr under N$_2$ atmosphere. The reaction mixture was quenched with H$_2$O (30 mL) and extracted with CH$_2$Cl$_2$ (20 mL×2). The combined organic layers were washed with brine (50 mL), dried over Na$_2$SO$_4$, filtered, and concentrated under reduced pressure. After purified by silica gel flash chromatography (Eluent of 0%~25% EtOAc in petroleum ether), 3-(3-(4-(((tert-butyldimethylsilyl)oxy)methyl)phenyl)-5-(5-(methoxy-d$_3$)pyridin-2-yl)-3H-imidazo[4,5-b]pyridin-2-yl)pyridin-2-amine (240 mg, yield: 44% for two steps) was obtained as a black solid. MS: m/z=542.4 [M+H]$^+$. D %: 3D %=95.3%. $^1$H NMR (400 MHz, Dimethylsulfoxide-d$_6$) δ 8.39-8.34 (m, 2H), 8.26 (d, J=8.4 Hz, 1H), 8.12 (d, J=8.8 Hz, 1H), 8.00 (dd, J=4.4, 1.6 Hz, 1H), 7.51-7.48 (m, 4H), 7.47-7.45 (m, 1H), 7.19 (dd, J=7.6, 1.6 Hz, 1H), 7.01 (s, 2H), 6.39 (dd, J=7.6, 4.8 Hz, 1H), 4.84 (s, 2H), 0.93 (s, 9H), 0.12 (s, 6H).

Step 3: (4-(2-(2-Aminopyridin-3-yl)-5-(5-(methoxy-<h)pyridin-2-yl)-3H-imidazo[4,5-b]pyridin-3-yl)phenyl)methanol To a solution of 3-(3-(4-(((tert-butyldimethylsilyl)oxy)methyl)phenyl)-5-(5-(methoxy-d3)pyridin-2-yl)-3H-imidazo[4,5-b]pyridin-2-yl)pyridin-2-amine (200 mg, 369 μmol) in THF (3 mL) was added TBAF (3.7 mL, 3.7 mmol, 1 M in THF). The mixture was stirred at 25° C. for 2 hr. The reaction mixture was quenched with H$_2$O (5 mL) at 25° C. and extracted with CH$_2$Cl$_2$ (15 mL×2). The combined organic layers were washed with brine (30 mL×2), dried over Na$_2$SO$_4$, filtered and concentrated under reduced pressure. After triturated with EtOAc:petroleum ether=1:10 (11 mL) at 25° C. for 10 min, (4-(2-(2-aminopyridin-3-yl)-5-(5-(methoxy-d$_6$)pyridin-2-yl)-3H-imidazo[4,5-b]pyridin-3-yl)phenyl)methanol (155 mg, crude) was obtained as a brown solid. MS: m/z=428.0 [M+H]$^+$. D %: 3D %=99.5%. $^1$H NMR (400 MHz, Dimethylsulfoxide-d$_6$) δ 8.40-8.34 (m, 2H), 8.26 (d, J=8.4 Hz, 1H), 8.13 (d, J=9.2 Hz, 1H), 8.00 (dd, J=4.8, 1.6 Hz, 1H), 7.53-7.41 (m, 5H), 7.22 (dd, J=8.0, 1.6 Hz, 1H), 6.97 (s, 2H), 6.42 (dd, J=7.6, 4.8 Hz, 1H), 5.40-5.30 (m, 1H), 4.61 (d, J=5.2 Hz, 2H).

Step 4: 3-(3-(4-(Chloromethyl)phenyl)-5-(5-(methoxy-d$_6$)pyridin-2-yl)-3H-imidazo[4,5-b]pyridin-2-yl)pyridin-2-amine To a solution of (4-(2-(2-aminopyridin-3-yl)-5-(5-(methoxy-d$_6$)pyridin-2-yl)-3H-imidazo[4,5-b]pyridin-3-yl)phenyl)methanol (150 mg, 351 μmol) in CH$_2$Cl$_2$ (3 mL) was added SOCl$_2$ (209 mg, 1.7 mmol). The mixture was stirred at 40° C. for 1 hr. The reaction was concentrated under reduced pressure to give 3-(3-(4-(chloromethyl)phenyl)-5-(5-(methoxy-d$_3$)pyridin-2-yl)-3H-imidazo[4,5-b]pyridin-2-yl)pyridin-2-amine (Intermediate 232, 150 mg, HCl salt, crude) as a yellow solid. MS: m/z=446.0 [M+H]$^+$. D %: 3D=99.7%.

Intermediate 233: 3-(3-(4-(Chloromethyl)phenyl)-5-(5-(difluoromethoxy)pyridin-2-yl)-3H-imidazo[4,5-b]pyridin-2-yl)pyridin-2-amine

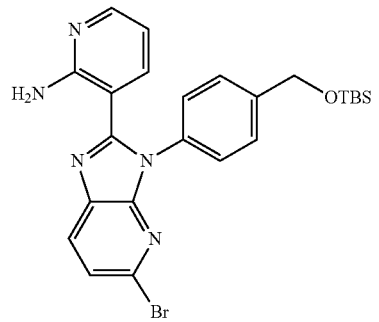

Intermediate 129

Step 1

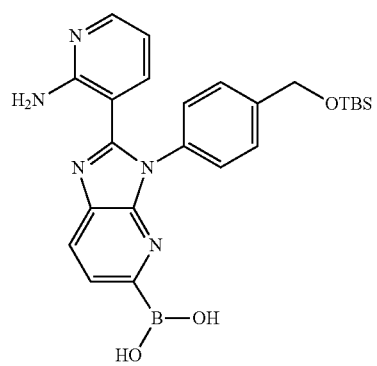

Step 2

Step 3

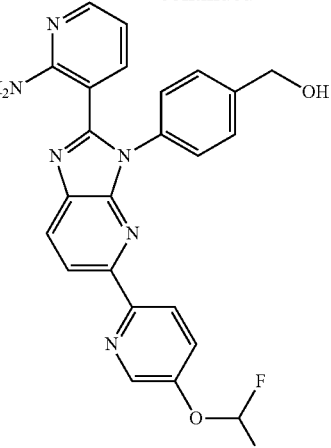

Step 4

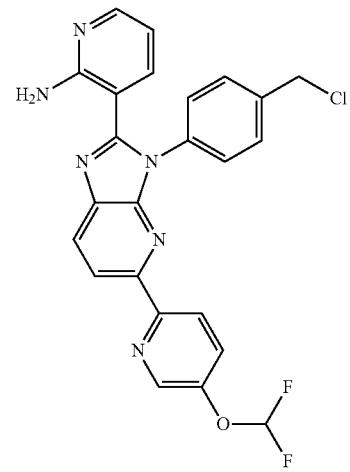

Intermediate 233

Step 1: (2-(2-Aminopyridin-3-yl)-3-(4-(((ter-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl$_2$ (143 mg, 196 mmol) in 1,4-dioxane (5 mL) was degassed and purged with N$_2$ three times. The mixture was stirred at 90° C. for 16 hr under N$_2$ atmosphere. (2-(2-Aminopyridin-3-yl)-3-(4-(((tert-butyldimethylsilyl)oxy)methyl)phenyl)-3H-imidazo[4,5-h]pyridin-5-yl)boronic acid was obtained as a black liquid, which was used in the next step without work-up and purification. MS: m/z=476.2 [M+H]$^+$.

Step 2: 3-(3-(4-(((tert-Butyldimethylsilyl)oxy)methyl)phenyl)-5-(5-(difluoromethoxy)pyridin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (470 mg, 989 μmol), 2-bromo-5-(difluoromethoxy)pyridine (266 mg, 1.19 mmol), Pd(dppf)Cl$_2$ (72.3 mg, 98.9 μmol) and Cs$_2$CO$_3$ (966 mg, 2.97 mmol) in 1,4-dioxane (4 mL) and H$_2$O (1 mL) was degassed and purged with N$_2$ three times. The mixture was stirred at 90°

C. for 16 hr under $N_2$ atmosphere. The reaction mixture was poured into $H_2O$ (15 mL) and extracted with EtOAc (15 mL×3). The combined organic phases were dried over anhydrous $Na_2SO_4$, filtered and concentrated under reduced pressure. After purified by silica gel flash chromatography (Eluent of 0%~56%/EtOAc in petroleum ether), 3-(3-(4-(((tert-butyldimethylsilyl)oxy)methyl)phenyl)-5-(5-(difluoromethoxy)pyridin-2-yl)-3H-imidazo[4,5-b]pyridin-2-yl)pyridin-2-amine (210 mg, yield: 37% for two steps) was obtained as a brown solid. MS: m/z=575.2 [M+H]$^+$. $^1$H NMR (400 MHz, Dimethysulfoxide-d$_6$) δ 8.57 (d, J=8.4 Hz, 1H), 8.40 (d, J=8.4 Hz, 1H), 8.31 (d, J=8.4 Hz, 1H), 8.21 (d, J=8.8 Hz, 1H), 8.00 (dd, J=4.8, 2.0 Hz, 1H), 7.76 (dd, J=8.4, 2.4 Hz, 1H), 7.54-7.45 (m, 4H), 7.41-7.27 (m, 1H), 7.22-7.16 ((m, 1H), 7.00 (s, 2H), 6.34 (dd, J=7.6, 4.8 Hz, 1H), 4.82 (s, 2H), 0.93 (s, 9H), 0.12 (s, 6H). $^{19}$F NMR (400 MHz, Dimethysulfoxide-d$_6$) δ −82.487.

Step 3: (4-(2-(2-Aminopyridin-3-yl)-5-(5-(difluoromethoxy)pyridin-2-yl)-3H-imidazo[4,5-b]pyridin-3-yl)phenyl)methanol To a solution of 3-(3-(4-(((tert-butyldimethylsilyl)oxy)methyl)phenyl)-5-(5-(difluoromethoxy)pyridin-2-yl)-3H-imidazo[4,5-b]pyridin-2-yl)pyridin-2-amine (210 mg, 365 μmol) in THF (3 mL) was added TBAF (1 mL, 1 M in THF). The mixture was stirred at 25° C. for 0.3 hr. The reaction mixture was poured into $H_2O$ (15 mL) and extracted with EtOAc (15 mL×3). The combined organic layers were dried over anhydrous $Na_2SO_4$, filtered, and concentrated under reduced pressure. (4-(2-(2-Aminopyridin-3-yl)-5-(5-(difluoromethoxy)pyridin-2-yl)-3H-imidazo[4,5-b]pyridin-3-yl)phenyl)methanol (101 mg, crude) was obtained as a brown solid. MS: m/z=461.1 [M+H]$^+$.

Step 4: 3-(3-(4-(Chloromethyl)phenyl)-5-(5-(difluoromethoxy)pyridin-2-yl)-3H-imidazo[4,5-b]pyridin-2-yl)pyridin-2-amine To a solution of (4-(2-(2-aminopyridin-3-yl)-5-(5-(difluoromethoxy)pyridin-2-yl)-3H-imidazo[4,5-b]pyridin-3-yl)phenyl)methanol (101 in, 219 μmol) in $CH_2Cl_2$ (4 mL) was added $SOCl_2$ (1 mL). The mixture was stirred at 25° C. for 1 hr. The reaction was concentrated under reduced pressure to give 3-(3-(4-(chloromethyl)phenyl)-5-(5-(difluoromethoxy)pyridin-2-yl)-3H-imidazo[4,5-b]pyridin-2-yl)pyridin-2-amine (Intermediate 233, 115 mg, HCl salt) as a brown solid. MS: m/z=479.1 [M+H]$^+$.

Intermediate 234:
2-Bromo-5-(fluoromethoxy)pyridine

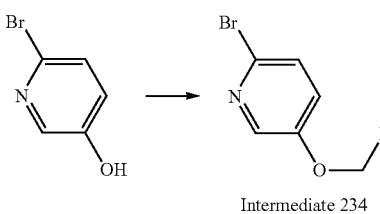

Intermediate 234

To a solution of 6-bromopyridin-3-ol (1 g, 5.8 mmol) and $K_2CO_3$ (2.4 g, 17.2 mmol) in DMF (10 mL) was added bromofluoromethane (974 mg, 8.6 mmol) at 0° C. The mixture was stirred at 0° C. for 2 hr. The mixture was quenched with $H_2O$ (50 mL) and extracted with $CH_2Cl_2$ (20 mL×2). The combined organic layers were washed with brine (50 mL×3), dried over $Na_2SO_4$, filtered and concentrated. After purified by silica gel flash chromatography (Eluent of 0%~15% EtOAc in petroleum ether), 2-bromo-5-(fluoromethoxy)pyridine (Intermediate 234, 1 g, yield: 84%) was obtained as a light yellow oil. MS: m/z=205.7, 207.7 [M+H]$^+$. $^1$H NMR (400 MHz, Dimethylsulfoxide-d$_6$) δ 8.27 (d, J=3.0 Hz, 1H), 7.66 (d, J=8.8 Hz, 1H), 7.61-7.55 (m, 1H), 5.93 (d, J=53.6 Hz, 2H). $^{19}$F NMR (400 MHz, Dimethylsulfoxide-d$_6$) δ −152.277.

Intermediate 235: 3-(3-(4-(Chloromethyl)phenyl)-5-(5-(fluoromethoxy)pyridin-2-yl)-3H-imidazo[4,5-b]pyridin-2-yl)pyridin-2-amine

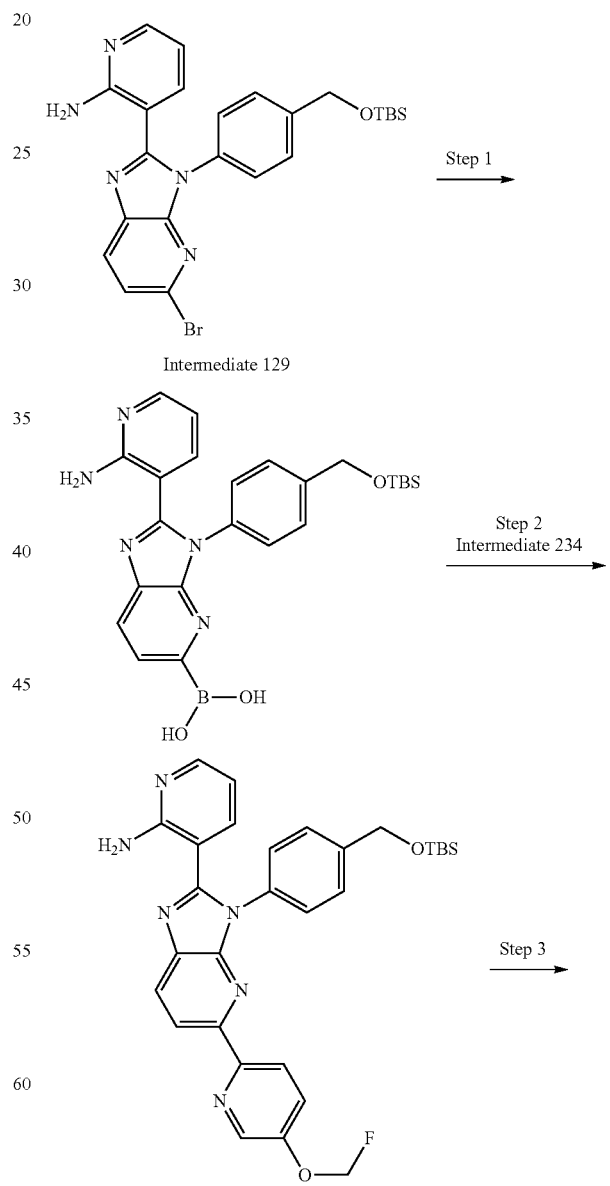

-continued

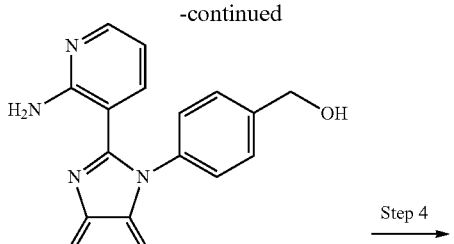

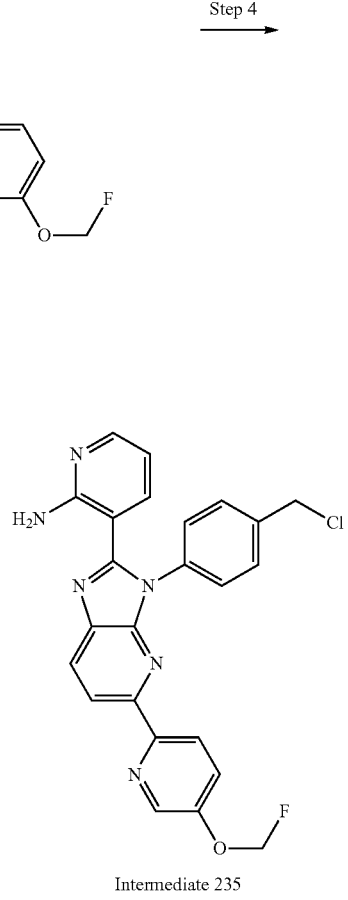

Intermediate 235

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1.5 g, 2.9 mmol), 4,4,4',4',5,5,5',5'-octamethyl-2,2'-bi(1,3,2-dioxaborolane) (1.1 g, 4.4 mmol), KOAc (865 mg, 8.8 mmol) and Pd(dppf)Cl$_2$ (120 mg, 147 μmol) in 1,4-dioxane (15 mL) was degassed and purged with N$_2$ three times. The mixture was stirred at 110° C. for 2 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((tert-Butyldimethylsilyl)oxy)methyl)phenyl)-5-(5-(fluoromethoxy)pyridin-2-yl)-3H-imidazo[4,5-b]pyridin-2-yl)pyridin-2-amine A mixture of (2-(2-Aminopyridin-3-yl)-3-(4-(((tert-butyldimethylsilyl)oxy)methyl)phenyl)-3H-imidazo[4,5-b]pyridin-5-yl)boronic acid (426 mg, 897 μmol), Intermediate 234 (221 mg, 1.1 mmol), Pd(dppf)Cl$_2$ (73 mg, 90 μmol) and Cs$_2$CO$_3$ (876 mg, 2.7 mmol) in 1,4-dioxane (5 mL) was degassed and purged with N$_2$ three times. The mixture was stirred at 95° C. for 12 hr under N$_2$ atmosphere. The reaction mixture was quenched with H$_2$O (30 mL) and extracted with CH$_2$Cl$_2$ (20 mL×2). The combined organic layers were washed with brine (50 mL), dried over Na$_2$SO$_4$, filtered, and concentrated under reduced pressure. After purified by silica gel flash chromatography (Eluent of 0%~25% EtOAc in petroleum ether), 3-(3-(4-(((tert-butyldimethylsilyl)oxy)methyl)phenyl)-5-(5-(fluoromethoxy)pyridin-2-yl)-3H-imidazo[4,5-b]pyridin-2-yl)pyridin-2-amine (260 mg, yield: 46% for two steps) was obtained as a brown solid. MS: m/z=557.3 [M+H]$^+$. $^1$H NMR (400 MHz, Dimethylsulfoxide-d$_6$) δ 8.51 (d, J=2.8 Hz, 1H), 8.39 (d, J=8.4 Hz, 1H), 8.29 (d, J=8.4 Hz, 1H), 8.17 (d, J=8.8 Hz, 1H), 8.00 (dd, J=4.8, 1.6 Hz, 1H), 7.67 (dd, J=8.8, 2.8 Hz, 1H), 7.51-7.47 (m, 4H), 7.20 (dd, J=7.6, 2.0 Hz, 1H), 7.00 (s, 2H), 6.39 (dd, J=7.6, 4.8 Hz, 1H), 5.96 (d, J=53.6 Hz, 2H), 4.84 (s, 2H), 0.93 (s, 9H), 0.12 (s, 6H). $^{19}$F NMR (400 MHz, Dimethylsulfoxide-d$_6$) δ −151.294.

Step 3: (4-(2-(2-Aminopyridin-3-yl)-5-(5-(fluoromethoxy)pyridin-2-yl)-3H-imidazo[4,5-b]pyridin-3-yl)phenyl)methanol To a solution of 3-(3-(4-(((tert-butyldimethylsilyl)oxy)methyl)phenyl)-5-(5-(fluoromethoxy)pyridin-2-yl)-3H-imidazo[4,5-b]pyridin-2-yl)pyridin-2-amine (200 mg, 359 μmol) in THF (3 mL) was added TBAF (3.6 mL, 3.6 mmol, 1 M in THF). The mixture was stirred at 25° C. for 2 hr. The reaction mixture was quenched with H$_2$O (5 mL) at 25° C. and extracted with CH$_2$Cl$_2$ (15 mL×2). The combined organic layers were washed with brine (30 mL×2), dried over Na$_2$SO$_4$, filtered and concentrated under reduced pressure. After triturated with EtOAc:petroleum ether=1:10 (11 mL) at 25° C. for 10 min, (4-(2-(2-aminopyridin-3-yl)-5-(5-(fluoromethoxy)pyridin-2-yl)-3H-imidazo[4,5-b]pyridin-3-yl)phenyl)methanol (155 mg, crude) was obtained as a brown solid. MS: m/z=442.9 [M+H]$^+$. $^1$H NMR (400 MHz, Dimethylsulfoxide-d$_6$) δ 8.51 (d, J=2.8 Hz, 1H), 8.39 (d, J=8.4 Hz, 1H), 8.29 (d, J=8.4 Hz, 1 H), 8.18 (d, J=8.8 Hz, 1H), 8.01 (dd, J=4.8, 1.6 Hz, 1H), 7.69 (dd, J=8.8, 2.8 Hz, 1H), 7.52-7.45 (m, 4H), 7.23 (dd, J=7.6, 1.6 Hz, 1H), 6.96 (s, 2H), 6.42 (dd, J=7.6, 4.8 Hz, 1H), 5.96 (d, J=53.6 Hz, 2H), 5.43-5.33 (m, 1H), 4.61 (s, 2H). $^{19}$F NMR (400 MHz, Dimethylsulfoxide-d$_6$) δ −151.294.

Step 4: 3-(3-(4-(Chloromethyl)phenyl)-5-(5-(fluoromethoxy)pyridin-2-yl)-3H-imidazo[4,5-b]pyridin-2-yl)pyridin-2-amine To a solution of (4-(2-(2-aminopyridin-3-yl)-5-(5-(fluoromethoxy)pyridin-2-yl)-3H-imidazo[4,5-b]pyridin-3-yl)phenyl)methanol (150 mg, 339 μmol) in CH$_2$Cl$_2$ (5 mL) was added SOCl$_2$ (209 mg, 1.7 mmol). The mixture was stirred at 40° C. for 1 hr. The reaction was concentrated under reduced pressure to give 3-(3-(4-(chloromethyl)phenyl)-5-(5-(fluoromethoxy)pyridin-2-yl)-3H-imidazo[4,5-b]pyridin-2-yl)pyridin-2-amine (intermediate 235, 150 mg, HCl salt, crude) as a yellow solid. MS: m/z=460.9 [M+H]$^+$.

Intermediate 236: 3-(3-(4-(Chloromethyl)phenyl)-5-(5-methoxypyrimidin-2-yl)-3H-imidazo[4,5-b]pyridin-2-yl)pyridin-2-amine

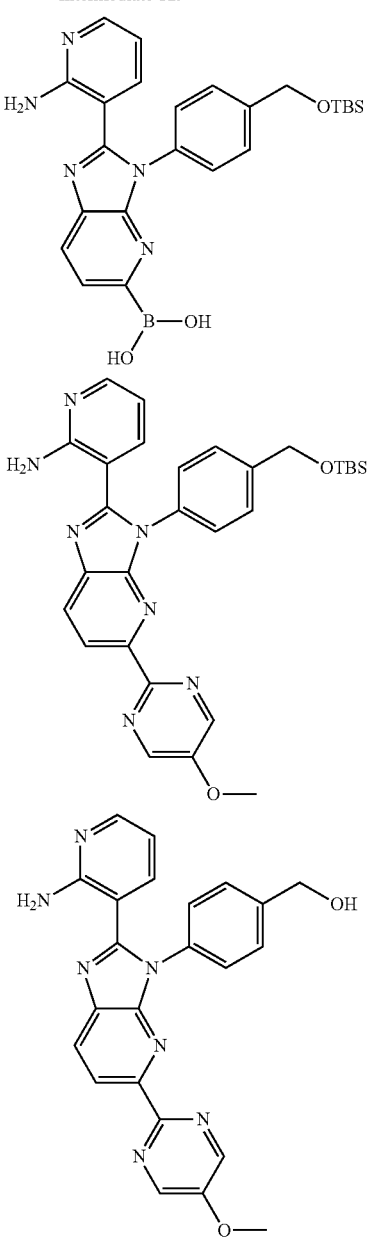

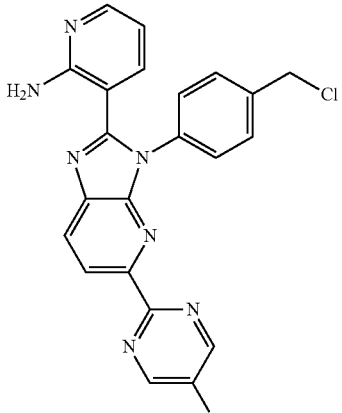

Intermediate 236

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (500 mg, 979 μmol), 4,4,4',4',5,5,5',5'-octamethyl-2,2'-bi(1,3,2-dioxaborolane) (497 mg, 1.96 mmol), KOAc (288 mg, 2.94 mmol) and Pd(dppf)Cl₂ (71.7 mg, 97.9 μmol) in 1,4-dioxane (2 mL) was degassed and purged with N₂ three times. The mixture was stirred at 80° C. for 16 hr under N₂ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]⁺.

Step 2: 3-(3-(4-(((tert-Butyldimethylsilyl)oxy)methyl)phenyl)-5-(5-methoxypyrimidin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (465 mg, 978 μmol), 2-bromo-5-methoxypyrimidine (185 mg, 978 μmol), Pd(dppf)Cl₂ (71.6 mg, 97.8 μmol) and Cs₂CO₃ (956 mg, 2.93 mmol) in 1,4-dioxane (5 mL) and H₂O (1 mL) was degassed and purged with N₂ three times. The mixture was stirred at 90° C. for 2 hr under N₂ atmosphere. The reaction mixture was quenched with H₂O (5 mL), diluted with CH₂Cl₂ (10 mL), and extracted with CH₂Cl₂ (15 mL×2). The combined organic layers were washed with brine (50 mL), dried over Na₂SO₄, filtered and concentrated under reduced pressure. After purified by silica gel flash chromatography (Eluent of 30%~60% EtOAc in petroleum ether), 3-(3-(4-(((tert-butyldimethylsilyl)oxy)methyl)phenyl)-5-(5-methoxypyrimidin-2-yl)-3H-imidazo[4,5-b]pyridin-2-yl)pyridin-2-amine (280 mg, yield: 46% for two steps) was obtained as a black solid. MS: m/z=540.2 [M+H]⁺. ¹H NMR (400 MHz, Chloroform-d) δ 8.53 (s, 2H), 8.48 (d, J=8.4 Hz, 1H), 8.19 (d, J=8.4 Hz, 1H), 8.06 (dd, J=4.8, 1.6 Hz, 1H), 7.51-7.41 (m, 4H), 7.08 (dd, J=7.6, 1.6 Hz, 1H), 6.62 (br s, 2H), 6.36 (dd, J=7.6, 4.8 Hz, 1H), 4.83 (s, 2H), 3.96 (s, 3H), 0.97 (s, 9H), 0.14 (s, 6H).

Step 3: (4-(2-(2-Aminopyridin-3-yl)-5-(5-methoxypyrimidin-2-yl)-3H-imidazo[4,5-b]pyridin-3-yl)phenyl)methanol To a solution of 3-(3-(4-(((tert-butyldimethylsilyl)oxy)methyl)phenyl)-5-(5-methoxypyrimidin-2-yl)-3H-imidazo

[4,5-b]pyridin-2-yl)pyridin-2-amine (260 mg, 481.75 μmol) in THF (5 mL) was added TBAF (378 mg, 1.45 mmol, 1 M in THF). The mixture was stirred at 25° C. for 1 hr. The reaction mixture was quenched with H₂O (5 mL) at 25° C. and extracted with CH₂Cl₂ (15 mL×2). The combined organic layers were washed with brine (30 mL×2), dried over Na₂SO₄, filtered and concentrated under reduced pressure. After triturated with EtOAc:petroleum ether=1:10 (11 mL) at 25° C. for 10 min, (4-(2-(2-aminopyridin-3-yl)-5-(5-methoxypyrimidin-2-yl)-3H-imidazo[4,5-b]pyridin-3-yl) phenyl)methanol (200 mg, yield: 92%) was obtained as a black solid. MS: m/z=426.2 [M+H]⁺. ¹H NMR (400 MHz, Dimethylsulfoxide-d₆) δ 8.66 (s, 2H), 8.39 (d, J=8.4 Hz, 1H), 8.29 (d, J=8.4 Hz, 1H), 7.99 (d, J=3.2 Hz, 1H), 7.52-7.47 (m, 2H), 7.45-7.40 (m, 2H), 7.22 (d, J=6.4 Hz, 1H), 6.98 (br s, 2H), 6.41 (dd, J=7.6, 4.8 Hz, 1H), 5.40 (t, J=5.6 Hz, 1H), 4.60 (d, J=5.6 Hz, 2H), 3.96 (s, 3H).

Step 4: 3-(3-(4-(Chloromethyl)phenyl)-5-(5-methoxypyrimidin-2-yl)-3H-imidazo[4,5-b]pyridin-2-yl)pyridin-2-amine To a solution of (4-(2-(2-aminopyridin-3-yl)-5-(5-methoxypyrimidin-2-yl)-3H-imidazo[4,5-b]pyridin-3-yl)phenyl)methanol (200 mg, 470 μmol) in CH₂Cl₂ (3 mL) was added SOCl₂ (280 mg, 2.35 mmol). The mixture was stirred at 25° C. for 0.5 hr. The reaction was concentrated under reduced pressure to give 3-(3-(4-(chloromethyl)phenyl)-5-(5-methoxypyrimidin-2-yl)-3H-imidazo[4,5-b]pyridin-2-yl) pyridin-2-amine (Intermediate 236, 226 mg, HCl salt) as a purple solid. MS: m/z=444.1 [M+H]⁺. ¹H NMR (400 MHz, Methanol-d₄) δ 8.96 (s, 2H), 8.75 (d, J=8.4 Hz, 1H), 8.54 (d, J=8.4 Hz, 1H), 8.05 (dd, J=6.0, 1.2 Hz, 1H), 7.85 (dd, J=7.6, 1.2 Hz, 1H), 7.74-7.70 (m, 2H), 7.64-7.60 (m, 2H), 6.87 (dd, J=7.2, 6.4 Hz, 1H), 4.80 (s, 2H), 4.16 (s, 3H).

Intermediate 237: 3-(3-(4-(Chloromethyl)phenyl)-5-(5-methylpyrazin-2-yl)-3H-imidazo[4,5-b]pyridin-2-yl)pyridin-2-amine

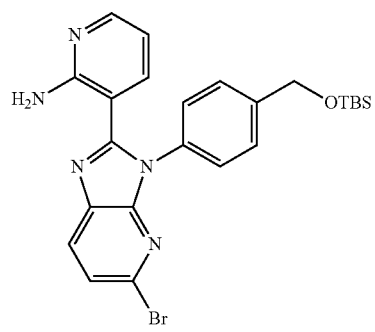

Intermediate 129

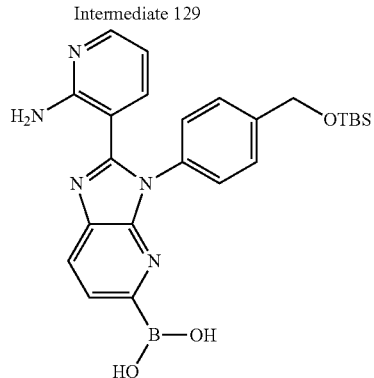

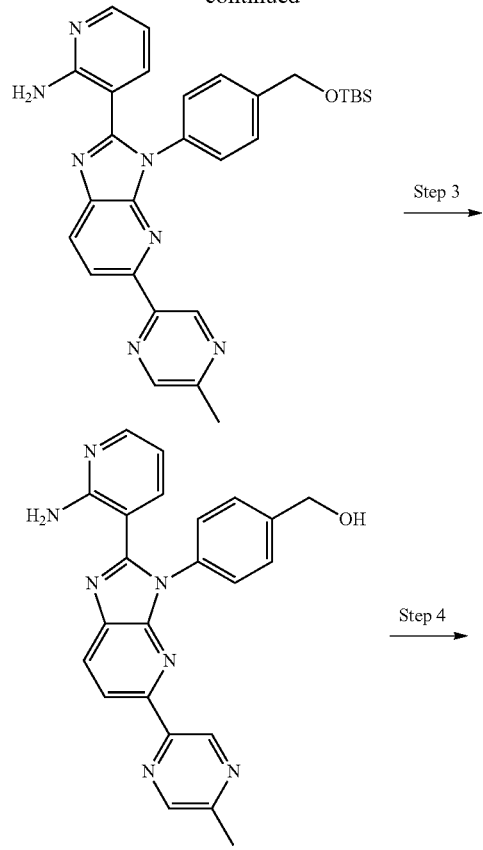

Intermediate 237

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (746 mg, 2.94 mmol), KOAc (577 mg, 5.88 mmol) and Pd(dppf)Cl₂ (80 mg, 98 μmol) in 1,4-dioxane (10 mL) was degassed and purged with N₂ three times. The mixture was stirred at 80° C. for 12 hr under N₂ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in next step without work-up and purification. MS: m/z=476.2 [M+H]⁺.

Step 2: 3-(3-(4-(((tert-Butyldimethylsilyl)oxy) methyl)phenyl)-5-(5-methylpyrazin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (500 mg, 1.0 mmol), 2-bromo-5-methylpyrazine (218 mg, 1.3 mmol), Pd(dppf)Cl$_2$ (86 mg, 105 μmol) and Cs$_2$CO$_3$ (1.0 g, 3.2 mmol) in 1,4-dioxane (5 mL) and H$_2$O (1 mL) was degassed and purged with N$_2$ three times. The mixture was stirred at 90° C. for 2 hr under N$_2$ atmosphere. The reaction mixture was diluted with H$_2$O (15 mL) and extracted with EtOAc (15 mL×3). The combined organic layers were washed with brine (30 mL), dried over Na$_2$SO$_4$, filtered and concentrated under reduced pressure. After purified by silica gel flash chromatography (Eluent of 0%~48% EtOAc in petroleum ether), 3-(3-(4-(((tert-butyldimethylsilyl)oxy)methyl)phenyl)-5-(5-methylpyrazin-2-yl)-3H-imidazo[4,5-b]pyridin-2-yl)pyridin-2-amine (240 mg, yield: 55% for two steps) was obtained as a black solid. MS: m/z=524.2 [M+H]$^+$. $^1$H NMR (400 MHz, Dimethylsulfoxide-d$_6$) δ 9.19 (s, 1H), 8.61 (s, 1H), 8.35 (d, J=2.4 Hz, 2H), 8.02 (dd, J=4.8, 1.6 Hz, 1H), 7.50-7.48 (m, 4H), 7.23 (dd, J=8.0, 2.0 Hz, 1H), 7.01 (s, 2H), 6.41 (dd, J=7.6, 4.8 Hz, 1H), 4.83 (s, 2H), 0.93-0.91 (m, 12H), 0.11 (s, 6H)

Step 3: 4-(2-(2-Aminopyridin-3-yl)-5-(5-methylpyrazin-2-yl)-3H-imidazo[4,5-b]pyridin-3-yl)phenyl)methanol A mixture of 3-(3-(4-(((tert-butyldimethylsilyl)oxy)methyl)phenyl)-5-(5-methylpyrazin-2-yl)-3H-imidazo[4,5-b]pyridin-2-yl)pyridin-2-amine (240 mg, 458 μmol) in THF (20 mL) was added TBAF (1 M, 917 μL). The mixture was stirred at 25° C. for 1 hr. The reaction mixture was diluted with H$_2$O (10 mL) and extracted with EtOAc (10 mL×3). The combined organic layers were washed with brine (30 mL), dried over Na$_2$SO$_4$, filtered and concentrated under reduced pressure. (4-(2-(2-Aminopyridin-3-yl)-5-(5-methylpyrazin-2-yl)-3H-imidazo[4,5-b]pyridin-3-yl)phenyl) methanol (171 mg, yield: 91%) was obtained as a yellow solid. MS: m/z=410.2 [M+H]$^+$.

Step 4: 3-(3-(4-(Chloromethyl)phenyl)-5-(5-methylpyrazin-2-yl)-3H-imidazo[4,5-b]pyridin-2-yl)pyridin-2-amine To a solution of (4-(2-(2-Aminopyridin-3-yl)-5-(5-methylpyrazin-2-yl)-3H-imidazo[4,5-b]pyridin-3-yl)phenyl) methanol (171 mg, 417 μmol) in CH2Cl$_2$ (10 mL) was added SOCl2 (163 mg, 1.37 mmol). The mixture was stirred at 40° C. for 1 hr. The mixture was concentrated under reduced pressure to give 3-(3-(4-(chloromethyl)phenyl)-5-(5-methylpyrazin-2-yl)-3H-imidazo[4,5-b]pyridin-2-yl)pyridin-2-amine (Intermediate 237, 158 mg, HCl salt, yield: 79%) as a yellow solid. MS: m/z=428.1 [M+H]$^+$.

Intermediate 238: 3-(3-(4-(Chloromethyl)phenyl)-5-(5-methoxypyrazin-2-yl)-3H-imidazo[4,5-b]pyridin-2-yl)pyridin-2-amine

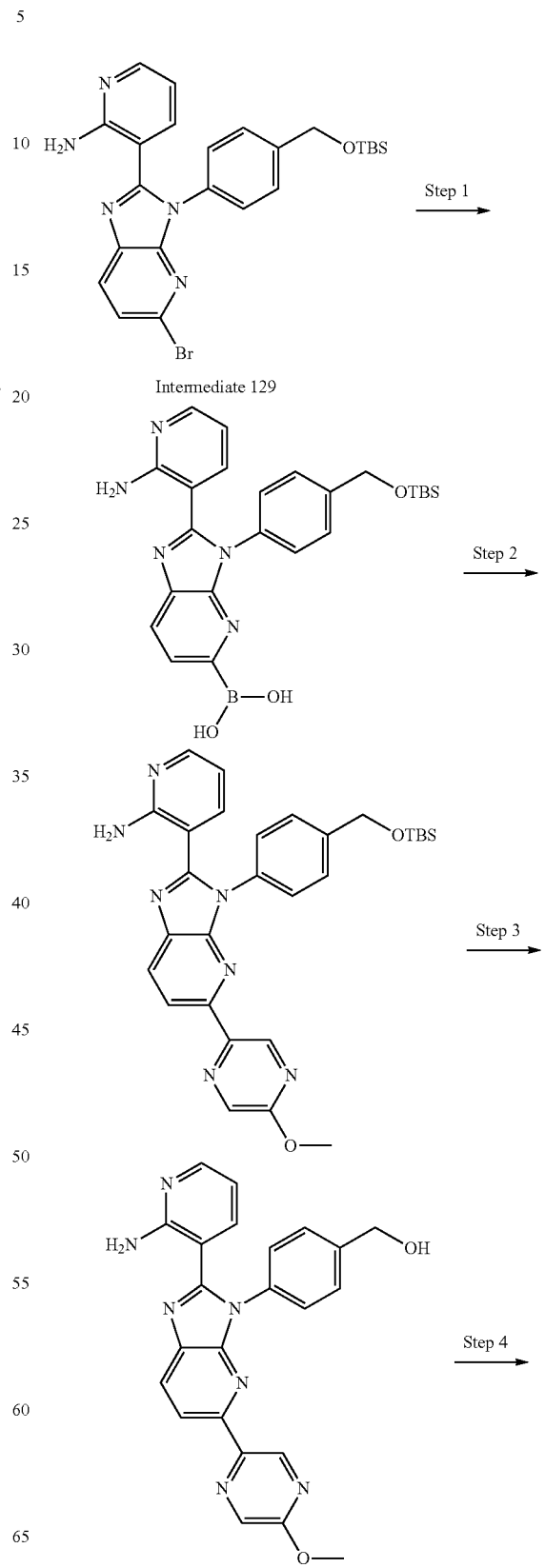

Intermediate 129

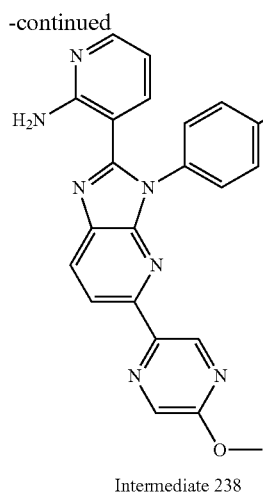

Intermediate 238

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (746 mg, 2.94 mmol), KOAc (577 mg, 5.88 mmol) and Pd(dppf)Cl$_2$ (80 mg, 98 μmol) in 1,4-dioxane (10 mL) was degassed and purged with N$_2$ three times. The mixture was stirred at 80° C. for 12 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((tert-Butyldimethylsilyl)oxy)methyl)phenyl)-5-(5-methoxypyrazin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (500 mg, 1.0 mmol), 2-bromo-5-methoxypyrazine (218 mg, 1.3 mmol), Pd(dppf)Cl$_2$ (86 mg, 105 μmol) and Cs$_2$CO$_3$ (1.0 g, 3.2 mmol) in 1,4-dioxane (5 mL) and H$_2$O (1 mL) was degassed and purged with N$_2$ three times. The mixture was stirred at 90° C. for 2 hr under N$_2$ atmosphere. The reaction mixture was diluted with H$_2$O (15 mL) and extracted with EtOAc (15 mL×3). The combined organic layers were washed with brine (30 mL), dried over Na$_2$SO$_4$, filtered and concentrated under reduced pressure. After purified by silica gel flash chromatography (Eluent of 0%~45% EtOAc in petroleum ether), 3-(3-(4-(((tert-butyldimethylsilyl)oxy)methyl)phenyl)-5-(5-methoxypyrazin-2-yl)-3H-imidazo[4,5-b]pyridin-2-yl)pyridin-2-amine (280 mg, yield: 70% for two steps) was obtained as a black solid. MS: m/z=540.2 [M+H]$^+$. $^1$H NMR (400 MHz, Dimethylsulfoxide-d$_6$) δ 8.90 (s, J H), 8.39 (s, 1H), 8.31 (d, J=8.4 Hz, 1H), 8.25 (d, J=8.0 Hz, 1H), 8.01 (dd, J=4.8, 2.0 Hz, 1H), 7.50 (d, J=2.0 Hz, 4H), 7.23 (dd, J=7.2, 1.6 Hz, 1H), 7.02 (s, 2H), 6.40 (dd, J=7.6, 4.8 Hz, 1H), 4.83 (s, 2H), 0.93-0.92 (m, 12H), 0.12 (s, 6H)

Step 3: (4-(2-(2-Aminopyridin-3-yl)-5-(5-methoxypyrazin-2-yl)-3H-imidazo[4,5-b]pyridin-3-yl)phenyl)methanol To a mixture of 3-(3-(4-(((tert-butyldimethylsilyl)oxy)methyl)phenyl)-5-(5-methoxypyrazin-2-yl)-3H-imidazo[4,5-b]pyridin-2-yl)pyridin-2-amine (280 mg, 519 μmol) in THF (20 mL) was added TBAF (1 M, 1.04 mL). The mixture was stirred at 25° C. for 0.5 hr. The reaction mixture was diluted with H$_2$O (10 mL) and extracted with EtOAc (10 mL×3). The combined organic layers were washed with brine (30 mL), dried over Na$_2$SO$_4$, filtered and concentrated under reduced pressure. (4-(2-(2-Aminopyridin-3-yl)-5-(5-methoxypyrazin-2-yl)-3H-imidazo[4,5-b]pyridin-3-yl)phenyl)methanol (210 mg, yield: 77%) was obtained as a yellow solid. MS: m/z=426.1 [M+H]$^+$.

Step 4: 3-(3-(4-(Chloromethyl)phenyl)-5-(5-methoxypyrazin-2-yl)-3H-imidazo[4,5-b]pyridin-2-yl)pyridin-2-amine To a solution of (4-(2-(2-aminopyridin-3-yl)-5-(5-methoxypyrazin-2-yl)-3H-imidazo[4,5-b]pyridin-3-yl)phenyl)methanol (210 mg, 486 μmol) in CH$_2$Cl$_2$ (10 mL) was added SOCl$_2$ (163 mg, 1.37 mmol). The mixture was stirred at 40° C. for 1 hr. The mixture was concentrated under reduced pressure to give 3-(3-(4-(chloromethyl)phenyl)-5-(5-methoxypyrazin-2-yl)-3H-imidazo[4,5-b]pyridin-2-yl)pyridin-2-amine (Intermediate 238, 250 mg, HCl salt, yield: 74%) as a yellow solid. MS: m/z=444.1 [M+H]$^+$.

Intermediate 239: 3-(3-(4-(Chloromethyl)phenyl)-5-(5-ethoxypyridin-2-yl)-3H-imidazo[4,5-b]pyridin-2-yl)pyridin-2-amine

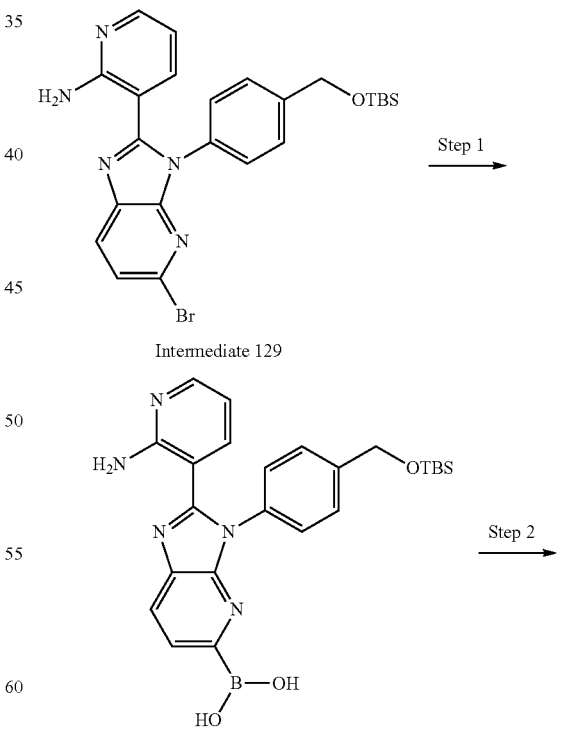

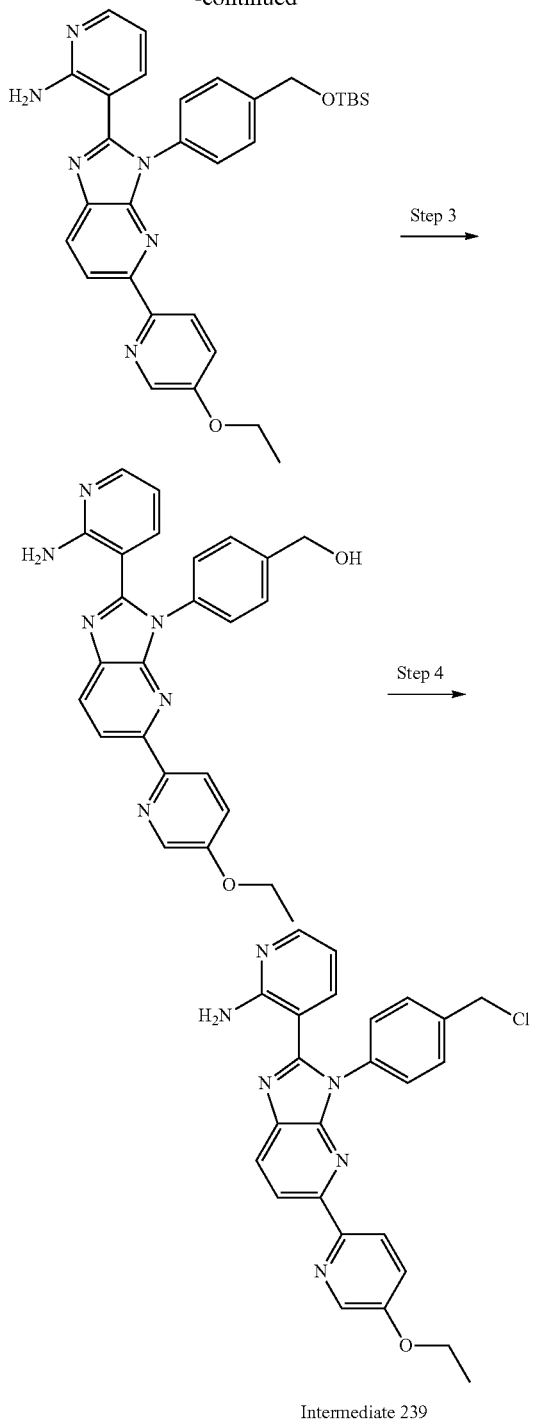

Intermediate 239

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl$_2$ (143 mg, 196 μmol) in 1,4-dioxane (10 mL) was degassed and purged with N$_2$ three times. The mixture was stirred at 80° C. for 4 hr under N2 atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]$^+$.

Step 2: 3-(3-(4-(((tert-Butyldimethylsilyl)oxy)methyl)phenyl)-5-(5-ethoxypyridin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (465 mg, 978 μmol), 2-bromo-5-ethoxypyridine (217 mg, 1.08 mmol), Pd(dppf)Cl$_2$ (71.6 mg, 97.8 μmol) and Cs$_2$CO$_3$ (956 mg, 2.93 mmol) in 1,4-dioxane (5 mL) and H$_2$O (1 mL) was degassed and purged with N$_2$ three times. The mixture was stirred at 80° C. for 16 hr under N$_2$ atmosphere. The reaction mixture was quenched with H$_2$O (5 mL) and extracted with CH$_2$Cl$_2$ (15 mL×2). The combined organic layers were washed with brine (30 mL), dried over Na$_2$SO$_4$, filtered, and concentrated under reduced pressure. After purified by silica gel flash chromatography (Eluent of 15%~43% EtOAc in petroleum ether), 3-(3-(4-(((tert-butyldimethylsilyl)oxy)methyl)phenyl)-5-(5-ethoxypyridin-2-yl)-3H-imidazo[4,5-b]pyridin-2-yl)pyridin-2-amine (360 mg, yield: 57% for two steps) was obtained as a green solid. MS: m/z=553.6 [M+H]$^+$. $^1$H NMR (400 MHz, Dimethylsulfoxide-d$_6$) δ 8.40-8.32 (m, 2H), 8.29-8.23 (m, 1H), 8.10 (d, J=8.8 Hz, 1H), 8.00 (d, J=4.4 Hz, 1H), 7.52-7.44 (m, 5H), 7.19 (d, J=7.6 Hz, 1H), 7.02 (br s, 2H), 6.42-6.36 (m, 1H), 4.83 (s, 2H), 4.15 (q, J=6.8 Hz, 2H), 1.36 (t, J=6.8 Hz, 3H), 0.93 (s, 9H), 0.12 (s, 6H).

Step 3: (4-(2-(2-Aminopyridin-3-yl)-5-(5-ethoxypyridin-2-yl)-3H-imidazo[4,5-b]pyridin-3-yl)phenyl)methanol To a solution of 3-(3-(4-(((tert-butyldimethylsilyl)oxy)methyl)phenyl)-5-(5-ethoxypyridin-2-yl)-3H-imidazo[4,5-b]pyridin-2-yl)pyridin-2-amine (360 mg, 651 μmol) in THF (3 mL) was added TBAF (511 mg, 1.95 mmol, 1 M in THF). The mixture was stirred at 25° C. for 1 hr. The reaction mixture was quenched with H$_2$O (5 mL) at 25° C. and extracted with CH$_2$Cl$_2$ (15 mL×3). The combined organic layers were washed with brine (50 mL×3), dried over Na$_2$SO$_4$, filtered and concentrated under reduced pressure. After triturated with EtOAc (10 mL) at 25° C. for 10 min, (4-(2-(2-aminopyridin-3-yl)-5-(5-ethoxypyridin-2-yl)-3H-imidazo[4,5-b]pyridin-3-yl)phenyl)methanol (200 mg, yield: 67%) was obtained as a black solid. MS: m/z=439.1 [M+H]$^+$. $^1$H NMR (400 MHz, Dimethylsulfoxide-d$_6$) δ 8.39-8.32 (m, 2H), 8.26 (d, J=8.4 Hz, 1H), 8.11 (d, J=8.8 Hz, 1H), 8.00 (d, J=4.0 Hz, 1H), 7.52-7.44 (m, 5H), 7.22 (d, J=7.6 Hz, 1H), 6.98 (br s, 2H), 6.42 (dd, J=7.6, 5.2 Hz, 1H), 5.37 (t, J=5.6 Hz, 1H), 4.61 (d, J=5.6 Hz, 2H), 4.15 (q, J=6.8 Hz, 2H), 1.36 (t, J=6.8 Hz, 3H).

Step 4: 3-(3-(4-(Chloromethyl)phenyl)-5-(5-ethoxypyridin-2-yl)-3H-imidazo[4,5-b]pyridin-2-yl)pyridin-2-amine To a solution of (4-(2-(2-aminopyridin-3-yl)-5-(5-ethoxypyridin-2-yl)-3H-imidazo[4,5-b]pyridin-3-yl)phenyl)methanol (200 mg, 456 μmol) in CH$_2$Cl$_2$ (5 mL) was added SOCl$_2$ (163 mg, 1.37 mmol). The mixture was stirred at 25° C. for 0.5 hr. The reaction was concentrated under reduced pressure to give 3-(3-(4-(chloromethyl)phenyl)-5-(5- ethoxypyridin-2-yl)-3H-imidazo[4,5-b]pyridin-2-yl)pyridin-2-amine (Intermediate 239, 225 mg, HCl salt) as a brown solid. MS: m/z=457.0 [M+H]⁺. ¹H NMR (400 MHz, Methanol-d₄) δ 8.73 (d, J=9.6 Hz, 1H), 8.55 (d, J=8.4 Hz, 1H), 8.45 (d, J=2.8 Hz, 1H), 8.39 (d, J=8.4 Hz, 1H), 8.32 (dd, J=9.2, 2.8 Hz, 1H), 8.05 (dd, J=6.4, 1.6 Hz, 1H), 7.84 (dd, J=7.6, 1.2 Hz, 1H), 7.76-7.71 (m, 2H), 7.66-7.60 (m, 2H), 6.90-6.84 (m, 1H), 4.80 (s, 2H), 4.37 (q, J=7.2 Hz, 2H), 1.52 (t, J=7.2 Hz, 3H).

Intermediate 240: 3-(3-(4-(Chloromethyl)phenyl)-5-(2-methyl-2H-1,2,3-triazol-4-yl)-3H-imidazo[4,5-b]pyridin-2-yl)pyrazin-2-amine

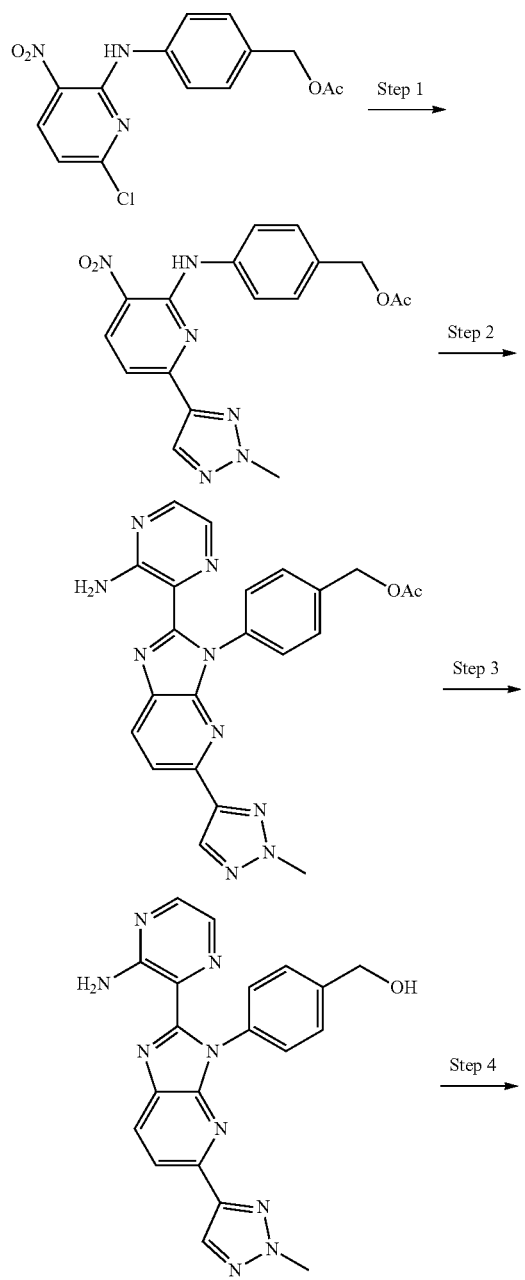

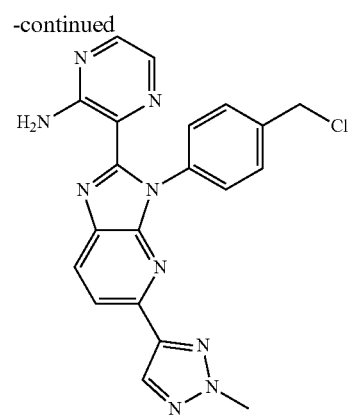

Intermediate 240

Step 1: 4-((6-(2-Methyl-2H-1,2,3-triazol-4-yl)-3-nitropyridin-2-yl)amino)benzyl acetate A mixture of 4-((6-chloro-3-nitropyridin-2-yl)amino)benzyl acetate (refer to Intermediate 178 for detail procedures, 515 mg, 1.60 mmol), (2-methyl-2H-1,2,3-triazol-4-yl)boronic acid (203 mg, 1.60 mmol), Cs₂CO₃ (1.56 g, 4.80 mmol) and Pd(dppf)Cl₂ (117 mg, 160 μmol) in 1,4-dioxane (6 mL) and H₂O (1.2 mL) was degassed and purged with N₂ three times. The mixture was stirred at 80° C. for 3 hr under N₂ atmosphere. The reaction mixture was quenched with H₂O (10 mL) at 25° C., diluted with CH₂Cl₂ (10 mL) and extracted with CH₂Cl₂ (15 mL×2). The combined organic layers were washed with brine (30 mL), dried over anhydrous Na₂SO₄, filtered, and concentrated under reduced pressure. After purified by silica gel flash chromatography (Eluent of 5%~30% EtOAc in petroleum ether), 4-((6-(2-methyl-2H-1,2,3-triazol-4-yl)-3-nitropyridin-2-yl)amino)benzyl acetate (450 mg, yield: 73%) was obtained as a red solid. MS: m/z=368.9 [M+H]⁺. ¹H NMR (400 MHz, Dimethylsulfoxide-d₆) δ 10.16 (s, 1H), 8.65 (d, J=8.8 Hz, 1H), 8.18 (s, 1H), 7.82 (d, J=8.4 Hz, 2H), 7.50-7.41 (m, 3H), 5.08 (s, 2H), 4.27 (s, 3H), 2.08 (s, 3H).

Step 2: 4-(2-(3-Aminopyrazin-2-yl)-5-(2-methyl-2H-1,2,3-triazol-4-yl)-3H-imidazo[4,5-b]pyridin-3-yl)benzyl acetate To a solution of 4-((6-(2-methyl-2H-1,2,3-triazol-4-yl)-3-nitropyridin-2-yl)amino)benzyl acetate (415 mg, 1.13 mmol) in DMSO (5 mL) was added Na₂S₂O₄ (892 mg, 4.51 mmol, 88% purity) and 3-aminopyrazine-2-carbaldehyde (166 mg, 1.35 mmol). The mixture was stirred at 100° C. for 3 hr. The reaction mixture was quenched with H₂O (30 mL) at 25° C. and diluted with CH₂Cl₂ (20 mL) and extracted with CH₂Cl₂ (15 mL×2). The combined organic layers were washed with brine (50 mL×3), dried over anhydrous Na₂SO₄, filtered, and concentrated under reduced pressure. After purified by silica gel flash chromatography (Eluent of 10%~35% EtOAc in petroleum ether), 4-(2-(3-aminopyrazin-2-yl)-5-(2-methyl-2H-1,2,3-triazol-4-yl)-3H-imidazo[4,5-b]pyridin-3-yl)benzyl acetate (70 mg, yield: 13%) was obtained as a yellow solid. MS: m/z=442.1 [M+H]⁺. ¹H NMR (400 MHz, Chloroform-d) δ 8.15 (d, J=8.4 Hz, 1H), 8.02-7.96 (m, 3H), 7.59 (d, J=2.4 Hz, 1H), 7.49 (d, J=8.0 Hz, 2H), 7.39 (d, J=8.4 Hz, 2H), 7.18-6.98 (m, 2H), 5.24 (s, 2H), 4.25 (s, 3H), 2.18 (s, 3H).

Step 3: (4-(2-(3-Aminopyrazin-2-yl)-5-(2-methyl-2H-1,2,3-triazol-4-yl)-3H-imidazo[4,5-b]pyridin-3-yl)phenyl)methanol To a solution of 4-(2-(3-aminopyrazin-2-yl)-5-(2-methyl-2H-1,2,3-triazol-4-yl)-3H-imidazo[4,5-b]pyridin-3-yl)benzyl acetate (70 mg, 159 µmol) in THF (1 mL), MeOH (1 mL) and H$_2$O (1 mL) was added K$_2$CO$_3$ (65.8 mg, 476 µmol). The mixture was stirred at 25° C. for 1 hr. The reaction mixture was quenched with H$_2$O (10 mL) at 25° C., diluted with CH$_2$Cl$_2$ (10 mL) and extracted with CH$_2$Cl$_2$ (15 mL×3). The combined organic layers were washed with brine (30 mL), dried over Na$_2$SO$_4$, filtered and concentrated under reduced pressure. (4-(2-(3-Aminopyrazin-2-yl)-5-(2-methyl-2H-1,2,3-triazol-4-yl)-3H-imidazo[4,5-b]pyridin-3-yl)phenyl)methanol (70 mg) was obtained as a yellow solid. MS: m/z=400.1 [M+H]$^+$. $^1$H NMR (400 MHz, Chloroform-d) δ 8.15 (d, J=8.4 Hz, 1H), 8.03-7.95 (m, 3H), 7.59 (d, 1=2.4 Hz, 1H), 7.51 (d, J=8.4 Hz, 2H), 7.38 (d, J=8.0 Hz, 2H), 7.14-6.90 (m, 2H), 4.85 (s, 2H), 4.24 (s, 3H).

Step 4: 3-(3-(4-(Chloromethyl)phenyl)-5-(2-methyl-2H-1,2,3-triazol-4-yl)-3H-imidazo[4,5-b]pyridin-2-yl)pyrazin-2-amine To a solution of (4-(2-(3-aminopyrazin-2-yl)-5-(2-methyl-2H-1,2,3-triazol-4-yl)-3H-imidazo[4,5-b]pyridin-3-yl)phenyl)methanol (70 mg, 175 µmol) in CH$_2$Cl$_2$ (4 in L) was added SOCl$_2$ (62.6 mg, 526 µmol). The mixture was stirred at 25° C. for 0.5 hr. The reaction was concentrated under reduced pressure to give 3-(3-(4-(chloromethyl)phenyl)-5-(2-methyl-2H-1,2,3-triazol-4-yl)-3H-imidazo[4,5-b]pyridin-2-yl)pyrazin-2-amine (Intermediate 240, 80 mg, HCl salt) as a yellow solid. MS: m/z=418.1 [M+H]$^+$. $^1$H NMR (400 MHz, Methanol-d$_4$) δ 8.32 (d, J=8.4 Hz, 1H), 8.10 (d, J=8.4 Hz, 1H), 7.98 (s, 1H), 7.90 (d, J=2.8 Hz, 1H), 7.69 (d, J=2.8 Hz, 1H), 7.61 (d, J=8.4 Hz, 2H), 7.45 (d, J=8.4 Hz, 2H), 4.79 (s, 2H), 4.22 (s, 3H).

Intermediate 241: 2-(2-(2-Aminopyridin-3-yl)-3-(4-(chloromethyl)phenyl)-3H-imidazo[4,5-b]pyridin-5-yl)isonicotinonitrile

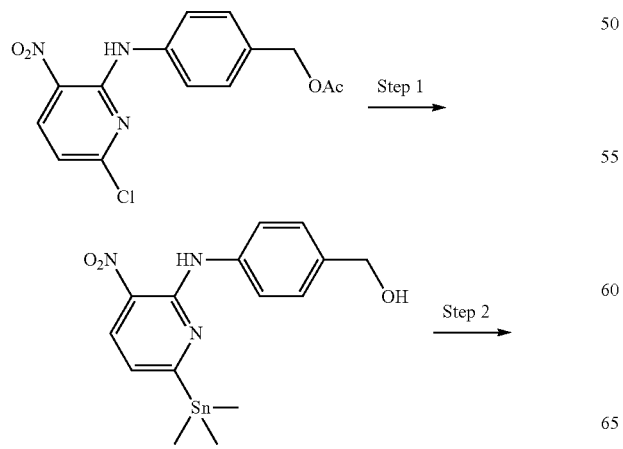

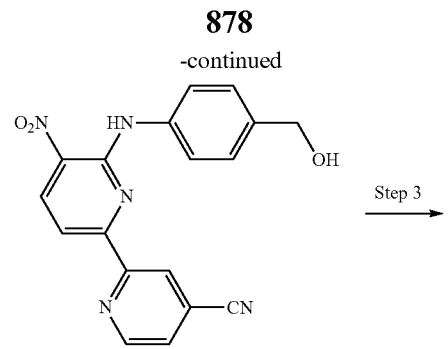

-continued

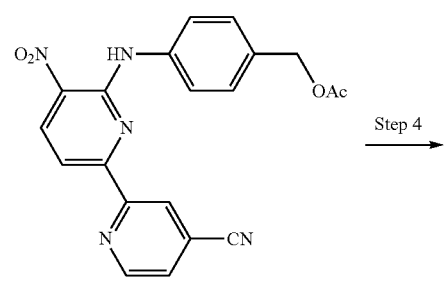

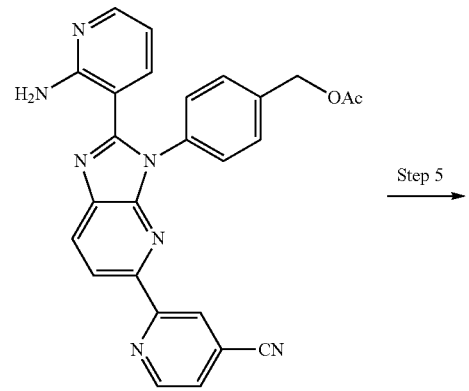

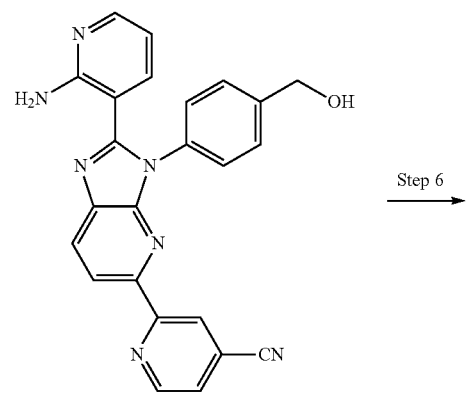

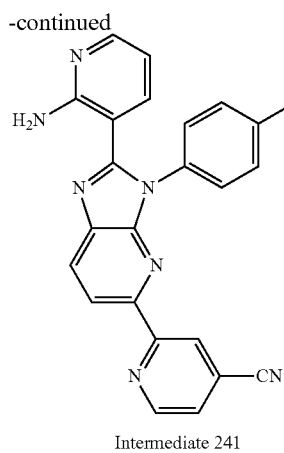

Intermediate 241

Step 1: (4-((3-Nitro-6-(trimethylstannyl)pyridin-2-yl)amino)phenyl)methanol

To a solution of 4-((6-chloro-3-nitropyridin-2-yl)amino)benzyl acetate (refer to Intermediate 178 for detail procedures, 5 g, 15.5 mmol), Pd(PPh$_3$)$_4$ (1.8 g, 1.55 mmol) and 1,1,1,2,2,2-hexamethyldistannane (14.4 g, 44 mmol) in 1,4-dioxane (50 mL) was degassed and purged with N$_2$ three times. The mixture was stirred at 125° C. for 2 hr under N$_2$ atmosphere. (4-((3-Nitro-6-(trimethylstannyl)pyridin-2-yl)amino)phenyl)methanol was obtained as a black liquid, which was used in the next step without work-up and purification. MS: m/z=409.9 [M+H]$^+$.

Step 2: 6'-((4-(Hydroxymethyl)phenyl)amino)-5'-nitro-[2,2'-bipyridine]-4-carbonitrile A mixture of (4-((3-nitro-6-(trimethylstannyl)pyridin-2-yl)amino)phenyl)methanol (6.34 g, 15.5 mmol), 2-bromoisonicotinonitrile (2.84 g, 15.5 mmol), Pd(PPh$_3$)$_4$ (1.79 g, 1.55 mmol) in 1,4-dioxane (100 mL) was degassed and purged with N$_2$ three times. The mixture was stirred at 100° C. for 16 hr under N$_2$ atmosphere. The reaction was concentrated under reduced pressure. After purified by silica gel flash chromatography (Eluent of 5~100% EtOAc in petroleum ether), 6'-((4-(hydroxymethyl)phenyl)amino)-5'-nitro-[2,2'-bipyridine]-4-carbonitrile (1.4 g, yield: 28% for two steps) was obtained as a black solid. MS: m/z=348.0 [M+H]$^+$.

Step 3: 4-((4'-Cyano-5-nitro-[2,2'-bipyridin]-6-yl)amino)benzyl acetate

To a solution of 6'-((4-(hydroxymethyl)phenyl)amino)-5'-nitro-[2,2'-bipyridine]-4-carbonitrile (1.3 g, 3.74 mmol) in CH$_2$Cl$_2$ (15 mL) were added TEA (1.14 g, 11.2 mmol), DMAP (45.7 mg, 374 μmol), and Ac$_2$O (573 mg, 5.61 mmol). The mixture was stirred at 25° C. for 1 hr. The reaction mixture was quenched with H$_2$O (30 mL) at 25° C., diluted with CH$_2$Cl$_2$ (30 mL) and extracted with CH$_2$Cl$_2$ (50 mL×2). The combined organic layers were washed with brine (50 mL), dried over Na$_2$SO$_4$, filtered, and concentrated under reduced pressure. After purified by silica gel flash chromatography (Eluent of 10~30% EtOAc in petroleum ether), 4-((4'-cyano-5-nitro-[2,2'-bipyridin]-6-yl)amino)benzyl acetate (1.4 g, yield: 40%) was obtained as a black solid. MS: m/z=390.0 [M+H]$^+$.

Step 4: 4-(2-(2-Aminopyridin-3-yl)-5-(4-cyanopyridin-2-yl)-3H-imidazo[4,5-b]pyridin-3-yl)benzyl acetate To a solution of 4-((4'-cyano-5-nitro-[2,2'-bipyridin]-6-yl)amino)benzyl acetate (1.2 g, 3.08 mmol) in DMSO (10 mL) were added Na$_2$S$_2$O$_4$ (2.38 g, 12.3 mmol, 90% purity) and 2-aminonicotinaldehyde (452 mg, 3.70 mmol). The mixture was stirred at 100° C. for 2 hr. The reaction mixture was quenched with H$_2$O (50 mL) at 25° C., diluted with CH$_2$Cl$_2$ (30 mL) and extracted with CH$_2$Cl$_2$ (30 mL×3). The combined organic layers were washed with brine (50 mL×3), dried over Na$_2$SO$_4$, filtered, and concentrated under reduced pressure. After purified by silica gel flash chromatography (Eluent of 10%~70% EtOAc in petroleum ether), 4-(2-(2-aminopyridin-3-yl)-5-(4-cyanopyridin-2-yl)-3H-imidazo[4,5-b]pyridin-3-yl)benzyl acetate (80 mg, yield: 5.6%) was obtained as a yellow solid. MS: m/z=462.0 [M+H]$^+$. $^1$H NMR (400 MHz, Chloroform-d) δ 8.81 (d, J=4.8 Hz, 1H), 8.55-8.52 (m, 2H), 8.21 (d, J=8.4 Hz, 1H), 8.10 (dd, J=4.8, 1.6 Hz, 1H), 7.60-7.56 (m, 2H), 7.47-7.44 (m, 3H), 7.12 (dd, J=7.6, 1.6 Hz, 1H), 6.66 (br s, 2H), 6.41 (dd, J=8.0, 4.8 Hz, 1H), 5.27 (s, 2H), 2.20 (s, 3H).

Step 5: 2-(2-(2-Aminopyridin-3-yl)-3-(4-(hydroxymethyl)phenyl)-3H-imidazo[4,5-b]pyridin-5-yl)isonicotinonitrile To a solution of 4-(2-(2-aminopyridin-3-yl)-5-(4-cyanopyridin-2-yl)-3H-imidazo[4,5-b]pyridin-3-yl)benzyl acetate (80 mg, 173 μmol) in THF (2 mL), MeOH (2 mL) and H$_2$O (1 mL) was added the K$_2$CO$_3$ (71.9 mg, 520 μmol). The mixture was stirred at 25° C. for 2 hr. The reaction mixture was diluted with H$_2$O (10 mL) and extracted with CH$_2$Cl$_2$ (15 mL×2). The combined organic layers were washed with brine (15 mL), dried over Na$_2$SO$_4$, filtered and concentrated under reduced pressure. 2-(2-(2-Aminopyridin-3-yl)-3-(4-(hydroxymethyl)phenyl)-3H-imidazo[4,5-b]pyridin-5-yl)isonicotinonitrile (60 mg) was obtained as a yellow solid. MS: m/z=420.0 [M+H]$^+$.

Step 6: 2-(2-(2-Aminopyridin-3-yl)-3-(4-(chloromethyl)phenyl)-3H-imidazo[4,5-b]pyridin-5-yl)isonicotinonitrile To a solution of 2-(2-(2-aminopyridin-3-yl)-3-(4-(hydroxymethyl)phenyl)-3H-imidazo[4,5-b]pyridin-5-yl)isonicotinonitrile (60 mg, 143 μmol) in CH$_2$Cl$_2$ (5 mL) was added SOCl$_2$ (51.1 mg, 429 μmol). The mixture was stirred at 40° C. for 0.4 hr. The reaction was concentrated under reduced pressure to give 2-(2-(2-aminopyridin-3-yl)-3-(4-(chloromethyl)phenyl)-3H-imidazo[4,5-b]pyridin-5-yl)isonicotinonitrile (Intermediate 241, 67.9 mg, HCl salt) was obtained as a yellow solid. MS: m/z=437.9 [M+H]$^+$.

Intermediate 242: 3-(3-(4-(Chloromethyl)phenyl)-5-(5-methoxypyridin-2-yl)-3H-imidazo[4,5-b]pyridin-2-yl)pyridin-2-amine

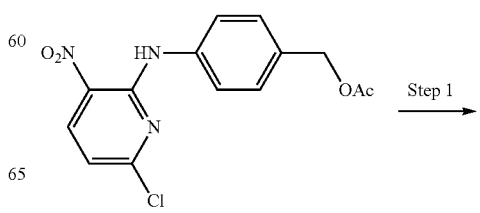

Step 1

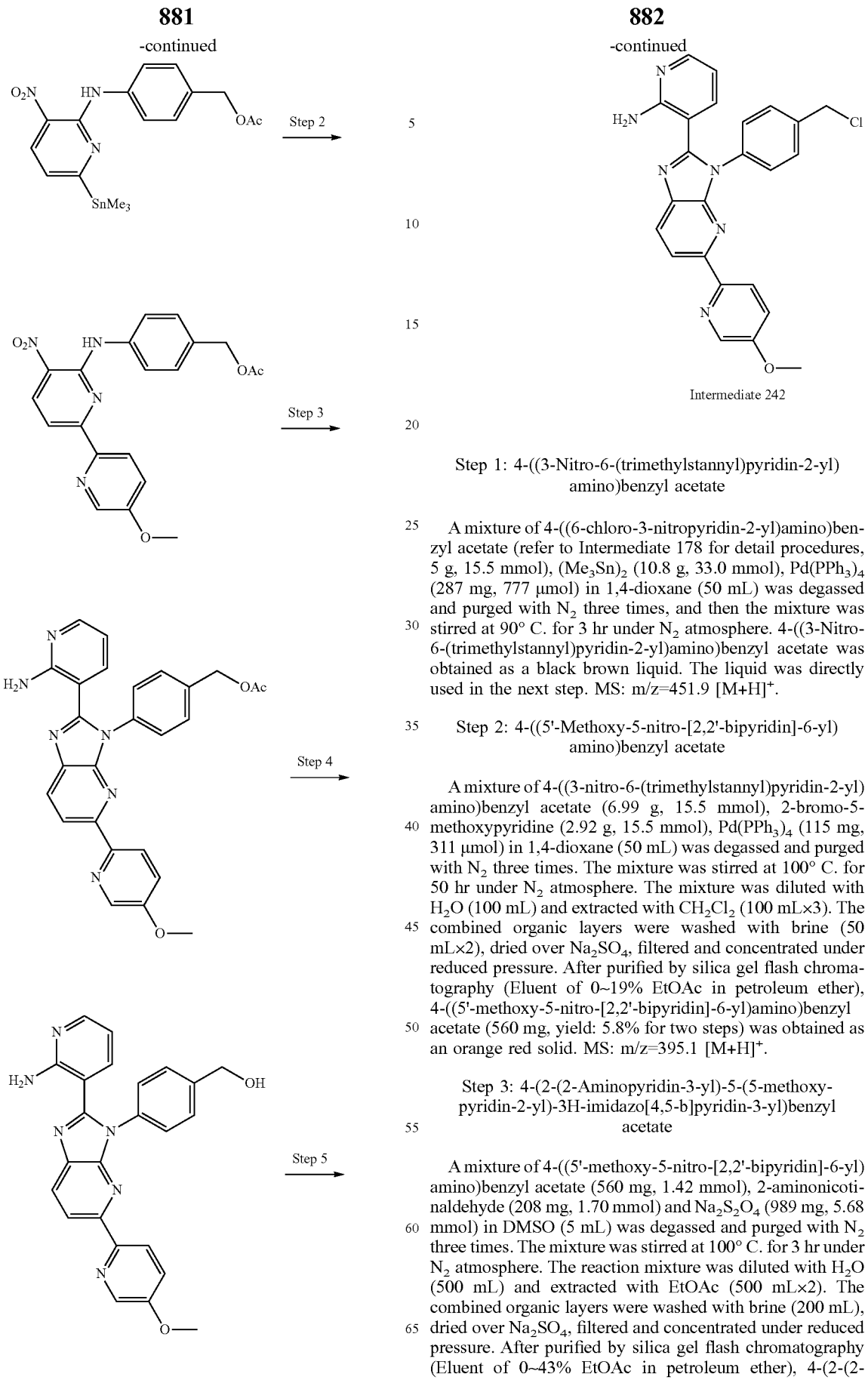

Intermediate 242

Step 1: 4-((3-Nitro-6-(trimethylstannyl)pyridin-2-yl) amino)benzyl acetate

A mixture of 4-((6-chloro-3-nitropyridin-2-yl)amino)benzyl acetate (refer to Intermediate 178 for detail procedures, 5 g, 15.5 mmol), (Me₃Sn)₂ (10.8 g, 33.0 mmol), Pd(PPh₃)₄ (287 mg, 777 μmol) in 1,4-dioxane (50 mL) was degassed and purged with N₂ three times, and then the mixture was stirred at 90° C. for 3 hr under N₂ atmosphere. 4-((3-Nitro-6-(trimethylstannyl)pyridin-2-yl)amino)benzyl acetate was obtained as a black brown liquid. The liquid was directly used in the next step. MS: m/z=451.9 [M+H]⁺.

Step 2: 4-((5'-Methoxy-5-nitro-[2,2'-bipyridin]-6-yl) amino)benzyl acetate

A mixture of 4-((3-nitro-6-(trimethylstannyl)pyridin-2-yl)amino)benzyl acetate (6.99 g, 15.5 mmol), 2-bromo-5-methoxypyridine (2.92 g, 15.5 mmol), Pd(PPh₃)₄ (115 mg, 311 μmol) in 1,4-dioxane (50 mL) was degassed and purged with N₂ three times. The mixture was stirred at 100° C. for 50 hr under N₂ atmosphere. The mixture was diluted with H₂O (100 mL) and extracted with CH₂Cl₂ (100 mL×3). The combined organic layers were washed with brine (50 mL×2), dried over Na₂SO₄, filtered and concentrated under reduced pressure. After purified by silica gel flash chromatography (Eluent of 0~19% EtOAc in petroleum ether), 4-((5'-methoxy-5-nitro-[2,2'-bipyridin]-6-yl)amino)benzyl acetate (560 mg, yield: 5.8% for two steps) was obtained as an orange red solid. MS: m/z=395.1 [M+H]⁺.

Step 3: 4-(2-(2-Aminopyridin-3-yl)-5-(5-methoxypyridin-2-yl)-3H-imidazo[4,5-b]pyridin-3-yl)benzyl acetate A mixture of 4-((5'-methoxy-5-nitro-[2,2'-bipyridin]-6-yl)amino)benzyl acetate (560 mg, 1.42 mmol), 2-aminonicotinaldehyde (208 mg, 1.70 mmol) and Na₂S₂O₄ (989 mg, 5.68 mmol) in DMSO (5 mL) was degassed and purged with N₂ three times. The mixture was stirred at 100° C. for 3 hr under N₂ atmosphere. The reaction mixture was diluted with H₂O (500 mL) and extracted with EtOAc (500 mL×2). The combined organic layers were washed with brine (200 mL), dried over Na₂SO₄, filtered and concentrated under reduced pressure. After purified by silica gel flash chromatography (Eluent of 0~43% EtOAc in petroleum ether), 4-(2-(2- aminopyridin-3-yl)-5-(5-methoxypyridin-2-yl)-3H-imidazo[4,5-b]pyridin-3-yl)benzyl acetate (200 mg, yield: 21%) was obtained as a light yellow solid. MS: m/z=467.1 [M+H]⁺.

Step 4: (4-(2-(2-Aminopyridin-3-yl)-5-(5-methoxypyridin-2-yl)-3H-imidazo[4,5-b]pyridin-3-yl)phenyl)methanol To a solution of 4-(2-(2-aminopyridin-3-yl)-5-(5-methoxypyridin-2-yl)-3H-imidazo[4,5-b]pyridin-3-yl)benzyl acetate (200 mg, 429 μmol) in THF (1 mL), MeOH (1 mL) and H$_2$O (0.5 mL) was added K$_2$CO$_3$ (178 mg, 1.29 mmol). The mixture was stirred at 25° C. for 0.5 hr. The reaction mixture was diluted with H$_2$O (50 mL) and extracted with EtOAc (50 mL×2). The combined organic layers were washed with brine (15 mL), dried over Na$_2$SO$_4$, filtered and concentrated under reduced pressure. (4-(2-(2-Aminopyridin-3-yl)-5-(5-methoxypyridin-2-yl)-3H-imidazo[4,5-b]pyridin-3-yl)phenyl)methanol (160 mg) was obtained as a light yellow solid. MS: m/z=425.1 [M+H]⁺. ¹H NMR (400 MHz, Chloroform-d) δ 8.85 (d, J=7.6 Hz, 1H), 8.73-8.54 (m, 1H), 8.43 (d, J=7.2 Hz, 2H), 7.95-7.83 (m, 2H), 7.72 (s, 2H), 7.65-7.53 (m, 3H), 7.22-7.11 (m, 1H), 6.62 (d, J=2.0 Hz, 1H), 4.73 (s, 2H), 4.08 (s, 3H).

Step 5: 3-(3-(4-(Chloromethyl)phenyl)-5-(5-methoxypyridin-2-yl)-3H-imidazo[4,5-b]pyridin-2-yl)pyridin-2-amine To a solution of (4-(2-(2-aminopyridin-3-yl)-5-(5-methoxypyridin-2-yl)-3H-imidazo[4,5-b]pyridin-3-yl)phenyl)methanol (160 mg, 377 μmol) in CH$_2$Cl$_2$ (2 mL) was added SOCl$_2$ (51.1 mg, 429 μmol). The mixture was stirred at 40° C. for 0.5 hr and concentrated under reduced pressure to give 3-(3-(4-(chloromethyl)phenyl)-5-(5-methoxypyridin-2-yl)-3H-imidazo[4,5-b]pyridin-2-yl)pyridin-2-amine (Intermediate 242, 160 mg, HCl salt) as a light yellow solid. MS: m/z=443.1 [M+H]⁺.

Intermediate 243: 2-(2-Aminopyridin-3-yl)-1-(4-(chloromethyl)phenyl)-1H-imidazo[4,5-b]pyrazine-5,6-dicarbonitrile

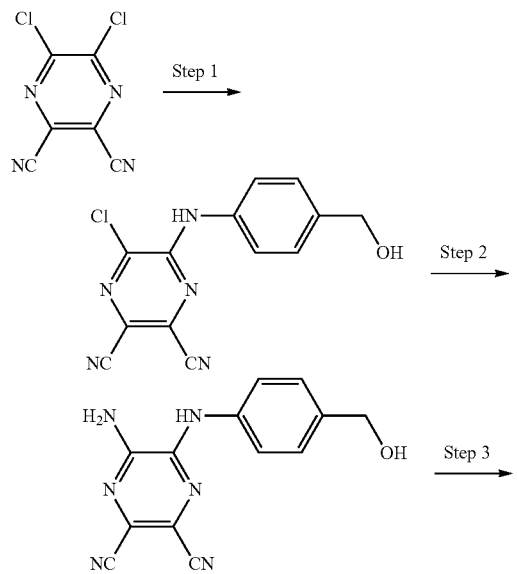

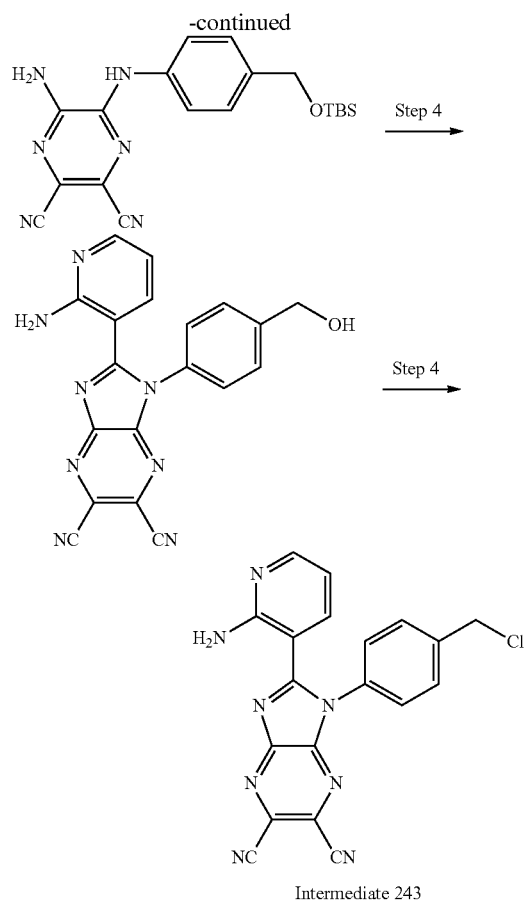

Intermediate 243

Step 1: 5-Chloro-6-((4-(hydroxymethyl)phenyl)amino)pyrazine-2,3-dicarbonitrile

To a solution of 5,6-dichloropyrazine-2,3-dicarbonitrile (10 g, 50.3 mmol) in THF (100 mL) was added (4-aminophenyl)methanol (12.4 g, 101 mmol) in THF (100 mL) dropwise slowly under ice bath. The mixture was degassed and purged with N$_2$ three times and stirred at 0° C. for 3 hr under N$_2$. The reaction mixture was filtered and concentrated under reduced pressure. 5-Chloro-6-((4-(hydroxymethyl)phenyl)amino)pyrazine-2,3-dicarbonitrile (13.2 g, yield: 90%) was obtained as a yellow solid. ¹H NMR (400 MHz, Dimethylsulfoxide-d$_6$) δ 10.27 (br s, 1H), 7.55 (d, J=8.4 Hz, 2H), 7.44 (d, J=8.4 Hz, 2H), 4.57 (s, 2H);

Step 2: 5-Amino-6-((4-(hydroxymethyl)phenyl)amino)pyrazine-2,3-dicarbonitrile

To a solution of 5-chloro-6-((4-(hydroxymethyl)phenyl)amino)pyrazine-2,3-dicarbonitrile (13 g, 45.5 mmol) in DMF (150 mL) was stirred at 0° C. under NH$_3$ atmosphere for 0.5 hr. The reaction mixture was quenched with H$_2$O (500 mL) and filtered. The filtered cake was dried under reduced pressure to give 5-amino-6-((4-(hydroxymethyl)phenyl)amino)pyrazine-2,3-dicarbonitrile (10.7 g, yield: 85%) as a yellow solid. MS: m/z=267.0 [M+H]⁺. ¹H NMR (400 MHz, Dimethylsulfoxide-d$_6$) δ 9.22 (br s, 1H), 8.02-7.81 (m, 2H), 7.59 (d, J=8.4 Hz, 2H), 7.34 (d, J=8.4 Hz, 2H), 5.17 (t, J=5.6 Hz, 1H), 4.48 (d, J=5.6 Hz, 2H).

Step 3: 5-Amino-6-((4-(((tert-butyldimethylsilyl)oxy)methyl)phenyl)amino)pyrazine-2,3-dicarbonitrile To a solution of 5-amino-6-((4-(hydroxymethyl)phenyl)amino)pyrazine-2,3-dicarbonitrile (1 g, 3.76 mmol) in $CH_2Cl_2$ (10 mL) were added TBSCl (679 mg, 4.51 mmol), TEA (1.57 mL, 11.3 mmol) and DMAP (45.9 mg, 376 gmol). The mixture was degassed and purged with $N_2$ three times and stirred at 25° C. for 1 hr under $N_2$. The reaction mixture was diluted with $CH_2Cl_2$ (100 mL), washed with brine (100 mL×2), separated, dried over $Na_2SO_4$, filtered and concentrated under reduced pressure. After purified by silica gel flash chromatography (MeOH in $CH_2Cl_2$=1 to 10%), 5-amino-6-((4-(((tert-butyldimethylsilyl)oxy)methyl)phenyl)amino)pyrazine-2,3-dicarbonitrile (680 mg, yield: 47%) was obtained as a red solid. $^1$H NMR (400 MHz, Dimethylsulfoxide-$d_6$) 9.33 (br s, 1H), 7.99 (br s, 2H), 7.64 (d, J=8.4 Hz, 2H), 7.33 (d, J=8.4 Hz, 2H), 4.69 (s, 2H), 0.90 (s, 9H), 0.08 (s, 6H).

Step 4: 2-(2-Aminopyridin-3-yl)-1-(4-(hydroxymethyl)phenyl)-1H-imidazo[4,5-b]pyrazine-5,6-dicarbonitrile To a solution of 5-amino-6-((4-(((tert-butyldimethylsilyl)oxy)methyl)phenyl)amino)pyrazine-2,3-dicarbonitrile (1.5 g, 3.94 mmol) in DMSO (100 mL) were added $Na_2S_2O_4$ (2.06 g, 11.8 mmol) and 2-aminonicotinaldehyde (481 mg, 3.94 mmol). The mixture was degassed, purged with $N_2$ three times, and stirred at 100° C. for 2 hr under $N_2$. The reaction mixture was diluted with $CH_2Cl_2$ (500 mL) and filtered. The filtrate was washed with brine (300 mL×3), separated, dried over $Na_2SO_4$, filtered and concentrated under reduced pressure. After purified by silica gel flash chromatography (Ethyl acetate in petroleum ether=1% to 100%), 2-(2-aminopyridin-3-yl)-1-(4-(hydroxymethyl)phenyl)-1H-imidazo[4,5-b]pyrazine-5,6-dicarbonitrile (366 mg, yield: 23%) was obtained as a yellow solid. MS: m/z=369.0 [M+H]$^+$. $^1$H NMR (400 MHz, Dimethylsulfoxide-$d_6$) δ 8.13 (dd, J=4.8, 2.0 Hz, 1H), 7.56-7.51 (m, 2H), 7.48-7.43 (m, 2H), 7.36 (dd, J=8.0, 2.0 Hz, 1H), 7.18 (br s, 2H), 6.49 (dd, J=8.0, 4.8 Hz, 1H), 5.39 (t, J=5.6 Hz, 1H), 4.60 (d, J=5.4 Hz, 2H).

Step 5: 2-(2-Aminopyridin-3-yl)-1-(4-(chloromethyl)phenyl)-1H-imidazo[4,5-b]pyrazine-5,6-dicarbonitrile To a solution of 2-(2-aminopyridin-3-yl)-1-(4-(hydroxymethyl)phenyl)-1H-imidazo[4,5-b]pyrazine-5,6-dicarbonitrile (366 mg, 894 μmol) in $CH_2Cl_2$ (5 mL) was added $SOCl_2$ (649 μL, 8.94 mmol) dropwise. The mixture was degassed and purged with $N_2$ three times and stirred at 25° C. for 1 hr under $N_2$. The reaction mixture was concentrated under reduced pressure to give 2-(2-aminopyridin-3-yl)-1-(4-(chloromethyl)phenyl)-1H-imidazo[4,5-b]pyrazine-5,6-dicarbonitrile (Intermediate 243, 379 mg, crude, HCl salt) as a yellow solid, which was used in the next step without further purification. MS: m/z=387.1 [M+H]$^+$.

Intermediate 244: 2-(2-Aminopyridin-3-yl)-3-(4-(chloromethyl)phenyl)-5-(4-fluorophenyl)-3H-imidazo[4,5-b]pyridine-6-carbonitrile

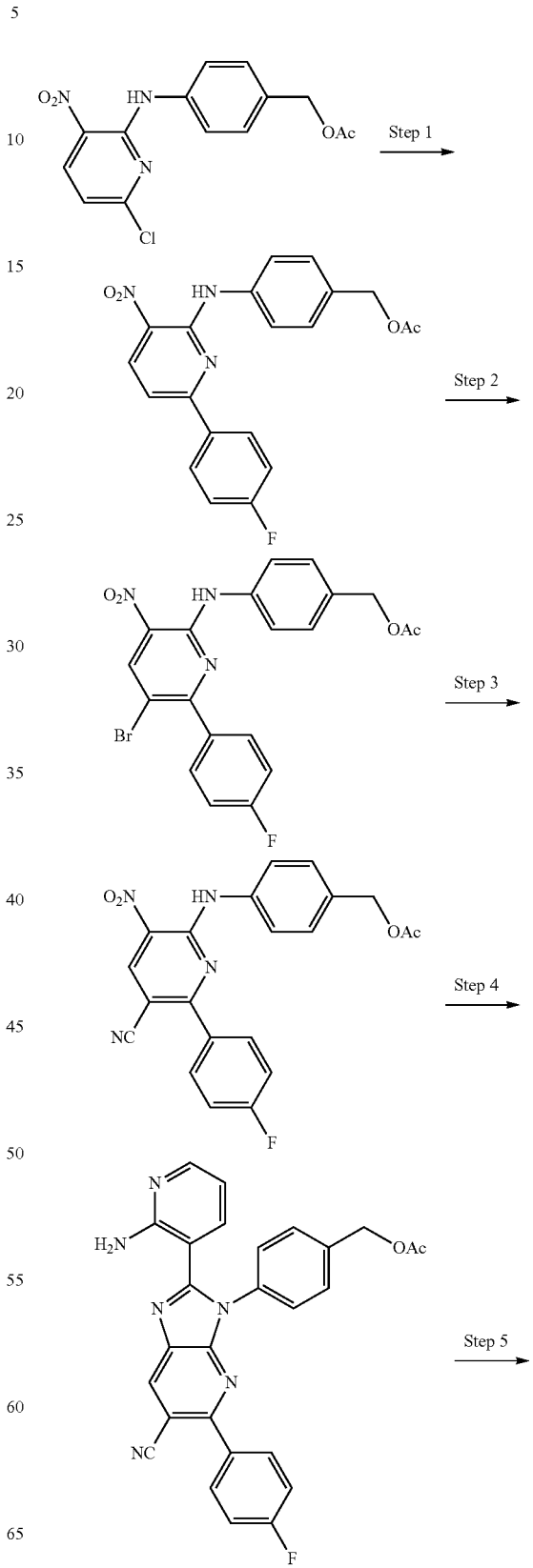

-continued

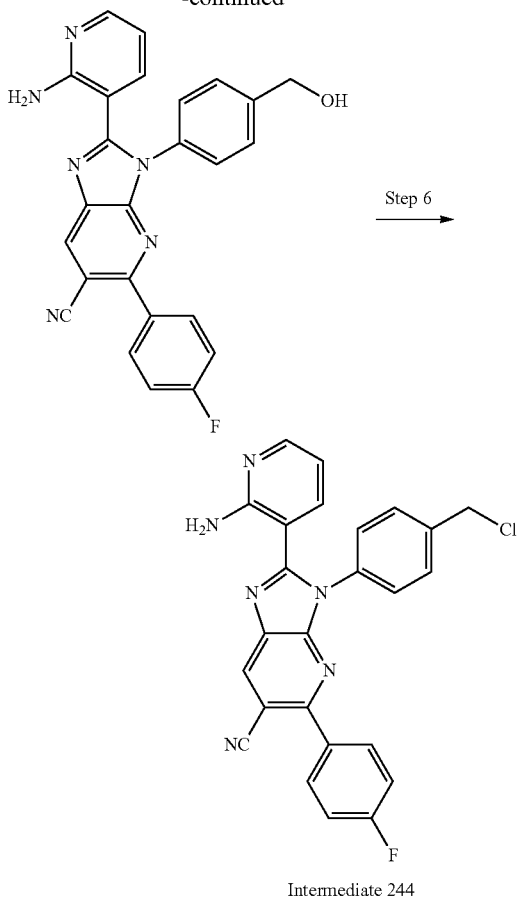

Intermediate 244

Step 1: 4-((6-(4-Fluorophenyl)-3-nitropyridin-2-yl)amino)benzyl acetate

A mixture of 4-((6-chloro-3-nitropyridin-2-yl)amino)benzyl acetate (refer to Intermediate 178 for detail procedures, 500 mg, 1.55 mmol), (4-fluorophenyl)boronic acid (217 mg, 1.55 mmol), $Cs_2CO_3$ (1.52 g, 4.66 mmol) and $Pd(dppf)Cl_2$ (114 mg, 155 μmol) in 1,4-dioxane (10 mL) and $H_2O$ (2 mL) was degassed and purged with $N_2$ three times. The mixture was stirred at 80° C. for 16 hr under $N_2$ atmosphere. The mixture was filtered and concentrated. After purified by silica gel flash chromatography (Eluent of 10%~20% EtOAc in petroleum ether), 4-((6-(4-fluorophenyl)-3-nitropyridin-2-yl)amino)benzyl acetate (300 mg, yield: 48%) was obtained as a yellow solid. MS: m/z=381.9 [M+H]$^+$. $^1$H NMR (400 MHz, Dimethylsulfoxide-$d_6$) δ 10.12 (s, 1H), 8.61 (d, J=8.8 Hz, 1H), 8.20-8.13 (m, 2H), 7.74 (d, J=8.4 Hz, 2H), 7.59 (d, J=8.8 Hz, 1H), 7.44-7.34 (m, 4H), 5.09 (s, 2H), 2.08 (s, 3H).

Step 2: 4-((5-Bromo-6-(4-fluorophenyl)-3-nitropyridin-2-yl)amino)benzyl acetate To a solution of 4-((6-(4-fluorophenyl)-3-nitropyridin-2-yl)amino)benzyl acetate (100 mg, 262 μmol) in DMF (2 mL) was added NBS (51.3 mg, 288 μmol). The mixture was stirred at 25° C. for 2 hr. The mixture was poured into water (10 mL) at 0° C. and filtrated. The solid was dried and purified by prep-HPLC (column: Phenomenex C18 150×25 mm×10 μm; mobile phase: [water ($NH_4HCO_3$)-ACN]; gradient: 65%-85% B over 11 min) to give 4-((5-bromo-6-(4-fluorophenyl)-3-nitropyridin-2-yl)amino)benzyl acetate (100 mg, yield: 41%) as a red solid. $^1$H NMR (400 MHz, Dimethylsulfoxide-$d_6$) δ 10.02 (s, 1H), 8.80 (s, 1H), 7.80-7.75 (m, 2H), 7.67 (d, J=8.4 Hz, 2H), 7.38-7.31 (m, 4H), 5.03 (s, 2H), 2.05 (s, 3H).

Step 3: 4-((5-Cyano-6-(4-fluorophenyl)-3-nitropyridin-2-yl)amino)benzyl acetate A mixture of 4-((5-bromo-6-(4-fluorophenyl)-3-nitropyridin-2-yl)amino)benzyl acetate (1.7 g, 3.69 mmol) and CuCN (1.65 g, 18.5 mmol) in DMF (20 mL) was degassed and purged with N2 three times. The mixture was stirred at 140° C. for 3 hr under $N_2$ atmosphere. The reaction mixture was quenched with $H_2O$ (50 mL) at 25° C. and extracted with EtOAc (50 mL×3). The combined organic layers were washed with brine (100 mL×3), dried over $Na_2SO_4$, filtered, and concentrated under reduced pressure. After purified by silica gel flash chromatography (Eluent of 5%~15% EtOAc in petroleum ether), 4-((5-cyano-6-(4-fluorophenyl)-3-nitropyridin-2-yl)amino)benzyl acetate (1.02 g, yield: 68%) was obtained as a yellow solid. MS: m/z=406.9 [M+H]$^+$. $^1$H NMR (400 MHz, Dimethylsulfoxide-$d_6$) δ 10.41 (s, 1H), 9.10 (s, 1H), 7.98-7.89 (m, 2H), 7.68 (d, J=8.8 Hz, 2H), 7.49-7.37 (m, 4H), 5.08 (s, 2H), 2.08 (s, 3H).

Step 4: 4-(2-(2-Aminopyridin-3-yl)-6-cyano-5-(4-fluorophenyl)-3H-imidazo[4,5-b]pyridin-3-yl)benzyl acetate To a solution of 4-((5-cyano-6-(4-fluorophenyl)-3-nitropyridin-2-yl)amino)benzyl acetate (950 mg, 2.34 mmol) in DMSO (10 mL) were added $Na_2S_2O_4$ (1.85 g, 9.35 mmol, 88% purity) and 2-aminonicotinaldehyde (343 mg, 2.81 mmol). The mixture was stirred at 100° C. for 4 hr. The reaction mixture was quenched with $H_2O$ (30 mL) at 25° C., diluted with $CH_2Cl_2$ (30 mL), and extracted with $CH_2Cl_2$ (50 mL×2). The combined organic layers were washed with brine (100 mL×3), dried over $Na_2SO_4$, filtered, and concentrated under reduced pressure. After purified by silica gel flash chromatography (Eluent of 20%~40% EtOAc in petroleum ether), 4-(2-(2-aminopyridin-3-yl)-6-cyano-5-(4-fluorophenyl)-3H-imidazo[4,5-b]pyridin-3-yl)benzyl acetate (300 mg, yield: 27%) was obtained as a yellow solid. MS: m/z=479.0 [M+H]$^+$. $^1$H NMR (400 MHz, Chloroform-d) δ 8.44 (s, 1H), 8.14-8.08 (m, 1H), 7.89 (dd, J=8.4, 5.2 Hz, 2H), 7.52 (d, J=8.0 Hz, 2H), 7.40 (d, J=8.4 Hz, 2H), 7.17 (t, J=8.4 Hz, 2H), 7.09 (d, J=7.6 Hz, 1H), 6.68 (br s, 2H), 6.40 (dd, J=8.0, 4.8 Hz, 1H), 5.21 (s, 2H), 2.16 (s, 3H).

Step 5: 2-(2-Aminopyridin-3-yl)-5-(4-fluorophenyl)-3-(4-(hydroxymethyl)phenyl)-3H-imidazo[4,5-b]pyridine-6-carbonitrile To a solution of 4-(2-(2-aminopyridin-3-yl)-6-cyano-5-(4-fluorophenyl)-3H-imidazo[4,5-b]pyridin-3-yl)benzyl acetate (290 mg, 606 μmol) in THF (5 mL), MeOH (5 mL) and $H_2O$ (5 mL) was added $K_2CO_3$ (251 mg, 1.82 mmol). The mixture was stirred at 25° C. for 1 hr. The reaction mixture was quenched with $H_2O$ (10 mL) at 25° C., diluted with $CH_2Cl_2$ (10 mL), and extracted with $CH_2Cl_2$ (15 mL×2). The combined organic layers were washed with brine (30 mL), dried over $Na_2SO_4$, filtered and concentrated under reduced pressure. 2-(2-Aminopyridin-3-yl)-5-(4-fluorophenyl)-3-(4-(hydroxymethyl)phenyl)-3H-imidazo[4,5-b]

pyridine-6-carbonitrile (270 mg) was obtained as a yellow solid. MS: m/z=437.0 [M+H]. $^1$H NMR (400 MHz, Dimethylsulfoxide-d$_6$) δ 8.90 (s, 1H), 8.02 (dd, J=4.8, 1.6 Hz, 1H), 7.85-7.80 (m, 2H), 7.48-7.43 (m, 4H), 7.40-7.36 (m, 2H), 7.27 (dd, J=7.6, 1.6 Hz, 1H), 6.90 (br s, 2H), 6.44 (dd, J=7.6, 4.8 Hz, 1H), 5.34 (t, J=5.6 Hz, 1H), 4.57 (d, J=5.6 Hz, 2H).

Step 6: 2-(2-Aminopyridin-3-yl)-3-(4-(chloromethyl)phenyl)-5-(4-fluorophenyl)-3H-imidazo[4,5-b]pyridine-6-carbonitrile %01 To a solution of 2-(2-aminopyridin-3-yl)-5-(4-fluorophenyl)-3-(4-(hydroxymethyl)phenyl)-3H-imidazo[4,5-b]pyridine-6-carbonitrile (270 mg, 619 μmol) in CH$_2$Cl$_2$ (10 mL) was added SOCl$_2$ (221 mg, 1.86 mmol) at 0° C. The mixture was stirred at 40° C. for 0.3 hr. The reaction was concentrated under reduced pressure to give 2-(2-aminopyridin-3-yl)-3-(4-(chloromethyl)phenyl)-5-(4-fluorophenyl)-3H-imidazo[4,5-b]pyridine-6-carbonitrile (Intermediate 244, 304 mg, HCl salt) as a yellow solid. MS: m/z=455.0 [M+H]$^+$. $^1$H NMR (400 MHz, Methanol-d$_4$) δ 8.76 (s, 1H), 8.04 (dd, J=6.4, 1.2 Hz, 1H), 7.93-7.85 (m, 3H), 7.67 (d, J=8.4 Hz, 2H), 7.55 (d, J=8.4 Hz, 2H), 7.24-7.22 (m, 2H), 6.92-6.84 (m, 1H), 4.76 (s, 2H).

Intermediate 245: 3-(6-Bromo-3-(4-(chloromethyl)phenyl)-5-(4-fluorophenyl)-3H-imidazo[4,5-b]pyridin-2-yl)pyridin-2-amine

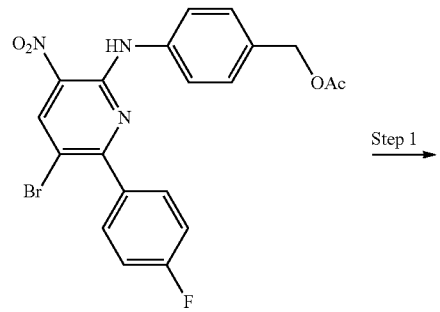

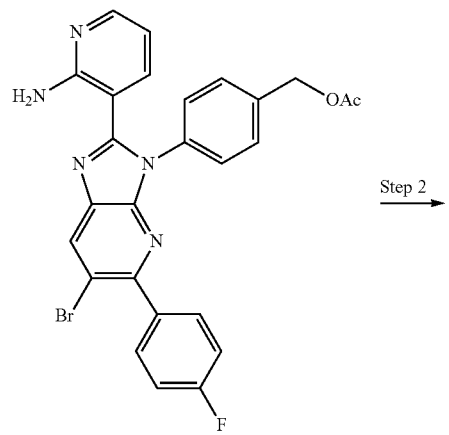

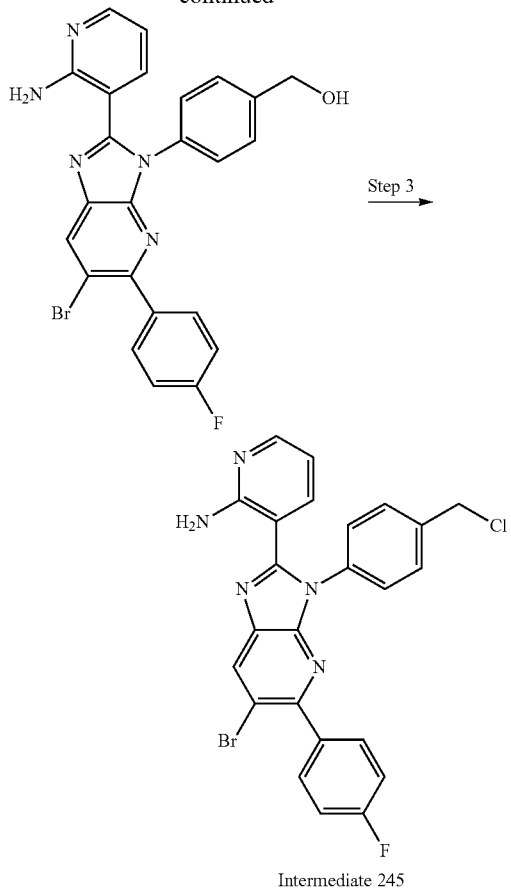

Intermediate 245

Step 1: 4-(2-(2-Aminopyridin-3-yl)-6-bromo-5-(4-fluorophenyl)-3H-imidazo[4,5-b]pyridin-3-yl)benzyl acetate To a solution of 4-((5-bromo-6-(4-fluorophenyl)-3-nitropyridin-2-yl)amino)benzyl acetate (refer to Intermediate 244 for detail procedures, 1 g, 2.17 mmol) in DMSO (10 mL) was added Na$_2$S$_2$O$_4$ (1.72 g, 8.69 mmol, 88% purity) and 2-aminonicotinaldehyde (318 mg, 2.61 mmol). The mixture was stirred at 100° C. for 4 hr. The reaction mixture was quenched with H$_2$O (50 mL) at 25° C., diluted with CH$_2$Cl$_2$ (50 mL), and extracted with CH$_2$Cl$_2$ (25 mL×2). The combined organic layers were washed with brine (100 mL×3), dried over Na$_2$SO$_4$, filtered, and concentrated under reduced pressure. After purified by silica gel flash chromatography (Eluent of 30%~50% EtOAc in petroleum ether), 4-(2-(2-aminopyridin-3-yl)-6-bromo-5-(4-fluorophenyl)-3H-imidazo[4,5-b]pyridin-3-yl)benzyl acetate (280 mg, yield: 24%) was obtained as a yellow solid. MS: m/z=531.9, 533.9 [M+H]$^+$. $^1$H NMR (400 MHz, Dimethylsulfoxide-d$_6$) δ 8.65 (s, 1H), 8.02 (dd, J=4.8, 1.6 Hz, 1H), 7.60 (dd, J=8.4, 5.6 Hz, 2H), 7.52-7.45 (m, 4H), 7.32-7.27 (m, 2H), 7.24 (dd, J=7.6, 1.6 Hz, 1H), 6.86 (br s, 2H), 6.44 (dd, J=7.6, 5.2 Hz, 1H), 5.13 (s, 2H), 2.09 (s, 3H).

Step 2: (4-(2-(2-Aminopyridin-3-yl)-6-bromo-5-(4-fluorophenyl)-3H-imidazo[4,5-b]pyridin-3-yl)phenyl)methanol To a solution of 4-(2-(2-aminopyridin-3-yl)-6-bromo-5-(4-fluorophenyl)-3H-imidazo[4,5-b]pyridin-3-yl)benzyl acetate (240 mg, 451 µmol) in THF (2 mL), MeOH (2 mL) and H$_2$O (2 mL) was added K$_2$CO$_3$ (187 mg, 1.35 mmol). The mixture was stirred at 25° C. for 1 hr. The reaction mixture was quenched with H$_2$O (20 mL) at 25° C., diluted with CH$_2$Cl$_2$ (20 mL) and extracted with CH$_2$Cl$_2$ (25 mL×2). The combined organic layers were washed with brine (50 mL), dried over Na$_2$SO$_4$, filtered and concentrated under reduced pressure. (4-(2-(2-Aminopyridin-3-yl)-6-bromo-5-(4-fluorophenyl)-3H-imidazo[4,5-b]pyridin-3-yl)phenyl) methanol (240 mg) was obtained as a yellow solid. MS: m/z=490.0, 492.0 [M+H]. $^1$H NMR (400 MHz, Dimethylsulfoxide-d$_6$) δ 8.63 (s, 1H), 8.00 (dd, J=4.8, 1.6 Hz, 1H), 7.62-7.57 (m, 2H), 7.44-7.38 (m, 4H), 7.28-7.26 (m, 2H), 7.21 (dd, J=7.6, 2.0 Hz, 1H), 6.93 (br s, 2H), 6.42 (dd, J=7.6, 4.4 Hz, 1H), 5.32 (t, J=5.2 Hz, 1H), 4.55 (d, J=5.2 Hz, 2H).

Step 3: 3-(6-Bromo-3-(4-(chloromethyl)phenyl)-5-(4-fluorophenyl)-3H-imidazo[4,5-b]pyridin-2-yl)pyridin-2-amine To a solution of (4-(2-(2-aminopyridin-3-yl)-6-bromo-5-(4-fluorophenyl)-3H-imidazo[4,5-b]pyridin-3-yl)phenyl) methanol (240 mg, 489 µmol) in CH$_2$Cl$_2$ (10 mL) was added SOCl$_2$ (175 mg, 1.47 mmol) at 0° C. The mixture was stirred at 40° C. for 0.3 hr. The reaction was concentrated under reduced pressure to give 3-(6-bromo-3-(4-(chloromethyl) phenyl)-5-(4-fluorophenyl)-3H-imidazo[4,5-b]pyridin-2-yl) pyridin-2-amine (Intermediate 245, 266 mg, HCl salt) as a yellow solid. MS: m/z=508.0, 509.8 [M+H]$^+$.

Intermediate 246: 2-(2-Aminopyridin-3-yl)-1-(4-(chloromethyl)phenyl)-1H-imidazo[4,5-c]pyridine-6-carbonitrile Step 1: (4-((2-Bromo-5-nitropyridin-4-yl)amino) phenyl)methanol To a solution of 2,4-dibromo-5-nitropyridine (4 g, 14.2 mmol) in DMSO (50 mL) were added DIEA (5.50 g, 42.6 mmol) and (4-aminophenyl)methanol (1.75 g, 14.2 mmol). The mixture was stirred at 100° C. for 16 hr. The reaction mixture was quenched with H$_2$O (500 mL) at 25° C., diluted with EtOAc (500 mL), and extracted with EtOAc (500 mL×2). The combined organic layers were washed with brine (500 mL×3), dried over Na$_2$SO$_4$, filtered and concentrated under reduced pressure to give (4-((2-bromo-5-nitropyridin-4-yl)amino)phenyl)methanol (4.6 g, yield: 88%) as a light yellow solid. MS: m/z=323.9, 325.9 [M+H]$^+$. $^1$H NMR (400 MHz, Chloroform-d) δ 9.80 (s, 1H), 9.22 (s, 1H), 7.70 (d, J=8.0 Hz, 2H), 7.45 (d, J=8.4 Hz, 3H), 4.96 (s, 2H).

Step 2: 4-((2-Bromo-5-nitropyridin-4-yl)amino)benzyl acetate

To a solution of (4-((2-bromo-5-nitropyridin-4-yl)amino) phenyl)methanol (4.5 g, 13.9 mmol) in CH$_2$Cl$_2$ (50 mL) were added DMAP (170 mg, 1.39 mmol), Ac$_2$O (1.42 g, 13.9 mmol) and TEA (4.21 g, 41.7 mmol). The mixture was stirred at 25° C. for 1 hr. The reaction mixture was quenched with H$_2$O (100 mL) at 25° C., diluted with CH$_2$Cl$_2$ (50 mL), and extracted with CH$_2$Cl$_2$ (50 mL×2). The combined organic layers were washed with brine (50 mL), dried over Na$_2$SO$_4$, filtered, and concentrated under reduced pressure. After purified by silica gel flash chromatography (Eluent of 0%~19% EtOAc in petroleum ether), 4-((2-bromo-5-nitropyridin-4-yl)amino)benzyl acetate (1.5 g, yield: 29%) was obtained as a yellow solid. MS: m/z=365.9, 367.9 [M+H]$^+$. $^1$H NMR (400 MHz, Chloroform-d) δ 9.62 (s, 1H), 9.03 (s, 1H), 7.50 (d, J=8.4 Hz, 2H), 7.28 (d, J=8.4 Hz, 2H), 7.10 (s, 1H), 5.15 (s, 2H), 2.14 (s, 3H).

Step 3: 4-((2-Cyano-5-nitropyridin-4-yl)amino)benzyl acetate

A mixture of 4-((2-bromo-5-nitropyridin-4-yl)amino)benzyl acetate (1.5 g, 4.10 mmol), dicyanozinc (2.28 g, 19.4 mmol), Pd(PPh$_3$)$_4$ (473 mg, 410 µmol) in DMF (15 mL) was degassed and purged with N$_2$ three times, then stirred at 80° C. for 3 hr under N$_2$ atmosphere. The reaction mixture was quenched with H$_2$O (500 mL) at 25° C. and extracted with CH$_2$Cl$_2$ (500 mL×3). The combined organic layers were washed with brine (100 mL×3), dried over Na$_2$SO$_4$, filtered, and concentrated under reduced pressure. After purified by silica gel flash chromatography (Eluent of 5%~15% EtOAc in petroleum ether), 4-((2-cyano-5-nitropyridin-4-yl)amino) benzyl acetate (1.1 g, yield: 86%) was obtained as a light yellow solid. MS: m/z=312.9 [M+H]$^+$.

Step 4: 4-(2-(2-Aminopyridin-3-yl)-6-cyano-1H-imidazo[4,5-c]pyridin-1-yl)benzyl acetate To a solution of 4-((2-cyano-5-nitropyridin-4-yl)amino) benzyl acetate (1 g, 3.20 mmol) in DMSO (20 mL) were added Na$_2$S$_2$O$_4$ (2.23 g, 12.8 mmol, 88% purity) and 2-aminonicotinaldehyde (469 mg, 3.84 mmol). The mixture was stirred at 100° C. for 16 hr. The reaction mixture was quenched with H$_2$O (300 mL) at 25° C., diluted with CH$_2$Cl$_2$ (300 mL) and extracted with CH$_2$Cl$_2$ (300 mL×2). The combined organic layers were washed with brine (500 mL), dried over Na$_2$SO$_4$, filtered and concentrated under reduced pressure. After purified by silica gel flash chromatography (Eluent of 0%~27% EtOAc in petroleum ether), 4-(2-(2-aminopyridin-3-yl)-6-cyano-1H-imidazo[4,5-c]pyridin-1-yl)benzyl acetate (160 mg, yield: 11%) was obtained as a light yellow solid. MS: m/z=385.1 [M+H]$^+$.

Step 5: 2-(2-Aminopyridin-3-yl)-1-(4-(hydroxymethyl)phenyl)-1H-imidazo[4,5-c]pyridine-6-carbonitrile To a solution of 4-(2-(2-aminopyridin-3-yl)-6-cyano-1H-imidazo[4,5-c]pyridin-1-yl)benzyl acetate (160 mg, 416 µmol) in THF (2 mL), MeOH (2 mL) and H$_2$O (1 mL) was added K$_2$C$_0$ (173 mg, 1.25 mmol). The mixture was stirred at 25° C. for 0.5 hr. The reaction mixture was diluted with H$_2$O (50 mL) and extracted with CH$_2$Cl$_2$ (50 mL×2). The combined organic layers were washed with brine (100 mL), dried over Na$_2$SO$_4$, filtered and concentrated under reduced pressure. 2-(2-Aminopyridin-3-yl)-1-(4-(hydroxymethyl) phenyl)-1H-imidazo[4,5-c]pyridine-6-carbonitrile (160 mg crude) was obtained as a light yellow solid. MS: m/z=343.1 [M+H]$^+$.

Step 6: 2-(2-Aminopyridin-3-yl)-1-(4-(chloromethyl)phenyl)-1H-imidazo[4,5-c]pyridine-6-carbonitrile To a solution of 2-(2-aminopyridin-3-yl)-1-(4-(hydroxymethyl)phenyl)-1H-imidazo[4,5-c]pyridine-6-carbonitrile (160 mg, 467 µmol) in CH$_2$Cl$_2$ (2 mL) was added SOCl$_2$ (167 mg, 1.40 mmol). The mixture was stirred at 40° C. for 0.5 hr. The reaction was concentrated under reduced pressure to give 2-(2-aminopyridin-3-yl)-1-(4-(chloromethyl)phenyl)-1H-imidazo[4,5-c]pyridine-6-carbonitrile (Intermediate 246, 160 mg, HCl salt) as a light yellow solid. MS: m/z=361.0 [M+H]⁺.

Intermediate 247: 3-(3-(4-(Chloromethyl)phenyl)-5-(1-methyl-1H-1,2,4-triazol-3-yl)-3H-imidazo[4,5-b]pyridin-2-yl)pyridin-2-amine

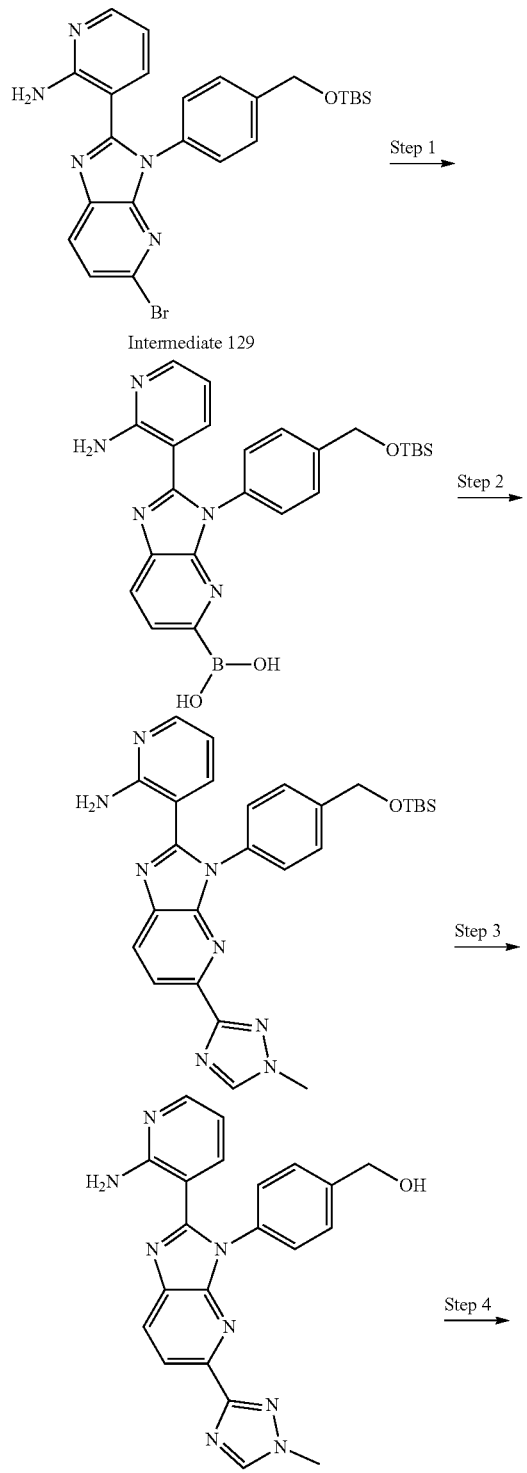

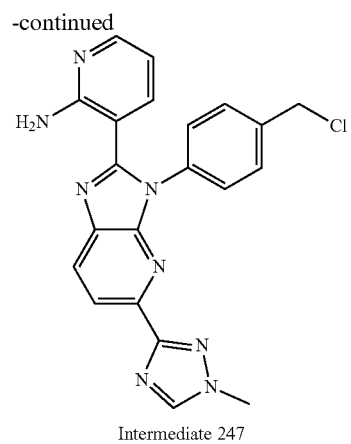

Intermediate 247

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl₂ (143 mg, 196 μmol) in 1,4-dioxane (20 mL) was degassed and purged with N₂ three times. The mixture was stirred at 80° C. for 2 hr under N₂ atmosphere. The mixture was used in the next step without work-up and purification. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black solution. MS: m/z=476.2 [M+H]⁺.

Step 2: 3-(3-(4-(((tert-Butyldimethylsilyl)oxy)methyl)phenyl)-5-(1-methyl-1H-1,2,4-triazol-3-yl)-3H-imidazo[4,5-b]pyridin-2-yl)pyridin-2-amine To a solution of (2-(2-aminopyridin-3-yl)-3-(4-(((tert-butyldimethylsilyl)oxy)methyl)phenyl)-3H-imidazo[4,5-b]pyridin-5-yl)boronic acid in H₂O (2 mL) and 1,4-dioxane (10 mL) were added 3-bromo-1-methyl-1H-1,2,4-triazole (348 mg, 2.15 mmol), Pd(dppf)Cl₂ (131 mg, 179 gmol) and Cs₂CO₃ (1.75 g, 5.36 mmol). The mixture was degassed and purged with N₂ three times and stirred at 80° C. for 16 hr under N₂ atmosphere. The reaction mixture was quenched with H₂O (50 mL) and extracted with CH₂Cl₂ (50 mL×2). The combined organic layers were washed with brine (50 mL), dried over Na₂SO₄, filtered, and concentrated under reduced pressure. After purified by silica gel flash chromatography (Eluent of 20%~80% EtOAc in petroleum ether), 3-(3-(4-(((tert-butyldimethylsilyl)oxy)methyl)phenyl)-5-(1-methyl-1H-1,2,4-triazol-3-yl)-3H-imidazo[4,5-b]pyridin-2-yl)pyridin-2-amine (310 mg, yield: 31% for two steps) was obtained as a black solid. MS: m/z=513.2 [M+H]⁺. ¹H NMR (400 MHz, Dimethylsulfoxide-d₆) δ 8.52 (s, 1H), 8.27 (d, J=8.4 Hz, 1H), 8.11 (d, J=8.4 Hz, 1H), 8.01-7.97 (m, 1H), 7.52-7.42 (m, 4H), 7.18 (dd, J=7.6, 1.6 Hz, 1H), 6.99 (s, 2H), 6.37 (dd, J=7.6, 4.8 Hz, 1H), 4.83 (s, 2H), 3.92 (s, 3H), 0.94 (s, 9H), 0.13 (s, 6H).

Step 3: (4-(2-(2-Aminopyridin-3-yl)-5-(1-methyl-1H-1,2,4-triazol-3-yl)-3H-imidazo[4,5-b]pyridin-3-yl)phenyl)methanol To a solution of 3-(3-(4-(((tert-butyldimethylsilyl)oxy)methyl)phenyl)-5-(1-methyl-1H-1,2,4-triazol-3-yl)-3H-imidazo[4,5-b]pyridin-2-yl)pyridin-2-amine (310 mg, 605 µmol) in THF (5 mL) was added TBAF (1.21 mL, 1 M in THF). The mixture was stirred at 25° C. for 0.5 hr. The reaction mixture was quenched with $H_2O$ (20 mL) at 25° C. and extracted with $CH_2Cl_2$ (20 mL×3). The combined organic layers were washed with brine (20 mL×2), dried over $Na_2SO_4$, filtered and concentrated under reduced pressure. (4-(2-(2-Aminopyridin-3-yl)-5-(1-methyl-1H-1,2,4-triazol-3-yl)-3H-imidazo[4,5-b]pyridin-3-yl)phenyl)methanol (150 mg, yield: 62%) was obtained as a black solid. MS: m/z=399.1 $[M+H]^+$. $^1H$ NMR (400 MHz, Dimethylsulfoxide-$d_6$) δ 8.52 (s, 1H), 8.26 (d, J=8.4 Hz, 1H), 8.10 (d, J=8.4 Hz, 1H), 8.00-7.97 (m, 1H), 7.50-7.41 (m, 4H), 7.24-7.20 (m, 1H), 6.96 (s, 2H), 6.40 (dd, J=7.6, 5.2 Hz, 1H), 5.39-5.33 (m, 1H), 4.60 (d, J=6.0 Hz, 2H), 3.92 (s, 3H).

Step 4: 3-(3-(4-(Chloromethyl)phenyl)-5-(1-methyl-1H-1,2,4-triazol-3-yl)-3H-imidazo[4,5-b]pyridin-2-yl)pyridin-2-amine To a solution of (4-(2-(2-aminopyridin-3-yl)-5-(1-methyl-1H-1,2,4-triazol-3-yl)-3H-imidazo[4,5-b]pyridin-3-yl)phenyl)methanol (160 mg, 376 µmol) in $CH_2Cl_2$ (5 mL) was added $SOCl_2$ (135 mg, 1.13 mmol). The mixture was stirred at 25° C. for 0.5 hr. The reaction was concentrated under reduced pressure to give 3-(3-(4-(chloromethyl)phenyl)-5-(1-methyl-1H-1,2,4-triazol-3-yl)-3H-imidazo[4,5-b]pyridin-2-yl)pyridin-2-amine (Intermediate 247, 156 mg) as a brown solid. MS: m/z=417.1 $[M+H]^+$.

Intermediate 248: 2-(2-Aminopyridin-3-yl)-3-(4-(chloromethyl)phenyl)-5-methyl-3H-imidazo[4,5-b]pyridine-6-carbonitrile

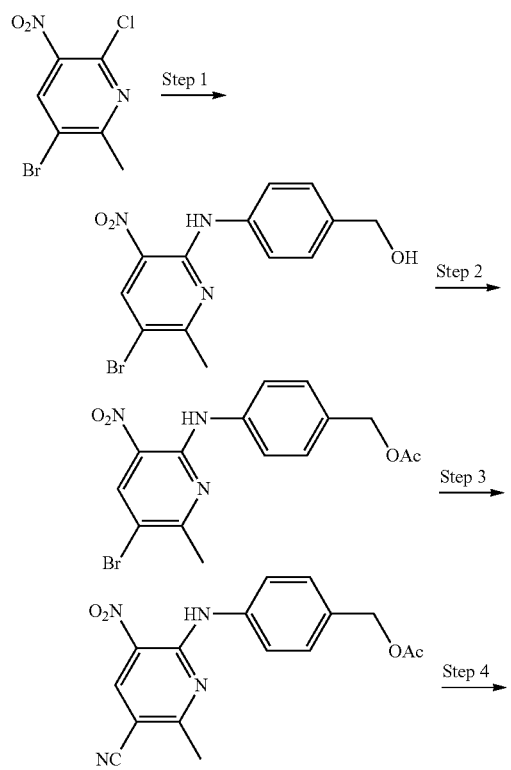

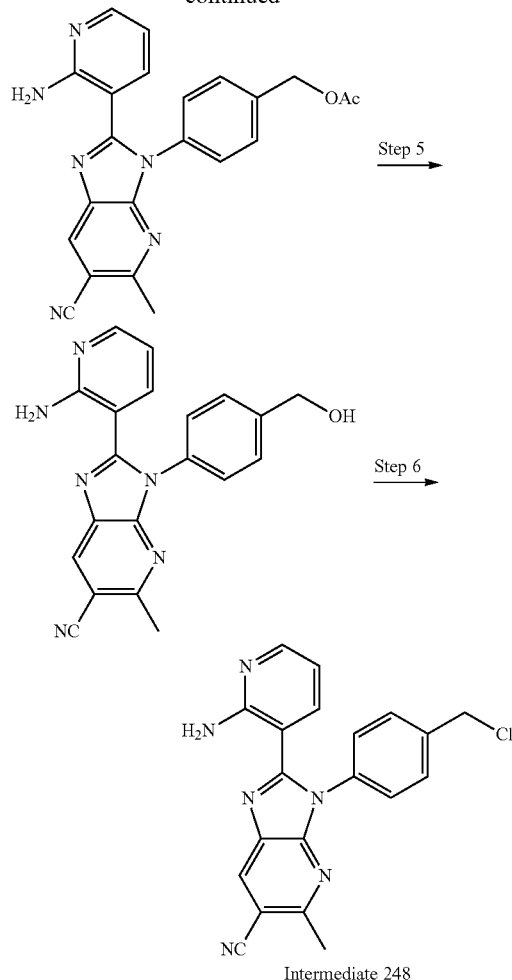

Intermediate 248

Step 1: (4-((5-Bromo-6-methyl-3-nitropyridin-2-yl)amino)phenyl)methanol

To a solution of 3-bromo-6-chloro-2-methyl-5-nitropyridine (1 g, 3.98 mmol) in DMSO (10 mL) were added DIEA (1.54 g, 11.9 mmol) and (4-aminophenyl)methanol (490 mg, 3.98 mmol). The mixture was stirred at 100° C. for 16 hr. The reaction mixture was quenched with $H_2O$ (50 mL) at 25° C., diluted with $CH_2Cl_2$ (50 mL), and extracted with $CH_2Cl_2$ (50 mL×2). The combined organic layers were washed with brine (50 mL×3), dried over $Na_2SO_4$, filtered and concentrated under reduced pressure. (4-((5-Bromo-6-methyl-3-nitropyridin-2-yl)amino)phenyl)methanol (1.3 g) was obtained as a black solid. MS: m/z=337.8, 339.8 $[M+H]^+$. $^1H$ NMR (400 MHz, Dimethylsulfoxide-$d_6$) δ 9.96 (s, 1H), 8.60 (s, 1H), 7.60 (d, J=8.4 Hz, 2H), 7.31 (d, J=8.4 Hz, 2H), 5.16 (t, J=6.0 Hz, 1H), 4.48 (d, J=5.2 Hz, 2H), 2.52 (s, 3H).

Step 2: 4-((5-Bromo-6-methyl-3-nitropyridin-2-yl)amino)benzyl acetate

To a solution of (4-((5-bromo-6-methyl-3-nitropyridin-2-yl)amino)phenyl)methanol (1.3 g, 3.84 mmol) in $CH_2Cl_2$ (15 mL) were added DMAP (93.9 mg, 769 µmol), $Ac_2O$ (589 mg, 5.77 mmol) and TEA (1.17 g, 11.5 mmol). The mixture was stirred at 25° C. for 1 hr. The reaction mixture was quenched with H₂O (25 mL) at 25° C., diluted with CH₂Cl₂ (50 mL) and extracted with CH₂Cl₂ (50 mL×2). The combined organic layers were washed with brine (50 mL), dried over Na₂SO₄, filtered, and concentrated under reduced pressure. After purified by silica gel flash chromatography (Eluent of 1%~10% EtOAc in petroleum ether), 4-((5-bromo-6-methyl-3-nitropyridin-2-yl)amino)benzyl acetate (850 mg, yield: 58% for two steps) was obtained as a red solid. MS: m/z=377.8, 379.8 [M+H]⁺. ¹H NMR (400 MHz, Dimethylsulfoxide-d₆) δ 9.98 (s, 1H), 8.62 (s, 1H), 7.68 (d, J=8.4 Hz, 2H), 7.36 (d, J=8.4 Hz, 2H), 5.05 (s, 2H), 2.54 (s, 3H), 2.07 (s, 3H).

Step 3: 4-((5-Cyano-6-methyl-3-nitropyridin-2-yl)amino)benzyl acetate

A mixture of 4-((5-bromo-6-methyl-3-nitropyridin-2-yl)amino)benzyl acetate (1 g, 2.63 mmol) and CuCN (471 mg, 5.26 mmol) in DMF (10 mL) was degassed and purged with N₂ three times. The mixture was stirred at 140° C. for 3 hr under N₂ atmosphere. The reaction mixture was quenched with H₂O (50 mL) at 25° C. and extracted with EtOAc (50 mL×3). The combined organic layers were washed with brine (100 mL×3), dried over Na₂SO₄, filtered and concentrated under reduced pressure. After purified by silica gel flash chromatography (Eluent of 5%~15% EtOAc in petroleum ether), 4-((5-cyano-6-methyl-3-nitropyridin-2-yl)amino)benzyl acetate (480 mg, yield: 56%) was obtained as a yellow solid. MS: m/z=326.9 [M+H]⁺. ¹H NMR (400 MHz, Dimethylsulfoxide-d₆) δ 10.32 (s, 1H), 8.94 (s, 1H), 7.65 (d, J=8.8 Hz, 2H), 7.39 (d, J=8.4 Hz, 2H), 5.08 (s, 2H), 2.56 (s, 3H), 2.07 (s, 3H).

Step 4: 4-(2-(2-Aminopyridin-3-yl)-6-cyano-5-methyl-3H-imidazo[4,5-b]pyridin-3-yl)benzyl acetate To a solution of 4-((5-cyano-6-methyl-3-nitropyridin-2-yl)amino)benzyl acetate (700 mg, 2.15 mmol) in DMSO (1 mL) were added Na₂S₂O₄ (1.70 g, 8.58 mmol, 88% purity) and 2-aminonicotinaldehyde (314 mg, 2.57 mmol). The mixture was stirred at 100° C. for 6 hr. The reaction mixture was quenched with H₂O (30 mL) at 25° C., diluted with CH₂Cl₂ (30 mL) and extracted with CH₂Cl₂ (50 mL×2). The combined organic layers were washed with brine (50 mL), dried over Na₂SO₄, filtered and concentrated under reduced pressure. After purified by silica gel flash chromatography (Eluent of 20%~50% EtOAc in petroleum ether), 4-(2-(2-aminopyridin-3-yl)-6-cyano-5-methyl-3H-imidazo[4,5-b]pyridin-3-yl)benzyl acetate (200 mg, yield: 23%) was obtained as a light yellow solid. MS: m/z=399.0 [M+H]⁺. ¹H NMR (400 MHz, Dimethylsulfoxide-d₆) δ 8.72 (s, 1H), 8.00 (dd, J=4.8, 2.0 Hz, 1H), 7.54-7.50 (m, 2H), 7.48-7.43 (m, 2H), 7.25 (dd, J=7.6, 1.6 Hz, 1H), 6.82 (br s, 2H), 6.43 (dd, J=7.6, 4.8 Hz, 1H), 5.15 (s, 2H), 2.70 (s, 3H), 2.11 (s, 3H).

Step 5: 2-(2-Aminopyridin-3-yl)-3-(4-(hydroxymethyl)phenyl)-5-methyl-3H-imidazo[4,5-b]pyridine-6-carbonitrile To a solution of 4-(2-(2-aminopyridin-3-yl)-6-cyano-5-methyl-3H-imidazo[4,5-b]pyridin-3-yl)benzyl acetate (180 mg, 452 μmol) in THF (2 mL) and MeOH (2 mL) was added K₂CO₃ (187 mg, 1.36 mmol). The mixture was stirred at 25° C. for 1 hr. The reaction mixture was diluted with H₂O (30 mL) and extracted with CH₂Cl₂ (50 mL×2). The combined organic layers were washed with brine (100 mL), dried over Na₂SO₄, filtered and concentrated under reduced pressure. 2-(2-Aminopyridin-3-yl)-3-(4-(hydroxymethyl)phenyl)-5-methyl-3H-imidazo[4,5-b]pyridine-6-carbonitrile (170 mg) was obtained as a yellow solid. MS: m/z=357.0 [M+H]⁺. ¹H NMR (400 MHz, Dimethylsulfoxide-d₆) δ 8.71 (s, 1H), 8.00 (dd, J=4.8, 1.6 Hz, 1H), 7.48-7.44 (m, 2H), 7.42-7.37 (m, 2H), 7.24 (dd, J=7.6, 1.6 Hz, 1H), 6.90 (br s, 2H), 6.41 (dd, J=7.6, 4.8 Hz, 1H), 5.35 (t, J=5.6 Hz, 1H), 4.58 (d, J=5.6 Hz, 2H), 2.69 (s, 3H).

Step 6: 2-(2-Aminopyridin-3-yl)-3-(4-(chloromethyl)phenyl)-5-methyl-3H-imidazo[4,5-b]pyridine-6-carbonitrile To a solution of 2-(2-aminopyridin-3-yl)-3-(4-(hydroxymethyl)phenyl)-5-methyl-3H-imidazo[4,5-b]pyridine-6-carbonitrile (170 mg, 477 μmol) in CH₂Cl₂ (5 mL) was added SOCl₂ (170 mg, 1.43 mmol). The mixture was stirred at 25° C. for 1 hr. The reaction was concentrated under reduced pressure, 2-(2-aminopyridin-3-yl)-3-(4-(chloromethyl)phenyl)-5-methyl-3H-imidazo[4,5-b]pyridine-6-carbonitrile (Intermediate 248, 196 mg, HCl salt) was obtained as a yellow solid. MS: m/z=375.0 [M+H]⁺.

Intermediate 249 & 250: 4-((6-(3-Methyl-4H-1,2,4-triazol-4-yl)-3-nitropyridin-2-yl)amino)benzyl acetate & 4-((6-(3-Methyl-1H-1,2,4-triazol-1-yl)-3-nitropyridin-2-yl)amino)benzyl acetate

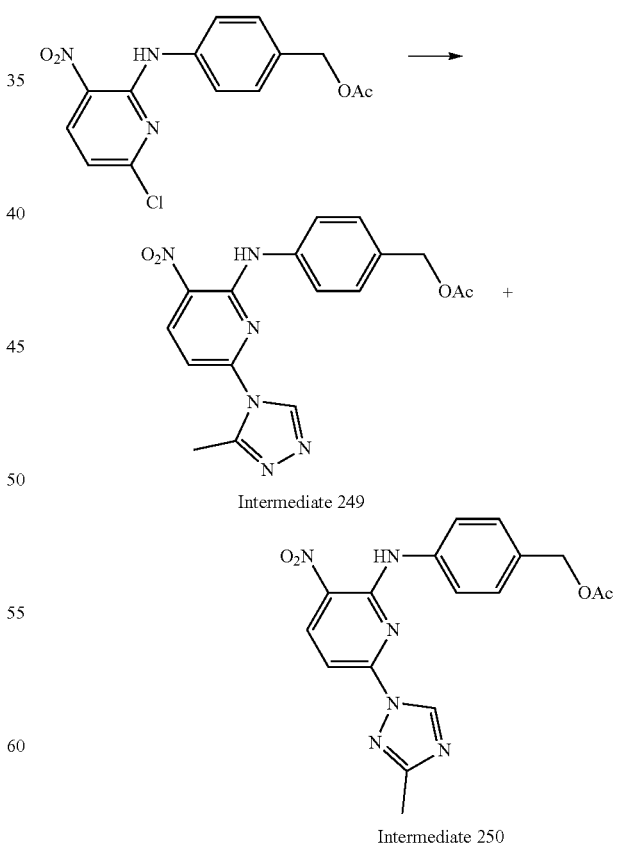

Intermediate 249

Intermediate 250

To a solution of 4-((6-chloro-3-nitropyridin-2-yl)amino)benzyl acetate (Refer to Intermediate 178 for detail procedures, 3 g, 9.33 mmol) and 3-methyl-4H-1,2,4-triazole (929 mg, 11.19 mmol) in DMSO (30 mL) was added DIEA (4.87 mL). The mixture was stirred at 100° C. for 16 hr. The reaction mixture was diluted with H$_2$O (100 mL) and extracted with CH$_2$Cl$_2$ (200 mL). The combined organic layers were washed with brine (100 mL), dried over anhydrous Na$_2$SO$_4$, filtered and concentrated under reduced pressure. After purified by prep-HPLC (column: Phenomenex luna C18 (250×70 mm, 10 μm); mobile phase: [water (HCl)-ACN]; gradient: 32%-72% B over 28 min), 4-((6-(3-methyl-4H-1,2,4-triazol-4-yl)-3-nitropyridin-2-yl)amino)benzyl acetate (Intermediate 249, 475 mg, yield: 14%) was obtained as a yellow solid. MS: m/z=369.1 [M+H]+ 1H NMR (400 MHz, Dimethylsulfoxide-d$_6$) δ 10.20 (br s, 1H), 8.72 (d, J=8.8 Hz, 1H), 8.11 (s, 1H), 7.49 (d, J=8.4 Hz, 2H), 7.41 (d, J=8.4 Hz, 2H), 7.34 (d, J=9.2 Hz, 1H), 5.09 (s, 2H), 2.27 (s, 3H), 2.08 (s, 3H), 4-((6-(3-Methyl-1H-1,2,4-triazol-1-yl)-3-nitropyridin-2-yl)amino)benzyl acetate (Intermediate 250, 1.1 g, yield: 32%) was obtained as a yellow solid. MS: m/z=369.2 [M+H]$^+$. $^1$H NMR (400 MHz, Dimethylsulfoxide-d$_6$) δ 10.25 (br s, 1H), 8.88 (s, 1H), 8.75 (d, J=8.4, 1H), 7.71 (d, J=7.2 Hz, 2H), 7.44 (d, J=7.2 Hz, 2H), 7.30 (d, J=8.4 Hz, 1H), 5.09 (s, 2H), 2.27 (s, 3H), 2.08 (s, 3H).

Intermediate 251: 3-(3-(4-(Chloromethyl)phenyl)-5-(3-methyl-4H-1,2,4-triazol-4-yl)-3H-imidazo[4,5-b]pyridin-2-yl)pyridin-2-amine

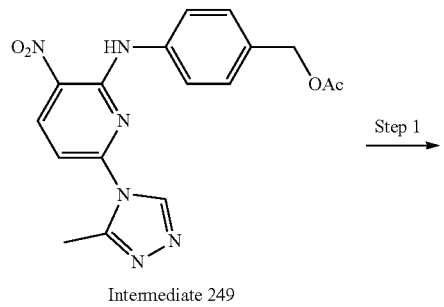

Intermediate 249

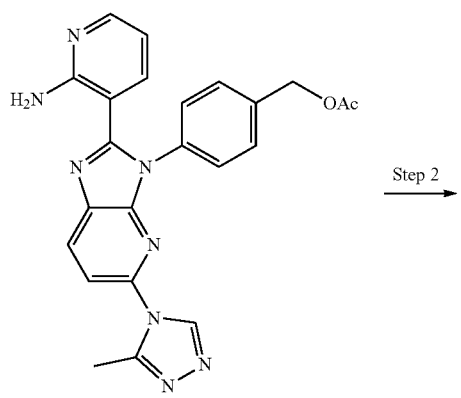

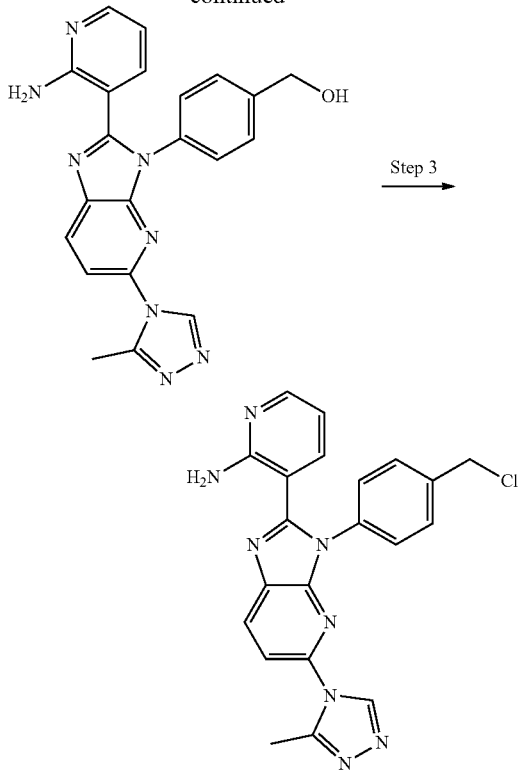

Intermediate 251

Step 1: 4-(2-(2-Aminopyridin-3-yl)-5-(3-methyl-4H-1,2,4-triazol-4-yl)-3H-imidazo[4,5-b]pyridin-3-yl)benzyl acetate To a solution of Intermediate 249 (400 mg, 1.09 mmol), 2-aminonicotinaldehyde (146 mg, 1.19 mmol) in DMSO (20 mL) was added Na$_2$S$_2$O$_4$ (869 mg, 4.34 mmol). The mixture was stirred at 100° C. for 16 hr. The reaction mixture was poured into H$_2$O (20 mL), extracted with EtOAc (15 mL×3). The combined organic phases were dried over anhydrous Na$_2$SO$_4$, filtered and concentrated under reduced pressure. After purified by silica gel flash chromatography (Eluent of 0%~69% EtOAc in petroleum ether), 4-(2-(2-aminopyridin-3-yl)-5-(3-methyl-4H-1,2,4-triazol-4-yl)-3H-imidazo[4,5-b]pyridin-3-yl)benzyl acetate (150 mg, yield: 31%) was obtained as a gray solid. MS: m/z=441.3 [M+H]$^+$.

Step 2: (4-(2-(2-Aminopyridin-3-yl)-5-(3-methyl-4H-1,2,4-triazol-4-yl)-3H-imidazo[4,5-b]pyridin-3-yl)phenyl)methanol To mixture of 4-(2-(2-aminopyridin-3-yl)-5-(3-methyl-4H-1,2,4-triazol-4-yl)-3H-imidazo[4,5-b]pyridin-3-yl)benzyl acetate (150 mg, 341 μmol) in THF (1.5 mL) and MeOH (1.5 mL) was added K$_2$CO$_3$ (94.1 mg, 681 μmol) in H$_2$O (1 mL). The mixture was stirred at 25° C. for 0.5 hr. The reaction mixture was concentrated under reduced pressure. The residue was diluted with H$_2$O (5 mL) and extracted with EtOAc (10 mL×3). The organic phase was dried over anhydrous Na$_2$SO$_4$, filtered and concentrated under reduced pressure. (4-(2-(2-Aminopyridin-3-yl)-5-(3-methyl-4H-1,2,4-triazol-4-yl)-3H-imidazo[4,5-b]pyridin-3-yl)phenyl)methanol (145 mg) was obtained as a gray solid. MS: m/z=399.2 [M+H]$^+$.

Step 3: 3-(3-(4-(Chloromethyl)phenyl)-5-(3-methyl-4H-1,2,4-triazol-4-yl)-3H-imidazo[4,5-b]pyridin-2-yl)pyridin-2-amine To a solution of (4-(2-(2-aminopyridin-3-yl)-5-(3-methyl-4H-1,2,4-triazol-4-yl)-3H-imidazo[4,5-b]pyridin-3-yl)phenyl)methanol (145 mg, 364 μmol) in CH₂Cl₂ (2 mL) was added SOCl₂ (1 mL). The mixture was stirred at 25° C. for 0.5 hr. The reaction mixture was concentrated under reduced pressure. 3-(3-(4-(Chloromethyl)phenyl)-5-(3-methyl-4H-1,2,4-triazol-4-yl)-3H-imidazo[4,5-b]pyridin-2-yl)pyridin-2-amine (Intermediate 251, 166 mg) was obtained as a gray solid. MS: m/z=417.1, 419.1 [M+H]⁺.

Intermediate 252: 3-(3-(4-(Chloromethyl)phenyl)-5-(3-methyl-1H-1,2,4-triazol-1-yl)-3H-imidazo[4,5-b]pyridin-2-yl)pyridin-2-amine

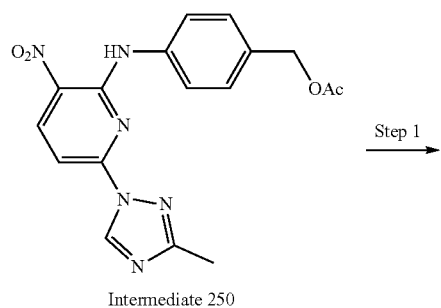

Intermediate 250

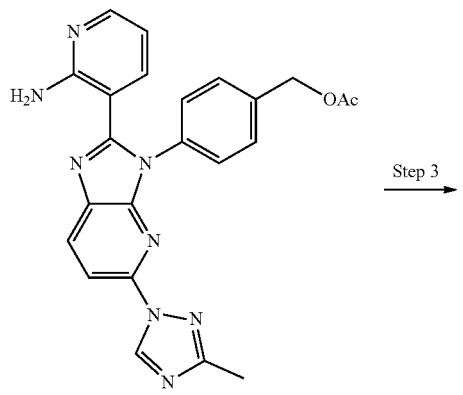

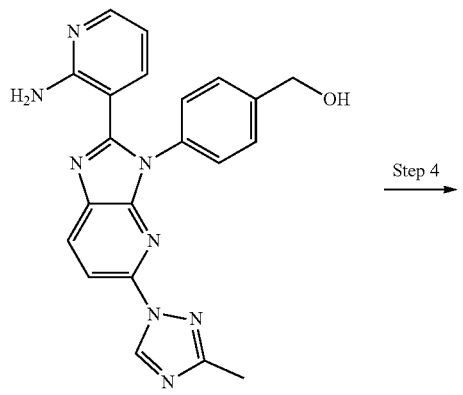

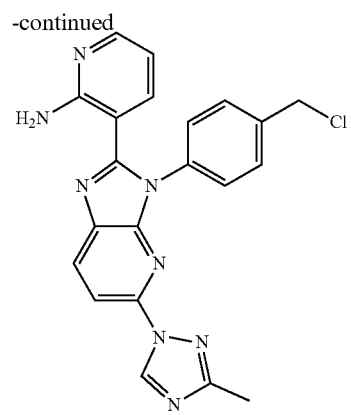

Intermediate 252

Step 1: 4-(2-(2-Aminopyridin-3-yl)-5-(3-methyl-1H-1,2,4-triazol-1-yl)-3H-imidazo[4,5-b]pyridin-3-yl)benzyl acetate To a solution of Intermediate 250 (550 mg, 1.49 mmol) in DMSO (5 mL) were added Na₂S₂O₄ (1.04 g, 5.97 mmol, 88% purity) and 2-aminonicotinaldehyde (219 mg, 1.79 mmol). The mixture was stirred at 100° C. for 6 hr. The reaction mixture was quenched with H₂O (50 mL) at 25° C., diluted with EtOAc (50 mL), and extracted with EtOAc (50 mL×2). The combined organic layers were washed with brine (50 mL), dried over Na₂SO₄, filtered and concentrated under reduced pressure. After purified by silica gel flash chromatography (Eluent of 0%~63% EtOAc in petroleum ether), 4-(2-(2-aminopyridin-3-yl)-5-(3-methyl-1H-1,2,4-triazol-1-yl)-3H-imidazo[4,5-b]pyridin-3-yl)benzyl acetate (200 mg, yield: 24%) was obtained as a light yellow solid. MS: m z=441.1 [M+H]⁺. ¹H NMR (400 MHz, Chloroform-d) δ 8.86 (s, 1H), 8.22 (d, J=8.8 Hz, 1H), 8.09 (d, J=3.2 Hz, 1H), 7.91 (d, J=8.4 Hz, 1H), 7.54 (d, J=8.0 Hz, 2H), 7.40 (d, J=8.4 Hz, 2H), 7.09 (br d, J=7.6 Hz, 1H), 6.61 (s, 2H), 6.40 (dd, J=7.6, 4.8 Hz, 1H), 5.24 (s, 2H), 2.50 (s, 3H), 2.18 (s, 3H)

Step 2: (4-(2-(2-Aminopyridin-3-yl)-5-(3-methyl-1H-1,2,4-triazol-1-yl)-3H-imidazo[4,5-b]pyridin-3-yl)phenyl)methanol To a solution of 4-(2-(2-aminopyridin-3-yl)-5-(3-methyl-1H-1,2,4-triazol-1-yl)-3H-imidazo[4,5-b]pyridin-3-yl)benzyl acetate (200 mg, 454 μmol) in THF (2 mL), MeOH (2 mL) and H₂O (1 mL) was added K₂CO₃ (188 mg, 1.36 mmol). The mixture was stirred at 25° C. for 1 hr. The reaction mixture was diluted with H₂O (50 mL) and extracted with EtOAc (50 mL×2). The combined organic layers were washed with brine (100 mL), dried over Na₂SO₄, filtered and concentrated under reduced pressure. (4-(2-(2-Aminopyridin-3-yl)-5-(3-methyl-1H-1,2,4-triazol-1-yl)-3H-imidazo[4,5-b]pyridin-3-yl)phenyl)methanol (150 mg) was obtained as a light yellow solid. MS: m/z=399.2 [M+H]⁺.

Step 3: 3-(3-(4-(Chloromethyl)phenyl)-5-(3-methyl-1H-1,2,4-triazol-1-yl)-3H-imidazo[4,5-b]pyridin-2-yl)pyridin-2-amine To a solution of (4-(2-(2-aminopyridin-3-yl)-5-(3-methyl-1H-1,2,4-triazol-1-yl)-3H-imidazo[4,5-b]pyridin-3-yl)phenyl)methanol (150 mg, 376 μmol) in CH$_2$Cl$_2$ (3 mL) was added SOCl$_2$ (0.1 mL). The mixture was stirred at 40° C. for 0.5 hr. The reaction was concentrated under reduced pressure to give 3-(3-(4-(chloromethyl)phenyl)-5-(3-methyl-1H-1,2,4-triazol-1-yl)-3H-imidazo[4,5-b]pyridin-2-yl)pyridin-2-amine (Intermediate 252, 150 mg HCl salt) as a light yellow solid. MS: m/z=417.2, 419.2 [M+H]$^+$.

Intermediate 253: 3-(3-(4-(Chloromethyl)phenyl)-5-(1H-1,2,4-triazol-1-yl)-3H-imidazo[4,5-b]pyridin-2-yl)pyridin-2-amine

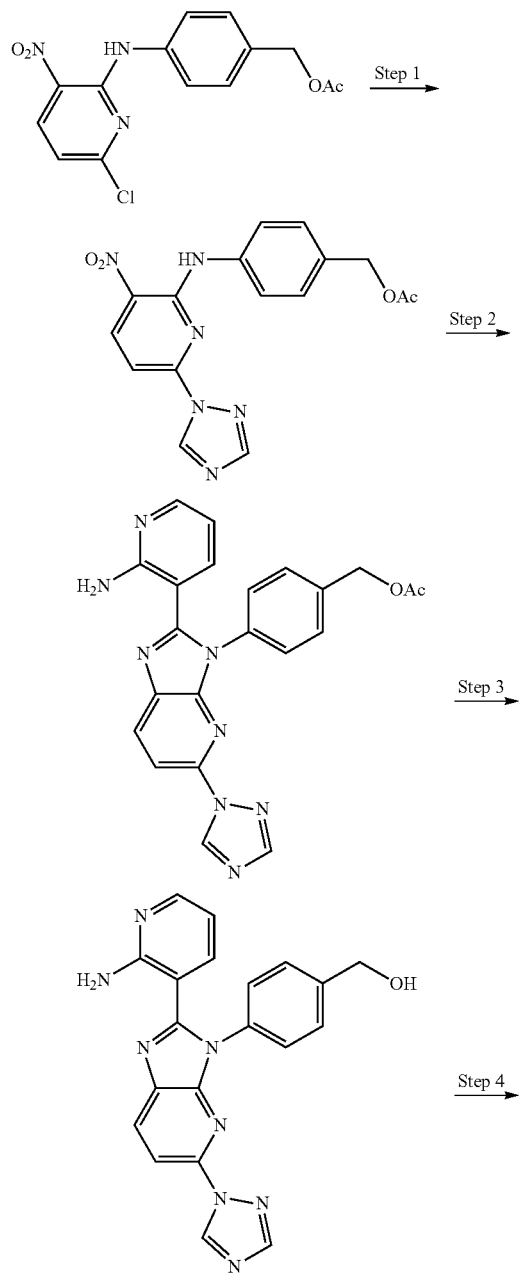

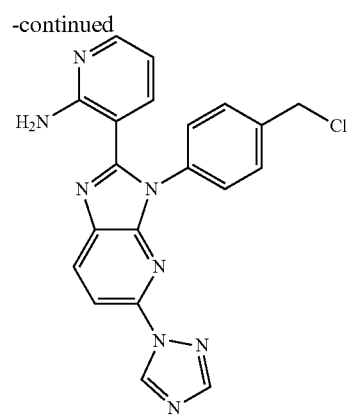

Intermediate 253

Step 1: 4-((3-Nitro-6-(1H-1,2,4-triazol-1-yl)pyridin-2-yl)amino)benzyl acetate To a solution of 4-((6-chloro-3-nitropyridin-2-yl)amino)benzyl acetate (refer to Intermediate 178 for detail procedures, 2 g, 6.22 mmol) and 4H-1,2,4-triazole (429 mg, 6.22 mmol) in DMF (30 mL) were added K$_2$CO$_3$ (4.30 g, 31.1 mmol) and NaI (93.2 mg, 622 μmol). The mixture was stirred at 80° C. for 1 hr. The reaction mixture was quenched with H$_2$O (500 mL) at 25° C., diluted with CH$_2$Cl$_2$ (500 mL), and extracted with CH$_2$Cl$_2$ (500 mL×2). The combined organic layers were washed with brine (300 mL×3), dried over Na$_2$SO$_4$, filtered and concentrated under reduced pressure. After purified by silica gel flash chromatography (Eluent of 0%~25% EtOAc in petroleum ether), 4-((3-nitro-6-(1H-1,2,4-triazol-1-yl)pyridin-2-yl)amino)benzyl acetate (1.1 g, yield: 48%) was obtained as a light yellow solid. MS: m/z=377.0 [M+Na]$^+$. $^1$H NMR (400 MHz, Chloroform-d) δ 10.27 (s, 1H), 8.97 (s, 1H), 8.75 (d, J=8.8 Hz, 1H), 8.12 (s, 1H), 7.58 (d, J=8.4 Hz, 2H), 7.44 (dd, J=9.6, 8.8 Hz, 3H), 5.15 (s, 2H), 2.15 (s, 3H).

Step 2: 4-(2-(2-Aminopyridin-3-yl)-5-(1H-1,2,4-triazol-1-yl)-3H-imidazo[4,5-b]pyridin-3-yl)benzyl acetate To a solution of 4-((3-nitro-6-(1H-1,2,4-triazol-1-yl)pyridin-2-yl)amino)benzyl acetate (1 g, 2.82 mmol) in DMSO (10 mL) were added Na$_2$S$_2$O$_4$ (1.97 g, 11.3 mmol, 88% purity) and 2-aminonicotinaldehyde (414 mg, 3.39 mmol). The mixture was stirred at 100° C. for 6 hr. The reaction mixture was quenched with H$_2$O (50 mL) at 25° C., and then diluted with EtOAc (50 mL) and extracted with EtOAc (50 mL×2). The combined organic layers were washed with brine (50 mL), dried over Na$_2$SO$_4$, filtered and concentrated under reduced pressure. After purified by silica gel flash chromatography (Eluent of 0%~53% EtOAc in petroleum ether), 4-(2-(2-aminopyridin-3-yl)-5-(1H-1,2,4-triazol-1-yl)-3H-imidazo[4,5-b]pyridin-3-yl)benzyl acetate (200 mg, yield: 16%) was obtained as a light yellow solid. MS: m/z=427.1 [M+H]$^+$. $^1$H NMR (400 MHz, Chloroform-d) δ 9.00 (s, 1H), 8.25 (d, J=8.4 Hz, 1H), 8.14-8.06 (m, 2H), 7.97 (d, J=8.4 Hz, 1H), 7.54 (d, J=8.4 Hz, 2H), 7.41 (d, J=8.4 Hz, 2H), 7.10 (d, J=7.6 Hz, 1H), 6.63 (s, 2H), 6.41 (dd, J=7.6, 4.8 Hz, 1H), 5.24 (s, 2H), 2.19 (s, 3H).

Step 3: (4-(2-(2-Aminopyridin-3-yl)-5-(1H-1,2,4-triazol-1-yl)-3H-imidazo[4,5-b]pyridin-3-yl)phenyl)methanol To a solution of 4-(2-(2-aminopyridin-3-yl)-5-(1H-1,2,4-triazol-1-yl)-3H-imidazo[4,5-b]pyridin-3-yl)benzyl acetate (200 mg, 469 μmol) in THF (2 mL), MeOH (2 mL) and H$_2$O (1 mL) was added K$_2$CO$_3$ (194 mg, 1.41 mmol). The mixture was stirred at 25° C. for 1 hr. The reaction mixture was diluted with H$_2$O (50 mL) and extracted with EtOAc (50 mL×2). The combined organic layers were washed with brine (100 mL), dried over Na$_2$SO$_4$, filtered and concentrated under reduced pressure. (4-(2-(2-Aminopyridin-3-yl)-5-(1H-1,2,4-triazol-1-yl)-3H-imidazo[4,5-b]pyridin-3-yl)phenyl)methanol (150 mg) was obtained as a light yellow solid. MS: m/z=385.2 [M+H]$^+$.

Step 4: 3-(3-(4-(Chloromethyl)phenyl)-5-(1H-1,2,4-triazol-1-yl)-3H-imidazo[4,5-b]pyridin-2-yl)pyridin-2-amine To a solution of (4-(2-(2-aminopyridin-3-yl)-5-(1H-1,2,4-triazol-1-yl)-3H-imidazo[4,5-b]pyridin-3-yl)phenyl)methanol (150 mg, 390 μmol) in CH$_2$Cl$_2$ (3 mL) was added SOCl$_2$ (0.1 mL). The mixture was stirred at 40° C. for 0.5 hr. The mixture was concentrated under reduced pressure to give 3-(3-(4-(chloromethyl)phenyl)-5-(1H-1,2,4-triazol-1-yl)-3H-imidazo[4,5-b]pyridin-2-yl)pyridin-2-amine (Intermediate 253, 150 mg, HCl salt) was obtained as a light yellow solid. MS: m/z=403.2, 405.1 [M+H]$^+$.

Intermediate 254 & 255: 4-((3-Nitro-6-(1H-1,2,3-triazol-1-yl)pyridin-2-yl)amino)benzyl acetate & 4-((3-Nitro-6-(2H-1,2,3-triazol-2-yl)pyridin-2-yl)amino)benzyl acetate

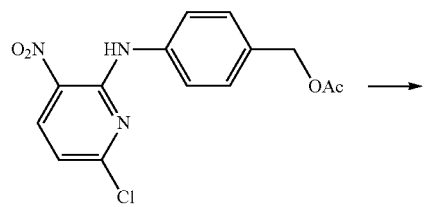

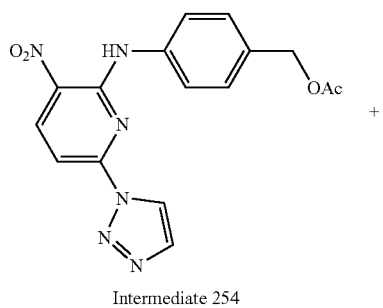

Intermediate 254

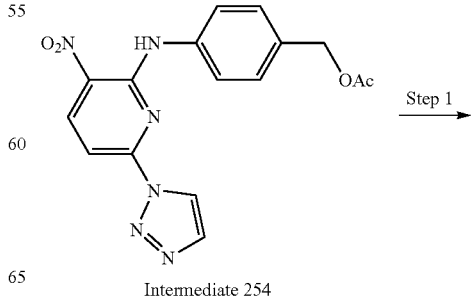

Intermediate 254

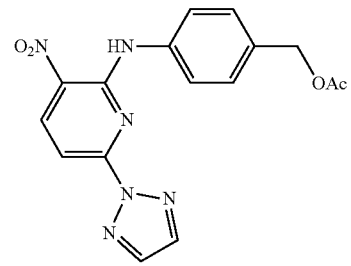

Intermediate 255

To a solution of 4-((6-chloro-3-nitropyridin-2-yl)amino)benzyl acetate (3 g, 9.33 mmol) 1H-1,2,3-triazole (644 mg, 9.33 mmol) in DMSO (30 mL) was added DIEA (4.87 mL, 28.0 mmol). The mixture was degassed and purged with N$_2$ for 3 times and stirred at 100° C. for 2 hr under N$_2$. The reaction mixture was quenched with H$_2$O (100 mL) at 25° C. and extracted with CH$_2$Cl$_2$ (100 mL×2). The combined organic layers were washed with brine (100 mL×3), dried over Na$_2$SO$_4$, filtered, and concentrated under reduced pressure. After purified by prep-HPLC (column: Phenomenex luna C18 (250×70 mm, 15 um); mobile phase: [water (NH$_4$HCO$_3$)-ACN]; gradient: 35%-65% B over 22 min), 4-((3-nitro-6-(1H-1,2,3-triazol-1-yl)pyridin-2-yl)amino)benzyl acetate (Intermediate 254, 360 mg, yield 10%) was obtained as a yellow solid. MS: m/z=355.0 [M+H]$^+$. $^1$H NMR (400 MHz, Chloroform-d) 10.30 (br s, 1H), 8.77 (d, J=8.8 Hz, 1H), 8.38-8.32 (m, 1H), 7.85-7.81 (m, 1H), 7.74 (d, J=8.8 Hz, 1H), 7.58 (d, J=8.0 Hz, 2H), 7.45 (d, J=8.0 Hz, 2H), 5.15 (s, 2H), 2.14 (s, 3H), 4-((3-Nitro-6-(2H-1,2,3-triazol-2-yl)pyridin-2-yl)amino)benzyl acetate (Intermediate 255, 840 mg, yield 24%) was obtained as a red solid. MS: m/z=355.0 [M+H]$^+$. $^1$H NMR (400 MHz, Chloroform-d) 10.52 (br s, 1H), 8.73 (dd, J=9.2, 1.6 Hz, 1H), 8.01-7.93 (m, 4H), 7.59 (dd, J=9.2, 2.0 Hz, 1H), 7.50-7.40 (m, 2H), 5.12 (s, 2H), 2.11 (s, 3H).

Intermediate 256: 3-(3-(4-(Chloromethyl)phenyl)-5-(1H-1,2,3-triazol-1-yl)-3H-imidazo[4,5-b]pyridin-2-yl)pyridin-2-amine Step 1

-continued

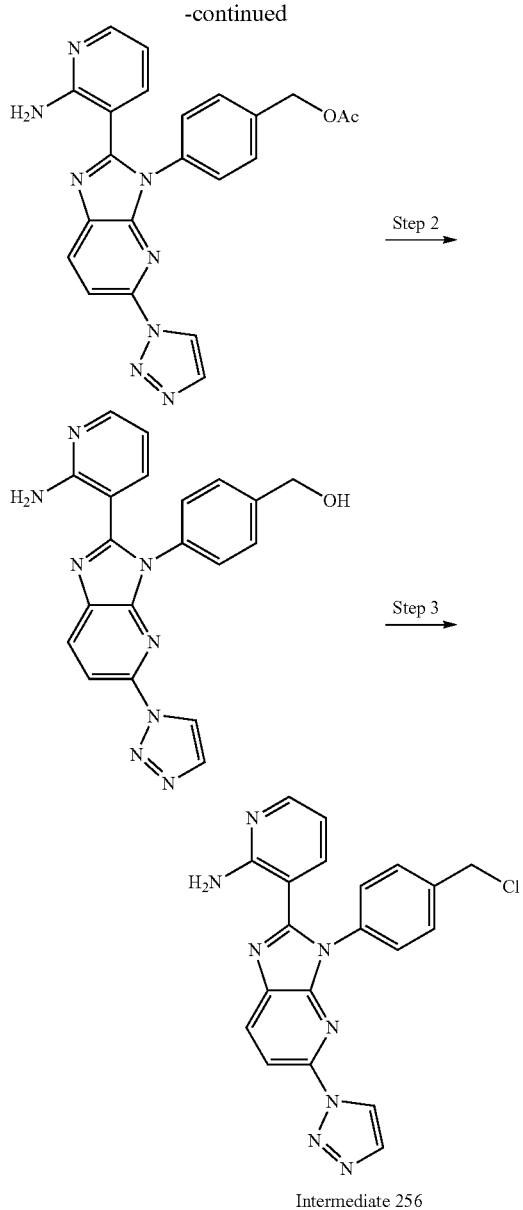

Intermediate 256

Step 1: 4-(2-(2-Aminopyridin-3-yl)-5-(1H-1,2,3-triazol-1-yl)-3H-imidazo[4,5-b]pyridin-3-yl)benzyl acetate To a solution of Intermediate 254 (300 mg, 847 µmol) in DMSO (5 mL) were added Na$_2$S$_2$O$_4$ (442 mg, 2.54 mmol) and 2-aminonicotinaldehyde (114 mg, 931 µmol). The mixture was degassed and purged with N$_2$ for 3 times and stirred at 100° C. for 16 hr under N$_2$. The reaction mixture was poured into H$_2$O (50 mL). The mixture was extracted with CH$_2$Cl$_2$ (200 mL×2). The combined organic layers were washed with brine (100 mL×3), dried over Na$_2$SO$_4$, filtered and concentrated under reduced pressure. After purified by silica gel flash chromatography (Ethyl acetate in petroleum ether=50% to 80%), 4-(2-(2-aminopyridin-3-yl)-5-(1H-1,2,3-triazol-1-yl)-3H-imidazo[4,5-b]pyridin-3-yl)benzyl acetate (51 mg, yield 13%) was obtained as an orange solid. MS: m/z=427.1 [M+H]$^+$. $^1$H NMR (400 MHz, Chloroform-d) δ 8.44 (s, 1H), 8.28 (d, J=2.8 Hz, 2H), 8.16-8.05 (m, 1H), 7.78 (d, J=1.6 Hz, 1H), 7.58-7.48 (m, 2H), 7.45-7.36 (m, 2H), 7.09 (d, J=7.6 Hz, 1H), 6.62 (br s, 2H), 6.45-6.35 (m, 1H), 5.24 (s, 2H), 2.18 (s, 3H).

Step 2: (4-(2-(2-Aminopyridin-3-yl)-5-(1H-1,2,3-triazol-1-yl)-3H-imidazo[4,5-b]pyridin-3-yl)phenyl)methanol To a solution of 4-(2-(2-aminopyridin-3-yl)-5-(1H-1,2,3-triazol-1-yl)-3H-imidazo[4,5-b]pyridin-3-yl)benzyl acetate (51 mg, 120 gmol) in THF (0.5 mL), H$_2$O (0.5 mL), and MeOH (0.5 mL) was added K$_2$CO$_3$ (33.1 mg, 239 µmol). The mixture was degassed and purged with N$_2$ for 3 times and stirred at 25° C. for 0.5 hr under N$_2$. The reaction mixture was filtered and concentrated under reduced pressure. (4-(2-(2-Aminopyridin-3-yl)-5-(1H-1,2,3-triazol-1-yl)-3H-imidazo[4,5-b]pyridin-3-yl)phenyl)methanol (46.0 mg, crude) was obtained as a yellow solid which was used into the next step directly. MS: m/z=385.2 [M+H]$^+$.

Step 3: 3-(3-(4-(Chloromethyl)phenyl)-5-(1H-1,2,3-triazol-1-yl)-3H-imidazo[4,5-b]pyridin-2-yl)pyridin-2-amine To a solution of (4-(2-(2-aminopyridin-3-yl)-5-(1H-1,2,3-triazol-1-yl)-3H-imidazo[4,5-b]pyridin-3-yl)phenyl)methanol (46.0 mg, 120 µmol) in CH$_2$Cl$_2$ (1 mL) was added SOCl$_2$ (142 mg, 1.20 mmol). The mixture was stirred at 25° C. for 0.5 hr. The reaction mixture was concentrated under reduced pressure to give 3-(3-(4-(chloromethyl)phenyl)-5-(1H-1,2,3-triazol-1-yl)-3H-imidazo[4,5-b]pyridin-2-yl)pyridin-2-amine (Intermediate 256, 48.2 mg, crude, HCl) as a yellow solid, which was used in the next step. MS: m/z=403.1 [M+H]$^+$.

Intermediate 257: 3-(3-(4-(Chloromethyl)phenyl)-5-(2H-1,2,3-triazol-2-yl)-3H-imidazo[4,5-b]pyridin-2-yl)pyridin-2-amine

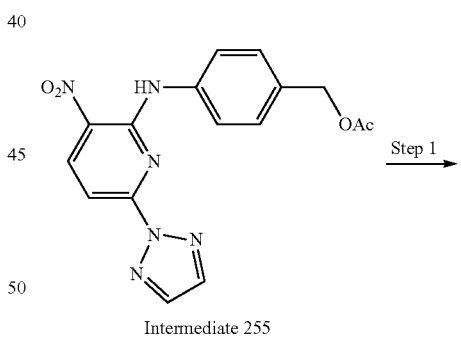

Intermediate 255

Step 1

-continued

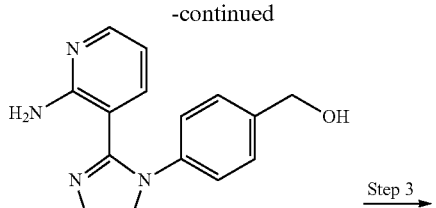

Step 3 →

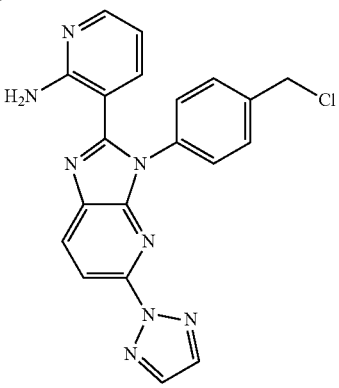

Intermediate 257

Step 1: 4-(2-(2-Aminopyridin-3-yl)-5-(2H-1,2,3-triazol-2-yl)-3H-imidazo[4,5-b]pyridin-3-yl)benzyl acetate To a solution of Intermediate 255 (750 mg, 2.12 mmol) in DMSO (10 mL) were added Na$_2$S$_2$O$_4$ (1.11 g, 6.35 mmol) and 2-aminonicotinaldehyde (284 mg, 2.33 mmol). The mixture was degassed and purged with N$_2$ for 3 times and stirred at 100° C. for 16 hr under N$_2$. The reaction mixture was poured into H$_2$O (50 mL). The mixture was extracted with CH$_2$Cl$_2$ (200 mL×2). The combined organic layers were washed with brine (100 mL×3), dried over Na$_2$SO$_4$, filtered and concentrated under reduced pressure. After purified by silica gel flash chromatography (Ethyl acetate in petroleum ether=50% to 80%), 4-(2-(2-aminopyridin-3-yl)-5-(2H-1,2,3-triazol-2-yl)-3H-imidazo[4,5-b]pyridin-3-yl) benzyl acetate (102 mg, yield 9.7%) was obtained as an orange solid. MS: m/z=449.1 [M+Na]$^+$. $^1$H NMR (400 MHz, Chloroform-d) δ 8.30-8.21 (m, 1H), 8.17-8.05 (m, 2H), 7.88 (d, J=1.6 Hz, 2H), 7.58-7.39 (m, 4H), 7.11-7.02 (m, 1H), 6.57 (brs, 2H), 6.46-6.35 (m, 1H), 5.19 (s, 2H), 2.16 (s, 3H).

Step 2: (4-(2-(2-Aminopyridin-3-yl)-5-(2H-1,2,3-triazol-2-yl)-3H-imidazo[4,5-b]pyridin-3-yl)phenyl)methanol To a solution of 4-(2-(2-aminopyridin-3-yl)-5-(2H-1,2,3-triazol-2-yl)-3H-imidazo[4,5-b]pyridin-3-yl)benzyl acetate (100 mg, 235 μmol) in THF (1 mL), H$_2$O (1 mL), and MeOH (1 mL) was added K$_2$CO$_3$ (64.8 mg, 469 μmol). The mixture was degassed and purged with N$_2$ for 3 times and stirred at 25° C. for 0.5 hr under N$_2$. The reaction mixture was filtered and concentrated under reduced pressure to give (4-(2-(2-aminopyridin-3-yl)-5-(2H-1,2,3-triazol-2-yl)-3H-imidazo[4,5-b]pyridin-3-yl)phenyl)methanol (90.1 mg, crude) as a yellow solid, which was used in the next step directly. MS: m/z=385.1 [M+H]$^+$.

Step 3: 3-(3-(4-(Chloromethyl)phenyl)-5-(2H-1,2,3-triazol-2-yl)-3H-imidazo[4,5-b]pyridin-2-yl)pyridin-2-amine To a solution of (4-(2-(2-aminopyridin-3-yl)-5-(2H-1,2,3-triazol-2-yl)-3H-imidazo[4,5-b]pyridin-3-yl)phenyl)methanol (90.1 mg, 235 μmol) in CH$_2$Cl$_2$ (1 mL) was added SOCl$_2$ (279 mg, 2.34 mmol). The mixture was degassed and purged with N$_2$ for 3 times and stirred at 25° C. for 0.5 hr under N$_2$. The reaction mixture was concentrated under reduced pressure to give 3-(3-(4-(chloromethyl)phenyl)-5-(2H-1,2,3-triazol-2-yl)-3H-imidazo[4,5-b]pyridin-2-yl)pyridin-2-amine (Intermediate 257, 103 mg, crude, HCl) as a yellow solid which was used into the next step directly. MS: m/z=403.1 [M+H]$^+$.

Intermediate 258 & 259: 4-((6-(4-Methyl-1H-1,2,3-triazol-1-yl)-3-nitropyridin-2-yl)amino)benzyl acetate & 4-((6-(4-Methyl-2H-1,2,3-triazol-2-yl)-3-nitropyridin-2-yl)amino)benzyl acetate

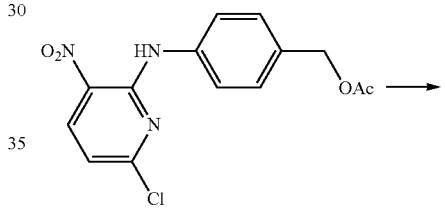

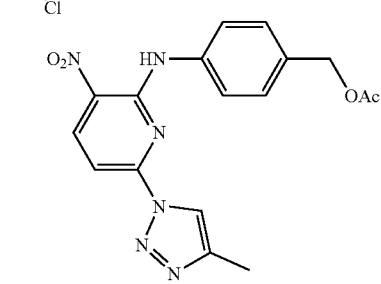

Intermediate 258

+

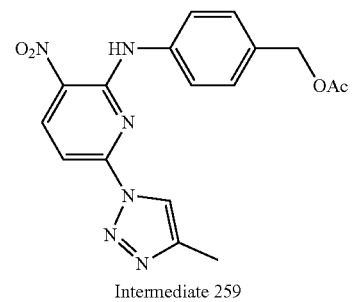

Intermediate 259

To a solution of 4-((6-chloro-3-nitropyridin-2-yl)amino) benzyl acetate (refer to Intermediate 178 for detail procedures, 3 g, 9.33 mmol) and 4-methyl-1H-1,2,3-triazole (775 mg, 9.33 mmol) in DMSO (20 mL) was added DIEA (3.62 g, 28 mmol). The mixture was stirred at 80° C. for 16 hr. The reaction mixture was quenched with H$_2$O (100 mL) at 25° C.

and extracted with CH₂Cl₂ (100 mL×2). The combined organic layers were washed with brine (100 mL×3), dried over Na₂SO₄, filtered and concentrated under reduced pressure. After purified by prep-HPLC (column: Phenomenex C₁₈ 150×25 mm×10 μm; mobile phase: [water (NH₄HCO₃)-ACN]; gradient: 35%-65% B over 22 min), 4-((6-(4-methyl-1H-1,2,3-triazol-1-yl)-3-nitropyridin-2-yl)amino)benzyl acetate (Intermediate 258, 720 mg, yield: 20%) was obtained as a red solid. MS: m/z=391.2 [M+Na]⁺. ¹H NMR (400 MHz, Dimethylsulfoxide-d₆) δ 10.27 (s, 1H), 8.78 (d, J=8.8 Hz, 1H), 8.23-8.21 (m, 1H), 7.70 (d, J=8.4 Hz, 2H), 7.58 (d, J=8.8 Hz, 1H), 7.45 (d, J=8.4 Hz, 2H), 5.10 (s, 2H), 2.36 (s, 3H), 2.09 (s, 3H), 4-((6-(4-Methyl-2H-1,2,3-triazol-2-yl)-3-nitropyridin-2-yl)amino)benzyl acetate (Intermediate 259, 1.4 g, yield: 39%) was obtained as a red solid. MS: m/z=369.1 [M+Na]⁺. ¹H NMR (400 MHz, Dimethylsulfoxide-d₆) δ 10.30 (s, 1H), 8.71 (d, J=9.2 Hz, 1H), 8.1 (s, 1H), 7.96 (d, J=8.4 Hz, 2H), 7.46 (d, J=8.8 Hz, 1H), 7.38 (d, J=8.4 Hz, 2H), 5.07 (s, 2H), 2.36 (s, 3H), 2.07 (s, 3H).

Intermediate 260: 3-(3-(4-(Chloromethyl)phenyl)-5-(4-methyl-1H-1,2,3-triazol-1-yl)-3H-imidazo[4,5-b]pyridin-2-yl)pyridin-2-amine

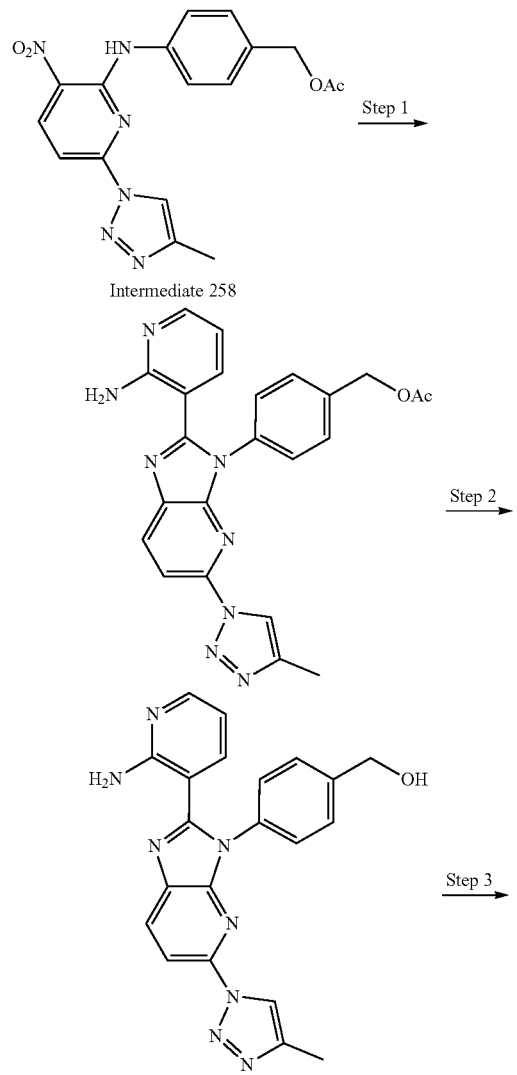

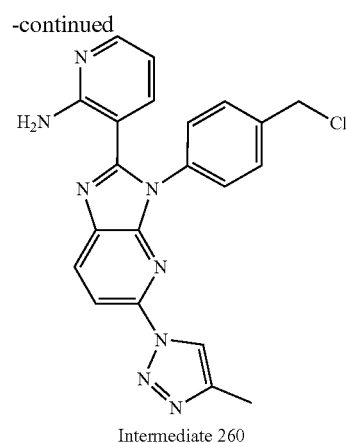

Intermediate 260

Step 1: 4-(2-(2-Aminopyridin-3-yl)-5-(4-methyl-1H-1,2,3-triazol-1-yl)-3H-imidazo[4,5-b]pyridin-3-yl)benzyl acetate To a solution of Intermediate 258 (650 mg, 1.7 mmol) in DMSO (10 mL) were added 2-aminonicotinaldehyde (258 mg, 2.0 mmol) and Na₂S₂O₄ (1.2 g, 7.0 mmol) at 25° C. The mixture was stirred at 100° C. for 16 hr. The reaction mixture was poured into H₂O (50 mL) and extracted with CH₂Cl₂ (200 mL×2). The combined organic layers were washed with brine (400 mL), dried over anhydrous Na₂SO₄, filtered and concentrated. After purified by silica gel flash chromatography (Eluent of 1%~3% MeOH in CH₂Cl₂), 4-(2-(2-aminopyridin-3-yl)-5-(4-methyl-1H-1,2,3-triazol-1-yl)-3H-imidazo[4,5-b]pyridin-3-yl)benzyl acetate (720 mg, yield: 61%) was obtained as a yellow solid. MS: m/z=441.0 [M+H]⁺. ¹H NMR (400 MHz, Dimethylsulfoxide-d₆) δ 8.47 (d, J=8.4 Hz, 1H), 8.35 (s, 11H), 8.08 (d, J=8.4 Hz, 1H), 8.01 (d, J=4.0 Hz, 1H), 7.55-7.50 (m, 4H), 7.26 (d, J=7.6 Hz, 1H), 6.81 (br s, 2H), 6.48-6.42 (m, 1H), 5.17 (s, 2H), 2.32 (s, 3H), 2.12 (s, 3H)

Step 2: (4-(2-(2-Aminopyridin-3-yl)-5-(4-methyl-1H-1,2,3-triazol-1-yl)-3H-imidazo[4,5-b]pyridin-3-yl)phenyl)methanol To a solution of 4-(2-(2-aminopyridin-3-yl)-5-(4-methyl-1H-1,2,3-triazol-1-yl)-3H-imidazo[4,5-b]pyridin-3-yl)benzyl acetate (200 mg, 454 μmol) in MeOH (5 mL), H₂O (1 mL) and THF (5 mL) was added K₂CO₃ (125 mg, 908 μmol). The mixture was stirred at 25° C. for 1 hr. The reaction mixture was quenched with H₂O (20 mL) at 25° C. and extracted with CH₂Cl₂ (15 mL×2). The combined organic layers were washed with brine (30 mL×2), dried over Na₂SO₄, filtered and concentrated under reduced pressure. (4-(2-(2-Aminopyridin-3-yl)-5-(4-methyl-1H-1,2,3-triazol-1-yl)-3H-imidazo[4,5-b]pyridin-3-yl)phenyl)methanol (180 mg, crude) was obtained as a yellow solid. MS: m/z=399.0 [M+H]⁺.

Step 3: 3-(3-(4-(Chloromethyl)phenyl)-5-(4-methyl-1H-1,2,3-triazol-1-yl)-3H-imidazo[4,5-b]pyridin-2-yl)pyridin-2-amine To a solution of (4-(2-(2-aminopyridin-3-yl)-5-(4-methyl-1H-1,2,3-triazol-1-yl)-3H-imidazo[4,5-b]pyridin-3-yl)phenyl)methanol (132 mg, 331 μmol) in CH₂Cl₂ (2 mL) was added SOCl₂ (1 mL). The mixture was stirred at 25° C. for 0.5 hr. The reaction mixture was concentrated under reduced pressure to give 3-(3-(4-(chloromethyl)phenyl)-5-(4-methyl-1H-1,2,3-triazol-1-yl)-3H-imidazo[4,5-b]pyridin-2-yl)pyridin-2-amine (Intermediate 260, 146 mg HCl salt) was obtained as a gray solid. MS: m/z=417.1, 419.1 [M+H]⁺.

Intermediate 261: 3-(3-(4-(Chloromethyl)phenyl)-5-(oxazol-4-yl)-3H-imidazo[4,5-b]pyridin-2-yl)pyridin-2-amine

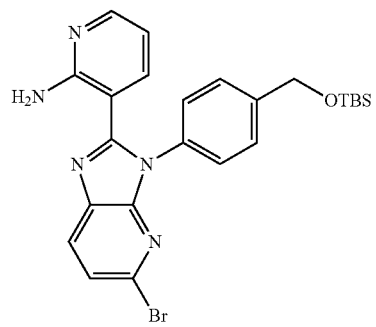

Intermediate 129

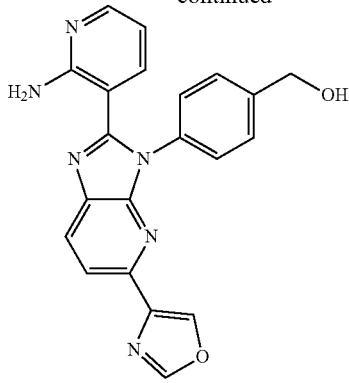

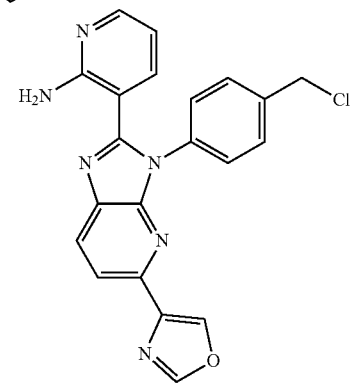

Intermediate 261

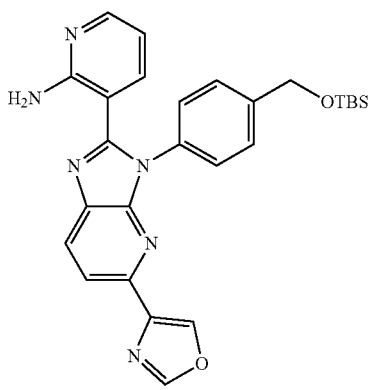

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (500 mg, 979 μmol), 4,4,4',4',5,5,5',5'-octamethyl-2,2'-bi(1,3,2-dioxaborolane) (498 mg, 1.96 mmol), KOAc (288 mg, 2.94 mmol) and Pd(dppf)Cl₂ (71.7 mg, 97.9 μmol) in 1,4-dioxane (5 mL) was degassed and purged with N₂ three times. The mixture was stirred at 90° C. for 8 hr under N₂ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used for next step directly and without work-up and purification. MS: m/z=476.2 [M+H]⁺.

Step 2: 3-(3-(4-(((tert-Butyldimethylsilyl)oxy)methyl)phenyl)-5-(oxazol-4-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (466 mg, 980 μmol), 4-bromooxazole (145 mg, 980 μmol), Pd(dppf)Cl₂ (71.7 mg, 98 μmol) and Cs₂CO₃ (958 mg, 2.94 mmol) in 1,4-dioxane (5 mL) and H₂O (1 mL) was degassed and purged with N₂ three times. The mixture was stirred at 90° C. for 16 hr under N₂ atmosphere. The reaction mixture was quenched with H₂O (5 mL) and extracted with CH₂Cl₂ (15 mL×2). The combined organic layers were washed with brine (30 mL), dried over Na₂SO₄, filtered and concentrated under reduced pressure. After purified by silica gel flash chromatography (Eluent of 30%~60% EtOAc in petroleum ether), 3-(3-(4-

(((tert-butyldimethylsilyl)oxy)methyl)phenyl)-5-(oxazol-4-yl)-3H-imidazo[4,5-b]pyridin-2-yl)pyridin-2-amine (150 mg, yield: 31% for two steps) was obtained as a black solid. MS: m/z=499.3 [M+H]$^+$. $^1$H NMR (400 MHz, Chloroform-d) δ 8.17-7.90 (m, 4H), 7.54-7.44 (m, 2H), 7.39-7.33 (m, 2H), 7.16-7.06 (m, 1H), 6.67-6.65 (m, 2H), 6.36 (dd, J=7.6, 4.8 Hz, 1H), 4.92-4.81 (m, 2H), 1.02-0.95 (m, 9H), 0.24-0.04 (m, 6H).

Step 3: (4-(2-(2-Aminopyridin-3-yl)-5-(oxazol-4-yl)-3H-imidazo[4,5-b]pyridin-3-yl)phenyl)methanol To a solution of 3-(3-(4-(((tert-butyldimethylsilyl)oxy)methyl)phenyl)-5-(oxazol-4-yl)-3H-imidazo[4,5-b]pyridin-2-yl)pyridin-2-amine (150 mg, 301 μmol) in THF (5 mL) was added TBAF (236 mg, 1 M in THF). The mixture was stirred at 25° C. for 1 hr. The reaction mixture was quenched with H$_2$O (5 mL) at 25° C. and extracted with EtOAc (15 mL×3). The combined organic layers were washed with brine (50 mL×3), dried over Na$_2$SO$_4$, filtered and concentrated under reduced pressure. (4-(2-(2-Aminopyridin-3-yl)-5-(oxazol-4-yl)-3H-imidazo[4,5-b]pyridin-3-yl)phenyl)methanol (130 mg) was obtained as a brown solid. MS: m/z=385.1 [M+H]$^+$.

Step 4: 3-(3-(4-(Chloromethyl)phenyl)-5-(oxazol-4-yl)-3H-imidazo[4,5-b]pyridin-2-yl)pyridin-2-amine To a solution of (4-(2-(2-aminopyridin-3-yl)-5-(oxazol-4-yl)-3H-imidazo[4,5-b]pyridin-3-yl)phenyl)methanol (120 mg, 312 μmol) in CH$_2$Cl$_2$ (5 mL) was added SOCl$_2$ (112 mg, 937 μmol). The mixture was stirred at 40° C. for 0.5 hr. The reaction was concentrated under reduced pressure to give 3-(3-(4-(chloromethyl)phenyl)-5-(oxazol-4-yl)-3H-imidazo[4,5-b]pyridin-2-yl)pyridin-2-amine (Intermediate 261, 122 mg, HCl salt) as a yellow solid. MS: m/z=403.0 [M+H]$^+$.

Intermediate 262: 3-(3-(4-(Chloromethyl)phenyl)-5-(4-fluoropyridin-3-yl)-3H-imidazo[4,5-b]pyridin-2-yl)pyridin-2-amine

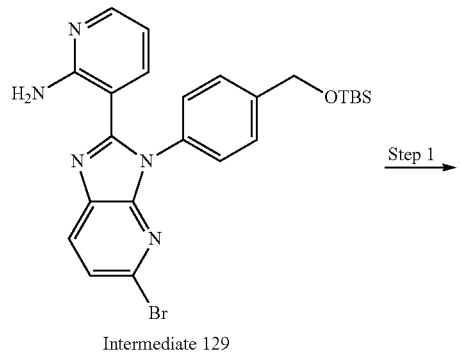

Intermediate 129

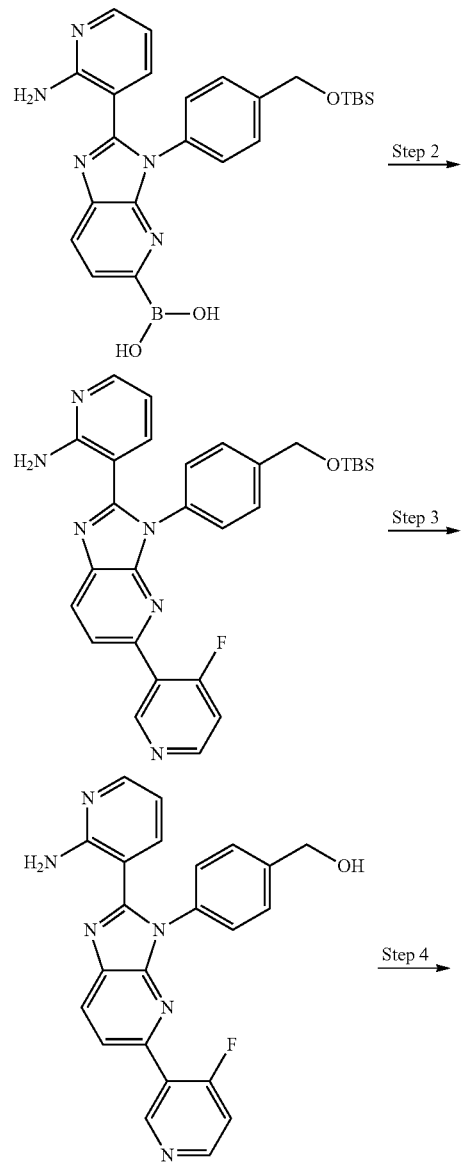

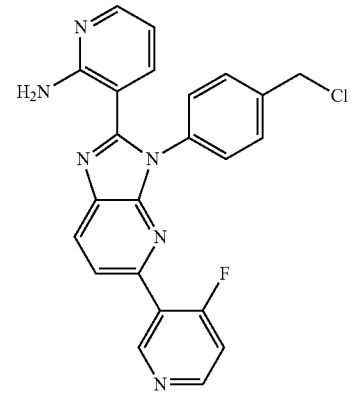

Intermediate 262

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid To a solution of Intermediate 129 (500 mg, 979 µmol) in 1,4-dioxane (6 mL) were added 4,4,4',4',5,5,5',5'-octamethyl-2,2'-bi(1,3,2-dioxaborolane) (497 mg, 2.0 mmol), KOAc (288 mg, 2.9 mmol) and Pd(dppf)Cl$_2$ (71.7 mg, 97.9 µmol). The reaction mixture was stirred at 85° C. for 2 hr under N$_2$. (2-(2-Aminopyridin-3-yl)-3-(4-(((tert-butyldimethylsilyl)oxy)methyl)phenyl)-3H-imidazo[4,5-b]pyridin-5-yl)boronic acid (466 mg, 979 µmol, crude) was obtained as brown liquid and used to the next step without further purification. MS: m/z=476.2 [M+H]$^+$.

Step 2: 3-(3-(4-(((Tert-butyldimethylsilyl)oxy)methyl)phenyl)-5-(4-fluoropyridin-3-yl)-3H-imidazo[4,5-b]pyridin-2-yl)pyridin-2-amine To a solution of (2-(2-aminopyridin-3-yl)-3-(4-(((tert-butyldimethylsilyl)oxy)methyl)phenyl)-3H-imidazo[4,5-b]pyridin-5-yl)boronic acid (512 mg, 1.1 mmol) in 1,4-dioxane (5 mL) and H$_2$O (1 mL) were added 3-bromo-4-fluoropyridine (227 mg, 1.3 mmol), Cs$_2$CO$_3$ (1.1 g, 3.2 mmol), and Pd(dppf)Cl$_2$ (78.8 mg, 108 µmol). The reaction mixture was stirred at 100° C. for 2 hr under N$_2$. The mixture was diluted with H$_2$O (10 mL) and extracted with EtOAc (6 mL×2). The combined organic layers were washed with brine (10 mL), dried over anhydrous Na$_2$SO$_4$, filtered and concentrated. After purified by silica gel flash chromatography (Eluent of 0~51% EtOAc in petroleum ether), 3-(3-(4-(((tert-butyldimethylsilyl)oxy)methyl)phenyl)-5-(4-fluoropyridin-3-yl)-3H-imidazo[4,5-b]pyridin-2-yl)pyridin-2-amine (567 mg, yield: 97.7%) was obtained as a black solid. MS: m/z=527.2 [M+H]$^+$. $^1$H NMR (400 MHz, Chloroform-d) δ 9.20 (d, J=10.4 Hz, 1H), 8.54 (dd, J=7.2, 5.6 Hz, 1H), 8.16 (d, J=8.4 Hz, 1H), 8.07 (dd, J=4.8, 1.6 Hz, 1H), 7.84 (dd, J=8.4, 1.6 Hz, 1H), 7.49 (d, J=8.4 Hz, 2H), 7.38 (d, J=8.4 Hz, 2H), 7.15 (dd, J=8.0, 2.0 Hz, 1H), 7.11 (dd, J=10.8, 5.2 Hz, 1H), 6.68 (br s, 2H), 6.38 (dd, J=7.6, 4.8 Hz, 1H), 4.85 (s, 2H), 0.97 (s, 9H), 0.14 (s, 6H). $^{19}$F NMR (400 MHz, Dimethylsulfoxide-d$_6$) δ −107.329.

Step 3: (4-(2-(2-Aminopyridin-3-yl)-5-(4-fluoropyridin-3-yl)-3H-imidazo[4,5-b]pyridin-3-yl)phenyl)methanol To a solution of 3-(3-(4-(((tert-butyldimethylsilyl)oxy)methyl)phenyl)-5-(4-fluoropyridin-3-yl)-3H-imidazo[4,5-b]pyridin-2-yl)pyridin-2-amine (350 mg, 665 µmol) in THF (4 mL) was added TBAF (1 M in THF, 1.06 mL). The mixture was stirred at 25° C. for 1 hr under N$_2$. The mixture was diluted with H$_2$O (10 mL) was added to the mixture, the aqueous layer was extracted with EtOAc (5 mL×3). The combined organic phase was washed with brine (20 mL), dried over anhydrous Na$_2$SO$_4$, filtered and concentrated. (4-(2-(2-Aminopyridin-3-yl)-5-(4-fluoropyridin-3-yl)-3H-imidazo[4,5-b]pyridin-3-yl)phenyl)methanol (274 mg, 665 µmol, crude) was obtained as a brown solid, which was used to the next step without further purification. MS: m/z=413.1 [M+H]$^+$.

Step 4: 3-(3-(4-(Chloromethyl)phenyl)-5-(4-fluoropyridin-3-yl)-3H-imidazo[4,5-b]pyridin-2-yl)pyridin-2-amine To a solution of (4-(2-(2-aminopyridin-3-yl)-5-(4-fluoropyridin-3-yl)-3H-imidazo[4,5-b]pyridin-3-yl)phenyl)methanol (274 mg, 664 µmol) in CH$_2$Cl$_2$ (3 mL) was added SOCl$_2$ (237 mg, 2.0 mmol). The reaction mixture was stirred at 25° C. for 12 hr under N$_2$. The mixture was concentrated to give 3-(3-(4-(chloromethyl)phenyl)-5-(4-fluoropyridin-3-yl)-3H-imidazo[4,5-b]pyridin-2-yl)pyridin-2-amine (Intermediate 262, 286 mg, 664 µmol, crude) as a brown solid, which was used in the next step without further purification. MS: m/z=431.1 [M+H]$^+$.

Intermediate 263: 3-(3-(4-(Chloromethyl)phenyl)-5-(4-methylpyridin-2-yl)-3H-imidazo[4,5-b]pyridin-2-yl)pyridin-2-amine

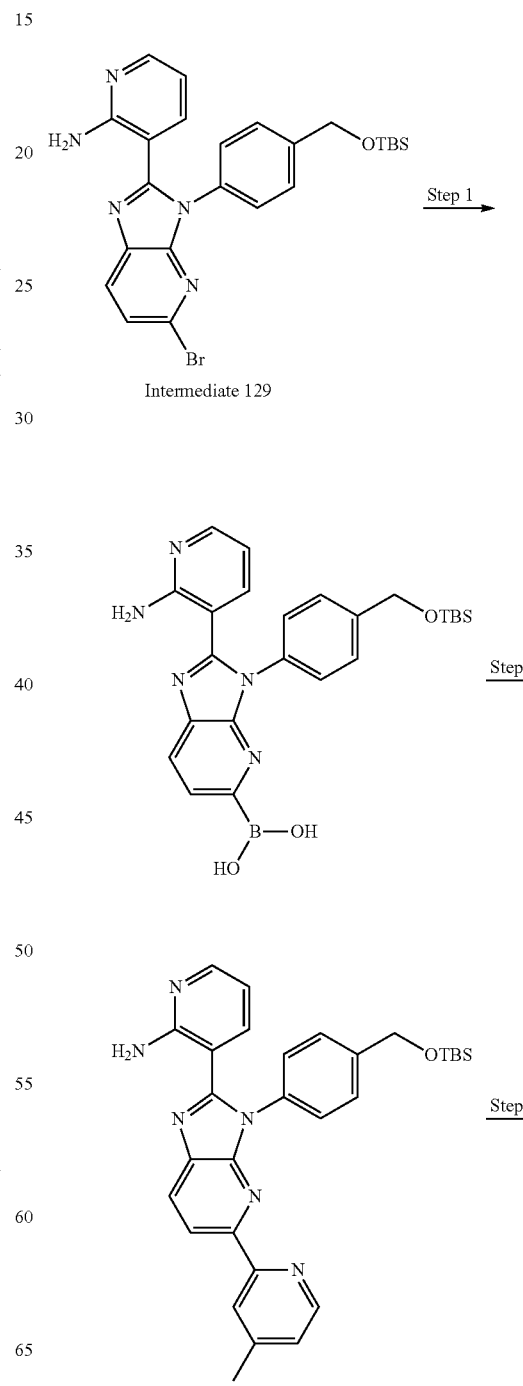

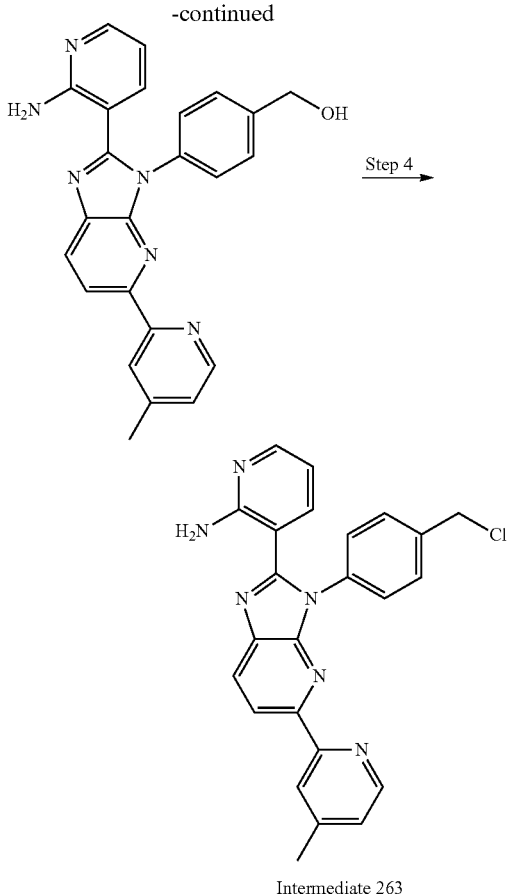

Intermediate 263

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (500 mg, 980 μmol), 4,4,4',4',5,5,5',5'-octamethyl-2,2'-bi(1,3,2-dioxaborolane) (497 mg, 1.96 mmol), KOAc (289 mg, 2.94 mmol) and Pd(dppf)Cl$_2$ (72 mg, 98.0 μmol) in 1,4-dioxane (5 mL) was degassed and purged with N$_2$ three times. The mixture was stirred at 80° C. for 4 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]$^+$.

Step 2: 3-(3-(4-(((Tert-butyldimethylsilyl)oxy)methyl)phenyl)-5-(4-methylpyridin-2-yl)-3H-imidazo[4,5-b]pyridin-2-yl)pyridin-2-amine To a solution of (2-(2-aminopyridin-3-yl)-3-(4-(((tert-butyldimethylsilyl)oxy)methyl)phenyl)-3H-imidazo[4,5-b]pyridin-5-yl)boronic acid (490 mg, 1.03 mmol) and 2-bromo-4-methylpyridine (177 mg, 1.03 mmol) in 1,4-dioxane (10 mL) and H$_2$O (2 mL) were added Pd(dppf)Cl$_2$ (75.4 mg, 103 μmol) and Cs$_2$CO$_3$ (1.01 g, 3.09 mmol) at 25° C. The mixture was degassed and purged with N$_2$ for 3 times and stirred at 100° C. for 2 hr. The mixture was quenched with H$_2$O (20 mL) and the aqueous layer was extracted with EtOAc (20 mL×3). The combined organic layers were washed with brine (20 mL), dried over anhydrous Na$_2$SO$_4$, filtered and concentrated. After purified by silica gel flash chromatography (EtOAc in petroleum ether=0-40%), 3-(3-(4-(((tert-butyldimethylsilyl)oxy)methyl)phenyl)-5-(4-methylpyridin-2-yl)-3H-imidazo[4,5-b]pyridin-2-yl)pyridin-2-amine (350 mg, 670 gmol, yield: 65% for two steps) was obtained as a green solid. MS: m/z=523.3 [M+H]$^+$. $^1$H NMR (400 MHz, Dimethylsulfoxide-d$_6$) δ 8.52 (d, J=4.8 Hz, 1H), 8.46 (d, J=8.4 Hz, 1H), 8.29 (d, J=8.4 Hz, 1H), 7.02-7.99 (m, 1H), 7.99-7.97 (m, 1H), 7.55-7.46 (m, 4H), 7.25-7.17 (m, 2H), 7.04-6.98 (m, 2H), 6.39 (dd, J=7.6, 4.8 Hz, 1H), 4.83 (s, 2H), 2.34 (s, 3H), 0.92 (s, 9H), 0.11 (s, 6H).

Step 3: (4-(2-(2-Aminopyridin-3-yl)-5-(4-methylpyridin-2-yl)-3H-imidazo[4,5-b]pyridin-3-yl)phenyl)methanol To a solution of 3-(3-(4-(((tert-butyldimethylsilyl)oxy)methyl)phenyl)-5-(4-methylpyridin-2-yl)-3H-imidazo[4,5-b]pyridin-2-yl)pyridin-2-amine (320 mg, 612 μmol) in THF (5 mL) was added TBAF (1 M in THF, 1.84 mL) at 25° C. The mixture was stirred at 25° C. for 1 hr. The mixture was quenched with H$_2$O (20 mL) and extracted with EtOAc (20 mL×3). The combined organic layers were washed with brine (20 mL), dried over anhydrous Na$_2$SO$_4$, filtered and concentrated. (4-(2-(2-Aminopyridin-3-yl)-5-(4-methylpyridin-2-yl)-3H-imidazo[4,5-b]pyridin-3-yl)phenyl)methanol (250 mg, 612 μmol) was obtained as a brown solid which was used into the next step directly. MS: m/z=409.2 [M+H]$^+$.

Step 4: 3-(3-(4-(Chloromethyl)phenyl)-5-(4-methylpyridin-2-yl)-3H-imidazo[4,5-b]pyridin-2-yl)pyridin-2-amine To a mixture of (4-(2-(2-aminopyridin-3-yl)-5-(4-methylpyridin-2-yl)-3H-imidazo[4,5-b]pyridin-3-yl)phenyl)methanol (250 mg, 612 μmol) in CH$_2$Cl$_2$ (3 mL) was added SOCl$_2$ (218 mg, 1.84 mmol). The reaction mixture was stirred at 20° C. for 1 hr. The mixture was concentrated under reduced pressure to give 3-(3-(4-(chloromethyl)phenyl)-5-(4-methylpyridin-2-yl)-3H-imidazo[4,5-b]pyridin-2-yl)pyridin-2-amine (Intermediate 263, 261 mg, 611 μmol) as a brown solid. MS: m/z=427.2, 429.2 [M+H]$^+$.

Intermediate 264:
5-bromo-2-(methoxy-d$_3$)pyridine-6-d

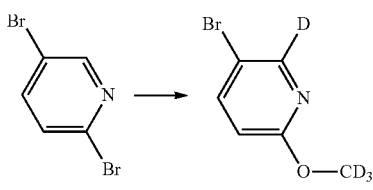

Intermediate 264

To a solution of 2,5-dibromopyridine (1 g, 4.22 mmol) in CD$_3$OD (10 mL) was added NaOH (338 mg, 8.44 mmol). The mixture was stirred at 70° C. for 2 hr. The reaction mixture was quenched with H$_2$O (20 mL) at 25° C. and extracted with CH$_2$Cl$_2$ (25 mL×2). The combined organic layers were washed with brine (30 mL), dried over anhydrous Na$_2$SO$_4$, filtered and concentrated under reduced pressure. After purified by silica gel flash chromatography (Eluent of 0%~1% EtOAc in petroleum ether), 5-bromo-2-(methoxy-d3)pyridine-6-d (Intermediate 264, 600 mg, yield: 74%) was obtained as a colorless oil. MS: m/z=190.9, 192.9 [M+H]⁺. D %: 3D %=66.6%, 4D %=33.4%. ¹H NMR (400 MHz, Dimethylsulfoxide-$d_6$) δ 8.28 (s, 1H), 7.89 (dd, J=9.2, 2.8 Hz, 1H), 6.86-6.79 (m, 1H).

Intermediate 265: 3-(3-(4-(Chloromethyl)phenyl)-5-(6-(methoxy-$d_3$)pyridin-3-yl-2-d)-3H-imidazo[4,5-b]pyridin-2-yl)pyridin-2-amine

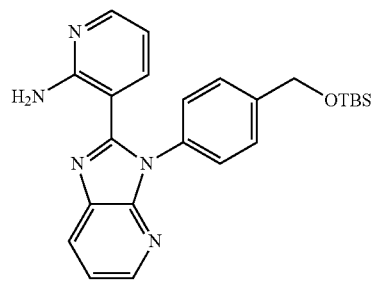

Intermediate 129

Step 1

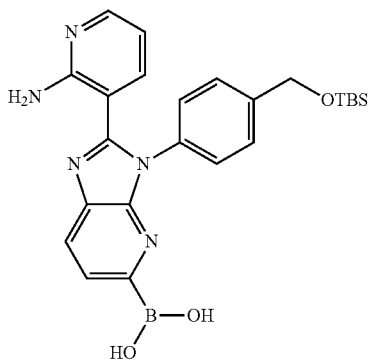

Step 2
Intermediate 264

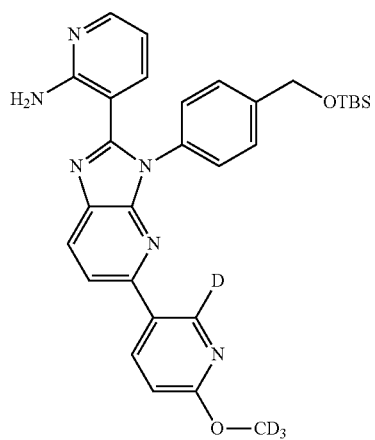

Step 3

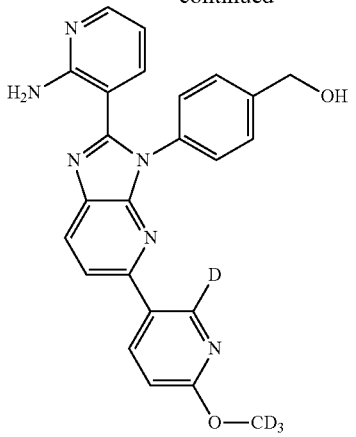

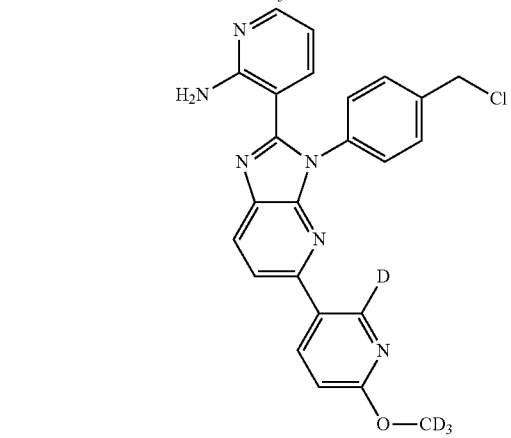

Intermediate 265

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (600 mg, 1.18 mmol), 4,4,4',4',5,5,5',5'-octamethyl-2,2'-bi(1,3,2-dioxaborolane) (448 mg, 1.76 mmol), KOAc (346 mg, 3.53 mmol) and Pd(dppf)Cl₂ (86 mg, 118 μmol) in 1,4-dioxane (6 mL) was degassed and purged with N₂ three times. The mixture was stirred at 90° C. for 3 hr under N₂ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]⁺.

Step 2: 3-(3-(4-(((tert-Butyldimethylsilyl)oxy)methyl)phenyl)-5-(6-(methoxy-$d_3$)pyridin-3-yl-2-d)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (559 mg, 1.18 mmol), Intermediate 264 (225 mg, 1.18 mmol), Cs₂CO₃ (1.15 g, 3.53 mmol) and Pd(dppf)Cl₂ (86 mg, 118 μmol) in 1,4-dioxane (7 mL) and H₂O (1.5 mL) was degassed and purged with N₂ three times. The mixture was stirred at 80° C. for 16 hr under N₂ atmosphere. The reaction mixture was quenched with H₂O (20 mL) and extracted with EtOAc (15 mL×2). The combined organic layers were washed with brine (30 mL), dried over Na₂SO₄, filtered and concentrated under reduced pressure. After purified by silica gel flash chromatography (Eluent of 20%~41% EtOAc in petroleum ether), 3-(3-(4-(((tert-butyldimethylsilyl)oxy)methyl)phenyl)-5-(6-(methoxy-d₃)pyridin-3-yl-2-d)-3H-imidazo[4,5-b]pyridin-2-yl)pyridin-2-amine (350 mg, yield: 49% for two steps) was obtained as a black solid. MS: m z=542.3 [M+H]⁺. D %: 3D %4=68.2%, 4D %=30.4%. ¹H NMR (400 MHz, Chloroform-d) δ 8.84 (s, 1H), 8.27-8.01 (m, 3H), 7.71 (d, J=8.4 Hz, 1H), 7.48 (d, J=8.0 Hz, 2H), 7.38 (d, J=8.4 Hz, 2H), 7.16-7.12 (m, 1H), 6.82-6.75 (m, 1H), 6.65 (br s, 2H), 6.37 (dd, J=8.0, 5.2 Hz, 1H), 4.86 (s, 2H), 0.98 (s, 9H), 0.15 (s, 6H).

Step 3: (4-(2-(2-Aminopyridin-3-yl)-5-(6-(methoxy-d₃)pyridin-3-yl-2-d)-3H-imidazo[4,5-b]pyridin-3-yl)phenyl)methanol To a solution of 3-(3-(4-(((tert-butyldimethylsilyl)oxy)methyl)phenyl)-5-(6-(methoxy-d3)pyridin-3-yl-2-d)-3H-imidazo[4,5-b]pyridin-2-yl)pyridin-2-amine (350 mg, 646 μmol) in THF (3 m L) was added TBAF (507 mg, 1.94 mmol, 1 M in THF). The mixture was stirred at 25° C. for 1 hr. The reaction mixture was quenched with H₂O (20 mL) at 25° C. and extracted with EtOAc (15 mL×2). The combined organic layers were washed with brine (50 mL×3), dried over Na₂SO₄, filtered and concentrated under reduced pressure. After triturated with EtOAc (10 mL) at 25° C. for 10 min, (4-(2-(2-aminopyridin-3-yl)-5-(6-(methoxy-d₃)pyridin-3-yl-2-d)-3H-imidazo[4,5-b]pyridin-3-yl)phenyl)methanol (200 mg, yield: 69%) was obtained as a black solid. MS: m/z=428.2 [M+H]⁺. D %: 3D %=66.4%, 4D %=31.9%. ¹H NMR (400 MHz, Chloroform-d) δ 8.83 (d, J=0.8 Hz, 1H), 8.21 (dd, J=8.4, 2.4 Hz, 1H), 8.12 (d, J=8.4 Hz, 1H), 8.07 (dd, J=4.8, 1.6 Hz, 1H), 7.71 (d, J=8.4 Hz, 1H), 7.56-7.52 (m, 2H), 7.45-7.40 (m, 2H), 7.14 (dd, J=8.0, 1.6 Hz, 1H), 6.90-6.70 (m, 1H), 6.62 (br s, 2H), 6.39 (dd, J=7.6, 4.8 Hz, 1H), 4.83 (s, 2H).

Step 4: 3-(3-(4-(Chloromethyl)phenyl)-5-(6-(methoxy-d₃)pyridin-3-yl-2-d)-3H-imidazo[4,5-b]pyridin-2-yl)pyridin-2-amine To a solution of (4-(2-(2-aminopyridin-3-yl)-5-(6-(methoxy-d₃)pyridin-3-yl-2-d)-3H-imidazo[4,5-b]pyridin-3-yl)phenyl)methanol (200 mg, 468 μmol) in CH₂Cl₂ (5 mL) was added SOCl₂ (167 mg, 1.40 mmol). The mixture was stirred at 25° C. for 1 hr. The reaction was concentrated under reduced pressure to give 3-(3-(4-(chloromethyl)phenyl)-5-(6-(methoxy-d₃)pyridin-3-yl-2-d)-3H-imidazo[4,5-b]pyridin-2-yl)pyridin-2-amine (Intermediate 265, 226 mg, HCl salt) was obtained as a brown solid. MS: m/z=446.1 [M+H]⁺. D %: 3D %=66.8%, 4D %=32.9%. ¹H NMR (400 MHz, Methanol-d₆) δ 9.07 (dd, J=9.2, 2.4 Hz, 1H), 8.97 (s, 1H), 8.42 (d, J=8.4 Hz, 1H), 8.16 (d, J=8.4 Hz, 1H), 8.03 (dd, J=6.0, 1.2 Hz, 1H), 7.87 (dd, J=7.6, 1.6 Hz, 1H), 7.71 (d, J=8.4 Hz, 2H), 7.63-7.58 (m, 3H), 6.87 (dd, J=7.6, 6.4 Hz, 1H), 4.79 (s, 2H).

Intermediate 266: 5-Bromo-2-(methoxy-d₃)pyridine

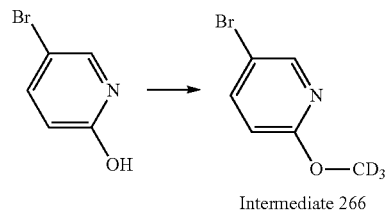 [SMILES: Oc1ccc(Br)cn1 ; [2H]C([2H])([2H])Oc1ccc(Br)cn1]

Intermediate 266

To a solution of 5-bromopyridin-2-ol (1 g, 5.75 mmol) and Ag₂CO₃ (1.11 g, 4.02 mmol) in CH₂Cl₂ (10 mL) was added CD₃I (979 mg, 6.9 mmol). The mixture was stirred at 50° C. for 16 hr. The reaction mixture was quenched with H₂O (50 mL) at 25° C. and extracted with CH₂Cl₂ (50 mL×3). The combined organic layers were washed with brine (50 mL×3), dried over Na₂SO₄, filtered and concentrated under reduced pressure. After purified by silica gel flash chromatography (Eluent of 0%~5% EtOAc in petroleum ether), 5-bromo-2-(methoxy-d₃)pyridine (Intermediate 266, 480 mg, yield: 43%) was obtained as a colorless oil. MS: m/z=190.9, 192.9 [M+H]⁺. 3D %=100%. ¹H NMR (400 MHz, Dimethylsulfoxide-d₆) δ 8.29 (d, J=2.4 Hz, 1H), 7.89 (dd, J=8.8, 2.4 Hz, 1H), 6.84 (d, J=8.8 Hz, 1H).

Intermediate 267: 3-(3-(4-(Chloromethyl)phenyl)-5-(6-(methoxy-d₆)pyridin-3-yl)-3H-imidazo[4,5-b]pyridin-2-yl)pyridin-2-amine

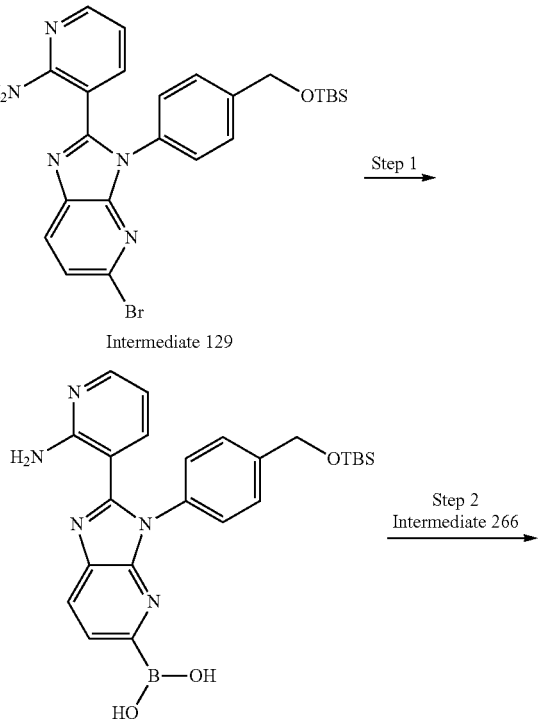

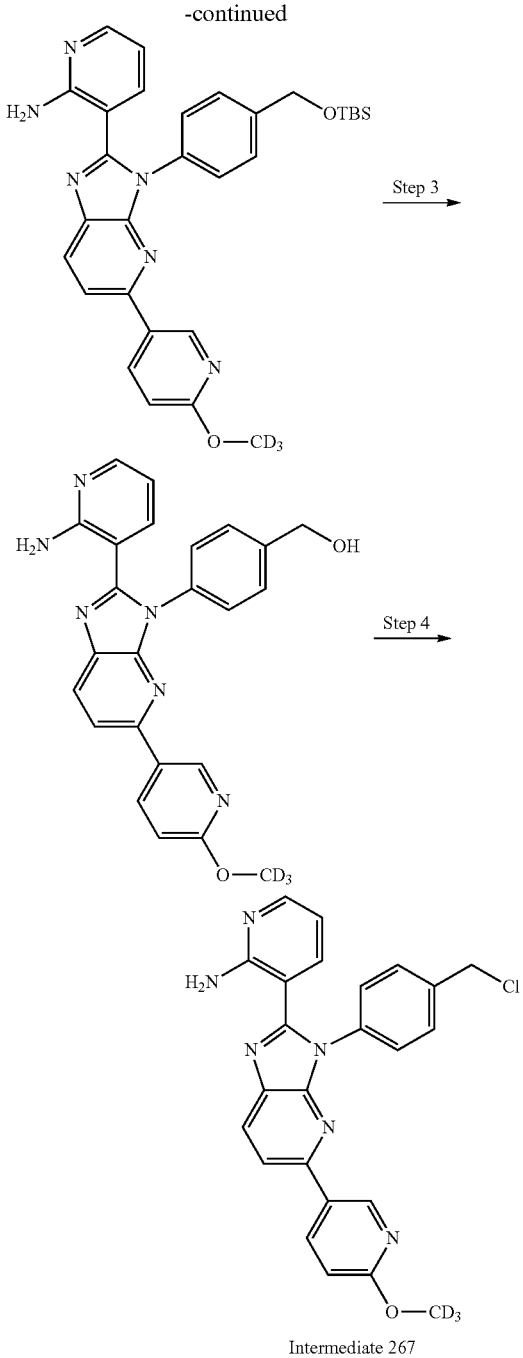

Intermediate 267

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl$_2$ (143 mg, 196 μmol) in 1,4-dioxane (10 mL) was degassed and purged with N$_2$ three times. The mixture was stirred at 80° C. for 4 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((tert-Butyldimethylsilyl)oxy)methyl)phenyl)-5-(6-(methoxy-d$_3$)pyridin-3-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (930 mg, 1.96 mmol), Intermediate 266 (374 mg, 1.96 mmol), Pd(dppf)Cl$_2$ (143 mg, 196 μmol) and Cs$_2$CO$_3$ (1.91 g, 5.87 mmol) in 1,4-dioxane (10 mL) and H$_2$O (2 mL) was degassed and purged with N$_2$ three times. The mixture was stirred at 80° C. for 2 hr under N$_2$ atmosphere. The reaction mixture was quenched with H$_2$O (50 mL) and extracted with CH$_2$Cl$_2$ (50 mL×2). The combined organic layers were washed with brine (50 mL), dried over Na$_2$SO$_4$, filtered and concentrated under reduced pressure.

After purified by silica gel flash chromatography (Eluent of 10%~40% EtOAc in petroleum ether), 3-(3-(4-(((tert-butyldimethylsilyl)oxy)methyl)phenyl)-5-(6-(methoxy-d$_3$)pyridin-3-yl)-3H-imidazo[4,5-b]pyridin-2-yl)pyridin-2-amine (440 mg, yield: 39% for two steps) was obtained as a yellow solid. MS: m/z=542.4 [M+H]$^+$. $^1$H NMR (400 MHz, Dimethylsulfoxide-d$_6$) δ 8.84 (d, J=2.4 Hz, 1H), 8.32-8.19 (m, 2H), 8.03-7.93 (m, 2H), 7.53-7.43 (m, 4H), 7.20-7.17 (m, 1H), 7.03 (s, 2H), 6.89 (d, J=8.8 Hz, 1H), 6.38 (dd, 1=7.6, 4.8 Hz, 1H), 4.82 (s, 2H), 0.92 (s, 9H), 0.10 (s, 6H).

Step 3: (4-(2-(2-Aminopyridin-3-yl)-5-(6-(methoxy-d$_3$)pyridin-3-yl)-3H-imidazo[4,5-b]pyridin-3-yl)phenyl)methanol To a solution of 3-(3-(4-(((tert-butyldimethylsilyl)oxy)methyl)phenyl)-5-(6-(methoxy-d$_3$)pyridin-3-yl)-3H-imidazo[4,5-b]pyridin-2-yl)pyridin-2-amine (440 mg, 812 μmol) in THF (5 mL) was added TBAF (425 mg, 1.62 mmol, 1 M in THF). The mixture was stirred at 25° C. for 1 hr. The reaction mixture was quenched with H$_2$O (20 mL) at 25° C. and extracted with CH$_2$Cl$_2$ (20 mL×3). The combined organic layers were washed with brine (20 mL×3), dried over Na$_2$SO$_4$, filtered and concentrated under reduced pressure. (4-(2-(2-Aminopyridin-3-yl)-5-(6-(methoxy-d$_6$)pyridin-3-yl)-3H-imidazo[4,5-b]pyridin-3-yl)phenyl)methanol 340 mg, yield: 98%) was obtained as a brown solid. MS: m/z=428.2 [M+H]$^+$. $^1$H NMR (400 MHz, Dimethylsulfoxide-d$_6$) δ 8.84 (d, J=2.4 Hz, 1H), 8.33-8.20 (m, 2H), 8.02-7.94 (m, 2H), 7.53-7.41 (m, 4H), 7.21 (dd, J=7.6, 1.6 Hz, 1H), 7.00 (s, 2H), 6.90 (d, J=8.8 Hz, 1H), 6.41 (dd, J=7.6, 4.8 Hz, 1H), 5.36 (t, J=5.6 Hz, 1H), 4.60 (d, J=5.6 Hz, 2H).

Step 4: 3-(3-(4-(Chloromethyl)phenyl)-5-(6-(methoxy-d$_3$)pyridin-3-yl)-3H-imidazo[4,5-b]pyridin-2-yl)pyridin-2-amine To a solution of (4-(2-(2-aminopyridin-3-yl)-5-(6-(methoxy-d$_6$)pyridin-3-yl)-3H-imidazo[4,5-b]pyridin-3-yl)phenyl)methanol (340 mg, 795 μmol) in CH$_2$Cl$_2$ (5 mL) was added SOCl$_2$ (284 mg, 2.39 mmol). The mixture was stirred at 40° C. for 0.5 hr. The reaction was concentrated under reduced pressure to give 3-(3-(4-(chloromethyl)phenyl)-5-(6-(methoxy-d$_3$)pyridin-3-yl)-3H-imidazo[4,5-b]pyridin-2- yl)pyridin-2-amine (Intermediate 267, 380 mg, HCl salt) was obtained as a brown solid. MS: m/z=446.1 [M+H]$^+$.

Intermediate 268: 2-(2-Aminopyridin-3-yl)-3-(4-(bromomethyl)phenyl)-5-hydroxy-3H-imidazo[4,5-b]pyridine-6-carbonitrile

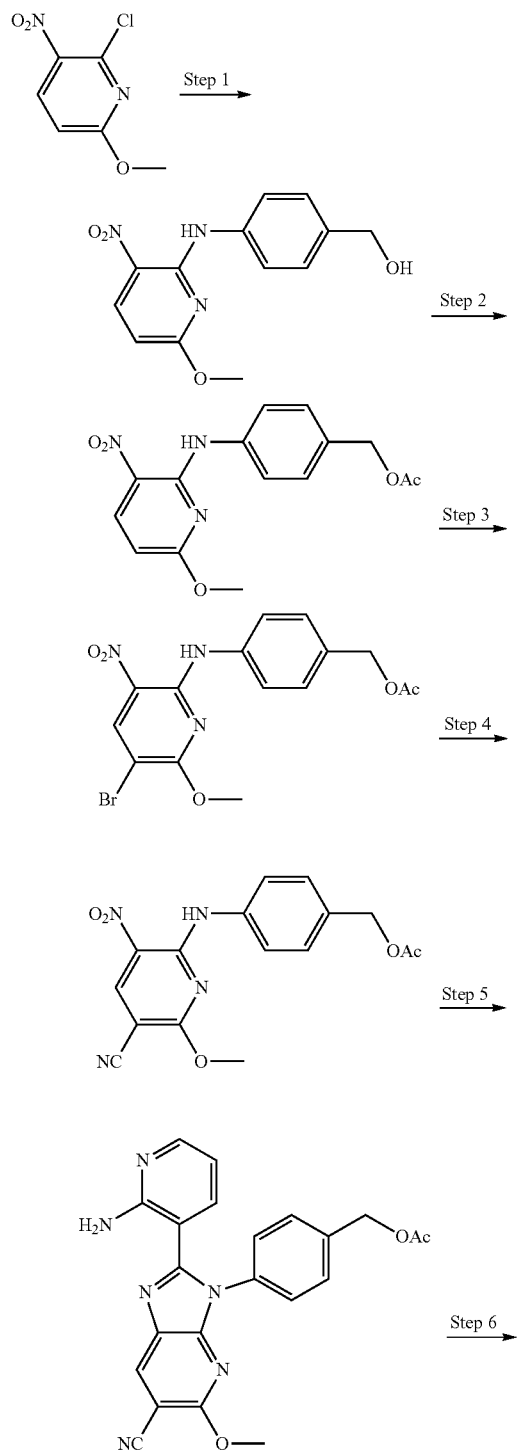

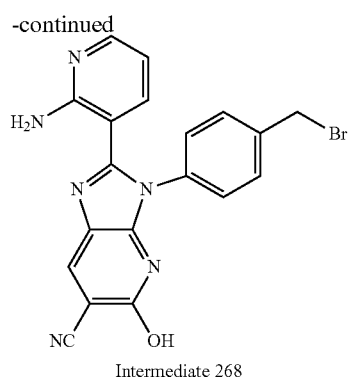

Intermediate 268

Step 1: (4-((6-Methoxy-3-nitropyridin-2-yl)amino)phenyl)methanol

To a solution of 2-chloro-6-methoxy-3-nitropyridine (12 g, 64 mmol), and DIEA (25 g, 191 mmol) in DMSO (100 mL) was added (4-aminophenyl)methanol (7.8 g, 64 mmol) at 25° C. The mixture was stirred at 80° C. for 12 hr. The mixture was quenched with H$_2$O (300 mL) and extracted with CH$_2$Cl$_2$ (100 mL×2). The combined organic layers were washed with brine (200 mL×3), dried over Na$_2$SO$_4$, filtered and concentrated. (4-((6-Methoxy-3-nitropyridin-2-yl)amino)phenyl)methanol (15 g, yield: 79%) was obtained as a yellow solid. MS: m/z=275.8 [M+H]$^+$. $^1$H NMR (400 MHz, Dimethylsulfoxide-d$_6$) δ 10.45 (s, 1H), 8.43 (d, J=9.2 Hz, 1H), 7.66 (d, J=8.4 Hz, 2H), 7.33 (d, J=8.4 Hz, 2H), 6.36 (d, J=9.2 Hz, 1H), 5.18 (t, J=5.6 Hz, 1H), 4.49 (d, J=5.6 Hz, 2H), 3.88 (s, 3H).

Step 2: 4-((6-Methoxy-3-nitropyridin-2-yl)amino)benzyl acetate

To a solution of (4-((6-methoxy-3-nitropyridin-2-yl)amino)phenyl)methanol (15 g, 54 mmol), TEA (16 g, 163 mmol), and DMAP (666 g, 5.4 mmol) in CH$_2$Cl$_2$ (100 mL) was added acetic anhydride (6.7 g, 65 mmol) at 0° C. The mixture was stirred at 0° C. for 2 hr. The mixture was quenched with H$_2$O (300 mL) and extracted with CH$_2$Cl$_2$ (100 mL×2). The combined organic layers were washed with brine (200 mL×3), dried over Na$_2$SO$_4$, filtered and concentrated. After purified by silica gel flash chromatography (Eluent of 0%~40% EtOAc in petroleum ether), 4-((6-methoxy-3-nitropyridin-2-yl)amino)benzyl acetate (16.5 g, yield: 88%) was obtained as a yellow solid. MS: m/z=318.0 [M+H]$^+$. $^1$H NMR (400 MHz, Dimethylsulfoxide-d$_6$) δ 10.47 (s, 1H), 8.44 (d, J=9.2 Hz, 1H), 7.73 (d, J=8.8 Hz, 2H), 7.39 (d, J=8.4 Hz, 2H), 6.38 (d, J=9.2 Hz, 1H), 5.06 (s, 2H), 3.89 (s, 3H), 2.07 (s, 3H).

Step 3: 4-((5-Bromo-6-methoxy-3-nitropyridin-2-yl)amino)benzyl acetate

To a solution of 4-((6-methoxy-3-nitropyridin-2-yl)amino)benzyl acetate (12 g, 38 mmol) in DMF (50 mL) was added NBS (8.0 g, 45 mmol) at 25° C. The mixture was stirred at 90° C. for 2 hr. The mixture was quenched with H$_2$O (300 mL) and extracted with CH$_2$Cl$_2$ (100 mL×2). The combined organic layers were washed with brine (200 mL×3), dried over Na$_2$SO$_4$, filtered and concentrated. 4-((5-Bromo-6-methoxy-3-nitropyridin-2-yl)amino)benzyl acetate (14 g, crude) was obtained as a yellow solid. MS: m/z=396.0, 397.8[M+H]+. 1H NMR (400 MHz, Dimethylsulfoxide-d6) δ 10.37 (s, 1H), 8.65 (s, 1H), 7.70 (d, J=8.4 Hz, 2H), 7.39 (d, J=8.8 Hz, 2H), 5.07 (s, 2H), 3.94 (s, 3H), 2.07 (s, 3H).

Step 4: 4-((5-Cyano-6-methoxy-3-nitropyridin-2-yl)amino)benzyl acetate

A mixture of 4-((5-bromo-6-methoxy-3-nitropyridin-2-yl)amino)benzyl acetate (5 g, 12.6 μmol) and CuCN (5.6 g, 63 mmol) in DMF (20 mL) was stirred at 180° C. for 2 hr. The mixture was quenched with H2O (200 mL) and extracted with CH2Cl2 (100 mL×2). The combined organic layers were washed with brine (200 mL×3), dried over Na2SO4, filtered and concentrated. After purified by silica gel flash chromatography (Eluent of 0%~15% EtOAc in petroleum ether), 4-((5-cyano-6-methoxy-3-nitropyridin-2-yl)amino)benzyl acetate (3.3 g, yield: 69% for two steps) was obtained as a yellow solid. 1H NMR (400 MHz, Dimethylsulfoxide-d6) δ 10.61 (s, 1H), 8.99 (s, 1H), 7.68 (d, J=8.0 Hz, 2H), 7.41 (d, J=8.4 Hz, 2H), 5.08 (s, 2H), 3.94 (s, 3H), 2.07 (s, 3H).

Step 5: 4-(2-(2-Aminopyridin-3-yl)-6-cyano-5-methoxy-3H-imidazo[4,5-b]pyridin-3-yl)benzyl acetate To a solution of 4-((5-cyano-6-methoxy-3-nitropyridin-2-yl)amino)benzyl acetate (1.2 g, 3.5 mmol) in DMSO (50 mL) were added 2-aminonicotinaldehyde (514 mg, 4.2 mmol) and Na2S2O4 (2.4 g, 14 mmol) at 25° C. The mixture was stirred at 100° C. for 12 hr. The reaction mixture was poured into H2O (200 mL) and extracted with CH2Cl2 (50 mL×2). The combined organic layers were washed with brine (200 mL), dried over anhydrous Na2SO4, filtered and concentrated under reduced pressure. After purified by silica gel flash chromatography (Eluent of 0%~25% EtOAc in petroleum ether), 4-(2-(2-aminopyridin-3-yl)-6-cyano-5-methoxy-3H-imidazo[4,5-b]pyridin-3-yl)benzyl acetate (400 mg, yield: 24%) was obtained as a yellow solid. MS: m/z=414.9 [M+H]+. 1H NMR (400 MHz, Dimethylsulfoxide-d6) δ 8.74 (s, 1H), 8.00 (dd, J=4.8, 2.0 Hz, 1H), 7.53-7.44 ((m, 4H), 7.20 (dd, J=7.6, 2.0 Hz, 1H), 6.72 (s, 2H), 6.43 (dd, J=7.6, 4.8 Hz, 1H), 5.15 (s, 2H), 3.90 (s, 3H), 2.10 (s, 3H).

Step 6: 2-(2-Aminopyridin-3-yl)-3-(4-(bromomethyl)phenyl)-5-hydroxy-3H-imidazo[4,5-b]pyridine-6-carbonitrile To a solution of 4-(2-(2-aminopyridin-3-yl)-6-cyano-5-methoxy-3H-imidazo[4,5-b]pyridin-3-yl)benzyl acetate (400 mg, 965 μmol) in DCE (10 mL) was added BBr3 (4.8 mL, 4.8 mmol, 1 M in CH2Cl2). The mixture was stirred at 80° C. for 12 hr. The reaction mixture was quenched with H2O (20 mL) at 25° C. The pH of the mixture was adjusted to 8 with saturated aq. NaHCO3. The mixture was extracted with CH2Cl2 (15 mL×2). The combined organic layers were washed with brine (30 mL×2), dried over Na2SO4, filtered and concentrated under reduced pressure. 2-(2-Aminopyridin-3-yl)-3-(4-(bromomethyl)phenyl)-5-hydroxy-3H-imidazo[4,5-h]pyridine-6-carbonitrile (Intermediate 268, 350 mg, crude) was obtained as a yellow solid. MS: m/z=420.8, 422.7 [M+H]+.

Intermediate 269: 2-Amino-4-fluoronicotinaldehyde

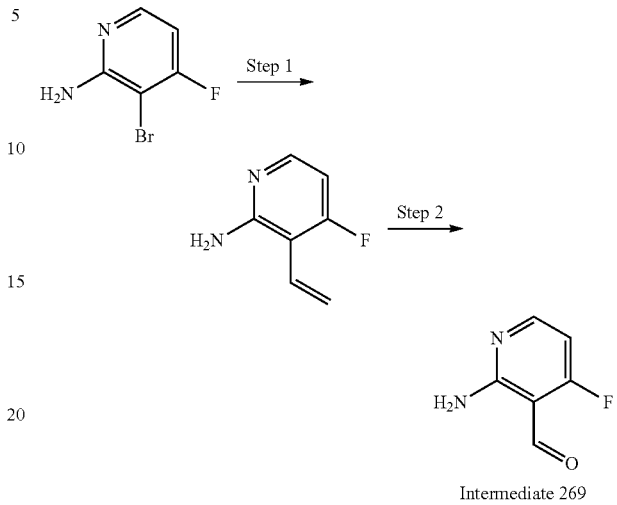

Intermediate 269

Step 1: 4-Fluoro-3-vinylpyridin-2-amine

A mixture of 3-bromo-4-fluoropyridin-2-amine (1 g, 5.24 mmol), 4,4,5,5-tetramethyl-2-vinyl-1,3,2-dioxaborolane (1.21 g, 7.85 mmol), Cs2CO3 (5.12 g, 15.7 mmol) and Pd(dppf)Cl2 (383 mg, 524 μmol) in 1,4-dioxane (20 mL) and H2O (4 mL) was degassed and purged with N2 three times. The mixture was stirred at 80° C. for 16 hr under N2 atmosphere. The reaction mixture was quenched with H2O (50 mL) at 25° C. and extracted with EtOAc (50 mL×2). The combined organic layers were washed with brine (50 mL), dried over anhydrous Na2SO4, filtered and concentrated under reduced pressure. After purified by silica gel flash chromatography (Eluent of 0%~15% EtOAc in petroleum ether), 4-fluoro-3-vinylpyridin-2-amine (700 mg, yield: 77%) was obtained as a light-yellow oil. MS: m/z=139.0 [M+H]+. 1H NMR (400 MHz, Chloroform-d) δ 7.94-7.88 (m, 1H), 6.56-6.42 (m, 2H), 5.78 (d, J=17.6 Hz, 1H), 5.63 (d, J=11.6 Hz, 1H), 4.80 (br s, 2H). 19F NMR (400 MHz, Chloroform-d) δ −106.82.

Step 2: 2-Amino-4-fluoronicotinaldehyde

To a solution of 4-fluoro-3-vinylpyridin-2-amine (700 mg, 5.07 mmol) in H2O (5 mL) and THF (15 mL) were added Na1O4 (3.25 g, 15.2 mmol) and K2OsO4·2H2O (560 mg, 1.52 mmol). The mixture was stirred at 25° C. for 1 hr. The reaction mixture was quenched with aqueous Na2SO3 (50 mL) at 25° C. and extracted with CH2Cl2 (30 mL×2). The combined organic layers were washed with brine (50 mL), dried over anhydrous Na2SO4, filtered and concentrated under reduced pressure. After purified by silica gel flash chromatography (Eluent of 5%~13% EtOAc in petroleum ether), 2-amino-4-fluoronicotinaldehyde (Intermediate 269, 275 mg, yield: 38%) was obtained as a white solid. MS: m/z=141.0 [M+H]+. 1H NMR (400 MHz, Dimethylsulfoxide-d6) δ 10.19 (s, 1H), 8.26 (dd, J=8.8, 5.6 Hz, 1H), 7.96 (br s, 2H), 6.56 (dd, J=10.8, 5.6 Hz, 1H).

Intermediate 270: 3-(3-(4-(Chloromethyl)phenyl)-5-(5-fluoropyridin-2-yl)-3H-imidazo[4,5-b]pyridin-2-yl)-4-fluoropyridin-2-amine

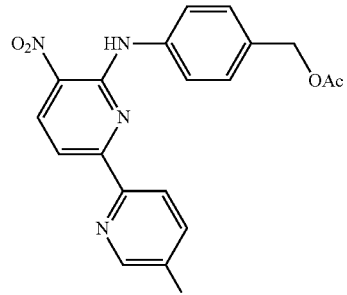

Intermediate 225

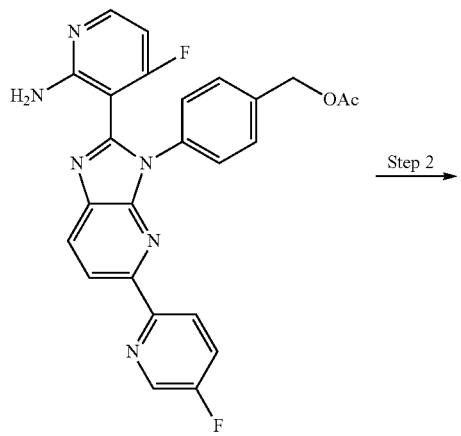

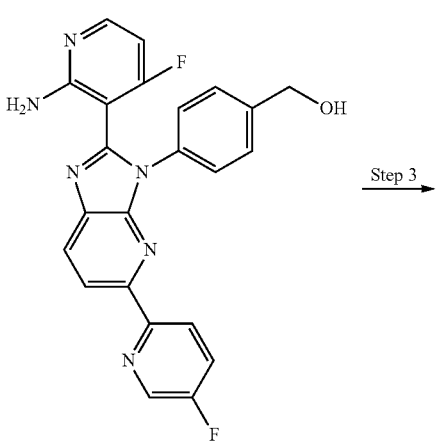

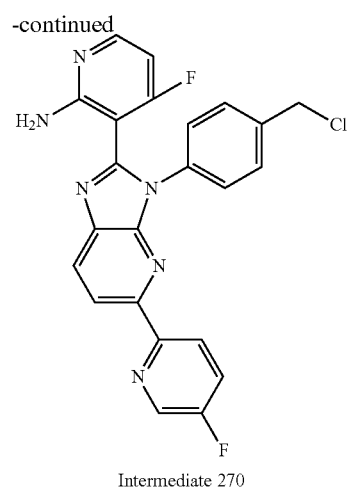

Intermediate 270

Step 1: 4-(2-(2-Amino-4-fluoropyridin-3-yl)-5-(5-fluoropyridin-2-yl)-3H-imidazo[4,5-b]pyridin-3-yl)benzyl acetate To a solution of Intermediate 269 (200 mg, 1.43 mmol) in DMSO (10 mL) were added $Na_2S_2O_4$ (1.03 g, 5.19 mmol, 88% purity) and Intermediate 225 (496 mg, 1.30 mmol). The mixture was stirred at 60° C. for 16 hr. The reaction mixture was quenched with $H_2O$ (50 mL) and extracted with $CH_2Cl_2$ (15 mL×2). The combined organic layers were washed with brine (50 mL×3), dried over $Na_2SO_4$, filtered and concentrated under reduced pressure. After purified by prep-HPLC (column: Phenomenex C18 150×25 mm×10 μm; mobile phase: [water ($NH_4HCO_3$)-ACN]; gradient: 32%-62% B over 11 min), 4-(2-(2-amino-4-fluoropyridin-3-yl)-5-(5-fluoropyridin-2-yl)-3H-imidazo[4,5-b]pyridin-3-yl)benzyl acetate (20 mg, yield: 1.3%) was obtained as a yellow solid. MS: m/z=495.1 [M+Na]$^+$. $^1$H NMR (400 MHz, Chloroform-d) δ 8.51-8.50 (m, 1H), 8.44-8.41 (m, 2H), 8.24-8.20 (m, 2H), 8.09 (dd, J=8.4, 5.6 Hz, 1H), 7.87-7.83 (m, 1H), 7.49-7.45 (m, 3H), 7.32 (br s, 2H), 7.14 (d, J=8.0 Hz, 1H), 5.20 (s, 2H), 2.16 (s, 3H).

Step 2: (4-(2-(2-Amino-4-fluoropyridin-3-yl)-5-(5-fluoropyridin-2-yl)-3H-imidazo[4,5-b]pyridin-3-yl)phenyl)methanol To a solution of 4-(2-(2-amino-4-fluoropyridin-3-yl)-5-(5-fluoropyridin-2-yl)-3H-imidazo[4,5-b]pyridin-3-yl)benzyl acetate (20 mg, 42.3 μmol) in THF (1 mL), MeOH (1 mL) and $H_2O$ (1 mL) was added $K_2CO_3$ (17.6 mg, 127 μmol). The mixture was stirred at 25° C. for 1 hr. The reaction mixture was quenched with $H_2O$ (5 mL) at 25° C. and extracted with $CH_2Cl_2$ (15 mL×2). The combined organic layers were washed with brine (30 mL), dried over $Na_2SO_4$, filtered and concentrated under reduced pressure. (4-(2-(2-Amino-4-fluoropyridin-3-yl)-5-(5-fluoropyridin-2-yl)-3H-imidazo[4,5-b]pyridin-3-yl)phenyl)methanol (18 mg) was obtained as a yellow solid. MS: m/z=431.1 [M+H]$^+$.

Step 3: 3-(3-(4-(Chloromethyl)phenyl)-5-(5-fluoropyridin-2-yl)-3H-imidazo[4,5-b]pyridin-2-yl)-4-fluoropyridin-2-amine To a solution of (4-(2-(2-amino-4-fluoropyridin-3-yl)-5-(5-fluoropyridin-2-yl)-3H-imidazo[4,5-b]pyridin-3-yl)phenyl)methanol (18 mg, 41.8 µmol) in CH₂Cl₂ (3 mL) was added SOCl₂ (14.9 mg, 125 µmol). The mixture was stirred at 25° C. for 0.5 hr. The reaction was concentrated under reduced pressure to give 3-(3-(4-(chloromethyl)phenyl)-5-(5-fluoropyridin-2-yl)-3H-imidazo[4,5-b]pyridin-2-yl)-4-fluoropyridin-2-amine (Intermediate 270, 20 mg, HCl salt) as a yellow solid. MS: m/z=449.0 [M+H]⁺.

Intermediate 271: 3-(4-(Chloromethyl)phenyl)-5-(5-fluoropyridin-2-yl)-2-(pyrimidin-5-yl)-3H-imidazo[4,5-b]pyridine

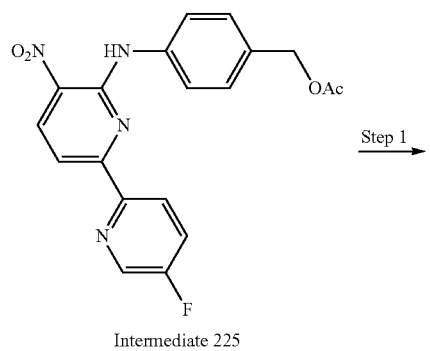

Intermediate 225

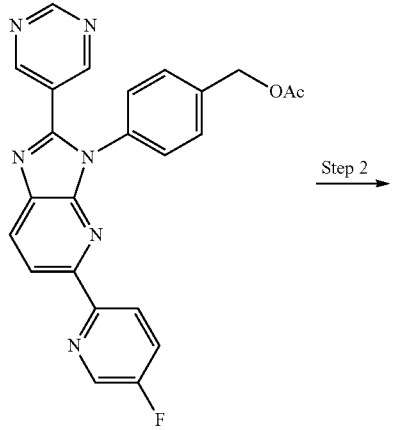

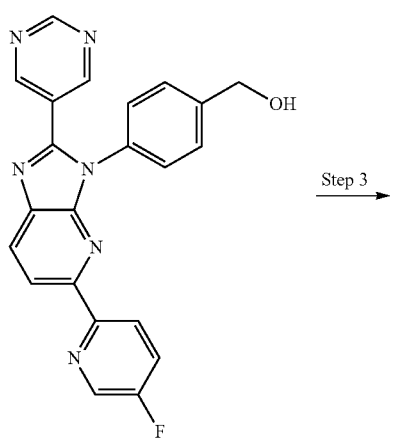

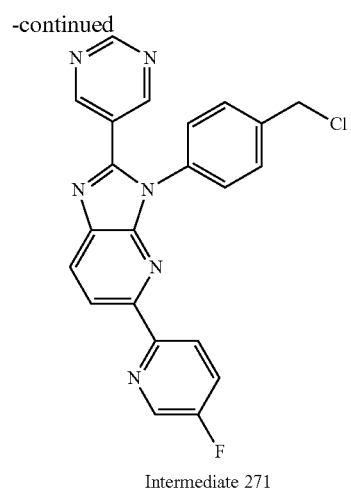

Intermediate 271

Step 1: 4-(5-(5-Fluoropyridin-2-yl)-2-(pyrimidin-5-yl)-3H-imidazo[4,5-b]pyridin-3-yl)benzyl acetate To a solution of Intermediate 225 (1 g, 2.62 mmol) in DMSO (15 mL) were added Na₂S₂O₄ (1.82 g, 10.46 mmol, 88% purity) and pyrimidine-5-carbaldehyde (339 mg, 3.14 mmol). The mixture was stirred at 100° C. for 16 hr. The reaction mixture was quenched with H₂O (100 mL) at 25° C., diluted with EtOAc (100 mL), and extracted with EtOAc (100 mL×2). The combined organic layers were washed with brine (100 mL), dried over Na₂SO₄, filtered and concentrated under reduced pressure. After purified by silica gel flash chromatography (Eluent of 0%~35% EtOAc in petroleum ether), 4-(5-(5-fluoropyridin-2-yl)-2-(pyrimidin-5-yl)-3H-imidazo[4,5-b]pyridin-3-yl)benzyl acetate (550 mg, yield: 28%) was obtained as a light yellow solid. MS: m/z=441.1 [M+H]⁺.

Step 2: (4-(5-(5-Fluoropyridin-2-yl)-2-(pyrimidin-5-yl)-3H-imidazo[4,5-b]pyridin-3-yl)phenyl)methanol To a solution of 4-(5-(5-fluoropyridin-2-yl)-2-(pyrimidin-5-yl)-3H-imidazo[4,5-b]pyridin-3-yl)benzyl acetate (550 mg, 1.25 mmol) in THF (4 mL), MeOH (4 mL) and H₂O (2 mL) was added K₂CO₃ (518 mg, 3.75 mmol). The mixture was stirred at 25° C. for 1 hr. The reaction mixture was diluted with H₂O (100 mL) and extracted with EtOAc (100 mL×2). The combined organic layers were washed with brine (100 mL), dried over Na₂SO₄, filtered and concentrated under reduced pressure. (4-(5-(5-Fluoropyridin-2-yl)-2-(pyrimidin-5-yl)-3H-imidazo[4,5-b]pyridin-3-yl)phenyl)methanol (490 mg) was obtained as a light yellow solid. MS: m/z=399.1 [M+H]⁺.

Step 3: 3-(4-(Chloromethyl)phenyl)-5-(5-fluoropyridin-2-yl)-2-(pyrimidin-5-yl)-3H-imidazo[4,5-b]pyridine To a solution of (4-(5-(5-fluoropyridin-2-yl)-2-(pyrimidin-5-yl)-3H-imidazo[4,5-b]pyridin-3-yl)phenyl)methanol (490 mg, 1.23 mmol) in CH₂Cl₂ (3 mL) was added SOCl₂ (439 mg, 3.69 mmol). The mixture was stirred at 40° C. for 0.5 hr. The reaction was concentrated under reduced pressure to give 3-(4-(chloromethyl)phenyl)-5-(5-fluoropyridin-2-yl)-2-(pyrimidin-5-yl)-3H-imidazo[4,5-b]pyridine (Inter- Intermediate 272: 3-(1-(4-(Chloromethyl)phenyl)-6-(5-fluoropyridin-2-yl)-1H-benzo[d]imidazol-2-yl)pyridin-2-amine

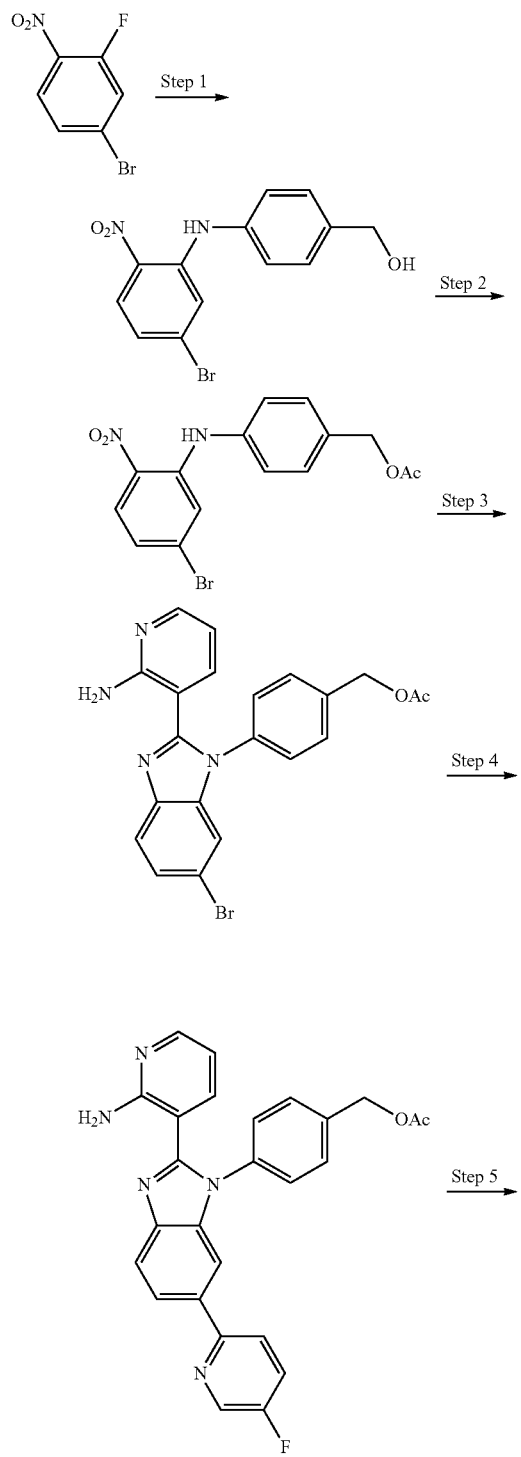

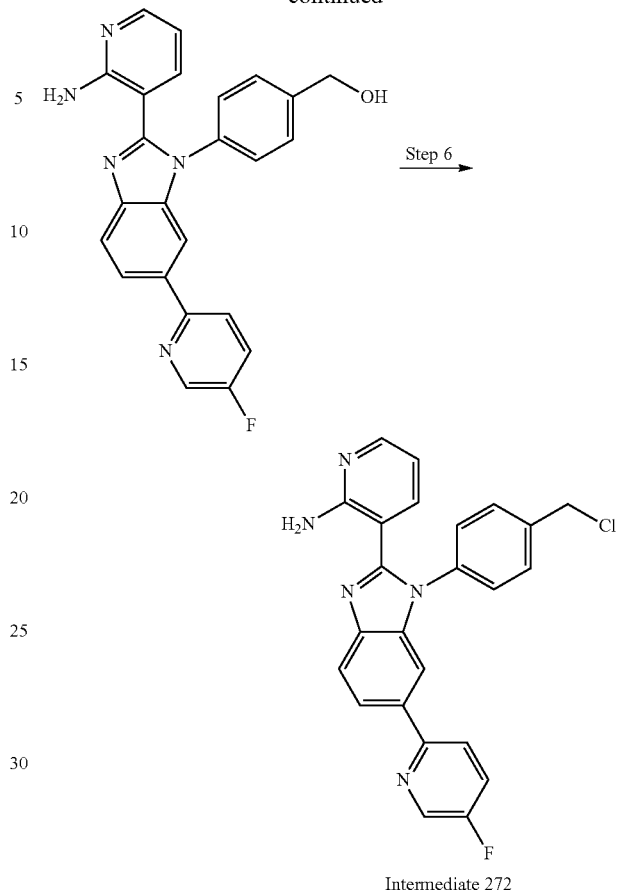

Intermediate 272

Step 1: (4-((5-Bromo-2-nitrophenyl)amino)phenyl)methanol

To a solution of 4-bromo-2-fluoro-1-nitrobenzene (9 g, 40.91 mmol) in 1,4-dioxane (100 mL) were added DIEA (15.86 g, 122.73 mmol) and (4-aminophenyl)methanol (5.04 g, 40.91 mmol). The mixture was degassed and purged with $N_2$ three times and stirred at 80° C. for 16 hr under $N_2$. The reaction mixture was diluted with $H_2O$ (500 mL) and extracted with $CH_2Cl_2$ (500 mL×3). The combined organic layers were washed with brine (200 mL), dried over $Na_2SO_4$, filtered and concentrated under reduced pressure. After purified by silica gel flash chromatography ($SiO_2$, petroleum ether/ethyl acetate=99/1 to 7/3), (4-((5-bromo-2-nitrophenyl)amino)phenyl)methanol (3.1 g, yield: 23%) was obtained as a yellow solid. $^1$H NMR (400 MHz, Dimethyl-sulfoxide-$d_6$) δ 9.48 (s, 1H), 8.04 (d, J=9.2 Hz, 1H), 7.40 (d, J=8.4 Hz, 2H), 7.29 (d, J=8.0 Hz, 2H), 7.10 (s, 1H), 7.00 (dd, J=9.2, 7.2 Hz, 1H), 5.23-5.21 (m, 1H), 4.53-4.51 (m, 2H).

Step 2: 4-((5-Bromo-2-nitrophenyl)amino)benzyl acetate

To a solution of (4-(5-bromo-2-nitrophenyl)amino)phenyl)methanol (2.54 g, 7.86 mmol) and TEA (2.39 g, 25.6 mmol) in $CH_2Cl_2$ (30 mL) were added $Ac_2O$ (802 mg, 7.86 mmol) and DMAP (96.0 mg, 786 μmol). The mixture was stirred at 0° C. for 1 hr. The reaction mixture was diluted with $H_2O$ (500 mL) and extracted with $CH_2Cl_2$ (500 mL×3). The combined organic layers were washed with brine (200 mL), dried over Na$_2$SO$_4$, filtered and concentrated under reduced pressure. After purified by silica gel flash chromatography (Eluent of 0~15% EtOAc in petroleum ether), 4-((5-bromo-2-nitrophenyl)amino)benzyl acetate (2.7 g, yield: 92%) was obtained as a yellow solid. $^1$H NMR (400 MHz, Chloroform-d) δ 9.41 (s, 1H), 7.98 (d, J=9.2 Hz, 1H), 7.35 (d, J=8.4 Hz, 2H), 7.17-7.15 (m, 3H), 6.80 (dd, J=9.2, 2.0 Hz, 1H), 5.04 (s, 2H), 2.05 (s, 3H).

Step 3: 4-(2-(2-Aminopyridin-3-yl)-6-bromo-1H-benzo[d]imidazol-1-yl)benzyl acetate To a solution of 4-((5-bromo-2-nitrophenyl)amino)benzyl acetate (2.7 g, 7.39 mmol) in DMSO (10 mL) were added Na$_2$S$_2$O$_4$ (5.12 g, 29.6 mmol, 87% purity) and 2-aminonicotinaldehyde (1.08 g, 8.87 mmol). The mixture was stirred at 100° C. for 3 hr. The reaction mixture was quenched with H$_2$O (500 mL) and extracted with EtOAc (500 mL×2). The combined organic layers were washed with brine (500 mL), dried over Na$_2$SO$_4$, filtered and concentrated under reduced pressure. After purified by silica gel flash chromatography (Eluent of 0%~40% EtOAc in petroleum ether), 4-(2-(2-aminopyridin-3-yl)-6-bromo-1H-benzo[d]imidazol-1-yl)benzyl acetate (1.1 g, yield: 33%) was obtained as a light yellow solid. MS: m/z=437.0, 438.9 [M+H]$^+$. $^1$H NMR (400 MHz, Chloroform-d) δ 8.05 (dd, J=4.8, 1.6 Hz, 1H), 7.68 (d, J=8.4 Hz, 1H), 7.53 (d, J=8.4 Hz, 2H), 7.44 (dd, J=8.4, 1.6 Hz, 1H), 7.34 (d, J=1.6 Hz, 1H), 7.31 (d, J=8.4 Hz, 2H), 7.02 (dd, J=7.6, 1.6 Hz, 1H), 6.59 (s, 2H), 6.35 (dd, J=4.8, 7.8 Hz, 1H), 5.21 (s, 2H), 2.18 (s, 3H).

Step 4: 4-(2-(2-Aminopyridin-3-yl)-6-(5-fluoropyridin-2-yl)-1H-benzo[d]imidazol-1-yl)benzyl acetate A mixture of 4-(2-(2-aminopyridin-3-yl)-6-bromo-1H-benzo[d]imidazol-1-yl)benzyl acetate (500 mg, 1.14 mmol), (5-fluoropyridin-2-yl)boronic acid (483 mg, 3.43 mmol), Pd(dppf)Cl$_2$ (83.7 mg, 114 μmol), Cs$_2$CO$_3$ (1.12 g, 3.43 mmol) and CuBr 65.6 mg, 457 μmol) in 1,4-dioxane (7.5 mL) and H$_2$O (1.5 mL) was degassed and purged with N$_2$ three times. The mixture was stirred at 100° C. for 16 hr under N$_2$ atmosphere. The reaction mixture was quenched with H$_2$O (100 mL), diluted with CH$_2$Cl$_2$ (100 mL), and extracted with CH$_2$Cl$_2$ (100 mL×2). The combined organic layers were washed with brine (100 mL), dried over Na$_2$SO$_4$, filtered and concentrated under reduced pressure. After purified by silica gel flash chromatography (Eluent of 0%~56% EtOAc in petroleum ether), 4-(2-(2-aminopyridin-3-yl)-6-(5-fluoropyridin-2-yl)-1H-benzo[d]imidazol-1-yl)benzyl acetate (380 mg, yield: 59%) was obtained as a light yellow solid. MS: m/z=454.2 [M+H]$^+$.

Step 5: (4-(2-(2-Aminopyridin-3-yl)-6-(5-fluoropyridin-2-yl)-1H-benzo[d]imidazol-1-yl)phenyl)methanol To a solution of 4-(2-(2-aminopyridin-3-yl)-6-(5-fluoropyridin-2-yl)-1H-benzo[d]imidazol-1-yl)benzyl acetate (380 mg, 838 μmol) in THF (4 mL) and MeOH (4 mL) was added K$_2$CO$_3$ (347 mg, 2.51 mmol) in H$_2$O (4 mL). The mixture was stirred at 25° C. for 1 hr. The reaction mixture was quenched with H$_2$O (100 mL) at 25° C. and extracted with EtOAc (100 mL×2). The combined organic layers were washed with brine (100 mL×2), dried over Na$_2$SO$_4$, filtered and concentrated under reduced pressure. (4-(2-(2-Aminopyridin-3-yl)-6-(5-fluoropyridin-2-yl)-1H-benzo[d]imidazol-1-yl)phenyl)methanol (340 mg, yield: 85%) was obtained as a light yellow solid. MS: m/z=412.2 [M+H]$^+$.

Step 6: 3-(1-(4-(Chloromethyl)phenyl)-6-(5-fluoropyridin-2-yl)-1H-benzo[d]imidazol-2-yl)pyridin-2-amine To a solution of (4-(2-(2-aminopyridin-3-yl)-6-(5-fluoropyridin-2-yl)-1H-benzo[d]imidazol-1-yl)phenyl)methanol (400 mg, 972 μmol) in CH$_2$Cl$_2$ (6 mL) was added SOCl$_2$ (347 mg, 2.92 mmol). The mixture was stirred at 40° C. for 0.5 hr. The reaction was concentrated under reduced pressure to give 3-(1-(4-(chloromethyl)phenyl)-6-(5-fluoropyridin-2-yl)-1H-benzo[d]imidazol-2-yl)pyridin-2-amine (Intermediate 272, 400 mg, HCl salt) as a light yellow solid. MS: m/z=430.1 [M+H]$^+$.

Intermediate 273: 3-(3-(4-(Chloromethyl)phenyl)-5-(5-fluoropyrimidin-2-yl)-3H-imidazo[4,5-b]pyridin-2-yl)pyridin-2-amine

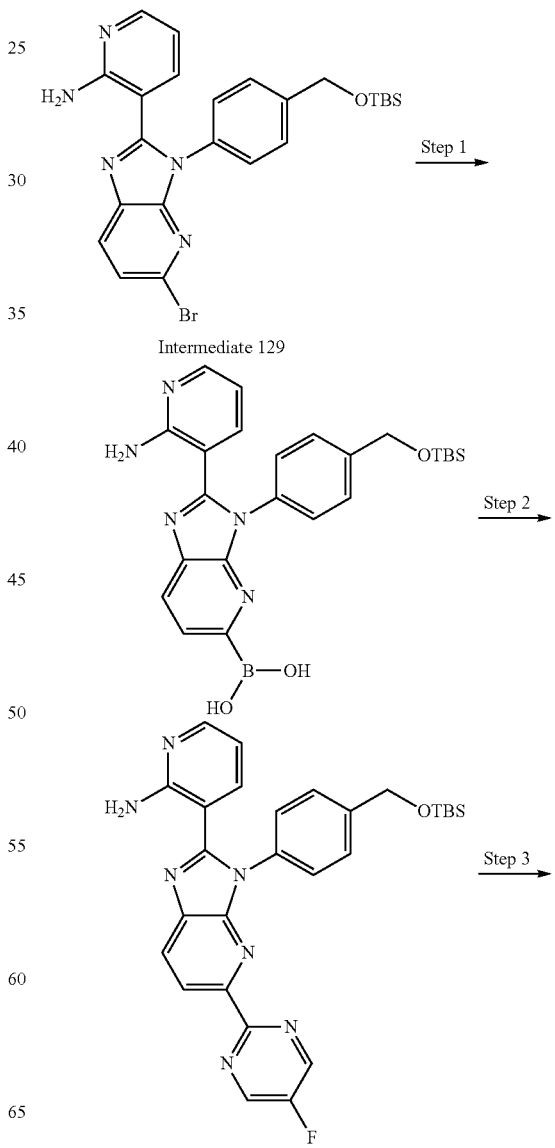

-continued

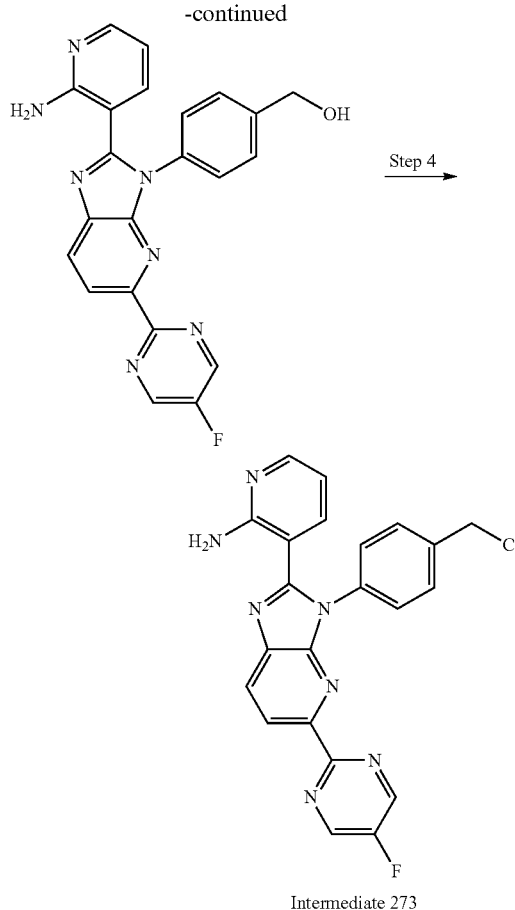

Intermediate 273

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (500 mg, 947 μmol), 4,4,5,5-tetramethyl-2-(4,4,5,5-tetramethyl-1,3,2-dioxaborolan-2-yl)-1,3,2-dioxaborolane (497 mg, 1.96 mmol), KOAc (288 mg, 2.94 mmol), and Pd(dppf)Cl$_2$ (72 mg, 98 μmol) in 1,4-dioxane (5 mL) was degassed and purged with N$_2$ three times. The mixture was stirred at 80° C. for 16 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black brown liquid, which was used in the next step without work-up and purification. MS: m/z=476.3 [M+H]$^+$.

Step 2: 3-(3-(4-(((tert-Butyldimethylsilyl)oxy)methyl)phenyl)-5-(5-fluoropyrimidin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (500 mg, 1.05 mmol), 2-chloro-5-fluoropyrimidine (139 mg, 1.05 mmol), Pd(dppf)Cl$_2$ (76.9 mg, 105 μmol), and Cs$_2$CO$_3$ (1.03 g, 3.16 mmol) in 1,4-dioxane (4 mL) and H$_2$O (1 mL) was degassed and purged with N$_2$ three times. The mixture was stirred at 90° C. for 16 hr under N$_2$ atmosphere. The reaction mixture was diluted with H$_2$O (20 mL) and extracted with EtOAc (20 mL). The combined organic layers were washed with brine (30 mL), dried over Na$_2$SO$_4$, filtered and concentrated under reduced pressure. After purified by silica gel flash chromatography (Eluent of 0~50% EtOAc in petroleum ether), 3-(3-(4-(((tert-butyldimethylsilyl)oxy)methyl)phenyl)-5-(5-fluoropyrimidin-2-yl)-3H-imidazo[4,5-b]pyridin-2-yl)pyridin-2-amine (410 mg, yield: 65% for two steps) was obtained as a black brown solid. MS: m/z=528.2 [M+H]$^+$. $^1$H NMR (400 MHz, Dimethylsulfoxide-d$_6$) δ 9.00 (s, 2H), 8.43 (d, J=8.4 Hz, 1H), 8.34 (d, J=8.4 Hz, 1H), 8.08-7.91 (m, 1H), 7.53-7.44 (m, 4H), 7.19 (dd, J=7.6, 1.6 Hz, 1H), 7.02 (s, 2H), 6.38 (dd, J=7.6, 4.8 Hz, 1H), 4.82 (s, 2H), 0.93 (s, 9H), 0.12 (s, 6H).

Step 3: (4-(2-(2-Aminopyridin-3-yl)-5-(5-fluoropyrimidin-2-yl)-3H-imidazo[4,5-b]pyridin-3-yl)phenyl)methanol To a solution of 3-(3-(4-(((tert-butyldimethylsilyl)oxy)methyl)phenyl)-5-(5-fluoropyrimidin-2-yl)-3H-imidazo[4,5-b]pyridin-2-yl)pyridin-2-amine (410 mg, 777 μmol) in THF (5 mL) was added TBAF (406 mg, 1.55 mmol, 1 M in THF). The mixture was stirred at 25° C. for 1 hr. The mixture was diluted with H$_2$O (20 mL) and extracted with EtOAc (20 mL×2). The combined organic layers were washed with brine (20 mL), dried over Na$_2$SO$_4$, filtered and concentrated under reduced pressure. After triturated with EtOAc (10 mL) at 25° C. for 1 hr, (4-(2-(2-aminopyridin-3-yl)-5-(5-fluoropyrimidin-2-yl)-3H-imidazo[4,5-b]pyridin-3-yl)phenyl)methanol (260 mg, crude) was obtained as a black brown solid. MS: m/z=414.1 [M+H]$^+$.

Step 4: 3-(3-(4-(Chloromethyl)phenyl)-5-(5-fluoropyrimidin-2-yl)-3H-imidazo[4,5-b]pyridin-2-yl)pyridin-2-amine To a solution of (4-(2-(2-aminopyridin-3-yl)-5-(5-fluoropyrimidin-2-yl)-3H-imidazo[4,5-b]pyridin-3-yl)phenyl)methanol (260 mg, 629 μmol) in CH$_2$Cl$_2$ (4 mL) was added SOCl$_2$ (2 mL). The mixture was stirred at 25° C. for 1 hr. The mixture was concentrated under reduced pressure to give 3-(3-(4-(chloromethyl)phenyl)-5-(5-fluoropyrimidin-2-yl)-3H-imidazo[4,5-b]pyridin-2-yl)pyridin-2-amine (Intermediate 273, 300 mg, crude, HCl salt) as a black brown solid. The crude product was used into the next step without further purification. MS: m/z=432.1 [M+H]$^+$.

Intermediate 274: 3-(3-(4-(Chloromethyl)phenyl)-5-(5-methylpyrimidin-2-yl)-3H-imidazo[4,5-b]pyridin-2-yl)pyridin-2-amine

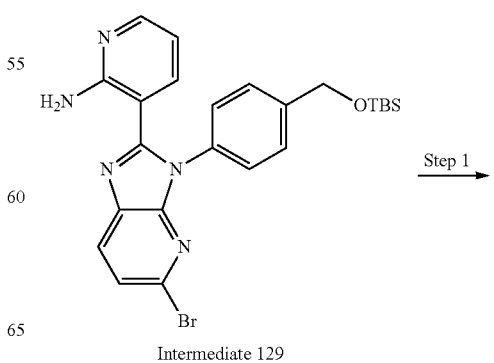

Intermediate 129

-continued

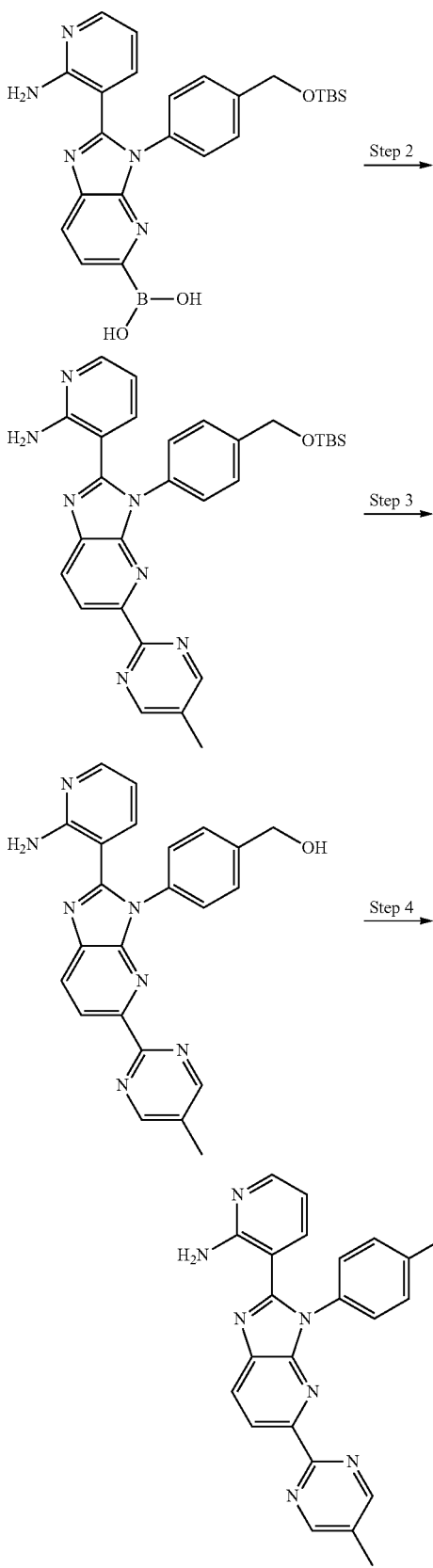

Intermediate 274

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (500 mg, 947 μmol), 4,4,4',4',5,5,5',5'-octamethyl-2,2'-bi(1,3,2-dioxaborolane) (497 mg, 1.96 mmol), KOAc (288 mg, 2.94 mmol), Pd(dppf)Cl$_2$ (72 mg, 98 μmol) in 1,4-dioxane (5 mL) was degassed and purged with N$_2$ three times. The mixture was stirred at 80° C. for 16 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((tert-Butyldimethylsilyl)oxy)methyl)phenyl)-5-(5-methylpyrimidin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (400 mg, 841 μmol), 2-chloro-5-methylpyrimidine (108 mg, 841 μmol), Pd(dppf)Cl$_2$ (61.56 mg, 84 μmol), Cs$_2$CO$_3$ (822 mg, 2.52 mmol) and H$_2$O (0.5 mL) in 1,4-dioxane (2 mL) was degassed and purged with N$_2$ three times. The mixture was stirred at 90° C. for 16 hr under N$_2$ atmosphere. The reaction mixture was diluted with H$_2$O (10 mL) and extracted with EtOAc (10 mL×3). The combined organic layers were washed with brine (20 mL), dried over Na$_2$SO$_4$, filtered and concentrated under reduced pressure. After purified by silica gel flash chromatography (Eluent of 0%~50% EtOAc in petroleum ether), 3-(3-(4-(((tert-butyldimethylsilyl)oxy)methyl)phenyl)-5-(5-methylpyrimidin-2-yl)-3H-imidazo[4,5-b]pyridin-2-yl)pyridin-2-amine (240 mg, yield: 44% for two steps) was obtained as a black brown solid. MS: m/z=524.3 [M+H]$^+$. $^1$H NMR (400 MHz, Dimethysulfoxide-d) δ 8.89-8.66 (m, 2H), 8.45 (d, J=8.0 Hz, 1H), 8.31 (d, J=8.0 Hz, 1H), 8.05-7.90 (m, 1H), 7.54-7.42 (m, 4H), 7.19 (d, J=7.2 Hz, 1H), 7.01 (br s, 2H), 6.44-6.30 (m, 1H), 4.83 (s, 2H), 2.32 (s, 3H), 0.94 (s, 9H), 0.12 (s, 6H)

Step 3: (4-(2-(2-Aminopyridin-3-yl)-5-(5-methylpyrimidin-2-yl)-3H-imidazo[4,5-b]pyridin-3-yl)phenyl)methanol To a solution of 3-(3-(4-(((tert-butyldimethylsilyl)oxy)methyl)phenyl)-5-(5-methylpyrimidin-2-yl)-3H-imidazo[4,5-b]pyridin-2-yl)pyridin-2-amine (220 mg, 420 μmol) in THF (2 mL) was added TBAF (220 mg, 1 M in THF). The mixture was stirred at 25° C. for 1 hr. The reaction mixture was diluted with H$_2$O (30 mL) and extracted with EtOAc (20 mL). The combined organic layers were washed with brine (30 mL), dried over Na$_2$SO$_4$, filtered and concentrated under reduced pressure. After triturated with EtOAc in petroleum ether=1:1 (10 mL) at 25° C. for 16 hr, (4-(2-(2-aminopyridin-3-yl)-5-(5-methylpyrimidin-2-yl)-3H-imidazo[4,5-b]pyridin-3-yl)phenyl)methanol (180 mg) was obtained as a yellow solid. MS: m/z=410.2 [M+H]$^+$.

Step 4: 3-(3-(4-(Chloromethyl)phenyl)-5-(5-methylpyrimidin-2-yl)-3H-imidazo[4,5-b]pyridin-2-yl)pyridin-2-amine To a solution of (4-(2-(2-aminopyridin-3-yl)-5-(5-methylpyrimidin-2-yl)-3H-imidazo[4,5-b]pyridin-3-yl)phenyl)

methanol in CH$_2$Cl$_2$ (2 mL) was added SOCl$_2$ (1 mL). The mixture was stirred at 25° C. for 0.5 hr. The mixture was concentrated under reduced pressure to give 3-(3-(4-(chloromethyl)phenyl)-5-(5-methylpyrimidin-2-yl)-3H-imidazo[4,5-b]pyridin-2-yl)pyridin-2-amine (Intermediate 274, 142 mg, HCl salt) as a light yellow solid. MS: m/z=428.2 [M+H]$^+$.

Intermediate 275: 3-(3-(4-(Chloromethyl)phenyl)-5-(5-fluoropyrazin-2-yl)-3H-imidazo[4,5-b]pyridin-2-yl)pyridin-2-amine

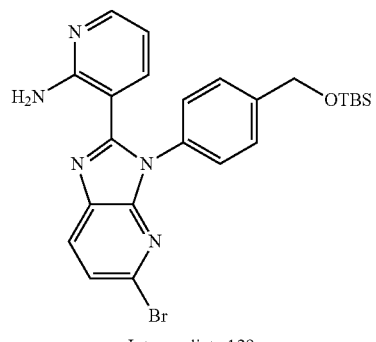

Intermediate 129

Step 1

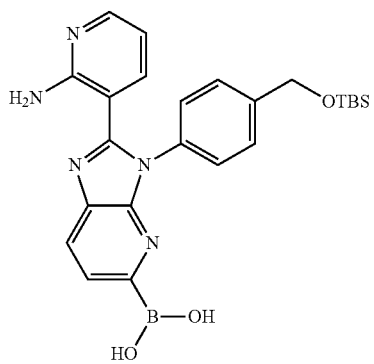

Step 2

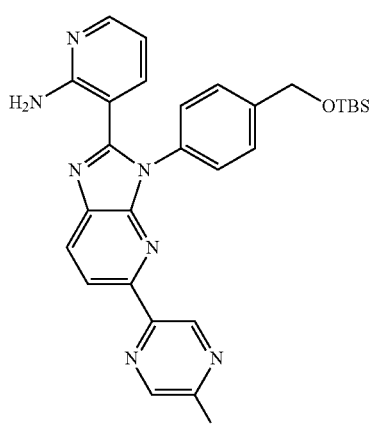

Step 3

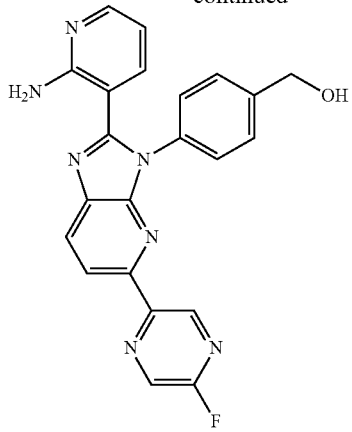

Step 4

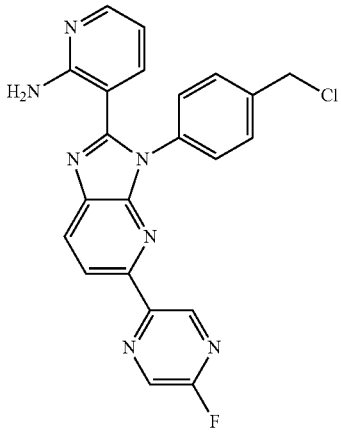

Intermediate 275

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl$_2$ (143 mg, 196 mmol) in 1,4-dioxane (5 mL) was degassed and purged with N$_2$ three times. The mixture was stirred at 90° C. for 16 hr under N$_2$ atmosphere. (2-(2-aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]$^+$.

Step 2: 3-(3-(4-(((tert-Butyldimethylsilyl)oxy)methyl)phenyl)-5-(5-fluoropyrazin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (410 mg, 862 µmol), 2-bromo-5-fluoropyrazine (168 mg, 949 µmol), Pd(dppf)Cl$_2$ (63.1 mg, 86.2 µmol) and Cs$_2$CO$_3$ (843 mg, 2.59 mmol) in 1,4-dioxane (4 mL) and H$_2$O (1 mL) was degassed and purged with N$_2$ three times. The mixture was stirred at 90° C. for 16 hr under N$_2$ atmosphere. The reaction mixture was poured into H$_2$O (15 mL) and extracted with EtOAc (15 mL×3). The combined organic layers were dried over anhydrous Na$_2$SO$_4$, filtered and concentrated under reduced pressure. After purified by silica gel flash chromatography (Eluent of 0%~25% EtOAc in petroleum ether), 3-(3-(4-(((tert-butyldimethylsilyl)oxy)methyl)phenyl)-5-(5-fluoropyrazin-2-yl)-3H-imidazo[4,5-b]pyridin-2-yl)pyridin-2-amine (480 mg, yield: 40% for two steps) was obtained as a brown solid. MS: m/z=528.3 [M+H]⁺.

Step 3: 4-(2-(2-Aminopyridin-3-yl)-5-(5-fluoropyrazin-2-yl)-3H-imidazo[4,5-b]pyridin-3-yl)phenyl)methanol To a solution of 3-(3-(4-(((tert-butyldimethylsilyl)oxy)methyl)phenyl)-5-(5-fluoropyrazin-2-yl)-3H-imidazo[4,5-b]pyridin-2-yl)pyridin-2-amine (480 mg, 910 μmol) in THF (4 mL) was added TBAF (1.5 mL, 1 M in THF). The mixture was stirred at 25° C. for 0.5 hr. The reaction mixture was poured into H₂O (15 mL) and extracted with EtOAc (15 mL×3). After purified by silica gel flash chromatography (Eluent of 0%~65% EtOAc in petroleum ether), 4-(2-(2-aminopyridin-3-yl)-5-(5-fluoropyrazin-2-yl)-3H-imidazo[4,5-b]pyridin-3-yl)phenyl)methanol (153 mg, yield: 41%) was obtained as a yellow solid. MS: m/z=414.1 [M+H]⁺. ¹H NMR (400 MHz, Dimethysulfoxide-d₆) δ 9.03-8.88 (m, 1H), 8.72 (d, J=8.8 Hz, 1H), 8.42-8.25 (m, 2H), 8.01 (dd, J=4.8, 1.6 Hz, 1H), 7.55-7.39 (m, 4H), 7.34-7.16 (m, 1H), 7.08-6.89 (s, 2H), 6.44 (dd, J=8.0, 5.2 Hz, 1H), 5.49-5.22 (m, 1H), 4.61-4.60 (m, 2H). ¹⁹F NMR (400 MHz, Dimethysulfoxide-d₆) δ -82.690.

Step 4: 3-(3-(4-(Chloromethyl)phenyl)-5-(5-fluoropyrazin-2-yl)-3H-imidazo[4,5-b]pyridin-2-yl)pyridin-2-amine To a solution of 4-(2-(2-aminopyridin-3-yl)-5-(5-fluoropyrazin-2-yl)-3H-imidazo[4,5-b]pyridin-3-yl)phenyl)methanol (153 mg, 370 μmol) in CH₂Cl₂ (2 mL) was added SOCl₂ (1 mL). The mixture was stirred at 40° C. for 0.3 hr. The reaction was concentrated under reduced pressure to give 3-(3-(4-(chloromethyl)phenyl)-5-(5-fluoropyrazin-2-yl)-3H-imidazo[4,5-b]pyridin-2-yl)pyridin-2-amine (Intermediate 275, 146 mg, HCl salt) was obtained as a yellow solid. MS: m/z=432.1 [M+H]⁺.

Intermediate 276:
5-Bromo-2-(fluoromethoxy)pyridine

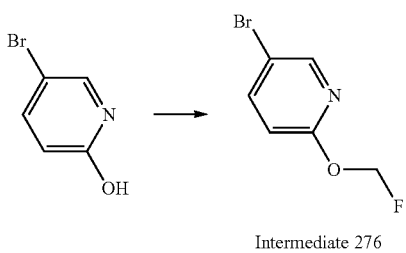 [SMILES: Oc1ccc(Br)cn1 ; FCOc1ccc(Br)cn1]

Intermediate 276

To a solution of 5-bromopyridin-2-ol (1 g, 5.8 mmol) and K₂CO₃ (2.4 g, 17.2 mmol) in DMF (10 mL) was added fluoromethyl 4-methylbenzenesulfonate (1.2 g, 5.8 mmol) at 25° C. The mixture was stirred at 50° C. for 2 hr. The mixture was quenched with H₂O (50 mL) and extracted with CH₂Cl₂ (20 mL×2). The combined organic layers were washed with brine (50 mL×3), dried over Na₂SO₄, filtered and concentrated. After purified by silica gel flash chromatography (Eluent of 0~15% Ethyl acetate in petroleum ether), 5-bromo-2-(fluoromethoxy)pyridine (Intermediate 276, 1 g, yield: 84%) was obtained as a yellow oil. MS: m, J=205.8, 207.8 [M+H]⁺. ¹H NMR (400 MHz, Dimethylsulfoxide-d₆) δ 8.18 (d, J=2.8 Hz, 1H), 7.61 (dd, J=9.6, 2.8 Hz, 1H), 6.47 (d, J=9.6 Hz, 1H), 5.90-5.75 (m, 2H). ¹⁹F NMR (400 MHz, Dimethylsulfoxide-d₆) δ -172.73.

Intermediate 277: 3-(3-(4-(Chloromethyl)phenyl)-5-(6-(fluoromethoxy)pyridin-3-yl)-3H-imidazo[4,5-b]pyridin-2-yl)pyridin-2-amine

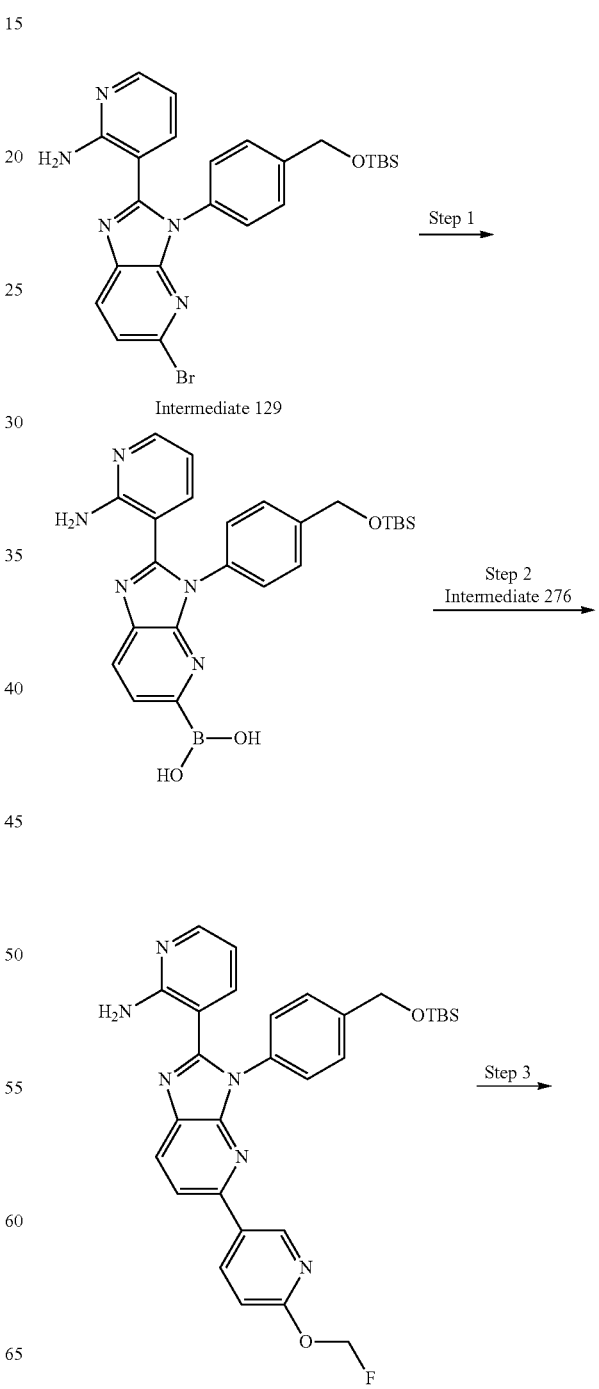

-continued

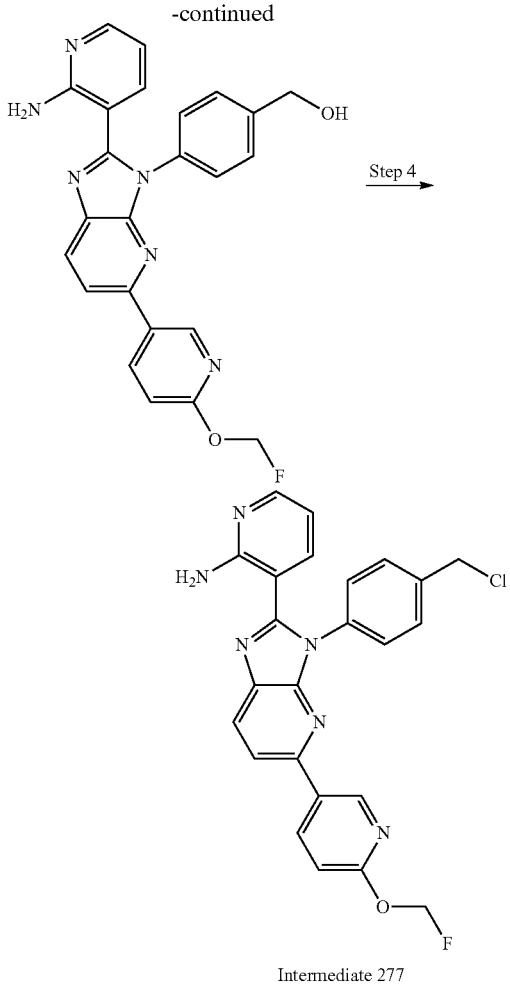

Intermediate 277

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl₂ (143 mg, 196 μmol) in 1,4-dioxane (10 mL) was degassed and purged with N₂ three times. The mixture was stirred at 90° C. for 8 hr under N₂ atmosphere. (2-(2-aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]⁺.

Step 2: 3-(3-(4-(((tert-Butyldimethylsilyl)oxy)methyl)phenyl)-5-(6-(fluoromethoxy)pyridin-3-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (466 mg, 980 μmol), Intermediate 276 (202 mg, 980 μmol), Pd(dppf)Cl₂ (71.7 mg, 98 μmol) and Cs₂CO₃ (958 mg, 2.94 mmol) in 1,4-dioxane (5 mL) and H₂O (1 mL) was degassed and purged with N₂ for 3 times. The mixture was stirred at 90° C. for 16 hr under N₂ atmosphere. The reaction mixture was quenched with H₂O (5 mL) and extracted with EtOAc (10 mL×3). The combined organic layers were washed with brine (30 mL), dried over Na₂SO₄, filtered and concentrated under reduced pressure. After purified by silica gel flash chromatography (Eluent of 15%~37% EtOAc in petroleum ether), 3-(3-(4-(((tert-butyldimethylsilyl)oxy)methyl)phenyl)-5-(6-(fluoromethoxy)pyridin-3-yl)-3H-imidazo[4,5-b]pyridin-2-yl)pyridin-2-amine (300 mg, yield: 55% for two steps) was obtained as a purple solid. MS: m/z=557.7 [M+H]⁺. ¹H NMR (400 MHz, Dimethylsulfoxide-d₆) δ 8.90 (d, J=2.0 Hz, 1H), 8.41 (dd, J=8.8, 2.4 Hz, 1H), 8.29 (d, J=8.4 Hz, 1H), 8.05-7.97 (m, 2H), 7.51-7.46 (m, 4H), 7.20 (dd, J=7.6, 2.0 Hz, 1H), 7.10-7.00 (m, 3H), 6.39 (dd, J=7.6, 4.8 Hz, 1H), 6.21-6.04 (m, 2H), 4.82 (s, 2H), 0.92 (s, 9H), 0.11 (s, 6H). ¹⁹F NMR (400 MHz, Dimethylsulfoxide-d₆) δ -154.37.

Step 3: (4-(2-(2-Aminopyridin-3-yl)-5-(6-(fluoromethoxy)pyridin-3-yl)-3H-imidazo[4,5-b]pyridin-3-yl)phenyl)methanol To a solution of 3-(3-(4-(((tert-butyldimethylsilyl)oxy)methyl)phenyl)-5-(6-(fluoromethoxy)pyridin-3-yl)-3H-imidazo[4,5-b]pyridin-2-yl)pyridin-2-amine (300 mg, 539 μmol) in THF (5 mL) was added TBAF (423 mg, 1.62 mmol, 1 M in THF). The mixture was stirred at 25° C. for 1 hr. The reaction mixture was quenched with H₂O (5 mL) at 25° C. and extracted with EtOAc (10 mL×3). The combined organic layers were washed with brine (50 mL×3), dried over Na₂SO₄, filtered and concentrated under reduced pressure. (4-(2-(2-Aminopyridin-3-yl)-5-(6-(fluoromethoxy)pyridin-3-yl)-3H-imidazo[4,5-b]pyridin-3-yl)phenyl)methanol (240 mg) was obtained as a brown solid. MS: m/z=443.1 [M+H]⁺. ¹H NMR (400 MHz, Dimethylsulfoxide-d₆) δ 8.94-8.87 (m, 1H), 8.46-8.38 (m, 1H), 8.29 (d, J=8.0 Hz, 1H), 8.08-7.93 (m, 2H), 7.56-7.36 (m, 4H), 7.23 (d, J=7.6 Hz, 1H), 7.09 (d, J=8.4 Hz, 1H), 7.05-6.92 (m, 2H), 6.47-6.37 (m, 11H), 6.25-5.99 (m, 2H), 5.48-5.29 (m, 1H), 4.70-4.49 (m, 2H). ¹⁹F NMR (400 MHz, Dimethylsulfoxide-d₆) δ -154.36.

Step 4: 3-(3-(4-(Chloromethyl)phenyl)-5-(6-(fluoromethoxy)pyridin-3-yl)-3H-imidazo[4,5-b]pyridin-2-yl)pyridin-2-amine To a solution of (4-(2-(2-aminopyridin-3-yl)-5-(6-(fluoromethoxy)pyridin-3-yl)-3H-imidazo[4,5-b]pyridin-3-yl)phenyl)methanol (240 mg, 542 μmol) in CH₂Cl₂ (5 mL) was added SOCl₂ (194 mg, 1.63 mmol). The mixture was stirred at 40° C. for 0.5 hr. The reaction was concentrated under reduced pressure to give 3-(3-(4-(chloromethyl)phenyl)-5-(6-(fluoromethoxy)pyridin-3-yl)-3H-imidazo[4,5-b]pyridin-2-yl)pyridin-2-amine (Intermediate 277, 250 mg, HCl salt) as a yellow solid. MS: m/z=461.0 [M+H]⁺.

Intermediate 278:
5-Bromo-1-(fluoromethyl)pyridin-2(1H)-one

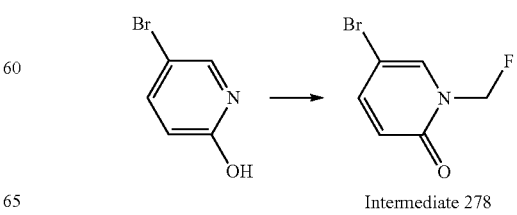

Intermediate 278

To a solution of 5-bromopyridin-2-ol (3 g, 17.2 mmol), and K$_2$CO$_3$ (7.1 g, 52 mmol) in DMF (10 mL) was added bromofluoromethane (2.9 g, 26 mmol) at 0° C. The mixture was stirred at 0° C. for 2 hr. The mixture was quenched with H$_2$O (50 mL) and extracted with CH$_2$Cl$_2$ (20 mL×2). The combined organic layers were washed with brine (50 mL×3), dried over Na$_2$SO$_4$, filtered and concentrated. After purified by silica gel flash chromatography (Eluent of 0~15% Ethyl acetate in petroleum ether), 5-Bromo-1-(fluoromethyl)pyridin-2(1H)-one (Intermediate 278, 2.7 g, yield: 76%) was obtained as a yellow oil. MS: m/z=205.7, 207.7 [M+H]$^+$. $^1$H NMR (400 MHz, Dimethylsulfoxide-d$_6$) δ 8.19 (d, J=2.8 Hz, 1H), 7.61 (dd, J=9.6, 2.8 Hz, 1H), 6.47 (d, J=9.6 Hz, 1H), 5.88 (d, J=51.2 Hz, 2H). $^9$F NMR (400 MHz, Dimethylsulfoxide-d$_6$) δ −172.733.

Intermediate 279: 5-(2-(2-Aminopyridin-3-yl)-3-(4-(chloromethyl)phenyl)-3H-imidazo[4,5-b]pyridin-5-yl)-1-(fluoromethyl)pyridin-2(1H)-one

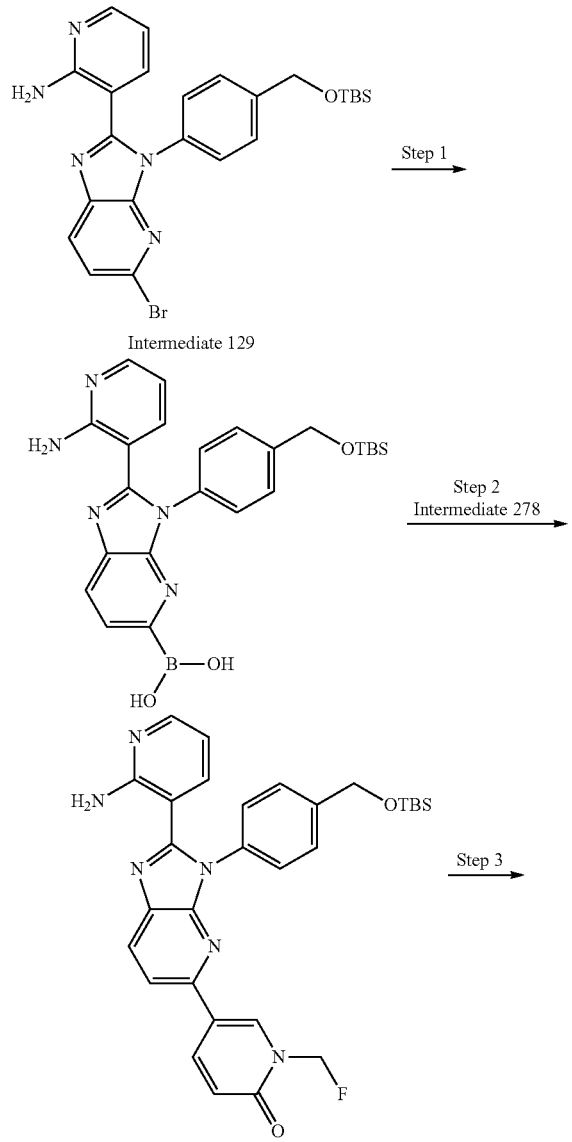

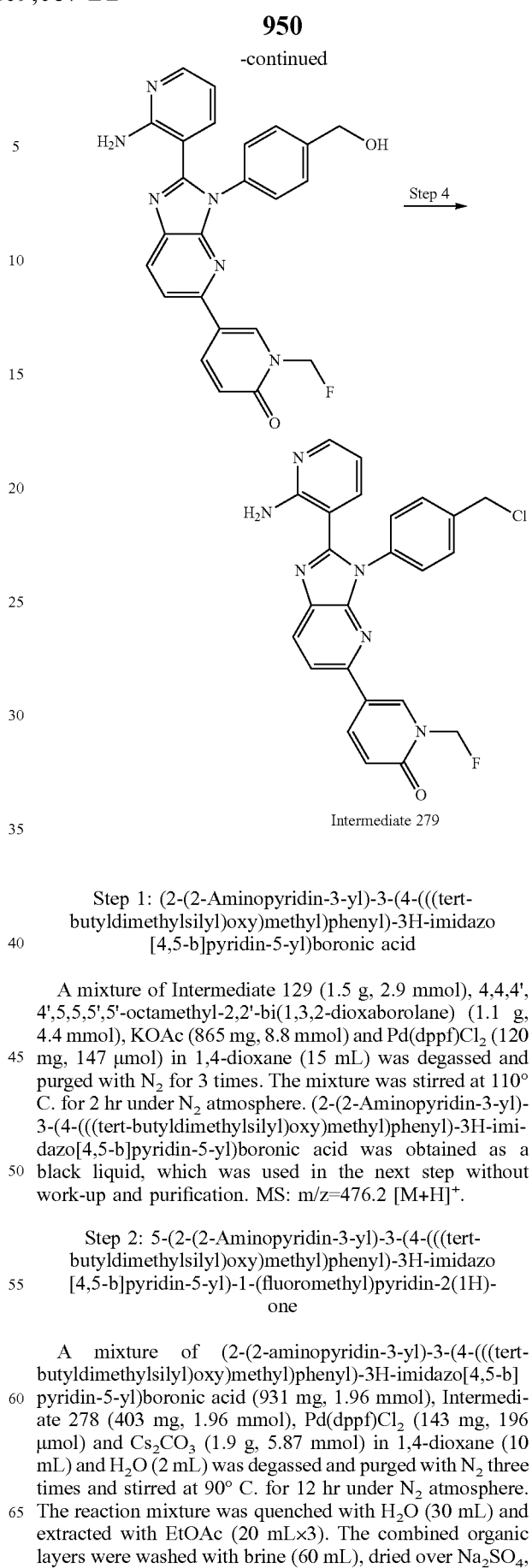

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1.5 g, 2.9 mmol), 4,4,4',4',5,5,5',5'-octamethyl-2,2'-bi(1,3,2-dioxaborolane) (1.1 g, 4.4 mmol), KOAc (865 mg, 8.8 mmol) and Pd(dppf)Cl$_2$ (120 mg, 147 μmol) in 1,4-dioxane (15 mL) was degassed and purged with N$_2$ for 3 times. The mixture was stirred at 110° C. for 2 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 5-(2-(2-Aminopyridin-3-yl)-3-(4-(((tert-butyldimethylsilyl)oxy)methyl)phenyl)-3H-imidazo[4,5-b]pyridin-5-yl)-1-(fluoromethyl)pyridin-2(1H)-one A mixture of (2-(2-aminopyridin-3-yl)-3-(4-(((tert-butyldimethylsilyl)oxy)methyl)phenyl)-3H-imidazo[4,5-b]pyridin-5-yl)boronic acid (931 mg, 1.96 mmol), Intermediate 278 (403 mg, 1.96 mmol), Pd(dppf)Cl$_2$ (143 mg, 196 μmol) and Cs$_2$CO$_3$ (1.9 g, 5.87 mmol) in 1,4-dioxane (10 mL) and H$_2$O (2 mL) was degassed and purged with N$_2$ three times and stirred at 90° C. for 12 hr under N$_2$ atmosphere. The reaction mixture was quenched with H$_2$O (30 mL) and extracted with EtOAc (20 mL×3). The combined organic layers were washed with brine (60 mL), dried over Na$_2$SO$_4$, filtered and concentrated under reduced pressure. After purified by silica gel flash chromatography (Eluent of 20%~65% EtOAc in petroleum ether), 5-(2-(2-aminopyridin-3-yl)-3-(4-(((tert-butyldimethylsilyl)oxy)methyl)phenyl)-3H-imidazo[4,5-b]pyridin-5-yl)-1-(fluoromethyl)pyridin-2(1H)-one (570 mg, yield: 52% for two steps) was obtained as a brown solid. MS: m/z=557.2 [M+H]+.

Step 3: 5-(2-(2-Aminopyridin-3-yl)-3-(4-(hydroxymethyl)phenyl)-3H-imidazo[4,5-b]pyridin-5-yl)-1-(fluoromethyl)pyridin-2(1H)-one To a solution of 5-(2-(2-aminopyridin-3-yl)-3-(4-(((tert-butyldimethylsilyl)oxy)methyl)phenyl)-3H-imidazo[4,5-b]pyridin-5-yl)-1-(fluoromethyl)pyridin-2(1H)-one (570 mg, 1.02 mmol) in THF (10 mL) was added TBAF (0.8 mL, 1 M in THF). The mixture was stirred at 25° C. for 1 hr. The reaction mixture was quenched with $H_2O$ (20 mL) at 25° C. and extracted with EtOAc (10 mL×3). The combined organic layers were washed with brine (20 mL×3), dried over $Na_2SO_4$, filtered and concentrated under reduced pressure. 5-(2-(2-Aminopyridin-3-yl)-3-(4-(hydroxymethyl)phenyl)-3H-imidazo[4,5-b]pyridin-5-yl)-1-(fluoromethyl)pyridin-2(11H)-one (440 mg) was obtained as a brown solid. MS: m/z=442.9 [M+H]+. $^1$H NMR (400 MHz, Dimethylsulfoxide-$d_6$) δ 8.60 (d, J=2.4 Hz, 1H), 8.26 (d, J=8.4 Hz, 1H), 8.16 (dd, J=9.6, 2.4 Hz, 1H), 7.99 (dd, J=4.8, 2.0 Hz, 1H), 7.85 (d, J=8.4 Hz, 1H), 7.50-7.46 (m, 2H), 7.45-7.41 (m, 2H), 7.22-7.16 (m, 1H), 6.99-6.92 (m, 2H), 6.61 (d, J=10.0 Hz, 1H), 6.41 (dd, J=7.6, 4.8 Hz, 1H), 6.03 (d, J=50.8 Hz, 2H), 5.38-5.33 (m, 1H), 4.62-4.57 (m, 2H). $^{19}$F NMR (400 MHz, Dimethylsulfoxide-$d_6$) δ −172.572.

Step 4: 5-(2-(2-Aminopyridin-3-yl)-3-(4-(chloromethyl)phenyl)-3H-imidazo[4,5-b]pyridin-5-yl)-1-(fluoromethyl)pyridin-2(1H)-one To a solution of 5-(2-(2-aminopyridin-3-yl)-3-(4-(hydroxymethyl)phenyl)-3H-imidazo[4,5-b]pyridin-5-yl)-1-(fluoromethyl)pyridin-2(1H)-one (440 mg, 994 μmol) in $CH_2Cl_2$ (5 mL) was added $SOCl_2$ (355 mg, 2.98 mmol). The mixture was stirred at 40° C. for 0.5 hr. The reaction was concentrated under reduced pressure to give 5-(2-(2-aminopyridin-3-yl)-3-(4-(chloromethyl)phenyl)-3H-imidazo[4,5-b]pyridin-5-yl)-1-(fluoromethyl)pyridin-2(1H)-one (Intermediate 297, 458 mg, HCl salt) as a yellow solid. MS: m/z=461.0, 462.7 [M+H]+.

Intermediate 280: 4-Bromo-2-(methyl-$d_3$)-2H-1,2,3-triazole

Step 1: 4,5-Dibromo-2H-1,2,3-triazole

To a solution of 2H-1,2,3-triazole (25 g, 362 mmol) in $H_2O$ (300 mL) was added dropwise $Br_2$ (75.2 g, 471 mmol) at 0° C. under $N_2$ atmosphere. The mixture was stirred at 25° C. for 16 hr under $N_2$ atmosphere. The reaction mixture was filtered. After triturated with MeOH (100 mL) at 25° C. for 10 min, 4,5-dibromo-2H-1,2,3-triazole (48 g, yield: 58%) was obtained as a white solid. MS: m/z=226.0, 228.0, 230.0 [M+H]+.

Step 2: 4,5-Dibromo-2-(methyl-$d_3$)-2H-1,2,3-triazole

To a solution of 4,5-dibromo-2H-1,2,3-triazole (20 g, 88.2 mmol) and $K_2CO_3$ (24.4 g, 176 mmol) in DMF (100 mL) was added dropwise $CD_3I$ (25 g, 176 mmol) at 0° C. The mixture was stirred at 25° C. for 16 hr. The reaction mixture was quenched with $H_2O$ (200 mL) at 25° C. and extracted with $CH_2Cl_2$ (200 mL×3). The combined organic layers were washed with brine (200 mL×3), dried over $Na_2SO_4$, filtered and concentrated under reduced pressure.

After purified by silica gel flash chromatography (Eluent of 0%~30% EtOAc in petroleum ether), 4,5-dibromo-2-(methyl-$d_6$)-2H-1,2,3-triazole (10 g, yield: 47%) was obtained as a colorless oil. MS: m/z=243.0, 245.0, 247.0 [M+H]+.

Step 3: 4-Bromo-2-(methyl-$d_6$)-2H-1,2,3-triazole

To a solution of 4,5-dibromo-2-(methyl-$d_3$)-2H-1,2,3-triazole (10 g, 41 mmol) in THF (100 mL) was added dropwise n-BuLi (5.25 g, 82 mmol, 2.5 M in THF) at −78° C. The mixture was stirred at −78° C. for 1 hr. The reaction mixture was quenched with $H_2O$ (200 mL) at 25° C. and extracted with $CH_2Cl_2$ (200 mL×3). The combined organic layers were washed with brine (200 mL×3), dried over $Na_2SO_4$, filtered and concentrated under reduced pressure. 4-Bromo-2-(methyl-$d_3$)-2H-1,2,3-triazole (Intermediate 280, 3.6 g, yield: 53%) was obtained as a yellow oil. $^1$H NMR (400 MHz, Dimethylsulfoxide-$d_6$) δ 7.94 (s, 1H).

Intermediate 281: 3-(3-(4-(Chloromethyl)phenyl)-5-(2-(methyl-$d_6$)-2H-1,2,3-triazol-4-yl)-3H-imidazo[4,5-b]pyridin-2-yl)pyridin-2-amine

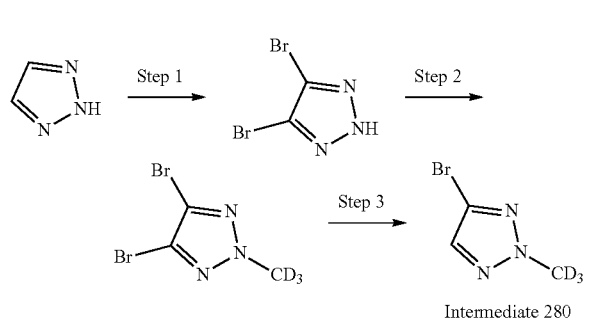

Intermediate 280

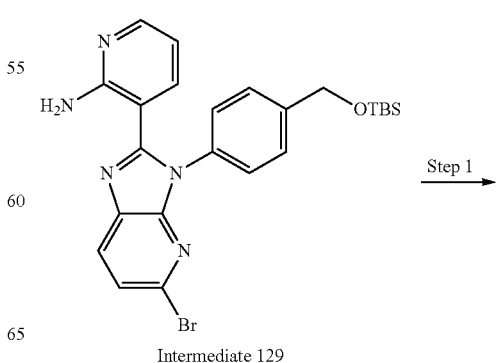

Intermediate 129

-continued

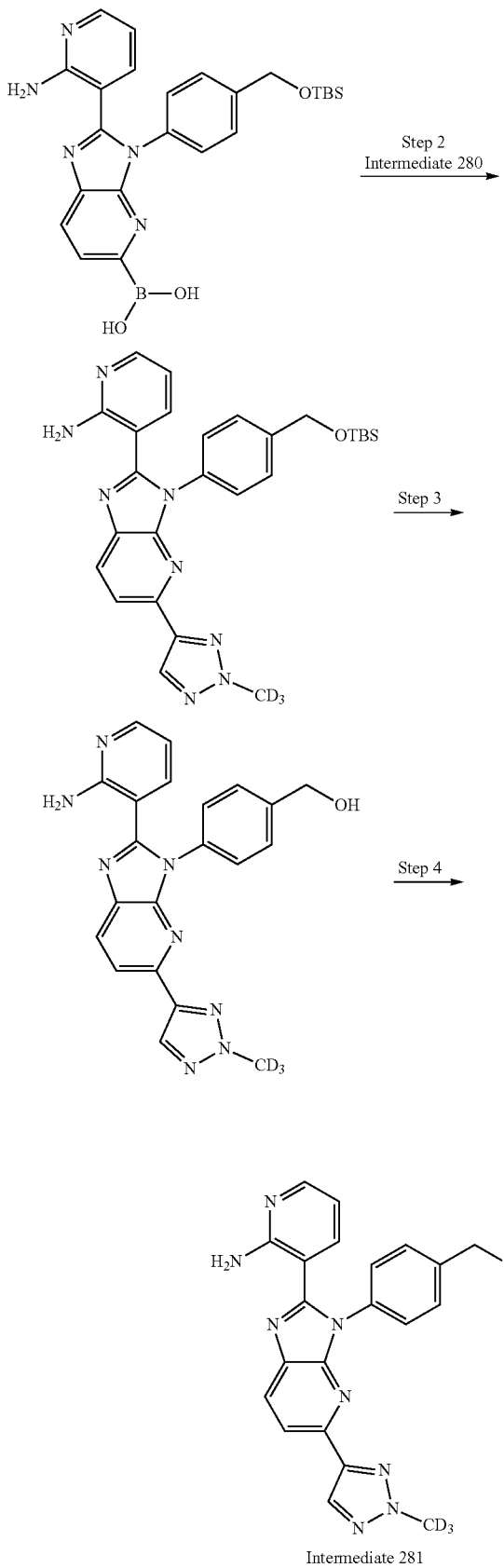

Intermediate 281

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (11 g, 21.6 mmol), 4,4,4',4',5,5,5',5'-octamethyl-2,2'-bi(1,3,2-dioxaborolane) (10.9 g, 43.1 mmol), KOAc (6.34 g, 64.6 mmol) and Pd(dppf)Cl$_2$ (1.58 g, 2.15 mmol) in 1,4-dioxane (100 mL) was degassed and purged with N$_2$ three times. The mixture was stirred at 80° C. for 4 hr under N2 atmosphere. (2-(2-aminopyridin-3-yl)-3-(4-(((tert-butyldimethylsilyl)oxy)methyl)phenyl)-3H-imidazo[4,5-b]pyridin-5-yl)boronic acid was obtained as a black liquid, the mixture was used for next step directly and without work-up and purification. MS: m/z=476.1 [M+H]$^+$.

Step 2: 3-(3-(4-(((tert-Butyldimethylsilyl)oxy)methyl)phenyl)-5-(2-(methyl-d$_3$)-2H-1,2,3-triazol-4-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (10 g, 21 mmol), Intermediate 280 (3.47 g, 21 mmol), Pd(dppf)Cl$_2$ (1.54 g, 2.1 mmol) and Cs$_2$CO$_3$ (20.6 g, 63.1 mmol) in 1,4-dioxane (100 mL) and H$_2$O (20 mL) was degassed and purged with N$_2$ three times. The mixture was stirred at 80° C. for 16 hr under N$_2$ atmosphere. The reaction mixture was quenched with H$_2$O (200 mL) and extracted with CH$_2$Cl$_2$ (200 mL×2). The combined organic layers were washed with brine (200 mL), dried over Na$_2$SO$_4$, filtered and concentrated under reduced pressure. After purified by silica gel flash chromatography (Eluent of 10%~45% EtOAc in petroleum ether), 3-(3-(4-(((tert-butyldimethylsilyl)oxy)methyl)phenyl)-5-(2-(methyl-d$_6$)-2H-1,2,3-triazol-4-yl)-3H-imidazo[4,5-b]pyridin-2-yl)pyridin-2-amine (200 mg, yield: 4.1% for two steps) was obtained as a brown solid. MS: m/z=516.1 [M+H]$^+$. $^1$H NMR (400 MHz, Dimethylsulfoxide-d$_6$) δ 8.27 (d, J=8.4 Hz, 1H), 8.05-7.87 (m, 3H), 7.51-7.44 (m, 4H), 7.18 (dd, J=7.6, 1.6 Hz, 1H), 6.97 (s, 2H), 6.38 (dd, J=7.6, 4.8 Hz, 1H), 4.82 (s, 2H), 0.93 (s, 9H), 0.11 (s, 6H).

Step 3: (4-(2-(2-Aminopyridin-3-yl)-5-(2-(methyl-d$_3$)-2H-1,2,3-triazol-4-yl)-3H-imidazo[4,5-b]pyridin-3-yl)phenyl)methanol To a solution of 3-(3-(4-(((tert-butyldimethylsilyl)oxy)methyl)phenyl)-5-(2-(methyl-d$_6$)-2H-1,2,3-triazol-4-yl)-3H-imidazo[4,5-b]pyridin-2-yl)pyridin-2-amine (500 mg, 970 μmol) in THF (5 mL) was added TBAF (507 mg, 1.94 mmol, 1 M in THF). The mixture was stirred at 25° C. for 1 hr. The reaction mixture was quenched with H$_2$O (20 mL) at 25° C. and extracted with CH$_2$Cl$_2$ (20 mL×3). The combined organic layers were washed with brine (20 mL×3), dried over Na$_2$SO$_4$, filtered and concentrated under reduced pressure. (4-(2-(2-Aminopyridin-3-yl)-5-(2-(methyl-d$_6$)-2H-1,2,3-triazol-4-yl)-3H-imidazo[4,5-b]pyridin-3-yl)phenyl)methanol (380 mg, yield: 84%) was obtained as a brown solid. MS: m/z=402.2 [M+H]$^+$. $^1$H NMR (400 MHz, Dimethylsulfoxide-d$_6$) δ 8.27 (d, J=8.4 Hz, 1H), 8.04 (s, 1H), 8.00 (dd, J=4.8, 1.6 Hz, 1H), 7.93 (d, J=8.4 Hz, 1H), 7.52-7.40 (m, 4H), 7.25-7.16 (m, 1H), 6.93 (s, 2H), 6.41 (dd, J=7.6, 4.8 Hz, 1H), 5.37 (t, J=5.6 Hz, 1H), 4.60 (d, J=5.6 Hz, 2H).

Step 4: 3-(3-(4-(Chloromethyl)phenyl)-5-(2-(methyl-d$_6$)-2H-1,2,3-triazol-4-yl)-3H-imidazo[4,5-b]pyridin-2-yl)pyridin-2-amine To a solution of (4-(2-(2-aminopyridin-3-yl)-5-(2-(methyl-d$_6$)-2H-1,2,3-triazol-4-yl)-3H-imidazo[4,5-b]pyridin-3-yl)phenyl)methanol (380 mg, 947 μmol) in CH$_2$Cl$_2$ (5 mL) was added SOCl$_2$ (338 mg, 2.84 mmol). The mixture was stirred at 40° C. for 0.5 hr. The reaction was concentrated under reduced pressure to give 3-(3-(4-(chloromethyl)phenyl)-5-(2-(methyl-d$_3$)-2H-1,2,3-triazol-4-yl)-3H-imidazo[4,5-b]pyridin-2-yl)pyridin-2-amine (Intermediate 281, 420 mg, HCl salt) as a brown solid. MS: m/z=420.2 [M+H]$^+$.

Intermediate 282 & 283: 4,5-Dibromo-2-ethyl-2H-1,2,3-triazole & 4,5-Dibromo-1-ethyl-1H-1,2,3-triazole

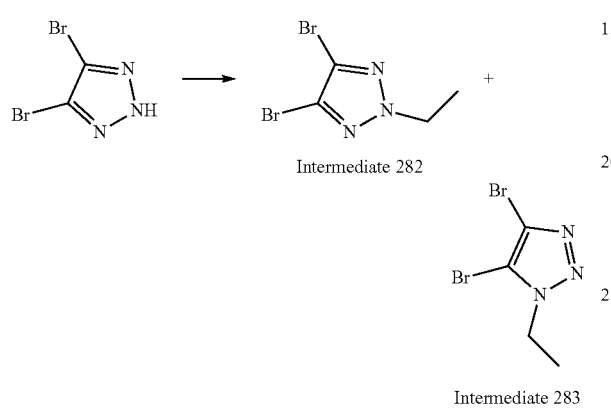

To a solution of 4,5-dibromo-2H-triazole (2 g, 8.82 mmol) in DMF (20 mL) were added K$_2$CO$_3$ (1.83 g, 13.2 mmol) and iodoethane (1.38 g, 8.82 mmol, 705 μL) at 20° C. The reaction mixture was stirred at 20° C. for 12 hr. The reaction mixture was diluted with H$_2$O (100 mL) and extracted with EtOAc (100 mL). The organic layer was separated, dried over anhydrous Na$_2$SO$_4$, filtered and concentrated under vacuum. After purified by silica gel flash chromatography (EtOAc in petroleum ether=0-5%), 4,5-dibromo-2-ethyl-2H-1,2,3-triazole (Intermediate 282, 3.1 g, yield: 69%) was obtained as a yellow oil. $^1$H NMR (400 MHz, Dimethylsulfoxide-d$_6$) δ 4.45 (q, J=7.2 Hz, 2H), 1.43 (t, J=7.2 Hz, 3H), 4,5-Dibromo-1-ethyl-1H-1,2,3-triazole (Intermediate 283, 780 mg, yield: 17%) was obtained as a white solid. $^1$H NMR (400 MHz, Dimethylsulfoxide-d$_6$) δ 4.42 (q, J=7.2 Hz, 2H), 1.41 (t, J=7.2 Hz, 3H).

Intermediate 284:
4-Bromo-2-ethyl-2H-1,2,3-triazole

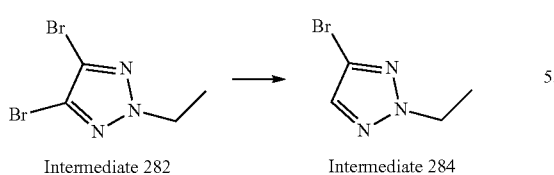

To a mixture of Intermediate 282 (1 g, 3.92 mmol) in THF (10 mL) was added n-BuLi (2.5M in hexane, 1.73 mL) at −70° C. under N$_2$. The mixture was stirred at −70° C. for 1 hr under N$_2$. The reaction mixture was quenched with H$_2$O (20 mL) at −70° C. under N$_2$ and extracted with EtOAc (20 mL×3). The combined organic layers were washed with brine (10 mL), dried over anhydrous Na$_2$SO$_4$, filtered and concentrated under reduced pressure. 4-Bromo-2-ethyl-2H-1,2,3-triazole (Intermediate 284, 600 mg, 3.41 mmol, yield: 87%) was obtained as a yellow oil. MS: m/z=175.7, 177.7 [M+H]$^+$. $^1$H NMR (400 MHz, Dimethylsulfoxide-d$_6$) δ 7.95 (s, 1H), 4.44 (q, J=7.2 Hz, 2H), 1.43 (t, J=7.2 Hz, 3H).

Intermediate 285: 3-(3-(4-(Chloromethyl)phenyl)-5-(2-ethyl-2H-1,2,3-triazol-4-yl)-3H-imidazo[4,5-b]pyridin-2-yl)pyridin-2-amine

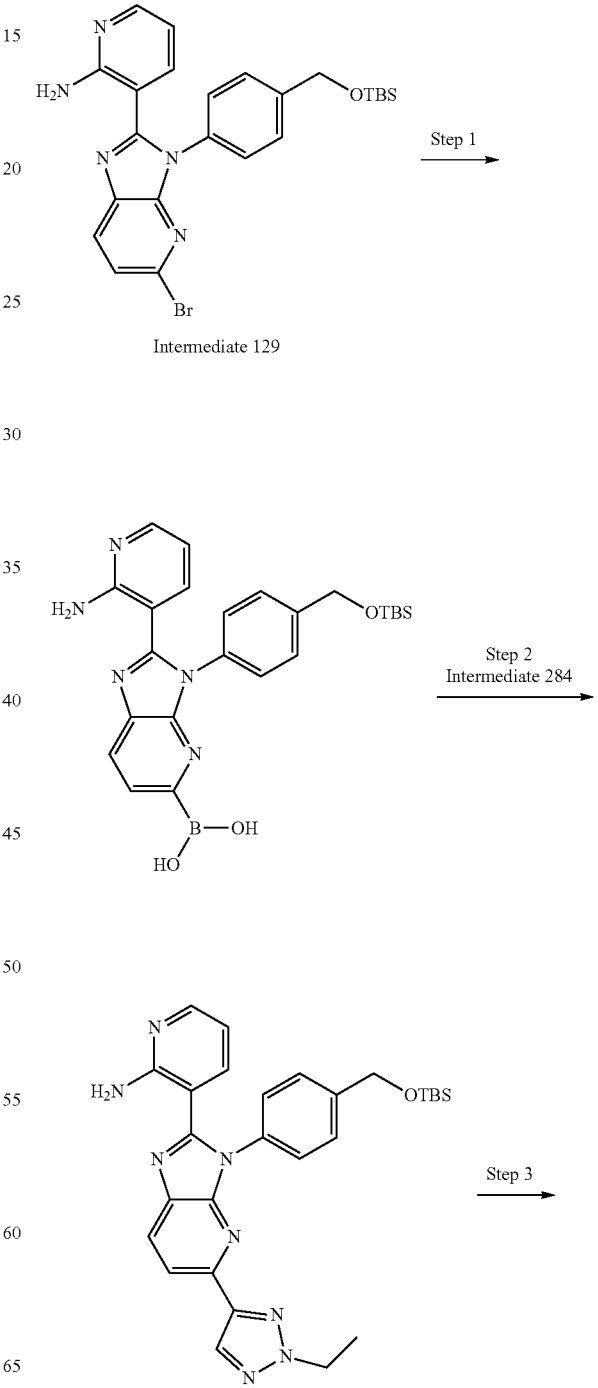

-continued

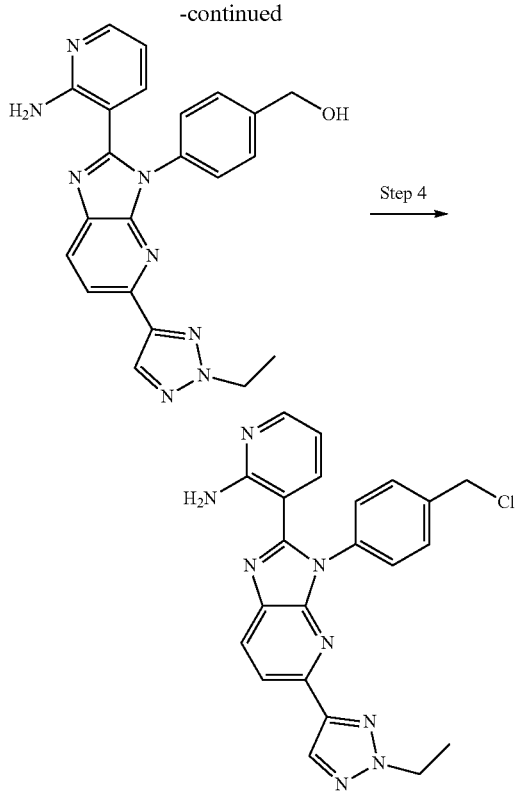

Intermediate 285

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (320 mg, 0.63 mmol), 4,4,4',4',5,5,5',5'-octamethyl-2,2'-bi(1,3,2-dioxaborolane) (318 mg, 1.25 mmol), KOAc (184 mg, 1.88 mmol) and Pd(dppf)Cl$_2$ (46 mg, 63 μmol) in 1,4-dioxane (5 mL) was degassed and purged with N$_2$ three times. The mixture was stirred at 80° C. for 4 hr under N2 atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]$^+$.

Step 2: 3-(3-(4-(((tert-Butyldimethylsilyl)oxy)methyl)phenyl)-5-(2-ethyl-2H-1,2,3-triazol-4-yl)-3H-imidazo[4,5-b]pyridin-2-yl)pyridin-2-amine To a mixture of (2-(2-aminopyridin-3-yl)-3-(4-(((tert-butyldimethylsilyl)oxy)methyl)phenyl)-3H-imidazo[4,5-b]pyridin-5-yl)boronic acid (300 mg, 631 μmol) and Intermediate 284 (122 mg, 694 μmol) in 1,4-dioxane (6 mL) and H$_2$O (2 mL) were added Cs$_2$CO$_3$ (617 mg, 1.89 mmol) and Pd(dppf)Cl$_2$ (46.2 mg, 63.1 μmol). The mixture was stirred at 100° C. for 2 hr under N$_2$. The mixture was diluted with H$_2$O (20 mL) and extracted with EtOAc (20 mL×2). The combined organic layers were washed with brine (20 mL), dried over anhydrous Na$_2$SO$_4$, filtered and concentrated. After purified by silica gel flash chromatography (EtOAc in petroleum ether=0-50%), 3-(3-(4-(((tert-butyldimethylsilyl)oxy)methyl)phenyl)-5-(2-ethyl-2H-1,2,3-triazol-4-yl)-3H-imidazo[4,5-b]pyridin-2-yl)pyridin-2-amine (260 mg, 494 μmol, yield: 78% for two steps) was obtained as a yellow solid. MS: m/z=527.3 [M+H]$^+$. $^1$H NMR (400 MHz, Dimethylsulfoxide-d$_6$) δ 8.27 (d, J=8.4 Hz, 1H), 8.03 (s, 1H), 7.99 (dd, J=4.8, 2.0 Hz, 1H), 7.94 (d, J=8.0 Hz, 1H), 7.50-7.43 (m, 4H), 7.18 (dd, J=7.6, 2.0 Hz, 1H), 6.97 (s, 2H), 6.38 (dd, J=8.0, 5.2 Hz, 1H), 4.81 (s, 2H), 4.50 (q, J=7.2 Hz, 2H), 1.49 (t, J=7.2 Hz, 3H), 0.92 (s, 9H), 0.11 (s, 6H).

Step 3: (4-(2-(2-Aminopyridin-3-yl)-5-(2-ethyl-2H-1,2,3-triazol-4-yl)-3H-imidazo[4,5-b]pyridin-3-yl)phenyl)methanol To a mixture of 3-(3-(4-(((tert-butyldimethylsilyl)oxy)methyl)phenyl)-5-(2-ethyl-2H-1,2,3-triazol-4-yl)-3H-imidazo[4,5-b]pyridin-2-yl)pyridin-2-amine (210 mg, 399 μmol) in THF (5 mL) was added TBAF (1M in THF, 598 μL), the mixture was stirred at 20° C. for 1 hr. The mixture was diluted with H$_2$O (10 mL) and extracted with EtOAc (10 mL×2). The combined organic layers were washed with brine (10 mL), dried over anhydrous Na$_2$SO$_4$, filtered and concentrated, (4-(2-(2-aminopyridin-3-yl)-5-(2-ethyl-2H-1,2,3-triazol-4-yl)-3H-imidazo[4,5-b]pyridin-3-yl)phenyl)methanol (164 mg, 398 μmol, yield: 100%) was obtained as a yellow solid. MS: m/z=413.2 [M+H]$^+$. $^1$H NMR (400 MHz, Dimethylsulfoxide-d$_6$) δ 8.27 (d, J=8.0 Hz, 1H), 8.04 (s, 1H), 7.99 (dd, J=4.8, 2.0 Hz, 1H), 7.94 (d, J=8.4 Hz, 1H), 7.51-7.40 (m, 4H), 7.21 (dd, J=7.6, 2.0 Hz, 1H), 6.92 (s, 2H), 6.41 (dd, J=7.6, 4.8 Hz, 1H), 5.37 (t, J=5.6 Hz, 1H), 4.60 (d, J=5.6 Hz, 2H), 4.50 (q, J=7.6 Hz, 2H), 1.49 (t, J=7.6 Hz, 3H).

Step 4: 3-(3-(4-(Chloromethyl)phenyl)-5-(2-ethyl-2H-1,2,3-triazol-4-yl)-3H-imidazo[4,5-b]pyridin-2-yl)pyridin-2-amine To a mixture of (4-(2-(2-aminopyridin-3-yl)-5-(2-ethyl-2H-1,2,3-triazol-4-yl)-3H-imidazo[4,5-b]pyridin-3-yl)phenyl)methanol (164 mg, 398 μmol) in CH$_2$Cl$_2$ (2 mL) was added SOCl$_2$ (86.6 μL, 1.19 mmol), the mixture was stirred at 20° C. for 1 hr. The mixture was concentrated, 3-(3-(4-(chloromethyl)phenyl)-5-(2-ethyl-2H-1,2,3-triazol-4-yl)-3H-imidazo[4,5-b]pyridin-2-yl)pyridin-2-amine (Intermediate 285, 171 mg, 397 μmol, yield: 100%) was obtained as a yellow solid. MS: m/z=431.2, 433.1 [M+H]$^+$.

Intermediate 286 & 287: 4,5-Dibromo-2-isopropyl-2H-1,2,3-triazole & 4,5-Dibromo-1-isopropyl-1H-1,2,3-triazole

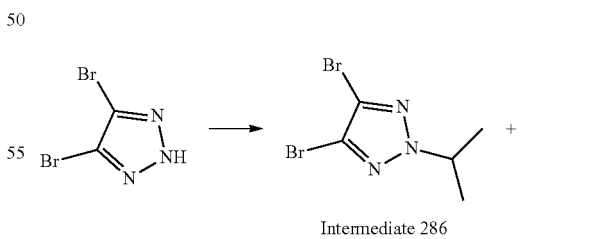

Intermediate 286

Intermediate 287

To a solution of 4,5-dibromo-2H-1,2,3-triazole (2 g, 8.82 mmol, 1 eq) in DMF (10 mL) were added $K_2CO_3$ (1.83 g, 13.2 mmol) and 2-iodopropane (1.50 g, 8.82 mmol, 880 μL) at 20° C. The reaction mixture was stirred at 20° C. for 12 hr. The mixture was diluted with $H_2O$ (50 mL) and extracted with EtOAc (50 mL). The organic layer was separated, dried over anhydrous $Na_2SO_4$ and concentrated under reduced pressure. After purified by silica gel flash chromatography (0-10% EtOAc in petroleum ether), 4,5-dibromo-2-isopropyl-2H-1,2,3-triazole (Intermediate 286, 1.7 g, yield: 71.7%) was obtained as a colorless liquid. $^1$H NMR (400 MHz, Chloroform-d) δ 4.82-4.71 (m, 1H), 1.55 (d, J=6.8 Hz, 6H), 4,5-Dibromo-1-isopropyl-1H-1,2,3-triazole (Intermediate 287, 320 mg, yield: 13.5%) was obtained as a colorless liquid. $^1$H NMR (400 MHz, Chloroform-d) δ 4.83-4.71 (m, 1H), 1.64 (d, J=6.8 Hz, 6H).

Intermediate 288:
4-Bromo-2-isopropyl-2H-1,2,3-triazole

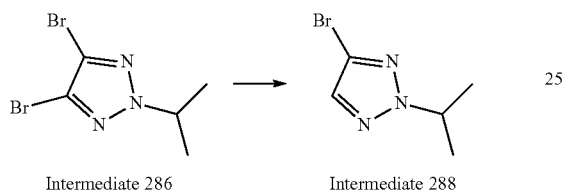

Intermediate 286      Intermediate 288

To a solution of Intermediate 286 (1 g, 3.72 mmol) in THF (9 mL) was added n-BuLi (2.5 M in hexane, 1.56 mL) at −70° C. The reaction mixture was stirred at −70° C. for 0.5 hr under $N_2$. The reaction mixture was quenched with saturated aq. $NH_4C_1$ (30 mL) dropwise at −70° C. under $N_2$. The mixture was then diluted with $H_2O$ (20 mL) and extracted with EtOAc (30 mL×2). The combined organic layers were washed with brine (30 mL), dried over anhydrous $Na_2SO_4$, filtered and concentrated under reduced pressure. 4-Bromo-2-isopropyl-2H-1,2,3-triazole (Intermediate 288, 590 mg, 3.10 mmol, yield: 83.5%) was obtained as a colorless liquid, which was used in the next step directly. MS: m/z=190.0, 192.0[M+H]$^+$. $^1$H NMR (400 MHz, Chloroform-d) δ=7.51 (s, 1H), 4.87-4.73 (m, 1H), 1.56 (d, J=6.8 Hz, 6H).

Intermediate 289: 3-(3-(4-(Chloromethyl)phenyl)-5-(2-isopropyl-2H-1,2,3-triazol-4-yl)-3H-imidazo[4,5-b]pyridin-2-yl)pyridin-2-amine

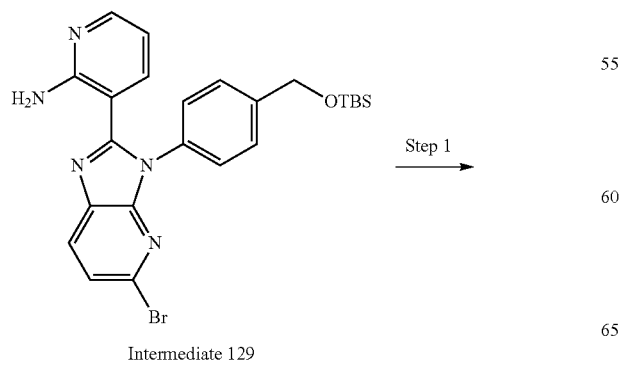

Intermediate 129

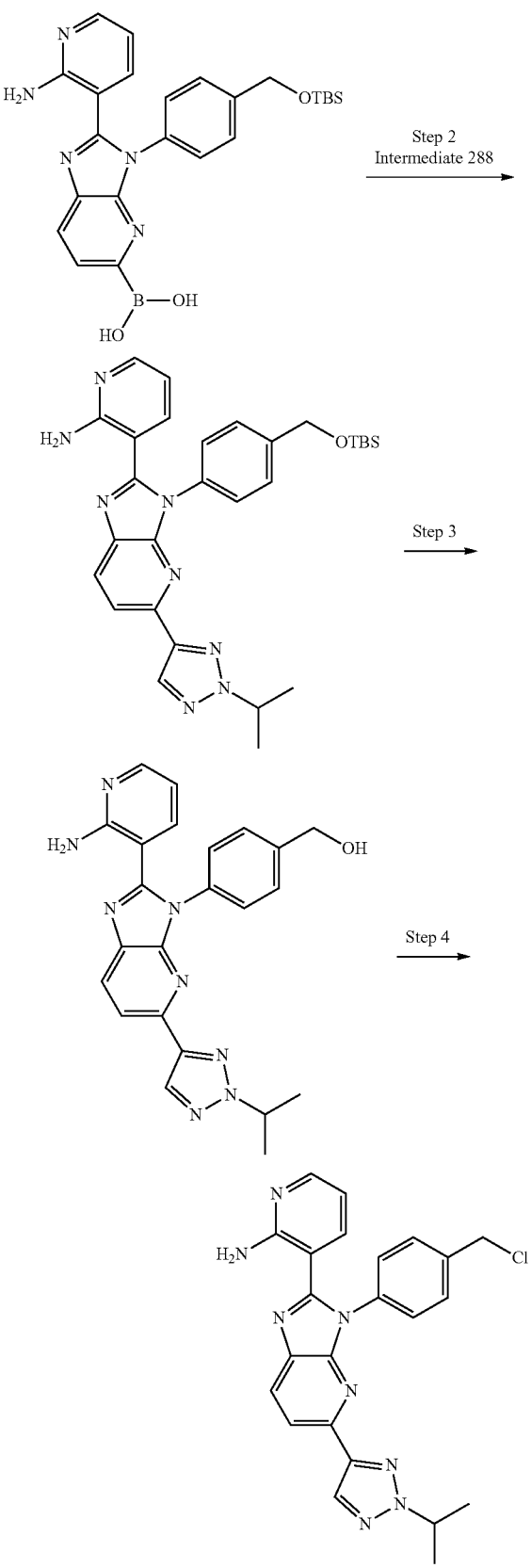

Intermediate 289

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl$_2$ (143 mg, 196 µmol) in 1,4-dioxane (10 mL) was degassed and purged with N$_2$ three times. The mixture was stirred at 80° C. for 4 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]$^+$.

Step 2: 3-(3-(4-(((tert-Butyldimethylsilyl)oxy)methyl)phenyl)-5-(2-isopropyl-2H-1,2,3-triazol-4-yl)-3H-imidazo[4,5-b]pyridin-2-yl)pyridin-2-amine To a solution of (2-(2-aminopyridin-3-yl)-3-(4-(((tert-butyldimethylsilyl)oxy)methyl)phenyl)-3H-imidazo[4,5-b]pyridin-5-yl)boronic acid (373 mg, 784 µmol) and 4-bromo-2-isopropyl-triazole (179 mg, 940 µmol) in 1,4-dioxane (12.5 mL) and H$_2$O (2.5 mL) were added Pd(dppf)Cl$_2$ (57.3 mg, 78.4 µmol) and Cs$_2$CO$_3$ (766 mg, 2.35 mmol) at 20° C. The mixture was stirred at 100° C. for 2 hr under N$_2$. The mixture was diluted with H$_2$O (20 mL) and extracted with EtOAc (20 mL×2). The combined organic layers were washed with brine (20 mL), dried over anhydrous Na$_2$SO$_4$, filtered and concentrated. After purified by silica gel flash chromatography (40-80% EtOAc in petroleum ether), 3-(3-(4-(((tert-butyldimethylsilyl)oxy)methyl)phenyl)-5-(2-isopropyl-2H-1,2,3-triazol-4-yl)-3H-imidazo[4,5-b]pyridin-2-yl)pyridin-2-amine (180 mg, 333 µmol, yield: 42.5% for two steps) was obtained as a yellow oil. MS: m/z=541.3 [M+H]$^+$. $^1$H NMR (400 MHz, Dimethylsulfoxide-d$_6$) δ 8.27 (d, J=8.4 Hz, 1H), 8.03-7.93 (m, 3H), 7.51-7.41 (m, 4H), 7.18 (dd, J=7.6, 2.0, Hz, 1H), 6.98 (s, 2H), 6.38 (dd, J=7.6, 4.8 Hz, 1H), 4.93-4.79 (m, 3H), 1.53 (d, J=6.8 Hz, 6H), 0.92 (s, 9H), 0.11 (s, 6H).

Step 3: (4-(2-(2-Aminopyridin-3-yl)-5-(2-isopropyl-2H-1,2,3-triazol-4-yl)-3H-imidazo[4,5-b]pyridin-3-yl)phenyl)methanol To a solution of 3-(3-(4-(((tert-butyldimethylsilyl)oxy)methyl)phenyl)-5-(2-isopropyl-2H-1,2,3-triazol-4-yl)-3H-imidazo[4,5-b]pyridin-2-yl)pyridin-2-amine (180 mg, 333 µmol) was added TBAF (1 M in THF, 533 µL). The reaction mixture was stirred at 20° C. for 0.5 hr. The mixture was diluted with H$_2$O (10 mL) and extracted with EtOAc (10 mL×2). The combined organic layers were washed with brine (10 mL), dried over anhydrous Na$_2$SO$_4$, filtered and concentrated. (4-(2-(2-Aminopyridin-3-yl)-5-(2-isopropyl-2H-1,2,3-triazol-4-yl)-3H-imidazo[4,5-b]pyridin-3-yl)phenyl)methanol (140 mg, 328 µmol) was obtained as a brown oil, which was used in the next step directly. MS: m/z=427.3 [M+H]$^+$. $^1$H NMR (400 MHz, Dimethylsulfoxide-d$_6$) δ 8.26 (d, J=8.4 Hz, 1H), 8.10-7.92 (m, 3H), 7.55-7.37 (m, 4H), 7.20 (d, J=7.6 Hz, 1H), 6.93 (s, 2H), 6.52-6.35 (m, 1H), 5.37 (s, 1H), 4.97-4.82 (m, 11H), 4.60 (s, 2H), 1.53 (d, J=6.8 Hz, 6H).

Step 4: 3-(3-(4-(Chloromethyl)phenyl)-5-(2-isopropyl-2H-1,2,3-triazol-4-yl)-3H-imidazo[4,5-b]pyridin-2-yl)pyridin-2-amine To a solution of (4-(2-(2-aminopyridin-3-yl)-5-(2-isopropyl-2H-1,2,3-triazol-4-yl)-3H-imidazo[4,5-b]pyridin-3-yl)phenyl)methanol (140 mg, 328 µmol) in CH$_2$Cl$_2$ (5 mL) was added SOCl$_2$ (117 mg, 985 µmol, 71.5 µL). The reaction mixture was stirred at 20° C. for 1 hr. The reaction mixture was concentrated to give 3-(3-(4-(chloromethyl)phenyl)-5-(2-isopropyl-2H-1,2,3-triazol-4-yl)-3H-imidazo[4,5-b]pyridin-2-yl)pyridin-2-amine (Intermediate 289, 146 mg, 328 µmol) as a brown oil, which was used in the next step directly. MS: m/z=445.2 [M+H]$^+$.

Intermediate 290: 4-Bromo-1-isopropyl-1H-1,2,3-triazole

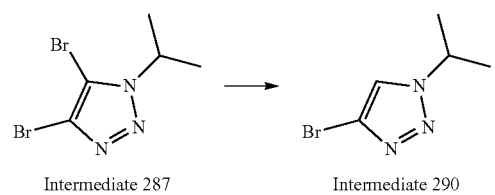

Intermediate 287 → Intermediate 290

To a solution of Intermediate 287 (300 mg, 1.12 mmol) in THF (3 mL) was added n-BuLi (2.5 M in hexane, 469 µL) at −70° C. The reaction mixture was stirred at −70° C. for 0.5 hr under N$_2$. The reaction mixture was quenched with sat. aq. NH$_4$Cl (10 mL) dropwise at −70° C. under N$_2$. The mixture was diluted with H$_2$O (5 mL) and extracted with EtOAc (10 mL×2). The combined organic layers were washed with brine (20 mL), dried over anhydrous Na$_2$SO$_4$, filtered and concentrated under reduced pressure. 4-Bromo-1-isopropyl-1H-1,2,3-triazole (Intermediate 290, 210 mg, yield: 99%) was obtained as colorless liquid, which was used in the next step directly. MS: m/z=188.0, 190.0 [M+H]$^+$. $^1$H NMR (400 MHz, Chloroform-d) δ 7.56 (s, 1H), 4.87-4.78 (m, 1H), 1.58 (d, J=6.8 Hz, 6H).

Intermediate 291: 3-(3-(4-(Chloromethyl)phenyl)-5-(1-isopropyl-1H-1,2,3-triazol-4-yl)-3H-imidazo[4,5-b]pyridin-2-yl)pyridin-2-amine

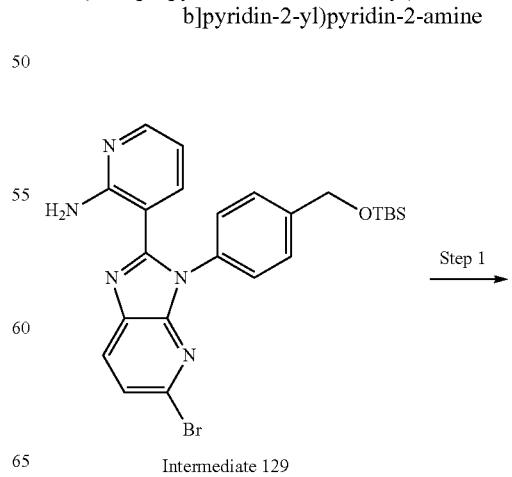

Intermediate 129

963
-continued

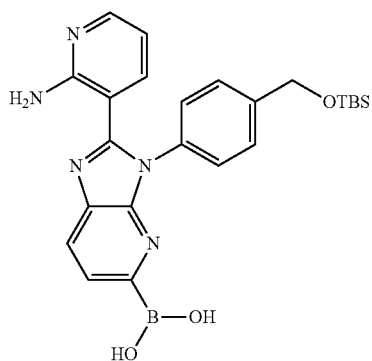

Step 2
Intermediate 290
→

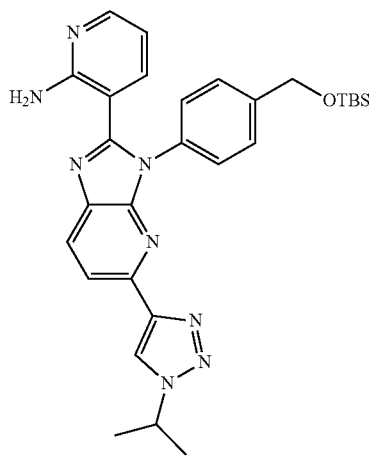

Step 3
→

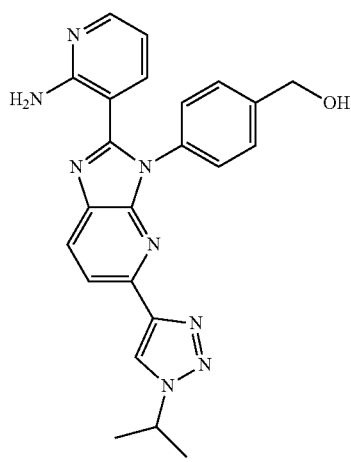

Step 4
→

964
-continued

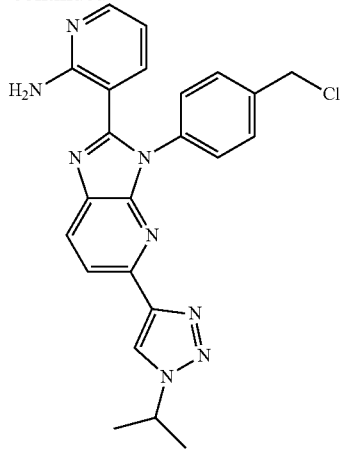

Intermediate 291

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl$_2$ (143 mg, 196 µmol) in 1,4-dioxane (10 mL) was degassed and purged with N$_2$ for 3 times. The mixture was stirred at 80° C. for 4 hr under N2 atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]$^+$.

Step 2: 3-(3-(4-(((tert-Butyldimethylsilyl)oxy)methyl)phenyl)-5-(1-isopropyl-1H-1,2,3-triazol-4-yl)-3H-imidazo[4,5-b]pyridin-2-yl)pyridin-2-amine To a solution of (2-(2-aminopyridin-3-yl)-3-(4-(((tert-butyldimethylsilyl)oxy)methyl)phenyl)-3H-imidazo[4,5-b]pyridin-5-yl)boronic acid (373 mg, 784 µmol) and Intermediate 290 (194 mg, 1.02 mmol) in 1,4-dioxane (12.5 mL) and H$_2$O (2.5 mL) were added Pd(dppf)Cl$_2$ (57.3 mg, 78.4 µmol) and Cs$_2$CO$_3$ (766 mg, 2.35 mmol) at 20° C. The mixture was stirred at 100° C. for 2 hr under N$_2$. The mixture was diluted with H$_2$O (30 mL) and extracted with EtOAc (30 mL×2). The combined organic layers were washed with brine (30 mL), dried over anhydrous Na$_2$SO$_4$, filtered and concentrated. After purified by silica gel flash chromatography (Eluent of 40%~80% EtOAc in petroleum ether), 3-(3-(4-(((tert-butyldimethylsilyl)oxy)methyl)phenyl)-5-(1-isopropyl-1H-1,2,3-triazol-4-yl)-3H-imidazo[4,5-b]pyridin-2-yl)pyridin-2-amine (280 mg, yield: 66% for two steps) was obtained as a brown solid. MS: m/z=541.3 [M+H]$^+$. $^1$H NMR (400 MHz, Dimethylsulfoxide-d$_6$) δ 8.39 (s, 1H), 8.27 (d, J=8.4 Hz, 1H), 8.09 (d, J=8.4 Hz, 1H), 7.98 (dd, J=4.8, 1.6 Hz, 1H), 7.49-7.43 (m, 4H), 7.15 (dd, J=7.6, 1.6, Hz, 1H), 6.97 (br s, 2H), 6.40-6.34 (m, 1H), 4.89-4.85 (m, 1H), 4.82 (s, 2H), 1.51 (d, J=6.8 Hz, 6H), 0.93 (s, 9H), 0.11 (s, 6H).

Step 3: (4-(2-(2-Aminopyridin-3-yl)-5-(1-isopropyl-1H-1,2,3-triazol-4-yl)-3H-imidazo[4,5-b]pyridin-3-yl)phenyl)methanol To a solution of 3-(3-(4-(((tert-butyldimethylsilyl)oxy)methyl)phenyl)-5-(1-isopropyl-1H-1,2,3-triazol-4-yl)-3H- imidazo[4,5-b]pyridin-2-yl)pyridin-2-amine (280 mg, 518 µmol) in THF (8 mL) was added TBAF (1 M in THF, 829 µL). The reaction mixture was stirred at 20° C. for 0.5 hr. The mixture was diluted with H₂O (10 mL) and extracted with EtOAc (10 mL×2). The combined organic layers were washed with brine (10 mL), dried over anhydrous Na₂SO₄, filtered and concentrated. (4-(2-(2-Aminopyridin-3-yl)-5-(1-isopropyl-1H-1,2,3-triazol-4-yl)-3H-imidazo[4,5-b]pyridin-3-yl)phenyl)methanol (220 mg) was obtained as yellow oil, which was used in the next step directly. MS: m/z=427.3 [M+H]⁺. ¹H NMR (400 MHz, Dimethylsulfoxide-d₆) δ 8.41 (s, 1H), 8.27 (d, J=8.4 Hz, 1H), 8.08 (d, J=8.4 Hz, 1H), 7.98 (dd, J=4.8, 1.6 Hz, 1H), 7.50-7.46 (m, 2H), 7.44-7.39 (m, 2H), 7.18 (dd, J=7.6, 1.6 Hz, 1H), 6.92 (br s, 2H), 6.40 (dd, J=7.6, 4.8 Hz, 1H), 4.93-4.84 (m, 1H), 4.60 (s, 2H), 1.52 (d, J=6.8 Hz, 6H).

Step 4: 3-(3-(4-(Chloromethyl)phenyl)-5-(1-isopropyl-1H-1,2,3-triazol-4-yl)-3H-imidazo[4,5-b]pyridin-2-yl)pyridin-2-amine To a solution of (4-(2-(2-aminopyridin-3-yl)-5-(1-isopropyl-1H-1,2,3-triazol-4-yl)-3H-imidazo[4,5-b]pyridin-3-yl)phenyl)methanol (220 mg, 516 µmol) in CH₂Cl₂ (8 mL) was added SOCl₂ (184 mg, 1.55 mmol, 112 µL). The reaction mixture was stirred at 20° C. for 1 hr. The reaction mixture was concentrated to give 3-(3-(4-(chloromethyl)phenyl)-5-(1-isopropyl-1H-1,2,3-triazol-4-yl)-3H-imidazo[4,5-b]pyridin-2-yl)pyridin-2-amine (Intermediate 291, 220 mg, HCl salt) as a brown oil, which was used in the next step directly. MS: m/z=445.2, 447.2 [M+H]⁺.

Intermediate 292: 4-Bromo-2-methyl-5-(methyl-d₃)-2H-1,2,3-triazole

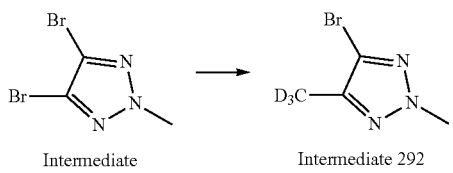

Intermediate                Intermediate 292

To a solution of 4,5-dibromo-2-methyl-2H-1,2,3-triazole (1 g, 4.2 mmol) in THF (10 mL) was degassed and purged with N₂ three times. n-BuLi (2.49 mL, 6.2 mmol, 2.5 M in n-hexane) was added at 0° C. and stirred at 0° C. for 0.5 hr under N₂ atmosphere. The mixture was added CD₃I (884 mg, 6.2 mmol) at 0° C. and stirred at 0° C. for 2 hr under N₂ atmosphere. The mixture was quenched with H₂O (100 mL) and extracted with CH₂Cl₂ (50 mL×2). The combined organic layers were washed with brine (50 mL×3), dried over Na₂SO₄, filtered and concentrated. 4-Bromo-2-methyl-5-(methyl-d₃)-2H-1,2,3-triazole (Intermediate 292, 550 mg, crude) was obtained as a yellow oil, which was used in the next step without purification.

Intermediate 293: 3-(3-(4-(Chloromethyl)phenyl)-5-(2-methyl-5-(methyl-d₆)-2H-1,2,3-triazol-4-yl)-3H-imidazo[4,5-b]pyridin-2-yl)pyridin-2-amine

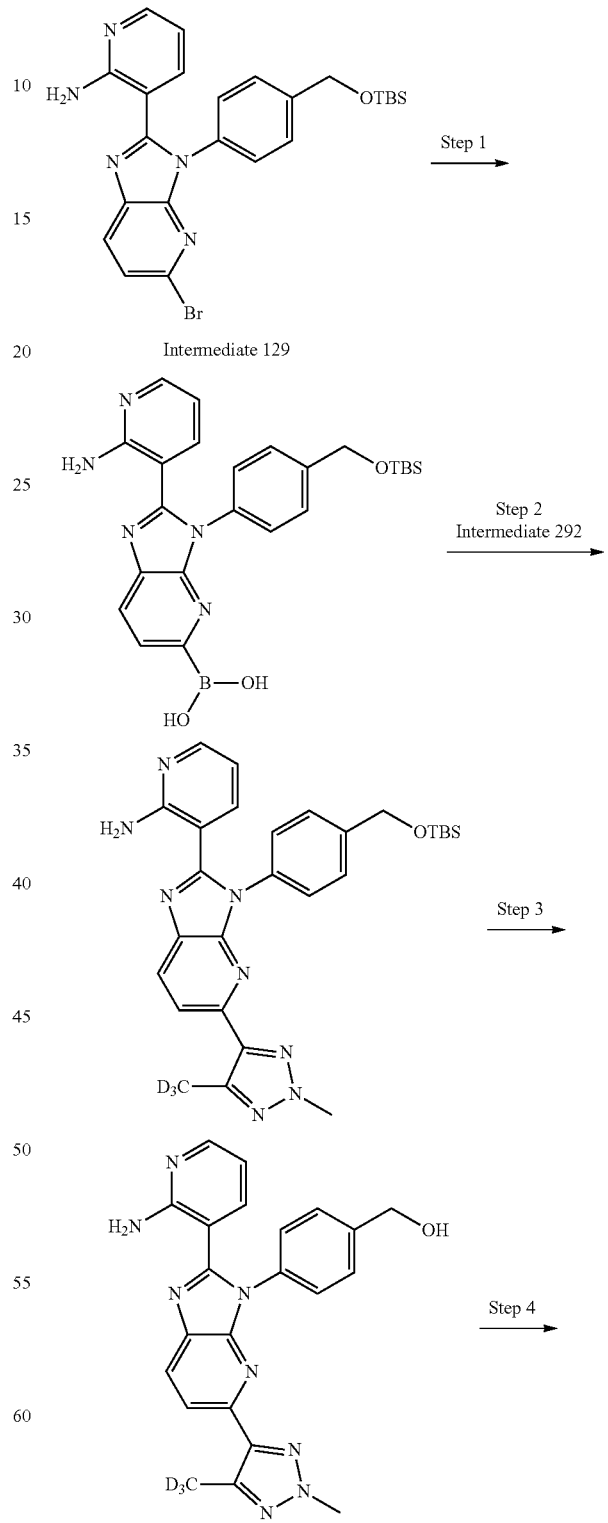

Intermediate 129

Step 2
Intermediate 292

-continued

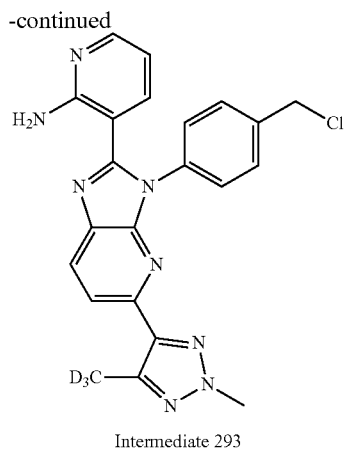

Intermediate 293

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.9 mmol), 4,4,4',4',5,5,5',5'-octamethyl-2,2'-bi(1,3,2-dioxaborolane) (746 mg, 2.9 mmol), KOAc (577 mg, 5.9 mmol), and Pd(dppf)Cl$_2$ (80 mg, 98 μmol) in 1,4-dioxane (10 mL) was degassed and purged with N$_2$ three times. The mixture was stirred at 110° C. for 2 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]$^+$.

Step 2: 3-(3-(4-(((Tert-butyldimethylsilyl)oxy)methyl)phenyl)-5-(2-methyl-5-(methyl-d$_3$)-2H-1,2,3-triazol-4-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (500 mg, 1.0 mmol), Intermediate 292 (244 mg, 1.3 mmol), Pd(dppf)Cl$_2$ (86 mg, 105 μmol), and Cs$_2$CO$_3$ (1 g, 3.1 mmol) in 1,4-dioxane (5 mL) was degassed and purged with N$_2$ three times. The mixture was stirred at 95° C. for 12 hr under N$_2$ atmosphere. The reaction mixture was quenched with H$_2$O (30 mL) and extracted with CH$_2$Cl$_2$ (20 mL×2). The combined organic layers were washed with brine (50 mL), dried over Na$_2$SO$_4$, filtered and concentrated under reduced pressure. After purified by silica gel flash chromatography (Eluent of 0%~25% EtOAc in petroleum ether), 3-(3-(4-(((tert-butyldimethylsilyl)oxy)methyl)phenyl)-5-(2-methyl-5-(methyl-d$_3$)-2H-1,2,3-triazol-4-yl)-3H-imidazo[4,5-b]pyridin-2-yl)pyridin-2-amine (200 mg, yield: 26% for three steps) was obtained as a yellow solid. MS: m/z=530.2 [M+H]$^+$. D %: 3D %=99.9% $^1$H NMR (400 MHz, Dimethylsulfoxide-d$_6$) δ 8.25 (d, J=8.4 Hz, 1H), 8.01-7.98 (m, 1H), 7.93-7.90 (m, 1H), 7.47-7.46 (m, 4H), 7.22 (dd, J=8.0, 1.6 Hz, 1H), 7.05-6.98 (m, 2H), 6.42-6.38 (m, 1H), 4.80 (s, 2H), 4.13 (s, 3H), 0.91 (s, 9H), 0.08 (s, 6H).

Step 3: (4-(2-(2-Aminopyridin-3-yl)-5-(2-methyl-5-(methyl-d$_3$)-2H-1,2,3-triazol-4-yl)-3H-imidazo[4,5-b]pyridin-3-yl)phenyl)methanol To a solution of 3-(3-(4-(((tert-butyldimethylsilyl)oxy)methyl)phenyl)-5-(2-methyl-5-(methyl-d$_3$)-2H-1,2,3-tri-azol-4-yl)-3H-imidazo[4,5-b]pyridin-2-yl)pyridin-2-amine (200 mg, 377 μmol) in THF (3 mL) was added TBAF (3.8 mL, 1 M in THF). The mixture was stirred at 25° C. for 2 hr. The reaction mixture was quenched with H$_2$O (5 mL) at 25° C. and extracted with CH$_2$Cl$_2$ (15 mL×2). The combined organic layers were washed with brine (30 mL×2), dried over Na$_2$SO$_4$, filtered and concentrated under reduced pressure. After triturated with EtOAc:petroleum ether=1:10 (11 mL) at 25° C. for 10 min, (4-(2-(2-aminopyridin-3-yl)-5-(2-methyl-5-(methyl-d$_3$)-2H-1,2,3-triazol-4-yl)-3H-imidazo[4,5-b]pyridin-3-yl)phenyl)methanol (150 mg, crude) was obtained as a yellow solid. MS: m/z=416.0 [M+H]. $^1$H NMR (400 MHz, Dimethylsulfoxide-d$_6$) δ 8.25 (d, J=8.4 Hz, 1H), 8.02-8.00 (m, 1H), 7.93-7.90 (m, 1H), 7.48-7.43 (m, 5H), 7.26-7.22 (m, 1H), 6.99-6.94 (m, 2H), 6.45-6.42 (m, 1H), 4.59-4.57 (m, 2H), 4.13 (s, 3H).

Step 4: 3-(3-(4-(Chloromethyl)phenyl)-5-(2-methyl-5-(methyl-d$_3$)-2H-1,2,3-triazol-4-yl)-3H-imidazo[4,5-b]pyridin-2-yl)pyridin-2-amine To a solution of (4-(2-(2-aminopyridin-3-yl)-5-(2-methyl-5-(methyl-d$_3$)-2H-1,2,3-triazol-4-yl)-3H-imidazo[4,5-b]pyridin-3-yl)phenyl)methanol (150 mg, 339 μmol) in CH$_2$Cl$_2$ (2 mL) was added SOCl$_2$ (262 μL, 3.61 mmol). The mixture was stirred at 25° C. for 1 hr. The reaction was concentrated under reduced pressure to give 3-(3-(4-(chloromethyl)phenyl)-5-(2-methyl-5-(methyl-d$_6$)-2H-1,2,3-tri-azol-4-yl)-3H-imidazo[4,5-b]pyridin-2-yl)pyridin-2-amine (Intermediate 293, 170 mg, crude, HCl salt) as a green solid which was used into next step directly. MS: m/z=434.2 [M+H]$^+$.

Intermediate 294: 3-(3-(4-(Chloromethyl)phenyl)-5-(2,5-dimethyl-2H-1,2,3-triazol-4-yl)-3H-imidazo[4,5-b]pyridin-2-yl)pyridin-2-amine

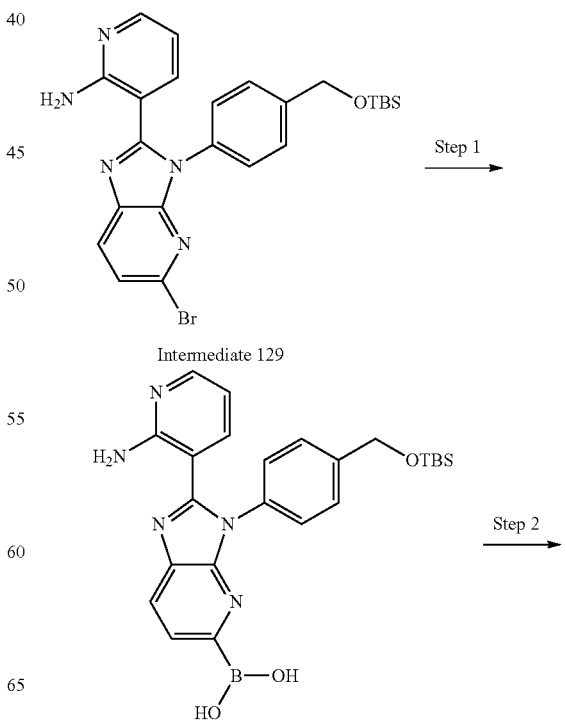

-continued

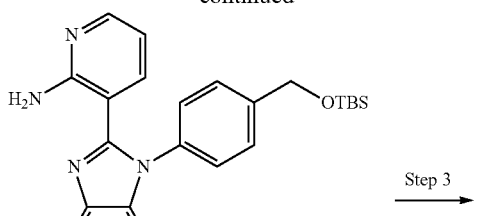

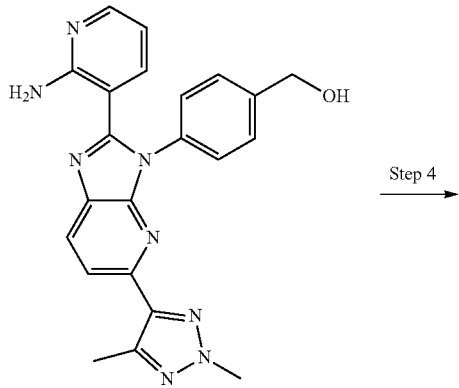

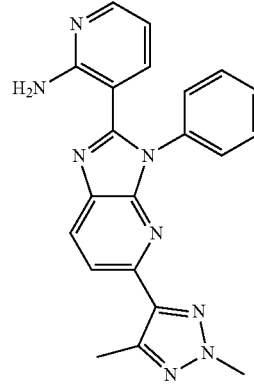

Intermediate 294

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid To a mixture of Intermediate 129 (500 mg, 979 μmol) in 1,4-dioxane (5 mL) were added potassium acetate (288 mg, 2.94 mmol) and 4,4,4',4',5,5,5',5'-octamethyl-2,2'-bi(1,3,2-dioxaborolane) (497 mg, 1.96 mmol), and Pd(dppf)Cl$_2$ (71.7 mg, 97.9 μmol). The mixture was degassed and purged with N$_2$ three times and stirred at 85° C. for 2 hr under N$_2$. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((tert-Butyldimethylsilyl)oxy)methyl)phenyl)-5-(2,5-dimethyl-2H-1,2,3-triazol-4-yl)-3H-imidazo[4,5-b]pyridin-2-yl)pyridin-2-amine To a mixture of (2-(2-aminopyridin-3-yl)-3-(4-(((tert-butyldimethylsilyl)oxy)methyl)phenyl)-3H-imidazo[4,5-b]pyridin-5-yl)boronic acid (465 mg, 978 μmol) and 4-bromo-2,5-dimethyl-2H-1,2,3-triazole (206 mg, 1.17 mmol) in 1,4-dioxane (10 mL) and H$_2$O (2 mL) were added Cs$_2$CO$_3$ (956 mg, 2.93 mmol) and Pd(dppf)Cl$_2$ (71.6 mg, 97.8 μmol). The mixture was degassed and purged with N$_2$ three times and stirred at 100° C. for 2 hr under N$_2$. The mixture was diluted with H$_2$O (20 mL) and extracted with EtOAc (50 mL×2). The combined organic layers were washed with brine (30 mL), dried over anhydrous Na$_2$SO$_4$, filtered and concentrated. After purified by silica gel flash chromatography (EtOAc in petroleum ether=0-50%), 3-(3-(4-(((tert-butyldimethylsilyl)oxy)methyl)phenyl)-5-(2,5-dimethyl-2H-1,2,3-triazol-4-yl)-3H-imidazo[4,5-b]pyridin-2-yl)pyridin-2-amine (380 mg, yield: 74% for two steps) was obtained as a brown solid. MS: m/z=527.3 [M+H]$^+$. $^1$H NMR (400 MHz, Dimethylsulfoxide-d$_6$) δ 8.25 (d, J=8.4 Hz, 1H), 8.01 (dd, J=4.8, 1.6 Hz, 1H), 7.91 (d, J=8.4 Hz, 1H), 7.49-7.42 (m, 4H), 7.22 (dd, J=7.6, 1.6 Hz, 1H), 7.02 (s, 2H), 6.40 (dd, J=7.6, 4.8 Hz, 1H), 4.80 (s, 2H), 4.13 (s, 3H), 2.36 (s, 3H), 0.91 (s, 9H), 0.08 (s, 6H).

Step 3: (4-(2-(2-Aminopyridin-3-yl)-5-(2,5-dimethyl-2H-1,2,3-triazol-4-yl)-3H-imidazo[4,5-b]pyridin-3-yl)phenyl)methanol To a mixture of 3-(3-(4-(((tert-butyldimethylsilyl)oxy)methyl)phenyl)-5-(2,5-dimethyl-2H-1,2,3-triazol-4-yl)-3H-imidazo[4,5-b]pyridin-2-yl)pyridin-2-amine (380 mg, 721 μmol) in THF (4 mL) was added TBAF (1M in THF, 1.08 mL). The mixture was stirred at 20° C. for 1 hr. The mixture was diluted with H$_2$O (20 mL) and extracted with EtOAc (50 mL×2). The combined organic layers were washed with brine (20 mL), dried over anhydrous Na$_2$SO$_4$, filtered and concentrated to give (4-(2-(2-aminopyridin-3-yl)-5-(2,5-dimethyl-2H-1,2,3-triazol-4-yl)-3H-imidazo[4,5-b]pyridin-3-yl)phenyl)methanol (270 mg, 655 μmol, yield: 91%) as a brown solid. MS: m/z=413.2 [M+H]$^+$. $^1$H NMR (400 MHz, Dimethylsulfoxide-d$_6$) δ 8.25 (d, J=8.4 Hz, 1H), 8.01 (dd, J=4.8, 2.0 Hz, 1H), 7.91 (d, J=8.4 Hz, 1H), 7.49-7.42 (m, 4H), 7.24 (dd, J=8.0, 2.0 Hz, 1H), 6.96 (s, 2H), 6.43 (dd, J=7.6, 4.8 Hz, 1H), 5.35 (t, J=6.0 Hz, 1H), 4.59 (d, J=6.0 Hz, 2H), 4.13 (s, 3H), 2.39 (s, 3H).

Step 4: 3-(3-(4-(Chloromethyl)phenyl)-5-(2,5-dimethyl-2H-1,2,3-triazol-4-yl)-3H-imidazo[4,5-b]pyridin-2-yl)pyridin-2-amine To a mixture of (4-(2-(2-aminopyridin-3-yl)-5-(2,5-dimethyl-2H-1,2,3-triazol-4-yl)-3H-imidazo[4,5-b]pyridin-3-yl)phenyl)methanol (270 mg, 654 μmol) in CH$_2$Cl$_2$ (3 mL) was added SOCl$_2$ (143 μL, 1.96 mmol). The mixture was stirred at 20° C. for 1 hr. The mixture was concentrated to give 3-(3-(4-(chloromethyl)phenyl)-5-(2,5-dimethyl-2H-1,2,3-triazol-4-yl)-3H-imidazo[4,5-b]pyridin-2-yl)pyridin-2-amine (Intermediate 294, 282 mg) was obtained as a brown solid. MS: m/z=431.2, 433.1 [M+H]$^+$.

Intermediate 295: 3-(3-(4-(Chloromethyl)phenyl)-5-(2-cyclopropyl-2H-1,2,3-triazol-4-yl)-3H-imidazo[4,5-b]pyridin-2-yl)pyridin-2-amine

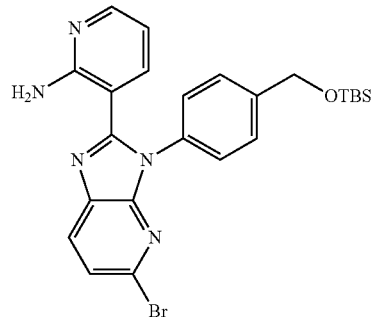

Intermediate 129

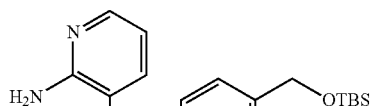

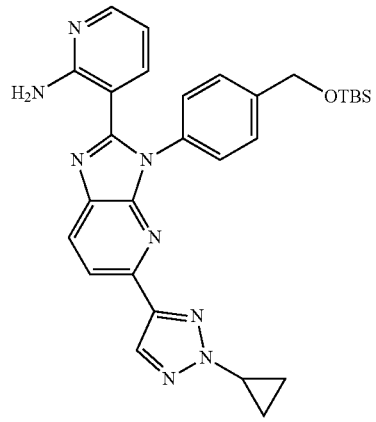

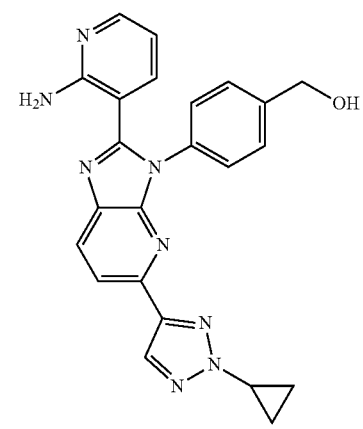

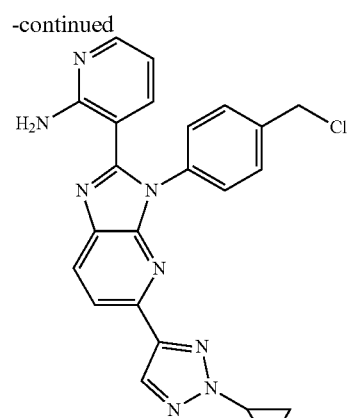

Intermediate 295

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (500 mg, 980 μmol), 4,4,4',4',5,5,5',5'-octamethyl-2,2'-bi(1,3,2-dioxaborolane) (497 mg, 1.96 mmol), KOAc (289 mg, 2.94 mmol) and Pd(dppf)Cl$_2$ (72 mg, 98.0 μmol) in 1,4-dioxane (5 mL) was degassed and purged with N$_2$ three times. The mixture was stirred at 80° C. for 4 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]$^+$.

Step 2: 3-(3-(4-(((tert-Butyldimethylsilyl)oxy)methyl)phenyl)-5-(2-cyclopropyl-2H-1,2,3-triazol-4-yl)-3H-imidazo[4,5-b]pyridin-2-yl)pyridin-2-amine To a solution of (2-(2-aminopyridin-3-yl)-3-(4-(((tert-butyldimethylsilyl)oxy)methyl)phenyl)-3H-imidazo[4,5-b]pyridin-5-yl)boronic acid (466 mg, 979 μmol) and 4-bromo-2-cyclopropyl-triazole (221 mg, 1.18 mmol) in 1,4-dioxane (15 mL) and H$_2$O (3 mL) were added Pd(dppf)Cl$_2$ (71.7 mg, 97.9 μmol) and Cs$_2$CO$_3$ (957 mg, 2.94 mmol) at 20° C. The mixture was stirred at 80° C. for 2 hr. The mixture was diluted with H$_2$O (50 mL) and extracted with EtOAc (50 mL×2). The combined organic layers were washed with brine (50 mL), dried over anhydrous Na$_2$SO$_4$, filtered and concentrated under reduced pressure. After purified by silica gel flash chromatography (EtOAc in petroleum ether=35%-100%), 3-(3-(4-(((tert-butyldimethylsilyl)oxy)methyl)phenyl)-5-(2-cyclopropyl-2H-1,2,3-triazol-4-yl)-3H-imidazo[4,5-b]pyridin-2-yl)pyridin-2-amine (440 mg, yield: 83% for two steps) was obtained as a black oil. MS: m/z=539.3 [M+H]$^+$. $^1$H NMR (400 MHz, Dimethylsulfoxide-d$_6$) δ 8.27 (d, J=8.4 Hz, 1H), 8.01-7.98 (m, 2H), 7.93 (d, J=8.4 Hz, 1H), 7.50-7.44 (m, 4H), 7.18 (dd, J=7.6, 1.6 Hz, 1H), 6.97 (br s, 2H), 6.38 (dd, J=7.6, 4.8 Hz, 1H), 4.82 (s, 2H), 1.27-1.22 (m, 3H), 1.15-1.10 (m, 2H), 0.92 (s, 9H), 0.11 (s, 6H).

Step 3: (4-(2-(2-Aminopyridin-3-yl)-5-(2-cyclopropyl-2H-1,2,3-triazol-4-yl)-3H-imidazo[4,5-b]pyridin-3-yl)phenyl)methanol To a solution of 3-(3-(4-(((tert-butyldimethylsilyl)oxy)methyl)phenyl)-5-(2-cyclopropyl-2H-1,2,3-triazol-4-yl)-

3H-imidazo[4,5-b]pyridin-2-yl)pyridin-2-amine (220 mg, 408 μmol) in THF (5 mL) was added TBAF (1M in THF, 613 μL) at 20° C. The reaction mixture was stirred at 20° C. for 0.5 hr. The mixture was diluted with H$_2$O (10 mL) and extracted with EtOAc (10 mL×2). The combined organic layers were washed with brine (10 mL), dried over anhydrous Na$_2$SO$_4$, filtered and concentrated. (4-(2-(2-Aminopyridin-3-yl)-5-(2-cyclopropyl-2H-1,2,3-triazol-4-yl)-3H-imidazo[4,5-b]pyridin-3-yl)phenyl)methanol (170 mg) was obtained as a gray solid and used in the next step directly. MS: m/z=425.2 [M+H]$^+$.

Step 4: 3-(3-(4-(Chloromethyl)phenyl)-5-(2-cyclopropyl-2H-1,2,3-triazol-4-yl)-3H-imidazo[4,5-b]pyridin-2-yl)pyridin-2-amine To a solution of (4-(2-(2-aminopyridin-3-yl)-5-(2-cyclopropyl-2H-1,2,3-triazol-4-yl)-3H-imidazo[4,5-b]pyridin-3-yl)phenyl)methanol (170 mg, 401 μmol) in CH$_2$Cl$_2$ (5 mL) was added SOCl$_2$ (143 mg, 1.20 mmol, 87.3 μL). The reaction mixture was stirred at 20° C. for 1 hr and concentrated under reduced pressure. 3-(3-(4-(Chloromethyl)phenyl)-5-(2-cyclopropyl-2H-1,2,3-triazol-4-yl)-3H-imidazo[4,5-b]pyridin-2-yl)pyridin-2-amine (Intermediate 295, 170 mg) was obtained as a gray solid and used in the next step directly. MS: m/z=443.1, 445.2 [M+H]$^+$.

Intermediate 296:
4-Bromo-2-methyl-2H-1,2,3-triazole-5-d

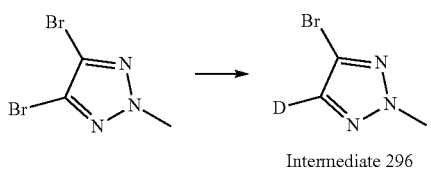

Intermediate 296

To a solution of 4,5-dibromo-2-methyl-2H-1,2,3-triazole (1 g, 4.15 mmol) in THF (10 mL) was degassed and purged with N$_2$ three times. n-BuLi (2.5 M, 2.49 mL) was added at −78° C. under N$_2$ atmosphere. The mixture was stirred at −78° C. for 0.5 hr under N$_2$ atmosphere. The reaction mixture was quenched with D$_2$O (166 mg, 8.30 mmol) at −78° C. and stirred at −78° C. for 2 hr under N$_2$ atmosphere. The reaction mixture was diluted with H$_2$O (10 mL) and extracted with CH$_2$Cl$_2$ 30 mL (15 mL×2). The combined organic layers were washed with brine (30 mL), dried over anhydrous Na$_2$SO$_4$, filtered and concentrated under reduced pressure. 4-Bromo-2-methyl-2H-1,2,3-triazole-5-d (Intermediate 296, 200 mg, yield: 30%) was obtained as a light-yellow oil. $^1$H NMR (400 MHz, Chloroform-d) δ 4.18 (s, 3H).

Intermediate 297: 3-(3-(4-(Chloromethyl)phenyl)-5-(2-methyl-2H-1,2,3-triazol-4-yl-5-d)-3H-imidazo[4,5-b]pyridin-2-yl)pyridin-2-amine

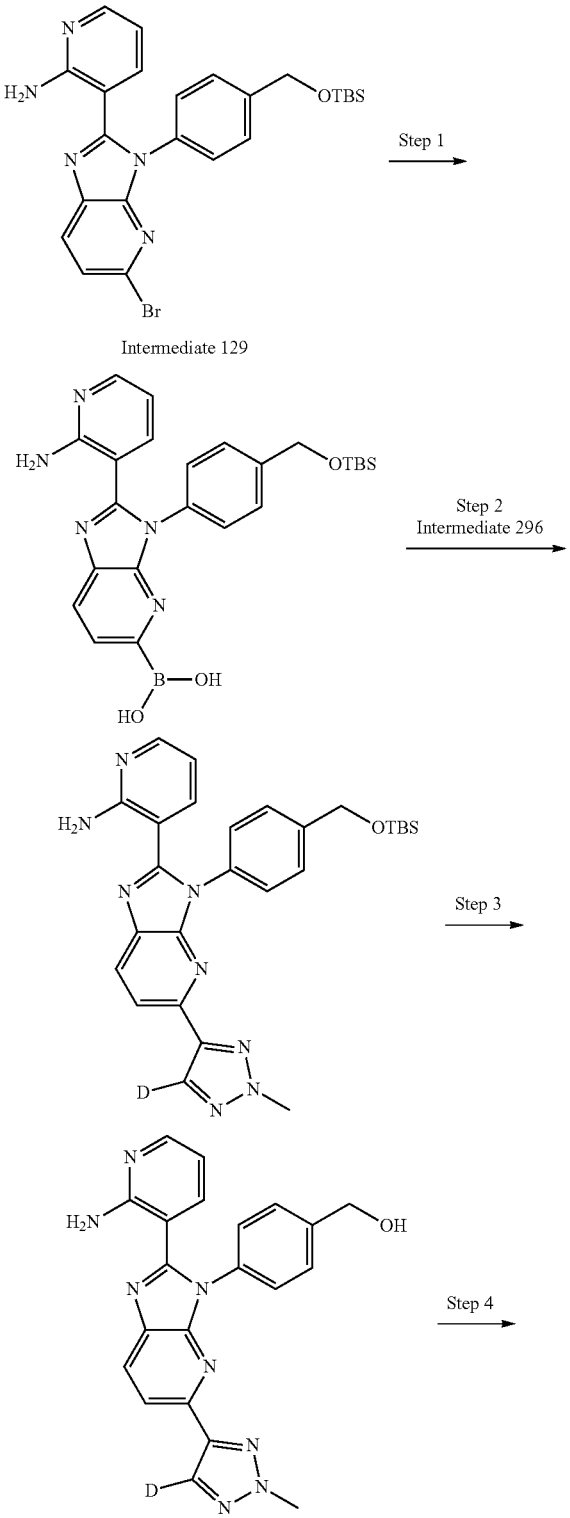

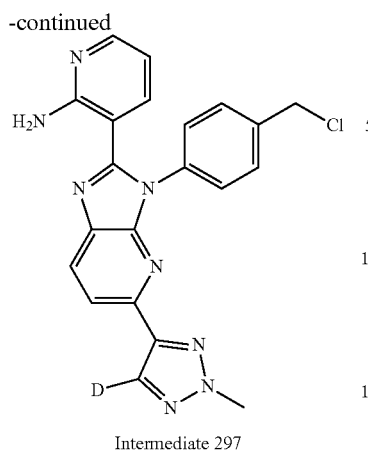

Intermediate 297

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (250 mg, 490 μmol), 4,4,4',4',5,5,5',5'-octamethyl-2,2'-bi(1,3,2-dioxaborolane) (187 mg, 735 μmol), KOAc (144 mg, 1.47 mmol) and Pd(dppf)Cl$_2$ (35.8 mg, 50 μmol) in 1,4-dioxane (3 mL) was degassed and purged with N$_2$ three times. The mixture was stirred at 90° C. for 2 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((tert-Butyldimethylsilyl)oxy)methyl)phenyl)-5-(2-methyl-2H-1,2,3-triazol-4-yl-5-d)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (200 mg, 421 μmol), Intermediate 296 (68.6 mg, 421 μmol), Cs$_2$CO$_3$ (411 mg, 1.26 mmol) and Pd(dppf)Cl$_2$ (30.8 mg, 42.1 μmol) in 1,4-dioxane (5 mL) and H$_2$O (1 mL) was degassed and purged with N$_2$ three 3 times. The mixture was stirred at 80° C. for 16 hr under N$_2$ atmosphere. The reaction mixture was quenched with H$_2$O (20 mL) and extracted with CH$_2$Cl$_2$ (15 mL×2). The combined organic layers were washed with brine (30 mL), dried over Na$_2$SO$_4$, filtered and concentrated under reduced pressure. After purified by silica gel flash chromatography (Eluent of 10%~40% EtOAc in petroleum ether), 3-(3-(4-(((tert-butyldimethylsilyl)oxy)methyl)phenyl)-5-(2-methyl-2H-1,2,3-triazol-4-yl-5-d)-3H-imidazo[4,5-b]pyridin-2-yl)pyridin-2-amine (130 mg, yield: 39% for two steps) was obtained as a brown solid. MS: m/z=514.1 [M+H]$^+$. $^1$H NMR (400 MHz, Chloroform-d) δ 8.12 (d, J=8.4 Hz, 1H), 8.07-8.03 (m, 1H), 7.38 (d, J=8.0 Hz, 2H), 7.31 (d, J=8.4 Hz, 2H), 7.13 (d, J=7.6 Hz, 1H), 7.02 (d, J=8.0 Hz, 1H), 6.72 (s, 2H), 6.32 (dd, J=8.0, 5.2 Hz, 1H), 4.86 (s, 2H), 4.25 (s, 3H), 0.98 (s, 9H), 0.15 (s, 6H).

Step 3: (4-(2-(2-Aminopyridin-3-yl)-5-(2-methyl-2H-1,2,3-triazol-4-yl-5-d)-3H-imidazo[4,5-b]pyridin-3-yl)phenyl)methanol To a solution of 3-(3-(4-(((tert-butyldimethylsilyl)oxy)methyl)phenyl)-5-(2-methyl-2H-1,2,3-triazol-4-yl-5-d)-3H-imidazo[4,5-b]pyridin-2-yl)pyridin-2-amine (130 mg, 253 μmol) in THF (2 mL) was added TBAF (506 μL, 1 M in THF). The mixture was stirred at 25° C. for 1 hr. The reaction mixture was quenched with H$_2$O (20 mL) at 25° C. and extracted with EtOAc (15 mL×2). The combined organic layers were washed with brine (50 mL×3), dried over Na$_2$SO$_4$, filtered and concentrated under reduced pressure. After triturated with CH$_2$Cl$_2$ (10 mL) at 25° C. for 10 min, the liquid was collected and concentrated under reduced pressure. (4-(2-(2-Aminopyridin-3-yl)-5-(2-methyl-2H-1,2,3-triazol-4-yl-5-d)-3H-imidazo[4,5-b]pyridin-3-yl)phenyl)methanol (80 mg, yield: 47%) was obtained as a brown solid. MS: m/z=400.2 [M+H]$^+$.

Step 4: 3-(3-(4-(Chloromethyl)phenyl)-5-(2-methyl-2H-1,2,3-triazol-4-yl-5-d)-3H-imidazo[4,5-b]pyridin-2-yl)pyridin-2-amine To a solution of (4-(2-(2-aminopyridin-3-yl)-5-(2-methyl-2H-1,2,3-triazol-4-yl-5-d)-3H-imidazo[4,5-b]pyridin-3-yl)phenyl)methanol (80 mg, 200 μmol) in CH$_2$Cl$_2$ (3 mL) was added SOCl$_2$ (71.5 mg, 600 μmol). The mixture was stirred at 40° C. for 0.2 hr. The reaction was concentrated under reduced pressure. And the solid was diluted with NaHCO$_3$ (10 mL) and extracted with CH$_2$Cl$_2$ (15 mL×2). The combined organic layers were washed with brine (30 mL), dried over anhydrous Na$_2$SO$_4$, filtered and concentrated under reduced pressure. After purified by silica gel flash chromatography (Eluent of 0%~4% MeOH in CH$_2$Cl$_2$), 3-(3-(4-(chloromethyl)phenyl)-5-(2-methyl-2H-1,2,3-triazol-4-yl-5-d)-3H-imidazo[4,5-b]pyridin-2-yl)pyridin-2-amine (Intermediate 297, 23 mg, yield: 27%) was obtained as a yellow solid. MS: m/z=418.1 [M+H]$^+$.

Intermediate 298: 4-(2-(3-Aminopyrazin-2-yl)-5-bromo-3H-imidazo[4,5-b]pyridin-3-yl)benzyl acetate

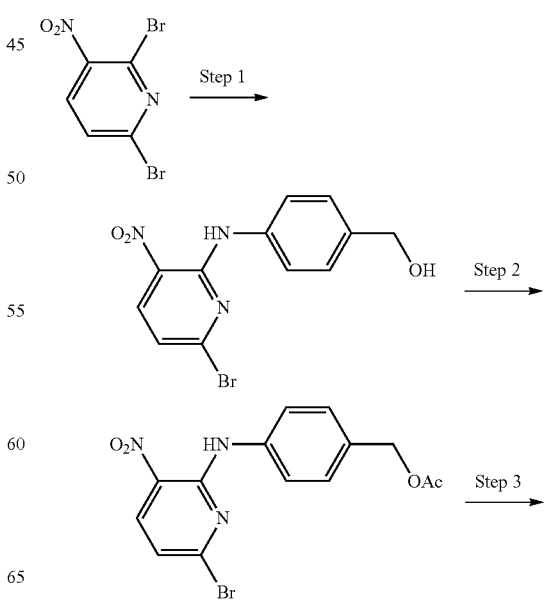

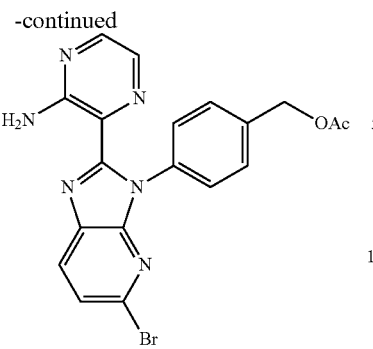

Intermediate 298

Step 1: (4-((6-Bromo-3-nitropyridin-2-yl)amino)phenyl)methanol

A mixture of 2,6-dibromo-3-nitropyridine (5 g, 17.7 mmol), (4-aminophenyl)methanol (2.18 g, 17.7 mmol), DIEA (6.88 g, 53.2 mmol) in 1,4-dioxane (50 mL) was degassed and purged with $N_2$ three times and stirred at 45° C. for 2 hr under $N_2$ atmosphere. The reaction mixture was quenched with $H_2O$ (100 mL) at 25° C. and extracted with $CH_2Cl_2$ (100 mL×2). The combined organic layers were washed with brine (100 mL), dried over anhydrous $Na_2SO_4$, filtered and concentrated under reduced pressure. (4-((6-Bromo-3-nitropyridin-2-yl)amino)phenyl)methanol (5.75 g) was obtained as a yellow solid. MS: m/z=324.1, 326.1 [M+H]$^+$. $^1$H NMR (400 MHz, Chloroform-d) δ 10.24 (br s, 1H), 8.33 (d, J=8.8 Hz, 1H), 7.71-7.58 (m, 2H), 7.43-7.40 (m, 2H), 6.97 (d, J=8.4 Hz, 1H), 4.71 (br s, 2H).

Step 2: 4-((6-Bromo-3-nitropyridin-2-yl)amino)benzyl acetate

To a solution of (4-((6-bromo-3-nitropyridin-2-yl)amino)phenyl)methanol (5.75 g, 17.7 mmol) in $CH_2Cl_2$ (60 mL) were added DMAP (217 mg, 1.77 mmol), TEA (5.39 g, 53.2 mmol) and $AC_2O$ (2.72 g, 26.6 mmol). The mixture was stirred at 25° C. for 2 hr. The reaction mixture was quenched with $H_2O$ (100 mL) at 25° C. and extracted with $CH_2Cl_2$ (100 mL×2). The combined organic layers were washed with brine (100 mL), dried over anhydrous $Na_2SO_4$, filtered, and concentrated under reduced pressure. After purified by silica gel flash chromatography (Eluent of 0%~15% EtOAc in petroleum ether), 4-((6-bromo-3-nitropyridin-2-yl)amino)benzyl acetate (4.9 g, yield: 75% for two steps) was obtained as a yellow solid. $^1$H NMR (400 MHz, Chloroform-d) δ 10.25 (br s, 1H), 8.33 (d, J=8.4 Hz, 1H), 7.66 (d, J=8.4 Hz, 2H), 7.40 (d, J=8.4 Hz, 2H), 6.98 (d, J=8.4 Hz, 1H), 5.11 (s, 2H), 2.11 (s, 3H).

Step 3: 4-(2-(3-Aminopyrazin-2-yl)-5-bromo-3H-imidazo[4,5-b]pyridin-3-yl)benzyl acetate To a solution of 4-((6-bromo-3-nitropyridin-2-yl)amino)benzyl acetate (1 g, 2.73 mmol) in DMSO (10 mL) were added $Na_2S_2O_4$ (2.16 g, 10.9 mmol, 88% purity) and 3-aminopyrazine-2-carbaldehyde (403 mg, 3.28 mmol). The mixture was stirred at 100° C. for 3 hr. The reaction mixture was quenched with $H_2O$ (50 mL) at 25° C. and extracted with $CH_2Cl_2$ (50 mL×2). The combined organic layers were washed with brine (50 mL×3), dried over anhydrous $Na_2SO_4$, filtered and concentrated under reduced pressure. After purified by silica gel flash chromatography (Eluent of 0%~22% EtOAc in petroleum ether), 4-(2-(3-aminopyrazin-2-yl)-5-bromo-3H-imidazo[4,5-b]pyridin-3-yl)benzyl acetate (Intermediate 298, 270 mg, yield: 21%) was obtained as a yellow solid. MS: m/z=439.1, 441.1 [M+H]$^+$. $^1$H NMR (400 MHz, Chloroform-do 67.99-7.93 (m, 2H), 7.56 (d, J=2.4 Hz, 1H), 7.50-7.44 (m, 3H), 7.33-7.29 (m, 2H), 7.17-6.85 (m, 2H), 5.21 (s, 2H), 2.17 (s, 3H).

Intermediate 299: (1-(Difluoromethyl)-6-oxo-1,6-dihydropyridin-3-yl)boronic acid

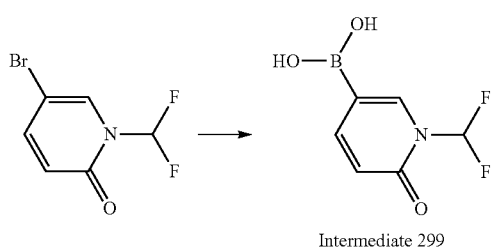 [SMILES: O=c1ccc(Br)cn1C(F)F ; O=c1ccc(B(O)O)cn1C(F)F]

Intermediate 299

A mixture of 5-bromo-1-(difluoromethyl)pyridin-2(1H)-one (50 mg, 223 μmol), 4,4,4',4',5,5,5',5'-octamethyl-2,2'-bi(1,3,2-dioxaborolane) (113 mg, 446 μmol), Pd(dppf)Cl$_2$ (16.3 mg, 22.3 μmol) and KOAc (65.7 mg, 670 μmol) in 1,4-dioxane (2 mL) was degassed and purged with $N_2$ three times. The mixture was stirred at 80° C. for 2 hr under $N_2$ atmosphere. (1-(Difluoromethyl)-6-oxo-1,6-dihydropyridin-3-yl)boronic acid (Intermediate 299) was obtained as a black liquid, the mixture was used for next step directly and without work-up and purification. MS: m/z=189.7 [M+H]$^+$.

Intermediate 300 & 301: 4-Bromo-2-(fluoromethyl)-2H-1,2,3-triazole & 4-Bromo-1-(fluoromethyl)-1H-1,2,3-triazole

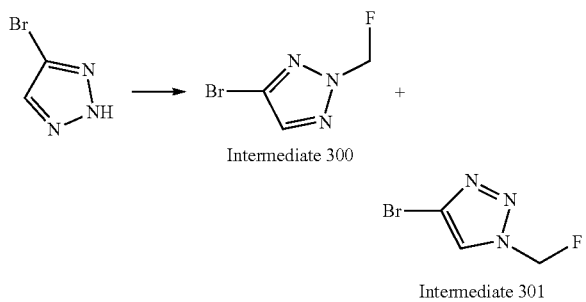

Intermediate 300

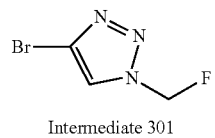

Intermediate 301

A mixture of 4-bromo-2H-1,2,3-triazole (3 g, 20.3 mmol), bromofluoromethane (4.58 g, 40.6 mmol), DIEA (7.86 g, 60.8 mmol) in DMF (50 mL) was degassed and purged with $N_2$ three times. The mixture was stirred at 80° C. for 1 hr under $N_2$ atmosphere. The reaction mixture was diluted with $H_2O$ (100 mL) and extracted with $CH_2Cl_2$ (50 mL×3). The combined organic layers were washed with brine (50 mL×3), dried over $Na_2SO_4$, filtered and concentrated under reduced pressure. The mixture (3.2 g, crude) of 4-bromo-2-(fluoromethyl)-2H-1,2,3-triazole (Intermediate 300) and 4-bromo-1-(fluoromethyl)-1/H-1,2,3-triazole (Intermediate 301) was obtained as a brown solid. $^1$H NMR (400 MHz, Chloroform-d) δ 7.73 (s, 1H), 6.27-6.12 (m, 2H). ¹⁹F NMR (400 MHz, Chloroform-d) δ −166.057. ¹H NMR (400 MHz, Chloroform-d) 7.87 (s, 1H), 6.35-6.20 (m, 2H). ¹⁹F NMR (400 MHz, Chloroform-d) δ −167.648.

Intermediate 302 & 303: 3-(3-(4-(((tert-Butyldimethylsilyl)oxy)methyl)phenyl)-5-(2-(fluoromethyl)-2H-1,2,3-triazol-4-yl)-3H-imidazo[4,5-b]pyridin-2-yl)pyridin-2-amine & 3-(3-(4-(((tert-Butyldimethylsilyl)oxy)methyl)phenyl)-5-(1-(fluoromethyl)-1H-1,2,3-triazol-4-yl)-3H-imidazo[4,5-b]pyridin-2-yl)pyridin-2-amine

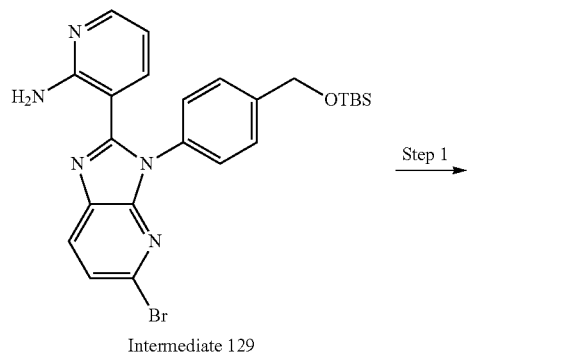

Intermediate 129

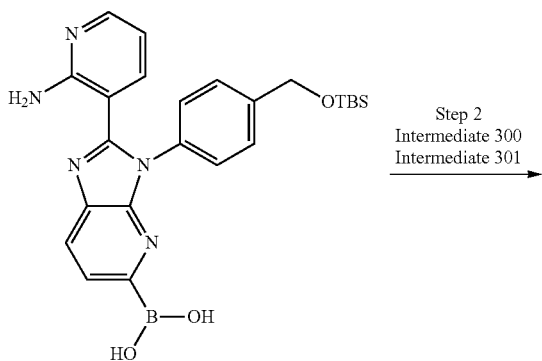

Step 2
Intermediate 300
Intermediate 301

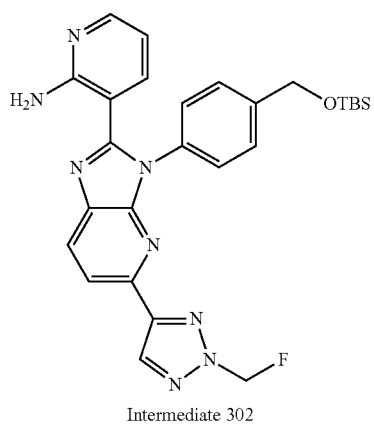

Intermediate 302

+

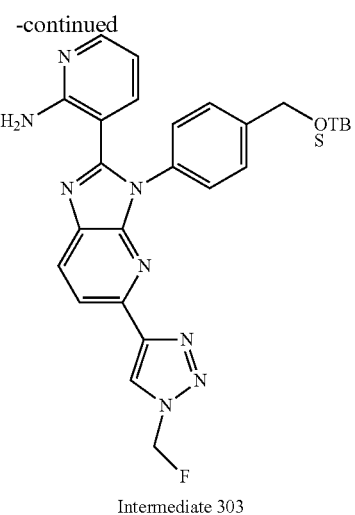

Intermediate 303

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (5 g, 9.79 mmol), 4,4,4',4',5,5,5',5'-octamethyl-2,2'-bi(1,3,2-dioxaborolane) (4.97 g, 19.6 mmol), KOAc (2.88 g, 29.4 mmol) and Pd(dppf)Cl₂ (717 mg, 979 μmol) in 1,4-dioxane (60 mL) was degassed and purged with N₂ three times. The mixture was stirred at 90° C. for 2 hr under N₂ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m, J=476.4 [M+H]⁺.

Step 2: 3-(3-(4-(((tert-Butyldimethylsilyl)oxy)methyl)phenyl)-5-(2-(fluoromethyl)-2H-1,2,3-triazol-4-yl)-3H-imidazo[4,5-b]pyridin-2-yl)pyridin-2-amine & 3-(3-(4-(((Tert-butyldimethylsilyl)oxy)methyl)phenyl)-5-(1-(fluoromethyl)-1H-1,2,3-triazol-4-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (4 g, 8.41 mmol), Intermediate 300 (1.51 g, 8.41 mmol, contained Intermediate 301), Pd(dppf)Cl₂ (616 mg, 841 μmol), Cs₂CO₃ (8.22 g, 25.2 mmol) in 1,4-dioxane (40 mL) and H₂O (10 mL) was degassed and purged with N₂ three times. The mixture was stirred at 100° C. for 4 hr under N₂ atmosphere. The residue was diluted with H₂O (50 mL) and extracted with CH₂Cl₂ (50 mL×3). The combined organic layers were washed with brine (20 mL×2), dried over Na₂SO₄, filtered and concentrated under reduced pressure. After purified by prep-HPLC (column: Phenomenex luna C18 (250×70 mm, 10 m); mobile phase: [water (NH₄HCO₃)-ACN]; gradient: 60%-90% B over 5 min), 3-(3-(4-(((tert-butyldimethylsilyl)oxy)methyl)phenyl)-5-(2-(fluoromethyl)-2H-1,2,3-triazol-4-yl)-3H-imidazo[4,5-b]pyridin-2-yl)pyridin-2-amine as a yellow solid (Intermediate 302, 2.2 g, yield: 48% for two steps) was obtained as a yellow solid. MS: m/z=531.2 [M+H]⁺. ¹H NMR (400 MHz, Chloroform-d) δ 8.21 (s, 1H), 8.17-8.13 (m, 1H), 8.09-8.04 (m, 2H), 7.51 (d, J=8.0 Hz, 2H), 7.39 (d, J=8.4 Hz, 2H), 7.13 (dd, J=7.6, 1.6 Hz, 1H), 6.67 (br s, 2H), 6.38 (dd, J=8.0, 5.2 Hz, 1H), 6.28 (d, J=52.0 Hz, 2H), 4.87 (s, 2H), 0.98 (s, 9H), 0.16 (s, 6H). $^{19}$F NMR (400 MHz, Chloroform-d) δ −166.057. 3-(3-(4-((tert-butyldimethylsilyl)oxy)methyl)phenyl)-5-(1-(fluoromethyl)-1H-1,2,3-triazol-4-yl)-3H-imidazo[4,5-b]pyridin-2-yl)pyridin-2-amine (Intermediate 303, 550 mg, yield: 8.9% for two steps) was obtained as a brown solid. MS: m/z=531.1 [M+H]$^+$. $^1$H NMR (400 MHz, Chloroform-d) δ 8.30-8.23 (m, 2H), 8.18-8.14 (m, 1H), 8.09-8.06 (m, 1H), 7.50 (d, J=8.4 Hz, 2H), 7.37 (d, J=8.4 Hz, 2H), 7.11 (dd, J=8.0, 1.6 Hz, 1H), 6.67 (br s, 2H), 6.39-6.35 (m, 2H), 6.24-6.22 (m, 1H), 4.87 (s, 2H), 0.99 (s, 9H), 0.17 (s, 6H). $^{19}$F NMR (400 MHz, Chloroform-d) δ −167.296.

Intermediate 304: 3-(3-(4-(Chloromethyl)phenyl)-5-(2-(fluoromethyl)-2H-1,2,3-triazol-4-yl)-3H-imidazo[4,5-b]pyridin-2-yl)pyridin-2-amine

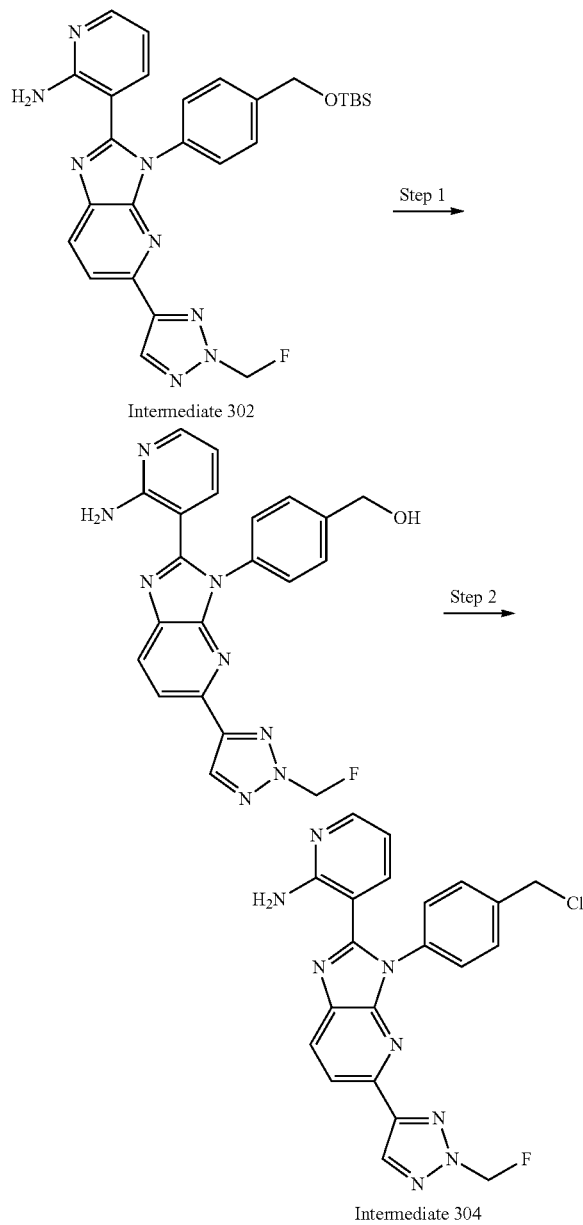

Step 1: (4-(2-(2-Aminopyridin-3-yl)-5-(2-(fluoromethyl)-2H-1,2,3-triazol-4-yl)-3H-imidazo[4,5-b]pyridin-3-yl)phenyl)methanol To a solution of Intermediate 302 (2.2 g, 4.15 mmol) in THF (20 mL) was added TBAF (6.22 mL, 1 M in THF). The residue was diluted with H$_2$O (50 mL) and extracted with CH$_2$Cl$_2$ (50 mL×3). The combined organic layers were washed with brine (20 mL×2), dried over Na$_2$SO$_4$, filtered and concentrated under reduced pressure. (4-(2-(2-Aminopyridin-3-yl)-5-(2-(fluoromethyl)-2H-1,2,3-triazol-4-yl)-3H-imidazo[4,5-b]pyridin-3-yl)phenyl)methanol (1.5 g, crude) was obtained as a brown solid which was used into the next step directly. MS: m/z=417.3 [M+H]$^+$. $^1$H NMR (400 MHz, Dimethylsulfoxide-d$_6$) δ 8.38-8.27 (m, 2H), 8.07-7.95 (m, 2H), 7.51-7.42 (m, 4H), 7.23 (dd, J=7.6, 1.6 Hz, 1H), 6.91 (br s, 2H), 6.55-6.53 (m, 1H), 6.44-6.40 (m, 2H), 5.37 (br t, J=5.6 Hz, 1H), 4.60 (d, J=5.6 Hz, 2H). $^{19}$F NMR (400 MHz, Dimethylsulfoxide-d$_6$) δ −166.272.

Step 2: 3-(3-(4-(Chloromethyl)phenyl)-5-(2-(fluoromethyl)-2H-1,2,3-triazol-4-yl)-3H-imidazo[4,5-b]pyridin-2-yl)pyridin-2-amine To a solution of (4-(2-(2-aminopyridin-3-yl)-5-(2-(fluoromethyl)-2H-1,2,3-triazol-4-yl)-3H-imidazo[4,5-b]pyridin-3-yl)phenyl)methanol (1.5 g, 3.60 mmol) in CH$_2$Cl$_2$ (5 mL) was added SOCl$_2$ (857 mg, 7.20 mmol). The reaction mixture was stirred at 40° C. for 1 hr. The reaction mixture was concentrated. 3-(3-(4-(Chloromethyl)phenyl)-5-(2-(fluoromethyl)-2H-1,2,3-triazol-4-yl)-3H-imidazo[4,5-b]pyridin-2-yl)pyridin-2-amine (Intermediate 304, 1.6 g, crude, HCl salt) was obtained as a yellow solid, which was used into the next step directly. MS: m/z=435.0, 437.0 [M+H]$^+$.

Intermediate 305: 3-(3-(4-(Chloromethyl)phenyl)-5-(1-(fluoromethyl)-1H-1,2,3-triazol-4-yl)-3H-imidazo[4,5-b]pyridin-2-yl)pyridin-2-amine

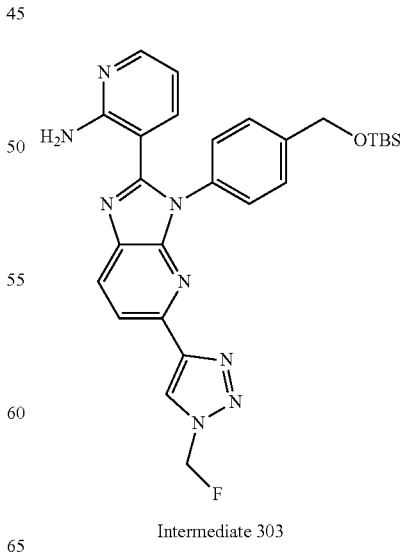

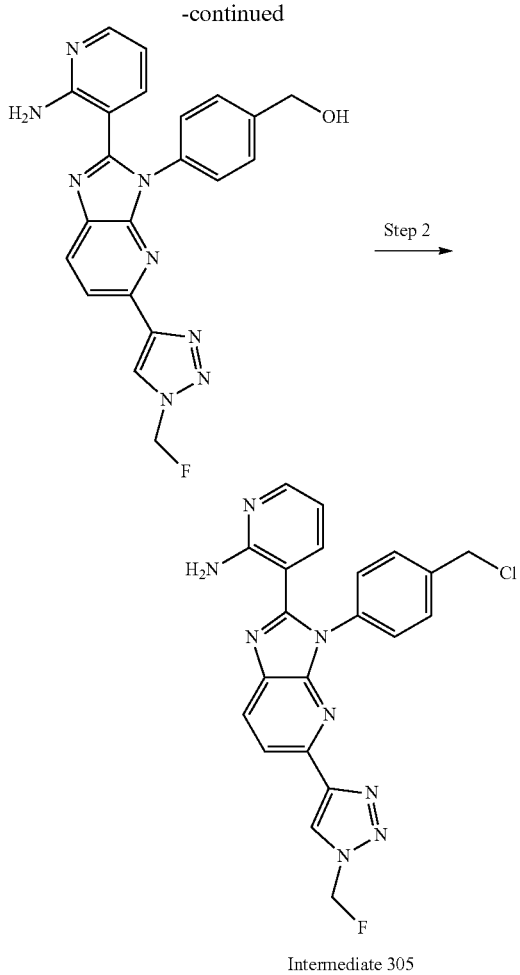

Intermediate 305

Step 1: (4-(2-(2-Aminopyridin-3-yl)-5-(1-(fluoromethyl)-1H-1,2,3-triazol-4-yl)-3H-imidazo[4,5-b]pyridin-3-yl)phenyl)methanol To a solution of Intermediate 303 (550 mg, 1.04 mmol) in THF (20 mL) was added TBAF (1.55 mL, 1 M in THF). The residue was diluted with H$_2$O (10 mL) and extracted with CH$_2$Cl$_2$ (20 mL×3). The combined organic layers were washed with brine (20 mL×2), dried over Na$_2$SO$_4$, filtered and concentrated under reduced pressure. (4-(2-(2-Aminopyridin-3-yl)-5-(1-(fluoromethyl)-1H-1,2,3-triazol-4-yl)-3H-imidazo[4,5-b]pyridin-3-yl)phenyl)methanol (420 mg, crude) was obtained as a yellow solid which was used into the next step directly. MS: m/z=417.1 [M+H]$^+$. $^1$H NMR (400 MHz, Dimethylsulfoxide-d$_6$) δ 8.77 (s, 1H), 8.31 (d, J=8.0 Hz, 1H), 8.12 (d, J=8.4 Hz, 1H), 8.01-7.98 (m, 1H), 7.51-7.40 (m, 4H), 7.22 (dd, J=7.6, 1.6 Hz, 1H), 6.92 (br s, 2H), 6.54 (br s, 1H), 6.44-6.38 (m, 2H), 5.42-5.37 (m, 1H), 4.60 (d, J=5.6 Hz, 2H). $^{19}$F NMR (400 MHz, Dimethylsulfoxide-d$_6$) δ −166.677.

Step 2: 3-(3-(4-(Chloromethyl)phenyl)-5-(1-(fluoromethyl)-11H-1,2,3-triazol-4-yl)-3H-imidazo[4,5-b]pyridin-2-yl)pyridin-2-amine To a solution of (4-(2-(2-aminopyridin-3-yl)-5-(1-(fluoromethyl)-1H-1,2,3-triazol-4-yl)-3H-imidazo[4,5-b]pyridin-3-yl)phenyl)methanol (420 mg 1.01 mmol) in CH$_2$Cl$_2$ (5 mL) was added SOCl$_2$ (120 mg, 1.01 mmol). The reaction mixture was stirred at 40° C. for 1 hr. The reaction mixture was concentrated. 3-(3-(4-(Chloromethyl)phenyl)-5-(1-(fluoromethyl)-1H-1,2,3-triazol-4-yl)-3H-imidazo[4,5-b]pyridin-2-yl)pyridin-2-amine (Intermediate 305, 450 mg crude, HCl salt) was obtained as a yellow solid, which was used into the next step directly. MS: m/z=435.1, 437.1 [M+H]$^+$.

Intermediate 306: 4-Bromo-2-(difluoromethyl)-2H-1,2,3-triazole

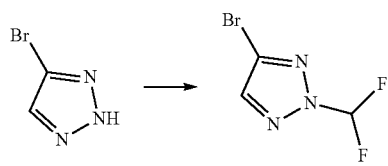

Intermediate 306

To a solution of 4-bromo-2H-1,2,3-triazole (1 g, 6.76 mmol) and Cs$_2$CO$_3$ (6.6 g, 20.3 mmol) in DMSO (30 mL) was added sodium 2-chloro-2,2-difluoroacetate (2.06 g, 13.5 mmol) at 25° C. The mixture was stirred at 90° C. for 16 hr. The mixture was quenched with H$_2$O (30 mL) and extracted with EtOAc (30 mL×3). The combined organic layers were washed with brine (30 mL×5), dried over Na$_2$SO$_4$, filtered and concentrated. After purified by silica gel flash chromatography (Eluent of 0%~5% EtOAc in petroleum ether), 4-bromo-2-(difluoromethyl)-2H-1,2,3-triazole (Intermediate 306, 150 mg, yield: 11%) was obtained as a yellow oil. $^1$H NMR (400 MHz, Dimethylsulfoxide-d$_6$) δ 9.11 (s, 1H), 8.43-8.09 (m, 1H). $^{19}$F NMR (400 MHz, Dimethylsulfoxide-d$_6$) δ −96.77.

Intermediate 307: 3-(3-(4-(Chloromethyl)phenyl)-5-(2-(difluoromethyl)-2H-1,2,3-triazol-4-yl)-3H-imidazo[4,5-b]pyridin-2-yl)pyridin-2-amine

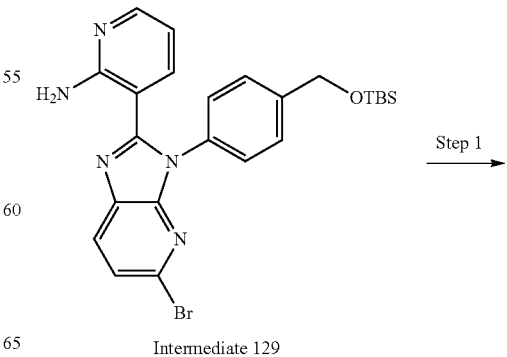

Intermediate 129

985
-continued

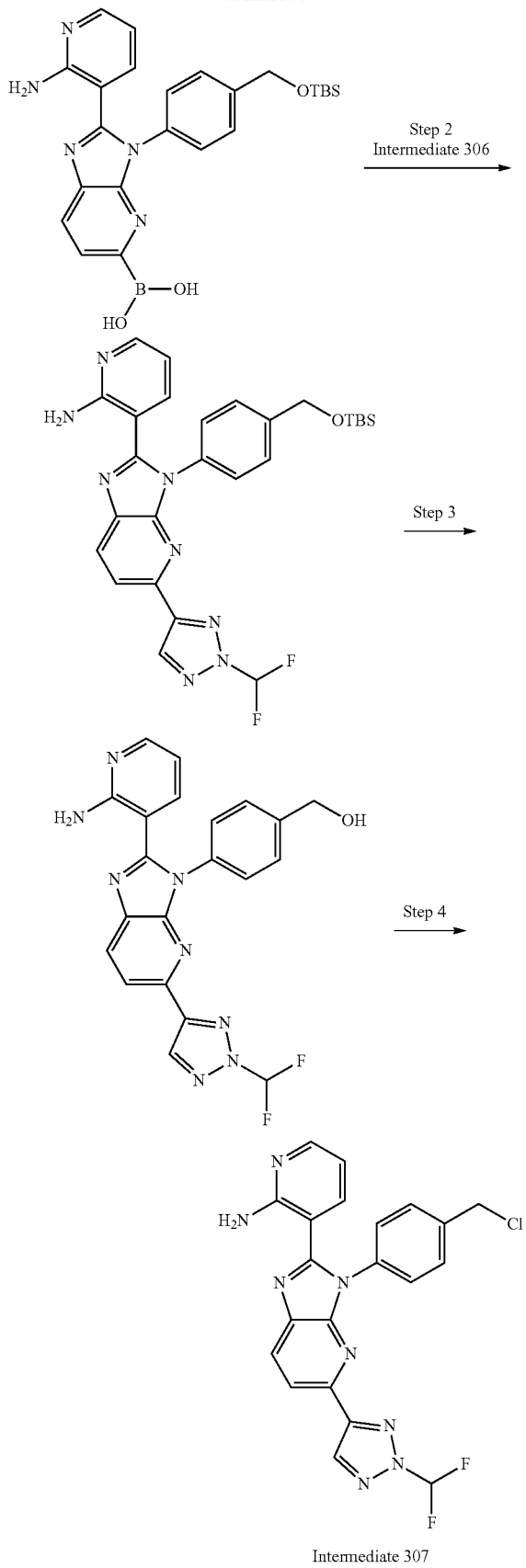

Intermediate 307

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl$_2$ (143 mg, 196 μmol) in 1,4-dioxane (10 mL) was degassed and purged with N$_2$ three times. The mixture was stirred at 90° C. for 8 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((Tert-butyldimethylsilyl)oxy)methyl)phenyl)-5-(2-(difluoromethyl)-2H-1,2,3-triazol-4-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (931 mg, 1.96 mmol), Intermediate 306 (388 mg, 1.96 mmol), Pd(dppf)Cl$_2$ (143 mg, 196 μmol) and Cs$_2$CO$_3$ (1.91 mg, 5.87 mmol) in 1,4-dioxane (10 mL) and H$_2$O (2 mL) was degassed and purged with N$_2$ three times. The mixture was stirred at 90° C. for 16 hr under N$_2$ atmosphere. The reaction mixture was quenched with H$_2$O (10 mL) and extracted with EtOAc (30 mL×3). The combined organic layers were washed with brine (90 mL), dried over Na$_2$SO$_4$, filtered and concentrated under reduced pressure. After purified by prep-HPLC (column: Daisogel SP ODS RPS 150×25 mm×5 μm; mobile phase: [water (NH$_4$HCO$_3$)-ACN]; gradient: 60%-90% B over 11 min), 3-(3-(4-(((tert-butyldimethylsilyl)oxy)methyl)phenyl)-5-(2-(difluoromethyl)-2H-1,2,3-triazol-4-yl)-3H-imidazo[4,5-b]pyridin-2-yl)pyridin-2-amine (350 mg, yield: 33% for two steps) was obtained as a yellow solid. MS: m/z=549.2 [M+H]$^+$. $^1$H NMR (400 MHz, Dimethylsulfoxide-d$_6$) δ 8.93 (s, 1H), 8.33 (d, J=8.4 Hz, 1H), 8.24-8.02 (m, 2H), 7.99 (dd, J=4.8, 1.6 Hz, 1H), 7.53-7.40 (m, 4H), 7.19 (dd, J=7.6, 1.6 Hz, 1H), 6.93 (s, 2H), 6.38 (dd, J=7.6, 4.8 Hz, 1H), 4.80 (s, 2H), 0.92 (s, 9H), 0.10 (s, 6H). $^{19}$F NMR (400 MHz, Dimethylsulfoxide-d$_6$) δ −96.38.

Step 3: (4-(2-(2-Aminopyridin-3-yl)-5-(2-(difluoromethyl)-2H-1,2,3-triazol-4-yl)-3H-imidazo[4,5-b]pyridin-3-yl)phenyl)methanol To a solution of 3-(3-(4-(((tert-butyldimethylsilyl)oxy)methyl)phenyl)-5-(2-(difluoromethyl)-2H-1,2,3-triazol-4-yl)-3H-imidazo[4,5-b]pyridin-2-yl)pyridin-2-amine (320 mg, 583 μmol) in THF (5 mL) was added TBAF (0.5 mL, 1 M in THF). The mixture was stirred at 25° C. for 1 hr. The reaction mixture was quenched with H$_2$O (5 mL) at 25° C. and extracted with EtOAc (10 mL×3). The combined organic layers were washed with brine (50 mL×3), dried over Na$_2$SO$_4$, filtered and concentrated under reduced pressure. (4-(2-(2-Aminopyridin-3-yl)-5-(2-(difluoromethyl)-2H-1,2,3-triazol-4-yl)-3H-imidazo[4,5-b]pyridin-3-yl)phenyl)methanol (300 mg) was obtained as a yellow solid. MS: m/z=435.1 [M+H]$^+$. $^1$H NMR (400 MHz, Dimethylsulfoxide-d$_6$) δ 8.96 (s, 1H), 8.40-8.27 (m, 1H), 8.26-8.05 (m, 2H), 8.00 (dd, J=4.8, 1.6 Hz, 1H), 7.52-7.39 (m, 4H), 7.22 (dd, J=7.6, 1.6 Hz, 1H), 6.93 (brs, 2H), 6.42 (dd, J=7.6, 4.8 Hz, 1H), 5.45-5.32 (m, 1H), 4.60 (d, J=5.6 Hz, 2H). $^{19}$F NMR (400 MHz, Dimethylsulfoxide-d$_6$) δ −96.39.

Step 4: 3-(3-(4-(Chloromethyl)phenyl)-5-(2-(difluoromethyl)-2H-1,2,3-triazol-4-yl)-3H-imidazo[4,5-b]pyridin-2-yl)pyridin-2-amine To a solution of (4-(2-(2-aminopyridin-3-yl)-5-(2-(difluoromethyl)-2H-1,2,3-triazol-4-yl)-3H-imidazo[4,5-b]pyridin-3-yl)phenyl)methanol (300 mg, 691 μmol) in CH$_2$Cl$_2$ (5 mL) was added SOCl$_2$ (246 mg, 2.07 mmol). The mixture was stirred at 40° C. for 0.5 hr. The reaction was concentrated under reduced pressure to give 3-(3-(4-(chloromethyl)phenyl)-5-(2-(difluoromethyl)-2H-1,2,3-triazol-4-yl)-3H-imidazo[4,5-b]pyridin-2-yl)pyridin-2-amine (Intermediate 307, 312 mg, HCl salt) was obtained as a yellow solid. MS: m/z=453.1, 455.1 [M+H]$^+$.

Intermediate 308: 3-(3-(4-(Chloromethyl)phenyl)-5-(2-(methyl-d$_3$)-2H-1,2,3-triazol-4-yl)-3H-imidazo[4,5-b]pyridin-2-yl)pyrazin-2-amine

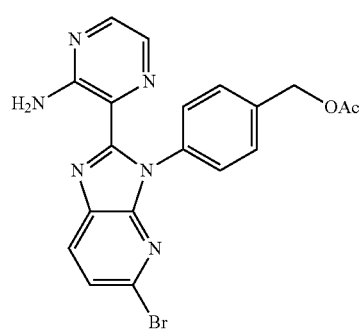

Intermediate 129

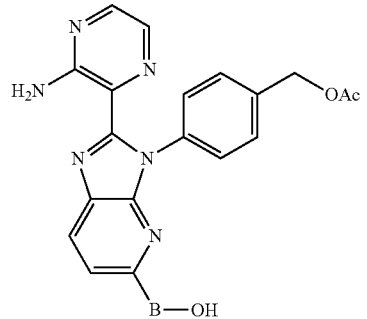

Step 2
Intermediate 280

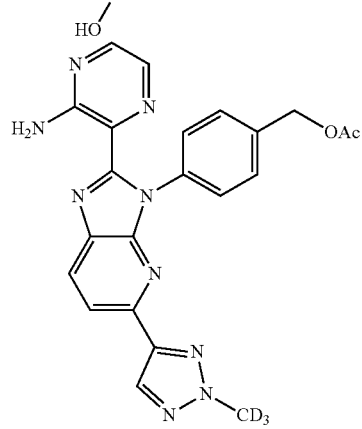

Step 3

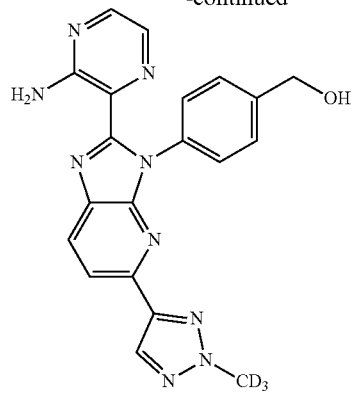

Step 4

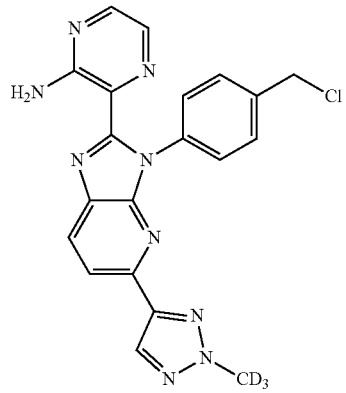

Intermediate 308

Step 1: (3-(4-(Acetoxymethyl)phenyl)-2-(3-aminopyrazin-2-yl)-3H-imidazo[4,5-b]pyridin-5-yl)boronic acid A mixture of Intermediate 129, 4,4,4',4',5,5,5',5'-octamethyl-2,2'-bi(1,3,2-dioxaborolane) (578 mg, 2.28 mmol), Pd(dppf)Cl$_2$ (83.3 mg, 114 μmol) and KOAc (335 mg, 3.41 mmol) in 1,4-dioxane (5 mL) was degassed and purged with N$_2$ three times. The mixture was stirred at 80° C. for 2 hr under N$_2$ atmosphere. (3-(4-(Acetoxymethyl)phenyl)-2-(3-aminopyrazin-2-yl)-3H-imidazo[4,5-b]pyridin-5-yl)boronic acid was obtained as a black liquid, which was used in the next step without work-up and purification. MS: m/z=405.3 [M+H]$^+$.

Step 2: 4-(2-(3-Aminopyrazin-2-yl)-5-(2-(methyl-d$_6$)-2H-1,2,3-triazol-4-yl)-3H-imidazo[4,5-b]pyridin-3-yl)benzyl acetate A mixture of (3-(4-(acetoxymethyl)phenyl)-2-(3-aminopyrazin-2-yl)-3H-imidazo[4,5-b]pyridin-5-yl)boronic acid (460 mg, 1.14 mmol), Intermediate 280 (188 mg, 1.14 mmol), Cs$_2$CO$_3$ (1.11 g, 3.41 mmol) and Pd(dppf)Cl$_2$ (83.3 mg, 114 μmol) in 1,4-dioxane (10 mL) and H$_2$O (2 mL) was degassed and purged with N$_2$ three times. The mixture was stirred at 80° C. for 2 hr under N$_2$ atmosphere. The reaction mixture was quenched with H$_2$O (20 mL) and extracted with CH$_2$Cl$_2$ (20 mL×2). The combined organic layers were washed with brine (20 m L), dried over Na$_2$SO$_4$, filtered and concentrated under reduced pressure. After purified by silica gel flash chromatography (Eluent of 10%~38% EtOAc in petroleum ether), 4-(2-(3-aminopyrazin-2-yl)-5-(2-(methyl-d$_6$)-2H-1,2,3-triazol-4-yl)-3H-imidazo[4,5-b]pyridin-3-yl) benzyl acetate (240 mg, yield: 45% for two steps) was obtained as a yellow solid. MS: m/z=445.2 [M+H]$^+$. $^1$H NMR (400 MHz, Dimethylsulfoxide-d$_6$) δ 8.35 (d, J=8.0 Hz, 1H), 8.09-8.00 (m, 2H), 7.97 (d, J=8.4 Hz, 1H), 7.77 (br s, 2H), 7.54-7.48 (m, 3H), 7.45-7.41 (m, 2H), 5.19 (s, 2H), 2.13 (s, 3H).

Step 3: (4-(2-(3-Aminopyrazin-2-yl)-5-(2-(methyl-d$_3$)-2H-1,2,3-triazol-4-yl)-3H-imidazo[4,5-b]pyridin-3-yl)phenyl)methanol To a solution of 4-(2-(3-aminopyrazin-2-yl)-5-(2-(methyl-d$_6$)-2H-1,2,3-triazol-4-yl)-3H-imidazo[4,5-b]pyridin-3-yl)benzyl acetate (240 mg, 540 μmol) in THF (5 mL), MeOH (5 mL) and H$_2$O (5 mL) was added K$_2$CO$_3$ (224 mg, 1.62 mmol). The mixture was stirred at 25° C. for 1 hr. The reaction mixture was quenched with H$_2$O (20 mL) at 25° C. and extracted with CH$_2$Cl$_2$ (25 mL×2). The combined organic layers were washed with brine (30 mL), dried over Na$_2$SO$_4$, filtered and concentrated under reduced pressure. (4-(2-(3-Aminopyrazin-2-yl)-5-(2-(methyl-d$_6$)-2H-1,2,3-triazol-4-yl)-3H-imidazo[4,5-b]pyridin-3-yl)phenyl)methanol (200 mg, yield: 70%) was obtained as a yellow solid. MS: m/z=403.1 [M+H]$^+$. $^1$H NMR (400 MHz, Dimethylsulfoxide-d$_6$) δ 8.34 (d, J=8.4 Hz, 1H), 8.07-7.98 (m, 2H), 7.96 (d, J=8.0 Hz, 1H), 7.73 (br s, 2H), 7.53 (d, J=2.4 Hz, 1H), 7.46-7.42 (m, 2H), 7.39-7.34 (m, 2H), 5.34 (br t, J=5.6 Hz, 1H), 4.61 (d, J=5.6 Hz, 2H).

Step 4: 3-(3-(4-(Chloromethyl)phenyl)-5-(2-(methyl-d$_3$)-2H-1,2,3-triazol-4-yl)-3H-imidazo[4,5-b]pyridin-2-yl)pyrazin-2-amine To a solution of (4-(2-(3-aminopyrazin-2-yl)-5-(2-(methyl-d$_3$)-2H-1,2,3-triazol-4-yl)-3H-imidazo[4,5-b]pyridin-3-yl)phenyl)methanol (200 mg, 497 μmol) in CH$_2$Cl$_2$ (3 mL) was added SOCl$_2$ (296 mg, 2.49 mmol). The mixture was stirred at 40° C. for 0.5 hr. The reaction was concentrated under reduced pressure to give 3-(3-(4-(chloromethyl)phenyl)-5-(2-(methyl-d$_3$)-2H-1,2,3-triazol-4-yl)-3H-imidazo[4,5-b]pyridin-2-yl)pyrazin-2-amine (Intermediate 308, 220 mg, HCl salt) as a brown solid. MS: m/z=421.1, 423.1 [M+H]$^+$.

Intermediate 309: tert-Butyl N-tert-butoxycarbonyl-N-(4-formylisoxazol-3-yl)carbamate

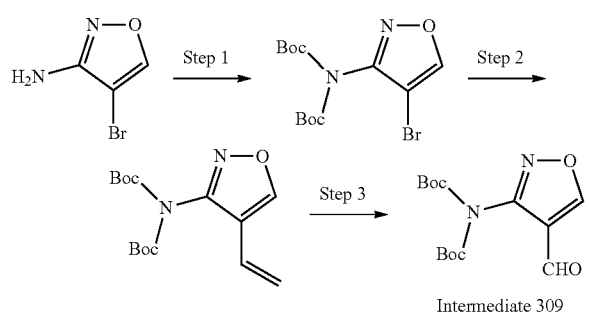

Intermediate 309

Step 1: tert-Butyl N-(4-bromoisoxazol-3-yl)-N-tert-butoxycarbonyl-carbamate

To a solution of 4-bromoisoxazol-3-amine (1 g, 6.14 mmol) in CH$_2$Cl$_2$ (10 mL) were added Boc$_2$O (3.35 g, 15.3 mmol), DMAP (75.0 mg, 614 μmol) and TEA (3.42 mL, 24.5 mmol). The mixture was degassed and purged with N$_2$ three times and stirred at 25° C. for 2 hr under N$_2$ atmosphere. The reaction mixture was quenched with CH$_2$Cl$_2$ (30 mL), washed with H$_2$O (30 mL×3), dried over Na$_2$SO$_4$, filtered and concentrated under reduced pressure. tert-Butyl N-(4-bromoisoxazol-3-yl)-N-tert-butoxycarbonyl-carbamate (2.40 g, crude) was obtained as a brown solid, which was used in the next step directly. MS: m/z=206.9, 208.9 [M-156+H]$^+$. $^1$H NMR (400 MHz, Chloroform-d) δ 8.43 (s, 1H), 1.44 (s, 18H).

Step 2: tert-Butyl N-tert-butoxycarbonyl-N-(4-vinylisoxazol-3-yl)carbamate

To a solution of tert-butyl N-(4-bromoisoxazol-3-yl)-N-tert-butoxycarbonyl-carbamate (2.40 g, 6.61 mmol) in 1,4-dioxane (30 mL) and H$_2$O (6 mL) were added Pd(dppf)Cl$_2$ (484 mg, 661 μmol), Cs$_2$CO$_3$ (6.46 g, 19.8 mmol) and 4,4,5,5-tetramethyl-2-vinyl-1,3,2-dioxaborolane (2.24 mL, 13.2 mmol). The mixture was degassed and purged with N$_2$ for 3 times and stirred at 90° C. for 2 hr. The reaction mixture was quenched with EtOAc (100 mL), washed with brine (100 mL×3), dried over Na$_2$SO$_4$, filtered and concentrated under reduced pressure. After purified by silica gel flash chromatography (Eluent of 0%~10% EtOAc in petroleum ether), tert-butyl N-tert-butoxycarbonyl-N-(4-vinylisoxazol-3-yl)carbamate (1.26 g, yield: 58% for two steps) was obtained as a pink oil. MS: m/z=643.2 [2M+Na]i. $^1$H NMR (400 MHz, Chloroform-d) δ 8.42 (s, 1H), 6.33 (dd, J=18.0, 11.2 Hz, 1H), 5.54 (d, J=18.0 Hz, 1H), 5.34 (d, J 11.2 Hz, 1H), 1.42 (s, 18H)

Step 3: tert-Butyl N-tert-butoxycarbonyl-N-(4-formylisoxazol-3-yl)carbamate

To a solution of tert-butyl N-tert-butoxycarbonyl-N-(4-vinylisoxazol-3-yl)carbamate (1.12 g, 3.61 mmol) in THF (20 mL) were added NaIO$_4$ (1.54 g, 7.22 mmol) and K$_2$OsO$_4$·2H$_2$O (133 mg, 361 μmol). The mixture was degassed and purged with N$_2$ three times and stirred at 0° C. for 2 hr under N$_2$. The reaction mixture was quenched with Sat. Na$_2$SO$_3$ (30 mL) at 0° C. and extracted with EtOAc (30 mL×3). The combined organic layers were washed with brine (50 mL×2), dried over Na$_2$SO$_4$, filtered and concentrated under reduced pressure. After purified by silica gel flash chromatography (Eluent of 0%~10% EtOAc in petroleum ether), tert-butyl N-tert-butoxycarbonyl-N-(4-formylisoxazol-3-yl)carbamate (Intermediate 309, 178 mg, yield: 16%) was obtained as a white solid. $^1$H NMR (400 MHz, Chloroform-d) δ 9.93 (s, 1H), 8.97 (s, 1H), 1.45 (s, 18H).

Intermediate 310: 4-(3-(4-(Chloromethyl)phenyl)-5-(5-fluoropyridin-2-yl)-3H-imidazo[4,5-b]pyridin-2-yl)isoxazol-3-amine

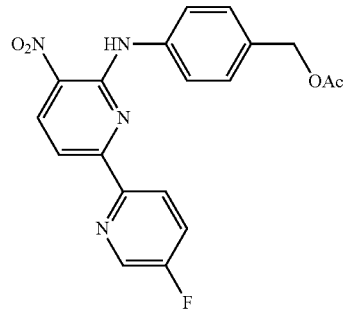

Intermediate 225

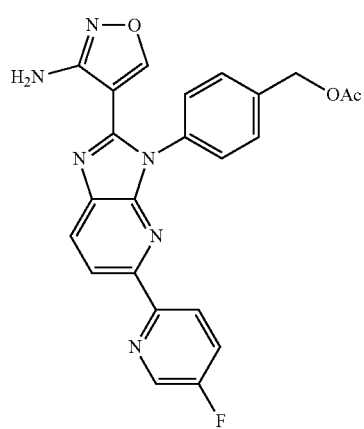

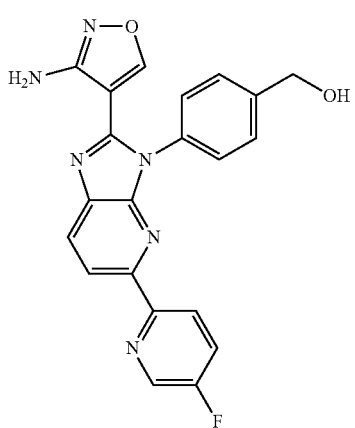

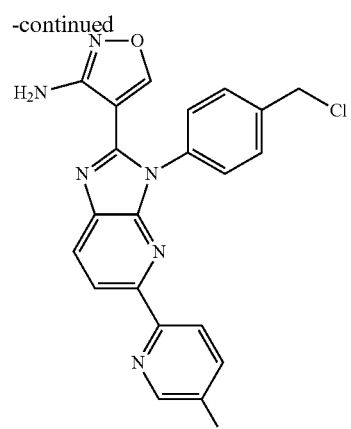

Intermediate 310

Step 1: 4-(2-(3-Aminoisoxazol-4-yl)-5-(5-fluoropyridin-2-yl)-3H-imidazo[4,5-b]pyridin-3-yl)benzyl acetate To a solution of Intermediate 225 (184 mg, 480 μmol) in DMSO (5 mL) were added $Na_2S_2O_4$ (251 mg, 1.44 mmol) and Intermediate 309 (150 mg, 480 μmol). The mixture was degassed and purged with $N_2$ three times and stirred at 100° C. for 2 hr under $N_2$. The reaction mixture was quenched with $H_2O$ (20 mL) and extracted with $CH_2Cl_2$ (10 mL×3). The combined organic layers were washed with brine (20 mL×2), dried over $Na_2SO_4$, filtered and concentrated under reduced pressure. The residue was dissolved in $CH_2Cl_2$ (5 mL) and then TFA (1 mL) was added. The result mixture was stirred at 25° C. for 1 hr. The reaction mixture was quenched with $H_2O$ (10 mL). The pH of the mixture was adjusted to pH to 8 with Sat. aq. $NaHCO_3$. The mixture was extracted with $CH_2Cl_2$ (10 mL×3). The combined organic layers were washed with brine (20 mL×2), dried over $Na_2SO_4$, filtered and concentrated under reduced pressure. After purified by silica gel flash chromatography (Eluent of 0%~30% EtOAc in petroleum ether), 4-(2-(3-aminoisoxazol-4-yl)-5-(5-fluoropyridin-2-yl)-3H-imidazo[4,5-b]pyridin-3-yl)benzyl acetate (57.0 mg, yield: 25%) was obtained as a yellow solid. MS: m/z=445.0 $[M+H]^+$. $^1H$ NMR (400 MHz, Chloroform-d) δ 8.48 (d, J=2.4 Hz, 1H), 8.44 (d, J=8.4 Hz, 1H), 8.26 (dd, J=8.8, 4.8 Hz, 1H), 8.15 (d, J=8.4 Hz, 1H), 7.66 (d, J=8.4 Hz, 2H), 7.51 (d, J=8.4 Hz, 2H), 7.44-7.38 (m, 2H), 5.84 (br s, 2H), 5.30 (s, 2H), 2.21 (s, 3H). $^{19}F$ NMR (400 MHz, Chloroform-d) δ −127.668.

Step 2: (4-(2-(3-Aminoisoxazol-4-yl)-5-(5-fluoropyridin-2-yl)-3H-imidazo[4,5-b]pyridin-3-yl)phenyl)methanol To a solution of 4-(2-(3-Aminoisoxazol-4-yl)-5-(5-fluoropyridin-2-yl)-3H-imidazo[4,5-b]pyridin-3-yl)benzyl acetate (57 mg, 128) in THF (1 mL), MeOH (1 mL) and $H_2O$ (1 mL) was added $K_2CO_3$ (35.5 mg, 257 μmol). The mixture was degassed and purged with $N_2$ three times and stirred at 25° C. for 0.5 hr under $N_2$. The reaction mixture was quenched with EtOAc (20 mL), washed with brine (10 mL×2), dried over $Na_2SO_4$, filtered and concentrated under reduced pressure. (4-(2-(3-Aminoisoxazol-4-yl)-5-(5-fluoropyridin-2-yl)-3H-imidazo[4,5-b]pyridin-3-yl)phenyl)

methanol (51.6 mg) was obtained as a yellow solid, which was used in the next step directly. MS: m/z=403.0 [M+H]+.

Step 3: 4-(3-(4-(Chloromethyl)phenyl)-5-(5-fluoropyridin-2-yl)-3H-imidazo[4,5-b]pyridin-2-yl)isoxazol-3-amine To a solution of (4-(2-(3-aminoisoxazol-4-yl)-5-(5-fluoropyridin-2-yl)-3H-imidazo[4,5-b]pyridin-3-yl)phenyl)methanol (51.6 mg, 128 μmol) in CH$_2$Cl$_2$ (1 mL) was added SOCl$_2$ (153 mg, 1.28 mmol). The mixture was degassed and purged with N$_2$ for 3 times and stirred at 25° C. for 1 hr. The reaction mixture was concentrated under reduced pressure to give 4-(3-(4-(chloromethyl)phenyl)-5-(5-fluoropyridin-2-yl)-3H-imidazo[4,5-b]pyridin-2-yl)isoxazol-3-amine (Intermediate 310, 58.7 mg, HCl salt) as a yellow solid which was used into the next step directly. MS: m/z=420.8, 422.8 [M+H]+.

Intermediate 311 & 312: 5-Bromo-2-(fluoromethoxy-d$_2$)pyridine & 5-Bromo-1-(fluoromethyl-d$_2$)pyridin-2(1H)-one

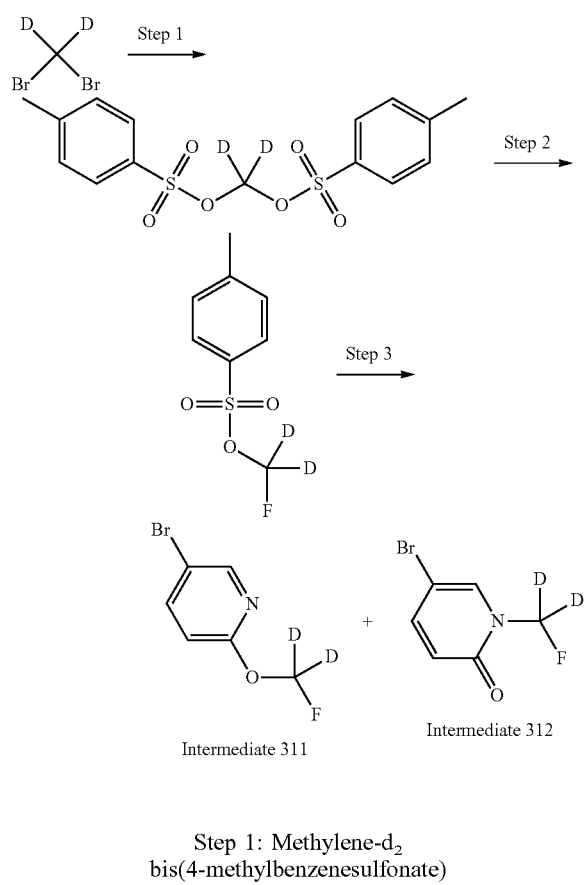

Step 1: Methylene-d$_2$ bis(4-methylbenzenesulfonate)

To a solution of (tosyloxy)silver (52 g, 186 mmol) in MeCN (200 mL) was added dibromomethane-d$_2$ (14.9 g, 84.7 mmol). The mixture was stirred at 80° C. for 16 hr. The reaction mixture was filtered to remove all the salts. The filtrate was collected and concentrated under reduced pressure. The crude was triturated with CH$_2$Cl$_2$ (150 mL) at 25° C. for 3 hr. The filtrate was collected and concentrated under reduced pressure to give methylene-d$_2$ bis(4-methylbenzenesulfonate) (18 g, yield: 59%) was obtained as an off-white solid. MS: m/z=381.0 [M+Na]+. $^1$H NMR (400 MHz, Dimethylsulfoxide-d$_6$) δ 7.60 (d, J=8.4 Hz, 4H), 7.40 (d, J=8.0 Hz, 4H), 2.42 (s, 6H).

Step 2: Fluoromethyl-d$_2$ 4-methylbenzenesulfonate

To a solution of methylene-d$_2$ bis(4-methylbenzenesulfonate) (3.2 g, 8.93 mmol) in MeCN (80 mL) were added CsF (2.03 g, 13.4 mmol) and 3,6,9,12,15-pentaoxaheptadecane-1,17-diol (3.78 g, 13.4 mmol). The mixture was stirred at 80° C. for 16 hr. The residue was diluted with H$_2$O (10 mL) and extracted with CH$_2$Cl$_2$ (10 mL×3). The combined organic layers were washed with brine (5 mL×2), dried over Na$_2$SO$_4$, filtered and concentrated under reduced pressure. After purified by silica gel flash chromatography (Eluent of 0%~5% EtOAc in petroleum ether), fluoromethyl-d$_2$ 4-methylbenzenesulfonate (18 g, yield: 48%) was obtained as a colorless oil. $^1$H NMR (400 MHz, Dimethylsulfoxide-d$_6$) δ 7.85 (d, J=8.4 Hz, 2H), 7.51 (d, J=8.0 Hz, 2H), 2.43 (s, 3H). $^{19}$F NMR (400 MHz, Dimethylsulfoxide-d$_6$) δ −154.079.

Step 3: 5-Bromo-2-(fluoromethoxy-d$_2$)pyridine & 5-Bromo-1-(fluoromethyl-d$_2$)pyridin-2(11H)-one To a solution of fluoromethyl-d$_2$ 4-methylbenzenesulfonate (890 mg, 4.32 mmol), 5-bromopyridin-2-ol (751 mg, 4.32 mmol) in DMF (15 mL) was added K$_2$CO$_3$ (1.79 g, 13.0 mmol). The mixture was stirred at 50° C. for 2 hr. The residue was diluted with H$_2$O (10 mL) and extracted with CH$_2$Cl$_2$ (10 mL×3). The combined organic layers were washed with brine (5 mL×2), dried over Na$_2$SO$_4$, filtered and concentrated under reduced pressure. After purified by silica gel flash chromatography (Eluent of 0%~15% EtOAc in petroleum ether), 5-bromo-2-(fluoromethoxy-d$_2$)pyridine (Intermediate 311,490 mg, yield: 55%) was obtained as a colorless oil. $^1$H NMR (400 MHz, Dimethylsulfoxide-d$_6$) δ 8.38 (d, J=2.4 Hz, 1H), 8.06 (dd, J=8.8, 2.4 Hz, 1H), 7.01 (d, J=8.8 Hz, 1H). $^{19}$F NMR (400 MHz, Dimethylsulfoxide-d$_6$) δ −156.130. 5-Bromo-1-(fluoromethyl-d$_2$)pyridin-2(1H)-one (Intermediate 312, 490 mg, yield: 19%) was obtained as a colorless oil. $^1$H NMR (400 MHz, Dimethylsulfoxide-d$_6$) δ 8.19 (d, J=2.8 Hz, 1H), 7.62 (dd, J=10.0, 2.8 Hz, 1H), 6.47 (d, J=10.0 Hz, 1H). $^{19}$F NMR (400 MHz, Dimethylsulfoxide-d$_6$) δ −173.825.

Intermediate 313: 3-(3-(4-(Chloromethyl)phenyl)-5-(6-(fluoromethoxy-d$_2$)pyridin-3-yl)-3H-imidazo[4,5-b]pyridin-2-yl)pyridin-2-amine

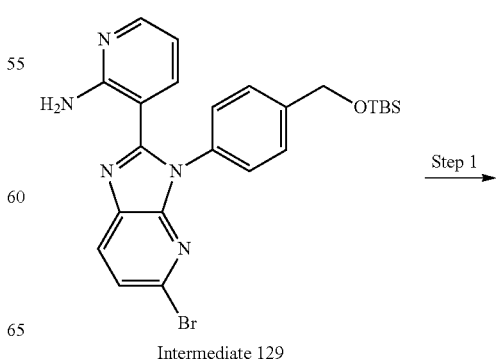

Intermediate 129

995

-continued

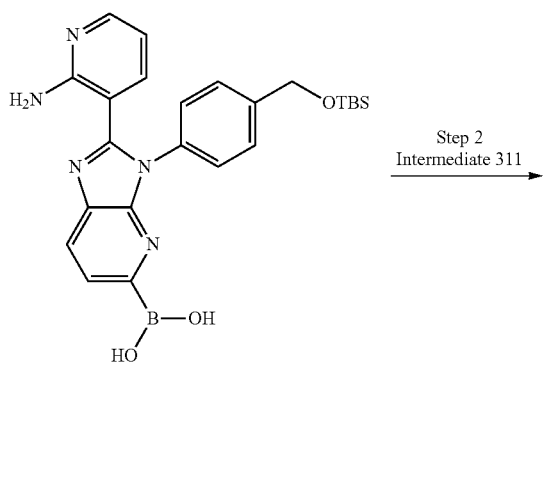

Step 2
Intermediate 311

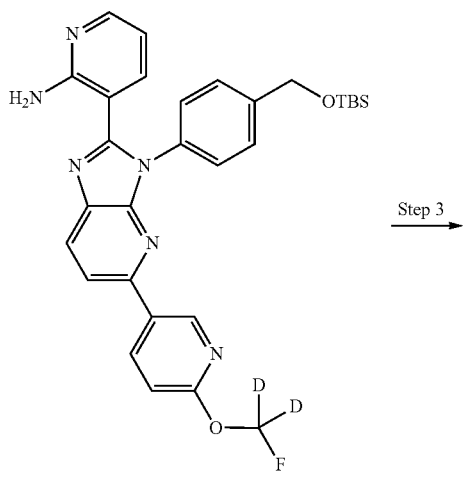

Step 3

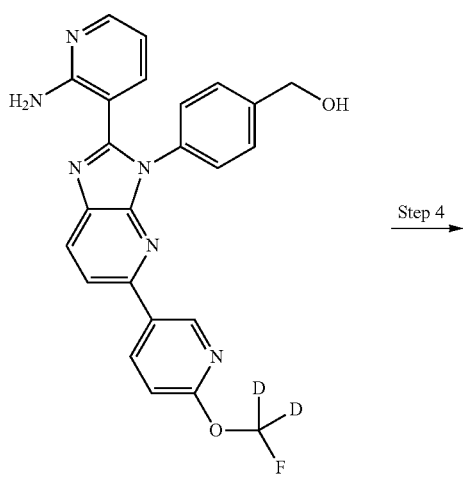

Step 4

996

-continued

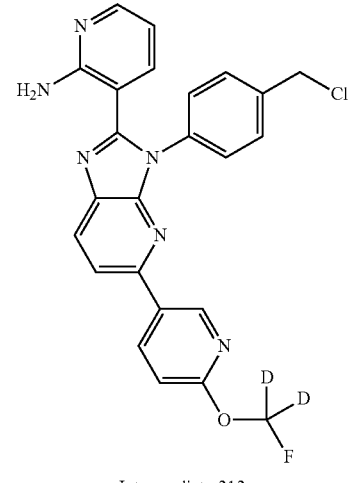

Intermediate 313

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (550 mg, 1.25 mmol), 4,4,4',4',5,5,5',5'-octamethyl-2,2'-bi(1,3,2-dioxaborolane) (547 mg, 2.15 mmol), Pd(dppf)Cl$_2$ (78.8 mg, 108 μmol) and KOAc (317 mg, 3.23 mmol) in 1,4-dioxane (10 mL) was degassed and purged with N$_2$ three times. The mixture was stirred at 90° C. for 2 hr under N$_2$ atmosphere. (2-(2-Aminopyridin-3-yl)-3-(4-(((tert-butyldimethylsilyl)oxy) methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((tert-butyldimethylsilyl)oxy) methyl)phenyl)-5-(6-(fluoromethoxy-d$_2$)pyridin-3-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b] pyridin-5-yl)boronic acid (450 mg, 967 μmol), Intermediate 311 (197 mg, 967 μmol), Cs$_2$CO$_3$ (925 mg, 2.84 mmol) and Pd(dppf)Cl$_2$ (69.3 mg, 94.7 μmol) in 1,4-dioxane (10 mL) and H$_2$O (2 mL) was degassed and purged with N$_2$ three times. The mixture was stirred at 100° C. for 3 hr under N$_2$ atmosphere. The reaction mixture was quenched with H$_2$O (20 mL) and extracted with CH$_2$Cl$_2$ (15 mL×2). The combined organic layers were washed with brine (30 mL), dried over Na$_2$SO$_4$, filtered and concentrated under reduced pressure. After purified by silica gel flash chromatography (Eluent of 20%~30% EtOAc in petroleum ether), 3-(3-(4-(((tert-butyldimethylsilyl)oxy)methyl)phenyl)-5-(6-(fluoromethoxy-d$_2$)pyridin-3-yl)-3H-imidazo[4,5-b]pyridin-2-yl)pyridin-2-amine (350 mg, yield: 63% for two steps) was obtained as a gray solid. MS: m/z=559.3 [M+H]$^+$. $^1$H NMR (400 MHz, Dimethylsulfoxide-d$_6$) δ 8.93-8.88 (m, 1H), 8.48-8.35 (m, 1H), 8.32-8.26 (m, 1H), 8.06-7.95 (m, 2H), 7.49-7.47 (m, 1H), 7.23-7.18 (m, 4H), 7.10-7.06 (m, 1H), 7.04-6.98 (m, 2H), 6.41-6.36 (m, 1H), 4.83 (s, 2H), 0.92 (s, 9H), 0.11 (s, 6H). $^{19}$F NMR (400 MHz, Dimethylsulfoxide-d$_6$) δ −155.567.

Step 3: (4-(2-(2-Aminopyridin-3-yl)-5-(6-(fluoromethoxy-d₂)pyridin-3-yl)-3H-imidazo[4,5-b]pyridin-3-yl)phenyl)methanol To a solution of 3-(3-(4-(((tert-butyldimethylsilyl)oxy)methyl)phenyl)-5-(6-(fluoromethoxy-d₂)pyridin-3-yl)-3H-imidazo[4,5-b]pyridin-2-yl)pyridin-2-amine (350 mg, 626 μmol) in THF (5 mL) was added TBAF (1 M in THF, 940 μL). The mixture was stirred at 25° C. for 1 hr. The mixture was stirred at 25° C. for 1 hr. The reaction mixture was quenched with H₂O (10 mL) at 25° C. and extracted with CH₂Cl₂ (10 mL×3). The combined organic layers were washed with brine (10 mL×2), dried over Na₂SO₄, filtered and concentrated under reduced pressure. (4-(2-(2-Aminopyridin-3-yl)-5-(6-(fluoromethoxy-d₂)pyridin-3-yl)-3H-imidazo[4,5-b]pyridin-3-yl)phenyl)methanol (270 mg, yield: 97%) was obtained as a gray solid.

MS: m/z=445.2 [M+H]-¹H NMR (400 MHz, Dimethylsulfoxide-d₆) δ 8.90 (d, J=2.0 Hz, 1H), 8.42 (dd, J=8.8, 2.4 Hz, 1H), 8.29 (d, J=8.8 Hz, 1H), 8.05-7.98 (m, 2H), 7.52-7.42 (m, 4H), 7.22 (dd, J=7.6, 1.2 Hz, 1H), 7.09 (d, J=8.4 Hz, 1H), 7.00 (br s, 2H), 6.42 (dd, J=7.6, 4.8 Hz, 1H), 5.43-5.33 (m, 1H), 4.60 (br d, J=5.6 Hz, 2H). ¹⁹F NMR (400 MHz, Dimethylsulfoxide-d₆) δ −155.567.

Step 4: 3-(3-(4-(Chloromethyl)phenyl)-5-(6-(fluoromethoxy-d₂)pyridin-3-yl)-3H-imidazo[4,5-b]pyridin-2-yl)pyridin-2-amine To a solution of (4-(2-(2-aminopyridin-3-yl)-5-(6-(fluoromethoxy-d₂)pyridin-3-yl)-3H-imidazo[4,5-b]pyridin-3-yl)phenyl)methanol (270 mg, 607 μmol) in CH₂Cl₂ (5 mL) was added SOCl₂ (145 mg, 1.21 mmol). The mixture was stirred at 25° C. for 1 hr. The reaction was concentrated under reduced pressure. 3-(3-(4-(Chloromethyl)phenyl)-5-(6-(fluoromethoxy-d₂)pyridin-3-yl)-3H-imidazo[4,5-b]pyridin-2-yl)pyridin-2-amine (Intermediate 313, 300 mg, HCl salt) was obtained as a brown solid. MS: m/z=463.0, 465.0 [M+H]⁺.

Intermediate 314: 5-(2-(2-Aminopyridin-3-yl)-3-(4-(chloromethyl)phenyl)-3H-imidazo[4,5-b]pyridin-5-yl)-1-(fluoromethyl-d₂)pyridin-2(11H)-one

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 29 (350 mg, 686 μmol), 4,4,4',4',5,5,5',5'-octamethyl-2,2'-bi(1,3,2-dioxaborolane) (348 mg, 1.37 mmol), Pd(dppf)Cl$_2$ (50.2 mg, 68.6 μmol) and KOAc (202 mg, 2.06 mmol) in 1,4-dioxane (5 mL) was degassed and purged with N$_2$ three times. The mixture was stirred at 80° C. for 2 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 5-(2-(2-Aminopyridin-3-yl)-3-(4-(((tert-butyldimethylsilyl)oxy)methyl)phenyl)-3H-imidazo[4,5-b]pyridin-5-yl)-1-(fluoromethyl-d$_6$)pyridin-2(1H)-one A mixture of (2-(2-aminopyridin-3-yl)-3-(4-(((tert-butyldimethylsilyl)oxy)methyl)phenyl)-3H-imidazo[4,5-b]pyridin-5-yl)boronic acid (320 mg, 673 μmol), Intermediate 312 (140 mg, 673 μmol), Cs$_2$CO$_3$ (658 mg, 2.02 mmol) and Pd(dppf)Cl$_2$ (49.3 mg, 67.3 μmol) in 1,4-dioxane (5 mL) and H$_2$O (1 mL) was degassed and purged with N$_2$ three times. The mixture was stirred at 80° C. for 2 hr under N$_2$ atmosphere. The reaction mixture was quenched with H$_2$O (20 mL) and extracted with CH$_2$Cl$_2$ (20 mL×2). The combined organic layers were washed with brine (20 mL), dried over Na$_2$SO$_4$, filtered and concentrated under reduced pressure. After purified by silica gel flash chromatography (Eluent of 10%~68% EtOAc in petroleum ether), 5-(2-(2-aminopyridin-3-yl)-3-(4-(((tert-butyldimethylsilyl)oxy)methyl)phenyl)-3H-imidazo[4,5-b]pyridin-5-yl)-1-(fluoromethyl-d$_2$)pyridin-2(1H)-one (175 mg, yield: 43% for two steps) was obtained as a yellow solid. MS: m/z=559.3 [M+H]$^+$. $^1$H NMR (400 MHz, Dimethylsulfoxide-d$_6$) δ 8.59 (d, J=2.0 Hz, 1H), 8.27 (d, J=8.4 Hz, 1H), 8.16 (dd, J=9.6, 2.4 Hz, 1H), 7.99 (dd, J=4.8, 1.6 Hz, 1H), 7.85 (d, J=8.4 Hz, 1H), 7.51-7.43 (m, 4H), 7.16 (dd, J=7.6, 1.6 Hz, 1H), 7.00 (br s, 2H), 6.59 (d, J=10.0 Hz, 1H), 6.38 (dd, J=7.6, 4.8 Hz, 1H), 4.82 (s, 2H), 0.92 (s, 9H), 0.10 (s, 6H). $^{19}$F NMR (400 MHz, Dimethylsulfoxide-d$_6$) δ −173.761.

Step 3: 5-(2-(2-Aminopyridin-3-yl)-3-(4-(hydroxymethyl)phenyl)-3H-imidazo[4,5-b]pyridin-5-yl)-1-(fluoromethyl-d$_2$)pyridin-2(1H)-one To a solution of 5-(2-(2-aminopyridin-3-yl)-3-(4-(((tert-butyldimethylsilyl)oxy)methyl)phenyl)-3H-imidazo[4,5-b]pyridin-5-yl)-1-(fluoromethyl-d$_2$)pyridin-2(1H)-one (175 mg, 313 gmol) in THF (5 mL) was added TBAF (0.5 mL, 1 M in THF). The mixture was stirred at 25° C. for 1 hr. The reaction mixture was quenched with H$_2$O (20 mL) at 25° C. and extracted with CH$_2$Cl$_2$ (20 mL×3). The combined organic layers were washed with brine (20 mL×3), dried over Na$_2$SO$_4$, filtered and concentrated under reduced pressure. 5-(2-(2-Aminopyridin-3-yl)-3-(4-(hydroxymethyl)phenyl)-3H-imidazo[4,5-b]pyridin-5-yl)-1-(fluoromethyl-d$_2$)pyridin-2(1H)-one (90 mg, yield: 65%) was obtained as a yellow solid. MS: m/z=445.1 [M+H]$^+$. $^1$H NMR (400 MHz, Dimethylsulfoxide-d$_6$) δ 8.61 (d, J=2.4 Hz, 1H), 8.26 (d, J=8.4 Hz, 1H), 8.16 (dd, J=9.6, 2.4 Hz, 1H), 8.02-7.93 (m, 1H), 7.86 (d, J=8.4 Hz, 1H), 7.51-7.41 (m, 4H), 7.23-7.15 (m, 1H), 6.96 (br s, 2H), 6.61 (d, J=9.6 Hz, 1H), 6.41 (dd, J=7.6, 4.8 Hz, 1H), 5.37 (br t, J=5.6 Hz, 1H), 4.60 (d, J=5.6 Hz, 2H).

Step 4: 5-(2-(2-Aminopyridin-3-yl)-3-(4-(chloromethyl)phenyl)-3H-imidazo[4,5-b]pyridin-5-yl)-1-(fluoromethyl-d$_2$)pyridin-2(1H)-one To a solution of 5-(2-(2-aminopyridin-3-yl)-3-(4-(hydroxymethyl)phenyl)-3H-imidazo[4,5-b]pyridin-5-yl)-1-(fluoromethyl-d$_2$)pyridin-2(1H)-one (90 mg, 202 μmol) in CH$_2$Cl$_2$ (3 mL) was added SOCl$_2$ (72 mg, 606 μmol). The mixture was stirred at 40° C. for 0.5 hr. The reaction was concentrated under reduced pressure to give 5-(2-(2-aminopyridin-3-yl)-3-(4-(chloromethyl)phenyl)-3H-imidazo[4,5-b]pyridin-5-yl)-1-(fluoromethyl-d$_2$)pyridin-2(1H)-one (Intermediate 314, 101 mg, HCl salt) was obtained as a yellow solid. MS: m/z=463.1, 465.1 [M+H]$^+$.

Intermediate 315: 4-Bromo-1-ethyl-1H-1,2,3-triazole

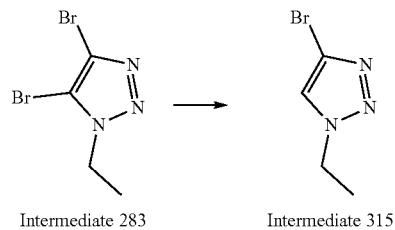

Intermediate 283          Intermediate 315

To a mixture of Intermediate 283 (680 mg, 2.67 mmol) in THF (2 mL) was added n-BuLi (2.5M in hexane, 1.07 m L) at −70° C. under N$_2$, the mixture was stirred at −70° C. for 1 hr. The mixture was diluted with H$_2$O (20 mL) and extracted with EtOAc (20 mL×2). The combined organic layers were washed with brine (20 mL), dried over anhydrous Na$_2$SO$_4$, filtered and concentrated. 4-Bromo-1-ethyl-1H-1,2,3-triazole (Intermediate 315, 440 mg, 2.50 mmol, yield: 94%) was obtained as a yellow oil. MS: m/z=175.8, 177.8 [M+H]$^+$. $^1$H NMR (400 MHz, Dimethylsulfoxide-d$_6$) δ 8.42 (s, 1H), 4.40 (q, J=7.2 Hz, 2H), 1.42 (t, J=7.2 Hz, 3H).

Intermediate 316: 3-(3-(4-(Chloromethyl)phenyl)-5-(1-ethyl-1H-1,2,3-triazol-4-yl)-3H-imidazo[4,5-h]pyridin-2-yl)pyridin-2-amine

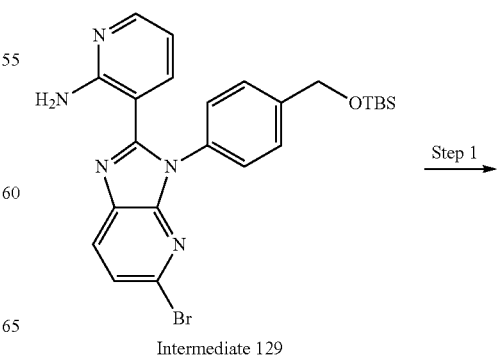

Intermediate 129

1001

-continued

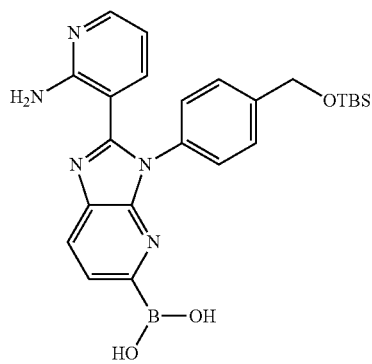

Step 2
Intermediate 315
→

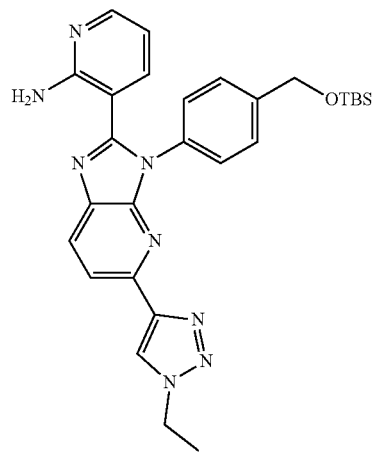

Step 3
→

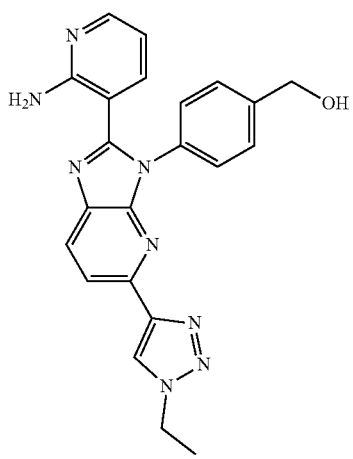

Step 4
→

1002

-continued

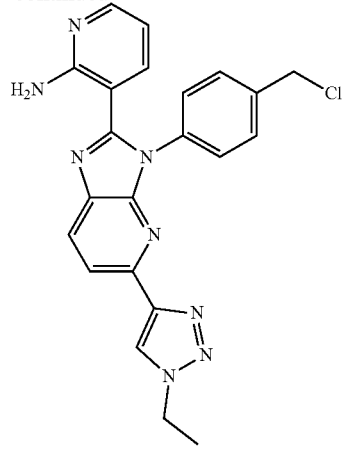

Intermediate 316

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (550 mg 1.25 mmol), 4,4,4',4',5,5,5',5'-octamethyl-2,2'-bi(1,3,2-dioxaborolane) (547 mg, 2.15 mmol), Pd(dppf)Cl$_2$ (78.8 mg, 108 µmol) and KOAc (317 mg, 3.23 mmol) in 1,4-dioxane (10 mL) was degassed and purged with N$_2$ three times. The mixture was stirred at 90° C. for 2 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((tert-Butyldimethylsilyl)oxy)methyl)phenyl)-5-(1-ethyl-1H-1,2,3-triazol-4-yl)-3H-imidazo[4,5-b]pyridin-2-yl)pyridin-2-amine To a mixture of (2-(2-aminopyridin-3-yl)-3-(4-(((tert-butyldimethylsilyl)oxy)methyl)phenyl)-3H-imidazo[4,5-b]pyridin-5-yl)boronic acid (330 mg, 694 µmol) and Intermediate 315 (134 mg 764 µmol) in 1,4-dioxane (6 mL) and H$_2$O (2 mL) were added Cs$_2$CO$_3$ (678 mg, 2.08 mmol) and Pd(dppf)Cl$_2$ (50.8 mg, 69.4 µmol). The mixture was stirred at 100° C. for 2 hr under N$_2$. The mixture was diluted with H$_2$O (20 mL) and extracted with EtOAc (20 mL×2). The combined organic layers were washed with brine (20 mL), dried over anhydrous Na$_2$SO$_4$, filtered and concentrated. After purified by silica gel flash chromatography (EtOAc in petroleum ether=0-50%), 3-(3-(4-(((tert-butyldimethylsilyl)oxy)methyl)phenyl)-5-(1-ethyl-1H-1,2,3-triazol-4-yl)-3H-imidazo[4,5-b]pyridin-2-yl)pyridin-2-amine (210 mg, 399 µmol, yield: 57%) was obtained as a yellow solid. MS: m/z=527.3 [M+H]$^+$. $^1$H NMR (400 MHz, Dimethylsulfoxide-d$_6$) δ 8.39 (s, 1H), 8.27 (d, J=8.0 Hz, 1H), 8.08 (d, J=8.0 Hz, 1H), 7.98 (dd, J=4.8, 1.6 Hz, 1H), 7.51-7.41 (m, 4H), 7.16 (dd, J=7.6, 1.6 Hz, 1H), 6.96 (br s, 2H), 6.37 (dd, J=7.6, 4.8 Hz, 1H), 4.82 (s, 2H), 4.42 (q, J=7.6 Hz, 2H), 1.44 (t, J=7.6 Hz, 3H), 0.93 (s, 9H), 0.11 (s, 6H).

Step 3: (4-(2-(2-Aminopyridin-3-yl)-5-(1-ethyl-1H-1,2,3-triazol-4-yl)-3H-imidazo[4,5-b]pyridin-3-yl)phenyl)methanol To a mixture of 3-(3-(4-(((tert-butyldimethylsilyl)oxy)methyl)phenyl)-5-(1-ethyl-1H-1,2,3-triazol-4-yl)-3H-imidazo[4,5-b]pyridin-2-yl)pyridin-2-amine (210 mg, 399 μmol) in THF (2 mL) was added TBAF (1M in THF, 598 μL). The mixture was stirred at 20° C. for 1 hr. The mixture was diluted with H₂O (20 mL) and extracted with EtOAc (20 mL×2). The combined organic layers were washed with brine (10 mL), dried over anhydrous Na₂SO₄, filtered and concentrated. (4-(2-(2-Aminopyridin-3-yl)-5-(1-ethyl-1H-1,2,3-triazol-4-yl)-3H-imidazo[4,5-b]pyridin-3-yl)phenyl)methanol (164 mg, 398 gmol) was obtained as a yellow solid. MS: m/z=413.2 [M+H]⁺. ¹H NMR (400 MHz, Dimethylsulfoxide-d₆) δ 8.40 (s, 1H), 8.27 (d, J=8.0 Hz, 1H), 8.08 (d, J=8.4 Hz, 1H), 8.01-7.97 (m, 1H), 7.50-7.47 (m, 2H), 7.44-7.41 (m, 2H), 7.20 (dd, J=7.6, 2.0 Hz, 1H), 6.93 (br s, 2H), 6.41 (dd, J=7.6, 4.8 Hz, 1H), 5.40 (t, J=5.6 Hz, 1H), 4.60 (d, J=5.6 Hz, 2H), 4.43 (q, J=7.6 Hz, 2H), 1.45 (t, J=7.6 Hz, 3H).

Step 4: 3-(3-(4-(Chloromethyl)phenyl)-5-(1-ethyl-1H-1,2,3-triazol-4-yl)-3H-imidazo[4,5-b]pyridin-2-yl)pyridin-2-amine To a mixture of (4-(2-(2-aminopyridin-3-yl)-5-(1-ethyl-1H-1,2,3-triazol-4-yl)-3H-imidazo[4,5-b]pyridin-3-yl)phenyl)methanol (160 mg, 388 μmol) in CH₂Cl₂ (2 mL) was added SOCl₂ (28.2 μL, 388 gmol). The mixture was stirred at 20° C. for 1 hr. The mixture was concentrated to give 3-(3-(4-(chloromethyl)phenyl)-5-(1-ethyl-1H-1,2,3-triazol-4-yl)-3H-imidazo[4,5-b]pyridin-2-yl)pyridin-2-amine (Intermediate 316, 167 mg, 388 μmol) was obtained as a yellow solid. MS: mm/z=431.2, 433.1 [M+H]⁺.

Intermediate 317:
2-(4-Bromo-2H-1,2,3-triazol-2-yl)acetonitrile

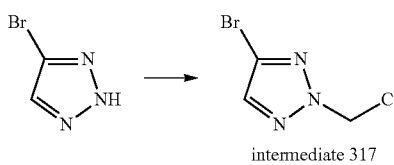

intermediate 317

To a solution of 4-bromo-2H-1,2,3-triazole (300 mg, 2.03 mmol) and 2-bromoacetonitrile (121 mg, 1.01 mmol) in DMF (5 mL) was added K₂CO₃ (841 mg, 6.08 mmol). The mixture was stirred at 25° C. for 2 hr under N₂. The reaction mixture was quenched with NaHSO₃ (10 mL), diluted with H₂O (10 mL), and extracted with CH₂Cl₂ (5 mL×2). The combined organic layers were washed with brine (10 mL), dried over Na₂SO₄, filtered and concentrated under reduced pressure. 2-(4-Bromo-2H-1,2,3-triazol-2-yl)acetonitrile (Intermediate 317, 379 mg) was obtained as a light yellow oil. ¹H NMR (400 MHz, Dimethylsulfoxide-d₆) δ 8.18 (s, 1H), 5.94 (s, 2H).

Intermediate 318: 2-(4-(2-(2-Aminopyridin-3-yl)-3-(4-(chloromethyl)phenyl)-3H-imidazo[4,5-b]pyridin-5-yl)-2H-1,2,3-triazol-2-yl)acetonitrile

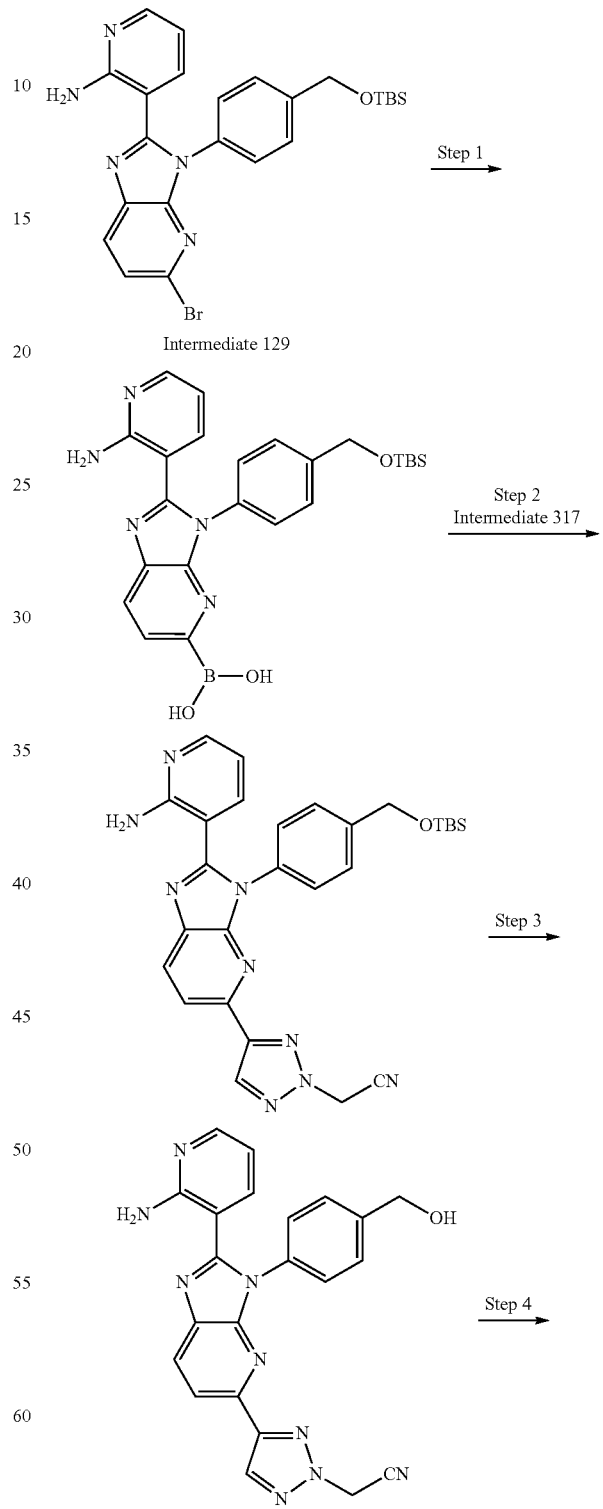

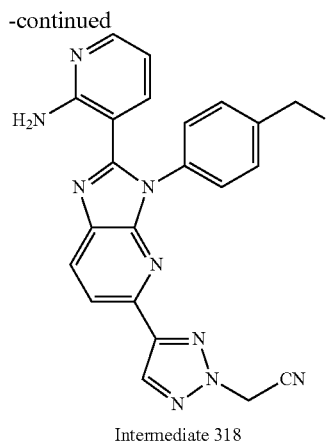

Intermediate 318

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid To a solution of Intermediate 129 (300 mg, 588 μmol) and 4,4,4',4',5,5,5',5'-octamethyl-2,2'-bi(1,3,2-dioxaborolane) (299 mg, 1.18 mmol) in 1,4-dioxane (1 mL) were added KOAc (173 mg, 1.76 mmol) and Pd(dppf)Cl$_2$ (43.0 mg, 58.8 μmol). The mixture was stirred at 85° C. for 2 hr under N$_2$, (2-(2-aminopyridin-3-yl)-3-(4-(((tert-butyldimethylsilyl)oxy)methyl)phenyl)-3H-imidazo[4,5-b]pyridin-5-yl)boronic acid was obtained as a light yellow liquid, which was used in the next step without work up. MS: m/z=476.3 [M+H]$^+$.

Step 2: 2-(4-(2-(2-Aminopyridin-3-yl)-3-(4-((tert-butyldimethylsilyl)oxy)methyl)phenyl)-3H-imidazo[4,5-b]pyridin-5-yl)-2H-1,2,3-triazol-2-yl)acetonitrile To a solution of 3-(5-bromo-3-(4-(((tert-butyldimethylsilyl)oxy)methyl)phenyl)-3H-imidazo[4,5-b]pyridin-2-yl)pyridin-2-amine (279 mg, 588 μmol) and Intermediate 317 (110 mg, 588 μmol) in H$_2$O (0.2 mL) and 1,4-dioxane (1 mL) were added Cs$_2$CO$_3$ (574 mg, 1.76 mmol) and Pd(dppf)Cl$_2$ (43.0 mg, 58.8 μmol). The mixture was stirred at 100° C. for 2 hr under N$_2$ atmosphere. The reaction mixture was quenched with H$_2$O (20 mL) and extracted with CH$_2$Cl$_2$ (15 mL×2). The combined organic layers were washed with brine (30 mL), dried over Na$_2$SO$_4$, filtered and concentrated under reduced pressure. After purified by silica gel flash chromatography (Eluent of 0%~50% ethyl acetate in petroleum ether), 2-(4-(2-(2-aminopyridin-3-yl)-3-(4-(((tert-butyldimethylsilyl)oxy)methyl)phenyl)-3H-imidazo[4,5-b]pyridin-5-yl)-2H-1,2,3-triazol-2-yl)acetonitrile (170 mg, yield: 54% for two steps) was obtained as a light yellow solid. MS: m/z=538.3 [M+H]$^+$ Step 3: 2-(4-(2-(2-Aminopyridin-3-yl)-3-(4-(hydroxymethyl)phenyl)-3H-imidazo[4,5-b]pyridin-5-yl)-2H-1,2,3-triazol-2-yl)acetonitrile To a solution of 2-(4-(2-(2-aminopyridin-3-yl)-3-(4-(((tert-butyldimethylsilyl)oxy)methyl)phenyl)-3H-imidazo[4,5-b]pyridin-5-yl)-2H-1,2,3-triazol-2-yl)acetonitrile (170 mg, 316 μmol) in THF (2 mL) were added TBAF (1 M in THF, 411 μL). The mixture was stirred at 25° C. for 0.5 hr. H$_2$O (10 mL) was added and the aqueous was extracted with EtOAc (10 mL×2). The combined organic layers were dried over anhydrous Na$_2$SO$_4$, filtered and concentrated. 2-(4-(2-(2-Aminopyridin-3-yl)-3-(4-(hydroxymethyl)phenyl)-3H-imidazo[4,5-b]pyridin-5-yl)-2H-1,2,3-triazol-2-yl)acetonitrile (134 mg) was obtained as light yellow oil. MS: m/z=424.2 [M+H]$^+$.

Step 4: 2-(4-(2-(2-Aminopyridin-3-yl)-3-(4-(chloromethyl)phenyl)-3H-imidazo[4,5-b]pyridin-5-yl)-2H-1,2,3-triazol-2-yl)acetonitrile To a solution of 2-(4-(2-(2-aminopyridin-3-yl)-3-(4-(hydroxymethyl)phenyl)-3H-imidazo[4,5-b]pyridin-5-yl)-2H-1,2,3-triazol-2-yl)acetonitrile (134 mg, 316 μmol) in CH$_2$Cl$_2$ (1 mL) was added SOCl$_2$ (68.9 μL). The mixture was stirred at 25° C. for 1 hr. The reaction was concentrated to give 2-(4-(2-(2-aminopyridin-3-yl)-3-(4-(chloromethyl)phenyl)-3H-imidazo[4,5-b]pyridin-5-yl)-2H-1,2,3-triazol-2-yl)acetonitrile (Intermediate 318, 140 mg) was obtained as a light yellow solid. MS: m/z=442.1, 444.1[M+H]$^+$ Intermediate 319 & 320: 4-(2-(3-Aminopyrazin-2-yl)-5-(2-(fluoromethyl)-2H-1,2,3-triazol-4-yl)-3H-imidazo[4,5-b]pyridin-3-yl)benzyl acetate & 4-(2-(3-Aminopyrazin-2-yl)-5-(1-(fluoromethyl)-1H-1,2,3-triazol-4-yl)-3H-imidazo[4,5-b]pyridin-3-yl)benzyl acetate

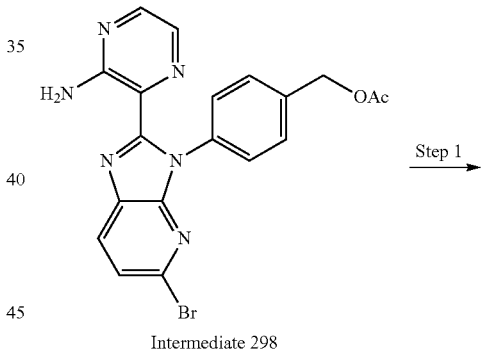

Intermediate 298

Step 1

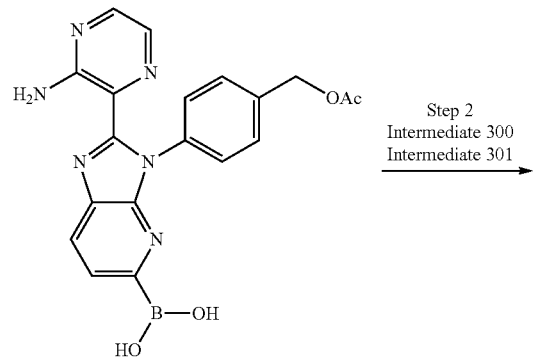

Step 2
Intermediate 300
Intermediate 301

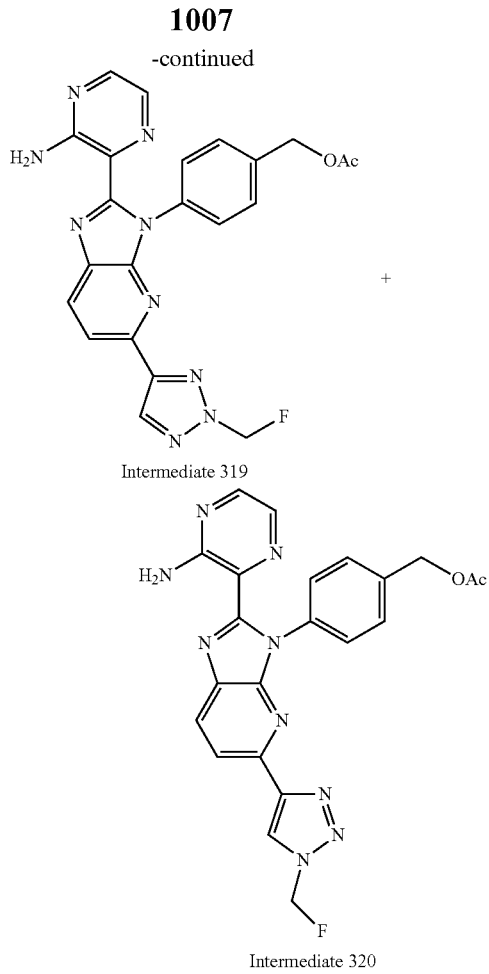

Intermediate 319

Intermediate 320

Step 1: (3-(4-(Acetoxymethyl)phenyl)-2-(3-amino-pyrazin-2-yl)-3H-imidazo[4,5-b]pyridin-5-yl)boronic acid A mixture of Intermediate 298 (500 mg, 1.14 mmol), 4,4,4',4',5,5,5',5'-octamethyl-2,2'-bi(1,3,2-dioxaborolane) (578 mg, 2.28 mmol), KOAc (335 mg, 3.41 mmol) and Pd(dppf)Cl$_2$ (83.3 mg, 114 μmol) in 1,4-dioxane (5 mL) was degassed and purged with N$_2$ three times. The mixture was stirred at 90° C. for 2 hr under N$_2$ atmosphere. (3-(4-(Acetoxymethyl)phenyl)-2-(3-aminopyrazin-2-yl)-3H-imidazo[4,5-b]pyridin-5-yl)boronic acid was obtained as a black liquid, which was used in the next step without work-up and purification. MS: m/z=405.2 [M+H]$^+$.

Step 2: 4-(2-(3-Aminopyrazin-2-yl)-5-(2-(fluoromethyl)-2H-1,2,3-triazol-4-yl)-3H-imidazo[4,5-b]pyridin-3-yl)benzyl acetate & 4-(2-(3-Aminopyrazin-2-yl)-5-(1-(fluoromethyl)-1H-1,2,3-triazol-4-yl)-3H-imidazo[4,5-b]pyridin-3-yl)benzyl acetate A mixture of (3-(4-(acetoxymethyl)phenyl)-2-(3-amino-pyrazin-2-yl)-3H-imidazo[4,5-b]pyridin-5-yl)boronic acid (450 mg, 1.11 mmol), Intermediate 300 (200 mg, 1.11 mmol, contained Intermediate 301), Pd(dppf)Cl$_2$ (81.5 mg, 111 μmol), Cs$_2$CO$_3$ (1.09 g, 3.34 mmol) in 1,4-dioxane (10 mL) and H$_2$O (2.5 mL) was degassed and purged with N$_2$ three times. The mixture was stirred at 100° C. for 16 hr under N$_2$ atmosphere. The residue was diluted with H$_2$O (10 mL) and extracted with CH$_2$Cl$_2$ (10 mL×3). The combined organic layers were washed with brine (5 mL×2), dried over Na$_2$SO$_4$, filtered and concentrated under reduced pressure. After purified by prep-HPLC (column: Waters Xbridge BEH C18 250×50 mm×10 μm; mobile phase: [water (NH$_4$HCO$_3$)-ACN]; gradient: 33%-63% B over 10 min), 4-(2-(3-amino-pyrazin-2-yl)-5-(2-(fluoromethyl)-2H-1,2,3-triazol-4-yl)-3H-imidazo[4,5-b]pyridin-3-yl)benzyl acetate (Intermediate 319, 200 mg, yield: 36% for two steps) was obtained as a gray solid. MS: m/z=460.1 [M+H]$^+$. $^1$H NMR (400 MHz, Dimethylsulfoxide-d$_6$) δ 8.41 (d, J=8.4 Hz, 1H), 8.35 (s, 1H), 8.09-7.98 (m, 2H), 7.78 (br s, 2H), 7.56-7.41 (m, 5H), 6.49 (d, J=51.6 Hz, 2H), 5.20 (s, 2H), 2.13 (s, 3H). $^{19}$F NMR (400 MHz, Dimethylsulfoxide-d$_6$) δ −166.385. 4-(2-(3-Aminopyrazin-2-yl)-5-(1-(fluoromethyl)-1H-1,2,3-triazol-4-yl)-3H-imidazo[4,5-b]pyridin-3-yl)benzyl acetate (Intermediate 320, 80 mg, yield: 15% for two steps) was also obtained as a gray solid. MS: m/z=460.1 [M+H]$^+$. $^1$H NMR (400 MHz, Dimethylsulfoxide-d$_6$) δ 8.77 (s, 1H), 8.39 (d, J=8.4 Hz, 1H), 8.16 (d, J=8.4 Hz, 1H), 8.02 (d, J=2.0 Hz, 1H), 7.78 (br s, 2H), 7.53-7.42 (m, 5H), 6.49 (d, J=50.4 Hz, 2H), 5.19 (s, 2H), 2.13 (s, 3H). $^{19}$F NMR (400 MHz, Dimethylsulfoxide-d$_6$) δ −166.760.

Intermediate 321: 3-(3-(4-(Chloromethyl)phenyl)-5-(2-(fluoromethyl)-2H-1,2,3-triazol-4-yl)-3H-imidazo[4,5-b]pyridin-2-yl)pyrazin-2-amine

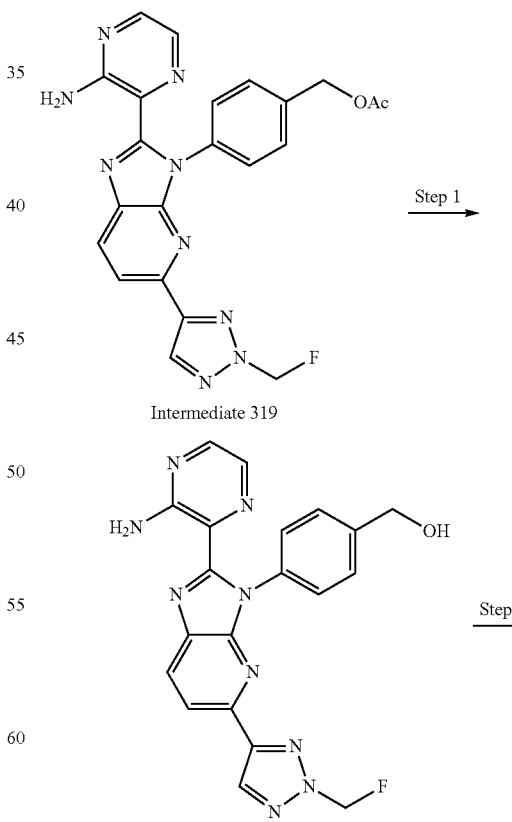

1009
-continued

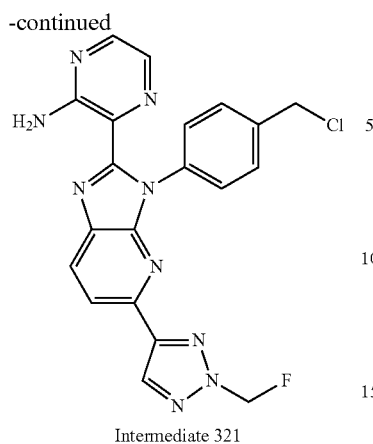

Intermediate 321

Step 1: (4-(2-(3-Aminopyrazin-2-yl)-5-(2-(fluoromethyl)-2H-1,2,3-triazol-4-yl)-3H-imidazo[4,5-b]pyridin-3-yl)phenyl)methanol To a solution of Intermediate 319 (200 mg, 435 μmol) in MeOH (2 mL), THF (2 mL) and H$_2$O (0.5 mL) was added K$_2$CO$_3$ (180 mg, 1.31 mmol). The mixture was stirred at 25° C. for 0.5 hr. The residue was diluted with H$_2$O (8 mL) and extracted with CH$_2$Cl$_2$ (10 mL×3). The combined organic layers were washed with brine (5 mL×2), dried over Na$_2$SO$_4$, filtered and concentrated under reduced pressure. (4-(2-(3-Aminopyrazin-2-yl)-5-(2-(fluoromethyl)-2H-1,2,3-triazol-4-yl)-3H-imidazo[4,5-b]pyridin-3-yl)phenyl)methanol (160 mg, crude) was obtained as a yellow solid which was used into the next step directly. MS: m/z=417.9 [M+H]$^+$. $^1$H NMR (400 MHz, Dimethylsulfoxide-d$_6$) δ 8.40 (d, J=8.0 Hz, 1H), 8.33 (s, 1H), 8.08-7.99 (m, 2H), 7.74 (br s, 2H), 7.55 (d, J=2.4 Hz, 1H), 7.47-7.42 (m, 2H), 7.41-7.35 (m, 2H), 6.48 (d, J=51.6 Hz, 2H), 5.34 (br t, J=5.6 Hz, 1H), 4.61 (d, J=5.6 Hz, 2H). $^{19}$F NMR (400 MHz, Dimethylsulfoxide-d$_6$) δ −166.387.

Step 2: 3-(3-(4-(Chloromethyl)phenyl)-5-(2-(fluoromethyl)-2H-1,2,3-triazol-4-yl)-3H-imidazo[4,5-b]pyridin-2-yl)pyrazin-2-amine To a solution of (4-(2-(3-aminopyrazin-2-yl)-5-(2-(fluoromethyl)-2H-1,2,3-triazol-4-yl)-3H-imidazo[4,5-b]pyridin-3-yl)phenyl)methanol (200 mg, 479 μmol) in CH$_2$Cl$_2$ (5 mL) was added SOCl$_2$ (114 mg, 958 μmol). The reaction mixture was stirred at 40° C. for 1 hr. The reaction mixture was concentrated under reduced pressure to give 3-(3-(4-(chloromethyl)phenyl)-5-(2-(fluoromethyl)-2H-1,2,3-triazol-4-yl)-3H-imidazo[4,5-b]pyridin-2-yl)pyrazin-2-amine (Intermediate 321, 200 mg, crude, HCl salt) as a gray solid, which was used in the next step directly. MS: m/z=435.8, 437.8 [M+H]$^+$.

1010

Intermediate 322: 3-(3-(4-(Chloromethyl)phenyl)-5-(1-(fluoromethyl)-1H-1,2,3-triazol-4-yl)-3H-imidazo[4,5-b]pyridin-2-yl)pyrazin-2-amine

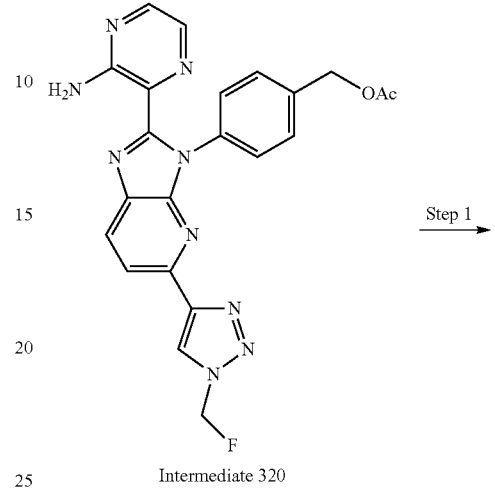

Intermediate 320

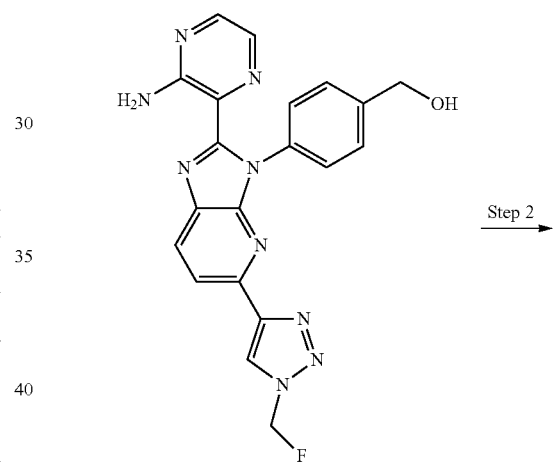

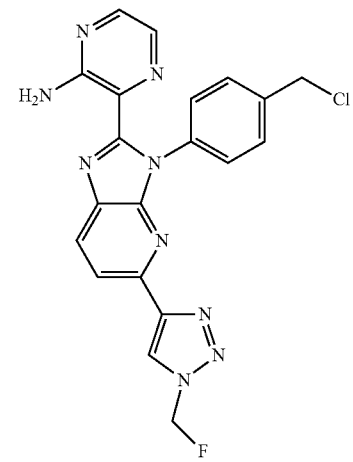

Intermediate 322

Step 1: (4-(2-(3-Aminopyrazin-2-yl)-5-(1-(fluoromethyl)-1H-1,2,3-triazol-4-yl)-3H-imidazo[4,5-b]pyridin-3-yl)phenyl)methanol To a solution of Intermediate 320 (80 mg, 174 µmol) in MeOH (1 mL), THF (1 mL) and H₂O (0.5 mL) was added K₂CO₃ (72.2 mg, 522 mmol). The mixture was stirred at 25° C. for 0.5 hr. The residue was diluted with H₂O (5 mL) and extracted with CH₂Cl₂ (5 mL×3). The combined organic layers were washed with brine (3 mL×2), dried over Na₂SO₄, filtered and concentrated under reduced pressure. (4-(2-(3-Aminopyrazin-2-yl)-5-(1-(fluoromethyl)-1H-1,2,3-triazol-4-yl)-3H-imidazo[4,5-b]pyridin-3-yl)phenyl)methanol (80 mg, crude) was obtained as a yellow solid which was used into the next step directly. MS: m/z=417.9 [M+H]⁺. ¹H NMR (400 MHz, Dimethylsulfoxide-d₆) δ 8.75 (s, 1H), 8.38 (d, J=8.4 Hz, 1H), 8.16 (d, J=8.4 Hz, 1H), 8.01 (d, J=2.4 Hz, 1H), 7.75 (br s, 2H), 7.53 (d, J=2.4 Hz, 1H), 7.47-7.35 (m, 4H), 6.48 (d, J=50.8 Hz, 2H), 5.35 (br t, J=5.6 Hz, 1H), 4.61 (d, J=5.6 Hz, 2H). ¹⁹F NMR (400 MHz, Dimethylsulfoxide-d₆) δ −166.770.

Step 2: 3-(3-(4-(Chloromethyl)phenyl)-5-(1-(fluoromethyl)-1H-1,2,3-triazol-4-yl)-3H-imidazo[4,5-b]pyridin-2-yl)pyrazin-2-amine To a solution of (4-(2-(3-aminopyrazin-2-yl)-5-(1-(fluoromethyl)-1H-1,2,3-triazol-4-yl)-3H-imidazo[4,5-b]pyridin-3-yl)phenyl)methanol (80 mg, 192 µmol) in CH₂Cl₂ (3 mL) was added SOCl₂ (45.6 mg, 383 µmol). The reaction mixture was stirred at 40° C. for 1 hr. The reaction mixture was concentrated under reduced pressure to give 3-(3-(4-(chloromethyl)phenyl)-5-(1-(fluoromethyl)-1H-1,2,3-triazol-4-yl)-3H-imidazo[4,5-b]pyridin-2-yl)pyrazin-2-amine (Intermediate 322, 75 mg, crude, HCl salt) as a gray solid, which was used in the next step directly. MS: m/z=435.8, 437.8 [M+H]⁺.

Intermediate 323: 3-(3-(4-(Chloromethyl)phenyl)-5-(2-ethyl-2H-1,2,3-triazol-4-yl)-3H-imidazo[4,5-b]pyridin-2-yl)pyrazin-2-amine

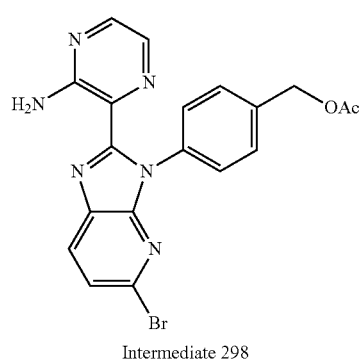

Intermediate 298

Step 1

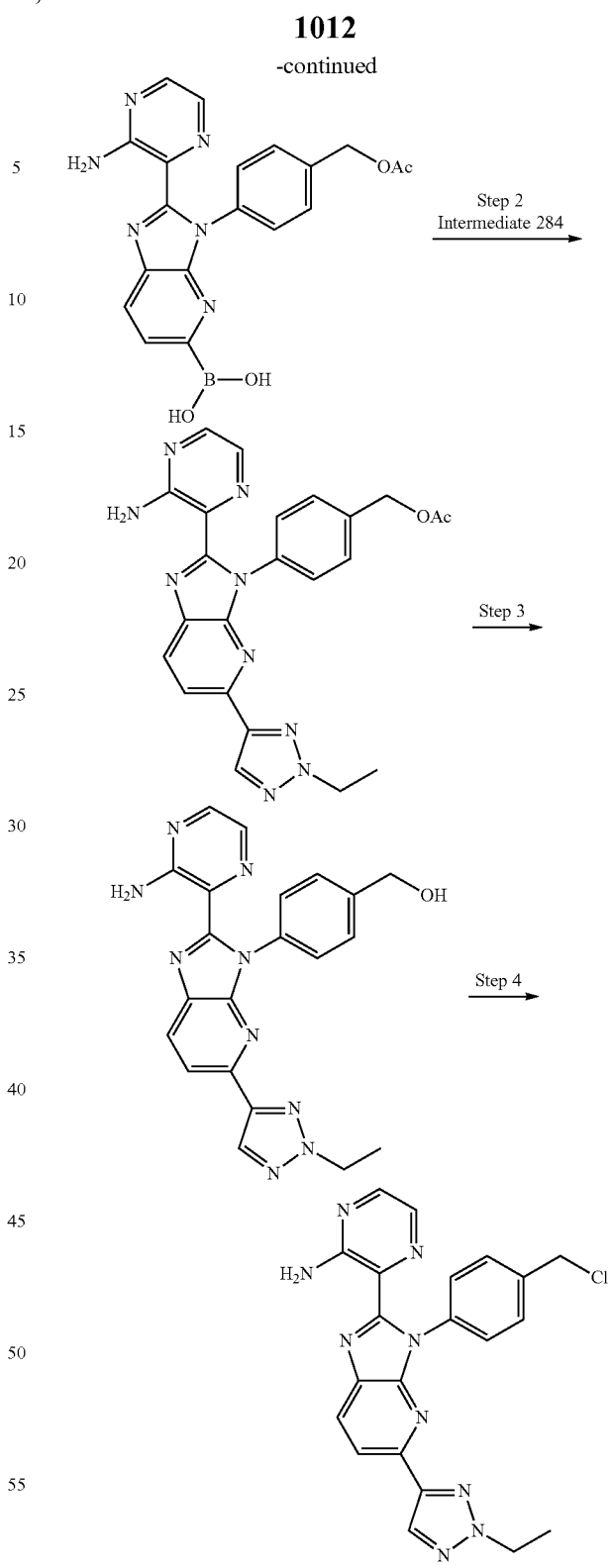

Step 1: (3-(4-(Acetoxymethyl)phenyl)-2-(3-aminopyrazin-2-yl)-3H-imidazo[4,5-b]pyridin-5-yl)boronic acid To a mixture of Intermediate 298 (380 mg, 865 µmol) and 4,4,4',4',5,5,5',5'-octamethyl-2,2'-bi(1,3,2-dioxaborolane)

(439 mg, 1.73 mmol) in 1,4-dioxane (8 mL) were added Pd(dppf)Cl$_2$ (63.3 mg, 86.5 μmol) and KOAc (255 mg, 2.60 mmol). The mixture was stirred at 85° C. for 1 hr. (3-(4-(Acetoxymethyl)phenyl)-2-(3-aminopyrazin-2-yl)-3H-imidazo[4,5-b]pyridin-5-yl)boronic acid was obtained as a black liquid, which was used in the next step without work-up and purification. MS: m/z=405.1 [M+H]$^+$.

Step 2: 4-(2-(3-Aminopyrazin-2-yl)-5-(2-ethyl-2H-1,2,3-triazol-4-yl)-3H-imidazo[4,5-b]pyridin-3-yl) benzyl acetate To a mixture of (3-(4-(acetoxymethyl)phenyl)-2-(3-aminopyrazin-2-yl)-3H-imidazo[4,5-b]pyridin-5-yl)boronic acid (270 mg, 668 μmol) and Intermediate 284 (235 mg, 1.34 mmol) in 1,4-dioxane (10 mL) and H$_2$O (2 mL) were added Cs$_2$CO$_3$ (653 mg, 2.00 mmol) and Pd(dppf)Cl$_2$ (48.9 mg, 66.8 μmol). The mixture was stirred at 100° C. for 1 hr. The reaction mixture was quenched with H$_2$O (50 mL) and extracted with EtOAc (50 mL×2). The combined organic layers were washed with brine (50 mL), dried over anhydrous Na$_2$SO$_4$, filtered and concentrated. After purified by silica gel flash chromatography (EtOAc in petroleum ether=0-50%), 4-(2-(3-aminopyrazin-2-yl)-5-(2-ethyl-2H-1,2,3-triazol-4-yl)-3H-imidazo[4,5-b]pyridin-3-yl)benzyl acetate (250 mg, yield 82% for two steps) was obtained as a yellow solid. MS: m/z=456.2 [M+H]$^+$. $^1$H NMR (400 MHz, Dimethylsulfoxide-d$_6$) δ 8.35 (d, J=8.4 Hz, 1H), 8.05 (s, 1H), 8.02 (d, J=2.4 Hz, 1H), 7.98 (d, J=8.4 Hz, 1H), 7.77 (br s, 2H), 7.56-7.48 (m, 3H), 7.46-7.41 (m, 2H), 5.19 (s, 2H), 4.51 (q, J=7.2 Hz, 2H), 2.13 (s, 3H), 1.49 (t, J=7.2 Hz, 3H).

Step 3: (4-(2-(3-Aminopyrazin-2-yl)-5-(2-ethyl-2H-1,2,3-triazol-4-yl)-3H-imidazo[4,5-b]pyridin-3-yl) phenyl)methanol To a mixture of 4-(2-(3-aminopyrazin-2-yl)-5-(2-ethyl-2H-1,2,3-triazol-4-yl)-3H-imidazo[4,5-b]pyridin-3-yl)benzyl acetate (240 mg, 527 μmol) in THF (1 mL), MeOH (1 mL) and H$_2$O (0.5 mL) was added K$_2$CO$_3$ (218 mg, 1.58 mmol). The mixture was stirred at 20° C. for 0.5 hr. The reaction mixture was quenched with H$_2$O (50 mL) and extracted with EtOAc (30 mL×2). The combined organic layers were washed with brine (30 mL), dried over anhydrous Na$_2$SO$_4$, filtered and concentrated, (4-(2-(3-aminopyrazin-2-yl)-5-(2-ethyl-2H-1,2,3-triazol-4-yl)-3H-imidazo[4,5-b]pyridin-3-yl)phenyl)methanol (210 mg, yield: 96%) was obtained as a yellow solid. MS: m/z=414.2 [M+H]$^+$. $^1$H NMR (400 MHz, Dimethylsulfoxide-d$_6$) δ 8.34 (d, J=8.4 Hz, 1H), 8.03 (s, 1H), 8.01 (d, J=2.4 Hz, 1H), 7.97 (d, J=8.4 Hz, 1H), 7.74 (br s, 2H), 7.53 (d, J=2.4 Hz, 1H), 7.46-7.42 (m, 2H), 7.40-7.34 (m, 2H), 5.34 (t, J=5.6 Hz, 1H), 4.61 (d, J=6.0 Hz, 2H), 4.50 (q, J=7.2 Hz, 2H), 1.49 (t, J=7.2 Hz, 3H).

Step 4: 3-(3-(4-(Chloromethyl)phenyl)-5-(2-ethyl-2H-1,2,3-triazol-4-yl)-3H-imidazo[4,5-b]pyridin-2-yl)pyrazin-2-amine To a mixture of (4-(2-(3-aminopyrazin-2-yl)-5-(2-ethyl-2H-1,2,3-triazol-4-yl)-3H-imidazo[4,5-b]pyridin-3-yl)phenyl)methanol (200 mg, 484 μmol) in CH$_2$Cl$_2$ (0.5 mL) was added SOCl$_2$ (105 μL, 1.45 mmol). The mixture was stirred at 20° C. for 0.5 hr. The reaction was concentrated under reduced pressure. 3-(3-(4-(Chloromethyl)phenyl)-5-(2-ethyl-2H-1,2,3-triazol-4-yl)-3H-imidazo[4,5-b]pyridin-2-yl)pyrazin-2-amine (Intermediate 323, 209 mg) was obtained as a yellow solid. MS: m/z=432.0, 434.0 [M+H]$^+$.

Intermediate 324: 3-(3-(4-(Chloromethyl)phenyl)-5-(2-isopropyl-2H-1,2,3-triazol-4-yl)-3H-imidazo[4,5-b]pyridin-2-yl)pyrazin-2-amine

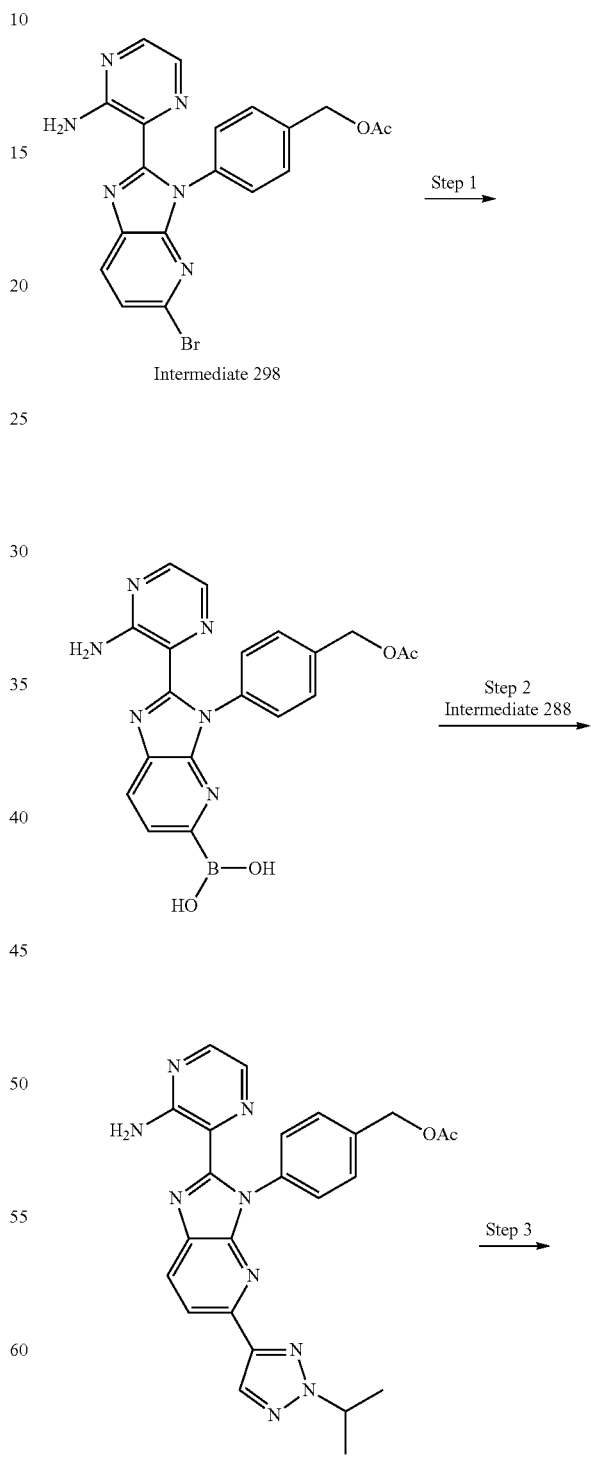

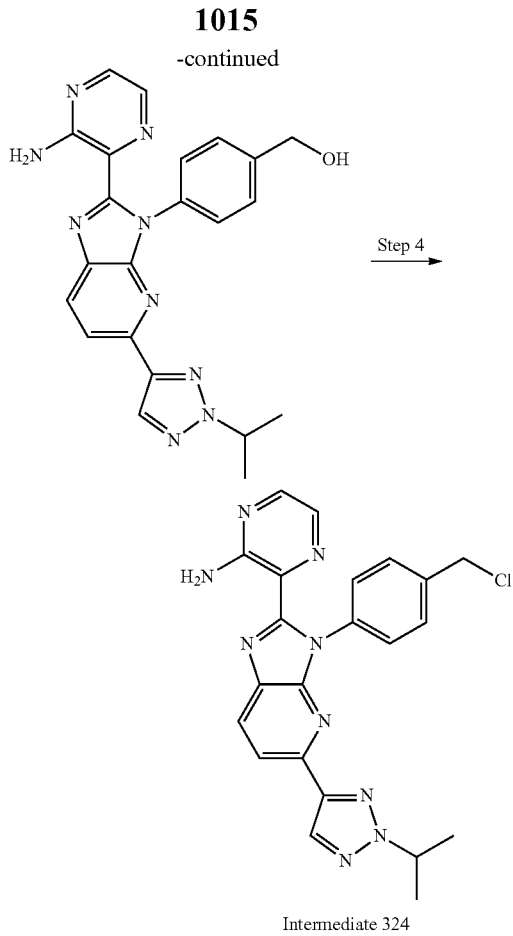

Intermediate 324

Step 1: (3-(4-(Acetoxymethyl)phenyl)-2-(3-aminopyrazin-2-yl)-3H-imidazo[4,5-b]pyridin-5-yl)boronic acid To a solution of Intermediate 298 (300 mg, 683 µmol) in 1,4-dioxane (12.5 mL) were added 4,4,4',4',5,5,5',5'-octamethyl-2,2'-bi(1,3,2-dioxaborolane) (347 mg, 1.37 mmol), KOAc (201 mg, 2.05 mmol) and Pd(dppf)Cl$_2$ (50.0 mg, 68.3 µmol) at 20° C. The reaction mixture was degassed and purged with N$_2$ three times and stirred at 80° C. for 2 hr under N$_2$. (3-(4-(Acetoxymethyl)phenyl)-2-(3-aminopyrazin-2-yl)-3H-imidazo[4,5-b]pyridin-5-yl)boronic acid was obtained as a black liquid, which was used in the next step without work-up and purification. MS: m/z=405.1 [M+H]$^+$.

Step 2: 4-(2-(3-Aminopyrazin-2-yl)-5-(2-isopropyl-2H-1,2,3-triazol-4-yl)-3H-imidazo[4,5-b]pyridin-3-yl)benzyl acetate To a solution of (3-(4-(acetoxymethyl)phenyl)-2-(3-aminopyrazin-2-yl)-3H-imidazo[4,5-b]pyridin-5-yl)boronic acid (276 mg, 683 µmol) and Intermediate 288 (195 mg, 1.02 mmol) in 1,4-dioxane (12.5 mL) and H$_2$O (2.5 mL) were added Cs$_2$CO$_3$ (668 mg, 2.05 mmol) and Pd(dppf)Cl$_2$ (50 mg, 68.3 µmol) at 20° C. The mixture was stirred at 100° C. for 1.5 hr under N$_2$. The mixture was diluted with H$_2$O (20 mL) and extracted with EtOAc (20 mL×2). The combined organic layers were washed with brine (20 mL), dried over anhydrous Na$_2$SO$_4$, filtered and concentrated. After purified by silica gel flash chromatography (EtOAc in petroleum ether=0-60%), 4-(2-(3-aminopyrazin-2-yl)-5-(2-isopropyl-2H-1,2,3-triazol-4-yl)-3H-imidazo[4,5-b]pyridin-3-yl)benzyl acetate (230 mg, 490 µmol, 72% yield for 2 steps) was obtained as a yellow solid. MS: m z=470.2 [M+H]$^+$. $^1$H NMR (400 MHz, Dimethylsulfoxide-d$_6$) δ 8.35 (d, J=8.4 Hz, 1H), 8.05-7.95 (m, 3H), 7.77 (s, 2H), 7.54-7.48 (m, 3H), 7.46-7.41 (m, 2H), 5.19 (s, 2H), 4.93-4.84 (m, 1H), 2.11 (s, 3H), 1.53 (d, J=6.8 Hz, 6H).

Step 3: (4-(2-(3-Aminopyrazin-2-yl)-5-(2-isopropyl-2H-1,2,3-triazol-4-yl)-3H-imidazo[4,5-b]pyridin-3-yl)phenyl)methanol To a solution of 4-(2-(3-aminopyrazin-2-yl)-5-(2-isopropyl-2H-1,2,3-triazol-4-yl)-3H-imidazo[4,5-b]pyridin-3-yl)benzyl acetate (200 mg, 426 µmol) in THF (4 mL), MeOH (4 mL) and H$_2$O (2 mL) was added K$_2$CO$_3$ (177 mg, 1.28 mmol). The mixture was stirred at 20° C. for 0.5 hr. The mixture was diluted with H$_2$O (20 mL) and extracted with EtOAc (20 mL×2). The combined organic layers were washed with brine (20 mL), dried over anhydrous Na$_2$SO$_4$, filtered and concentrated. (4-(2-(3-Aminopyrazin-2-yl)-5-(2-isopropyl-2H-1,2,3-triazol-4-yl)-3H-imidazo[4,5-b]pyridin-3-yl)phenyl)methanol (180 mg, 421 µmol) was obtained as a yellow solid, which was used in the next step directly. MS: m/z=428.2 [M+H]$^+$. $^1$H NMR (400 MHz, Dimethylsulfoxide-d$_6$) δ 8.34 (d, J=8.4 Hz, 1H), 8.03-7.95 (m, 3H), 7.74 (s, 2H), 7.53 (d, J=2.4 Hz, 1H), 7.46-7.34 (m, 4H), 5.35 (t, J=6.0 Hz, 1H), 4.94-4.83 (m, 1H), 4.61 (d, J=5.6 Hz, 2H), 1.53 (d, J=6.8 Hz, 6H).

Step 4: 3-(3-(4-(Chloromethyl)phenyl)-5-(2-isopropyl-2H-1,2,3-triazol-4-yl)-3H-imidazo[4,5-b]pyridin-2-yl)pyrazin-2-amine To a solution of (4-(2-(3-aminopyrazin-2-yl)-5-(2-isopropyl-2H-1,2,3-triazol-4-yl)-3H-imidazo[4,5-b]pyridin-3-yl)phenyl)methanol (180 mg, 421 µmol) in CH$_2$Cl$_2$ (8 mL) was added SOCl$_2$ (150 mg, 1.26 mmol, 92.0 µL). The reaction mixture was stirred at 20° C. for 1 hr. The mixture was concentrated to give 3-(3-(4-(chloromethyl)phenyl)-5-(2-isopropyl-2H-1,2,3-triazol-4-yl)-3H-imidazo[4,5-b]pyridin-2-yl)pyrazin-2-amine (Intermediate 324, 187 mg, 419 µmol) as a yellow solid, which was used in the next step directly. MS: m/z=446.1, 448.1 [M+H]$^+$. $^1$H NMR (400 MHz, Dimethylsulfoxide-d$_6$) δ 8.35 (d, J=8.4 Hz, 1H), 8.04-8.01 (m, 2H), 7.99 (d, J=8.4 Hz, 1H), 7.57 (d, J=8.4 Hz, 2H), 7.52 (d, J=2.4 Hz, 1H), 7.44 (d, J=8.4 Hz, 2H), 4.93-4.84 (m, 3H), 1.53 (d, J=6.8 Hz, 6H).

Intermediate 325: 3-(3-(4-(Chloromethyl)phenyl)-5-(2-cyclopropyl-2H-1,2,3-triazol-4-yl)-3H-imidazo[4,5-b]pyridin-2-yl)pyrazin-2-amine

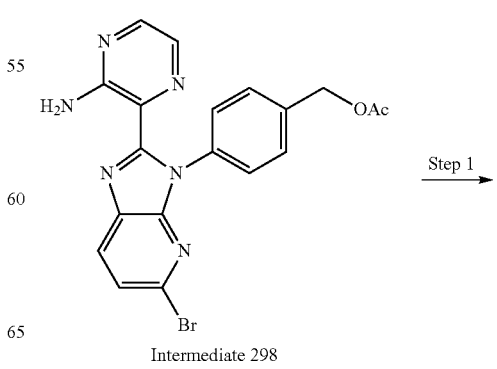

Intermediate 298

-continued

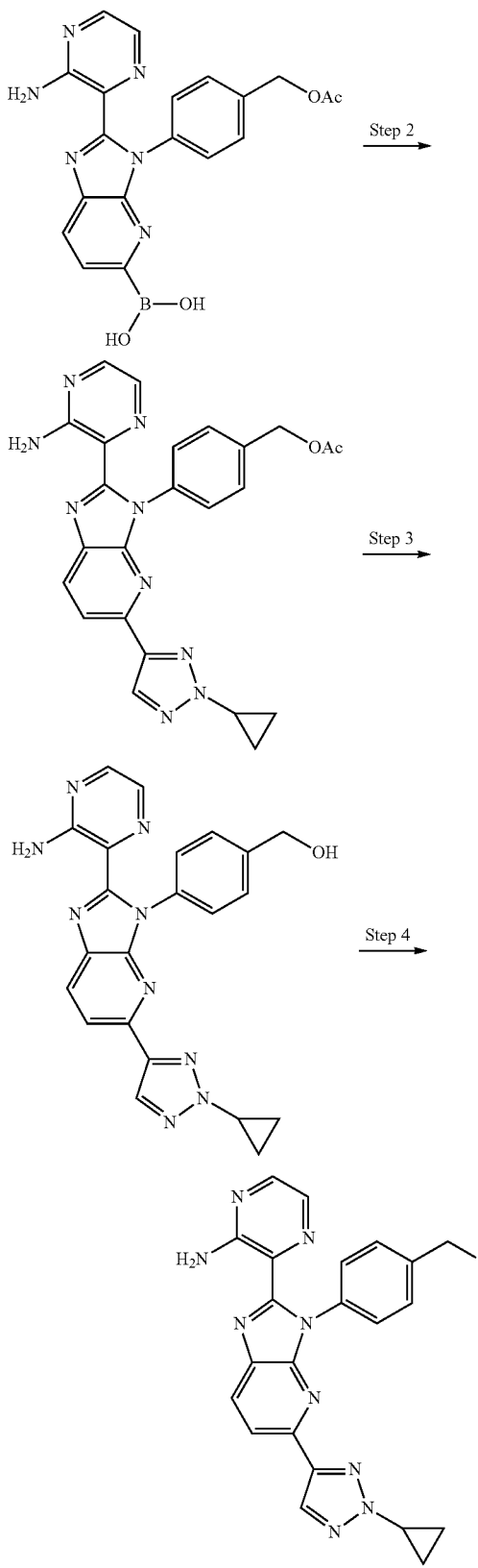

Intermediate 325

Step 1: (3-(4-(Acetoxymethyl)phenyl)-2-(3-amino-pyrazin-2-yl)-3H-imidazo[4,5-b]pyridin-5-yl)boronic acid To a solution of Intermediate 298 (350 mg, 797 μmol) and 4,4,4',4',5,5,5',5'-octamethyl-2,2'-bi(1,3,2-dioxaborolane) (405 mg, 1.59 mmol) in 1,4-dioxane (3 mL) were added Pd(dppf)Cl$_2$ (58.3 mg, 79.7 μmol) and KOAc (234.6 mg, 2.39 mmol). The reaction mixture was stirred at 85° C. for 2 hr under N$_2$ atmosphere. (3-(4-(Acetoxymethyl)phenyl)-2-(3-aminopyrazin-2-yl)-3H-imidazo[4,5-b]pyridin-5-yl) boronic acid (322 mg) was obtained as a black brown liquid, which was used in the next step without work-up and purification. MS: m/z=405.1 [M+H]$^+$.

Step 2: 4-(2-(3-Aminopyrazin-2-yl)-5-(2-cyclopropyl-2H-1,2,3-triazol-4-yl)-3H-imidazo[4,5-b]pyridin-3-yl)benzyl acetate To a solution of (3-(4-(acetoxymethyl)phenyl)-2-(3-aminopyrazin-2-yl)-3H-imidazo[4,5-b]pyridin-5-yl)boronic acid (322 mg, 797 μmol) and 4-bromo-2-cyclopropyl-2H-1,2,3-triazole (180 mg, 956 μmol) in 1,4-dioxane (4 mL) and H$_2$O (0.8 mL) were added Cs$_2$CO$_3$ (779 mg, 2.39 mmol) and Pd(dppf)Cl$_2$ (58.3 mg, 79.7 μmol). The mixture was stirred at 100° C. for 2 hr under N$_2$ atmosphere. The mixture was diluted with H$_2$O (20 mL) and extracted with ethyl acetate (10 mL×2). The combined organic layers were dried over anhydrous Na$_2$SO$_4$, filtered and concentrated. After purified by silica gel flash chromatography (Eluent of 0%~45% EtOAc in petroleum ether), 4-(2-(3-aminopyrazin-2-yl)-5-(2-cyclopropyl-2H-1,2,3-triazol-4-yl)-3H-imidazo[4,5-b]pyridin-3-yl)benzyl acetate (300 mg, yield: 81% for two steps) was obtained as a yellow solid. MS: m/z=468.2 [M+H]$^+$. $^1$H NMR (400 MHz, Dimethylsulfoxide-d$_6$) δ. 8.35 (d, J=8.4 Hz, 1H), 8.04-8.00 (m, 2H), 7.97 (d, J=8.0 Hz, 1H), 7.77 (br s, 2H), 7.53 (d, J=2.4 Hz, 1H), 7.50 (d, J=8.4 Hz, 2H), 7.43 (d, J=8.4 Hz, 2H), 5.19 (s, 2H), 4.26-4.19 (m, 1H), 2.13 (s, 3H), 1.29-1.22 (m, 2H), 1.16-1.09 (m, 2H).

Step 3: (4-(2-(3-Aminopyrazin-2-yl)-5-(2-cyclopropyl-2H-1,2,3-triazol-4-yl)-3H-imidazo[4,5-b]pyridin-3-yl)phenyl)methanol To a solution of 4-(2-(3-aminopyrazin-2-yl)-5-(2-cyclopropyl-2H-1,2,3-triazol-4-yl)-3H-imidazo[4,5-b]pyridin-3-yl)benzyl acetate (250 mg, 535 μmol) in THF (2 mL), H$_2$O (1 mL) and MeOH (2 mL) was added K$_2$CO$_3$ (222 mg, 1.60 mmol). The mixture was stirred at 25° C. for 1 hr. The reaction was concentrated, diluted with (5 mL) and extracted with ethyl acetate (5 mL×2). The combined organic layers were dried over anhydrous Na$_2$SO$_4$, filtered and concentrated. (4-(2-(3-Aminopyrazin-2-yl)-5-(2-cyclopropyl-2H-1,2,3-triazol-4-yl)-3H-imidazo[4,5-b]pyridin-3-yl)phenyl) methanol (228 mg) was obtained as a light yellow oil. MS: m/z=426.2 [M+H]$^+$ Step 4: 3-(3-(4-(Chloromethyl)phenyl)-5-(2-cyclopropyl-2H-1,2,3-triazol-4-yl)-3H-imidazo[4,5-b]pyridin-2-yl)pyrazin-2-amine To a solution of (4-(2-(3-aminopyrazin-2-yl)-5-(2-cyclopropyl-2H-1,2,3-triazol-4-yl)-3H-imidazo[4,5-b]pyridin-3-yl)phenyl)methanol (228 mg, 535 μmol) in CH$_2$Cl$_2$ (1 mL) was added SOCl$_2$ (191 mg, 1.60 mmol). The mixture was stirred at 25° C. for 1 hr under N$_2$. The reaction was concentrated to give 3-(3-(4-(chloromethyl)phenyl)-5-(2- cyclopropyl-2H-1,2,3-triazol-4-yl)-3H-imidazo[4,5-b]pyridin-2-yl)pyrazin-2-amine (Intermediate 325, 237 mg, HCl salt) as a light yellow solid. MS: m z=444.1, 446.1 [M+H]+.

Intermediate 326 & 327: 2-(4-(2-(3-Aminopyrazin-2-yl)-3-(4-(chloromethyl)phenyl)-3H-imidazo[4,5-b]pyridin-5-yl)-2H-1,2,3-triazol-2-yl)acetonitrile and 2-(4-(2-(3-aminopyrazin-2-yl)-3-(4-(chloromethyl)phenyl)-3H-imidazo[4,5-b]pyridin-5-yl)-2H-1,2,3-triazol-2-yl)acetamide

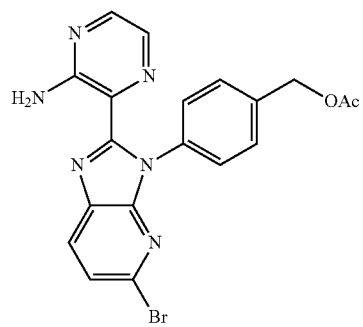

Intermediate 298

$\xrightarrow{\text{Step 1}}$

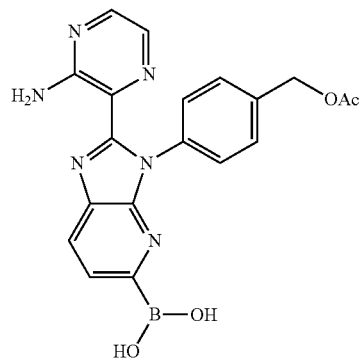

$\xrightarrow[\text{Intermediate 317}]{\text{Step 2}}$

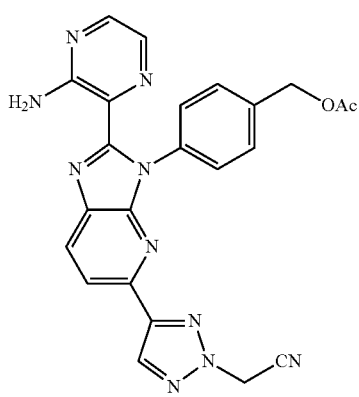

$\xrightarrow{\text{Step 3}}$

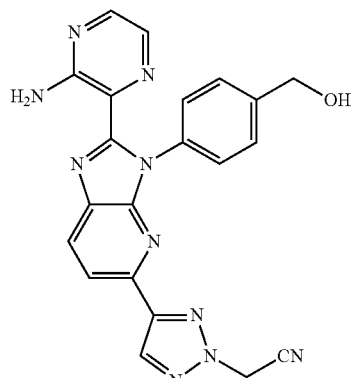

+

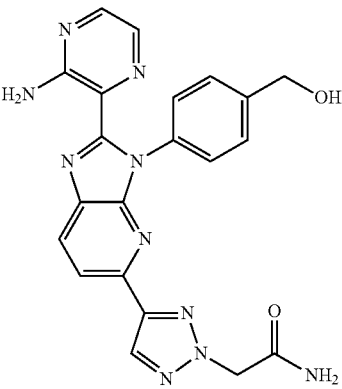

$\xrightarrow{\text{Step 4}}$

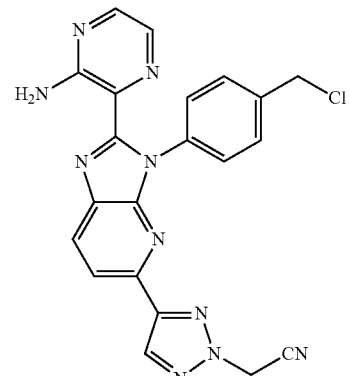

Intermediate 326

+

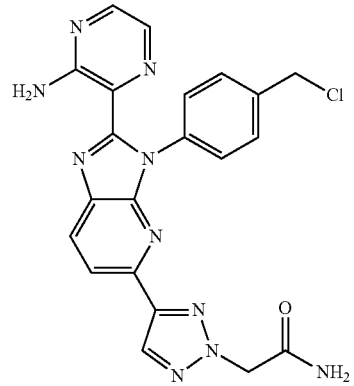

Intermediate 327

Step 1: (3-(4-(Acetoxymethyl)phenyl)-2-(3-aminopyrazin-2-yl)-3H-imidazo[4,5-b]pyridin-5-yl)boronic acid To a solution of Intermediate 298 (360 mg, 820 μmol) and 4,4,4',4',5,5,5',5'-octamethyl-2,2'-bi(1,3,2-dioxaborolane) (416 mg, 1.64 mmol) in 1,4-dioxane (2 mL) were added Pd(dppf)Cl$_2$ (60.0 mg, 82.0 μmol) and KOAc (241 mg, 2.46 mmol). The mixture was stirred at 85° C. for 2 hr under N$_2$ atmosphere. (3-(4-(Acetoxymethyl)phenyl)-2-(3-aminopyrazin-2-yl)-3H-imidazo[4,5-b]pyridin-5-yl)boronic acid was obtained as a black liquid, which was used in the next step without work-up and purification. MS: m/z=405.1 [M+H]$^+$.

Step 2: 4-(2-(3-Aminopyrazin-2-yl)-5-(2-(cyanomethyl)-2H-1,2,3-triazol-4-yl)-3H-imidazo[4,5-b]pyridin-3-yl)benzyl acetate To a solution of (3-(4-(acetoxymethyl)phenyl)-2-(3-aminopyrazin-2-yl)-3H-imidazo[4,5-b]pyridin-5-yl)boronic acid (331 mg, 819 μmol) and Intermediate 317 (184 mg, 983 μmol) in 1,4-dioxane (4 mL) and H$_2$O (0.8 mL) were added Pd(dppf)Cl$_2$ (59.9 mg, 81.9 μmol) and Cs$_2$CO$_3$ (801 mg, 2.46 mmol). The mixture was stirred at 100° C. for 2 hr under N$_2$ atmosphere. The mixture was diluted with water (20 mL) and extracted with EtOAc (20 mL×2). The combined organic layers were dried over anhydrous Na$_2$SO$_4$, filtered and concentrated. After purified by silica gel flash chromatography (Eluent of 0%~30% EtOAc in petroleum ether), 4-(2-(3-aminopyrazin-2-yl)-5-(2-(cyanomethyl)-2H-1,2,3-triazol-4-yl)-3H-imidazo[4,5-b]pyridin-3-yl)benzyl acetate (300 mg, yield: 79% for two steps) was obtained as a light yellow solid. MS: m/z=467.2 [M+H]$^+$.

Step 3: 2-(4-(2-(3-Aminopyrazin-2-yl)-3-(4-(hydroxymethyl)phenyl)-3H-imidazo[4,5-b]pyridin-5-yl)-2H-1,2,3-triazol-2-yl)acetonitrile & 2-(4-(2-(3-aminopyrazin-2-yl)-3-(4-(hydroxymethyl)phenyl)-3H-imidazo[4,5-b]pyridin-5-yl)-2H-1,2,3-triazol-2-yl)acetamide To a solution of 4-(2-(3-aminopyrazin-2-yl)-5-(2-(cyanomethyl)-2H-1,2,3-triazol-4-yl)-3H-imidazo[4,5-b]pyridin-3-yl)benzyl acetate (200 mg, 429 μmol) in THF (2 mL) and H$_2$O (1 mL) was added LiOH (30.8 mg, 1.29 mmol). The mixture was stirred at 25° C. for 2 hr. The mixture was diluted with water (10 mL) and extracted with EtOAc (10 mL×2). The combined organic layers were dried over anhydrous Na$_2$SO$_4$, filtered and concentrated. The mixture (100 mg) of 2-(4-(2-(3-aminopyrazin-2-yl)-3-(4-(hydroxymethyl)phenyl)-3H-imidazo[4,5-b]pyridin-5-yl)-2H-1,2,3-triazol-2-yl)acetonitrile and 2-(4-(2-(3-aminopyrazin-2-yl)-3-(4-(hydroxymethyl)phenyl)-3H-imidazo[4,5-b]pyridin-5-yl)-2H-1,2,3-triazol-2-yl)acetamide was obtained as a light yellow oil. MS: m/z=447.0 [M+Na]$^+$ & MS: m/z=443.1 [M+H]$^+$.

Step 4: 2-(4-(2-(3-Aminopyrazin-2-yl)-3-(4-(chloromethyl)phenyl)-3H-imidazo[4,5-b]pyridin-5-yl)-2H-1,2,3-triazol-2-yl)acetonitrile & 2-(4-(2-(3-aminopyrazin-2-yl)-3-(4-(chloromethyl)phenyl)-3H-imidazo[4,5-b]pyridin-5-yl)-2H-1,2,3-triazol-2-yl)acetamide To a solution of 2-(4-(2-(3-aminopyrazin-2-yl)-3-(4-(hydroxymethyl)phenyl)-3H-imidazo[4,5-b]pyridin-5-yl)-2H-1,2,3-triazol-2-yl)acetonitrile (100 mg, 236 μmol, contained 2-(4-(2-(3-aminopyrazin-2-yl)-3-(4-(hydroxymethyl)phenyl)-3H-imidazo[4,5-b]pyridin-5-yl)-2H-1,2,3-triazol-2-yl)acetamide) in CH$_2$Cl$_2$ (0 mL) was added SOCl$_2$ (84.1 mg, 707 μmol). The mixture was stirred at 25° C. for 2 hr. The reaction was concentrated to give a mixture (104 mg, HCl salt, crude) of 2-(4-(2-(3-aminopyrazin-2-yl)-3-(4-(chloromethyl)phenyl)-3H-imidazo[4,5-b]pyridin-5-yl)-2H-1,2,3-triazol-2-yl)acetonitrile (Intermediate 326) and 2-(4-(2-(3-aminopyrazin-2-yl)-3-(4-(chloromethyl)phenyl)-3H-imidazo[4,5-b]pyridin-5-yl)-2H-1,2,3-triazol-2-yl)acetamide (Intermediate 327) as a light yellow solid, which was used in the next step without purification. MS: m/z=443.1, 445.1 [M+H]$^+$. MS: m/z=483.0, 485.0 [M+Na].

Intermediate 328: 3-(3-(4-(Chloromethyl)phenyl)-5-(5-(trifluoromethyl)pyridin-2-yl)-3H-imidazo[4,5-b]pyridin-2-yl)pyridin-2-amine

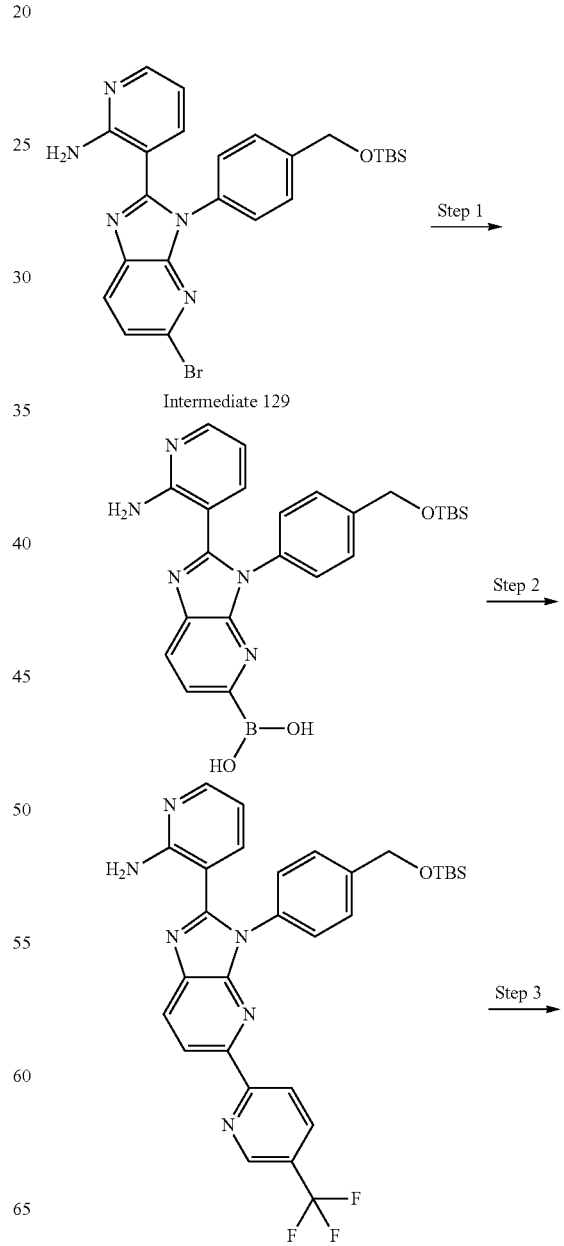

-continued

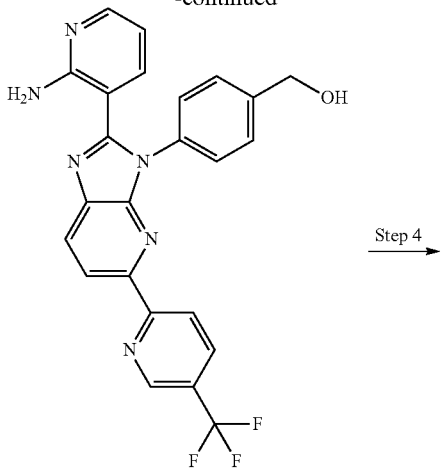

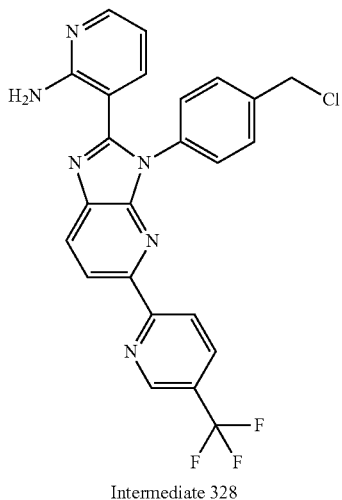 [SMILES: Nc1ncccc1-c1nc2ccc(-c3ccc(C(F)(F)F)cn3)nc2n1-c1ccc(CCl)cc1]

Intermediate 328

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (500 mg, 979 μmol), 4,4,4',4',5,5,5',5'-octamethyl-2,2'-bi(1,3,2-dioxaborolane) (498 mg, 1.96 mmol), KOAc (288 mg, 2.94 mmol) and Pd(dppf)Cl$_2$ (71.7 mg, 97.9 μmol) in 1,4-dioxane (5 mL) was degassed, purged with N$_2$ three times, and stirred at 90° C. for 8 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((tert-Butyldimethylsilyl)oxy)methyl)phenyl)-5-(5-(trifluoromethyl)pyridin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (465 mg, 978 μmol), 2-bromo-5-(trifluoromethyl)pyridine (221 mg, 978 μmol), Pd(dppf)Cl$_2$ (71.6 mg, 98 μmol) and Cs$_2$CO$_3$ (957 mg, 2.93 mmol) in 1,4-dioxane (10 mL) and H$_2$O (2 mL) was degassed, purged with N$_2$ three times, and stirred at 80° C. for 16 hr under N$_2$ atmosphere. The reaction mixture was quenched with H$_2$O (20 mL) and extracted with EtOAc (20 mL×3). The combined organic layers were washed with brine (60 mL), dried over Na$_2$SO$_4$, filtered and concentrated under reduced pressure. After purified by silica gel flash chromatography (Eluent of 15%~30% EtOAc in petroleum ether), 3-(3-(4-(((tert-butyldimethylsilyl)oxy)methyl)phenyl)-5-(5-(trifluoromethyl)pyridin-2-yl)-3H-imidazo[4,5-b]pyridin-2-yl)pyridin-2-amine (340 mg, yield: 54% for two steps) was obtained as a brown solid. MS: m/z=577.2 [M+H]$^+$. $^1$H NMR (400 MHz, Dimethylsulfoxide-d$_6$) δ 9.06 (s, 1H), 8.53 (d, J=8.4 Hz, 1H), 8.42-8.25 (m, 3H), 8.01 (dd, J=4.8, 2.0 Hz, 1H), 7.57-7.43 (m, 4H), 7.22 (dd, J=7.6, 1.6 Hz, 1H), 7.02 (br s, 2H), 6.42-6.36 (m, 1H), 4.84 (s, 2H), 0.93 (s, 9H), 0.12 (s, 6H). $^{19}$F NMR (400 MHz, Dimethylsulfoxide-d6) δ −60.75.

Step 3: (4-(2-(2-Aminopyridin-3-yl)-5-(5-(trifluoromethyl)pyridin-2-yl)-3H-imidazo[4,5-b]pyridin-3-yl)phenyl)methanol To a solution of 3-(3-(4-(((tert-butyldimethylsilyl)oxy)methyl)phenyl)-5-(5-(trifluoromethyl)pyridin-2-yl)-3H-imidazo[4,5-b]pyridin-2-yl)pyridin-2-amine (340 mg, 590 gmol) in THF (5 mL) was added TBAF (1.8 mL, I M in THF). The mixture was stirred at 25° C. for 1 hr. The reaction mixture was quenched with H$_2$O (20 mL) at 25° C. and extracted with EtOAc (20 mL×3). The combined organic layers were washed with brine (20 mL×3), dried over Na$_2$SO$_4$, filtered and concentrated under reduced pressure. The crude product was triturated with CH$_2$Cl$_2$: petroleum ether=1: 10 (6 mL) at 25° C. for 10 min. (4-(2-(2-Aminopyridin-3-yl)-5-(5-(trifluoromethyl)pyridin-2-yl)-3H-imidazo[4,5-b]pyridin-3-yl)phenyl)methanol (220 mg, yield: 75%) was obtained as a brown solid. MS: m/z=463.1 [M+H]$^+$. $^1$H NMR (400 MHz, Dimethylsulfoxide-d$_6$) δ 9.06 (s, 1H), 8.53 (d, J=8.4 Hz, 1H), 8.39-8.26 (m, 3H), 8.01 (dd, J=4.8, 2.0 Hz, 1H), 7.54-7.45 (m, 4H), 7.25 (dd, J=7.6, 1.6 Hz, 1H), 6.95 (br s, 2H), 6.43 (dd, J=7.6, 4.8 Hz, 1H), 5.39 (brt, J=5.6 Hz, 1H), 4.62 (d, J=5.6 Hz, 2H). $^{19}$F NMR (400 MHz, Dimethylsulfoxide-d6) δ −60.757.

Step 4: 3-(3-(4-(Chloromethyl)phenyl)-5-(5-(trifluoromethyl)pyridin-2-yl)-3H-imidazo[4,5-b]pyridin-2-yl)pyridin-2-amine To a solution of (4-(2-(2-aminopyridin-3-yl)-5-(5-(trifluoromethyl)pyridin-2-yl)-3H-imidazo[4,5-b]pyridin-3-yl)phenyl)methanol (220 mg, 476 μmol) in CH$_2$Cl$_2$ (5 mL) was added SOCl$_2$ (104 μL, 1.43 mmol). The mixture was stirred at 40° C. for 0.5 hr. The reaction was concentrated under reduced pressure to give 3-(3-(4-(chloromethyl)phenyl)-5-(5-(trifluoromethyl)pyridin-2-yl)-3H-imidazo[4,5-b]pyridin-2-yl)pyridin-2-amine (Intermediate 328, 246 mg, HCl salt) as a brown solid. MS: m/z=481.1, 483.1 [M+H]$^+$.

Intermediate 329: 3-(3-(4-(Chloromethyl)phenyl)-5-(2-methyl-2H-1,2,3-triazol-4-yl-5-d)-3H-imidazo[4,5-b]pyridin-2-yl)pyrazin-2-amine

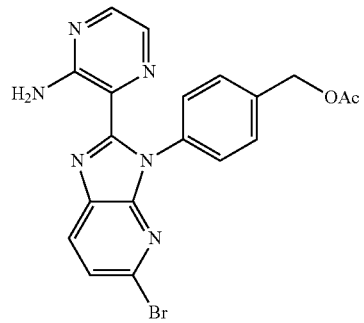

Intermediate 298

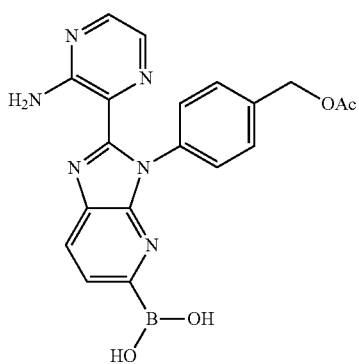

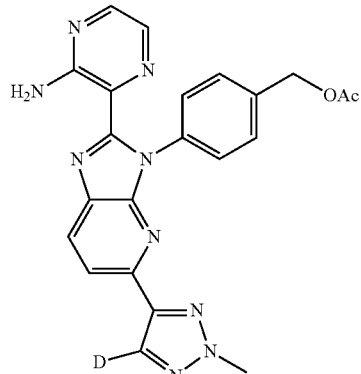

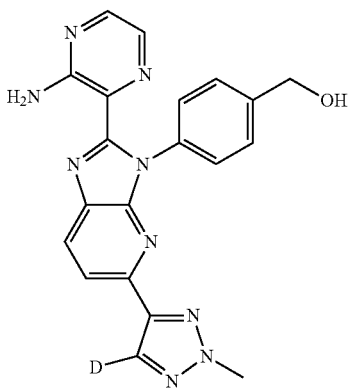

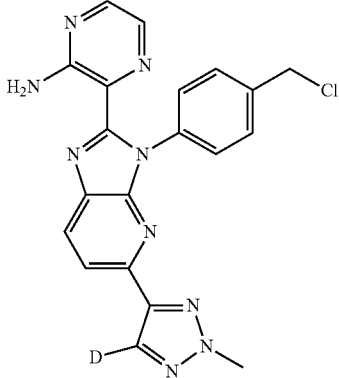

Intermediate 329

Step 1: (3-(4-(Acetoxymethyl)phenyl)-2-(3-aminopyrazin-2-yl)-3H-imidazo[4,5-b]pyridin-5-yl)boronic acid A mixture of Intermediate 298 (500 mg, 1.14 mmol), 4,4,4',4',5,5,5',5'-octamethyl-2,2'-bi(1,3,2-dioxaborolane) (578 mg, 2.28 mmol), Pd(dppf)Cl$_2$ (83.3 mg, 114 µmol) and KOAc (335 mg, 3.41 mmol) in 1,4-dioxane (5 mL) was degassed and purged with N$_2$ three times and was stirred at 90° C. for 2 hr under N$_2$ atmosphere. (3-(4-(Acetoxymethyl) phenyl)-2-(3-aminopyrazin-2-yl)-3H-imidazo[4,5-b]pyridin-5-yl)boronic acid was obtained as a black liquid, which was used in the next step without work-up and purification. MS: m/z=405.0 [M+H]$^+$.

Step 2: 4-(2-(3-Aminopyrazin-2-yl)-5-(2-methyl-2H-1,2,3-triazol-4-yl-5-d)-3H-imidazo[4,5-b]pyridin-3-yl)benzyl acetate A mixture of (3-(4-(acetoxymethyl)phenyl)-2-(3-aminopyrazin-2-yl)-3H-imidazo[4,5-b]pyridin-5-yl)boronic acid (460 mg, 1.14 mmol), Intermediate 296 (371 mg, 2.28 mmol), Cs$_2$CO$_3$ (1.11 g, 3.41 mmol) and Pd(dppf)Cl$_2$ (83.3 mg, 114 µmol) in 1,4-dioxane (6 mL) and H$_2$O (1.5 mL) was degassed, purged with N$_2$ three times and stirred at 90° C. for 1 hr under N$_2$ atmosphere. The reaction mixture was quenched with H$_2$O (5 mL) and extracted with CH$_2$Cl$_2$ (15 mL×2). The combined organic layers were washed with brine (50 mL), dried over Na$_2$SO$_4$, filtered and concentrated under reduced pressure. After purified by silica gel flash chromatography (Eluent of 5%~45% EtOAc in petroleum ether), 4-(2-(3-aminopyrazin-2-yl)-5-(2-methyl-2H-1,2,3-triazol-4-yl-5-d)-3H-imidazo[4,5-b]pyridin-3-yl)benzyl acetate (380 mg, yield: 72% for two steps) was obtained as a yellow solid. MS: m-=465.1 [M+Na]$^+$. D %: 1D %=94.1%. $^1$H NMR (400 MHz, Dimethylsulfoxide-d$_6$) δ 8.35 (d, J=8.4 Hz, 1H), 8.02 (d, J=2.4 Hz, 1H), 7.97 (d, J=8.4 Hz, 1H), 7.77 (br s, 2H), 7.54-7.49 (m, 3H), 7.46-7.41 (m, 2H), 5.19 (s, 2H), 4.22 (s, 3H), 2.13 (s, 3H).

Step 3: (4-(2-(3-Aminopyrazin-2-yl)-5-(2-methyl-2H-1,2,3-triazol-4-yl-5-d)-3H-imidazo[4,5-b]pyridin-3-yl)phenyl)methanol To a solution of 4-(2-(3-aminopyrazin-2-yl)-5-(2-methyl-2H-1,2,3-triazol-4-yl-5-d)-3H-imidazo[4,5-b]pyridin-3-yl) benzyl acetate (380 mg, 859 µmol) in THF (10 mL), MeOH (10 mL) and H$_2$O (10 mL) was added K$_2$CO$_3$ (593 mg, 4.29 mmol). The mixture was stirred at 25° C. for 1 hr. The reaction mixture was quenched with $H_2O$ (20 mL) at 25° C. and extracted with $CH_2Cl_2$ (25 mL×2). The combined organic layers were washed with brine (30 mL), dried over $Na_2SO_4$, filtered and concentrated under reduced pressure. (4-(2-(3-Aminopyrazin-2-yl)-5-(2-methyl-2H-1,2,3-triazol-4-yl-5-d)-3H-imidazo[4,5-b]pyridin-3-yl)phenyl)methanol (340 mg) was obtained as a yellow solid. MS: m/z=401.0 [M+H]+. 1H NMR (400 MHz, Dimethylsulfoxide-d6) δ 8.34 (d, J=8.4 Hz, 1H), 8.05-7.94 (m, 2H), 7.74 (br s, 2H), 7.54 (d, J=2.4 Hz, 1H), 7.46-7.41 (m, 2H), 7.39-7.34 (m, 2H), 5.33 (br t, J=5.6 Hz, 1H), 4.61 (d, J=6.0 Hz, 2H), 4.21 (s, 3H).

Step 4: 3-(3-(4-(Chloromethyl)phenyl)-5-(2-methyl-2H-1,2,3-triazol-4-yl-5-d)-3H-imidazo[4,5-b]pyridin-2-yl)pyrazin-2-amine To a solution of (4-(2-(3-aminopyrazin-2-yl)-5-(2-methyl-2H-1,2,3-triazol-4-yl-5-d)-3H-imidazo[4,5-b]pyridin-3-yl)phenyl)methanol (330 mg, 824 μmol) in $CH_2Cl_2$ (10 mL) was added $SOCl_2$ (490 mg, 4.12 mmol). The mixture was stirred at 25° C. for 1 hr. The reaction was concentrated under reduced pressure to give 3-(3-(4-(chloromethyl)phenyl)-5-(2-methyl-2H-1,2,3-triazol-4-yl-5-d)-3H-imidazo[4,5-b]pyridin-2-yl)pyrazin-2-amine (Intermediate 329, 375 mg, HCl salt) as a yellow solid. MS: m/z=419.1, 421.1 [M+H]+. 1H NMR (400 MHz, Methanol-d4) δ 8.33 (d, J=8.8 Hz, 1H), 8.11 (d, J=8.4 Hz, 1H), 7.89 (d, J=3.2 Hz, 1H), 7.71 (d, J=2.8 Hz, 1H), 7.64-7.60 (m, 2H), 7.48-7.43 (m, 2H), 4.80 (s, 2H), 4.22 (s, 3H).

Intermediate 330: 3-(3-(4-(Chloromethyl)phenyl)-5-(2,5-dimethyl-2H-1,2,3-triazol-4-yl)-3H-imidazo[4,5-b]pyridin-2-yl)pyrazin-2-amine

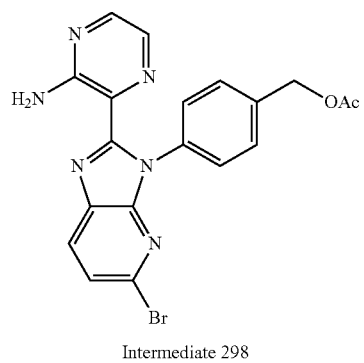

Intermediate 298

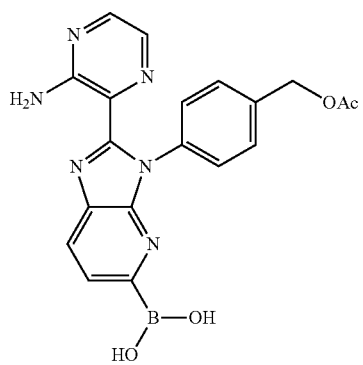

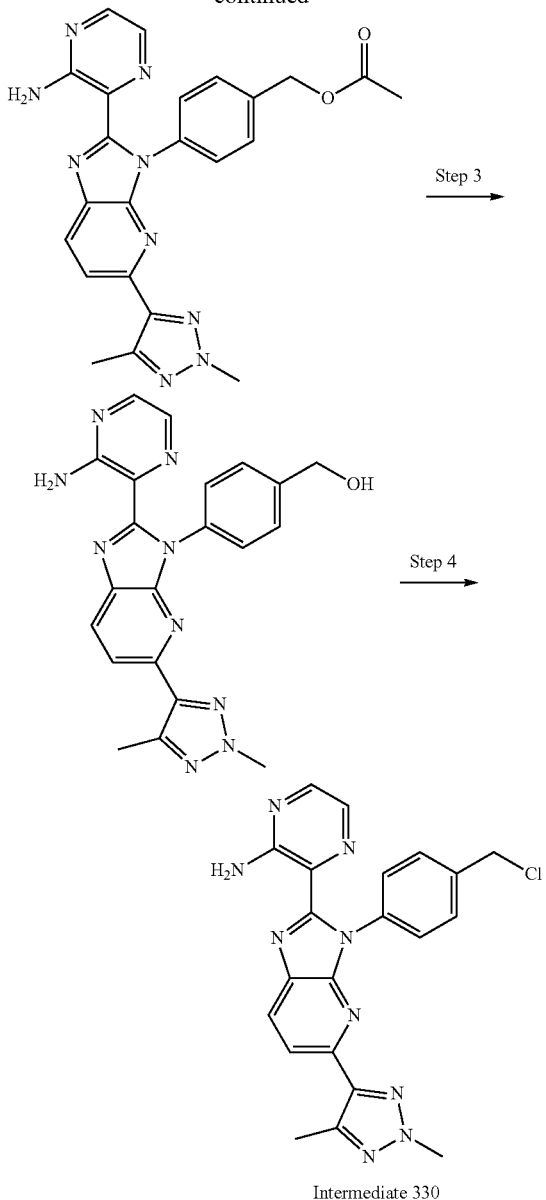

Intermediate 330

Step 1: (3-(4-(Acetoxymethyl)phenyl)-2-(3-aminopyrazin-2-yl)-3H-imidazo[4,5-b]pyridin-5-yl)boronic acid To a mixture of Intermediate 298 (350 mg, 797 μmol), 4,4,4',4',5,5,5',5'-octamethyl-2,2'-bi(1,3,2-dioxaborolane) (405 mg, 1.59 mmol), Pd(dppf)Cl2 (58.3 mg, 79.7 μmol) and KOAc (235 mg, 2.39 mmol) in 1,4-dioxane (0.8 mL) was degassed and purged with $N_2$ three times. The mixture was stirred at 85° C. for 1 hr under $N_2$ atmosphere. (3-(4-(Acetoxymethyl)phenyl)-2-(3-aminopyrazin-2-yl)-3H-imidazo[4,5-b]pyridin-5-yl)boronic acid was obtained as a black liquid, which was used in the next step directly. MS: m/z=405.1 [M+H]+.

Step 2: 4-(2-(3-Aminopyrazin-2-yl)-5-(2,5-dimethyl-2H-1,2,3-triazol-4-yl)-3H-imidazo[4,5-b]pyridin-3-yl)benzyl acetate To a mixture of (3-(4-(acetoxymethyl)phenyl)-2-(3-aminopyrazin-2-yl)-3H-imidazo[4,5-b]pyridin-5-yl)boronic acid (322 mg, 797 μmol), 4-bromo-2,5-dimethyl-2H-1,2,3-triazole (280 mg, 1.59 mmol), $Cs_2CO_3$ (779 mg, 2.39 mmol) and Pd(dppf)$Cl_2$ (58.3 mg, 79.7 μmol) in 1,4-dioxane (0.8 mL) and $H_2O$ (0.2 mL) was degassed and purged with $N_2$ for 3 times, the mixture was stirred at 100° C. for 1 hr under $N_2$. The mixture was diluted with $H_2O$ (50 mL) and extracted with EtOAc (30 mL×2). The combined organic layers were washed with brine (20 mL), dried over anhydrous $Na_2SO_4$, filtered and concentrated. After purified by silica gel flash chromatography (Eluent of 0~44% EtOAc in Petroleum ether), 4-(2-(3-aminopyrazin-2-yl)-5-(2,5-dimethyl-2H-1,2,3-triazol-4-yl)-3H-imidazo[4,5-b]pyridin-3-yl)benzyl acetate (251 mg, yield: 69% for two steps) was obtained as a light yellow solid. MS: m/z=456.2 [M+H]$^+$. $^1$H NMR (400 MHz, Dimethylsulfoxide-$d_6$) 8.32 (d, J=8.4 Hz, 1H), 8.03 (d, J=2.4 Hz, 1H), 7.94 (d, J=8.4 Hz, 1H), 7.82 (br s, 2H), 7.55-7.52 (m, 2H), 7.49-7.45 (m, 4H), 5.18 (s, 2H), 4.13 (s, 3H), 2.34 (s, 3H),

Step 3: (4-(2-(3-Aminopyrazin-2-yl)-5-(2,5-dimethyl-2H-1,2,3-triazol-4-yl)-3H-imidazo[4,5-b]pyridin-3-yl)phenyl)methanol To a solution of 4-(2-(3-aminopyrazin-2-yl)-5-(2,5-dimethyl-2H-1,2,3-triazol-4-yl)-3H-imidazo[4,5-b]pyridin-3-yl)benzyl acetate (155 mg, 340 μmol,) in MeOH (1.5 mL), THF (1.5 mL), $H_2O$ (0.75 mL) was added $K_2CO_3$ (141 mg, 1.02 mmol). The mixture was stirred at 25° C. for 2 hr under $N_2$. The mixture was diluted with $H_2O$ (50 mL) and extracted with EtOAc (30 mL×3). The combined organic layers were washed with brine (30 mL), dried over anhydrous $Na_2SO_4$, filtered and concentrated. (4-(2-(3-Aminopyrazin-2-yl)-5-(2,5-dimethyl-2H-1,2,3-triazol-4-yl)-3H-imidazo[4,5-b]pyridin-3-yl)phenyl)methanol (135 mg) was obtained as a brown solid, which was used in the next step without further purification. MS: m/z=414.2 [M+H]$^+$. $^1$H NMR (400 MHz, Dimethylsulfoxide-$d_6$) δ 31 (d, J=8.8 Hz, 1H), 8.02 (d, J=2.4 Hz, 1H), 7.94 (d, J=8.4 Hz, 1H), 7.76 (br s, 2H), 7.56 (d, J=2.4 Hz, 1H), 7.43-7.40 (m, 2H), 7.39-7.36 (m, 2H), 5.34 (t, J=5.6 Hz, 1H), 4.60 (d, J=5.6 Hz, 2H), 4.13 (s, 3H), 2.36 (s, 3H).

Step 4: 3-(3-(4-(Chloromethyl)phenyl)-5-(2,5-dimethyl-2H-1,2,3-triazol-4-yl)-3H-imidazo[4,5-b]pyridin-2-yl)pyrazin-2-amine To a solution of (4-(2-(3-aminopyrazin-2-yl)-5-(2,5-dimethyl-2H-1,2,3-triazol-4-yl)-3H-imidazo[4,5-b]pyridin-3-yl)phenyl)methanol (125 mg, 302 μmol) in $CH_2Cl_2$ (2.5 mL) was added $SOCl_2$ (108 mg, 907 μmol). The mixture was stirred at 25° C. for 2 hr under $N_2$. The reaction mixture was concentrated, 3-(3-(4-(chloromethyl)phenyl)-5-(2,5-dimethyl-2H-1,2,3-triazol-4-yl)-3H-imidazo[4,5-b]pyridin-2-yl)pyrazin-2-amine (Intermediate 330, 110 mg) was obtained as a yellow solid, which was used in the next step without further purification. MS: m/z=432.1, 434.1[M+H]$^+$.

Intermediate 331: 3-(3-(4-(Chloromethyl)phenyl)-5-(6-methoxypyridin-3-yl)-3H-imidazo[4,5-b]pyridin-2-yl)pyrazin-2-amine

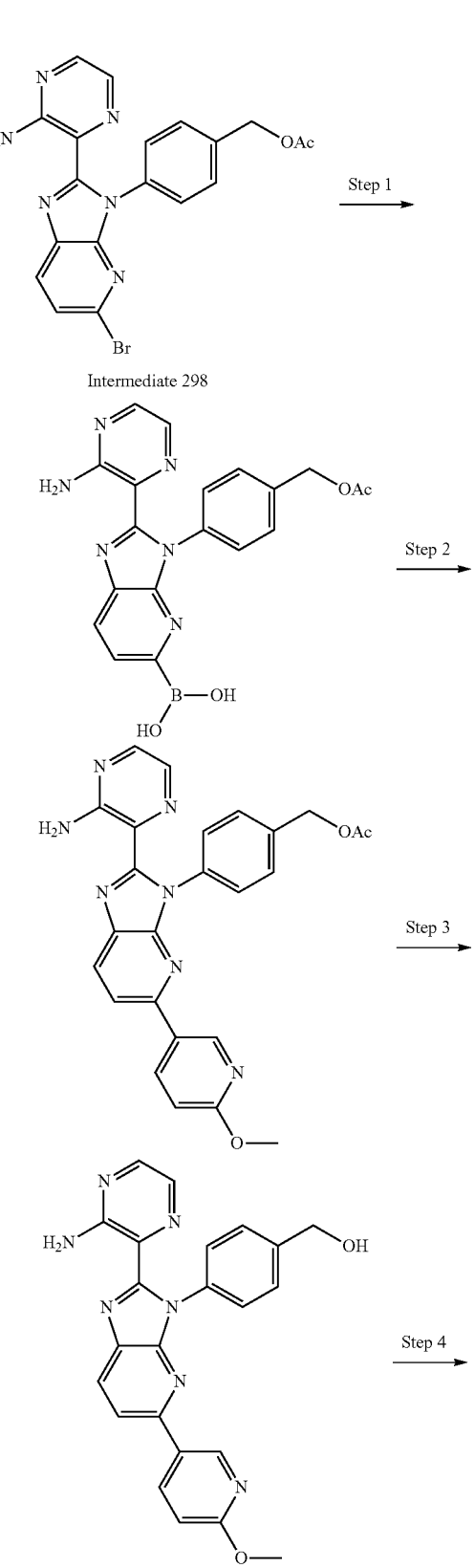

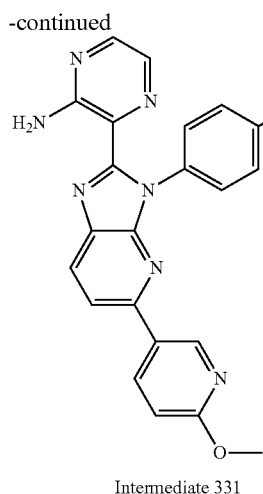

Intermediate 331

Step 1: (3-(4-(Acetoxymethyl)phenyl)-2-(3-aminopyrazin-2-yl)-3H-imidazo[4,5-b]pyridin-5-yl)boronic acid A mixture of Intermediate 298 (250 mg, 569 μmol), 4,4,4',4',5,5,5',5'-octamethyl-2,2'-bi(1,3,2-dioxaborolane) (289 mg, 1.14 mmol), Pd(dppf)Cl$_2$ (41.6 mg, 56.9 μmol) and KOAc (168 mg, 1.71 mmol) in 1,4-dioxane (3 mL) was degassed, purged with N$_2$ three times and stirred at 90° C. for 2 hr under N$_2$ atmosphere. (3-(4-(Acetoxymethyl)phenyl)-2-(3-aminopyrazin-2-yl)-3H-imidazo[4,5-b]pyridin-5-yl)boronic acid was obtained as a black liquid, which was used in the next step without work-up and purification. MS: m/z=405.1 [M+H]$^+$.

Step 2: 4-(2-(3-Aminopyrazin-2-yl)-5-(6-methoxypyridin-3-yl)-3H-imidazo[4,5-b]pyridin-3-yl)benzyl acetate A mixture of (3-(4-(acetoxymethyl)phenyl)-2-(3-aminopyrazin-2-yl)-3H-imidazo[4,5-b]pyridin-5-yl)boronic acid (230 mg, 569 gmol), 5-bromo-2-methoxypyridine (128 mg, 683 μmol), Cs$_2$CO$_3$ (556 mg, 1.71 mmol) and Pd(dppf)Cl$_2$ (41.6 mg, 56.9 μmol) in 1,4-dioxane (6 mL) and H$_2$O (1.2 mL) was degassed, purged with N$_2$ three times and stirred at 90° C. for 1 hr under N$_2$ atmosphere. The reaction mixture was quenched with H$_2$O (5 mL) and extracted with CH$_2$Cl$_2$ (15 mL×2). The combined organic layers were washed with brine (50 mL), dried over Na$_2$SO$_4$, filtered, and concentrated under reduced pressure. After purified by silica gel flash chromatography (Eluent of 10%~50% EtOAc in petroleum ether), 4-(2-(3-aminopyrazin-2-yl)-5-(6-methoxypyridin-3-yl)-3H-imidazo[4,5-b]pyridin-3-yl)benzyl acetate (195 mg, yield: 66% for two steps) was obtained as a yellow solid. MS: m/z=490.2 [M+Na]$^+$. $^1$H NMR (400 MHz, Chloroform-d) δ 8.83 (d, J=2.4 Hz, 1H), 8.20 (dd, J=8.4, 2.4 Hz, 1H), 8.15 (d, J=8.4 Hz, 1H), 7.96 (d, J=2.4 Hz, 1H), 7.74 (d, J=8.4 Hz, 1H), 7.60 (d, J=2.4 Hz, 1H), 7.49-7.45 (m, 2H), 7.40-7.36 (m, 2H), 7.19-6.93 (m, 2H), 6.80 (d, J=8.8 Hz, 1H), 5.24 (s, 2H), 3.98 (s, 3H), 2.18 (s, 3H).

Step 3: (4-(2-(3-Aminopyrazin-2-yl)-5-(6-methoxypyridin-3-yl)-3H-imidazo[4,5-b]pyridin-3-yl)phenyl)methanol To a solution of 4-(2-(3-aminopyrazin-2-yl)-5-(6-methoxypyridin-3-yl)-3H-imidazo[4,5-b]pyridin-3-yl)benzyl acetate (195 mg, 417 μmol) in THF (5 mL), MeOH (5 mL) and H$_2$O (5 mL) was added K$_2$CO$_3$ (173 mg, 1.25 mmol). The mixture was stirred at 25° C. for 1 hr. The reaction mixture was quenched with H$_2$O (20 mL) at 25° C. and extracted with CH$_2$Cl$_2$ (25 mL×2). The combined organic layers were washed with brine (30 mL), dried over Na$_2$SO$_4$, filtered and concentrated under reduced pressure. (4-(2-(3-Aminopyrazin-2-yl)-5-(6-methoxypyridin-3-yl)-3H-imidazo[4,5-b]pyridin-3-yl)phenyl)methanol (177 mg) was obtained as a yellow solid. MS: m/z=426.2 [M+H]$^+$. $^1$H NMR (400 MHz, Dimethylsulfoxide-d$_6$) δ 8.84 (d, J=2.0 Hz, 1H), 8.36-8.26 (m, 2H), 8.07-7.98 (m, 2H), 7.80 (br s, 2H), 7.54 (d, J=2.4 Hz, 1H), 7.49-7.42 (m, 2H), 7.41-7.34 (m, 2H), 6.92 (d, J=8.4 Hz, 1H), 5.33 (br t, J=5.2 Hz, 1H), 4.61 (d, J=5.2 Hz, 2H), 3.89 (s, 3H).

Step 4: 3-(3-(4-(Chloromethyl)phenyl)-5-(6-methoxypyridin-3-yl)-3H-imidazo[4,5-b]pyridin-2-yl)pyrazin-2-amine To a solution of (4-(2-(3-aminopyrazin-2-yl)-5-(6-methoxypyridin-3-yl)-3H-imidazo[4,5-b]pyridin-3-yl)phenyl)methanol (175 mg, 411 μmol) in CH$_2$Cl$_2$ (3 mL) was added SOCl$_2$ (245 mg, 2.06 mmol). The mixture was stirred at 25° C. for 0.5 hr. The reaction was concentrated under reduced pressure to give 3-(3-(4-(chloromethyl)phenyl)-5-(6-methoxypyridin-3-yl)-3H-imidazo[4,5-b]pyridin-2-yl)pyrazin-2-amine (Intermediate 331, 197 mg, HCl salt) as a yellow solid. MS: m/z=444.0, 446.0 [M+H]$^+$. $^1$H NMR (400 MHz, Methanol-d$_4$) δ 9.00-8.90 (m, 2H), 8.44 (d, J=8.4 Hz, 1H), 8.14 (d, J=8.4 Hz, 1H), 7.91 (d, J=3.2 Hz, 1H), 7.72 (d, J=3.6 Hz, 1H), 7.65-7.61 (m, 2H), 7.56-7.46 (m, 3H), 4.80 (s, 2H), 4.23 (s, 3H).

Intermediate 332: 3-(3-(4-(Chloromethyl)phenyl)-5-(6-(methoxy-d$_1$)pyridin-3-yl)-3H-imidazo[4,5-b]pyridin-2-yl)pyrazin-2-amine

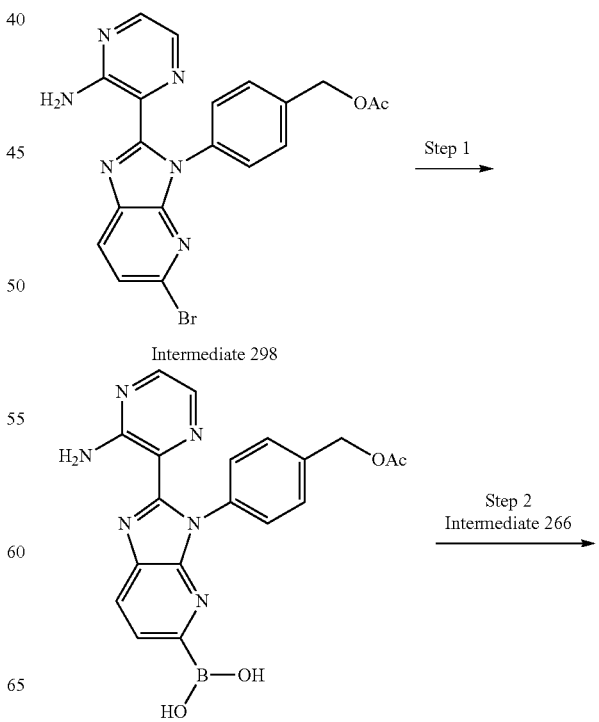

-continued

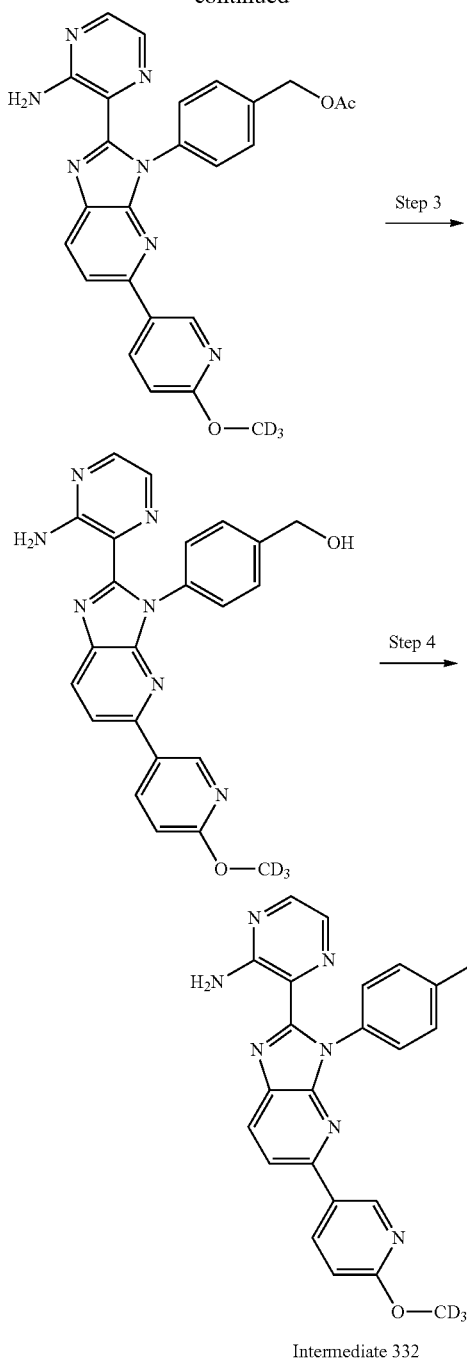

Intermediate 332

Step 1: (3-(4-(Acetoxymethyl)phenyl)-2-(3-amino-pyrazin-2-yl)-3H-imidazo[4,5-b]pyridin-5-yl)boronic acid A mixture of Intermediate 298 (500 mg, 1.14 mmol), 4,4,4',4',5,5,5',5'-octamethyl-2,2-bi(1,3,2-dioxaborolane) (578 mg, 2.28 mmol), Pd(dppf)C$_2$ (83.3 mg, 114 μmol) and KOAc (335 mg, 3.41 mmol) in 1,4-dioxane (5 mL) was degassed. purged with N$_2$ three times, and stirred at 90° C. for 2 hr under N$_2$ atmosphere. (3-(4-(Acetoxymethyl)phenyl)-2-(3-aminopyrazin-2-yl)-3H-imidazo[4,5-b]pyri din-5-yl)boronic acid was obtained as a black liquid, which was used in the next step without work-up and purification. MS: m/z=405.0 [M+H]$^+$.

Step 2: 4-(2-(3-Aminopyrazin-2-yl)-5-(6-(methoxy-d$_3$)pyridin-3-yl)-3H-imidazo[4,5-b]pyridin-3-yl) benzyl acetate A mixture of (3-(4-(acetoxymethyl)phenyl)-2-(3-amino-pyrazin-2-yl)-3H-imidazo[4,5-b]pyridin-5-yl)boronic acid (460 mg, 1.14 mmol), Intermediate 266 (326 mg, 1.71 mmol), Cs$_2$CO$_3$ (1.11 g, 3.41 mmol) and Pd(dppf)Cl$_2$ (83.3 mg, 114 μmol) in 1,4-dioxane (6 mL) and H$_2$O (1.2 mL) was degassed, purged with N$_2$ three times, and stirred at 90° C. for 1 hr under N$_2$ atmosphere. The reaction mixture was quenched with H$_2$O (20 mL) and extracted with CH$_2$Cl$_2$ (15 mL×2). The combined organic layers were washed with brine (30 mL), dried over Na$_2$SO$_4$, filtered and concentrated under reduced pressure. After purified by silica gel flash chromatography (Eluent of 10%~42% EtOAc in petroleum ether), 4-(2-(3-aminopyrazin-2-yl)-5-(6-(methoxy-d$_3$)pyri-din-3-yl)-3H-imidazo[4,5-b]pyri din-3-yl)benzyl acetate (380 mg, yield: 71% for two steps) was obtained as a yellow solid. MS: m/z=471.1 [M+H]$^+$. D %: 3D %=99.2%. $^1$H NMR (400 MHz, Dimethylsulfoxide-d$_6$) δ 8.84 (d, J=2.4 Hz, 1H), 8.37-8.27 (m, 2H), 8.06-7.99 (m, 2H), 7.82 (br s, 2H), 7.54-7.44 (m, 5H), 6.92 (d, J=8.8 Hz, 1H), 5.19 (s, 2H), 2.13 (s, 3H).

Step 3: (4-(2-(3-Aminopyrazin-2-yl)-5-(6-(methoxy-d$_3$)pyridin-3-yl)-3H-imidazo[4,5-b]pyridin-3-yl) phenyl)methanol To a solution of 4-(2-(3-aminopyrazin-2-yl)-5-(6-(methoxy-d$_3$)pyridin-3-yl)-3H-imidazo[4,5-b]pyridin-3-yl) benzyl acetate (380 mg, 808 μmol) in THF (10 mL), MeOH (10 mL) and H$_2$O (10 mL) was added K$_2$CO$_3$ (335 mg, 4.42 mmol). The mixture was stirred at 25° C. for 1 hr. The reaction mixture was quenched with H$_2$O (20 mL) at 25° C. and extracted with CH$_2$Cl$_2$ (25 mL×2). The combined organic layers were washed with brine (50 mL), dried over Na$_2$SO$_4$, filtered and concentrated under reduced pressure. (4-(2-(3-Aminopyrazin-2-yl)-5-(6-(methoxy-d$_3$)pyridin-3-yl)-3H-imidazo[4,5-b]pyridin-3-yl)phenyl)methanol (346 mg) was obtained as a yellow solid. MS: m/z=429.0 [M+H]$^+$. $^1$H NMR (400 MHz, Dimethylsulfoxide-d$_6$) δ 8.84 (d, J=2.4 Hz, 1H), 8.38-8.26 (m, 2H), 8.02 (dd, J=5.6, 3.2 Hz, 2H), 7.79 (br s, 2H), 7.54 (d, J=2.4 Hz, 1H), 7.47-7.36 (m, 4H), 6.91 (d, J=8.8 Hz, 1H), 5.33 (br t, J=5.6 Hz, 1H), 4.62 (d, J=5.6 Hz, 2H).

Step 4: 3-(3-(4-(Chloromethyl)phenyl)-5-(6-(methoxy-d$_3$)pyridin-3-yl)-3H-imidazo[4,5-b]pyri-din-2-yl)pyrazin-2-amine To a solution of (4-(2-(3-aminopyrazin-2-yl)-5-(6-(methoxy-d$_3$)pyridin-3-yl)-3H-imidazo[4,5-b]pyridin-3-yl) phenyl)methanol (345 mg, 805 μmol) in CH$_2$Cl$_2$ (5 mL) was added SOCl$_2$ (479 mg, 4.03 mmol). The mixture was stirred at 25° C. for 1 hr. The reaction was concentrated under reduced pressure to give 3-(3-(4-(chloromethyl)phenyl)-5-(6-(methoxy-d$_3$)pyridin-3-yl)-3H-imidazo[4,5-b]pyridin-2-yl)pyrazin-2-amine (Intermediate 332, 389 mg, HCl salt) was obtained as a yellow solid. MS: m/z=447.2, 449.2 [M+H]$^+$. $^1$H NMR (400 MHz, Methanol-d$_6$) δ 8.98-8.89 (m, 2H), 8.43 (d, J=8.4 Hz, 1H), 8.13 (d, J=8.4 Hz, 1H), 7.91 (d, J=3.2 Hz, 1H), 7.72 (d, J=2.8 Hz, 1H), 7.63 (d, J=8.0 Hz, 2H), 7.54-7.44 (m, 3H), 4.80 (s, 2H).

Intermediate 333: 2-Bromo-5-(methoxy-d₃)pyridine

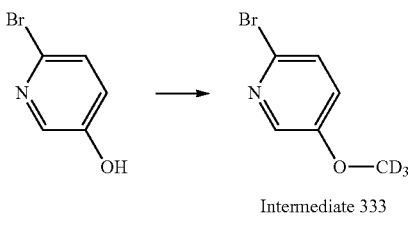 [SMILES: Oc1ccc(Br)nc1 ; [2H]C([2H])([2H])Oc1ccc(Br)nc1]

Intermediate 333

To a solution of 6-bromopyridin-3-ol (1.0 g, 5.75 mmol) in 1,4-dioxane (3 mL) were added CD₃OD (1.24 g, 34.5 mmol), PPh₃ (1.66 g, 6.32 mmol) and DIAD (1.39 g, 6.90 mmol) at 0° C. The mixture was stirred at 25° C. for 3 hr. The reaction mixture was diluted with H₂O (30 mL) and extracted with CH₂Cl₂ (25 mL×2). The combined organic layers were washed with brine (50 mL), dried over anhydrous Na₂SO₄, filtered and concentrated under reduced pressure. After purified by silica gel flash chromatography (Eluent of 0%~15% EtOAc in petroleum ether), 2-bromo-5-(methoxy-d)pyridine (Intermediate 333, 1.0 g, yield: 71%) was obtained as a yellow oil. MS: m/z=190.9, 192.9 [M+H]⁺. D %: 3D %=99.3%. ¹H NMR (400 MHz, Dimethylsulfoxide-d₆) δ 8.12 (d, J=3.2 Hz, 1H), 7.55 (d, J=8.4 Hz, 1H), 7.39 (dd, J=8.8, 3.2 Hz, 1H).

Intermediate 334: 3-(3-(4-(Chloromethyl)phenyl)-5-(5-(methoxy-d₃)pyridin-2-yl)-3H-imidazo[4,5-b]pyridin-2-yl)pyrazin-2-amine

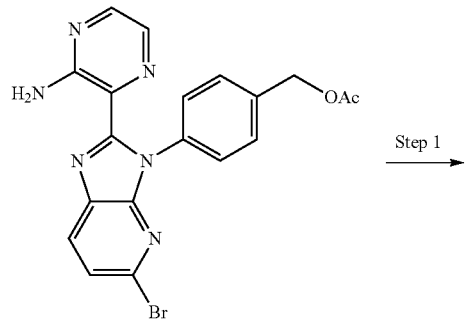

Intermediate 298

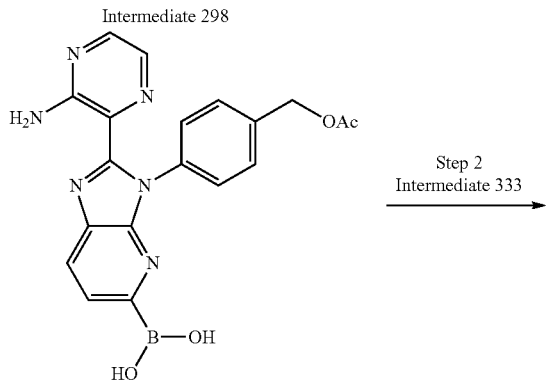

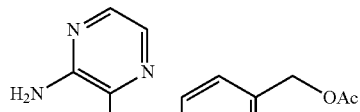

-continued

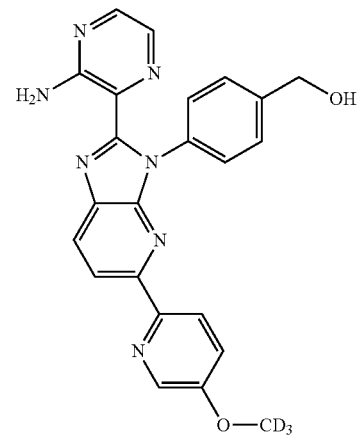

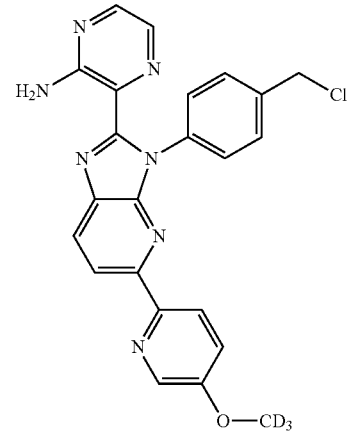

Intermediate 334

Step 1: (3-(4-(Acetoxymethyl)phenyl)-2-(3-aminopyrazin-2-yl)-3H-imidazo[4,5-b]pyridin-5-yl)boronic acid A mixture of Intermediate 298 (500 mg, 1.14 mmol), 4,4,4',4',5,5,5',5'-octamethyl-2,2'-bi(1,3,2-dioxaborolane) (578 mg, 2.28 mmol), Pd(dppf)Cl₂ (83.3 mg, 114 μmol) and KOAc (335 mg, 3.41 mmol) in 1,4-dioxane (5 mL) was degassed, purged with N₂ three times, and stirred at 90° C. for 2 hr under N₂ atmosphere. (3-(4-(Acetoxymethyl)phenyl)-2-(3-aminopyrazin-2-yl)-3H-imidazo[4,5-b]pyridin-5- yl)boronic acid was obtained as a black liquid, which was used in the next step without work-up and purification. MS: m/z=405.0 [M+H]$^+$.

Step 2: 4-(2-(3-Aminopyrazin-2-yl)-5-(5-(methoxy-d$_3$)pyridin-2-yl)-3H-imidazo[4,5-b]pyridin-3-yl) benzyl acetate A mixture of (3-(4-(acetoxymethyl)phenyl)-2-(3-amino-pyrazin-2-yl)-3H-imidazo[4,5-b]pyridin-5-yl)boronic acid (460 mg, 1.14 mmol), Intermediate 333 (434 mg, 2.28 mmol), Cs$_2$CO$_3$ (1.11 g, 3.41 mmol) and Pd(dppf)Cl$_2$ (83.3 mg, 114 μmol) in 1,4-dioxane (6 mL) and H$_2$O (1.5 mL) was degassed, purged with N$_2$ three times, and stirred at 90° C. for 1 hr under N$_2$ atmosphere. The reaction mixture was quenched with H$_2$O (20 mL) and extracted with CH$_2$Cl$_2$ (25 mL×2). The combined organic layers were washed with brine (50 mL), dried over Na$_2$SO$_4$, filtered and concentrated under reduced pressure. After purified by silica gel flash chromatography (Eluent of 15%~50% EtOAc in petroleum ether), 4-(2-(3-aminopyrazin-2-yl)-5-(5-(methoxy-d$_3$)pyridin-2-yl)-3H-imidazo[4,5-b]pyridin-3-yl)benzyl acetate (350 mg, yield: 62% for two steps) was obtained as a brown solid. MS: m/z=471.2 [M+H]$^+$. D %: 3D %=95.5%. $^1$H NMR (400 MHz, Dimethylsulfoxide-d$_6$) δ 8.43-8.31 (m, 3H), 8.11 (d, J=8.4 Hz, 1H), 8.02 (d, J=2.4 Hz, 1H), 7.80 (br s, 2H), 7.54-7.46 (m, 6H), 5.21 (s, 2H), 2.14 (s, 3H).

Step 3: (4-(2-(3-Aminopyrazin-2-yl)-5-(5-(methoxy-d$_6$)pyridin-2-yl)-3H-imidazo[4,5-b]pyridin-3-yl) phenyl)methanol To a solution of 4-(2-(3-aminopyrazin-2-yl)-5-(5-(methoxy-d$_3$)pyridin-2-yl)-3H-imidazo[4,5-b]pyridin-3-yl) benzyl acetate (350 mg, 744 gmol) in THF (10 mL), MeOH (10 mL) and H$_2$O (10 mL) was added K$_2$CO$_3$ (308 mg, 2.23 mmol). The mixture was stirred at 25° C. for 1 hr. The reaction mixture was quenched with H$_2$O (20 mL) at 25° C. and extracted with CH$_2$Cl$_2$ (25 mL×2). The combined organic layers were washed with brine (50 mL), dried over Na$_2$SO$_4$, filtered and concentrated under reduced pressure. (4-(2-(3-Aminopyrazin-2-yl)-5-(5-(methoxy-d$_3$)pyridin-2-yl)-3H-imidazo[4,5-b]pyridin-3-yl)phenyl)methanol (320 mg) was obtained as a yellow solid. MS: m/z=429.2 [M+H]$^+$. $^1$H NMR (400 MHz, Dimethylsulfoxide-d$_6$) δ 8.43-8.28 (m, 3H), 8.10 (d, J=8.8 Hz, 1H), 8.02 (d, J=2.4 Hz, 1H), 7.78 (br s, 2H), 7.54 (d, J=2.4 Hz, 1H), 7.50 (dd, J=8.8, 2.8 Hz, 1H), 7.47-7.43 (m, 2H), 7.41-7.37 (m, 2H), 5.36 (br s, 1H), 4.62 (s, 2H).

Step 4: 3-(3-(4-(Chloromethyl)phenyl)-5-(5-(methoxy-d$_3$)pyridin-2-yl)-3H-imidazo[4,5-b]pyridin-2-yl)pyrazin-2-amine To a solution of (4-(2-(3-aminopyrazin-2-yl)-5-(5-(methoxy-d)pyridin-2-yl)-3H-imidazo[4,5-b]pyridin-3-yl) phenyl)methanol (320 mg, 747 μmol) in CH$_2$Cl$_2$ (10 mL) was added SOCl$_2$ (444 mg, 3.74 mmol). The mixture was stirred at 25° C. for 1 hr. The reaction was concentrated under reduced pressure to give 3-(3-(4-(chloromethyl)phenyl)-5-(5-(methoxy-d$_3$)pyridin-2-yl)-3H-imidazo[4,5-b] pyridin-2-yl)pyrazin-2-amine (Intermediate 334, 360 mg, HCl salt) as a yellow solid. MS: m/z=447.1, 449.1 [M+H]$^+$.

Intermediate 335: 3-(3-(4-(Chloromethyl)phenyl)-5-(6-(fluoromethoxy)pyridin-3-yl)-3H-imidazo[4,5-b] pyridin-2-yl)pyrazin-2-amine

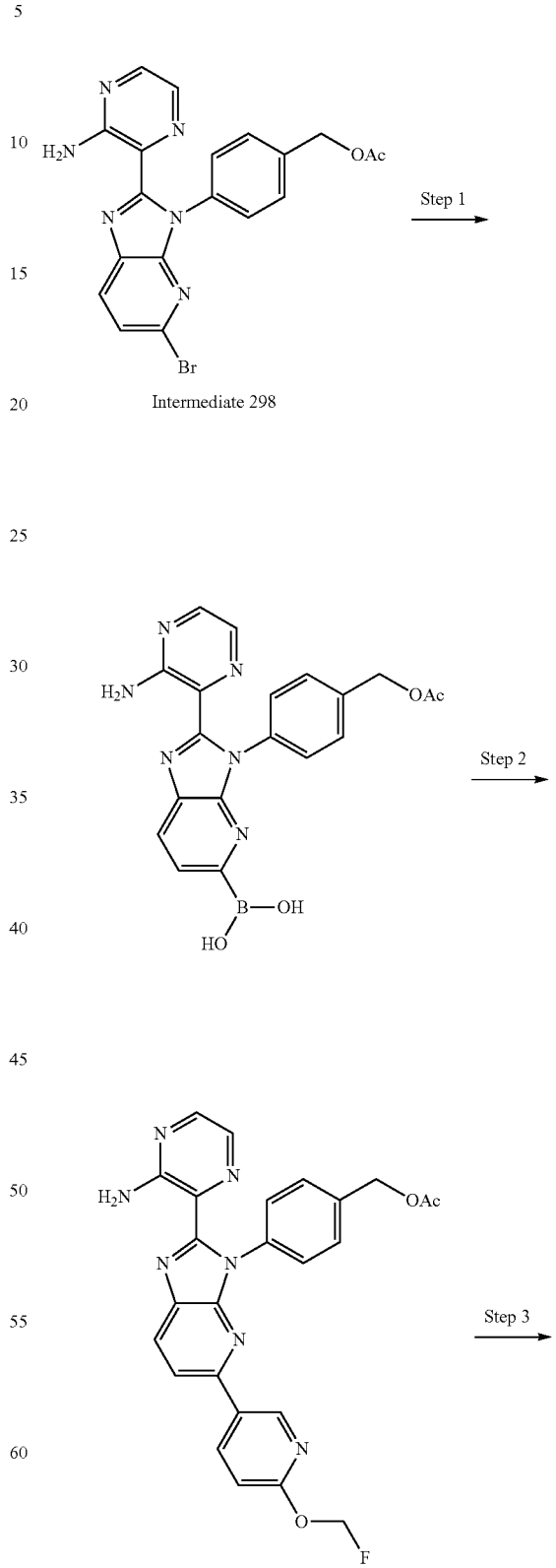

-continued

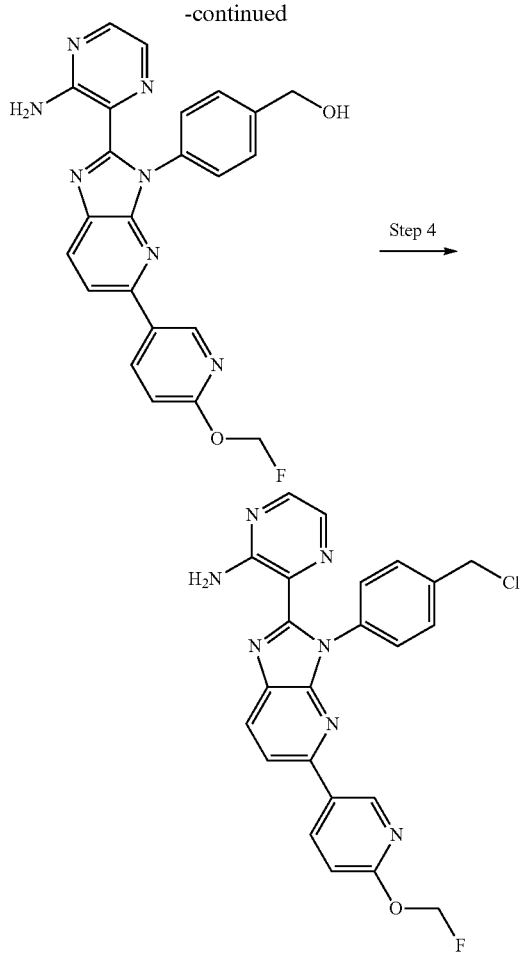

Intermediate 335

Step 1: (3-(4-(Acetoxymethyl)phenyl)-2-(3-aminopyrazin-2-yl)-3H-imidazo[4,5-b]pyridin-5-yl)boronic acid A mixture of Intermediate 298 (500 mg, 1.14 mmol), 4,4,4',4',5,5,5',5'-octamethyl-2,2'-bi(1,3,2-dioxaborolane) (578 mg, 2.28 mmol), KOAc (355 mg, 3.41 mmol) and Pd(dppf)Cl$_2$ (83.3 mg, 114 μmol) in 1,4-dioxane (5 mL) was degassed, purged with N$_2$ three times, and stirred at 100° C. for 3 hr under N$_2$ atmosphere. (3-(4-(Acetoxymethyl)phenyl)-2-(3-aminopyrazin-2-yl)-3H-imidazo[4,5-b]pyridin-5-yl)boronic acid was obtained as a black liquid, which was used in the next step without work-up and purification. MS: m/z=404.9 [M+H]$^+$.

Step 2: 4-(2-(3-Aminopyrazin-2-yl)-5-(6-(fluoromethoxy)pyridin-3-yl)-3H-imidazo[4,5-b]pyridin-3-yl)benzyl acetate A mixture of (3-(4-(acetoxymethyl)phenyl)-2-(3-aminopyrazin-2-yl)-3H-imidazo[4,5-b]pyridin-5-yl)boronic acid (470 mg, 1.16 mmol), 5-bromo-2-(fluoromethoxy)pyridine (264 mg, 1.28 mmol), Cs$_2$CO$_3$ (1.14 g, 3.49 mmol), Pd(dppf)Cl$_2$ (85.1 mg, 116 μmol) in 1,4-dioxane (5 mL) and H$_2$O (1 mL) was degassed and purged with N$_2$ three times. The mixture was stirred at 90° C. for 3 hr under N$_2$ atmosphere. The reaction mixture was poured into H$_2$O (15 mL), extracted with EtOAc (15 mL×3). The combined organic layers were washed with brine (30 mL×3), dried over anhydrous Na$_2$SO$_4$, filtered and concentrated under reduced pressure. After purified by silica gel flash chromatography (Eluent of 0%~30% EtOAc in petroleum ether), 4-(2-(3-aminopyrazin-2-yl)-5-(6-(fluoromethoxy)pyridin-3-yl)-3H-imidazo[4,5-b]pyridin-3-yl)benzyl acetate (385 mg, yield: 68% for two steps) was obtained as a brown solid. MS: m/z=486.0 [M+H]$^+$. $^1$H NMR (400 MHz, Dimethysulfoxide-d$_6$) δ 8.90 (d, J=2.0 Hz, 1H), 8.51-8.27 (m, 2H), 8.16-7.98 (m, 2H), 7.82 (br s, 2H), 7.58-7.43 (m, 5H), 7.10 (d, J=8.4 Hz, 1H), 6.12 (d, J=52.4 Hz, 2H), 5.19 (s, 2H), 2.13 (s, 3H). $^{19}$F NMR (400 MHz, Dimethysulfoxide-d$_6$) δ −154.404.

Step 3: (4-(2-(3-Aminopyrazin-2-yl)-5-(6-(fluoromethoxy)pyridin-3-yl)-3H-imidazo[4,5-b]pyridin-3-yl)phenyl)methanol To a solution of 4-(2-(3-aminopyrazin-2-yl)-5-(6-(fluoromethoxy)pyridin-3-yl)-3H-imidazo[4,5-b]pyridin-3-yl)benzyl acetate (385 mg, 793 μmol) in MeOH (8 mL) and THF (8 mL) was added K$_2$CO$_3$ (219 mg, 1.59 mmol) in H$_2$O (2 mL). The mixture was stirred at 25° C. for 0.5 hr. The reaction mixture was concentrated under reduced pressure, diluted with H$_2$O (20 mL), and extracted with EtOAc (50 mL×3). The combined organic layers were dried over anhydrous Na$_2$SO$_4$, filtered and concentrated under reduced pressure. (4-(2-(3-Aminopyrazin-2-yl)-5-(6-(fluoromethoxy)pyridin-3-yl)-3H-imidazo[4,5-b]pyridin-3-yl)phenyl)methanol (360 mg, crude) was obtained as a yellow solid. MS: m/z=444.0 [M+H]$^+$.

Step 4: 3-(3-(4-(Chloromethyl)phenyl)-5-(6-(fluoromethoxy)pyridin-3-yl)-3H-imidazo[4,5-b]pyridin-2-yl)pyrazin-2-amine To a solution of 4-(2-(3-aminopyrazin-2-yl)-5-(6-(fluoromethoxy)pyridin-3-yl)-3H-imidazo[4,5-b]pyridin-3-yl)phenyl)methanol (360 mg, 812 μmol) in CH$_2$Cl$_2$ (5 mL) was added SOCl$_2$ (2 mL). The mixture was stirred at 40° C. for 0.3 hr. The reaction was concentrated under reduced pressure to give 3-(3-(4-(chloromethyl)phenyl)-5-(6-(fluoromethoxy)pyridin-3-yl)-3H-imidazo[4,5-b]pyridin-2-yl)pyrazin-2-amine (Intermediate 335, 420 mg, HCl salt) was obtained as a yellow solid. MS: m/z=461.9, 463.7 [M+H]$^+$.

Intermediate 336: 3-(3-(4-(Chloromethyl)phenyl)-5-(6-(fluoromethoxy-d$_2$)pyridin-3-yl)-3H-imidazo[4,5-b]pyridin-2-yl)pyrazin-2-amine

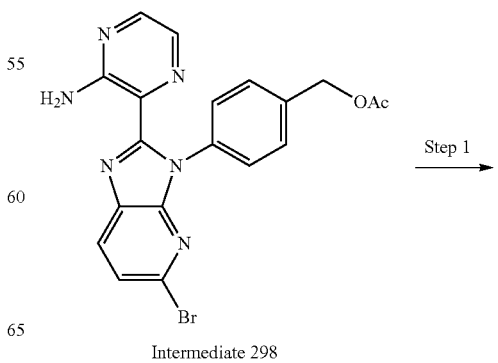

Intermediate 298

Step 1 →

1041

-continued

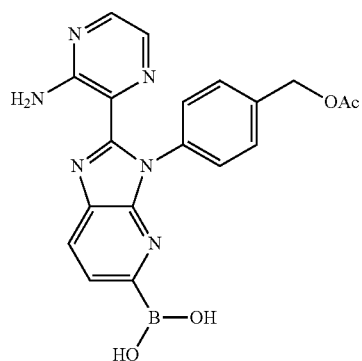

Step 2
Intermediate 311

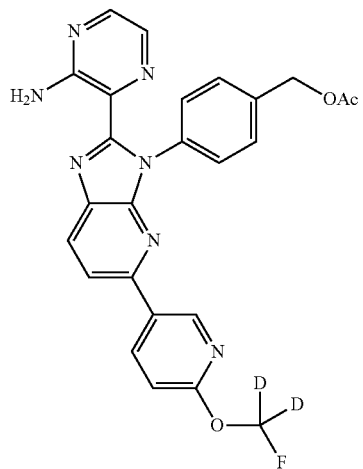

Step 3

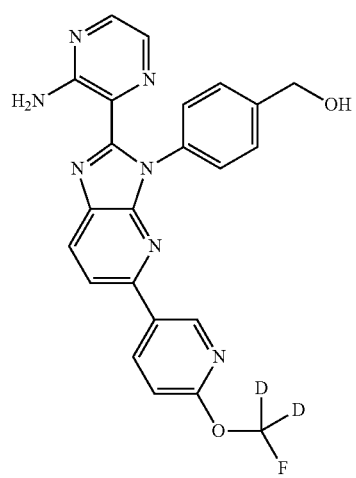

Step 4

1042

-continued

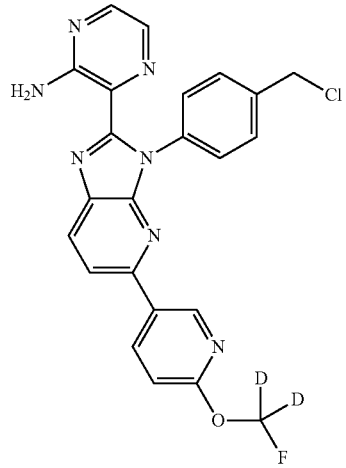

Intermediate 336

Step 1: (3-(4-(Acetoxy methyl)phenyl)-2-(3-amino-pyrazin-2-yl)-3H-imidazo[4,5-b]pyridin-5-yl)boronic acid A mixture of Intermediate 298 (550 mg, 1.25 mmol), 4,4,4',4',5,5,5',5'-octamethyl-2,2'-bi(1,3,2-dioxaborolane) (636 mg, 2.50 mmol), Pd(dppf)Cl$_2$ (91.6 mg, 125 μmol) and KOAc (369 mg, 3.76 mmol) in 1,4-dioxane (12 mL) was degassed, purged with N$_2$ three times, and stirred at 80° C. for 16 hr under N$_2$ atmosphere. (3-(4-(Acetoxymethyl)phenyl)-2-(3-aminopyrazin-2-yl)-3H-imidazo[4,5-b]pyridin-5-yl)boronic acid was obtained as a black liquid, which was used in the next step without work-up and purification. MS: m/z=405.0 [M+H]M.

Step 2: 4-(2-(3-Aminopyrazin-2-yl)-5-(6-(fluoromethoxy-d$_2$)pyridin-3-yl)-3H-imidazo[4,5-b]pyridin-3-yl)benzyl acetate A mixture of (3-(4-(acetoxymethyl)phenyl)-2-(3-aminopyrazin-2-yl)-3H-imidazo[4,5-b]pyridin-5-yl)boronic acid (350 mg, 865 μmol), Intermediate 311 (198 mg, 952 μmol), Cs$_2$CO$_3$ (846 mg, 2.60 mmol) and Pd(dppf)Cl$_2$ (63.3 mg, 86.5 μmol) in 1,4-dioxane (10 mL) and H$_2$O (2 mL) was degassed, purged with N$_2$ three times, and stirred at 90° C. for 1 hr under N$_2$ atmosphere. The reaction mixture was quenched with H$_2$O (20 mL) and extracted with CH$_2$Cl$_2$ (15 mL×2). The combined organic layers were washed with brine (30 mL), dried over Na$_2$SO$_4$, filtered and concentrated under reduced pressure. After purified by silica gel flash chromatography (Eluent of 15%~50% EtOAc in petroleum ether), 4-(2-(3-aminopyrazin-2-yl)-5-(6-(fluoromethoxy-d$_2$)pyridin-3-yl)-3H-imidazo[4,5-b]pyridin-3-yl)benzyl acetate (255 mg, yield: 55% for two steps) was obtained as a yellow solid. MS: m/z=488.1 [M+H]$^+$. D %: 2D %=93.7%. $^1$H NMR (400 MHz, Dimethylsulfoxide-d$_6$) δ 8.90 (d, J=2.4 Hz, 1H), 8.45-8.32 (m, 2H), 8.10-8.00 (m, 2H), 7.82 (br s, 2H), 7.54 (d, J=2.4 Hz, 1H), 7.52-7.45 (m, 4H), 7.10 (d, J=8.4 Hz, 1H), 5.19 (s, 2H), 2.13 (s, 3H). $^{19}$F NMR (400 MHz, Dimethylsulfoxide-d$_6$) δ −155.60.

Step 3: (4-(2-(3-Aminopyrazin-2-yl)-5-(6-(fluoromethoxy-d$_2$)pyridin-3-yl)-3H-imidazo[4,5-b]pyridin-3-yl)phenyl)methanol To a solution of 4-(2-(3-aminopyrazin-2-yl)-5-(6-(fluoromethoxy-d$_2$)pyridin-3-yl)-3H-imidazo[4,5-b]pyridin-3- yl)benzyl acetate (255 mg, 523 μmol) in THF (10 mL), MeOH (10 mL) and H$_2$O (6 mL) was added K$_2$CO$_3$ (217 mg, 1.57 mmol). The mixture was stirred at 25° C. for 1 hr. The reaction mixture was quenched with H$_2$O (20 mL) at 25° C. and extracted with CH$_2$Cl$_2$ (30 mL×2). The combined organic layers were washed with brine (50 mL), dried over Na$_2$SO$_4$, filtered and concentrated under reduced pressure. After purified by triturated with CH$_2$Cl$_2$ (10 mL) at 25° C. for 10 min, (4-(2-(3-aminopyrazin-2-yl)-5-(6-(fluoromethoxy-d$_2$)pyridin-3-yl)-3H-imidazo[4,5-b]pyridin-3-yl)phenyl)methanol (185 mg, yield: 79%) was obtained as a yellow solid. MS: m/z=446.1 [M+H]$^+$. $^1$H NMR (400 MHz, Dimethylsulfoxide-d$_6$) δ 8.90 (d, J=2.0 Hz, 1H), 8.41 (dd, J=8.8, 2.4 Hz, 1H), 8.36 (d, J=8.4 Hz, 1H), 8.07 (d, J=8.8 Hz, 1H), 8.02 (d, J=2.4 Hz, 1H), 7.79 (br s, 2H), 7.55 (d, J=2.4 Hz, 1H), 7.47-7.43 (m, 2H), 7.41-7.37 (m, 2H), 7.09 (d, J=8.8 Hz, 1H), 5.42-5.28 (m, 1H), 4.61 (br s, 2H).

Step 4: 3-(3-(4-(Chloromethyl)phenyl)-5-(6-(fluoromethoxy-d$_2$)pyridin-3-yl)-3H-imidazo[4,5-b]pyridin-2-yl)pyrazin-2-amine To a solution of (4-(2-(3-aminopyrazin-2-yl)-5-(6-(fluoromethoxy-d$_2$)pyridin-3-yl)-3H-imidazo[4,5-b]pyridin-3-yl)phenyl)methanol (185 mg, 415 μmol) in CH$_2$Cl$_2$ (10 mL) was added SOCl$_2$ (819 mg, 6.89 mmol). The mixture was stirred at 25° C. for 1 hr. The reaction was concentrated under reduced pressure to give 3-(3-(4-(chloromethyl)phenyl)-5-(6-(fluoromethoxy-d$_2$)pyridin-3-yl)-3H-imidazo[4,5-b]pyridin-2-yl)pyrazin-2-amine (Intermediate 336, 208 mg, HCl salt) was obtained as a yellow solid. MS: m/z=464.0, 466.0 [M+H]$^+$. $^1$H NMR (400 MHz, Dimethylsulfoxide-d$_6$) δ 8.94-8.87 (m, 1H), 8.44-8.35 (m, 2H), 8.11-8.01 (m, 2H), 7.61-7.45 (m, 5H), 7.10 (d, J=8.8 Hz, 1H), 4.89 (s, 2H).

Intermediate 337: 3-(3-(4-(Chloromethyl)phenyl)-5-(6-cyclopropoxypyridin-3-yl)-3H-imidazo[4,5-b]pyridin-2-yl)pyridin-2-amine

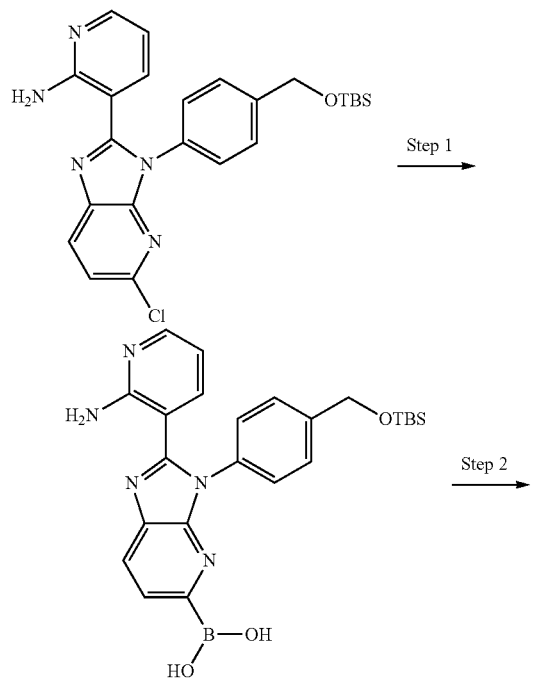

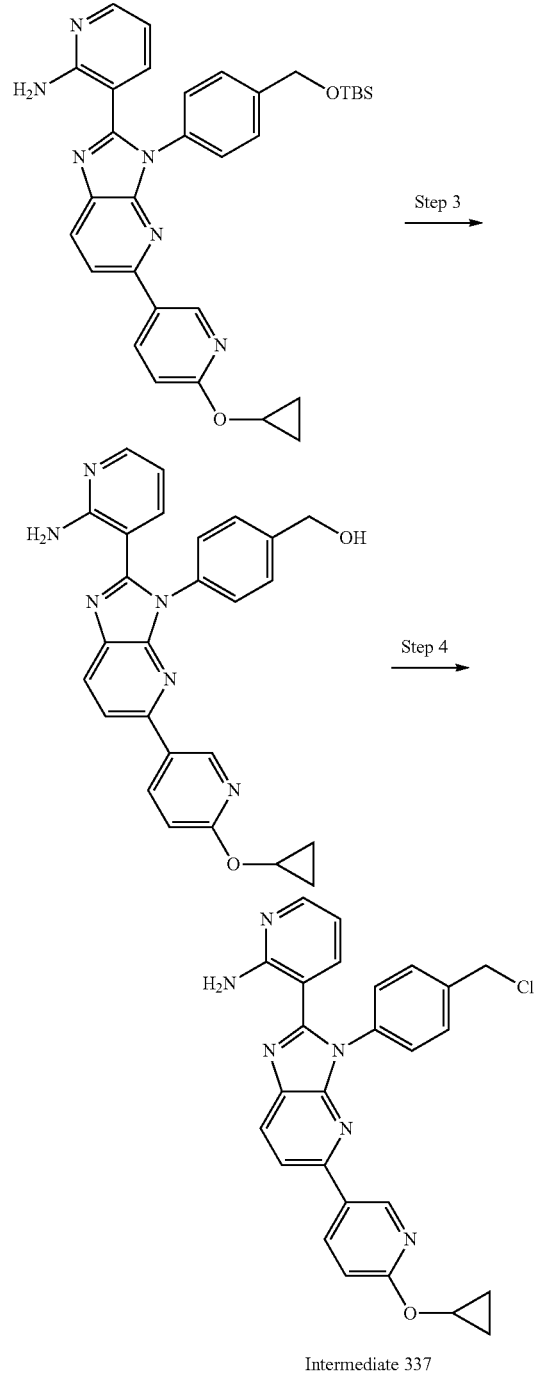

Intermediate 337

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid To a mixture of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 500 mg, 1.07 mmol) and 4,4,4',4',5,5,5',5'-octamethyl-2,2'-bi(1,3,2-dioxaborolane) (545 mg, 2.15 mmol) in 1,4-dioxane (10 mL) were added KOAc (316 mg, 3.22 mmol) and Pd(dppf)Cl$_2$ (78.5 mg, 107 μmol). The mixture was stirred at 100° C. for 1 hr. (2-(2-Aminopyridin- 3-yl)-3-(4-(((tert-butyldimethylsilyl)oxy)methyl)phenyl)-3H-imidazo[4,5-b]pyridin-5-yl)boronic acid was obtained as a black liquid, which was used in the next step directly. MS: m/z=476.2 [M+H]⁺.

Step 2: 3-(3-(4-(((tert-Butyldimethylsilyl)oxy)methyl)phenyl)-5-(6-cyclopropoxypyridin-3-yl)-3H-imidazo[4,5-b]pyridin-2-yl)pyridin-2-amine To a mixture of (2-(2-aminopyridin-3-yl)-3-(4-(((tert-butyldimethylsilyl)oxy)methyl)phenyl)-3H-imidazo[4,5-b]pyridin-5-yl)boronic acid (510 mg, 1.07 mmol) and 5-bromo-2-cyclopropoxypyridine (230 mg, 1.07 mmol) in 1,4-dioxane (10 mL) and H₂O (2 mL) were added Cs₂CO₃ (1.05 g, 3.22 mmol) and Pd(dppf)Cl₂ (78.5 mg, 107 μmol), The mixture was stirred at 100° C. for 2 hr. The mixture was dilute with H₂O (50 m L) and extracted with EtOAc (50 mL×2). The combined organic layers were washed with brine (50 mL), dried over anhydrous Na₂SO₄, filtered and concentrated. After purified by silica gel flash chromatography (EtOAc in petroleum ether=0-50%), 3-(3-(4-(((tert-butyldimethylsilyl)oxy)methyl)phenyl)-5-(6-cyclopropoxypyridin-3-yl)-3H-imidazo[4,5-b]pyridin-2-yl)pyridin-2-amine (250 mg, yield: 41% for 2 steps) was obtained as a yellow solid. MS: m/z=565.3 [M+H]⁺. ¹H NMR (400 MHz, Dimethylsulfoxide-d₆) δ 8.86 (d, J=2.0 Hz, 1H), 8.35-8.24 (m, 2H), 8.03-7.97 (m, 2H), 7.50-7.44 (m, 4H), 7.20 (dd, J=7.6, 2.0 Hz, 1H), 7.03 (br s, 2H), 6.94 (d, J=8.8 Hz, 1H), 6.39 (dd, J=8.0, 4.8 Hz, 1H), 4.82 (s, 2H), 4.28-4.21 (m, 1H), 0.92 (s, 9H), 0.81-0.75 (m, 2H), 0.71-0.66 (m, 2H), 0.11 (s, 6H).

Step 3: (4-(2-(2-Aminopyridin-3-yl)-5-(6-cyclopropoxypyridin-3-yl)-3H-imidazo[4,5-b]pyridin-3-yl)phenyl)methanol To a mixture of 3-(3-(4-(((tert-butyldimethylsilyl)oxy)methyl)phenyl)-5-(6-cyclopropoxypyridin-3-yl)-3H-imidazo[4,5-b]pyridin-2-yl)pyridin-2-amine (230 mg, 407 μmol) in THF (3 mL) was added TBAF (1M in THF, 611 μL). The mixture was stirred at 20° C. for 0.5 hr. The mixture was diluted with H₂O (50 mL) and extracted with EtOAc (50 mL×2). The combined organic layers were washed with brine (50 mL), dried over anhydrous Na₂SO₄, filtered and concentrated to give (4-(2-(2-aminopyridin-3-yl)-5-(6-cyclopropoxypyridin-3-yl)-3H-imidazo[4,5-b]pyridin-3-yl)phenyl)methanol (184 mg) was obtained as a brown solid. MS: m/z=451.2 [M+H]⁺.

Step 4: 3-(3-(4-(Chloromethyl)phenyl)-5-(6-cyclopropoxypyridin-3-yl)-3H-imidazo[4,5-b]pyridin-2-yl)pyridin-2-amine To a mixture of (4-(2-(2-aminopyridin-3-yl)-5-(6-cyclopropoxypyridin-3-yl)-3H-imidazo[4,5-b]pyridin-3-yl)phenyl)methanol (183 mg, 407 μmol) in CH₂Cl₂ (2 mL) was added SOCl₂ (88.7 μL, 1.22 mmol,). The mixture was stirred at 20° C. for 0.5 hr. The mixture was filtered and concentrated to give 3-(3-(4-(chloromethyl)phenyl)-5-(6-cyclopropoxypyridin-3-yl)-3H-imidazo[4,5-b]pyridin-2-yl)pyridin-2-amine (Intermediate 337, 191 mg) as a yellow solid. MS: m/z=469.2, 471.1 [M+H]⁺.

Intermediate 338: 3-(3-(4-(Chloromethyl)phenyl)-5-(6-isopropoxypyridin-3-yl)-3H-imidazo[4,5-b]pyridin-2-yl)pyridin-2-amine

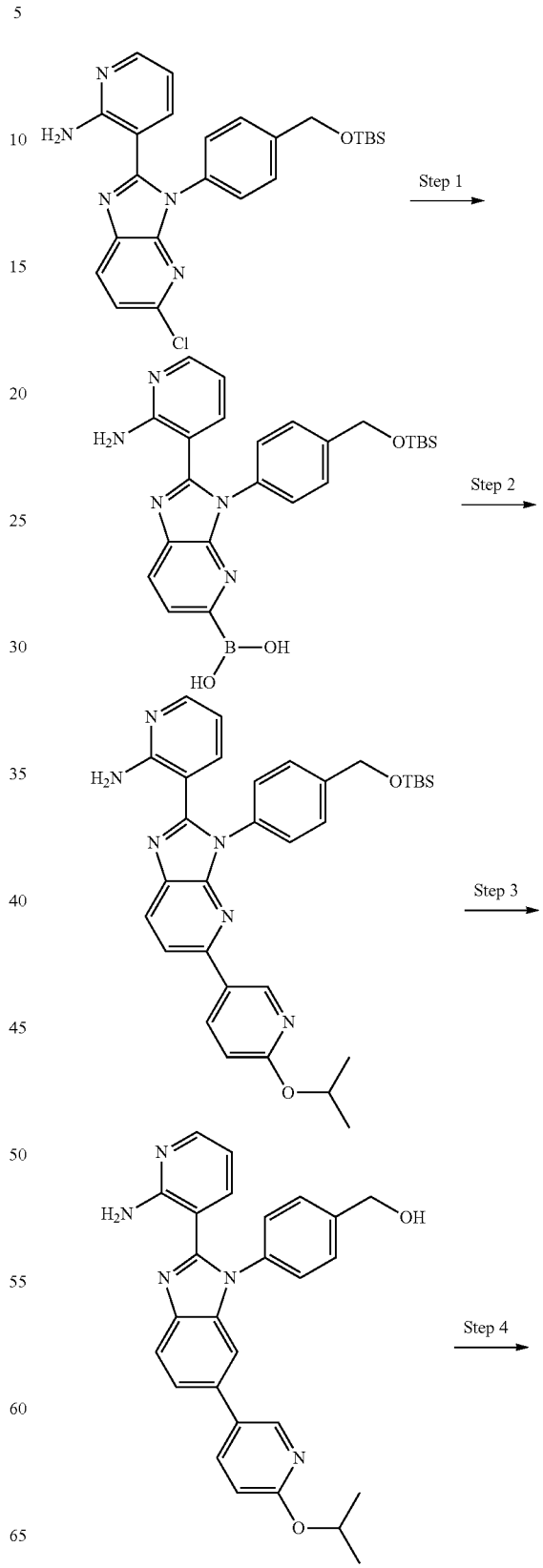

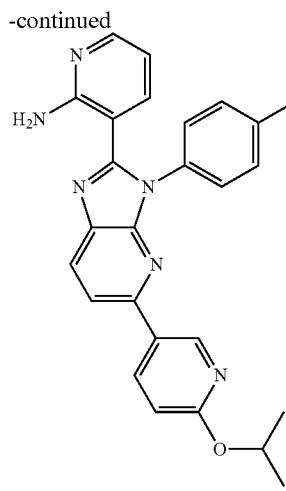

Intermediate 338

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid To a mixture of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 400 mg, 784 µmol) and 4,4,4',4',5,5,5',5'-octamethyl-2,2'-bi(1,3,2-dioxaborolane) (398 mg, 1.57 mmol) in 1,4-dioxane (10 mL) were added KOAc (231 mg, 2.35 mmol) and Pd(dppf)Cl$_2$ (57.3 mg, 78.4 µmol). The mixture was stirred at 85° C. for 1 hr. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used into the next step directly. MS: m/z=476.2 [M+H]$^+$.

Step 2: 3-(3-(4-(((tert-butyldimethylsilyl)oxy)methyl)phenyl)-5-(6-isopropoxypyridin-3-yl)-3H-imidazo[4,5-b]pyridin-2-yl)pyridin-2-amine To a mixture of (2-(2-aminopyridin-3-yl)-3-(4-(((tert-butyldimethylsilyl)oxy)methyl)phenyl)-3H-imidazo[4,5-b]pyridin-5-yl)boronic acid (372 mg, 782 µmol) and 5-bromo-2-isopropoxypyridine (186 mg, 861 µmol) in 1,4-dioxane (10 mL) and H$_2$O (2 mL) were added Cs$_2$CO$_3$ (765 mg, 2.35 mmol) and Pd(dppf)Cl$_2$ (57.3 mg, 78.3 µmol). The mixture was stirred at 100° C. for 1 hr. The reaction mixture was quenched with H$_2$O (50 mL) and extracted with EtOAc (50 mL×2). The combined organic layers were washed with brine (50 mL), dried over anhydrous Na$_2$SO$_4$, filtered and concentrated. After purified by silica gel flash chromatography (EtOAc in petroleum ether=0-50%), 3-(3-(4-(((tert-butyldimethylsilyl)oxy)methyl)phenyl)-5-(6-isopropoxypyridin-3-yl)-3H-imidazo[4,5-b]pyridin-2-yl)pyridin-2-amine (300 mg, yield: 68% for two steps) was obtained as a yellow solid. MS: m/z=567.3 [M+H]$^+$.

Step 3: (4-(2-(2-Aminopyridin-3-yl)-5-(6-isopropoxypyridin-3-yl)-3H-imidazo[4,5-b]pyridin-3-yl)phenyl)methanol To a mixture of 3-(3-(4-(((tert-butyldimethylsilyl)oxy)methyl)phenyl)-5-(6-isopropoxypyridin-3-yl)-3H-imidazo[4,5-b]pyridin-2-yl)pyridin-2-amine (250 mg, 441 µmol) in THF (4 mL) was added TBAF (1M in THF) (1M, 662 µL). The mixture was stirred at 20° C. for 0.5 hr. The reaction mixture was quenched with H$_2$O (50 mL) and extracted with EtOAc (50 mL×2). The combined organic layers were washed with brine (20 mL), dried over anhydrous Na$_2$SO$_4$, filtered and concentrated under reduced pressure. (4-(2-(2-Aminopyridin-3-yl)-5-(6-isopropoxypyridin-3-yl)-3H-imidazo[4,5-b]pyridin-3-yl)phenyl)methanol (199.60 mg) was obtained as a brown solid which was used in the next step without purification. MS: m/z=453.2 [M+H]$^+$. $^1$H NMR (400 MHz, Dimethylsulfoxide-d$_6$) δ 8.83 (d, J=2.4 Hz, 1H), 8.30-8.22 (m, 2H), 8.03-7.95 (m, 2H), 7.51-7.43 (m, 4H), 7.26-7.16 (m, 1H), 7.00 (br s, 2H), 6.83 (d, J=8.8 Hz, 1H), 6.42 (dd, J=7.6, 4.8 Hz, 1H), 5.36 (t, J=6.0 Hz, 1H), 5.28-5.24 (m, 1H), 4.60 (d, J=6.0 Hz, 2H), 1.32-1.29 (m, 6H).

Step 4: 3-(3-(4-(Chloromethyl)phenyl)-5-(6-isopropoxypyridin-3-yl)-3H-imidazo[4,5-b]pyridin-2-yl)pyridin-2-amine To a mixture of (4-(2-(2-aminopyridin-3-yl)-5-(6-isopropoxypyridin-3-yl)-3H-imidazo[4,5-b]pyridin-3-yl)phenyl)methanol (199 mg, 441 µmol) in CH$_2$Cl$_2$ (2 mL) was added SOCl$_2$ (96.11 µL, 1.32 mmol). The mixture was stirred at 20° C. for 1 hr. The reaction was concentrated under reduced pressure. 3-(3-(4-(Chloromethyl)phenyl)-5-(6-isopropoxypyridin-3-yl)-3H-imidazo[4,5-b]pyridin-2-yl)pyridin-2-amine (Intermediate 338, 207 mg, 440 µmol) was obtained as a yellow solid. MS: m/z=471.2, 473.1 [M+H]$^+$.

Intermediate 339: 3-(3-(4-(Chloromethyl)phenyl)-5-(5-cyclopropoxypyridin-2-yl)-3H-imidazo[4,5-b]pyridin-2-yl)pyridin-2-amine

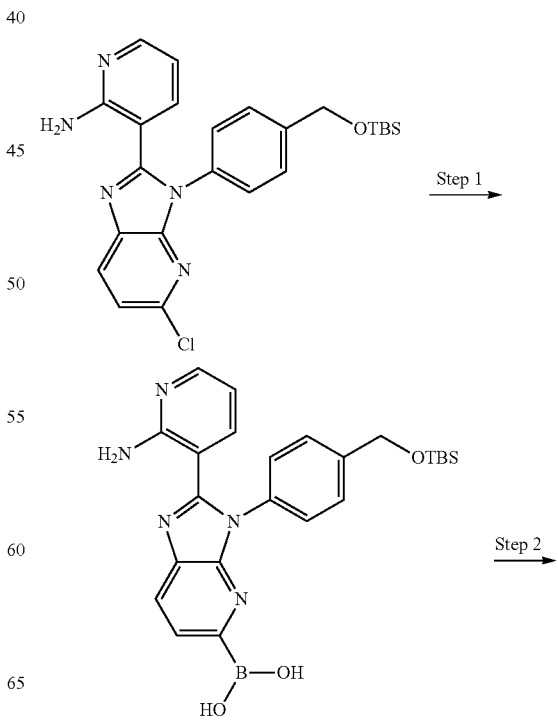

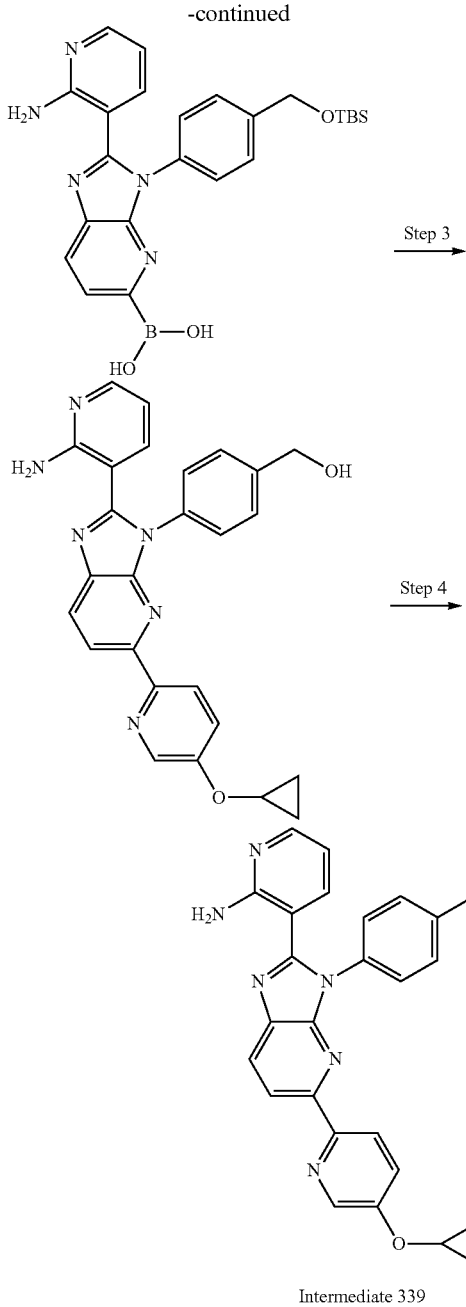

Intermediate 339

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 500 mg, 1.07 mmol) and 4,4,4',4',5,5,5',5'-octamethyl-2,2'-bi(1,3,2-dioxaborolane) (409 mg, 1.61 mmol) in 1,4-dioxane (10 mL) were added Pd(dppf)Cl$_2$ (78.5 mg, 107 µmol) and KOAc (316 mg, 3.22 mmol). The mixture was stirred at 85° C. for 2 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((Tert-butyldimethylsilyl)oxy)methyl)phenyl)-5-(5-cyclopropoxypyridin-2-yl)-3H-imidazo[4,5-b]pyridin-2-yl)pyridin-2-amine To a solution of (2-(2-aminopyridin-3-yl)-3-(4-(((tert-butyldimethylsilyl)oxy)methyl)phenyl)-3H-imidazo[4,5-b]pyridin-5-yl)boronic acid (510 mg, 1.07 mmol) and 2-bromo-5-cyclopropoxypyridine (230 mg, 1.07 mmol) in 1,4-dioxane (6 mL) and H$_2$O (1 mL) were added Cs$_2$CO$_3$ (1.05 g, 3.22 mmol) and Pd(dppf)Cl$_2$ (78.5 mg, 107 µmol). The mixture was stirred at 100° C. for 2 hr under N$_2$ atmosphere. The mixture was diluted with H$_2$O (10 mL) and extracted with EtOAc (10 mL×2). The combined organic layers were dried over anhydrous Na$_2$SO$_4$, filtered and concentrated. After purified by silica gel flash chromatography (Eluent of 0%~50% EtOAc in petroleum ether), 3-(3-(4-(((tert-butyldimethylsilyl)oxy)methyl)phenyl)-5-(5-cyclopropoxypyridin-2-yl)-3H-imidazo[4,5-b]pyridin-2-yl)pyridin-2-amine (320 mg, yield: 53% for two steps) was obtained as a light yellow oil. MS: m/z=565.3 [M+H]$^+$. $^1$H NMR (400 MHz, Dimethylsulfoxide-d$_6$) δ 8.45 (d, J=2.8 Hz, 1H), 8.36 (d, J=8.4 Hz, 1H), 8.7 (d, J=8.4 Hz, 1H), 8.13 (d, J=8.8 Hz, 1H), 8.00 (dd, J=4.8, 2.0 Hz, 1H), 7.59 (dd, J=8.8, 2.8 Hz, 1H), 7.52-7.47 (m, 4H), 7.20 (dd, J=7.6, 1.6 Hz, 1H), 7.02 (br s, 2H), 6.39 (dd, J=7.6, 4.8 Hz, 1H), 4.83 (s, 2H), 4.04-3.98 (m, 1H), 0.93 (s, 9H), 0.86-0.81 (m, 2H), 0.75-0.67 (m, 2H), 0.12 (m, 6H).

Step 3: (4-(2-(2-Aminopyridin-3-yl)-5-(5-cyclopropoxypyridin-2-yl)-3H-imidazo[4,5-b]pyridin-3-yl)phenyl)methanol To a solution of 3-(3-(4-(((tert-butyldimethylsilyl)oxy)methyl)phenyl)-5-(5-cyclopropoxypyridin-2-yl)-3H-imidazo[4,5-b]pyridin-2-yl)pyridin-2-amine (200 mg, 354 µmol) in THF (2 mL) was added TBAF (1 M in THF, 354.14 µL). The mixture was stirred at 25° C. for 0.5 hr. The mixture was diluted with H$_2$O (10 mL) and extracted with EtOAc (10 mL×2). The combined organic layers were dried over anhydrous Na$_2$SO$_4$, filtered and concentrated to give (4-(2-(2-aminopyridin-3-yl)-5-(5-cyclopropoxypyridin-2-yl)-3H-imidazo[4,5-b]pyridin-3-yl)phenyl)methanol (160 mg) as a light yellow oil. MS: m/z=451.2 [M+H]$^+$ Step 4: 3-(3-(4-(Chloromethyl)phenyl)-5-(5-cyclopropoxypyridin-2-yl)-3H-imidazo[4,5-b]pyridin-2-yl)pyridin-2-amine To a solution of (4-(2-(2-aminopyridin-3-yl)-5-(5-cyclopropoxypyridin-2-yl)-3H-imidazo[4,5-b]pyridin-3-yl)phenyl)methanol (160 mg, 354 µmol) in CH$_2$Cl$_2$ (2 mL) was added SOCl$_2$ (126 mg, 1.06 mmol). The mixture was stirred at 25° C. for 1 hr. The reaction was concentrated to give 3-(3-(4-(chloromethyl)phenyl)-5-(5-cyclopropoxypyridin-2-yl)-3H-imidazo[4,5-b]pyridin-2-yl)pyridin-2-amine (Intermediate 339, 166 mg, HCl salt) as a light yellow solid. MS: m/z=469.2, 471.2 [M+H]$^+$.

Intermediate 340: 3-(3-(4-(Chloromethyl)phenyl)-5-(5-isopropoxypyridin-2-yl)-3H-imidazo[4,5-b]pyridin-2-yl)pyridin-2-amine

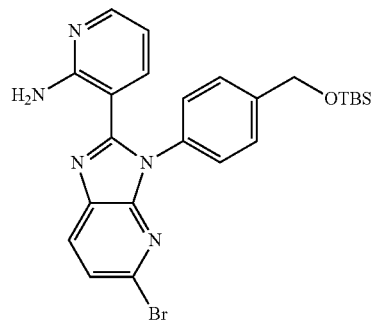

Intermediate 129

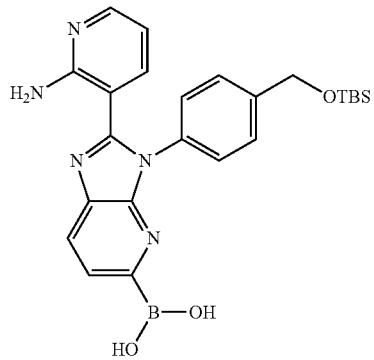

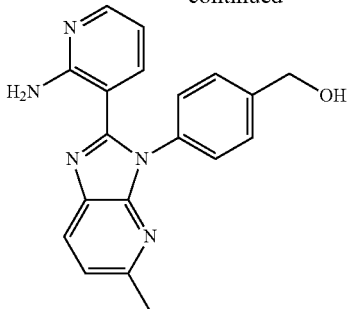

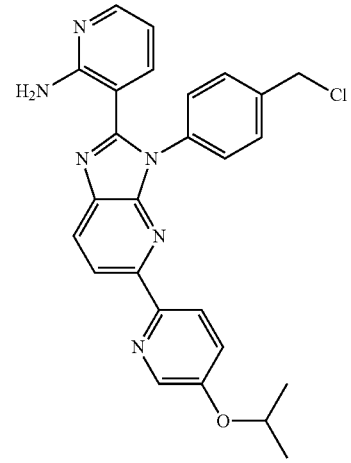

Intermediate 340

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid To a solution of Intermediate 129 (400 mg, 784 μmol) and 4,4,4',4',5,5,5',5'-octamethyl-2,2'-bi(1,3,2-dioxaborolane) (398 mg, 1.57 mmol) in 1,4-dioxane (4 mL) were added KOAc (231 mg, 2.35 mmol) and Pd(dppf)Cl$_2$ (57.3 mg, 78.4 μmol). The mixture was stirred at 85° C. for 2 hr under N$_2$. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a light yellow liquid, which was used in the next step without work up and purification. MS: m/z=476.3 [M+H]$^+$.

Step 2: 3-(3-(4-(((tert-Butyldimethylsilyl)oxy)methyl)phenyl)-5-(5-isopropoxypyridin-2-yl)-3H-imidazo[4,5-b]pyridin-2-yl)pyridin-2-amine To a solution of (2-(2-aminopyridin-3-yl)-3-(4-(((tert-butyldimethylsilyl)oxy)methyl)phenyl)-3H-imidazo[4,5-b]pyridin-5-yl)boronic acid (203 mg, 940 μmol), 2-bromo-5-isopropoxypyridine (220 mg, 1.06 mmol) in 1,4-dioxane (4 mL) and H$_2$O (0.8 mL) were added Cs$_2$CO$_3$ (766 mg, 2.35 mmol) and Pd(dppf)Cl$_2$ (57.3 mg, 78.4 mol). The mixture was stirred at 100° C. for 2 hr under N$_2$. The mixture was diluted with H$_2$O (10 mL) and extracted with EtOAc (10 mL×2). The combined organic layers were dried over anhydrous Na$_2$SO$_4$, filtered and concentrated. After purified by silica gel flash chromatography (Eluent of 0%~40% EtOAc in petroleum ether), 3-(3-(4-(((tert-butyldimethylsilyl)oxy)methyl)phenyl)-5-(5-isopropoxypyridin-2-yl)-3H-imidazo[4,5-b]pyridin-2-yl)pyridin-2-amine (270 mg, yield: 60.8% for two steps) was obtained as a yellow oil. MS: m/z=567.3 [M+H]$^+$.

Step 3: (4-(2-(2-Aminopyridin-3-yl)-5-(5-isopropoxypyridin-2-yl)-3H-imidazo[4,5-b]pyridin-3-yl)phenyl)methanol To a solution of 3-(3-(4-(((tert-butyldimethylsilyl)oxy)methyl)phenyl)-5-(5-isopropoxypyridin-2-yl)-3H-imidazo[4,5-b]pyridin-2-yl)pyridin-2-amine (240 mg, 424 μmol) in THF (3 mL) was added TBAF (1 M in THF, 551 μL). The mixture was stirred at 25° C. for 0.5 hr. The mixture was diluted with H$_2$O (10 mL) and extracted with EtOAc (5 mL×2). The combined organic layers were dried over anhydrous Na$_2$SO$_4$, filtered and concentrated. (4-(2-(2-Aminopyridin-3-yl)-5-(5-isopropoxypyridin-2-yl)-3H-imidazo[4,5-b]pyridin-3-yl)phenyl)methanol (192 mg) was obtained as light yellow oil. MS: m/z=453.2 [M+H]$^+$ Step 4: 3-(3-(4-(Chloromethyl)phenyl)-5-(5-isopropoxypyridin-2-yl)-3H-imidazo[4,5-b]pyridin-2-yl)pyridin-2-amine To a solution of (4-(2-(2-aminopyridin-3-yl)-5-(5-isopropoxypyridin-2-yl)-3H-imidazo[4,5-b]pyridin-3-yl)phenyl)methanol (192 mg, 424 μmol) in CH$_2$Cl$_2$ (1 mL) was added SOCl$_2$ (151 mg, 1.27 mmol). The mixture was stirred at 25° C. for 1 hr. The reaction was concentrated to give 3-(3-(4-(Chloromethyl)phenyl)-5-(5-isopropoxypyridin-2-yl)-3H-imidazo[4,5-b]pyridin-2-yl)pyridin-2-amine (Intermediate 340, 199 mg) as a light yellow solid. MS: m/z=471.3, 473.3 [M+H]$^+$.

Intermediate 341: 3-(3-(4-(Chloromethyl)phenyl)-5-(6-cyclopropylpyridin-3-yl)-3H-imidazo[4,5-b]pyridin-2-yl)pyridin-2-amine

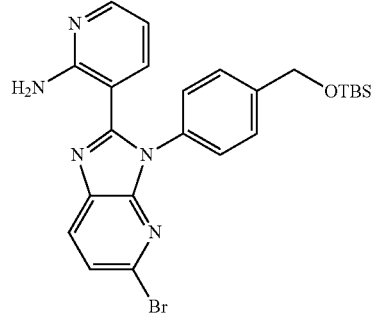

Intermediate 129

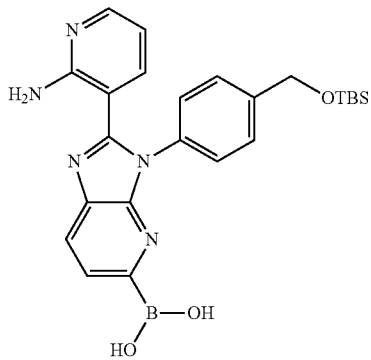

Step 2

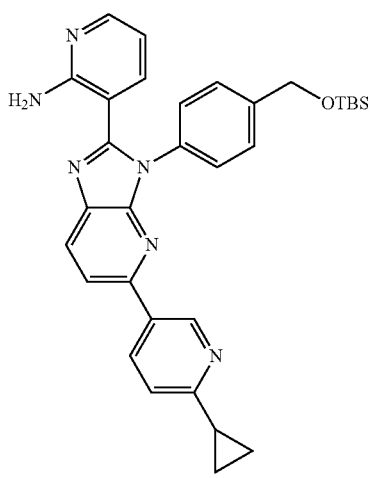

Step 3

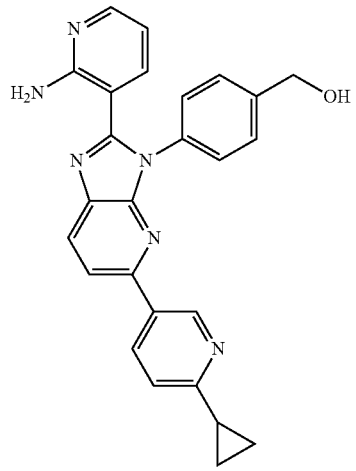

Step 4

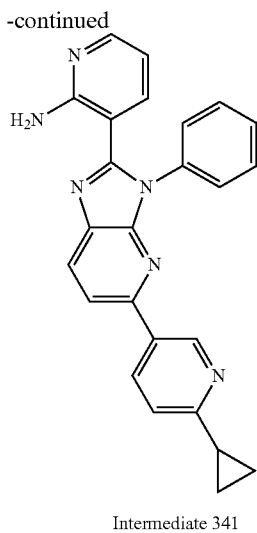

Intermediate 341

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid To a solution of Intermediate 129 (500 mg, 1.07 mmol) and 4,4,4',4',5,5,5',5'-octamethyl-2,2'-bi(1,3,2-dioxaborolane) (409 mg, 1.61 mmol) in 1,4-dioxane (10 mL) were added Pd(dppf)Cl$_2$ (78.5 mg, 107 µmol) and KOAc (316 mg, 3.22 mmol). The mixture was stirred at 100° C. for 2 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.2 [M+H]$^+$.

Step 2: 3-(3-(4-(((Tert-butyldimethylsilyl)oxy)methyl)phenyl)-5-(6-cyclopropylpyridin-3-yl)-3H-imidazo[4,5-b]pyridin-2-yl)pyridin-2-amine To a solution of (2-(2-aminopyridin-3-yl)-3-(4-(((tert-butyldimethylsilyl)oxy)methyl)phenyl)-3H-imidazo[4,5-b]pyridin-5-yl)boronic acid (510 mg, 1.07 mmol) and 5-bromo-2-cyclopropylpyridine (255 mg, 1.29 mmol) in 1,4-dioxane (10 mL) and H$_2$O (2 mL) were added Cs$_2$CO$_3$ (1.05 g, 3.22 mmol) and Pd(dppf)Cl$_2$ (78.5 mg, 107 µmol). The mixture was stirred at 100° C. for 2 hr under N$_2$ atmosphere. The mixture was diluted with H$_2$O (10 mL) and extracted with EtOAc (5 mL×2). The combined organic layers were dried over anhydrous Na$_2$SO$_4$, filtered and concentrated. After purified by silica gel flash chromatography (Eluent of 0%~50% EtOAc in petroleum ether), 3-(3-(4-(((tert-butyldimethylsilyl)oxy)methyl)phenyl)-5-(6-cyclopropylpyridin-3-yl)-3H-imidazo[4,5-b]pyridin-2-yl)pyridin-2-amine (300 mg, yield: 51% for two steps) was obtained as a yellow oil. MS: m/z=549.3 [M+H]$^+$.

Step 3: (4-(2-(2-Aminopyridin-3-yl)-5-(6-cyclopropylpyridin-3-yl)-3H-imidazo[4,5-b]pyridin-3-yl)phenyl)methanol To a solution of 3-(3-(4-(((tert-butyldimethylsilyl)oxy)methyl)phenyl)-5-(6-cyclopropylpyridin-3-yl)-3H-imidazo[4,5-b]pyridin-2-yl)pyridin-2-amine (300 mg, 547 µmol) in THF (2 mL) was added TBAF (1 M in THF, 711 µL). The mixture was stirred at 25° C. for 0.5 hr. The mixture was diluted with H$_2$O (10 mL) and extracted with EtOAc (10 mL×2). The combined organic layers were dried over anhydrous Na$_2$SO$_4$, filtered and concentrated. (4-(2-(2-Aminopyridin-3-yl)-5-(6-cyclopropylpyridin-3-yl)-3H-imidazo[4,5-b]pyridin-3-yl)phenyl)methanol (238 mg) was obtained as a light yellow oil. MS: m/z=435.2 [M+H]+

Step 4: 3-(3-(4-(Chloromethyl)phenyl)-5-(6-cyclopropylpyridin-3-yl)-3H-imidazo[4,5-b]pyridin-2-yl)pyridin-2-amine To a solution of (4-(2-(2-aminopyridin-3-yl)-5-(6-cyclopropylpyridin-3-yl)-3H-imidazo[4,5-b]pyridin-3-yl)phenyl)methanol (238 mg, 547 µmol) in CH$_2$Cl$_2$ (2 mL) was added SOCl$_2$ (195 mg, 1.64 mmol). The mixture was stirred at 25° C. for 1 hr. The reaction was concentrated. 3-(3-(4-(Chloromethyl)phenyl)-5-(6-cyclopropylpyridin-3-yl)-3H-imidazo[4,5-b]pyridin-2-yl)pyridin-2-amine (Intermediate 341, 248 mg, HCl salt) was obtained as a light yellow solid. MS: m/z=453.2, 455.2 [M+H]$^+$. $^1$H NMR (400 MHz, Dimethylsulfoxide-d$_6$) δ 9.15 (s, 1H), 8.90 (d, J=8.4 Hz, 1H), 8.48 (d, J=8.4 Hz, 2H), 8.31 (d, J=8.4 Hz, 1H), 8.17 (d, J=5.6 Hz, 1H), 7.93 (d, J=7.2 Hz, 1H), 7.72 (d, J=8.8 Hz, 1H), 7.68-7.59 (m, 4H), 6.92 (t, J=6.8 Hz, 1H), 4.88 (s, 2H), 1.60-1.54 (m, 1H), 1.41-1.33 (m, 2H), 1.26-1.20 (m, 2H).

Intermediate 342: 3-(3-(4-(Chloromethyl)phenyl)-5-(6-isopropylpyridin-3-yl)-3H-imidazo[4,5-b]pyridin-2-yl)pyridin-2-amine

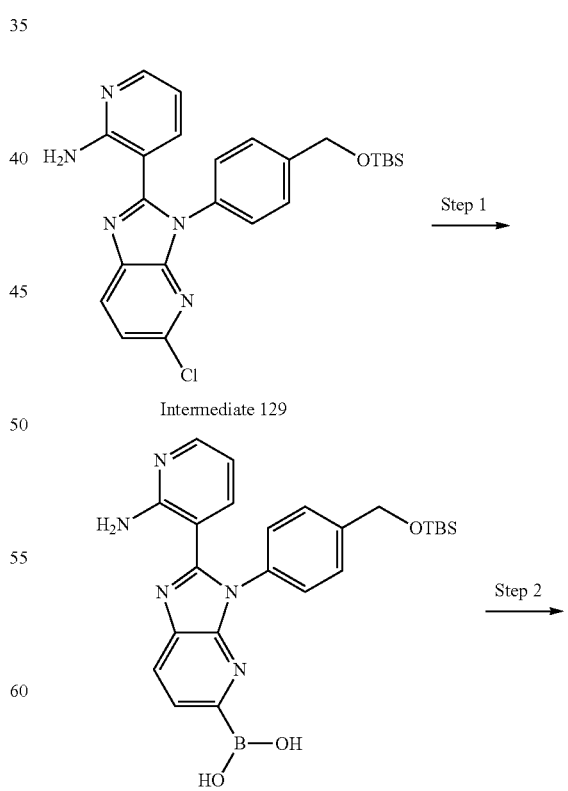

Intermediate 129

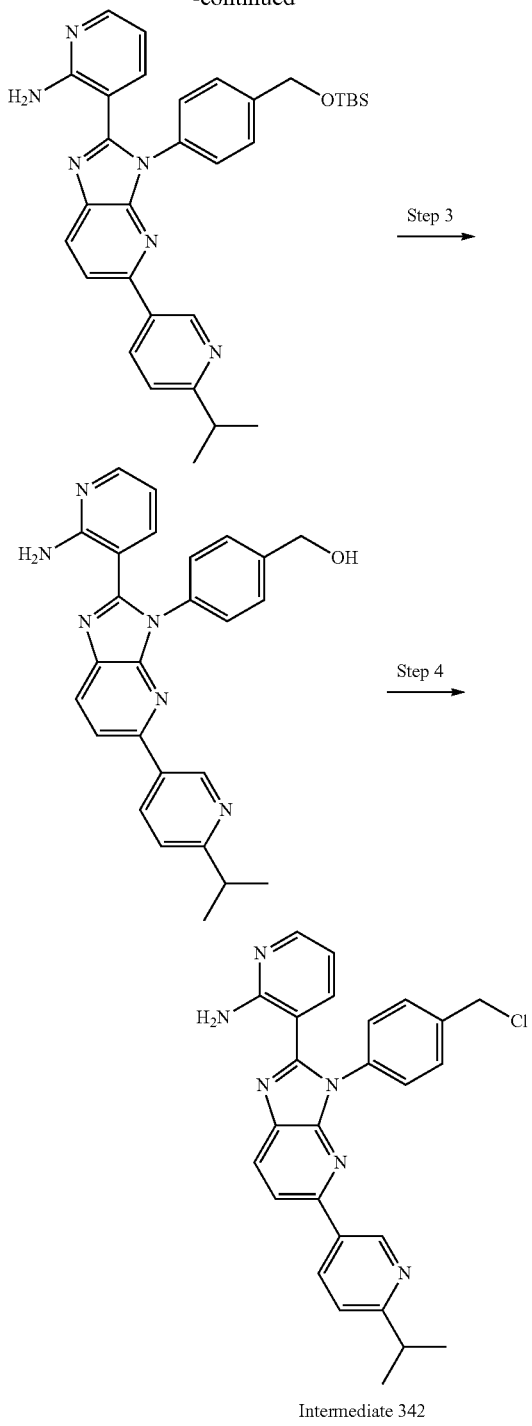

Intermediate 342

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid To a solution of 3-(3-(4-(((tert-butyldimethylsilyl)oxy)methyl)phenyl)-5-chloro-3H-imidazo[4,5-b]pyridin-2-yl)pyridin-2-amine (500 mg, 1.07 mmol) and 4,4,4',4',5,5,5',5'-octamethyl-2,2'-bi(1,3,2-dioxaborolane) (545 mg, 2.15 mmol) in 1,4-dioxane (15 mL) were added Pd(dppf)Cl$_2$ (78.5 mg, 107 μmol) and KOAc (316 mg, 3.22 mmol) at 20° C. The mixture was stirred at 110° C. for 2 hr under N$_2$. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step directly. MS: m/z=476.2 [M+H]$^+$.

Step 2: 3-(3-(4-(((tert-Butyldimethylsilyl)oxy)methyl)phenyl)-5-(6-isopropylpyridin-3-yl)-3H-imidazo[4,5-b]pyridin-2-yl)pyridin-2-amine To a solution of (2-(2-aminopyridin-3-yl)-3-(4-(((tert-butyldimethylsilyl)oxy)methyl)phenyl)-3H-imidazo[4,5-b]pyridin-5-yl)boronic acid (510 mg, 1.07 mmol) and 5-bromo-2-isopropylpyridine (258 mg, 1.29 mmol) in 1,4-dioxane (15 mL) and H$_2$O (3 mL) were added Pd(dppf)Cl$_2$ (78.5 mg, 107 μmol) and Cs$_2$CO$_3$ (1.05 g, 3.22 mmol) at 20° C. The mixture was stirred at 100° C. for 2 hr under N$_2$. The mixture was diluted with H$_2$O (30 mL) and extracted with EtOAc (30 mL×2). The combined organic layers were washed with brine (30 mL), dried over anhydrous Na$_2$SO$_4$, filtered and concentrated. After purified by silica gel flash chromatography (30~100% EtOAc in petroleum ether), 3-(3-(4-(((tert-butyldimethylsilyl)oxy)methyl)phenyl)-5-(6-isopropylpyridin-3-yl)-3H-imidazo[4,5-b]pyridin-2-yl)pyridin-2-amine (250 mg, 454 μmol, yield: 42% for 2 steps) was obtained as a brown solid. MS: m/z=551.3 [M+H]$^+$. $^1$H NMR (400 MHz, Dimethylsulfoxide-d$_6$) δ 9.13-9.09 (m, 1H), 8.32-8.23 (m, 2H), 8.04-7.98 (m, 2H), 7.52-7.46 (m, 4H), 7.35 (d, J=8.4 Hz, 1H), 7.20 (dd, J=7.6, 2.0 Hz, 1H), 7.03 (s, 2H), 6.42-6.36 (m, 1H), 4.82 (s, 2H), 3.10-2.99 (m, 1H), 1.24 (d, J=6.8 Hz, 6H), 0.92 (s, 9H), 0.11 (s, 6H).

Step 3: (4-(2-(2-Aminopyridin-3-yl)-5-(6-isopropylpyridin-3-yl)-3H-imidazo[4,5-b]pyridin-3-yl)phenyl)methanol To a solution of 3-(3-(4-(((tert-butyldimethylsilyl)oxy)methyl)phenyl)-5-(6-isopropylpyridin-3-yl)-3H-imidazo[4,5-b]pyridin-2-yl)pyridin-2-amine (250 mg, 454 μmol) in THF (6 mL) was added TBAF (1 M in THF, 681 μL). The reaction mixture was stirred at 20° C. for 0.5 hr. The mixture was diluted with H$_2$O (20 mL) and extracted with EtOAc (20 mL×2). The combined organic layers were washed with brine (20 mL), dried over anhydrous Na$_2$SO$_4$, filtered and concentrated. (4-(2-(2-Aminopyridin-3-yl)-5-(6-isopropylpyridin-3-yl)-3H-imidazo[4,5-b]pyridin-3-yl)phenyl)methanol (198 mg, 454 μmol) was obtained as a gray solid, which was used directly in the next step. MS: m/z=437.3 [M+H]$^+$. $^1$H NMR (400 MHz, Dimethylsulfoxide-d$_6$) δ 9.14-9.09 (m, 1H), 8.32-8.23 (m, 2H), 8.04-7.99 (m, 2H), 7.51-7.43 (m, 4H), 7.36 (d, J=8.0 Hz, 1H), 7.23 (dd, J=7.6, 2.0, Hz, 1H), 6.99 (s, 2H), 6.42 (dd, J=8.0, 4.8 Hz, 1H), 5.54-5.24 (m, 1H), 4.60 (s, 2H), 3.11-2.99 (m, 1H), 1.25 (d, J=6.8 Hz, 6H).

Step 4: 3-(3-(4-(Chloromethyl)phenyl)-5-(6-isopropylpyridin-3-yl)-3H-imidazo[4,5-b]pyridin-2-yl)pyridin-2-amine To a solution of (4-(2-(2-aminopyridin-3-yl)-5-(6-isopropylpyridin-3-yl)-3H-imidazo[4,5-b]pyridin-3-yl)phenyl)methanol (198 mg, 454 μmol) in CH$_2$Cl$_2$ (8 mL) was added SOCl$_2$ (162 mg, 1.36 mmol, 98.8 μL). The reaction mixture was stirred at 20° C. for 1 hr. The reaction mixture was concentrated. 3-(3-(4-(Chloromethyl)phenyl)-5-(6-isopropylpyridin-3-yl)-3H-imidazo[4,5-b]pyridin-2-yl)pyridin-2- amine (Intermediate 342, 206 mg, 453 μmol) was obtained as a gray solid, which was used directly in the next step. MS: m/z=455.2, 457.2 [M+H]⁺.

Intermediate 343: 3-(3-(4-(Chloromethyl)phenyl)-5-(5-cyclopropylpyridin-2-yl)-3H-imidazo[4,5-b]pyridin-2-yl)pyridin-2-amine

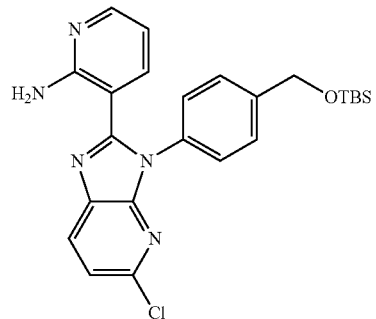

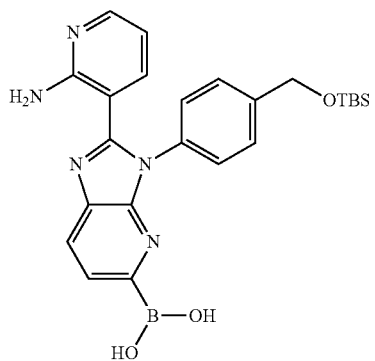

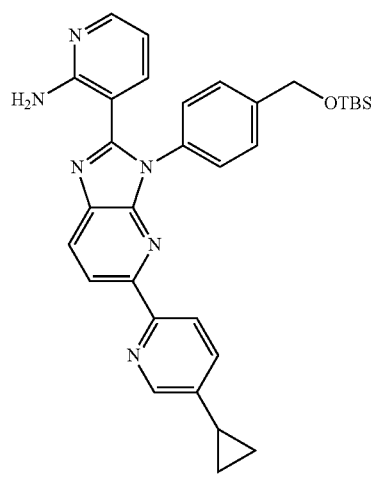

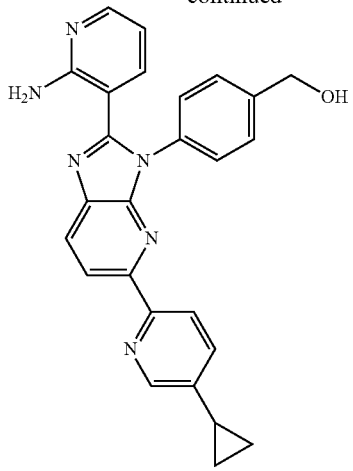

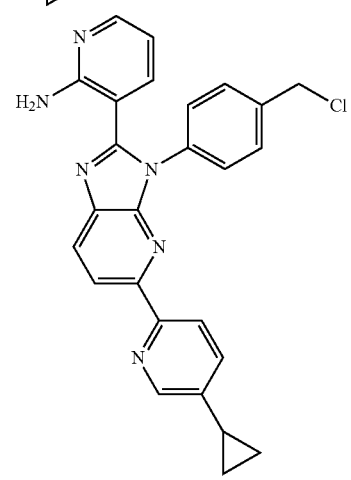

Intermediate 343

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 500 mg, 1.07 mmol) in 1,4-dioxane (6 mL) were added 4,4,4',4',5,5,5',5'-octamethyl-2,2'-bi(1,3,2-dioxaborolane) (545 mg, 2.15 mmol), KOAc (316 mg, 3.22 mmol), Pd(dppf)Cl₂ (78.5 mg, 107 μmol). The mixture was stirred at 100° C. for 12 hr under N₂. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.3 [M+H]⁺.

Step 2: 3-(3-(4-(((Tert-butyldimethylsilyl)oxy)methyl)phenyl)-5-(5-cyclopropylpyridin-2-yl)-3H-imidazo[4,5-b]pyridin-2-yl)pyridin-2-amine To a solution of (2-(2-aminopyridin-3-yl)-3-(4-(((tert-butyldimethylsilyl)oxy)methyl)phenyl)-3H-imidazo[4,5-b]pyridin-5-yl)boronic acid (510 mg, 1.07 mmol) in 1,4-dioxane (10 mL) and H₂O (2 mL) were added 2-bromo-5-cyclopropylpyridine (255 mg, 1.29 mmol), Cs₂CO₃ (1.05 g, 3.22 mmol), Pd(dppf)Cl₂ (78.5 mg, 107 μmol). The mixture was stirred at 100° C. for 2 hr under N₂. The mixture was diluted with H₂O (50 mL) and extracted with EtOAc (20 mL×3). The combined organic layers were washed with brine (50 mL), dried over anhydrous Na₂SO₄, filtered and concentrated. After purified by silica gel flash chromatography (0-30% EtOAc in petroleum ether), 3-(3-(4-(((tert-butyldimethylsilyl)oxy)methyl)phenyl)-5-(5-cyclopropylpyridin-2-yl)-3H-imidazo[4,5-b]pyridin-2-yl)pyridin-2-amine (383 mg, yield: 65% for two steps) was obtained as a light yellow solid. MS: m/z=549.3 [M+H]⁺. ¹H NMR (400 MHz, Chloroform-d) δ 8.47-8.44 (m, 2H), 8.19 (d, J=8.4 Hz, 1H), 8.15 (d, J=8.8 Hz, 1H), 8.06 (dd, J=4.8, 2 Hz, 1H), 7.52-7.48 (m, 2H), 7.43-7.38 (m, 2H), 7.33 (dd, =8, 2 Hz, 1H), 7.13 (dd, =7.6, 1.6 Hz, 1H), 6.65 (br s, 2H), 6.37 (dd, J=7.6, 4.8 Hz, 1H), 4.87 (s, 2H), 1.90-1.97 (m, 1H), 1.07-1.03 (m, 2H), 0.98 (s, 9H), 0.78-0.74 (m, 2H), 0.16 (s, 6H).

Step 3: (4-(2-(2-Aminopyridin-3-yl)-5-(5-cyclopropylpyridin-2-yl)-3H-imidazo[4,5-b]pyridin-3-yl)phenyl)methanol To a solution of 3-(3-(4-(((tert-butyldimethylsilyl)oxy)methyl)phenyl)-5-(5-cyclopropylpyridin-2-yl)-3H-imidazo[4,5-b]pyridin-2-yl)pyridin-2-amine (363 mg, 662 μmol) in THF (4 mL) was added TBAF (1M in THF, 992 μL). The mixture was stirred at 25° C. for 1 hr under N₂. The mixture was diluted with H₂O (20 mL) and extracted with EtOAc (10 mL×3). The combined organic layers were washed with brine (20 mL), dried over anhydrous Na₂SO₄, filtered and concentrated. (4-(2-(2-Aminopyridin-3-yl)-5-(5-cyclopropylpyridin-2-yl)-3H-imidazo[4,5-b]pyridin-3-yl)phenyl)methanol (268 mg) was obtained as a light yellow solid, which was used in the next step without further purification. MS: m/z=435.2. [M+H]⁺.

Step 4: 3-(3-(4-(Chloromethyl)phenyl)-5-(5-cyclopropylpyridin-2-yl)-3H-imidazo[4,5-b]pyridin-2-yl)pyridin-2-amine To a solution of (4-(2-(2-aminopyridin-3-yl)-5-(5-cyclopropylpyridin-2-yl)-3H-imidazo[4,5-b]pyridin-3-yl)phenyl)methanol (248 mg, 571 μmol) in CH₂Cl₂ (2 mL) was added SOCl₂ (204 mg, 1.71 mmol). The mixture was stirred at 25° C. for 2 hr under N₂. The reaction mixture was concentrated, 3-(3-(4-(chloromethyl)phenyl)-5-(5-cyclopropylpyridin-2-yl)-3H-imidazo[4,5-b]pyridin-2-yl)pyridin-2-amine (Intermediate 343, 258 mg) was obtained as a light yellow solid, which was used in the next step without further purification. MS: m/z=453.2, 455.1[M+H]⁺.

Intermediate 344: 3-(3-(4-(Chloromethyl)phenyl)-5-(6-(difluoromethyl)pyridin-3-yl)-3H-imidazo[4,5-b]pyridin-2-yl)pyridin-2-amine

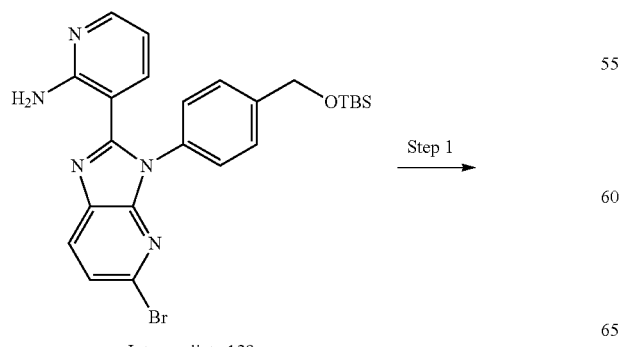

Intermediate 129

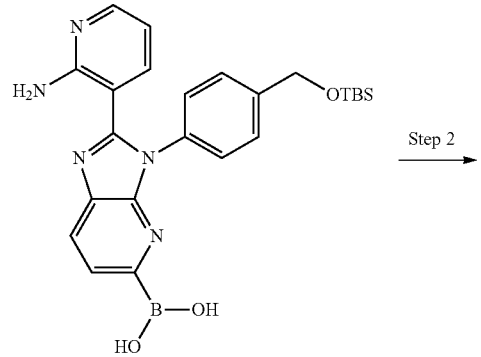

Step 2

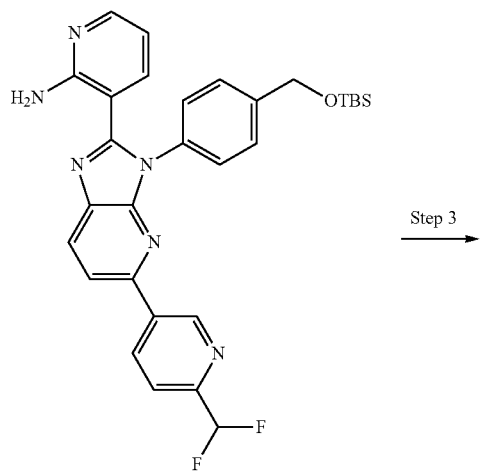

Step 3

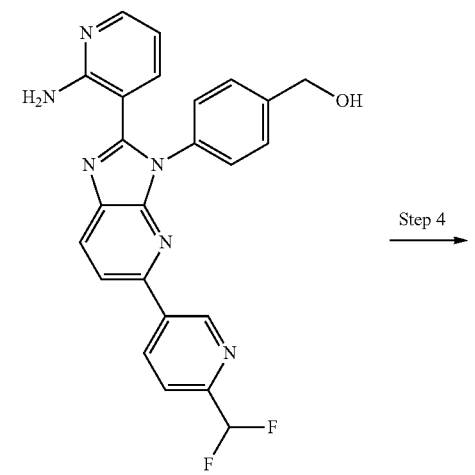

Step 4

-continued

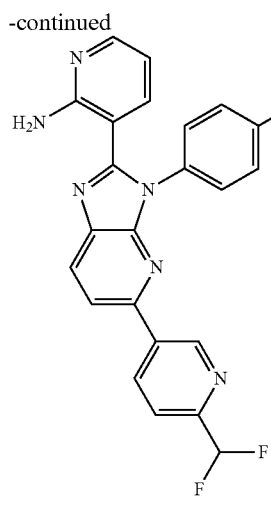

Intermediate 344

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl$_2$ (143 mg, 196 mmol) in 1,4-dioxane (5 mL) was degassed, purged with N$_2$ three times, and stirred at 90° C. for 16 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]$^+$.

Step 2: 3-(3-(4-(((tert-Butyldimethylsilyl)oxy)methyl)phenyl)-5-(6-(difluoromethyl)pyridin-3-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (465 mg, 978 μmol), 5-bromo-2-(difluoromethyl)pyridine (224 mg, 1.08 mmol), Pd(dppf)Cl$_2$ (71.6 mg, 97.8 μmol) and Cs$_2$CO$_3$ (956 mg, 2.93 mmol) in 1,4-dioxane (5 mL) and H$_2$O (1 mL) was degassed, purged with N$_2$ three times, and stirred at 80° C. for 16 hr under N$_2$ atmosphere. The reaction mixture was poured into H$_2$O (20 mL) and extracted with EtOAc (30 mL×3). The combined organic layers were dried over anhydrous Na$_2$SO$_4$, filtered and concentrated under reduced pressure. After purified by silica gel flash chromatography (Eluent of 0%~30% EtOAc in petroleum ether), 3-(3-(4-(((tert-butyldimethylsilyl)oxy)methyl)phenyl)-5-(6-(difluoromethyl)pyridin-3-yl)-3H-imidazo[4,5-b]pyridin-2-yl)pyridin-2-amine (402 mg, yield: 74% for two steps) was obtained as a brown solid. MS: m/z=559.2 [M+H]$^+$. $^1$H NMR (400 MHz, Dimethysulfoxide-d$_6$) δ 9.32 (s, 1H), 8.64-8.46 (m, 1H), 8.36 (d, J=8.4 Hz, 1H), 8.15 (d, J=8.4 Hz, 1H), 8.05-7.92 (m, 1H), 7.79 (d, J=8.0 Hz, 1H), 7.52-7.48 (m, 4H), 7.28-7.17 (m, 1H), 7.16-6.83 (m, 3H), 6.40 (dd, J=7.6, 4.8 Hz, 1H), 4.83 (s, 2H), 0.93 (s, 9H), 0.11 (s, 6H). $^{19}$F NMR (400 MHz, Dimethysulfoxide-d$_6$) δ −115.381.

Step 3: (4-(2-(2-Aminopyridin-3-yl)-5-(6-(difluoromethyl)pyridin-3-yl)-3H-imidazo[4,5-b]pyridin-3-yl)phenyl)methanol To a solution of 3-(3-(4-(((tert-butyldimethylsilyl)oxy)methyl)phenyl)-5-(6-(difluoromethyl)pyridin-3-yl)-3H-imidazo[4,5-b]pyridin-2-yl)pyridin-2-amine (402 mg, 720 μmol) in THF (5 mL) was added TBAF (2 mL, 1 M in THF). The mixture was stirred at 25° C. for 1 hr. The reaction mixture was quenched with H$_2$O (10 mL) and extracted with EtOAc (20 mL×3). The combined organic layers were washed with brine (20 mL×2), dried over Na$_2$SO$_4$, filtered and concentrated under reduced pressure. (4-(2-(2-Aminopyridin-3-yl)-5-(6-(difluoromethyl)pyridin-3-yl)-3H-imidazo[4,5-b]pyridin-3-yl)phenyl)methanol (365 mg) was obtained as a brown solid. MS: m/z=445.1 [M+H]$^+$.

Step 4: 3-(3-(4-(Chloromethyl)phenyl)-5-(6-(difluoromethyl)pyridin-3-yl)-3H-imidazo[4,5-b]pyridin-2-yl)pyridin-2-amine To a solution of (4-(2-(2-aminopyridin-3-yl)-5-(6-(difluoromethyl)pyridin-3-yl)-3H-imidazo[4,5-b]pyridin-3-yl)phenyl)methanol (365 mg, 821 μmol) in CH$_2$Cl$_2$ (5 mL) was added SOCl$_2$ (2 mL). The mixture was stirred at 40° C. for 2 hr. The reaction was concentrated under reduced pressure to give 3-(3-(4-(chloromethyl)phenyl)-5-(6-(difluoromethyl)pyridin-3-yl)-3H-imidazo[4,5-b]pyridin-2-yl)pyridin-2-amine (Intermediate 344, 405 mg, HCl salt) as a brown solid. MS: m/z=463.2, 465.2 [M+H]$^+$.

Intermediate 345: 3-(3-(4-(Chloromethyl)phenyl)-5-(6-(trifluoromethyl)pyridin-3-yl)-3H-imidazo[4,5-b]pyridin-2-yl)pyridin-2-amine

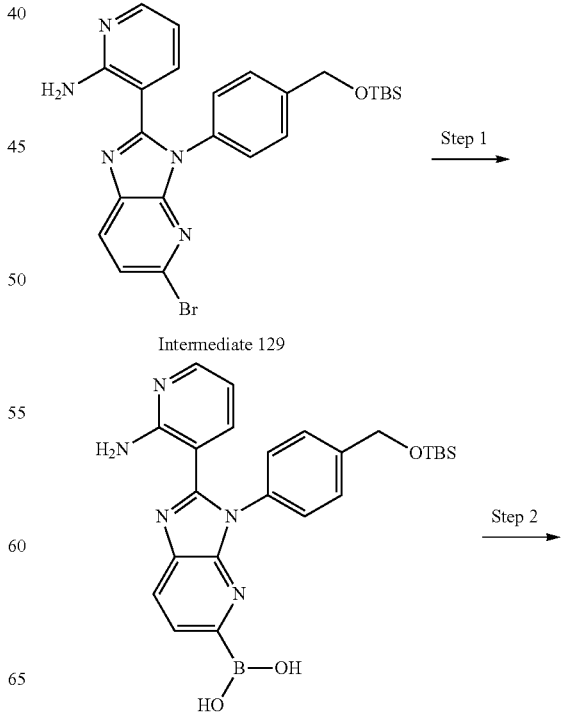

Intermediate 129

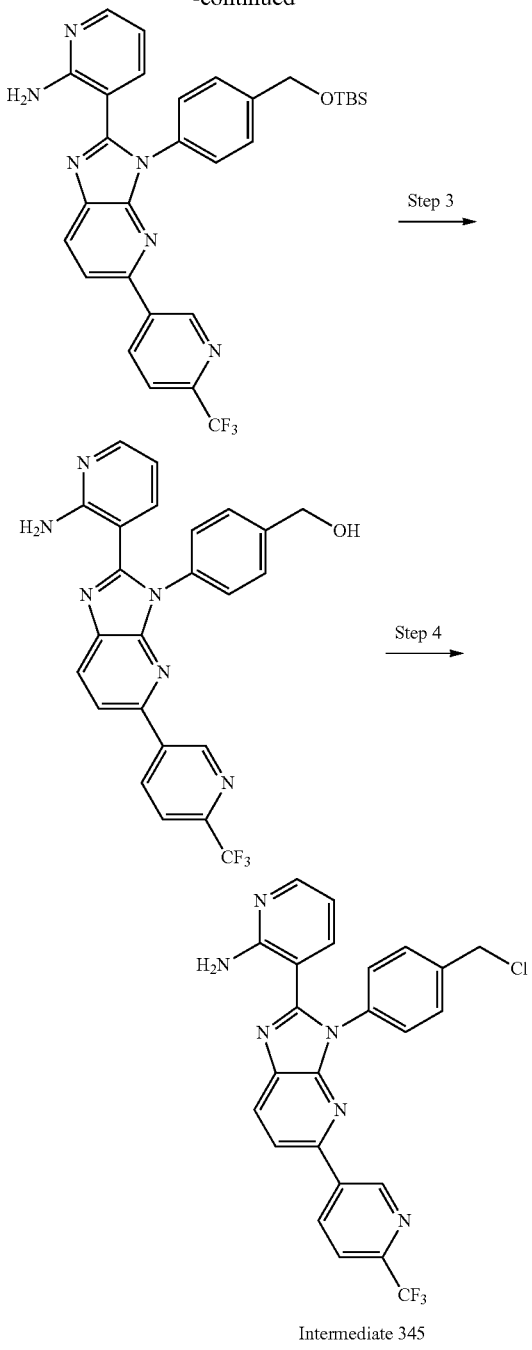

Intermediate 345

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (1 g, 1.96 mmol), 4,4,4',4',5,5,5',5'-octamethyl-2,2'-bi(1,3,2-dioxaborolane) (995 mg, 3.92 mmol), KOAc (577 mg, 5.88 mmol) and Pd(dppf)Cl₂ (143 mg, 196 mmol) in 1,4-dioxane (5 mL) was degassed, purged with N₂ three times, and stirred at 90° C. for 16 hr under N₂ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]⁺.

Step 2: 3-(3-(4-(((Tert-butyldimethylsilyl)oxy)methyl)phenyl)-5-(6-(trifluoromethyl)pyridin-3-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (465 mg, 978 µmol), 5-bromo-2-(trifluoromethyl)pyridine (265 mg, 1.17 mmol), Pd(dppf)Cl₂ (71.6 mg, 97.8 µmol) and Cs₂CO₃ (956 mg, 2.93 mmol) in 1,4-dioxane (5 mL) and H₂O (1 mL) was degassed, purged with N₂ three times, and stirred at 80° C. for 16 hr under N2 atmosphere. The reaction mixture was poured into H₂O (20 mL) and extracted with EtOAc (20 mL×3). The combined organic layers were dried over anhydrous Na₂SO₄, filtered and concentrated under reduced pressure. After purified by silica gel flash chromatography (Eluent of 0%~27% EtOAc in petroleum ether), 3-(3-(4-(((tert-butyldimethylsilyl)oxy)methyl)phenyl)-5-(6-(trifluoromethyl)pyridin-3-yl)-3H-imidazo[4,5-b]pyridin-2-yl)pyridin-2-amine (365 mg, yield: 58% for two steps) was obtained as a brown solid. MS: m/z=577.2 [M+H]⁺. ¹H NMR (400 MHz, Dimethysulfoxide-d₆) δ 9.40 (s, 1H), 8.76-8.51 (m, 1H), 8.38 (d, J=8.4 Hz, 1H), 8.20 (d, J=8.4 Hz, 1H), 8.09-7.90 (m, 2H), 7.52-7.48 (m, 4H), 7.28-7.15 (m, 1H), 7.03 (br s, 2H), 6.40 (dd, J=7.6, 5.6 Hz, 1H), 4.83 (s, 2H), 0.93 (s, 9H), 0.11 (s, 6H). ¹⁹F NMR (400 MHz, Dimethysulfoxide-d₆) δ −66.315.

Step 3: (4-(2-(2-Aminopyridin-3-yl)-5-(6-(trifluoromethyl)pyridin-3-yl)-3H-imidazo[4,5-b]pyridin-3-yl)phenyl)methanol To a solution of 3-(3-(4-(((tert-butyldimethylsilyl)oxy)methyl)phenyl)-5-(6-(trifluoromethyl)pyridin-3-yl)-3H-imidazo[4,5-b]pyridin-2-yl)pyridin-2-amine (326 mg, 565 gmol) in THF (3 mL) was added TBAF (1 mL, 1 M in THF). The mixture was stirred at 25° C. for 0.5 hr. The reaction mixture was quenched with H₂O (10 mL) and extracted with EtOAc (20 mL×3). The combined organic layers were washed with brine (20 mL×2), dried over Na₂SO₄, filtered and concentrated under reduced pressure to give (4-(2-(2-aminopyridin-3-yl)-5-(6-(trifluoromethyl)pyridin-3-yl)-3H-imidazo[4,5-b]pyridin-3-yl)phenyl)methanol (263 mg) as a brown solid. MS: m/z=463.2 [M+H]⁺.

Step 4: 3-(3-(4-(Chloromethyl)phenyl)-5-(6-(trifluoromethyl)pyridin-3-yl)-3H-imidazo[4,5-b]pyridin-2-yl)pyridin-2-amine To a solution of (4-(2-(2-aminopyridin-3-yl)-5-(6-(trifluoromethyl)pyridin-3-yl)-3H-imidazo[4,5-b]pyridin-3-yl)phenyl)methanol (263 mg, 569 µmol) in CH₂Cl₂ (2 mL) was added SOCl₂ (1 mL). The mixture was stirred at 25° C. for 0.5 hr. The reaction was concentrated under reduced pressure to give 3-(3-(4-(chloromethyl)phenyl)-5-(6-(trifluoromethyl)pyridin-3-yl)-3H-imidazo[4,5-b]pyridin-2-yl)pyridin-2-amine (Intermediate 345, 276 mg, HCl salt) as a yellow solid. MS: m/z=481.1, 483.1 [M+H]⁺.

Intermediate 346: 3-(3-(4-(Chloromethyl)phenyl)-5-(5-ethylpyridin-2-yl)-3H-imidazo[4,5-b]pyridin-2-yl)pyridin-2-amine

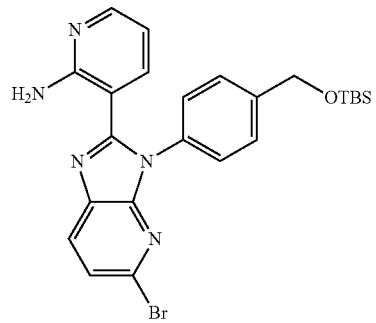

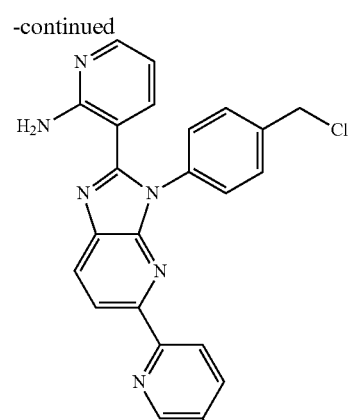

Intermediate 346

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (600 mg, 1.18 mmol), 4,4,4',4',5,5,5',5'-octamethyl-2,2'-bi(1,3,2-dioxaborolane) (596 mg, 2.35 mmol), KOAc (346 mg, 3.53 mmol) and Pd(dppf)Cl$_2$ (86.0 mg, 118 μmol) in 1,4-dioxane (6 mL) was degassed, purged with N$_2$ three times, and stirred at 90° C. for 2 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step without work-up and purification. MS: m/z=476.1 [M+H]$^+$.

Step 2: 3-(3-(4-(((tert-Butyldimethylsilyl)oxy)methyl)phenyl)-5-(5-ethylpyridin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (558 mg, 1.17 mmol), 2-bromo-5-ethylpyridine (262 mg, 1.41 mmol), Pd(dppf)Cl$_2$ (85.9 mg, 117 μmol) and Cs$_2$CO$_3$ (1.15 g, 3.52 mmol) in 1,4-dioxane (6 mL) and H$_2$O (1 mL) was degassed, purged with N$_2$ three times, and stirred at 80° C. for 5 hr under N$_2$ atmosphere. The reaction mixture was quenched with H$_2$O (20 mL) and extracted with CH$_2$Cl$_2$ (25 mL×2). The combined organic layers were washed with brine (30 mL), dried over Na$_2$SO$_4$, filtered and concentrated under reduced pressure. After purified by silica gel flash chromatography (Eluent of 15%-32% EtOAc in petroleum ether), 3-(3-(4-(((tert-butyldimethylsilyl)oxy)methyl)phenyl)-5-(5-ethylpyridin-2-yl)-3H-imidazo[4,5-b]pyridin-2-yl)pyridin-2-amine (320 mg, yield: 43% for two steps) was obtained as a yellow solid. MS: m/z=537.3 [M+H]$^+$. $^1$H NMR (400 MHz, Chloroform-d) δ 8.54-8.46 (m, 2H), 8.23 (d, J=8.0 Hz, 1H), 8.16 (d, J=8.4 Hz, 1H), 8.08-8.04 (m, 1H), 7.58-7.54 (m, 1H), 7.52-7.48 (m, 2H), 7.44-7.38 (m, 2H), 7.16-7.11 (m, 1H), 6.68 (br s, 2H), 6.39-6.34 (m, 1H), 4.87 (s, 2H), 2.69 (q, J=7.6 Hz, 2H), 1.29-1.25 (m, 3H), 0.98 (s, 9H), 0.16 (s, 6H).

Step 3: (4-(2-(2-Aminopyridin-3-yl)-5-(5-ethylpyridin-2-yl)-3H-imidazo[4,5-b]pyridin-3-yl)phenyl)methanol To a solution of 3-(3-(4-(((tert-butyldimethylsilyl)oxy)methyl)phenyl)-5-(5-ethylpyridin-2-yl)-3H-imidazo[4,5-b]

pyridin-2-yl)pyridin-2-amine (320 mg, 596 μmol) in THF (5 mL) was added TBAF (1.79 mL, 1 M in THF). The mixture was stirred at 25° C. for 1 hr. The reaction mixture was quenched with H₂O (20 mL) at 25° C. and extracted with CH₂Cl₂ (25 mL×2). The combined organic layers were washed with brine (50 mL×5), dried over Na₂SO₄, filtered and concentrated under reduced pressure. After purified by triturated with EtOAc (10 mL) at 25° C. for 10 min, (4-(2-(2-aminopyridin-3-yl)-5-(5-ethylpyridin-2-yl)-3H-imidazo[4,5-b]pyridin-3-yl)phenyl)methanol (210 mg, yield: 79%) was obtained as a yellow solid. MS: m/z=423.0 [M+H]⁺. ¹H NMR (400 MHz, Dimethylsulfoxide-d₆) δ 8.53 (d, J=2.0 Hz, 1H), 8.43 (d, J=8.4 Hz, 1H), 8.28 (d, J=8.4 Hz, 1H), 8.10 (d, J=8.4 Hz, 1H), 8.00 (dd, J=4.8, 2.0 Hz, 1H), 7.74 (dd, J=8.4, 2.4 Hz, 1H), 7.53-7.49 (m, 2H), 7.47-7.44 (m, 2H), 7.23 (dd, J=7.6, 2.0 Hz, 1H), 6.95 (br s, 2H), 6.42 (dd, J=8.0, 4.8 Hz, 1H), 5.37 (br t, J=6.0 Hz, 1H), 4.61 (d, J=5.6 Hz, 2H), 2.66 (q, J=7.6 Hz, 2H), 1.21 (t, J=7.6 Hz, 3H).

Step 4: 3-(3-(4-(Chloromethyl)phenyl)-5-(5-ethylpyridin-2-yl)-3H-imidazo[4,5-b]pyridin-2-yl)pyridin-2-amine To a solution of (4-(2-(2-aminopyridin-3-yl)-5-(5-ethylpyridin-2-yl)-3H-imidazo[4,5-b]pyridin-3-yl)phenyl)methanol (210 mg, 497 μmol) in CH₂Cl₂ (5 mL) was added SOCl₂ (177 mg, 1.49 mmol). The mixture was stirred at 40° C. for 0.5 hr. The reaction was concentrated under reduced pressure to give 3-(3-(4-(chloromethyl)phenyl)-5-(5-ethylpyridin-2-yl)-3H-imidazo[4,5-b]pyridin-2-yl)pyridin-2-amine (Intermediate 346, 237 mg, HCl salt) as a yellow solid. MS: m/z=441.1, 443.1 [M+H]⁺. ¹H NMR (400 MHz, Dimethylsulfoxide-d₆) δ 8.60 (s, 1H), 8.55-8.47 (m, 1H), 8.46-8.27 (m, 2H), 8.23 (d, J=8.0 Hz, 1H), 8.13 (d, J=5.6 Hz, 1H), 7.99-7.87 (m, 2H), 7.71-7.58 (m, 4H), 6.94-6.88 (m, 1H), 4.88 (s, 2H), 2.75-2.69 (m, 2H), 1.23 (t, J=7.6 Hz, 3H).

Intermediate 347: 2-Bromo-5-(fluoromethyl)pyridine

To a solution of (6-bromopyridin-3-yl)methanol (1 g, 5.32 mmol) in CH₂Cl₂ (25 mL) was added DAST (857 mg, 5.32 mmol) at 0° C. The mixture was stirred at 0° C. for 1 hr. The reaction mixture was quenched with NaHCO₃ (30 mL) at 0° C. and extracted with CH₂Cl₂ (50 mL×2). The combined organic layers were washed with brine (50 mL), dried over Na₂SO₄, filtered and concentrated under reduced pressure. After purified by silica gel flash chromatography (Eluent of 0%~5% EtOAc in petroleum ether), 2-bromo-5-(fluoromethyl)pyridine (Intermediate 347, 300 mg, yield: 28%) was obtained as a light yellow oil. MS: m/z=189.8, 191.8 [M+H]⁺. ¹H NMR (400 MHz, Chloroform-d) δ 8.39 (s, 11H), 7.71-7.47 (m, 2H), 5.37 (d, J=47.2 Hz, 2H). ¹⁹F NMR (400 MHz, Chloroform-d) δ −211.43.

Intermediate 348: 3-(3-(4-(Chloromethyl)phenyl)-5-(5-(fluoromethyl)pyridin-2-yl)-3H-imidazo[4,5-b]pyridin-2-yl)pyridin-2-amine

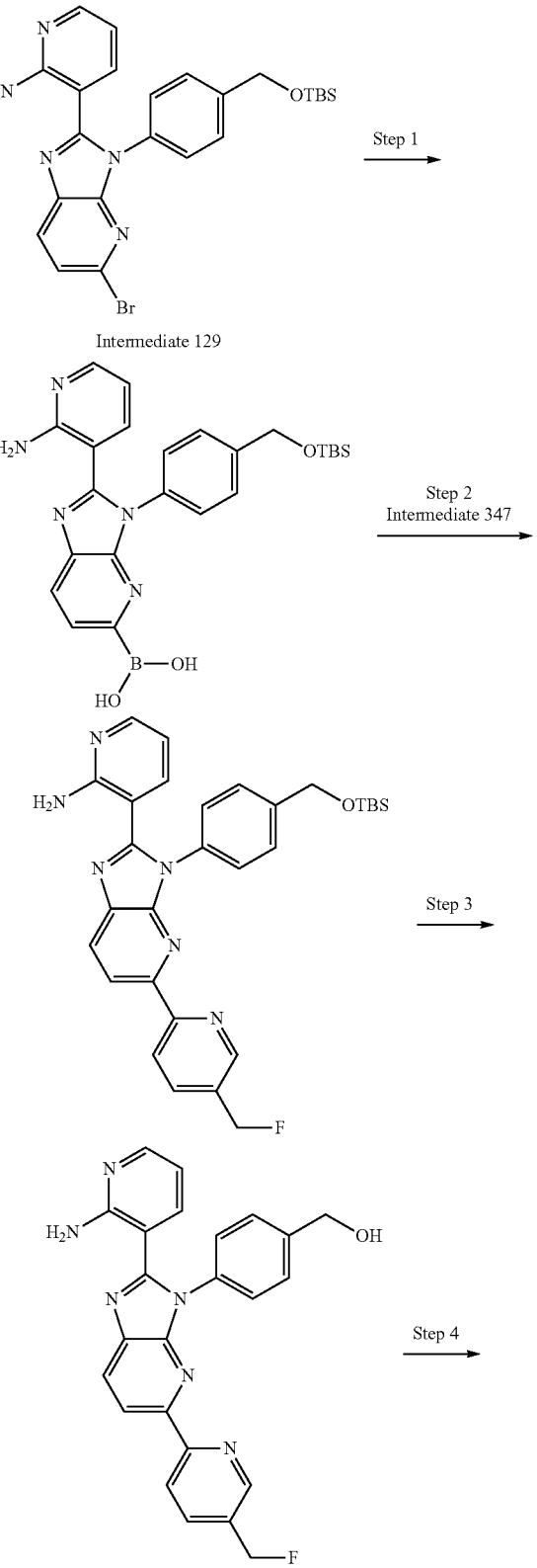

-continued

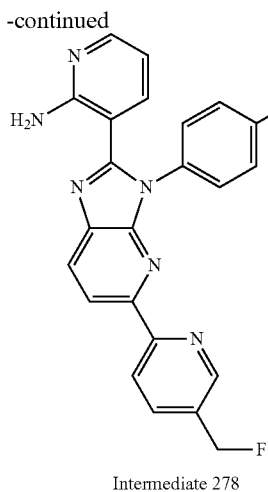

Intermediate 278

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (550 mg, 1.08 mmol), 4,4,4',4',5,5,5',5'-octamethyl-2,2'-bi(1,3,2-dioxaborolane) (547 mg, 2.15 mmol), KOAc (317 mg, 3.23 mmol) and Pd(dppf)Cl$_2$ (78.8 mg, 108 μmol) in 1,4-dioxane (6 mL) was degassed, purged with N$_2$ three times, and stirred at 90° C. for 2 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, the mixture was used for next step directly and without work-up and purification. MS: m/z=476.0 [M+H]$^+$.

Step 2: 3-(3-(4-(((tert-butyldimethylsilyl)oxy)methyl)phenyl)-5-(5-(fluoromethyl)pyridin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (512 mg, 1.08 mmol), Intermediate 347 (286 mg, 1.51 mmol), Cs$_2$CO$_3$ (1.05 g, 3.23 mmol) and Pd(dppf)Cl$_2$ (78.8 mg, 108 μmol) in 1,4-dioxane (6 mL) and H$_2$O (1 mL) was degassed, purged with N$_2$ three times, and stirred at 80° C. for 16 hr under N$_2$ atmosphere. The reaction mixture was quenched with H$_2$O (20 mL) and extracted with CH$_2$Cl$_2$ (25 mL×2). The combined organic layers were washed with brine (50 mL), dried over Na$_2$SO$_4$, filtered and concentrated under reduced pressure. After purified by silica gel flash chromatography (Eluent of 10%~32% EtOAc in petroleum ether), 3-(3-(4-(((tert-butyldimethylsilyl)oxy)methyl)phenyl)-5-(5-(fluoromethyl)pyridin-2-yl)-3H-imidazo[4,5-b]pyridin-2-yl)pyridin-2-amine (310 mg, yield: 51% for two steps) was obtained as a yellow solid. MS: m/z=541.3 [M+H]$^+$. $^1$H NMR (400 MHz, Dimethylsulfoxide-d$_6$) δ 8.73 (s, 1H), 8.49 (d, J=8.4 Hz, 1H), 8.32 (d, J=8.8 Hz, 1H), 8.21 (d, J=8.0 Hz, 1H), 8.01 (d, J=2.8 Hz, 1H), 7.95 (d, J=8.4 Hz, 1H), 7.52-7.48 (m, 4H), 7.23-7.19 (m, 1H), 7.00 (br s, 2H), 6.39 (dd, J=7.6, 5.2 Hz, 1H), 5.54 (d, J=47.6 Hz, 2H), 4.84 (s, 2H), 0.93 (s, 9H), 0.12 (s, 6H). $^{19}$F NMR (400 MHz, Dimethylsulfoxide-d$_6$) δ −206.805.

Step 3: (4-(2-(2-Aminopyridin-3-yl)-5-(5-(fluoromethyl)pyridin-2-yl)-3H-imidazo[4,5-b]pyridin-3-yl)phenyl)methanol To a solution of 3-(3-(4-(((tert-butyldimethylsilyl)oxy)methyl)phenyl)-5-(5-(fluoromethyl)pyridin-2-yl)-3H-imidazo[4,5-b]pyridin-2-yl)pyridin-2-amine (310 mg, 573 μmol) in THF (5 mL) was added TBAF (1.72 mL, 1 M in THF). The mixture was stirred at 25° C. for 1 hr. The reaction mixture was quenched with H$_2$O (20 mL) at 25° C. and extracted with CH$_2$Cl$_2$ (25 mL×2). The combined organic layers were washed with brine (50 mL×5), dried over Na$_2$SO$_4$, filtered and concentrated under reduced pressure. (4-(2-(2-Aminopyridin-3-yl)-5-(5-(fluoromethyl)pyridin-2-yl)-3H-imidazo[4,5-b]pyridin-3-yl)phenyl)methanol (140 mg) was obtained as a yellow solid. MS: m/z=427.1 [M+H]$^+$. $^1$H NMR (400 MHz, Dimethylsulfoxide-d$_6$) δ 8.73 (s, 1H), 8.49 (d, J=8.0 Hz, 1H), 8.32 (d, J=8.4 Hz, 1H), 8.22 (d, J=8.0 Hz, 1H), 8.01 (dd, J=4.8, 1.6 Hz, 1H), 7.99-7.95 (m, 1H), 7.53-7.46 (m, 4H), 7.24 (dd, J=7.6, 2.0 Hz, 1H), 6.96 (br s, 2H), 6.43 (dd, J=7.6, 4.8 Hz, 1H), 5.53 (d, J=47.6 Hz, 2H), 5.37 (br t, J=6.0 Hz, 1H), 4.62 (d, J=5.6 Hz, 2H). $^{19}$F NMR (400 MHz, Dimethylsulfoxide-d$_6$) δ −206.75.

Step 4: 3-(3-(4-(Chloromethyl)phenyl)-5-(5-(fluoromethyl)pyridin-2-yl)-3H-imidazo[4,5-b]pyridin-2-yl)pyridin-2-amine To a solution of (4-(2-(2-aminopyridin-3-yl)-5-(5-(fluoromethyl)pyridin-2-yl)-3H-imidazo[4,5-b]pyridin-3-yl)phenyl)methanol (140 mg, 328 μmol) in CH$_2$Cl$_2$ (5 mL) was added SOCl$_2$ (117 mg, 985 μmol). The mixture was stirred at 40° C. for 0.5 hr. The reaction was concentrated under reduced pressure to give 3-(3-(4-(chloromethyl)phenyl)-5-(5-(fluoromethyl)pyridin-2-yl)-3H-imidazo[4,5-b]pyridin-2-yl)pyridin-2-amine (Intermediate 348, 158 mg, HCl salt) as a yellow solid. MS: m/z=445.1, 447.1 [M+H]$^+$. $^1$H NMR (400 MHz, Dimethylsulfoxide-d$_6$) δ 8.76 (s, 1H), 8.57 (d, J=8.4 Hz, 1H), 8.46-8.35 (m, 2H), 8.28 (d, J=8.4 Hz, 1H), 8.14 (dd, J=6.4, 1.6 Hz, 1H), 8.05-8.00 (m, 1H), 7.94 (dd, J=7.6, 1.2 Hz, 1H), 7.68-7.61 (m, 4H), 6.93 (dd, J=7.2, 6.4 Hz, 1H), 5.55 (d, J=47.6 Hz, 2H), 4.88 (s, 2H). $^{19}$F NMR (400 MHz, Dimethylsulfoxide-d$_6$) δ −207.28.

Intermediate 349: 3-(3-(4-(Chloromethyl)phenyl)-5-(5-(difluoromethyl)pyridin-2-yl)-3H-imidazo[4,5-b]pyridin-2-yl)pyridin-2-amine

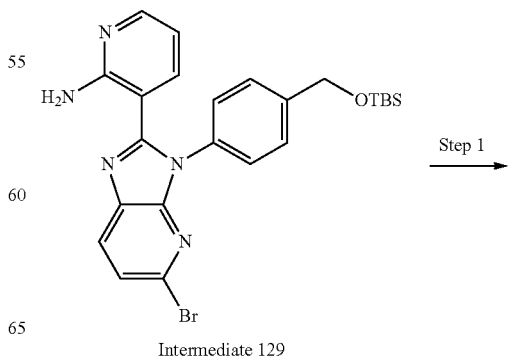

Intermediate 129

Step 1 →

1073
-continued

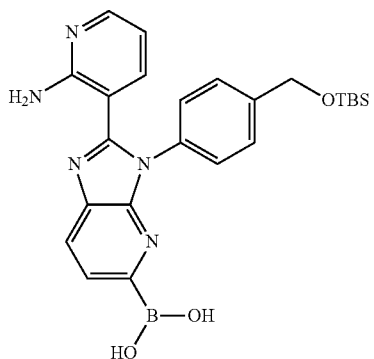

Step 2

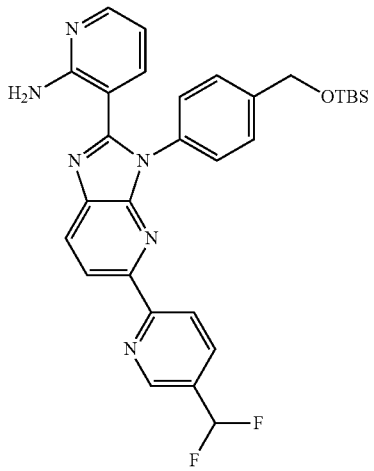

Step 3

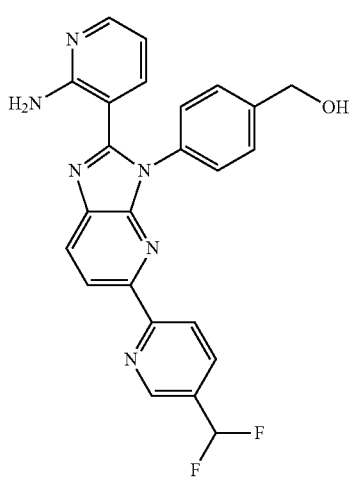

Step 4

1074
-continued

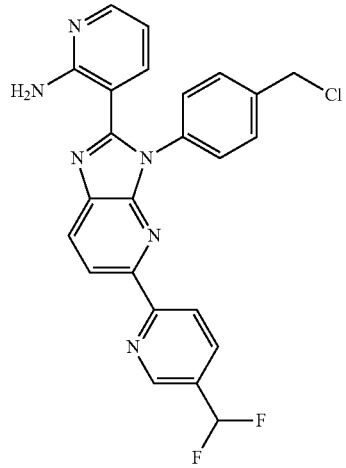

Intermediate 349

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (500 mg, 979 μmol), 4,4,4',4',5,5,5',5'-octamethyl-2,2'-bi(1,3,2-dioxaborolane) (498 mg, 1.96 mmol), KOAc (288 mg, 2.94 mmol) and Pd(dppf)Cl$_2$ (71.7 mg, 97.9 μmol) in 1,4-dioxane (5 mL) was degassed, purged with N$_2$ three times, and stirred at 90° C. for 8 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, the mixture was used for next step directly and without work-up and purification. MS: m/z=476.2 [M+H]$^+$.

Step 2: 3-(3-(4-(((tert-Butyldimethylsilyl)oxy)methyl)phenyl)-5-(5-(difluoromethyl)pyridin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (465 mg, 978 μmol), 2-bromo-5-(difluoromethyl)pyridine (203 mg, 978 μmol), Pd(dppf)Cl$_2$ (71.6 mg, 98 μmol) and Cs$_2$CO$_3$ (957 mg, 2.93 mmol) in 1,4-dioxane (10 mL) and H$_2$O (2 mL) was degassed and purged with N$_2$ three times. The mixture was stirred at 80° C. for 16 hr under N$_2$ atmosphere. The reaction mixture was quenched with H$_2$O (20 mL) and extracted with EtOAc (20 mL×3). The combined organic layers were washed with brine (60 mL), dried over Na$_2$SO$_4$, filtered and concentrated under reduced pressure. After purified by silica gel flash chromatography (Eluent of 10%~37% EtOAc in petroleum ether), 3-(3-(4-(((tert-butyldimethylsilyl)oxy)methyl)phenyl)-5-(5-(difluoromethyl)pyridin-2-yl)-3H-imidazo[4,5-b]pyridin-2-yl)pyridin-2-amine (370 mg, yield: 52% for two steps) was obtained as a brown solid. MS: m/z=559.2 [M+H]$^+$. $^1$H NMR (400 MHz, Dimethylsulfoxide-d$_6$) δ 8.87 (s, 1H), 8.51 (d, J=8.4 Hz, 1H), 8.38-8.26 (m, 2H), 8.16-8.05 (m, 1H), 8.04-7.95 (m, 1H), 7.58-7.37 (m, 5H), 7.23-7.19 (m, 1H), 7.00 (br s, 2H), 6.42-6.35 (m, 1H), 4.86-4.79 (m, 2H), 0.95-0.91 (m, 9H), 0.14-0.10 (m, 6H). $^{19}$F NMR (400 MHz, Dimethylsulfoxide-d$_6$) δ −111.254.

Step 3: (4-(2-(2-Aminopyridin-3-yl)-5-(5-(difluoromethyl)pyridin-2-yl)-3H-imidazo[4,5-b]pyridin-3-yl)phenyl)methanol To a solution of 3-(3-(4-(((tert-butyldimethylsilyl)oxy)methyl)phenyl)-5-(5-(difluoromethyl)pyridin-2-yl)-3H-imidazo[4,5-b]pyridin-2-yl)pyridin-2-amine (370 mg, 662 μmol) in THF (5 mL) was added TBAF (2 mL, 1 M in THF). The mixture was stirred at 25° C. for 1 hr. The reaction mixture was quenched with H₂O (20 mL) at 25° C. and extracted with EtOAc (20 mL×3). The combined organic layers were washed with brine (60 mL×3), dried over Na₂SO₄, filtered and concentrated under reduced pressure. The crude product was triturated with CH₂Cl₂:petroleum ether=1:10 (6 mL) at 25° C. for 10 min. (4-(2-(2-Aminopyridin-3-yl)-5-(5-(difluoromethyl)pyridin-2-yl)-3H-imidazo[4,5-b]pyridin-3-yl)phenyl)methanol (240 mg, yield: 58%) was obtained as a brown solid. MS: m/z=445.1 [M+H]⁺. ¹H NMR (400 MHz, Dimethylsulfoxide-d₆) δ 8.87 (d, J=0.8 Hz, 1H), 8.51 (d, J=8.4 Hz, 1H), 8.37-8.25 (m, 2H), 8.12 (d, J=8.0 Hz, 1H), 8.05-7.96 (m, 1H), 7.54-7.44 (m, 4H), 7.37-7.33 (m, 0.4H), 7.24 (dd, J=7.6, 2.0 Hz, 1H), 7.20-7.19 (m, 0.4H), 7.07-7.05 (m, 0.2H), 6.99-6.91 (m, 2H), 6.46-6.40 (m, 1H), 5.42-5.33 (m, 11H), 4.65-4.59 (m, 2H). ¹⁹F NMR (400 MHz, Dimethylsulfoxide-d₆) δ −111.245.

Step 4: 3-(3-(4-(Chloromethyl)phenyl)-5-(5-(difluoromethyl)pyridin-2-yl)-3H-imidazo[4,5-b]pyridin-2-yl)pyridin-2-amine To a solution of (4-(2-(2-aminopyridin-3-yl)-5-(5-(difluoromethyl)pyridin-2-yl)-3H-imidazo[4,5-b]pyridin-3-yl)phenyl)methanol (240 mg, 540 μmol) in CH₂Cl₂ (5 mL) was added SOCl₂ (118 μL, 1.62 mmol). The mixture was stirred at 40° C. for 0.5 hr. The reaction was concentrated under reduced pressure to give 3-(3-(4-(chloromethyl)phenyl)-5-(5-(difluoromethyl)pyridin-2-yl)-3H-imidazo[4,5-b]pyridin-2-yl)pyridin-2-amine (Intermediate 349, 270 mg, HCl salt) as a brown solid. MS: m/z=463.1, 465.1 [M+H]⁺.

Example 1: 6-((1-(4-(2-(2-Aminopyridin-3-yl)-3H-imidazo[4,5-b]pyridin-3-yl)benzyl)piperidin-4-yl)oxy)nicotinonitrile

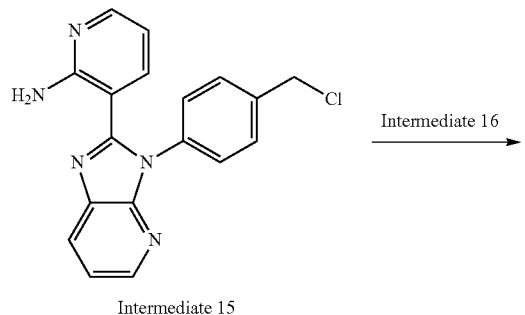

Intermediate 15

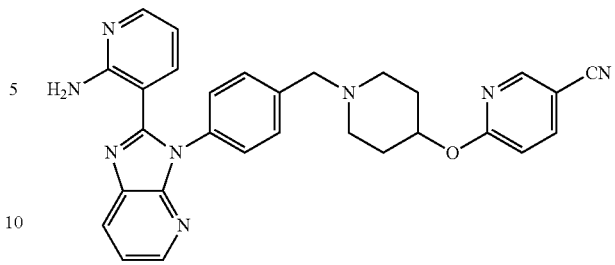

Example 1

To a solution of Intermediate 15 (50 mg, 149 μmol) in DMF (2 mL) was added NaI (3 mg, 14.9 μmol), K₂CO₃ (41 mg, 298 μmol) and Intermediate 16 (36 mg, 179 μmol). The mixture was stirred at 80° C. for 2 hr. The mixture was diluted with 20 mL H₂O and extracted with EtOAc (20 mL×2). The combined organic layers were washed with 20 mL brine, dried over Na₂SO₄, filtered, and concentrated under reduced pressure to give a residue. The crude product was purified by flash chromatography on silica gel (Eluent of 0~8% MeOH in CH₂Cl₂) to give 6-((1-(4-(2-(2-aminopyridin-3-yl)-3H-imidazo[4,5-b]pyridin-3-yl)benzyl)piperidin-4-yl)oxy)nicotinonitrile (Example 1, 24.1 mg, yield: 32%) as a light yellow solid. MS: m/z=503.1 [M+H]⁺. ¹H NMR (400 MHz, Dimethylsulfoxide-d₆) δ 8.68 (d, J=1.6 Hz, 1H), 8.32 (d, J=4.0 Hz, 1H), 8.20 (d, J=7.6 Hz, 1H), 8.13 (dd, J=8.8, 2.0 Hz, 1H), 7.98 (br d, J=3.2 Hz, 1H), 7.46 (d, J=8.0 Hz, 2H), 7.40-7.37 (m, 3H), 7.16 (d, J=6.4 Hz, 1H), 7.01-6.96 (m, 3H), 6.37 (dd, J=7.6, 4.8 Hz, 1H), 5.15-5.09 (m, 1H), 3.58 (s, 2H), 2.76-2.70 (m, 2H), 2.32-2.25 (m, 2H), 2.03-1.98 (m, 2H), 1.77-1.68 (m, 2H).

Example 2: 6-((1-(4-(2-(2-Aminopyridin-3-yl)-5-phenyl-3H-imidazo[4,5-b]pyridin-3-yl)benzyl)piperidin-4-yl)oxy)nicotinonitrile

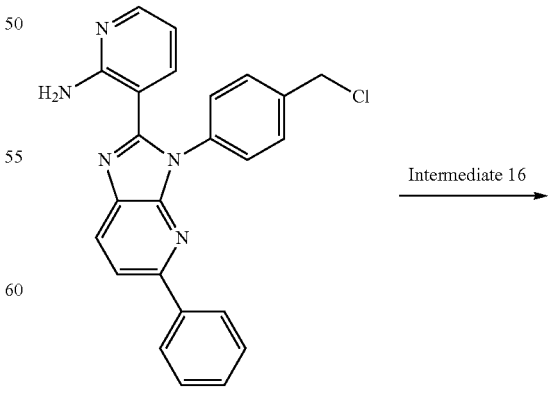

Intermediate 14

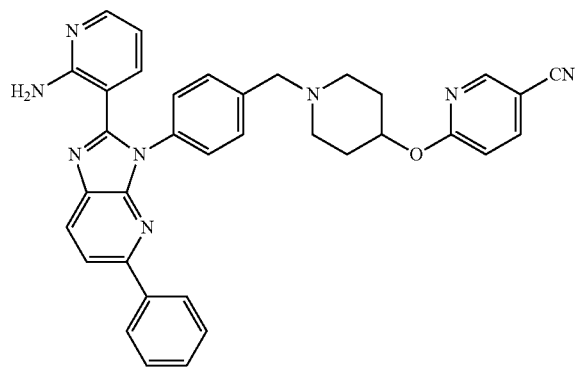

Example 2

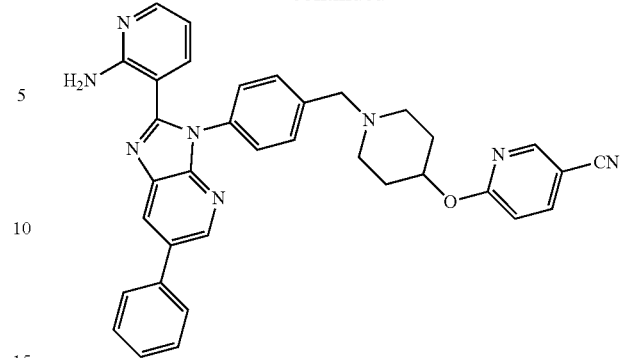

Example 3

To a solution of Intermediate 14 (200 mg, 485 μmol) and 6-(4-piperidyloxy)pyridine-3-carbonitrile (128 mg, 631 μmol) in DMF (1 mL) was added K$_2$CO$_3$ (134 mg, 971 μmol) and NaI (7.28 mg, 48.5 μmol,). The mixture was stirred at 80° C. for 2 hr. The reaction mixture was diluted with H$_2$O (5 mL) and then filtered and concentrated under reduced pressure to give a residue. The residue was purified by silica gel flash chromatography (Eluent of 0~6% MeOH in CH$_2$Cl$_2$), and then purified by prep-TLC (CH$_2$Cl$_2$: MeOH=10:1). 6-((1-(4-(2-(2-aminopyridin-3-yl)-5-phenyl-3H-imidazo[4,5-b]pyridin-3-yl)benzyl)piperidin-4-yl)oxy) nicotinonitrile (Example 2, 21.0 mg, yield: 7.5%) was obtained as a light-yellow powder. MS: m/z=579.3 [M+H]$^+$. $^1$H NMR (400 MHz, Dimethylsulfoxide-d$_6$) δ 8.68 (d, J=2.4 Hz, 1H), 8.27 (d, J=8.4 Hz, 1H), 8.13 (dd, J=8.4, 2.4 Hz, 1H), 8.04-7.97 (m, 4H), 7.50-7.44 (m, 6H), 7.43-7.35 (m, 1H), 7.15 (dd, J=8.0, 2.0 Hz, 1H), 7.02 (br s, 2H), 6.98 (d, J=8.8 Hz, 1H), 6.38 (dd, J=7.6, 4.8 Hz, 1H), 5.15-5.09 (m, 1H), 3.61 (s, 2H), 2.77-2.72 (m, 2H), 2.34-2.28 (m, 2H), 2.05-1.99 (m, 2H), 1.77-1.71 (m, 2H).

Example 3: 6-((1-(4-(2-(2-aminopyridin-3-yl)-6-phenyl-3H-imidazo[4,5-b]pyridin-3-yl)benzyl)piperidin-4-yl)oxy)nicotinonitrile Following the general procedure of Example 2, the reaction of Intermediate 20 (200 mg, 486 μmol) with Intermediate 16 (109 mg, 534 μmol) was carried out. After purified by prep-HPLC (column: Waters Xbridge 150*25 mm*5 μm; mobile phase: [water (NH$_4$HCO$_3$)-ACN]; B %: 54%-84%, 8 min), 6-((1-(4-(2-(2-aminopyridin-3-yl)-6-phenyl-3H-imidazo[4,5-b]pyridin-3-yl)benzyl)piperidin-4-yl)oxy)nicotinonitrile (Example 3, 10.2 mg, yield: 3.6%) was obtained as a yellow oil. MS: m/z=579.1 [M+H]$^+$. $^1$H NMR (400 MHz, Chloroform-d) δ 8.67 (s, 1H), 8.50-8.46 (m, 1H), 8.34 (s, 1H), 8.08-7.98 (m, 2H), 7.91 (d, J=3.6 Hz, 1H), 7.84 (dd, J=8.0, 2.0 Hz, 1H), 7.64 (d, J=7.2 Hz, 2H), 7.57-7.49 (m, 6H), 7.46-7.36 (m, 2H), 6.85 (d, J=8.8 Hz, 1H), 6.67-6.41 (m, 1H), 5.64-5.34 (m, 1H), 4.26 (s, 2H), 3.58-3.30 (m, 2H), 3.27-2.98 (m, 2H), 2.90-2.66 (m, 2H), 2.36-2.24 (m, 2H).

Example 4: 6-((1-(4-(2-(2-Aminopyridin-3-yl)-3H-imidazo[4,5-b]pyridin-3-yl)benzyl)piperidin-4-yl)oxy)picolinonitrile

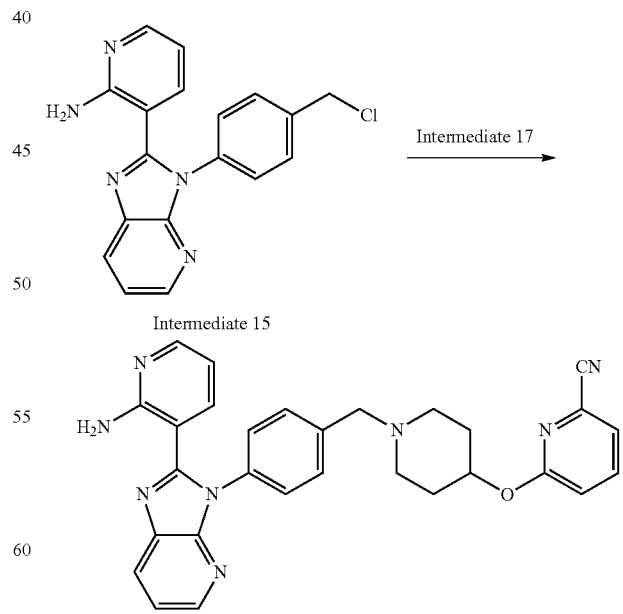

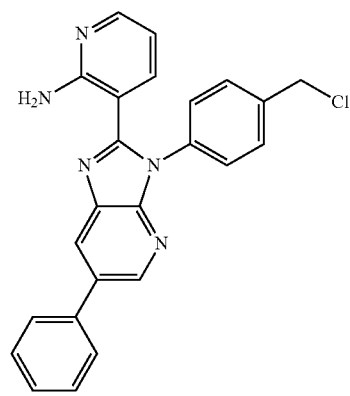

Intermediate 20

To a solution of Intermediate 15 (150 mg, 0.447 mmol) and Intermediate 17 (100 mg, 0.491 mmol) in DMF (3 mL)

was added NaI (7 mg, 45 μmol) and K₂CO₃ (123 mg, 0.893 mmol). The mixture was stirred at 80° C. for 2 hr. The mixture was diluted with H₂O (10 mL) and extracted with EtOAc (10 mL×2). The combined organic layers were washed with brine (10 mL), dried over Na₂SO₄, filtered, and concentrated under reduced pressure to give a residue. The residue was purified by prep-HPLC (column. Welch Ultimate C18 150*25 mm*5 μm; mobile phase: [water (NH₄HCO₃)-CAN]; B %: 34%-64%, 10 min), 6-((1-(4-(2-(2-Aminopyridin-3-yl)-3H-imidazo[4,5-b]pyridin-3-yl)benzyl)piperidin-4-yl)oxy)picolinonitrile (Example 4, 32.8 mg, yield: 14.6%) was obtained as a light-yellow solid. MS: m/z=503.3 [M+H]⁺. ¹H NMR (400 MHz, Dimethylsulfoxide-d₆) δ 8.33 (dd, J=4.8, 1.2 Hz, 1H), 8.20 (dd, J=8.0, 1.2 Hz, 1H), 7.99 (dd, J=4.4, 1.6 Hz, 1H), 7.91 (dd, J=8.4, 7.2 Hz, 1H), 7.62 (d, J=7.2 Hz, 1H), 7.46 d, J=8.4 Hz, 2H), 7.41-7.37 (m, 3H), 7.18-7.15 (m, 2H), 7.01 (br s, 2H), 6.38 (dd, J=7.6, 4.8 Hz, 1H), 5.08-5.00 (m, 1H), 3.59 (s, 2H), 2.76-2.69 (m, 2H), 2.36-2.28 (m, 2H), 2.05-1.97 (m, 2H), 1.77-1.68 (m, 2H).

Example 5: 2-((1-(4-(2-(2-aminopyridin-3-yl)-3H-imidazo[4,5-b]pyridin-3-yl)benzyl)piperidin-4-yl)oxy)isonicotinonitrile

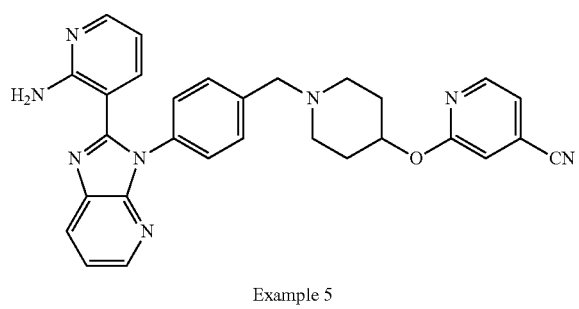

Example 5

Following the general procedure of Example 4, the reaction of Intermediate 15 (150 mg, 0.447 mmol) with Intermediate 18 (100 mg, 0.491 mmol) was carried out. After purified by prep-HPLC (column: Welch Xtimate C18 150*25 mm*5 μm; mobile phase: [water (HCl)-CAN]; B %: 0%-27%, 11 min), 2-((1-(4-(2-(2-aminopyridin-3-yl)-3H-imidazo[4,5-b]pyridin-3-yl)benzyl)piperidin-4-yl)oxy)isonicotinonitrile (Example 5, 12 mg, yield: 5.3%) was obtained as a white solid. MS: m/z=503.3 [M+H]⁺. ¹H NMR (400 MHz, Dimethylsulfoxide-d₆) δ 8.39 (d, J=5.2 Hz, 1H), 8.33 (d, J=4.4 Hz, 1H), 8.20 (d, J=8.0 Hz, 1H), 7.98 (, J=3.6 Hz, 1H), 7.45 (d, J=8.4 Hz, 2H), 7.40-7.34 (m, 5H), 7.16 (d, J=8.0 Hz, 1H), 7.00 (br s, 2H), 6.37 (dd, J=7.6, 4.8 Hz, 1H), 5.09-5.03 (m, 1H), 3.58 (s, 2H), 2.77-2.69 (m, 2H), 2.32-2.26 (m, 2H), 2.04-1.98 (m, 2H), 1.75-1.68 (m, 2H).

Example 6: 2-((1-(4-(2-(2-aminopyridin-3-yl)-3H-imidazo[4,5-b]pyridin-3-yl)benzyl)piperidin-4-yl)oxy)nicotinonitrile

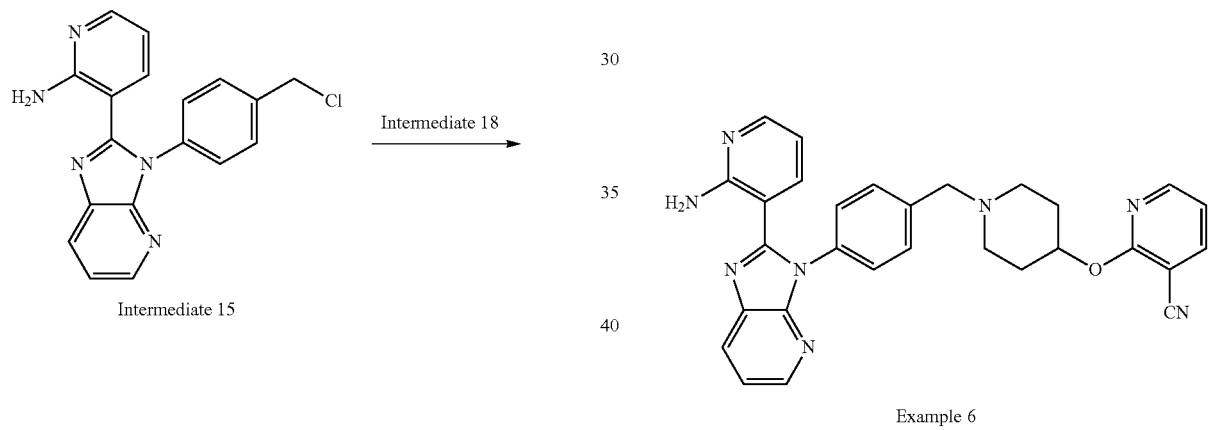

Example 6

Following the general procedure of Example 4, the reaction of Intermediate 15 (150 mg, 0.447 mmol) with Intermediate 19 (100 mg, 0.491 mmol) was carried out. After purified by prep-HPLC (column: Welch Xtimate C18 150× 25 mm 5 μm; mobile phase: [water (HCl)-ACN]; B %: 0%-27%, 11 min), 2-((1-(4-(2-(2-aminopyridin-3-yl)-3H-imidazo[4,5-b]pyridin-3-yl)benzyl)piperidin-4-yl)oxy)nicotinonitrile (Example 6, 24.5 mg, yield: 11%) was obtained as a white solid. MS: m/z=503.4 [M+H]⁺ ¹H NMR (400 MHz, Dimethylsulfoxide-d₆) δ 8.45 (d, J=4.8 Hz, 1H), 8.33 (d, J=4.8 Hz, 1H), 8.26 (d, J=7.6 Hz, 1H), 8.20 (d, J=8.0 Hz, 1H), 7.98 (d, J=4.0 Hz, 1H), 7.48 (d, J=8.4 Hz, 2H), 7.41-7.36 (m, 3H), 7.18-7.14 (m, 2H), 7.00 (br s, 2H), 6.38 (dd, J=8.0, 4.8 Hz, 1H), 5.25-5.16 (m, 1H), 3.59 (s, 2H), 2.73-2.66 (m, 2H), 2.40-2.32 (m, 2H), 2.05-1.98 (m, 2H), 1.82-1.74 (m, 2H).

Example 7: 6-((1-(4-(2-(2-Aminopyridin-3-yl)-5-phenyl-3H-imidazo[4,5-b]pyridin-3-yl)benzyl)piperidin-4-yl)oxy)picolinonitrile

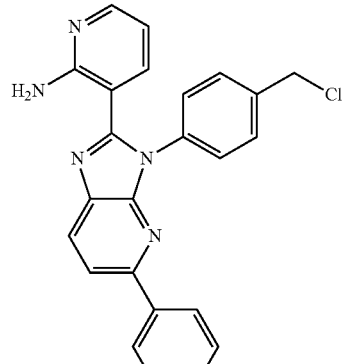

Intermediate 14

→ Intermediate 17

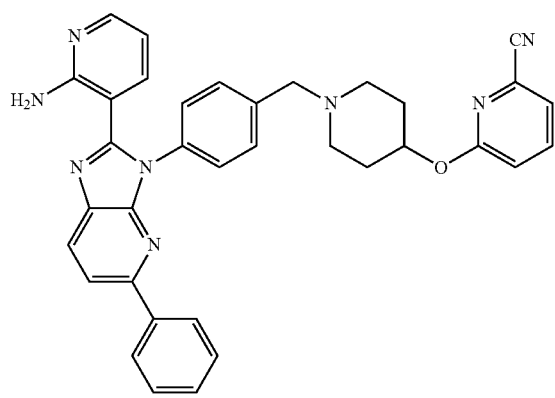

Example 7

To a solution of Intermediate 14 (150 mg, 364 μmol) and Intermediate 17 (81.4 mg, 401 μmol) in DMF (1 mL) was added NaI (5.46 mg, 36.4 μmol) and $K_2CO_3$ (101 mg, 728 μmol). The mixture was stirred at 80° C. for 2 hr. Then the mixture was purified by prep-HPLC (column: Phenomenex C18 150*25 mm*10 μm; mobile phase: [water ($NH_4HCO_3$)-ACN]; B %: 60%-90%, 8 min), 6-((1-(4-(2-(2-aminopyridin-3-yl)-5-phenyl-3H-imidazo[4,5-b]pyridin-3-yl)benzyl)piperidin-4-yl)oxy)picolinonitrile (Example 7, 11.5 mg, yield: 5.5%) as light-yellow solid. MS: m/z=579.3 [M+H]$^+$. $^1$H NMR (400 MHz, Dimethylsulfoxide-$d_6$) δ 8.27 (d, J=8.4 Hz, 1H), 8.06-7.96 (m, 4H), 7.95-7.88 (m, 1H), 7.62 (d, J=7.6 Hz, 1H), 7.52-7.43 (m, 6H), 7.41-7.39 (m, 1H), 7.19-7.12 (m, 2H), 7.02 (br s, 2H), 6.38 (dd, J=8.0, 5.2 Hz, 1H), 5.10-4.96 (m, 1H), 3.62 (s, 2H), 2.75-2.71 (m, 2H), 2.23-2.31 (m, 2H), 2.04-1.99 (m, 2H), 1.76-1.68 (m, 2H).

Example 8: 2-((1-(4-(2-(2-Aminopyridin-3-yl)-5-phenyl-3H-imidazo[4,5-b]pyridin-3-yl)benzyl)piperidin-4-yl)oxy)isonicotinonitrile


Intermediate 14

→ Intermediate 18

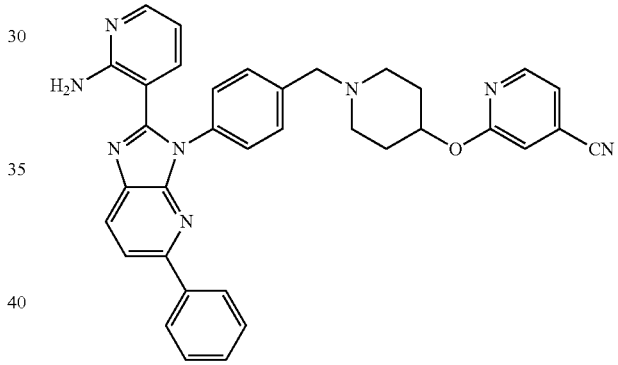

Example 8

Following the general procedure of Example 7, Intermediate 14 (100 mg, 243 μmol) with Intermediate 18 (54.3 mg, 267 μmol) was carried out. After purified by prep-HPLC (column: Phenomenex C18 150*25 mm*10 μm; mobile phase: [water ($NH_4HCO_3$)-ACN]; B %: 58%-88%, 8 min), 2-((1-(4-(2-(2-aminopyridin-3-yl)-5-phenyl-3H-imidazo[4,5-b]pyridin-3-yl)benzyl)piperidin-4-yl)oxy)isonicotinonitrile (Example 8, 18.1 mg, yield: 13%) was obtained as an off-white solid. MS: m/z=579.1 [M+H]$^+$. $^1$H NMR (400 MHz, Dimethylsulfoxide-$d_6$) δ 8.39 (d, J=5.2 Hz, 1H), 8.27 (d, J=8.4 Hz, 1H), 8.06-7.97 (m, 4H), 7.51-7.44 (m, 6H), 7.41-7.34 (m, 3H), 7.16 (d, J=7.6 Hz, 1H), 7.02 (br s, 2H), 6.38 (dd, J=8.0, 4.8 Hz, 1H), 5.10-5.03 (m, 1H), 3.61 (s, 2H), 2.77-2.73 (m, 2H), 2.34-2.24 (m, 2H), 2.05-1.99 (m, 2H), 1.77-1.68 (m, 2H).

Example 9: 2-((1-(4-(2-(2-Aminopyridin-3-yl)-5-phenyl-3H-imidazo[4,5-b]pyridin-3-yl)benzyl)piperidin-4-yl)oxy)nicotinonitrile Example 10: 6-((1-(4-(2-(2-Aminopyridin-3-yl)-6-phenyl-3H-imidazo[4,5-b]pyridin-3-yl)benzyl)piperidin-4-yl)oxy)picolinonitrile

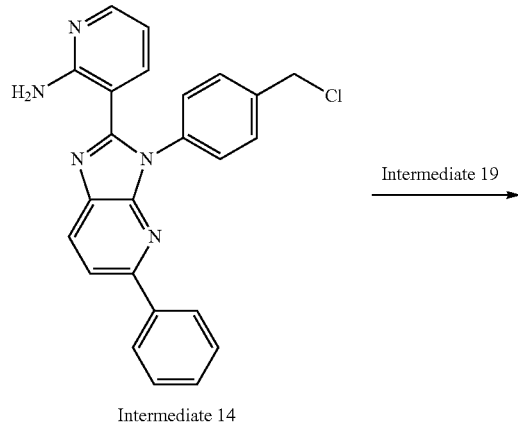

Intermediate 14

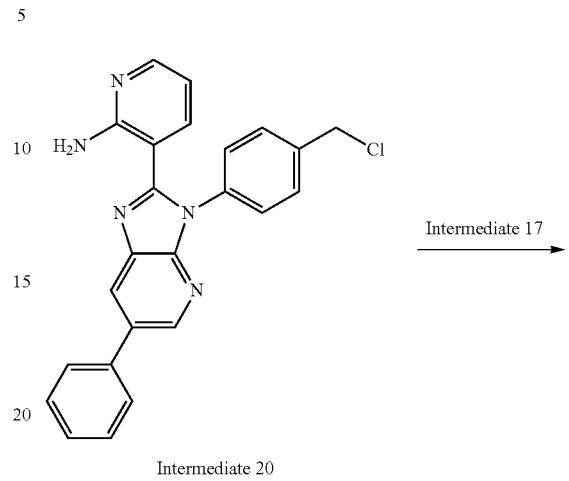

Intermediate 20

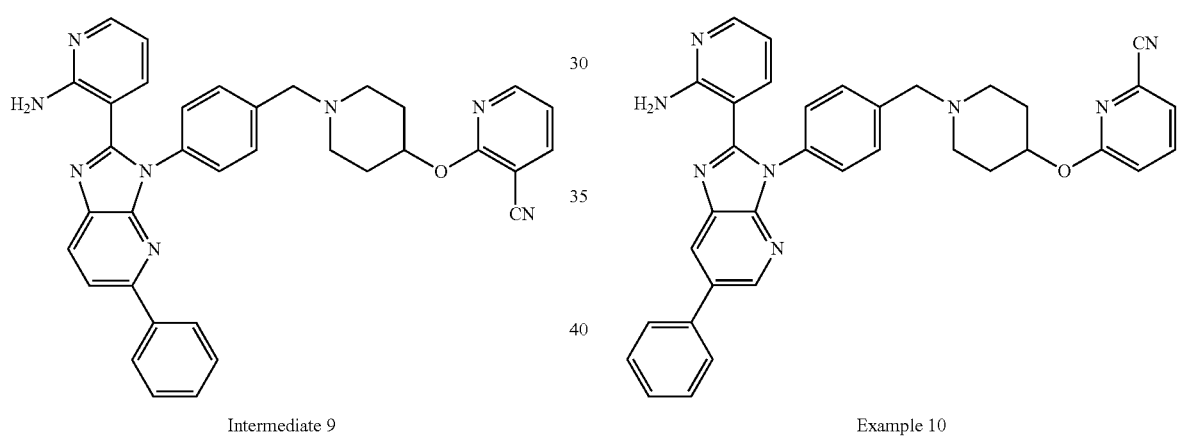

Intermediate 9

Example 10

Following the general procedure of Example 7, the reaction of Intermediate 14 (100 mg, 243 μmol) with Intermediate 19 (54.3 mg, 267 μmol) was carried out. After purified by prep-HPLC (column: Phenomenex C18 150*25 mm*10 μm; mobile phase: [water (NH$_4$HCO$_3$)-ACN]; B %: 58%-88%, 8 min), 2-((1-(4-(2-(2-aminopyridin-3-yl)-5-phenyl-3H-imidazo[4,5-b]pyridin-3-yl)benzyl)piperidin-4-yl)oxy)nicotinonitrile (Example 9, 15 mg, yield: 11%) was obtained as an off-white solid. MS: m/z=579.1 [M+H]$^+$. $^1$H NMR (400 MHz, Dimethylsulfoxide-d$_6$) δ 8.46 (dd, J=5.2, 2.0 Hz, 1H), 8.30-8.23 (m, 2H), 8.05-7.97 (m, 4H), 7.53-7.44 (m, 6H), 7.41-7.39 (m, 1H), 7.19-7.13 (m, 2H), 7.02 (br s, 2H), 6.38 (dd, J=8.0, 5.2 Hz, 1H), 5.28-5.16 (m, 1H), 3.62 (s, 2H), 2.68-2.66 (m, 2H), 2.40-2.35 (m, 2H), 2.06-2.00 (m, 2H), 1.83-1.75 (m, 2H).

Following the general procedure of Example 7, the reaction of Intermediate 20 (100 mg, 243 μmol) with Intermediate 17 (54 mg, 267 μmol) was carried out. After purified by prep-HPLC (column: Phenomenex C18 150*25 mm*10 μm; mobile phase: [water (NH$_4$HCO$_3$)-ACN]; B %: 56%-86%, 8 min), 6-((1-(4-(2-(2-aminopyridin-3-yl)-6-phenyl-3H-imidazo[4,5-b]pyridin-3-yl)benzyl)piperidin-4-yl)oxy)picolinonitrile (Example 10, 11 mg, yield: 7.8%) was obtained as a yellow solid. MS: m/z=579.3 [M+H]$^+$. $^1$H NMR (400 MHz, Dimethylsulfoxide-d$_6$) δ 8.64 (d, J=2.0 Hz, 1H), 8.47 (d, J=2.0 Hz, 1H), 8.00 (dd, J=4.8, 1.6 Hz, 1H), 7.92 (dd, J=8.0, 8.0 Hz, 1H), 7.78 (d, J=7.6 Hz, 2H), 7.62 (d, J=7.2 Hz, 1H), 7.54-7.47 (m, 4H), 7.45-7.40 (m, 3H), 7.25-7.13 (m, 2H), 7.05 (br s, 2H), 6.39 (dd, J=7.6, 4.8 Hz, 1H), 5.09-5.01 (m, 1H), 3.60 (s, 2H), 2.76-2.70 (m, 2H), 2.37-2.29 (m, 2H), 2.07-1.99 (m, 2H), 1.77-1.68 (m, 2H).

Example 11: 2-((1-(4-(2-(2-Aminopyridin-3-yl)-6-phenyl-3H-imidazo[4,5-b]pyridin-3-yl)benzyl)piperidin-4-yl)oxy)isonicotinonitrile Example 12: 2-((1-(4-(2-(2-Aminopyridin-3-yl)-6-phenyl-3H-imidazo[4,5-b]pyridin-3-yl)benzyl)piperidin-4-yl)oxy)nicotinonitrile

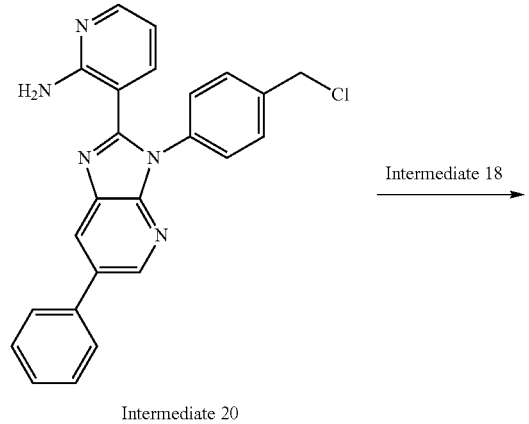

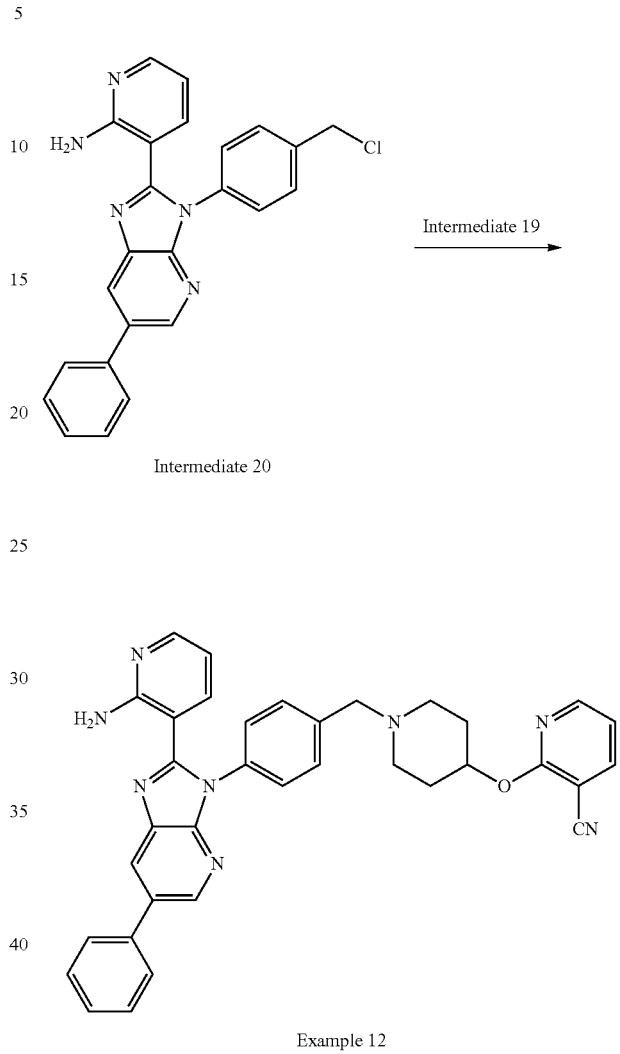

Following the general procedure of Example 7, the reaction of Intermediate 20 (100 mg, 243 μmol) with Intermediate 18 (54 mg, 267 μmol) was carried out. After purified by prep-HPLC (column: Phenomenex C18 150*25 mm*10 μm; mobile phase: [water (NH$_4$HCO$_3$)-ACN]; B %: 50%-80%, 8 min), 2-((1-(4-(2-(2-aminopyridin-3-yl)-6-phenyl-3H-imidazo[4,5-b]pyridin-3-yl)benzyl)piperidin-4-yl)oxy)isonicotinonitrile (Example 11, 10.6 mg, yield: 7.5%) was obtained as a yellow solid. MS: m/z=579.3 [M+H]$^+$. $^1$H NMR (400 MHz, Dimethylsulfoxide-d$_6$) δ 8.63 (d, J=2.0 Hz, 1H), 8.46 (d, J=2.0 Hz, 1H), 8.39 (d, J=5.2 Hz, 1H), 8.03-7.94 (m, 1H), 7.78 (d, J=7.2 Hz, 2H), 7.55-7.47 (m, 4H), 7.45-7.39 (m, 3H), 7.39-7.32 (m, 2H), 7.20 (dd, J=7.6, 1.2 Hz, 1H), 7.04 (br s, 2H), 6.39 (dd, J=7.6, 4.8 Hz, 1H), 5.11-5.03 (m, 1H), 3.61 (s, 2H), 2.84-2.72 (m, 2H), 2.39-2.19 (m, 2H), 2.03-1.95 (m, 2H), 1.76-1.65 (m, 2H).

Following the general procedure of Example 7, the reaction of Intermediate 20 (170 mg, 413 μmol) with Intermediate 19 (93 mg, 454 μmol) was carried out. After purified by prep-HPLC (column: Phenomenex C18 150*25 mm*10 μm; mobile phase: [water (NH$_4$HCO$_3$)-ACN]; B %: 52%-82%, 8 min), 2-((1-(4-(2-(2-aminopyridin-3-yl)-6-phenyl-3H-imidazo[4,5-b]pyridin-3-yl)benzyl)piperidin-4-yl)oxy)nicotinonitrile (Example 12, 15.6 mg, yield: 6.5%) was obtained as a yellow solid. MS: m/z=579.2 [M+H]$^+$. $^1$H NMR (400 MHz, Dimethylsulfoxide-d$_6$) δ 8.64 (d, J=1.8 Hz, 1H), 8.49-8.43 (m, 2H), 8.26 (dd, J=7.6, 1.6 Hz, 1H), 8.00 (dd, J=4.8, 1.6 Hz, 1H), 7.79 (d, J=7.6 Hz, 2H), 7.54-7.48 (m, 4H), 7.44-7.40 (m, 3H), 7.21-7.14 (m, 2H), 7.05 (br s, 2H), 6.39 (dd, J=7.6, 4.8 Hz, 1H), 5.26-5.16 (m, 1H), 3.60 (s, 2H), 2.75-2.63 (m, 2H), 2.39-2.30 (m, 2H), 2.09-1.97 (m, 2H), 1.83-1.74 (m, 2H).

Example 13: 4-(4-(4-(2-(2-Aminopyridin-3-yl)-3H-imidazo[4,5-b]pyridin-3-yl)benzyl)piperazin-1-yl)picolinonitrile

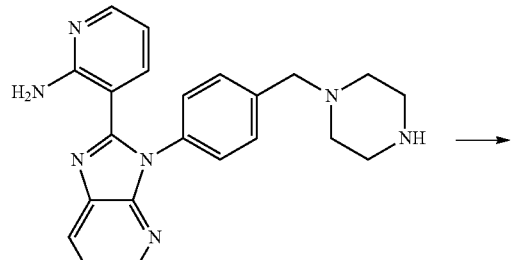

Intermediate 2

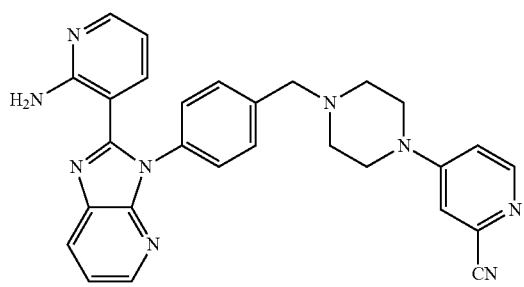

Example 13

To a solution of Intermediate 2 (200 mg, 519 μmol) in DMF (2 mL) was added DIEA (201 mg, 1.6 mmol), and 4-fluoropyridine-2-carbonitrile (76 mg, 623 μmol). The mixture was stirred at 100° C. for 2 hr. The mixture was diluted with H$_2$O (10 mL) and extracted with EtOAc (5 mL×2). The combined organic layers were washed with brine (10 mL), dried over Na$_2$SO$_4$, filtered, and concentrated under reduced pressure to give a residue. The crude product was purified by prep-HPLC (column: Phenomenex luna C18 150*25 mm*10 μm; mobile phase: [water (FA)-ACN]; B %: 0%-23%, 9 min), 4-(4-(4-(2-(2-aminopyridin-3-yl)-3H-imidazo[4,5-b]pyridin-3-yl)benzyl)piperazin-1-yl)picolinonitrile (Example 13, 9.6 mg, yield: 3.8%) was obtained as a yellow solid. MS: m/z=488.1 [M+H]$^+$. $^1$H NMR (400 MHz, Chloroform-d) δ 8.44 (dd, J=4.8, 4.2 Hz, 1H), 8.30 (d, J=6.0 Hz, 1H), 8.14 (dd, J=8.0, 1.2 Hz, 1H), 7.97-7.93 (m, 1H), 7.82 (br s, 2H), 7.56 (d, J=8.4 Hz, 2H), 7.42-7.32 (m, 3H), 7.21 (dd, J=7.6, 1.6 Hz, 1H), 7.04 (d, J=2.8 Hz, 1H), 6.80-6.74 (m, 1H), 6.40 (dd, J=7.6, 4.8 Hz, 1H), 3.67 (s, 2H), 3.44-3.39 (m, 4H), 2.68-2.62 (m, 4H).

Example 14: 5-(4-(4-(2-(2-Aminopyridin-3-yl)-3H-imidazo[4,5-b]pyridin-3-yl)benzyl)piperazin-1-yl)picolinonitrile

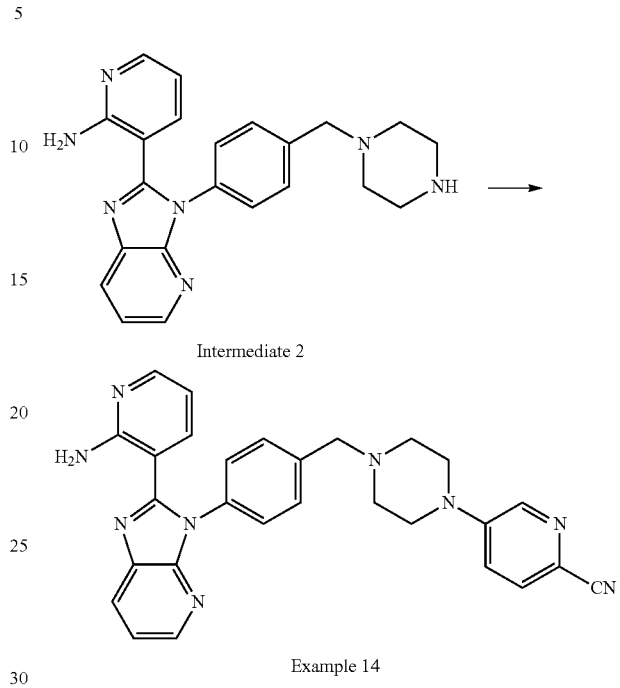

Intermediate 2

Example 14

To a solution of Intermediate 2 (200 mg, 519 μmol) and 5-fluoropyridine-2-carbonitrile (76 mg, 623 μmol) in DMF (2 mL) was added DIEA (325 μmol). The reaction mixture stirred at 100° C. for 16 hr. Then the mixture was purified by prep-HPLC (column: Waters xbridge 150*25 mm 10 um; mobile phase: [water (NH$_4$HCO$_3$)-ACN]; B %: 24%-54%, 8 min), 5-(4-(4-(2-(2-aminopyridin-3-yl)-3H-imidazo[4,5-b]pyridin-3-yl)benzyl)piperazin-1-yl)picolinonitrile (Example 14, 21.8 mg, yield: 8.3%) as a yellow solid. MS: m/z=488.2 [M+H]$^+$. $^1$H NMR (400 MHz, Dimethylsulfoxide-d$_6$) δ 8.43 (d, J=2.8 Hz, 1H), 8.34 (dd, J=4.8, 1.2 Hz, 1H), 8.21 (dd, J=8.0, 1.2 Hz, 1H), 7.99 (dd, J=4.8, 1.2 Hz, 1H), 7.75 (d, J=8.8 Hz, 1H), 7.49 (d, J=8.4 Hz, 2H), 7.42-7.34 (m, 4H), 7.17 (dd, J=7.6, 1.6 Hz, 1H), 7.01 (br s, 2H), 6.37 (dd, J=7.6, 4.8 Hz, 1H), 3.63 (s, 2H), 3.50-3.40 (m, 4H), 2.55-2.48 (m, 4H).

Example 15: 6-(4-(4-(2-(2-Aminopyridin-3-yl)-3H-imidazo[4,5-b]pyridin-3-yl)benzyl)piperazin-1-yl)picolinonitrile

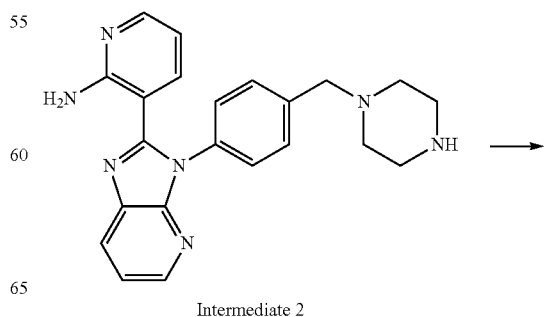

Intermediate 2

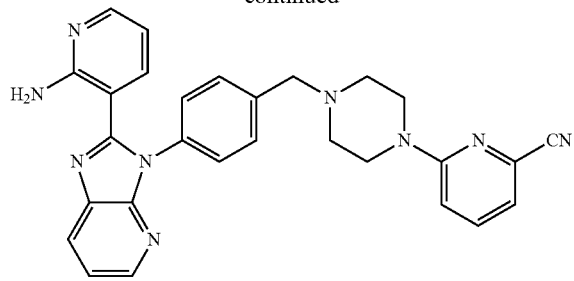

Example 15

A mixture of Intermediate 2 (200 mg, 519 μmol), 6-fluoropicolinonitrile (76 mg, 622 μmol) and DIEA (134 mg, 1.0 mmol) in DMSO (3 mL) was stirred at 120° C. for 24 hr. The reaction mixture was poured into H$_2$O (50 mL). The resulting mixture was extracted with CH$_2$Cl$_2$ (50 mL×3). The combined organic layers were dried over anhydrous Na$_2$SO$_4$, filtered, and concentrated to dryness. The residue was purified by prep-HPLC (column: Waters Xbridge BEH C18 250*50 mm*10 μm; mobile phase: [water (ammonia hydroxide v/v)-ACN]; B %: 31%-61%, 0 min), 6-(4-(4-(2-(2-aminopyridin-3-yl)-3H-imidazo[4,5-b]pyridin-3-yl)benzyl)piperazin-1-yl)picolinonitrile (Example 15, 10.5 mg, yield: 4.2%) as a light-yellow lyophilized powder. MS: m/z=488.3 [M+H]$^+$. $^1$H NMR (400 MHz, Chloroform-d) 8.41 (d, J=4.4 Hz, 1H), 8.02-8.16 (m, 2H), 7.57-7.48 (m, 3H), 7.42-7.30 (m, 3H), 7.09 (d, J=7.6 Hz, 1H), 6.97 (d, J=7.2 Hz, 1H), 6.82 (d, J=8.8 Hz, 1H), 6.63 (br s, 2H), 6.40-6.31 (m, 1H), 3.70-3.54 (m, 6H), 2.65-2.53 (m, 2H), 2.06-1.96 (m, 2H).

Example 16: 5-(4-(4-(2-(2-Aminopyridin-3-yl)-3H-imidazo[4,5-b]pyridin-3-yl)benzyl)piperazin-1-yl) nicotinonitrile

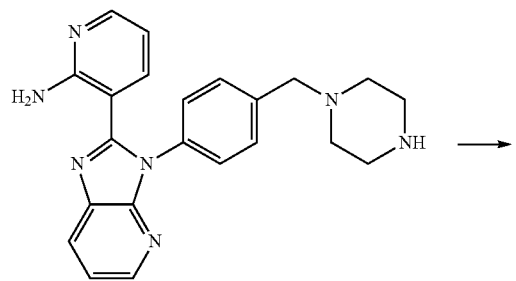

Intermediate 2

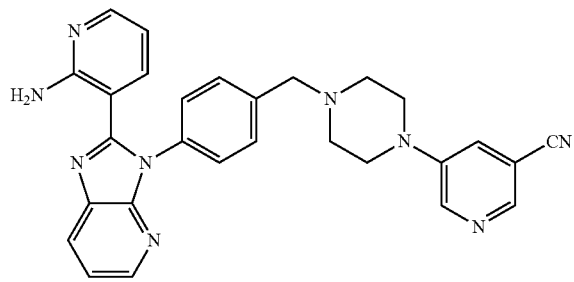

Example 16

Following the general procedure of Example 15, the reaction of Intermediate 2 (200 mg, 519 μmol) with 5-fluoronicotinonitrile (63.3 mg, 519 μmol) was carried out. After purified by prep-HPLC (column: Waters xbridge 150*25 mm 10 μm; mobile phase: [water (NH$_4$HCO$_3$)-ACN]; B %: 23%-53%, 11 min), 5-(4-(4-(2-(2-aminopyridin-3-yl)-3H-imidazo[4,5-b]pyridin-3-yl)benzyl)piperazin-1-yl)nicotinonitrile (Example 16, 5.2 mg, yield: 2.0%) was obtained as a yellow solid. MS: m/z=488.3 [M+H]$^+$. $^1$H NMR (400 MHz, Dimethylsulfoxide-d$_6$) δ 8.59 (d, J=2.8 Hz, 1H), 8.40-8.28 (m, 2H), 8.21 (dd, J=8.0, 1.2 Hz, 1H), 7.99 (dd, J=4.8, 1.6 Hz, 1H), 7.77 (s, 1H), 7.49 (d, J=8.4 Hz, 2H), 7.44-7.36 (m, 3H), 7.17 (dd, J=8.0, 2.0 Hz, 1H), 7.01 (br s, 2H), 6.38 (dd, J=7.6, 4.8 Hz, 1H), 3.62 (s, 2H), 3.37-3.33 (m, 4H), 2.58-2.52 (m, 4H).

Example 17: 2-(4-(4-(2-(2-Aminopyridin-3-yl)-3H-imidazo[4,5-b]pyridin-3-yl)benzyl)piperazin-1-yl) isonicotinonitrile

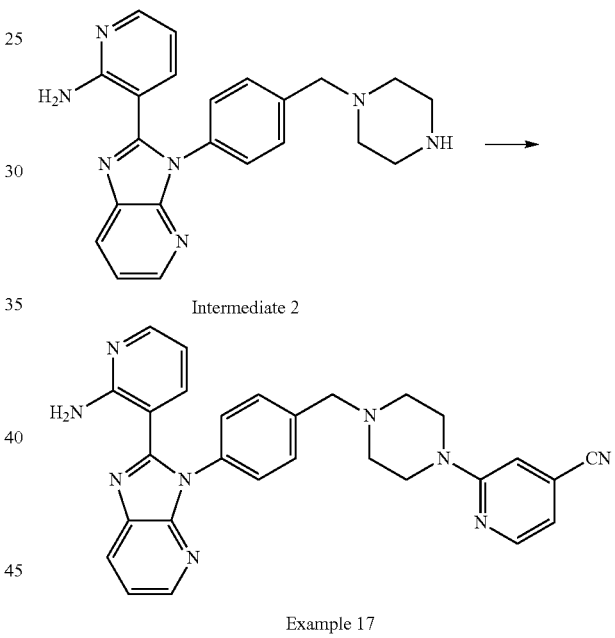

A solution of Intermediate 2 (200 mg, 519 μmol), 2-chloroisonicotinonitrile (143 mg, 1.03 mmol) and DIEA (134 mg, 1.0 mmol) in NMP (3 mL) were taken up into a microwave tube at 25° C. The sealed tube was heated at 160° C. for 1 hr under microwave. The reaction mixture was poured into H$_2$O (50 mL). The resulting mixture was extracted with CH$_2$Cl$_2$ (50 mL×3). The combined organic dried over anhydrous Na$_2$SO$_4$, filtered and concentrated to dryness. The residue was purified by prep-HPLC (column: Waters xbridge 150*25 mm 10 μm; mobile phase: [water (NH$_4$HCO$_3$)-ACN]; B %: 30%-60%, 8 min), 2-(4-(4-(2-(2-aminopyridin-3-yl)-3H-imidazo[4,5-b]pyridin-3-yl)benzyl) piperazin-1-yl)isonicotinonitrile (Example 17, 13.1 mg, yield: 5.2%) was obtained as a yellow lyophilized powder. MS: m/z=488.3 [M+H]$^+$. $^1$H NMR (400 MHz, Dimethylsulfoxide-d$_6$) δ 8.34 (dd, J=4.8, 1.2 Hz, 1H), 8.29 (d, J=5.2 Hz, 1H), 8.21 (dd, J=8.0, 1.2 Hz, 1H), 7.99 (dd, =4.8, 1.6 Hz, 1H), 7.49 (d, J=8.0 Hz, 2H), 7.42-7.37 (m, 3H), 7.31 (s, 1H), 7.16 (dd, J=8.0, 2.0 Hz, 1H), 7.01 (br s, 2H), 6.95 (d, J=5.2 Hz, 1H), 6.36 (dd, J=7.6, 4.8 Hz, 1H), 3.63-3.57 (m, 6H), 2.49-2.43 (m, 4H).

Example 18: 4-(4-(4-(2-(2-Aminopyridin-3-yl)-3H-imidazo[4,5-b]pyridin-3-yl)benzyl)piperazin-1-yl)pyrimidine-2-carbonitrile

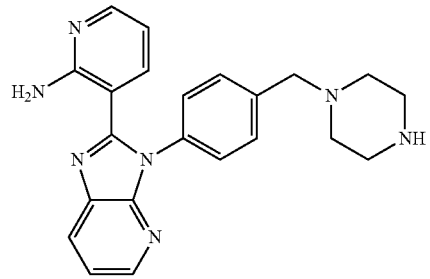

Intermediate 2

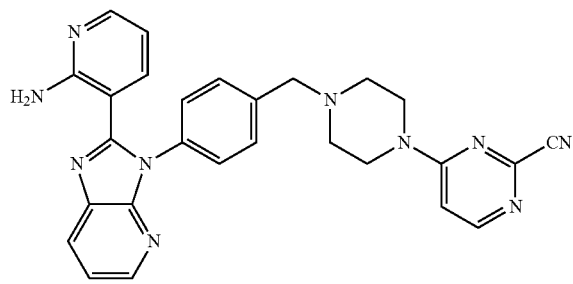

Example 18

Following the general procedure of Example 17, the reaction of Intermediate 2 (200 mg, 519 μmol) with 4-chloropyrimidine-2-carbonitrile (72.4 mg, 519 μmol) was carried out at 130° C. After purified by prep-HPLC (column: Waters xbridge 150*25 mm 10 μm; mobile phase: [water (NH$_4$HCO$_3$)-ACN]; B %: 28%-58%, 10 min), 4-(4-(4-(2-(2-aminopyridin-3-yl)-3H-imidazo[4,5-b]pyridin-3-yl)benzyl)piperazin-1-yl)pyrimidine-2-carbonitrile (Example 18, 10.5 mg, yield: 4.1%) was obtained as a brown lyophilized powder. MS: m/z=489.4 [M+H]$^+$. $^1$H NMR (400 MHz, Dimethylsulfoxide-d$_6$) δ 8.33 (dd, J=4.8, 1.6 Hz, 1H), 8.26 (d, J=6.4 Hz, 1H), 8.20 (dd, J=8.0, 1.2 Hz, 1H), 7.98 (dd, J=4.8, 2.0 Hz, 1H), 7.48 (d, J=8.0 Hz, 2H), 7.42-7.36 (m, 3H), 7.16 (dd, J=7.6, 1.6 Hz, 1H), 7.10 (d, J=6.4 Hz, 1H), 7.00 (br s, 2H), 6.36 (dd, J=7.6, 4.8 Hz, 1H), 3.76-3.63 (m, 4H), 3.62 (s, 2H), 2.49-2.43 (m, 4H).

Example 19: 6-(4-(4-(2-(2-Aminopyridin-3-yl)-3H-imidazo[4,5-b]pyridin-3-yl)benzyl)piperazin-1-yl)pyrazine-2-carbonitrile

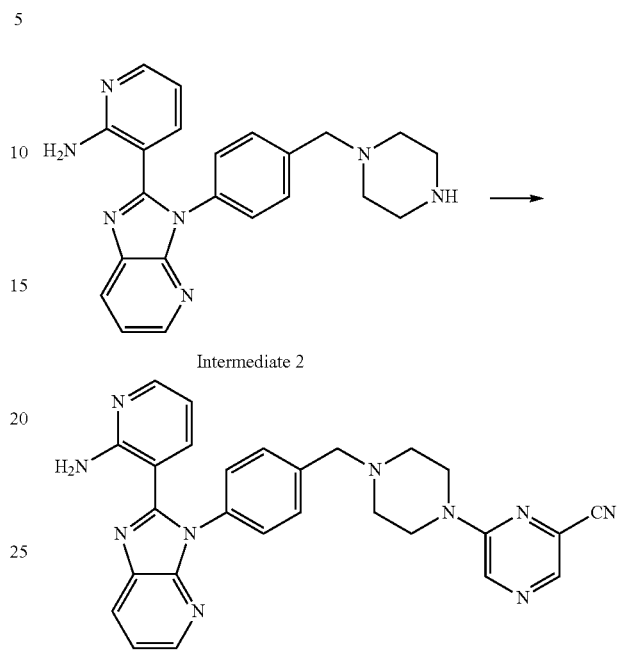

Example 19

Following the general procedure of Example 17, the reaction of Intermediate 2 (200 mg, 519 μmol) with 6-chloropyrazine-2-carbonitrile (144 mg, 1.03 mmol) was carried out. After purified by prep-HPLC (column: Waters xbridge 150*25 mm 10 μm; mobile phase: [water (NH$_4$HCO$_3$)-ACN]; B %: 27%-57%, 8 min), 6-(4-(4-(2-(2-aminopyridin-3-yl)-3H-imidazo[4,5-b]pyridin-3-yl)benzyl)piperazin-1-yl)pyrazine-2-carbonitrile (Example 19, 50.5 mg, yield: 20%) was obtained as a yellow solid. MS: m/z=489.3 [M+H]$^+$. $^1$H NMR (400 MHz, Dimethylsulfoxide-d$_6$) δ 8.65 (s, 1H), 8.34 (dd, J=4.4, 1.2 Hz, 1H), 8.30 (s, 1H), 8.21 (dd, J=8.0, 1.6 Hz, 1H), 7.99 (dd, J=5.2, 2.0 Hz, 1H), 7.49 (d, J=8.4 Hz, 2H), 7.43-7.37 (m, 3H), 7.17 (dd, J=7.6, 1.6 Hz, 1H), 7.01 (br s, 2H), 6.37 (dd, J=7.6, 4.8 Hz, 1H), 3.70-3.64 (m, 4H), 3.62 (s, 2H), 2.55-2.51 (m, 4H).

Example 20: 2-(4-(4-(2-(2-aminopyridin-3-yl)-3H-imidazo[4,5-b]pyridin-3-yl)benzyl)piperazin-1-yl)pyrimidine-4-carbonitrile

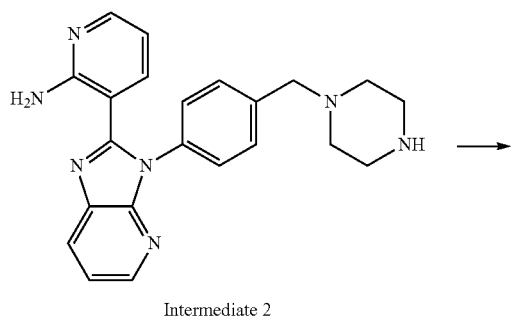

Intermediate 2

-continued

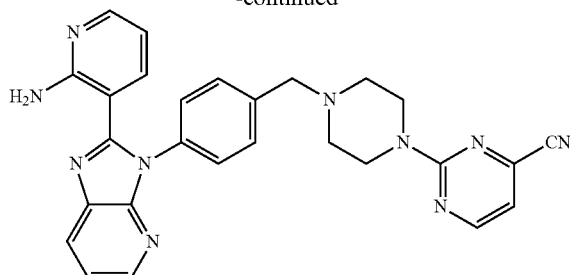

Example 20

Following the general procedure of Example 17, the reaction of Intermediate 2 (200 mg, 519 μmol) with 2-chloropyrimidine-4-carbonitrile (144 mg, 1.03 mmol) was carried out. After purified by prep-HPLC (column: Waters xbridge 150*25 mm 10 μm; mobile phase: [water (NH$_4$HCO$_3$)-ACN]; B %: 27%-57%, 8 min), 2-(4-(4-(2-(2-aminopyridin-3-yl)-3H-imidazo[4,5-b]pyridin-3-yl)benzyl)piperazin-1-yl)pyrimidine-4-carbonitrile (Example 20, 49.3 mg, yield: 19%) was obtained as a yellow solid. MS: m/z=489.3 [M+H]$^+$. $^1$H NMR (400 MHz, Dimethylsulfoxide-d$_6$) δ 8.64 (d, J=4.8 Hz, 1H), 8.33 (dd, J=4.8, 1.6 Hz, 1H), 8.21 (dd, J=8.0, 1.6 Hz, 1H), 7.99 (dd, J=4.8, 2.0 Hz, 1H), 7.48 (d, J=8.4 Hz, 2H), 7.42-7.36 (m, 3H), 7.20-7.12 (m, 2H), 7.00 (br s, 2H), 6.37 (dd, J=7.6, 4.8 Hz, 1H), 3.82-3.74 (m, 4H), 3.61 (s, 2H), 2.49-2.43 (m, 4H).

Example 21: 6-(4-(4-(2-(2-Aminopyridin-3-yl)-3H-imidazo[4,5-b]pyridin-3-yl)benzyl)piperazin-1-yl)pyrimidine-4-carbonitrile

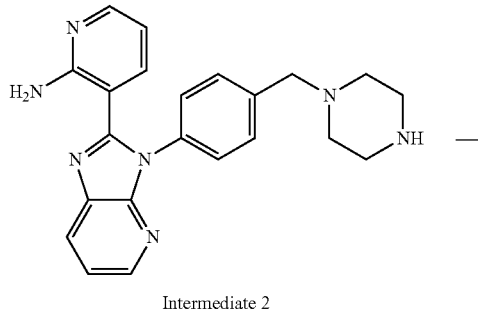

Intermediate 2

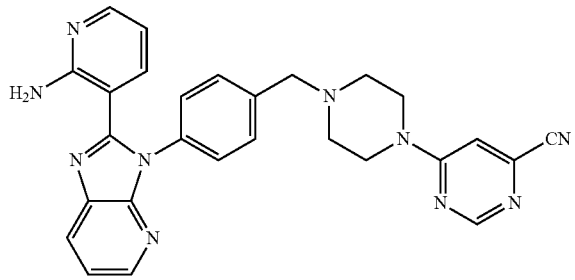

Example 21

Following the general procedure of Example 17, the reaction of Intermediate 2 (200 mg, 519 μmol) with 6-chloropyrimidine-4-carbonitrile (144 mg, 1.03 mmol) was carried out. After purified by prep-HPLC (column: Waters xbridge 150*25 mm 10 μm; mobile phase: [water (NH$_4$HCO$_3$)-ACN]; B %: 27%-57%, 8 min), 6-(4-(4-(2-(2-aminopyridin-3-yl)-3H-imidazo[4,5-b]pyridin-3-yl)benzyl)piperazin-1-yl)pyrimidine-4-carbonitrile (Example 21, 11 mg, yield: 4.3%) was obtained as a brown solid. MS: m/z=489.3 [M+H]$^+$. $^1$H NMR (400 MHz, Dimethylsulfoxide-d$_6$) δ 8.57 (s, 1H), 8.33 (d, J=4.8 Hz, 1H), 8.20 (d, J=8.0 Hz, 1H), 8.02-7.94 (m, 1H), 7.56 (s, 1H), 7.48 (d, J=8.0 Hz, 2H), 7.43-7.37 (m, 3H), 7.16 (dd, J=7.6, 1.2 Hz, 1H), 7.01 (brs, 2H), 6.36 (dd, J=7.6, 4.8 Hz, 1H), 3.98-3.68 (m, 4H), 3.64 (s, 2H), 2.58-2.52 (m, 4H).

Example 22: 6-(4-(4-(2-(2-Aminopyridin-3-yl)-3H-imidazo[4,5-b]pyridin-3-yl)benzyl)piperazin-1-yl)pyridazine-4-carbonitrile

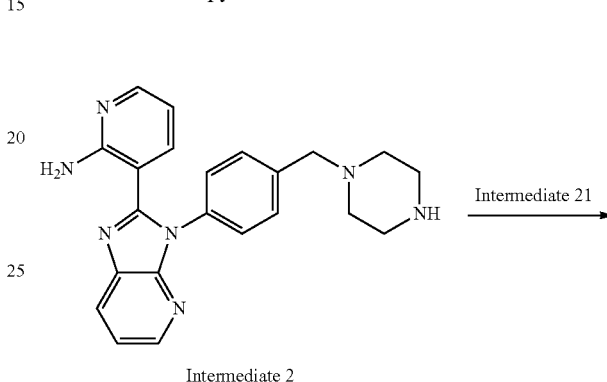

Intermediate 2

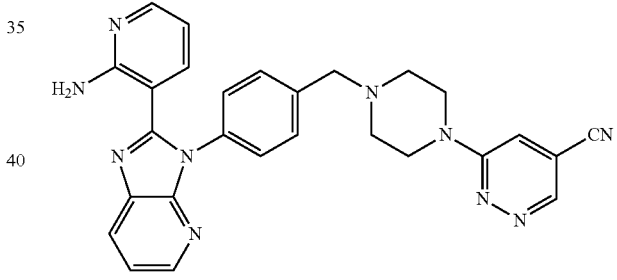

Example 22

Following the general procedure of Example 17, the reaction of Intermediate 2 (24 mg, 63 μmol) with Intermediate 21 (9 mg, 63 μmol) was carried out. After purified by prep-HPLC (column: Waters xbridge 150*25 mm 10 μm; mobile phase: [water (NH$_4$HCO$_3$)-ACN]; B %: 22%-52%, 10 min), 6-(4-(4-(2-(2-aminopyridin-3-yl)-3H-imidazo[4,5-b]pyridin-3-yl)benzyl)piperazin-1-yl)pyridazine-4-carbonitrile (Example 22, 8.5 mg, yield: 28%) was obtained as a light-gray solid. MS: m/z=489.1 [M+H]$^+$. $^1$H NMR (400 MHz, Dimethylsulfoxide-d$_6$) δ 8.83 (d, J=1.2 Hz, 1H), 8.33 (dd, J=4.8, 1.2 Hz, 1H), 8.20 (dd, J=8.0, 1.2 Hz, 1H), 7.99 (dd, J=4.8, 1.6 Hz, 1H), 7.86 (d, J=1.2 Hz, 1H), 7.49 (d, J=8.4 Hz, 2H), 7.42-7.36 (m, 3H), 7.16 (dd, J=7.8, 1.6 Hz, 1H), 7.00 (br s, 2H), 6.36 (dd, J=7.6, 4.8 Hz, 1H), 3.75-3.67 (m, 4H), 3.62 (s, 2H), 2.55-2.52 (m, 4H).

Example 23: N-(1-(4-(2-(2-aminopyridin-3-yl)-3H-imidazo[4,5-b]pyridin-3-yl)benzyl)piperidin-4-yl)-2-cyanoisonicotinamide

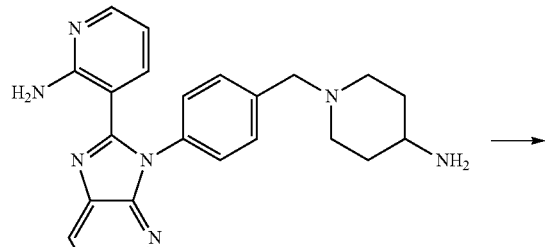

Intermediate 3

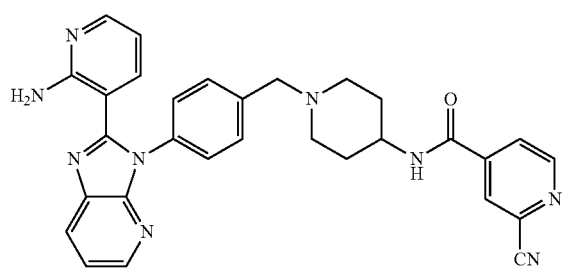

Example 23

To a solution of Intermediate 3 (200 mg, 500 μmol) in DMF (3 mL) was added HATU (381 mg, 1.00 mmol), 2-cyanopyridine-4-carboxylic acid (89 mg, 600 μmol) and DIEA (324 mg, 2.50 mmol). The mixture was stirred at 25° C. for 16 hr. The reaction mixture was poured into H$_2$O (5 mL) and extracted with EtOAc (10 mL×2). The combined organic layers were concentrated under reduced pressure to give a residue. The crude product was purified by prep-HPLC (column: Waters xbridge 150*25 mm 10 μm; mobile phase: [water (NH$_4$HCO$_3$)-ACN]; B %: 21%-51%, 11 min), N-(1-(4-(2-(2-aminopyridin-3-yl)-3H-imidazo[4,5-b]pyridin-3-yl)benzyl)piperidin-4-yl)-2-cyanoisonicotinamide (Example 23, 76 mg, yield: 29%) was obtained as a light-yellow solid. MS: m/z=530.2 [M+H]$^+$. $^1$H NMR (400 MHz, Dimethylsulfoxide-d$_6$) δ 8.90 (d, J=5.2 Hz, 1H), 8.73 (d, J=7.6 Hz, 1H), 8.37 (s, 1H), 8.33 (d, J=4.4 Hz, 1H), 8.20 (d, J=8.0 Hz, 1H), 8.07 (dd, J=4.8, 1.2 Hz, 1H), 7.99 (dd, J=4.8, 1.6 Hz, 1H), 7.45 (d, J=8.0 Hz, 2H), 7.41-7.37 (m, 3H), 7.18-7.15 (m, 1H), 7.01 (br s, 2H), 6.37 (dd, J=7.6, 4.8 Hz, 1H), 3.87-3.76 (m, 1H), 3.57 (s, 2H), 2.86 (d, J=11.6 Hz, 2H), 2.12-2.07 (m, 2H), 1.88-1.80 (m, 2H), 1.66-1.55 (m, 2H).

Example 24: N-(1-(4-(2-(2-Aminopyridin-3-yl)-3H-imidazo[4,5-b]pyridin-3-yl)benzyl)piperidin-4-yl)-6-cyanonicotinamide

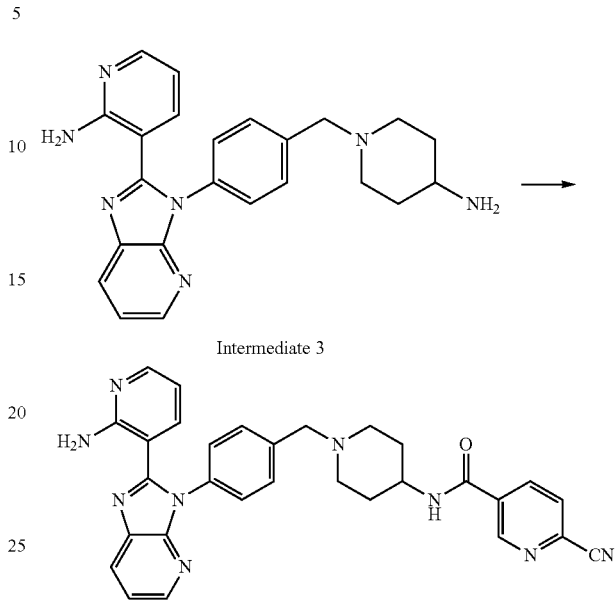

Intermediate 3

Example 24

Following the general procedure of Example 23, the reaction of Intermediate 3 (200 mg, 500 μmol) with 6-cyanopyridine-3-carboxylic acid (88.9 mg, 601 μmol) was carried out. After purified by prep-HPLC (column: Phenomenex C18 250*50 mm*10 μm; mobile phase: [water (NH$_4$HCO$_3$)-ACN]; B %: 20%-50%, 8 min), N-(1-(4-(2-(2-aminopyridin-3-yl)-3H-imidazo[4,5-b]pyridin-3-yl)benzyl)piperidin-4-yl)-6-cyanonicotinamide (Example 24, 74 mg, yield: 28%) was obtained as an off-white solid. MS: m/z=530.2 [M+H]$^+$. $^1$H NMR (400 MHz, Dimethylsulfoxide-d$_6$) δ 9.10 (s, 1H), 8.72 (d, J=7.6 Hz, 1H), 8.39 (dd, J=8.0, 2.0 Hz, 1H), 8.33 (dd, J=8.4, 1.2 Hz, 1H), 8.21 (dd, J=8.0, 1.2 Hz, 1H), 8.17 (dd, =8.0 Hz, 1H), 7.99 (dd, J=8.4, 1.6 Hz, 1H), 7.45 (d, J=8.4 Hz, 2H), 7.42-7.36 (m, 3H), 7.16 (dd, J=7.6, 2.0 Hz, 1H), 7.01 (br s, 2H), 6.37 (dd, J=7.6, 4.8 Hz, 1H), 3.88-3.76 (m, 1H), 3.57 (s, 2H), 2.86 (d, J=11.6 Hz, 2H), 2.09 (t, J=11.6 Hz, 2H), 1.85 (d, J=10.0 Hz, 2H), 1.66-1.56 (m, 2H).

Example 25: N-(1-(4-(2-(2-Aminopyridin-3-yl)-3H-imidazo[4,5-b]pyridin-3-yl)benzyl)piperidin-4-yl)-5-cyanopicolinamide

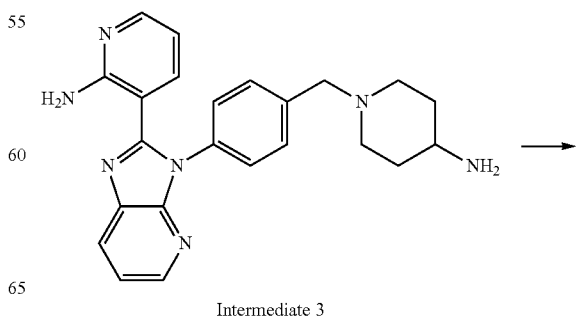

Intermediate 3

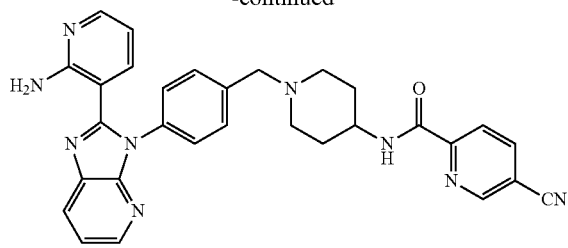

Example 25

Following the general procedure of Example 23, the reaction of Intermediate 3 (200 mg, 500 μmol) with 5-cyanopyridine-2-carboxylic acid (89 mg, 600 μmol) was carried out. After purified by prep-HPLC (column: Phenomenex luna C18 150*25 mm*10 μm; mobile phase: [water (NH$_4$HCO$_3$)-ACN]; B %: 22%-52%, 8 min), N-(1-(4-(2-(2-aminopyridin-3-yl)-3H-imidazo[4,5-b]pyridin-3-yl)benzyl)piperidin-4-yl)-5-cyanopicolinamide (Example 25, 12.7 mg, yield: 4.8%) was obtained as an off-white solid. MS: m/z=530.1 [M+H]$^+$. $^1$H NMR (400 MHz, Dimethylsulfoxide-d$_6$) δ 9.10 (d, J=1.6 Hz, 1H), 8.80 (d, J=8.4 Hz, 1H), 8.51 (dd, J=8.0, 2.0 Hz, 1H), 8.33 (dd, J=4.8, 1.2 Hz, 1H), 8.24-8.13 (m, 2H), 7.99 (dd, J=4.8, 1.6 Hz, 1H), 7.45 (d, J=8.4 Hz, 2H), 7.41-7.35 (m, 3H), 7.17 (dd, J=7.6, 1.6 Hz, 1H), 7.01 (brs, 2H), 6.37 (dd, J=7.6, 4.8 Hz, 1H), 3.88-3.78 (m, 1H), 3.56 (s, 2H), 2.84 (d, J=12.0 Hz, 2H), 2.15-2.05 (m, 2H), 1.80-1.70 (m, 4H).

Example 26: N-(1-(4-(2-(2-aminopyridin-3-yl)-3H-imidazo[4,5-b]pyridin-3-yl)benzyl)piperidin-4-yl)-5-cyanonicotinamide

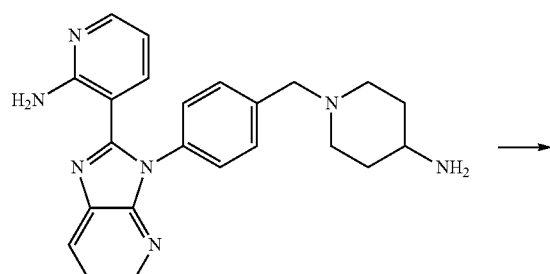

Intermediate 3

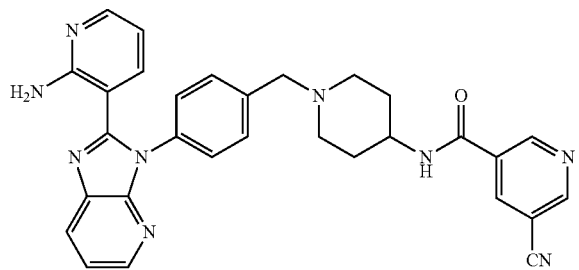

Example 28

Following the general procedure of Example 23, the reaction of Intermediate 3 (200 mg, 500 μmol) with 5-cyanopyridine-3-carboxylic acid (89 mg, 600 μmol) was carried out. After purified by prep-HPLC (column: Phenomenex Luna C18 150*25 mm*10 μm; mobile phase: [water (NH$_4$HCO$_3$)-ACN]; B %: 18%-48%, 8 min), N-(1-(4-(2-(2-aminopyridin-3-yl)-3H-imidazo[4,5-b]pyridin-3-yl)benzyl)piperidin-4-yl)-5-cyanonicotinamide (Example 26, 26.8 mg, yield: 10.1%) was obtained as a yellow solid. MS: m/z=530.2 [M+H]$^+$. $^1$H NMR (400 MHz, Dimethylsulfoxide-d$_6$) 9.21 (d, J=2.0 Hz, 1H), 9.16 (d, J=2.0 Hz, 1H), 8.70-8.58 (m, 2H), 8.33 (dd, J=4.8, 1.2 Hz, 1H), 8.21 (dd, J=8.0, 1.2 Hz, 1H), 7.99 (dd, J=4.8, 1.6 Hz, 1H), 7.46 (d, J=8.4 Hz, 2H), 7.43-7.33 (m, 3H), 7.17 (dd, J=7.6, 1.6 Hz, 1H), 7.01 (br s, 2H), 6.37 (dd, J=7.6, 4.8 Hz, 1H), 3.87-3.75 (m, 1H), 3.57 (s, 2H), 2.86 (d, J=11.6 Hz, 2H), 2.10 (t, J=11.6 Hz, 2H), 1.89-1.80 (m, 2H), 1.67-1.54 (m, 2H).

Example 27: N-(1-(4-(2-(2-Aminopyridin-3-yl)-3H-imidazo[4,5-b]pyridin-3-yl)benzyl)piperidin-4-yl)-2-cyanonicotinamide

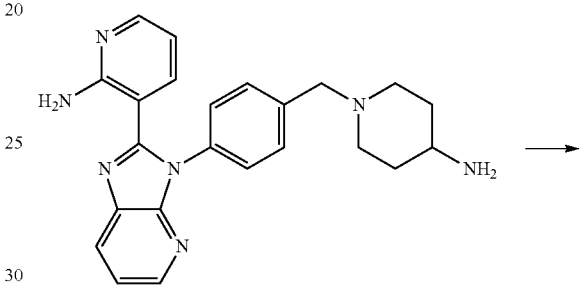

Intermediate 3

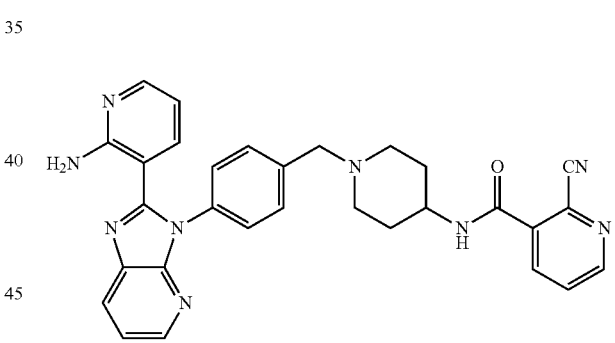

Example 27

Following the general procedure of Example 23, the reaction of Intermediate 3 (200 mg, 500 μmol) 2-cyanopyridine-3-carboxylic acid (89 mg, 600 μmol) was carried out. After purified by prep-HPLC (column: Waters xbridge 150*25 mm 10 μm; mobile phase: [water (NH$_4$HCO$_3$)-ACN]; B %: 16%-46%, 8 min), N-(1-(4-(2-(2-aminopyridin-3-yl)-3H-imidazo[4,5-b]pyridin-3-yl)benzyl)piperidin-4-yl)-2-cyanonicotinamide (Example 27, 19.8 mg, yield: 7.5%) was obtained as a yellow solid. MS: m/z=530.3 [M+H]$^+$. $^1$H NMR (400 MHz, Dimethylsulfoxide-d$_6$) δ 9.88 (s, 1H), 8.92 (dd, J=4.8, 1.6 Hz, 1H), 8.33 (dd, J=4.8, 1.2 Hz, 1H), 8.26-8.01 (m, 2H), 7.98 (dd, J=4.8, 1.6 Hz, 1H), 7.73 (dd, J=7.6, 4.8 Hz, 1H), 7.48 (d, J=8.0 Hz, 2H), 7.42-7.36 (m, 3H), 7.17 (dd, J=7.6, 1.8 Hz, 1H), 7.02 (br s, 2H), 6.37 (dd, J=7.6, 4.8 Hz, 1H), 4.36-4.24 (m, 1H), 3.59 (s, 2H), 2.99-2.89 (m, 2H), 2.61-2.56 (m, 2H), 2.14-2.03 (m, 2H), 1.67 (d, J=11.6 Hz, 2H).

Example 28: N-(1-(4-(2-(2-Aminopyridin-3-yl)-3H-imidazo[4,5-b]pyridin-3-yl)benzyl)piperidin-4-yl)-3-cyanopicolinamide

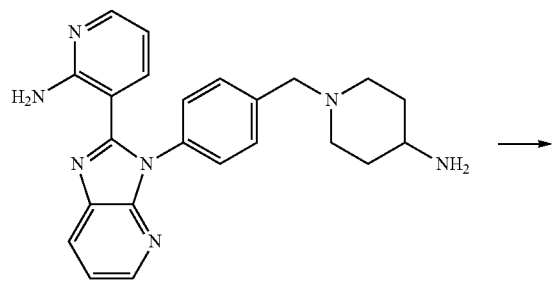

Intermediate 3

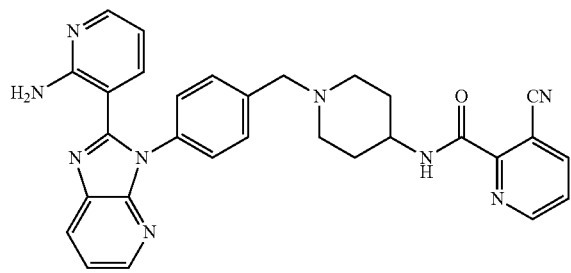

Example 28

Following the general procedure of Example 23, the reaction of 3-(3-(4-((4-aminopiperidin-1-yl)methyl)phenyl)-3H-imidazo[4,5-b]pyridin-2-yl)pyridin-2-amine (200 mg, 500 μmol) with 3-cyanopyridine-2-carboxylic acid (89 mg, 600 μmol) was carried out. After purified by prep-HPLC (column: Waters xbridge 150*25 mm 10 μm; mobile phase: [water (NH$_4$HCO$_3$)-ACN]; B %: 18%-48%, 8 min), N-(1-(4-(2-(2-aminopyridin-3-yl)-3H-imidazo[4,5-b]pyridin-3-yl)benzyl)piperidin-4-yl)-3-cyanopicolinamide (Example 28, 40.7 mg, yield: 15%) was obtained as a pink solid. MS: m/z=529.9 [M+H]$^+$. $^1$H NMR (400 MHz, Chloroform-d) δ 8.95-8.90 (m, 1H), 8.87-8.67 (m, 1H), 8.40 (dd, J=4.8, 1.2 Hz, 1H), 8.10 (dd, J=8.0, 1.2 Hz, 1H), 8.06-7.85 (m, 2H), 7.63-7.50 (m, 3H), 7.34 (d, J=8.4 Hz, 2H), 7.32-7.29 (m, 1H), 7.10 (dd, J=7.6, 1.6 Hz, 1H), 6.62 (brs, 2H), 6.35 (dd, J=7.6, 4.8 Hz, 1H), 4.58-4.44 (m, 1H), 3.63 (s, 2H), 3.08 (d, J=11.2 Hz, 2H), 2.96-2.68 (m, 2H), 2.26-2.16 (m, 2H), 1.77-1.73 (m, 2H).

Example 29: N-(1-(4-(2-(2-Aminopyridin-3-yl)-3H-imidazo[4,5-b]pyridin-3-yl)benzyl)piperidin-4-yl)-4-cyanonicotinamide

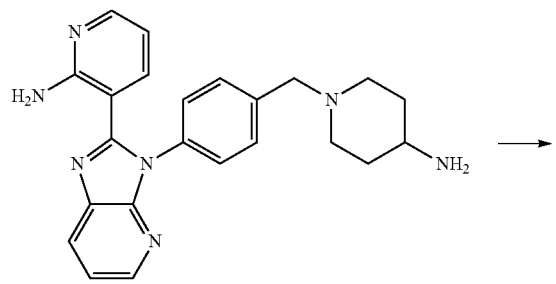

Intermediate 3

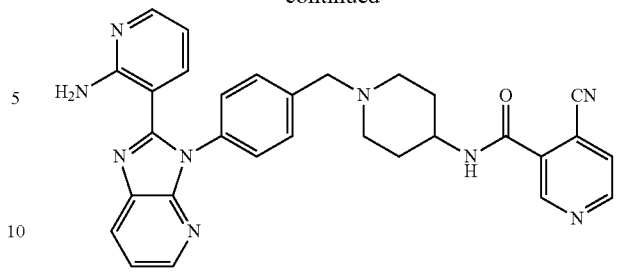

Example 29

Following the general procedure of Example 23, the reaction of Intermediate 3 (200 mg, 500 μmol) with 4-cyanopyridine-3-carboxylic acid (89 mg, 600 μmol) was carried out. After purified by prep-HPLC (column: Phenomenex C18 150*25 mm*10 μm; mobile phase: [water (NH$_4$HCO$_3$)-ACN]; B %: 14%-44%, 8 min), N-(1-(4-(2-(2-aminopyridin-3-yl)-3H-imidazo[4,5-b]pyridin-3-yl)benzyl)piperidin-4-yl)-4-cyanonicotinamide (Example 29, 40.8 mg, yield: 15%) was obtained as a yellow solid. MS: m/z=530.1 [M+H]$^+$. $^1$H NMR (400 MHz, Dimethylsulfoxide-d$_6$) δ 10.59 (s, 1H), 9.05-8.97 (m, 2H), 8.33 (dd, J=4.8, 1.2 Hz, 1H), 8.21 (dd, J=8.0, 1.2 Hz, 1H), 8.15 (d, J=5.2 Hz, 1H), 7.99 (dd, J=4.8, 1.6 Hz, 1H), 7.48 (d, J=8.4 Hz, 2H), 7.41-7.35 (m, 3H), 7.17 (dd, J=7.6, 1.6 Hz, 1H), 7.01 (br s, 2H), 6.38 (dd, J=4.6, 4.8 Hz, 1H), 4.35-4.22 (m, 1H), 3.59 (s, 2H), 2.96 (d, J=11.2 Hz, 2H), 2.64-2.53 (m, 2H), 2.08 (t, J=11.2 Hz, 2H), 1.63 (d, J=9.6 Hz, 2H).

Example 30: N-(1-(4-(2-(2-Aminopyridin-3-yl)-3H-imidazo[4,5-b]pyridin-3-yl)benzyl)piperidin-4-yl)-6-cyanopicolinamide

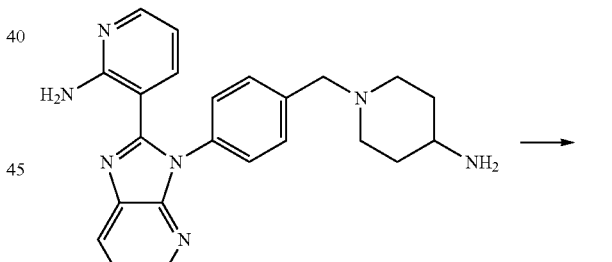

Intermediate 3

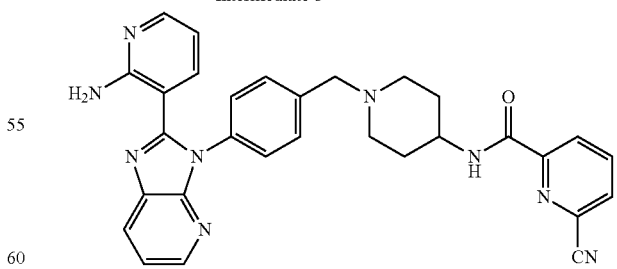

Example 30

Following the general procedure of Example 23, the reaction of Intermediate 3 (200 mg, 500 μmol) with, 6-cyanopyridine-2-carboxylic acid (89 mg, 600 μmol) was carried out. After purified by prep-HPLC (column: Phenomenex luna C18 150*25 mm*10 μm; mobile phase: [water (NH₄HCO₃)-ACN]; B %: 22%-52%, 8 min), N-(1-(4-(2-(2-aminopyridin-3-yl)-3H-imidazo[4,5-b]pyridin-3-yl)benzyl)piperidin-4-yl)-6-cyanopicolinamide (Example 30, 36.7 mg, yield: 14%) was obtained as a yellow solid. MS: m/z=530.1 [M+H]⁺. ¹H NMR (400 MHz, Dimethylsulfoxide-d₆) δ 8.71 (d, J=8.4 Hz, 1H), 8.33 (dd, J=4.8, 1.2 Hz, 1H), 8.30-8.26 (m, 1H), 8.24-8.21 (m, 2H), 8.20-8.06 (m, 1H), 7.99 (dd, J=4.8, 1.6 Hz, 1H), 7.46 (d, J=8.4 Hz, 2H), 7.42-7.36 (m, 3H), 7.17 (dd, J=7.6, 1.6 Hz, 1H), 7.01 (br s, 2H), 6.37 (dd, J=7.2, 4.8 Hz, 1H), 3.91-3.77 (m, 1H), 3.57 (s, 2H), 2.86 (d, J=11.2 Hz, 2H), 2.16-2.05 (m, 2H), 1.81-1.70 (m, 4H).

Example 31: N-(1-(4-(2-(2-Aminopyridin-3-yl)-3H-imidazo[4,5-b]pyridin-3-yl)benzyl)piperidin-4-yl)-4-cyanopicolinamide

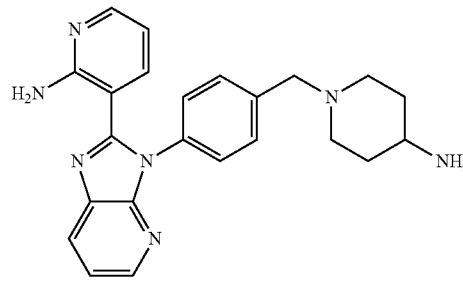

Intermediate 3

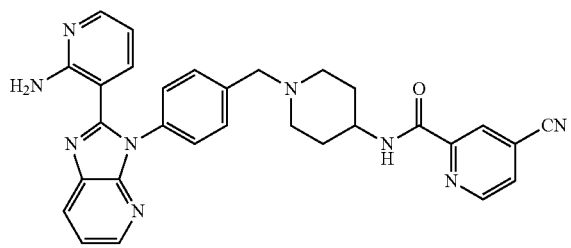

Example 31

Following the general procedure of Example 138, the reaction of Intermediate 3 (150 mg, 375 μmol) with 4-cyanopyridine-2-carboxylic acid (55.6 mg, 375 μmol) was carried out. After purified by prep-HPLC (column: Waters xbridge 150×25 mm 10 μm; mobile phase: [water (NH₄HCO₃)-ACN]; B %: 23%-53%, 8 min), N-(1-(4-(2-(2-aminopyridin-3-yl)-3H-imidazo[4,5-b]pyridin-3-yl)benzyl)piperidin-4-yl)-4-cyanopicolinamide (Example 31, 17.7 mg, yield: 9%) was obtained as a yellow solid. MS: m/z=530.1 [M+H]⁺. ¹H NMR (400 MHz, Chloroform-d) δ 8.74 (d, J=5.2 Hz, 1H), 8.44-8.37 (m, 2H), 8.10 (dd, J=8.0, 1.2 Hz, 1H), 8.05 (dd, J=4.8, 1.6 Hz, 1H), 7.91 (d, J=8.0 Hz, 1H), 7.67 (dd, J=4.8, 1.6 Hz, 1H), 7.56 (d, J=8.0 Hz, 2H), 7.36 (d, J=8.4 Hz, 2H), 7.32 (dd, J=8.0, 4.8 Hz, 1H), 7.07 (dd, J=8.0 1.6 Hz, 1H), 6.64 (br s, 2H), 6.34 (dd, J=8.0, 4.8 Hz, 1H), 4.12-4.03 (m, 11H), 3.70 (s, 2H), 3.07-2.97 (m, 2H), 2.39-2.30 (m, 2H), 2.10-2.05 (m, 2H), 1.84-1.78 (m, 2H).

Example 32: N-(1-(4-(2-(2-Aminopyridin-3-yl)-3H-imidazo[4,5-b]pyridin-3-yl)benzyl)piperidin-4-yl)-2-cyanopyrimidine-4-carboxamide

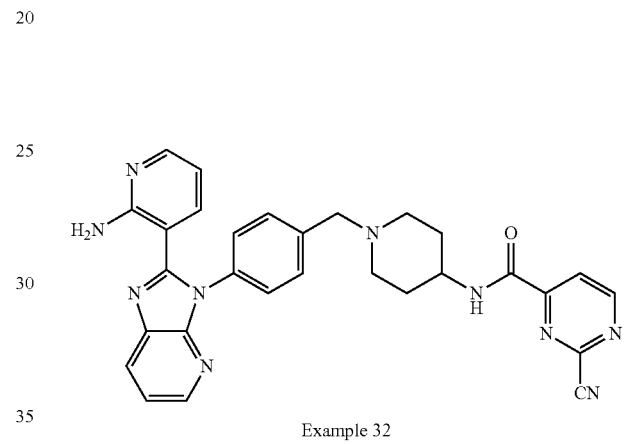

To a solution of Intermediate 3 (130 mg, 325 μmol), 2-cyanopyrimidine-4-carboxylic acid (64.7 mg, 391 μmol), EDCI (81.1 mg, 423 μmol) and HOBt (57.2 mg, 423 μmol) in CH₂Cl₂ (2 mL) was added DIEA (210 mg, 1.63 mmol). The mixture was stirred at 25° C. for 14 hr. The reaction mixture was diluted with H₂O (5 mL) and extracted with CH₂Cl₂ (10 mL×3). The combined organic layers were washed with brine (10 mL), dried over Na₂SO₄, filtered, and concentrated under reduced pressure to give a residue. The crude product was purified by prep-HPLC (column: Waters xbridge 150×25 mm 10 μm; mobile phase: [water (NH₄HCO₃)-ACN]; B %: 25%-55%, 15 min), N-(1-(4-(2-(2-aminopyridin-3-yl)-3H-imidazo[4,5-b]pyridin-3-yl)benzyl)piperidin-4-yl)-2-cyanopyrimidine-4-carboxamide (Example 32, 10.0 mg, yield: 5.8%) was obtained as a light-yellow solid. MS: m/z=531.0 [M+H]⁺. ¹H NMR (400 MHz, Dimethylsulfoxide-d₆) δ 9.22 (d, J=5.2 Hz, 1H), 9.04 (d, J=8.4 Hz, 1H), 8.36-8.30 (m, 1H), 8.26 (d, J=5.2 Hz, 1H), 8.22-8.19 (m, 1H), 7.99 (dd, J=4.8, 1.6 Hz, 1H), 7.48-7.36 (m, 5H), 7.19-7.15 (m, 1H), 7.01 (br s, 2H), 6.37 (dd, J=7.6, 4.8 Hz, 1H), 3.90-3.75 (m, 1H), 3.56 (s, 2H), 2.91-2.83 (m, 2H), 2.13-2.04 (m, 2H), 1.80-1.71 (m, 4H).

Example 33: N-(1-(4-(2-(2-Aminopyridin-3-yl)-3H-imidazo[4,5-b]pyridin-3-yl)benzyl)piperidin-4-yl)-6-cyanopyrimidine-4-carboxamide

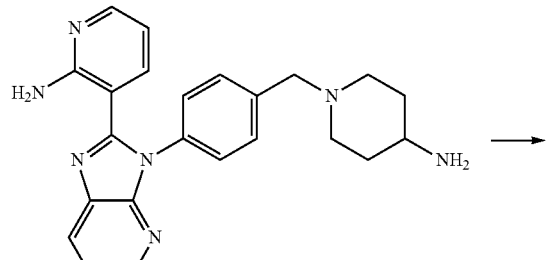

Intermediate 3

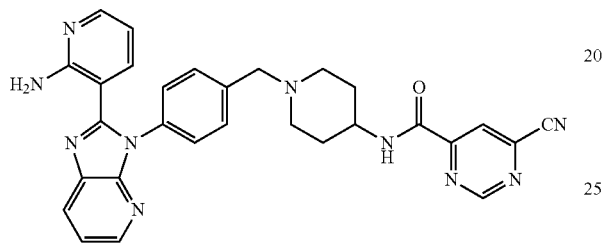

Example 33

Following the general procedure of Example 113, the reaction of Intermediate 3 (200 mg, 501 μmol) with 6-cyanopyrimidine-4-carboxylic acid (74.7 mg, 501 μmol) was carried out. After purified by prep-HPLC (column: Waters xbridge 150×25 mm 10 μm; mobile phase: [water (NH$_4$HCO$_3$)-ACN]; B %: 22%-5 2%, 8 min), N-(1-(4-(2-(2-aminopyridin-3-yl)-3H-imidazo[4,5-b]pyridin-3-yl)benzyl)piperidin-4-yl)-6-cyanopyrimidine-4-carboxamide (Example 33, 32.7 mg, yield: 12%) was obtained as a yellow solid. MS: m/z=531.1 [M+H]$^+$. $^1$H NMR (400 MHz, Dimethylsulfoxide-d$_6$) δ 9.53 (d, J=1.6 Hz, 1H), 9.05 (d, J=8.4 Hz, 1H), 8.53 (d, J=1.6 Hz, 1H), 8.33 (dd, J=4.4, 1.2 Hz, 1H), 8.20 (dd, J=8.0, 1.6 Hz, 1H), 7.99 (dd, J=4.8, 2.0 Hz, 1H), 7.45 (d, J=8.4 Hz, 2H), 7.41-7.36 (m, 3H), 7.17 (dd, J=7.6, 2.0 Hz, 1H), 7.00 (br s, 2H), 6.37 (dd, J=7.6, 4.8 Hz, 1H), 3.90-3.77 (m, 1H), 3.56 (s, 2H), 2.85 (d, J=11.6 Hz, 2H), 2.13-2.05 (m, 2H), 1.78-1.71 (m, 4H).

Example 34: N-(1-(4-(2-(2-aminopyridin-3-yl)-3H-imidazo[4,5-b]pyridin-3-yl)benzyl)piperidin-4-yl)-2-cyanobenzo[d]thiazole-5-carboxamide

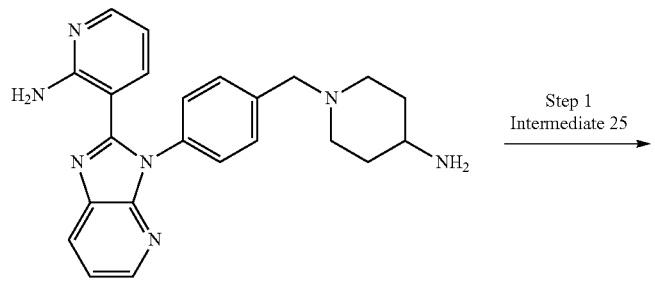

Intermediate 3

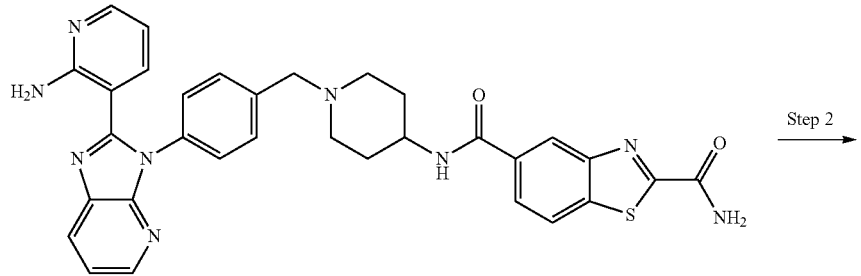

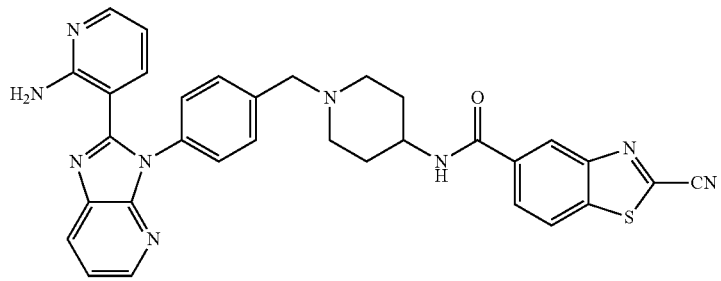

Example 34

Step 1: N⁵-(1-(4-(2-(2-Aminopyridin-3-yl)-3H-imidazo[4,5-b]pyridin-3-yl)benzyl)piperidin-4-yl)benzo[d]thiazole-2,5-dicarboxamide Following the general procedure Example 173 step 1, the reaction of Intermediate 3 (300 mg, 751 μmol) with Intermediate 25 (200 mg, 901 μmol) was carried out. After purified by prep-HPLC (column: Phenomenex C18 150*25 mm*10 μm; mobile phase: [water (NH₄HCO₃)-ACN]; B %: 16%-46%, 8 min), N⁵-(1-(4-(2-(2-aminopyridin-3-yl)-3H-imidazo[4,5-b]pyridin-3-yl)benzyl)piperidin-4-yl)benzo[d]thiazole-2,5-dicarboxamide (28.3 mg, yield: 6.2%) was obtained as an off-white solid. MS: m/z=604.2 [M+H]⁺. ¹H NMR (400 MHz, Dimethylsulfoxide-d₆) δ 8.58 (d, J=1.2 Hz, 1H), 8.53 (d, J=7.2 Hz, 1H), 8.46 (s, 1H), 8.34 (dd, J=4.8, 1.2 Hz, 1H), 8.29 (d, J=8.4 Hz, 1H), 8.21 (dd, J=7.6, 1.2 Hz, 1H), 8.15 (s, 1H), 8.03 (dd, J=8.4, 1.2 Hz, 1H), 7.99 (dd, J=4.8, 1.6 Hz, 1H), 7.47 (d, J=8.0 Hz, 2H), 7.42-7.37 (m, 3H), 7.17 (dd, J=7.6, 4.8 Hz, 1H), 7.01 (br s, 2H), 6.38 (dd, J=7.6, 4.8 Hz, 1H), 3.92-3.79 (m, 1H), 3.58 (s, 2H), 2.92-2.86 (m, 2H), 2.16-2.07 (m, 2H), 1.86 (d, J=10.4 Hz, 2H), 1.71-1.61 (m, 2H).

Step 2: N⁵-(1-(4-(2-(2-aminopyridin-3-yl)-3H-imidazo[4,5-b]pyridin-3-yl)benzyl)piperidin-4-yl)benzo[d]thiazole-2,5-dicarboxamide Following the general procedure of Example 173 step 2, the reaction of N⁵-(1-(4-(2-(2-aminopyridin-3-yl)-3H-imidazo[4,5-b]pyridin-3-yl)benzyl)piperidin-4-yl)benzo[d]thiazole-2,5-dicarboxamide (50 mg, 45 μmol) with POCl₃ (173 mg, 1.0 mmol) was carried out. The crude product was purified by reversed-phase HPLC (0.1% NH₃HCO₃), N-(1-(4-(2-(2-aminopyridin-3-yl)-3H-imidazo[4,5-b]pyridin-3-yl)benzyl)piperidin-4-yl)-2-cyanobenzo[d]thiazole-5-carboxamide (Example 34, 4.2 mg, yield: 16%) was obtained as a light-green solid. MS: m/z=586.2 [M+H]⁺. ¹H NMR (400 MHz, Chloroform-d) δ 8.55 (s, 1H), 8.40 (d, J=4.4 Hz, 1H), 8.15-8.02 (m, 4H), 7.52 (d, J=7.6 Hz, 2H), 7.37-7.30 (m, 3H), 7.08 (d, J=8.0 Hz, 1H), 6.66 (br s, 2H), 6.38-6.30 (m, 1H), 6.17 (d, J=8.0 Hz, 1H), 4.17-4.03 (m, 1H), 3.63 (s, 2H), 3.01-2.87 (m, 2H), 2.28 (t, J=10.8 Hz, 2H), 2.11 (d, J=12.4 Hz, 2H), 1.65-1.61 (m, 2H).

Example 35: N-(1-(4-(2-(2-Aminopyridin-3-yl)-3H-imidazo[4,5-b]pyridin-3-yl)benzyl)piperidin-4-yl)-2-cyano-5-fluorobenzo[d]thiazole-7-carboxamide

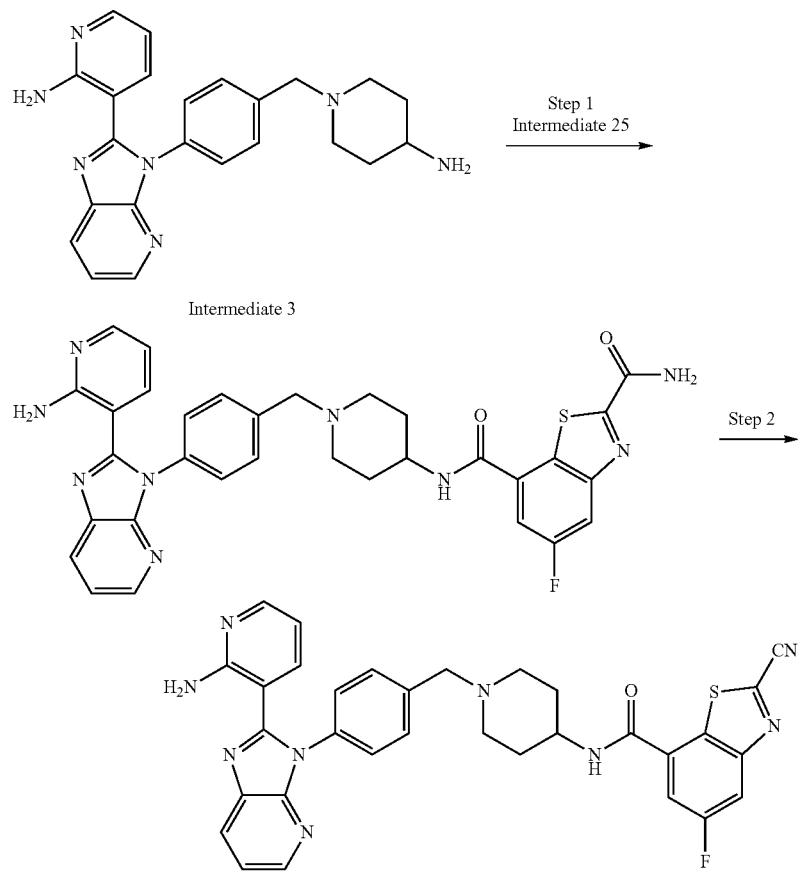

Example 35

Step 1: N⁷-(1-(4-(2-(2-Aminopyridin-3-yl)-3H-imidazo[4,5-b]pyridin-3-yl)benzyl)piperidin-4-yl)-5-fluorobenzo[d]thiazole-2,7-dicarboxamide Following the general procedure of Example 173 step 1, the reaction of Intermediate 3 (50 mg, 125 μmol) with Intermediate 26 (30 mg, 125 μmol) was carried out. After purified by prep-HPLC (column: Waters xbridge 150×25 mm 10 μm; mobile phase: [water (NH₄HCO₃)-ACN]; B %:

20%-50%, 11 min), N⁷-(1-(4-(2-(2-aminopyridin-3-yl)-3H-imidazo[4,5-b]pyridin-3-yl)benzyl)piperidin-4-yl)-5-fluorobenzo[d]thiazole-2,7-dicarboxamide (12.7 mg, yield: 15.2%) was obtained as a yellow lyophilized powder. MS: m/z=622.2 [M+H]⁺. ¹H NMR (400 MHz, Dimethylsulfoxide-d₆) δ 8.76 (d, J=4.8 Hz, 1H), 8.45 (s, 1H), 8.33 (dd, J=4.8, 1.2 Hz, 1H), 8.26 (dd, J=10.0, 2.0 Hz, 1H), 8.20 (dd, J=8.0, 1.6 Hz, 1H), 8.14 (dd, J=8.8, 2.0 Hz, 1H), 8.08 (s, 1H), 7.99 (dd, J=4.8, 1.6 Hz, 1H), 7.46 (d, J=8.0 Hz, 2H), 7.42-7.36 (m, 3H), 7.16 (dd, J=7.6, 2.0 Hz, 1H), 7.01 (br s, 2H), 6.38 (dd, J=7.6, 4.8 Hz, 1H), 3.93-3.83 (m, 1H), 3.58 (s, 2H), 2.92-2.83 (m, 2H), 2.15-2.09 (m, 2H), 1.89-1.85 (m, 2H), 1.72-1.60 (m, 2H). ¹⁹F NMR (400 MHz, Dimethylsulfoxide-d₆) δ −114.6.

Step 2: N-(1-(4-(2-(2-Aminopyridin-3-yl)-3H-imidazo[4,5-b]pyridin-3-yl)benzyl)piperidin-4-yl)-2-cyano-5-fluorobenzo[d]thiazole-7-carboxamide Following the general procedure of Example 173 step 2, the reaction of N⁷-(1-(4-(2-(2-aminopyridin-3-yl)-3H-imidazo[4,5-b]pyridin-3-yl)benzyl)piperidin-4-yl)-5-fluorobenzo[d]thiazole-2,7-dicarboxamide (30 mg, 48 µmol) with POCl₃ was carried out. After purified by prep-HPLC (column: Phenomenex C18 150×25 mm×10 µm; mobile phase: [water (NH₄HCO₃)-ACN]; B %: 36%-66%, 8 min), N-(1-(4-(2-(2-aminopyridin-3-yl)-3H-imidazo[4,5-b]pyridin-3-yl)benzyl)piperidin-4-yl)-2-cyano-5-fluorobenzo[d]thiazole-7-carboxamide (Example 35, 5 mg yield: 17%) was obtained as an off-white lyophilized powder. MS: m/z=604.3 [M+H]⁺. ¹H NMR (400 MHz, Dimethylsulfoxide-d₆) δ 8.96 (d, J=7.6 Hz, 1H), 8.47 (dd, J=9.6, 2.4 Hz, 1H), 8.41 (dd, J=8.8, 2.4 Hz, 1H), 8.33 (dd, J=4.8, 1.2 Hz, 1H), 8.21 (dd, J=8.0, 1.2 Hz, 1H), 7.99 (dd, J=4.8, 1.2 Hz, 1H), 7.47 (d, J=8.4 Hz, 2H), 7.42-7.36 (m, 3H), 7.17 (dd, J=7.6, 2.0 Hz, 1H), 7.01 (br s, 2H), 6.38 (dd, J=7.6, 4.8 Hz, 1H), 3.90-3.86 (m, 1H), 3.58 (s, 2H), 2.89 (d, J=11.2 Hz, 2H), 2.11 (t, J=11.2 Hz, 2H), 1.89-1.85 (m, 2H), 1.72-1.60 (m, 2H). ¹⁹F NMR (400 MHz, Dimethylsulfoxide-d₆) δ −113.1.

Example 36: N-(1-(4-(2-(2-Aminopyridin-3-yl)-3H-imidazo[4,5-b]pyridin-3-yl)benzyl)piperidin-4-yl)-3-cyanoisonicotinamide

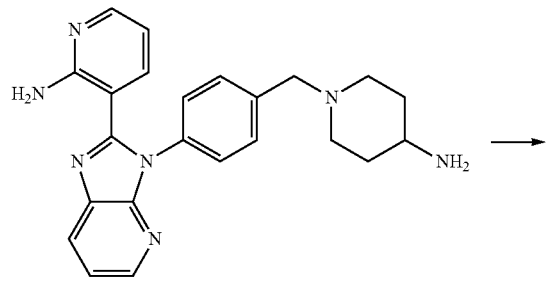

Intermediate 3

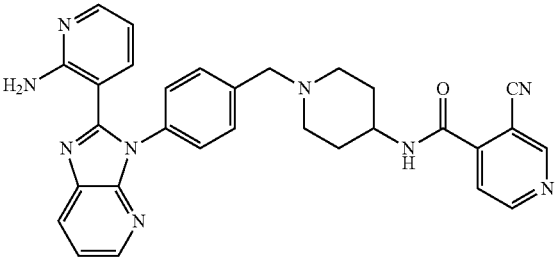

Example 36

Following the general procedure of Example 23, the reaction of Intermediate 3 (150 mg, 375 µmol) with 3-cyanopyridine-4-carboxylic acid (67 mg, 451 µmol) was carried out. After purified by prep-HPLC (column: Waters xbridge 150*25 mm 10 µm; mobile phase: [water (NH₄HCO₃)-ACN]; B %: 18%-48%, 8 min), N-(1-(4-(2-(2-aminopyridin-3-yl)-3H-imidazo[4,5-b]pyridin-3-yl)benzyl)piperidin-4-yl)-3-cyanoisonicotinamide (Example 36, 38.6 mg, yield: 19%) was obtained as a pink solid. MS: m/z=530.2 [M+H]⁺. ¹H NMR (400 MHz, Dimethylsulfoxide-d₆) δ 10.52 (s, 1H), 9.40 (s, 1H), 8.94 (d, J=4.8 Hz, 1H), 8.38-8.28 (m, 1H), 8.20 (d, J=8.0 Hz, 1H) 8.03-7.92 (m, 1H), 7.77 (d, J=4.8 Hz, 1H), 7.48 (d, J=8.0 Hz, 2H), 7.44-7.36 (m, 3H), 7.22-7.14 (m, 1H), 7.01 (brs, 2H), 6.37 (dd, J=7.6, 4.8 Hz, 1H), 4.42-4.17 (m, 1H), 3.59 (s, 2H), 3.04-2.90 (m, 2H), 2.54 (br s, 2H), 2.14-2.02 (m, 2H), 1.70-1.55 (m, 2H).

Example 37: N-(3-(2-(2-Aminopyridin-3-yl)-3-(4-((4-(2-cyanopyridin-4-yl)piperazin-1-yl)methyl)phenyl)-3H-imidazo[4,5-b]pyridin-5-yl)phenyl)acetamide

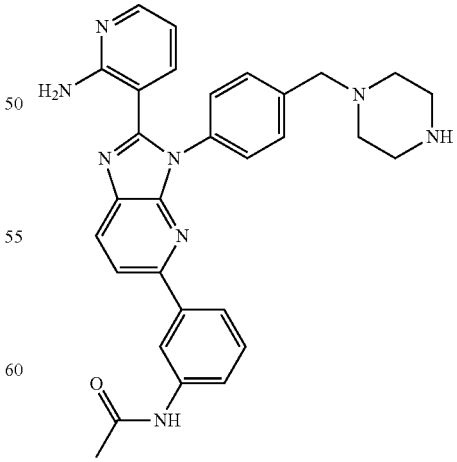

Intermediate 6

1109

-continued

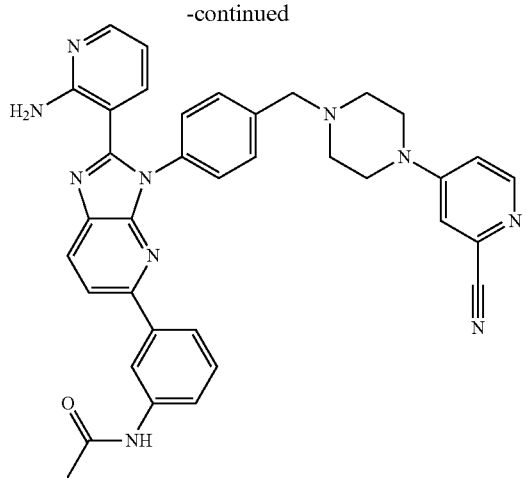

Example 37

1110

-continued

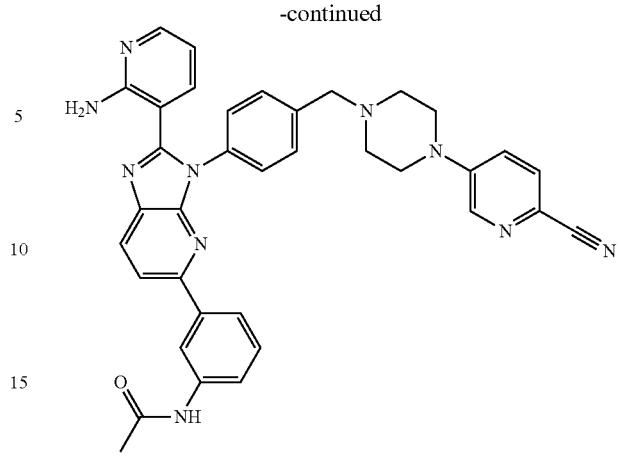

Example 38

To a solution of Intermediate 6 (150 mg, 289 μmol), 4-fluoropicolinonitrile (38.8 mg, 318 μmol) in DMF (2 mL) was added DIEA (112 mg, 868 μmol). The mixture was degassed and purged with $N_2$ three times and stirred at 100° C. for 16 hr under $N_2$. The reaction mixture was filtered and concentrated under reduced pressure to give a residue. The residue was purified by prep-HPLC (column: Waters xbridge 150*25 mm 10 μm; mobile phase: [water ($NH_4HCO_3$)-ACN]; B %: 26%-56%, 8 min), N-(3-(2-(2-aminopyridin-3-yl)-3-(4-((4-(2-cyanopyridin-4-yl)piperazin-1-yl)methyl)phenyl)-3H-imidazo[4,5-b]pyridin-5-yl)phenyl)acetamide (Example 37, 155 mg, yield: 86%) was obtained as a yellow solid. MS: m/z=621.2 [M+H]$^+$. $^1$H NMR (400 MHz, Chloroform-d) δ 8.30 (d, J=6.0 Hz, 1H), 8.16-8.11 (m, 2H), 8.08 (dd, J=4.8, 1.2 Hz, 1H), 7.81 (d, J=8.0 Hz, 1H), 7.77 (d, J=7.6 Hz, 1H), 7.56 (d, J=8.0 Hz, 1H), 7.51 (d, J=8.0 Hz, 2H), 7.45-7.35 (m, 4H), 7.09 (d, J=8.0 Hz, 1H), 7.04 (d, J=1.6 Hz, 1H), 6.80-5.75 (m, 1H), 6.61 (br s, 2H), 6.37 (dd, J=7.6, 4.8 Hz, 1H), 3.65 (s, 2H), 3.49-3.42 (m, 4H), 2.59-2.52 (m, 4H), 2.05 (s, 3H).

Example 38: N-(3-(2-(2-Aminopyridin-3-yl)-3-(4-((4-(6-cyanopyridin-3-yl)piperazin-1-yl)methyl)phenyl)-3H-imidazo[4,5-b]pyridin-5-yl)phenyl)acetamide Following the general procedure of Example 37, the reaction of Intermediate 6 (150 mg, 289 μmol) with 5-fluoropicolinonitrile (38.8 mg, 318 μmol) was carried out. After purified by prep-HPLC (column: Phenomenex Luna C18 150*25 mm*10 μm; mobile phase: [water ($NH_4HCO_3$)-ACN]; B %: 35%-65%, 8 min), N-(3-(2-(2-aminopyridin-3-yl)-3-(4-((4-(6-cyanopyridin-3-yl)piperazin-1-yl)methyl)phenyl)-3H-imidazo[4,5-b]pyridin-5-yl)phenyl)acetamide (Example 38, 105 mg, yield: 58%) was obtained as a white solid. MS: m/z=621.2 [M+H]$^+$. $^1$H NMR (400 MHz, Dimethylsulfoxide-d$_6$) δ 10.05 (s, 1H), 8.43 (d, J=2.8 Hz, 1H), 8.28 (d, J=8.4 Hz, 1H), 8.16 (s, 1H), 8.00 (dd, J=4.8 Hz, 1H), 7.86 (d, J=8.4 Hz, 1H), 7.75 (d, J=8.8 Hz, 1H), 7.69-7.63 (m, 2H), 7.54-7.44 (m, 4H), 7.41-7.33 (m, 2H), 7.14 (dd, J=7.6, 1.6 Hz, 1H), 6.99 (br s, 2H), 6.37 (dd, J=7.6, 4.8 Hz, 1H), 3.65 (s, 2H), 3.49-3.42 (m, 4H), 2.59-2.52 (m, 4H), 2.05 (s, 3H).

Example 39: N-(3-(2-(2-Aminopyridin-3-yl)-3-(4-((4-(6-cyanopyridin-2-yl)piperazin-1-yl)methyl)phenyl)-3H-imidazo[4,5-b]pyridin-5-yl)phenyl)acetamide

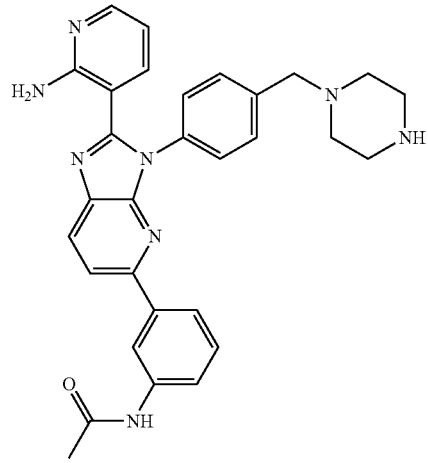

Intermediate 6

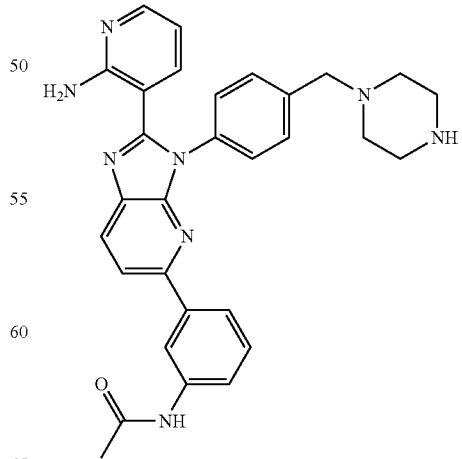

Intermediate 6

-continued

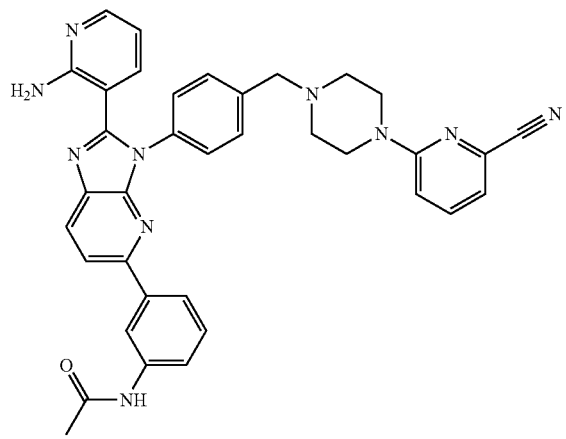

Example 39

-continued

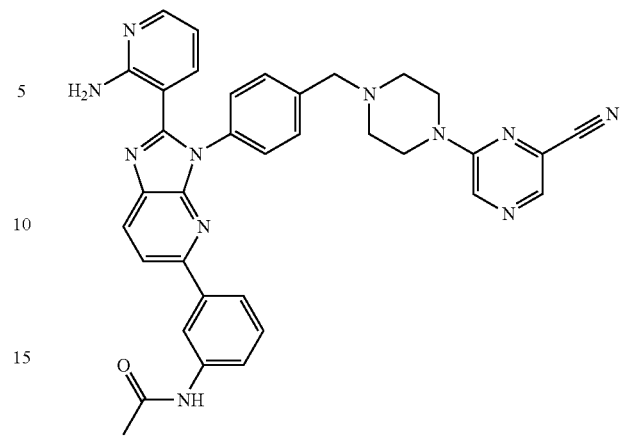

Example 40

Following the general procedure of Example 37, the reaction of Intermediate 6 (200 mg, 386 μmol) with 6-fluoropicolinonitrile (51.8 mg, 424 μmol) was carried out. After purified by prep-HPLC (column: Phenomenex C18 150*25 mm*10 μm; mobile phase: [water (NH$_4$HCO$_3$)-ACN]; B %: 40%-70%, 8 min), N-(3-(2-(2-aminopyridin-3-yl)-3-(4-((4-(6-cyanopyridin-2-yl)piperazin-1-yl)methyl)phenyl)-3H-imidazo[4,5-b]pyridin-5-yl)phenyl)acetamide (Example 39, 56 mg, yield: 23%) was obtained as a white solid. MS: m/z=621.2 [M+H]$^+$. $^1$H NMR (400 MHz, Dimethylsulfoxide-d$_6$) δ 10.04 (s, 1H), 8.28 (d, J=8.4 Hz, 1H), 8.8 (s, 1H), 8.00 (dd, J=4.8, 1.6 Hz, 1H), 7.87 (d, J=8.4 Hz, 1H), 7.73-7.61 (m, 3H), 7.55-7.43 (m, 4H), 7.38 (dd, J=8.0, 8.0 Hz, 1H), 7.23-7.12 (m, 3H), 7.00 (br s, 2H), 6.37 (dd, J=7.6, 4.8 Hz, 1H), 3.64 (s, 2H), 3.61-3.56 (m, 4H), 2.54-2.51 (m, 4H), 2.07 (s, 3H).

Following the general procedure of Example 37, the reaction of Intermediate 6 (200 mg, 386 μmol) with 6-chloropyrazine-2-carbonitrile (59.2 mg, 424 μmol) was carried out. After purified by prep-HPLC (column: Phenomenex C18 150*25 mm*10 μm; mobile phase: [water (NH$_4$HCO$_3$)-ACN]; B %: 35%-65%, 8 min), N-(3-(2-(2-aminopyridin-3-yl)-3-(4-((4-(6-cyanopyrazin-2-yl)piperazin-1-yl)methyl)phenyl)-3H-imidazo[4,5-b]pyridin-5-yl)phenyl)acetamide (Example 40, 61.3 mg, yield: 26%) was obtained as a brown solid. MS: m/z=622.2 [M+H]$^+$. $^1$H NMR (400 MHz, Dimethylsulfoxide-d$_6$) δ 10.04 (s, 1H), 8.65 (s, 1H), 8.31-8.25 (m, 2H), 8.19 (s, 1H), 8.00 (dd, J=4.8 Hz, 1H), 7.87 (d, J=8.4 Hz, 1H), 7.70-7.61 (m, 2H), 7.54-7.44 (m, 4H), 7.38 (dd, J=8.0, 8.0 Hz, 1H), 7.15 (dd, J=7.6, 2.0 Hz, 1H), 7.00 (br s, 2H), 6.37 (dd, J=7.6, 4.8 Hz, 1H), 3.70-3.65 (m, 4H), 3.64 (s, 2H), 2.55-2.52 (m, 4H), 2.06 (s, 3H).

Example 40: N-(3-(2-(2-aminopyridin-3-yl)-3-(4-((4-(6-cyanopyrazin-2-yl)piperazin-1-yl)methyl)phenyl)-3H-imidazo[4,5-b]pyridin-5-yl)phenyl)acetamide Example 41: N-(3-(2-(2-Aminopyridin-3-yl)-3-(4-((4-(6-cyanopyrimidin-4-yl)piperazin-1-yl)methyl)phenyl)-3H-imidazo[4,5-b]pyridin-5-yl)phenyl)acetamide

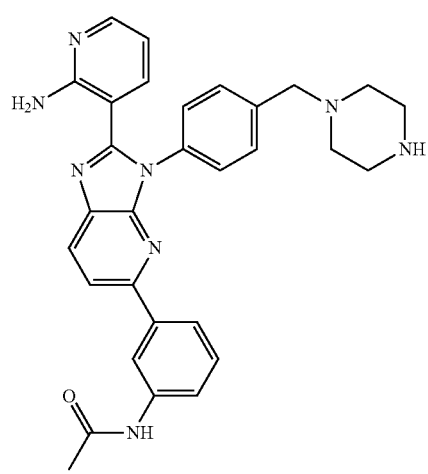

Intermediate 6

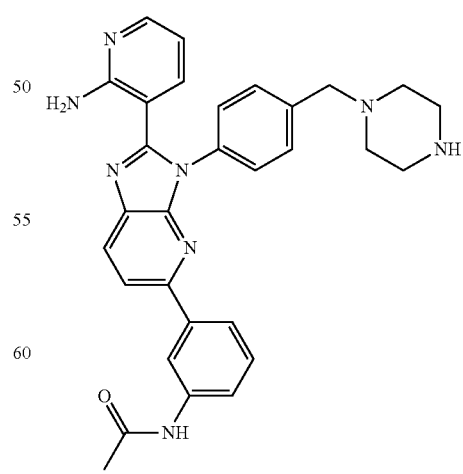

Intermediate 6

1113

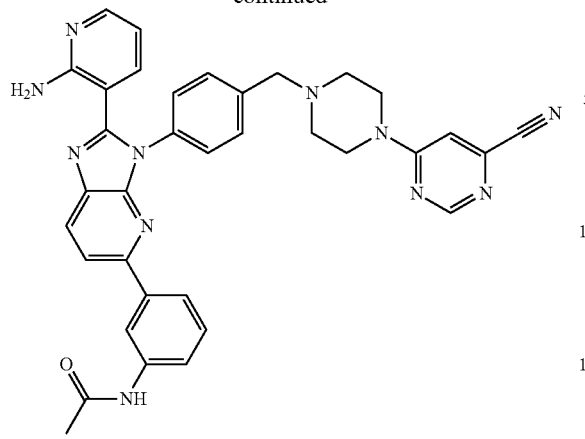

Example 41

Following the general procedure of Example 37, the reaction of Intermediate 6 (200 mg, 386 μmol) with 6-chloropyrimidine-4-carbonitrile (59.2 mg, 424 μmol) was carried out. After purified by prep-HPLC (column: Phenomenex C18 150*25 mm*10 μm; mobile phase: [water (NH$_4$HCO$_3$)-ACN]; B %: 32%-62%, 8 min), N-(3-(2-(2-aminopyridin-3-yl)-3-(4-((4-(6-cyanopyrimidin-4-yl)piperazin-1-yl)methyl)phenyl)-3H-imidazo[4,5-b]pyridin-5-yl)phenyl)acetamide (Example 41, 59.4 mg, yield: 25%) was obtained as a white solid. MS: m/z=622.2 [M+H]$^+$. $^1$H NMR (400 MHz, Dimethylsulfoxide-d$_6$) δ 10.04 (s, 1H), 8.56 (d, J=1.2 Hz, 1H), 8.28 (d, J=8.4 Hz, 1H), 8.17 (s, 1H), 7.99 (dd, J=4.8, 2.0 Hz, 1H), 7.87 (d, J=8.4 Hz, 1H), 7.70-7.61 (m, 2H), 7.56 (s, 1H), 7.53-7.44 (m, 4H), 7.38 (dd, J=8.0, 8.0 Hz, 1H), 7.14 (dd, J=7.6, 2.0 Hz, 1H), 6.99 (br s, 2H), 6.35 (dd, J=7.6, 4.8 Hz, 1H), 3.89-3.66 (m, 4H), 3.64 (s, 2H), 2.49-2.47 (m, 4H), 2.06 (s, 3H).

Example 42: N-(3-(2-(2-Aminopyridin-3-yl)-3-(4-((4-(2-cyanopyrimidin-5-yl)piperazin-1-yl)methyl)phenyl)-3H-imidazo[4,5-b]pyridin-5-yl)phenyl)acetamide

1114

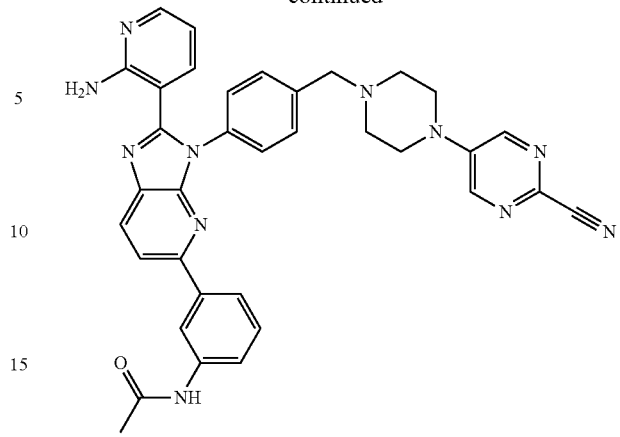

Example 42

To a solution of Intermediate 6 (200 mg, 386 μmol) and 2-chloropyrimidine-4-carbonitrile (59 mg, 424 μmol) in 1,4-dioxane (4 mL) was added DIEA (199 mg, 1.54 mmol). The mixture was stirred at 80° C. for 12 hr. The reaction was filtered and concentrated under reduced pressure to give a residue. The crude product was purified by prep-HPLC (column: Waters xbridge 150*25 mm 10 μm; mobile phase: [water (NH$_4$HCO$_3$)-ACN]; B %: 38%-68%, 10 min), N-(3-(2-(2-aminopyridin-3-yl)-3-(4-((4-(2-cyanopyrimidin-5-yl)piperazin-1-yl)methyl)phenyl)-3H-imidazo[4,5-b]pyridin-5-yl)phenyl)acetamide (Example 42, 36.8 mg, yield: 14%) was obtained as a light-yellow solid. MS: m/z=622.3 [M+H]$^+$. $^1$H NMR (400 MHz, Dimethylsulfoxide-d$_6$) δ 10.05 (s, 1H), 8.58 (s, 2H), 8.28 (d, J=8.4 Hz, 1H), 8.17 (s, 1H), 8.00 (dd, J=4.8, 1.6 Hz, 1H), 7.86 (d, J=8.4 Hz, 1H), 7.66 (d, J=8.0 Hz, 2H), 7.57-7.45 (m, 4H), 7.38 (dd, J=8.0, 8.0 Hz, 1H), 7.14 (d, J=7.6 Hz, 1H), 6.99 (br s, 2H), 6.37 (dd, J=7.6, 4.8 Hz, 1H), 3.65 (s, 2H), 3.56-3.48 (m, 4H), 2.60-2.52 (m, 4H), 2.05 (s, 3H).

Example 43: N-(3-(2-(2-Aminopyridin-3-yl)-3-(4-((4-(6-cyanopyridazin-4-yl)piperazin-1-yl)methyl)phenyl)-3H-imidazo[4,5-b]pyridin-5-yl)phenyl)acetamide

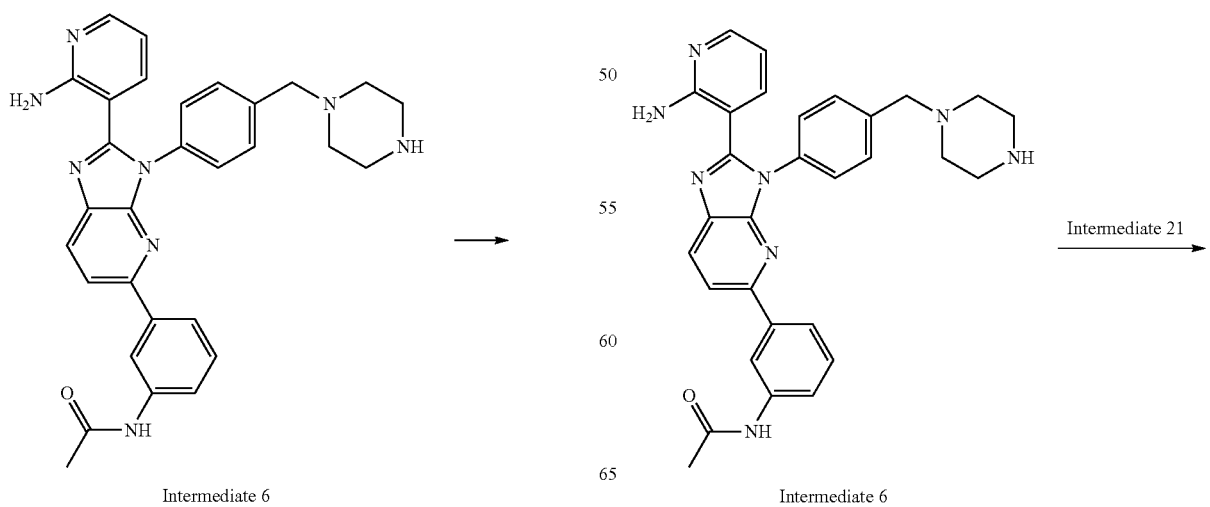

Intermediate 6        Intermediate 6

Intermediate 21 →

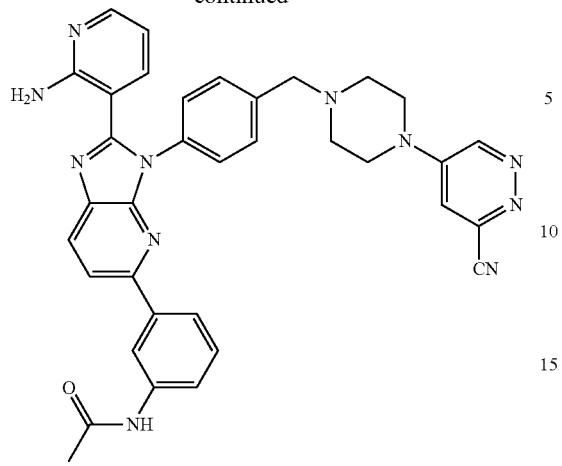

Example 43

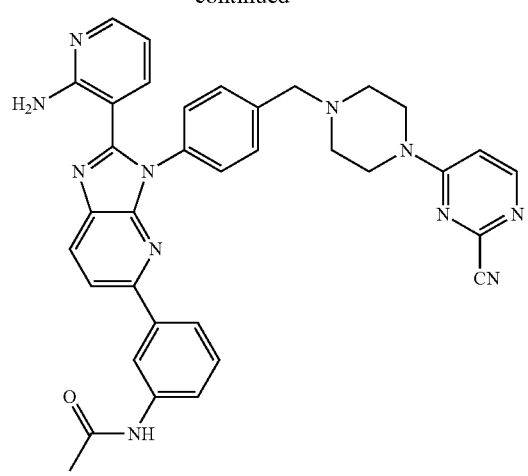

Example 44

Following the general procedure of Example 47, the reaction of Intermediate 6 (200 mg, 385 μmol) with Intermediate 21 (54 mg, 385 μmol) was carried out. After purified by prep-HPLC (column: Waters xbridge 150*25 mm 10 μm; mobile phase: [water (NH₄HCO₃)-ACN]; B %: 25%-55%, 10 min), N-(3-(2-(2-aminopyridin-3-yl)-3-(4-((4-(6-cyanopyridazin-4-yl)piperazin-1-yl)methyl)phenyl)-3H-imidazo[4,5-b]pyridin-5-yl)phenyl)acetamide (Example 43, 54.6 mg, yield: 23%) was obtained as a yellow solid. MS: m/z=622.4 [M+H]⁺. ¹H NMR (400 MHz, Dimethylsulfoxide-d₆) δ 10.05 (s, 1H), 9.14 (d, J=3.2 Hz, 1H), 8.28 (d, J=8.41 Hz, 1H), 8.16 (s, 1H), 7.99 (dd, J=4.8, 1.6 Hz, 1H), 7.86 (d, J=8.4 Hz, 1H), 7.71-7.59 (m, 4H), 7.54-7.44 (m, 5H), 7.41-7.35 (m, 1H), 7.14 (dd, J=7.6, 1.6 Hz, 1H), 7.00 (br s, 2H), 6.35 (dd, J=8.0, 4.8 Hz, 1H), 3.65 (s, 2H), 3.61-3.55 (m, 4H), 2.56-2.52 (m, 4H), 2.06 (s, 3H).

Example 44: N-(3-(2-(2-Aminopyridin-3-yl)-3-(4-((4-(2-cyanopyrimidin-4-yl)piperazin-1-yl)methyl)phenyl)-3H-imidazo[4,5-b]pyridin-5-yl)phenyl)acetamide Following the general procedure of Example 47, the reaction of Intermediate 6 (200 mg, 385 μmol) with 4-chloropyrimidine-2-carbonitrile (54 mg, 385 μmol) was carried out. After purified by prep-HPLC (column: Waters xbridge 150*25 mm 10 μm; mobile phase: [water (NH₄HCO₃)-ACN]; B %: 32%-62%, 10 min), N-(3-(2-(2-aminopyridin-3-yl)-3-(4-((4-(2-cyanopyrimidin-4-yl)piperazin-1-yl)methyl)phenyl)-3H-imidazo[4,5-b]pyridin-5-yl)phenyl)acetamide (Example 44, 37.6 mg, yield: 16%) was obtained as a yellow solid. MS: m/z=622.5 [M+H]⁺. ¹H NMR (400 MHz, Dimethylsulfoxide-d₆) δ 10.05 (s, 1H), 8.34-8.24 (m, 2H), 8.20 (s, 1H), 8.00 (dd, J=4.8, 2.0 Hz, 1H), 7.88 (d, J=8.4 Hz, 1H), 7.70-7.62 (m, 2H), 7.57-7.45 (m, 4H), 7.42-7.36 (m, 1H), 7.18-7.10 (m, 2H), 7.00 (br s, 2H), 6.38 (dd, J=7.6, 4.8 Hz, 1H), 3.74-3.64 (m, 4H), 3.65 (s, 2H), 2.56-2.52 (m, 4H), 2.07 (s, 3H).

Example 45: N-(3-(2-(2-Aminopyridin-3-yl)-3-(4-((4-(5-cyanopyridazin-3-yl)piperazin-1-yl)methyl)phenyl)-3H-imidazo[4,5-b]pyridin-5-yl)phenyl)acetamide

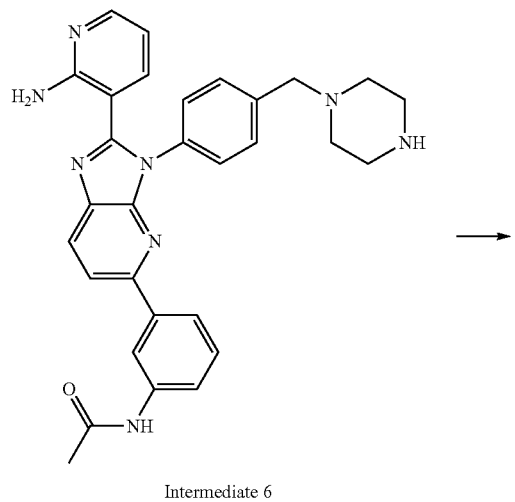

Intermediate 6

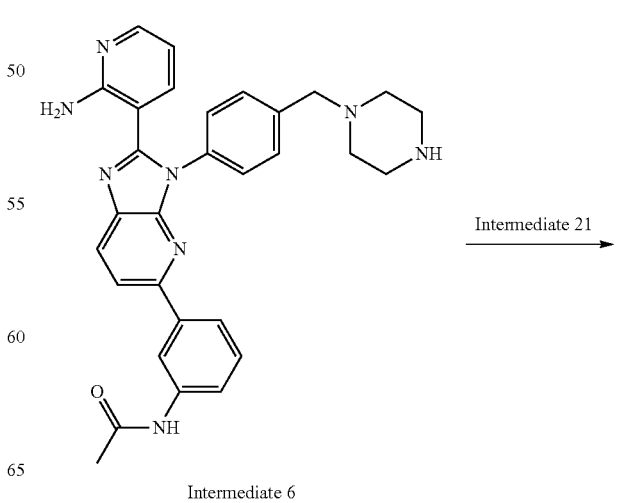

Intermediate 6 →  Intermediate 21

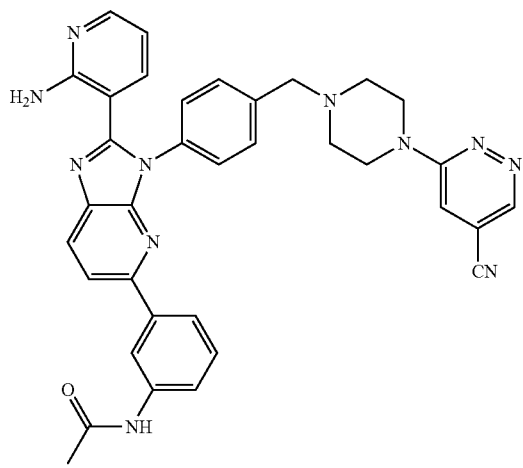

Example 45

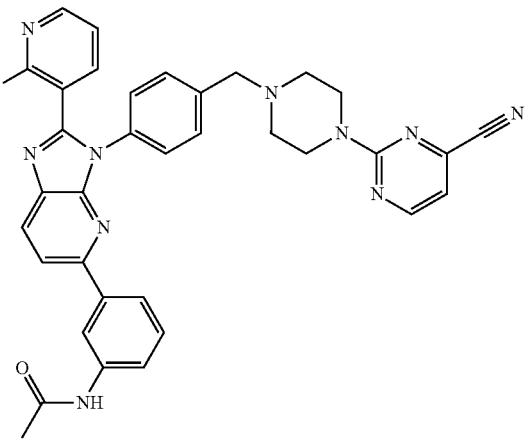

Example 46

Following the general procedure of Example 50, the reaction of Intermediate 6 (250 mg, 482 μmol) with Intermediate 21 (74 mg, 530 μmol) was carried out. After purified by prep-HPLC (column: Waters xbridge 150*25 mm 10 μm; mobile phase. [water (NH$_4$HCO$_3$)-ACN]; B %: 25%-55%, 10 min), N-(3-(2-(2-aminopyridin-3-yl)-3-(4-((4-(5-cyanopyridazin-3-yl)piperazin-1-yl)methyl)phenyl)-3H-imidazo[4,5-b]pyridin-5-yl)phenyl)acetamide (Example 45, 6 mg, yield: 2%) was obtained as a yellow solid. MS: m/z=622.2 [M+H]$^+$. $^1$H NMR (400 MHz, Dimethylsulfoxide-d$_6$) δ 8.68 (s, 1H), 8.25-8.16 (m, 2H), 7.99 (dd, J=5.2, 1.2 Hz, 1H), 7.92 (d, J=8.4 Hz, 1H), 7.77 (d, J=8.0 Hz, 1H), 7.67 (s, 1H), 7.64-7.56 (m, 3H), 7.47 (d, J=8.4 Hz, 2H), 7.41-7.30 (m, 2H), 6.47 (dd, J=7.6, 4.8 Hz, 1H), 3.79-3.74 (m, 4H), 3.70 (s, 2H), 2.70-2.63 (m, 4H), 2.14 (s, 3H).

Example 46: N-(3-(2-(2-Aminopyridin-3-yl)-3-(4-((4-(4-cyanopyrimidin-2-yl)piperazin-1-yl)methyl)phenyl)-3H-imidazo[4,5-b]pyridin-5-yl)phenyl)acetamide To a solution of Intermediate 6 (200 mg, 386 μmol) and 2-chloropyrimidine-4-carbonitrile (59 mg, 424 μmol) in 1,4-dioxane (4 mL) was added DIEA (199 mg, 1.54 mmol). The mixture was stirred at 80° C. for 12 hr. The reaction was filtered and concentrated under reduced pressure to give a residue. The crude product was purified by prep-HPLC (column: Waters xbridge 150*25 mm 10 μm; mobile phase: [water (NH$_4$HCO$_3$)-ACN]; B %: 38%-68%, 10 min), N-(3-(2-(2-aminopyridin-3-yl)-3-(4-((4-(4-cyanopyrimidin-2-yl)piperazin-1-yl)methyl)phenyl)-3H-imidazo[4,5-b]pyridin-5-yl)phenyl)acetamide (Example 46, 36.8 mg, yield: 14%) was obtained as a light-yellow solid. MS: m/z=622.3 [M+H]$^+$. $^1$H NMR (400 MHz, Dimethylsulfoxide-d$_6$) δ 10.04 (s, 1H), 8.64 (d, J=4.4 Hz, 1H), 8.28 (d, J=8.4 Hz, 1H), 8.19 (s, 1H), 7.99 (dd, J=4.8, 2.0 Hz, 1H), 7.87 (d, J=8.4 Hz, 1H), 7.70-7.60 (m, 2H), 7.57-7.43 (m, 4H), 7.40-7.34 (m, 1H), 7.24-7.09 (m, 2H), 6.99 (br s, 2H), 6.37 (dd, J=7.6, 4.8 Hz, 1H), 3.83-3.73 (m, 4H), 3.63 (s, 2H), 3.33-3.31 (m, 4H), 2.06 (s, 3H).

Example 47: 4-((4-(2-(2-Aminopyridin-3-yl)-3H-imidazo[4,5-b]pyridin-3-yl)benzyl)amino)pyrimidine-2-carbonitrile

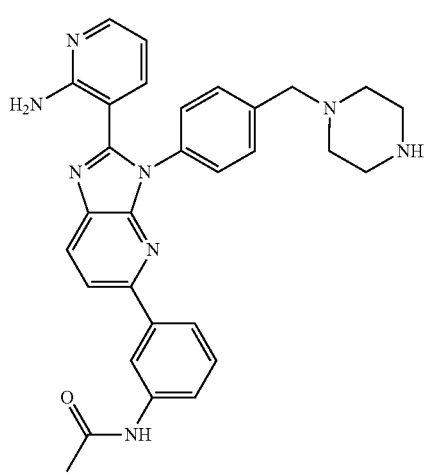

Intermediate 6

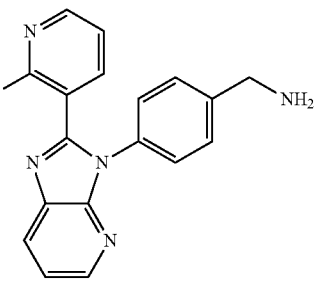

Intermediate 1

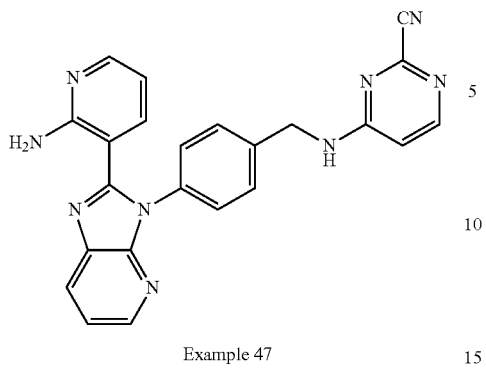

Example 47

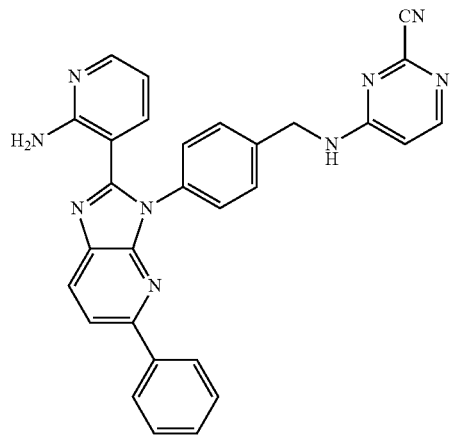

Example 48

A mixture of Intermediate 1 (200 mg, 632 μmol), 4-chloropyrimidine-2-carbonitrile (88 mg, 632 μmol) and DIEA (408 mg, 3.16 mmol) in NMP (3 mL) was stirred at 130° C. for 1 hr under microwave. The reaction mixture was poured into H$_2$O (50 mL). The resulting mixture was extracted with CH$_2$Cl$_2$ (50 mL×3). The combined organic dried over anhydrous Na$_2$SO$_4$, filtered and concentrated to dryness. The residue was purified by prep-HPLC (column: Waters xbridge 150*25 mm 10 μm; mobile phase: [water (NH$_4$HCO$_3$)-ACN]; B %: 20%-50%, 10 min), 4-((4-(2-(2-aminopyridin-3-yl)-3H-imidazo[4,5-b]pyridin-3-yl)benzyl)amino)pyrimidine-2-carbonitrile (Example 47, 26.3 mg, yield: 10%) as a light-yellow lyophilized powder. MS: m/z=420.3 [M+H]$^+$. $^1$H NMR (400 MHz, Dimethylsulfoxide-d$_6$) δ 8.70-8.56 (m, 1H), 8.31 (d, J=4.8 Hz, 1H), 8.26-8.13 (m, 2H), 7.99 (dd, J=4.8, 1.6 Hz, 1H), 7.47 (d, J=8.4 Hz, 2H), 7.45-7.37 (m, 3H), 7.22 (d, J=7.6 Hz, 1H), 6.96 (br s, 2H), 6.81 (d, J=6.0 Hz, 1H), 6.40 (dd, J=6.8, 4.8 Hz, 1H), 4.63 (d, J=5.2 Hz, 2H).

Example 48: 4-((4-(2-(2-Aminopyridin-3-yl)-5-phenyl-3H-imidazo[4,5-b]pyridin-3-yl)benzyl)amino)pyrimidine-2-carbonitrile Following the general procedure of Example 47, the reaction of Intermediate 4 (200 mg, 509 μmol) with 4-chloropyrimidine-2-carbonitrile (71 mg, 509 μmol) was carried out. After purified by prep-HPLC (column: Waters xbridge 150*25 mm 10 μm; mobile phase: [water (NH$_4$HCO$_3$)-ACN]; B %: 40%-70%, 10 min), 4-((4-(2-(2-aminopyridin-3-yl)-5-phenyl-3H-imidazo[4,5-b]pyridin-3-yl)benzyl)amino)pyrimidine-2-carbonitrile (Example 48, 36.4 mg, yield: 14.4%) was obtained as a yellow solid. MS: m/z=496.4 [M+H]$^+$. $^1$H NMR (400 MHz, Dimethylsulfoxide-d$_6$) δ 64 (t, J=5.6 Hz, 1H), 8.27 (d, J=8.4 Hz, 1H), 8.17 (d, J=5.6 Hz, 1H), 8.05-7.97 (m, 4H), 7.52-7.44 (m, 6H), 7.42-7.36 (m, 1H), 7.24-7.15 (m, 1H), 6.96 (br s, 2H), 6.82 (d, J=6.0 Hz, 1H), 6.44-6.36 (m, 1H), 4.66 (J=5.6 Hz, 2H).

Example 49: 4-(4-(4-(2-(2-Aminopyridin-3-yl)-5-phenyl-3H-imidazo[4,5-b]pyridin-3-yl)benzyl)piperazin-1-yl)pyrimidine-2-carbonitrile

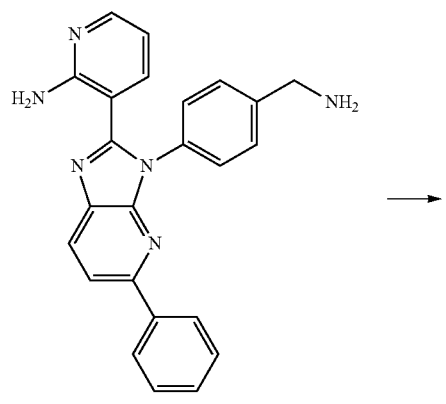

Intermediate 4

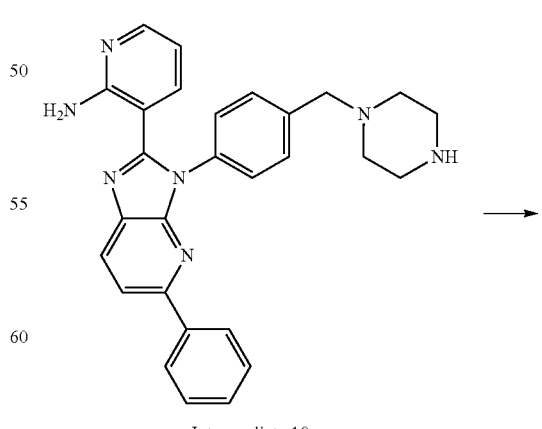

Intermediate 10

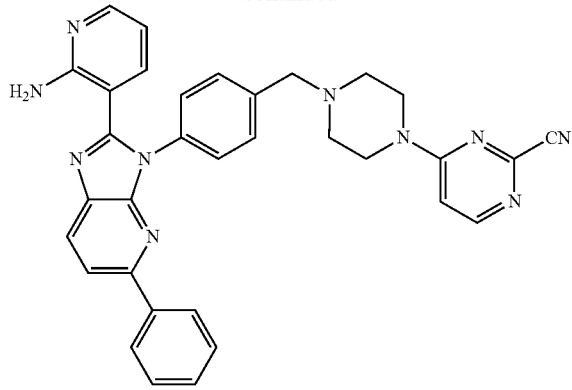

Example 49

Following the general procedure of Example 47, the reaction of Intermediate 10 (200 mg, 433 μmol) with 4-chloropyrimidine-2-carbonitrile (60 mg, 433 μmol) was carried out. After purified by prep-HPLC (column: Waters xbridge 150*25 mm 10 μm; mobile phase: [water (NH$_4$HCO$_3$)-ACN]; B %: 47%-77%, 10 min), 4-(4-(4-(2-(2-aminopyridin-3-yl)-5-phenyl-3H-imidazo[4,5-b]pyridin-3-yl)benzyl)piperazin-1-yl)pyrimidine-2-carbonitrile (Example 49, 73.9 mg, yield: 30%) was obtained as a yellow solid. MS: m/z=565.4 [M+H]$^+$. $^1$H NMR (400 MHz, Dimethylsulfoxide-d$_6$) δ 8.32-8.22 (m, 2H), 8.07-7.95 (m, 4H), 7.54-7.44 (m, 6H), 7.43-7.37 (m, 1H), 7.18-7.08 (m, 2H), 7.03 (br s, 2H), 6.37 (dd, J=7.6, 4.8 Hz, 1H), 3.72-3.66 (m, 4H), 3.65 (s, 2H), 2.57-2.51 (m, 4H).

Example 50: 6-((4-(2-(2-Aminopyridin-3-yl)-3H-imidazo[4,5-b]pyridin-3-yl)benzyl)amino)pyridazine-4-carbonitrile

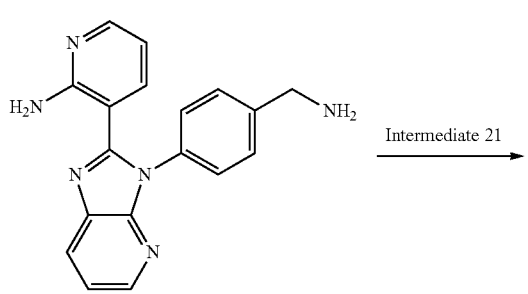

Intermediate 1

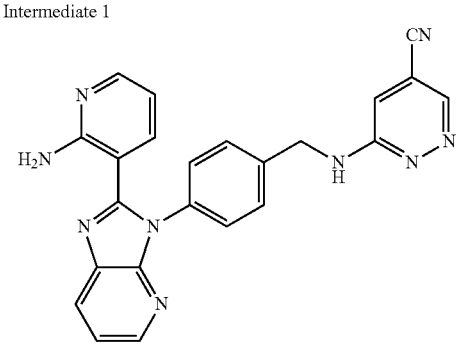

Example 50

To a solution of Intermediate 1 in NMP (2 mL) was added Intermediate 21 (106 mg, 759 μmol) and DIEA (408 mg, 3.16 mmol). The mixture was stirred at microwave 160° C. for 1 hr. The mixture was concentrated under reduced pressure to give a residue. The mixture was purified by prep-HPLC (column: Welch Xtimate C18 150*25 mm*5 μm; mobile phase: [water (HCl)-ACN]; B %: 18%-48%, 10 min) to give 6-((4-(2-(2-aminopyridin-3-yl)-3H-imidazo[4,5-b]pyridin-3-yl)benzyl)amino)pyridazine-4-carbonitrile (Example 50, 11.3 mg, yield: 4.3%) was a light-gray solid. MS: m/z=420.1 [M+H]$^+$. $^1$H NMR (400 MHz, Dimethylsulfoxide-d$_6$) δ 8.75 (d, J=1.6 Hz, 1H), 8.30 (dd, J=4.8, 1.2 Hz, 1H), 8.19 (dd, J=8.0, 1.2 Hz, 1H), 8.08-7.92 (m, 2H), 7.49 (d, J=8.4 Hz, 2H), 7.44-7.29 (m, 4H), 7.21 (dd, J=7.6, 1.6 Hz, 1H), 6.96 (br s, 2H), 6.39 (dd, J=7.6, 4.8 Hz, 1H), 4.70 (d, J=5.6 Hz, 2H).

Example 51: 6-((1-(4-(2-(2-Aminopyridin-3-yl)-3H-imidazo[4,5-b]pyridin-3-yl)benzyl)piperidin-4-yl)amino)pyridazine-4-carbonitrile

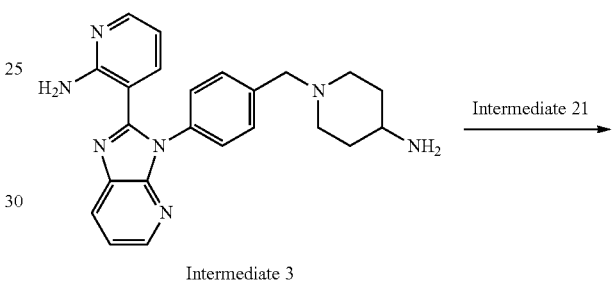

Intermediate 3

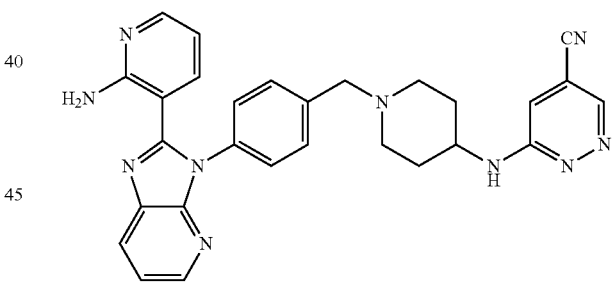

Example 51

Following the general procedure of Example 50, the reaction of Intermediate 3 (20 mg, 50 μmol) with Intermediate 21 (8.4 mg, 60 μmol) was carried out. After purified by prep-HPLC (column: Phenomenex C18 150*25 mm*10 μm; mobile phase: [water (NH$_4$HCO$_3$)-ACN]; B %: 25%-55%, 8 min), 6-((1-(4-(2-(2-aminopyridin-3-yl)-3H-imidazo[4,5-b]pyridin-3-yl)benzyl)piperidin-4-yl)amino)pyridazine-4-carbonitrile (Example 51, 9 mg, yield: 36%) was obtained as a light-gray solid. MS: m/z=503.2 [M+H]$^+$. $^1$H NMR (400 MHz, Dimethylsulfoxide-d$_6$) δ 8.68 (d, J=1.6 Hz, 1H), 8.33 (dd, J=4.8, 1.2 Hz, 1H), 8.20 (dd, J=8.0, 1.2 Hz, 1H), 7.98 (dd, J=4.8, 1.6 Hz, 1H), 7.46 (d, J=8.4 Hz, 2H), 7.42-7.32 (m, 4H), 7.22 (s, 1H), 7.17 (dd, J=7.6, 1.6 Hz, 1H), 7.00 (br s, 2H), 6.37 (dd, J=7.6, 4.8 Hz, 1H), 3.96-3.76 (m, 1H), 3.57 (s, 2H), 2.83 (d, J=11.2 Hz, 2H), 2.14 (t, J=11.2 Hz, 2H), 1.96 (d, J=10.0 Hz, 2H), 1.58-1.44 (m, 2H).

Example 52: 6-((4-(2-(2-Aminopyridin-3-yl)-5-phenyl-3H-imidazo[4,5-b]pyridin-3-yl)benzyl)amino)pyridazine-4-carbonitrile

Example 53: 6-(4-(4-(2-(2-Aminopyridin-3-yl)-5-phenyl-3H-imidazo[4,5-b]pyridin-3-yl)benzyl)piperazin-1-yl)pyridazine-4-carbonitrile

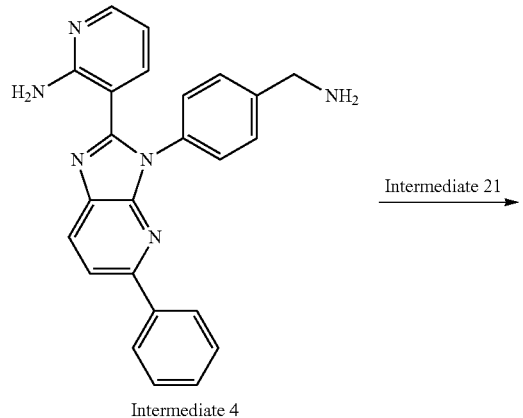

Intermediate 4

→ Intermediate 21

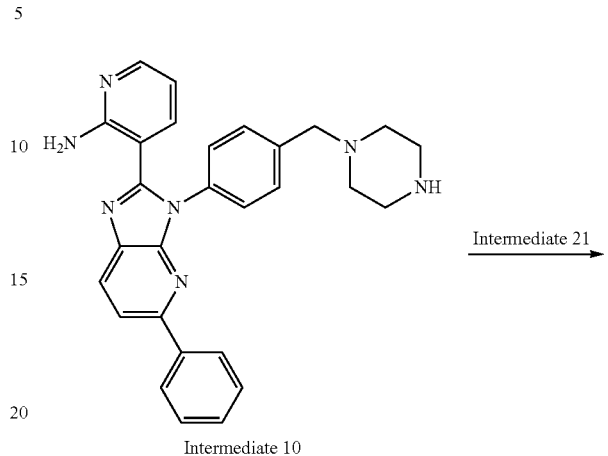

Intermediate 10

→ Intermediate 21

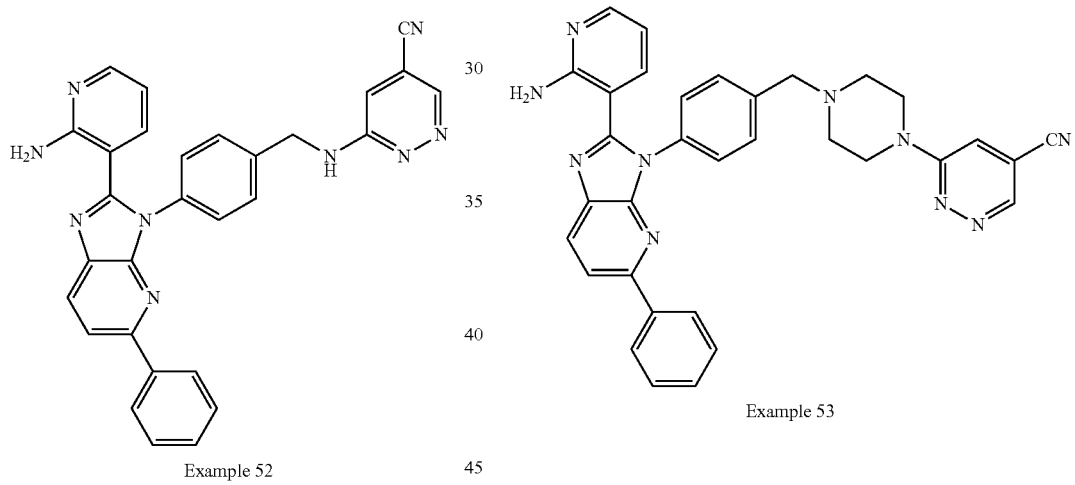

Example 52

Example 53

Following the general procedure of Example 50, the reaction of Intermediate 4 (20 mg, 50 µmol) with Intermediate 21 (8.5 mg, 61 µmol) was carried out. After purified by prep-HPLC (column: Phenomenex C18 150*25 mm*10 µm; mobile phase: [water (NH₄HCO₃)-ACN]; B %: 30%-60%, 8 min), 6-((4-(2-(2-aminopyridin-3-yl)-5-phenyl-3H-imidazo[4,5-b]pyridin-3-yl)benzyl)amino)pyridazine-4-carbonitrile (Example 52, 9 mg, yield: 34%) was obtained as a light-gray solid. MS: m/z=496.1 [M+H]⁺. ¹H NMR (400 MHz, Dimethylsulfoxide-d₆) δ 8.77 (d, J=1.6 Hz, 1H), 8.26 (d, J=8.4 Hz, 1H), 8.05-7.95 (m, 5H), 7.56-7.50 (m, 2H), 7.50-7.44 (m, 4H), 7.41-7.38 (m, 1H), 7.35 (d, J=1.6 Hz, 1H), 7.20 (dd, J=7.6, 1.6 Hz, 1H), 6.95 (br s, 2H), 6.40 (dd, J=7.6, 4.8 Hz, 1H), 4.74 (d, J=5.6 Hz, 2H).

Following the general procedure of Example 50, the reaction of Intermediate 10 (200 mg, 433 µmol) with Intermediate 21 (73 mg, 520 µmol) was carried out. After purified by prep-HPLC (column: Waters xbridge 150*25 mm 10 µm; mobile phase. [water (NH₄HCO₃)-ACN]; B %: 42%-72%, 10 min) to 6-(4-(4-(2-(2-aminopyridin-3-yl)-5-phenyl-3H-imidazo[4,5-b]pyridin-3-yl)benzyl)piperazin-1-yl)pyridazine-4-carbonitrile (Example 53, 15.2 mg, yield: 6.2%) was obtained as a light-gray solid. MS: m/z=565.2 [M+H]⁺. ¹H NMR (400 MHz, Dimethylsulfoxide-d₆) δ 8.84 (d, J=1.2 Hz, 1H), 8.27 (d, J=8.4 Hz, 1H), 8.16-7.96 (m, 4H), 7.87 (d, J=1.2 Hz, 1H), 7.56-7.51 (m, 2H), 7.51-7.44 (m, 4H), 7.43-7.37 (m, 1H), 7.16 (dd, J=7.6, 1.6 Hz, 1H), 7.04 (br s, 2H), 6.37 (dd, J=7.6, 4.8 Hz, 1H), 3.75-3.68 (m, 4H), 3.65 (s, 2H), 2.56-2.53 (m, 4H).

Example 54: 6-((1-(4-(2-(2-Aminopyridin-3-yl)-5-phenyl-3H-imidazo[4,5-b]pyridin-3-yl)benzyl)piperidin-4-yl)amino)pyridazine-4-carbonitrile

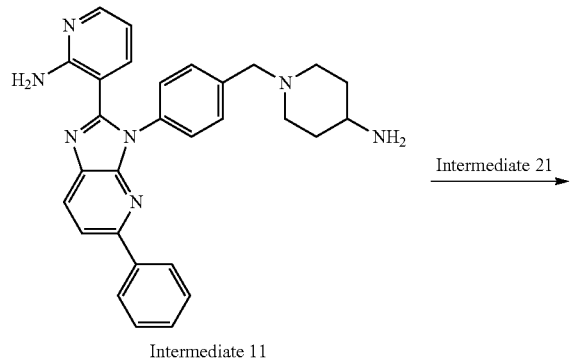

Intermediate 11

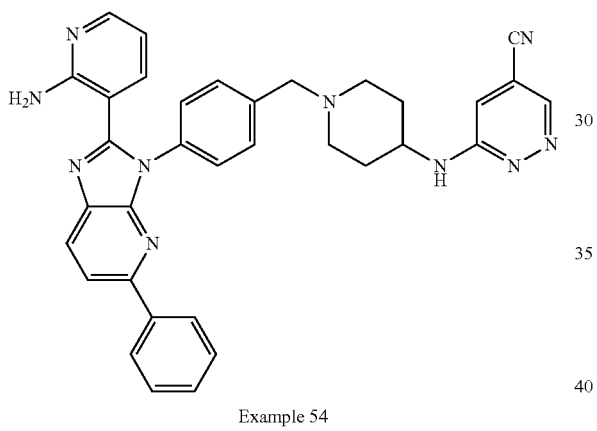

Example 54

Example 55: N-(1-(4-(2-(2-Aminopyridin-3-yl)-5-phenyl-3H-imidazo[4,5-b]pyridin-3-yl)benzyl)piperidin-4-yl)-2-cyanoisonicotinamide

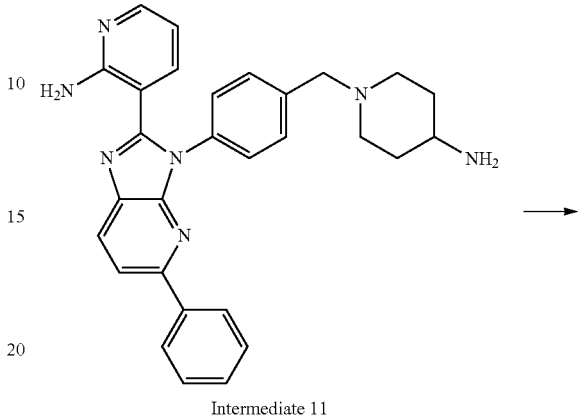

Intermediate 11

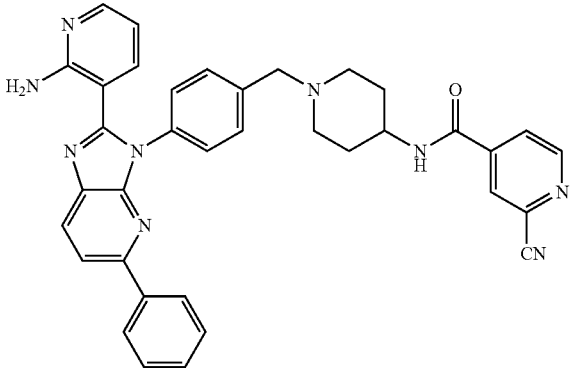

Example 55

Following the general procedure of Example 50, the reaction of Intermediate 11 (20 mg, 42 μmol) with Intermediate 21 (7 mg, 50 μmol) was carried out. After purified by prep-HPLC (column: Phenomenex C18 150*25 mm*10 μm; mobile phase: [water (NH$_4$HCO$_3$)-ACN]; B %: 35%-65%, 8 min), 6-((1-(4-(2-(2-aminopyridin-3-yl)-5-phenyl-3H-imidazo[4,5-b]pyridin-3-yl)benzyl)piperidin-4-yl)amino)pyridazine-4-carbonitrile (Example 54, 10 mg, yield: 41%) was obtained as a light-gray solid. MS: m/z=579.3 [M+H]$^+$. $^1$H NMR (400 MHz, Dimethylsulfoxide-d$_6$) δ 8.68 (d, J=1.6 Hz, 1H), 8.27 (d, J=8.4 Hz, 1H), 8.09-7.93 (m, 4H), 7.57-7.42 (m, 6H), 7.41-7.36 (m, 2H), 7.22 (s, 1H), 7.16 (dd, J=7.6, 1.6 Hz, 1H), 7.03 (br s, 2H), 6.37 (dd, J=7.6, 4.8 Hz, 1H), 3.95-3.75 (m, 1H), 3.59 (s, 2H), 2.84 (d, J=11.2 Hz, 2H), 2.16 (t, J=11.2 Hz, 2H), 1.97 (d, J=11.6 Hz, 2H), 1.60-1.43 (m, 2H).

Following the general procedure of Example 23, the reaction of Intermediate 11 (165 mg, 347 μmol) with 2-cyanopyridine-4-carboxylic acid ((61.7 mg, 416 μmol) was carried out. After purified by prep-HPLC (column: Waters xbridge 150*25 mm 10 μm; mobile phase: [water (NH$_4$HCO$_3$)-ACN]; B %: 38%-68%, 8 min), N-(1-(4-(2-(2-aminopyridin-3-yl)-5-phenyl-3H-imidazo[4,5-b]pyridin-3-yl)benzyl)piperidin-4-yl)-2-cyanoisonicotinamide (Example 55, 102 mg, yield: 48%) was obtained as a off-white solid. MS: m/z=606.2 [M+H]$^+$. $^1$H NMR (400 MHz, Chloroform-d) δ 8.84 (d, J=4.8 Hz, 1H), 8.13 (d, J=8.4 Hz, 1H), 8.07 (dd, J=5.2, 1.6 Hz, 1H), 8.04-8.00 (m, 3H), 7.84-7.79 (m, 2H), 7.50 (d, J=8.4 Hz, 2H), 7.45-7.37 (m, 5H), 7.09 (dd, J=8.0, 1.6 Hz, 1H), 6.59 (br s, 2H), 6.36 (dd, J=7.6, 4.8 Hz, 1H), 6.16 (br s, 1H), 4.14-4.01 (m, 1H), 3.65 (s, 2H), 2.97 (d, J=11.6 Hz, 2H), 2.31-2.24 (m, 2H), 2.11-2.05 (m, 2H), 1.75-1.68 (m, 2H).

Example 56: N-(1-(4-(2-(2-Aminopyridin-3-yl)-5-phenyl-3H-imidazo[4,5-b]pyridin-3-yl)benzyl)piperidin-4-yl)-6-cyanopicolinamide Example 57: N-(1-(4-(2-(2-Aminopyridin-3-yl)-5-phenyl-3H-imidazo[4,5-h]pyridin-3-yl)benzyl)piperidin-4-yl)-5-cyanonicotinamide

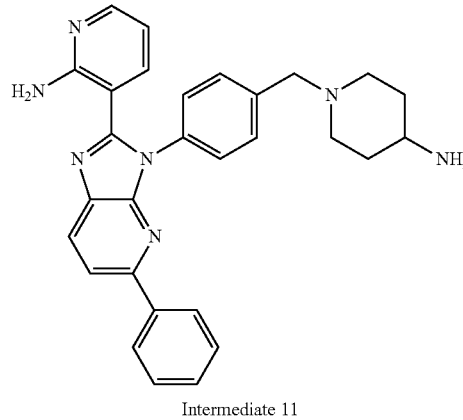

Intermediate 11

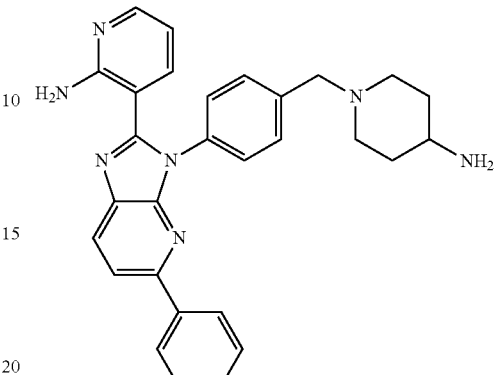

Intermediate 11

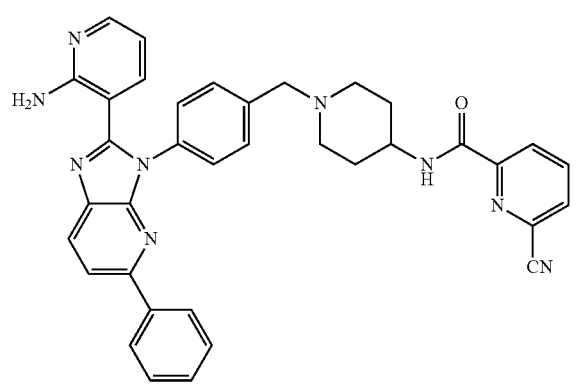

Example 56

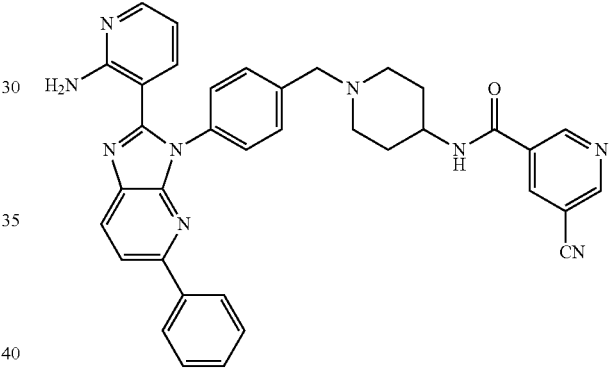

Example 57

Following the general procedure of Example 23, the reaction of Intermediate 11 (250 mg, 526 μmol) with 6-cyanopyridine-2-carboxylic acid (93 mg, 631 μmol) was carried out. After purified by prep-HPLC (column: Phenomenex C18 150*25 mm*10 μm; mobile phase: [water (NH$_4$HCO$_3$)-ACN]; B %: 33%-63%, 8 min), N-(1-(4-(2-(2-aminopyridin-3-yl)-5-phenyl-3H-imidazo[4,5-h]pyridin-3-yl)benzyl)piperidin-4-yl)-6-cyanopicolinamide (Example 56, 57.3 mg, yield: 18%) was obtained as a yellow solid. MS: m/z=606.2 [M+H]$^+$. $^1$H NMR (400 MHz, Chloroform-d) δ 8.42 (d, J=8.0 Hz, 1H), 8.13 (d, J=8.4 Hz, 1H), 8.06 (dd, J=4.8, 1.6 Hz, 1H), 8.05-7.99 (m, 3H), 7.85-7.79 (m, 3H), 7.57 (d, J=8.0 Hz, 2H), 7.47-7.41 (m, 4H), 7.40-7.34 (m, 1H), 7.11 (dd, J=7.6, 1.2 Hz, 1H), 6.65 (br s, 2H), 6.37 (dd, J=7.6, 4.8 Hz, 1H), 4.13-4.01 (m, 1H), 3.73 (s, 2H), 310-2.96 (m, 2H), 2.45-2.31 (m, 2H), 2.10 (d, J=10.8 Hz, 2H), 1.87-1.80 (m, 2H).

Following the general procedure of Example 23, the reaction of Intermediate 11 (250 mg, 526 μmol) with and 5-cyanopyridine-3-carboxylic acid (93 mg, 631 μmol) was carried out. After purified by prep-HPLC (column: Phenomenex C18 150*25 mm*10 μm; mobile phase: [water (NH$_4$HCO$_3$)-ACN]; B %: 40%-70%, 8 min), N-(1-(4-(2-(2-aminopyridin-3-yl)-5-phenyl-3H-imidazo[4,5-h]pyridin-3-yl)benzyl)piperidin-4-yl)-5-cyanonicotinamide (Example 57, 80.9 mg, yield: 25%) was obtained as a yellow solid. MS: m/z=606.2 [M+H]$^+$. $^1$H NMR (400 MHz, Chloroform-d) δ 9.16 (d, J=2.0 Hz, 1H), 8.96 (d, J=2.0 Hz, 1H), 8.48-8.40 (m, 1H), 8.13 (d, J=8.4 Hz, 1H), 8.06 (dd, J=4.8, 1.6 Hz, 1H), 8.03-7.99 (m, 2H), 7.80 (d, J=8.4 Hz, 1H), 7.52 (d, J=8.4 Hz, 2H), 7.45-7.40 (m, 4H), 7.39-7.35 (m, 1H), 7.08 (dd, J=7.6, 1.6 Hz, 1H), 6.59 (br s, 2H), 6.43 (br s, 1H), 6.35 (dd, J=7.6, 4.8 Hz, 1H), 4.15-4.05 (m, 1H), 3.70 (s, 2H), 3.02 (d, J=11.2 Hz, 2H), 2.33 (t, J=11.2 Hz, 2H), 2.10 (d, J=10.0 Hz, 2H), 1.81-1.71 (m, 2H).

Example 58: N-(1-(4-(2-(2-Aminopyridin-3-yl)-5-phenyl-3H-imidazo[4,5-h]pyridin-3-yl)benzyl)piperidin-4-yl)-2-cyanonicotinamide

Example 59: N-(1-(4-(2-(2-Aminopyridin-3-yl)-5-phenyl-3H-imidazo[4,5-b]pyridin-3-yl)benzyl)piperidin-4-yl)-3-cyanoisonicotinamide

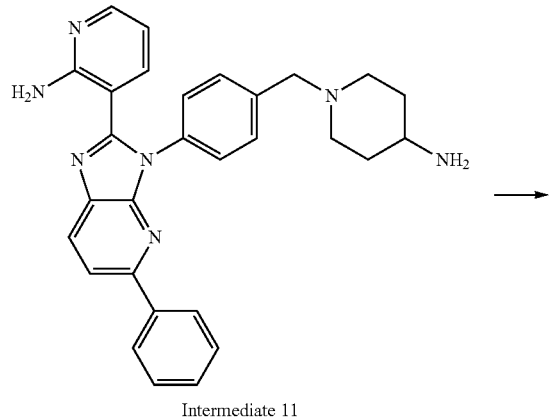

Intermediate 11

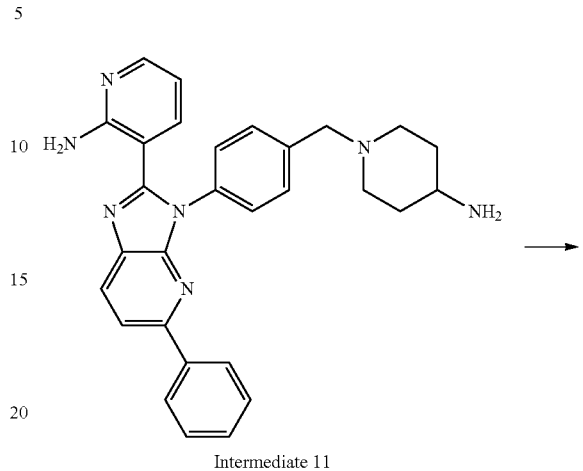

Intermediate 11

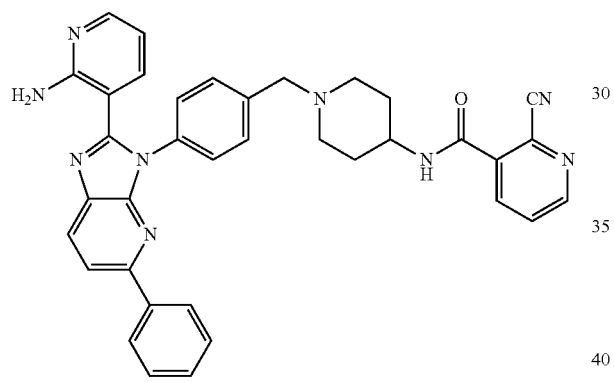

Example 58

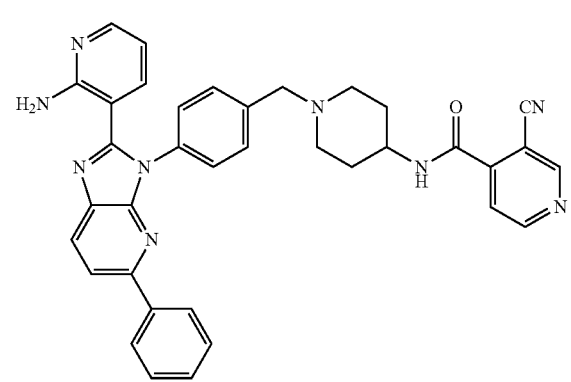

Example 59

Following the general procedure of Example 23, the reaction of Intermediate 11 (200 mg, 421 μmol) with 2-cyanopyridine-3-carboxylic acid (75 mg, 505 μmol) was carried out. After purified by prep-HPLC (column: Waters xbridge 150*25 mm 10 μm; mobile phase: [water (NH$_4$HCO$_3$)-ACN]; B %: 34%-64%, 8 min), N-(1-(4-(2-(2-aminopyridin-3-yl)-5-phenyl-3H-imidazo[4,5-h]pyridin-3-yl)benzyl)piperidin-4-yl)-2-cyanonicotinamide (Example 58, 55.9 mg, yield: 22%) was obtained as a yellow solid. MS: m/z=606.4 [M+H]$^+$. $^1$H NMR (400 MHz, Dimethylsulfoxide-d$_6$) δ 9.89 (s, 1H), 8.92 (d, J=4.4 Hz, 1H), 8.33-8.19 (m, 2H), 8.03 (d, J=7.6 Hz, 2H), 8.01-7.93 (m, 2H), 7.73 (dd, J=7.6, 5.2 Hz, 1H), 7.57-7.50 (m, 2H), 7.50-7.42 (m, 4H), 7.41-7.34 (m, 1H), 7.17 (d, J=6.8 Hz, 1H), 7.04 (br s, 2H), 6.38 (dd, J=7.6, 4.8 Hz, 1H), 4.38-4.25 (m, 1H), 3.62 (s, 2H), 2.98 (d, J=11.2 Hz, 2H), 2.64-2.55 (m, 2H), 2.16-2.04 (m, 2H), 1.67 (d, J=10.0 Hz, 2H).

Following the general procedure of Example 23, the reaction of Intermediate 11 (200 mg, 421 μmol) with 3-cyanopyridine-4-carboxylic acid (75 mg, 505 μmol) was carried out. After purified by prep-HPLC (column: Waters xbridge 150*25 mm 10 μm; mobile phase. [water (NH$_4$HCO$_3$)-ACN]; B %: 33%-63%, 8 min), N-(1-(4-(2-(2-aminopyridin-3-yl)-5-phenyl-3H-imidazo[4,5-b]pyridin-3-yl)benzyl)piperidin-4-yl)-3-cyanoisonicotinamide (Example 59, 67.8 mg, yield: 27%) was obtained as a yellow solid. MS: m/z=606.2 [M+H]$^+$. $^1$H NMR (400 MHz, Dimethylsulfoxide-d$_6$) δ 10.54 (s, 1H), 9.40 (s, 1H), 8.94 (d, J=4.8 Hz, 1H), 8.27 (d, J=8.4 Hz, 1H), 8.04 (d, J=7.6 Hz, 2H), 8.01-7.96 (m, 2H), 7.78 (d, J=4.8 Hz, 1H), 7.57-7.50 (m, 2H), 7.50-7.42 (m, 4H), 7.42-7.36 (m, 1H), 7.20-7.14 (m, 1H), 7.01 (br s, 2H), 6.38 (dd, J=7.6, 4.8 Hz, 1H), 4.34-4.24 (m, 1H), 3.64 (s, 2H), 3.00 (d, J=10.0 Hz, 2H), 2.63-2.56 (m, 2H), 2.21-2.06 (m, 2H), 1.65 (d, J=10.0 Hz, 2H).

1131

Example 60: N-(1-(4-(2-(2-Aminopyridin-3-yl)-5-phenyl-3H-imidazo[4,5-b]pyridin-3-yl)benzyl)piperidin-4-yl)-4-cyanonicotinamide

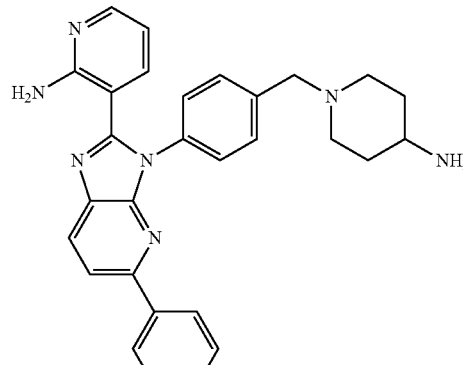

Intermediate 11

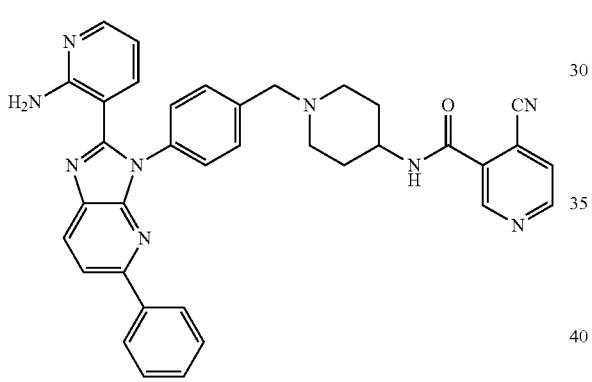

Example 60

Following the general procedure of Example 23, the reaction of Intermediate 11 (200 mg, 421 μmol) with 4-cyanopyridine-3-carboxylic acid (75 mg, 505 μmol). After purified by prep-HPLC (column: Phenomenex C18 150*25 mm*10 μm; mobile phase: [water (NH$_4$HCO$_3$)-ACN]; B %: 33%-63%, 8 min), N-(1-(4-(2-(2-aminopyridin-3-yl)-5-phenyl-3H-imidazo[4,5-b]pyridin-3-yl)benzyl)piperidin-4-yl)-4-cyanonicotinamide (Example 60, 58.8 mg, yield: 23%) was obtained as a yellow solid. MS: m/z=606.3 [M+H]$^+$. $^1$H NMR (400 MHz, Dimethylsulfoxide-d$_6$) δ 10.60 (s, 1H), 9.10-8.93 (m, 2H), 8.27 (d, J=8.4 Hz, 1H), 8.19-8.12 (m, 1H), 8.03 (d, J=7.2 Hz, 2H), 8.01-7.95 (m, 2H), 7.57-7.49 (m, 2H), 7.49-7.43 (m, 4H), 7.42-7.34 (m, 1H), 7.17 (dd, J=7.6, 1.6 Hz, 1H), 7.03 (brs, 2H), 6.38 (dd, J=7.6, 4.8 Hz, 1H), 4.34-4.21 (m, 1H), 3.62 (s, 2H), 2.98 (d, J=11.2 Hz, 2H), 2.64-2.52 (m, 2H), 2.09 (t, J=11.2 Hz, 2H), 1.69-1.56 (m, 2H).

1132

Example 61: N-(1-(4-(2-(2-Aminopyridin-3-yl)-5-phenyl-3H-imidazo[4,5-b]pyridin-3-yl)benzyl)piperidin-4-yl)-3-cyanopicolinamide

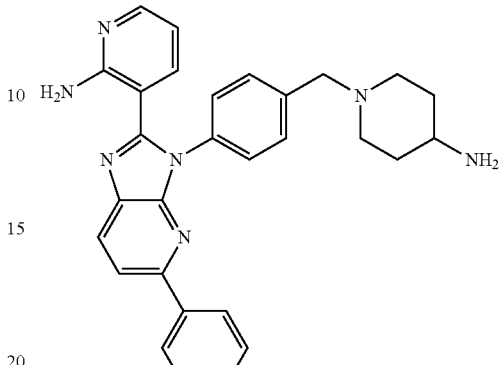

Intermediate 11

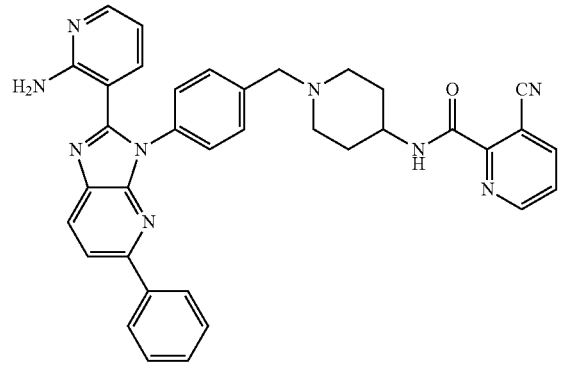

Example 61

Following the general procedure of Example 23, the reaction of Intermediate 11 (200 mg, 421 μmol) with and 3-cyanopyridine-2-carboxylic acid (75 mg, 505 μmol) was carried out. After purified by prep-HPLC (column: Phenomenex C18 150*25 mm*10 μm; mobile phase: [water (NH$_4$HCO$_3$)-ACN]; B %: 36%-66%, 8 min), N-(1-(4-(2-(2-aminopyridin-3-yl)-5-phenyl-3H-imidazo[4,5-b]pyridin-3-yl)benzyl)piperidin-4-yl)-3-cyanopicolinamide (Example 61, 25.2 mg, yield: 10%) was obtained as an off-white solid. MS: m/z=606.1 [M+H]$^+$. $^1$H NMR (400 MHz, Dimethylsulfoxide-d$_6$) δ 10.45 (s, 1H), 8.87 (dd, J=4.8, 1.2 Hz, 1H), 8.55 (dd, J=7.6, 1.2 Hz, 1H), 8.27 (d, J=8.4 Hz, 1H), 8.04 (d, J=7.2 Hz, 2H), 8.01-7.97 (m, 2H), 7.76 (dd, J=7.6, 4.8 Hz, 1H), 7.55-7.50 (m, 2H), 7.49-7.45 (m, 4H), 7.41-7.37 (m, 1H), 7.17 (dd, J=7.6, 1.6 Hz, 1H), 7.04 (brs, 2H), 6.38 (dd, J=7.6, 4.8 Hz, 1H), 4.38-4.30 (m, 1H), 3.63 (s, 2H), 2.99 (d, J=10.8 Hz, 2H), 2.66-2.52 (m, 2H), 2.15-2.06 (m, 2H), 1.65 (d, J=10.0 Hz, 2H).

Example 62: 4-((1-(4-(2-(2-Aminopyridin-3-yl)-3H-imidazo[4,5-b]pyridin-3-yl)benzyl)piperidin-4-yl)amino)picolinonitrile

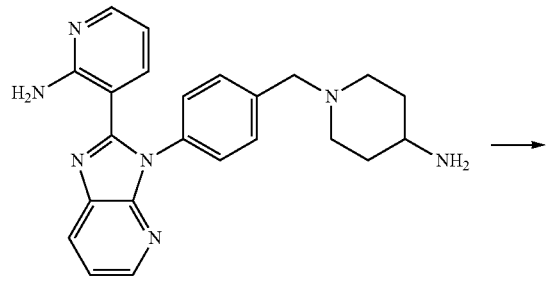

Intermediate 3

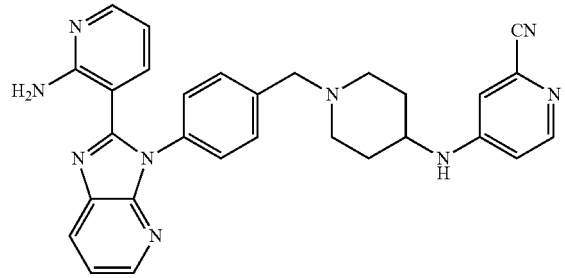

Example 62

To a solution of Intermediate 3 (200 mg, 501 μmol) and 4-fluoropyridine-2-carbonitrile (73 mg, 601 μmol) in DMSO (2 mL) was added DIEA (324 mg, 2.50 mmol). The mixture was stirred at 100 C for 16 hr. Then the mixture was purified by prep-HPLC (column: Phenomenex C18 150*25 mm*10 μm; mobile phase: [water (NH$_4$HCO$_3$)-ACN]; B %: 28%-58%, 8 min), 4-((1-(4-(2-(2-aminopyridin-3-yl)-3H-imidazo[4,5-b]pyridin-3-yl)benzyl)piperidin-4-yl)amino)picolinonitrile (Example 62, 23.8 mg, yield: 9.5%) as a light-yellow solid. MS: m/z=502.4 [M+H]$^+$. $^1$H NMR (400 MHz, Dimethylsulfoxide-d$_6$) δ 8.34 (dd, J=4.8, 1.2 Hz, 1H), 8.21 (dd, J=8.0, 1.2 Hz, 1H), 8.09 (d, J=5.6 Hz, 1H), 8.03-7.95 (m, 1H), 7.46 (d, J=8.4 Hz, 2H), 7.44-7.36 (m, 3H), 7.17 (dd, J=8.0, 2.0 Hz, 1H), 7.12-7.04 (m, 2H), 7.01 (br s, 2H), 6.75 (dd, J=6.0, 2.4 Hz, 1H), 6.38 (dd, J=7.6, 4.8 Hz, 1H), 3.57 (s, 2H), 2.86-2.77 (m, 3H), 2.20-2.11 (m, 2H), 1.93-1.85 (m, 2H), 1.50-1.37 (m, 2H).

Example 63: 6-((1-(4-(2-(2-Aminopyridin-3-yl)-3H-imidazo[4,5-b]pyridin-3-yl)benzyl)piperidin-4-yl)amino)picolinonitrile

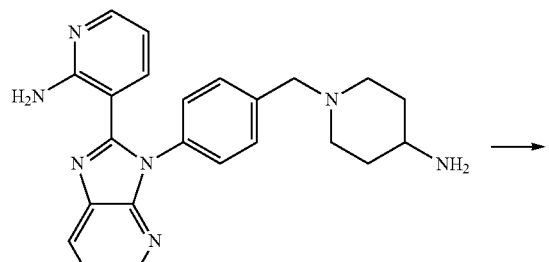

Intermediate 3

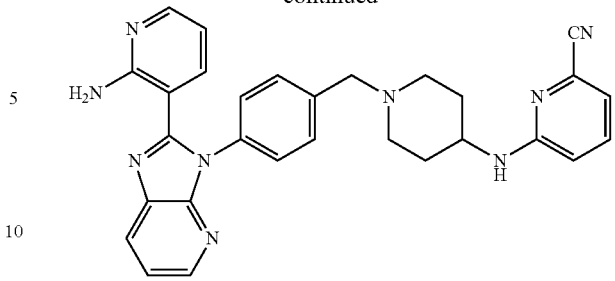

Example 63

Following the general procedure of Example 62, the reaction of Intermediate 3 (200 mg, 501 μmol) with 6-fluoropyridine-2-carbonitrile (73 mg, 601 μmol) was carried out. After purified by prep-HPLC (column: Phenomenex C18 150*25 mm*10 μm; mobile phase: [water (NH$_4$HCO$_3$)-ACN]; B %: 22%-52%, 8 min), 6-((1-(4-(2-(2-aminopyridin-3-yl)-3H-imidazo[4,5-b]pyridin-3-yl)benzyl)piperidin-4-yl)amino)picolinonitrile (Example 63, 15.0 mg, yield: 6.0%) was obtained as a light-green solid. MS: m/z=502.2 [M+H]$^+$. $^1$H NMR (400 MHz, Dimethylsulfoxide-d$_6$) δ 8.34 (d, J=4.8 Hz, 1H), 8.21 (d, J=8.0 Hz, 1H), 8.05-7.95 (m, 1H), 7.54-7.44 (m, 3H), 7.43-7.34 (m, 3H), 7.17 (d, J=7.2 Hz, 1H), 7.11 (d, J=7.6 Hz, 1H), 7.08-6.98 (m, 3H), 6.77 (d, J=8.4 Hz, 1H), 6.40-6.37 (m, 1H), 3.72-3.67 (m, 1H), 3.57 (br s, 2H), 2.84-2.79 (m, 2H), 2.19-2.10 (m, 2H), 1.94-1.87 (m, 2H), 1.51-1.41 (m, 2H).

Example 64: 6-((1-(4-(2-(2-aminopyridin-3-yl)-3H-imidazo[4,5-b]pyridin-3-yl)benzyl)piperidin-4-yl)amino)pyrimidine-4-carbonitrile

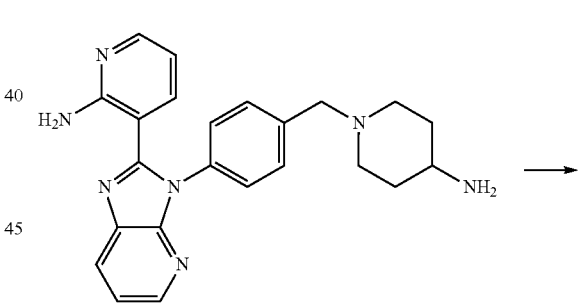

Intermediate 3

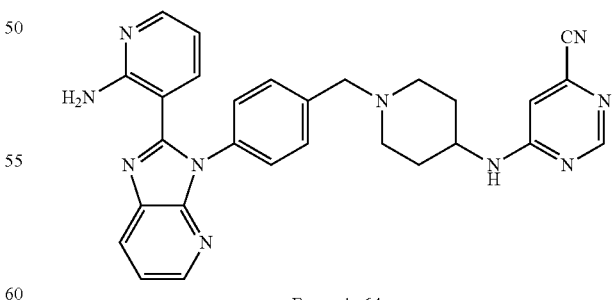

Example 64

Following the general procedure of Example 62, the reaction of Intermediate 3 (250 mg, 626 μmol) with 6-chloropyrimidine-4-carbonitrile (105 mg, 751 μmol) was carried out under microwave 130° C. After purified by prep-HPLC (column: Phenomenex C18 150*25 mm*10 μm; mobile phase: [water (NH₄HCO₃)-ACN]; B %: 20%-50%, 8 min), 6-((1-(4-(2-(2-aminopyridin-3-yl)-3H-imidazo[4,5-b]pyridin-3-yl)benzyl)piperidin-4-yl)amino)pyrimidine-4-carbonitrile (Example 64, 44.2 mg, yield: 14%) was obtained as a yellow solid. MS: m/z=503.1 [M+H]⁺. ¹H NMR (400 MHz, Chloroform-d) δ 8.56 (s, 1H), 8.39 (dd, J=4.8, 1.2 Hz, 1H), 8.10 (dd, J=8.0, 1.2 Hz, 1H), 8.04 (dd, J=4.8, 1.6 Hz, 1H), 7.52 (d, J=7.8 Hz, 2H), 7.36-7.29 (m, 3H), 7.06 (dd, J=7.6, 1.6 Hz, 1H), 6.68 (s, 1H), 6.62 (br s, 2H), 6.33 (dd, J=7.6, 4.8 Hz, 1H), 5.56-5.27 (m, 1H), 4.33-3.84 (m, 1H), 3.66 (s, 2H), 3.01-2.91 (m, 2H), 2.35-2.26 (m, 2H), 2.06 (d, J=11.2 Hz, 2H), 1.71-1.62 (m, 2H).

Example 65: 5-(4-(4-(2-(2-Aminopyridin-3-yl)-5-phenyl-3H-imidazo[4,5-b]pyridin-3-yl)benzyl)piperazin-1-yl)nicotinonitrile

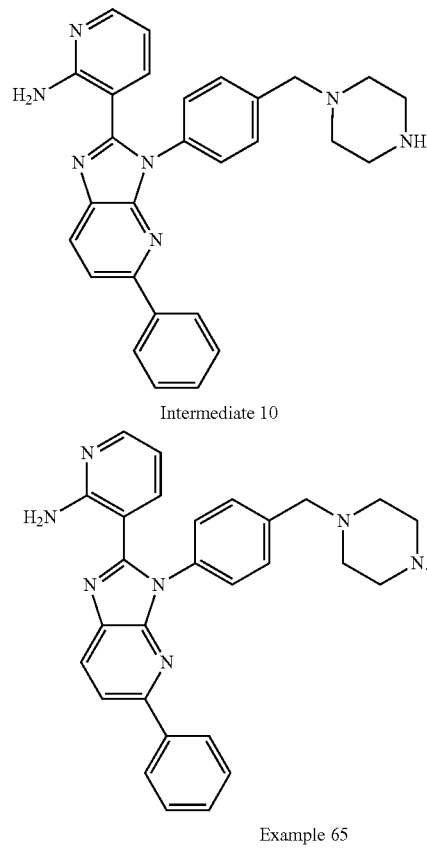

Intermediate 10

Example 65

Following the general procedure of Example 62, the reaction of Intermediate 10 (200 mg, 433 μmol) with 5-fluoropyridine-3-carbonitrile (63.5 mg, 520 μmol) was carried out. After purified by prep-HPLC (column: Phenomenex C18 150*25 mm*10 μm; mobile phase: [water (NH₄HCO₃)-ACN]; B %: 40%-70%, 8 min), 5-(4-(4-(2-(2-aminopyridin-3-yl)-5-phenyl-3H-imidazo[4,5-b]pyridin-3-yl)benzyl)piperazin-1-yl)nicotinonitrile (Example 65, 18.5 mg, yield: 7.6%) was obtained as a yellow solid. MS: m/z=564.1 [M+H]⁺. ¹H NMR (400 MHz, Chloroform-d) δ 8.48 (d, J=3.2 Hz, 1H), 8.30 (d, J=1.6 Hz, 1H), 8.14 (d, J=8.4 Hz, 1H), 8.10-8.04 (m, 1H), 8.02 (d, J=7.2 Hz, 2H), 7.81 (d, J=8.4 Hz, 1H), 7.52 (d, J=8.4 Hz, 2H), 7.45-7.41 (m, 4H), 7.40-7.38 (m, 1H), 7.34-7.32 (m, 1H), 7.12 (dd, J=7.6, 1.6 Hz, 1H), 6.67 (br s, 2H), 6.38 (dd, J=7.6, 4.8 Hz, 11H), 3.69 (s, 2H), 3.35-3.31 (m, 4H), 2.72-2.68 (m, 4H).

Example 66: 2-(4-(4-(2-(2-Aminopyridin-3-yl)-5-phenyl-3H-imidazo[4,5-b]pyridin-3-yl)benzyl)piperazin-1-yl)isonicotinonitrile

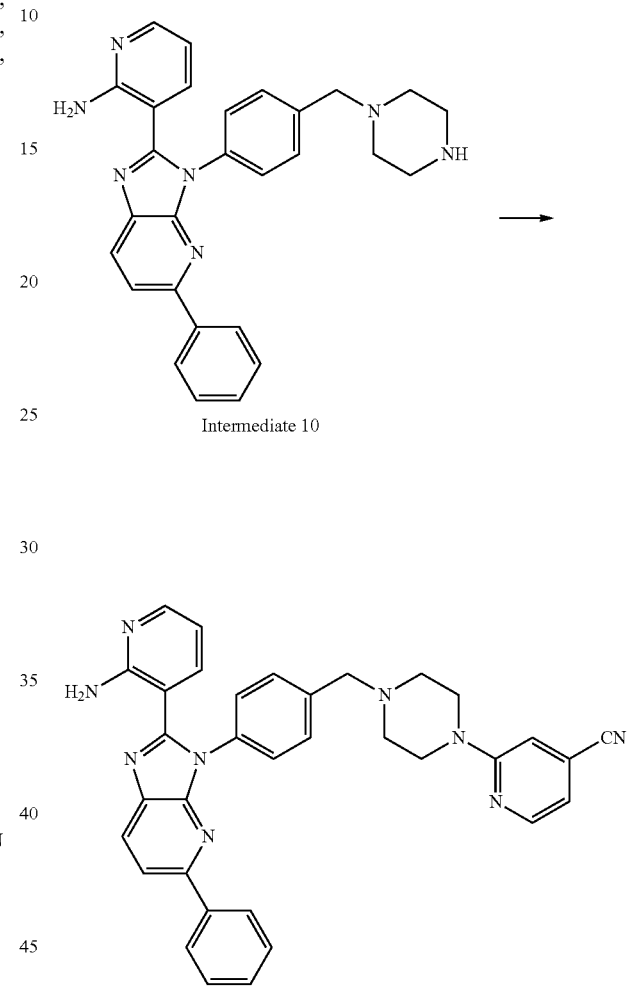

Intermediate 10

Example 66

Following the general procedure of Example 62, the reaction of Intermediate 10 (150 mg, 325 μmol) with 2-chloropyridine-4-carbonitrile (90 mg, 650 μmol) was carried out under microwave 130° C. After purified by prep-HPLC (column: Waters xbridge 150*25 mm 10 μm; mobile phase: [water (NH₄HCO₃)-ACN]; B %: 51%-81%, 8 min), 2-(4-(4-(2-(2-aminopyridin-3-yl)-5-phenyl-3H-imidazo[4,5-b]pyridin-3-yl)benzyl)piperazin-1-yl)isonicotinonitrile (Example 66, 16.6 mg, yield: 9.1%) was obtained as a yellow solid. MS: m/z=564.2 [M+H]⁺. ¹H NMR (400 MHz, Chloroform-d) δ 8.28 (d, J=5.2 Hz, 1H), 8.14 (d, J=8.4 Hz, 1H), 8.07 (dd, J=4.8, 1.6 Hz, 1H), 8.02 (d, J=6.8 Hz, 2H), 7.81 (d, J=8.4 Hz, 1H), 7.52 (d, J=8.4 Hz, 2H), 7.49-7.41 (m, 4H), 7.40-7.35 (m, 1H), 7.10 (dd, J=7.6, 1.6 Hz, 1H), 6.82 (s, 1H), 6.76 (d, J=5.2, 1.2 Hz, 1H), 6.61 (br s, 2H), 6.36 (dd, J=7.6, 4.8 Hz, 1H), 3.66 (s, 2H), 3.66-3.58 (m, 4H), 2.68-2.56 (m, 4H).

1137
Example 67: 6-(4-(4-(2-(2-Aminopyridin-3-yl)-5-phenyl-3H-imidazo[4,5-b]pyridin-3-yl)benzyl)piperazin-1-yl)pyrazine-2-carbonitrile

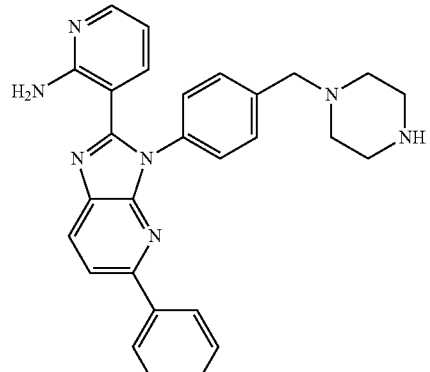

Intermediate 10

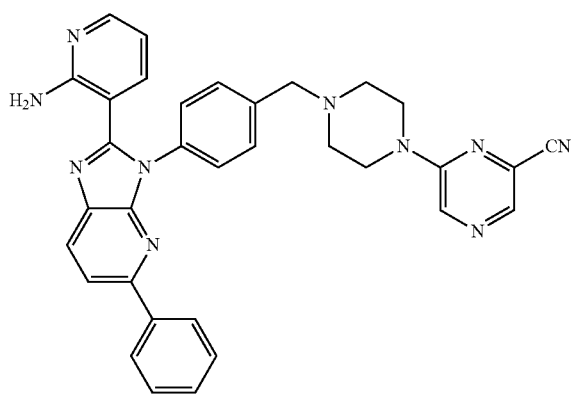

Example 67

Following the general procedure of Example 62, the reaction of Intermediate 10 (150 mg, 325 μmol) with 6-chloropyrazine-2-carbonitrile (91 mg, 650 μmol) was carried out under microwave 130° C. After purified by prep-HPLC (column: Waters xbridge 150*25 mm 10 μm; mobile phase: [water (NH$_4$HCO$_3$)-ACN]; B %: 18%-48%, 8 min), 6-(4-(4-(2-(2-aminopyridin-3-yl)-5-phenyl-3H-imidazo[4,5-b]pyridin-3-yl)benzyl)piperazin-1-yl)pyrazine-2-carbonitrile (Example 67, 25.6 mg, 14% yield) was obtained as a yellow solid. MS: m/z=565.4 [M+H]$^+$. $^1$H NMR (400 MHz, Chloroform-d) δ 8.29 (s, 1H), 8.18-8.10 (m, 2H), 8.08 (d, J=4.8 Hz, 1H), 8.02 (d, J=8.0 Hz, 2H), 7.81 (d, J=8.4 Hz, 1H), 7.52 (d, J=8.0 Hz, 2H), 7.47-7.42 (m, 4H), 7.41-4.35 (m, 1H), 7.11 (d, J=7.6 Hz, 1H), 6.66 (br s, 2H), 6.38 (dd, J=7.6, 4.8 Hz, 1H), 3.74-3.69 (m, 4H), 3.67 (s, 2H), 2.63 (t, J=4.8 Hz, 4H).

1138
Example 68: 2-(4-(4-(2-(2-Aminopyridin-3-yl)-5-phenyl-3H-imidazo[4,5-b]pyridin-3-yl)benzyl)piperazin-1-yl)pyrimidine-4-carbonitrile

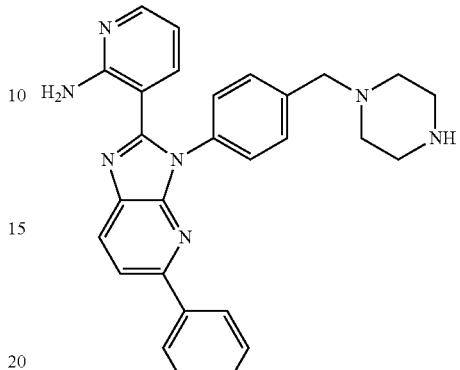

Intermediate 10

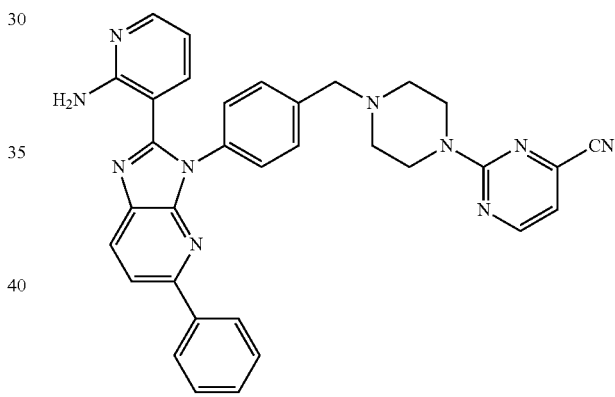

Example 68

Following the general procedure of Example 62, the reaction of Intermediate 10 (200 mg, 433 μmol) with 2-chloropyridine-4-carbonitrile (72 mg, 520 μmol) was carried out under microwave 130° C. After purified by prep-HPLC (column: Waters xbridge 150*25 mm 10 μm; mobile phase: [water (NH$_4$HCO$_3$)-ACN]; B %: 50%-80%, 8 min), 2-(4-(4-(2-(2-aminopyridin-3-yl)-5-phenyl-3H-imidazo[4,5-b]pyridin-3-yl)benzyl)piperazin-1-yl)pyrimidine-4-carbonitrile (Example 68, 31.0 mg, yield: 13%) was obtained as a yellow solid. MS: m/z=565.2 [M+H]$^+$. $^1$H NMR (400 MHz, Chloroform-d) δ 8.45 (d, J=4.8 Hz, 1H), 8.14 (d, J=8.4 Hz, 1H), 8.07 (d, J=4.4 Hz, 1H), 8.02 (d, J=7.6 Hz, 2H), 7.81 (d, J=8.4 Hz, 1H), 7.53 (d, J=8.0 Hz, 2H), 7.48-7.41 (m, 4H), 7.41-7.36 (m, 1H), 7.11 (d, J=7.6 Hz, 1H), 6.75 (d, J=4.8 Hz, 1H), 6.67 (br s, 2H), 6.37 (dd, J=7.6, 4.8 Hz, 1H), 3.94-3.87 (m, 4H), 3.66 (s, 2H), 2.58 (t, J=4.8 Hz, 4H).

Example 69: 6-(4-(4-(2-(2-Aminopyridin-3-yl)-3H-imidazo[4,5-b]pyridin-3-yl)benzyl)piperazine-1-carbonyl)picolinonitrile

Example 70: 4-(4-(4-(2-(2-Aminopyridin-3-yl)-5-phenyl-3H-imidazo[4,5-b]pyridin-3-yl)benzyl)piperazine-1-carbonyl)pyridazine-3-carbonitrile

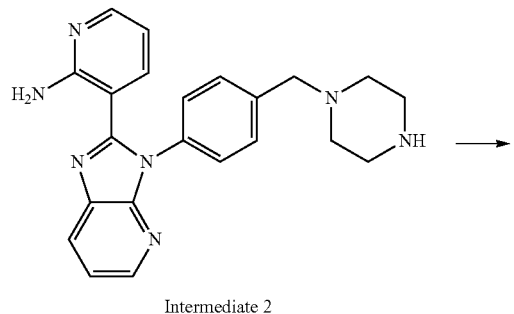

Intermediate 2

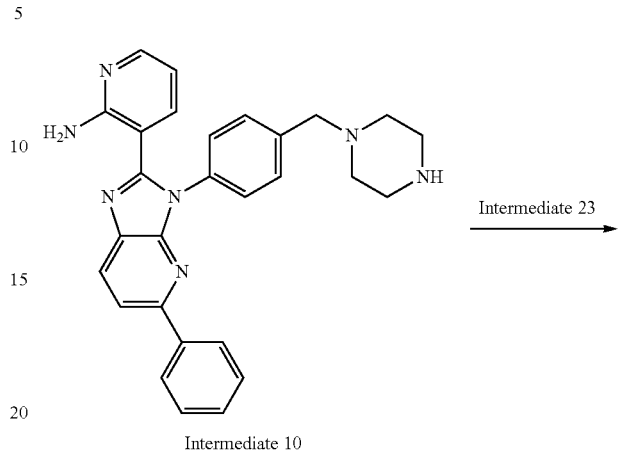

Intermediate 10

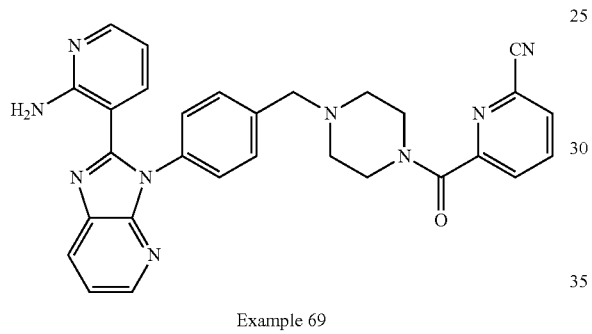

Example 69

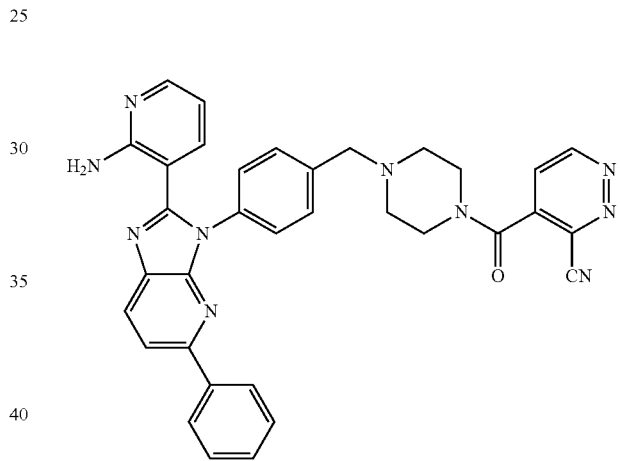

Example 70

To a solution of Intermediate 2 and 6-cyanopicolinic acid (84.5 mg, 570 μmol) in DMF (3 mL) was added HATU (395 mg, 1.04 mmol) and DIEA (201 mg, 1.56 mmol), then the reaction mixture was stirred at 25° C. for 4 hr. The reaction mixture was poured into H$_2$O (50 mL). The resulting mixture was extracted with CH$_2$Cl$_2$ (50 mL×3). The combined organic dried over anhydrous Na$_2$SO$_4$, filtered and concentrated to dryness. The residue was purified by prep-HPLC (column: Waters xbridge 150*40 mm 15 μm; mobile phase: [water (NH$_4$HCO$_3$)-ACN]; B %: 26%-56%, 8 min), 6-(4-(4-(2-(2-aminopyridin-3-yl)-3H-imidazo[4,5-b]pyridin-3-yl)benzyl)piperazine-1-carbonyl)picolinonitrile (Example 69, 36.6 mg, yield: 14%) was obtained as an off-white lyophilized powder. MS: m/z=516.1 [M+H]$^+$. $^1$H NMR (400 MHz, Dimethylsulfoxide-d$_6$) δ 8.33 (dd, J=4.8, 1.6 Hz, 1H), 8.25-8.16 (m, 2H), 8.15-8.09 (m, 1H), 7.98 (dd, J=4.8, 2.0 Hz, 1H), 7.90 (dd, J=7.6, 1.2 Hz, 1H), 7.47 (d, J=8.4 Hz, 2H), 7.43-7.32 (m, 3H), 7.16 (dd, J=7.6, 1.6 Hz, 1H), 7.00 (br s, 2H), 6.38 (dd, J=8.0, 5.2 Hz, 1H), 3.73-3.65 (m, 2H), 3.62 (s, 2H), 3.41-3.36 (m, 2H), 2.47-2.36 (m, 4H).

Following the general procedure of Example 69, the reaction of Intermediate 10 (200 mg, 433 μmol) with Intermediate 23 (71 mg, 476 μmol) was carried out. After purified by prep-HPLC (column: Waters xbridge 150*25 mm 10 μm; mobile phase: [water (NH$_4$HCO$_3$)-ACN]; B %: 35%-65%, 10 min), 4-(4-(4-(2-(2-aminopyridin-3-yl)-5-phenyl-3H-imidazo[4,5-b]pyridin-3-yl)benzyl)piperazine-1-carbonyl)pyridazine-3-carbonitrile (Example 70, 14.1 mg, yield: 5.5%) was obtained as a yellow solid. MS: m/z=593.3 [M+H]$^+$. $^1$H NMR (400 MHz, Dimethylsulfoxide-d$_6$) δ 9.61 (d, J=5.2 Hz, 1H), 8.27 (d, J=8.4 Hz, 1H), 8.07 (d, J=5.2 Hz, 1H), 8.05-8.01 (m, 2H), 8.00-7.96 (m, 2H), 7.54-7.44 (m, 6H), 7.42-7.36 (m, 1H), 7.15 (dd, J=7.6, 1.6 Hz, 1H), 7.01 (br s, 2H), 6.38 (dd, J=7.6, 4.8 Hz, 1H), 3.76-3.70 (m, 2H), 3.65 (s, 2H), 3.37-3.31 (m, 2H), 2.58-2.52 (m, 2H), 2.46-2.40 (m, 2H).

1141
Example 71: N-(1-(4-(2-(2-Aminopyridin-3-yl)-5-phenyl-3H-imidazo[4,5-b]pyridin-3-yl)benzyl)piperidin-4-yl)-3-cyanopyridazine-4-carboxamide

1142
Example 72: 4-(4-(4-(2-(2-Aminopyridin-3-yl)-5-phenyl-3H-imidazo[4,5-b]pyridin-3-yl)benzyl)piperazine-1-carbonyl)pyrimidine-5-carbonitrile

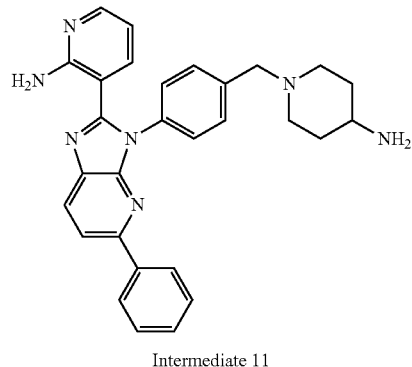

Intermediate 11

$\xrightarrow{\text{Intermediate 23}}$

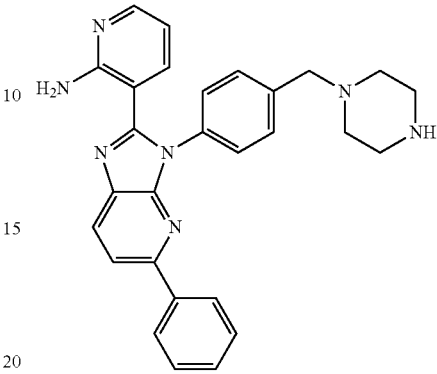

Intermediate 10

$\xrightarrow{\text{Intermediate 24}}$

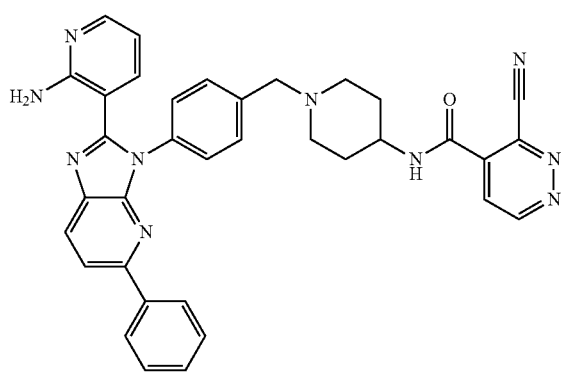

Example 71

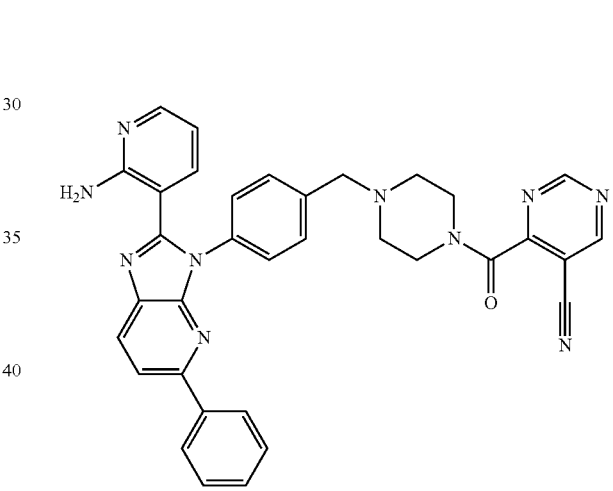

Example 72

Following the general procedure of Example 69, the reaction of Intermediate 11 (200 mg, 420 μmol) with Intermediate 23 (69 mg, 462 μmol) was carried out. The residue was purified by silica gel flash chromatography (Eluent of 0~7% MeOH in $CH_2Cl_2$), N-(1-(4-(2-(2-aminopyridin-3-yl)-5-phenyl-3H-imidazo[4,5-b]pyridin-3-yl)benzyl)piperidin-4-yl)-3-cyanopyridazine-4-carboxamide (Example 71, 22.6 mg, yield: 8.9%) was obtained as a yellow solid. MS: m/z=607.4 $[M+H]^+$. $^1$H NMR (400 MHz, Dimethylsulfoxide-$d_6$) δ 10.52 (s, 1H), 9.59 (d, J=5.6 Hz, 1H), 8.27 (d, J=8.4 Hz, 1H), 8.14 (d, J=5.2 Hz, 1H), 8.05-7.97 (m, 4H), 7.54-7.44 (m, 6H), 7.41-7.35 (m, 1H), 7.17 (d, J=7.6 Hz, 1H), 7.04 (br s, 2H), 6.38 (dd, J=8.0, 4.4 Hz, 1H), 4.42-4.28 (m, 1H), 3.63 (s, 2H), 2.99 (d, J=9.6 Hz, 2H), 2.64-2.56 (m, 2H), 2.14-2.08 (m, 2H), 1.70 (d, J=10.4 Hz, 2H).

Following the general procedure of Example 69, the reaction of Intermediate 10 (150 mg, 325 μmol) with Intermediate 24 (48 mg, 325 μmol) was carried out. The residue was purified by silica gel flash chromatography (Eluent of 0~7% MeOH in $CH_2Cl_2$), 4-(4-(4-(2-(2-aminopyridin-3-yl)-5-phenyl-3H-imidazo[4,5-b]pyridin-3-yl)benzyl)piperazine-1-carbonyl)pyrimidine-5-carbonitrile (Example 72, 44.8 mg, yield: 23%) was obtained as a yellow solid. MS: m/z=593.4 $[M+H]^+$. $^1$H NMR (400 MHz, Dimethylsulfoxide-$d_6$) δ 9.48 (d, J=5.2 Hz, 2H), 8.27 (d, J=8.4 Hz, 1H), 8.05-7.95 (m, 4H), 7.54-7.44 (m, 6H), 7.41-7.35 (m, 1H), 7.14 (dd, J=8.0, 1.6 Hz, 1H), 7.02 (br s, 2H), 6.38 (dd, J=7.6, 4.8 Hz, 1H), 3.77-3.71 (m, 2H), 3.65 (s, 2H), 3.39-3.31 (m, 2H), 2.59-2.51 (m, 2H), 2.48-2.42 (m, 2H).

Example 73: N-(1-(4-(2-(2-Aminopyridin-3-yl)-5-phenyl-3H-imidazo[4,5-b]pyridin-3-yl)benzyl)piperidin-4-yl)-5-cyanopyrimidine-4-carboxamide

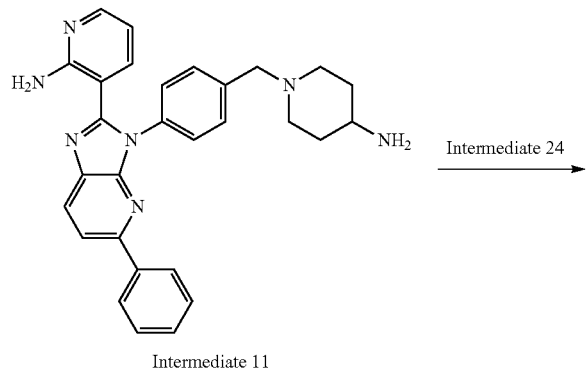

Intermediate 11

Example 74: 5-((1-(4-(2-(2-Aminopyridin-3-yl)-3H-imidazo[4,5-b]pyridin-3-yl)benzyl)piperidin-4-yl)amino)nicotinonitrile

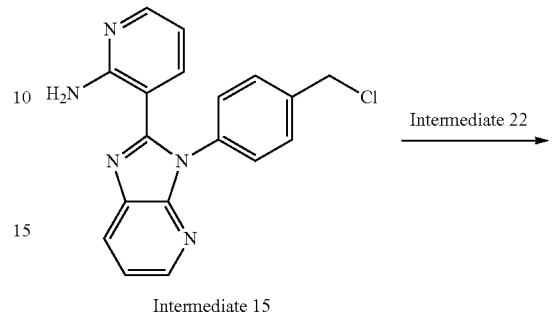

Intermediate 15

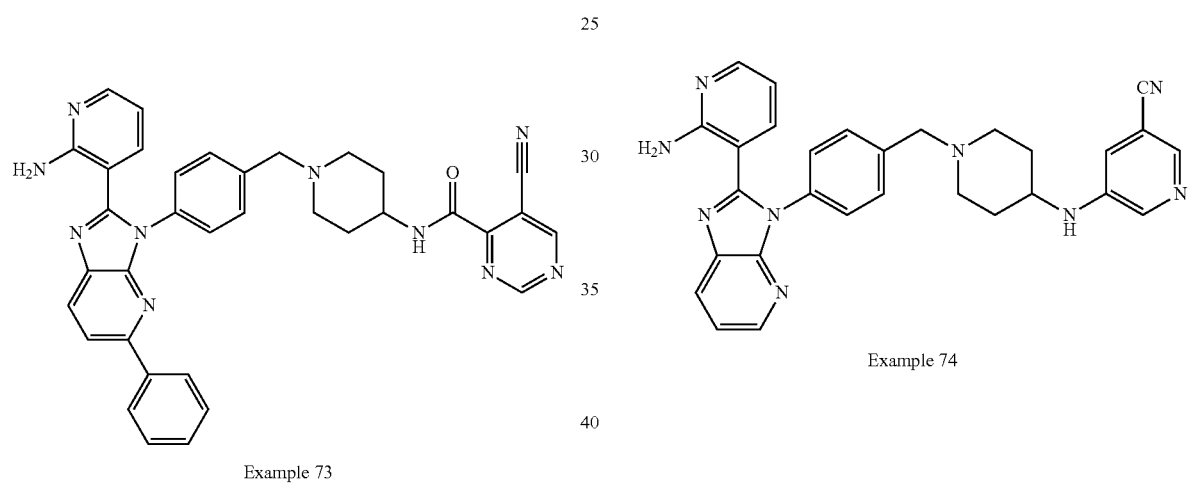

Example 73

Example 74

Following the general procedure of Example 69, the reaction of Intermediate 11 (150 mg, 315 μmol) with Intermediate 24 (51 mg, 346 μmol) was carried out. After purified by silica gel flash chromatography (Eluent of 0~7% MeOH in CH$_2$Cl$_2$), N-(1-(4-(2-(2-aminopyridin-3-yl)-5-phenyl-3H-imidazo[4,5-b]pyridin-3-yl)benzyl)piperidin-4-yl)-5-cyanopyrimidine-4-carboxamide (Example 73, 34.0 mg, yield: 18%) was obtained as a yellow solid. MS: m/z=607.3 [M+H]$^+$. $^1$H NMR (400 MHz, Dimethylsulfoxide-d$_6$) δ 9.62-9.43 (m, 2H), 9.09 (d, J=8.0 Hz, 1H), 8.27 (d, J=8.4 Hz, 1H), 8.05-7.97 (m, 4H), 7.54-7.42 (m, 6H), 7.41-7.35 (m, 1H), 7.17 (d, J=7.2 Hz, 1H), 7.03 (br s, 2H), 6.38 (dd, J=7.6, 4.8 Hz, 1H), 3.90-3.76 (m, 1H), 3.59 (s, 2H), 2.95-2.79 (m, 2H), 2.16-2.06 (m, 2H), 1.85-1.62 (m, 4H).

To a solution of Intermediate 15 and Intermediate 22 (90.4 mg, 447 μmol) in DMF (2 mL) was added K$_2$CO$_3$ (124 mg, 893 μmol) and NaI (7 mg, 45 μmol). The mixture was stirred at 80° C. for 2 hr. The reaction mixture was diluted with 20 mL H$_2$O and extracted with EtOAc (20 mL×2). The combined organic layers were washed with 30 mL brine, dried over Na$_2$SO$_4$, filtered and concentrated under reduced pressure to give a residue The residue was purified by prep-HPLC (column: Waters xbridge 150*25 mm 10 μm; mobile phase: [water (NH$_4$HCO$_3$)-ACN]; B %: 20%-50%, 11 min), 5-((1-(4-(2-(2-aminopyridin-3-yl)-3H-imidazo[4,5-b]pyridin-3-yl)benzyl)piperidin-4-yl)amino)nicotinonitrile (Example 74, 15 mg, yield: 6.3%) was obtained as a light-yellow solid. MS: m/z=502.4 [M+H]$^+$. $^1$H NMR (400 MHz, Dimethylsulfoxide-d$_6$) δ 8.33 (dd, J=4.4, 1.2 Hz, 1H), 8.23-8.19 (m, 2H), 8.06 (d, J=1.6 Hz, 1H), 7.98 (dd, J=4.8, 2.0 Hz, 1H), 7.45 (d, J=8.0, 2H), 7.43-7.35 (m, 4H), 7.33-7.31 (m, 1H), 7.16 (dd, J=7.6, 1.6 Hz, 1H), 7.00 (br s, 2H), 6.37 (dd, J=7.6, 4.8 Hz, 1H), 3.57 (s, 2H), 2.83-2.78 (m, 2H), 2.19-2.16 (m, 2H), 1.93-1.88 (m, 2H), 1.46-1.38 (m, 2H).

Example 75: 2-((1-(4-(2-(2-Aminopyridin-3-yl)-3H-imidazo[4,5-b]pyridin-3-yl)benzyl)piperidin-4-yl)amino)isonicotinonitrile

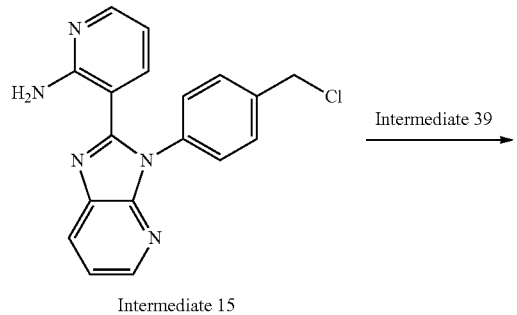

Intermediate 15

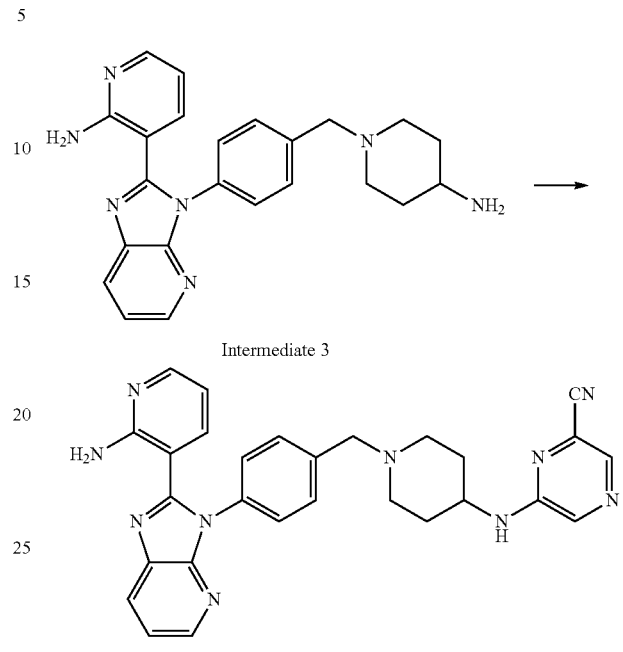

Example 75

To a solution of Intermediate 15 (150 mg, 446 μmol) in DMF (2 mL) was added NaI (6.7 mg, 44.7 μmol), K₂CO₃ (124 mg, 893 μmol) and Intermediate 39 (108 mg, 536 μmol). The mixture was stirred at 80° C. for 2 hr. The reaction mixture was quenched with H₂O (5 mL) at 25° C., and then diluted with CH₂Cl₂ (5 mL) and extracted with CH₂Cl₂ (10 mL×3). The combined organic layers were washed with brine (20 mL), dried over Na₂SO₄, filtered, and concentrated under reduced pressure to give a residue. The crude product was purified by prep-HPLC (column: Phenomenex C18 150×25 mm×10 μm; mobile phase: [water (NH₄HCO₃)-ACN]; B %: 26%-56%, 8 min), 2-((1-(4-(2-(2-aminopyridin-3-yl)-3H-imidazo[4,5-b]pyridin-3-yl)benzyl)piperidin-4-yl)amino)isonicotinonitrile (Example 75, 25.9 mg, yield: 12%) was obtained as a yellow solid. MS: m/z=502.1 [M+H]⁺. ¹H NMR (400 MHz, Dimethylsulfoxide-d₆) δ 8.33 (d, J=4.8 Hz, 1H), 8.21 (dd, J=8.0, 1.2 Hz, 1H), 8.15 (d, J=5.2 Hz, 1H), 7.99 (dd, J=5.2, 1.6 Hz, 1H), 7.45 (d, J=8.4 Hz, 2H), 7.42-7.35 (m, 3H), 7.16 (dd, J=7.6, 2.0 Hz, 1H), 7.05 (d, J=7.6 Hz, 1H), 7.01 (br s, 2H), 6.80 (s, 1H), 6.75 (d, J=5.2 Hz, 1H), 6.437 (dd, J=7.6, 4.8 Hz, 1H), 3.79-3.66 (m, 1H), 3.55 (s, 2H), 2.86-2.76 (m, 2H), 2.18-2.05 (m, 2H), 1.91-1.81 (m, 2H), 1.53-1.39 (m, 2H).

Example 76: 6-((1-(4-(2-(2-Aminopyridin-3-yl)-3H-imidazo[4,5-b]pyridin-3-yl)benzyl)piperidin-4-yl)amino)pyrazine-2-carbonitrile

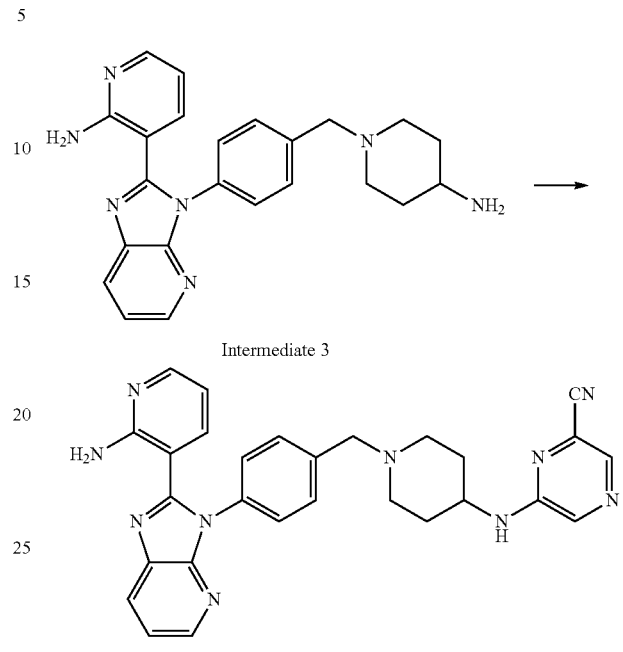

To a solution of Intermediate 3 (200 mg, 501 μmol) and 6-chloropyrazine-2-carbonitrile (84 mg, 601 μmol) in NMP (2 mL) was added DIEA (324 mg, 2.5 mmol). The mixture was stirred under microwave at 130° C. for 0.5 hr. Then the mixture was purified by prep-HPLC (column: Waters Xbridge 150*25 mm*5 μm; mobile phase: [water (NH₄HCO₃)-ACN]; B %: 30%-60%, 8 min), 6-((1-(4-(2-(2-aminopyridin-3-yl)-3H-imidazo[4,5-b]pyridin-3-yl)benzyl)piperidin-4-yl)amino)pyrazine-2-carbonitrile (Example 76, 12.6 mg, yield: 5.0%) as light-pink solid. MS: m/z=503.2 [M+H]⁺. ¹H NMR (400 MHz, Dimethylsulfoxide-d₆) δ 8.33 (d, J=4.8 Hz, 1H), 8.21 (d, J=8.0 Hz, 1H), 8.09 (d, J=10.4 Hz, 2H), 7.98 (d, J=4.8 Hz, 1H), 7.80-7.71 (m, 1H), 7.45 (m, J=7.6 Hz, 2H), 7.42-7.36 (m, 3H), 7.16 (d, J=8.4 Hz, 1H), 7.01 (br s, 2H), 6.37 (dd, J=7.6, 4.8 Hz, 1H), 3.71-3.68 (m, 1H), 3.57 (s, 2H), 2.83-2.79 (m, 2H), 2.18-2.12 (m, 2H), 1.94-1.88 (m, 2H), 1.53-1.44 (m, 2H).

Example 77: 2-((1-(4-(2-(2-Aminopyridin-3-yl)-3H-imidazo[4,5-b]pyridin-3-yl)benzyl)piperidin-4-yl)amino)pyrimidine-4-carbonitrile

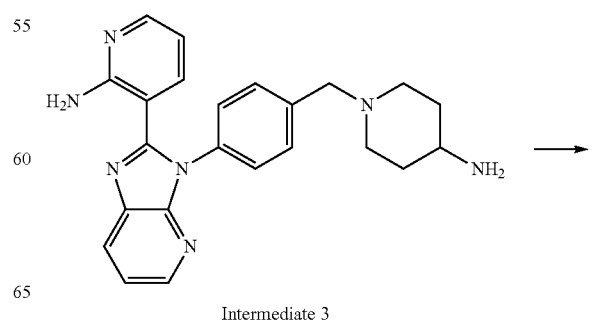

Intermediate 3

1147
-continued

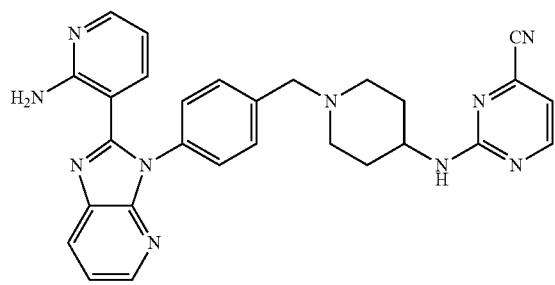

Example 77

Following the general procedure of Example 76, the reaction of Intermediate 3 (200 mg, 501 μmol) with 2-chloropyrimidine-4-carbonitrile (84 mg, 601 μmol) was carried out. After purified by prep-HPLC (column: Phenomenex C18 150*25 mm*10 μm; mobile phase: [water (NH$_4$HCO$_3$)-ACN]; B %: 25%-55%, 8 min) and then (column: Phenomenex luna C18 150*25 mm*10 μm; mobile phase: [water (FA)-ACN]; B %: 0%-30%, 58 min), 2-((1-(4-(2-(2-aminopyridin-3-yl)-3H-imidazo[4,5-b]pyridin-3-yl)benzyl)piperidin-4-yl)amino)pyrimidine-4-carbonitrile (Example 77, 5.7 mg, 3 HCOOH salt, yield: 2.3%) was obtained as an off-white solid. MS: m/z=503.3 [M+H]$^+$. $^1$H NMR (400 MHz, Methanol-d$_4$) δ 8.49 (d, J=4.8 Hz, 1H), 8.35 (d, J=4.8 Hz, 1H), 8.24-8.16 (m, 4H), 8.02-7.95 (m, 1H), 7.68 (d, J=8.4 Hz, 2H), 7.54 (d, J=8.0 Hz, 2H), 7.45 (dd, J=8.0, 4.8 Hz, 1H), 7.39-7.33 (m, 1H), 6.96 (d, J=4.4 Hz, 1H), 6.49 (dd, J=7.6, 4.8 Hz, 1H), 4.33 (br s, 2H), 4.11-4.03 (m, 1H), 3.47 (d, J=12.4 Hz, 2H), 3.11 (t, J=11.2 Hz, 2H), 2.24 (d, J=12.4 Hz, 2H), 1.94-1.80 (m, 2H).

Example 78: 6-(4-(4-(2-(2-Aminopyridin-3-yl)-5-phenyl-3H-imidazo[4,5-b]pyridin-3-yl)benzyl)piperazin-1-yl)pyrimidine-4-carbonitrile

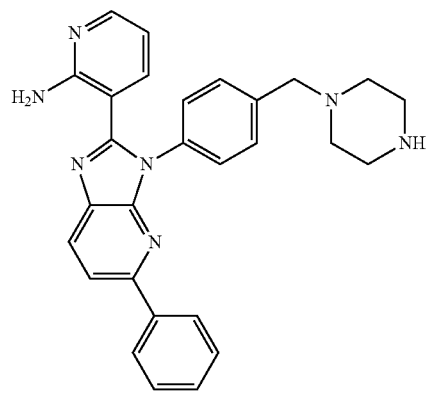

Intermediate 10

1148
-continued

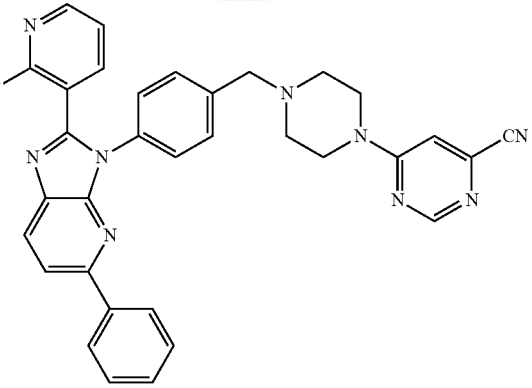

Example 78

Following the general procedure of Example 76, the reaction of Intermediate 10 (150 mg, 325 μmol) with 6-chloropyrimidine-4-carbonitrile (68 mg, 487 μmol) was carried out. After purified by prep-HPLC (column: Waters xbridge 150*25 m 10 μm; mobile phase: [water (NH$_4$HCO$_3$)-ACN]; B %: 44%-74%, 8 min), 6-(4-(4-(2-(2-aminopyridin-3-yl)-5-phenyl-3H-imidazo[4,5-b]pyridin-3-yl)benzyl)piperazin-1-yl)pyrimidine-4-carbonitrile (Example 78, 21.1 mg, yield: 11.5%) was obtained as a green solid. MS: m/z=565.2 [M+H]$^+$. $^1$H NMR (400 MHz, Chloroform-d$_6$) δ 8.60 (s, 1H), 8.14 (d, J=8.4 Hz, 1H), 8.07 (d, J=4.8 Hz, 1H), 8.02 (d, J=7.6 Hz, 2H), 7.81 (d, J=8.4 Hz, 1H), 7.51 (d, J=8.0 Hz, 1H), 7.47-7.42 (m, 4H), 7.41-7.36 (m, 1H), 7.11 (d, J=7.6 Hz, 1H), 6.84 (s, 1H), 6.66 (br s, 2H), 6.37 (dd, J=7.6, 4.8 Hz, 1H), 3.88-3.68 (m, 4H), 3.67 (s, 2H), 2.61 (t, J=4.8 Hz, 4H).

Example 79: 5-(4-(4-(2-(2-Aminopyridin-3-yl)-3H-imidazo[4,5-b]pyridin-3-yl)benzyl)piperazine-1-carbonyl)nicotinonitrile

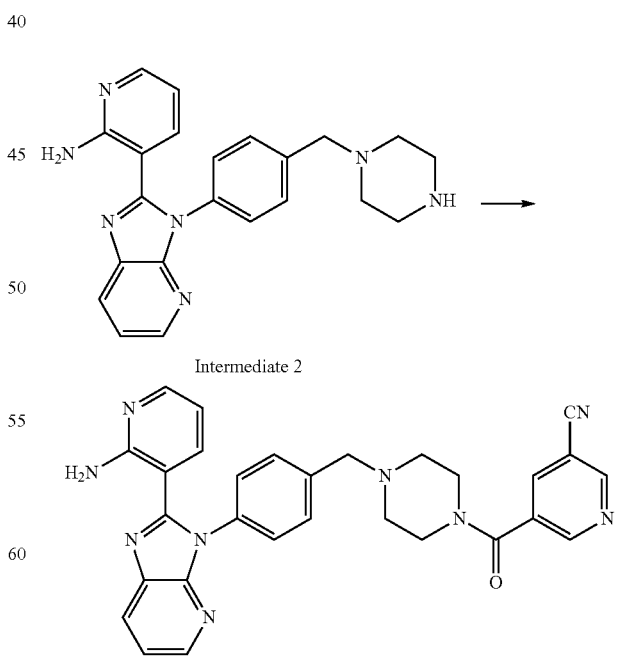

Intermediate 2

Example 79

Following the general procedure of Example 23, the reaction of Intermediate 2 (200 mg, 519 µmol) with 5-cyanopyridine-3-carboxylic acid (92 mg, 623 µmol) was carried out. After purified by prep-HPLC (column: Phenomenex Luna C18 150*25 mm*10 µm; mobile phase: [water (NH₄HCO₃)-ACN]; B %: 23%-53%, 8 min), 5-(4-(4-(2-(2-aminopyridin-3-yl)-3H-imidazo[4,5-b]pyridin-3-yl)benzyl)piperazine-1-carbonyl)nicotinonitrile (Example 79, 47.6 mg, yield: 18%) was obtained as a yellow solid. MS: m/z=516.2 [M+H]⁺. ¹H NMR (400 MHz, Chloroform-d) δ 8.93 (d, J=2.0 Hz, 1H), 8.85 (d, J=2.0 Hz, 1H), 8.40 (dd, J=4.8, 1.2 Hz, 1H), 8.11 (dd, J=8.0, 1.2 Hz, 1H), 8.07-8.04 (m, 2H), 7.50 (d, J=8.0 Hz, 2H), 7.36 (d, J=8.4 Hz, 2H), 7.33-7.30 (m, 1H), 7.07 (dd, J=7.6, 1.6 Hz, 1H), 6.62 (br s, 2H), 6.33 (dd, J=8.0, 4.8 Hz, 1H), 3.89-3.79 (m, 2H), 3.64 (s, 2H) 3.50-3.39 (m, 2H), 2.64-2.57 (m, 2H), 2.54-2.46 (m, 2H).

Example 80: 6-(4-(4-(2-(2-Aminopyridin-3-yl)-3H-imidazo[4,5-b]pyridin-3-yl)benzyl)piperazine-1-carbonyl)nicotinonitrile Example 81: N-(1-(4-(2-(2-Aminopyridin-3-yl)-5-phenyl-3H-imidazo[4,5-b]pyridin-3-yl)benzyl)piperidin-4-yl)-5-cyanopicolinamide

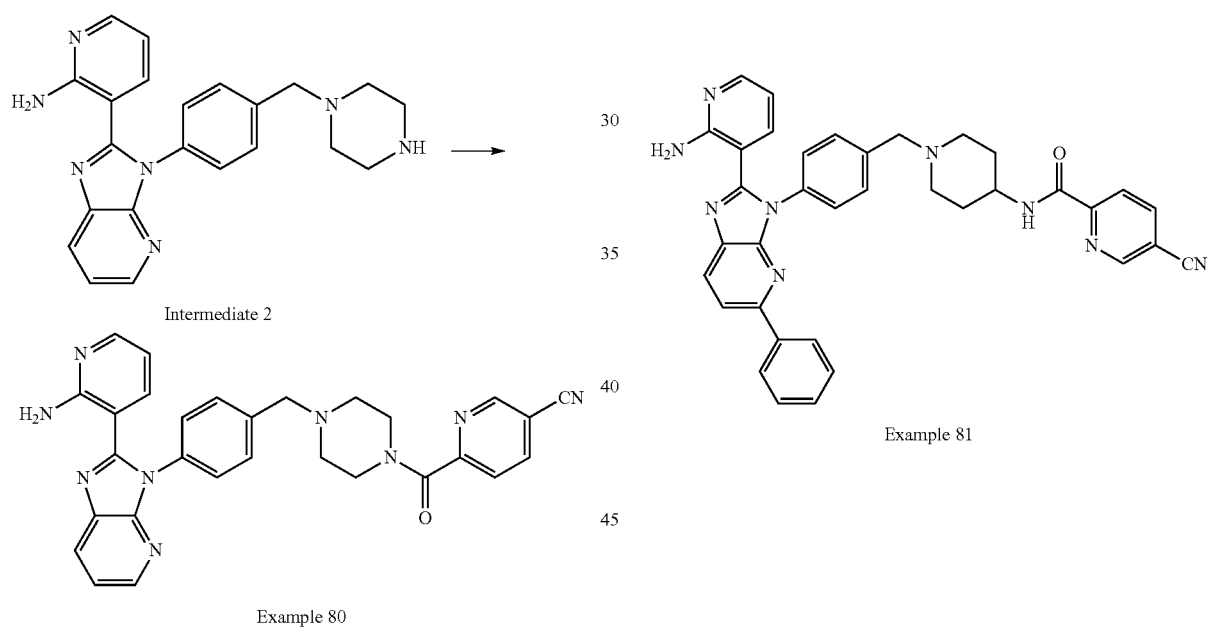

Intermediate 2

Intermediate 11

Example 80

Example 81

Following the general procedure of Example 23, the reaction of Intermediate 2 (200 mg, 519 µmol) with 5-cyanopyridine-2-carboxylic acid (92 mg. 623 µmol,) was carried out. After purified by prep-HPLC (column: Phenomenex Luna C18 150*25 mm*10 µm; mobile phase: [water (NH₄HCO₃)-ACN]; B %: 23%-53%, 8 min), 6-(4-(4-(2-(2-aminopyridin-3-yl)-3H-imidazo[4,5-b]pyridin-3-yl)benzyl)piperazine-1-carbonyl)nicotinonitrile (Example 80, 41.4 mg, yield: 15%) was obtained as a yellow solid. MS: m/z=516.2 [M+H]⁺. ¹H NMR (400 MHz, Chloroform-d) δ 8.86 (d, J=1.6 Hz, 1H), 8.40 (dd, J=4.8, 1.2 Hz, 1H), 8.12-8.04 (m, 3H), 7.81 (d, J=7.6 Hz, 1H), 7.51 (d, J=8.0 Hz, 2H), 7.38-7.30 (m, 3H), 7.08 (dd, J=7.6, 1.6 Hz, 1H), 6.75 (br s, 2H), 6.34 (dd, J=7.6, 4.8 Hz, 1H), 3.89-3.84 (m, 2H), 3.64 (s, 2H), 3.62-3.59 (m, 2H), 2.65-2.61 (m, 2H), 2.55-2.51 (m, 2H).

Following the general procedure of Example 23, the reaction of Intermediate 11 (187 mg, 351 µmol,) with 5-cyanopicolinic acid (57.0 mg, 386 µmol) was carried out. After purified by prep-HPLC (column: Phenomenex luna C18 150×25 mm×10 µm; mobile phase: [water (FA)-ACN]; B %: 8%-38%, 9 min), N-(1-(4-(2-(2-aminopyridin-3-yl)-5-phenyl-3H-imidazo[4,5-b]pyridin-3-yl)benzyl)piperidin-4-yl)-5-cyanopicolinamide (Example 81, 51.8 mg, yield: 24%) was obtained as an off-white lyophilized powder. MS: m/z=606.4 [M+H]⁺. ¹H NMR (400 MHz, Dimethylsulfoxide-d₆) δ 9.16-9.05 (m, 1H), 8.80 (d, J=8.4 Hz, 1H), 8.51 (dd, J=8.4, 2.0 Hz, 1H), 8.27 (d, J=8.4 Hz, 1H), 8.17 (d, J=8.0 Hz, 1H), 8.07-7.95 (m, 4H), 7.51-7.43 (m, 6H), 7.42-7.36 (m, 1H), 7.16 (dd, J=7.6, 1.6 Hz, 1H), 7.03 (br s, 2H), 6.38 (dd, J=7.6, 4.8 Hz, 1H), 3.93-3.79 (m, 1H), 3.58 (s, 2H), 2.87-2.84 (m, 2H), 2.17-2.06 (m, 2H), 1.79-1.67 (m, 4H).

Example 82: 4-(4-(4-(2-(2-Aminopyridin-3-yl)-5-phenyl-3H-imidazo[4,5-b]pyridin-3-yl)benzyl)piperazin-1-yl)picolinonitrile

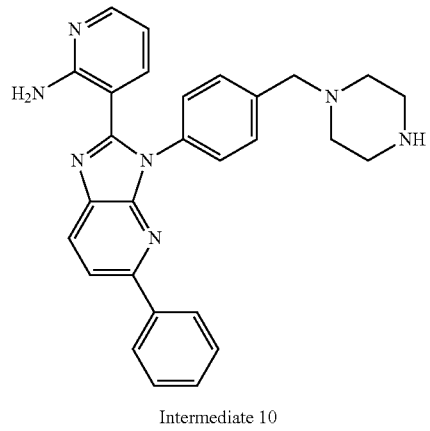

Intermediate 10

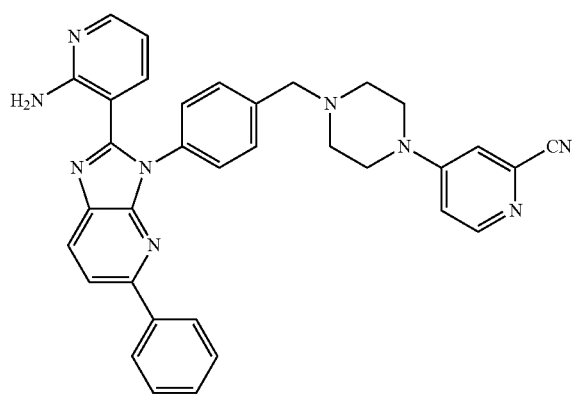

Example 82

Following the general procedure of Example 14, the reaction of Intermediate 10 (130 mg, 281 μmol) with 4-fluoropicolinonitrile (38.0 mg, 310 μmol) was carried out. After purified by prep-HPLC (column: Welch Xtimate C18 150*25 mm*5 μm; mobile phase: [water (NH$_4$HCO$_3$)-ACN]; B %: 37%-67%, 2 min), 4-(4-(4-(2-(2-aminopyridin-3-yl)-5-phenyl-3H-imidazo[4,5-b]pyridin-3-yl)benzyl)piperazin-1-yl)picolinonitrile (Example 82, 47.0 mg, yield: 30%) was obtained as a light-yellow lyophilized powder. MS: m/z=564.4 [M+H]$^+$. $^1$H NMR (400 MHz, Dimethylsulfoxide-d$_6$) δ 8.27 (d, J=8.4 Hz, 1H), 8.23 (d, J=6.0 Hz, 1H), 8.07-7.96 (m, 4H), 7.56-7.44 (m, 7H), 7.43-7.37 (m, 1H), 7.15 (dd, J=7.6, 1.6 Hz, 1H), 7.07 (dd, J=6.4, 2.8 Hz, 1H), 7.03 (br s, 2H), 6.36 (dd, J=7.6, 4.8 Hz, 1H), 3.64 (s, 2H), 3.50-3.43 (m, 4H), 2.55-2.51 (m, 4H).

Example 83: 6-(4-(4-(2-(2-Aminopyridin-3-yl)-5-phenyl-3H-imidazo[4,5-b]pyridin-3-yl)benzyl)piperazin-1-yl)picolinonitrile

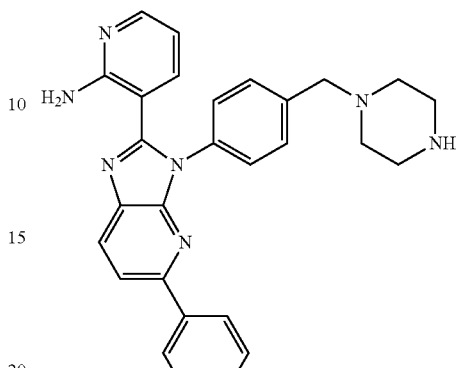

Intermediate 10

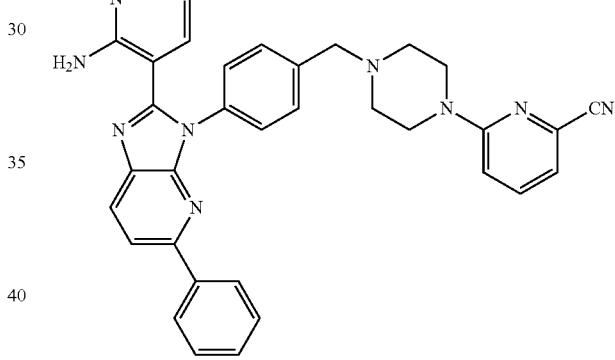

Example 83

Following the general procedure Example 14, the reaction of Intermediate 10 (130 mg, 281 μmol) with 6-fluoropicolinonitrile (35.0 mg, 287 μmol) was carried out. After purified by prep-HPLC (column: Welch Xtimate C18 150-25 mm×5 μm; mobile phase: [water (NH$_4$HCO$_3$)-ACN]; B %: 37%-67%, 2 min), 6-(4-(4-(2-(2-aminopyridin-3-yl)-5-phenyl-3H-imidazo[4,5-b]pyridin-3-yl)benzyl)piperazin-1-yl)picolinonitrile (Example 83, 34.3 mg, yield: 22%) was obtained as a light-yellow lyophilized powder. MS: m/z=564.3 [M+H]$^+$. $^1$H NMR (400 MHz, Dimethylsulfoxide-d$_6$) δ 8.27 (d, J=8.4 Hz, 1H), 8.09-7.96 (m, 4H), 7.70 (dd, J=8.8, 7.6 Hz, 1H), 7.54-7.50 (m, 2H), 7.50-7.44 (m, 4H), 7.43-7.37 (m, 1H), 7.24-7.13 (m, 3H), 7.03 (br s, 2H), 6.37 (dd, J=8.0, 4.8 Hz, 1H), 3.64 (s, 2H), 3.62-3.56 (m, 4H), 2.54-2.51 (m, 4H).

Example 84: 5-((1-(4-(2-(2-Aminopyridin-3-yl)-5-phenyl-3H-imidazo[4,5-b]pyridin-3-yl)benzyl)piperidin-4-yl)amino)picolinonitrile

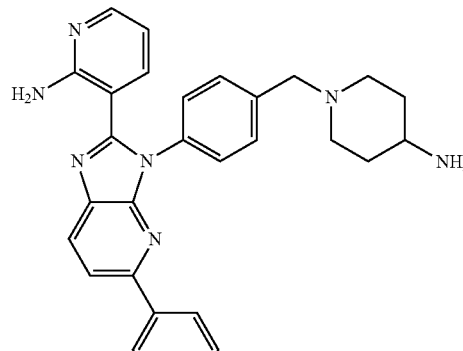

Intermediate 11

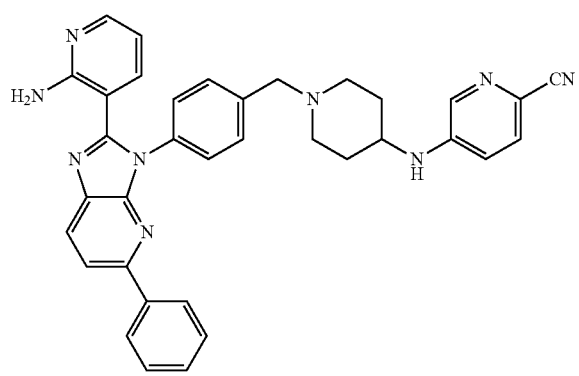

Example 84

Example 85: 4-((1-(4-(2-(2-Aminopyridin-3-yl)-5-phenyl-3H-imidazo[4,5-b]pyridin-3-yl)benzyl)piperidin-4-yl)amino)picolinonitrile

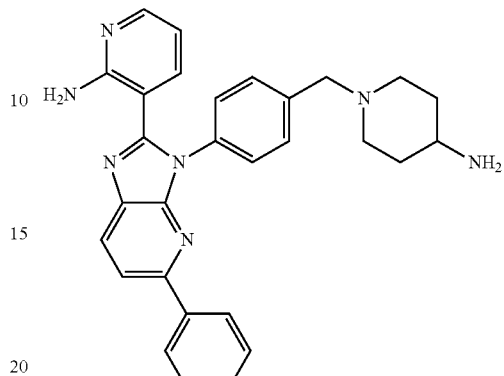

Intermediate 11

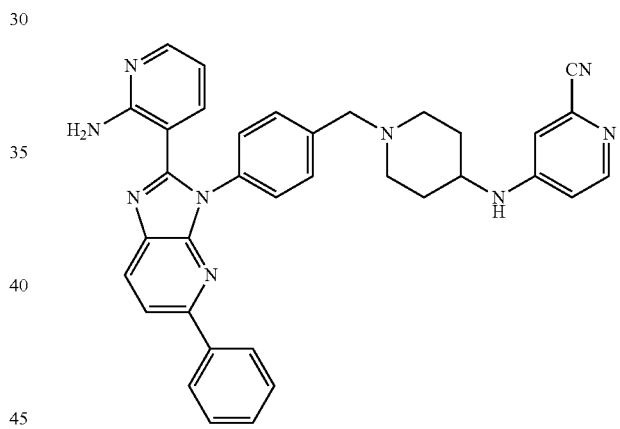

Example 85

To a solution of Intermediate 11 (150 mg, 315 μmol) in DMF (2 mL) was added 5-fluoropyridine-2-carbonitrile (46.2 mg, 378 μmol) and DIEA (204 mg, 1.58 mmol). The mixture was stirred at 100° C. for 16 hr. The mixture was concentrated under reduced pressure to give a residue. The mixture was purified by prep-HPLC (column: Waters Xbridge 150×25 mm×5 μm; mobile phase: [water (NH$_4$HCO$_3$)-ACN]; B %: 35%-75%, 8 min). to give 5-((1-(4-(2-(2-aminopyridin-3-yl)-5-phenyl-3H-imidazo[4,5-b]pyridin-3-yl)benzyl)piperidin-4-yl)amino)picolinonitrile (Example 84, 24.7 mg, yield: 14%) as a light-yellow lyophilized powder. MS: m/z=578.2 [M+H]$^+$. $^1$H NMR (400 MHz, Chloroform-d) δ 8.15 (d, J=8.4 Hz, 1H), 8.07 (dd, J=4.8, 1.2 Hz, 1H), 8.04-8.01 (m, 3H), 7.82 (d, J=8.4 Hz, 1H), 7.57-7.51 (m, 2H), 7.48-7.35 (m, 7H), 7.10 (dd, J=7.8, 1.2 Hz, 1H), 6.82 (dd, J=8.4, 2.8 Hz, 1H), 6.64 (br s, 1H), 6.37 (dd, J=7.6, 4.8 Hz, 1H), 4.29 (br s, 1H), 3.71 (s, 2H), 3.49-3.35 (m, 1H), 3.09-2.93 (m, 2H), 2.33-2.30 (m, 2H), 2.17-2.05 (m, 2H), 1.68-1.67 (m, 2H).

Following the general procedure of Example 84, the reaction of Intermediate 11 (150 mg, 315 μmol) with 4-fluoropyridine-2-carbonitrile (46.2 mg, 378 μmol) was carried out in DMSO (3 mL). After purified by prep-HPLC (column: Waters Xbridge BEH C18 100×30 mm×10 μm; mobile phase: [water (NH$_4$HCO$_3$)-ACN]; B %: 44%-74%, 2 min), 4-((1-(4-(2-(2-aminopyridin-3-yl)-5-phenyl-3H-imidazo[4,5-b]pyridin-3-yl)benzyl)piperidin-4-yl)amino)picolinonitrile (Example 85, 31.7 mg, yield: 17%) was obtained as a light-yellow lyophilized powder. MS: m/z=578.2 [M+H]$^+$. $^1$H NMR (400 MHz, Chloroform-d) δ 8.22 (d, J=5.6 Hz, 1H), 8.15 (d, J=8.4 Hz, 1H), 8.07 (dd, J=4.8, 1.6 Hz, 1H), 8.04-8.01 (m, 2H), 7.82 (d, J=8.4 Hz, 1H), 7.58-7.53 (m, 2H), 7.47-7.43 (m, 4H), 7.41-7.36 (m, 1H), 7.11 (dd, J=7.6, 1.6 Hz, 1H), 6.83 (d, J=2.4 Hz, 1H), 6.68 (br s, 2H), 6.57 (dd, J=5.6, 2.4 Hz, 1H), 6.37 (dd, J=7.6, 4.8 Hz, 1H), 4.52 (br s, 1H), 3.75 (s, 2H), 3.49-3.38 (m, 1H), 3.10-3.00 (m, 2H), 2.43-2.32 (m, 2H), 2.14-2.07 (m, 2H), 1.76-1.75 (m, 2H)

Example 86: 6-((1-(4-(2-(2-Aminopyridin-3-yl)-5-phenyl-3H-imidazo[4,5-b]pyridin-3-yl)benzyl)piperidin-4-yl)amino)picolinonitrile

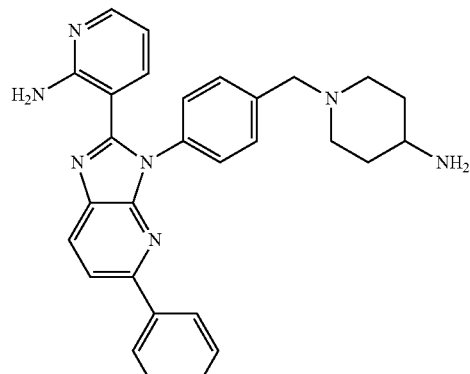

Intermediate 11

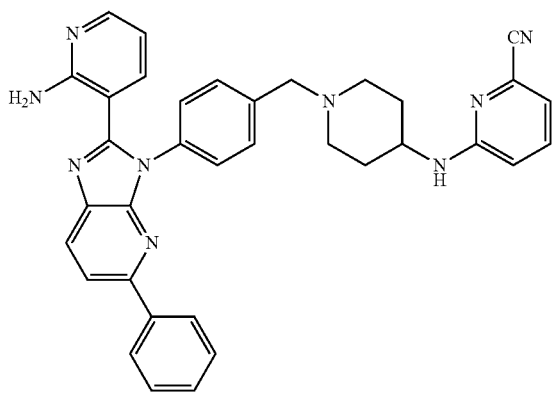

Example 86

Following the general procedure of Example 84, the reaction of Intermediate 11 (150 mg, 315 μmol) with 6-fluoropyridine-2-carbonitrile (46.2 mg, 378 μmol) was carried out in DMSO (3 mL). After purified by prep-HPLC (column: Phenomenex C18 150×25 mm×10 μm; mobile phase: [water (NH$_4$HCO$_3$)-ACN]; B %: 45%-75%, 8 min), 6-((1-(4-(2-(2-aminopyridin-3-yl)-5-phenyl-3H-imidazo[4,5-b]pyridin-3-yl)benzyl)piperidin-4-yl)amino)picolinonitrile (Example 86, 15.6 mg, yield: 8.6%) was obtained as a light-yellow lyophilized powder. MS: m/z=578.2 [M+H]$^+$. $^1$H NMR (400 MHz, Chloroform-d) δ 8.16 (d, J=8.4 Hz, 1H), 8.08 (dd, J=4.8, 1.2 Hz, 1H), 8.02 (d, J=7.2 Hz, 2H), 7.86-7.82 (m, 2H), 7.58-7.53 (m, 2H), 7.49-7.37 (m, 5H), 7.10 (dd, J=7.6, 1.2 Hz, 1H), 7.02-6.96 (m, 1H), 6.74 (br s, 2H), 6.62 (d, J=8.4 Hz, 1H), 6.41 (dd, J=7.6, 4.8 Hz, 1H), 4.90-4.88 (m, 1H), 4.26-4.06 (m, 3H), 3.51-3.49 (m, 2H), 2.89-2.70 (m, 2H), 2.28-2.27 (m, 2H), 1.37-1.23 (m, 2H).

Example 87: 2-((1-(4-(2-(2-Aminopyridin-3-yl)-5-phenyl-3H-imidazo[4,5-b]pyridin-3-yl)benzyl)piperidin-4-yl)amino)isonicotinonitrile

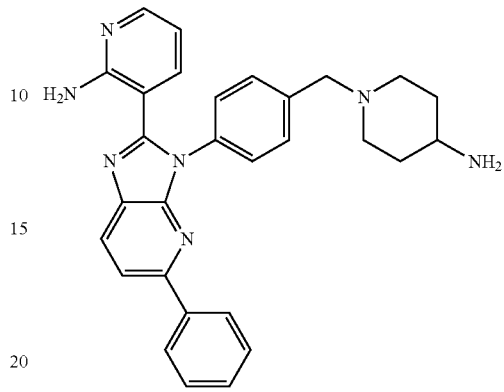

Intermediate 11

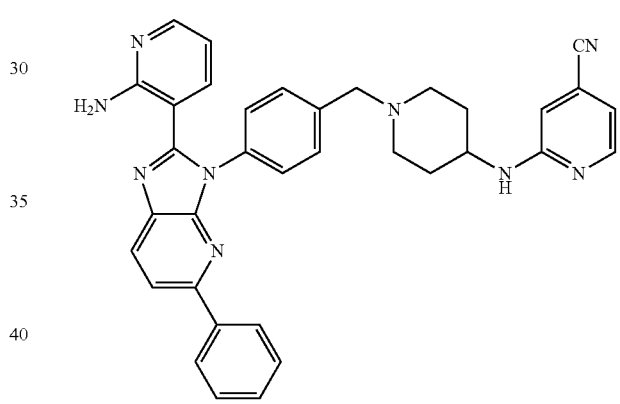

Example 87

Following the general procedure of Example 84, the reaction of Intermediate 11 (208 mg, 420 μmol) with 2-chloropyridine-4-carbonitrile (58.3 mg. 420 μmol) was carried out under microwave at 160° C. for 2 hr. After purified by prep-HPLC (column: Phenomenex C18 150×25 mm×10 μm; mobile phase: [water (NH$_4$HCO$_3$)-ACN]; B %: 51%-81%, 8 min), 2-((1-(4-(2-(2-aminopyridin-3-yl)-5-phenyl-3H-imidazo[4,5-b]pyridin-3-yl)benzyl)piperidin-4-yl) amino)isonicotinonitrile (Example 87, 5.2 mg, yield: 2.1%) was obtained as a light-yellow lyophilized powder. MS: m/z=578.3 [M+H]$^+$. $^1$H NMR (400 MHz, Dimethylsulfoxide-d$_6$) δ 8.27 (d, J=8.0 Hz, 1H), 8.15 (d, J=5.2 Hz, 1H), 8.03 (d, J=7.6 Hz, 2H), 8.01-7.97 (m, 2H), 7.52-7.42 (m, 7H), 7.41-7.37 (m, 1H), 7.18-7.13 (m, 1H), 7.03 (br s, 2H), 6.80 (s, 1H), 6.78-6.72 (m, 1H), 6.38 (dd, J=7.6, 4.8 Hz, 1H), 3.79-3.65 (m, 1H), 3.58 (s, 2H), 2.88-2.80 (m, 2H), 2.16-2.10 (m, 2H), 1.94-1.87 (m, 2H), 1.52-1.42 (m, 2H).

Example 88: 4-((1-(4-(2-(2-Aminopyridin-3-yl)-5-phenyl-3H-imidazo[4,5-b]pyridin-3-yl)benzyl)piperidin-4-yl)amino)pyrimidine-2-carbonitrile

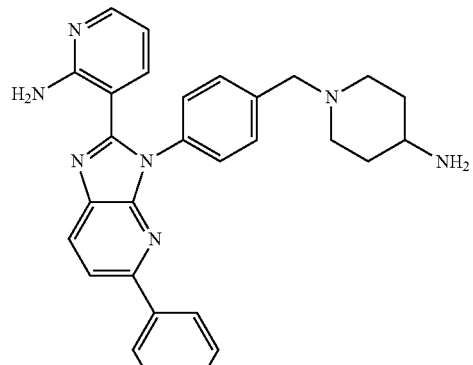

Intermediate 11

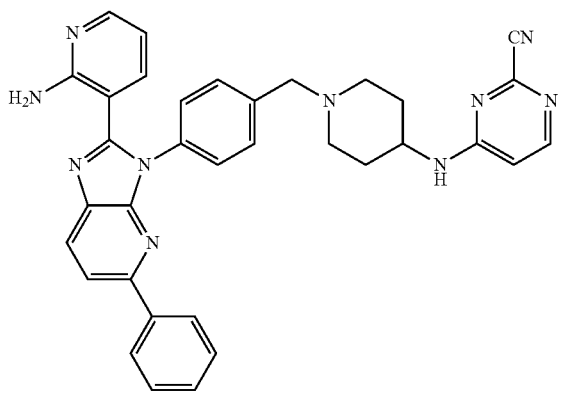

Example 88

Example 89: 6-((1-(4-(2-(2-Aminopyridin-3-yl)-5-phenyl-3H-imidazo[4,5-b]pyridin-3-yl)benzyl)piperidin-4-yl)amino)pyrazine-2-carbonitrile

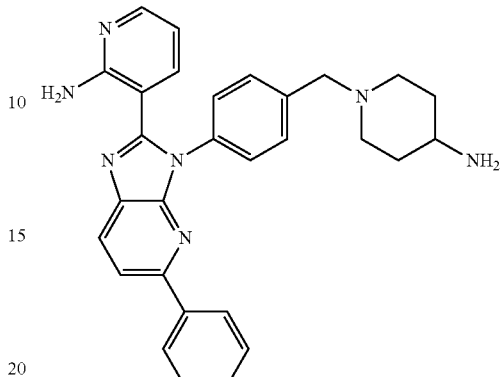

Intermediate 11

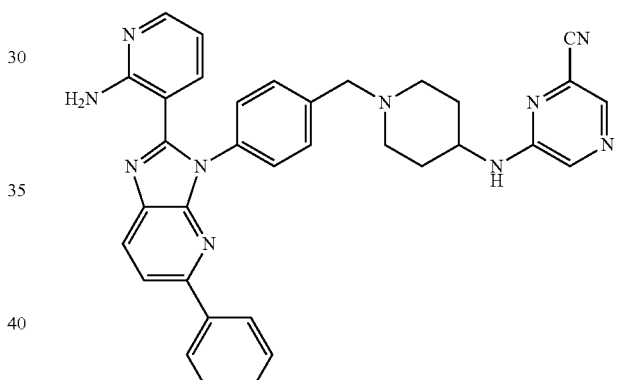

Example 89

Following the general procedure of Example 84, the reaction of Intermediate 11 (1 g, 2.0 mmol) with 4-chloropyrimidine-2-carbonitrile (278 mg, 2.0 mmol) was carried out under microwave at 130° C. for 0.5 hr. After purified by silica gel flash chromatography (Eluent of 0~100% EtOAc in petroleum ether and 8% MeOH in $CH_2Cl_2$), 4-((1-(4-(2-(2-Aminopyridin-3-yl)-5-phenyl-3H-imidazo[4,5-b]pyridin-3-yl)benzyl)piperidin-4-yl)amino)pyrimidine-2-carbonitrile (Example 88, 601 mg, yield: 52%) was obtained as a light-yellow solid. MS: m/z=579.4 [M+H]$^+$. $^1$H NMR (400 MHz, Dimethylsulfoxide-$d_6$) δ 8.27 (d, J=8.4 Hz, 1H), 8.10-7.97 (m, 6H), 7.51-7.43 (m, 6H), 7.41-7.37 (m, 1H), 7.16 (dd, J=7.6, 1.6 Hz, 1H), 7.03 (br s, 2H), 6.67 (d, J=5.6 Hz, 1H), 6.38 (dd, J=7.6, 4.8 Hz, 1H), 3.84-3.79 (m, 1H), 3.59 (s, 2H), 2.87-2.80 (m, 2H), 2.15-2.13 (m, 2H), 1.90-1.89 (m, 2H), 1.55-1.44 (m, 2H).

Following the general procedure of Example 84, the reaction of Intermediate 11 (150 mg, 315 μmol) with 6-chloropyrazine-2-carbonitrile (52.8 mg, 378 μmol) was carried out under microwave at 130° C. for 0.5 hr. After purified by prep-HPLC (column: Waters xbridge 150×25 mm×10 μm; mobile phase: [water ($NH_4HCO_3$)-ACN]; B %: 45%-75%, 9 min), 6-((1-(4-(2-(2-Aminopyridin-3-yl)-5-phenyl-3H-imidazo[4,5-b]pyridin-3-yl)benzyl)piperidin-4-yl)amino)pyrazine-2-carbonitrile (Example 89, 20.1 mg, yield: 11%) was obtained as a light-yellow lyophilized powder. MS: m/z=579.1 [M+H]$^+$. $^1$H NMR (400 MHz, Chloroform-d) δ 8.15 (d, J=8.4 Hz, 1H), 8.11-8.05 (m, 3H), 8.04-8.00 (m, 2H), 7.82 (d, J=8.4 Hz, 1H), 7.66-7.59 (m, 2H), 7.49-7.43 (m, 4H), 7.41-7.37 (m, 1H), 7.10 (dd, J=7.6, 1.6 Hz, 1H), 6.63 (br s, 2H), 6.38 (dd, J=7.6, 4.8 Hz, 1H), 5.59-4.63 (m, 1H), 4.03-3.80 (m, 3H), 3.27-3.02 (m, 2H), 2.59-2.40 (m, 2H), 2.20-2.13 (m, 2H), 1.93-1.84 (m, 2H).

Example 90: 2-((1-(4-(2-(2-Aminopyridin-3-yl)-5-phenyl-3H-imidazo[4,5-b]pyridin-3-yl)benzyl)piperidin-4-yl)amino)pyrimidine-4-carbonitrile Example 91: 6-((1-(4-(2-(2-Aminopyridin-3-yl)-5-phenyl-3H-imidazo[4,5-b]pyridin-3-yl)benzyl)piperidin-4-yl)amino)pyrimidine-4-carbonitrile

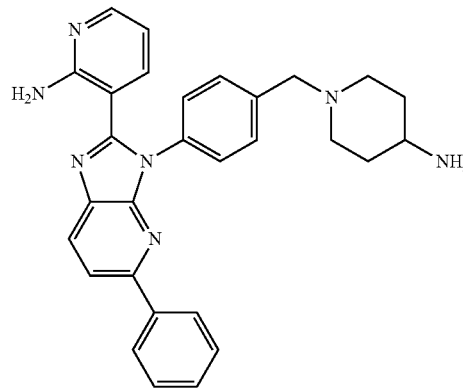

Intermediate 11

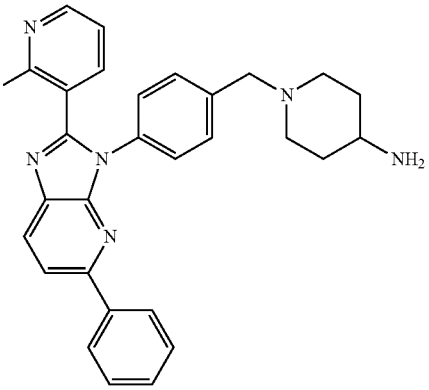

Intermediate 11

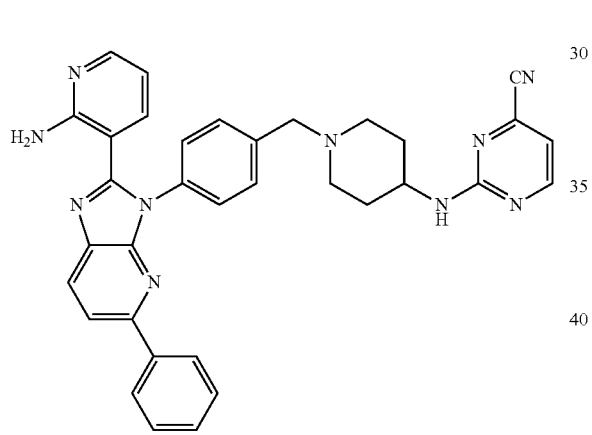

Example 90

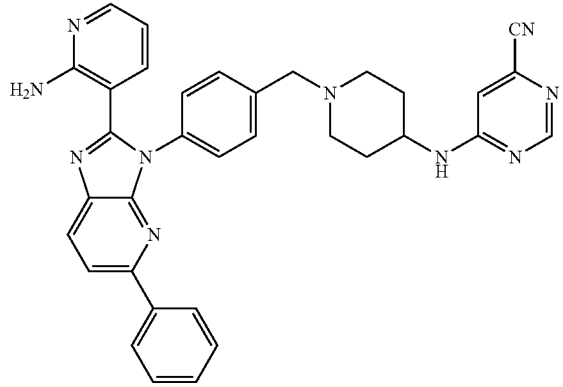

Example 91

Following the general procedure of Example 84, the reaction of Intermediate 11 (150 mg, 315 μmol) with 2-chloropyrimidine-4-carbonitrile (52.8 mg, 378 μmol) was carried out under microwave at 130° C. for 0.5 hr. After purified by prep-HPLC (column: Waters xbridge 150×25 mm×10 μm; mobile phase: [water (NH$_4$HCO$_3$)-ACN]; B %: 45%-75%, 9 min), 2-((1-(4-(2-(2-aminopyridin-3-yl)-5-phenyl-3H-imidazo[4,5-b]pyridin-3-yl)benzyl)piperidin-4-yl)amino)pyrimidine-4-carbonitrile (Example 90, 30.9 mg, yield: 17%) was obtained as a light gray Lyophilized powder. MS: m/z=579.1 [M+H]$^+$. $^1$H NMR (400 MHz, Chloroform-d) δ 8.44 (d, J=2.4 Hz, 1H), 8.14 (d, J=8.4 Hz, 1H), 8.08 (dd, =4.8, 1.6 Hz, 1H), 8.03 (d, J=7.2 Hz, 2H), 7.82 (d, J=8.4 Hz, 1H), 7.57 (d, J=7.6 Hz, 2H), 7.49-7.42 (m, 4H), 7.41-7.35 (m, 1H), 7.11 (dd, J=7.6, 1.2 Hz, 1H), 6.83 (d, J=4.8 Hz, 1H), 6.63 (br s, 2H), 6.38 (dd, J=7.6, 4.8 Hz, 1H), 5.41 (br s, 1H), 4.00-3.90 (m, 1H), 3.74 (s, 2H), 3.18-2.90 (m, 2H), 2.39-2.37 (m, 2H), 2.14-2.11 (m, 2H), 1.79-1.78 (m, 2H).

Following the general procedure of Example 84, the reaction of Intermediate 11 (150 mg. 315 μmol) with 6-chloropyrimidine-4-carbonitrile (52.8 mg, 378 μmol) was carried out under microwave at 130° C. for 0.5 hr. After purified by silica gel flash chromatography (Eluent of 0-20% MeOH in CH$_2$Cl$_2$), 6-((1-(4-(2-(2-Aminopyridin-3-yl)-5-phenyl-3H-imidazo[4,5-b]pyridin-3-yl)benzyl)piperidin-4-yl)amino)pyrimidine-4-carbonitrile (Example 91, 31.3 mg, yield: 17%) was obtained as a yellow-green lyophilized powder. MS: m/z=579.2 [M+H]$^+$. $^1$H NMR (400 MHz, Dimethylsulfoxide-d$_6$) δ 8.50 (s, 1H), 8.27 (d, J=8.4 Hz, 1H), 8.09-7.97 (m, 5H), 7.50-7.44 (m, 6H), 7.42-7.36 (m, 1H), 7.16 (dd, J=7.6, 1.6 Hz, 1H), 7.02 (br s, 2H), 6.93 (s, 1H), 6.38 (dd, J=7.6, 4.8 Hz, 1H), 3.94-3.80 (m, 1H), 3.59 (s, 2H), 2.87-2.80 (m, 2H), 2.17-2.07 (m, 2H), 1.95-1.83 (m, 2H), 1.55-1.47 (m, 2H).

Example 92: 4-((1-(4-(2-(2-Aminopyridin-3-yl)-3H-imidazo[4,5-b]pyridin-3-yl)benzyl)piperidin-4-yl)amino)pyrimidine-2-carbonitrile

Example 93: 5-((1-(4-(2-(2-Aminopyridin-3-yl)-5-phenyl-3H-imidazo[4,5-b]pyridin-3-yl)benzyl)piperidin-4-yl)amino)nicotinonitrile

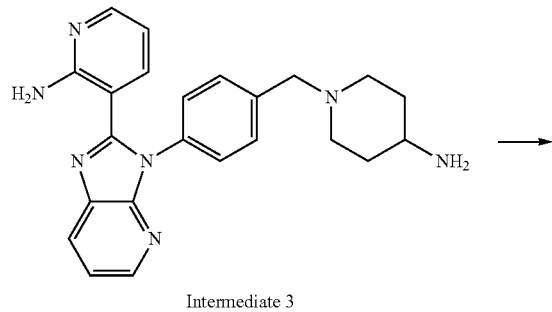

Intermediate 3

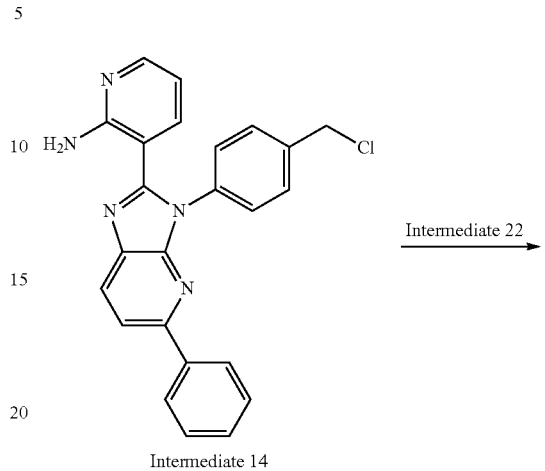

Intermediate 14

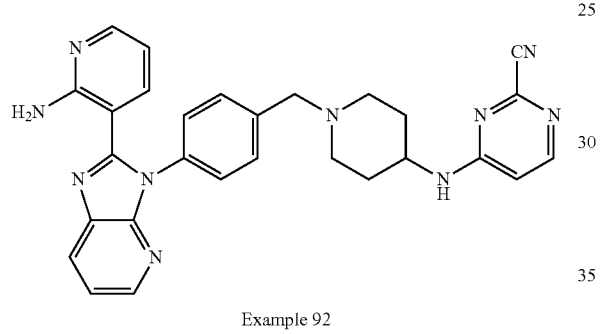

Example 92

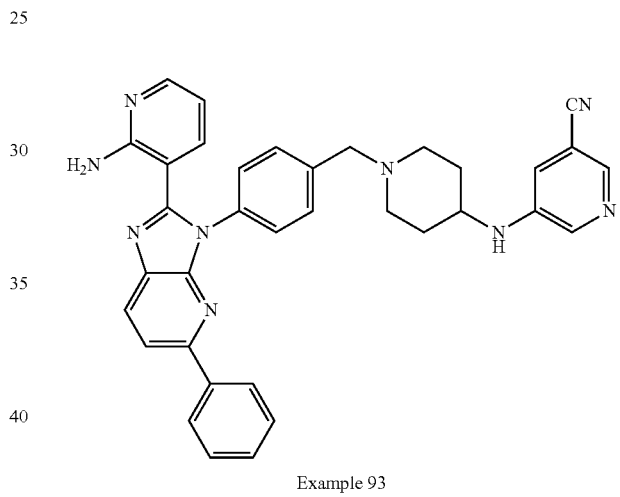

Example 93

Following the general procedure of Example 84, the reaction of Intermediate 3 (150 mg, 375 μmol) with 6-chloropyrimidine-4-carbonitrile (52.4 mg, 375 μmol) was carried out under microwave at 130° C. for 0.5 hr. After purified by silica gel flash chromatography (Eluent of 0-13% EtOAc in petroleum ether) and then prep-TLC (CH$_2$Cl$_2$:MeOH=10:1), 4-((1-(4-(2-(2-aminopyridin-3-yl)-3H-imidazo[4,5-b]pyridin-3-yl)benzyl)piperidin-4-yl)amino)pyrimidine-2-carbonitrile (Example 92, 24.7 mg, yield: 13%) was obtained as a light-gray solid. MS: m/z=503.3 [M+H]$^+$. $^1$H NMR (400 MHz, Dimethylsulfoxide-d$_6$) δ 8.33 (dd, J=4.6, 1.2 Hz, 1H), 8.20 (dd, J=8.0, 1.2 Hz, 1H), 8.11-8.03 (m, 2H), 7.99 (dd, J=4.8, 1.6 Hz, 1H), 7.45 (d, J=8.4 Hz, 2H), 7.41-7.36 (m, 3H), 7.16 (dd, J=7.6, 1.6 Hz, 1H), 7.01 (br s, 2H), 6.67 (d, J=5.6 Hz, 1H), 6.37 (dd, J=7.6, 4.8 Hz, 1H), 3.84-3.80 (m, 1H), 3.56 (s, 2H), 2.81 (d, J=11.2 Hz, 2H), 2.18-2.11 (m, 2H), 1.89-1.87 (m, 2H), 1.53-1.44 (m, 2H).

To a solution of Intermediate 14 (120 mg, 291 μmol), Intermediate 22 (64.8 mg, 320 μmol) in DMF (1 mL) were added NaI (4.37 mg, 29.1 μmol) and K$_2$CO$_3$ (80.5 mg, 582 μmol). The mixture was stirred at 80° C. for 2 hr. The reaction mixture was diluted with H$_2$O (5 mL) and then filtered and concentrated under reduced pressure to give a residue. The residue was purified by prep-TLC (CH$_2$Cl$_2$:MeOH=10:1), 5-((1-(4-(2-(2-aminopyridin-3-yl)-5-phenyl-3H-imidazo[4,5-b]pyridin-3-yl)benzyl)piperidin-4-yl)amino)nicotinonitrile (Example 93, 13.7 mg, yield: 8.2%) was obtained as a light-yellow powder. MS: m/z=578.4 [M+H]$^+$. $^1$H NMR (400 MHz, Dimethylsulfoxide-d$_6$) δ 8.27 (d, J=8.4 Hz, 1H), 8.22 (d, J=2.8 Hz, 1H), 8.08-7.97 (m, 5H), 7.51-7.44 (m, 6H), 7.43-7.36 (m, 1H), 7.32 (s, 1H), 7.16 (dd, J=7.6, 2.0 Hz, 1H), 7.02 (br s, 2H), 6.42-6.32 (m, 2H), 3.59 (s, 2H), 3.30-3.10 (m, 1H), 2.95-2.75 (m, 2H), 2.18 (t, J=9.6 Hz, 2H), 1.92-1.85 (m, 2H), 1.46-1.38 (m, 2H).

Example 94: 5-(4-(4-(2-(2-Aminopyridin-3-yl)-5-phenyl-3H-imidazo[4,5-b]pyridin-3-yl)benzyl)piperazin-1-yl)picolinonitrile

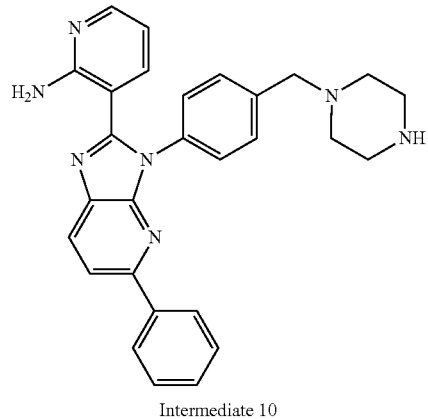

Intermediate 10

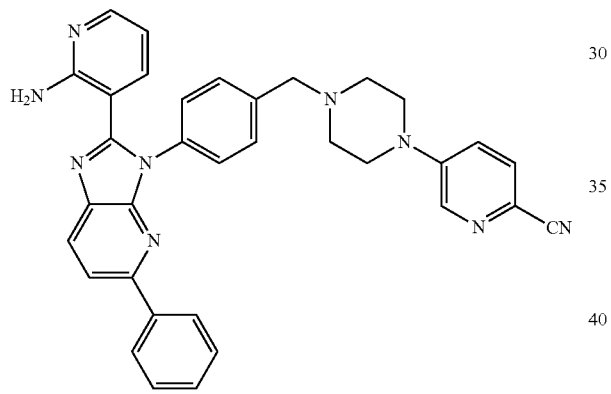

Example 94

Following the general procedure of Example 14, the reaction of Intermediate 10 (200 mg, 433 μmol) with 5-fluoropicolinonitrile (63.4 mg, 520 μmol) was carried out. After purified by prep-HPLC (column: Waters xbridge 150*25 mm 10 um; mobile phase: [water (NH4HCO3)-ACN]; B %: 44%-74%, 8 min), 5-(4-(4-(2-(2-Aminopyridin-3-yl)-5-phenyl-3H-imidazo[4,5-b]pyridin-3-yl)benzyl)piperazin-1-yl)picolinonitrile (Example 94, 49.5 mg, yield: 20%) was obtained as an orange solid. MS: m/z=564.0 [M+H]+. 1H NMR (400 MHz, Dimethylsulfoxide-d6) δ 8.44 (d, J=2.8 Hz, 1H), 8.28 (d, J=8.4 Hz, 1H), 8.06-7.98 (m, 4H), 7.75 (d, J=9.2 Hz, 1H), 7.530 (d, J=8.4 Hz, 2H), 7.50-7.44 (m, 4H), 7.43-7.35 (m, 2H), 7.16 (dd, J=7.6, 1.6 Hz, 1H), 7.04 (br s, 2H), 6.38 (dd, J=7.6, 4.8 Hz, 1H), 3.66 (s, 2H), 3.46 (t, J=4.8 Hz, 4H), 2.56 (t, J=4.8 Hz, 4H).

Example 95: 5-((4-(2-(2-Aminopyridin-3-yl)-3H-imidazo[4,5-b]pyridin-3-yl)benzyl)amino)pyrimidine-2-carbonitrile

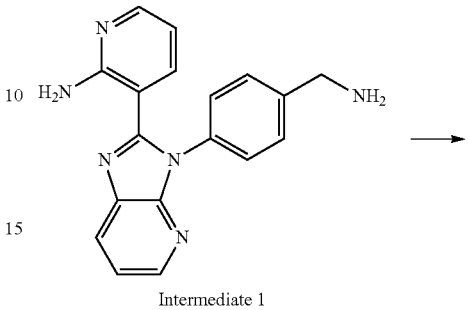

Intermediate 1

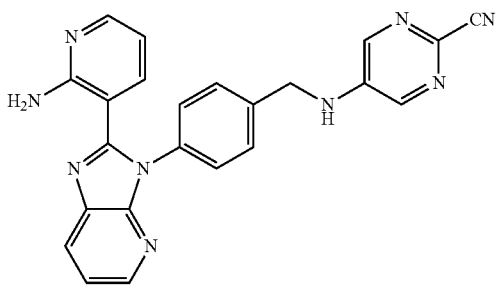

Example 95

To a solution of Intermediate 1 (200 mg, 0.632 mmol) and 5-fluoropyrimidine-2-carbonitrile (77.8 mg, 0.632 mmol) in DMF (4 mL) was added DIEA (245 mg, 1.90 mmol). The mixture was stirred at 100° C. for 12 hr. The reaction mixture was filtered. Then the filtrate was purified by prep-HPLC (column: Waters xbridge 150*25 mm 10 μm; mobile phase: [water (NH4HCO3)-ACN]; B %: 17%-47%, 10 min), 5-((4-(2-(2-aminopyridin-3-yl)-3H-imidazo[4,5-b]pyridin-3-yl)benzyl)amino)pyrimidine-2-carbonitrile (Example 95, 52.8 mg, yield: 20%) was obtained as a white solid. MS: m/z=420.1 [M+H]+. 1H NMR (400 MHz, Dimethylsulfoxide-d6) δ 8.31 (dd, J=4.8, 1.6 Hz, 1H), 8.26 (s, 2H), 8.20 (dd, J=8.0, 1.2 Hz, 1H), 7.99 (m, dd, J=8.8, 2.0 Hz, 1H), 7.85 (d, J=6.0, 6.0 Hz, 1H), 7.52 (d, J=8.4 Hz, 2H), 7.45-7.33 (m, 31H), 7.17 (dd, J=7.6, 1.6 Hz, 1H), 6.97 (br s, 2H), 6.36 (dd, J=7.6, 4.8 Hz, 1H), 4.55 (d, J=6.0 Hz, 2H).

Example 96: 5-((4-(2-(2-Aminopyridin-3-yl)-5-phenyl-3H-imidazo[4,5-b]pyridin-3-yl)benzyl)amino)pyrimidine-2-carbonitrile Example 97: 5-(4-(4-(2-(2-aminopyridin-3-yl)-5-phenyl-3H-imidazo[4,5-b]pyridin-3-yl)benzyl)piperazin-1-yl)pyrimidine-2-carbonitrile

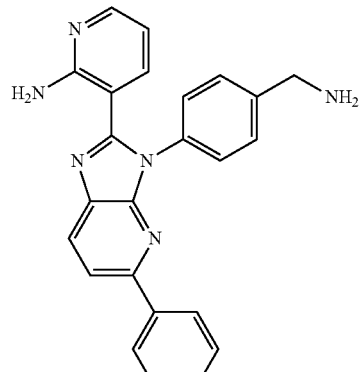

Intermediate 4

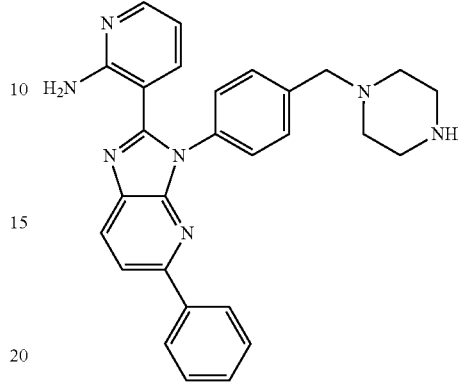

Intermediate 10

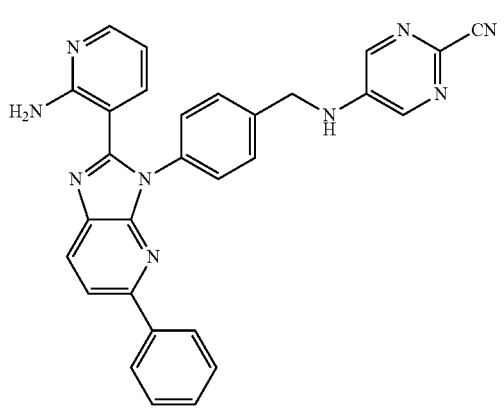

Example 96

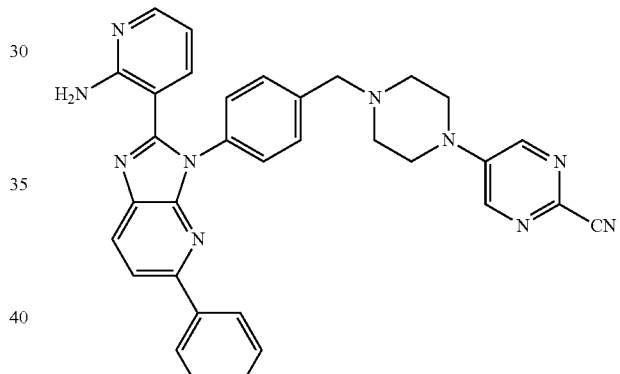

Example 97

Following the general procedure of Example 95, the reaction of Intermediate 4 (200 mg, 509 µmol) with 5-fluoropyrimidine-2-carbonitrile (63 mg, 509 µmol) was carried out. After purified by prep-HPLC (column: Waters xbridge 150*25 mm 10 µm; mobile phase: [water (NH$_4$HCO$_3$)-ACN]; B %: 35%-65%, 10 min), 5-((4-(2-(2-aminopyridin-3-yl)-5-phenyl-3H-imidazo[4,5-b]pyridin-3-yl)benzyl)amino)pyrimidine-2-carbonitrile (Example 96, 55 mg, yield: 22%) was obtained as an off-white lyophilized powder. MS: m/z=496.3 [M+H]$^+$. $^1$H NMR (400 MHz, Dimethylsulfoxide-d$_6$) δ 8.36-8.20 (m, 3H), 8.09-7.95 (m, 4H), 7.87-7.77 (m, 1H), 7.60-7.36 (m, 7H), 7.21-7.14 (m, 1H), 6.99 (br s, 2H), 6.44-6.31 (m, 1H), 4.57 (d, J=5.2 Hz, 2H).

Following the general procedure of Example 95, the reaction of Intermediate 10 (200 mg, 433 µmol) with 5-fluoropyrimidine-2-carbonitrile (53.3 mg, 433 µmol) was carried out. After purified by prep-HPLC (column: Waters xbridge 150*25 mm 10 µm; mobile phase: [water (NH$_4$HCO$_3$)-ACN]; B %: 42%-72%, 10 min), 5-(4-(4-(2-(2-aminopyridin-3-yl)-5-phenyl-3H-imidazo[4,5-b]pyridin-3-yl)benzyl)piperazin-1-yl)pyrimidine-2-carbonitrile (Example 97, 18 mg, yield: 7.4%) was obtained as a yellow solid. MS: m/z=565.3 [M+H]$^+$. $^1$H NMR (400 MHz, Dimethylsulfoxide-d$_6$) δ 8.58 (s, 2H), 8.27 (d, J=8.4 Hz, 1H), 8.10-7.95 (m, 4H), 7.56-7.44 (m, 6H), 7.43-7.34 (m, 1H), 7.15 (d, J=6.0 Hz, 1H), 7.03 (br s, 2H), 6.37 (dd, J=7.6, 4.8 Hz, 1H), 3.65 (s, 2H), 3.58-3.46 (m, 4H), 2.63-2.39 (m, 4H).

Example 98: N-(4-(2-(2-Aminopyridin-3-yl)-3H-imidazo[4,5-b]pyridin-3-yl)benzyl)-2-cyanonicotinamide

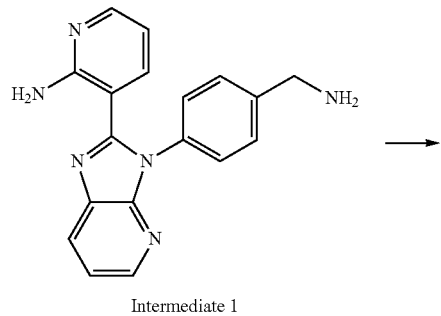

Intermediate 1

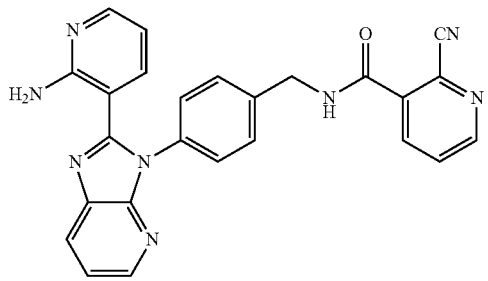

Example 98

Following the general procedure of Example 23, the reaction of Intermediate 1 (200 mg, 632 μmol) with 2-cyanonicotinic acid (93.6 mg, 632 μmol) was carried out. After purified by prep-HPLC (column: Waters xbridge 150×25 mm×10 μm; mobile phase: [water (NH$_4$HCO$_3$)-ACN]; B %: 20%-50%, 10 min), N-(4-(2-(2-aminopyridin-3-yl)-3H-imidazo[4,5-b]pyridin-3-yl)benzyl)-2-cyanonicotinamide (Example 98, 14.7 mg, yield: 5.2%) was obtained as a yellow solid. MS: m/z=447.2 [M+H]$^+$. $^1$H NMR (400 MHz, Dimethylsulfoxide-d$_6$) δ 10.01 (s, 1H), 8.96 (d, J=4.8 Hz, 1H), 8.32-8.27 (m, 2H), 8.18 (d, J=8.0 Hz, 1H), 7.98 (d, J=4.8 Hz, 1H), 7.76 (dd, J=6.4 Hz, 5.2 Hz, 1H), 7.48 (d, J=8.0 Hz, 2H), 7.39-7.35 (m, 3H), 7.20 (d, J=7.6 Hz, 1H), 6.95 (br s, 2H), 6.41 (dd, J=8.0 Hz, 4.8 Hz, 1H), 5.05 (s, 2H).

Example 99: N-(4-(2-(2-Aminopyridin-3-yl)-3H-imidazo[4,5-b]pyridin-3-yl)benzyl)-3-cyanoisonicotinamide

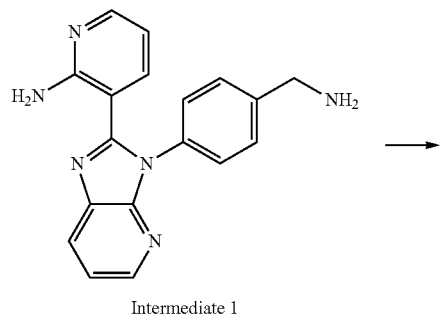

Intermediate 1

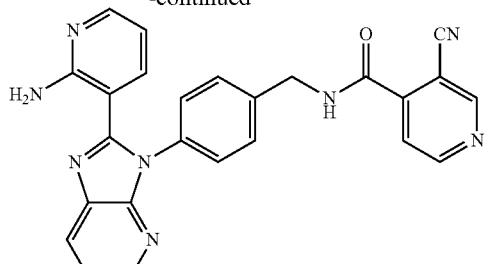

Example 99

Following the general procedure of Example 23, the reaction of Intermediate 1 (50 mg, 158 μmol) with 3-cyanopyridine-4-carboxylic acid (23.4 mg, 158 μmol) was carried out. After purified by prep-HPLC (column: Waters Xbridge BEH C18 100×30 mm×10 μm; mobile phase: [water (NH$_4$HCO$_3$)-ACN]; B %: 14%-45%, 2 min), N-(4-(2-(2-aminopyridin-3-yl)-3H-imidazo[4,5-b]pyridin-3-yl)benzyl)-3-cyanoisonicotinamide (Example 99, 4.5 mg, yield: 6.4%) was obtained as an off-white lyophilized powder MS: m/z=447.0 [M+H]$^+$. $^1$H NMR (400 MHz, Chloroform-d) δ 9.12 (s, 1H), 9.07-8.92 (m, 2H), 8.46-8.39 (m, 1H), 8.19-8.10 (m, 1H), 7.94-7.83 (m, 1H), 7.80 (d, J=4.8 Hz, 1H), 7.77-7.56 (m, 2H), 7.39-7.31 (m, 4H), 7.23 (br s, 2H), 6.54-6.43 (m, 1H), 5.15 (s, 2H).

Example 100: N-(4-(2-(2-Aminopyridin-3-yl)-3H-imidazo[4,5-b]pyridin-3-yl)benzyl)-4-cyanonicotinamide

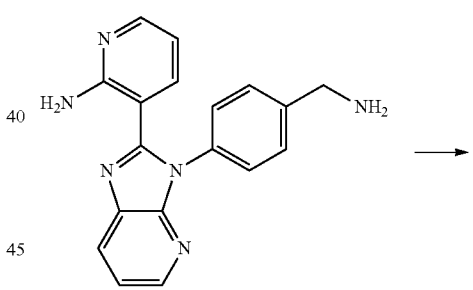

Intermediate 1

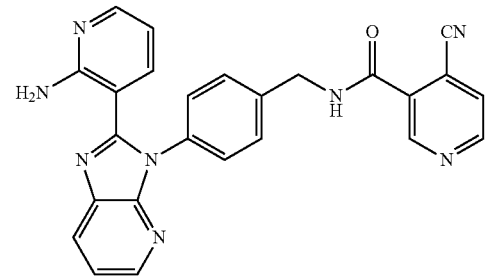

Example 100

Following the general procedure of Example 23, the reaction of Intermediate 1 (50 mg. 158 μmol) with 4-cyanopyridine-3-carboxylic acid (23.4 mg, 158 μmol) was carried out. After purified by prep-HPLC (column: Waters Xbridge BEH C18 100×30 mm×10 μm; mobile phase: [water (NH$_4$HCO$_3$)-ACN]; B %: 15%-45%, 2 min), N-(4-

(2-(2-aminopyridin-3-yl)-3H-imidazo[4,5-b]pyridin-3-yl)benzyl)-4-cyanonicotinamide (Example 100, 8.7 mg, yield: 12.3%) was obtained as an off-white lyophilized powder. MS: m/z=447.1 [M+H]⁺. ¹H NMR (400 MHz, Chloroform-d) δ 9.20 (s, 1H), 9.05 (m, 2H), 8.40 (d, J=4.8 Hz, 1H), 8.15-8.02 (m, 2H), 8.01-7.87 (m, 2H), 7.73-7.59 (m, 3H), 7.41-7.30 (m, 4H), 6.48-6.43 (m, 1H), 5.13 (br s, 2H).

Example 101: N-(4-(2-(2-Aminopyridin-3-yl)-3H-imidazo[4,5-b]pyridin-3-yl)benzyl)-3-cyanopicolinamide

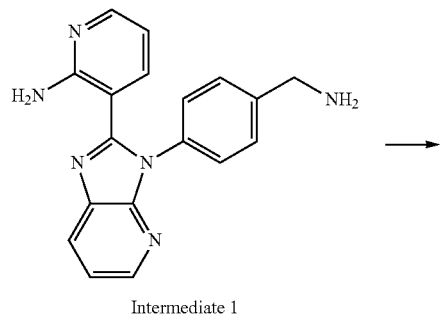

Intermediate 1

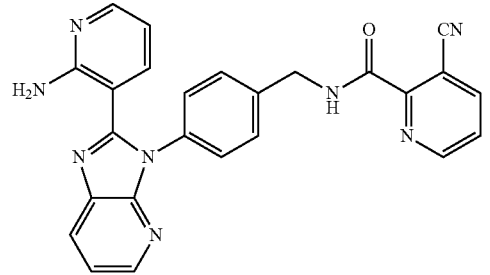

Example 101

Example 102: 5-(4-(4-(2-(2-Aminopyridin-3-yl)-3H-imidazo[4,5-b]pyridin-3-yl)benzyl)piperazine-1-carbonyl)picolinonitrile

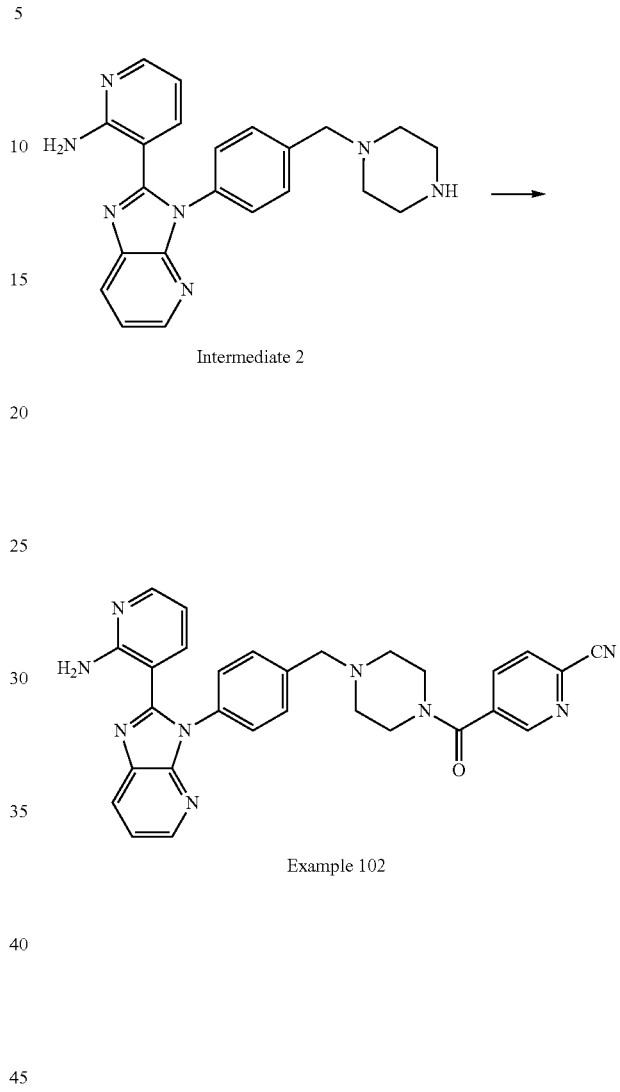

Following the general procedure of Example 23, the reaction of Intermediate 1 (200 mg, 632 μmol) with 3-cyanopyridine-2-carboxylic acid (93.6 mg, 632 μmol) was carried out. After purified by prep-HPLC (column: Waters xbridge 150×25 mm×10 μm; mobile phase: [water (NH₄HCO₃)-ACN]; B %: 15%-45%, 10 min), N-(4-(2-(2-aminopyridin-3-yl)-3H-imidazo[4,5-b]pyridin-3-yl)benzyl)-3-cyanopicolinamide (Example 101, 6.8 mg, yield: 2.4%) was obtained as a yellow solid. MS: m/z=447.1 [M+H]⁺. ¹H NMR (400 MHz, Methanol-d₄) δ 8.90 (dd, J=4.8, 1.2 Hz, 11H), 8.48 (dd, J=8.0, 1.2 Hz, 11H), 8.29 (dd, J=4.8, 1.6 Hz, 1H), 8.18 (dd, J=8.0, 1.6 Hz, 1H), 7.96 (d, J=5.2 Hz, 1H), 7.77 (dd, J=8.0, 5.2 Hz, 1H), 7.61 (d, J=8.0 Hz, 2H), 7.43-7.37 (m, 3H), 7.31 (dd, J=8.0, 2.0 Hz, 1H), 6.46 (dd, J=7.6, 5.2 Hz, 1H), 5.16 (s, 2H).

Following the general procedure of Example 23, the reaction of Intermediate 2 (150 mg, 389 μmol) with 6-cyanopyridine-3-carboxylic acid (63.4 mg, 428 μmol) was carried out. After purified by prep-HPLC (column: Waters xbridge 150×25 mm×10 μm; mobile phase: [water (NH₄HCO₃)-ACN]; B %: 19%-49%, 9 min), 5-(4-(4-(2-(2-aminopyridin-3-yl)-3H-imidazo[4,5-b]pyridin-3-yl)benzyl)piperazine-1-carbonyl)picolinonitrile (Example 102, 87 mg, yield: 43%) was obtained as a yellow solid. MS: m/z=516.2 [M+H]⁺. ¹H NMR (400 MHz, Chloroform-d) δ 8.76 (d, J=1.6 Hz, 1H), 8.40 (dd, J=4.8, 1.2 Hz, 1H), 8.11 (dd, J=8.0, 1.2 Hz, 1H), 8.05 (dd, J=4.8, 1.6 Hz, 1H), 7.91 (dd, J=8.0, 2.4 Hz, 1H), 7.77 (d, J=8.4 Hz, 1H), 7.50 (d, J=8.4 Hz, 2H), 7.39-7.27 (m, 3H), 7.07 (dd, J=8.0, 2.0 Hz, 1H), 6.67 (br s, 2H), 6.34 (dd, J=8.0, 5.2 Hz, 1H), 3.90-3.79 (m, 2H), 3.64 (s, 2H), 3.51-3.36 (m, 2H), 2.67-2.43 (m, 4H).

Example 103: N-(4-(2-(2-Aminopyridin-3-yl)-5-phenyl-3H-imidazo[4,5-b]pyridin-3-yl)benzyl)-2-cyanonicotinamide

Example 104: N-(4-(2-(2-Aminopyridin-3-yl)-5-phenyl-3H-imidazo[4,5-b]pyridin-3-yl)benzyl)-3-cyanoisonicotinamide

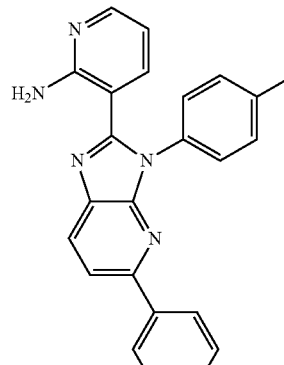

Intermediate 4

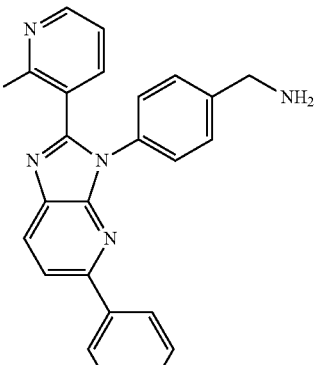

Intermediate 4

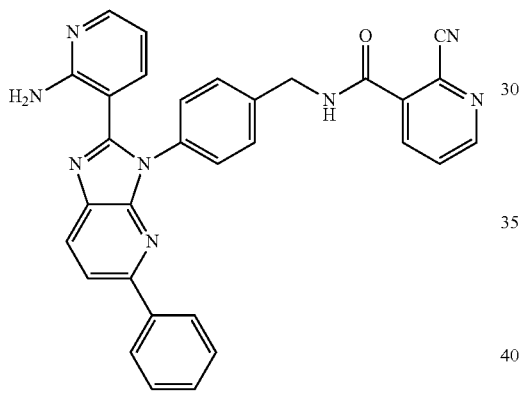

Example 103

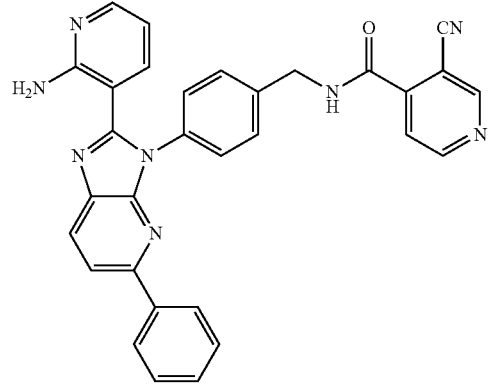

Example 104

Following the general procedure of Example 23, the reaction of Intermediate 4 (120 mg, 306 μmol) with 2-cyanopyridine-3-carboxylic acid (45.3 mg, 306 μmol) was carried out. After purified by prep-HPLC (column: Phenomenex C18 150×25 mm×10 μm; mobile phase: [water (NH$_4$HCO$_3$)-ACN]; B %: 35%-65%, 8 min), N-(4-(2-(2-aminopyridin-3-yl)-5-phenyl-3H-imidazo[4,5-b]pyridin-3-yl)benzyl)-2-cyanonicotinamide (Example 103, 38.5 mg, yield: 24%) was obtained as an off-white solid. MS: m/z=523.2 [M+H]$^+$. $^1$H NMR (400 MHz, Dimethylsulfoxide-d$_6$) δ 10.01 (s, 1H), 8.96 (dd, J=4.8, 1.2 Hz, 1H), 8.31 (dd, J=8.0, 1.6 Hz, 1H), 8.25 (d, J=8.4 Hz, 1H), 8.02-7.95 (m, 4H), 7.77 (dd, J=8.0, 5.2 Hz, 1H), 7.51 (d, J=8.8 Hz, 2H), 7.48-7.43 (m, 4H), 7.41-7.36 (m, 1H), 7.18 (dd, J=7.6, 1.6 Hz, 1H), 6.91 (br s, 2H), 6.40 (dd, J=7.6, 4.8 Hz, 1H), 5.07 (s, 2H).

Following the general procedure of Example 23, the reaction of Intermediate 4 (50 mg, 127 μmol) with 3-cyanopyridine-4-carboxylic acid (18.9 mg, 127 μmol) was carried out. After purified by prep-HPLC (column: Waters Xbridge BEH C18 100×30 mm×10 μm; mobile phase: [water (NH$_4$HCO$_3$)-ACN]; B %: 33%-63%, 2 min), N-(4-(2-(2-aminopyridin-3-yl)-5-phenyl-3H-imidazo[4,5-b]pyridin-3-yl)benzyl)-3-cyanoisonicotinamide (Example 104, 10.5 mg, yield: 16%) was obtained as an off-white solid. MS: m/z=523.2 [M+H]$^+$. $^1$H NMR (400 MHz, Chloroform-d) δ 9.22-9.03 (m, 3H), 8.96 (d, J=5.6 Hz, 1H), 8.12 (d, J=8.4 Hz, 1H), 7.93-7.88 (m, 2H), 7.80 (d, J=8.4 Hz, 1H), 7.76 (d, J=8.8 Hz, 1H), 7.74-7.70 (m, 1H), 7.61 (d, J=8.0 Hz, 2H), 7.40-7.30 (m, 7H), 6.47 (dd, J=7.2, 6.4 Hz, 1H), 5.19 (s, 2H).

Example 105: N-(4-(2-(2-Aminopyridin-3-yl)-5-phenyl-3H-imidazo[4,5-b]pyridin-3-yl)benzyl)-4-cyanonicotinamide Example 106: N-(4-(2-(2-Aminopyridin-3-yl)-6-phenyl-3H-imidazo[4,5-b]pyridin-3-yl)benzyl)-6-cyanonicotinamide

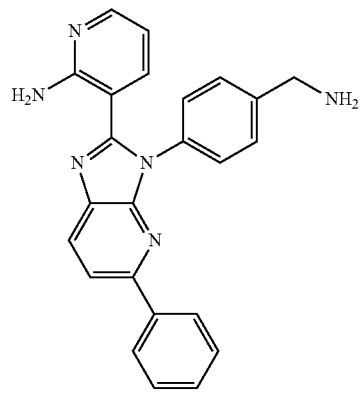

Intermediate 4

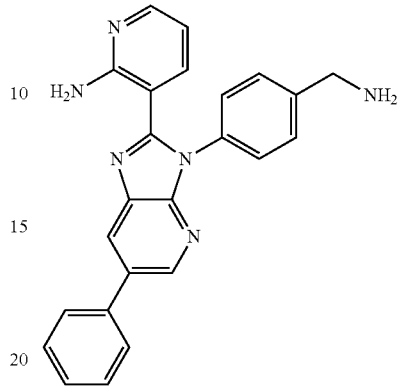

Intermediate 7

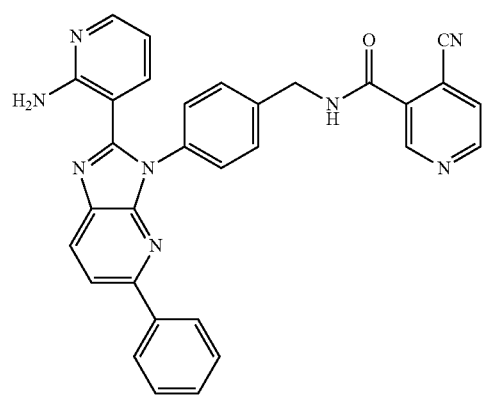

Example 105

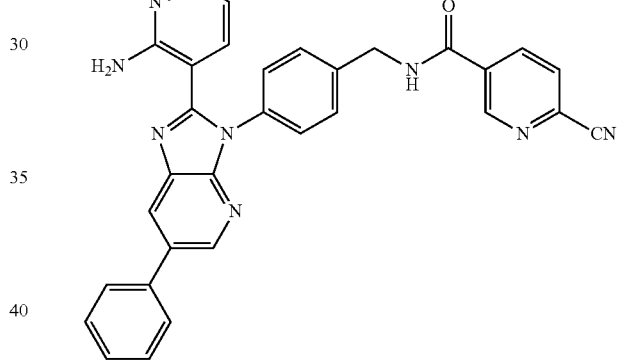

Example 106

Following the general procedure of Example 23, the reaction of Intermediate 4 (50 mg, 127 μmol) with 4-cyanopyridine-3-carboxylic acid (18.9 mg, 127 μmol) was carried out. After purified by prep-HPLC (column: Waters Xbridge BEH C18 100×30 mm×10 μm; mobile phase: [water (NH$_4$HCO$_3$)-ACN]; B %: 33%-63%, 2 min), N-(4-(2-(2-aminopyridin-3-yl)-5-phenyl-3H-imidazo[4,5-b]pyridin-3-yl)benzyl)-4-cyanonicotinamide (Example 105, 10.2 mg, yield: 15%) was obtained as an off-white solid. MS: m/z=523.2 [M+H]$^+$. $^1$H NMR (400 MHz, Chloroform-d) δ 9.23 (s, 1H), 9.06 (d, J=6.0 Hz, 1H), 8.20 (d, J=8.4 Hz, 1H), 7.97 (d, J=8.0 Hz, 2H), 7.87 (d, J=8.0 Hz, 1H), 7.80-7.64 (m, 4H), 7.52-7.37 (m, 7H), 7.25-7.22 (m, 2H), 6.59-6.52 (m, 1H), 5.19 (s, 2H).

Following the general procedure of Example 23, the reaction of Intermediate 7 (150 mg, 382 μmol) with 6-cyanopyridine-3-carboxylic acid (68 mg, 459 μmol) was carried out. After purified by prep-HPLC (column: Waters xbridge 150*25 mm 10 μm; mobile phase: [water (NH$_4$HCO$_3$)-ACN], B %: 30%-60%, 8 min), N-(4-(2-(2-aminopyridin-3-yl)-6-phenyl-3H-imidazo[4,5-b]pyridin-3-yl)benzyl)-6-cyanonicotinamide (Example 106, 52 mg, yield: 26%) was obtained as an off-white solid. MS: m/z=523.2 [M+H]$^+$. $^1$H NMR (400 MHz, Dimethylsulfoxide-d$_6$) δ 9.52 (t, J=6.0 Hz, 1H), 9.20 (d, J=1.6 Hz, 1H), 8.61 (d, J=2.0 Hz, 1H), 8.51-8.44 (m, 2H), 8.20 (d, J=8.0 Hz, 1H), 8.01 (dd, J=4.8, 1.6 Hz, 1H), 7.78 (d, J=7.6 Hz, 2H), 7.55-7.49 (m, 4H), 7.46-7.39 (m, 3H), 7.27 (dd, J=7.6, 1.6 Hz, 1H), 6.99 (br s, 2H), 6.43 (dd, J=7.6, 4.8 Hz, 1H), 4.62 (d, J=6.0 Hz, 2H).

Example 107: N-(1-(4-(2-(2-Aminopyridin-3-yl)-6-phenyl-3H-imidazo[4,5-b]pyridin-3-yl)benzyl)piperidin-4-yl)-2-cyanoisonicotinamide

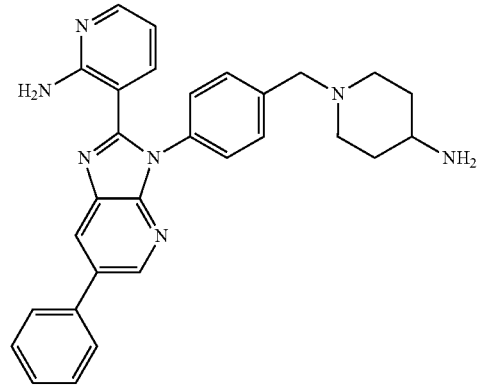

Intermediate 9

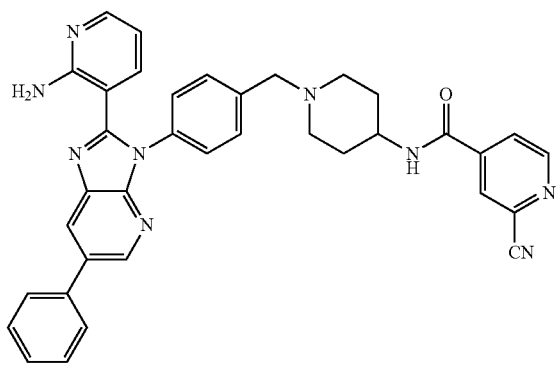

Example 107

Following the general procedure of Example 23, the reaction of Intermediate 9 (150 mg, 315 μmol) with 2-cyanopyridine-4-carboxylic acid (46.7 mg, 315 μmol) was carried out. After purified by prep-HPLC (column: Waters Xbridge 150×25 mm×5 μm; mobile phase: [water (NH$_4$HCO$_3$)-ACN]; B %: 35%-65%, 9 min), N-(1-(4-(2-(2-aminopyridin-3-yl)-6-phenyl-3H-imidazo[4,5-b]pyridin-3-yl)benzyl)piperidin-4-yl)-2-cyanoisonicotinamide (Example 107, 117 mg, yield: 60%) was obtained as a white solid. MS: m/z=606.3 [M+H]$^+$. $^1$H NMR (400 MHz, Dimethylsulfoxide-d$_6$) δ 8.90 (d, J=4.8 Hz, 1H), 8.74 (d, J=7.6 Hz, 1H), 8.64 (d, J=2.0 Hz, 1H), 8.46 (d, J=2.0 Hz, 1H), 8.37 (s, 1H), 8.07 (dd, J=5.2, 1.6 Hz, 1H), 8.01 (dd, J=4.8, 1.6 Hz, 1H), 7.78 (d, J=7.2 Hz, 2H), 7.55-7.50 (m, 2H), 7.48 (m, J=8.4 Hz, 2H), 7.44-7.39 (m, 3H), 7.20 (dd, J=7.6, 1.6 Hz, 1H), 7.07 (br s, 2H), 6.39 (dd, J=7.6, 4.8 Hz, 1H), 3.84-3.76 (m, 1H), 3.58 (s, 2H), 2.87 (br d, J=11.6 Hz, 2H), 2.16-2.07 (m, 2H), 1.88-1.81 (m, 2H), 1.67-1.58 (m, 2H).

Example 108: N-(4-(2-(2-Aminopyridin-3-yl)-3H-imidazo[4,5-b]pyridin-3-yl)benzyl)-6-cyanopicolinamide

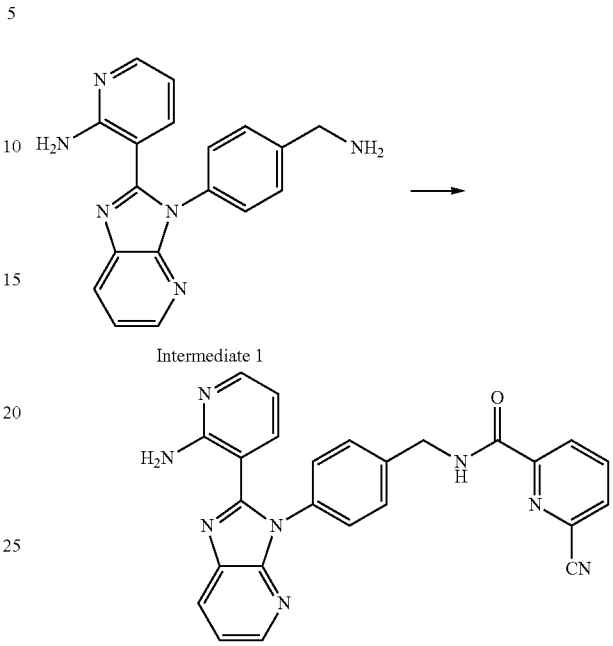

Following the general procedure of Example 23, the reaction of Intermediate 1 (180 mg, 569 μmol) with 6-cyanopicolinic acid (92.7 mg, 626 μmol) was carried out. After purified by prep-HPLC (column: Waters xbridge 150×25 mm 10 μm; mobile phase: [water (NH$_4$HCO$_3$)-ACN]; B %: 21%-51%, 8 min), N-(4-(2-(2-aminopyridin-3-yl)-3H-imidazo[4,5-b]pyridin-3-yl)benzyl)-6-cyanopicolinamide (Example 108 130 mg, yield: 50%) was obtained as a light-yellow solid. MS: m/z=447.1 [M+H]$^+$. $^1$H NMR (400 MHz, Dimethylsulfoxide-d$_6$) δ 9.60 (t, J=6.4 Hz, 1H), 8.35-8.32 (m, 1H), 8.31-8.28 (m, 1H), 8.28-8.22 (m, 2H), 8.19 (dd, J=8.0, 1.6 Hz, 1H), 7.99 (dd, J=4.8, 2.0 Hz, 1H), 7.47 (d, J=8.4 Hz, 2H), 7.40-7.36 (m, 3H), 7.23 (dd, J=7.6, 2.0 Hz, 1H), 6.96 (br s, 2H), 6.41 (dd, J=7.6, 4.8 Hz, 1H), 4.58 (d, J=6.4 Hz, 2H).

Example 109: 4-(4-(4-(2-(2-Aminopyridin-3-yl)-3H-imidazo[4,5-b]pyridin-3-yl)benzyl)piperazine-1-carbonyl)picolinonitrile

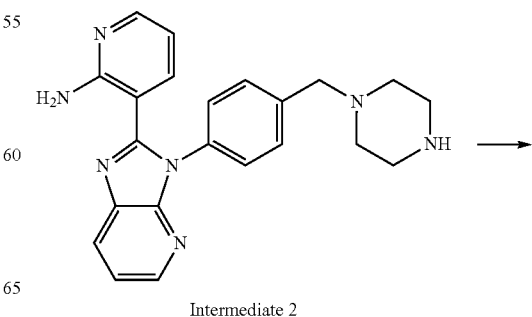

Intermediate 2

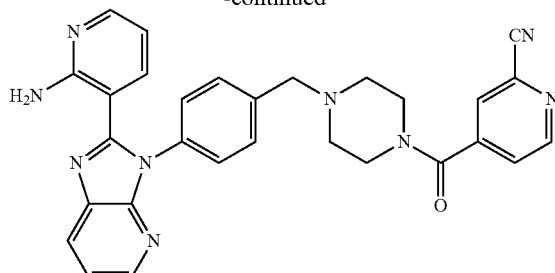

Example 109

Following the general procedure of Example 23, the reaction of Intermediate 2 (200 mg, 519 μmol) with 2-cyanoisonicotinic acid (76.9 mg, 519 μmol) was carried out. After purified by prep-HPLC (column: Waters xbridge 150× 25 mm 10 μm; mobile phase: [water (NH₄HCO₃)-ACN]; B %: 21%-51%, 8 min), (column: Waters xbridge 150×25 mm 10 μm; mobile phase: [water (NH₄HCO₃)-ACN]; B %: 21%-51%, 8 min), 4-(4-(4-(2-(2-aminopyridin-3-yl)-3H-imidazo[4,5-b]pyridin-3-yl)benzyl)piperazine-1-carbonyl)picolinonitrile (Example 109, 110 mg, yield: 41%) was obtained as a light-yellow solid. MS: m/z=516.3 [M+H]⁺. ¹H NMR (400 MHz, Dimethylsulfoxide-$d_6$) δ 8.84 (d, J=5.2 Hz, 1H), 8.32 (dd, J=4.8, 1.6 Hz, 1H), 8.20 (dd, J=8.0, 1.2 Hz, 1H), 8.11 (s, 1H), 7.98 (dd, J=4.8, 1.6 Hz, 1H), 7.75 (dd, J=4.8, 1.6 Hz, 1H), 7.46 (d, J=8.0 Hz, 2H), 7.41-7.37 (m, 3H), 7.16 (dd, J=7.6, 1.6 Hz, 1H), 7.00 (br s, 2H), 6.38 (dd, J=7.6, 4.8 Hz, 1H), 3.69-3.64 (m, 2H), 3.60 (s, 2H), 3.31-3.27 (m, 2H), 2.60-2.54 (m, 2H), 2.42-2.37 (m, 2H).

Example 110: 2-(4-(4-(2-(2-Aminopyridin-3-yl)-3H-imidazo[4,5-b]pyridin-3-yl)benzyl)piperazine-1-carbonyl)nicotinonitrile

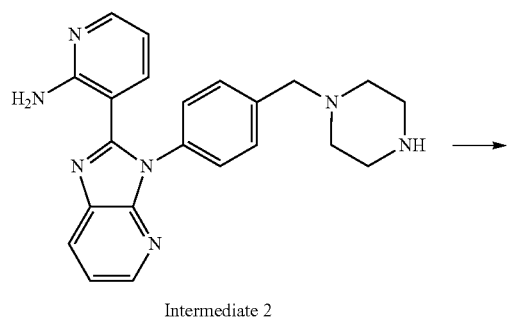

Intermediate 2

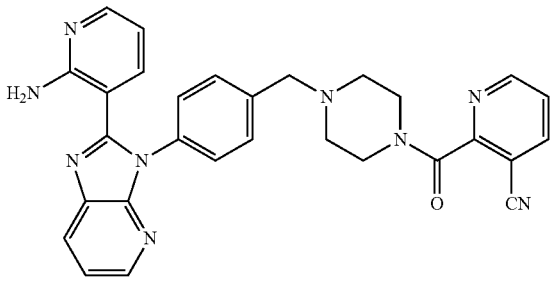

Example 110

Following the general procedure of Example 23, the reaction of Intermediate 2 (200 mg, 518 μmol) with 3-cyanopicolinic acid (115 mg, 778 μmol) was carried out. After purified by prep-HPLC (column: Waters Xbridge BEH C18 150*25 mm*5 μm; mobile phase: [water (NH₄HCO₃)-ACN]; B %: 15%-45%, 10 min), 2-(4-(4-(2-(2-aminopyridin-3-yl)-3H-imidazo[4,5-b]pyridin-3-yl)benzyl)piperazine-1-carbonyl)nicotinonitrile (Example 110, 10.5 mg, yield: 3.9%) was obtained as a light-yellow powder. MS: m/z=516.0 [M+H]⁺. ¹H NMR (400 MHz, Dimethylsulfoxide-$d_6$) δ 8.86 (dd, J=4.8, 1.6 Hz, 1H), 8.47 (dd, J=8.0, 1.6 Hz, 1H), 8.32 (dd, J=4.8, 1.2 Hz, 11H), 8.20 (dd, J=8.0, 1.6 Hz, 1H), 7.98 (dd, J=4.8, 2.0 Hz, 1H), 7.70 (dd, J=8.0, 4.8 Hz, 1H), 7.47 (d, J=8.4 Hz, 2H), 7.42-7.34 (m, 3H), 7.15 (dd, J=7.6, 1.6 Hz, 1H), 7.00 (br s, 2H), 6.38 (dd, J=7.6, 4.8 Hz, 1H), 3.75-3.70 (m, 2H), 3.62 (s, 2H), 3.29-3.26 (m, 2H), 2.54-2.52 (m, 2H), 2.43-2.39 (m, 2H).

Example 111: 5-(4-(4-(2-(2-Aminopyridin-3-yl)-6-phenyl-3H-imidazo[4,5-b]pyridin-3-yl)benzyl)piperazine-1-carbonyl)picolinonitrile

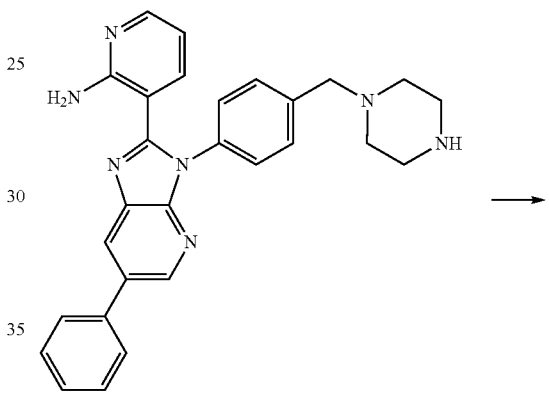

Intermediate 8

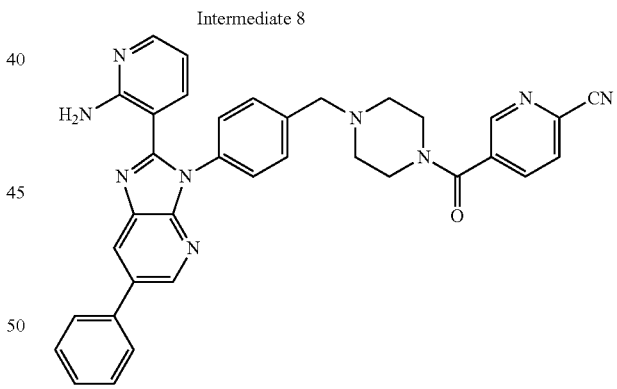

Example 111

Following the general procedure of Example 23, the reaction of Intermediate 8 (150 mg, 325 μmol) with 6-cyanopyridine-3-carboxylic acid (58 mg, 389 μmol) was carried out. After purified by prep-HPLC (column: Waters xbridge 150*25 mm 10 μm; mobile phase: [water (NH₄HCO₃)-ACN]; B %: 35%-65%, 9 min), 5-(4-(4-(2-(2-aminopyridin-3-yl)-6-phenyl-3H-imidazo[4,5-b]pyridin-3-yl)benzyl)piperazine-1-carbonyl)picolinonitrile (Example 111, 25.5 mg, yield: 13.3%) was obtained as a yellow solid. MS: m/z=592.1 [M+H]⁺. ¹H NMR (400 MHz, Chloroform-$d_6$) δ 8.78 (s, 1H), 8.64 (d, J=1.6 Hz, 1H), 8.29 (d, J=2.0 Hz, 1H), 8.08 (d, J=4.8 Hz, 1H), 7.93 (dd, J=8.0, 2.0 Hz, 1H), 7.79 (d, J=8.0 Hz, 1H), 7.65 (d, J=7.2 Hz, 1H), 7.55-7.49 (m, 4H), 7.45-7.36 (m, 3H), 7.12 (d, J=7.6 Hz, 1H), 6.78 (br s, 2H), 6.35 (dd, J=7.6, 4.8 Hz, 1H), 3.91-3.79 (m, 2H), 3.65 (s, 2H), 3.52-3.38 (m, 2H), 2.69-2.57 (m, 2H), 2.56-2.45 (m, 2H).

Example 112: 5-((4-(2-(2-Aminopyridin-3-yl)-5-phenyl-3H-imidazo[4,5-b]pyridin-3-yl)benzyl) amino)pyridazine-3-carbonitrile

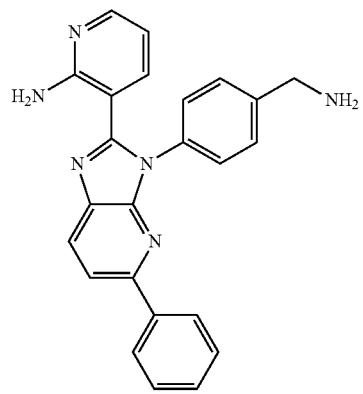

Intermediate 4

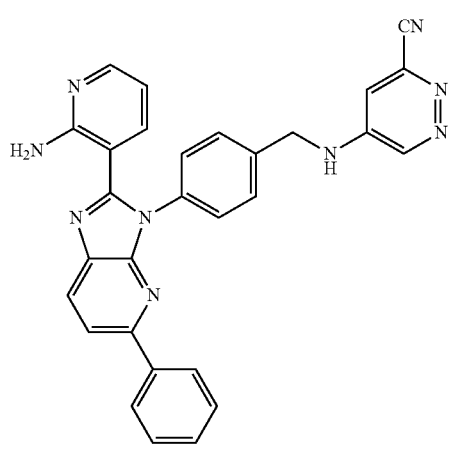

Example 112

Following the general procedure of Example 47, the reaction of Intermediate 4 (150 mg, 382 μmol) with Intermediate 21 (53 mg, 382 μmol) was carried out. After purified by prep-HPLC (column: Waters xbridge 150*25 mm 10 μm; mobile phase: [water (NH₄HCO₃)-ACN]; B %: 40%-70%, 10 min), 5-((4-(2-(2-aminopyridin-3-yl)-5-phenyl-3H-imidazo[4,5-b]pyridin-3-yl)benzyl)amino)pyridazine-3-carbonitrile (Example 112, 81.9 mg, yield: 43%) was obtained as a yellow solid. MS: m/z=496.2 [M+H]⁺. ¹H NMR (400 MHz, Dimethylsulfoxide-d₆) δ 8.83 (d, J=2.8 Hz, 1H), 8.29-8.19 (m, 2H), 8.04-7.96 (m, 4H), 7.55-7.45 (m, 6H), 7.43-7.37 (m, 1H), 7.32 (d, J=2.8 Hz, 1H), 7.18 (dd, J=7.6, 1.6 Hz, 1H), 6.97 (br s, 2H), 6.38 (dd, J=7.6, 4.8 Hz, 1H), 4.56 (d, J=6.0 Hz, 2H).

Example 113: N-(4-(2-(2-Aminopyridin-3-yl)-3H-imidazo[4,5-b]pyridin-3-yl)benzyl)-6-cyanopyrimidine-4-carboxamide

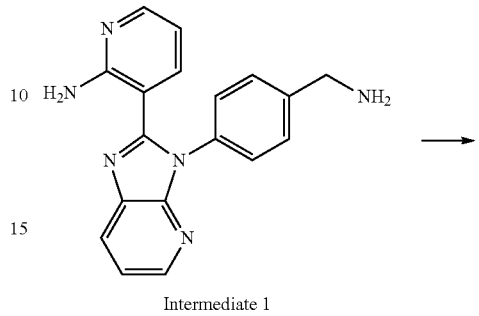

Intermediate 1

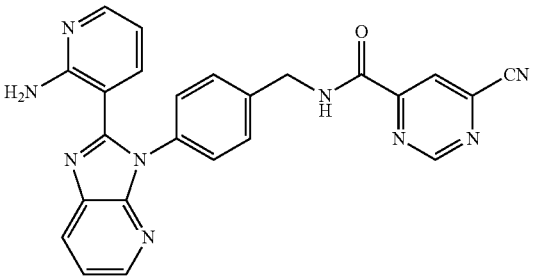

Example 113

To a solution of Intermediate 1 (200 mg, 632 μmol), 6-cyanopyrimidine-4-carboxylic acid (94.3 mg, 632 μmol), EDCI (182 mg, 948 μmol) and HOBt (128 mg, 948 μmol) in CH₂Cl₂ (2 mL) was added DIEA (409 mg, 3.16 mmol). The mixture was stirred at 25° C. for 16 hr. The reaction was concentrated under reduced pressure to give a residue. The crude product was purified by prep-HPLC (column: Waters xbridge 150×25 mm 10 μm; mobile phase: [water (NH₄HCO₃)-ACN]; B %: 18%-48%, 8 min), N-(4-(2-(2-aminopyridin-3-yl)-3H-imidazo[4,5-b]pyridin-3-yl)benzyl)-6-cyanopyrimidine-4-carboxamide (Example 113, 57.5 mg, yield: 20%) was obtained as a yellow solid. MS: m/z=448.2 [M+H]⁺. ¹H NMR (400 MHz, Dimethylsulfoxide-d₆) δ 9.89 (t, J=6.4 Hz, 1H), 9.56 (d, J=1.2 Hz, 1H), 8.58 (d, J=1.2 Hz, 1H), 8.29 (dd, J=4.8, 1.6 Hz, 1H), 8.19 (dd, J=8.0, 1.2 Hz, 1H), 7.98 (dd, J=4.8, 1.6 Hz, 1H), 7.47 (d, J=8.4 Hz, 2H), 7.40-7.36 (m, 3H), 7.23 (dd, J=7.6, 2.0 Hz, 1H), 6.94 (br s, 2H), 6.40 (dd, J=8.0, 4.8 Hz, 1H), 4.59 (d, J=6.4 Hz, 2H).

Example 114: 6-(4-(4-(2-(2-Aminopyridin-3-yl)-3H-imidazo[4,5-b]pyridin-3-yl)benzyl)piperazine-1-carbonyl)pyrimidine-4-carbonitrile

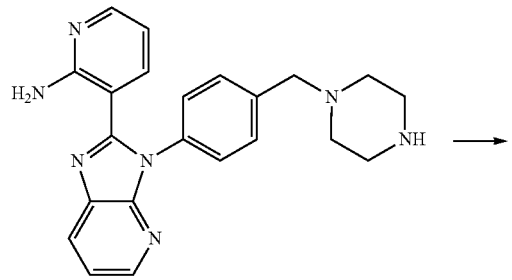

Intermediate 2

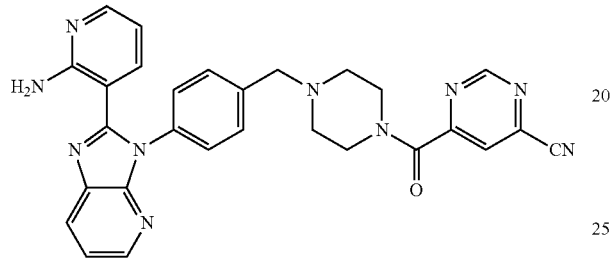

Example 114

Following the general procedure of Example 113, the reaction of Intermediate 2 (200 mg, 519 µmol) with 6-cyanopyrimidine-4-carboxylic acid (77.4 mg, 519 µmol) was carried out. After purified by prep-HPLC (column: Waters xbridge 150×25 mm 10 µm; mobile phase: [water (NH$_4$HCO$_3$)-ACN]; B %: 20%-50%, 8 min), 6-(4-(4-(2-(2-aminopyridin-3-yl)-3H-imidazo[4,5-b]pyridin-3-yl)benzyl)piperazine-1-carbonyl)pyrimidine-4-carbonitrile (Example 114, 37.3 mg, yield: 13%) was obtained as a yellow solid. MS: m/z=517.1 [M+H]$^+$. $^1$H NMR (400 MHz, Dimethylsulfoxide-d$_6$) δ 9.45 (s, 1H), 8.36 (s, 1H), 8.33 (dd, J=4.8, 1.6 Hz, 1H), 8.20 (dd, J=8.0, 1.6 Hz, 1H), 7.98 (dd, J=4.8, 1.6 Hz, 1H), 7.47 (d, J=8.0 Hz, 2H), 7.41-7.37 (m, 3H), 7.16 (dd, J=8.0, 2.0 Hz, 1H), 6.99 (br s, 2H), 6.38 (dd, J=7.6, 4.8 Hz, 1H), 3.73-3.65 (m, 2H), 3.62 (s, 2H), 3.44-3.39 (m, 2H), 2.53-2.51 (m, 2H), 2.42-2.38 (m, 2H).

Example 115: N-(4-(2-(2-Aminopyridin-3-yl)-5-phenyl-3H-imidazo[4,5-b]pyridin-3-yl)benzyl)-6-cyanopyrimidine-4-carboxamide

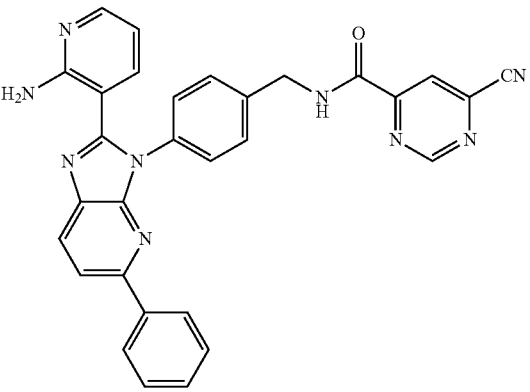

Example 115

Following the general procedure of Example 113, the reaction of Intermediate 4 (200 mg, 510 µmol) with 6-cyanopyrimidine-4-carboxylic acid (76 mg, 510 µmol) was carried out. After purified by prep-HPLC (column: Welch Ultimate C18 150×25 mm×5 µm; mobile phase: [water (FA)-ACN]; B %: 25%-55%, 10 min), N-(4-(2-(2-aminopyridin-3-yl)-5-phenyl-3H-imidazo[4,5-b]pyridin-3-yl)benzyl)-6-cyanopyrimidine-4-carboxamide (Example 115, 24.1 mg, yield: 8%) was obtained as a yellow solid. MS: m/z=523.9 [M+H]$^+$. $^1$H NMR (400 MHz, Dimethylsulfoxide-d$_6$) δ 9.89 (t, J=6.0 Hz, 1H), 9.57 (d, J=1.2 Hz, 1H), 8.59 (d, J=1.2 Hz, 1H), 8.26 (d, J=8.4 Hz, 1H), 8.03-7.96 (m, 4H), 7.51-7.44 (m, 6H), 7.41-7.37 (m, 1H), 7.21 (dd, J=7.6, 2.0 Hz, 1H), 6.92 (br s, 2H), 6.41 (dd, J=7.6, 4.8 Hz, 1H), 4.63 (d, J=6.0 Hz, 2H).

Example 116: 6-(4-(4-(2-(2-Aminopyridin-3-yl)-5-phenyl-3H-imidazo[4,5-b]pyridin-3-yl)benzyl)piperazine-1-carbonyl)pyrimidine-4-carbonitrile

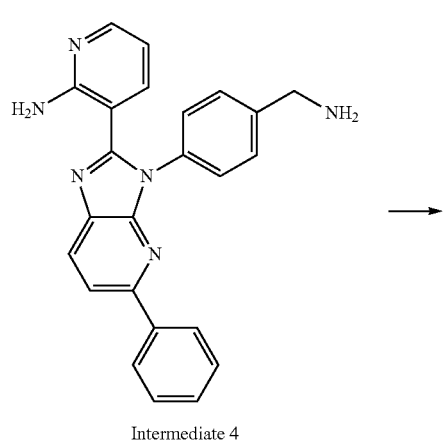

Intermediate 4

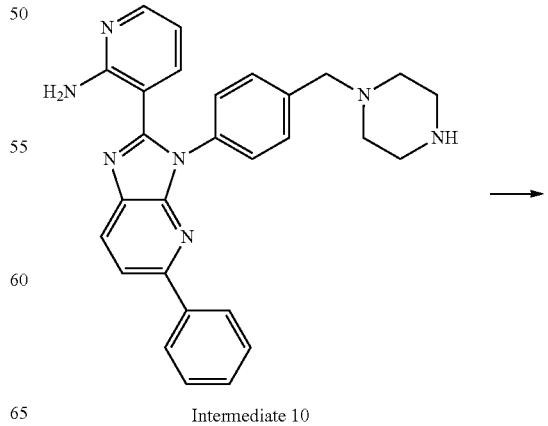

Intermediate 10

1183

-continued

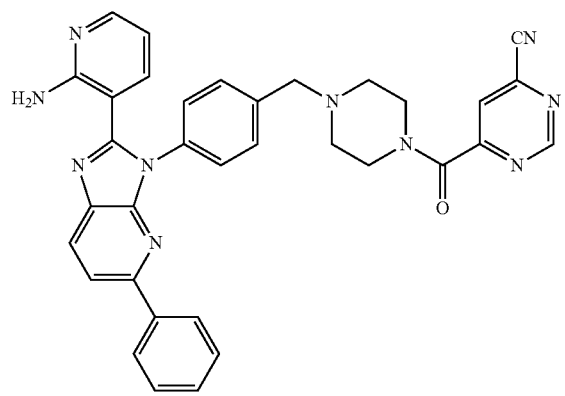

Example 116

Following the general procedure of Example 113, the reaction of Intermediate 10 (200 mg, 433 μmol) with 6-cyanopyrimidine-4-carboxylic acid (65 mg, 433 μmol) was carried out. After purified by prep-HPLC (column: Waters xbridge 150×25 mm 10 μm; mobile phase: [water (NH$_4$HCO$_3$)-ACN]; B %: 37%-67%, 8 min), 6-(4-(4-(2-(2-aminopyridin-3-yl)-5-phenyl-3H-imidazo[4,5-b]pyridin-3-yl)benzyl)piperazine-1-carbonyl)pyrimidine-4-carbonitrile (Example 116, 46.6 mg, yield: 17%) was obtained as a yellow solid. MS: m/z=593.2 [M+H]$^+$. $^1$H NMR (400 MHz, Chloroform-d) δ 9.35 (d, J=1.6 Hz, 1H), 8.15 (d, J=8.4 Hz, 1H), 8.03-7.98 (m, 4H), 7.82 (d, J=8.4 Hz, 1H), 7.52 (d, J=8.0 Hz, 1H), 7.45-7.38 (m, 5H), 7.16 (dd, J=7.6, 1.2 Hz, 1H), 7.13-7.02 (m, 2H), 6.38 (dd, J=7.6, 5.2 Hz, 1H), 3.91-3.86 (m, 2H), 3.72-3.62 (m, 4H), 2.68-2.58 (m, 4H).

Example 117: N-(1-(4-(2-(2-aminopyridin-3-yl)-5-phenyl-3H-imidazo[4,5-b]pyridin-3-yl)benzyl)piperidin-4-yl)-6-cyanopyrimidine-4-carboxamide

1184

-continued

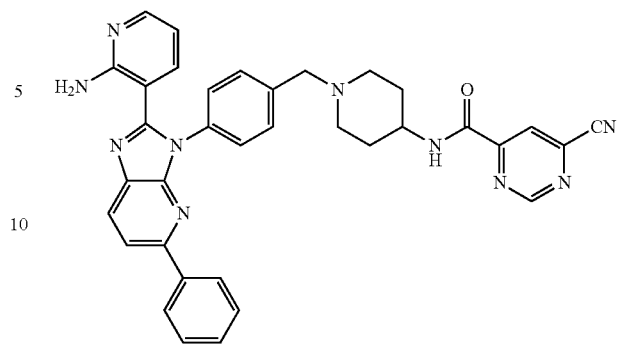

Example 117

Following the general procedure of Example 113, the reaction of Intermediate 11 (200 mg, 421 μmol) with 6-cyanopyrimidine-4-carboxylic acid (63 mg, 421 μmol) was carried out. After purified by prep-HPLC (column: Waters xbridge 150×25 mm 10 μm; mobile phase: [water (NH$_4$HCO$_3$)-ACN]; B %: 40%-70%, 8 min), N-(1-(4-(2-(2-aminopyridin-3-yl)-5-phenyl-3H-imidazo[4,5-b]pyridin-3-yl)benzyl)piperidin-4-yl)-6-cyanopyrimidine-4-carboxamide (Example 117, 28.4 mg, yield: 11%) was obtained as a yellow solid. MS: m/z=607.2 [M+H]$^+$. $^1$H NMR (400 MHz, Dimethylsulfoxide-d$_6$) δ 9.53 (d, J=1.6 Hz, 11H), 9.06 (d, J=8.0 Hz, 1H), 8.54 (d, J=1.2 Hz, 1H), 8.27 (d, J=8.4 Hz, 1H), 8.05-7.97 (m, 4H), 7.50-7.44 (m, 6H), 7.42-7.37 (m, 1H), 7.16 (dd, J=7.6, 1.6 Hz, 1H), 7.03 (br s, 2H), 6.38 (dd, J=8.0, 5.2 Hz, 1H), 3.88-3.80 (m, 1H), 3.59 (s, 2H), 2.87 (d, J=11.6 Hz, 2H), 2.15-2.08 (m, 2H), 1.80-1.71 (m, 4H).

Example 118: N-(4-(2-(2-aminopyridin-3-yl)-5-phenyl-3H-imidazo[4,5-b]pyridin-3-yl)benzyl)-3-cyanopicolinamide

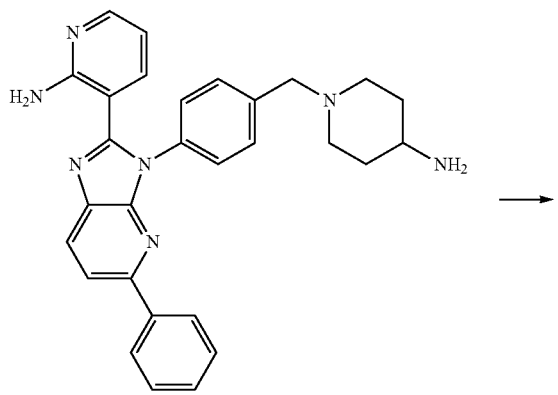

Intermediate 11

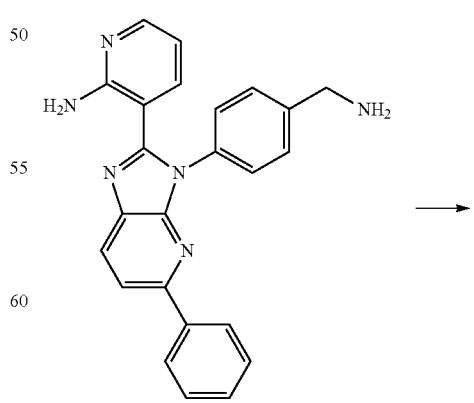

Intermediate 4

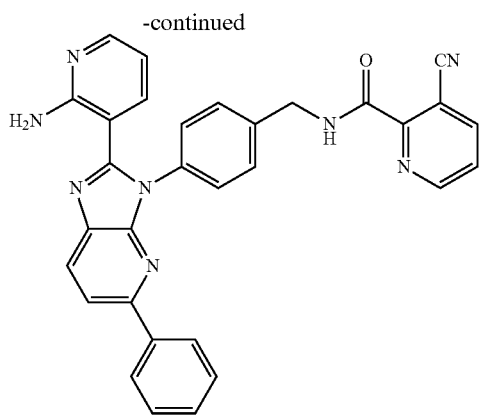

Example 118

Following the general procedure of Example 113, the reaction of Intermediate 4 (200 mg, 510 μmol) with 3-cyanopicolinic acid (76 mg, 510 μmol) was carried out. After purified by prep-HPLC (column: Phenomenex C18 150×25 mm×10 μm; mobile phase: [water (NH₄HCO₃)-ACN]; B %: 36%-66%, 8 min), N-(4-(2-(2-aminopyridin-3-yl)-5-phenyl-3H-imidazo[4,5-b]pyridin-3-yl)benzyl)-3-cyanopicolinamide (Example 118, 19.6 mg, yield: 7%) was obtained as a yellow solid. MS: m/z=523.3 [M+H]⁺. ¹H NMR (400 MHz, Dimethylsulfoxide-d₆) δ 10.52 (s, 1H), 8.92 (dd, J=4.8, 1.6 Hz, 1H), 8.60 (dd, J=8.0, 1.6 Hz, 1H), 8.26 (d, J=8.4 Hz, 1H), 8.02-7.96 (m, 4H), 7.80 (dd, J=7.6, 4.8 Hz, 1H), 7.50-7.44 (m, 6H), 7.41-7.36 (m, 1H), 7.18 (dd, J=7.6, 1.6 Hz, 1H), 6.91 (br s, 2H), 6.40 (dd, J=7.6, 4.8 Hz, 1H), 5.07 (s, 2H).

Example 119: N-(4-(2-(2-Aminopyridin-3-yl)-3H-imidazo[4,5-b]pyridin-3-yl)benzyl)-2-cyanopyrimidine-5-carboxamide

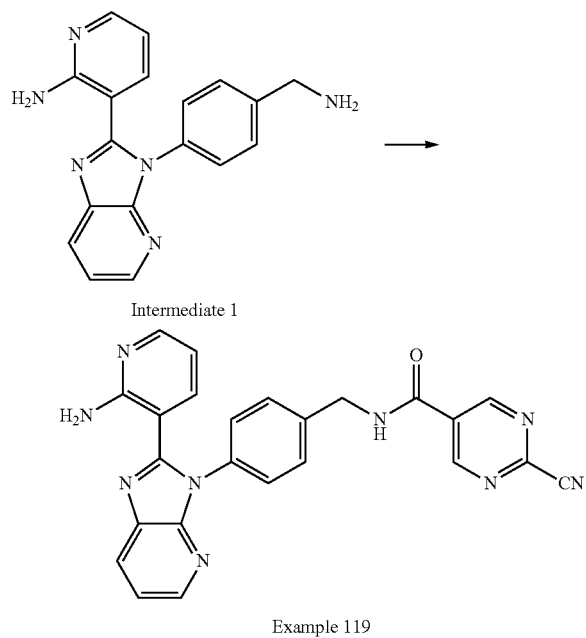

Example 119

To a solution of Intermediate 1, 2-cyanopyrimidine-5-carboxylic acid (94.3 mg, 632 μmol) and HATU (361 mg, 948 μmol) in DMF (1 mL) was added DIEA (409 mg, 3.16 mmol). The mixture was stirred at 25° C. for 16 hr. The reaction mixture was filtered to give filter liquor. The filter liquor was purified by prep-HPLC (column: Phenomenex C18 150×25 mm×10 μm; mobile phase: [water (NH₄HCO₃)-ACN]; B %: 18%-48%, 8 min), N-(4-(2-(2-aminopyridin-3-yl)-3H-imidazo[4,5-b]pyridin-3-yl)benzyl)-2-cyanopyrimidine-5-carboxamide (Intermediate 119, 42.5 mg, yield: 15%) was obtained as an off-white lyophilized powder. MS: m/z=448.3 [M+H]⁺. ¹H NMR (400 MHz, Dimethylsulfoxide-d₆) δ 9.66 (t, J=5.6 Hz, 1H), 9.39 (s, 2H), 8.30 (dd, J=4.8, 1.2 Hz, 1H), 8.20 (dd, J=8.0, 1.6 Hz, 1H), 7.99 (dd, J=4.8, 1.6 Hz, 1H), 7.51 (d, J=8.8 Hz, 2H), 7.44-7.36 (m, 3H), 7.24 (dd, J=7.6, 1.6 Hz, 1H), 6.92 (br s, 2H), 6.41 (dd, J=8.0, 5.2 Hz, 1H), 4.63 (d, J=5.6 Hz, 2H).

Example 120: N-(4-(2-(2-Aminopyridin-3-yl)-5-phenyl-3H-imidazo[4,5-b]pyridin-3-yl)benzyl)-2-cyanopyrimidine-5-carboxamide

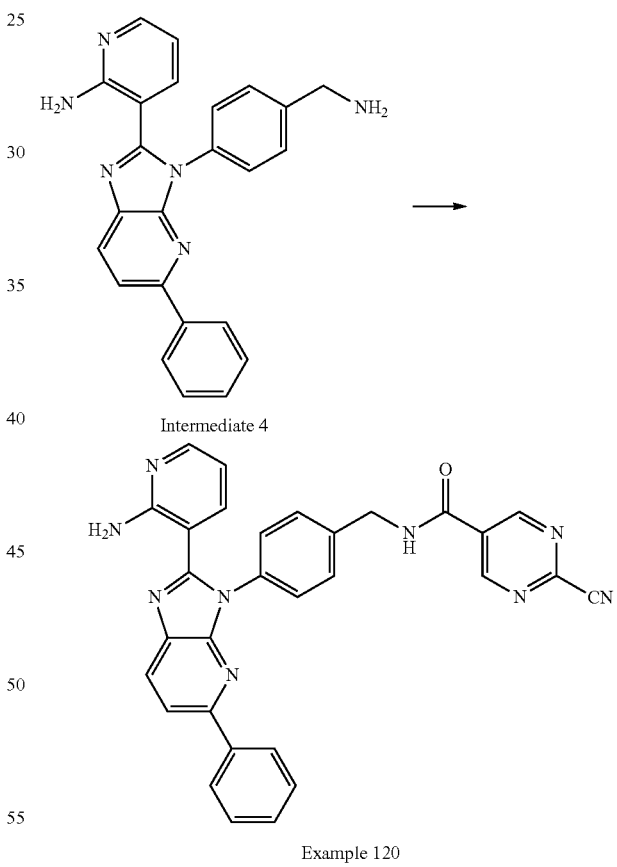

Example 120

To a solution of Intermediate 4 (135 mg, 344 μmol), 2-cyanopyrimidine-5-carboxylic acid (51.3 mg, 344 μmol) and HATU (196 mg, 516 μmol) in DMF (1 mL) was added DIEA (222 mg, 1.72 mmol). The mixture was stirred at 25° C. for 16 hr. The reaction mixture was filtered to give filter liquor. The filter liquor was purified by prep-HPLC (column: Phenomenex C18 150×25 mm×10 μm; mobile phase: [water (NH₄HCO₃)-ACN]; B %: 18%-48%, 8 min), N-(4-(2-(2-aminopyridin-3-yl)-5-phenyl-3H-imidazo[4,5-b]pyridin-3- yl)benzyl)-2-cyanopyrimidine-5-carboxamide (Example 120, 34.7 mg yield: 19.3%) was obtained as a gray solid. MS: m/z=524.3 [M+H]+. 1H NMR (400 MHz, Dimethylsulfoxide-d6) δ 9.67 (t, J=5.6 Hz, 1H), 9.40 (s, 2H), 8.27 (d, J=8.4 Hz, 1H), 8.05-8.02 (m, 1H), 8.01-7.96 (m, 3H), 7.56-7.52 (m, 2H), 7.51-7.48 (m, 2H), 7.45-7.43 (m, 2H), 7.42-7.37 (m, 1H), 7.23 (dd, J=7.6, 2.0 Hz, 1H), 6.91 (br s, 2H), 6.42 (dd, J=7.6, 4.8 Hz, 1H), 4.67 (d, J=5.6 Hz, 2H).

Example 121: N-(4-(2-(2-Aminopyridin-3-yl)-3H-imidazo[4,5-b]pyridin-3-yl)benzyl)-6-cyanonicotinamide

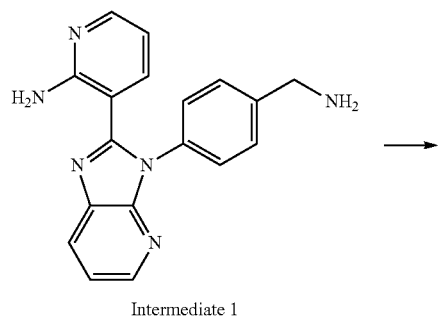

Intermediate 1

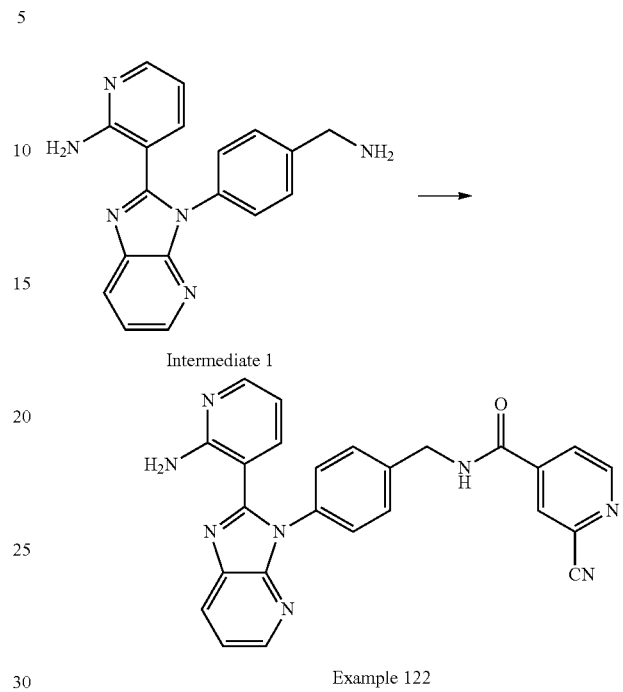

Example 122

Example 121

To a solution of Intermediate 1 and 6-cyanonicotinic acid (84 mg, 570 µmol) in DMF (2 mL) was added HATU (270 mg, 711 µmol) and DIEA (306 mg, 2.4 mmol). The resulting mixture was stirred at 25° C. for 16 hr. The reaction mixture was filtered. The filter liquor was concentrated to dryness to give a residue. The residue was purified by prep-HPLC (column: Waters xbridge 150×25 mm 10 µm; mobile phase: [water (NH4HCO3)-ACN]; B %: 16%-46%, 8 min), N-(4-(2-(2-aminopyridin-3-yl)-3H-imidazo[4,5-b]pyridin-3-yl)benzyl)-6-cyanonicotinamide (Example 121, 89.6 mg, yield: 42%) was obtained as a light yellow solid. MS: m/z=447.3 [M+H]+. 1H NMR (400 MHz, Dimethylsulfoxide-d6) δ 9.54 (t, J=6.0 Hz, 1H), 9.19 (d, J=1.6 Hz, 1H), 8.47 (dd, J=8.0, 2.4 Hz, 1H), 8.30 (dd, J=4.8, 1.6 Hz, 1H), 8.20 (d, J=8.0 Hz, 2H), 7.99 (dd, J=4.8, 2.0 Hz, 1H), 7.50 (d, J=8.4 Hz, 2H), 7.43-7.36 (m, 3H), 7.24 (dd, J=7.6, 1.6 Hz, 1H), 6.94 (br s, 2H), 6.41 (dd, J=7.8, 4.8 Hz, 1H), 4.61 (d, J=6.0 Hz, 2H).

Example 122, N-(4-(2-(2-Aminopyridin-3-yl)-3H-imidazo[4,5-b]pyridin-3-yl)benzyl)-2-cyanoisonicotinamide Following the general procedure of Example 121, the reaction of Intermediate 1 (150 mg, 474 µmol) with 2-cyanoisonicotinic acid (70 mg, 474 µmol) was carried out. After purified by prep-HPLC (column: Waters xbridge 150×25 mm 10 µm; mobile phase: [water (NH4HCO3)-ACN]; B %: 26%-56%, 8 min), N-(4-(2-(2-aminopyridin-3-yl)-3H-imidazo[4,5-b]pyridin-3-yl)benzyl)-2-cyanoisonicotinamide (Example 122, 84 mg, yield: 39%) was obtained as a light yellow solid. MS: m/z=447.1 [M+H]+. 1H NMR (400 MHz, Dimethylsulfoxide-d6) δ 9.57 (t, J=6.0 Hz, 1H), 8.92 (d, J=5.2 Hz, 1H), 8.43 (s, 1H), 8.30 (d, J=4.8 Hz, 1H), 8.19 (d, J=8.0 Hz, 1H), 8.14 (d, J=4.8 Hz, 1H), 8.95 (d, J=4.4 Hz, 1H), 7.49 (d, J=8.0 Hz, 1H), 7.44-7.35 (m, 3H), 7.24 (d, J=7.6 Hz, 1H), 6.94 (br s, 2H), 6.41 (dd, J=7.8, 4.8 Hz, 1H), 4.61 (d, J=6.0 Hz, 2H).

Example 123: N-(4-(2-(2-Aminopyridin-3-yl)-3H-imidazo[4,5-b]pyridin-3-yl)benzyl)-5-cyanonicotinamide

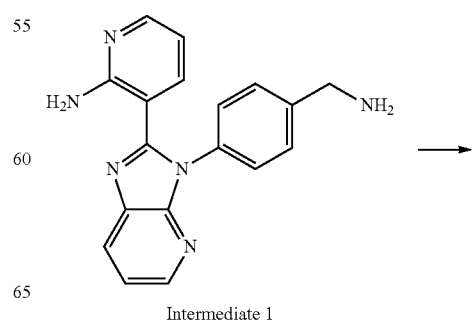

Intermediate 1

-continued

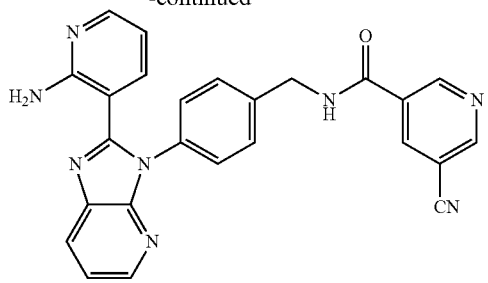

Example 123

Following the general procedure of Example 121, the reaction of Intermediate 1 (150 mg, 474 µmol) with 5-cyanonicotinic acid (70 mg, 474 µmol) was carried out. After purified by prep-HPLC (column: Waters xbridge 150×25 mm 10 µm; mobile phase: [water (NH₄HCO₃)-ACN]; B %: 14%-44%, 8 min), N-(4-(2-(2-aminopyridin-3-yl)-3H-imidazo[4,5-b]pyridin-3-yl)benzyl)-5-cyanonicotinamide (Example 123, 91.7 mg, yield: 41%) was obtained as a yellow solid. MS: m/z=447.0 [M+H]⁺. ¹H NMR (400 MHz, Dimethylsulfoxide-d₆) δ 9.47 (t, J=6.0 Hz, 1H), 9.29 (d, J=2.0 Hz, 1H), 9.18 (d, J=2.0 Hz, 1H), 8.74 (t, J=2.0 Hz, 1H), 8.31 (dd, J=4.8, 1.2 Hz, 1H), 8.20 (dd, J=8.0, 1.2 Hz, 1H), 7.99 (dd, J=4.8, 2.0 Hz, 1H), 7.49 (d, J=8.4 Hz, 1H), 7.42-7.36 (m, 3H), 7.24 (dd, J=8.0, 2.0 Hz, 1H), 6.94 (br s, 2H), 6.41 (dd, J=8.0, 4.8 Hz, 1H), 4.61 (d, J=6.0 Hz, 2H).

Example 124: N-(4-(2-(2-Aminopyridin-3-yl)-3H-imidazo[4,5-b]pyridin-3-yl)benzyl)-5-cyanopicolinamide

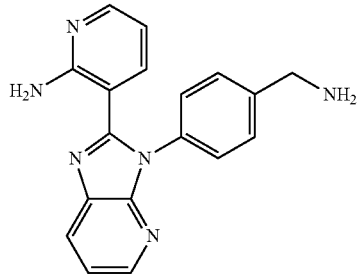

Intermediate 1

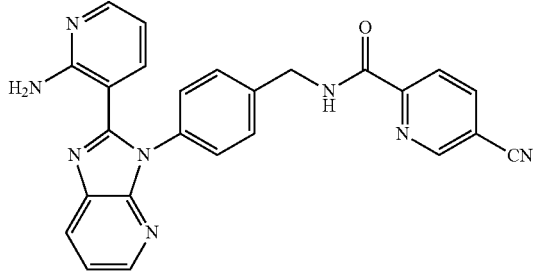

Example 124

Following the general procedure of Example 121, the reaction of Intermediate 1 (150 mg, 474 µmol) with 5-cyanopicolinic acid (70 mg, 474 µmol) was carried out. After purified by prep-HPLC (column: Waters xbridge 150×25 mm 10 µm; mobile phase: [water (NH₄HCO₃)-ACN]; B %: 19%-49%, 8 min), N-(4-(2-(2-aminopyridin-3-yl)-3H-imidazo[4,5-b]pyridin-3-yl)benzyl)-5-cyanopicolinamide (Example 124, 96.3 mg, yield: 45%) was obtained as a yellow solid. MS: m/z=447.0 [M+H]⁺. ¹H NMR (400 MHz, Dimethylsulfoxide-d₆) δ 9.69 (t, J=6.4 Hz, 1H), 9.15 (d, J=2.0 Hz, 1H), 8.52 (dd, J=8.0, 2.0 Hz, 1H), 8.29 (dd, J=4.8, 1.2 Hz, 1H), 8.20-8.12 (m, 2H), 7.98 (dd, J=4.8, 1.6 Hz, 1H), 7.46 (d, J=8.4 Hz, 2H), 7.44-7.38 (m, 3H), 7.22 (dd, J=7.6, 1.6 Hz, 1H), 6.96 (br s, 2H), 6.40 (dd, J=7.6, 4.8 Hz, 1H), 4.56 (d, J=6.4 Hz, 2H).

Example 125: N-(4-(2-(2-Aminopyridin-3-yl)-5-phenyl-3H-imidazo[4,5-b]pyridin-3-yl)benzyl)-5-cyanonicotinamide

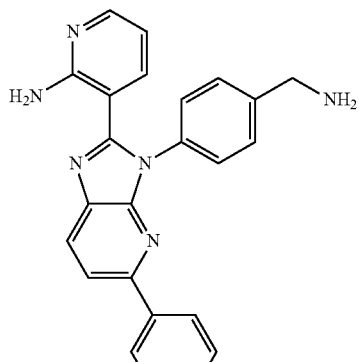

Intermediate 4

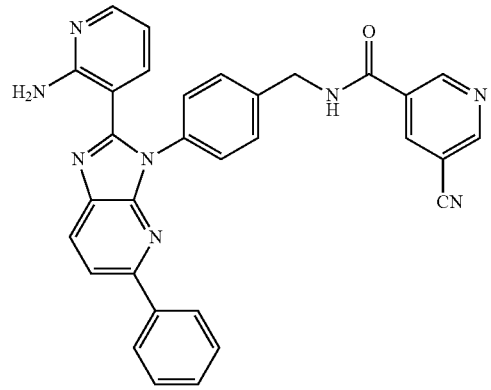

Example 125

Following the general procedure of Example 121, the reaction of Intermediate 4 (150 mg, 382 µmol) with 5-cyanonicotinic acid (57 mg, 382 µmol) was carried out. After purified by prep-HPLC (column: Waters xbridge 150×25 mm 10 µm; mobile phase: [water (NH₄HCO₃)-ACN]; B %: 32%-62%, 8 min), N-(4-(2-(2-aminopyridin-3-yl)-5-phenyl-3H-imidazo[4,5-b]pyridin-3-yl)benzyl)-5-cyanonicotinamide (Example 125, 7.7 mg, yield: 3.9%) was obtained as a yellow solid. MS: m/z=523.4 [M+H]⁺. ¹H NMR (400 MHz, Dimethylsulfoxide-d₆) δ 9.46 (t, J=5.6 Hz, 1H), 9.29 (d, J=2.0 Hz, 1H), 9.18 (d, J=2.4 Hz, 1H), 8.74 (t, J=2.0 Hz, 1H), 8.26 (d, J=8.4 Hz, 1H), 8.03-7.96 (m, 4H), 7.54-7.44 (m, 6H), 7.41-7.36 (m, 1H), 7.22 (dd, J=7.6, 1.6 Hz, 1H), 6.92 (br s, 2H), 6.42 (dd, J=7.6, 4.8 Hz, 1H), 4.64 (d, J=5.6 Hz, 2H).

Example 126: N-(4-(2-(2-Aminopyridin-3-yl)-5-phenyl-3H-imidazo[4,5-b]pyridin-3-yl)benzyl)-5-cyanopicolinamide

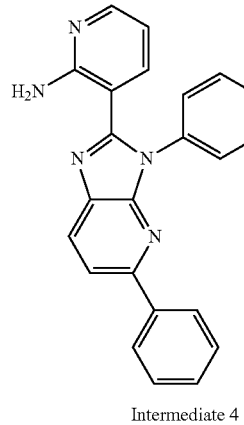

Intermediate 4

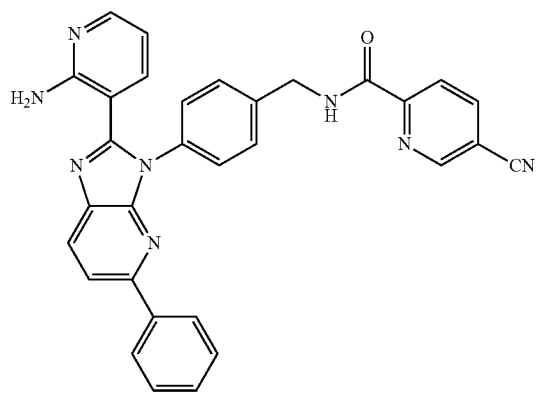

Example 126

Following the general procedure of Example 121, the reaction of Intermediate 4 (150 mg, 382 μmol) with 5-cyanopicolinic acid (57 mg, 382 μmol) was carried out. After purified by prep-HPLC (column: Waters xbridge 150×25 mm 10 μm; mobile phase: [water (NH$_4$HCO$_3$)-ACN]; B %: 36%-66%, 8 min), N-(4-(2-(2-aminopyridin-3-yl)-5-phenyl-3H-imidazo[4,5-b]pyridin-3-yl)benzyl)-5-cyanopicolinamide (Example 126, 28.3 mg, yield: 15%) was obtained as a yellow solid. MS: m/z=523.4 [M+H]$^+$. $^1$H NMR (400 MHz, Dimethylsulfoxide-d$_6$) δ 9.70 (t, J=6.4 Hz, 1H), 9.15 (d, J=1.2 Hz, 1H), 8.54 (dd, J=8.4, 2.0 Hz, 1H), 8.28-8.16 (m, 2H), 8.03-7.96 (m, 4H), 7.49-7.37 (m, 7H), 7.20 (dd, J=7.6, 1.6 Hz, 1H), 6.93 (br s, 2H), 6.41 (dd, J=7.6, 4.8 Hz, 1H), 4.62 (d, J=6.4 Hz, 2H).

Example 127: 4-((4-(2-(2-Aminopyridin-3-yl)-3H-imidazo[4,5-b]pyridin-3-yl)benzyl)amino)picolinonitrile

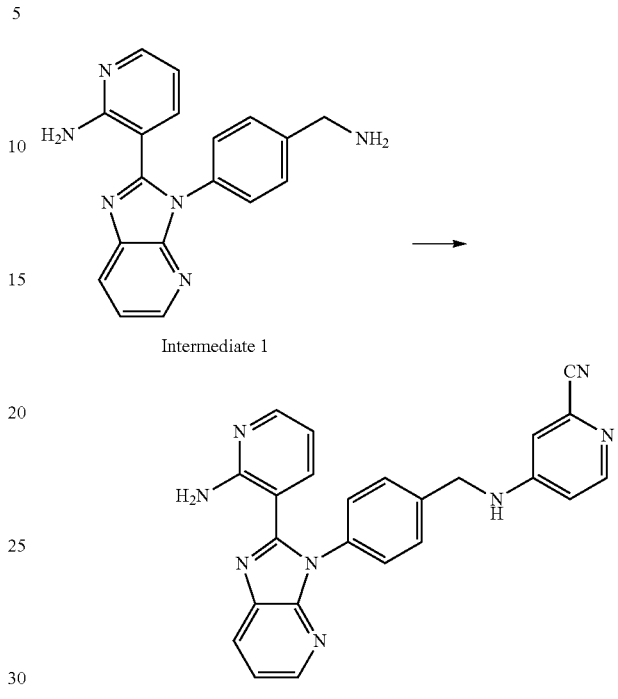

Intermediate 1

Example 127

To a solution of Intermediate 1 (150 mg, 474 μmol) and 4-fluoropyridine-2-carbonitrile (58 mg, 474 μmol) in DMSO (2 mL) was added DIEA (306 mg, 2.4 mmol). The mixture was stirred at 100 C for 16 hr. Then the mixture was purified by prep-HPLC (column: Waters xbridge 150×25 mm 10 μm; mobile phase: [water (NH$_4$HCO$_3$)-ACN]; B %: 18%-48%, 8 min), 4-((4-(2-(2-aminopyridin-3-yl)-3H-imidazo[4,5-b]pyridin-3-yl)benzyl)amino)picolinonitrile (Example 127, 48.6 mg, yield: 24%) was obtained as a yellow solid. MS: m/z=419.0 [M+H]$^+$. $^1$H NMR (400 MHz, Dimethylsulfoxide-d$_6$) δ 8.31 (dd, J=4.8, 1.2 Hz, 1H), 8.20 (dd, J=7.6, 1.2 Hz, 1H), 8.14 (d, J=5.6 Hz, 1H), 7.99 (dd, J=4.8, 2.0 Hz, 1H), 7.76 (t, J=6.0 Hz, 1H), 7.48 (d, J=8.4 Hz, 1H), 7.43-7.36 (m, 3H), 7.17 (dd, J=7.6, 2.0 Hz, 1H), 7.12 (d, J=2.0 Hz, 1H), 6.98 (br s, 2H), 6.79 (d, J=3.6 Hz, 1H), 6.36 (dd, J=7.6, 4.8 Hz, 1H), 4.48 (d, J=6.0 Hz, 2H).

Example 128: 5-((4-(2-(2-Aminopyridin-3-yl)-3H-imidazo[4,5-b]pyridin-3-yl)benzyl)amino)picolinonitrile

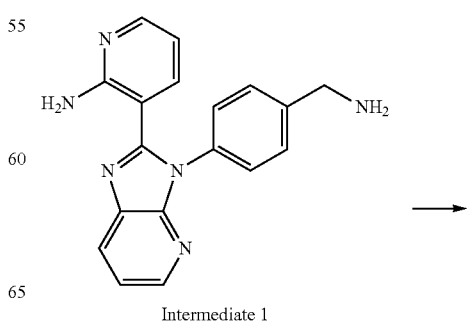

Intermediate 1

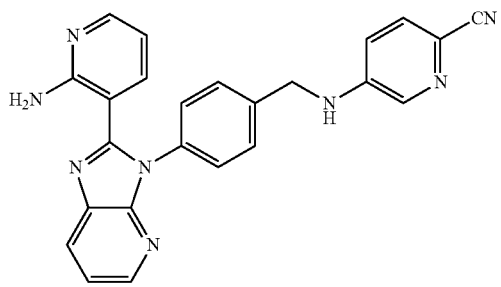

Example 128

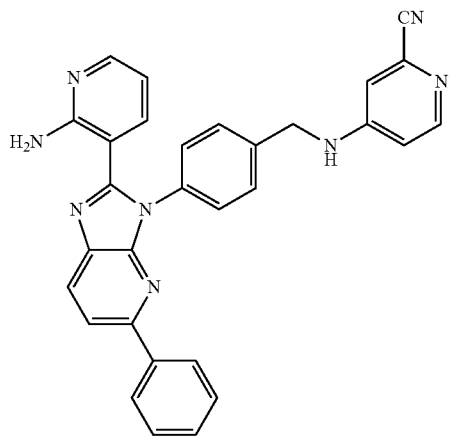

Example 129

Following the general procedure of Example 127, the reaction of Intermediate 1 (150 mg, 474 μmol) with 5-fluoropicolinonitrile (58 mg, 474 μmol) was carried out. After purified by prep-HPLC (column: Waters xbridge 150×25 mm 10 μm; mobile phase: [water (NH$_4$HCO$_3$)-ACN]; B %: 18%-48%, 8 min), 5-((4-(2-(2-aminopyridin-3-yl)-3H-imidazo[4,5-b]pyridin-3-yl)benzyl)amino)picolinonitrile (Example 128, 53.1 mg, yield: 26%) was obtained as a yellow solid. MS: m/z=419.1 [M+H]$^+$. $^1$H NMR (400 MHz, Dimethylsulfoxide-d$_6$) δ 8.31 (d, J=3.6 Hz, 1H), 8.20 (d, J=8.0 Hz, 1H), 8.12 (d, J=2.8 Hz, 1H), 7.99 (dd, J=4.8, 1.6 Hz, 1H), 7.67-7.60 (m, 2H), 7.49 (d, J=8.0 Hz, 1H), 7.43-7.36 (m, 3H), 7.17 (dd, J=7.6, 1.6 Hz, 1H), 7.01-6.95 (m, 3H), 6.37 (dd, J=8.0, 4.8 Hz, 1H), 4.49 (d, J=6.0 Hz, 2H).

Example 129: 4-((4-(2-(2-Aminopyridin-3-yl)-5-phenyl-3H-imidazo[4,5-b]pyridin-3-yl)benzyl)amino)picolinonitrile

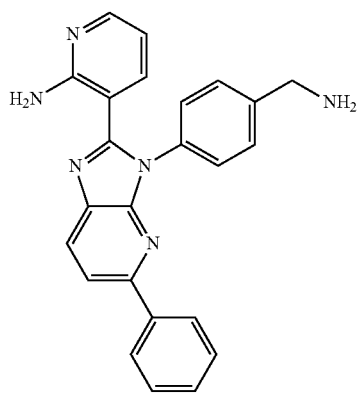

Intermediate 4

Following the general procedure of Example 127, the reaction of Intermediate 4 (200 mg, 510 μmol) with 4-fluoropyridine-2-carbonitrile (62 mg, 510 μmol) was carried out. After purified by prep-HPLC (column: Waters xbridge 150×25 mm 10 μm; mobile phase: [water (NH$_4$HCO$_3$)-ACN]; B %: 35%-65%, 8 min), 4-((4-(2-(2-aminopyridin-3-yl)-5-phenyl-3H-imidazo[4,5-b]pyridin-3-yl)benzyl)amino)picolinonitrile (Example 129, 16.3 mg, yield: 6%) was obtained as a yellow solid. MS: m/z=495.3 [M+H]$^+$. $^1$H NMR (400 MHz, Dimethylsulfoxide-d$_6$) δ 8.27 (d, J=8.4 Hz, 1H), 8.14 (d, J=5.6 Hz, 1H), 8.03-7.97 (m, 4H), 7.77 (t, J=6.0 Hz, 1H), 7.53-7.44 (m, 6H), 7.42-7.37 (m, 1H), 7.17 (dd, J=7.6, 1.6 Hz, 1H), 7.12 (d, J=2.0 Hz, 1H), 6.99 (br s, 2H), 6.85-6.79 (m, 1H), 6.37 (dd, J=8.0, 5.2 Hz, 1H), 4.51 (d, J=6.0 Hz, 2H).

Example 130: 6-((4-(2-(2-Aminopyridin-3-yl)-3H-imidazo[4,5-b]pyridin-3-yl)benzyl)amino)picolinonitrile

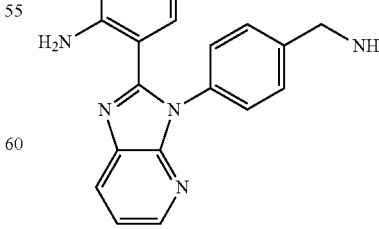

Intermediate 1

-continued

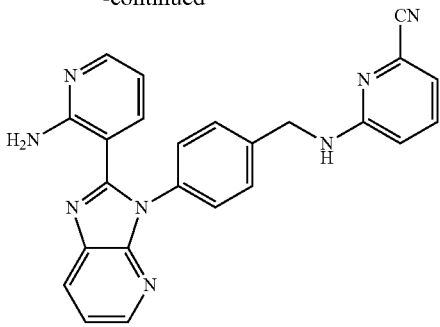

Example 130

A mixture of Intermediate 1 (200 mg, 632 μmol), 6-fluoropyridine-2-carbonitrile (92.6 mg, 759 μmol), DIEA (163 mg, 1.26 mmol) in DMSO (1 mL) was stirred under microwave at 120° C. for 1 hr. The reaction mixture was filtered, the filter liquor was purified by prep-HPLC (column: Waters xbridge 150×25 mm 10 μm; mobile phase: [water (NH$_4$HCO$_3$)-ACN]; B %. 30%-60%, 9 min), 6-((4-(2-(2-aminopyridin-3-yl)-3H-imidazo[4,5-b]pyridin-3-yl)benzyl)amino)picolinonitrile (Example 130, 74.5 mg, yield: 28%) was obtained as a brown lyophilized powder. MS: m/z=419.1 [M+H]$^+$. $^1$H NMR (400 MHz, Dimethylsulfoxide-d$_6$) δ 8.31 (dd, J=4.8, 1.6 Hz, 1H), 8.22-8.16 (m, 1H), 7.98 (dd, J=4.8, 2.0 Hz, 1H), 7.79-7.53 (m, 1H), 7.56 (dd, J=8.4, 7.2 Hz, 1H), 7.46 (d, J=8.4 Hz, 2H), 7.35-7.41 (m, 3H), 7.20 (dd, J=7.6, 2.0 Hz, 1H), 7.11-7.08 (m, 1H), 6.97 (br s, 2H), 6.86 (d, J=8.4 Hz, 1H), 6.38 (dd, J=7.6, 4.8 Hz, 1H), 4.55 (d, J=6.0 Hz, 2H).

Example 131: 5-((4-(2-(2-Aminopyridin-3-yl)-3H-imidazo[4,5-b]pyridin-3-yl)benzyl)amino)nicotinonitrile

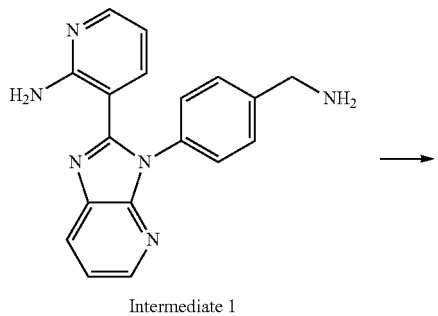

Intermediate 1

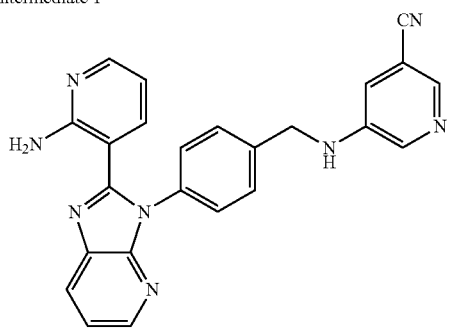

Example 131

Following the general procedure of Example 130, the reaction of 3-(3-(4-(aminomethyl)phenyl)-3H-imidazo[4,5-b]pyridin-2-yl)pyridin-2-amine (200 mg, 632 μmol) with 5-fluoropyridine-3-carbonitrile (92.6 mg, 758 μmol) was carried out. After purified by prep-HPLC (column: Waters xbridge 150×25 mm 10 μm; mobile phase: [water (NH$_4$HCO$_3$)-ACN]; B %: 25%-55%, 10 min), 5-((4-(2-(2-aminopyridin-3-yl)-3H-imidazo[4,5-b]pyridin-3-yl)benzyl)amino)nicotinonitrile (Example 131, 5.0 mg, yield: 1.9%) was obtained as a yellow solid. MS: m/z=419.1 [M+H]$^+$. $^1$H NMR (400 MHz, Dimethylsulfoxide-d$_6$) δ 8.36-8.30 (m, 2H), 8.19 (d, J=8.0 Hz, 1H), 8.13 (s, 1H), 8.00-7.97 (m, 1H), 7.50 (d, J=8.4 Hz, 2H), 7.43-7.36 (m, 3H), 7.30 (s, 1H), 7.20-7.12 (m, 2H), 7.00 (br s, 2H), 6.35 (dd, J=7.6, 4.8 Hz, 1H), 4.44 (d, J=6.0 Hz, 2H).

Example 132: 2-((4-(2-(2-Aminopyridin-3-yl)-3H-imidazo[4,5-b]pyridin-3-yl)benzyl)amino)isonicotinonitrile

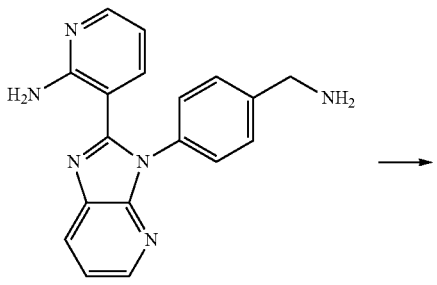

Intermediate 1

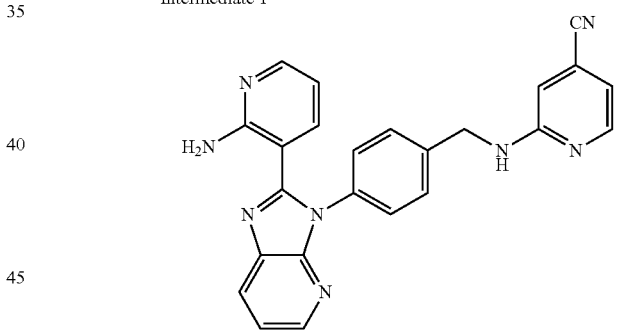

Example 132

To a solution of Intermediate 1 (200 mg, 632 μmol) and 2-chloropyridine-4-carbonitrile (87.6 mg, 632 μmol) in NMP (2 mL) was added DIEA (245 mg, 1.90 mmol). The mixture was stirred under microwave at 160° C. for 1 hr. The reaction mixture was filtered to give filter liquor. The filter liquor was purified by prep-HPLC (column: Welch Xtimate C18 150×25 mm×5 μm; mobile phase: [water (NH$_3$H$_2$O)-ACN]; B %: 22%-52%, 8 min), 2-((4-(2-(2-aminopyridin-3-yl)-3H-imidazo[4,5-b]pyridin-3-yl)benzyl)amino)isonicotinonitrile (Example 132, 12.7 mg, yield: 4.8%) was obtained as an off-white lyophilized powder. MS: m/z=419.1 [M+H]$^+$. $^1$H NMR (400 MHz, Dimethylsulfoxide-d$_6$) δ 8.30 (d, J=6.0 Hz, 1H), 8.22-8.16 (m, 2H), 8.01-7.95 (m, 1H), 7.74-7.71 (m, 1H), 7.45 (d, J=8.4 Hz, 2H), 7.40-7.35 (m, 3H), 7.20 (d, J=7.6 Hz, 1H), 6.95 (br s, 2H), 6.90 (s, 1H), 6.83 (d, J=5.2 Hz, 1H), 6.38 (dd, J=7.6, 4.8 Hz, 1H), 4.59 (d, J=6.0 Hz, 2H).

Example 133: 6-((4-(2-(2-Aminopyridin-3-yl)-3H-imidazo[4,5-b]pyridin-3-yl)benzyl)amino)pyrazine-2-carbonitrile

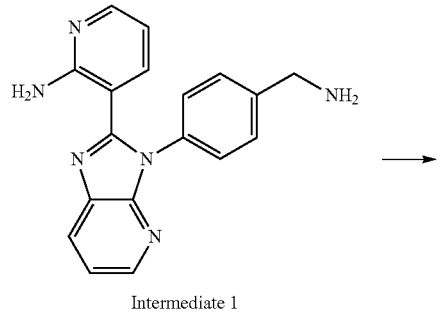

Intermediate 1

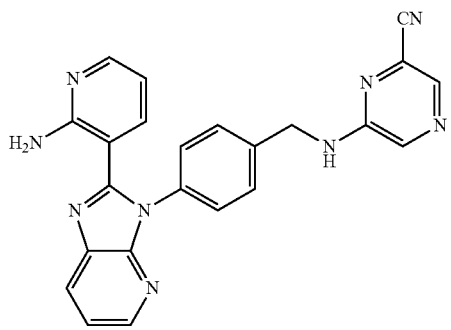

Example 133

To a solution of Intermediate 1 (200 mg, 632 μmol) and 6-chloropyrazine-2-carbonitrile (88.2 mg, 632 μmol) in NMP (2 mL) was added DIEA (245 mg, 1.9 mmol). The mixture was stirred under microwave at 130° C. for 0.5 hr. The reaction mixture was filtered to give filter liquor. The filter liquor was purified by prep-HPLC (column: Waters Xbridge BEH C18 100×30 mm×10 μm; mobile phase: [water (ammonia hydroxide v/v)-ACN]; B %: 22%-52%, 10 min), 6-((4-(2-(2-aminopyridin-3-yl)-3H-imidazo[4,5-b]pyridin-3-yl)benzyl)amino)pyrazine-2-carbonitrile (Example 133, 15.6 mg, yield: 5.9%) was obtained as a yellow lyophilized powder. MS: m/z=420.1 [M+H]$^+$. $^1$H NMR (400 MHz, Dimethylsulfoxide-d$_6$) δ 8.40-8.27 (m, 3H), 8.24-8.16 (m, 2H), 8.00-7.98 (m, 1H), 7.49 (d, J=8.0 Hz, 2H), 7.43-7.37 (m, 3H), 7.25-7.17 (m, 1H), 6.97 (br s, 2H), 6.35 (dd, J=7.6, 4.8 Hz, 1H), 4.57 (d, J=6.0 Hz, 2H).

Example 134: 2-((4-(2-(2-Aminopyridin-3-yl)-3H-imidazo[4,5-b]pyridin-3-yl)benzyl)amino)pyrimidine-4-carbonitrile

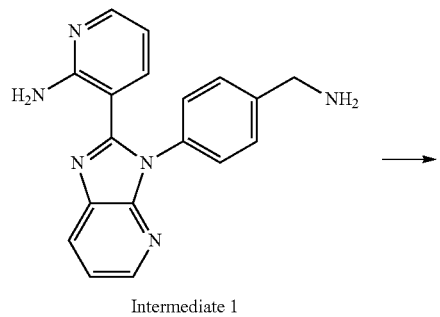

Intermediate 1

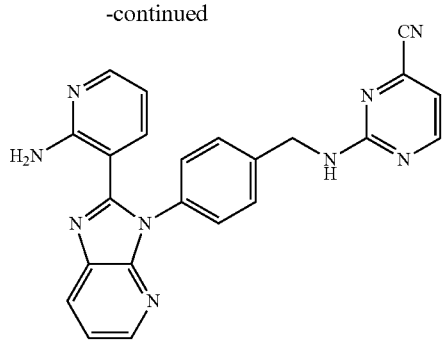

Example 134

Following the general procedure of Example 133, the reaction of Intermediate 1 (200 mg, 632 μmol) with 2-chloropyrimidine-4-carbonitrile (88.2 mg, 632 μmol) was carried out. After purified by prep-HPLC (column: Waters Xbridge BEH C18 100×30 mm×10 μm; mobile phase. [water (ammonia hydroxide v/v)-ACN]; B %: 32%-62%, 10 min), 2-((4-(2-(2-aminopyridin-3-yl)-3H-imidazo[4,5-b]pyridin-3-yl)benzyl)amino)pyrimidine-4-carbonitrile (Example 134, 6.4 mg, yield: 2.4%) was obtained as a yellow lyophilized powder. MS: m/z=420.0 [M+H]$^+$. $^1$H NMR (400 MHz, Dimethylsulfoxide-d$_6$) δ 8.59 (d, J=4.8 Hz, 1H), 8.51-8.47 (m, 1H), 8.32-8.29 (m, 1H), 8.20 (dd, J=8.0, 1.6 Hz, 1H), 7.98 (dd, J=4.8, 2.0 Hz, 1H), 7.46-7.42 (m, 2H), 7.40-7.35 (m, 3H), 7.20 (dd, J=7.6, 1.6 Hz, 1H), 7.15 (d, J=4.8 Hz, 1H), 6.98 (br s, 2H), 6.38 (dd, J=7.6, 5.2 Hz, 1H), 4.62-4.53 (m, 2H).

Example 135: 6-((4-(2-(2-aminopyridin-3-yl)-3H-imidazo[4,5-b]pyridin-3-yl)benzyl)amino)pyrimidine-4-carbonitrile

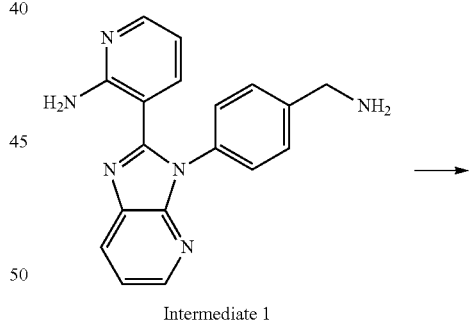

Intermediate 1

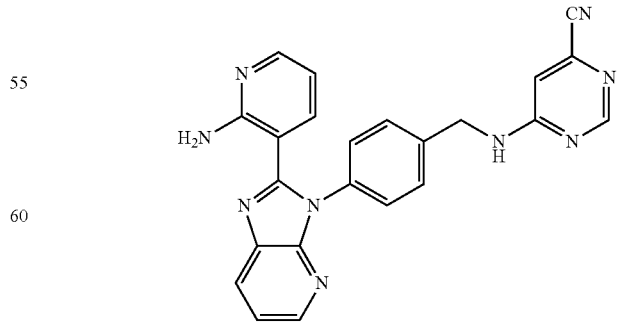

Example 135

Following the general procedure of Example 133, the reaction of Intermediate 1 (150 mg, 474 μmol) with 6-chloropyrimidine-4-carbonitrile (99.2 mg, 711 μmol) was carried out. After purified by prep-HPLC (column: Phenomenex C18 150×25 mm×10 μm; mobile phase: [water (NH$_4$HCO$_3$)-ACN]; B %: 23%-53%, 8 min), 6-((4-(2-(2-aminopyridin-3-yl)-3H-imidazo[4,5-b]pyridin-3-yl)benzyl)amino)pyrimidine-4-carbonitrile (Example 135, 27.1 mg, yield: 13.6%) was obtained as a black brown lyophilized powder. MS: m/z=420.0 [M+H]$^+$. $^1$H NMR (400 MHz, Dimethylsulfoxide-d$_6$) δ 8.70-8.60 (m, 1H), 8.54 (s, 1H), 8.30 (dd, J=4.8, 1.2 Hz, 1H), 8.19 (dd, J=8.0, 1.2 Hz, 1H), 7.98 (dd, J=4.8, 1.6 Hz, 1H), 7.45 (d, J=8.0 Hz, 2H), 7.42-7.36 (m, 3H), 7.25-7.18 (m, 1H), 7.08 (s, 1H), 6.93 (br s, 2H), 6.39 (dd, J=7.6, 4.8 Hz, 1H), 4.66 (d, J=4.8 Hz, 2H).

Example 136: 6-((4-(2-(2-Aminopyridin-3-yl)-5-phenyl-3H-imidazo[4,5-b]pyridin-3-yl)benzyl) amino)pyrimidine-4-carbonitrile

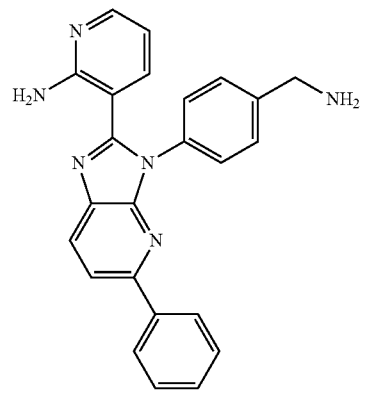

Intermediate 4

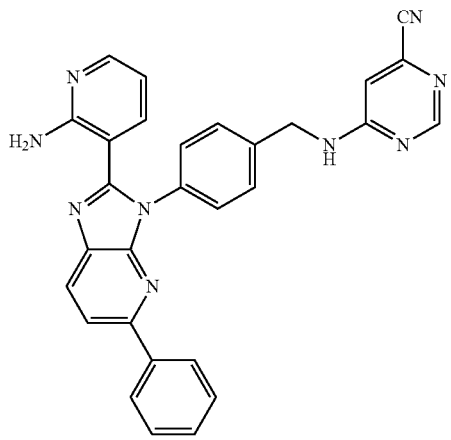

Example 136

A mixture of Intermediate 4 (150 mg, 382 μmol), 6-chloropyrimidine-4-carbonitrile (80.0 mg, 573 μmol), DIEA (148 mg, 1.15 mmol) in NMP (2 mL) was stirred under microwave at 130° C. for 0.5 hr. The reaction mixture was filtered to give filter liquor. The filter liquor was purified by prep-HPLC (column: Waters xbridge 150×25 mm×10 μm; mobile phase: [water (NH$_4$HCO$_3$)-ACN]; B %: 41%-71%, 8 min), 6-((4-(2-(2-aminopyridin-3-yl)-5-phenyl-3H-imidazo [4,5-b]pyridin-3-yl)benzyl)amino)pyrimidine-4-carbonitrile (Example 136, 20 mg, yield: 10.6%) was obtained as a black brown lyophilized powder. MS: m/z=496.1 [M+H]$^+$. $^1$H NMR (400 MHz, Dimethylsulfoxide-d$_6$) δ 8.69-8.62 (m, 1H), 8.55 (s, 1H), 8.26 (d, J=8.4 Hz, 1H), 8.03-7.96 (m, 4H), 7.49-7.43 (m, 6H), 7.42-7.37 (m, 1H), 7.23-7.18 (m, 1H), 7.09 (s, 1H), 6.95 (br s, 2H), 6.40 (dd, J=7.6, 4.8 Hz, 1H), 4.70 (d, J=5.6 Hz, 2H).

Example 137: 4-(4-(4-(2-(2-Aminopyridin-3-yl)-6-phenyl-3H-imidazo[4,5-b]pyridin-3-yl)benzyl)piperazine-1-carbonyl)picolinonitrile

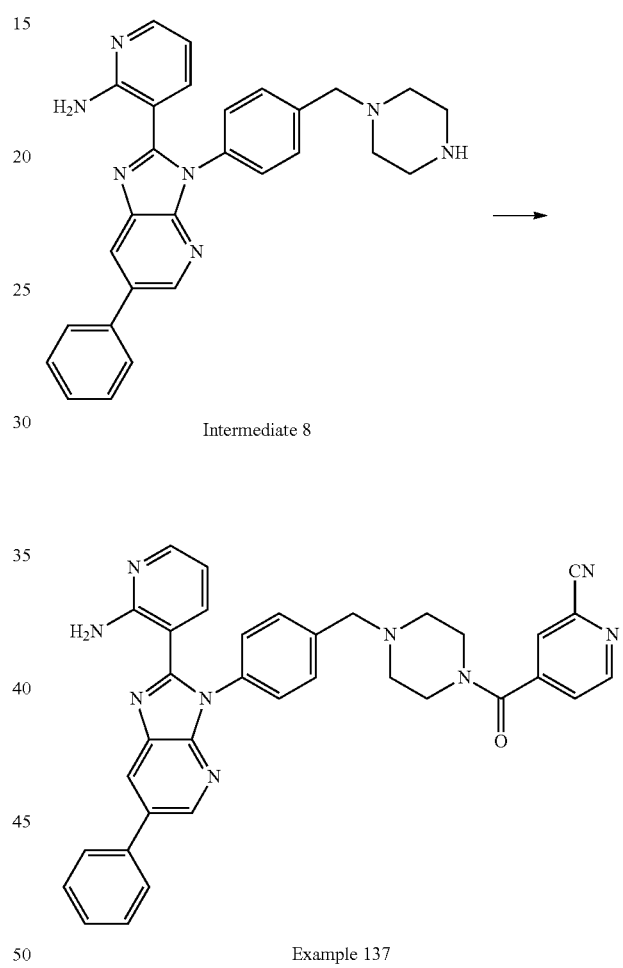

Following the general procedure of Example 23, the reaction of Intermediate 8 (150 mg, 324 μmol) with 2-cyanoisonicotinic acid (48 mg, 324 μmol) at 25° C. for 1 hr. After purified by triturated with 2 mL MeOH at 25° C. for 1 hr, 4-(4-(4-(2-(2-aminopyridin-3-yl)-6-phenyl-3H-imidazo[4,5-b]pyridin-3-yl)benzyl)piperazine-1-carbonyl)picolinonitrile (Example 137, 34.3 mg, yield: 18%) was obtained as an off-white solid. MS: m/z=592.3 [M+H]$^+$. $^1$H NMR (400 MHz, Dimethylsulfoxide-d$_6$) δ 8.84 (d, J=4.8 Hz, 1H), 8.63 (d, J=2.0 Hz, 1H), 8.46 (d, J=2.0 Hz, 1H), 8.11 (s, 1H), 8.00 (dd, J=4.8, 1.6 Hz, 1H), 7.81-7.72 (m, 3H), 7.55-7.47 (m, 4H), 7.45-7.40 (m, 3H), 7.19 (dd, J=7.6, 1.6 Hz, 1H), 7.04 (br s, 2H), 6.39 (dd, J=7.6, 4.8 Hz, 1H), 3.72-3.64 (m, 2H), 3.62 (s, 2H), 3.31-3.27 (m, 2H), 2.54-2.51 (m, 2H), 2.43-2.37 (m, 2H).

Example 138: 6-(4-(4-(2-(2-Aminopyridin-3-yl)-5-phenyl-3H-imidazo[4,5-b]pyridin-3-yl)benzyl)piperazine-1-carbonyl)picolinonitrile

Example 139: 5-(4-(4-(2-(2-Aminopyridin-3-yl)-5-phenyl-3H-imidazo[4,5-b]pyridin-3-yl)benzyl)piperazine-1-carbonyl)nicotinonitrile

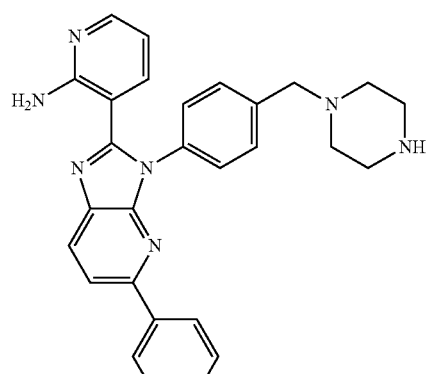

Intermediate 10

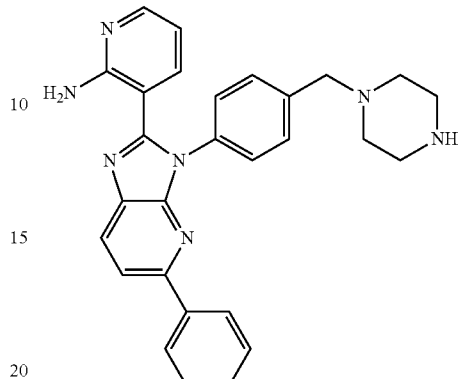

Intermediate 10

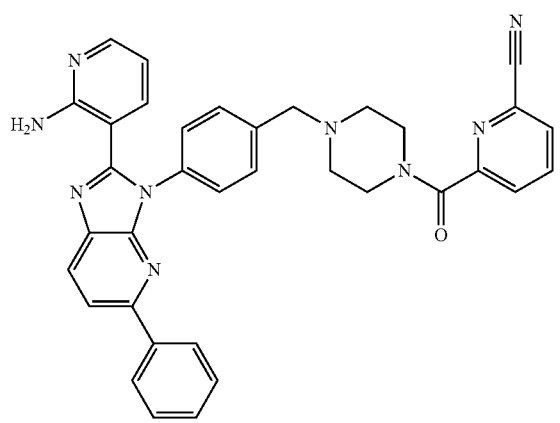

Example 138

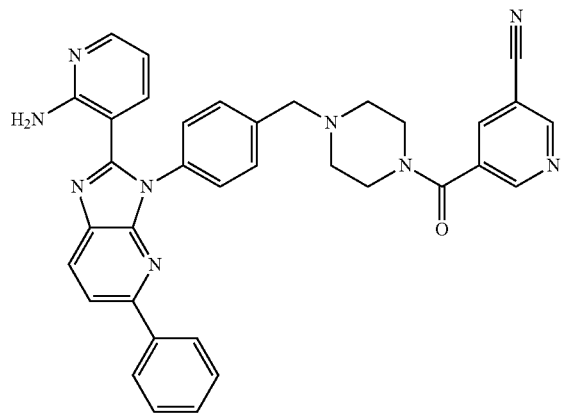

Example 139

To a solution of Intermediate 10 (200 mg, 433 μmol), 6-cyanopicolinic acid (65.4 mg, 442 μmol) in DMF (2 mL) was added EDCI (115 mg, 602 μmol), DIEA (208 mg, 1.61 mmol) and HOBt (81.4 mg, 602 μmol). The mixture was degassed and purged with $N_2$ three times and stirred at 25° C. for 16 h under $N_2$. The reaction mixture was filtered and concentrated under reduced pressure to give a residue. The residue was purified by prep-HPLC (column: Phenomenex C18 150*25 mm*10 μm; mobile phase: [water ($NH_4HCO_3$)-ACN]; B %: 16%-46%, 8 min), 6-(4-(4-(2-(2-aminopyridin-3-yl)-5-phenyl-3H-imidazo[4,5-b]pyridin-3-yl)benzyl)piperazine-1-carbonyl)picolinonitrile (Example 138, 71.4 mg, yield: 28%) was obtained as a light-yellow solid. MS: m/z=592.1 [M+H]$^+$. $^1$H NMR (400 MHz, Dimethylsulfoxide-$d_6$) δ 8.27 (d, J=8.4 Hz, 1H), 8.22-8.17 (m, 1H), 8.13 (d, J=7.6 Hz, 1H), 8.06-7.95 (m, 4H), 7.90 (d, J=7.6 Hz, 1H), 7.54-7.42 (m, 6H), 7.42-7.35 (m, 1H), 7.15 (dd, J=7.6, 2.0 Hz, 1H), 7.02 (br s, 2H), 6.39 (dd, J=7.6, 4.8 Hz, 1H), 3.73-3.68 (m, 2H), 3.64 (s, 2H), 3.44-3.35 (m, 2H), 2.54-2.51 (m, 2H), 2.46-2.39 (m, 2H).

Following the general procedure of Example 138, the reaction of Intermediate 10 (150 mg, 325 μmol) with 5-cyanonicotinic acid (49 mg, 331 μmol) was carried out. After purified by prep-HPLC (column: Waters xbridge 150*25 mm 10 μm; mobile phase: [water ($NH_4HCO_3$)-ACN]; B %: 34%-64%, 8 min), 5-(4-(4-(2-(2-aminopyridin-3-yl)-5-phenyl-3H-imidazo[4,5-b]pyridin-3-yl)benzyl)piperazine-1-carbonyl)nicotinonitrile (Example 139, 86 mg, yield: 45%) was obtained as a white solid. MS: m/z=592.4 [M+H]$^+$. $^1$H NMR (400 MHz, Dimethylsulfoxide-$d_6$) δ 9.10 (d, J=2.0 Hz, 1H), 8.89 (d, J=2.0 Hz, 1H), 8.43-8.40 (m, 1H), 8.27 (d, J=8.0 Hz, 1H), 8.06-7.94 (m, 4H), 7.53-7.43 (m, 6H), 7.42-7.37 (m, 1H), 7.15 (dd, J=7.6, 1.6 Hz, 1H), 7.01 (br s, 2H), 6.39 (dd, J=7.6, 4.8 Hz, 1H), 3.72-3.65 (m, 2H), 3.63 (s, 2H), 3.41-3.35 (m, 2H), 2.55-2.51 (m, 2H), 2.46-2.40 (m, 2H).

Example 140: 2-(4-(4-(2-(2-Aminopyridin-3-yl)-5-phenyl-3H-imidazo[4,5-b]pyridin-3-yl)benzyl)piperazine-1-carbonyl)isonicotinonitrile

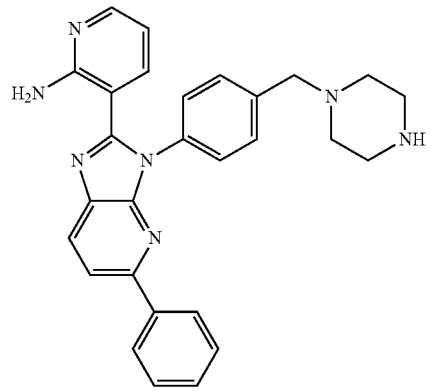

Intermediate 10

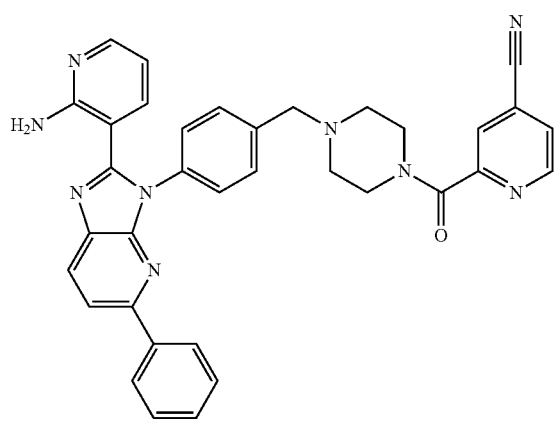

Example 140

Following the general procedure of Example 138, the reaction of Intermediate 10 (150 mg, 375 μmol) with 4-cyanopyridine-2-carboxylic acid (48.1 mg, 325 μmol) was carried out. After purified by prep-HPLC (column: Waters xbridge 150×25 mm 10 μm; mobile phase: [water (NH$_4$HCO$_3$)-ACN]; B %: 36%-66%, 8 min), 2-(4-(4-(2-(2-aminopyridin-3-yl)-5-phenyl-3H-imidazo[4,5-b]pyridin-3-yl)benzyl)piperazine-1-carbonyl)isonicotinonitrile (Example 140, 39.3 mg, yield: 20%) was obtained as a yellow solid. MS: m/z=592.1 [M+H]$^+$. $^1$H NMR (400 MHz, Chloroform-d) δ 8.76 (d, J=4.8 Hz, 1H), 8.15 (d, J=8.4 Hz, 1H), 8.02-7.99 (m, 3H), 7.95 (s, 1H), 7.82 (d, J=8.4 Hz, 1H), 7.59-7.52 (m, 3H), 7.48-7.44 (m, 3H), 7.43-7.41 (m, 2H), 7.41-7.33 (m, 2H), 7.18 (dd, J=7.6, 1.2 Hz, 1H), 6.40 (dd, J=8.0, 5.2 Hz, 1H), 3.96-3.87 (m, 2H), 3.73-3.69 (m, 4H), 2.72-2.68 (m, 2H), 2.62-2.58 (m, 2H).

Example 141: 4-(4-(4-(2-(2-Aminopyridin-3-yl)-5-phenyl-3H-imidazo[4,5-b]pyridin-3-yl)benzyl)piperazine-1-carbonyl)pyrimidine-2-carbonitrile

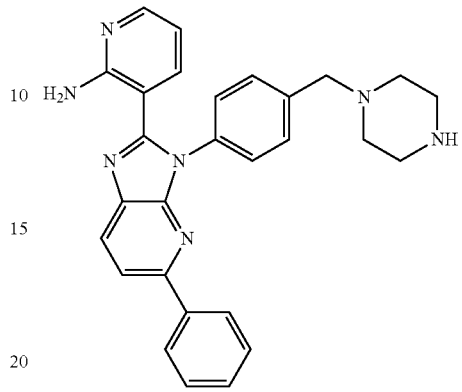

Intermediate 10

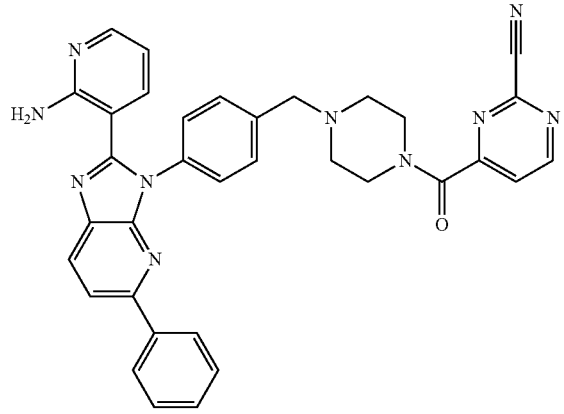

Example 141

Following the general procedure of Example 138, the reaction of Intermediate 10 (200 mg, 433 μmol) with 2-cyanopyrimidine-4-carboxylic acid (64.6 mg, 433 μmol) was carried out. After purified by prep-HPLC (column: Waters xbridge 150×25 mm 10 μm; mobile phase: [water (NH$_4$HCO$_3$)-ACN]; B %: 37%-67%, 8 min), 4-(4-(4-(2-(2-aminopyridin-3-yl)-5-phenyl-3H-imidazo[4,5-b]pyridin-3-yl)benzyl)piperazine-1-carbonyl)pyrimidine-2-carbonitrile (Example 141, 55.9 mg, yield: 21%) was obtained as a yellow solid. MS: m/z=593.1 [M+H]$^+$. $^1$H NMR (400 MHz, Chloroform-d)) δ 9.00 (d, J=5.2 Hz, 1H), 8.14 (d, J=8.4 Hz, 1H), 8.07 (br s, 1H), 8.01 (d, J=7.2 Hz, 2H), 7.86 (d, J=5.2 Hz, 1H), 7.81 (d, J=8.4 Hz, 1H), 7.54-7.49 (m, 2H), 7.47-7.41 (m, 4H), 7.40-7.34 (m, 1H), 7.11 (d, J=8.0 Hz, 1H), 6.70 (br s, 2H), 6.43-6.34 (m, 1H), 3.90-3.83 (m, 2H), 3.70-3.64 (m, 4H), 2.69-2.57 (m, 4H).

Example 142: 6-(4-(4-(2-(2-Aminopyridin-3-yl)-5-phenyl-3H-imidazo[4,5-b]pyridin-3-yl)benzyl)piperazine-1-carbonyl)nicotinonitrile Example 143: 3-(4-(4-(2-(2-Aminopyridin-3-yl)-5-phenyl-3H-imidazo[4,5-b]pyridin-3-yl)benzyl)piperazine-1-carbonyl)picolinonitrile

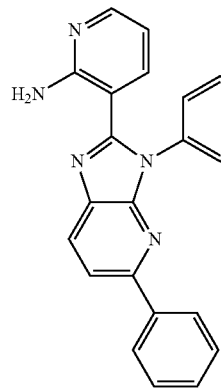

Intermediate 10

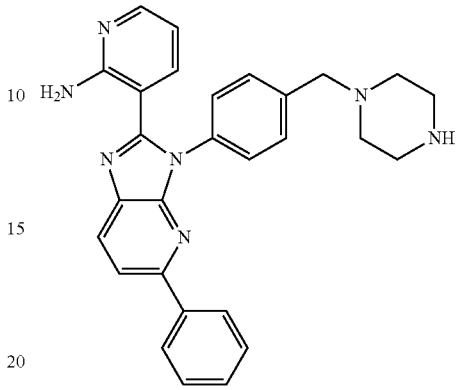

Intermediate 10

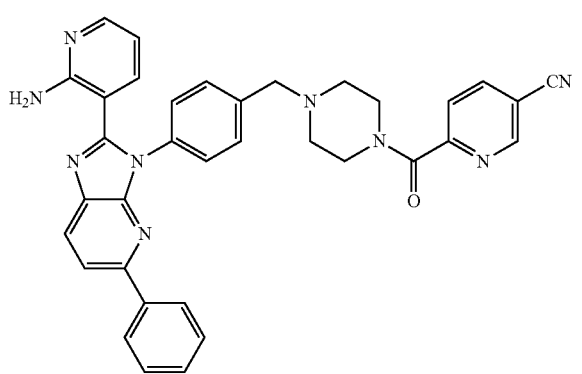

Example 142

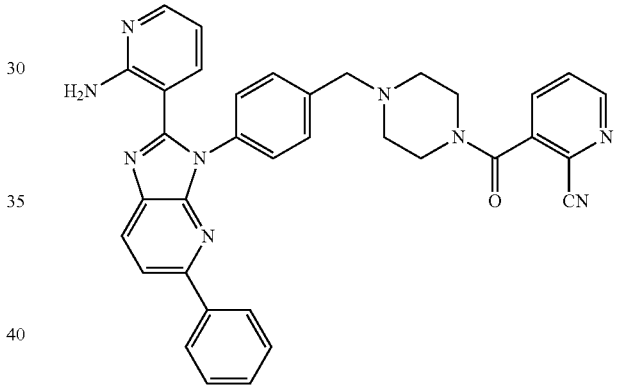

Example 143

Following the general procedure of Example 138, the reaction of Intermediate 10 (150 mg, 325 μmol) with 5-cyanopicolinic acid (53 mg, 357 μmol) was carried out. After purified by prep-HPLC (column: Waters xbridge 150*25 mm 10 μm; mobile phase: [water (NH$_4$HCO$_3$)-ACN]; B %: 35%-65%, 9 min), 6-(4-(4-(2-(2-aminopyridin-3-yl)-5-phenyl-3H-imidazo[4,5-b]pyridin-3-yl)benzyl)piperazine-1-carbonyl)nicotinonitrile (Example 142, 49 mg, yield: 26%) was obtained as a white solid. MS: m/z=592.2 [M+H]$^+$. $^1$H NMR (400 MHz, Chloroform-d) δ 8.85 (s, 1H), 8.14 (d, J=8.4 Hz, 1H), 8.08 (dd, J=8.4, 2.0 Hz, 1H), 8.06-7.98 (m, 3H), 7.81 (d, J=8.4 Hz, 2H), 7.52 (d, J=8.4 Hz, 2H), 7.47-7.35 (m, 5H), 7.12 (dd, J=7.6, 1.6 Hz, 1H), 6.82 (br s, 2H), 6.37 (dd, J=7.6, 4.8 Hz, 1H), 3.88 (t, J=4.4 Hz, 1H), 3.67 (s, 2H), 3.63 (t, J=4.8 Hz, 2H), 2.66 (t, J=4.4 Hz, 2H), 2.56 (t, J=4.8 Hz, 2H).

Following the general procedure of Example 138, the reaction of Intermediate 10 (150 mg, 325 μmol) with 2-cyanonicotinic acid (53 mg, 357 μmol) was carried out. After purified by prep-HPLC (column: Phenomenex C18 150*25 mm*10 μm; mobile phase: [water (NH$_4$HCO$_3$)-ACN]; B %: 35%-65%, 8 min), (3-(4-(4-(2-(2-aminopyridin-3-yl)-5-phenyl-3H-imidazo[4,5-b]pyridin-3-yl)benzyl)piperazine-1-carbonyl)picolinonitrile (Example 143, 23.5 mg, yield: 12%) was obtained as a light-yellow solid. MS: m/z=592.2 [M+H]$^+$. $^1$H NMR (400 MHz, Dimethylsulfoxide-d$_6$) δ 8.82 (d, J=4.8 Hz, 1H), 8.26 (d, J=8.4 Hz, 1H), 8.09 (dd, J=8.0, 1.2 Hz, 1H), 8.05-7.95 (m, 4H), 7.83 (dd, J=8.0, 4.8 Hz, 1H), 7.53-7.35 (m, 7H), 7.15 (dd, J=7.6, 1.6 Hz, 1H), 7.02 (br s, 2H), 6.39 (dd, J=7.6, 4.8 Hz, 1H), 3.79-3.69 (m, 2H), 3.64 (s, 2H), 3.32-3.28 (m, 2H), 2.56-2.52 (m, 2H), 2.47-2.40 (m, 2H).

Example 144: 4-(4-(4-(2-(2-Aminopyridin-3-yl)-5-phenyl-3H-imidazo[4,5-b]pyridin-3-yl)benzyl)piperazine-1-carbonyl)nicotinonitrile

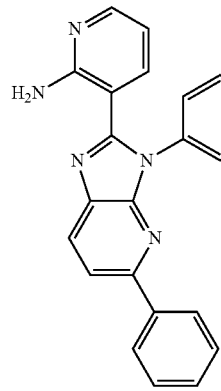

Intermediate 10

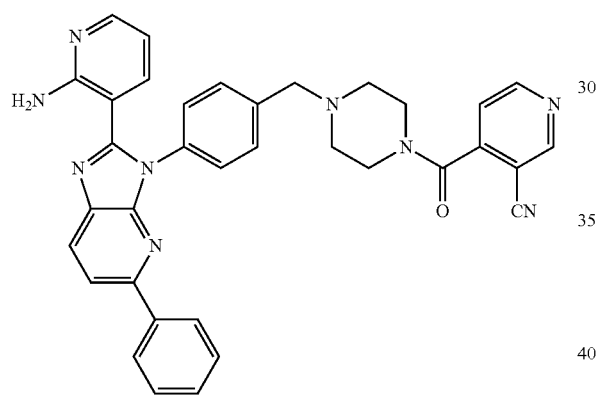

Example 144

Following the general procedure of Example 138, the reaction of Intermediate 10 (212 mg, 460 μmol) with 3-cyanopyridine-4-carboxylic acid (75 mg, 506 μmol) was carried out. After purified by prep-HPLC (column: Phenomenex C18 150×25 mm×10 μm; mobile phase: [water (NH$_4$HCO$_3$)-ACN]; B %: 33%-63%, 8 min), 4-(4-(4-(2-(2-aminopyridin-3-yl)-5-phenyl-3H-imidazo[4,5-b]pyridin-3-yl)benzyl)piperazine-1-carbonyl)nicotinonitrile (Example 144, 17.0 mg, yield: 6.3%) was obtained as a yellow lyophilized powder. MS: m/z=592.3 [M+H]$^+$. $^1$H NMR (400 MHz, Dimethylsulfoxide-d$_6$) δ 9.14 (s, 1H), 8.94 (d, J=4.8 Hz, 1H), 8.27 (d, J=8.4 Hz, 1H), 8.04-8.00 (m, 2H), 8.00-7.96 (m, 2H), 7.65 (d, J=5.2 Hz, 1H), 7.52-7.48 (m, 2H), 7.47-7.43 (m, 4H), 7.42-7.37 (m, 1H), 7.15 (dd, J=7.6, 2.0 Hz, 1H), 7.01 (br s, 2H), 6.39 (dd, J=7.6, 4.8 Hz, 1H), 3.76-3.69 (m, 2H), 3.64 (s, 2H), 3.28-3.25 (m, 2H), 2.54-2.52 (m, 2H), 2.45-2.41 (m, 2H).

Example 145: 3-(4-(4-(2-(2-Aminopyridin-3-yl)-5-phenyl-3H-imidazo[4,5-b]pyridin-3-yl)benzyl)piperazine-1-carbonyl)isonicotinonitrile

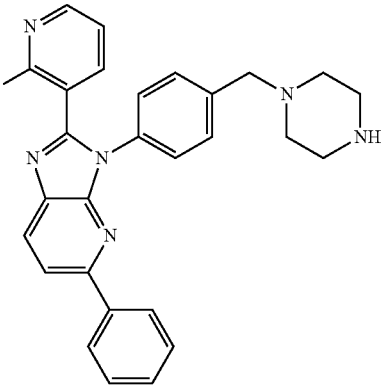

Intermediate 10

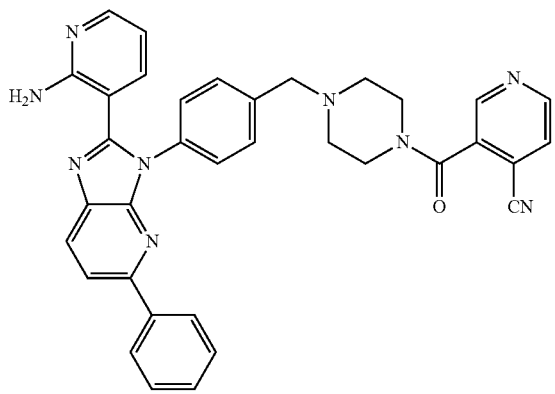

Example 145

Following the general procedure of Example 138, the reaction of Intermediate 10 (150 mg, 325 μmol) with 4-cyanonicotinic acid (53 mg, 357 μmol) was carried out. After purified by prep-HPLC (column: Phenomenex C18 150*25 mm*10 μm; mobile phase: [water (NH$_4$HCO$_3$)-ACN]; B %: 35%-65%, 8 min), 3-(4-(4-(2-(2-aminopyridin-3-yl)-5-phenyl-3H-imidazo[4,5-b]pyridin-3-yl)benzyl)piperazine-1-carbonyl)isonicotinonitrile (Example 145, 7.2 mg, yield: 3.7%) was obtained as a light-yellow solid. MS: m/z=592.2 [M+H]$^+$. $^1$H NMR (400 MHz, Dimethylsulfoxide-d$_6$) δ 8.90 (d, J=5.2 Hz, 1H), 8.86 (s, 1H), 8.27 (d, J=8.4 Hz, 1H), 8.06-7.94 (m, 5H), 7.54-7.36 (m, 7H), 7.15 (dd, J=7.6, 1.6 Hz, 1H), 7.01 (br s, 2H), 6.39 (dd, J=7.6, 4.8 Hz, 1H), 3.78-3.68 (m, 2H), 3.64 (s, 2H), 3.38-3.35 (m, 2H), 2.56-2.52 (m, 2H), 2.47-2.40 (m, 2H).

Example 146: 2-(4-(4-(2-(2-Aminopyridin-3-yl)-5-phenyl-3H-imidazo[4,5-b]pyridin-3-yl)benzyl)piperazine-1-carbonyl)nicotinonitrile

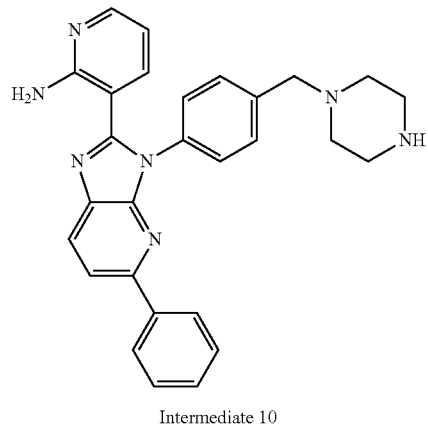

Intermediate 10

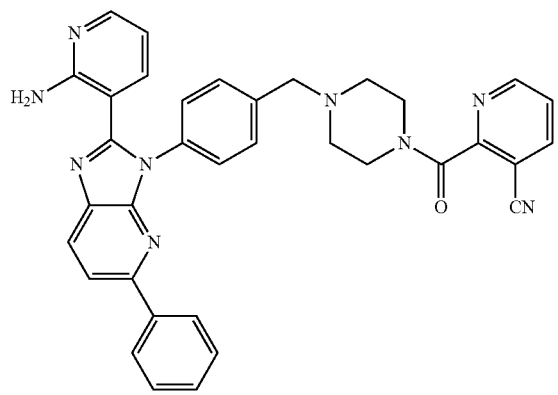

Example 146

Following the general procedure of Example 138, the reaction of Intermediate 10 (150 mg, 325 μmol) with 3-cyanopicolinic acid (53 mg, 357 μmol) was carried out. After purified by prep-HPLC (column: Phenomenex C18 150*25 mm*10 μm; mobile phase: [water (NH₄HCO₃)-ACN]; B %: 35%-65%, 8 min), 2-(4-(4-(2-(2-aminopyridin-3-yl)-5-phenyl-3H-imidazo[4,5-b]pyridin-3-yl)benzyl)piperazine-1-carbonyl)nicotinonitrile (Example 146, 38.7 mg, yield: 20%) was obtained as a light-yellow solid. MS: m/z=592.2 [M+H]$^+$. $^1$H NMR (400 MHz, Dimethylsulfoxide-d₆) δ 8.86 (d, J=4.8 Hz, 1H), 8.47 (dd, J=8.0, 1.2 Hz, 1H), 8.27 (d, J=8.4 Hz, 1H), 8.08-7.93 (m, 4H), 7.70 (dd, J=8.0, 4.8 Hz, 1H), 7.53-7.42 (m, 6H), 7.42-7.36 (m, 1H), 7.14 (dd, J=7.6, 1.6 Hz, 1H), 7.02 (br s, 2H), 6.39 (dd, J=7.6, 4.8 Hz, 1H), 3.77-3.70 (m, 2H), 3.64 (s, 2H), 3.31-3.26 (m, 2H), 2.56-2.52 (m, 2H), 2.46-2.39 (m, 2H).

Example 147: N-(4-(2-(2-Aminopyridin-3-yl)-3H-imidazo[4,5-b]pyridin-3-yl)benzyl)-4-cyanopicolinamide

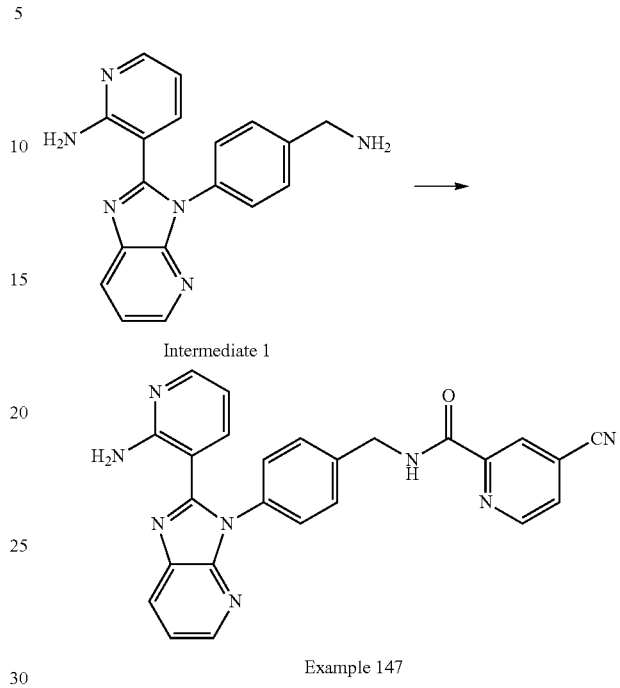

Intermediate 1

Example 147

Following the general procedure of Example 138, the reaction of Intermediate 1 (200 mg, 632 μmol) with 4-cyanopyridine-2-carboxylic acid (93.6 mg, 632 μmol) was carried out. After purified by prep-HPLC (column: Phenomenex luna C18 150×25 mm×10 μm; mobile phase: [water (FA)-ACN]; B %: 7%-37%, 10 min), N-(4-(2-(2-aminopyridin-3-yl)-3H-imidazo[4,5-b]pyridin-3-yl)benzyl)-4-cyanopicolinamide (Example 147, 19.3 mg, yield: 7%) was obtained as a yellow solid. MS: m/z=447.3 [M+H]$^+$. $^1$H NMR (400 MHz, Dimethylsulfoxide-d₆) δ 9.64 (t, J=6.4 Hz, 1H), 8.93 (d, J=5.2 Hz, 1H), 8.38 (s, 1H), 8.29 (dd, J=4.8, 1.6 Hz, 1H), 8.19 (dd, J=8.0, 1.2 Hz, 1H), 8.11 (dd, J=4.8, 1.6 Hz, 1H), 7.98 (dd, J=4.8, 2.0 Hz, 1H), 7.46 (d, J=8.4 Hz, 2H), 7.39-7.36 (m, 3H), 7.22 (dd, J=7.6, 2.0 Hz, 1H), 6.96 (br s, 2H), 6.40 (dd, J=7.6, 4.8 Hz, 1H), 4.59 (d, J=6.4 Hz, 2H).

Example 148: N-(4-(2-(2-Aminopyridin-3-yl)-3H-imidazo[4,5-b]pyridin-3-yl)benzyl)-2-cyanopyrimidine-4-carboxamide

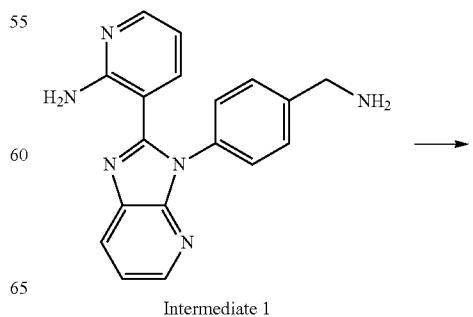

Intermediate 1

-continued

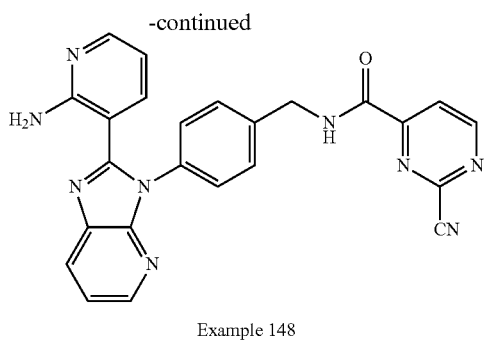

Example 148

Following the general procedure of Example 138, the reaction of Intermediate 1 (100 mg, 316 µmol) with 2-cyanopyrimidine-4-carboxylic acid (47.1 mg, 316 µmol) was carried out. After purified by prep-HPLC (column: Waters xbridge 150×25 mm 10 µm; mobile phase: [water (NH$_4$HCO$_3$)-ACN]; B %: 19%-49%, 8 min), N-(4-(2-(2-aminopyridin-3-yl)-3H-imidazo[4,5-b]pyridin-3-yl)benzyl)-2-cyanopyrimidine-4-carboxamide (Example 148, 8 mg, yield: 5%) was obtained as a white solid. MS: m/z=448.1 [M+H]$^+$. $^1$H NMR (400 MHz, Chloroform-d)) δ 9.13 (d, J=5.2 Hz, 1H), 8.41 (dd, J=4.8, 1.2 Hz, 1H), 8.37 (d, J=5.2 Hz, 1H), 8.28-8.22 (m, 1H), 8.12 (dd, J=8.0, 1.6 Hz, 1H), 8.02 (dd, J=5.2, 1.6 Hz, 1H), 7.56 (d, J=8.4 Hz, 2H), 7.41 (d, J=8.4 Hz, 2H), 7.36-7.27 (m, 3H), 7.21 (dd, J=7.6, 1.6 Hz, 1H), 6.45 (dd, J=8.0, 5.2 Hz, 1H), 4.80 (d, J=6.4 Hz, 2H).

Example 149: 2-(4-(4-(2-(2-Aminopyridin-3-yl)-3H-imidazo[4,5-b]pyridin-3-yl)benzyl)piperazine-1-carbonyl)isonicotinonitrile

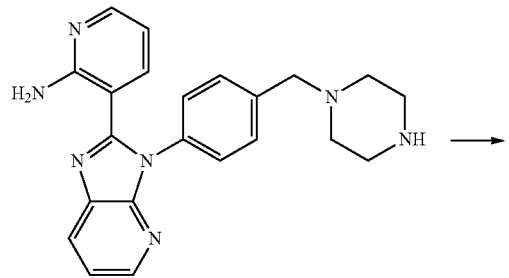

Intermediate 2

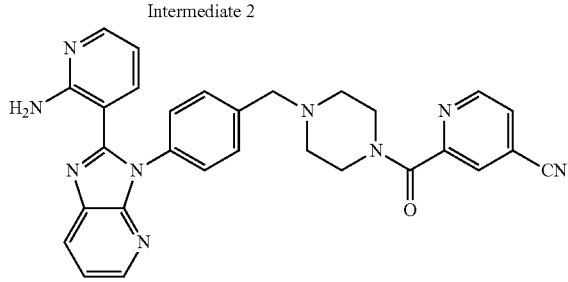

Example 149

Following the general procedure of Example 138, the reaction of Intermediate 2 (200 mg, 519 µmol) with 4-cyanopyridine-2-carboxylic acid (76.8 mg, 519 µmol) was carried out. After purified by prep-HPLC (column: Waters Xbridge 150×25 mm×5 µm; mobile phase: [water (NH$_4$HCO$_3$)-ACN]; B %: 17%-47%, 8 min), 2-(4-(4-(2-(2-aminopyridin-3-yl)-3H-imidazo[4,5-b]pyridin-3-yl)benzyl)piperazine-1-carbonyl)isonicotinonitrile (Example 149, 31.1 mg, yield: 11%) was obtained as a yellow solid. MS: m/z=516.1 [M+H]$^+$. $^1$H NMR (400 MHz, Dimethylsulfoxide-d$_6$) δ 8.76 (d, J=4.8 Hz, 1H), 8.40 (dd, J=4.8, 1.2 Hz, 1H), 8.10 (dd, J=8.0, 1.2 Hz, 1H), 8.05 (dd, J=4.8, 1.6 Hz, 1H), 7.94 (s, 1H), 7.57 (dd, J=5.2, 1.6 Hz, 1H), 7.51 (d, J=8.4 Hz, 2H), 7.36-7.30 (m, 3H), 7.07 (dd, J=8.0, 1.6 Hz, 1H), 6.62 (br s, 2H), 6.33 (dd, J=7.6, 4.8 Hz, 1H), 3.88-3.84 (m, 2H), 3.67-3.67 (m, 4H), 2.63 (t, J=4.8 Hz, 2H), 2.55-2.49 (m, 2H).

Example 150: N-(1-(4-(2-(2-Aminopyridin-3-yl)-5-phenyl-3H-imidazo[4,5-b]pyridin-3-yl)benzyl)piperidin-4-yl)-4-cyanopicolinamide

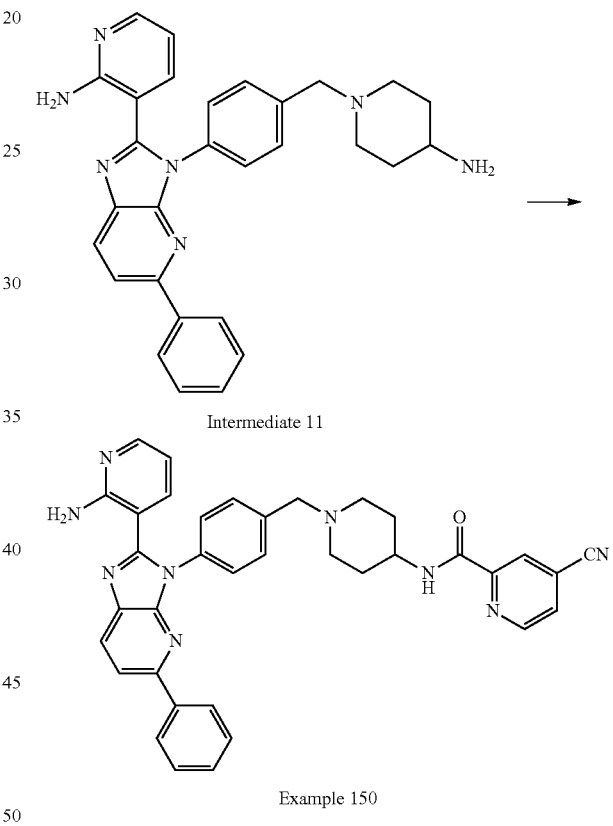

To a solution of Intermediate 11 (150 mg, 315 µmol) and 4-cyanopyridine-2-carboxylic acid (90.7 mg, 473 µmol) in CH$_2$Cl$_2$ (2 mL) was added EDCI (90.7 mg, 473 µmol), HOBt (63.9 mg, 473 µmol) and DIEA (163 mg, 1.26 mmol). The resulting mixture was stirred at 25° C. for 16 hr. Then the reaction mixture was diluted with 5 mL H$_2$O and extracted with EtOAc (5 mL×2). The combined organic layers were dried over Na$_2$SO$_4$, filtered and concentrated under reduced pressure to give a residue. The residue was purified by prep-HPLC (column: Waters xbridge 150×25 mm 10 µm; mobile phase. [water (NH$_4$HCO$_3$)-ACN]; B %: 41%-71%, 8 min), N-(1-(4-(2-(2-aminopyridin-3-yl)-5-phenyl-3H-imidazo[4,5-b]pyridin-3-yl)benzyl)piperidin-4-yl)-4-cyanopicolinamide (Example 150, 30 mg, yield: 15%) was obtained as a yellow solid. MS: m/z=606.1 [M+H]$^+$. $^1$H NMR (400 MHz, Chloroform-d) δ 8.75 (d, J=5.2 Hz, 1H), 8.41 (s, 1H), 8.14 (d, J=8.4 Hz, 1H), 8.06 (dd, J=4.8, 1.6 Hz, 1H), 8.01 (d, J=7.6 Hz, 2H), 7.99-7.93 (m, 1H), 7.81 (d, J=8.4 Hz, 1H), 7.70-7.60 (m, 3H), 7.55-7.41 (m, 5H), 7.40-7.35 (m, 1H), 7.09 (dd, J=7.6, 1.6 Hz, 1H), 6.67 (br s, 1H), 6.37 (dd, J=7.6, 4.8 Hz, 1H), 4.19-4.09 (m, 1H), 3.95-3.69 (m, 2H), 3.30-3.04 (m, 2H), 2.65-2.46 (m, 2H), 2.22-2.03 (m, 4H).

Example 151: N-(1-(4-(2-(2-Aminopyridin-3-yl)-5-phenyl-3H-imidazo[4,5-b]pyridin-3-yl)benzyl)piperidin-4-yl)-2-cyanopyrimidine-4-carboxamide

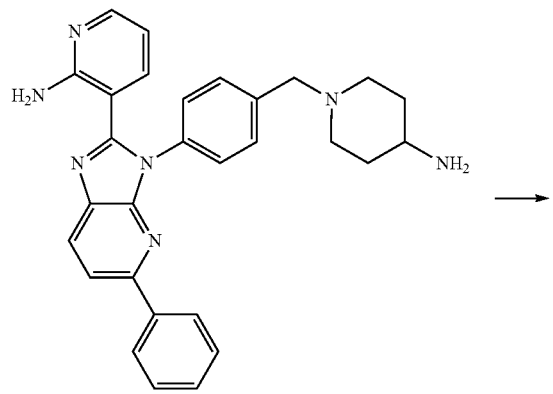

Intermediate 11

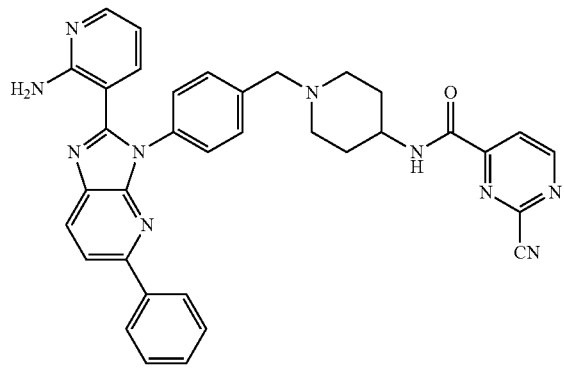

Example 151

Following the general procedure of Example 150, the reaction of Intermediate 11 (150 mg, 315 μmol) with 2-cyanopyrimidine-4-carboxylic acid (47 mg, 315 μmol) was carried out. After purified by prep-HPLC (column: Waters xbridge 150×25 mm 10 μm; mobile phase: [water (NH4HCO3)-ACN]; B %: 41%-71%, 8 min), N-(1-(4-(2-(2-aminopyridin-3-yl)-5-phenyl-3H-imidazo[4,5-b]pyridin-3-yl)benzyl)piperidin-4-yl)-2-cyanopyrimidine-4-carboxamide (Example 151, 35.2 mg, yield: 18%) was obtained as a yellow solid. MS: m/z=607.1 [M+H]+. 1H NMR (400 MHz, Chloroform-d)) δ 9.08 (d, J=5.2 Hz, 1H), 8.32 (d, J=5.2 Hz, 1H), 8.13 (d, J=8.4 Hz, 1H), 8.11-8.04 (m, 1H), 8.02 (d, J=7.6 Hz, 1H), 7.80 (d, J=8.4 Hz, 1H), 7.74 (d, J=8.0 Hz, 1H), 7.51 (d, J=8.4 Hz, 2H), 7.46-7.40 (m, 4H), 7.39-7.35 (m, 1H), 7.10 (d, J=7.6 Hz, 1H), 6.61 (br s, 2H), 6.36 (dd, J=7.6, 4.8 Hz, 1H), 4.12-3.96 (m, 1H), 3.65 (s, 2H), 2.95 (d, J=11.6 Hz, 2H), 2.34-2.25 (m, 2H), 2.11-2.01 (m, 2H), 1.82-1.73 (m, 2H).

Example 152: 4-(4-(4-(2-(2-aminopyridin-3-yl)-3H-imidazo[4,5-b]pyridin-3-yl)benzyl)piperazine-1-carbonyl)pyrimidine-2-carbonitrile

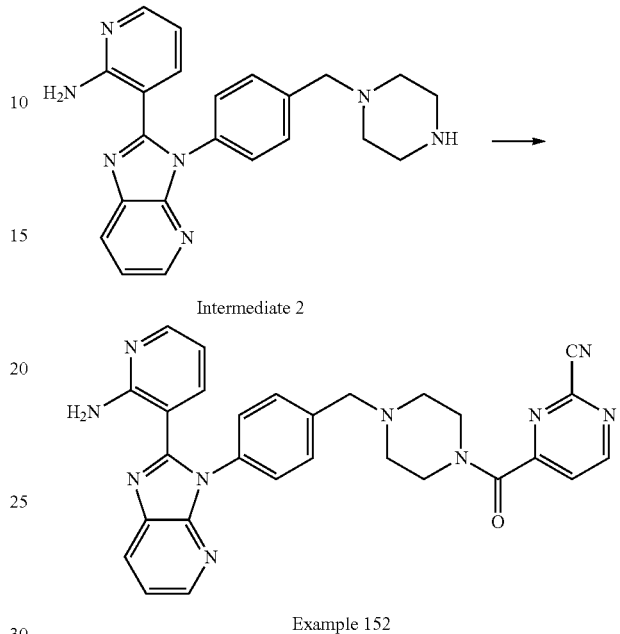

Intermediate 2

Example 152

Following the general procedure Example 150, the reaction of Intermediate 2 (130 mg, 337 μmol) with 2-cyanopyrimidine-4-carboxylic acid (67.1 mg, 405 μmol) was carried out. After purified by prep-HPLC (column: Phenomenex C18 150×25 mm 10 μm; mobile phase: [water (NH4HCO3)-ACN]; B %: 18%-48%, 8 min), 4-(4-(4-(2-(2-aminopyridin-3-yl)-3H-imidazo[4,5-b]pyridin-3-yl)benzyl)piperazine-1-carbonyl)pyrimidine-2-carbonitrile (Example 152, 20 mg, yield: 11%) was obtained as a yellow solid. MS: m/z=517.2 [M+H]+. 1H NMR (400 MHz, Dimethylsulfoxide-d6) δ 9.15 (d, J=5.2 Hz, 1H), 8.33 (dd, J=4.8, 1.2 Hz, 1H), 8.20 (dd, J=8.0, 1.2 Hz, 1H), 8.01-7.96 (m, 2H), 7.49-7.45 (m, 2H), 7.41-7.36 (m, 3H), 7.16 (dd, J=7.6, 1.6 Hz, 1H), 7.00 (br s, 2H), 6.38 (dd, J=7.6, 4.8 Hz, 1H), 3.71-3.66 (m, 2H), 3.62 (s, 2H), 3.41-3.38 (m, 2H), 2.59-2.55 (m, 2H), 2.43-2.39 (m, 2H).

Example 153: 3-(4-(4-(2-(2-Aminopyridin-3-yl)-3H-imidazo[4,5-b]pyridin-3-yl)benzyl)piperazine-1-carbonyl)picolinonitrile

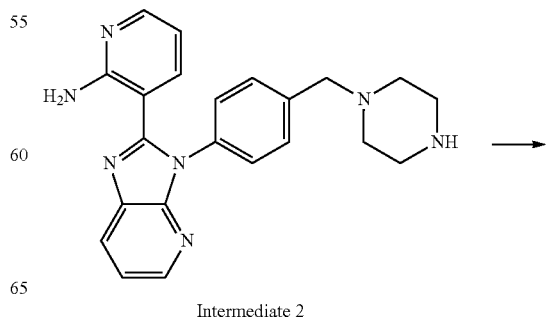

Intermediate 2

-continued

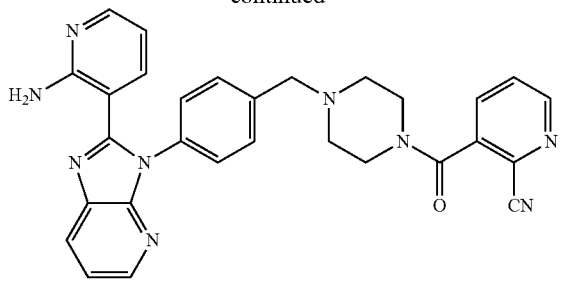

Example 153

Following the general procedure of Example 150, the reaction of Intermediate 2 (200 mg, 518 μmol) with 2-cyanonicotinic acid (115 mg, 778 μmol) was carried out. After purified by prep-HPLC (column: Phenomenex C18 150×25 mm 10 μm; mobile phase: [water (NH$_4$HCO$_3$)-ACN]; B %: 16%-46%, 8 min), 33-(4-(4-(2-(2-aminopyridin-3-yl)-3H-imidazo[4,5-b]pyridin-3-yl)benzyl)piperazine-1-carbonyl)picolinonitrile (Example 153, 11.8 mg, yield: 4.4%) was obtained as a light-yellow powder. MS: m/z=516.4 [M+H]$^+$. $^1$H NMR (400 MHz, Dimethylsulfoxide-d$_6$) δ 8.82 (dd, J=4.8, 1.6 Hz, 1H), 8.31 (dd, J=4.8, 1.6 Hz, 1H), 8.20 (dd, J=8.0, 1.2 Hz, 1H), 8.09 (dd, J=8.0, 1.6 Hz, 1H), 7.98 (dd, J=4.8, 2.0 Hz, 1H), 7.83 (dd, J=8.0, 4.8 Hz, 1H), 7.47 (d, J=8.4 Hz, 2H), 7.41-7.36 (m, 3H), 7.16 (dd, J=7.6, 1.6 Hz, 1H), 6.99 (br s, 2H), 6.38 (dd, J=7.6, 4.8 Hz, 1H), 3.78-3.71 (m, 2H), 3.61 (s, 2H), 3.32-3.28 (m, 2H), 2.56-2.51 (m, 2H), 2.45-2.45 (m, 2H).

Example 154: 4-(4-(4-(2-(2-Aminopyridin-3-yl)-3H-imidazo[4,5-b]pyridin-3-yl)benzyl)piperazine-1-carbonyl)nicotinonitrile

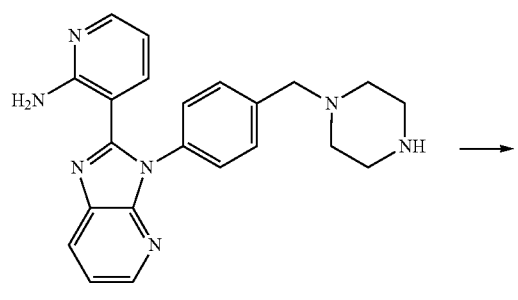

Intermediate 2

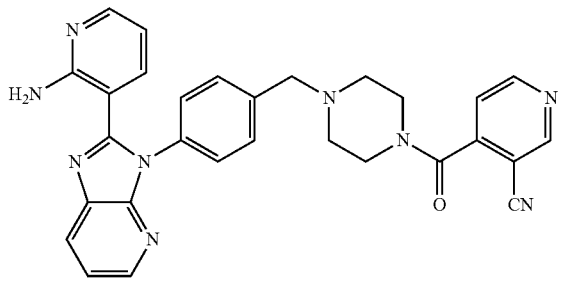

Example 154

Following the general procedure of Example 150, the reaction of Intermediate 2 (300 mg, 778 μmol) with 3-cyanoisonicotinic acid (172 mg. 1.17 mmol) was carried out. After purified by silica gel flash chromatography (Eluent of 0~8% EtOAc in petroleum ether), then by prep-TLC (CH$_2$Cl$_2$:MeOH=10:1), 4-(4-(4-(2-(2-aminopyridin-3-yl)-3H-imidazo[4,5-b]pyridin-3-yl)benzyl)piperazine-1-carbonyl)nicotinonitrile (Example 154, 34 mg, yield: 7.9%) was obtained as a light-yellow powder. MS: m/z=516.3 [M+H]$^+$. $^1$H NMR (400 MHz, Dimethylsulfoxide-d$_6$) δ 9.14 (s, 1H), 8.93 (d, J=4.8 Hz, 1H), 8.31 (dd, J=4.8, 3.6 Hz, 1H), 8.20 (dd, J=8.0, 1.2 Hz, 1H), 7.98 (dd, J=4.8, 1.6 Hz, 1H), 7.65 (d, J=4.8 Hz, 1H), 7.47 (d, J=8.4 Hz, 2H), 7.41-7.37 (m, 3H), 7.16 (dd, J=7.6, 1.6 Hz, 1H), 6.99 (br s, 2H), 6.38 (dd, J=7.6, 4.8 Hz, 1H), 3.73-3.68 (m, 2H), 3.61 (s, 2H), 3.27-3.25 (m, 2H), 2.54-2.52 (m, 2H), 2.42-2.39 (m, 2H).

Example 155: 3-(4-(4-(2-(2-Aminopyridin-3-yl)-3H-imidazo[4,5-b]pyridin-3-yl)benzyl)piperazine-1-carbonyl)isonicotinonitrile

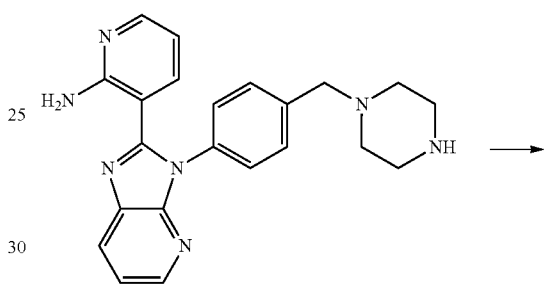

Intermediate 2

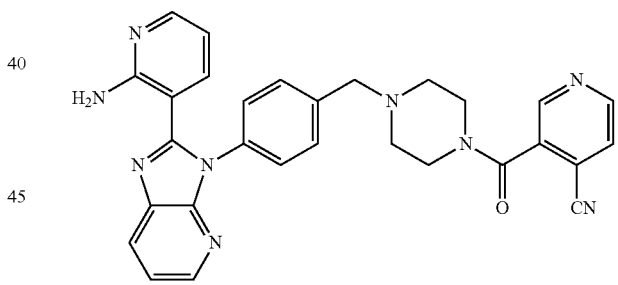

Example 155

Following the general procedure of Example 150, the reaction of Intermediate 2 (200 mg, 518 μmol) with 4-cyanonicotinic acid (115 mg, 778 μmol) was carried out. After purified by prep-HPLC (column: Phenomenex C18 150×25 mm 10 μm; mobile phase: [water (NH$_4$HCO$_3$)-ACN]; B %: 16%-46%, 8 min), 3-(4-(4-(2-(2-aminopyridin-3-yl)-3H-imidazo[4,5-b]pyridin-3-yl)benzyl)piperazine-1-carbonyl)isonicotinonitrile (Example 155, 12.1 mg, yield: 4.4%) was obtained as a light-yellow powder. MS: m/z=516.2 [M+H]$^+$. $^1$H NMR (400 MHz, Dimethylsulfoxide-d$_6$) δ 8.90 (d, J=4.8 Hz, 1H), 8.86 (s, 1H), 8.31 (dd, J=4.8, 1.2 Hz, 1H), 8.20 (dd, J=8.0, 1.6 Hz, 1H), 8.01-7.96 (m, 2H), 7.47 (d, J=8.0 Hz, 2H), 7.47-7.35 (m, 3H), 7.16 (dd, J=7.6, 1.6 Hz, 1H), 6.99 (br s, 2H), 6.38 (dd, J=7.6, 4.8 Hz, 1H), 3.76-3.70 (m, 2H), 3.61 (s, 2H), 3.33-3.29 (m, 2H), 2.55-2.51 (m, 2H), 2.45-2.39 (m, 2H).

1217

Example 156: 4-((1-(4-(2-(2-Aminopyridin-3-yl)-5-phenyl-3H-imidazo[4,5-b]pyridin-3-yl)benzyl)piperidin-4-yl)(methyl)amino)pyrimidine-2-carbonitrile

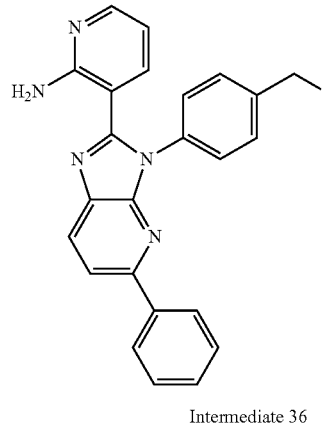

Intermediate 36

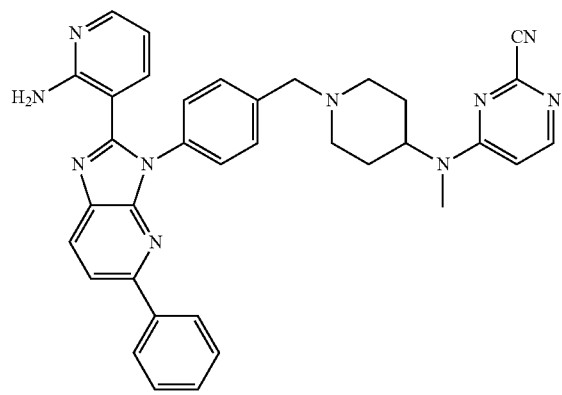

Example 156

To a solution of Intermediate 36 (130 mg, 266 μmol) in DMF (2 mL) was added 4-chloropyrimidine-2-carbonitrile (44 mg, 319 μmol), NaI (3.98 mg, 27 μmol) and K$_2$CO$_3$ (110 mg, 797 μmol). The mixture was stirred at 80° C. for 2 hr. The reaction mixture was poured into H$_2$O (10 mL), extracted with EtOAc (15 mL). The organic phase was dried over anhydrous Na$_2$SO$_4$, filtered, and concentrated under reduced pressure to give a residue. The residue was purified by silica gel flash chromatography (Eluent of 0~63% EtOAc in petroleum ether), 4-((1-(4-(2-(2-aminopyridin-3-yl)-5-phenyl-3H-imidazo[4,5-b]pyridin-3-yl)benzyl)piperidin-4-yl)(methyl)amino)pyrimidine-2-carbonitrile (Example 156, 59.4 mg, yield: 37%) was obtained as a yellow solid. MS: m/z=593.4 [M+H]$^+$. $^1$H NMR (400 MHz, Methanol-d$_4$) δ8.18-8.16 (m, 2H), 8.02-8.00 (m, 2H), 7.97 (dd, J=5.2, 2.0 Hz, 1H), 7.93 (d, J=8.8 Hz, 1H), 7.56 (d, J=8.4 Hz, 2H), 7.48-7.30 (m, 6H), 6.89-6.76 (m, 1H), 6.47 (dd, J=7.6, 5.2 Hz, 1H), 3.75 (s, 2H), 3.35-3.31 (m, 1H), 3.14-3.11 (m, 2H), 2.98 (s, 3H), 2.39-2.33 (m, 2H), 1.98-1.87 (m, 2H), 1.72-1.69 (m, 2H).

1218

Example 157: 5-((1-(4-(2-(2-aminopyridin-3-yl)-3H-imidazo[4,5-b]pyridin-3-yl)benzyl)piperidin-4-yl)amino)picolinonitrile

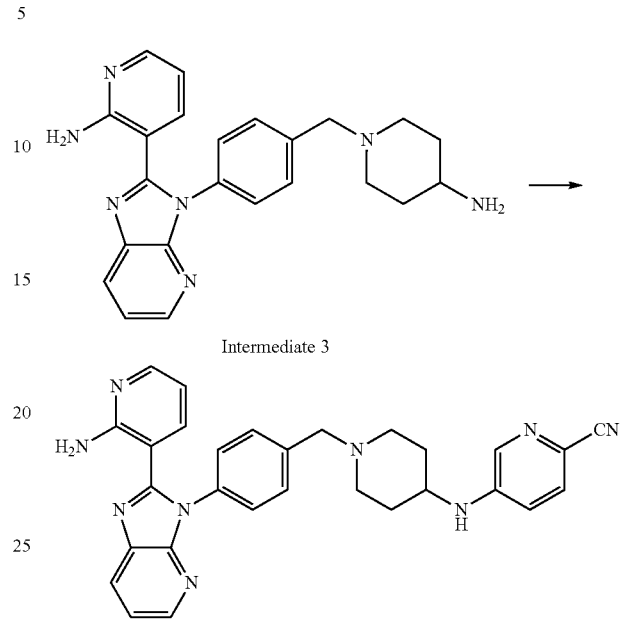

Intermediate 3

Example 157

Following the general procedure of Example 84, the reaction of Intermediate 3 (180 mg, 451 μmol) with 5-fluoropicolinonitrile (110 mg, 901 μmol) was carried out. After purified by prep-HPLC (column: Phenomenex C18 150×25 mm 10 μm; mobile phase: [water (NH$_4$HCO$_3$)-ACN]; B %: 16%-46%, 8 min), 5-((1-(4-(2-(2-aminopyridin-3-yl)-3H-imidazo[4,5-b]pyridin-3-yl)benzyl)piperidin-4-yl)amino)picolinonitrile (Example 157, 20.6 mg, yield: 8.5%) was obtained as an off-white solid. MS: m/z=502.1 [M+H]$^+$. $^1$H NMR (400 MHz, Dimethylsulfoxide-d$_6$) δ 8.34 (dd, J=4.8, 1.2 Hz, 1H), 8.21 (dd, J=8.0, 1.2 Hz, 1H), 8.06 (d, J=2.8 Hz, 1H), 7.99 (dd, J=4.8, 1.6 Hz, 1H), 7.61 (d, J=8.8 Hz, 1H), 7.46 (d, J=8.4 Hz, 2H), 7.42-7.37 (m, 3H), 7.17 (dd, J=7.6, 1.6 Hz, 1H), 7.04-6.96 (m, 3H), 6.91 (d, J=7.6 Hz, 1H), 6.38 (dd, J=7.6, 4.8 Hz, 1H), 3.58 (s, 2H), 2.90-2.75 (m, 3H), 2.21-2.12 (m, 2H), 1.96-1.87 (m, 2H), 1.50-1.40 (m, 2H).

Example 158: 5-((1-(4-(2-(2-Aminopyridin-3-yl)-5-phenyl-3H-imidazo[4,5-b]pyridin-3-yl)benzyl)piperidin-4-yl)amino)pyridazine-3-carbonitrile

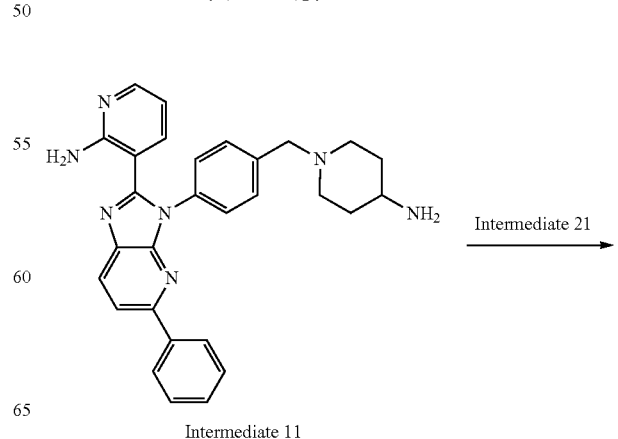

Intermediate 11

1219

-continued

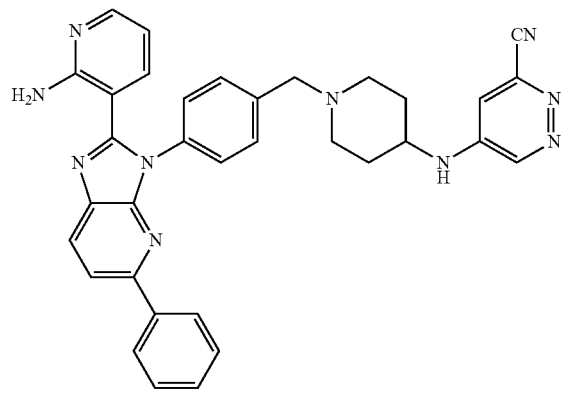

Example 158

Following the general procedure of Example 47, the reaction of Intermediate 11 (200 mg, 420 μmol) with Intermediate 21 (58 mg, 420 μmol) was carried out. After purified by prep-HPLC (column: Waters xbridge 150*25 mm 10 μm; mobile phase: [water (NH$_4$HCO$_3$)-ACN]; B %: 37%-67%, 10 min), 5-((1-(4-(2-(2-aminopyridin-3-yl)-5-phenyl-3H-imidazo[4,5-b]pyridin-3-yl)benzyl)piperidin-4-yl)amino)pyridazine-3-carbonitrile (Example 158, 75.3 mg, yield: 31%) was obtained as a yellow solid. MS: m/z=579.4 [M+H]$^+$. $^1$H NMR (400 MHz, Dimethylsulfoxide-d$_6$) δ 8.71 (br s, 1H), 8.27 (d, J=8.4 Hz, 1H), 8.06-7.95 (m, 4H), 7.67-7.57 (m, 1H), 7.53-7.43 (m, 6H), 7.41-7.37 (m, 1H), 7.37-7.29 (m, 1H), 7.16 (dd, J=7.6, 1.6 Hz, 1H), 7.03 (br s, 2H), 6.38 (dd, J=7.6, 4.8 Hz, 1H), 3.60 (s, 2H), 3.51-3.37 (m, 1H), 2.83 (d, J=11.6 Hz, 2H), 2.22-2.12 (m, 2H), 1.95-1.85 (m, 2H), 1.52-1.40 (m, 2H).

Example 159: 5-(4-(4-(2-(2-Aminopyridin-3-yl)-5-phenyl-3H-imidazo[4,5-b]pyridin-3-yl)benzyl)piperazin-1-yl)pyridazine-3-carbonitrile

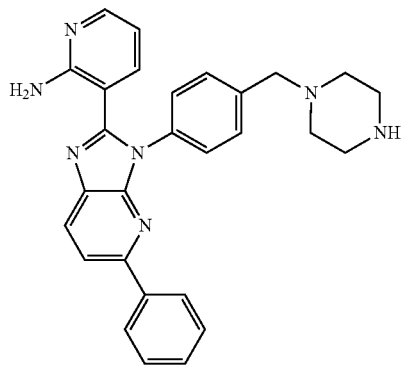

Intermediate 10

1220

-continued

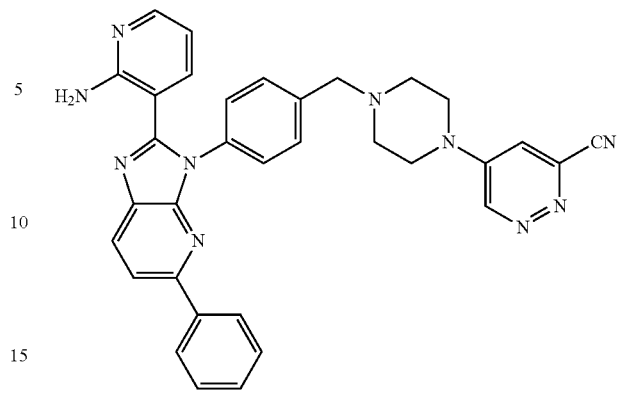

example 159

Following the general procedure of Example 47, the reaction of Intermediate 10 (200 mg, 433 μmol) with Intermediate 21 (60 mg, 433 μmol) was carried out. After purified by prep-HPLC (column: Waters xbridge 150*25 mm 10 μm; mobile phase: [water (NH$_4$HCO$_3$)-ACN]; B %: 35%-65%, 10 min), 5-(4-(4-(2-(2-aminopyridin-3-yl)-5-phenyl-3H-imidazo[4,5-b]pyridin-3-yl)benzyl)piperazin-1-yl)pyridazine-3-carbonitrile (Example 159, 48.7 mg, yield: 20%) was obtained as a yellow solid. MS: m/z=565.4 [M+H]$^+$. $^1$H NMR (400 MHz, Dimethylsulfoxide-d$_6$) δ 9.15 (d, J=3.2 Hz, 1H), 8.28 (d, J=8.4 Hz, 1H), 8.06-8.02 (m, 2H), 8.01-7.97 (m, 2H), 7.65 (d, J=3.2 Hz, 1H), 7.54-7.50 (m, 2H), 7.49-7.43 (m, 4H), 7.42-7.36 (m, 1H), 7.15 (dd, J=7.6, 1.6 Hz, 1H), 7.03 (br s, 2H), 6.36 (dd, J=7.6, 4.8 Hz, 1H), 3.65 (s, 2H), 3.61-3.53 (m, 4H), 2.56-2.50 (m, 4H).

Example 160: N-(4-(2-(2-Aminopyridin-3-yl)-5-phenyl-3H-imidazo[4,5-b]pyridin-3-yl)benzyl)-6-cyanonicotinamide Intermediate 21 →

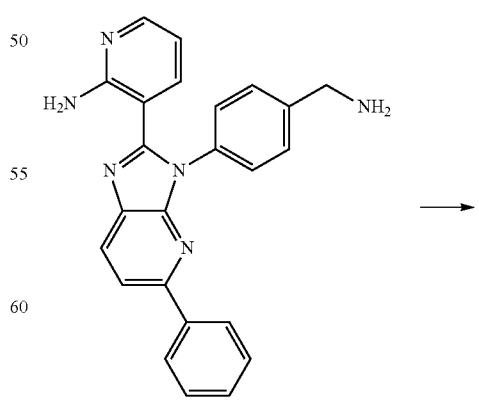

Intermediate 4

→

1221

-continued

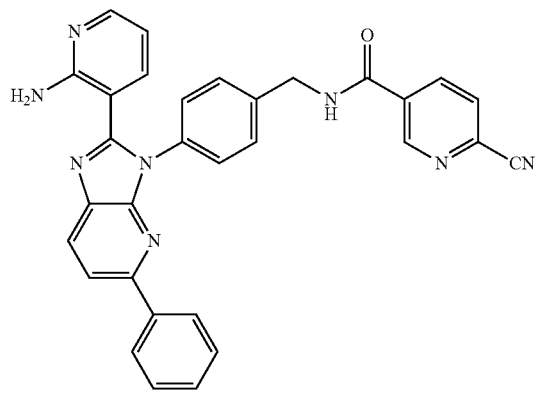

Example 160

1222

-continued

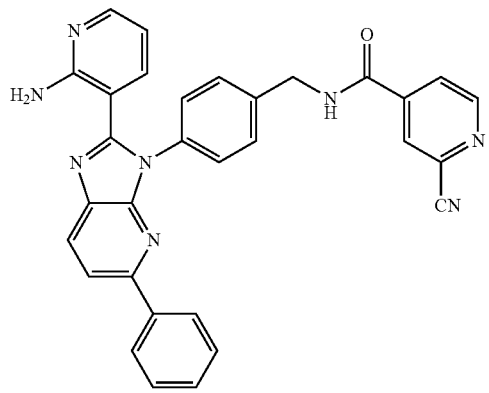

Example 161

Following the general procedure of Example 23, the reaction of Intermediate 4 (200 mg, 510 μmol) with 6-cyanonicotinic acid (75 mg, 510 μmol) was carried out. After purified by prep-HPLC (column: Phenomenex luna C18 150×25 mm×10 μm; mobile phase: [water (FA)-ACN]; B %: 20%-50%, 10 min), N-(4-(2-(2-aminopyridin-3-yl)-5-phenyl-3H-imidazo[4,5-b]pyridin-3-yl)benzyl)-6-cyanonicotinamide (Example 160, 41.1 mg, yield: 15%) was obtained as a yellow solid. MS: m/z=523.2 [M+H]$^+$. $^1$H NMR (400 MHz, Dimethylsulfoxide-d$_6$) δ 9.56 (t, J=5.6 Hz, 1H), 9.20 (d, J=1.6 Hz, 1H), 8.48 (dd, J=2.4, 8.0 Hz, 1H), 8.26 (d, J=8.0 Hz, 1H), 8.20 (d, J=8.0 Hz, 1H), 8.04-7.97 (m, 4H), 7.54-7.50 (m, 2H), 7.49-7.47 (m, 2H), 7.47-7.44 (m, 2H), 7.42-7.37 (m, 1H), 7.22 (dd, J=1.6, 7.6 Hz, 1H), 6.92 (br s, 2H), 6.42 (dd, J=7.6, 4.8 Hz, 1H), 4.65 (d, J=5.6 Hz, 2H).

Example 161: N-(4-(2-(2-Aminopyridin-3-yl)-5-phenyl-3H-imidazo[4,5-b]pyridin-3-yl)benzyl)-2-cyanoisonicotinamide

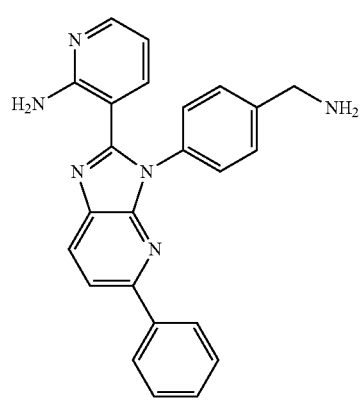

Intermediate 4

Following the general procedure of Example 23, the reaction of Intermediate 4 (150 mg, 382 μmol) with 2-cyanoisonicotinic acid (56.6 mg, 382 μmol) was carried out. After purified by prep-HPLC (column: Welch Xtimate C$_{18}$ 150×25 mm×5 μm; mobile phase: [water (NH$_4$HCO$_3$)-ACN]; B %: 33%-63%, 2 min), N-(4-(2-(2-aminopyridin-3-yl)-5-phenyl-3H-imidazo[4,5-b]pyridin-3-yl)benzyl)-2-cyanoisonicotinamide (Example 161, 30.2 mg, yield: 14%) was obtained as a yellow solid. MS: m/z=523.2 [M+H]$^+$. $^1$H NMR (400 MHz, Dimethylsulfoxide-d$_6$) δ 9.59 (t, J=5.6 Hz, 1H), 8.93 (d, J=4.8 Hz, 1H), 8.45 (s, 1H), 8.26 (d, J=8.4 Hz, 1H), 8.15 (dd, J=5.2, 1.6 Hz, 1H), 8.09-7.95 (m, 4H), 7.57-7.43 (m, 6H), 7.42-7.36 (m, 1H), 7.22 (dd, J=7.6, 2.0 Hz, 1H), 6.92 (br s, 2H), 6.42 (dd, J=7.6, 4.8 Hz, 1H), 4.65 (d, J=5.6 Hz, 2H).

Example 162: N-(4-(2-(2-Aminopyridin-3-yl)-5-phenyl-3H-imidazo[4,5-b]pyridin-3-yl)benzyl)-6-cyanopicolinamide

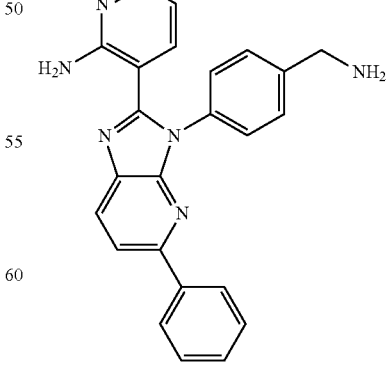

Intermediate 4

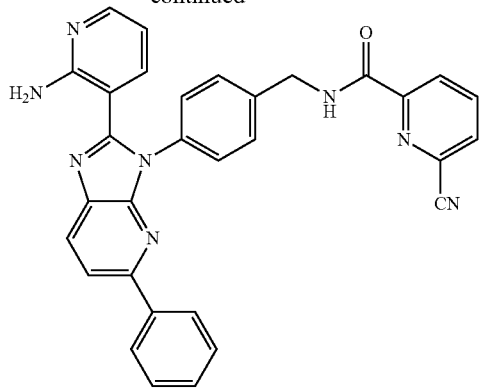

Example 162

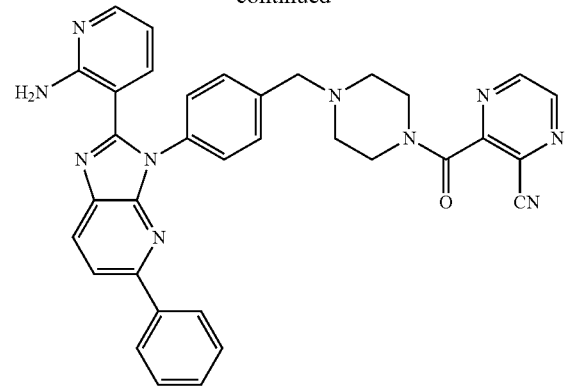

Example 163

Following the general procedure of Example 23, the reaction of Intermediate 4 (150 mg, 382 μmol) with 6-cyanopicolinic acid (56.6 mg, 382 μmol) was carried out. After purified by prep-HPLC (column: Waters xbridge 150×25 mm 10 μm; mobile phase: [water (NH$_4$HCO$_3$)-ACN]; B %: 36%-66%, 8 min), N-(4-(2-(2-aminopyridin-3-yl)-5-phenyl-3H-imidazo[4,5-b]pyridin-3-yl)benzyl)-6-cyanopicolinamide (Example 162, 41.2 mg, yield: 20%) was obtained as a yellow solid. MS: m/z=523.2 [M+H]$^+$. $^1$H NMR (400 MHz, Dimethylsulfoxide-d$_6$) δ 9.62 (t, J=6.4 Hz, 1H), 8.36-8.32 (m, 1H), 8.28-8.23 (m, 3H), 8.04-7.95 (m, 4H), 7.52-7.43 (m, 6H), 7.41-7.35 (m, 1H), 7.21 (dd, J=7.6, 1.6 Hz, 1H), 6.93 (br s, 2H), 6.42 (dd, J=7.6, 4.8 Hz, 1H), 4.62 (d, J=6.4 Hz, 2H). 1002%11 Example 163: 3-(4-(4-(2-(2-aminopyridin-3-yl)-5-phenyl-3H-imidazo[4,5-b]pyridin-3-yl)benzyl)piperazine-1-carbonyl)pyrazine-2-carbonitrile Following the general procedure of Example 23, the reaction of Intermediate 10 (250 mg, 812 μmol) with 3-carbamoylpyrazine-2-carboxylic acid (136 mg, 812 μmol) was carried out. After purified by prep-HPLC (column: Phenomenex C18 250*50 mm*10 μm; mobile phase: [water (NH$_4$HCO$_3$)-ACN]; B %: 30%-60%, 8 min), 3-(4-(4-(2-(2-aminopyridin-3-yl)-5-phenyl-3H-imidazo[4,5-b]pyridin-3-yl)benzyl)piperazine-1-carbonyl)pyrazine-2-carbonitrile (Example 163, 100 mg, yield: 28%) was obtained as a yellow lyophilized powder. MS: m/z=593.3 [M+H]$^+$. $^1$H NMR (400 MHz, Dimethylsulfoxide-d$_6$) δ 8.96 (dd, J=11.2, 2.4 Hz, 2H), 8.27 (d, J=8.4 Hz, 1H), 8.06-7.95 (m, 4H), 7.54-7.43 (m, 6H), 7.42-7.37 (m, 1H), 7.18-7.11 (m, 1H), 7.02 (br s, 2H), 6.36 (dd, J=7.6, 4.8 Hz, 1H), 3.79-3.73 (m, 2H), 3.65 (s, 2H), 3.45-3.39 (m, 2H), 2.58-2.52 (m, 2H), 2.45-2.42 (m, 2H).

Example 164: 3-(4-(4-(2-(2-Aminopyridin-3-yl)-3H-imidazo[4,5-b]pyridin-3-yl)benzyl)piperazine-1-carbonyl)pyrazine-2-carbonitrile

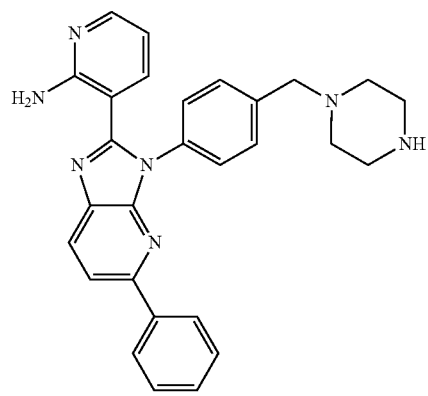

Intermediate 10

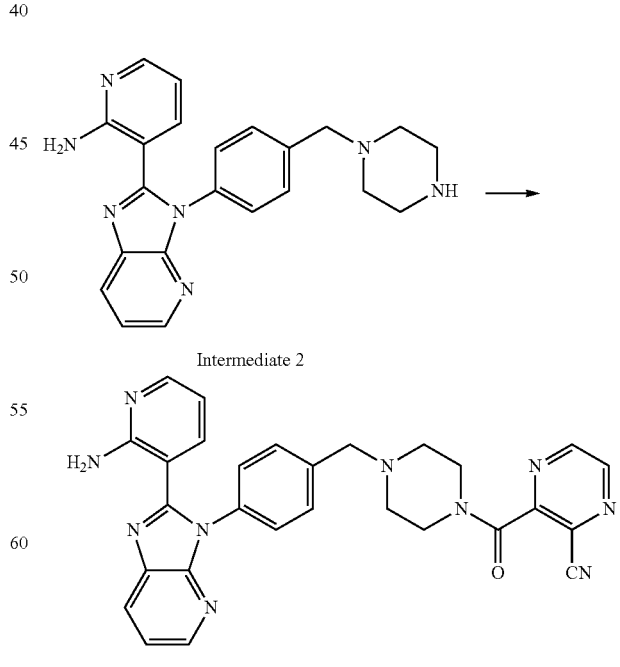

Intermediate 2

Example 164

To a solution of 3-carbamoylpyrazine-2-carboxylic acid (156 mg, 934 µmol) in DMF (1 mL) was added DIEA (402 mg, 3.11 mmol), EDCI (224 mg, 1.17 mmol), HOBt (158 mg, 1.17 mmol) and Intermediate 2 (300 mg, 778 µmol). The mixture was stirred at 25° C. for 16 hr to give an orange liquid, which was filtered and concentrated under reduced pressure to give a residue. The residue was purified by reversed-phase HPLC (neutral condition: column: Phenomenex C18 150*25 mm*10 µm; mobile phase: (water-ACN); B %: 20%-50%, 15 min), 3-(4-(4-(2-(2-aminopyridin-3-yl)-3H-imidazo[4,5-b]pyridin-3-yl)benzyl)piperazine-1-carbonyl)pyrazine-2-carbonitrile (Example 164, 8.0 mg, yield: 1.9%) was obtained as a yellow powder. MS: m/z=517.3 [M+H]$^+$. $^1$H NMR (400 MHz, Methanol-d$_4$) δ 8.90-8.82 (m, 2H), 8.34 (d, J=4.8 Hz, 1H), 8.20 (dd, J=8.0, 1.2 Hz, 1H), 7.97 (dd, J=5.2, 1.6 Hz, 1H), 7.56 (d, J=8.4 Hz, 2H), 7.47-7.37 (m, 3H), 7.33 (dd, J=7.6, 1.6 Hz, 1H), 6.47 (dd, J=7.6, 5.2 Hz, 1H), 3.93-3.85 (m, 2H), 3.72 (s, 2H), 3.51-3.44 (m, 2H), 2.69 (t, J=4.8 Hz, 2H), 2.62-2.54 (m, 2H).

Example 165: N-(1-(4-(2-(2-aminopyridin-3-yl)-6-phenyl-3H-imidazo[4,5-b]pyridin-3-yl)benzyl)piperidin-4-yl)-6-cyanonicotinamide

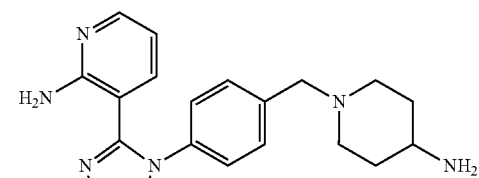

Intermediate 9

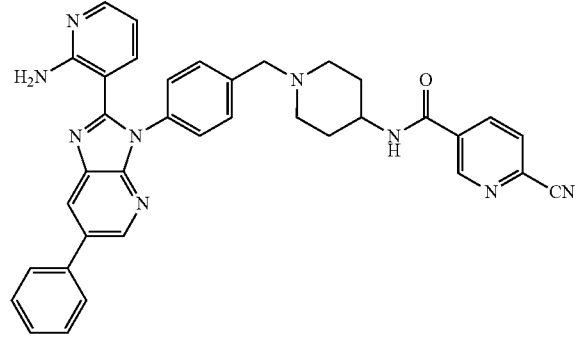

Example 165

Following the general procedure of Example 23, the reaction of Intermediate 9 (250 mg, 526 µmol) with 6-cyanopyridine-3-carboxylic acid (85.7 mg, 578 µmol) was carried out. After prep-HPLC (column: Waters xbridge 150*25 mm 10 µm; mobile phase: [water (NH$_4$HCO$_3$)-ACN]; B %: 19%-49%, 9 min), N-(1-(4-(2-(2-aminopyridin-3-yl)-6-phenyl-3H-imidazo[4,5-b]pyridin-3-yl)benzyl)piperidin-4-yl)-6-cyanonicotinamide (Example 165, 82 mg, yield: 25%) was obtained as a light-yellow solid. MS: m/z=606.2 [M+H]$^+$. $^1$H NMR (400 MHz, Dimethylsulfoxide-d$_6$) δ 9.11 (d, J=1.6 Hz, 1H), 8.72 (d, J=7.6 Hz, 1H), 8.64 (d, J=2.0 Hz, 1H), 8.47 (d, J=2.0 Hz, 1H), 8.41-8.38 (m, 1H), 8.17 (d, J=8.0 Hz, 1H), 8.00 (dd, J=4.8, 1.6 Hz, 1H), 7.78 (d, J=7.2 Hz, 2H), 7.54-7.47 (m, 4H), 7.43-7.40 (m, 3H), 7.2 (dd, J=8, 1.6 Hz, 1H), 7.07 (br s, 2H), 6.39 (dd, J=8, 4.8 Hz, 1H), 3.85-3.78 (m, 1H), 3.58 (s, 2H), 2.87 (d, J=11.2 Hz, 2H), 2.1 (t, J=11.2 Hz, 2H), 1.85 (d, J=10.0 Hz, 2H), 1.65-1.57 (m, 2H).

Example 166: 5-(4-(4-(2-(2-Aminopyridin-3-yl)-5-phenyl-3H-imidazo[4,5-b]pyridin-3-yl)benzyl)piperazine-1-carbonyl)picolinonitrile

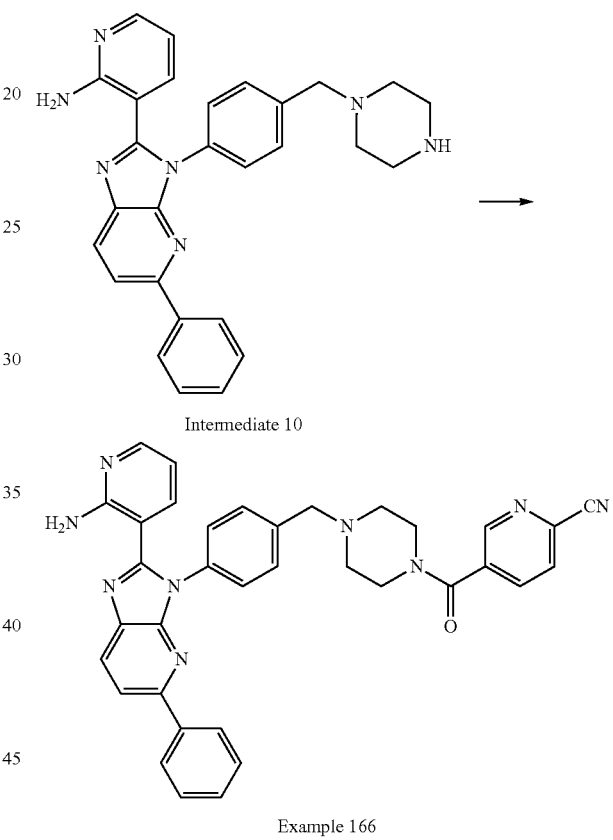

Intermediate 10

Example 166

Following the general procedure of Example 138, the reaction of Intermediate 10 (150 mg, 325 µmol) with 6-cyanonicotinic acid (53 mg, 357 µmol) was carried out. After purified by prep-HPLC (column: Waters xbridge 150*25 mm 10 µm; mobile phase: [water (NH$_4$HCO$_3$)-ACN]; B %: 42%-72%, 9 min), 5-(4-(4-(2-(2-aminopyridin-3-yl)-5-phenyl-3H-imidazo[4,5-b]pyridin-3-yl)benzyl)piperazine-1-carbonyl)picolinonitrile (Example 166, 27.5 mg, yield: 14%) was obtained as a yellow solid. MS: m/z=592.2 [M+H]$^+$. $^1$H NMR (400 MHz, Chloroform-d) δ 8.76 (s, 1H), 8.14 (d, J=8.4 Hz, 1H), 8.08-7.98 (m, 3H), 7.91 (dd, J=7.6, 2.0 Hz, 1H), 7.83-7.75 (m, 2H), 7.51-7.36 (m, 7H), 7.11 (d, J=7.6 Hz, 1H), 6.94-6.64 (m, 2H), 6.40-6.33 (m, 1H), 3.93-3.79 (m, 2H), 3.66 (s, 2H), 3.48-3.39 (m, 2H), 2.67-2.58 (m, 2H), 2.55-2.46 (m, 2H).

Example 167: N-(1-(4-(2-(2-Aminopyridin-3-yl)-5-phenyl-3H-imidazo[4,5-b]pyridin-3-yl)benzyl)piperidin-4-yl)-6-cyanonicotinamide Example 168: N-(4-(2-(2-Aminopyridin-3-yl)-6-phenyl-3H-imidazo[4,5-b]pyridin-3-yl)benzyl)-6-cyanopicolinamide

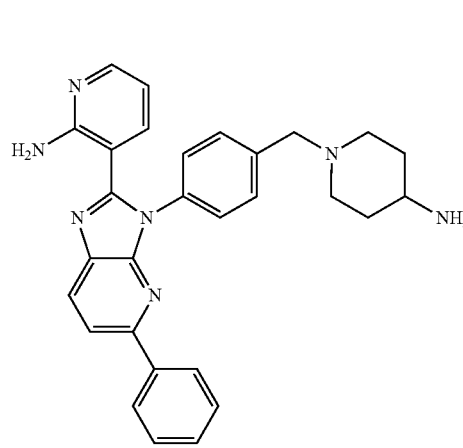

Intermediate 11

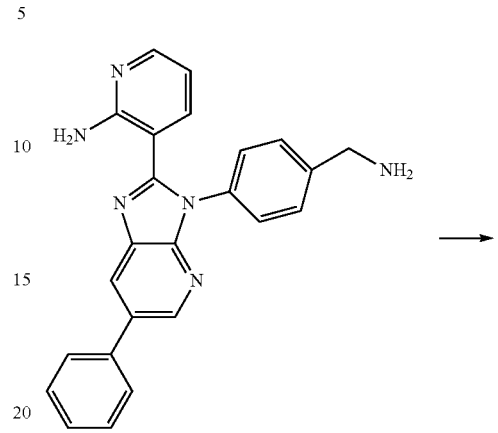

Intermediate 7

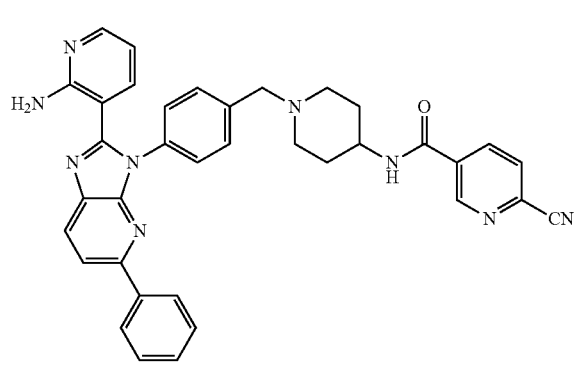

Example 167

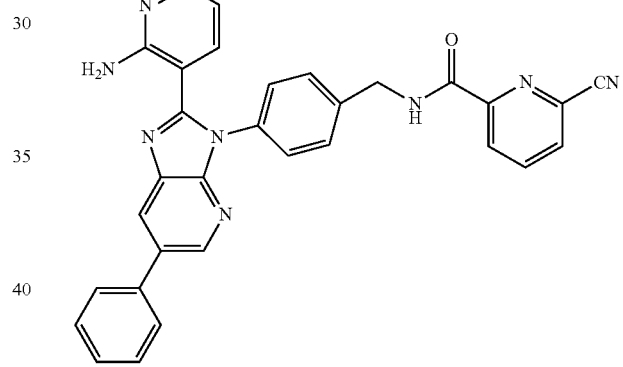

Example 168

Following the general procedure of Example 138, the reaction of Intermediate 11 (200 mg, 421 μmol) with 6-cyanonicotinic acid (69 mg, 463 μmol) was carried out. After purified by prep-HPLC (column: Waters xbridge 150*25 mm 10 μm; mobile phase: [water (NH$_4$HCO$_3$)-ACN]; B %: 35%-65%, 8 min), N-(1-(4-(2-(2-aminopyridin-3-yl)-5-phenyl-3H-imidazo[4,5-b]pyridin-3-yl)benzyl)piperidin-4-yl)-6-cyanonicotinamide (Example 167, 97.3 mg, yield: 37%) was obtained as a yellow solid. MS: m/z=606.2 [M+H]$^+$. $^1$H NMR (400 MHz, Dimethylsulfoxide-d$_6$) δ 9.11 (s, 1H), 8.71 (d, J=7.6 Hz, 1H), 8.40 (dd, J=8.0, 2.0 Hz, 1H), 8.27 (d, J=8.4 Hz, 1H), 8.17 (d, J=8.0 Hz, 1H), 8.08-7.96 (m, 4H), 7.51-7.37 (m, 7H), 7.16 (dd, J=7.6, 1.6 Hz, 1H), 7.04 (br s, 2H), 6.37 (dd, J=7.6, 4.8 Hz, 1H), 3.88-3.76 (m, 1H), 3.59 (s, 2H), 2.92-2.83 (m, 2H), 2.18-2.06 (m, 2H), 1.85 (d, J=10.8 Hz, 2H), 1.67-1.56 (m, 2H).

Following the general procedure of Example 138, the reaction of Intermediate 7 (150 mg, 382 μmol) with 6-cyanopicolinic acid (62 mg, 420 μmol) was carried out. After purified by prep-HPLC (column: Waters xbridge 150*25 mm 10 μm; mobile phase: [water (NH$_4$HCO$_3$)-ACN]; B %: 39%-69%, 9 min), N-(4-(2-(2-Aminopyridin-3-yl)-6-phenyl-3H-imidazo[4,5-b]pyridin-3-yl)benzyl)-6-cyanopicolinamide (Example 168, 88.5 mg, yield: 44%) was obtained as a yellow solid. MS: m/z=523.2 [M+H]$^+$. $^1$H NMR (400 MHz, Dimethylsulfoxide-d$_6$) δ 9.61 (t, J=6.4 Hz, 1H), 8.60 (s, 1H), 8.46 (s, 1H), 8.36-8.23 (m, 3H), 8.04-7.98 (m, 1H), 7.77 (d, J=7.6 Hz, 2H), 7.55-7.40 (m, 7H), 7.29-7.23 (m, 1H), 7.01 (s, 2H), 6.45-6.41 (m, 1H), 4.59 (d, J=6.4 Hz, 2H).

Example 169: N-(4-(2-(2-Aminopyridin-3-yl)-6-phenyl-3H-imidazo[4,5-b]pyridin-3-yl)benzyl)-2-cyanoisonicotinamide

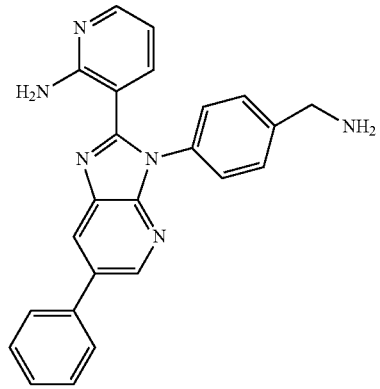

Intermediate 7

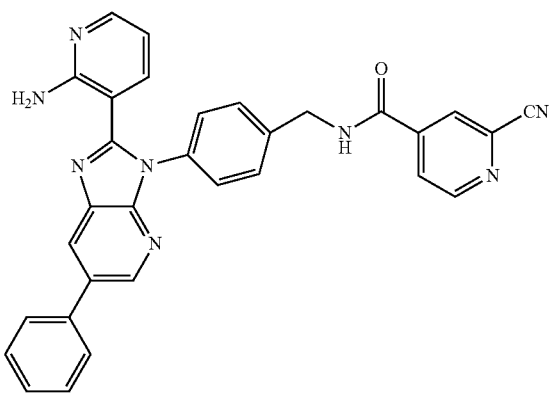

Example 169

Following the general procedure of Example 138, the reaction of Intermediate 7 (150 mg, 382 μmol) with 2-cyanoisonicotinic acid (62 mg, 420 μmol) was carried out. After purified by prep-HPLC (column: Waters xbridge 150*25 mm 10 μm; mobile phase: [water (NH$_4$HCO$_3$)-ACN]; B %: 30%-60%, 8 min), N-(4-(2-(2-aminopyridin-3-yl)-6-phenyl-3H-imidazo[4,5-b]pyridin-3-yl)benzyl)-2-cyanoisonicotinamide (Example 169, 93.1 mg, yield: 46%) was obtained as a yellow solid. MS: m/z=523.10 [M+H]$^+$. $^1$H NMR (400 MHz, Dimethylsulfoxide-d$_6$) δ 9.58 (t, J=5.6 Hz, 1H), 8.93 (d, J=5.2 Hz, 1H), 8.61 (s, 1H), 8.48-8.43 (m, 2H), 8.15 (d, J=5.2 Hz, 1H), 8.04-7.97 (m, 1H), 7.78 (d, J=7.2 Hz, 2H), 7.55-7.50 (m, 4H), 7.47-7.40 (m, 3H), 7.28 (dd, J=7.6, 2.0 Hz, 1H), 6.99 (br s, 2H), 6.43 (dd, J=7.6, 4.8 Hz, 1H), 4.62 (d, J=5.6 Hz, 2H).

Example 170: N-(4-(2-(2-Aminopyridin-3-yl)-5-phenyl-3H-imidazo[4,5-b]pyridin-3-yl)benzyl)-4-cyanopicolinamide

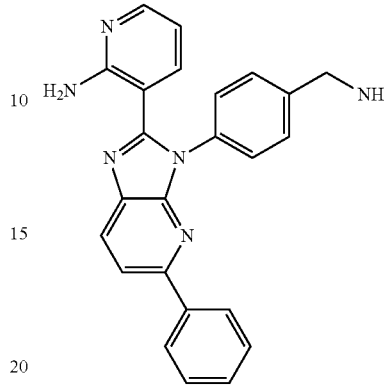

Intermediate 4

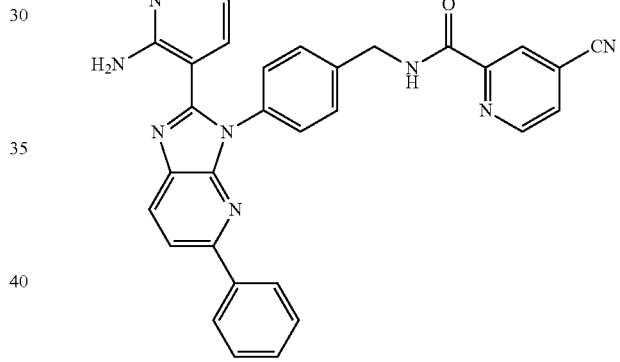

Example 170

Following the general procedure of Example 138, the reaction of Intermediate 4 (200 mg, 510 μmol) with 4-cyanopyridine-2-carboxylic acid (83 mg, 560 μmol) in DCM was carried out. After purified by prep-HPLC (column: Waters xbridge 150×25 mm 10 μm; mobile phase: [water (NH$_4$HCO$_3$)-ACN]; B %: 37%-67%, 8 min), N-(4-(2-(2-aminopyridin-3-yl)-5-phenyl-3H-imidazo[4,5-b]pyridin-3-yl)benzyl)-4-cyanopicolinamide (Example 170, 31.7 mg, yield: 11%) was obtained as a yellow solid. MS: m/z=523.1 [M+H]$^+$. $^1$H NMR (400 MHz, Dimethylsulfoxide-d$_6$) δ 9.65 (t, J=6.4 Hz, 1H), 8.93 (d, J=4.8 Hz, 1H), 8.39 (s, 1H), 8.26 (d, J=8.0 Hz, 1H), 8.11 (dd, J=5.2, 1.6 Hz, 1H), 8.04-7.96 (m, 4H), 7.50-7.43 (m, 6H), 7.41-7.37 (m, 1H), 7.21 (dd, J=7.6, 2.0 Hz, 1H), 6.93 (br s, 2H), 6.41 (dd, J=7.6, 4.8 Hz, 1H), 4.63 (d, J=6.4 Hz, 2H).

Example 171: N-(4-(2-(2-Aminopyridin-3-yl)-5-phenyl-3H-imidazo[4,5-b]pyridin-3-yl)benzyl)-2-cyanopyrimidine-4-carboxamide Example 172: 4-(4-(4-(2-(2-Aminopyridin-3-yl)-5-phenyl-3H-imidazo[4,5-b]pyridin-3-yl)benzyl)piperazine-1-carbonyl)picolinonitrile

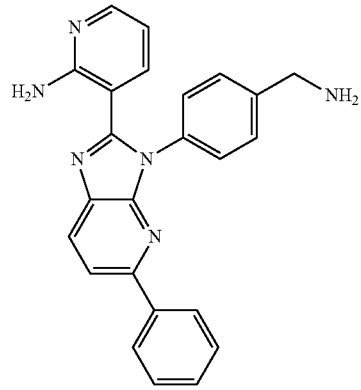

Intermediate 4

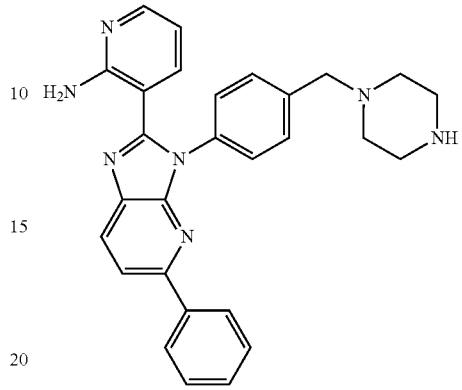

Intermediate 10

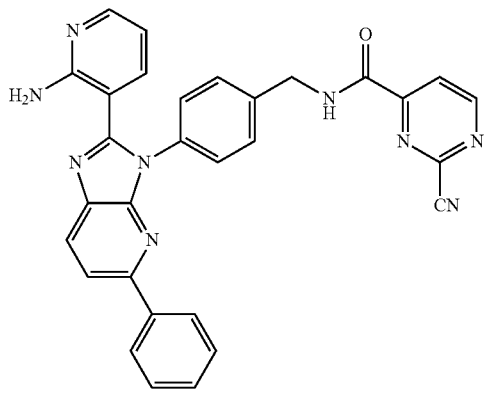

Example 171

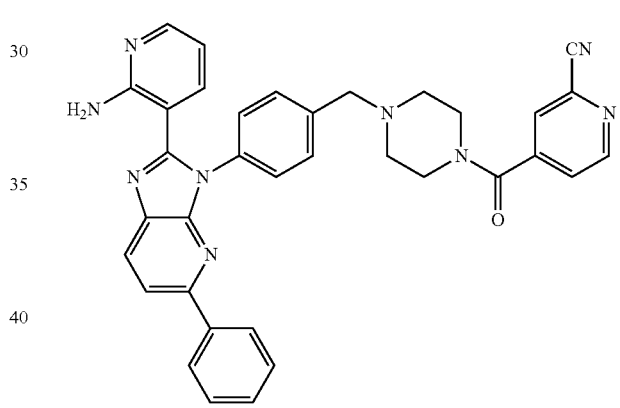

Example 172

Following the general procedure of Example 138, the reaction of Intermediate 4 (150 mg, 382 μmol) with 2-cyanopyrimidine-4-carboxylic acid (57 mg, 382 μmol) in DCM was carried out. After purified by prep-HPLC (column: Phenomenex 150×25 mm 10 μm; mobile phase: [water (NH$_4$HCO$_3$)-ACN]; B %: 42%-72%, 8 min), N-(4-(2-(2-aminopyridin-3-yl)-5-phenyl-3H-imidazo[4,5-b]pyridin-3-yl)benzyl)-2-cyanopyrimidine-4-carboxamide (Example 171, 19.1 mg, yield: 9.3%) was obtained as a yellow solid. MS: m/z=524.1 [M+H]$^+$. $^1$H NMR (400 MHz, Dimethylsulfoxide-d$_6$)) δ 9.88 (t, J=6.4 Hz, 1H), 9.25 (d, J=5.2 Hz, 1H), 8.32 (d, J=5.2 Hz, 1H), 8.26 (d, J=8.4 Hz, 1H), 8.03-7.96 (m, 4H), 7.52-7.44 (m, 6H), 7.41-7.36 (m, 1H), 7.21 (dd, J=7.6, 2.0 Hz, 1H), 6.91 (br s, 2H), 6.42 (dd, J=7.6, 4.8 Hz, 1H), 4.62 (d, J=6.4 Hz, 2H).

Following the general procedure of Example 138, the reaction of Intermediate 10 (150 mg, 325 μmol) with 2-cyanoisonicotinic acid (58 mg, 390 μmol) in DCM was carried out. After purified by prep-HPLC (column: Waters xbridge 150*25 mm 10 μm; mobile phase: [water (NH$_4$HCO$_3$)-ACN]; B %: 40%-70%, 11 min), 4-(4-(4-(2-(2-aminopyridin-3-yl)-5-phenyl-3H-imidazo[4,5-b]pyridin-3-yl)benzyl)piperazine-1-carbonyl)picolinonitrile (Example 172, 50 mg, yield: 24%) was obtained as a white solid. MS: m/z=592.2 [M+H]$^+$. $^1$H NMR (400 MHz, Dimethylsulfoxide-d$_6$) δ 8.84 (d, J=4.8 Hz, 1H), 8.27 (d, J=8.4 Hz, 1H), 8.12 (s, 1H), 8.06-7.96 (m, 4H), 7.78-7.73 (m, 1H), 7.52-7.43 (m, 6H), 7.43-7.35 (m, 1H), 7.18-7.13 (m, 1H), 7.02 (br s, 2H), 6.43-6.36 (m, 1H), 3.71-3.60 (m, 4H), 3.32-3.27 (m, 2H), 2.44-2.38 (m, 4H).

Example 173: N-(4-(2-(2-aminopyridin-3-yl)-3H-imidazo[4,5-b]pyridin-3-yl)benzyl)-2-cyano-5-fluorobenzo[d]thiazole-7-carboxamide

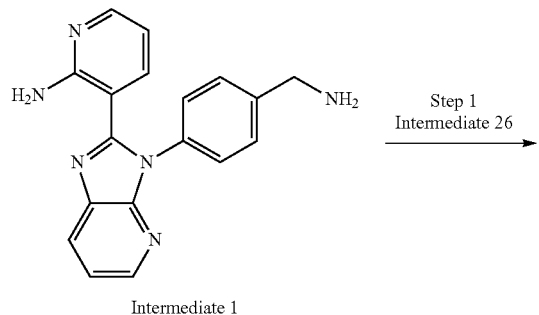

Intermediate 1

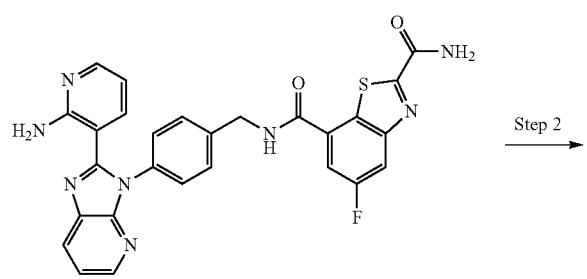

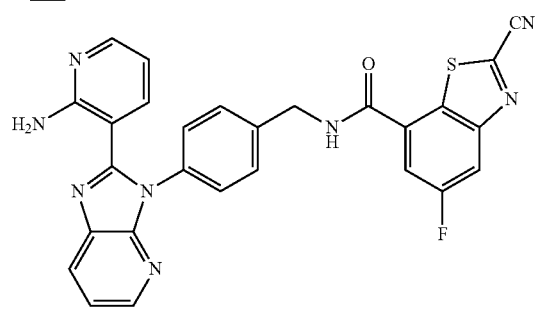

Example 173

Step 1: N⁷-(4-(2-(2-Aminopyridin-3-yl)-3H-imidazo[4,5-b]pyridin-3-yl)benzyl)-5-fluorobenzo[d]thiazole-2,7-dicarboxamide A mixture of Intermediate 1 (300 mg, 948 μmol), Intermediate 26 (227.8 mg, 948 μmol), HATU (540.9 mg, 1.42 mmol), DIEA (613 mg, 4.74 mmol) in DMF (2 mL) was stirred at 25° C. for 16 hr. This reaction was filtered and concentrated to give the residue. The residue was purified by prep-HPLC (column: Welch Xtimate C18 150×25 mm×5 μm; mobile phase: [water (NH$_3$H$_2$O)-ACN]; B %: 15%-45%, 8 min), N⁷-(4-(2-(2-aminopyridin-3-yl)-3H-imidazo[4,5-b]pyridin-3-yl)benzyl)-5-fluorobenzo[d]thiazole-2,7-dicarboxamide (39.5 mg, yield: 12%) was obtained as a light-yellow solid. MS: m/z=539.2 [M+H]⁺. ¹H NMR (400 MHz, Dimethylsulfoxide-d$_6$) δ 9.65 (t, J=5.6 Hz, 1H), 8.47 (s, 1H), 8.32-8.26 ((m, 2H), 8.21-8.15 (m, 2H), 8.09 (s, 1H), 7.99 (dd, J=4.8, 1.6 Hz, 1H), 7.51 (d, J=8.0 Hz, 2H), 7.44-7.36 (m, 3H), 7.24 (dd, J=7.6, 1.6 Hz, 1H), 6.95 (br s, 2H), 6.41 (dd, J=7.6, 4.8 Hz, 1H), 4.67 (d, J-=5.6 Hz, 2H). ¹⁹F NMR (400 MHz, Dimethylsulfoxide-d$_6$) δ -114.4.

Step 2: N-(4-(2-(2-Aminopyridin-3-yl)-3H-imidazo[4,5-b]pyridin-3-yl)benzyl)-2-cyano-5-fluorobenzo[d]thiazole-7-carboxamide To a solution of N⁷-(4-(2-(2-aminopyridin-3-yl)-3H-imidazo[4,5-b]pyridin-3-yl)benzyl)-5-fluorobenzo[d]thiazole-2,7-dicarboxamide (20 mg, 37.1 μmol) in pyridine (2 mL), then POCl$_3$ (142 mg, 928 μmol) was added dropwise over 5 min, the mixture was stirred at 20° C. for 2 hr. The reaction mixture was filtered to give filter liquor. The residue was purified by prep-HPLC (column: Welch Xtimate C18 150× 25 mm×5 μm; mobile phase: [water (NH$_4$HCO$_3$)-ACN]; B %: 31%-61%, 2 min), N-(4-(2-(2-aminopyridin-3-yl)-3H-imidazo[4,5-b]pyridin-3-yl)benzyl)-2-cyano-5-fluorobenzo[d]thiazole-7-carboxamide (Example 173, 9.2 mg, yield: 47%) was obtained as a white lyophilized powder. MS: m/z=521.0 [M+H]⁺. ¹H NMR (400 MHz, Dimethylsulfoxide-d$_6$) δ 9.83 (t, J=5.2 Hz, 1H), 8.51-8.41 (m, 2H), 8.30 (d, J=4.8 Hz, 1H), 8.19 (d, J=8.0 Hz, 1H), 8.02-7.96 (m, 1H), 7.51 (d, J=8.0 Hz, 2H), 7.43-7.35 (m, 3H), 7.24 (d, J=7.6 Hz, 1H), 6.93 (br s, 2H), 6.41 (dd, J=7.6, 4.8 Hz, 1H), 4.68 (d, J=5.2 Hz, 2H). ¹⁹F NMR (400 MHz, Dimethylsulfoxide-d$_6$) δ -112.9.

Example 174: N-(4-(2-(2-aminopyridin-3-yl)-3H-imidazo[4,5-b]pyridin-3-yl)benzyl)-2-cyano-6-fluorobenzo[d]thiazole-4-carboxamide

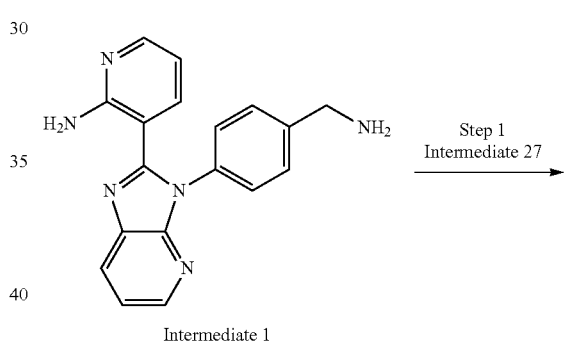

Intermediate 1

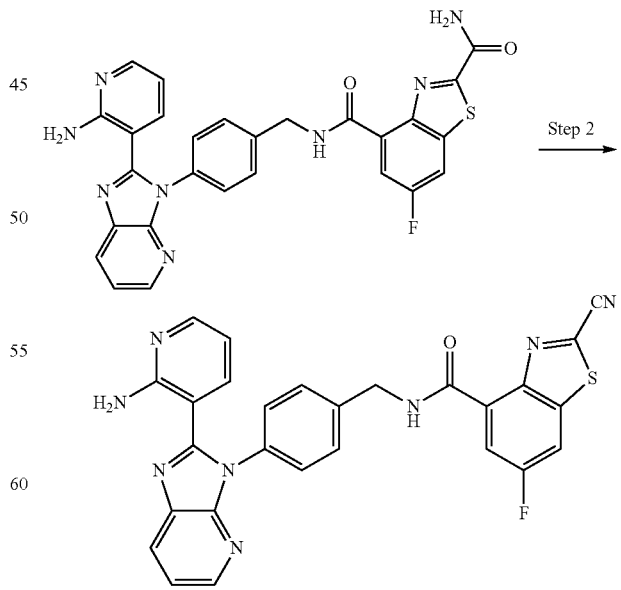

Example 174

Step 1: N⁴-(4-(2-(2-Aminopyridin-3-yl)-3H-imidazo[4,5-b]pyridin-3-yl)benzyl)-6-fluorobenzo[d]thiazole-2,4-dicarboxamide Following the general procedure of Example 173 step 1, the reaction of Intermediate 1 (50 mg, 158 μmol) with Intermediate 27 (38 mg, 158 μmol) was carried out. After purified by prep-HPLC (column: Welch Xtimate C18 150×25 mm×5 μm; mobile phase: [water (NH₄HCO₃)-ACN]; B %: 21%-51%, 10 min), N⁴-(4-(2-(2-aminopyridin-3-yl)-3H-imidazo[4,5-b]pyridin-3-yl)benzyl)-6-fluorobenzo[d]thiazole-2,4-dicarboxamide (30 mg, yield: 32%) was obtained as a light-yellow lyophilized powder. MS: m/z=539.1 [M+H]⁺. ¹H NMR (400 MHz, Dimethylsulfoxide-d₆) δ 10.05 (t, J=6.0 Hz, 1H), 9.13 (s, 1H), 8.42-8.35 (m, 1H), 8.32-8.27 (m, 2H), 8.19 (d, J=7.6 Hz, 1H), 8.11-8.05 (m, 1H), 8.00-7.96 (m, 1H), 7.48 (d, J=8.0 Hz, 2H), 7.41-7.34 (m, 3H), 7.24 (d, J=7.6 Hz, 1H), 6.95 (br s, 2H), 6.39 (dd, J=7.6, 4.8 Hz, 1H), 4.79 (br d, J=6.0 Hz, 2H). ¹⁹F NMR (400 MHz, Dimethylsulfoxide-d₆) δ −112.7.

Step 2: N-(4-(2-(2-Aminopyridin-3-yl)-3H-imidazo[4,5-b]pyridin-3-yl)benzyl)-2-cyano-6-fluorobenzo[d]thiazole-4-carboxamide Following the general procedure of Example 173 step 2, the reaction of N⁴-(4-(2-(2-aminopyridin-3-yl)-3H-imidazo[4,5-b]pyridin-3-yl)benzyl)-6-fluorobenzo[d]thiazole-2,4-dicarboxamide (30 mg, 56 μmol) with POCl₃ was carried out. After purified by prep-HPLC (column: Phenomenex C18 150×25 mm×10 μm; mobile phase: [water (NH₄HCO₃)-ACN]; B %: 30%-60%, 8 min), N-(4-(2-(2-aminopyridin-3-yl)-3H-imidazo[4,5-b]pyridin-3-yl)benzyl)-2-cyano-6-fluorobenzo[d]thiazole-4-carboxamide (Example 174, 4.8 mg, yield: 16%) was obtained as a light-yellow lyophilized powder. MS: m/z=521.1 [M+H]⁺. ¹H NMR (400 MHz, Methanol-d₄) δ 8.32 (dd, J=4.8, 1.6 Hz, 1H), 8.21-8.13 (m, 3H), 7.97 (dd, J=5.2, 2.0 Hz, 1H), 7.63 (d, J=8.4 Hz, 2H), 7.44-7.40 (m, 3H), 7.36-7.33 (m, 1H), 6.48 (dd, J=8.0, 5.2 Hz, 1H), 4.58 (s, 2H). ¹⁹F NMR (400 MHz, Methanol-d₄) δ−111.1.

Example 175: 7-(4-(4-(2-(2-aminopyridin-3-yl)-3H-imidazo[4,5-b]pyridin-3-yl)benzyl)piperazine-1-carbonyl)-5-fluorobenzo[d]thiazole-2-carbonitrile

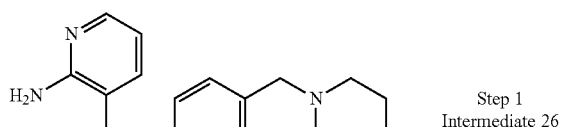

Intermediate 2

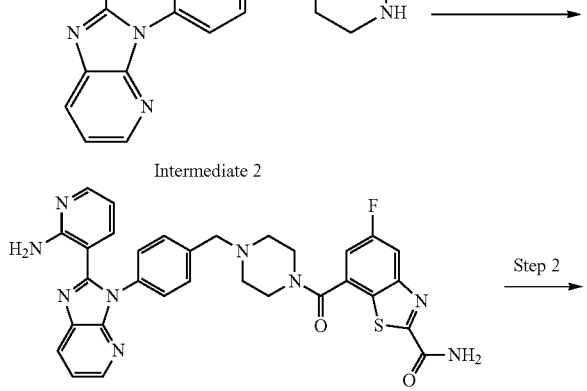

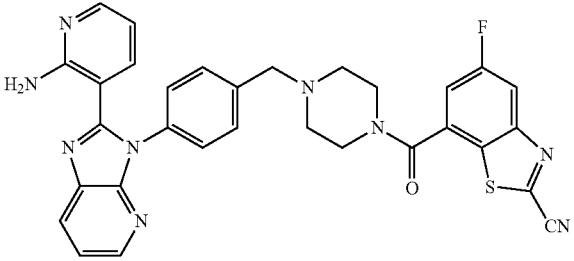

Example 175

Step 1: 7-(4-(4-(2-(2-Aminopyridin-3-yl)-3H-imidazo[4,5-b]pyridin-3-yl)benzyl)piperazine-1-carbonyl)-5-fluorobenzo[d]thiazole-2-carboxamide Following the general procedure of Example 173 step 1, the reaction of Intermediate 2 (50 mg, 130 μmol) with Intermediate 26 (30 mg, 130 μmol) was carried out. After purified by prep-HPLC (column: Phenomenex C18 150×25 mm×10 μm; mobile phase. [water (NH₄HCO₃)-ACN]; B %: 20%-50%, 8 min), 7-(4-(4-(2-(2-aminopyridin-3-yl)-3H-imidazo[4,5-b]pyridin-3-yl)benzyl)piperazine-1-carbonyl)-5-fluorobenzo[d]thiazole-2-carboxamide (8.7 mg, yield: 11%) was obtained as an off-white lyophilized powder. MS: m/z=608.2 [M+H]⁺. ¹H NMR (400 MHz, Dimethylsulfoxide-d₆) δ 8.57 (s, 1H), 8.32 (dd, J=4.8, 1.2 Hz, 1H), 8.23-8.15 (m, 2H), 8.07 (dd, J=8.0, 2.4 Hz, 1H), 7.98 (dd, J=4.8, 2.0 Hz, 1H), 7.63 (dd, J=8.0 2.4 Hz, 1H), 7.47 (d, J=8.4 Hz, 2H), 7.42-7.35 (m, 3H), 7.16 (dd, J=7.6, 2.0 Hz, 1H), 7.00 (br s, 2H), 6.37 (dd, J=7.6, 4.8 Hz, 1H), 3.67-3.56 (m, 4H), 3.31-3.22 (m, 2H), 2.49-2.39 (m, 4H). ¹⁹F NMR (400 MHz, Dimethylsulfoxide-d₆) δ −113.8.

Step 2: 7-(4-(4-(2-(2-Aminopyridin-3-yl)-3H-imidazo[4,5-b]pyridin-3-yl)benzyl)piperazine-1-carbonyl)-5-fluorobenzo[d]thiazole-2-carbonitrile Following the general procedure of Example 173 step 2, the reaction of 7-(4-(4-(2-(2-aminopyridin-3-yl)-3H-imidazo[4,5-b]pyridin-3-yl)benzyl)piperazine-1-carbonyl)-5-fluorobenzo[d]thiazole-2-carboxamide (30 mg, 49 μmol) with POCl₃ was carried out. After purified by prep-HPLC (column: Phenomenex C18 150×25 mm×10 μm; mobile phase: [water (NH₄HCO₃)-ACN]; B %: 30%-60%, 14 min), 7-(4-(4-(2-(2-aminopyridin-3-yl)-3H-imidazo[4,5-b]pyridin-3-yl)benzyl)piperazine-1-carbonyl)-5-fluorobenzo[d]thiazole-2-carbonitrile (Example 175, 2.3 mg, yield: 7.4%) was obtained as light-yellow lyophilized powder. MS: m/z=590.3 [M+H]⁺. ¹H NMR (400 MHz, Methanol-d₄) δ 8.34 (dd, J=4.8, 1.2 Hz, 1H), 8.20 (dd, J=8.0, 5.2 Hz, 1H), 8.14-8.09 (m, 1H), 7.97 (dd, J=4.8, 1.6 Hz, 1H), 7.72 (dd, J=8.8, 2.4 Hz, 1H), 7.55 (d, J=8.4 Hz, 2H), 7.45-7.41 (m, 1H), 7.40-7.38 (m, 2H), 7.32 (dd, J=7.6, 2.0 Hz, 1H), 6.46 (dd, J=7.6, 4.8 Hz, 11H), 3.81-3.70 (m, 4H), 3.68 (s, 2H), 2.60-2.52 (m, 4H). ¹⁹F NMR (400 MHz, Methanol-d₄) δ −113.8.

Example 176: N-(4-(2-(2-Aminopyridin-3-yl)-5-phenyl-3H-imidazo[4,5-b]pyridin-3-yl)benzyl)-2-cyano-5-fluorobenzo[d]thiazole-7-carboxamide

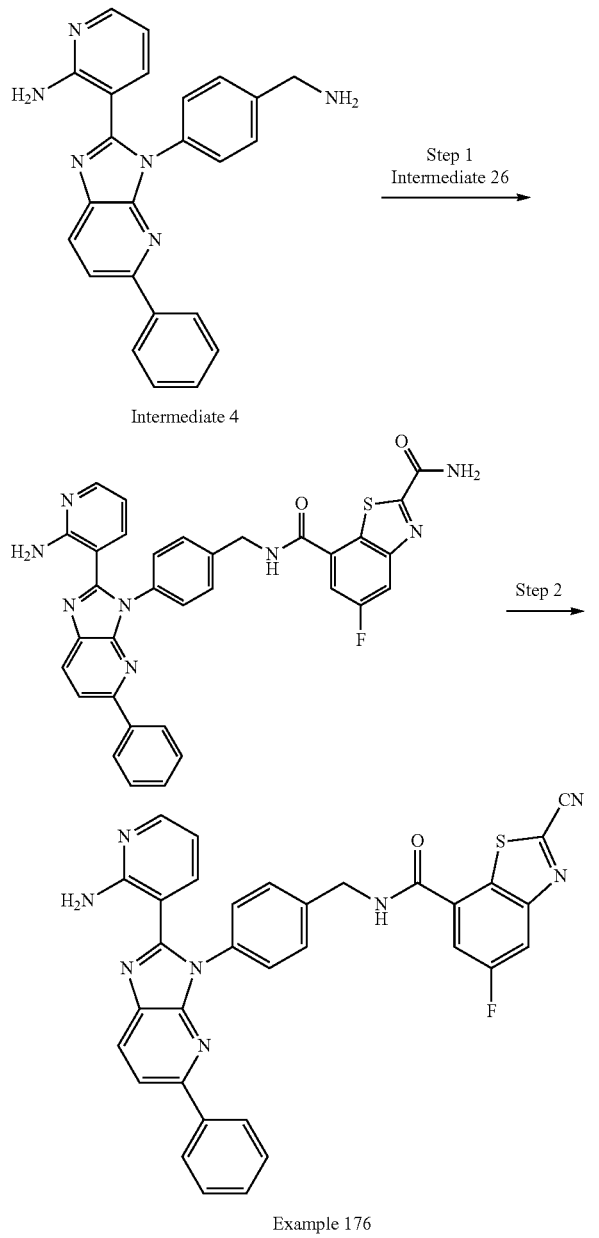

Step 1: N⁷-(4-(2-(2-Aminopyridin-3-yl)-5-phenyl-3H-imidazo[4,5-b]pyridin-3-yl)benzyl)-5-fluorobenzo[d]thiazole-2,7-dicarboxamide Following the general procedure of Example 173 step 1, the reaction of Intermediate 4 (50 mg, 127 μmol) with Intermediate 26 (30.6 mg, 127 μmol) was carried out. After purified by prep-HPLC (column: Welch Xtimate C18 150×25 mm×5 μm; mobile phase: [water (NH₃H₂O)-ACN]; B %: 35%-65%, 8 min), N⁷-(4-(2-(2-aminopyridin-3-yl)-5-phenyl-3H-imidazo[4,5-b]pyridin-3-yl)benzyl)-5-fluorobenzo[d]thiazole-2,7-dicarboxamide (35 mg, yield: 41%) was obtained as a yellow lyophilized powder. MS: m/z=615.3 [M+H]⁺. ¹H NMR (400 MHz, Dimethylsulfoxide-d₆) δ 10.10-10.03 (m, 1H), 9.15 (s, 1H), 8.39 (dd, J=8.0, 2.8 Hz, 1H), 8.32-8.28 (m, 1H), 8.26 (d, J=8.4 Hz, 1H), 8.09 (dd, J=9.6, 2.8 Hz, 1H), 8.03-7.96 (m, 4H), 7.52-7.44 (m, 6H), 7.41-7.35 (m, 1H), 7.23 (dd, J=7.6, 1.6 Hz, 1H), 6.91 (br s, 2H), 6.41 (dd, J=7.6, 4.8 Hz, 1H), 4.83 (d, J=6.8 Hz, 2H). ¹⁹F NMR (400 MHz, Dimethylsulfoxide-d₆) δ -112.7.

Step 2: N-(4-(2-(2-Aminopyridin-3-yl)-5-phenyl-3H-imidazo[4,5-b]pyridin-3-yl)benzyl)-2-cyano-5-fluorobenzo[d]thiazole-7-carboxamide Following the general procedure of Example 173 step 2, the reaction of N⁷-(4-(2-(2-aminopyridin-3-yl)-5-phenyl-3H-imidazo[4,5-b]pyridin-3-yl)benzyl)-5-fluorobenzo[d]thiazole-2,7-dicarboxamide (30 mg, 48 μmol) was carried out. After purified by prep-HPLC (column: Phenomenex C18 150×25 mm×10 μm; mobile phase: [water (NH₄HCO₃)-ACN]; B %: 36%-66%, 8 min), N-(4-(2-(2-Aminopyridin-3-yl)-5-phenyl-3H-imidazo[4,5-b]pyridin-3-yl)benzyl)-2-cyano-5-fluorobenzo[d]thiazole-7-carboxamide (Example 176, 4.5 mg, yield: 15%) was obtained as a light-yellow lyophilized powder. MS: m/z=597.1 [M+H]⁺. ¹H NMR (400 MHz, Methanol-d₄) δ 8.21-8.15 (m, 3H), 8.03-8.00 (m, 2H), 7.97 (dd, J=4.8, 1.6 Hz, 1H), 7.93 (d, J=8.4 Hz, 1H), 7.59 (d, J=8.4 Hz, 2H), 7.47 (d, J=8.4 Hz, 2H), 7.43-7.37 (m, 3H), 7.36-7.32 (m, 2H), 6.48 (dd, J=7.6, 5.2 Hz, 1H), 4.77 (s, 2H). ¹⁹F NMR (400 MHz, Methanol-d₄) δ -114.4.

Example 177: N-(4-(2-(2-Aminopyridin-3-yl)-5-phenyl-3H-imidazo[4,5-b]pyridin-3-yl)benzyl)-2-cyano-6-fluorobenzo[d]thiazole-4-carboxamide

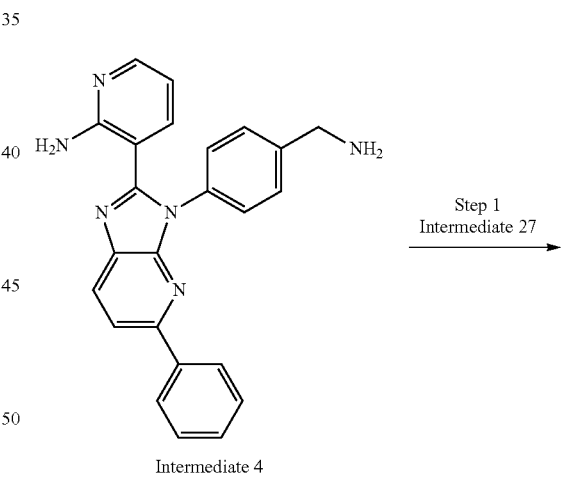

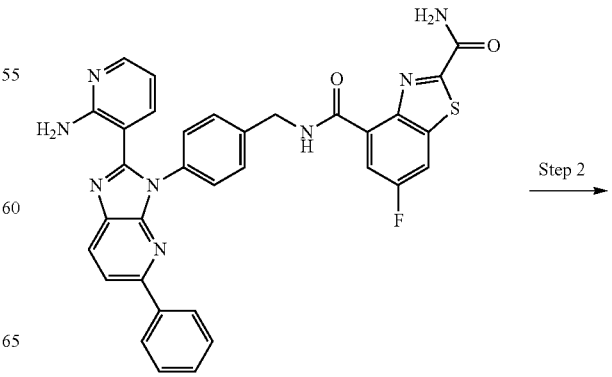

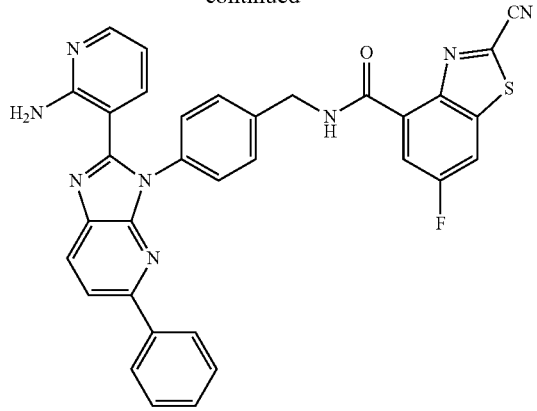

Example 177

Step 1: N⁴-(4-(2-(2-Aminopyridin-3-yl)-5-phenyl-3H-imidazo[4,5-b]pyridin-3-yl)benzyl)-6-fluorobenzo[d]thiazole-2,4-dicarboxamide Following the general procedure of Example 173 step 1, the reaction of Intermediate 4 (50 mg, 127 μmol) with Intermediate 27 (30.6 mg, 127 μmol) was carried out. After purified by prep-HPLC (column: Welch Xtimate C18 150× 25 mm×5 μm; mobile phase: [water (NH$_3$H$_2$O)-ACN]; B %: 36%-66%, 8 min), N⁴-(4-(2-(2-aminopyridin-3-yl)-5-phenyl-3H-imidazo[4,5-b]pyridin-3-yl)benzyl)-6-fluorobenzo[d]thiazole-2,4-dicarboxamide (40 mg, yield: 46%) was obtained as a yellow lyophilized powder. MS: m/z=615.4 [M+H]⁺. ¹H NMR (400 MHz, Dimethylsulfoxide-d$_6$) δ 10.06 (t, J=6.0, 1H), 9.14 (s, 1H), 8.39 (dd, J=7.8, 2.8 Hz, 1H), 8.30 (s, 1H), 8.26 (d, J=8.4 Hz, 1H), 8.09 (dd, J=10.0, 2.8 Hz, 1H), 8.03-7.96 (m, 4H), 7.52-7.43 (m, 6H), 7.41-7.35 (m, 1H), 7.23 (dd, J=7.6, 1.6 Hz, 1H), 6.91 (br s, 2H), 6.41 (dd, J=7.6, 4.8 Hz, 1H), 4.83 (d, J=6.0 Hz, 2H). ¹⁹F NMR (400 MHz, Dimethylsulfoxide-d$_6$) δ −112.7.

Step 2: N-(4-(2-(2-Aminopyridin-3-yl)-5-phenyl-3H-imidazo[4,5-b]pyridin-3-yl)benzyl)-2-cyano-6-fluorobenzo[d]thiazole-4-carboxamide Following the general procedure of Example 173 step 2, the reaction of N⁴-(4-(2-(2-aminopyridin-3-yl)-5-phenyl-3H-imidazo[4,5-b]pyridin-3-yl)benzyl)-6-fluorobenzo[d]thiazole-2,4-dicarboxamide (40 mg, 65 μmol) with POCl$_3$ was carried out. After purified by prep-HPLC (column: Phenomenex C18 150×25 mm×10 μm; mobile phase: [water (NH$_4$HCO$_3$)-ACN]; B %: 35%-60%, 8 min), N-(4-(2-(2-aminopyridin-3-yl)-5-phenyl-3H-imidazo[4,5-b]pyridin-3-yl)benzyl)-2-cyano-6-fluorobenzo[d]thiazole-4-carboxamide (Example 177, 11.4 mg, yield: 28%) was obtained as a yellow lyophilized powder. MS: m/z=597.3 [M+H]⁺. ¹H NMR (400 MHz, Dimethylsulfoxide-d$_6$) 9.60-9.55 (m, 1H), 8.46-8.42 (m, 1H), 8.26 (d, J=8.4 Hz, 1H), 8.07-7.94 (m, 6H), 7.59-7.57 (m, 2H), 7.50-7.43 (m, 4H), 7.41-7.36 (m, 1H), 7.24-7.21 (m, 1H), 6.93 (br s, 2H), 6.46-6.40 (m, 1H), 4.77 (d, J=5.6 Hz, 2H). ¹⁹F NMR (400 MHz, Dimethylsulfoxide-d$_6$) δ −109.8.

Example 178: N-(4-(5-(3-Acetamidophenyl)-2-(2-aminopyridin-3-yl)-3H-imidazo[4,5-b]pyridin-3-yl)benzyl)-2-cyano-5-fluorobenzo[d]thiazole-7-carboxamide

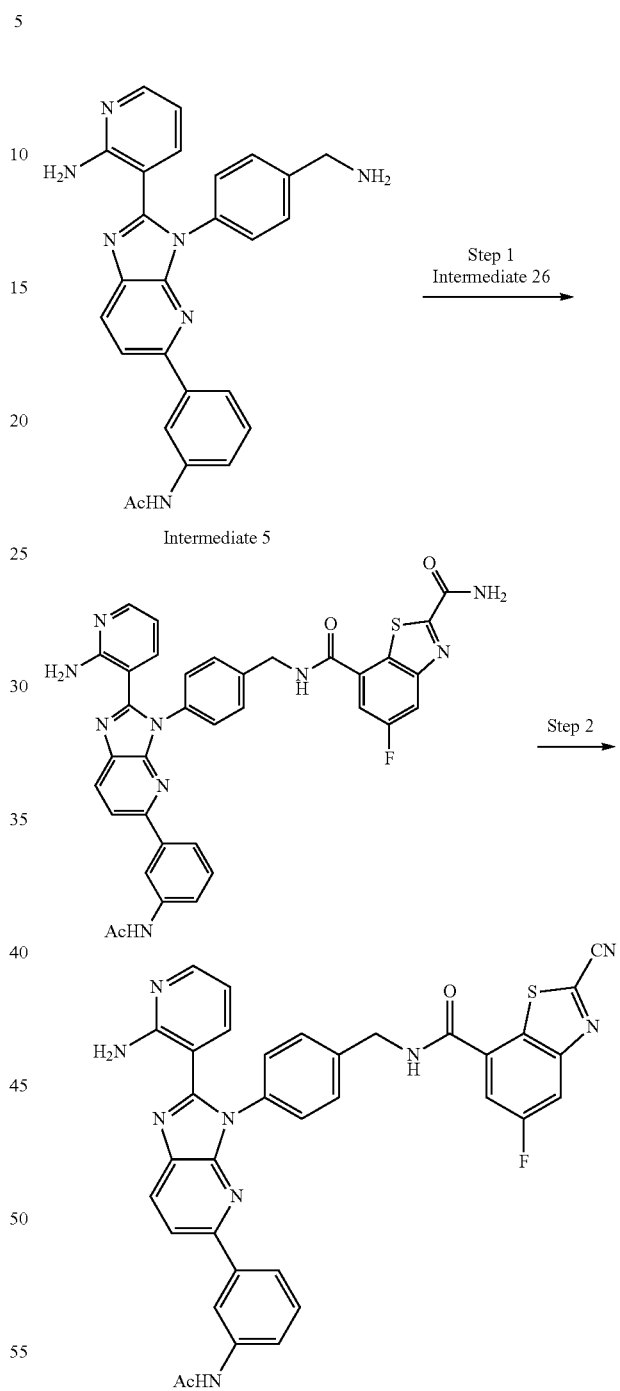

Example 178

Step 1: N⁷-(4-(5-(3-acetamidophenyl)-2-(2-aminopyridin-3-yl)-3H-imidazo[4,5-b]pyridin-3-yl)benzyl)-5-fluorobenzo[d]thiazole-2,7-dicarboxamide Following the general procedure of Example 173 step 1, the reaction of Intermediate 5 (200 mg, 445 μmol) with Intermediate 26 (106.9 mg, 445 μmol) was carried out. After purified by prep-HPLC (column: Phenomenex C18 150×25 mm×10 μm; mobile phase: [water (NH$_4$HCO$_3$)-ACN]; B %: 26%-56%, 8 min), N$^7$-(4-(5-(3-acetamidophenyl)-2-(2-aminopyridin-3-yl)-3H-imidazo[4,5-b]pyridin-3-yl)benzyl)-5-fluorobenzo[d]thiazole-2,7-dicarboxamide (30 mg, yield: 7.9%) was obtained as an off-white lyophilized powder. MS: m/z=672.4

Step 2: N-(4-(5-(3-Acetamidophenyl)-2-(2-aminopyridin-3-yl)-3H-imidazo[4,5-b]pyridin-3-yl)benzyl)-2-cyano-5-fluorobenzo[d]thiazole-7-carboxamide Following the general procedure of Example 173 step 2, the reaction of N$^7$-(4-(5-(3-acetamidophenyl)-2-(2-aminopyridin-3-yl)-3H-imidazo[4,5-b]pyridin-3-yl)benzyl)-5-fluorobenzo[d]thiazole-2,7-dicarboxamide (30 mg, 45 μmol) with POCl$_3$ was carried out. After purified by prep-HPLC (column: Phenomenex C18 150×25 mm×10 μm; mobile phase: [water (NH$_4$HCO$_3$)-ACN]; B %: 33%-63%, 14 min), N-(4-(5-(3-acetamidophenyl)-2-(2-aminopyridin-3-yl)-3H-imidazo[4,5-b]pyridin-3-yl)benzyl)-2-cyano-5-fluorobenzo[d]thiazole-7-carboxamide (Example 178, 3.4 mg, yield: 11%) was obtained as an off-white lyophilized powder. MS: m/z=654.2 [M+H]$^+$. $^1$H NMR (400 MHz, Methanol-d$_4$) δ 8.23-8.16 (m, 4H), 7.98 (dd, J=5.2, 1.6 Hz, 1H), 7.91 (d, J=8.4 Hz, 1H), 7.76-7.74 (m, 1H), 7.62-7.57 (m, 3H), 7.48 (d, J=8.4 Hz, 2H), 7.38-7.33 (m, 2H), 6.48 (dd, J=7.6, 4.8 Hz, 1H), 4.77 (s, 2H), 2.11 (s, 3H).

Example 179: N-(4-(5-(3-acetamidophenyl)-2-(2-aminopyridin-3-yl)-3H-imidazo[4,5-b]pyridin-3-yl)benzyl)-2-cyano-6-fluorobenzo[d]thiazole-4-carboxamide

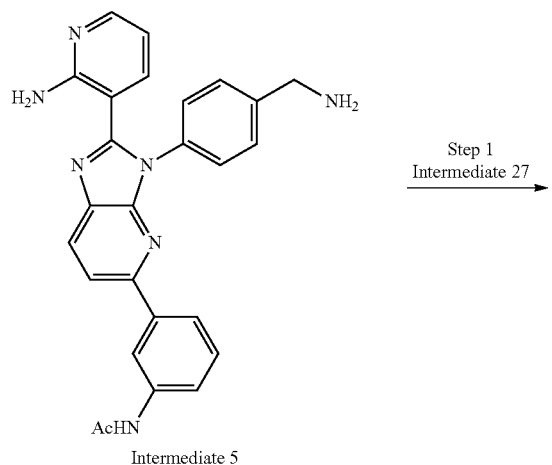

Intermediate 5

Step 1
Intermediate 27

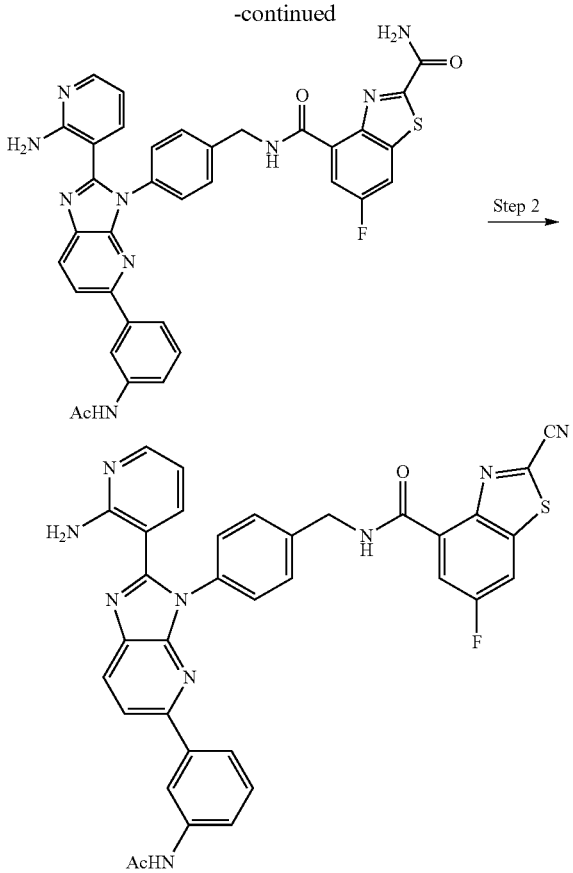

Example 179

Step 1: N$^4$-(4-(5-(3-Acetamidophenyl)-2-(2-aminopyridin-3-yl)-3H-imidazo[4,5-b]pyridin-3-yl)benzyl)-6-fluorobenzo[d]thiazole-2,4-dicarboxamide Following the general procedure of Example 173 step 1, the reaction of Intermediate 5 (50 mg, 111 μmol) with Intermediate 27 (26.7 mg, 111 μmol) was carried out. After purified by prep-HPLC (column: Welch Xtimate C18 150× 25 mm×5 μm; mobile phase: [water (ammonia hydroxide v/v)-ACN]; B %: 25%-55%, 2 min), N$^4$-(4-(5-(3-acetamidophenyl)-2-(2-aminopyridin-3-yl)-3H-imidazo[4,5-b]pyridin-3-yl)benzyl)-6-fluorobenzo[d]thiazole-2,4-dicarboxamide (30 mg, yield: 40%) was obtained as a yellow lyophilized powder. MS: m/z=672.5 [M+H]$^+$. $^1$H NMR (400 MHz, Dimethylsulfoxide-d$_6$) δ 10.09-10.04 (m, 2H), 9.15 (s, 1H), 8.39 (dd, J=7.6, 2.8 Hz, 1H), 8.31 (s, 1H), 8.27 (d, J=8.4 Hz, 1H), 8.12-8.06 (m, 2H), 7.98 (dd, J=4.8, 2.0 Hz, 1H), 7.83 (d, J=8.4 Hz, 1H), 7.71-7.67 (m, 1H), 7.65-7.62 (m, 1H), 7.51-7.44 (m, 4H), 7.39-7.34 (m, 1H), 7.22 (dd, J=7.6, 1.6 Hz, 1H), 6.85 (br s, 2H), 6.40 (dd, J=7.6, 4.8 Hz, 1H), 4.82 (d, J=6.0 Hz, 2H), 2.02 (s, 3H). $^{19}$F NMR (400 MHz, Dimethylsulfoxide-d$_6$) δ −112.7.

Step 2: N-(4-(5-(3-Acetamidophenyl)-2-(2-aminopyridin-3-yl)-3H-imidazo[4,5-b]pyridin-3-yl)benzyl)-2-cyano-6-fluorobenzo[d]thiazole-4-carboxamide Following the general procedure of Example 173 step 2, the reaction of N4-(4-(5-(3-acetamidophenyl)-2-(2-aminopyridin-3-yl)-3H-imidazo[4,5-b]pyridin-3-yl)benzyl)-6-fluorobenzo[d]thiazole-2,4-dicarboxamide (30 mg, 45 μmol) with POCl₃ was carried out. After purified by prep-HPLC (column: Waters Xbridge BEH C18 150×25 mm×5 μm; mobile phase: [water-ACN]; B %: 43%-73%, 10 min), N-(4-(5-(3-acetamidophenyl)-2-(2-aminopyridin-3-yl)-3H-imidazo[4,5-b]pyridin-3-yl)benzyl)-2-cyano-6-fluorobenzo[d]thiazole-4-carboxamide (Example 179, 6.1 mg, yield: 20%) was obtained as a light-yellow lyophilized powder. MS: m/z=654.4 [M+H]⁺. ¹H NMR (400 MHz, Methanol-d₄) δ 8.21-8.13 (m, 4H), 7.98-7.90 (m, 1H), 7.91 (d, J=8.0 Hz, 1H), 7.77-7.74 (m, 1H), 7.67-7.61 (m, 3H), 7.48 (d, J=8.4 Hz, 2H), 7.39-7.32 (m, 2H), 6.51 (dd, J=7.6, 4.8 Hz, 1H), 4.79 (s, 2H), 2.12 (s, 3H). ¹⁹F NMR (400 MHz, Methanol-d₄) δ −111.1.

Example 180: 7-(4-(4-(2-(2-Aminopyridin-3-yl)-5-phenyl-3H-imidazo[4,5-b]pyridin-3-yl)benzyl)piperazine-1-carbonyl)-5-fluorobenzo[d]thiazole-2-carbonitrile

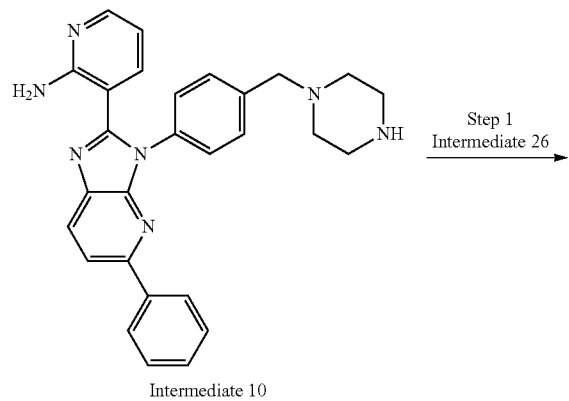

Step 1: 7-(4-(4-(2-(2-Aminopyridin-3-yl)-5-phenyl-3H-imidazo[4,5-b]pyridin-3-yl)benzyl)piperazine-1-carbonyl)-5-fluorobenzo[d]thiazole-2-carboxamide Following the general procedure of Example 173 step 1, the reaction of Intermediate 10 (200 mg, 433 μmol) with Intermediate 26 (104 mg, 433 μmol) was carried out. After purified by prep-HPLC (column: Waters xbridge 150×25 mm 10 μm; mobile phase: [water (NH₄HCO₃)-ACN]; B %: 35%-65%, 11 min), 7-(4-(4-(2-(2-aminopyridin-3-yl)-5-phenyl-3H-imidazo[4,5-b]pyridin-3-yl)benzyl)piperazine-1-carbonyl)-5-fluorobenzo[d]thiazole-2-carboxamide (40 mg, yield: 13%) was obtained as an off-white solid. MS: m/z=684.5 [M+H]⁺. ¹H NMR (400 MHz, Dimethylsulfoxide-d₆) δ 8.57 (s, 1H), 8.27 (d, J=8.4 Hz, 1H), 8.17 (s, 1H), 8.07 (dd, J=9.2, 2.4 Hz, 1H), 8.04-8.00 (m, 2H), 8.00-7.97 (m, 2H), 7.63 (dd, J=9.2, 2.4 Hz, 1H), 7.53-7.49 (m, 2H), 7.48-7.43 (m, 4H), 7.42-7.36 (m, 1H), 7.15 (dd, J=7.6, 1.6 Hz, 1H), 7.01 (br s, 2H), 6.38 (dd, J=7.6, 4.8 Hz, 1H), 3.67-3.58 (m, 4H), 3.32-3.27 (m, 2H), 2.63-2.55 (m, 2H), 2.47-2.39 (m, 2H). ¹⁹F NMR (400 MHz, Dimethylsulfoxide-d₆) δ −113.8.

Step 2: 7-(4-(4-(2-(2-Aminopyridin-3-yl)-5-phenyl-3H-imidazo[4,5-b]pyridin-3-yl)benzyl)piperazine-1-carbonyl)-5-fluorobenzo[d]thiazole-2-carbonitrile Following the general procedure of Example 173 step 2, the reaction of 7-(4-(4-(2-(2-aminopyridin-3-yl)-5-phenyl-3H-imidazo[4,5-b]pyridin-3-yl)benzyl)piperazine-1-carbonyl)-5-fluorobenzo[d]thiazole-2-carboxamide (30 mg, 44 μmol) with POCl₃ was carried out. After purified by prep-HPLC (column: Phenomenex C18 150×25 mm×10 μm; mobile phase: [water (NH₄HCO₃)-ACN]; B %: 48%-78%, 8 min), 7-(4-(4-(2-(2-aminopyridin-3-yl)-5-phenyl-3H-imidazo[4,5-b]pyridin-3-yl)benzyl)piperazine-1-carbonyl)-5-fluorobenzo[d]thiazole-2-carbonitrile (Example 180, 3.8 mg, yield: 13%) was obtained as a light-yellow lyophilized powder. MS: m/z=666.4 [M+H]⁺. ¹H NMR (400 MHz, Dimethylsulfoxide-d₆) δ 8.34 (dd, J=8.8, 2.4 Hz, 1H), 8.27 (d, J=8.4 Hz, 1H), 8.04-7.96 (m, 4H), 7.85 (dd, J=9.2, 2.0 Hz, 1H), 7.53-7.49 (m, 2H), 7.49-7.43 (m, 4H), 7.42-7.36 (m, 1H), 7.16 (dd, J=7.6, 1.8 Hz, 1H), 7.01 (br s, 2H), 6.38 (dd, J=7.6, 4.8 Hz, 1H), 3.75-3.59 (m, 6H), 3.44-3.40 (m, 4H). ¹⁹F NMR (400 MHz, Dimethylsulfoxide-d₆) δ −112.4.

Example 181: 4-(4-(4-(2-(2-Aminopyridin-3-yl)-5-phenyl-3H-imidazo[4,5-b]pyridin-3-yl)benzyl)piperazine-1-carbonyl)-6-fluorobenzo[d]thiazole-2-carbonitrile

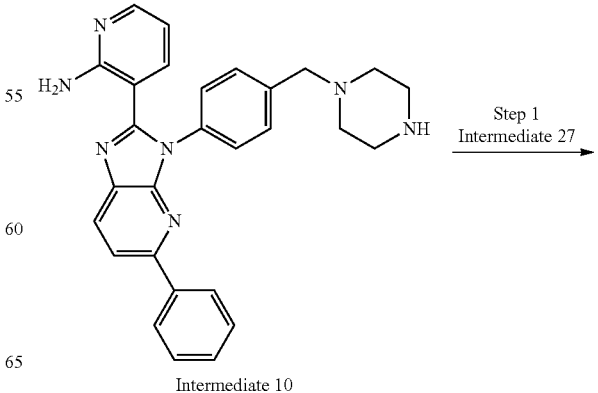

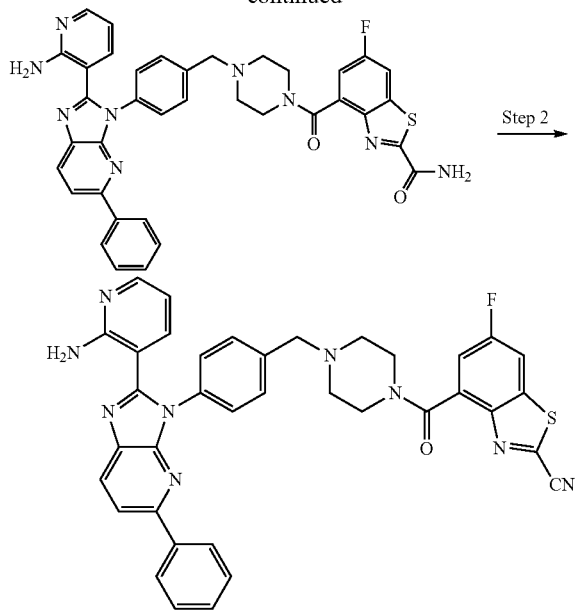

Example 181

Step 1: 4-(4-(4-(2-(2-aminopyridin-3-yl)-5-phenyl-3H-imidazo[4,5-b]pyridin-3-yl)benzyl)piperazine-1-carbonyl)-6-fluorobenzo[d]thiazole-2-carboxamide Following the general procedure of Example 173 step 1, the reaction of Intermediate 10 (50 mg, 108 μmol) with Intermediate 27 (26 mg, 108 μmol) was carried out. After purified by prep-HPLC (column: Welch Xtimate C18 150× 25 mm×5 μm; mobile phase: [water (NH$_3$H$_2$O)-ACN]; B %: 35%-65%, 8 min), 4-(4-(4-(2-(2-aminopyridin-3-yl)-5-phenyl-3H-imidazo[4,5-b]pyridin-3-yl)benzyl)piperazine-1-carbonyl)-6-fluorobenzo[d]thiazole-2-carboxamide (15.3 mg yield: 20%) was obtained as light yellow lyophilized powder. MS: m/z=684.4 [M+H]$^+$. $^1$H NMR (400 MHz, Dimethylsulfoxide-d$_6$) δ 8.28-8.24 (m, 2H), 8.22-8.16 (m, 2H), 8.03-7.96 (m, 4H), 7.53-7.36 (m, 8H), 7.15 (d, J=7.2 Hz, 1H), 7.01 (br s, 2H), 6.37 (dd, J=7.6, 4.8 Hz, 1H), 4.00-3.86 (m, 1H), 3.80-3.47 (m, 4H), 3.24-3.11 (m, 3H), 2.81-2.70 (m, 1H), 2.28-2.16 (m, 1H). $^{19}$F NMR (400 MHz, Dimethylsulfoxide-d$_6$) δ −112.8.

Step 2: 4-(4-(4-(2-(2-Aminopyridin-3-yl)-5-phenyl-3H-imidazo[4,5-b]pyridin-3-yl)benzyl)piperazine-1-carbonyl)-6-fluorobenzo[d]thiazole-2-carbonitrile Following the general procedure of Example 173 step 2, the reaction of 4-(4-(4-(2-(2-aminopyridin-3-yl)-5-phenyl-3H-imidazo[4,5-b]pyridin-3-yl)benzyl)piperazine-1-carbonyl)-6-fluorobenzo[d]thiazole-2-carboxamide (30 mg, 44 μmol) with POCl$_3$ was carried out. After purified by prep-HPLC (column: Phenomenex C18 150×25 mm×10 μm; mobile phase: [water (NH$_4$HCO$_3$)-ACN]; B %: 50%-80%, 8 min), 4-(4-(4-(2-(2-aminopyridin-3-yl)-5-phenyl-3H-imidazo[4,5-b]pyridin-3-yl)benzyl)piperazine-1-carbonyl)-6-fluorobenzo[d]thiazole-2-carbonitrile (Example 181, 4.8 mg, yield: 16%) was obtained as light-yellow lyophilized powder. MS: m/z=666.1 [M+H]$^+$. $^1$H NMR (400 MHz, Methanol-d$_4$) δ 8.19 (d, J=8.4 Hz, 1H), 8.06 (dd, J=8.0, 2.4 Hz, 1H), 8.04-8.00 (m, 2H), 7.97-7.91 (m, 2H), 7.58-7.52 (m, 3H), 7.47-7.33 (m, 5H), 7.32 (dd, J=7.6, 2.0 Hz, 1H), 6.46 (dd, J=7.6, 4.8 Hz, 1H), 4.60 (s, 2H), 3.99-3.84 (m, 2H), 3.70 (s, 2H), 2.73-2.65 (m, 2H), 2.53-2.43 (m, 2H). $^{19}$F NMR (400 MHz, Methanol-d$_4$) δ −111.0.

Example 182: N-(1-(4-(2-(2-aminopyridin-3-yl)-5-phenyl-3H-imidazo[4,5-b]pyridin-3-yl)benzyl)piperidin-4-yl)-2-cyano-5-fluorobenzo[d]thiazole-7-carboxamide

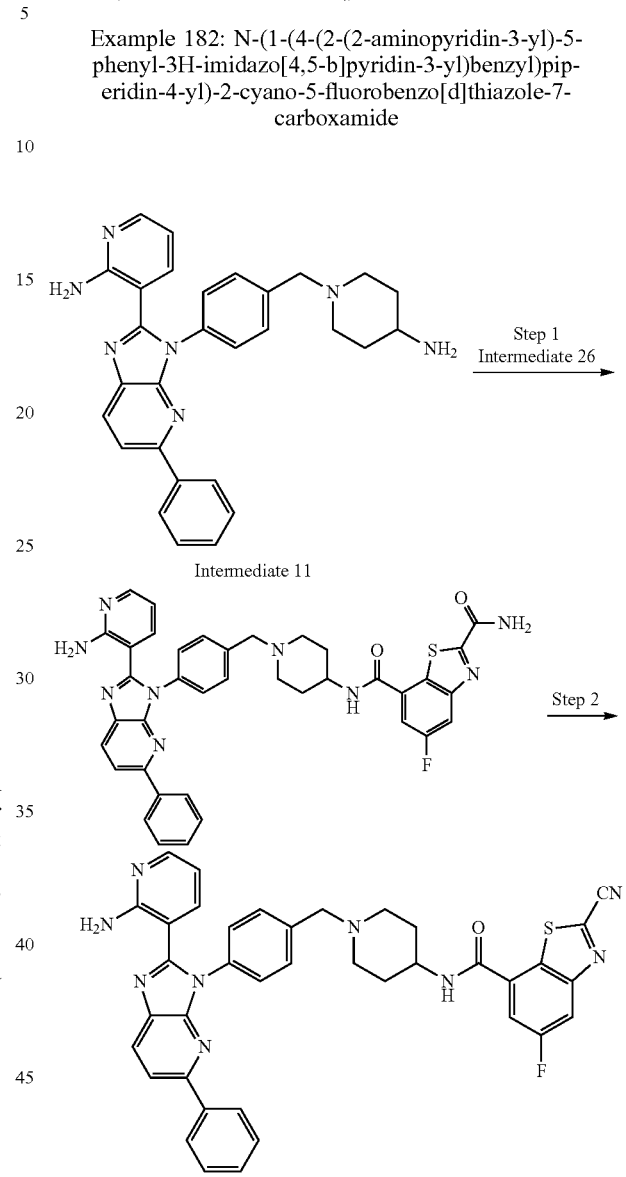

Example 182

Step 1: N$^7$-(1-(4-(2-(2-aminopyridin-3-yl)-5-phenyl-3H-imidazo[4,5-b]pyridin-3-yl)benzyl)piperidin-4-yl)-5-fluorobenzo[d]thiazole-2,7-dicarboxamide Following the general procedure of Example 173 step 1, the reaction of Intermediate 11 (50 mg, 105 μmol) with Intermediate 26 (25.3 mg, 105 μmol) was carried out. After purified by prep-HPLC (column: Welch Xtimate C18 150× 25 mm×5 μm; mobile phase: [water (NH$_3$H$_2$O)-ACN]; B %: 38%-68%, 8 min), N$^7$-(1-(4-(2-(2-aminopyridin-3-yl)-5-phenyl-3H-imidazo[4,5-b]pyridin-3-yl)benzyl)piperidin-4-yl)-5-fluorobenzo[d]thiazole-2,7-dicarboxamide (8.6 mg, yield: 11%) was obtained as pink solid. MS: m/z=698.2 [M+H]$^+$. $^1$H NMR (400 MHz, Dimethylsulfoxide-d$_6$) δ 8.77 (d, J=8.0 Hz, 1H), 8.46 (s, 1H), 8.29-8.24 (m, 2H), 8.14 (dd, J=8.8, 2.0 Hz, 1H), 8.08 (s, 1H), 8.05-7.97 ((m, 4H), 7.53-7.45 (m, 6H), 7.42-7.37 (m, 1H), 7.17 (dd, J=7.6, 2.0 Hz, 1H), 7.04 (br s, 2H), 6.39 (dd, J=7.6, 4.8 Hz, 1H), 3.93-3.85 (m, 1H), 3.61 (s, 2H), 2.95-2.87 (m, 2H), 2.18-2.09 (m, 2H), 1.92-1.85 (m, 2H), 1.72-1.62 (m, 2H). $^{19}$F NMR (400 MHz, Dimethylsulfoxide-d$_6$) δ −114.6.

Step 2: N-(1-(4-(2-(2-Aminopyridin-3-yl)-5-phenyl-3H-imidazo[4,5-b]pyridin-3-yl)benzyl)piperidin-4-yl)-2-cyano-5-fluorobenzo[d]thiazole-7-carboxamide Following the general procedure of Example 173 step 2, the reaction of N$^7$-(1-(4-(2-(2-aminopyridin-3-yl)-5-phenyl-3H-imidazo[4,5-b]pyridin-3-yl)benzyl)piperidin-4-yl)-5-fluorobenzo[d]thiazole-2,7-dicarboxamide (20 mg, 29 μmol) was carried out. After purified by prep-HPLC (column: Phenomenex C18 150×25 mm×10 μm; mobile phase: [water (NH$_4$HCO$_3$)-ACN]; B %: 50%-80%, 8 min), N-(1-(4-(2-(2-aminopyridin-3-yl)-5-phenyl-3H-imidazo[4,5-b]pyridin-3-yl)benzyl)piperidin-4-yl)-2-cyano-5-fluorobenzo[d]thiazole-7-carboxamide (Example 182, 3.7 mg, yield: 18%) was obtained as off-white lyophilized powder. MS: m/z=680.2 [M+H]$^+$. $^1$H NMR (400 MHz, Dimethylsulfoxide-d$_6$) δ $^1$H NMR (400 MHz, Dimethylsulfoxide-d$_6$) δ 9.01 (d, J=6.8 Hz, 1H), 8.41 (d, J=7.2 Hz, 1H), 8.27 (d, J=8.0 Hz, 1H), 8.07-7.90 (m, 6H), 7.54-7.43 (m, 5H), 7.39 (d, J=7.2 Hz, 1H), 7.17 (d, J=6.4 Hz, 1H), 7.00 (br s, 2H), 6.44-6.34 (m, 1H), 4.06-3.94 (m, 2H), 3.64-3.62 (m, 1H), 2.96-2.77 (m, 4H), 2.03-1.92 (m, 2H), 1.79-1.60 (m, 2H). $^{19}$F NMR (400 MHz, Dimethylsulfoxide-d$_6$) δ −109.8.

Example 183: N-(1-(4-(2-(2-aminopyridin-3-yl)-5-phenyl-3H-imidazo[4,5-b]pyridin-3-yl)benzyl)piperidin-4-yl)-2-cyano-6-fluorobenzo[d]thiazole-4-carboxamide

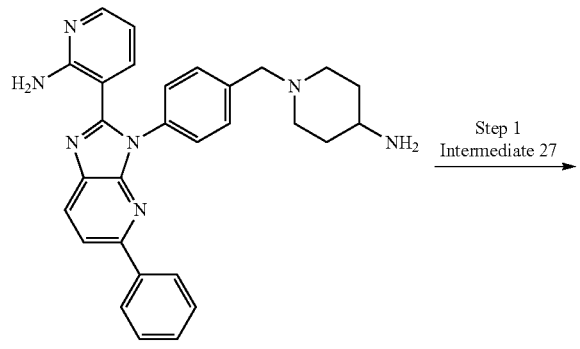

Intermediate 11

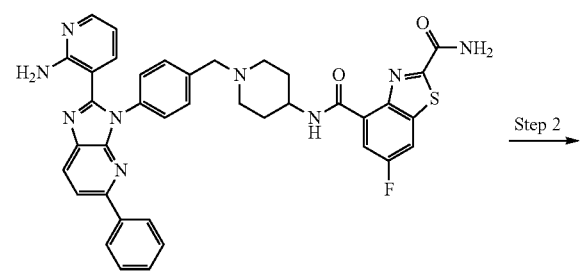

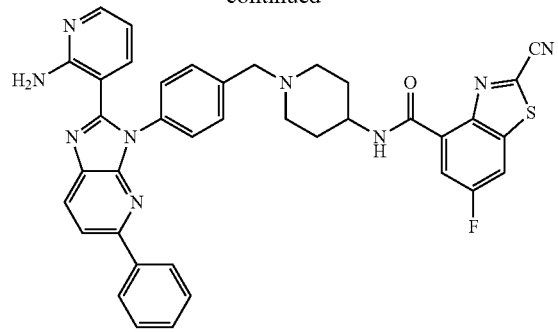

Example 183

Step 1: N$^4$-(1-(4-(2-(2-aminopyridin-3-yl)-5-phenyl-3H-imidazo[4,5-b]pyridin-3-yl)benzyl)piperidin-4-yl)-6-fluorobenzo[d]thiazole-2,4-dicarboxamide Following the general procedure of Example 173 step 1, the reaction of Intermediate 11 (50 mg, 105 μmol) with Intermediate 27 (25.2 mg, 105 μmol) was carried out. After purified by prep-HPLC (column: Waters Xbridge BEH C18 100×30 mm×10 μm; mobile phase: [water (ammonia hydroxide v/v)-ACN]; B %: 46%-76%, 2 min), N$^4$-(1-(4-(2-(2-aminopyridin-3-yl)-5-phenyl-3H-imidazo[4,5-b]pyridin-3-yl)benzyl)piperidin-4-yl)-6-fluorobenzo[d]thiazole-2,4-dicarboxamide (10.5 mg, yield: 14%) was obtained as a light-yellow lyophilized powder. MS: m/z=698.2 [M+H]$^+$. $^1$H NMR (400 MHz, Dimethylsulfoxide-d$_6$) δ 9.20 (d, J=7.6 Hz, 1H), 8.67 (s, 1H), 8.36-8.26 (m, 3H), 8.05-7.97 (m, 5H), 7.53-7.45 (m, 6H), 7.42-7.38 (m, 1H), 7.16 (dd, J=7.6, 1.8 Hz, 1H), 7.04 (br s, 2H), 6.38 (dd, J=7.6, 4.8 Hz, 1H), 4.02-3.89 (m, 1H), 3.60 (s, 2H), 2.95-2.84 (m, 2H), 2.22-2.11 (m, 2H), 1.98-1.84 (m, 4H). $^{19}$F NMR (400 MHz, Dimethylsulfoxide-d$_6$) δ −112.7.

Step 2: N-(1-(4-(2-(2-aminopyridin-3-yl)-5-phenyl-3H-imidazo[4,5-b]pyridin-3-yl)benzyl)piperidin-4-yl)-2-cyano-6-fluorobenzo[d]thiazole-4-carboxamide Following the general procedure of Example 173 step 2, the reaction of N$^4$-(1-(4-(2-(2-aminopyridin-3-yl)-5-phenyl-3H-imidazo[4,5-b]pyridin-3-yl)benzyl)piperidin-4-yl)-6-fluorobenzo[d]thiazole-2,4-dicarboxamide (40 mg, 57 μmol) with POCl$_3$ was carried out. After purified by prep-HPLC (column: Phenomenex C18 150×25 mm×10 μm; mobile phase: [water (NH$_4$HCO$_3$)-ACN]; B %: 50%-80%, 8 min), N-(1-(4-(2-(2-aminopyridin-3-yl)-5-phenyl-3H-imidazo[4,5-b]pyridin-3-yl)benzyl)piperidin-4-yl)-2-cyano-6-fluorobenzo[d]thiazole-4-carboxamide (Example 183, 14.6 mg, yield: 37%) was obtained as an off-white yellow lyophilized powder. MS: m/z=680.2 [M+H]$^+$. $^1$H NMR (400 MHz, Dimethylsulfoxide-d$_6$) δ 8.97 (d, J=7.6 Hz, 1H), 8.46 (dd, J=9.6, 1.6 Hz, 1H), 8.39-8.33 (m, 1H), 8.25 (d, J=8.4 Hz, 1H), 8.04-7.95 (m, 4H), 7.52-7.48 (m, 2H), 7.48-7.43 (m, 4H), 7.41-7.36 (m, 1H), 7.18-7.12 (m, 1H), 7.03 (br s, 2H), 6.37 (dd, J=7.6, 4.8 Hz, 1H), 3.94-3.82 (m, 1H), 3.61 (s, 2H), 2.96-2.85 (m, 2H), 2.19-2.08 (m, 2H), 1.93-1.83 (m, 2H), 1.74-1.61 (m, 2H). $^{19}$F NMR (400 MHz, Dimethylsulfoxide-d$_6$) δ −113.04.

Example 184: 5-(4-(4-(2-(2-aminopyridin-3-yl)-5-phenyl-3H-imidazo[4,5-b]pyridin-3-yl)benzyl)piperazine-1-carbonyl)benzo[d]thiazole-2-carbonitrile Step 1: 5-(4-(4-(2-(2-Aminopyridin-3-yl)-5-phenyl-3H-imidazo[4,5-b]pyridin-3-yl)benzyl)piperazine-1-carbonyl)benzo[d]thiazole-2-carboxamide

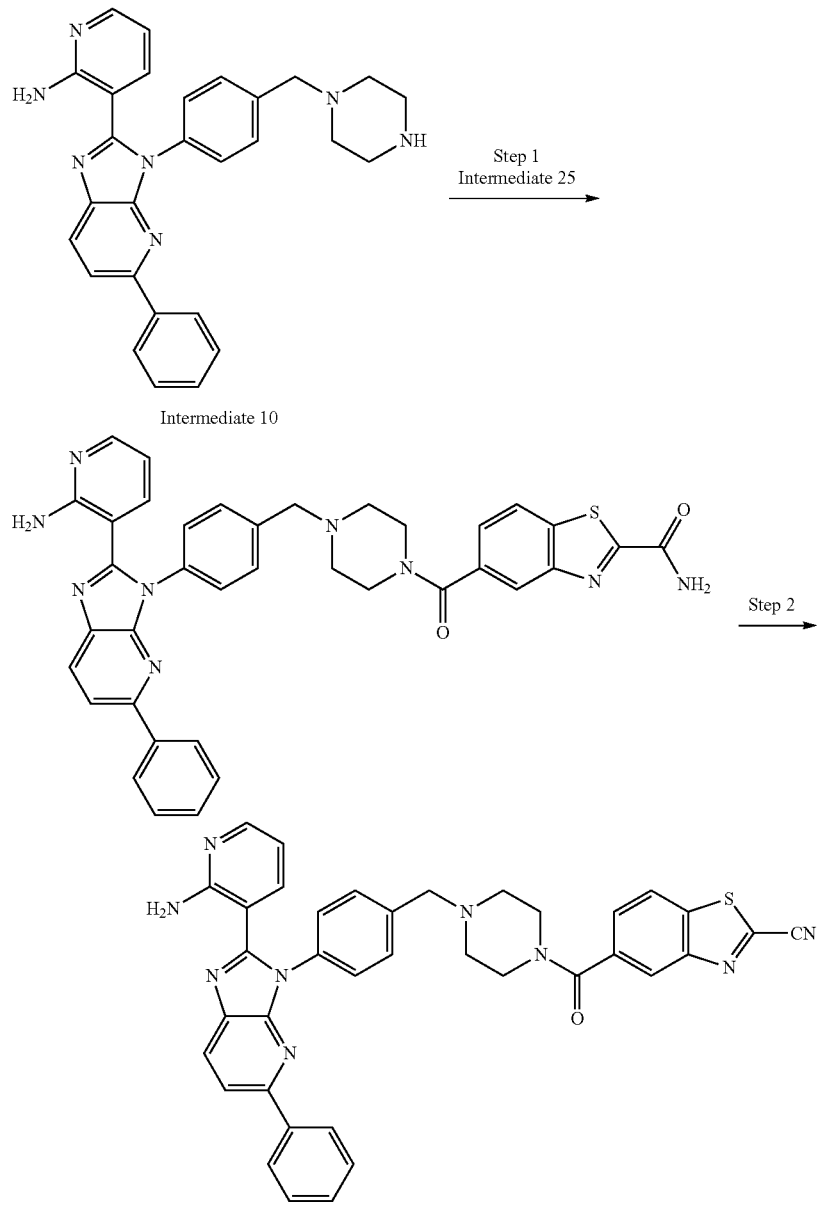

Following the general procedure of Example 173 step 1, the reaction of Intermediate 10 (360 mg, 778 μmol) with Intermediate 25 (208 mg, 934 μmol) was carried out. After purified by prep-HPLC (column: Waters Xbridge 150*25 mm*5 μm; mobile phase: [water (NH$_4$HCO$_3$)-ACN]; B %: 34%-64%, 8 min), 5-(4-(4-(2-(2-aminopyridin-3-yl)-5-phenyl-3H-imidazo[4,5-b]pyridin-3-yl)benzyl)piperazine-1-carbonyl)benzo[d]thiazole-2-carboxamide (64.7 mg, yield: 12%) was obtained as a yellow solid. MS: m/z=666.1 [M+H]$^+$. $^1$H NMR (400 MHz, Chloroform-d) δ 8.18-8.10 (m, 2H), 8.08-7.96 (m, 3H), 7.80 (d, J=8.4 Hz, 1H), 7.58 (dd, J=8.4, 1.2 Hz, 1H), 7.50 (d, J=8.0 Hz, 2H), 7.45-7.39 (m, 4H), 7.38-7.34 (m, 1H), 7.30 (s, 1H), 7.09 (dd, J=7.6, 1.6 Hz, 1H), 6.64 (br s, 2H), 6.35 (dd, J=7.6, 4.8 Hz, 1H), 5.76 (s, 1H), 4.03-3.77 (m, 2H), 3.68 (s, 2H), 3.62-3.41 (m, 2H), 2.71-2.43 (m, 4H).

Step 2: 5-(4-(4-(2-(2-Aminopyridin-3-yl)-5-phenyl-3H-imidazo[4,5-b]pyridin-3-yl)benzyl)piperazine-1-carbonyl)benzo[d]thiazole-2-carbonitrile Following the general procedure of Example 173 step 2, the reaction of 5-(4-(4-(2-(2-aminopyridin-3-yl)-5-phenyl-3H-imidazo[4,5-b]pyridin-3-yl)benzyl)piperazine-1-carbonyl)benzo[d]thiazole-2-carboxamide (50 mg, 45 µmol) with POCl$_3$ (173 mg, 1.0 mmol) was carried out. The crude product was purified by reversed-phase HPLC (0.1% NH$_3$HCO$_3$), 5-(4-(4-(2-(2-aminopyridin-3-yl)-5-phenyl-3H-imidazo[4,5-b]pyridin-3-yl)benzyl)piperazine-1-carbonyl)benzo[d]thiazole-2-carbonitrile (Example 184, 4.5 mg, yield: 15%) was obtained as a light-green solid. MS: m/z=648.4 [M+H]$^+$. $^1$H NMR (400 MHz, Chloroform-d) δ 8.26 (s, 1H), 8.14 (d, J=8.4 Hz, 1H), 8.07-8.03 (m, 2H), 8.00 (d, J=7.2 Hz, 2H), 7.81 (d, J=8.4 Hz, 1H), 7.72 (dd, J=8.4, 1.2 Hz, 1H), 7.51 (d, J=8.0 Hz, 2H), 7.46-7.40 (m, 4H), 7.38 (d, J=7.2 Hz, 1H), 7.13-7.09 (m, 1H), 6.83 (br s, 2H), 6.36 (dd, J=7.6, 5.2 Hz, 1H), 4.00-3.82 (m, 2H), 3.67 (s, 2H), 3.60-3.43 (m, 2H), 2.69-2.47 (m, 4H).

Example 185: N-(1-(4-(2-(2-aminopyridin-3-yl)-5-phenyl-3H-imidazo[4,5-b]pyridin-3-yl)benzyl)piperidin-4-yl)-2-cyanobenzo[d]thiazole-5-carboxamide Step 1: N$^3$-(1-(4-(2-(2-Aminopyridin-3-yl)-5-phenyl-3H-imidazo[4,5-b]pyridin-3-yl)benzyl)piperidin-4-yl)benzo[d]thiazole-2,5-dicarboxamide

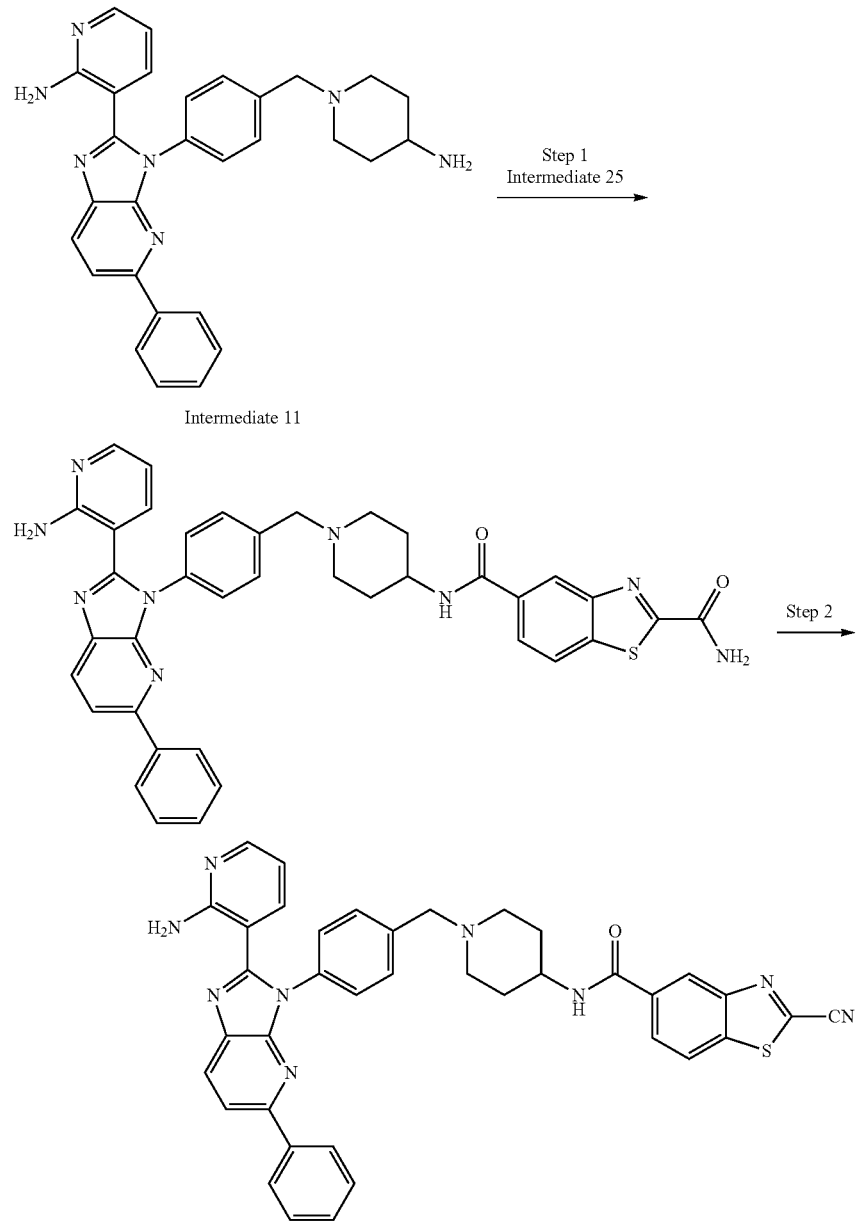

Example 185

Following the general procedure of Example 173 step 1, the reaction of Intermediate 11 (370 mg, 778 μmol) with Intermediate 25 (208 mg, 934 μmol) was carried out. After purified by prep-HPLC (column: Phenomenex C18 150*25 mm*10 μm; mobile phase: [water (NH₄HCO₃)-ACN]; B %: 33%-63%, 8 min), N-(1-(4-(2-(2-aminopyridin-3-yl)-5-phenyl-3H-imidazo[4,5-b]pyridin-3-yl)benzyl)piperidin-4-yl)benzo[d]thiazole-2,5-dicarboxamide (39.7 mg, yield. 7.5%) was obtained as a yellow solid. MS: m/z=680.2 [M+H]⁺. ¹H NMR (400 MHz, Chloroform-d) δ 8.46 (d, J=1.2 Hz, 1H), 8.13 (d, J=8.4 Hz, 1H), 8.07-7.93 (m, 5H), 7.81 (d, J=8.4 Hz, 1H), 7.51 (d, J=8.0 Hz, 2H), 7.46-7.40 (m, 4H), 7.39-7.35 (m, 1H), 7.31 (br s, 1H), 7.10 (dd, J=7.6, 1.6 Hz, 1H), 6.61 (br s, 2H), 6.36 (dd, J=7.6, 4.8 Hz, 1H), 6.16 (d, J=7.6 Hz, 1H), 5.78 (s, 1H), 4.15-4.07 (m, 1H), 3.66 (s, 2H), 2.97 (d, J=11.6 Hz, 2H), 2.31 (t, J=10.8 Hz, 2H), 2.13 (d, J=10.0 Hz, 2H), 1.74-1.68 (m, 2H).

Step 2: N-(1-(4-(2-(2-aminopyridin-3-yl)-5-phenyl-3H-imidazo[4,5-b]pyridin-3-yl)benzyl)piperidin-4-yl)-2-cyanobenzo[d]thiazole-5-carboxamide Following the general procedure of Example 173 step 2, the reaction of N⁵-(1-(4-(2-(2-aminopyridin-3-yl)-5-phenyl-3H-imidazo[4,5-b]pyridin-3-yl)benzyl)piperidin-4-yl)benzo[d]thiazole-2,5-dicarboxamide (24 mg, 35 μmol) with POCl₃ (133 mg, 865 μmol) was carried out. The crude product was purified by reversed-phase HPLC (0.1% NH₃HCO₃), N-(1-(4-(2-(2-aminopyridin-3-yl)-5-phenyl-3H-imidazo[4,5-b]pyridin-3-yl)benzyl)piperidin-4-yl)-2-cyanobenzo[d]thiazole-5-carboxamide (Example 185, 3.9 mg, yield: 17%) was obtained as a yellow solid. MS: m/z=662.5 [M+H]⁺. ¹H NMR (400 MHz, Chloroform-d) δ 8.55 (s, 11H), 8.14 (d, J=8.4 Hz, 11H), 8.10-8.05 (m, 3H), 8.02 (d, J=7.2 Hz, 2H), 7.81 (d, J=8.4 Hz, 1H), 7.57-7.51 (m, 2H), 7.47-7.35 (m, 5H), 7.10 (dd, J=7.6, 1.6 Hz, 1H), 6.61 (br s, 2H), 6.37 (dd, J=7.6, 4.8 Hz, 1H), 6.28-6.13 (m, 1H), 4.19-4.08 (m, 1H), 3.71 (s, 2H), 3.10-2.95 (m, 2H), 2.42-2.31 (m, 2H), 2.17-2.11 (m, 2H), 1.83-1.74 (m, 2H).

Example 186: 6-((4-(2-(2-Aminopyridin-3-yl)-5-phenyl-3H-imidazo[4,5-b]pyridin-3-yl)benzyl)amino)picolinonitrile

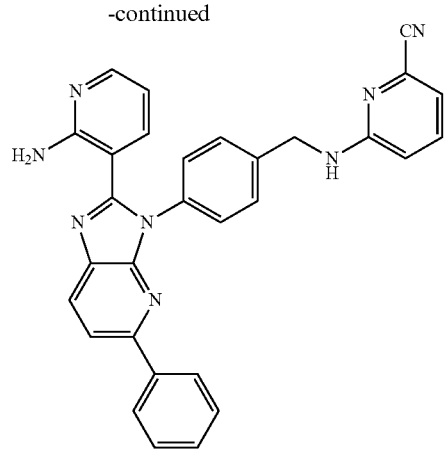

Example 186

To a solution of Intermediate 4 (100 mg, 255 μmol) and 6-fluoropyridine-2-carbonitrile (34.2 mg, 280 μmol) in NMP (2 mL) was added DIEA (164 mg, 1.27 mmol). The mixture was stirred under microwave at 135° C. for 1 hr. The reaction was filtered and concentrated under reduced pressure to give a residue. The crude product was purified by prep-HPLC (column: Phenomenex C18 150*25 mm*10 μm; mobile phase: [water (NH₄HCO₃)-ACN]; B %: 47%-77%, 8 min), 6-((4-(2-(2-aminopyridin-3-yl)-5-phenyl-3H-imidazo[4,5-b]pyridin-3-yl)benzyl)amino)picolinonitrile (Example 186, 53 mg, yield: 42%) was obtained as a light-yellow solid. MS: m/z=495.1 [M+H]⁺. ¹H NMR (400 MHz, Dimethylsulfoxide-d₆) δ 8.27 (d, J=8 Hz, 1H), 8.04-7.98 (m, 4H), 7.79 (t, J=6.0 Hz, 1H), 7.58 (dd, J=8.8, 7.2 Hz, 1H), 7.52-7.45 (m, 6H), 7.41-7.38 (m, 1H), 7.2 (dd, J=7.6, 1.6 Hz, 1H), 7.12 (d, J=6.4 Hz, 1H), 6.99 (br s, 2H), 6.88 (d, J=8.4 Hz, 1H), 6.40 (dd, J=7.6, 4.8 Hz, 1H), 4.6 (d, J=6.0 Hz, 2H).

Example 187: 5-((4-(2-(2-Aminopyridin-3-yl)-5-phenyl-3H-imidazo[4,5-b]pyridin-3-yl)benzyl)amino)picolinonitrile

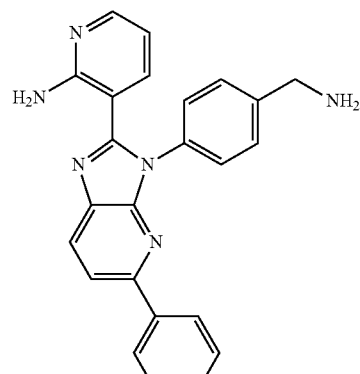

Intermediate 4

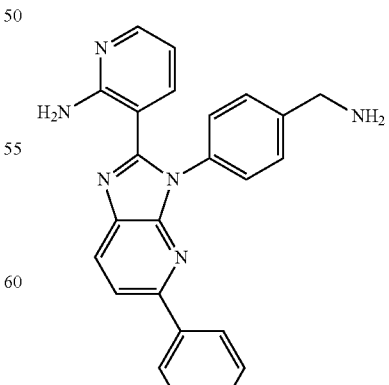

Intermediate 4

1255
-continued

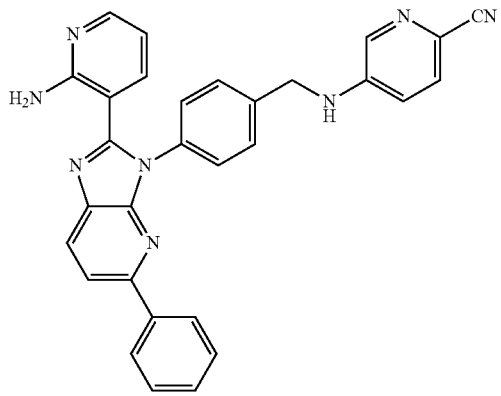

Example 187

1256
-continued

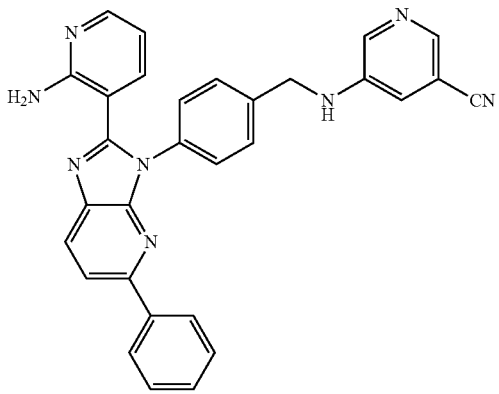

Example 188

To a solution of Intermediate 4 (150 mg, 382 μmol) and 5-fluoropyridine-2-carbonitrile (51.3 mg, 420 μmol) in DMSO (3 mL) was added DIEA (247 mg, 1.91 mmol). The mixture was stirred at 100° C. for 12 hr. The reaction was filtered and concentrated under reduced pressure to give a residue. The crude product was purified by prep-HPLC (column. Waters xbridge 150*25 mm 10 μm; mobile phase: [water (NH$_4$HCO$_3$)-ACN]; B %: 36%-66%, 8 min), 5-((4-(2-(2-aminopyridin-3-yl)-5-phenyl-3H-imidazo[4,5-b]pyridin-3-yl)benzyl)amino)picolinonitrile (Example 187, 22 mg, yield: 11.6%) was obtained as a light-yellow solid. MS: m/z=495.1 [M+H]$^+$. $^1$H NMR (400 MHz, Dimethylsulfoxide-d$_6$) δ 8.26 (d, J=8.4 Hz, 1H), 8.14 (d, J=2.4 Hz, 1H), 8.02-7.97 (m, 4H), 7.67-7.61 (m, 2H), 7.54-7.39 (m, 7H), 7.16 (dd, J=7.6, 2 Hz, 1H), 7.02-7.01 (m, 1H), 6.8 (br s, 2H), 6.37 (dd, J=7.6, 4.8 Hz, 1H), 4.51 (d, J=6.0 Hz, 2H).

Example 188: 5-((4-(2-(2-Aminopyridin-3-yl)-5-phenyl-3H-imidazo[4,5-b]pyridin-3-yl)benzyl) amino)nicotinonitrile To a solution of Intermediate 4 (150 mg, 382 μmol) and 5-fluoropyridine-3-carbonitrile (56.0 mg, 459 μmol) in DMSO (3 mL) was added DIEA (247 mg, 1.91 mmol). The mixture was stirred at 100° C. for 12 hr. The reaction was filtered and concentrated under reduced pressure to give a residue. The crude product was purified by prep-HPLC (column: Phenomenex C18 150*25 mm*10 μm; mobile phase: [water (NH$_4$HCO$_3$)-ACN]; B %: 41%-71%, 8 min), 5-((4-(2-(2-aminopyridin-3-yl)-5-phenyl-3H-imidazo[4,5-b]pyridin-3-yl)benzyl)amino)nicotinonitrile (Example 188, 7.0 mg, yield: 3.7%) was obtained as a yellow solid. MS: m/z=495.5 [M+H]$^+$. $^1$H NMR (400 MHz, Dimethylsulfoxide-d$_6$) δ 8.31 (d, J=2.8 Hz, 1H), 8.26 (d, J=8.4 Hz, 1H), 8.14 (d, J=2.0 Hz, 1H), 8.03-7.97 (m, 4H), 7.54 (d, J=8.4 Hz, 2H), 7.49-7.37 (m, 5H), 7.32-7.24 (m, 1H), 7.19-7.14 (m, 2H), 7.01 (br s, 2H), 6.36 (dd, J=7.6, 4.8 Hz, 1H), 4.47 (d, J=6.0 Hz, 1H).

Example 189: 2-((4-(2-(2-Aminopyridin-3-yl)-5-phenyl-3H-imidazo[4,5-b]pyridin-3-yl)benzyl) amino)isonicotinonitrile

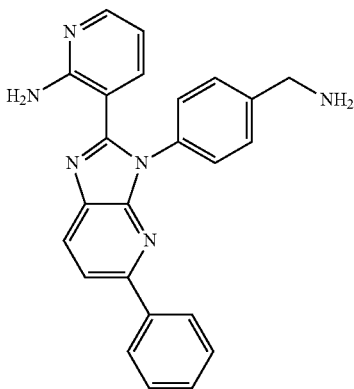

Intermediate 4

→

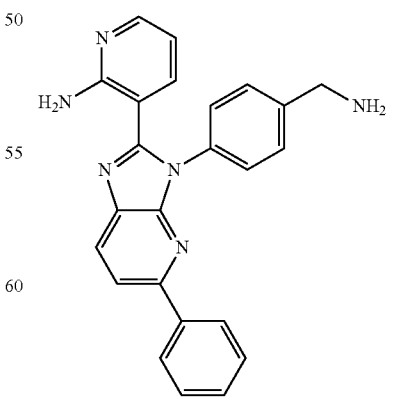

Intermediate 4

→

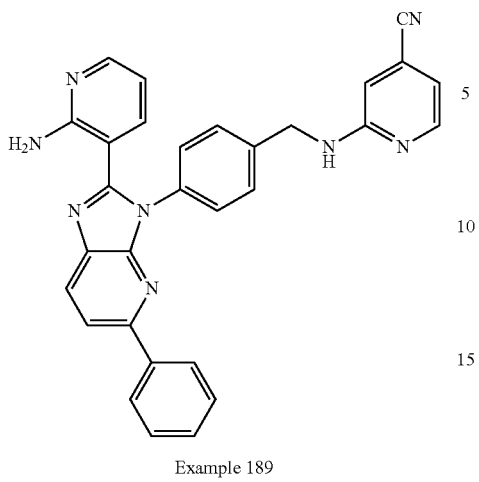

Example 189

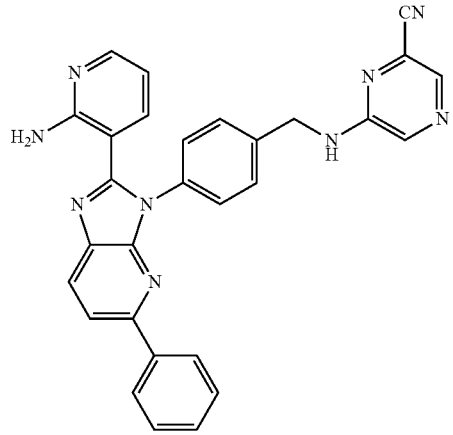

Example 190

To a solution of Intermediate 4 (150 mg, 382 μmol) and 2-chloropyridine-4-carbonitrile (58.3 mg, 420 μmol) in NMP (3 mL) was added DIEA (247 mg, 1.91 mmol). The mixture was stirred under microwave at 160° C. for 1 hr. The reaction was filtered and concentrated under reduced pressure to give a residue. The crude product was purified by prep-HPLC (column: Waters xbridge 150*25 mm 10 μm; mobile phase: [water (NH$_4$HCO$_3$)-ACN]; B %: 55%-85%, 5 min), 2-((4-(2-(2-aminopyridin-3-yl)-5-phenyl-3H-imidazo[4,5-b]pyridin-3-yl)benzyl)amino)isonicotinonitrile (Example 189, 4.4 mg, yield: 2.3%) was obtained as a light yellow solid. MS: m/z=495.2 [M+H]$^+$. $^1$H NMR (400 MHz, Dimethylsulfoxide-d$_6$) δ 8.26 (d, J=8.4 Hz, 1H), 8.19 (d, J=5.2 Hz, 1H), 8.03-7.97 (m, 4H), 7.75-7.73 (m, 1H), 7.50-7.42 (m, 6H), 7.41-7.39 (m, 1H), 7.19 (dd, J=7.6, 1.6 Hz, 1H), 6.97 (br s, 2H), 6.91 (s, 1H), 6.84 (dd, J=5.2, 1.2 Hz, 1H), 6.39 (dd, J=7.6, 4.8 Hz, 1H), 4.63 (d, J=5.6 Hz, 2H).

Example 190: 6-((4-(2-(2-Aminopyridin-3-yl)-5-phenyl-3H-imidazo[4,5-b]pyridin-3-yl)benzyl)amino)pyrazine-2-carbonitrile To a solution of Intermediate 4 (150 mg, 382 μmol) and 6-chloropyrazine-2-carbonitrile (58.7 mg, 420 μmol) in NMP (3 mL) was added DIEA (247 mg, 1.91 mmol). The mixture was stirred under microwave at 135° C. for 1 hr. The reaction was filtered and concentrated under reduced pressure to give a residue. The crude product was purified by prep-HPLC (column: Waters xbridge 150*25 mm 10 μm; mobile phase: [water (NH$_4$HCO$_3$)-ACN]; B %: 19%-49%, 9 min), 6-((4-(2-(2-aminopyridin-3-yl)-5-phenyl-3H-imidazo[4,5-b]pyridin-3-yl)benzyl)amino)pyrazine-2-carbonitrile (Example 190, 6.0 mg, yield: 3.2%) was obtained as a brown solid. MS: m/z=496.3 [M+H]$^+$. $^1$H NMR (400 MHz, Dimethylsulfoxide-d$_6$) δ 8.37 (t, J=6.0 Hz, 1H), 8.29-8.22 (m, 3H), 8.03-7.97 (m, 4H), 7.53-7.51 (m, 2H), 7.49-7.44 (m, 4H), 7.41-7.37 (m, 1H), 7.20 (dd, J=7.6, 1.6 Hz, 1H), 6.96 (br s, 2H), 6.4 (dd, J=7.6, 4.8 Hz, 1H), 4.60 (d, J=6.0 Hz, 2H).

Example 191: 2-((4-(2-(2-Aminopyridin-3-yl)-5-phenyl-3H-imidazo[4,5-b]pyridin-3-yl)benzyl)amino)pyrimidine-4-carbonitrile

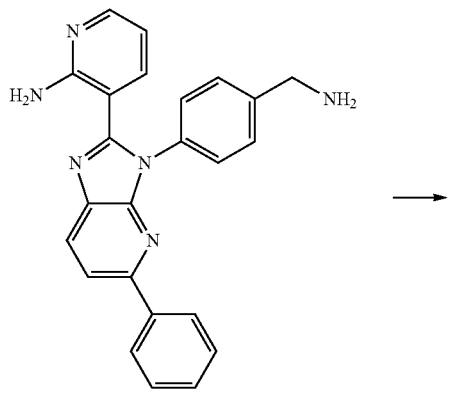

Intermediate 4

→

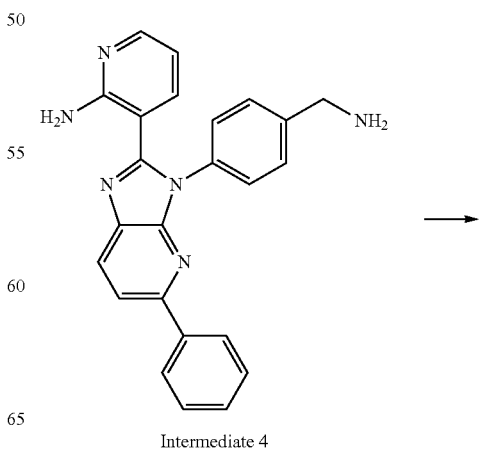

Intermediate 4

→

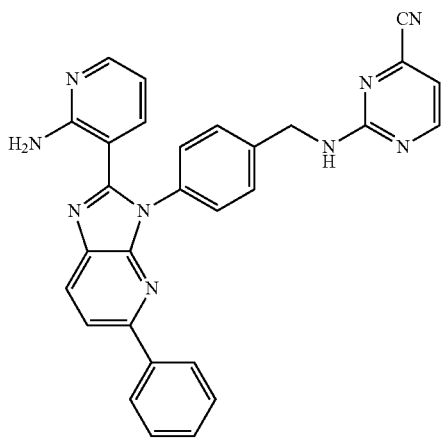

Example 191

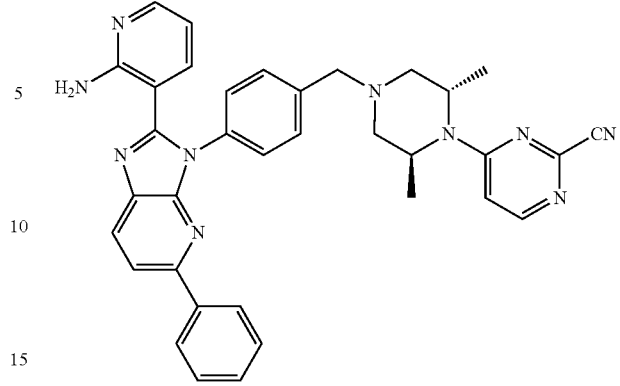

Example 192

To a solution of Intermediate 4 (150 mg, 382 μmol) and 2-chloropyrimidine-4-carbonitrile (58.7 mg, 420 μmol) in NMP (3 mL) was added DIEA (247 mg, 1.91 mmol). The mixture was stirred under microwave at 135° C. for 1 hr. The reaction was filtered and concentrated under reduced pressure to give a residue. The crude product was purified by prep-HPLC (column: Waters xbridge 150*25 mm 10 μm; mobile phase: [water (NH₄HCO₃)-ACN]; B %: 39%-69%, 8 min), 2-((4-(2-(2-aminopyridin-3-yl)-5-phenyl-3H-imidazo[4,5-b]pyridin-3-yl)benzyl)amino)pyrimidine-4-carbonitrile (Example 191, 7.4 mg, yield: 3.9%) was obtained as a brown solid. MS: m/z=496.2 [M+H]⁺. ¹H NMR (400 MHz, Dimethylsulfoxide-d₆) δ 8.60 (d, J=4.4 Hz, 1H), 8.51-8.48 (m, 1H), 8.26 (d, J=8.4 Hz, 1H), 8.03-7.97 (m, 4H), 7.48-7.44 (m, 6H), 7.41-7.37 (m, 1H), 7.19-7.17 (m, 1H), 7.15 (d, J=4.8 Hz, 1H), 6.97 (br s, 2H), 6.39 (dd, J=7.6, 4.8 Hz, 1H), 4.66-4.58 (br s, 2H).

Example 192: 4-((2S,6S)-4-(4-(2-(2-Aminopyridin-3-yl)-5-phenyl-3H-imidazo[4,5-b]pyridin-3-yl)benzyl)-2,6-dimethylpiperazin-1-yl)pyrimidine-2-carbonitrile Intermediate 28 (100 mg, 204 μmol), 4-chloropyrimidine-2-carbonitrile (28.5 mg, 204 μmol) and DIEA (106 mg, 817 μmol) were taken up into a microwave tube in NMP (2 mL). The sealed tube was heated at 160° C. for 1 hr under microwave. The reaction mixture was quenched with H₂O (5 mL) at 0° C., and then diluted with CH₂Cl₂ (10 mL) and extracted with CH₂Cl₂ 30 mL (15 mL×2). The combined organic layers were washed with 15 mL aqueous NaCl, dried over Na₂SO₄, filtered and concentrated under reduced pressure to give a residue. After purified by prep-HPLC (column: Welch Xtimate C18 150×25 mm 5 μm; mobile phase: [water (NH₄HCO₃)-ACN]; B %: 60%-90%, 20 min), 4-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile (Example 192, 10.5 mg, yield: 8.3%) was obtained as a brown lyophilized powder. MS: m/z=593.3 [M+H]⁺. ¹H NMR (400 MHz, Dimethylsulfoxide-d₆) 8.33-8.26 (m, 2H), 8.05-7.98 (m, 4H), 7.55-7.52 (m, 2H), 7.51-7.36 (m, 6H), 7.18 (dd, J=7.6, 1.6 Hz, 1H), 7.04 (br s, 2H), 6.39 (dd, J=7.6, 4.8 Hz, 1H), 4.24-4.18 (m, 2H), 3.94 (d, J=13.6 Hz, 1H), 3.80 (d, J=13.6 Hz, 1H), 3.11 (dd, J=12.0, 4.0 Hz, 2H), 2.68 (dd, J=12.0, 3.6 Hz, 2H), 1.27 (d, J=6.4 Hz, 6H).

Example 193: 2-((2S,6S)-4-(4-(2-(2-Aminopyridin-3-yl)-5-phenyl-3H-imidazo[4,5-b]pyridin-3-yl)benzyl)-2,6-dimethylpiperazin-1-yl)pyrimidine-4-carbonitrile

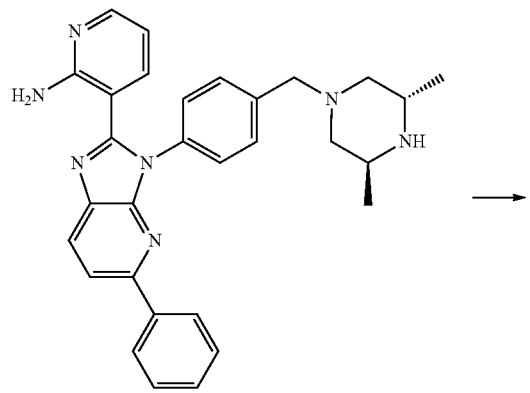

Intermediate 28

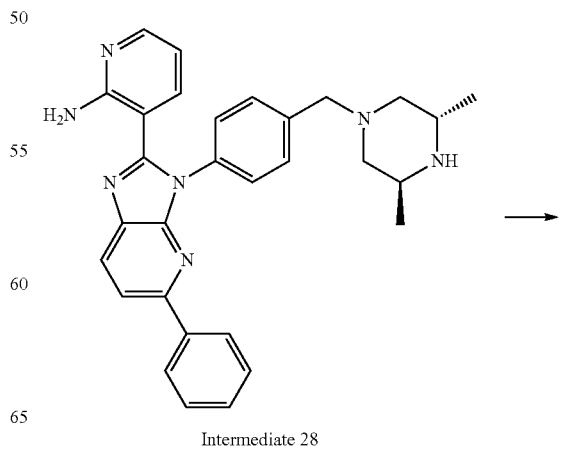

Intermediate 28

1261
-continued

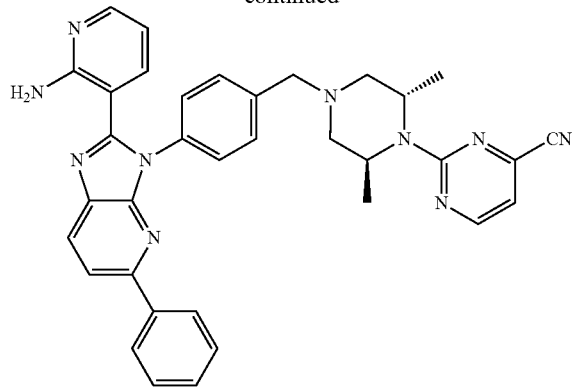

Example 193

Intermediate 28 (100 mg, 204 μmol), 2-chloropyrimidine-4-carbonitrile (28.5 mg, 204 μmol) and DIEA (106 mg, 817 μmol) were taken up into a microwave tube in NMP (2 mL). The sealed tube was heated at 160° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with 15 mL aqueous NaCl, dried over Na$_2$SO$_4$, filtered and concentrated under reduced pressure to give a residue. After purified by prep-HPLC (column: Welch Xtimate C18 150×25 mm 5 μm; mobile phase: [water (NH$_4$HCO$_3$)-ACN]; B %: 60%-90%, 20 min), 2-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile (Example 193, 6.1 mg, yield: 4.9%) was obtained as a brown lyophilized powder. MS: m/z=593.5 [M+H]$^+$. $^1$H NMR (400 MHz, Dimethylsulfoxide-d$_6$) 8.72 (d, J=4.4 Hz, 1H), 8.27 (d, J=8.4 Hz, 1H), 8.05-7.97 (m, 4H), 7.56-7.52 (m, 2H), 7.49-7.37 (m, 5H), 7.25 (d, J=4.8 Hz, 1H), 7.17 (dd, J=7.6, 1.6 Hz, 1H), 7.05 (br s, 2H), 6.39 (dd, =7.6, 4.8 Hz, 1H), 4.33-4.26 (m, 2H), 3.87 (d, J=13.6 Hz, 1H), 3.69 (d, J=13.6 Hz, 1H), 2.95 (dd, J=11.6, 3.6 Hz, 2H), 2.56 (dd, J=12.0, 4.8 Hz, 2H), 1.26 (d, J=6.4 Hz, 6H).

Example 194: 6-((2S,6S)-4-(4-(2-(2-Aminopyridin-3-yl)-5-phenyl-3H-imidazo[4,5-b]pyridin-3-yl)benzyl)-2,6-dimethylpiperazin-1-yl)pyrimidine-4-carbonitrile 1262
-continued Example 194

Intermediate 28 (100 mg, 204 μmol), 6-chloropyrimidine-4-carbonitrile (28.5 mg, 204 μmol) and DIEA (106 mg, 817 μmol) were taken up into a microwave tube in NMP (2 mL). The sealed tube was heated at 160° C. for 1 hr under microwave. The reaction mixture was quenched with H$_2$O (5 mL) at 0° C., and then diluted with 10 mL CH$_2$Cl$_2$ (10 mL) and extracted with CH$_2$Cl$_2$ 30 mL (15 mL×2). The combined organic layers were washed with 15 mL aqueous NaCl, dried over Na$_2$SO$_4$, filtered, and concentrated under reduced pressure to give a residue. After purified by prep-HPLC (column. Welch Xtimate C18 150×25 mm 5 μm; mobile phase: [water (NH$_4$HCO$_3$)-ACN]; B %: 55%-85%, 20 min), 6-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile (Example 194, 8.5 mg, yield: 6.9%) was obtained as a brown lyophilized powder. MS: m/z=593.3 [M+H]$^+$. $^1$H NMR (400 MHz, Dimethylsulfoxide-d$_6$) δ 8.64 (s, 1H), 8.27 (d, J=8.4 Hz, 1H), 8.05-7.97 (m, 4H), 7.56-7.52 (m, 2H), 7.49-7.44 (m, 5H), 7.42-7.37 (m, 1H), 7.17 (dd, J=7.6, 1.6 Hz, 1H), 7.04 (br s, 2H), 6.38 (dd, J=7.6, 4.8 Hz, 1H), 4.29-4.22 (m, 2H), 3.95 (d, J=14.0 Hz, 1H), 3.82 (d, J=13.6 Hz, 1H), 3.14 (dd, J=12.0, 4.0 Hz, 2H), 2.69 (dd, J=12.0, 3.2 Hz, 2H), 1.27 (d, J=6.4 Hz, 6H).

Example 195: 4-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile

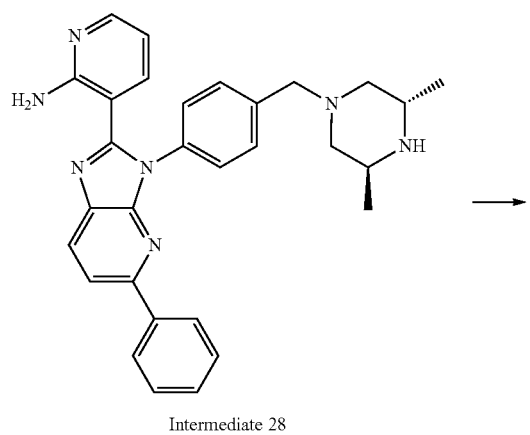

Intermediate 28

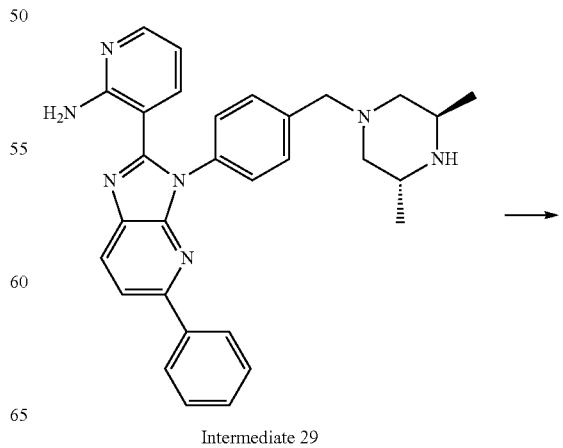

Intermediate 29

1263
-continued

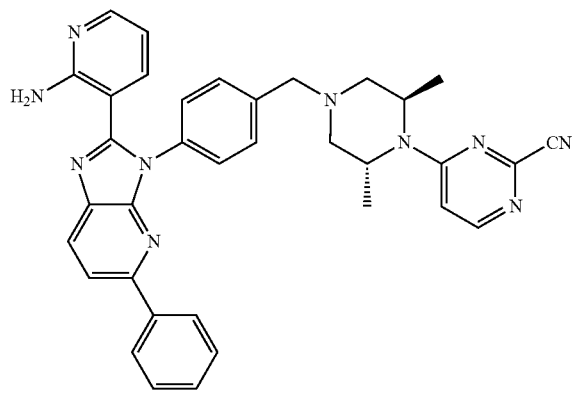

Example 195

To a solution of 4-chloropyrimidine-2-carbonitrile (31 mg, 225 μmol) in NMP (2 mL) was added DIEA (105 mg, 817 μmol) and Intermediate 29 (100 mg, 204 μmol). The mixture was heated under microwave and stirred at 160° C. for 1 hr, the reaction mixture was filtered to get a liquid. The liquid was purified by prep-HPLC (column: Phenomenex C18 150*25 mm*10 μm; mobile phase: [water ($NH_4HCO_3$)-ACN]; B %: 50%-80%, 14 min), 4-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile (Example 195, 18.3 mg, yield: 12.3%) was obtained as a white lyophilized powder. MS: m/z=593.4 $[M+H]^+$. $^1$H NMR (400 MHz, Methanol-$d_4$) δ 8.25-8.13 (m, 2H), 8.03 (d, J=7.2 Hz, 2H), 7.98 (dd, J=5.2, 1.6 Hz, 1H), 7.93 (d, J=8.4 Hz, 1H), 7.56 (d, J=8.4 Hz, 2H), 7.46-7.40 (m, 4H), 7.37 (d, J=7.2 Hz, 1H), 7.32 (dd, J=7.6, 1.6 Hz, 1H), 6.91 (d, J=6.4 Hz, 1H), 6.47 (dd, J=7.6, 5.2 Hz, 1H), 4.32-4.19 (m, 2H), 3.94 (d, J=13.6 Hz, 1H), 3.81 (m, J=13.6 Hz, 1H), 3.20-3.12 (m, 2H), 2.78-2.70 m, 2H), 1.36 (d, J=6.4 Hz, 6H).

Example 196: 2-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile

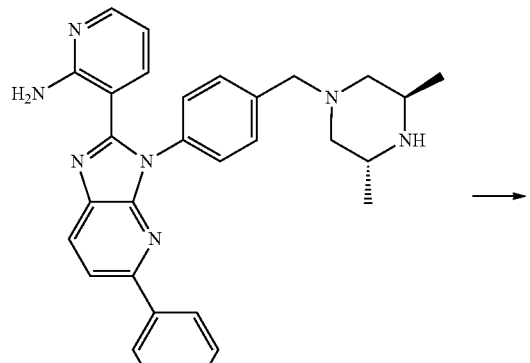

Intermediate 29

1264
-continued

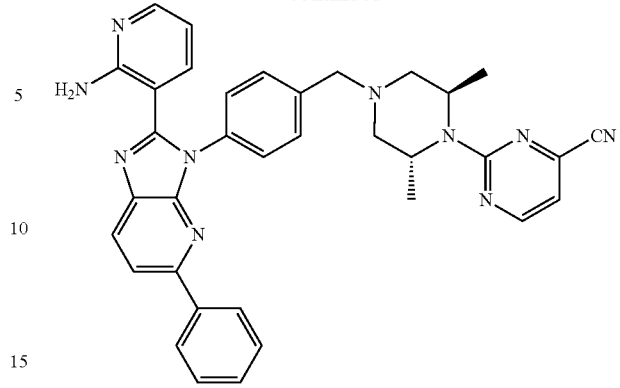

Example 196

To a solution of 2-chloropyrimidine-4-carbonitrile (31 mg, 225 μmol) in NMP (2 mL) was added DIEA (106 mg, 817 μmol) and Intermediate 29 (100 mg, 204 μmol). The mixture was heated under microwave irradiation and was stirred at 160° C. for 1 hr. The reaction mixture was quenched with $H_2O$ (10 mL) at 25° C. and extracted with EtOAc (10 mL×4). The combined organic layers were washed with brine (10 mL×2), dried over $Na_2SO_4$, filtered, and concentrated under reduced pressure to give a residue. The residue was purified by column chromatography (eluent of 0-10% MeOH in $CH_2Cl_2$) and then purified by prep-HPLC (column: Phenomenex C18 150*25 mm*10 um; mobile phase: [water ($NH_4HCO_3$)-ACN]; B %: 60%-90%, 8 min), 2-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile (Example 196, 30 mg, yield. 12.3%) was obtained as a brown lyophilized powder. MS: m/z=593.3 $[M+H]^+$. $^1$H NMR (400 MHz, Dimethyl-sulfoxide-$d_6$) δ 8.72 (d, J=4.8 Hz, 1H), 8.27 (d, J=8.4 Hz, 1H), 8.05-7.97 (m, 4H), 7.54 (d, J=8.4 Hz, 2H), 7.49-7.44 (m, 4H), 7.42-7.38 (m, 1H), 7.25 (d, J=4.8 Hz, 1H), 7.17 (dd, J=7.6, 1.6 Hz, 1H), 7.05 (br s, 2H), 6.45-6.32 (m, 1H), 4.35-4.20 (m, 2H), 3.87 (d, J=14.0 Hz, 1H), 3.69 (d, J=14.0 Hz, 1H), 3.01-2.88 (m, 2H), 2.58-2.57 (m, 1H), 2.55-2.54 (m, 1H), 1.26 (d, =6.4 Hz, 6H).

Example 197: 6-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile

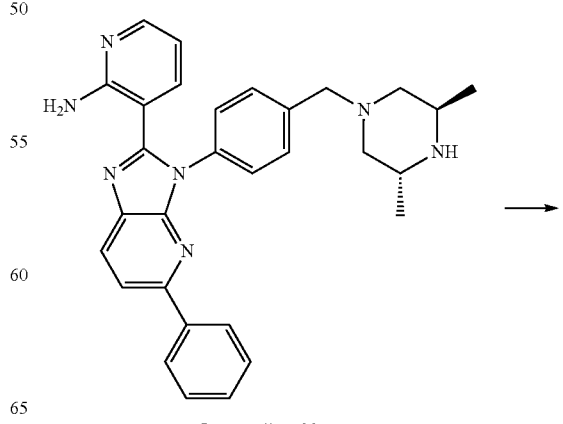

Intermediate 29

1265
-continued

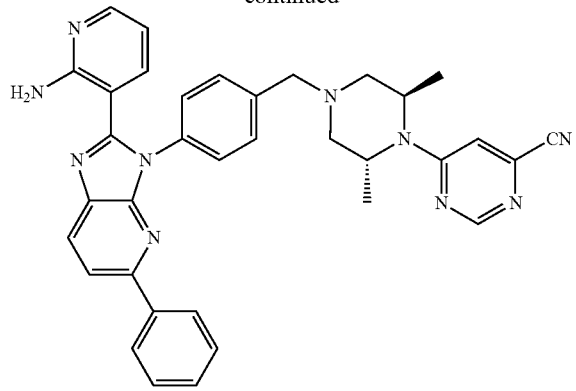

Example 197

1266
-continued

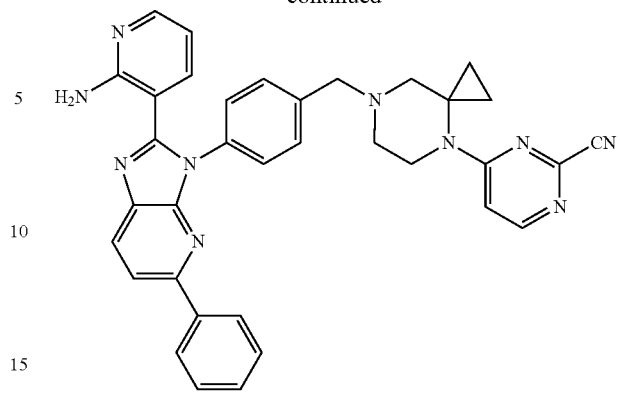

Example 198

To a solution of Intermediate 29 (100 mg, 204 μmol) in NMP (2 mL) was added DIEA (106 mg, 817 μmol) and 6-chloropyrimidine-4-carbonitrile (31 mg, 225 μmol). The mixture was heated under microwave irradiation and stirred at 160° C. for 1 hr, the reaction mixture was filtered to get a liquid. The liquid was purified by prep-HPLC (column: Waters xbridge 150*25 mm 10 um; mobile phase: [water ($NH_4HCO_3$)-ACN]; B %: 52%-82%, 8 min), 6-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile (Example 197, 31.3 mg, yield: 25%) was obtained as a gray lyophilized powder. MS: m/z=593.4 [M+H]$^+$. $^1$H NMR (400 MHz, Methanol-d$_4$) δ 8.58 (s, 1H), 8.19 (d, J=8.4 Hz, 1H), 8.03 (d, J=7.2 Hz, 2H), 7.98 (dd, J=4.8, 1.6 Hz, 1H), 7.94 (d, J=8.4 Hz, 1H), 7.57 (d, J=8.4 Hz, 2H), 7.47-7.40 (m, 5H), 7.33 (dd, J=8.0, 1.6 Hz, 1H), 7.23 (s, 1H), 6.48 (dd, J=7.6, 5.2 Hz, 1H), 4.34-4.24 (m, 2H), 3.96 (d, J=13.6 Hz, 1H), 3.84 (d, J=13.6 Hz, 1H), 3.24-3.16 (m, 2H), 2.80-2.72 (m, 2H), 1.36 (d, J=6.4 Hz, 6H).

Example 198: 4-(7-(4-(2-(2-Aminopyridin-3-yl)-5-phenyl-3H-imidazo[4,5-b]pyridin-3-yl)benzyl)-4,7-diazaspiro[2.5]octan-4-yl)pyrimidine-2-carbonitrile To a solution of Intermediate 30 (50 mg, 103 μmol) and 2-chloropyrimidine-4-carbonitrile (14.3 mg, 103 μmol) in NMP (1 mL) was added DIEA (66.3 mg, 513 μmol). The mixture was stirred at 130° C. for 0.5 hr under microwave. The reaction mixture was filtered. The residue was purified by prep-HPLC (column: Waters xbridge 150×25 mm 10 μm; mobile phase: [water ($NH_4HCO_3$)-ACN]; B %: 47%-77%, 10 min), 4-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-2-carbonitrile (Example 198, 15 mg, yield: 24%) was obtained as an off-white lyophilized powder. MS: m/z=591.4 [M+H]$^+$. $^1$H NMR (400 MHz, Dimethylsulfoxide-d$_6$) δ 8.35 (d, J=6.0 Hz, 1H), 8.27 (d, J=8.4 Hz, 1H), 8.07-7.93 (m, 4H), 7.52-7.34 (m, 7H), 7.23 (d, J=6.4 Hz, 1H), 7.12 (dd, J=7.6, 1.6 Hz, 1H), 7.04 (s, 2H), 6.29 (dd, J=7.6, 4.8 Hz, 1H), 3.59 (s, 2H), 2.51-2.50 (m, 6H), 1.25-0.75 (m, 4H).

Example 199: 2-(7-(4-(2-(2-Aminopyridin-3-yl)-5-phenyl-3H-imidazo[4,5-b]pyridin-3-yl)benzyl)-4,7-diazaspiro[2.5]octan-4-yl)pyrimidine-4-carbonitrile

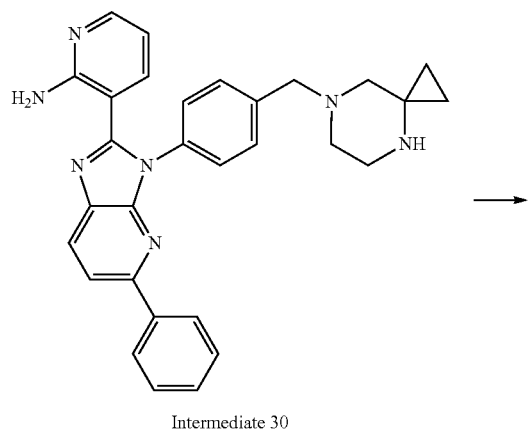

Intermediate 30

→

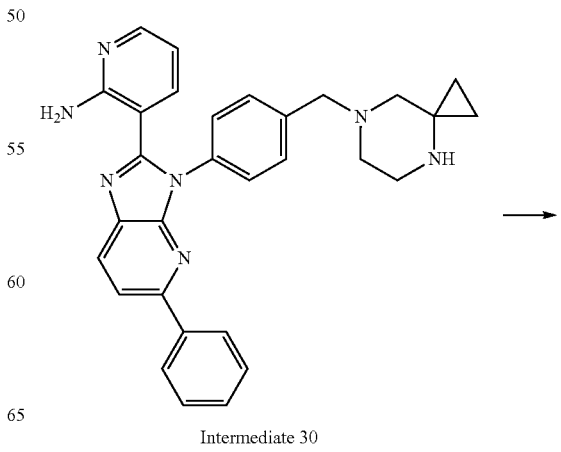

Intermediate 30

→

| 1267 -continued | 1268 -continued |
|---|---|
| 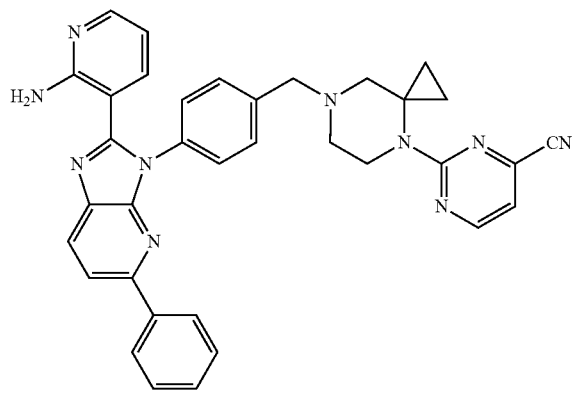 Example 199 | 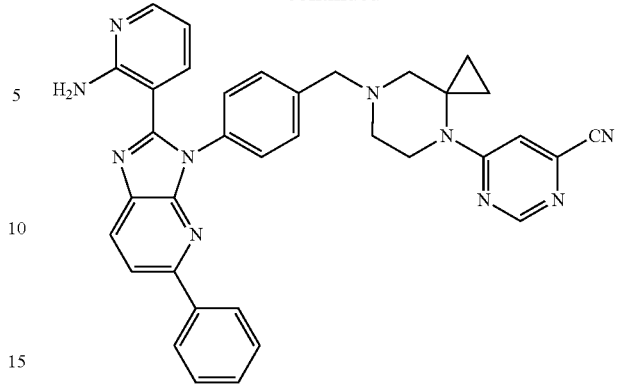 Example 200 |

To a solution of Intermediate 30 (100 mg, 205 μmol) and 2-chloropyrimidine-4-carbonitrile (28.6 mg, 205 μmol) in NMP (1 mL) was added DIEA (133 mg, 1.03 mmol). The mixture was stirred at 130° C. for 0.5 hr under microwave. The reaction mixture was filtered. The residue was purified by prep-HPLC (column: Waters xbridge 150×25 mm 10 μm; mobile phase: [water (NH$_4$HCO$_3$)-ACN]; B %: 59%-89%, 10 min), 2-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-4-carbonitrile (Example 199, 13.9 mg, yield: 10%) was obtained as a yellow lyophilized powder. MS: m/z=591.4 [M+H]$^+$. $^1$H NMR (400 MHz, Dimethylsulfoxide-d$_6$) δ 8.70 (d, J=4.8 Hz, 1H), 8.27 (d, J=8.4 Hz, 1H), 8.08-7.93 (m, 4H), 7.51-7.38 (m, 7H), 7.26 (d, J=4.8 Hz, 1H), 7.11 (dd, J=7.6, 1.6 Hz, 1H), 7.05 (s, 2H), 6.34-6.27 (dd, J=8.0, 4.8 Hz, 1H), 4.05-3.97 (m, 2H), 3.56 (s, 2H), 3.34-3.33 (m, 2H), 2.33 (s, 2H), 0.98-0.95 (m, 2H), 0.80-0.75 (m, 2H), Example 200: 6-(7-(4-(2-(2-Aminopyridin-3-yl)-5-phenyl-3H-imidazo[4,5-b]pyridin-3-yl)benzyl)-4,7-diazaspiro[2.5]octan-4-yl)pyrimidine-4-carbonitrile To a solution of 3-(3-(4-((4,7-diazaspiro[2.5]octan-7-yl)methyl)phenyl)-5-phenyl-3H-imidazo[4,5-b]pyridin-2-yl)pyridin-2-amine (50 mg, 103 μmol) and 6-chloropyrimidine-4-carbonitrile (14.3 mg, 103 μmol) in NMP (1 mL) was added DIEA (66.3 mg, 513 μmol). The mixture was stirred at 130° C. for 0.5 hr under microwave. The reaction mixture was filtered. The residue was purified by prep-HPLC (column: Waters xbridge 150×25 mm 10 μm; mobile phase: [water (NH$_4$HCO$_3$)-ACN]; B %: 49%-79%, 10 min), 6-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-4-carbonitrile (Example 200, 18.9 mg, yield: 29%) was obtained as an off-white lyophilized powder. MS: m/z=591.4 [M+H]$^+$. $^1$H NMR (400 MHz, Dimethylsulfoxide-d$_6$) δ 8.66 (d, J=1.2 Hz, 1H), 8.10-7.86 (m, 4H), 7.54 (s, 1H), 7.49-7.39 (m, 7H), 7.12 (dd, J=7.2, 1.6 Hz, 1H), 7.07-6.96 (m, 2H), 6.29 (dd, J=7.6, 4.8 Hz, 1H), 3.59 (br s, 2H), 2.48-2.44 (m, 6H), 1.25-0.75 (m, 4H).

Example 201: 4-((3-(4-(2-(2-Aminopyridin-3-yl)-5-phenyl-3H-imidazo[4,5-b]pyridin-3-yl)benzyl)-3-azabicyclo[3.2.1]octan-8-yl)amino)pyrimidine-2-carbonitrile

| 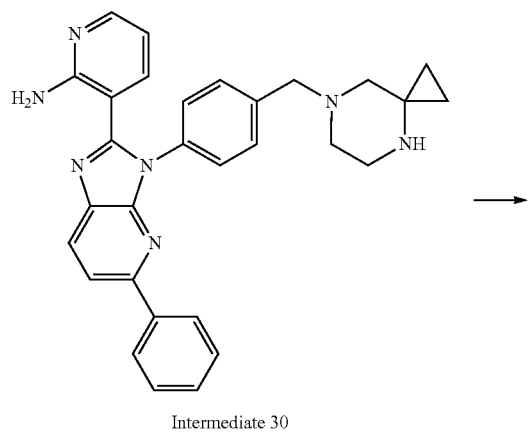 Intermediate 30 → | 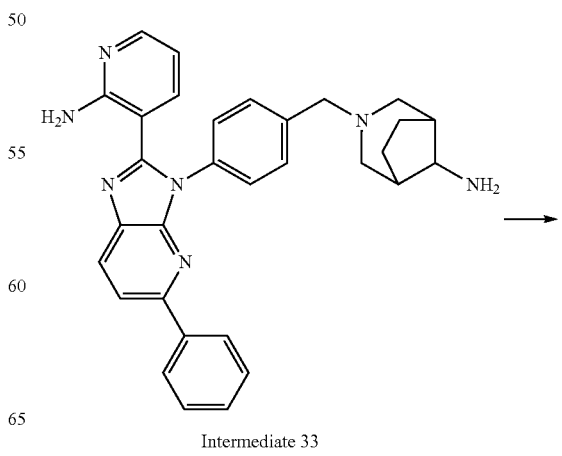 Intermediate 33 → |
|---|---|

| 1269 | 1270 |
|---|---|
| -continued | -continued |

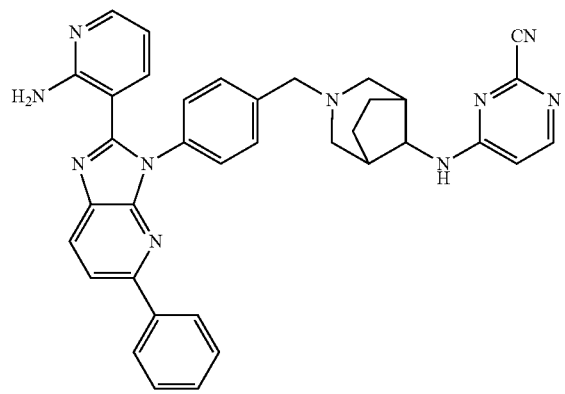

Example 201

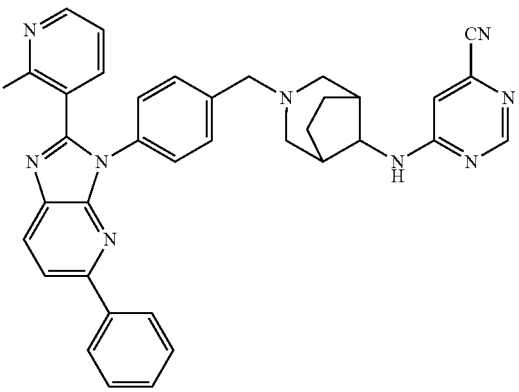

Example 202

Intermediate 33 (100 mg, 199 μmol), 4-chloropyrimidine-2-carbonitrile (27.8 mg, 199 μmol) and DIEA (129 mg. 997 μmol) were taken up into a microwave tube in NMP (2 mL). The sealed tube was heated at 160° C. for 1 hr under microwave. After purified by prep-HPLC (column: Welch Xtimate 150×25 mm×5 μm; mobile phase: [water (NH$_4$HCO$_3$)-ACN]; B %: 60%-90%, 20 min), 4-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-2-carbonitrile (Example 201, 12 mg, yield: 9.3%) was obtained as a brown solid. MS: m/z=605.4 [M+H]$^+$. $^1$H NMR (400 MHz, Dimethylsulfoxide-d$_6$) δ 8.27 (d, =8.4 Hz, 1H), 8.14 (d, J=6.4 Hz, 1H), 8.06-7.98 (m, 5H), 7.51-7.44 (m, 6H), 7.42-7.37 ((m, 1H), 7.15 (dd, J=7.6, 1.2 Hz, 1H), 7.06 (br s, 2H), 6.98 (d, J=5.2 Hz, 1H), 6.36 (dd, J=7.6, 4.8 Hz, 1H), 3.87-3.82 (m, 1H), 3.62 (s, 2H), 2.54-2.52 (m, 4H), 2.28-2.22 (m, 2H), 1.81-1.73 (m, 4H).

Intermediate 33 (100 mg, 199 μmol), 4-chloropyrimidine-2-carbonitrile (27.8 mg, 199 μmol) and DIEA (129 mg, 997 μmol) were taken up into a microwave tube in NMP (2 mL). The sealed tube was heated at 160° C. for 1 hr under microwave. After purified by prep-HPLC (column: Welch Xtimate 150×25 mm×5 μm; mobile phase: [water (NH$_4$HCO$_3$)-ACN]; B %: 60%-90%, 20 min), 6-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-4-carbonitrile (Example 202, 14.4 mg, yield: 11%) was obtained as a brown solid. MS: m/z=605.3 [M+H]$^+$. $^1$H NMR (400 MHz, Dimethylsulfoxide-d$_6$) δ 8.57-8.46 (m, 1H), 8.27 (d, J=8.4 Hz, 1H), 8.08 (d, J=5.6 Hz, 1H), 8.04-7.97 (m, 4H), 7.50-7.43 (m, 6H), 7.41-7.37 (m, 1H), 7.22 (s, 1H), 7.15 (dd, J=7.6, 1.6 Hz, 1H), 7.05 (s, 2H), 6.35 (dd, J=7.6, 4.8 Hz, 1H), 3.94-3.88 (m, 1H), 3.61 (s, 2H), 2.53-2.51 (m, 4H), 2.27-2.22 (m, 2H), 1.79-1.69 (m, 4H).

Example 202: 6-((3-(4-(2-(2-Aminopyridin-3-yl)-5-phenyl-3H-imidazo[4,5-b]pyridin-3-yl)benzyl)-3-azabicyclo[3.2.1]octan-8-yl)amino)pyrimidine-4-carbonitrile Example 203: 4-(3-(4-(2-(2-Aminopyridin-3-yl)-5-phenyl-3H-imidazo[4,5-b]pyridin-3-yl)benzyl)-3,8-diazabicyclo[3.2.1]octan-8-yl)pyrimidine-2-carbonitrile

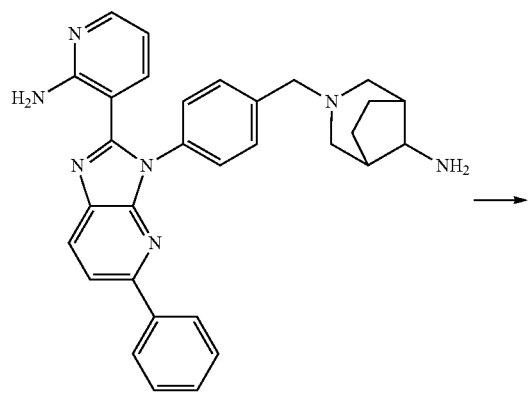

Intermediate 33

→

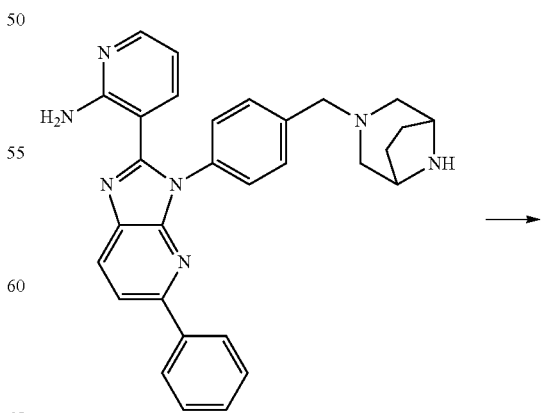

Intermediate 31

→

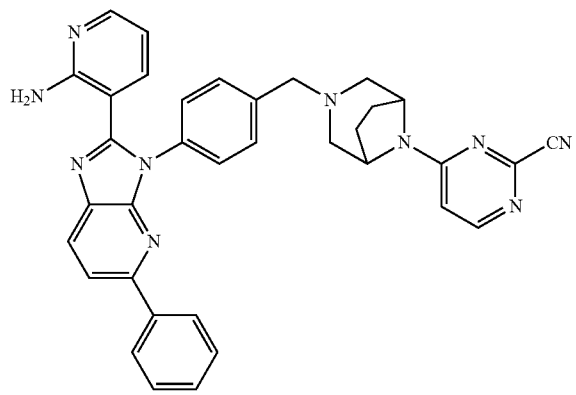

Example 203

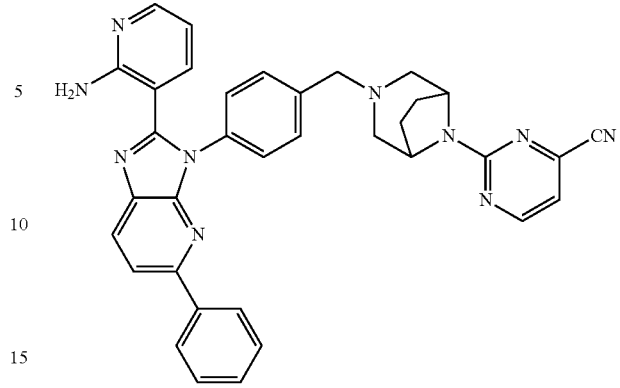

Example 204

A solution of Intermediate 31 (80 mg, 164 μmol), 4-chloropyrimidine-2-carbonitrile (25.2 mg, 180 μmol) and DIEA (106 mg, 820 μmol) were taken up into a microwave tube in NMP (2 mL). The sealed tube was heated at 130° C. for 1 hr under microwave. The reaction mixture was filtered, the filtrate was concentrated under reduced pressure to give a residue. The residue was purified by prep-HPLC (column: Waters xbridge 150*25 mm 10 μm; mobile phase: [water (NH$_4$HCO$_3$)-ACN]; B %: 55%-85%, 10 min), 4-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-2-carbonitrile (Example 203, 10.5 mg, yield: 11%) was obtained as a light-yellow solid. MS: m/z=591.4 [M+H]$^+$. $^1$H NMR (400 MHz, Dimethylsulfoxide-d$_6$) δ 8.27 (d, J=8.4 Hz, H), 8.24 (d, J=6.4 Hz, H), 8.04-7.97 (m, 4H), 7.50-7.44 (m, 6H), 7.42-7.38 (m, 1H), 7.11 (dd, J=7.6, 1.6 Hz, 1H), 7.05 (br s, 2H), 7.02 (d, J=6.4 Hz, 1H), 6.31 (dd, J=7.6, 4.8 Hz, 1H), 4.84-4.76 (m, 1H), 4.57-4.51 (m, 1H), 3.59 (s, 2H), 2.75-2.68 (m, 2H), 2.31-2.26 (m, 2H), 2.06-1.82 (m, 4H).

Example 204: 2-(3-(4-(2-(2-Aminopyridin-3-yl)-5-phenyl-3H-imidazo[4,5-b]pyridin-3-yl)benzyl)-3,8-diazabicyclo[3.2.1]octan-8-yl)pyrimidine-4-carbonitrile Following the general procedure of Example 203 the reaction of Intermediate 31 (80 mg, 164 μmol) with 2-chloropyrimidine-4-carbonitrile (25.2 mg, 180 μmol) was carried out. After purified by prep-HPLC (column: Waters xbridge 150*25 mm 10 um; mobile phase: [water (NH$_4$HCO$_3$)-ACN]; B %: 63%-93%, 10 min), 2-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-4-carbonitrile (Example 204, 6.7 mg, yield: 6.9%) was obtained as a light-yellow powder. MS: m/z=591.5 [M+H]$^+$. $^1$H NMR (400 MHz, Dimethylsulfoxide-d$_6$) δ 8.64 (d, J=4.8 Hz, 1H), 8.26 (d, J=8.4 Hz, 1H), 8.05-7.97 (m, 4H), 7.50-7.43 (m, 6H), 7.41-7.37 (m, 1H), 7.15-7.11 (m, 2H), 7.05 (br s, 2H), 6.33 (dd, J=7.6, 4.8 Hz, 1H), 4.72-4.64 (m, 2H), 3.58 (s, 2H), 2.72 (d, J=9.2 Hz, 2H), 2.30 (d, J=10.4 Hz, 2H), 2.04-1.96 (m, 2H), 1.90-1.85 (m, 2H).

Example 205: 6-(3-(4-(2-(2-Aminopyridin-3-yl)-5-phenyl-3H-imidazo[4,5-b]pyridin-3-yl)benzyl)-3,8-diazabicyclo[3.2.1]octan-8-yl)pyrimidine-4-carbonitrile

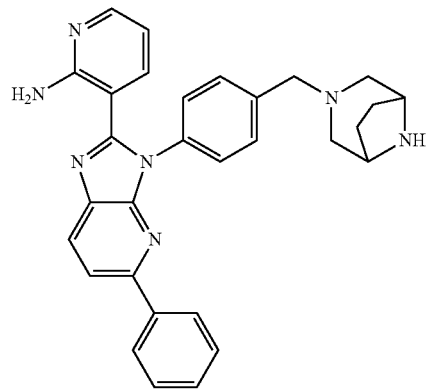

Intermediate 31

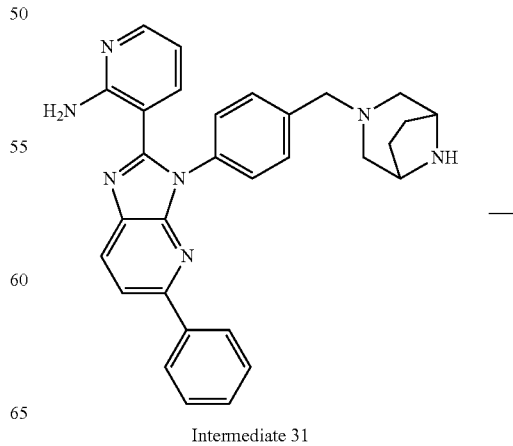

Intermediate 31

1273
-continued

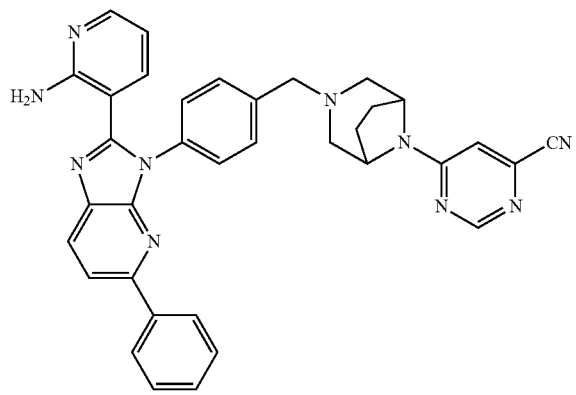

Example 205

1274
-continued

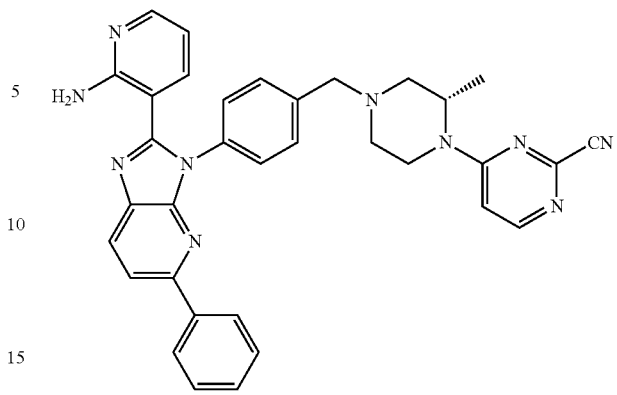

Example 206

Following the general procedure of Example 203, the reaction of Intermediate 31 (80 mg, 164 μmol) with 6-chloropyrimidine-4-carbonitrile (25.2 mg, 180 μmol) was carried out. After purified by prep-HPLC (column: Waters xbridge 150*25 mm 10 um; mobile phase: [water (NH$_4$HCO$_3$)-ACN]; B %: 55%-85%, 10 min), 6-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-4-carbonitrile (Example 205, 11 mg, yield: 11.4%) was obtained as a light-yellow powder. MS: m/z=591.5 [M+H]$^+$. $^1$H NMR (400 MHz, Dimethylsulfoxide-d$_6$) δ 8.54 (s, 1H), 8.27 (d, J=8.4 Hz, 1H), 8.05-7.97 (m, 4H), 7.50-7.43 (m, 7H), 7.41-7.37 (m, 1H), 7.13 (dd, J=7.6, 1.6 Hz, 1H), 7.05 (br s, 2H), 6.30 (dd, J=7.6, 4.4 Hz, 1H), 4.90-4.84 (m, 1H), 4.59-4.53 (m, 1H), 3.59 (s, 2H), 2.72 (d, J=11.2 Hz, 2H), 2.30 (d, J=10.4 Hz, 2H), 2.05-2.00 (m, 2H), 1.90-1.85 (m, 2H).

Example 206: (S)-4-(4-(4-(2-(2-Aminopyridin-3-yl)-5-phenyl-3H-imidazo[4,5-b]pyridin-3-yl)benzyl)-2-methylpiperazin-1-yl)pyrimidine-2-carbonitrile To a solution of Intermediate 34 (50 mg, 105 μmol) and 2-chloropyrimidine-4-carbonitrile (14.7 mg, 105 μmol) in NMP (1 mL) was added DIEA (67.9 mg, 526 μmol). The mixture was stirred at 130° C. for 0.5 hr under microwave. The reaction mixture was filtered. The reaction mixture was purified by prep-HPLC (column: Waters xbridge 150×25 mm 10 μm; mobile phase: [water (NH$_4$HCO$_3$)-ACN]; B %: 53%-83%, 10 min), (S)-4-(4-(4-(2-(2-aminopyridin-3-yl)-5-phenyl-3H-imidazo[4,5-b]pyridin-3-yl)benzyl)-2-methylpiperazin-1-yl)pyrimidine-2-carbonitrile (Example 206.28 mg, yield: 44%) was obtained as an off-white lyophilized powder. MS: m/z=579.4 [M+H]$^+$. $^1$H NMR (400 MHz, Dimethylsulfoxide-d$_6$) δ 8.31-8.25 (m, 2H), 8.07-7.97 (m, 4H), 7.55-7.53 (m, 2H), 7.50-7.45 (m, 4H), 7.42-7.37 (m, 1H), 7.17 (dd, J=7.6, 1.6 Hz, 1H), 7.10-7.01 (m, 3H), 6.39 (dd, J=7.6, 4.8 Hz, 1H), 4.56 (br s, 1H), 4.22 (br s, 1H), 3.71 (d, J=14.0 Hz, 1H), 3.60-3.52 (d, J=14.0 Hz, 1H), 3.23-3.16 (m, 1H), 2.98 (br d, J=11.2 Hz, 1H), 2.76 (d, J=14.0 Hz 1H), 2.21 (dd, J=11.2, 3.2 Hz, 1H), 2.16-2.02 (m, 1H), 1.24 (d, J=6.8 Hz, 3H).

Example 207: (S)-2-(4-(4-(2-(2-Aminopyridin-3-yl)-5-phenyl-3H-imidazo[4,5-b]pyridin-3-yl)benzyl)-2-methylpiperazin-1-yl)pyrimidine-4-carbonitrile

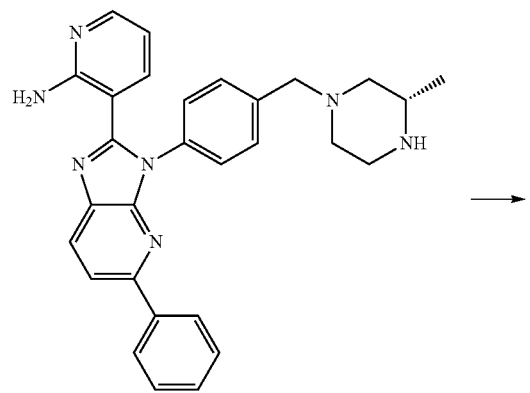

Intermediate 34

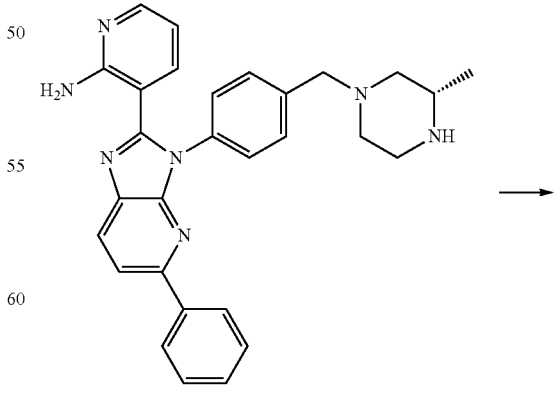

Intermediate 34

1275
-continued

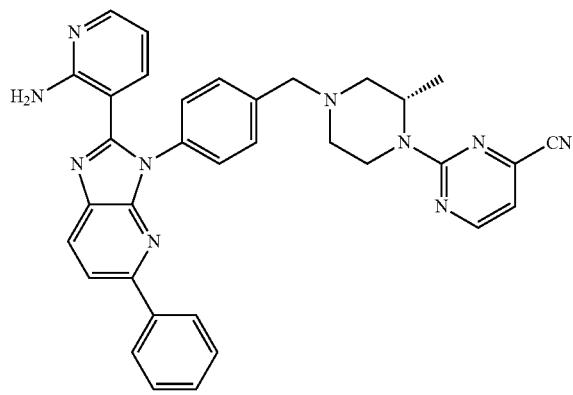

Exampls 207

1276
-continued

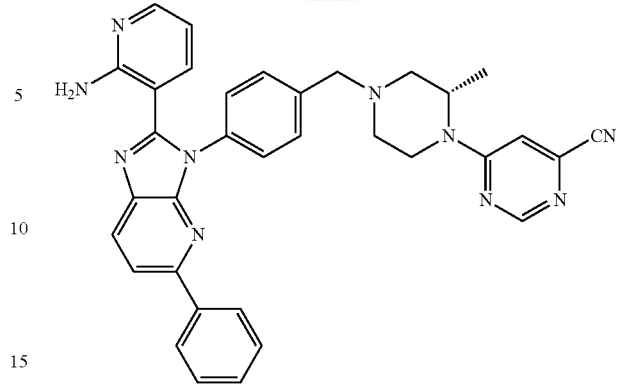

Exampls 208

To a solution of Intermediate 207 (100 mg, 210 μmol) and 2-chloropyrimidine-4-carbonitrile (29.3 mg, 210 μmol) in NMP (2 mL) was added DIEA (136 mg, 1.05 mmol). The mixture was stirred at 130° C. for 0.5 hr under microwave. The reaction mixture was filtered. The reaction mixture was purified by prep-HPLC (column: Waters xbridge 150×25 mm 10 μm; mobile phase: [water (NH$_4$HCO$_3$)-ACN]; B %: 59%-89%, 10 min), (S)-2-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile (Example 207, 28.5 mg, yield: 23%) was obtained as a yellow lyophilized powder. MS: m/z=579.4 [M+H]$^+$. $^1$H NMR (400 MHz, Dimethylsulfoxide-d$_6$) δ 8.65 (d, J=4.4 Hz, 1H), 8.27 (d, J=8.4 Hz, 1H), 8.08-7.96 (m, 4H), 7.56-7.53 (m, 2H), 7.49-7.44 (m, 4H), 7.42-7.37 (m, 1H), 7.20-7.12 (m, 2H), 7.05 (s, 2H), 6.39 (dd, J=7.6, 4.8 Hz, 1H), 4.76 (br s, 1H), 4.39 (d, J=12.0 Hz, 1H), 3.70 (d, J=13.6 Hz, 1H), 3.54 (d, J=14.0 Hz, 1H), 3.20 (dt, J=13.2, 3.2 Hz, 1H), 2.96 (d, J=11.2 Hz, 1H), 2.74 (d, J=11.2 Hz, 1H), 2.20 (dd, J=11.2, 4.0 Hz, 1H), 2.14-2.09 (m, 1H), 1.23 (d, J=6.4 Hz, 3H).

Example 208: (S)-6-(4-(4-(2-(2-Aminopyridin-3-yl)-5-phenyl-3H-imidazo[4,5-b]pyridin-3-yl)benzyl)-2-methylpiperazin-1-yl)pyrimidine-4-carbonitrile To a solution of Intermediate 34 (50 mg, 105 μmol) and 6-chloropyrimidine-4-carbonitrile (14.7 mg, 105 μmol) in NMP (1 mL) was added DIEA (67.9 mg, 526 μmol). The mixture was stirred at 130° C. for 0.5 hr under microwave. The reaction mixture was filtered. The residue was purified by prep-HPLC (column: Waters xbridge 150×25 mm 10 μm; mobile phase: [water (NH$_4$HCO$_3$)-ACN]; B %: 53%-83%, 10 min), (S)-6-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile (Example 208, 25.2 mg, 40.6% yield) was obtained as an off-white lyophilized powder. MS: m/z=579.4 [M+H]$^+$. $^1$H NMR (400 MHz, Dimethylsulfoxide-d$_6$) δ 8.58 (s, 1H), 8.27 (d, J=8.4 Hz, 1H), 8.08-7.95 (m, 4H), 7.56-7.44 (m, 7H), 7.41-7.37 (m, 1H), 7.16 (dd, J=8.0, 2.0 Hz, 1H), 7.04 (s, 2H), 6.38 (dd, J=7.6, 4.8 Hz, 1H), 4.63-4.29 (m, 2H), 3.70 (d, J=13.2 Hz, 1H), 3.55 (d, J=13.2 Hz, 1H), 3.22-3.19 (m, 1H), 2.97 (d, J=11.2 Hz, 1H), 2.73 (d, J=11.2 Hz, 1H), 2.20 (dd, J=11.2, 3.2 Hz, 1H), 2.13-2.07 (m, 1H), 1.24 (d, J=6.8 Hz, 3H).

Example 209: 4-((4-(2-(2-Aminopyridin-3-yl)-5-phenyl-3H-imidazo[4,5-b]pyridin-3-yl)benzyl)amino)-1,3,5-triazine-2-carbonitrile

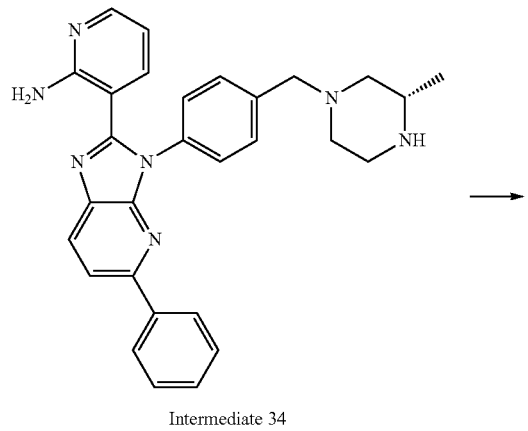

Intermediate 34

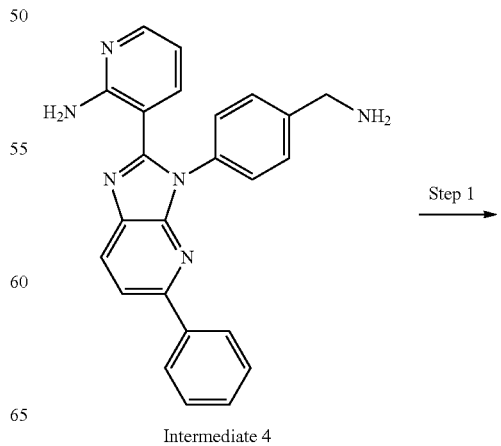

Step 1

Intermediate 4

-continued

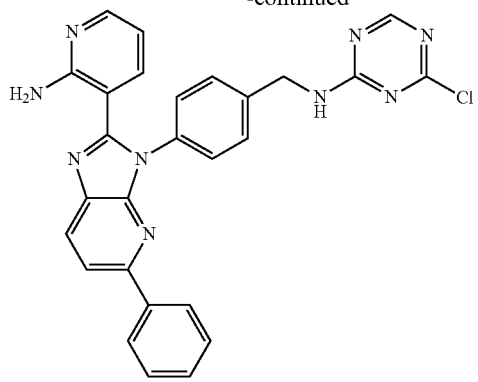

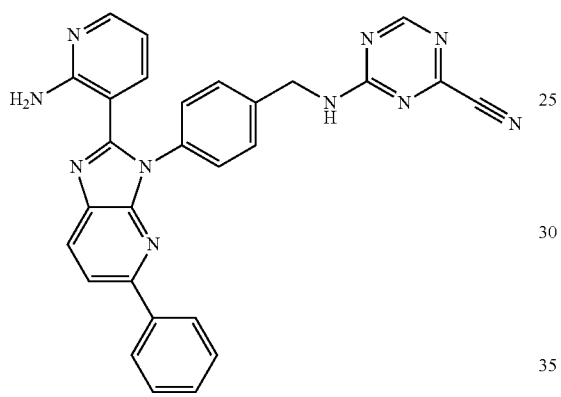

Example 209

Step 1: N-[[4-[2-(2-amino-3-pyridyl)-5-phenyl-imidazo[4,5-b]pyridin-3-yl]phenyl]methyl]-4-chloro-1,3,5-triazin-2-amine To a solution of Intermediate 4 (140 mg, 357 µmol) in THF (4 mL) and H₂O (1 mL) was added K₂CO₃ (148 mg, 1.07 mmol) and stirred at 0° C. for 15 min. Then 2,4-dichloro-1,3,5-triazine (70 mg, 464 µmol) in THF (1 mL) was added into the mixture and stirred at 0° C. for 1.5 hr. The reaction was filtered to give the filter liquor and concentrated under reduced pressure to give a residue. The residue was purified by prep-TLC (MeOH:CH₂Cl₂=1:10) to give N-[[4-[2-(2-amino-3-pyridyl)-5-phenyl-imidazo[4,5-b]pyridin-3-yl]phenyl]methyl]-4-chloro-1,3,5-triazin-2-amine (6.8 mg, yield: 3.4%) as a light-yellow solid. MS: m/z=506.3 [M+H]⁺. ¹H NMR (400 MHz, Dimethylsulfoxide-d₆) δ 9.28-9.19 (m, 1H), 8.51-8.44 (m, 1H), 8.26 (d, J=8.4 Hz, 1H), 8.04-7.97 (m, 4H), 7.49-7.43 (m, 5H), 7.44-7.36 (m, 2H), 7.21 (d, J=7.2 Hz, 1H), 6.95 (d, J=7.2 Hz, 1H), 6.44-6.37 (m, 1H), 4.71-4.59 (m, 2H).

Step 2: 4-((4-(2-(2-aminopyridin-3-yl)-5-phenyl-3H-imidazo[4,5-b]pyridin-3-yl)benzyl)amino)-1,3,5-triazine-2-carbonitrile To a solution of N-(4-(2-(2-aminopyridin-3-yl)-5-phenyl-3H-imidazo[4,5-b]pyridin-3-yl)benzyl)-4-chloro-1,3,5-triazin-2-amine (110 mg, 217 µmol) and DABCO (4.88 mg, 43.5 µmol) in DMSO (1 mL) was added KCN (28.3 mg, 435 µmol) and stirred at 0° C. for 15 min. Then the mixture was stirred at 60° C. for 16 hr. The mixture was quenched with 15 mL H₂O and extracted with CH₂Cl₂ (15 mL×3), the combined organic phase was dried over anhydrous Na₂SO₄, filtered, and concentrated to give a residue. The residue was purified by prep-HPLC (column: Waters xbridge 150×25 mm 10 µm; mobile phase: [water (NH₄HCO₃)-ACN]; B %: 37%-67%, 9 min), 4-((4-(2-(2-aminopyridin-3-yl)-5-phenyl-3H-imidazo[4,5-b]pyridin-3-yl)benzyl)amino)-1,3,5-triazine-2-carbonitrile (Example 209, 7.9 mg, yield: 7.3%) was obtained as a yellow solid. MS: m/z=497.2 [M+H]⁺. ¹H NMR (400 MHz, Dimethylsulfoxide-d₆) δ 9.44 (t, J=6.4 Hz, 1H), 8.71 (d, J=22.0 Hz, 1H), 8.26 (d, J=8.4 Hz, 1H), 8.04-7.96 (m, 4H), 7.50-7.44 (m, 6H), 7.42-7.37 (m, 1H), 7.22-7.19 (m, 1H), 6.93 (d, J=9.2 Hz, 2H), 6.41 (dd, J=7.6, 4.8 Hz, 1H), 4.72-4.64 (m, 1H).

Example 210: 4-((4-(2-(2-aminopyridin-3-yl)-5-phenyl-3H-imidazo[4,5-b]pyridin-3-yl)benzyl)amino)-6-hydroxy-1,3,5-triazine-2-carbonitrile

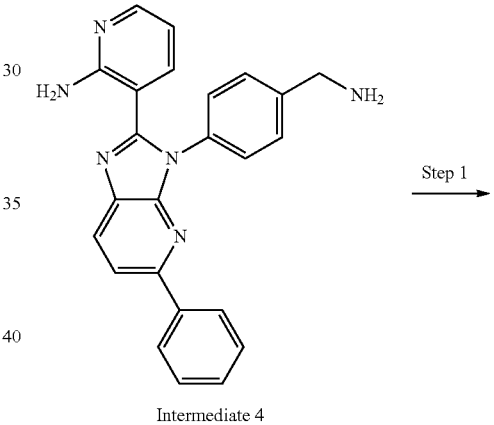

Intermediate 4

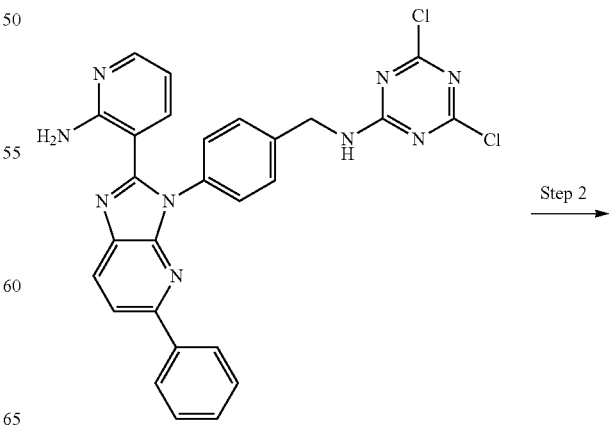

Step 2

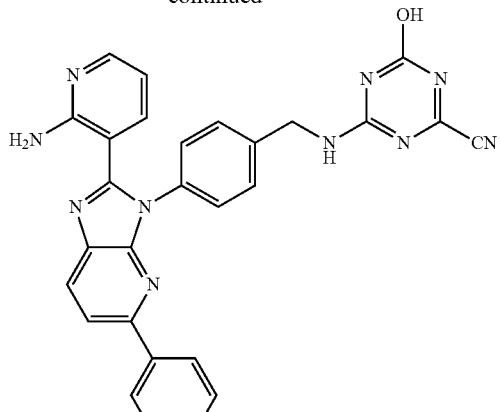

Example 210

Step 1: N-(4-(2-(2-Aminopyridin-3-yl)-5-phenyl-3H-imidazo[4,5-b]pyridin-3-yl)benzyl)-4,6-dichloro-1,3,5-triazin-2-amine Following the general procedure of Example 209 step 1, the reaction of Intermediate 4 (200 mg, 404 μmol) with 2,4,6-trichloro-1,3,5-triazine (103 mg, 561 μmol) was carried out. After silica gel flash chromatography (Eluent of 50~75% EtOAc in petroleum ether), N-(4-(2-(2-aminopyridin-3-yl)-5-phenyl-3H-imidazo[4,5-b]pyridin-3-yl)benzyl)-4,6-dichloro-1,3,5-triazin-2-amine (120 mg, yield: 42%) was obtained as a yellow solid. MS: m/z=540.2 [M+H]$^+$. $^1$H NMR (400 MHz, Dimethylsulfoxide-d$_6$) δ 9.66 (t, J=6.4 Hz, 1H), 8.27 (d, J=8.4 Hz, 1H), 8.05-7.96 (m, 4H), 7.51-7.47 (m, 4H), 7.47-7.43 (m, 2H), 7.42-7.38 (m, 1H), 7.21 (dd, J=7.6, 2.0 Hz, 1H), 6.95 (br s, 2H), 6.41 (dd, J=7.6, 4.8 Hz, 1H), 4.65 (d, J=6.4 Hz, 2H).

Step 2: 4-((4-(2-(2-aminopyridin-3-yl)-5-phenyl-3H-imidazo[4,5-b]pyridin-3-yl)benzyl)amino)-6-hydroxy-1,3,5-triazine-2-carbonitrile To a solution of N-(4-(2-(2-aminopyridin-3-yl)-5-phenyl-3H-imidazo[4,5-b]pyridin-3-yl)benzyl)-4,6-dichloro-1,3,5-triazin-2-amine (130 mg, 241 μmol) in DMSO (3 mL) was added DABCO (5.4 mg, 48.1 μmol) and KCN (50 mg, 768 μmol), the mixture was stirred at 60° C. for 16 hr. The reaction mixture was diluted with H$_2$O (5 mL) and extracted with CH$_2$Cl$_2$ (10 mL×3). The combined organic layers were washed with 10 mL brine, dried over Na$_2$SO$_4$, filtered, and concentrated under reduced pressure to give a residue. After purified by prep-HPLC (column: Welch Xtimate C18 150× 25 mm 5 μm; mobile phase: [water (NH$_4$HCO$_3$)-ACN]; B %: 22%-52%, 12 min), 4-((4-(2-(2-aminopyridin-3-yl)-5-phenyl-3H-imidazo[4,5-b]pyridin-3-yl)benzyl)amino)-6-hydroxy-1,3,5-triazine-2-carbonitrile (Example 210, 5.2 mg, yield: 4.2%) was obtained as a light-yellow lyophilized powder. MS: m/z=513.3 [M+H]$^+$. $^1$H NMR (400 MHz, Dimethylsulfoxide-d$_6$) δ 12.16 (br s, 1H), 8.39 (br s, 1H), 8.27 (d, J=8.4 Hz, 1H), 8.04-7.97 (m, 4H), 7.50-7.44 (m, 6H), 7.42-7.38 (m, 1H), 7.22 (d, J=7.6 Hz, 1H), 6.94 (br s, 2H), 6.42 (dd, J=7.6, 4.8 Hz, 1H), 4.67-4.58 (m, 2H).

Example 211: 4-(8-(4-(2-(2-Aminopyridin-3-yl)-5-phenyl-3H-imidazo[4,5-b]pyridin-3-yl)benzyl)-3,8-diazabicyclo[3.2.1]octan-3-yl)pyrimidine-2-carbonitrile

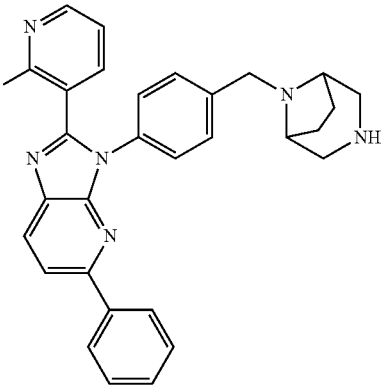

Intermediate 32

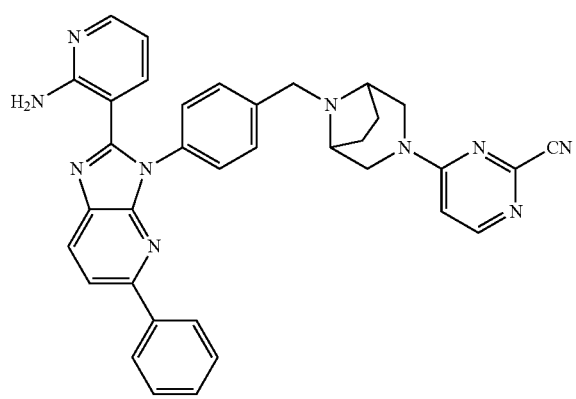

Example 211

Following the general procedure of Example 203, the reaction of Intermediate 32 (80 mg, 164 μmol) with 4-chloropyrimidine-2-carbonitrile (25.2 mg, 180 μmol) was carried out. After purified by prep-HPLC (column: Waters xbridge 150*25 mm 10 μm; mobile phase: [water (NH$_4$HCO$_3$)-ACN]; B %: 50%-80%, 10 min), 4-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-2-carbonitrile (Example 211, 8.4 mg, yield. 8.7%) was obtained as a light-yellow powder. MS: m/z=591.4 [M+H]$^+$. $^1$H NMR (400 MHz, Dimethylsulfoxide-d$_6$) δ 8.27 (d, J=5.6 Hz, 1H), 8.26 (d, J=3.6 Hz, 1H), 8.05-7.97 (m, 4H), 7.59 (d, J=8.4 Hz, 2H), 7.50-7.43 (m, 4H), 7.41-7.37 (m, 1H), 7.18 (dd, J=7.6, 2.0 Hz, 1H), 7.03-7.00 (m, 3H), 6.41 (dd, J=7.6, 4.8 Hz, 1H), 4.28-4.20 (m, 1H), 3.75-3.68 (m, 3H), 3.40-3.37 (m, 2H), 3.24-3.06 (m, 2H), 2.05-2.00 (m, 2H), 1.57-1.50 (m, 2H).

Example 212: 2-(8-(4-(2-(2-Aminopyridin-3-yl)-5-phenyl-3H-imidazo[4,5-b]pyridin-3-yl)benzyl)-3,8-diazabicyclo[3.2.1]octan-3-yl)pyrimidine-4-carbonitrile Example 213: 6-(8-(4-(2-(2-Aminopyridin-3-yl)-5-phenyl-3H-imidazo[4,5-b]pyridin-3-yl)benzyl)-3,8-diazabicyclo[3.2.1]octan-3-yl)pyrimidine-4-carbonitrile

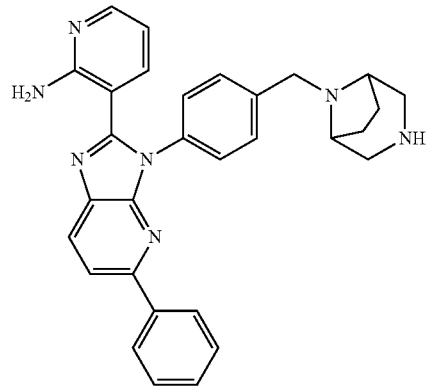

Intermediate 32

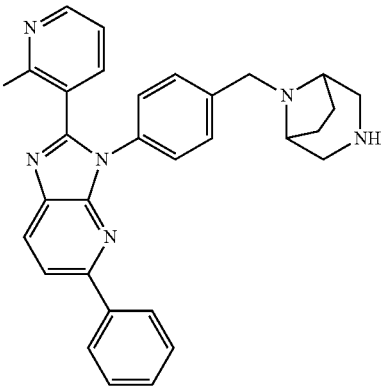

Intermediate 32

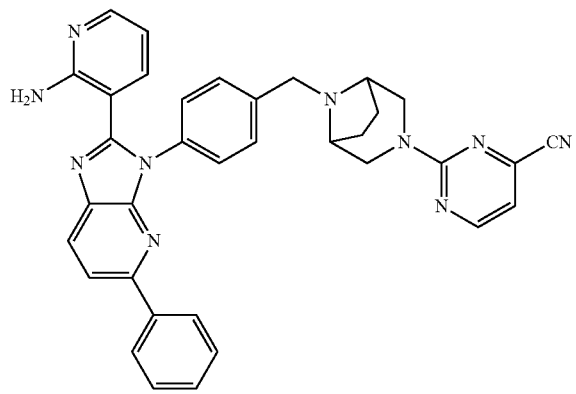

Example 212

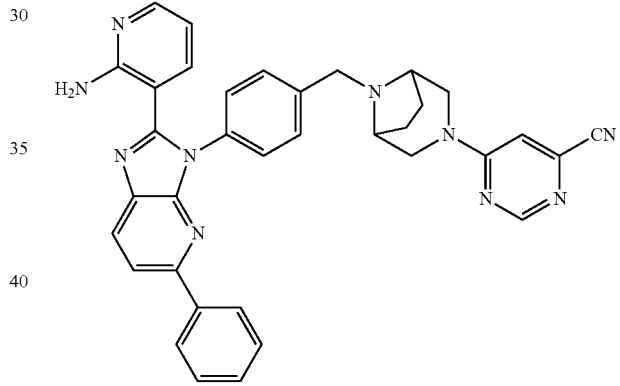

Example 213

Following the general procedure of Example 203, the reaction of Intermediate 32 (80 mg, 164 μmol) with 2-chloropyrimidine-4-carbonitrile (25.2 mg, 180 μmol) was carried out. After purified by prep-HPLC (column: Waters xbridge 150*25 mm 10 μm; mobile phase: [water (NH$_4$HCO$_3$)-ACN]; B %: 57%-87%, 10 min), 2-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-4-carbonitrile (Example 212, 7.3 mg, yield: 7.7%) as a light yellow-powder. MS: m/z=591.3 [M+H]$^+$. $^1$H NMR (400 MHz, Dimethylsulfoxide-d$_6$) δ 8.63 (d, J=4.4 Hz, 1H), 8.27 (d, J=8.4 Hz, 1H), 8.05-7.97 (m, 4H), 7.59 (d, J=8.4 Hz, 2H), 7.50-7.45 (m, 4H), 7.42-7.37 (m, 1H), 7.18 (dd, J=6.0, 1.6 Hz, 1H), 7.16 (d, J=4.4 Hz, 1H), 7.01 (br s, 2H), 6.41 (dd, J=7.6, 4.8 Hz, 1H), 4.25-4.12 (m, 2H), 3.68 (s, 2H), 3.37-3.35 (m, 2H), 3.18-3.16 (m, 2H), 2.03-1.98 (m, 2H), 1.56-1.48 (m, 2H).

Following the general procedure of Example 203, the reaction of Intermediate 32 (80 mg, 164 μmol) with 6-chloropyrimidine-4-carbonitrile (25.2 mg, 180 μmol) was carried out. After purified by prep-HPLC (column: Waters xbridge 150*25 mm 10 μm; mobile phase: [water (NH$_4$HCO$_3$)-ACN]; B %: 50%-80%, 10 min), 6-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-4-carbonitrile (Example 213, 13.2 mg, yield: 13.6%) was obtained as a light-yellow powder. MS: m/z=591.3 [M+H]$^+$. $^1$H NMR (400 MHz, Dimethylsulfoxide-d$_6$) δ 8.56 (s, 1H), 8.27 (d, J=8.4 Hz, 1H), 8.05-7.97 (m, 4H), 7.58 (d, J=8.4 Hz, 2H), 7.50-7.45 (m, 4H), 7.42-7.37 (m, 1H), 7.17 (dd, J=8.0, 1.6 Hz, 1H), 7.01 (br s, 2H), 6.41 (dd, J=7.6, 4.8 Hz, 1H), 4.45-4.30 (m, 1H), 3.78-3.68 (m, 3H), 3.45-3.37 (m, 2H), 3.26-3.18 (m, 2H), 3.14-3.03 (m, 1H), 2.05-2.00 (m, 2H), 1.57-1.46 (m, 2H).

Example 214: 4-(4-(4-(2-(2-Aminopyridin-3-yl)-5-phenyl-3H-imidazo[4,5-b]pyridin-3-yl)benzyl)-1,4-diazepan-1-yl)pyrimidine-2-carbonitrile Example 215: 6-(4-(4-(2-(2-aminopyridin-3-yl)-5-phenyl-3H-imidazo[4,5-b]pyridin-3-yl)benzyl)-1,4-diazepan-1-yl)pyrimidine-4-carbonitrile

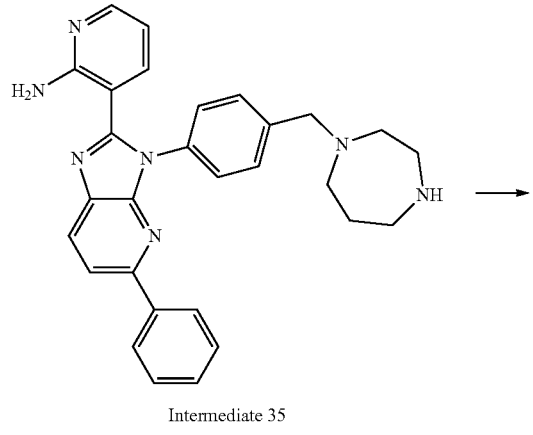

Intermediate 35

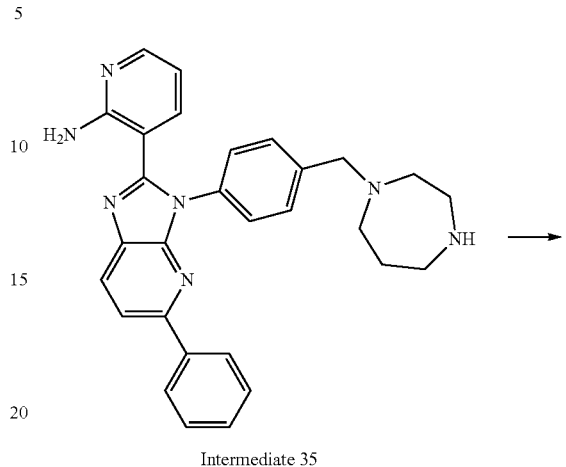

Intermediate 35

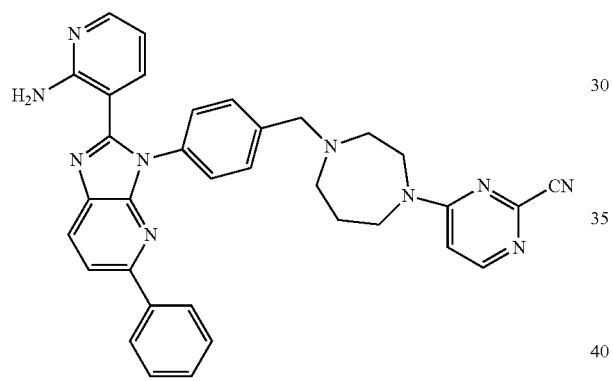

Example 214

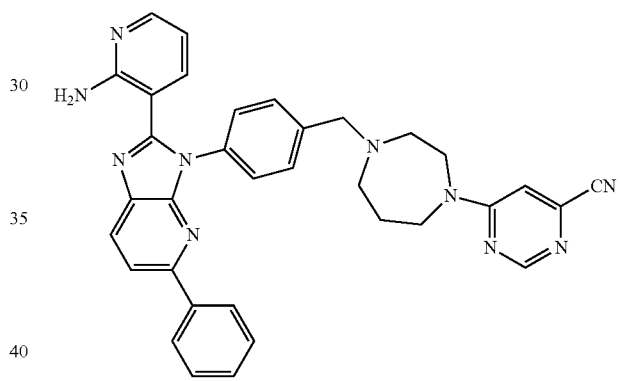

Example 215

Intermediate 35 (70 mg, 147 μmol), 4-chloropyrimidine-2-carbonitrile (20.5 mg, 147 μmol) and DIEA (95.1 mg, 736 μmol) were taken up into a microwave tube in NMP (3 mL). The sealed tube was heated at 160° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with brine (5 mL), dried over Na$_2$SO$_4$, filtered, and concentrated under reduced pressure to give a residue. The residue was purified by prep-TLC (CH2Cl$_2$: MeOH=10:1), 4-(4-(4-(2-(2-Aminopyridin-3-yl)-5-phenyl-3H-imidazo[4,5-b]pyridin-3-yl)benzyl)-1,4-diazepan-1-yl)pyrimidine-2-carbonitrile (Example 214, 8.1 mg, yield: 9.5%) was obtained as a light-yellow solid. MS: m/z=579.2 [M+H]$^+$. $^1$H NMR (400 MHz, Methanol-d$_4$) 8.24-8.10 (m, 2H), 8.07-8.01 (m, 2H), 7.99-7.99 (m, 1H), 7.95-7.91 (m, 1H), 7.52 (d, J=8.0 Hz, 2H), 7.46-7.40 (m, 4H), 7.40-7.29 (m, 2H), 6.89-6.80 (m, 1H), 6.52-6.41 (m, 1H), 4.02-3.91 (m, 2H), 3.77 (s, 2H), 3.68-3.59 (m, 2H), 2.88-2.82 (m, 2H), 2.75-2.68 (m, 2H), 2.04-1.95 (m, 2H).

Intermediate 35 (80 mg, 168 μmol), 6-chloropyrimidine-4-carbonitrile (23.5 mg, 168 μmol) and DIEA (109 mg, 841 μmol) were taken up into a microwave tube in NMP (3 mL). The sealed tube was heated at 130° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with brine (15 mL), dried over Na$_2$SO$_4$, filtered, and concentrated under reduced pressure to give a residue. The residue was purified by prep-TLC (CH$_2$Cl$_2$: MeOH=10:1), 6-(4-(4-(2-(2-aminopyridin-3-yl)-5-phenyl-3H-imidazo[4,5-b]pyridin-3-yl)benzyl)-1,4-diazepan-1-yl)pyrimidine-4-carbonitrile (Example 215, 14.0 mg, yield: 14.4%) was obtained as a yellow solid. MS: m/z=579.3 [M+H]$^+$. $^1$H NMR (400 MHz, Dimethylsulfoxide-d$_6$) 8.56 (d, J=5.6 Hz, 1H), 8.27 (d, J=8.4 Hz, 1H), 8.08-7.96 (m, 4H), 7.49-7.37 (m, 8H), 7.13 (d, J=7.6 Hz, 1H), 7.05 (br s, 2H), 6.41-6.29 (m, 1H), 3.93-3.83 (m, 2H), 3.73 (d, J=8.0 Hz, 2H), 3.68-3.59 (m, 2H), 2.77-2.72 (m, 2H), 2.63-2.58 (m, 2H), 1.93-1.82 (m, 2H).

Example 216: 4-((1R,4R)-5-(4-(2-(2-Aminopyridin-3-yl)-5-phenyl-3H-imidazo[4,5-b]pyridin-3-yl)benzyl)-2,5-diazabicyclo[2.2.1]heptan-2-yl)pyrimidine-2-carbonitrile

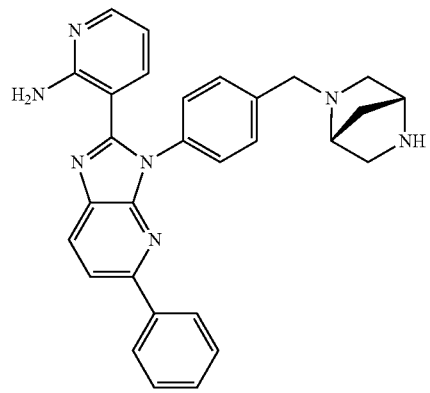

Intermediate 37

→

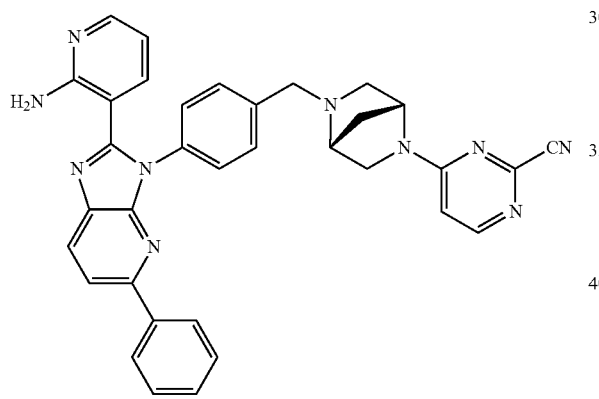

Example 216

Example 217: 2-((1R,4R)-5-(4-(2-(2-Aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile

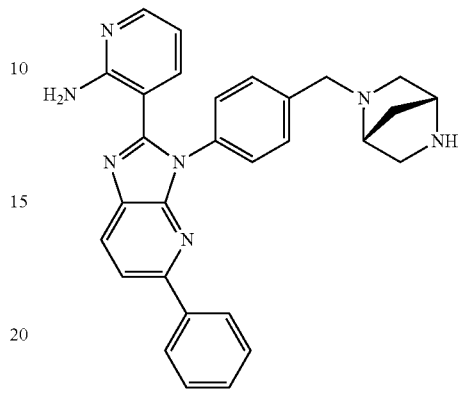

Intermediate 37

→

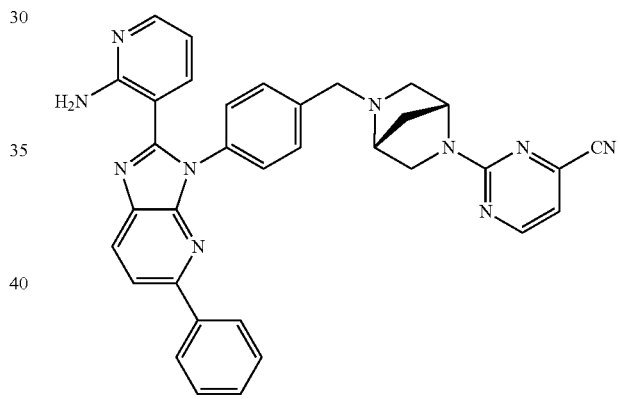

Example 217

To a solution of Intermediate 37 (80 mg, 169 μmol) and 4-chloropyrimidine-2-carbonitrile (23.6 mg, 169 μmol) in NMP (2 mL) was added DIEA (109 mg, 845 μmol). The mixture was stirred under microwave at 130° C. for 0.5 hr. The reaction was filtered and concentrated under reduced pressure to give a residue. The crude product was purified by prep-HPLC (column: Waters xbridge 150*25 mm 10 μm; mobile phase: [water (NH$_4$HCO$_3$)-ACN]; B %: 48%-78%, 10 min), 4-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-2-carbonitrile (Example 216, 22 mg, yield: 23%) was obtained as a yellow solid. MS: m/z=577.3 [M+H]$^+$. $^1$H NMR (400 MHz, Dimethylsulfoxide-d$_6$) δ 8.27-8.18 (m, 2H), 8.03-7.97 (m, 4H), 7.52-7.37 (m, 8H), 7.16 (dd, J=7.6, 1.6 Hz, 1H), 6.99 (br s, 2H), 6.41-6.37 (m, 1H), 4.89-4.68 (m, 1H), 3.84 (s, 2H), 3.70-3.67 (m, 2H), 3.56-3.53 (m, 1H), 3.42-3.41 (m, 1H), 2.94 (t, J=8.0 Hz, 1H), 2.07-1.97 (m, 1H), 1.86-1.78 (m, 1H).

To a solution of Intermediate 37 (80 mg, 169 μmol) and 2-chloropyrimidine-4-carbonitrile (23.6 mg, 169 μmol) in NMP (2 m L) was added DIEA (109 mg, 845 μmol). The mixture was stirred under microwave at 130° C. for 0.5 hr. The reaction was filtered and concentrated under reduced pressure to give a residue. The crude product was purified by prep-HPLC (column: Waters xbridge 150*25 mm 10 μm; mobile phase: [water (NH$_4$HCO$_3$)-ACN]; B %: 48%-78%, 10 min), 2-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile (Example 217, 27.2 mg, yield: 28%) was obtained as a yellow solid. MS: m/z=577.4 [M+H]$^+$. $^1$H NMR (400 MHz, Dimethylsulfoxide-d$_6$) δ 8.63-8.59 (m, 1H), 8.26 (d, J=8.4 Hz, 1H), 8.05-7.95 (m, 4H), 7.51-7.37 (m, 7H), 7.16 (dd, J=8.0, 1.6 Hz, 1H), 7.12 (d, J=4.4 Hz, 1H), 6.99 (br s, 2H), 6.39 (dd, J=7.6, 5.2 Hz, 1H), 4.81-4.73 (m, 1H), 3.87 (s, 2H), 3.69-3.62 (m, 2H), 3.45-3.40 (m, 2H), 2.96-2.94 (m, 1H), 1.99-1.97 (m, 1H), 1.84-1.82 (m, 1H).

Example 218: 6-((1R,4R)-5-(4-(2-(2-Aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile Example 219: 4-(5-(4-(2-(2-Aminopyridin-3-yl)-5-phenyl-3H-imidazo[4,5-b]pyridin-3-yl)benzyl)-2,5-diazabicyclo[2.2.2]octan-2-yl)pyrimidine-2-carbonitrile

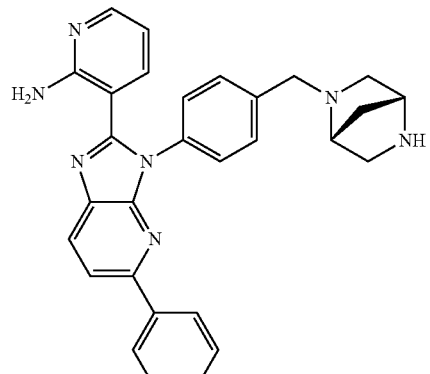

Intermediate 37

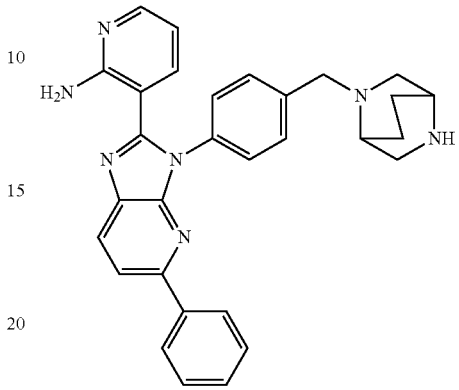

Intermediate 38

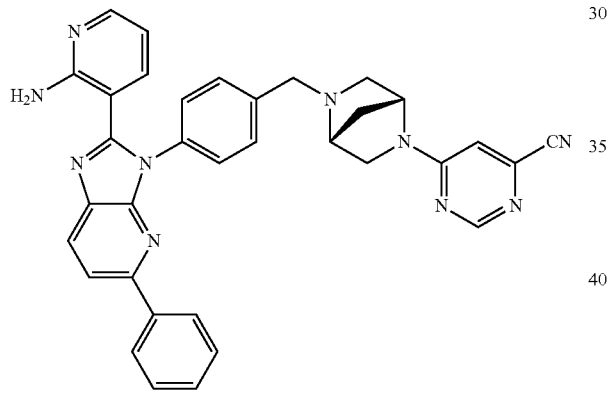

Example 218

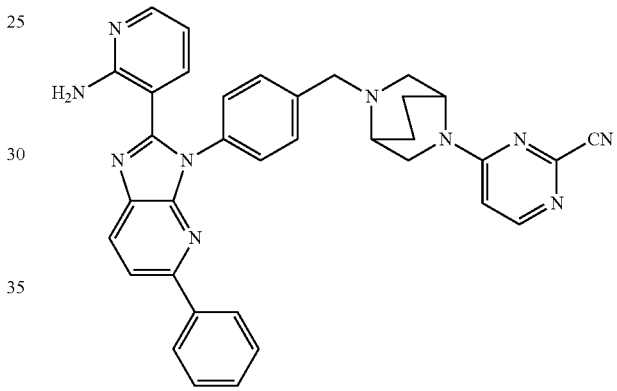

Example 219

To a solution of Intermediate 37 (80 mg, 169 μmol) and 6-chloropyrimidine-4-carbonitrile (23.6 mg, 169 μmol) in NMP (2 mL) was added DIEA (109 mg, 845 μmol). The mixture was stirred under microwave at 130° C. for 0.5 hr. The reaction was filtered and concentrated under reduced pressure to give a residue. The crude product was purified by prep-HPLC (column: Waters xbridge 150*25 mm 10 μm; mobile phase: [water (NH$_4$HCO$_3$)-ACN]; B %: 50%-80%, 10 min), 6-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile (Example 218, 11.4 mg, yield: 11.7%) was obtained as a yellow solid. MS: m/z=577.4 [M+H]$^+$. $^1$H NMR (400 MHz, Dimethylsulfoxide-d$_6$) δ 8.52 (d, J=12.4 Hz, 1H), 8.26 (d, J=8.4 Hz, 1H), 8.04-8.00 (m, 3H), 7.99-7.97 (m, 1H), 7.51-7.41 (m, 7H), 7.17-7.15 (m, 2H), 6.99 (br s, 2H), 6.39 (dd, J=7.6, 4.8 Hz, 1H), 4.94-4.71 (m, 1H), 3.84-3.82 (m, 2H), 3.72-3.67 (m, 2H), 3.60-3.58 (m, 1H), 3.43-3.42 (m, 1H), 2.95-2.90 (m, 1H), 2.04-1.97 (m, 1H), 1.8-1.78 (m, 1H).

Intermediate 38 (100 mg, 205 μmol), 4-chloropyrimidine-2-carbonitrile (28.6 mg, 206 μmol) and DIEA (132 mg, 1.0 mmol) were taken up into a microwave tube in NMP (2 mL). The sealed tube was heated at 130° C. for 1 hr under microwave. The reaction mixture was quenched with H$_2$O (5 mL) at 0° C., and then diluted with 10 mL CH$_2$Cl$_2$ (10 mL) and extracted with CH$_2$Cl$_2$ (15 mL×2). The combined organic layers were washed with 15 mL aqueous NaCl, dried over Na$_2$SO$_4$, filtered, and concentrated under reduced pressure to give a residue. After purified by prep-HPLC (column: Waters xbridge 150×25 mm 10 μm; mobile phase: [water (NH$_4$HCO$_3$)-ACN]; B %: 52%-82%, 8 min), 4-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-2-carbonitrile (Example 219, 24.4 mg, yield: 20%) was obtained as a yellow lyophilized powder. MS: m/z=591.3 [M+H]$^+$. $^1$H NMR (400 MHz, Dimethylsulfoxide-d$_6$) 8.28-8.18 (m, 2H), 8.04-7.97 (m, 4H), 7.53 (d, J=8.4 Hz, 2H), 7.49-7.43 (m, 4H), 7.42-7.37 (m, 1H), 7.16 (dd, J=7.6, 1.6 Hz, 1H), 7.01 (s, 2H), 6.76 (d, J=6.4 Hz, 1H), 6.42-6.35 (m, 1H), 4.76-4.73 (m, 0.6H), 4.24-4.21 (m, 0.4H), 3.89-3.80 (m, 3H), 3.49-3.52 (m, 1H), 3.02-3.07 (m, 1H), 2.94-2.88 (m, 2H), 2.20-2.03 (m, 1H), 1.89-1.80 (m, 2H), 1.71-1.63 (m, 1H).

Example 220: 2-(5-(4-(2-(2-Aminopyridin-3-yl)-5-phenyl-3H-imidazo[4,5-b]pyridin-3-yl)benzyl)-2,5-diazabicyclo[2.2.2]octan-2-yl)pyrimidine-4-carbonitrile

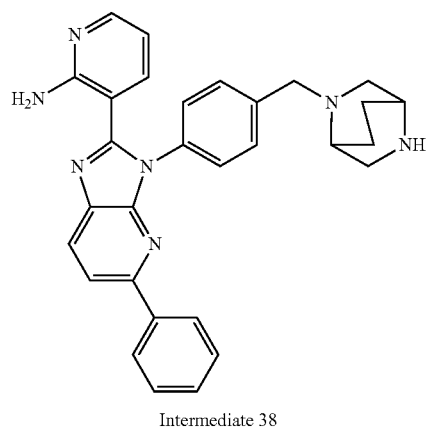

Intermediate 38

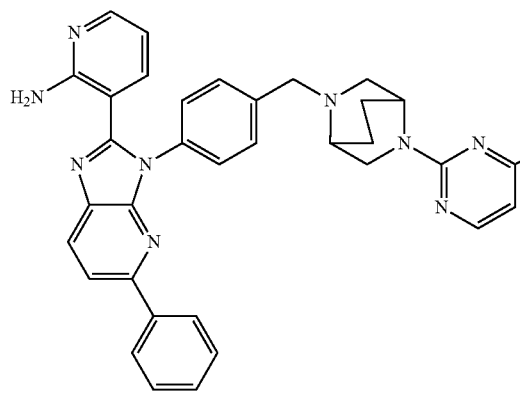

Example 220

Intermediate 38 (100 mg, 205 μmol), 4-chloropyrimidine-2-carbonitrile (28.6 mg, 206 μmol) and DIEA (132 mg, 1.0 mmol) were taken up into a microwave tube in NMP (2 mL). The sealed tube was heated at 130° C. for 1 hr under microwave. The reaction mixture was quenched with $H_2O$ (5 mL) at 0° C., and then diluted with $CH_2Cl_2$ (10 mL) and extracted with $CH_2Cl_2$ (15 mL×2). The combined organic layers were washed with brine (15 mL), dried over $Na_2SO_4$, filtered, and concentrated under reduced pressure to give a residue. After purified by prep-HPLC (column: Waters xbridge 150×25 mm 10 μm; mobile phase: [water ($NH_4HCO_3$)-ACN]; B %: 55%-85%, 10 min), 2-(5-(4-(2-(2-Aminopyridin-3-yl)-5-phenyl-3H-imidazo[4,5-b]pyridin-3-yl)benzyl)-2,5-diazabicyclo[2.2.2]octan-2-yl)pyrimidine-4-carbonitrile (Example 220, 18.9 mg, yield: 15%) was obtained as a yellow lyophilized powder. MS: m/z=591.4 [M+H]$^+$. $^1$H NMR (400 MHz, Dimethylsulfoxide-d$_6$) 8.68-8.54 (m, 1H), 8.27 (d, J=8.0 Hz, 1H), 8.06-7.95 (m, 4H), 7.53 (d, J=8.4 Hz, 2H), 7.49-7.43 (m, 4H), 7.42-7.37 (m, 1H), 7.16 (dd, J=7.6, 2.0 Hz, 1H), 7.11 (d, J=4.8 Hz, 1H), 7.02 (s, 2H), 6.39 (dd, J=7.6, 4.8 Hz, 1H), 4.73-4.55 (m, 1H), 3.92-3.80 (m, 3H), 3.49-3.44 (m, 1H), 3.03-3.05 (m, 1H), 2.96-2.85 (m, 2H), 2.16-2.06 (m, 1H), 1.89-1.79 (m, 2H), 1.71-1.61 (m, 1H).

Example 221: 6-(5-(4-(2-(2-Aminopyridin-3-yl)-5-phenyl-3H-imidazo[4,5-b]pyridin-3-yl)benzyl)-2,5-diazabicyclo[2.2.2]octan-2-yl)pyrimidine-4-carbonitrile

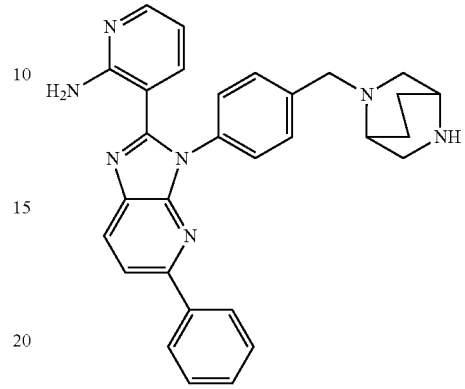

Intermediate 38

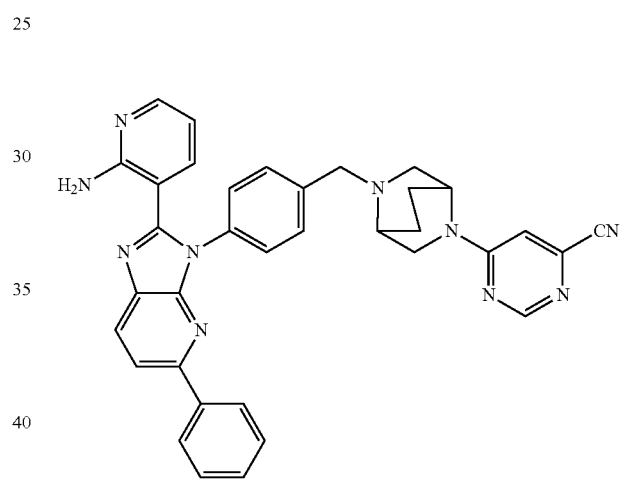

Example 221

Intermediate 38 (100 mg, 205 μmol), 4-chloropyrimidine-2-carbonitrile (28.6 mg, 206 μmol) and DIEA (132 mg, 1.0 mmol) were taken up into a microwave tube in NMP (2 mL). The sealed tube was heated at 130° C. for 1 hr under microwave. The reaction mixture was quenched with $H_2O$ (5 mL) at 0° C., and then diluted with $CH_2Cl_2$ (10 mL) and extracted with $CH_2Cl_2$ (15 mL×2). The combined organic layers were washed with brine (15 mL), dried over $Na_2SO_4$, filtered and concentrated under reduced pressure to give a residue. After purified by prep-HPLC (column: Waters xbridge 150×25 mm 10 μm; mobile phase: [water ($NH_4HCO_3$)-ACN]; B %: 48-78%, 10 min), 6-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-4-carbonitrile (Example 221, 17.8 mg, yield: 14%) was obtained as a yellow lyophilized powder. MS: m/z=591.3 [M+H]$^+$. $^1$H NMR (400 MHz, Dimethylsulfoxide-d$_6$) 8.60-8.48 (m, 1H), 8.27 (d, J=8.4 Hz, 1H), 8.05-7.97 (m, 4H), 7.52 (d, J=8.4 Hz, 2H), 7.49-7.43 (m, 4H), 7.42-7.37 (m, 1H), 7.24-7.10 (m, 2H), 7.01 (s, 2H), 6.40-6.36 (m, 1H), 4.25-4.85 (m, 1H), 3.90-3.78 (m, 3H), 3.56-3.49 (m, 1H), 3.05-3.07 (m, 1H), 2.94-2.86 (m, 2H), 2.17-2.08 (m, 1H), 1.90-1.79 (m, 2H), 1.71-1.63 (m, 1H).

Example 222: 4-((1-((4-(2-(2-Aminopyridin-3-yl)-5-phenyl-3H-imidazo[4,5-h]pyridin-3-yl)phenyl)methyl-d2)piperidin-4-yl)amino)pyrimidine-2-carbonitrile

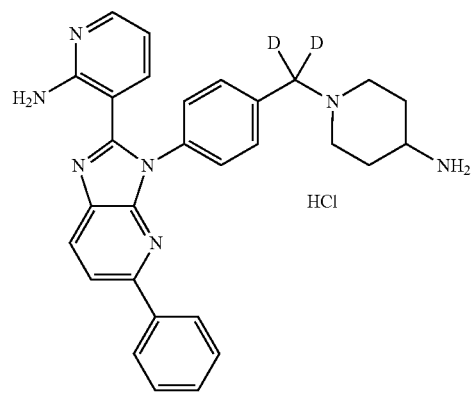

Intermediate 40

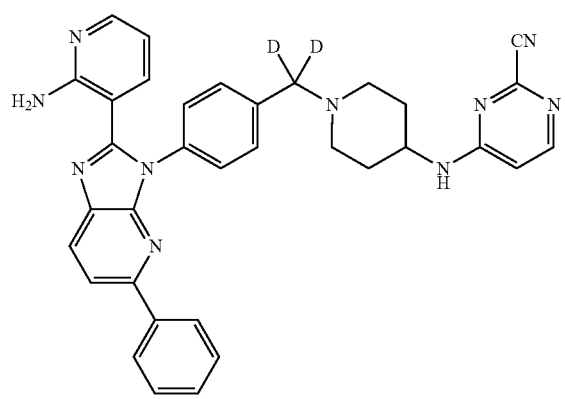

Example 222

To a solution of Intermediate 40 (50.0 mg, 105 μmol) in NMP (1 mL) were added 4-chloropyrimidine-2-carbonitrile (16.1 mg, 115 μmol) and DIEA (67.6 mg, 523 μmol, 91.2 μL) under $N_2$ atmosphere. The mixture was stirred at 130° C. for 30 min under microwave. Water (5 mL) was added to the mixture and the mixture was extracted with EtOAc (3×5 mL). The combined organic layers were washed with brine (10 mL), dried over $Na_2SO_4$, filtered, and concentrated. The residue was purified by prep-HPLC (column: Phenomenex C18 80*40 mm*3 μm; mobile phase: [water ($NH_4OH$+ $NH_4HCO_3$)-ACN]; B %: 51%-81%, 8 min) to give 4-((1-((4-(2-(2-Aminopyridin-3-yl)-5-phenyl-3H-imidazo[4,5-h]pyridin-3-yl)phenyl)methyl-d2)piperidin-4-yl)amino)pyrimidine-2-carbonitrile (Example 222, 20.3 mg, yield: 33%) was obtained as an off-white solid. MS: m/z=581.3 [M+H]$^+$. $^1$H NMR (400 MHz, Methanol-$d_4$) δ 8.24 (d, J=8.4 Hz, 1H), 8.10 (d, J=6.0 Hz, 1H), 8.04-7.95 (m, 4H), 7.77 (d, J=8.4 Hz, 2H), 7.67 (d, J=8.0 Hz, 2H), 7.50-7.38 (m, 4H), 6.67 (s, 1H), 6.59 (dd, J=7.6, 5.6 Hz, 1H), 4.25-4.19 (m, 1H), 3.62-3.58 (m, 2H), 3.38-3.33 (m, 1H), 3.29-3.19 (m, 1H), 2.29-2.26 (m, 2H), 1.86-1.80 (m, 2H).

Example 223: 4-((1-(4-(2-(2-aminopyridin-3-yl)-5-phenyl-3H-imidazo[4,5-b]pyridin-3-yl)benzyl)piperidin-4-yl)(methyl)amino)-1,3,5-triazine-2-carbonitrile

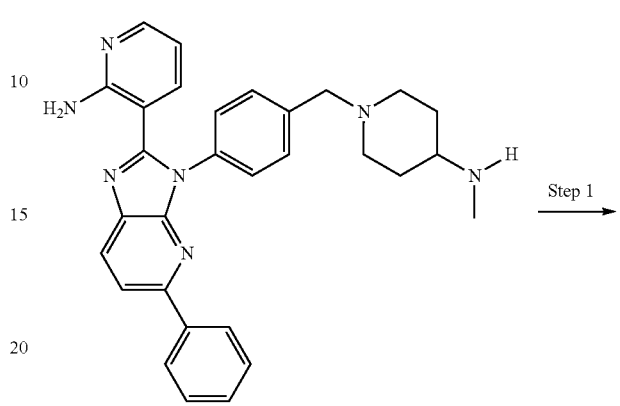

Intermediate 36

Step 1

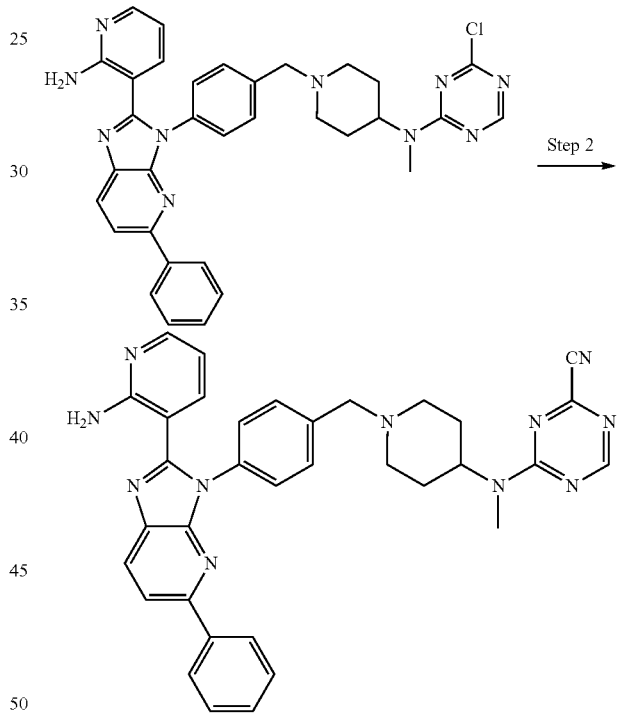

Example 223

Step 1: N-(1-(4-(2-(2-Aminopyridin-3-yl)-5-phenyl-3H-imidazo[4,5-b]pyridin-3-yl)benzyl)piperidin-4-yl)-4-chloro-N-methyl-1,3,5-triazin-2-amine To a solution of Intermediate 36 (110 mg, 225 μmol) in THF (15 mL) was added DIEA (87.1 mg, 674 μmol). The mixture was stirred at 0° C. for 10 min. Then 2,4-dichloro-1,3,5-triazine (37.1 mg, 247 μmol) in THF (2 mL) was added to the mixture. The mixture was stirred at 0° C. for 1 hr. The reaction mixture was concentrated, and purified by silica gel flash chromatography (Eluent of 0~100% EtOAc in petroleum ether) to give N-(1-(4-(2-(2-aminopyridin-3-yl)-5-phenyl-3H-imidazo[4,5-b]pyridin-3-yl)benzyl)piperidin-4-yl)-

4-chloro-N-methyl-1,3,5-triazin-2-amine. (40 mg, yield: 30%) as a light-yellow solid. MS: m/z=603.2 [M+H]⁺.

Step 2: 4-((1-(4-(2-(2-Aminopyridin-3-yl)-5-phenyl-3H-imidazo[4,5-b]pyridin-3-yl)benzyl)piperidin-4-yl)(methyl)amino)-1,3,5-triazine-2-carbonitrile To a solution of N-(1-(4-(2-(2-aminopyridin-3-yl)-5-phenyl-3H-imidazo[4,5-b]pyridin-3-yl)benzyl)piperidin-4-yl)-4-chloro-N-methyl-1,3,5-triazin-2-amine (40 mg, 66.3 μmol) in DMSO (1 mL) were added KCN (13.0 mg, 199 μmol) and DABCO (1.5 mg, 13.3 μmol). The mixture was stirred at 25° C. for 1 hr. The reaction mixture was poured into water (5 mL). The resulting mixture was extracted with CH₂Cl₂ (5 mL×2). The combined organic layers were washed with brine (5 ml) and dried over anhydrous Na₂SO₄, filtered and concentrated under reduced pressure. The residue was purified by prep-HPLC (column: Waters xbridge 150*25 mm 10 um; mobile phase: [water (NH₄HCO₃)-ACN]; gradient: 53%-83% B over 14 min) to give 4-((1-(4-(2-(2-aminopyridin-3-yl)-5-phenyl-3H-imidazo[4,5-b]pyridin-3-yl)benzyl)piperidin-4-yl)(methyl)amino)-1,3,5-triazine-2-carbonitrile (Example 223, 14.0 mg, yield: 36%) as a yellow solid. MS: m/z=594.2 [M+H]⁺. ¹H NMR (400 MHz, Acetonitrile-d₃) δ 8.58 (d, J=6.8 Hz, 1H), 8.20 (d, J=8.4 Hz, 1H), 8.11-7.99 (m, 3H), 7.93 (d, J=8.4 Hz, 1H), 7.57-7.52 (m, 2H), 7.51-7.40 (m, 5H), 7.18 (dd, J=7.6, 1.2 Hz, 1H), 6.60 (br s, 2H), 6.41 (dd, J=7.6, 4.8 Hz, 1H), 4.63-4.53 (m, 1H), 3.66 (d, J=4.4 Hz, 2H), 3.11-3.07 (m, 3H), 3.07-3.01 (m, 2H), 2.23-2.19 (m, 2H), 1.95-1.88 (m, 2H), 1.72-1.69 (m, 2H).

Example 224: (S)-4-((1-(4-(2-(2-Aminopyridin-3-yl)-5-phenyl-3H-imidazo[4,5-b]pyridin-3-yl)benzyl)piperidin-3-yl)amino)-1,3,5-triazine-2-carbonitrile

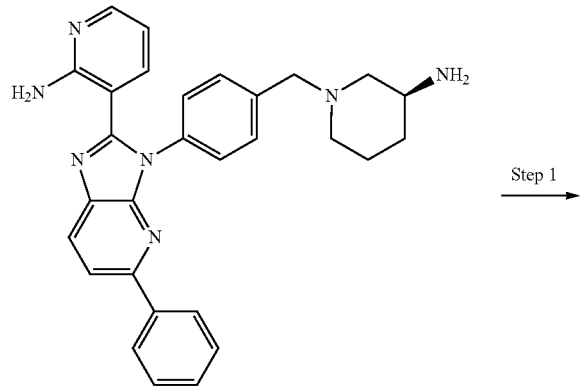

Intermediate 173

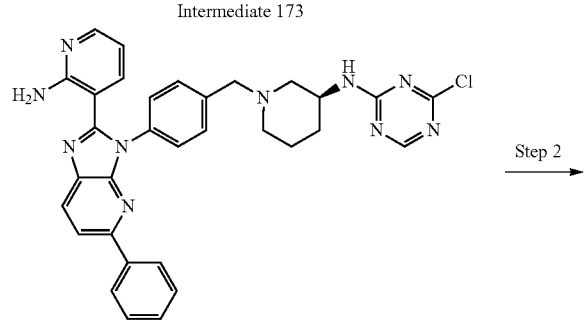

Step 2

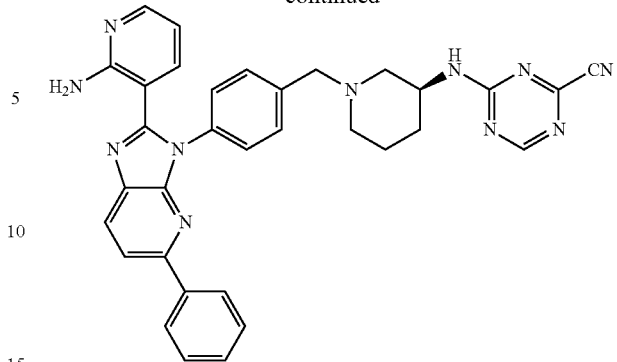

Example 224

Step 1: (S)—N-(1-(4-(2-(2-Aminopyridin-3-yl)-5-phenyl-3H-imidazo[4,5-b]pyridin-3-yl)benzyl)piperidin-3-yl)-4-chloro-1,3,5-triazin-2-amine To a solution of Intermediate 173 (50 mg, 105 mol) in THF (8 mL) was added DIEA (40.7 mg, 315 μmol). The 2,4-dichloro-1,3,5-triazine (17.3 mg, 116 μmol) in THF (2 mL) was added into the mixture at 0° C. The mixture was stirred at 0° C. for 0.5 hr. The mixture was concentrated under reduced pressure. After purified by prep-TLC (EtOAc), (S)—N-(1-(4-(2-(2-aminopyridin-3-yl)-5-phenyl-3H-imidazo[4,5-b]pyridin-3-yl)benzyl)piperidin-3-yl)-4-chloro-1,3,5-triazin-2-amine (14.9 mg, yield: 23%) was obtained as a light-yellow solid. MS: m/z=589.3 [M+H]⁺. ¹H NMR (400 MHz, Methanol-d₄) δ 8.32-8.26 (m, 1H), 8.18 (d, J=8.4 Hz, 1H), 8.05-7.99 (m, 2H), 7.98-7.91 (m, 2H), 7.59-7.50 (m, 2H), 7.46-7.33 (m, 5H), 7.31-7.26 (m, 1H), 6.42-6.37 (m, 1H), 4.13-4.09 (m, 1H), 3.73-3.62 (m, 2H), 2.96-2.91 (m, 1H), 2.81-2.72 (m, 1H), 2.33-2.09 (m, 2H), 1.93-1.90 (m, 1H), 1.84-1.77 (m, 1H), 1.73-1.63 (m, 1H), 1.52-1.38 (m, 1H).

Step 2: (S)-4-((1-(4-(2-(2-Aminopyridin-3-yl)-5-phenyl-3H-imidazo[4,5-b]pyridin-3-yl)benzyl)piperidin-3-yl)amino)-1,3,5-triazine-2-carbonitrile To a solution of (S)—N-(1-(4-(2-(2-aminopyridin-3-yl)-5-phenyl-3H-imidazo[4,5-b]pyridin-3-yl)benzyl)piperidin-3-yl)-4-chloro-1,3,5-triazin-2-amine (50 mg, 84.9 μmol) in DMSO (1 mL) were added KCN (60 mg, 921 μmol) and DABCO (1.9 mg, 17 μmol). The mixture was stirred at 25° C. for 2 hr. The reaction mixture was poured into H₂O (10 mL). The resulting mixture was extracted with EtOAc (10 mL×2). The combined organic layers were washed with brine (10 mL) and dried over anhydrous Na₂SO₄, filtered and concentrated. After purified by silica gel flash chromatography (Eluent of 0~8% MeOH in CH₂Cl₂), (S)-4-((1-(4-(2-(2-Aminopyridin-3-yl)-5-phenyl-3H-imidazo[4,5-b]pyridin-3-yl)benzyl)piperidin-3-yl)amino)-1,3,5-triazine-2-carbonitrile (Example 224, 10 mg, yield: 18%) as a light-yellow solid. MS: m/z=580.3 [M+H]⁺. 1 H NMR (400 MHz, Dimethylsulfoxide-d₆) δ 8.86 (dd, J=8.4, 2.8 Hz, 1H), 8.64 (d, J=16.0 Hz, 1H), 8.27 (d, J=8.0 Hz, 1H), 8.04-7.99 (m, 3H), 7.97-7.96 (m, 1H), 7.52-7.48 (m, 2H), 7.46-7.43 (m, 4H), 7.40-7.36 (m, 1H), 7.15-7.12 (m, 1H), 7.03 (d, J=8.4 Hz, 2H), 6.33-6.27 (m, 1H), 4.02-3.93 (m, 1H), 3.62 (d, J=8.0 Hz, 2H), 2.91-2.84 (m, 1H), 2.74-2.69 (m, 1H), 2.03-1.98 (m, 2H), 1.87-1.82 (m, 1H), 1.76-1.71 (m, 1H), 1.57-1.50 (m, 1H), 1.36-1.32 (m, 1H).

Example 225: (R)-4-(4-(4-(2-(2-Aminopyridin-3-yl)-5-phenyl-3H-imidazo[4,5-h]pyridin-3-yl)benzyl)-2-methylpiperazin-1-yl)pyrimidine-2-carbonitrile

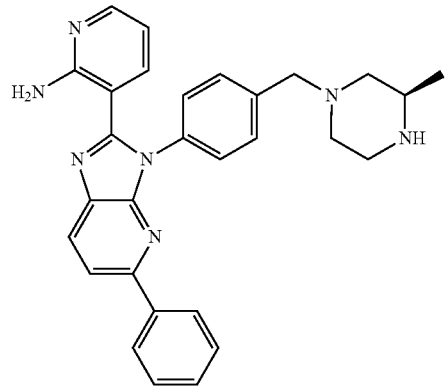

Intermediate 164

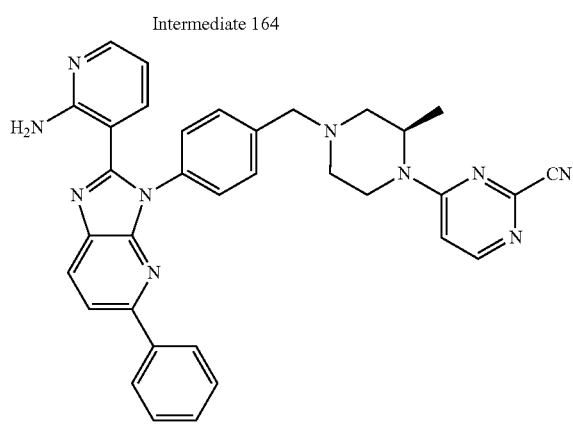

Example 225

A mixture of Intermediate 164 (100 mg, 210 µmol), 4-chloropyrimidine-2-carbonitrile (29.3 mg, 210 µmol) and DIEA (136 mg, 1.05 mmol) in NMP (2 mL) was taken up into a microwave tube. The sealed tube was heated at 130° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with brine (15 mL), dried over Na$_2$SO$_4$, filtered and concentrated under reduced pressure. After purified by prep-HPLC (column: Welch Xtimate C18 150×25 mm×5 µm; mobile phase: [water (HCl)-ACN]; B %: 13%-43%, 10 min), (R)-4-(4-(4-(2-(2-aminopyridin-3-yl)-5-phenyl-3H-imidazo[4,5-b]pyridin-3-yl)benzyl)-2-methylpiperazin-1-yl)pyrimidine-2-carbonitrile (Example 225, 14.5 mg HCl salt, yield: 12%) was obtained as a yellow solid. MS: m/z=579.3 [M+H]$^+$. $^1$H NMR (400 MHz, Methanol-d$_4$) δ 8.36-8.31 (m, 2H), 8.05-8.01 (m, 4H), 7.92 (d, J=8.4 Hz, 2H), 7.87 (dd, J=7.6, 1.2 Hz, 1H), 7.76 (d, J=8.4 Hz, 2H), 7.47-7.41 (m, 3H), 7.09 (d, J=6.4 Hz, 1H), 6.87 (dd, J=7.6, 6.4 Hz, 1H), 3.72 (d, J=11.6 Hz, 1H), 3.63-3.55 (m, 2H), 3.49-3.36 (m, 2H), 3.35-3.31 (m, 2H), 2.86-2.66 (m, 2H), 1.46 (d, J=6.8 Hz, 3H).

Example 226: (R)-2-(4-(4-(2-(2-Aminopyridin-3-yl)-5-phenyl-3H-imidazo[4,5-b]pyridin-3-yl)benzyl)-2-methylpiperazin-1-yl)pyrimidine-4-carbonitrile

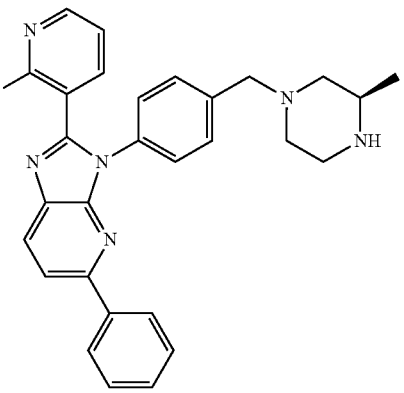

Intermediate 164

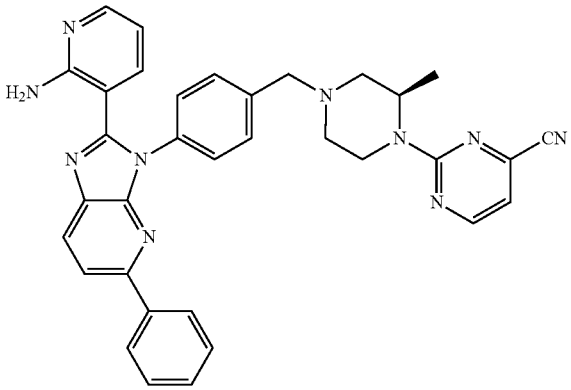

Example 226

A mixture of Intermediate 164 (100 mg, 210 µmol), 2-chloropyrimidine-4-carbonitrile (29.3 mg, 210 µmol) and DIEA (136 mg, 1.05 mmol) in NMP (3 mL) was taken up into a microwave tube. The sealed tube was heated at 130° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with brine (15 mL), dried over Na$_2$SO$_4$, filtered, and concentrated under reduced pressure. After purified by prep-HPLC (column: Welch Xtimate C18 150×25 mm×5 µm; mobile phase: [water (HCl)-ACN]; B %: 15%-45%, 10 min), (R)-2-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile (Example 226, 14.1 mg, yield: 11%) was obtained as a yellow solid. MS: m/z=579.3 [M+H]$^+$. $^1$H NMR (400 MHz, Methanol-d$_4$) δ 8.65 (d, J=4.8 Hz, 1H), 8.33 (d, J=8.4 Hz, 1H), 8.06-8.01 (m, 4H), 7.92 (d, J=8.0 Hz, 2H), 7.87 (d, J=7.2 Hz, 1H), 7.76 (d, J=8.0 Hz, 2H), 7.47-7.40 (m, 3H), 7.10 (d, J=4.8 Hz, 1H), 6.86 (t, J=0.2 Hz, 1H), 3.71 (d, J=10.41 Hz, 1H), 3.55 (t, J=12.4 Hz, 2H), 3.49-3.32 (m, 4H), 3.30-3.19 (m, 2H), 1.43 (d, J=7.2 Hz, 3H).

Example 227: (R)-6-(4-(4-(2-(2-Aminopyridin-3-yl)-5-phenyl-3H-imidazo[4,5-b]pyridin-3-yl)benzyl)-2-methylpiperazin-1-yl)pyrimidine-4-carbonitrile

Example 228: 2-(4-(4-(2-(2-Aminopyridin-3-yl)-5-phenyl-3H-imidazo[4,5-b]pyridin-3-yl)benzyl)-1,4-diazepan-1-yl)pyrimidine-4-carbonitrile

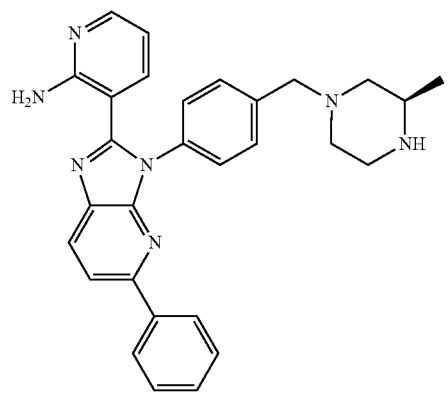

Intermediate 164

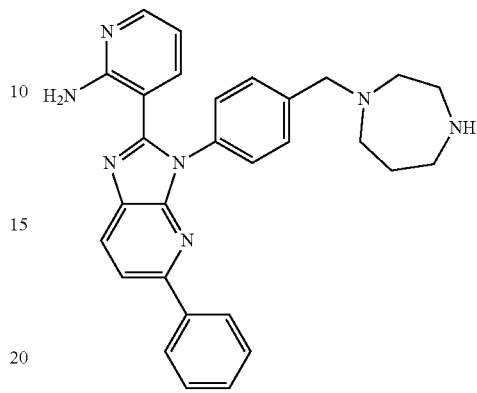

Intermediate 35

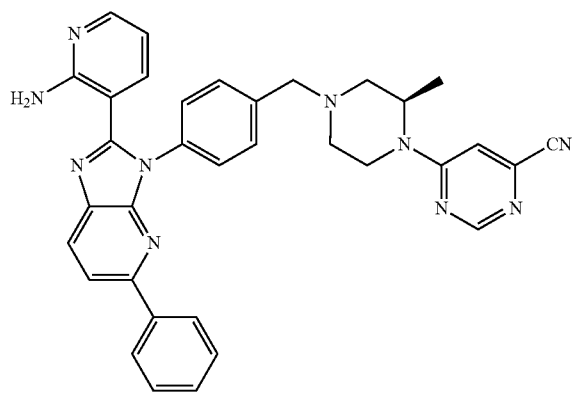

Example 227

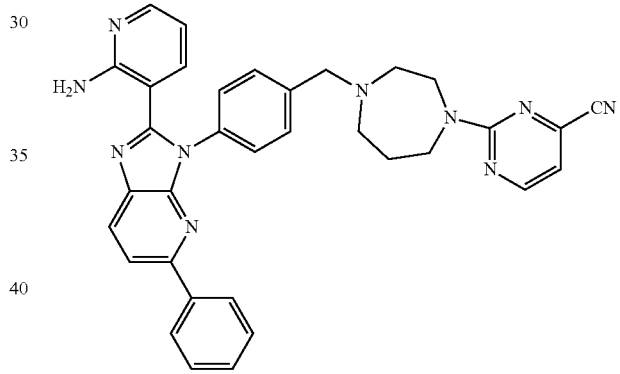

Example 228

A mixture of Intermediate 164 (94.5 mg, 206 μmol), 6-chloropyrimidine-4-carbonitrile (28.6 mg, 206 μmol) and DIEA (132 mg, 1.0 mmol) in NMP (3 mL) was taken up into a microwave tube. The sealed tube was heated at 130° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with brine (15 mL), dried over Na$_2$SO$_4$, filtered and concentrated under reduced pressure. After purified by prep-HPLC (column: Welch Xtimate C18 150×25 mm×5 μm; mobile phase: [water (HCl)-ACN]; B %: 12%-42%, 10 min), (R)-6-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile (Example 227, 19.8 mg, yield: 16%) was obtained as a yellow solid. MS: m/z=579.3 [M+H]$^+$. $^1$H NMR (400 MHz, Methanol-d$_4$) δ 8.65 (s, 1H), 8.33 (d, J=8.4 Hz, 1H), 8.05-8.02 (m, 4H), 7.93 (d, J=8.4 Hz, 2H), 7.88 (dd, J=7.6, 1.2 Hz, 1H), 7.76 (d, J=8.4 Hz, 2H), 7.47-7.42 (m, 4H), 6.87 (dd, J=7.6, 6.4 Hz, 1H), 3.76-3.69 (m, 1H), 3.63-3.55 (m, 2H), 3.51-3.32 (m, 4H), 3.30-3.22 (m, 2H), 1.46 (d, J=7.2 Hz, 3H).

A mixture of Intermediate 35 (80 mg, 168 μmol), 2-chloropyrimidine-4-carbonitrile (23.5 mg, 168 μmol) and DIEA (109 mg, 841 μmol) in NMP (3 mL) was taken up into a microwave tube. The sealed tube was heated at 130° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with brine (15 mL), dried over Na$_2$SO$_4$, filtered and concentrated under reduced pressure. After purified by prep-HPLC (column: Waters xbridge 150*25 mm*10 μm; mobile phase: [water (NH$_4$HCO$_3$)-ACN]; B %: 54%-84%, 8 min), 2-(4-(4-(2-(2-aminopyridin-3-yl)-5-phenyl-3H-imidazo[4,5-b]pyridin-3-yl)benzyl)-1,4-diazepan-1-yl)pyrimidine-4-carbonitrile (Example 228, 2.4 mg, yield: 2.3%) was obtained as a light-yellow solid. MS: m/z=579.3 [M+H]$^+$. $^1$H NMR (400 MHz, Dimethylsulfoxide-d$_6$) δ 8.74-8.56 (m, 1H), 8.27 (d, J=8.4 Hz, 1H), 8.04-7.97 (m, 4H), 7.50-7.43 (m, 7H), 7.15-7.11 (m, 2H), 7.04 (br s, 2H), 6.37-6.32 (m, 1H), 3.87-3.77 (m, 4H), 3.74 (s, 2H), 2.81-2.70 (m, 4H), 1.90-1.84 (m, 2H).

Example 229: N-(3-(4-(2-(2-aminopyridin-3-yl)-5-phenyl-3H-imidazo[4,5-b]pyridin-3-yl)benzyl)-3-azabicyclo[3.2.1]octan-8-yl)-2-cyanopyrimidine-4-carboxamide

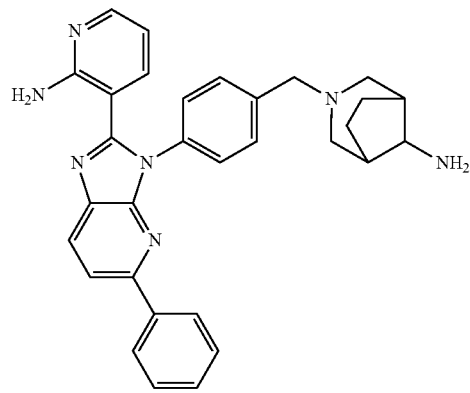

Intermediate 33

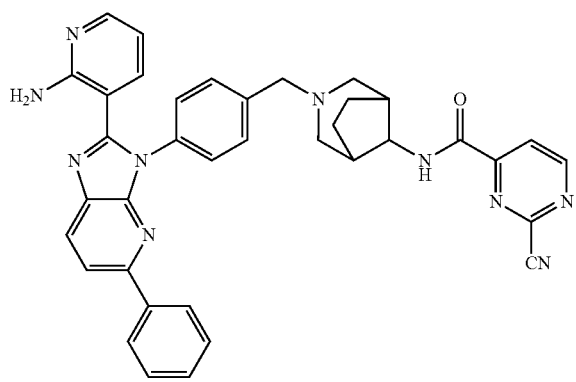

Example 229

To a solution of Intermediate 33 (100 mg, 199 μmol), 2-cyanopyrimidine-4-carboxylic acid (44.6 mg, 299 μmol), EDCI (57.3 mg, 299 μmol) and HOBt (40.4 mg, 299 μmol) in CH$_2$Cl$_2$ (2 mL) was added DIEA (103 mg, 797 μmol). The mixture was stirred at 25° C. for 16 hr. The reaction mixture was diluted with H$_2$O (10 mL) and extracted with CH$_2$Cl$_2$ (20 mL×2). The combined organic layers were washed with brine (10 mL), dried over Na$_2$SO$_4$, filtered and concentrated under reduced pressure. The crude product was purified by prep-HPLC (column: Welch Xtimate C18 150×25 mm×5 μm; mobile phase: [water (HCl)-ACN]; B %: 7%-37%, 10 min) to give N-(3-(4-(2-(2-aminopyridin-3-yl)-5-phenyl-3H-imidazo[4,5-b]pyridin-3-yl)benzyl)-3-azabicyclo[3.2.1]octan-8-yl)-2-cyanopyrimidine-4-carboxamide (Example 229, 12.4 mg, yield: 9.2%, HCl salt) as a yellow solid. MS: m/z=633.3 [M+H]$^+$. $^1$H NMR (400 MHz, Methanol-d$_4$) δ 9.17 (d, J=4.8 Hz, 1H), 8.72-8.60 (m, 1H), 8.34-8.25 (m, 2H), 8.04-8.01 (m, 3H), 7.92 (d, J=7.6 Hz, 2H), 7.85 (d, J=7.2 Hz, 1H), 7.73 (d, J=7.6 Hz, 2H), 7.48-7.40 (m, 3H), 6.90-6.87 (m, 1H), 4.52 (s, 2H), 4.21-4.16 (m, 1H), 3.55-3.43 (m, 4H), 2.81-2.73 (m, 2H), 2.23-2.14 (m, 2H), 2.05-2.00 (m, 2H).

Example 230: N-(3-(4-(2-(2-aminopyridin-3-yl)-5-phenyl-3H-imidazo[4,5-b]pyridin-3-yl)benzyl)-3-azabicyclo[3.2.1]octan-8-yl)-6-cyanopyrimidine-4-carboxamide

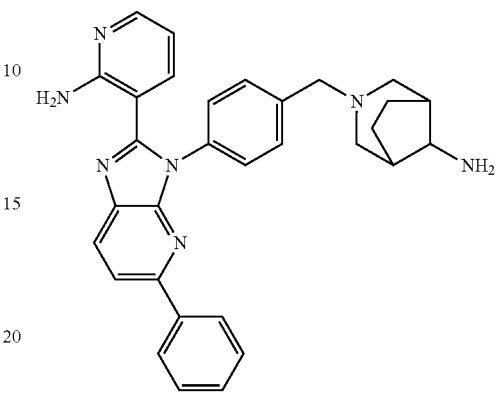

Intermediate 33

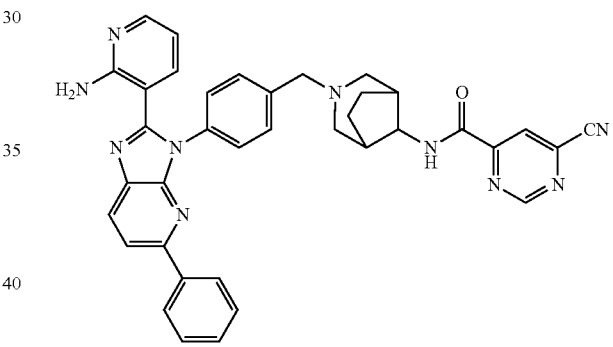

Example 230

To a solution of Intermediate 33 (100 mg, 199 μmol), 6-cyanopyrimidine-4-carboxylic acid (38.6 mg, 259 μmol), EDCI (57.3 mg, 299 μmol) and HOBt (40.4 mg, 299 μmol) in CH$_2$Cl$_2$ (2 mL) was added DIEA (103 mg, 797 μmol). The mixture was stirred at 25° C. for 16 hr. The reaction mixture was diluted with H$_2$O (10 mL) and extracted with CH$_2$Cl$_2$ (20 mL×2). The combined organic layers were washed with brine (10 mL), dried over Na$_2$SO$_4$, filtered, and concentrated under reduced pressure. The crude product was purified by prep-HPLC (column: Welch Xtimate Cis 150×25 mm×5 μm; mobile phase: [water (HCl)-ACN]; B %: 7%-37%, 10 min) to give N-(3-(4-(2-(2-aminopyridin-3-yl)-5-phenyl-3H-imidazo[4,5-b]pyridin-3-yl)benzyl)-3-azabicyclo[3.2.1]octan-8-yl)-6-cyanopyrimidine-4-carboxamide (Example 230, 11.7 mg, yield: 8.2%, HCl salt) as a yellow solid. MS: m/z=633.3 [M+H]$^+$. $^1$H NMR (400 MHz, Methanol-d$_4$) 9.16 (s, 1H), 8.33 (d, J=8.8 Hz, 1H), 8.17 (d, J=1.2 Hz, 1H), 8.08-8.03 (m, 2H), 7.97-7.94 (m, 2H), 7.91-7.87 (m, 2H), 7.85 (dd, J=7.6, 1.6 Hz, 1H), 7.74 (d, J=8.4 Hz, 2H), 7.44-7.40 (m, 3H), 6.88-6.81 (m, 1H), 4.51 (s, 2H), 3.85 (t, J=4.4 Hz, 1H), 3.52-3.47 (m, 2H), 3.38-3.34 (m, 2H), 2.87-2.82 (m, 2H), 2.15-2.09 (m, 2H), 2.06-1.98 (m, 2H).

Example 231: 2-((3-(4-(2-(2-Aminopyridin-3-yl)-5-phenyl-3H-imidazo[4,5-b]pyridin-3-yl)benzyl)-3-azabicyclo[3.2.1]octan-8-yl)amino)pyrimidine-4-carbonitrile

Example 232: 4-((1-(4-(2-(2-Aminopyridin-3-yl)-5-phenyl-3H-imidazo[4,5-b]pyridin-3-yl)benzyl)piperidin-4-yl)(methyl-d₃)amino)pyrimidine-2-carbonitrile

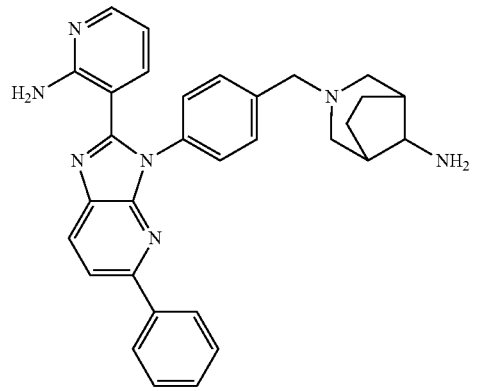

Intermediate 33

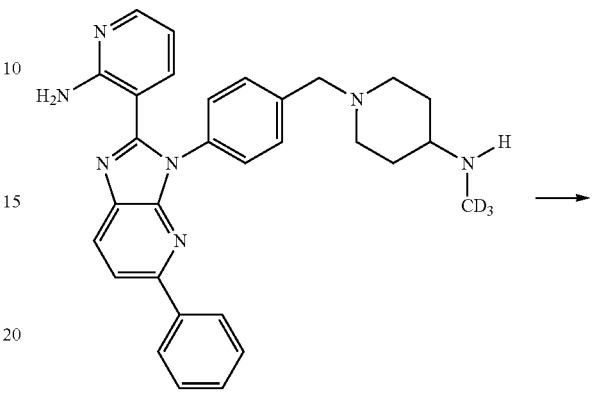

Intermediate 41

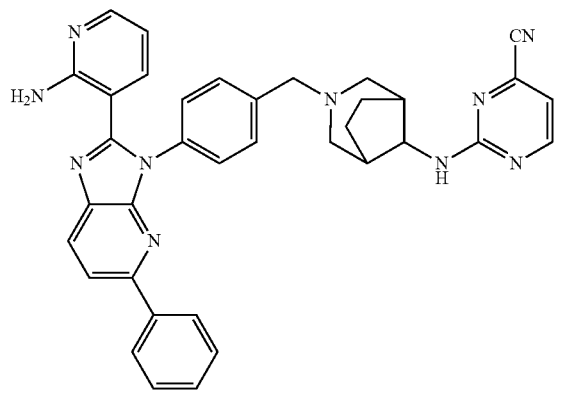

Example 231

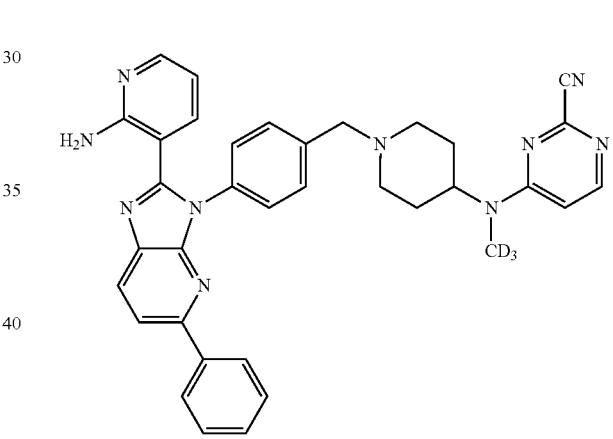

Example 232

A mixture of Intermediate 33 (100 mg, 199 μmol), 2-chloropyrimidine-4-carbonitrile (27.8 mg, 199 μmol) and DIEA (129 mg, 997 μmol) in NMP (3 mL) was taken up into a microwave tube. The sealed tube was heated at 160° C. for 1 hr under microwave. After purified by prep-HPLC (column: Welch Xtimate C$_{18}$ 150×25 mm×5 μm; mobile phase: [water (NH$_3$H$_2$O)-ACN]; B %: 60%-90%, 20 min), 2-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-4-carbonitrile (Example 231, 31.1 mg, yield: 25%) was obtained as a yellow solid. MS: m/z=605.3 [M+H]$^+$. $^1$H NMR (400 MHz, Dimethylsulfoxide-d$_6$) δ 8.61 (d, J=4.8 Hz, 1H), 8.27 (d, J=8.4 Hz, 1H), 8.05-7.97 (m, 4H), 7.95-7.71 (m, 1H), 7.52-7.44 (m, 6H), 7.42-7.36 (m, 1H), 7.17-7.04 (m, 4H), 6.40-6.34 (m, 1H), 3.62-3.58 (m, 2H), 2.75-2.56 (m, 4H), 2.46-2.40 (m, 1H), 2.29-2.24 (m, 2H), 1.86-1.63 (m, 4H).

To a solution of Intermediate 41 (100 mg, 203 μmol) in NMP (2 mL) were added 4-chloropyrimidine-2-carbonitrile (28.3 mg, 203 μmol) and DIEA (78.7 mg, 609 μmol). The mixture was stirred at 130° C. for 0.5 hr under microwave. The mixture was filtered and the filtrate was purified by prep-HPLC (column: Waters xbridge 150×25 mm 10 μm; mobile phase: [water (NH$_4$HCO$_3$)-ACN]; B %: 46%-76%, 15 min) to give 4-((1-(4-(2-(2-aminopyridin-3-yl)-5-phenyl-3H-imidazo[4,5-b]pyridin-3-yl)benzyl)piperidin-4-yl)(methyl-d$_3$)amino)pyrimidine-2-carbonitrile (Example 232, 23.7 mg, yield: 20%) as a light-yellow lyophilized powder. MS: m/z=596.2 [M+H]$^+$. $^1$H NMR (400 MHz, Methanol-d$_4$) δ 8.19 (d, J=8.4 Hz, 1H), 8.16 (d, J=6.4 Hz, 1H), 8.03 (d, J=7.2 Hz, 2H), 7.99 (dd, J=4.8, 1.6 Hz, 1H), 7.94 (d, J=8.4 Hz, 1H), 7.58-7.54 (m, 2H), 7.47 (d, J=8.4 Hz, 2H), 7.45-7.36 (m, 3H), 7.33 (dd, J=7.6, 1.6 Hz, 1H), 6.93-6.71 (m, 1H), 6.48 (dd, J=7.6, 5.2 Hz, 1H), 3.71 (s, 2H), 3.40-3.35 (m, 1H), 3.10 (d, J=12.0 Hz, 2H), 2.35-2.24 (m, 2H), 2.00-1.90 (m, 2H), 1.78-1.67 (m, 2H).

Example 233: 4-((1-(4-(2-(2-Aminopyridin-3-yl)-5-phenyl-3H-imidazo[4,5-b]pyridin-3-yl)benzyl)piperidin-4-yl)(methyl-d$_3$)amino)-1,3,5-triazine-2-carbonitrile

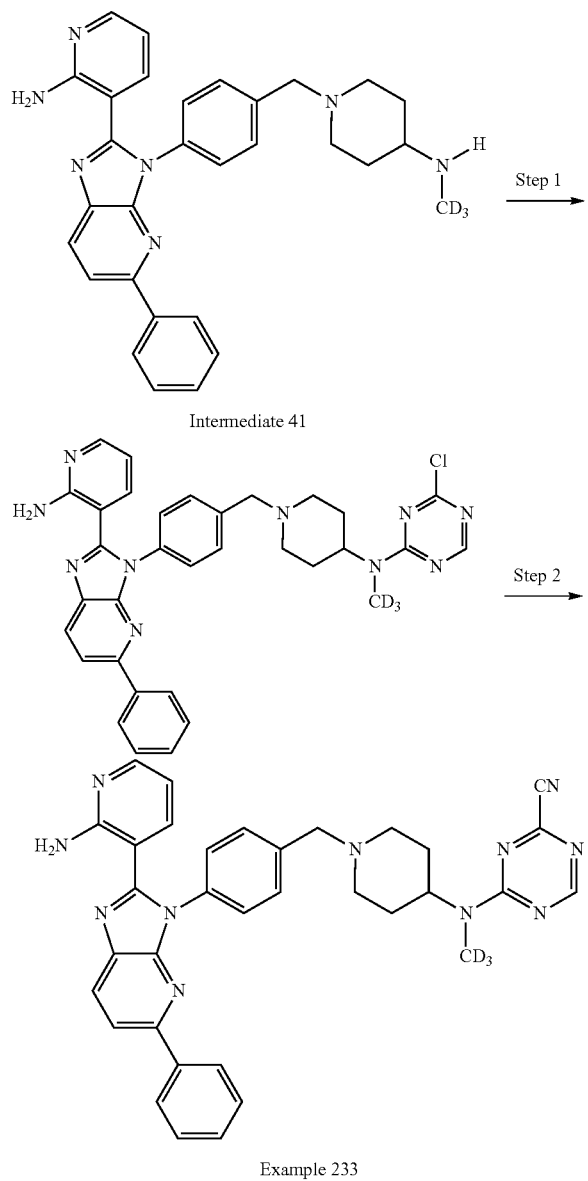

Intermediate 41

Step 1

Step 2

Example 233

Step 1: N-(1-(4-(2-(2-Aminopyridin-3-yl)-5-phenyl-3H-imidazo[4,5-b]pyridin-3-yl)benzyl)piperidin-4-yl)-4-chloro-N-(methyl-d$_6$)-1,3,5-triazin-2-amine To a solution of Intermediate 41 (100 mg, 203 μmol) in THF (8 mL) was added DIEA (78.7 mg, 609 μmol), and then the 2,4-dichloro-1,3,5-triazine (36.5 mg, 244 μmol) in THF (2 mL) was added into the mixture at 0° C. The mixture was stirred at 0° C. for 1 hr. The mixture was concentrated under reduced pressure. The residue was purified by silica gel flash chromatography (Eluent of 0~5% MeOH in CH$_2$Cl$_2$) to give N-(1-(4-(2-(2-Aminopyridin-3-yl)-5-phenyl-3H-imidazo[4,5-b]pyridin-3-yl)benzyl)piperidin-4-yl)-4-chloro-N-(methyl-d)-1,3,5-triazin-2-amine (50 mg crude, yield. 44%) as a light-yellow solid. MS: m/z=606.3 [M+H]$^+$. $^1$H NMR (400 MHz, Methanol-d$_4$) δ 8.35 (d, J=6.4 Hz, 1H), 8.20 (d, J=8.4 Hz, 1H), 8.05-8.02 (m, 2H), 7.98 (dd, J=4.8, 1.6 Hz, 1H), 7.94 (d, J=8.4 Hz, 1H), 7.56-7.54 (m, 2H), 7.48-7.32 (m, 6H), 6.51-6.46 (m, 1H), 3.68 (d, J=6.4 Hz, 1H), 3.35 (s, 2H), 3.12-3.05 (m, 2H), 2.30-2.20 (m, 2H), 1.99-1.90 (m, 2H), 1.75-1.70 (m, 2H).

Step 2: 4-((1-(4-(2-(2-Aminopyridin-3-yl)-5-phenyl-3H-imidazo[4,5-b]pyridin-3-yl)benzyl)piperidin-4-yl)(methyl-d$_3$)amino)-1,3,5-triazine-2-carbonitrile To a solution of N-(1-(4-(2-(2-aminopyridin-3-yl)-5-phenyl-3H-imidazo[4,5-b]pyridin-3-yl)benzyl)piperidin-4-yl)-4-chloro-N-(methyl-d$_3$)-1,3,5-triazin-2-amine (50 mg, 82.5 μmol) in DMSO (1 mL) were added DABCO (1.85 mg, 16.5 μmol) and KCN (10 mg, 156 μmol). The mixture was stirred at 0° C. for 1 hr. The reaction mixture was poured into water (10 mL). The resulting mixture was extracted with EtOAc (10 mL×2). The combined organic layers were washed with brine (10 mL), dried over anhydrous Na$_2$SO$_4$, filtered and concentrated. The residue was purified by silica gel flash chromatography (Eluent of 0~7% MeOH in CH$_2$Cl$_2$) to give 4-((1-(4-(2-(2-Aminopyridin-3-yl)-5-phenyl-3H-imidazo[4,5-b]pyridin-3-yl)benzyl)piperidin-4-yl)(methyl-d$_3$)amino)-1,3,5-triazine-2-carbonitrile (Example 233, 18.4 mg, yield: 34%) as a light-yellow solid. MS: m/z=597.4 [M+H]$^+$. $^1$H NMR (400 MHz, Methanol-d$_4$) δ 8.58 (d, J=6.8 Hz, 1H), 8.20 (d, J=8.4 Hz, 1H), 8.04 (d, J=7.2 Hz, 2H), 8.01-7.97 (m, 1H), 7.95 (d, J=8.4 Hz, 1H), 7.58-7.53 (m, 2H), 7.49-7.41 (m, 4H), 7.38-7.32 (m, 2H), 6.54-6.43 (m, 1H), 3.68 (d, J=7.6 Hz, 2H), 3.52-3.40 (m, 1H), 3.11-3.06 (m, 2H), 2.28-2.19 (m, 2H), 2.00-1.97 (m, 2H), 1.75-1.69 (m, 2H).

Example 234: N-(1-(4-(2-(2-Aminopyridin-3-yl)-5-phenyl-3H-imidazo[4,5-b]pyridin-3-yl)benzyl)piperidin-4-yl)-2-cyano-N-(methyl-d$_6$)pyrimidine-4-carboxamide

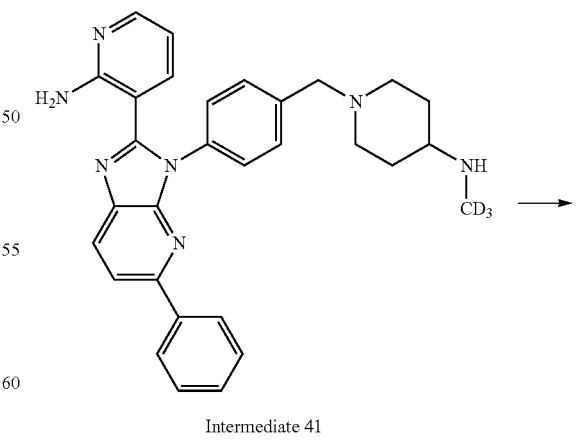

Intermediate 41

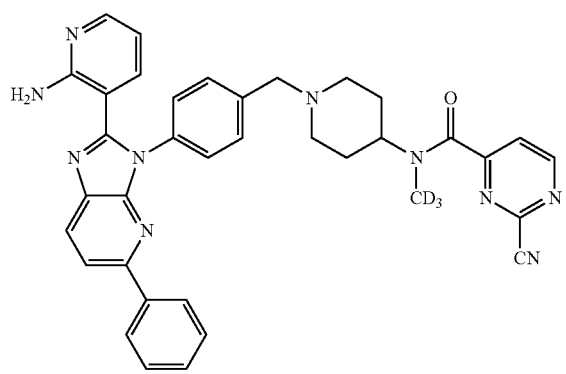

Example 234

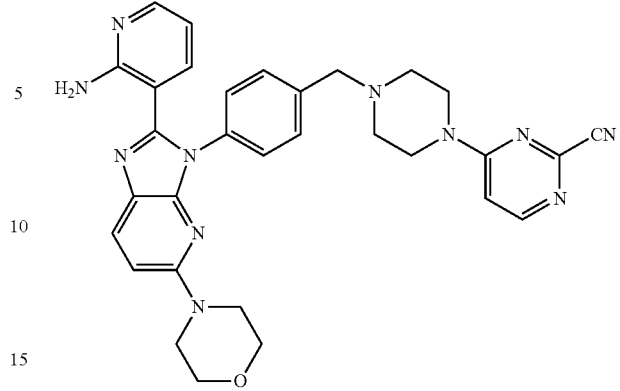

Example 235

To solution of Intermediate 41 (50 mg, 102 μmol), 2-cyanopyrimidine-4-carboxylic acid (19.7 mg, 132 μmol), EDCI (29.2 mg, 152 μmol) and HOBt (20.6 mg, 152 μmol) in CH₂Cl₂ (2 mL) was added DIEA (52.5 mg, 406 μmol). The mixture was stirred at 25° C. for 16 hr. The reaction mixture was diluted with H₂O (10 mL) and extracted with CH₂Cl₂ (20 mL×2). The combined organic layers were washed with brine (10 mL), dried over Na₂SO₄, filtered, and concentrated under reduced pressure. The crude product was purified by prep-TLC (CH₂Cl₂:MeOH=20:1) to give N-(1-(4-(2-(2-aminopyridin-3-yl)-5-phenyl-3H-imidazo[4,5-b]pyridin-3-yl)benzyl)piperidin-4-yl)-2-cyano-N-(methyl-d₃)pyrimidine-4-carboxamide (Example 234, 15.5 mg, yield: 24%) as a yellow solid. MS: m/z=624.4 [M+H]⁺. ¹H NMR (400 MHz, Dimethylsulfoxide-d₆) δ 9.23-9.03 (m, 1H), 8.28 (d, J=7.6 Hz, 1H), 8.06-7.97 (m, 5H), 7.54-7.39 (m, 7H), 7.19-7.13 (m, 1H), 7.06-6.96 (m, 2H), 6.43-6.34 (m, 1H), 3.66-3.39 (m, 2H), 3.14-2.96 (m, 1H), 2.94-2.74 (m, 1H), 2.21-2.12 (m, 1H), 1.93-1.85 (m, 2H), 1.73-1.60 (m, 2H), 1.30-1.19 (m, 2H).

Example 235: 4-(4-(4-(2-(2-Aminopyridin-3-yl)-5-morpholino-3H-imidazo[4,5-b]pyridin-3-yl)benzyl)piperazin-1-yl)pyrimidine-2-carbonitrile A mixture of Intermediate 46 (100 mg, 213 μmol), 4-chloropyrimidine-2-carbonitrile (29.7 mg, 213 μmol) and DIEA (110 mg, 850 μmol) in NMP (2 mL) was taken up into a microwave tube. The sealed tube was heated at 130° C. for 1 hr under microwave. The reaction mixture was quenched with H₂O (5 mL) at 0° C., and then diluted with CH₂Cl₂ (10 mL) and extracted with CH₂Cl₂ (15 mL×2). The combined organic layers were washed with brine (15 mL), dried over Na₂SO₄, filtered, and concentrated under reduced pressure. After purified by prep-HPLC (column: Phenomenex C18 150*25 mm*5 μm; mobile phase: [water (NH₄HCO₃)-ACN]; B %: 30%-60%, over 14 min), 4-(4-(4-(2-(2-aminopyridin-3-yl)-5-morpholino-3H-imidazo[4,5-b]pyridin-3-yl)benzyl)piperazin-1-yl)pyrimidine-2-carbonitrile (Example 235, 15.9 mg, yield: 13%) was obtained as a brown lyophilized powder. MS: m/z=574.3 [M+H]⁺. ¹H NMR (400 MHz, Dimethylsulfoxide-d₆) δ 8.27 (d, J=6.4 Hz, 1H), 7.98 (d, J=8.8 Hz, 1H), 7.93 (dd, J=4.8, 2.0 Hz, 1H), 7.46 (d, J=8.4 Hz, 2H), 7.33 (d, J=8.4 Hz, 2H), 7.12 (d, J=6.4 Hz, 1H), 7.04 (br s, 2H), 6.98 (dd, J=8.0, 2.0 Hz, 1H), 6.90 (d, J=9.2 Hz, 1H), 6.30 (dd, J=7.6, 4.8 Hz, 1H), 3.72-3.64 (m, 8H), 3.62 (s, 2H), 3.42-3.38 (m, 4H), 2.49-2.45 (m, 4H).

Example 236: 2-(4-(4-(2-(2-Aminopyridin-3-yl)-5-morpholino-3H-imidazo[4,5-b]pyridin-3-yl)benzyl)piperazin-1-yl)pyrimidine-4-carbonitrile

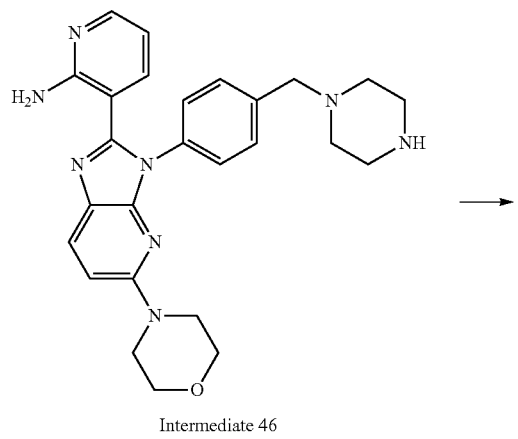

Intermediate 46

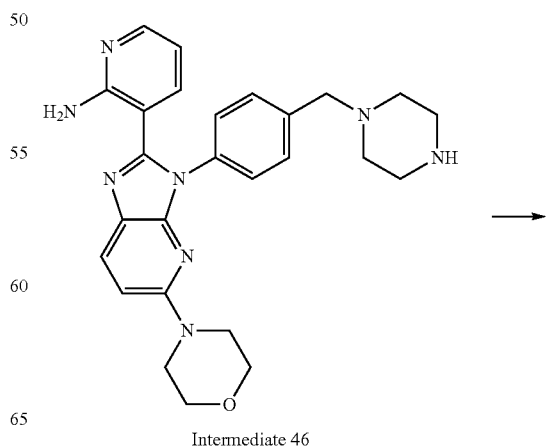

Intermediate 46

1307
-continued

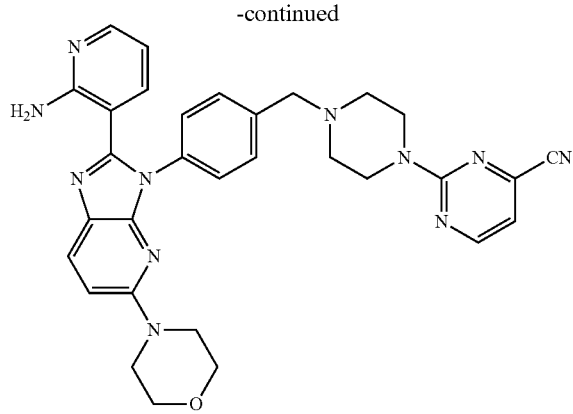

Example 236

1308
-continued

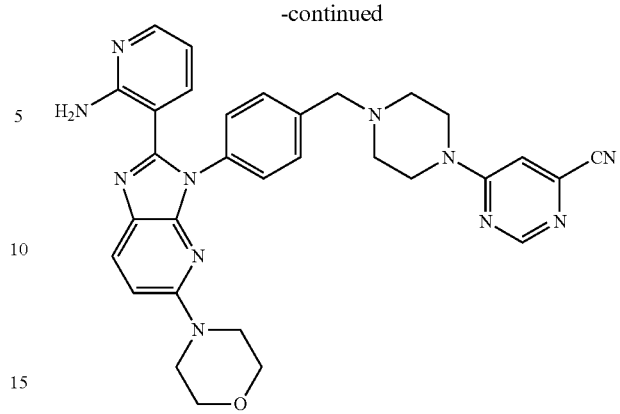

Example 237

A mixture of Intermediate 46 (200 mg, 425 μmol), 2-chloropyrimidine-4-carbonitrile (59.3 mg, 425 μmol) and DIEA (220 mg, 1.7 mmol) in NMP (2 mL) was taken up into a microwave tube. The sealed tube was heated at 130° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with brine (15 mL), dried over Na$_2$SO$_4$, filtered and concentrated under reduced pressure. After purified by prep-HPLC (column: Phenomenex C18 150*25 mm*5 μm; mobile phase: [water (NH$_4$HCO$_3$)-ACN]; B %: 41%-71%, over 14 min), 2-(4-(4-(2-(2-aminopyridin-3-yl)-5-morpholino-3H-imidazo[4,5-b]pyridin-3-yl)benzyl)piperazin-1-yl)pyrimidine-4-carbonitrile (Example 236, 52.9 mg, yield: 22%) was obtained as a brown lyophilized powder. MS: m/z=574.3 [M+H]$^+$. $^1$H NMR (400 MHz, Dimethylsulfoxide-d$_6$) δ 8.65 (d, J=4.8 Hz, 1H), 7.99 (d, J=8.8 Hz, 1H), 7.93 (dd, J=4.8, 1.6 Hz, 1H), 7.47 (d, J=8.4 Hz, 2H), 7.34 (d, J=8.4 Hz, 2H), 7.16 (d, J=4.8 Hz, 1H), 7.03 (br s, 2H), 6.99 (dd, J=8.0, 2.0 Hz, 1H), 6.90 (d, J=9.2 Hz, 1H), 6.31 (dd, J=8.0, 5.2 Hz, 1H), 3.82-3.76 (m, 4H), 3.71-3.66 (m, 4H), 3.62 (s, 2H), 3.42-3.38 (m, 4H), 2.49-2.44 (m, 4H).

Example 237: 6-(4-(4-(2-(2-Aminopyridin-3-yl)-5-morpholino-3H-imidazo[4,5-b]pyridin-3-yl)benzyl)piperazin-1-yl)pyrimidine-4-carbonitrile A mixture of Intermediate 46 (200 mg, 425 μmol), 6-chloropyrimidine-4-carbonitrile (59.3 mg, 425 μmol) and DIEA (220 mg, 1.7 mmol) in NMP (2 mL) was taken up into a microwave tube The sealed tube was heated at 130° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with brine (15 mL), dried over Na$_2$SO$_4$, filtered and concentrated under reduced pressure. After purified by prep-HPLC (column: Phenomenex C18 150*25 mm*5 μm; mobile phase: [water (NH$_4$HCO$_3$)-ACN]; B %: 40%-70%, over 10 min), 6-(4-(4-(2-(2-aminopyridin-3-yl)-5-morpholino-3H-imidazo[4,5-b]pyridin-3-yl)benzyl)piperazin-1-yl)pyrimidine-4-carbonitrile (Example 237, 42.2 mg, yield: 17%) was obtained as a brown lyophilized powder. MS: m/z=574.2 [M+H]Y. $^1$H NMR (400 MHz, Dimethylsulfoxide-d$_6$) δ 8.57 (s, 1H), 7.98 (d, J=8.8 Hz, 1H), 7.93 (dd, J=4.8, 1.6 Hz, 1H), 7.57 (s, 1H), 7.46 (d, J=8.4 Hz, 2H), 7.33 (d, J=8.4 Hz, 2H), 7.03 (br s, 2H), 6.98 (dd, J=7.6, 1.6 Hz, 1H), 6.90 (d, J=8.8 Hz, 1H), 6.28 (dd, J=7.6, 4.8 Hz, 1H), 3.81-3.65 (m, 8H), 3.61 (s, 2H), 3.42-3.38 (m, 4H), 2.49-2.44 (m, 4H).

Example 238: 4-(4-(4-(2-(2-Aminopyridin-3-yl)-5-(6-oxo-1,6-dihydropyridin-2-yl)-3H-imidazo[4,5-b]pyridin-3-yl)benzyl)piperazin-1-yl)pyrimidine-2-carbonitrile

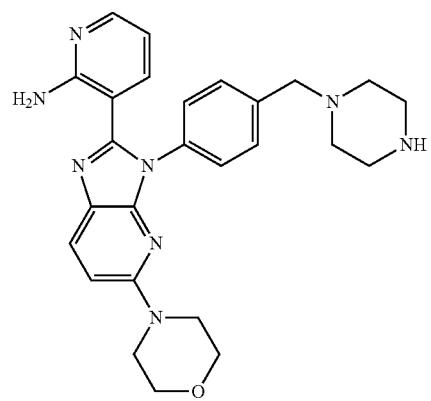

Intermediate 46

→

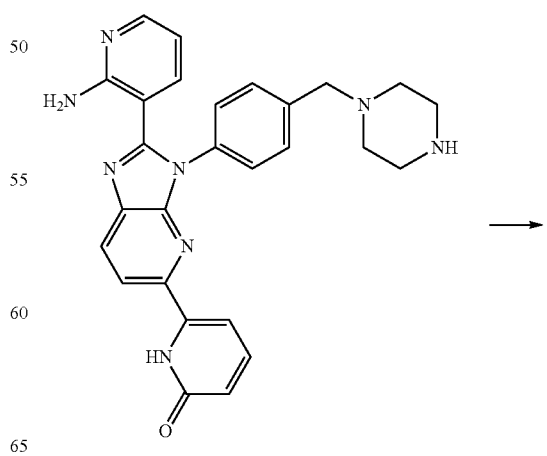

Intermediate 47

→

1309
-continued

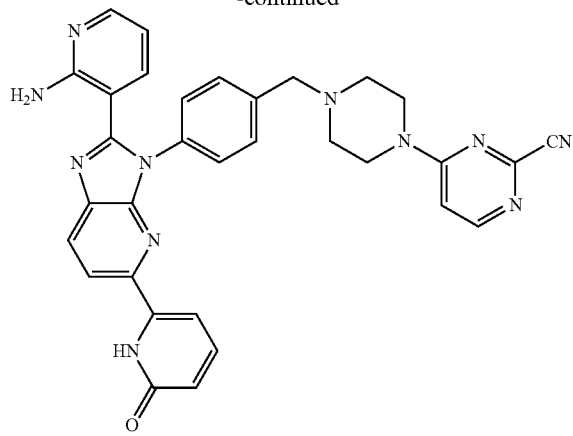

Example 238

A mixture of Intermediate 47 (100 mg, 209 μmol), 4-chloropyrimidine-2-carbonitrile (35 mg, 251 μmol) and DIEA (108 mg, 836 μmol) in NMP (2 mL) was taken up into a microwave tube. The sealed tube was heated at 130° C. for 1 hr under microwave. The reaction mixture was quenched with H₂O (5 mL) at 0° C., and then diluted with CH₂Cl₂ (10 mL) and extracted with CH₂Cl₂ (15 mL×2). The combined organic layers were washed with brine (15 mL), dried over Na₂SO₄, filtered and concentrated under reduced pressure. After purified by prep-HPLC (column: Phenomenex C18 150*25 mm*10 μm; mobile phase: [water (NH₄HCO₃)-ACN]; B %: 20%-50%, over 14 min), 4-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-2-carbonitrile (Example 238, 19.3 mg, yield: 16%) was obtained as a brown lyophilized powder. MS: m/z=582.2 [M+H]⁺. ¹H NMR (400 MHz, Dimethylsulfoxide-d₆) δ 10.80 (br s, 1H), 8.34 (d, J=8.0 Hz, 1H), 8.27 (d, J=6.4 Hz, 1H), 8.21-8.11 (m, 1H), 8.01 (dd, J=4.8, 1.6 Hz, 1H), 7.67-7.45 (m, 6H), 7.17-7.15 (m, 1H), 7.12 (d, J=6.4 Hz, 1H), 7.03 (br s, 2H), 6.52-6.42 (m, 1H), 6.38 (dd, J=7.6, 4.8 Hz, 1H), 3.79-3.67 (m, 4H), 3.66 (s, 2H), 2.60-2.52 (m, 4H).

Example 239: 4-((1-(4-(2-(2-Aminopyridin-3-yl)-5-morpholino-3H-imidazo[4,5-b]pyridin-3-yl)benzyl) piperidin-4-yl)amino)pyrimidine-2-carbonitrile

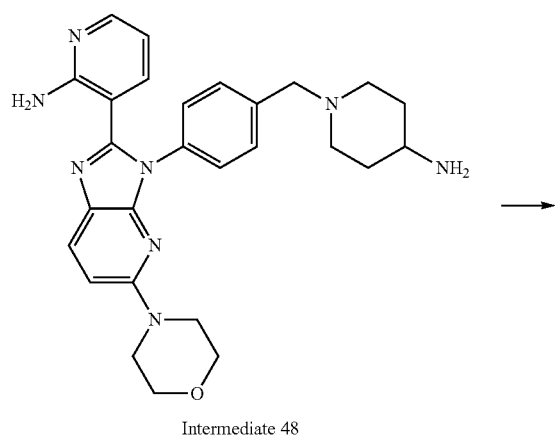

Intermediate 48

1310
-continued

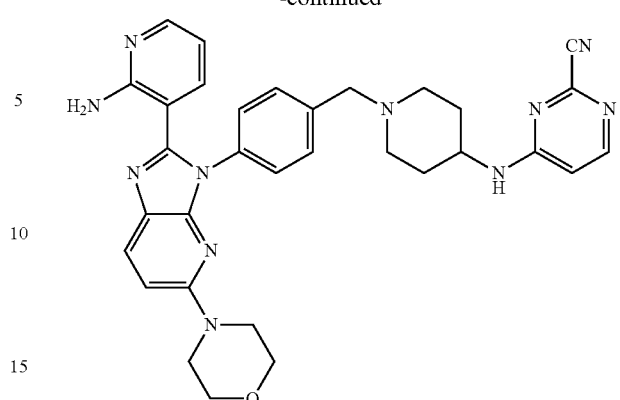

Example 239

A mixture of Intermediate 48 (100 mg, 206 μmol), 4-chloropyrimidine-2-carbonitrile (28.8 mg, 206 μmol) and DIEA (133 mg, 1.03 mmol) in NMP (2 mL) was taken up into a microwave tube. The sealed tube was heated at 130° C. for 30 min under microwave. The reaction mixture was filtered. After purified by prep-HPLC (column: Waters xbridge 150*25 mm 10 μm; mobile phase: [water (NH₄HCO₃)-ACN]; gradient: 28%-58% B over 18 min), 4-((1-(4-(2-(2-aminopyridin-3-yl)-5-morpholino-3H-imidazo[4,5-b]pyridin-3-yl)benzyl)piperidin-4-yl)amino)pyrimidine-2-carbonitrile (Example 239, 39.3 mg, yield: 32%) was obtained as a light-yellow powder. MS: m/z=588.4 [M+H]⁺. ¹H NMR (400 MHz, Dimethylsulfoxide-d₆) δ 8.08 (d, J=6.0 Hz, 1H), 8.04 (d, J=6.4 Hz, 1H), 7.98 (d, J=8.8 Hz, 1H), 7.93 (dd, J=4.4, 1.2 Hz, 1H), 7.42 (d, J=8.0 Hz, 2H), 7.31 (d, J=8.4 Hz, 2H), 7.03 (br s, 2H), 7.00-6.97 (m, 1H), 6.89 (d, J=9.2 Hz, 1H), 6.67 (d, J=6.0 Hz, 1H), 6.30 (dd, J=7.6, 5.2 Hz, 1H), 3.86-3.75 (m, 1H), 3.70-3.65 (m, 4H), 3.56 (s, 2H), 3.45-3.35 (m, 4H), 2.84-2.75 (m, 2H), 2.20-2.15 (m, 2H), 1.90-1.82 (m, 2H), 1.54-1.45 (m, 2H).

Example 240: 2-((1-(4-(2-(2-Aminopyridin-3-yl)-5-morpholino-3H-imidazo[4,5-b]pyridin-3-yl)benzyl) piperidin-4-yl)amino)pyrimidine-4-carbonitrile

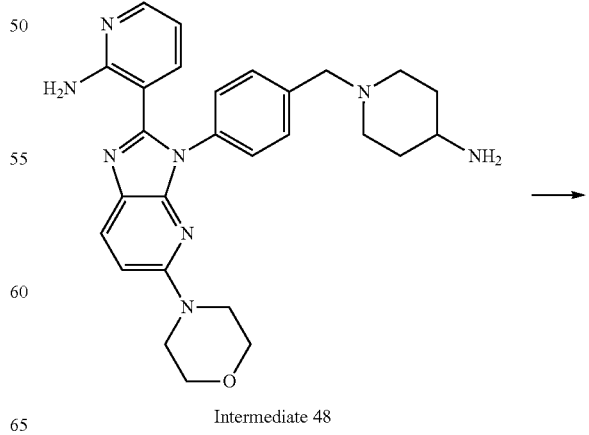

Intermediate 48

1311

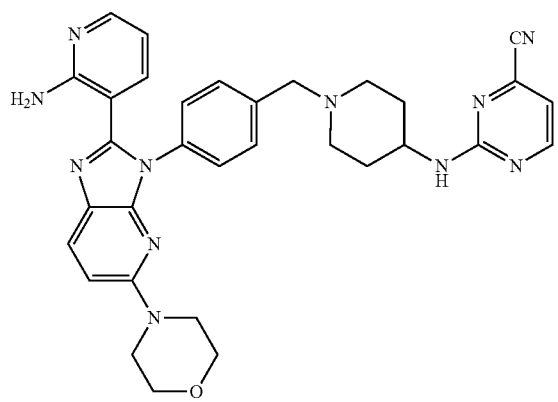

Example 240

A mixture of Intermediate 48 (200 mg, 413 μmol), 2-chloropyrimidine-4-carbonitrile (57.6 mg, 413 μmol) and DIEA (267 mg, 2.06 mmol) in NMP (3 mL) was taken up into a microwave tube. The sealed tube was heated at 130° C. for 30 min under microwave. The reaction mixture was filtered. After purified by prep-HPLC (column: Phenomenex C18 150*25 mm*10 μm; mobile phase: [water ($NH_4HCO_3$)-ACN]; gradient: 35%-65% B over 10 min), 2-((1-(4-(2-(2-aminopyridin-3-yl)-5-morpholino-3H-imidazo[4,5-b]pyridin-3-yl)benzyl)piperidin-4-yl)amino)pyrimidine-4-carbonitrile (Example 240, 23.9 mg, 25% yield) was obtained as a yellow powder. MS: m/z=588.3 [M+H]$^+$. $^1$H NMR (400 MHz, Dimethylsulfoxide-d$_6$) δ 8.60-8.46 (m, 1H), 7.97 (d, J=9.2 Hz, 1H), 7.93 (dd, J=4.8, 1.6 Hz, 1H), 7.85 (d, J=7.6 Hz, 1H), 7.41 (d, J=8.4 Hz, 2H), 7.30 (d, J=8.4 Hz, 2H), 7.06 (d, J=4.8 Hz, 1H), 7.03 (br s, 2H), 6.99 (dd, J=8.0, 2.0 Hz, 1H), 6.88 (d, J=9.2 Hz, 1H), 6.30 (dd, J=8.0, 5.2 Hz, 1H), 3.68-3.65 (m, 4H), 3.54 (s, 2H), 3.41-3.38 (m, 5H), 2.85-2.75 (m, 2H), 2.10-2.00 (m, 2H), 1.88-1.78 (m, 2H), 1.59-1.48 (m, 2H).

Example 241: 6-((1-(4-(2-(2-Aminopyridin-3-yl)-5-morpholino-3H-imidazo[4,5-b]pyridin-3-yl)benzyl)piperidin-4-yl)amino)pyrimidine-4-carbonitrile

1312

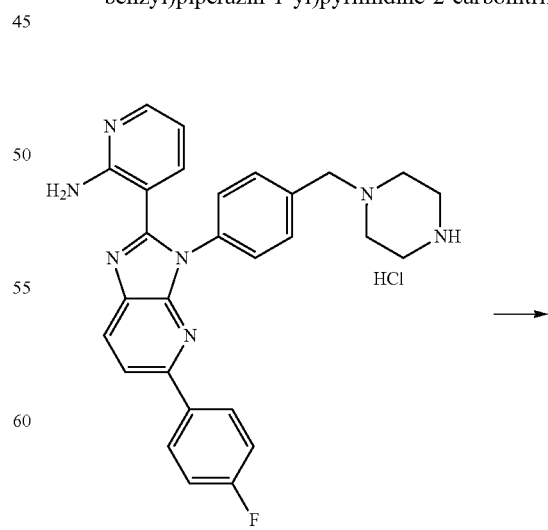

Example 241

A mixture of Intermediate 48 (200 mg, 413 μmol), 6-chloropyrimidine-4-carbonitrile (57.6 mg, 413 μmol) and DIEA (267 mg, 2.06 mmol) in NMP (2 mL) was taken up into a microwave tube. The sealed tube was heated at 130° C. for 30 min under microwave. The reaction mixture was filtered. After purified by prep-HPLC (column: Waters xbridge 150*25 mm 10 μm; mobile phase: [water ($NH_4HCO_3$)-ACN]; gradient: 31%-61% B over 10 min), 6-((1-(4-(2-(2-aminopyridin-3-yl)-5-morpholino-3H-imidazo[4,5-b]pyridin-3-yl)benzyl)piperidin-4-yl)amino)pyrimidine-4-carbonitrile (Example 241, 79.9 mg, 31% yield) was obtained as a yellow powder. MS: m/z=588.3 [M+H]$^+$. $^1$H NMR (400 MHz, Dimethylsulfoxide-d$_6$) δ 8.49 (s, 1H), 8.07 (d, J=6.8 Hz, 1H), 7.97 (d, J=8.8 Hz, 1H), 7.95-7.89 (m, 1H), 7.42 (d, J=8.4 Hz, 2H), 7.31 (d, J=8.4 Hz, 2H), 7.04 (br s, 2H), 7.00-6.96 (m, 1H), 6.95-6.85 (m, 2H), 6.30 (dd, J=7.6, 4.8 Hz, 1H), 3.90-3.75 (m, 1H), 3.70-3.60 (m, 4H), 3.55 (s, 2H), 3.43-3.35 (m, 4H), 2.85-2.75 (m, 2H), 2.15-2.04 (m, 2H), 1.90-1.75 (m, 2H), 1.55-1.43 (m, 2H).

Example 242: 4-(4-(4-(2-(2-Aminopyridin-3-yl)-5-(4-fluorophenyl)-3H-imidazo[4,5-b]pyridin-3-yl)benzyl)piperazin-1-yl)pyrimidine-2-carbonitrile

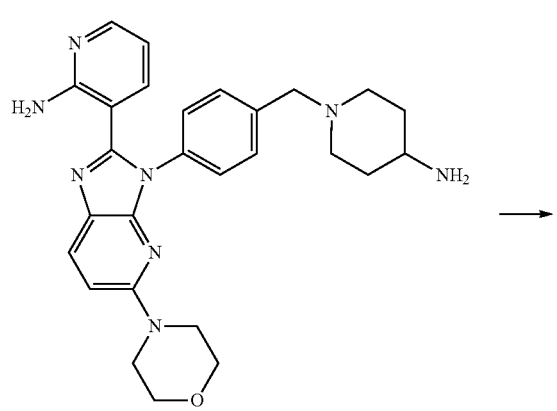

Intermediate 48

Intermediate 49

1313

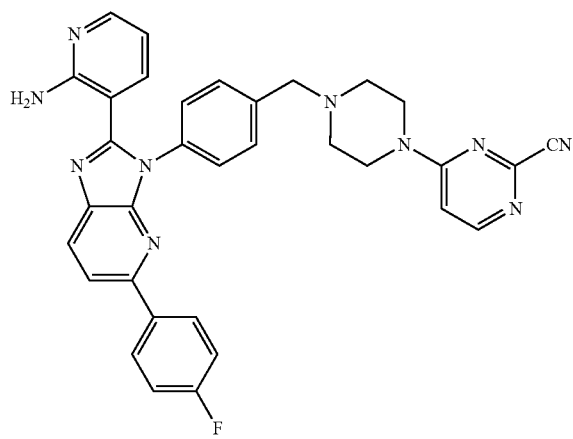

Example 242

A mixture of Intermediate 49 (100 mg, 209 μmol), 4-chloropyrimidine-2-carbonitrile (29.1 mg, 209 μmol) and DIEA (27 mg, 209 μmol) in NMP (2 mL) was taken up into a microwave tube. The sealed tube was heated at 130° C. for 1 hr under microwave. After purified by prep-HPLC (column: Waters xbridge 150×25 mm×10 μm; mobile phase: [water (NH$_4$HCO$_3$)-ACN]; B %: 45%-75%, 10 min), 4-(4-(4-(2-(2-aminopyridin-3-yl)-5-(4-fluorophenyl)-3H-imidazo[4,5-b]pyridin-3-yl)benzyl)piperazin-1-yl)pyrimidine-2-carbonitrile (Example 242, 35.2 mg, yield: 29%) was obtained as a yellow solid. MS: m/z=583.3 [M+H]$^+$. $^1$H NMR (400 MHz, Dimethylsulfoxide-d$_6$) δ 8.27 (d, J=7.6 Hz, 2H), 8.08 (dd, J=8.4, 6.0 Hz, 2H), 8.01-7.95 (m, 2H), 7.54-7.45 (m, 4H), 7.30 (t, J=8.8 Hz, 2H), 7.16-7.10 (m, 2H), 7.03 (s, 2H), 6.39-6.32 (m, 1H), 3.78-3.65 (m, 4H), 3.65 (s, 2H), 2.52-2.51 (m, 4H). $^{19}$F NMR (400 MHz, Dimethylsulfoxide-d$_6$) δ −113.56.

Example 243: 2-(4-(4-(2-(2-Aminopyridin-3-yl)-5-(4-fluorophenyl)-3H-imidazo[4,5-b]pyridin-3-yl)benzyl)piperazin-1-yl)pyrimidine-4-carbonitrile

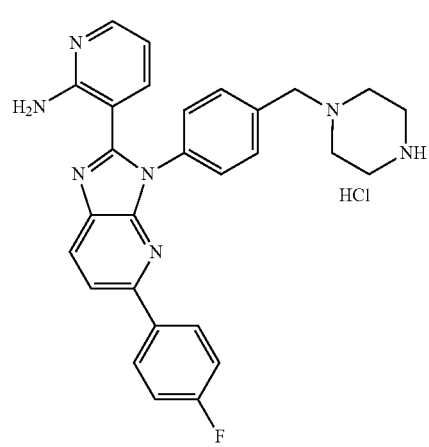

Intermediate 49

1314

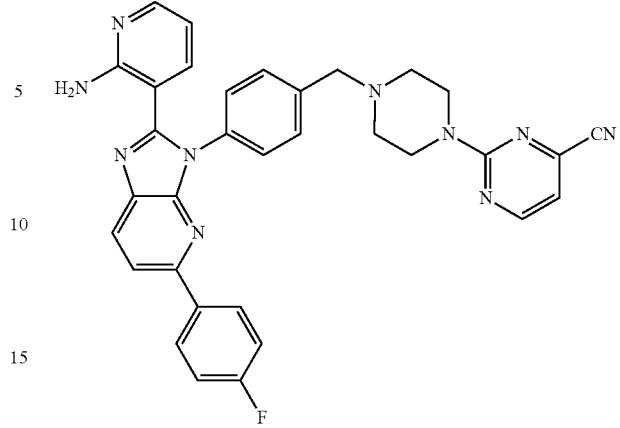

Example 243

A mixture of Intermediate 49 (80 mg, 167 μmol), 2-chloropyrimidine-4-carbonitrile (23.3 mg, 167 μmol), and DIEA (43.1 mg, 334 μmol) in NMP (2 mL) was taken up into a microwave tube. The sealed tube was heated at 130° C. for 1 hr under microwave. After purified by prep-HPLC (column: Waters xbridge 150×25 mm×10 μm; mobile phase: [water (NH$_4$HCO$_3$)-ACN]; B %: 56%-86%, 10 min), 2-(4-(4-(2-(2-aminopyridin-3-yl)-5-(4-fluorophenyl)-3H-imidazo[4,5-b]pyridin-3-yl)benzyl)piperazin-1-yl)pyrimidine-4-carbonitrile (Example 243, 56.3 mg, yield: 58%) was obtained as a brown solid. MS: m/z=583.3 [M+H]$^+$. $^1$H NMR (400 MHz, Dimethylsulfoxide-d$_6$) δ 8.65 (d, J=4.8 Hz, 1H), 8.27 (d, J=8.4 Hz, 1H), 8.11-8.06 (m, 2H), 8.01-7.97 (m, 2H), 7.53-7.45 (m, 4H), 7.33-7.28 (m, 2H), 7.17-7.13 (m, 2H), 7.03 (s, 2H), 6.37 (dd, J=8.0, 4.8 Hz, 1H), 3.82-3.77 (m, 4H), 3.64 (s, 2H), 2.51-2.51 (m, 4H). $^{19}$F NMR (400 MHz, Dimethylsulfoxide-d$_6$) δ −113.56.

Example 244: N-(4-(2-(2-Aminopyridin-3-yl)-3H-imidazo[4,5-b]pyridin-3-yl)benzyl)-2-cyanothiazole-4-carboxamide

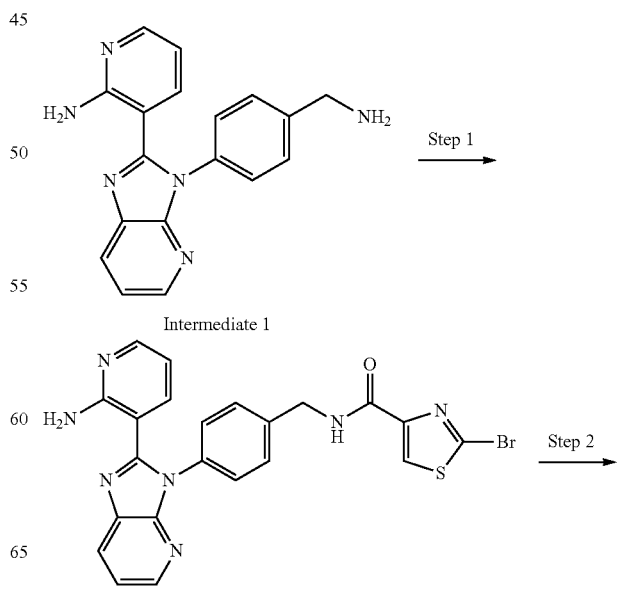

1315

-continued

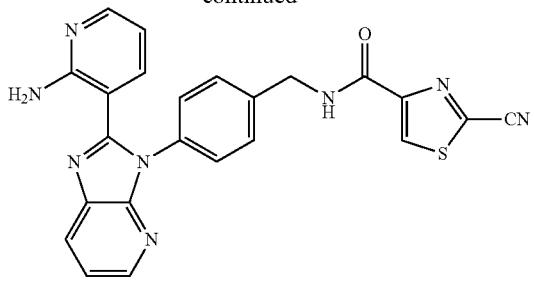

Example 244

Step 1: N-(4-(2-(2-aminopyridin-3-yl)-3H-imidazo[4,5-b]pyridin-3-yl)benzyl)-2-bromothiazole-4-carboxamide To a solution of 3-(3-(4-(aminomethyl)phenyl)-3H-imidazo[4,5-b]pyridin-2-yl)pyridin-2-amine (138 mg, 437 μmol) and 2-bromothiazole-4-carboxylic acid (100 mg, 480 μmol) in DMF (2 mL) were added EDCI (125 mg, 655 μmol), HOBt (88 mg, 655 μmol), and DIEA (282 mg, 2.2 mmol). The mixture was stirred at 25° C. for 3 hr. The mixture was quenched with water (20 mL) and extracted with EtOAc (25 mL×3). The combined organic layers were dried over $Na_2SO_4$, filtered, concentrated and purified by silica gel flash chromatography (eluent of 0~3% MeOH in $CH_2Cl_2$), N-(4-(2-(2-aminopyridin-3-yl)-3H-imidazo[4,5-b]pyridin-3-yl)benzyl)-2-bromothiazole-4-carboxamide (53 mg, yield: 43%) was obtained as a yellow solid. MS: m/z=506.1, 508.0 [M+H]⁺. ¹H NMR (400 MHz, Dimethylsulfoxide-d₆) δ 9.20 (t, J=6.4 Hz, 1H), 8.35-8.28 (m, 2H), 8.19 (dd, J=8.0, 1.2 Hz, 1H), 7.99 (dd, J=4.8, 1.6 Hz, 1H), 7.47-7.41 (m, 2H), 7.41-7.35 (m, 3H), 7.23 (dd, J=7.6, 1.6 Hz, 1H), 6.97 (br s, 2H), 6.41 (dd, J=7.6, 4.8 Hz, 1H), 4.51 (d, J=6.4 Hz, 2H).

Step 2: N-(4-(2-(2-aminopyridin-3-yl)-3H-imidazo[4,5-b]pyridin-3-yl)benzyl)-2-cyanothiazole-4-carboxamide To a solution of N-[[4-[2-(2-amino-3-pyridyl)imidazo[4,5-b]pyridin-3-yl]phenyl]methyl]-2-bromo-thiazole-4-carboxamide (100 mg, 198 μmol) in pyridine (3.5 mL) was added CuCN (37.1 mg, 415 μmol) at 25° C. The mixture was stirred at 145° C. for 6 hr. The mixture was filtered and concentrated under reduced pressure. The residue was purified by prep-HPLC (column: Waters xbridge 150*25 mm 10 μm; mobile phase: [water ($NH_4HCO_3$)-ACN]; gradient: 15%-45% B over 10 min) to give N-(4-(2-(2-aminopyridin-3-yl)-3H-imidazo[4,5-b]pyridin-3-yl)benzyl)-2-cyanothiazole-4-carboxamide (Example 244, 15 mg, yield: 17%) was obtained as a light-yellow solid. MS: m/z=453.0 [M+H]⁺. ¹H NMR (400 MHz, Dimethylsulfoxide-d₆) δ 8.49 (d, J=0.8 Hz, 1H), 8.30 (dt, J=4.8, 1.2 Hz, 1H), 8.19 (br s, 1H), 8.10 (d, J=8.0 Hz, 1H), 8.00 (d, J=4.8 Hz, 1H), 7.50 (d, J=8.0 Hz, 2H), 7.38-7.32 (m, 3H), 7.20 (d, J=7.6 Hz, 1H), 6.52 (br s, 2H), 6.38 (dd, J=7.6, 4.8 Hz, 1H), 4.64 (d, J=6.4 Hz, 2H).

1316

Example 245: N-(4-(2-(2-Aminopyridin-3-yl)-5-phenyl-3H-imidazo[4,5-b]pyridin-3-yl)benzyl)-2-cyanothiazole-5-carboxamide

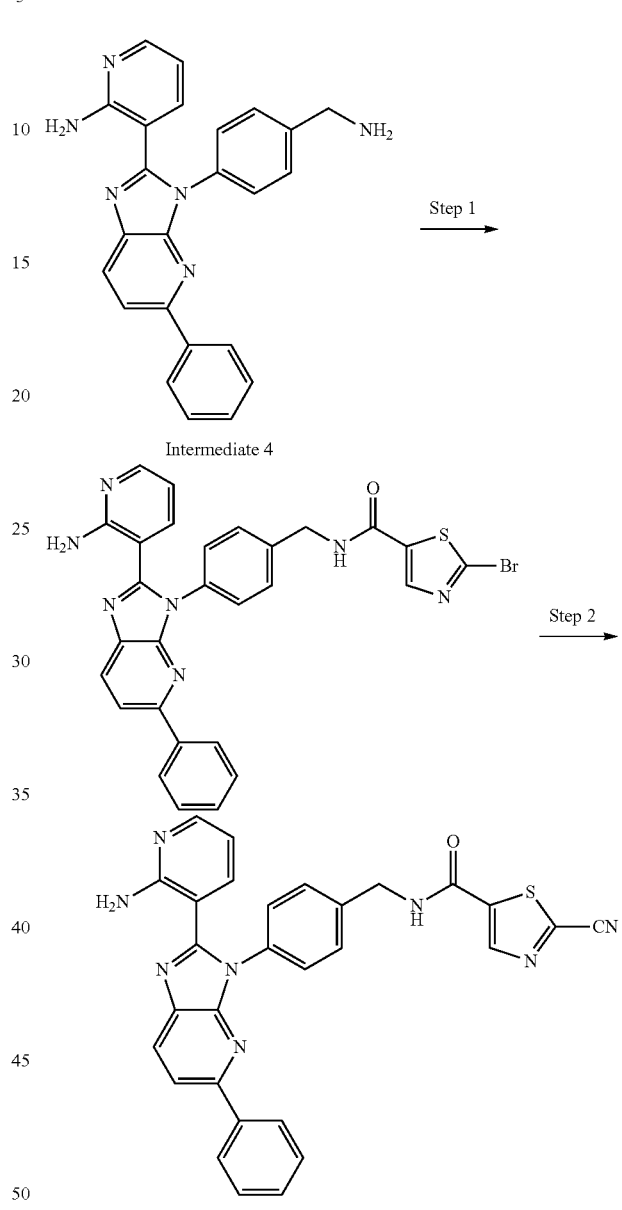

Example 245

Step 1: N-(4-(2-(2-Aminopyridin-3-yl)-5-phenyl-3H-imidazo[4,5-b]pyridin-3-yl)benzyl)-2-bromothiazole-5-carboxamide To a solution of Intermediate 4 (300 mg, 764 μmol) in dimethylformamide (2 mL) were added HATU (436 mg, 1.15 mmol), DIEA (395 mg, 3 mmol) and 2-bromothiazole-5-carboxylic acid (175 mg, 841 μmol). The mixture was stirred at 25° C. for 16 hr. The reaction mixture was quenched with $H_2O$ (10 mL) at 25° C., and then extracted with EtOAc (10 mL×4). The combined organic layers were washed with brine (10 mL×2), dried over $Na_2SO_4$, filtered, concentrated and purified by prep-HPLC (neutral condition:

column: Waters xbridge 150*25 mm 10 μm; mobile phase: [water (NH₄HCO₃)-ACN]; B %: 40%-70%, 9 min) to give N-(4-(2-(2-aminopyridin-3-yl)-5-phenyl-3H-imidazo[4,5-b]pyridin-3-yl)benzyl)-2-bromothiazole-5-carboxamide (142 mg, yield: 32%) as a light-yellow lyophilized powder. MS: m/z=582.2, 584.2 [M+H]⁺. ¹H NMR (400 MHz, Dimethylsulfoxide-d₆) δ 9.44 (t, J=6.0 Hz, 1H), 8.33-8.24 (m, 2H), 8.05-7.97 (m, 4H), 7.50-7.44 (m, 6H), 7.41-7.37 (m, 1H), 7.22 (dd, J=7.6, 1.6 Hz, 1H), 6.93 (br s, 2H), 6.42 (dd, =7.6, 5.2 Hz, 1H), 4.58 (d, J=6.0 Hz, 2H).

Step 2: N-(4-(2-(2-Aminopyridin-3-yl)-5-phenyl-3H-imidazo[4,5-b]pyridin-3-yl)benzyl)-2-cyanothiazole-5-carboxamide To a solution of N-[[4-[2-(2-amino-3-pyridyl)-5-phenyl-imidazo[4,5-b]pyridin-3-yl]phenyl]methyl]-2-bromo-thiazole-5-carboxamide (100 mg, 172 μmol) in pyridine (4 mL) was added CuCN (32.3 mg, 361 gmol) at 25° C. The mixture was stirred at 145° C. for 6 hr. Filtered and concentrated under reduced pressure. The residue was purified by prep-HPLC (column: Waters xbridge 150*25 mm 10 μm; mobile phase: [water (NH₄HCO₃)-ACN]; gradient: 35%-65% B over 10 min) to give N-(4-(2-(2-aminopyridin-3-yl)-5-phenyl-3H-imidazo[4,5-b]pyridin-3-yl)benzyl)-2-cyanothiazole-5-carboxamide (Example 245, 5 mg, yield: 5.5%) as a light-yellow solid. MS: m/z=529.2 [M+H]⁺. ¹H NMR (400 MHz, Dimethylsulfoxide-d₆) δ 8.42 (s, 1H), 8.17 (d, J=8.4 Hz, 1H), 8.05-7.88 (m, 5H), 7.54 (d, J=8.0 Hz, 2H), 7.47-7.36 (m, 5H), 7.18 (d, J=7.6 Hz, 1H), 6.52 (br s, 2H), 6.39 (dd, J=7.6, 4.8 Hz, 1H), 4.65 (d, J=6.0 Hz, 2H).

Example 246: N-(4-(2-(2-Aminopyridin-3-yl)-5-phenyl-3H-imidazo[4,5-b]pyridin-3-yl)benzyl)-2-cyanothiazole-4-carboxamide

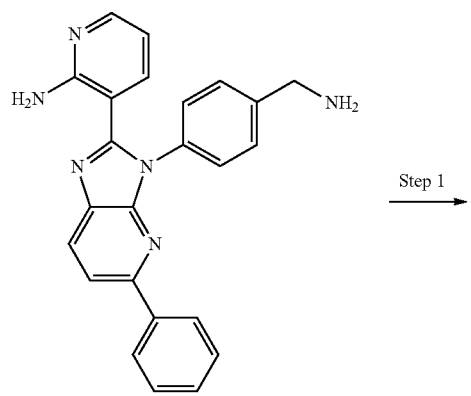

Intermediate 4

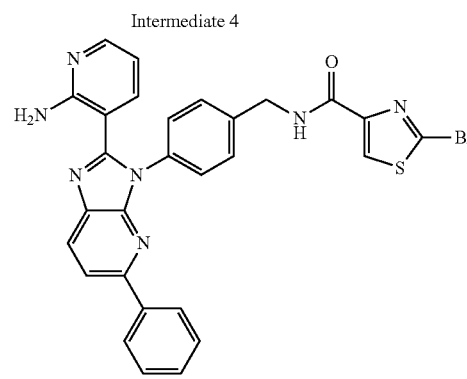

Step 2

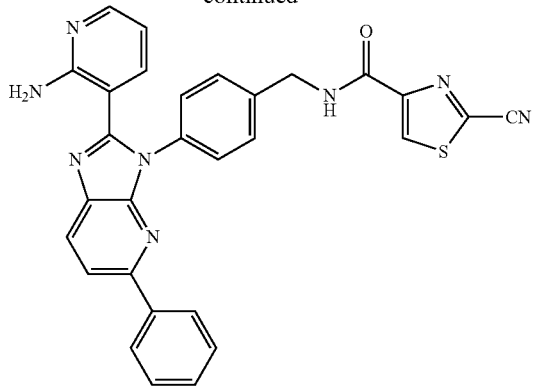

Example 246

Step 1: N-(4-(2-(2-Aminopyridin-3-yl)-5-phenyl-3H-imidazo[4,5-b]pyridin-3-yl)benzyl)-2-bromothiazole-4-carboxamide To a solution of Intermediate 4 (292 mg, 1.40 mmol) in DMF (1 mL) was added EDCI (366 mg, 1.91 mmol), HOBt (258 mg, 1.91 mmol), DIEA (659 mg, 5.10 mmol) and 3-[3-[4-(aminomethyl)phenyl]-5-phenyl-imidazo[4,5-b]pyridin-2-yl]pyridin-2-amine (500 mg, 1.27 mmol). The mixture was stirred at 25° C. for 12 hr. Then it was filtered and concentrated under reduced pressure. The residue was purified by silica gel flash chromatography (eluent of 0-10% MeOH in CH₂Cl₂) to give N-(4-(2-(2-aminopyridin-3-yl)-5-phenyl-3H-imidazo[4,5-b]pyridin-3-yl)benzyl)-2-bromothiazole-4-carboxamide (440 mg, 59% yield) as a yellow solid. MS: m/z=582.1, 584.1 [M+H]⁺. ¹H NMR (400 MHz, Dimethylsulfoxide-d₆) δ 9.21 (t, J=6.4 Hz, 1H), 8.34 (s, 1H), 8.25 (d, J=8.0 Hz, 1H), 8.05-7.95 (m, 4H), 7.49-7.43 (m, 6H), 7.41-7.36 (m, 1H), 7.20 (dd, J=7.6, 2.0 Hz, 1H), 6.95 (s, 2H), 6.41 (dd, J=7.6, 4.8 Hz, 1H), 4.54 (d, J=6.4 Hz, 2H).

Step 2: N-(4-(2-(2-Aminopyridin-3-yl)-5-phenyl-3H-imidazo[4,5-b]pyridin-3-yl)benzyl)-2-cyanothiazole-4-carboxamide To a solution of N-[[4-[2-(2-amino-3-pyridyl)-5-phenyl-imidazo[4,5-b]pyridin-3-yl]phenyl]methyl]-2-bromo-thiazole-4-carboxamide (100 mg, 172 μmol) in pyridine (4 mL) was added CuCN (32.3 mg, 361 μmol) at 25° C. The mixture was stirred at 145° C. for 6 hr, and then was filtered and concentrated under reduced pressure. The residue was purified by prep-HPLC (column: Waters xbridge 150*25 mm 10 m; mobile phase: [water (NH₄HCO₃)-ACN]; B %: 37%-67%, 10 min) to give N-(4-(2-(2-Aminopyridin-3-yl)-5-phenyl-3H-imidazo[4,5-b]pyridin-3-yl)benzyl)-2-cyanothiazole-4-carboxamide (Example 246, 30 mg, yield: 31%) as a light-yellow solid. MS: m/z=529.2 [M+H]⁺. ¹H NMR (400 MHz, Dimethylsulfoxide-d₆) δ 8.28 (s, 1H), 8.03-7.93 (m, 2H), 7.82-7.76 (m, 3H), 7.66 (d, J=8.4 Hz, 1H), 7.33-7.16 (m, 7H), 6.97 (dd, J=7.6, 1.6 Hz, 1H), 6.29 (br s, 2H), 6.18 (dd, J=7.6, 4.8 Hz, 1H), 4.45 (d, J=6.4 Hz, 1H).

Example 247: 4-(4-(4-(2-(2-Aminopyridin-3-yl)-5-phenyl-3H-imidazo[4,5-b]pyridin-3-yl)benzyl)piperazine-1-carbonyl)thiazole-2-carbonitrile

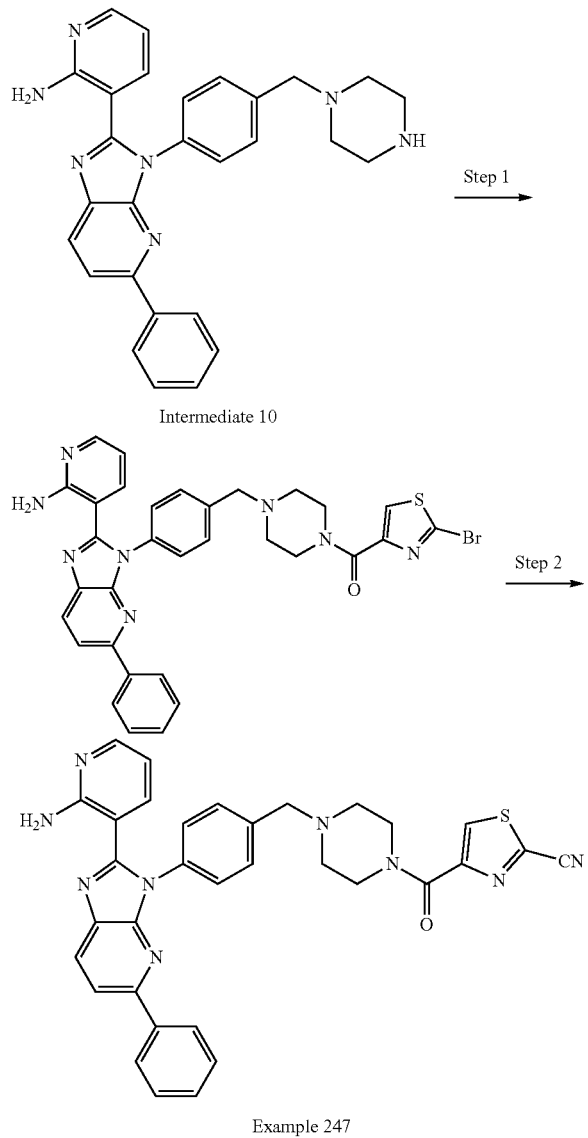

Step 1: (4-(4-(2-(2-Aminopyridin-3-yl)-5-phenyl-3H-imidazo[4,5-b]pyridin-3-yl)benzyl)piperazin-1-yl)(2-bromothiazol-4-yl)methanone To a solution of Intermediate 10 (300 mg, 645 μmol) and 2-bromothiazole-4-carboxylic acid (149 mg, 715 μmol) in DMF (5 mL) were added EDCI (187 mg, 975 μmol), HOBt (132 mg, 975 μmol), and DIEA (336 mg, 2.60 mmol) at 0° C. The mixture was stirred at 25° C. for 12 hr, and then was filtered and concentrated under reduced pressure. The residue was purified by silica gel flash chromatography (eluent of 0-10% MeOH in $CH_2Cl_2$) to give (4-(4-(2-(2-Aminopyridin-3-yl)-5-phenyl-3H-imidazo[4,5-b]pyridin-3-yl)benzyl)piperazin-1-yl)(2-bromothiazol-4-yl)methanone (212 mg, yield: 50%) was obtained as a yellow solid. MS: m/z=651.2, 653.1 [M+H]+. $^1$H NMR (400 MHz, Dimethylsulfoxide-$d_6$) δ 8.26 (d, J=8.4 Hz, 1H), 8.13 (s, 1H), 8.05-7.95 (m, 4H), 7.51-7.37 (m, 7H), 7.15 (dd, J=7.6, 1.6 Hz, 1H), 7.02 (s, 2H), 6.39 (dd, J=7.6, 4.8 Hz, 1H), 3.66-3.60 (m, 6H), 3.34-3.29 (m, 2H), 2.47-2.43 (m, 2H).

Step 2: 4-(4-(4-(2-(2-Aminopyridin-3-yl)-5-phenyl-3H-imidazo[4,5-b]pyridin-3-yl)benzyl)piperazine-1-carbonyl)thiazole-2-carbonitrile To a solution of [4-[[4-[2-(2-amino-3-pyridyl)-5-phenyl-imidazo[4,5-b]pyridin-3-yl]phenyl]methyl]piperazin-1-yl]-(2-bromothiazol-4-yl)methanone (150 mg, 230 μmol) in pyridine (4 mL) was added CuCN (41.2 mg, 460 μmol) at 25° C. The mixture was stirred at 145° C. for 6 hr. The reaction mixture was filtered and concentrated under reduced pressure. The residue was purified by prep-HPLC (column: Waters xbridge 150*25 mm 10 μm; mobile phase: [water ($NH_4HCO_3$)-ACN]; B %: 42%-72%, 10 min) to give 4-(4-(4-(2-(2-Aminopyridin-3-yl)-5-phenyl-3H-imidazo[4,5-b]pyridin-3-yl)benzyl)piperazine-1-carbonyl)thiazole-2-carbonitrile (Example 247, 30 mg, yield: 22%) was obtained as a light-yellow solid. MS: m/z=598.2 [M+H]+. $^1$H NMR (400 MHz, Dimethylsulfoxide-$d_6$) δ 8.02 (s, 1H), 7.97 (d, J=8.4 Hz, 1H), 7.83-7.80 (m, 3H), 7.69 (d, J=8.8 Hz, 1H), 7.34-7.20 (m, 7H), 6.94 (dd, J=7.6, 1.6 Hz, 1H), 6.38 (br s, 2H), 6.17 (dd, J=7.6, 4.8 Hz, 1H), 3.53 (s, 2H), 3.47-3.43 (m, 4H), 2.37-2.33 (m, 2H), 2.30-2.25 (m, 2H).

Example 248: 4-((7-(4-(2-(2-aminopyridin-3-yl)-5-phenyl-3H-imidazo[4,5-b]pyridin-3-yl)benzyl)-7-azaspiro[3.5]nonan-2-yl)amino)-1,3,5-triazine-2-carbonitrile

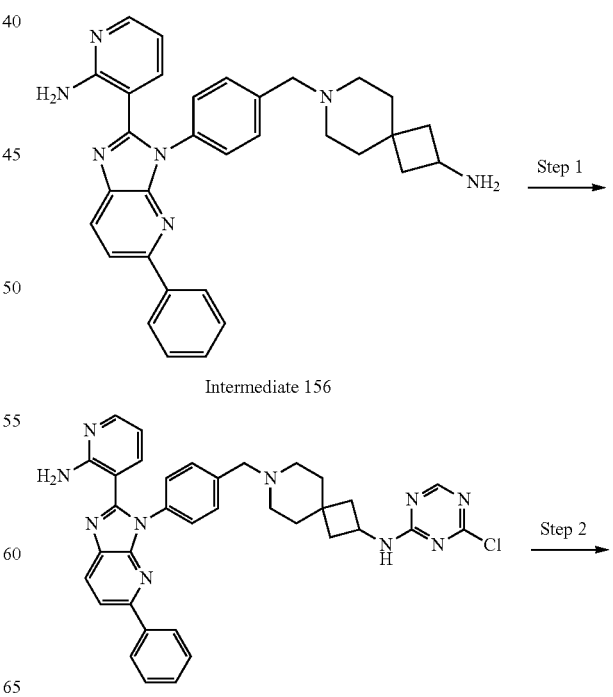

-continued

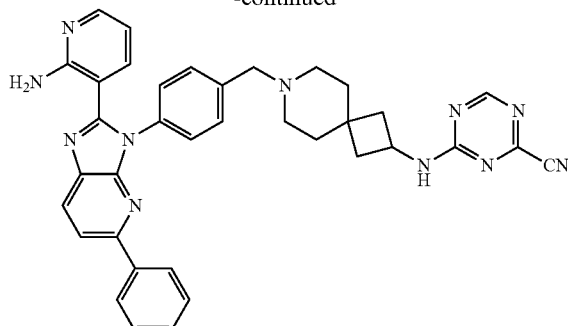

Example 248

Step 1: 7-(4-(2-(2-Aminopyridin-3-yl)-5-phenyl-3H-imidazo[4,5-b]pyridin-3-yl)benzyl)-N-(4-chloro-1,3,5-triazin-2-yl)-7-azaspiro[3.5]nonan-2-amine To a solution of Intermediate 156 (100 mg, 181 μmol) in THF (20 mL) was added DIEA (70.2 mg, 543 μmol). The mixture was stirred at 0° C. for 10 min. Then 2,4-dichloro-1,3,5-triazine (32.6 mg, 217 μmol) in THF (1 mL) was added to the mixture. The mixture was stirred at 0° C. for 0.5 hr, then was partitioned between EtOAc (50 mL) and H$_2$O (30 mL). The organic layer was washed with brine (60 mL) and dried over Na$_2$SO$_4$, filtered, and concentrated. The residue was purified by prep-TLC (CH$_2$Cl$_2$:MeOH=10:1) to give 7-(4-(2-(2-aminopyridin-3-yl)-5-phenyl-3H-imidazo[4,5-b]pyridin-3-yl)benzyl)-N-(4-chloro-1,3,5-triazin-2-yl)-7-azaspiro[3.5]nonan-2-amine (8.4 mg, yield: 7.1%) as a light-yellow solid. MS: m/z=629.3 [M+H]$^+$. $^1$H NMR (400 MHz, Dimethylsulfoxide-d$_6$) δ 8.95-8.93 (m, 1H), 8.51-8.31 (m, 1H), 8.27 (d, J=8.4 Hz, 1H), 8.04-7.96 (m, 4H), 7.48-7.37 (m, 7H), 7.16-7.14 (m, 1H), 7.02 (br s, 2H), 6.37 (dd, J=7.6, 4.8 Hz, 1H), 4.13-4.03 (m, 1H), 3.53 (s, 2H), 2.34-2.23 (m, 4H), 2.21-2.15 (m, 2H), 1.80-1.73 (m, 2H), 1.63-1.52 (m, 4H).

Step 2: 4-((7-(4-(2-(2-aminopyridin-3-yl)-5-phenyl-3H-imidazo[4,5-b]pyridin-3-yl)benzyl)-7-azaspiro[3.5]nonan-2-yl)amino)-1,3,5-triazine-2-carbonitrile To a solution of 7-(4-(2-(2-aminopyridin-3-yl)-5-phenyl-3H-imidazo[4,5-b]pyridin-3-yl)benzyl)-N-(4-chloro-1,3,5-triazin-2-yl)-7-azaspiro[3.5]nonan-2-amine (50 mg, 79.5 μmol) in DMSO (2 mL) were added KCN (30 mg, 461 μmol) and DABCO (1.78 mg, 15.9 μmol). The mixture was stirred at 25° C. for 1 hr. The mixture was quenched with H$_2$O (10 mL) and extracted with EtOAc (30 mL), the combined organic phases were dried over anhydrous sodium sulfate, filtered and concentrated. The residue was purified by prep-TLC (CH$_2$Cl$_2$:MeOH=10:1) to give 4-((7-(4-(2-(2-amino-pyridin-3-yl)-5-phenyl-3H-imidazo[4,5-b]pyridin-3-yl)benzyl)-7-azaspiro[3.5]nonan-2-yl)amino)-1,3,5-triazine-2-carbonitrile (Example 248, 6.3 mg, yield: 12.3%) as a light-yellow solid. MS: m/z=620.4 [M+H]$^+$. $^1$H NMR (400 MHz, Chloroform-d) δ 8.72-8.46 (m, 1H), 8.14 (d, J=8.4 Hz, 1H), 8.08-8.05 (m, 1H), 8.02 (d, J=8.0 Hz, 2H), 7.81 (d, J=8.4 Hz, 1H), 7.67-7.51 (m, 2H), 7.48-7.41 (m, 4H), 7.39-7.35 (m, 1H), 7.08 (d, J=7.6 Hz, 1H), 6.60 (br s, 2H), 6.38-6.33 (m, 1H), 5.99-5.91 (m, 1H), 4.50-4.41 (m, 1H), 3.77-3.54 (m, 2H), 2.55-2.39 (m, 4H), 1.65-1.53 (m, 8H).

Example 249: 4-(7-(4-(2-(2-aminopyridin-3-yl)-5-phenyl-3H-imidazo[4,5-b]pyridin-3-yl)benzyl)-2,7-diazaspiro[3.5]nonan-2-yl)-1,3,5-triazine-2-carbonitrile

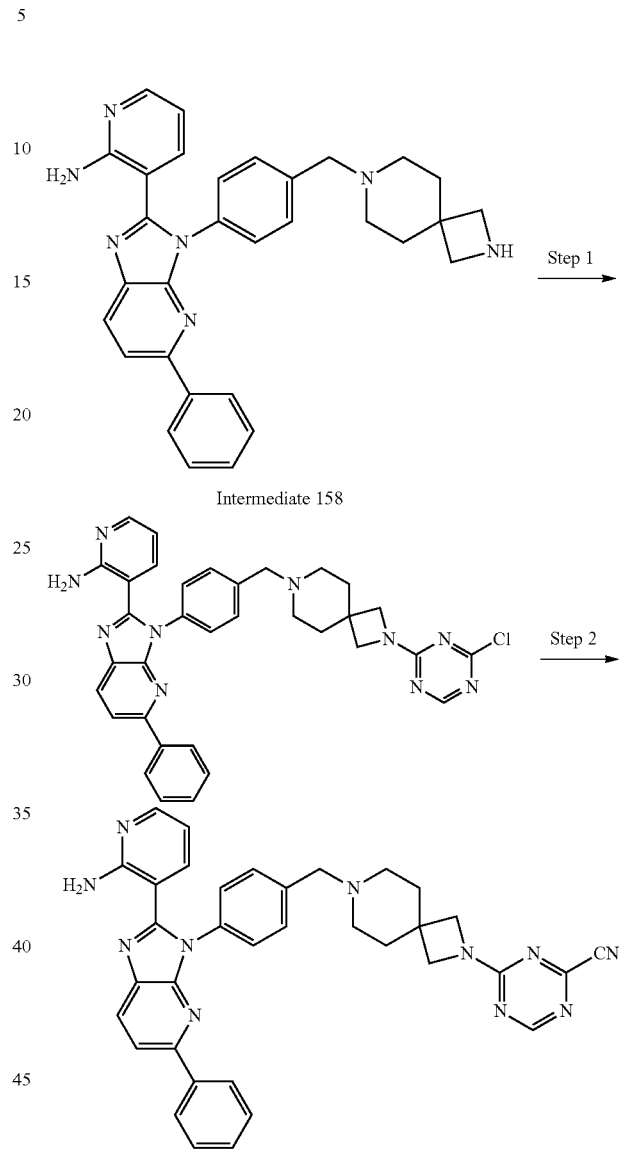

Intermediate 158

Example 249

Step 1: 3-(3-(4-((2-(4-Chloro-1,3,5-triazin-2-yl)-2,7-diazaspiro[3.5]nonan-7-yl)methyl)phenyl)-5-phenyl-3H-imidazo[4,5-b]pyridin-2-yl)pyridin-2-amine To a solution of Intermediate 158 (100 mg, 186 μmol) in THF (20 mL) was added DIEA (72.1 mg, 558 μmol). The mixture was stirred at 0° C. for 10 min. Then 2,4-dichloro-1,3,5-triazine (33.4 mg, 223 μmol) in THF (1 mL) was added to the mixture. The mixture was stirred at 0° C. for 0.5 hr, and then was partitioned between EtOAc (50 mL) and H$_2$O (30 mL). The organic layer was washed with brine (60 mL) and dried over Na$_2$SO$_4$, filtered, and concentrated. The residue was purified by prep-TLC (CH$_2$Cl$_2$:MeOH=10:1) to give 3-(3-(4-((2-(4-chloro-1,3,5-triazin-2-yl)-2,7-diazaspiro[3.5]nonan-7-yl)methyl)phenyl)-5-phenyl-3H-imidazo[4,5- b]pyridin-2-yl)pyridin-2-amine (12.0 mg, yield: 10%) as a light-yellow solid. MS: m/z=615.3 [M+H]⁺. ¹H NMR (400 MHz, Dimethylsulfoxide-d₆) δ 8.43 (s, 1H), 8.27 (d, J=8.4 Hz, 1H), 8.05-7.97 (m, 4H), 7.50-7.39 (m, 7H), 7.18-7.14 (m, 1H), 7.03 (br s, 2H), 6.38 (dd, J=7.6, 4.8 Hz, 1H), 3.84 (d, J=4.8 Hz, 4H), 3.56 (s, 2H), 2.40-2.31 (m, 4H), 1.81-1.74 (m, 4H).

Step 2: 4-(7-(4-(2-(2-Aminopyridin-3-yl)-5-phenyl-3H-imidazo[4,5-b]pyridin-3-yl)benzyl)-2,7-diazaspiro[3.5]nonan-2-yl)-1,3,5-triazine-2-carbonitrile To a solution of 7-(4-(2-(2-aminopyridin-3-yl)-5-phenyl-3H-imidazo[4,5-b]pyridin-3-yl)benzyl)-N-(4-chloro-1,3,5-triazin-2-yl)-7-azaspiro[3.5]nonan-2-amine (40 mg, 67.9 μmol) in DMSO (2 mL) were added KCN (8.84 mg, 136 μmol) and DABCO (1.52 mg, 13.6 μmol). The mixture was stirred at 25° C. for 1 hr. The reaction mixture was quenched with H₂O (10 mL) and extracted with EtOAc (30 mL). The combined organic layers were dried over anhydrous sodium sulfate, filtered and concentrated. The residue was purified by prep-TLC (CH₂Cl₂:MeOH=10:1) to give 4-(7-(4-(2-(2-aminopyridin-3-yl)-5-phenyl-3H-imidazo[4,5-b]pyridin-3-yl)benzyl)-2,7-diazaspiro[3.5]nonan-2-yl)-1,3,5-triazine-2-carbonitrile (Example 249, 22.9 mg, yield: 25%) as a light-yellow solid. MS: m/z=606.4 [M+H]⁺. ¹H NMR (400 MHz, Dimethylsulfoxide-d₆) δ 8.68 (s, 1H), 8.27 (d, J=8.4 Hz, 1H), 8.03-7.98 (m, 4H), 7.48-7.44 (m, 6H), 7.42-7.38 (m, 1H), 7.16 (dd, J=7.6, 1.6 Hz, 1H), 7.03 (br s, 2H), 6.38 (dd, J=7.6, 4.8 Hz, 1H), 3.87 (s, 4H), 3.58 (s, 2H), 2.42-2.34 (m, 4H), 1.82-1.48 (m, 4H).

Example 250: 4-(4-(4-(2-(2-Aminopyridin-3-yl)-5-phenyl-3H-imidazo[4,5-b]pyridin-3-yl)benzyl)-1,4-diazepan-1-yl)-1,3,5-triazine-2-carbonitrile

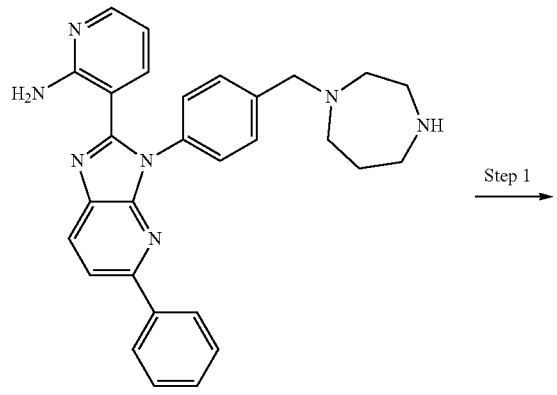

Intermediate 35

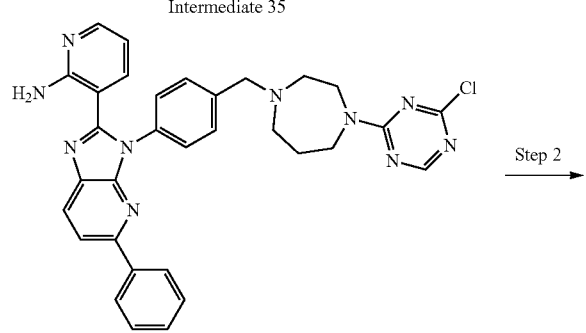

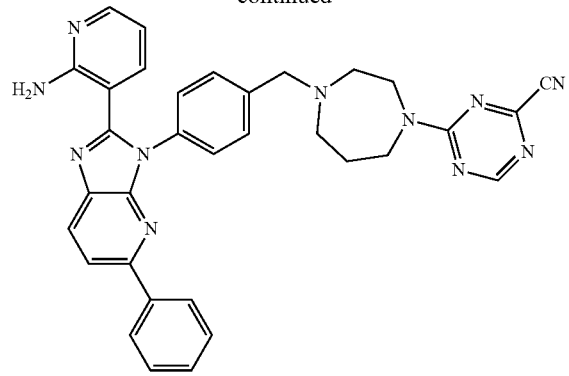

Example 250

Step 1: 3-(3-(4-((4-(4-Chloro-1,3,5-triazin-2-yl)-1,4-diazepan-1-yl)methyl)phenyl)-5-phenyl-3H-imidazo[4,5-b]pyridin-2-yl)pyridin-2-amine To a solution of Intermediate 35 (100 mg, 195 μmol) in THF (20 mL) was added DIEA (75.7 mg, 586 μmol). The mixture was stirred at 0° C. for 10 min. Then 2,4-dichloro-1,3,5-triazine (35.2 mg, 234 μmol) in THF (1 mL) was added to the mixture. The mixture was stirred at 0° C. for 0.5 hr. The mixture was partitioned between EtOAc (50 mL) and H₂O (30 mL). The separated organic layer was washed with brine (60 mL) and dried over Na₂SO₄, filtered and concentrated. The residue was purified by prep-TLC (CH₂Cl₂:MeOH=10:1) to give 3-(3-(4-((4-(4-chloro-1,3,5-triazin-2-yl)-1,4-diazepan-1-yl)methyl)phenyl)-5-phenyl-3H-imidazo[4,5-b]pyridin-2-yl)pyridin-2-amine (9.2 mg, yield: 7.7%) was obtained as a light-yellow solid. MS: m/z=589.3 [M+H]⁺. ¹H NMR (400 MHz, Dimethylsulfoxide-d₆) δ 8.48 (d, J=8.4 Hz, 1H), 8.26 (d, J=8.4 Hz, 1H), 8.05-7.97 (m, 4H), 7.50-7.39 (m, 7H), 7.16-7.11 (m, 1H), 7.04 (br s, 2H), 6.39-6.30 (m, 1H), 3.86-3.78 (m, 4H), 3.74-3.72 (m, 2H), 2.80-2.75 (m, 2H), 2.65-2.62 (m, 2H), 1.88-1.85 (m, 2H).

Step 2: 4-(4-(4-(2-(2-Aminopyridin-3-yl)-5-phenyl-3H-imidazo[4,5-b]pyridin-3-yl)benzyl)-1,4-diazepan-1-yl)-1,3,5-triazine-2-carbonitrile To a solution of 3-(3-(4-((4-(4-chloro-1,3,5-triazin-2-yl)-1,4-diazepan-1-yl)methyl)phenyl)-5-phenyl-3H-imidazo[4,5-b]pyridin-2-yl)pyridin-2-amine (90 mg, 146 μmol) in DMSO (2 mL) were added KCN (19.1 mg, 293 μmol) and DABCO (3.28 mg, 29.3 μmol). The mixture was stirred at 25° C. for 1 hr. The mixture was quenched with H₂O (10 mL) and extracted with EtOAc (30 mL), the combined organic phases were dried over anhydrous Na₂SO₄, filtered and concentrated. The residue was purified by prep-TLC (CH₂Cl₂:MeOH=10:1) to give 4-(4-(4-(2-(2-aminopyridin-3-yl)-5-phenyl-3H-imidazo[4,5-b]pyridin-3-yl)benzyl)-1,4-diazepan-1-yl)-1,3,5-triazine-2-carbonitrile (Example 250, 6.5 mg, yield: 15.7%) as a light-yellow solid. MS: m/z=580.3 [M+H]⁺. ¹H NMR (400 MHz, Chloroform-d) δ 8.56 (d, J=10.4 Hz, 1H), 8.14 (d, J=8.4 Hz, 1H), 8.07-8.05 (m, 1H), 8.03-8.00 (m, 3H), 7.81 (d, J=8.4 Hz, 1H), 7.51-7.48 (m, 2H), 7.44-7.40 (m, 4H), 7.13-7.09 (m, 1H), 6.75 (br s, 2H), 6.39-6.35 (m, 1H), 3.95-3.91 (m, 2H), 3.90-3.87 (m, 2H), 3.77 (s, 2H), 2.87-2.83 (m, 2H), 2.74-2.70 (m, 2H), 2.02-2.00 (m, 2H).

Example 251: 4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile

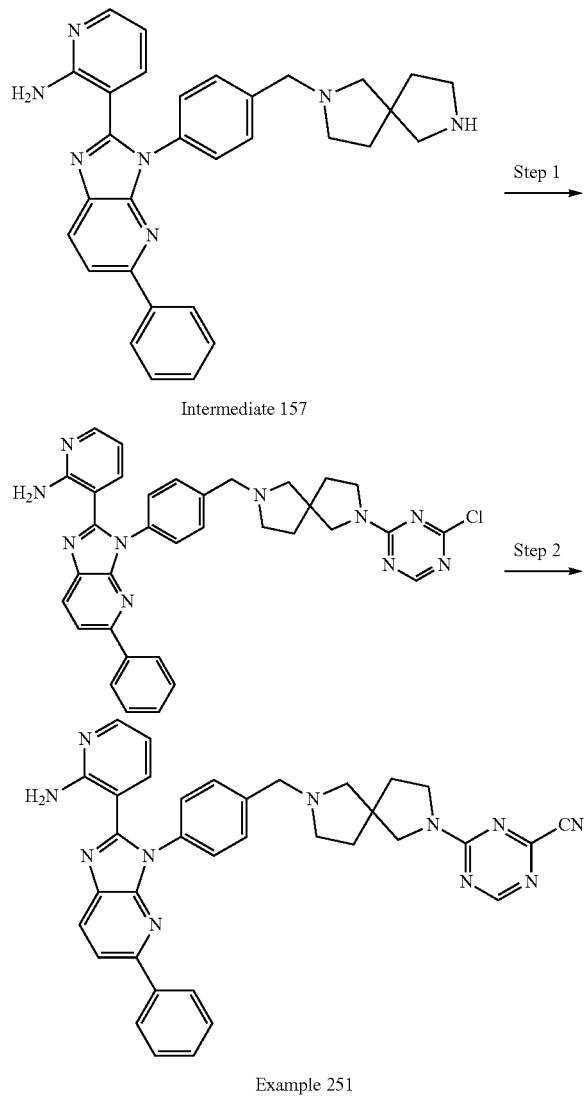

Step 1: 3-(3-(4-((7-(4-Chloro-1,3,5-triazin-2-yl)-2,7-diazaspiro[4.4]nonan-2-yl)methyl)phenyl)-5-phenyl-3H-imidazo[4,5-b]pyridin-2-yl)pyridin-2-amine To a solution of Intermediate 157 (120 mg, 239 µmol) in THF (10 mL) was added DIEA (93 mg, 718 µmol). The 2,4-dichloro-1,3,5-triazine (39 mg, 263 µmol) in THF (2 mL) was added into the mixture at 0° C. The mixture was stirred at 0° C. for 0.5 hr. The mixture was concentrated under reduced pressure at 40° C. After purified by prep-TLC (CH$_2$Cl$_2$:MeOH=20:1), 3-(3-(4-((7-(4-chloro-1,3,5-triazin-2-yl)-2,7-diazaspiro[4.4]nonan-2-yl)methyl)phenyl)-5-phenyl-3H-imidazo[4,5-b]pyridin-2-yl)pyridin-2-amine (80 mg, yield: 49%) was obtained as a yellow oil. MS: m/z=615.2 [M+H]$^+$.

Step 2: 4-(7-(4-(2-(2-Aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile To a solution of 3-(3-(4-((7-(4-chloro-1,3,5-triazin-2-yl)-2,7-diazaspiro[4.4]nonan-2-yl)methyl)phenyl)-5-phenyl-3H-imidazo[4,5-b]pyridin-2-yl)pyridin-2-amine (80 mg, 130 µmol) and KCN (17 mg, 261 µmol) in DMSO (2 mL) was added DABCO (2.9 mg, 26 µmol). The mixture was stirred at 25° C. for 2 hr. The reaction mixture was poured into water (5 mL). The resulting mixture was extracted with EtOAc (6 mL). The organic layer was washed with brine (5 mL), dried over anhydrous Na$_2$SO$_4$, filtered and concentrated to dryness. The residue was purified by silica gel flash chromatography (Eluent of 0~7% MeOH in CH$_2$Cl$_2$) to give 4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile (Example 251, 23.0 mg, yield: 28%) as a light-yellow solid. MS: m/z=606.4 [M+H]$^+$. $^1$H NMR (400 MHz, Acetonitrile-d$_3$) δ 8.51 (d, J=8.4 Hz, 1H), 8.14 (d, J=8.4 Hz, 1H), 8.04-7.95 (m, 3H), 7.87 (d, J=8.4 Hz, 1H), 7.51-7.37 (m, 7H), 7.13-7.11 (m, 1H), 6.60 (br s, 2H), 6.31 (dd, J=7.6, 4.8 Hz, 1H), 3.73-3.67 (m, 2H), 3.64-3.55 (m, 2H), 3.54-3.42 (m, 2H), 2.76-2.69 (m, 1H), 2.67-2.61 (m, 1H), 2.59-2.55 (m, 1H), 2.51-2.47 (m, 1H), 2.08-1.97 (m, 2H), 1.89-1.82 (m, 2H).

Example 252: 4-(2-(4-(2-(2-Aminopyridin-3-yl)-5-phenyl-3H-imidazo[4,5-b]pyridin-3-yl)benzyl)-2,8-diazaspiro[4.5]decan-8-yl)-1,3,5-triazine-2-carbonitrile

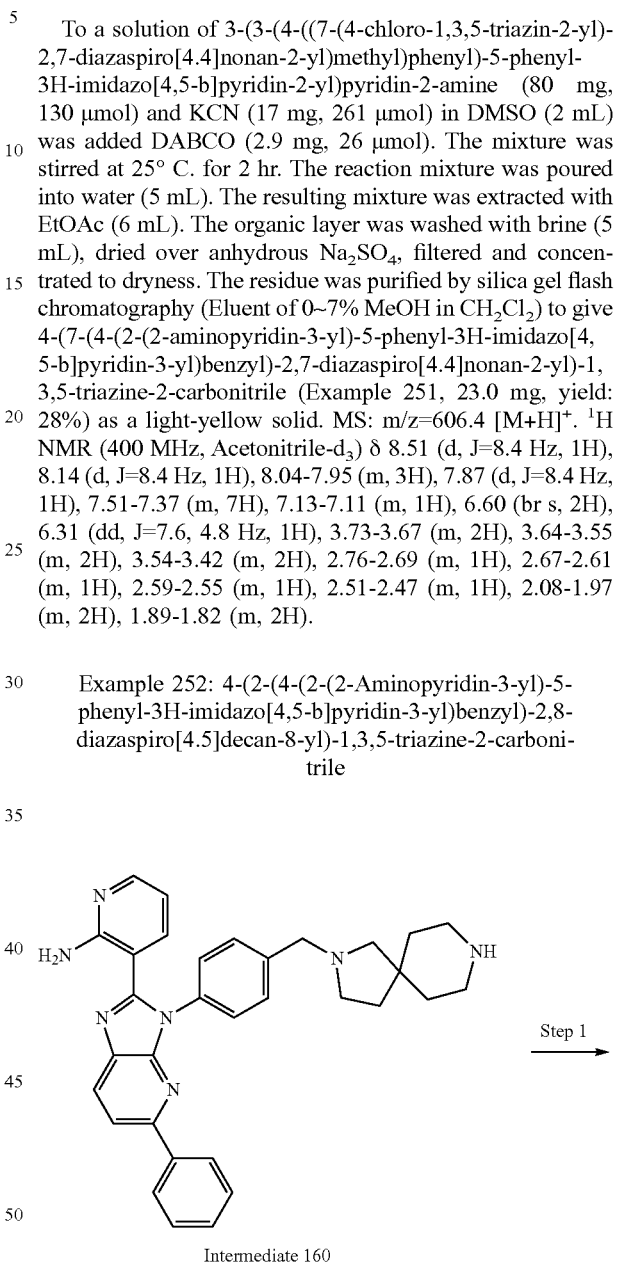

-continued

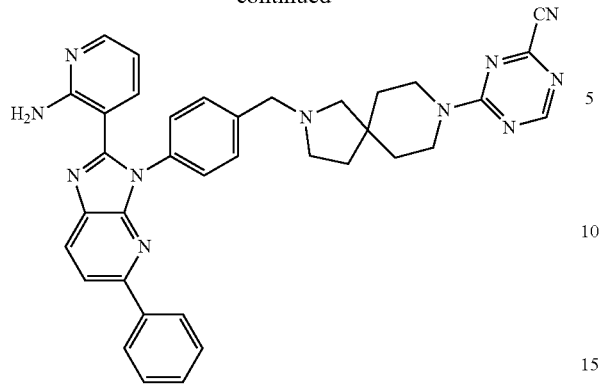

Example 252

Step 1: 3-(3-(4-((8-(4-Chloro-1,3,5-triazin-2-yl)-2,8-diazaspiro[4.5]decan-2-yl)methyl)phenyl)-5-phenyl-3H-imidazo[4,5-b]pyridin-2-yl)pyridin-2-amine To a solution of Intermediate 160 (150 mg, 291 μmol) in THF (10 mL) was added DIEA (113 mg, 873 μmol). The 2,4-dichloro-1,3,5-triazine (48 mg, 320 μmol) in THF (2 mL) was added into the mixture at 0° C. The mixture was stirred at 0° C. for 0.5 hr. The mixture was concentrated under reduced pressure at 40° C. The residue was purified by silica gel flash chromatography (Eluent of 0~7% MeOH in CH$_2$Cl$_2$) to give 3-(3-(4-((8-(4-chloro-1,3,5-triazin-2-yl)-2,8-diazaspiro[4.5]decan-2-yl)methyl)phenyl)-5-phenyl-3H-imidazo[4,5-b]pyridin-2-yl)pyridin-2-amine (140 mg, yield: 65%) as a yellow oil. MS: m/z=629.2 [M+H]$^+$.

Step 2: 4-(2-(4-(2-(2-Aminopyridin-3-yl)-5-phenyl-3H-imidazo[4,5-b]pyridin-3-yl)benzyl)-2,8-diazaspiro[4.5]decan-8-yl)-1,3,5-triazine-2-carbonitrile To a solution of 3-(3-(4-((8-(4-chloro-1,3,5-triazin-2-yl)-2,8-diazaspiro[4.5]decan-2-yl)methyl)phenyl)-5-phenyl-3H-imidazo[4,5-b]pyridin-2-yl)pyridin-2-amine (80 mg, 130 μmol) and KCN (40 mg, 614 μmol) in DMSO (2 mL) was added DABCO (5 mg, 45 μmol). The mixture was stirred at 25° C. for 2 hr. The reaction mixture was poured into water (5 mL). The resulting mixture was extracted with EtOAc (6 mL). The organic layer was washed with brine (2 ml) and dried over anhydrous Na$_2$SO$_4$, filtered and concentrated to dryness. The residue was purified by prep-HPLC (column: Phenomenex C18 150*25 mm*10 μm; mobile phase: [water (NH$_4$HCO$_3$)-ACN]; gradient: 52%-82% B over 10 min) to give 4-(2-(4-(2-(2-aminopyridin-3-yl)-5-phenyl-3H-imidazo[4,5-b]pyridin-3-yl)benzyl)-2,8-diazaspiro[4.5]decan-8-yl)-1,3,5-triazine-2-carbonitrile (Example 252, 2.6 mg, yield: 1.8%) as an off-white solid. MS: m/z=620.3 [M+H]$^+$. $^1$H NMR (400 MHz, Acetonitrile-d$_3$) δ 8.52 (s, 1H), 8.17 (d, J=8.4 Hz, 1H), 8.07-7.94 (m, 3H), 7.90 (d, J=8.4 Hz, 1H), 7.53 (d, J=8.4 Hz, 2H), 7.47-7.37 (m, 5H), 7.17 (dd, J=7.6, 1.6 Hz, 1H), 6.57 (br s, 2H), 6.37 (dd, J=7.6, 4.8 Hz, 1H), 3.92-3.75 (m, 4H), 3.73 (s, 2H), 2.70 (t, J=6.4 Hz, 2H), 2.52 (s, 2H), 1.72-1.69 (m, 2H), 1.67-1.62 (m, 4H).

Example 253: 4-(2-(4-(2-(2-Aminopyridin-3-yl)-5-phenyl-3H-imidazo[4,5-b]pyridin-3-yl)benzyl)-2,7-diazaspiro[4.5]decan-7-yl)-1,3,5-triazine-2-carbonitrile

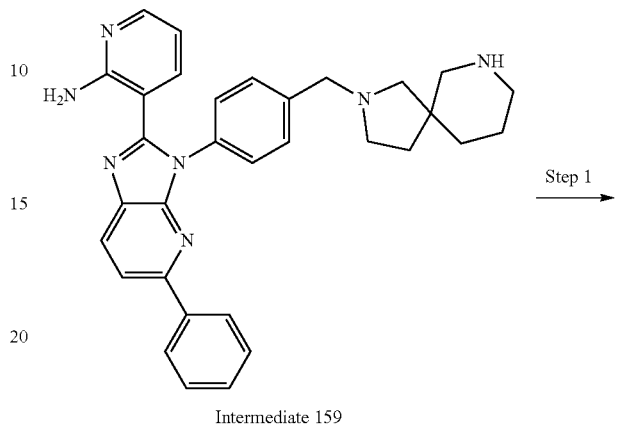

Intermediate 159

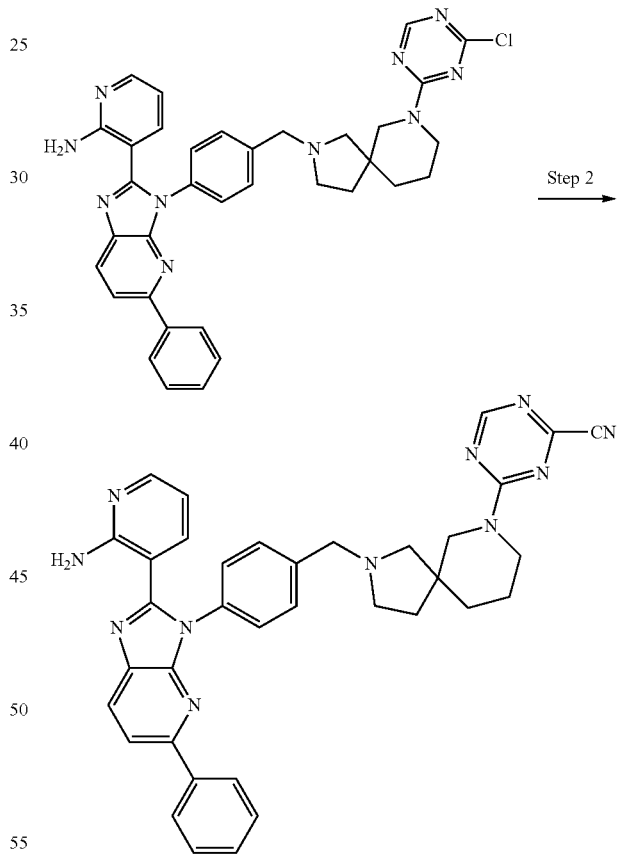

Example 253

Step 1: 3-(3-(4-(7-(4-Chloro-1,3,5-triazin-2-yl)-2,7-diazaspiro[4.5]decan-2-yl)phenyl)-5-phenyl-3H-imidazo[4,5-b]pyridin-2-yl)pyridin-2-amine To a solution of Intermediate 159 (150 mg, 291 μmol) in THF (8 mL) was added DIEA (113 mg, 873 μmol). The 2,4-dichloro-1,3,5-triazine (48 mg, 320 μmol) in THF (2 mL) was added into the mixture at 0° C. The mixture was stirred at 0° C. for 1 hr. The mixture was concentrated under reduced pressure at 42° C. The residue was purified by silica gel flash chromatography (Eluent of 0~6% MeOH in CH$_2$Cl$_2$) to give 3-(3-(4-(7-(4-chloro-1,3,5-triazin-2-yl)-2,7-diazaspiro[4.5]decan-2-yl)phenyl)-5-phenyl-3H-imidazo[4,5-b]pyridin-2-yl)pyridin-2-amine (100 mg, yield: 49%) as a yellow oil. MS: m/z=629.2 [M+H]$^+$.

Step 2: 4-(2-(4-(2-(2-aminopyridin-3-yl)-5-phenyl-3H-imidazo[4,5-b]pyridin-3-yl)benzyl)-2,7-diazaspiro[4.5]decan-7-yl)-1,3,5-triazine-2-carbonitrile To a solution of 3-(3-(4-(7-(4-chloro-1,3,5-triazin-2-yl)-2,7-diazaspiro[4.5]decan-2-yl)phenyl)-5-phenyl-3H-imidazo[4,5-b]pyridin-2-yl)pyridin-2-amine (100 mg, 160 µmol) and KCN (50 mg, 770 µmol) in DMSO (2 mL) was added DABCO (3.6 mg, 32 µmol). The mixture was stirred at 25° C. for 0.5 hr. The reaction mixture was poured into water (5 mL). The resulting mixture was extracted with EtOAc (6 mL). The organic layer was washed with brine (2 ml) and dried over anhydrous Na$_2$SO$_4$, filtered and concentrated to dryness. The residue was purified by silica gel flash chromatography (Eluent of 0~8% MeOH in CH$_2$Cl$_2$) to give 4-(2-(4-(2-(2-aminopyridin-3-yl)-5-phenyl-3H-imidazo[4,5-b]pyridin-3-yl)benzyl)-2,7-diazaspiro[4.5]decan-7-yl)-1,3,5-triazine-2-carbonitrile (Example 253, 18.5 mg, yield: 18%) as a light-yellow solid. MS: m/z=620.5 [M+H]$^+$. $^1$H NMR (400 MHz, Acetonitrile-d$_3$) δ 8.60-8.37 (m, 1H), 8.17 (dd, J=8.4, 1.2 Hz, 1H), 8.06-7.96 (m, 3H), 7.89 (d, J=8.4 Hz, 1H), 7.53-7.37 (m, 7H), 7.21-7.08 (m, 1H), 6.61 (br s, 2H), 6.33 (dd, J=7.6, 4.8 Hz, 1H), 3.95-3.82 (m, 2H), 3.80-3.73 (m, 1H), 3.69-3.62 (m, 2H), 3.61-3.51 (m, 1H), 2.89-2.83 (m, 1H), 2.58 (d, J=9.2 Hz, 1H), 2.52-2.48 (m, 1H), 1.97-1.95 (m, 1H), 1.73-1.63 (m, 4H), 1.61-1.53 (m, 2H).

Example 254: 4-(9-(4-(2-(2-Aminopyridin-3-yl)-5-phenyl-3H-imidazo[4,5-b]pyridin-3-yl)benzyl)-2,9-diazaspiro[5.5]undecan-2-yl)-1,3,5-triazine-2-carbonitrile

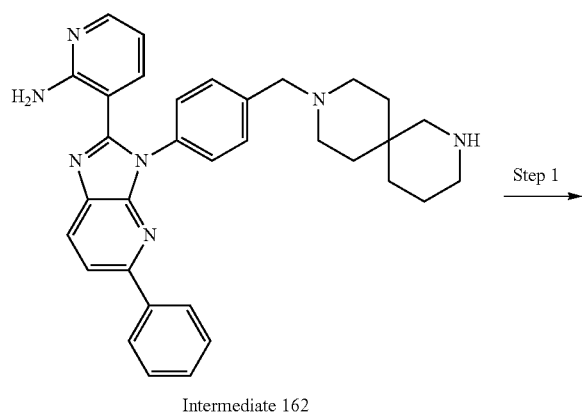

Intermediate 162

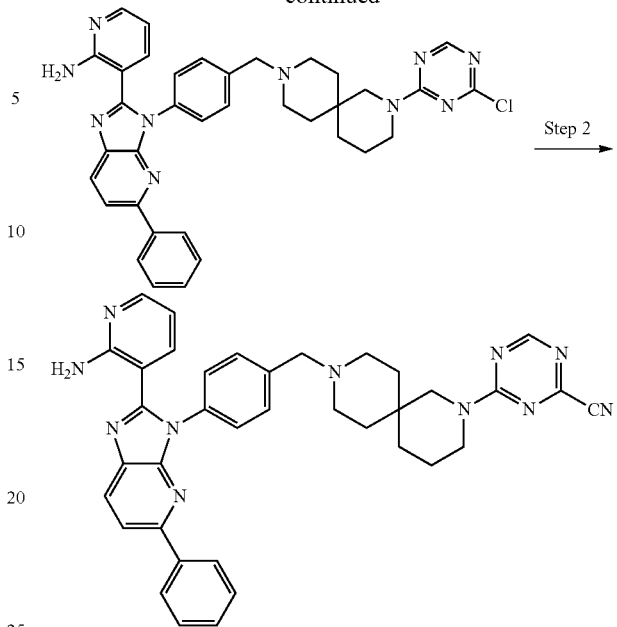

Example 254

Step 1: 3-(3-(4-((2-(4-Chloro-1,3,5-triazin-2-yl)-2,9-diazaspiro[5.5]undecan-9-yl)methyl)phenyl)-5-phenyl-3H-imidazo[4,5-b]pyridin-2-yl)pyridin-2-amine To a mixture of Intermediate 162 (100 mg, 189 µmol) in THF (2 mL) and H$_2$O (0.5 mL) was added K2CO3 (78.3 mg, 566 µmol) at 0° C. The mixture was stirred at 0° C. for 15 minutes and 2,4-dichloro-1,3,5-triazine (28.3 mg, 189 µmol) was added. The mixture was stirred at 0° C. for 15 minutes, and then was quenched with H$_2$O (20 mL), extracted with EtOAc (20 mL×3). The combined organic phases were washed with brine (20 mL), dried over anhydrous Na$_2$SO$_4$, filtered and concentrated. The mixture was purified by silica gel flash chromatography (eluent 0~8% MeOH in CH$_2$Cl$_2$) and prep-TLC (10% MeOH in CH$_2$Cl$_2$) to give 3-(3-(4-((2-(4-chloro-1,3,5-triazin-2-yl)-2,9-diazaspiro[5.5]undecan-9-yl)methyl)phenyl)-5-phenyl-3H-imidazo[4,5-b]pyridin-2-yl)pyridin-2-amine (17.4 mg, yield: 29%) as a yellow solid. MS: m/z=665.3 [M+Na]$^+$. $^1$H NMR (400 MHz, Chloroform-d) δ 8.25 (d, J=2.0 Hz, 1H), 8.06 (d, J=8.0 Hz, 1H), 8.00-7.93 (m, 3H), 7.73 (d, J=8.4 Hz, 1H), 7.50-7.44 (m, 2H), 7.38-7.29 (m, 5H), 7.06-6.98 (m, 1H), 6.54 (br s, 2H), 6.33-6.25 (m, 1H), 3.77-3.59 (m, 6H), 2.63-2.38 (m, 4H), 1.61-1.48 (m, 8H).

Step 2: 4-(9-(4-(2-(2-Aminopyridin-3-yl)-5-phenyl-3H-imidazo[4,5-b]pyridin-3-yl)benzyl)-2,9-diazaspiro[5.5]undecan-2-yl)-1,3,5-triazine-2-carbonitrile To a solution of 3-[3-[4-[[2-(4-chloro-1,3,5-triazin-2-yl)-2,9-diazaspiro[5.5]undecan-9-yl]methyl]phenyl]-5-phenyl-imidazo[4,5-h]pyridin-2-yl]pyridin-2-amine (150 mg, 233 µmol) in DMSO (dry) (5 mL) were added KCN (330 mg, 5.07 mmol) and DABCO (5.23 mg, 46.6 µmol) at 20° C. The mixture was stirred at 20° C. for 12 hr. Water (10 mL) was added to the mixture. The aqueous layer was extracted with EtOAc (20 mL×2). The combined organic layers were washed with H₂O (15 mL×2), brine (15 mL), dried over anhydrous Na₂SO₄, filtered and concentrated. The residue was purified by prep-TLC (CH₂Cl₂:MeOH=10:1) to give 4-(9-(4-(2-(2-aminopyridin-3-yl)-5-phenyl-3H-imidazo[4,5-b]pyridin-3-yl)benzyl)-2,9-diazaspiro[5.5]undecan-2-yl)-1,3,5-triazine-2-carbonitrile (Example 254, 38.1 mg, yield: 26%) as a yellow solid. MS: m/z=634.3 [M+H]⁺. ¹H NMR (400 MHz, Dimethylsulfoxide-d₆) δ 8.67 (d, J=3.2 Hz, 1H), 8.27 (d, J=8.4 Hz, 1H), 8.03-7.97 (m, 4H), 7.47-7.37 (m, 7H), 7.18-7.13 (m, 1H), 7.04 (d, J=6.4 Hz, 2H), 6.36 (dd, J=7.6, 4.8 Hz, 1H), 3.80-3.78 (m, 1H), 3.73 (s, 2H), 3.67-3.65 (m, 1H), 3.59 (d, J=8.8 Hz, 2H), 2.46-2.44 (m, 2H), 2.38-2.30 (m, 2H), 1.61-1.51 (m, 4H), 1.48-1.38 (m, 4H).

Example 255: (R)-4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile

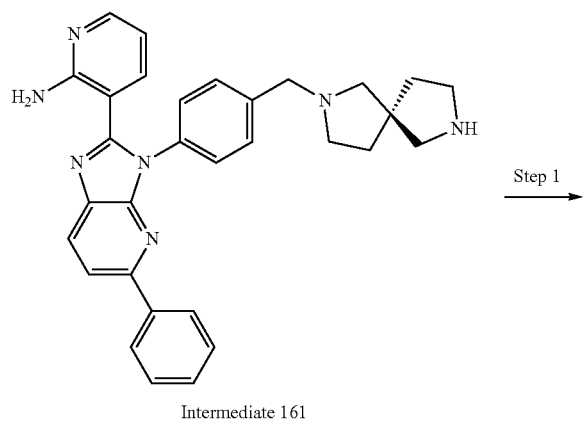

Intermediate 161

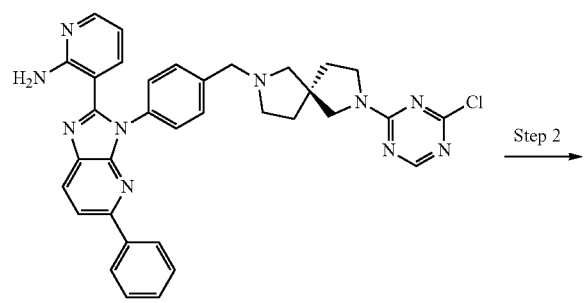

Example 255

Step 1: (R)-3-(3-(4-((7-(4-chloro-1,3,5-triazin-2-yl)-2,7-diazaspiro[4.4]nonan-2-yl)methyl)phenyl)-5-phenyl-3H-imidazo[4,5-b]pyridin-2-yl)pyridin-2-amine To a solution of Intermediate 161 (200 mg, 372 μmol, HCl salt) in THF (8 mL) and H₂O (2 mL) were added K₂CO₃ (154 mg, 1.12 mmol) and 2,4-dichloro-1,3,5-triazine (61.3 mg, 409 mol) at 0° C. This mixture was stirred at 0° C. for 0.5 hr and then H₂O (35 mL) was added to the mixture. The aqueous phase was extracted with EtOAc (30 mL×3). The combined organic layers were washed with brine (30 mL), dried over anhydrous Na₂SO₄, filtered and concentrated. The residue was purified by prep-TLC (DCM:MeOH=20:1) to give (R)-3-(3-(4-((7-(4-chloro-1,3,5-triazin-2-yl)-2,7-diazaspiro[4.4]nonan-2-yl)methyl)phenyl)-5-phenyl-3H-imidazo[4,5-b]pyridin-2-yl)pyridin-2-amine (90.0 mg, yield: 39%) as yellow oil. MS: m/z=615.3 [M+H]⁺.

Step 2: (R)-4-(7-(4-(2-(2-Aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile To a solution of (R)-3-(3-(4-((7-(4-chloro-1,3,5-triazin-2-yl)-2,7-diazaspiro[4.4]nonan-2-yl)methyl)phenyl)-5-phenyl-3H-imidazo[4,5-b]pyridin-2-yl)pyridin-2-amine (90.0 mg, 146 μmol) in DMSO (1 mL) were added KCN (10 mg, 154 μmol) and DABCO (3.28 mg, 29.3 μmol) at 25° C. This mixture was stirred at 25° C. for 16 hr and then H₂O (35 mL) was added to the mixture. The aqueous phase was extracted with EtOAc (30 mL×3). The combined organic phase was washed with brine (30 mL), dried over anhydrous Na₂SO₄, filtered and concentrated. The residue was purified by prep-TLC (CH₂Cl₂:MeOH=20:1) to give (R)-4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile (Example 255, 6.30 mg, yield: 7.0%) as a light-yellow solid. MS: m/z=606.3 [M+H]⁺. ¹H NMR (400 MHz, Methanol-d₄) δ=8.54 (d, J=4.0 Hz, 1H), 8.18 (d, J=8.4 Hz, 1H), 8.05-7.99 (m, 2H), 7.98-7.91 (m, 2H), 7.58-7.51 (m, 2H), 7.49-7.32 (m, 5H), 7.33-7.28 (m, 1H), 6.44 (dd, J=7.2, 4.8 Hz, 1H), 3.77 (d, J=2.8 Hz, 2H), 3.69-3.52 (m, 4H), 2.86-2.58 (m, 4H), 2.10-1.99 (m, 2H), 1.96-1.87 (m, 2H).

Example 256: 4-((2R,6R)-4-(4-(2-(2-Aminopyridin-3-yl)-5-phenyl-3H-imidazo[4,5-b]pyridin-3-yl)benzyl)-2,6-dimethylpiperazin-1-yl)-1,3,5-triazine-2-carbonitrile

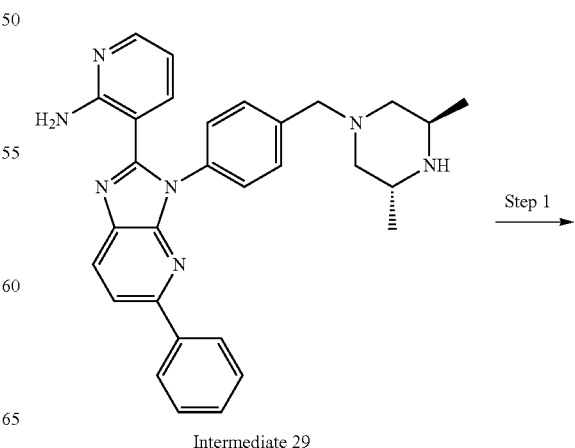

Intermediate 29

-continued

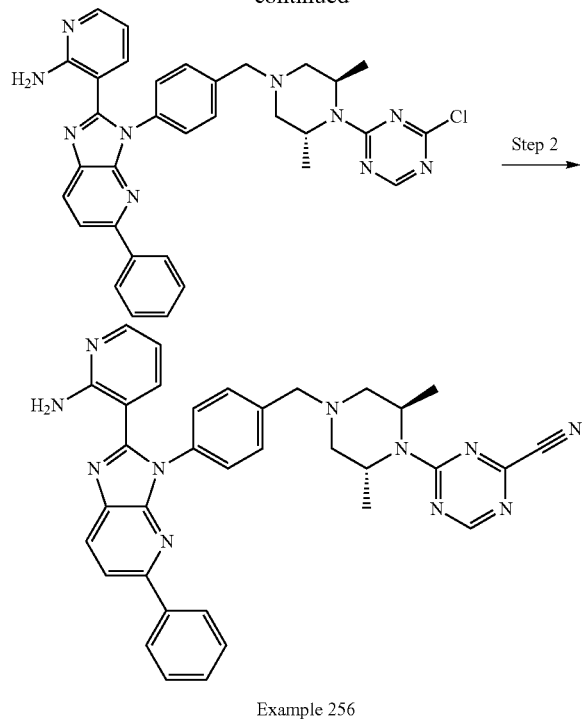

Example 256

Step 1: 3-(3-(4-(((3R,5R)-4-(4-Chloro-1,3,5-triazin-2-yl)-3,5-dimethylpiperazin-1-yl)methyl)phenyl)-5-phenyl-3H-imidazo[4,5-b]pyridin-2-yl)pyridin-2-amine To a solution of Intermediate 29 (100 mg, 204 µmol) and DIEA (66.0 mg, 511 µmol) in THF (6 mL) and DMF (6 mL) was added 2,4-dichloro-1,3,5-triazine (33.7 mg, 225 µmol). The mixture was stirred at 0° C. for 1 hr. The mixture was partitioned between EtOAc (50 mL) and $H_2O$ (30 mL). The separated organic layer was washed with $H_2O$ (25 mL×3) and dried over $Na_2SO_4$, filtered, and concentrated. The residue was purified by prep-TLC ($CH_2Cl_2$:MeOH=15:1) to give 3-(3-(4-(((3R,5R)-4-(4-chloro-1,3,5-triazin-2-yl)-3,5-dimethylpiperazin-1-yl)methyl)phenyl)-5-phenyl-3H-imidazo[4,5-b]pyridin-2-yl)pyridin-2-amine (36.5 mg, yield: 30%) as a yellow solid. MS: m/z=603.3 [M+H]$^+$. $^1$H NMR (400 MHz, Methanol-d$_4$) δ 8.39 (s, 1H), 8.19 (d, J=8.4 Hz, 1H), 8.06-7.91 (m, 4H), 7.57 (d, J=8.4 Hz, 2H), 7.48-7.32 (m, 6H), 6.48 (dd, J=7.6, 5.2 Hz, 1H), 4.50-4.44 (m, 2H), 3.98-3.79 (m, 2H), 3.19-3.10 (m, 2H), 2.78-2.70 (m, 2H), 1.43 (d, J=6.4 Hz, 6H).

Step 2: 4-((2R,6R)-4-(4-(2-(2-Aminopyridin-3-yl)-5-phenyl-3H-imidazo[4,5-b]pyridin-3-yl)benzyl)-2,6-dimethylpiperazin-1-yl)-1,3,5-triazine-2-carbonitrile To a solution of 3-(3-(4-(((3R,5R)-4-(4-chloro-1,3,5-triazin-2-yl)-3,5-dimethylpiperazin-1-yl)methyl)phenyl)-5-phenyl-3H-imidazo[4,5-b]pyridin-2-yl)pyridin-2-amine (60 mg. 99.5 µmol) in DMSO (1 mL) were added KCN (13.0 mg, 199 µmol) and DABCO (1.12 mg, 9.95 µmol). The mixture was stirred at 25° C. for 16 hr. The mixture was quenched with $H_2O$ (10 mL) and extracted with EtOAc (10 mL×3). The combined organic layers were dried over anhydrous $Na_2SO_4$, filtered and concentrated. The residue was purified by prep-HPLC (column: Waters xbridge 150×25 mm 10 µm; mobile phase: [water (NH$_4$HCO$_3$)-ACN]; B %: 65%-95%, 10 min) to give 4-((2R,6R)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile (Example 256, 8.8 mg, yield: 15%) as a yellow lyophilized powder. MS: m/z=594.3 [M+H]$^+$. $^1$H NMR (400 MHz, Dimethylsulfoxide-d$_6$) δ 8.76 (s, 1H), 8.27 (d, J=8.4 Hz, 1H), 8.08-7.95 (m, 4H), 7.57-7.36 (m, 7H), 7.18 (dd, J=7.6, 1.6 Hz, 1H), 7.03 (br s, 2H), 6.39 (dd, J=7.6, 4.8 Hz, 1H), 4.40-4.33 (m, 2H), 4.00-3.79 (m, 2H), 3.18-3.09 (m, 2H), 2.77-2.68 (m, 2H), 1.35 (d, J=6.4 Hz, 6H).

Example 257: 4-(5-(4-(2-(2-Aminopyridin-3-yl)-5-phenyl-3H-imidazo[4,5-b]pyridin-3-yl)benzyl)-2,5-diazabicyclo[2.2.2]octan-2-yl)-1,3,5-triazine-2-carbonitrile

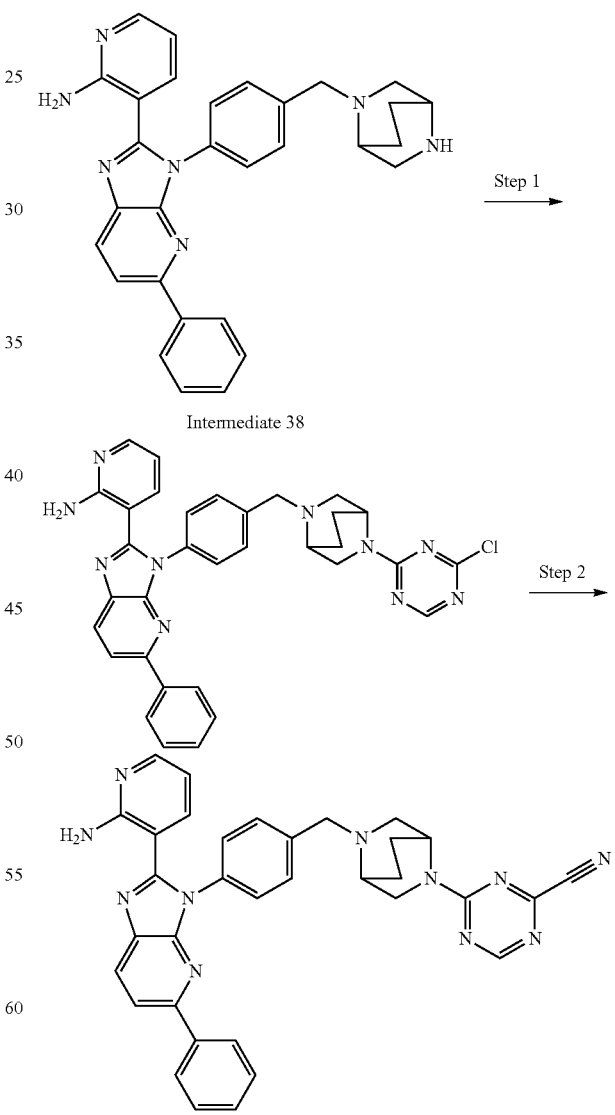

Intermediate 38

Example 257

Step 1: 3-(3-(4-((5-(4-Chloro-1,3,5-triazin-2-yl)-2,5-diazabicyclo[2.2.2]octan-2-yl)methyl)phenyl)-5-phenyl-3H-imidazo[4,5-b]pyridin-2-yl)pyridin-2-amine To a solution of Intermediate 38 (100 mg, 205 μmol) and 2,4-dichloro-1,3,5-triazine (33.8 mg, 226 μmol) in THF (5 mL) was added DIEA (133 mg, 1.0 mmol). The mixture was stirred at 0° C. for 1 hr. The reaction mixture was quenched with H₂O (10 mL) at 25° C., then mixture was extracted with CH₂Cl₂ (10 mL×3). The combined organic layers were washed with brine (30 mL), dried over Na₂SO₄, filtered, and concentrated under reduced pressure. The crude 3-(3-(4-((5-(4-chloro-1,3,5-triazin-2-yl)-2,5-diazabicyclo[2.2.2]octan-2-yl)methyl)phenyl)-5-phenyl-3H-imidazo[4,5-b]pyridin-2-yl)pyridin-2-amine (120 mg, yield: 78%) was obtained as a yellow solid. MS: m/z=601.4 [M+H]⁺.

Step 2: 4-(5-(4-(2-(2-Aminopyridin-3-yl)-5-phenyl-3H-imidazo[4,5-b]pyridin-3-yl)benzyl)-2,5-diazabicyclo[2.2.2]octan-2-yl)-1,3,5-triazine-2-carbonitrile To a solution of 3-(3-(4-((5-(4-chloro-1,3,5-triazin-2-yl)-2,5-diazabicyclo[2.2.2]octan-2-yl)methyl)phenyl)-5-phenyl-3H-imidazo[4,5-b]pyridin-2-yl)pyridin-2-amine (50 mg, 83.2 μmol) in DMSO (1 mL) were added KCN (16.3 mg, 250 μmol) and DABCO (1.87 mg, 16.6 μmol). The mixture was stirred at 25° C. for 16 hr. The mixture was quenched with H₂O (10 mL) and extracted with ethyl acetate (10 mL×3). The combined organic layers were dried over anhydrous Na₂SO₄, filtered and concentrated. The residue was purified by prep-TLC (MeOH:CH₂Cl₂=1:10) to give 4-(5-(4-(2-(2-aminopyridin-3-yl)-5-phenyl-3H-imidazo[4,5-b]pyridin-3-yl)benzyl)-2,5-diazabicyclo[2.2.2]octan-2-yl)-1,3,5-triazine-2-carbonitrile (Example 257, 9.5 mg, yield: 18%) as a yellow solid. MS: m/z=592.2 [M+H]⁺. ¹H NMR (400 MHz, Acetonitrile-d₃) δ 8.52-8.39 (m, 1H), 8.17 (d, J=8.4 Hz, 1H), 8.04-7.97 (m, 3H), 7.89 (d, J=8.4 Hz, 1H), 7.54 (d, J=8.4 Hz, 2H), 7.50-7.35 (m, 5H), 7.15 (d, J=6.0 Hz, 1H), 6.57 (br s, 2H), 6.38 (dd, J=7.6, 4.8 Hz, 1H), 4.76-4.62 (m, 1H), 3.95-3.81 (m, 3H), 3.58-3.46 (m, 1H), 3.08-3.04 (m, 1H), 3.06 (s, 1H), 1.78-1.66 (m, 2H), 1.30-1.24 (m, 2H).

Example 258: 4-(4-(4-(2-(2-Aminopyridin-3-yl)-5-cyclopropyl-3H-imidazo[4,5-b]pyridin-3-yl)benzyl)piperazin-1-yl)pyrimidine-2-carbonitrile

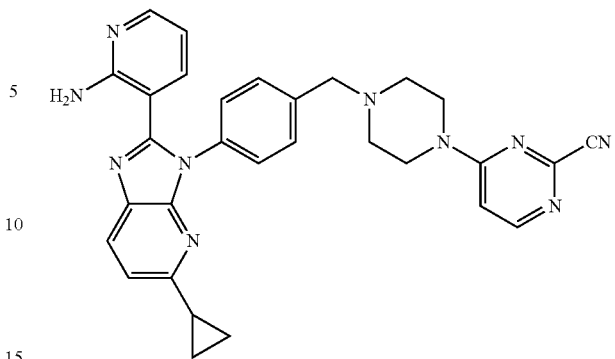

Example 258

To a solution of Intermediate 53 (147 mg, 485 μmol, TFA salt) and Intermediate 50 (200 mg, 485 μmol, HCl salt) in DMF (5 mL) were added NaI (36.3 mg, 242 μmol) and K₂CO₃ (335 mg, 2.43 mmol). The mixture was stirred at 50° C. for 2 hr. The reaction mixture was diluted with H₂O (20 mL) and extracted with EtOAc (30 mL×3). The combined organic layers were washed with brine (30 mL), dried over Na₂SO₄, filtered, and concentrated under reduced pressure. The residue was purified by silica gel flash chromatography (Eluent of 0~7% MeOH in CH₂C2) to give 4-(4-(4-(2-(2-aminopyridin-3-yl)-5-cyclopropyl-3H-imidazo[4,5-b]pyridin-3-yl)benzyl)piperazin-1-yl)pyrimidine-2-carbonitrile (Example 258, 46.2 mg, yield: 17%) as yellow solid. MS: m/z=529.3 [M+H]⁺. ¹H NMR (400 MHz, Methanol-d₄) δ 8.20 (d, J=6.4 Hz, 1H), 8.01-7.96 (m, 2H), 7.54 (d, J=8.0 Hz, 2H), 7.37 (d, J=8.4 Hz, 2H), 7.30-7.25 (m, 2H), 6.97 (d, J=6.4 Hz, 1H), 6.47 (dd, J=7.6, 5.2 Hz, 1H), 3.85-3.75 (m, 4H), 3.65 (s, 2H), 2.64-2.59 (m, 4H), 2.23-2.15 (m, 1H), 1.00-0.93 (m, 4H).

Example 259: 4-(4-(4-(2-(2-Aminopyridin-3-yl)-5-(2-oxo-1,2-dihydropyridin-3-yl)-3H-imidazo[4,5-b]pyridin-3-yl)benzyl)piperazin-1-yl)pyrimidine-2-carbonitrile

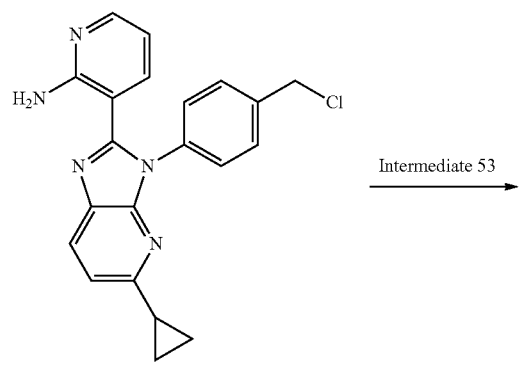

Intermediate 50

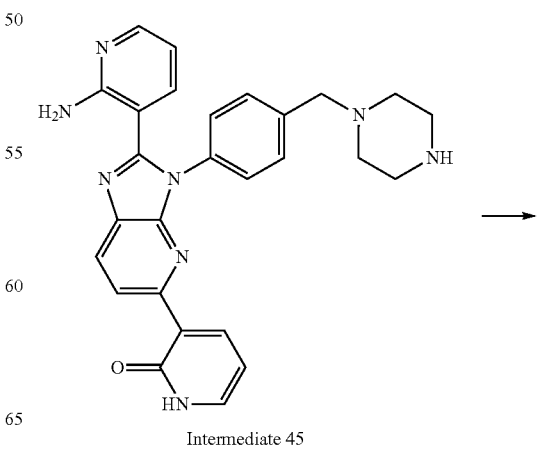

Intermediate 45

1337
-continued

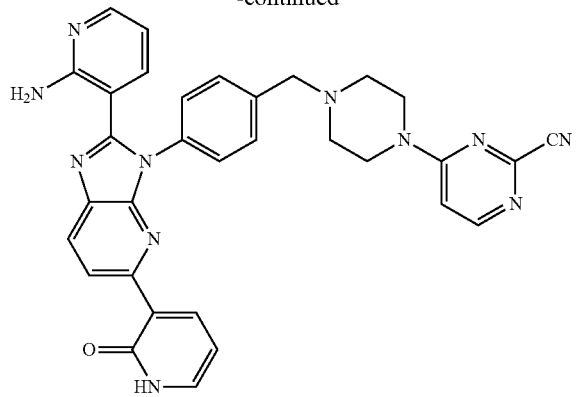

Example 259

1338
-continued

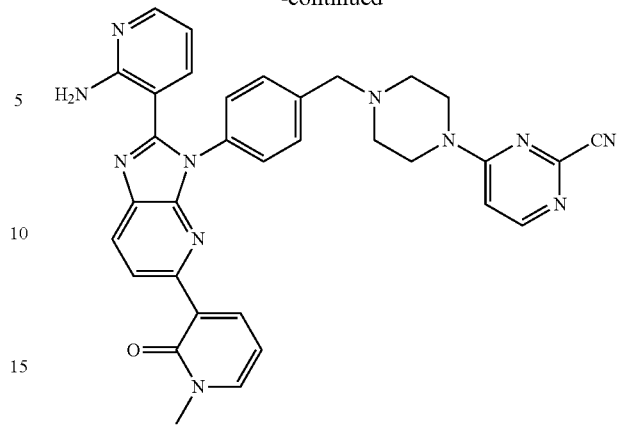

Example 260

A mixture of Intermediate 45 (100 mg, 209 μmol), 4-chloropyrimidine-2-carbonitrile (29 mg, 209 μmol) and DIEA (135 mg, 1.04 mmol) in NMP (2 mL) was taken up into a microwave tube. The sealed tube was heated at 130° C. for 1 hr under microwave. The reaction mixture was quenched with H$_2$O (5 mL) at 0° C., and then extracted with CH$_2$Cl$_2$ (15 mL×2). The combined organic layers were washed with brine (15 mL), dried over Na$_2$SO$_4$, filtered, and concentrated under reduced pressure. After purified by prep-HPLC (column: Phenomenex C18 150*25 mm*10 μm; mobile phase: [water (NH$_4$HCO$_3$)-ACN]; B %: 20%-50%, over 14 min) and prep-TLC (CH$_2$Cl$_2$:MeOH=10:1), 4-(4-(4-(2-(2-aminopyridin-3-yl)-5-(2-oxo-1,2-dihydropyridin-3-yl)-3H-imidazo[4,5-b]pyridin-3-yl)benzyl)piperazin-1-yl)pyrimidine-2-carbonitrile (Example 259, 13.8 mg, yield: 11%) was obtained as a brown solid. MS: m/z=582.3 [M+H]$^+$. $^1$H NMR (400 MHz, Methanol-d$_4$) δ 8.51 (d, J=8.4 Hz, 1H), 8.35 (dd, J=7.2, 2.0 Hz, 1H), 8.20-8.13 (m, 2H), 7.98 (dd, J=4.8, 1.6 Hz, 1H), 7.56 (d, J=8.4 Hz, 2H), 7.52-7.48 (m, 1H), 7.45 (d, J=8.4 Hz, 2H), 7.32 (dd, J=7.6, 1.6 Hz, 1H), 6.95 (d, J=6.4 Hz, 1H), 6.54-6.49 (m, 1H), 6.47 (dd, J=8.0, 5.2 Hz, 1H), 3.83-3.73 (m, 4H), 3.68 (s, 2H), 2.62-2.57 (m, 4H).

Example 260: 4-(4-(4-(2-(2-aminopyridin-3-yl)-5-(1-methyl-2-oxo-1,2-dihydropyridin-3-yl)-3H-imidazo[4,5-b]pyridin-3-yl)benzyl)piperazin-1-yl)pyrimidine-2-carbonitrile To a solution of Intermediate 57 (150 mg, 339 μmol) and Intermediate 53 (103 mg, 339 μmol, TFA) in DMF (2 mL) were added K$_2$CO$_3$ (234 mg, 1.69 mmol) and NaI (10.2 mg, 67.7 μmol). The mixture was stirred at 80° C. for 16 hr. The reaction mixture was quenched with H$_2$O (5 mL) at 25° C., and then diluted with CH$_2$Cl$_2$ (10 mL) and extracted with H$_2$O (15 mL×2). The combined organic layers were washed with brine (15 mL), dried over Na$_2$SO$_4$, filtered and concentrated under reduced pressure. After purified by prep-HPLC (column: Waters xbridge 150*25 mm*10 μm; mobile phase: [water (NH$_4$HCO$_3$)-ACN]; gradient: 30%-50% B over 14 min), 4-(4-(4-(2-(2-aminopyridin-3-yl)-5-(1-methyl-2-oxo-1,2-dihydropyridin-3-yl)-3H-imidazo[4,5-b]pyridin-3-yl)benzyl)piperazin-1-yl)pyrimidine-2-carbonitrile (Example 260, 10.6 mg, yield: 5.3%) was obtained as a yellow solid. MS: m/z=596.3 [M+H]$^+$. $^1$H NMR (400 MHz, Methanol-d$_4$) δ 8.46 (d, J=8.4 Hz, 1H), 8.27-8.22 (m, 1H), 8.20-8.14 (m, 2H), 8.00-7.96 (m, 1H), 7.74 (dd, J=6.8, 2.4 Hz, 1H), 7.56 (d, J=8.4 Hz, 2H), 7.45 (d, J=8.4 Hz, 2H), 7.32 (dd, J=8.0, 2.0 Hz, 1H), 7.01-6.92 (m, 1H), 6.52-6.42 (m, 2H), 3.83-3.74 (m, 4H), 3.70-3.67 (m, 5H), 2.62-2.57 (m, 4H).

Example 261: 4-((1-(4-(2-(2-Aminopyridin-3-yl)-5-(1-methyl-2-oxo-1,2-dihydropyridin-3-yl)-3H-imidazo[4,5-b]pyridin-3-yl)benzyl)piperidin-4-yl)amino)pyrimidine-2-carbonitrile

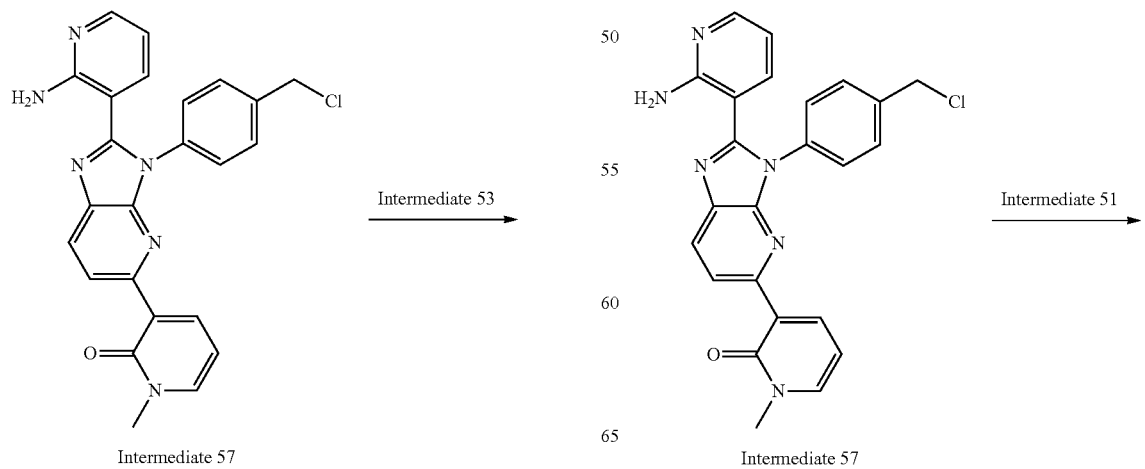

1339
-continued

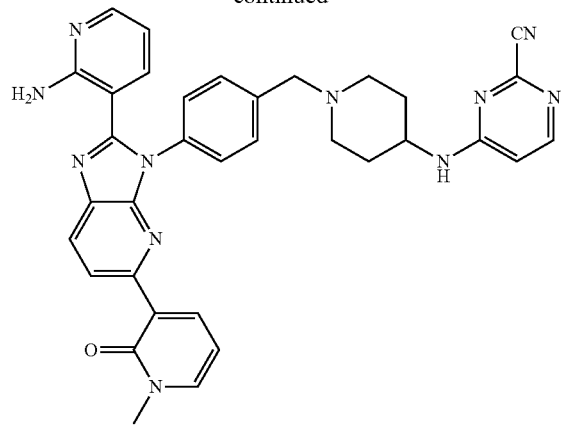

Example 261

To a solution of Intermediate 57 (160 mg, 361 μmol) and Intermediate 51 (88.1 mg, 278 μmol) in DMF (5 mL) were added NaI (10.8 mg, 72.3 μmol) and K₂CO₃ (299 mg, 2.17 mmol). The mixture was stirred at 50° C. for 2 hr. The reaction mixture was diluted with H₂O (50 mL) and extracted with EtOAc (50 mL×2). The combined organic layers were washed with brine (50 mL×2), dried over Na₂SO₄, filtered, and concentrated under reduced pressure. After purified by silica gel flash chromatography (Eluent of 0~10% MeOH in CH₂Cl₂) and then purified by prep-HPLC (column: Waters Xbridge 150×25 mm×5 um; mobile phase. [water (NH₄HCO₃)-ACN]; gradient: 22%-52% B over 10 min), 4-((1-(4-(2-(2-aminopyridin-3-yl)-5-(1-methyl-2-oxo-1,2-dihydropyridin-3-yl)-3H-imidazo[4,5-b]pyridin-3-yl)benzyl)piperidin-4-yl)amino)pyrimidine-2-carbonitrile (Example 261, 54.5 mg, yield: 24%) was obtained as a light-yellow lyophilized powder. MS: m/z=610.4 [M+H]⁺. ¹H NMR (400 MHz, Dimethylsulfoxide-d₆) δ 8.64 (d, J=8.4 Hz, 1H), 8.21-8.17 (m, 2H), 8.09-8.05 (m, 2H), 7.99 (dd, J=4.8, 1.6 Hz, 1H), 7.85 (dd, J=6.8, 2.0 Hz, 1H), 7.50-7.48 (m, 4H), 7.13 (dd, J=7.6, 1.6 Hz, 1H), 7.04 (br s, 2H), 6.67 (d, J=6.0 Hz, 1H), 6.40-6.35 (m, 2H), 3.88-3.76 (m, 1H), 3.59 (s, 2H), 3.55 (s, 3H), 2.85-2.80 (m, 2H), 2.19-2.10 (m, 2H), 1.98-1.83 (m, 2H), 1.55-1.43 (m, 2H)

Example 262: 4-((1-(4-(2-(2-Aminopyridin-3-yl)-5-cyclobutyl-3H-imidazo[4,5-h]pyridin-3-yl)benzyl)piperidin-4-yl)amino)pyrimidine-2-carbonitrile

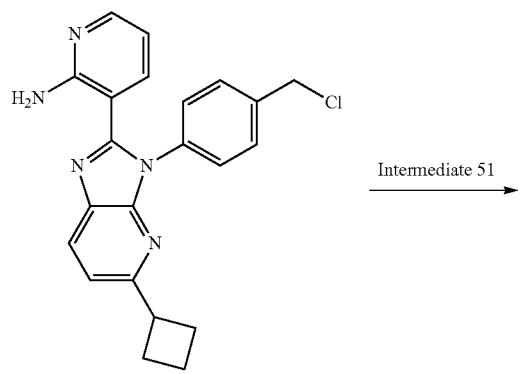

Intermediate 58

1340
-continued

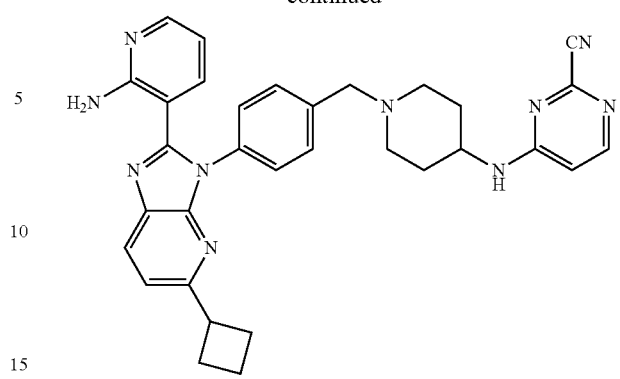

Example 262

To a solution of Intermediate 58 (281 mg, 659 μmol, HCl salt) and Intermediate 51 (209 mg 659 μmol, TFA) in DMF (5 mL) were added K₂CO₃ (273 mg, 1.98 mmol) and NaI (19.7 mg, 132 μmol). The mixture was stirred at 60° C. for 1 hr. The mixture was filtered, and the filtrate was concentrated to give the crude product. After purified by prep-HPLC (column: Waters xbridge 150*25 mm*10 μm; mobile phase: [water (NH₄HCO₃)-ACN]; gradient: 37%-67% B over 14 min), 4-((1-(4-(2-(2-aminopyridin-3-yl)-5-cyclobutyl-3H-imidazo[4,5-b]pyridin-3-yl)benzyl)piperidin-4-yl)amino)pyrimidine-2-carbonitrile (Example 262, 67.7 mg, yield: 18%) was obtained as an off-white lyophilized powder. MS: m/z=557.4 [M+H]⁺. ¹H NMR (400 MHz, Dimethylsulfoxide-d₆) δ 8.25-8.02 (m, 3H), 7.97 (dd, J=4.8, 2.0 Hz, 1H), 7.45 (d, J=8.4 Hz, 2H), 7.30 (d, J=8.4 Hz, 2H), 7.30 (d, J=8.4 Hz, 1H), 7.09 (dd, J=7.6, 1.6 Hz, 1H), 6.97 (br s, 2H), 6.67 (d, J=6.0 Hz, 1H), 6.35 (dd, J=7.6, 4.8 Hz, 1H), 3.86-3.76 (m, 1H), 3.74-3.64 (m, 1H), 3.58 (s, 2H), 2.87-2.75 (m, 2H), 2.28-2.09 (m, 6H), 1.99-1.74 (m, 4H), 1.56-1.42 (m, 2H).

Example 263: 4-((1-(4-(2-(2-Aminopyridin-3-yl)-5-(cyclohex-1-en-1-yl)-3H-imidazo[4,5-b]pyridin-3-yl)benzyl)piperidin-4-yl)amino)pyrimidine-2-carbonitrile

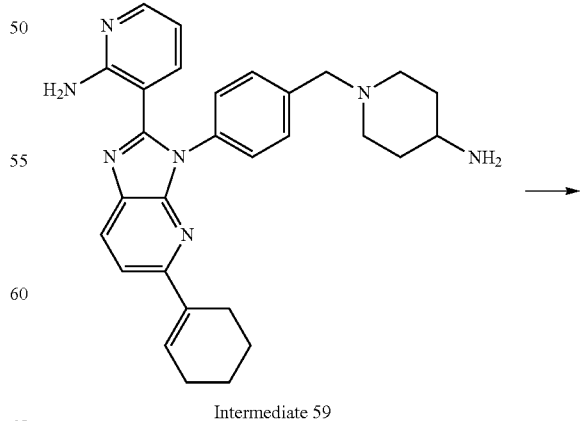

Intermediate 59

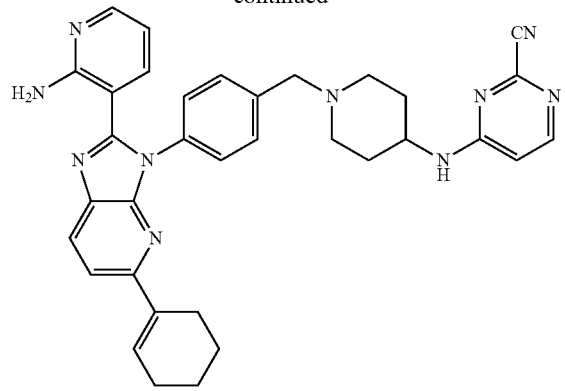

Example 263

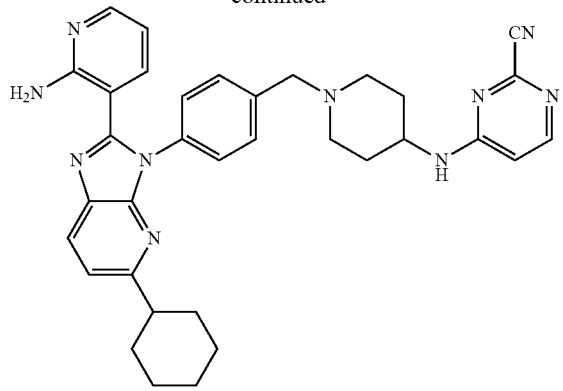

Example 264

A mixture of Intermediate 59 (80 mg, 167 μmol), 4-chloropyrimidine-2-carbonitrile (25.6 mg, 183 μmol) and DIEA (65 mg. 500 μmol) in NMP (2 mL) was taken up into a microwave tube. The sealed tube was stirred at 130° C. for 0.5 hr under microwave. The reaction mixture was poured into H$_2$O (10 mL), extracted with CH$_2$Cl$_2$ (15 mL). The organic layer was dried over anhydrous Na$_2$SO$_4$, filtered and concentrated under reduced pressure. The residue was purified by prep-HPLC (column: Phenomenex C18 150*25 mm*10 μm; mobile phase: [water (NH$_4$HCO$_3$)-ACN]; gradient: 45%-75% B over 14 min) to give 4-((1-(4-(2-(2-Aminopyridin-3-yl)-5-(cyclohex-1-en-1-yl)-3H-imidazo[4,5-b]pyridin-3-yl)benzyl)piperidin-4-yl)amino)pyrimidine-2-carbonitrile (Example 263, 17.3 mg, yield: 18%) as a brown lyophilized powder. MS: m/z=583.4 [M+H]$^+$. $^1$H NMR (400 MHz, Dimethylsulfoxide-d6) δ 8.22-8.01 (m, 3H), 7.97 (dd, J=4.8, 2.0 Hz, 1H), 7.52 (d, J=8.4 Hz, 1H), 7.48-7.41 (m, 2H), 7.40-7.33 (m, 2H), 7.97 (dd, J=8.0, 2.0 Hz, 1H), 7.06-6.95 (m, 3H), 6.76-6.53 (m, 2H), 6.34 (dd, J=8.0, 5.2 Hz, 1H), 3.91-3.69 (m, 1H), 3.61 (s, 2H), 2.83-2.77 (m, 2H), 2.46-2.42 (m, 2H), 2.22-2.09 (m, 4H), 1.89-1.87 (m, 2H), 1.72-1.64 (m, 2H), 1.62-1.54 (m, 2H), 1.53-1.38 (m, 2H).

Example 264: 4-((1-(4-(2-(2-Aminopyridin-3-yl)-5-cyclohexyl-3H-imidazo[4,5-b]pyridin-3-yl)benzyl)piperidin-4-yl)amino)pyrimidine-2-carbonitrile A mixture of Intermediate 60 (50 mg, 104 μmol), 4-chloropyrimidine-2-carbonitrile (15.9 mg, 114 μmol) and DIEA (40 mg. 311 μmol) in NMP (2 mL) was taken up into a microwave tube. The sealed tube was stirred at 130° C. for 0.5 hr under microwave. The reaction mixture was poured into H$_2$O (10 mL), extracted with CH$_2$Cl$_2$ (15 mL×3). The organic phase was dried over anhydrous Na$_2$SO$_4$, filtered and concentrated under reduced pressure. The residue was purified by prep-HPLC (column: Phenomenex C18 150*25 mm*10 μm, mobile phase: [water (NH$_4$HCO$_3$)-ACN]; gradient: 47%-77% B over 14 min) to give 4-((1-(4-(2-(2-Aminopyridin-3-yl)-5-cyclohexyl-3H-imidazo[4,5-b]pyridin-3-yl)benzyl)piperidin-4-yl)amino)pyrimidine-2-carbonitrile (Example 264, 4.8 mg, yield: 8%) as an off-white lyophilized powder. MS: m/z=585.4. [M+H]$^+$. $^1$H NMR (400 MHz, Methanol-d$_4$) δ 8.03 (d, J=8.0 Hz, 1H), 8.01-7.96 (m, 1H), 7.94 (dd, J=5.2, 2.0 Hz, 1H), 7.50 (d, J=8.4 Hz, 2H), 7.37 (d, J=8.4 Hz, 2H), 7.33-7.22 (m, 2H), 6.68-6.57 (m, 1H), 6.44 (dd, J=7.6, 4.8 Hz, 1H), 4.06-3.85 (m, 1H), 3.64 (s, 2H), 2.95 (d, J=11.6 Hz, 2H), 2.81-2.73 (m, 1H), 2.31-2.19 (m, 2H), 2.03-1.96 (m, 2H), 1.93-1.87 (m, 2H), 1.86-1.79 (m, 2H), 1.77-1.68 (m, 1H), 1.66-1.51 (m, 4H), 1.46-1.35 (m, 2H), 1.33-1.24 (m, 1H).

Example 265: 4-((1-(4-(2-(2-Aminopyridin-3-yl)-5-(3-cyanophenyl)-3H-imidazo[4,5-b]pyridin-3-yl)benzyl)piperidin-4-yl)amino)pyrimidine-2-carbonitrile

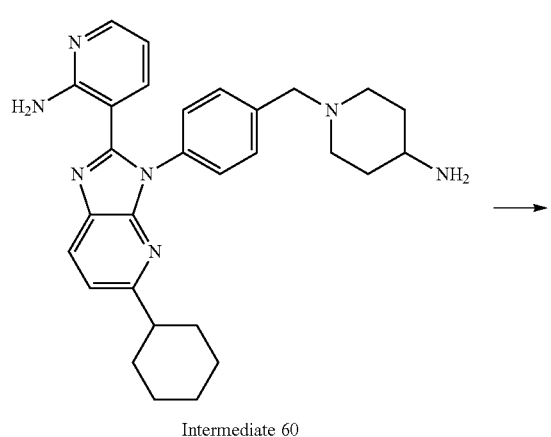

Intermediate 60

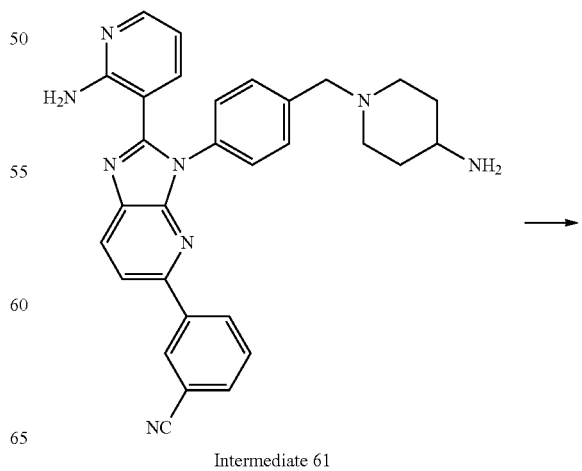

Intermediate 61

1343
-continued

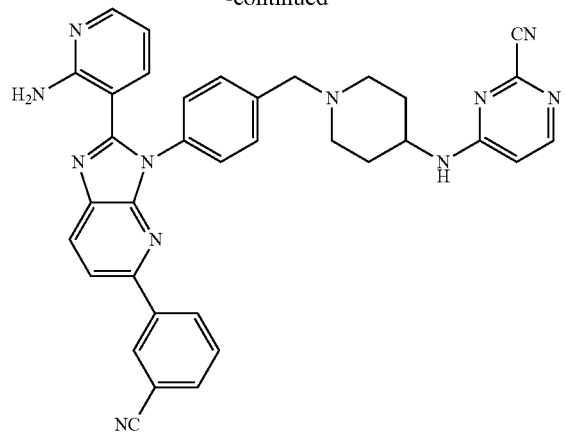

Example 265

1344
-continued

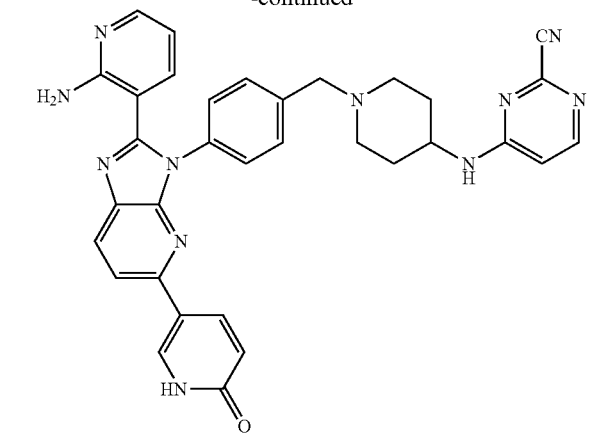

Example 266

A mixture of Intermediate 61 (60 mg. 200 μmol), 4-chloropyrimidine-2-carbonitrile (18.4 mg, 132 μmol) and DIEA (47 mg, 360 μmol) in NMP (2 mL) was taken up into a microwave tube. The sealed tube was stirred at 130° C. for 0.5 hr under microwave. The reaction mixture was poured into H₂O (10 mL), extracted with CH₂Cl₂ (15 mL×3). The organic phase was dried over anhydrous Na₂SO₄, filtered and concentrated under reduced pressure. The residue was purified by prep-HPLC (column: Phenomenex C18 150*25 mm*10 μm; mobile phase: [water (NH₄HCO₃)-ACN]; gradient: 40%-70% B over 14 min) to give 4-((1-(4-(2-(2-Aminopyridin-3-yl)-5-(3-cyanophenyl)-3H-imidazo[4,5-b]pyridin-3-yl)benzyl)piperidin-4-yl)amino)pyrimidine-2-carbonitrile (Example 265, 5.9 mg, yield: 8%) as an off-white lyophilized powder. MS: m/z=604.4 [M+H]⁺. ¹H NMR (400 MHz, Methanol-d₄) δ 8.43-8.29 (m, 2H), 8.23 (d, J=8.4 Hz, 1H), 8.04-7.93 (m, 3H), 7.74-7.68 (m, 1H), 7.63-7.54 (m, 3H), 7.46 (d, J=8.4 Hz, 2H), 7.33 (dd, J=7.6, 1.6 Hz, 1H), 6.67-6.51 (m, 1H), 6.47 (dd, J=7.6, 4.8 Hz, 1H), 4.09-3.86 (m, 1H), 3.66 (s, 2H), 3.01-2.92 (m, 2H), 2.32-2.23 (m, 2H), 2.03-1.98 (m, 2H), 1.66-1.55 (m, 2H).

Example 266: 4-((1-(4-(2-(2-Aminopyridin-3-yl)-5-(6-oxo-1,6-dihydropyridin-3-yl)-3H-imidazo[4,5-b]pyridin-3-yl)benzyl)piperidin-4-yl)amino)pyrimidine-2-carbonitrile A mixture of Intermediate 62 (100 mg, 203 μmol), 4-chloropyrimidine-2-carbonitrile (31 mg, 223 μmol) and DIEA (79 mg, 609 μmol) in NMP (2 mL) was taken up into a microwave tube. The sealed tube was stirred at 130° C. for 30 min under microwave. The reaction mixture was filtered. The residue was purified by prep-HPLC (column: Waters xbridge 150*25 mm 10 μm; mobile phase: [water (NH₄HCO₃)-ACN]; B %: 26%-56%, 14 min) to give 4-((1-(4-(2-(2-aminopyridin-3-yl)-5-(6-oxo-1,6-dihydropyridin-3-yl)-3H-imidazo[4,5-b]pyridin-3-yl)benzyl)piperidin-4-yl)amino)pyrimidine-2-carbonitrile (Example 266, 1.2 mg, yield. 1%,) as a light-yellow solid. MS: m/z=596.4 [M+H]⁺. ¹H NMR (400 MHz, Dimethylsulfoxide-d₆) δ 11.92-11.76 (m, 1H), 8.20 (d, J=8.4 Hz, 1H), 8.13 (dd, J=9.2, 2.4 Hz, 1H), 8.10-8.03 (m, 3H), 7.99 (dd, J=4.8, 1.6 Hz, 1H), 7.83 (d, J=8.4 Hz, 1H), 7.49-7.46 (m, 2H), 7.44-7.40 (m, 2H), 7.11 (d, J=6.0 Hz, 1H), 7.04 (br s, 2H), 6.70-6.66 (m, 1H), 6.43 (d, J=9.6 Hz, 1H), 6.36 (dd, J=7.6, 4.4 Hz, 1H), 3.86-3.78 (m, 1H), 3.58 (s, 2H), 2.85-2.81 (m, 2H), 2.20-2.12 (m, 2H), 1.94-1.86 (m, 2H), 1.54-1.45 (m, 2H).

Example 267: 4-((1-(4-(2-(2-Aminopyridin-3-yl)-5-(6-oxo-1,6-dihydropyridin-2-yl)-3H-imidazo[4,5-b]pyridin-3-yl)benzyl)piperidin-4-yl)amino)pyrimidine-2-carbonitrile

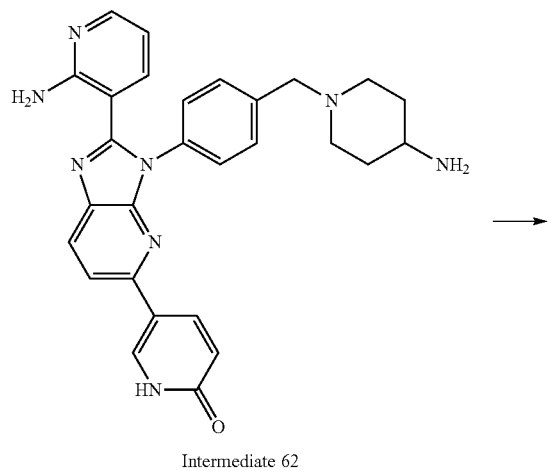

Intermediate 62

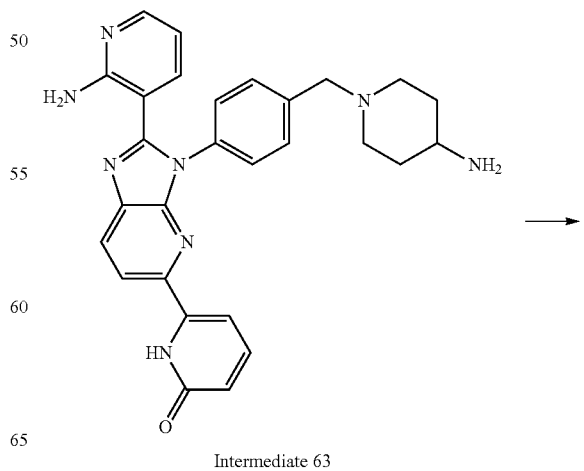

Intermediate 63

1345
-continued

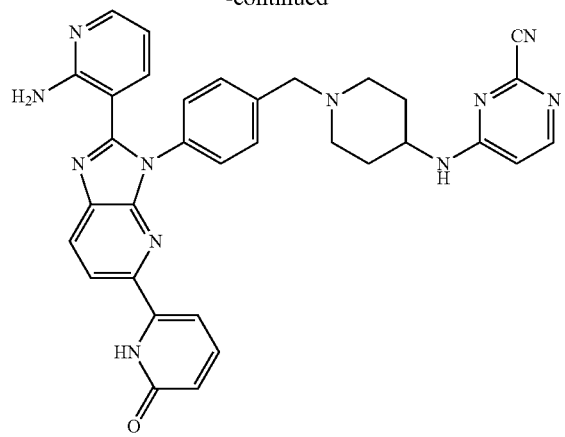

Example 267

1346
-continued

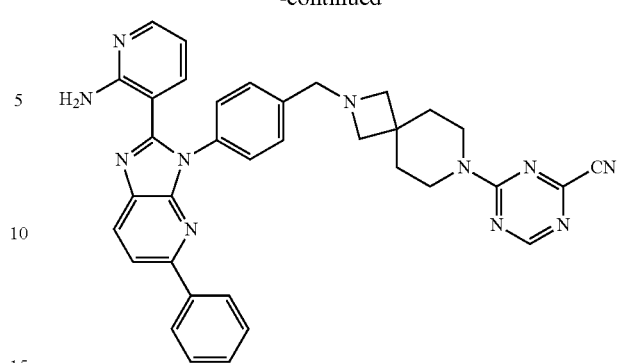

Example 268

To a solution of Intermediate 63 (80 mg, 162 μmol) and 4-chloropyrimidine-2-carbonitrile (23 mg, 162 μmol) in ACN (3 mL) were added NaI (2.4 mg, 16 μmol) and K₂CO₃ (67 mg, 487 μmol). The mixture was stirred at 80° C. for 2 hr. The reaction mixture was quenched with H₂O (10 mL) at 25° C., and extracted with EtOAc (15 mL×2). The combined organic layers were washed with brine (20 mL), dried over Na₂SO₄, filtered and concentrated under reduced pressure. The residue was purified by prep-HPLC (column: Waters xbridge 150*25 mm 10 μm; mobile phase: [water (NH₄HCO₃)-ACN]; B %: 22%-52%, 18 min) to give 4-((1-(4-(2-(2-aminopyridin-3-yl)-5-(6-oxo-1,6-dihydropyridin-2-yl)-3H-imidazo[4,5-b]pyridin-3-yl)benzyl)piperidin-4-yl)amino)pyrimidine-2-carbonitrile (Example 267, 15.5 mg, yield: 16%) as a yellow solid. MS: m/z=596.1 [M+H]⁺. ¹H NMR (400 MHz, Dimethylsulfoxide-d₆) δ 10.77 (br s, 1H), 8.33 (d, J=8.4 Hz, 1H), 8.21-8.13 (m, 1H), 8.10-8.00 (m, 3H), 7.67-7.42 (m, 6H), 7.16 d, J=6.8 Hz, 1H), 7.03 (br s, 2H), 6.67 (d, J=5.6 Hz, 1H), 6.50-6.42 (m, 1H), 6.39 (dd, J=7.6, 4.8 Hz, 1H), 3.88-3.76 (m, 1H), 3.60 (s, 2H), 2.86-2.80 (m, 2H), 2.22-2.12 (m, 2H), 1.93-1.85 (m, 2H), 1.56-1.45 (m, 2H).

Example 268: 4-(2-(4-(2-(2-Aminopyridin-3-yl)-5-phenyl-3H-imidazo[4,5-b]pyridin-3-yl)benzyl)-2,7-diazaspiro[3.5]nonan-7-yl)-1,3,5-triazine-2-carbonitrile To a solution of Intermediate 14 (233 mg, 565 μmol) and Intermediate 64 (130 mg, 565 μmol, TFA salt) in DMF (5 mL) were added K₂CO₃ (390 mg, 2.82 mmol) and NaI (8.46 mg, 56.5 μmol). The mixture was stirred at 25° C. for 16 hr. After purified by prep-HPLC (column: Phenomenex C₁₈ 150*25 mm*10 μm; mobile phase: [water (NH₄HCO₃)-ACN]; gradient: 50%-80% B over 10 min), 4-(2-(4-(2-(2-aminopyridin-3-yl)-5-phenyl-3H-imidazo[4,5-b]pyridin-3-yl)benzyl)-2,7-diazaspiro[3.5]nonan-7-yl)-1,3,5-triazine-2-carbonitrile (Example 268, 13.6 mg, yield: 3.8%) was obtained as a white solid. MS: m/z=606.3 [M+H]⁺. ¹H NMR (400 MHz, Acetonitrile-d₃) δ 8.52 (s, 1H), 8.17 (d, J=8.4 Hz, 1H), 8.02-7.99 (m, 3H), 7.89 (d, J=8.4 Hz, 1H), 7.48-7.39 (m, 7H), 7.17-7.12 (m, 1H), 6.55 (br s, 2H), 6.40-6.33 (m, 1H), 3.81-3.73 (m, 6H), 3.11 (s, 4H), 1.82-1.78 (m, 4H).

Example 269: (S)-4-(7-(4-(2-(2-Aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile

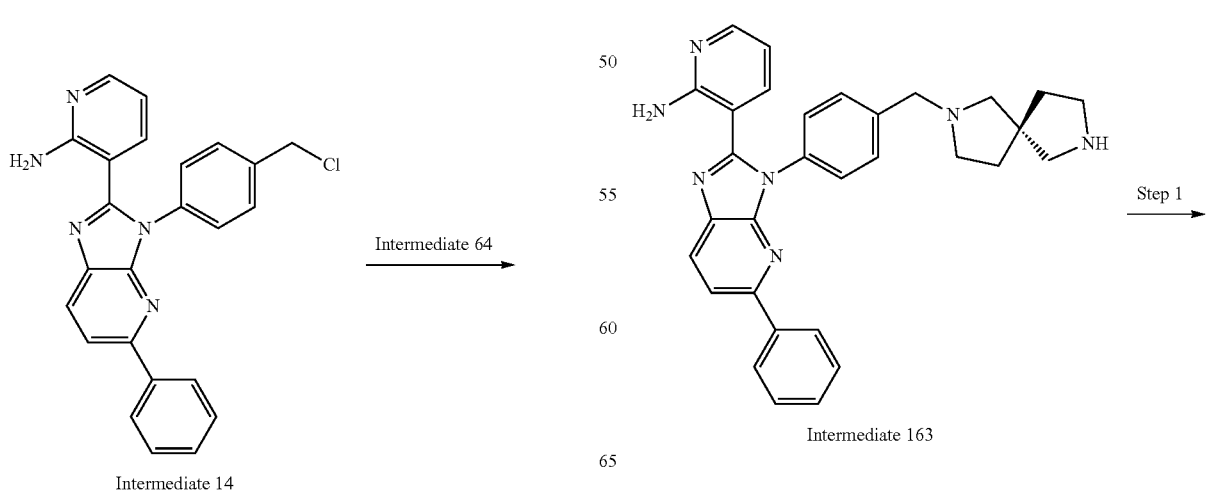

-continued

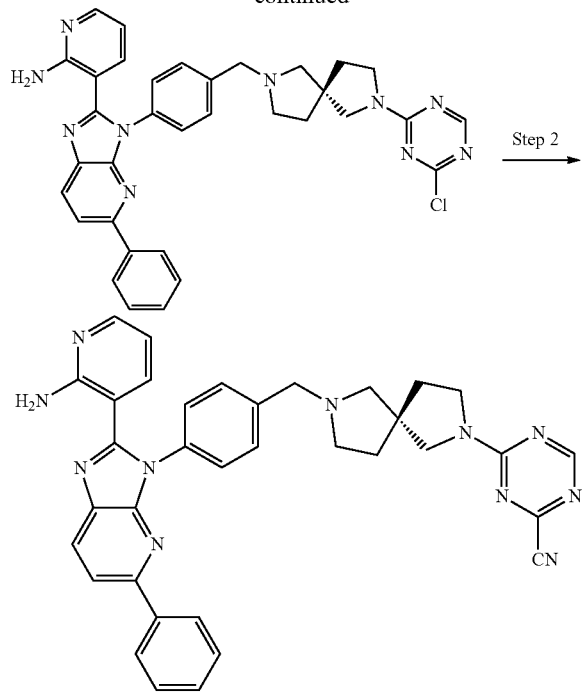

Example 269

Step 1: (S)-3-(3-(4-((7-(4-Chloro-1,3,5-triazin-2-yl)-2,7-diazaspiro[4.4]nonan-2-yl)methyl)phenyl)-5-phenyl-3H-imidazo[4,5-b]pyridin-2-yl)pyridin-2-amine To a solution of Intermediate 163 (80 mg, 159 μmol) and 2,4-dichloro-1,3,5-triazine (26.3 mg, 175 μmol) in THF (5 mL) and H$_2$O (1 mL) was added DIEA (103 mg, 797 μmol). The mixture was stirred at 0° C. for 1 hr. The reaction mixture was quenched with H$_2$O (50 mL) at 25° C. and extracted with CH$_2$Cl$_2$ (50 mL×2). The combined organic layers were washed with brine (100 mL), dried over Na$_2$SO$_4$, filtered and concentrated under reduced pressure. The crude was purified by silica gel flash chromatography (Eluent of 1~10% MeOH in CH$_2$Cl$_2$) to give (S)-3-(3-(4-((7-(4-chloro-1,3,5-triazin-2-yl)-2,7-diazaspiro[4.4]nonan-2-yl)methyl)phenyl)-5-phenyl-3H-imidazo[4,5-b]pyridin-2-yl)pyridin-2-amine (30 mg, yield: 30%) as a yellow solid. MS: m/z=615.6 [M+H]$^+$.

Step 2: (S)-4-(7-(4-(2-(2-Aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile To a solution of (S)-3-(3-(4-((7-(4-chloro-1,3,5-triazin-2-yl)-2,7-diazaspiro[4.4]nonan-2-yl)methyl)phenyl)-5-phenyl-3H-imidazo[4,5-b]pyridin-2-yl)pyridin-2-amine (30 mg, 48.8 μmol) and in DMSO (1 mL) were added KCN (6.35 mg, 97.5 μmol) and DABCO (1.09 mg, 9.75 μmol). The mixture was stirred at 25° C. for 16 hr. The mixture was quenched with H$_2$O (10 mL) and extracted with EtOAc (10 mL×3). The combined organic layers were dried over anhydrous Na$_2$SO$_4$, filtered and concentrated. The residue was purified by prep-TLC (CH$_2$Cl$_2$:MeOH=10:1) to give (S)-4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile (Example 269, 3.3 mg, yield: 11.2%) as a yellow solid. MS: m/z=606.4 [M+H]$^+$. $^1$H NMR (400 MHz, Chloroform-d) δ 8.54 (d, J=4.8 Hz, 1H), 8.13 (d, J=8.4 Hz, 1H), 8.05 (dd, J=4.8, 1.6 Hz, 1H), 8.01 (d, J=8.0 Hz, 2H), 7.80 (d, J=8.4 Hz, 1H), 7.51-7.37 (m, 7H), 7.11-7.03 (m, 1H), 6.63 (br s, 2H), 6.34 (dd, J=7.6, 5.2 Hz, 1H), 3.74-3.56 (m, 6H), 2.79-2.72 (m, 2H), 2.62-2.57 (m, 2H), 2.10-2.04 (m, 2H), 2.01-1.91 (m, 2H).

Example 270: 4-(3-(4-(2-(2-Aminopyridin-3-yl)-5-phenyl-3H-imidazo[4,5-b]pyridin-3-yl)benzyl)-3,8-diazabicyclo[3.2.1]octan-8-yl)-1,3,5-triazine-2-carbonitrile

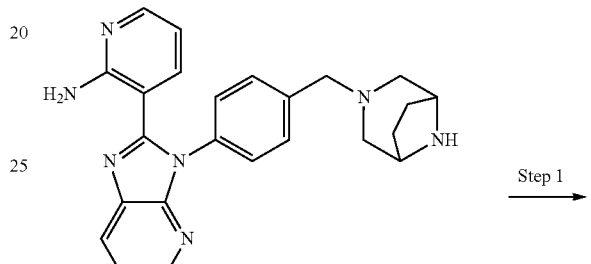

Intermediate 31

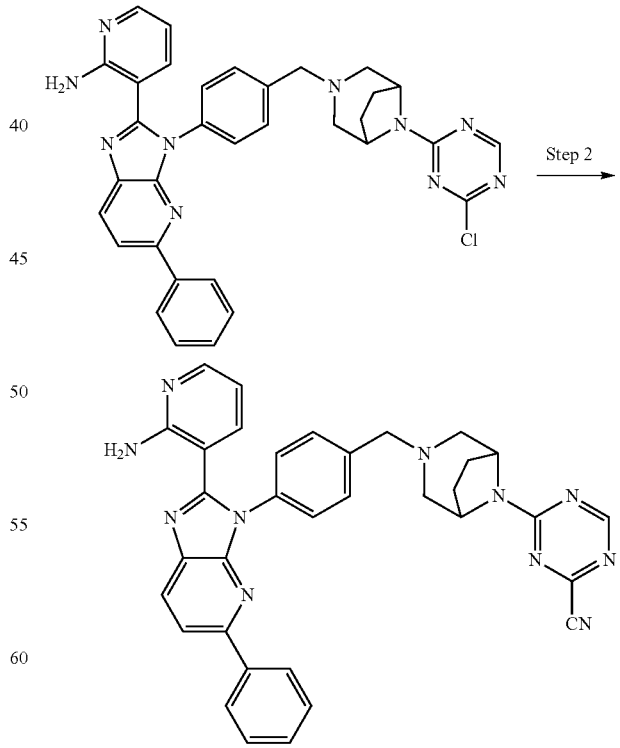

Example 270

Step 1: 3-(3-(4-((8-(4-Chloro-1,3,5-triazin-2-yl)-3,8-diazabicyclo[3.2.1]octan-3-yl)methyl)phenyl)-5-phenyl-3H-imidazo[4,5-b]pyridin-2-yl)pyridin-2-amine To a solution of Intermediate 31 (80 mg, 164 µmol) and 2,4-dichloro-1,3,5-triazine (27.1 mg, 180 µmol) in THF (4 mL) and DMF (4 mL) was added DIEA (106 mg, 820 µmol). The mixture was stirred at 0° C. for 2 hr. The reaction was filtered and concentrated under reduced pressure. The residue was purified by prep-HPLC (column: Waters xbridge 150*25 mm 10 µm; mobile phase: [water (NH$_3$H$_2$O)-ACN]; B %: 60%-90%, 10 min). 3-(3-(4-((8-(4-Chloro-1,3,5-triazin-2-yl)-3,8-diazabicyclo[3.2.1]octan-3-yl)methyl)phenyl)-5-phenyl-3H-imidazo[4,5-b]pyridin-2-yl)pyridin-2-amine (7.0 mg, yield: 7.1%) was obtained as a yellow solid. MS: m/z=601.3 [M+H]$^+$. $^1$H NMR (400 MHz, Dimethylsulfoxide-d$_6$) δ 8.46 (s, 1H), 8.27 (d, J=8.4 Hz, 1H), 8.03 (d, J=7.6 Hz, 2H), 7.98 (dd, J=5.6, 2.4 Hz, 2H), 7.51-7.36 (m, 7H), 7.12 (dd, J=8.0, 2.0 Hz, 1H), 7.05 (br s, 2H), 6.32 (dd, J=7.6, 4.8 Hz, 1H), 4.77-4.73 (m, 1H), 4.68-4.63 (m, 1H), 3.62 (s, 2H), 2.80-2.72 (m, 2H), 2.33-2.27 (m, 2H), 2.03-1.99 (m, 2H), 1.92-1.85 (m, 2H).

Step 2: 4-(3-(4-(2-(2-Aminopyridin-3-yl)-5-phenyl-3H-imidazo[4,5-b]pyridin-3-yl)benzyl)-3,8-diazabicyclo[3.2.1]octan-8-yl)-1,3,5-triazine-2-carbonitrile To a solution of 3-(3-(4-((8-(4-chloro-1,3,5-triazin-2-yl)-3,8-diazabicyclo[3.2.1]octan-3-yl)methyl)phenyl)-5-phenyl-3H-imidazo[4,5-b]pyridin-2-yl)pyridin-2-amine (30 mg, 49.9 mol) in DMSO (1 mL) were added KCN (6.50 mg, 99.8 µmol) and DABCO (1.12 mg, 9.98 gmol). The mixture was stirred at 25° C. for 16 hr. The reaction was filtered and concentrated under reduced pressure. The mixture was quenched with H$_2$O (10 mL) and extracted with EtOAc (10 mL×3). The combined organic layers were dried over anhydrous Na$_2$SO$_4$, filtered and concentrated. The residue was purified by prep-TLC (CH$_2$Cl$_2$:MeOH=10:1) to give 4-(3-(4-(2-(2-aminopyridin-3-yl)-5-phenyl-3H-imidazo[4,5-b]pyridin-3-yl)benzyl)-3,8-diazabicyclo[3.2.1]octan-8-yl)-1,3,5-triazine-2-carbonitrile (Example 270, 9.4 mg, yield: 32%) as a yellow solid. MS: m/z=592.4 [M+H]$^+$. $^1$H NMR (400 MHz, Chloroform-d) δ 8.52 (s, 1H), 8.14 (d, J=8.4 Hz, 1H), 8.08 (dd, J=4.8, 1.6 Hz, 1H), 8.04-8.01 (m, 2H), 7.81 (d, J=8.4 Hz, 1H), 7.50-7.38 (m, 7H), 7.09 (dd, J=7.6, 1.6 Hz, 1H), 6.63 (br s, 2H), 6.36 (dd, J=7.6, 4.8 Hz, 1H), 4.83-4.79 (m, 2H), 3.62 (s, 2H), 2.86-2.80 (m, 2H), 2.42-2.36 (m, 2H), 2.13-2.10 (m, 2H), 1.99-1.95 (m, 2H).

Example 271: 4-(8-(4-(2-(2-Aminopyridin-3-yl)-5-phenyl-3H-imidazo[4,5-b]pyridin-3-yl)benzyl)-3,8-diazabicyclo[3.2.1]octan-3-yl)-1,3,5-triazine-2-carbonitrile

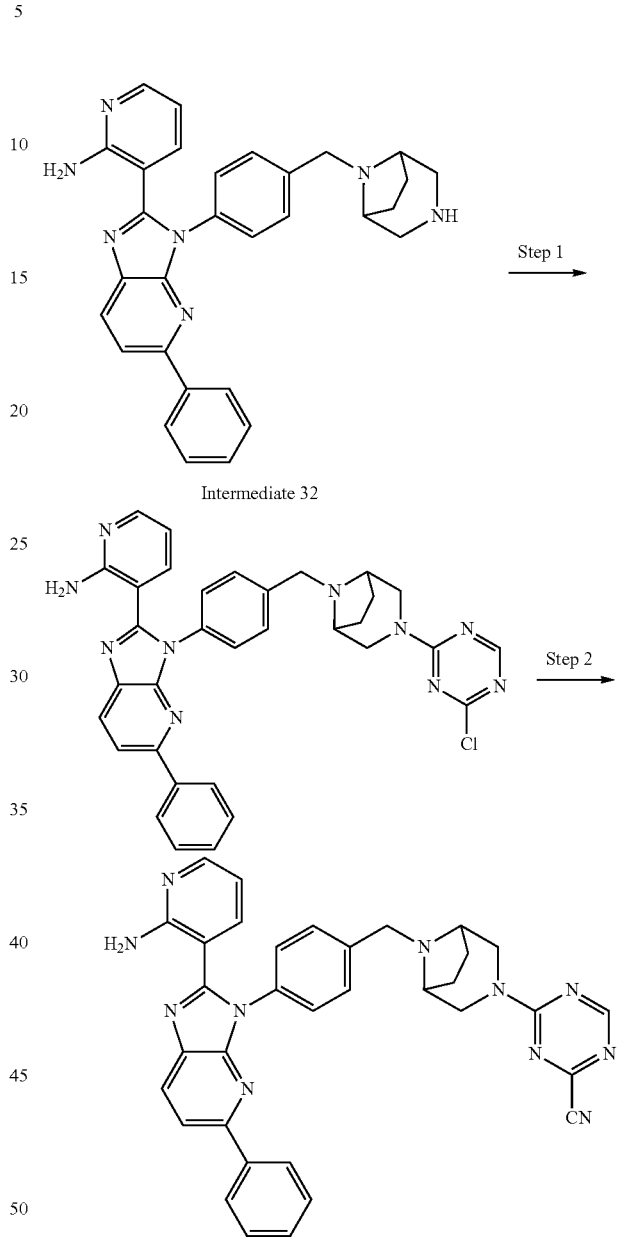

Intermediate 32

Step 1

Step 2

Example 271

Step 1: 3-(3-(4-((3-(4-Chloro-1,3,5-triazin-2-yl)-3,8-diazabicyclo[3.2.1]octan-8-yl)methyl)phenyl)-5-phenyl-3H-imidazo[4,5-b]pyridin-2-yl)pyridin-2-amine To a solution of Intermediate 32 (50 mg, 103 µmol) and 2,4-dichloro-1,3,5-triazine (18.4 mg, 123 µmol) in THF (2 mL) and DMF (2 mL) was added DIEA (66.3 mg, 513 µmol). The mixture was stirred at 25° C. for 2 hr, and then filtered and concentrated under reduced pressure. The residue was purified by prep-HPLC (column: Waters xbridge 150*25 mm 10 µm; mobile phase: [water (NH$_4$HCO$_3$)-

ACN]; B %: 56%-86%, 10 min) to 3-(3-(4-((3-(4-chloro-1,3,5-triazin-2-yl)-3,8-diazabicyclo[3.2.1]octan-8-yl)methyl)phenyl)-5-phenyl-3H-imidazo[4,5-b]pyridin-2-yl)pyridin-2-amine (40 mg, 65% yield) as a light-yellow solid. MS: m/z=601.3 [M+H]$^+$. $^1$H NMR (400 MHz, Dimethylsulfoxide-d$_6$) δ 8.47 (s, 1H), 8.27 (d, J=8.4 Hz, 1H), 8.05-7.95 (m, 4H), 7.60 (d, J=8.4 Hz, 2H), 7.50-7.39 (m, 5H), 7.17 (dd, J=7.6, 1.6 Hz, 1H), 7.00 (br s, 2H), 6.41 (dd, J=7.6, 4.8 Hz, 1H), 4.32-4.27 (m, 1H), 4.20-4.15 (m, 1H), 3.67 (s, 2H), 3.24-3.18 (m, 2H), 2.55-2.52 (m, 2H), 2.04-1.98 (m, 2H), 1.54-1.47 (m, 2H).

Step 2: 4-(8-(4-(2-(2-Aminopyridin-3-yl)-5-phenyl-3H-imidazo[4,5-b]pyridin-3-yl)benzyl)-3,8-diazabicyclo[3.2.1]octan-3-yl)-1,3,5-triazine-2-carbonitrile To a solution of 3-(3-(4-((3-(4-chloro-1,3,5-triazin-2-yl)-3,8-diazabicyclo[3.2.1]octan-8-yl)methyl)phenyl)-5-phenyl-3H-imidazo[4,5-b]pyridin-2-yl)pyridin-2-amine (30.0 mg, 49.9 gmol) in DMSO (1 mL) were added KCN (6.50 mg, 99.8 μmol) and DABCO (1.12 mg, 9.98 μmol). The mixture was stirred at 25° C. for 16 hr. The reaction was filtered and concentrated under reduced pressure. The mixture was quenched with H$_2$O (10 mL) and extracted with EtOAc (10 mL×3). The combined organic layers were dried over anhydrous Na$_2$SO$_4$, filtered and concentrated. The residue was purified by prep-TLC (CH$_2$Cl$_2$:MeOH=10:1) to give 4-(8-(4-(2-(2-aminopyridin-3-yl)-5-phenyl-3H-imidazo[4,5-b]pyridin-3-yl)benzyl)-3,8-diazabicyclo[3.2.1]octan-3-yl)-1,3,5-triazine-2-carbonitrile (Example 271, 4.3 mg, yield: 15%) as a yellow solid. MS: m/z=592.4 [M+H]$^+$. $^1$H NMR (400 MHz, Chloroform-d) δ 8.55 (s, 1H), 8.14 (d, J=8.4 Hz, 1H), 8.08 (d, J=3.6 Hz, 1H), 8.04-8.01 (m, 2H), 7.81 (d, J=8.4 Hz, 1H), 7.57 (d, J=8.0 Hz, 2H) 7.47-7.38 (m, 5H), 7.13 (dd, J=8.0, 1.2 Hz, 1H), 6.70 (br s, 2H), 6.39 (dd, J=7.6, 4.8 Hz, 1H), 4.42-4.33 (m, 2H), 3.69 (s, 2H), 3.40-3.36 (m, 2H), 3.27 (d, J=12.8 Hz, 2H), 2.12-2.06 (m, 2H), 1.32-1.30 (m, 2H).

Example 272: 4-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile

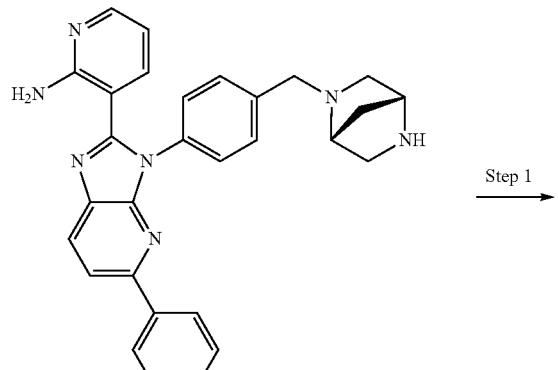

Intermediate 37

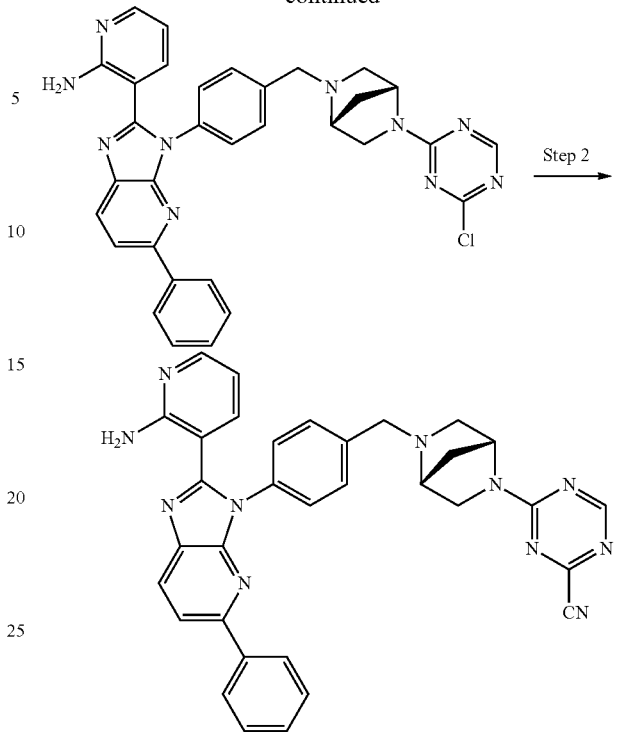

Example 272

Step 1: 3-(3-(4-(((1R,4R)-5-(4-Chloro-1,3,5-triazin-2-yl)-2,5-diazabicyclo[2.2.1]heptan-2-yl)methyl)phenyl)-5-phenyl-3H-imidazo[4,5-b]pyridin-2-yl)pyridin-2-amine To a solution of Intermediate 37 (80 mg, 168 μmol) and 2,4-dichloro-1,3,5-triazine (27.8 mg, 185 μmol) in THF (4 mL) and DMF (4 mL) was added DIEA (109 mg, 844 μmol). The mixture was stirred at 0° C. for 2 hr. The reaction mixture was quenched with H$_2$O (20 mL) and extracted with EtOAc (20 mL×3). The combined organic layers were washed with brine (20 mL×2), dried over Na$_2$SO$_4$, filtered and concentrated under reduced pressure. The residue was purified by prep-HPLC (column: Waters xbridge 150*25 mm 10 μm; mobile phase: [water (NH$_3$H$_2$O)-ACN]; B %: 46%-76%, 10 min) to give 3-(3-(4-(((1R,4R)-5-(4-chloro-1,3,5-triazin-2-yl)-2,5-diazabicyclo[2.2.1]heptan-2-yl)methyl)phenyl)-5-phenyl-3H-imidazo[4,5-b]pyridin-2-yl)pyridin-2-amine (21.7 mg, yield: 22%) as a yellow solid. MS: m/z=587.3 [M+H]$^+$. $^1$H NMR (400 MHz, Methanol-d$_4$), δ 8.33 (d, J=12.8 Hz, 1H), 8.18 (d, J=8.4 Hz, 1H), 8.05-8.02 (m, 2H), 7.98 (dd, J=4.8, 1.6 Hz, 1H), 7.93 (d, J=8.4 Hz, 1H), 7.56 (d, J=8.0 Hz, 2H), 7.45-7.30 (m, 6H), 6.49-6.45 (m, 1H), 4.98-4.92 (m, 1H), 3.89 (s, 2H), 3.85-3.79 (m, 1H), 3.75-3.72 (m, 1H), 3.49-3.44 (m, 1H), 3.06-2.98 (m, 1H), 2.76-2.27 (m, 1H), 2.11 (d, J=10.4 Hz, 1H), 1.89 (d, J=10.0 Hz, 1H).

Step 2: 4-((1R,4R)-5-(4-(2-(2-Aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile To a solution of 3-(3-(4-(((1R,4R)-5-(4-chloro-1,3,5-triazin-2-yl)-2,5-diazabicyclo[2.2.1]heptan-2-yl)methyl)phenyl)-5-phenyl-3H-imidazo[4,5-b]pyridin-2-yl)pyridin-2-amine (60 mg, 102 μmol) in DMSO (1 mL) was added KCN (13.3 mg, 204 gmol) and DABCO (2.29 mg, 20.4 gmol). The mixture was stirred at 25° C. for 16 hr. The mixture was quenched with H₂O (10 mL) and extracted with EtOAc (10 mL×3), the combined organic layers were dried over anhydrous Na₂SO₄, filtered and concentrated. The residue was purified by prep-TLC (CH₂Cl₂:MeOH=10:1) to give 4-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile (Example 272, 13.4 mg, yield: 23%) as a yellow solid. MS: m/z=578.3 [M+H]⁺. ¹H NMR (400 MHz, Chloroform-d) δ 8.54 (d, J=18.4 Hz, 1H), 8.13 (d, J=8.4 Hz, 1H), 8.08-8.05 (m, 1H), 8.01 (d, J=7.2 Hz, 2H), 7.80 (d, J=8.4 Hz, 1H), 7.52-7.35 (m, 7H), 7.09 (dd, J=8.0, 1.6 Hz, 1H), 6.62 (s, 2H), 6.38-6.34 (m, 1H), 4.98-4.95 (m, 1H), 3.87 (s, 2H), 3.85-3.81 (m, 1H), 3.75-3.70 (m, 1H), 3.47-3.42 (m, 1H), 3.06 (d, J=10.0 Hz, 1H), 2.72 (dd, J=13.2, 10.8 Hz, 1H), 2.12 (d, J=10.0 Hz, 1H), 1.87 (d, J=10.0 Hz, 1H).

Example 273: (R)-4-(4-(4-(2-(2-Aminopyridin-3-yl)-5-phenyl-3H-imidazo[4,5-b]pyridin-3-yl)benzyl)-2-methylpiperazin-1-yl)-1,3,5-triazine-2-carbonitrile

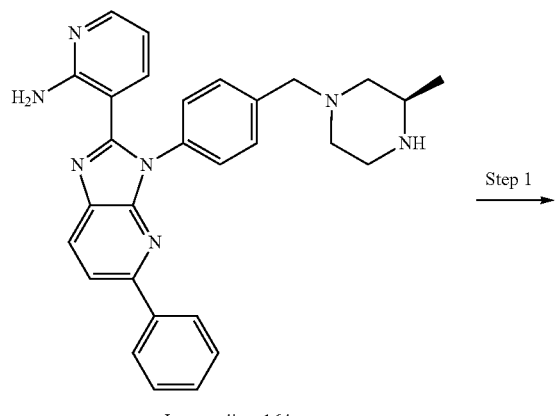

Intermediate 164

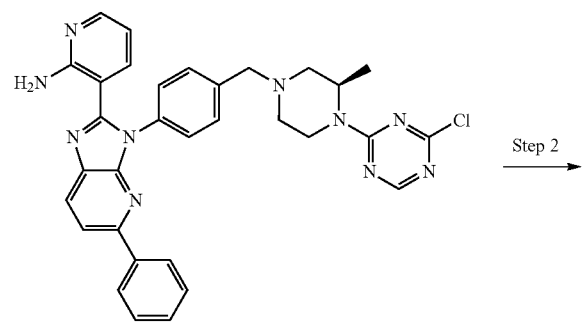

Step 2

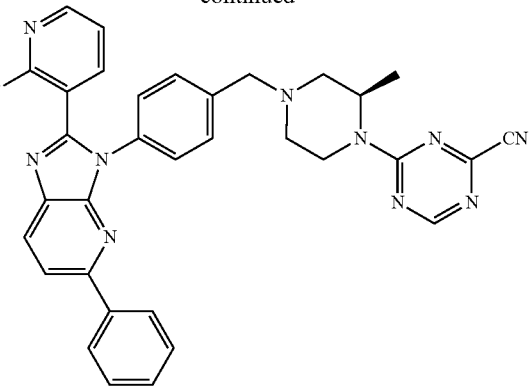

Example 273

Step 1: (R)-3-(3-(4-((4-(4-Chloro-1,3,5-triazin-2-yl)-3-methylpiperazin-1-yl)methyl)phenyl)-5-phenyl-3H-imidazo[4,5-b]pyridin-2-yl)pyridin-2-amine To a solution of Intermediate 164 (100 mg, 210 μmol) in THF (10 mL) was added DIEA (81.5 mg, 631 μmol). Then 2,4-dichloro-1,3,5-triazine (35 mg, 231 μmol) in THF (3 mL) was added into the mixture at 0° C. and the reaction mixture was stirred at 0° C. for 1 hr. The mixture was diluted with H₂O (5 mL) and extracted with CH₂Cl₂ (15 mL×2). The combined organic layers were washed with brine (15 mL), dried over Na₂SO₄, filtered and concentrated under reduced pressure (≤35° C.) to give a crude product. After purified by silica gel flash chromatography (Eluent of 1%~3% MeOH in CH₂Cl₂), (R)-3-(3-(4-((4-(4-chloro-1,3,5-triazin-2-yl)-3-methylpiperazin-1-yl)methyl)phenyl)-5-phenyl-3H-imidazo[4,5-b]pyridin-2-yl)pyridin-2-amine (40 mg, yield: 31%) was obtained as a yellow solid. MS: m/z=589.3 [M+H]⁺.

Step 2: (R)-4-(4-(4-(2-(2-Aminopyridin-3-yl)-5-phenyl-3H-imidazo[4,5-b]pyridin-3-yl)benzyl)-2-methylpiperazin-1-yl)-1,3,5-triazine-2-carbonitrile To a solution of (R)-3-(3-(4-((4-(4-chloro-1,3,5-triazin-2-yl)-3-methylpiperazin-1-yl)methyl)phenyl)-5-phenyl-3H-imidazo[4,5-b]pyridin-2-yl)pyridin-2-amine (40 mg, 67.9 μmol) in DMSO (1 mL) was added KCN (8.84 mg, 136 μmol) and DABCO (1.52 mg, 13.6 gmol). The mixture was stirred at 25° C. for 16 hr. The reaction mixture was poured into H₂O (10 mL). The resulting mixture was extracted with EtOAc (10 mL×2). The combined organic layers were washed with brine (10 mL), dried over Na₂SO₄, filtered and concentrated under reduced pressure. The crude product was purified by prep-TLC (100% EtOAc) to give (R)-4-(4-(4-(2-(2-aminopyridin-3-yl)-5-phenyl-3H-imidazo[4,5-b]pyridin-3-yl)benzyl)-2-methylpiperazin-1-yl)-1,3,5-triazine-2-carbonitrile (Example 273, 8 mg, yield: 18%) as a yellow solid. MS: m/z=580.3 [M+H]⁺. ¹H NMR (400 MHz, Acetonitrile-d₃) δ 8.56 (d, J=4.8 Hz, 1H), 8.18 (d, J=8.4 Hz, 1H), 8.05-8.02 (m, 3H), 7.90 (d, J=8.0 Hz, 1H), 7.57 (d, J=8.4 Hz, 2H), 7.49-7.39 (m, 5H), 7.16 (dd, J=8.0, 1.6 Hz, 1H), 6.60 (br s, 1H), 6.39 (dd, J=8.0, 4.8 Hz, 1H), 4.95-4.74 (m, 1H), 4.60-4.40 (m, 1H), 3.72-3.54 (m, 2H), 3.36-3.23 (m, 1H), 3.02-2.91 (m, 1H), 2.84-2.73 (m, 1H), 2.29-2.24 (m, 1H), 2.18-2.16 (m, 1H), 1.35-1.32 (m, 3H).

Example 274: (S)-4-(4-(4-(2-(2-Aminopyridin-3-yl)-5-phenyl-3H-imidazo[4,5-b]pyridin-3-yl)benzyl)-2-methylpiperazin-1-yl)-1,3,5-triazine-2-carbonitrile

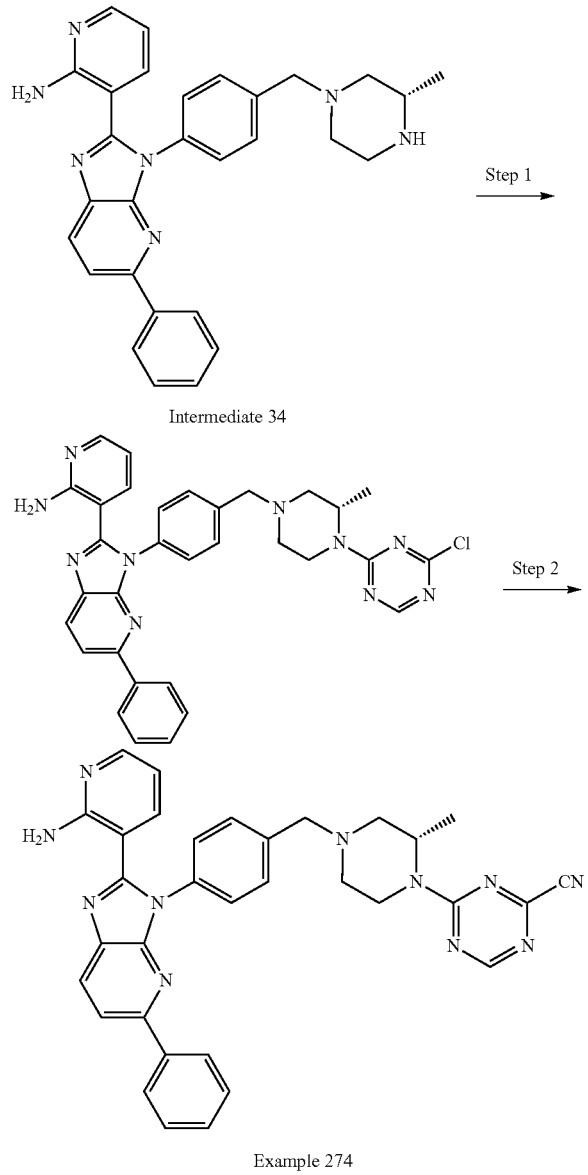

Intermediate 34

Example 274

Step 1: (S)-3-(3-(4-((4-(4-Chloro-1,3,5-triazin-2-yl)-3-methylpiperazin-1-yl)methyl)phenyl)-5-phenyl-3H-imidazo[4,5-b]pyridin-2-yl)pyridin-2-amine Following the general procedure of Example 273, the reaction of Intermediate 34 (100 mg, 210 μmol) with 2,4-dichloro-1,3,5-triazine (35 mg, 231 μmol) was carried out. After purified by silica gel flash chromatography (Eluent of 10~65% EtOAc in petroleum ether), (S)-3-(3-(4-((4-(4-chloro-1,3,5-triazin-2-yl)-3-methylpiperazin-1-yl)methyl)phenyl)-5-phenyl-3H-imidazo[4,5-b]pyridin-2-yl)pyridin-2-amine (40 mg, yield: 25%) was obtained as a yellow solid. MS: m/z=589.4 [M+H]$^+$.

Step 2: (S)-4-(4-(4-(2-(2-Aminopyridin-3-yl)-5-phenyl-3H-imidazo[4,5-b]pyridin-3-yl)benzyl)-2-methylpiperazin-1-yl)-1,3,5-triazine-2-carbonitrile To a solution of (S)-3-(3-(4-((4-(4-chloro-1,3,5-triazin-2-yl)-3-methylpiperazin-1-yl)methyl)phenyl)-5-phenyl-3H-imidazo[4,5-b]pyridin-2-yl)pyridin-2-amine (40 mg, 67.9 μmol) in DMSO (1 mL) were added KCN (8 mg, 136 μmol) and then DABCO (1.52 mg, 13.6 μmol). The mixture was stirred at 25° C. for 16 hr. The reaction mixture was poured into H$_2$O (10 mL). The resulting mixture was extracted with EtOAc (10 mL×2). The combined organic layers were washed with brine (10 mL), dried over Na$_2$SO$_4$, filtered and concentrated under reduced pressure. The crude product was purified by prep-TLC (100% EtOAc) to give (S)-4-(4-(4-(2-(2-aminopyridin-3-yl)-5-phenyl-3H-imidazo[4,5-b]pyridin-3-yl)benzyl)-2-methylpiperazin-1-yl)-1,3,5-triazine-2-carbonitrile (Example 274, 13.8 mg, yield: 33%) as a yellow solid. MS: m/z=580.4 [M+H]$^+$. $^1$H NMR (400 MHz, Acetonitrile-d$_3$) δ 8.57 (d, J=4.4 Hz, 1H), 8.19 (d, J=8.4 Hz, 1H), 8.07-8.01 (m, 3H), 7.91 (d, J=8.0 Hz, 1H), 7.58 (d, J=8.0 Hz, 2H), 7.50-7.40 (m, 5H), 7.19-7.14 (m, 1H), 6.62 (br s, 2H), 6.40 (dd, J=7.6, 5.2 Hz, 1H), 4.99-4.74 (m, 1H), 4.63-4.39 (m, 1H), 3.73-3.55 (m, 2H), 3.36-3.27 (m, 1H), 3.03-2.95 (m, 1H), 2.84-2.75 (m, 1H), 2.29-2.23 (m, 1H), 2.13-2.09 (m, 1H), 1.35-1.32 (m, 3H).

Example 275: 4-((2S,6S)-4-(4-(2-(2-Aminopyridin-3-yl)-5-phenyl-3H-imidazo[4,5-b]pyridin-3-yl)benzyl)-2,6-dimethylpiperazin-1-yl)-1,3,5-triazine-2-carbonitrile

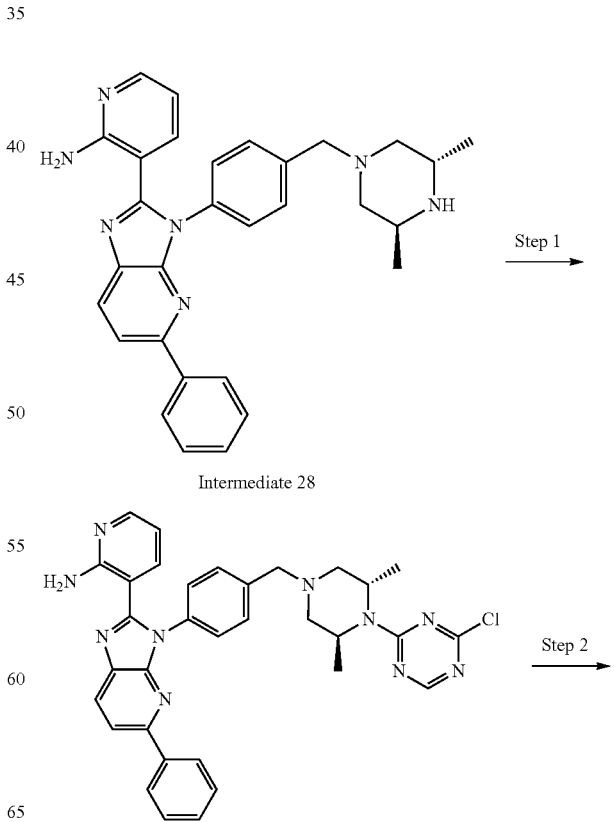

Intermediate 28

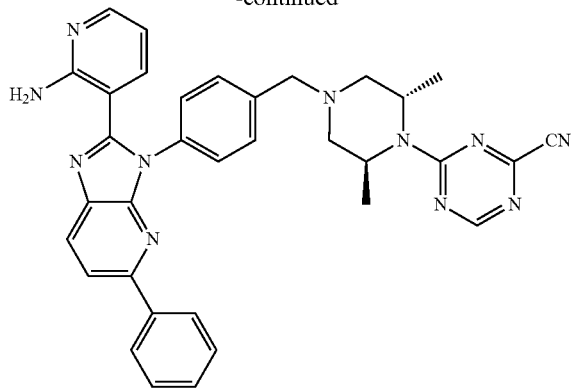

Example 275

Step 1: 3-(3-(4-(((3S,5S)-4-(4-Chloro-1,3,5-triazin-2-yl)-3,5-dimethylpiperazin-1-yl)methyl)phenyl)-5-phenyl-3H-imidazo[4,5-b]pyridin-2-yl)pyridin-2-amine To a solution of Intermediate 28 (100 mg, 204 μmol) in THF (5 mL) and DMF (5 Ml) was added DIEA (79.2 mg, 613 μmol). Then 2,4-dichloro-1,3,5-triazine (35 mg, 231 μmol) in THF (3 mL) was added into the mixture at 0° C. and the reaction mixture was stirred at 0° C. for 1 hr. The mixture was diluted with $H_2O$ (5 mL) and extracted with $CH_2Cl_2$ (15 mL×2). The combined organic layers were washed with brine (15 mL), dried over $Na_2SO_4$, filtered and concentrated under reduced pressure (≤35° C.) to give a crude product. After purified by prep-TLC ($CH_2Cl_2$:MeOH=10:1), 3-(3-(4-(((3S,5S)-4-(4-chloro-1,3,5-triazin-2-yl)-3,5-dimethylpiperazin-1-yl)methyl)phenyl)-5-phenyl-3H-imidazo[4,5-b]pyridin-2-yl)pyridin-2-amine (50 mg, yield: 33%) was obtained as a yellow solid. MS: m/z=603.4 [M+H]⁺. ¹H NMR (400 MHz, Methanol-d₄) δ8.39 (s, 1H), 8.20 (d, J=8.4 Hz, 1H), 8.06-8.03 (m, 2H), 7.99 (dd, J=5.2, 2.0 Hz, 1H), 7.95 (d, J=8.4 Hz, 1H), 7.58 (d, J=8.4 Hz, 2H), 7.47-7.37 (m, 5H), 7.34 (dd, J=7.6, 1.6 Hz, 1H), 6.49 (dd, J=7.6, 4.8 Hz, 1H), 4.55-4.36 (m, 2H), 3.95 (d, J=13.2 Hz, 1H), 3.82 (d, J=13.2 Hz, 1H), 3.17-3.13 (m, 2H), 2.74 (dd, J=12.0, 4.0 Hz, 2H), 1.44 (d, J=6.4 Hz, 6H).

Step 2: 4-((2S,6S)-4-(4-(2-(2-Aminopyridin-3-yl)-5-phenyl-3H-imidazo[4,5-b]pyridin-3-yl)benzyl)-2,6-dimethylpiperazin-1-yl)-1,3,5-triazine-2-carbonitrile To a solution of 3-(3-(4-(((3S,5S)-4-(4-chloro-1,3,5-triazin-2-yl)-3,5-dimethylpiperazin-1-yl)methyl)phenyl)-5-phenyl-3H-imidazo[4,5-b]pyridin-2-yl)pyridin-2-amine (40 mg, 66.3 μmol) in DMSO (1 mL) were added KCN (8.64 mg, 133 μmol) and DABCO (1.49 mg, 13.3 μmol). The mixture was stirred at 25° C. for 16 hr. The reaction mixture was poured into $H_2O$ (10 mL). The resulting mixture was extracted with EtOAc (10 mL×2). The combined organic layers were washed with brine (10 mL), dried over $Na_2SO_4$, filtered and concentrated under reduced pressure. The crude was purified by prep-TLC (100% EtOAc) to give 4-((2S,6S)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile (Example 275, 9.8 mg, yield: 22%) as a yellow solid. MS: m/z=594.4 [M+H]⁺. ¹H NMR (400 MHz, Acetonitrile-d₃) δ 8.59 (s, 1H), 8.17 (d, J=8.4 Hz, 1H), 8.05-7.96 (m, 3H), 7.90 (d, J=8.4 Hz, 1H), 7.60-7.53 (m, 2H), 7.49-7.39 (m, 5H), 7.19-7.11 (m, 1H), 6.62 (br s, 2H), 6.38 (dd, J=7.6, 4.8 Hz, 1H), 4.41 (br s, 2H), 3.96-3.78 (m, 2H), 3.22-3.11 (m, 2H), 2.74 (dd, J=12.4, 3.6 Hz, 2H), 1.40 (d, J=6.4 Hz, 6H).

Example 276: 4-(7-(4-(2-(2-aminopyridin-3-yl)-5-phenyl-3H-imidazo[4,5-b]pyridin-3-yl)benzyl)-4,7-diazaspiro[2.5]octan-4-yl)-1,3,5-triazine-2-carbonitrile

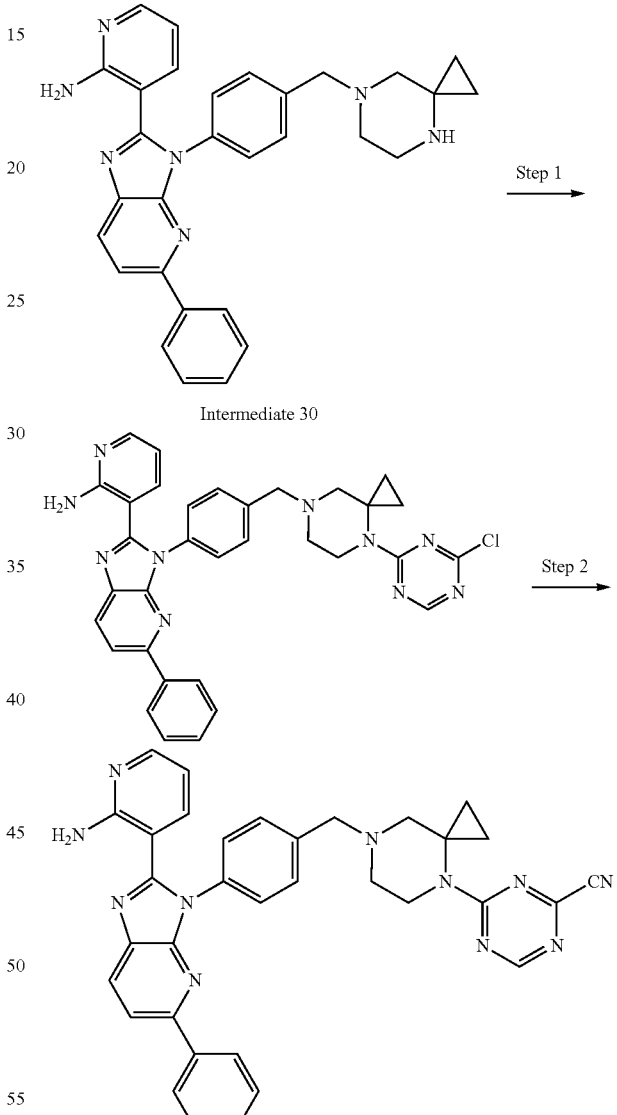

Example 276

Step 1: 3-(3-(4-((4-(4-Chloro-1,3,5-triazin-2-yl)-4,7-diazaspiro[2.5]octan-7-yl)methyl)phenyl)-5-phenyl-3H-imidazo[4,5-b]pyridin-2-yl)pyridin-2-amine Following the general procedure of Example 273, the reaction of Intermediate 30 (150 mg, 308 μmol) with 2,4-dichloro-1,3,5-triazine (50.8 mg, 338 μmol) was carried out.

After purified by silica gel flash chromatography (Eluent of 1~100% EtOAc in petroleum ether), 3-(3-(4-((4-(4-chloro-1,3,5-triazin-2-yl)-4,7-diazaspiro[2.5]octan-7-yl)methyl)phenyl)-5-phenyl-3H-imidazo[4,5-b]pyridin-2-yl)pyridin-2-amine (45 mg, yield: 21%) was obtained as a yellow solid. MS: m/z=601.1 [M+H]$^+$.

Step 2: 4-(7-(4-(2-(2-Aminopyridin-3-yl)-5-phenyl-3H-imidazo[4,5-b]pyridin-3-yl)benzyl)-4,7-diazaspiro[2.5]octan-4-yl)-1,3,5-triazine-2-carbonitrile To a solution of 3-(3-(4-((4-(4-chloro-1,3,5-triazin-2-yl)-4,7-diazaspiro[2.5]octan-7-yl)methyl)phenyl)-5-phenyl-3H-imidazo[4,5-b]pyridin-2-yl)pyridin-2-amine (45 mg, 74.9 μmol) in DMSO (1 mL) were added KCN (100 mg, 1.54 mmol) and then DABCO (1.68 mg, 15 μmol). The mixture was stirred at 25° C. for 16 hr. The reaction mixture was poured into H$_2$O (10 mL). The resulting mixture was extracted with EtOAc (10 mL×2). The combined organic layers were washed with brine (10 mL), dried over Na$_2$SO$_4$, filtered and concentrated under reduced pressure. The crude product was purified by prep-TLC (100% EtOAc) to give 4-(7-(4-(2-(2-aminopyridin-3-yl)-5-phenyl-3H-imidazo[4,5-b]pyridin-3-yl)benzyl)-4,7-diazaspiro[2.5]octan-4-yl)-1,3,5-triazine-2-carbonitrile (Example 276, 6.2 mg, yield: 14%) as an off-white solid. MS: m/z=592.3 [M+H]$^+$. $^1$H NMR (400 MHz, Acetonitrile-d$_3$) δ 8.60 (d, J=4.0 Hz, 1H), 8.18 (d, J=8.4 Hz, 1H), 8.05-8.00 (m, 3H), 7.91 (d, J=8.4 Hz, 1H), 7.54-7.41 (m, 7H), 7.14 (dd, J=7.6, 1.6 Hz, 1H), 6.58 (br s, 2H), 6.35 (dd, J=7.6, 4.8 Hz, 1H), 4.11-3.98 (m, 2H), 3.61 (s, 2H), 2.66-2.57 (m, 2H), 2.47-2.41 (m, 2H), 1.00-0.95 (m, 2H), 0.90-0.85 (m, 2H).

Example 277: 4-((2R,6S)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile

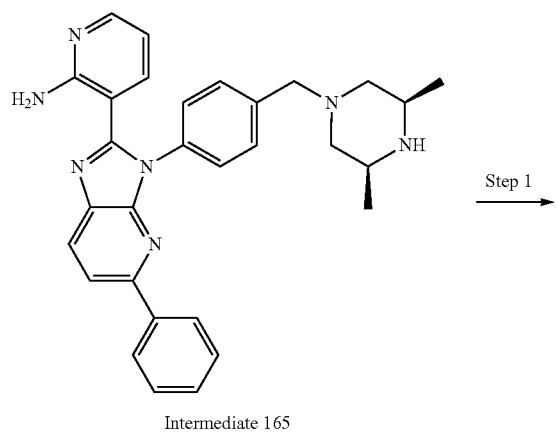

Intermediate 165

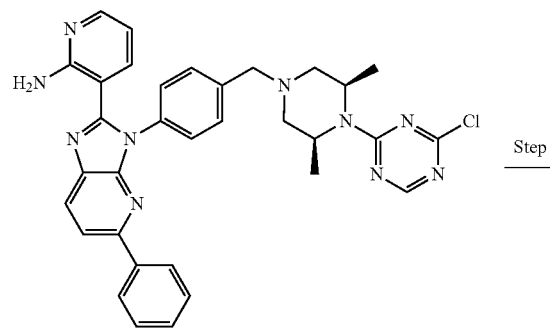

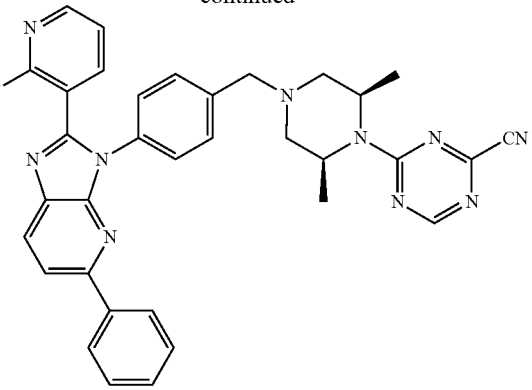

Example 277

Step 1: 3-(3-(4-(((3S,5R)-4-(4-Chloro-1,3,5-triazin-2-yl)-3,5-dimethylpiperazin-1-yl)methyl)phenyl)-5-phenyl-3H-imidazo[4,5-b]pyridin-2-yl)pyridin-2-amine To a solution of Intermediate 165 (50 mg, 102 μmol) and K$_2$CO$_3$ (42.3 mg, 306 μmol) in THF (4 mL) and H$_2$O (1 mL) was added 2,4-dichloro-1,3,5-triazine (15.3 mg, 102 μmol). The mixture was stirred at 0° C. for 2 hr. The mixture was filtered and concentrated. The residue was purified by prep-HPLC (column: Waters xbridge 150×25 mm 10 μm; mobile phase: [water (NH$_4$HCO$_3$)-ACN]; B %: 61%-91%, 14 min) to give 3-(3-(4-(((3S,5R)-4-(4-chloro-1,3,5-triazin-2-yl)-3,5-dimethylpiperazin-1-yl)methyl)phenyl)-5-phenyl-3H-imidazo[4,5-b]pyridin-2-yl)pyridin-2-amine (1.8 mg, yield: 2.8%) as an off-white solid. MS: m/z=603.4 [M+H]$^+$. $^1$H NMR (400 MHz, Methanol-d$_4$) δ 8.38 (s, 1H), 8.20 (d, J=8.4 Hz, 1H), 8.08-8.03 (m, 2H), 7.99 (dd, J=5.2, 1.6 Hz, 1H), 7.97-7.92 (m, 1H), 7.63-7.61 (m, 2H), 7.48-7.44 (m, 2H), 7.43-7.39 (m, 2H), 7.38-7.32 (m, 2H), 6.49 (dd, J=7.6, 4.8 Hz, 1H), 3.67 (s, 2H), 2.87-2.84 (m, 2H), 2.36-2.28 (M, 2H), 2.20-2.04 (m, 2H), 1.40 (d, J=7.2 Hz, 6H).

Step 2: 4-((2R,6S)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile To a solution of 3-(3-(4-(((3S,5R)-4-(4-chloro-1,3,5-triazin-2-yl)-3,5-dimethylpiperazin-1-yl)methyl)phenyl)-5-phenyl-3H-imidazo[4,5-b]pyridin-2-yl)pyridin-2-amine (55 mg, 91.2 μmol) in DMSO (1 mL) was added KCN (6 mg, 92.1 μmol). The mixture was stirred at 0° C. for 0.5 hr, then DABCO (2.05 mg, 18.2 μmol) was added. The mixture was stirred at 25° C. for 16 hr. The mixture was quenched with water (10 mL) and extracted with EtOAc (10 mL×3). The combined organic layers were dried over anhydrous Na$_2$SO$_4$, filtered and concentrated. The residue was purified by prep-HPLC (column: Waters xbridge 150×25 mm×10 μm; mobile phase: [water (NH$_4$HCO$_3$)-ACN]; B %: 58%-88%, 14 min) to give 4-((2R,6S)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile (Example 277, 5.9 mg, yield: 111%) as an off-white solid. MS: m/z=594.4 [M+H]$^+$. $^1$H NMR (400 MHz, Chloroform-d) δ 8.60 (s, 1H), 8.16 (d, J=8.4 Hz, 1H), 8.08-8.02 (m, 3H), 7.84 (d, J=8.4 Hz, 1H), 7.59 (d, J=8.4 Hz, 2H), 7.47-7.39 (m, 5H), 7.18-7.16 (m, 1H), 6.88 (br s, 2H), 6.39 (dd, J=7.6, 4.8

Hz, 1H), 4.78-4.70 (m, 2H), 3.67 (s, 2H), 2.84 (d, J=11.6 Hz, 2H), 2.38-2.32 (m, 2H), 1.41 (d, J=6.8 Hz, 6H).

Example 278: 4-((1-(4-(2-(2-Aminopyridin-3-yl)-5-phenyl-3H-imidazo[4,5-b]pyridin-3-yl)benzyl)azepan-4-yl)amino)-1,3,5-triazine-2-carbonitrile

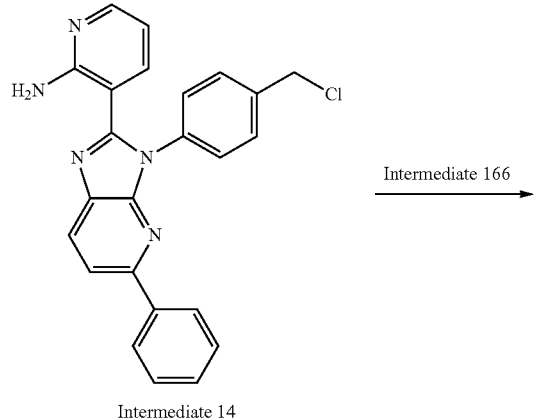

Intermediate 14

$\xrightarrow{\text{Intermediate 166}}$

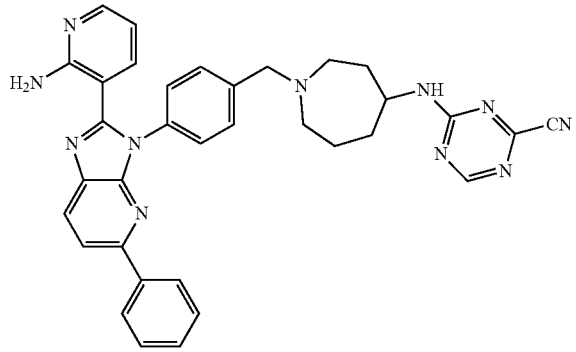

Example 278

Example 279: 4-((4-(4-(2-(2-Aminopyridin-3-yl)-5-phenyl-3H-imidazo[4,5-b]pyridin-3-yl)benzyl)-1,4-oxazepan-6-yl)amino)-1,3,5-triazine-2-carbonitrile

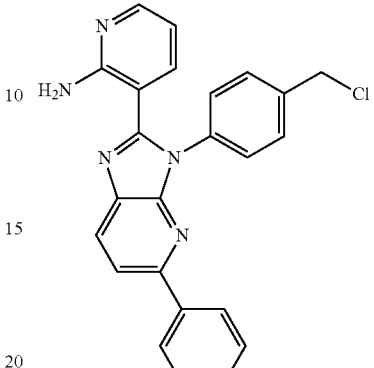

Intermediate 14

$\xrightarrow{\text{Intermediate 167}}$

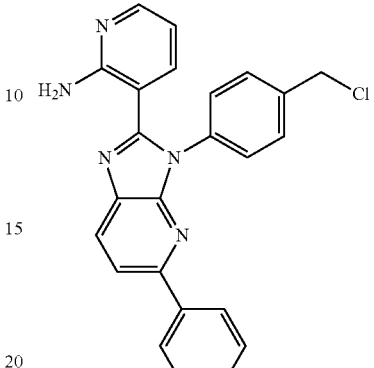

Example 279

To a solution of Intermediate 14 (250 mg, 1.15 mmol) and Intermediate 166 (472 mg, 1.15 mmol) in DMF (3 mL) were added NaI (34.3 mg, 229.1 μmol) and K2CO3 (475 mg, 3.44 mmol). The mixture was stirred at 25° C. for 16 hr. The reaction mixture was filtered to give a filter liquid. The residue was purified by prep-HPLC (column: Waters xbridge 150×25 mm×10 μm; mobile phase: [water (NH$_4$HCO$_3$)-ACN]; B %: 50%-80%, over 10 min) to give 4-((1-(4-(2-(2-aminopyridin-3-yl)-5-phenyl-3H-imidazo[4,5-b]pyridin-3-yl)benzyl)azepan-4-yl)amino)-1,3,5-triazine-2-carbonitrile (Example 278, 73 mg, yield: 9.9%) as yellow lyophilized powder. MS: m/z=594.4 [M+H]$^+$. $^1$H NMR (400 MHz, Dimethylsulfoxide-d$_6$) δ 8.92-8.89 (m, 1H), 8.71-8.54 (m, 1H), 8.27 (d, J=8.4 Hz, 1H), 8.04-7.97 (m, 4H), 7.54-7.49 (m, 2H), 7.48-7.43 (m, 4H), 7.40-7.36 (m, 1H), 7.15 (d, J=7.6 Hz, 1H), 7.05 (br s, 2H), 6.38-6.34 (m, 1H), 4.14-3.99 (m, 1H), 3.76-3.65 (m, 2H), 2.67-2.63 (m, 2H), 1.98-1.50 (m, 8H).

To a solution of Intermediate 14 (330 mg, 736 μmol) and Intermediate 167 (246 mg, 736 mol, TFA salt) in DMF (3 mL) were added K$_2$CO$_3$ (509 mg, 3.68 mmol) and NaI (55.2 mg, 368 μmol). The mixture was stirred at 50° C. for 2 hr. The mixture was quenched with H$_2$O (25 mL) and extracted with EtOAc (50 mL). The organic layer was dried over anhydrous Na$_2$SO$_4$, filtered and concentrated. The residue was purified by prep-TLC (CH$_2$Cl$_2$:MeOH=20:1) to give 4-((4-(4-(2-(2-aminopyridin-3-yl)-5-phenyl-3H-imidazo[4,5-b]pyridin-3-yl)benzyl)-1,4-oxazepan-6-yl)amino)-1,3,5-triazine-2-carbonitrile (Example 279, 55.4 mg, yield: 13%) as a light-yellow solid. MS: m/z=596.4 [M+H]$^+$. $^1$H NMR (400 MHz, Dimethylsulfoxide-d$_6$) δ 8.91-8.84 (m, 1H), 8.65-8.58 (m, 1H), 8.29-8.24 (m, 1H), 8.04-7.96 (m, 4H), 7.59-7.54 (m, 2H), 7.48-7.40 (m, 5H), 7.12-7.03 (m, 3H), 6.34-6.24 (m, 1H), 4.39-4.14 (m, 2H), 3.96-3.91 (m, 1H), 3.85-3.79 (m, 2H), 3.71-3.68 (m, 2H), 3.00-2.88 (m, 2H), 2.82-2.74 (m, 2H).

Example 280: 4-((1-(4-(2-(2-Aminopyridin-3-yl)-5-methyl-3H-imidazo[4,5-b]pyridin-3-yl)benzyl)piperidin-4-yl)amino)pyrimidine-2-carbonitrile

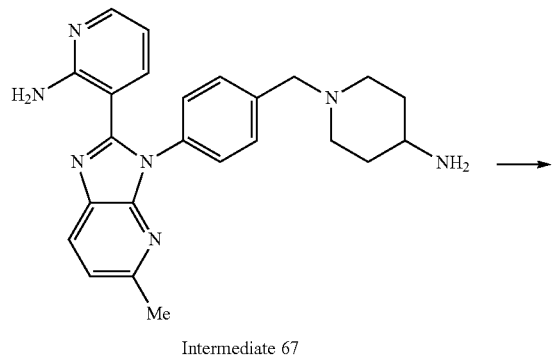

Intermediate 67

Example 281: 4-(4-(4-(2-(2-Aminopyridin-3-yl)-5-(2-fluorophenyl)-3H-imidazo[4,5-b]pyridin-3-yl)benzyl)piperazin-1-yl)pyrimidine-2-carbonitrile

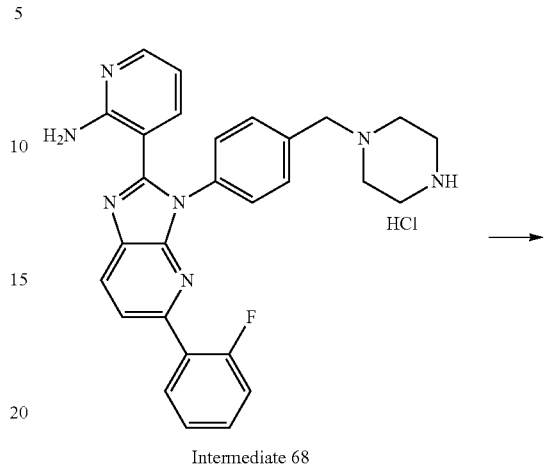

Intermediate 68

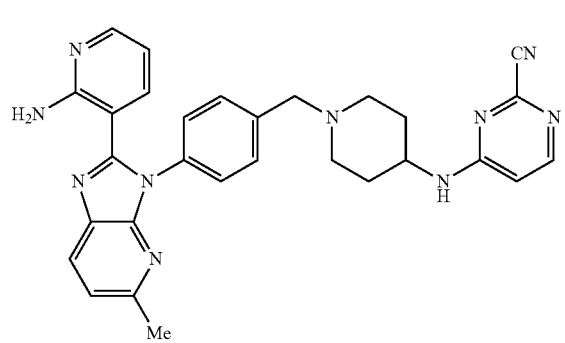

Example 280

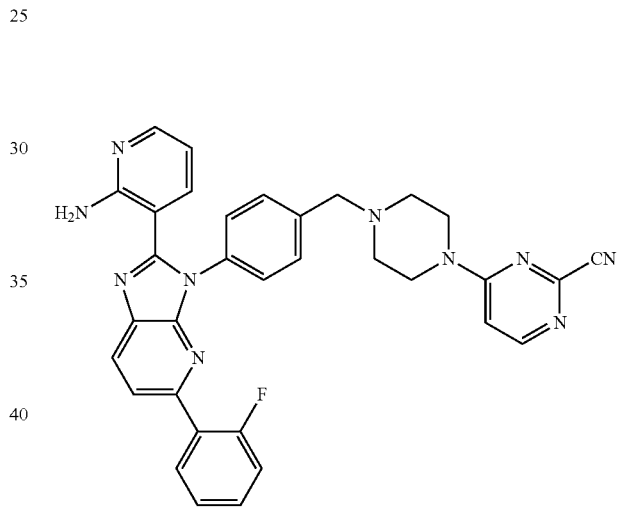

Example 281

A mixture of Intermediate 67 (80 mg, 193 μmol), 4-chloropyrimidine-2-carbonitrile (29.7 mg, 213 μmol) and DIEA (75 mg, 580 μmol) in NMP (2 mL) was taken up into a microwave tube. The sealed tube was stirred at 130° C. for 0.5 hr under microwave. The reaction mixture was poured into H$_2$O (10 mL), extracted with CH$_2$Cl$_2$ (15 mL). The organic phase was dried over anhydrous Na$_2$SO$_4$, filtered and concentrated under reduced pressure. The residue was purified by prep-HPLC (column: Phenomenex C18 150*25 mm*10 μm; mobile phase: [water (NH$_4$HCO$_3$)-ACN]; gradient: 22%-52% B over 14 min). 4-((1-(4-(2-(2-Aminopyridin-3-yl)-5-methyl-3H-imidazo[4,5-b]pyridin-3-yl)benzyl)piperidin-4-yl)amino)pyrimidine-2-carbonitrile (Example 280, 10.7 mg, yield: 11%) was obtained as an off-white lyophilized powder. MS: m/z=517.2 [M+H]$^+$. $^1$H NMR (400 MHz, Dimethylsulfoxide-d6) δ 8.13-8.03 (m, 3H), 7.99 (dd, J=4.8, 2.0 Hz, 1H) 7.45 (d, J=8.0 Hz, 2H), 7.36 (d, J=8.4 Hz, 2H), 7.25 (d, J=8.0 Hz, 1H), 7.09 (dd, J=7.6, 1.6 Hz, 1H), 7.01 (br s, 2H), 6.68 (d, J=6.0 Hz, 1H), 6.34 (dd, J=8.0, 5.2 Hz, 1H), 3.89-3.74 (m, JH), 3.57 (s, 2H), 2.85-2.79 (m, 2H), 2.52 (s, 3H), 2.19-2.10 (m, 2H), 1.94-1.85 (m, 2H), 1.57-1.43 (m, 2H).

A mixture of Intermediate 68 (100 mg, 209 μmol), 4-chloropyrimidine-2-carbonitrile (29.1 mg, 209 μmol) and DIEA (27 mg, 209 μmol) in NMP (2 mL) was taken up into a microwave tube. The sealed tube was heated at 130° C. for 1 hr under microwave. After purified by prep-HPLC (column: Waters xbridge 150×25 mm×10 μm; mobile phase: [water (NH$_4$HCO$_3$)-ACN]; B %: 45%-75%, 10 min), 4-(4-(4-(2-(2-Aminopyridin-3-yl)-5-(2-fluorophenyl)-3H-imidazo[4,5-b]pyridin-3-yl)benzyl)piperazin-1-yl)pyrimidine-2-carbonitrile (Example 281, 18.1 mg, yield: 15%) was obtained as a yellow solid. MS: m/z=583.3 [M+H]$^+$. $^1$H NMR (400 MHz, Dimethylsulfoxide-d$_6$) δ 8.31-8.26 (m, 2H), 8.00 (dd, J=4.8, 1.2 Hz, 1H), 7.85-7.76 (m, 2H), 7.52-7.42 (m, 5H), 7.37-7.27 (m, 2H), 7.18-7.14 (m, 1H), 7.11 (d, J=6.4 Hz, 1H), 7.00 (br s, 2H), 6.37 (dd, J=7.2, 4.8 Hz, 1H), 3.80-3.63 (m, 4H), 3.62 (s, 2H), 2.49-2.46 (m, 4H). $^{19}$F NMR (400 MHz, Dimethylsulfoxide-d$_6$) δ −117.17.

Example 282: 2-(4-(4-(2-(2-Aminopyridin-3-yl)-5-(2-fluorophenyl)-3H-imidazo[4,5-b]pyridin-3-yl)benzyl)piperazin-1-yl)pyrimidine-4-carbonitrile Example 283: 2-(4-(4-(2-(2-Aminopyridin-3-yl)-5-(3-oxo-1,4-diazepan-1-yl)-3H-imidazo[4,5-b]pyridin-3-yl)benzyl)piperazin-1-yl)pyrimidine-4-carbonitrile

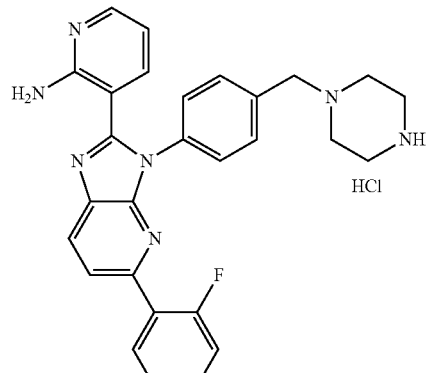

Intermediate 88

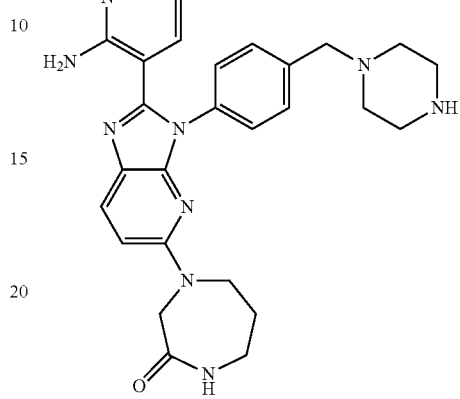

Intermediate 70

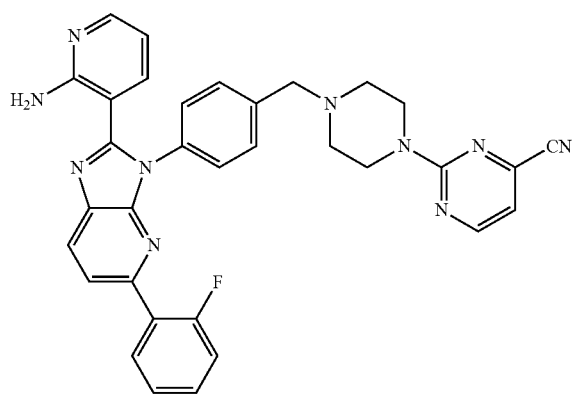

Example 282

Example 283

A mixture of Intermediate 68 (80 mg, 167 μmol), 2-chloropyrimidine-4-carbonitrile (23.3 mg, 167 μmol) and DIEA (43.1 mg, 334 μmol) in NMP (2 mL) was taken up into a microwave tube. The sealed tube was heated at 130° C. for 1 hr under microwave. After purified by prep-HPLC (column: Waters xbridge 150×25 mm×10 μm; mobile phase: [water (NH$_4$HCO$_3$)-ACN]; B %: 65%-95%, 10 min), 2-(4-(4-(2-(2-Aminopyridin-3-yl)-5-(2-fluorophenyl)-3H-imidazo[4,5-b]pyridin-3-yl)benzyl)piperazin-1-yl)pyrimidine-4-carbonitrile (Example 282, 60.4 mg, yield: 62%) was obtained as a brown solid. MS: m/z=583.3 [M+H]$^+$. $^1$H NMR (400 MHz, Dimethylsulfoxide-d$_6$) δ 8.64 (d, J=4.8 Hz, 1H), 8.30 (d, J=8.4 Hz, 1H), 8.00 (dd, J=4.8, 2.0 Hz, 1H), 7.84-7.76 (m, 2H), 7.51-7.43 (m, 5H), 7.38-7.30 (m, 2H), 7.20-7.13 (m, 2H), 6.99 (br s, 2H), 6.38 (dd, J=7.6, 4.8 Hz, 1H), 3.80-3.73 (m, 4H), 3.62 (s, 2H), 2.54-2.52 (m, 4H). $^{19}$F NMR (400 MHz, Dimethylsulfoxide-d$_6$) δ −117.18.

A mixture of Intermediate 70 (250 mg, 502 μmol), 2-chloropyrimidine-4-carbonitrile (70.1 mg, 502 μmol) and DIEA (260 mg, 2.01 mmol) in NMP (3 mL) was taken up into a microwave tube. The sealed tube was heated at 130° C. for 1 hr under microwave. The reaction mixture was quenched with H$_2$O (5 mL) at 0° C., and then extracted with CH$_2$Cl$_2$ (15 mL×3). The combined organic layers were washed with brine (15 mL), dried over Na$_2$SO$_4$, filtered and concentrated under reduced pressure. After purified by prep-HPLC (column: Phenomenex C18 150*25 mm*10 μm; mobile phase: [water (NH$_4$HCO$_3$)-ACN]; B %: 30%-60%, over 10 min), 2-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-4-carbonitrile (Example 283, 98.8 mg, yield: 33%) was obtained as a yellow solid. MS: m/z=601.4 [M+H]$^+$. $^1$H NMR (400 MHz, Dimethylsulfoxide-d$_6$) δ 8.64 (d, J=4.8 Hz, 1H), 8.00-7.89 (m, 2H), 7.47-7.42 (m, 3H), 7.34 (d, J=8.0 Hz, 2H), 7.15 (d, J=4.4 Hz, 1H), 7.03-6.95 (m, 3H), 6.80 (d, J=8.8 Hz, 1H), 6.32 (dd, J=7.6, 4.8 Hz, 1H), 4.18 (s, 2H), 3.86-3.73 (m, 6H), 3.61 (s, 2H), 3.20-3.15 (m, 2H), 2.48-2.46 (m, 4H), 1.68-1.61 (m, 2H).

Example 284: 6-(4-(4-(2-(2-Aminopyridin-3-yl)-5-(3-oxo-1,4-diazepan-1-yl)-3H-imidazo[4,5-b]pyridin-3-yl)benzyl)piperazin-1-yl)pyrimidine-4-carbonitrile

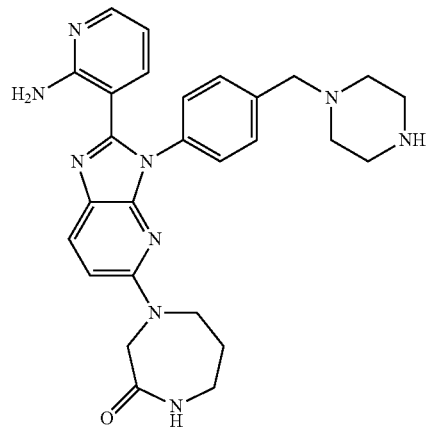

Intermediate 70

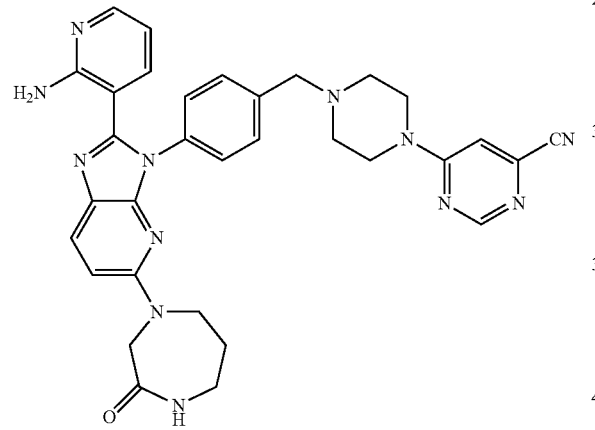

Example 284

A mixture of Intermediate 70 (250 mg, 502 μmol), 6-chloropyrimidine-4-carbonitrile (70.1 mg, 502 μmol) and DIEA (260 mg, 2.01 mmol) in NMP (3 mL) was taken up into a microwave tube. The sealed tube was heated at 130° C. for 1 hr under microwave. The reaction mixture was quenched with H$_2$O (5 mL) at 0° C., and then extracted with CH$_2$Cl$_2$ (15 mL×3). The combined organic layers were washed with aqueous NaCl (15 mL), dried over Na$_2$SO$_4$, filtered and concentrated under reduced pressure. After purified by prep-HPLC (column: Phenomenex C18 150*25 mm*10 μm; mobile phase: [water (NH$_4$HCO$_3$)-ACN]; B %: 23%-53%, over 10 min), 6-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-4-carbonitrile (Example 284, 63.2 mg, yield: 21%) was obtained as a yellow solid. MS: m/z=601.4 [M+H]$^+$. $^1$H NMR (400 MHz, Dimethylsulfoxide-d$_6$) δ 8.56 (d, J=0.8 Hz, 1H), 7.95 (d, J=9.2 Hz, 1H), 7.93 (dd, J=4.8, 2.0 Hz, 1H), 7.57 (s, 1H), 7.46-7.42 (m, 3H), 7.35 (d, J=8.0 Hz, 2H), 7.02-6.96 (m, 3H), 6.80 (d, J=8.8 Hz, 1H), 6.30 (dd, J=7.6, 4.8 Hz, 1H), 4.18 (s, 2H), 3.83-3.80 (m, 2H), 3.77-3.67 (m, 4H), 3.61 (s, 2H), 3.20-3.16 (m, 2H), 2.48-2.45 (m, 4H), 1.67-1.62 (m, 2H).

Example 285: 4-(8-(4-(2-(2-Aminopyridin-3-yl)-5-morpholino-3H-imidazo[4,5-b]pyridin-3-yl)benzyl)-3,8-diazabicyclo[3.2.1]octan-3-yl)-1,3,5-triazine-2-carbonitrile

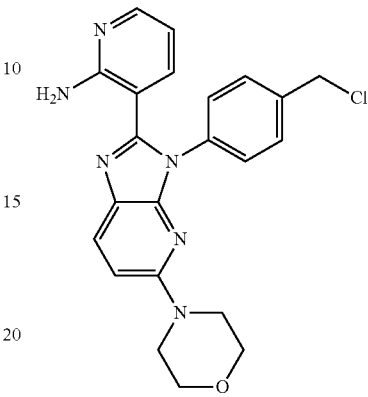

Intermediate 56

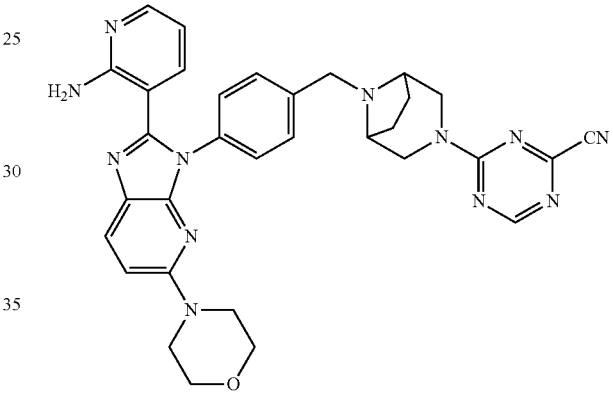

Example 285

To a solution of Intermediate 56 (300 mg, 656 μmol) and Intermediate 71 (200 mg, 606 μmol, TFA salt) in CH$_3$CN (10 mL) were added NaI (19.7 mg, 132 μmol) and K$_2$CO$_3$ (544 mg, 3.94 mmol). The mixture was stirred at 50° C. for 5 hr. The reaction mixture was diluted with H$_2$O (10 mL) and extracted with CH$_2$Cl$_2$ (10 mL×2). The combined organic layers were washed with brine (10 mL×2), dried over Na$_2$SO$_4$, filtered and concentrated under reduced pressure. The residue was purified by silica gel flash chromatography (Eluent of 0~5% MeOH in CH$_2$Cl$_2$), and then the crude product was triturated with CH$_3$CN (5 mL) at 25° C. for 30 min. After purified again by prep-TLC (100% EtOAc), 4-(8-(4-(2-(2-aminopyridin-3-yl)-5-morpholino-3H-imidazo[4,5-b]pyridin-3-yl)benzyl)-3,8-diazabicyclo[3.2.1]octan-3-yl)-1,3,5-triazine-2-carbonitrile (Example 285, 21.7 mg, yield: 5.2%) was obtained as a light-yellow solid. MS: m/z=601.5 [M+H]$^+$. $^1$H NMR (400 MHz, Dimethylsulfoxide-d$_6$) δ 8.71 (s, 1H), 8.02-7.94 (m, 2H), 7.53 (d, J=8.0 Hz, 2H), 7.33 (d, J=8.0 Hz, 2H), 7.04-6.98 (m, 3H), 6.90 (d, J=8.8 Hz, 1H), 6.35 (dd, J=7.6, 4.8 Hz, 1H), 4.29 (d, J=12.0 Hz, 1H), 4.18 (d, J=12.0 Hz, 1H), 3.71-3.66 (m, 4H), 3.64 (s, 2H), 3.44-3.35 (m, 6H), 3.19 (d, J=12.8 Hz, 2H), 2.03-1.96 (m, 2H), 1.54-1.43 (m, 2H).

Example 286: 4-((1-(4-(2-(2-Aminopyridin-3-yl)-5-isopropyl-3H-imidazo[4,5-b]pyridin-3-yl)benzyl)piperidin-4-yl)amino)pyrimidine-2-carbonitrile

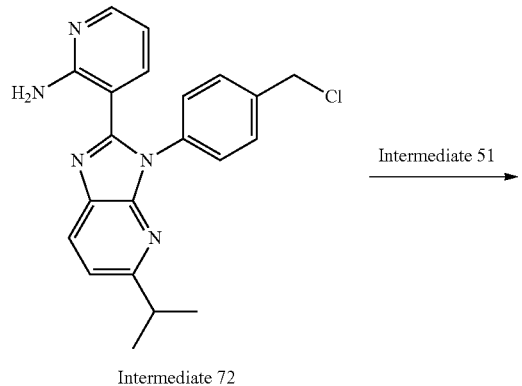

Intermediate 72 →(Intermediate 51)

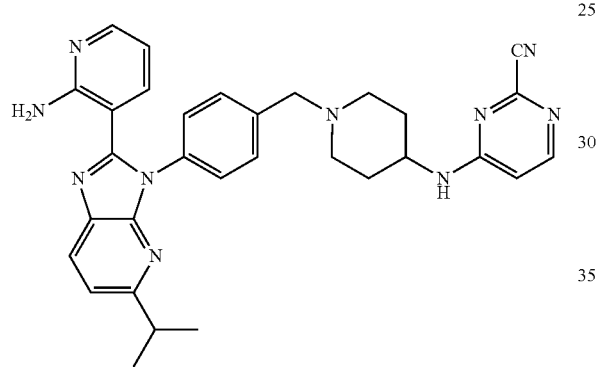

Example 286

A mixture of Intermediate 72 (220 mg, 582 μmol) and Intermediate 51 (130 mg, 640 μmol) in DMF (3 mL) were added NaI (26.1 mg, 174 μmol) and K$_2$CO$_3$ (402 mg, 2.91 mmol). The mixture was stirred at 50° C. for 1 hr. The reaction mixture was diluted with H$_2$O (20 mL) and extracted with EtOAc (30 mL×3). The combined organic layers were washed with H$_2$O (30 mL×3), dried over Na$_2$SO$_4$, filtered and concentrated under reduced pressure. After purified by silica gel flash chromatography (eluent 0~10% MeOH in CH$_2$Cl$_2$), then triturated with MeCN, 4-((1-(4-(2-(2-aminopyridin-3-yl)-5-isopropyl-3H-imidazo[4,5-b]pyridin-3-yl)benzyl)piperidin-4-yl)amino)pyrimidine-2-carbonitrile (Example 286, 71.1 mg, yield: 22%) as a yellow solid. MS: m/z=545.2 [M+H]$^+$. 1H NMR (400 MHz, Dimethylsulfoxide-d$_6$) δ 8.29-8.01 (m, 3H), 7.97 (dd, J=4.8, 1.6 Hz, 1H), 7.44 (d, J=8.4 Hz, 2H), 7.36 (d, J=8.4 Hz, 2H), 7.30 (d, J=8.4 Hz, 1H), 7.00 (dd, J=7.6, 1.6 Hz, 1H), 6.94 (br s, 2H), 6.67 (d, J=6.4 Hz, 1H), 6.35 (dd, J=8.0, 5.2 Hz, 1H), 3.92-3.69 (m, 1H), 3.57 (s, 2H), 3.13-2.99 (m, 1H), 2.81-2.75 (m, 2H), 2.20-2.14 (m, 2H), 1.92-1.80 (m, 2H), 1.55-1.43 (m, 2H), 1.23 (d, J=6.8 Hz, 6H).

Example 287: 4-((1-(4-(2-(2-Aminopyridin-3-yl)-5-methoxy-3H-imidazo[4,5-b]pyridin-3-yl)benzyl)piperidin-4-yl)amino)pyrimidine-2-carbonitrile

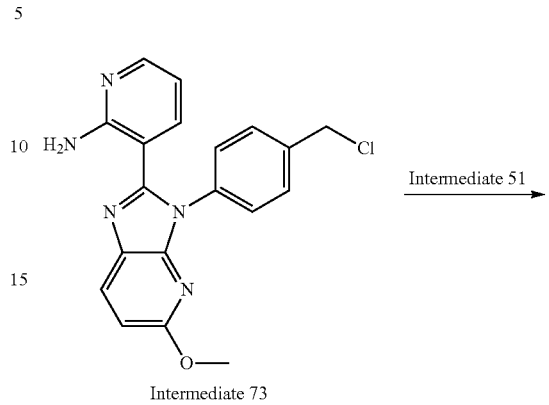

Intermediate 73 →(Intermediate 51)

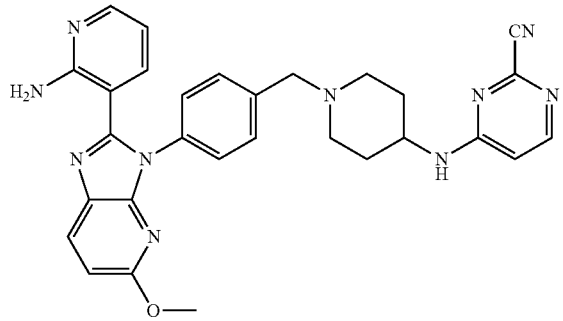

Example 287

To a solution of Intermediate 73 (500 mg, 1.24 mmol) and Intermediate 51 (315 mg, 994 μmol, TFA) in DMF (4 mL) were added K$_2$CO$_3$ (859 mg, 6.21 mmol) and NaI (55.9 mg, 373 mol). The mixture was stirred at 50° C. for 2 hr. The reaction mixture was diluted with H$_2$O (20 mL) and extracted with EtOAc (30 mL×3). The combined organic layers were washed with H$_2$O (30 mL×3), dried over Na$_2$SO$_4$, filtered and concentrated under reduced pressure. After purified by silica gel flash chromatography (Eluent of 0~10% MeOH in CH$_2$Cl$_2$), and then triturated with MeCN (5 mL), 4-((1-(4-(2-(2-aminopyridin-3-yl)-5-methoxy-3H-imidazo[4,5-b]pyridin-3-yl)benzyl)piperidin-4-yl)amino)pyrimidine-2-carbonitrile (Example 287, 82.4 mg, yield: 12%) was obtained as a light-yellow lyophilized powder. MS: m/z=533.2 [M+H]$^+$. $^1$H NMR (400 MHz, Dimethylsulfoxide-d$_6$) δ 8.13-8.03 (m, 3H), 7.95 (dd, J=4.8, 1.2 Hz, 1H), 7.46-7.43 (m, 2H), 7.38-7.34 (m, 2H), 7.04 (dd, J=7.6, 1.6 Hz, 1H), 6.96 (br s, 2H), 6.81 (d, J=8.8 Hz, 1H), 6.67 (d, J=6.0 Hz, 1H), 6.34 (dd, J=7.6, 4.8 Hz, 1H), 3.81-3.75 (m, 4H), 3.57 (s, 2H), 2.82-2.79 (m, 2H), 2.16-2.11 (m, 2H), 1.90-1.87 (m, 2H), 1.53-1.43 (m, 2H).

Example 288: 2-(2-Aminopyridin-3-yl)-3-(4-((4-((2-cyanopyrimidin-4-yl)amino)piperidin-1-yl)methyl)phenyl)-3H-imidazo[4,5-h]pyridine-5-carboxamide Example 289: 2-(2-Aminopyridin-3-yl)-3-(4-((4-((2-cyanopyrimidin-4-yl)amino)piperidin-1-yl)methyl)phenyl)-N,N-dimethyl-3H-imidazo[4,5-h]pyridine-5-carboxamide

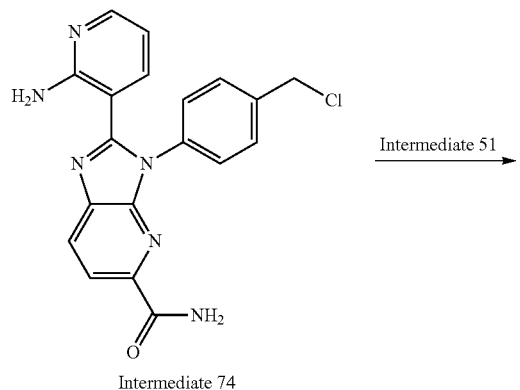

Intermediate 74

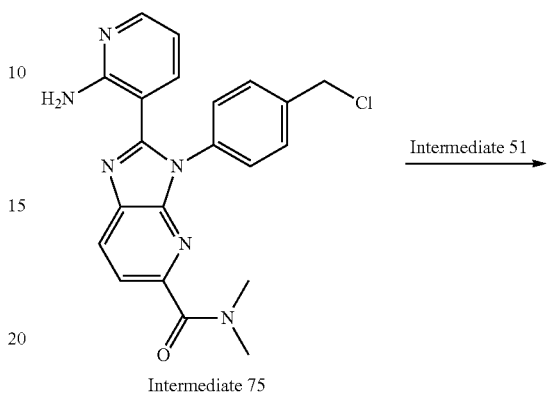

Intermediate 75

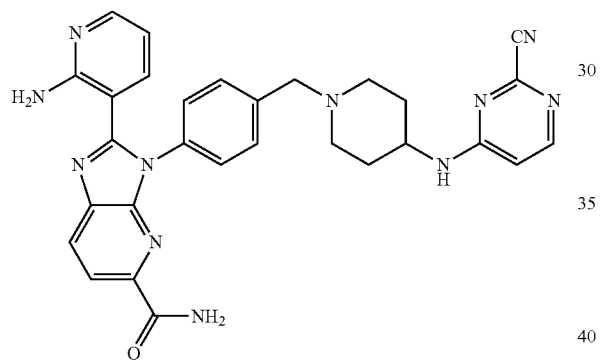

Example 288

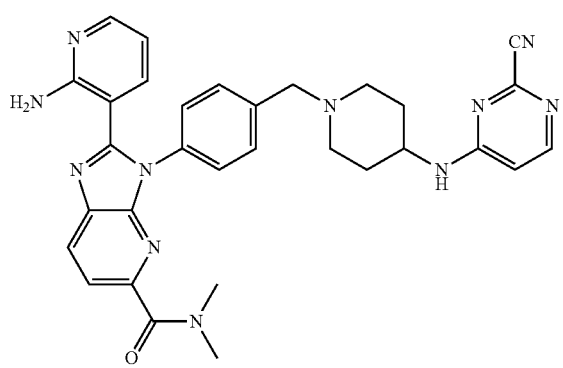

Example 289

To a solution of Intermediate 74 (400 mg, 1.06 mmol) and Intermediate 51 (335 mg, 1.06 mmol, TFA) in DMF (5 mL) were added K$_2$CO$_3$ (730 mg, 5.28 mmol) and NaI (15.8 mg, 106 μmol). The mixture was stirred at 60° C. for 1 hr. After purified by prep-HPLC (column: Waters xbridge 150*25 mm*10 μm; mobile phase: [water (NH$_4$HCO$_3$)-ACN]; gradient: 18%-38% B over 14 min), 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxamide (Example 288, 258.3 mg, yield: 45%) was obtained as a yellow solid. MS: m/z=546.2 [M+H]$^+$. $^1$H NMR (400 MHz, Dimethylsulfoxide-d$_6$) δ 8.32 (d, J=8.4 Hz, 1H), 8.10-8.00 (m, 4H), 7.63-7.57 (m, 2H), 7.45 (br s, 4H), 7.22-7.17 (m, 1H), 6.95 (br s, 2H), 6.67 (d, J=6.0 Hz, 1H), 6.42-6.37 (m, 1H), 3.89-3.74 (m, 1H), 3.57 (s, 2H), 2.86-2.80 (m, 2H), 2.22-2.13 (m, 2H), 1.91-1.81 (m, 2H), 1.52-1.43 (m, 2H).

To a solution of Intermediate 75 (330 mg, 811 μmol) and Intermediate 51 (257 mg, 811 μmol, TFA) in DMF (4 mL) were added K$_2$CO$_3$ (336 mg, 2.43 mmol) and NaI (24.3 mg, 162 μmol). The mixture was stirred at 50° C. for 1 hr. The mixture was filtered, and the filtrate was concentrated to give the crude product. After purified by prep-HPLC (column. Waters xbridge 150*25 mm*10 μm; mobile phase: [water (NH$_4$HCO$_3$)-ACN]; gradient: 16%-46% B over 14 min), 2-(2-aminopyridin-3-yl)-3-(4-((4-((2-cyanopyrimidin-4-yl)amino)piperidin-1-yl)methyl)phenyl)-N,N-dimethyl-3H-imidazo[4,5-b]pyridine-5-carboxamide (Example 289, 204.2 mg, yield: 44%) was obtained as an off-white lyophilized powder. MS: m/z=574.4 [M+H]$^+$. $^1$H NMR (400 MHz, Dimethylsulfoxide-d$_6$) δ 8.28 (d, J=8.0 Hz, 1H), 8.12-8.03 (m, 2H), 8.00 (dd, J=4.8, 1.6 Hz, 1H), 7.58 (d, J=8.0 Hz, 1H), 7.45 (d, J=8.4 Hz, 2H), 7.40 (d, J=8.4 Hz, 2H), 7.18 (dd, J=7.6, 1.6 Hz, 1H), 6.98 (br s, 2H), 6.67 (d, J=6.0 Hz, 1H), 6.39 (dd, J=8.0, 5.2 Hz, 1H), 3.88-3.74 (m, 1H), 3.57 (s, 2H), 2.98 (s, 3H), 2.95 (s, 3H), 2.85-2.76 (m, 2H), 2.19-2.05 (m, 2H), 1.95-1.81 (m, 2H), 1.56-1.39 (m, 2H).

Example 290: 6-(4-(4-(2-(2-Aminopyridin-3-yl)-5-cyclopropyl-3H-imidazo[4,5-b]pyridin-3-yl)benzyl)piperazin-1-yl)pyrimidine-4-carbonitrile Example 291: 6-((1-(4-(2-(2-Aminopyridin-3-yl)-5-cyclopropyl-3H-imidazo[4,5-b]pyridin-3-yl)benzyl)piperidin-4-yl)amino)pyrimidine-4-carbonitrile

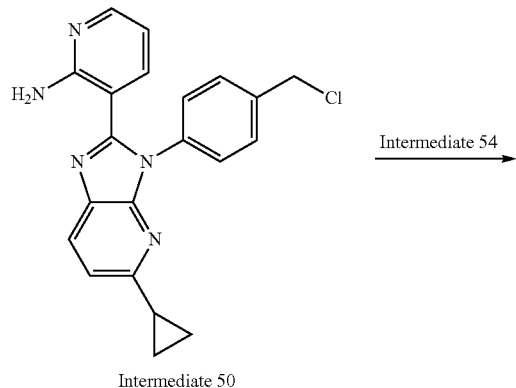

Intermediate 50

→ Intermediate 54

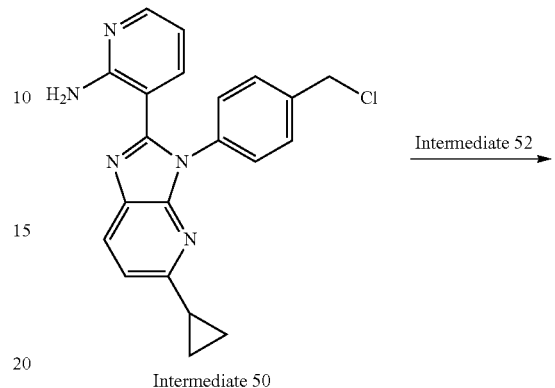

Intermediate 50

→ Intermediate 52

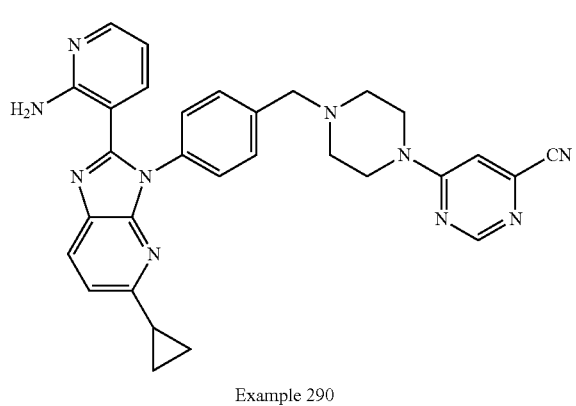

Example 290

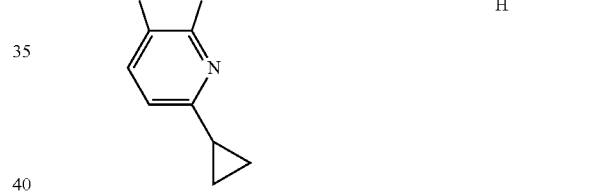

Example 291

To a solution of Intermediate 50 (200 mg, 485 μmol) and Intermediate 54 (147 mg, 485 μmol) in DMF (2 mL) were added NaI (72.7 mg, 485 μmol) and K$_2$CO$_3$ (335 mg, 2.43 mmol). The mixture was stirred at 50° C. for 1 hr. The reaction mixture was filtered. The residue was purified by prep-HPLC (column: [water (NH$_4$HCO$_3$)-ACN]; B %: 38%-68%, 14 min) to give 6-(4-(4-(2-(2-aminopyridin-3-yl)-5-cyclopropyl-3H-imidazo[4,5-b]pyridin-3-yl)benzyl)piperazin-1-yl)pyrimidine-4-carbonitrile (Example 290, 64.4 mg, yield: 25%) as a yellow solid. MS: m/z=529.4 [M+H]$^+$. $^1$H NMR (400 MHz, Dimethylsulfoxide-d$_6$) δ 8.57 (d, J=1.2 Hz, 1H), 8.04 (d, J=8.0 Hz, 1H), 7.96 (dd, J=4.8, 2.0 Hz, 1H), 7.57 (d, J=0.8 Hz, 1H), 7.46 (d, J=8.4 Hz, 2H), 7.34 (d, J=8.4 Hz, 2H), 7.25 (d, J=8.4 Hz, 1H), 7.06 (dd, J=7.6, 1.6 Hz, 1H), 6.97 (brs, 2H), 6.32 (dd, J=7.6, 4.8 Hz, 1H), 3.84-3.66 (m, 4H), 3.62 (s, 2H), 2.49-2.45 (m, 4H), 2.21-2.13 (m, 1H), 0.96-0.89 (m, 2H), 0.85-0.79 (m, 2H).

To a solution of Intermediate 50 (200 mg, 485 μmol) and Intermediate 52 (154 mg, 485 μmol) in DMF (2 mL) were added NaI (36.3 mg, 242 μmol) and K$_2$CO$_3$ (335 mg, 2.43 mmol). The mixture was stirred at 50° C. for 1 hr. The reaction mixture was filtered. The residue was purified by prep-HPLC (column: [water (NH$_4$HCO$_3$)-ACN]; B %: 42%-72%, 14 min) to give 6-((1-(4-(2-(2-aminopyridin-3-yl)-5-cyclopropyl-3H-imidazo[4,5-b]pyridin-3-yl)benzyl)piperidin-4-yl)amino)pyrimidine-4-carbonitrile (Example 291, 62.3 mg, yield: 24%) was obtained as a yellow solid. MS: m/z=543.4 [M+H]$^+$. $^1$H NMR (400 MHz, Dimethylsulfoxide-d$_6$) δ 8.50 (m, 1H), 8.08 (d, J=7.2 Hz, 1H), 8.03 (d, J=8.0 Hz, 1H), 7.96 (dd, J=4.8, 1.6 Hz, 1H), 7.43 (d, J=8.4 Hz, 2H), 7.33 (d, J=8.4 Hz, 2H), 7.24 (d, J=8.4 Hz, 1H), 7.07 (dd, J=7.6, 1.8 Hz, 1H), 7.01-6.87 (m, 3H), 6.34 (dd, J=7.6, 4.8 Hz, 1H), 3.95-3.79 (m, 1H), 3.56 (s, 2H), 2.81 (d, J=11.2 Hz, 2H), 2.20-2.08 (m, 3H), 1.90 (m, 2H), 1.59-1.42 (m, 2H), 0.97-0.89 (m, 2H), 0.86-0.78 (m, 2H).

Example 292: 4-(4-(4-(2-(2-Aminopyridin-3-yl)-5-morpholino-3H-imidazo[4,5-b]pyridin-3-yl)benzyl)piperazin-1-yl)-1,3,5-triazine-2-carbonitrile

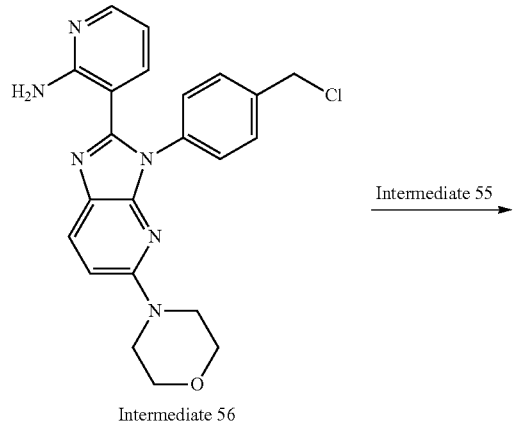

Intermediate 56

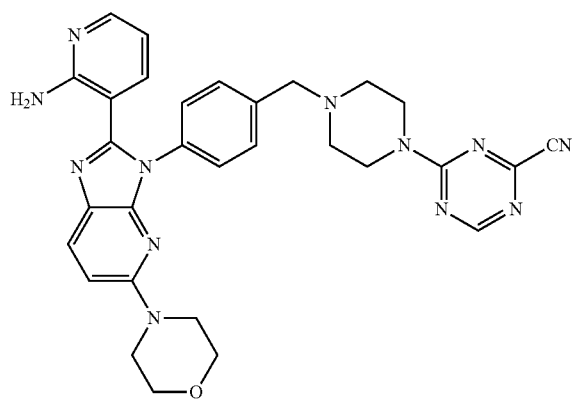

Example 292

To a solution of Intermediate 56 (300 mg, 656 μmol) and Intermediate 55 (200 mg, 656 μmol) in DMF (3 mL) was added NaI (49.2 mg, 328 μmol), $K_2CO_3$ (453 mg, 3.28 mmol). The mixture was stirred at 25° C. for 2 hr. The mixture was quenched with $H_2O$ (30 mL) and extracted with EtOAc (60 mL), the combined organic phase was dried over anhydrous $Na_2SO_4$, filtered and concentrated. The residue was purified by prep-TLC ($CH_2Cl_2$:MeOH=20:1) to give 4-(4-(4-(2-(2-aminopyridin-3-yl)-5-morpholino-3H-imidazo[4,5-b]pyridin-3-yl)benzyl)piperazin-1-yl)-1,3,5-triazine-2-carbonitrile (Example 292, 73.6 mg, yield: 18%) as a light-yellow solid. MS: m/z=575.4 [M+H]+. 1H NMR (400 MHz, Dimethylsulfoxide-$d_6$) δ 8.72 (s, 1H), 7.98 (d, J=8.8 Hz, 1H), 7.95-7.91 (m, 1H), 7.46 (d, J=7.6 Hz, 2H), 7.33 (d, J=8.4 Hz, 2H), 7.03-6.97 (m, 3H), 6.90 (d, J=9.2 Hz, 1H), 6.32 (dd, J=7.2, 4.4 Hz, 1H), 3.87-3.79 (m, 4H), 3.72-3.59 (m, 8H), 3.42-3.38 (m, 4H), 3.34-3.33 (m, 2H).

Example 293: 4-(4-(4-(2-(2-Aminopyridin-3-yl)-5-(2-cyanophenyl)-3H-imidazo[4,5-b]pyridin-3-yl)benzyl)piperazin-1-yl)pyrimidine-2-carbonitrile

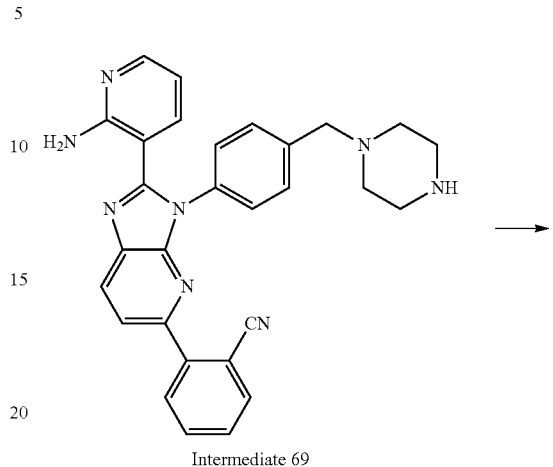

Intermediate 69

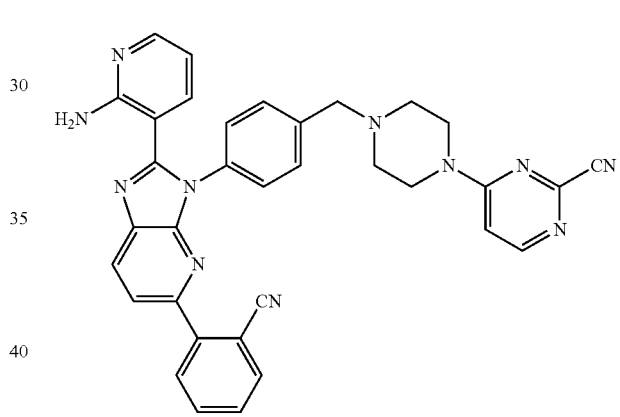

Example 293

A mixture of Intermediate 69 (100 mg, 206 μmol), 4-chloropyrimidine-2-carbonitrile (29 mg, 206 μmol) and DIEA (133 mg, 1.03 mmol) in NMP (3 mL) was taken up into a microwave tube. The sealed tube was heated at 130° C. for 1 hr under microwave. The reaction mixture was quenched with $H_2O$ (5 mL) at 0° C., and then diluted with $CH_2Cl_2$ (10 mL) and extracted with $CH_2Cl_2$ (15 mL×2). The combined organic layers were washed with brine (15 mL), dried over $Na_2SO_4$, filtered and concentrated under reduced pressure. After purified by prep-HPLC (column: Waters xbridge 150*25 mm 10 μm; mobile phase: [water ($NH_4HCO_3$)-ACN]; gradient: 33%-63% B over 14 min), 4-(4-(4-(2-(2-aminopyridin-3-yl)-5-(2-cyanophenyl)-3H-imidazo[4,5-b]pyridin-3-yl)benzyl)piperazin-1-yl)pyrimidine-2-carbonitrile (Example 293, 35.1 mg, yield: 29%) was obtained as a yellow powder. MS: m/z=590.2 [M+H]+. 1H NMR (400 MHz, Dimethylsulfoxide-$d_6$) δ 8.38 (d, J=8.0 Hz, 1H), 8.26 (d, J=6.4 Hz, 1H), 8.01 (dd, J=4.8, 2.0 Hz, 1H), 7.95 (d, J=8.0 Hz, 1H), 7.92-7.77 (m, 3H), 7.67-7.57 (m, 1H), 7.49-7.43 (m, 4H), 7.19 (dd, J=7.6, 2.0 Hz, 1H), 7.10 (d, J=6.8 Hz, 1H), 7.00 (br s, 2H), 6.39 (dd, J=7.6, 4.8 Hz, 1H), 3.68-3.67 (m, 4H), 3.61 (s, 2H), 2.49-2.45 (m, 4H).

Example 294: 4-(4-(4-(2-(2-Aminopyridin-3-yl)-5-(4-cyanophenyl)-3H-imidazo[4,5-b]pyridin-3-yl)benzyl)piperazin-1-yl)pyrimidine-2-carbonitrile Example 295: 4-(4-(4-(2-(2-Aminopyridin-3-yl)-5-(3-fluorophenyl)-3H-imidazo[4,5-b]pyridin-3-yl)benzyl)piperazin-1-yl)pyrimidine-2-carbonitrile

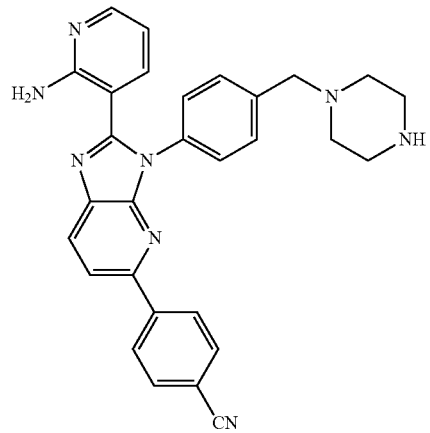

Intermediate 78

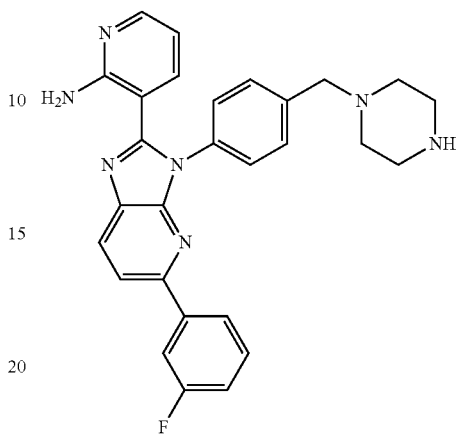

Intermediate 79

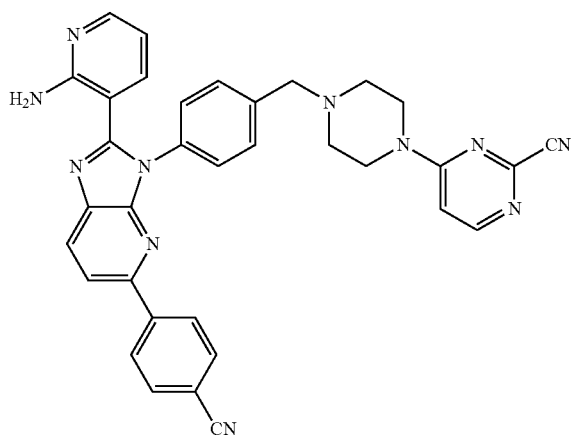

Example 294

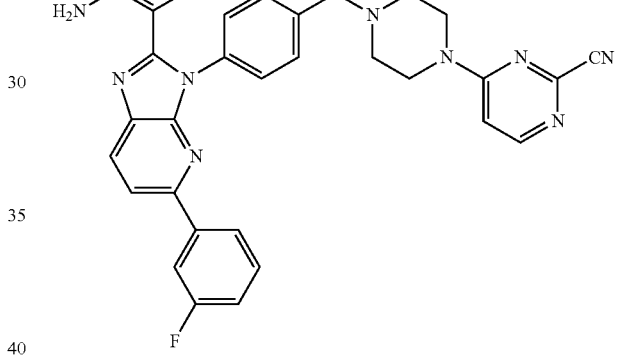

Example 295

A mixture of Intermediate 78 (100 mg, 206 μmol), 4-chloropyrimidine-2-carbonitrile (29 mg, 210 μmol) and DIEA (136 mg, 1.05 mmol) in NMP (3 mL) was taken up into a microwave tube. The sealed tube was heated at 130° C. for 1 hr under microwave. The reaction mixture was quenched with H$_2$O (5 mL) at 0° C., and then extracted with CH$_2$Cl$_2$ (15 mL×2). The combined organic layers were washed with brine (15 mL), dried over Na$_2$SO$_4$, filtered and concentrated under reduced pressure. After purified by prep-HPLC (column: Waters xbridge 150*25 mm 10 μm; mobile phase: [water (NH$_4$HCO$_3$)-ACN]; gradient: 45%-75% B over 10 min), 4-(4-(4-(2-(2-aminopyridin-3-yl)-5-(4-cyanophenyl)-3H-imidazo[4,5-b]pyridin-3-yl)benzyl)piperazin-1-yl)pyrimidine-2-carbonitrile (Example 294, 13.6 mg, yield: 10%) was obtained as a yellow powder. MS: m/z=590.3 [M+H]$^+$. $^1$H NMR (400 MHz, Methanol-d$_4$) δ 8.25 (dd, J=8.4, 2.0 Hz, 3H), 8.18 (d, J=6.8 Hz, 1H), 8.06 (d, J=8.4 Hz, 1H), 8.00 (dd, J=5.2, 2.0 Hz, 1H), 7.80 (d, J=8.8 Hz, 2H), 7.58 (d, J=8.8 Hz, 2H), 7.47 (d, J=8.4 Hz, 2H), 7.34 (dd, J=7.6, 2.0 Hz, 1H), 6.95 (d, J=6.4 Hz, 1H), 6.48 (dd, J=7.6, 5.2 Hz, 1H), 3.83-3.74 (m, 4H), 3.70 (s, 2H), 2.63-2.57 (m, 4H).

A mixture of Intermediate 79 (100 mg, 209 μmol), 4-chloropyrimidine-2-carbonitrile (29 mg, 210 μmol) and DIEA (136 mg, 1.05 mmol) in NMP (3 mL) was taken up into a microwave tube. The sealed tube was heated at 130° C. for 1 hr under microwave. The reaction mixture was quenched with H$_2$O (5 mL) at 0° C., and then extracted with CH$_2$Cl$_2$ (15 mL×3). The combined organic layers were washed with brine (15 mL), dried over Na$_2$SO$_4$, filtered and concentrated under reduced pressure. After purified by prep-HPLC (column: Waters xbridge 150*25 mm 10 μm; mobile phase: [water (NH$_4$HCO$_3$)-ACN]; gradient: 44%-74% B over 14 min), 4-(4-(4-(2-(2-aminopyridin-3-yl)-5-(3-fluorophenyl)-3H-imidazo[4,5-b]pyridin-3-yl)benzyl)piperazin-1-yl)pyrimidine-2-carbonitrile (Example 295, 43 mg, yield: 33%) was obtained as a yellow powder. MS: m/z=583.3 [M+H]$^+$. $^1$H NMR (400 MHz, Methanol-d$_4$) δ 8.23-8.16 (m, 2H), 8.01-7.95 (m, 2H), 7.87 (d, J=8.4 Hz, 1H), 7.81-7.76 (m, 1H), 7.59 (d, J=8.4 Hz, 2H), 7.49-7.44 (m, 3H), 7.34 (dd, J=7.6, 4.6 Hz, 1H), 7.13-7.09 (m, 1H), 6.95 (d, J=6.4 Hz, 1H), 6.48 (dd, J=7.6, 5.2 Hz, 1H), 3.78-3.76 (m, 4H), 3.70 (s, 2H), 2.61 (t, J=4.8 Hz, 4H). $^{19}$F NMR (400 MHz, Methanol-d$_4$) δ −115.26.

Example 296: 4-(4-(4-(2-(2-Aminopyridin-3-yl)-5-(3-chlorophenyl)-3H-imidazo[4,5-b]pyridin-3-yl)benzyl)piperazin-1-yl)pyrimidine-2-carbonitrile

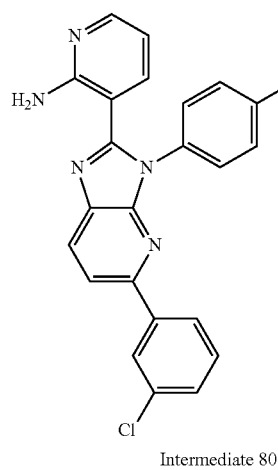

Intermediate 80

→

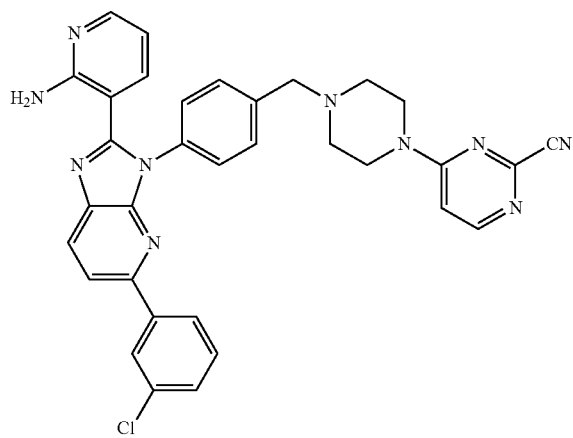

Example 296

A mixture of Intermediate 80 (100 mg, 202 μmol), 4-chloropyrimidine-2-carbonitrile (28 mg, 202 μmol) and DIEA (130 mg, 1.01 mmol) in NMP (3 mL) was taken up into a microwave tube. The sealed tube was heated at 130° C. for 1 hr under microwave. The reaction mixture was quenched with H$_2$O (5 mL) at 0° C., and then extracted with CH$_2$Cl$_2$ (15 mL×3). The combined organic layers were washed with brine (15 mL), dried over Na$_2$SO$_4$, filtered and concentrated under reduced pressure. After purified by prep-HPLC (column: Phenomenex C18 150×25 mm×10 μm; mobile phase: [water (NH$_4$HCO$_3$)-ACN]; gradient: 55%-85% B over 10 min), 4-(4-(4-(2-(2-Aminopyridin-3-yl)-5-(3-chlorophenyl)-3H-imidazo[4,5-b]pyridin-3-yl)benzyl)piperazin-1-yl)pyrimidine-2-carbonitrile (Example 296, 45.7 mg, yield: 36%) was obtained as a brown solid. MS: m/z=599.2 [M+H]$^+$. $^1$H NMR (400 MHz, Methanol-d$_4$) δ 8.23-8.16 (m, 2H), 8.05 (s, 1H), 8.00-7.95 (m, 3H), 7.59 (d, J=8.4 Hz, 2H), 7.47 (d, J=8.4 Hz, 2H), 7.46-7.36 (m, 2H), 7.34 (dd, J=7.6, 1.6 Hz, 1H), 6.94 (d, J=6.4 Hz, 1H), 6.48 (dd, J=7.6, 4.8 Hz, 1H), 3.73-3.80 (m, 4H), 3.70 (s, 2H), 2.63-2.59 (m, 4H).

Example 297: 2-(4-(4-(2-(2-Aminopyridin-3-yl)-5-(3-chlorophenyl)-3H-imidazo[4,5-b]pyridin-3-yl)benzyl)piperazin-1-yl)pyrimidine-4-carbonitrile

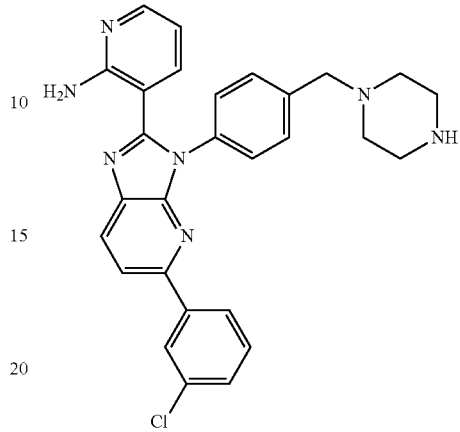

Intermediate 80

→

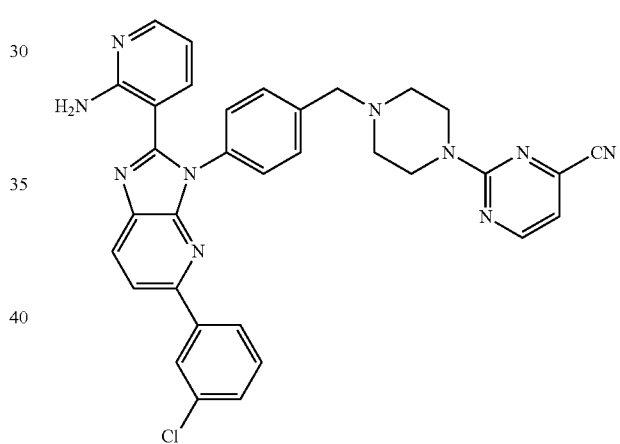

Example 297

To a solution of Intermediate 80 (100 mg, 202 μmol) and 2-chloropyrimidine-4-carbonitrile (28 mg, 202 μmol) and DIEA (130 mg, 1.01 mmol) in NMP (3 mL) was taken up into a microwave tube. The sealed tube was heated at 130° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with brine (15 mL), dried over Na$_2$SO$_4$, filtered and concentrated under reduced pressure. After purified by prep-HPLC (column: Waters xbridge 150*25 mm 10 μm; mobile phase: [water (NH$_4$HCO$_3$)-ACN]; gradient: 60%-80% B over 14 min), 2-(4-(4-(2-(2-Aminopyridin-3-yl)-5-(3-chlorophenyl)-3H-imidazo[4,5-b]pyridin-3-yl)benzyl)piperazin-1-yl)pyrimidine-4-carbonitrile (Example 297, 79 mg, yield: 65%) was obtained as a yellow lyophilized powder. MS: m/z=599.4 [M+H]$^+$. $^1$H NMR (400 MHz, Dimethylsulfoxide-d$_6$) δ 8.65 (d, J=4.8 Hz, 1H), 8.29 (d, J=8.4 Hz, 1H), 8.07-8.00 (m, 4H), 7.54-7.45 (m, 6H), 7.19-7.14 (m, 2H), 7.05 (br s, 2H), 6.38 (dd, J=7.2, 5.2 Hz, 1H), 3.79-3.77 (m, 4H), 3.65 (s, 2H), 2.47-2.35 (m, 4H).

Example 298: 4-((1-(4-(2-(2-Aminopyridin-3-yl)-5-cyclopropyl-3H-imidazo[4,5-b]pyridin-3-yl)benzyl)piperidin-4-yl)amino)pyrimidine-2-carbonitrile

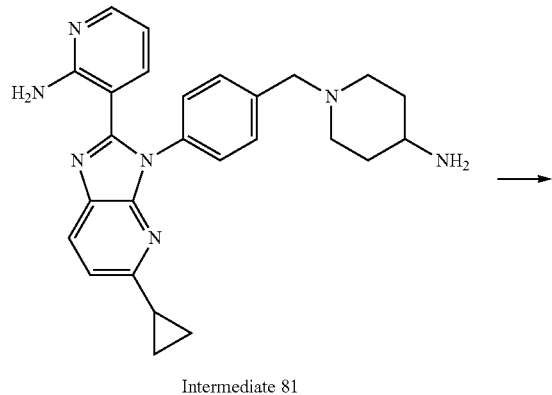

Intermediate 81

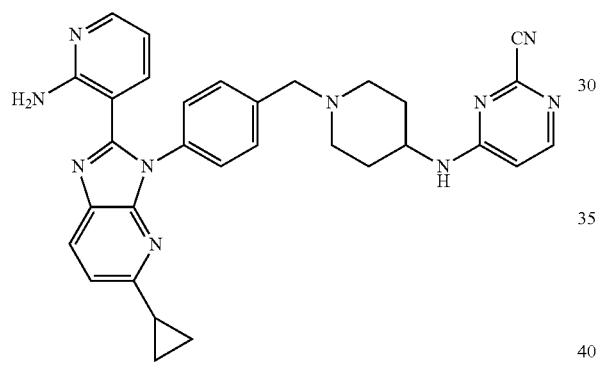

Example 298

A mixture of Intermediate 81 (110 mg, 250 µmol), 4-chloropyrimidine-2-carbonitrile (38 mg, 275 µmol) and DIEA (97 mg, 751 µmol) in NMP (2 mL) was taken up into a microwave tube. The sealed tube was stirred at 130° C. for 30 min under microwave. The reaction mixture was filtered. The residue was purified by prep-HPLC (column: Waters xbridge 150*25 mm 10 µm; mobile phase: [water (NH$_4$HCO$_3$)-ACN]; B %: 33%-63%, 14 min), 4-((1-(4-(2-(2-aminopyridin-3-yl)-5-cyclopropyl-3H-imidazo[4,5-b]pyridin-3-yl)benzyl)piperidin-4-yl)amino)pyrimidine-2-carbonitrile (Example 298, 19.4 mg, yield: 14%) was obtained as a light-pink solid. MS: m/z=543.3 [M+H]$^+$. $^1$H NMR (400 MHz, Dimethylsulfoxide-d$_6$) δ 8.10-8.01 (m, 3H), 7.96 (dd, J=4.8, 1.6 Hz, 1H), 7.43 (d, J=8.0 Hz, 2H), 7.33 (d, =8.0 Hz, 2H), 7.24 (d, J=8.0 Hz, 1H), 7.06 (dd, J=7.6, 1.6 Hz, 1H), 6.98 (br s, 2H), 6.67 (d, J=6.4 Hz, 1H), 6.34 (dd, J=7.6, 4.8 Hz, 1H), 3.88-3.75 (m, 1H), 3.57 (s, 2H), 2.85-2.78 (m, 2H), 2.20-2.11 (m, 3H), 1.93-1.89 (m, 2H), 1.56-1.45 (m, 2H), 0.96-0.90 (m, 2H), 0.85-0.80 (m, 2H).

Example 299: 4-((1-(4-(2-(2-Aminopyridin-3-yl)-5-(tetrahydro-2H-pyran-4-yl)-3H-imidazo[4,5-b]pyridin-3-yl)benzyl)piperidin-4-yl)amino)pyrimidine-2-carbonitrile

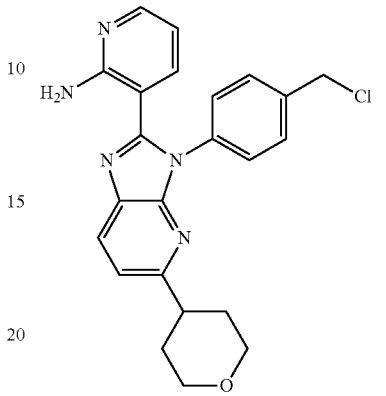

Intermediate 82

→ Intermediate 51 →

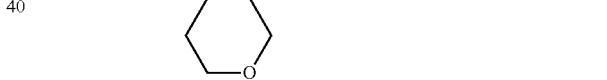

Example 299

To a solution of Intermediate 82 (300 mg, 714 µmol) and Intermediate 51 (174 mg, 857 gmol) in DMF (3 mL) were added NaI (21 mg, 143 µmol) and K$_2$CO$_3$ (296 mg, 2.1 mmol). The mixture was stirred at 50° C. for 2 hr. Then the mixture was diluted with H$_2$O (20 mL) and extracted with EtOAc (20 mL×2). The combined organic layers were washed with brine (20 mL), dried over Na$_2$SO$_4$, filtered and concentrated under reduced pressure. The crude product was purified by silica gel flash chromatography (Eluent of 0~6% MeOH in CH$_2$Cl$_2$) to give 4-((1-(4-(2-(2-aminopyridin-3-yl)-5-(tetrahydro-2H-pyran-4-yl)-3H-imidazo[4,5-b]pyridin-3-yl)benzyl)piperidin-4-yl)amino)pyrimidine-2-carbonitrile (Example 299, 44.2 mg, yield: 10%) as a light yellow solid. MS: m/z=587.2 [M+H]$^+$. $^1$H NMR (400 MHz, Dimethylsulfoxide-d$_6$) δ 8.16-8.01 (m, 3H), 7.97 (dd, J=4.8, 1.6 Hz, 1H), 7.47-7.42 (m, 2H), 7.39-7.30 (m, 3H), 7.09 (dd, J=8.0, 1.6 Hz, 1H), 6.94 (br s, 2H), 6.67 (d, J=6.0 Hz, 1H), 6.35 (dd, J=7.6, 4.8 Hz, 1H), 3.96-3.88 (m, 2H), 3.87-3.75 (m, 1H), 3.57 (s, 2H), 3.47-3.39 (m, 2H), 3.04-2.94 (m, 1H), 2.86-2.77 (m, 2H), 2.21-2.08 (m, 2H), 1.95-1.83 (m, 2H), 1.79-1.71 (m, 4H), 1.55-1.43 (m, 2H).

Example 300: 4-((1-(4-(2-(2-Aminopyridin-3-yl)-5-phenyl-3H-imidazo[4,5-b]pyridin-3-yl)benzyl)azetidin-3-yl)amino)-1,3,5-triazine-2-carbonitrile Example 301: 4-(6-(4-(2-(2-Aminopyridin-3-yl)-5-phenyl-3H-imidazo[4,5-b]pyridin-3-yl)benzyl)-2,6-diazaspiro[3.4]octan-2-yl)-1,3,5-triazine-2-carbonitrile

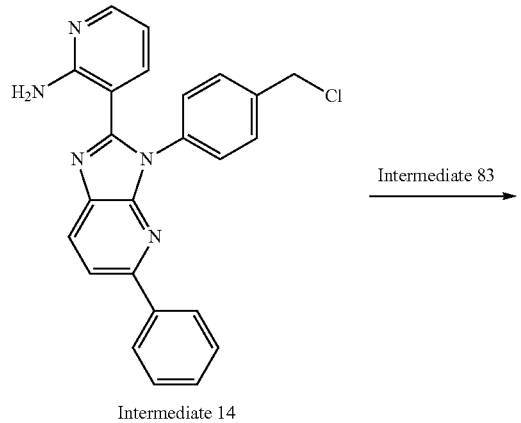

Intermediate 14

→ Intermediate 83

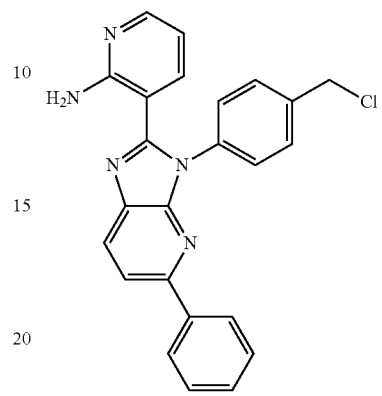

Intermediate 14

→ Intermediate 84

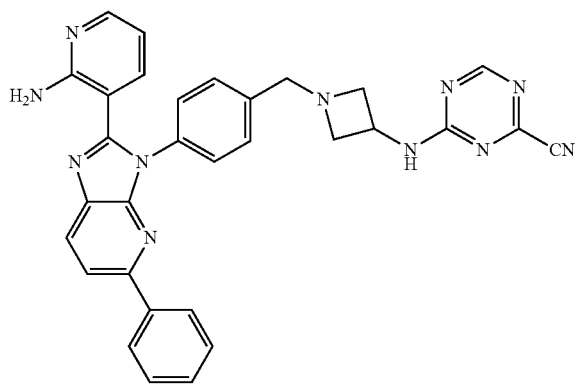

Example 300

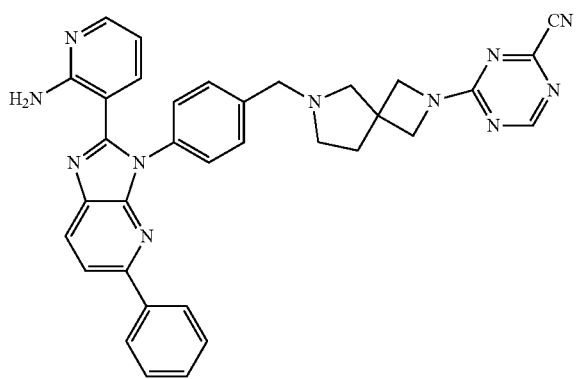

Example 301

To a solution of Intermediate 14 (180 mg, HCl salt, 401 μmol) and Intermediate 83 (116 mg TFA salt, 401 μmol) in DMF (2 mL) were added NaI (30.1 mg, 200 μmol) and K₂CO₃ (277 mg, 2.01 mmol). The mixture was stirred at 50° C. for 2 hr. The mixture was concentrated under reduced pressure. The residue was purified by prep-HPLC (column: [water (NH₄HCO₃)-ACN]; B %: 39%-69%, 14 min) give 4-((1-(4-(2-(2-aminopyridin-3-yl)-5-phenyl-3H-imidazo[4,5-b]pyridin-3-yl)benzyl)azetidin-3-yl)amino)-1,3,5-triazine-2-carbonitrile (Example 300, 50 mg, yield: 14%) as a yellow solid. MS: m/z=552.4 [M+H]⁺. ¹H NMR (400 MHz, Dimethylsulfoxide-d₆) δ 9.40 (d, J=6.4 Hz, 1H), 8.76-8.63 (m, 1H), 8.27 (d, J=8.4 Hz, 1H), 8.05-7.96 (m, 4H), 7.49-7.37 (m, 7H), 7.16 (dd, J=7.6, 2.0 Hz, 1H), 7.00 (br s, 2H), 6.39 (dd, J=7.6, 4.8 Hz, 1H), 4.51-4.36 (m, 1H), 3.70 (s, 2H), 3.61 (t, J=7.2 Hz, 2H), 3.15-3.05 (m, 2H).

To a solution of Intermediate 14 (200 mg, 486 μmol) in DMF (8 mL) were added Intermediate 84 (115 mg, 534 μmol), NaI (15 mg, 97 μmol) and K₂CO₃ (201 mg. 1.46 mmol) at 25° C., the mixture was stirred at 50° C. for 3 hr. The reaction mixture was poured into H₂O (50 mL). The mixture was extracted with CH₂Cl₂ (20 mL×2). The combined organic layers were washed with brine (40 mL), dried over anhydrous Na₂SO₄, filtered and concentrated to dryness. The residue was purified by silica gel flash chromatography (Eluent of 0~8% MeOH in CH₂Cl₂) to give 4-(6-(4-(2-(2-aminopyridin-3-yl)-5-phenyl-3H-imidazo[4,5-b]pyridin-3-yl)benzyl)-2,6-diazaspiro[3.4]octan-2-yl)-1,3,5-triazine-2-carbonitrile (Example 301, 19.3 mg yield: 6%) as a yellow solid. MS: m/z=592.3 [M+H]⁺. ¹H NMR (400 MHz, Dimethylsulfoxide-d₆) δ 8.67 (s, 1H), 8.27 (d, J=8.4 Hz, 1H), 8.06-7.96 (m, 4H), 7.52-7.43 (m, 6H), 7.41-7.36 (m, 1H), 7.17 (dd, J=8.0, 2.0 Hz, 1H), 7.02 (brs, 2H), 6.38 (dd, J=7.6, 4.8 Hz, 1H), 4.12 (s, 4H), 3.69 (s, 2H), 2.78 (s, 2H), 2.62-2.58 (m, 2H), 2.16-2.10 (m, 2H).

Example 302: 4-(7-(4-(2-(2-Aminopyridin-3-yl)-5-phenyl-3H-imidazo[4,5-b]pyridin-3-yl)benzyl)-2,7-diazaspiro[4.4]nonan-2-yl)pyrimidine-2-carbonitrile Example 303: 4-(6-(4-(2-(2-Aminopyridin-3-yl)-5-phenyl-3H-imidazo[4,5-b]pyridin-3-yl)benzyl)-2,6-diazaspiro[3.3]heptan-2-yl)-1,3,5-triazine-2-carbonitrile

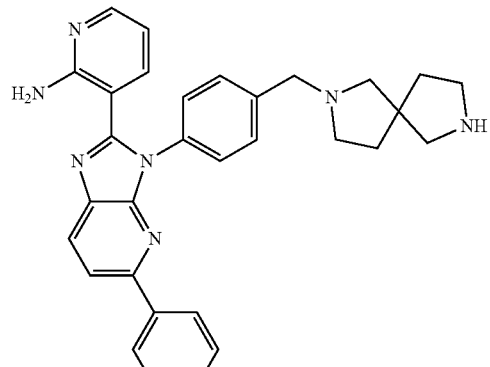

Intermediate 157

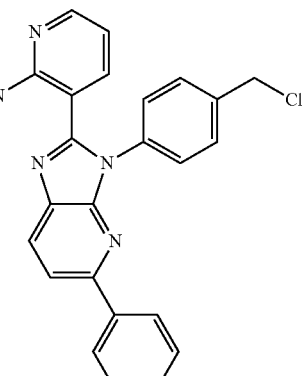

Intermediate 14

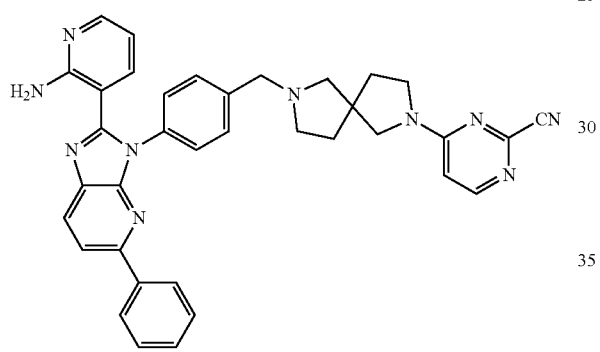

Example 302

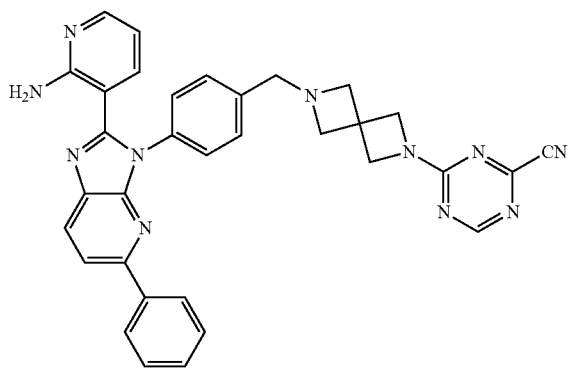

Example 303

To a solution of Intermediate 157 (200 mg, 372 μmol) and 4-chloropyrimidine-2-carbonitrile (62 mg, 446 μmol) in DMF (1 mL) were added $K_2CO_3$ (257 mg, 2.0 mmol) and NaI (56 mg, 372 μmol). The mixture was stirred at 80° C. for 1 hr. The reaction mixture was diluted with $H_2O$ (20 mL) and extracted with EtOAc (40 mL). The combined organic layers were washed with brine (30 mL), dried over $Na_2SO_4$, filtered and concentrated under reduced pressure. The residue was purified by prep-HPLC (column: Phenomenex C18 150*25 mm*10 μm; mobile phase: [water ($NH_4HCO_3$)-ACN]; gradient: B: 50%-80%, 14 min) to give 4-(7-(4-(2-(2-aminopyridin-3-yl)-5-phenyl-3H-imidazo[4,5-b]pyridin-3-yl)benzyl)-2,7-diazaspiro[4.4]nonan-2-yl)pyrimidine-2-carbonitrile (Example 302, 11 mg, yield: 5%) as an off-white solid. MS: m/z=605.3 [M+H]$^+$. $^1$H NMR (400 MHz, Methanol-$d_4$) δ 8.19 (d, J=8.4 Hz, 1H), 8.14-8.10 (m, 1H), 8.02 (d, J=7.2 Hz, 2H), 7.97-7.91 (m, 2H), 7.56 (d, J=8.4 Hz, 2H), 7.47-7.37 (m, 5H), 7.34-7.28 (m, 1H), 6.64 (d, J=6.4 Hz, 1H), 6.46-6.39 (m, 1H), 3.76 (s, 2H), 3.67-3.54 (m, 2H), 3.47-3.41 (m, 2H), 2.88-2.81 (m, 1H), 2.77-2.66 (m, 2H), 2.65-2.55 (m, 1H), 2.15-2.03 (m, 2H), 1.98-1.90 (m, 2H).

To a solution of Intermediate 14 (200 mg, 486 μmol) in DMF (8 mL) were added Intermediate 85 (108 mg, 534 μmol), NaI (15 mg, 97 μmol) and $K_2CO_3$ (201 mg, 1.46 mmol) at 25° C. The mixture was stirred at 50° C. for 3 hr. The reaction mixture was poured into $H_2O$ (50 mL). The mixture was extracted with $CH_2Cl_2$ (20 mL×2). The combined organic layers were washed with brine (40 mL), dried over anhydrous $Na_2SO_4$, filtered and concentrated to dryness. The residue was purified by silica gel flash chromatography (Eluent of 0~8% MeOH in $CH_2Cl_2$) to give 4-(6-(4-(2-(2-aminopyridin-3-yl)-5-phenyl-3H-imidazo[4,5-b]pyridin-3-yl)benzyl)-2,6-diazaspiro[3.3]heptan-2-yl)-1,3,5-triazine-2-carbonitrile (Example 303, 17.6 mg, yield: 6%) as a white solid. MS: m/z=578.3 [M+H]$^+$. $^1$H NMR (400 MHz, Dimethylsulfoxide-$d_6$) δ 8.67 (s, 11H), 8.27 (d, J=8.4 Hz, 1H), 8.07-7.97 (m, 4H), 7.49-7.39 (m, 7H), 7.15 (dd, J=7.6, 1.6 Hz, 1H), 7.00 (br s, 2H), 6.44-6.38 (m, 1H), 4.28 (s, 4H), 3.64 (s, 2H), 3.40 (s, 4H).

Example 304: 4-(4-(4-(2-(2-Aminopyridin-3-yl)-5-(2-chlorophenyl)-3H-imidazo[4,5-b]pyridin-3-yl)benzyl)piperazin-1-yl)-1,3,5-triazine-2-carbonitrile

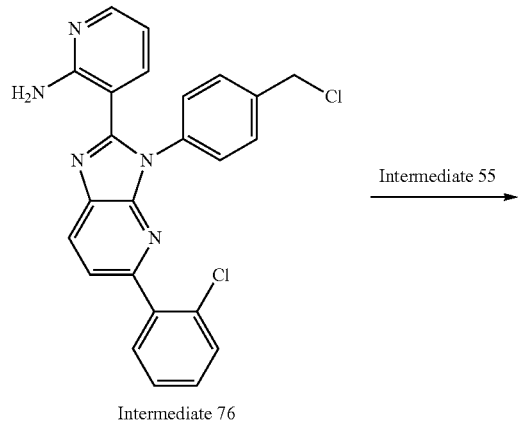

Intermediate 76

→ Intermediate 55

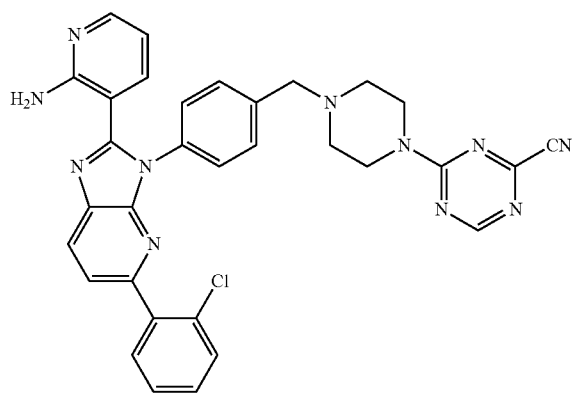

Example 304

To a solution of Intermediate 76 (300 mg, 621 μmol) and Intermediate 55 (189 mg, 621 mol) in DMF (2 mL) were added NaI (46.6 mg, 310 μmol) and K₂CO₃ (429 mg, 3.11 mmol). The mixture was stirred at 50° C. for 2 hr. The reaction mixture was filtered and the residue was purified by prep-HPLC (column: [water (NH₄HCO₃)-ACN]; B %: 47%-77%, 14 min) to give 4-(4-(4-(2-(2-aminopyridin-3-yl)-5-(2-chlorophenyl)-3H-imidazo[4,5-b]pyridin-3-yl)benzyl)piperazin-1-yl)-1,3,5-triazine-2-carbonitrile (Example 304, 102 mg, yield: 25%) as a yellow solid. MS: m/z=600.4 [M+H]⁺. ¹H NMR (400 MHz, Dimethylsulfoxide-d₆) δ 8.71 (s, 1H), 8.29 (d, J=8.0 Hz, 1H), 8.02-7.98 (m, 1H), 7.63 (d, J=8.4 Hz, 1H), 7.58-7.53 (m, 2H), 7.47-7.43 (m, 6H), 7.16 (dd, J=7.6, 1.2 Hz, 1H), 6.95 (br s, 2H), 6.39 (dd, J=7.6, 4.8 Hz, 1H), 3.85-3.77 (m, 4H), 3.60 (s, 2H), 2.60-2.54 (m, 4H).

Example 305: 4-((1-(4-(2-(2-Aminopyridin-3-yl)-5-(2-chlorophenyl)-3H-imidazo[4,5-b]pyridin-3-yl)benzyl)piperidin-4-yl)amino)pyrimidine-2-carbonitrile

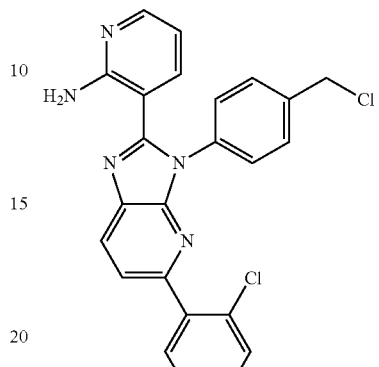

Intermediate 76

→ Intermediate 51

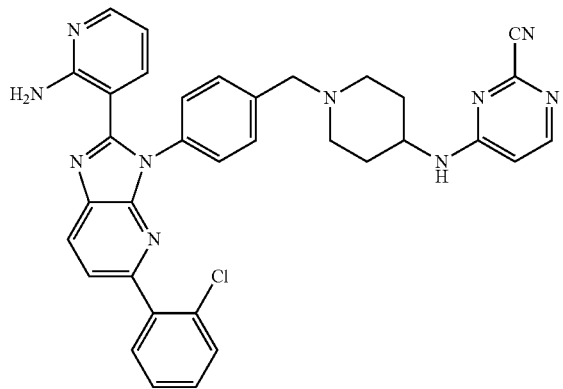

Example 305

To a solution of Intermediate 76 (250 mg HCl salt, 517 μmol) and Intermediate 51 (164 mg TFA salt, 517 μmol) in DMF (2 mL) were added NaI (15.5 mg, 103 gmol) and K₂CO₃ (357 mg, 2.59 mmol). The mixture was stirred at 50° C. for 1 hr. The reaction mixture was diluted with water (10 mL) and extracted with EtOAc (10 mL×2). The combined organic layers were washed with brine (10 mL), dried over Na₂SO₄, filtered and concentrated under reduced pressure. The residue was purified by silica gel flash chromatography (Eluent of 0~7% MeOH in CH₂Cl₂) to give 4-((1-(4-(2-(2-aminopyridin-3-yl)-5-(2-chlorophenyl)-3H-imidazo[4,5-b]pyridin-3-yl)benzyl)piperidin-4-yl)amino)pyrimidine-2-carbonitrile (Example 305, 45.4 mg, yield: 14%,) as a yellow solid. MS: m/z=613.4 [M+H]⁺. ¹H NMR (400 MHz, Dimethylsulfoxide-d₆) δ 8.29 (d, J=8.4 Hz, 1H), 8.11-7.98 (m, 3H), 7.63 (d, J=8.0 Hz, 1H), 7.59-7.52 (m, 2H), 7.46-7.40 (m, 6H), 7.16 (d, J=7.2 Hz, 1H), 6.97 (br s, 2H), 6.66 (d, J=6.0 Hz, 1H), 6.38 (dd, J=7.6, 4.8 Hz, 1H), 3.86-3.72 (m, 1H), 3.54 (s, 2H), 2.79 (m, 2H), 2.19-2.06 (m, 2H), 1.86 (m, 2H), 1.54-1.39 (m, 2H).

Example 306: 2-((1-(4-(2-(2-Aminopyridin-3-yl)-5-(2-chlorophenyl)-3H-imidazo[4,5-b]pyridin-3-yl)benzyl)piperidin-4-yl)amino)pyrimidine-4-carbonitrile

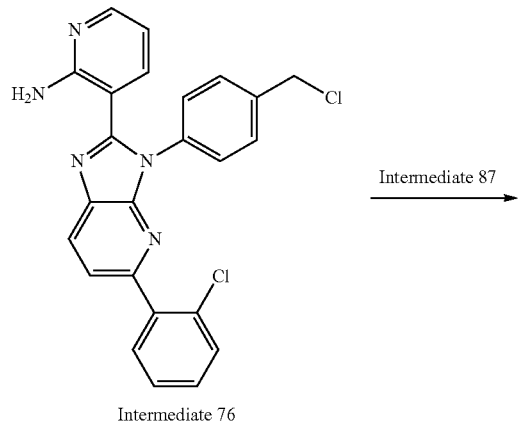

Intermediate 76 → Intermediate 87

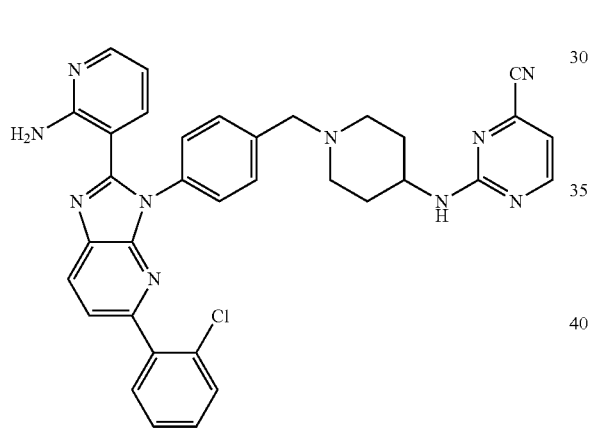

Example 306

To a solution of Intermediate 76 (200 mg, 414 μmol) and Intermediate 87 (131 mg, 414 μmol) in DMF (3 mL) were added NaI (31.1 mg, 207 μmol) and K₂CO₃ (286 mg, 2.07 mmol). The mixture was stirred at 50° C. for 0.5 hr. The reaction mixture was filtered. The residue was purified by prep-HPLC (column: Waters xbridge 150*25 mm*10 μm; mobile phase: [water (NH₄HCO₃)-ACN]; gradient: B: 50%-70% 14 min) to give 2-((1-(4-(2-(2-aminopyridin-3-yl)-5-(2-chlorophenyl)-3H-imidazo[4,5-b]pyridin-3-yl)benzyl)piperidin-4-yl)amino)pyrimidine-4-carbonitrile (Example 306, 45 mg, yield: 17%) as a light-yellow solid. MS: m/z=613.3 [M+H]⁺. ¹H NMR (400 MHz, Dimethylsulfoxide-d₆) δ 8.61 (d, J=4.8 Hz, 1H), 8.29 (d, J=8 Hz, 1H), 8.00 (d, J=4.8 Hz, 1H), 7.63 (d, J=8.4 Hz, 1H), 7.57-7.37 (m, 9H), 7.21 (d, J=7.6 Hz, 1H), 7.09 (d, J=4.4 Hz, 1H), 6.96 (br s, 2H), 6.40 (dd, J=7.6, 4.8 Hz, 1H), 4.42-4.33 (m, 2H), 3.82 (s, 2H), 3.37-3.35 (m, 2H), 3.17-3.09 (m, 2H), 2.78-2.70 (m, 1H), 1.93-1.86 (m, 2H).

Example 307: 6-((1-(4-(2-(2-Aminopyridin-3-yl)-5-(2-chlorophenyl)-3H-imidazo[4,5-b]pyridin-3-yl)benzyl)piperidin-4-yl)amino)pyrimidine-4-carbonitrile

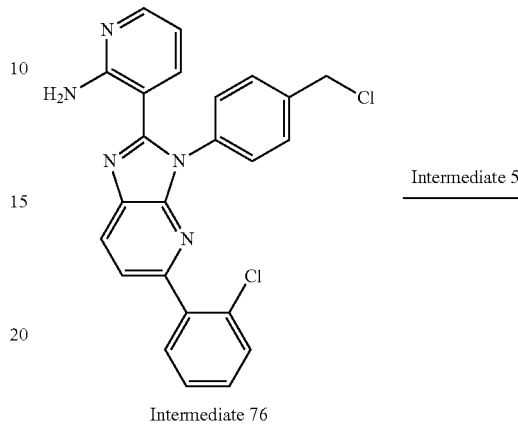

Intermediate 76 → Intermediate 52

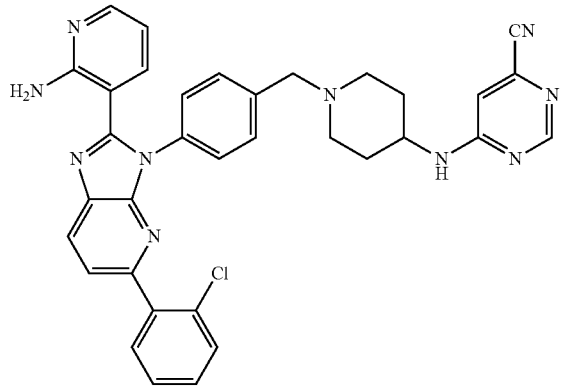

Example 307

To a solution of Intermediate 76 (200 mg, 414 μmol, HCl) and Intermediate 52 (131 mg, 414 μmol, TFA) in DMF (3 mL) were added NaI (31.1 mg, 207 μmol) and K₂CO₃ (286 mg, 2.07 mmol). The mixture was stirred at 50° C. for 1 hr. After cooling to 25° C., the reaction mixture was diluted with H₂O (20 mL) and extracted with EtOAc (15 mL×2). The combined organic layers were washed with brine (30 mL), dried over anhydrous Na₂SO₄, filtered and concentrated under reduced pressure. After purified by prep-HPLC (column: Waters xbridge 150×25 mm 10 μm; mobile phase: [water (NH₄HCO₃)-ACN]; gradient: 45%-75% B over 14 min), 6-((1-(4-(2-(2-aminopyridin-3-yl)-5-(2-chlorophenyl)-3H-imidazo[4,5-h]pyridin-3-yl)benzyl)piperidin-4-yl)amino)pyrimidine-4-carbonitrile (Example 307, 43.3 mg, yield: 17%) was obtained as a yellow solid. MS: m/z=613.4 [M+H]⁺. ¹H NMR (400 MHz, Dimethylsulfoxide-d₆) δ 8.49 (s, 1H), 8.29 (d, J=8.4 Hz, 1H), 8.06 (d, J=6.8 Hz, 1H), 8.00 (dd, J=5.2, 2.0 Hz, 1H), 7.63 (d, J=8.4 Hz, 1H), 7.58-7.53 (m, 2H), 7.45-7.42 (m, 6H), 7.16 (dd, J=7.6, 2.0 Hz, 1H), 6.97 (br s, 2H), 6.92 (s, 1H), 6.38 (dd, J=7.6, 4.8 Hz, 1H), 3.93-3.75 (m, 1H), 3.54 (s, 2H) 2.85-2.75 (m, 2H), 2.16-2.07 (m, 2H), 1.93-1.84 (m, 2H), 1.52-1.43 (m, 2H).

Example 308: 4-((1-(4-(2-(2-Aminopyridin-3-yl)-5-(4-chlorophenyl)-3H-imidazo[4,5-b]pyridin-3-yl)benzyl)piperidin-4-yl)amino)pyrimidine-2-carbonitrile

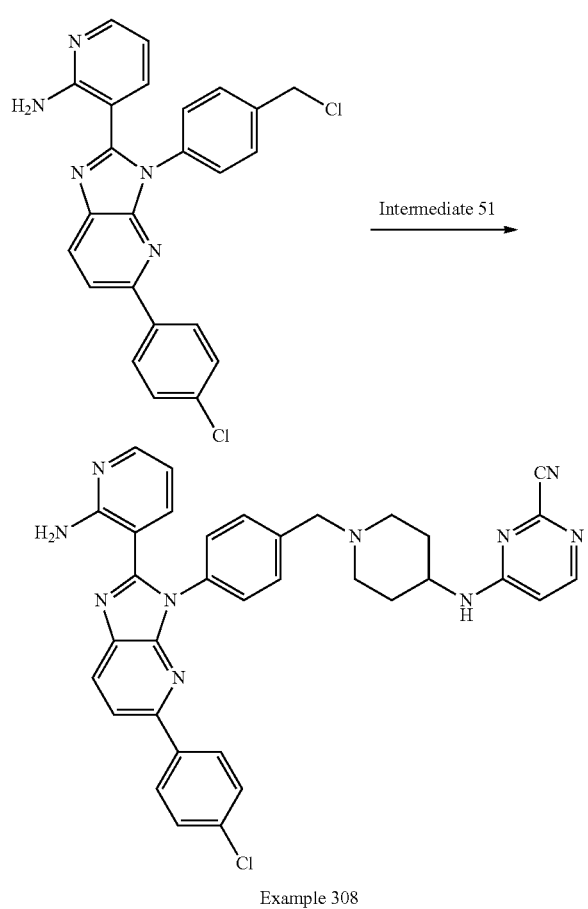

Example 308

To a solution of 3-(3-(4-(chloromethyl)phenyl)-5-(4-chlorophenyl)-3H-imidazo[4,5-b]pyridin-2-yl)pyridin-2-amine (refer to Intermediate 43 for detail procedures, 250 mg, 518 μmol) and Intermediate 51 (164 mg, 518 μmol) in DMF (2 mL) were added NaI (15.5 mg, 104 gmol) and K$_2$CO$_3$ (358 mg, 2.59 mmol). The mixture was stirred at 50° C. for 1 hr. The reaction mixture was diluted with water (10 mL) and extracted with EtOAc (10 mL×2). The combined organic layers were washed with brine (10 mL), dried over Na$_2$SO$_4$, filtered and concentrated under reduced pressure. The residue was purified by silica gel flash chromatography (Eluent of 0~7% MeOH in CH$_2$Cl$_2$) to give 4-((1-(4-(2-(2-aminopyridin-3-yl)-5-(4-chlorophenyl)-3H-imidazo[4,5-b]pyridin-3-yl)benzyl)piperidin-4-yl)amino)pyrimidine-2-carbonitrile (Example 308, 40.6 mg, yield: 12%) as a yellow solid. MS: m/z=613.2 [M+H]$^+$. $^1$H NMR (400 MHz, Dimethylsulfoxide-d$_6$) δ 8.28 (d, J=8.4 Hz, 1H), 8.11-7.98 (m, 6H), 7.54-7.44 (m, 6H), 7.15 (dd, J=7.6, 1.6 Hz, 1H), 7.03 (br s, 2H), 6.68 (d, J=6.0 Hz, 1H), 6.37 (dd, J=7.6, 4.8 Hz, 1H), 3.88-3.75 (m, 1H), 3.59 (s, 2H), 2.87-2.79 (d, J=11.2 Hz, 2H), 2.16 (m, 2H), 1.90 (d, J=11.2 Hz, 2H), 1.56-1.43 (m, 2H).

Example 309: 2-(4-(4-(2-(2-Aminopyridin-3-yl)-5-(3-fluorophenyl)-3H-imidazo[4,5-b]pyridin-3-yl)benzyl)piperazin-1-yl)pyrimidine-4-carbonitrile

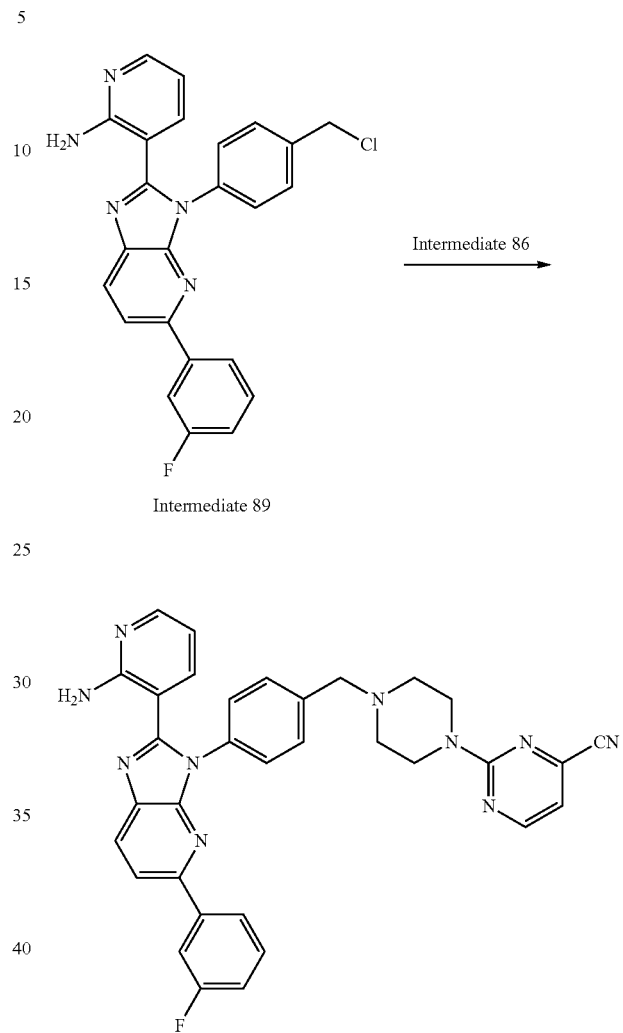

Example 309

To a solution of Intermediate 89 (200 mg, 429 μmol) and Intermediate 86 (130 mg, 429 μmol) in DMF (2 mL) were added NaI (32.1 mg, 214 μmol) and K$_2$CO$_3$ (296 mg, 2.14 mmol). The mixture was stirred at 50° C. for 0.5 hr. The reaction mixture was filtered. The residue was purified by prep-HPLC (column: Waters xbridge 150*25 mm*10 μm; mobile phase: [water (NH$_4$HCO$_3$)-ACN]; gradient: 54%-74% B over 14 min) to give 2-(4-(4-(2-(2-aminopyridin-3-yl)-5-(3-fluorophenyl)-3H-imidazo[4,5-b]pyridin-3-yl)benzyl)piperazin-1-yl)pyrimidine-4-carbonitrile (Example 309, 51.5 mg, yield: 20%) as a light-yellow solid. MS: m/z=583.4 [M+H]$^+$. $^1$H NMR (400 MHz, Dimethylsulfoxide-d$_6$) δ 8.65 (d, J=4.4 Hz, 1H), 8.29 (d, J=8.4 Hz, 1H), 8.05 (d, J=8.4 Hz, 1H), 8.02-7.99 (m, 1H), 7.91 (d, J=8.0 Hz, 1H), 7.83 (d, J=10.0 Hz, 1H), 7.54-7.46 (m, 5H), 7.27-7.21 (m, 1H), 7.19-7.14 (m, 2H), 7.04 (br s, 2H), 6.38 (dd, J=8.0, 5.2 Hz, 1H), 3.83-3.75 (m, 4H), 3.65 (s, 2H), 3.38-3.33 (m, 4H). $^{19}$F NMR (400 MHz, Dimethylsulfoxide-d$_6$) δ −112.91.

Example 310: 6-(4-(4-(2-(2-Aminopyridin-3-yl)-5-(3-fluorophenyl)-3H-imidazo[4,5-b]pyridin-3-yl)benzyl)piperazin-1-yl)pyrimidine-4-carbonitrile Example 311: 6-((1-(4-(2-(2-Aminopyridin-3-yl)-5-(3-fluorophenyl)-3H-imidazo[4,5-b]pyridin-3-yl)benzyl)piperidin-4-yl)amino)pyrimidine-4-carbonitrile

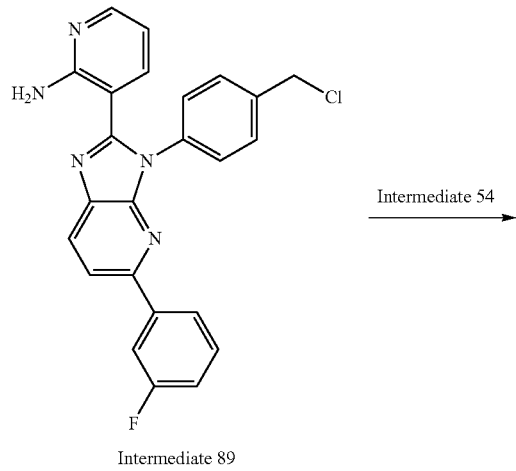

Intermediate 89

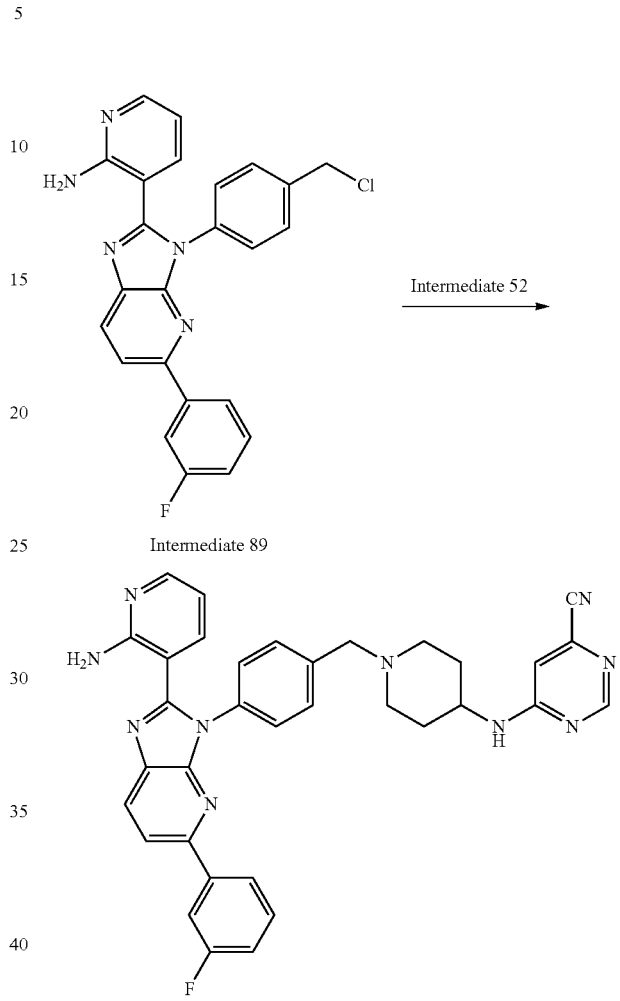

Intermediate 89

Example 310

Example 311

To a solution of Intermediate 89 (200 mg, 429 μmol) and Intermediate 54 (130 mg, 429 μmol) in DMF (3 mL) were added NaI (32.1 mg, 214 μmol) and K$_2$CO$_3$ (296 mg, 2.14 mmol). The mixture was stirred at 50° C. for 0.5 hr. The reaction mixture was filtered. The residue was purified by prep-HPLC (column: Waters xbridge 150*25 mm*10 μm; mobile phase: [water (NH$_4$HCO$_3$)-ACN]; gradient: 46%-66% B over 14 min) to give 6-(4-(4-(2-(2-aminopyridin-3-yl)-5-(3-fluorophenyl)-3H-imidazo[4,5-b]pyridin-3-yl)benzyl)piperazin-1-yl)pyrimidine-4-carbonitrile (Example 310, 24.6 mg, yield: 9.6%) as a light-yellow solid. MS: m/z=583.4 [M+H]$^+$. $^1$H NMR (400 MHz, Dimethylsulfoxide-d$_6$) δ 8.57 (s, 1H), 8.29 (d, J=8.4 Hz, 1H), 8.05 (d, J=8.4 Hz, 1H), 8.00 (dd, J=4.8, 1.6 Hz, 1H), 7.91 (d, J=7.6 Hz, 1H), 7.83 (d, J=10.4 Hz, 1H), 7.58-7.56 (m, 1H), 7.54-7.47 (m, 5H), 7.27-7.21 (m, 1H), 7.16 (dd, J=7.6, 1.6 Hz, 1H), 7.04 (br s, 2H), 6.36 (dd, J=7.6, 4.8 Hz, 1H), 3.83-3.69 (m, 4H), 3.65 (s, 2H), 3.38-3.34 (m, 2H), 3.30-3.26 (m, 2H). $^{19}$F NMR (377 MHz, Dimethylsulfoxide-d$_6$) δ −112.89.

To a solution of Intermediate 89 (200 mg, HCl salt, 429 μmol) and Intermediate 52 (87.2 mg, TFA salt, 275 μmol) in DMF (3 mL) were added NaI (32.1 mg, 214 μmol) and K$_2$CO$_3$ (296 mg, 2.14 mmol). The mixture was stirred at 50° C. for 1 hr. After cooling to room temperature, the reaction mixture was diluted with H$_2$O (20 mL) and extracted with EtOAc (15 mL×2). The combined organic layers were washed with brine (30 mL), dried over anhydrous Na$_2$SO$_4$, filtered and concentrated under reduced pressure. After purified by prep-HPLC (column: Waters xbridge 150×25 mm 10 μm; mobile phase: [water (NH$_4$HCO$_3$)-ACN]; gradient: 45%-75% B over 14 min), 6-((1-(4-(2-(2-aminopyridin-3-yl)-5-(3-fluorophenyl)-3H-imidazo[4,5-b]pyridin-3-yl)benzyl)piperidin-4-yl)amino)pyrimidine-4-carbonitrile (Example 311, 9.6 mg, yield: 3.5%) was obtained as a yellow solid. MS: m/z=597.4 [M+H]$^+$. $^1$H NMR (400 MHz, Dimethylsulfoxide-d$_6$) δ 8.51-8.42 (m, 1H), 8.29 (d, J=8.4 Hz, 1H), 8.10-8.04 (m, 2H), 8.00 (dd, J=4.8, 2.0 Hz, 1H), 7.91 (d, J=10.8 Hz, 1H), 7.84-7.81 (m, 1H), 7.52-7.45 (m, 5H), 7.25-7.16 (m, 2H), 7.04 (br s, 2H), 6.93 (s, 1H), 6.38 (dd, J=7.6, 4.8 Hz, 1H), 3.92-3.81 (m, 1H), 3.59 (s, 2H), 2.86-2.81 (m, 2H), 2.16-2.10 (m, 2H), 1.94-1.86 (m, 2H), 1.55-1.46 (m, 2H). $^{19}$F NMR (400 MHz, Dimethylsulfoxide-$d_6$) δ −112.913.

Example 312: 4-(4-(4-(2-(2-Aminopyridin-3-yl)-5-(2-fluorophenyl)-3H-imidazo[4,5-b]pyridin-3-yl)benzyl)piperazin-1-yl)-1,3,5-triazine-2-carbonitrile

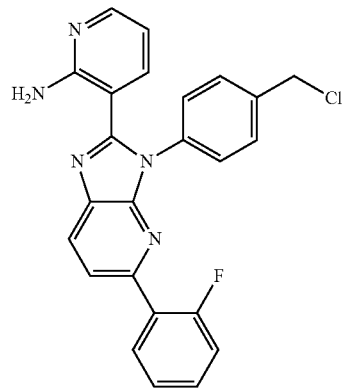

Intermediate 90

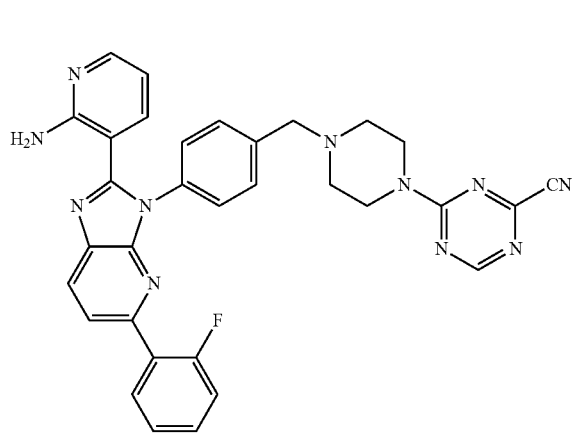

Example 312

To a solution of Intermediate 90 (300 mg, 643 μmol) and Intermediate 55 (196 mg, 643 μmol) in DMF (2 mL) were added NaI (48.2 mg, 322 μmol) and K$_2$CO$_3$ (445 mg, 3.22 mmol). The mixture was stirred at 50° C. for 2 hr. The reaction mixture was filtered and the residue was purified by prep-HPLC (column: [water (NH$_4$HCO$_3$)-ACN]; B %: 47%-77%, 14 min) to give 4-(4-(4-(2-(2-aminopyridin-3-yl)-5-(2-fluorophenyl)-3H-imidazo[4,5-b]pyridin-3-yl)benzyl)piperazin-1-yl)-1,3,5-triazine-2-carbonitrile (Example 312, 103 mg, yield: 26%) as a yellow solid. MS: m/z=584.2 [M+H]$^+$. $^1$H NMR (400 MHz, Dimethylsulfoxide-$d_6$) δ 8.72 (s, 1H), 8.30 (d, J=8.4 Hz, 1H), 8.00 (dd, J=4.8, 2.0 Hz, 1H), 7.83-7.77 (m, 2H), 7.51-7.44 (m, 5H), 7.36-7.29 (m, 2H), 7.17 (dd, J=7.6, 2.0 Hz, 1H), 6.98 (br s, 2H), 6.39 (dd, J=7.6, 4.8 Hz, 1H), 3.87-3.79 (m, 4H), 3.63 (s, 2H), 2.54-2.51 (m, 4H). $^{19}$F NMR (400 MHz, Dimethylsulfoxide-$d_6$) δ −117.168.

Example 313: 2-((1-(4-(2-(2-Aminopyridin-3-yl)-5-(2-fluorophenyl)-3H-imidazo[4,5-b]pyridin-3-yl)benzyl)piperidin-4-yl)amino)pyrimidine-4-carbonitrile

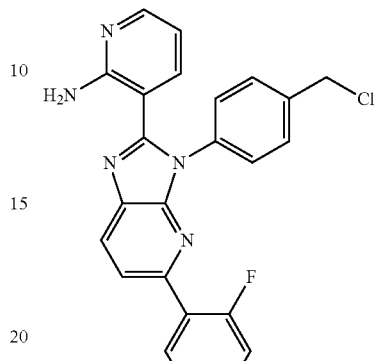

Intermediate 90

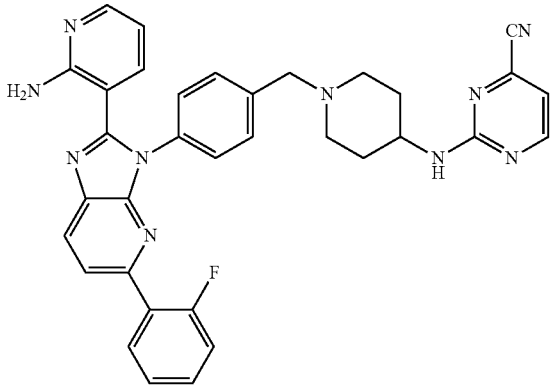

Example 313

To a solution of Intermediate 90 (193 mg, 449 μmol) and Intermediate 87 (143 mg, 702 μmol) in DMF (3 mL) were added NaI (33.7 mg, 225 μmol) and K$_2$CO$_3$ (311 mg, 2.25 mmol). The mixture was stirred at 50° C. for 0.5 hr. The reaction mixture was filtered. The residue was purified by prep-HPLC (column: Phenomenex C18 150*25 mm*10 μm; mobile phase: [water (NH$_4$HCO$_3$)-ACN]; gradient: 49%-79% B over 10 min) to give 2-((1-(4-(2-(2-aminopyridin-3-yl)-5-(2-fluorophenyl)-3H-imidazo[4,5-b]pyridin-3-yl)benzyl)piperidin-4-yl)amino)pyrimidine-4-carbonitrile (Example 313, 18.5 mg, yield: 6.8%) as a light-yellow solid. MS: m/z=597.4 [M+H]$^+$. $^1$H NMR (400 MHz, Dimethylsulfoxide-$d_6$) δ 8.61 (d, J=4.4 Hz, 1H), 8.29 (d, J=8.4 Hz, 1H), 8.00 (dd, J=4.8, 1.6 Hz, 1H), 7.83-7.77 (m, 2H), 7.52-7.39 (m, 6H), 7.35-7.29 (m, 2H), 7.20 (dd, J=7.6, 0.8 Hz, 1H), 7.10 (d, J=4.8 Hz, 1H), 6.98 (br s, 2H), 6.40 (dd, J=7.6, 5.2 Hz, 1H), 4.41-4.37 (m, 1H), 3.83 (s, 2H), 3.14 (t, J=11.2 Hz 2H), 2.81-2.70 (m, 2H), 1.93-1.87 (m, 2H), 1.30-1.23 (m, 2H). $^{19}$F NMR (377 MHz, Dimethylsulfoxide-$d_6$) δ −117.15.

Example 314: 6-(4-(4-(2-(2-Aminopyridin-3-yl)-5-(2-fluorophenyl)-3H-imidazo[4,5-b]pyridin-3-yl)benzyl)piperazin-1-yl)pyrimidine-4-carbonitrile

Example 315: 6-((1-(4-(2-(2-Aminopyridin-3-yl)-5-(2-fluorophenyl)-3H-imidazo[4,5-b]pyridin-3-yl)benzyl)piperidin-4-yl)amino)pyrimidine-4-carbonitrile

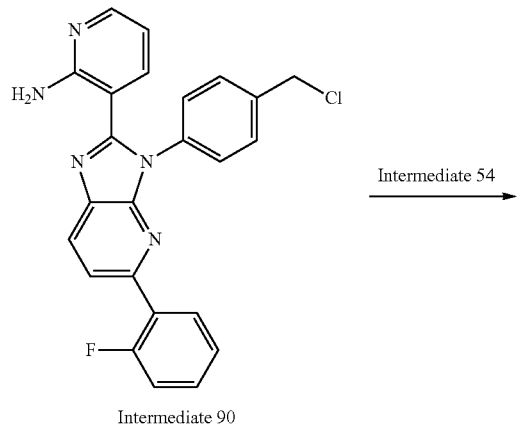

Intermediate 90

→ Intermediate 54

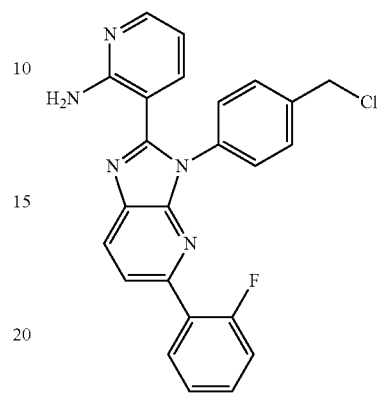

Intermediate 90

→ Intermediate 52

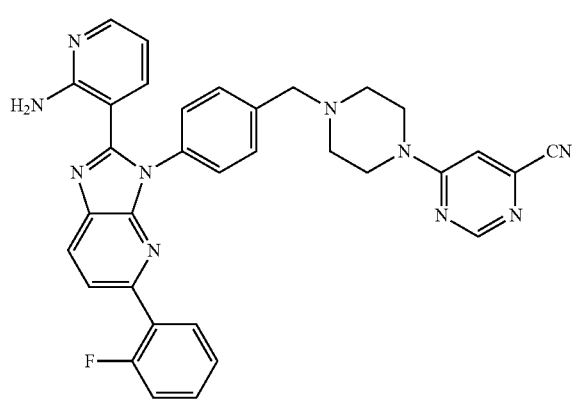

Example 314

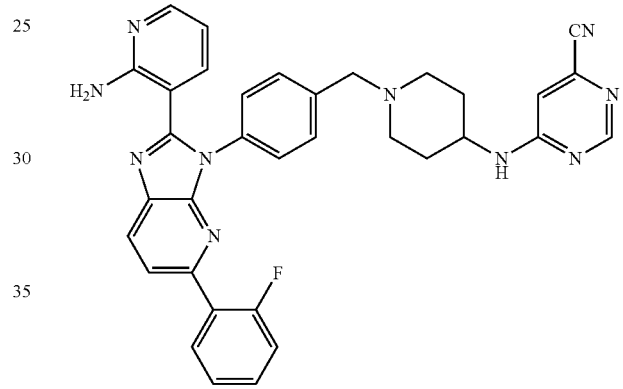

Example 315

To a solution of Intermediate 90 (200 mg, 429 µmol) and Intermediate 54 (130 mg, 429 µmol) in DMF (3 mL) were added NaI (32.1 mg, 214 µmol) and K₂CO₃ (296 mg, 2.14 mmol). The mixture was stirred at 50° C. for 0.5 hr. The reaction mixture was filtered. The residue was purified by prep-HPLC (column: Waters xbridge 150*25 mm*10 µm; mobile phase: [water (NH₄HCO₃)-ACN]; gradient: 47%-77% B over 14 min) to give 6-(4-(4-(2-(2-Aminopyridin-3-yl)-5-(2-fluorophenyl)-3H-imidazo[4,5-b]pyridin-3-yl)benzyl)piperazin-1-yl)pyrimidine-4-carbonitrile (Example 314, 46.5 mg, yield: 17%) as a light-yellow solid. MS: m/z=583.4 [M+H]⁺. ¹H NMR (400 MHz, Dimethylsulfoxide-d₆) δ 8.56 (s, 1H), 8.30 (d, J=8.4 Hz, 1H), 8.00 (d, J=4.4 Hz, 1H), 7.83-7.78 (m, 2H), 7.56 (s, 1H), 7.50-7.45 (m, 5H), 7.36-7.28 (m, 2H), 7.16 (d, J=7.6 Hz, 1H), 7.00 (br s, 2H), 6.36 (dd, J=7.6, 4.8 Hz, 1H), 3.78-3.70 (m, 4H), 3.62 (s, 2H), 2.48-2.46 (m, 4H). ¹⁹F NMR (377 MHz, Dimethylsulfoxide-d₆) δ −117.16.

To a solution of Intermediate 90 (200 mg HCl salt, 429 µmol) and Intermediate 52 (136 mg, 429 µmol, TFA) in DMF (3 mL) were added NaI (32.1 mg, 214 µmol) and K₂CO₃ (296 mg, 2.14 mmol). The mixture was stirred at 50° C. for 1 hr. After cooling to 25° C., the reaction mixture was diluted with H₂O (20 mL) and extracted with EtOAc (15 mL×2). The combined organic layers were washed with brine (30 mL), dried over anhydrous Na₂SO₄, filtered and concentrated under reduced pressure. After purified by prep-HPLC (column: Waters xbridge 150×25 mm 10 µm; mobile phase: [water (NH₄HCO₃)-ACN]; gradient: 44%-74% B over 14 min), 6-((1-(4-(2-(2-aminopyridin-3-yl)-5-(2-fluorophenyl)-3H-imidazo[4,5-b]pyridin-3-yl)benzyl)piperidin-4-yl)amino)pyrimidine-4-carbonitrile (Example 315, 15 mg, 5.6% yield) was obtained as a yellow solid. MS: m/z=597.4 [M+H]⁺. ¹H NMR (400 MHz, Dimethylsulfoxide-d₆) δ 8.52-8.42 (m, 1H), 8.29 (d, J=12.0 Hz, 1H), 8.07 (d, J=7.6 Hz, 1H), 8.00 (dd, J=4.8, 2.0 Hz, 1H), 7.83-7.78 (m, 2H), 7.48-7.43 (m, 5H), 7.35-7.29 (m, 2H), 7.16 (dd, J=7.6, 1.6 Hz, 1H), 6.99 (br s, 2H), 6.92 (s, 1H), 6.38 (dd, J=7.6, 4.8 Hz, 1H), 3.93-3.80 (m, 1H), 3.56 (s, 2H), 2.83-2.78 (m, 2H), 2.15-2.08 (m, 2H), 1.93-1.83 (m, 2H), 1.54-1.44 (m, 2H). ¹⁹F NMR (400 MHz, Dimethylsulfoxide-d₆) δ −117.177.

Example 316: 4-((1-(4-(2-(2-Aminopyridin-3-yl)-5-(2-fluorophenyl)-3H-imidazo[4,5-b]pyridin-3-yl)benzyl)piperidin-4-yl)amino)pyrimidine-2-carbonitrile

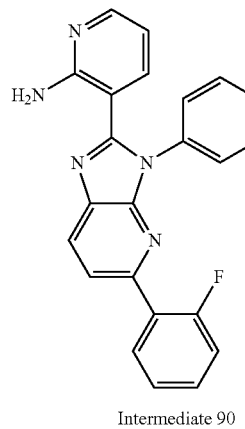

Intermediate 90

→ Intermediate 51

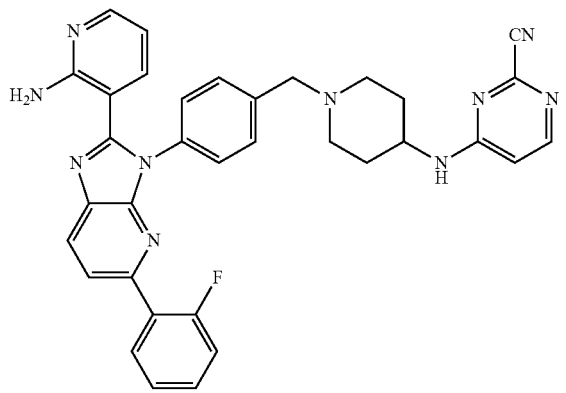

Example 316

To a solution of Intermediate 90 (250 mg HCl salt, 517 μmol) and Intermediate 51 (164 mg TFA salt, 517 μmol) in DMF (2 mL) were added NaI (15.5 mg, 103 μmol) and K₂CO₃ (357 mg, 2.59 mmol). The mixture was stirred at 50° C. for 1 hr. The reaction mixture was diluted with water (10 mL) and extracted with EtOAc (10 mL×2). The combined organic layers were washed with brine (10 mL), dried over Na₂SO₄, filtered and concentrated under reduced pressure. The residue was purified by silica gel flash chromatography (Eluent of 0~7% MeOH in CH₂C2) to give 4-((1-(4-(2-(2-aminopyridin-3-yl)-5-(2-fluorophenyl)-3H-imidazo[4,5-b]pyridin-3-yl)benzyl)piperidin-4-yl)amino)pyrimidine-2-carbonitrile (Example 316, 55.3 mg, yield: 17%,) as a yellow solid. MS: m/z=597.4 [M+H]⁺. ¹H NMR (400 MHz, Dimethylsulfoxide-d₆) δ 8.30 (d, J=8.0 Hz, 1H), 8.13-7.96 (m, 3H), 7.84-7.75 (m, 2H), 7.50-7.42 (m, 5H), 7.36-7.28 (m, 2H), 7.16 (dd, J=7.6, 1.6 Hz, 1H), 7.00 (br s, 2H), 6.67 (d, J=6.0 Hz, 1H), 6.38 (dd, J=8.0, 4.8 Hz, 1H), 3.87-3.74 (m, 1H), 3.57 (s, 2H), 2.85-2.76 (m, 2H), 2.14 (m, 2H), 1.88 (d, J=10.0 Hz, 2H), 1.54-1.41 (m, 2H). ¹⁹F NMR (400 MHz, Dimethylsulfoxide-d₆) δ −117.176.

Example 317: 4-(4-(4-(2-(2-Aminopyridin-3-yl)-5-(3-oxo-1,4-diazepan-1-yl)-3H-imidazo[4,5-b]pyridin-3-yl)benzyl)piperazin-1-yl)pyrimidine-2-carbonitrile

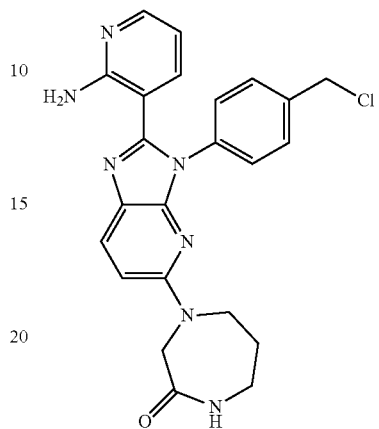

Intermediate 91

→ Intermediate 53

Example 317

To a solution of Intermediate 91 (150 mg, 335 μmol) and Intermediate 53 (117 mg, 368 μmol) in DMF (5 mL) were added NaI (10.0 mg, 66.9 μmol) and K₂CO₃ (139 mg, 1.00 mmol) in one portion at 20° C. The mixture was stirred at 20° C. for 12 hr and 80° C. for 2 hr. Water (10 mL) was added at 20° C. and extracted with EtOAc (20 mL×3). The combined organic layers were washed with water (20 mL×2), dried over anhydrous Na₂SO₄, filtered and concentrated under reduced pressure. The residue was purified by prep-HPLC (column: Phenomenex C18 75×30 mm×3 μm; mobile phase: [water (NH₃H₂O+NH₄HCO₃)-ACN]; gradient: 28%-58% B over 7 min) to give 4-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-2-carbonitrile (Example 317, 40.8 mg, yield: 20%) as a yellow solid. MS: m/z=601.2 [M+H]⁺. ¹H NMR (400 MHz, Dimethylsulfoxide-d₆) δ 8.27 (d, J=6.4 Hz, 1H), 7.97-7.92 (m, 2H), 7.47-7.42 (m, 3H), 7.35 (d, J=8.0 Hz, 2H), 7.12 (d, J=6.4 Hz, 1H), 7.02-6.79 (m, 3H), 6.80 (d, J=8.8 Hz, 1H), 6.32 (dd, J=7.6, 5.2 Hz 1H), 4.18 (s, 2H), 3.82-3.68 (m, 6H), 3.62 (s, 2H), 3.25-3.05 (m, 2H), 2.49-2.42 (m, 4H), 1.65-1.62 (m, 2H).

Example 318: 4-((1-(4-(2-(2-Aminopyridin-3-yl)-5-(3-oxo-1,4-diazepan-1-yl)-3H-imidazo[4,5-b]pyridin-3-yl)benzyl)piperidin-4-yl)amino)pyrimidine-2-carbonitrile

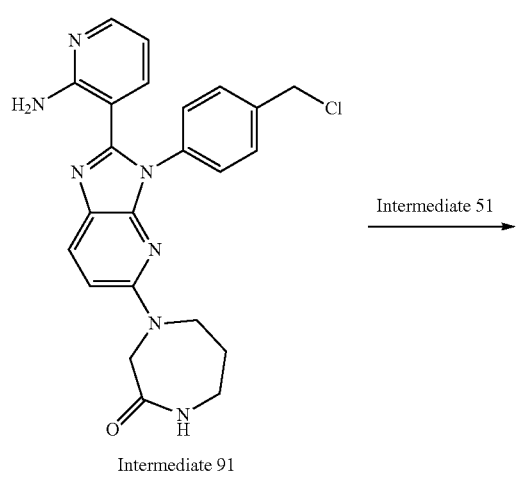

Intermediate 91

→ Intermediate 51

Example 318

To a solution of Intermediate 91 (200 mg, 447 μmol) and Intermediate 51 (99.8 mg, 491 μmol) in DMF (5 m L) were added K$_2$CO$_3$ (185 mg, 1.34 mmol) and NaI (13.4 mg, 89.3 μmol) in one portion at 20° C. The mixture was stirred at 20° C. for 12 hr. The reaction mixture was stirred at 80° C. for 2 hr. Water (10 mL) was added at 20° C. and extracted with EtOAc (20 mL×3). The combined organic layers were washed with water (20 mL×2), dried over anhydrous Na$_2$SO$_4$, filtered and concentrated under reduced pressure. The residue was purified by prep-HPLC (column: Boston Prime C18 150×30 mm×5 μm; mobile phase: [water (NH$_3$H$_2$O+NH$_4$HCO$_3$)-ACN]; gradient: 37%-67% B over 7 min) to give 4-((1-(4-(2-(2-aminopyridin-3-yl)-5-(3-oxo-1,4-diazepan-1-yl)-3H-imidazo[4,5-b]pyridin-3-yl)benzyl)piperidin-4-yl)amino)pyrimidine-2-carbonitrile (Example 318, 33.1 mg, yield: 12%) as an off-white solid. MS: m/z=615.2 [M+H]$^+$. $^1$H NMR (400 MHz, Dimethylsulfoxide-d$_6$) δ 8.09-7.95 (m, 2H), 7.94-7.92 (m, 2H), 7.46-7.43 (m, 1H), 7.41 (d, J=8.0 Hz, 2H), 7.33 (d, J=8.4 Hz, 2H), 7.02-6.99 (m, 3H), 6.80 (d, J=9.2 Hz, 1H), 6.65 (d, J=8.0 Hz, 1H), 6.34-6.30 (m, 1H), 4.17 (s, 2H), 3.83-3.75 (m, 3H), 3.56 (s, 2H), 3.19-3.15 (m, 2H), 2.82-2.78 (m, 2H), 2.16-2.09 (m, 2H), 1.89-1.86 (m, 2H), 1.68-1.62 (m, 2H), 1.49-1.45 (m, 2H).

Example 319: 2-(4-(4-(2-(2-Aminopyridin-3-yl)-5-(4-cyanophenyl)-3H-imidazo[4,5-b]pyridin-3-yl)benzyl)piperazin-1-yl)pyrimidine-4-carbonitrile

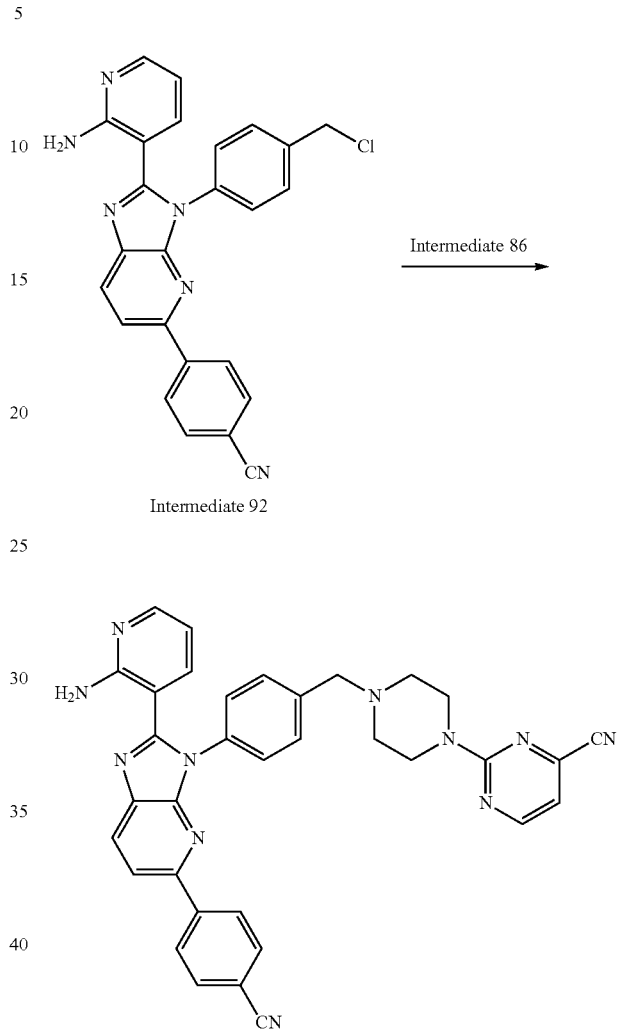

Intermediate 92

→ Intermediate 86

Example 319

To a solution of Intermediate 92 (100 mg, 229 μmol) and Intermediate 86 (43 mg, 229 μmol) in DMF (2 mL) were added K$_2$CO$_3$ (94.9 mg, 687 μmol) and NaI (6.86 mg, 45.8 μmol). The mixture was stirred at 50° C. for 0.5 hr. The reaction mixture was filtered to give a filter liquid. After purified by prep-HPLC (column: Phenomenex Cis 150×25 mm×10 μm; mobile phase: [water (NH$_4$HCO$_3$)-ACN]: B: 48%-68%, 14 min), 2-(4-(4-(2-(2-aminopyridin-3-yl)-5-(4-cyanophenyl)-3H-imidazo[4,5-b]pyridin-3-yl)benzyl)piperazin-1-yl)pyrimidine-4-carbonitrile (Example 319, 23.2 mg, yield: 17%) was obtained as a yellow solid. MS: m/z=590.2 [M+H]$^+$. $^1$H NMR (400 MHz, Dimethylsulfoxide-d$_6$) δ 8.65 (d, J=4.8 Hz, 1H), 8.34 (d, J=8.4 Hz, 1H), 8.24 (d, J=8.4 Hz, 2H), 8.13 (d, J=8.4 Hz, 1H), 8.01 (dd, J=4.8, 2.0 Hz, 1H), 7.94 (d, J=8.4 Hz, 2H), 7.54-7.46 (m, 4H), 7.19-7.14 (m, 2H), 7.03 (br s, 2H), 6.38 (dd, J=7.6, 4.8 Hz, 1H), 3.84-3.78 (m, 4H), 3.64 (s, 2H), 3.30-3.29 (m, 4H).

Example 320: 4-((1-(4-(2-(2-Aminopyridin-3-yl)-5-(4-cyanophenyl)-3H-imidazo[4,5-b]pyridin-3-yl)benzyl)piperidin-4-yl)amino)pyrimidine-2-carbonitrile

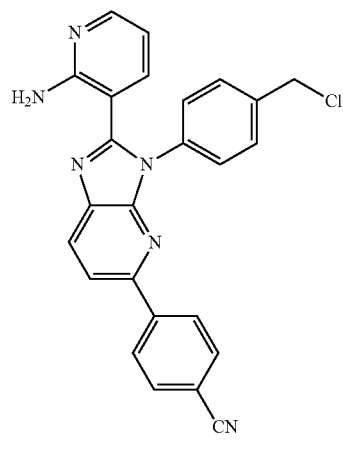

Intermediate 92

→ Intermediate 51

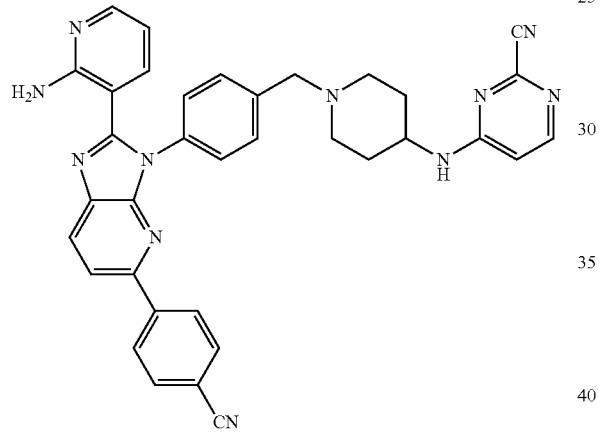

Example 320

To a solution of Intermediate 92 (100 mg, 229 μmol) and Intermediate 51 (46.5 mg, 229 μmol) in DMF (2 mL) were added K$_2$CO$_3$ (94.9 mg, 687 μmol) and NaI (6.86 mg, 45.8 μmol). The mixture was stirred at 50° C. for 0.5 hr. The reaction mixture was filtered. After purified by prep-HPLC (column: Phenomenex Luna C18 150×25 mm×10 μm; mobile phase: [water (HCl)-ACN]; gradient: 15%-45% B over 14 min), the preparation solution was diluted with H$_2$O (10 mL) and adjust pH=7 with NaHCO$_3$, and then extracted with CH$_2$Cl$_2$ (5 mL×2). The combined organic layers were washed with aqueous brine (15 mL), dried over Na$_2$SO$_4$, filtered and concentrated under reduced pressure to give 4-((1-(4-(2-(2-aminopyridin-3-yl)-5-(4-cyanophenyl)-3H-imidazo[4,5-b]pyridin-3-yl)benzyl)piperidin-4-yl)amino)pyrimidine-2-carbonitrile (Example 320, 42.6 mg, yield: 30%) as a yellow solid. MS: m/z=604.2 [M+H]$^+$. $^1$H NMR (400 MHz, Methanol-d$_4$) δ 8.27-8.22 (m, 3H), 8.05 (d, J=8.4 Hz, 1H), 8.03-7.97 (m, 2H), 7.79 (d, J=8.8 Hz, 2H), 7.56 (d, J=8.4 Hz, 2H), 7.46 (d, J=8.4 Hz, 2H), 7.34 (dd, J=7.6, 1.6 Hz 1H), 6.65-6.57 (m, 1H), 6.48 (dd, J=7.6, 5.2 Hz, 1H), 4.02-3.92 (m, 1H), 3.68 (s, 2H), 3.03-2.95 (m, 2H), 2.33-2.25 (m, 2H), 2.03-2.00 (m, 1H), 1.69-1.54 (m, 3H).

Example 321: 2-((1-(4-(2-(2-Aminopyridin-3-yl)-5-(4-cyanophenyl)-3H-imidazo[4,5-b]pyridin-3-yl)benzyl)piperidin-4-yl)amino)pyrimidine-4-carbonitrile

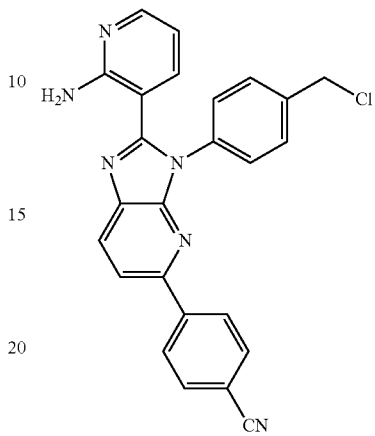

Intermediate 92

→ Intermediate 87

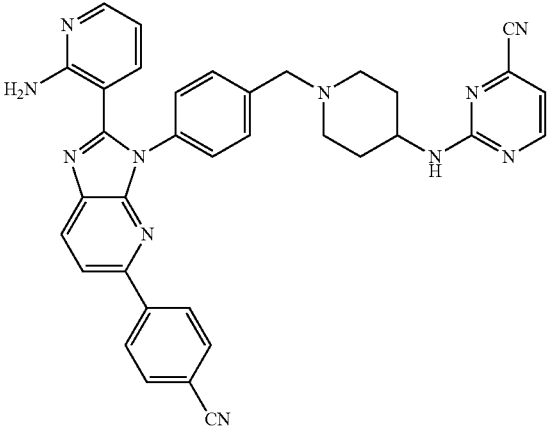

Example 321

To a solution of Intermediate 92 (100 mg, 229 μmol) and Intermediate 87 (46.5 mg, 229 μmol) in DMF (2 mL) were added K$_2$CO$_3$ (94.9 mg, 687 μmol) and NaI (6.86 mg, 45.8 μmol). The mixture was stirred at 50° C. for 0.5 hr. The reaction mixture was filtered. After purified by prep-HPLC (column: Phenomenex C$_{18}$ 150×25 mm×10 μm; mobile phase: [water (NH$_4$HCO$_3$)-ACN]: B: 43%-73%, 10 min), 2-((1-(4-(2-(2-aminopyridin-3-yl)-5-(4-cyanophenyl)-3H-imidazo[4,5-b]pyridin-3-yl)benzyl)piperidin-4-yl)amino) pyrimidine-4-carbonitrile (Example 321, 35 mg, yield: 43%) was obtained as a yellow solid. MS: m/z=604.4 [M+H]$^+$. $^1$H NMR (400 MHz, Chloroform-d) δ 8.44 (br s, 1H), 8.19-8.11 (m, 3H), 8.09 (dd, J=4.8, 1.6 Hz, 1H), 7.84 (d, J=8.4 Hz, 1H), 7.72 (d, J=8.4 Hz, 2H), 7.53 (d, J=8.4 Hz, 2H), 7.40 (d, J=8.4 Hz, 2H), 7.11 (dd, J=7.6, 1.6 Hz, 1H), 6.83 (d, J=4.8 Hz, 1H), 6.65 (br s, 2H), 6.37 (dd, J=7.6, 4.8 Hz, 1H), 5.34 (d, J=8.0 Hz, 1H), 3.98-3.84 (m, 1H), 3.65 (s, 2H), 2.94-2.88 (m, 2H), 2.36-2.23 (m, 2H), 2.14-2.05 (m, 2H), 1.68-1.62 (m, 2H).

1405

Example 322: 2-(4-(4-(2-(2-Aminopyridin-3-yl)-5-(2-cyanophenyl)-3H-imidazo[4,5-b]pyridin-3-yl)benzyl)piperazin-1-yl)pyrimidine-4-carbonitrile

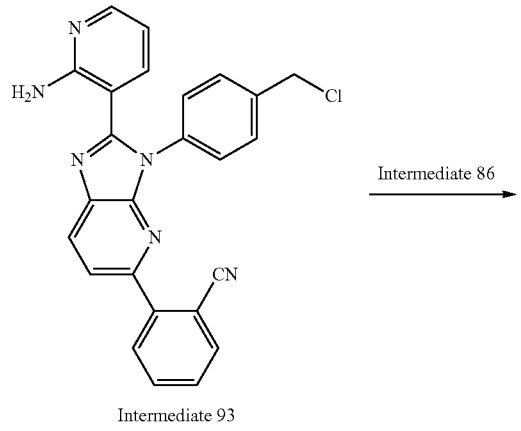

Intermediate 93

→ Intermediate 86

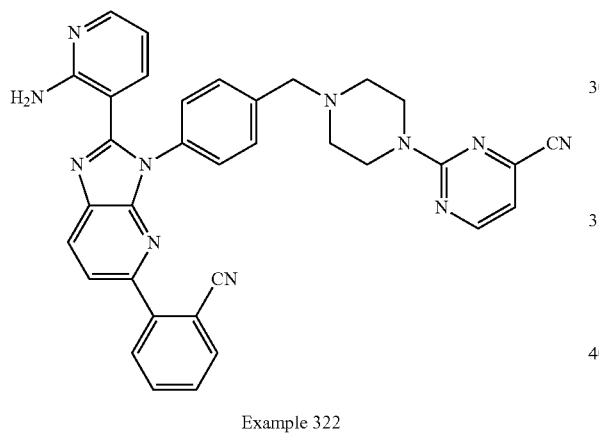

Example 322

To a solution of Intermediate 93 (200 mg, 458 μmol) and Intermediate 86 (95.3 mg, 503 μmol) in DMF (3 mL) were added NaI (13.7 mg, 91.5 μmol), K$_2$CO$_3$ (189 mg, 1.37 mmol). The mixture was stirred at 80° C. for 12 hr. The reaction mixture was filtered and purified by prep-HPLC (column: Waters xbridge 150*25 mm*10 μm; mobile phase: [water (NH$_4$HCO$_3$)-ACN]; gradient: 50%-70% B over 14 min) to give 2-(4-(4-(2-(2-aminopyridin-3-yl)-5-(2-cyanophenyl)-3H-imidazo[4,5-b]pyridin-3-yl)benzyl)piperazin-1-yl)pyrimidine-4-carbonitrile (Example 322, 81 mg, yield: 30%) as a light-yellow solid. MS: m/z=590.2 [M+H]$^+$. $^1$H NMR (400 MHz, Dimethylsulfoxide-d$_6$) δ 8.62 (d, J=4.4 Hz, 1H), 8.38 (d, J=8.0 Hz, 1H), 8.02-8.00 (m, 1H), 7.63 (d, J=7.6 Hz, 1H), 7.87-7.80 (m, 3H), 7.61-7.58 (m, 1H), 7.51-7.44 (m, 4H), 7.19-7.10 (m, 2H), 6.99 (br s, 2H), 6.40 (dd, J=7.6, 4.8 Hz, 1H), 3.76-3.74 (m, 4H), 3.46 (s, 2H), 2.50-2.46 (m, 4H).

1406

Example 323: 4-((1-(4-(2-(2-Aminopyridin-3-yl)-5-(5-oxo-1,4-diazepan-1-yl)-3H-imidazo[4,5-b]pyridin-3-yl)benzyl)piperidin-4-yl)amino)pyrimidine-2-carbonitrile

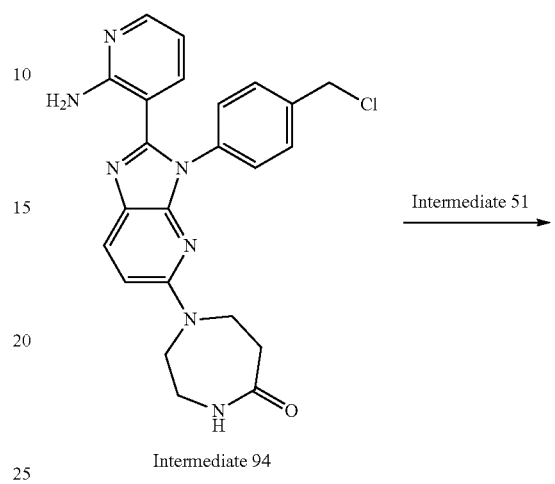

Intermediate 94

→ Intermediate 51

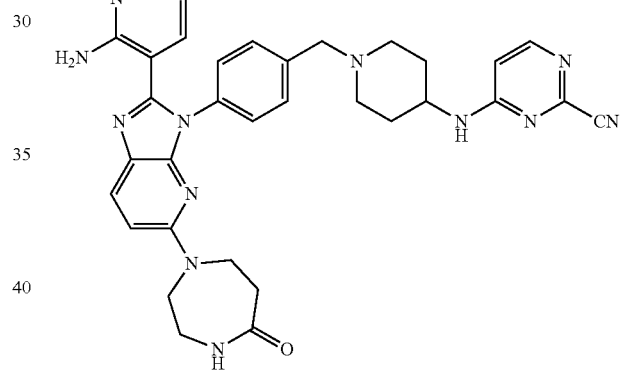

Example 323

To a solution of Intermediate 94 (52.2 mg, 116 μmol) in DMF (3 mL) were added Intermediate 51 (26.0 mg, 128 μmol) and DIEA (60.2 mg, 81 μL). The mixture was stirred at 80° C. for 12 hr and then concentrated. The residue was purified by prep-HPLC column: Boston Prime C18 150×30 mm×5 μm; mobile phase: [water (NH$_3$H$_2$O+NH$_4$HCO$_3$)-ACN]; gradient: B: 35%-65%, 7 min to give 4-((1-(4-(2-(2-aminopyridin-3-yl)-5-(5-oxo-1,4-diazepan-1-yl)-3H-imidazo[4,5-b]pyridin-3-yl)benzyl)piperidin-4-yl)amino)pyrimidine-2-carbonitrile (Example 323, 7.1 mg, yield: 9.9%) as a white solid. MS: m/z=615.5 [M+H]$^+$. $^1$H NMR (400 MHz, Dimethylsulfoxide-d$_6$) 8.92-7.81 (m, 4H), 7.59-7.55 (m, 1H), 7.51-7.22 (m, 4H), 7.14-6.94 (m, 3H), 6.87 (d, J=7.6 Hz, 1H), 6.67-6.66 (m, 1H), 6.32-6.31 (m, 1H), 3.92-3.62 (m, 5H), 3.56 (s, 2H), 3.21-3.09 (m, 2H), 2.81-2.78 (m, 2H), 2.38-2.49 (m, 2H), 2.13-2.11 (m, 2H), 1.92-1.81 (m, 2H), 1.56-1.41 (m, 2H).

1407

Example 324: 4-(4-(4-(2-(2-Aminopyridin-3-yl)-5-(2-chlorophenyl)-3H-imidazo[4,5-b]pyridin-3-yl)benzyl)piperazin-1-yl)pyrimidine-2-carbonitrile

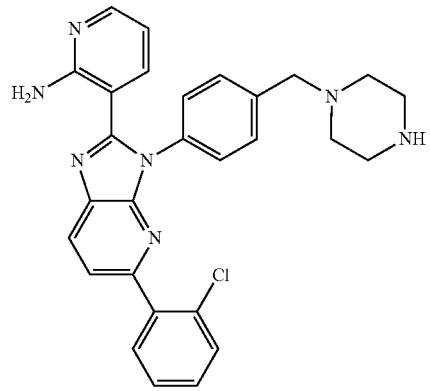

Intermedaite 77

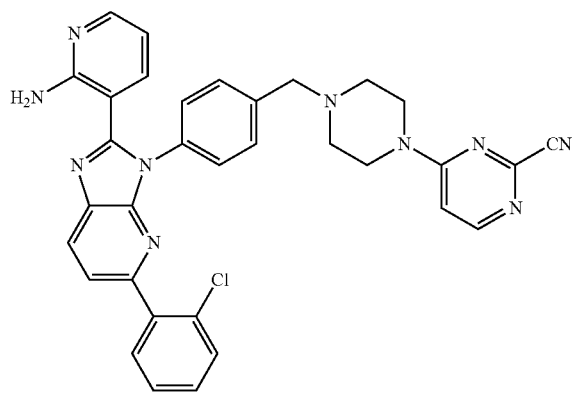

Example 324

A mixture of Intermediate 77 (28.1 mg, 202 μmol) and DIEA (52.1 mg, 403 μmol) in NMP (2 mL) were taken up into a microwave tube. The sealed tube was heated at 130° C. for 1 hr under microwave. The reaction mixture was filtered and concentrated under reduced pressure. The residue was purified by prep-HPLC (column: Waters xbridge 150*25 mm 10 μm; mobile phase: [water (NH$_4$HCO$_3$)-ACN]; gradient: 49%-79% B over 10 min) to give 4-(4-(4-(2-(2-Aminopyridin-3-yl)-5-(2-chlorophenyl)-3H-imidazo[4,5-b]pyridin-3-yl)benzyl)piperazin-1-yl)pyrimidine-2-carbonitrile (Example 324, 34 mg, 28.2% yield) as a light-yellow solid. MS: m/z=599.1 [M+H]$^+$. $^1$H NMR (400 MHz, Dimethylsulfoxide-d$_6$) δ 8.30-8.25 (m, 2H), 8.00 (dd, J=4.8, 2.0 Hz, 1H), 7.63 (d, J=8.0 Hz, 1H), 7.58-7.53 (m, 2H), 7.47-7.42 (m, 6H), 7.15 (dd, J=7.6, 2.0 Hz, 1H), 7.09 (d, J=6.4 Hz, H), 6.96 (br s, 2H), 6.37 (dd, J=7.6, 4.8 Hz, 1H), 3.72-3.58 (m, 6H), 2.49-2.46 (m, 4H).

1408

Example 325: 2-(4-(4-(2-(2-Aminopyridin-3-yl)-5-(2-chlorophenyl)-3H-imidazo[4,5-b]pyridin-3-yl)benzyl)piperazin-1-yl)pyrimidine-4-carbonitrile

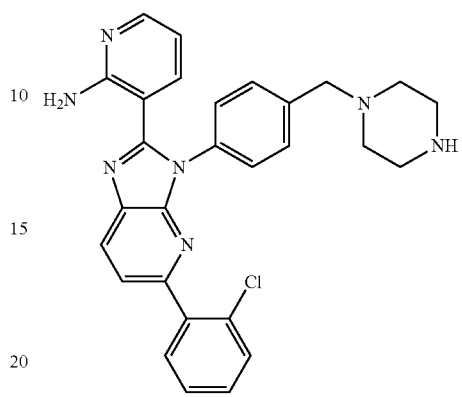

Intermediaet 77

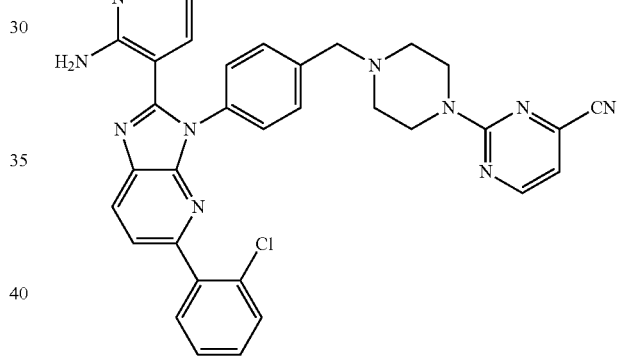

Example 325

A mixture of Intermediate 77 (100 mg, 202 μmol) and 2-chloropyrimidine-4-carbonitrile (28.1 mg, 202 μmol) and DIEA (78.2 mg, 605 μmol) in NMP (2 mL) was taken up into a microwave tube. The sealed tube was heated at 130° C. for 1 hr under microwave. The reaction mixture was filtered and purified by prep-HPLC (column: Phenomenex C$_{18}$ 150×25 mm×10 μm; mobile phase: [water (NH$_4$HCO$_3$)-ACN]; B %: 48%-78%, over 14 min) to give 2-(4-(4-(2-(2-aminopyridin-3-yl)-5-(2-chlorophenyl)-3H-imidazo[4,5-b]pyridin-3-yl)benzyl)piperazin-1-yl)pyrimidine-4-carbonitrile (Example 325, 35.8 mg, yield: 29%) as a yellow solid. MS: m/z=599.3 [M+H]$^+$. $^1$H NMR (400 MHz, Dimethylsulfoxide-d$_6$) δ 8.63 (d, J=4.8 Hz, 1H), 8.29 (d, J=8.4 Hz, 1H), 8.03-7.99 (m, 1H), 7.63 (d, J=8.4 Hz, 1H), 7.59-7.53 (m, 2H), 7.48-7.42 (m, 6H), 7.18-7.13 (m, 2H), 6.97 (br s, 2H), 6.38 (dd, J=8.0, 4.8 Hz, 1H), 3.83-3.73 (m, 4H), 3.59 (s, 2H), 2.49-2.44 (m, 4H).

Example 326: 6-(4-(4-(2-(2-Aminopyridin-3-yl)-5-(2-chlorophenyl)-3H-imidazo[4,5-b]pyridin-3-yl)benzyl)piperazin-1-yl)pyrimidine-4-carbonitrile

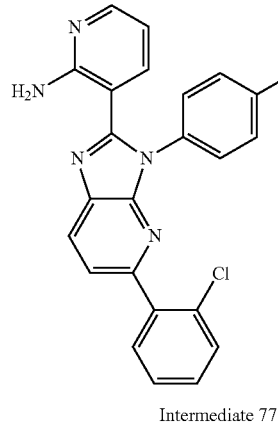

Intermediate 77

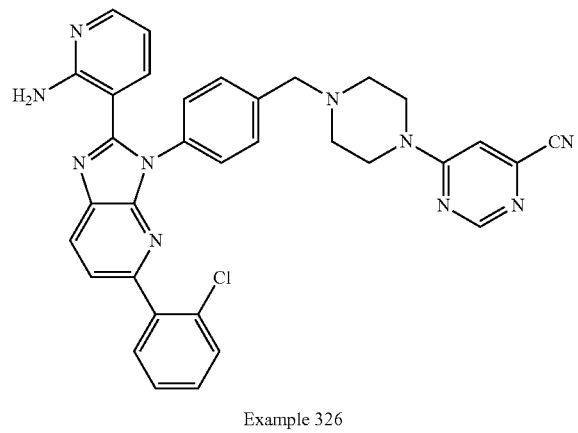

Example 326

A mixture of Intermediate 77 (100 mg, 302 µmol), 6-chloropyrimidine-4-carbonitrile (28.1 mg, 202 µmol) and DIEA (78.2 mg, 605 µmol) in NMP (2 mL) was taken up into a microwave tube. The sealed tube was heated at 130° C. for 1 hr under microwave. The reaction mixture was filtered to give a filter liquid. After purified by prep-HPLC (column: Phenomenex C18 150×25 mm×10 µm; mobile phase: [water (NH$_4$HCO$_3$)-ACN]; B %: 40%-70%, over 14 min), 6-(4-(4-(2-(2-aminopyridin-3-yl)-5-(2-chlorophenyl)-3H-imidazo[4,5-b]pyridin-3-yl)benzyl)piperazin-1-yl)pyrimidine-4-carbonitrile (Example 326, 26.4 mg, yield: 21%) was obtained as a yellow lyophilized powder. MS: m/z=599.4 [M+H]$^+$. $^1$H NMR (400 MHz, Dimethylsulfoxide-d$_6$) δ 8.55 (s, 1H), 8.29 (d, J=8.4 Hz, 1H), 8.00 (dd, J=4.8, 1.6 Hz, 1H), 7.63 (d, J=8.4 Hz, 1H), 7.59-7.53 (m, 3H), 7.48-7.41 (m, 6H), 7.16 (dd, J=7.6, 1.6 Hz, 1H), 6.97 (br s, 2H), 6.36 (dd, J=7.6, 4.8 Hz, 1H), 3.85-3.62 (m, 4H), 3.59 (s, 2H), 2.48-2.44 (m, 4H).

Example 327: 5-(4-(4-(2-(2-Aminopyridin-3-yl)-5-phenyl-3H-imidazo[4,5-b]pyridin-3-yl)benzyl)piperazine-1-carbonyl)thiazole-2-carbonitrile

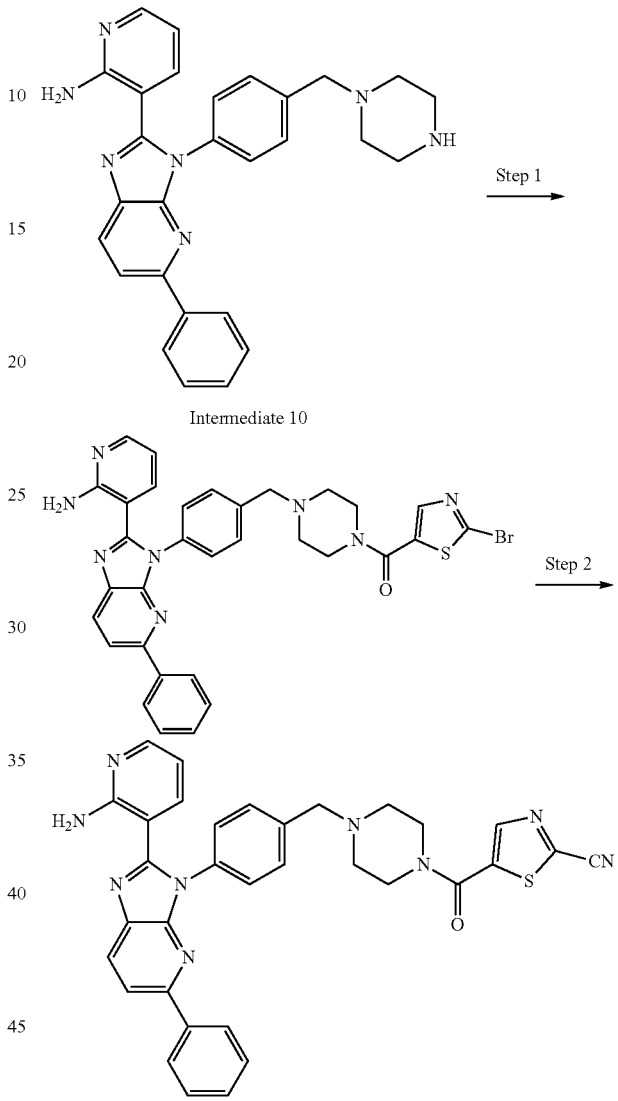

Step 1: (4-(4-(2-(2-Aminopyridin-3-yl)-5-phenyl-3H-imidazo[4,5-b]pyridin-3-yl)benzyl)piperazin-1-yl) (2-bromothiazol-5-yl)methanone To a solution of Intermediate 10 (100 mg, 217 µmol) and 2-bromothiazole-5-carboxylic acid (49.6 mg, 238 µmol) in CH$_2$Cl$_2$ (3 mL) was added HATU (98.9 mg, 260 µmol), followed by addition of DIEA (84.0 mg, 650 µmol). The resulting mixture was stirred at 25° C. for 2 hr. Then the mixture was added to water (3 mL) and extracted with EtOAc (5 mL×3). The combined organic layers were washed with brine (5 mL), dried over anhydrous Na$_2$SO$_4$, filtered and concentrated. The crude was purified by silica gel flash chromatography (Eluent of 0-8% MeOH in CH$_2$Cl$_2$) to give (4-(4-(2-(2-Aminopyridin-3-yl)-5-phenyl-

1411

3H-imidazo[4,5-b]pyridin-3-yl)benzyl)piperazin-1-yl)(2-bromothiazol-5-yl)methanone (70 mg, yield: 50%) as a yellow solid. MS: m/z=651.4, 652.3 [M+H]+. 1H NMR (400 MHz, Chloroform-d) δ 8.17 (d, J=8.0 Hz, 1H), 8.02-8.00 (m, 3H), 7.84 (d, J=8.0 Hz, 1H), 7.71 (s, 1H), 7.52-7.49 (m, 2H) 7.46-7.39 (m, 6H), 6.42 (dd, J=8.0, 5.6 Hz, 1H), 3.82-3.76 (m, 4H), 3.69 (s, 2H), 2.60-2.54 (m, 4H).

Step 2: 5-(4-(4-(2-(2-Aminopyridin-3-yl)-5-phenyl-3H-imidazo[4,5-b]pyridin-3-yl)benzyl)piperazine-1-carbonyl)thiazole-2-carbonitrile To a solution of (4-(4-(2-(2-aminopyridin-3-yl)-5-phenyl-3H-imidazo[4,5-b]pyridin-3-yl)benzyl)piperazin-1-yl)(2-bromothiazol-5-yl)methanone (100 mg, 153 μmol) in pyridine (4 mL) was added CuCN (29 mg, 322 μmol) at 25° C. The mixture was stirred at 145° C. for 6 hr. Then the mixture was filtered and concentrated under reduced pressure. The residue was purified by prep-HPLC (column: Waters xbridge 150*25 mm 10 μm; mobile phase: [water (NH4HCO3)-ACN]; gradient. 40%-70% B over 10 min) to give 5-(4-(4-(2-(2-aminopyridin-3-yl)-5-phenyl-3H-imidazo[4,5-b]pyridin-3-yl)benzyl)piperazine-1-carbonyl)thiazole-2-carbonitrile. (Example 327, 8 mg, 8.7% yield) as a light-yellow solid. MS: m/z=598.3 [M+H]+. 1H NMR (400 MHz, Acetonitrile-d3) δ 8.23-8.18 (m, 2H), 8.06-8.04 (m, 3H), 7.92 (d, J=8.0 Hz, 1H), 7.57-7.43 (m, 7H), 7.17 (dd, J=7.6, 1.6 Hz, 1H), 6.60 (b rs, 2H), 6.40 (dd, J=7.6, 4.8 Hz, 1H), 3.75-3.67 (m, 6H), 2.59-2.52 (m, 4H).

Example 328: 4-(4-(4-(2-(2-Aminopyridin-3-yl)-5-phenyl-3H-imidazo[4,5-b]pyridin-3-yl)benzyl)piperazin-1-yl)-1,3,5-triazine-2-carbonitrile

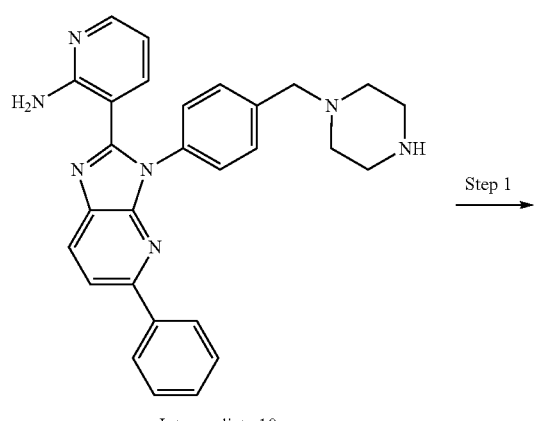

Intermediate 10

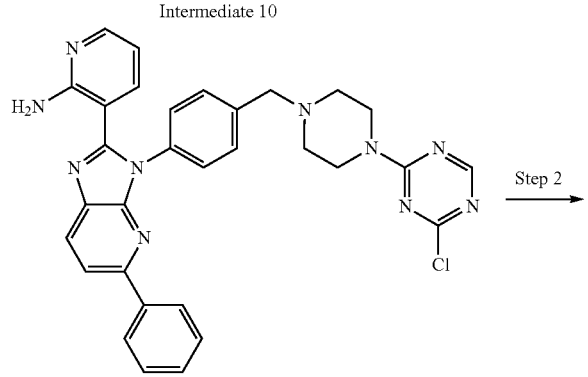

1412

-continued

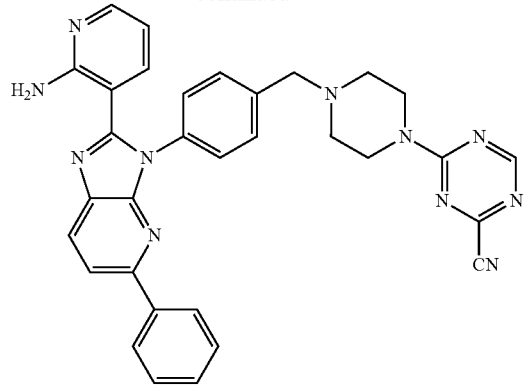

Example 328

Step 1: 3-(3-(4-((4-(4-Chloro-1,3,5-triazin-2-yl)piperazin-1-yl)methyl)phenyl)-5-phenyl-3H-imidazo[4,5-b]pyridin-2-yl)pyridin-2-amine To a solution of Intermediate 10 (200 mg, 433 μmol) in CH2Cl2 (5 mL) was added 2,4-dichloro-1,3,5-triazine (65.0 mg, 433 μmol), followed by addition of DIEA (168 mg, 1.30 mmol) at 0° C. The reaction mixture was stirred at 0° C. for 1 hr and concentrated under reduced pressure. The residue was purified by prep-TLC (CH2Cl2:MeOH=10:1) to give 3-(3-(4-((4-(4-chloro-1,3,5-triazin-2-yl)piperazin-1-yl)methyl)phenyl)-5-phenyl-3H-imidazo[4,5-b]pyridin-2-yl)pyridin-2-amine (30 mg, yield: 12%) as a white solid. MS: m/z=575.2 [M+H]+. 1H NMR (400 MHz, Chloroform-d) 8.37 (s, 1H), 8.19 (d, J=8.0 Hz, 1H), 8.01 (d, J=8.0 Hz, 2H), 7.93 (d, J=4.0 Hz, 1H), 7.85 (d, J=8.4 Hz, 1H), 7.62-7.58 (m, 2H), 7.54-7.49 (m, 1H), 7.46-7.44 (m, 4H), 7.42-7.40 (m, 1H), 6.47-6.42 (m, 1H), 4.02-3.95 (m, 4H), 3.73 (s, 2H), 2.70-2.61 (m, 4H).

Step 2: 4-(4-(4-(2-(2-Aminopyridin-3-yl)-5-phenyl-3H-imidazo[4,5-b]pyridin-3-yl)benzyl)piperazin-1-yl)-1,3,5-triazine-2-carbonitrile To a mixture of 3-(3-(4-((4-(4-chloro-1,3,5-triazin-2-yl)piperazin-1-yl)methyl)phenyl)-5-phenyl-3H-imidazo[4,5-b]pyridin-2-yl)pyridin-2-amine (30 mg, 52.2 μmol) in DMSO (1 mL) were added KCN (10 mg, 154 μmol) and DABCO (585 μg, 5.22 μmol). The mixture was stirred at 60° C. for 1 hr. H2O (20 ml) was added to the mixture and extracted with EtOAc (20 mL×3), washed with brine (20 mL), dried over Na2SO4, filtered, and concentrated and purified by prep-HPLC (column: Phenomenex C18 80×40 mm×3 μm; mobile phase: [water (NH4HCO3)-ACN]; B %: 54%-84%, 8 min) to give 4-(4-(4-(2-(2-aminopyridin-3-yl)-5-phenyl-3H-imidazo[4,5-b]pyridin-3-yl)benzyl)piperazin-1-yl)-1,3,5-triazine-2-carbonitrile (Example 328, 1.1 mg, yield: 5.5%) as a white solid. MS: m/z=566.3 [M+H]+. 1H NMR (400 MHz, Chloroform-d) 8.56 (s, 1H), 8.15 (d, J=8.0 Hz, 1H), 8.05-8.01 (m, 3H), 7.82 (d, J=8.0 Hz, 1H), 7.53-7.51 (m, 2H), 7.45-7.43 (m, 4H), 7.41-7.39 (m, 1H), 7.13 (d, J=4.0 Hz, 1H), 6.91 (br s, 2H), 6.40-6.36 (m, 1H), 3.97-3.92 (m, 4H), 3.67 (s, 2H), 2.61-2.57 (m, 4H).

Example 329: 4-(4-(4-(2-(2-Aminopyridin-3-yl)-5-(cyclohex-1-en-1-yl)-3H-imidazo[4,5-b]pyridin-3-yl)benzyl)piperazin-1-yl)pyrimidine-2-carbonitrile

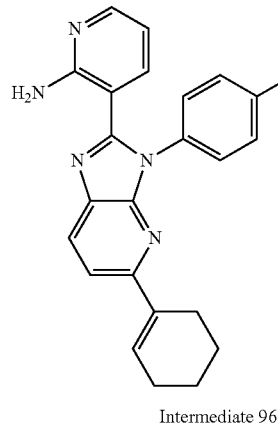

Intermediate 96

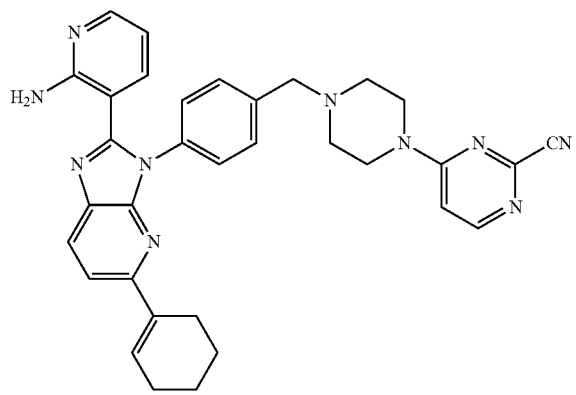

Example 329

Example 330: 4-(4-(4-(2-(2-Aminopyridin-3-yl)-5-(3,6-dihydro-2H-pyran-4-yl)-3H-imidazo[4,5-b]pyridin-3-yl)benzyl)piperazin-1-yl)pyrimidine-2-carbonitrile

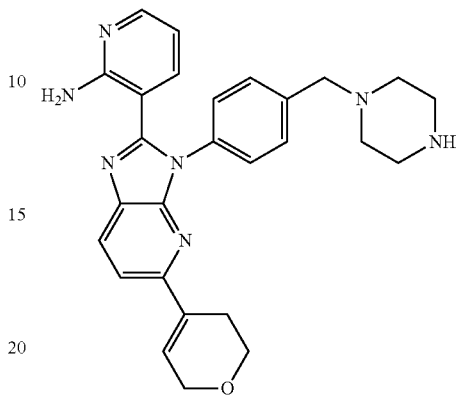

Intermediate 97

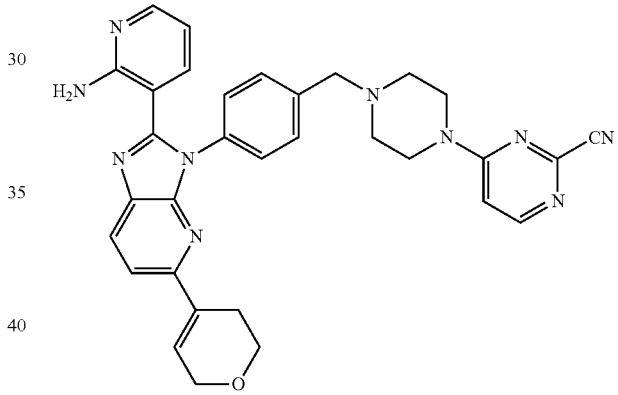

Example 330

To a solution of Intermediate 96 (100 mg, HCl salt, 199 μmol) and 4-chloropyrimidine-2-carbonitrile (27.8 mg, 199 gmol) in NMP (4 mL) was added DIEA (129 mg, 173 μL). The mixture was stirred at 160° C. for 1 hr under microwave. The mixture was quenched with water (10 mL) at 0° C. and extracted with EtOAc (20 mL×3). The combined organic phases were washed with brine (30 mL), dried over anhydrous $Na_2SO_4$, filtered and concentrated. The residue was purified by prep-HPLC (column. Phenomenex C18 75×30 mm×3 μm; mobile phase: [water ($NH_3H_2O+NH_4HCO_3$)-ACN]; gradient: 60%-90% B over 8 min) to give 4-(4-(4-(2-(2-aminopyridin-3-yl)-5-(cyclohex-1-en-1-yl)-3H-imidazo[4,5-b]pyridin-3-yl)benzyl)piperazin-1-yl)pyrimidine-2-carbonitrile (Example 329, 20.8 mg, yield: 21%) as a yellow solid. MS: m/z=569.2 [M+H]$^+$. $^1$H NMR (400 MHz, Dimethylsulfoxide-d6) δ 8.27 (d, J=6.4 Hz, 1H), 8.11 (d, J=8.0 Hz, 1H), 8.02-7.94 (m, 1H), 7.53 (d, J=8.4 Hz, 1H), 7.48 (d, J=8.0 Hz, 2H), 7.38 (d, J=8.4 Hz, 2H), 7.15-7.07 (m, 2H), 7.03 (br s, 2H), 6.68-6.60 (m, 1H), 6.34 (dd, J=7.6, 4.8 Hz, 1H), 3.77-3.57 (m, 6H), 3.31 (s, 2H), 2.45-2.39 (m, 4H), 2.20-2.18 (m, 2H), 1.72-1.56 (m, 4H).

To a solution of Intermediate 97 (100 mg, HCl salt, 198 μmol) and 4-chloropyrimidine-2-carbonitrile (27.7 mg, 198 μmol) in NP (4 mL) was added DIEA (128 mg, 992 μmol, 173 μL). The mixture was stirred at 160° C. for 1 hr under microwave. The mixture was quenched with water (10 mL) at 0° C. and then phase was extracted with EtOAc (20 mL×3). The combined organic layers were washed with brine (30 mL), dried over anhydrous $Na_2SO_4$, filtered and concentrated. The residue was purified by prep-HPLC (column: Boston Prime C18 150×30 mm×5 μm; mobile phase: [water ($NH_3H_2O+NH_4HCO_3$)-ACN]; gradient: 53%-83% B over 7 min) to give 4-(4-(4-(2-(2-aminopyridin-3-yl)-5-(3,6-dihydro-2H-pyran-4-yl)-3H-imidazo[4,5-b]pyridin-3-yl)benzyl)piperazin-1-yl)pyrimidine-2-carbonitrile. (Example 330, 18.9 mg, yield: 19%) as a yellow solid. MS: m/z=571.1 [M+H]$^+$. $^1$H NMR (400 MHz, Dimethylsulfoxide-d$_6$) δ 8.27 (d, J=6.0 Hz, 1H), 8.16 (d, J=8.4 Hz, 1H), 7.98 (dd, J=4.8, 1.6 Hz, 1H), 7.59 (d, J=8.0 Hz, 1H), 7.48 (d, J=8.4 Hz, 2H), 7.39 (d, J=8.4 Hz, 2H), 7.14-7.08 (m, 2H), 7.02 (br s, 2H), 6.69-6.68 (m, 11H), 6.35 (dd, J=7.6, 4.8 Hz, 1H), 4.28-4.22 (m, 2H), 3.80 (t, J=5.6 Hz, 2H), 3.75-3.58 (m, 6H), 3.32-3.31 (m, 6H).

Example 331: 4-(4-(4-(2-(2-Aminopyridin-3-yl)-5-(3-cyanophenyl)-3H-imidazo[4,5-b]pyridin-3-yl)benzyl)piperazin-1-yl)pyrimidine-2-carbonitrile Example 332: 4-(4-(4-(2-(2-Aminopyridin-3-yl)-5-(6-oxo-1,6-dihydropyridin-3-yl)-3H-imidazo[4,5-b]pyridin-3-yl)benzyl)piperazin-1-yl)pyrimidine-2-carbonitrile

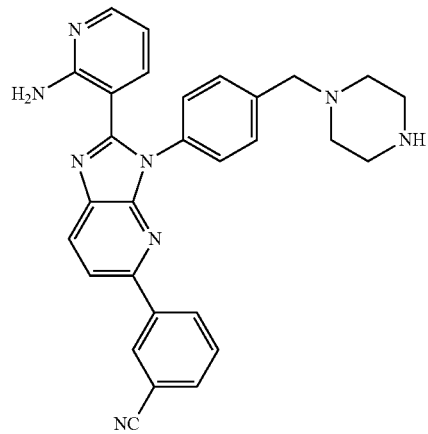

Intermediate 98

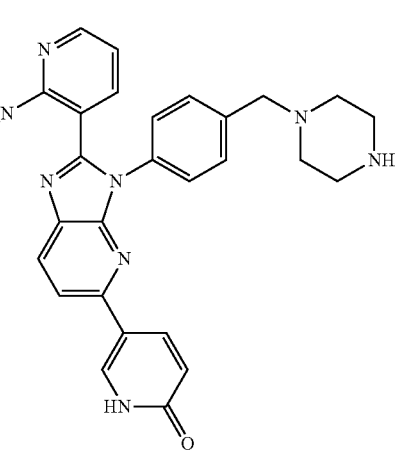

Intermediate 99

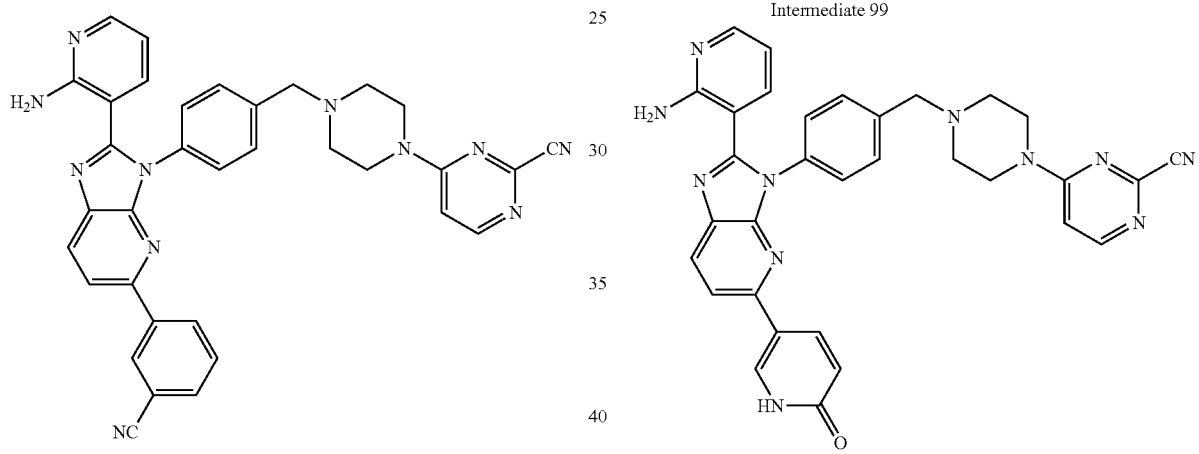

Example 331

Example 332

A mixture of Intermediate 98 (100 mg, 206 µmol), 4-chloropyrimidine-2-carbonitrile (29 mg, 210 µmol) and DIEA (136 mg, 1.05 mmol) in NMP (3 mL) was taken up into a microwave tube. The sealed tube was heated at 130° C. for 1 hr under microwave. The reaction mixture was quenched with $H_2O$ (5 mL) at 0° C. and extracted with $CH_2Cl_2$ (15 mL×2). The combined organic layers were washed with brine (15 mL), dried over $Na_2SO_4$, filtered, and concentrated under reduced pressure. After purified by prep-HPLC (column: Waters xbridge 150*25 mm 10 µm; mobile phase: [water ($NH_4HCO_3$)-ACN]; gradient: 45%-75% B over 10 min), 4-(4-(4-(2-(2-aminopyridin-3-yl)-5-(3-cyanophenyl)-3H-imidazo[4,5-b]pyridin-3-yl)benzyl)piperazin-1-yl)pyrimidine-2-carbonitrile (Example 331, 37.6 mg, yield: 29%) was obtained as a brown solid. MS: m/z=590.4 [M+H]$^+$. $^1$H NMR (400 MHz, Dimethylsulfoxide-$d_6$) δ 8.48-8.43 (m, 1H), 8.38 (d, J=8.4 Hz, 1H), 8.33 (d, J=8.4 Hz, 1H), 8.27 (d, J=6.4 Hz, 1H), 8.12 (d, J=8.4 Hz, 1H), 8.01 (dd, J=4.8, 2.0 Hz, 1H), 7.87 (d, J=7.6 Hz, 1H), 7.69 (dd, J=7.6, 7.6 Hz, 1H), 7.54-7.47 (m, 4H), 7.16 (dd, J=7.6, 1.6 Hz, 1H), 7.11 (d, J=6.8 Hz, 1H), 7.05 (br s, 2H), 6.37 (dd, J=7.6, 4.8 Hz, 1H), 3.70-3.69 (m, 4H), 3.65 (s, 2H), 2.49-2.47 (m, 4H).

A mixture of Intermediate 99 (120 mg, 251 µmol), 4-chloropyrimidine-2-carbonitrile (35 mg, 206 µmol) and DIEA (162 mg, 1.25 mmol) in NMP (3 mL) was taken up into a microwave tube. The sealed tube was heated at 130° C. for 1 hr under microwave. The reaction mixture was quenched with $H_2O$ (5 mL) at 0° C. and extracted with $CH_2Cl_2$ (15 mL×3). The combined organic layers were washed with brine (30 mL), dried over $Na_2SO_4$, filtered and concentrated under reduced pressure. After purified by prep-HPLC (column: Waters xbridge 150*25 mm 10 µm; mobile phase: [water ($NH_4HCO_3$)-ACN]; gradient: 20%-50% B over 10 min)), 4-(4-(4-(2-(2-aminopyridin-3-yl)-5-(6-oxo-1,6-dihydropyridin-3-yl)-3H-imidazo[4,5-b]pyridin-3-yl)benzyl)piperazin-1-yl)pyrimidine-2-carbonitrile (Example 332, 16 mg, yield: 10%) was obtained as a yellow solid. MS: m/z=582.2 [M+H]$^+$. $^1$H NMR (400 MHz, Dimethylsulfoxide-$d_6$) δ 12.01-11.61 (m, 1H), 8.27 (d, J=6.0 Hz, 1H), 8.20 (d, J=8.0 Hz, 1H), 8.13 (dd, J=9.6, 2.8 Hz, 1H), 8.08-8.03 (m, 1H), 7.98 (dd, J=4.4, 1.2 Hz, 1H), 7.84 (d, J=8.4 Hz, 1H), 7.53-7.41 (m, 4H), 7.15-7.09 (m, 2H), 7.04 (br s, 2H), 6.43 (d, J=9.6 Hz, 1H), 6.35 (dd, J=8.0, 5.2 Hz, 1H), 3.78-3.66 (m, 4H), 3.64 (s, 2H), 2.52-2.51 (m, 4H).

Example 333: 2-(4-(4-(2-(2-Aminopyridin-3-yl)-5-(6-oxo-1,6-dihydropyridin-2-yl)-3H-imidazo[4,5-b]pyridin-3-yl)benzyl)piperazin-1-yl)pyrimidine-4-carbonitrile Example 334: 6-(4-(4-(2-(2-Aminopyridin-3-yl)-5-(6-oxo-1,6-dihydropyridin-2-yl)-3H-imidazo[4,5-b]pyridin-3-yl)benzyl)piperazin-1-yl)pyrimidine-4-carbonitrile

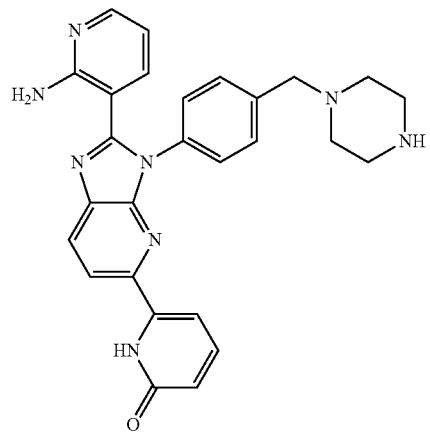

Intermediate 47

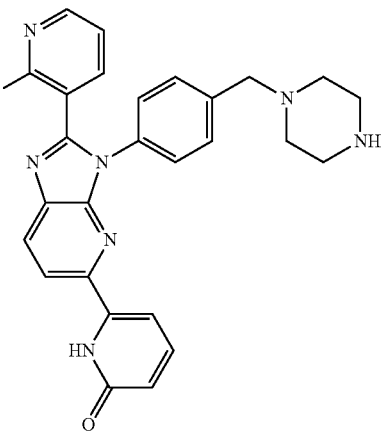

Intermediate 47

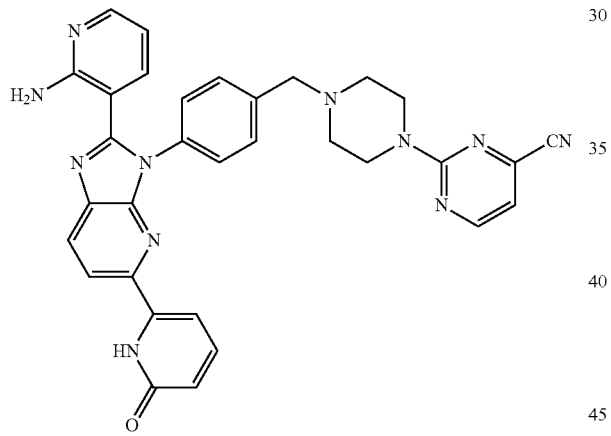

Example 333

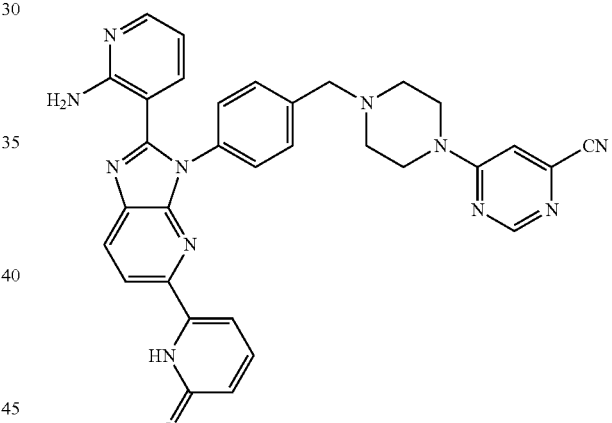

Example 334

A mixture of Intermediate 47 (149 mg, 312 μmol), 2-chloropyrimidine-4-carbonitrile (43.6 mg, 312 μmol) and DIEA (101 mg, 780 μmol) in NMP (2.5 mL) was taken up into a microwave tube. The sealed tube was heated at 130° C. for 1 hr under microwave. The reaction was filtered and concentrated under reduced pressure. The crude was purified by prep-HPLC (column: Waters xbridge 150*25 mm 10 μm; mobile phase: [water (NH$_4$HCO$_3$)-ACN]; gradient: 29%-59% B over 10 min) to give 2-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-4-carbonitrile (Example 333, 15.8 mg, yield: 8.7%) as a yellow solid. MS: m/z=582.2 [M+H]$^+$. $^1$H NMR (400 MHz, Dimethylsulfoxide-d$_6$) δ 10.81 (br s, 1H), 8.65 (d, J=4.8 Hz, 1H), 8.33 (d, J=8.4 Hz, 1H), 8.18-8.16 (m, 1H), 8.01 (dd, J=4.4, 1.2 Hz, 1H), 7.64-7.46 (m, 6H), 7.18-7.14 (m, 2H), 7.03 (br s, 2H), 6.50-6.43 (m, 1H), 6.38 (dd, J=7.6, 4.8 Hz, 1H), 3.82-3.76 (m, 4H), 3.65 (s, 2H), 2.65-2.55 (m, 4H).

A mixture of Intermediate 47 (100 mg, 209 μmol), 6-Chloropyrimidine-4-carbonitrile (29.2 mg, 209 μmol), and DIEA (67.5 mg, 522 μmol) in NMP (2 mL) was taken up into a microwave tube. The sealed tube was heated at 130° C. for 1 hr under microwave. The mixture was filtered and concentrated under reduced pressure. The crude was purified by prep-HPLC (column: Waters xbridge 150*25 mm 10 μm; mobile phase: [water (NH$_4$HCO$_3$)-ACN]; gradient: 22%-52% B over 10 min) to give 6-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-4-carbonitrile (Example 334, 50 mg, yield: 41%) as a light-yellow solid. MS: m/z=582.3 [M+H]$^+$. $^1$H NMR (400 MHz, Dimethylsulfoxide-d$_6$) δ 10.80 (br s, 1H), 8.56 (s, 1H), 8.33 (d, J=8.0 Hz, 1H), 8.20-8.14 (m, 11H), 8.00 (dd, J=4.8, 2.0 Hz, 1H), 7.64-7.46 (m, 7H), 7.15 (dd, J=7.6, 2.0 Hz, 1H), 7.03 (br s, 2H), 6.47 (d, J=8.4 Hz, 1H), 6.37 (dd, J=7.6, 4.8 Hz, 1H), 3.82-3.76 (m, 4H), 3.65 (s, 2H), 2.53-2.52 (m, 4H).

Example 335: 4-((1-(4-(2-(2-Aminopyridin-3-yl)-5-(2-cyanophenyl)-3H-imidazo[4,5-b]pyridin-3-yl)benzyl)piperidin-4-yl)amino)pyrimidine-2-carbonitrile

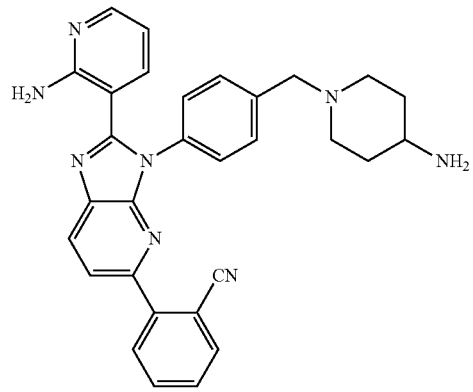

Intermediate 100

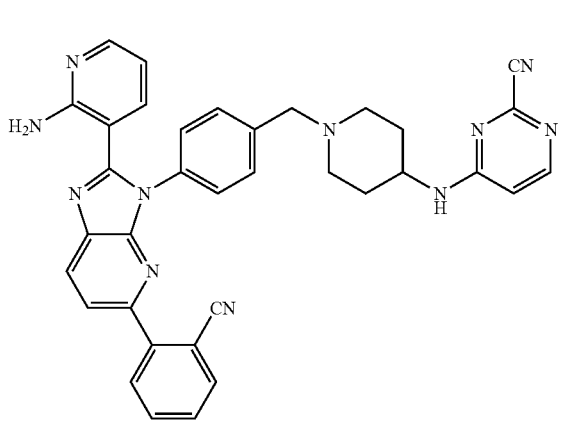

Example 335

Example 336: N-(1-(4-(2-(2-aminopyridin-3-yl)-5-phenyl-3H-imidazo[4,5-b]pyridin-3-yl)benzyl)piperidin-4-yl)-2-cyano-N-methylpyrimidine-4-carboxamide

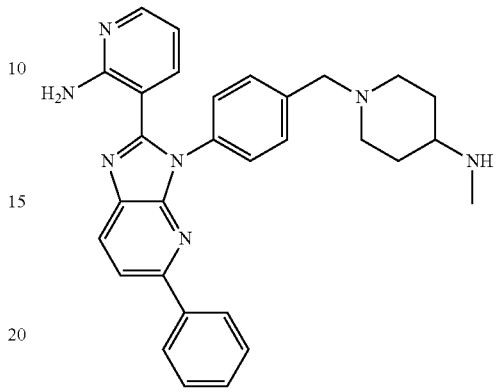

Intermediate 36

Example 336

To a solution of Intermediate 100 (80 mg, 160 μmol) in DMF (2 mL) were added 4-chloropyrimidine-2-carbonitrile (27 mg, 192 μmol), NaI (2.4 mg, 16 μmol) and $K_2CO_3$ (66 mg, 479 μmol). The mixture was stirred at 80° C. for 1 hr. The reaction mixture was poured into $H_2O$ (15 mL) and extracted with EtOAc (45 mL×2). The combined organic layers were dried over anhydrous $Na_2SO_4$, filtered and concentrated under reduced pressure. The residue was purified by silica gel flash chromatography (Eluent of 0~6% MeOH in $CH_2Cl_2$) to give 4-((1-(4-(2-(2-aminopyridin-3-yl)-5-(2-cyanophenyl)-3H-imidazo[4,5-b]pyridin-3-yl)benzyl)piperidin-4-yl)amino)pyrimidine-2-carbonitrile (Example 335, 24 mg, yield: 25%) as a yellow solid. MS: m/z=604.3 [M+H]$^+$. $^1$H NMR (400 MHz, Methanol-$d_4$) δ 8.28 (d, J=8.4 Hz, 1H), 8.08-7.95 (m, 2H), 7.91-7.78 (m, 3H), 7.75-7.71 (m, 1H), 7.57-7.50 (m, 5H), 7.39-7.29 (m, 1H), 6.66-6.54 (m, 1H), 6.53-6.42 (m, 1H), 4.07-3.89 (m, 1H), 3.73 (s, 2H), 3.07-2.95 (m, 2H), 2.43-2.29 (m, 2H), 2.02-1.94 (m, 2H), 1.67-1.56 (m, 2H).

To solution of Intermediate 36 (50 mg, 102 μmol), 2-cyanopyrimidine-4-carboxylic acid (19.8 mg, 133 μmol), EDCI (29.4 mg, 153 μmol) and HOBt (20.7 mg, 153 μmol) in $CH_2Cl_2$ (2 mL) was added DIEA (52.8 mg, 408 μmol). The mixture was stirred at 25° C. for 16 hr. The reaction mixture was diluted with $H_2O$ (10 mL) and extracted with $CH_2Cl_2$ (20 mL×2). The combined organic layers were washed with brine (10 mL), dried over $Na_2SO_4$, filtered and concentrated under reduced pressure. The crude was purified by prep-TLC ($CH_2Cl_2$:MeOH=20:1) to give N-(1-(4-(2-(2-aminopyridin-3-yl)-5-phenyl-3H-imidazo[4,5-b]pyridin-3-yl)benzyl)piperidin-4-yl)-2-cyano-N-methylpyrimidine-4-carboxamide (Example 336, 24.3 mg, yield: 38%) as a yellow solid. MS: m/z=621.3 [M+H]$^+$. $^1$H NMR (400 MHz, Dimethylsulfoxide-$d_6$) δ 9.15 (dd, J=5.2, 3.2 Hz, 1H), 8.30-8.24 (m, 1H), 8.05-7.96 (m, 5H), 7.51-7.40 (m, 7H), 7.17-7.10 (m, 1H), 7.03 (d, J=4.8 Hz, 2H), 6.42-6.31 (m, 1H), 3.61-3.51 (m, 2H), 2.95-2.77 (m, 5H), 2.19-2.11 (m, 1H), 1.91-1.84 (m, 2H), 1.70-1.63 (m, 2H), 1.36-1.07 (m, 2H).

Example 337: (R)-4-((1-(4-(2-(2-Aminopyridin-3-yl)-5-phenyl-3H-imidazo[4,5-b]pyridin-3-yl)benzyl)piperidin-3-yl)amino)-1,3,5-triazine-2-carbonitrile Example 338: 4-((1S,4S)-5-(4-(2-(2-Aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile

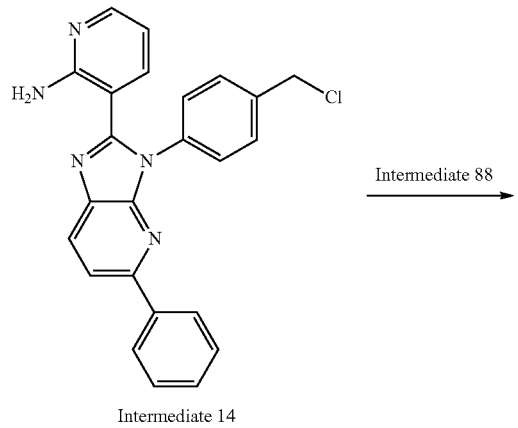

Intermediate 14

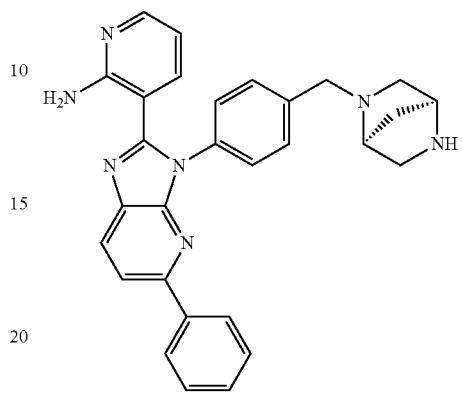

Intermediate 109

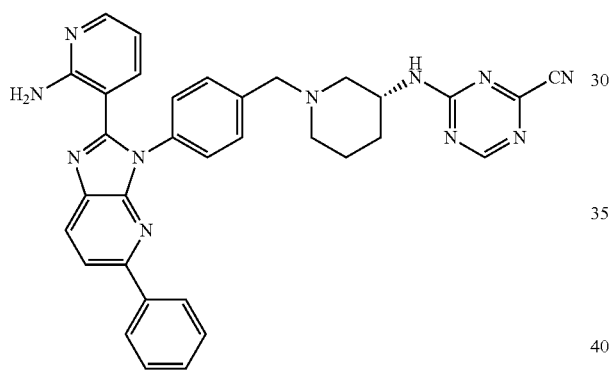

Example 337

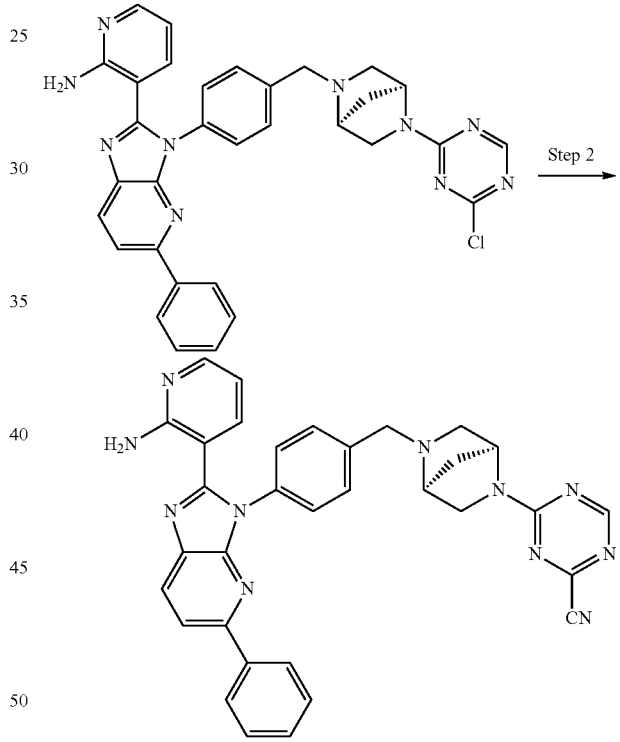

Example 338

To a solution of Intermediate 14 (180 mg, HCl salt, 401 μmol) and Intermediate 88 (127 mg TFA salt, 401 μmol) in DMF (2 mL) were added NaI (30.1 mg, 200 μmol) and $K_2CO_3$ (277 mg, 2.01 mmol). The mixture was stirred at 50° C. for 2 hr. The mixture was concentrated under reduced pressure. The residue was purified by prep-HPLC (column: [water ($NH_4HCO_3$)-ACN]; B %: 50%-80%, 14 min) to give (R)-4-((1-(4-(2-(2-aminopyridin-3-yl)-5-phenyl-3H-imidazo[4,5-b]pyridin-3-yl)benzyl)piperidin-3-yl)amino)-1,3,5-triazine-2-carbonitrile (Example 337, 75.8 mg, yield: 32%) as a yellow solid. MS: m/z=580.4 [M+H]$^+$. $^1$H NMR (400 MHz, Dimethylsulfoxide-$d_6$) δ 8.87 (br s, 1H), 8.63 (d, J=16.8 Hz, 1H), 8.27 (d, J=8.4 Hz, 1H), 8.25-7.97 (m, 4H), 7.52-7.38 (m, 7H), 7.13 (d, J=7.6 Hz, 1H), 7.04 (d, J=7.6 Hz, 2H), 6.33-6.27 (m, 1H), 4.08-3.88 (m, 1H), 3.62 (d, J=8.0 Hz, 2H), 2.93-2.86 (m, 1H), 2.75-2.69 (m, 1H), 2.05-1.95 (m, 3H), 1.88-1.82 (m, 1H), 1.76-1.69 (m, 1H), 1.59-1.49 (m, 1H).

Step 1: 3-(3-(4-(((1S,4S)-5-(4-Chloro-1,3,5-triazin-2-yl)-2,5-diazabicyclo[2.2.1]heptan-2-yl)methyl)phenyl)-5-phenyl-3H-imidazo[4,5-b]pyridin-2-yl)pyridin-2-amine To a solution of Intermediate 109 (80.0 mg, 169 μmol) and 2,4-dichloro-1,3,5-triazine (27.8 mg, 186 μmol) in THF (5 mL) and $H_2O$ (1 mL) was added DIEA (109 mg, 845 μmol). The mixture was stirred at 0° C. for 1 hr. The mixture was quenched with water (10 mL) and extracted with EtOAc (10 mL×3). The combined organic layers were dried over anhydrous $Na_2SO_4$, filtered and concentrated to give 3-(3-

(4-(((1S,4S)-5-(4-Chloro-1,3,5-triazin-2-yl)-2,5-diazabicyclo[2.2.1]heptan-2-yl)methyl)phenyl)-5-phenyl-3H-imidazo[4,5-b]pyridin-2-yl)pyridin-2-amine (99.2 mg) as a yellow solid, which was used in the next step without further purification. MS: m/z=587.1 [M+H]⁺.

Step 2: 4-((1S,4S)-5-(4-(2-(2-Aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile To a solution of 3-(3-(4-(((3-(4-chloro-1,3,5-triazin-2-yl)-3,8-diazabicyclo[3.2.1]octan-8-yl)methyl)phenyl)-5-phenyl-3H-imidazo[4,5-b]pyridin-2-yl)pyridin-2-amine (70 mg, 119 μmol) in DMSO (1 mL) were added KCN (15.5 mg, 238 μmol) and DABCO (2.67 mg, 23.8 mol). The mixture was stirred at 25° C. for 16 hr. The reaction was filtered and concentrated under reduced pressure. The mixture was quenched with H₂O (10 mL) and extracted with EtOAc (10 mL×3). The combined organic layers were dried over anhydrous Na₂SO₄, filtered and concentrated. The residue was purified by prep-TLC (CH₂Cl₂:MeOH=10:1) to give 4-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile (Example 338, 3.4 mg, yield: 5%) as a yellow solid. MS: m/z=578.3 [M+H]⁺. ¹H NMR (400 MHz, Chloroform-d) δ 8.54 (d, J=18.4 Hz, 1H), 8.13 (d, J=8.0 Hz, 1H), 8.06 (d, J=4.4 Hz, 1H), 8.01 (d, J=7.2 Hz, 2H), 7.80 (d, J=8.4 Hz, 1H), 7.51-7.38 (m, 7H), 7.10 (dd, J=7.6, 1.6 Hz, 1H), 6.65 (br s, 2H), 6.39-6.35 (m, 1H), 4.97-4.95 (m, 1H), 3.87 (s, 2H), 3.85-3.82 (m, 1H), 3.74-3.72 (m, 1H), 3.49-3.43 (m, 1H), 3.08-3.04 (m, 1H), 2.76-2.68 (m, 1H), 2.21-2.14 (m, 1H), 1.89-1.85 (m, 1H).

Example 339: 4-((3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile

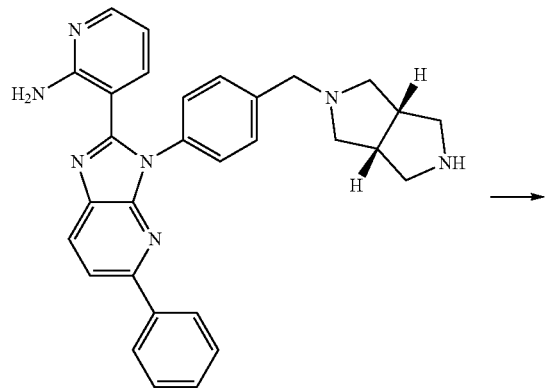

Intermediate 101

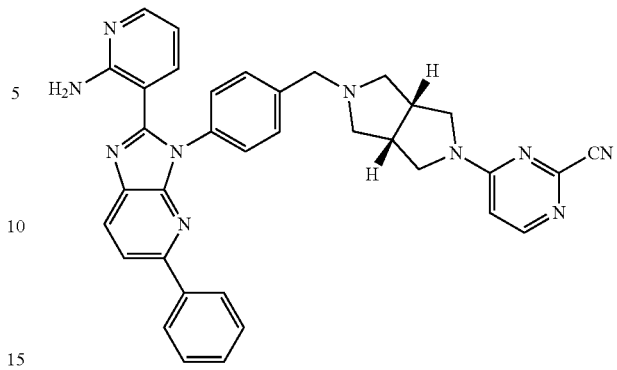

Example 339

A mixture of Intermediate 101 (100 mg, 205 μmol), 4-chloropyrimidine-2-carbonitrile (28.6 mg, 205 μmol), and DIEA (79.5 mg, 107.17 μL) in NMP (1 mL) was taken up into a microwave tube. The sealed tube was heated at 160° C. for 1 hr under microwave. Water (10 mL) was added to the mixture, and the mixture was extracted with EtOAc (20 mL×2). The combined organic layers were washed with brine (10 mL), dried over anhydrous Na₂SO₄, filtered and concentrated. The residue was purified by silica gel flash chromatography (Eluent of 0~10% MeOH in CH₂Cl₂) and purified by prep-HPLC (column: Boston Prime C18 150×30 mm×5 μm; mobile phase: [water (NH₃H₂O+NH₄HCO₃)-ACN]; gradient: 66%-96% B over 7 min) to give 4-((3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile (Example 339, 8.7 mg, 7.2% yield) as a yellow solid. MS: m/z=591.2 [M+H]⁺. ¹H NMR (400 MHz, Dimethylsulfoxide-d₆) δ 8.38-8.16 (m, 2H), 8.09-7.90 (m, 4H), 7.53-7.33 (m, 7H), 7.15 (d, J=7.6 Hz, 1H), 7.02 (br s, 2H), 6.78 (d, J=5.6 Hz, 1H), 6.37-6.35 (m, 1H), 3.82-3.60 (m, 4H), 2.98-2.96 (m, 2H), 2.65-2.53 (m, 6H).

Example 340: 4-((3aR,6aS)-5-(4-(2-(2-Aminopyridin-3-yl)-5-phenyl-3H-imidazo[4,5-b]pyridin-3-yl)benzyl)hexahydropyrrolo[3,4-c]pyrrol-2(1H)-yl)-1,3,5-triazine-2-carbonitrile

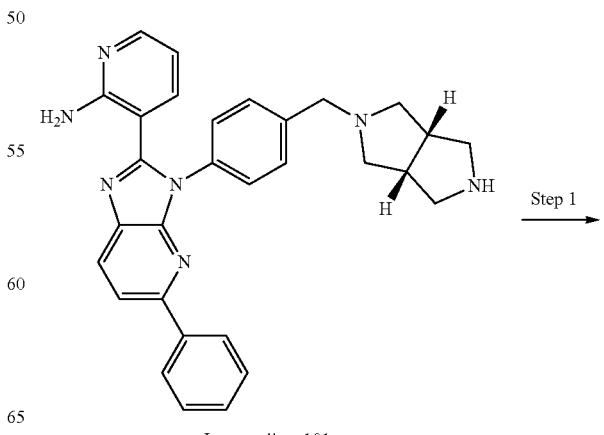

Intermediate 101

-continued

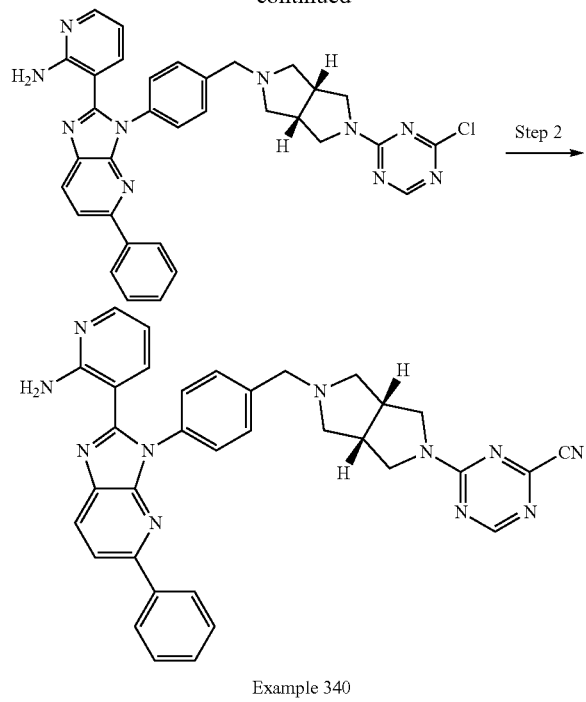

Example 340

Step 1: 3-(3-(4-(((3aR,6aS)-5-(4-Chloro-1,3,5-triazin-2-yl)hexahydropyrrolo[3,4-c]pyrrol-2(1H)-yl)methyl)phenyl)-5-phenyl-3H-imidazo[4,5-b]pyridin-2-yl)pyridin-2-amine To a solution of Intermediate 101 (200 mg, HCl salt, 382 µmol) in THF (4 mL) and H$_2$O (1 mL) were added DIEA (158 mg, 1.14 mmol) and 2,4-dichloro-1,3,5-triazine (63.0 mg, 420 µmol) at 0° C. This mixture was stirred at 0° C. for 0.5 hr. H$_2$O (5 mL) was added to the mixture. The aqueous phase was extracted with EtOAc (20 mL×3). The combined organic phases were washed with brine (30 mL), dried over anhydrous Na$_2$SO$_4$, filtered and concentrated. The residue was purified by prep-TLC (EtOAc:petroleum ether=1:0) to give 3-(3-(4-(((3aR,6aS)-5-(4-chloro-1,3,5-triazin-2-yl)hexahydropyrrolo[3,4-c]pyrrol-2(1H)-yl)methyl)phenyl)-5-phenyl-3H-imidazo[4,5-b]pyridin-2-yl)pyridin-2-amine (110 mg, yield: 48%) as a light-yellow solid. MS: m/z=601.4 [M+H]$^+$.

Step 2: 4-((3aR,6aS)-5-(4-(2-(2-Aminopyridin-3-yl)-5-phenyl-3H-imidazo[4,5-b]pyridin-3-yl)benzyl)hexahydropyrrolo[3,4-c]pyrrol-2(1H)-yl)-1,3,5-triazine-2-carbonitrile To a solution of 3-(3-(4-(((3aR,6aS)-5-(4-chloro-1,3,5-triazin-2-yl)hexahydropyrrolo[3,4-c]pyrrol-2(1H)-yl)methyl)phenyl)-5-phenyl-3H-imidazo[4,5-b]pyridin-2-yl)pyridin-2-amine (50.0 mg, 83.2 µmol) in DMSO (2 mL) was added KCN (170 mg, 2.61 mmol) and DABCO (2 mg, 16.6 µmol) at 25° C. This mixture was stirred at 25° C. for 16 hr. H$_2$O (5 mL) was added to the mixture. The aqueous phase was extracted with EtOAc (20 mL×3). The combined organic layers were washed with brine (30 mL), dried over anhydrous Na$_2$SO$_4$, filtered and concentrated. The residue was purified by prep-TLC (CH$_2$Cl$_2$:MeOH=30:1) to give 4-((3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)-1,3,5-triazine-2-carbonitrile (Example 340, 5.50 mg, yield: 11%) as an off-white solid. MS: m/z=592.4 [M+H]$^+$. $^1$H NMR (400 MHz, Methanol-d$_4$) δ 8.54 (s, 1H), 8.19 (d, J=8.8 Hz, 1H), 8.03 (d, J=7.6 Hz, 2H), 7.98 (d, J=4.8 Hz, 1H), 7.94 (d, J=8.0 Hz, 1H), 7.50 (d, J=8.0 Hz, 2H), 7.46-7.35 (m, 5H), 7.32 (d, J=7.6 Hz, 1H), 6.48 (dd, J=7.6, 5.2 Hz, 1H), 3.91-3.81 (m, 2H), 3.75-3.58 (m, 4H), 3.08-3.02 (m, 2H), 2.80-2.72 (m, 2H), 2.67-2.58 (m, 2H).

Example 341: 4-((3aR,6aR)-5-(4-(2-(2-Aminopyridin-3-yl)-5-phenyl-3H-imidazo[4,5-b]pyridin-3-yl)benzyl)hexahydropyrrolo[3,4-c]pyrrol-2(1/H)-yl)pyrimidine-2-carbonitrile

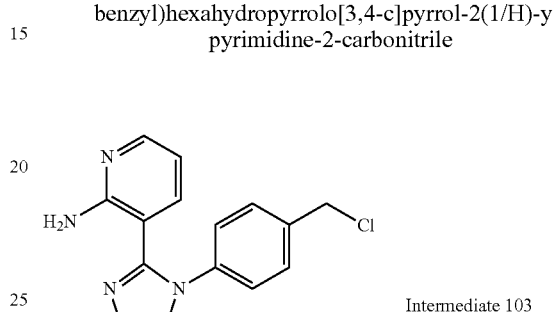

Intermediate 14

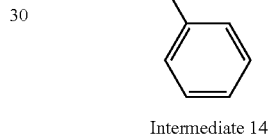

Intermediate 103

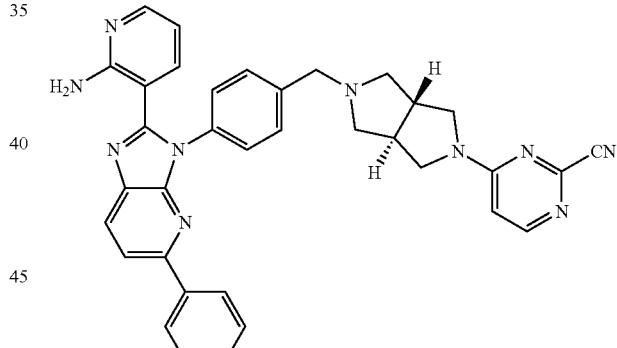

Example 341

To a mixture of Intermediate 103 (87.9 mg, TFA salt, 267 µmol) and Intermediate 14 (100 mg, 243 µmol) in DMF (1 mL) was added DIEA (126 mg, 169 µL). The mixture was stirred at 80° C. for 12 hr. The mixture was quenched with H$_2$O (50 mL) and extracted with EtOAc (30 mL×2). The combined organic layers were washed with brine (20 mL), dried over Na$_2$SO$_4$, filtered and concentrated. The mixture was purified by prep-HPLC (column: Phenomenex C18 80*40 mm*3 um; mobile phase: [water (NH$_3$H$_2$O+ NH$_4$HCO$_3$)-ACN]; gradient: 62%-92% B over 7 min) to give 4-((3aR,6aR)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile (Example 341, 25.4 mg, yield: 18%) as a yellow solid. MS: m/z=591.4 [M+H]$^+$. $^1$H NMR (400 MHz, Dimethylsulfoxide-d$_6$) 8.32-8.15 (m, 2H), 8.05-7.97 (m, 4H), 7.53-7.43 (m, 6H), 7.42-

7.37 (m, 1H), 7.17 (dd, J=7.6, 1.6 Hz, 1H), 7.02 (br s, 2H), 6.74 (d, J=6.4 Hz, 1H), 6.43-6.34 (m, 1H), 4.04-3.91 (m, 2H), 3.86-3.78 (m, 1H), 3.65-3.57 (m, 1H), 3.16-3.06 (m, 2H), 2.96-2.86 (m, 2H), 2.73-2.62 (m, 2H), 2.44-2.26 (m, 2H).

Example 342: 4-(4-(4-(2-(2-Aminopyridin-3-yl)-5-(4-chlorophenyl)-3H-imidazo[4,5-b]pyridin-3-yl)benzyl)piperazin-1-yl)pyrimidine-2-carbonitrile

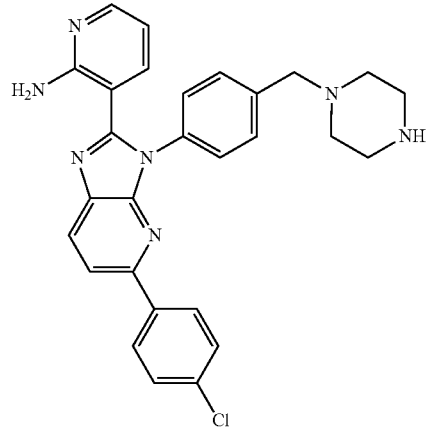

Intermediate 43

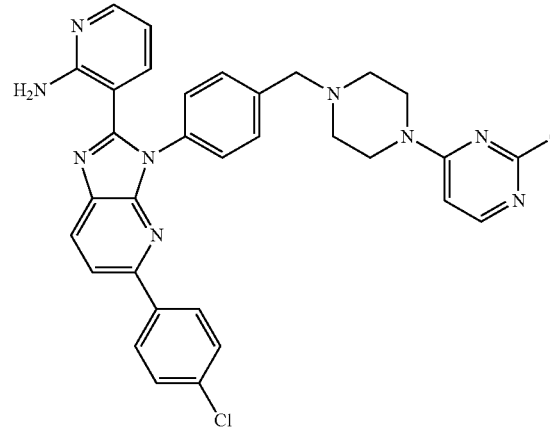

Example 342

A mixture of Intermediate 43 (100 mg, 202 μmol), 4-chloropyrimidine-2-carbonitrile (33.8 mg, 242 μmol) and DIEA (104 mg, 806 μmol) in NMP (2 mL) was taken up into a microwave tube. The sealed tube was heated at 130° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with brine (15 mL), dried over Na$_2$SO$_4$, filtered and concentrated under reduced pressure. After purified by prep-HPLC (column: Phenomenex C18 150*25 mm*10 μm; mobile phase: [water (NH$_4$HCO$_3$)-ACN]; B %: 54%-84%, over 14 min), 4-(4-(4-(2-(2-aminopyridin-3-yl)-5-(4-chlorophenyl)-3H-imidazo[4,5-b]pyridin-3-yl)benzyl)piperazin-1-yl)pyrimidine-2-carbonitrile (Example 342, 27.1 mg, yield: 22%) was obtained as a purple lyophilized powder. MS: m/z=599.4 [M+H]$^+$. $^1$H NMR (400 MHz, Dimethylsulfoxide-d$_6$) δ 8.30-8.26 (m, 2H), 8.08-7.99 (m, 4H), 7.55-7.50 (m, 4H), 7.49-7.45 (m, 2H), 7.17-7.10 (m, 2H), 7.03 (br s, 2H), 6.36 (dd, J=8.0, 4.8 Hz, 1H), 3.81-3.66 (m, 4H), 3.65 (s, 2H), 2.49-2.46 (m, 4H).

Example 343: 2-(4-(4-(2-(2-Aminopyridin-3-yl)-5-(4-chlorophenyl)-3H-imidazo[4,5-b]pyridin-3-yl)benzyl)piperazin-1-yl)pyrimidine-4-carbonitrile

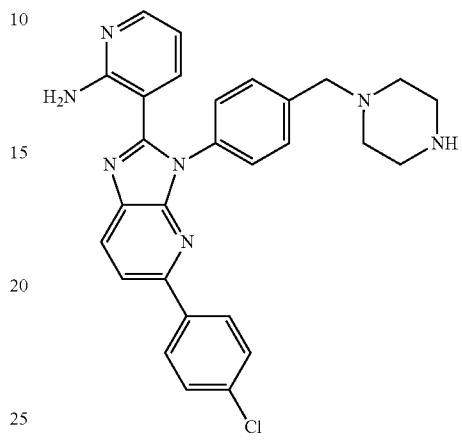

Intermediate 43

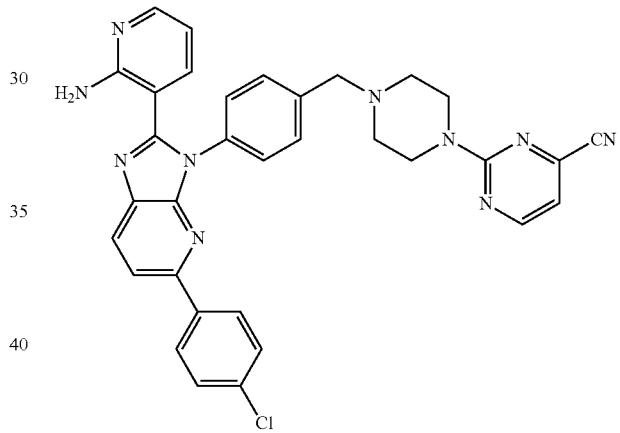

Example 343

A mixture of Intermediate 43 (150 mg, 302 μmol), 2-chloropyrimidine-4-carbonitrile (50.6 mg, 363 μmol) and DIEA (156 mg, 1.21 mmol) in NMP (2 mL) was taken up into a microwave tube. The sealed tube was heated at 130° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with brine (10 mL), dried over Na$_2$SO$_4$, filtered and concentrated under reduced pressure. After purified by prep-HPLC (column: Phenomenex C18 150*25 mm*10 μm; mobile phase: [water (NH$_4$HCO$_3$)-ACN]; B %: 55%-85%, over 10 min), 2-(4-(4-(2-(2-aminopyridin-3-yl)-5-(4-chlorophenyl)-3H-imidazo[4,5-b]pyridin-3-yl)benzyl)piperazin-1-yl)pyrimidine-4-carbonitrile (Example 343, 25.3 mg, yield: 14%) was obtained as a brown lyophilized powder. MS: m/z=599.2 [M+H]$^+$. $^1$H NMR (400 MHz, Dimethylsulfoxide-d$_6$) δ 8.65 (d, J=4.8 Hz, 1H), 8.28 (d, J=8.4 Hz, 1H), 8.08-7.99 (m, 4H), 7.55-7.50 (m, 4H), 7.49-7.44 (m, 2H), 7.18-7.12 (m, 2H), 7.03 (br s, 2H), 6.37 (dd, J=8.0, 4.8 Hz, 1H), 3.82-3.77 (m, 4H), 3.64 (s, 2H), 2.61-2.54 (m, 4H).

Example 344: 6-(4-(4-(2-(2-Aminopyridin-3-yl)-5-(4-chlorophenyl)-3H-imidazo[4,5-b]pyridin-3-yl)benzyl)piperazin-1-yl)pyrimidine-4-carbonitrile

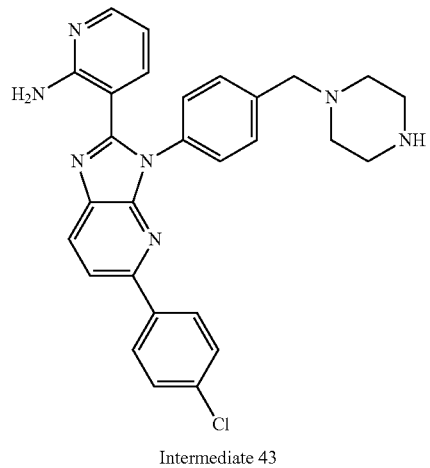

Intermediate 43

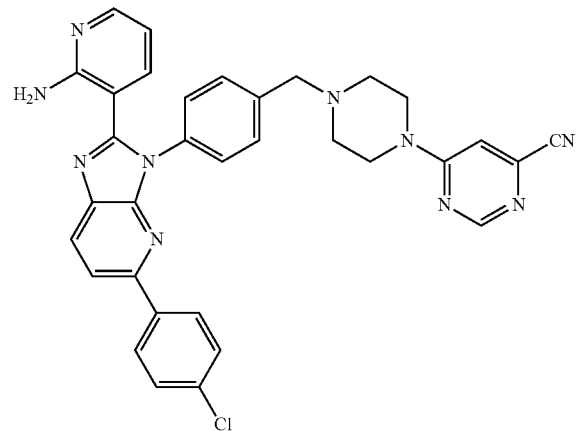

Example 344

Example 345: 4-(4-(4-(2-(2-Aminopyridin-3-yl)-5-(4-methyl-5-oxo-1,4-diazepan-1-yl)-3H-imidazo[4,5-b]pyridin-3-yl)benzyl)piperazin-1-yl)pyrimidine-2-carbonitrile

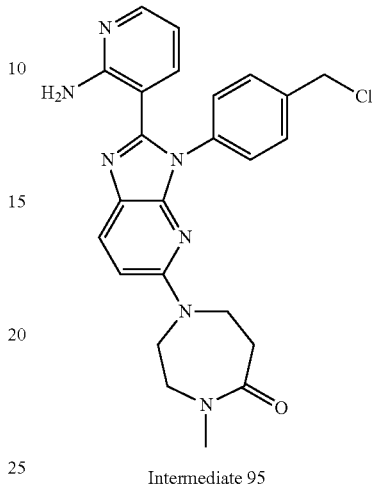

Intermediate 95

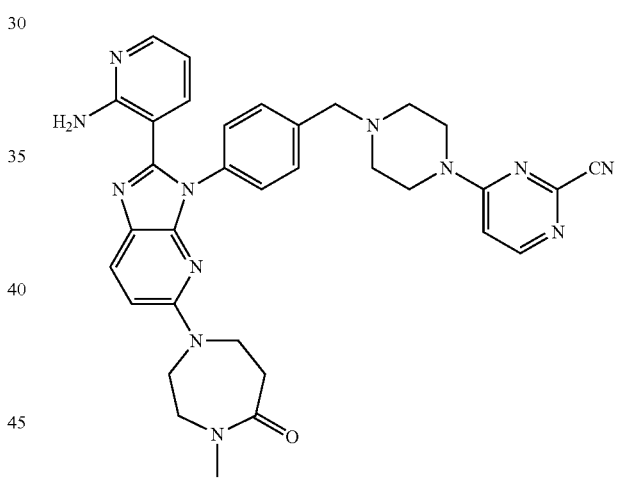

Example 345

A mixture of Intermediate 43 (150 mg, 302 μmol), 6-chloropyrimidine-4-carbonitrile (50.6 mg, 363 μmol) and DIEA (156 mg, 1.21 mmol) in NMP (2 mL) was taken up into a microwave tube. The sealed tube was heated at 130° C. for 1 hr under microwave. The reaction mixture was quenched with H$_2$O (5 mL) at 0° C., and then diluted with CH$_2$Cl$_2$ (10 mL) and extracted with CH$_2$Cl$_2$ (15 mL×2). The combined organic layers were washed with brine (15 mL), dried over Na$_2$SO$_4$, filtered and concentrated under reduced pressure. After purified by prep-HPLC (column: Phenomenex C18 150*25 mm*5 μm; mobile phase: [water (NH$_4$HCO$_3$)-ACN]; B %: 52%-82%, over 10 min), 6-(4-(4-(2-(2-aminopyridin-3-yl)-5-(4-chlorophenyl)-3H-imidazo[4,5-b]pyridin-3-yl)benzyl)piperazin-1-yl)pyrimidine-4-carbonitrile (Example 344, 29.5 mg, yield: 16%) was obtained as a brown lyophilized powder. MS: m/z=599.2 [M+H]$^+$. $^1$H NMR (400 MHz, Dimethylsulfoxide-d$_6$) δ 8.57 (s, 1H), 8.28 (d, J=8.4 Hz, 1H), 8.09-7.99 (m, 4H), 7.58-7.45 (m, 7H), 7.14 (dd, J=7.6, 1.6 Hz, 1H), 7.03 (br s, 2H), 6.35 (dd, J=7.6, 4.8 Hz, 1H), 3.87-3.66 (m, 4H), 3.64 (s, 2H), 2.49-2.44 (m, 4H).

To a solution of Intermediate 95 (85.4 mg, 185 μmol) in DMF (1 mL) were added DIEA (71.7 mg, 96.6 μL) and Intermediate 53 (38.5 mg, 203 μmol). The mixture was stirred at 80° C. for 2 hr. The mixture was filtered and concentrated under reduced pressure. After purified by prep-HPLC (column: Phenomenex C18 75×30 mm×3 um; mobile phase: [water (NH$_3$H$_2$O+NH$_4$HCO$_3$)-ACN]; gradient: 38%-68% B over 7 min), 4-(4-(4-(2-(2-aminopyridin-3-yl)-5-(4-methyl-5-oxo-1,4-diazepan-1-yl)-3H-imidazo[4,5-b]pyridin-3-yl)benzyl)piperazin-1-yl)pyrimidine-2-carbonitrile (Example 345, 10.3 mg, yield: 9.1%) was obtained as a light yellow solid. MS: m/z=615.3 [M+H]$^+$. $^1$H NMR (400 MHz, Dimethylsulfoxide-d$_6$) δ 8.27 (d, J=6.4 Hz, 1H), 7.99-7.91 (m, 2H), 7.46 (d, J=8.4 Hz, 2H), 7.33 (d, J=8.4 Hz, 2H), 7.12 (d, J=6.4 Hz, 1H), 7.05-6.98 (m, 3H), 6.90 (d, J=8.8 Hz, 1H), 6.31 (dd, J=7.6, 4.4 Hz, 1H), 3.78-3.65 (m, 9H), 3.62 (s, 2H), 3.52-3.40 (m, 2H), 2.82 (s, 3H), 2.62-2.57 (m, 5H).

Example 346: 4-((1-(4-(2-(2-Aminopyridin-3-yl)-5-(4-methyl-5-oxo-1,4-diazepan-1-yl)-3H-imidazo[4,5-b]pyridin-3-yl)benzyl)piperidin-4-yl)amino)pyrimidine-2-carbonitrile

Example 347: 2-((1-(4-(2-(2-Aminopyridin-3-yl)-5-(3-oxo-1,4-diazepan-1-yl)-3H-imidazo[4,5-b]pyridin-3-yl)benzyl)piperidin-4-yl)amino)pyrimidine-4-carbonitrile

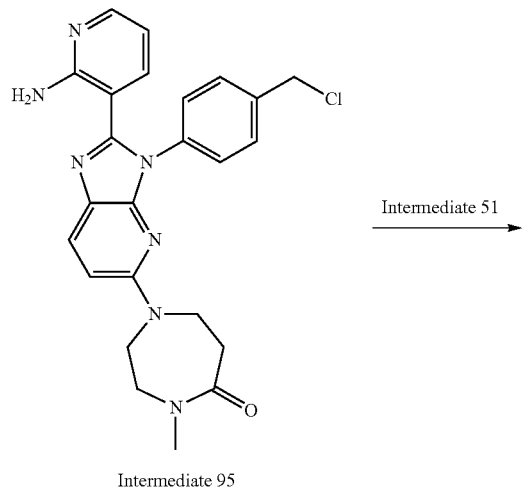

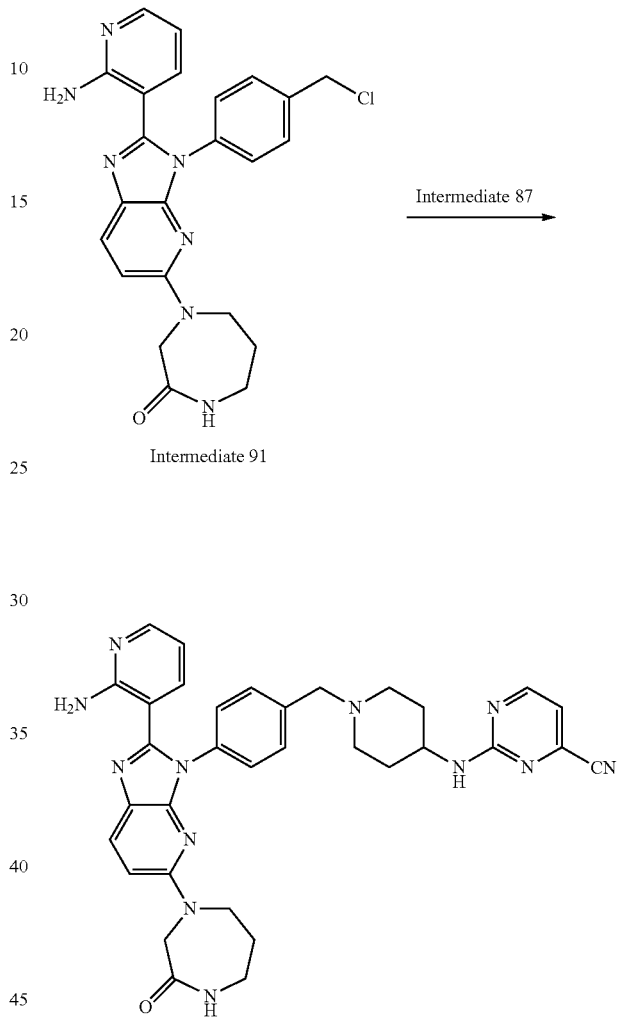

To a solution of Intermediate 95 (100 mg, 217 μmol) in DMF (2 mL) were added DIEA (83.9 mg, 113 μL) and Intermediate 51 (52.8 mg, 260 μmol). The mixture was stirred at 80° C. for 2 hr. The reaction was concentrated. Water (2 mL) was added and the aqueous was extracted with CH2Cl2 (2 mL×2). The combined organic layers were dried over anhydrous Na2SO4, filtered and concentrated. The residue was purified by prep-HPLC (column: Phenomenex C18 75×30 mm×3 μm; mobile phase: [water (NH$_3$H$_2$O+NH$_4$HCO$_3$)-ACN]; gradient: 40%-70% B over 7 min) to give 4-((1-(4-(2-(2-aminopyridin-3-yl)-5-(4-methyl-5-oxo-1,4-diazepan-1-yl)-3H-imidazo[4,5-b]pyridin-3-yl)benzyl)piperidin-4-yl)amino)pyrimidine-2-carbonitrile (Example 346, 9.4 mg, yield: 6.9%) as a light-yellow solid. MS: m/z=629.4 [M+H]$^+$. $^1$H NMR (400 MHz, Dimethylsulfoxide-d$_6$) δ 8.12-8.03 (m, 2H), 7.98-7.92 (m, 2H), 7.43 (d, J=8.0 Hz, 2H), 7.32 (d, J=8.0 Hz, 2H), 7.05-6.98 (m, 3H), 6.89 (d, J=8.8 Hz, 1H), 6.67 (d, J=6.0 Hz, 1H), 6.32 (dd, J=7.6, 4.8 Hz, 1H), 3.81-3.66 (m, 5H), 3.57 (s, 2H), 3.48-3.44 (m, 2H), 2.81-2.79 (m, 5H), 2.63-2.57 (m, 2H), 2.20-2.09 (m, 2H), 1.94-1.83 (m, 2H), 1.53-1.44 (m, 2H).

To a solution of Intermediate 87 (105 mg, 516 μmol) and Intermediate 91 (210 mg, 469 μmol) in NMP (0.5 mL) were added K$_2$CO$_3$ (194 mg, 1.41 mmol) and NaI (14.1 mg, 93.8 mol). The mixture was stirred at 80° C. for 1 hr. The crude product was concentrated. The filtrate was purified by prep-HPLC column: Phenomenex C18 75×30 mm×3 μm; mobile phase: [water (NH$_3$H$_2$O+NH$_4$HCO$_3$)-ACN]; gradient: 35%-75%, B over 7 min) to give 2-((1-(4-(2-(2-Aminopyridin-3-yl)-5-(3-oxo-1,4-diazepan-1-yl)-3H-imidazo[4,5-b]pyridin-3-yl)benzyl)piperidin-4-yl)amino)pyrimidine-4-carbonitrile (Example 347, 21.9 mg, yield: 7.6%) as a light-yellow solid. MS: m/z=615.5 [M+H]$^+$. $^1$H NMR (400 MHz, Dimethylsulfoxide-d$_6$) δ 8.54 (br s, 1H), 8.02-7.89 (m, 2H), 7.84 (d, J=7.2 Hz, 1H), 7.50-7.27 (m, 5H), 7.12-6.92 (m, 4H), 6.80 (d, J=8.8 Hz, 1H), 6.32 (dd, J=7.2, 5.2 Hz 1H), 4.17 (s, 2H), 3.82-3.81 (m, 2H), 3.76-3.63 (m, 1H), 3.55 (s, 2H), 3.18-3.17 (m, 2H), 2.91-2.77 (m, 2H), 2.00-2.16 (m, 2H), 1.87-1.79 (m, 2H), 1.65-1.64 (m, 2H), 1.61-1.43 (m, 2H).

Example 348: 4-(4-(4-(2-(2-Aminopyridin-3-yl)-5-(1-methyl-6-oxo-1,6-dihydropyridin-3-yl)-3H-imidazo[4,5-b]pyridin-3-yl)benzyl)piperazin-1-yl)pyrimidine-2-carbonitrile

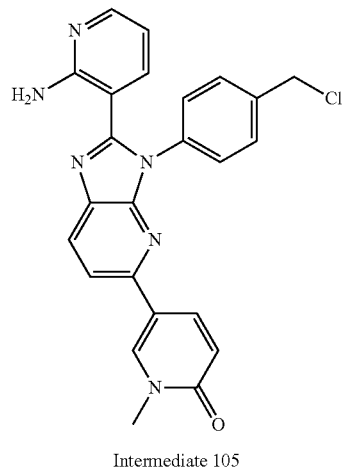

Intermediate 105

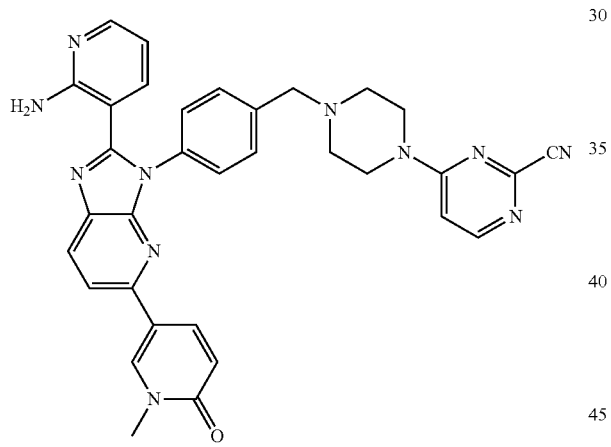

Example 348

Example 349: 4-(4-(4-(2-(2-Aminopyridin-3-yl)-5-(1-methyl-2-oxo-1,2-dihydropyridin-4-yl)-3H-imidazo[4,5-b]pyridin-3-yl)benzyl)piperazin-1-yl)pyrimidine-2-carbonitrile

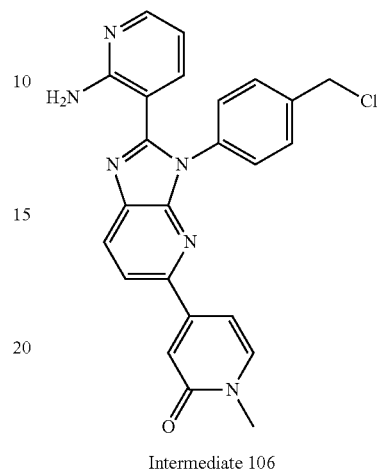

Intermediate 106

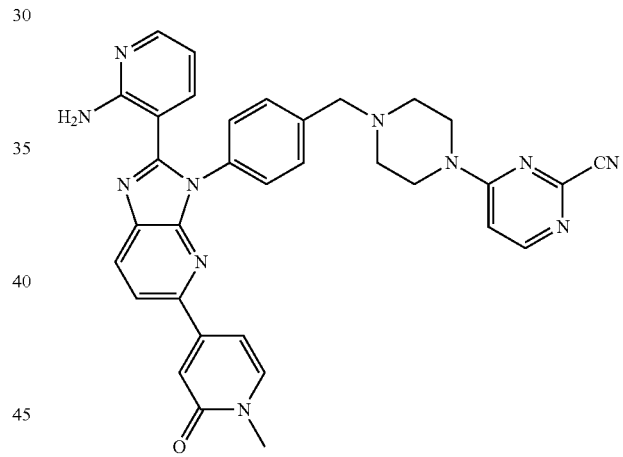

Example 349

To a mixture of Intermediate 105 (80 mg, 181 μmol) and Intermediate 53 (37.6 mg, 199 μmol) in DMF (1 mL) was added DIEA (93.4 mg, 126 μL). The mixture was stirred at 80° C. for 1 hr. The mixture was concentrated and purified by prep-HPLC (column: Phenomenex C18 75*30 mm*3 μm; mobile phase: [water (NH$_3$H$_2$O+NH$_4$HCO$_3$)-ACN]; gradient: 28%-58% B over 7 min) to give 4-(4-(4-(2-(2-aminopyridin-3-yl)-5-(1-methyl-6-oxo-1,6-dihydropyridin-3-yl)-3H-imidazo[4,5-b]pyridin-3-yl)benzyl)piperazin-1-yl)pyrimidine-2-carbonitrile (Example 348, 54.3 mg, yield: 51%) as a yellow solid. MS: m/z=596.1 [M+H]$^+$. $^1$H NMR (400 MHz, Dimethylsulfoxide-d$_6$) δ 8.48 (d, J=2.8 Hz, 1H), 8.30-8.20 (m, 2H), 8.08 (dd, J=9.6, 2.8 Hz, 1H), 7.99 (dd, J=4.8, 2.0 Hz, 1H), 7.84 (d, J=8.8 Hz, 1H), 7.53-7.47 (m, 2H), 7.46-7.38 (m, 2H), 7.16-7.09 (m, 2H), 7.03 (br s, 2H), 6.49 (d, J=9.6 Hz, 1H), 6.35 (dd, J=7.6, 4.8 Hz, 1H), 3.82-3.65 (m, 4H), 3.64 (s, 2H), 3.52 (s, 3H), 3.35-3.33 (m, 4H).

To a mixture of Intermediate 106 (100 mg, 226 μmol) and Intermediate 53 (47.0 mg, 248 mol) in DMF (1 mL) was added DIEA (117 mg, 157 μL). The mixture was stirred at 80° C. for 1 hr. The mixture was concentrated. After purified by prep-HPLC (column: Phenomenex C18 75*30 mm*3 μm; mobile phase: [water (NH$_3$H$_2$O+NH$_4$HCO$_3$)-ACN]; gradient: 30%-60% B over 7 min), 4-(4-(4-(2-(2-aminopyridin-3-yl)-5-(1-methyl-2-oxo-1,2-dihydropyridin-4-yl)-3H-imidazo[4,5-b]pyridin-3-yl)benzyl)piperazin-1-yl)pyrimidine-2-carbonitrile (Example 349, 89.1 mg, yield: 66%) was obtained as a yellow solid. MS: m/z=596.2 [M+H]$^+$. $^1$H NMR (400 MHz, Dimethylsulfoxide-d$_6$) δ 8.33-8.24 (m, 2H), 8.05 (d, J=8.4 Hz, 1H), 8.01 (dd, J=4.8, 2.0 Hz, 1H), 7.76 (d, J=7.2 Hz, 1H), 7.55-7.49 (m, 2H), 7.48-7.43 (m, 2H), 7.17 (dd, J=7.6, 1.6 Hz, 1H), 7.11 (d, J=6.8 Hz, 1H), 7.08-6.98 (m, 3H), 6.86 (dd, J=7.2, 2.0 Hz, 1H), 6.37 (dd, J=7.6, 4.4 Hz, 1H), 3.93-3.66 (m, 4H), 3.64 (s, 2H), 3.44 (s, 3H), 3.35-3.32 (m, 4H).

Example 350: 2-(4-(4-(2-(2-Aminopyridin-3-yl)-5-cyclopropyl-3H-imidazo[4,5-b]pyridin-3-yl)benzyl)piperazin-1-yl)pyrimidine-4-carbonitrile

Example 351: 2-((1-(4-(2-(2-Aminopyridin-3-yl)-5-cyclopropyl-3H-imidazo[4,5-b]pyridin-3-yl)benzyl)piperidin-4-yl)amino)pyrimidine-4-carbonitrile

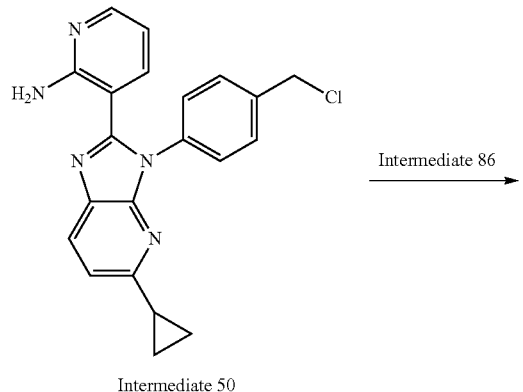
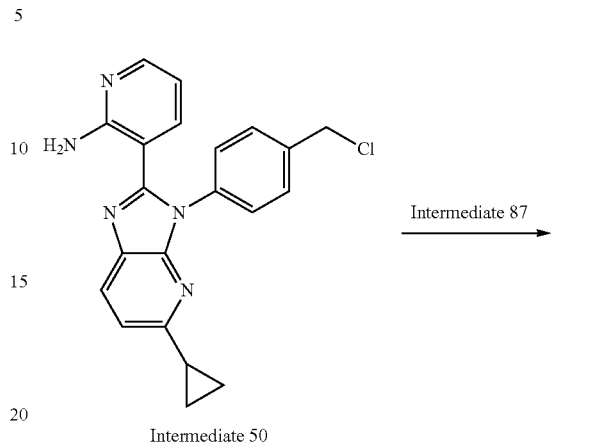

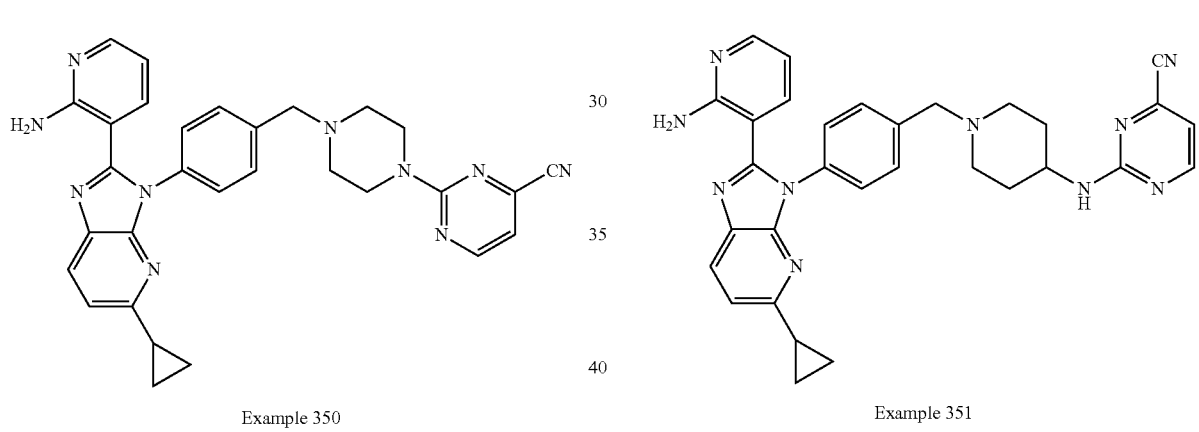

To a solution of Intermediate 50 (200 mg, 485 μmol) and Intermediate 86 (147 mg, 485 gmol) in DMF (2 mL) were added NaI (36.4 mg, 242 μmol) and K$_2$CO$_3$ (335 mg, 2.43 mmol). The mixture was stirred at 50° C. for 1 hr. The reaction mixture was filtered. The residue was purified by prep-HPLC (column; [water (NH$_4$HCO$_3$)-ACN]; B %. 51%-81%, 14 min), 2-(4-(4-(2-(2-aminopyridin-3-yl)-5-cyclopropyl-3H-imidazo[4,5-b]pyridin-3-yl)benzyl)piperazin-1-yl)pyrimidine-4-carbonitrile (Example 350, 85.2 mg, yield: 33%) was obtained as a yellow solid. MS: m/z=529.4 [M+H]$^+$. $^1$H NMR (400 MHz, Dimethylsulfoxide-d$_6$) δ 8.64 (d, J=4.8 Hz, 1H), 8.04 (d, J=8.0 Hz, 1H), 7.96 (dd, J=4.4, 1.6 Hz, 1H), 7.47 (d, J=8.4 Hz, 2H), 7.34 (d, J=8.0 Hz, 2H), 7.24 (d, J=8.4 Hz, 1H), 7.16 (d, J=4.4 Hz, 1H), 7.06 (dd, J=7.6, 2.0 Hz, 1H), 6.97 (br s, 2H), 6.34 (dd, J=8.0, 4.8 Hz, 1H), 3.82-3.74 (m, 4H), 3.62 (s, 2H), 2.49-2.45 (m, 4H), 2.21-2.12 (m, 1H), 0.97-0.90 (m, 2H), 0.86-0.80 (m, 2H).

To a solution of Intermediate 50 (200 mg, 485 μmol) and Intermediate 87 (153 mg, 485 μmol) in DMF (2 mL) were added NaI (36.3 mg, 242 μmol) and K$_2$CO$_3$ (335 mg, 2.43 mmol). The mixture was stirred at 50° C. for 1 hr. The reaction mixture was filtered. The residue was purified by prep-HPLC (column: [water (NH$_4$HCO$_3$)-ACN]; B %: 45%-75%, 14 min) to give 2-((1-(4-(2-(2-aminopyridin-3-yl)-5-cyclopropyl-3H-imidazo[4,5-b]pyridin-3-yl)benzyl)piperidin-4-yl)amino)pyrimidine-4-carbonitrile (Example 351, 15.9 mg, yield: 6%) as a yellow solid. MS: m/z=543.4 [M+H]$^+$. $^1$H NMR (400 MHz, Dimethylsulfoxide-d$_6$) δ 8.62 (d, J=4.8 Hz, 1H), 8.03 (d, J=8.0 Hz, 1H), 7.99-7.94 (m, 1H), 7.49 (d, J=8.0 Hz, 2H), 7.31 (d, J=8.0 Hz, 2H), 7.25 (d, J=8.4 Hz, 1H), 7.13-7.07 (m, 2H), 6.95 (br s, 2H), 6.36 (dd, J=7.6, 4.8 Hz, 1H), 4.48-4.32 (m, 2H), 3.84 (s, 2H), 3.18-3.10 (m, 2H), 2.80-2.69 (m, 1H), 2.32-2.22 (m, 1H), 2.22-2.11 (m, 1H), 1.95-1.87 (m, 2H), 1.33-1.23 (m, 2H), 0.95-0.89 (m, 2H), 0.84-0.79 (m, 2H).

Example 352: 2-((1-(4-(2-(2-Aminopyridin-3-yl)-5-(4-fluorophenyl)-3H-imidazo[4,5-b]pyridin-3-yl)benzyl)piperidin-4-yl)amino)pyrimidine-4-carbonitrile Example 353: 4-((1-(4-(2-(2-Aminopyridin-3-yl)-5-(3-chlorophenyl)-3H-imidazo[4,5-b]pyridin-3-yl)benzyl)piperidin-4-yl)amino)pyrimidine-2-carbonitrile

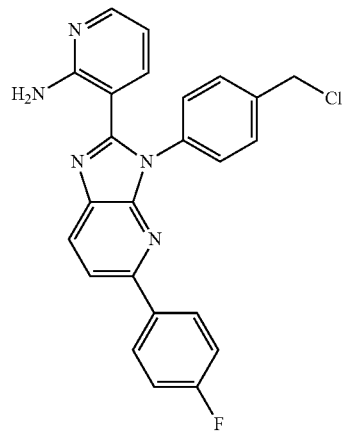

Intermediate 107

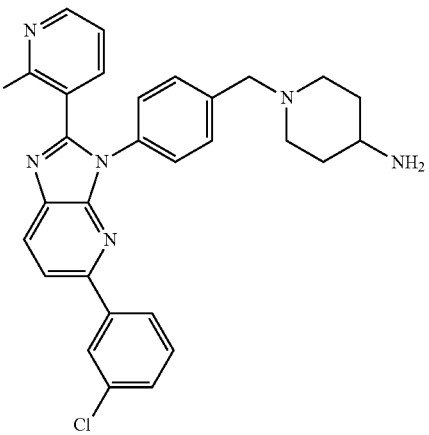

Intermediate 113

Intermediate 87 →

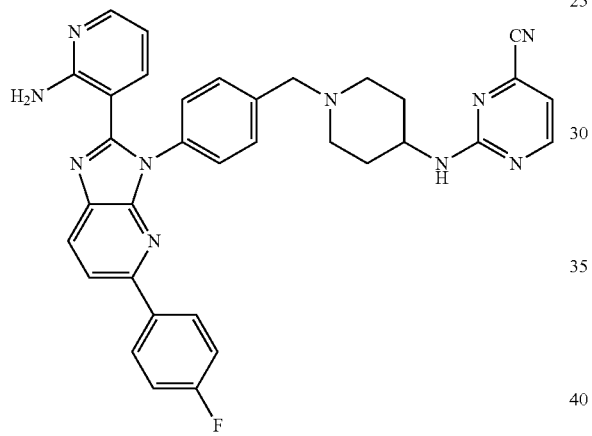

Example 352

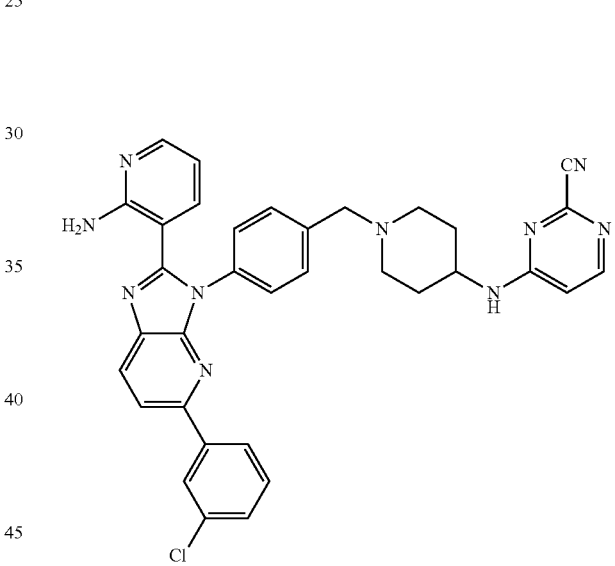

Example 353

To a solution of Intermediate 107 (200 mg, 429 μmol) and Intermediate 87 (136 mg, 429 mol) in DMF (2 mL) were added NaI (32.3 mg, 214 μmol) and K₂CO₃ (296 mg, 2.14 mmol). The mixture was stirred at 50° C. for 1 hr. The reaction mixture was filtered. The residue was purified by prep-HPLC (column: [water (NH₄HCO₃)-ACN]; B %: 53%-83%, 14 min) to give 2-((1-(4-(2-(2-aminopyridin-3-yl)-5-(4-fluorophenyl)-3H-imidazo[4,5-b]pyridin-3-yl)benzyl)piperidin-4-yl)amino)pyrimidine-4-carbonitrile (Example 352, 72.1 mg, yield: 28%) as a yellow solid. MS: m/z=597.4 [M+H]$^+$. $^1$H NMR (400 MHz, Dimethylsulfoxide-d₆) δ 8.62 (d, J=4.4 Hz, 1H), 8.26 (d, J=8.4 Hz, 1H), 8.11-8.04 (m, 2H), 8.02-7.94 (m, 2H), 7.54 (d, J=8.0 Hz, 2H), 7.43 (d, J=8.0 Hz, 2H), 7.34-7.26 (m, 2H), 7.19 (dd, J=7.6, 2.0 Hz, 1H), 7.10 (d, J=4.8 Hz, 1H), 7.02 (br s, 2H), 6.40 (dd, J=8.0, 5.2 Hz, 1H), 4.44-4.38 (m, 2H), 3.86 (s, 2H), 3.20-3.09 (m, 2H), 2.81-2.71 (m, 1H), 2.45-2.19 (m, 1H), 1.95-1.89 (m, 2H), 1.34-1.21 (m, 2H). $^{19}$H NMR (400 MHz, Dimethylsulfoxide-d₆) δ −113.573.

To a solution of Intermediate 113 (100 mg, 196 μmol), 4-chloropyrimidine-2-carbonitrile (30.1 mg, 216 μmol) and DIEA (76 mg, 588 μmol) in NMP (2 mL) was taken up into a microwave tube. The mixture was stirred at 130° C. for 0.5 hr. After cooling to 25° C., the reaction mixture was filtered. After purified by prep-HPLC (column: Waters xbridge 150*25 mm*10 μm; mobile phase: [water (NH₄HCO₃)-ACN]; gradient: 47%-77% B over 18 min), 4-((1-(4-(2-(2-aminopyridin-3-yl)-5-(3-chlorophenyl)-3H-imidazo[4,5-b]pyridin-3-yl)benzyl)piperidin-4-yl)amino)pyrimidine-2-carbonitrile (Example 353, 13.3 mg, yield: 11%) was obtained as a purple solid. MS: m/z=613.4 [M+H]$^+$. $^1$H NMR (400 MHz, Methanol-d₄) δ 8.22 (d, J=8.4 Hz, 1H), 8.07-8.03 (m, 1H), 8.03-7.93 (m, 4H), 7.58 (d, J=8.0 Hz, 2H), 7.48-7.32 (m, 5H), 6.63-6.56 (m, 1H), 6.48 (dd, J=7.6, 5.2 Hz, 1H), 4.03-3.89 (m, 1H), 3.68 (s, 2H), 3.04-2.93 (m, 2H), 2.35-2.25 (m, 2H), 2.05-1.99 (m, 2H), 1.67-1.58 (m, 2H).

Example 354: 2-(4-(4-(2-(2-Aminopyridin-3-yl)-5-(1-methyl-6-oxo-1,6-dihydropyridin-3-yl)-3H-imidazo[4,5-b]pyridin-3-yl)benzyl)piperazin-1-yl)pyrimidine-4-carbonitrile

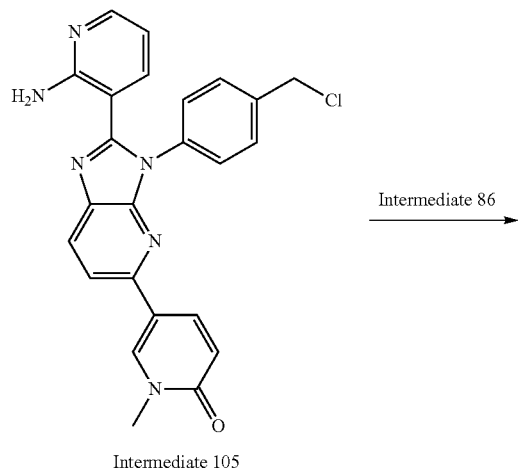

Intermediate 105

→ Intermediate 86

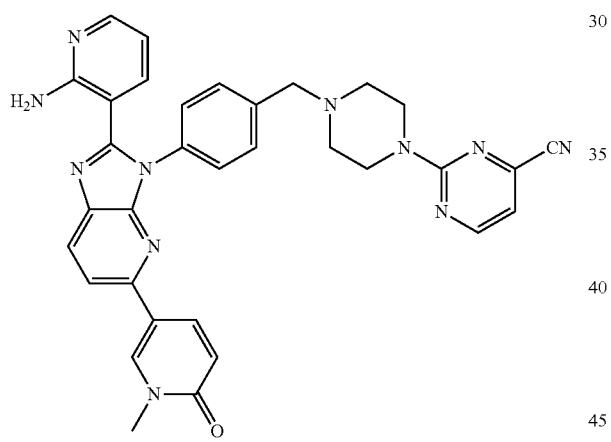

Example 354

To a mixture of Intermediate 105 (50 mg, 113 μmol) and Intermediate 86 (21.4 mg, 113 μmol) in DMF (1 mL) was added DIEA (58.4 mg, 452 μmol). The mixture was stirred at 80° C. for 1 hr. Then it was concentrated and purified by prep-HPLC (column: Phenomenex C18 75*30 mm*3 μm; mobile phase: [water (NH$_3$H$_2$O+NH$_4$HCO$_3$)-ACN]; gradient: 35%-65% B over 7 min) to give 2-(4-(4-(2-(2-Aminopyridin-3-yl)-5-(1-methyl-6-oxo-1,6-dihydropyridin-3-yl)-3H-imidazo[4,5-b]pyridin-3-yl)benzyl)piperazin-1-yl)pyrimidine-4-carbonitrile (Example 354, 13.8 mg, yield: 21%) as a yellow solid. MS: m/z=596.2 [M+H]$^+$. $^1$H NMR (400 MHz, Dimethylsulfoxide-d$_6$) δ 8.65 (d, J=4.8 Hz, 1H), 8.47 (d, J=2.8 Hz, 1H), 8.23 (d, J=8.4 Hz, 1H), 8.09 (dd, J=9.6, 2.8 Hz, 1H), 7.99 (dd, J=5.2, 2.0 Hz, 1H), 7.84 (d, J=8.4 Hz, 1H), 7.55-7.48 (m, 2H), 7.45-7.38 (m, 2H), 7.18-7.10 (m, 2H), 7.02 (br s, 2H), 6.49 (d, J=9.6 Hz, 1H), 6.36 (dd, J=7.6, 5.2 Hz, 1H), 3.82-3.76 (m, 4H), 3.64 (s, 2H), 3.52 (s, 3H), 3.35-3.32 (m, 4H).

Example 355: 4-((1-(4-(2-(2-Aminopyridin-3-yl)-5-(1-methyl-6-oxo-1,6-dihydropyridin-3-yl)-3H-imidazo[4,5-b]pyridin-3-yl)benzyl)piperidin-4-yl)amino)pyrimidine-2-carbonitrile

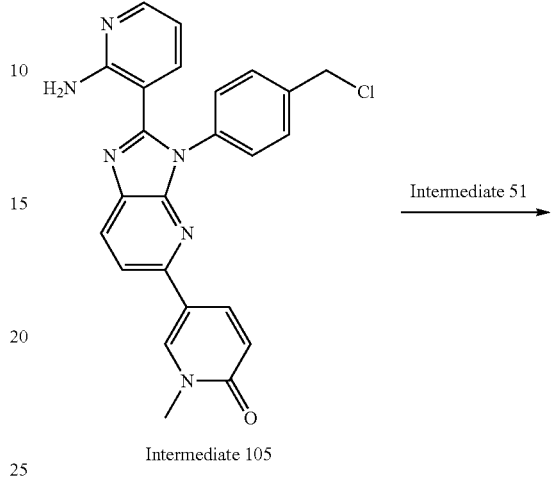

Intermediate 105

→ Intermediate 51

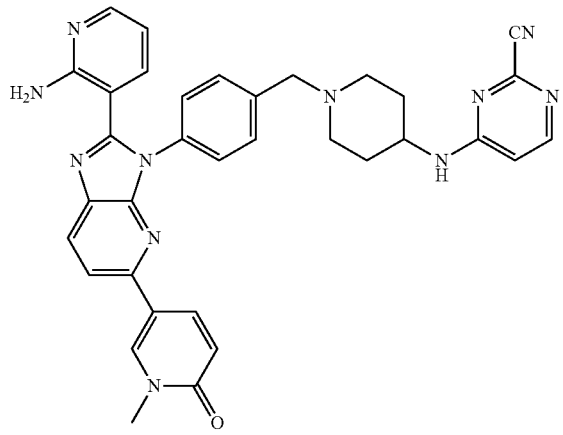

Example 355

To a mixture of Intermediate 105 (150 mg, 339 μmol) and Intermediate 51 (75.7 mg, 373 μmol) in DMF (1 mL) was added DIEA (175 mg, 1.35 mmol). The mixture was stirred at 80° C. for 1 hr. Then it was concentrated and purified by prep-HPLC (column: Phenomenex C18 75*30 mm*3 μm; mobile phase: [water (NH$_3$H$_2$O+NH$_4$HCO$_3$)-ACN]; gradient: 30%-60% B over 7 min) to give 4-((1-(4-(2-(2-Aminopyridin-3-yl)-5-(1-methyl-6-oxo-1,6-dihydropyridin-3-yl)-3H-imidazo[4,5-b]pyridin-3-yl)benzyl)piperidin-4-yl)amino)pyrimidine-2-carbonitrile (Example 355, 55.4 mg, yield: 27%) as a yellow solid. MS: m/z=610.2 [M+H]$^+$. $^1$H NMR (400 MHz, Dimethylsulfoxide-d$_6$) δ 8.47 (d, J=2.4 Hz, 1H), 8.23 (d, J=8.8 Hz, 1H), 8.14-8.00 (m, 3H), 7.99 (dd, J=4.8, 2.0 Hz, 1H), 7.83 (d, J=8.4 Hz, 1H), 7.50-7.45 (m, 2H), 7.44-7.35 (m, 2H), 7.12 (dd, J=8.0, 2.0 Hz, 1H), 7.02 (br s, 2H), 6.67 (d, J=6.0 Hz, 1H), 6.48 (d, J=9.6 Hz, 1H), 6.36 (dd, J=7.6, 4.8 Hz, 1H), 3.91-3.74 (m, 1H), 3.59 (s, 2H), 3.52 (s, 3H), 2.89-2.78 (m, 2H), 2.21-2.07 (m, 2H), 1.95-1.79 (m, 2H), 1.58-1.40 (m, 2H).

Example 356: 2-((1-(4-(2-(2-Aminopyridin-3-yl)-5-(1-methyl-6-oxo-1,6-dihydropyridin-3-yl)-3H-imidazo[4,5-b]pyridin-3-yl)benzyl)piperidin-4-yl)amino)pyrimidine-4-carbonitrile

Example 357: 4-((1-(4-(2-(2-Aminopyridin-3-yl)-5-(3-fluorophenyl)-3H-imidazo[4,5-b]pyridin-3-yl)benzyl)piperidin-4-yl)amino)pyrimidine-2-carbonitrile

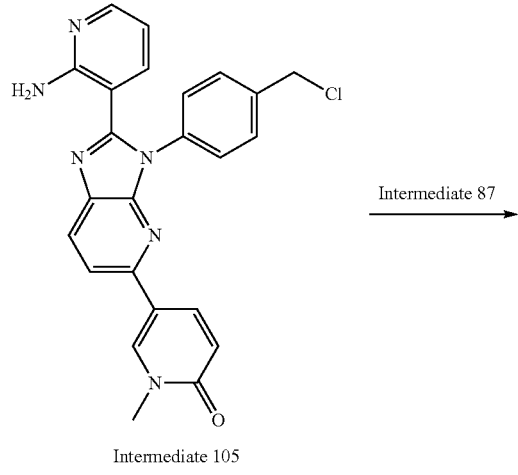

Intermediate 105

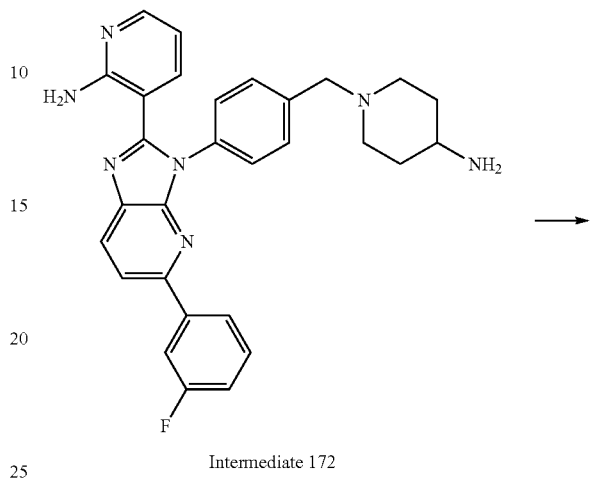

Intermediate 172

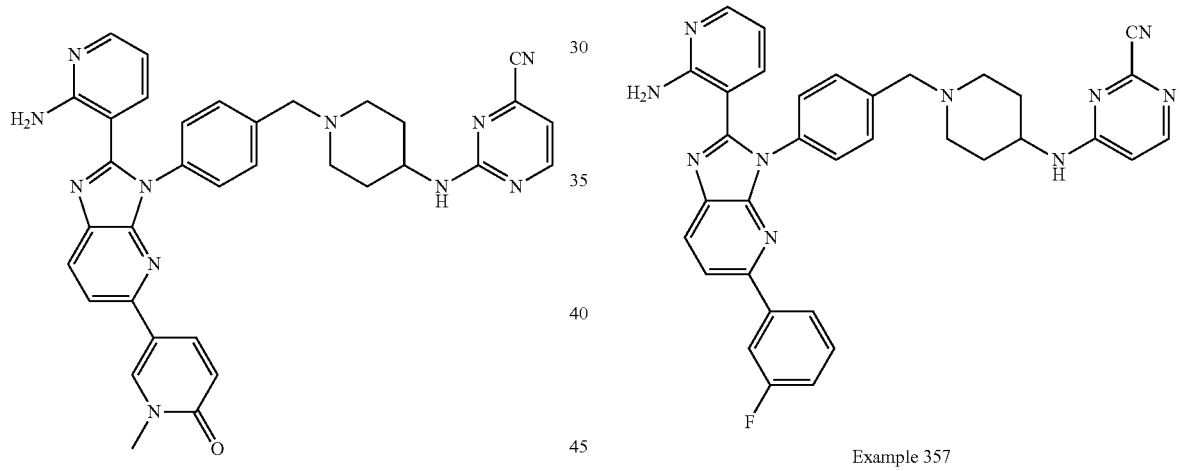

Example 356

Example 357

To a mixture of Intermediate 105 (50 mg, 113 μmol) and Intermediate 87 (25.2 mg, 124 gmol) in DMF (1 mL) was added DIEA (58.4 mg, 452 μmol). The mixture was stirred at 80° C. for 1 hr. Then it was concentrated and purified by prep-HPLC (column: Phenomenex C18 75*30 mm*3 μm; mobile phase: [water ($NH_3H_2O+NH_4HCO_3$)-ACN]; gradient: 30%-60% B over 7 min) to give 2-((1-(4-(2-(2-Aminopyridin-3-yl)-5-(1-methyl-6-oxo-1,6-dihydropyridin-3-yl)-3H-imidazo[4,5-b]pyridin-3-yl)benzyl)piperidin-4-yl)amino)pyrimidine-4-carbonitrile (Example 356, 7.3 mg, yield: 11%) as a yellow solid. MS: m/z=610.2 [M+H]$^+$. $^1$H NMR (400 MHz, Dimethylsulfoxide-$d_6$) δ 8.64-8.51 (m, 1H), 8.46 (d, J=2.0 Hz, 1H), 8.22 (d, J=8.4 Hz, 1H), 8.08 (dd, J=9.6, 2.0 Hz, 1H), 7.99 (d, J=3.6 Hz, 1H), 7.90-7.77 (m, 2H), 7.50-7.44 (m, 2H), 7.43-7.36 (m, 2H), 7.12 (d, J=7.6 Hz, 1H), 7.07 (d, J=4.4 Hz, 1H), 7.03 (br s, 2H), 6.48 (d, J=9.2 Hz, 1H), 6.35 (dd, J=7.6, 5.2 Hz, 1H), 3.80-3.64 (m, 1H), 3.57 (s, 2H), 3.51 (s, 3H), 2.90-2.74 (m, 2H), 2.20-2.00 (m, 2H), 1.91-1.76 (m, 2H), 1.62-1.42 (m, 2H).

A solution of Intermediate 172 (110 mg, 223 μmol), 4-chloropyrimidine-2-carbonitrile (34.2 mg, 245 μmol) and DIEA (86.4 mg, 669 μmol) in NMP (2 mL) were taken up into a microwave tube. The mixture was heated at 130° C. for 0.5 hr using microwave irradiation. After cooling to 25° C., the reaction mixture was filtered. After purified by prep-HPLC (column: Waters xbridge 150×25 mm 10 μm; mobile phase: [water ($NH_4HCO_3$)-ACN]; gradient: 43%-73% B over 18 min), 4-((1-(4-(2-(2-aminopyridin-3-yl)-5-(3-fluorophenyl)-3H-imidazo[4,5-b]pyridin-3-yl)benzyl)piperidin-4-yl)amino)pyrimidine-2-carbonitrile (Example 357, 11.5 mg, yield: 9%) was obtained as a light-yellow solid. MS: m/z=597.5 [M+H]$^+$. $^1$H NMR (400 MHz, Methanol-$d_4$) δ 8.23 (d, J=8.4 Hz, 1H), 8.06-7.96 (m, 3H), 7.89 (d, J=8.4 Hz, 1H), 7.82-7.78 (m, 1H), 7.59 (d, J=8.4 Hz, 2H), 7.50-7.44 (m, 3H), 7.37-7.35 (m, 1H), 7.16-7.09 (m, 1H), 6.66-6.59 (m, 1H), 6.51 (d, J=7.6, 5.2 Hz, 1H), 3.91-3.89 (m, 1H), 3.70 (s, 2H), 3.04-2.97 (m, 2H), 2.36-2.28 (m, 2H), 2.06-2.01 (m, 2H), 1.68-1.59 (m, 2H); $^{19}$F NMR (400 MHz, Methanol-$d_4$) δ −115.29.

Example 358: 2-((1-(4-(2-(2-Aminopyridin-3-yl)-5-(3-fluorophenyl)-3H-imidazo[4,5-b]pyridin-3-yl)benzyl)piperidin-4-yl)amino)pyrimidine-4-carbonitrile

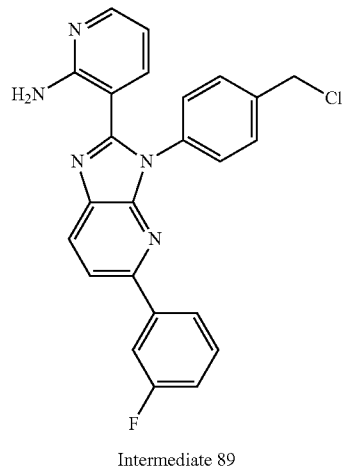

Intermediate 89

→ Intermediate 87

Example 359: 4-((1-(4-(2-(2-Aminopyridin-3-yl)-5-(1-methyl-2-oxo-1,2-dihydropyridin-4-yl)-3H-imidazo[4,5-b]pyridin-3-yl)benzyl)piperidin-4-yl)amino)pyrimidine-2-carbonitrile

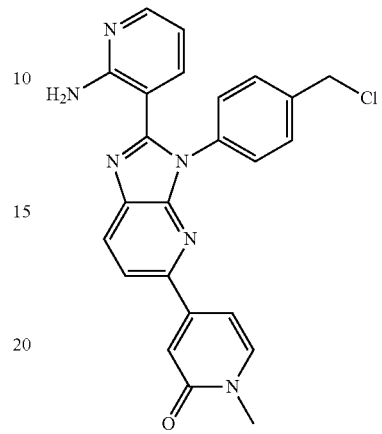

Intermediate 106

→ Intermediate 51

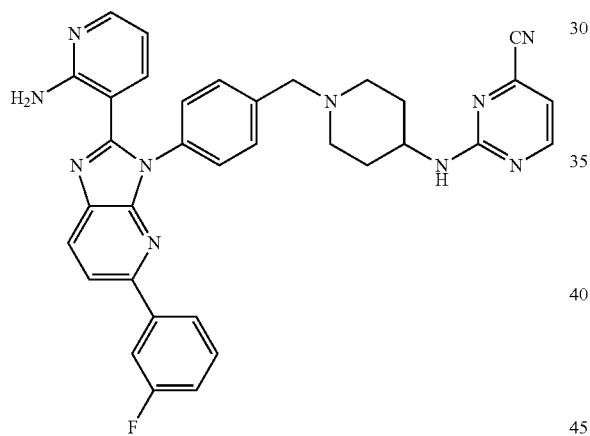

Example 358

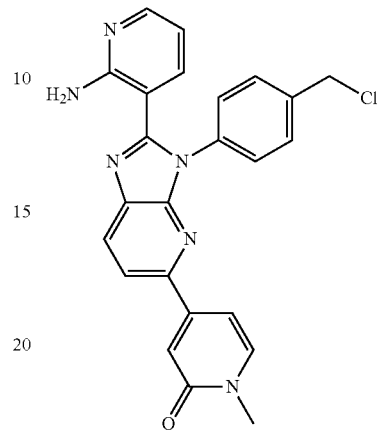

Example 359

To a solution of Intermediate 89 (200 mg HCl salt, 429 μmol) and Intermediate 87 (136 mg TFA salt, 429 μmol) in DMF (5 mL) was added NaI (32.1 mg, 214 μmol) and $K_2CO_3$ (296 mg, 2.14 mmol). The mixture was stirred at 50° C. for 1 hr. The reaction mixture was filtered. After purified by prep-HPLC (column: Waters Xbridge C18 150×50 mm×10 μm; mobile phase: [water ($NH_4HCO_3$)-ACN]; gradient: 52%-82% B over 10 min), 2-((1-(4-(2-(2-aminopyridin-3-yl)-5-(3-fluorophenyl)-3H-imidazo[4,5-b]pyridin-3-yl)benzyl)piperidin-4-yl)amino)pyrimidine-4-carbonitrile (Example 358, 21.2 mg, yield: 8%) was obtained as a yellow solid. MS: m/z=597.3 [M+H]$^+$. $^1$H NMR (400 MHz, Dimethylsulfoxide-$d_6$) δ 8.62 (d, J=4.8 Hz, 1H), 8.28 (d, J=8.4 Hz, 1H), 8.05 (d, J=8.4 Hz, 1H), 8.01-8.01 (m, 1H), 7.90 (d, J=7.6 Hz, 1H), 7.82 (d, J=10.8 Hz, 1H), 7.57-7.48 (m, 4H), 7.44 (d, J=8.4 Hz, 2H), 7.23-7.19 (m, 2H), 7.10 (d, J=4.4 Hz, 1H), 7.02 (br s, 2H), 6.41 (dd, J=7.6, 4.8 Hz, 1H), 4.48-4.41 (m, 2H), 3.87 (s, 2H), 3.17-3.11 (m, 2H), 2.77-2.74 (m, 1H), 1.94-1.89 (m, 2H), 1.31-1.24 (m, 2H). $^{19}$F NMR (400 MHz, Dimethylsulfoxide-$d_6$) δ −112.913.

To a mixture of Intermediate 106 (100 mg, 226 gmol) and Intermediate 51 (50.5 mg, 248 mol) in DMF (1 mL) was added DIEA (117 mg, 903 μmol). The mixture was stirred at 80° C. for 1 hr. The mixture was concentrated and purified by prep-HPLC (column: Phenomenex C18 75*30 mm*3 μm; mobile phase: [water ($NH_3H_2O+NH_4HCO_3$)-ACN]; gradient: 30%-60% B over 7 min) to give 4-((1-(4-(2-(2-aminopyridin-3-yl)-5-(1-methyl-2-oxo-1,2-dihydropyridin-4-yl)-3H-imidazo[4,5-b]pyridin-3-yl)benzyl)piperidin-4-yl)amino)pyrimidine-2-carbonitrile (Example 359, 85.7 mg, yield: 62%) as a yellow solid. MS: m/z=610.2 [M+H]$^+$. $^1$H NMR (400 MHz, Dimethylsulfoxide-$d_6$) δ 8.28 (d, J=8.4 Hz, 1H), 8.12-7.93 (m, 4H), 7.75 (d, J=7.2 Hz, 1H), 7.53-7.39 (m, 4H), 7.17 (dd, J=7.6, 1.6 Hz, 1H), 7.08-6.98 (m, 3H), 6.85 (dd, J=7.2, 2.0 Hz, 1H), 6.67 (d, J=6.0 Hz, 1H), 6.38 (dd, J=7.6, 4.8 Hz, 1H), 3.87-3.73 (m, 1H), 3.59 (s, 2H), 3.43 (s, 3H), 2.89-2.79 (m, 2H), 2.22-2.08 (m, 2H), 1.95-1.81 (m, 2H), 1.59-1.39 (m, 2H).

1445

Example 360: 2-((1-(4-(2-(2-Aminopyridin-3-yl)-5-(1-methyl-2-oxo-1,2-dihydropyridin-4-yl)-3H-imidazo[4,5-b]pyridin-3-yl)benzyl)piperidin-4-yl)amino)pyrimidine-4-carbonitrile

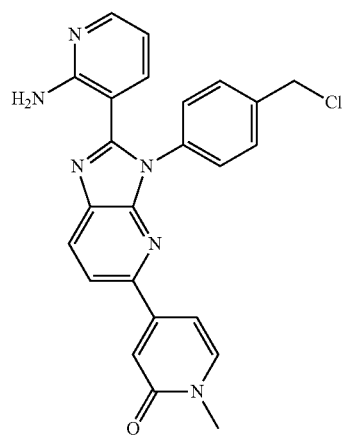

Intermediate 106

→ Intermediate 87 →

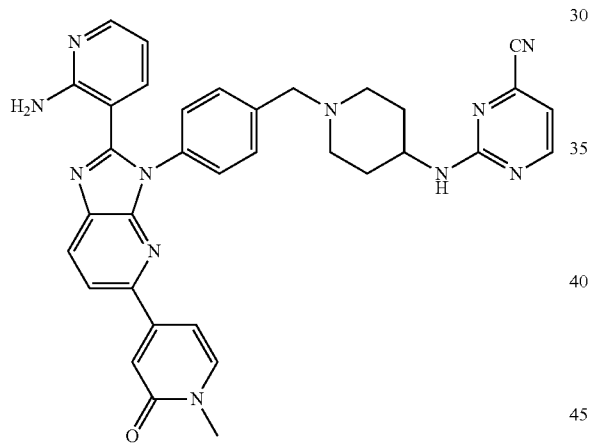

Example 360

1446

Example 361: 4-(7-(4-(2-(2-Aminopyridin-3-yl)-5-phenyl-3H-imidazo[4,5-b]pyridin-3-yl)benzyl)-2,7-diazaspiro[3.5]nonan-2-yl)pyrimidine-2-carbonitrile

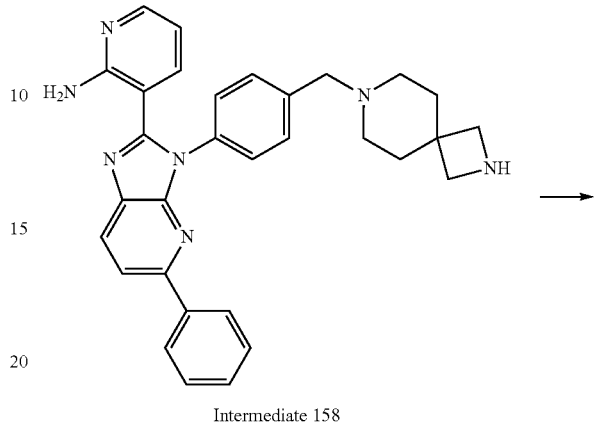

Intermediate 158

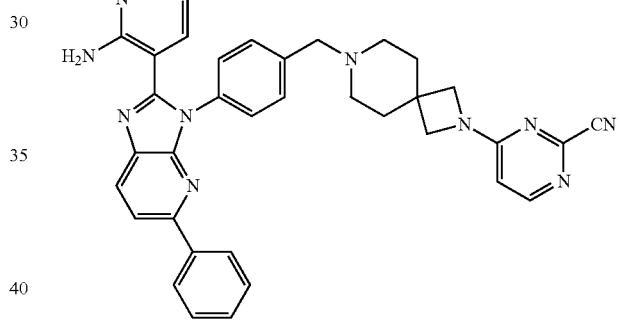

Example 381

To a mixture of Intermediate 106 (50 mg, 113 μmol) and Intermediate 87 (25.2 mg, 124 gmol) in DMF (1 mL) was added DIEA (58.3 mg, 452 μmol), the mixture was stirred at 80° C. for 1 hr. Then it was concentrated. After purified by prep-HPLC (column: Phenomenex C18 75*30 mm*3 μm; mobile phase: [water (NH$_3$H$_2$O+NH$_4$HCO$_3$)-ACN]; gradient: 30%-60% B over 7 min), 2-((1-(4-(2-(2-aminopyridin-3-yl)-5-(1-methyl-2-oxo-1,2-dihydropyridin-4-yl)-3H-imidazo[4,5-b]pyridin-3-yl)benzyl)piperidin-4-yl)amino)pyrimidine-4-carbonitrile (Example 360, 17.2 mg, yield: 25%) as a yellow solid. MS: m/z=610.1 [M+H]$^+$. $^1$H NMR (400 MHz, Dimethylsulfoxide-d$_6$) δ 8.61-8.49 (m, 1H), 8.29 (d, J=8.4 Hz, 1H), 8.09-7.97 (m, 2H), 7.89-7.82 (m, 1H), 7.75 (d, J=7.2 Hz, 1H), 7.52-7.40 (m, 4H), 7.18 (dd, J=7.6, 1.2 Hz, 1H), 7.09-6.99 (m, 4H), 6.86 (dd, J=7.2, 2.0 Hz, 1H), 6.38 (dd, J=7.6, 4.8 Hz, 1H), 3.78-3.64 (m, 1H), 3.58 (s, 2H), 3.43 (s, 3H), 2.88-2.80 (m, 2H), 2.16-2.03 (m, 2H), 1.89-1.80 (m, 2H), 1.62-1.48 (m, 2H).

To a solution of Intermediate 158 (100 mg, 199 μmol) and 4-chloropyrimidine-2-carbonitrile (30.6 mg, 219 μmol) in DMF (2 mL) were added NaI (2.99 mg, 19.9 μmol) and K$_2$CO$_3$ (55.1 mg, 399 μmol). The mixture was stirred at 80° C. for 2 hr. The reaction mixture was filtered. After purified by prep-HPLC (column: Phenomenex C18 150*25 mm*10 μm; mobile phase: [water (NH$_4$HCO$_3$)-ACN]; gradient: 50%-80% B over 10 min), 4-(7-(4-(2-(2-aminopyridin-3-yl)-5-phenyl-3H-imidazo[4,5-b]pyridin-3-yl)benzyl)-2,7-diazaspiro[3.5]nonan-2-yl)pyrimidine-2-carbonitrile (Example 361, 19.9 mg, yield: 16%) was obtained as a light-yellow solid. MS: m/z=605.4 [M+H]$^+$. $^1$H NMR (400 MHz, Dimethylsulfoxide-d$_6$) δ 8.29-8.20 (m, 2H), 8.04-7.97 (m, 4H), 7.50-7.44 (m, 6H), 7.42-7.37 (m, 1H), 7.17 (d, J=7.6 Hz, 1H), 7.03 (br s, 2H), 6.63 (d, J=6 Hz, 1H), 6.38 (dd, J=7.6, 4.8 Hz, 1H), 3.80 (s, 4H), 3.56 (s, 2H), 3.31-3.27 (m, 2H), 2.37-2.35 (m, 2H), 1.82-1.76 (m, 4H).

Example 362: 4-((7-(4-(2-(2-Aminopyridin-3-yl)-5-phenyl-3H-imidazo[4,5-b]pyridin-3-yl)benzyl)-7-azaspiro[3.5]nonan-2-yl)amino)pyrimidine-2-carbonitrile

Example 363: 4-(8-(4-(2-(2-Aminopyridin-3-yl)-5-phenyl-3H-imidazo[4,5-b]pyridin-3-yl)benzyl)-2,8-diazaspiro[4.5]decan-2-yl)-1,3,5-triazine-2-carbonitrile

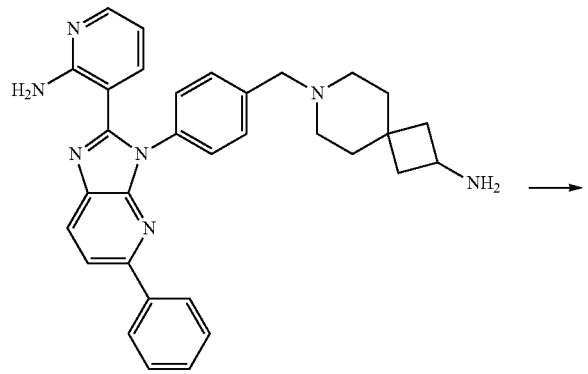

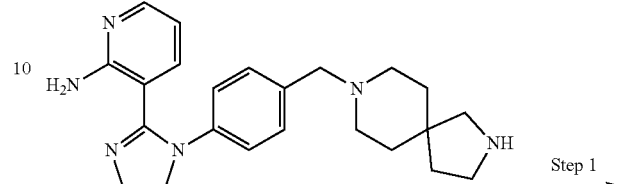

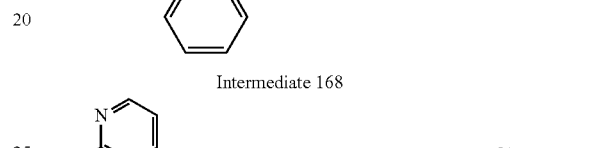

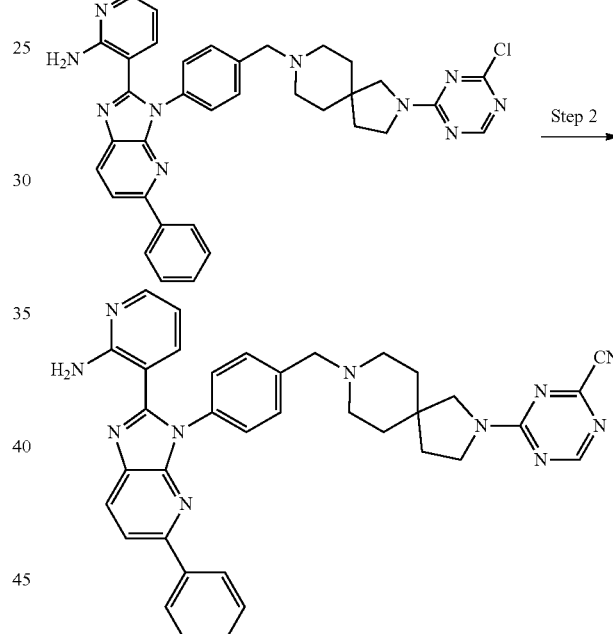

To a solution of Intermediate 156 (100 mg, 194 μmol) and 4-chloropyrimidine-2-carbonitrile (29.8 mg, 213 μmol) in DMF (2 mL) were added NaI (2.91 mg, 19.4 μmol) and K₂CO₃ (53.6 mg, 388 μmol). The mixture was stirred at 80° C. for 2 hr. The reaction mixture was filtered and purified by prep-HPLC (column: Phenomenex C18 150*25 mm*10 μm; mobile phase: [water (NH₄HCO₃)-ACN]; gradient: 42%-72% B over 14 min) to give 4-((7-(4-(2-(2-aminopyridin-3-yl)-5-phenyl-3H-imidazo[4,5-b]pyridin-3-yl)benzyl)-7-azaspiro[3.5]nonan-2-yl)amino)pyrimidine-2-carbonitrile (Example 362, 3.0 mg, yield: 1.2%) as a light-yellow solid. MS: m/z=619.4 [M+H]⁺. ¹H NMR (400 MHz, Dimethylsulfoxide-d₆) δ 8.50-8.32 (m, 1H), 8.28 (d, J=8.4 Hz, 1H), 8.05-7.96 (m, 4H), 7.50-7.43 (m, 7H), 7.42-7.36 (m, 1H), 7.16 (dd, J=8.0, 2.0 Hz, 1H), 7.04 (br s, 2H), 6.65 (d, J=6.0 Hz, 1H), 6.37 (dd, J=7.6, 4.8 Hz, 1H), 4.48-4.17 (m, 1H), 3.54 (s, 2H), 3.31-3.29 (m, 2H), 2.35-2.31 (m, 2H), 2.30-2.23 (m, 4H), 1.67-1.64 (m, 2H), 1.58-1.54 (m, 2H).

Step 1: 3-(3-(4-((2-(4-Chloro-1,3,5-triazin-2-yl)-2,8-diazaspiro[4.5]decan-8-yl)methyl)phenyl)-5-phenyl-3H-imidazo[4,5-b]pyridin-2-yl)pyridin-2-amine To a solution of Intermediate 168 (80 mg, 155 μmol) in THF (8 mL) and H₂O (2 mL) was added DIEA (60 mg, 465 μmol). Then 4-Chloro-1,3,5-triazine-2-carbonitrile (28 mg, 186 μmol) in THF (2 mL) was added into the mixture at 0° C. The mixture was stirred at 0° C. for 1 hr. The reaction mixture was extracted with CH₂Cl₂ (30 mL). The organic phase was separated, dried over anhydrous Na₂SO₄, filtered and concentrated under reduced pressure. After purified by prep-TLC (CH₂Cl₂:MeOH=10:1), 3-(3-(4-((2-(4-chloro-1,3,5-triazin-2-yl)-2,8-diazaspiro[4.5]decan-8-yl)methyl)phenyl)-5-phenyl-3H-imidazo[4,5-b]pyridin-2-yl)pyridin-2-amine (4.2 mg, yield: 4%) was obtained as a yellow solid.

MS: m/z=629.3 [M+H]⁺. ¹H NMR (400 MHz, Methanol-d₄) δ 8.32 (d, J=6.8 Hz, 1H), 8.19 (d, J=8.4 Hz, 1H), 8.07-7.99 (m, 2H), 7.99-7.91 (m, 2H), 7.58-7.51 (m, 2H), 7.48-7.30 (m, 6H), 6.52-6.42 (m, 1H), 3.68-3.60 (m, 4H), 3.48 (d, J=10.0 Hz, 2H), 2.69-2.59 (m, 2H), 2.52-2.41 (m, 2H), 1.95-1.86 (m, 2H), 1.69-1.64 (m, 4H).

Step 2: 4-(8-(4-(2-(2-Aminopyridin-3-yl)-5-phenyl-3H-imidazo[4,5-b]pyridin-3-yl)benzyl)-2,8-diazaspiro[4.5]decan-2-yl)-1,3,5-triazine-2-carbonitrile To a solution 3-(3-(4-((2-(4-chloro-1,3,5-triazin-2-yl)-2,8-diazaspiro[4.5]decan-8-yl)methyl)phenyl)-5-phenyl-3H-imidazo[4,5-b]pyridin-2-yl)pyridin-2-amine (80 mg, 127 μmol) in DMSO (1 mL) was added KCN (0.1 g, 1.5 mmol) and DABCO (2.9 mg, 25 μmol). The mixture was stirred at 25° C. for 16 hr. The reaction mixture was poured into water (5 mL) and extracted with CH₂Cl₂ (6 mL). The combined organic layers were washed with brine (2 ml) and dried over anhydrous Na₂SO₄, filtered and concentrated to dryness. After purified by prep-TLC (CH₂Cl₂:MeOH=10:1), 4-(8-(4-(2-(2-aminopyridin-3-yl)-5-phenyl-3H-imidazo[4,5-b]pyridin-3-yl)benzyl)-2,8-diazaspiro[4.5]decan-2-yl)-1,3,5-triazine-2-carbonitrile (Example 363, 4.4 mg, yield: 5%) was obtained as a yellow solid. MS: m/z=620.3 [M+H]⁺. ¹H NMR (400 MHz, Chloroform-d) δ 8.55 (d, J=11.2 Hz, 1H), 8.14 (d, J=8.4 Hz, 1H), 8.06 (d, J=5.2 Hz, 1H), 8.01 (d, J=7.6 Hz, 2H), 7.81 (d, J=8.0 Hz, 1H), 7.65-7.60 (m, 1H), 7.51-7.39 (m, 6H), 7.10 (d, J=8.0 Hz, 1H), 6.69 (br s, 2H), 6.37 (dd, J=7.6, 4.8 Hz, 1H), 3.93-3.76 (m, 2H), 3.71-3.66 (m, 2H), 3.52 (s, 2H), 2.88-2.49 (m, 4H), 2.05-1.92 (m, 6H).

Example 364: 4-(9-(4-(2-(2-Aminopyridin-3-yl)-5-phenyl-3H-imidazo[4,5-b]pyridin-3-yl)benzyl)-3,9-diazaspiro[5.5]undecan-3-yl)pyrimidine-2-carbonitrile

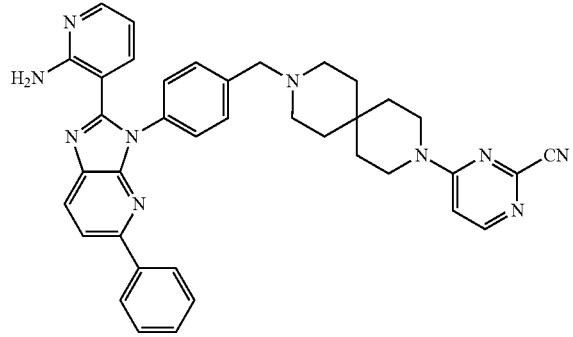

Example 364

A mixture of Intermediate 169 (80 mg, 151 μmol), 4-chloropyrimidine-2-carbonitrile (23 mg, 166 μmol) and DIEA (58 mg, 453 μmol) in NMP (2 mL) were taken up into a microwave tube. The sealed tube was heated at 130° C. for 0.5 hr under microwave. The reaction mixture was poured into H₂O (10 mL) at 0° C. and extracted with CH₂Cl₂ (45 mL). The organic layer was dried over anhydrous Na₂SO₄, filtered and concentrated under reduced pressure. After purified by prep-HPLC (column: Phenomenex C18 150*25 mm*10 μm; mobile phase: [water (NH₄HCO₃)-ACN]; gradient: 48%-78% B over 14 min), 4-(9-(4-(2-(2-aminopyridin-3-yl)-5-phenyl-3H-imidazo[4,5-b]pyridin-3-yl)benzyl)-3,9-diazaspiro[5.5]undecan-3-yl)pyrimidine-2-carbonitrile (Example 364, 7.5 mg, yield: 7.7%) was obtained as a pink lyophilized powder. MS: m/z=633.5 [M+H]⁺. ¹H NMR (400 MHz, Dimethylsulfoxide-d₆) δ. 8.27 (d, J=8.4 Hz, 1H), 8.21 (d, J=6.8 Hz, 1H), 8.05-7.96 (m, 4H), 7.48-7.38 (m, 7H), 7.15 (dd, J=7.6, 1.6 Hz, 1H), 7.08 (d, J=6.8 Hz, 1H), 7.03 (br s, 2H), 6.36 (dd, J=7.6, 4.8 Hz, 1H), 3.68-3.61 (m, 2H), 3.59 (s, 2H), 3.31-3.27 (m, 2H), 2.44-2.38 (m, 4H), 1.56-1.45 (m, 8H).

Example 365: 4-(9-(4-(2-(2-Aminopyridin-3-yl)-5-phenyl-3H-imidazo[4,5-b]pyridin-3-yl)benzyl)-3,9-diazaspiro[5.5]undecan-3-yl)-1,3,5-triazine-2-carbonitrile

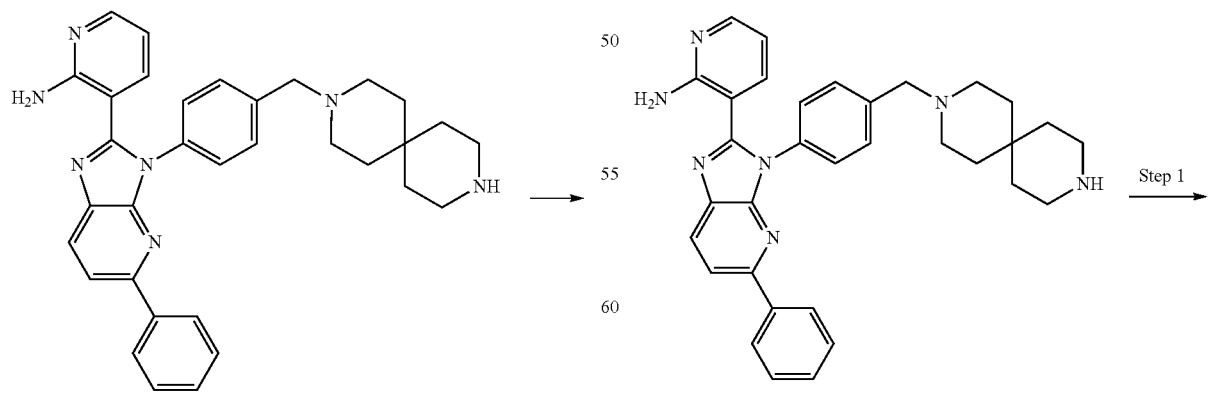

Intermediate 169              Intermediate 169

-continued

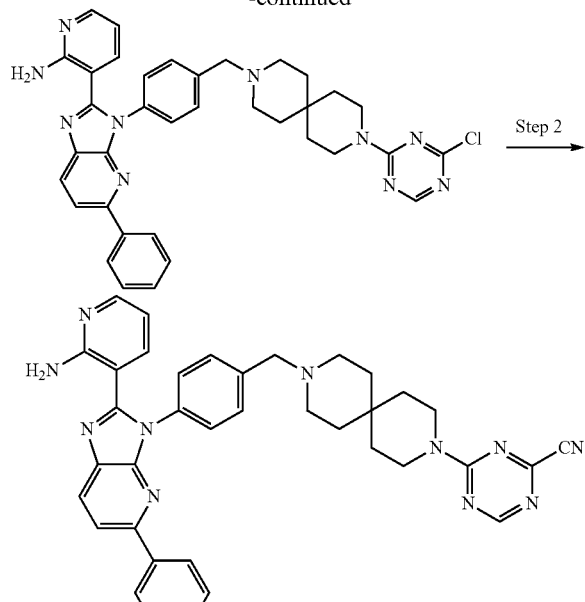

Example 365

Step 1: 3-(3-(4-((9-(4-Chloro-1,3,5-triazin-2-yl)-3,9-diazaspiro[5.5]undecan-3-yl)methyl)phenyl)-5-phenyl-3H-imidazo[4,5-b]pyridin-2-yl)pyridin-2-amine To a solution of Intermediate 169 (80 mg, 151 μmol) in THF (8 mL) and H$_2$O (2 mL) was added DIEA (59 mg, 453 μmol). The mixture was stirred at 0° C. for 10 min. Then 4-chloro-1,3,5-triazine-2-carbonitrile (27 mg, 181 μmol) in THF (1.5 mL) was added to the mixture. The mixture was stirred at 0° C. for 1 hr. The reaction mixture was extracted with CH$_2$Cl$_2$ (30 mL). The organic phase layers were dried over anhydrous Na$_2$SO$_4$, filtered and concentrated under reduced pressure. After purified by prep-TLC (CH$_2$Cl$_2$:MeOH=10:1), 3-(3-(4-((9-(4-chloro-1,3,5-triazin-2-yl)-3,9-diazaspiro[5.5]undecan-3-yl)methyl)phenyl)-5-phenyl-3H-imidazo[4,5-b]pyridin-2-yl)pyridin-2-amine (13.8 mg, yield: 14%) was obtained as a yellow solid. MS: m/z=643.2 [M+H]$^+$. $^1$H NMR (400 MHz, Methanol-d$_4$) δ 8.29 (s, 1H), 0.8.19 (d, J=8.4 Hz, 1H), 8.05-8.01 (m, 2H), 8.00-7.96 (m, 1H), 7.96-7.88 (m, 1H), 8.19 (d, J=8.4 Hz, 2H), 7.47-7.31 (m, 6H), 6.51-6.43 (m, 1H), 3.90-3.86 (m, 2H), 3.85-3.80 (m, 2H), 3.65 (s, 2H), 2.61-2.51 (m, 4H), 1.68-1.63 (m, 4H), 1.59-1.54 (m, 4H).

Step 2: 4-(9-(4-(2-(2-Aminopyridin-3-yl)-5-phenyl-3H-imidazo[4,5-b]pyridin-3-yl)benzyl)-3,9-diazaspiro[5.5]undecan-3-yl)-1,3,5-triazine-2-carbonitrile To a solution of 3-(3-(4-((9-(4-chloro-1,3,5-triazin-2-yl)-3,9-diazaspiro[5.5]undecan-3-yl)methyl)phenyl)-5-phenyl-3H-imidazo[4,5-b]pyridin-2-yl)pyridin-2-amine (80 mg, 124 μmol) in DMSO (1 mL) was added KCN (57 mg, 871 μmol) and DABCO (2.8 mg, 25 μmol). The mixture was stirred at 25° C. for 16 hr. The reaction mixture was poured into water (5 mL). The resulting mixture was extracted with CH$_2$Cl$_2$ (6 mL). The combined organic layers were washed with brine (2 ml) and dried over anhydrous Na$_2$SO$_4$, filtered and concentrated to dryness. After purified by prep-TLC (CH2Cl$_2$:MeOH=10:1), 4-(9-(4-(2-(2-aminopyridin-3-yl)-5-phenyl-3H-imidazo[4,5-b]pyridin-3-yl)benzyl)-3,9-diazaspiro[5.5]undecan-3-yl)-1,3,5-triazine-2-carbonitrile (Example 365, 10.8 mg, yield: 13%) was obtained as a yellow solid. MS: m/z=634.3 [M+H]$^+$. $^1$H NMR (400 MHz, Chloroform-d) δ 8.53 (s, 1H), 8.14 (d, J=8.4 Hz, 1H), 8.09-8.05 (m, 1H), 8.02 (d, J=7.6 Hz, 2H), 7.81 (d, J=8.4 Hz, 1H), 7.61-7.51 (m, 2H), 7.47-7.41 (m, 4H), 7.40-7.36 (m, 1H), 7.09 (d, J=6.4 Hz, 1H), 6.60 (br s, 2H), 6.36 (dd, J=7.6, 4.8 Hz, 1H), 3.87-3.81 (m, 4H), 3.79-3.64 (m, 2H), 2.77-2.51 (m, 4H), 1.61-1.60 (m, 8H).

Example 366: 4-(6-(4-(2-(2-Aminopyridin-3-yl)-5-phenyl-3H-imidazo[4,5-b]pyridin-3-yl)benzyl)-2,6-diazaspiro[3.3]heptan-2-yl)pyrimidine-2-carbonitrile

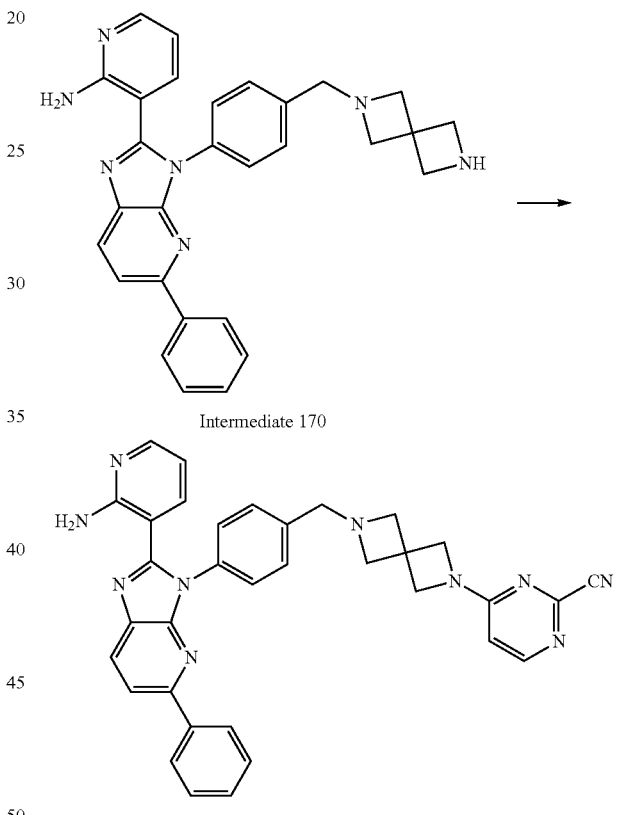

Intermediate 170

Example 366

To a solution of Intermediate 170 (80 mg, 169 gmol) in DMF (2 mL) were added 4-chloropyrimidine-2-carbonitrile (26 mg, 186 μmol) and DIEA (66 mg, 507 μmol). The mixture was stirred at 80° C. for 1.5 hr. The reaction mixture was poured into H$_2$O (15 mL), extracted with EtOAc (45 mL). The organic layers were dried over anhydrous Na$_2$SO$_4$, filtered and concentrated under reduced pressure. After purified by prep-HPLC (column: Phenomenex C18 150*25 mm*10 μm; mobile phase: [water (NH$_4$HCO$_3$)-ACN]; gradient: 37%-67% B over 14 min), 4-(6-(4-(2-(2-aminopyridin-3-yl)-5-phenyl-3H-imidazo[4,5-b]pyridin-3-yl)benzyl)-2,6-diazaspiro[3.3]heptan-2-yl)pyrimidine-2-carbonitrile (Example 366, 6.1 mg, yield: 6%) was obtained as an off-white lyophilized powder. MS: m/z=577.3 [M+H]$^+$. $^1$H NMR (400 MHz, Dimethylsulfoxide-d$_6$) δ 8.32-8.14 (m, 2H), 8.08-7.94 (m, 4H), 7.50-7.37 (m, 7H), 7.15 (d, J=7.6 Hz, 1H), 7.01 (br s, 2H), 6.62 (d, J=5.6 Hz, 1H), 6.46-6.32 (m, 1H), 4.20 (s, 4H), 3.64 (s, 2H), 3.38 (s, 4H).

Example 367: 4-((3aS,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile

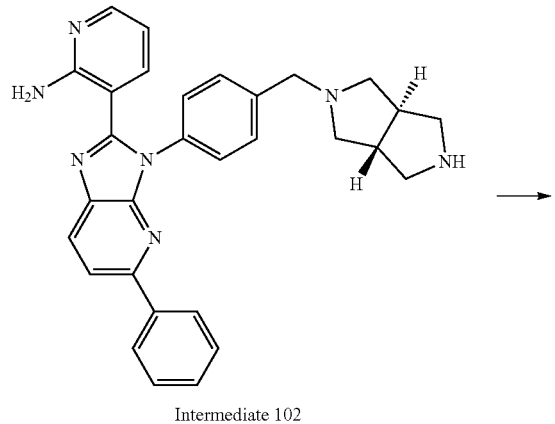

Intermediate 102

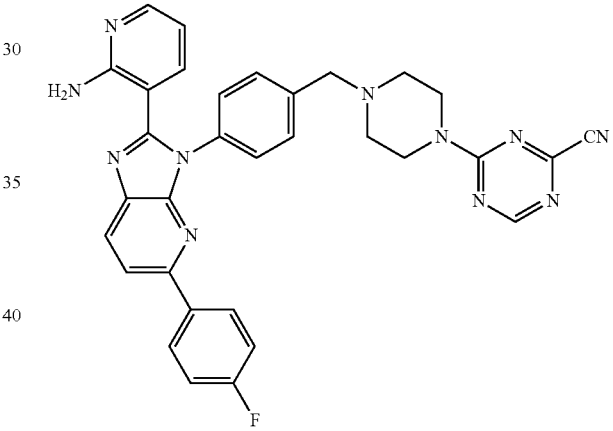

Example 367

To a solution of Intermediate 102 (81.0 mg HCl salt, 155 µmol) in NMP (0.8 mL) were added 4-chloropyrimidine-2-carbonitrile (21.6 mg, 155 µmol) and DIEA (59.9 mg, 81 µL). The mixture was stirred at 5° C. for 10 min. The residue was purified by pre-HPLC column: Welch Xtimate C18 150×25 mm×5 µm; mobile phase: [water (NH$_3$H$_2$O+NH$_4$HCO$_3$)-ACN]; gradient: 60%-90% B over 7 min to give 4-((3aS,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile (Example 367, 11.0 mg, yield: 12%) as a white solid. MS: m/z=591.3 [M+H]$^+$. $^1$H NMR (400 MHz, Dimethylsulfoxide-d$_6$) δ 8.27 (d, J=8.0 Hz, 1H), 8.22 (d, J=6.4 Hz, 1H), 8.06-8.01 (m, 2H), 8.01-7.97 (m, 2H), 7.53-7.37 (m, 7H), 7.17 (dd, J=7.6, 1.6 Hz, 1H), 7.03 (br s, 2H), 6.74 (d, J=6.4 Hz, 1H), 6.39 (dd, J=7.6, 4.8 Hz, 1H), 4.02-3.91 (m, 2H), 3.83 (dd, J=10.8, 6.8 Hz, 1H), 3.61 (dd, J=9.2, 6.4 Hz, 1H), 3.13-3.07 (m, 2H), 2.95-2.88 (m, 2H), 2.72-2.62 (m, 2H), 2.44-2.29 (m, 2H).

Example 368: 4-(4-(4-(2-(2-Aminopyridin-3-yl)-5-(4-fluorophenyl)-3H-imidazo[4,5-b]pyridin-3-yl)benzyl)piperazin-1-yl)-1,3,5-triazine-2-carbonitrile

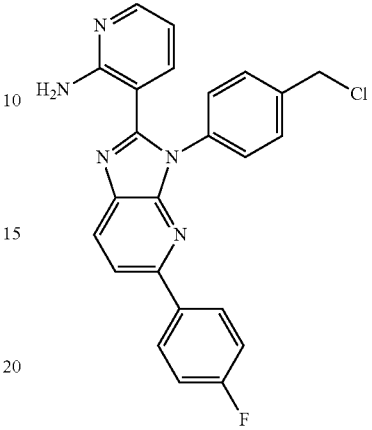

Intermediate 89

Example 368

To a solution of Intermediate 89 (300 mg, 643 µmol) and Intermediate 55 (196 mg, 643 µmol) in DMF (2 mL) were added NaI (48.2 mg, 322 µmol) and K$_2$CO$_3$ (445 mg, 3.22 mmol). The mixture was stirred at 50° C. for 0.5 hr. The reaction mixture was filtered and purified by prep-HPLC (column: Waters xbridge 150*25 mm*10 µm; mobile phase: [water (NH$_4$HCO$_3$)-ACN]; gradient. 50%-80% B over 10 min) to give 4-(4-(4-(2-(2-aminopyridin-3-yl)-5-(4-fluorophenyl)-3H-imidazo[4,5-b]pyridin-3-yl)benzyl)piperazin-1-yl)-1,3,5-triazine-2-carbonitrile (Example 368, 22.4 mg, yield: 5.7%) as a light-yellow solid. MS: m/z=584.4 [M+H]$^+$. $^1$H NMR (400 MHz, Dimethylsulfoxide-d$_6$) δ 8.73 (s, 1H), 8.27 (d, J=8.4 Hz, 1H), 8.08 (dd, J=8.8, 6.0 Hz, 2H), 8.01-7.97 (m, 2H), 7.53-7.50 (m, 2H), 7.48-7.45 (m, 2H), 7.33-7.28 (m, 2H), 7.15 (d, J=6.8 Hz, 1H), 7.02 (br s, 1H), 6.39 (dd, J=8.0, 4.8 Hz, 1H), 3.89-3.79 (m, 4H), 3.65 (s, 2H), 3.37-3.33 (m, 2H), 3.32-3.26 (m, 2H). $^{19}$F NMR (377 MHz, Dimethylsulfoxide-d$_6$) δ −113.57.

Example 369: 4-(4-(4-(2-(2-Aminopyridin-3-yl)-5-(4-chlorophenyl)-3H-imidazo[4,5-b]pyridin-3-yl)benzyl)piperazin-1-yl)-1,3,5-triazine-2-carbonitrile

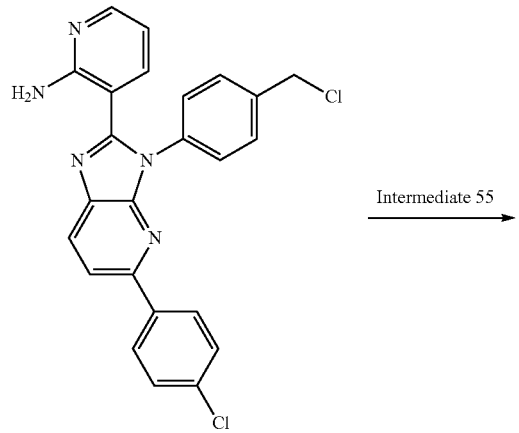

Intermediate 55 →

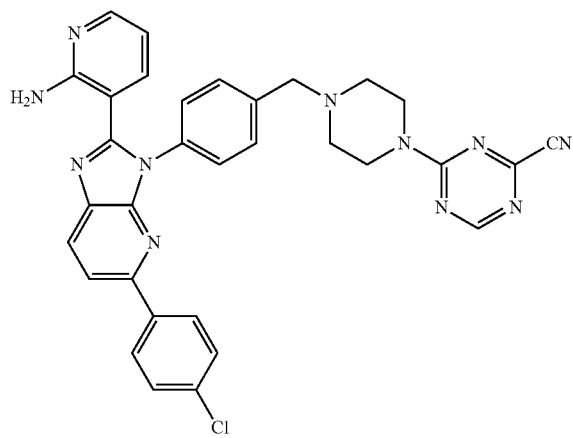

Example 369

Example 370: 4-((1-(4-(2-(2-Aminopyridin-3-yl)-5-(4-fluorophenyl)-3H-imidazo[4,5-b]pyridin-3-yl)benzyl)piperidin-4-yl)amino)pyrimidine-2-carbonitrile

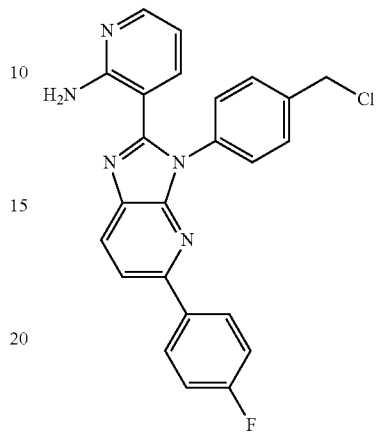

Intermediate 107

Intermediate 51 →

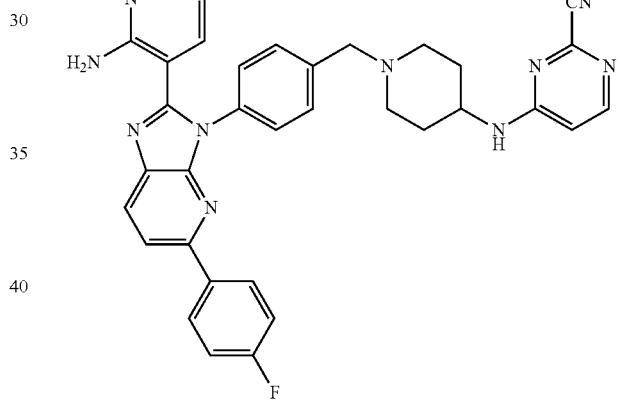

Example 370

To a solution of 3-(3-(4-(chloromethyl)phenyl)-5-(4-chlorophenyl)-3H-imidazo[4,5-b]pyridin-2-yl)pyridin-2-amine (refer to Intermediate 43 for detail procedures, 300 mg, 621 μmol) and Intermediate 55 (189 mg, 621 μmol) in DMF (2 mL) were added NaI (46.4 mg, 311 μmol) and $K_2CO_3$ (429 mg, 3.11 mmol). The mixture was stirred at 50° C. for 2 hr. The reaction mixture was filtered and purified by prep-HPLC (column: Waters xbridge 150*25 mm*10 μm; mobile phase: [water ($NH_4HCO_3$)-ACN]; gradient: 58%-88% B over 10 min) to give 4-(4-(4-(2-(2-aminopyridin-3-yl)-5-(4-chlorophenyl)-3H-imidazo[4,5-b]pyridin-3-yl)benzyl)piperazin-1-yl)-1,3,5-triazine-2-carbonitrile (Example 369, 12 mg, yield: 3.1%) as a light-yellow solid. MS: m/z=600.4 [M+H]$^+$. $^1$H NMR (400 MHz, Dimethylsulfoxide-$d_6$) δ 8.73 (s, 1H), 8.29 (d, J=8.4 Hz, 1H), 8.06 (d, J=8.4 Hz, 2H), 8.01 (d, J=8.0 Hz, 2H), 7.55-7.52 (m, 4H), 7.49-7.46 (m, 2H), 7.16 (d, J=7.2 Hz, 1H), 7.03 (br s, 2H), 6.39 (dd, J=7.6, 4.8 Hz, 1H), 3.89-3.80 (m, 4H), 3.65 (s, 2H), 3.37-3.34 (m, 2H), 3.31-3.26 (m, 2H).

To a solution of Intermediate 107 (250 mg, 581 μmol) and Intermediate 51 (180 mg, 567 μmol) in ACN (10 mL) were added $K_2CO_3$ (482 mg, 3.49 mmol) and NaI (17.4 mg, 116 μmol). The mixture was stirred at 80° C. for 3 hr. The reaction mixture was diluted with $H_2O$ (50 mL) and extracted with $CH_2Cl_2$ (50 mL×2). The combined organic layers were washed with brine (50 mL×2), dried over $Na_2SO_4$, filtered and concentrated under reduced pressure. After purified by silica gel flash chromatography (Eluent of 0~8% MeOH in $CH_2Cl_2$), 4-((1-(4-(2-(2-aminopyridin-3-yl)-5-(4-fluorophenyl)-3H-imidazo[4,5-b]pyridin-3-yl)benzyl)piperidin-4-yl)amino)pyrimidine-2-carbonitrile (Example 370, 76.6 mg, yield: 22%) was obtained as a light-yellow solid. MS: m/z=597.4 [M+H]$^+$. $^1$H NMR (400 MHz, Dimethylsulfoxide-$d_6$) δ 8.27 (d, J=8.4 Hz, 1H), 8.15-8.01 (m, 4H), 8.01-7.92 (m, 2H), 7.52-7.49 (m, 4H), 7.33-7.28 (m, 2H), 7.14 (d, J=6.8 Hz, 1H), 7.03 (br s, 2H), 6.67 (d, J=6.4 Hz, 1H), 6.37 (dd, J=7.6, 4.8 Hz, 1H), 3.95-3.73 (m, 1H), 3.59 (s, 2H), 2.87-2.80 (m, 2H), 2.20-2.18 (m, 2H), 1.95-1.86 (m, 2H), 1.57-1.41 (m, 2H).

Example 371: 2-((1-(4-(2-(2-Aminopyridin-3-yl)-5-(4-chlorophenyl)-3H-imidazo[4,5-b]pyridin-3-yl)benzyl)piperidin-4-yl)amino)pyrimidine-4-carbonitrile

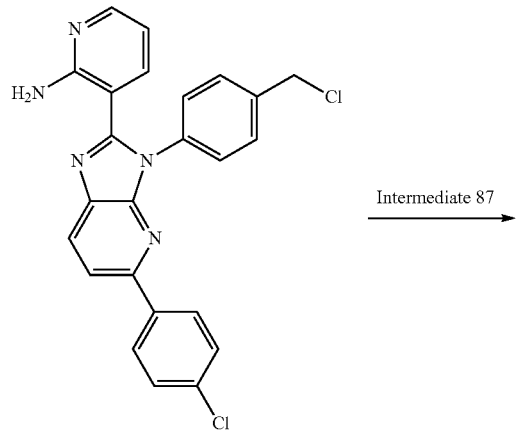

Intermediate 87

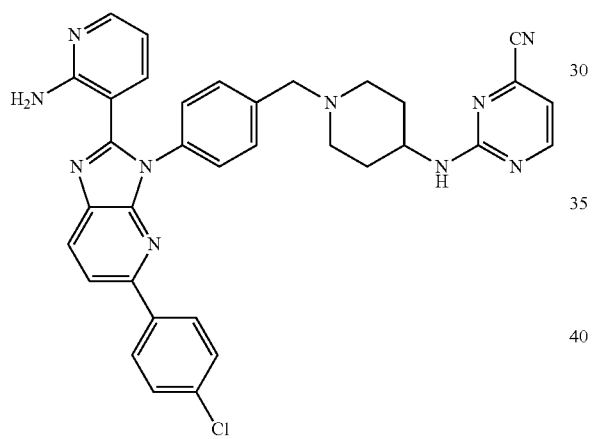

Example 371

Example 372: 2-((1-(4-(2-(2-Aminopyridin-3-yl)-5-(3-chlorophenyl)-3H-imidazo[4,5-b]pyridin-3-yl)benzyl)piperidin-4-yl)amino)pyrimidine-4-carbonitrile

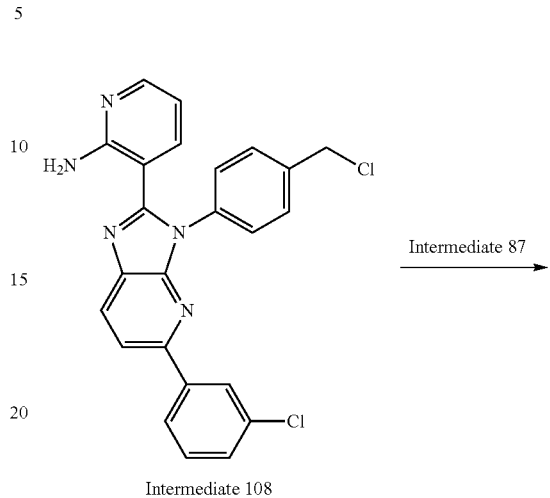

Intermediate 87

Intermediate 108

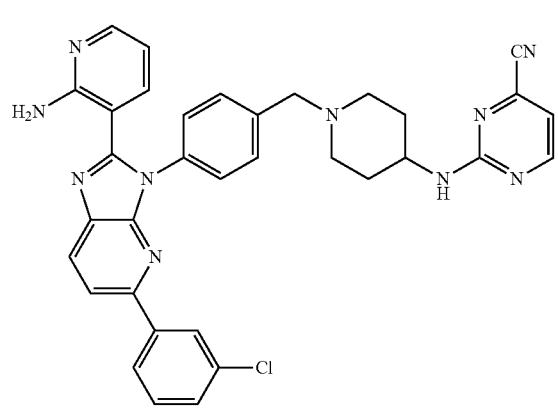

Example 372

To a solution of 3-(3-(4-(chloromethyl)phenyl)-5-(4-chlorophenyl)-3H-imidazo[4,5-b]pyridin-2-yl)pyridin-2-amine (refer to Intermediate 43 for detail procedures, 200 mg HCl salt, 414 μmol) and Intermediate 87 (131 mg TFA salt, 414 μmol) in DMF (5 mL) were added NaI (32 mg, 207 μmol) and K$_2$CO$_3$ (286 mg, 2.07 mmol). The mixture was stirred at 50° C. for 1 hr. The reaction mixture was filtered. After purified by prep-HPLC (column: Waters xbridge 150×25 mm 10 μm; mobile phase: [water (NH$_4$HCO$_3$)-ACN]; gradient: 59%-89% B over 14 min), 2-((1-(4-(2-(2-aminopyridin-3-yl)-5-(4-chlorophenyl)-3H-imidazo[4,5-b]pyridin-3-yl)benzyl)piperidin-4-yl)amino)pyrimidine-4-carbonitrile (Example 371, 48.1 mg, yield: 19%) was obtained as a yellow solid. MS: m/z=613.4 [M+H]$^+$. $^1$H NMR (400 MHz, Dimethylsulfoxide-d$_6$) δ 8.62 (d, J=4.8 Hz, 1H), 8.28 (d, J=9.2 Hz, 1H), 8.08-8.03 (m, 2H), 8.02-7.98 (m, 2H), 7.56-7.50 (m, 4H), 7.43 (d, J=8.4 Hz, 2H), 7.19 (dd, J=7.6, 1.6 Hz, 1H), 7.10 (d, J=4.8 Hz, 1H), 7.01 (br s, 2H), 6.40 (dd, J=8.0, 4.8 Hz, 1H), 4.41 (d, J=12.8 Hz, 2H), 3.86 (s, 2H), 3.18-3.11 (m, 2H), 2.79-2.70 (m, 1H), 1.95-1.86 (m, 2H), 1.32-1.22 (m, 2H).

To a solution of Intermediate 108 (200 mg HCl salt, 414 μmol) and intermediate 87 (131 mg TFA salt, 414 μmol) in DMF (4 mL) were added NaI (31 mg, 207 μmol) and K$_2$CO$_3$ (286 mg, 2.07 mmol). The mixture was stirred at 50° C. for 1 hr. The reaction mixture was filtered. After purified by prep-HPLC (column: Waters xbridge 150×25 mm 10 μm; mobile phase: [water (NH$_4$HCO$_3$)-ACN]; gradient: 56%-86% B over 10 min), 2-((1-(4-(2-(2-aminopyridin-3-yl)-5-(3-chlorophenyl)-3H-imidazo[4,5-b]pyridin-3-yl)benzyl)piperidin-4-yl)amino)pyrimidine-4-carbonitrile (Example 372, 28.3 mg, yield: 11%) was obtained as a yellow solid. MS: m/z=613.3 [M+H]$^+$. $^1$H NMR (400 MHz, Dimethylsulfoxide-d$_6$) δ 8.62 (d, J=4.4 Hz, 1H), 8.29 (d, J=8.4 Hz, 1H), 8.07-8.04 (m, 2H), 8.03-7.99 (m, 2H), 7.55 (d, J=8.4 Hz, 2H), 7.53-7.40 (m, 5H), 7.22-7.18 (m, 1H), 7.10 (d, J=4.8 Hz, 1H), 7.01 (br s, 2H), 6.40 (dd, J=7.6, 4.8 Hz, 1H), 4.43-4.36 (m, 2H), 3.87 (s, 2H), 3.18-3.10 (m, 2H), 2.78-2.72 (m, 1H), 1.93-1.89 (m, 2H), 1.32-1.24 (m, 2H).

Example 373: 6-((1-(4-(2-(2-Aminopyridin-3-yl)-5-(3-chlorophenyl)-3H-imidazo[4,5-b]pyridin-3-yl)benzyl)piperidin-4-yl)amino)pyrimidine-4-carbonitrile

Example 374: 6-(4-(4-(2-(2-Aminopyridin-3-yl)-5-(3-chlorophenyl)-3H-imidazo[4,5-b]pyridin-3-yl)benzyl)piperazin-1-yl)pyrimidine-4-carbonitrile

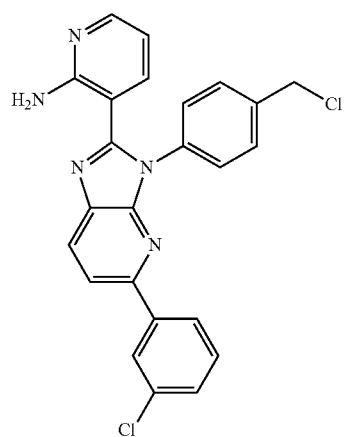

Intermediate 108

$\xrightarrow{\text{Intermediate 52}}$

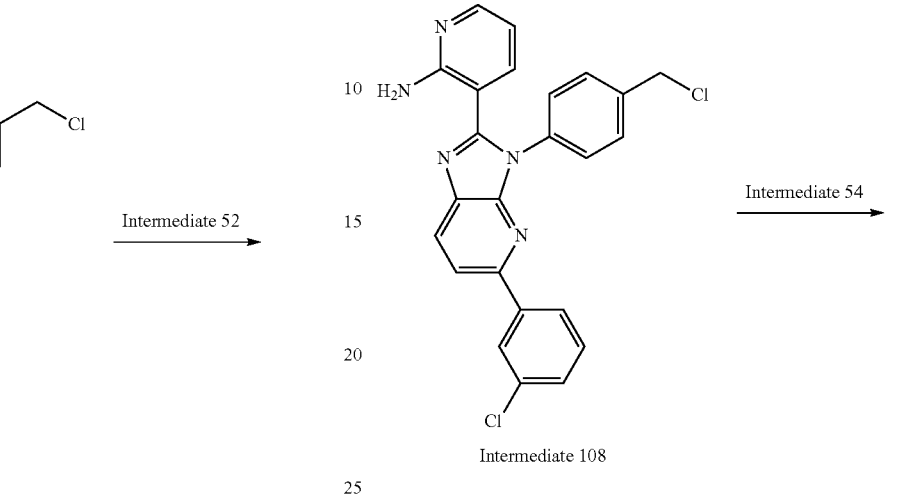

Intermediate 108

$\xrightarrow{\text{Intermediate 54}}$

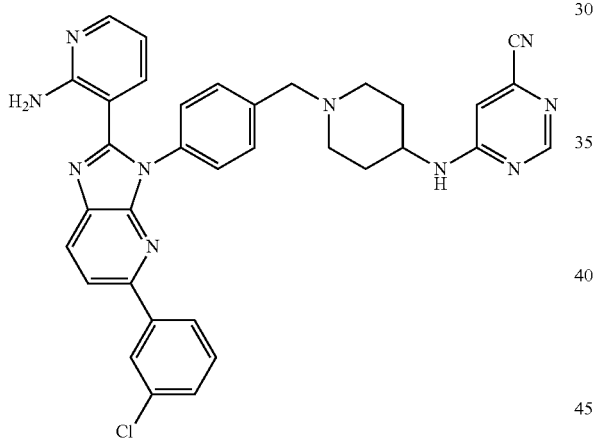

Example 373

Example 374

To a solution of Intermediate 108 (200 mg HCl salt, 414 μmol) and Intermediate 52 (131 mg TFA salt, 414 μmol) in DMF (5 mL) were added NaI (31 mg, 207 μmol) and K$_2$CO$_3$ (286 mg, 2.07 mmol). The mixture was stirred at 50° C. for 1 hr. The reaction mixture was filtered. After purified by prep-HPLC (column: Waters xbridge 150×25 mm 10 μm; mobile phase: [water (NH$_4$HCO$_3$)-ACN]; gradient: 50%-80% B over 14 min), 6-((1-(4-(2-(2-aminopyridin-3-yl)-5-(3-chlorophenyl)-3H-imidazo[4,5-b]pyridin-3-yl)benzyl)piperidin-4-yl)amino)pyrimidine-4-carbonitrile (Example 373, 97.1 mg, yield: 38%) was obtained as a yellow solid. MS: m/z=613.4 [M+H]$^+$. $^1$H NMR (400 MHz, Dimethylsulfoxide-d$_6$) δ 8.49 (s, 1H), 8.29 (d, J=8.4 Hz, 1H), 8.08-7.98 (m, 5H), 7.52-7.44 (m, 6H), 7.17 (dd, J=8.0, 2.0 Hz, 1H), 7.04 (s, 2H), 6.92 (s, 1H), 6.38 (dd, J=8.0, 4.8 Hz, 1H), 4.00-3.76 (m, 1H), 3.59 (s, 2H), 2.87-2.80 (m, 2H), 2.16-2.09 (m, 2H), 1.93-1.82 (m, 2H), 1.56-1.45 (m, 2H).

To a solution of Intermediate 108 (207 mg, 429 μmol) and Intermediate 54 (130 mg, 429 μmol) in DMF (3 mL) were added NaI (32.1 mg, 214 μmol) and K$_2$CO$_3$ (296 mg, 2.14 mmol). The mixture was stirred at 50° C. for 0.5 hr. The reaction mixture was filtered. After purified by prep-HPLC (column: Waters xbridge 150*25 mm*10 μm; mobile phase: [water (NH$_4$HCO$_3$)-ACN]; gradient: 54%-84% B over 14 min), 6-(4-(4-(2-(2-aminopyridin-3-yl)-5-(3-chlorophenyl)-3H-imidazo[4,5-b]pyridin-3-yl)benzyl)piperazin-1-yl)pyrimidine-4-carbonitrile (Example 374, 79.4 mg, yield: 30%) was obtained as a light-yellow solid. MS: m/z=599.4 [M+H]$^+$. $^1$H NMR (400 MHz, Dimethylsulfoxide-d$_6$) δ 8.57 (s, 1H), 8.29 (d, J=8.4 Hz, 1H), 8.07-8.04 (m, 2H), 8.03-7.99 (m, 2H), 7.58-7.56 (m, 1H), 7.54-7.50 (m, 3H), 7.49-7.46 (m, 3H), 7.16 (dd, J=7.6, 1.6 Hz, 1H), 7.05 (br s, 2H), 6.36 (dd, J=7.6, 4.8 Hz, 1H), 3.81-3.69 (m, 4H), 3.65 (s, 2H), 3.36-3.34 (m, 2H), 3.32-3.29 (m, 2H).

Example 375: 4-((1S,4S)-5-(4-(2-(2-Aminopyridin-3-yl)-5-phenyl-3H-imidazo[4,5-b]pyridin-3-yl)benzyl)-2,5-diazabicyclo[2.2.1]heptan-2-yl)pyrimidine-2-carbonitrile

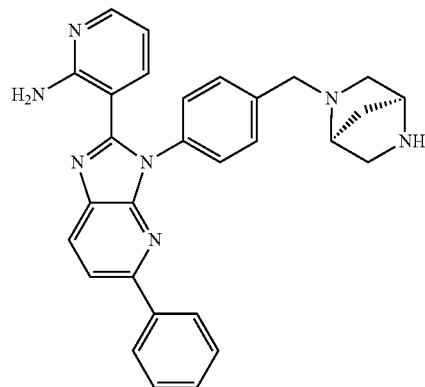

Intermediate 109

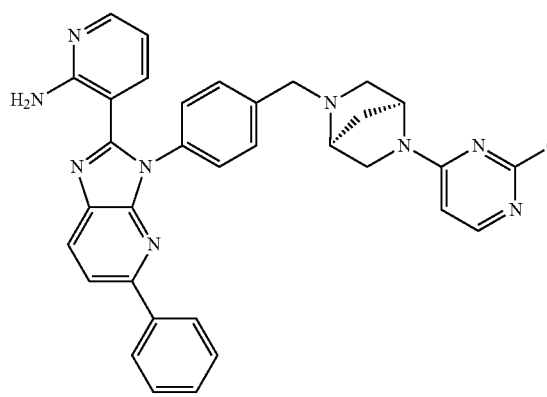

Example 375

A mixture of Intermediate 109 (100 mg, 211 μmol), 4-chloropyrimidine-2-carbonitrile (29 mg, 211 μmol) and DIEA (184 μL, 1.06 mmol) in NMP (1 mL) was taken up into a microwave tube. The sealed tube was heated at 130° C. for 1 hr under microwave. The reaction mixture was filtered and concentrated under reduced pressure. The residue was purified by prep-HPLC (column: Waters xbridge 150×25 mm 10 μm; mobile phase: [water (NH$_4$HCO$_3$)-ACN]; B %: 42%-72%, 10 min) to 4-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-2-carbonitrile (Example 375, 21.6 mg, yield: 17%) as a yellow solid. MS: m/z=577.3 [M+H]$^+$. $^1$H NMR (400 MHz, Dimethylsulfoxide-d$_6$) δ 8.26 (d, J=8.4 Hz, 1H), 8.24-8.18 (m, 1H), 8.04-7.96 (m, 4H), 7.52-7.39 (m, 7H), 7.16 (dd, J=7.6, 1.6 Hz, 1H), 7.00 (br s, 2H), 6.42-6.35 (m, 1H), 6.99-6.67 (m, 1H),), 4.94-4.65 (m, 1H), 3.84 (s, 2H), 3.71-3.53 (m, 2H), 3.44-3.38 (m, 2H), 3.00-2.89 (m, 1H), 2.06-1.95 (m, 1H), 1.88-1.76 (m, 1H).

Example 376: 6-((1S,4S)-5-(4-(2-(2-Aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile

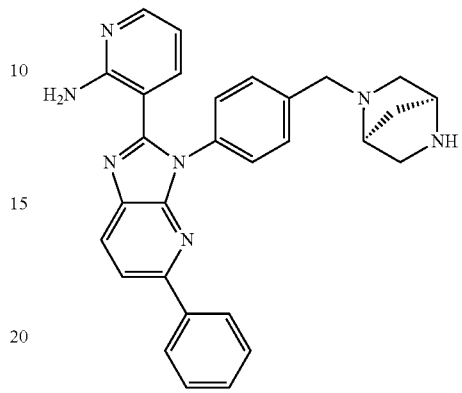

Intermediate 109

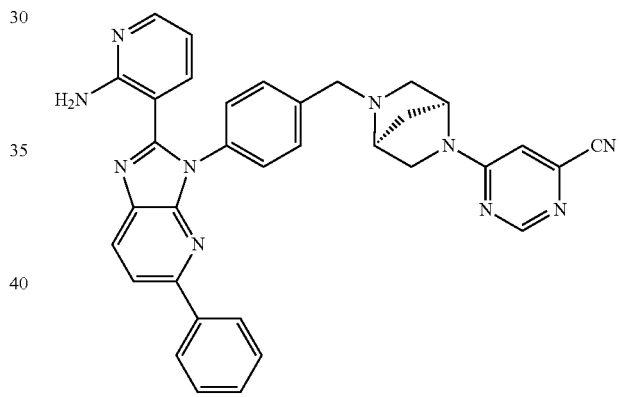

Example 376

A mixture of Intermediate 109 (100 mg, 211 μmol), 6-chloropyrimidine-4-carbonitrile (29 mg, 211 μmol) and DIEA (184 μL, 1.06 mmol) in NMP (1 mL) was taken up into a microwave tube. The sealed tube was heated at 130° C. for 1 hr under microwave. The reaction mixture was filtered and concentrated under reduced pressure. The residue was purified by prep-HPLC (column: Waters xbridge 150×25 mm 10 μm; mobile phase: [water (NH$_4$HCO$_3$)-ACN]; B %: 44%-74%, 10 min) to give 6-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl) pyrimidine-4-carbonitrile (Example 376, 24.7 mg, yield: 20%) as a yellow solid. MS: m/z=577.3 [M+H]$^+$. $^1$H NMR (400 MHz, Dimethylsulfoxide-d$_6$) δ 8.52 (d, J=12.8 Hz, 1H), 8.26 (d, J=8.0 Hz, 1H), 8.04-7.97 (m, 4H), 7.53-7.37 (m, 8H), 7.17-7.15 (m, 1H), 7.00 (br s, 2H), 6.39 (dd, J=8.0, 4.8 Hz, 1H), 5.00-4.67 (m, 1H), 3.86-3.79 (m, 2H), 3.72-3.57 (m, 2H), 3.45-3.36 (m, 2H), 2.96-2.89 (m, 1H), 2.05-1.96 (m, 1H), 1.87-1.78 (m, 1H).

Example 377: 2-((1S,4S)-5-(4-(2-(2-Aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile Example 378: 4-((2S,6R)-4-(4-(2-(2-Aminopyridin-3-yl)-5-phenyl-3H-imidazo[4,5-b]pyridin-3-yl)benzyl)-2,6-dimethylpiperazin-1-yl)pyrimidine-2-carbonitrile

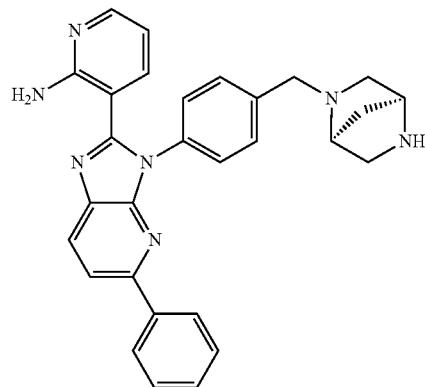

Intermediate 109

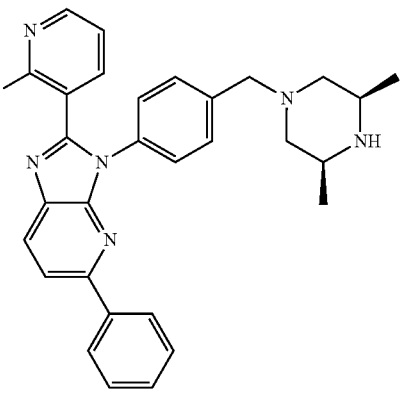

Intermediate 165

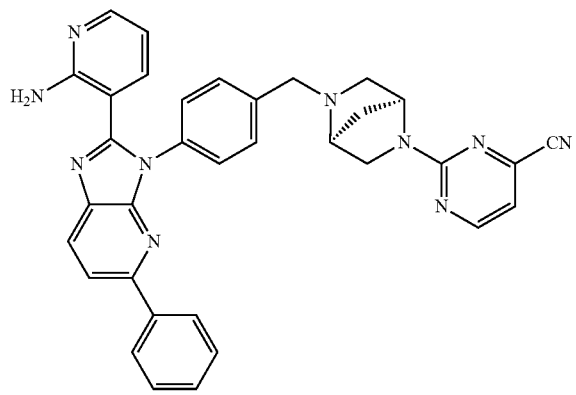

Example 377

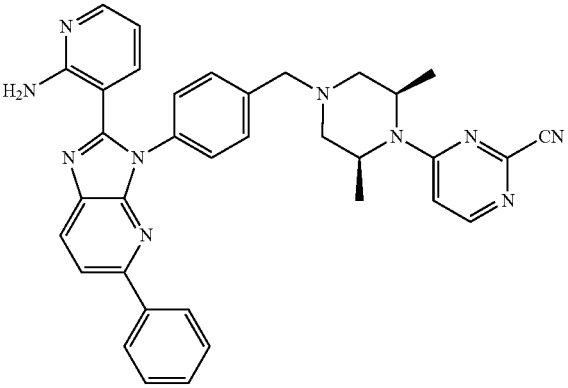

Example 378

A mixture of Intermediate 109 (100 mg, 211 μmol), 2-chloropyrimidine-4-carbonitrile (29 mg, 211 μmol) and DIEA (184 μL, 1.06 mmol) in NMP (1 mL) was taken up into a microwave tube. The sealed tube was heated at 130° C. for 1 hr under microwave. The reaction mixture was filtered and concentrated under reduced pressure. The residue was purified by prep-HPLC (column: Waters xbridge 150×25 mm 10 μm; mobile phase: [water (NH$_4$HCO$_3$)-ACN]; B %: 50%-80%, 10 min) to give 2-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl) pyrimidine-4-carbonitrile (Example 377, 13.1 mg, yield: 10%) as a yellow solid. MS: m/z=577.3 [M+H]$^+$. $^1$H NMR (400 MHz, Dimethylsulfoxide-d$_6$) δ 8.61 (dd, J=13.2, 4.8 Hz, 1H), 8.26 (d, J=8.0 Hz, 1H), 8.04-7.96 (m, 4H), 7.52-7.49 (m, 2H), 7.47-7.43 (m, 3H), 7.42-7.37 (m, 2H), 7.16 (dd, J=7.6, 1.6 Hz, 1H), 7.13 (d, J=4.8 Hz, 1H), 7.01 (br s, 2H), 6.39 (dd, J=7.2, 4.4 Hz, 1H), 4.84-4.70 (m, 1H), 3.83 (s, 2H), 3.70-3.64 (m, 2H), 3.45-3.35 (m, 2H), 2.98-2.93 (m, 1H), 2.59-2.52 (m, 2H), 2.00-1.96 (m, 1H), 1.85-1.81 (m, 1H).

A mixture of Intermediate 165 (80 mg, 164 μmol), 4-chloropyrimidine-2-carbonitrile (22.8 mg, 164 μmol) and DIEA (106 mg, 817 μmol) in NMP (2 mL) was taken up into a microwave tube. The sealed tube was heated at 160° C. for 1 hr under microwave. The reaction mixture was filtered to give a filter liquor. The filter liquor was purified by prep-HPLC (column: Welch Xtimate C18 150×25 mm×5 μm; mobile phase: [water (NH$_4$HCO$_3$)-ACN]; B %: 57%-87%, 10 min) to give 4-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile (Example 378, 6.4 mg, yield: 6.6%) as a gray solid. MS: m/z=593.4 [M+H]$^+$. $^1$H NMR (400 MHz, Methanol-d$_4$) 8.21-8.18 (m, 2H), 8.06-8.04 (m, 2H), 8.00-7.98 (m, 1H), 7.95 (d, J=8.4 Hz, 1H), 7.62 (d, J=8.0 Hz, 2H), 7.48-7.41 (m, 4H), 7.39-7.37 (m, 1H), 7.35 (dd, J=7.2, 1.6 Hz, 1H), 6.88 (d, J=6.4 Hz, 1H), 6.48 (dd, J=7.6, 4.8 Hz, 1H), 3.67 (s, 2H), 3.30-3.27 (m, 2H), 2.89-2.87 (m, 1H), 2.89-2.85 (m, 1H), 2.39-2.31 (m, 2H), 1.26 (d, J=6.0 Hz, 6H).

Example 379: 2-((2S,6R)-4-(4-(2-(2-Aminopyridin-3-yl)-5-phenyl-3H-imidazo[4,5-b]pyridin-3-yl)benzyl)-2,6-dimethylpiperazin-1-yl)pyrimidine-4-carbonitrile Example 380: 6-((2S,6R)-4-(4-(2-(2-Aminopyridin-3-yl)-5-phenyl-3H-imidazo[4,5-b]pyridin-3-yl)benzyl)-2,6-dimethylpiperazin-1-yl)pyrimidine-4-carbonitrile

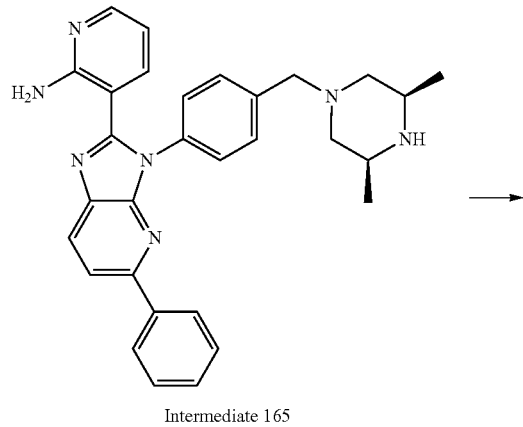

Intermediate 165

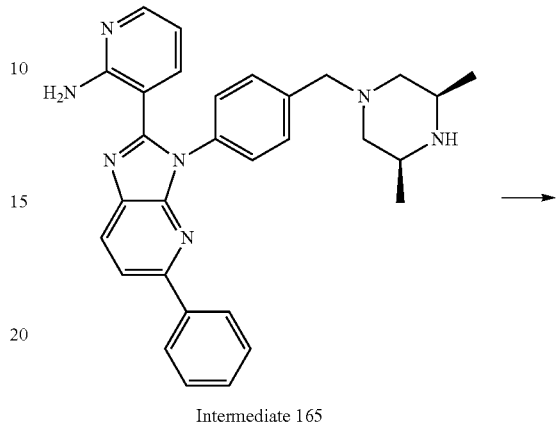

Intermediate 165


Example 379


Example 380

A mixture of Intermediate 165 (80 mg, 164 μmol), 2-chloropyrimidine-4-carbonitrile (22.8 mg, 164 μmol) and DIEA (106 mg, 817 μmol) in NMP (2 mL) was taken up into a microwave tube. The sealed tube was heated at 160° C. for 1 hr under microwave. The reaction mixture was filtered to give a filter liquor. The filter liquor was purified by prep-HPLC (column: Welch Xtimate C18 150×25 mm×5 μm; mobile phase: [water (NH$_4$HCO$_3$)-ACN]; B %: 66%-96%, 10 min) to give 2-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile (Example 379, 3.7 mg, yield: 3.7%) as a brown lyophilized powder. MS: m/z=593.2 [M+H]$^+$. $^1$H NMR (400 MHz, Dimethylsulfoxide-d$_6$) 8.67 (d, J=4.8 Hz, 1H), 8.27 (d, J=8.4 Hz, 1H), 8.06-8.03 (m, 2H), 8.02-7.98 (m, 2H), 7.60 (d, J=8.4 Hz, 2H), 7.49 (d, J=8.4 Hz, 2H), 7.46-7.43 (m, 2H), 7.41-7.38 (m, 1H), 7.19-7.15 (m, 2H), 7.06 (br s, 2H), 6.40 (dd, J=7.6, 4.8 Hz, 1H), 4.60-4.59 (m, 2H), 3.65 (s, 2H), 2.78 (d, J=11.2 Hz, 2H), 2.27-2.23 (m, 2H), 1.28 (d, J=6.4 Hz, 6H).

A mixture of Intermediate 165 (80 mg, 164 μmol), 6-chloropyrimidine-4-carbonitrile (22.8 mg, 164 μmol) and DIEA (106 mg, 817 μmol) in NMP (2 mL) was taken up into a microwave tube. The sealed tube was heated at 160° C. for 1 hr under microwave. The reaction mixture was filtered to give a filter liquor. The filter liquor was purified by prep-HPLC (column: Welch Xtimate C18 150×25 mm×5 μm; mobile phase: [water (NH$_4$HCO$_3$)-ACN]; B %: 55%-85%, 10 min) to 6-((2S,6R)-4-(4-(2-(2-Aminopyridin-3-yl)-5-phenyl-3H-imidazo[4,5-b]pyridin-3-yl)benzyl)-2,6-dimethylpiperazin-1-yl)pyrimidine-4-carbonitrile (Example 380, 8.5 mg, yield: 8.7%) as a brown lyophilized powder. MS: m/z=593.4 [M+H]$^+$. $^1$H NMR (400 MHz, Methanol-d$_4$) δ 8.54 (s, 1H), 8.20 (d, J=8.4 Hz, 1H), 8.05 (d, J=7.2 Hz, 2H), 7.99 (dd, J=5.2, 1.6 Hz, 1H), 7.95 (d, J=8.4 Hz, 1H), 7.62 (d, J=8.4 Hz, 2H), 7.43-7.41 (m, 4H), 7.39-7.37 (m, 1H), 7.34 (dd, J=7.6, 1.6 Hz, 1H), 7.23 (s, 1H), 6.49 (dd, J=7.6, 4.8 Hz, 1H), 3.69 (s, 2H), 3.34-3.30 (m, 2H), 2.86 (d, J=11.2 Hz, 2H), 2.33 (d, J=11.2 Hz, 2H), 1.37 (d, J=6.4 Hz, 6H).

Example 381: 4-((1-(4-(2-(2-Aminopyridin-3-yl)-5-(2-oxo-1,2-dihydropyridin-3-yl)-3H-imidazo[4,5-b]pyridin-3-yl)benzyl)piperidin-4-yl)amino)pyrimidine-2-carbonitrile

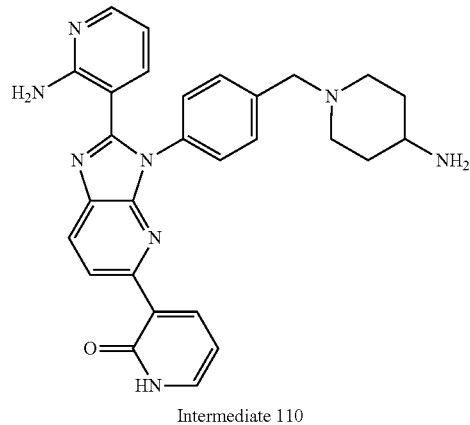

Intermediate 110

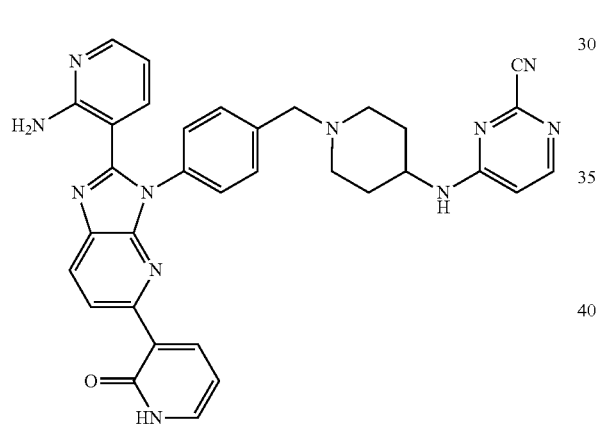

Example 381

A mixture of Intermediate 110 (85 mg, 173 μmol), 4-chloropyrimidine-2-carbonitrile (26.5 mg, 190 μmol) and DIEA (67 mg, 518 μmol) in NMP (2 mL) was taken up into a microwave tube. The sealed tube was heated at 130° C. for 30 min under microwave. The reaction mixture was filtered. The residue was purified by prep-HPLC (column: Waters xbridge 150*25 mm 10 μm; mobile phase: [water (NH$_4$HCO$_3$)-ACN]; B %: 6%-46%, 14 min) to give 4-((1-(4-(2-(2-aminopyridin-3-yl)-5-(2-oxo-1,2-dihydropyridin-3-yl)-3H-imidazo[4,5-b]pyridin-3-yl)benzyl)piperidin-4-yl)amino)pyrimidine-2-carbonitrile (Example 381, 10.2 mg, yield: 9.3%) as a light yellow solid. MS: m/z=596.3 [M+H]$^+$. $^1$H NMR (400 MHz, Dimethylsulfoxide-d$_6$) δ 11.98 (br s, 1H), 8.68 (d, J=8.4 Hz, 1H), 8.23 (dd, J=7.2, 2.0 Hz, 1H), 8.18 (d, J=8.4 Hz, 1H), 8.12-7.01 (m, 2H), 8.01-7.97 (m, 1H), 7.49-7.41 (m, 5H), 7.13 (d, J=7.6 Hz, 1H), 7.04 (br s, 2H), 6.67 (d, J=6.0 Hz, 1H), 6.39-6.34 (m, 2H), 3.90-3.75 (m, 1H), 3.59 (s, 2H), 2.86-2.80 (m, 2H), 2.20-2.10 (m, 2H), 1.94-1.84 (m, 2H), 1.56-1.45 (m, 2H).

Example 382: 4-((1-(4-(2-(2-Aminopyridin-3-yl)-5-(4-chlorophenyl)-3H-imidazo[4,5-b]pyridin-3-yl)benzyl)piperidin-4-yl)amino)-1,3,5-triazine-2-carbonitrile

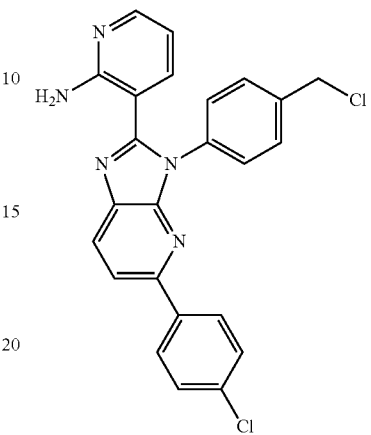

Intermediate 176

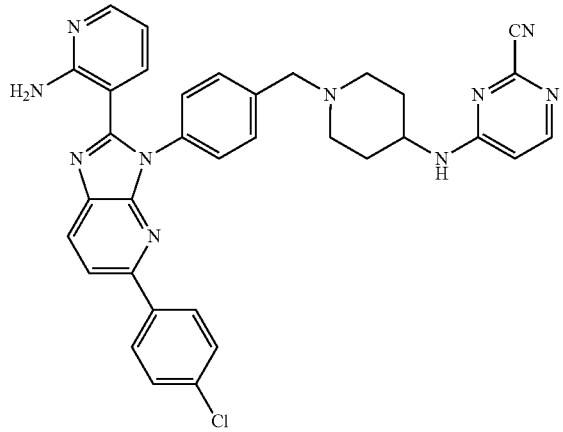

Example 382

A mixture of 3-(3-(4-(chloromethyl)phenyl)-5-(4-chlorophenyl)-3H-imidazo[4,5-b]pyridin-2-yl)pyridin-2-amine (refer to Intermediate 43 for detail procedures, 300 mg, 621 μmol), Intermediate 175 (198 mg, 621 μmol), NaI (47 mg, 311 μmol), and K$_2$CO$_3$ (429 mg, 3 mmol) in DMF (5 mL) was degassed and purged with N$_2$ three times, and then the mixture was stirred at 50° C. for 1 hr under N$_2$ atmosphere. After purified by prep-HPLC (column: Phenomenex C18 250×50 mm×10 μm; mobile phase: [water (NH$_4$HCO$_3$)-ACN]; gradient: 47%-77% B over 11 min), 4-((1-(4-(2-(2-aminopyridin-3-yl)-5-(4-chlorophenyl)-3H-imidazo[4,5-b]pyridin-3-yl)benzyl)piperidin-4-yl)amino)-1,3,5-triazine-2-carbonitrile (Example 382, 22.8 mg, yield: 5.6%) was obtained as yellow solid. MS: m/z=614.4 [M+H]$^+$. $^1$H NMR (400 MHz, Dimethyl sulfoxide-d$_6$) δ 8.97-8.90 (m, 1H), 8.68-8.61 (m, 1H), 8.28 (d, J=8.4 Hz, 1H), 8.09-7.97 (m, 4H), 7.53 (d, J=8.4 Hz, 2H), 7.50-7.43 (m, 4H), 7.15 (d, J=7.6 Hz, 1H), 7.03 (br s, 2H), 6.36-6.35 (m, 1H), 3.84-3.69 (m, 1H), 3.57 (s, 2H), 2.89-2.81 (m, 2H), 2.15-2.02 (m, 2H), 1.86-1.80 (m, 2H), 1.64-1.50 (m, 2H).

Example 383: 4-(4-(4-(2-(2-Aminopyridin-3-yl)-5-(4-cyanopyridin-3-yl)-3H-imidazo[4,5-b]pyridin-3-yl)benzyl)piperazin-1-yl)pyrimidine-2-carbonitrile

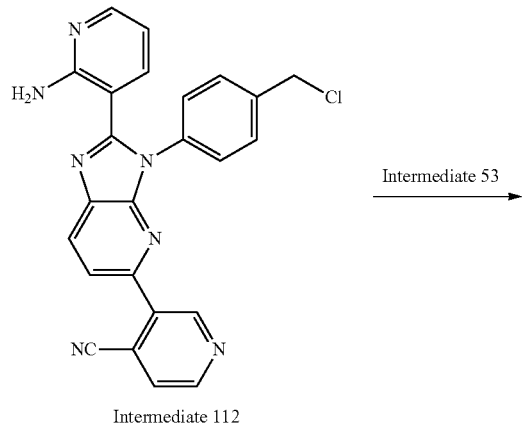

Intermediate 112

→ Intermediate 53

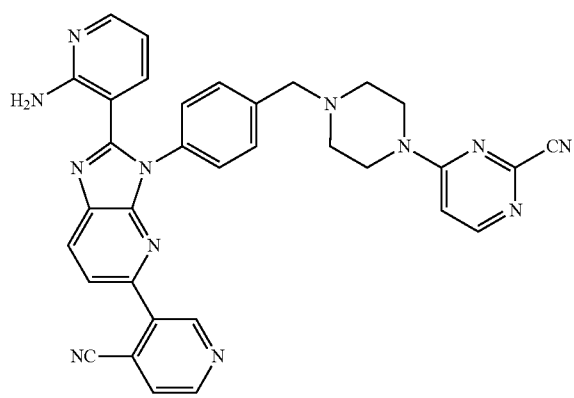

Example 383

To a solution of Intermediate 112 (100 mg, 228 μmol) and Intermediate 53 (43 mg, 228 μmol) in DMF (5 mL) were added NaI (17 mg, 114 μmol) and K$_2$CO$_3$ (158 mg, 1.0 mmol). The mixture was stirred at 50° C. for 1 hr. The reaction mixture was diluted with water (20 mL) and extracted with EtOAc (50 mL×2). The combined organic layers were washed with brine (30 mL), dried over Na$_2$SO$_4$, filtered and concentrated under reduced pressure. After purified by silica gel flash chromatography (Eluent of 0~7% MeOH in CH$_2$Cl$_2$), 4-(4-(4-(2-(2-aminopyridin-3-yl)-5-(4-cyanopyridin-3-yl)-3H-imidazo[4,5-b]pyridin-3-yl)benzyl)piperazin-1-yl)pyrimidine-2-carbonitrile (Example 383, 40.9 mg, yield: 30%) was obtained as a yellow solid. MS: m/z=591.4 [M+H]$^+$. $^1$H NMR (400 MHz, Dimethylsulfoxide-d$_6$) δ 9.20 (s, 1H), 8.84 (d, J=5.2 Hz, 1H), 8.43 (d, J=8.4 Hz, 1H), 8.26 (d, J=6.4 Hz, 1H), 8.04-7.96 (m, 3H), 7.51-7.45 (m, 4H), 7.21 (d, J=6.0 Hz, 1H), 7.11 (d, J=6.4 Hz, 1H), 7.01 (br s, 2H), 6.40 (dd, J=7.6, 5.2 Hz, 1H), 3.76-3.63 (m, 4H), 3.61 (s, 2H), 2.48-2.43 (m, 4H).

Example 384: 4-((1-(4-(2-(2-Aminopyridin-3-yl)-5-(4-cyanopyridin-3-yl)-3H-imidazo[4,5-b]pyridin-3-yl)benzyl)piperidin-4-yl)amino)pyrimidine-2-carbonitrile

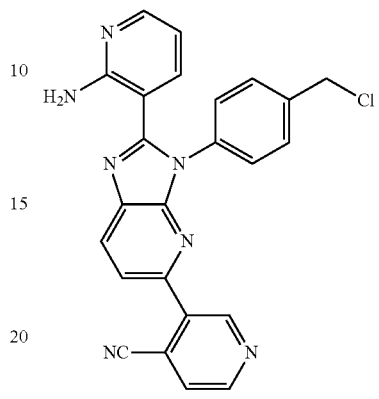

Intermediate 112

→ Intermediate 51

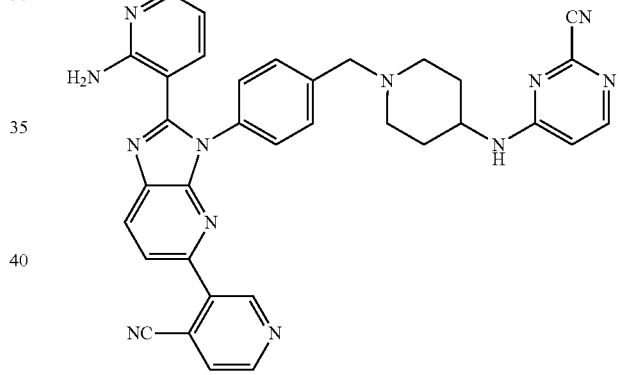

Example 384

To a solution of Intermediate 112 (100 mg, 228 μmol) and Intermediate 51 (72 mg, 357 μmol) in DMF (5 mL) were added NaI (17 mg, 114 μmol) and K$_2$CO$_3$ (158 mg, 1.0 mmol). The mixture was stirred at 50° C. for 1 hr. The reaction mixture was diluted with water (20 mL) and extracted with EtOAc (50 mL×2). The combined organic layers were washed with brine (30 mL), dried over Na$_2$SO$_4$, filtered and concentrated under reduced pressure. After purified by silica gel flash chromatography (Eluent of 0~7% MeOH in CH$_2$Cl$_2$), 4-((1-(4-(2-(2-aminopyridin-3-yl)-5-(4-cyanopyridin-3-yl)-3H-imidazo[4,5-b]pyridin-3-yl)benzyl)piperidin-4-yl)amino)pyrimidine-2-carbonitrile (Example 384, 24.2 mg, yield: 18%) was obtained as a yellow solid. MS: m/z=605.4 [M+H]$^+$. $^1$H NMR (400 MHz, Dimethylsulfoxide-d$_6$) δ 9.25-9.24 (m, 1H), 8.84 (d, J=4.8 Hz, 1H), 8.43 (d, J=8.0 Hz, 1H), 8.09-8.02 (m, 3H), 7.97 (d, J=4.8 Hz, 1H), 7.65 (s, 1H), 7.51-7.41 (m, 4H), 7.25-7.19 (m, 1H), 7.01 (br s, 2H), 6.67-6.66 (m, 1H), 6.44-6.38 (m, 1H), 4.06-3.69 (m, 1H), 3.55 (s, 2H), 2.82-2.80 (m, 2H), 2.15-2.08 (m, 2H), 1.92-1.81 (m, 2H), 1.52-1.42 (m, 2H).

Example 385: 4-((1-((4-(2-(2-Aminopyridin-3-yl)-3H-imidazo[4,5-b]pyridin-3-yl)phenyl)methyl-d$_2$)piperidin-4-yl)amino)pyrimidine-2-carbonitrile Example 386: 4-(4-(4-(2-(2-Aminopyridin-3-yl)-5-(4-methyl-3-oxo-1,4-diazepan-1-yl)-3H-imidazo[4,5-b]pyridin-3-yl)benzyl)piperazin-1-yl)pyrimidine-2-carbonitrile

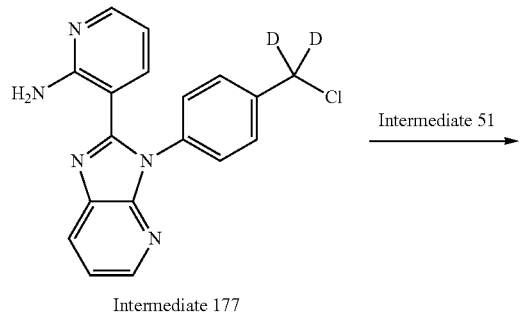

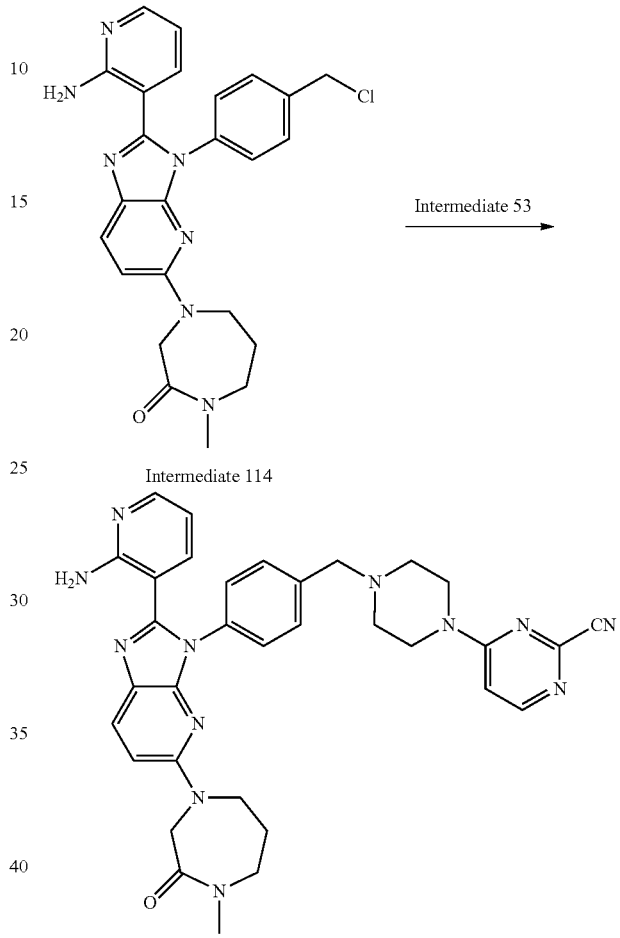

To a solution of Intermediate 177 (90 mg, 266 μmol) and Intermediate 51 (81 mg, 399 gmol) in DMF (2 mL) were added NaI (4.0 mg, 27 μmol) and K$_2$CO$_3$ (110 mg, 799 μmol). The mixture was stirred at 80° C. for 2 hr. The mixture was diluted with H$_2$O (10 mL) and extracted with EtOAc (10 mL×2). The combined organic layers were washed with brine (10 mL), dried over Na$_2$SO$_4$, filtered and concentrated under reduced pressure to give a residue. After purified by silica gel flash chromatography (Eluent of 0~7% MeOH in CH$_2$Cl$_2$), 4-((1-((4-(2-(2-aminopyridin-3-yl)-3H-imidazo[4,5-b]pyridin-3-yl)phenyl)methyl-d)piperidin-4-yl)amino)pyrimidine-2-carbonitrile (Example 385, 32.4 mg, yield: 24%) was obtained as a light yellow solid. MS: m/z=505.2 [M+H]$^+$. $^1$H NMR (400 MHz, Dimethylsulfoxide-d$_6$) δ 8.33 (d, J=4.4 Hz, 1H), 8.21 (d, J=8.0 Hz, 1H), 8.11-8.03 (m, 2H), 7.99 (d, J=4.4 Hz, 1H), 7.47-7.43 (m, 2H), 7.41-7.37 (m, 3H), 7.16 (d, J=8.0 Hz, 1H), 7.02 (br s, 2H), 6.67 (d, J=6.0 Hz, 1H), 6.37 (dd, J=7.6, 4.8 Hz, 1H), 3.87-3.74 (m, 1H), 2.85-2.78 (m, 2H), 2.20-2.09 (m, 2H), 1.93-1.83 (m, 2H), 1.53-1.43 (m, 2H)

To a solution of Intermediate 114 (250 mg, 541 μmol) and Intermediate 53 (113 mg, 595 μmol) in DMF (3 mL) was added DIEA (280 mg, 2.16 mmol). The mixture was stirred at 80° C. for 2 hr under N$_2$. The mixture was concentrated. After purified by prep-HPLC (column: Phenomenex C18 80*40 mm*3 μm; mobile phase: [water (NH$_3$H$_2$O+ NH$_4$HCO$_3$)-ACN]; gradient: 42%-72% B over 7 min), 4-(4-(4-(2-(2-aminopyridin-3-yl)-5-(4-methyl-3-oxo-1,4-diazepan-1-yl)-3H-imidazo[4,5-b]pyridin-3-yl)benzyl)piperazin-1-yl)pyrimidine-2-carbonitrile (Example 386, 9 mg, yield: 2.7%) was obtained as a yellow solid. MS: m/z=615.3 [M+H]$^+$. $^1$H NMR (400 MHz, Dimethylsulfoxide-d$_6$) δ 8.27 (d, J=6.4 Hz, 1H), 8.00-7.90 (m, 2H), 7.44 (d, J=8.4 Hz, 2H), 7.34 (d, J=8.4 Hz, 2H), 7.11 (d, J=6.4 Hz, 1H), 7.05-6.92 (m, 3H), 6.80 (d, J=8.8 Hz, 1H), 6.30 (dd, J=7.6, 4.8 Hz, 1H), 4.27 (s, 2H), 3.83-3.77 (m, 2H), 3.75-3.65 (m, 6H), 3.62 (s, 2H), 3.48-3.43 (m, 2H), 2.76 (s, 3H), 2.46-2.44 (m, 2H), 1.74-1.67 (m, 2H).

Example 387: 4-((1-(4-(2-(2-Aminopyridin-3-yl)-5-(3-oxomorpholino)-3H-imidazo[4,5-b]pyridin-3-yl)benzyl)piperidin-4-yl)amino)pyrimidine-2-carbonitrile Example 388: 4-((1-(4-(2-(2-Aminopyridin-3-yl)-5-cyclopentyl-3H-imidazo[4,5-b]pyridin-3-yl)benzyl)piperidin-4-yl)amino)pyrimidine-2-carbonitrile

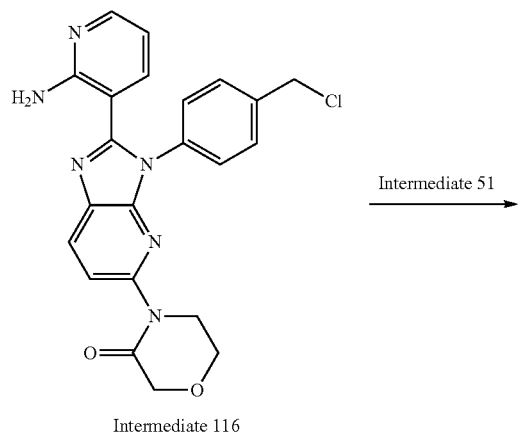

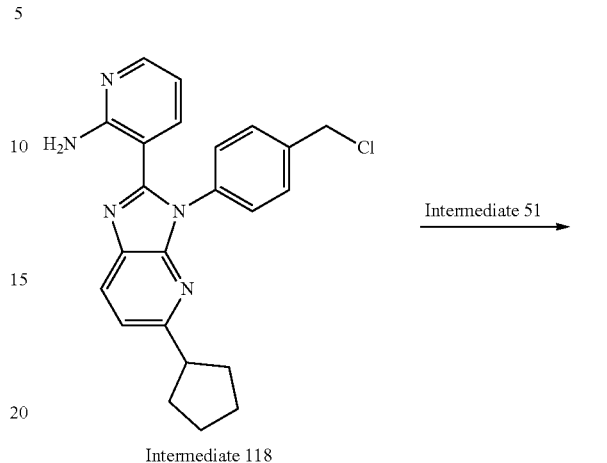

To a solution of Intermediate 116 (156 mg HCl salt, 331 μmol) and Intermediate 51 (105 mg TFA salt, 331 μmol) in DMF (2 mL) were added K$_2$CO$_3$ (137 mg, 993 μmol) and NaI (50 mg, 331 μmol). The mixture was stirred at 25° C. for 1 hr. The reaction mixture was diluted with H$_2$O (40 mL) and extracted with EtOAc (30 mL×2). The combined organic layers were washed with brine (30 mL), dried over Na$_2$SO$_4$, filtered and concentrated under reduced pressure. After purified by silica gel flash chromatography (Eluent of 0~7%, MeOH in CH$_2$Cl$_2$), 4-((1-(4-(2-(2-aminopyridin-3-yl)-5-(3-oxomorpholino)-3H-imidazo[4,5-b]pyridin-3-yl)benzyl)piperidin-4-yl)amino)pyrimidine-2-carbonitrile (Example 387, 26.5 mg, yield: 12%) was obtained as a yellow solid. MS: m/z=602.4 [M+H]$^+$. $^1$H NMR (400 MHz, Dimethylsulfoxide-d$_6$) δ 8.24 (d, J=8.4 Hz, 1H), 8.12-8.03 (m, 2H), 7.98 (dd, J=4.8, 1.6 Hz, 1H), 7.84 (d, J=8.8 Hz, 1H), 7.48-7.42 (m, 2H), 7.41-7.36 (m, 2H), 7.12 (dd, J=7.6, 1.6 Hz, 1H), 6.95 (br s, 2H), 6.67 (d, J=6.0 Hz, 1H), 6.37 (dd, J=7.6, 4.8 Hz, 1H), 4.25 (s, 2H), 3.98-3.92 (m, 2H), 3.86-3.83 (m, 2H), 3.57 (s, 2H), 3.18-3.13 (m, 1H), 2.82-2.79 (m, 2H), 2.16-2.11 (m, 2H), 1.92-1.84 (m, 2H), 1.55-1.47 (m, 2H).

To a solution of Intermediate 118 (100 mg, 248 gmol) and Intermediate 51 (86.4 mg, 272 mol) in DMF (1 mL) were added NaI (11 mg, 74 μmol) and K$_2$CO$_3$ (171 mg, 1.2 mmol). The mixture was stirred at 50° C. for 0.5 hr. The reaction mixture was poured into H$_2$O (15 mL), extracted with EtOAc (15 mL×3). The combined organic layers were dried over anhydrous Na$_2$SO$_4$, filtered and concentrated under reduced pressure. After purified by silica gel flash chromatography (Eluent of 0~15% MeOH in CH$_2$Cl$_2$), 4-((1-(4-(2-(2-aminopyridin-3-yl)-5-cyclopentyl-3H-imidazo[4,5-b]pyridin-3-yl)benzyl)piperidin-4-yl)amino)pyrimidine-2-carbonitrile (Example 388, 38.3 mg, yield: 27%) was obtained as a yellow solid. MS: m/z=571.2 [M+H]$^+$. $^1$H NMR (400 MHz, Dimethylsulfoxide-d$_6$) δ 8.13-8.03 (m, 3H), 7.97 (dd, J=4.8, 1.6 Hz, 1H), 7.44 (d, J=7.2 Hz, 2H), 7.39-7.34 (m, 2H), 7.30 (d, J=8.0 Hz, 1H), 7.09 (dd, J=4.8, 1.6 Hz, 1H), 6.94 (br s, 2H), 6.67 (d, J=6.0 Hz, 1H), 6.35 (dd, J=7.6, 4.8 Hz, 1H), 3.85-3.75 (m, 1H), 3.57 (s, 2H), 3.22-3.18 (m, 1H), 2.85-2.76 (m, 2H), 2.19-2.10 (m, 2H), 2.00-1.95 (m, 2H), 1.90-1.76 (m, 2H), 1.75-1.68 (m, 4H), 1.62-1.57 (m, 2H), 1.52-1.43 (m, 2H).

1475

Example 389: 4-((1-(4-(2-(2-Aminopyridin-3-yl)-5-(dimethylamino)-3H-imidazo[4,5-b]pyridin-3-yl)benzyl)piperidin-4-yl)amino)pyrimidine-2-carbonitrile

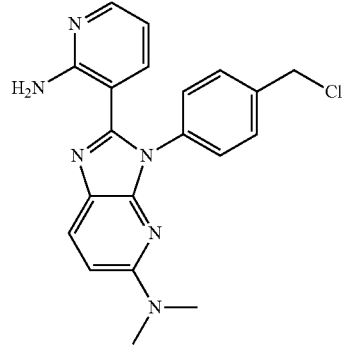

Intermediate 75

→ Intermediate 51

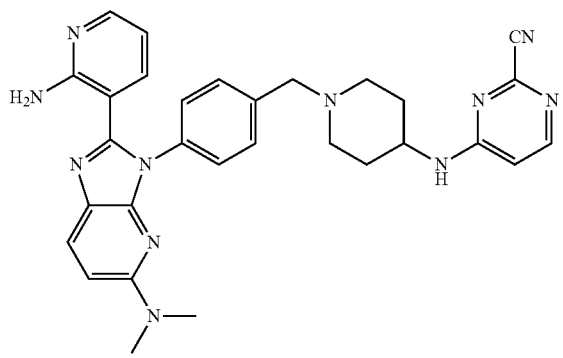

Example 389

To a solution of Intermediate 75 (300 mg, 792 μmol) and Intermediate 51 (161 mg TFA salt, 792 μmol) in DMF (5 mL) were added K$_2$CO$_3$ (547 mg, 3.96 mmol) and NaI (59.4 mg, 396 μmol). The mixture was stirred at 25° C. for 16 hr. The mixture was filtered, and the filtrate was concentrated to give the crude. After purified by prep-HPLC (column: Waters xbridge 150*25 mm 10 μm; mobile phase: [water (NH$_4$HCO$_3$)-ACN]; gradient: 33%-63% B over 14 min), 4-((1-(4-(2-(2-aminopyridin-3-yl)-5-(dimethylamino)-3H-imidazo[4,5-b]pyridin-3-yl)benzyl)piperidin-4-yl)amino) pyrimidine-2-carbonitrile (Example 389, 86.6 mg, yield: 20%) was obtained as a yellow powder. MS: m/z=546.4 [M+H]$^+$. $^1$H NMR (400 MHz, Methanol-d$_4$) δ 8.06-7.95 (m, 1H), 7.92 (dd, J=4.8, 1.6 Hz, 1H), 7.86 (d, J=9.2 Hz, 1H), 7.47 (d, J=8.4 Hz, 2H), 7.36 (d, J=8.4 Hz, 2H), 7.21 (dd, J=7.6, 1.6 Hz, 1H), 6.71 (d, J=9.2 Hz, 1H), 6.63-6.56 (m, 1H), 6.44 (dd, J=7.6, 4.8 Hz, 1H), 4.09-3.79 (m, 1H), 3.63 (s, 2H), 3.07 (s, 6H), 2.96-2.93 (m, 2H), 2.30-2.20 (m, 2H), 1.98-1.04 (m, 2H), 1.55-1.64 (m, 2H).

1476

Example 390: 4-((1-(4-(2-(2-Aminopyridin-3-yl)-3H-imidazo[4,5-b]pyridin-3-yl)benzyl)piperidin-4-yl)(methyl)amino)pyrimidine-2-carbonitrile

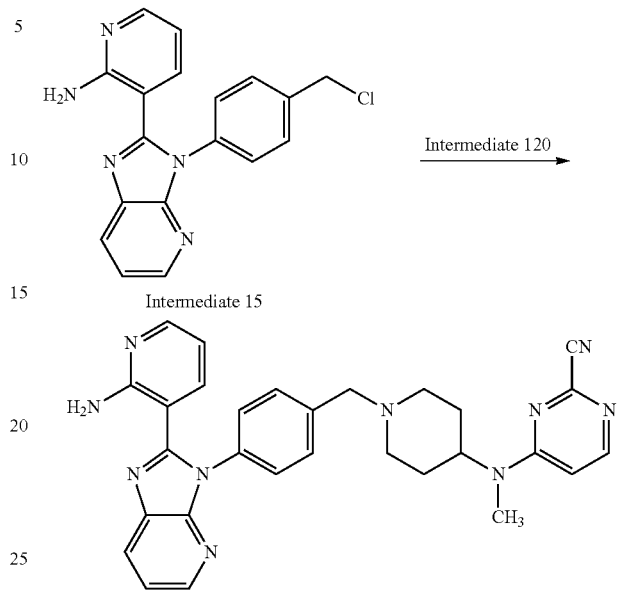

Intermediate 15

→ Intermediate 120

Example 390

To a solution of Intermediate 15 (150 mg, 447 μmol) and Intermediate 120 (116 mg, 536 μmol) in DMF (3 mL) were added NaI (6.7 mg, 45 μmol) and K$_2$CO$_3$ (185 mg, 1.3 mmol). The mixture was stirred at 50° C. for 1 hr. After purified by silica gel flash chromatography (Eluent of 0~7% MeOH in CH$_2$Cl$_2$), 4-((1-(4-(2-(2-Aminopyridin-3-yl)-3H-imidazo[4,5-b]pyridin-3-yl)benzyl)piperidin-4-yl)(methyl) amino)pyrimidine-2-carbonitrile (Example 390, 176.7 mg, yield: 98%) was obtained as a light-yellow solid. MS: m/z=517.2 [M+H]$^+$. $^1$H NMR (400 MHz, Dimethylsulfoxide-d$_6$) δ 8.33 (d, J=4.4 Hz, 1H), 8.26-8.18 (m, 2H), 7.99 (d, J=4.0 Hz, 1H), 7.49-7.44 (m, 2H), 7.42-7.36 (m, 3H), 7.17 (d, J=7.6 Hz, 1H), 7.08-6.84 (m, 3H), 6.38 (dd, J=7.2, 4.8 Hz, 1H), 4.91-4.34 (m, 1H), 3.59 (s, 2H), 2.99-2.84 (m, 5H), 2.23-2.10 (m, 2H), 1.91-1.77 (m, 2H), 1.65-1.53 (m, 2H).

Example 391: 4-((1-(4-(2-(2-Aminopyridin-3-yl)-5-phenyl-3H-imidazo[4,5-b]pyridin-3-yl)benzyl)piperidin-4-yl)amino)-1,3,5-triazine-2-carbonitrile

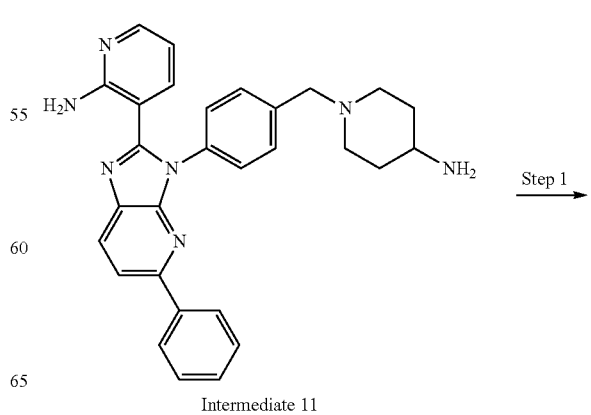

Intermediate 11

→ Step 1

-continued

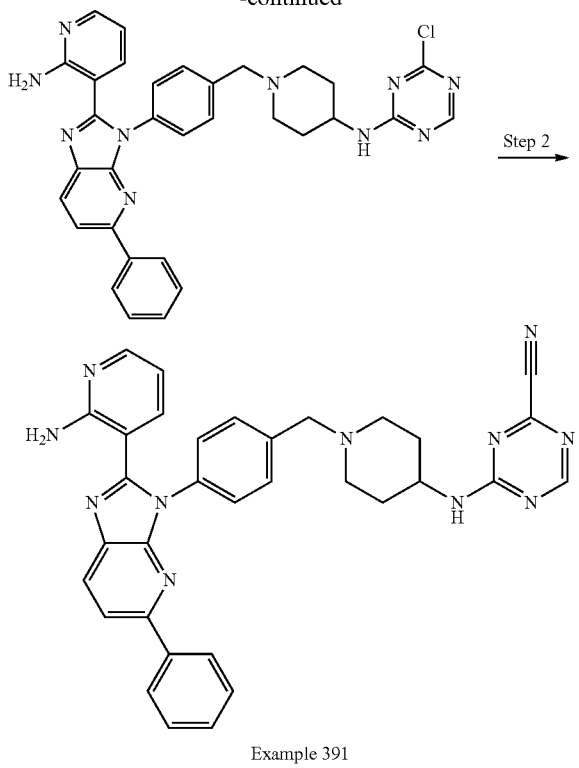

Example 391

Step 1: N-(1-(4-(2-(2-Aminopyridin-3-yl)-5-phenyl-3H-imidazo[4,5-b]pyridin-3-yl)benzyl)piperidin-4-yl)-4-chloro-1,3,5-triazin-2-amine To a solution of Intermediate 11 (200 mg, 404 μmol) in THF (4 mL) and H$_2$O (1 mL) was added K$_2$CO$_3$ (148 mg, 1.07 mmol) and stirred at 0° C. for 15 min. Then 2,4-dichloro-1,3,5-triazine (60.6 mg, 404 μmol) in THF (1 mL) was added into the mixture and stirred at 0° C. for 1.5 hr. The reaction was filtered to give the filter liquor and concentrated under reduced pressure. The residue was purified by prep-TLC (MeOH:CH$_2$Cl$_2$=1:10) to give N-(1-(4-(2-(2-amino-pyridin-3-yl)-5-phenyl-3H-imidazo[4,5-b]pyridin-3-yl)ben-zyl)piperidin-4-yl)-4-chloro-1,3,5-triazin-2-amine (6.3 mg, yield: 2.4%) as a light-yellow lyophilized powder. MS: m/z=589.3 [M+H]$^+$. $^1$H NMR (400 MHz, Dimethylsulfox-ide-d$_6$) δ 8.71 (br s, 1H), 8.49-8.35 (m, 1H), 8.27 (d, J=8.4 Hz, 1H), 8.06-7.95 (m, 5H), 7.55-7.35 (m, 6H), 7.16 (d, J=7.4 Hz, 1H), 7.02 (br s, 2H), 6.41-6.33 (m, 1H), 3.81-3.65 (m, 1H), 3.57 (s, 2H), 2.89-2.80 (m, 2H), 2.12-2.02 (m, 2H), 1.86-1.77 (m, 2H), 1.60-1.50 (m, 2H).

Step 2

To a solution of N-(1-(4-(2-(2-aminopyridin-3-yl)-5-phe-nyl-3H-imidazo[4,5-b]pyridin-3-yl)benzyl)piperidin-4-yl)-4-chloro-1,3,5-triazin-2-amine (150 mg, 255 μmol) and DABCO (5.71 mg, 51 μmol) in DMSO (1 mL) was added KCN (49.7 mg, 764 μmol). Then the mixture was stirred at 25° C. for 16 hr. The mixture was quenched with H$_2$O (15 mL) and extracted with CH$_2$Cl$_2$ (15 mL×3). The combined organic layers were dried over anhydrous Na$_2$SO$_4$, filtered and concentrated. The residue was purified by prep-HPLC (column: Waters xbridge 150×25 mm 10 μm; mobile phase: [water (NH$_4$HCO$_3$)-ACN]; B %: 49%-79%, 10 min) to give 4-((1-(4-(2-(2-aminopyridin-3-yl)-5-phenyl-3H-imidazo[4,5-b]pyridin-3-yl)benzyl)piperidin-4-yl)amino)-1,3,5-triaz-ine-2-carbonitrile (Example 391, 2.9 mg, yield: 1.8%) as a yellow solid. MS: m/z=580.2 [M+H]$^+$. $^1$H NMR (400 MHz, Acetonitrile-d$_3$) δ 8.61-8.47 (m, 1H), 8.17 (d, J=8.4 Hz, 1H), 8.06-7.98 (m, 3H), 7.90 (d, J=8.4 Hz, 1H), 7.52-7.39 (m, 7H), 7.16 (dd, J=7.6, 1.6 Hz, 1H), 6.94-6.74 (m, 1H), 6.57 (br s, 2H), 6.42-6.33 (m, 1H), 3.96-3.78 (m, 1H), 3.62 (s, 2H), 2.96-2.84 (m, 2H), 2.25-2.18 (m, 2H), 1.66-1.57 (m, 2H), 1.34-1.21 (m, 2H).

Example 392: 4-((1-(4-(2-(2-Aminopyridin-3-yl)-3H-imidazo[4,5-b]pyridin-3-yl)benzyl)-4-methylpip-eridin-4-yl)amino)pyrimidine-2-carbonitrile

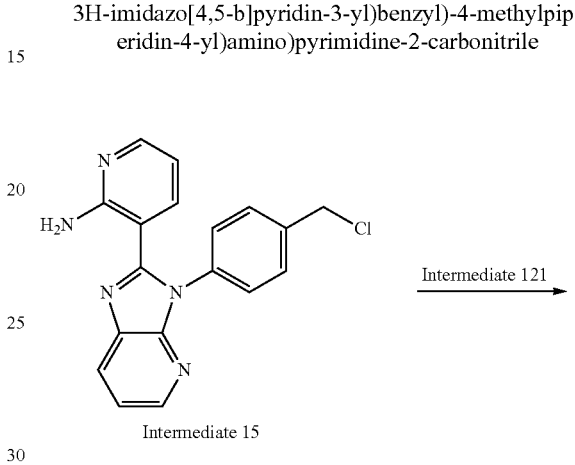

Intermediate 15

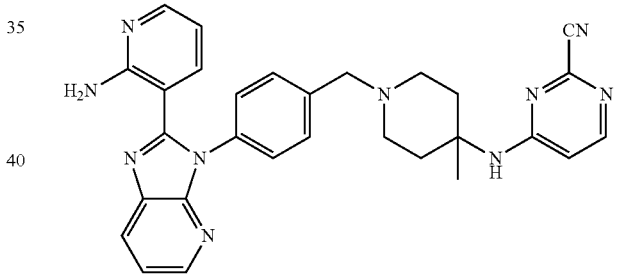

Example 392

To a solution of Intermediate 15 (80 mg, 238 μmol) and Intermediate 121 (62 mg, 286 μmol) in DMF (3 mL) were added KI (4 mg, 24 μmol) and K$_2$CO$_3$ (99 mg, 715 μmol). The mixture was stirred at 50° C. for 1 hr. The reaction mixture was poured into H$_2$O (10 mL), extracted with EtOAc (10 mL×2). The combined organic layers were dried over anhydrous Na$_2$SO$_4$, filtered and concentrated under reduced pressure. The crude was purified by silica gel flash chromatography (Eluent of 0~7% MeOH in CH$_2$Cl$_2$) to give 4-((1-(4-(2-(2-aminopyridin-3-yl)-3H-imidazo[4,5-b]pyri-din-3-yl)benzyl)-4-methylpiperidin-4-yl)amino)pyrimidine-2-carbonitrile (Example 392, 27.2 mg, yield: 22%) as a light-yellow solid. MS: m/z=517.2 [M+H]$^+$. $^1$H NMR (400 MHz, Dimethylsulfoxide-d$_6$) δ 8.33 (dd, J=4.8, 1.3 Hz, 1H), 8.20 (dd, J=8.0, 1.6 Hz, 1H), 8.09 (d, J=6.0 Hz, 1H), 8.00-7.97 (m, 1H), 7.61 (brs, 1H), 7.46-7.42 (m, 2H), 7.41-7.34 (m, 3H), 7.16 (dd, J=7.6, 1.6 Hz, 1H), 7.08-6.93 (m, 2H), 6.81 (d, J=6.4 Hz, 1H), 6.36 (dd, J=8.0, 5.2 Hz, 1H), 3.57-3.48 (m, 2H), 3.30 (s, 2H), 2.33-2.17 (m, 4H), 1.73-1.62 (m, 2H), 1.40 (s, 3H).

1479

Example 393: 4-((1-(4-(2-(2-Aminopyridin-3-yl)-5-(1-methyl-6-oxo-1,6-dihydropyridin-2-yl)-3H-imidazo[4,5-b]pyridin-3-yl)benzyl)piperidin-4-yl)amino)pyrimidine-2-carbonitrile

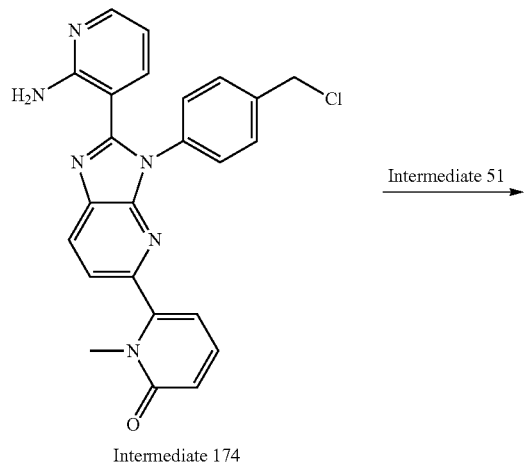

Intermediate 174

→ Intermediate 51

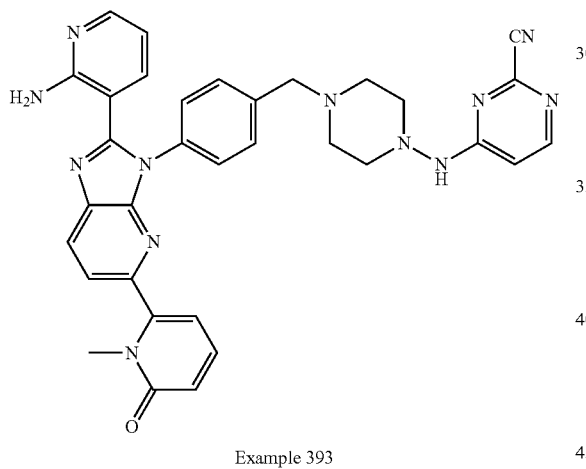

Example 393

To a solution of Intermediate 174 (120 mg, 271 μmol) and Intermediate 51 (55.1 mg, 271 μmol) in DMF (2 mL) were added NaI (8.12 mg, 54.2 μmol) and $K_2CO_3$ (112 mg, 813 μmol). The mixture was stirred at 25° C. for 16 hr. The reaction mixture was filtered. After purified by prep-HPLC (column: Phenomenex C18 80*40 mm*3 μm; mobile phase: [water ($NH_3H_2O+NH_4HCO_3$)-ACN]; gradient: 27%-57% B over 7 min), 4-((1-(4-(2-(2-aminopyridin-3-yl)-5-(1-methyl-6-oxo-1,6-dihydropyridin-2-yl)-3H-imidazo[4,5-b]pyridin-3-yl)benzyl)piperidin-4-yl)amino)pyrimidine-2-carbonitrile (Example 393, 30.2 mg, yield. 18%) was obtained as a yellow lyophilized powder. MS: m/z=610.5 [M+H]$^+$. $^1$H NMR (400 MHz, Dimethylsulfoxide-$d_6$) δ 8.36 (d, J=8.0 Hz, 1H), 8.12-8.03 (m, 2H), 8.01 (dd, J=4.8, 2.0 Hz, 1H), 7.66 (d, J=8.4 Hz, 1H), 7.49-7.40 (m, 5H), 7.19 (dd, J=7.6, 1.6 Hz, 1H), 7.00 (br s, 2H), 6.66 (d, J=6.0 Hz, 1H), 6.47 (dd, J=9.2, 1.2 Hz, 1H), 6.40 (dd, J=8.0, 4.8 Hz, 1H), 6.33 (dd, J=6.8, 1.2 Hz, 1H), 3.84-3.73 (m, 1H), 3.55 (s, 2H), 3.30 (s, 3H), 2.84-2.76 (m, 2H), 2.18-2.09 (m, 2H), 1.89-1.85 (m, 2H), 1.54-1.42 (m, 2H).

1480

Example 394: 4-(4-(4-(2-(2-Aminopyridin-3-yl)-5-(1-methyl-6-oxo-1,6-dihydropyridin-2-yl)-3H-imidazo[4,5-b]pyridin-3-yl)benzyl)piperazin-1-yl)pyrimidine-2-carbonitrile

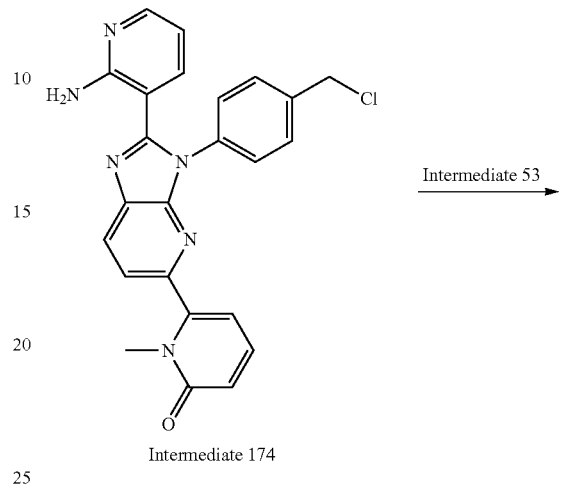

Intermediate 174

→ Intermediate 53

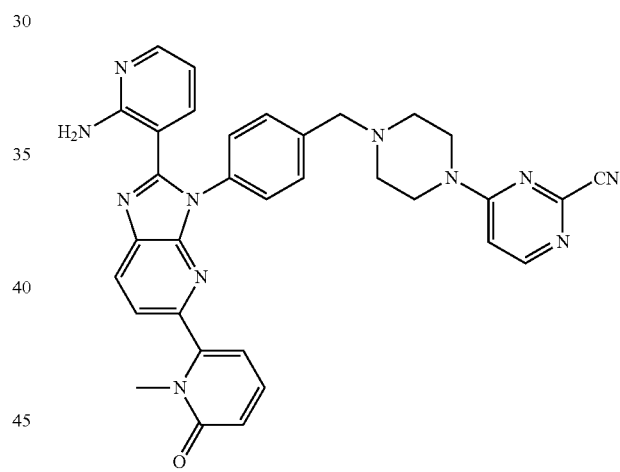

Example 394

To a solution of Intermediate 174 (120 mg, 271 μmol) and Intermediate 53 (51.3 mg, 271 μmol) in DMF (2 mL) were added NaI (8.12 mg, 54.2 μmol), $K_2CO_3$ (112 mg, 813 μmol). The mixture was stirred at 25° C. for 16 hr. The reaction mixture was filtered. After purified by prep-HPLC (column: Phenomenex C18 80*40 mm*3 μm; mobile phase: [water ($NH_3H_2O+NH_4HCO_3$)-ACN]; gradient: 40%-70% B over 7 min), 4-(4-(4-(2-(2-aminopyridin-3-yl)-5-(1-methyl-6-oxo-1,6-dihydropyridin-2-yl)-3H-imidazo[4,5-b]pyridin-3-yl)benzyl)piperazin-1-yl)pyrimidine-2-carbonitrile (Example 394, 24.7 mg, yield: 14%) was obtained as a yellow lyophilized powder. MS: m/z=596.1 [M+H]$^+$. $^1$H NMR (400 MHz, Dimethylsulfoxide-$d_6$) δ 8.37 (d, J=8.4 Hz, 1H), 8.31-8.24 (m, 1H), 8.05-7.97 (m, 1H), 7.66 (d, J=8.0 Hz, 1H), 7.51-7.42 (m, 5H), 7.21-7.17 (m, 1H), 7.11 (d, J=6.0 Hz, 1H), 7.00 (br s, 2H), 6.48 (d, J=9.2 Hz, 1H), 6.40 (dd, J=7.6, 4.8 Hz, 1H), 6.33 (d, J=6.8 Hz, 1H), 3.75-3.64 (m, 4H), 3.62 (s, 2H), 3.31 (s, 3H), 2.48-2.44 (m, 4H).

Example 395: 4-((1-(4-(2-(2-Aminopyridin-3-yl)-5-(3-methoxyphenyl)-3H-imidazo[4,5-b]pyridin-3-yl)benzyl)piperidin-4-yl)amino)pyrimidine-2-carbonitrile

Example 396: 4-((1-(4-(2-(2-Aminopyridin-3-yl)-5-(tert-butyl)-3H-imidazo[4,5-b]pyridin-3-yl)benzyl)piperidin-4-yl)amino)pyrimidine-2-carbonitrile

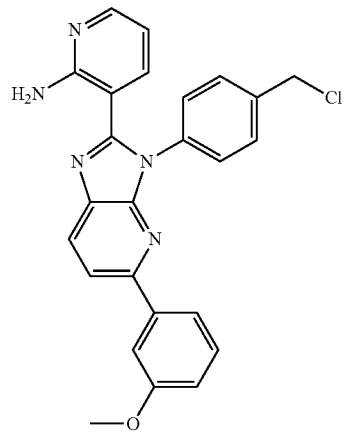

Intermediate 121

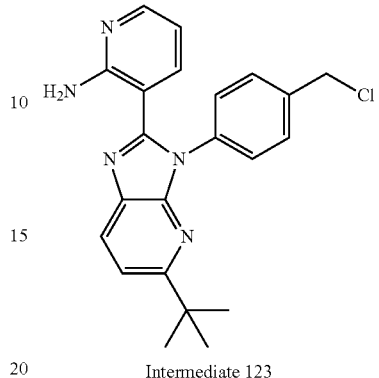

Intermediate 123

→ Intermediate 51

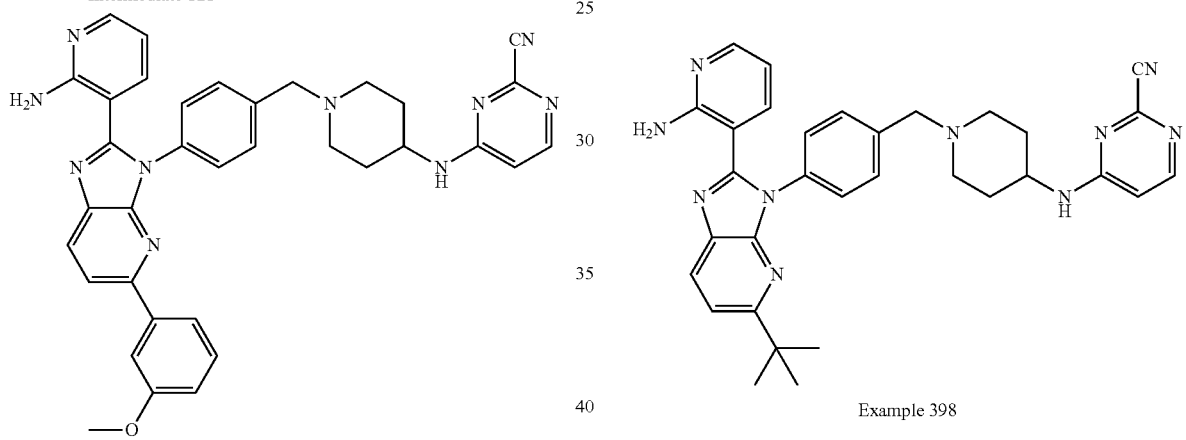

Example 395 (left)    Example 398 (right)

To a solution of Intermediate 122 (250 mg, 566 μmol) and Intermediate 51 (126 mg, 622 μmol) in DMF (5 mL) were added NaI (17 mg, 113 μmol) and $K_2CO_3$ (235 mg, 1.7 mmol). The mixture was stirred at 50° C. for 2 hr. The reaction mixture was diluted with $H_2O$ (15 mL) and extracted with EtOAc (20 mL). The organic layers were washed with brine (10 mL), dried over $Na_2SO_4$, filtered and concentrated under reduced pressure. After purified by prep-HPLC (column: Phenomenex C18 80*40 mm*3 um; mobile phase: [water ($NH_4HCO_3$)-ACN]; gradient: 54%-84% B over 8 min), 4-((1-(4-(2-(2-aminopyridin-3-yl)-5-(3-methoxyphenyl)-3H-imidazo[4,5-b]pyridin-3-yl)benzyl)piperidin-4-yl)amino)pyrimidine-2-carbonitrile (Example 395, 29 mg, yield: 8%) was obtained as a yellow solid. MS: m/z=609.5 $[M+H]^+$. $^1$H NMR (400 MHz, Dimethylsulfoxide-$d_6$) δ 8.26 (d, J=8.4 Hz, 1H), 8.17-8.02 (m, 2H), 8.02-7.98 (m, 2H), 7.63-7.57 (m, 2H), 7.50-7.43 (m, 4H), 7.41-7.35 (m, 1H), 7.18 (dd, J=8.0, 2.0 Hz, 1H), 7.11-7.01 (m, 2H), 6.97 (dd, J=8.0, 2.0 Hz, 1H), 6.68 (d, J=6.0 Hz, 1H), 6.39 (dd, J=8.0, 4.8 Hz, 1H), 3.85-3.80 (m, 1H), 3.79 (s, 3H), 3.59 (s, 2H), 3.30-3.29 (m, 2H), 2.86-2.79 (m, 2H), 2.19-2.11 (m, 2H), 1.93-1.84 (m, 2H).

To a solution of Intermediate 123 (200 mg, 510 mmol) and Intermediate 51 (178 mg TFA salt, 561 μmol) in DMF (4 mL) were added $K_2CO_3$ (353 mg, 2.55 mmol) and NaI (23 mg, 153 μmol), The mixture was stirred at 50° C. for 2 hr. The reaction mixture was poured into $H_2O$ (15 mL), extracted with EtOAc (15 mL×3). The combined organic layers were dried over anhydrous $Na_2SO_4$, filtered and concentrated under reduced pressure. After purified by silica gel flash chromatography (Eluent of 0~18%, MeOH in $CH_2Cl_2$), 4-((1-(4-(2-(2-aminopyridin-3-yl)-5-(tert-butyl)-3H-imidazo[4,5-b]pyridin-3-yl)benzyl)piperidin-4-yl)amino)pyrimidine-2-carbonitrile (Example 396, 60.4 mg, yield: 21%) was obtained as a light-yellow solid. MS: m/z=559.2 $[M+H]^+$. $^1$H NMR (400 MHz, Acetonitrile-$d_3$) δ 8.17-7.87 (m, 3H), 7.49-7.43 (m, 3H), 7.36 (d, J=8.0 Hz, 2H), 7.09 (d, J=7.6 Hz) 6.63-6.54 (m, 1H), 6.48 (br s, 2H), 6.36 (dd, J=8.0, 5.2 Hz, 1H), 6.33-6.20 (m, 1H), 4.06-3.76 (m, 1H), 3.63 (s, 2H), 2.92-2.84 (m, 2H), 2.31-2.27 (m, 2H), 2.02-1.97 (m, 2H), 1.62-1.52 (m, 2H), 1.34 (s, 9H).

Example 397: 4-((1-(4-(2-(2-Aminopyridin-3-yl)-5-ethyl-3H-imidazo[4,5-b]pyridin-3-yl)benzyl)piperidin-4-yl)amino)pyrimidine-2-carbonitrile

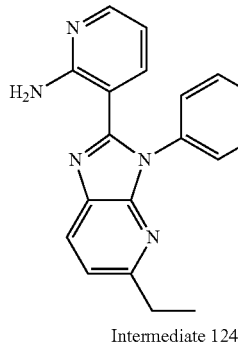

Intermediate 124

→ Intermediate 51

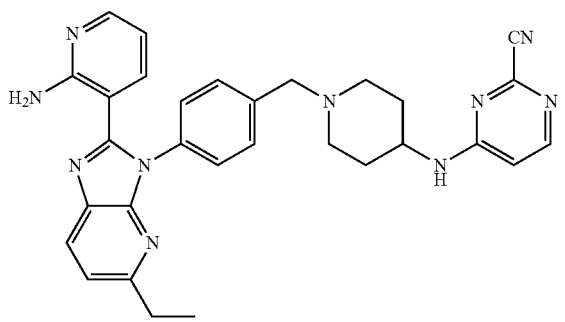

Example 397

To a solution of Intermediate 124 (170 mg HCl salt, 424 μmol) and Intermediate 51 (161 mg TFA salt, 509 μmol) in DMF (2 mL) were added NaI (31.8 mg, 212 μmol) and K₂CO₃ (293 mg, 2.12 mmol). The mixture was stirred at 50° C. for 1 hr. The reaction mixture was diluted with water (10 mL) and extracted with EtOAc (2×20 mL). The combined organic layers were washed with brine (30 mL), dried over Na₂SO₄, filtered and concentrated under reduced pressure. After purified by silica gel flash chromatography (Eluent of 0~5%, MeOH in CH₂Cl₂), 4-((1-(4-(2-(2-aminopyridin-3-yl)-5-ethyl-3H-imidazo[4,5-b]pyridin-3-yl)benzyl)piperidin-4-yl)amino)pyrimidine-2-carbonitrile (Example 397, 131.7 mg, yield: 57%) was obtained as an off white solid. MS: m/z=531.2 [M+H]⁺. ¹H NMR (400 MHz, Dimethylsulfoxide-d₆) δ 8.12-8.01 (m, 3H), 7.97 (dd, J=4.8, 2.0 Hz, 1H), 7.47-7.42 (m, 2H), 7.38-7.34 (m, 2H), 7.28 (d, J=8.4 Hz, 1H), 7.08 (dd, J=7.6, 1.6 Hz, 1H), 6.97 (br s, 2H), 6.67 (d, J=6.0 Hz, 1H), 6.34 (dd, J=7.2, 4.4 Hz, 1H), 3.89-7.73 (m, 1H), 3.57 (s, 2H), 2.84-2.76 (m, 4H), 2.18-2.12 (m, 2H), 1.95-1.81 (m, 2H), 1.55-1.44 (m, 2H), 1.21 (t, J=7.6 Hz, 3H).

Example 398: 2-(2-Aminopyridin-3-yl)-3-(4-((4-((2-cyanopyrimidin-4-yl)amino)piperidin-1-yl)methyl)phenyl)-N-methyl-3H-imidazo[4,5-h]pyridine-5-carboxamide

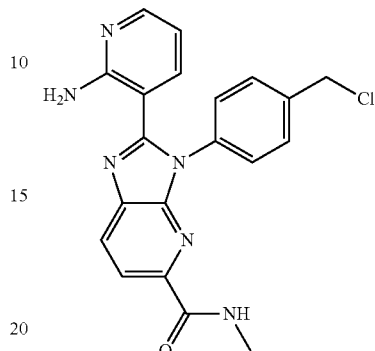

Intermediate 125

→ Intermediate 51

Example 398

To a solution of Intermediate 125 (200 mg, 509 μmol) and Intermediate 51 (103 mg, 326 μmol) in DMF (2 mL) were added K₂CO₃ (352 mg, 2.6 mmol) and NaI (23 mg, 153 μmol). The mixture was stirred at 50° C. for 0.6 hr. The reaction mixture was poured into H₂O (10 mL), extracted with EtOAc (45 mL). The organic phase was dried over anhydrous Na₂SO₄, filtered and concentrated under reduced pressure. After purified by prep-HPLC (column: Waters xbridge 150*25 mm 10 μm; mobile phase: [water (NH₄HCO₃)-ACN]; gradient: 18%-48% B over 14 min), 2-(2-aminopyridin-3-yl)-3-(4-((4-((2-cyanopyrimidin-4-yl)amino)piperidin-1-yl)methyl)phenyl)-N-methyl-3H-imidazo[4,5-b]pyridine-5-carboxamide (Example 398, 84.2 mg, yield: 29%) was obtained as an off-white lyophilized powder. MS: m/z=560.2 [M+H]⁺. ¹H NMR (400 MHz, Dimethylsulfoxide-d₆) δ 8.32 (d, J=8.0 Hz, 1H), 8.14-8.13 (m, 1H), 8.12-8.02 (m, 3H), 8.00 (d, J=4.4 Hz, 1H), 7.51-7.39 (m, 4H), 7.15 (d, J=7.6 Hz, 1H), 6.96 (br s, 2H), 6.67 (d, J=6.0 Hz, 1H), 6.38 (dd, J=7.2, 4.8 Hz, 1H), 3.98-3.69 (m, 1H), 3.57 (s, 2H), 2.89-2.78 (m, 5H), 2.18-2.12 (m, 2H), 1.97-1.81 (m, 2H), 1.52-1.45 (m, 2H).

Example 399: 4-(4-(4-(2-(2-Aminopyridin-3-yl)-5-(3-cyanopyridin-4-yl)-3H-imidazo[4,5-b]pyridin-3-yl)benzyl)piperazin-1-yl)pyrimidine-2-carbonitrile Example 400: 4-((1-(4-(2-(2-Aminopyridin-3-yl)-5-(3-cyanopyridin-4-yl)-3H-imidazo[4,5-b]pyridin-3-yl)benzyl)piperidin-4-yl)amino)pyrimidine-2-carbonitrile

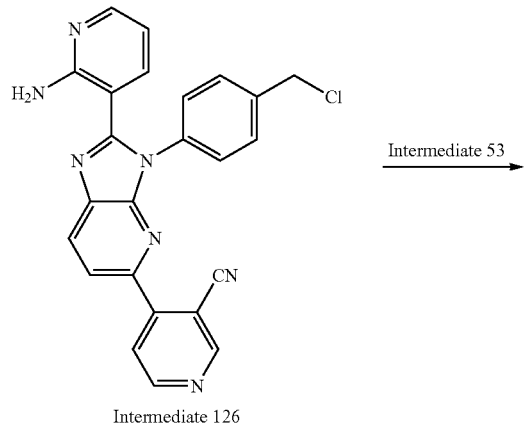

Intermediate 126

→ Intermediate 53

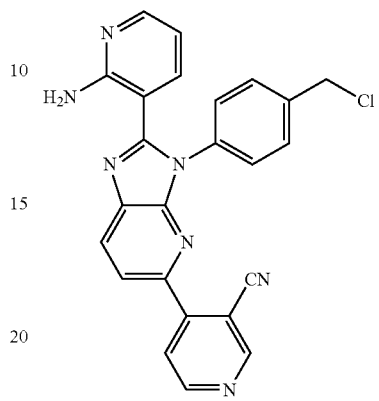

Intermediate 126

→ Intermediate 51

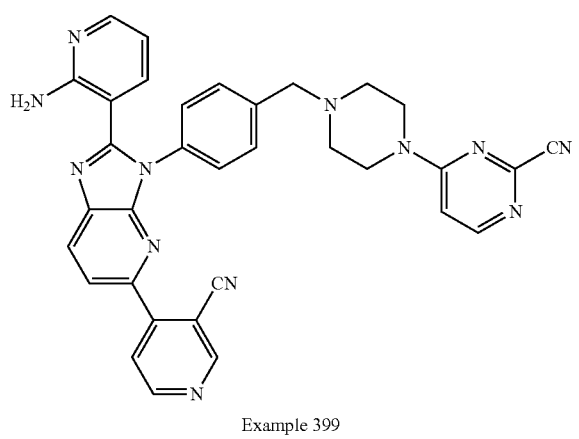

Example 399

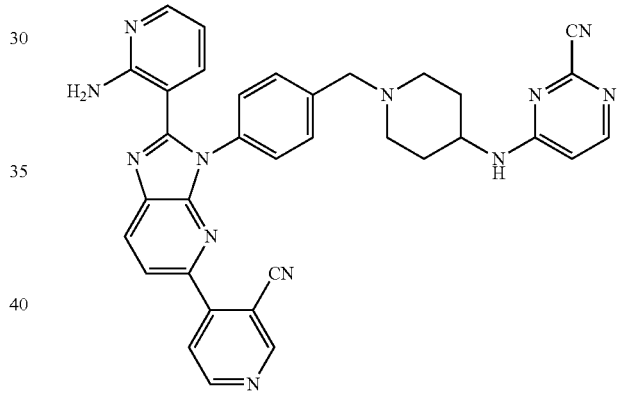

Example 400

To a solution of Intermediate 126 (200 mg, 456 μmol) and Intermediate 53 (138 mg TFA salt, 456 μmol) in DMF (2 mL) were added NaI (34 mg, 228 μmol) and K$_2$CO$_3$ (315 mg, 2.28 μmol). The mixture was stirred at 50° C. for 1 hr. The reaction mixture was filtered. After purified by prep-HPLC (column: [water (NH$_4$HCO$_3$)-ACN]; B %: 34%-64%, 14 min), 4-(4-(4-(2-(2-aminopyridin-3-yl)-5-(3-cyanopyridin-4-yl)-3H-imidazo[4,5-b]pyridin-3-yl)benzyl)piperazin-1-yl)pyrimidine-2-carbonitrile (Example 399, 32 mg, yield: 12%) was obtained as a yellow solid. MS: m/z=591.3 [M+H]$^+$. $^1$H NMR (400 MHz, Dimethylsulfoxide-d$_6$) δ 9.09 (s, 1H), 8.91 (d, J=5.6 Hz, 1H), 8.45 (d, J=8.4 Hz, 1H), 8.26 (d, J=6.4 Hz, 1H), 8.04-7.99 (m, 3H), 7.51-7.45 (m, 4H), 7.24-7.21 (m, 1H), 7.11 (d, J=6.4 Hz, 1H), 7.01 (br s, 2H), 6.40 (dd, J=7.6, 5.2 Hz, 1H), 3.70-3.60 (m, 6H), 2.48-2.45 (m, 4H).

To a solution of Intermediate 126 (120 mg, 235 gmol) and Intermediate 51 (74.7 mg TFA salt, 235 μmol) in DMF (2 mL) were added NaI (17.6 mg, 117 μmol) and K$_2$CO$_3$ (97.7 mg, 707 μmol). The mixture was stirred at 50° C. for 1 hr. The reaction mixture was diluted with water (10 mL) and extracted with EtOAc (2×10 mL). The combined organic layers were washed with brine (10 mL), dried over Na$_2$SO$_4$, filtered and concentrated under reduced pressure. The residue was purified by silica gel flash chromatography (Eluent of 0~6% MeOH in CH$_2$Cl$_2$) to give 4-((1-(4-(2-(2-aminopyridin-3-yl)-5-(3-cyanopyridin-4-yl)-3H-imidazo[4,5-b]pyridin-3-yl)benzyl)piperidin-4-yl)amino)pyrimidine-2-carbonitrile (Example 400, 53.7 mg, yield: 36%) as a yellow solid. MS: m/z=605.4 [M+H]$^+$. $^1$H NMR (400 MHz, Dimethylsulfoxide-d$_6$) δ 9.08 (s, 1H), 8.91 (d, J=5.2 Hz, 1H), 8.45 (d, J=8.4 Hz, 1H), 8.10-7.96 (m, 5H), 7.52-7.46 (m, 2H), 7.46-7.40 (m, 2H), 7.22 (dd, J=8.0, 1.6 Hz, 1H), 7.01 (br s, 2H), 6.67 (d, J=6.0 Hz, 1H), 6.41 (dd, J=7.6, 4.8 Hz, 11H), 3.91-3.69 (m, 1H), 3.56 (s, 2H), 2.87-2.75 (m, 2H), 2.20-2.05 (m, 2H), 1.93-1.79 (m, 2H), 1.55-1.41 (m, 2H).

Example 401: 4-((1-(4-(2-(2-Aminopyridin-3-yl)-5-fluoro-3H-imidazo[4,5-b]pyridin-3-yl)benzyl)piperidin-4-yl)amino)pyrimidine-2-carbonitrile

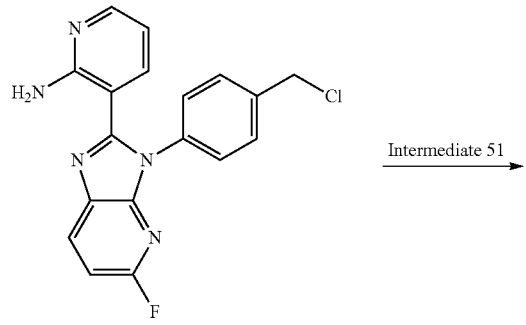

Intermediate 127

Intermediate 51 →

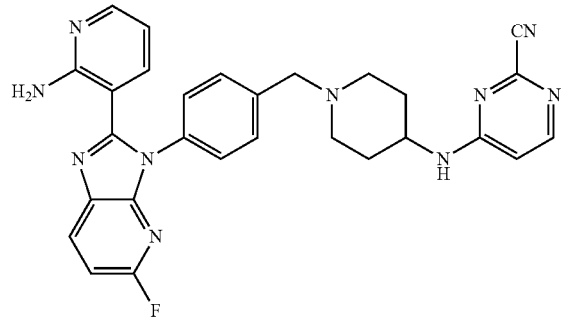

Example 401

To a solution of Intermediate 127 (200 mg, 565 μmol) and Intermediate 51 (179 mg TFA salt, 565 μmol) in DMF (2 mL) were added NaI (42.3 mg, 282 μmol) and K$_2$CO$_3$ (399 mg, 2.83 μmol). The mixture was stirred at 50° C. for 1 hr. The reaction mixture was filtered. After purified by prep-HPLC (column: [water (NH$_4$HCO$_3$)-ACN]; B %: 33%-63%, 14 min), 4-((1-(4-(2-(2-aminopyridin-3-yl)-5-fluoro-3H-imidazo[4,5-b]pyridin-3-yl)benzyl)piperidin-4-yl)amino)pyrimidine-2-carbonitrile (Example 401, 51.6 mg, yield: 18%) was obtained as a yellow solid. MS: m/z=521.4 [M+H]$^+$. $^1$H NMR (400 MHz, Dimethylsulfoxide-d$_6$) δ 8.41-8.35 (m, 1H), 8.12-8.01 (m, 2H), 7.98 (dd, J=4.8, 2.0 Hz, 1H), 7.47-7.43 (m, 2H), 7.40-7.37 (m, 2H), 7.17-7.14 (m, 2H), 6.91 (br s, 2H), 6.67 (d, J=6.0 Hz, 1H), 6.38 (dd, J=7.6, 4.8 Hz, 1H), 3.84-3.76 (m, 1H), 3.56 (s, 2H), 2.81 (d, J=11.2 Hz, 2H), 2.14 (t, J=10.8 Hz, 2H), 1.91-1.83 (m, 2H), 1.53-1.44 (m, 2H), $^1$H NMR (400 MHz, Dimethylsulfoxide-d$_6$) δ −74.090.

Example 402: 4-((1-(4-(2-(2-Aminopyridin-3-yl)-6-fluoro-3H-imidazo[4,5-b]pyridin-3-yl)benzyl)piperidin-4-yl)amino)pyrimidine-2-carbonitrile

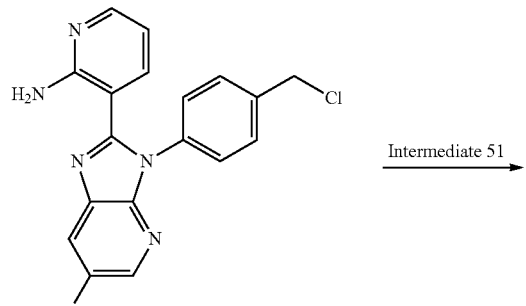

Intermediate 128

Intermediate 51 →

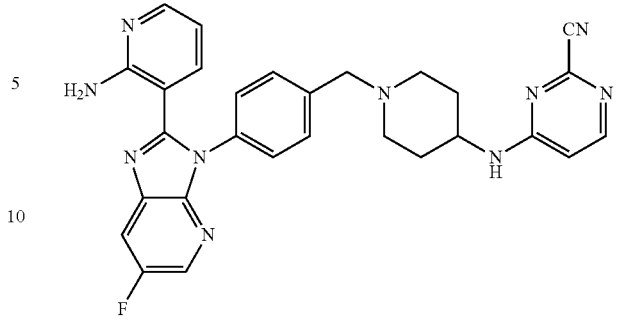

Example 402

To a solution of Intermediate 128 (284 mg, 803 μmol) and Intermediate 51 (180 mg, 883 μmol) in DMF (2 mL) were added K$_2$CO$_3$ (333 mg, 2.4 mmol) and NaI (24 mg, 161 μmol). The mixture was stirred at 50° C. for 0.5 hr. The reaction mixture was diluted with H$_2$O (20 mL) and extracted with EtOAc (30 mL). The organic layers were washed with brine (30 mL), dried over Na$_2$SO$_4$, filtered and concentrated under reduced pressure. After purified by silica gel flash chromatography (Eluent of 0~5% MeOH in CH$_2$Cl$_2$), 4-((1-(4-(2-(2-aminopyridin-3-yl)-6-fluoro-3H-imidazo[4,5-b]pyridin-3-yl)benzyl)piperidin-4-yl)amino)pyrimidine-2-carbonitrile (Example 402, 115.8 mg, yield: 26%) was obtained as a pink solid. MS: m/z=521.1 [M+H]$^+$. $^1$H NMR (400 MHz, Acetonitrile-d$_3$) δ 8.26 (s, 1H), 8.21-7.95 (m, 2H), 7.90 (dd, J=8.8, 2.8 Hz, 1H), 7.51 (d, J=8.8 Hz, 2H), 7.35 (d, J=8.8 Hz, 2H), 7.16 (d, J=8.8 Hz, 1H), 6.75-6.49 (m, 3H), 6.37 (dd, J=8.8, 2.8 Hz, 1H), 6.27 (br s, 1H), 4.02-3.83 (m, 1H), 3.63 (s, 2H), 2.88 (d, J=11.2 Hz, 2H), 2.26-2.21 (m, 2H), 2.17-2.13 (m, 2H), 1.60-1.49 (m, 2H). $^{19}$F NMR (376 MHz, Acetonitrile-d$_3$) 5-136.38.

Example 403: 4-((1-(4-(2-(2-Aminopyridin-3-yl)-5-(2-oxooxazolidin-3-yl)-3H-imidazo[4,5-b]pyridin-3-yl)benzyl)piperidin-4-yl)amino)pyrimidine-2-carbonitrile

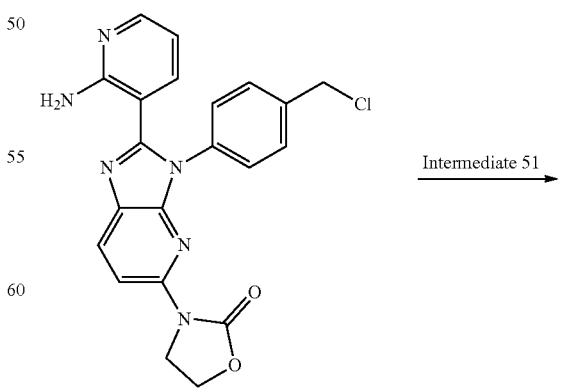

Intermediate 130

1489
-continued

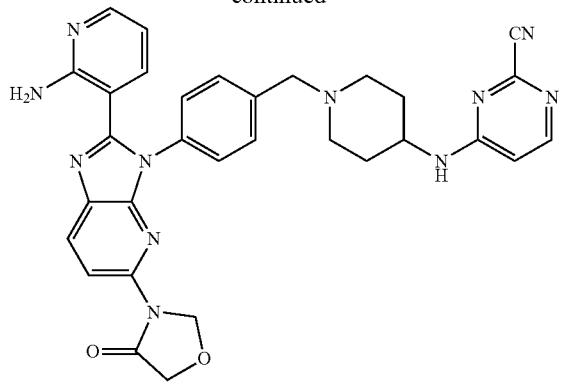

Example 403

To a solution of Intermediate 130 (90 mg HCl salt, 196 μmol) and Intermediate 51 (63 mg TFA salt, 196 μmol) in DMF (3 mL) w added K₂CO₃ (136 mg, 984 μmol) and NaI (30 mg, 196 μmol). The mixture was stirred at 25° C. for 1 hr. The reaction mixture was diluted with H₂O (100 mL) and extracted with EtOAc (50 mL×2). The combined organic layers were washed with brine (100 mL), dried over Na₂SO₄, filtered and concentrated under reduced pressure. The residue was purified by silica gel flash chromatography (Eluent of 0~7% MeOH in CH₂Cl₂) to give 4-((1-(4-(2-(2-aminopyridin-3-yl)-5-(2-oxooxazolidin-3-yl)-3H-imidazo[4,5-b]pyridin-3-yl)benzyl)piperidin-4-yl)amino)pyrimidine-2-carbonitrile (Example 403, 50.1 mg, yield: 41%) was obtained as a yellow solid. MS: m/z=588.1 [M+H]⁺. ¹H NMR (400 MHz, Dimethylsulfoxide-d₆) δ 8.25 (d, J=8.8 Hz, 1H), 8.15-8.02 (m, 3H), 7.98-7.97 (m, 1H), 7.46-7.42 (m, 2H), 7.40-7.35 (m, 2H), 7.10-7.08 (m, 1H), 6.97 (br s, 2H), 6.67 (d, J=6.0 Hz, 1H), 6.36 (dd, J=7.6, 4.8 Hz, 1H), 4.41 (t, J=8.0 Hz, 2H), 4.07 (t, J=8.0 Hz, 2H), 3.88-3.72 (m, 1H), 3.57 (s, 2H), 2.82-2.79 (m, 2H), 2.18-2.10 (m, 2H), 1.92-1.83 (m, 2H), 1.54-1.44 (m, 2H).

Example 404: 4-((1-(4-(2-(2-Aminopyridin-3-yl)-5-(6-fluoropyridin-3-yl)-3H-imidazo[4,5-b]pyridin-3-yl)benzyl)piperidin-4-yl)amino)pyrimidine-2-carbonitrile 1490
-continued

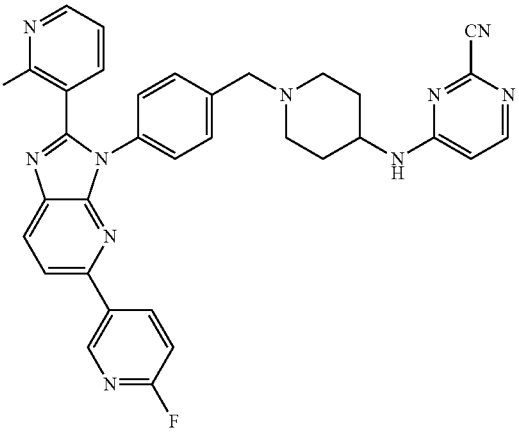

Example 404

To a solution of Intermediate 131 (200 mg, 464 μmol) and Intermediate 51 (147 mg, 464 μmol) in DMF (5 mL) were added NaI (34.8 mg, 232 μmol) and K₂CO₃ (321 mg, 2.32 mmol). The mixture was stirred at 50° C. for 1 hr. The reaction mixture was filtered. After purified by prep-HPLC (column: Waters xbridge 150*25 mm 10 μm; mobile phase: [water (NH₄HCO₃)-ACN]; gradient: 38%-68% B over 14 min), 4-((1-(4-(2-(2-aminopyridin-3-yl)-5-(6-fluoropyridin-3-yl)-3H-imidazo[4,5-b]pyridin-3-yl)benzyl)piperidin-4-yl) amino)pyrimidine-2-carbonitrile (Example 404, 56 mg, yield: 20%) was obtained as a yellow solid. MS: m/z=598.4 [M+H]⁺. ¹H NMR (400 MHz, Dimethylsulfoxide-d₆) δ 8.89 (d, J=2.4 Hz, 1H), 8.61-8.53 (m, 1H), 8.33 (d, J=8.4 Hz, 1H), 8.14-8.03 (m, 3H), 8.01 (dd, J=4.8, 1.6 Hz, 1H), 7.50-7.43 (m, 4H), 7.30 (dd, J=8.8, 2.8 Hz, 1H), 7.20-7.14 (m, 1H), 7.04 (br s, 2H), 6.67 (d, J=6.0 Hz, 1H), 6.39 (dd, J=7.6, 5.2 Hz, 1H), 3.85-3.77 (m, 1H), 3.59 (s, 2H), 2.83 (d, J=12.0 Hz, 2H), 2.20-2.11 (m, 2H), 1.93-1.83 (m, 2H), 1.54-1.43 (m, 2H). ¹⁹F NMR (400 MHz, Dimethylsulfoxide-d₆) δ −69.579.

Example 405: 4-((1-(4-(2-(2-Aminopyridin-3-yl)-5-chloro-3H-imidazo[4,5-b]pyridin-3-yl)benzyl)piperidin-4-yl)amino)pyrimidine-2-carbonitrile

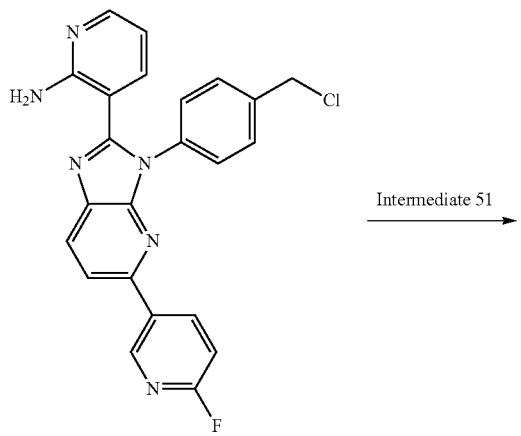

Intermediate 131

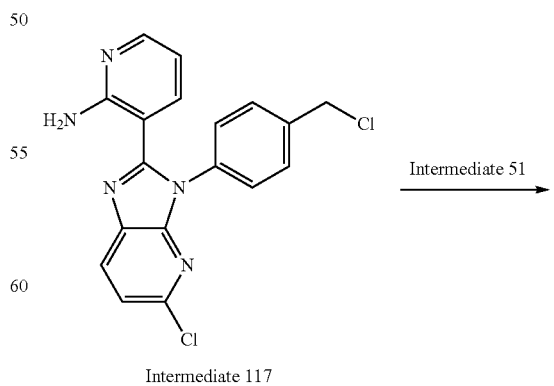

Intermediate 117

1491

-continued

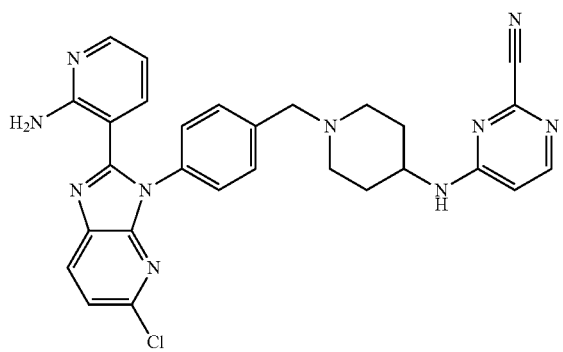

Example 405

To a solution of Intermediate 51 (165 mg, 810 gmol) and Intermediate 117 (300 mg, 810 μmol) in DMF (3 mL) was added DIEA (314 mg, 2.43 mmol). The mixture was degassed and purged with $N_2$ three times, and stirred at 25° C. for 16 hr under $N_2$. The reaction mixture was quenched with $H_2O$ (10 mL) at 25° C. and extracted with $CH_2Cl_2$ (5 mL×3). The combined organic layers were washed with brine (10 mL×2), dried over $Na_2SO_4$, filtered and concentrated under reduced pressure. The residue was purified by silica gel flash chromatography (Eluent of 1~8% MeOH in $CH_2Cl_2$) to give 4-((1-(4-(2-(2-aminopyridin-3-yl)-5-chloro-3H-imidazo[4,5-b]pyridin-3-yl)benzyl)piperidin-4-yl)amino)pyrimidine-2-carbonitrile (Example 405, 226 mg, yield: 52%) as a light yellow solid. MS: m/z=537.2 [M+H]$^+$. $^1$H NMR (400 MHz, Dimethylsulfoxide-d$_6$) δ 8.27 (d, J=8.0 Hz, 1H), 8.14-8.02 (m, 2H), 7.99 (dd, J=4.8, 1.6 Hz, 1H), 7.52-7.36 (m, 5H), 7.16 (dd, J=7.6, 1.6 Hz, 1H), 6.94 (br s, 2H), 6.67 (d, J=6.0 Hz, 1H), 6.38 (dd, J=7.6, 4.8 Hz, 1H), 3.88-3.74 (m, 1H), 3.57 (s, 2H), 2.86-2.75 (m, 2H), 2.20-2.07 (m, 2H), 1.94-1.79 (m, 2H), 1.57-1.40 (m, 2H).

Example 406: 2-(2-Aminopyridin-3-yl)-3-(4-((4-((2-cyanopyrimidin-4-yl)amino)piperidin-1-yl)methyl) phenyl)-3H-imidazo[4,5-b]pyridine-5-carbonitrile

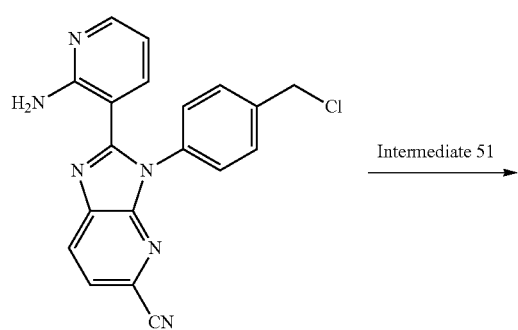

Intermediate 132

1492

-continued

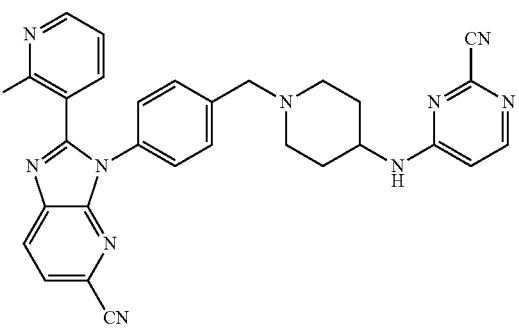

Example 406

To a solution of Intermediate 132 (235 mg, 651 μmol) and Intermediate 51 (207 mg, 651 μmol, TFA) in DMF (5 mL) were added $K_2CO_3$ (450 mg, 3.26 mmol) and NaI (9.76 mg, 65.1 μmol). The mixture was stirred at 60° C. for 1 hr. After purified by prep-HPLC (column: Waters xbridge 150*25 mm*10 μm; mobile phase: [water (NH$_4$HCO$_3$)-ACN]; gradient: 25%-55% B over 14 min), 2-(2-aminopyridin-3-yl)-3-(4-((4-((2-cyanopyrimidin-4-yl)amino)piperidin-1-yl) methyl)phenyl)-3H-imidazo[4,5-b]pyridine-5-carbonitrile (Example 406, 36.2 mg, yield: 11%) was obtained as a yellow solid. MS: m/z=528.3 [M+H]$^+$. $^1$H NMR (400 MHz, Dimethylsulfoxide-d$_6$) δ 8.42 (d, J=8.0 Hz, 1H), 8.13-7.97 (m, 4H), 7.50-7.41 (m, 4H), 7.22 (d, J=8.0 Hz, 1H), 6.99 (s, 2H), 6.67 (d, J=6.0 Hz, 1H), 6.43-6.33 (m, 1H), 3.92-3.69 (m, 1H), 3.57 (s, 2H), 2.87-2.78 (m, 2H), 2.21-2.12 (m, 2H), 1.94-1.84 (m, 2H), 1.55-1.45 (m, 2H).

Example 407: 4-(4-(4-(2-(2-Aminopyridin-3-yl)-5-(3-cyanopyridin-2-yl)-3H-imidazo[4,5-b]pyridin-3-yl)benzyl)piperazin-1-yl)pyrimidine-2-carbonitrile

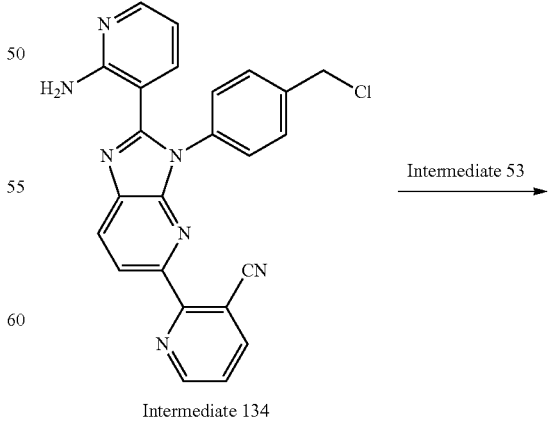

Intermediate 134

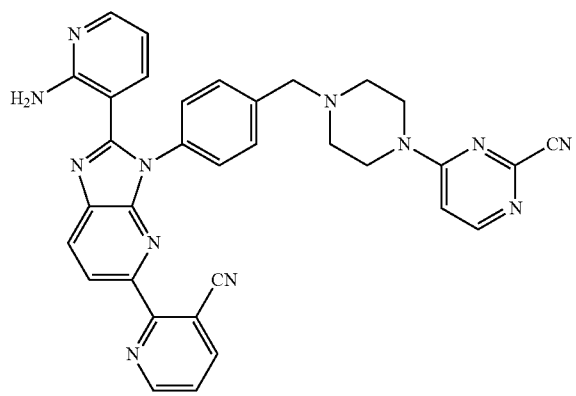

Example 407

Example 408

To a solution of Intermediate 134 (100 mg, 211 µmol) and Intermediate 53 (63.9 mg TFA salt, 211 µmol) in DMF (2 mL) were added $K_2CO_3$ (146 mg, 1.05 mmol) and NaI (9.48 mg, 63.3 µmol). The mixture was stirred at 50° C. for 0.5 hr. The mixture was filtered and concentrated to give the crude. After purified by prep-HPLC (column: Phenomenex C18 80*40 mm*3 µm; mobile phase: [water ($NH_4HCO_3$)-ACN]; gradient: 49%-79% B over 8 min), 4-(4-(4-(2-(2-aminopyridin-3-yl)-5-(3-cyanopyridin-2-yl)-3H-imidazo[4,5-b]pyridin-3-yl)benzyl)piperazin-1-yl)pyrimidine-2-carbonitrile (Example 407, 31.6 mg delivered, yield: 25%) was obtained as light-yellow solid. MS: m/z=591.1 [M+H]$^+$. $^1$H NMR (400 MHz, Dimethylsulfoxide-d$_6$) δ 8.93 (dd, J=4.8, 1.6 Hz, 1H), 8.46-8.35 (m, 2H), 8.29-8.20 (m, 2H), 8.02 (dd, J=4.8, 2.0 Hz, 1H), 7.64 (dd, J=8.0, 4.8 Hz, 1H), 7.54-7.49 (m, 2H), 7.48-7.39 (m, 2H), 7.24 (dd, J=8.0, 2.0 Hz, 1H), 7.11 (d, J=6.4 Hz, 1H), 7.01 (br s, 2H), 6.41 (dd, J=7.6, 4.8 Hz, 1H), 3.71-3.66 (m, 2H), 3.61 (s, 2H), 3.31-3.29 (m, 2H), 2.53-2.51 (m, 2H), 2.48-2.44 (m, 2H).

Example 408: 4-((1-(4-(2-(2-Aminopyridin-3-yl)-5-(3-cyanopyridin-2-yl)-3H-imidazo[4,5-b]pyridin-3-yl)benzyl)piperidin-4-yl)amino)pyrimidine-2-carbonitrile To a solution of Intermediate 134 (140 mg, 320 µmol) and Intermediate 51 (65.0 mg TFA salt, 320 µmol) in DMF (2 mL) were added $K_2CO_3$ (221 mg, 1.60 mmol) and NaI (14.4 mg, 95.9 µmol). The mixture was stirred at 50° C. for 0.5 hr. The mixture was filtered, and the filtrate was concentrated to give the crude product. After purified by prep-HPLC (column: Waters xbridge 150*25 mm*10 µm; mobile phase: [water ($NH_4HCO_3$)-ACN]; gradient: 28%-58% B over 14 min), 4-((1-(4-(2-(2-aminopyridin-3-yl)-5-(3-cyanopyridin-2-yl)-3H-imidazo[4,5-b]pyridin-3-yl)benzyl)piperidin-4-yl)amino)pyrimidine-2-carbonitrile (Example 408, 24.1 mg, yield: 12%) was obtained as light-yellow solid. MS: m/z=605.4 [M+H]$^+$. $^1$H NMR (400 MHz, Dimethylsulfoxide-d$_6$) δ 8.93 (dd, J=4.8, 1.6 Hz, 1H), 8.42-8.36 (m, 2H), 8.24 (d, J=8.4 Hz, 1H), 8.10-8.00 (m, 3H), 7.63 (dd, J=7.6, 4.4 Hz, 1H), 7.50 (d, J=8.4 Hz, 2H), 7.42 (d, J=8.4 Hz, 2H), 7.23 (dd, J=7.6, 1.6 Hz, 1H), 7.02 (br s, 2H), 6.72-6.60 (m, 1H), 6.41 (dd, J=7.6, 5.2 Hz, 1H), 3.95-3.68 (m, 1H), 3.56 (s, 2H), 2.86-2.79 (m, 2H), 2.17-2.09 (m, 2H), 1.92-1.83 (m, 2H), 1.52-1.41 (m, 2H).

Example 409: 4-((1-(4-(2-(2-Aminopyridin-3-yl)-5-(2-cyanopyridin-3-yl)-3H-imidazo[4,5-b]pyridin-3-yl)benzyl)piperidin-4-yl)amino)pyrimidine-2-carbonitrile

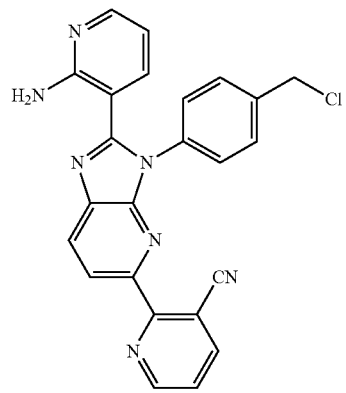

Intermediate 134

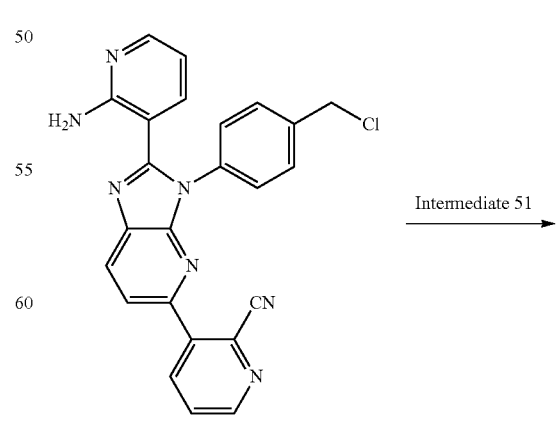

Intermediate 135

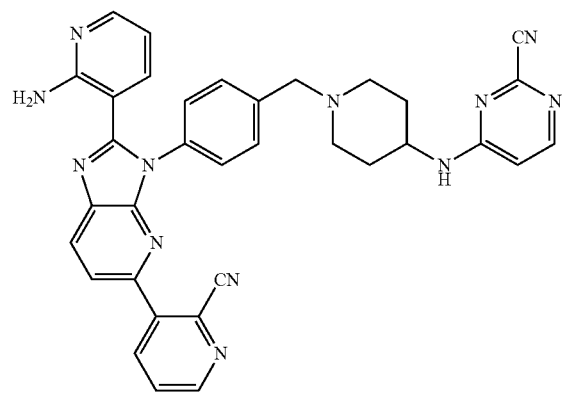

Example 409

To a solution of Intermediate 135 (100 mg, 228 μmol) and Intermediate 51 (86.9 mg, 274 μmol) in DMF (2 mL) were added NaI (6.85 mg, 45.7 μmol) and K$_2$CO$_3$ (189 mg, 1.37 mmol). The mixture was stirred at 50° C. for 2 hr. The reaction mixture was diluted with H$_2$O (100 mL) and extracted with CH$_2$Cl$_2$ (50 mL×2). The combined organic layers were washed with brine (100 mL×2), dried over Na$_2$SO$_4$, filtered and concentrated under reduced pressure. After purified by silica gel flash chromatography (Eluent of 0~10% MeOH in CH$_2$Cl$_2$), 4-((1-(4-(2-(2-aminopyridin-3-yl)-5-(2-cyanopyridin-3-yl)-3H-imidazo[4,5-b]pyridin-3-yl)benzyl)piperidin-4-yl)amino)pyrimidine-2-carbonitrile (Example 409, 35.7 mg, yield: 25%) was obtained as a yellow solid. MS: m/z=605.4 [M+H]$^+$. $^1$H NMR (400 MHz, Dimethylsulfoxide-d$_6$) δ 8.78 (d, J=4.4 Hz, 1H), 8.43 (d, J=8.0 Hz, 1H), 8.36 (d, J=8.0 Hz, 1H), 8.11-7.99 (m, 3H), 7.94 (d, J=8.0 Hz, 1H), 7.84 (dd, J=8.0, 4.4 Hz, 1H), 7.54-7.38 (m, 4H), 7.21 (d, J=7.2 Hz, 1H), 7.01 (br s, 2H), 6.66 (d, J=5.6 Hz, 1H), 6.41 (dd, J=7.2, 4.8 Hz, 1H), 3.88-3.71 (m, 1H), 3.56 (s, 2H), 2.86-2.73 (m, 2H), 2.22-2.05 (m, 2H), 1.93-1.76 (m, 2H), 1.55-1.40 (m, 2H).

Example 410: 4-((1-(4-(2-(2-Aminopyridin-3-yl)-5-(trifluoromethyl)-3H-imidazo[4,5-b]pyridin-3-yl)benzyl)piperidin-4-yl)amino)pyrimidine-2-carbonitrile

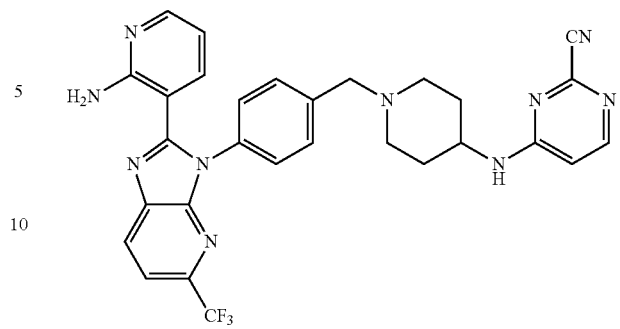

Example 410

To a solution of Intermediate 136 (450 mg, 792 gmol) and Intermediate 51 (335 mg, 1.06 mmol, TFA) in DMF (5 mL) was added K$_2$CO$_3$ (424 mg, 3.07 mmol) and NaI (15.3 mg, 102 μmol). The mixture was stirred at 25° C. for 16 hr. The mixture was filtered, and the filtrate was concentrated to give the crude product. After purified by prep-HPLC (column: Phenomenex C18 75*30 mm*3 μm; mobile phase: [water (NH$_3$H$_2$O+NH$_4$HCO$_3$)-ACN]; gradient: 47%-77% B over 7 min), 4-((1-(4-(2-(2-aminopyridin-3-yl)-5-(trifluoromethyl)-3H-imidazo[4,5-b]pyridin-3-yl)benzyl)piperidin-4-yl)amino)pyrimidine-2-carbonitrile (Example 410, 104.3 mg, yield: 18%) was obtained as a yellow powder. MS: m/z=571.3 [M+H]$^+$. $^1$H NMR (400 MHz, Dimethylsulfoxide-d$_6$) δ 8.44 (d, J=8.0 Hz, 1H), 8.24-7.97 (m, 3H), 7.87 (d, J=8.0 Hz, 1H), 7.51-7.40 (m, 4H), 7.21 (dd, J=7.6, 1.6 Hz, 1H), 6.91 (s, 2H), 6.67 (d, J=6.0 Hz, 1H), 6.40 (dd, J=7.6, 4.8 Hz, 1H), 3.96-3.65 (m, J=5.0 Hz, 1H), 3.57 (s, 2H), 2.88-2.76 (m, 2H), 2.23-2.09 (m, 2H), 1.89 (m, 2H), 1.57-1.42 (m, 2H). $^{19}$F NMR (400 MHz, Dimethylsulfoxide-d$_6$) δ −64.17.

Example 411: 2-(2-Aminopyridin-3-yl)-3-(4-((4-((2-cyanopyrimidin-4-yl)amino)piperidin-1-yl)methyl)phenyl)-3H-imidazo[4,5-b]pyridine-6-carbonitrile

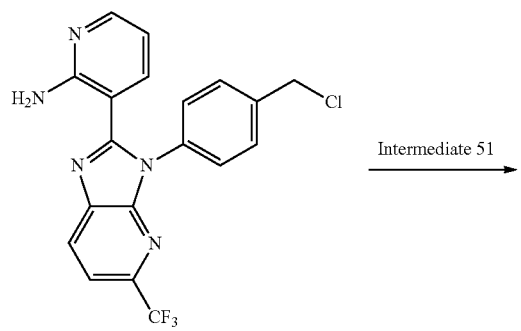

Intermediate 136 →[Intermediate 51]

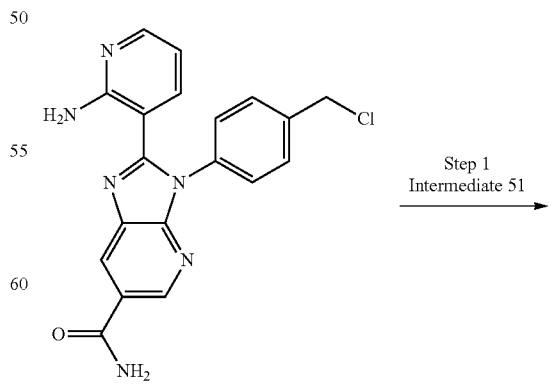

Intermediate 137 →[Step 1, Intermediate 51]

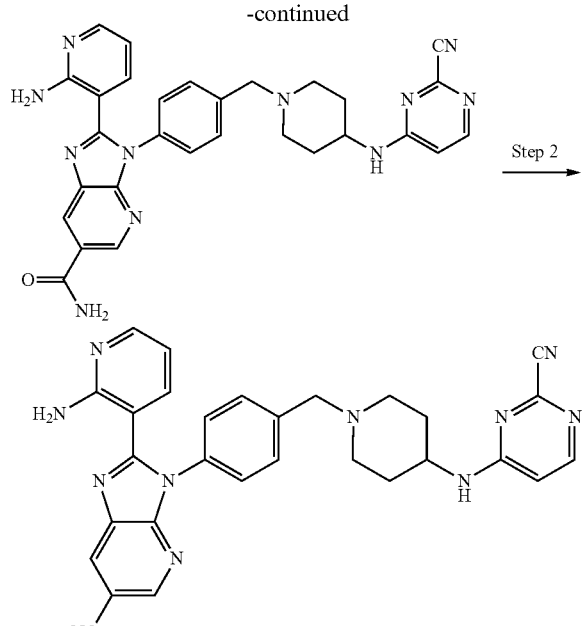

Example 411

Step 1: 2-(2-Aminopyridin-3-yl)-3-(4-((4-((2-cyano-pyrimidin-4-yl)amino)piperidin-1-yl)methyl)phenyl)-3H-imidazo[4,5-b]pyridine-6-carboxamide To a solution of Intermediate 137 (270 mg, 713 μmol) and Intermediate 51 (145 mg, 713 μmol) in DMF (5 mL) were added $K_2CO_3$ (493 mg, 3.56 mmol) and NaI (10.7 mg, 71.3 μmol). The mixture was stirred at 60° C. for 1 hr. The reaction mixture was diluted with $H_2O$ (50 mL) and extracted with $CH_2Cl_2$ (50 mL×2). The combined organic layers were washed with brine (50 mL), dried over $Na_2SO_4$, filtered and concentrated under reduced pressure to give 2-(2-aminopyridin-3-yl)-3-(4-((4-((2-cyanopyrimidin-4-yl)amino)piperidin-1-yl)methyl)phenyl)-3H-imidazo[4,5-b]pyridine-6-carboxamide (230 mg, yield: 38%) as a yellow solid. MS: m/z=546.3 [M+H]$^+$. $^1$H NMR (400 MHz, Dimethylsulfoxide-d$_6$) δ 8.85 (d, J=2.0 Hz, 1H), 8.65 (d, J=1.6 Hz, 1H), 8.22-8.17 (m, 1H), 8.09-8.07 (m, 1H), 8.01-7.99 (m, 1H), 7.61-7.50 (m, 2H), 7.48-7.39 (m, 4H), 7.21-7.17 ((m, 1H), 6.95 (s, 2H), 6.70-6.66 (m, 1H), 6.39 (dd, J=7.6, 4.8 Hz, 1H), 3.86-3.77 (m, 1H), 3.56 (s, 2H), 2.85-2.77 (m, 2H), 2.18-2.13 (m, 2H), 1.90-1.85 (m, 2H), 1.50-1.43 (m, 2H).

Step 2: 2-(2-Aminopyridin-3-yl)-3-(4-((4-((2-cyano-pyrimidin-4-yl)amino)piperidin-1-yl)methyl)phenyl)-3H-imidazo[4,5-b]pyridine-6-carbonitrile To a solution of 2-(2-aminopyridin-3-yl)-3-(4-((4-((2-cyanopyrimidin-4-yl)amino)piperidin-1-yl)methyl)phenyl)-3H-imidazo[4,5-b]pyridine-6-carboxamide (200 mg, 367 μmol) in $CH_2Cl_2$ (2 mL) was added Burgess reagent (174 mg, 733 μmol). The mixture was stirred at 25° C. for 1 hr. The reaction mixture was quenched with $NaHCO_3$ (10 mL) at 0° C., and then diluted with $H_2O$ (20 mL) and extracted with $CH_2Cl_2$ (20 mL×2). The combined organic layers were washed with brine (40 mL), dried over $Na_2SO_4$, filtered and concentrated under reduced pressure. After purified by prep-HPLC (column: Phenomenex Cis 75*30 mm*3 μm; mobile phase: [water ($NH_3H_2O+NH_4HCO_3$)-ACN]; gradient: 33%-63% B over 7 min), 2-(2-aminopyridin-3-yl)-3-(4-((4-((2-cyanopyrimidin-4-yl)amino)piperidin-1-yl)methyl)phenyl)-3H-imidazo[4,5-b]pyridine-6-carbonitrile (Example 411, 6.1 mg, yield: 3.1%) was obtained as a yellow solid. MS: m/z=528.4 [M+H]$^+$. $^1$H NMR (400 MHz, Acetonitrile-d$_3$) δ 8.64 (d, J=2.0 Hz, 1H), 8.47 (d, J=2.0 Hz, 1H), 8.06-8.04 (m, 1H), 7.52 (d, J=8.4 Hz, 2H), 7.36 (d, J=8.0 Hz, 2H), 7.19-7.15 (m, 1H), 6.59-6.57 (m, 2H), 6.37 (dd, J=8.0, 4.8 Hz, 1H), 6.29-6.22 (m, 1H), 4.01-3.76 (m, 1H), 3.61 (s, 2H), 2.93-2.78 (m, 2H), 2.26-2.19 (m, 2H), 2.00-1.96 (m, 2H), 1.60-1.46 (m, 2H).

Example 412: 4-((1-(4-(2-(2-Aminopyridin-3-yl)-5, 6-dimethyl-3H-imidazo[4,5-b]pyridin-3-yl)benzyl) piperidin-4-yl)amino)pyrimidine-2-carbonitrile

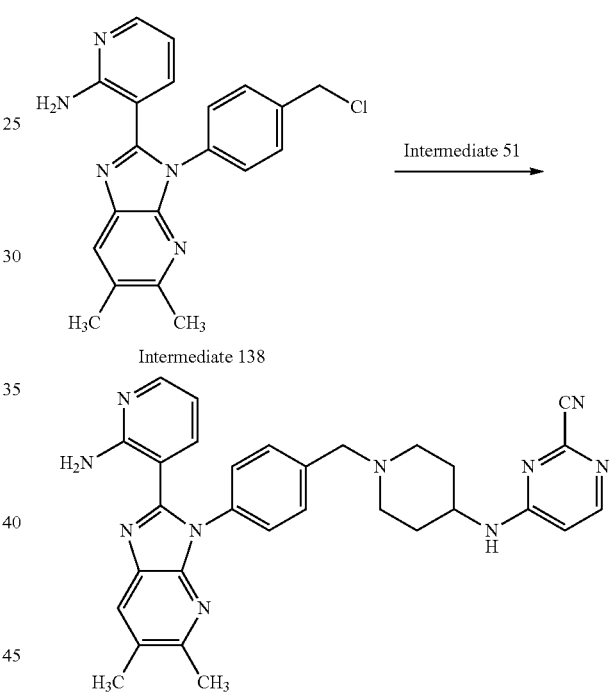

Example 412

To a solution of Intermediate 138 (200 mg, 549 μmol) and Intermediate 51 (174 mg, 549 μmol) in DMF (5 mL) were added NaI (41.2 mg, 275 μmol) and $K_2CO_3$ (379 mg, 2.75 mmol). The mixture was stirred at 50° C. for 1 hr. The reaction mixture was filtered and purified by prep-HPLC (column: Waters xbridge 150*25 mm 10 μm; mobile phase: [water ($NH_4HCO_3$)-ACN]; gradient: 37%-67% B over 14 min) to give 4-((1-(4-(2-(2-aminopyridin-3-yl)-5,6-dimethyl-3H-imidazo[4,5-b]pyridin-3-yl)benzyl)piperidin-4-yl)amino)pyrimidine-2-carbonitrile (Example 412, 54.7 mg, yield: 18%) as a yellow lyophilized powder. MS: m/z=531.4 [M+H]$^+$. $^1$H NMR (400 MHz, Dimethylsulfoxide-d$_6$) δ 8.12-8.03 (m, 2H), 7.97-7.94 (m, 2H), 7.45 (d, J=8.0 Hz, 2H), 7.33 (d, J=8.4 Hz, 2H), 7.07-7.02 (m, 3H), 6.67 (d, J=5.6 Hz, 1H), 6.33 (dd, J=7.6, 4.8 Hz, 1H), 3.90-3.72 (m, 1H), 3.57 (s, 2H), 2.86-2.79 (m, 2H), 2.45 (s, 3H), 2.38 (s, 3H), 2.18-2.11 (m, 2H), 1.92-1.85 (m, 2H), 1.54-1.45 (m, 2H).

Example 413: 4-((1-(4-(2-(2-aminopyridin-3-yl)-1H-imidazo[4,5-b]pyrazin-1-yl)benzyl)piperidin-4-yl)amino)pyrimidine-2-carbonitrile

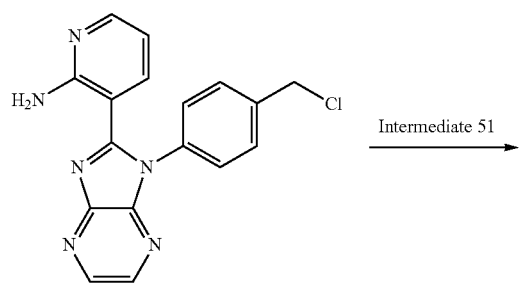

Intermediate 139

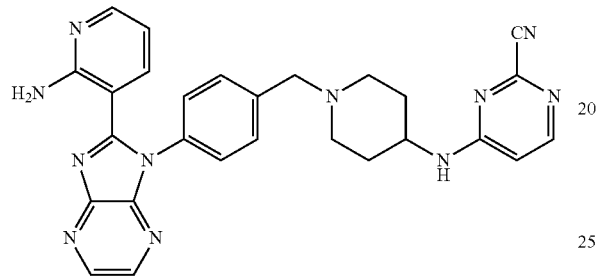

Example 413

A mixture of Intermediate 139 (100 mg, 296 μmol) and Intermediate 51 (72.4 mg, 356 mol) in DMF (3 mL) were added K₂CO₃ (205 mg, 1.48 mmol) and NaI (13.3 mg, 89 gmol), and then the mixture was stirred at 40° C. for 1 hr. The reaction mixture diluted with H₂O (30 mL) and extracted with EtOAc (30 mL×3). The combined organic layers were washed with H₂O (20 mL×4), dried over Na₂SO₄, filtered and concentrated under reduced pressure. After purified by silica gel flash chromatography (Eluent of 0~5% MeOH in CH₂Cl₂), 4-((1-(4-(2-(2-aminopyridin-3-yl)-1H-imidazo[4,5-b]pyrazin-1-yl)benzyl)piperidin-4-yl)amino)pyrimidine-2-carbonitrile (Example 413, 67.4 mg, yield: 45%) was obtained as a yellow powder. MS: m/z=504.1 [M+H]⁺. ¹H NMR (400 MHz, Dimethylsulfoxide-d₆) δ 8.58 (d, J=2.4 Hz, 1H), 8.38 (d, J=2.4 Hz, 1H), 8.14-8.00 (m, 3H), 7.49-7.40 (m, 4H), 7.27 (dd, J=8.0, 1.6 Hz, 1H), 6.96 (br s, 2H), 6.67 (d, J=6.0 Hz, 1H), 6.42 (dd, J=7.6, 4.8 Hz, 1H), 3.91-3.66 (m, 1H), 3.56 (s, 2H), 2.85-2.70 (m, 2H), 2.20-2.05 (m, 2H), 1.94-1.81 (m, 2H), 1.54-1.42 (m, 2H).

Example 414: Methyl 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylate

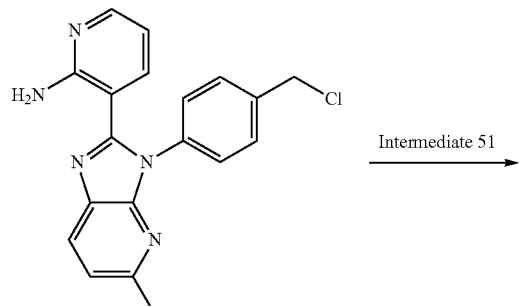

Intermediate 140

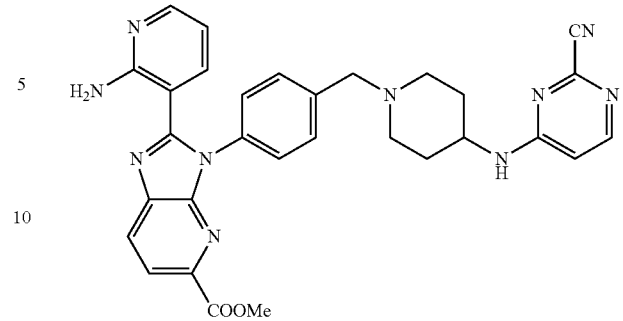

Example 414

To a solution of Intermediate 140 (340 mg, 863 μmol) and Intermediate 51 (274 mg, 863 mol, TFA) in DMF (5 mL) were added K₂CO₃ (597 mg, 4.32 mmol) and NaI (12.9 mg, 86.3 μmol). The mixture was stirred at 60° C. for 1 hr. The reaction mixture diluted with H₂O (10 mL) and extracted with CH₂Cl₂ (10 mL×3). The combined organic layers were washed with brine (10 mL×2), dried over Na₂SO₄, filtered and concentrated under reduced pressure. After purified by prep-HPLC (column: Waters xbridge 150*25 mm*10 μm; mobile phase: [water (NH₄HCO₃)-ACN]; gradient: 32%-62% B over 10 min), methyl 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylate (Example 414, 265.3 mg, 65.3 mg delivered, yield: 54%) was obtained as a yellow solid. MS: m/z=561.3 [M+H]⁺. ¹H NMR (400 MHz, Dimethylsulfoxide-d₆) δ 8.33 (d, J=8.4 Hz, 1H), 8.15-7.99 (m, 4H), 7.50-7.40 (m, 4H), 7.17 (dd, J=7.6 2.0 Hz, 1H), 6.98 (s, 2H), 6.68 (d, J=6.0 Hz, 1H), 6.38 (dd, J=7.6, 4.8 Hz, 1H), 3.85 (s, 3H), 3.84-3.67 (m, 1H), 3.58 (s, 2H), 2.88-2.79 (m, 2H), 2.22-2.10 (m, 2H), 1.94-1.82 (m, 2H), 1.57-1.44 (m, 2H).

Example 415: 2-(2-Aminopyridin-3-yl)-3-(4-((4-((2-cyanopyrimidin-4-yl)amino)piperidin-1-yl)methyl)phenyl)-3H-imidazo[4,5-b]pyridine-5-carboxylic acid

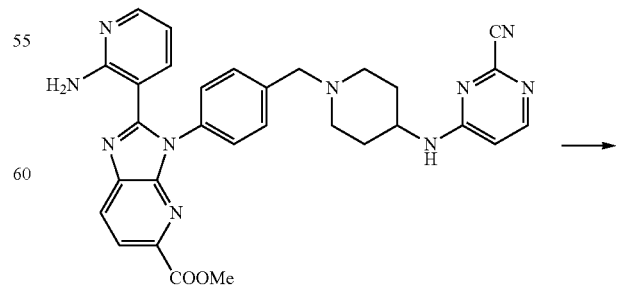

Example 414

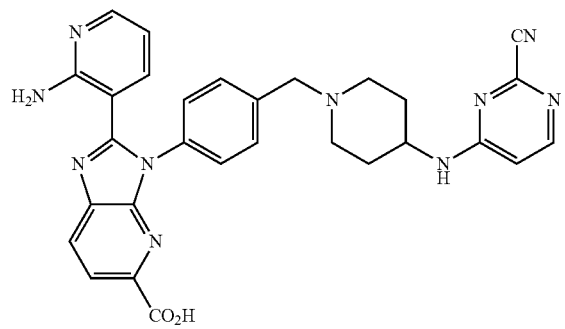

Example 415

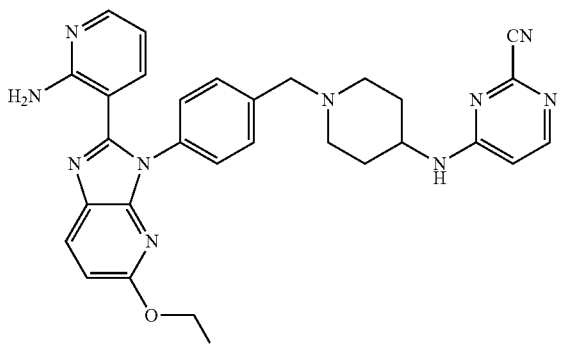

Example 416

To a solution of Example 414 (200 mg, 357 μmol) in THF (2 mL) and H₂O (2 mL) was added LiOH·H₂O (15 mg, 357 μmol). After purified by prep-HPLC (column: Waters xbridge 150*25 mm*10 μm; mobile phase: [water (NH₄HCO₃)-ACN]; gradient: 11/%-41% B over 10 min), 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylic acid (Example 415, 120 mg, yield: 44%) was obtained as a yellow solid. MS: m/z=547.4 [M+H]⁺. ¹H NMR (400 MHz, Methanol-d₄) δ8.42 (d, J=8.4 Hz, 1H), 8.31 (d, J=8.0 Hz, 1H), 8.22-8.13 (m, 1H), 8.08 (d, J=5.2 Hz, 1H), 7.96-7.88 (m, 3H), 7.70 (d, J=7.2 Hz, 2H), 6.98-6.81 (m, 2H), 4.58-4.49 (m, 2H), 4.48-4.25 (m, 1H), 3.77-3.63 (m, 2H), 3.60-3.35 (m, 2H), 2.37-2.27 (m, 2H), 2.18-1.99 (m, 2H).

Example 416: 4-((1-(4-(2-(2-Aminopyridin-3-yl)-5-(fluoromethoxy)-3H-imidazo[4,5-b]pyridin-3-yl)benzyl)piperidin-4-yl)amino)pyrimidine-2-carbonitrile To a solution of Intermediate 141 (290 mg HCl salt, 690 μmol) and Intermediate 51 (240 mg TFA salt, 759 μmol) in DMF (2 mL) were added NaI (51.7 mg, 345 gmol) and K₂CO₃ (476 mg, 3.45 mmol). The mixture was stirred at 50° C. for 1 hr. The reaction mixture was diluted with water (10 mL) and extracted with EtOAc (2×10 mL). The combined organic layers were washed with brine (10 mL), dried over Na₂SO₄ filtered and concentrated under reduced pressure. After purified by silica gel flash chromatography (Eluent of 0~4%, MeOH in CH₂Cl₂), 4-((1-(4-(2-(2-aminopyridin-3-yl)-5-(fluoromethoxy)-3H-imidazo[4,5-b]pyridin-3-yl)benzyl)piperidin-4-yl)amino)pyrimidine-2-carbonitrile (Example 416, 169 mg, yield. 43%) was obtained as a yellow solid. MS: m/z=551.1 [M+H]⁺. ¹H NMR (400 MHz, Dimethylsulfoxide-d₆) δ 8.25 (d, J=8.4 Hz, 1H), 8.15-8.00 (m, 2H), 7.97 (dd, J=4.8, 1.6 Hz, 1H), 7.45 (d, J=8.0 Hz, 2H), 7.37 (d, J=8.0 Hz, 2H), 7.10 (dd, J=7.6, 2.0 Hz, 1H), 6.98 (d, J=8.8 Hz, 1H), 6.90 (br s, 2H), 6.67 (d, J=6.4 Hz, 1H), 6.36 (dd, J=7.6, 4.8 Hz, 1H), 6.10-5.92 (m, 2H), 3.88-3.73 (m, 1H), 3.57 (s, 2H), 2.81 (d, J=11.2 Hz, 2H), 2.18-2.10 (m, 2H), 1.93-1.83 (m, 2H), 1.59-1.38 (m, 2H), ¹⁹F NMR (400 MHz, Dimethylsulfoxide-d₆) 8-153.916.

Example 417: 4-((1-(4-(2-(2-Aminopyridin-3-yl)-5-(tetrahydrofuran-3-yl)-3H-imidazo[4,5-b]pyridin-3-yl)benzyl)piperidin-4-yl)amino)pyrimidine-2-carbonitrile

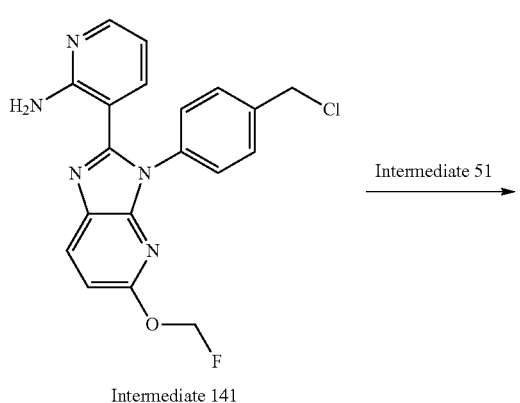

Intermediate 141 →Intermediate 51

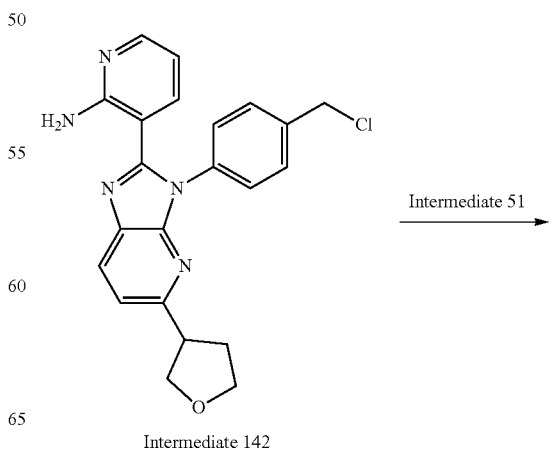

Intermediate 142 →Intermediate 51

1503
-continued

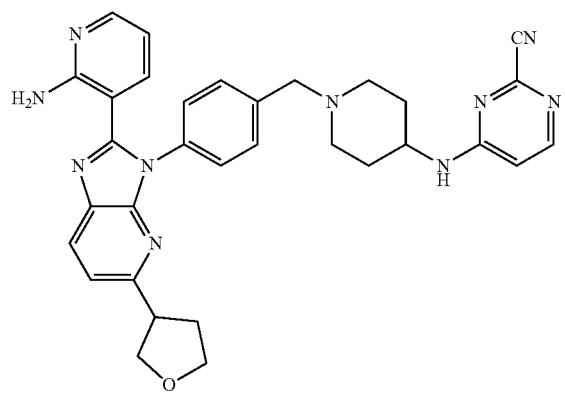

Example 417

To a solution of Intermediate 142 (200 mg, 492 μmol) and Intermediate 51 (156 mg, 492 mol, TFA) in DMF (4 mL) were added NaI (36.9 mg, 246 μmol) and K₂CO₃ (340 mg, 2.46 gmol). The mixture was stirred at 50° C. for 1 hr. The reaction mixture was filtered. After purified by prep-HPLC (column: [water (NH₄HCO₃)-ACN]; B %: 32%-62%, 14 min), 4-((1-(4-(2-(2-aminopyridin-3-yl)-5-(tetrahydrofuran-3-yl)-3H-imidazo[4,5-b]pyridin-3-yl)benzyl)piperidin-4-yl)amino)pyrimidine-2-carbonitrile (Example 417, 84.5 mg, yield: 26%) was obtained as a yellow solid. MS: m/z=573.4 [M+H]⁺. ¹H NMR (400 MHz, Dimethylsulfoxide-d₆) δ 8.18-8.02 (m, 3H), 7.98 (dd, J=4.8, 2.0 Hz, 1H), 7.45 (d, J=8.4 Hz, 2H), 7.40-7.33 (m, 3H), 7.11 (dd, J=8.0, 2.0 Hz, 1H), 6.96 (br s, 2H), 6.67 (d, J=6.4 Hz, 1H), 6.36 (dd, J=7.6, 4.8 Hz, 1H), 4.05 (t, J=8.0 Hz, 1H), 3.93-3.87 (m, 1H), 3.84-3.68 (m, 3H), 3.65-3.55 (m, 3H), 2.86-2.79 (m, 2H), 2.31-2.22 (m, 1H), 2.19-2.07 (m, 3H), 1.96-1.82 (m, 2H), 1.58-1.43 (m, 2H).

Example 418: 4-((1-(4-(2-(2-Aminopyridin-3-yl)-5-(5-cyanopyridin-2-yl)-3H-imidazo[4,5-b]pyridin-3-yl)benzyl)piperidin-4-yl)amino)pyrimidine-2-carbonitrile

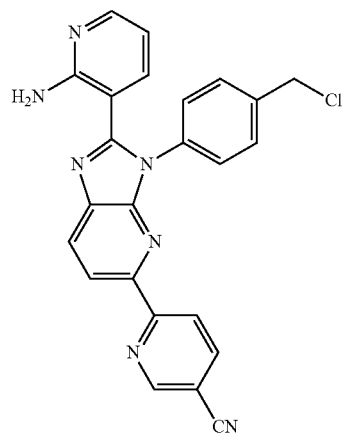

Intermediate 143

1504
-continued

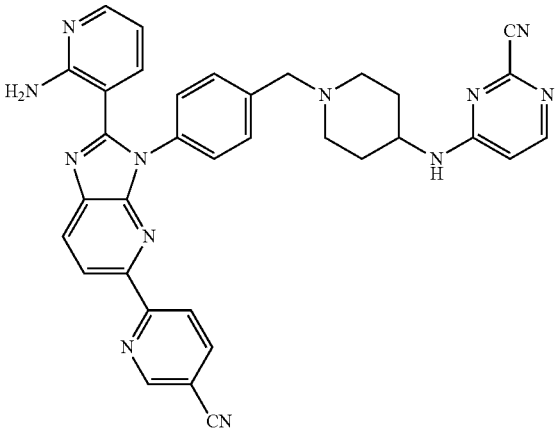

Example 418

To a solution of Intermediate 143 (70 mg, 148 μmol, HCl salt) in DMF (1 mL) were added Intermediate 51 (30 mg, 148 μmol), NaI (2.21 mg, 14.8 μmol) and K₂CO₃ (61.2 mg, 443 μmol). The mixture was stirred at 50° C. for 16 hr. The reaction was concentrated under reduced pressure. After purified by prep-TLC (CH₂Cl₂:MeOH=10:1), 4-((1-(4-(2-(2-aminopyridin-3-yl)-5-(5-cyanopyridin-2-yl)-3H-imidazo[4,5-b]pyridin-3-yl)benzyl)piperidin-4-yl)amino)pyrimidine-2-carbonitrile (Example 418, 7.3 mg, yield: 8.2%) was obtained as a yellow solid. MS: m/z=605.0 [M+H]⁺. ¹H NMR (400 MHz, Chloroform-d) δ 8.90 (s, 1H), 8.59 (dd, J=8.4, 1.2 Hz, 1H), 8.44 (d, J=8.4 Hz, 1H), 8.21 (dd, J=8.4, 1.2 Hz, 1H), 8.19-8.13 (m, 1H), 8.11-8.07 (m, 1H), 7.97 (d, J=8.4 Hz, 1H), 7.61-7.54 (m, 2H), 7.42 (d, J=7.6 Hz, 2H), 7.10 (d, J=8.0 Hz, 1H), 6.67 (brs, 2H), 6.46 (d, J=6.4 Hz, 1H), 6.39-6.35 (m, 1H), 4.39-3.80 (m, 1H), 3.73 (s, 2H), 3.23-2.88 (m, 2H), 2.51-2.30 (m, 2H), 2.17-2.07 (m, 2H), 1.37-1.27 (m, 2H).

Example 419: 4-((1-(4-(2-(2-Aminopyridin-3-yl)-5-(6-cyanopyridin-3-yl)-3H-imidazo[4,5-b]pyridin-3-yl)benzyl)piperidin-4-yl)amino)pyrimidine-2-carbonitrile

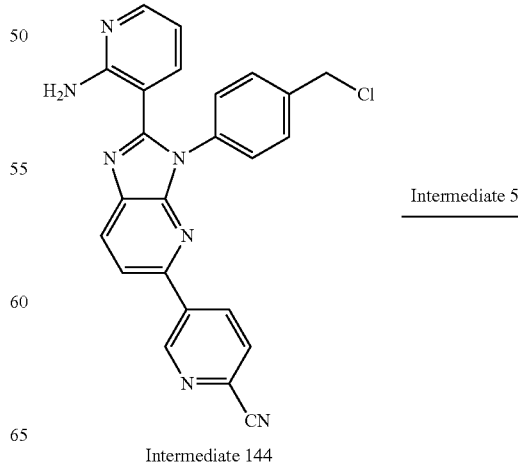

Intermediate 144

1505

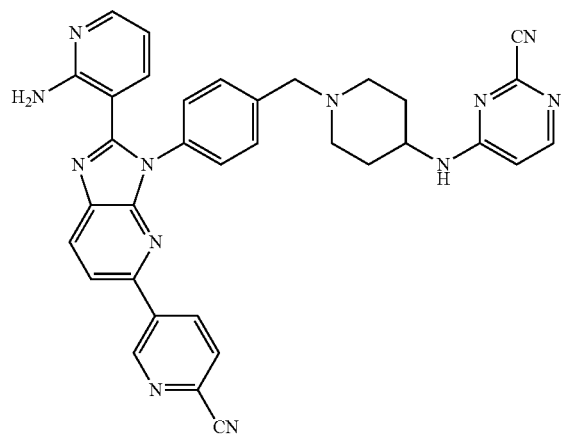

Example 419

To a solution of Intermediate 144 (120 mg, 274 μmol, HCl salt) in DMF (2 mL) were added Intermediate 51 (55.7 mg, 274 μmol), NaI (8.22 mg, 54.8 μmol) and K₂CO₃ (114 mg, 822 mol). The mixture was stirred at 50° C. for 16 hr. The mixture was filtered, and the filtrate was concentrated to give the crude product. After purified by prep-HPLC (column: Phenomenex C18 75*30 mm*3 μm; mobile phase: [water (NH₃H₂O+NH₄HCO₃)-ACN]; gradient: 47%-77% B over 7 min), 4-((1-(4-(2-(2-aminopyridin-3-yl)-5-(6-cyanopyridin-3-yl)-3H-imidazo[4,5-b]pyridin-3-yl)benzyl)piperidin-4-yl)amino)pyrimidine-2-carbonitrile (Example 419, 56.2 mg, yield: 34%) was obtained as a yellow lyophilized powder. MS: m/z=605.1 [M+H]⁺. ¹H NMR (400 MHz, Dimethyl-sulfoxide-d₆) δ 9.41 (d, J=2.0 Hz, 1H), 8.62 (dd, J=8.0, 2.0 Hz, 1H), 8.38 (d, J=8.4 Hz, 1H), 8.23 (d, J=8.4 Hz, 1H), 8.14 (d, J=8.4 Hz, 1H), 8.12-8.04 (m, 2H), 8.02 (dd, J=4.8, 2.0 Hz, 1H), 7.54-7.45 (m, 4H), 7.18 (dd, J=7.6, 1.6 Hz, 1H), 7.05 (br s, 2H), 6.67 (d, J=6.4 Hz, 1H), 6.40 (dd, J=7.6, 4.8 Hz, 1H), 3.90-3.73 (m, 1H), 3.59 (s, 2H), 2.88-2.78 (m, 2H), 2.23-2.09 (m, 2H), 1.94-1.82 (m, 2H), 1.56-1.44 (m, 2H).

Example 420: 4-((1-(4-(2-(2-Aminopyridin-3-yl)-5-(oxetan-3-yl)-3H-imidazo[4,5-h]pyridin-3-yl)benzyl)piperidin-4-yl)amino)pyrimidine-2-carbonitrile

1506

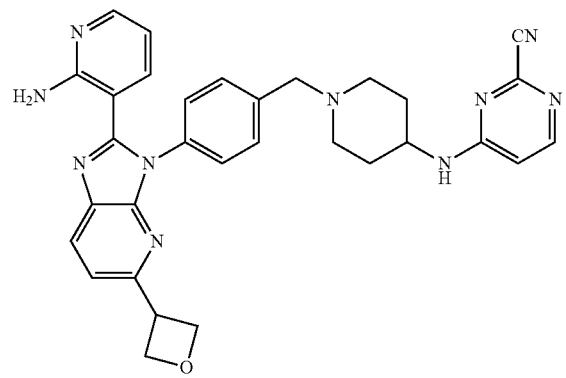

Example 420

To a solution of Intermediate 145 (60.5 mg, 134 μmol) in DMF (1 mL) were added DIEA (69.2 mg, 536 μmol) and Intermediate 51 (29.9 mg, 147 μmol). The mixture was stirred at 25° C. for 12 hr under N₂. After purified by prep-HPLC (column: Welch Xtimate C18 150*25 mm*5 μm; mobile phase: [water (NH₄HCO₃)-ACN]; gradient: 37%-67% B over 7 min), 4-((1-(4-(2-(2-aminopyridin-3-yl)-5-(oxetan-3-yl)-3H-imidazo[4,5-b]pyridin-3-yl)benzyl)piperidin-4-yl)amino)pyrimidine-2-carbonitrile (Example 420, 1.9 mg, yield: 2.5% for 2 steps) was obtained as yellow solid. MS: m/z=559.1 [M+H]⁺. ¹H NMR (400 MHz, Dimethylsulfoxide-d₆) δ 8.18 (d, J=6.8 Hz, 11H), 8.10-8.00 (m, 2H), 8.00-7.95 (m, 1H), 7.50-7.30 (m, 5H), 7.10 (dd, J=6.4, 1.6 Hz, 1H), 6.97 (br s, 2H), 6.68 (d, J=4.8 Hz, 1H), 6.40-6.30 (m, 1H), 4.88 (dd, J=6.8, 4.4 Hz, 2H), 4.78-4.70 (m, 2H), 4.55-4.40 (m, 1H), 3.85-3.75 (m, 1H), 3.65-3.50 (m, 2H), 2.90-2.75 (m, 2H), 2.25-2.05 (m, 2H), 1.95-1.80 (m, 2H), 1.55-1.45 (m, 2H).

Example 421: 4-((1-(4-(2-(2-Aminopyridin-3-yl)-5-(4-methoxyphenyl)-3H-imidazo[4,5-b]pyridin-3-yl)benzyl)piperidin-4-yl)amino)pyrimidine-2-carbonitrile

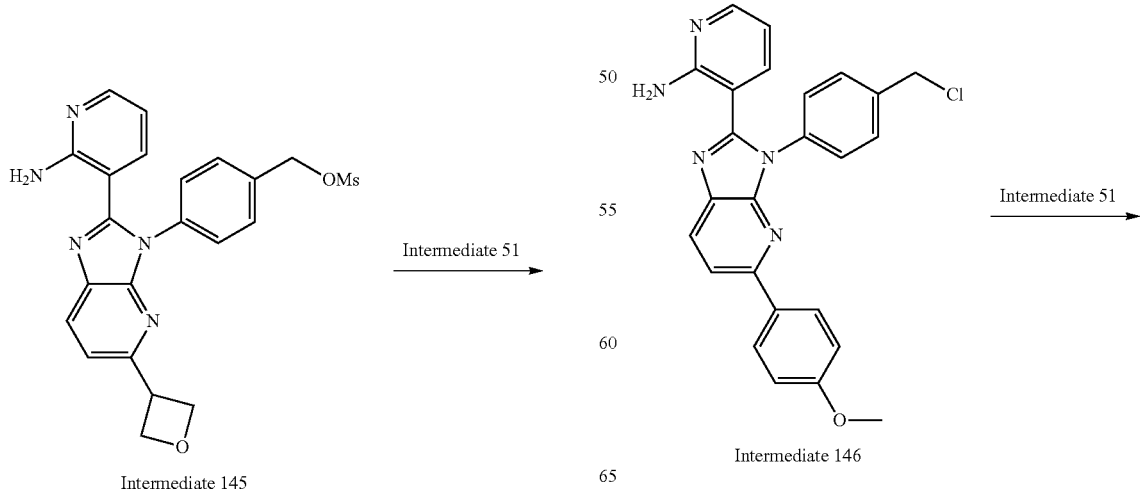

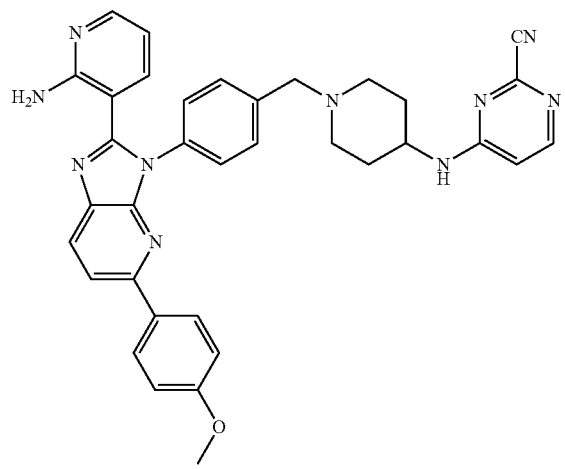

Example 421

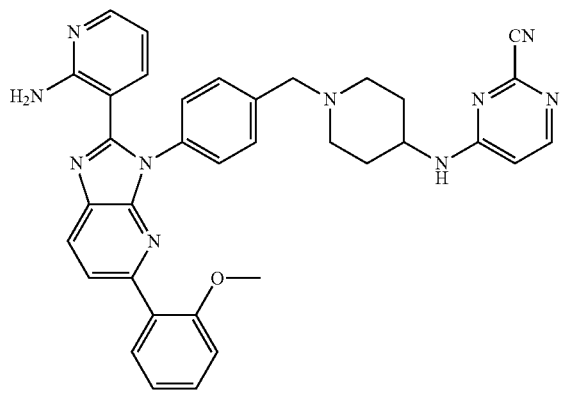

Example 422

To a solution of Intermediate 146 (200 mg, 453 μmol) in DMF (3 mL) were added DIEA (234 mg, 1.81 mmol) and Intermediate 51 (101 mg, 498 μmol). The mixture was stirred at 80° C. for 2 hr under $N_2$. After purified by prep-HPLC (column: Phenomenex C18 80*40 mm*3 μm; mobile phase: [water ($NH_3H_2O+NH_4HCO_3$)-ACN]; gradient: 62%-92% B over 7 min), 4-((1-(4-(2-(2-aminopyridin-3-yl)-5-(4-methoxyphenyl)-3H-imidazo[4,5-b]pyridin-3-yl)benzyl)piperidin-4-yl)amino)pyrimidine-2-carbonitrile (Example 421, 41.3 mg, yield: 15%) was obtained as a yellow solid. MS: m/z=609.2 [M+H]$^+$. $^1$H NMR (400 MHz, Dimethylsulfoxide-$d_6$) δ 8.22 (d, J=8.0 Hz, 1H), 8.08 (d, J=6.0 Hz, 2H), 8.03-7.90 (m, 3H), 7.91 (d, J=8.8 Hz, 1H), 7.50-7.40 (m, 4H), 7.18-7.00 (m, 5H), 6.68 (d, J=6.0 Hz, 1H), 6.40-6.30 (m, 1H), 4.00-3.70 (m, 4H), 3.59 (s, 2H), 2.83 (d, J=10.8 Hz, 2H), 2.30-2.10 (m, 2H), 2.00-1.80 (m, 2H), 1.60-1.40 (m, 2H).

Example 422: 4-((1-(4-(2-(2-Aminopyridin-3-yl)-5-(2-methoxyphenyl)-3H-imidazo[4,5-b]pyridin-3-yl)benzyl)piperidin-4-yl)amino)pyrimidine-2-carbonitrile To a solution of Intermediate 147 (320 mg, 724 μmol) and Intermediate 51 (147 mg, 724 μmol) in DMF (3 mL) were added NaI (21.7 mg, 145 μmol) and $K_2CO_3$ (400 mg, 2.90 mmol). The mixture was stirred at 50° C. for 1 hr. The mixture was diluted with water (10 mL) and extracted with CH2Cl2 (20 mL×3). The combined organic layers were washed with brine (20 mL×2), dried over $Na_2SO_4$, filtered and concentrated under reduced pressure. After purified by silica gel flash chromatography (Eluent of 4~5% MeOH in $CH_2Cl_2$), 4-((1-(4-(2-(2-aminopyridin-3-yl)-5-(2-methoxyphenyl)-3H-imidazo[4,5-b]pyridin-3-yl)benzyl)piperidin-4-yl)amino)pyrimidine-2-carbonitrile (Example 422, 35 mg, yield. 7.7%) was obtained as a yellow lyophilized powder. MS: m/z=609.1 [M+H]$^+$. $^1$H NMR (400 MHz, Methanol-$d_4$) δ 8.14 (d, J=8.4 Hz, 1H), 8.03-8.01 (m, 1H), 7.99-7.95 (m, 1H), 7.90 (d, J=8.8 Hz, 1H), 7.64 (dd, J=7.2 Hz, 1.2 Hz, 1H), 7.55 (d, J=7.2 Hz, 2H), 7.47 (d, J=8.0 Hz, 2H), 7.38-7.32 (m, 2H), 7.11 (d, J=8.4 Hz, 1H), 7.00 (t, J=7.2 Hz, 1H), 6.61-6.58 (m, 1H), 6.48 (dd, J=7.2, 5.2 Hz, 1H), 4.06-3.94 (m, 1H), 3.86 (s, 3H), 3.83-3.73 (m, 2H), 3.09-3.02 (m, 2H), 2.54-2.31 (m, 2H), 2.10-2.01 (m, 2H), 1.66-1.58 (m, 2H).

Example 423: 4-((1-(4-(2-(2-Aminopyridin-3-yl)-5-(trifluoromethoxy)-3H-imidazo[4,5-b]pyridin-3-yl)benzyl)piperidin-4-yl)amino)pyrimidine-2-carbonitrile

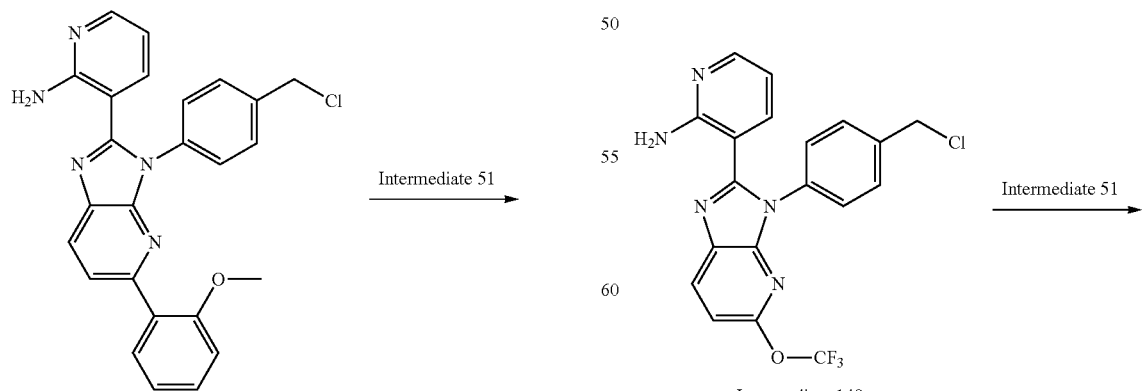

1509
-continued

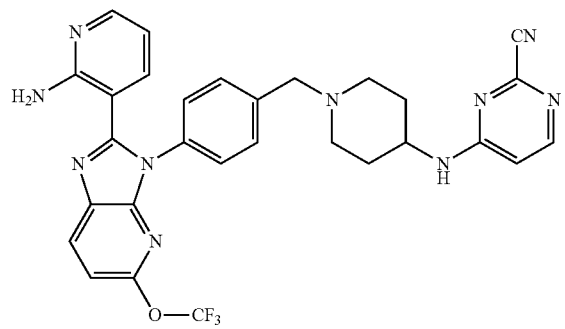

Example 423

1510
-continued

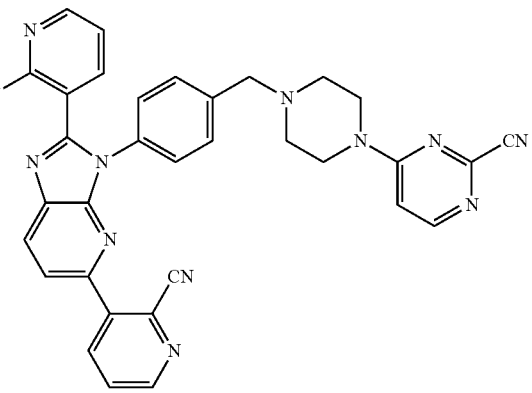

Example 424

To a solution of Intermediate 148 (150 mg, 357 μmol) and Intermediate 51 (79.9 mg, μmol) in DMF (3 mL) were added K₂CO₃ (148 mg, 1.07 mmol) and NaI (10.7 mg. 71.5 μmol) at 25° C. This mixture was stirred at 80° C. for 2 hr. The mixture was quenched with H₂O (20 mL) and extracted with EtOAc (20 mL×3). The combined organic phase was filtered and concentrated to give the residue. After by prep-HPLC (column: Phenomenex C18 75×30 mm×3 μm; mobile phase: [water (NH₃H₂O+NH₄HCO₃)-ACN]; gradient: 47%-77% B over 7 min), 4-((1-(4-(2-(2-aminopyridin-3-yl)-5-(trifluoromethoxy)-3H-imidazo[4,5-b]pyridin-3-yl)benzyl)piperidin-4-yl)amino)pyrimidine-2-carbonitrile (Example 423, 40.9 mg, yield: 20% for 2 steps) was obtained as a light yellow solid. MS: m/z=587.1 [M+H]⁺. ¹H NMR (400 MHz, Dimethylsulfoxide-d₆) δ 8.41 (d, J=8.4 Hz, 1H), 8.12-7.98 (m, 3H), 7.45 (d, J=8.4 Hz, 2H), 7.38 (d, J=8.0 Hz, 2H), 7.28 (d, J=8.4 Hz, 1H), 7.18 (dd, J=7.6, 1.6 Hz, 1H), 6.85 (s, 2H), 6.67 (d, J=6.0 Hz, 1H), 6.39 (dd, J=7.6, 4.8 Hz, 1H), 3.88-3.74 (m, 1H), 3.56 (s, 2H), 2.83-2.74 (m, 2H), 2.18-2.09 (m, 2H), 1.94-1.82 (m, 2H), 1.56-1.44 (m, 2H). ¹⁹F NMR (400 MHz, Dimethylsulfoxide-d₆) δ −55.510.

Example 424: 4-(4-(4-(2-(2-Aminopyridin-3-yl)-5-(2-cyanopyridin-3-yl)-3H-imidazo[4,5-b]pyridin-3-yl)benzyl)piperazin-1-yl)pyrimidine-2-carbonitrile To a solution of Intermediate 126 (200 mg HCl salt, 457 μmol) and Intermediate 53 (138 mg TFA salt, 457 μmol) in DMF (2 mL) was added NaI (34 mg, 228 μmol) and K₂CO₃ (315 mg, 2.28 μmol). The mixture was stirred at 50° C. for 1 hr. The reaction mixture was filtered and the residue was purified by prep-HPLC (column: [water (NH₄HCO₃)-ACN]; B %: 36%-66%, 14 min), 4-(4-(4-(2-(2-aminopyridin-3-yl)-5-(2-cyanopyridin-3-yl)-3H-imidazo[4,5-b]pyridin-3-yl)benzyl)piperazin-1-yl)pyrimidine-2-carbonitrile (Example 424, 32 mg, yield: 29%) was obtained as a purple solid. MS: m/z=591.4 [M+H]⁺. ¹H NMR (400 MHz, Dimethylsulfoxide-d₆) δ 8.79 (dd, J=4.8, 1.2 Hz, 1H), 8.43 (d, J=8.0 Hz, 1H), 8.37 (dd, J=8.0, 1.2 Hz, 1H), 8.26 (d, J=6.4 Hz, 1H), 8.02 (dd, J=4.8, 1.6 Hz, 1H), 7.94 (d, J=8.4 Hz, 1H), 7.85 (dd, J=8.0, 4.8 Hz, 1H), 7.51-7.46 (m, 4H), 7.21 (dd, J=7.6, 1.6 Hz, 1H), 7.11 (d, J=6.8 Hz, 1H), 7.01 (br s, 2H), 6.40 (dd, J=7.6, 4.4 Hz, 1H), 3.74-3.64 (m, 4H), 3.61 (s, 2H), 2.49-2.43 (m, 4H).

Example 425: 4-((1-(4-(2-(2-Aminopyridin-3-yl)-5-isopropoxy-3H-imidazo[4,5-b]pyridin-3-yl)benzyl)piperidin-4-yl)amino)pyrimidine-2-carbonitrile

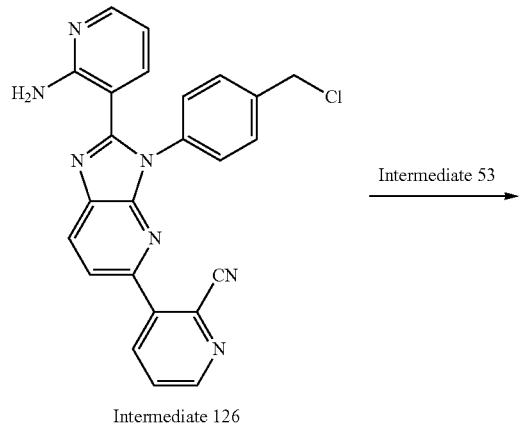

Intermediate 53 →

Intermediate 126

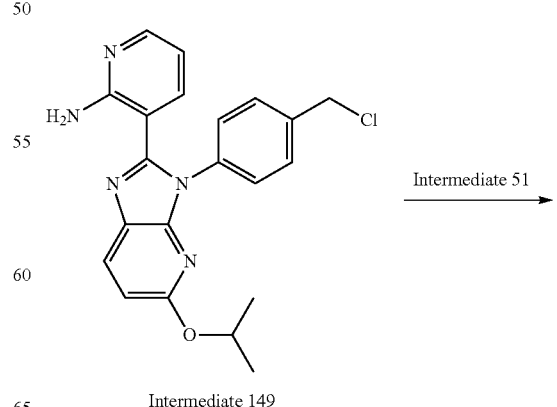

Intermediate 51 →

Intermediate 149

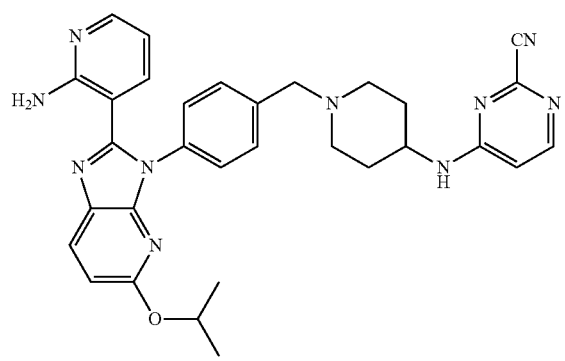

Example 425

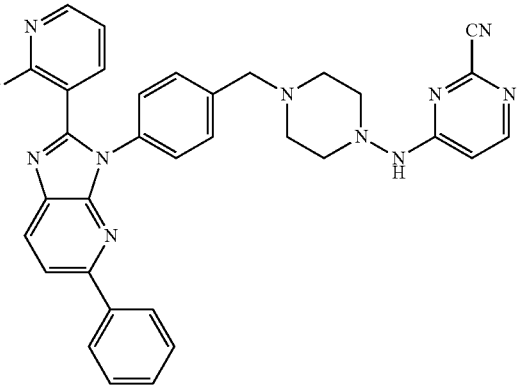

Example 426

To a mixture of Intermediate 149 (200 mg, 508 μmol) and Intermediate 51 (103 mg, 508 μmol) in DMF (2 mL) was added DIEA (354 μL, 2.03 mmol). The mixture was stirred at 80° C. for 1 hr. The mixture was concentrated. After purified by prep-HPLC (column: Phenomenex C18 80*40 mm*3 μm; mobile phase. [water ($NH_3H_2O+NH_4HCO_3$)-ACN]; gradient: 55%-85% B over 7 min), 4-((1-(4-(2-(2-aminopyridin-3-yl)-5-isopropoxy-3H-imidazo[4,5-b]pyridin-3-yl)benzyl)piperidin-4-yl)amino)pyrimidine-2-carbonitrile (Example 425, 44.4 mg, yield: 16%) was obtained as a yellow solid. MS: m/z=561.1 [M+H]$^+$. $^1$H NMR (400 MHz, Dimethylsulfoxide-$d_6$) δ 8.20-8.02 (m, 3H), 7.95 (dd, J=4.8, 1.6 Hz, 1H), 7.47-7.41 (m, 2H), 7.38-7.31 (m, 2H), 7.06 (dd, J=7.6, 1.6 Hz, 1H), 6.97 (br s, 2H), 6.73 (d, J=8.4 Hz, 1H), 6.67 (d, J=6.0 Hz, 1H), 6.34 (dd, J=7.6, 4.8 Hz, 1H), 5.08-4.98 (m, 1H), 3.93-3.72 (m, 1H), 3.57 (s, 2H), 2.85-2.74 (m, 2H), 2.22-2.07 (m, 2H), 1.96-1.78 (m, 2H), 1.56-1.41 (m, 2H), 1.24 (d, J=6.4 Hz, 6H).

Example 426: 4-((4-(4-(2-(2-Aminopyridin-3-yl)-5-phenyl-3H-imidazo[4,5-b]pyridin-3-yl)benzyl)piperazin-1-yl)amino)pyrimidine-2-carbonitrile A mixture of Intermediate 111 (100 mg HCl salt, 195 μmol), 4-chloropyrimidine-2-carbonitrile (27.2 mg, 195 μmol), and DIEA (126 mg, 975 μmol, 170 μL) in NMP (3 mL) was taken up into a microwave tube. The sealed tube was heated at 160° C. for 1 hr under microwave. The crude was diluted with $CH_2Cl_2$ (5 mL) and $H_2O$ (5 mL) and extracted with $CH_2Cl_2$ (15 mL×3). The combined organic layers were washed with brine (5 mL), dried over anhydrous $Na_2SO_4$, filtered and concentrated. The residue was purified by prep-HPLC (column: Phenomenex C18 75×30 mm×3 μm; mobile phase: [water ($NH_3H_2O+NH_4HCO_3$)-ACN]; gradient: 50%-80% B over 8 min) to give 4-((4-(4-(2-(2-aminopyridin-3-yl)-5-phenyl-3H-imidazo[4,5-b]pyridin-3-yl)benzyl)piperazin-1-yl)amino)pyrimidine-2-carbonitrile (Example 426, 3 mg, yield: 2.6%) as a light-yellow solid. MS: m/z=580.4 [M+H]$^+$. $^1$H NMR (400 MHz, Dimethyl-sulfoxide-$d_6$) δ 9.34 (s, 1H), 8.32-8.22 (m, 2H), 8.06-7.95 (m, 4H), 7.52-7.42 (m, 6H), 7.45-7.36 (m, 1H), 7.16 (dd, J=7.6, 1.6 Hz, 1H), 7.03 (br s, 2H), 7.01-6.97 (m, 1H), 6.38 (dd, J=8.0, 4.8 Hz, 1H), 3.61 (s, 2H), 3.32-3.31 (m, 2H), 2.98-2.66 (m, 6H).

Example 427: 4-((1-(4-(2-(2-Aminopyridin-3-yl)-5-(methoxy-$d_3$)-3H-imidazo[4,5-b]pyridin-3-yl)benzyl)piperidin-4-yl)amino)pyrimidine-2-carbonitrile

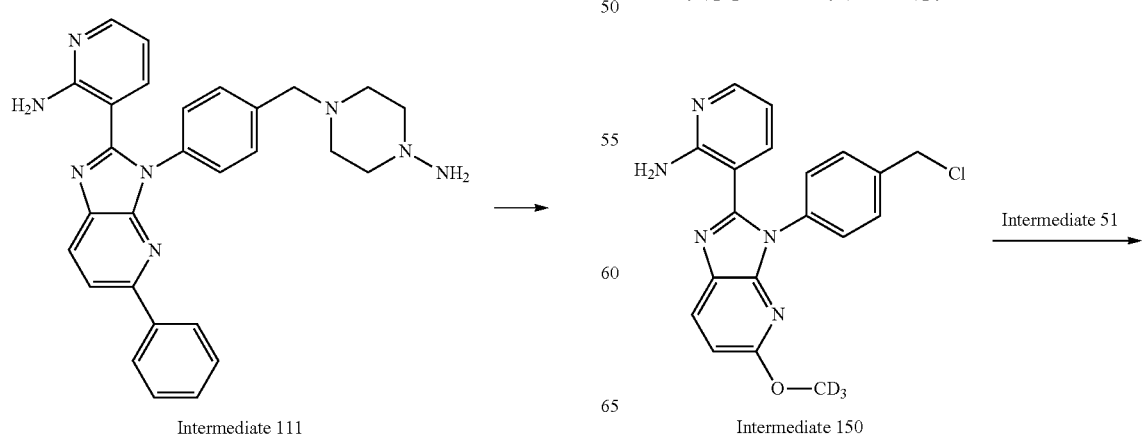

Intermediate 111

Intermediate 150

Intermediate 51

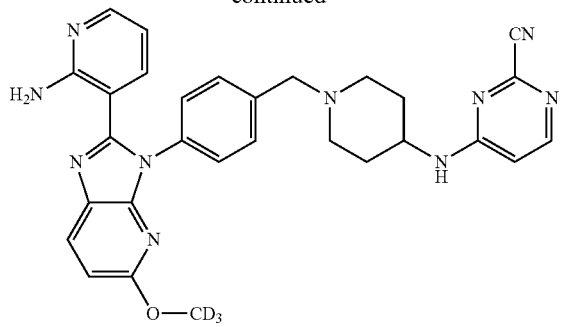

Example 427

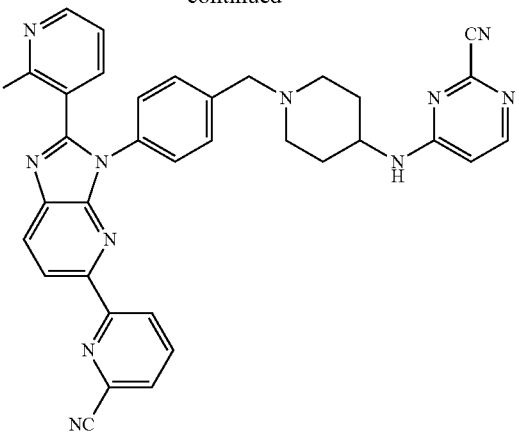

Example 428

To a solution of Intermediate 150 (105 mg, 285 μmol) and Intermediate 51 (63.8 mg, 314 μmol) in DMF (3 mL) were added K$_2$CO$_3$ (118 mg, 856 μmol) and NaI (8.56 mg, 57.1 μmol) in one portion at 20° C. The reaction mixture was stirred at 50° C. for 2 hr. H$_2$O (10 mL) was added at 20° C. and the mixture was extracted with EtOAc (10 mL×3). The combined organic layers were washed with brine (10 mL×2), dried over anhydrous Na$_2$SO$_4$, filtered and concentrated under reduced pressure. The residue purified by prep-HPLC (column: Welch Xtimate C18 150×25 mm×5 μm; mobile phase: [water (NH$_4$HCO$_3$)-ACN]; gradient: 45%-75% B over 7 min) to give 4-((1-(4-(2-(2-aminopyridin-3-yl)-5-(methoxy-d$_3$)-3H-imidazo[4,5-b]pyridin-3-yl)benzyl)piperidin-4-yl)amino)pyrimidine-2-carbonitrile (Example 427, 37.5 mg, yield: 12%) as an off-white solid. MS: m/z=536.1 [M+H]$^+$. $^1$H NMR (400 MHz, Dimethylsulfoxide-d$_6$) δ 8.13-8.04 (m, 3H), 7.95 (dd, J=4.8, 1.6 Hz, 1H), 7.46-7.42 (m, 2H), 7.39-7.35 (m, 2H), 7.04 (dd, J=7.6, 1.6 Hz, 1H), 6.96 (s, 2H), 6.81 (d, J=8.4 Hz, 1H), 6.67 (d, J=6.0 Hz, 1H), 6.34 (dd, J=7.6, 4.8 Hz, 1H), 3.81-3.79 (m, 1H), 3.57 (s, 2H), 2.84-2.71 (m, 2H), 2.18-2.09 (m, 2H), 1.92-1.84 (m, 2H), 1.52-1.43 (m, 2H).

Example 428: 4-((1-(4-(2-(2-Aminopyridin-3-yl)-5-(6-cyanopyridin-2-yl)-3H-imidazo[4,5-b]pyridin-3-yl)benzyl)piperidin-4-yl)amino)pyrimidine-2-carbonitrile To a mixture of Intermediate 151 (320 mg, 730 μmol) and Intermediate 51 (148 mg, 731 gmol) in DMF (5 mL) was added DIEA (509 μL, 2.92 mmol). The mixture was stirred at 80° C. for 1 hr. H$_2$O (50 mL) was added, and the aqueous layer was extracted with EtOAc (30 mL×2). The combined organic layers were washed with brine (20 mL), dried over Na$_2$SO$_4$, filtered and concentrated. After purified by prep-HPLC (column: Phenomenex C18 75*30 mm*3 μm; mobile phase: [water (NH$_3$H$_2$O+NH$_4$HCO$_3$)-ACN]; gradient: 45%-75% B over 7 min), 4-((1-(4-(2-(2-aminopyridin-3-yl)-5-(6-cyanopyridin-2-yl)-3H-imidazo[4,5-b]pyridin-3-yl)benzyl)piperidin-4-yl)amino)pyrimidine-2-carbonitrile (Example 428, 170.3 mg, yield: 39% for 2 steps) was obtained as a yellow solid. MS: m/z=605.1 [M+H]$^+$. $^1$H NMR (400 MHz, Dimethylsulfoxide-d$_6$) δ 8.48-8.40 (m, 2H), 8.38-8.33 (m, 1H), 8.26-7.97 (m, 5H), 7.56-7.43 (m, 4H), 7.18 (dd, J=7.6, 1.6 Hz, 1H), 7.03 (s, 2H), 6.67 (d, J=6.0 Hz, 1H), 6.39 (dd, J=8.0, 5.2 Hz, 1H), 3.91-3.73 (m, 1H), 3.50 (s, 2H), 2.88-2.79 (m, 2H), 2.20-2.10 (m, 2H), 1.94-1.81 (m, 2H), 1.56-1.39 (m, 2H).

Example 429: 4-((1-(4-(2-(2-Aminopyridin-3-yl)-5-(2-cyanopyridin-4-yl)-3H-imidazo[4,5-b]pyridin-3-yl)benzyl)piperidin-4-yl)amino)pyrimidine-2-carbonitrile

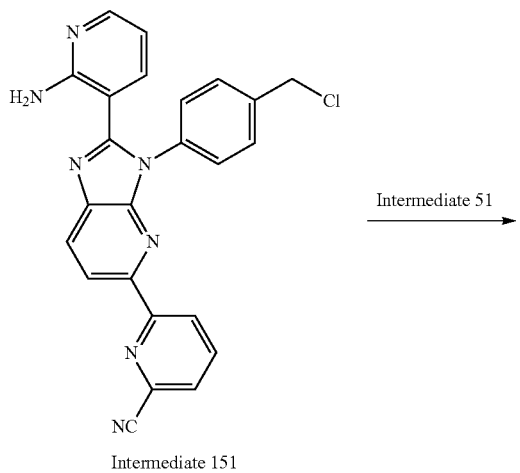

Intermediate 151 → Intermediate 51

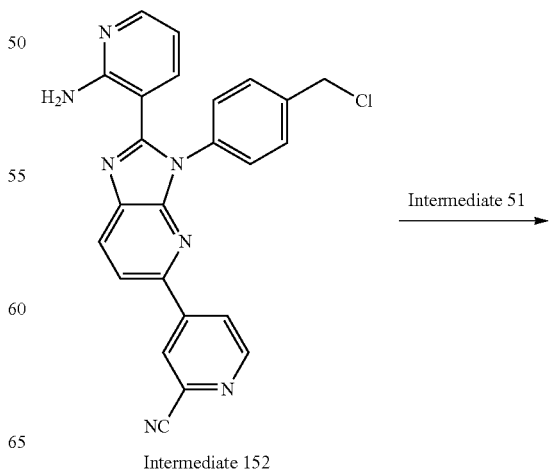

Intermediate 152 → Intermediate 51

1515

-continued

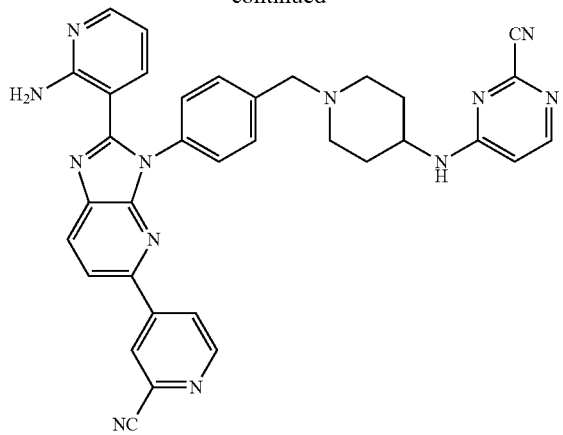

Example 429

1516

-continued

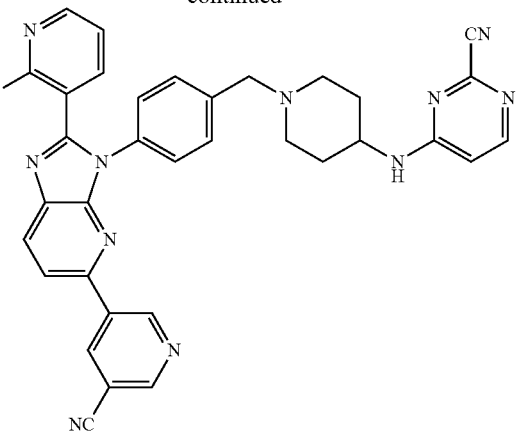

Example 430

To a solution of Intermediate 152 (400 mg, 913 μmol) and Intermediate 51 (204 mg, 1.00 μmol) in DMF (5 mL) were added K$_2$CO$_3$ (379 mg, 2.74 mmol) and NaI (13.7 mg, 91.4 μmol) at 25° C. This mixture was stirred at 80° C. for 1 hr. The mixture was quenched with H$_2$O (50 mL) and then extracted with EtOAc (30 mL×3). The combined organic phase was filtered and concentrated. After purified by prep-HPLC (column: Welch Xtimate C18 150*25 mm*5 μm; mobile phase: [water (NH$_4$HCO$_3$)-ACN]; gradient: 50%-80% B over 7 min), 4-((1-(4-(2-(2-aminopyridin-3-yl)-5-(2-cyanopyridin-4-yl)-3H-imidazo[4,5-b]pyridin-3-yl)benzyl)piperidin-4-yl)amino)pyrimidine-2-carbonitrile (Example 429, 370 mg, yield: 67%) was obtained as a yellow solid. MS: m/z=605.2 [M+H]$^+$. $^1$H NMR (400 MHz, Dimethyl-sulfoxide-d$_6$) 8.82 (d, J=5.2 Hz, 1H), 8.62 (s, 1H), 8.39 (d, J=8.0 Hz, 1H), 8.32 (dd, J=4.8, 1.6 Hz, 1H), 8.28 (d, J=8.4 Hz, 1H), 8.11-8.04 (m, 2H), 8.02 (dd, J=4.8, 1.6 Hz, 1H), 7.52-7.45 (m, 4H), 7.18 (dd, J=7.6, 1.6 Hz, 1H), 7.06 (s, 2H), 6.67 (d, J=6.0 Hz, 1H), 6.39 (dd, J=7.6, 4.8 Hz, 1H), 3.87-3.74 (m, 1H), 3.60 (s, 2H), 2.89-2.80 (m, 2H), 2.20-2.11 (m, 2H), 1.95-1.82 (m, 2H), 1.58-1.43 (m, 2H).

Example 430: 4-((1-(4-(2-(2-Aminopyridin-3-yl)-5-(5-cyanopyridin-3-yl)-3H-imidazo[4,5-b]pyridin-3-yl)benzyl)piperidin-4-yl)amino)pyrimidine-2-carbo-nitrile To a solution of Intermediate 153 (240 mg, 548 μmol) and Intermediate 51 (134 mg, 658 μmol) in DMF (8 mL) were added NaI (16.4 mg, 110 μmol) and K$_2$CO$_3$ (227 mg, 1.64 mmol) at 20° C. The reaction mixture was stirred at 80° C. for 16 hr. H$_2$O (10 mL) was added at 20° C. and the mixture was extracted with EtOAc (10 mL×3). The combined organic layers were washed with water (10 mL×2), dried over anhydrous Na$_2$SO$_4$, filtered and concentrated under reduced pressure. After purified by prep-HPLC (column: Boston Prime C18 150×30 mm×5 μm; mobile phase: [water (NH$_3$H$_2$O+NH$_4$HCO$_3$)-ACN]; gradient: 52%-82% B over 7 min), 4-((1-(4-(2-(2-aminopyridin-3-yl)-5-(5-cyanopyridin-3-yl)-3H-imidazo[4,5-b]pyridin-3-yl)benzyl)piperidin-4-yl)amino)pyrimidine-2-carbonitrile (Example 430, 90.8 mg, yield: 12.9% for 4 steps) was obtained as an off-white solid MS: m/z=605.3 [M+H]$^+$. $^1$H NMR (400 MHz, Dimethyl-sulfoxide-d$_6$) δ 9.48 (d, J=2.0 Hz, 1H), 9.03 (s, 1H), 8.86 (s, 1H), 8.38 (d, J=8.4 Hz, 1H), 8.18 (d, J=8.4 Hz, 1H), 8.13-7.99 (m, 3H), 7.54-7.45 (m, 4H), 7.18 (d, J=6.8 Hz, 1H), 7.06 (s, 2H), 6.67 (d, J=6.0 Hz, 1H), 6.40 (dd, J=7.6, 4.8 Hz, 1H), 3.82-3.81 (m, 1H), 3.60 (s, 2H), 2.89-2.76 (m, 2H), 2.21-2.09 (m, 2H), 1.94-1.81 (m, 2H), 1.61-1.43 (m, 2H).

Example 431: 4-((1-(4-(2-(2-Aminopyridin-3-yl)-5-(pyridin-3-yl)-3H-imidazo[4,5-b]pyridin-3-yl)benzyl)piperidin-4-yl)amino)pyrimidine-2-carbonitrile

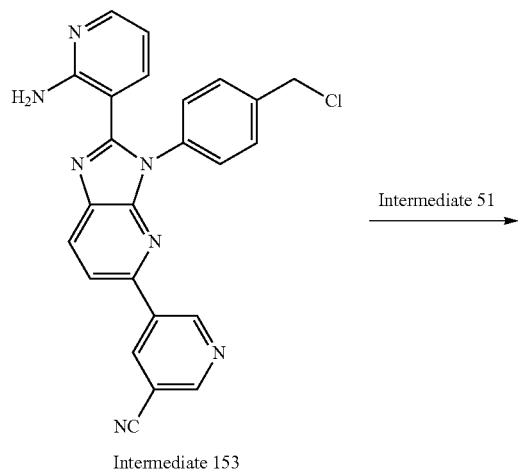

Intermediate 153

→ Intermediate 51

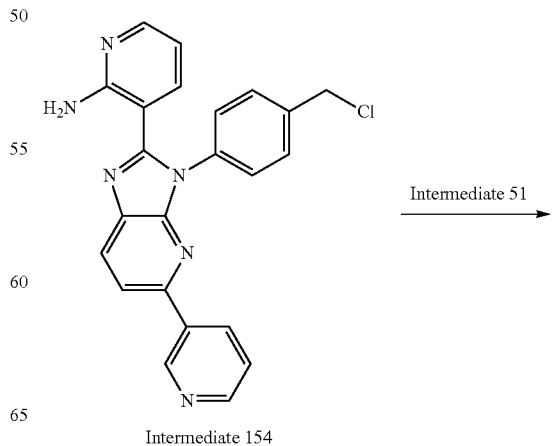

Intermediate 154

→ Intermediate 51

1517

-continued

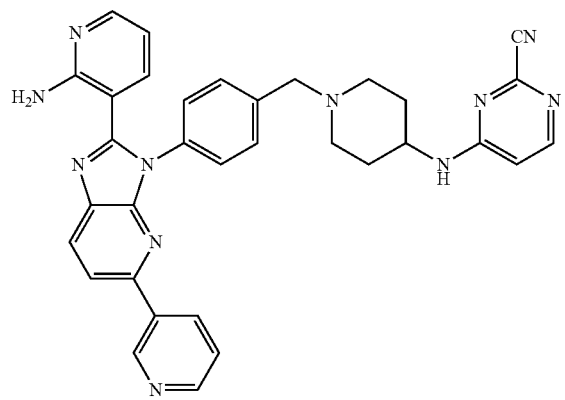

Example 431

1518

-continued

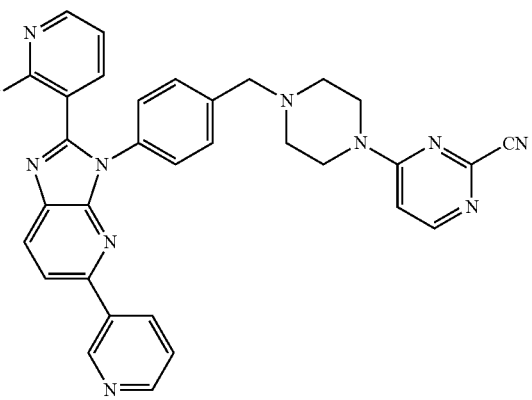

Example 432

To a solution of Intermediate 154 (210 mg, 508 μmol) and Intermediate 51 (113 mg, 559 μmol) in DMF (3 mL) was added DIEA (263 mg, 2.03 mmol). The mixture was stirred at 80° C. for 2 hr under $N_2$. The mixture was concentrated and purified by prep-HPLC (column: Phenomenex C18 80*40 mm*3 μm; mobile phase: [water ($NH_3H_2O$+ $NH_4HCO_3$)-ACN]; gradient: 50%-80% B over 7 min) to give 4-((1-(4-(2-(2-aminopyridin-3-yl)-5-(pyridin-3-yl)-3H-imidazo[4,5-b]pyridin-3-yl)benzyl)piperidin-4-yl)amino) pyrimidine-2-carbonitrile (Example 431, 37.7 mg, yield. 13%) as a yellow solid. MS: m/z=580.3 [M+H]+. $^1$H NMR (400 MHz, Dimethylsulfoxide-$d_6$) δ 9.23 (d, J=1.6 Hz, 1H), 8.70-8.50 (m, 1H), 8.40-8.25 (m, 2H), 8.20-7.90 (m, 4H), 7.60-7.40 (m, 5H), 7.30-7.10 (m, 1H), 7.10-6.90 (m, 1H), 6.67 (d, J=6.4 Hz, 1H), 6.38 (dd, J=7.2, 4.8 Hz, 1H), 3.81-3.80 (m, 1H), 3.59 (s, 2H), 2.83-2.81 (m, 2H), 2.25-2.05 (m, 2H), 1.95-1.70 (m, 2H), 1.60-1.40 (m, 2H).

Example 432:4-(1-(4-(2-(2-Aminopyridin-3-yl)-5-(pyridin-3-yl)-3H-imidazo[4,5-b]pyridin-3-yl)benzyl)piperidin-4-yl)pyrimidine-2-carbonitrile To a solution of Intermediate 154 (170 mg, 412 μmol) and Intermediate 53 (85.7 mg, 453 μmol) in DMF (3 mL) was added DIEA (213 mg, 1.65 mmol). The mixture was stirred at 80° C. for 2 hr under $N_2$. After purified by prep-HPLC (column: Boston Prime C18 150*30 mm*5 μm; mobile phase: [water ($NH_3H_2O$+$NH_4HCO_3$)-ACN]; gradient: 45%-75% B over 7 min), 4-(1-(4-(2-(2-aminopyridin-3-yl)-5-(pyridin-3-yl)-3H-imidazo[4,5-b]pyridin-3-yl)benzyl)piperidin-4-yl)pyrimidine-2-carbonitrile (Example 432, 15.1 mg, yield: 6.5%) was obtained as a yellow solid. MS: m/z=566.3 [M+H]+. $^1$H NMR (400 MHz, Dimethylsulfoxide-$d_6$) δ 9.23 (br s, 1H), 8.59 (d, J=2.8 Hz, 1H), 8.40-8.20 (m, 3H), 8.10-7.90 (m, 2H), 7.60-7.40 (m, 5H), 7.25-7.00 (m, 4H), 6.50-6.30 (m, 1H), 4.00-3.50 (m, 8H), 3.30-3.10 (m, 2H).

Example 433: 4-((1-(4-(2-(2-Aminopyridin-3-yl)-5-(pyridin-4-yl)-3H-imidazo[4,5-b]pyridin-3-yl)benzyl)piperidin-4-yl)amino)pyrimidine-2-carbonitrile

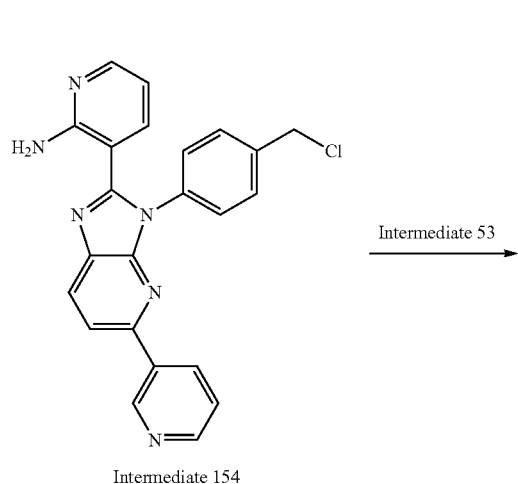

Intermediate 154

Intermediate 53 →

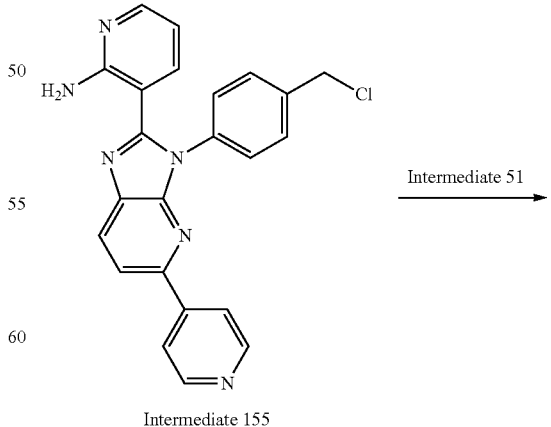

Intermediate 155

Intermediate 51 →

1519
-continued

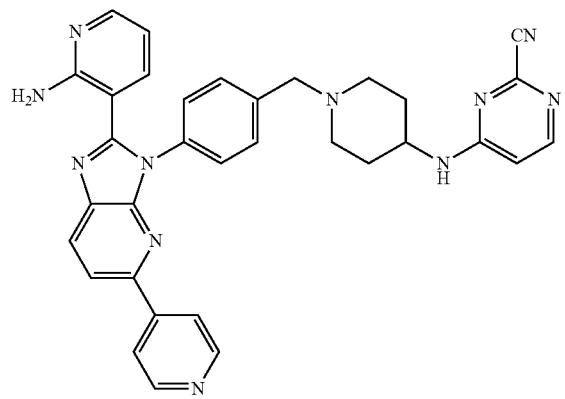

Example 433

1520
-continued

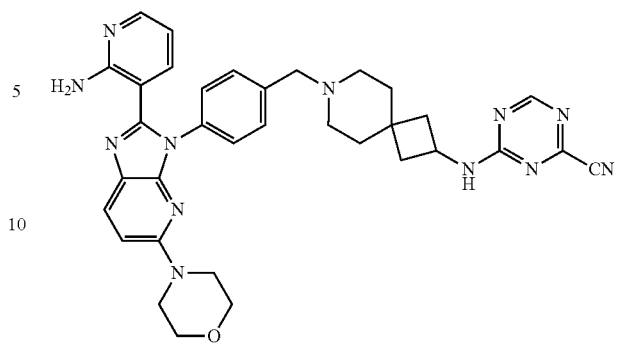

Example 434

To a solution of Intermediate 155 (104 mg, 253 μmol) and Intermediate 51 (72.0 mg, 354 μmol) in DMF (1 mL) was added DIEA (130 mg, 1.01 mmol). The mixture was stirred at 25° C. for 12 hr. After purified by prep-HPLC (column: Welch Xtimate C18 150*25 mm*5 μm; mobile phase: [water (NH$_4$HCO$_3$)-ACN]; gradient: 40%-70% B over 7 min), 4-((1-(4-(2-(2-aminopyridin-3-yl)-5-(pyridin-4-yl)-3H-imidazo[4,5-b]pyridin-3-yl)benzyl)piperidin-4-yl)amino)pyrimidine-2-carbonitrile (Example 433, 58.4 mg, yield: 40%) was obtained as a light yellow solid. MS: m/z=580.4 [M+H]$^+$. $^1$H NMR (400 MHz, Dimethylsulfoxide-d$_6$) 8.68-8.64 (m, 2H), 8.35 (d, J=8.4 Hz, 1H), 8.16 (d, J=8.8 Hz, 1H), 8.11-8.05 (m, 2H), 8.03-7.99 (m, 3H), 7.52-7.45 (m, 4H), 7.18 (dd, J=7.6, 2.0 Hz, 1H), 7.04 (br s, 2H), 6.68 (d, J=6.4 Hz, 1H), 6.39 (dd, J=8.0, 4.8 Hz, 1H), 3.90-3.73 (m, 1H), 3.60 (s, 2H), 2.84-2.82 (m, 2H), 2.22-2.09 (m, 2H), 1.95-1.81 (m, 2H), 1.57-1.43 (m, 2H).

Example 434: 4-((7-(4-(2-(2-Aminopyridin-3-yl)-5-morpholino-3H-imidazo[4,5-b]pyridin-3-yl)benzyl)-7-azaspiro[3.5]nonan-2-yl)amino)-1,3,5-triazine-2-carbonitrile To a solution of Intermediate 56 (200 mg, 475 μmol) and Intermediate 65 (139 mg, 570 μmol) in DMF (5 mL) was added NaI (71 mg, 475 μmol) and K$_2$CO$_3$ (328 mg, 2 mmol). The mixture was stirred at 50° C. for 1 hr. The reaction mixture was diluted with H$_2$O (10 mL) and extracted with EtOAc (20 mL). The combined organic layers were washed with brine (20 mL), dried over Na$_2$SO$_4$, filtered and concentrated under reduced pressure. The residue was purified by prep-HPLC (basic condition MeCN/H$_2$O: 0%~65%) to give 4-((7-(4-(2-(2-Aminopyridin-3-yl)-5-morpholino-3H-imidazo[4,5-b]pyridin-3-yl)benzyl)-7-azaspiro[3.5]nonan-2-yl)amino)-1,3,5-triazine-2-carbonitrile (Example 434, 46 mg, yield: 14%) as a yellow solid. MS: m/z=629.3 [M+H]$^+$. $^1$H NMR (400 MHz, Dimethylsulfoxide-d$_6$) δ 9.27-9.08 (m, 1H), 8.74-8.56 (m, 1H), 8.08-7.81 (m, 2H), 7.40 (d, J=7.6 Hz, 2H), 7.36-7.25 (m, 2H), 7.04 (s, 2H), 7.01-6.95 (m, 1H), 6.92-6.86 (m, 1H), 6.29 (dd, J=7.6, 4.8 Hz, 1H), 4.39-4.21 (m, 1H), 3.75-3.65 (m, 4H), 3.50 (s, 2H), 3.45-3.35 (m, 4H), 2.37-2.14 (m, 6H), 1.81-1.72 (m, 2H), 1.64-1.57 (m, 2H), 1.56-1.49 (m, 2H).

Example 435: 4-((1-(4-(2-(2-Aminopyridin-3-yl)-5-(methylthio)-3H-imidazo[4,5-b]pyridin-3-yl)benzyl)piperidin-4-yl)amino)pyrimidine-2-carbonitrile

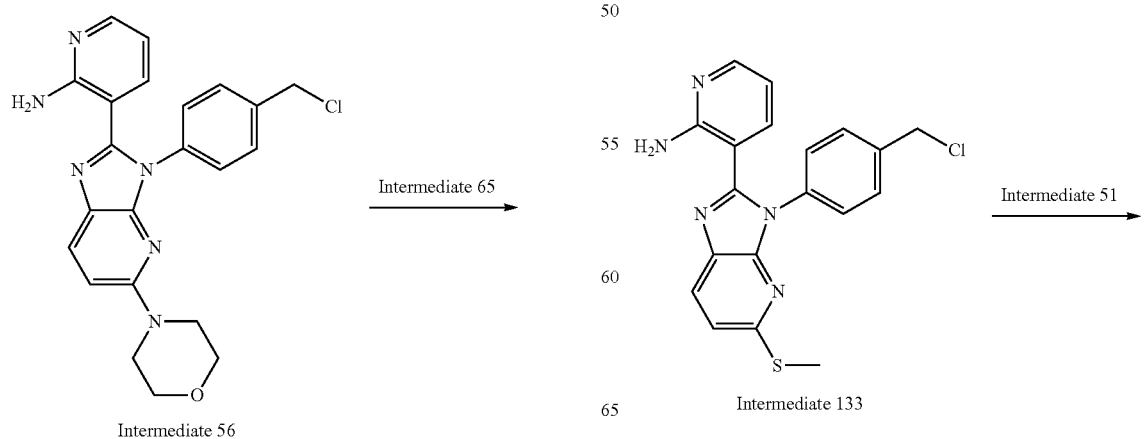

1521 -continued

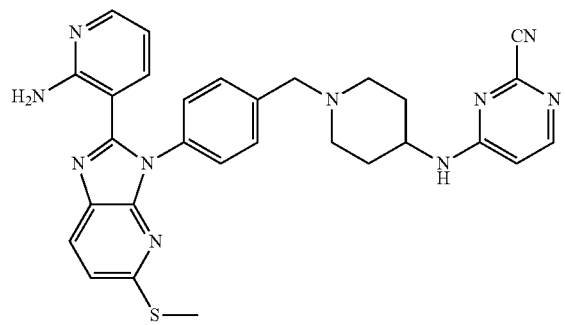

Example 435

To a solution of Intermediate 133 (200 mg, 524 μmol) and Intermediate 51 (106 mg, 524 μmol) in DMF (3 mL) were added NaI (15.7 mg, 105 μmol) and K$_2$CO$_3$ (217 mg. 1.57 mmol). The mixture was stirred at 25° C. for 16 hr. The residue was diluted with H$_2$O (10 mL) and extracted with CH$_2$Cl$_2$ (20 mL×3). The combined organic layers were washed with brine (20 mL×2), dried over Na$_2$SO$_4$, filtered and concentrated under reduced pressure. After purified by prep-HPLC column: Phenomenex C18 75*30 mm*3 μm; mobile phase: [water (0.05% NH$_3$H$_2$O 10 mM NH$_4$HCO$_3$)-ACN]; gradient: 41%-71% B over 7 min, 4-[[1-[[4-[2-(2-amino-3-pyridyl)-5-methylsulfanyl-imidazo[4,5-b]pyridin-3-yl]phenyl]methyl]-4-piperidyl]amino]pyrimidine-2-carbonitrile (Example 435, 24.4 mg, yield: 8.5%) was obtained as light yellow solid. MS: m/z=571.0 [M+Na]$^+$. $^1$H NMR (400 MHz, DMSO-d$_6$) δ 8.11-8.04 (m, 3H), 7.97 (dd, J=4.8, 2.0 Hz, 1H), 7.45 (d, J=8.4 Hz, 2H), 7.38 (d, J=8.4 Hz, 2H), 7.27 (d, J=8.4 Hz, 1H), 7.11 (dd, J=7.6, 1.6 Hz, 1H), 7.0 (br s, 2H), 6.67 (d, J=6.0 Hz, 1H), 6.36 (dd, J=8.0, 5.2 Hz, 1H), 3.91-3.70 (m, 1H), 3.57 (s, 2H), 2.86-2.75 (m, 2H), 2.46 (s, 3H), 2.19-2.07 (m, 2H), 1.94-1.81 (m, 2H), 1.54-1.40 (m, 2H).

Example 436: 4-((1-(4-(2-(2-Aminopyridin-3-yl)-5-(methylsulfonyl)-3H-imidazo[4,5-b]pyridin-3-yl)benzyl)piperidin-4-yl)amino)pyrimidine-2-carbonitrile

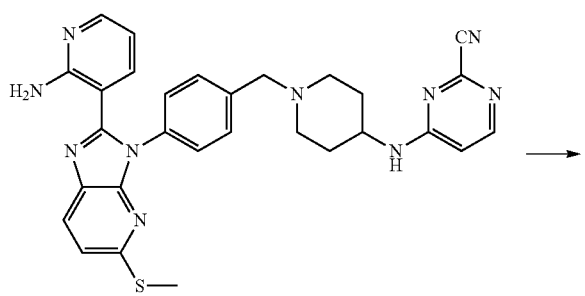

Example 435

1522 -continued

Example 436

To a solution of Example 435 (50 mg, 91.1 μmol) in THF (2 mL) and MeOH (0.5 mL) was added oxone (280 mg, 456 μmol). The mixture was stirred at 25° C. for 16 hr. After purified by prep-HPLC (column: Waters xbridge 150*25 mm 10 μm; mobile phase: [water (NH$_4$HCO$_3$)-ACN]; gradient: 18%-48% B over 14 min), 4-((1-(4-(2-(2-Aminopyridin-3-yl)-5-(methylsulfonyl)-3H-imidazo[4,5-h]pyridin-3-yl)benzyl)piperidin-4-yl)amino)pyrimidine-2-carbonitrile (Example 436, 9.1 mg, yield: 16%) was obtained as light yellow solid. MS: m/z=581.3 [M+H]$^+$. $^1$H NMR (400 MHz, Chloroform-d) δ 8.27 (d, J=8.4 Hz, 1H), 8.18-8.08 (m, 3H), 7.51 (d, J=8.0 Hz, 2H), 7.34 (d, J=8.0 Hz, 2H), 7.09 (dd, J=8.0, 1.6 Hz, 1H), 6.67 (br s, 2H), 6.44 (d, J=6.0 Hz, 1H), 6.36 (dd, J=7.6, 4.8 Hz, 1H), 3.65 (s, 2H), 3.19 (s, 3H), 2.99-2.89 (m, 2H), 2.33-2.25 (m, 2H), 2.10-2.04 (m, 2H), 1.76-1.66 (m, 3H).

Example 437: 4-((1-(4-(2-(2-Aminopyridin-3-yl)-5-(4-methoxypyridin-2-yl)-3H-imidazo[4,5-b]pyridin-3-yl)benzyl)piperidin-4-yl)amino)pyrimidine-2-carbonitrile

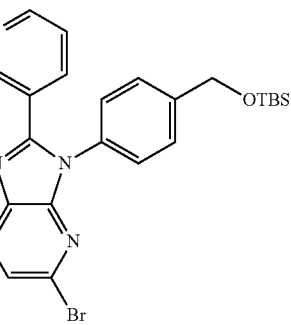

Intermediate 129

Step 1

1523
-continued

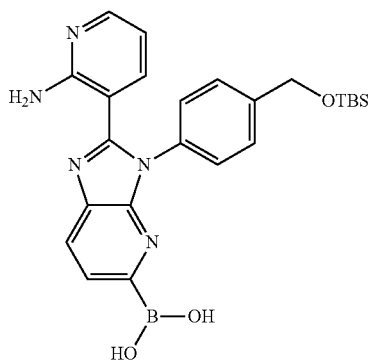

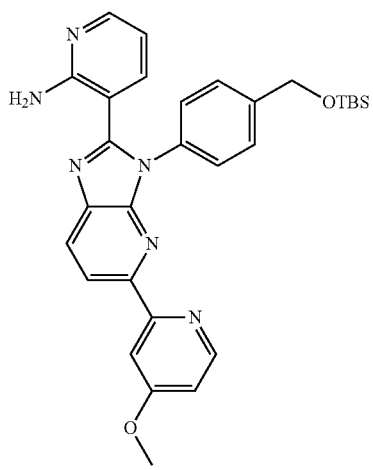

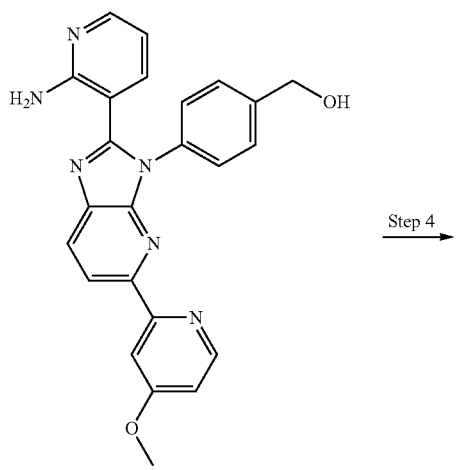

1524
-continued

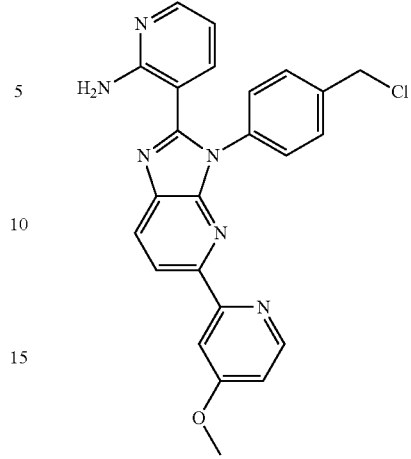

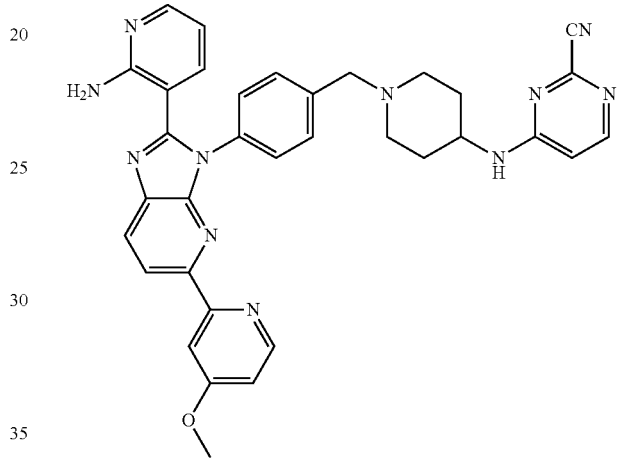

Example 437

Step 1: (2-(2-Aminopyridin-3-yl)-3-(4-(((tert-butyldimethylsilyl)oxy)methyl)phenyl)-3H-imidazo[4,5-b]pyridin-5-yl)boronic acid A mixture of Intermediate 129 (200 mg, 392 μmol), 4,4,4',4',5,5,5',5'-octamethyl-2,2'-bi(1,3,2-dioxaborolane) (199 mg, 784 μmol), KOAc (115 mg, 1.18 mmol) and Pd(dppf)Cl$_2$ (28.7 mg, 39.2 μmol) in 1,4-dioxane (2 mL) was degassed and purged with N$_2$ three times. The mixture was stirred at 80° C. for 2 hr under N$_2$ atmosphere. (2-(2-Aminopyridin-3-yl)-3-(4-(((tert-butyldimethylsilyl)oxy)methyl)phenyl)-3H-imidazo[4,5-b]pyridin-5-yl)boronic acid was obtained as a black liquid, which was used in the next step directly without work-up and purification. MS: m/z=476.1 [M+H]$^+$.

Step 2: 3-(3-(4-(((tert-butyldimethylsilyl)oxy)methyl)phenyl)-5-(4-methoxypyridin-2-yl)-3H-imidazo[4,5-b]pyridin-2-yl)pyridin-2-amine A mixture of (2-(2-aminopyridin-3-yl)-3-(4-(((tert-butyldimethylsilyl)oxy)methyl)phenyl)-3H-imidazo[4,5-b]pyridin-5-yl)boronic acid (460 mg, 968 μmol), 2-bromo-4-methoxypyridine (182 mg, 968 μmol), Pd(dppf)Cl$_2$ (70.8 mg, 96.8 μmol) and Cs$_2$CO$_3$ (946 mg, 2.90 mmol) in 1,4-dioxane (5 mL) and H$_2$O (1 mL) was degassed and purged with N$_2$ three times. The mixture was stirred at 80°

C. for 16 hr under N₂ atmosphere. The reaction mixture was quenched with H₂O (10 mL), diluted with EtOAc (10 mL) and extracted with EtOAc (15 mL×2). The combined organic layers were washed with brine (30 mL), dried over Na₂SO₄, filtered, and concentrated under reduced pressure. After purified by silica gel flash chromatography (Eluent of 10%~40% EtOAc in petroleum ether), 3-(3-(4-(((tert-butyldimethylsilyl)oxy)methyl)phenyl)-5-(4-methoxypyridin-2-yl)-3H-imidazo[4,5-b]pyridin-2-yl)pyridin-2-amine (250 mg, yield: 56% for two steps) was obtained as a black solid. MS: m/z=539.2 [M+H]⁺. ¹H NMR (400 MHz, Chloroform-d) δ 8.54-8.46 (m, 2H), 8.17 (d, J=8.4 Hz, 1H), 8.06 (dd, J=4.8, 1.6 Hz, 1H), 7.88 (d, J=2.4 Hz, 1H), 7.52-7.48 (m, 2H), 7.43-7.38 (m, 2H), 7.14 (dd, J=7.6, 1.2 Hz, 1H), 6.80 (dd, J=5.6, 2.4 Hz, 1H), 6.71 (br s, 2H), 6.38 (dd, J=7.6, 4.8 Hz, 1H), 4.86 (s, 2H), 3.87 (s, 3H), 0.98 (s, 9H), 0.15 (s, 6H).

Step 3; (4-(2-(2-Aminopyridin-3-yl)-5-(4-methoxypyridin-2-yl)-3H-imidazo[4,5-b]pyridin-3-yl)phenyl)methanol To a solution of 3-(3-(4-(((tert-butyldimethylsilyl)oxy)methyl)phenyl)-5-(4-methoxypyridin-2-yl)-3H-imidazo[4,5-b]pyridin-2-yl)pyridin-2-amine (250 mg, 464 μmol) in THF (3 mL) was added TBAF (364 mg, 1.39 mmol, 1 M in THF). The mixture was stirred at 25° C. for 0.5 hr. The reaction mixture was quenched with H₂O (5 mL) at 25° C., diluted with CH₂Cl₂ (10 mL) and extracted with CH₂Cl₂ (15 mL×3). The combined organic layers were washed with brine (50 mL×2), dried over Na₂SO₄, filtered and concentrated under reduced pressure. The mixture was triturated with EtOAc:petroleum ether=1:10 at 25° C. for 10 min. (4-(2-(2-Aminopyridin-3-yl)-5-(4-methoxypyridin-2-yl)-3H-imidazo[4,5-b]pyridin-3-yl)phenyl)methanol (160 mg, yield: 81%) was obtained as a black solid. MS: m/z=425.5 [M+H]⁺. ¹H NMR (400 MHz, Dimethylsulfoxide-d₆) δ 8.52 (d, J=5.6 Hz, 1H), 8.44 (d, J=8.4 Hz, 1H), 8.29 (d, J=8.4 Hz, 1H), 8.01 (dd, J=4.8, 2.0 Hz, 1H), 7.70 (d, J=2.4 Hz, 1H), 7.54-7.45 (m, 4H), 7.25 (dd, J=7.6, 2.0 Hz, 1H), 7.03 (dd, J=5.6, 2.4 Hz, 1H), 6.97 (br s, 2H), 6.43 (dd, J=7.6, 4.8 Hz, 1H), 5.36 (t, J=5.6 Hz, 1H), 4.61 (d, J=5.6 Hz, 2H), 3.85 (s, 3H).

Step 4: 3-(3-(4-(Chloromethyl)phenyl)-5-(4-methoxypyridin-2-yl)-3H-imidazo[4,5-b]pyridin-2-yl)pyridin-2-amine To a solution of (4-(2-(2-aminopyridin-3-yl)-5-(4-methoxypyridin-2-yl)-3H-imidazo[4,5-b]pyridin-3-yl)phenyl)methanol (160 mg, 377 μmol) in CH₂Cl₂ (5 mL) was added SOCl₂ (135 mg, 1.13 mmol). The mixture was stirred at 25° C. for 0.4 hr. The reaction was concentrated under reduced pressure to give 3-(3-(4-(chloromethyl)phenyl)-5-(4-methoxypyridin-2-yl)-3H-imidazo[4,5-b]pyridin-2-yl)pyridin-2-amine (180 mg, HCl salt) as a yellow solid. MS: m/z=443.0 [M+H]⁺. ¹H NMR (400 MHz, Methanol-d₄) δ8.62 (d, J=6.8 Hz, 1H), 8.58-8.55 (m, 1H), 8.52-8.48 (m, 1H), 8.24 (d, J=2.4 Hz, 1H), 8.07-8.04 (m, 1H), 7.85 (d, J=6.4 Hz, 1H), 7.73 (d, J=8.0 Hz, 2H), 7.63 (d, J=8.4 Hz, 2H), 7.55 (dd, J=7.2, 2.4 Hz, 1H), 6.91-6.84 (m, 1H), 4.80 (s, 2H), 4.26 (s, 3H).

Step 5: 4-((1-(4-(2-(2-Aminopyridin-3-yl)-5-(4-methoxypyridin-2-yl)-3H-imidazo[4,5-b]pyridin-3-yl)benzyl)piperidin-4-yl)amino)pyrimidine-2-carbonitrile To a solution of 3-(3-(4-(chloromethyl)phenyl)-5-(4-methoxypyridin-2-yl)-3H-imidazo[4,5-b]pyridin-2-yl)pyridin-2-amine (180 mg, 376 μmol, HCl salt) and Intermediate 55 (119 mg, 376 μmol, TFA salt) in DMF (4 mL) were added K₂CO₃ (259 mg, 1.88 mmol) and NaI (5.63 mg, 37.6 μmol). The mixture was stirred at 50° C. for 1 hr. The reaction mixture was quenched with H₂O (5 mL) at 25° C., diluted with CH₂Cl₂ (10 mL) and extracted with CH₂Cl₂ (15 mL×2). The combined organic layers were washed with brine (50 mL×3), dried over Na₂SO₄, filtered, and concentrated under reduced pressure. After purified by silica gel flash chromatography (Eluent of 1%~7% MeOH in CH₂Cl₂), 4-((1-(4-(2-(2-aminopyridin-3-yl)-5-(4-methoxypyridin-2-yl)-3H-imidazo[4,5-b]pyridin-3-yl)benzyl)piperidin-4-yl)amino)pyrimidine-2-carbonitrile (Example 437, 93.9 mg, yield: 40% for two steps) was obtained as a yellow solid. MS: m/z=610.2 [M+H]⁺. ¹H NMR (400 MHz, Dimethylsulfoxide-d₆) δ 8.51 (d, J=5.6 Hz, 1H), 8.45 (d, J=8.4 Hz, 1H), 8.30 (d, J=8.4 Hz, 1H), 8.14-7.98 (m, 3H), 7.74-7.71 (m, 1H), 7.54-7.45 (m, 4H), 7.22 (d, J=7.2 Hz, 1H), 7.06-7.00 (m, 3H), 6.68 (d, J=5.6 Hz, 1H), 6.41 (dd, J=7.6, 4.8 Hz, 1H), 3.83 (s, 3H), 3.82-3.75 (m, 1H), 3.61 (s, 2H), 2.87-2.80 (m, 2H), 2.20-2.11 (m, 2H), 1.95-1.85 (m, 2H), 1.57-1.46 (m, 2H).

Example 438: 4-((1-(4-(2-(2-Aminopyridin-3-yl)-5-(1-methyl-1H-1,2,3-triazol-4-yl)-3H-imidazo[4,5-b]pyridin-3-yl)benzyl)piperidin-4-yl)amino)pyrimidine-2-carbonitrile

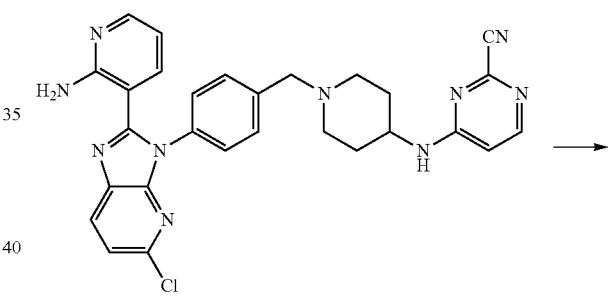

Example 405

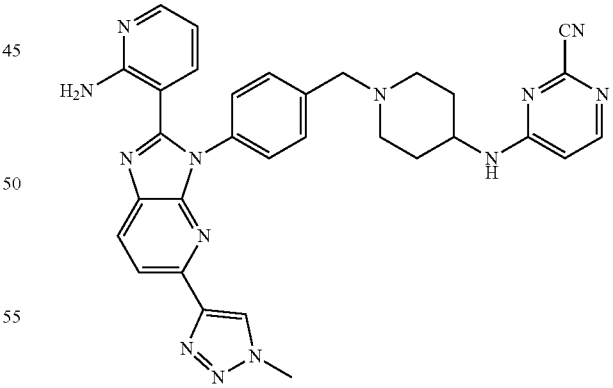

Example 438

To a solution of 4-bromo-1-methyl-1H-1,2,3-triazole (400 mg, 2.5 mmol) and 4-(4,4,5,5-tetramethyl-1,3,2-dioxaborolan-2-yl)pyridine-2-carbonitrile (272 mg, 1.18 mmol) in 1,4-dioxane (4 mL) were added Pd(dppf)Cl₂ (101 mg, 123 μmol) and KOAc (1.05 g, 3.22 mmol) at 25° C. The mixture was degassed and purged with N₂ three times and stirred at 100° C. for 12 hr. Then 4-((1-(4-(2-(2-aminopyridin-3-yl)-

5-chloro-3H-imidazo[4,5-b]pyridin-3-yl)benzyl)piperidin-4-yl)amino)pyrimidine-2-carbonitrile (200 mg, 372 mmol), Cs$_2$CO$_3$ (360 mg, 1.1 mmol) and Pd(dppf)Cl$_2$ (30 mg, 37 μmol) at 25° C. were added to the above mixture. The mixture was degassed and purged with N$_2$ three times and stirred at 100° C. for 12 hr. The mixture was quenched with H$_2$O (50 mL) and extracted with EtOAc (50 mL×3). The combined organic layers were washed with brine (50 mL×3), dried over Na$_2$SO$_4$, filtered and concentrated. After purified by silica gel flash chromatography (Eluent of 0~7% MeOH in CH$_2$Cl$_2$), 4-((1-(4-(2-(2-aminopyridin-3-yl)-5-(1-methyl-1H-1,2,3-triazol-4-yl)-3H-imidazo[4,5-b]pyridin-3-yl)benzyl)piperidin-4-yl)amino)pyrimidine-2-carbonitrile (Example 438, 18.7 mg, yield: 8% for two steps) was obtained as an off white solid. MS: m/z=584.2 [M+1]$^+$. $^1$H NMR (400 MHz, Methanol-d$_4$) δ 8.15 (s, 1H), 8.09 (d, J=8.4 Hz, 1H), 7.98 (d, J=8.4 Hz, 1H), 7.93-7.83 (m, 2H), 7.42 (d, J=8.4 Hz, 2H), 7.31 (d, J=8.4 Hz, 2H), 7.16 (dd, J=7.6, 1.6 Hz, 1H), 6.50 (d, J=4.4 Hz, 1H), 6.35 (dd, J=7.6, 5.2 Hz, 1H), 4.01 (s, 3H), 3.93-3.79 (m, 1H), 3.57 (s, 2H), 2.92-2.81 (m, 2H), 2.25-2.13 (m, 2H), 1.93-1.89 (m, 2H), 1.58-1.45 (m, 2H).

Example 439: 4-((1-(4-(2-(2-Aminopyridin-3-yl)-5-(4-fluoro-3-methoxyphenyl)-3H-imidazo[4,5-h]pyridin-3-yl)benzyl)piperidin-4-yl)amino)pyrimidine-2-carbonitrile mixture was quenched with water (20 mL) and extracted with EtOAc (20 mL×3). The combined organic layers were washed with brine (20 mL), dried over Na$_2$SO$_4$, filtered and concentrated. After purified by prep-HPLC (column: C18 150×30 mm; mobile phase: [water (NH$_3$H$_2$O+NH$_4$HCO$_3$)-ACN]; gradient: 5%-84% B over 7 min), 4-((1-(4-(2-(2-aminopyridin-3-yl)-5-(4-fluoro-3-methoxyphenyl)-3H-imidazo[4,5-b]pyridin-3-yl)benzyl)piperidin-4-yl)amino)pyrimidine-2-carbonitrile (Example 439, 130 mg, yield: 56%) was obtained as a light yellow solid. MS: m/z=627.3 [M+H]$^+$. $^1$H NMR (400 MHz, Dimethylsulfoxide-d$_6$) δ 8.27 (d, J=8.4 Hz, 1H), 8.14-7.96 (m, 4H), 7.81 (dd, J=8.4, 1.6 Hz, 1H), 7.68-7.59 (m, 1H), 7.52-7.42 (m, 4H), 7.29 (dd, J=11.2, 8.8 Hz, 1H), 7.18 (dd, J=7.6, 1.6 Hz, 1H), 7.06 (s, 2H), 6.68 (d, J=6.0 Hz, 1H), 6.39 (dd, J=7.6, 4.8 Hz, 1H), 3.89 (s, 3H), 3.86-3.74 (m, 1H), 3.59 (s, 2H), 2.88-2.77 (m, 2H), 2.21-2.09 (m, 2H), 1.96-1.81 (m, 2H), 1.58-1.40 (m, 2H). $^{19}$F NMR (400 MHz, Dimethylsulfoxide-d$_6$) δ −135.378.

Example 440: N-(3-(2-(2-Aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)acetamide

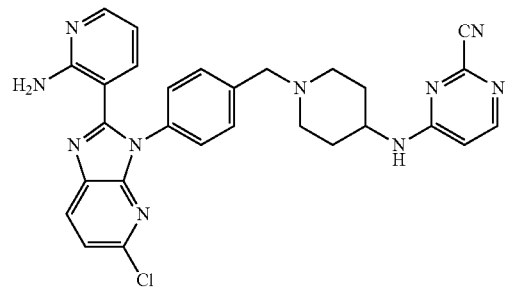

Example 405

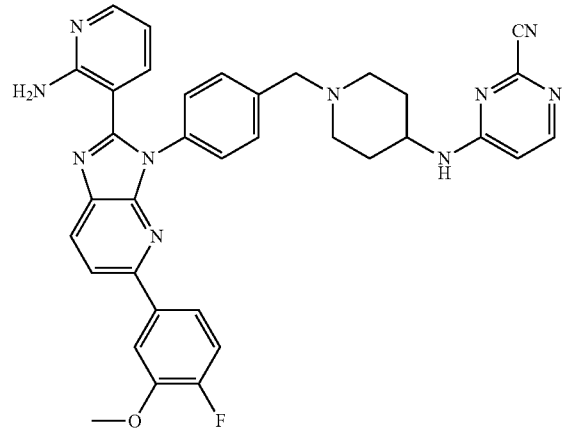

Example 439

To a solution of Example 405 (200 mg, 372 μmol) and (4-fluoro-3-methoxy-phenyl)boronic acid (69.6 mg, 410 μmol) in 1,4-dioxane (10 mL) and H$_2$O (2 mL) were added Cs$_2$CO$_3$ (364 mg, 1.12 mmol) and Pd(PPh$_3$)$_4$ (43.1 mg, 37.2 μmol) at 25° C. The mixture was degassed and purged with N$_2$ three times and stirred at 100° C. for 2 hr. The reaction

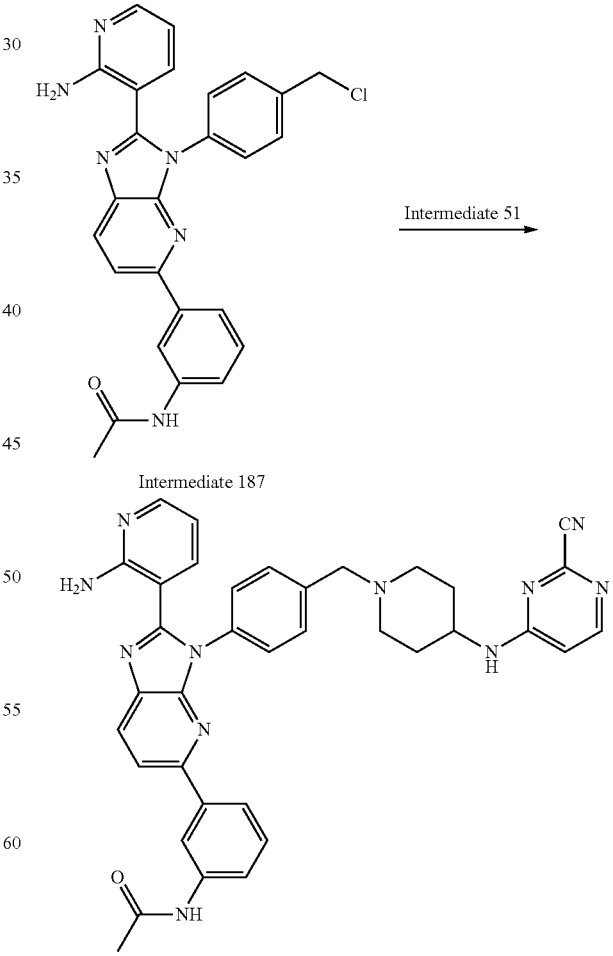

Intermediate 187

Example 440

1529

To a solution of Intermediate 187 (220 mg, 469 μmol) and Intermediate 51 (200 mg, 630 mol) in DMF (10 mL) were added K₂CO₃ (324 mg, 2.35 mmol) and NaI (21.1 mg, 140 μmol). The mixture was stirred at 50° C. for 1 hr. The reaction mixture was diluted with H₂O (50 mL) and extracted with EtOAc (50 mL×2). The combined organic layers were washed with H₂O (50 mL×6), dried over Na₂SO₄, filtered, and concentrated under reduced pressure. After purified by prep-HPLC (column: Daisogel SP ODS RPS 150*25 mm*5 μm; mobile phase: [water (NH₄HCO₃)-ACN]; gradient: 32%-62% B over 12 min), N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)acetamide (Example 440, 101.5 mg, yield: 32%) was obtained as a light-yellow powder. MS: m/z=636.2 [M+H]⁺. ¹H NMR (400 MHz, Dimethylsulfoxide-d₆) δ 10.05 (s, 1H), 8.28 (d, J=8.4 Hz, 1H), 8.15 (s, 1H), 8.13-8.01 (m, 2H), 7.99 (dd, J=4.8, 1.6 Hz, 1H), 7.86 (d, J=8.4 Hz, 1H), 7.69-7.63 (m, 2H), 7.50-7.43 (m, 4H), 7.38 (t, J=8.0 Hz, 1H), 7.14 (dd, J=7.6, 1.6 Hz, 1H), 7.01 (br s, 2H), 6.67 (d, J=6.0 Hz, 1H), 6.37 (dd, J=7.6, 4.8 Hz, 1H), 3.95-3.68 (m, 1H), 3.59 (s, 2H), 2.88-2.79 (m, 2H), 2.19-2.11 (m, 2H), 2.03 (s, 3H), 1.95-1.75 (m, 2H), 1.56-1.43 (m, 2H).

Example 441: 4-((1-(4-(2-(2-Aminopyridin-3-yl)-5-(4-fluorophenyl)-3H-imidazo[4,5-b]pyridin-3-yl)benzyl)piperidin-4-yl)(methyl-d3)amino)pyrimidine-2-carbonitrile

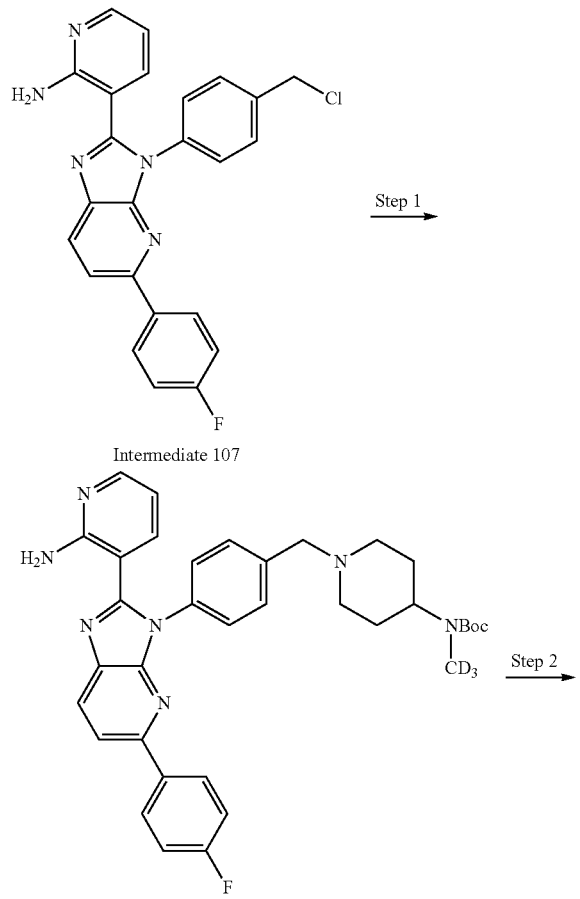

Intermediate 107

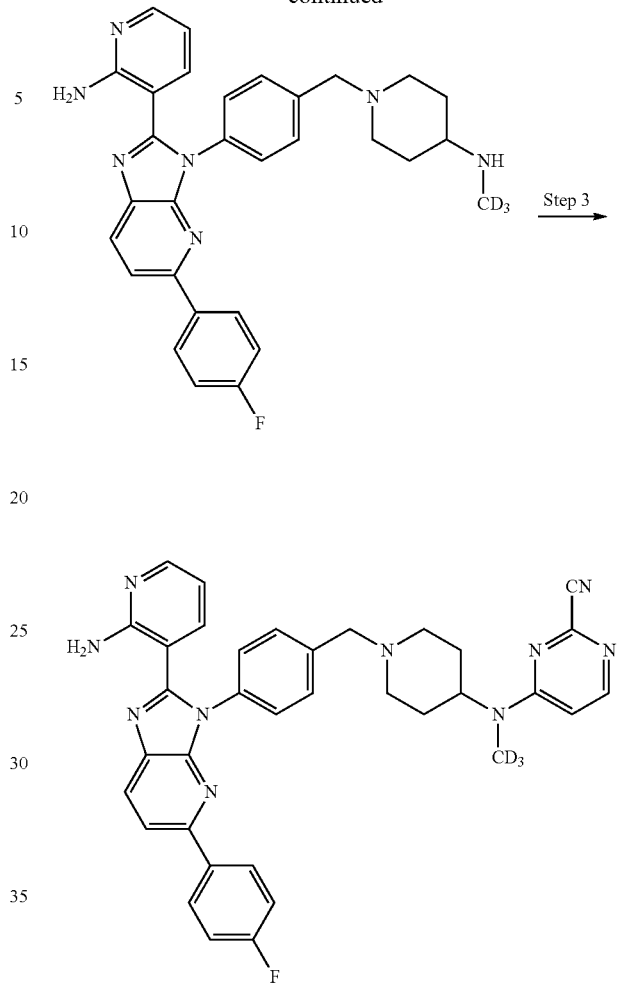

Example 441

Step 1: Tert-butyl (1-(4-(2-(2-aminopyridin-3-yl)-5-(4-fluorophenyl)-3H-imidazo[4,5-b]pyridin-3-yl)benzyl)piperidin-4-yl)(methyl-d3)carbamate To a solution of Intermediate 107 (100 mg, 232 μmol) in DMF (3 mL) were added tert-butyl (methyl-d3)(piperidin-4-yl)carbamate (refer to Intermediate 41 for detail procedures, 60 mg, 279 μmol), NaI (35 mg, 233 μmol) and K₂CO₃ (129 mg, 930 μmol) at 25° C. The mixture was stirred at 50° C. for 1 hr. The reaction mixture was poured into H₂O (50 mL). The mixture was extracted with CH₂Cl₂ (20 mL×2). The combined organic layers were washed with brine (40 mL), dried over anhydrous Na₂SO₄, filtered, and concentrated to dryness. After purified by silica gel flash chromatography (MeOH in CH₂Cl₂=0% to 3%), tert-butyl (1-(4-(2-(2-aminopyridin-3-yl)-5-(4-fluorophenyl)-3H-imidazo[4,5-b]pyridin-3-yl)benzyl)piperidin-4-yl)(methyl-d3)carbamate (130 mg, yield: 71%) was obtained as a yellow solid. MS: m/z=611.1 [M+H]⁺. ¹H NMR (400 MHz, Dimethylsulfoxide-d₆) δ 8.27 (d, J=8.4 Hz, 1H), 8.12-8.05 (m, 2H), 8.01-7.96 (m, 2H), 7.50-7.41 (m, 4H), 7.34-7.27 (m, 2H), 7.15 (dd, J=8.0, 2.0 Hz, 1H), 7.02 (s, 2H), 6.37 (dd, J=7.6, 4.8 Hz, 1H), 3.88-3.67 (m, 1H), 3.57 (s, 2H), 2.96-2.86 (m, 2H), 2.08-1.97 (m, 2H), 1.74-1.63 (m, 2H), 1.56-1.47 (m, 2H), 1.40 (s, 9H). ¹⁹F NMR (400 MHz, Dimethylsulfoxide-d₆) δ −113.59 (s, 1F).

Step 2: 3-(5-(4-Fluorophenyl)-3-(4-((4-((methyl-d3) amino)piperidin-1-yl)methyl)phenyl)-3H-imidazo[4, 5-b]pyridin-2-yl)pyridin-2-amine To a solution of tert-butyl (1-(4-(2-(2-aminopyridin-3-yl)-5-(4-fluorophenyl)-3H-imidazo[4,5-b]pyridin-3-yl)benzyl) piperidin-4-yl)(methyl-d3)carbamate (130 mg, 213 μmol) in CH$_2$Cl$_2$ (5 mL) was added TFA (121 mg, 1.1 mmol) at 25° C. The reaction mixture was stirred at 25° C. for 1 hr. The reaction mixture was concentrated under reduced pressure. 3-(5-(4-Fluorophenyl)-3-(4-((4-((methyl-d3)amino)piperidin-1-yl)methyl)phenyl)-3H-imidazo[4,5-b]pyridin-2-yl) pyridin-2-amine (100 mg) was used into the next step without further purification. MS: m/z=511.2 [M+H]$^+$.

Step 3: 4-((1-(4-(2-(2-Aminopyridin-3-yl)-5-(4-fluorophenyl)-3H-imidazo[4,5-b]pyridin-3-yl)benzyl) piperidin-4-yl)(methyl-d3)amino)pyrimidine-2-carbonitrile To a solution of 3-(5-(4-fluorophenyl)-3-(4-((4-((methyl-d3)amino)piperidin-1-yl)methyl)phenyl)-3H-imidazo[4,5-b]pyridin-2-yl)pyridin-2-amine (100 mg, 196 μmol) and 4-chloropyrimidine-2-carbonitrile (33 mg, 235 μmol) in NMP (3 mL) was added DIEA (76 mg, 588 μmol) at 25° C. The mixture was stirred at 130° C. for 1 hr. The reaction mixture was poured into H$_2$O (50 mL) and extracted with CH$_2$Cl$_2$ (20 mL×2). The combined organic layers were washed with brine (40 mL), dried over anhydrous Na$_2$SO$_4$, filtered and concentrated. After purified by silica gel flash chromatography (Eluent of 0~5% MeOH in CH$_2$Cl$_2$), 4-((1-(4-(2-(2-aminopyridin-3-yl)-5-(4-fluorophenyl)-3H-imidazo[4,5-b]pyridin-3-yl)benzyl)piperidin-4-yl)(methyl-d3) amino)pyrimidine-2-carbonitrile (Example 441, 21.6 mg, yield: 17% for two steps) was obtained as a yellow solid. MS: m/z=614.7 [M+H]$^+$. $^1$H NMR (400 MHz, Dimethylsulfoxide-d$_6$) δ 8.27 (d, J=8.4 Hz, 1H), 8.24 (d, J=6.4 Hz, 1H), 8.10-8.06 (m, 2H), 8.01-7.97 (m, 2H), 7.52-7.43 (m, 5H), 7.30 (t, J=8.8 Hz, 2H), 7.15 (dd, J=7.6, 1.6 Hz, 1H), 7.03 (s, 2H), 6.38 (dd, J=7.6, 4.8 Hz, 1H), 3.62 (s, 2H), 3.29-3.28 (m, 1H), 2.99-2.91 (m, 2H), 2.21-2.14 (m, 2H), 1.89-1.79 (m, 2H), 1.63-1.56 (m, 2H). $^{19}$F NMR (400 MHz, Dimethylsulfoxide-d$_6$) δ −113.58.

Example 442: 4-((1-((4-(2-(2-Aminopyridin-3-yl)-5-(4-fluorophenyl)-3H-imidazo[4,5-b]pyridin-3-yl) phenyl)methyl-d2)piperidin-4-yl)(methyl-d3)amino) pyrimidine-2-carbonitrile

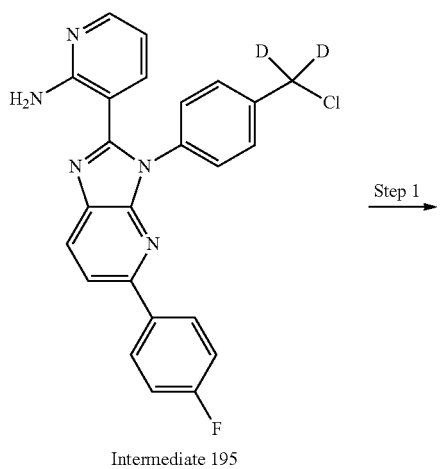

Intermediate 195

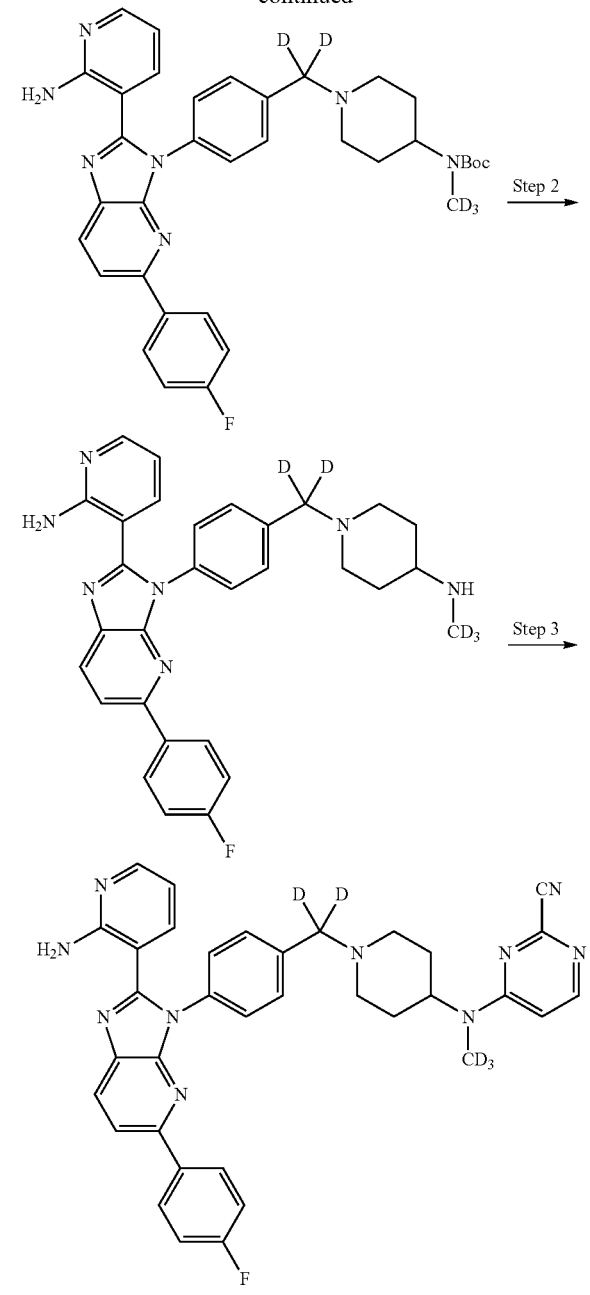

Example 442

Step 1: Teri-butyl (1-((4-(2-(2-aminopyridin-3-yl)-5-(4-fluorophenyl)-3H-imidazo[4,5-b]pyridin-3-yl) phenyl)methyl-d2)piperidin-4-yl)(methyl-d3)carbamate To a solution of Intermediate 195 (100 mg, 232 μmol) in DMF (3 mL) were added tert-butyl (methyl-d3)(piperidin-4-yl)carbamate (refer to Intermediate 41 for detail procedures, 60 mg, 279 μmol), NaI (35 mg, 232 μmol) and K$_2$CO$_3$ (128 mg, 926 μmol) at 25° C., the mixture was stirred at 50° C. for 1 hr. The reaction mixture was poured into H$_2$O (50 mL), extracted with CH$_2$Cl$_2$ (20 mL×2). The combined organic layers were washed with brine (40 mL), dried over anhydrous Na$_2$SO$_4$, filtered and concentrated. After purified by silica gel flash chromatography (Eluent of 0~3% MeOH in CH$_2$Cl$_2$), tert-butyl (1-((4-(2-(2-aminopyridin-3-yl)-5-(4-fluorophenyl)-3H-imidazo[4,5-b]pyridin-3-yl)phenyl)methyl-d2)piperidin-4-yl)(methyl-d3)carbamate (130 mg, yield: 70%) was obtained as a yellow solid. MS: m/z=613.2 [M+H]$^+$. $^1$H NMR (400 MHz, Dimethylsulfoxide-d$_6$) δ 8.27 (d, J=8.4 Hz, 1H), 8.11-8.04 (m, 2H), 8.01-7.94 (m, 2H), 7.51-7.40 (m, 4H), 7.30 (t, J=8.8 Hz, 2H), 7.14 (dd, J=7.6, 2.0 Hz, 1H), 7.03 (s, 2H), 6.37 (dd, J=8.0, 4.8 Hz, 1H), 3.81-3.79 (m, 1H), 2.95-2.85 (m, 2H), 2.07-1.99 (m, 2H), 1.76-1.62 (m, 2H), 1.56-1.47 ((m, 2H), 1.39 (s, 9H). $^{19}$F NMR (400 MHz, Dimethylsulfoxide-d$_6$) δ -113.59.

Step 2: 3-(5-(4-Fluorophenyl)-3-(4-((4-((methyl-d3)amino)piperidin-1-yl)methyl-d2)phenyl)-3H-imidazo[4,5-b]pyridin-2-yl)pyridin-2-amine To a solution of tert-butyl (1-((4-(2-(2-aminopyridin-3-yl)-5-(4-fluorophenyl)-3H-imidazo[4,5-b]pyridin-3-yl)phenyl)methyl-d2)piperidin-4-yl)(methyl-d3)carbamate (130 mg, 212 µmol) in CH$_2$Cl$_2$ (5 mL) was added TFA (121 mg, 1.1 mmol) at 25° C. The reaction mixture was stirred at 25° C. for 1 hr. The reaction mixture was concentrate under reduced pressure. The crude product 3-(5-(4-fluorophenyl)-3-(4-((4-((methyl-d3)amino)piperidin-1-yl)methyl-d2)phenyl)-3H-imidazo[4,5-b]pyridin-2-yl)pyridin-2-amine (105 mg) was used into the next step without further purification. MS: m/z=513.1 [M+H]$^+$.

Step 3: 4-((1-((4-(2-(2-Aminopyridin-3-yl)-5-(4-fluorophenyl)-3H-imidazo[4,5-b]pyridin-3-yl)phenyl)methyl-d2)piperidin-4-yl)(methyl-d3)amino)pyrimidine-2-carbonitrile To a solution of 3-(5-(4-fluorophenyl)-3-(4-((4-((methyl-d3)amino)piperidin-1-yl)methyl-d2)phenyl)-3H-imidazo[4,5-b]pyridin-2-yl)pyridin-2-amine (100 mg, 195 µmol) and 4-chloropyrimidine-2-carbonitrile (33 mg, 235 µmol) in NMP (3 mL) was added DIEA (76 mg, 588 µmol) at 25° C. The mixture was stirred at 130° C. for 1 hr. The reaction mixture was poured into H$_2$O (50 mL), extracted with CH$_2$Cl$_2$ (20 mL×2). The combined organic layers were washed with brine (40 mL), dried over anhydrous Na$_2$SO$_4$, filtered and concentrated. After purified by silica gel flash chromatography (Eluent of 0~5% MeOH in CH$_2$Cl$_2$), 4-((1-((4-(2-(2-aminopyridin-3-yl)-5-(4-fluorophenyl)-3H-imidazo[4,5-b]pyridin-3-yl)phenyl)methyl-d2)piperidin-4-yl)(methyl-d3)amino)pyrimidine-2-carbonitrile (Example 442, 20.5 mg, yield: 17% for two steps) was obtained as a yellow solid. MS: m/z=616.5 [M+H]$^+$. $^1$H NMR (400 MHz, Dimethylsulfoxide-d$_6$) δ 8.27 (d, J=8.4 Hz, 1H), 8.24 (d, J=6.4 Hz, 1H), 8.08 (dd, J=8.8, 5.6 Hz, 2H), 8.01-7.97 (m, 2H), 7.55-7.42 (m, 5H), 7.30 (t, J=8.8 Hz, 2H), 7.15 (dd, J=7.6, 1.6 Hz, 1H), 7.07-6.92 (m, 2H), 6.38 (dd, J=7.6, 4.8 Hz, 1H), 3.29-3.28 (m, 1H), 2.99-2.92 (m, 2H), 2.22-2.13 (m, 2H), 1.88-1.79 (m, 2H), 1.65-1.55 (m, 2H). $^{19}$F NMR (400 MHz, Dimethylsulfoxide-d$_6$) δ -113.58.

Example 443: 4-((1-(4-(2-(2-Aminopyridin-3-yl)-5-(4-fluorophenyl)-3H-imidazo[4,5-b]pyridin-3-yl)benzyl)azetidin-3-yl)amino)pyrimidine-2-carbonitrile

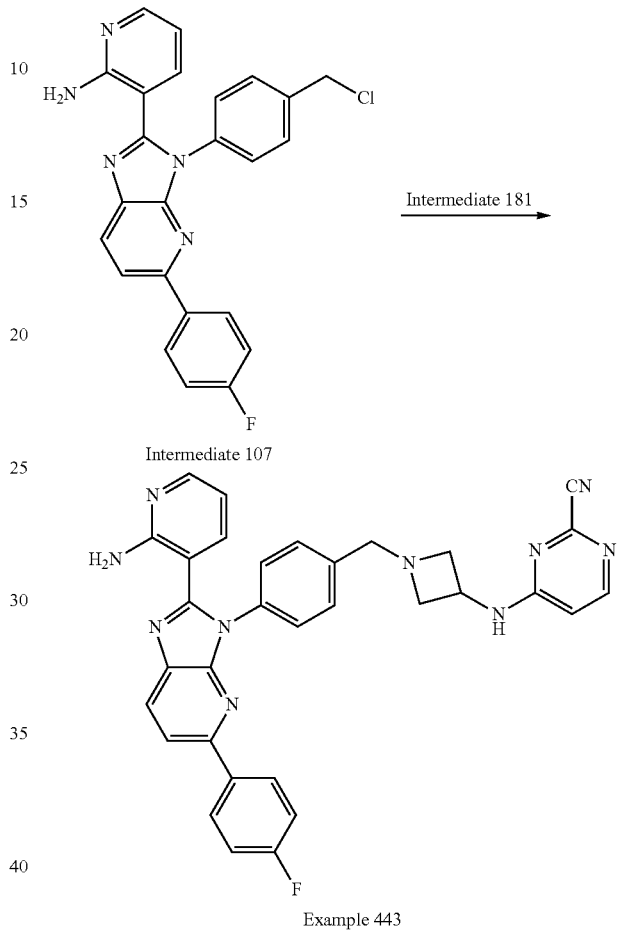

To a solution of Intermediate 107 3 (200 mg, 465 µmol), Intermediate 181 (148 mg, 512 µmol, TFA salt) in DMF (2 mL) were added NaI (21 mg, 140 µmol) and K$_2$CO$_3$ (322 mg, 2.33 mmol). The mixture was stirred at 50° C. for 1 hr. The reaction mixture was poured into H$_2$O (10 mL) and extracted with EtOAc (15 mL×3). The combined organic layers were dried over anhydrous Na$_2$SO$_4$, filtered and concentrated under reduced pressure. After purified by prep-HPLC (column: Waters Xbridge 150×25 mm×5 µm; mobile phase: [water (NH$_3$H$_2$O+NH$_4$HCO$_3$)-ACN]; gradient: 43%-73% B over 11 min), 4-((1-(4-(2-(2-aminopyridin-3-yl)-5-(4-fluorophenyl)-3H-imidazo[4,5-b]pyridin-3-yl)benzyl)azetidin-3-yl)amino)pyrimidine-2-carbonitrile (Example 443, 93.2 mg, yield: 35%) was obtained as a yellow lyophilized powder. MS: m/z=569.3 [M+H]$^+$. $^1$H NMR (400 MHz, Dimethylsulfoxide-d$_6$) δ 8.64 (d, J=6.8 Hz, 1H), 8.27 (d, J=8.4 Hz, 1H), 8.15 (d, J=6.0 Hz, 1H), 8.11-8.05 (m, 2H), 8.02-7.97 (m, 2H), 7.49-7.42 (m, 4H), 7.30 (t, J=8.8 Hz, 2H), 7.16 (dd, J=7.6, 1.6 Hz, 1H), 7.01 (br s, 2H), 6.73 (d, J=6.0 Hz, 1H), 6.40 (dd, J=7.6, 4.8 Hz, 1H), 4.56-4.38 (m, 1H), 3.71 (s, 2H), 3.68-3.61 (m, 2H), 3.04 (t, J=6.4 Hz, 2H). $^{19}$F NMR (400 MHz, Dimethylsulfoxide-d$_6$) δ -113.566.

Example 444: 4-((7-(4-(2-(2-Aminopyridin-3-yl)-5-(4-fluorophenyl)-3H-imidazo[4,5-b]pyridin-3-yl)benzyl)-7-azaspiro[3.5]nonan-2-yl)amino)pyrimidine-2-carbonitrile

Example 445: 4-((2-(4-(2-(2-Aminopyridin-3-yl)-5-(4-fluorophenyl)-3H-imidazo[4,5-b]pyridin-3-yl)benzyl)-2-azaspiro[3.3]heptan-6-yl)amino)pyrimidine-2-carbonitrile

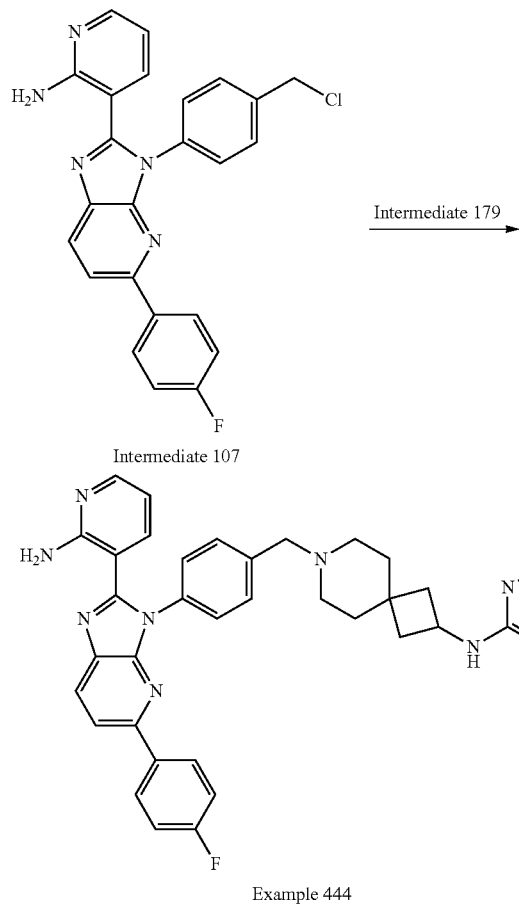

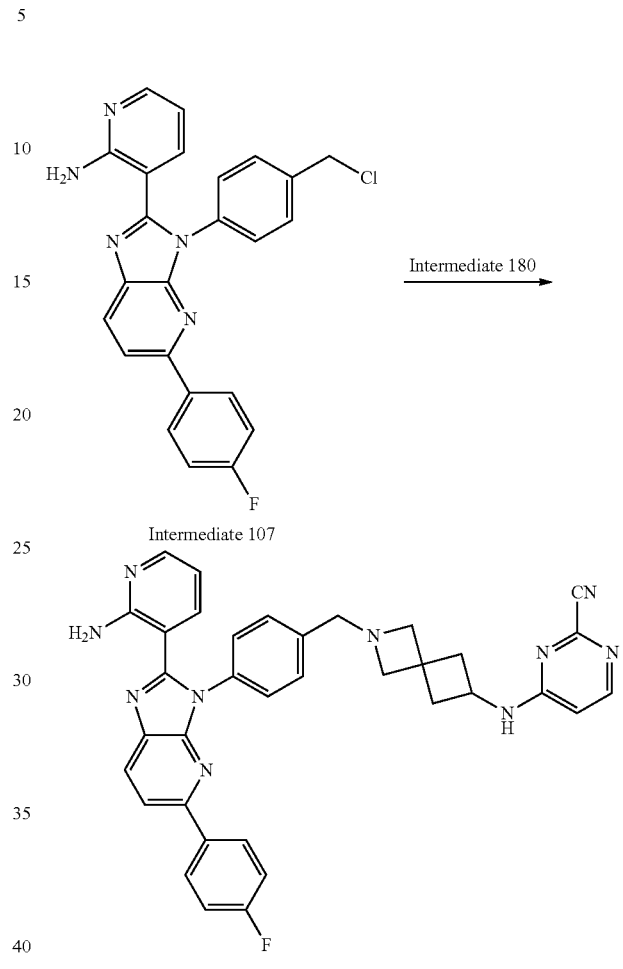

To a solution of Intermediate 107 (200 mg, 465 gmol), Intermediate 179 (183 mg, 512 μmol, TFA salt) in DMF (2 mL) were added NaI (21 mg, 140 μmol) and K$_2$CO$_3$ (322 mg, 2.33 mmol). The mixture was stirred at 50° C. for 1 hr. The reaction mixture was poured into H$_2$O (10 mL) and extracted with EtOAc (15 mL×3). The organic phase was dried over anhydrous Na$_2$SO$_4$, filtered, and concentrated under reduced pressure. After purified by prep-HPLC (column: Daisogel SP ODS RPS 150×25 mm×5 μm; mobile phase: [water (NH$_4$HCO$_3$)-ACN]; gradient: 50%-80% B over 10 min), 4-((7-(4-(2-(2-aminopyridin-3-yl)-5-(4-fluorophenyl)-3H-imidazo[4,5-b]pyridin-3-yl)benzyl)-7-azaspiro[3.5]nonan-2-yl)amino)pyrimidine-2-carbonitrile (Example 444, 54 mg, yield: 18%) was obtained as an off white lyophilized powder. MS: m/z=637.4 [M+H]$^+$. $^1$H NMR (400 MHz, Dimethylsulfoxide-d$_6$) δ 8.44-8.31 (m, 1H), 8.27 (d, J=8.4 Hz, 1H), 8.14-8.02 (m, 3H), 8.01-7.93 (m, 2H), 7.50-7.39 (m, 4H), 7.29 (t, J=8.8 Hz, 2H), 7.19-7.11 (m, 1H), 7.04 (br s, 2H), 6.64 (d, J=6.0 Hz, 1H), 6.36 (dd, J=7.6, 4.8 Hz, 1H), 4.47-4.19 (m, 1H), 3.53 (s, 2H), 2.41-2.33 (m, 2H), 2.32-2.19 (m, 4H), 1.75-1.61 (m, 4H), 1.60-1.51 (m, 2H). $^{19}$F NMR (400 MHz, Dimethylsulfoxide-d$_6$) δ −113.573.

To a solution of Intermediate 107 (200 mg, 465 μmol), Intermediate 180 (110 mg, 512 μmol, TFA salt) in DMF (2 mL) were added NaI (21 mg, 140 μmol) and K$_2$CO$_3$ (322 mg, 2.33 mmol). The mixture was stirred at 50° C. for 1 hr. The reaction mixture was poured into H$_2$O (10 mL), extracted with EtOAc (15 mL×3). The organic phase was dried over anhydrous Na$_2$SO$_4$, filtered, and concentrated under reduced pressure. After purified by prep-HPLC (column: Waters xbridge 150×25 mm 10 μm; mobile phase: [water (NH$_4$HCO$_3$)-ACN]; gradient: 42%-72% B over 10 min), 4-((2-(4-(2-(2-aminopyridin-3-yl)-5-(4-fluorophenyl)-3H-imidazo[4,5-b]pyridin-3-yl)benzyl)-2-azaspiro[3.3]heptan-6-yl)amino)pyrimidine-2-carbonitrile (Example 445, 45.1 mg, yield: 16%) was obtained as an off white lyophilized powder. MS: m/z=609.3 [M+H]$^+$. $^1$H NMR (400 MHz, Dimethylsulfoxide-d$_6$) δ 8.43-8.29 (m, 1H), 8.26 (d, J=8.4 Hz, 1H), 8.08 (dd, J=8.8, 5.6 Hz, 3H), 8.00 (dd, J=4.8, 1.6 Hz, 1H), 7.97 (d, J=8.4 Hz, 1H), 7.51-7.36 (m, 4H), 7.30 (t, J=8.4 Hz, 2H), 7.15 (dd, J=7.6, 1.6 Hz, 1H), 7.00 (br s, 2H), 6.63 (d, J=6.0 Hz, 1H), 6.40 (dd, J=7.6, 4.4 Hz, 1H), 4.35-4.14 (m, 1H), 3.60 (s, 2H), 3.30-3.25 (m, 2H), 3.20-3.05 (m, 2H), 2.58-2.52 (m, 2H), 2.20-1.94 (m, 2H). $^{19}$F NMR (400 MHz, Dimethylsulfoxide-d$_6$) δ −113.587.

Example 446: 4-((2-(4-(2-(2-Aminopyridin-3-yl)-5-(4-fluorophenyl)-3H-imidazo[4,5-b]pyridin-3-yl)benzyl)-2-azaspiro[3.5]nonan-7-yl)amino)pyrimidine-2-carbonitrile

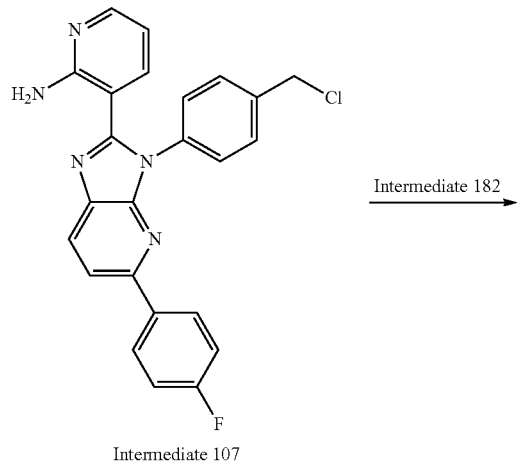

Intermediate 107

→ Intermediate 182

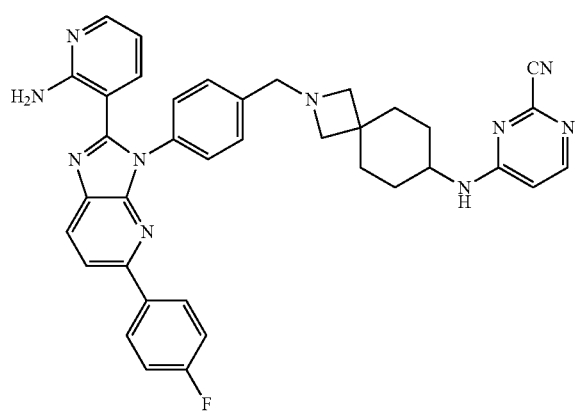

Example 446

To a solution of Intermediate 107 (200 mg, 465 μmol), Intermediate 182 (125 mg, 348 μmol, TFA salt) in DMF (2 mL) were added NaI (21 mg, 140 μmol) and $K_2CO_3$ (322 mg, 2.33 mmol). The mixture was stirred at 50° C. for 1 hr. The reaction mixture was poured into $H_2O$ (15 mL), extracted with EtOAc (15 mL×3). The organic phase was dried over anhydrous $Na_2SO_4$, filtered, and concentrated under reduced pressure. After purified by prep-HPLC (column: Waters xbridge 150×25 mm×10 μm; mobile phase: [water ($NH_4HCO_3$)-ACN]; gradient: 40%-70% B over 11 min), 4-((2-(4-(2-(2-aminopyridin-3-yl)-5-(4-fluorophenyl)-3H-imidazo[4,5-b]pyridin-3-yl)benzyl)-2-azaspiro[3.5]nonan-7-yl)amino)pyrimidine-2-carbonitrile (Example 446, 37.2 mg, yield: 13%) was obtained as a yellow lyophilized powder. MS: m/z=637.4 [M+H]+. 1H NMR (400 MHz, Dimethylsulfoxide-$d_6$) δ 8.27 (d, J=8.4 Hz, 1H), 8.12-8.03 (m, 3H), 8.02-7.92 (m, 3H), 7.51-7.38 (m, 4H), 7.30 (t, J=8.8 Hz, 2H), 7.19-7.12 (m, 1H), 6.99 (br s, 2H), 6.65 (d, J=6.0 Hz, 1H), 6.39 (dd, J=7.6, 4.8 Hz, 1H), 3.85-3.74 (m, 1H), 3.67 (s, 2H), 3.06-2.89 (m, 4H), 1.95-1.87 (m, 2H), 1.84-1.74 (m, 2H), 1.60-1.50 (m, 2H), 1.27-1.22 (m, 2H). 19F NMR (400 MHz, Dimethylsulfoxide-$d_6$) δ −113.580.

Example 447: 4-(6-(4-(2-(2-Aminopyridin-3-yl)-5-(4-fluorophenyl)-3H-imidazo[4,5-b]pyridin-3-yl)benzyl)-2,6-diazaspiro[3.3]heptan-2-yl)pyrimidine-2-carbonitrile

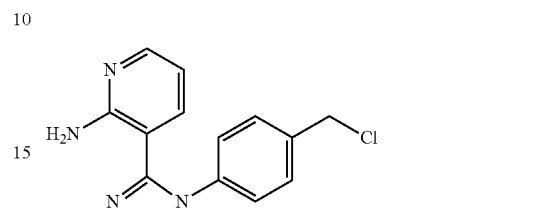

Intermediate 107 → Intermediate 183

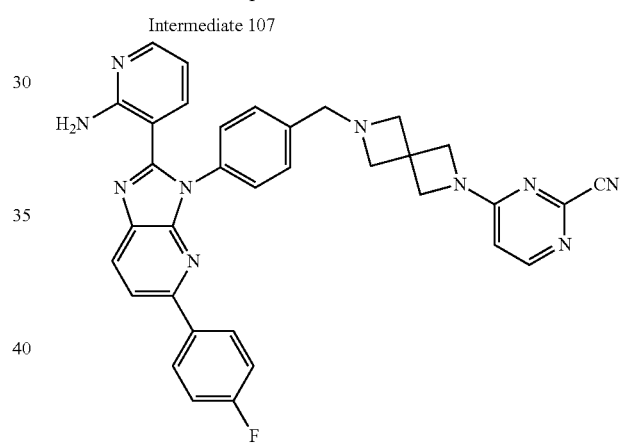

Example 447

To a solution of Intermediate 107 (200 mg, 465 μmol), Intermediate 183 (161 mg, 512 μmol, TFA salt) in DMF (2 mL) were added NaI (70 mg, 465 μmol) and $K_2CO_3$ (322 mg, 2.33 mmol). The mixture was stirred at 50° C. for 1 hr. The reaction mixture was poured into $H_2O$ (15 mL), extracted with EtOAc (15 mL×3). The organic phase was dried over anhydrous $Na_2SO_4$, filtered, and concentrated under reduced pressure. After purified by prep-HPLC (column: Waters xbridge 150×25 mm 10 μm; mobile phase: [water ($NH_4HCO_3$)-ACN]; gradient: 45%-75% B over 10 min), 4-(6-(4-(2-(2-aminopyridin-3-yl)-5-(4-fluorophenyl)-3H-imidazo[4,5-b]pyridin-3-yl)benzyl)-2,6-diazaspiro[3.3]heptan-2-yl)pyrimidine-2-carbonitrile (Example 447, 52.5 mg, yield: 19%) was obtained as a yellow lyophilized powder. MS: m/z=595.3 [M+H]+. 1H NMR (400 MHz, Dimethylsulfoxide-$d_6$) δ 8.26 (d, J=8.4 Hz, 1H), 8.22 (d, J=6.0 Hz, 1H), 8.07 (dd, J=8.4, 5.6 Hz, 2H), 8.01-7.94 (m, 2H), 7.43 (s, 4H), 7.29 (t, J=8.8 Hz, 2H), 7.17-7.10 (m, 1H), 7.05-6.92 (m, 2H), 6.70-6.52 (m, 1H), 6.39 (dd, J=7.6, 4.8 Hz, 1H), 4.26-4.15 (m, 4H), 3.63 (s, 2H), 3.42-3.35 (s, 4H). 19F NMR (400 MHz, Dimethylsulfoxide-$d_6$) δ −113.581.

Example 448: 4-(8-(4-(2-(2-Aminopyridin-3-yl)-5-(4-fluorophenyl)-3H-imidazo[4,5-b]pyridin-3-yl)benzyl)-3,8-diazabicyclo[3.2.1]octan-3-yl)pyrimidine-2-carbonitrile

Example 449: 4-((3aR,6aS)-5-(4-(2-(2-Aminopyridin-3-yl)-5-(4-fluorophenyl)-3H-imidazo[4,5-b]pyridin-3-yl)benzyl)hexahydropyrrolo[3,4-c]pyrrol-2(1H)-yl)pyrimidine-2-carbonitrile

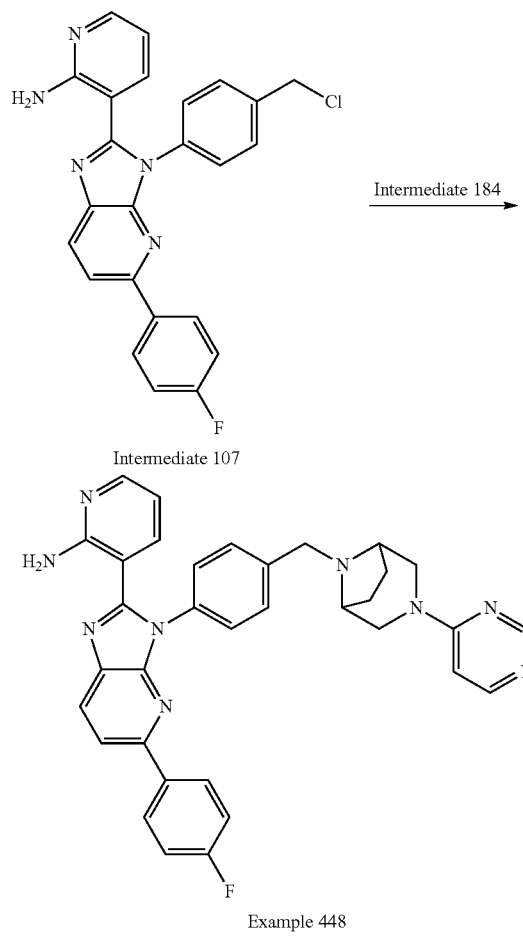

Example 448

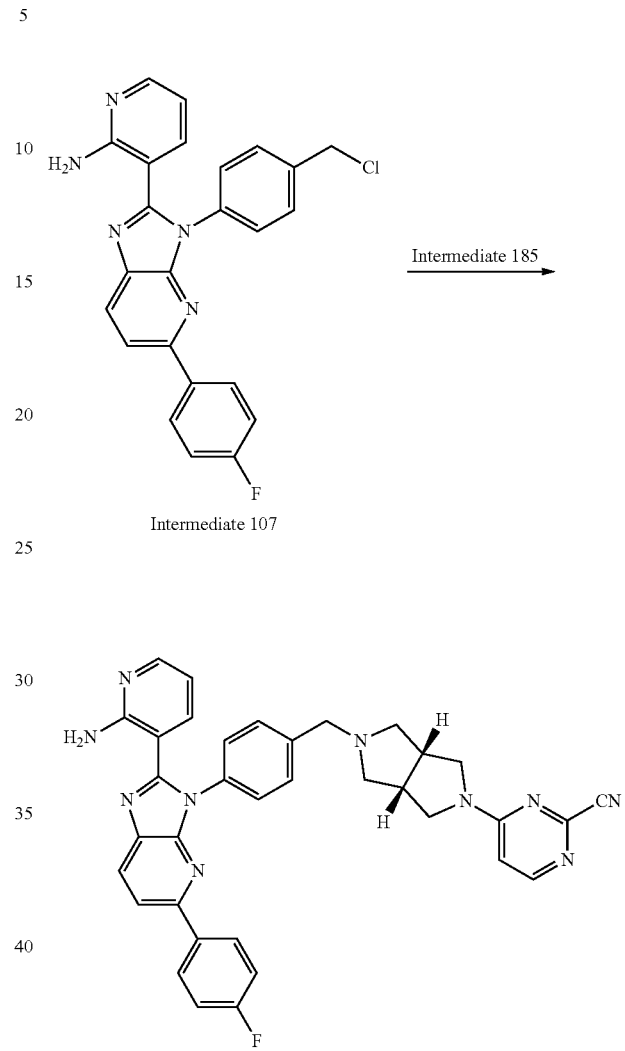

Example 449

To a solution of Intermediate 107 (200 mg, 465 μmol), Intermediate 184 (169 mg, 512 μmol, TFA salt) in DMF (2 mL) were added NaI (21 mg, 140 μmol) and K$_2$CO$_3$ (322 mg, 2.33 mmol). The mixture was stirred at 50° C. for 1 hr. The reaction mixture was poured into H$_2$O (10 mL), extracted with EtOAc (15 mL×3). The organic phase was dried over anhydrous Na$_2$SO$_4$, filtered, and concentrated under reduced pressure. After purified by prep-HPLC (column: Daisogel SP ODS RPS 150×25 mm×5 μm; mobile phase: [water (NH$_4$HCO$_3$)-ACN]; gradient: 54%-84% B over 10 min), 4-(8-(4-(2-(2-aminopyridin-3-yl)-5-(4-fluorophenyl)-3H-imidazo[4,5-b]pyridin-3-yl)benzyl)-3,8-diazabicyclo[3.2.1]octan-3-yl)pyrimidine-2-carbonitrile (Example 448, 45.7 mg, yield: 16%) was obtained as an off white lyophilized powder. MS: m/z=609.2 [M+H]$^+$. $^1$H NMR (400 MHz, Dimethylsulfoxide-d$_6$) δ 8.33-8.20 (m, 2H), 8.08 (dd, J=8.8, 5.6 Hz, 2H), 8.00 (dd, J=4.8, 1.6 Hz, 1H), 7.97 (d, J=8.4 Hz, 1H), 7.58 (d, J=8.4 Hz, 2H), 7.46 (d, J=8.0 Hz, 2H), 7.30 (t, J=8.8 Hz, 2H), 7.17 (dd, J=7.6, 1.6 Hz, 1H), 7.08-6.95 (m, 3H), 6.41 (dd, J=7.6, 4.8 Hz, 1H), 4.44-4.11 (m, 1H), 3.84-3.57 (m, 3H), 3.33 (s, 2H), 3.26-3.03 (m, 2H), 2.06-1.97 (m, 2H), 1.65-1.42 (m, 2H). $^{19}$F NMR (400 MHz, Dimethylsulfoxide-d$_6$) δ −113.573.

To a solution of Intermediate 107 (240 mg, 558 μmol), Intermediate 185 (202 mg, 614 μmol, TFA salt) in DMF (2 mL) were added NaI (25 mg. 167 μmol) and K$_2$CO$_3$ (386 mg. 2.79 mmol). The mixture was stirred at 50° C. for 1 hr. The reaction mixture was poured into H$_2$O (10 mL), extracted with EtOAc (15 mL×3). The organic phase was dried over anhydrous Na$_2$SO$_4$, filtered and concentrated under reduced pressure. After purified by prep-HPLC (column: Waters Xbridge BEH C18 150×25 mm×5 μm; mobile phase: [water (NH$_4$HCO$_3$)-ACN]; gradient: 50%-80% B over 10 min), 4-((3aR,6aS)-5-(4-(2-(2-aminopyridin-3-yl)-5-(4-fluorophenyl)-3H-imidazo[4,5-b]pyridin-3-yl)benzyl) hexahydropyrrolo[3,4-c]pyrrol-2(1H)-yl)pyrimidine-2-carbonitrile (Example 449, 57.2 mg, yield: 17%) was obtained as an off white lyophilized powder. MS: m/z=609.3 [M+H]$^+$. $^1$H NMR (400 MHz, Dimethylsulfoxide-d$_6$) δ 8.34-8.16 (m, 2H), 8.07 (dd, =8.8, 5.6 Hz, 2H), 8.02-7.94 (m, 2H), 7.54-7.35 (m, 4H), 7.29 (t, J=8.8 Hz, 2H), 7.14 (dd, J=7.6, 1.6 Hz, 1H), 7.01 (s, 2H), 6.79 (d, J=6.0 Hz, 1H), 6.37 (dd, J=7.6, 4.8 Hz, 1H), 3.87-3.73 (m, 1H), 3.68 (s, 2H), 3.53-3.42 (m, 1H), 3.04-2.90 (m, 2H), 2.71-2.52 (m, 6H). $^{19}$F NMR (400 MHz, Dimethylsulfoxide-d$_6$) δ −113.558.

Example 450: 4-((3aS,6aS)-5-(4-(2-(2-Aminopyridin-3-yl)-5-(4-fluorophenyl)-3H-imidazo[4,5-b]pyridin-3-yl)benzyl)hexahydropyrrolo[3,4-c]pyrrol-2(1H)-yl)pyrimidine-2-carbonitrile

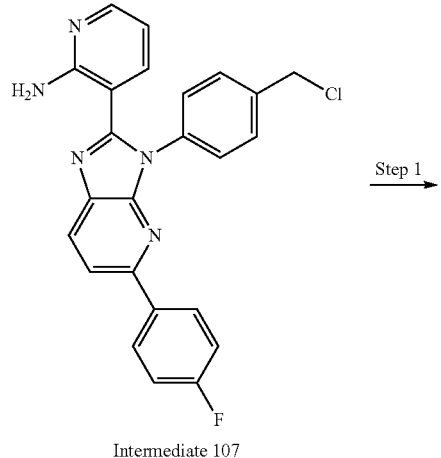

Intermediate 107

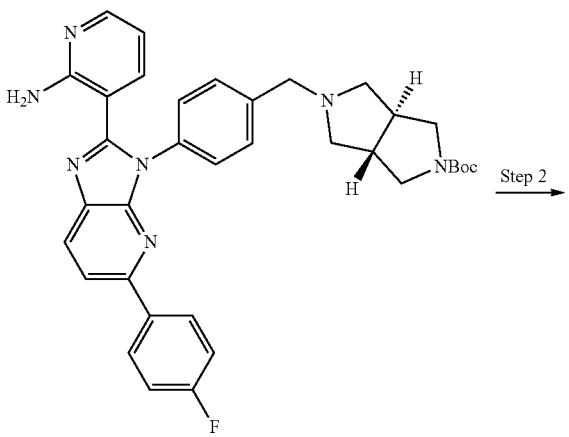

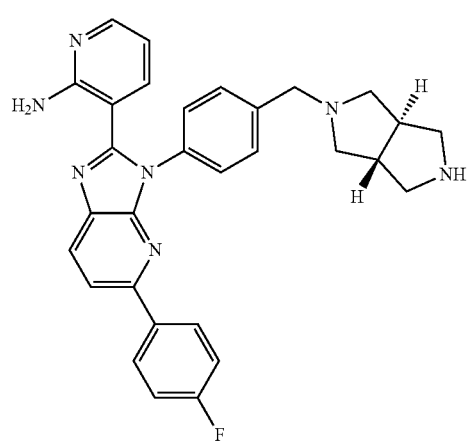

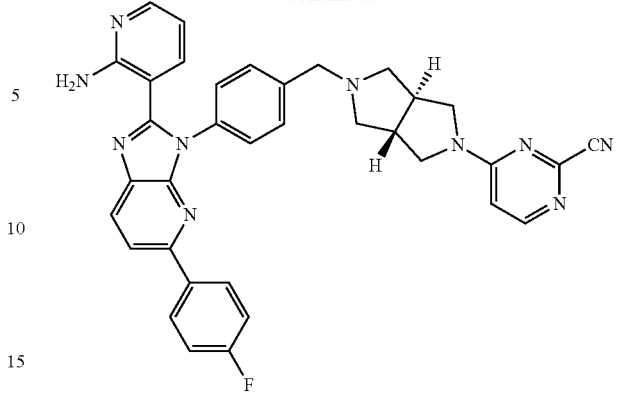

Example 450

Step 1: Tert-butyl (3aS,6aS)-5-(4-(2-(2-aminopyridin-3-yl)-5-(4-fluorophenyl)-3H-imidazo[4,5-b]pyridin-3-yl)benzyl)hexahydropyrrolo[3,4-c]pyrrole-2(1H)-carboxylate To a solution of Intermediate 107 (200 mg, 465 gmol), tert-butyl (3aS,6aS)-hexahydropyrrolo[3,4-c]pyrrole-2(1H)-carboxylate (109 mg, 512 μmol) in DMF (2 mL) were added K$_2$CO$_3$ (129 mg, 931 μmol) and NaI (6.97 mg, 46.5 μmol). The mixture was stirred at 80° C. for 2 hr. The reaction mixture was poured into H$_2$O (15 mL), extracted with EtOAc (15 mL×3). The organic phase was dried over anhydrous Na$_2$SO$_4$, filtered, and concentrated under reduced pressure. After purified by silica gel flash chromatography (Eluent of 0%~52% EtOAc in petroleum ether), tert-butyl (3aS,6aS)-5-(4-(2-(2-aminopyridin-3-yl)-5-(4-fluorophenyl)-3H-imidazo[4,5-b]pyridin-3-yl)benzyl)hexahydropyrrolo[3,4-c]pyrrole-2(1H)-carboxylate (190 mg, yield: 67%) was obtained as a yellow oil. MS: m/z=606.1 [M+H]$^+$.

Step 2: 3-(5-(4-Fluorophenyl)-3-(4-(((3aR,6aR)-hexahydropyrrolo[3,4-c]pyrrol-2(1H)-yl)methyl)phenyl)-3H-imidazo[4,5-b]pyridin-2-yl)pyridin-2-amine To a solution of (3aS,6aS)-5-(4-(2-(2-aminopyridin-3-yl)-5-(4-fluorophenyl)-3H-imidazo[4,5-b]pyridin-3-yl)benzyl)hexahydropyrrolo[3,4-c]pyrrole-2(1H)-carboxylate (190 mg, 314 μmol) in 1,4-dioxane (2 mL) was added HCl in 1,4-dioxane (4 M, 2 mL). The mixture was stirred at 25° C. for 2 hr. The reaction mixture was concentrated directly. 3-(5-(4-fluorophenyl)-3-(4-(((3aR,6aR)-hexahydropyrrolo[3,4-c]pyrrol-2(1H)-yl)methyl)phenyl)-3H-imidazo[4,5-b]pyridin-2-yl)pyridin-2-amine (160 mg, HCl salt, yield. 94%) was obtained as a yellow solid. $^1$H NMR (400 MHz, Dimethylsulfoxide-d$_6$) δ 12.29 (s, 1H), 10.05 (s, 1H), 9.78 (s, 1H), 8.37 (d, J=8.4 Hz, 2H), 8.17-8.02 (m, 4H), 7.93-7.79 (m, 3H), 7.66 (d, J=8.4 Hz, 2H), 7.32 (t, J=8.8 Hz, 2H), 6.91 (dd, J=7.2, 6.4 Hz, 1H), 4.70-4.49 (m, 2H), 3.50-3.41 (m, 2H), 3.40-3.28 (m, 4H), 3.18-3.08 (m, 1H), 3.05-2.91 (m, 2H), 2.90-2.75 (m, 1H), 2.45-2.32 (m, 2H).

Step 3: 4-((3aS,6aS)-5-(4-(2-(2-Aminopyridin-3-yl)-5-(4-fluorophenyl)-3H-imidazo[4,5-b]pyridin-3-yl)benzyl)hexahydropyrrolo[3,4-c]pyrrol-2(1H)-yl)pyrimidine-2-carbonitrile To a solution of 3-(5-(4-fluorophenyl)-3-(4-(((3aR,6aR)-hexahydropyrrolo[3,4-c]pyrrol-2(1H)-yl)methyl)phenyl)-

3H-imidazo[4,5-b]pyridin-2-yl)pyridin-2-amine (113 mg, 223.50 gmol, HCl salt), 4-chloropyrimidine-2-carbonitrile (37.4 mg, 268 μmol) in DMF (2 mL) were added K₂CO₃ (92.7 mg, 671 μmol) and NaI (3.35 mg, 22.4 μmol). The mixture was stirred at 25° C. for 1 hr. The reaction mixture was poured into H₂O (15 mL), extracted with EtOAc (15 mL×3). The organic phase was dried over Na₂SO₄, filtered and concentrated under reduced pressure. After purified by prep-HPLC (column: Phenomenex C18 150×25 mm×10 μm; mobile phase: [water (NH₄HCO₃)-ACN]; gradient: 50%-80% B over 11 min), 4-((3aS,6aS)-5-(4-(2-(2-amino-pyridin-3-yl)-5-(4-fluorophenyl)-3H-imidazo[4,5-b]pyridin-3-yl)benzyl)hexahydropyrrolo[3,4-c]pyrrol-2(1H)-yl)pyrimidine-2-carbonitrile (Example 450, 10 mg, yield: 7%) was obtained as a light yellow lyophilized powder. MS: m/z=609.4 [M+H]⁺. ¹H NMR (400 MHz, Dimethylsulfox-ide-d₆) δ 8.31-8.20 (m, 2H), 6.91 (dd, J=8.8, 5.6 Hz, 2H), 8.04-7.92 (m, 2H), 7.51 (d, J=8.4 Hz, 2H), 7.44 (d, J=8.0 Hz, 2H), 7.30 (t, J=8.8 Hz, 2H), 7.16 (dd, J=8.0, 1.6 Hz, 1H), 7.01 (br s, 2H), 6.75 (d, J=6.4 Hz, 1H), 7.16 (dd, J=8.0, 5.2 Hz, 1H), 4.04-3.90 (m, 2H), 3.88-3.78 (m, 1H), 3.67-3.56 (m, 1H), 3.15-3.07 (m, 2H), 2.97-2.87 (m, 2H), 2.71-2.64 (m, 2H), 2.41-2.31 (m, 2H). ¹⁹F NMR (400 MHz, Dimethylsulfoxide-d₆) δ -113.580.

Example 451: 4-((1-(4-(2-(2-Aminopyridin-3-yl)-5-(4-fluorophenyl)-3H-imidazo[4,5-b]pyridin-3-yl)benzyl)piperidin-4-yl-4-d)amino)pyrimidine-2-carbonitrile To a solution of Intermediate 107 (80 mg, 186 μmol), Intermediate 186 (38 mg, 186 μmol) in DMF (2 mL) were added NaI (5.58 mg, 37.2 μmol) and K₂CO₃ (77.2 mg, 558 μmol). The mixture was stirred at 50° C. for 1 hr. The mixture was diluted with H₂O (5 mL) and extracted with CH₂Cl₂ (5 mL×3). The combined organic layers were washed with brine (5 mL×2), dried over Na₂SO₄, filtered, and concentrated under reduced pressure. After purified by silica gel flash chromatography (Eluent of 5~6% MeOH in CH₂Cl₂), 4-((1-(4-(2-(2-Aminopyridin-3-yl)-5-(4-fluorophenyl)-3H-imidazo[4,5-b]pyridin-3-yl)benzyl)piperidin-4-yl-4-d)amino)pyrimidine-2-carbonitrile (Example 451, 49.5 mg, yield: 42%) was obtained as a yellow solid. MS: m/z=598.7 [M+H]⁺. ¹H NMR (400 MHz, Dimethylsulfox-ide-d₆) δ 8.27 (d, J=8.4 Hz, 1H), 8.11-8.03 (m, 4H), 8.01-7.96 (m, 2H), 7.47 (q, J=8.4 Hz, 4H), 7.29 (t, J=8.8 Hz, 2H), 7.15 (dd, J=7.6, 2.0 Hz, 1H), 7.03 (s, 2H), 6.67 (br d, J=6.0 Hz, 1H), 6.37 (dd, J=7.6, 4.8 Hz, 1H), 3.59 (s, 2H), 2.85-2.80 (m, 2H), 2.16 (t, J=10.4 Hz, 2H), 1.90-1.86 (m, 2H), 1.52-1.46 (m, 2H). ¹⁹F NMR (400 MHz, Dimethylsulfoxide-d₆) δ -113.6.

Example 452: 4-((1-(4-(2-(2-Aminopyridin-3-yl)-5,6-dimethyl-3H-imidazo[4,5-b]pyridin-3-yl)benzyl)piperidin-4-yl-4-d)amino)pyrimidine-2-carbonitrile

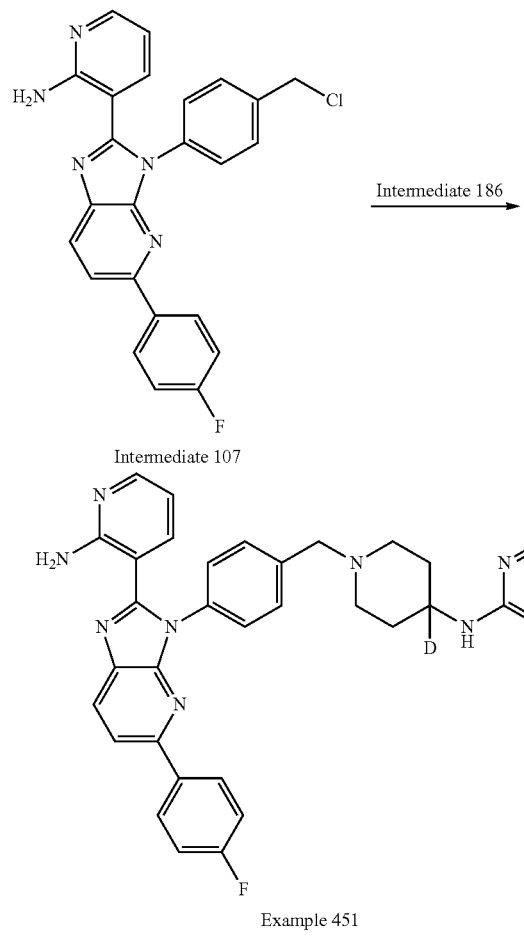

Example 451

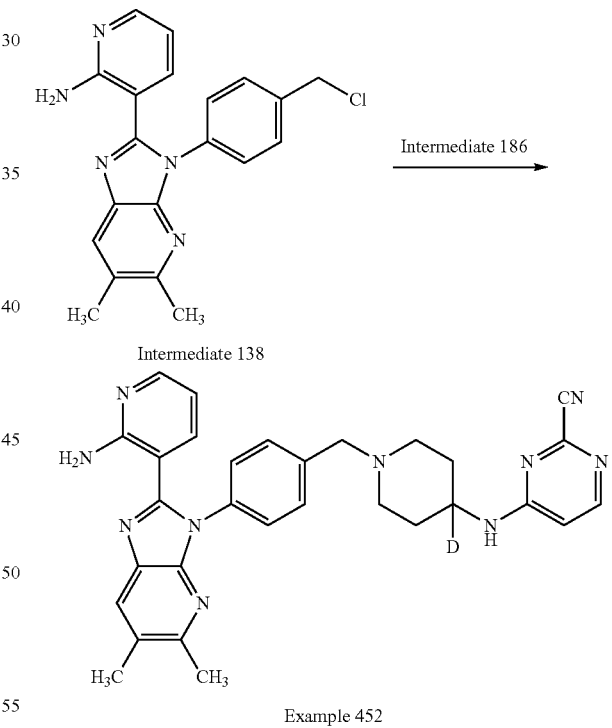

Example 452

To a solution of Intermediate 138 (100 mg, 275 μmol) and Intermediate 186 (56 mg, 275 μmol) in DMF (3 mL) were added NaI (8.24 mg, 55 μmol) and K₂CO₃ (114 mg, 825 μmol). The mixture was stirred at 50° C. for 1 hr. The mixture was diluted with H₂O (5 mL) and extracted with CH₂Cl₂ (5 mL×3). The combined organic layers were washed with brine (5 mL×2), dried over Na₂SO₄, filtered, and concentrated under reduced pressure. After purified by silica gel flash chromatography (Eluent of 5~6% MeOH in CH2Cl2) and then purified by prep-TLC (MeOH in CH2Cl2=1:10), 4-((1-(4-(2-(2-Aminopyridin-3-yl)-5,6-dimethyl-3H-imidazo[4,5-b]pyridin-3-yl)benzyl)piperidin-4-yl-4-d)amino)pyrimidine-2-carbonitrile (Example 452, 12.3 mg, yield. 17%) was obtained as a yellow solid. MS: m/z=532.7 [M+H]Y. $^1$H NMR (400 MHz, Methanol-$d_4$) δ 8.00 (d, J=5.6 Hz, 1H), 7.94 (dd, J=5.2, 1.6 Hz, 1H), 7.89 (s, 1H), 7.51 (d, J=8.4 Hz, 2H), 7.35 (d, J=8.4 Hz, 2H), 7.23 (dd, J=7.6, 1.6 Hz, 1H), 6.59 (d, J=5.6 Hz, 1H), 6.43 (dd, J=7.6, 5.2 Hz, 1H), 3.65 (s, 2H), 2.95 (d, J=11.6 Hz, 2H), 2.53 (s, 3H), 2.44 (s, 3H), 2.27 (t, J=11.2 Hz, 2H), 1.99 (d, J=12.8 Hz, 2H), 1.64-1.56 (m, 2H).

Example 453: 4-((1-(4-(2-(2-Aminopyridin-3-yl)-5-(cyclopent-1-en-1-yl)-3H-imidazo[4,5-b]pyridin-3-yl)benzyl)piperidin-4-yl)amino)pyrimidine-2-carbonitrile

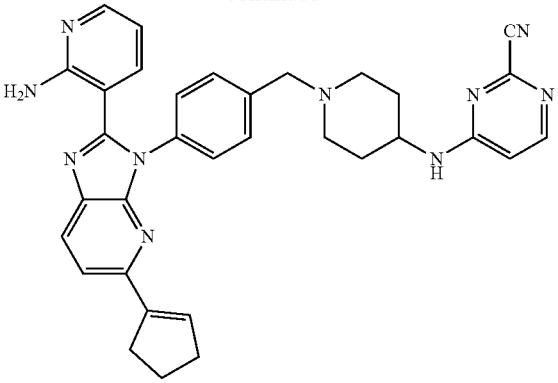

-continued

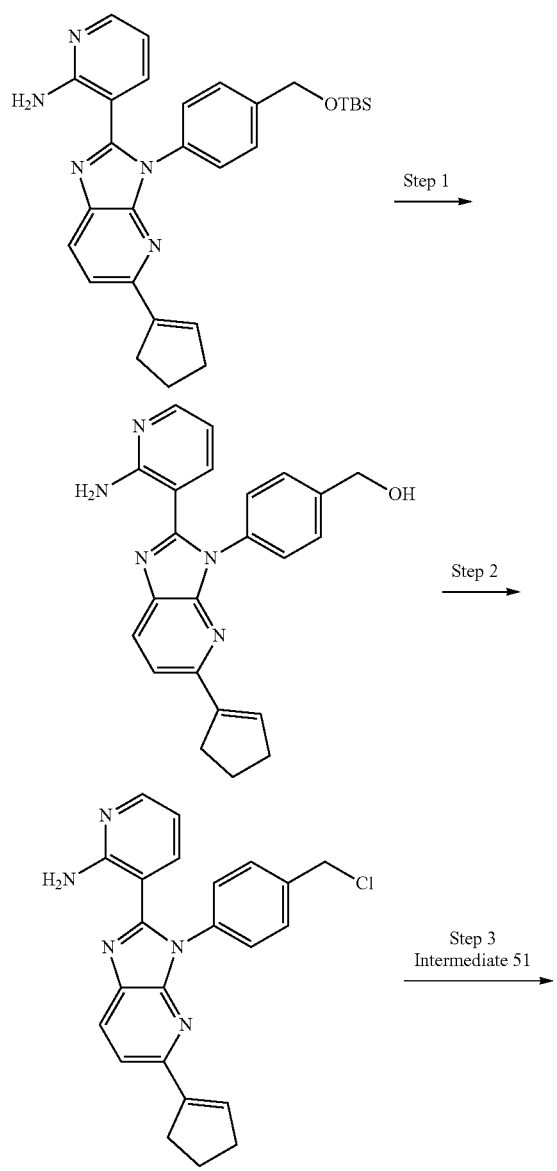

Example 453

Step 1: (4-(2-(2-Aminopyridin-3-yl)-5-(cyclopent-1-en-1-yl)-3H-imidazo[4,5-b]pyridin-3-yl)phenyl)methanol A mixture of 3-(3-(4-(((tert-butyldimethylsilyl)oxy)methyl)phenyl)-5-(cyclopent-1-en-1-yl)-3H-imidazo[4,5-b]pyridin-2-yl)pyridin-2-amine (refer to Intermediate 118 for detail procedures, 275 mg, 553 μmol) in TBAF (2.5M in THF, 4 mL) was degassed and purged with $N_2$ three times. The mixture was stirred at 25° C. for 0.5 hr under $N_2$ atmosphere. The reaction mixture was poured into $H_2O$ (15 mL), extracted with EtOAc (15 mL×3). The organic phase was dried over anhydrous $Na_2SO_4$, filtered and concentrated under reduced pressure, (4-(2-(2-aminopyridin-3-yl)-5-(cyclopent-1-en-1-yl)-3H-imidazo[4,5-b]pyridin-3-yl)phenyl)methanol (220 mg, crude) was obtained as a gray solid. MS: m/z=384.1 [M+H]$^+$.

Step 2: 3-(3-(4-(Chloromethyl)phenyl)-5-(cyclopent-1-en-1-yl)-3H-imidazo[4,5-b]pyridin-2-yl)pyridin-2-amine To a solution of (4-(2-(2-aminopyridin-3-yl)-5-(cyclopent-1-en-1-yl)-3H-imidazo[4,5-b]pyridin-3-yl)phenyl)methanol (220 mg, 574 μmol) in $CH_2Cl_2$ (4 mL) was added $SOCl_2$ (68 mg, 574 μmol). The mixture was stirred at 45° C. for 0.3 hr. The mixture was concentrated under reduced pressure, 3-(3-(4-(chloromethyl)phenyl)-5-(cyclopent-1-en-1-yl)-3H-imidazo[4,5-b]pyridin-2-yl)pyridin-2-amine (251 mg, crude) was obtained as a yellow solid. MS: m/z=402.0 [M+H]$^+$.

Step 3: 4-((1-(4-(2-(2-Aminopyridin-3-yl)-5-(cyclopent-1-en-1-yl)-3H-imidazo[4,5-b]pyridin-3-yl)benzyl)piperidin-4-yl)amino)pyrimidine-2-carbonitrile To a solution of 3-(3-(4-(chloromethyl)phenyl)-5-(cyclopent-1-en-1-yl)-3H-imidazo[4,5-b]pyridin-2-yl)pyridin-2-amine (251 mg, 625 μmol) and Intermediate 51 (218 mg, 687 μmol) in DMF (2 mL) were added $K_2CO_3$ (432 mg, 3.1 mmol) and NaI (28.1 mg, 187 μmol). The mixture was stirred at 50° C. for 1 hr. The reaction mixture was poured into $H_2O$ (15 mL), extracted with EtOAc (15 mL×3). The organic phase was dried over $Na_2SO_4$, filtered, and concentrated under reduced pressure. After purified by silica gel flash chromatography (Eluent of 0~15% MeOH in $CH_2Cl_2$), 4-((1-(4-(2-(2-aminopyridin-3-yl)-5-(cyclopent-1-en-1-yl)-

3H-imidazo[4,5-b]pyridin-3-yl)benzyl)piperidin-4-yl)amino)pyrimidine-2-carbonitrile (Example 453, 107.8 mg, yield: 30%) was obtained as an off white solid. MS: m/z=569.3 [M+H]+. 1H NMR (400 MHz, Dimethylsulfoxide-d6) δ 8.26-8.03 (m, 3H), 7.98 (dd, J=4.8, 2.0 Hz, 1H), 7.57 (d, J=8.4 Hz, 1H), 7.48-7.42 (m, 2H), 7.40-7.33 (m, 2H), 7.11 (dd, J=8.0, 2.0 Hz, 1H), 7.03 (br s, 2H), 6.67 (d, J=6.0 Hz, 1H), 6.53 (t, J=1.6 Hz, 1H), 6.36 (dd, J=7.6, 4.8 Hz, 1H), 3.89-3.71 (m, 1H), 3.57 (s, 2H), 3.35-3.34 (m, 2H), 2.86-2.76 (m, 2H), 2.71-2.65 (m, 2H), 2.20-2.10 (m, 2H), 1.99-1.83 (m, 4H), 1.54-1.44 (m, 2H).

Example 454: 4-((1-(4-(2-(2-Aminopyridin-3-yl)-5-vinyl-3H-imidazo[4,5-b]pyridin-3-yl)benzyl)piperidin-4-yl)amino)pyrimidine-2-carbonitrile

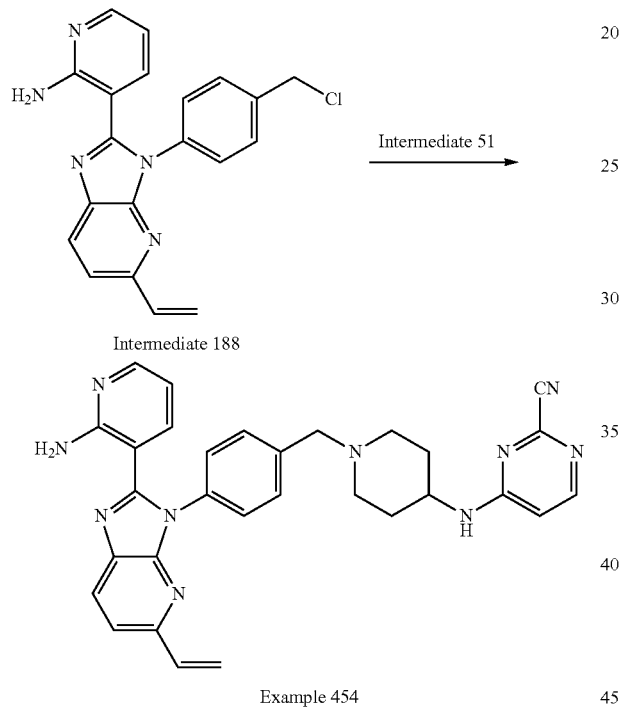

To a solution of Intermediate 188 (240 mg, 602 μmol, HCl) and Intermediate 51 (191 mg, 602 μmol, TFA) in DMF (2 mL) was added NaI (45.1 mg, 302 μmol) and K2CO3 (416 mg, 3.01 mmol). The mixture was stirred at 50° C. for 1 hr. The reaction mixture was diluted with water (10 mL) and extracted with EtOAc (2×20 mL). The combined organic layers were washed with brine (30 mL), dried over Na2SO4, filtered, and concentrated under reduced pressure. After purified by silica gel flash chromatography (Eluent of 0~7% MeOH in CH2Cl2), 4-((1-(4-(2-(2-aminopyridin-3-yl)-5-vinyl-3H-imidazo[4,5-b]pyridin-3-yl)benzyl)piperidin-4-yl)amino)pyrimidine-2-carbonitrile (Example 454, 145.4 mg, yield: 44%) was obtained as an off white solid. MS: m/z=529.2 [M+H]+. 1H NMR (400 MHz, Dimethylsulfoxide-d6) δ 8.16 (d, J=8.4 Hz, 1H), 8.07 (dd, J=13.6, 6.0 Hz, 2H), 7.98 (dd, J=4.4, 1.2 Hz, 1H), 7.57 (d, J=8.0 Hz, 1H), 7.50-7.43 (m, 2H), 7.42-7.34 (m, 2H), 7.12 (dd, J=8.0, 1.6 Hz, 1H), 7.02 (br s, 2H), 6.85 (dd, J=17.6, 10.4 Hz, 1H), 6.67 (br d, J=5.6 Hz, 1H), 6.36 (dd, J=7.6, 4.8 Hz, 1H), 6.11 (d, J=16.8 Hz, 1H), 5.40 (d, J=12.0 Hz, 1H), 3.89-3.74 (m, 1H), 3.58 (s, 2H), 2.82 (d, J=10.4 Hz, 2H), 2.23-2.09 (m, 2H), 1.95-1.82 (m, 2H), 1.57-1.42 (m, 2H).

Example 455: 4-((1-(4-(2-(2-Aminopyridin-3-yl)-5,6-dimethyl-3H-imidazo[4,5-b]pyridin-3-yl)benzyl)piperidin-4-yl)(methyl-d3)amino)pyrimidine-2-carbonitrile

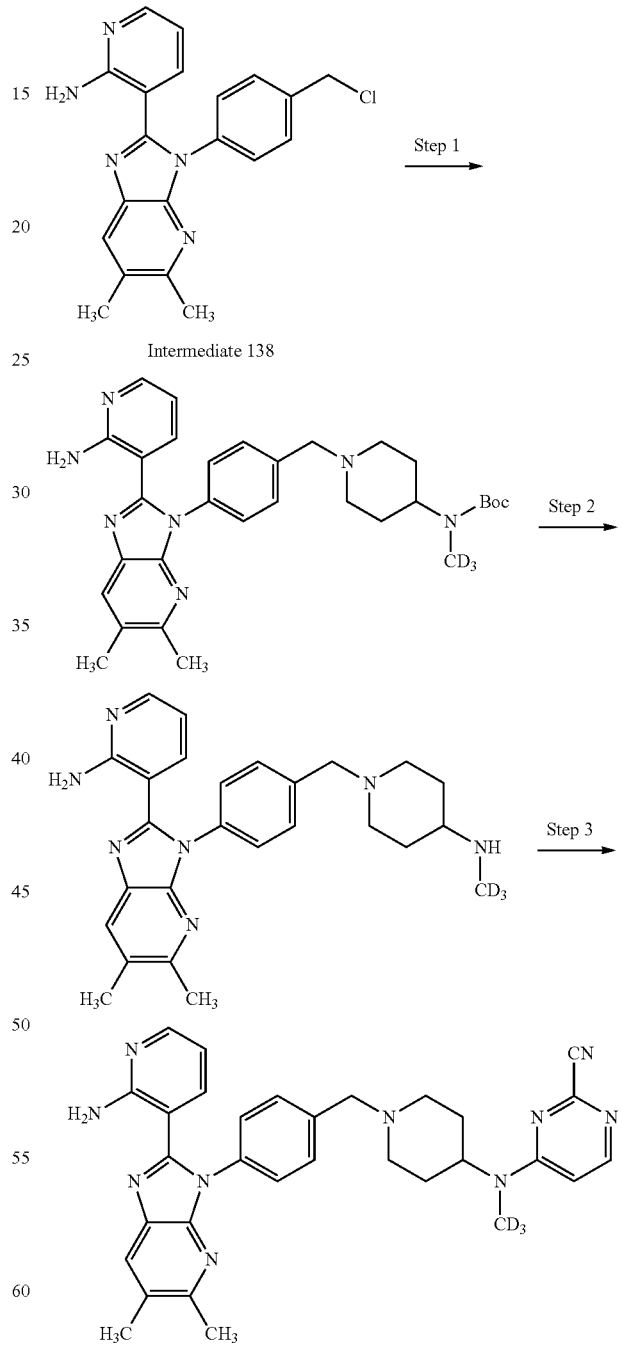

Step 1: Tert-butyl (1-(4-(2-(2-aminopyridin-3-yl)-5, 6-dimethyl-3H-imidazo[4,5-b]pyridin-3-yl)benzyl)piperidin-4-yl)(methyl-d₃)carbamate To a solution of Intermediate 138 (200 mg, 549 μmol) and tert-butyl (methyl-d₃)(piperidin-4-yl)carbamate (refer to Intermediate 41 for detail procedures, 143 mg, 660 μmol) in DMF (5 mL) were added $K_2CO_3$ (228 mg, 1.7 mmol) and NaI (82.4 mg, 550 μmol). The mixture was stirred at 50° C. for 8 hr. The mixture was concentrated under reduced pressure. After purified by silica gel flash chromatography (MeOH in $CH_2Cl_2$=0 to 15%), tert-butyl (1-(4-(2-(2-amino-pyridin-3-yl)-5,6-dimethyl-3H-imidazo[4,5-b]pyridin-3-yl)benzyl)piperidin-4-yl)(methyl-d₃)carbamate (165 mg, yield: 47%) was obtained as a yellow solid. MS: m/z=545.3 [M+H]⁺.

Step 2: 3-(5,6-Dimethyl-3-(4-((4-((methyl-d₃)amino)piperidin-1-yl)methyl)phenyl)-3H-imidazo[4,5-h]pyridin-2-yl)pyridin-2-amine To a solution of tert-butyl (1-(4-(2-(2-aminopyridin-3-yl)-5,6-dimethyl-3H-imidazo[4,5-b]pyridin-3-yl)benzyl)piperidin-4-yl)(methyl-d₃)carbamate (160 mg, 294 μmol) in $CH_2Cl_2$ (2 mL) was added TFA (1.54 g, 13.5 mmol). The mixture was stirred at 25° C. for 1 hr. The mixture was concentrated under reduced pressure, 3-(5,6-dimethyl-3-(4-((4-((methyl-d₃)amino)piperidin-1-yl)methyl)phenyl)-3H-imidazo[4,5-b]pyridin-2-yl)pyridin-2-amine (160 mg, crude) was obtained as a yellow solid. MS: m/z=445.1 [M+H]⁺.

Step 3: 4-((1-(4-(2-(2-Aminopyridin-3-yl)-5,6-dimethyl-3H-imidazo[4,5-b]pyridin-3-yl)benzyl)piperidin-4-yl)(methyl-d₃)amino)pyrimidine-2-carbonitrile 4-Chloropyrimidine-2-carbonitrile (60.3 mg, 432 μmol), 3-(5,6-dimethyl-3-(4-((4-((methyl-d₃)amino)piperidin-1-yl)methyl)phenyl)-3H-imidazo[4,5-b]pyridin-2-yl)pyridin-2-amine (160 mg, 360 μmol) and DIEA (93 mg, 720 μmol) were taken up into a microwave tube in NMP (2 mL). The sealed tube was heated at 130° C. for 0.5 hr under microwave. The reaction mixture was diluted with $H_2O$ (10 mL) and extracted with EtOAc (10 mL×2). The combined organic layers were washed with brine (30 mL), dried over $Na_2SO_4$, filtered and concentrated under reduced pressure. After purified by prep-HPLC (column: Waters xbridge 150× 25 mm 10 μm; mobile phase: [water ($NH_4HCO_3$)-ACN]; gradient: 38%-58% B over 11 min), 4-((1-(4-(2-(2-aminopyridin-3-yl)-5,6-dimethyl-3H-imidazo[4,5-b]pyridin-3-yl)benzyl)piperidin-4-yl)(methyl-d₃)amino)pyrimidine-2-carbonitrile (Example 455, 13.5 mg, yield: 7% for two steps) was obtained as a yellow solid. MS: m/z=548.3 [M+H]⁺. ¹H NMR (400 MHz, Methanol-d₄) δ8.16 (d, J=6.4 Hz, 1H), 7.95 (dd, J=5.2, 1.6 Hz, 1H), 7.92-7.89 (m, 1H), 7.53 (d, J=8.4 Hz, 2H), 7.37 (d, J=8.4 Hz, 2H), 7.26 (dd, J=7.6, 1.6 Hz, 1H), 6.91-6.76 (m, 1H), 6.45 (dd, J=7.6, 5.2 Hz, 1H), 4.91-4.89 (m, 1H), 3.67 (s, 2H), 3.07 (d, J=11.2 Hz, 2H), 2.54 (s, 3H), 2.46 (s, 3H), 2.31-2.23 (m, 2H), 2.00-1.89 (m, 2H), 1.74-1.65 (m, 2H).

Example 456: 4-((1-(4-(2-(2-Aminopyridin-3-yl)-5-(5-fluoropyridin-2-yl)-3H-imidazo[4,5-b]pyridin-3-yl)benzyl)piperidin-4-yl)amino)pyrimidine-2-carbonitrile

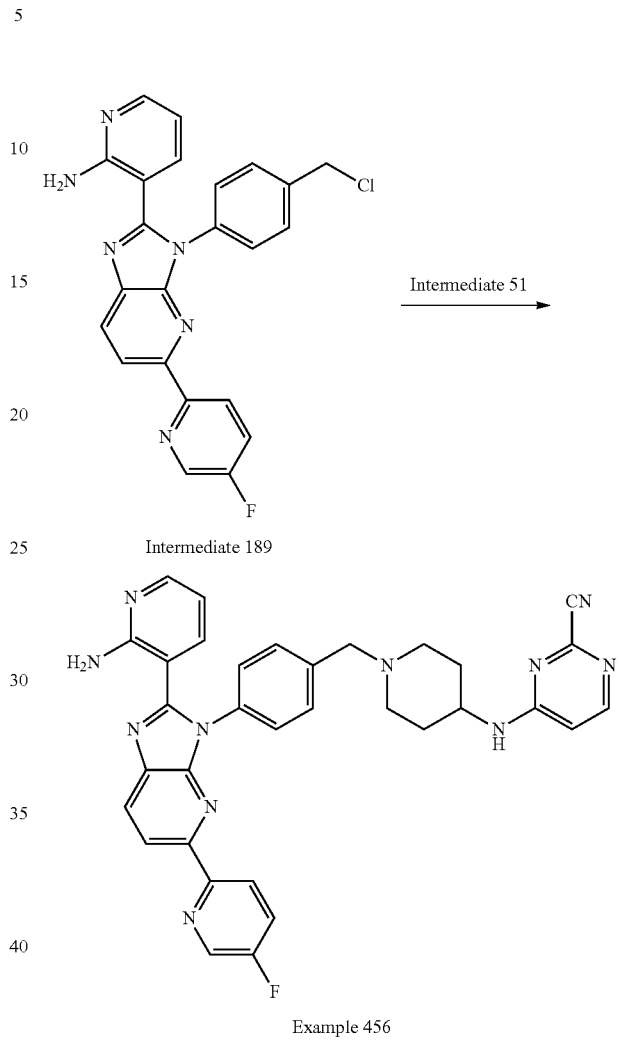

To a solution of Intermediate 189 (200 mg, 484 μmol) in DMF (5 mL) were added Intermediate 51 (113 mg, 557 μmol), NaI (35 mg, 232 μmol) and $K_2CO_3$ (256 mg, 1.86 mmol) at 25° C. The mixture was stirred at 50° C. for 3 hr. The reaction mixture was poured into $H_2O$ (50 mL) and extracted with $CH_2Cl_2$ (20 mL×2). The combined organic layers were washed with brine (40 mL), dried over anhydrous $Na_2SO_4$, filtered, and concentrated to dryness. After purified by silica gel flash chromatography (Eluent of 0~7% MeOH in $CH_2Cl_2$), 4-((1-(4-(2-(2-aminopyridin-3-yl)-5-(5-fluoropyridin-2-yl)-3H-imidazo[4,5-b]pyridin-3-yl)benzyl)piperidin-4-yl)amino)pyrimidine-2-carbonitrile (Example 456, 40.2 mg, yield: 14%) was obtained as an off white solid. MS: m/z=598.2 [M+H]⁺. ¹H NMR (400 MHz, Dimethylsulfoxide-d₆) δ 8.68 (d, J=2.8 Hz, 1H), 8.41 (d, J=8.4 Hz, 1H), 8.33 (d, J=8.4 Hz, 1H), 8.24 (dd, J=8.8, 4.8 Hz, 1H), 8.15-8.04 (m, 2H), 8.03-7.98 (m, 1H), 7.87-7.79 (m, 1H), 7.53-7.43 (m, 4H), 7.18 (dd, J=8.0, 2.0 Hz, 1H), 7.03 (br s, 2H), 6.69 (d, J=6.4 Hz, 1H), 6.39 (dd, J=7.6, 4.8 Hz, 1H), 3.91-3.74 (m, 1H), 3.61 (s, 2H), 2.89-2.78 (m, 2H), 2.24-2.13 (m, 2H), 1.97-1.84 (m, 2H), 1.60-1.44 (m, 2H).

1551

Example 457: 4-((1-(4-(2-(2-Aminopyridin-3-yl)-5-(methylamino)-3H-imidazo[4,5-b]pyridin-3-yl)benzyl)piperidin-4-yl)amino)pyrimidine-2-carbonitrile

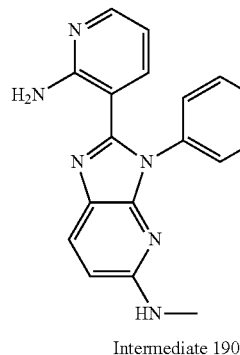

Intermediate 190

→ Intermediate 51

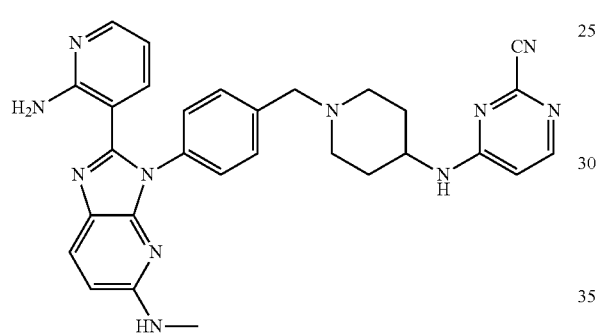

Example 457

To a solution of Intermediate 190 (220 mg, 603 μmol) and Intermediate 51 (229 mg, 723 μmol) in DMF (10 mL) were added K$_2$CO$_3$ (416 mg, 3.02 mmol) and NaI (27.1 mg, 180 μmol). The mixture was stirred at 50° C. for 1 hr. The reaction mixture was diluted with H$_2$O (30 mL) and extracted with EtOAc (30 mL×3). The combined organic layers were washed with H$_2$O (50 mL×3), dried over Na$_2$SO$_4$, filtered, and concentrated under reduced pressure. After purified by prep-HPLC (column: Waters xbridge 150*25 mm 10 μm; mobile phase: [water (NH$_4$HCO$_3$)-ACN]; gradient: 29%-59% B over 14 min), 4-((1-(4-(2-(2-aminopyridin-3-yl)-5-(methylamino)-3H-imidazo[4,5-b]pyridin-3-yl)benzyl)piperidin-4-yl)amino)pyrimidine-2-carbonitrile (Example 457, 120.6 mg, yield: 36%) was obtained as a yellow powder. MS: m/z=532.2 [M+H]$^+$. $^1$H NMR (400 MHz, Dimethylsulfoxide-d$_6$) δ 8.25-7.94 (m, 2H), 7.90 (dd, J=4.8, 1.6 Hz, 1H), 7.80 (d, J=8.4 Hz, 1H), 7.42 (d, J=8.4 Hz, 2H), 7.31 (d, J=8.4 Hz, 2H), 7.05 (br s, 2H), 6.93 (dd, J=8.0, 2.0 Hz, 1H), 6.84-6.52 (m, 2H), 6.48 (d, J=8.8 Hz, 1H), 6.28 (dd, J=8.0, 5.2 Hz, 1H), 3.93-3.65 (m, 1H), 3.56 (s, 2H), 2.85-2.75 (m, 2H), 2.71 (d, J=4.4 Hz, 3H), 2.20-2.10 (m, 2H), 1.93-1.80 (m, 2H), 1.54-1.41 (m, 2H).

1552

Example 458: 4-((1-(4-(2-(2-Aminopyridin-3-yl)-5-(bis(methyl-d$_3$)amino)-3H-imidazo[4,5-b]pyridin-3-yl)benzyl)piperidin-4-yl)amino)pyrimidine-2-carbonitrile

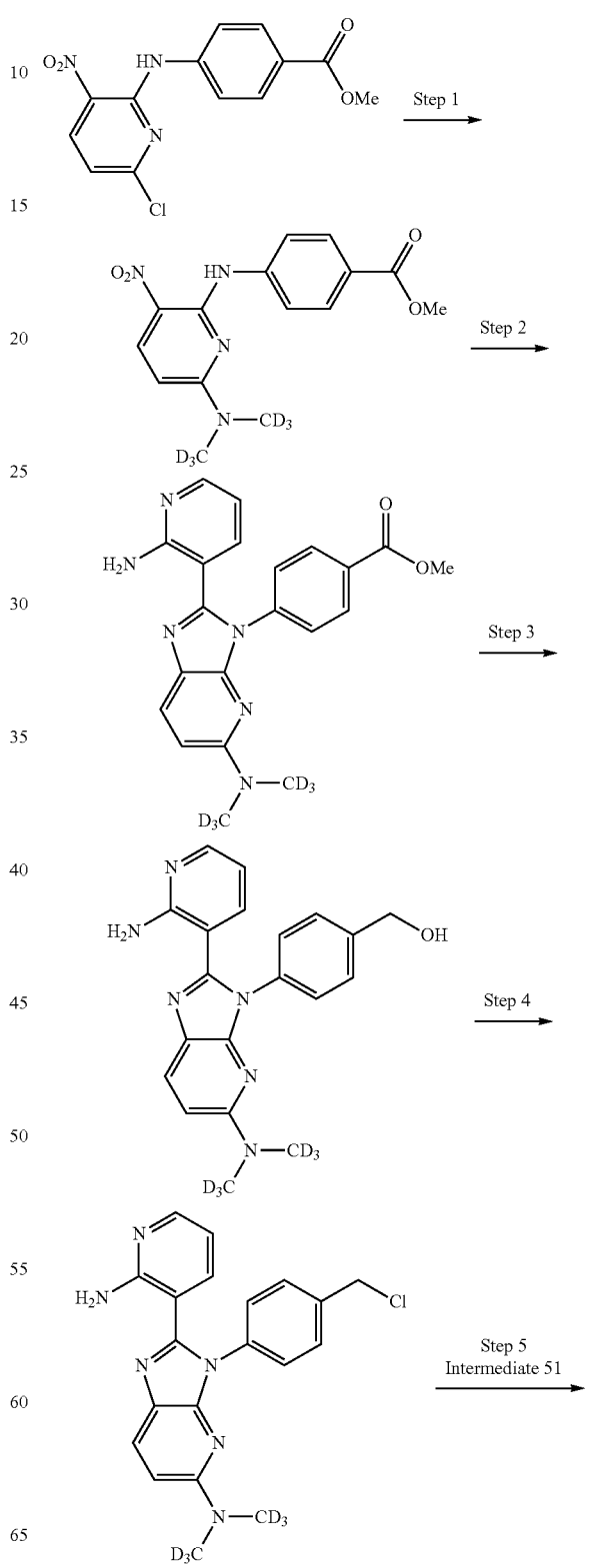

-continued

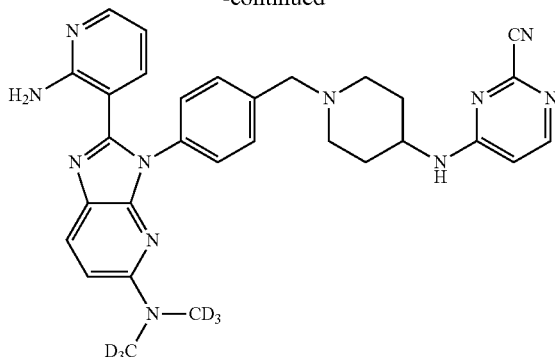

Example 458

Step 1: Methyl 4-((6-(bis(methyl-d₃)amino)-3-nitro-pyridin-2-yl)amino)benzoate

To a mixture of methyl 4-((6-chloro-3-nitropyridin-2-yl)amino)benzoate (refer to Intermediate 13 for detail procedures, 10.8 g, 35.2 mmol), bis(methyl-d₃)amine (2.0 g, 39.1 mmol) in ACN (120 mL) was added DIEA (15.1 g, 117 mmol). The mixture was degassed and purged with $N_2$ three times and stirred at 80° C. for 2 hr under $N_2$ atmosphere. The reaction mixture was filtered, methyl 4-((6-(bis(methyl-d₃)amino)-3-nitropyridin-2-yl)amino)benzoate (8.0 g, yield: 51%) was obtained as a yellow solid. MS: m/z=323.0 [M+H]⁺. ¹H NMR (400 MHz, Chloroform-d) δ 11.02 (s, 11H), 8.30 (d, J=9.6 Hz, 11H), 8.05-8.02 (m, 2H), 7.81-7.78 (m, 2H), 6.13 (d, J=9.6 Hz, 1H), 3.91 (s, 3H).

Step 2: Methyl 4-(2-(2-aminopyridin-3-yl)-5-(bis(methyl-d₃)amino)-3H-imidazo[4,5-b]pyridin-3-yl)benzoate A mixture of methyl 4-((6-(bis(methyl-d₃)amino)-3-nitropyridin-2-yl)amino)benzoate (6.4 g 19.8 mmol), 2-aminonicotinaldehyde (2.67 g, 21.8 mmol) and $Na_2S_2O_4$ (13.8 g, 79.4 mmol) in DMSO (150 mL) was degassed and purged with $N_2$ three times. The mixture was stirred at 100° C. for 16 hr under $N_2$ atmosphere. The reaction mixture was diluted with $H_2O$ (200 mL) and extracted with EtOAc (200 mL×3). The combined organic layers were washed with brine (200 mL), dried over $Na_2SO_4$, filtered and concentrated under reduced pressure. After purified by silica gel flash chromatography (Eluent of 0~29% EtOAc in petroleum ether), methyl 4-(2-(2-aminopyridin-3-yl)-5-(bis(methyl-d₃)amino)-3H-imidazo[4,5-b]pyridin-3-yl)benzoate (5.0 g, yield: 59%) was obtained as a yellow solid. MS: m/z=395.3 [M+H]+, ¹H NMR (400 MHz, Chloroform-d) δ 8.14 (d, J=8.8 Hz, 2H), 8.00 (dd, J=5.2, 2.0 Hz, 1H), 7.84 (d, J=8.8 Hz, 1H), 7.48 (d, J=8.4 Hz, 2H), 7.00-6.96 (m, 1H), 6.56 (d, J=8.8 Hz, 3H), 6.35 (dd, J=7.6, 5.2 Hz, 1H), 3.95 (s, 3H).

Step 3: (4-(2-(2-Aminopyridin-3-yl)-5-(bis(methyl-d3)amino)-3H-imidazo[4,5-b]pyridin-3-yl)phenyl)methanol To a mixture of methyl 4-(2-(2-aminopyridin-3-yl)-5-(bis(methyl-d₃)amino)-3H-imidazo[4,5-b]pyridin-3-yl)benzoate (5.0 g, 12.7 mmol) in THF (150 mL) was added LiAlH₄ (2.5 M in THF, 7.61 mL). The mixture was degassed and purged with $N_2$ three times and stirred at 0° C. for 2 hr under $N_2$ atmosphere. The reaction mixture was quenched with $Na_2SO_4 \cdot 10H_2O$ (1.5 g) at 0° C. and filtered. The filtrate was concentrated under reduced pressure, (4-(2-(2-aminopyridin-3-yl)-5-(bis(methyl-d₃)amino)-3H-imidazo[4,5-b]pyridin-3-yl)phenyl)methanol (4.6 g, yield: 91%) was obtained as a yellow solid. MS: m/z=367.2 [M+H]⁺.

Step 4: 2-(2-Aminopyridin-3-yl)-3-(4-(chloromethyl)phenyl)-N,N-bis(methyl-d3)-3H-imidazo[4,5-b]pyridin-5-amine To a solution of (4-(2-(2-aminopyridin-3-yl)-5-(bis(methyl-d₃)amino)-3H-imidazo[4,5-b]pyridin-3-yl)phenyl)methanol (600 mg, 715 µmol) in $CH_2Cl_2$ (50 mL) was added $SOCl_2$ (8.96 g, 75.3 mmol). The mixture was stirred at 40° C. for 1 hr. The mixture was concentrated under reduced pressure, 2-(2-aminopyridin-3-yl)-3-(4-(chloromethyl)phenyl)-N,N-bis(methyl-d₃)-3H-imidazo[4,5-b]pyridin-5-amine (5.0 mg, yield: 97%) was obtained as a yellow solid. MS: m/z=385.0 [M+H]⁺.

Step 5: 4-((1-(4-(2-(2-Aminopyridin-3-yl)-5-(bis(methyl-d₃)amino)-3H-imidazo[4,5-b]pyridin-3-yl)benzyl)piperidin-4-yl)amino)pyrimidine-2-carbonitrile To a solution of 2-(2-aminopyridin-3-yl)-3-(4-(chloromethyl)phenyl)-N,N-bis(methyl-d₃)-3H-imidazo[4,5-b]pyridin-5-amine (300 mg, 779 µmol) and Intermediate 51 (158 mg, 779 µmol) in DMF (5 mL) were added NaI (58.4 mg, 390 µmol) and $K_2CO_3$ (539 mg, 3.90 mmol). The mixture was stirred at 50° C. for 1 hr. The reaction mixture was diluted with $H_2O$ (20 mL) and extracted with EtOAc (50 mL×2). The combined organic layers were washed with brine (30 mL), dried over $Na_2SO_4$, filtered and concentrated under reduced pressure. After purified by silica gel flash chromatography (Eluent of 0~6% MeOH in $CH_2Cl_2$), 4-((1-(4-(2-(2-aminopyridin-3-yl)-5-(bis(methyl-d3)amino)-3H-imidazo[4,5-b]pyridin-3-yl)benzyl)piperidin-4-yl)amino)pyrimidine-2-carbonitrile (Example 458, 89 mg, yield: 20%) was obtained as a yellow solid. MS: m/z=552.0 [M+H]⁺. ¹H NMR (400 MHz, Dimethylsulfoxide-d₆) δ 8.15 (dd, J=17.6, 6.0 Hz, 2H), 7.94-7.89 (m, 2H), 7.43 (d, J=8.0 Hz, 2H), 7.31 (d, J=8.4 Hz, 2H), 7.06 (s, 2H), 6.97 (dd, J=7.6, 1.6 Hz, 1H), 6.71-6.64 (m, 2H), 6.30 (dd, J=7.6, 4.8 Hz, 1H), 3.86-3.73 (m, 1H), 3.57 (s, 2H), 2.81 (d, J=10.4 Hz, 2H), 2.17-2.10 (m, 2H), 1.91-1.84 (m, 2H), 1.52-1.43 (m, 2H).

Example 459: 4-((1-(4-(2-(2-Aminopyridin-3-yl)-5-((methyl-d₃)amino)-3H-imidazo[4,5-b]pyridin-3-yl)benzyl)piperidin-4-yl)amino)pyrimidine-2-carbonitrile

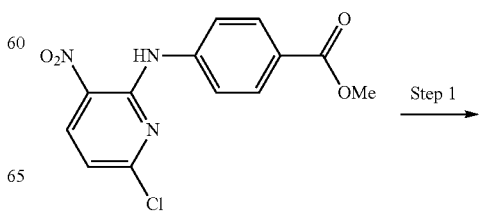

Step 1

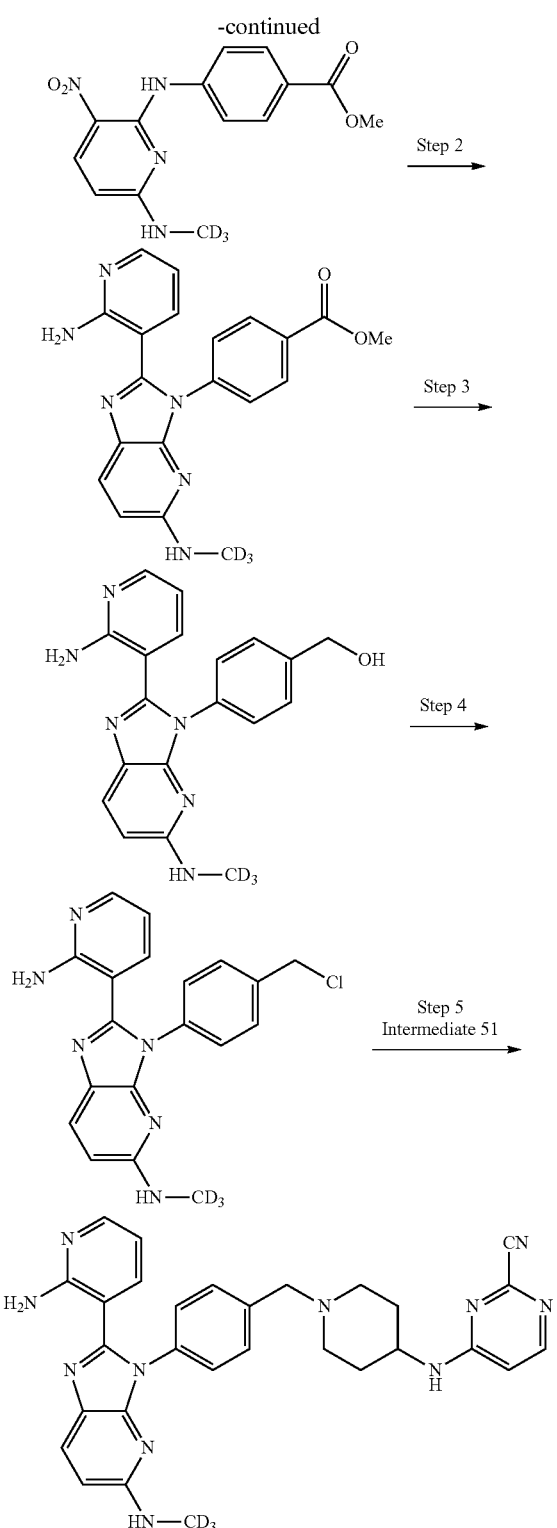

Example 459

Step 1: Methyl 4-((6-((methyl-d₃)amino)-3-nitropyridin-2-yl)amino)benzoate

To a mixture of methyl 4-((6-chloro-3-nitropyridin-2-yl)amino)benzoate (refer to Intermediate 13 for detail procedures, 2.5 g, 8.13 mmol) and CD₃NH₂·HCl (713 mg, 10.5 mmol) in CH₃CN (30 mL) was added DIEA (3.15 g, 24.3 mmol). The mixture was stirred at 90° C. for 2 hr. The reaction mixture was filtered and concentrated under reduced pressure. The crude product was triturated with EtOAc (50 mL) at 25° C. for 10 min, methyl 4-((6-((methyl-d₃)amino)-3-nitropyridin-2-yl)amino)benzoate (2.3 g, yield: 76%) was obtained as a yellow solid. MS: m/z=305.9 [M+H]⁺. ¹H NMR (400 MHz, Dimethylsulfoxide-d₆) δ 11.06 (s, 1H), 8.43 (s, 1H), 8.09 (d, J=9.6 Hz, 1H), 7.98-7.92 (m, 4H), 6.19 (d, J=9.6 Hz, 1H), 3.83 (s, 3H).

Step 2: Methyl 4-(2-(2-aminopyridin-3-yl)-5-((methyl-d₃)amino)-3H-imidazo[4,5-h]pyridin-3-yl)benzoate To a mixture of methyl 4-((6-((methyl-d₃)amino)-3-nitropyridin-2-yl)amino)benzoate (2.30 g, 7.53 mmol), 2-aminonicotinaldehyde (1.10 g, 9.04 mmol) in DMSO (40 mL) was added Na₂S₂O₄ (5.25 g, 30.1 mmol). The mixture was stirred at 100° C. for 16 hr under N₂ atmosphere. The reaction mixture was diluted with H₂O (150 mL) and extracted with EtOAc (100 mL×3). The combined organic layers were washed with H₂O (100 mL×3), dried over Na₂SO₄, filtered and concentrated under reduced pressure to give a residue. After purified by column chromatography (eluent of 0-45% EtOAc in petroleum ether), methyl 4-(2-(2-aminopyridin-3-yl)-5-((methyl-d₃)amino)-3H-imidazo[4,5-b]pyridin-3-yl)benzoate (1.0 g, yield: 35%) was obtained as a yellow solid. MS: m/z=378.1 [M+H]⁺. ¹H NMR (400 MHz, Dimethylsulfoxide-d₆) δ 8.08-8.04 (m, 2H), 7.93 (dd, J=4.8, 1.6 Hz, 1H), 7.81 (d, J=8.8 Hz, 1H), 7.54-7.50 (m, 2H), 6.99 (dd, J=7.6, 2.0 Hz, 1H), 6.95-6.82 (m, 2H), 6.71 (s, 1H), 6.50 (d, J=8.8 Hz, 1H), 6.36 (dd, J=7.6, 4.8 Hz, 1H), 3.88 (s, 3H)

Step 3: (4-(2-(2-Aminopyridin-3-yl)-5-((methyl-d₃)amino)-3H-imidazo[4,5-b]pyridin-3-yl)phenyl)methanol To a mixture of methyl 4-(2-(2-aminopyridin-3-yl)-5-((methyl-d₃)amino)-3H-imidazo[4,5-b]pyridin-3-yl)benzoate (1 g, 2.65 mmol) in THF (50 mL) was added LiAlH₄ (2.5 M, 1.59 mL). The mixture was stirred at 25° C. for 1 hr under N₂ atmosphere. The reaction mixture was quenched with Na₂SO₄·10H₂O (2 g) at 0° C., filtered and concentrated under reduced pressure to give (4-(2-(2-aminopyridin-3-yl)-5-((methyl-d₃)amino)-3H-imidazo[4,5-b]pyridin-3-yl)phenyl)methanol (900 mg, yield: 81%) as a yellow solid. MS: m/z=350.3 [M+H]⁺.

Step 4: 2-(2-Aminopyridin-3-yl)-3-(4-(chloromethyl)phenyl)-N-(methyl-d₃)-3H-imidazo[4,5-b]pyridin-5-amine To a mixture of (4-(2-(2-aminopyridin-3-yl)-5-((methyl-d₃)amino)-3H-imidazo[4,5-b]pyridin-3-yl)phenyl)methanol (900 mg, 2.58 mmol) in CH₂Cl₂ (5 mL) was added SOCl₂ (3.28 g, 27.5 mmol). The mixture was stirred at 40° C. for 1 hr. The reaction mixture was concentrated under reduced pressure to give 2-(2-aminopyridin-3-yl)-3-(4-(chloromethyl)phenyl)-N-(methyl-d₃)-3H-imidazo[4,5-b]pyridin-5-amine (950 mg, yield: 98%) as a brown solid. MS: m/z=368.1 [M+H]⁺.

Step 5: 4-((1-(4-(2-(2-Aminopyridin-3-yl)-5-((methyl-d₃)amino)-3H-imidazo[4,5-b]pyridin-3-yl)benzyl)piperidin-4-yl)amino)pyrimidine-2-carbonitrile To a mixture of 2-(2-aminopyridin-3-yl)-3-(4-(chloroethyl)phenyl)-N-(methyl-d₃)-3H-imidazo[4,5-b]pyridin-5- amine (300 mg, 815 μmol) and Intermediate 51 (200 mg, 984 μmol) in DMF (10 mL) were added K$_2$CO$_3$ (563 mg, 4.08 mmol) and NaI (36.6 mg, 244 μmol). The mixture was stirred at 50° C. for 1 hr. The reaction mixture was diluted with H$_2$O (50 mL) and extracted with EtOAc (50 mL×3). The combined organic layers were washed with H$_2$O (50 mL×3), dried over Na$_2$SO$_4$, filtered and concentrated under reduced pressure to give a residue. After purified by column chromatography (eluent of 0~8% MeOH in CH$_2$Cl$_2$), 4-((1-(4-(2-(2-aminopyridin-3-yl)-5-((methyl-d$_3$)amino)-3H-imidazo[4,5-b]pyridin-3-yl)benzyl)piperidin-4-yl)amino)pyrimidine-2-carbonitrile (Example 459, 123.1 mg, yield: 28%) was obtained as a yellow solid. MS: m/z=535.1 [M+H]$^+$. $^1$H NMR (400 MHz, Dimethylsulfoxide-d$_6$) δ 8.15-7.97 (m, 2H), 7.93-7.85 (m, 1H), 7.80 (d, J=8.8 Hz, 1H), 7.42 (d, J=7.2 Hz, 2H), 7.30 (d, J=7.6 Hz, 2H), 7.05 (br s, 2H), 6.93 (d, J=7.2 Hz, 1H), 6.72-6.60 (m, 2H), 6.47 (d, J=8.4 Hz, 1H), 6.32-6.24 (m, 1H), 3.85-3.75 (m, 1H), 3.56 (s, 2H), 2.85-2.75 (m, 2H), 2.20-2.10 (m, 2H), 1.94-1.81 (m, 2H), 1.52-1.40 (m, 2H).

Example 460: 4-((1-(4-(2-(2-Aminopyridin-3-yl)-5-(azetidin-1-yl)-3H-imidazo[4,5-b]pyridin-3-yl)benzyl)piperidin-4-yl)amino)pyrimidine-2-carbonitrile

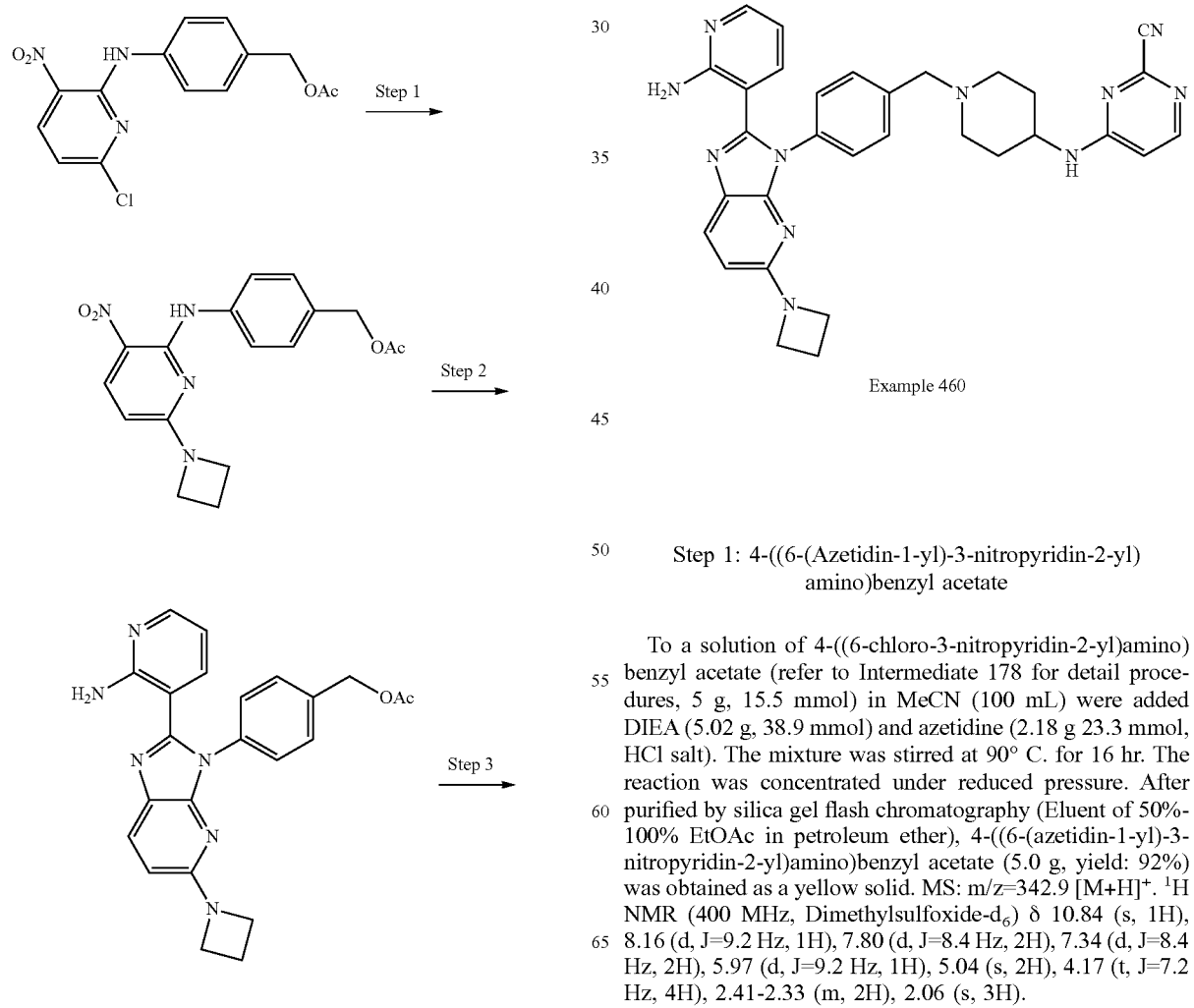

Example 460

Step 1: 4-((6-(Azetidin-1-yl)-3-nitropyridin-2-yl)amino)benzyl acetate

To a solution of 4-((6-chloro-3-nitropyridin-2-yl)amino)benzyl acetate (refer to Intermediate 178 for detail procedures, 5 g, 15.5 mmol) in MeCN (100 mL) were added DIEA (5.02 g, 38.9 mmol) and azetidine (2.18 g 23.3 mmol, HCl salt). The mixture was stirred at 90° C. for 16 hr. The reaction was concentrated under reduced pressure. After purified by silica gel flash chromatography (Eluent of 50%-100% EtOAc in petroleum ether), 4-((6-(azetidin-1-yl)-3-nitropyridin-2-yl)amino)benzyl acetate (5.0 g, yield: 92%) was obtained as a yellow solid. MS: m/z=342.9 [M+H]$^+$. $^1$H NMR (400 MHz, Dimethylsulfoxide-d$_6$) δ 10.84 (s, 1H), 8.16 (d, J=9.2 Hz, 1H), 7.80 (d, J=8.4 Hz, 2H), 7.34 (d, J=8.4 Hz, 2H), 5.97 (d, J=9.2 Hz, 1H), 5.04 (s, 2H), 4.17 (t, J=7.2 Hz, 4H), 2.41-2.33 (m, 2H), 2.06 (s, 3H).

Step 2: 4-(2-(2-Aminopyridin-3-yl)-5-(azetidin-1-yl)-3H-imidazo[4,5-b]pyridin-3-yl)benzyl acetate To a solution of 4-((6-(azetidin-1-yl)-3-nitropyridin-2-yl)amino)benzyl acetate (500 mg, 1.46 mmol) in DMSO (20 mL) were added Na$_2$S$_2$O$_4$ (1.17 g, 5.84 mmol, 87% purity) and 2-aminonicotinaldehyde (214 mg, 1.75 mmol). The mixture was stirred at 100° C. for 4 hr. The reaction mixture was quenched with H$_2$O (25 mL) at 25° C., then diluted with CH$_2$Cl$_2$ (50 mL) and washed with H$_2$O (50 mL×3) and brine (100 mL), dried over Na$_2$SO$_4$, filtered and concentrated under reduced pressure. After purified by silica gel flash chromatography (Eluent of 30%-60% EtOAc in petroleum ether), 4-(2-(2-aminopyridin-3-yl)-5-(azetidin-1-yl)-3H-imidazo[4,5-b]pyridin-3-yl)benzyl acetate (280 mg, yield: 46%) was obtained as a green solid. MS: m/z=415.4 [M+H]$^+$. $^1$H NMR (400 MHz, Dimethylsulfoxide-d$_6$) δ 7.96-7.88 (m, 2H), 7.48 (d, J=8.4 Hz, 2H), 7.36 (d, J=8.4 Hz, 2H), 7.01 (dd, J=7.6, 1.6 Hz, 1H), 6.90 (br s, 2H), 6.41-6.31 (m, 2H), 5.15 (s, 2H), 3.91 (t, J=7.2 Hz, 4H), 2.33-2.23 (m, 2H), 2.10 (s, 3H).

Step 3: (4-(2-(2-Aminopyridin-3-yl)-5-(azetidin-1-yl)-3H-imidazo[4,5-b]pyridin-3-yl)phenyl)methanol To a solution of 4-(2-(2-aminopyridin-3-yl)-5-(azetidin-1-yl)-3H-imidazo[4,5-b]pyridin-3-yl)benzyl acetate (280 mg, 676 μmol) in THF (4 mL), MeOH (4 mL) and H$_2$O (1 mL) was added K$_2$CO$_3$ (280 mg, 2.03 mmol). The mixture was stirred at 25° C. for 0.5 hr. The reaction mixture was quenched with H$_2$O (5 mL) at 25° C., and extracted with CH$_2$Cl$_2$ (20 mL×3). The combined organic layers were washed with brine (50 mL), dried over Na$_2$SO$_4$, filtered, and concentrated under reduced pressure to give (4-(2-(2-aminopyridin-3-yl)-5-(azetidin-1-yl)-3H-imidazo[4,5-b]pyridin-3-yl)phenyl)methanol (240 mg, yield: 95%) as a yellow solid. MS: m/z=373.1 [M+H]$^+$. $^1$H NMR (400 MHz, Dimethylsulfoxide-d$_6$) δ 7.96-7.87 (m, 2H), 7.43 (d, J=8.0 Hz, 2H), 7.30 (d, J=8.0 Hz, 2H), 7.00-6.97 (m, 3H), 6.37 (d, J=8.8 Hz, 1H), 6.33 (dd, J=7.6, 4.8 Hz, 1H), 5.34 (t, J=6.0 Hz, 1H), 4.57 (d, J=6.0 Hz, 2H), 3.90 (t, J=7.2 Hz, 4H), 2.32-2.22 (m, 2H).

Step 4: 4-(2-(2-Aminopyridin-3-yl)-5-(azetidin-1-yl)-3H-imidazo[4,5-b]pyridin-3-yl)benzyl methanesulfonate To a solution of (4-(2-(2-aminopyridin-3-yl)-5-(azetidin-1-yl)-3H-imidazo[4,5-b]pyridin-3-yl)phenyl)methanol (140 mg, 376 μmol) in CH$_2$Cl$_2$ (15 mL) were added TEA (114 mg, 1.13 mmol) and MsCl (140 mg, 1.22 mmol) at 0° C. The mixture was stirred at 0° C. for 1 hr. Additional MsCl (100 mg, 873 μmol) was added at 0° C. The mixture was stirred at 0° C. for 15 minutes. The reaction mixture was quenched with saturated NaHCO$_3$ aqueous (20 mL) at 0° C. and was then diluted with CH$_2$Cl$_2$ (10 mL) and extracted with CH$_2$Cl$_2$ (15 mL×2). The combined organic layers were washed with brine (50 mL), dried over Na$_2$SO$_4$, filtered and concentrated under reduced pressure. 4-(2-(2-Aminopyridin-3-yl)-5-(azetidin-1-yl)-3H-imidazo[4,5-b]pyridin-3-yl)benzyl methanesulfonate (170 mg) was obtained as a yellow solid. MS: m/z=451.0 [M+H]$^+$.

Step 5: 4-((1-(4-(2-(2-Aminopyridin-3-yl)-5-(azetidin-1-yl)-3H-imidazo[4,5-b]pyridin-3-yl)benzyl)piperidin-4-yl)amino)pyrimidine-2-carbonitrile To a solution of 4-(2-(2-aminopyridin-3-yl)-5-(azetidin-1-yl)-3H-imidazo[4,5-b]pyridin-3-yl)benzyl methanesulfonate (170 mg, 377 μmol) and Intermediate 51 (120 mg, 377 μmol, TFA) in DMF (2 mL) were added K$_2$CO$_3$ (209 mg, 1.51 mmol) and NaI (11.3 mg, 75.5 μmol). The mixture was stirred at 50° C. for 1 hr. The mixture was filtered through Celite and concentrated under reduced pressure. After purified by prep-HPLC (column: Waters xbridge 150× 25 mm×10 μm; mobile phase: [water (NH$_3$H$_2$O+ NH$_4$HCO$_3$)-ACN]; gradient: 30%-60% B over 11 min), 4-((1-(4-(2-(2-Aminopyridin-3-yl)-5-(azetidin-1-yl)-3H-imidazo[4,5-b]pyridin-3-yl)benzyl)piperidin-4-yl)amino)pyrimidine-2-carbonitrile (Example 460, 17.7 mg, yield: 8.4% for two steps) was obtained as a yellow solid. MS: m/z=558.5 [M+H]$^+$. $^1$H NMR (400 MHz, Dimethylsulfoxide-d$_6$) δ 8.08-8.05 (d, J=6.8 Hz, 2H), 7.94-7.89 (m, 2H), 7.42 (d, J=8.4 Hz, 2H), 7.30 (d, J=8.4 Hz, 2H), 7.01 (br s, 2H), 6.94 (d, J=6.8 Hz, 1H), 6.67 (d, J=6.4 Hz, 1H), 6.37 (d, J=8.4 Hz, 1H), 6.29 (dd, J=7.6, 4.8 Hz, 1H), 3.91 (t, J=7.6 Hz, 4H), 3.84-3.75 (m, 1H), 3.56 (s, 2H), 2.85-2.77 (m, 2H), 2.32-2.24 (m, 2H), 2.19-2.09 (m, 2H), 1.94-1.82 (m, 2H), 1.53-1.43 (m, 2H).

Example 461: 4-((1-(4-(2-(2-Aminopyridin-3-yl)-5-(isoxazol-4-yl)-3H-imidazo[4,5-b]pyridin-3-yl)benzyl)piperidin-4-yl)amino)pyrimidine-2-carbonitrile

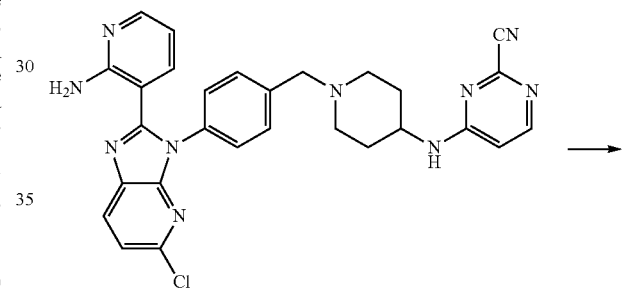

Example 405

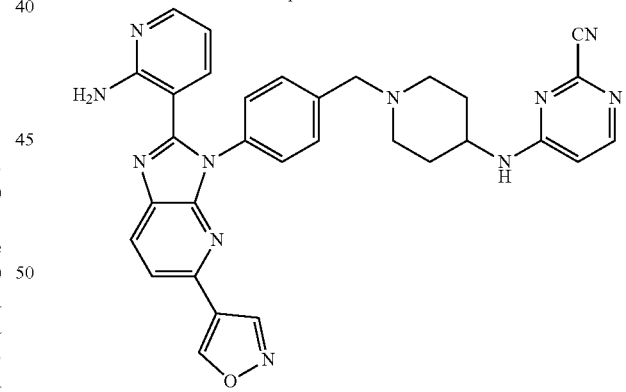

Example 461

A mixture of Example 405 (50 mg, 93.1 μmol), isoxazol-4-ylboronic acid (26.3 mg, 233 μmol), cata CXium A PdG$_3$ (67.8 mg, 93.1 μmol), K$_3$PO$_4$ (59.3 mg, 279 μmol) and PCy$_3$ (13.1 mg, 46.6 μmol) in DMF (2 mL) was degassed and purged with N$_2$ three times, and then was stirred at 80° C. for 3 hr under N$_2$ atmosphere. The reaction mixture was filtered and concentrated. After purified by prep-HPLC (column: Waters xbridge 150×25 mm 10 μm; mobile phase: [water (NH$_4$HCO$_3$)-ACN]; gradient: 40%-70% B over 11 min), 4-((1-(4-(2-(2-aminopyridin-3-yl)-5-(isoxazol-4-yl)-3H- imidazo[4,5-b]pyridin-3-yl)benzyl)piperidin-4-yl)amino)pyrimidine-2-carbonitrile (Example 461, 19.0 mg, yield: 35%) was obtained as a light-yellow lyophilized powder. MS: m/z=570.3 [M+H]⁺. ¹H NMR (400 MHz, Dimethylsulfoxide-d₆) δ 8.14-8.09 (m, 2H), 8.01-7.94 (m, 2H), 7.61-7.38 (m, 6H), 7.32-7.14 (m, 1H), 7.12-7.06 (m, 1H), 7.01 (d, J=6.4 Hz, 2H), 6.68 (d, J=5.6 Hz, 1H), 6.39-6.34 (m, 1H), 4.06-3.77 (m, 3H), 3.09-2.98 (m, 2H), 2.61-2.55 (m, 2H), 2.02-1.94 (m, 2H), 1.63-1.54 (m, 2H).

Example 462: 4-((1-(4-(2-(2-Aminopyridin-3-yl)-5-(oxazol-5-yl)-3H-imidazo[4,5-b]pyridin-3-yl)benzyl)piperidin-4-yl)amino)pyrimidine-2-carbonitrile

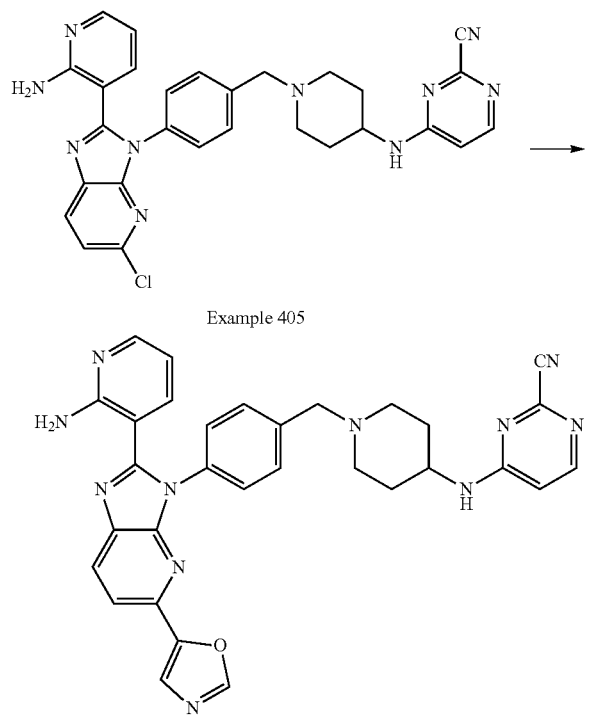

Example 405

Example 462

A mixture of Example 405 (200 mg, 372 μmol), 5-(4,4,5,5-tetramethyl-1,3,2-dioxaborolan-2-yl)-2-(triisopropylsilyl)oxazole (196 mg, 559 μmol), cata CXium A PdG₃ (271 mg, 372 μmol), K₃PO₄ (52.2 mg, 186 μmol) and PCy₃ (237 mg, 1.12 mmol) in DMF (1 mL) was degassed and purged with N₂ three times, and then was stirred at 80° C. for 3 hr under N₂ atmosphere. The reaction mixture was filtered and concentrated. The crude product was purified by prep-HPLC (column: Phenomenex C18 150×25 mm×10 μm; mobile phase: [water (NH₄HCO₃)-ACN]; gradient: 30%-60% B over 10 min). 4-((1-(4-(2-(2-Aminopyridin-3-yl)-5-(oxazol-5-yl)-3H-imidazo[4,5-b]pyridin-3-yl)benzyl)piperidin-4-yl)amino)pyrimidine-2-carbonitrile (Example 462, 14.1 mg, yield: 6.6%) was obtained as a light-yellow lyophilized powder. MS: m/z=570.2 [M+H]⁺. ¹H NMR (400 MHz, Methanol-d4) δ 8.29 (s, 1H), 8.24 (d, J=8.4 Hz, 1H), 8.03-7.97 (m, 2H), 7.86 (d, J=8.4 Hz, 1H), 7.60 (s, 1H), 7.55 (d, J=8.4 Hz, 2H), 7.43 (d, J=8.4 Hz, 2H), 7.31 (dd, J=7.6, 1.6 Hz, 1H), 6.60 (d, J=5.6 Hz, 1H), 6.47 (dd, J=7.6, 5.2 Hz, 1H), 4.06-3.87 (m, 1H), 3.67 (s, 2H), 2.98 (d, J=14.0 Hz, 2H), 2.33-2.25 (m, 2H), 2.02 (d, J=11.2 Hz, 2H), 1.67-1.57 (m, 2H).

Example 463: 4-((1-(4-(2-(2-Aminopyridin-3-yl)-5-(5-methylisoxazol-4-yl)-3H-imidazo[4,5-b]pyridin-3-yl)benzyl)piperidin-4-yl)amino)pyrimidine-2-carbonitrile

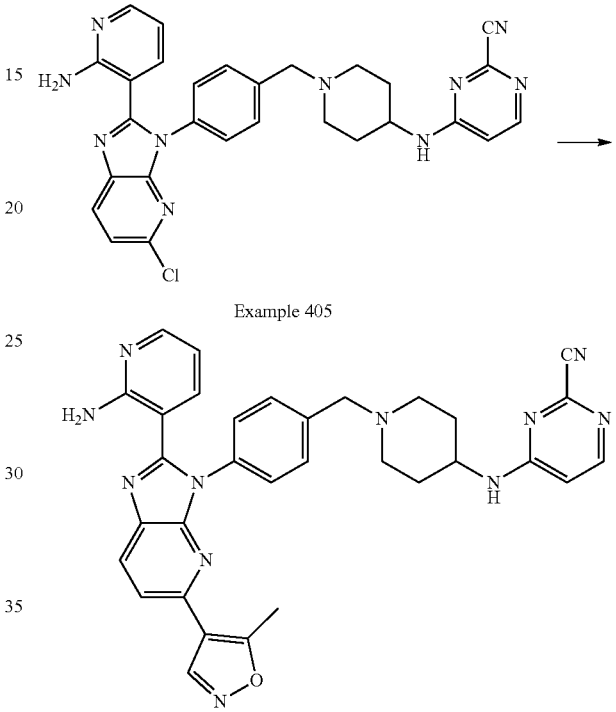

Example 405

Example 463

A mixture of Example 405 (180 mg, 335 μmol), 5-methyl-4-(4,4,5,5-tetramethyl-1,3,2-dioxaborolan-2-yl)isoxazole (140 mg, 670 μmol), cataCXiumAPdG3 (122 mg, 168 μmol), K₃PO₄ (142 mg, 670 μmol) and PCy₃ (9.40 mg, 34 μmol) in DMF (2 mL) was degassed and purged with N₂ three times. The mixture was stirred at 120° C. for 16 hr under N₂ atmosphere. The reaction mixture was poured into H₂O (15 mL), extracted with EtOAc (15 mL×3). The organic phase was dried over anhydrous Na₂SO₄, filtered and concentrated under reduced pressure. After purified by prep-HPLC (column: Waters xbridge 150×25 mm 10 m; mobile phase: [water (NH₄HCO₃)-ACN]; gradient: 32%-62% B over 11 min), 4-((1-(4-(2-(2-aminopyridin-3-yl)-5-(5-methylisoxazol-4-yl)-3H-imidazo[4,5-b]pyridin-3-yl)benzyl)piperidin-4-yl)amino)pyrimidine-2-carbonitrile (Example 463, 20.8 mg, yield: 11%) was obtained as an off white lyophilized powder. MS: m/z=584.3 [M+H]⁺. ¹H NMR (400 MHz, Methanol-d₄) δ8.29 (d, J=8.8 Hz, 1H), 8.11-7.87 (m, 2H), 7.59 (d, J=8.4 Hz, 2H), 7.50 (d, J=8.4 Hz, 1H), 7.42 (d, J=8.4 Hz, 2H), 7.36 (dd, J=8.0, 2.0 Hz, 1H), 6.68-6.52 (m, 1H), 6.46 (dd, J=8.0, 5.2 Hz, 1H), 4.95-4.89 (m, 1H), 4.05-3.80 (m, 1H), 3.69 (s, 2H), 3.05-2.86 (m, 2H), 2.30 (s, 3H), 2.30-2.23 (m, 2H), 2.06-1.97 (m, 2H), 1.68-1.56 (m, 2H).

Example 464: 4-((1-(4-(2-(2-Aminopyridin-3-yl)-5-(3-methylisoxazol-4-yl)-3H-imidazo[4,5-b]pyridin-3-yl)benzyl)piperidin-4-yl)amino)pyrimidine-2-carbonitrile

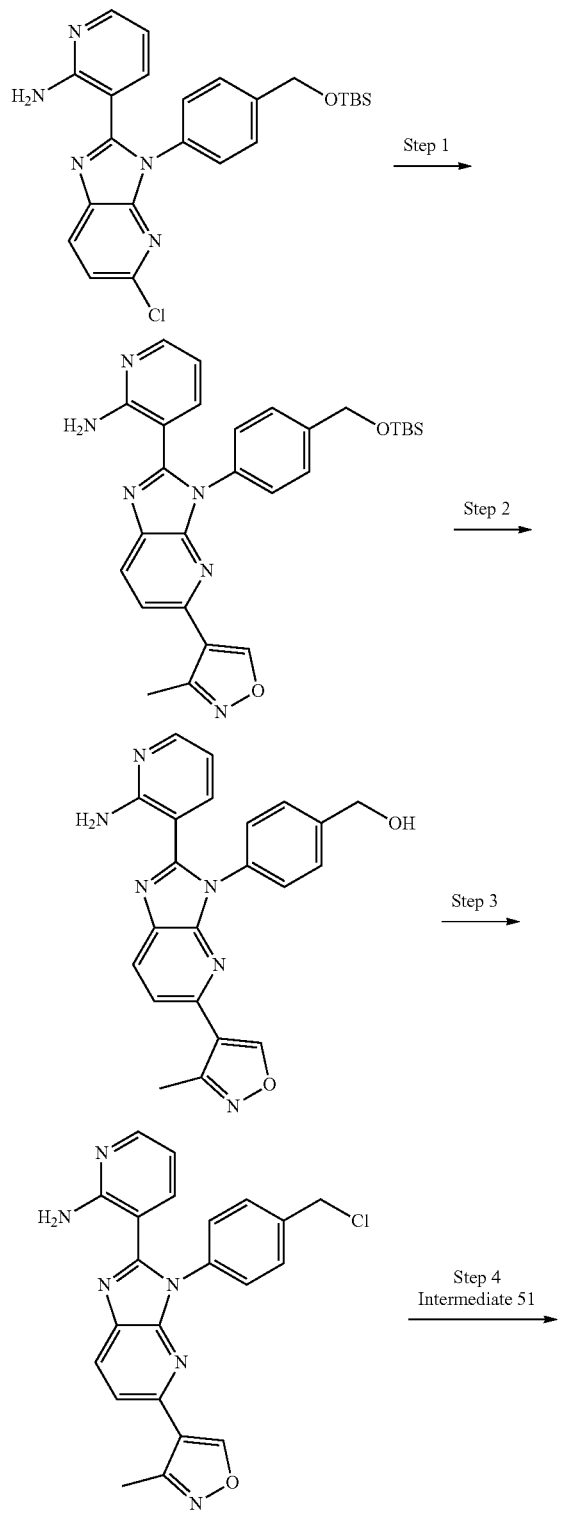

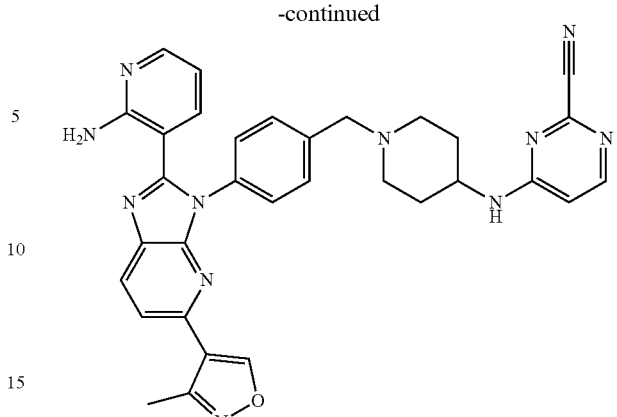

Example 464

Step 1: 3-(3-(4-(((Tert-butyldimethylsilyl)oxy)methyl)phenyl)-5-(3-methylisoxazol-4-yl)-3H-imidazo[4,5-b]pyridin-2-yl)pyridin-2-amine To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 500 mg, 1.07 mmol) and (3-methylisoxazol-4-yl)boronic acid (150 mg, 1.18 mmol) in 1,4-dioxane (10 mL) and H$_2$O (2 mL) were added Pd(dppf)Cl$_2$ (78.5 mg, 107 μmol) and Cs$_2$CO$_3$ (1.05 g, 3.22 mmol). The mixture was degassed and purged with N$_2$ three times, and then was stirred at 100° C. for 16 hr under N$_2$ atmosphere. The reaction mixture was diluted with H$_2$O (100 mL) and extracted with CH$_2$Cl$_2$ (100 mL×2). The combined organic layers were washed with brine (100 mL), dried over Na$_2$SO$_4$, filtered, and concentrated under reduced pressure. After purified by silica gel flash chromatography (Eluent of 20%~50% EtOAc in petroleum ether), 3-(3-(4-(((tert-butyldimethylsilyl)oxy)methyl)phenyl)-5-(3-methylisoxazol-4-yl)-3H-imidazo[4,5-b]pyridin-2-yl)pyridin-2-amine (180 mg, yield: 30%) was obtained as a brown solid. MS: m/z=513.1 [M+H]$^+$. $^1$H NMR (400 MHz, Dimethylsulfoxide-d$_6$) δ 9.47 (s, 1H), 8.27 (d, J=8.4 Hz, 1H), 8.02-7.98 (m, 1H), 7.78 (d, J=8.4 Hz, 1H), 7.50-7.44 (m, 4H), 7.21 (dd, J=7.6, 1.6 Hz, 1H), 7.04 (s, 2H), 6.40 (dd, J=7.6, 4.8 Hz, 1H), 4.81 (s, 2H), 2.38 (s, 3H), 0.91 (s, 9H), 0.09 (s, 6H).

Step 2: (4-(2-(2-Aminopyridin-3-yl)-5-(3-methylisoxazol-4-yl)-3H-imidazo[4,5-b]pyridin-3-yl)phenyl)methanol To a solution of 3-(3-(4-(((tert-butyldimethylsilyl)oxy)methyl)phenyl)-5-(3-methylisoxazol-4-yl)-3H-imidazo[4,5-b]pyridin-2-yl)pyridin-2-amine (180 mg, 351 μmol) in THF (5 mL) was added TBAF (1 M, 0.7 mL). The mixture was stirred at 25° C. for 0.5 hr. The reaction mixture was diluted with H$_2$O (20 mL) and extracted with CH$_2$Cl$_2$ (20 mL×2). The combined organic layers were washed with brine (20 mL×2), dried over Na$_2$SO$_4$, filtered, and concentrated under reduced pressure. (4-(2-(2-Aminopyridin-3-yl)-5-(3-methylisoxazol-4-yl)-3H-imidazo[4,5-b]pyridin-3-yl)phenyl)methanol (110 mg, yield: 79%) was obtained as a yellow solid. MS: m/z=398.9 [M+H]$^+$. $^1$H NMR (400 MHz, Dimethylsulfoxide-d$_6$) δ 9.45 (s, 1H), 8.25 (d, J=8.4 Hz, 1H), 8.00 (dd, J=4.8, 2.0 Hz, 1H), 7.76 (d, J=8.4 Hz, 1H), 7.48-7.41 (m, 4H), 7.21 (dd, J=7.6, 2.0 Hz, 1H), 6.98 (s, 2H), 6.44-6.39 (m, 1H), 5.34 (t, J=5.6 Hz, 1H), 4.58 (d, J=5.2 Hz, 2H), 2.39 (s, 3H).

Step 3: 3-(3-(4-(Chloromethyl)phenyl)-5-(3-methylisoxazol-4-yl)-3H-imidazo[4,5-b]pyridin-2-yl)pyridin-2-amine To a solution of (4-(2-(2-aminopyridin-3-yl)-5-(3-methylisoxazol-4-yl)-3H-imidazo[4,5-b]pyridin-3-yl)phenyl)methanol (110 mg, 276 μmol) in CH₂Cl₂ (2 mL) was added SOCl₂ (98.5 mg, 828 μmol). The mixture was stirred at 40° C. for 0.5 hr. The reaction was concentrated under reduced pressure to give 3-(3-(4-(chloromethyl)phenyl)-5-(3-methylisoxazol-4-yl)-3H-imidazo[4,5-b]pyridin-2-yl)pyridin-2-amine (130 mg, crude) as a yellow solid and used directly in the next step without purification. MS: m/z=417.0 [M+H]⁺.

Step 4: 4-((1-(4-(2-(2-Aminopyridin-3-yl)-5-(3-methylisoxazol-4-yl)-3H-imidazo[4,5-b]pyridin-3-yl)benzyl)piperidin-4-yl)amino)pyrimidine-2-carbonitrile To a solution of 3-(3-(4-(chloromethyl)phenyl)-5-(3-methylisoxazol-4-yl)-3H-imidazo[4,5-b]pyridin-2-yl)pyridin-2-amine (130 mg, 312 μmol) and Intermediate 51 (98.9 mg, 312 μmol, TFA salt) in DMF (2 mL) were added K₂CO₃ (216 mg, 1.56 mmol) and NaI (4.67 mg, 31.2 μmol). The mixture was stirred at 60° C. for 1 hr. After purified by prep-HPLC (column: Waters xbridge 150×25 mm×10 μm; mobile phase: [water (NH₄HCO₃)-ACN]; gradient: 35%-65% B over 10 min), 4-((1-(4-(2-(2-aminopyridin-3-yl)-5-(3-methylisoxazol-4-yl)-3H-imidazo[4,5-b]pyridin-3-yl)benzyl)piperidin-4-yl)amino)pyrimidine-2-carbonitrile (Example 464, 40.7 mg yield: 22% for two steps) was obtained as a yellow solid. MS: m/z=584.4 [M+H]⁺. ¹H NMR (400 MHz, Dimethylsulfoxide-d₆) δ 9.47 (s, 1H), 8.26 (d, J=8.4 Hz, 1H), 8.10-7.98 (m, 3H), 7.77 (d, J=8.4 Hz, 1H), 7.48-7.41 (m, 4H), 7.22 (dd, J=7.6, 1.6 Hz, 1H), 7.08 (s, 2H), 6.66 (d, J=6.0 Hz, 1H), 6.43-6.37 (m, 1H), 3.91-3.72 (m, 1H), 3.57 (s, 2H), 2.82-2.76 (m, 21H) 2.34 (s, 3H), 2.14-2.08 (m, 2H), 1.90-1.83 (m, 2H), 1.51-1.42 (m, 2H).

Example 465: 4-((1-(4-(2-(2-Aminopyridin-3-yl)-5-(3-methyl-1H-pyrazol-5-yl)-3H-imidazo[4,5-b]pyridin-3-yl)benzyl)piperidin-4-yl)amino)pyrimidine-2-carbonitrile

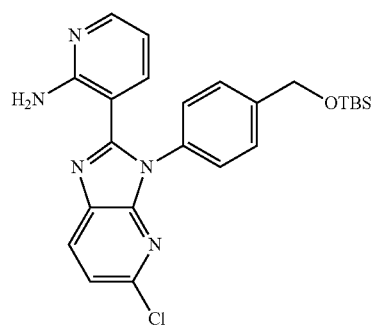

Step 1 →

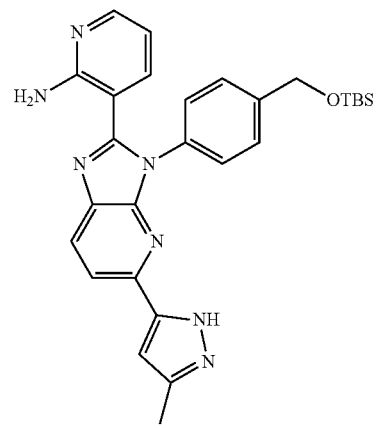

Step 2 →

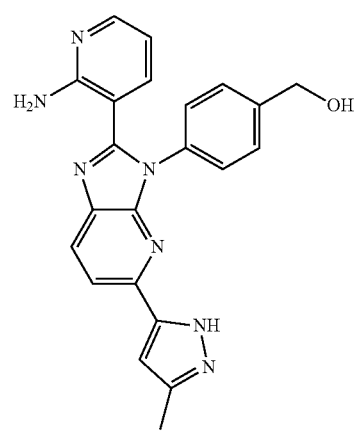

Step 3 →

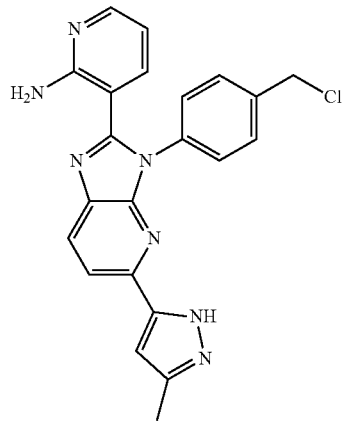

Step 4
Intermediate 51 →

-continued

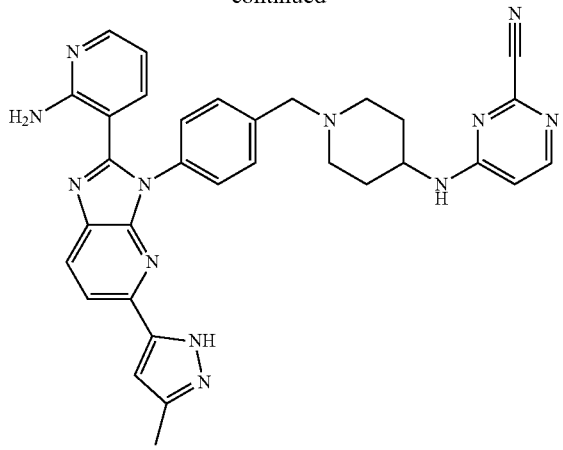

Example 465

Step 1: 3-(3-(4-(((Tert-butyldimethylsilyl)oxy) methyl)phenyl)-5-(3-methyl-1H-pyrazol-5-yl)-3H-imidazo[4,5-b]pyridin-2-yl)pyridin-2-amine To a solution of 3-(3-(4-(((tert-butyldimethylsilyl)oxy) methyl)phenyl)-5-chloro-3H-imidazo[4,5-b]pyridin-2-yl) pyridin-2-amine (refer to Intermediate 117 for detail procedures, 500 mg, 1.07 mmol) and (3-methyl-1H-pyrazol-5-yl) boronic acid (149 mg, 1.18 mmol) in 1,4-dioxane (10 mL) and H$_2$O (2 mL) were added Pd(dppf)Cl$_2$ (78.5 mg, 107 µmol) and Cs$_2$CO$_3$ (1.05 g, 3.22 mmol). The mixture was degassed and purged with N$_2$ three times and stirred at 100° C. for 16 hr under N$_2$ atmosphere. The reaction mixture was diluted with H$_2$O (100 mL) and extracted with CH$_2$Cl$_2$ (100 mL×2). The combined organic layers were washed with brine (100 mL), dried over Na$_2$SO$_4$, filtered and concentrated under reduced pressure. After purified by silica gel flash chromatography (Eluent of 20%~ 70% EtOAc in petroleum ether), 3-(3-(4-(((tert-butyldimethylsilyl)oxy) methyl)phenyl)-5-(3-methyl-1H-pyrazol-5-yl)-3H-imidazo [4,5-b]pyridin-2-yl)pyridin-2-amine (240 mg, yield: 41%) was obtained as a yellow solid. MS: m/z=512.2 [M+H]$^+$. $^1$H NMR (400 MHz, Dimethylsulfoxide-d$_6$) δ 12.64 (s, 1H), 8.17 (d, J=8.4 Hz, 1H), 8.00-7.93 (m, 2H), 7.49-7.43 (m, 4H), 7.18-7.13 (m, 1H), 7.00 (s, 2H), 6.40-6.34 (m, 2H), 4.82 (s, 2H), 2.24 (s, 3H), 0.93 (s, 9H), 0.11 (s, 6H).

Step 2: (4-(2-(2-Aminopyridin-3-yl)-5-(3-methyl-1H-pyrazol-5-yl)-3H-imidazo[4,5-b]pyridin-3-yl) phenyl)methanol To a solution of 3-(3-(4-(((tert-butyldimethylsilyl)oxy) methyl)phenyl)-5-(3-methyl-1H-pyrazol-5-yl)-3H-imidazo [4,5-b]pyridin-2-yl)pyridin-2-amine (240 mg, 469 µmol) in THF (5 m L) was added TBAF (1 M, 0.9 mL). The mixture was stirred at 25° C. for 1 hr. The reaction mixture was diluted with H$_2$O (20 mL) and extracted with CH$_2$Cl$_2$ (20 mL×2). The combined organic layers were washed with brine (20 mL×2), dried over Na$_2$SO$_4$, filtered and concentrated under reduced pressure, (4-(2-(2-aminopyridin-3-yl)-5-(3-methyl-1H-pyrazol-5-yl)-3H-imidazo[4,5-b]pyridin-3-yl)phenyl)methanol (110 mg, yield: 59%) was obtained as a yellow solid. MS: m/z=398.0 [M+H]$^+$. $^1$H NMR (400 MHz, Dimethylsulfoxide-d$_6$) δ 12.64 (s, 1H), 8.22-8.12 (m, 1H), 8.01-7.89 (m, 2H), 7.50-7.40 (m, 4H), 7.19 (dd, J=7.6, 1.6 Hz, 1H), 6.95 (s, 2H), 6.45-6.29 (m, 2H), 5.35 (t, J=5.6 Hz, 1H), 4.60 (d, J=5.6 Hz, 2H), 2.24 (s, 3H).

Step 3: 3-(3-(4-(Chloromethyl)phenyl)-5-(3-methyl-1H-pyrazol-5-yl)-3H-imidazo[4,5-b]pyridin-2-yl) pyridin-2-amine To a solution of (4-(2-(2-aminopyridin-3-yl)-5-(3-methyl-1H-pyrazol-5-yl)-3H-imidazo[4,5-b]pyridin-3-yl)phenyl) methanol (110 mg, 277 µmol) in CH$_2$Cl$_2$ (2 mL) was added SOCl$_2$ (98.8 mg, 830 µmol). The mixture was stirred at 40° C. for 0.5 hr. The reaction was concentrated under reduced pressure, 3-(3-(4-(chloromethyl)phenyl)-5-(3-methyl-1H-pyrazol-5-yl)-3H-imidazo[4,5-b]pyridin-2-yl)pyridin-2-amine (120 mg, crude) was obtained as a yellow solid. MS: m/z=416.0 [M+H]$^+$.

Step 4: 4-((1-(4-(2-(2-Aminopyridin-3-yl)-5-(3-methyl-1H-pyrazol-5-yl)-3H-imidazo[4,5-b]pyridin-3-yl)benzyl)piperidin-4-yl)amino)pyrimidine-2-carbonitrile To a solution of 3-(3-(4-(chloromethyl)phenyl)-5-(3-methyl-1H-pyrazol-5-yl)-3H-imidazo[4,5-b]pyridin-2-yl) pyridin-2-amine (120 mg, 289 µmol) and Intermediate 51 (91.6 mg, 289 µmol, TFA salt) in DMF (2 mL) were added K$_2$CO$_3$ (199 mg, 1.44 mmol) and NaI (4.33 mg, 28.9 µmol). The mixture was stirred at 60° C. for 1 hr. After purified by prep-HPLC (column: Waters xbridge 150×25 mm×10 µm; mobile phase: [water (NH$_4$HCO$_3$)-ACN]; gradient: 27%-57% B over 10 min), 4-((1-(4-(2-(2-aminopyridin-3-yl)-5-(3-methyl-1H-pyrazol-5-yl)-3H-imidazo[4,5-b]pyridin-3-yl)benzyl)piperidin-4-yl)amino)pyrimidine-2-carbonitrile (Example 465, 28.6 mg, yield: 16% for two steps) was obtained as a light yellow solid. MS: m/z=583.3 [M+H]$^+$. $^1$H NMR (400 MHz, Dimethylsulfoxide-d$_6$) δ 12.64 (s, 1H), 8.21-7.92 (m, 5H), 7.52-7.39 (m, 4H), 7.14-7.09 (m, 1H), 6.99 (s, 2H), 6.67 (d, J=5.6 Hz, 1H), 6.48-6.23 (m, 2H), 3.88-3.75 (m, 1H), 3.58 (s, 2H), 2.89-2.80 (m, 2H), 2.24 (s, 3H), 2.17-2.09 (m, 2H), 1.94-1.84 (m, 2H), 1.54-1.45 (m, 2H).

Example 466: 4-((1-(4-(2-(2-Aminopyridin-3-yl)-5-(1-ethyl-1H-pyrazol-4-yl)-3H-imidazo[4,5-b]pyridin-3-yl)benzyl)piperidin-4-yl)amino)pyrimidine-2-carbonitrile

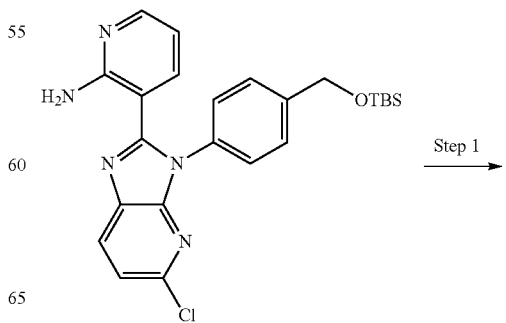

Step 1

1569
-continued

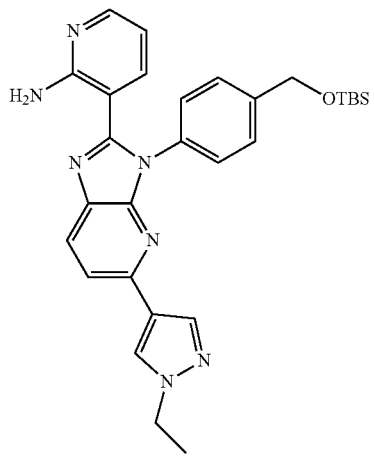

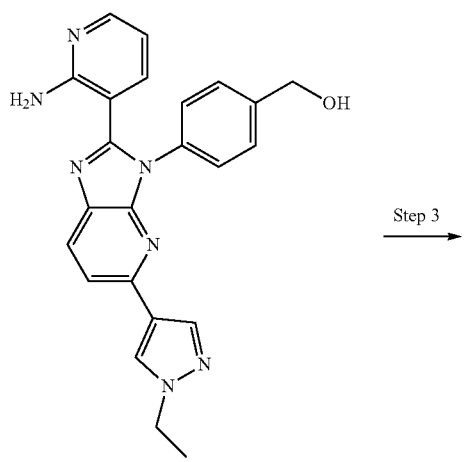

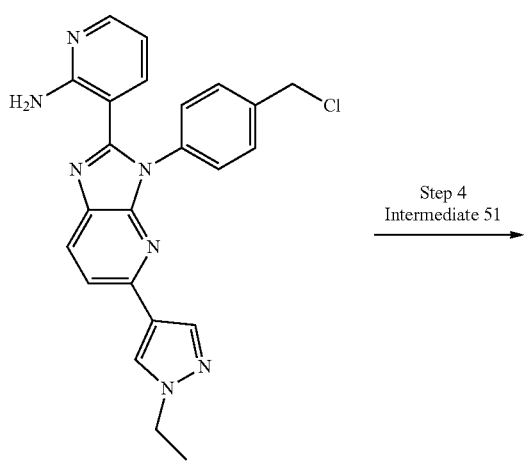

1570
-continued

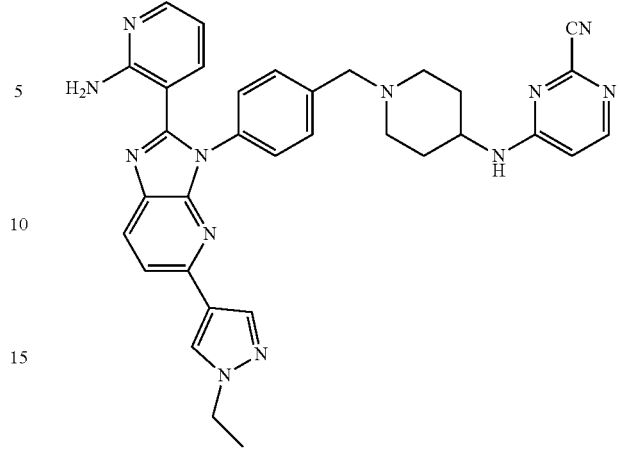

Example 466

Step 1: 3-(3-(4-(((Tert-butyldimethylsilyl)oxy)methyl)phenyl)-5-(1-ethyl-1H-pyrazol-4-yl)-3H-imidazo[4,5-b]pyridin-2-yl)pyridin-2-amine A mixture of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 500 mg, 1.07 mmol), (1-ethyl-1H-pyrazol-4-yl)boronic acid (150 mg, 1.07 mmol), $Cs_2CO_3$ (1.05 g, 3.22 mmol) and $Pd(dppf)Cl_2$ (78.5 mg, 107 μmol) in 1,4-dioxane (5 mL) and $H_2O$ (1 mL) was degassed and purged with $N_2$ three times, and then was stirred at 80° C. for 16 hr under $N_2$ atmosphere. The reaction mixture was diluted with $CH_2Cl_2$ (10 mL) and extracted with $CH_2Cl_2$ (15 mL×3). The combined organic layers were washed with brine (50 mL), dried over $Na_2SO_4$, filtered, and concentrated under reduced pressure. After purified by silica gel flash chromatography (Eluent of 1%~50% EtOAc in petroleum ether), 3-(3-(4-((tert-butyldimethylsilyl)oxy)methyl)phenyl)-5-(1-ethyl-1H-pyrazol-4-yl)-3H-imidazo[4,5-b]pyridin-2-yl)pyridin-2-amine (400 mg, yield: 71%) was obtained as a purple oil. MS: m/z=526.6 $[M+H]^+$. $^1H$ NMR (400 MHz, Dimethylsulfoxide-$d_6$) δ 8.19-8.13 (m, 2H), 7.98 (dd, J=4.8, 1.6 Hz, 1H), 7.92 (s, 1H), 7.68 (d, J=8.0 Hz, 1H), 7.51-7.46 (m, 2H), 7.45-7.39 (m, 2H), 7.13 (dd, J=7.6, 1.6 Hz, 1H), 6.99 (br s, 2H), 6.36 (dd, J=7.6, 4.8 Hz, 1H), 4.82 (s, 2H), 4.15 (q, J=7.2 Hz, 2H), 0.93 (s, 9H), 0.11 (s, 6H).

Step 2: (4-(2-(2-Aminopyridin-3-yl)-5-(1-ethyl-1H-pyrazol-4-yl)-3H-imidazo[4,5-b]pyridin-3-yl)phenyl)methanol To a solution of 3-(3-(4-(((tert-butyldimethylsilyl)oxy)methyl)phenyl)-5-(1-ethyl-1H-pyrazol-4-yl)-3H-imidazo[4,5-b]pyridin-2-yl)pyridin-2-amine (400 mg, 761 μmol) in THF (6 mL) was added TBAF (1.52 mmol, 1 M in THF). The mixture was stirred at 25° C. for 1 hr. The reaction mixture was quenched with $H_2O$ (10 mL) at 25° C., and extracted with $CH_2Cl_2$ (20 mL×3). The combined organic layers were washed with brine (50 mL), dried over $Na_2SO_4$, filtered and concentrated under reduced pressure. After purified by silica gel flash chromatography (Eluent of 1%~80% EtOAc in petroleum ether), (4-(2-(2-aminopyridin-3-yl)-5-(1-ethyl-1H-pyrazol-4-yl)-3H-imidazo[4,5-b]pyridin-3-yl)phenyl)methanol (120 mg, yield: 38%) was obtained as a yellow solid. MS: m/z=412.4 [M+H]⁺. $^1$H NMR (400 MHz, Dimethylsulfoxide-$d_6$) δ 8.20-8.12 (m, 2H), 8.07-7.94 (m, 2H), 7.70 (d, J=8.0 Hz, 1H), 7.52-7.45 (m, 2H), 7.45-7.38 (m, 2H), 7.28-6.84 (m, 3H), 6.51-6.38 (m, 1H), 5.57-5.17 (m, 1H), 4.61 (s, 2H), 4.16 (q, =7.2 Hz, 2H), 1.38 (t, J=7.6 Hz, 3H).

Step 3: 3-(3-(4-(Chloromethyl)phenyl)-5-(1-ethyl-1H-pyrazol-4-yl)-3H-imidazo[4,5-b]pyridin-2-yl)pyridin-2-amine To a solution of (4-(2-(2-aminopyridin-3-yl)-5-(1-ethyl-1H-pyrazol-4-yl)-3H-imidazo[4,5-b]pyridin-3-yl)phenyl)methanol (120 mg, 292 μmol) in CH₂Cl₂ (5 mL) was added SOCl₂ (69.4 mg, 583 μmol) at 0° C. The mixture was stirred at 40° C. for 0.5 hr. The reaction mixture was quenched with H₂O (1 mL) at 25° C., and concentrated under reduced pressure, 3-(3-(4-(chloromethyl)phenyl)-5-(1-ethyl-1H-pyrazol-4-yl)-3H-imidazo[4,5-b]pyridin-2-yl)pyridin-2-amine (136 mg, HCl salt) was obtained as a yellow solid. MS: m/z=430.1 [M+H]⁺.

Step 4: 4-((1-(4-(2-(2-Aminopyridin-3-yl)-5-(1-ethyl-1H-pyrazol-4-yl)-3H-imidazo[4,5-b]pyridin-3-yl)benzyl)piperidin-4-yl)amino)pyrimidine-2-carbonitrile To a solution of 3-(3-(4-(chloromethyl)phenyl)-5-(1-ethyl-1H-pyrazol-4-yl)-3H-imidazo[4,5-b]pyridin-2-yl)pyridin-2-amine (136 mg, 292 μmol, HCl salt) and Intermediate 51 (92.5 mg, 292 μmol, TFA) in DMF (2 mL) were added K₂CO₃ (202 mg, 1.46 mmol) and NaI (8.74 mg, 58.3 μmol). The mixture was stirred at 50° C. for 16 hr. The mixture was filtered through Celite, and the filtrate was concentrated. After purified by prep-HPLC (column: Waters xbridge 150×25 mm×10 μm; mobile phase: [water (NH₃H₂O+NH₄HCO₃)-ACN]; gradient: 32%-62% B over 11 min), 4-((1-(4-(2-(2-aminopyridin-3-yl)-5-(1-ethyl-1H-pyrazol-4-yl)-3H-imidazo[4,5-b]pyridin-3-yl)benzyl)piperidin-4-yl)amino)pyrimidine-2-carbonitrile (Example 466, 39 mg, yield: 24% for two steps) was obtained as a light yellow lyophilized powder. MS: m/z=597.4 [M+H]⁺. $^1$H NMR (400 MHz, Dimethylsulfoxide-$d_6$) δ 8.20-8.13 (m, 2H), 8.02-8.11 (m, 2H), 7.98 (dd, J=4.8, 2.0 Hz, 1H), 7.93 (s, 1H), 7.68 (d, J=8.0 Hz, 1H), 7.50-7.44 (m, 2H), 7.43-7.38 (m, 2H), 7.10 (dd, J=7.6, 1.6 Hz, 1H), 7.01 (br s, 2H), 6.68 (d, J=6.0 Hz, 1H), 6.35 (dd, J=7.6, 4.8 Hz, 1H), 4.15 (q, J=7.2 Hz, 2H), 3.91-3.72 (m, 1H), 3.59 (s, 2H), 2.90-2.79 (m, 2H), 2.22-2.11 (m, 2H), 1.94-1.83 (m, 2H), 1.55-1.45 (m, 2H), 1.37 (t, J=7.6 Hz, 3H).

Example 467: 4-((1-(4-(2-(2-Aminopyridin-3-yl)-5-(1-methyl-1H-pyrazol-5-yl)-3H-imidazo[4,5-b]pyridin-3-yl)benzyl)piperidin-4-yl)amino)pyrimidine-2-carbonitrile

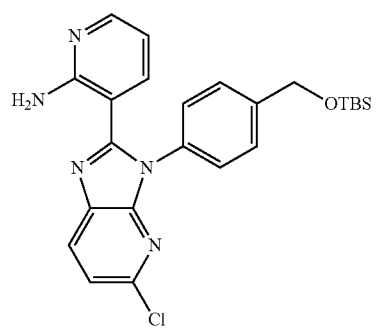

Step 1 →

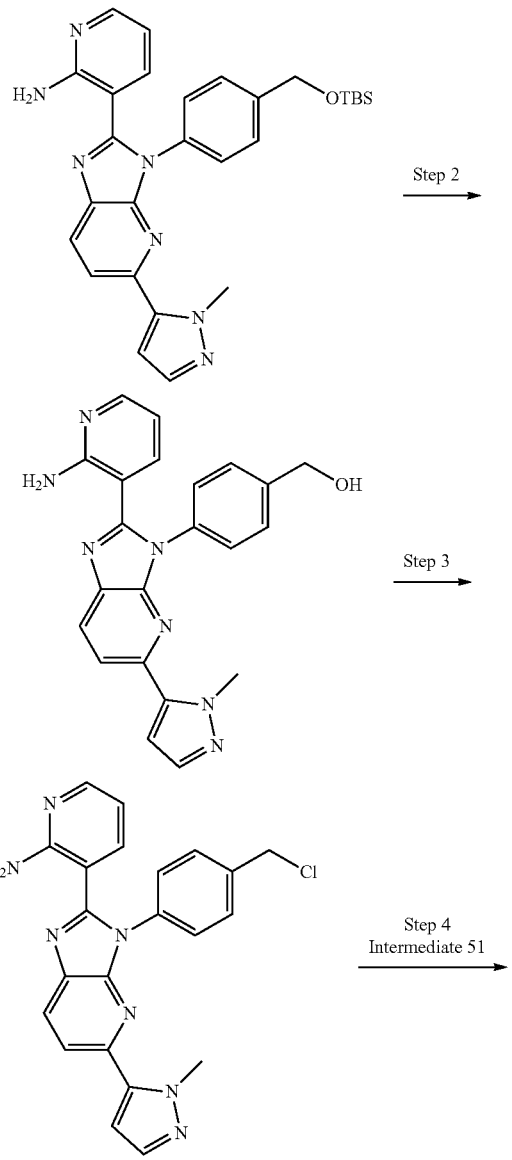

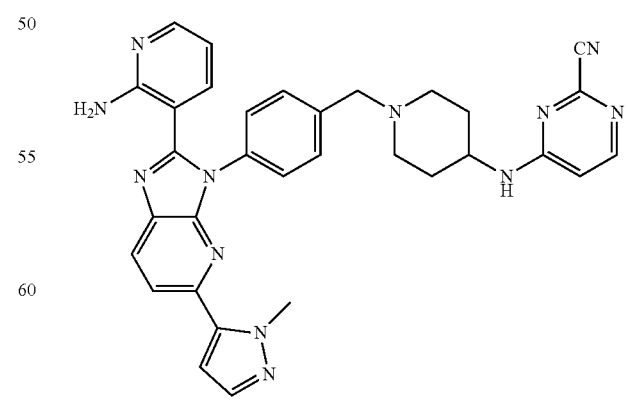

Example 467

Step 1: 3-(3-(4-(((Tert-butyldimethylsilyl)oxy) methyl)phenyl)-5-(1-methyl-1H-pyrazol-5-yl)-3H-imidazo[4,5-b]pyridin-2-yl)pyridin-2-amine To a solution of 3-(3-(4-(((tert-butyldimethylsilyl)oxy) methyl)phenyl)-5-chloro-3H-imidazo[4,5-b]pyridin-2-yl) pyridin-2-amine (refer to Intermediate 117 for detail procedures, 500 mg, 1 mmol) in 1,4-dioxane (5 mL) were added H$_2$O (1 mL), K$_2$CO$_3$ (445 mg, 3.2 mmol), (1-methyl-1H-pyrazol-5-yl)boronic acid (135 mg, 1 mmol) and Pd(dppf)Cl$_2$ (78 mg, 107 μmol) at 25° C. The mixture was degassed and purged with N$_2$ three times. The mixture was stirred at 85° C. for 12 hr under N$_2$. The reaction mixture was poured into H$_2$O (50 mL) and extracted with CH$_2$Cl$_2$ (20 mL×2). The combined organic layers were washed with brine (40 mL), dried over anhydrous Na$_2$SO$_4$, filtered and concentrated. After purified by silica gel flash chromatography (Eluent of 0~40% EtOAc in petroleum ether), 3-(3-(4-(((tert-butyldimethylsilyl)oxy)methyl)phenyl)-5-(1-methyl-1H-pyrazol-5-yl)-3H-imidazo[4,5-b]pyridin-2-yl)pyridin-2-amine (300 mg, yield: 46%) was obtained as a yellow solid. MS: m/z=512.3 [M+H]$^+$. $^1$H NMR (400 MHz, Dimethylsulfoxide-d$_6$) δ 8.28 (d, J=8.4 Hz, 1H), 8.01 (dd, J=4.8, 1.6 Hz, 1H), 7.81 (d, J=8.4 Hz, 1H), 7.48-7.46 (m, 5H), 7.23 (dd, J=7.6, 1.6 Hz, 1H), 7.04 (s, 2H), 6.83 (d, J=2.0 Hz, 1H), 6.40 (dd, J=8.0, 4.8 Hz, 1H), 4.80 (s, 2H), 3.98 (s, 3H), 0.91 (s, 9H), 0.09 (s, 6H).

Step 2: (4-(2-(2-Aminopyridin-3-yl)-5-(1-methyl-1H-pyrazol-5-yl)-3H-imidazo[4,5-b]pyridin-3-yl)phenyl)methanol To a solution of 3-(3-(4-(((tert-butyldimethylsilyl)oxy) methyl)phenyl)-5-(1-methyl-1H-pyrazol-5-yl)-3H-imidazo[4,5-b]pyridin-2-yl)pyridin-2-amine (300 mg, 586 μmol) in THF (5 mL) was added TBAF (1.8 mL, 1M) at 25° C. The mixture was stirred at 25° C. for 1 hr. The reaction mixture was poured into H$_2$O (20 mL). The mixture was extracted with CH$_2$Cl$_2$ (20 mL×2). The combined organic layers were washed with brine (40 mL), dried over anhydrous Na$_2$SO$_4$, filtered and concentrated, (4-(2-(2-aminopyridin-3-yl)-5-(1-methyl-1H-pyrazol-5-yl)-3H-imidazo[4,5-b]pyridin-3-yl) phenyl)methanol (220 mg, crude) was obtained as a yellow solid. MS: m/z=398.4 [M+H]$^+$. $^1$H NMR (400 MHz, Dimethylsulfoxide-d$_6$) δ 8.28 (d, J=8.0 Hz, 1H), 8.01 (dd, J=4.8, 2.0 Hz, 1H), 7.80 (d, J=8.4 Hz, 1H), 7.49-7.43 (m, 5H), 7.24 (dd, J=8.0, 2.0 Hz, 1H), 6.99 (s, 2H), 6.82 (d, J=2.0 Hz, 1H), 6.43 (dd, J=8.0, 5.2 Hz, 1H), 5.42-5.29 (m, 1H), 4.59 (s, 2H), 4.01 (s, 3H).

Step 3: 3-(3-(4-(Chloromethyl)phenyl)-5-(1-methyl-1H-pyrazol-5-yl)-3H-imidazo[4,5-b]pyridin-2-yl)pyridin-2-amine To a solution of (4-(2-(2-aminopyridin-3-yl)-5-(1-methyl-1H-pyrazol-5-yl)-3H-imidazo[4,5-b]pyridin-3-yl)phenyl) methanol (200 mg, 503 μmol) in CH$_2$Cl$_2$ (5 mL) was added SOCl$_2$ (299 mg, 2.5 mmol) at 25° C., the mixture was stirred at 40° C. for 0.5 hr. The reaction mixture was concentrated under reduced pressure, 3-(3-(4-(chloromethyl)phenyl)-5-(1-methyl-1H-pyrazol-5-yl)-3H-imidazo[4,5-b]pyridin-2-yl)pyridin-2-amine (200 mg, yield: 90% for 2 steps) was obtained as a yellow solid, which was used in the next step without further purification. MS: m/z=415.9 [M+H]$^+$. $^1$H NMR (400 MHz, Dimethylsulfoxide-d$_6$) δ 8.56-8.46 (m, 1H), 8.38 (d, J=8.4 Hz, 1H), 8.16 (dd, J=6.4, 1.2 Hz, 1H), 7.94-7.87 (m, 2H), 7.66-7.58 (m, 5H), 7.49 (d, J=2.0 Hz, 1H), 6.92 (dd, J=7.2, 6.4 Hz, 1H), 6.88 (d, J=2.0 Hz, 1H), 4.86 (s, 2H), 4.02 (s, 3H).

Step 4: 4-((1-(4-(2-(2-Aminopyridin-3-yl)-5-(1-methyl-1H-pyrazol-5-yl)-3H-imidazo[4,5-b]pyridin-3-yl)benzyl)piperidin-4-yl)amino)pyrimidine-2-carbonitrile To a solution of 3-(3-(4-(chloromethyl)phenyl)-5-(1-methyl-1H-pyrazol-5-yl)-3H-imidazo[4,5-b]pyridin-2-yl) pyridin-2-amine (100 mg, 240 μmol) in DMF (3 mL) were added Intermediate 51 (59 mg, 289 μmol), NaI (36 mg, 240 μmol) and K$_2$CO$_3$ (133 mg, 962 μmol) at 25° C., the mixture was stirred at 50° C. for 1 hr. The reaction mixture was poured into H$_2$O (50 mL) and extracted with CH$_2$Cl$_2$ (20 mL×2). The combined organic layers were washed with brine (40 mL), dried over anhydrous Na$_2$SO$_4$, filtered and concentrated. After purified by silica gel flash chromatography (Eluent of 0~6% MeOH in CH$_2$Cl$_2$), 4-((1-(4-(2-(2-aminopyridin-3-yl)-5-(1-methyl-1H-pyrazol-5-yl)-3H-imidazo[4,5-b]pyridin-3-yl)benzyl)piperidin-4-yl)amino) pyrimidine-2-carbonitrile (Example 467, 46.5 mg, yield: 32%) was obtained as a yellow solid. MS: m/z=583.4 [M+H]$^+$. $^1$H NMR (400 MHz, Dimethylsulfoxide-d$_6$) δ 8.29 (d, J=8.4 Hz, 1H), 8.13-7.98 (m, 3H), 7.81 (d, J=8.4 Hz, 1H), 7.51-7.40 (m, 5H), 7.23 (dd, J=7.2, 1.6 Hz, 1H), 7.08 (s, 2H), 6.84 (d, J=2.0 Hz, 1H), 6.67 (d, J=6.0 Hz, 1H), 6.41 (dd, J=7.6, 4.8 Hz, 1H), 3.98 (s, 3H), 3.88-3.74 (m, 1H), 3.63-3.57 (m, 2H), 2.86-2.74 (m, 2H), 2.21-2.07 (m, 2H), 1.92-1.85 (m, 2H), 1.55-1.44 (m, 2H).

Example 468: 4-((1-(4-(2-(2-Aminopyridin-3-yl)-5-(3-(2-oxopyrrolidin-1-yl)phenyl)-3H-imidazo[4,5-b]pyridin-3-yl)benzyl)piperidin-4-yl)amino)pyrimidine-2-carbonitrile

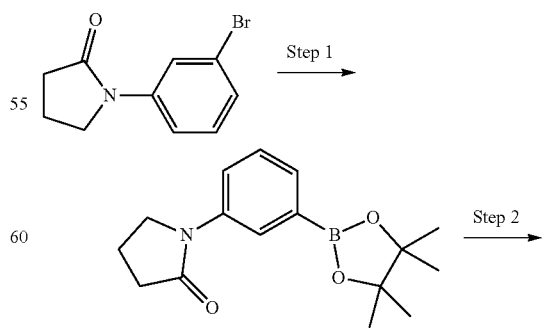

1575
-continued

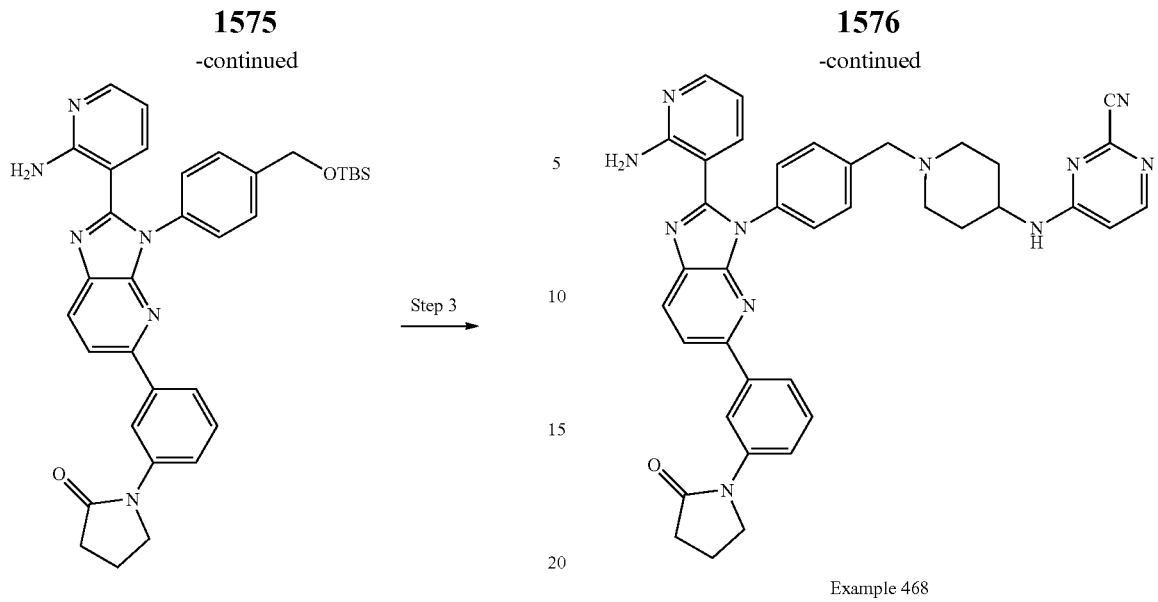

1576
-continued

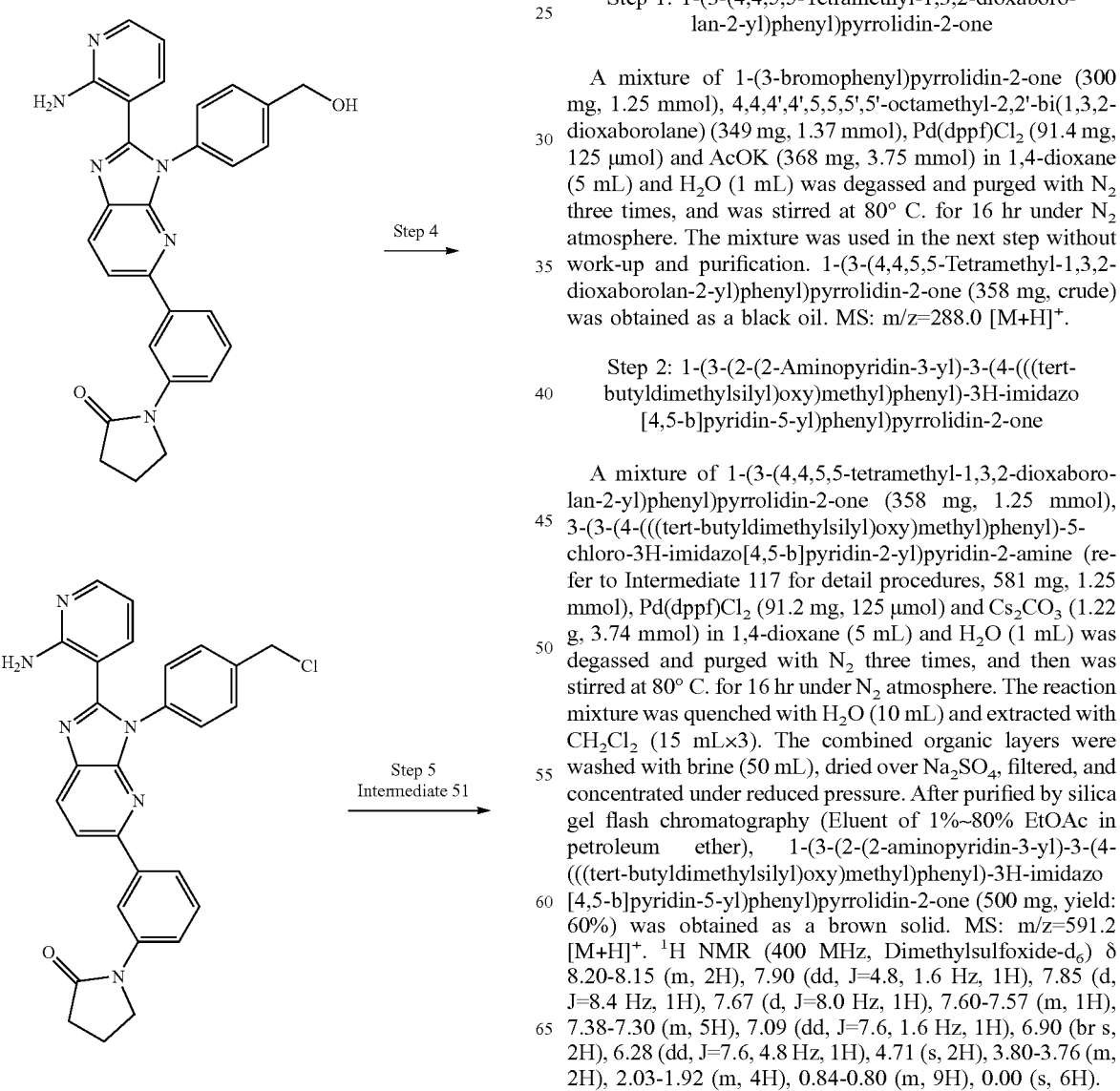

Example 468

Step 1: 1-(3-(4,4,5,5-Tetramethyl-1,3,2-dioxaborolan-2-yl)phenyl)pyrrolidin-2-one A mixture of 1-(3-bromophenyl)pyrrolidin-2-one (300 mg, 1.25 mmol), 4,4,4',4',5,5,5',5'-octamethyl-2,2'-bi(1,3,2-dioxaborolane) (349 mg, 1.37 mmol), Pd(dppf)Cl$_2$ (91.4 mg, 125 μmol) and AcOK (368 mg, 3.75 mmol) in 1,4-dioxane (5 mL) and H$_2$O (1 mL) was degassed and purged with N$_2$ three times, and was stirred at 80° C. for 16 hr under N$_2$ atmosphere. The mixture was used in the next step without work-up and purification. 1-(3-(4,4,5,5-Tetramethyl-1,3,2-dioxaborolan-2-yl)phenyl)pyrrolidin-2-one (358 mg, crude) was obtained as a black oil. MS: m/z=288.0 [M+H]$^+$.

Step 2: 1-(3-(2-(2-Aminopyridin-3-yl)-3-(4-(((tert-butyldimethylsilyl)oxy)methyl)phenyl)-3H-imidazo[4,5-b]pyridin-5-yl)phenyl)pyrrolidin-2-one A mixture of 1-(3-(4,4,5,5-tetramethyl-1,3,2-dioxaborolan-2-yl)phenyl)pyrrolidin-2-one (358 mg, 1.25 mmol), 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 581 mg, 1.25 mmol), Pd(dppf)Cl$_2$ (91.2 mg, 125 μmol) and Cs$_2$CO$_3$ (1.22 g, 3.74 mmol) in 1,4-dioxane (5 mL) and H$_2$O (1 mL) was degassed and purged with N$_2$ three times, and then was stirred at 80° C. for 16 hr under N$_2$ atmosphere. The reaction mixture was quenched with H$_2$O (10 mL) and extracted with CH$_2$Cl$_2$ (15 mL×3). The combined organic layers were washed with brine (50 mL), dried over Na$_2$SO$_4$, filtered, and concentrated under reduced pressure. After purified by silica gel flash chromatography (Eluent of 1%~80% EtOAc in petroleum ether), 1-(3-(2-(2-aminopyridin-3-yl)-3-(4-(((tert-butyldimethylsilyl)oxy)methyl)phenyl)-3H-imidazo[4,5-b]pyridin-5-yl)phenyl)pyrrolidin-2-one (500 mg, yield: 60%) was obtained as a brown solid. MS: m/z=591.2 [M+H]$^+$. $^1$H NMR (400 MHz, Dimethylsulfoxide-d$_6$) δ 8.20-8.15 (m, 2H), 7.90 (dd, J=4.8, 1.6 Hz, 1H), 7.85 (d, J=8.4 Hz, 1H), 7.67 (d, J=8.0 Hz, 1H), 7.60-7.57 (m, 1H), 7.38-7.30 (m, 5H), 7.09 (dd, J=7.6, 1.6 Hz, 1H), 6.90 (br s, 2H), 6.28 (dd, J=7.6, 4.8 Hz, 1H), 4.71 (s, 2H), 3.80-3.76 (m, 2H), 2.03-1.92 (m, 4H), 0.84-0.80 (m, 9H), 0.00 (s, 6H).

Step 3: 1-(3-(2-(2-Aminopyridin-3-yl)-3-(4-(hydroxymethyl)phenyl)-3H-imidazo[4,5-b]pyridin-5-yl)phenyl)pyrrolidin-2-one To a solution of 1-(3-(2-(2-aminopyridin-3-yl)-3-(4-(((tert-butyldimethylsilyl)oxy)methyl)phenyl)-3H-imidazo[4,5-b]pyridin-5-yl)phenyl)pyrrolidin-2-one (600 mg, 1.02 mmol) in THF (5 mL) was added TBAF (2.03 mmol, 1 M). The mixture was stirred at 25° C. for 1 hr. The reaction mixture was quenched with H₂O (10 mL) at 25° C., and extracted with CH₂Cl₂ (20 mL×3). The combined organic layers were washed with brine (50 mL), dried over Na₂SO₄, filtered and concentrated under reduced pressure. After purified by silica gel flash chromatography (Eluent of 1%~100% EtOAc in petroleum ether), 1-(3-(2-(2-aminopyridin-3-yl)-3-(4-(hydroxymethyl)phenyl)-3H-imidazo[4,5-b]pyridin-5-yl)phenyl)pyrrolidin-2-one (200 mg, yield: 40%) was obtained as a yellow solid. MS: m/z=477.1 [M+H]⁺.

Step 4: 1-(3-(2-(2-Aminopyridin-3-yl)-3-(4-(chloromethyl)phenyl)-3H-imidazo[4,5-b]pyridin-5-yl)phenyl)pyrrolidin-2-one To a solution of 1-(3-(2-(2-Aminopyridin-3-yl)-3-(4-(hydroxymethyl)phenyl)-3H-imidazo[4,5-b]pyridin-5-yl)phenyl)pyrrolidin-2-one (230 mg, 483 μmol) in CH₂Cl₂ (5 mL) was added SOCl₂ (115 mg, 965 μmol) at 0° C. The mixture was stirred at 40° C. for 0.5 hr. The reaction mixture was quenched with H₂O (1 mL) at 25° C. and concentrated under reduced pressure to give a residue. And the reaction mixture was diluted with aqueous Na₂CO₃ (10 mL) and extracted with CH₂Cl₂ (15 mL×2). The combined organic layers were washed with brine (15 mL), dried over Na₂SO₄, filtered and concentrated under reduced pressure, 1-(3-(2-(2-aminopyridin-3-yl)-3-(4-(chloromethyl)phenyl)-3H-imidazo[4,5-b]pyridin-5-yl)phenyl)pyrrolidin-2-one (180 mg) was obtained as a yellow solid. MS: m/z=495.0 [M+H]⁺. ¹H NMR (400 MHz, Dimethylsulfoxide-d₆) δ 8.32-8.26 (m, 2H), 8.02 (dd, J=4.8, 1.6 Hz, 1H), 7.97 (d, J=8.4 Hz, 1H), 7.79 (d, J=8.0 Hz, 1H), 7.71 (dd, J=8.0, 1.2 Hz, 1H), 7.64-7.59 (m, 2H), 7.56-7.52 (m, 2H), 7.49-7.43 (m, 1H), 7.32 (d, J=7.6 Hz, 1H), 7.08 (br s, 2H), 6.52-6.47 (m, 1H), 4.87 (s, 2H), 3.89 (t, J=7.2 Hz, 2H), 2.55-2.52 (m, 2H), 2.11-2.07 (m, 2H).

Step 5: 4-((1-(4-(2-(2-Aminopyridin-3-yl)-5-(3-(2-oxopyrrolidin-1-yl)phenyl)-3H-imidazo[4,5-b]pyridin-3-yl)benzyl)piperidin-4-yl)amino)pyrimidine-2-carbonitrile To a solution of 1-(3-(2-(2-aminopyridin-3-yl)-3-(4-(chloromethyl)phenyl)-3H-imidazo[4,5-b]pyridin-5-yl)phenyl)pyrrolidin-2-one (180 mg, 364 μmol) and Intermediate 51 (115 mg, 364 mol) in DMF (5 mL) were added K₂CO₃ (151 mg, 1.09 mmol) and NaI (10.9 mg, 72.7 gmol). The mixture was stirred at 50° C. for 16 hr. The mixture was filtered through Celite, and the filtrate was concentrated. After purified by prep-HPLC (column: Waters xbridge 150×25 mm×10 μm; mobile phase: [water (NH₃H₂O+NH₄HCO₃)-ACN]; gradient: 37%-67% B over 11 min), 4-((1-(4-(2-(2-aminopyridin-3-yl)-5-(3-(2-oxopyrrolidin-1-yl)phenyl)-3H-imidazo[4,5-b]pyridin-3-yl)benzyl)piperidin-4-yl)amino)pyrimidine-2-carbonitrile (Example 468, 41.8 mg, yield: 17% for two steps) was obtained as a light-yellow lyophilized powder. MS: m/z=662.4 [M+H]⁺. ¹H NMR (400 MHz, Dimethylsulfoxide-d₆) δ 8.30-8.26 (m, 2H), 8.09-8.05 (m, 2H), 8.00 (dd, J=4.8, 1.6 Hz, 1H), 7.97 (d, J=8.4 Hz, 1H), 7.79 (d, J=8.0 Hz, 1H), 7.69 (dd, J=8.0, 1.2 Hz, 1H), 7.49-7.42 (m, 5H), 7.18 (dd, J=7.6, 2.0 Hz, 1H), 7.04 (br s, 2H), 6.68 (br d, J=6.0 Hz, 1H), 6.39 (dd, J=8.0, 5.2 Hz, 1H), 3.87-3.75 (m, 3H), 3.59 (s, 2H), 2.86-2.78 (m, 2H), 2.49-2.47 (m, 2H), 2.21-2.12 (m, 2H), 2.10-2.04 (m, 2H), 1.95-1.86 (m, 2H), 1.59-1.48 (m, 2H).

Example 469: 4-((1-(4-(2-(2-Aminopyridin-3-yl)-5-(4-fluoro-2-methoxyphenyl)-3H-imidazo[4,5-b]pyridin-3-yl)benzyl)piperidin-4-yl)amino)pyrimidine-2-carbonitrile

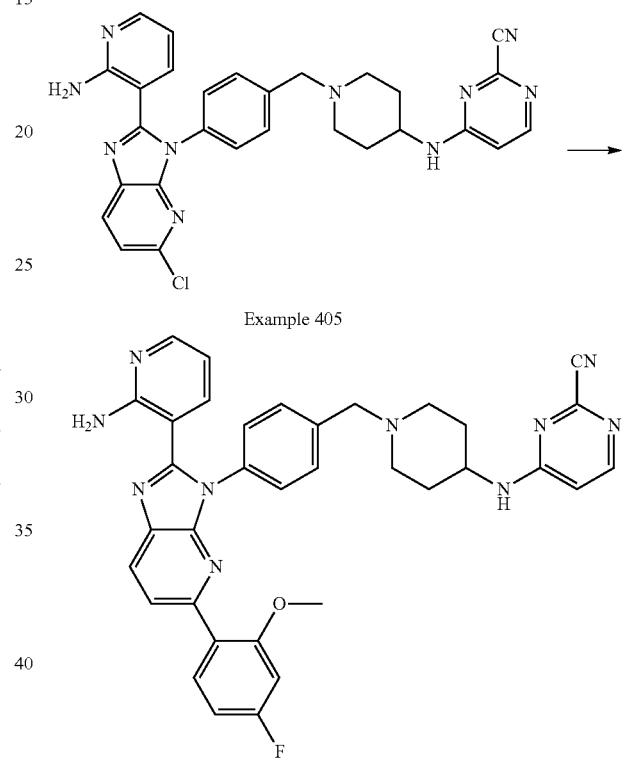

Example 405

Example 469

A mixture of Example 405 (200 mg, 372 μmol), (4-fluoro-2-methoxyphenyl)boronic acid (63.3 mg, 372 μmol), Cs₂CO₃ (364 mg, 1.12 mmol), Pd(dppf)Cl₂ (54.5 mg, 74.5 μmol) in 1,4-dioxane (2.5 mL) and H₂O (0.5 mL) were degassed and purged with N₂ three times, and then was stirred at 80° C. for 16 hr under N₂ atmosphere. The reaction mixture was filtered and concentrated under reduced pressure. After purified by prep-HPLC (column: Waters xbridge 150×25 mm 10 μm; mobile phase: [water (NH₄HCO₃)-ACN]; gradient: 44%-64% B over 11 min), 4-((1-(4-(2-(2-aminopyridin-3-yl)-5-(4-fluoro-2-methoxyphenyl)-3H-imidazo[4,5-b]pyridin-3-yl)benzyl)piperidin-4-yl)amino)pyrimidine-2-carbonitrile (Example 469, 37.4 mg, yield: 15%) was obtained as a light yellow lyophilized powder. MS: m/z=627.5 [M+H]⁺. ¹H NMR (400 MHz, Methanol-d₄) δ8.13 (d, J=8.4 Hz, 1H), 8.05-7.95 (m, 2H), 7.88 (d, J=8.4 Hz, 1H), 7.71-7.67 (m, 1H), 7.52 (d, J=8.4 Hz, 2H), 7.43 (d, J=8.4 Hz, 2H), 7.32 (dd, J=8.0, 2.0 Hz, 1H), 6.90 (dd, J=11.2, 2.4 Hz, 1H), 6.73 (td, J=16.0, 2.4 Hz, 1H), 6.60-6.58 (m, 1H), 6.47 (dd, J=7.6, 4.8 Hz, 1H), 3.99-3.91 (m, 1H), 3.88 (s, 3H), 3.65 (s, 2H), 2.97-2.91 (m, 2H), 2.34-2.20 (m, 2H), 2.07-1.93 (m, 2H), 1.68-1.55 (m, 2H). $^{19}$F NMR (400 MHz, Methanol-d$_4$) δ −112.4.

Example 470: 4-((1-(4-(2-(2-Aminopyridin-3-yl)-5-(2-(trifluoromethyl)phenyl)-3H-imidazo[4,5-b]pyridin-3-yl)benzyl)piperidin-4-yl)amino)pyrimidine-2-carbonitrile

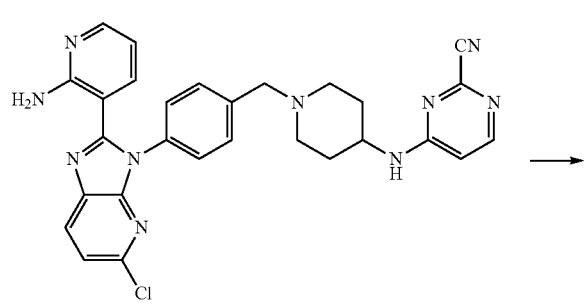

Example 405

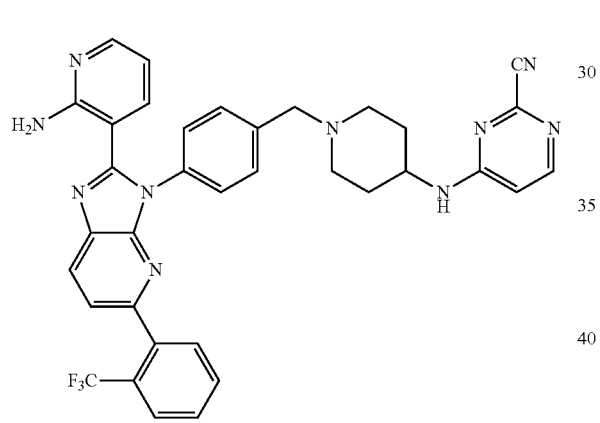

Example 470

A mixture of Example 405 (200 mg, 372 gmol), (2-(trifluoromethyl)phenyl)boronic acid (70.7 mg, 372 μmol), Cs$_2$CO$_3$ (364 mg, 1.12 mmol), and Pd(dppf)Cl$_2$ (54.5 mg, 74.5 μmol) in 1,4-dioxane (2.5 mL) and H$_2$O (0.5 mL) were degassed and purged with N$_2$ three times, and then was stirred at 80° C. for 16 hr under N$_2$ atmosphere. The reaction mixture was filtered and concentrated under reduced pressure. After purified by prep-HPLC (column: Waters xbridge 150×25 mm 10 μm; mobile phase: [water (NH$_3$H$_2$O)-ACN]; gradient: 47%-77% B over 15 min), 4-((1-(4-(2-(2-Aminopyridin-3-yl)-5-(2-(trifluoromethyl)phenyl)-3H-imidazo[4,5-b]pyridin-3-yl)benzyl)piperidin-4-yl)amino)pyrimidine-2-carbonitrile (Example 470, 64.1 mg, yield: 26%) was obtained as a gray lyophilized powder. MS: m/z=647.3 [M+H]$^+$. $^1$H NMR (400 MHz, Dimethylsulfoxide-d$_6$) δ 8.30 (d, J=8.4 Hz, 1H), 8.11-7.97 (m, 3H), 7.84 (d, J=7.6 Hz, 1H), 7.77-7.72 (m, 1H), 7.67-7.62 (m, 1H), 7.57 (d, J=8.0 Hz, 1H), 7.51 (d, J=8.4 Hz, 1H), 7.39 (q, J=8.4 Hz, 4H), 7.17 (dd, J=7.6, 1.6 Hz, 1H), 7.02 (br s, 2H), 6.66 (br d, J=6.0 Hz, 1H), 6.38 (dd, J=7.6, 4.4 Hz, 1H), 3.86-3.72 (m, 1H), 3.53 (s, 2H), 2.78 (br d, J=10.4 Hz, 2H), 2.16-2.07 (m, 2H), 1.90-1.80 (m, 2H), 1.48-1.44 (m, 2H). $^{19}$F NMR (400 MHz, Dimethylsulfoxide-d$_6$) δ −55.4.

Example 471: 4-((1-(4-(2-(2-Aminopyridin-3-yl)-5-(4-(trifluoromethyl)phenyl)-3H-imidazo[4,5-b]pyridin-3-yl)benzyl)piperidin-4-yl)amino)pyrimidine-2-carbonitrile

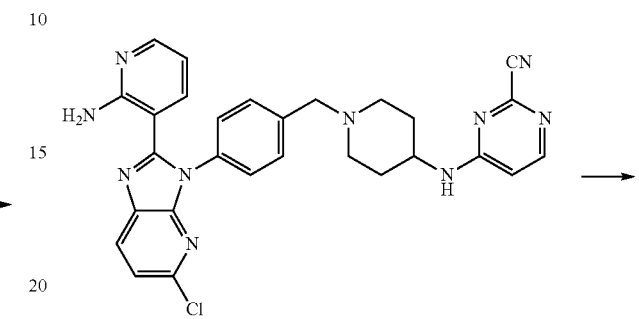

Example 405

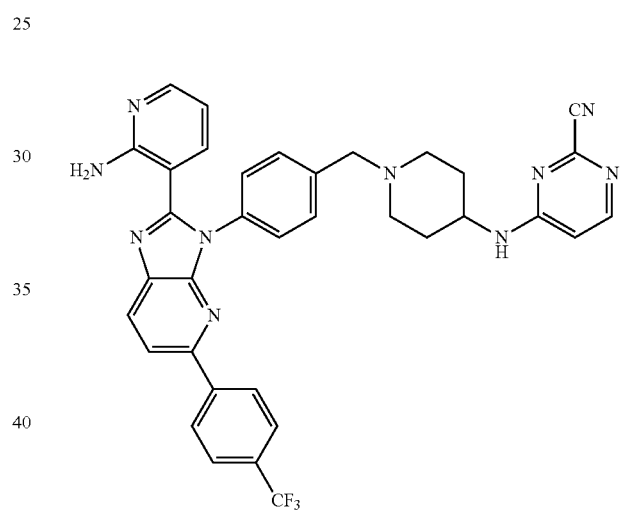

Example 471

A mixture of Example 405 (200 mg, 372 μmol), (4-(trifluoromethyl)phenyl)boronic acid (70.7 mg, 372 μmol), Cs$_2$CO$_3$ (364 mg, 1.12 mmol), and Pd(dppf)Cl2 (54.5 mg, 74.5 μmol) in 1,4-dioxane (2.5 mL) and H$_2$O (0.5 mL) were degassed and purged with N$_2$ three times, and then was stirred at 80° C. for 16 hr under N$_2$ atmosphere. The reaction mixture was filtered and concentrated under reduced pressure. After purified by prep-HPLC (column: Waters Xbridge 150×25 mm×5 μm; mobile phase: [water (NH$_3$H$_2$O+ NH$_4$HCO$_3$)-ACN]; gradient: 57%-87% B over 11 min), 4-((1-(4-(2-(2-aminopyridin-3-yl)-5-(4-(trifluoromethyl)phenyl)-3H-imidazo[4,5-b]pyridin-3-yl)benzyl)piperidin-4-yl)amino)pyrimidine-2-carbonitrile (Example 471, 38.1 mg, yield: 15%) was obtained as a gray lyophilized powder. MS: m/z=647.3 [M+H]$^+$. $^1$H NMR (400 MHz, Dimethylsulfoxide-d$_6$) δ 8.36-8.21 (m, 3H), 8.12-7.96 (m, 4H), 7.84-7.80 (m, 2H), 7.47 (br s, 4H), 7.16-7.14 (m, 1H), 7.03 (s, 2H), 6.67 (br s, 1H), 6.38 (br s, 1H), 3.88-3.74 (m, 1H), 3.59 (br s, 2H), 2.82-2.81 (m, 2H), 2.15-2.14 (m, 2H), 1.89-1.87 (m, 2H), 1.51-1.41 (m, 2H). $^{19}$F NMR (400 MHz, Dimethylsulfoxide-d$_6$) δ −61.0.

Example 472: 4-((1-(4-(2-(2-Aminopyridin-3-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile Example 473: 4-((1-(4-(2-(2-Aminopyridin-3-yl)-5-(3,5-dimethylisoxazol-4-yl)-3H-imidazo[4,5-b]pyridin-3-yl)benzyl)piperidin-4-yl)amino)pyrimidine-2-carbonitrile

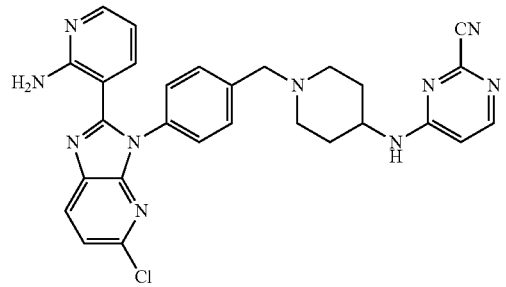

Example 405

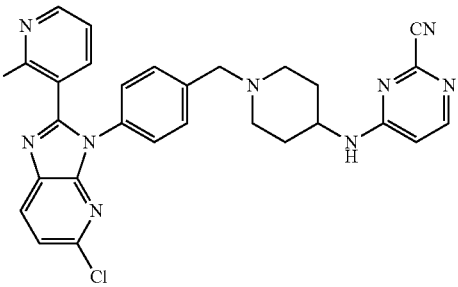

Example 405

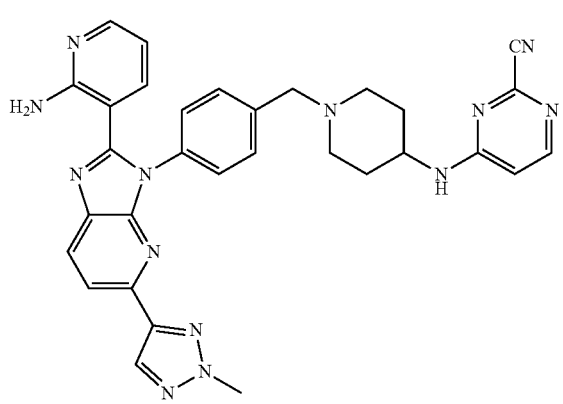

Example 472

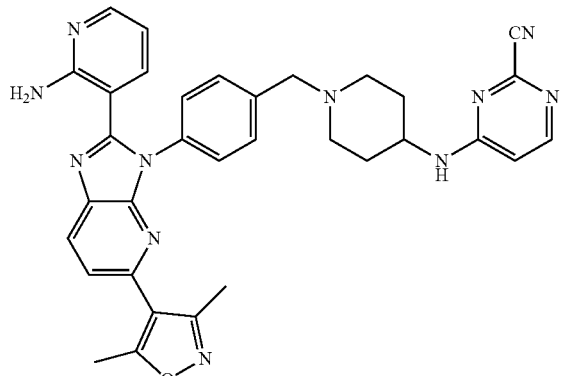

Example 473

A mixture of Example 405 (150 mg, 279 μmol), (2-methyl-2H-1,2,3-triazol-4-yl)boronic acid (43 mg, 335 μmol), cataCXiumAPdG$_3$ (118 mg, 540 μmol), K3PO$_4$ (119 mg, 559 μmol) and PCy$_3$ (7.8 mg, 28 μmol) in DMF (3 mL) was degassed and purged with N$_2$ three times. The mixture was stirred at 90° C. for 16 hr under N$_2$ atmosphere. The reaction mixture was poured into H$_2$O (15 mL) and extracted with EtOAc (15 mL×3). The combined organic phases were dried over anhydrous Na$_2$SO$_4$, filtered, and concentrated under reduced pressure. After purified by prep-HPLC (column; Waters xbridge 150×25 mm 5 μm; mobile phase: [water (NH$_4$HCO$_3$)-ACN]; gradient: 34%-64% B over 11 min), 4-((1-(4-(2-(2-aminopyridin-3-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile (Example 472, 20.5 mg, yield: 12%) was obtained as an off white lyophilized powder. MS: m/z=584.3 [M+H]$^+$. $^1$H NMR (400 MHz, Dimethylsulfoxide-d$_6$) δ 8.29 (d, J=8.0 Hz, 1H), 8.13-8.08 (m, 1H), 8.08-8.03 (m, 2H), 8.00 (dd, J=4.8, 1.6 Hz, 1H), 7.95 (d, J=8.0 Hz, 1H), 7.54-7.38 (m, 4H), 7.15 (dd, J=7.6, 2.0 Hz, 1H), 6.99 (br s, 2H), 6.68 (d, J=6.0 Hz, 1H), 6.38 (dd, J=7.6, 4.8 Hz, 1H), 4.22 (s, 3H), 3.90-3.73 (m, 1H), 3.60 (br s, 2H), 2.90-2.80 (m, 2H), 2.20-2.12 (m, 2H), 1.93-1.87 (m, 2H), 1.56-1.46 (m, 2H).

A mixture of Example 405 (200 mg, 372 μmol), (3,5-dimethylisoxazol-4-yl)boronic acid (58 mg, 410 μmol), K$_3$PO$_4$ (158 mg, 745 μmol), PCy$_3$ (10.4 mg, 37 μmol) and cataCXiumAPdG$_3$ (136 mg, 186 μmol) in DMF (3 mL) was degassed and purged with N$_2$ three times, and then was stirred at 120° C. for 2 hr under N$_2$ atmosphere. The reaction mixture was diluted with H$_2$O (10 mL) and extracted with EtOAc (10 mL×2). The combined organic layers were washed with brine (30 mL), dried over Na$_2$SO$_4$, filtered, and concentrated under reduced pressure. After purified by prep-HPLC (column: Waters Daisogel SP ODS RPS 150×25 mm×5 μm; mobile phase: [water (NH$_4$HCO$_3$)-ACN]; gradient: 36%-66% B over 10 min), 4-((1-(4-(2-(2-aminopyridin-3-yl)-5-(3,5-dimethylisoxazol-4-yl)-3H-imidazo[4,5-b]pyridin-3-yl)benzyl)piperidin-4-yl)amino)pyrimidine-2-carbonitrile (Example 473, 135.4 mg, yield: 61%) was obtained as an off white powder. MS: m/z=598.4 [M+H]$^+$. $^1$H NMR (400 MHz, Dimethysulfoxide-d$_6$) δ 8.28 (d, J=8.4 Hz, 1H), 8.23-7.94 (m, 3H), 7.55 (d, J=8.4 Hz, 1H), 7.50-7.37 (m, 4H), 7.22 (dd, J=8.0, 2.0 Hz, 1H), 7.09 (s, 2H), 6.67 (d, J=6.0 Hz, 1H), 6.40 (dd, J=7.6, 4.8 Hz, 1H), 3.89-3.69 (m, 1H), 3.57 (s, 2H), 2.79 (d, J=10.8 Hz, 2H), 2.52 (s, 3H), 2.31 (s, 3H), 2.17-2.06 (m, 2H), 1.92-1.80 (m, 2H), 1.54-1.41 (m, 2H).

Example 474: 4-((1-(4-(2-(2-Aminopyridin-3-yl)-5-(1-(difluoromethyl)-1H-pyrazol-4-yl)-3H-imidazo[4,5-b]pyridin-3-yl)benzyl)piperidin-4-yl)amino)pyrimidine-2-carbonitrile

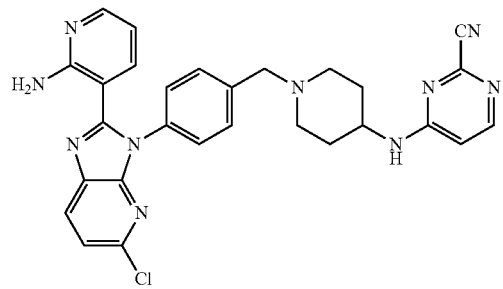

Example 405

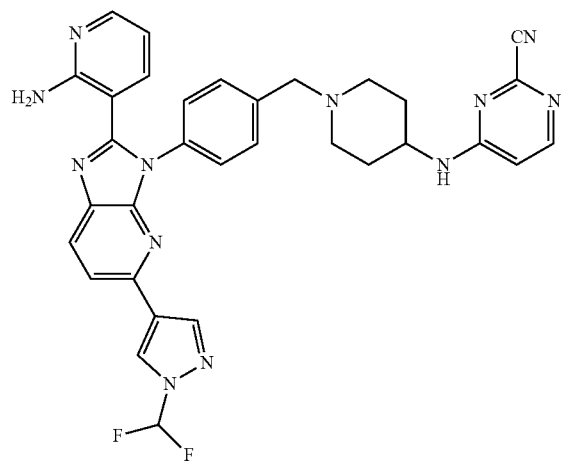

Example 474

A mixture of Example 405 (200 mg, 372 μmol), (1-(difluoromethyl)-1H-pyrazol-4-yl)boronic acid (66 mg, 410 μmol), K$_3$PO$_4$ (158 mg, 745 μmol), PCy$_3$ (10.4 mg, 37 μmol) and cataCXiumAPdG$_3$ (136 mg, 186 μmol) in DMF (3 mL) were degassed and purged with N$_2$ three times, and then was stirred at 120° C. for 2 hr under N$_2$ atmosphere. The reaction mixture was diluted with H$_2$O (10 mL) and extracted with EtOAc (10 mL×2). The combined organic layers were washed with brine (30 mL), dried over Na$_2$SO$_4$, filtered, and concentrated under reduced pressure. After purified by prep-HPLC (column: Waters Daisogel SP ODS RPS 150×25 mm×5 m; mobile phase: [water (NH$_4$HCO$_3$)-ACN]; gradient. 35%-65% B over 10 min), 4-((1-(4-(2-(2-aminopyridin-3-yl)-5-(1-(difluoromethyl)-1H-pyrazol-4-yl)-3H-imidazo[4,5-b]pyridin-3-yl)benzyl)piperidin-4-yl)amino)pyrimidine-2-carbonitrile (Example 474, 75.7 mg, yield: 33%) was obtained as an off white powder. MS: m/z=619.3 [M+H]$^+$. $^1$H NMR (400 MHz, Dimethysulfoxide-d$_6$) δ 8.71 (s, 1H), 8.29 (s, 1H), 8.24 (d, J=8.4 Hz, 1H), 8.13-7.96 (m, 3H), 7.91-7.59 (m, 2H), 7.51-7.40 (m, 4H), 7.13 (dd, J=7.6, 1.6 Hz, 1H), 7.00 (s, 2H), 6.68 (d, J=6.4 Hz, 1H), 6.37 (dd, J=7.6, 4.8 Hz, 1H), 3.92-3.72 (m, 1H), 3.59 (s, 2H), 2.91- 2.76 (m, 2H), 2.22-2.06 (m, 2H), 1.97-1.83 (m, 2H), 1.56-1.43 (m, 2H). $^{19}$F NMR (400 MHz, Dimethylsulfoxide-d$_6$) δ −94.48.

Example 475: 4-((1-(4-(2-(2-Aminopyridin-3-yl)-5-(2,4-difluorophenyl)-3H-imidazo[4,5-b]pyridin-3-yl)benzyl)piperidin-4-yl)amino)pyrimidine-2-carbonitrile

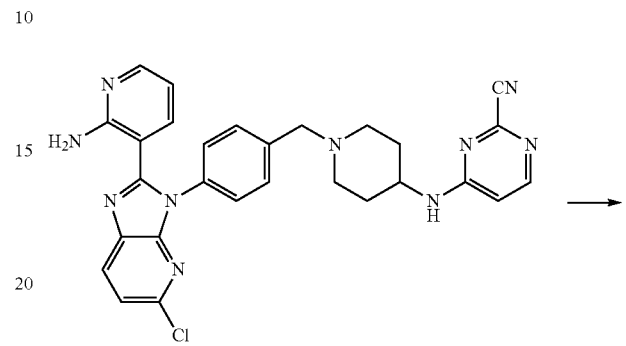

Example 405

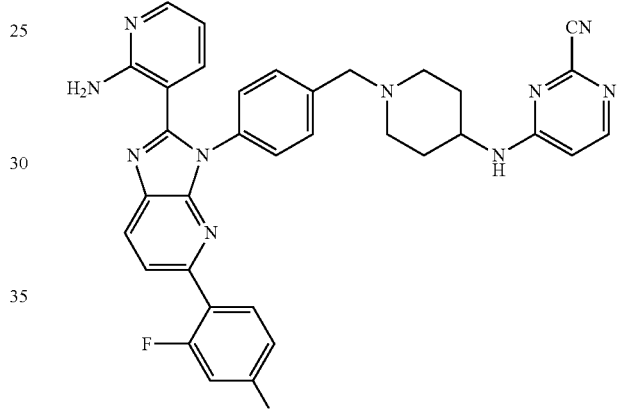

Example 475

A mixture of Example 405 (100 mg, 186 gmol), (2,4-difluorophenyl)boronic acid (32 mg, 205 μmol), K$_3$PO$_4$ (79 mg, 372 μmol), PCy$_3$ (5.2 mg. 19 μmol) and cataCXium-mAPdG3 (68 mg, 93 μmol) in DMF (3 mL) was degassed and purged with N$_2$ three times, and then was stirred at 120° C. for 2 hr under N$_2$ atmosphere. The reaction mixture was diluted with H$_2$O (10 mL) and extracted with EtOAc (10 mL×2). The combined organic layers were washed with brine (30 mL), dried over Na$_2$SO$_4$, filtered and concentrated. After purified by prep-HPLC (column: Waters xbridge 150× 25 mm×10 μm; mobile phase: [water (NH$_4$HCO$_3$)-ACN]; gradient: 40%-70% B over 11 min), 4-((1-(4-(2-(2-amino-pyridin-3-yl)-5-(2,4-difluorophenyl)-3H-imidazo[4,5-b]pyridin-3-yl)benzyl)piperidin-4-yl)amino)pyrimidine-2-carbonitrile (Example 475, 18.9 mg, yield: 17%) was obtained as a light yellow powder. MS: m/z=615.3 [M+H]$^+$. $^1$H NMR (400 MHz, Methanol-d$_4$) δ 8.21 (d, J=8.4 Hz, 1H), 8.09-7.88 (m, 3H), 7.84 (dd, J=8.4, 2.0 Hz, 1H), 7.58-7.51 (m, 2H), 7.48-7.42 (m, 2H), 7.33 (dd, J=7.8, 1.6 Hz, 1H), 7.12-6.97 (m, 2H), 6.65-6.44 (m, 1H), 6.48 (dd, J=7.6, 4.8 Hz, 1H), 4.15-3.78 (m, 1H), 3.67 (s, 2H), 3.01-2.91 (m, 2H), 2.33-2.21 (m, 2H), 2.05-1.96 (m, 2H), 1.66-1.55 (m, 2H). $^{19}$F NMR (400 MHz, Dimethylsulfoxide-d$_6$) δ −111.59, −114.05.

Example 476: 4-((1-(4-(2-(2-Aminopyridin-3-yl)-5-(6-methoxypyridin-2-yl)-3H-imidazo[4,5-b]pyridin-3-yl)benzyl)piperidin-4-yl)amino)pyrimidine-2-carbonitrile Example 477: 4-((1-(4-(2-(2-Aminopyridin-3-yl)-5-(2-methylpyridin-4-yl)-3H-imidazo[4,5-b]pyridin-3-yl)benzyl)piperidin-4-yl)amino)pyrimidine-2-carbonitrile

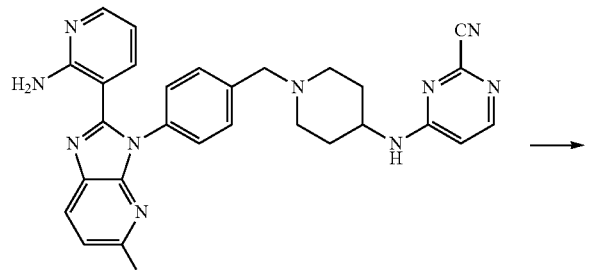

Example 405

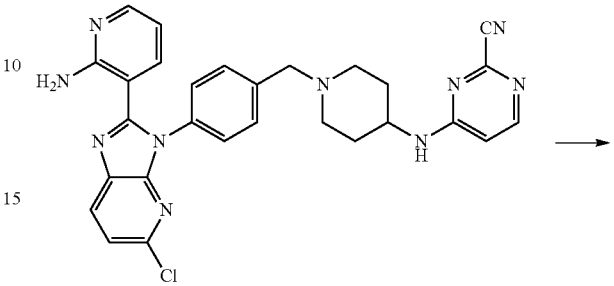

Example 405

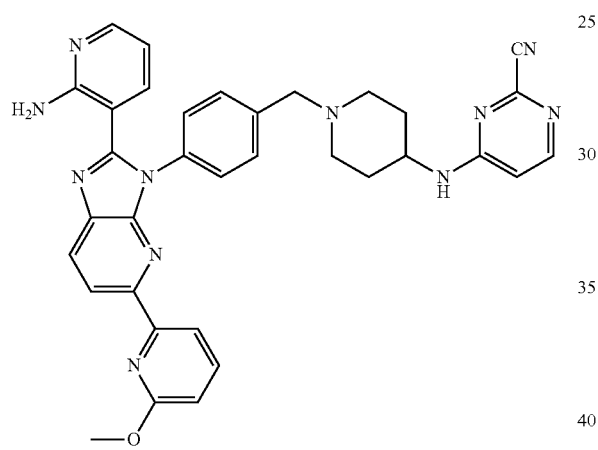

Example 476

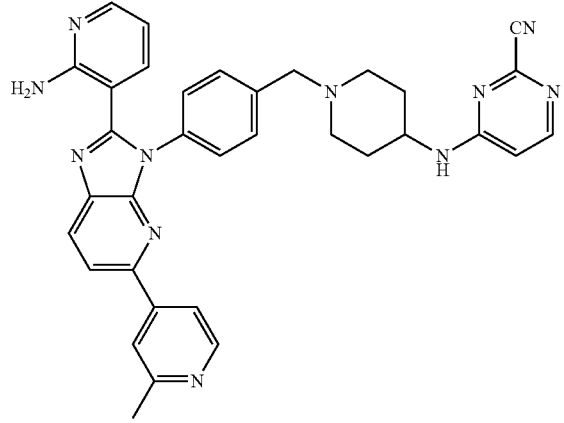

Example 477

A mixture of Example 405 (300 mg, 559 µmol), (6-methoxypyridin-2-yl)boronic acid (94 mg, 615 µmol), K₃PO₄ (237 mg, 1.12 mmol), PCy₃ (16 mg, 56 µmol) and cataCXiumAPdG3 (203 mg, 279 µmol) in DMF (3 mL) was degassed and purged with N₂ three times, and then was stirred at 120° C. for 2 hr under N₂ atmosphere. The reaction mixture was diluted with H₂O (10 mL) and extracted with EtOAc (10 mL×2). The combined organic layers were washed with brine (30 mL), dried over Na₂SO₄, filtered and concentrated. After purified by prep-HPLC (column: Phenomenex C18 150×25 mm×10 µm; mobile phase: [water (NH₄HCO₃)-ACN]; gradient: 48%-78% B over 11 min), 4-((1-(4-(2-(2-aminopyridin-3-yl)-5-(6-methoxypyridin-2-yl)-3H-imidazo[4,5-b]pyridin-3-yl)benzyl)piperidin-4-yl)amino)pyrimidine-2-carbonitrile (Example 476, 43.7 mg, yield: 13%) was obtained as a yellow powder. MS: m/z=610.5 [M+H]⁺. ¹H NMR (400 MHz, Methanol-d₄) δ 8.56 (d, J=8.4 Hz, 1H), 8.22 (d, J=8.8 Hz, 1H), 8.07-7.94 (m, 2H), 7.88 (d, J=7.6 Hz, 1H), 7.72-7.65 (m, 1H), 7.60-7.53 (m, 2H), 7.50-7.45 (m, 2H), 7.34 (dd, J=7.6, 2.0 Hz, 1H), 6.76 (d, J=8.0 Hz, 1H), 6.65-6.54 (m, 1H), 6.49 (dd, J=7.6, 5.2 Hz, 1H), 4.05 (s, 3H), 4.02-3.89 (m, 1H), 3.68 (s, 2H), 3.02-2.94 (m, 2H), 2.33-2.24 (m, 2H), 2.04-2.00 (m, 2H), 1.67-1.57 (m, 2H).

A mixture of Example 405 (200 mg, 372 µmol), (2-methylpyridin-4-yl)boronic acid (56 mg, 410 µmol), K₃PO₄ (158 mg, 745 µmol), PCy₃ (10.4 mg, 37 µmol) and cataCXiumAPdG₃ (136 mg, 186 µmol) in DMF (3 mL) were degassed and purged with N₂ three times, and then was stirred at 120° C. for 2 hr under N₂ atmosphere. The reaction mixture was diluted with H₂O (10 mL) and extracted with EtOAc (10 mL×2). The combined organic layers were washed with brine (30 mL), dried over Na₂SO₄, filtered, and concentrated under reduced pressure. After purified by prep-HPLC (column: Phenomenex C18 150×25 mm×10 µm; mobile phase: [water (NH₄HCO₃)-ACN]; gradient: 32%-62% B over 11 min), 4-((1-(4-(2-(2-aminopyridin-3-yl)-5-(2-methylpyridin-4-yl)-3H-imidazo[4,5-b]pyridin-3-yl)benzyl)piperidin-4-yl)amino)pyrimidine-2-carbonitrile (Example 477, 46.3 mg, yield: 21%) was obtained as a yellow powder. MS: m/z=594.3 [M+H]⁺. ¹H NMR (400 MHz, Methanol-d₄) δ 8.45 (d, J=5.2 Hz, 1H), 8.31-8.24 (m, 1H), 8.09 (d, J=8.4 Hz, 1H), 8.05-7.98 (m, 2H), 7.95 (s, 1H), 7.90-7.86 (m, 1H), 7.60-7.54 (m, 2H), 7.49-7.38 (m, 2H), 7.34 (dd, J=7.6, 2.0 Hz, 1H), 6.66-6.54 (m, 1H), 6.48 (dd, J=7.6, 4.8 Hz, 1H), 4.09-3.85 (m, 1H), 3.70-3.65 (m, 2H), 3.02-2.95 (m, 2H), 2.58 (s, 3H), 2.33-2.24 (m, 2H), 2.05-1.97 (m, 2H), 1.67-1.58 (m, 2H).

Example 478: 4-((1-(4-(2-(2-Aminopyridin-3-yl)-5-(5-methylpyridin-3-yl)-3H-imidazo[4,5-b]pyridin-3-yl)benzyl)piperidin-4-yl)amino)pyrimidine-2-carbonitrile Example 479: 4-((1-(4-(2-(2-Aminopyridin-3-yl)-5-(1-isopropyl-1H-pyrazol-4-yl)-3H-imidazo[4,5-b]pyridin-3-yl)benzyl)piperidin-4-yl)amino)pyrimidine-2-carbonitrile

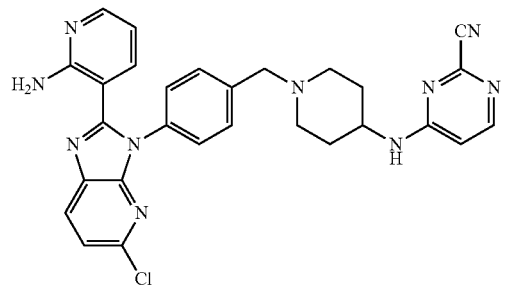

Example 405

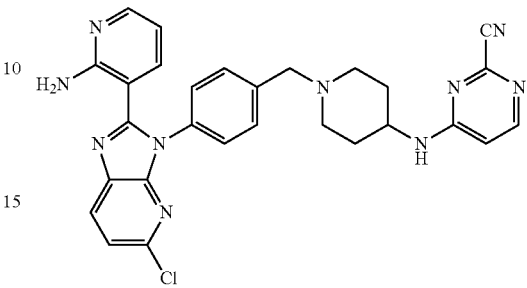

Example 405

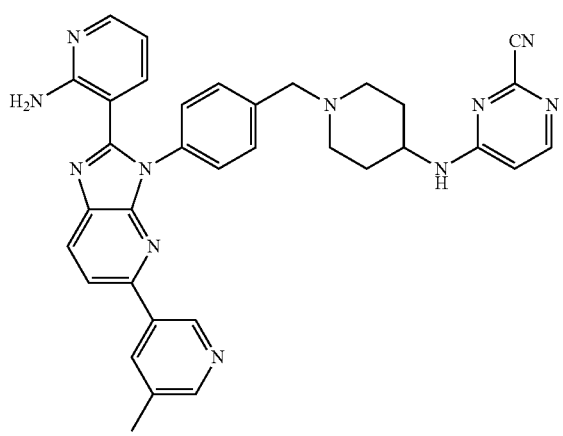

Example 478

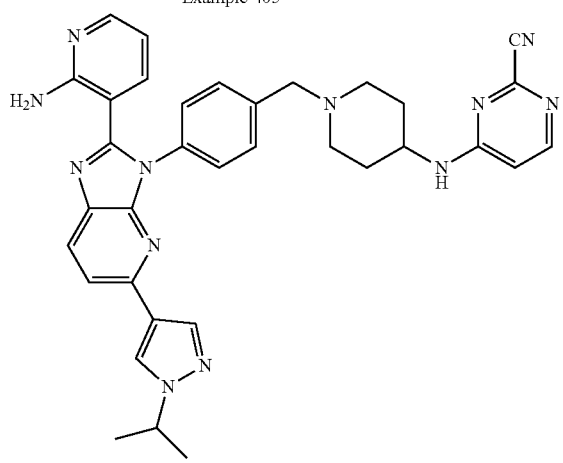

Example 479

A mixture of Example 405 (200 mg, 372 μmol), (5-methylpyridin-3-yl)boronic acid (56 mg, 410 μmol), K3PO₄ (158 mg, 745 μmol), PCy3 (10.4 mg, 37 μmol) and cataCXiumAPdG3 (136 mg, 186 μmol) in DMF (3 mL) were degassed and purged with N₂ three times, and then was stirred at 120° C. for 2 hr under N₂ atmosphere. The reaction mixture was diluted with H₂O (10 mL) and extracted with EtOAc (10 mL×2). The combined organic layers were washed with brine (30 mL), dried over Na₂SO₄, filtered, and concentrated under reduced pressure. After purified by prep-HPLC (column: Phenomenex C18 150×25 mm×10 μm; mobile phase: [water (NH₄HCO₃)-ACN]; gradient: 32%-62% B over 11 min), 4-((1-(4-(2-(2-aminopyridin-3-yl)-5-(5-methylpyridin-3-yl)-3H-imidazo[4,5-b]pyridin-3-yl)benzyl)piperidin-4-yl)amino)pyrimidine-2-carbonitrile (Example 478, 37.4 mg, yield: 17%) was obtained as a yellow powder. MS: m/z=594.4 [M+H]⁺. ¹H NMR (400 MHz, Methanol-d₄) δ 8.98 (d, J=2.0 Hz, 1H), 8.41-8.33 (m, 1H), 8.29-8.21 (m, 2H), 8.07-7.93 (m, 3H), 7.56 (d, J=8.4 Hz, 2H), 7.45 (d, J=8.4 Hz, 2H), 7.32 (dd, J=7.6, 1.6 Hz, 1H), 6.68-6.53 (m, 1H), 6.47 (dd, J=7.6, 5.2 Hz, 1H), 4.13-3.79 (m, 1H), 3.67 (s, 2H), 3.01-2.92 (m, 2H), 2.42 (s, 3H), 2.27 (t, J=12.0 Hz, 2H), 2.06-1.98 (m, 2H), 1.67-1.55 (m, 2H).

A mixture of Example 405 (200 mg, 372 μmol), (1-isopropyl-1H-pyrazol-4-yl)boronic acid (63 mg, 410 μmol), K₃PO₄ (158 mg, 745 μmol), PCy₃ (10.4 mg, 37 μmol) and cataCXiumAPdG₃ (135.61 mg, 186.21 μmol) in DMF (3 mL) was degassed and purged with N₂ three times, and then was stirred at 130° C. for 2 hr under N₂ atmosphere. The reaction mixture was diluted with H₂O (10 mL) and extracted with EtOAc (10 mL×2). The combined organic layers were washed with brine (30 mL), dried over Na₂SO₄, filtered, and concentrated under reduced pressure. After purified by prep-HPLC (column: Waters Xbridge BEH C18 150×25 mm×5 μm; mobile phase: [water (NH₄HCO₃)-ACN]; gradient: 32%-62% B over 10 min), 4-((1-(4-(2-(2-aminopyridin-3-yl)-5-(1-isopropyl-1H-pyrazol-4-yl)-3H-imidazo[4,5-b]pyridin-3-yl)benzyl)piperidin-4-yl)amino)pyrimidine-2-carbonitrile (Example 479, 22.8 mg, yield: 10%) was obtained as a yellow solid. MS: m/z=611.3 [M+H]⁺. ¹H NMR (400 MHz, Methanol-d₄) δ 8.15-8.10 (m, 1H), 8.04 (d, J=8.4 Hz, 1H), 8.01-7.96 (m, 1H), 7.96-7.91 (m, 2H), 7.64 (d, J=8.4 Hz, 1H), 7.47 (d, J=8.4 Hz, 2H), 7.36 (d, J=8.4 Hz, 2H), 7.20 (dd, J=7.6, 1.6 Hz, 1H), 6.58 (d, J=5.6 Hz, 1H), 6.41 (dd, J=7.6, 5.2 Hz, 1H), 4.55-4.45 (m, 1H), 4.00-3.85 (m, 1H), 3.59 (s, 2H), 2.91 (d, J=11.6 Hz, 2H), 2.25-2.16 (m, 2H), 1.98 (d, 0.1=10.4 Hz, 2H), 1.61-1.52 (m, 2H), 1.47 (d, J=6.4 Hz, 6H).

Example 480: 4-((1-(4-(2-(2-Aminopyridin-3-yl)-5-(isothiazol-4-yl)-3H-imidazo[4,5-b]pyridin-3-yl)benzyl)piperidin-4-yl)amino)pyrimidine-2-carbonitrile

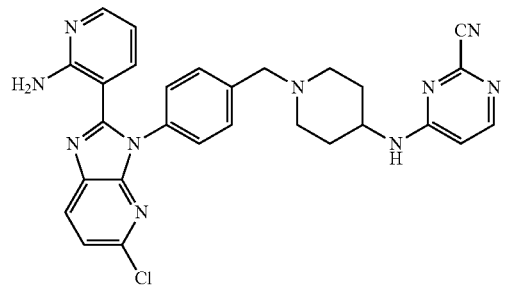

Example 405

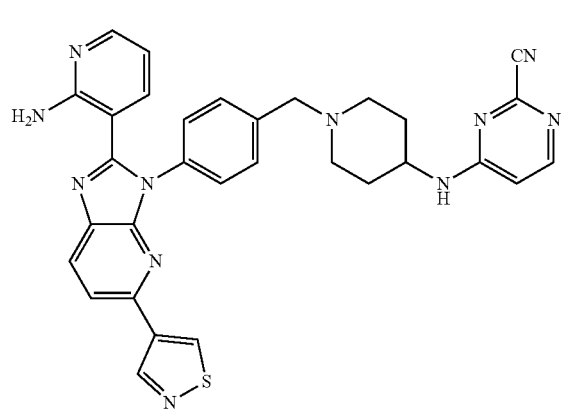

Example 480

A mixture of Example 405 (200 mg, 372 μmol), isothiazol-4-ylboronic acid (58 mg, 447 μmol), K3PO₄ (158 mg, 745 μmol), PCy₃ (10.4 mg, 37 μmol) and cataCXiumAPdG₃ (135.61 mg, 186.21 μmol) in DMF (3 mL) were degassed and purged with $N_2$ three times, and then was stirred at 120° C. for 2 hr under $N_2$ atmosphere. The reaction mixture was diluted with $H_2O$ (10 mL) and extracted with EtOAc (10 mL×2). The combined organic layers were washed with brine (30 mL), dried over $Na_2SO_4$, filtered, and concentrated under reduced pressure. After purified by prep-HPLC (column: Waters Xbridge 150×25 mm×10 μm; mobile phase: [water (NH₄HCO₃)-ACN]; gradient: 28%-58% B over 11 min), 4-((1-(4-(2-(2-aminopyridin-3-yl)-5-(isothiazol-4-yl)-3H-imidazo[4,5-b]pyridin-3-yl)benzyl)piperidin-4-yl)amino)pyrimidine-2-carbonitrile (Example 480, 21.9 mg, yield: 13%) was obtained as a yellow solid. MS: m/z=586.3 [M+H]⁺. ¹H NMR (400 MHz, Dimethysulfoxide-d₆) δ 9.46 (s, 1H), 9.11 (s, 1H), 8.29 (d, J=8.4 Hz, 1H), 8.09-8.04 (m, 2H), 8.02-7.92 (m, 2H), 7.52-7.38 (m, 4H), 7.22-7.11 (m, 1H), 7.08-6.96 (m, 2H), 6.67 (d, J=6.4 Hz, 1H), 6.38 (dd, J=7.6, 4.8 Hz, 1H), 3.92-3.73 (m, 1H), 3.59 (s, 2H), 2.88-2.79 (m, 2H), 2.16 (t, J=10.4 Hz, 2H), 1.93-1.87 (m, 2H), 1.58-1.43 (m, 2H).

Example 481: 4-((1-(4-(2-(2-Aminopyridin-3-yl)-5-(5-cyano-1-methyl-1H-pyrrol-3-yl)-3H-imidazo[4,5-b]pyridin-3-yl)benzyl)piperidin-4-yl)amino)pyrimidine-2-carbonitrile

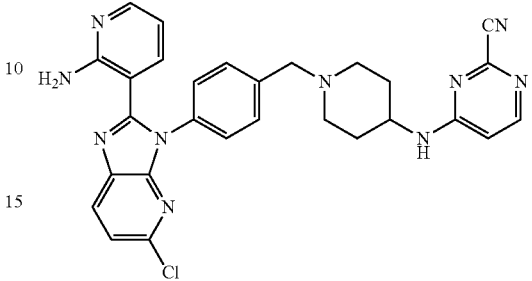

Example 405

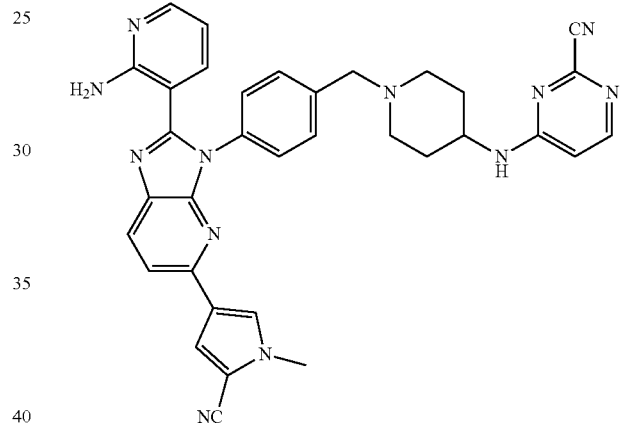

Example 481

A mixture of Example 405 (200 mg, 372 μmol), (5-cyano-1-methyl-1H-pyrrol-3-yl)boronic acid (67 mg, 447 μmol), K₃PO₄ (158 mg, 745 μmol), PCy₃ (10.4 mg, 37 μmol) and cataCXiumAPdG₃ (135.61 mg, 186.21 μmol) in DMF (5 mL) was degassed and purged with $N_2$ three times, and then was stirred at 120° C. for 2 hr under $N_2$ atmosphere. The reaction mixture was diluted with $H_2O$ (10 mL) and extracted with EtOAc (10 mL×2). The combined organic layers were washed with brine (30 mL), dried over $Na_2SO_4$, filtered and concentrated. After purified by prep-HPLC (column: Waters Xbridge 150×25 mm×10 μm; mobile phase: [water (NH₄HCO₃)-ACN]; gradient: 30%-60% B over 11 min), 4-((1-(4-(2-(2-aminopyridin-3-yl)-5-(5-cyano-1-methyl-1H-pyrrol-3-yl)-3H-imidazo[4,5-b]pyridin-3-yl)benzyl)piperidin-4-yl)amino)pyrimidine-2-carbonitrile (Example 481, 16.3 mg, yield: 7%) was obtained as a yellow solid. MS: m/z=607.3 [M+H]⁺. ¹H NMR (400 MHz, Methanol-d₄) δ 8.08 (d, J=8.4 Hz, 1H), 8.04-7.99 (m, 1H), 7.97 (dd, J=4.8, 1.2 Hz, 1H), 7.66 (d, J=8.4 Hz, 1H), 7.60-7.56 (m, 1H), 7.54 (d, J=8.0 Hz, 2H), 7.42 (d, J=8.4 Hz, 2H), 7.34-7.25 (m, 2H), 6.60 (d, J=6.4 Hz, 1H), 6.46 (dd, J=7.6, 5.2 Hz, 1H), 4.05-3.90 (m, 1H), 3.81 (s, 3H), 3.63 (s, 2H), 3.01-2.92 (m, 2H), 2.35-2.26 (m, 2H), 2.06-2.00 (m, 2H), 1.67-1.59 (m, 2H).

Example 482: 4-((1-(4-(2-(2-Aminopyridin-3-yl)-5-(thiazol-4-yl)-3H-imidazo[4,5-b]pyridin-3-yl)benzyl)piperidin-4-yl)amino)pyrimidine-2-carbonitrile Example 483: 4-((1-(4-(2-(2-Aminopyridin-3-yl)-5-(isothiazol-5-yl)-3H-imidazo[4,5-b]pyridin-3-yl)benzyl)piperidin-4-yl)amino)pyrimidine-2-carbonitrile

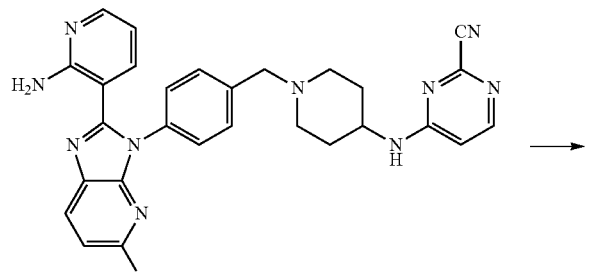

Example 405

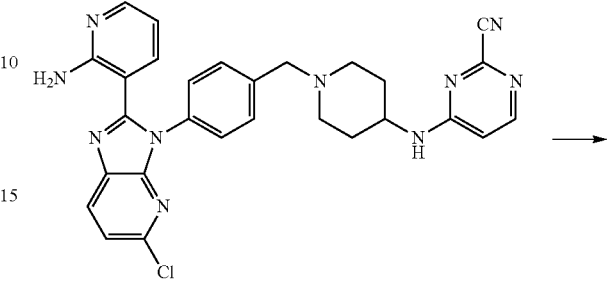

Example 405

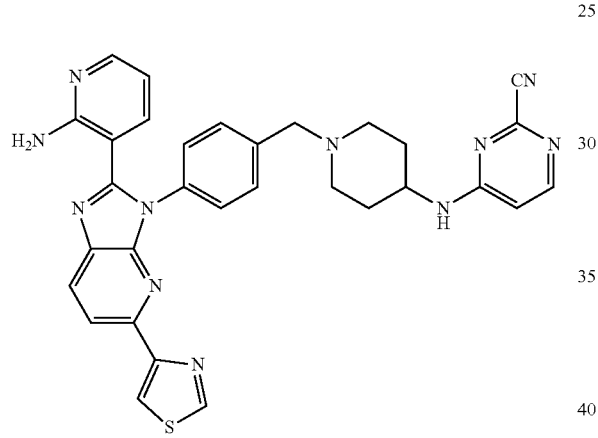

Example 482

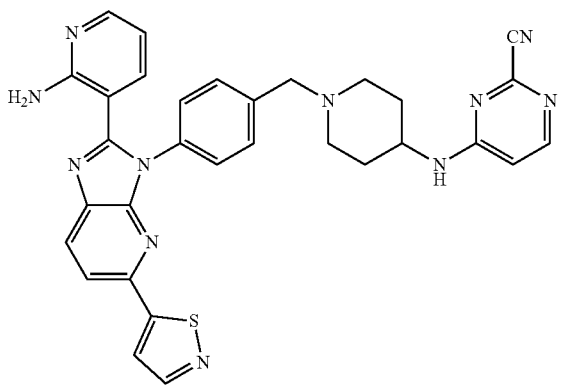

Example 483

A mixture of Example 405 (200 mg, 372 mol), thiazol-4-ylboronic acid (144 mg, 1.12 mmol), Pd(dppf)Cl$_2$ (27 mg, 37 μmol), Cs$_2$CO$_3$ (364 mg, 1.1 mmol) and 1,4-dioxane (4 mL) in H$_2$O (1 mL) was degassed and purged with N$_2$ three times, and then was stirred at 100° C. for 3 hr under N$_2$ atmosphere. The reaction mixture was diluted with H$_2$O (10 mL) and extracted with EtOAc (10 mL×2). The combined organic layers were washed with brine (30 mL), dried over Na$_2$SO$_4$, filtered, and concentrated under reduced pressure. After purified by prep-HPLC (column: Waters Xbridge 150×25 mm×10 μm; mobile phase: [water (NH$_4$HCO$_3$)-ACN]; gradient: 35%-65% B over 10 min), 4-((1-(4-(2-(2-aminopyridin-3-yl)-5-(thiazol-4-yl)-3H-imidazo[4,5-b]pyridin-3-yl)benzyl)piperidin-4-yl)amino)pyrimidine-2-carbonitrile (Example 482, 20.1 mg, yield: 9%) was obtained as an off white solid. MS: m/z=608.2 [M+Na]$^+$. $^1$H NMR (400 MHz, Methanol-d$_4$) δ 9.05 (s, 1H), 8.25-8.20 (m, 2H), 8.09-8.05 (m, 1H), 8.03-7.94 (m, 2H), 7.57-7.53 (m, 2H), 7.47-7.43 (m, 2H), 7.34-7.28 (m, 1H), 6.60 (d, J=5.6 Hz, 1H), 6.50-6.44 (m, 1H), 4.06-3.88 (m, 1H), 3.66 (s, 2H), 2.97 (d, J=11.2 Hz, 2H), 2.28 (t, J=11.2 Hz, 2H), 2.05-1.99 (m, 2H), 1.67-1.58 (m, 2H).

A mixture of Example 405 (200 mg, 372 μmol), 5-(4,4,5,5-tetramethyl-1,3,2-dioxaborolan-2-yl)isothiazole (94.3 mg, 447 μmol), Pd(dppf)Cl$_2$ (27 mg, 37 μmol), Cs$_2$CO$_3$ (364 mg, 1.1 mmol) and 1,4-dioxane (2 mL) in H$_2$O (0.5 mL) was degassed and purged with N$_2$ three times, and then was stirred at 100° C. for 1 hr under N$_2$ atmosphere. The reaction mixture was diluted with H$_2$O (10 mL) and extracted with EtOAc (10 mL×2). The combined organic layers were washed with brine (30 mL), dried over Na$_2$SO$_4$, filtered, and concentrated under reduced pressure. After purified by prep-HPLC (column: Waters Xbridge 150×25 mm×5 μm; mobile phase: [water (NH$_4$HCO$_3$)-ACN]; gradient: 30%-60% B over 10 min), 4-((1-(4-(2-(2-aminopyridin-3-yl)-5-(isothiazol-5-yl)-3H-imidazo[4,5-b]pyridin-3-yl)benzyl)piperidin-4-yl)amino)pyrimidine-2-carbonitrile (Example 483, 21.5 mg, yield: 10%) was obtained as an off white solid. MS: m/z=586.3 [M+H]$^+$. $^1$H NMR (400 MHz, Methanol-d$_4$) δ 8.49 (d, J=2.0 Hz, 1H), 8.23 (d, J=8.4 Hz, 1H), 8.11-7.90 (m, 3H), 7.84 (d, J=2.0 Hz, 1H), 7.57 (d, J=8.4 Hz, 2H), 7.44 (d, J=8.4 Hz, 2H), 7.33 (dd, J=7.6, 1.6 Hz, 1H), 6.66-6.54 (m, 1H), 6.48 (dd, J=7.6, 5.2 Hz, 1H), 4.09-3.86 (m, 1H), 3.68 (s, 2H), 2.98 (d, J=11.2 Hz, 2H), 2.35-2.24 (m, 2H), 2.02 (d, J=9.6 Hz, 2H), 1.68-1.55 (m, 2H).

Example 484: 4-((1-(4-(2-(2-Aminopyridin-3-yl)-5-(1,5-dimethyl-1H-pyrazol-4-yl)-3H-imidazo[4,5-b]pyridin-3-yl)benzyl)piperidin-4-yl)amino)pyrimidine-2-carbonitrile

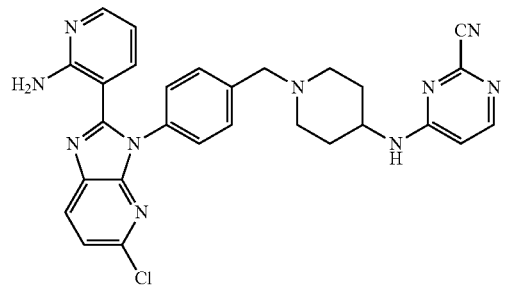

Example 405

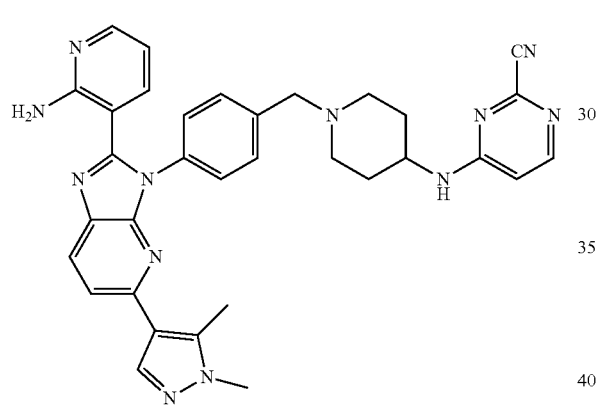

Example 484

Example 485: 4-((1-(4-(2-(2-Aminopyridin-3-yl)-5-bromo-3H-imidazo[4,5-b]pyridin-3-yl)benzyl)piperidin-4-yl)amino)pyrimidine-2-carbonitrile

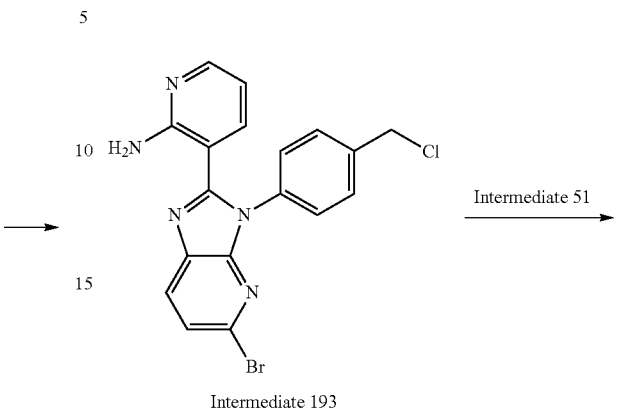

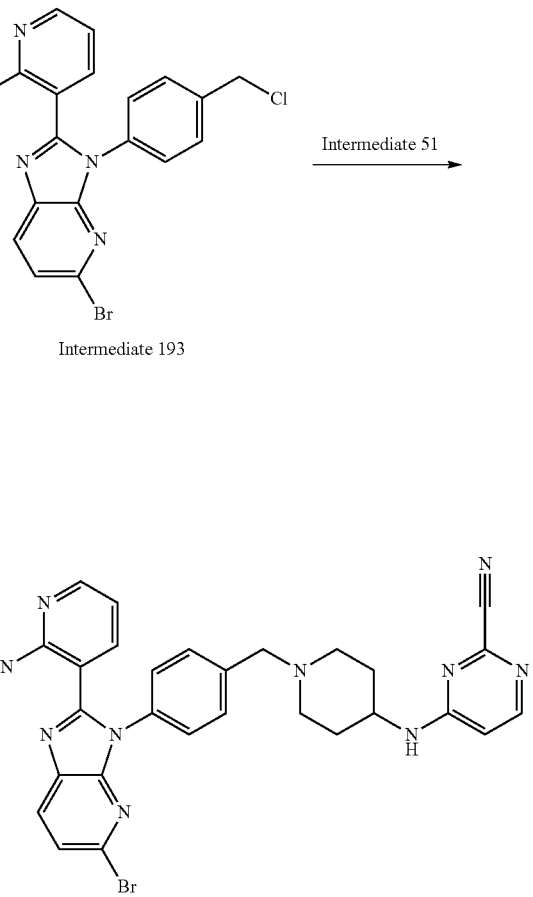

Example 485

A mixture of Example 405 (250 mg, 430 μmol), (1,5-dimethyl-1H-pyrazol-4-yl)boronic acid (72 mg, 516 μmol), Cs₂CO₃ (14 mg, 43 μmol), XphosPdG₄ (370 mg, 430 μmol) in 1,4-dioxane (2 mL) was degassed and purged with N₂ three times, and then was stirred at 90° C. for 16 hr under N₂ atmosphere. The reaction mixture was diluted with H₂O (20 mL) and extracted with EtOAc (20 mL×2). The combined organic layers were washed with brine (30 mL), dried over Na₂SO₄, filtered, and concentrated under reduced pressure. After purified by prep-HPLC (column: Waters Xbridge BEH C18 150×25 mm×5 μm; mobile phase: [water (NH₄HCO₃)-ACN]; gradient. 27%-57% B over 10 min), 4-((1-(4-(2-(2-aminopyridin-3-yl)-5-(1,5-dimethyl-1H-pyrazol-4-yl)-3H-imidazo[4,5-b]pyridin-3-yl)benzyl)piperidin-4-yl)amino)pyrimidine-2-carbonitrile (Example 484, 17 mg, yield: 6%) was obtained as a yellow solid. MS: m/z=597.2 [M+H]⁺. ¹H NMR (400 MHz, Methanol-d₄) δ 8.15-8.08 (m, 1H), 8.05-7.95 (m, 2H), 7.89 (s, 1H), 7.68-7.62 (m, 1H), 7.57-7.50 (m, 2H), 7.46-7.40 (m, 2H), 7.34 (dd, J=7.6, 1.6 Hz, 1H), 6.64-6.55 (m, 1H), 6.47 (dd, J=7.6, 5.2 Hz, 1H), 4.04-3.89 (m, 1H), 3.79 (s, 3H), 3.67 (s, 2H), 2.95 (d, J=11.6 Hz, 2H), 2.52 (s, 3H), 2.26 (t, J=11.2 Hz, 2H), 2.06-1.96 (m, 2H), 1.67-1.51 (m, 2H).

To a solution of Intermediate 193 (4.06 g, 9.79 mmol) and Intermediate 51 (2.19 g, 10.8 mmol) in DMF (50 mL) was added DIEA (17.1 mL, 97.94 mmol). The mixture was degassed and purged with N₂ three times and stirred at 60° C. for 2 hr under N₂. The reaction mixture was quenched with H₂O (150 mL) and then extracted with EtOAc (60 mL×3). The combined organic layers were washed with brine (100 mL×3), dried over Na₂SO₄, filtered and concentrated under reduced pressure. After purified by silica gel flash chromatography (MeOH in CH₂Cl₂=1 to 5%) and prep-HPLC (column: Waters xbridge 150×25 mm 10 μm; mobile phase: [water (NH₄HCO₃)-ACN]; gradient: 40%-70% B over 11 min), 4-((1-(4-(2-(2-aminopyridin-3-yl)-5-bromo-3H-imidazo[4,5-b]pyridin-3-yl)benzyl)piperidin-4-yl)amino)pyrimidine-2-carbonitrile (Example 485, 2.33 g, 39.6% yield for three steps) was obtained as a yellow solid. MS: m/z=581.2, 583.1 [M+H]⁺. ¹H NMR (400 MHz, Dimethylsulfoxide-d₆) 8.17 (d, J=8.4 Hz, 1H), 8.12-8.02 (m, 2H), 7.99 (dd, J=4.8, 2.0 Hz, 1H), 7.58 (d, J=8.4 Hz, 1H), 7.48-7.45 (m, 2H), 7.41-7.38 (m, 2H), 7.15 (dd, J=7.6, 1.6 Hz, 1H), 6.93 (br s, 2H), 6.68 (d, J=6.0 Hz, 1H), 6.37 (dd, J=7.6, 4.8 Hz, 1H), 3.86-3.76 (m, 1H), 3.57 (s, 2H), 2.85-2.78 (m, 2H), 2.15 (t, J=11.6 Hz, 2H), 1.93-1.84 (m, 2H), 1.54-1.44 (m, 2H).

Example 486: 4-((1-((4-(2-(2-Aminopyridin-3-yl)-5-bromo-3H-imidazo[4,5-b]pyridin-3-yl)phenyl)methyl-d2)piperidin-4-yl)amino)pyrimidine-2-carbonitrile

Example 487: 4-((1-(4-(2-(2-Aminopyridin-3-yl)-5-(4-fluorophenyl)-3H-imidazo[4,5-b]pyridin-3-yl)benzyl)piperidin-4-yl)amino)-1,3,5-triazine-2-carbonitrile

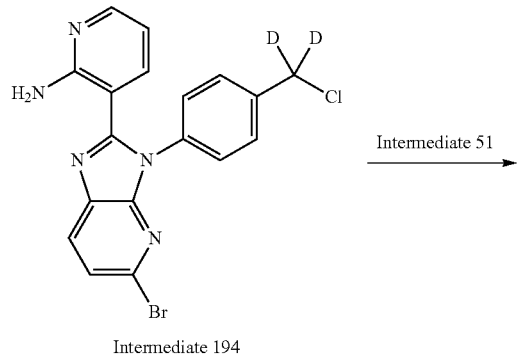

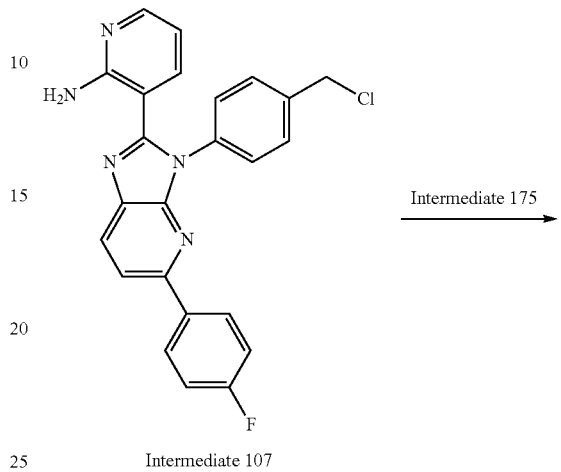

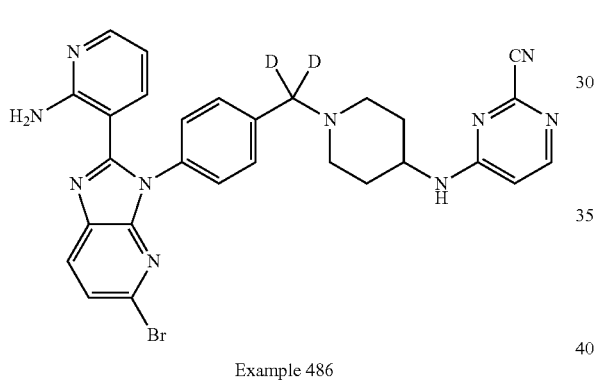

To a solution of Intermediate 194 (199 mg, 477 μmol) and Intermediate 51 (97.0 mg, 477 μmol) in DMF (3 mL) were added K$_2$CO$_3$ (198 mg, 1.43 mmol), NaI (71.5 mg. 477 μmol). The mixture was degassed and purged with N$_2$ three times and stirred at 25° C. for 16 hr under N$_2$. The reaction mixture was filtered and concentrated under reduced pressure. After purified by prep-HPLC (column: Phenomenex C18 150×25 mm×10 μm; mobile phase: [water (NH$_4$HCO$_3$)-ACN]; gradient: 38%-68% B over 11 min). 4-((1-((4-(2-(2-Aminopyridin-3-yl)-5-bromo-3H-imidazo[4,5-b]pyridin-3-yl)phenyl)methyl-d$_2$)piperidin-4-yl)amino)pyrimidine-2-carbonitrile (Example 486, 49.2 mg, 16.8% yield for three steps) was obtained as a light yellow solid. MS: m/z=583.2, 585.2 [M+H]$^+$. $^1$H NMR (400 MHz, Dimethylsulfoxide-d$_6$) δ 8.17 (d, J=8.4 Hz, 1H), 8.12-8.02 (m, 2H), 7.99 (dd, J=4.8, 1.6 Hz, 1H), 7.58 (d, J=8.4 Hz, 1H), 7.48-7.44 (m, 2H), 7.41-7.37 (m, 2H), 7.15 (dd, J=7.6, 1.6 Hz, 1H), 6.92 (br s, 2H), 6.67 (d, J=6.4 Hz, 1H), 6.37 (dd, J=7.6, 4.8 Hz, 1H), 3.87-3.76 (m, 1H), 2.85-2.78 (m, 2H), 2.19-2.11 (m, 2H), 1.93-1.84 (m, 2H), 1.54-1.44 (m, 2H).

To a solution of Intermediate 107 (100 mg, 233 μmol) in DMF (3 mL) were added Intermediate 175 (57 mg, 279 μmol), NaI (35 mg, 233 μmol) and K$_2$CO$_3$ (129 mg, 931 μmol) at 25° C. The mixture was stirred at 50° C. for 1 hr. The reaction mixture was poured into H$_2$O (50 mL) and extracted with CH$_2$Cl$_2$ (20 mL×2). The combined organic layers were washed with brine (40 mL), dried over anhydrous Na$_2$SO$_4$, filtered and concentrated. After purified by silica gel flash chromatography (Eluent of 0~5% MeOH in CH$_2$Cl$_2$), 4-((1-(4-(2-(2-aminopyridin-3-yl)-5-(4-fluorophenyl)-3H-imidazo[4,5-b]pyridin-3-yl)benzyl)piperidin-4-yl)amino)-1,3,5-triazine-2-carbonitrile (Example 487, 30.0 mg, yield: 20%) was obtained as an yellow solid. MS: m/z=598.3 [M+H]$^+$. $^1$H NMR (400 MHz, Dimethylsulfoxide-d$_6$) δ 8.92 (dd, J=7.6, 5.2 Hz, 1H), 8.65 (d, J=29.2 Hz, 1H), 8.27 (d, J=8.4 Hz, 1H), 8.08 (dd, J=8.4, 5.6 Hz, 2H), 8.02-7.95 (m, 2H), 7.51-7.42 (m, 4H), 7.30 (t, J=8.8 Hz, 2H), 7.17-7.13 (m, 1H), 7.03 (s, 2H), 6.41-6.34 (m, 1H), 3.86-3.69 (m, 1H), 3.58 (d, J=4.0 Hz, 2H), 2.91-2.79 (m, 2H), 2.18-2.03 (m, 2H), 1.88-1.78 ((m, 2H), 1.66-1.50 (m, 2H). $^{19}$F NMR (400 MHz, Dimethylsulfoxide-d$_6$) δ −113.58.

Example 488: 4-((1-((4-(2-(2-Aminopyridin-3-yl)-5-(4-fluorophenyl)-3H-imidazo[4,5-b]pyridin-3-yl)phenyl)methyl-d2)piperidin-4-yl)(methyl)amino)pyrimidine-2-carbonitrile

Example 489: 4-((1-((4-(2-(2-Aminopyridin-3-yl)-5-(4-fluorophenyl)-3H-imidazo[4,5-b]pyridin-3-yl)phenyl)methyl-d2)piperidin-4-yl)amino)pyrimidine-2-carbonitrile

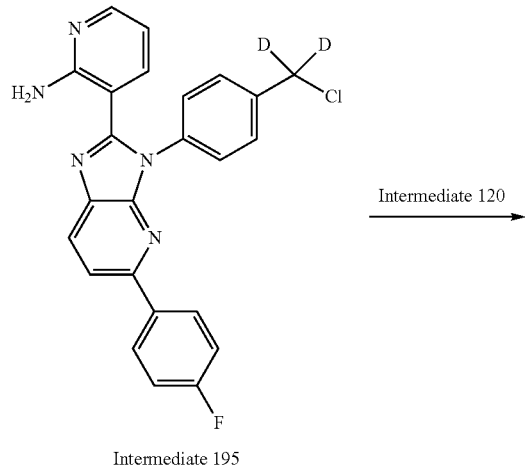

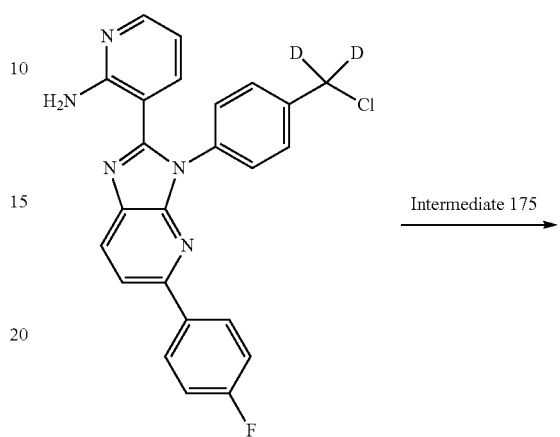

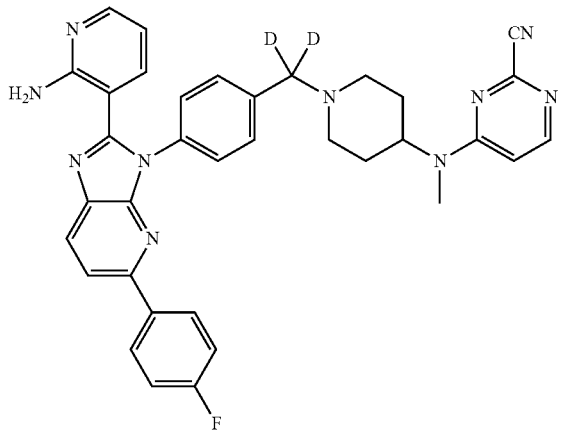

To a solution of Intermediate 195 (100 mg, 232 μmol) in DMF (3 mL) were added Intermediate 120 (60 mg, 278 μmol), NaI (35 mg, 232 μmol) and $K_2CO_3$ (128 mg, 926 μmol) at 25° C. The mixture was stirred at 50° C. for 1 hr. The reaction mixture was poured into $H_2O$ (50 mL) and extracted with $CH_2Cl_2$ (20 mL×2). The combined organic layers were washed with brine (40 mL), dried over anhydrous $Na_2SO_4$, filtered and concentrated. After purified silica gel flash chromatography (Eluent of 0~5% MeOH in $CH_2C_2$), 4-((1-((4-(2-(2-aminopyridin-3-yl)-5-(4-fluorophenyl)-3H-imidazo[4,5-b]pyridin-3-yl)phenyl)methyl-d2)piperidin-4-yl)(methyl)amino)pyrimidine-2-carbonitrile (Example 488, 20.9 mg, yield: 14%) was obtained as an off white solid. MS: m/z=613.4 [M+H]+. 1H NMR (400 MHz, Dimethylsulfoxide-$d_6$) δ 8.21-8.14 (m, 2H), 8.10-8.04 (m, 2H), 7.99 (dd, J=4.8, 1.6 Hz, 1H), 7.92 (d, J=8.4 Hz, 1H), 7.59-7.53 (m, 2H), 7.49-7.44 (m, 2H), 7.32 (dd, J=7.6, 1.6 Hz, 1H), 7.16 (t, J=8.8 Hz, 2H), 6.88-6.78 (m, 1H), 6.48 (dd, J=8.0, 5.2 Hz, 1H), 3.11-3.05 (m, 2H), 2.99 (s, 3H), 2.37-2.23 (m, 2H), 2.07-2.00 (m, 1H), 2.00-1.88 (m, 2H), 1.76-1.66 (m, 2H). 19F NMR (400 MHz, Dimethylsulfoxide-$d_6$) δ −115.70.

To a solution of Intermediate 195 (200 mg, 523 μmol) in DMF (3 mL) were added Intermediate 175 (113 mg, 556 μmol), NaI (69 mg, 463 μmol) and $K_2CO_3$ (256 mg, 1.9 mmol) at 25° C. The mixture was stirred at 50° C. for 1 hr. The reaction mixture was poured into $H_2O$ (50 mL) and extracted with $CH_2Cl_2$ (20 mL×2). The combined organic layers were washed with brine (40 mL), dried over anhydrous $Na_2SO_4$, filtered and concentrated. After purified silica gel flash chromatography (Eluent of 0~5% MeOH in $CH_2Cl_2$), 4-((1-((4-(2-(2-aminopyridin-3-yl)-5-(4-fluorophenyl)-3H-imidazo[4,5-b]pyridin-3-yl)phenyl)methyl-d2)piperidin-4-yl)amino)pyrimidine-2-carbonitrile (Example 489, 118.6 mg, yield: 42%) was obtained as an yellow solid. MS: m/z=599.3 [M+H]+. 1H NMR (400 MHz, Dimethylsulfoxide-$d_6$) δ 8.27 (d, J=8.4 Hz, 1H), 8.11-8.04 (m, 4H), 8.01-7.95 (m, 2H), 7.50-7.43 (m, 4H), 7.29 (t, J=8.8 Hz, 2H), 7.14 (dd, J=7.6, 1.6 Hz, 1H), 7.04 (s, 2H), 6.68 (d, J=6.0 Hz, 1H), 6.37 (dd, J=7.6, 4.8 Hz, 1H), 3.89-3.73 (m, 1H), 2.88-2.78 (m, 2H), 2.21-2.07 (m, 2H), 1.93-1.84 (m, 2H), 1.57-1.43 (m, 2H). 19F NMR (400 MHz, Dimethylsulfoxide-$d_6$) δ −113.56.

Example 490: 4-(7-(4-(2-(2-Aminopyridin-3-yl)-5-(4-fluorophenyl)-3H-imidazo[4,5-b]pyridin-3-yl)benzyl)-2,7-diazaspiro[3.5]nonan-2-yl)pyrimidine-2-carbonitrile

Example 491: 4-(2-(4-(2-(2-Aminopyridin-3-yl)-5-(4-fluorophenyl)-3H-imidazo[4,5-b]pyridin-3-yl)benzyl)-2,7-diazaspiro[3.5]nonan-7-yl)pyrimidine-2-carbonitrile

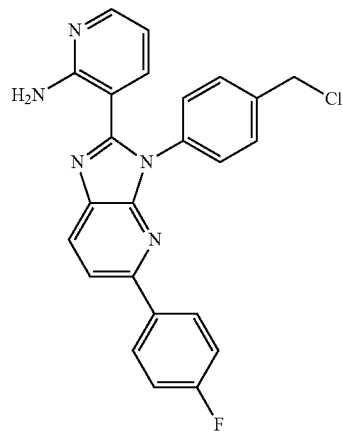

Intermediate 107

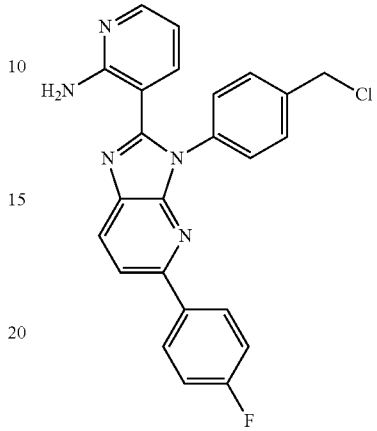

Intermediate 107

Intermediate 191 →

Intermediate 192 →

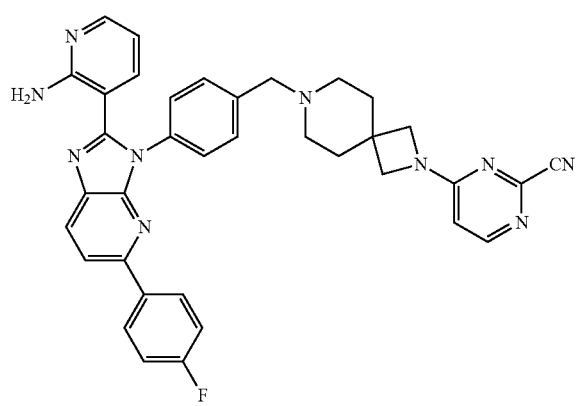

Example 490

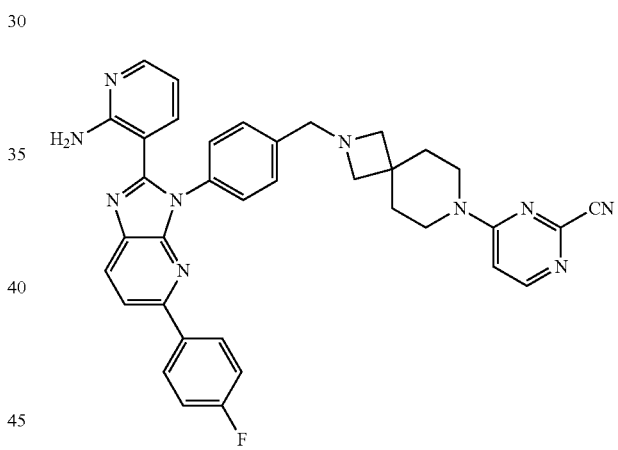

Example 491

To a solution of Intermediate 191 (107 mg, 465 μmol, TFA salt) and Intermediate 107 (200 mg, 465 μmol, HCl salt) in DMF (5 mL) were added NaI (35 mg, 233 μmol) and $K_2CO_3$ (335 mg, 2.43 mmol). The mixture was stirred at 50° C. for 1 hr. After purified by prep-HPLC (column: Waters xbridge 150×25 mm 10 μm; mobile phase: [water ($NH_4HCO_3$)-ACN]; gradient: 59%-89% B over 10 min), 4-(7-(4-(2-(2-aminopyridin-3-yl)-5-(4-fluorophenyl)-3H-imidazo[4,5-b]pyridin-3-yl)benzyl)-2,7-diazaspiro[3.5]nonan-2-yl)pyrimidine-2-carbonitrile (Example 490, 105.6 mg, yield: 35%) was obtained as a yellow solid. MS: m/z=623.3 [M+H]$^+$. $^1$H NMR (400 MHz, Dimethylsulfoxide-$d_6$) δ 8.28 (d, J=8.4 Hz, 1H), 8.22 (d, J=6.0 Hz, 1H), 8.10-8.06 (m, 2H), 8.02-7.97 (m, 2H), 7.50-7.43 (m, 4H), 7.33-7.28 (m, 2H), 7.16 (dd, J=7.6, 2.0 Hz, 1H), 7.03 (s, 2H), 6.64 (d, J=6.0 Hz, 1H), 6.39 (dd, J=7.6, 4.8 Hz, 1H), 3.81 (s, 4H), 3.57 (s, 2H), 2.42-2.31 (m, 4H), 1.81-1.77 (m, 4H).

To a solution of Intermediate 192 (107 mg, 465 μmol, TFA salt) and Intermediate 107 (200 mg, 465 μmol, HCl salt) in DMF (5 mL) were added NaI (35 mg, 233 μmol) and $K_2CO_3$ (322 mg, 2.33 mmol). The mixture was stirred at 50° C. for 1 hr. After purified by prep-HPLC (column: Waters xbridge 150×25 mm 10 μm; mobile phase: [water ($NH_4HCO_3$)-ACN]; gradient: 49%-79% B over 10 min), 4-(2-(4-(2-(2-aminopyridin-3-yl)-5-(4-fluorophenyl)-3H-imidazo[4,5-b]pyridin-3-yl)benzyl)-2,7-diazaspiro[3.5]nonan-7-yl)pyrimidine-2-carbonitrile (Example 491, 54.2 mg, yield: 18%) was obtained as a yellow solid. MS: m/z=623.3 [M+H]$^+$. $^1$H NMR (400 MHz, Dimethylsulfoxide-$d_6$) δ 8.27 (d, J=8.4 Hz, 1H), 8.22 (d, J=6.4 Hz, 1H), 8.09-8.05 (m, 2H), 8.01-7.96 (m, 2H), 7.45-7.42 (m, 4H), 7.32-7.27 (m, 2H), 7.16 (dd, J=8, 2 Hz, 1H), 7.12 (d, J=6.4 Hz, 1H), 6.99 (s, 2H), 6.39 (dd, J=7.2, 6.4 Hz, 1H), 3.70 (s, 2H), 3.60 (s, 4H), 3.07 (s, 4H), 1.77-1.72 (m, 4H). $^{19}$F NMR (400 MHz, Dimethylsulfoxide-d6) δ −113.588.

Example 492: 4-((1-(4-(2-(2-Aminopyridin-3-yl)-5-(methylsulfinyl)-3H-imidazo[4,5-b]pyridin-3-yl)benzyl)piperidin-4-yl)amino)pyrimidine-2-carbonitrile

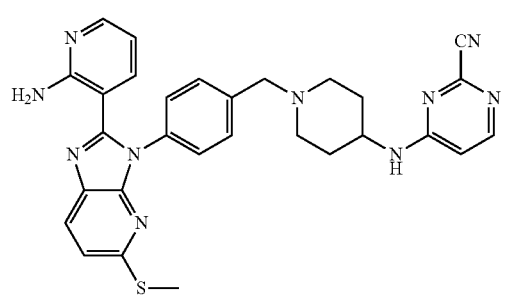

Example 435

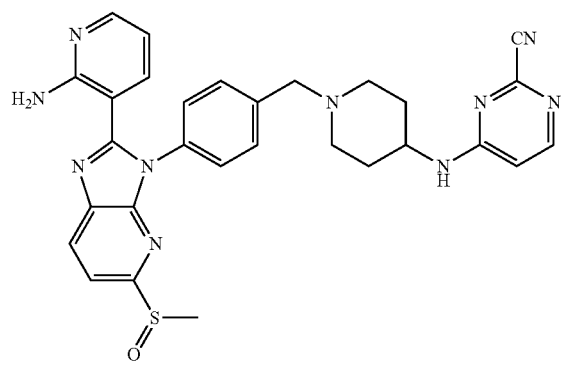

Example 492

Example 493: 4-((1-(4-(2-(2-Aminopyridin-3-yl)-5,7-dimethyl-3H-imidazo[4,5-b]pyridin-3-yl)benzyl)piperidin-4-yl)amino)pyrimidine-2-carbonitrile

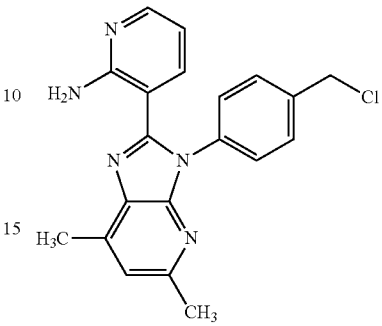

Intermediate 196

→ Intermediate 51

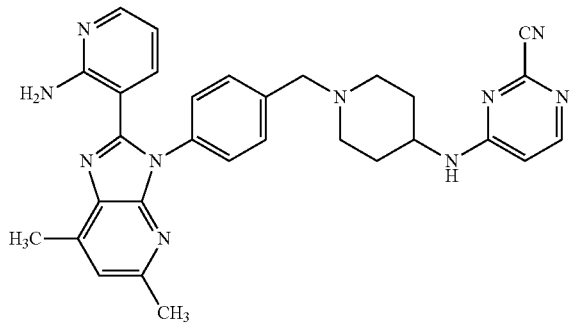

Example 493

To a solution of Example 435 (110 mg, 200 μmol) in THF (2 mL) and MeOH (0.5 mL) was added oxone (370 mg, 601 μmol). The mixture was stirred at 25° C. for 2 hr. The reaction mixture was concentrated under reduced pressure. After purified by prep-HPLC (column: Waters xbridge 150*25 mm 10 μm; mobile phase: [water ($NH_4HCO_3$)-ACN]; gradient: 20%-40% B over 11 min), 4-((1-(4-(2-(2-aminopyridin-3-yl)-5-(methylsulfinyl)-3H-imidazo[4,5-b]pyridin-3-yl)benzyl)piperidin-4-yl)amino)pyrimidine-2-carbonitrile (Example 492, 4.7 mg, yield: 4%) was obtained as light yellow solid. MS: m/z=565.2 [M+H]$^+$. $^1$H NMR (400 MHz, Methanol-$d_4$) δ 8.42 (d, J=8.0 Hz, 1H), 8.06-7.96 (m, 3H), 7.54 (d, J=8.0 Hz, 2H), 7.41 (d, J=8.0 Hz, 2H), 7.32 (dd, J=7.6, 1.2 Hz, 1H), 6.63-6.59 (m, 1H), 6.47 (dd, J=7.6, 5.2 Hz, 1H), 4.02-3.91 (m, 1H), 3.66 (s, 2H), 2.98-2.91 (m, 2H), 2.86 (s, 3H), 2.32-2.22 (m, 2H), 2.07-1.96 (m, 2H), 1.61-1.57 (m, 2H).

To a solution of Intermediate 196 (300 mg, 825 μmol) and Intermediate 51 (168 mg, 825 μmol) in DMF (5 mL) were added NaI (61.8 mg, 412 μmol) and $K_2CO_3$ (570 mg, 4.12 mmol). The mixture was stirred at 50° C. for 1 hr. The reaction mixture was diluted with $H_2O$ (100 mL) and extracted with EtOAc (100 mL×3). The combined organic layers were washed with brine (200 mL), dried over $Na_2SO_4$, filtered and concentrated under reduced pressure. After purified by silica gel flash chromatography (Eluent of 0~6% MeOH in $CH_2Cl_2$), 4-((1-(4-(2-(2-aminopyridin-3-yl)-5,7-dimethyl-3H-imidazo[4,5-b]pyridin-3-yl)benzyl)piperidin-4-yl)amino)pyrimidine-2-carbonitrile (Example 493, 154 mg, yield: 35%) was obtained as a yellow solid. MS: m/z=531.7 [M+H]$^+$. $^1$H NMR (400 MHz, Dimethylsulfoxide-$d_6$) δ 8.07 (dd, J=12.4, 6.0 Hz, 2H), 7.96 (dd, J=4.8, 1.6 Hz, 1H), 7.44 (d, J=8.0 Hz, 2H), 7.33 (d, J=8.0 Hz, 2H), 7.09-7.06 (m, 2H), 7.02 (s, 2H), 6.67 (br d, J=6.0 Hz, 1H), 6.34 (dd, J=7.6, 4.8 Hz, 1H), 3.86-3.76 (m, 1H), 3.56 (s, 2H), 2.85-2.80 (m, 2H), 2.61 (s, 3H), 2.47 (s, 3H), 2.18-2.11 (m, 2H), 1.92-1.84 (m, 1H), 1.53-1.44 (m, 2H).

1603

Example 494: 4-((1-(4-(8-(2-aminopyridin-3-yl)-6-hydroxy-9H-purin-9-yl)benzyl)piperidin-4-yl)amino)pyrimidine-2-carbonitrile

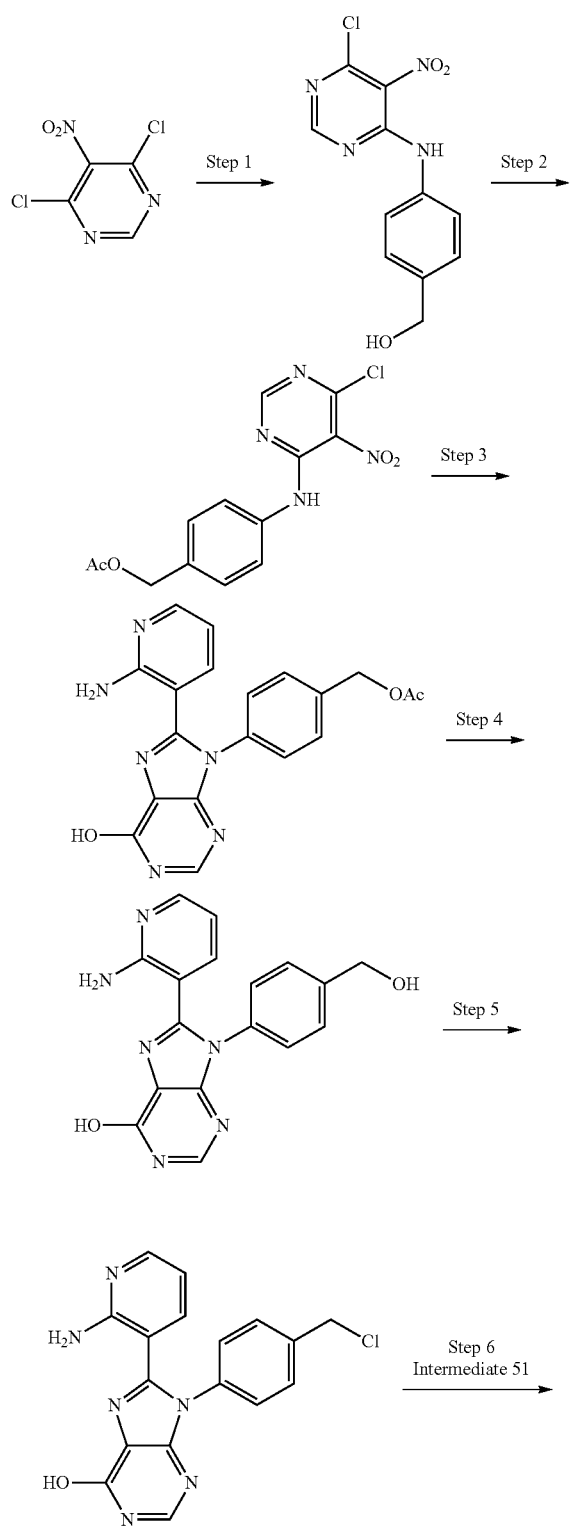

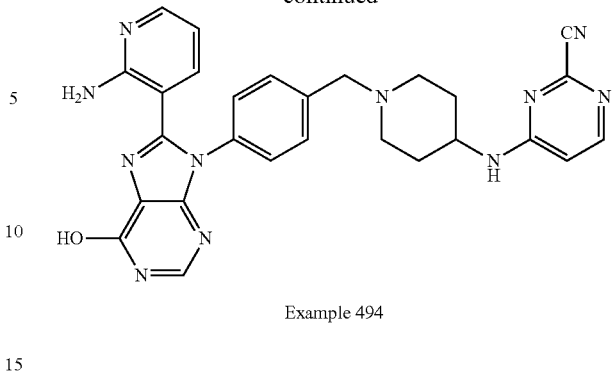

Example 494

Step 1: (4-((6-Chloro-5-nitropyrimidin-4-yl)amino)phenyl)methanol

A mixture of 4,6-dichloro-5-nitropyrimidine (10 g, 51.6 mmol), (4-aminophenyl)methanol (5.08 g, 41.2 mmol) in THF (300 mL) was added TEA (4.69 g, 46.4 mmol) at 0° C. The mixture was degassed and purged with $N_2$ three times, and then was stirred at 0° C. for 0.5 hr under $N_2$ atmosphere. And then it was stirred at 25° C. for 3 hr. The reaction mixture was diluted with water (400 mL) and extracted with EtOAc (300 mL×3). The combined organic layers were washed with brine (400 mL), dried over $Na_2SO_4$, filtered and concentrated under reduced pressure. After purified by silica gel flash chromatography (Eluent of 0~37% EtOAc in petroleum ether), (4-((6-chloro-5-nitropyrimidin-4-yl)amino)phenyl)methanol (8.6 g, yield: 59%) was obtained as an orange solid. MS: m/z=280.9 [M+H]$^+$. $^1$H NMR (400 MHz, Dimethylsulfoxide-d$_6$) δ 10.07 (s, 1H), 8.49 (s, 1H), 7.43 (d, J=8.4 Hz, 2H), 7.32 (d, J=8.4 Hz, 2H), 4.49 (s, 3H).

Step 2: 4-((6-Chloro-5-nitropyrimidin-4-yl)amino)benzyl acetate

A mixture of (4-((6-chloro-5-nitropyrimidin-4-yl)amino)phenyl)methanol (8 g, 28.5 mmol), DMAP (348 mg, 2.85 mmol) and TEA (8.65 g, 85.5 mmol) in $CH_2Cl_2$ (200 mL) was added $Ac_2O$ (2.91 g, 28.5 mmol). The mixture was degassed and purged with $N_2$ three times, and then was stirred at 0° C. for 2 hr under $N_2$ atmosphere. The reaction mixture was diluted with water (200 mL) and extracted with EtOAc (200 mL×3). The combined organic layers were washed with brine (200 mL), dried over $Na_2SO_4$, filtered and concentrated under reduced pressure. After purified by silica gel flash chromatography (Eluent of 0~100% EtOAc in petroleum ether), 4-((6-chloro-5-nitropyrimidin-4-yl)amino)benzyl acetate (1.0 g, yield: 9%) was obtained as a yellow solid. MS: m/z=304.8 [M+H]+, $^1$H NMR (400 MHz, Chloroform-d) δ 11.28 (s, 1H), 10.91 (s, 1H), 8.10-7.90 (m, 1H), 7.45 (d, J=8.0 Hz, 2H), 7.44 (d, J=8.0 Hz, 2H), 5.13 (s, 2H), 2.05 (s, 3H).

Step 3: 4-(8-(2-Aminopyridin-3-yl)-6-hydroxy-9H-purin-9-yl)benzyl acetate

A mixture of 4-((6-chloro-5-nitropyrimidin-4-yl)amino)benzyl acetate (343 mg, 3.10 mmol), 2-aminonicotinaldehyde (416 mg, 3.41 mmol) and $Na_2S_2O_4$ (2.16 g, 12.4 mmol) in DMSO (100 mL) was degassed and purged with $N_2$ three times. The mixture was stirred at 100° C. for 16 hr under $N_2$ atmosphere. The reaction mixture was diluted with $H_2O$ (100 mL) and extracted with EtOAc (100 mL×3). The combined organic layers were washed with brine (200 mL), dried over Na$_2$SO$_4$, filtered and concentrated under reduced pressure. After purified by silica gel flash chromatography (Eluent of 0-80% EtOAc in petroleum ether), 4-(8-(2-aminopyridin-3-yl)-6-hydroxy-9H-purin-9-yl)benzyl acetate (200 mg, yield: 12%) was obtained as a yellow solid. MS: m/z=376.9 [M+H]%, $^1$H NMR (400 MHz, Dimethylsulfoxide-d$_6$) δ 12.67-12.14 (m, 1H), 8.02 (s, 1H), 7.95 (dd, J=4.8, 1.6 Hz, 1H), 7.45 (d, J=8.8 Hz, 2H), 7.40 (d, J=8.0 Hz, 2H), 7.14 (dd, J=7.6, 1.6 Hz, 1H), 6.79 (s, 2H), 6.39 (dd, J=7.6, 4.8 Hz, 1H), 5.14 (s, 2H), 2.10 (s, 3H).

Step 4: 8-(2-Aminopyridin-3-yl)-9-(4-(hydroxymethyl)phenyl)-9H-purin-6-ol

To a mixture of 4-(8-(2-aminopyridin-3-yl)-6-hydroxy-9H-purin-9-yl)benzyl acetate (150 mg, 399 μmol) in MeOH (10 mL), THF (10 mL) and H$_2$O (5 mL) was added K$_2$CO$_3$ (55.1 mg 399 μmol). The mixture was stirred at 25° C. for 0.5 hr. The mixture was filtered and concentrated under reduced pressure to give 8-(2-aminopyridin-3-yl)-9-(4-(hydroxymethyl)phenyl)-9H-purin-6-ol (100 mg, yield: 75%) as a yellow solid. MS: m/z=335.0 [M+H]$^+$.

Step 5: 8-(2-Aminopyridin-3-yl)-9-(4-(chloromethyl)phenyl)-9H-purin-6-ol

To a solution of 8-(2-aminopyridin-3-yl)-9-(4-(hydroxymethyl)phenyl)-9H-purin-6-ol (100 mg, 299 μmol) in CH$_2$Cl$_2$ (10 mL) was added SOCl$_2$ (214 mg, 1.79 mmol). The mixture was stirred at 25° C. for 1 hr. The mixture was concentrated under reduced pressure to give 8-(2-aminopyridin-3-yl)-9-(4-(chloromethyl)phenyl)-9H-purin-6-ol (100 mg, yield: 95%) as a yellow solid. MS: m/z=353.1 [M+H]$^+$.

Step 6: 4-((1-(4-(8-(2-Aminopyridin-3-yl)-6-hydroxy-9H-purin-9-yl)benzyl)piperidin-4-yl)amino)pyrimidine-2-carbonitrile To a solution of 8-(2-aminopyridin-3-yl)-9-(4-(chloromethyl)phenyl)-9H-purin-6-ol (100 mg, 283 μmol) and Intermediate 51 (57.6 mg, 283 μmol) in DMF (5 mL) were added NaI (21.2 mg, 142 μmol) and K$_2$CO$_3$ (196 mg, 1.42 mmol). The mixture was stirred at 50° C. for 1 hr. The reaction mixture was filtered and concentrated. After purified by prep-HPLC (column: Waters xbridge 150×25 mm 10 μm; mobile phase: [water (NH$_4$HCO$_3$)-ACN]; gradient: 12%-42% B over 10 min), 4-((1-(4-(8-(2-aminopyridin-3-yl)-6-hydroxy-9H-purin-9-yl)benzyl)piperidin-4-yl)amino)pyrimidine-2-carbonitrile (Example 494, 15.3 mg, yield: 9%) was obtained as a yellow solid. MS: m/z=520.1 [M+H]$^+$. $^1$H NMR (400 MHz, Dimethylsulfoxide-d$_6$) δ 12.56-12.18 (m, 1H), 8.12-8.02 ((m, 3H), 7.94 (dd, J=4.8, 1.6 Hz, 1H), 7.43 (d, J=8.4 Hz, 2H), 7.34 (d, J=8.0 Hz, 2H), 7.06 (dd, J=8.0, 2.0 Hz, 1H), 6.89 (s, 2H), 6.67 (d, J=6.0 Hz, 1H), 6.34 (dd, J=8.0, 4.8 Hz, 1H), 3.86-3.75 (m, 1H), 3.55 (s, 2H), 2.79 (d, J=11.6 Hz, 2H), 2.17-2.09 (m, 2H), 1.91-1.82 (m, 2H), 1.53-1.43 (m, 2H).

Example 495: 4-((1-(4-(2-(2-Aminopyridin-3-yl)-5-(pyridin-2-yl)-3H-imidazo[4,5-b]pyridin-3-yl)benzyl)piperidin-4-yl)amino)pyrimidine-2-carbonitrile

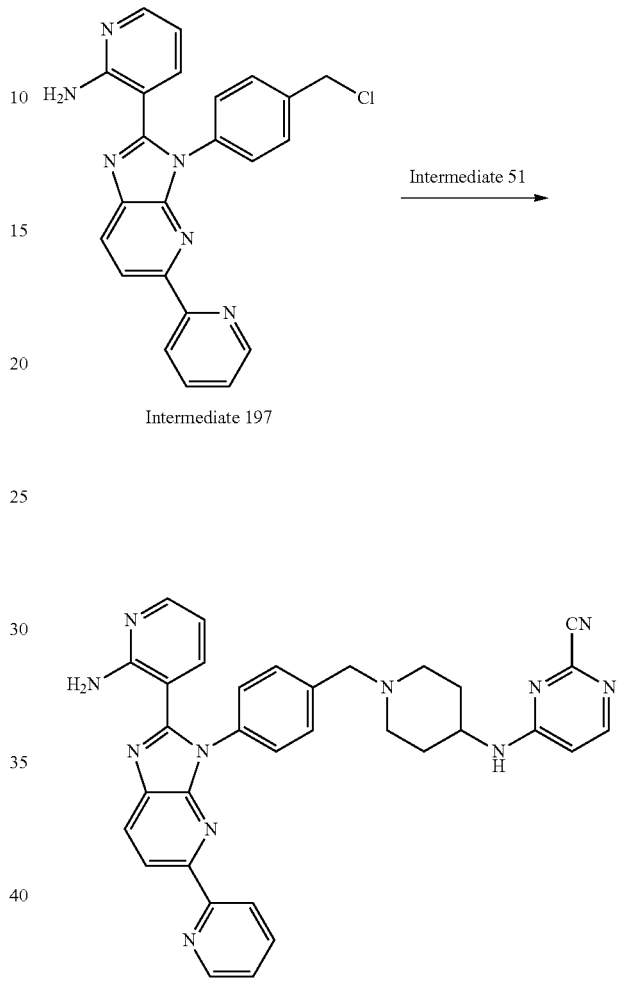

To a solution of Intermediate 197 (180 mg, 436 μmol) in DMF (3 mL) were added Intermediate 51 (106 mg, 523 μmol), NaI (65 mg, 436 μmol) and K$_2$CO$_3$ (241 mg, 1.7 mmol) at 25° C. The mixture was stirred at 50° C. for 1 hr. The reaction mixture was poured into H$_2$O (50 mL) and extracted with CH$_2$Cl$_2$ (20 mL×2). The combined organic layers were washed with brine (40 mL), dried over anhydrous Na$_2$SO$_4$, filtered, and concentrated to dryness. After purified by silica gel flash chromatography (Eluent of 0~5% MeOH in CH$_2$Cl$_2$), 4-((1-(4-(2-(2-aminopyridin-3-yl)-5-(pyridin-2-yl)-3H-imidazo[4,5-b]pyridin-3-yl)benzyl)piperidin-4-yl)amino)pyrimidine-2-carbonitrile (Example 495, 57.2 mg, yield: 22%) was obtained as a yellow solid. MS: m/z=580.3 [M+H]$^+$. $^1$H NMR (400 MHz, Dimethylsulfoxide-d$_6$) δ 8.67 (d, J=4.8 Hz, 1H), 8.47 (d, J=8.4 Hz, 1H), 8.31 (d, J=8.4 Hz, 1H), 8.19 (d, J=8.0 Hz, 1H), 8.14-8.03 (m, 2H), 8.03-7.97 (m, 11H), 7.93-7.86 (m, 1H), 7.53-7.44 (m, 4H), 7.40 (d, J=6.4, 4.8 Hz, 11H), 7.18 (d, J=6.8 Hz, 11H), 7.01 (s, 2H), 6.68 (d, J=5.2 Hz, 1H), 6.39 (dd, J=7.6, 4.8 Hz, 1H), 3.91-3.73 (m, 1H), 3.60 (s, 2H), 2.88-2.78 (m, 2H), 2.24-2.07 (m, 2H), 1.97-1.82 (m, 2H), 1.59-1.42 (m, 2H).

Example 496: 4-((1-(4-(2-(2-Aminopyridin-3-yl)-5-hydroxy-3H-imidazo[4,5-b]pyridin-3-yl)benzyl)piperidin-4-yl)amino)pyrimidine-2-carbonitrile

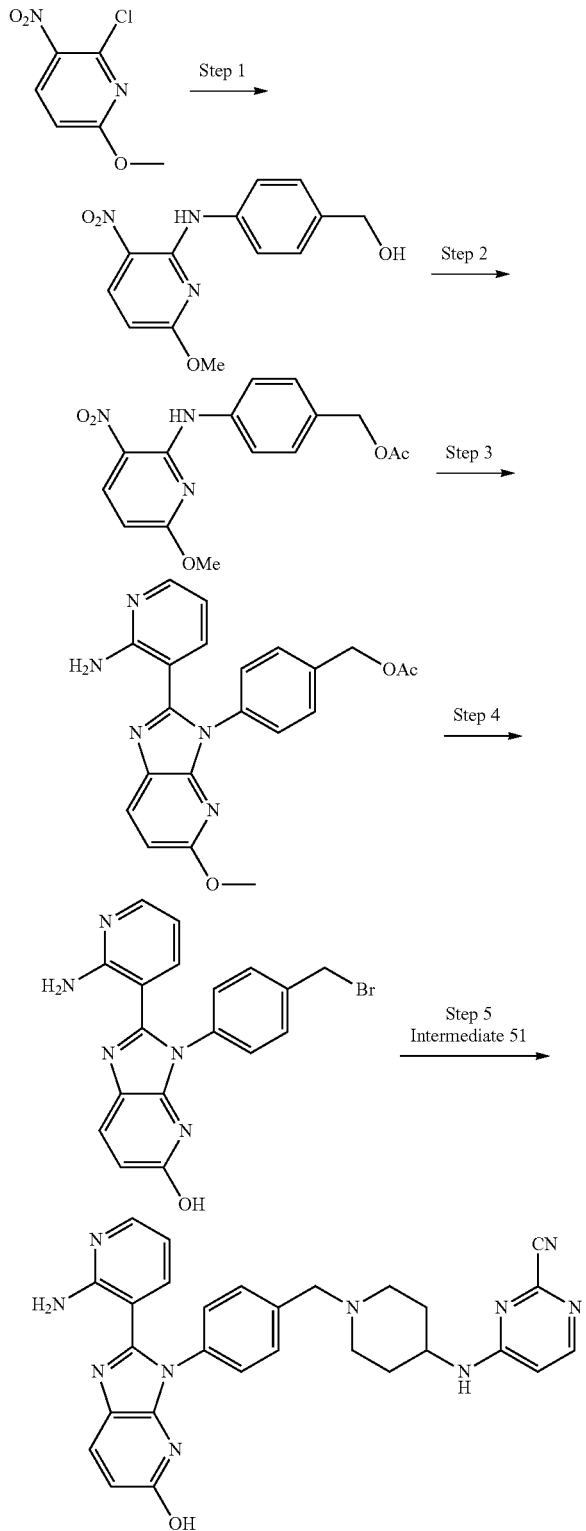

Example 496

Step 1: (4-((6-Methoxy-3-nitropyridin-2-yl)amino)phenyl)methanol

To a solution of 2-chloro-6-methoxy-3-nitropyridine (20 g, 106 mmol) and (4-aminophenyl)methanol (13.1 g, 106 mmol) in 1,4-dioxane (220 mL) was added DIEA (41.1 g, 318 mmol). The mixture was stirred at 110° C. for 16 hr. The reaction mixture was diluted with $H_2O$ (500 mL) and extracted with $CH_2Cl_2$ (500 mL×3). The combined organic layers were washed with brine (400 mL), dried over Na2SO4, filtered, and concentrated under reduced pressure. (4-((6-Methoxy-3-nitropyridin-2-yl)amino)phenyl)methanol (29 g, yield: 97%) was obtained as a yellow solid MS: m/z=276.0 [M+H]$^+$.

Step 2: 4-((6-Methoxy-3-nitropyridin-2-yl)amino)benzyl acetate

To a solution of (4-((6-methoxy-3-nitropyridin-2-yl)amino)phenyl)methanol (29 g, 105 mmol) and TEA (32.0 g, 316 mmol) in $CH_2Cl_2$ (160 mL) were added $Ac_2O$ (10.8 g, 105 mmol) and DMAP (1.29 g, 10.5 mmol). The mixture was stirred at 0° C. for 0.5 hr. The reaction mixture was diluted with $H_2O$ (500 mL) and extracted with $CH_2Cl_2$ (500 mL×3). The combined organic layers were washed with brine (200 mL), dried over $Na_2SO_4$, filtered and concentrated under reduced pressure. After purified by silica gel flash chromatography (Eluent of 0~43% EtOAc in petroleum ether), 4-((6-methoxy-3-nitropyridin-2-yl)amino)benzyl acetate (30 g, yield: 87%) was obtained as a yellow solid. MS: m/z=318.0 [M+H]$^+$. $^1$H NMR (400 MHz, Chloroform-d) δ 10.66 (s, 1H), 8.42 (d, J=9.2 Hz, 1H), 7.68 (d, J=8.4 Hz, 2H), 7.38 (d, J=8.4 Hz, 2H), 6.25 (d, J=8.8 Hz, 1H), 5.11 (s, 2H), 3.97 (s, 3H), 2.12 (s, 3H).

Step 3: 4-(2-(2-Aminopyridin-3-yl)-5-methoxy-3H-imidazo[4,5-b]pyridin-3-yl)benzyl acetate A mixture of 4-((6-methoxy-3-nitropyridin-2-yl)amino)benzyl acetate (15 g, 47.3 mmol), 2-aminonicotinaldehyde (6.93 g, 56.7 mmol), $Na_2S_2O_4$ (32.9 g, 189 mmol) in DMSO (100 mL) was degassed and purged with $N_2$ three times, and then was stirred at 100° C. for 16 hr under $N_2$ atmosphere. The reaction mixture was diluted with $H_2O$ (1500 mL) and extracted with EtOAc (500 mL×3). The combined organic layers were washed with brine (300 mL), dried over $Na_2SO_4$, filtered, and concentrated under reduced pressure. The product was triturated with $CH_2Cl_2$:EtOAc=2:1 (60 mL) and filtered. 4-(2-(2-Aminopyridin-3-yl)-5-methoxy-3H-imidazo[4,5-b]pyridin-3-yl)benzyl acetate (10 g, yield: 50%) was obtained as a brown solid. MS: m/z=390.1 [M+H]$^+$. $^1$H NMR (400 MHz, Chloroform-d) δ 9.42-8.88 (m, 2H), 8.02 (d, J=8.8 Hz, 1H), 7.74 (d, J=5.6 Hz, 1H), 7.56 (d, J=8.0 Hz, 2H), 7.41-7.33 (m, 3H), 6.83 (d, J=8.8 Hz, 1H), 6.55-6.48 (m, 1H), 5.25 (s, 2H), 3.86 (s, 3H), 2.19 (s, 3H).

Step 4: 2-(2-Aminopyridin-3-yl)-3-(4-(bromomethyl)phenyl)-3H-imidazo[4,5-b]pyridin-5-ol To a solution of 4-(2-(2-aminopyridin-3-yl)-5-methoxy-3H-imidazo[4,5-b]pyridin-3-yl)benzyl acetate (500 mg, 1.28 mmol) in $CH_2Cl_2$ (20 mL) was added $BBr_3$ (3.22 g, 12.8 mmol). The mixture was stirred at 80° C. for 12 hr. The mixture was concentrated under reduced pressure to give 2-(2-aminopyridin-3-yl)-3-(4-(bromomethyl)phenyl)-3H- imidazo[4,5-b]pyridin-5-ol (480 mg, crude) as a brown solid. MS: m/z=395.9, 397.9 [M+H]+.

Step 5: 4-((1-(4-(2-(2-Aminopyridin-3-yl)-5-hydroxy-3H-imidazo[4,5-b]pyridin-3-yl)benzyl)piperidin-4-yl)amino)pyrimidine-2-carbonitrile To a solution of 2-(2-aminopyridin-3-yl)-3-(4-(bromomethyl)phenyl)-3H-imidazo[4,5-b]pyridin-5-ol (200 mg, 505 μmol) and Intermediate 51 (103 mg, 323 μmol, TFA) in DMF (2 mL) were added K₂CO₃ (349 mg, 2.52 mmol) and NaI (22.7 mg, 151 μmol). The mixture was stirred at 50° C. for 0.5 hr. The reaction mixture was filtered and concentrated. After purified by prep-HPLC (column: Waters xbridge 150×25 mm 10 μm; mobile phase: [water (NH₄HCO₃)-ACN]; gradient: 40%-70% B over 11 min), 4-((1-(4-(2-(2-aminopyridin-3-yl)-5-hydroxy-3H-imidazo[4,5-b]pyridin-3-yl)benzyl)piperidin-4-yl)amino)pyrimidine-2-carbonitrile (Example 496, 23.1 mg delivered, yield: 8.4%) was obtained as a light yellow lyophilized powder. MS: m/z=519.2 [M+H]+. ¹H NMR (400 MHz, Dimethylsulfoxide-d₆) δ 11.02-10.64 (m, 1H), 8.10-8.01 (m, 3H), 7.92 (dd, J=4.8, 1.6 Hz, 1H), 7.46-7.42 (m, 2H), 7.37-7.34 (m, 2H), 7.05-6.99 (m, 3H), 6.69-6.61 (m, 2H), 6.31 (dd, J=7.6, 4.8 Hz, 1H), 3.88-3.77 (m, 1H), 3.56 (s, 2H), 2.83-2.78 (m, 2H), 2.17-2.10 (m, 2H), 1.92-1.84 (m, 2H), 1.54-1.44 (m, 2H).

Example 497: 4-((1-(4-(5-Amino-2-(2-aminopyridin-3-yl)-3H-imidazo[4,5-b]pyridin-3-yl)benzyl)piperidin-4-yl)amino)pyrimidine-2-carbonitrile

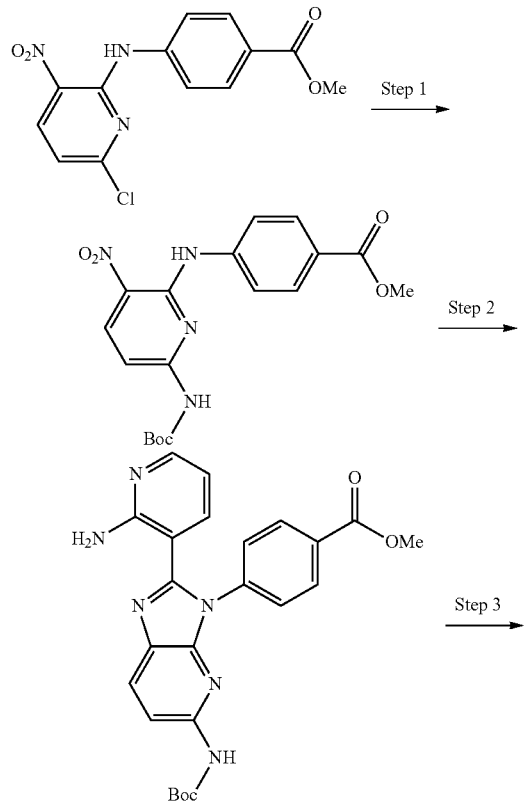

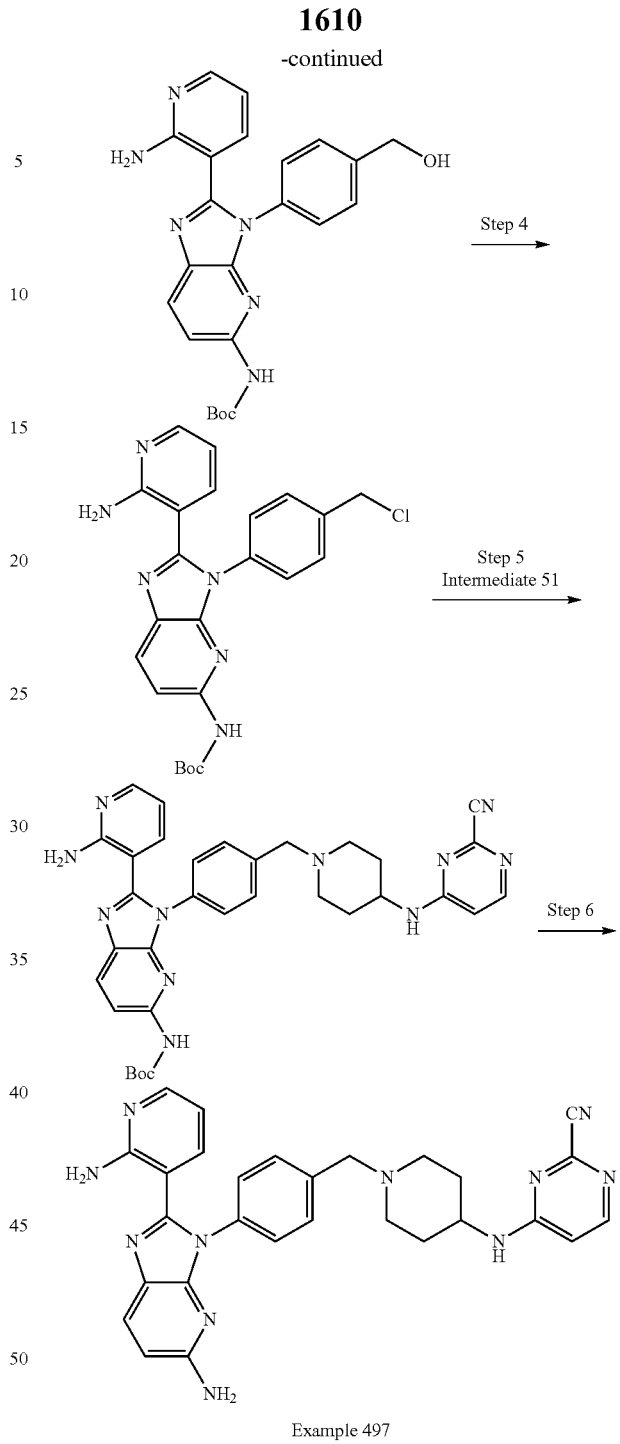

Example 497

Step 1: Methyl 4-((6-((tert-butoxycarbonyl)amino)-3-nitropyridin-2-yl)amino)benzoate A mixture of methyl 4-((6-chloro-3-nitropyridin-2-yl)amino)benzoate (refer to Intermediate 13 for detail procedures, 5 g, 16 mmol), tert-butyl carbamate (1.9 g, 16 mmol), Cs₂CO₃ (10.6 g, 32.5 mmol), XPhos (775 mg, 1.63 mmol) and Pd(OAc)2 (365 mg, 1.63 mmol) in 1,4-dioxane (60 mL) was degassed and purged with N₂ three times, and then was stirred at 100° C. for 16 hr under N₂ atmosphere. The reaction mixture was diluted with H₂O (100 mL) and extracted with CH₂Cl₂ (100 mL×3). The combined organic layers were washed with brine (50 mL×3), dried over Na₂SO₄, filtered, and concentrated under reduced pressure. Methyl 4-((6-((tert-butoxycarbonyl)amino)-3-nitropyridin-2-yl)amino)benzoate (6 g, yield: 77%) was obtained as a brown solid. MS: m/z=333.0 [M+H−t-Bu]⁺.

Step 2: Methyl 4-(2-(2-aminopyridin-3-yl)-5-((tert-butoxycarbonyl)amino)-3H-imidazo[4,5-b]pyridin-3-yl)benzoate To a solution of methyl 4-((6-((tert-butoxycarbonyl)amino)-3-nitropyridin-2-yl)amino)benzoate (2.55 g, 6.57 mmol) in DMSO (20 mL) were added Na₂S₂O₄ (5.38 g, 26.3 mmol, 85% purity) and 2-aminonicotinaldehyde (882 mg, 7.22 mmol). The mixture was stirred at 80° C. for 16 hr. The reaction mixture was quenched with H₂O (25 mL) at 25° C. The mixture was diluted with CH₂Cl₂ (50 mL), washed with H₂O (50 mL×3) and brine (100 mL), dried over Na₂SO₄, filtered, and concentrated under reduced pressure. After purified by silica gel flash chromatography (Eluent of 30%~50% EtOAc in petroleum ether), methyl 4-(2-(2-aminopyridin-3-yl)-5-((tert-butoxycarbonyl)amino)-3H-imidazo[4,5-b]pyridin-3-yl)benzoate (260 mg, yield: 33%) was obtained as a yellow solid. MS: m/z=461.1 [M+H]⁺. ¹H NMR (400 MHz, Dimethylsulfoxide-d₆) δ 9.71 (s, 1H), 8.15 (d, J=8.8 Hz, 1H), 8.06 (d, J=8.4 Hz, 2H), 7.98 (dd, J=4.8, 1.6 Hz, 1H), 7.88-7.76 (m, 1H), 7.58 (d, J=8.4 Hz, 2H), 7.14 (dd, J=7.6, 1.2 Hz, 1H), 6.83 (s, 2H), 6.41 (dd, J=7.6, 4.8 Hz, 1H), 3.89 (s, 3H), 1.45 (s, 9H).

Step 3: Tert-butyl (2-(2-aminopyridin-3-yl)-3-(4-(hydroxymethyl)phenyl)-3H-imidazo[4,5-b]pyridin-5-yl)carbamate To a solution of methyl 4-(2-(2-aminopyridin-3-yl)-5-((tert-butoxycarbonyl)amino)-3H-imidazo[4,5-b]pyridin-3-yl)benzoate (250 mg, 543 μmol) in THF (5 mL) was added LiAlH₄ (41.2 mg, 1.1 mmol) at 0° C. After addition, the resulting mixture was stirred at 25° C. for 1 hr.
Then the reaction mixture was filtered. The filtrate was concentrated to give tert-butyl (2-(2-aminopyridin-3-yl)-3-(4-(hydroxymethyl)phenyl)-3H-imidazo[4,5-b]pyridin-5-yl)carbamate (230 mg, yield: 66%) as a yellow solid. MS: m/z=433.1 [M+1]+.

Step 4: Tert-butyl (2-(2-aminopyridin-3-yl)-3-(4-(chloromethyl)phenyl)-3H-imidazo[4,5-b]pyridin-5-yl)carbamate To a solution of tert-butyl (2-(2-aminopyridin-3-yl)-3-(4-(hydroxymethyl)phenyl)-3H-imidazo[4,5-b]pyridin-5-yl)carbamate (230 mg, 532 μmol) in CH₂Cl₂ (5 mL) was added SOCl₂ (189 mg, 1.6 mmol) at 0° C. The mixture was stirred at 40° C. for 0.5 hr. The reaction mixture was quenched with H₂O (1 mL) at 25° C. and concentrated under reduced pressure. tert-Butyl (2-(2-aminopyridin-3-yl)-3-(4-(chloromethyl)phenyl)-3H-imidazo[4,5-b]pyridin-5-yl)carbamate (260 mg, HCl salt) was obtained as a yellow solid. MS: m/z=451.0 [M+H]⁺.

Step 5: Tert-butyl (2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)carbamate To a solution of tert-butyl (2-(2-aminopyridin-3-yl)-3-(4-(chloromethyl)phenyl)-3H-imidazo[4,5-b]pyridin-5-yl)carbamate (260 mg, 533 gmol, HCl salt) and Intermediate 51 (169 mg, 533 μmol, TFA) in DMF (5 mL) were added K₂CO₃ (369 mg, 2.67 mmol) and NaI (40 mg, 267 ol). The mixture was stirred at 50° C. for 1 hr. The reaction mixture was quenched with H₂O (25 mL) at 25° C., and then diluted with CH₂Cl₂ (50 mL). The organic layer was washed with H₂O (50 mL×3) and brine (100 mL), dried over Na₂SO₄, filtered and concentrated under reduced pressure. Tert-butyl (2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)carbamate (300 mg, yield: 67%) was obtained as a yellow solid. MS: m/z=618.1 [M+H]⁺.

Step 6: 4-((1-(4-(5-Amino-2-(2-aminopyridin-3-yl)-3H-imidazo[4,5-b]pyridin-3-yl)benzyl)piperidin-4-yl)amino)pyrimidine-2-carbonitrile A mixture of tert-butyl (2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)carbamate (260 mg, 421 μmol, HCl salt) in 4 M HCl in 1,4-dioxane (3 mL) was stirred at 25° C. for 2 hr. The reaction was concentrated under reduced pressure to give product as a yellow solid. The product was diluted with aqueous NaHCO₃ (10 mL) and extracted with CH₂Cl₂ (10 mL×3). The combined organic layers were washed with brine (20 mL), dried over Na₂SO₄, filtered, and concentrated under reduced pressure. After purified by prep-HPLC (column: Waters xbridge 150×25 mm 10 μm; mobile phase: [water (NH₄HCO₃)-ACN]; gradient: 16%-46% B over 11 min), 4-((1-(4-(5-amino-2-(2-aminopyridin-3-yl)-3H-imidazo[4,5-b]pyridin-3-yl)benzyl)piperidin-4-yl)amino)pyrimidine-2-carbonitrile (Example 497, 21.9 mg, yield: 10%) was obtained as a yellow powder. MS: m/z=518.2 [M+H]⁺. ¹H NMR (400 MHz, Dimethylsulfoxide-d₆) δ 8.06-7.95 (m, 1H), 7.90 (dd, J=4.8, 1.2 Hz, 1H), 7.82 (d, J=8.4 Hz, 1H), 7.53-7.45 (m, 2H), 7.33 (d, J=8.0 Hz, 2H), 7.19 (dd, J=7.6, 1.2 Hz, 1H), 6.67-6.50 (m, 2H), 6.42 (dd, J=7.6, 4.8 Hz, 1H), 4.08-3.75 (m, 1H), 3.64 (s, 2H), 2.97-2.86 (m, 2H), 2.25 (t, J=11.2 Hz, 2H), 2.05-1.95 (m, 2H), 1.67-1.55 (m, 2H).

Example 498: 4-((1-(4-(2-(2-Aminopyridin-3-yl)-5-(2-chloro-4-fluorophenyl)-3H-imidazo[4,5-b]pyridin-3-yl)benzyl)piperidin-4-yl)amino)pyrimidine-2-carbonitrile

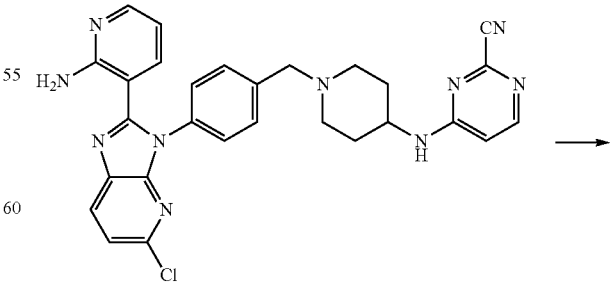

Example 405

1613
-continued

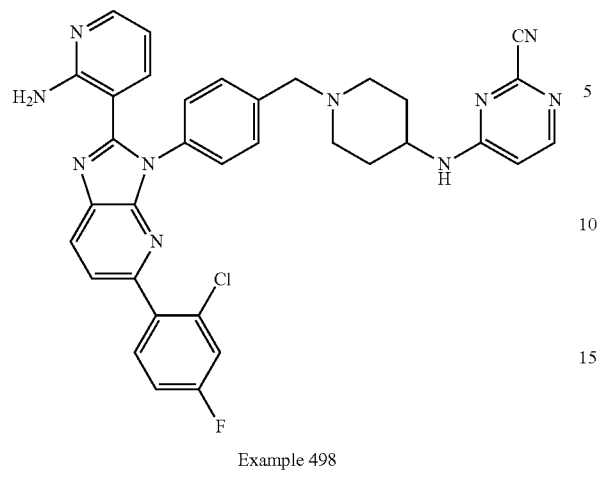

Example 498

A mixture of Example 405 (300 mg, 559 μmol), (2-chloro-4-fluorophenyl)boronic acid (107 mg, 615 μmol), K₂CO₃ (232 mg, 1.68 mmol) and Pd(PPh3)4 (65 mg, 56 μmol) in THF (2.5 mL) and H₂O (0.5 mL) was degassed and purged with N₂ three times, and then was stirred at 80° C. for 2 hr under N₂ atmosphere. The reaction mixture was diluted with H₂O (10 mL) and extracted with EtOAc (10 mL×2). The combined organic layers were washed with brine (30 mL), dried over Na₂SO₄, filtered, and concentrated under reduced pressure. After purified by prep-HPLC (column: Phenomenex C18 150×25 mm×10 μm; mobile phase: [water (NH₄HCO₃)-ACN]; gradient: 48%-78% B over 11 min), 4-((1-(4-(2-(2-aminopyridin-3-yl)-5-(2-chloro-4-fluorophenyl)-3H-imidazo[4,5-b]pyridin-3-yl)benzyl)piperidin-4-yl)amino)pyrimidine-2-carbonitrile (Example 498, 129.5 mg, yield. 37%) was obtained as a yellow powder. MS: m/z=631.3 [M+H]⁺. ¹H NMR (400 MHz, Dimethysulfoxide-d₆) δ 8.29 (d, J=8.0 Hz, 1H), 8.13-7.94 (m, 3H), 7.66-7.53 (m, 3H), 7.46-7.38 (m, 4H), 7.36-7.30 (m, 1H), 7.15 (dd, J=7.6, 1.6 Hz, 1H), 6.98 (s, 2H), 6.66 (d, J=6.0 Hz, 1H), 6.38 (dd, J=8.0, 5.2 Hz, 1H), 3.91-3.63 (m, 1H), 3.55 (s, 2H), 2.85-2.75 (m, 2H), 2.17-2.06 (m, 2H), 1.92-1.79 (m, 2H), 1.54-1.41 (m, 2H). ¹⁹F NMR (400 MHz, Dimethylsulfoxide-d₆) δ −111.64.

Example 499: 4-((1-(4-(2-(2-aminopyridin-3-yl)-5-(4-fluorophenyl)-6-methyl-3H-imidazo[4,5-b]pyridin-3-yl)benzyl)piperidin-4-yl)amino)pyrimidine-2-carbonitrile

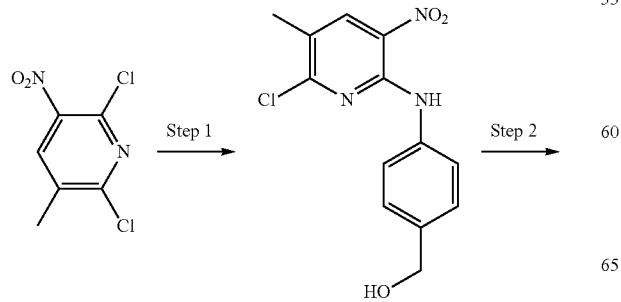

1614
-continued

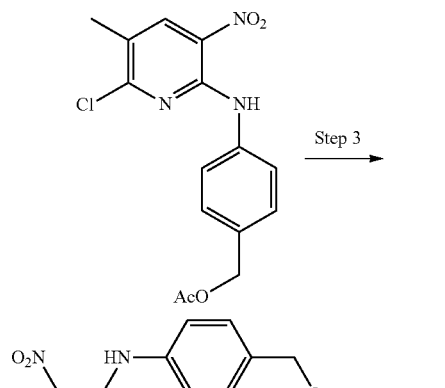

Step 3

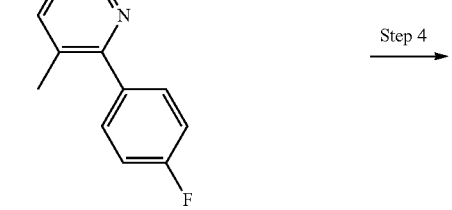

Step 4

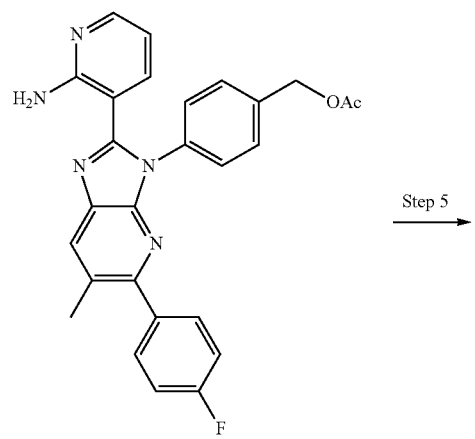

Step 5

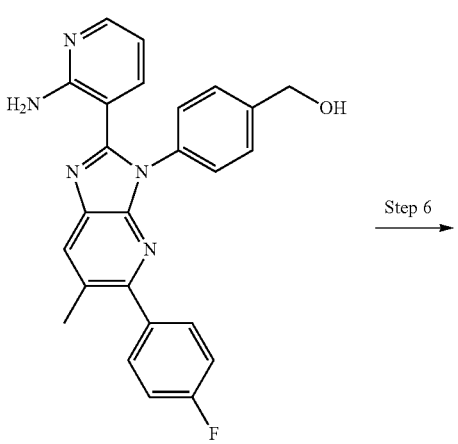

Step 6

1615

-continued

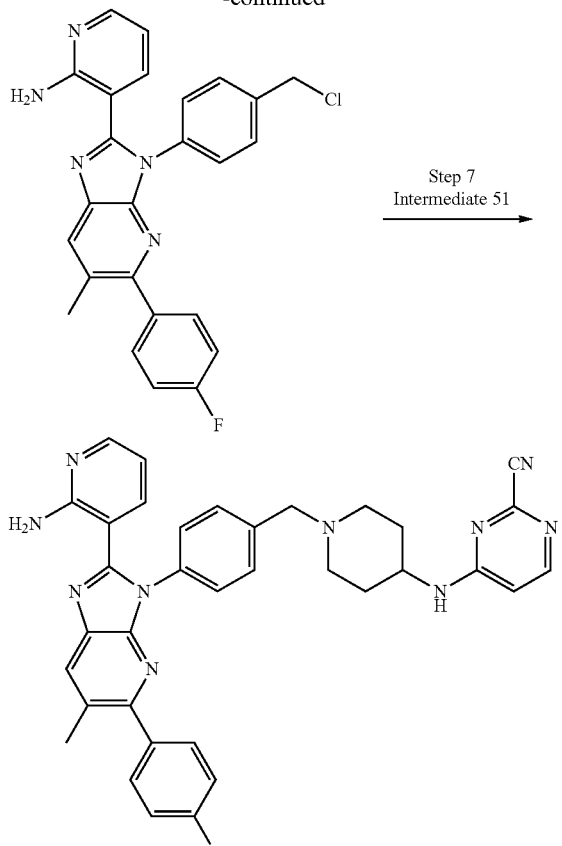

Example 499

Step 1: (4-((6-Chloro-5-methyl-3-nitropyridin-2-yl)amino)phenyl)methanol

To a solution of 2,6-dichloro-3-methyl-5-nitropyridine (2 g, 9.7 mmol) and (4-aminophenyl)methanol (1.2 g, 9.7 mmol) in 1,4-dioxane (25 mL) was added DIEA (2.5 g, 19.3 mmol) at 25° C. The mixture was stirred at 70° C. for 12 hr. The reaction mixture was poured into H$_2$O (100 mL) and extracted with CH$_2$Cl$_2$ (50 mL×2). The combined organic layers were washed with brine (40 mL), dried over anhydrous Na$_2$SO$_4$, filtered and concentrated. After purified by silica gel flash chromatography (Eluent of 0~60% EtOAc in petroleum ether), (4-((6-chloro-5-methyl-3-nitropyridin-2-yl)amino)phenyl)methanol (2.3 g, yield: 81%) was obtained as a yellow solid. MS: m/z=293.9 [M+H]$^+$. $^1$H NMR (400 MHz, Dimethylsulfoxide-d$_6$) δ 9.96 (s, 1H), 8.55 (d, J=0.6 Hz, 1H), 7.54 (d, J=8.4 Hz, 2H), 7.32 (d, J=8.4 Hz, 2H), 5.16 (t, J=6.4 Hz, 1H), 4.49 (d, J=6.0 Hz, 2H), 2.29 (s, 3H).

Step 2: 4-((6-Chloro-5-methyl-3-nitropyridin-2-yl)amino)benzyl acetate

To a solution of (4-((6-chloro-5-methyl-3-nitropyridin-2-yl)amino)phenyl)methanol (2.3 g, 7.8 mmol) and acetic anhydride (1.2 g, 11.8 mmol) in CH2Cl2 (25 mL) were added TEA (2.4 g, 23.5 mmol) and DMAP (96 g, 783 μmol) at 0° C. The mixture was stirred at 0° C. for 2 hr. The reaction mixture was poured into H$_2$O (100 mL) and extracted with CH$_2$Cl$_2$ (50 mL×2). The combined organic layers were washed with brine (40 mL), dried over anhydrous Na$_2$SO$_4$, filtered, and concentrated. After purified by silica gel flash chromatography (Eluent of 0~40% EtOAc in petroleum ether), 4-((6-chloro-5-methyl-3-nitropyridin-2-yl)amino)benzyl acetate (2.5 g, yield: 94%) was obtained as a yellow solid. MS: m/z=335.8 [M+H]$^+$. 9.98 (s, 1H), 8.57 (s, 1H), 7.61 (d, J=8.4 Hz, 2H), 7.38 (d, J=8.4 Hz, 2H), 5.06 (s, 2H), 2.30 (s, 3H), 2.07 (s, 3H).

Step 3: 4-((6-(4-Fluorophenyl)-5-methyl-3-nitropyridin-2-yl)amino)benzyl acetate To a solution of 4-((6-chloro-5-methyl-3-nitropyridin-2-yl)amino)benzyl acetate (2.2 g, 6.6 mmol) in 1,4-dioxane (30 mL) and H$_2$O (10 mL) were added Cs$_2$CO$_3$ (6.4 g, 20 mmol), (4-fluorophenyl)boronic acid (1 g, 7.2 mmol) and Pd(dppf)Cl$_2$ (240 mg, 328 μmol) at 25° C. The reaction mixture was degassed and purged with N$_2$ three times, and then was stirred at 85° C. for 12 hr under N$_2$. The reaction mixture was poured into H$_2$O (100 mL) and extracted with CH$_2$Cl$_2$ (50 mL×2). The combined organic layers were washed with brine (40 mL), dried over anhydrous Na$_2$SO$_4$, filtered and concentrated. After purified by silica gel flash chromatography (Eluent of 0~60% EtOAc in petroleum ether), 4-((6-(4-fluorophenyl)-5-methyl-3-nitropyridin-2-yl)amino)benzyl acetate (1.8 g, yield: 67%) was obtained as a yellow solid. MS: m/z=396.0 [M+H]$^+$. $^1$H NMR (400 MHz, Dimethylsulfoxide-d$_6$) δ 9.95 (s, 1H), 8.52 (s, 1H), 7.74-7.68 (m, 4H), 7.37-7.30 (m, 4H), 5.02 (s, 2H), 2.33 (s, 3H), 2.05 (s, 3H). $^{19}$F NMR (400 MHz, Dimethylsulfoxide-d$_6$) δ −111.84.

Step 4: 4-(2-(2-Aminopyridin-3-yl)-5-(4-fluorophenyl)-6-methyl-3H-imidazo[4,5-b]pyridin-3-yl)benzyl acetate To a solution of 4-((6-(4-fluorophenyl)-5-methyl-3-nitropyridin-2-yl)amino)benzyl acetate (1.8 mg, 4.6 mmol) in DMSO (50 mL) were added 2-aminonicotinaldehyde (667 mg, 5.5 mmol) and Na$_2$S$_2$O$_4$ (3.2 g, 18.2 mmol) at 25° C. The mixture was stirred at 100° C. for 12 hr. The reaction mixture was poured into H$_2$O (100 mL) and extracted with CH$_2$Cl$_2$ (50 mL×2). The combined organic layers were washed with brine (400 mL), dried over anhydrous Na$_2$SO$_4$, filtered and concentrated. After purified silica gel by flash chromatography (Eluent of 0~3% MeOH in CH$_2$Cl$_2$), 4-(2-(2-aminopyridin-3-yl)-5-(4-fluorophenyl)-6-methyl-3H-imidazo[4,5-b]pyridin-3-yl)benzyl acetate (1.4 g, yield: 52%) was obtained as a yellow solid. MS: m/z=468.1 [M+H]$^+$. $^1$H NMR (400 MHz, Dimethylsulfoxide-d$_6$) δ 8.14 (s, 1H), 7.99 (dd, J=4.8, 2.0 Hz, 1H), 7.56-7.51 (m, 2H), 7.50-7.43 (m, 4H), 7.27 (t, J=8.8 Hz, 2H), 7.18 (dd, J=7.6, 1.6 Hz, 1H), 6.92 (s, 2H), 6.41 (dd, J=7.6, 4.8 Hz, 1H), 5.13 (s, 2H), 2.43 (s, 3H), 2.08 (s, 3H). $^{19}$F NMR (400 MHz, Dimethylsulfoxide-d$_6$) δ −114.38.

Step 5: (4-(2-(2-Aminopyridin-3-yl)-5-(4-fluorophenyl)-6-methyl-3H-imidazo[4,5-b]pyridin-3-yl)phenyl)methanol To a solution of 4-(2-(2-aminopyridin-3-yl)-5-(4-fluorophenyl)-6-methyl-3H-imidazo[4,5-b]pyridin-3-yl)benzyl acetate (1.3 g, 2.8 mmol) in H$_2$O (1 mL), MeOH (3 mL) and THF (3 mL) was added K$_2$CO$_3$ (769 mg, 5.6 μmol) at 25° C. The mixture was stirred at 25° C. for 1 hr. The reaction mixture was poured into H$_2$O (50 mL) and extracted with CH$_2$Cl$_2$ (20 mL×2). The combined organic layers were washed with brine (40 mL), dried over anhydrous Na$_2$SO$_4$, filtered and concentrated. (4-(2-(2-Aminopyridin-3-yl)-5-(4-fluorophenyl)-6-methyl-3H-imidazo[4,5-b]pyridin-3-yl)phenyl)methanol (860 mg, yield: 57%) was obtained as a yellow solid. MS: m/z=426.1 [M+H]$^+$. $^1$H NMR (400 MHz, Dimethylsulfoxide-d$_6$) δ 8.13 (s, 1H), 7.99 (dd, J=4.8, 2.0 Hz, 1H), 7.53 (dd, J=8.4, 5.6 Hz, 2H), 7.45-7.36 (m, 4H), 7.26 (t, J=9.2 Hz, 2H), 7.18 (dd, J=7.6, 1.6 Hz, 1H), 7.00 (s, 2H), 6.40 (dd, J=7.85, 4.8 Hz, 1H), 5.31 (t, J=6.0 Hz, 1H), 4.55 (d, J=6.0 Hz, 2H), 2.43 (s, 3H). $^{19}$F NMR (400 MHz, Dimethylsulfoxide-d$_6$) δ −114.42.

Step 6: 3-(3-(4-(Chloromethyl)phenyl)-5-(4-fluorophenyl)-6-methyl-3H-imidazo[4,5-b]pyridin-2-yl)pyridin-2-amine To a solution of (4-(2-(2-aminopyridin-3-yl)-5-(4-fluorophenyl)-6-methyl-3H-imidazo[4,5-b]pyridin-3-yl)phenyl)methanol (200 mg, 470 µmol) in CH2Cl2 (5 mL) was added SOCl2 (280 mg, 2.4 mmol) at 25° C. The mixture was stirred at 40° C. for 0.5 hr. The reaction mixture was concentrated under reduced pressure to give 3-(3-(4-(chloromethyl)phenyl)-5-(4-fluorophenyl)-6-methyl-3H-imidazo[4,5-b]pyridin-2-yl)pyridin-2-amine (200 mg, crude) as a yellow solid, which was used in the next step without further purification. MS: m/z=444.0 [M+H]$^+$. $^1$H NMR (400 MHz, Dimethylsulfoxide-d$_6$) δ 8.15 (s, 1H), 8.00 (dd, J=4.8, 1.6 Hz, 1H), 7.60-7.51 (m, 4H), 7.45 (d, J=8.0 Hz, 2H), 7.27 (t, J=8.8 Hz, 2H), 7.22-7.17 (m, 1H), 6.97 (br s, 2H), 6.43 (dd, J=7.2, 4.8 Hz, 1H), 4.82 (s, 2H), 2.44 (s, 3H). $^{19}$F NMR (400 MHz, Dimethylsulfoxide-d$_6$) δ −114.34.

Step 7: 4-((1-(4-(2-(2-Aminopyridin-3-yl)-5-(4-fluorophenyl)-6-methyl-3H-imidazo[4,5-b]pyridin-3-yl)benzyl)piperidin-4-yl)amino)pyrimidine-2-carbonitrile To a solution of 3-(3-(4-(chloromethyl)phenyl)-5-(4-fluorophenyl)-6-methyl-3H-imidazo[4,5-b]pyridin-2-yl)pyridin-2-amine (200 mg, 451 µmol) in DMF (3 mL) were added Intermediate 51 (110 mg, 541 µmol), NaI (34 mg, 225 µmol) and K$_2$CO$_3$ (249 mg, 1.8 mmol) at 25° C. The mixture was stirred at 40° C. for 1 hr. The reaction mixture was poured into H$_2$O (50 mL) and extracted with CH$_2$Cl$_2$ (20 mL×2). The combined organic layers were washed with brine (40 mL), dried over anhydrous Na$_2$SO$_4$, filtered, and concentrated to dryness. After purified by silica gel flash chromatography (Eluent of 0~5% MeOH in CH$_2$Cl$_2$), 4-((1-(4-(2-(2-aminopyridin-3-yl)-5-(4-fluorophenyl)-6-methyl-3H-imidazo[4,5-b]pyridin-3-yl)benzyl)piperidin-4-yl)amino)pyrimidine-2-carbonitrile (Example 499, 126.3 mg, yield: 45% for two steps) was obtained as a yellow solid. MS: m/z=611.4 [M+H]$^+$. $^1$H NMR (400 MHz, Dimethylsulfoxide-d$_6$) δ 8.15 (s, 1H), 8.09 (d, J=6.0 Hz, 1H), 8.04 (d, J=7.2 Hz, 1H), 7.99 (dd, J=4.8, 1.6 Hz, 1H), 7.58-7.51 (m, 2H), 7.46-7.36 (m, 4H), 7.31-7.25 (m, 2H), 7.11 (dd, J=7.6, 1.6 Hz, 1H), 7.03 (s, 2H), 6.67 (d, J=6.0 Hz, 1H), 6.37 (dd, J=7.6, 4.4 Hz, 1H), 3.87-3.73 (m, 1H), 3.55 (s, 2H), 2.85-2.75 (m, 2H), 2.44 (s, 3H), 2.20-2.06 (m, 2H), 1.94-1.80 (m, 2H), 1.55-1.41 (m, 2H). $^{19}$F NMR (400 MHz, Dimethylsulfoxide-d$_6$) δ −114.39.

Example 500: 2-(2-Aminopyridin-3-yl)-1-(4-((4-((2-cyanopyrimidin-4-yl)amino)piperidin-1-yl)methyl)phenyl)-1H-benzo[d]imidazole-6-carbonitrile

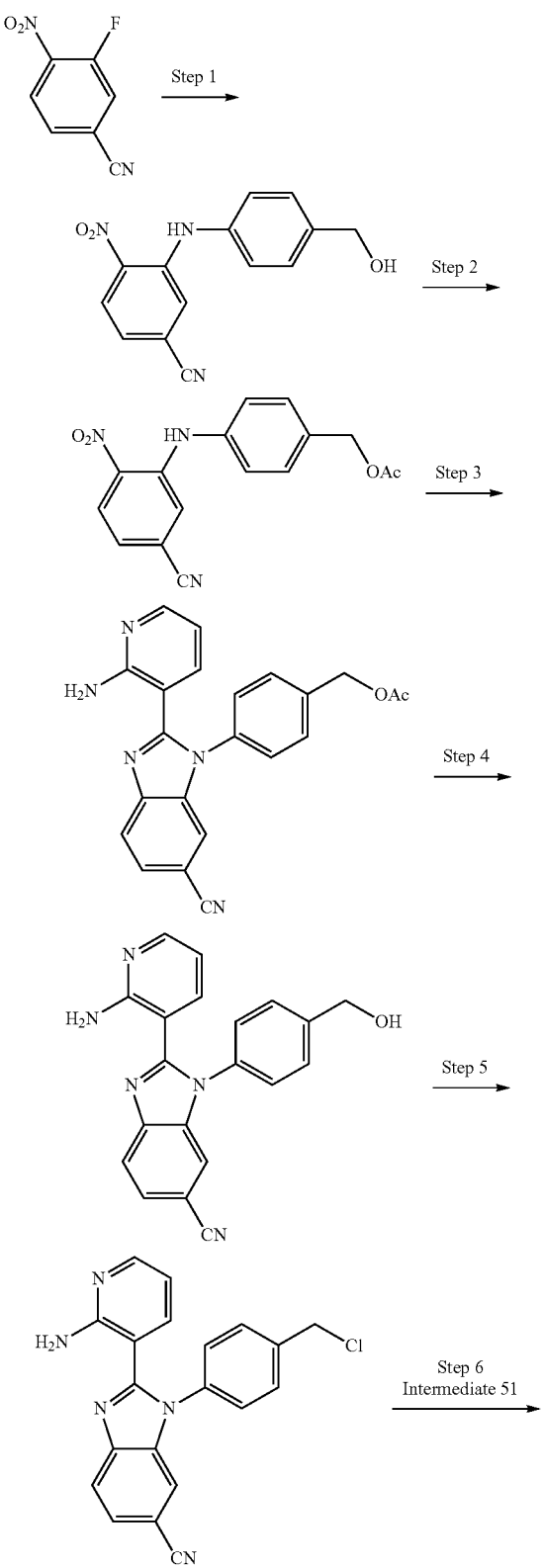

-continued

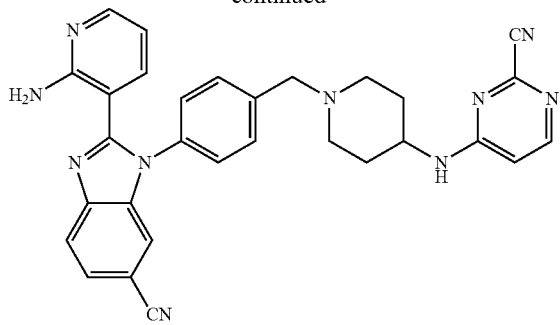

Example 500

Step 1: 3-((4-(Hydroxymethyl)phenyl)amino)-4-nitrobenzonitrile

To a solution of 3-fluoro-4-nitrobenzonitrile (6.74 g, 40.6 mmol) and (4-aminophenyl)methanol (5 g, 40.6 mmol) in DMSO (50 mL) was added DIEA (26 g, 203 mmol). The mixture was stirred at 100° C. for 16 hr. The reaction mixture was diluted with H$_2$O (100 mL) and extracted with CH$_2$Cl$_2$ (100 mL×3). The combined organic layers were washed with brine (120 mL), dried over Na$_2$SO$_4$, filtered and concentrated under reduced pressure. 3-((4-(Hydroxymethyl)phenyl)amino)-4-nitrobenzonitrile (10.5 g, crude) was obtained as a yellow solid. $^1$H NMR (400 MHz, Dimethylsulfoxide-d$_6$) δ 9.47 (s, 1H), 8.23 (d, J=8.8 Hz, 1H), 7.42-7.37 (m, 3H), 7.33-7.28 (m, 2H), 7.20 (dd, J=8.8, 2.0 Hz, 1H), 5.23 (t, J=5.6 Hz, 1H), 4.52 (d, J=6.0 Hz, 2H).

Step 2: 4-((5-Cyano-2-nitrophenyl)amino)benzyl acetate

To a solution of 3-((4-(hydroxymethyl)phenyl)amino)-4-nitrobenzonitrile (5 g, 18.6 mmol) and TEA (5.64 g, 56 mmol) in CH$_2$Cl$_2$ (50 mL) were added Ac$_2$O (2.84 g, 28 mmol) and DMAP (227 mg, 1.86 mmol). The mixture was stirred at 25° C. for 1 hr. The reaction mixture was diluted with H$_2$O (300 mL) and extracted with CH$_2$Cl$_2$ (200 mL×3). The combined organic layers were washed with brine (300 mL), dried over Na$_2$SO$_4$, filtered, and concentrated under reduced pressure. After purified by silica gel flash chromatography (Eluent of 0~10% EtOAc in petroleum ether), 4-((5-cyano-2-nitrophenyl)amino)benzyl acetate (5.5 g, yield: 95%) was obtained as a red solid. $^1$H NMR (400 MHz, Dimethylsulfoxide-d$_6$) δ 9.45 (s, 1H), 8.23 (d, J=8.8 Hz, 1H), 7.51 (d, J=1.6 Hz, 1H), 7.45-7.41 (m, 2H), 7.37-7.32 (m, 2H), 7.25 (dd, J=8.8, 1.6 Hz, 1H), 5.08 (s, 2H), 2.08 (s, 3H).

Step 3: 4-(2-(2-Aminopyridin-3-yl)-6-cyano-1H-benzo[d]imidazol-1-yl)benzyl acetate A mixture of 4-((5-cyano-2-nitrophenyl)amino)benzyl acetate (3 g, 9.65 mmol), 2-aminonicotinaldehyde (1.29 g, 10.6 mmol), Na$_2$S$_2$O$_4$ (7.9 g, 39 mmol) in DMSO (30 mL) was degassed and purged with N$_2$ three times, and then was stirred at 100° C. for 16 hr under N$_2$ atmosphere. The reaction mixture was diluted with H$_2$O (100 mL) and extracted with CH$_2$Cl$_2$ (200 mL×3). The combined organic layers were washed with brine (300 mL), dried over Na$_2$SO$_4$, and concentrated under reduced pressure. After purified by silica gel flash chromatography (Eluent of 10-50% EtOAc in petroleum ether and 50% CH$_2$Cl$_2$ in MeOH), 4-(2-(2-aminopyridin-3-yl)-6-cyano-1H-benzo[d]imidazol-1-yl)benzyl acetate (600 mg, yield: 16%) was obtained as a yellow solid. MS: m/z=384.1 [M+H]$^+$. $^1$H NMR (400 MHz, Dimethylsulfoxide-d$_6$) δ 8.03-7.94 (m, 2H), 7.76-7.68 (m, 2H), 7.59-7.46 (m, 4H), 7.21 (dd, J=7.6, 1.6 Hz, 1H), 6.91 (s, 2H), 6.42 (dd, J=7.6, 4.8 Hz, 1H), 5.17 (s, 2H), 2.11 (s, 3H).

Step 4: 2-(2-Aminopyridin-3-yl)-1-(4-(hydroxymethyl)phenyl)-1H-benzo[d]imidazole-6-carbonitrile To a solution of 4-(2-(2-aminopyridin-3-yl)-6-cyano-1H-benzo[d]imidazol-1-yl)benzyl acetate (570 mg, 1.49 mmol) in THF (2 mL) was added K$_2$CO$_3$ (616 mg, 4.46 mmol) in MeOH (2 mL) and H$_2$O (2 mL). The mixture was stirred at 25° C. for 1 hr. The reaction mixture was diluted with H$_2$O (20 mL) and extracted with EtOAc (20 mL×3). The combined organic layers were washed with brine (30 mL), dried over Na$_2$SO$_4$, filtered and concentrated under reduced pressure. 2-(2-Aminopyridin-3-yl)-1-(4-(hydroxymethyl)phenyl)-1H-benzo[d]imidazole-6-carbonitrile (500 mg, crude) was obtained as a yellow solid. MS: m/z=342.0 [M+H]$^+$.

Step 5: 2-(2-Aminopyridin-3-yl)-1-(4-(chloromethyl)phenyl)-1H-benzo[d]imidazole-6-carbonitrile To a solution of 2-(2-aminopyridin-3-yl)-1-(4-(hydroxymethyl)phenyl)-11H-benzo[d]imidazole-6-carbonitrile (500 mg, 1.46 mmol) in CH$_2$Cl$_2$ (2 mL) was added SOCl$_2$ (348 mg, 2.93 mmol). The mixture was stirred at 50° C. for 1 hr and then concentrated under reduced pressure. 2-(2-Aminopyridin-3-yl)-1-(4-(chloromethyl)phenyl)-1H-benzo[d]imidazole-6-carbonitrile (530 mg, crude) was obtained as a yellow solid. MS: m/z=360.0 [M+H]$^+$.

Step 6: 2-(2-Aminopyridin-3-yl)-1-(4-((4-((2-cyanopyrimidin-4-yl)amino)piperidin-1-yl)methyl)phenyl)-1H-benzo[d]imidazole-6-carbonitrile To a solution of 2-(2-aminopyridin-3-yl)-1-(4-(chloromethyl)phenyl)-1H-benzo[d]imidazole-6-carbonitrile (300 mg, 757 µmol) and Intermediate 51 (240 mg, 757 µmol) in DMF (3 mL) were added NaI (56.7 mg, 379 µmol) and K$_2$CO$_3$ (418 mg, 3.03 mmol). The mixture was stirred at 25° C. for 16 hr. The reaction mixture was diluted with H$_2$O (15 mL) and extracted with EtOAc (20 mL×2). The combined organic layers were washed with brine (30 mL), dried over Na$_2$SO$_4$, filtered, and concentrated under reduced pressure. After purified by prep-HPLC (column: Phenomenex C18 150×25 mm×10 µm; mobile phase: [water (NH$_4$HCO$_3$)-ACN]; gradient: 35%-65% B over 11 min), 2-(2-aminopyridin-3-yl)-1-(4-((4-((2-cyanopyrimidin-4-yl)amino)piperidin-1-yl)methyl)phenyl)-1H-benzo[d]imidazole-6-carbonitrile (Example 500, 157.7 mg, yield: 40%) was obtained as a yellow powder. MS: m/z=527.4 [M+H]$^+$. $^1$H NMR (400 MHz, Dimethylsulfoxide-d$_6$) δ 8.30-7.90 (m, 4H), 7.78-7.65 (m, 2H), 7.54-7.39 (m, 4H), 7.15 (dd, J=7.6, 1.6 Hz, 1H), 7.01 (s, 2H), 6.84-6.63 (m, 1H), 6.37 (dd, J=7.6, 4.8 Hz, 1H), 3.89-3.74 (m, 1H), 3.59 (s, 2H), 2.83 (d, J=11.2 Hz, 2H), 2.15 (t, J=10.8 Hz, 2H), 1.95-1.80 (m, 2H), 1.56-1.43 (m, 2H).

1621

Example 501: 2-(2-Aminopyridin-3-yl)-1-(4-((4-((2-cyanopyrimidin-4-yl)amino)piperidin-1-yl)methyl)phenyl)-1H-benzo[d]imidazole-5-carbonitrile

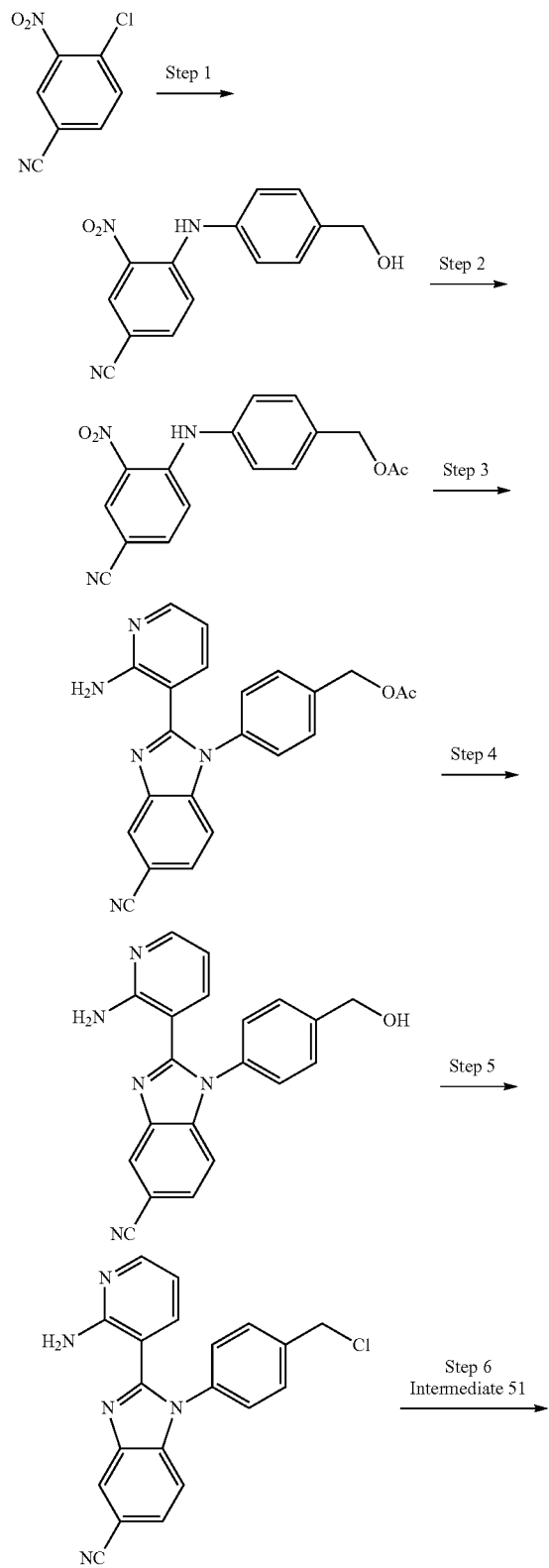

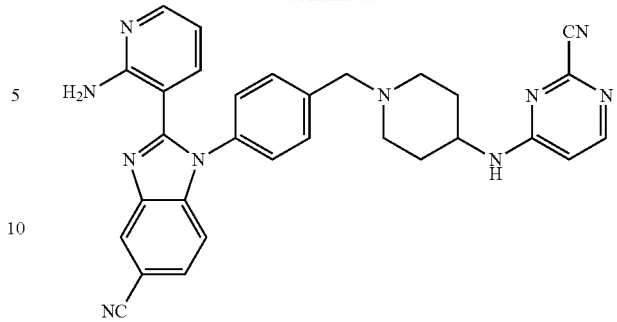

Example 501

Step 1: 4-((4-(Hydroxymethyl)phenyl)amino)-3-nitrobenzonitrile

To a solution of 4-chloro-3-nitrobenzonitrile (5 g, 27 mmol) and (4-aminophenyl)methanol (4.05 g, 33 mmol) in DMSO (50 mL) was added DIEA (8.85 g, 68 mmol). The mixture was stirred at 100° C. for 1 hr. The mixture was added $H_2O$ (500 mL), and stirred at 5° C. for 10 min. After filtration, 4-((4-(hydroxymethyl)phenyl)amino)-3-nitrobenzonitrile (7.7 g) was obtained as a yellow solid. $^1$H NMR (400 MHz, Dimethysulfoxide-$d_6$) δ 9.89 (s, 1H), 8.58 (d, J=2.0 Hz, 1H), 7.75 (dd, J=8.8, 2.0 Hz, 1H), 7.42 (d, J=8.4 Hz, 2H), 7.30 (d, J=8.4 Hz, 2H), 7.04 (d, J=9.2 Hz, 1H), 5.27 (t, J=5.6 Hz, 1H), 4.53 (d, J=5.6 Hz, 2H).

Step 2: 4-((4-Cyano-2-nitrophenyl)amino)benzyl acetate

To a solution of 4-((4-(hydroxymethyl)phenyl)amino)-3-nitrobenzonitrile (7.7 g, 28.6 mmol) and TEA (8.68 g, 86 mmol) in $CH_2Cl_2$ (70 mL) were added $Ac_2O$ (5.84 g, 57 mmol) and DMAP (349 mg, 2.9 mmol). The mixture was stirred at 25° C. for 1 hr. The reaction mixture was diluted with $H_2O$ (300 mL) and extracted with $CH_2Cl_2$ (200 mL×3). The combined organic layers were washed with brine (130 mL), dried over $Na_2SO_4$, filtered and concentrated under reduced pressure. After purified by silica gel flash chromatography (Eluent of 10~50% EtOAc in petroleum ether), 4-((4-cyano-2-nitrophenyl)amino)benzyl acetate (7.4 g, yield: 83%) was obtained as a yellow solid. $^1$H NMR (400 MHz, Dimethysulfoxide-$d_6$) δ 9.89 (s, 1H), 8.59 (d, J=2.0 Hz, 1H), 7.77 (dd, J=8.8, 2.0 Hz, 1H), 7.47 (d, J=8.4 Hz, 2H), 7.36 (d, J=8.4 Hz, 2H), 7.11 (d, J=8.8 Hz, 1H), 5.10 (s, 2H), 2.08 (s, 3H).

Step 3: 4-(2-(2-Aminopyridin-3-yl)-5-cyano-1H-benzo[d]imidazol-1-yl)benzyl acetate A mixture of 4-((4-cyano-2-nitrophenyl)amino)benzyl acetate (7.4 g, 24 mmol), 2-aminonicotinaldehyde (3.19 g, 26 mmol), $Na_2S_2O_4$ (16.6 g, 95 mmol) in DMSO (200 mL) was degassed and purged with $N_2$ three times, and then was stirred at 100° C. for 16 hr under $N_2$ atmosphere. The reaction mixture was diluted with $H_2O$ (300 mL) and extracted with $CH_2Cl_2$ (200 mL×3). The combined organic layers were washed with brine (150 mL), dried over $Na_2SO_4$, filtered, and concentrated under reduced pressure. After purified by silica gel flash chromatography (Eluent of 0~50% EtOAc in petroleum ether), 4-(2-(2-aminopyridin-3-yl)-5-cyano-1H-benzo[d]imidazol-1-yl)benzyl acetate (3.6 g, yield: 33%) was obtained as a yellow solid. MS: m/z=384.0 [M+H]⁺. ¹H NMR (400 MHz, Dimethylsulfoxide-d₆) δ 8.37 (s, 1H), 8.00 (dd, J=4.8, 1.6 Hz, 1H), 7.71-7.66 (m, 1H), 7.60-7.53 (m, 2H), 7.50-7.45 (m, 2H), 7.36-7.33 (m, 1H), 7.22 (dd, J=7.6, 2.0 Hz, 1H), 6.88 (br s, 2H), 6.42 (dd, J=7.6, 4.8 Hz, 1H), 5.17 (s, 2H), 2.11 (s, 3H).

Step 4: 2-(2-Aminopyridin-3-yl)-1-(4-(hydroxymethyl)phenyl)-1H-benzo[d]imidazole-5-carbonitrile To a solution of 4-(2-(2-aminopyridin-3-yl)-5-cyano-1H-benzo[d]imidazol-1-yl)benzyl acetate (700 mg, 1.83 mmol) in THF (2 mL) were added K₂CO₃ (757 mg, 5.48 mmol), MeOH (2 mL) and H₂O (2 mL). The mixture was stirred at 25° C. for 1 hr. The reaction mixture was diluted with H₂O (20 mL) and extracted with EtOAc (20 mL×3). The combined organic layers were washed with brine (30 mL), dried over Na₂SO₄, filtered and concentrated under reduced pressure. 2-(2-Aminopyridin-3-yl)-1-(4-(hydroxymethyl)phenyl)-1H-benzo[d]imidazole-5-carbonitrile (500 mg, crude) was obtained as a yellow solid. MS: m/z=342.0 [M+H]⁺.

Step 5: 2-(2-Aminopyridin-3-yl)-1-(4-(chloromethyl)phenyl)-1H-benzo[d]imidazole-5-carbonitrile To a solution of 2-(2-aminopyridin-3-yl)-1-(4-(hydroxymethyl)phenyl)-1H-benzo[d]imidazole-5-carbonitrile (500 mg, 1.46 mmol) in CH₂Cl₂ (2 mL) was added SOCl₂ (348 mg, 2.93 mmol). The mixture was stirred at 50° C. for 1 hr. The mixture was concentrated under reduced pressure to give 2-(2-aminopyridin-3-yl)-1-(4-(chloromethyl)phenyl)-1H-benzo[d]imidazole-5-carbonitrile (500 mg, crude) as a yellow solid. MS: m/z=359.9 [M+H]⁺.

Step 6: 2-(2-Aminopyridin-3-yl)-1-(4-((4-((2-cyanopyrimidin-4-yl)amino)piperidin-1-yl)methyl)phenyl)-1H-benzo[d]imidazole-5-carbonitrile To a solution of 2-(2-aminopyridin-3-yl)-1-(4-(chloromethyl)phenyl)-1H-benzo[d]imidazole-5-carbonitrile (200 mg, 556 μmol) and Intermediate 51 (212 mg, 667 μmol) in DMF (3 mL) were added NaI (83.3 mg, 556 μmol) and K₂CO₃ (230 mg, 1.67 mmol). The mixture was stirred at 50° C. for 1 hr. The reaction mixture was diluted with H₂O (15 mL) and extracted with EtOAc (20 mL×2). The combined organic layers were washed with brine (30 mL), dried over Na₂SO₄, filtered, and concentrated under reduced pressure. After purified by prep-HPLC (column: Phenomenex C18 150×25 mm×10 μm; mobile phase. [water (NH₄HCO₃)-ACN]; gradient: 35%-55% B over 11 min), 2-(2-aminopyridin-3-yl)-1-(4-((4-((2-cyanopyrimidin-4-yl)amino)piperidin-1-yl)methyl)phenyl)-1H-benzo[d]imidazole-5-carbonitrile (Example 501, 30.4 mg yield: 10%) was obtained as an off white solid. MS: m/z=527.1 [M+H]⁺. ¹H NMR (400 MHz, Methanol-d₄) δ 8.22 (d, J=1.2 Hz, 1H), 8.08-7.95 (m, 2H), 7.67-7.58 (m, 3H), 7.45-7.38 (m, 3H), 7.30 (dd, J=7.6, 1.6 Hz, 1H), 6.62 (d, J=5.2 Hz, 1H), 6.46 (dd, J=7.6, 5.2 Hz, 1H), 4.04-3.88 (m, 1H), 3.68 (s, 2H), 2.96 (d, J=11.6 Hz, 2H), 2.28 (t, J=10.8 Hz, 2H), 2.07-1.99 (m, 2H), 1.68-1.57 (m, 2H).

Example 502: 4-((1-((4-(2-(2-Aminopyridin-3-yl)-3H-imidazo[4,5-b]pyridin-3-yl)phenyl)methyl-d₂)piperidin-4-yl)(methyl-d₃)amino)pyrimidine-2-carbonitrile

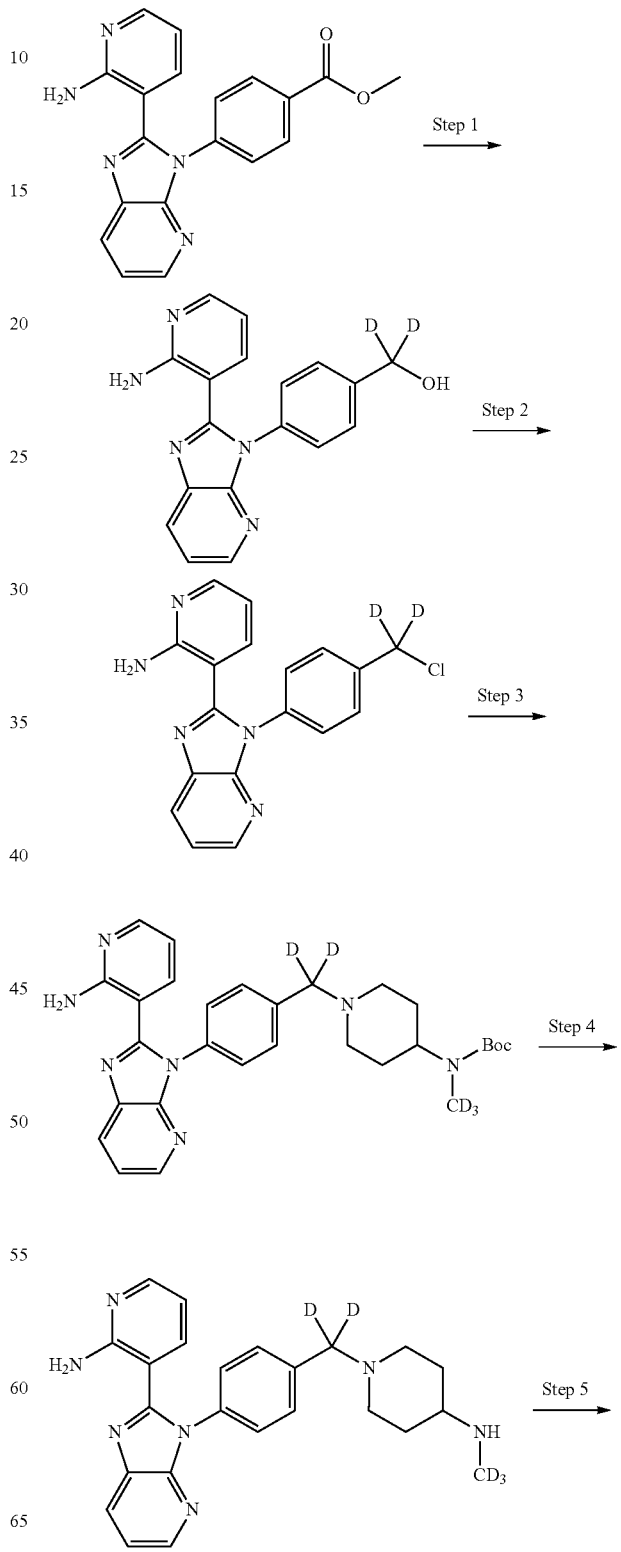

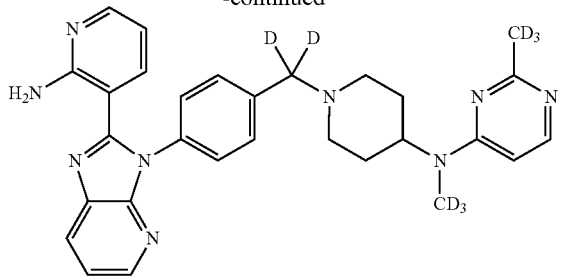

Example 502

Step 1: (4-(2-(2-Aminopyridin-3-yl)-3H-imidazo[4,5-b]pyridin-3-yl)phenyl)methan-d₂-ol To a mixture of methyl 4-(2-(2-aminopyridin-3-yl)-3H-imidazo[4,5-b]pyridin-3-yl)benzoate (300 mg, 869 μmol) in THF (5 mL) was added LiAlD₄ (42.9 mg, 1.13 mmol). The mixture was purged with N₂ three times and stirred at 25° C. for 1 hr under N₂ atmosphere. The reaction mixture was filtered and concentrated under reduced pressure. (4-(2-(2-Aminopyridin-3-yl)-3H-imidazo[4,5-b]pyridin-3-yl)phenyl)methan-d₂-ol (270 mg, yield: 97.3%) was obtained as a pink solid. MS: m/z=319.9 [M+H]⁺.

Step 2: 3-(3-(4-(Chloromethyl-d₂)phenyl)-3H-imidazo[4,5-b]pyridin-2-yl)pyridin-2-amine To a solution of (4-(2-(2-aminopyridin-3-yl)-3H-imidazo[4,5-b]pyridin-3-yl)phenyl)methan-d₂-ol (270 mg, 845 μmol) in CH₂Cl₂ (5 mL) was added SOCl₂ (101 mg, 845 μmol). The mixture was stirred at 40° C. for 1 hr. The reaction mixture was quenched with H₂O (0.5 mL) at 0° C., filtered and concentrated under reduced pressure. 3-(3-(4-(Chloromethyl-d₂)phenyl)-3H-imidazo[4,5-b]pyridin-2-yl)pyridin-2-amine (300 mg, HCl salt, yield: 94.8%) was obtained as a pink solid. MS: m/z=338.0 [M+H]⁺.

Step 3: Tert-butyl (1-((4-(2-(2-aminopyridin-3-yl)-3H-imidazo[4,5-b]pyridin-3-yl)phenyl)methyl-d₂)piperidin-4-yl)(methyl-d₃)carbamate To a solution of 3-(3-(4-(chloromethyl-d₂)phenyl)-3H-imidazo[4,5-b]pyridin-2-yl)pyridin-2-amine (300 mg, 802 μmol, HCl salt), tert-butyl (methyl-d₃)(piperidin-4-yl)carbamate (174 mg 802 μmol) in DMF (5 mL) were added NaI (24.0 mg, 160 μmol) and K₂CO₃ (332 mg, 2.40 mmol). The mixture was stirred at 50° C. for 1 hr. The mixture was diluted with H₂O (20 mL) and extracted with CH₂Cl₂ (30 mL×3). The combined organic layers were washed with brine (30 mL×4), dried over Na₂SO₄, filtered and concentrated under reduced pressure. After purified by silica gel flash chromatography (Eluent of 3~8% CH₂Cl₂ in MeOH), tert-butyl (1-((4-(2-(2-aminopyridin-3-yl)-3H-imidazo[4,5-b]pyridin-3-yl)phenyl)methyl-d₂)piperidin-4-yl)(methyl-d₃)carbamate (340 mg, yield: 67.1%) was obtained as a purple solid. MS: m/z=519.2 [M+H]⁺. ¹H NMR (400 MHz, Chloroform-d) δ 8.46-8.36 (m, 1H), 8.13-8.04 (m, 2H), 7.65-7.48 (m, 2H), 7.38-7.30 (m, 3H), 7.10-7.04 (m, 1H), 6.65-6.56 (m, 2H), 6.38-6.33 (m, 1H), 3.09-2.99 (m, 1H), 2.34-2.08 (m, 2H), 1.94-1.71 (m, 2H), 1.71-1.62 (m, 4H), 1.48 (s, 9H).

Step 4: 3-(3-(4-((4-((Methyl-d3)amino)piperidin-1-yl)methyl-d2)phenyl)-3H-imidazo[4,5-b]pyridin-2-yl)pyridin-2-amine To a solution of tert-butyl (1-((4-(2-(2-aminopyridin-3-yl)-3H-imidazo[4,5-b]pyridin-3-yl)phenyl)methyl-d₂)piperidin-4-yl)(methyl-d₃)carbamate (340 mg, 656 μmol) in MeOH (1 mL) was added HCl in dioxane (4 M, 163.88 μL). The mixture was stirred at 25° C. for 1 hr. The reaction mixture was filtered and concentrated under reduced pressure. 3-(3-(4-((4-((Methyl-d3)amino)piperidin-1-yl)methyl-d₂)phenyl)-3H-imidazo[4,5-b]pyridin-2-yl)pyridin-2-amine (280 mg, yield: 93.8%) was obtained as a pink solid. MS: m/z=419.3 [M+H]⁺. ¹H NMR (400 MHz, Methanol-d₄) δ 8.46 (dd, J=4.8, 1.2 Hz, 1H), 8.34 (dd, J=8.0, 1.2 Hz, 1H), 8.02 (dd, J=6.0, 1.2 Hz, 1H), 7.90-7.85 (m, 3H), 7.66 (d, J=8.4 Hz, 2H), 7.54 (dd, J=8.0, 4.8 Hz, 1H), 6.87 (dd, J=7.6, 6.4 Hz, 1H), 3.74-3.70 (m, 2H), 3.51-3.43 (m, 1H), 3.28-3.21 (m, 2H), 2.41-2.34 (m, 2H), 2.16-2.03 (m, 2H).

Step 5: 4-((1-((4-(2-(2-Aminopyridin-3-yl)-3H-imidazo[4,5-b]pyridin-3-yl)phenyl)methyl-d2)piperidin-4-yl)(methyl-d3)amino)pyrimidine-2-carbonitrile To a solution of 3-(3-(4-((4-((methyl-d₃)amino)piperidin-1-yl)methyl-d₂)phenyl)-3H-imidazo[4,5-b]pyridin-2-yl)pyridin-2-amine (150 mg, 358.38 μmol), 4-chloropyrimidine-2-carbonitrile (50.0 mg, 358 μmol) in NMP (3 mL) was added DIEA (139 mg, 1.08 mmol). The mixture was stirred at 130° C. for 0.5 hr. After purified by prep-HPLC (column: Welch Xtimate Cis 150×25 mm×5 μm; mobile phase: [water (HCl)-ACN]; gradient: 0%-25% B over 8 min), the crude product was neutralized with saturated NaHCO₃ and extracted with CH₂Cl₂ (10 mL×3). The combined organic layers were washed with brine (10 mL×2), dried over Na₂SO₄, filtered, and concentrated under reduced pressure. 4-((1-((4-(2-(2-Aminopyridin-3-yl)-3H-imidazo[4,5-b]pyridin-3-yl)phenyl)methyl-d₂)piperidin-4-yl)(methyl-d₃)amino)pyrimidine-2-carbonitrile (Example 502, 37.3 mg, yield: 18.2%) was obtained as a yellow solid. MS: m/z=522.3 [M+H]⁺. ¹H NMR (400 MHz, Methanol-d₄) δ 8.34 (dd, J=4.8, 1.2 Hz, 1H), 8.20 (dd, J=8.0, 1.2 Hz, 1H), 8.16 (d, J=6.4 Hz, 1H), 7.98 (dd, J=5.2, 2.0 Hz, 1H), 7.55 (d, J=8.4 Hz, 2H), 7.45-7.39 (m, 3H), 7.32 (dd, J=7.6, 2.0 Hz, 1H), 6.90-6.76 (m, 1H), 6.46 (dd, J=7.6, 5.2 Hz, 1H), 3.30-3.27 (m, 1H), 3.06 (br d, J=12.0 Hz, 2H), 2.31-2.23 (m, 2H), 1.99-1.90 (m, 2H), 1.71-1.67 (m, 2H).

Example 503: 4-((1-(4-(2-(2-Aminopyridin-3-yl)-3H-imidazo[4,5-b]pyridin-3-yl)benzyl)piperidin-4-yl-4-d)amino)pyrimidine-2-carbonitrile

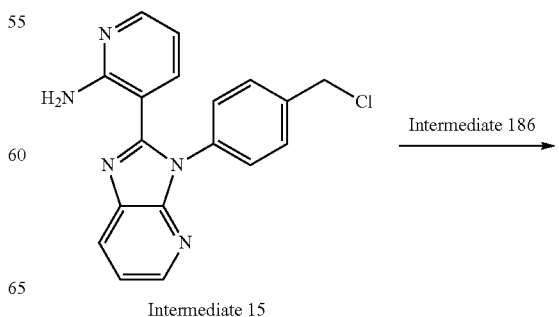

Intermediate 15

1627
-continued

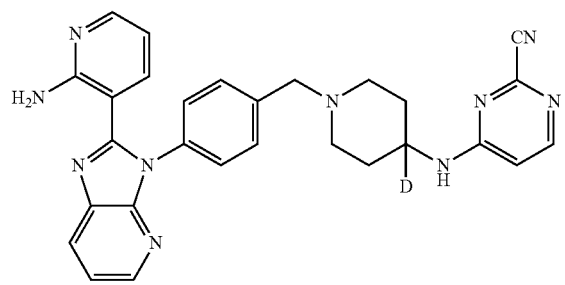

Example 503

To a solution of Intermediate 15 (90 mg, 268 μmol) and Intermediate 186 (60.2 mg, 295 μmol) in DMF (5 mL) were added NaI (8.04 mg, 53.6 μmol) and K$_2$CO$_3$ (111 mg, 804 μmol) at 20° C. The reaction mixture was stirred at 20° C. for 12 hr. The mixture was diluted with H$_2$O (20 mL) was added and extracted with EtOAc (20 mL×3). The combined organic layers were washed with brine (20 mL×2), dried over anhydrous Na$_2$SO$_4$, filtered, and concentrated under reduced pressure. After purified by prep-HPLC (column: Phenomenex C18 80×30 mm×5 μm; mobile phase: [water (NH$_3$H$_2$O+NH$_4$HCO$_3$)-ACN]; gradient: 38%-68% B over 7 min), 4-((1-(4-(2-(2-aminopyridin-3-yl)-3H-imidazo[4,5-b]pyridin-3-yl)benzyl)piperidin-4-yl-4-d)amino)pyrimidine-2-carbonitrile (Example 503, 17.6 mg, 13.0% yield) was obtained as an off-white solid. MS: m/z=504.2 [M+H]$^+$. $^1$H NMR (400 MHz, Dimethylsulfoxide-d$_6$) δ 8.33 (d, J=4.8 Hz, 1H), 8.21 (d, J=8.0 Hz, 1H), 8.12-8.03 (m, 2H), 7.99 (dd, J=4.4, 1.2 Hz, 1H), 7.47-7.43 (m, 2H), 7.41-7.36 (m, 3H), 7.16 (dd, J=7.6, 1.6 Hz, 1H), 7.01 (s, 2H), 6.67 (d, J=6.0 Hz, 1H), 6.37 (dd, J=7.6, 4.8 Hz, 1H), 3.56 (s, 2H) 2.85-2.77 (m, 2H), 2.19-2.09 (m, 2H), 1.92-1.82 (m, 2H), 1.53-1.43 (m, 2H).

Example 504: 4-((1-((4-(2-(2-Aminopyridin-3-yl)-5, 6-dimethyl-3H-imidazo[4,5-b]pyridin-3-yl)phenyl) methyl-d$_2$)piperidin-4-yl)amino)pyrimidine-2-carbonitrile

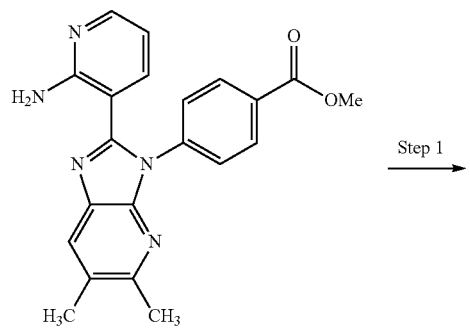

Step 1

1628
-continued

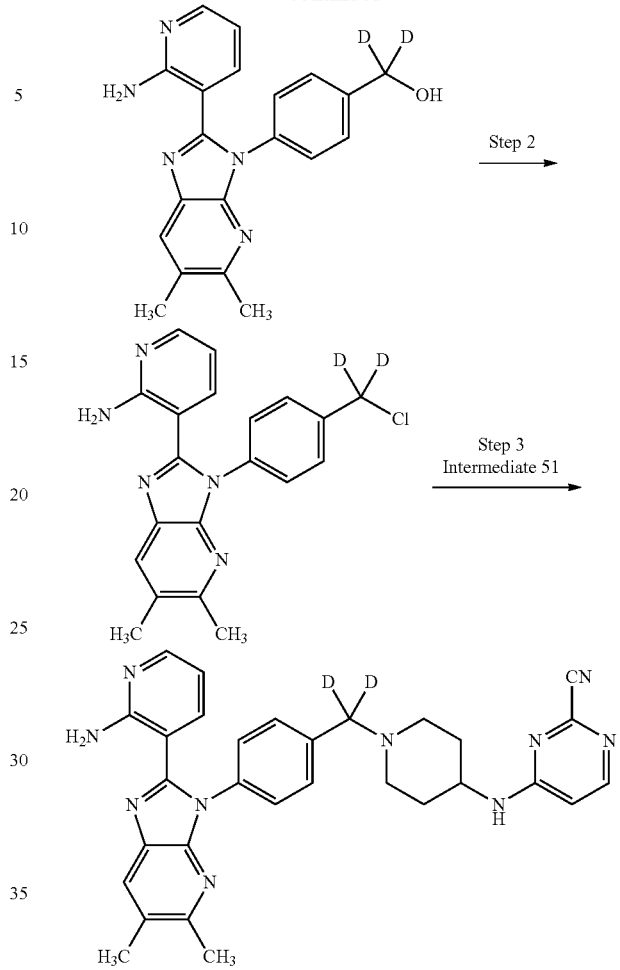

Example 504

Step 1: (4-(2-(2-Aminopyridin-3-yl)-5,6-dimethyl-3H-imidazo[4,5-b]pyridin-3-yl)phenyl)methan-d2-ol To a mixture of methyl 4-(2-(2-aminopyridin-3-yl)-5,6-dimethyl-3H-imidazo[4,5-b]pyridin-3-yl)benzoate (refer to Intermediate 138 for detail procedures, 290 mg, 777 μmol) in THF (20 mL) was added LiAlD$_4$ (2.5 M in THF, 80 μL). The mixture was degassed and purged with N$_2$ three times and stirred at 0° C. for 2 hr under N$_2$ atmosphere. The reaction mixture was quenched with Na$_2$SO$_4$·10H$_2$O (1.0 g) at 0° C., filtered, and concentrated. (4-(2-(2-Aminopyridin-3-yl)-5,6-dimethyl-3H-imidazo[4,5-b]pyridin-3-yl)phenyl) methan-d2-ol (260 mg, yield: 96%) was obtained as a yellow solid. MS: m/z=347.9 [M+H]$^+$.

Step 2: 3-(3-(4-(Chloromethyl-d2)phenyl)-5,6-dimethyl-3H-imidazo[4,5-b]pyridin-2-yl)pyridin-2-amine To a solution of (4-(2-(2-aminopyridin-3-yl)-5,6-dimethyl-3H-imidazo[4,5-b]pyridin-3-yl)phenyl)methan-d2-ol (260 mg, 748 μmol) in CH$_2$Cl$_2$ (15 mL) was added SOCl$_2$ (534 mg, 4.49 mmol). The mixture was stirred at 40° C. for 1 hr. The mixture was concentrated to give 3-(3-(4-(chloromethyl-d2)phenyl)-5,6-dimethyl-3H-imidazo[4,5-b]pyridin-2-yl)pyridin-2-amine (270 mg, yield: 99%) as a yellow solid. MS: m/z=366.0 [M+H]+.

Step 3: 4-((1-((4-(2-(2-Aminopyridin-3-yl)-5,6-dimethyl-3H-imidazo[4,5-b]pyridin-3-yl)phenyl)methyl-d$_2$)piperidin-4-yl)amino)pyrimidine-2-carbonitrile To a solution of 3-(3-(4-(chloromethyl-d2)phenyl)-5,6-dimethyl-3H-imidazo[4,5-b]pyridin-2-yl)pyridin-2-amine (250 mg, 683 µmol) and Intermediate 51 (139 mg, 683 µmol) in DMF (5 mL) were added NaI (51.2 mg, 342 µmol) and K$_2$CO$_3$ (472 mg, 342 µmol). The mixture was stirred at 50° C. for 1 hr. The reaction mixture was filtered. After purified by prep-HPLC (column: Waters xbridge 150×25 mm 10 µm; mobile phase: [water (NH$_4$HCO$_3$)-ACN]; gradient: 32%-62% B over 10 min), 4-((1-((4-(2-(2-aminopyridin-3-yl)-5,6-dimethyl-3H-imidazo[4,5-b]pyridin-3-yl)phenyl)methyl-d$_2$)piperidin-4-yl)amino)pyrimidine-2-carbonitrile (Example 504, 66 mg, yield: 18%) was obtained as a yellow solid. MS: m/z=533.2 [M+H]+. $^1$H NMR (400 MHz, Dimethylsulfoxide-d$_6$) δ 8.11-8.05 (m, 2H), 7.97-7.94 (m, 2H), 7.45 (d, J=8.0 Hz, 2H), 7.34 (d, J=8.0 Hz, 2H), 7.07-7.03 (m, 3H), 6.67 (d, J=6.0 Hz, 1H), 6.33 (dd, J=7.6, 4.8, 1H), 3.81-3.77 (m, 1H), 2.84-2.80 (m, 2H), 2.45 (s, 3H), 2.39 (s, 3H), 2.16-2.11 (m, 2H), 1.91-1.86 (m, 2H), 1.52-1.45 (m, 2H). 1003%01 Example 505: 4-((1-(4-(8-(2-Aminopyridin-3-yl)-9H-purin-9-yl)benzyl)piperidin-4-yl)amino)pyrimidine-2-carbonitrile

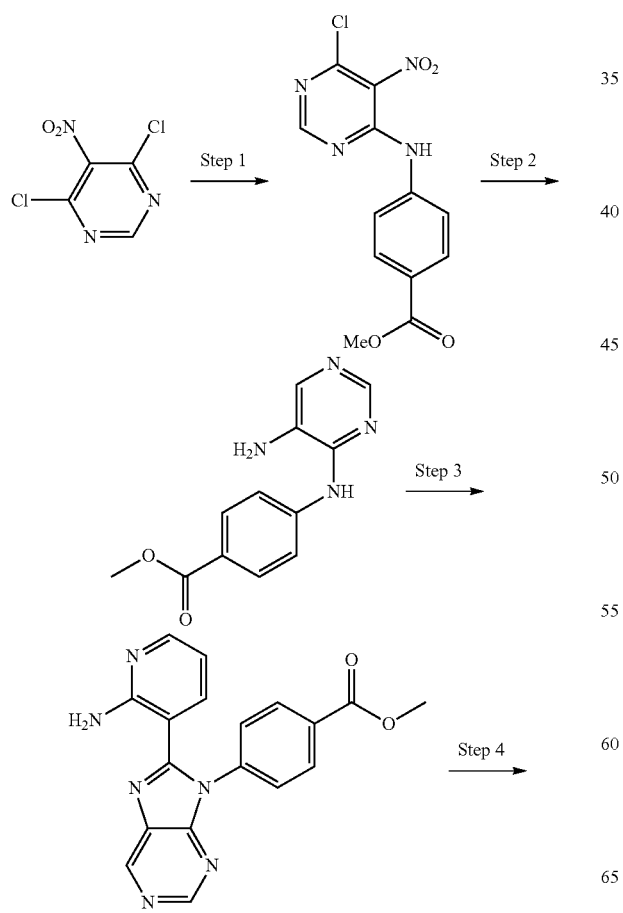

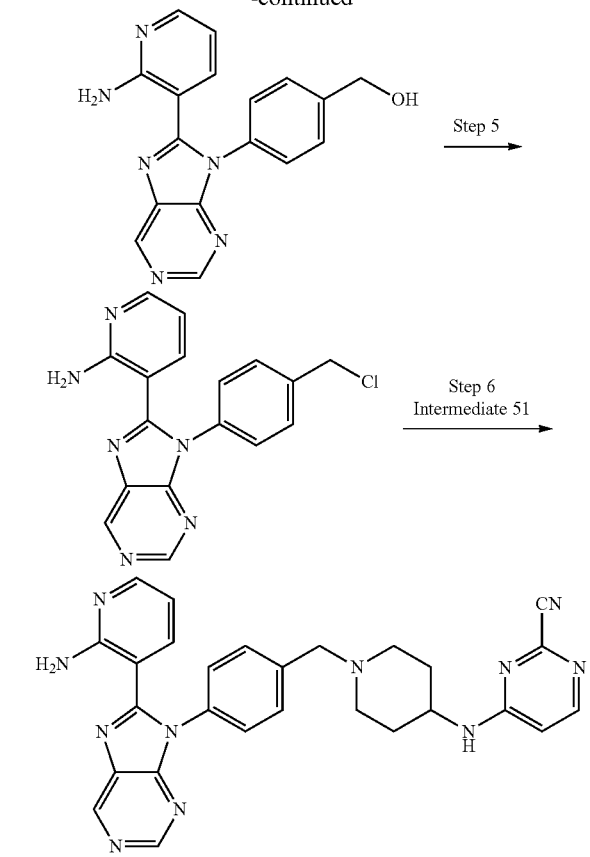

Example 505

Step 1: Methyl 4-((6-chloro-5-nitropyrimidin-4-yl)amino)benzoate

To a mixture of 4,6-dichloro-5-nitropyrimidine (3.0 g, 15.5 mmol) and methyl 4-aminobenzoate (1.87 g, 12.4 mmol) in THF (20 mL) was added TEA (1.41 g, 13.9 mmol). The mixture was degassed and purged with N$_2$ three times and stirred at 0° C. for 4 hr under N$_2$ atmosphere. The reaction mixture was diluted with water (100 mL) and extracted with EtOAc (50 mL×3). The combined organic layers were washed with brine (100 mL), dried over Na$_2$SO$_4$, filtered and concentrated under reduced pressure. After purified by silica gel flash chromatography (Eluent of 0~8% EtOAc in petroleum ether), methyl 4-((6-chloro-5-nitropyrimidin-4-yl)amino)benzoate (3.0 g, yield. 61%) was obtained as a yellow solid. MS: m/z=308.9 [M+H]+, $^1$H NMR (400 MHz, Dimethylsulfoxide-d$_6$) δ 10.32 (s, 1H), 8.63 (s, 1H), 7.97 (d, J=8.8 Hz, 2H), 7.74 (d, J=8.8 Hz, 2H), 3.85 (s, 3H)

Step 2: Methyl 4-((5-aminopyrimidin-4-yl)amino)benzoate

To a solution of methyl 4-((6-chloro-5-nitropyrimidin-4-yl)amino)benzoate (1.5 g, 4.86 mmol) in MeOH (20 mL) was added Pd/C (517 mg, 486 gmol, 10% purity). The mixture was degassed and purged with H$_2$ three times and stirred at 25° C. for 16 hr under H$_2$. The reaction mixture was filtered and concentrated to give methyl 4-((5-aminopyrimidin-4-yl)amino)benzoate (1 g, yield: 78%) as a brown solid. MS: m/z=244.9 [M+H]⁺. ¹H NMR (400 MHz, Dimethylsulfoxide-d₆) 10.31 (s, 1H), 8.45 (s, 1H), 7.99 (br.s, 4H), 7.82 (s, 1H), 6.77-5.98 (m, 2H), 3.85 (s, 3H).

Step 3: Methyl 4-(8-(2-aminopyridin-3-yl)-9H-purin-9-yl)benzoate

A mixture of methyl 4-((5-aminopyrimidin-4-yl)amino)benzoate (1.0 g, 4.09 mmol), 2-aminonicotinaldehyde (550 mg, 4.50 mmol) and Cu(Oac)₂ (149 mg, 819 mmol) in CH₃COOH (100 mL) was degassed and purged with N₂ three times. The mixture was stirred at 60° C. for 16 hr under N₂ atmosphere. The reaction mixture was neutralized with NH₃·H₂O (adjusted pH to 7-8). The reaction mixture was diluted with water (100 mL) and extracted with EtOAc (200 mL×3). The combined organic layers were washed with brine (200 mL), dried over Na₂SO₄, filtered and concentrated under reduced pressure. After purified by silica gel flash chromatography (Eluent of 0~8% MeOH in CH₂Cl₂), methyl 4-(8-(2-aminopyridin-3-yl)-9H-purin-9-yl)benzoate (300 mg yield: 17%) was obtained as a yellow solid. MS: m/z=347.0 [M+H]⁺, ¹H NMR (400 MHz, Dimethylsulfoxide-d₆) δ 9.29 (s, 1H), 8.94 (s, 1H), 8.10-8.08 (m, 2H), 8.04 (dd, J=4.8, 2.0 Hz, 1H), 7.63-7.61 (m, 2H), 7.35 (d, J=6.4 Hz, 1H), 6.79 (s, 2H), 6.50 (dd, J=7.6, 5.2 Hz, 1H), 3.89 (s, 3H)

Step 4: (4-(8-(2-Aminopyridin-3-yl)-9H-purin-9-yl)phenyl)methanol

To a mixture of methyl 4-(8-(2-aminopyridin-3-yl)-9H-purin-9-yl)benzoate (300 mg, 866 μmol) in THF (20 mL) was added LiAlH₄ (2.5 M in THF, 693 μL). The mixture was degassed and purged with N₂ three times and stirred at 0° C. for 2 hr under N₂ atmosphere. The reaction mixture was quenched with Na₂SO₄·10H₂O (1.0 g) at 0° C., filtered, and concentrated. (4-(8-(2-Aminopyridin-3-yl)-9H-purin-9-yl)phenyl)methanol (202 mg, yield: 73%) was obtained as a yellow solid. MS: m/z=319.0 [M+H]⁺.

Step 5: 3-(9-(4-(Chloromethyl)phenyl)-9H-purin-8-yl)pyridin-2-amine

To a solution of (4-(8-(2-aminopyridin-3-yl)-9H-purin-9-yl)phenyl)methanol (202 mg, 635 μmol) in CH₂Cl₂ (20 mL) was added SOCl₂ (453 mg, 3.81 mmol). The mixture was stirred at 40° C. for 1 hr. The mixture was concentrated to give 3-(9-(4-(chloromethyl)phenyl)-9H-purin-8-yl)pyridin-2-amine (103 mg, yield: 48%) as a yellow solid. MS: m/z=337.0 [M+H].

Step 6: 4-((1-(4-(8-(2-Aminopyridin-3-yl)-9H-purin-9-yl)benzyl)piperidin-4-yl)amino)pyrimidine-2-carbonitrile To a solution of 3-(9-(4-(chloromethyl)phenyl)-9H-purin-8-yl)pyridin-2-amine (103 mg, 306 μmol) and Intermediate 51 (62 mg, 306 μmol) in DMF (5 mL) were added NaI (22.3 mg, 153 μmol) and K₂CO₃ (127 mg, 918 μmol). The mixture was stirred at 50° C. for 1 hr. The reaction mixture was filtered. After purified by prep-HPLC (column: Waters xbridge 150×25 mm 10 μm; mobile phase: [water (NH₄HCO₃)-ACN]; gradient: 20%-50% B over 11 min), 4-((1-(4-(8-(2-Aminopyridin-3-yl)-9H-purin-9-yl)benzyl)piperidin-4-yl)amino)pyrimidine-2-carbonitrile (Example 505, 5 mg, yield: 3%) was obtained as a yellow solid. MS: m/z=504.1 [M+H]⁺. ¹H NMR (400 MHz, Dimethylsulfoxide-d₆) δ 9.26 (s, 1H), 8.91 (s, 1H), 8.10-8.01 (m, 3H), 7.43-7.41 (m, 4H), 7.25 (dd, J=8.0, 1.6 Hz, 1H), 6.87 (s, 2H), 6.67 (d, J=6.0 Hz, 1H), 6.41 (dd, J=7.6, 4.8 Hz, 1H), 3.84-3.78 (m, 1H), 3.56 (s, 2H), 2.83-2.77 (m, 2H), 2.17-2.09 (m, 2H), 1.91-1.82 (m, 2H), 1.52-1.43 (m, 2H)

Example 506 and 507: (S)-4-((1-(4-(2-(2-Aminopyridin-3-yl)-5-(tetrahydrofuran-3-yl)-3H-imidazo[4,5-b]pyridin-3-yl)benzyl)piperidin-4-yl)amino)pyrimidine-2-carbonitrile & (R)-4-((1-(4-(2-(2-Aminopyridin-3-yl)-5-(tetrahydrofuran-3-yl)-3H-imidazo[4,5-b]pyridin-3-yl)benzyl)piperidin-4-yl)amino)pyrimidine-2-carbonitrile

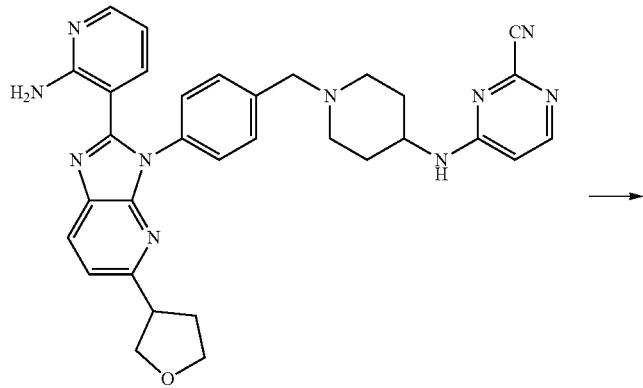

Example 417

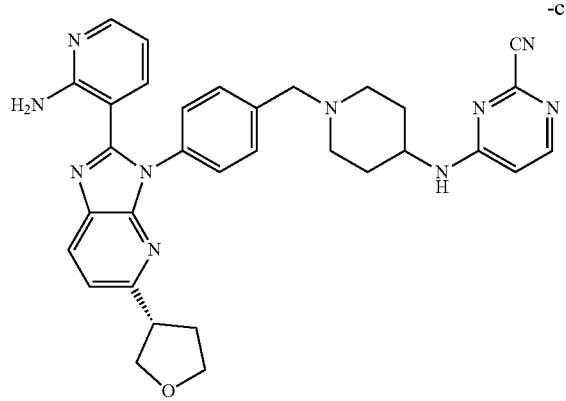

Example 506

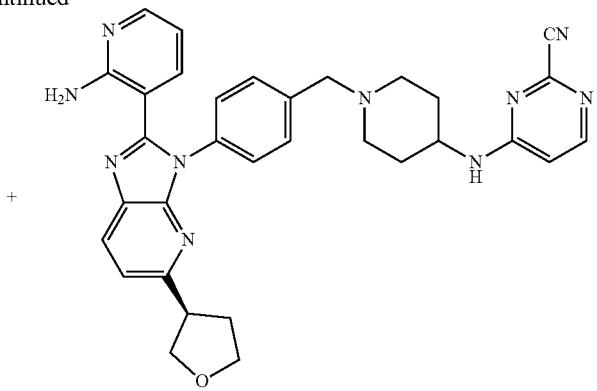

Example 507

Stereochemistry arbitrarily assigned

Example 417 (56 mg, 97.8 μmol) was submitted to SFC (column: DAICEL CHIRALPAK IG (250 mm×30 mm, 10 μm); mobile phase: [CO₂-i-PrOH (0.1% NH₃·H₂O)]; B %: 50%, isocratic elution mode). (S)-4-((1-(4-(2-(2-Aminopyridin-3-yl)-5-(tetrahydrofuran-3-yl)-3H-imidazo[4,5-b]pyridin-3-yl)benzyl)piperidin-4-yl)amino)pyrimidine-2-carbonitrile (Example 506, stereochemistry arbitrarily assigned, 12.9 mg, yield: 23%) was obtained as an off-white solid. MS: m/z=573.3 [M+H]⁺. ¹H NMR (400 MHz, Dimethylsulfoxide-d₆) δ 8.16-8.03 (m, 3H), 7.97 (dd, J=4.8, 1.6 Hz, 1H), 7.46-7.42 (m, 2H), 7.38-7.33 (m, 3H), 7.10 (d, J=7.6 Hz, 1H), 6.96 (s, 2H), 6.67 (d, J=6.0 Hz, 1H), 6.36 (dd, J=7.6, 4.8 Hz, 1H), 4.04 (t, J=8.0 Hz, 1H), 3.93-3.86 (m, 1H), 3.84-3.68 (m, 3H), 3.66-3.56 (m, 3H), 2.86-2.77 (m, 2H), 2.31-2.21 (m, 1H), 2.17-2.05 (m, 3H), 1.94-1.83 (m, 2H), 1.54-1.42 (m, 2H). (R)-4-((1-(4-(2-(2-aminopyridin-3-yl)-5-(tetrahydrofuran-3-yl)-3H-imidazo[4,5-b]pyridin-3-yl)benzyl)piperidin-4-yl)amino)pyrimidine-2-carbonitrile (Example 507, stereochemistry arbitrarily assigned, 15.9 mg, yield: 28%) was obtained as an off-white solid. MS: m/z=573.2 [M+H]⁺. ¹H NMR (400 MHz, Dimethylsulfoxide-d₆) δ 8.16-8.04 (m, 3H), 7.97 (dd, J=4.8, 1.6 Hz, 1H), 7.47-7.42 (m, 2H), 7.39-7.32 (m, 3H), 7.10 (dd, J=7.6, 1.2 Hz, 1H), 6.96 (s, 2H), 6.67 (d, J=6.0 Hz, 1H), 6.36 (dd, J=7.6, 4.8 Hz, 1H), 4.04 (t, J=8.0 Hz, 1H), 3.92-3.86 (m, 1H), 3.84-3.67 (m, 3H), 3.66-3.56 (m, 3H), 2.85-2.77 (m, 2H), 2.31-2.21 (m, 1H), 2.20-2.03 (m, 3H), 1.93-1.82 (m, 2H), 1.54-1.43 (m, 2H).

Example 508: 4-((1-(4-(2-(2-Aminopyridin-3-yl)-5-(hydroxymethyl)-3H-imidazo[4,5-b]pyridin-3-yl)benzyl)piperidin-4-yl)amino)pyrimidine-2-carbonitrile

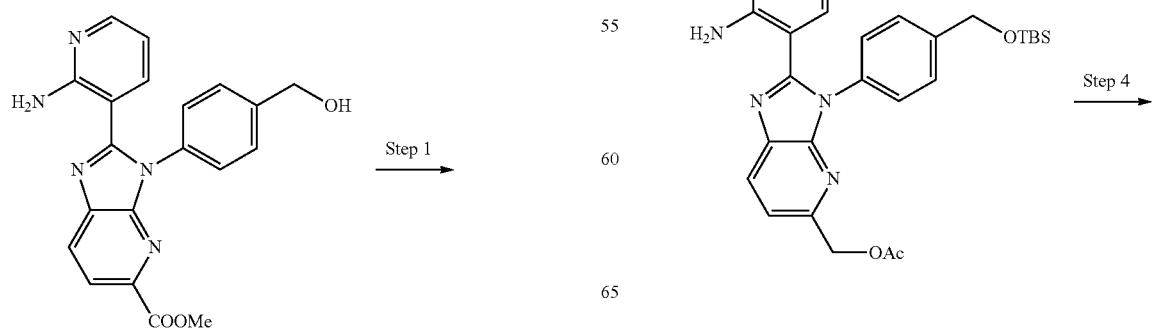

Step 1 →

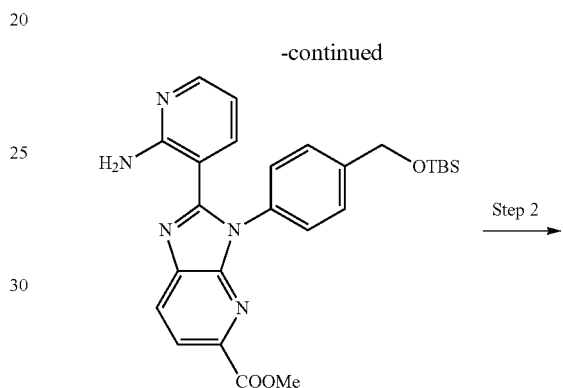

Step 2 →

Step 3 →

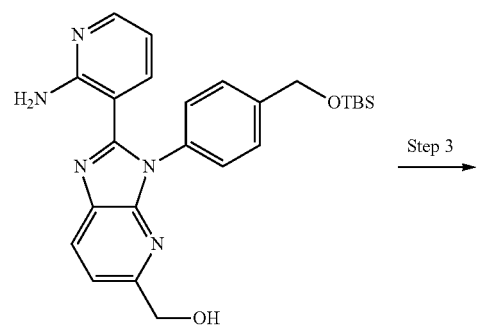

Step 4 →

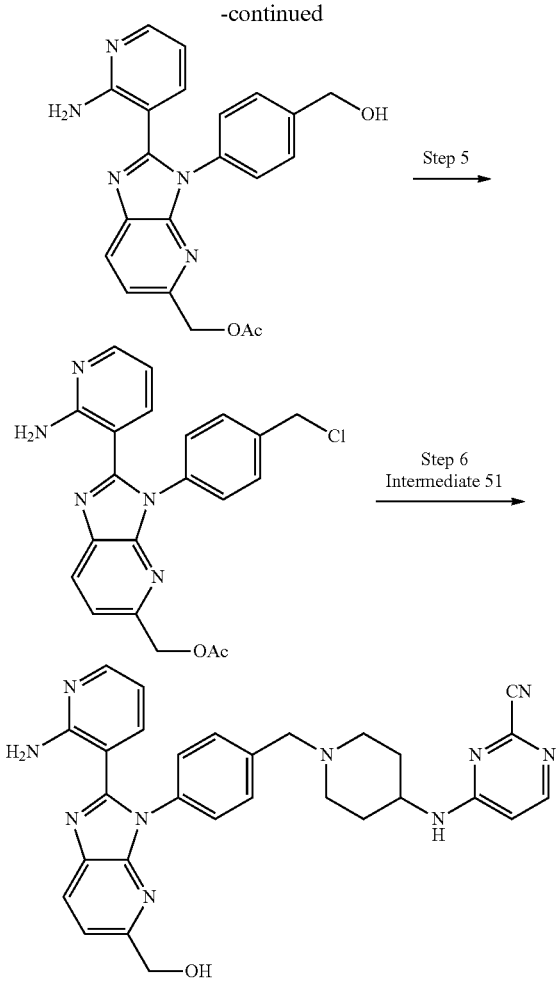

Example 508

Step 1: Methyl 2-(2-aminopyridin-3-yl)-3-(4-(((tert-butyldimethylsilyl)oxy)methyl)phenyl)-3H-imidazo[4,5-b]pyridine-5-carboxylate To a solution of methyl 2-(2-aminopyridin-3-yl)-3-(4-(hydroxymethyl)phenyl)-3H-imidazo[4,5-b]pyridine-5-carboxylate (refer to Intermediate 140 for detail procedures, 900 mg, 2.40 mmol) in CH$_2$Cl$_2$ (10 mL) were added imidazole (245 mg, 3.60 mmol) and TBSCl (470 mg, 3.12 mmol) at 0° C. This mixture was stirred at 25° C. for 1 hr. The mixture was quenched with H$_2$O (30 mL) and extracted with CH$_2$Cl$_2$ (30 mL×3). The combined organic layers were washed with brine (50 mL), dried over Na$_2$SO$_4$, filtered and concentrated. Methyl 2-(2-aminopyridin-3-yl)-3-(4-(((tert-butyldimethylsilyl)oxy)methyl)phenyl)-3H-imidazo[4,5-b]pyridine-5-carboxylate (110 g, yield: 93.7%) was obtained as a yellow solid. MS: m/z=490.4 [M+H]$^+$.

Step 2: (2-(2-Aminopyridin-3-yl)-3-(4-(((tert-butyldimethylsilyl)oxy)methyl)phenyl)-3H-imidazo[4,5-b]pyridin-5-yl)methanol To a solution of methyl 2-(2-aminopyridin-3-yl)-3-(4-(((tert-butyldimethylsilyl)oxy)methyl)phenyl)-3H-imidazo[4,5-b]pyridine-5-carboxylate (300 mg, 613 μmol) in THF (5 mL) was added LiAlH$_4$ (34.9 mg, 919 μmol) at 0° C. The mixture was degassed and purged with N$_2$ three times and stirred at 25° C. for 0.5 hr. The mixture was diluted with THF (20 mL). Na$_2$SO$_4$·10H$_2$O was added in portions until no bubbles were formed. The resulting mixture was stirred at 25° C. for 20 min and filtered. The filter cake was washed with THF (20 mL×2). The combined filtrate was concentrated to give (2-(2-aminopyridin-3-yl)-3-(4-(((tert-butyldimethylsilyl)oxy)methyl)phenyl)-3H-imidazo[4,5-b]pyridin-5-yl)methanol (244 mg, yield: 86.3%) as a yellow oil. MS: m/z=462.4 [M+H]$^+$.

Step 3: (2-(2-Aminopyridin-3-yl)-3-(4-(((tert-butyldimethylsilyl)oxy)methyl)phenyl)-3H-imidazo[4,5-b]pyridin-5-yl)methyl acetate To a solution of (2-(2-aminopyridin-3-yl)-3-(4-(((tert-butyldimethylsilyl)oxy)methyl)phenyl)-3H-imidazo[4,5-b]pyridin-5-yl)methanol (244 mg, 529 μmol) in CH$_2$Cl$_2$ (10 mL) were added TEA (160 mg, 1.59 mmol), DMAP (6.46 mg, 52.9 gmol) and Ac$_2$O (80.9 mg, 793 gmol) at 25° C. This mixture was stirred at 25° C. for 0.5 hr. The mixture was quenched with H$_2$O (50 mL) and extracted with EtOAc (30 mL×3). The combined organic layers were washed with brine (50 mL), dried over Na$_2$SO$_4$, filtered and concentrated. (2-(2-Aminopyridin-3-yl)-3-(4-(((tert-butyldimethylsilyl)oxy)methyl)phenyl)-3H-imidazo[4,5-b]pyridin-5-yl)methyl acetate (240 mg, yield: 90.2%) was obtained as a yellow oil. MS: m/z=504.4 [M+H]$^+$.

Step 4: (2-(2-aminopyridin-3-yl)-3-(4-(hydroxymethyl)phenyl)-3H-imidazo[4,5-b]pyridin-5-yl)methyl acetate To a solution of (2-(2-aminopyridin-3-yl)-3-(4-(((tert-butyldimethylsilyl)oxy)methyl)phenyl)-3H-imidazo[4,5-b]pyridin-5-yl)methyl acetate (240 mg, 476 μmol) in THF (10 mL) was added TBAF (1M in THF) (1 M, 714.76 μL) at 25° C. This mixture was stirred at 25° C. for 1 hr. The mixture was quenched with H$_2$O (50 mL) and extracted with EtOAc (30 mL×3). The combined organic layers were washed with brine (50 mL), dried over Na$_2$SO$_4$, filtered and concentrated. (2-(2-Aminopyridin-3-yl)-3-(4-(hydroxymethyl)phenyl)-3H-imidazo[4,5-b]pyridin-5-yl)methyl acetate (180 mg, yield: 97.0%) was obtained as a yellow oil. MS: m/z=390.2 [M+H]$^+$.

Step 5: (2-(2-Aminopyridin-3-yl)-3-(4-(chloromethyl)phenyl)-3H-imidazo[4,5-b]pyridin-5-yl)methyl acetate To a solution of (2-(2-aminopyridin-3-yl)-3-(4-(hydroxymethyl)phenyl)-3H-imidazo[4,5-b]pyridin-5-yl)methyl acetate (180 mg, 462 μmol) in CH$_2$Cl$_2$ (10 mL) was added SOCl$_2$ (82.5 mg, 693 gmol) at 25° C. This mixture was stirred at 25° C. for 1 hr. The reaction mixture was concentrated to give (2-(2-aminopyridin-3-yl)-3-(4-(chloromethyl)phenyl)-3H-imidazo[4,5-b]pyridin-5-yl)methyl acetate (180 mg, yield: 95.5%) as a yellow oil. MS: m/z=408.2 [M+H]$^+$.

Step 6: 4-((1-(4-(2-(2-Aminopyridin-3-yl)-5-(hydroxymethyl)-3H-imidazo[4,5-b]pyridin-3-yl)benzyl)piperidin-4-yl)amino)pyrimidine-2-carbonitrile To a solution of (2-(2-aminopyridin-3-yl)-3-(4-(chloromethyl)phenyl)-3H-imidazo[4,5-b]pyridin-5-yl)methyl acetate (230 mg, 564 μmol) and Intermediate (126 mg, 620

μmol) in DMF (3 mL) were added K₂CO₃ (117 mg, 846 μmol) and NaI (8.45 mg, 56.4 μmol) at 25° C. This mixture was stirred at 80° C. for 1 hr. The mixture was quenched with H₂O (30 mL) and extracted with EtOAc (30 mL×3). The combined organic layers were washed with brine (50 mL), dried over Na₂SO₄, filtered and concentrated. After purified by prep-HPLC (column: Phenomenex C18 75×30 mm×3 μm; mobile phase: [water (NH₃H₂O+NH₄HCO₃)-ACN]; gradient: 31%-61% B over 7 min), 4-((1-(4-(2-(2-aminopyridin-3-yl)-5-(hydroxymethyl)-3H-imidazo[4,5-h]pyridin-3-yl)benzyl)piperidin-4-yl)amino)pyrimidine-2-carbonitrile (Example 508, 94.5 mg, yield: 31.5%) was obtained as a yellow solid. MS: m/z=533.1 [M+H]⁺. ¹H NMR (400 MHz, Dimethylsulfoxide-d₆) 8.19 (d, J=8.0 Hz, 1H), 8.14-8.02 (m, 2H), 7.97 (dd, J=4.8, 2.0 Hz, 1H), 7.50 (d, J=8.4 Hz, 1H), 7.45 (d, J=8.0 Hz, 2H), 7.36 (d, J=8.4 Hz, 2H), 7.10 (dd, J=7.6, 1.6 Hz, 1H), 7.02 (s, 2H) 6.68 (d, J=6.0 Hz, 1H), 6.35 (dd, J=7.6, 4.8 Hz, 1H), 5.46 (t, J=6.0 Hz, 1H), 4.58 (d, J=6.0 Hz, 2H) 3.87-3.75 (m, 1H) 3.57 (s, 2H) 2.87-2.77 (m, 2H) 2.21-2.09 (m, 2H) 1.95-1.81 (m, 2H) 1.56-1.42 (m, 2H).

Example 509: 4-((1-(4-(2-(2-Aminopyridin-3-yl)-5-(fluoromethyl)-3H-imidazo[4,5-b]pyridin-3-yl)benzyl)piperidin-4-yl)amino)pyrimidine-2-carbonitrile

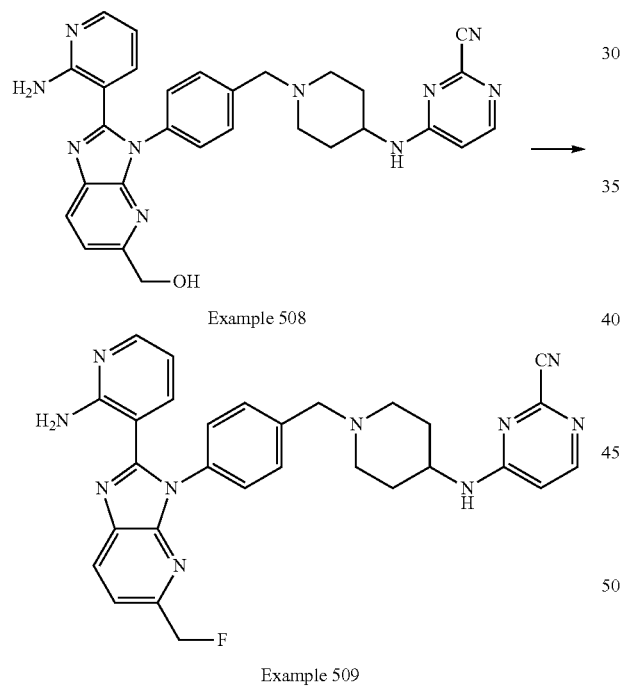

To a solution of Example 508 (70.0 mg, 131 μmol) in CH₂Cl₂ (3 mL) was added DAST (42.4 mg, 263 μmol) at 0° C. The mixture was stirred at 0° C. for 1 hr. The mixture was quenched with saturated NaHCO₃ (30 mL) and extracted with CH₂Cl₂ (30 mL×3). The combined organic layers were washed with brine (50 mL), dried over Na₂SO₄, filtered and concentrated. After purified by prep-HPLC (column: Phenomenex C18 75×30 mm×3 μm; mobile phase: [water (NH₃H₂O+NH₄HCO₃)-ACN]; gradient: 40%-70% B over 7 min), 4-((1-(4-(2-(2-aminopyridin-3-yl)-5-(fluoromethyl)-3H-imidazo[4,5-b]pyridin-3-yl)benzyl)piperidin-4-yl)amino)pyrimidine-2-carbonitrile (Example 509, 8.20 mg, yield: 11.7%) was obtained as a light yellow solid. MS: m/z=535.1 [M+H]⁺. ¹H NMR (400 MHz, Dimethylsulfoxide-d₆) 8.27 (d, J=8.0 Hz, 1H), 8.18-8.02 (m, 2H), 7.99 (d, J=3.6 Hz, 1H), 7.54 (d, J=8.4 Hz, 1H), 7.46 (d, J=8.0 Hz, 2H), 7.39 (d, J=8.0 Hz, 2H), 7.15 (d, J=7.6 Hz, 1H), 6.99 (s, 2H), 6.68 (d, J=6.0 Hz, 1H), 6.36 (dd, J=8.0, 5.2 Hz, 1H), 5.50 (d, J=47.2 Hz, 2H), 3.89-3.75 (m, 1H), 3.57 (s, 2H), 2.88-2.76 (m, 2H), 2.24-2.07 (m, 2H), 1.96-1.80 (m, 2H), 1.59-1.39 (m, 2H).

Example 510: 4-((1-(4-(2-(2-Aminopyridin-3-yl)-5-(pyrrolidin-1-yl)-3H-imidazo[4,5-b]pyridin-3-yl)benzyl)piperidin-4-yl)amino)pyrimidine-2-carbonitrile

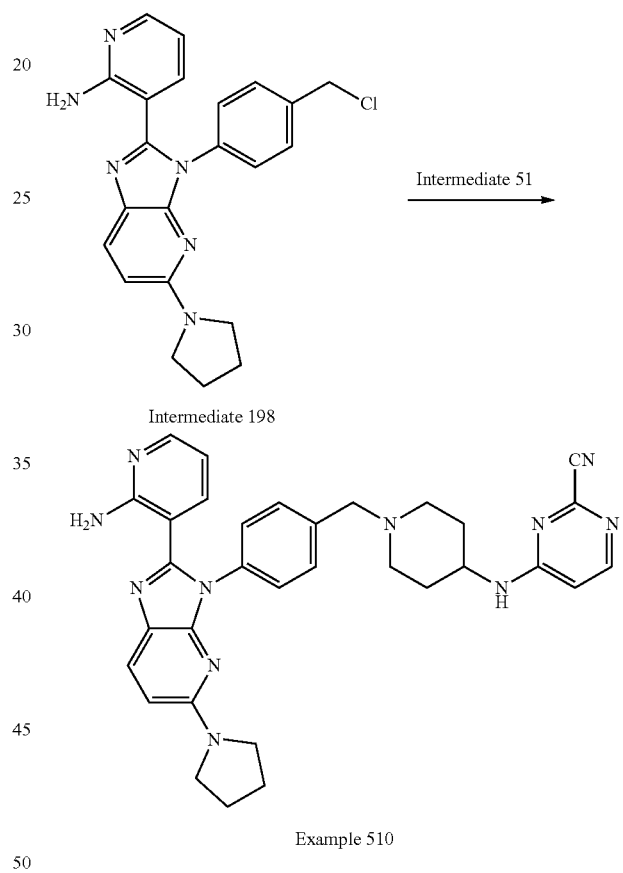

To a solution of Intermediate 198 (105 mg, 259 μmol) and Intermediate 51 (57.9 mg, 285 mol) in DMF (3 mL) were added NaI (7.76 mg, 51.8 μmol) and K₂CO₃ (107 mg, 776 μmol) at 20° C. The reaction mixture was stirred at 20° C. for 12 hr. The mixture was diluted with H₂O (10 mL) was added at 20° C. and extracted with EtOAc (10 mL×3). The combined organic layers were washed with brine (10 mL×2), dried over anhydrous Na₂SO₄, filtered, and concentrated under reduced pressure. After purified by prep-HPLC (column: Phenomenex C18 75×30 mm×3 μm; mobile phase: [water (NH₃H₂O+NH₄HCO₃)-ACN]; gradient: 50%-80% B over 7 min), 4-((1-(4-(2-(2-aminopyridin-3-yl)-5-(pyrrolidin-1-yl)-3H-imidazo[4,5-b]pyridin-3-yl)benzyl)piperidin-4-yl)amino)pyrimidine-2-carbonitrile (Example 510, 65.5 mg, yield: 44%) was obtained as a yellow solid. MS: m/z=572.4 [M+H]⁺. ¹H NMR (400 MHz, Dimethylsulfoxide-d$_6$) δ 8.11-8.04 (m, 2H), 7.92-7.88 (m, 2H), 7.42 (d, J=8.0 Hz, 2H), 7.31 (d, J=8.4 Hz, 2H), 7.08 (s, 2H), 6.94 (dd, J=7.6, 1.6 Hz, 1H), 6.67 (d, J=6.0 Hz, 1H), 6.50 (d, J=8.8 Hz, 1H), 6.29 (dd, J=8.0, 5.2 Hz, 1H), 3.81 (br.s, 1H), 3.56 (s, 2H), 3.34-3.30 (m, 3H), 2.83-2.78 (m, 2H), 2.17-2.08 (m, 2H), 1.95-1.80 (m, 7H), 1.53-1.42 (m, 2H).

Example 511: 4-((1-(4-(2-(2-Aminopyridin-3-yl)-5-(2-methoxypyridin-4-yl)-3H-imidazo[4,5-b]pyridin-3-yl)benzyl)piperidin-4-yl)amino)pyrimidine-2-carbonitrile 7.46-7.43 (m, 2H), 7.41 (s, 1H), 7.18 (dd, J=8.0, 1.6 Hz, 1H), 7.05 (s, 2H), 6.69 (d, J=5.6 Hz, 1H), 6.39 (dd, J=7.6, 4.8 Hz, 1H), 3.87 (s, 3H), 3.84-3.72 (m, 1H), 3.60 (s, 2H), 3.22-3.11 (m, 2H), 2.83-2.68 (m, 2H), 2.16-2.09 (m, 2H), 1.94-1.85 (m, 2H).

Example 512: 4-((1-(4-(2-(2-Aminopyridin-3-yl)-5-(5-methoxypyridin-3-yl)-3H-imidazo[4,5-b]pyridin-3-yl)benzyl)piperidin-4-yl)amino)pyrimidine-2-carbonitrile

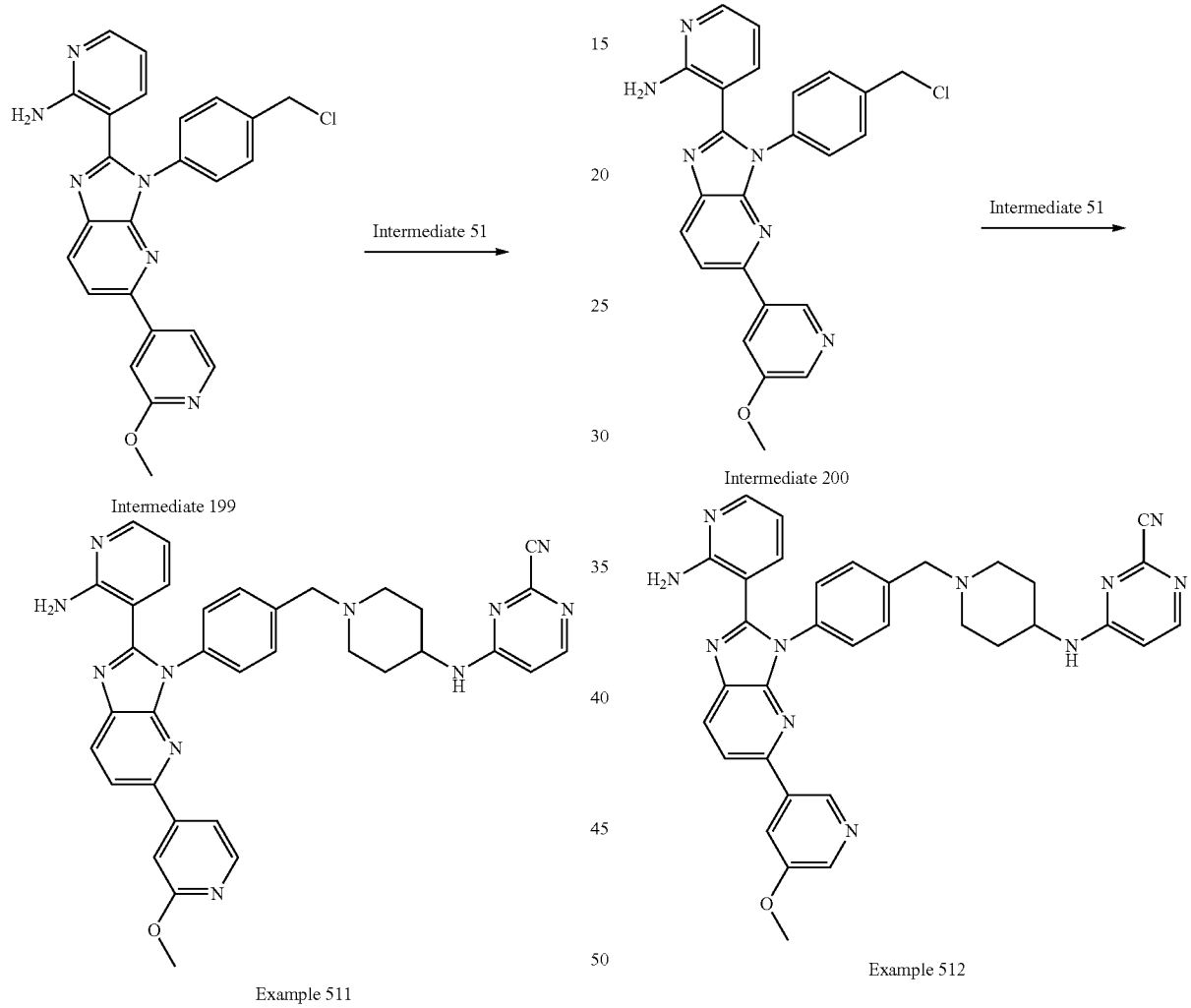

Example 511

Example 512

To a solution of Intermediate 199 (540 mg. 1.22 mmol) in DMF (5 mL) were added Intermediate 51 (273 mg, 1.34 mmol) and DIEA (4.88 mmol, 849 μL). The mixture was stirred at 80° C. for 8 hr. After purified by prep-HPLC (column: Phenomenex C18 75×30 mm×3 μm; mobile phase: [water (NH$_3$H$_2$O+NH$_4$HCO$_3$)-ACN]; gradient: 46%-76% B over 7 min), 4-((1-(4-(2-(2-aminopyridin-3-yl)-5-(2-methoxypyridin-4-yl)-3H-imidazo[4,5-b]pyridin-3-yl)benzyl)piperidin-4-yl)amino)pyrimidine-2-carbonitrile (Example 511, 169 mg, yield: 22.6%) was obtained as a light yellow solid. MS: m/z=610.1 [M+H]$^+$. $^1$H NMR (400 MHz, Dimethylsulfoxide-d$_6$) δ 8.31 (d, J=8.4 Hz, 1H), 8.24 (d, J=5.2 Hz, 1H), 8.16-8.04 (m, 3H), 8.01 (dd, J=4.8, 1.6 Hz, 1H), 7.62 (dd, J=5.6, 1.2 Hz, 1H), 7.52-7.47 (m, 2H), To a solution of Intermediate 200 (226 mg, 664 μmol) in DMF (3 mL) were added Intermediate 51 (135 mg, 664 μmol), DIEA (2.04 mmol, 356 μL). The mixture was stirred at 80° C. for 8 hr under N$_2$. The mixture was filtered and the filtrate was concentrated. After purified by prep-HPLC (column: Phenomenex C18 75×30 mm×3 μm; mobile phase: [water (NH$_3$H$_2$O+NH$_4$HCO$_3$)-ACN]; gradient: 42%-72% B over 7 min), 4-((1-(4-(2-(2-aminopyridin-3-yl)-5-(5-methoxypyridin-3-yl)-3H-imidazo[4,5-b]pyridin-3-yl)benzyl)piperidin-4-yl)amino)pyrimidine-2-carbonitrile (Example 512, 34.3 mg, yield: 11%) was obtained as a light yellow solid. MS: m/z=610.3 [M+H]$^+$. $^1$H NMR (400 MHz, Dimethylsulfoxide-d$_6$) δ 8.86 (d, J=1.6 Hz, 1H), 8.32-8.30 (m, 2H), 8.14-8.03 (m, 3H), 8.01 (dd, J=4.8, 2.0 Hz, 1H), 7.92 (dd, J=2.8, 2.0 Hz, 1H), 7.52-7.44 (m, 4H), 7.19 (dd, J=8.0, 2.0 Hz, 1H), 7.06 (s, 2H), 6.67 (d, J=6.0 Hz, 1H), 6.40 (dd, J=7.6, 4.8 Hz, 1H), 3.88 (s, 3H), 3.86-3.75 (m, 1H), 3.59 (s, 2H), 2.89-2.77 (m, 2H), 2.21-2.09 (m, 2H), 1.57-1.42 (m, 2H).

Example 513: 4-((1-(4-(2-(2-Aminopyridin-3-yl)-5-ethynyl-3H-imidazo[4,5-b]pyridin-3-yl)benzyl)piperidin-4-yl)amino)pyrimidine-2-carbonitrile

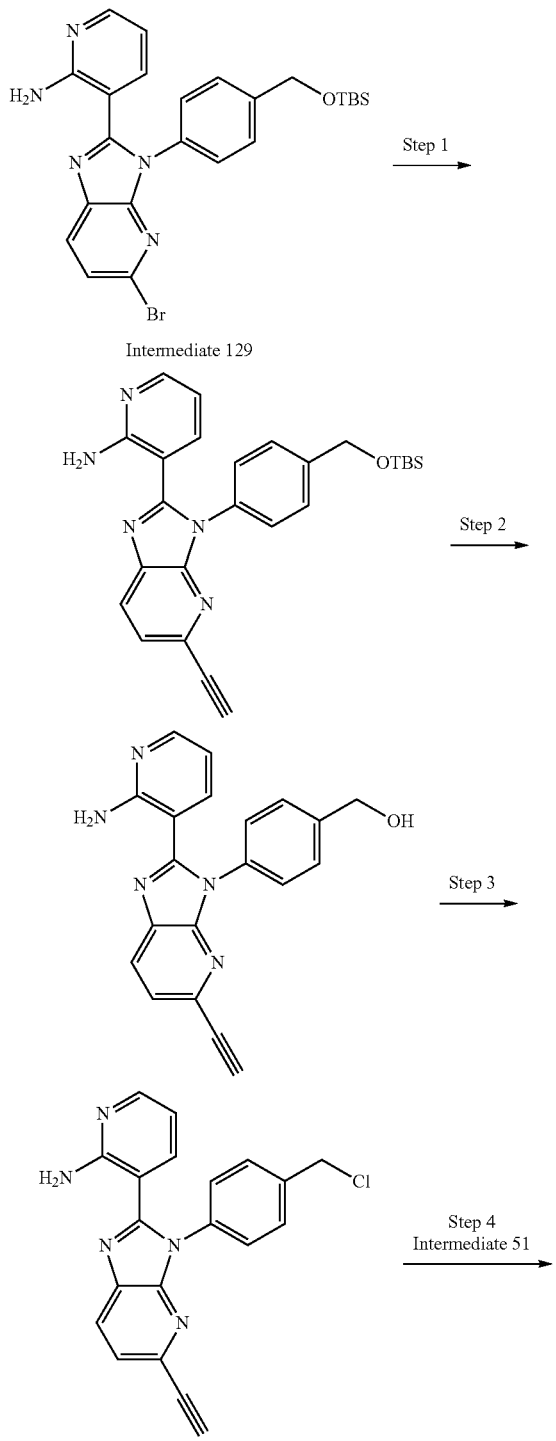

Intermediate 129

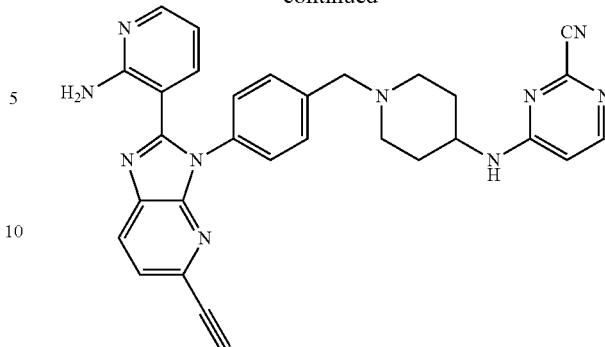

Example 513

Step 1: 3-(3-(4-(((Tert-butyldimethylsilyl)oxy)methyl)phenyl)-5-ethynyl-3H-imidazo[4,5-b]pyridin-2-yl)pyridin-2-amine A solution of Intermediate 129 (1 g, 1.96 mmol), Pd(PPh3)4 (113 mg, 98 μmol) and tributyl(ethynyl)stannane (1.23 g, 3.92 mmol) in 1,4-dioxane (10 mL) was degassed and purged with $N_2$ three times. The mixture was stirred at 100° C. for 16 hr under $N_2$ atmosphere.

The reaction was concentrated under reduced pressure. After purified by silica gel flash chromatography (Eluent of 30~50% EtOAc in petroleum ether), 3-(3-(4-(((tert-butyldimethylsilyl)oxy)methyl)phenyl)-5-ethynyl-3H-imidazo[4,5-b]pyridin-2-yl)pyridin-2-amine (900 mg, yield: 60%) was obtained as a black solid. MS: m/z=456.7 [M+H]$^+$.

Step 2: (4-(2-(2-Aminopyridin-3-yl)-5-ethynyl-3H-imidazo[4,5-b]pyridin-3-yl)phenyl)methanol To a solution of 3-(3-(4-(((tert-butyldimethylsilyl)oxy)methyl)phenyl)-5-ethynyl-3H-imidazo[4,5-b]pyridin-2-yl)pyridin-2-amine (160 mg, 351 μmol) in THF (4 mL) was added TBAF (92 mg, 351 μmol, 1 M). The mixture was stirred at 25° C. for 1 hr. The reaction mixture was quenched with $H_2O$ (10 mL) at 25° C., and extracted with EtOAc (20 mL×3). The combined organic layers were washed with brine (50 mL), dried over $Na_2SO_4$, filtered and concentrated under reduced pressure. (4-(2-(2-Aminopyridin-3-yl)-5-ethynyl-3H-imidazo[4,5-b]pyridin-3-yl)phenyl)methanol (130 mg, yield: 63%) was obtained as a brown solid. MS: m/z=341.9 [M+H]$^+$.

Step 3: 3-(3-(4-(Chloromethyl)phenyl)-5-ethynyl-3H-imidazo[4,5-b]pyridin-2-yl)pyridin-2-amine To a solution of (4-(2-(2-aminopyridin-3-yl)-5-ethynyl-3H-imidazo[4,5-b]pyridin-3-yl)phenyl)methanol (130 mg, 381 μmol) in $CH_2Cl_2$ (5 mL) was added $SOCl_2$ (90.7 mg, 762 μmol) at 0° C. The mixture was stirred at 40° C. for 0.5 hr. The reaction mixture was quenched with $H_2O$ (1 mL) at 25° C., and concentrated under reduced pressure to give 3-(3-(4-(chloromethyl)phenyl)-5-ethynyl-3H-imidazo[4,5-b]pyridin-2-yl)pyridin-2-amine (130 mg, yield: 52%) as a brown solid. MS: m/z=360.0.

Step 4: 4-((1-(4-(2-(2-Aminopyridin-3-yl)-5-ethynyl-3H-imidazo[4,5-b]pyridin-3-yl)benzyl)piperidin-4-yl)amino)pyrimidine-2-carbonitrile To a solution of 3-(3-(4-(chloromethyl)phenyl)-5-ethynyl-3H-imidazo[4,5-b]pyridin-2-yl)pyridin-2-amine (130 mg, 328 μmol) and Intermediate 51 (104 mg, 328 μmol) in DMF (5 mL) were added K₂CO₃ (226.7 mg, 1.64 mmol) and NaI (24.6 mg, 164 μmol). The mixture was stirred at 25° C. for 16 hr. The mixture was filtered, and concentrated. After purified by silica gel flash chromatography (Eluent of 0%-6% MeOH in CH₂Cl₂) and purified by prep-TLC (CH₂Cl₂:MeOH=10:1), 4-((1-(4-(2-(2-aminopyridin-3-yl)-5-ethynyl-3H-imidazo[4,5-b]pyridin-3-yl)benzyl)piperidin-4-yl)amino)pyrimidine-2-carbonitrile (Example 513, 42.5 mg, yield: 24%) was obtained as a yellow solid. MS: m/z=527.2 [M+H]⁺. ¹H NMR (400 MHz, Methanol-d₄) δ 8.18-8.09 (m, 1H), 8.08-7.94 (m, 2H), 7.61-7.51 (m, 3H), 7.39 (d, J=8.4 Hz, 2H), 7.30 (dd, J=7.6, 1.6 Hz, 1H), 6.60 (d, J=6.0 Hz, 1H), 6.45 (dd, J=7.6, 5.2 Hz, 1H), 4.12-3.82 (m, 1H), 3.75-3.59 (m, 3H), 3.01-2.91 (m, 2H), 2.28 (t, J=10.8 Hz, 2H), 2.04-1.98 (m, 2H), 1.66-1.59 (m, 2H).

Example 514: N-(3-(2-(2-Aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)-N-methylacetamide

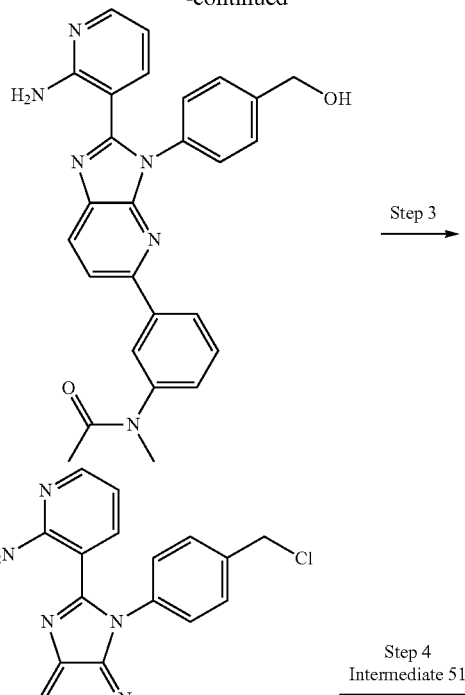

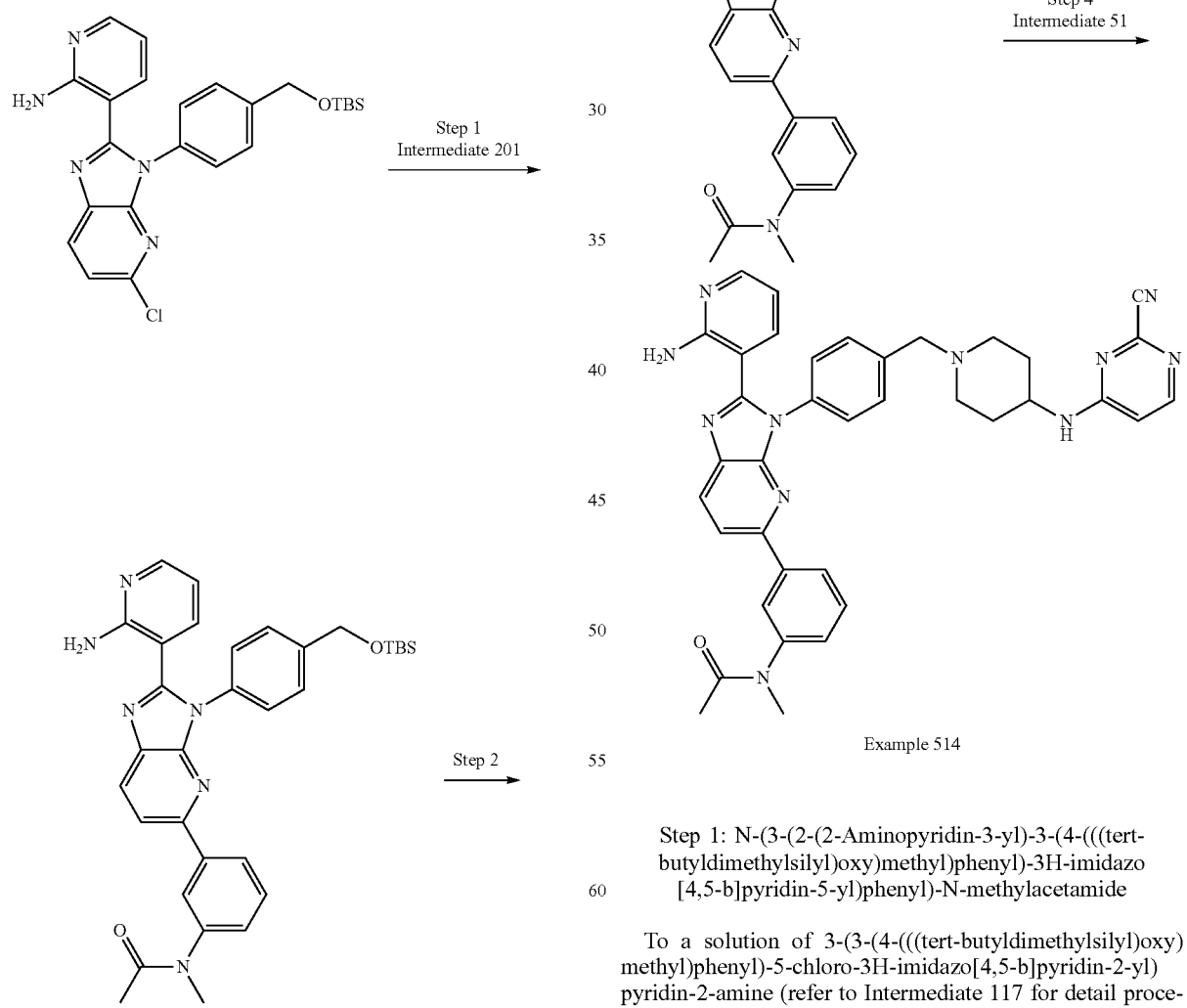

Step 1: N-(3-(2-(2-Aminopyridin-3-yl)-3-(4-(((tert-butyldimethylsilyl)oxy)methyl)phenyl)-3H-imidazo[4,5-b]pyridin-5-yl)phenyl)-N-methylacetamide To a solution of 3-(3-(4-(((tert-butyldimethylsilyl)oxy)methyl)phenyl)-5-chloro-3H-imidazo[4,5-b]pyridin-2-yl)pyridin-2-amine (refer to Intermediate 117 for detail procedures, 500 mg, 1.07 mmol) and Intermediate 201 (325 mg, 1.18 mmol) in 1,4-dioxane (25 mL) and H₂O (5 mL) were added Cs₂CO₃ (1.05 g, 3.22 mmol) and Pd(dppf)Cl₂ (78.5 mg, 107 μmol) at 25° C. The mixture was degassed and purged with N₂ three times and stirred at 100° C. for 2 hr. The mixture was quenched with H₂O (50 mL) and extracted with EtOAc (30 mL×3). The combined organic layers were washed with brine (50 mL), dried over Na₂SO₄, filtered and concentrated. After purified by silica gel flash chromatography (EtoAc in petroleum ether=0-80%), N-(3-(2-(2-aminopyridin-3-yl)-3-(4-(((tert-butyldimethylsilyl)oxy)methyl)phenyl)-3H-imidazo[4,5-b]pyridin-5-yl)phenyl)-N-methylacetamide (300 mg, yield: 48.3%) was obtained as a yellow solid. MS: m/z=579.4 [M+H]⁺.

Step 2: N-(3-(2-(2-Aminopyridin-3-yl)-3-(4-(hydroxymethyl)phenyl)-3H-imidazo[4,5-b]pyridin-5-yl)phenyl)-N-methylacetamide To a solution of N-(3-(2-(2-aminopyridin-3-yl)-3-(4-(((tert-butyldimethylsilyl)oxy)methyl)phenyl)-3H-imidazo[4,5-b]pyridin-5-yl)phenyl)-N-methylacetamide (300 mg, 518 μmol) in THF (5 mL) was added TBAF (1M in THF) (1 M, 778 μL) at 25° C. This mixture was stirred at 25° C. for 1 hr. The mixture was quenched with H₂O (20 mL) and extracted with EtOAc (20 mL×3). The combined organic layers were washed with brine (20 mL), dried over Na₂SO₄, filtered and concentrated. N-(3-(2-(2-Aminopyridin-3-yl)-3-(4-(hydroxymethyl)phenyl)-3H-imidazo[4,5-b]pyridin-5-yl)phenyl)-N-methylacetamide (150 mg, yield: 62.3%) was obtained as yellow oil, which was used directly without purification. MS: m/z=465.3 [M+H]⁺.

Step 3: N-(3-(2-(2-Aminopyridin-3-yl)-3-(4-(chloromethyl)phenyl)-3H-imidazo[4,5-b]pyridin-5-yl)phenyl)-N-methylacetamide To a solution of N-(3-(2-(2-aminopyridin-3-yl)-3-(4-(hydroxymethyl)phenyl)-3H-imidazo[4,5-b]pyridin-5-yl)phenyl)-N-methylacetamide (150 mg, 323 μmol) in CH₂Cl₂ (3 mL) was added SOCl₂ (57.6 mg, 484 μmol) at 25° C. This mixture was stirred at 25° C. for 2 hr. The reaction mixture was concentrated to give N-(3-(2-(2-aminopyridin-3-yl)-3-(4-(chloromethyl)phenyl)-3H-imidazo[4,5-b]pyridin-5-yl)phenyl)-N-methylacetamide (120 mg, yield: 76.9%) as a yellow solid, which was used directly without purification. MS: m/z=483.2 [M+H]⁺.

Step 4: N-(3-(2-(2-Aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)-N-methylacetamide To a solution of N-(3-(2-(2-aminopyridin-3-yl)-3-(4-(chloromethyl)phenyl)-3H-imidazo[4,5-b]pyridin-5-yl)phenyl)-N-methylacetamide (120 mg, 248.5 μmol) and Intermediate 51 (55.6 mg, 27 μmol) in DMF (3 mL) were added NaI (3.72 mg, 24.9 mol) and K₂CO₃ (103 mg, 745 μmol) at 25° C. The mixture was degassed and purged with N₂ three times and stirred at 80° C. for 2 hr. The mixture was quenched with H₂O (30 mL) and extracted with EtOAc (30 mL×3). The combined organic layers were washed with brine (50 mL), dried over Na₂SO₄, filtered and concentrated. After purified by prep-HPLC (column: Phenomenex C18 75×30 mm×3 μm; mobile phase: [water (NH₃H₂O+NH₄HCO₃)-ACN]; gradient: 43%-73% B over 7 min), N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)-N-methylacetamide (Example 514, 41.8 mg, yield: 25.9%) was obtained as a light yellow solid. MS: m/z=650.1 [M+H]⁺. ¹H NMR (400 MHz, Dimethylsulfoxide-d₆) δ 8.28 (d, J=8.4 Hz, 1H), 8.15-7.90 (m, 6H), 7.58-7.42 (m, 5H), 7.36 (d, J=7.2 Hz, 1H), 7.16 (dd, J=7.6, 1.6 Hz, 1H), 7.07 (s, 2H), 6.68 (d, J=6.0 Hz, 1H), 6.38 (dd, J=7.6, 4.8 Hz, 1H), 3.88-3.74 (m, 1H), 3.59 (s, 2H), 3.19 (s, 3H), 2.89-2.75 (m, 2H), 2.21-2.07 (m, 2H), 1.96-1.71 (m, 5H), 1.57-1.41 (m, 2H).

Example 515: 4-((1-(4-(2-(2-Aminopyridin-3-yl)-5-(3-methoxypyridin-4-yl)-3H-imidazo[4,5-b]pyridin-3-yl)benzyl)piperidin-4-yl)amino)pyrimidine-2-carbonitrile

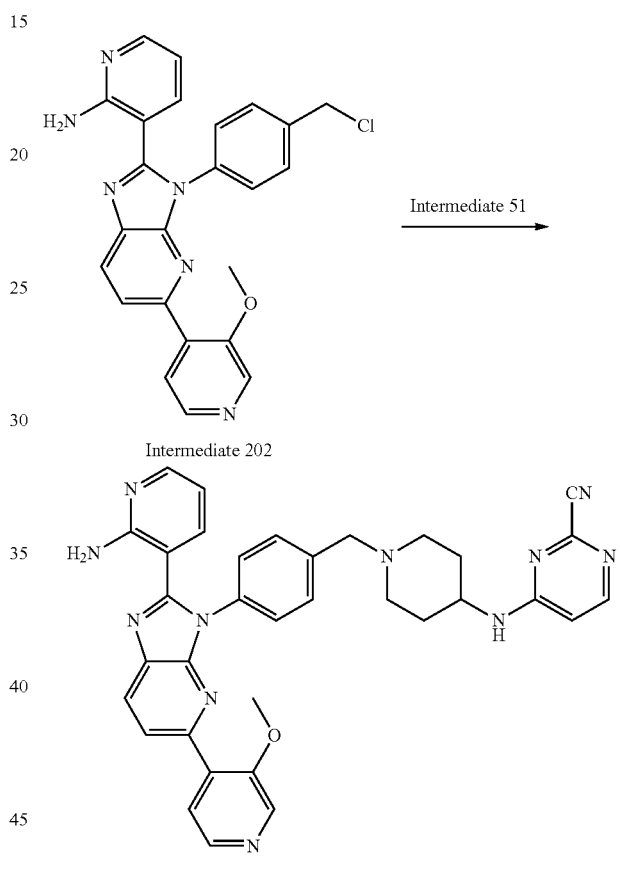

To a solution of Intermediate 202 (150 mg, 339 μmol) in DMF (3 mL) were added DIEA (175 mg, 1.35 mmol) and Intermediate 51 (89.5 mg, 440 μmol). The mixture was stirred at 80° C. for 2 hr. Water (50 mL) was added. The mixture was extracted with EtOAc (20 mL×2). The combined organic layers were dried over anhydrous Na₂SO₄, filtered and concentrated. After purified by prep-HPLC (column: Phenomenex C18 75×30 mm×3 μm; mobile phase: [water (NH₃H₂O+NH₄HCO₃)-ACN]; gradient: 40%-70% B over 7 min), 4-((1-(4-(2-(2-aminopyridin-3-yl)-5-(3-methoxypyridin-4-yl)-3H-imidazo[4,5-b]pyridin-3-yl)benzyl)piperidin-4-yl)amino)pyrimidine-2-carbonitrile (Example 515, 73.5 mg, yield: 36%) was obtained as a light yellow solid. MS: m/z=610.1 [M+H]⁺. ¹H NMR (400 MHz, Dimethylsulfoxide-d₆) δ 8.53 (s, 1H), 8.32-8.25 (m, 2H), 8.14-7.95 (m, 4H), 7.64 (d, J=4.8 Hz, 1H), 7.51-7.41 (m, 4H), 7.11 (d, J=7.6 Hz, 1H), 7.02 (s, 2H), 6.67 (d, J=6.4 Hz, 1H), 6.38 (dd, J=7.6, 4.8 Hz, 1H), 3.98 (s, 3H), 3.87-3.71 (m, 1H), 3.57 (s, 2H), 2.87-2.76 (m, 2H), 2.20-2.09 (m, 2H), 1.94-1.81 (m, 2H), 1.55-1.41 (m, 2H).

Example 516: 4-((1-(4-(2-(2-Aminopyridin-3-yl)-5-(6-methoxypyridin-3-yl)-3H-imidazo[4,5-b]pyridin-3-yl)benzyl)piperidin-4-yl)amino)pyrimidine-2-carbonitrile

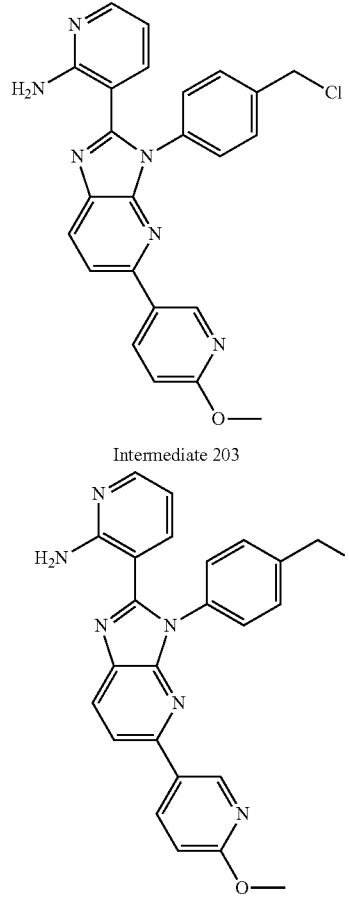

Intermediate 203

Example 516

To a solution of Intermediate 203 (240 mg, 542 μmol) in DMF (1 mL) were added DIEA (280 mg, 2.17 mmol) and Intermediate 51 (143 mg, 704 μmol). The mixture was stirred at 25° C. for 2 hr. After purified by prep-HPLC (column: Phenomenex C18 80×30 mm×5 μm; mobile phase: [water (NH₃H₂O+NH₃HCO₃)-ACN]; gradient: 50%-80% B over 7 min), 4-((1-(4-(2-(2-aminopyridin-3-yl)-5-(6-methoxypyridin-3-yl)-3H-imidazo[4,5-b]pyridin-3-yl)benzyl)piperidin-4-yl)amino)pyrimidine-2-carbonitrile (Example 516, 126 mg, yield: 38.3%) was obtained as a yellow solid. MS: m/z=610.2 [M+H]⁺. ¹H NMR (400 MHz, Dimethylsulfoxide-$d_6$) δ 8.85 (d, J=2.4 Hz, 1H), 8.40-8.20 (m, 2H), 8.15-7.90 (m, 4H), 7.60-7.40 (m, 4H), 7.15 (dd, J=7.6, 1.6 Hz, 1H), 7.05 (s, 2H), 6.92 (d, J=9.2 Hz, 1H), 6.67 (d, J=6.0 Hz, 1H), 6.37 (dd, J=7.6, 4.8 Hz 1H), 3.89 (s, 3H), 3.90-3.70 (m, 1H), 3.59 (s, 2H), 2.83-2.80 (m, 2H), 2.30-2.10 (m, 2H), 1.89-1.82 (m, 2H), 1.60-1.40 (m, 2H).

Example 517: 4-((1-(4-(5-(3-Aminophenyl)-2-(2-aminopyridin-3-yl)-3H-imidazo[4,5-b]pyridin-3-yl)benzyl)piperidin-4-yl)amino)pyrimidine-2-carbonitrile

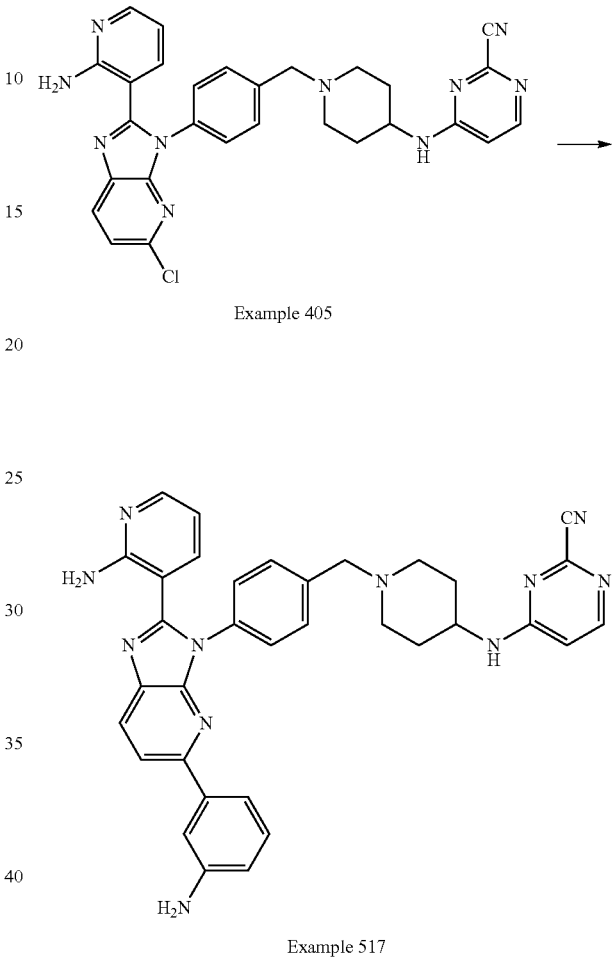

Example 405

Example 517

To a solution of Intermediate 405 (500 mg, 860 gmol) and (3-aminophenyl)boronic acid (130 mg, 946 μmol) in 1,4-dioxane (5 mL) and H₂O (1 mL) were added Pd(dppf)Cl₂ (62.9 mg, 86.0 μmol) and Cs₂CO₃ (841 mg, 2.58 mmol). The mixture was degassed and purged with N₂ three times and stirred at 90° C. for 16 hr under N₂. The reaction mixture was filtered and concentrated under reduced pressure. The crude product was purified by silica gel flash chromatography (MeOH in CH₂Cl₂=1 to 10%) and prep-HPLC (column: Waters xbridge 150×25 mm 10 μm; mobile phase: [water (NH₄HCO₃)-ACN]; gradient: 35%-55% B over 11 min). 4-((1-(4-(5-(3-Aminophenyl)-2-(2-aminopyridin-3-yl)-3H-imidazo[4,5-b]pyridin-3-yl)benzyl)piperidin-4-yl)amino) pyrimidine-2-carbonitrile (Example 517, 164 mg, yield: 31.1%) was obtained as a light yellow solid. MS: m/z=594.3 [M+H]⁺. ¹H NMR (400 MHz, Methanol-$d_4$) δ 8.16 (d, J=8.0 Hz, 1H), 8.05-7.92 (m, 2H), 7.87 (d, J=8.4 Hz, 1H), 7.56-7.52 (m, 2H), 7.47-7.43 (m, 2H), 7.41 (t, J=1.6 Hz, 1H), 7.37-7.33 (m, 1H), 7.31 (dd, J=7.6, 1.6 Hz, 1H), 7.17 (t, J=8.0 Hz, 1H), 6.75 (dd, J=7.6, 1.2 Hz, 1H), 6.64-6.55 (m, 1H), 6.47 (dd, J=7.6, 4.8 Hz, 1H), 4.10-3.81 (m, 1H), 3.66 (s, 2H), 3.01-2.93 (m, 2H), 2.32-2.23 (m, 2H), 2.04-1.98 (m, 2H), 1.66-1.58 (m, 2H).

Example 518 and 519: N-(3-(2-(2-Aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)isobutyramide & N-(3-(3-(4-((4-((2-cyanopyrimidin-4-yl)amino)piperidin-1-yl)methyl)phenyl)-2-(2-isobutyramidopyridin-3-yl)-3H-imidazo[4,5-b]pyridin-5-yl)phenyl)isobutyramide

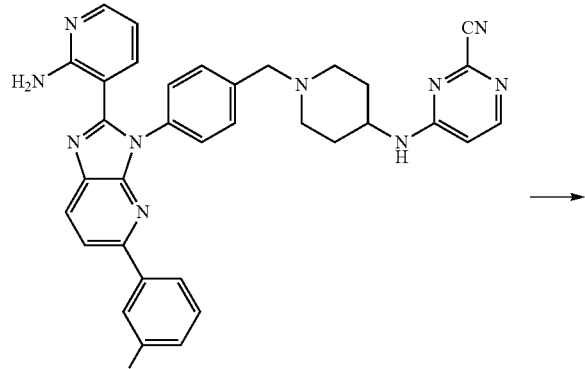

Example 517

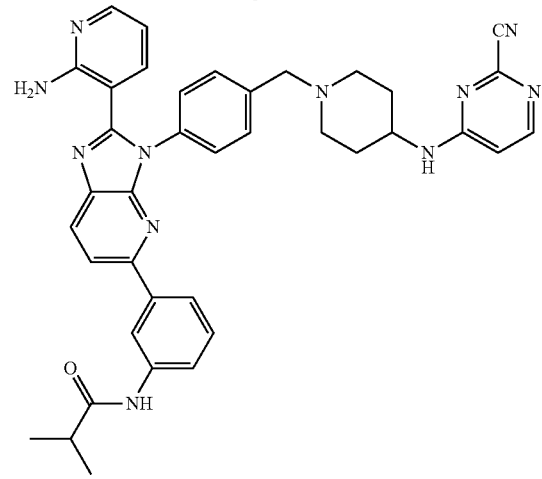

Example 518

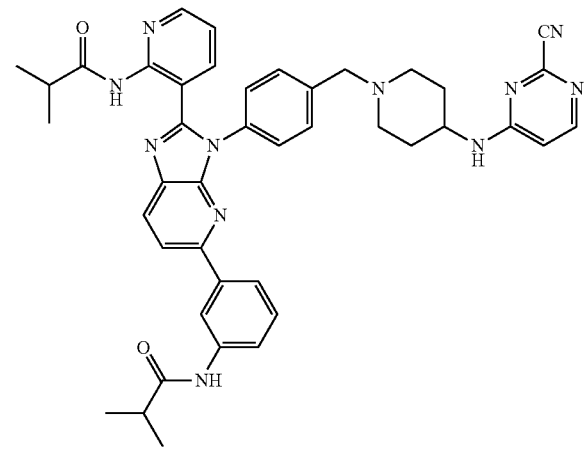

Example 519

To a solution of Example 517 (220 mg, 371 μmol) and TEA (103 μL, 741 μmol) in THF (5 mL) was added 2-methylpropanoyl chloride (43.4 mg, 408 μmol) dropwise. The mixture was degassed and purged with N2 three times and stirred at 0° C. for 0.5 hr under N2. The reaction mixture was filtered and concentrated under reduced pressure. After purified by silica gel flash chromatography (MeOH in CH$_2$Cl$_2$=1 to 10%) and prep-HPLC (column: Welch Xtimate C18 150×25 mm×5 μm; mobile phase: [water (HCl)-ACN]; gradient: 12%-42% B over 8 min), N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)isobutyramide (Example 518, 19.8 mg, yield: 7.6%) was obtained as a light yellow solid. MS: m/z=664.3 [M+H]$^+$. $^1$H NMR (400 MHz, Dimethylsulfoxide-d$_6$) δ 9.93 (br s, 1H), 8.28 (d, J=8.4 Hz, 1H), 8.21-8.16 (m, 1H), 8.12-8.03 (m, 2H), 8.00 (dd, J=4.8, 1.6 Hz, 1H), 7.87 (d, J=8.4 Hz, 1H), 7.71-7.64 (m, 2H), 7.50-7.43 (m, 4H), 7.37 (t, J=8.0 Hz, 1H), 7.15 (dd, J=7.6, 1.6 Hz, 1H), 6.99 (br s, 2H), 6.68 (d, J=5.6 Hz, 1H), 6.38 (dd, J=7.6, 4.8 Hz, 1H), 3.88-3.73 (m, 1H), 3.59 (s, 2H), 2.88-2.80 (m, 2H), 2.63-2.55 (m, 1H), 2.21-2.12 (m, 2H), 1.93-1.85 (m, 2H), 1.54-1.46 (m, 2H), 1.08 (d, J=6.8 Hz, 6H). N-(3-(3-(4-((4-((2-cyanopyrimidin-4-yl)amino)piperidin-1-yl)methyl)phenyl)-2-(2-isobutyramidopyridin-3-yl)-3H-imidazo[4,5-b]pyridin-5-yl)phenyl)isobutyramide (Example 519, 51 mg, yield: 17.5%) was obtained as a light yellow solid. MS: m/z=734.3 [M+H]$^+$. $^1$H NMR (400 MHz, Dimethylsulfoxide-d$_6$) 10.55 (br s, 1H), 9.94 (br s, 1H), 8.44 (dd, J=4.8, 1.6 Hz, 1H), 8.23-8.19 (m, 1H), 8.14 (d, J=8.4 Hz, 1H), 8.09-8.05 (m, 2H), 7.82 (d, J=8.0 Hz, 1H), 7.75-7.68 (m, 4H), 7.46-7.39 (m, 4H), 7.12 (dd, J=7.6, 4.8 Hz, 1H), 6.67 (d, J=6.0 Hz, 1H), 3.87-3.75 (m, 1H), 3.56 (s, 2H), 2.86-2.79 (m, 2H), 2.65-2.58 (m, 2H), 2.18-2.10 (m, 2H), 1.94-1.85 (m, 2H), 1.52-1.45 (m, 2H), 1.10 (d, J=6.8 Hz, 6H), 0.90 (d, J=6.8 Hz, 6H).

Example 520: Methyl (3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)carbamate

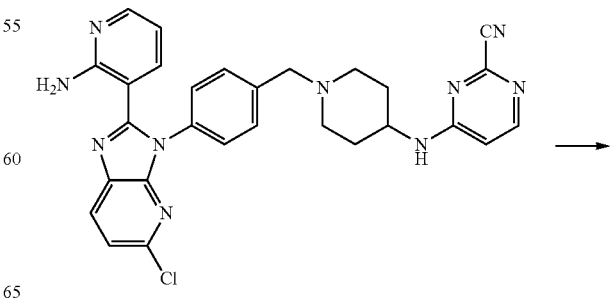

Example 405

1651
-continued

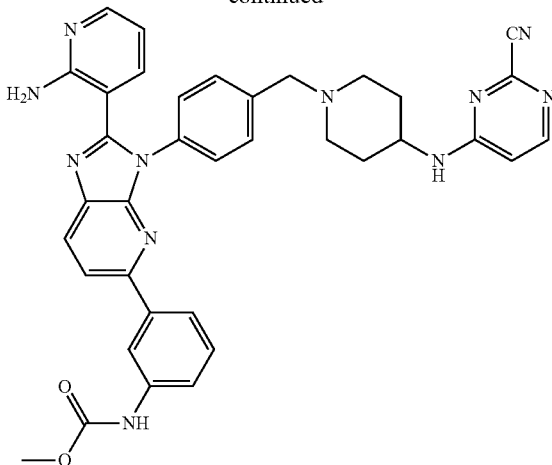

Example 520

1652
-continued

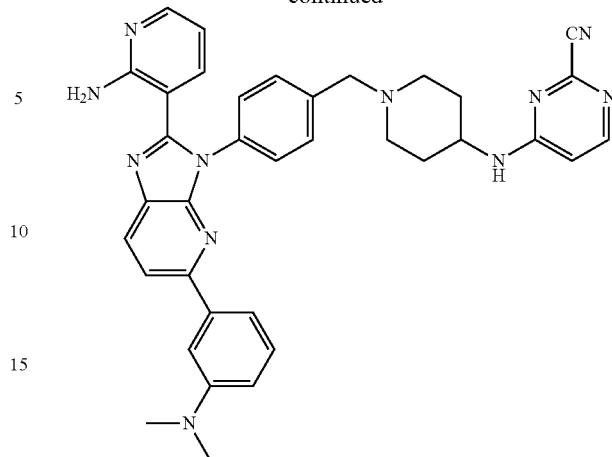

Example 521

To a solution of Intermediate 405 (250 mg, 466 μmol) and methyl (3-(4,4,5,5-tetramethyl-1,3,2-dioxaborolan-2-yl)phenyl)carbamate (142 mg, 512 μmol) in 1,4-dioxane (3 mL) and H$_2$O (0.6 mL) were added Pd(dppf)Cl$_2$ (68.1 mg, 93.1 μmol) and Cs$_2$CO$_3$ (455 mg, 1.40 mmol). The mixture was degassed and purged with N$_2$ three times and stirred at 100° C. for 16 hr under N$_2$. The reaction mixture was filtered and concentrated under reduced pressure. The crude product was purified by silica gel flash chromatography (MeOH in CH$_2$Cl$_2$=1 to 10%) and then purified by prep-HPLC (column: Welch Xtimate C18 150×25 mm×5 μm; mobile phase: [water (HCl)-ACN]; gradient: 10%-40% B over 8 min). Methyl (3-(2-(2-Aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)carbamate (Example 520, 80.8 mg, yield: 24.8%) was obtained as a light yellow solid. MS: m/z=652.2 [M+H]$^+$. $^1$H NMR (400 MHz, Dimethylsulfoxide-d$_6$) δ 9.74 (br s, 1H), 8.27 (d, J=8.0 Hz, 1H), 8.13-8.02 (m, 3H), 8.00 (dd, J=4.4, 1.6 Hz, 1H), 7.86 (d, J=8.4 Hz, 1H), 7.66-7.61 (m, 1H), 7.51-7.43 (m, 5H), 7.39-7.34 (m, 1H), 7.16 (dd, J=8.0, 2.0 Hz, 1H), 7.00 (br s, 2H), 6.67 (d, J=6.0 Hz, 1H), 6.38 (dd, J=7.6, 4.8 Hz, 1H), 3.87-3.75 (m, 1H), 3.67 (s, 3H), 3.59 (s, 2H), 2.87-2.80 (m, 2H), 2.20-2.11 (m, 2H), 1.93-1.85 (m, 2H), 1.54-1.45 (m, 2H).

Example 521: 4-((1-(4-(2-(2-Aminopyridin-3-yl)-5-(3-(dimethylamino)phenyl)-3H-imidazo[4,5-b]pyridin-3-yl)benzyl)piperidin-4-yl)amino)pyrimidine-2-carbonitrile To a solution of Example 405 (250 mg, 466 μmol) and (3-(dimethylamino)phenyl)boronic acid (84.5 mg, 512 μmol) in 1,4-dioxane (3 mL) and H$_2$O (0.6 mL) were added Pd(dppf)Cl$_2$ (68.1 mg, 93.1 μmol) and Cs$_2$CO$_3$ (455 mg, 1.40 mmol). The mixture was degassed and purged with N$_2$ three times and stirred at 100° C. for 16 hr under N$_2$. The reaction mixture was filtered and concentrated under reduced pressure. The crude product was purified by silica gel flash chromatography (MeOH in CH$_2$Cl$_2$=1 to 10%) and then purified by prep-HPLC (column: Waters xbridge 150× 25 mm 10 μm; mobile phase: [water (NH$_4$HCO$_3$)-ACN]; gradient: 42%-72% B over 11 min). 4-((1-(4-(2-(2-Aminopyridin-3-yl)-5-(3-(dimethylamino)phenyl)-3H-imidazo[4,5-b]pyridin-3-yl)benzyl)piperidin-4-yl)amino)pyrimidine-2-carbonitrile (Example 521, 53.1 mg, yield: 18.1%) was obtained as a light yellow solid. MS: m/z=622.3 [M+H]$^+$. $^1$H NMR (400 MHz, Dimethylsulfoxide-d$_6$) 8.23 (d, J=8.4 Hz, 1H), 8.09 (d, J=6.0 Hz, 1H), 8.05 (d, J=7.2 Hz, 1H), 8.00 (dd, J=4.8, 1.6 Hz, 1H), 7.96 (d, J=8.4 Hz, 1H), 7.49-7.44 (m, 4H), 7.42-7.40 (m, 1H), 7.34-7.31 (m, 1H), 7.27-7.23 (m, 1H), 7.19 (dd, J=7.6, 1.6 Hz, 1H), 7.06 (br s, 2H), 6.76 (dd, J=8.0, 2.0 Hz, 1H), 6.68 (d, J=6.0 Hz, 1H), 6.39 (dd, J=7.6, 4.8 Hz, 1H), 3.88-3.74 (m, 1H), 3.59 (s, 2H), 2.92 (s, 6H), 2.85-2.79 (m, 2H), 2.19-2.10 (m, 2H), 1.94-1.86 (m, 2H), 1.53-1.44 (m, 2H).

Example 522: N-(1-(3-(2-(2-Aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)piperidin-4-yl)-N-methylacetamide

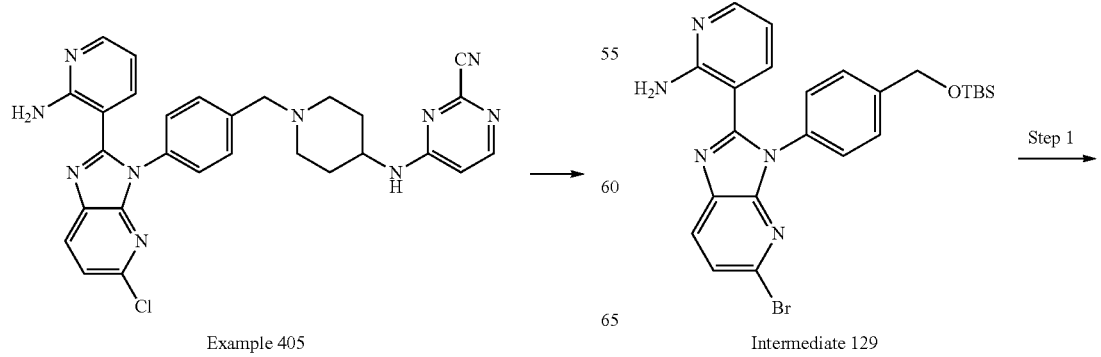

Example 405                Intermediate 129

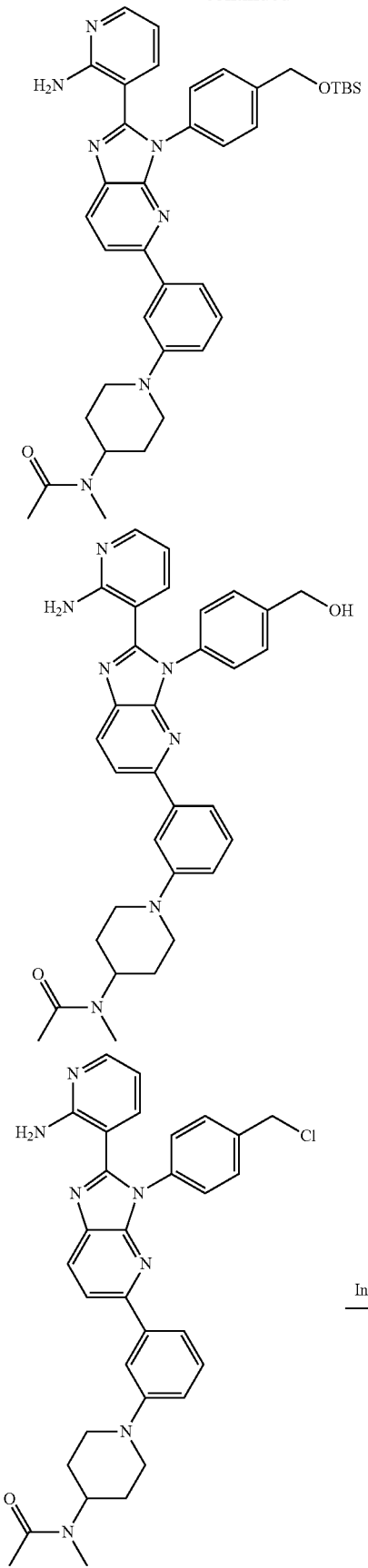

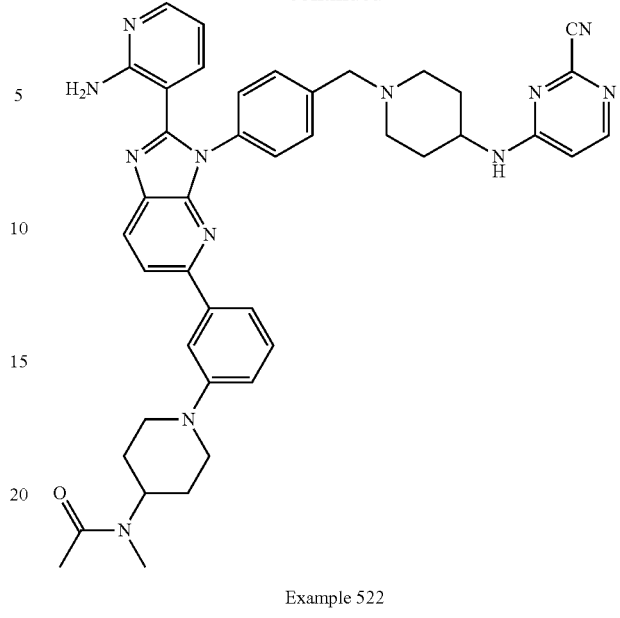

Example 522

Step 1: N-(1-(3-(2-(2-Aminopyridin-3-yl)-3-(4-(((tert-butyldimethylsilyl)oxy)methyl)phenyl)-3H-imidazo[4,5-b]pyridin-5-yl)phenyl)piperidin-4-yl)-N-methylacetamide To a solution of Intermediate 129 (500 mg, 833 μmol) in 1,4-dioxane (25 mL) and H$_2$O (5 mL) were added Intermediate 204 (328 mg, 916 μmol), Cs$_2$CO$_3$ (813.75 mg, 2.50 mmol) and Pd(dppf)Cl$_2$ (60.9 mg, 83.3 μmol) at 20° C. The reaction mixture was stirred at 100° C. for 2 hr. Water (30 mL) was added. The mixture was extracted with EtOAc (30 mL×3). The combined organic layers were washed with brine (30 mL×2), dried over anhydrous Na$_2$SO$_4$, filtered, and concentrated under reduced pressure. After purified by silica gel flash chromatography (MeOH in CH$_2$Cl$_2$=0-20%), N-(1-(3-(2-(2-aminopyridin-3-yl)-3-(4-(((tert-butyldimethylsilyl)oxy)methyl)phenyl)-3H-imidazo[4,5-b]pyridin-5-yl)phenyl)piperidin-4-yl)-N-methylacetamide (370 mg, 67.1% yield) was obtained as a purple solid. MS: m/z=662.4 [M+H]$^+$.

Step 2: N-(1-(3-(2-(2-Aminopyridin-3-yl)-3-(4-(hydroxymethyl)phenyl)-3H-imidazo[4,5-b]pyridin-5-yl)phenyl)piperidin-4-yl)-N-methylacetamide To a solution of -(1-(3-(2-(2-aminopyridin-3-yl)-3-(4-(((tert-butyldimethylsilyl)oxy)methyl)phenyl)-3H-imidazo[4,5-b]pyridin-5-yl)phenyl)piperidin-4-yl)-N-methylacetamide (360 mg, 544 μmol) in THF (12 mL) was added TBAF (1 M in THF, 816 μL). The reaction mixture was stirred at 20° C. for 1 hr. Water (20 mL) was added. The mixture was extracted with EtOAc (20 mL×3). The combined organic layers were washed with brine (20 mL×2), dried over anhydrous Na$_2$SO$_4$, filtered, and concentrated under reduced pressure. N-(1-(3-(2-(2-Aminopyridin-3-yl)-3-(4-(hydroxymethyl)phenyl)-3H-imidazo[4,5-b]pyridin-5-yl)phenyl)piperidin-4-yl)-N-methylacetamide (298 mg. 544 μmol, crude) was obtained as a purple solid, which was used directly into the next step. MS: m/z=548.3 [M+H]$^+$.

Step 3: N-(1-(3-(2-(2-Aminopyridin-3-yl)-3-(4-(chloromethyl)phenyl)-3H-imidazo[4,5-b]pyridin-5-yl)phenyl)piperidin-4-yl)-N-methylacetamide To a solution of N-(1-(3-(2-(2-aminopyridin-3-yl)-3-(4-(hydroxymethyl)phenyl)-3H-imidazo[4,5-b]pyridin-5-yl)phenyl)piperidin-4-yl)-N-methylacetamide (150 mg, 274 µmol) in CH$_2$Cl$_2$ (6 mL) was added SOCl$_2$ (97.8 mg, 822 µmol). The reaction mixture was stirred at 20° C. for 2 hr. The reaction mixture was concentrated to give N-(1-(3-(2-(2-aminopyridin-3-yl)-3-(4-(chloromethyl)phenyl)-3H-imidazo[4,5-b]pyridin-5-yl)phenyl)piperidin-4-yl)-N-methylacetamide (155 mg, 274 µmol, crude) as a gray solid, which was used directly into the next step. MS: m/z=566.1 [M+H]$^+$.

Step 4: N-(1-(3-(2-(2-Aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)piperidin-4-yl)-N-methylacetamide To a solution of N-(1-(3-(2-(2-aminopyridin-3-yl)-3-(4-(chloromethyl)phenyl)-3H-imidazo[4,5-b]pyridin-5-yl)phenyl)piperidin-4-yl)-N-methylacetamide (155 mg, 274 µmol) and Intermediate 51 (61.2 mg, 301 µmol) in DMF (5 mL) were added K$_2$CO$_3$ (114 mg, 822 gmol) and NaI (8.21 mg, 54.8 µmol) at 20° C. The reaction mixture was stirred at 80° C. for 2 hr. Water (20 mL) was added. The resulting mixture was extracted with EtOAc (20 mL×3). The combined organic layers were washed with brine (20 mL×2), dried over anhydrous Na$_2$SO$_4$, filtered, and concentrated under reduced pressure. The residue was re-crystallized from MeCN (5 mL). N-(1-(3-(2-(2-Aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)piperidin-4-yl)-N-methylacetamide (Example 522, 73.0 mg, yield: 36.4% for 3 steps) was obtained as a gray solid. MS: m/z=733.4 [M+H]$^+$. $^1$H NMR (400 MHz, Dimethylsulfoxide-d$_6$) δ 8.24 (d, J=8.4 Hz, 1H), 8.10-7.95 (m, 4H), 7.64 (s, 1H), 7.50-7.42 (m, 5H), 7.28 (t, J=8.0 Hz, 1H), 7.18 (d, J=8.4 Hz, 1H), 7.06 (s, 2H), 6.99 (d, J=8.0 Hz, 1H), 6.67 (s, 1H), 6.39 (s, 1H), 4.43 (s, 1H), 3.87-3.78 (m, 3H), 3.58 (s, 2H), 2.89 (s, 1H), 2.85-2.78 (m, 5H), 2.76-2.73 (m, 1H), 2.65 (s, 1H), 2.15 (s, 2H), 2.06 (s, 1H), 1.98 (s, 2H), 1.88-1.81 (m, 2H), 1.79-1.73 (m, 1H), 1.72-1.64 (m, 1H), 1.57-1.46 (m, 3H).

Example 523: 4-((1-(4-(2-(2-Aminopyridin-3-yl)-5-(4-fluoro-2-methylphenyl)-3H-imidazo[4,5-b]pyridin-3-yl)benzyl)piperidin-4-yl)amino)pyrimidine-2-carbonitrile

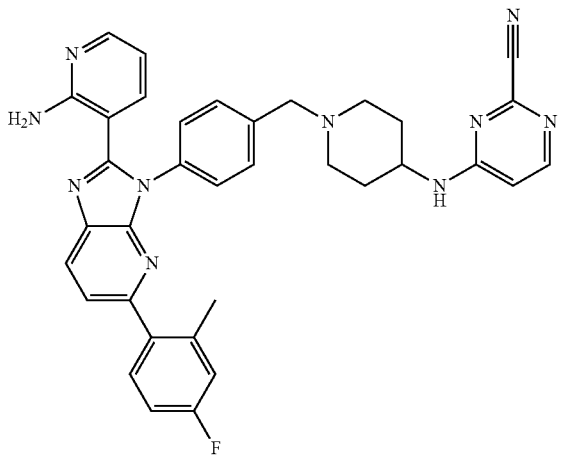

Example 523

To a solution of Intermediate 405 (180 mg, 335 µmol) in 1,4-dioxane (2 mL) and H$_2$O (0.4 mL) were added (4-fluoro-2-methylphenyl)boronic acid (67.1 mg, 436 µmol), Cs$_2$CO$_3$ (328 mg, 1.01 mmol) and Pd(dppf)Cl$_2$ (24.5 mg, 33.5 µmol). The mixture was Example stirred at 100° C. for 2 hr under N$_2$. The reaction mixture was filtered, and the filtrate was concentrated. After purified by prep-HPLC (column: Phenomenex C18 75×30 mm×3 µm; mobile phase: [water (NH$_3$H$_2$O+NH$_4$HCO$_3$)-ACN]; gradient: 52%-82% B over 7 min), 4-((1-(4-(2-(2-aminopyridin-3-yl)-5-(4-fluoro-2-methylphenyl)-3H-imidazo[4,5-b]pyridin-3-yl)benzyl)piperidin-4-yl)amino)pyrimidine-2-carbonitrile (Example 523, 63.1 mg, yield: 31%) was obtained as a light yellow solid. MS: m/z=611.4 [M+H]$^+$. $^1$H NMR (400 MHz, Dimethylsulfoxide-d$_6$) δ 8.27 (d, J=8.4 Hz, 1H), 8.11-8.02 (m, 2H), 8.00 (dd, J=4.8, 2.0 Hz, 1H), 7.52 (d, J=8.4 Hz, 1H), 7.47-7.37 (m, 5H), 7.20-7.07 (m, 3H), 7.02 (s, 2H), 6.66 (d, J=6.4 Hz, 1H), 6.38 (dd, J=7.6, 4.8 Hz, 1H), 3.85-3.74 (m, 1H), 3.55 (s, 2H), 2.79 (d, J=10.4 Hz, 2H), 2.32 (s, 3H), 2.18-2.08 (m, 2H), 1.92-1.79 (m, 2H), 1.53-1.41 (m, 2H). $^{19}$F NMR (400 MHz, Dimethylsulfoxide-d$_6$) δ −114.725.

Example 524: 2-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)-5-fluorobenzamide

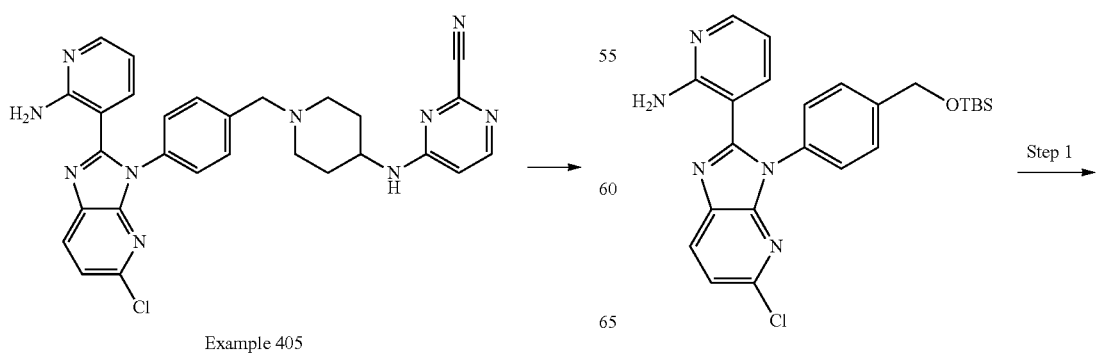

Example 405

Step 1

1657

-continued

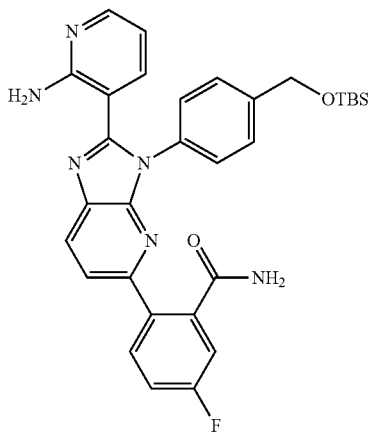

Step 2

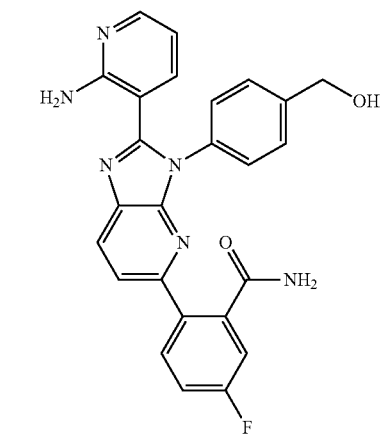

Step 3

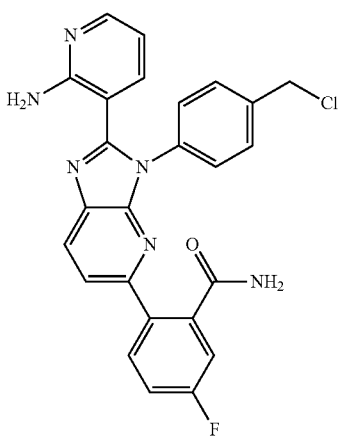

Step 4
Intermediate 51

1658

-continued

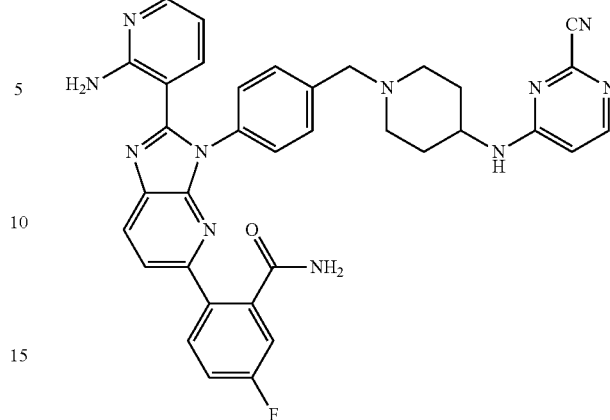

Example 524

Step 1: 2-(2-(2-Aminopyridin-3-yl)-3-(4-(((tert-butyldimethylsilyl)oxy)methyl)phenyl)-3H-imidazo[4,5-b]pyridin-5-yl)-5-fluorobenzamide To a mixture of 3-(3-(4-(((tert-butyldimthylsilyl)oxy)methyl)phenyl)-5-chloro-3H-imidazo[4,5-b]pyridin-2-yl)pyridin-2-amine (refer to Intermediate 117 for detail procedures, 300 mg, 644 μmol) and (2-cyano-4-fluorophenyl)boronic acid (117 mg, 708 μmol) in 1,4-dioxane (5 mL) and $H_2O$ (1 mL) were added $Cs_2CO_3$ (629.2 mg, 1.9 mmol, 3 eq) and Pd(dppf)Cl$_2$ (47.1 mg, 64.4 μmol). The mixture was stirred at 100° C. for 2 hr under $N_2$. The mixture was diluted with $H_2O$ (50 mL) and extracted with EtOAc (100 mL×2). The combined organic layers were washed with brine (100 mL), dried over anhydrous $Na_2SO_4$, filtered and concentrated. After purified by silica gel flash chromatography ((ethyl acetate in EtOH=3/1) in petroleum ether=0 to 40%), 2-(2-(2-aminopyridin-3-yl)-3-(4-(((tert-butyldimethylsilyl)oxy)methyl)phenyl)-3H-imidazo[4,5-b]pyridin-5-yl)-5-fluorobenzamide (300 mg, 81.6% yield) was obtained as a brown solid. MS: m/z=569.3 [M+H]$^+$. $^1$H NMR (400 MHz, Dimethylsulfoxide-d$_6$) δ 8.23 (d, J=8.4 Hz, 1H), 8.00 (dd, J=4.8, 1.6 Hz, 1H), 7.92-7.84 (m, 1H), 7.65 (dd, J=8.4, 5.6 Hz, 1H), 7.58 (d, J=8.4 Hz, 1H) 7.52-7.47 (m, 2H), 7.47-7.43 (m, 3H), 7.38-7.26 (m, 2H), 7.14 (dd, J=7.6, 1.6 Hz, 1H), 7.02-6.98 (m, 2H), 6.38 (dd, J=8.0, 5.2 Hz, 1H), 4.78 (s, 2H), 0.91 (s, 9H), 0.10 (s, 6H).

Step 2: 2-(2-(2-Aminopyridin-3-yl)-3-(4-(hydroxymethyl)phenyl)-3H-imidazo[4,5-b]pyridin-5-yl)-5-fluorobenzamide To a mixture of 2-(2-(2-aminopyridin-3-yl)-3-(4-(((tert-butyldimethylsilyl)oxy)methyl)phenyl)-3H-imidazo[4,5-b]pyridin-5-yl)-5-fluorobenzamide (290 mg, 510 μmol) in THF (1 mL) was added TBAF (1 M in THF, 765 IL), the mixture was stirred at 20° C. for 1 hr. $H_2O$ (50 mL) was added and extracted with EtOAc (30 mL×2). The combined organic layers were washed with brine (50 mL), dried over anhydrous $Na_2SO_4$, filtered and concentrated, 2-(2-(2-aminopyridin-3-yl)-3-(4-(hydroxymethyl)phenyl)-3H-imidazo[4,5-b]pyridin-5-yl)-5-fluorobenzamide (20 mg, yield. 94.9%) was obtained as a yellow solid. MS: m/z=455.2 [M+H]$^+$. $^1$H NMR (400 MHz, Dimethylsulfoxide-d$_6$) δ 8.22 (d, J=8.4 Hz, 1H), 8.00 (dd, J=4.8, 1.8 Hz, 1H), 7.89 (s, 1H), 7.65 (dd, J=8.4, 5.6 Hz, 1H), 7.58 (d, J=8.0 Hz, 1H), 7.49-7.44 (m, 3H), 7.42-7.38 (m, 2H), 7.37-7.31 (m, 1H), 7.30-7.24 (m, 1H), 7.17 (dd, J=7.6, 2.0 Hz, 1H), 7.09-6.88 (m, 1H), 6.42 (dd, J=7.6, 5.2 Hz, 1H), 4.56 (d, J=6.0 Hz, 1H).

Step 3: 2-(2-(2-Aminopyridin-3-yl)-3-(4-(chloromethyl)phenyl)-3H-imidazo[4,5-b]pyridin-5-yl)-5-fluorobenzamide To a mixture of 2-(2-(2-aminopyridin-3-yl)-3-(4-(hydroxymethyl)phenyl)-3H-imidazo[4,5-b]pyridin-5-yl)-5-fluorobenzamide (200 mg, 440 μmol) in CH₂Cl₂ (2 mL) was added SOCl₂ (157.1 mg, 1.32 mmol), the mixture was stirred at 20° C. for 1 hr. The mixture was concentrated, 2-(2-(2-aminopyridin-3-yl)-3-(4-(chloromethyl)phenyl)-3H-imidazo[4,5-b]pyridin-5-yl)-5-fluorobenzamide (208 mg, yield: 99.9%) was obtained as a yellow solid. MS: m/z=473.1 [M+H]⁺.

Step 4: 2-(2-(2-Aminopyridin-3-yl)-3-(4-((4-((2-cyanopyrimidin-4-yl)amino)piperidin-1-yl)methyl)phenyl)-3H-imidazo[4,5-b]pyridin-5-yl)-5-fluorobenzamide To a mixture of 2-(2-(2-aminopyridin-3-yl)-3-(4-(chloromethyl)phenyl)-3H-imidazo[4,5-b]pyridin-5-yl)-5-fluorobenzamide (200 mg, 423 μmol) and Intermediate 51 (94.6 mg, 465 μmol) in DMF (4 mL) was added DIEA (164 mg, 1.27 mmol). The mixture was stirred at 80° C. for 2 hr. H₂O (50 mL) was added and extracted with EtOAc (50 mL×2). The combined organic layers were washed with brine (50 mL), dried over anhydrous Na₂SO₄, filtered and concentrated. After purified by prep-HPLC (column: C18 150×30 mm; mobile phase: [water (NH₃H₂O+NH₄HCO₃)-ACN]; gradient: 46%-76% B over 7 min), 2-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)-5-fluorobenzamide (Example 524, 100 mg, yield: 37%) was obtained as a yellow solid. MS: m/z=640.2 [M+H]⁺. $^1$H NMR (400 MHz, Dimethylsulfoxide-$d_6$) δ 8.23 (d, J=8.0 Hz, 1H), 8.16-7.96 (m, 3H), 7.89 (s, 1H), 7.67 (dd, J=8.4, 5.6 Hz, 1H), 7.59 (d, J=8.4 Hz, 1H), 7.50-7.39 (m, 5H), 7.38-7.32 (m, 1H), 7.30-7.26 (m, 1H), 7.28 (dd, J=9.1, 2.0 Hz, 1H) 7.11 (dd, J=7.6, 2.0 Hz, 1H), 7.02 (br s, 2H), 6.67 (d, J=6.4 Hz, 1H), 6.38 (dd, J=7.6, 4.8 Hz, 1H), 3.88-3.74 (m, 1H), 3.54 (s, 2H), 2.85-2.75 (m, 2H), 2.21-2.06 (m, 2H), 1.94-1.79 (m, 2H), 1.57-1.41 (m, 2H). $^{19}$F NMR (400 MHz, Dimethylsulfoxide-$d_6$) δ -114.071.

Example 525: 4-((1-(4-(2-(2-Aminopyridin-3-yl)-5-(2-cyano-4-fluorophenyl)-3H-imidazo[4,5-b]pyridin-3-yl)benzyl)piperidin-4-yl)amino)pyrimidine-2-carbonitrile

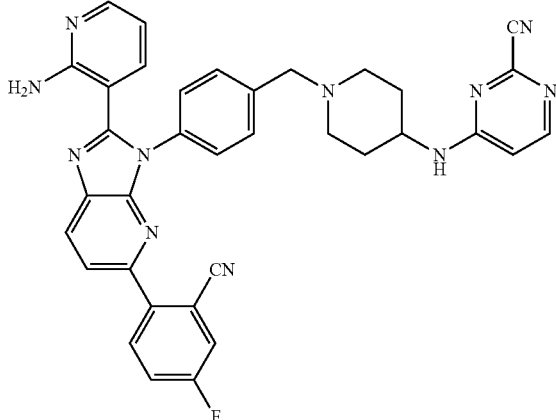

Example 525

To a mixture of Example 524 (60 mg, 93.8 μmol) in CH₂Cl₂ (1 mL) were added POCl₃ (86.3 mg, 563 gmol) and Py (59.4 mg, 750 μmol). The mixture was stirred at 25° C. for 1 hr. Water (20 mL) was added. The pH was adjusted to 10 with saturated NaHCO₃ (10 mL). The mixture was extracted with CH₂Cl₂ (30 mL×2). The combined organic layers were washed with brine (30 mL), dried over anhydrous Na₂SO₄, filtered and concentrated. After purified by prep-HPLC (column: Xtimate C18 150×40 mm×10 μm; mobile phase: [water (FA)-ACN]; gradient: 15%-45% B over 7 min), 4-((1-(4-(2-(2-aminopyridin-3-yl)-5-(2-cyano-4-fluorophenyl)-3H-imidazo[4,5-b]pyridin-3-yl)benzyl)piperidin-4-yl)amino)pyrimidine-2-carbonitrile (Example 525, 13.7 mg, yield: 23.5%) was obtained as a yellow solid. MS: m/z=622.1 [M+H]⁺. $^1$H NMR (400 MHz, Dimethylsulfoxide-$d_6$) δ 8.38 (d, J=8.4 Hz, 1H), 8.11-8.00 (m, 3H), 7.98-7.89 (m, 2H) 7.83 (d, J=8.4 Hz, 1H), 7.73-7.67 (m, 1H), 7.51-7.39 (m, 4H), 7.19 (dd, J=7.6, 1.6 Hz, 1H), 7.00 (br s, 2H), 6.66 (d, J=6.0 Hz, 1H), 6.40 (dd, J=8.0, 4.8 Hz, 1H), 3.87-3.72 (m, 1H), 3.55 (s, 2H), 2.86-2.73 (m, 2H), 2.19-2.05 (m, 2H), 1.94-1.79 (m, 2H), 1.57-1.40 (m, 2H). $^{19}$F NMR (376.5 MHz, Dimethylsulfoxide-$d_6$) δ -112.011.

Example 526: 4-((1-(4-(2-(2-Aminopyridin-3-yl)-5-(4-fluoro-2-(trifluoromethyl)phenyl)-3H-imidazo[4,5-b]pyridin-3-yl)benzyl)piperidin-4-yl)amino)pyrimidine-2-carbonitrile

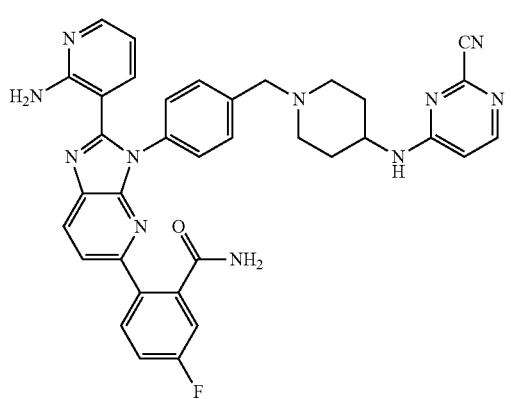

Example 524

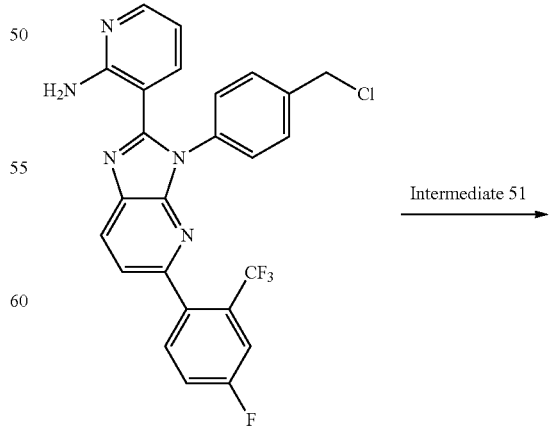

Intermediate 205

Intermediate 51

1661

-continued

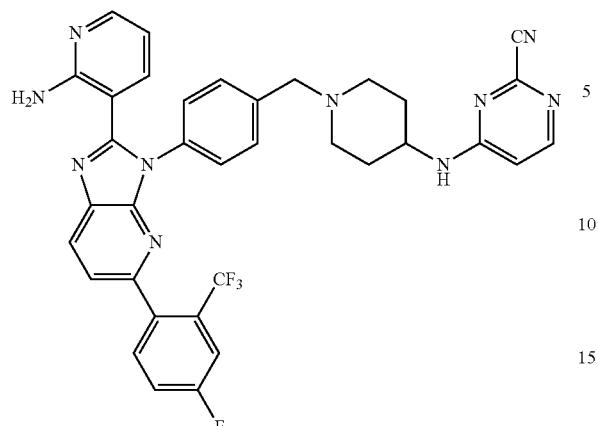

Example 526

To a mixture of Intermediate 205 (100 mg, 200.9 μmol) and Intermediate 51 (44.9 mg, 220.9 μmol) in DMF (2 mL) was added DIEA (77.9 mg, 602.6 μmol), the mixture was stirred at 80° C. for 12 hr. H$_2$O (50 mL) was added and extracted with EtOAc (50 mL×2). The combined organic layers were washed with brine (50 mL), dried over anhydrous Na$_2$SO$_4$, filtered and concentrated. After purified by prep-HPLC (column: C18 150-30 mm; mobile phase: [water (NH$_3$H$_2$O+NH$_4$HCO$_3$)-ACN]; gradient: 60%-90% B over 7 min), 4-((1-(4-(2-(2-aminopyridin-3-yl)-5-(4-fluoro-2-(trifluoromethyl)phenyl)-3H-imidazo[4,5-b]pyridin-3-yl)benzyl)piperidin-4-yl)amino)pyrimidine-2-carbonitrile (Example 526, 65.8 mg, yield: 49.3%) was obtained as a yellow solid. MS: m/z=665.1 [M+H]$^+$. $^1$H NMR (400 MHz, Dimethylsulfoxide-d$_6$) 8.30 (d, J=8.0 Hz, 1H), 8.20-7.93 (m, 3H), 7.74 (dd, J=8.2, 2.0 Hz, 1H), 7.66-7.60 (m, 2H), 7.52 (d, J=8.0 Hz, 1H), 7.45-7.33 (m, 4H), 7.17 (dd, J=7.6, 2.0 Hz, 1H), 7.03 (s, 2H), 6.66 (d, J=6.0 Hz, 1H), 6.38 (dd, J=7.6, 4.8 Hz, 1H), 3.84-3.73 (m, 1H), 3.53 (s, 2H), 2.86-2.74 (m, 2H), 2.19-2.08 (m, 2H), 1.92-1.78 (m, 2H), 1.57-1.37 (m, 2H). $^{19}$F NMR (400 MHz, Dimethylsulfoxide-d$_6$) δ −55.876, −111.904.

Example 527: 4-((1-(4-(2-(2-Aminopyridin-3-yl)-5-(o-tolyl)-3H-imidazo[4,5-b]pyridin-3-yl)benzyl)piperidin-4-yl)amino)pyrimidine-2-carbonitrile

1662

-continued

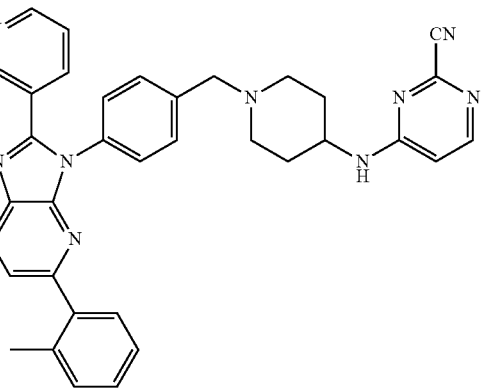

Example 527

To a solution of Example 405 (118 mg, 220 μmol) in 1,4-dioxane (1 mL) and H$_2$O (0.2 mL) were added o-tolylboronic acid (38.8 mg, 286 μmol), Pd(dppf)Cl$_2$ (16.1 mg, 22 μmol) and Cs$_2$CO$_3$ (215 mg, 659 μmol). The mixture was stirred at 100° C. for 2 hr under N$_2$. The reaction mixture was filtered and the filtrate was concentrated. After purified by prep-HPLC (column: Phenomenex C18 75×30 mm×3 μm; mobile phase: [water (NH$_3$H$_2$O+NH$_4$HCO$_3$)-ACN]; gradient: 52%-82% B over 7 min), 4-((1-(4-(2-(2-aminopyridin-3-yl)-5-(o-tolyl)-3H-imidazo[4,5-b]pyridin-3-yl)benzyl)piperidin-4-yl)amino)pyrimidine-2-carbonitrile (Example 527, 26.2 mg, yield: 20%) was obtained as a light-yellow solid. MS: m/z=593.2 [M+H]$^+$. $^1$H NMR (400 MHz, Dimethylsulfoxide-d$_6$) δ 8.26 (d, J=8.4 Hz, 1H), 8.12-7.95 (m, 3H), 7.53 (d, J=8.4 Hz, 1H), 7.47-7.37 (m, 5H), 7.31-7.25 (m, 3H), 7.17 (d, J=6.4 Hz, 1H), 7.02 (s, 2H), 6.67 (d, J=6.0 Hz, 1H), 6.38 (dd, J=7.6, 4.8 Hz, 1H), 3.83-3.73 (m, 1H), 3.55 (s, 2H), 2.79 (d, J=10.8 Hz, 2H), 2.31 (s, 3H), 2.18-2.05 (m, 2H), 1.93-1.79 (m, 2H), 1.54-1.39 (m, 2H).

Example 528: 4-((1-(4-(2-(2-Aminopyridin-3-yl)-5-(m-tolyl)-3H-imidazo[4,5-b]pyridin-3-yl)benzyl)piperidin-4-yl)amino)pyrimidine-2-carbonitrile

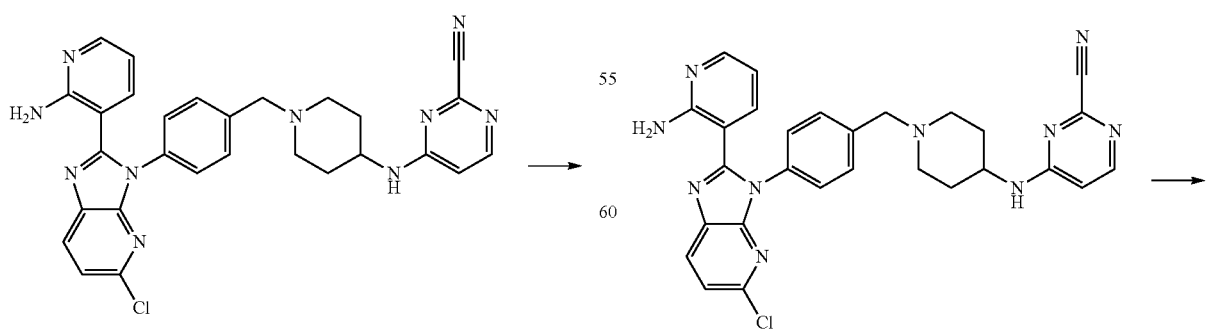

Example 405                              Example 405

1663

-continued

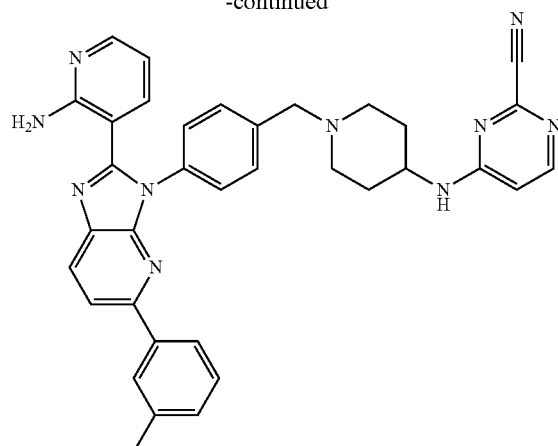

Example 528

To a solution of Example 405 (180 mg, 335 µmol) in 1,4-dioxane (2 mL) and H₂O (0.4 mL) were added m-tolylboronic acid (59.2 mg, 436 µmol), Pd(dppf)Cl₂ (24.5 mg, 33.5 µmol) and Cs₂CO₃ (328 mg, 1.01 mmol). The mixture was stirred at 100° C. for 2 hr under N₂. The reaction mixture was filtered, and the filtrate was concentrated. After purified by prep-HPLC (column: Phenomenex C18 75×30 mm×3 µm; mobile phase: [water (NH₃H₂O+NH₄HCO₃)-ACN]; gradient: 54%-84% B over 7 min), 4-((1-(4-(2-(2-aminopyridin-3-yl)-5-(m-tolyl)-3H-imidazo[4,5-b]pyridin-3-yl)benzyl)piperidin-4-yl)amino)pyrimidine-2-carbonitrile (Example 528, 67.8 mg, yield: 34%) was obtained as a light-yellow solid. MS: m/z=593.4 [M+H]⁺. ¹H NMR (400 MHz, Dimethylsulfoxide-d₆) δ 8.25 (dd, J=8.0, 3.2 Hz, 1H), 8.13-7.92 (m, 4H), 7.86-7.78 (m, 2H), 7.53-7.41 (m, 4H), 7.38-7.30 (m, 1H), 7.23-7.12 (m, 2H), 7.03 (s, 2H), 6.68 (s, 1H), 6.42-6.33 (m, 1H), 3.89-3.74 (m, 1H), 3.60 (s, 2H), 2.89-2.77 (m, 2H), 2.36 (s, 3H), 2.21-2.08 (m, 2H), 1.96-1.83 (m, 2H), 1.59-1.43 (m, 2H).

Example 529: 4-((1-(4-(2-(2-Aminopyridin-3-yl)-5-(p-tolyl)-3H-imidazo[4,5-b]pyridin-3-yl)benzyl)piperidin-4-yl)amino)pyrimidine-2-carbonitrile

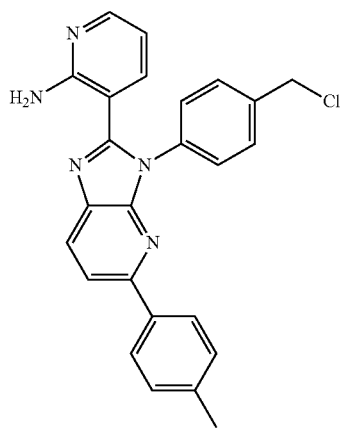

Intermediate 206

Intermediate 51
→

1664

-continued

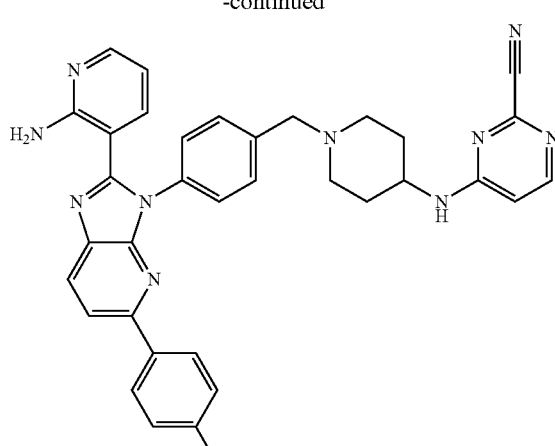

Example 529

To a solution of Intermediate 206 (125 mg, 294 µmol) in DMF (3 mL) were added Intermediate 51 (77.8 mg, 383 µmol) and DIEA (205.2 µL, 1.2 mmol). The mixture was stirred at 80° C. for 4 hr. After purified by prep-HPLC (column: Phenomenex C18 75×30 mm×3 µm; mobile phase: [water (NH₃H₂O+NH₄HCO₃)-ACN]; gradient: 54%-84% B over 7 min), 4-((1-(4-(2-(2-aminopyridin-3-yl)-5-(p-tolyl)-3H-imidazo[4,5-b]pyridin-3-yl)benzyl)piperidin-4-yl)amino)pyrimidine-2-carbonitrile (Example 529, 125 mg, yield: 37%) was obtained as a light yellow solid. MS: m/z=593.3 [M+H]⁺. ¹H NMR (400 MHz, Dimethylsulfoxide-d₆) δ 8.24 (d, J=8.4 Hz, 1H), 8.11-8.05 (m, 2H), 8.00 (dd, J=4.8, 1.8 Hz, 1H), 7.94-7.92 (m, J=8.4 Hz, 3H), 7.52-7.42 (m, 4H), 7.27 (d, J=8.0 Hz, 2H), 7.15 (dd, J=7.6, 2.0 Hz, 1H), 7.04 (br s, 2H), 6.68 (d, J=6.0 Hz, 1H), 6.38 (dd, J=7.6, 4.8 Hz, 1H), 3.88-3.76 (m, 1H), 3.60 (s, 2H), 2.97-2.77 (m, 2H), 2.34 (s, 3H), 2.23-2.07 (m, 2H), 1.98-1.77 (m, 2H), 1.55-1.42 (m, 2H).

Example 530: 4-((1-(4-(2-(2-Aminopyridin-3-yl)-5-(3-(trifluoromethyl)phenyl)-3H-imidazo[4,5-b]pyridin-3-yl)benzyl)piperidin-4-yl)amino)pyrimidine-2-carbonitrile

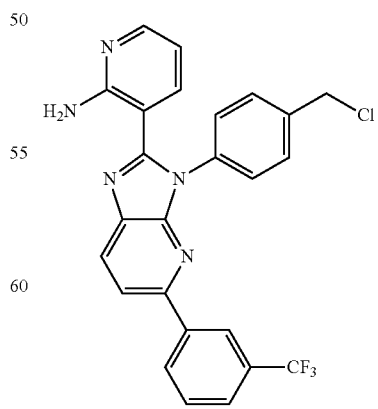

Intermediate 207

Intermediate 51
→

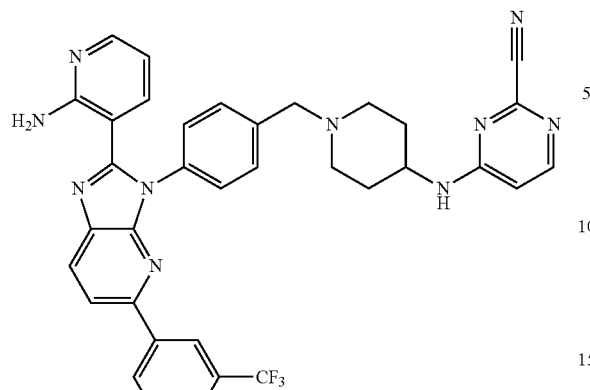

Example 530

To a solution of Intermediate 207 (277.6 mg, 578.4 μmol) in DMF (4 mL) were added Intermediate 51 (188.9 mg, 929.2 μmol) and DIEA (369.5 mg, 2.9 mmol). The mixture was stirred at 80° C. for 4 hr under $N_2$. After purified by prep-HPLC (column: Phenomenex C18 75×30 mm×3 μm; mobile phase: [water ($NH_3H_2O+NH_4HCO_3$)-ACN]; gradient: 56%-86% B over 7 min), 4-((1-(4-(2-(2-aminopyridin-3-yl)-5-(3-(trifluoromethyl)phenyl)-3H-imidazo[4,5-b]pyridin-3-yl)benzyl)piperidin-4-yl)amino)pyrimidine-2-carbonitrile (Example 530, 161.3 mg, yield: 34.9%) was obtained as a light yellow solid. MS: m/z=647.3 [M+H]$^+$. $^1$H NMR (400 MHz, Dimethylsulfoxide-$d_6$) δ 8.38-8.30 (m, 3H), 8.14 (d, J=8.4 Hz, 1H), 8.10-8.04 (m, 2H), 8.01 (dd, J=4.8, 2.0 Hz, 1H), 7.77-7.68 (m, 2H), 7.52-7.44 (m, 4H), 7.19 (dd, J=7.6, 1.6 Hz, 1H), 7.07 (s, 2H), 6.68 (br d, J=6.4 Hz, 1H), 6.39 (dd, J=8.0, 4.8 Hz, 1H), 3.81 (br s, 1H), 3.60 (s, 2H), 2.83-2.81 (m, 2H), 2.20-2.09 (m, 2H), 1.94-1.80 (m, 2H), 1.54-1.45 (m, 2H). $^{19}$F NMR (400 MHz, Dimethylsulfoxide-$d_6$) δ −61.256.

Example 531: Isopropyl 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylate

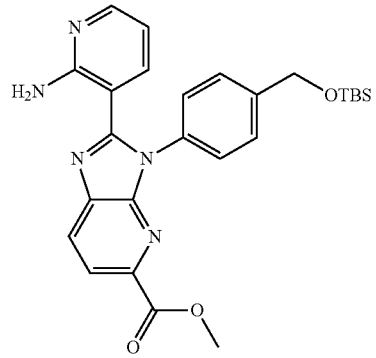

Step 1

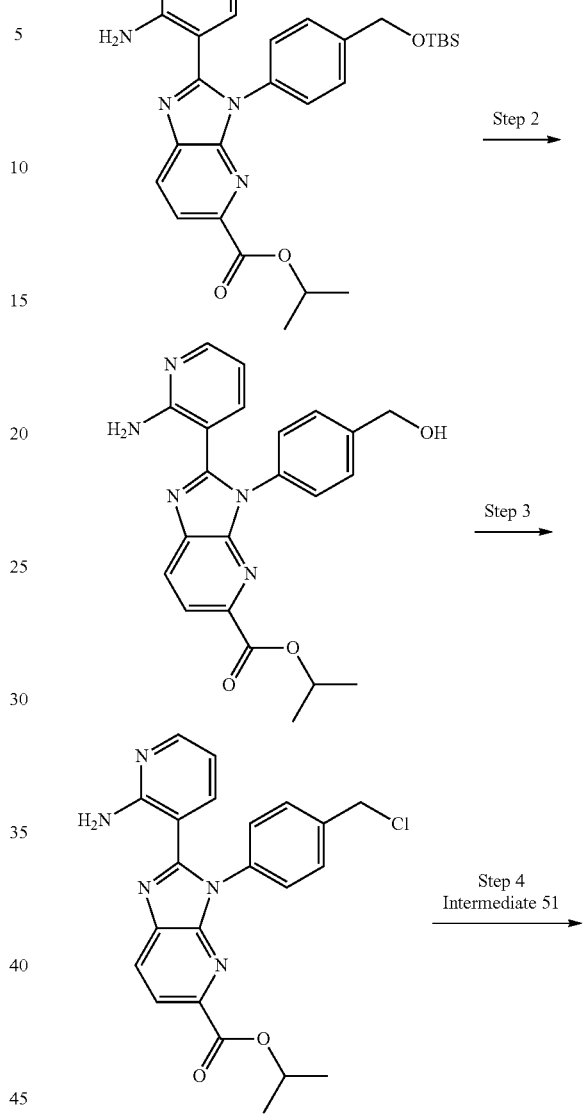

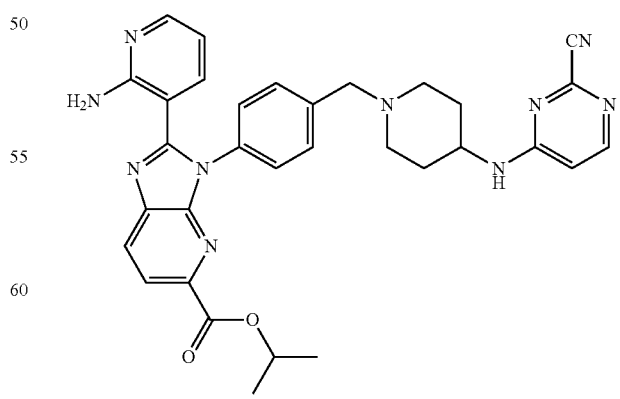

Example 531

Step 1: Isopropyl 2-(2-aminopyridin-3-yl)-3-(4-(((tert-butyldimethylsilyl)oxy)methyl)phenyl)-3H-imidazo[4,5-b]pyridine-5-carboxylate To a solution of methyl 2-(2-aminopyridin-3-yl)-3-(4-(((tert-butyldimethylsilyl)oxy)methyl)phenyl)-3H-imidazo[4,5-b]pyridine-5-carboxylate (refer to Example 508 for detail procedures, 280 mg, 572 μmol) in i-PrOH (10 mL) was added i-PrOLi (45.3 mg, 686 μmol). The reaction mixture was stirred at 65° C. for 0.5 hr. After cooling to 25° C., water (20 mL) was added. The mixture was extracted with EtOAc (20 mL×3). The combined organic layers were washed with brine (20 mL×2), dried over anhydrous $Na_2SO_4$, filtered, and concentrated under reduced pressure. After purified by silica gel flash chromatography (MeOH in $CH_2Cl_2$=0-20%), isopropyl 2-(2-aminopyridin-3-yl)-3-(4-(((tert-butyldimethylsilyl)oxy)methyl)phenyl)-3H-imidazo[4,5-b]pyridine-5-carboxylate (160 mg, yield: 54.1%) was obtained as a yellow solid. MS: m/z=518.3 $[M+H]^+$.

Step 2: Isopropyl 2-(2-aminopyridin-3-yl)-3-(4-(hydroxymethyl)phenyl)-3H-imidazo[4,5-b]pyridine-5-carboxylate To a solution of isopropyl 2-(2-aminopyridin-3-yl)-3-(4-(((tert-butyldimethylsilyl)oxy)methyl)phenyl)-3H-imidazo[4,5-b]pyridine-5-carboxylate (150 mg, 290 μmol) in THF (5 mL) was added TBAF (1 M in THF, 435 μL). The reaction mixture was stirred at 20° C. for 1 hr. Water (20 mL) was added. The mixture was extracted with EtOAc (20 mL×3). The combined organic layers were washed with brine (20 mL×2), dried over anhydrous $Na_2SO_4$, filtered, and concentrated under reduced pressure. Isopropyl 2-(2-aminopyridin-3-yl)-3-(4-(hydroxymethyl)phenyl)-3H-imidazo[4,5-b]pyridine-5-carboxylate (117 mg, crude) was obtained as a brown solid, which was used directly into the next step. MS: m/z=404.2 $[M+H]^+$.

Step 3: Isopropyl 2-(2-aminopyridin-3-yl)-3-(4-(chloromethyl)phenyl)-3H-imidazo[4,5-b]pyridine-5-carboxylate To a solution of isopropyl 2-(2-aminopyridin-3-yl)-3-(4-(hydroxymethyl)phenyl)-3H-imidazo[4,5-b]pyridine-5-carboxylate (107 mg, 265 μmol) in $CH_2Cl_2$ (3 mL) was added $SOCl_2$ (94.6 mg, 795 μmol). The reaction mixture was stirred at 20° C. for 2 hr. The reaction mixture was concentrated to give isopropyl 2-(2-aminopyridin-3-yl)-3-(4-(chloromethyl)phenyl)-3H-imidazo[4,5-b]pyridine-5-carboxylate (112 mg, 265 μmol, crude) as a yellow solid, which was used directly into the next step. MS: m/z=422.1 $[M+H]^+$.

Step 4: Isopropyl 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylate To a solution of isopropyl 2-(2-aminopyridin-3-yl)-3-(4-(chloromethyl)phenyl)-3H-imidazo[4,5-b]pyridine-5-carboxylate (112 mg, 265 μmol) and Intermediate 51 (59.2 mg, 291 μmol) in DMF (3 mL) were added NaI (7.94 mg, 53.0 μmol) and $K_2CO_3$ (110 mg, 795 μmol) at 20° C. The reaction mixture was stirred at 20° C. for 12 hr. The reaction mixture was diluted with $H_2O$ (20 ml) and extracted with EtOAc (20 ml). The organic layer was separated, dried over anhydrous $Na_2SO_4$ and concentrated. After purified by prep-HPLC (column: C18 150×30 mm; mobile phase: [water ($NH_3H_2O$+$NH_4HCO_3$)-ACN]; gradient: 50%-80% B over 7 min), isopropyl 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylate (Example 531, 28.4 mg, yield: 18.2% for 3 steps) was obtained as a yellow solid. MS: m/z=589.3 $[M+H]^+$. $^1$H NMR (400 MHz, Dimethylsulfoxide-$d_6$) δ 8.32 (d, J=8.4 Hz, 1H), 8.11-8.03 (m, 3H), 8.01 (dd, J=4.4, 1.6 Hz, 1H), 7.50-7.40 (m, 4H), 7.18 (dd, J=7.6, 1.6 Hz, 1H), 7.00 (s, 2H), 6.67 (d, J=6.0 Hz, 1H), 6.38 (dd, J=8.0, 5.2 Hz, 1H), 5.17-5.08 (m, 1H), 3.82 (br.s, 1H), 3.58 (s, 2H), 2.87-2.78 (m, 2H), 2.21-2.11 (m, 2H), 1.93-1.84 (m, 2H), 1.56-1.43 (m, 2H), 1.32 (d, J=6.4 Hz, 6H).

Example 532: 4-((1-(4-(2-(2-Aminopyridin-3-yl)-1H-benzo[d]imidazol-1-yl)benzyl)piperidin-4-yl)amino)pyrimidine-2-carbonitrile

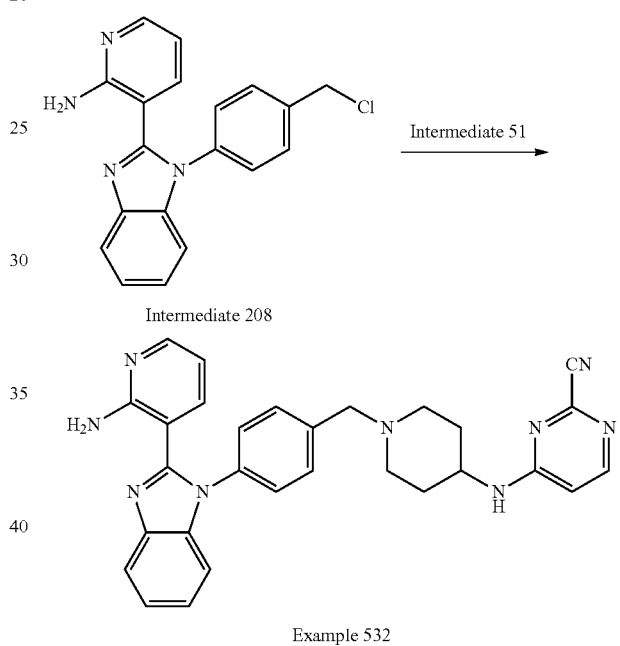

Example 532

To a solution of Intermediate 208 (180 mg, 537 gmol) and Intermediate 51 (131 mg, 645 gmol) in DMF (5 mL) were added NaI (16.1 mg, 107 μmol) and $K_2CO_3$ (223 mg, 1.61 mmol, 300 μL) at 20° C. The reaction mixture was stirred at 20° C. for 12 hr. The reaction mixture was diluted with $H_2O$ (20 ml) and extracted with EtOAc (20 mL). The organic layer was separated, dried over anhydrous $Na_2SO_4$ and concentrated. After purified by prep-HPLC (column: C18 150×30 mm; mobile phase: [water ($NH_3H_2O$+$NH_4HCO_3$)-ACN]; gradient: 57%-77% B over 7 min), 4-((1-(4-(2-(2-aminopyridin-3-yl)-1H-benzo[d]imidazol-1-yl)benzyl)piperidin-4-yl)amino)pyrimidine-2-carbonitrile (Example 532, 83.1 mg, yield: 30.8% for 2 steps) was obtained as a white solid. MS: m/z=502.3 $[M+H]^+$. $^1$H NMR (400 MHz, Dimethylsulfoxide-$d_6$) δ 8.13-8.02 (m, 2H), 7.96 (dd, J=4.8, 1.6 Hz, 1H), 7.80 (d, J=7.2 Hz, 1H), 7.49 (d, J=8.4 Hz, 2H), 7.37 (d, J=8.4 Hz, 2H), 7.35-7.27 (m, 2H), 7.20 (d, J=7.2 Hz, 1H), 7.11-7.06 (m, 3H), 6.67 (d, J=6.0 Hz, 1H), 6.34 (dd, =7.6, 4.8 Hz, 1H), 3.81 (s, 1H), 3.59 (s, 2H), 2.87-2.77 (m, 2H), 2.19-2.10 (m, 2H), 1.94-1.83 (m, 2H), 1.57-1.43 (m, 2H).

Example 533: 4-((1-(4-(2-(2-Aminopyridin-3-yl)-1H-imidazo[4,5-b]pyridin-1-yl)benzyl)piperidin-4-yl)amino)pyrimidine-2-carbonitrile

Example 534: 4-((1-(4-(2-(2-Aminopyridin-3-yl)-5-(6-methylpyridin-3-yl)-3H-imidazo[4,5-b]pyridin-3-yl)benzyl)piperidin-4-yl)amino)pyrimidine-2-carbonitrile

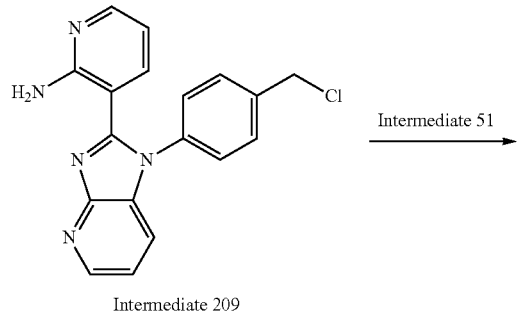

Intermediate 209

Intermediate 51 →

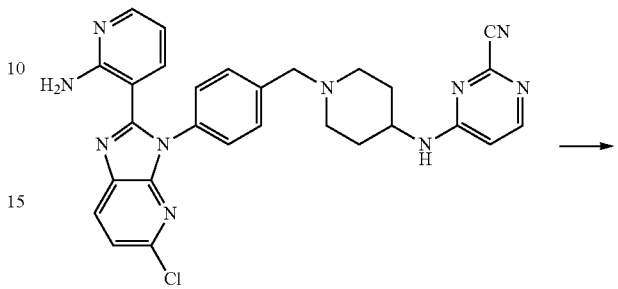

Example 405 →

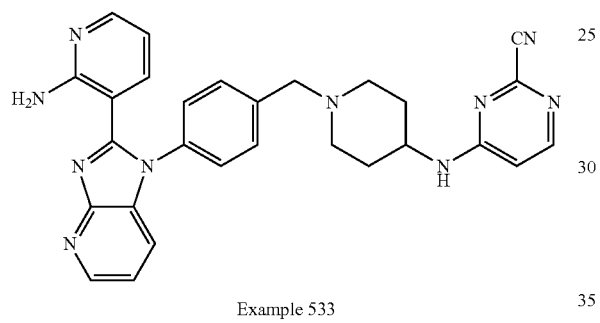

Example 533

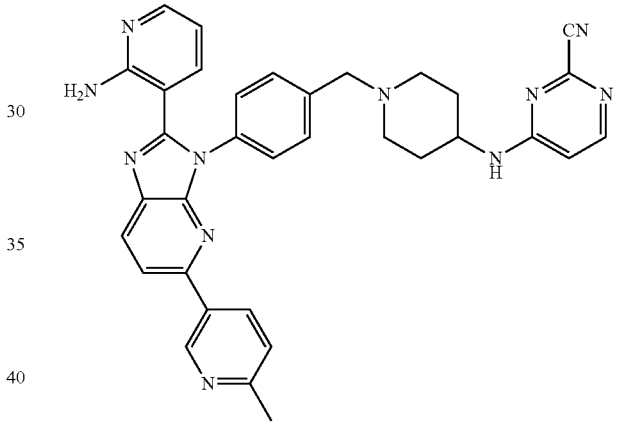

Example 534

To a solution of Intermediate 209 (106 mg, 315 μmol) and Intermediate 51 (70.5 mg, 347 μmol) in DMF (3 mL) were added $K_2CO_3$ (131 mg, 945 μmol) and NaI (9.45 mg, 63.0 μmol) at 20° C. The reaction mixture was stirred at 20° C. for 12 hr. The reaction mixture was diluted with $H_2O$ (20 mL) and extracted with EtOAc (20 mL). The organic layer was separated, dried over anhydrous $Na_2SO_4$, and concentrated under reduced pressure. After purified by prep-HPLC (column: C18 150×30 mm; mobile phase: [water ($NH_3H_2O$+$NH_4HCO_3$)-ACN]; gradient: 40%-70% B over 7 min), 4-((1-(4-(2-(2-aminopyridin-3-yl)-1H-imidazo[4,5-b]pyridin-1-yl)benzyl)piperidin-4-yl)amino)pyrimidine-2-carbonitrile (Example 533, 40.5 mg, yield: 25.6%) was obtained as an off-white solid. MS: m/z=503.4 [M+H]$^+$. $^1$H NMR (400 MHz, Dimethylsulfoxide-$d_6$) δ 8.51 (dd, J=4.8, 1.2 Hz, 1H), 8.12-8.03 (m, 2H), 8.00 (dd, J=4.8, 1.6 Hz, 1H), 7.65 (d, J=8.0 Hz, 1H), 7.52-7.47 (m, 2H), 7.44-7.39 (m, 2H), 7.32 (dd, J=8.0, 4.8 Hz, 1H), 7.15 (dd, J=7.6, 1.2 Hz, 1H), 7.05 (s, 2H), 6.67 (d, J=6.4 Hz, 1H), 6.38 (dd, J=7.6, 4.8 Hz, 1H), 3.81 (s, 1H), 3.59 (s, 2H), 2.86-2.77 (m, 2H), 2.22-2.07 (m, 2H), 1.93-1.83 (m, 2H), 1.56-1.43 (m, 2H).

To a solution of Example 405 (200 mg, 372 μmol) and (6-methyl-3-pyridyl)boronic acid (56.1 mg, 410 μmol) in 1,4-dioxane (5 mL) and $H_2O$ (1 mL) were added Pd(dppf)$Cl_2$ (27.3 mg, 37.2 μmol) and $Cs_2CO_3$ (364 mg, 1.12 mmol) at 25° C. The mixture was degassed and purged with $N_2$ three times, and stirred at 100° C. for 1 hr. The mixture was quenched with $H_2O$ (50 mL) and extracted with EtOAc (50 mL×3). The combined organic layers were washed with brine (50 mL), dried over $Na_2SO_4$, filtered, and concentrated. After purified by silica gel flash chromatography (MeOH in $CH_2Cl_2$=0-10%), 4-((1-(4-(2-(2-aminopyridin-3-yl)-5-(6-methylpyridin-3-yl)-3H-imidazo[4,5-b]pyridin-3-yl)benzyl)piperidin-4-yl)amino)pyrimidine-2-carbonitrile (Example 534, 87.7 mg, yield. 40%) was obtained as a yellow solid. MS: m/z=594.1 [M+H]$^+$. $^1$H NMR (400 MHz, Dimethylsulfoxide-d6) 9.10 (d, J=2.0 Hz, 1H), 8.34-8.22 (m, 2H), 8.13-7.97 (m, 4H), 7.53-7.43 (m, 4H), 7.34 (d, J=8.4 Hz, 1H), 7.16 (dd, J=7.6, 1.6 Hz, 1H), 7.04 (s, 2H), 6.68 (d, J=6.4 Hz, 1H), 6.39 (dd, J=7.6, 4.8 Hz, 1H), 3.90-3.75 (m, 1H), 3.59 (s, 2H), 2.90-2.76 (m, 2H), 2.50 (s, 3H), 2.23-2.11 (m, 2H), 1.96-1.84 (m, 2H), 1.58-1.40 (m, 2H).

Example 535: 4-((1-(4-(2-(2-Aminopyridin-3-yl)-5-(difluoromethoxy)-3H-imidazo[4,5-b]pyridin-3-yl)benzyl)piperidin-4-yl)amino)pyrimidine-2-carbonitrile Example 536: 4-((1-(4-(2-(2-Aminopyridin-3-yl)-5-(4-methoxypyridin-3-yl)-3H-imidazo[4,5-b]pyridin-3-yl)benzyl)piperidin-4-yl)amino)pyrimidine-2-carbonitrile

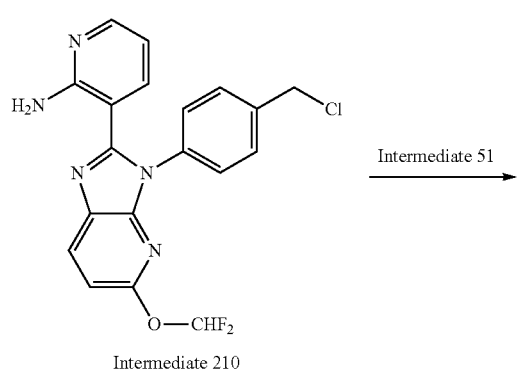

Intermediate 210

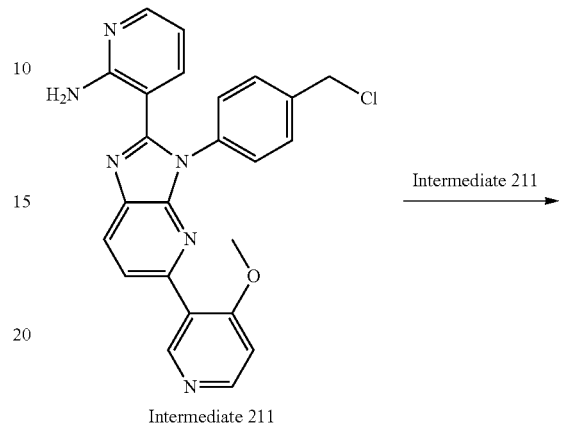

Intermediate 211

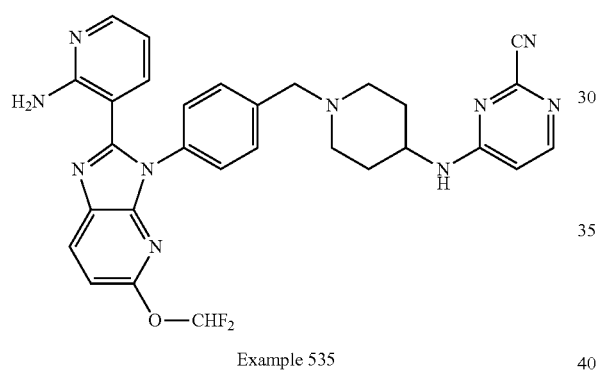

Example 535

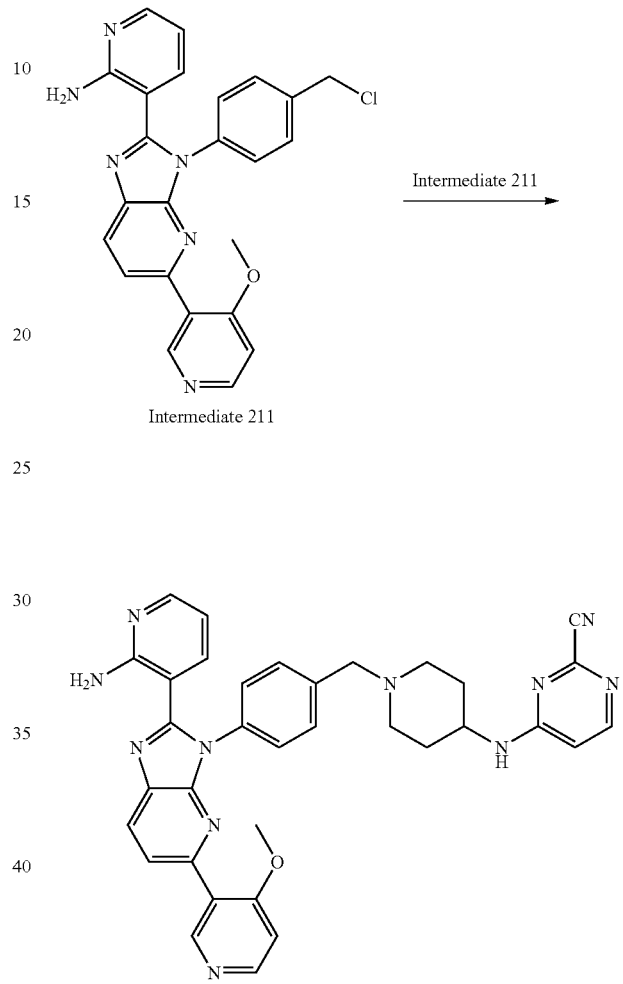

Example 536

To a solution of Intermediate 210 (123 mg, 306 µmol) and Intermediate 51 (68.3 mg, 336 µmol) in DMF (5 mL) were added NaI (9.16 mg, 61.1 gmol) and K$_2$CO$_3$ (127 mg, 917 µmol) at 20° C. The reaction mixture was stirred at 20° C. for 12 hr. The mixture was diluted with H$_2$O (20 mL) and extracted with EtOAc (20 mL×3). The combined organic layers were washed with brine (20 mL×2), dried over anhydrous Na$_2$SO$_4$, filtered, and concentrated under reduced pressure. After purified by prep-HPLC (column: Phenomenex C18 80×30 mm×5 µm; mobile phase: [water (NH$_3$H$_2$O+NH$_4$HCO$_3$)-ACN]; gradient: 52%-82% B over 7 min), 4-((1-(4-(2-(2-aminopyridin-3-yl)-5-(difluoromethoxy)-3H-imidazo[4,5-b]pyridin-3-yl)benzyl)piperidin-4-yl)amino)pyrimidine-2-carbonitrile (Example 535, 40.3 mg, yield: 23.2% for 3 steps) was obtained as an off-white solid. MS: m/z=569.3 [M+H]$^+$. $^1$H NMR (400 MHz, Dimethylsulfoxide-d$_6$) δ 8.33 (d, J=8.4 Hz, 1H), 8.07 (dd, J=9.6, 6.0 Hz, 2H), 7.98 (dd, J=4.8, 1.6 Hz, 1H), 7.75-7.51 (m, 1H), 7.48-7.42 (m, 2H), 7.39-7.35 (m, 2H), 7.13-7.05 (m, 2H), 6.89 (s, 2H), 6.67 (d, J=6.0 Hz, 1H), 6.37 (dd, J=7.6, 4.8 Hz, 1H), 3.84-3.78 (m, 11H), 3.57 (s, 2H), 2.87-2.77 (m, 2H), 2.21-2.08 (m, 2H), 1.95-1.82 (m, 2H), 1.57-1.42 (m, 2H). $^{19}$F NMR (400 MHz, Dimethylsulfoxide-d$_6$) δ −86.292.

To a solution of Intermediate 211 (190 mg, 429 µmol) in DMF (3 mL) were added DIEA (222 mg, 1.72 mmol) and Intermediate 51 (113 mg, 558 µmol). The mixture was stirred at 80° C. for 2 hr. After purified by prep-HPLC (column: Phenomenex C18 80×30 mm×5 µm; mobile phase: [water (NH$_3$H$_2$O+NH$_4$HCO$_3$)-ACN]; gradient: 38%-68% B over 7 min), 4-((1-(4-(2-(2-aminopyridin-3-yl)-5-(4-methoxypyridin-3-yl)-3H-imidazo[4,5-b]pyridin-3-yl)benzyl)piperidin-4-yl)amino)pyrimidine-2-carbonitrile (Example 536, 44.6 mg, yield: 17.1%) was obtained as a yellow solid. MS: m/z=610.3 [M+H]$^+$. $^1$H NMR (400 MHz, Dimethylsulfoxide-d$_6$) δ 8.66 (s, 1H), 8.46 (d, J=6.4 Hz, 1H), 8.25 (d, J=8.4 Hz, 1H), 8.10-8.03 (m, 2H), 8.02-7.96 (dd, J=4.8, 1.6 Hz, 1H), 7.85 (d, J=8.4 Hz, 1H), 7.46-7.42 (m, 4H), 7.20 (d, J=6.0 Hz, 1H), 7.17-7.13 (dd, J=7.6, 1.6 Hz, 1H), 7.03 (s, 2H), 6.66 (d, J=6.0 Hz, 1H), 6.41-6.35 (m, 1H), 3.92 (s, 3H), 3.85 (br.s, 1H), 3.56 (s, 2H), 2.80-2.75 (m, 2H), 2.30-2.10 (m, 2H), 1.89 (d, J=10.4 Hz, 2H), 1.60-1.40 (m, 2H).

Example 537 & 538: 4-((1-(4-(2-(2-Aminopyridin-3-yl)-5-(2-methoxypyridin-3-yl)-3H-imidazo[4,5-b]pyridin-3-yl)benzyl)piperidin-4-yl)amino)pyrimidine-2-carbonitrile & 4-((1-(4-(2-(2-Aminopyridin-3-yl)-5-(2-hydroxypyridin-3-yl)-3H-imidazo[4,5-b]pyridin-3-yl)benzyl)piperidin-4-yl)amino)pyrimidine-2-carbonitrile

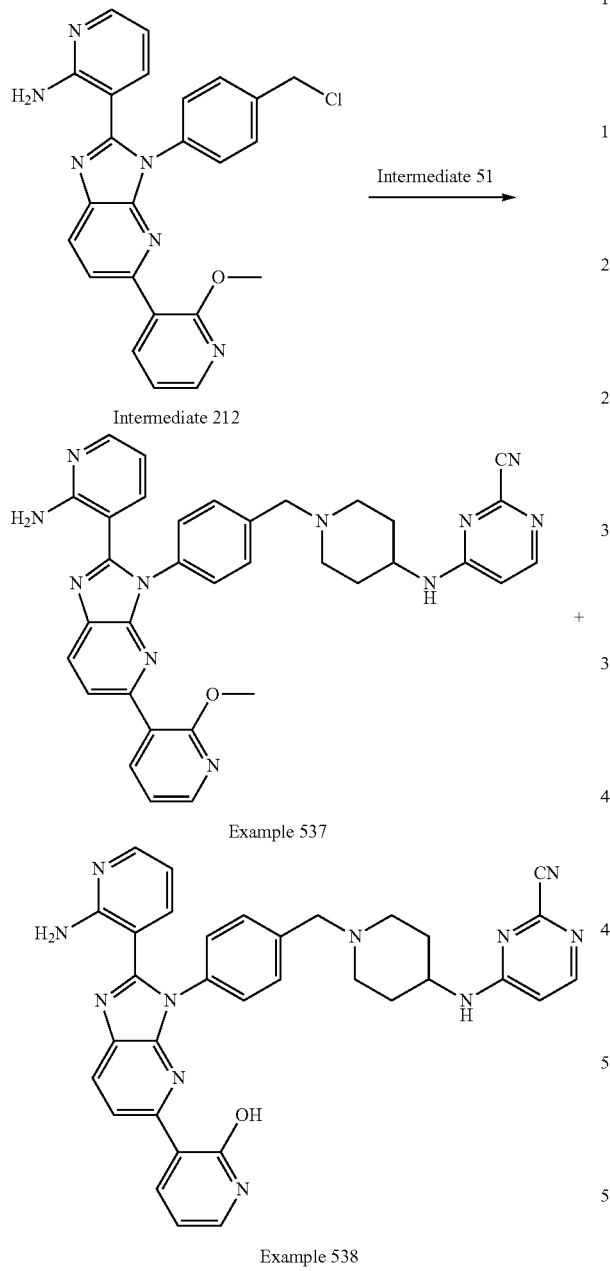

To a solution of Intermediate 212 (350 mg, 790 μmol) and Intermediate 51 (177 mg, 869 gmol) in DMF (12 mL) were added NaI (23.7 mg, 158 μmol) and K₂CO₃ (328 mg, 2.37 mmol) at 20° C. The reaction mixture was stirred at 80° C. for 2 hr. The mixture was diluted with H₂O (30 m L) and extracted with EtOAc (50 mL×3). The combined organic layers were washed with brine (50 mL×2), dried over anhydrous Na₂SO₄, filtered, and concentrated under reduced pressure. After purified by prep-HPLC (column: C18 150×30 mm; mobile phase: [water (NH₃H₂O+NH₄HCO₃)-ACN]; gradient: 50%-80% B over 7 min), 4-((1-(4-(2-(2-aminopyridin-3-yl)-5-(2-methoxypyridin-3-yl)-3H-imidazo[4,5-b]pyridin-3-yl)benzyl)piperidin-4-yl)amino)pyrimidine-2-carbonitrile (Example 537, 12.7 mg, yield: 2.6% for 4 steps) was obtained as an off-white solid. MS: m/z=610.4 [M+H]⁺. ¹H NMR (400 MHz, Dimethylsulfoxide-d₆) δ 8.27-8.21 (m, 2H), 8.12-8.03 (m, 3H), 8.00 (d, J=8.0 Hz, 2H), 7.48-7.42 (m, 4H), 7.16-7.09 (m, 2H), 7.02 (s, 2H), 6.67 (d, J=6.0 Hz, 1H), 6.38 (dd, J=8.0, 5.2 Hz, 1H), 3.96 (s, 3H), 3.87-3.73 (m, 1H), 3.57 (s, 2H), 2.87-2.76 (m, 2H), 2.20-2.09 (m, 2H), 1.93-1.80 (m, 2H), 1.57-1.41 (m, 2H). 4-((1-(4-(2-(2-aminopyridin-3-yl)-5-(2-hydroxypyridin-3-yl)-3H-imidazo[4,5-b]pyridin-3-yl)benzyl)piperidin-4-yl)amino)pyrimidine-2-carbonitrile (Example 538, 53.8 mg, yield. 11.4% for 4 steps) was obtained as an off-white solid. MS: m/z=596.1 [M+H]⁺. ¹H NMR (400 MHz, Dimethylsulfoxide-d₆) δ 11.99 (s, 1H), 8.68 (d, J=8.4 Hz, 1H), 8.25-8.17 (m, 2H), 8.14-8.03 (m, 2H), 7.99 (d, J=3.6 Hz, 1H), 7.50-7.41 (m, 5H), 7.13 (d, J=7.6 Hz, 1H), 7.05 (s, 2H), 6.67 (d, J=6.0 Hz, 1H), 6.40-6.33 (m, 2H), 3.93-3.73 (m, 1H), 3.59 (s, 2H), 2.87-2.78 (m, 2H), 2.22-2.09 (m, 2H), 1.94-1.83 (m, 2H), 1.58-1.42 (m, 2H).

Example 539: 4-((1-(4-(2-(2-Aminopyridin-3-yl)-5-(1,3-dimethyl-1H-pyrazol-4-yl)-3H-imidazo[4,5-b]pyridin-3-yl)benzyl)piperidin-4-yl)amino)pyrimidine-2-carbonitrile

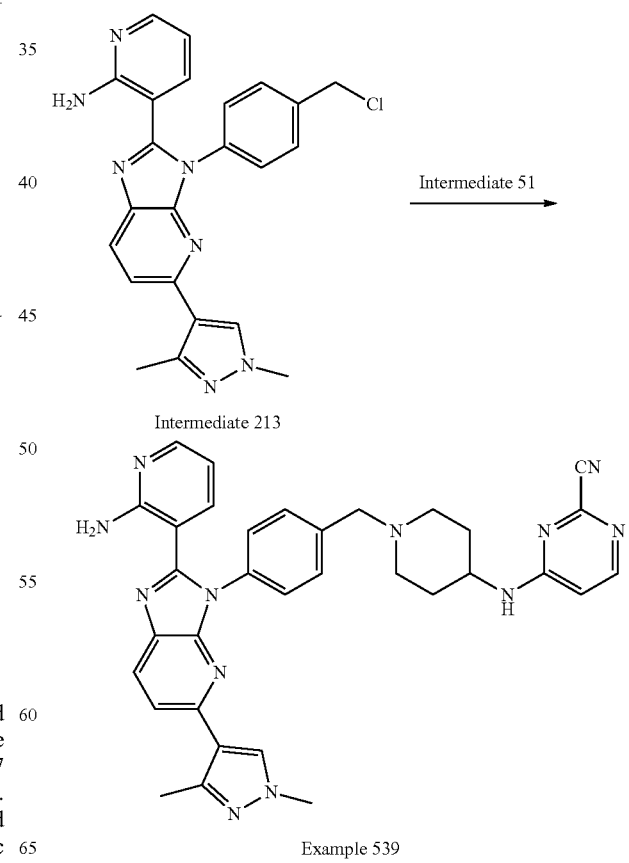

To a solution of Intermediate 213 (440 mg, 1.02 mmol) and Intermediate 51 (229 mg, 1.13 mmol) in DMF (16 mL) were added K₂CO₃ (424 mg, 3.07 mmol) and NaI (30.7 mg, 205 µmol) at 20° C. The reaction mixture was stirred at 80° C. for 2 hr. The mixture was diluted with H₂O (30 mL) and extracted with EtOAc (50 mL×3). The combined organic layers were washed with brine (50 mL×2), dried over anhydrous Na₂SO₄, filtered, and concentrated under reduced pressure. After purified by prep-HPLC (column: C18 150× 30 mm; mobile phase: [water (NH₃H₂O+NH₄HCO₃)-ACN]; gradient. 45%-75% B over 7 min), 4-((1-(4-(2-(2-amino-pyridin-3-yl)-5-(1,3-dimethyl-1H-pyrazol-4-yl)-3H-imi-dazo[4,5-b]pyridin-3-yl)benzyl)piperidin-4-yl)amino)py-rimidine-2-carbonitrile (Example 539, 139.6 mg, yield: 23% for 4 steps) was obtained as an off-white solid. MS: m/z=597.1 [M+H]⁺. ¹H NMR (400 MHz, Dimethylsulfoxide-d₆) δ 8.18 (s, 1H), 8.14 (d, J=8.4 Hz, 1H), 8.10-8.04 (m, 2H), 7.99 (dd, J=4.8, 2.0 Hz, 1H), 7.57 (d, J=8.4 Hz, 1H), 7.48-7.44 (m, 2H), 7.43-7.39 (m, 2H), 7.19 (dd, J=7.6, 1.6 Hz, 1H), 7.10 (s, 2H), 6.67 (d, J=6.0 Hz, 1H), 6.38 (dd, J=7.6, 4.8 Hz, 1H), 3.83-3.75 (m, 4H), 3.57 (s, 2H), 2.83-2.77 (m, 2H), 2.27 (s, 3H), 2.20-2.03 (m, 2H), 1.92-1.84 (m, 2H), 1.53-1.43 (m, 2H).

Example 540: 4-((1-(4-(2-(2-Aminopyridin-3-yl)-1H-imidazo[4,5-c]pyridin-1-yl)benzyl)piperidin-4-yl)amino)pyrimidine-2-carbonitrile

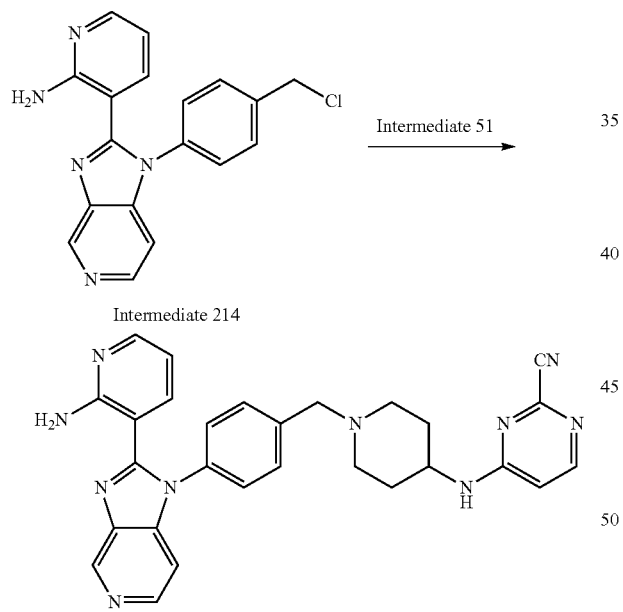

Example 540

To a solution of Intermediate 214 (100 mg, 298 µmol) and Intermediate 51 (66.6 mg, 328 µmol) in DMF (3 mL) were added K₂CO₃ (123 mg, 893 µmol) and NaI (4.46 mg. 29.8 µmol) at 25° C. This mixture was stirred at 25° C. for 12 hr. The mixture was quenched with water (20 ml) and extracted with EtOAc (20 mL×3). The combined organic layers were washed with brine (20 mL), dried over Na₂SO₄, filtered and concentrated. After purified by prep-HPLC (column: C18 150×30 mm; mobile phase: [water (NH₃H₂O+NH₄HCO₃)-ACN]; gradient: 38%-68% B over 7 min), 4-((1-(4-(2-(2-aminopyridin-3-yl)-1H-imidazo[4,5-c]pyridin-1-yl)benzyl) piperidin-4-yl)amino)pyrimidine-2-carbonitrile (Example 540, 38.0 mg, yield: 38%) was obtained as an off-white solid. MS: m/z=503.2 [M+H]⁺. ¹H NMR (400 MHz, Dimethylsulfoxide-d₆) δ 9.09 (s, 1H), 8.38 (d, J=5.6 Hz, 1H), 8.13-8.02 (m, 2H), 7.99 (dd, J=4.8, 2.0 Hz, 1H), 7.49 (d, J=8.4 Hz, 2H), 7.41 (d, J=8.0 Hz, 2H), 7.26 (d, J=5.2 Hz, 1H), 7.16 (dd, J=7.6, 1.6 Hz, 1H), 6.96 (s, 2H), 6.67 (d, J=6.0 Hz, 1H), 6.38 (dd, J=7.6, 4.8 Hz, 1H), 3.90-3.74 (m, 1H), 3.58 (s, 2H), 2.87-2.77 (m, 2H), 2.23-2.07 (m, 2H), 1.95-1.81 (m, 2H), 1.57-1.41 (m, 2H).

Example 541: 4-((1-(4-(2-(2-Aminopyridin-3-yl)-5-(4-fluorophenyl)-3H-imidazo[4,5-b]pyridin-3-yl)benzyl)piperidin-4-yl)((methyl)amino)pyrimidine-2-carbonitrile

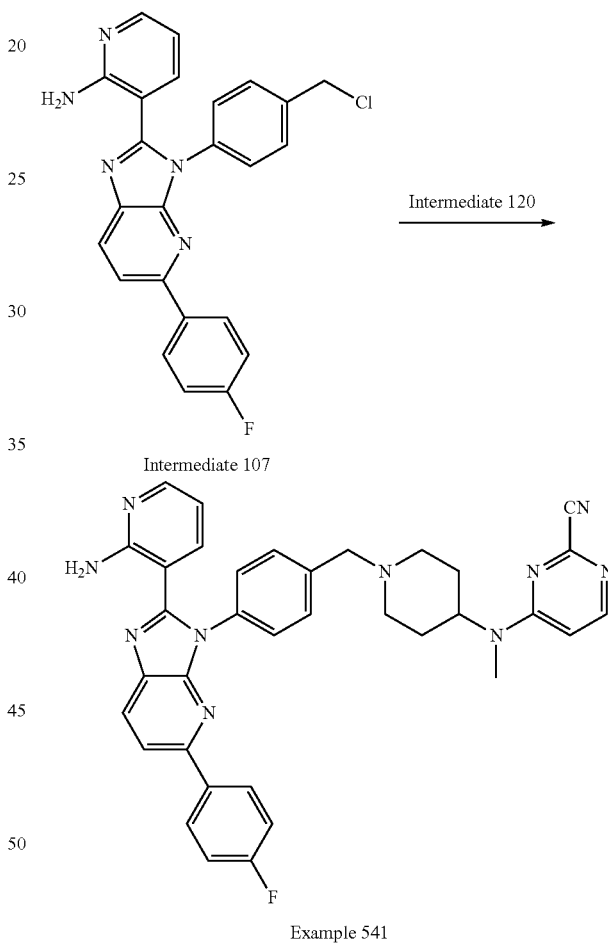

Example 541

To a solution of Intermediate 107 (100 mg, 233 µmol) in DMF (3 mL) were added Intermediate 120 (61 mg, 280 µmol), NaI (35 mg, 233 µmol) and K₂CO₃ (129 mg, 931 µmol) at 25° C. The mixture was stirred at 50° C. for 1 hr. The reaction mixture was poured into H₂O (50 mL) and extracted with CH₂Cl₂ (20 mL×2). The combined organic layers were washed with brine (40 mL), dried over anhydrous Na₂SO₄, filtered and concentrated. After purified by silica gel flash chromatography (Eluent of 0~5% MeOH in CH₂Cl₂), 4-((1-(4-(2-(2-aminopyridin-3-yl)-5-(4-fluorophenyl)-3H-imidazo[4,5-b]pyridin-3-yl)benzyl)piperidin-4-yl) (methyl)amino)pyrimidine-2-carbonitrile (Example 541, 25.8 mg, yield: 17%) was obtained as an off white solid. MS: m/z=611.3 [M+H]+. 1H NMR (400 MHz, Dimethylsulfoxide-d6) δ 8.27 (d, J=8.4 Hz, 1H), 8.24 (d, J=6.0 Hz, 1H), 8.10-8.05 (m, 2H), 8.01-7.96 (m, 2H), 7.52-7.43 (m, 4H), 7.30 (t, J=8.8 Hz, 2H), 7.15 (dd, J=8.0, 1.6 Hz, 1H), 7.02 (s, 3H), 6.38 (dd, J=7.6, 4.8 Hz, 1H), 3.62 (s, 2H), 2.94 (s, 6H), 2.22-2.13 (m, 2H), 1.89-1.80 (m, 2H), 1.65-1.56 (m, 2H). 19F NMR (400 MHz, Dimethylsulfoxide-d6) δ −113.59.

Example 542: 4-((1-(4-(2-(2-Aminopyridin-3-yl)-5-(6-(difluoromethoxy)pyridin-3-yl)-3H-imidazo[4,5-b]pyridin-3-yl)benzyl)piperidin-4-yl)amino)pyrimidine-2-carbonitrile

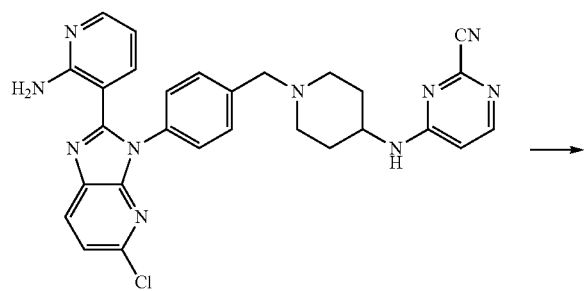

Example 405

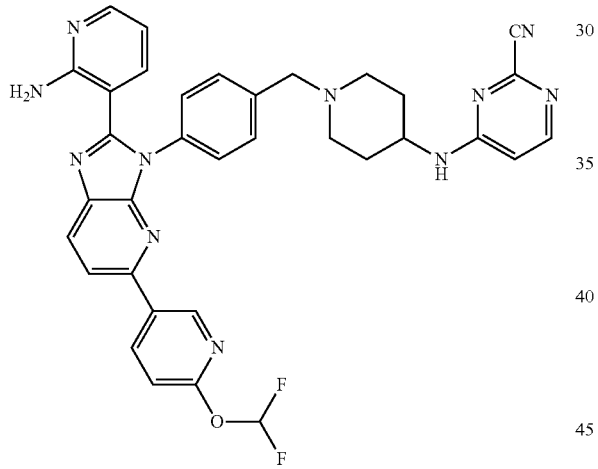

Example 542

A mixture of (6-(difluoromethoxy)pyridin-3-yl)boronic acid (101 mg, 536 μmol), Example 405 (240 mg, 447 μmol), Cs2CO3 (437 mg, 1.3 mmol), Pd(dppf)Cl2 (32.7 mg, 45 μmol) in H2O (1 mL) and 1,4-dioxane (5 mL) was degassed and purged with N2 three times. The mixture was stirred at 100° C. for 1 hr under N2 atmosphere. The reaction mixture was diluted with H2O (30 mL) and extracted with EtOAc (20 mL×3). The combined organic layers were washed with brine (30 mL), dried over Na2SO4, filtered and concentrated under reduced pressure. After purified by prep-HPLC (column: Phenomenex C18 150×25 mm×10 μm; mobile phase: [water (NH4HCO3)-ACN]; gradient: 47%-77% B over 11 min), 4-((1-(4-(2-(2-aminopyridin-3-yl)-5-(6-(difluoromethoxy)pyridin-3-yl)-3H-imidazo[4,5-b]pyridin-3-yl)benzyl)piperidin-4-yl)amino)pyrimidine-2-carbonitrile (Example 542, 68.7 mg, yield: 24%) was obtained as an off white solid. MS: m/z=646.3 [M+H]+. 1H NMR (400 MHz, Dimethylsulfoxide-d6) δ 8.92 (d, J=2.4 Hz, 1H), 8.50 (dd, J=8.8, 2.4 Hz, 1H), 8.31 (d, J=8.4 Hz, 1H), 8.15-7.96 (m, 4H), 7.95-7.77 (m, 1H), 7.52-7.43 (m, 4H), 7.22-7.13 (m, 2H), 7.04 (br s, 2H), 6.67 (d, J=6.0 Hz, 1H), 6.39 (dd, J=7.6, 4.8 Hz, 1H), 3.81 (dd, J=6.8, 2.4 Hz, 1H), 3.59 (s, 2H), 2.83 (d, J=10.8 Hz, 2H), 2.16 (t, J=10.8 Hz, 2H), 1.89 (d, J=10.4 Hz, 2H), 1.57-1.43 (m, 2H). 19F NMR (400 MHz, Dimethylsulfoxide-d6) δ −87.27.

Example 543: 4-((1-(4-(2-(2-Aminopyridin-3-yl)-5-(2-(difluoromethoxy)pyridin-4-yl)-3H-imidazo[4,5-h]pyridin-3-yl)benzyl)piperidin-4-yl)amino)pyrimidine-2-carbonitrile

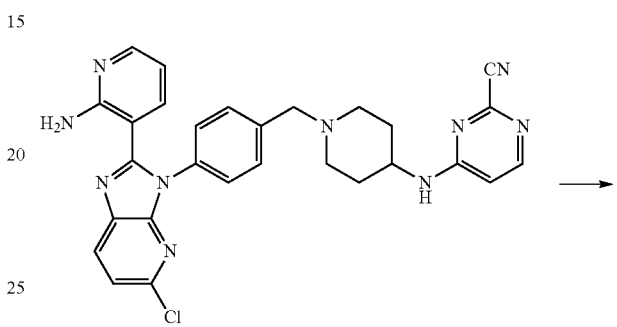

Example 405

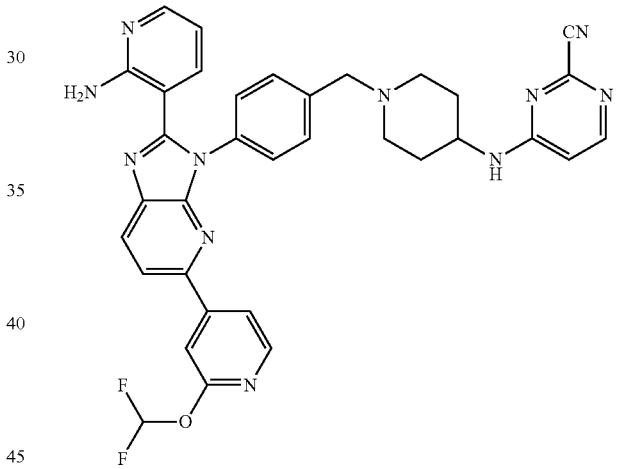

Example 543

A mixture of (2-(difluoromethoxy)pyridin-4-yl)boronic acid (93 mg, 492 μmol), Example 405 (220 mg, 410 μmol), Cs2CO3 (400 mg, 1.2 mmol), Pd(dppf)Cl2 (30 mg, 41 μmol) in H2O (0.5 mL) and 1,4-dioxane (1 mL) was degassed and purged with N2 three times. The mixture was stirred at 100° C. for 1 hr under N2 atmosphere. The reaction mixture was diluted with H2O (30 mL) and extracted with EtOAc (20 mL×3). The combined organic layers were washed with brine (30 mL), dried over Na2SO4, filtered, and concentrated under reduced pressure. After purified by prep-HPLC (column: Phenomenex C18 150×25 mm×10 μm; mobile phase: [water (NH4HCO3)-ACN]; gradient: 47%-77% B over 11 min), 4-((1-(4-(2-(2-aminopyridin-3-yl)-5-(2-(difluoromethoxy)pyridin-4-yl)-3H-imidazo[4,5-b]pyridin-3-yl)benzyl)piperidin-4-yl)amino)pyrimidine-2-carbonitrile (Example 543, 86.6 mg, yield: 32%) was obtained as an off white solid. MS: m/z=646.3 [M+H]+. 1H NMR (400 MHz, Dimethylsulfoxide-d6) δ 8.42-8.31 (m, 2H), 8.21 (d, J=8.4 Hz, 1H), 8.13-7.99 (m, 3H), 7.96-7.87 (m, 1.3H), 7.73 (s, 0.5H), 7.66 (s, 1H), 7.55 (s, 0.3H), 7.53-7.42 (m, 4H), 7.19 (dd, J=7.6, 1.6 Hz, 1H), 7.11-6.97 (m, 2H), 6.67 (d, J=6.0 Hz, 1H), 6.39 (dd, J=7.6, 4.8 Hz, 1H), 3.91-3.74 (m, 1H), 3.60 (s, 2H), 2.83 (d, J=11.2 Hz, 2H), 2.23-2.11 (m, 2H), 1.95-1.80 (m, 2H), 1.59-1.42 (m, 2H). $^{19}$F NMR (400 MHz, Dimethysulfoxide-$d_6$) δ −87.12.

Example 544: 4-((1-(4-(2-(2-Aminopyridin-3-yl)-5-(4-fluoro-2-hydroxyphenyl)-3H-imidazo[4,5-b]pyridin-3-yl)benzyl)piperidin-4-yl)amino)pyrimidine-2-carbonitrile

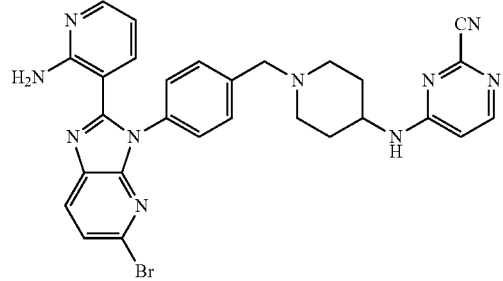

Example 485

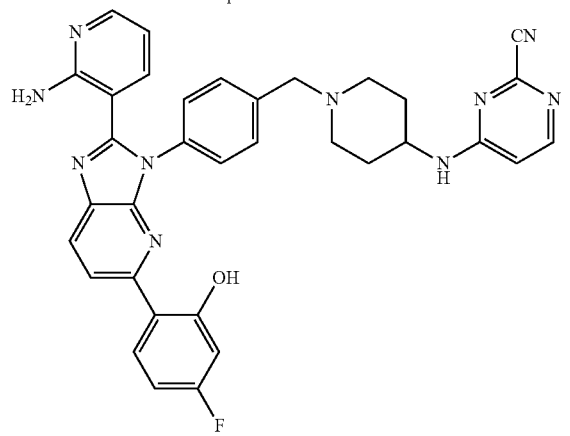

Example 544

To a solution of Example 485 (200 mg, 344 µmol) and (4-fluoro-2-hydroxy-phenyl)boronic acid (59.0 mg, 378 µmol) in 1,4-dioxane (10 mL) and H$_2$O (2 mL) were added Cs$_2$CO$_3$ (336 mg, 1.03 mmol) and Pd(dppf)Cl$_2$ (25.2 mg, 34.4 µmol) at 25° C. The mixture was degassed and purged with N$_2$ three times and stirred at 100° C. for 2 hr. The reaction mixture was quenched with water (20 mL) and extracted with EtOAc (20 mL×3). The combined organic layers were washed with brine (20 mL), dried over Na$_2$SO$_4$, filtered and concentrated. The crude was purified by silica gel flash chromatography (MeOH in CH$_2$Cl$_2$=0-20%) to give 4-((1-(4-(2-(2-aminopyridin-3-yl)-5-(4-fluoro-2-hydroxyphenyl)-3H-imidazo[4,5-b]pyridin-3-yl)benzyl)piperidin-4-yl)amino)pyrimidine-2-carbonitrile (Example 544, 35.2 mg, yield: 17%) as a yellow solid. MS: m/z=613.2 [M+H]$^+$. $^1$H NMR (400 MHz, Dimethylsulfoxide-$d_6$) δ 13.19 (s, 1H), 8.40 (d, J=8.4 Hz, 1H), 8.20-8.05 (m, 4H), 8.02 (dd, J=4.8, 1.6 Hz, 1H), 7.58-7.43 (m, 4H), 7.24 (d, J=6.8 Hz, 1H), 7.08 (s, 2H), 6.77 (td, J=8.4, 2.8 Hz, 1H), 6.71-6.62 (m, 2H), 6.47-6.34 (m, 1H), 3.92-3.69 (m, 1H), 3.61 (s, 2H), 2.93-2.72 (m, 2H), 2.27-2.09 (m, 2H), 1.97-1.83 (m, 2H), 1.57-1.47 (m, 2H). $^{19}$F NMR (400 MHz, Dimethylsulfoxide-$d_6$) δ −109.982.

Example 545: 4-((1-(4-(2-(2-Aminopyridin-3-yl)-5-(4-fluoro-3-hydroxyphenyl)-3H-imidazo[4,5-b]pyridin-3-yl)benzyl)piperidin-4-yl)amino)pyrimidine-2-carbonitrile

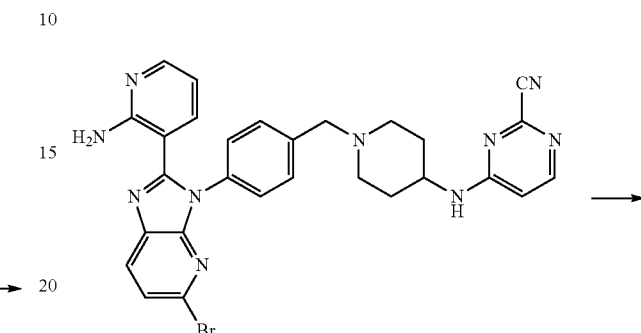

Example 485

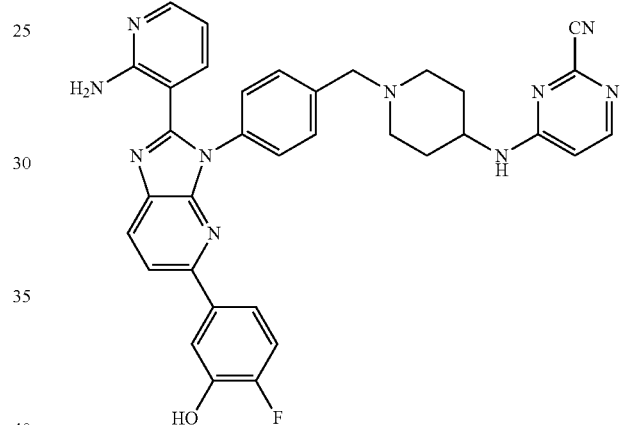

Example 545

To a solution of Example 485 (200 mg, 344 µmol) and (4-fluoro-3-hydroxyphenyl)boronic acid (59.0 mg, 378 µmol) in 1,4-dioxane (10 mL) and H$_2$O (2 mL) were added Cs$_2$CO$_3$ (336 mg, 1.03 mmol) and Pd(dppf)Cl$_2$ (25.2 mg, 34.4 µmol) at 25° C. The mixture was degassed and purged with N$_2$ three times and stirred at 100° C. for 2 hr. The reaction mixture was quenched with water (20 mL) and extracted with EtOAc (20 mL×3). The combined organic layers were washed with brine (20 mL), dried over Na$_2$SO$_4$, filtered and concentrated. After purified by silica gel flash chromatography (MeOH in CH$_2$Cl$_2$=0-20%), 4-((1-(4-(2-(2-aminopyridin-3-yl)-5-(4-fluoro-3-hydroxyphenyl)-3H-imidazo[4,5-b]pyridin-3-yl)benzyl)piperidin-4-yl)amino)pyrimidine-2-carbonitrile (Example 545, 30.0 mg, 14% yield) was obtained as a yellow solid. MS: m/z=613.2 [M+H]$^+$. $^1$H NMR (400 MHz, Dimethylsulfoxide-$d_6$) δ 10.00 (s, 1H), 8.24 (d, J=8.4 Hz, 1H), 8.15-8.03 (m, 2H), 8.01-7.96 (m, 1H), 7.88 (d, J=8.4 Hz, 1H), 7.63 (dd, J=9.2, 2.0 Hz, 1H), 7.52-7.40 (m, 5H), 7.26-7.17 (m, 1H), 7.15-7.11 (m, 1H), 7.01 (s, 2H), 6.72-6.64 (m, 1H), 6.42-6.30 (m, 1H), 3.95-3.69 (m, 1H), 3.60 (s, 2H), 2.95-2.78 (m, 2H), 2.23-2.07 (m, 2H), 1.98-1.81 (m, 2H), 1.62-1.53 (m, 2H). $^{19}$F NMR (400 MHz, Dimethylsulfoxide-$d_6$) δ −136.277.

Example 546: 4-((1-(4-(2-(2-Aminopyridin-3-yl)-5-(1-methyl-1H-imidazol-5-yl)-3H-imidazo[4,5-b]pyridin-3-yl)benzyl)piperidin-4-yl)amino)pyrimidine-2-carbonitrile

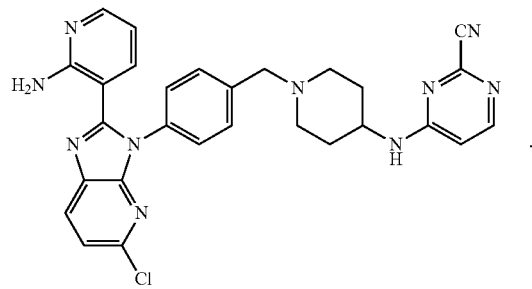

Example 405

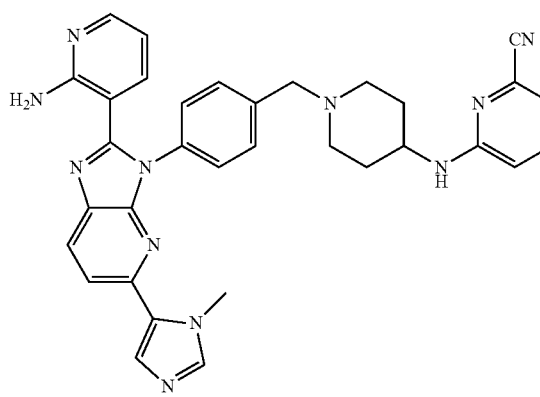

Example 546

A mixture of Example 405 (250 mg, 465 μmol), 1-methyl-5-(4,4,5,5-tetramethyl-1,3,2-dioxaborolan-2-yl)-1H-imidazole (194 mg, 931 μmol,), $Cs_2CO_3$ (455 mg, 1.4 mmol), Pd(dppf)$Cl_2$ (34 mg, 46 μmol) in $H_2O$ (1 mL) and 1,4-dioxane (3 mL) was degassed and purged with $N_2$ three times. The mixture was stirred at 100° C. for 1 hr under $N_2$ atmosphere. The reaction mixture was diluted with $H_2O$ (30 mL) and extracted with EtOAc (20 mL×3). The combined organic layers were washed with brine (30 mL), dried over $Na_2SO_4$, filtered, and concentrated under reduced pressure. After purified by prep-HPLC (column: Phenomenex C18 150×25 mm×10 μm; mobile phase: [water ($NH_4HCO_3$)-ACN]; gradient: 28%-58% B over 11 min), 4-((1-(4-(2-(2-aminopyridin-3-yl)-5-(1-methyl-1H-imidazol-5-yl)-3H-imidazo[4,5-b]pyridin-3-yl)benzyl)piperidin-4-yl)amino)pyrimidine-2-carbonitrile (Example 546, 78 mg, yield: 29%) was obtained as a yellow solid. MS: m/z=583.3 [M+H]$^+$. $^1$H NMR (400 MHz, Dimethysulfoxide-$d_6$) δ 8.21 (d, J=8.4 Hz, 1H), 8.16-7.92 (m, 3H), 7.76 (d, J=8.4 Hz, 1H), 7.67 (s, 1H), 7.55 (s, 1H), 7.49-7.39 (m, 4H), 7.21 (dd, J=7.6, 1.6 Hz, 1H), 7.09 (br s, 2H), 6.67 (d, J=6.0 Hz, 1H), 6.39 (dd, J=7.6, 4.8 Hz, 1H), 3.89-3.77 (m, 1H), 3.75 (s, 3H), 3.58 (s, 2H), 2.86-2.74 (m, 2H), 2.13 (t, J=10.8 Hz, 2H), 1.89 (d, J=10.8 Hz, 2H), 1.56-1.41 (m, 2H).

Example 547: 4-((1-(4-(2-(2-Aminopyridin-3-yl)-5-(5-methylpyridin-2-yl)-3H-imidazo[4,5-b]pyridin-3-yl)benzyl)piperidin-4-yl)amino)pyrimidine-2-carbonitrile

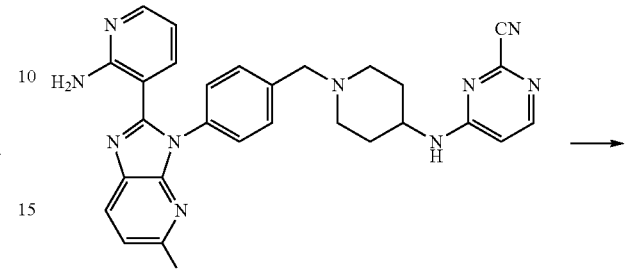

Example 405

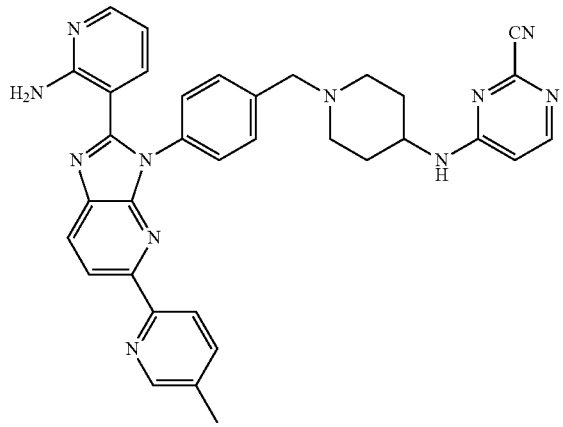

Example 547

A mixture of Example 405 (100 mg, 186 μmol), (5-methylpyridin-2-yl)boronic acid (76.5 mg, 559 μmol), cataCXium A Pd G3 (15.8 mg, 18.6 μmol), CuBr (20 mg, 140 μmol) and $Cs_2CO_3$ (182 mg, 559 μmol) in 1,4-dioxane (3 mL) was degassed and purged with $N_2$ three times. The mixture was stirred at 90° C. for 3 hr under $N_2$ atmosphere. The reaction mixture was poured into $H_2O$ (15 mL) and extracted with EtOAc (15 mL×3). The combined organic phases were dried over anhydrous $Na_2SO_4$, filtered and concentrated under reduced pressure. After purified by prep-HPLC (column: Waters Xbridge 150×25 mm×5 μm; mobile phase: [water ($NH_4HCO_3$)-ACN]; gradient: 34%-64% B over 11 min), 4-((1-(4-(2-(2-aminopyridin-3-yl)-5-(5-methylpyridin-2-yl)-3H-imidazo[4,5-b]pyridin-3-yl)benzyl)piperidin-4-yl)amino)pyrimidine-2-carbonitrile (Example 547, 15.5 mg, yield: 14%) was obtained as a yellow solid. MS: m/z=594.3 [M+H]$^+$. $^1$H NMR (400 MHz, Methanol-$d_4$) δ8.46-8.43 (m, 1H), 8.38 (d, J=6.0 Hz, 1H), 8.22 (d, J=8.0 Hz, 1H), 8.17 (d, J=8.0 Hz, 1H), 8.03-7.93 (m, 2H), 7.70-7.63 (m, 1H), 7.57-7.52 (m, 2H), 7.49-7.42 (m, 2H), 7.32 (dd, J=7.6, 1.6 Hz, 1H), 6.63-6.54 (m, 1H), 6.46 (dd, J=7.6, 5.2 Hz, 1H), 4.13-3.79 (m, 1H), 3.66 (s, 2H), 3.00-2.92 (m, 2H), 2.38 (s, 3H), 2.32-2.22 (m, 2H), 2.02-1.97 (m, 2H), 1.68-1.55 (m, 2H).

Example 548: 4-((1-(4-(2-(2-Aminopyridin-3-yl)-5-(4-cyanopyridin-2-yl)-3H-imidazo[4,5-b]pyridin-3-yl)benzyl)piperidin-4-yl)amino)pyrimidine-2-carbonitrile

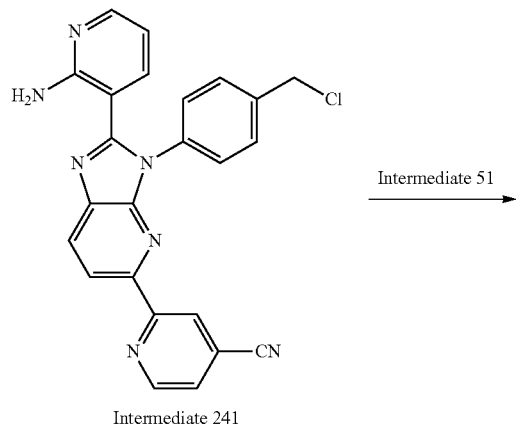

Intermediate 241

→ Intermediate 51

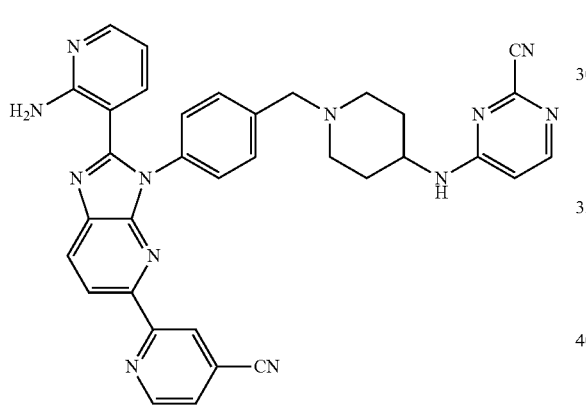

Example 548

To a solution of Intermediate 241 (67.9 mg, 143 μmol, HCl salt) and Intermediate 51 (40.8 mg, 129 μmol, TFA salt) in DMF (4 mL) were added K$_2$CO$_3$ (59.3 mg, 429 μmol) and NaI (4.29 mg, 28.6 μmol). The mixture was stirred at 50° C. for 1 hr. The reaction mixture was quenched with H$_2$O (10 mL) at 25° C., diluted with CH$_2$Cl$_2$ (10 mL), and extracted with CH$_2$Cl$_2$ (15 mL×2). The combined organic layers were washed with brine (30 mL×3), dried over Na$_2$SO$_4$, filtered, and concentrated under reduced pressure. After purified by prep-TLC (CH$_2$Cl$_2$:MeOH=10:1), 4-((1-(4-(2-(2-amino-pyridin-3-yl)-5-(4-cyanopyridin-2-yl)-3H-imidazo[4,5-b]pyridin-3-yl)benzyl)piperidin-4-yl)amino)pyrimidine-2-carbonitrile (Example 548, 5.4 mg, yield: 6.2% for three steps) was obtained as a light-yellow solid. MS: m/z=605.5 [M+H]$^+$. $^1$H NMR (400 MHz, Chloroform-d) δ 8.81 (d, J=4.8 Hz, 1H), 8.57-8.50 (m, 2H), 8.21 (d, J=8.0 Hz, 1H), 8.18-8.11 (m, 1H), 8.09 (d, J=4.8 Hz, 1H), 7.57 (d, J=8.4 Hz, 2H), 7.45 (d, J=4.8 Hz, 1H), 7.40 (d, J=8.4 Hz, 2H), 7.16 (d, J=7.6 Hz, 1H), 6.69 (br s, 2H), 6.43 (d, J=6.0 Hz, 1H), 6.38 (dd, J=8.0, 4.8 Hz, 1H), 4.22-3.79 (m, 1H), 3.69 (s, 2H), 2.99-2.91 (m, 2H), 2.35-2.27 (m, 2H), 2.12-2.06 (m, 2H), 1.38-1.28 (m, 2H).

Example 549: 4-((1-(4-(2-(2-Aminopyridin-3-yl)-6-bromo-5-(4-fluorophenyl)-3H-imidazo[4,5-b]pyridin-3-yl)benzyl)piperidin-4-yl)amino)pyrimidine-2-carbonitrile

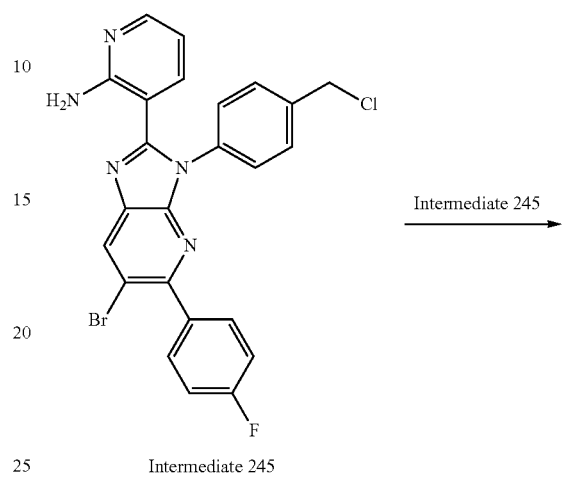

Intermediate 245

→ Intermediate 245

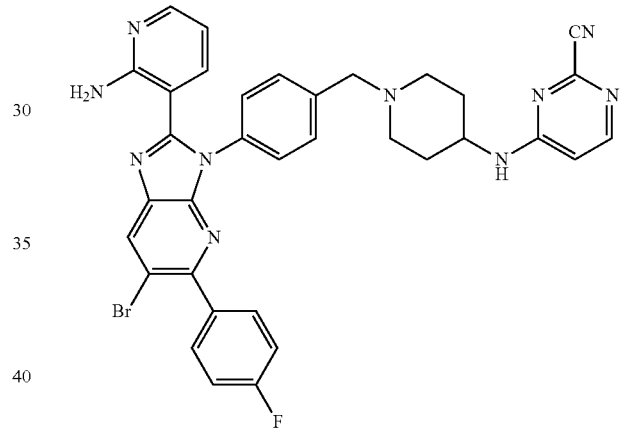

Example 549

To a solution of Intermediate 245 (266 mg, 488 μmol, HCl salt) and Intermediate 51 (139 mg, 439 μmol, TFA salt) in DMF (5 mL) were added K$_2$CO$_3$ (202 mg, 1.46 mmol) and NaI (14.6 mg, 97.6 μmol). The mixture was stirred at 50° C. for 1 hr. The reaction mixture was quenched with H$_2$O (10 mL) at 25° C., diluted with CH$_2$Cl$_2$ (10 mL), and extracted with CH$_2$Cl$_2$ (15 mL×2). The combined organic layers were washed with brine (30 mL×3), dried over Na$_2$SO$_4$, filtered, and concentrated under reduced pressure. After purified by silica gel flash chromatography (Eluent of 0%-6% MeOH in CH$_2$Cl$_2$), 4-((1-(4-(2-(2-aminopyridin-3-yl)-6-bromo-5-(4-fluorophenyl)-3H-imidazo[4,5-b]pyridin-3-yl)benzyl)piperidin-4-yl)amino)pyrimidine-2-carbonitrile (Example 549, 84.8 mg, yield: 26% for three steps) was obtained as a yellow solid. MS: m/z=675.0, 677.0 [M+H]$^+$. $^1$H NMR (400 MHz, Dimethylsulfoxide-d$_6$) δ 8.64 (s, 1H), 8.20-7.93 (m, 3H), 7.66-7.55 (m, 2H), 7.45-7.37 (m, 4H), 7.29-7.27 (m, 2H), 7.15 (dd, J=7.6, 1.6 Hz, 1H), 6.96 (br s, 2H), 6.66 (d, J=6.0 Hz, 1H), 6.38 (dd, J=7.6, 4.8 Hz, 1H), 3.85-3.71 (m, 1H), 3.54 (s, 2H), 2.83-2.72 (m, 2H), 2.18-2.08 (m, 2H), 1.92-1.77 (m, 2H), 1.53-1.38 (m, 2H).

Example 550: 2-(2-Aminopyridin-3-yl)-3-(4-((4-((2-cyanopyrimidin-4-yl)amino)piperidin-1-yl)methyl)phenyl)-5-methyl-3H-imidazo[4,5-b]pyridine-6-carbonitrile

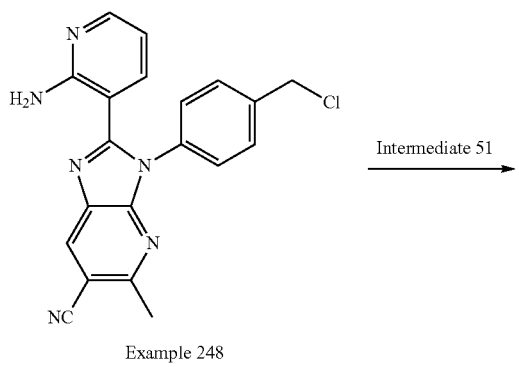

Example 248

Intermediate 51

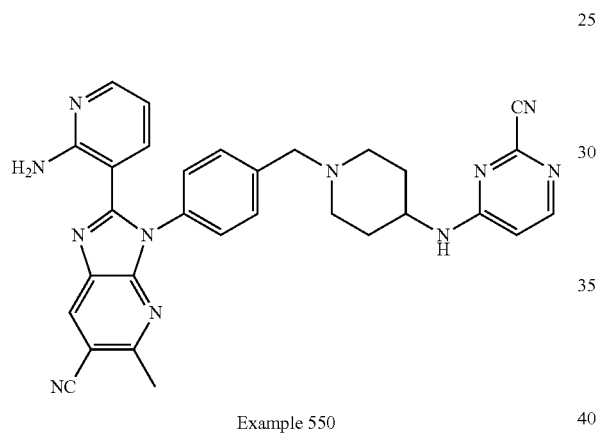

Example 550

Example 551: 4-((1-(4-(2-(2-aminopyridin-3-yl)-5-(3-fluoropyridin-4-yl)-3H-imidazo[4,5-b]pyridin-3-yl)benzyl)piperidin-4-yl)amino)pyrimidine-2-carbonitrile

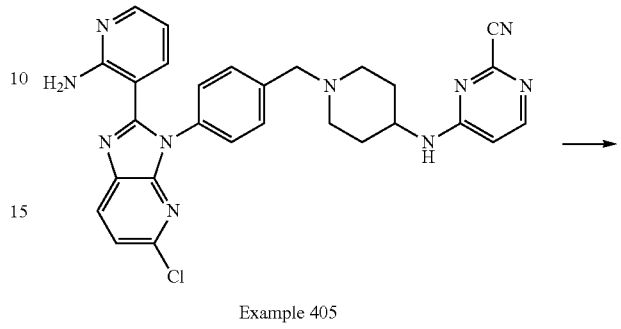

Example 405

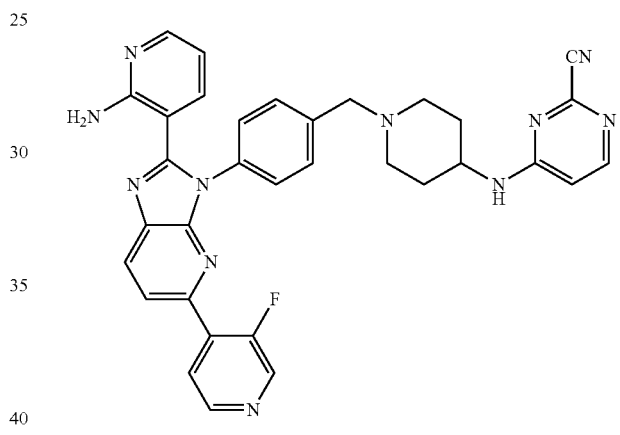

Example 551

To a solution of Example 248 (196 mg, 477 μmol, HCl salt) and Intermediate 51 (151 mg, 477 μmol, TFA salt) in DMF (5 mL) were added $K_2CO_3$ (198 mg, 1.43 mmol) and NaI (14.3 mg, 95.3 μmol). The mixture was stirred at 50° C. for 1 hr. The reaction mixture was quenched with $H_2O$ (10 mL) at 25° C., diluted with $CH_2Cl_2$ (10 mL), and extracted with $CH_2Cl_2$ (15 mL×2). The combined organic layers were washed with brine (30 mL×3), dried over $Na_2SO_4$, filtered, and concentrated under reduced pressure. After purified by silica gel flash chromatography (Eluent of 0%~6% MeOH in $CH_2Cl_2$), 2-(2-aminopyridin-3-yl)-3-(4-((4-((2-cyanopyrimidin-4-yl)amino)piperidin-1-yl)methyl)phenyl)-5-methyl-3H-imidazo[4,5-b]pyridine-6-carbonitrile (Example 550, 120 mg, yield: 46% for three steps) was obtained as a yellow solid. MS: m/z=542.2 [M+H]$^+$. $^1$H NMR (400 MHz, Dimethylsulfoxide-$d_6$) δ 8.72 (s, 1H), 8.13-8.03 (m, 2H), 8.00 (dd, J=4.4, 1.6 Hz, 1H), 7.51-7.43 (m, 2H), 7.42-7.36 (m, 2H), 7.16 (dd, J=7.6, 1.6 Hz, 1H), 6.93 (br s, 2H), 6.67 (d, J=6.0 Hz, 1H), 6.38 (dd, J=7.6, 4.8 Hz, 1H), 3.87-3.75 (m, 1H), 3.57 (s, 2H), 2.85-2.77 (m, 2H), 2.70 (s, 3H), 2.22-2.10 (m, 2H), 1.92-1.83 (m, 2H), 1.56-1.43 (m, 2H).

A mixture of Example 405 (100 mg, 186 μmol), (3-fluoropyridin-4-yl)boronic acid (26.2 mg, 186 μmol), $Na_2CO_3$ (59.2 mg, 559 μmol), Pd(dppf)Cl$_2$ (13.6 mg, 18.6 μmol) in $H_2O$ (0.5 mL) and 1,4-dioxane (2 mL) was degassed and purged with $N_2$ three times. The mixture was stirred at 100° C. for 16 hr under $N_2$ atmosphere. The reaction mixture was poured into $H_2O$ (15 mL) and extracted with EtOAc (15 mL×3). The combined organic layers were dried over anhydrous $Na_2SO_4$, filtered and concentrated under reduced pressure. After purified by prep-HPLC (column: Phenomenex C18 150×25 mm×10 μm; mobile phase: [water (NH$_4$HCO$_3$)-ACN]; gradient: 38%-68% B over 11 min), 4-((1-(4-(2-(2-aminopyridin-3-yl)-5-(3-fluoropyridin-4-yl)-3H-imidazo[4,5-b]pyridin-3-yl)benzyl)piperidin-4-yl)amino)pyrimidine-2-carbonitrile (Example 551, 19.2 mg, yield: 16%) was obtained as a pink lyophilized powder. MS: m/z=598.2 [M+H]$^+$. $^1$H NMR (400 MHz, Dimethylsulfoxide-$d_6$) δ 8.69 (d, J=2.8 Hz, 1H), 8.51 (d, J=4.8 Hz, 1H), 8.36 (d, J=8.0 Hz, 1H), 8.14-7.97 (m, 3H), 7.97-7.91 (m, 1H), 7.85 (dd, J=6.8, 5.2 Hz 1H), 7.48-7.43 (m, 4H), 7.18 (dd, J=7.6, 1.6 Hz 1H), 6.99 (s, 2H), 6.66 (d, J=6.4 Hz, 1H), 6.38 (dd, J=7.6, 4.8 Hz 1H), 3.90-3.71 (m, 1H), 3.57 (s, 2H), 2.87-2.74 (m, 2H), 2.21-2.05 (m, 2H), 1.94-1.81 (m, 2H), 1.58-1.37 (m, 2H). $^{19}$F NMR (400 MHz, Dimethylsulfoxide-$d_6$) δ −131.931.

Example 552: 4-((1-(4-(2-(2-Aminopyridin-3-yl)-5-(5-methoxypyridin-2-yl)-3H-imidazo[4,5-b]pyridin-3-yl)benzyl)piperidin-4-yl)amino)pyrimidine-2-carbonitrile

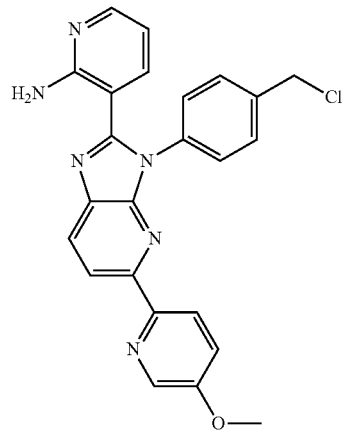

Intermediate 242

→ Intermediate 51

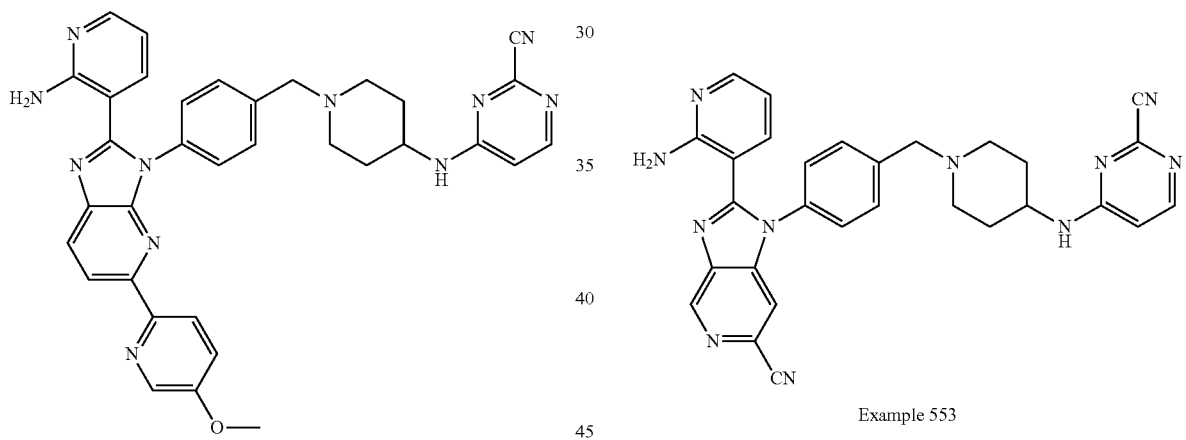

Example 552

To a solution of Intermediate 242 (150 mg, 339 µmol, HCl salt) and Intermediate 51 (103 mg, 325 µmol, TFA salt) in DMF (5 mL) were added K$_2$CO$_3$ (140 mg, 1.02 mmol) and NaI (10.2 mg, 67.7 µmol). The mixture was stirred at 50° C. for 0.5 hr. The reaction mixture was poured into H$_2$O (50 mL) and extracted with CH$_2$Cl$_2$ (15 mL×3). The combined organic layers were dried over anhydrous Na$_2$SO$_4$, filtered, and concentrated under reduced pressure. After purified by silica gel flash chromatography (Eluent of 0%~6% MeOH in CH$_2$Cl$_2$), 4-((1-(4-(2-(2-aminopyridin-3-yl)-5-(5-methoxypyridin-2-yl)-3H-imidazo[4,5-b]pyridin-3-yl)benzyl)piperidin-4-yl)amino)pyrimidine-2-carbonitrile (Example 552, 50.2 mg, yield: 24%) was obtained as a light-yellow solid. MS: m/z=610.2 [M+H]$^+$. $^1$H NMR (400 MHz, Dimethylsulfoxide-d$_6$) δ 8.39-8.33 (m, 2H), 8.26 (d, J=8.4 Hz, 1H), 8.13 (d, J=8.8 Hz, 1H), 8.09-8.03 (m, 2H), 8.00 (dd, J=4.8, 1.6 Hz, 1H), 7.51-7.44 (m, 5H), 7.15 (dd, J=7.6, 1.6 Hz, 1H), 7.02 (s, 2H), 6.68 (d, J=6.0 Hz, 1H), 6.38 (dd, J=7.6, 4.8 Hz, 1H), 3.87 (s, 3H). 3.85-3.77 (m, 1H), 3.60 (s, 2H), 2.88-2.79 (m, 2H), 2.22-2.12 (m, 2H), 1.96-1.84 (m, 2H), 1.56-1.45 (m, 2H).

Example 553: 2-(2-Aminopyridin-3-yl)-1-(4-((4-((2-cyanopyrimidin-4-yl)amino)piperidin-1-yl)methyl)phenyl)-1H-imidazo[4,5-c]pyridine-6-carbonitrile

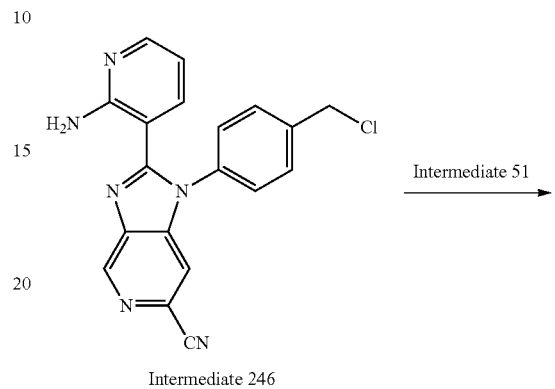

Intermediate 246

→ Intermediate 51

Example 553

To a solution of Intermediate 246 (160 mg, 443 µmol, HCl salt) and Intermediate 51 (141 mg, 443 µmol, TFA salt) in DMF (5 mL) were added K$_2$CO$_3$ (184 mg, 1.33 mmol) and NaI (13.3 mg, 88.7 µmol). The mixture was stirred at 50° C. for 0.5 hr. The reaction mixture was quenched with H$_2$O (50 mL) at 25° C., diluted with CH$_2$Cl$_2$ (50 mL), and extracted with CH$_2$Cl$_2$ (50 mL×2). The combined organic layers were washed with brine (30 mL×3), dried over Na$_2$SO$_4$, filtered, and concentrated under reduced pressure. After purified by silica gel flash chromatography (Eluent of 0%-6% MeOH in CH$_2$Cl$_2$), 2-(2-aminopyridin-3-yl)-1-(4-((4-((2-cyanopyrimidin-4-yl)amino)piperidin-1-yl)methyl)phenyl)-1H-imidazo[4,5-c]pyridine-6-carbonitrile (Example 553, 64.0 mg, yield: 27%) was obtained as a yellow solid. MS: m/z=528.2 [M+H]$^+$. $^1$H NMR (400 MHz, Dimethylsulfoxide-d$_6$) δ 9.22 (d, J=0.8 Hz, 1H), 8.12-8.04 (m, 3H), 8.03-8.02 (m, 1H), 7.51-7.48 (m, 2H), 7.45-7.43 (m, 2H), 7.22 (dd, J=7.6, 1.6 Hz, 1H), 6.88 (s, 2H), 6.67 (d, J=6.0 Hz, 1H), 6.41 (dd, J=7.6, 4.8 Hz, 1H), 3.88-3.73 (m, 1H), 3.58 (s, 2H), 2.82 (d, J=11.6 Hz, 2H), 2.18-2.12 (m, 2H), 1.89 (d, J=10.4 Hz, 2H), 1.54-1.47 (m, 2H).

Example 554: 4-((1-(4-(2-(2-Aminopyridin-3-yl)-5-(4-methyloxazol-5-yl)-3H-imidazo[4,5-b]pyridin-3-yl)benzyl)piperidin-4-yl)amino)pyrimidine-2-carbonitrile

Example 555: 4-((1-(4-(2-(2-Aminopyridin-3-yl)-5-(1-cyclopropyl-1H-pyrazol-4-yl)-3H-imidazo[4,5-b]pyridin-3-yl)benzyl)piperidin-4-yl)amino)pyrimidine-2-carbonitrile

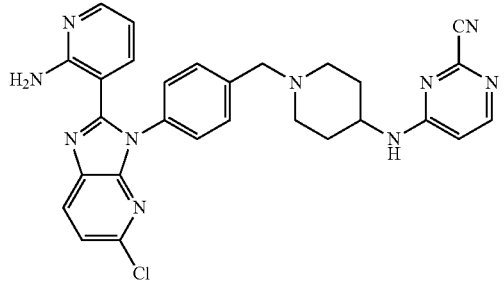

Example 405

→

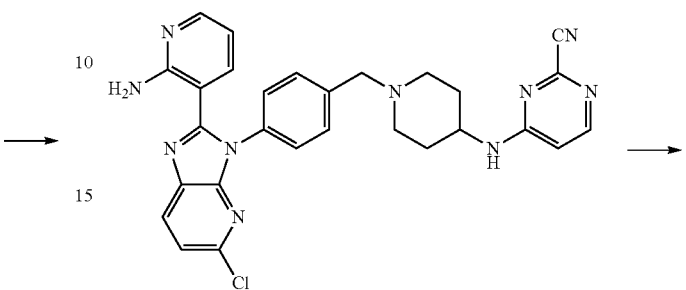

Example 405

→

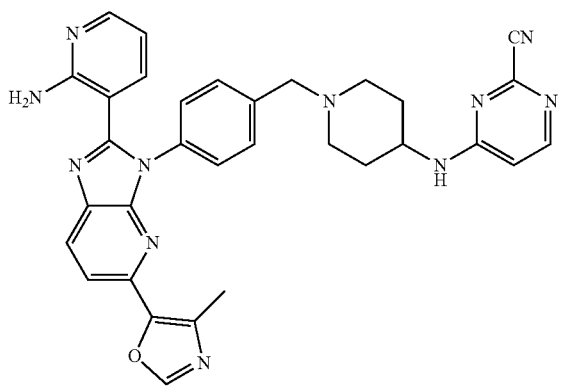

Example 554

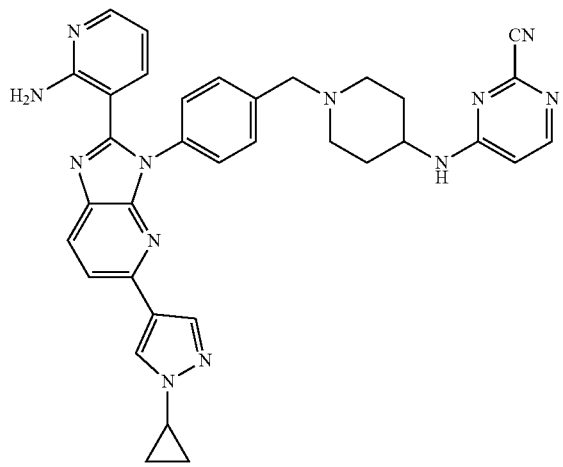

Example 555

A mixture of Example 405 (300 mg. 559 μmol), 4-methyl-5-(4,4,5,5-tetramethyl-1,3,2-dioxaborolan-2-yl)oxazole (128 mg, 615 μmol), $Cs_2CO_3$ (546 mg, 1.68 mmol), Pd(dppf)Cl$_2$ (40.9 mg, 55.9 μmol) in $H_2O$ (0.2 m L) and 1,4-dioxane (1 mL) was degassed and purged with $N_2$ three times. The mixture was stirred at 100° C. for 16 hr under $N_2$ atmosphere. The reaction mixture was poured into $H_2O$ (50 mL) and extracted with EtOAc (50 mL×3). The combined organic layers were dried over anhydrous $Na_2SO_4$, filtered, and concentrated under reduced pressure. After purified by prep-HPLC (column: Waters xbridge BEH C18 150×25 mm×5 μm; mobile phase: [water (NH$_4$HCO$_3$)-ACN]; gradient: 33%-63% B over 10 min), 4-((1-(4-(2-(2-aminopyridin-3-yl)-5-(4-methyloxazol-5-yl)-3H-imidazo[4,5-b]pyridin-3-yl)benzyl)piperidin-4-yl)amino)pyrimidine-2-carbonitrile (Example 554, 66.8 mg, yield: 19%) was obtained as a light-yellow lyophilized powder. MS: m/z=584.2 [M+H]$^+$. $^1$H NMR (400 MHz, Dimethylsulfoxide-d$_6$) δ 8.38 (s, 1H), 8.29 (d, J=8.4 Hz, 1H), 8.11-8.01 (m, 3H), 7.71 (d, J=8.4 Hz, 1H), 7.50-7.47 (m, 2H), 7.46-7.43 (m, 2H), 7.27-7.24 (m, 1H), 7.10 (s, 2H), 6.68 (d, J=6.0 Hz, 1H), 6.41 (dd, J=7.6, 4.8 Hz, 1H), 3.90-3.73 (m, 1H), 3.59 (s, 2H), 2.80 (d, J=10.8 Hz, 2H), 2.35 (s, 3H), 2.17-2.10 (m, 2H), 1.93-1.85 (m, 2H), 1.54-1.46 (m, 2H).

A mixture of Example 405 (300 mg, 559 μmol), (1-cyclopropyl-1H-pyrazol-4-yl)boronic acid (93.4 mg, 615 μmol), $Cs_2CO_3$ (546 mg, 1.68 mmol), Pd(dppf)Cl$_2$ (40.9 mg, 55.9 μmol) in $H_2O$ (0.2 mL) and 1,4-dioxane (1 mL) was degassed and purged with $N_2$ three times. The mixture was stirred at 100° C. for 16 hr under $N_2$ atmosphere. The reaction mixture was poured into $H_2O$ (50 mL) and extracted with EtOAc (50 mL×3). The combined organic layers were dried over anhydrous $Na_2SO_4$, filtered, and concentrated under reduced pressure. After purified by prep-HPLC (column: Waters xbridge BEH C18 150×25 mm×5 μm; mobile phase: [water (NH$_4$HCO$_3$)-ACN]; gradient: 31%-61% B over 10 min), 4-((1-(4-(2-(2-aminopyridin-3-yl)-5-(1-cyclopropyl-1H-pyrazol-4-yl)-3H-imidazo[4,5-b]pyridin-3-yl)benzyl)piperidin-4-yl)amino)pyrimidine-2-carbonitrile (Example 555, 77.6 mg, yield: 22%) was obtained as a light-yellow lyophilized powder. MS: m/z=609.3 [M+H]$^+$. $^1$H NMR (400 MHz, Dimethylsulfoxide-d$_6$) δ 8.25 (s, 1H), 8.15 (d, J=8.4 Hz, 1H), 8.11-8.03 (m, 2H), 7.98 (dd, J=4.8, 1.6 Hz, 1H), 7.89 (s, 1H), 7.68 (d, J=8.4 Hz, 1H), 7.49-7.45 (m, 2H), 7.42-7.38 (m, 2H), 7.10 (d, J=6.4 Hz, 1H), 7.00 (s, 2H), 6.68 (d, J=6.0 Hz, 1H), 6.36 (dd, J=7.6, 4.8 Hz, 1H), 3.88-3.71 (m, 2H), 3.59 (s, 2H), 2.83 (d, J=11.2 Hz, 2H), 2.20-2.11 (m, 2H), 1.94-1.85 (m, 2H), 1.55-1.45 (m, 2H), 1.09-1.04 (m, 2H), 1.00-0.93 (m, 2H).

Example 556: 2-(2-Aminopyridin-3-yl)-1-(4-((4-((2-cyanopyrimidin-4-yl)amino)piperidin-1-yl)methyl)phenyl)-1H-imidazo[4,5-b]pyrazine-5,6-dicarbonitrile Example 557: 2-(2-Aminopyridin-3-yl)-3-(4-((4-((2-cyanopyrimidin-4-yl)amino)piperidin-1-yl)methyl)phenyl)-5-(4-fluorophenyl)-3H-imidazo[4,5-b]pyridine-6-carbonitrile

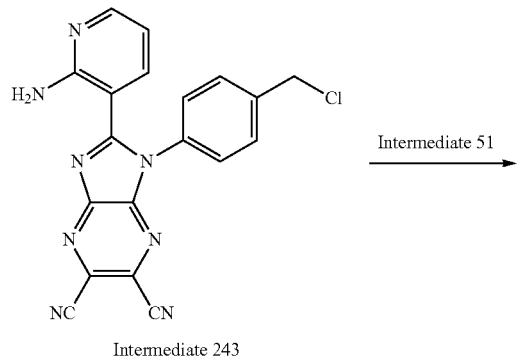

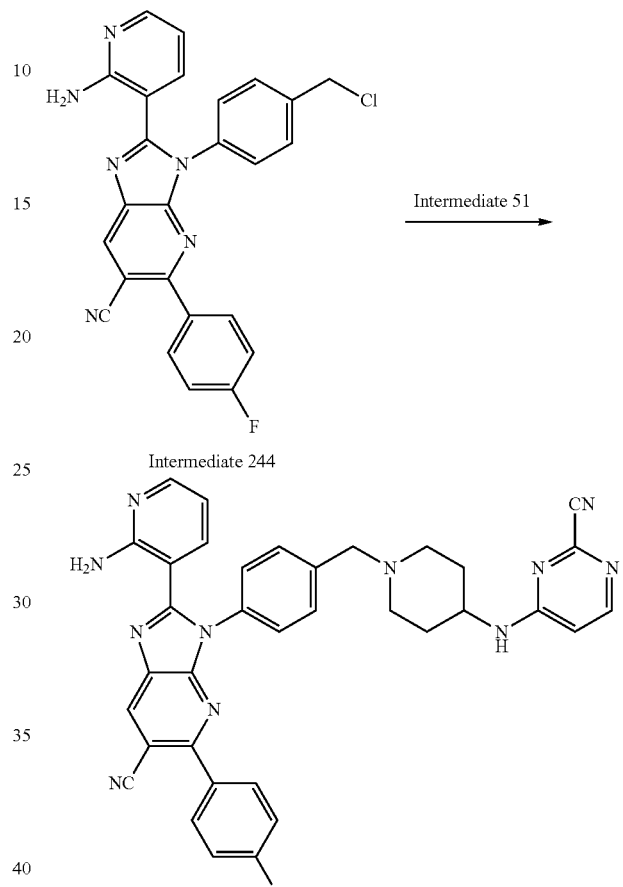

To a solution of Intermediate 243 (379 mg, 894 μmol, HCl salt) and Intermediate 51 (214 mg, 894 μmol, TFA) in DMF (5 mL) were added $K_2CO_3$ (371 mg, 2.68 mmol) and NaI (134 mg, 894 μmol). The mixture was degassed and purged with $N_2$ three times and stirred at 50° C. for 1 hr under $N_2$. The reaction mixture was diluted with $CH_2Cl_2$ (50 mL) at 25° C., washed with brine (30 mL×5), dried over $Na_2SO_4$, filtered and concentrated under reduced pressure. After purified by silica gel flash chromatography (MeOH in $CH_2Cl_2$=1% to 10%), 2-(2-aminopyridin-3-yl)-1-(4-((4-((2-cyanopyrimidin-4-yl)amino)piperidin-1-yl)methyl)phenyl)-1H-imidazo[4,5-b]pyrazine-5,6-dicarbonitrile (Example 556, 118 mg, yield: 23%) was obtained as a yellow solid. MS: m/z=554.2 [M+H]$^+$. $^1$H NMR (400 MHz, Dimethylsulfoxide-d$_6$) δ 8.13 (dd, J=4.4, 1.6 Hz, 1H), 8.09-8.05 (m, 2H), 7.56-7.51 (m, 2H), 7.48-7.44 (m, 2H), 7.29 (dd, J=8.0, 1.6 Hz, 1H), 7.20 (br s, 2H), 6.67 (d, J=6.0 Hz, 1H), 6.46 (dd, J=8.0, 4.8 Hz, 1H), 3.87-3.76 (m, 1H), 3.59 (s, 2H), 2.86-2.76 (m, 2H), 2.21-2.10 (m, 2H), 1.94-1.83 (m, 2H), 1.57-1.41 (m, 2H).

To a solution of Intermediate 244 (304 mg, 619 μmol, HCl salt) and Intermediate 51 (196 mg, 619 μmol, TFA salt) in DMF (5 mL) were added $K_2CO_3$ (257 mg, 1.86 mmol) and NaI (18.6 mg, 124 μmol). The mixture was stirred at 50° C. for 1 hr. The reaction mixture was quenched with $H_2O$ (10 mL) at 25° C., diluted with $CH_2Cl_2$ (10 mL), and extracted with $CH_2Cl_2$ (15 mL×2). The combined organic layers were washed with brine (30 mL×3), dried over $Na_2SO_4$, filtered, and concentrated under reduced pressure. After triturated with $CH_2Cl_2$ (20 mL) at 25° C. for 10 min, 2-(2-aminopyridin-3-yl)-3-(4-((4-((2-cyanopyrimidin-4-yl)amino)piperidin-1-yl)methyl)phenyl)-5-(4-fluorophenyl)-3H-imidazo[4,5-b]pyridine-6-carbonitrile (Example 557, 133 mg, yield: 34% for three steps) was obtained as a yellow solid. MS: m/z=622.2 [M+H]$^+$. $^1$H NMR (400 MHz, Dimethylsulfoxide-d$_6$) δ 8.90 (s, 1H), 8.13-7.99 (m, 3H), 7.83 (dd, J=8.4, 5.2 Hz, 2H), 7.48-7.42 (m, 4H), 7.38-7.36 (m, 2H), 7.19 (dd, J=7.6, 1.2 Hz, 1H), 6.94 (br s, 2H), 6.69 (d, J=6.0 Hz, 1H), 6.40 (dd, J=7.6, 4.8 Hz, 1H), 3.90-3.70 (m, 1H), 3.56 (s, 2H), 2.84-2.76 (m, 2H), 2.19-2.06 (m, 2H), 1.92-1.77 (m, 2H), 1.56-1.41 (m, 2H). $^{19}$F NMR (400 MHz, Dimethylsulfoxide-d$_6$) δ −111.61.

Example 558: 4-((1-(4-(2-(2-Aminopyridin-3-yl)-5-(2-fluoropyridin-3-yl)-3H-imidazo[4,5-b]pyridin-3-yl)benzyl)piperidin-4-yl)amino)pyrimidine-2-carbonitrile

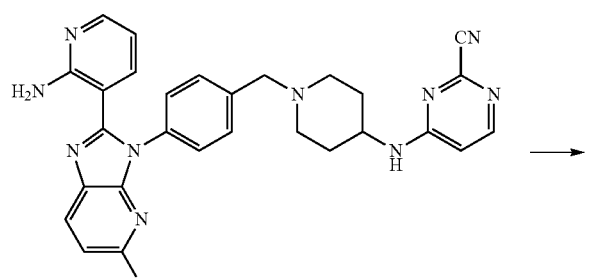

Example 405

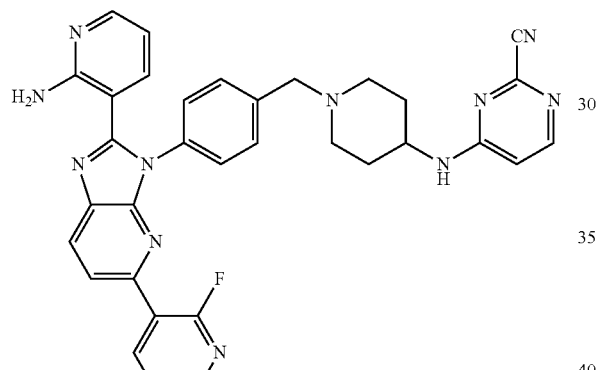

Exampel 558

A mixture of Example 405 (200 mg, 372 μmol), (2-fluoropyridin-3-yl)boronic acid (78.7 mg, 559 μmol), Cs₂CO₃ (364 mg, 1.12 mmol), Pd(dppf)Cl₂ (27.2 mg, 37.2 μmol) in H₂O (0 mL) and 1,4-dioxane (4 mL) was degassed and purged with N₂ three times. The mixture was stirred at 100° C. for 16 hr under N₂ atmosphere. The reaction mixture was poured into H₂O (15 mL) and extracted with EtOAc (15 mL×3). The combined organic layers were dried over anhydrous Na₂SO₄, filtered, and concentrated under reduced pressure. After purified by silica gel flash chromatography (Eluent of 0%~7% MeOH in CH₂Cl₂), 4-((1-(4-(2-(2-aminopyridin-3-yl)-5-(2-fluoropyridin-3-yl)-3H-imidazo[4,5-b]pyridin-3-yl)benzyl)piperidin-4-yl)amino)pyrimidine-2-carbonitrile (Example 558, 52.9 mg, yield: 24%) was obtained as a light brown solid. MS: m/z=598.1 [M+H]⁺. ¹H NMR (400 MHz, Dimethylsulfoxide-d₆) δ 8.43-8.24 (m, 3H), 8.16-7.94 (m, 3H), 7.88 (dd, J=8.0, 4.4 Hz, 1H), 7.53-7.40 (m, 5H), 7.17 (dd, J=7.6, 1.6 Hz, 1H), 6.99 (s, 2H), 6.73-6.61 (m, 1H), 6.39 (dd, J=7.6, 4.8 Hz, 1H), 3.90-3.75 (m, 1H), 3.58 (s, 2H), 2.89-2.77 (m, 2H), 2.22-2.09 (m, 2H), 1.97-1.79 (m, 2H), 1.56-1.34 (m, 2H). ¹⁹F NMR (400 MHz, Dimethylsulfoxide-d₆) δ −70.367.

Example 559: 4-((1-(4-(2-(2-Aminopyridin-3-yl)-5-(1-methyl-1H-1,2,4-triazol-3-yl)-3H-imidazo[4,5-b]pyridin-3-yl)benzyl)piperidin-4-yl)amino)pyrimidine-2-carbonitrile

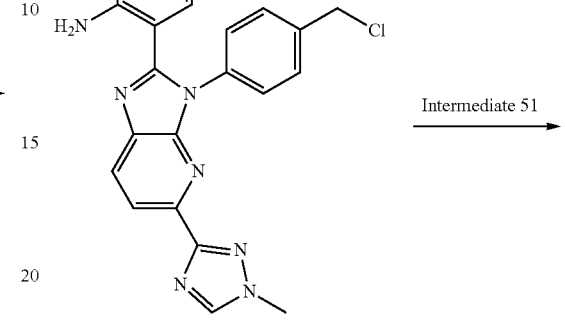

Intermediate 247

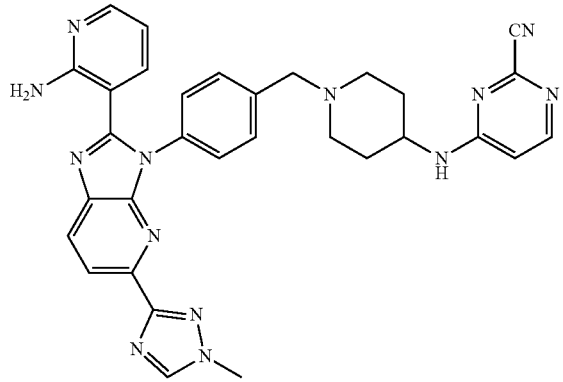

Example 559

To a solution of Intermediate 247 (156 mg, 374 μmol) and Intermediate 51 (119 mg, 374 gmol, TFA salt) in DMF (5 mL) were added K₂CO₃ (259 mg, 1.87 mmol) and NaI (5.61 mg, 37.4 μmol). The mixture was stirred at 50° C. for 1 hr. The reaction mixture was quenched with H₂O (50 mL) at 25° C. and extracted with CH₂Cl₂ (50 mL×2). The combined organic layers were washed with brine (50 mL×3), dried over Na₂SO₄, filtered, and concentrated under reduced pressure. After purified by silica gel flash chromatography (Eluent of 1%~ 8% MeOH in CH₂Cl₂), 4-((1-(4-(2-(2-aminopyridin-3-yl)-5-(1-methyl-1H-1,2,4-triazol-3-yl)-3H-imidazo[4,5-b]pyridin-3-yl)benzyl)piperidin-4-yl)amino)pyrimidine-2-carbonitrile (Example 559, 82.9 mg, yield: 37% for two steps) was obtained as a brown solid. MS: m/z=584.2 [M+H]⁺. ¹H NMR (400 MHz, Dimethylsulfoxide-d₆) δ 8.52 (s, 1H), 8.26 (d, J=8.4 Hz, 1H), 8.13-8.03 (m, 3H), 7.98 (dd, J=4.8, 1.6 Hz, 1H), 7.51-7.41 (m, 4H), 7.19-7.11 (m, 1H), 6.97 (s, 2H), 6.68 (d, J=5.2 Hz, 1H), 6.40-6.32 (m, 1H), 3.92 (s, 3H), 3.88-3.75 (m, 1H), 3.59 (s, 2H), 2.91-2.80 (m, 2H), 2.22-2.12 (m, 2H), 1.93-1.83 (m, 2H), 1.55-1.46 (m, 2H).

Example 560: 4-((1-(4-(2-(2-Aminopyridin-3-yl)-5-(5-ethoxypyridin-2-yl)-3H-imidazo[4,5-b]pyridin-3-yl)benzyl)piperidin-4-yl)amino)pyrimidine-2-carbonitrile

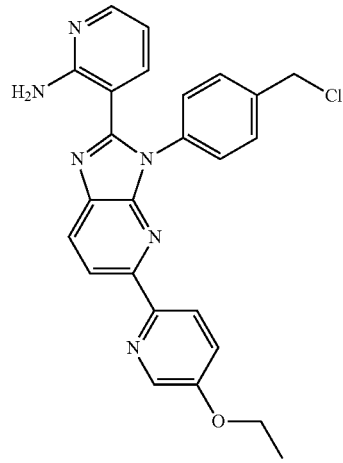

Intermediate 239

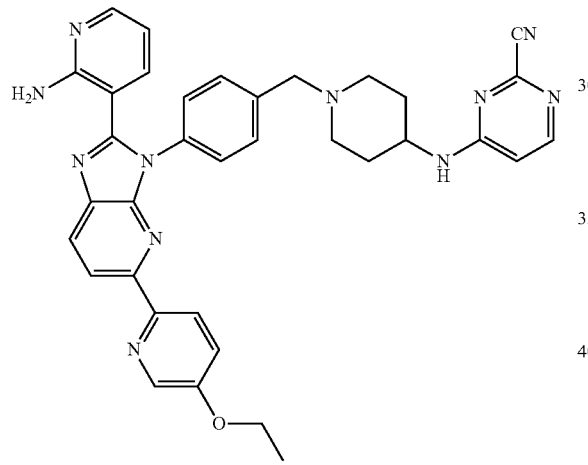

Example 560

To a solution of Intermediate 239 (225 mg, 456 μmol, HCl salt) and Intermediate 51 (145 mg, 456 μmol, TFA) in DMF (4 mL) were added $K_2CO_3$ (315 mg, 2.28 mmol) and NaI (6.84 mg, 45.6 μmol). The mixture was stirred at 50° C. for 1 hr. The reaction mixture was quenched with $H_2O$ (5 mL) at 25° C. and extracted with $CH_2Cl_2$ (15 mL×2). The combined organic layers were washed with brine (50 mL×3), dried over $Na_2SO_4$, filtered, and concentrated under reduced pressure. After purified by silica gel flash chromatography (Eluent of 1%-6% MeOH in $CH_2Cl_2$), 4-((1-(4-(2-(2-aminopyridin-3-yl)-5-(5-ethoxypyridin-2-yl)-3H-imidazo[4,5-b]pyridin-3-yl)benzyl)piperidin-4-yl)amino)pyrimidine-2-carbonitrile (Example 560, 176 mg, yield: 61% for two steps) was obtained as a yellow solid. MS: m/z=624.3 [M+H]+. 1H NMR (400 MHz, Dimethylsulfoxide-$d_6$) δ 8.39-8.32 (m, 2H), 8.26 (d, J=8.4 Hz, 1H), 8.15-8.03 (m, 3H), 8.00 (dd, J=5.2, 2.0 Hz, 1H), 7.52-7.43 (m, 5H), 7.16 (dd, J=7.6, 1.6 Hz, 1H), 7.02 (br s, 2H), 6.68 (d, J=6.0 Hz, 1H), 6.38 (dd, J=7.6, 4.8 Hz, 1H), 4.15 (q, J=6.8 Hz, 2H), 3.90-3.75 (m, 1H), 3.60 (s, 2H), 2.90-2.80 (m, 2H), 2.22-2.12 (m, 2H), 1.97-1.83 (m, 2H), 1.57-1.45 (m, 2H), 1.36 (t, J=7.2 Hz, 3H).

Example 561: 4-((1-(4-(2-(2-Aminopyridin-3-yl)-5-(2-fluoropyridin-4-yl)-3H-imidazo[4,5-b]pyridin-3-yl)benzyl)piperidin-4-yl)amino)pyrimidine-2-carbonitrile

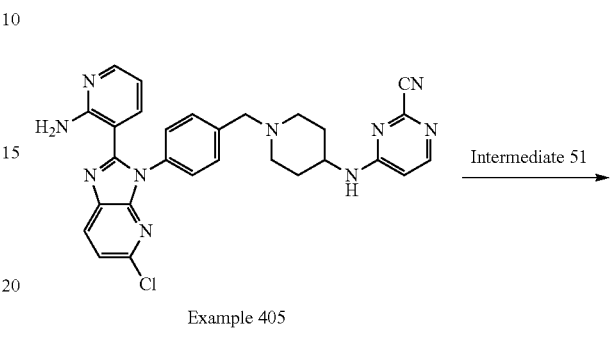

Example 405

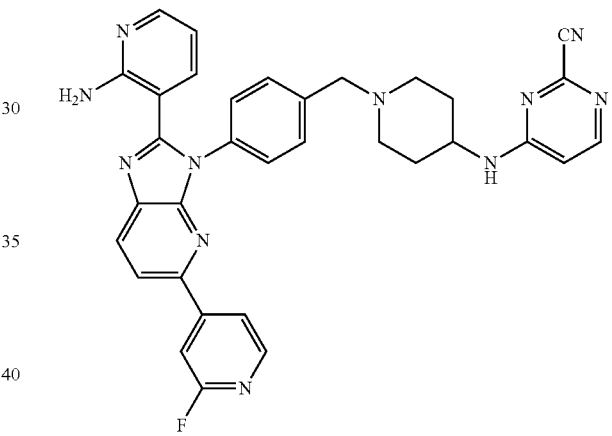

Example 561

To a mixture of Example 405 (300 mg, 559 μmol) and (2-fluoropyridin-4-yl)boronic acid (86.6 mg, 615 μmol) in 1,4-dioxane (2 mL) and $H_2O$ (0.5 mL) were added $Cs_2CO_3$ (546 mg, 1.68 mmol) and Pd(dppf)$Cl_2$ (40.9 mg, 55.9 μmol). The mixture was stirred at 100° C. for 2 hr under $N_2$. The mixture was diluted with $H_2O$ (50 mL) and extracted with EtOAc (100 mL×2). The combined organic layers were washed with brine (100 mL), dried over anhydrous $Na_2SO_4$, filtered and concentrated. After purified by prep-HPLC (column: Phenomenex C18 80×30 mm×5 μm; mobile phase: [water ($NH_3H_2O+NH_4HCO_3$)-ACN]; gradient: 47%-77% B over 7 min), 4-((1-(4-(2-(2-aminopyridin-3-yl)-5-(2-fluoropyridin-4-yl)-3H-imidazo[4,5-b]pyridin-3-yl)benzyl)piperidin-4-yl)amino)pyrimidine-2-carbonitrile (Example 561, 127.9 mg, yield: 38%) was obtained as a yellow solid. MS: m/z=598.3 [M+H]+. 1H NMR (400 MHz, Dimethylsulfoxide-$d_6$) δ 8.44-8.28 (m, 2H), 8.26-8.16 (m, 1H), 8.12-7.93 (m, 4H), 7.75 (s, 1H), 7.52-7.45 (m, 4H) 7.24-7.13 (m, 1H), 7.04 (br s, 2H), 6.72-6.60 (m, 1H), 6.45-6.33 (m, 1H), 3.88-3.75 (m, 1H), 3.60 (s, 2H), 2.89-2.77 (m, 2H), 2.26-2.08 (m, 2H), 1.96-1.81 (m, 2H), 1.59-1.43 (m, 2H). 19F NMR (400 MHz, Dimethylsulfoxide-$d_6$) δ −68.690.

Example 562: 4-((1-(4-(2-(3-Aminopyrazin-2-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile

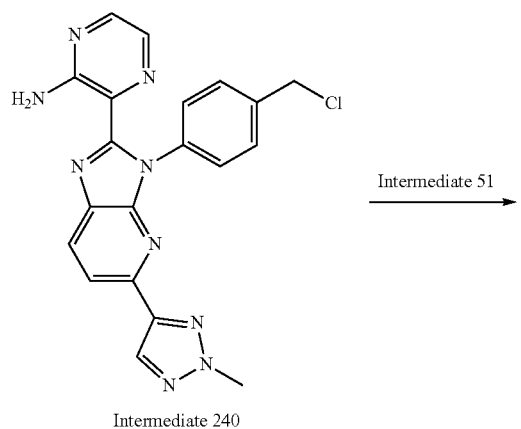

Example 563: 4-((1-(4-(2-(2-Aminopyridin-3-yl)-5-(3-methoxypyridin-2-yl)-3H-imidazo[4,5-b]pyridin-3-yl)benzyl)piperidin-4-yl)amino)pyrimidine-2-carbonitrile

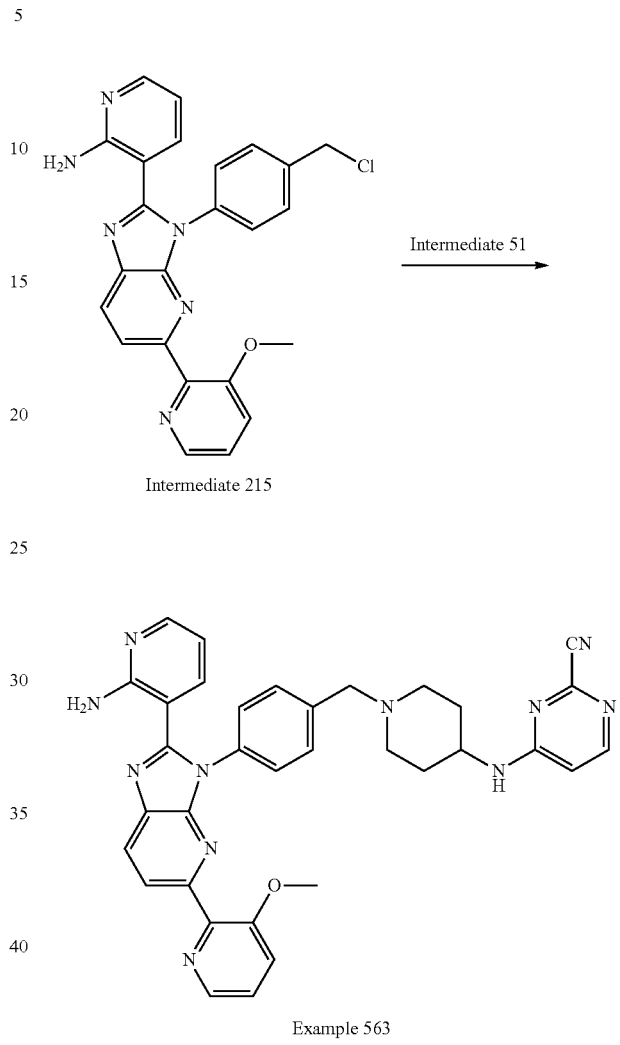

To a solution of Intermediate 240 (70 mg, 154 μmol, HCl salt) and Intermediate 51 (48.9 mg, 154 μmol, TFA salt) in DMF (2 mL) were added K$_2$CO$_3$ (106 mg, 770 μmol) and NaI (4.62 mg, 30.8 μmol). The mixture was stirred at 50° C. for 1 hr. The reaction mixture was quenched with H$_2$O (5 mL) at 25° C., diluted with CH$_2$Cl$_2$ (10 mL), and extracted with CH$_2$Cl$_2$ (15 mL×2). The combined organic layers were washed with brine (50 mL×3), dried over Na$_2$SO$_4$, filtered, and concentrated under reduced pressure. After purified by silica gel flash chromatography (Eluent of 1%~6% MeOH in CH$_2$Cl$_2$), 4-((1-(4-(2-(3-aminopyrazin-2-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile (Example 562, 43.2 mg, yield: 48% for three steps) was obtained as a yellow solid. MS: m/z=585.2 [M+H]$^+$. $^1$H NMR (400 MHz, Dimethylsulfoxide-d$_6$) δ 8.35 (d, J=8.0 Hz, 1H), 8.13-7.93 (m, 5H), 7.76 (br s, 2H), 7.48 (d, J=2.4 Hz, 1H), 7.44-7.40 (m, 2H), 7.38-7.33 (m, 2H), 6.68 (d, J=5.2 Hz, 1H), 4.21 (s, 3H), 3.90-3.76 (m, 1H), 3.60 (s, 2H), 2.93-2.82 (m, 2H), 2.25-2.12 (m, 2H), 1.98-1.84 (m, 2H), 1.59-1.43 (m, 2H).

To a solution of Intermediate 215 (197 mg, 411 μmol, HCl salt) and Intermediate 51 (130 mg, 411 μmol, TFA salt) in DMF (4 mL) were added K$_2$CO$_3$ (284 mg, 2.05 mmol) and NaI (6.16 mg, 41.1 μmol). The mixture was stirred at 25° C. for 3 hr. The reaction mixture was quenched with H$_2$O (5 mL) at 25° C. and extracted with CH$_2$Cl$_2$ (15 mL×2). The combined organic layers were washed with brine (50 mL×3), dried over Na$_2$SO$_4$, filtered, and concentrated under reduced pressure. After purified by prep-HPLC (column: Phenomenex C18 150×25 mm×10 μm; mobile phase: [water (NH$_4$HCO$_3$)-ACN]; B %: 56%, isocratic elution mode), 4-((1-(4-(2-(2-aminopyridin-3-yl)-5-(3-methoxypyridin-2-yl)-3H-imidazo[4,5-b]pyridin-3-yl)benzyl)piperidin-4-yl)amino)pyrimidine-2-carbonitrile (Example 563, 83.2 mg, yield: 33% for two steps) was obtained as a light yellow lyophilized powder. MS: m/z=610.2 [M+H]$^+$. $^1$H NMR (400 MHz, Dimethylsulfoxide-d$_6$) δ 8.26-8.20 (m, 2H), 8.12-8.02 (m, 2H), 7.99 (dd, J=4.8, 2.0 Hz, 1H), 7.69 (d, J=8.0 Hz, 1H), 7.60-7.56 (m, 1H), 7.45-7.39 (m, 5H), 7.16 (dd, J=7.6, 1.6 Hz, 1H), 7.00 (br s, 2H), 6.66 (d, J=6.0 Hz, 1H), 6.38 (dd, J=7.6, 4.8 Hz, 1H), 3.88-3.78 (m, 1H), 3.76 (s, 3H), 3.55 (s, 2H), 2.84-2.75 (m, 2H), 2.17-2.07 (m, 2H), 1.89-1.80 (m, 2H), 1.51-1.40 (m, 2H).

1699

Example 564: 4-((1-(4-(2-(2-Aminopyridin-3-yl)-5-(1-methyl-1H-1,2,3-triazol-5-yl)-3H-imidazo[4,5-b]pyridin-3-yl)benzyl)piperidin-4-yl)amino)pyrimidine-2-carbonitrile

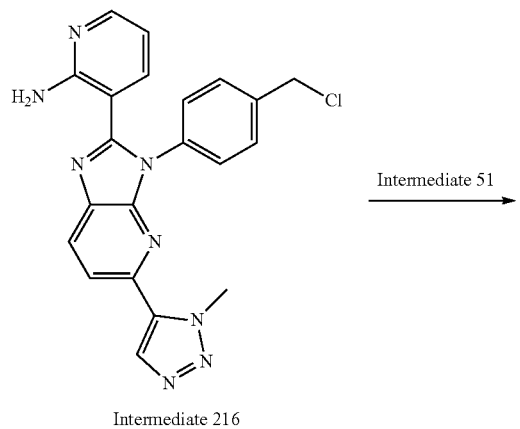

Intermediate 216

Example 564

1700

Example 565: 2-(2-Aminopyridin-3-yl)-3-(4-((4-((2-cyanopyrimidin-4-yl)amino)piperidin-1-yl)methyl)phenyl)-6-methyl-3H-imidazo[4,5-b]pyridine-5-carbonitrile

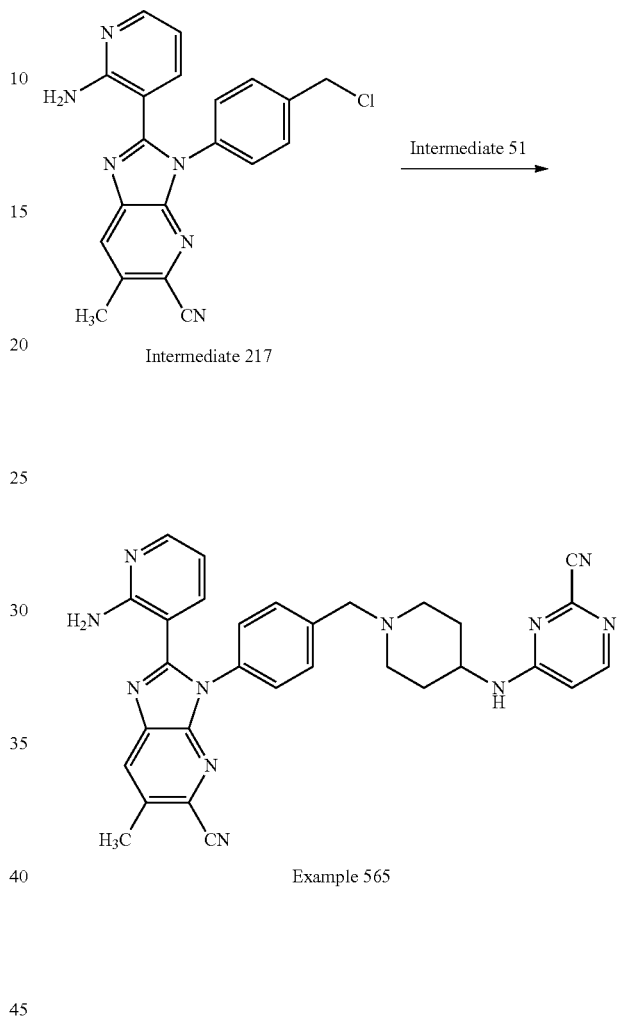

Intermediate 217

Example 565

To a solution of Intermediate 216 (155 mg, 372 μmol, HCl salt) and Intermediate 51 (118 mg, 372 μmol, TFA) in DMF (2 mL) were added $K_2CO_3$ (257 mg, 1.86 mmol) and NaI (16.7 mg, 112 μmol). The mixture was stirred at 25° C. for 16 hr. The reaction mixture was poured into $H_2O$ (15 mL) and extracted with EtOAc (15 mL×3). The combined organic layers were dried over anhydrous $Na_2SO_4$, filtered and concentrated under reduced pressure. After purified by silica gel flash chromatography (Eluent of 0%~8% MeOH in $CH_2Cl_2$), 4-((1-(4-(2-(2-aminopyridin-3-yl)-5-(1-methyl-1H-1,2,3-triazol-5-yl)-3H-imidazo[4,5-b]pyridin-3-yl)benzyl)piperidin-4-yl)amino)pyrimidine-2-carbonitrile (Example 564, 44.3 mg, yield: 20% for three steps) was obtained as an off white solid. MS: m/z=584.2 $[M+H]^+$. $^1H$ NMR (400 MHz, Dimethylsulfoxide-$d_6$) δ 8.40-8.31 (m, 2H), 8.14-7.97 (m, 3H), 7.89 (d, J=8.4 Hz, 1H), 7.55-7.40 (m, 4H), 7.24 (dd, J=7.6, 1.6 Hz, 1H), 7.09 (s, 2H), 6.67 (d, J=5.6 Hz, 1H), 6.41 (dd, J=8.0, 4.8 Hz, 1H), 4.16 (s, 3H), 3.89-3.72 (m, 1H), 3.58 (s, 2H), 2.85-2.73 (m, 2H), 2.20-2.08 (m, 2H), 1.97-1.81 (m, 2H), 1.57-1.41 (m, 2H).

To a solution of Intermediate 217 (28 mg, 68 μmol) and Intermediate 51 (21.6 mg, 68 μmol) in DMF (3 mL) were added NaI (5.1 mg, 34 μmol) and $K_2CO_3$ (38 mg, 2.7 μmol). The mixture was stirred at 25° C. for 16 hr. The reaction mixture was diluted with $H_2O$ (10 mL) and extracted with EtOAc (10 mL×3). The combined organic layers were washed with brine (30 mL), dried over $Na_2SO_4$, filtered, and concentrated under reduced pressure. After purified by prep-TLC ($CH_2Cl_2$:MeOH=10:1), 2-(2-aminopyridin-3-yl)-3-(4-((4-((2-cyanopyrimidin-4-yl)amino)piperidin-1-yl)methyl)phenyl)-6-methyl-3H-imidazo[4,5-b]pyridine-5-carbonitrile (Example 565, 10.2 mg, yield: 28% for three steps) as a yellow solid. MS: m/z=542.1 $[M+H]^+$. $^1H$ NMR (400 MHz, Methanol-$d_4$) δ 8.19 (s, 1H), 8.12-8.05 (m, 1H), 8.02 (dd, J=5.2, 2.0 Hz, 1H), 7.70 (d, J=8.0 Hz, 2H), 7.55 (d, J=8.0 Hz, 2H), 7.36 (dd, J=7.6, 1.6 Hz, 1H), 6.66 (d, J=6.0 Hz, 1H), 6.48 (dd, J=8.0, 5.2 Hz, 1H), 4.32-4.15 (m, 3H), 3.50-3.38 (m, 2H), 3.17-3.00 (m, 2H), 2.70 (s, 3H), 2.27-2.20 (m, 2H), 1.87-1.77 (m, 2H).

1701

Example 566: 4-((1-(4-(2-(2-Aminopyridin-3-yl)-5-(5-methyl-1,3,4-oxadiazol-2-yl)-3H-imidazo[4,5-b]pyridin-3-yl)benzyl)piperidin-4-yl)amino)pyrimidine-2-carbonitrile

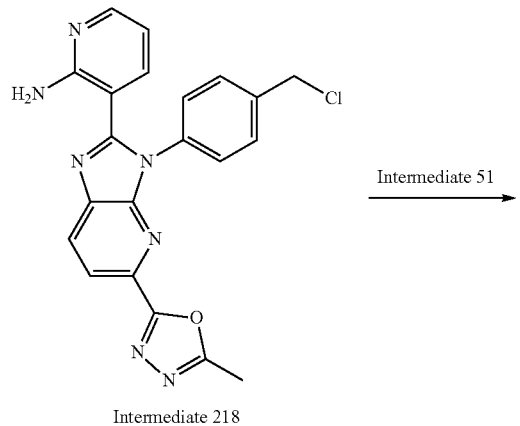

Intermediate 218

→ Intermediate 51

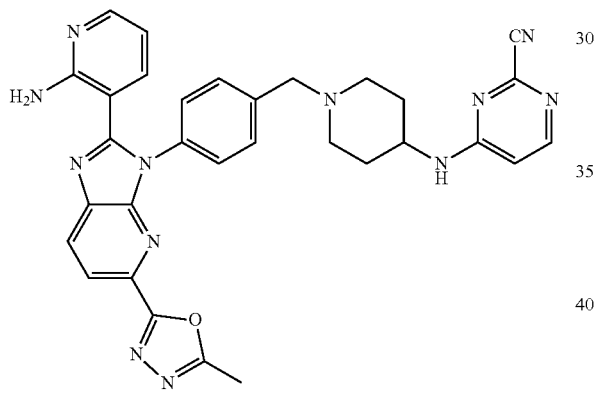

Example 566

To a solution of Intermediate 218 (100 mg, 220 μmol, HCl salt) and Intermediate 51 (105 mg, 330 μmol, TFA salt) in DMF (2 mL) were added NaI (16.5 mg, 110 μmol) and K₂CO₃ (91 mg, 660 μmol). The mixture was stirred at 50° C. for 1 hr. The reaction mixture was diluted with H₂O (30 mL) and extracted with EtOAc (20 mL×3). The combined organic layers were washed with brine (30 mL), dried over Na₂SO₄, filtered and concentrated under reduced pressure. After purified by prep-HPLC (column: Phenomenex luna C18 150×25 mm×10 μm; mobile phase: [water (FA)-ACN]; gradient: 1%-30% B over 8 min), 4-((1-(4-(2-(2-aminopyridin-3-yl)-5-(5-methyl-1,3,4-oxadiazol-2-yl)-3H-imidazo[4,5-b]pyridin-3-yl)benzyl)piperidin-4-yl)amino)pyrimidine-2-carbonitrile (Example 566, 7.3 mg, yield: 6%) was obtained as an off white solid. MS: m/z=585.2 [M+H]⁺. ¹H NMR (400 MHz, Chloroform-d) δ 8.35-8.27 (m, 1H), 8.27-8.20 (m, 2H), 8.19-8.10 (m, 1H), 8.06 (dd, J=4.8, 1.6 Hz, 1H), 7.54 (d, J=8.0 Hz, 2H), 7.41 (d, J=8.0 Hz, 2H), 7.08 (dd, J=7.6, 1.2 Hz, 1H), 6.95-6.83 (m, 2H), 6.50-6.43 (m, 1H), 6.36 (dd, J=7.6, 4.8 Hz, 1H), 5.47-5.24 (m, 1H), 3.74 (s, 2H), 3.11-2.94 (m, 2H), 2.63 (s, 3H), 2.35-2.28 (m, 2H), 2.09 (d, J=10.4 Hz, 2H), 1.75-1.62 (m, 2H).

1702

Example 567: 4-((1-(4-(2-(2-Aminopyridin-3-yl)-5-(1-methyl-1H-1,2,4-triazol-5-yl)-3H-imidazo[4,5-b]pyridin-3-yl)benzyl)piperidin-4-yl)amino)pyrimidine-2-carbonitrile

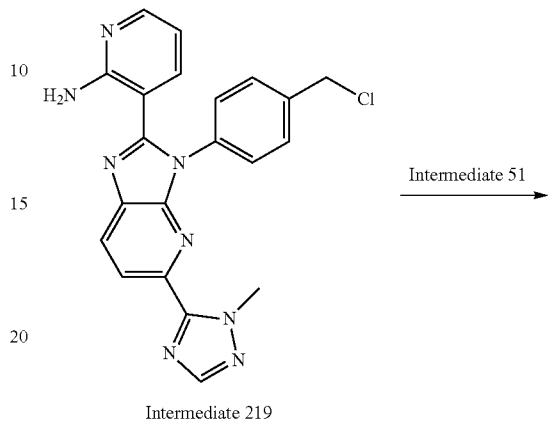

Intermediate 219

→ Intermediate 51

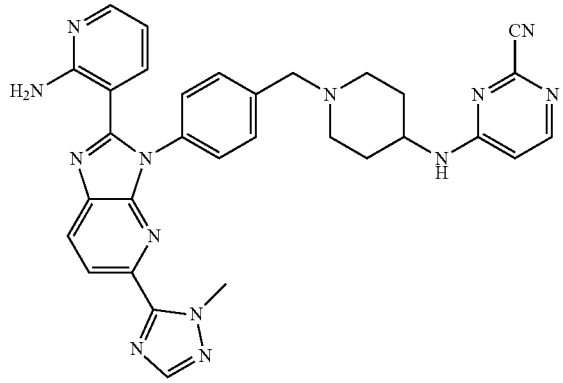

Example 567

To a solution of Intermediate 219 (180 mg, 432 μmol, HCl salt) and Intermediate 51 (140 mg, 432 μmol, TFA) in DMF (2 mL) were added K₂CO₃ (298 mg, 2.16 mmol) and NaI (19.4 mg, 130 μmol). The mixture was stirred at 25° C. for 16 hr. The reaction mixture was poured into H₂O (15 mL) and extracted with EtOAc (15 mL×3). The organic phase was dried over anhydrous Na₂SO₄, filtered, and concentrated under reduced pressure. After purified by silica gel flash chromatography (Eluent of 0%~8% MeOH in CH₂Cl₂), 4-((1-(4-(2-(2-aminopyridin-3-yl)-5-(1-methyl-1H-1,2,4-triazol-5-yl)-3H-imidazo[4,5-b]pyridin-3-yl)benzyl)piperidin-4-yl)amino)pyrimidine-2-carbonitrile (Example 567, 87.7 mg, yield: 35% for three steps) was obtained as a yellow solid. MS: m/z=584.2 [M+H]⁺. ¹H NMR (400 MHz, Dimethylsulfoxide-d₆) δ 8.37 (d, J=8.4 Hz, 1H), 8.16 (d, J=8.4 Hz, 1H), 8.11-7.98 (m, 4H), 7.51-7.40 (m, 4H), 7.26 (dd, J=7.6, 1.6 Hz, 1H), 7.09 (s, 2H), 6.67 (d, J=6.0 Hz, 1H), 6.42 (dd, J=7.6, 4.8 Hz, 1H), 4.08 (s, 3H), 3.88-3.72 (m, 1H), 3.58 (s, 2H), 2.85-2.73 (m, 2H), 2.19-2.09 (m, 2H), 1.93-1.82 (m, 2H), 1.53-1.42 (m, 2H).

Example 568: 4-((1-(4-(2-(2-Aminopyridin-3-yl)-5-(4-methyl-2H-1,2,3-triazol-2-yl)-3H-imidazo[4,5-b]pyridin-3-yl)benzyl)piperidin-4-yl)amino)pyrimidine-2-carbonitrile

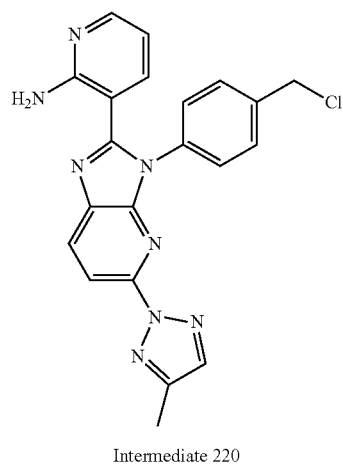

Intermediate 220

→ Intermediate 51

Example 568

To a solution of Intermediate 220 (170 mg, 375 μmol, HCl salt) and Intermediate 51 (119 mg, 375 μmol, TFA) in DMF (5 mL) were added $K_2CO_3$ (259 mg, 1.88 mmol) and NaI (5.62 mg, 37.5 μmol). The mixture was stirred at 50° C. for 1 hr. The reaction mixture was quenched with $H_2O$ (50 mL) at 25° C. and extracted with $CH_2Cl_2$ (50 mL×2). The combined organic layers were washed with brine (50 mL×3), dried over $Na_2SO_4$, filtered, and concentrated under reduced pressure. After purified by silica gel flash chromatography (Eluent of 1%~10% MeOH in $CH_2Cl_2$), 4-((1-(4-(2-(2-aminopyridin-3-yl)-5-(4-methyl-2H-1,2,3-triazol-2-yl)-3H-imidazo[4,5-b]pyridin-3-yl)benzyl)piperidin-4-yl)amino)pyrimidine-2-carbonitrile (Example 568, 105.2 mg, yield: 47% for two steps) was obtained as a pink solid. MS: m/z=584.2 [M+H]$^+$. $^1$H NMR (400 MHz, Dimethylsulfoxide-$d_6$) δ 8.40 (d, J=8.4 Hz, 1H), 8.12-7.96 (m, 4H), 7.90 (s, 1H), 7.52-7.43 (m, 4H), 7.15 (dd, J=7.6, 1.6 Hz, 1H), 6.95 (s, 2H), 6.68 (d, J=5.6 Hz, 1H), 6.41-6.35 (m, 1H), 3.94-3.68 (m, 1H), 3.59 (s, 2H), 2.87-2.79 (m, 2H), 2.36 (s, 3H), 2.22-2.13 (m, 2H), 1.93-1.85 (m, 2H), 1.59-1.48 (m, 2H).

Example 569: 4-((1-(4-(2-(2-Aminopyridin-3-yl)-5-(4-methyl-4H-1,2,4-triazol-3-yl)-3H-imidazo[4,5-b]pyridin-3-yl)benzyl)piperidin-4-yl)amino)pyrimidine-2-carbonitrile Intermediate 221

→ Intermediate 51

Example 569

To a solution of Intermediate 221 (160 mg, 384 μmol, HCl salt) and Intermediate 51 (122 mg, 384 μmol, TFA salt) in DMF (2 mL) were added $K_2CO_3$ (265 mg, 1.92 mmol) and NaI (17.3 mg, 115 μmol). The mixture was stirred at 25° C. for 16 hr. The reaction mixture was poured into $H_2O$ (15 mL) and extracted with EtOAc (15 mL×3). The combined organic phases were dried over anhydrous $Na_2SO_4$, filtered and concentrated under reduced pressure. After purified by silica gel flash chromatography (Eluent of 0%~6% MeOH in $CH_2Cl_2$), 4-((1-(4-(2-(2-aminopyridin-3-yl)-5-(4-methyl-4H-1,2,4-triazol-3-yl)-3H-imidazo[4,5-b]pyridin-3-yl)benzyl)piperidin-4-yl)amino)pyrimidine-2-carbonitrile (Example 569, 20.1 mg, yield: 9% for three steps) was obtained as a light brown solid. MS: m/z=584.2 [M+H]$^+$. $^1$H NMR (400 MHz, Dimethylsulfoxide-$d_6$) δ 8.53 (s, 1H), 8.36 (d, J=8.4 Hz, 1H), 8.17 (d, J=8.4 Hz, 1H), 8.12-7.99 (m, 3H), 7.49-7.45 (m, 4H), 7.25 (dd, J=8.0 Hz, 2.0 Hz, 1H), 7.08 (s, 2H), 6.67 (d, J=6.0 Hz, 1H), 6.41 (dd, J=7.6 Hz, 4.8 Hz, 1H), 3.85-3.81 (m, 1H), 3.80 (s, 3H), 3.58 (s, 2H), 2.83-2.75 (m, 2H), 2.20-2.08 (m, 2H), 1.95-1.83 (m, 2H), 1.54-1.43 (m, 2H).

Example 570: 4-((1-(4-(2-(2-Aminopyridin-3-yl)-5-(3-fluoropyridin-2-yl)-3H-imidazo[4,5-b]pyridin-3-yl)benzyl)piperidin-4-yl)amino)pyrimidine-2-carbonitrile

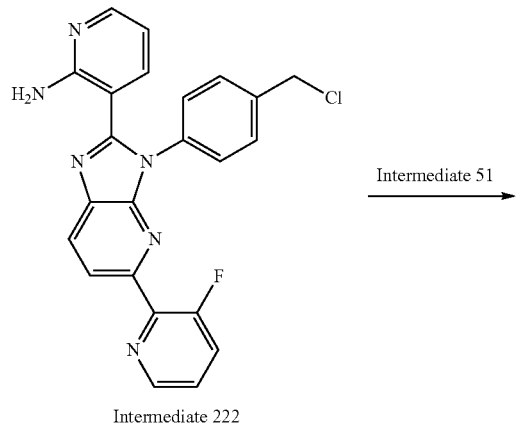

Intermediate 222

→ Intermediate 51

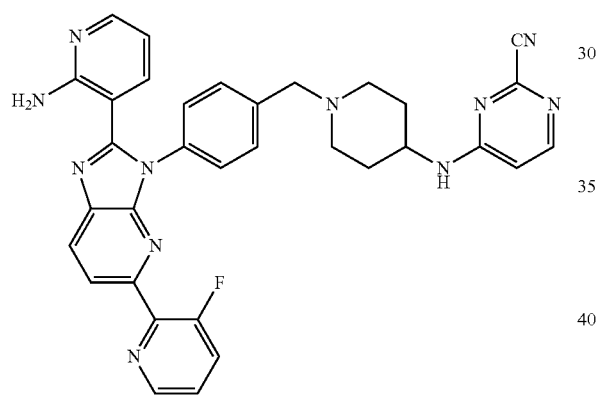

Example 570

To a mixture of Intermediate 222 (200 mg, 464 μmol) and Intermediate 51 (141 mg, 696 μmol) in DMF (3 mL) was added DIEA (179 mg, 1.39 mmol). The mixture was stirred at 80° C. for 1 hr. The mixture was diluted with $H_2O$ (20 mL) and extracted with EtOAc (20 mL×2). The combined organic layers were washed with brine (20 mL), dried over anhydrous $Na_2SO_4$, filtered and concentrated. After purified by prep-HPLC (column; C18 150×30 mm; mobile phase: [water ($NH_3H_2O+NH_4HCO_3$)-ACN]; gradient: 40%-70% B over 7 min), 4-((1-(4-(2-(2-aminopyridin-3-yl)-5-(3-fluoropyridin-2-yl)-3H-imidazo[4,5-b]pyridin-3-yl)benzyl)piperidin-4-yl)amino)pyrimidine-2-carbonitrile (Example 570, 30.7 mg, yield; 11%) was obtained as a yellow solid. MS: m/z=620.1 [M+Na]+. $^1$H NMR (400 MHz, Dimethylsulfoxide-$d_6$) δ 8.53 (d, J=4.8 Hz, 1H), 8.34 (d, J=8.0 Hz, 1H), 8.11-7.98 (m, 4H), 7.86-7.76 (m, 1H), 7.59-7.50 (m, 1H), 7.48-7.39 (m, 4H), 7.18 (d, J=7.6, 1H), 6.98 (br s, 2H), 6.72-6.64 (m, 1H), 6.39 (dd, J=7.6, 4.8 Hz, 1H), 3.86-3.77 (m, 1H), 3.56 (s, 2H), 2.87-2.75 (m, 2H), 2.21-2.09 (m, 2H), 1.94-1.79 (m, 2H), 1.56-1.41 (m, 2H). $^{19}$F NMR (400 MHz, Dimethylsulfoxide-$d_6$) δ −121.825.

Example 571: 4-((1-(4-(2-(2-Aminopyridin-3-yl)-5-(6-methylpyridin-2-yl)-3H-imidazo[4,5-b]pyridin-3-yl)benzyl)piperidin-4-yl)amino)pyrimidine-2-carbonitrile

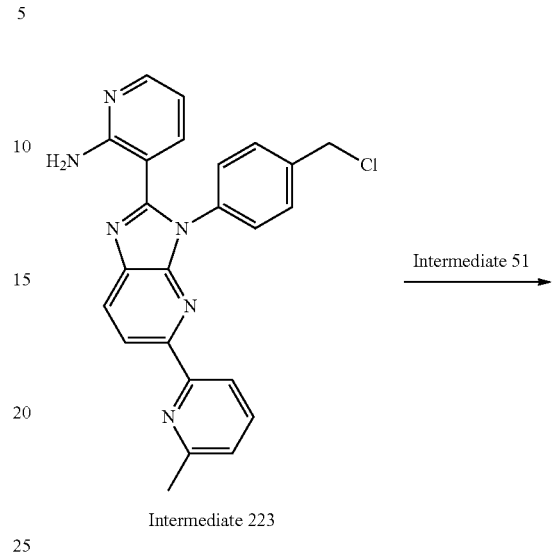

Intermediate 223

→ Intermediate 51

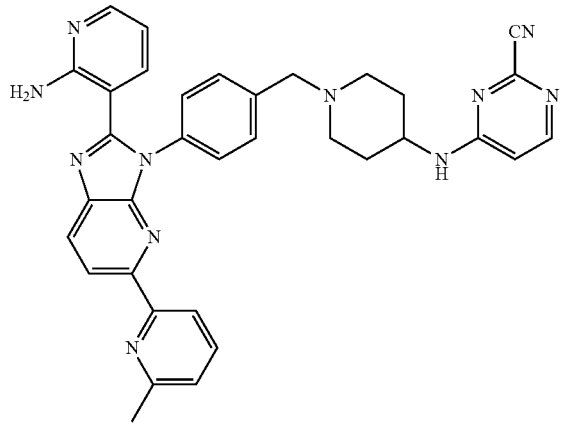

Example 571

To a mixture of Intermediate 223 (240 mg, 562 μmol) and Intermediate 51 (171 mg, 843 μmol) in DMF (2 mL) was added DIEA (218 mg, 1.69 mmol). The mixture was stirred at 80° C. for 1 hr. The mixture was diluted with $H_2O$ (20 mL) and extracted with EtOAc (20 mL×2). The combined organic layers were washed with brine (20 mL), dried over anhydrous $Na_2SO_4$, filtered and concentrated. After purified by prep-HPLC (column: C18 150×30 mm; mobile phase: [water ($NH_3H_2O+NH_4HCO_3$)-ACN]; gradient: 50%-80% B over 7 min), 4-((1-(4-(2-(2-aminopyridin-3-yl)-5-(6-methylpyridin-2-yl)-3H-imidazo[4,5-b]pyridin-3-yl)benzyl)piperidin-4-yl)amino)pyrimidine-2-carbonitrile (Example 571, 32 mg, yield: 9%) was obtained as a yellow solid. MS: m/z=616.1 [M+Na]$^+$. $^1$H NMR (400 MHz, Dimethylsulfoxide-$d_6$) δ 8.48 (d, J=8.4 Hz, 1H), 8.29 (d, J=8.4 Hz, 1H), 8.23-7.86 (m, 4H), 7.77 (t, J=8.0 Hz, 1H), 7.53-7.41 (m, 4H), 7.26 (d, J=7.6 Hz, 1H), 7.17 (dd, J=7.6, 1.6 Hz, 1H), 7.01 (br s, 2H), 6.67 (d, J=6.0 Hz, 1H), 6.39 (dd, J=7.6, 4.4 Hz, 1H), 3.90-3.75 (m, 1H), 3.60 (s, 2H), 2.92-2.78 (m, 2H), 2.57 (s, 3H), 2.24-2.11 (m, 2H), 1.95-1.76 (m, 2H), 1.60-1.40 (m, 2H).

Example 572: 4-((1-(4-(2-(2-Aminopyridin-3-yl)-5-(1-(difluoromethyl)-1H-1,2,4-triazol-3-yl)-3H-imidazo[4,5-b]pyridin-3-yl)benzyl)piperidin-4-yl)amino)pyrimidine-2-carbonitrile

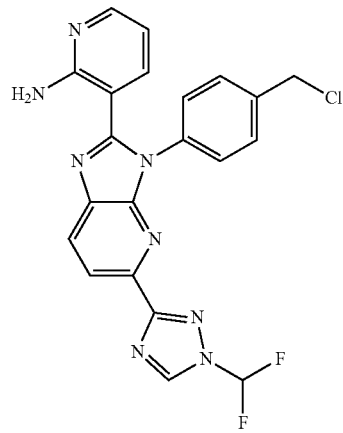

Intermediate 224

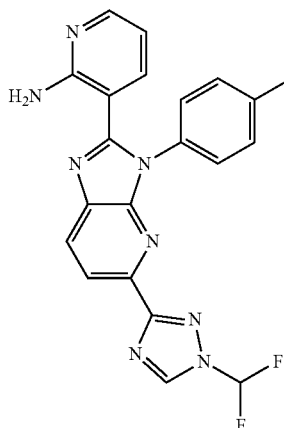

Example 572

To a solution of Intermediate 224 (52 mg, 115 μmol, HCl salt) and Intermediate 51 (36.4 mg, 115 μmol, TFA) in DMF (2 mL) were added $K_2CO_3$ (79.4 mg, 574 μmol) and NaI (1.72 mg, 11.5 μmol). The mixture was stirred at 50° C. for 1 hr. The reaction mixture was quenched with $H_2O$ (50 mL) at 25° C. and extracted with $CH_2Cl_2$ (50 mL×2). The combined organic layers were washed with brine (50 mL×3), dried over $Na_2SO_4$, filtered, and concentrated under reduced pressure. After purified by silica gel flash chromatography (Eluent of 1%~8% MeOH in $CH_2Cl_2$), 4-((1-(4-(2-(2-aminopyridin-3-yl)-5-(1-(difluoromethyl)-1H-1,2,4-triazol-3-yl)-3H-imidazo[4,5-b]pyridin-3-yl)benzyl)piperidin-4-yl)amino)pyrimidine-2-carbonitrile (Example 572, 26.1 mg, yield: 36% for two steps) was obtained as an off white solid. MS: m/z=620.1 [M+H]⁺. ¹H NMR (400 MHz, Dimethylsulfoxide-$d_6$) δ 9.18 (s, 1H), 8.34 (d, J=8.4 Hz, 1H), 8.19 (d, J=8.4 Hz, 1H), 8.11-7.84 (m, 4H), 7.51-7.41 (m, 4H), 7.19-7.12 (m, 1H), 6.99 (s, 2H), 6.68 (d, J=6.0 Hz, 1H), 6.40-6.35 (m, 1H), 3.88-3.77 (m, 1H), 3.59 (s, 2H), 2.89-2.81 (m, 2H), 2.23-2.13 (m, 2H), 1.95-1.84 (m, 2H), 1.54-1.43 (m, 2H). ¹⁹F NMR (400 MHz, Dimethylsulfoxide-$d_6$) δ −96.949.

Example 573: 4-((1-(4-(2-(4-Aminopyrimidin-5-yl)-5-(5-fluoropyridin-2-yl)-3H-imidazo[4,5-b]pyridin-3-yl)benzyl)piperidin-4-yl)amino)pyrimidine-2-carbonitrile

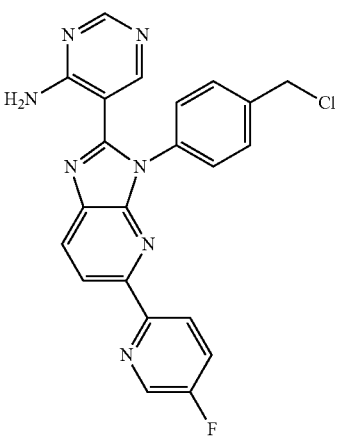

Intermediate 226

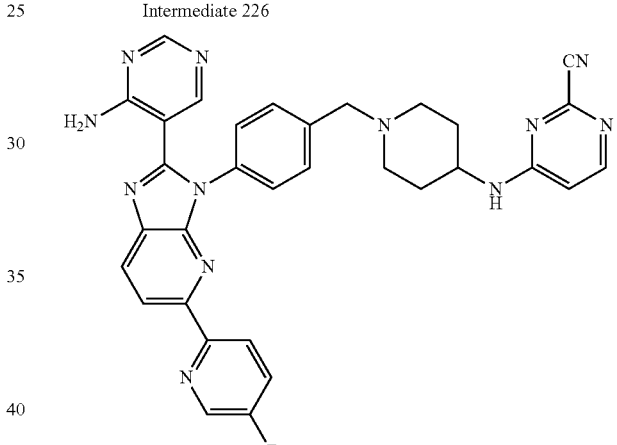

Example 573

To a solution of Intermediate 226 (509 mg, 1.09 mmol, HCl salt) and Intermediate 51 (345 mg, 1.09 mmol, TFA) in DMF (5 mL) were added $K_2CO_3$ (751 mg, 5.43 mmol) and NaI (16.3 mg, 109 μmol). The mixture was stirred at 50° C. for 1 hr. The reaction mixture was quenched with $H_2O$ (50 mL) at 25° C. and extracted with $CH_2Cl_2$ (50 mL×2). The combined organic layers were washed with brine (50 mL×3), dried over $Na_2SO_4$, filtered, and concentrated under reduced pressure. After purified by silica gel flash chromatography (Eluent of 1%~5% MeOH in $CH_2Cl_2$), 4-((1-(4-(2-(4-aminopyrimidin-5-yl)-5-(5-fluoropyridin-2-yl)-3H-imidazo[4,5-b]pyridin-3-yl)benzyl)piperidin-4-yl)amino)pyrimidine-2-carbonitrile (Example 573, 273.5 mg, yield: 40% for two steps) was obtained as a brown solid. MS: m/z=599.2 [M+H]⁺. ¹H NMR (400 MHz, Dimethylsulfoxide-$d_6$) δ 8.66 (d, J=2.0 Hz, 1H), 8.53-8.29 (m, 3H), 8.25-8.19 (m, 1H), 8.17-7.99 (m, 2H), 7.94 (s, 1H), 7.85-7.66 (m, 3H), 7.52 (s, 4H), 6.87-6.62 (m, 1H), 3.98-3.67 (m, 1H), 3.60 (s, 2H), 2.89-2.78 (m, 2H), 2.26-2.12 (m, 2H), 1.95-1.85 (m, 2H), 1.57-1.43 (m, 2H). ¹⁹F NMR (400 MHz, Dimethylsulfoxide-$d_6$) δ −127.659.

Example 574: 4-((1-(4-(2-(3-Aminopyrazin-2-yl)-5-(5-fluoropyridin-2-yl)-3H-imidazo[4,5-b]pyridin-3-yl)benzyl)piperidin-4-yl)amino)pyrimidine-2-carbonitrile

Example 575: 4-((1-(4-(5-(5-Fluoropyridin-2-yl)-2-(pyridin-3-yl)-3H-imidazo[4,5-b]pyridin-3-yl)benzyl)piperidin-4-yl)amino)pyrimidine-2-carbonitrile

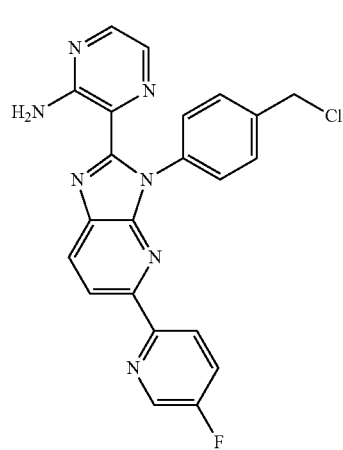

Intermediate 227

→ Intermediate 51 →

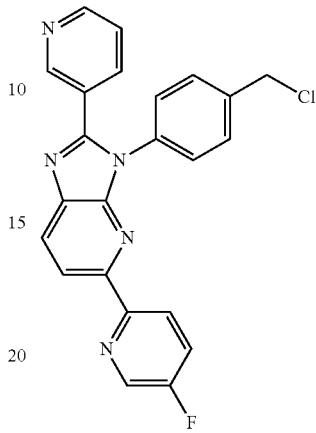

Intermediate 228

→ Intermediate 51 →

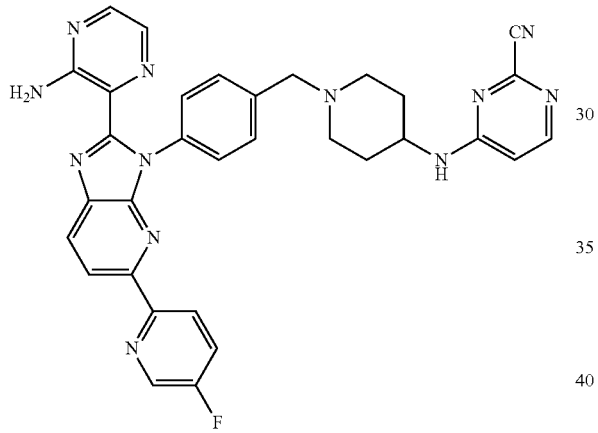

Example 574

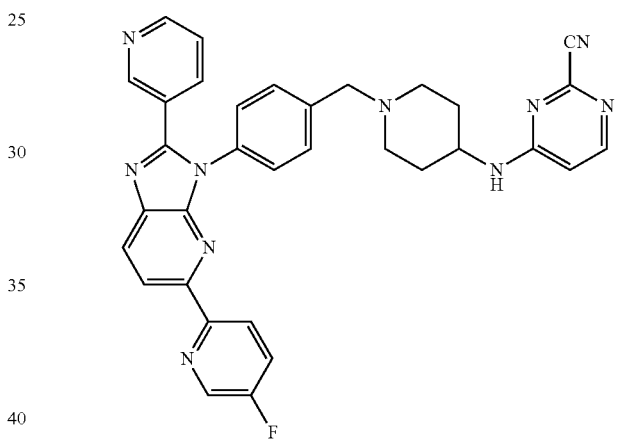

Example 575

To a solution of Intermediate 227 (238 mg, 508 μmol, HCl salt) and Intermediate 51 (161 mg, 508 μmol, TFA) in DMF (3 mL) were added NaI (38 mg, 254 μmol) and $K_2CO_3$ (281 mg, 2.03 mmol). The mixture was stirred at 25° C. for 16 hr. The reaction mixture was diluted with $H_2O$ (10 mL) and extracted with EtOAc (10 mL×3). The combined organic layers were washed with brine (30 mL), dried over $Na_2SO_4$, filtered, and concentrated under reduced pressure. After purified by prep-TLC ($CH_2Cl_2$:MeOH=10:1), 4-((1-(4-(2-(3-aminopyrazin-2-yl)-5-(5-fluoropyridin-2-yl)-3H-imidazo[4,5-b]pyridin-3-yl)benzyl)piperidin-4-yl)amino)pyrimidine-2-carbonitrile (Example 574, 36 mg, yield: 12% for three steps) was obtained as a yellow solid. MS: m/z=599.0 [M+H]+. $^1$H NMR (400 MHz, Dimethysulfoxide-$d_6$) δ 8.67 (d, J=2.4 Hz, 1H), 8.48-8.33 (m, 2H), 8.20 (dd, J=8.8, 4.8 Hz, 1H), 8.13-8.04 (m, 2H), 8.02 (d, J=2.0 Hz, 1H), 7.90-7.73 (m, 3H), 7.49 (d, J=2.4 Hz, 1H), 7.47-7.37 (m, 4H), 6.68 (d, J=6.0 Hz, 1H), 3.95-3.75 (m, 1H), 3.61 (s, 2H), 2.94-2.81 (m, 2H), 2.24-2.14 (m, 2H), 1.97-1.86 (m, 2H), 1.55-1.47 (m, 2H). $^{19}$F NMR (400 MHz, Dimethylsulfoxide-$d_6$) δ −127.539.

To a solution of Intermediate 228 (410 mg, 906 μmol, HCl salt) and Intermediate 51 (288 mg, 906 μmol, TFA) in DMF (5 mL) were added NaI (68 mg, 453 μmol) and $K_2CO_3$ (501 mg, 3.63 mmol). The mixture was stirred at 25° C. for 16 hr. The reaction mixture was diluted with $H_2O$ (10 mL) and extracted with EtOAc (10 mL×3). The combined organic layers were washed with brine (30 mL), dried over $Na_2SO_4$, filtered, and concentrated under reduced pressure. After purified by prep-HPLC (column: Phenomenex C18 150×25 mm×10 μm; mobile phase: [water ($NH_4HCO_3$)-ACN]; B %: 38%, isocratic elution mode), 4-((1-(4-(5-(5-fluoropyridin-2-yl)-2-(pyridin-3-yl)-3H-imidazo[4,5-b]pyridin-3-yl)benzyl)piperidin-4-yl)amino)pyrimidine-2-carbonitrile (Example 575, 208 mg, yield: 40% for three steps) was obtained as a white powder. MS: m/z=583.1 [M+H]+. $^1$H NMR (400 MHz, Dimethysulfoxide-$d_6$) δ 8.81-8.53 (m, 3H), 8.47-8.33 (m, 2H), 8.25 (dd, J=8.8, 4.8 Hz, 1H), 8.20-7.98 (m, 2H), 7.94-7.80 (m, 2H), 7.57-7.48 (m, 4H), 7.45 (dd, J=8.0, 4.8 Hz, 1H), 6.85-6.65 (m, 1H), 3.92-3.74 (m, 1H), 3.62 (s, 2H), 2.90-2.82 (m, 2H), 2.23-2.12 (m, 2H), 1.97-1.84 (m, 2H), 1.58-1.45 (m, 2H). 19F NMR (400 MHz, Dimethylsulfoxide-$d_6$) δ −127.614.

Example 576: 4-((1-(4-(2-(2-Aminophenyl)-5-(5-fluoropyridin-2-yl)-3H-imidazo[4,5-b]pyridin-3-yl)benzyl)piperidin-4-yl)amino)pyrimidine-2-carbonitrile

Example 577: 4-((1-(4-(5-(5-Fluoropyridin-2-yl)-2-phenyl-3H-imidazo[4,5-b]pyridin-3-yl)benzyl)piperidin-4-yl)amino)pyrimidine-2-carbonitrile

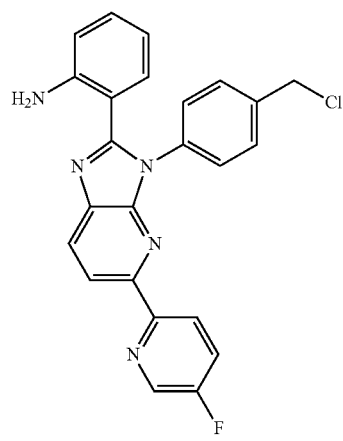

Intermediate 229

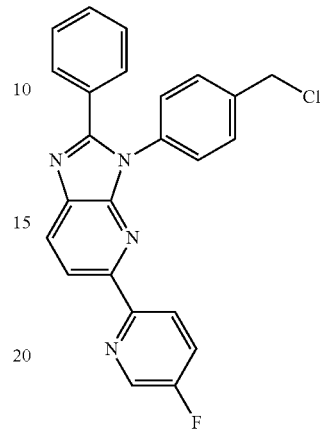

Intermediate 230

→ Intermediate 51

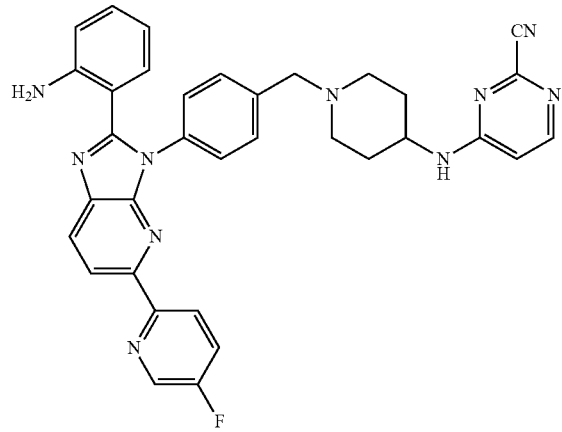

Example 576

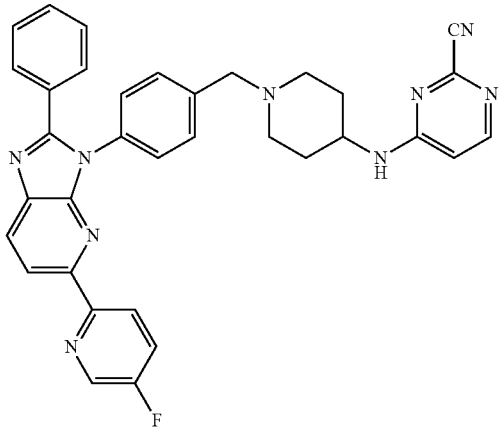

Example 577

To a solution of Intermediate 229 (175 mg, 407 μmol, HCl salt) and Intermediate 51 (124 mg, 611 gmol, TFA salt) in DMF (3 mL) were added NaI (61 mg, 407 μmol) and K$_2$CO$_3$ (169 mg, 1.22 mmol). The mixture was stirred at 25° C. for 16 hr. The reaction mixture was diluted with H$_2$O (30 mL) and extracted with EtOAc (20 mL×3). The combined organic layers were washed with brine (30 mL), dried over Na$_2$SO$_4$, filtered, and concentrated under reduced pressure. After purified by silica gel flash chromatography (Eluent of 0~9% MeOH in CH$_2$Cl$_2$), 4-((1-(4-(2-(2-aminophenyl)-5-(5-fluoropyridin-2-yl)-3H-imidazo[4,5-b]pyridin-3-yl)benzyl)piperidin-4-yl)amino)pyrimidine-2-carbonitrile (Example 576, 38.7 mg, yield: 16% for three steps) was obtained as a yellow solid. MS: m/z=597.2 [M+H]$^+$. $^1$H NMR (400 MHz, Dimethysulfoxide-d$_6$) δ 8.66 (d, J=2.8 Hz, 1H), 8.42-8.35 (m, 1H), 8.30-8.19 (m, 2H), 8.14-8.04 (m, 2H), 7.90-7.77 (m, 1H), 7.50-7.38 (m, 4H), 7.12-7.01 (m, 1H), 6.81 (d, J=8.0 Hz, 2H), 6.68 (d, J=6.0 Hz, 1H), 6.32-6.28 (m, 2H), 3.94-3.72 (m, 1H), 3.59 (s, 2H), 2.83 (d, J=10.8 Hz, 2H), 2.27-2.05 (m, 2H), 1.96-1.81 (m, 2H), 1.60-1.40 (m, 2H). $^{19}$F NMR (400 MHz, Dimethysulfoxide-d$_6$) δ −127.98.

To a solution of Intermediate 230 (103 mg, 248 μmol, HCl salt) and Intermediate 51 (78.8 mg, 248 μmol, TFA) in DMF (2 mL) were added K$_2$CO$_3$ (103 mg, 745 μmol) and NaI (7.44 mg, 49.7 μmol). The mixture was stirred at 50° C. for 0.5 hr. The reaction mixture was quenched with H$_2$O (50 mL) at 25° C. and extracted with CH$_2$Cl$_2$ (50 mL×3). The combined organic layers were washed with brine (50 mL×3), dried over Na$_2$SO$_4$, filtered and concentrated under reduced pressure. After purified by prep-HPLC (column: Waters xbridge 150×25 mm 10 m; mobile phase: [water (NH$_4$HCO$_3$)-ACN]; gradient: 42%-72% B over 10 min), 4-((1-(4-(5-(5-fluoropyridin-2-yl)-2-phenyl-3H-imidazo[4,5-b]pyridin-3-yl)benzyl)piperidin-4-yl)amino)pyrimidine-2-carbonitrile (Example 577, 23.9 mg, yield: 17% for two steps) was obtained as a light yellow lyophilized powder. MS: m/z=582.2 [M+H]$^+$. $^1$H NMR (400 MHz, Dimethylsulfoxide-d$_6$) δ 8.52 (d, J=2.8 Hz, 1H), 8.47 (d, J=8.4 Hz, 1H), 8.34 (dd, J=8.8, 4.4 Hz, 1H), 8.23 (d, J=8.4 Hz, 1H), 8.06-7.95 (m, 1H), 7.63-7.55 (m, 5H), 7.48-7.44 (m, 3H), 7.40 (d, J=7.6 Hz, 2H), 6.60 (d, J=4.8 Hz, 1H), 4.08-3.85 (m, 1H), 3.69 (s, 2H), 3.02-2.98 (m, 2H), 2.34-2.27 (m, 2H), 2.04-1.99 (m, 2H), 1.67-1.58 (m, 2H).

1713

Example 578: 4-((1-(4-(2-(2-Aminopyridin-3-yl)-5-(5-(methoxy-d)pyridin-2-yl)-3H-imidazo[4,5-b]pyridin-3-yl)benzyl)piperidin-4-yl)amino)pyrimidine-2-carbonitrile

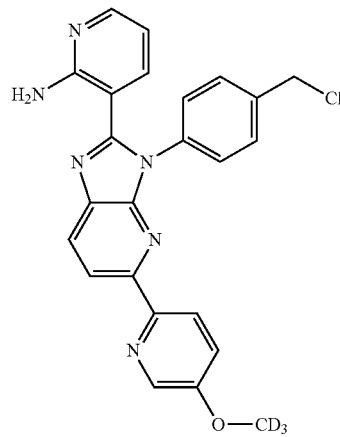

Intermediate 232

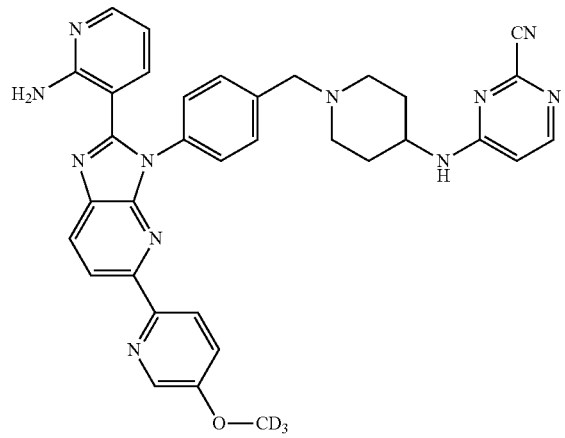

Example 578

To a solution of Intermediate 232 (150 mg, 446 µmol) and Intermediate 51 (82 mg, 404 µmol) in DMF (3 mL) were added K₂CO₃ (186 mg, 1.3 mmol) and NaI (2.5 mg, 17 µmol). The mixture was stirred at 50° C. for 1 hr. The reaction mixture was quenched with H₂O (10 mL) at 25° C. and extracted with CH₂Cl₂ (15 mL×2). The combined organic layers were washed with brine (50 mL×3), dried over Na₂SO₄, filtered and concentrated under reduced pressure. After purified by silica gel flash chromatography (Eluent of 0%~5% MeOH in CH₂Cl₂), 4-((1-(4-(2-(2-aminopyridin-3-yl)-5-(5-(methoxy-d4)pyridin-2-yl)-3H-imidazo[4,5-b]pyridin-3-yl)benzyl)piperidin-4-yl)amino)pyrimidine-2-carbonitrile (Example 578, 22.5 mg, yield: 11% for three steps) was obtained as a yellow solid. MS: m/z=613.2 [M+H]⁺. D %: 3D=99.3%. ¹H NMR (400 MHz, Dimethylsulfoxide-d₆) δ 8.39-8.34 (m, 2H), 8.27 (d, J=8.4 Hz, 1H), 8.14 (d, J=8.8 Hz, 1H), 8.07-8.02 (m, 2H), 8.00 (dd, J=4.8, 1.6 Hz, 1H), 7.51-7.44 (m, 5H), 7.16 (dd, J=7.6, 1.6 Hz, 1H), 7.02 (s, 2H), 6.68 (d, J=6.0 Hz, 1H), 6.38 (dd, J=7.6, 4.8 Hz, 1H), 3.92-3.72 (m, 1H), 3.60 (s, 2H), 2.87-2.80 (m, 2H), 2.21-2.12 (m, 2H), 1.95-1.85 (m, 2H), 1.55-1.45 (m, 2H).

1714

Example 579: 4-((1-(4-(2-(2-Aminopyridin-3-yl)-5-(5-(difluoromethoxy)pyridin-2-yl)-3H-imidazo[4,5-b]pyridin-3-yl)benzyl)piperidin-4-yl)amino)pyrimidine-2-carbonitrile

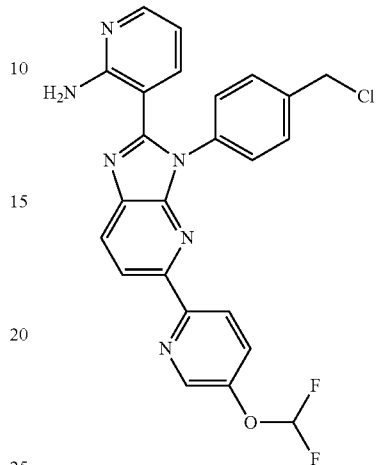

Intermediate 233

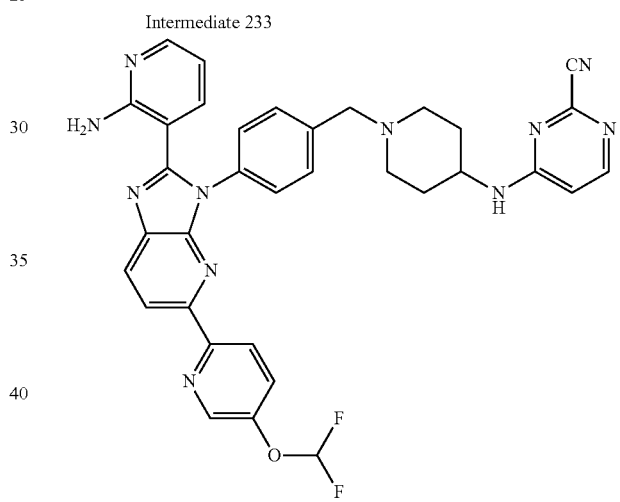

Example 579

To a solution of Intermediate 233 (115 mg, 240 gmol, HCl salt) and Intermediate 51 (76.2 mg, 240 µmol, TFA) in DMF (2 mL) were added K₂CO₃ (166 mg, 1.20 mmol) and NaI (10.8 mg, 72 µmol). The mixture was stirred at 25° C. for 16 hr. The reaction mixture was poured into H₂O (15 mL) and extracted with EtOAc (15 mL×3). The organic phase was dried over anhydrous Na₂SO₄, filtered and concentrated under reduced pressure. After purified by silica gel flash chromatography (Eluent of 0%~6% MeOH in CH₂Cl₂), 4-((1-(4-(2-(2-aminopyridin-3-yl)-5-(5-(difluoromethoxy)pyridin-2-yl)-3H-imidazo[4,5-b]pyridin-3-yl)benzyl)piperidin-4-yl)amino)pyrimidine-2-carbonitrile (Example 579, 54.5 mg, yield: 35% for three steps) was obtained as an off white solid. MS: m/z=646.3 [M+H]⁺. ¹H NMR (400 MHz, Dimethylsulfoxide-d₆) δ 8.57 (d, J=2.8 Hz, 1H), 8.41 (d, J=8.4 Hz, 1H), 8.41 (d, J=8.4 Hz, 1H), 8.23 (d, J=8.8 Hz, 1H), 8.12-8.03 (m, 2H), 8.03-7.98 (m, 1H), 7.77 (dd, J=8.8, 2.8 Hz, 1H), 7.57-7.52 (m, 0.5H), 7.51-7.46 (m, 3H), 7.39-7.31 (m, 0.5H), 7.19-7.12 (m, 1H), 7.09 (s, 2H), 6.78-6.60 (m, 1H), 6.39 (dd, J=7.6, 4.8 Hz, 11H), 3.93-3.74

(m, 1H), 3.60 (br s, 2H), 2.88-2.79 (m, 2H), 2.23-2.10 (m, 2H), 1.99-1.83 (m, 2H), 1.58-1.43 (m, 2H). $^{19}$F NMR (400 MHz, Dimethysulfoxide-d$_6$) δ −82.472.

Example 580: 4-((1-(4-(2-(2-Aminopyridin-3-yl)-5-(5-(fluoromethoxy)pyridin-2-yl)-3H-imidazo[4,5-b]pyridin-3-yl)benzyl)piperidin-4-yl)amino)pyrimidine-2-carbonitrile

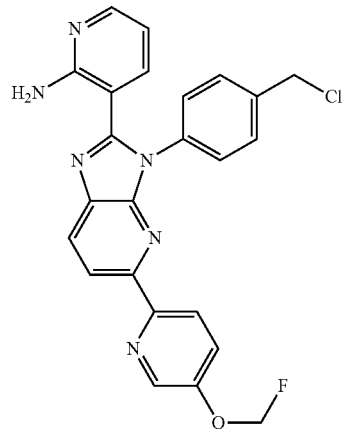

Intermediate 235

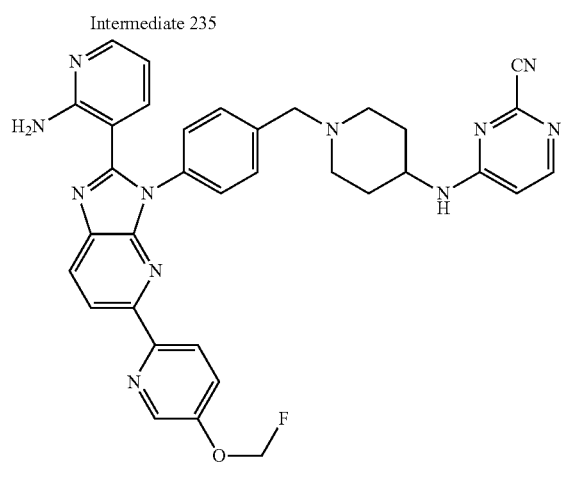

Example 580

To a solution of Intermediate 235 (150 mg, 325.4 μmol) and Intermediate 51 (79 mg, 390 gmol) in DMF (3 mL) were added K$_2$CO$_3$ (180 mg, 1.3 mmol) and NaI (2.4 mg, 16 μmol). The mixture was stirred at 50° C. for 1 hr. The reaction mixture was quenched with H$_2$O (10 mL) at 25° C. and extracted with CH$_2$Cl$_2$ (15 mL×2). The combined organic layers were washed with brine (50 mL×3), dried over Na$_2$SO$_4$, filtered, and concentrated under reduced pressure. After purified by silica gel flash chromatography (Eluent of 0%~8% MeOH in CH$_2$Cl$_2$), 4-((1-(4-(2-(2-aminopyridin-3-yl)-5-(5-(fluoromethoxy)pyridin-2-yl)-3H-imidazo[4,5-b]pyridin-3-yl)benzyl)piperidin-4-yl)amino)pyrimidine-2-carbonitrile (Example 580, 51.5 mg, yield: 25% for three steps) was obtained as a yellow solid. MS: m/z=628.2 [M+H]$^+$. $^1$H NMR (400 MHz, Dimethylsulfoxide-d$_6$) 8.51 (d, J=2.8 Hz, 1H), 8.39 (d, J=8.4 Hz, 1H), 8.30 (d, J=8.4 Hz, 1H), 8.19 (d, J=8.8 Hz, 1H), 8.25-8.01 (m, 2H), 8.00 (dd, J=4.8, 2.0 Hz, 1H), 7.68 (dd, J=8.8, 3.2 Hz, 1H), 7.51-7.45 (m, 4H), 7.17 (dd, J=7.6, 1.6 Hz, 1H), 7.01 (s, 2H), 6.68 (d, J=6.0 Hz, 1H), 6.38 (dd, J=7.6, 4.8 Hz, 1H), 5.96 (d, J=53.6 Hz, 2H), 3.87-3.76 (m, 1H), 3.60 (s, 2H), 2.90-2.80 (m, 2H), 2.24-2.10 (m, 2H), 1.95-1.85 (m, 2H), 1.57-1.44 (m, 2H). $^{19}$F NMR (400 MHz, Dimethylsulfoxide-d$_6$) δ −151.294.

Example 581: 4-((1-(4-(2-(2-Aminopyridin-3-yl)-5-(5-methoxypyrimidin-2-yl)-3H-imidazo[4,5-b]pyridin-3-yl)benzyl)piperidin-4-yl)amino)pyrimidine-2-carbonitrile

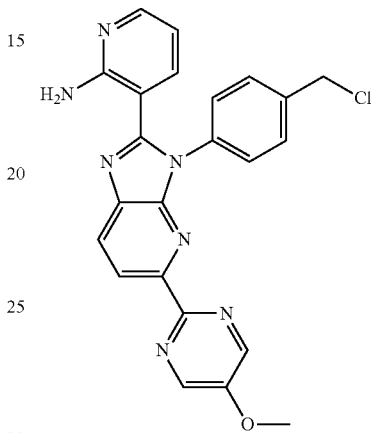

Intermediate 236

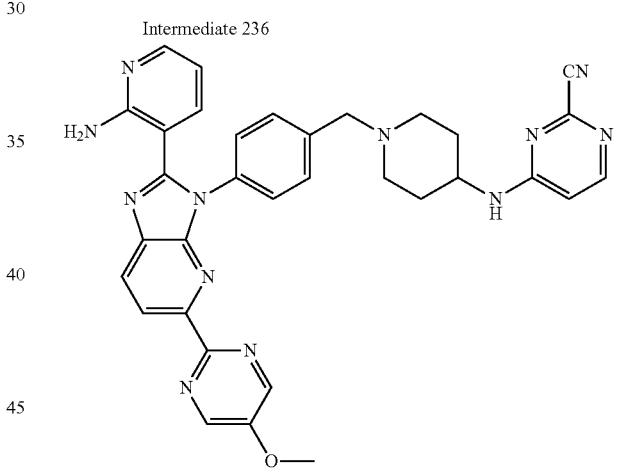

Example 581

To a solution of Intermediate 236 (226 mg, 470 μmol, HCl salt) and Intermediate 51 (149 mg, 470 μmol, TFA) in DMF (4 mL) were added K$_2$CO$_3$ (325 mg, 2.35 mmol) and NaI (7.05 mg, 47.0 μmol). The mixture was stirred at 25° C. for 3 hr. The reaction mixture was quenched with H$_2$O (10 mL) at 25° C. and extracted with CH$_2$Cl$_2$ (15 mL×2). The combined organic layers were washed with brine (50 mL×3), dried over Na$_2$SO$_4$, filtered and concentrated under reduced pressure. The crude product was triturated with DMF (5 mL) at 25° C. for 3 minutes and MeCN (10 mL) at 25° C. for 10 minutes. The solid was collected, washed with MeCN (5 mL×2), dried under reduced pressure to give 4-((1-(4-(2-(2-aminopyridin-3-yl)-5-(5-methoxypyrimidin-2-yl)-3H-imidazo[4,5-b]pyridin-3-yl)benzyl)piperidin-4-yl)amino)pyrimidine-2-carbonitrile (Example 581, 83.6 mg, yield: 27% for two steps) as a yellow solid. MS: m/z=611.3 [M+H]$^+$. $^1$H NMR (400 MHz, Dimethylsulfoxide-d$_6$) δ 8.66

(s, 2H), 8.42-8.38 (m, 1H), 8.33-8.28 ((m, 1H), 8.14 (d, J=7.2 Hz, 1H), 8.08 (d, J=6.0 Hz, 1H), 7.99 (dd, J=4.8, 1.6 Hz, 1H), 7.51-7.41 (m, 4H), 7.13 (dd, J=7.6, 1.6 Hz, 1H), 7.00 (br s, 2H), 6.70 (d, J=6.0 Hz, 1H), 6.37 (dd, J=7.6, 4.8 Hz, 1H), 3.96 (s, 3H), 3.88-3.73 (m, 1H), 3.59 (s, 2H), 2.86-2.79 (m, 2H), 2.22-2.12 (m, 2H), 1.94-1.85 (m, 2H), 1.57-1.46 (m, 2H).

Example 582: 4-((1-(4-(2-(2-Aminopyridin-3-yl)-5-(5-methylpyrazin-2-yl)-3H-imidazo[4,5-b]pyridin-3-yl)benzyl)piperidin-4-yl)amino)pyrimidine-2-carbonitrile

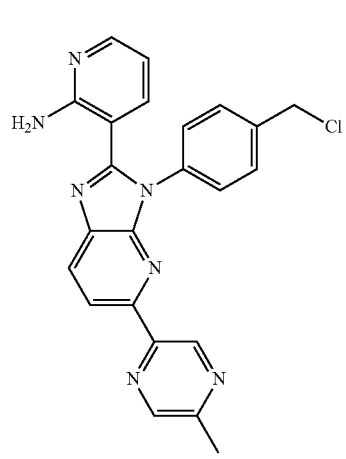

Intermediate 237

→ Intermediate 51

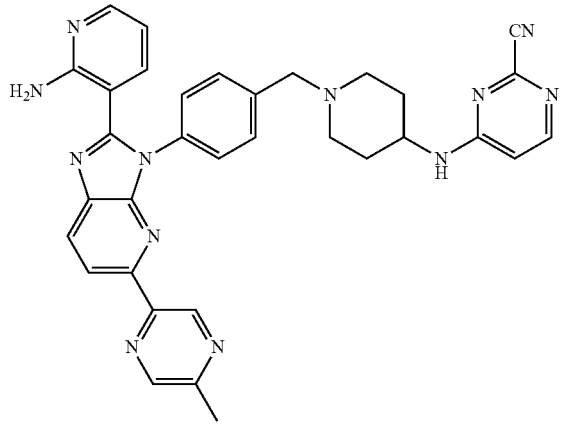

Example 582

MHz, Dimethylsulfoxide-d$_6$) δ 9.21 (s, 1H), 8.62 (s, 1H), 8.35-8.33 (m, 2H), 8.10-8.01 (m, 3H), 7.51-7.47 (m, 4H), 7.20 (dd, J=7.6, 1.6 Hz, 1H), 7.03 (s, 2H), 6.67 (d, J=6.4 Hz, 1H), 6.40 (dd, J=7.6, 4.8 Hz, 1H), 3.88-3.77 (m, 1H), 3.60 (s, 2H), 2.86-2.81 (m, 2H), 2.54 (s, 3H), 2.20-2.13 (m, 2H), 1.93-1.86 (m, 2H), 1.55-1.47 (m, 2H).

Example 583: 4-((1-(4-(2-(2-Aminopyridin-3-yl)-5-(5-methoxypyrazin-2-yl)-3H-imidazo[4,5-b]pyridin-3-yl)benzyl)piperidin-4-yl)amino)pyrimidine-2-carbonitrile

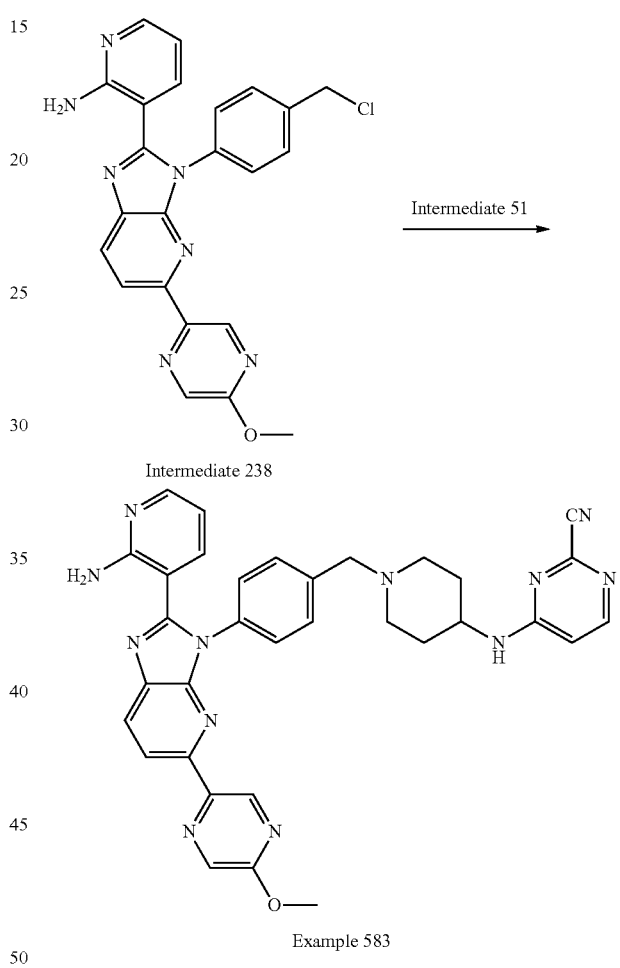

To a solution of Intermediate 237 (158 mg, 340 μmol, HCl salt) and Intermediate 51 (109 mg, 345 μmol, TFA) in DMF (5 mL) were added NaI (80.7 mg, 538 μmol) and K$_2$CO$_3$ (372 mg, 2.69 mmol). The mixture was stirred at 50° C. for 1 hr. The reaction mixture was diluted with H$_2$O (50 mL) and extracted with EtOAc (50 mL×3). The combined organic layers were washed with brine (100 mL), dried over Na$_2$SO$_4$, filtered and concentrated under reduced pressure. After purified by prep-HPLC (column: Waters xbridge 150× 25 mm 10 μm; mobile phase: [water (NH$_4$HCO$_3$)-ACN]; gradient: 30%-60% B over 10 min), 4-((1-(4-(2-(2-amino-pyridin-3-yl)-5-(5-methylpyrazin-2-yl)-3H-imidazo[4,5-b]pyridin-3-yl)benzyl)piperidin-4-yl)amino)pyrimidine-2-carbonitrile (Example 582, 106.9 mg, yield: 33%) was obtained as a yellow solid. MS: m/z=595.3 [M+H]$^+$. $^1$H NMR (400

To a solution of Intermediate 238 (250 mg, 520 μmol, HCl salt) and Intermediate 51 (106 mg, 333 μmol, TFA) in DMF (5 mL) were added NaI (78 mg, 520 μmol) and K$_2$CO$_3$ (360 mg, 2.60 mmol). The mixture was stirred at 50° C. for 1 hr. The reaction mixture was diluted with H$_2$O (50 mL) and extracted with EtOAc (50 mL×3). The combined organic layers were washed with brine (100 mL), dried over Na$_2$SO$_4$, filtered and concentrated under reduced pressure. After purified by prep-HPLC (column: Waters xbridge 150× 25 mm 10 μm; mobile phase. [water (NH$_4$HCO$_3$)-ACN]; gradient: 36%-66% B over 10 min), 4-((1-(4-(2-(2-amino-pyridin-3-yl)-5-(5-methoxypyrazin-2-yl)-3H-imidazo[4,5-b]pyridin-3-yl)benzyl)piperidin-4-yl)amino)pyrimidine-2-carbonitrile (Example 583, 110.2 mg, yield: 34%) was obtained as a yellow solid. MS: m/z=611.2 [M+H]$^+$. $^1$H NMR (400 MHz, Dimethylsulfoxide-d$_6$) δ 8.91 (d, J=1.2

Hz, 1H), 8.40 (d, J=1.2 Hz, 1H), 8.32 (d, J=8.4 Hz, 1H), 8.25 (d, J=8.4 Hz, 1H), 8.10-8.00 (m, 3H), 7.48 (dd, J=14.0, 8.4 Hz, 4H), 7.20 (dd, J=7.2, 1.6 Hz, 1H), 7.03 (s, 2H), 6.67 (d, J=6.0 Hz, 1H), 6.40 (dd, J=7.6, 4.8 Hz, 1H), 3.95 (s, 3H), 3.83-3.81 (m, 1H), 3.60 (s, 2H), 2.86-2.81 (m, 2H), 2.22-2.14 (m, 2H), 1.94-1.86 (m, 2H), 1.55-1.47 (m, 2H)

Example 584: 4-((1-(4-(2-(2-Aminopyridin-3-yl)-5-(6-ethoxypyridin-3-yl)-3H-imidazo[4,5-b]pyridin-3-yl)benzyl)piperidin-4-yl)amino)pyrimidine-2-carbonitrile

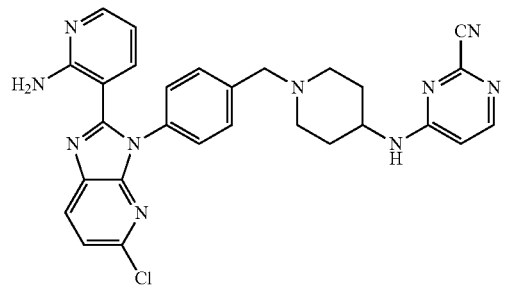

Example 405

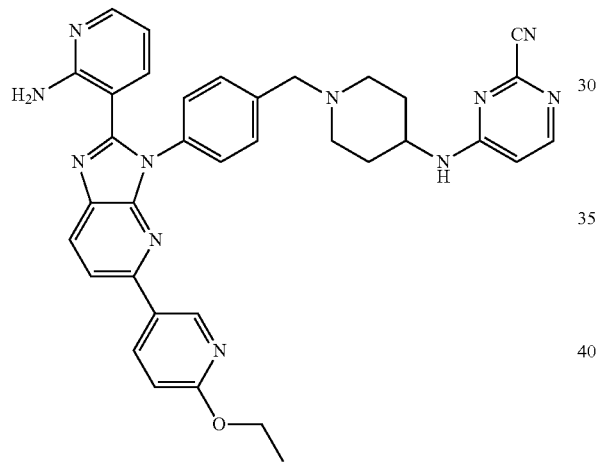

Example 584

To a mixture of Example 405 (300 mg, 559 μmol) and (6-ethoxypyridin-3-yl)boronic acid (103 mg, 615 μmol) in 1,4-dioxane (2 mL) and H$_2$O (0.5 mL) were added Cs$_2$CO$_3$ (546 mg, 1.68 mmol) and Pd(dppf)Cl$_2$ (40.9 mg, 55.9 μmol). The mixture was stirred at 100° C. for 2 hr under N$_2$. The mixture was diluted with H$_2$O (50 mL) and extracted with EtOAc (100 mL×2). The combined organic layers were washed with brine (100 mL), dried over anhydrous Na$_2$SO$_4$, filtered and concentrated. After purified by prep-HPLC (column: Phenomenex C18 80×30 mm×5 μm; mobile phase: [water (NH$_3$H$_2$O+NH$_4$HCO$_3$)-ACN]; gradient: 55%-85% B over 7 min), 4-((1-(4-(2-(2-aminopyridin-3-yl)-5-(6-ethoxypyridin-3-yl)-3H-imidazo[4,5-b]pyridin-3-yl)benzyl)piperidin-4-yl)amino)pyrimidine-2-carbonitrile (Example 584, 119.7 mg, yield: 34%) was obtained as a yellow solid. MS: m/z=624.1 [M+H]$^+$. $^1$H NMR (400 MHz, Dimethylsulfoxide-d$_6$) δ 8.83 (d, J=2.0 Hz, 1H), 8.34-8.22 (m, 2H), 8.13-7.94 (m, 4H), 7.51-7.42 (m, 4H), 7.15 (d, J=7.2 Hz, 1H), 7.04 (s, 2H), 6.88 (d, J=8.8 Hz, 1H), 6.73-6.63 (m, 1H), 6.38 (dd, J=8.0, 5.2 Hz, 1H), 4.34 (m, J=7.2 Hz, 2H), 3.87-3.76 (m, 1H), 3.59 (s, 2H), 2.92-2.74 (m, 2H), 2.22-2.09 (m, 2H), 1.93-1.78 (m, 2H), 1.56-1.44 (m, 2H), 1.33 (t, J=7.2 Hz, 3H).

Example 585: 4-((1-(4-(2-(2-Aminopyridin-3-yl)-5-(5-cyclopropoxypyridin-2-yl)-3H-imidazo[4,5-b]pyridin-3-yl)benzyl)piperidin-4-yl)amino)pyrimidine-2-carbonitrile

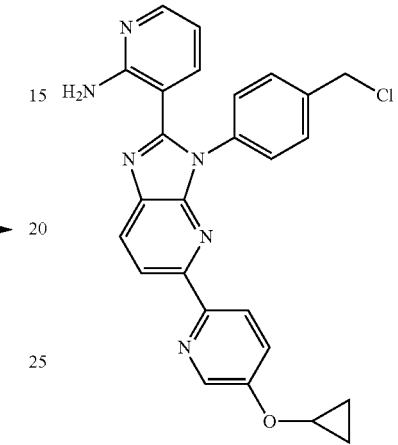

Intermediate 339

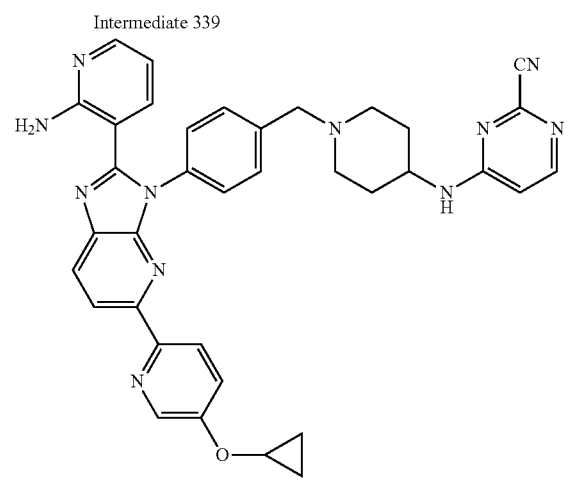

Example 585

To a solution of Intermediate 339 (166 mg, 354 μmol, HCl salt) and Intermediate 51 (108 mg, 531 μmol) in DMF (1 mL) were added K$_2$CO$_3$ (147 mg, 1.06 mmol) and NaI (5.31 mg, 35.4 μmol). The mixture was stirred at 80° C. for 8 hr. The mixture was diluted with H$_2$O (10 mL) and extracted with ethyl acetate (10 mL×2). The combined organic layers were dried over anhydrous Na$_2$SO$_4$, filtered and concentrated. After purified by prep-HPLC (column: C18 150×30 mm; mobile phase: [water (NH$_3$H$_2$O+NH$_4$HCO$_3$)-ACN]; gradient: 54%-84% B over 7 min), 4-((1-(4-(2-(2-aminopyridin-3-yl)-5-(5-cyclopropoxypyridin-2-yl)-3H-imidazo[4,5-b]pyridin-3-yl)benzyl)piperidin-4-yl)amino)pyrimidine-2-carbonitrile (Example 585, 45.5 mg, yield: 20% for three steps) was obtained as a light yellow solid. MS: m/z=658.2 [M+Na]$^+$. $^1$H NMR (400 MHz, Dimethylsulfoxide-d$_6$) δ 8.45 (d, J=3.2 Hz, 1H), 8.36 (d, J=8.4 Hz, 1H), 8.27 (d, J=8.4 Hz, 1H), 8.14 (d, J=8.8 Hz, 1H), 8.13-8.02 (m, 2H), 8.00 (dd, J=4.8, 2.0 Hz, 1H), 7.60 (dd, J=8.4, 2.8 Hz, 1H), 7.51-7.44 (m, 4H), 7.16 (dd, J=8.0, 2.0 Hz, 1H), 7.02 (br s, 2H), 6.67 (d, J=6.0 Hz, 1H), 6.38 (dd, J=7.6, 4.8 Hz, 1H), 4.01-3.96 (m, 1H), 3.89-3.73 (m, 1H), 3.60 (s, 2H), 2.92-2.79 (m, 2H), 2.21-2.12 (m, 2H), 1.95-1.82 (m, 2H), 1.56-1.44 (m, 2H), 0.85-0.80 (m, 2H), 0.73-0.69 (m, 2H).

Example 586: 4-((1-(4-(2-(2-Aminopyridin-3-yl)-5-(5-isopropoxypyridin-2-yl)-3H-imidazo[4,5-b]pyridin-3-yl)benzyl)piperidin-4-yl)amino)pyrimidine-2-carbonitrile

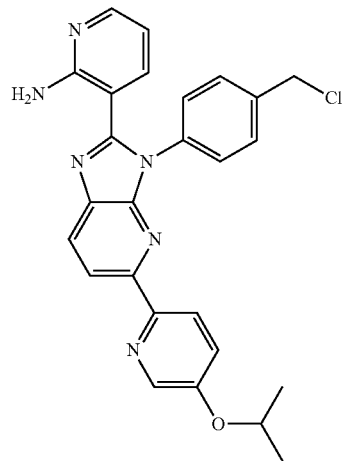

Intermediate 340

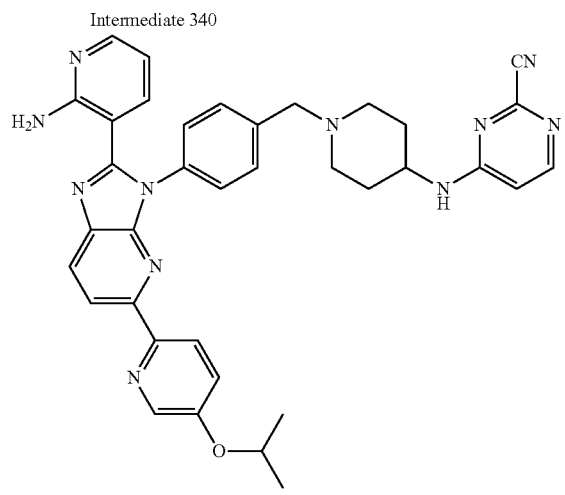

Example 586

To a solution of Intermediate 340 (199 mg, 424 μmol) and Intermediate 51 (112 mg, 551 gmol) in DMF (1 mL) were added NaI (6.35 mg, 42.4 μmol) and K$_2$CO$_3$ (176 mg, 1.27 mmol). The mixture was stirred at 25° C. for 12 hr. The mixture was diluted with and extracted with EtOAc (5 mL×2). The combined organic layers were dried over anhydrous Na$_2$SO$_4$, filtered and concentrated. After purified by prep-HPLC (column: C18 150×30 mm; mobile phase: [water (NH$_3$H$_2$O+NH$_4$HCO$_3$)-ACN]; gradient: 59%-89% B over 7 min), 4-((1-(4-(2-(2-aminopyridin-3-yl)-5-(5-isopropoxypyridin-2-yl)-3H-imidazo[4,5-b]pyridin-3-yl)benzyl)piperidin-4-yl)amino)pyrimidine-2-carbonitrile (Example 586, 79.5 mg, yield: 29.4% for three steps) was obtained as a light yellow solid. MS: m/z=638.4 [M+H]$^+$. $^1$H NMR (400 MHz, Dimethylsulfoxide-d$_6$) δ 8.39-8.30 (m, 2H), 8.25 (d, J=8.4 Hz, 1H), 8.14-8.01 (m, 3H), 8.00 (dd, J=4.8, 1.6 Hz, 1H), 7.51-7.43 (m, 5H), 7.15 (dd, J=7.6, 1.2 Hz, 1H), 7.03 (br s, 2H), 6.68 (br d, J=6.4 Hz, 1H), 6.37 (dd, J=7.6, 4.8 Hz, 1H), 4.77-4.68 (m, 1H), 3.82-3.81 (m, 1H), 3.60 (s, 2H), 2.84-2.82 (m, 2H), 2.19-2.13 (m, 2H), 1.95-1.83 (m, 2H), 1.55-1.42 (m, 2H), 1.30 (d, J=6.0 Hz, 6H).

Example 587: 4-((1-(4-(2-(2-Aminopyridin-3-yl)-5-(6-cyclopropylpyridin-3-yl)-3H-imidazo[4,5-b]pyridin-3-yl)benzyl)piperidin-4-yl)amino)pyrimidine-2-carbonitrile

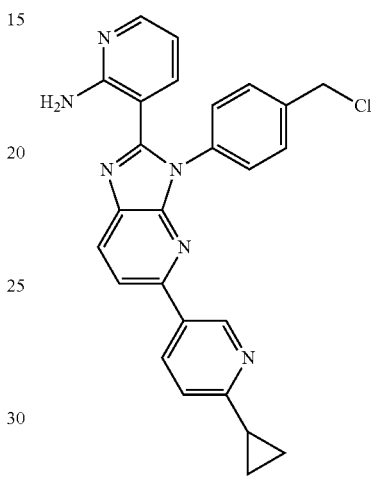

Intermediate 341

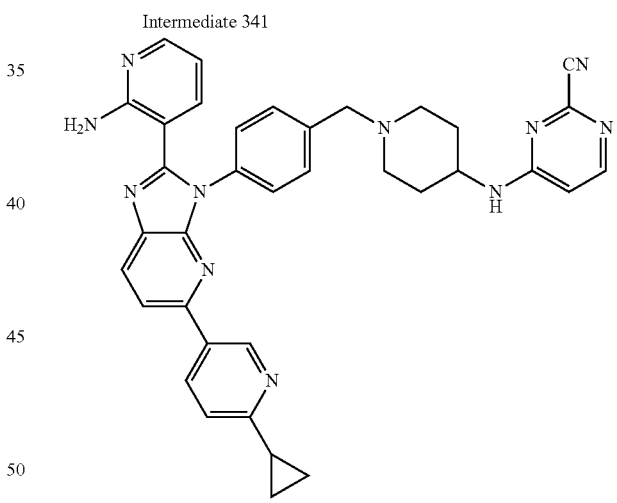

Example 587

To a solution of Intermediate 341 (190 mg, 420 μmol, HCl salt) and Intermediate 51 (102 mg, 503 μmol) in DMF (3 mL) were added K$_2$CO$_3$ (174 mg, 1.26 mmol) and NaI (6.29 mg, 42.0 μmol). The mixture was stirred at 25° C. for 12 hr. The mixture was diluted with H$_2$O (10 mL) and extracted with ethyl acetate (10 mL×2). The combined organic layers were dried over anhydrous Na$_2$SO$_4$, filtered and concentrated. After purified by prep-HPLC (column: C18 150×30 mm; mobile phase: [water (NH$_3$H$_2$O+NH$_4$HCO$_3$)-ACN]; gradient: 45%-75% B over 7 min), 4-((1-(4-(2-(2-aminopyridin-3-yl)-5-(6-cyclopropylpyridin-3-yl)-3H-imidazo[4,5-b]pyridin-3-yl)benzyl)piperidin-4-yl)amino)pyrimidine-2-carbonitrile (Example 587, 93.4 mg, yield: 36% for three steps) was obtained as a light yellow solid. MS: m/z=620.3 [M+H]+. 1H NMR (400 MHz, Dimethylsulfoxide-d6) δ 9.05 (d, J=2.4 Hz, 1H), 8.28 (d, J=8.4 Hz, 1H), 8.21 (dd, J=8.4, 2.4 Hz, 1H), 8.07 (dd, J=12.8, 6.0 Hz, 2H), 8.02-7.97 (m, 2H), 7.50-7.42 (m, 4H), 7.37 (d, J=8.4 Hz, 1H), 7.16 (dd, J=7.6, 1.6 Hz, 1H), 7.04 (brs, 2H), 6.67 (d, J=6.4 Hz, 1H), 6.38 (dd, J=7.6, 4.8 Hz, 1H), 3.95-3.71 (m, 1H), 3.59 (s, 2H), 2.90-2.75 (m, 2H), 2.21-2.09 (m, 3H), 1.99-1.82 (m, 2H), 1.59-1.45 (m, 2H), 0.99-0.93 (m, 4H).

Example 588: 4-((1-(4-(2-(2-Aminopyridin-3-yl)-5-(3-methyl-4H-1,2,4-triazol-4-yl)-3H-imidazo[4,5-b]pyridin-3-yl)benzyl)piperidin-4-yl)amino)pyrimidine-2-carbonitrile

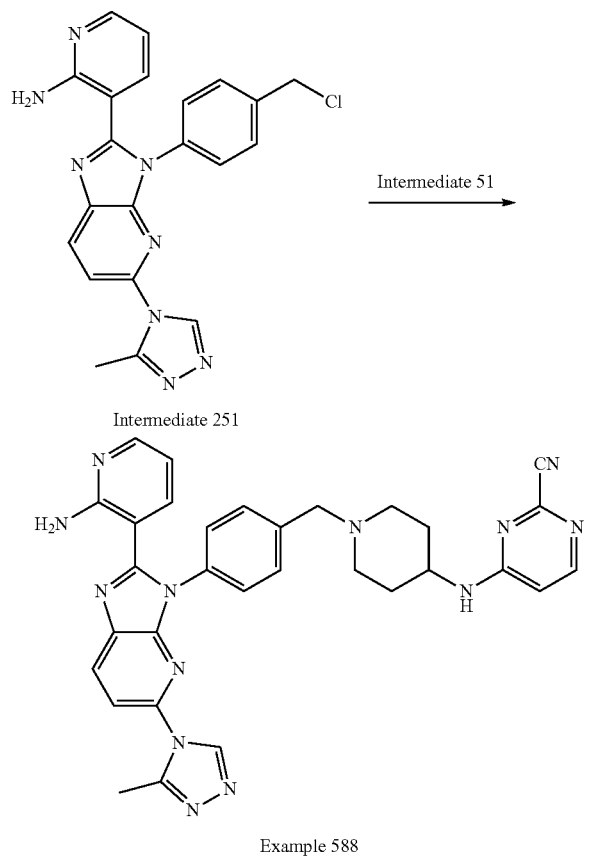

Example 588

To a solution of Intermediate 251 (166 mg, 366 μmol, HCl salt) and Intermediate 51 (213 mg, 671 μmol, TFA salt) in DMF (2 mL) were added K2CO3 (253 mg, 1.83 mmol) and NaI (16.5 mg, 110 μmol). The mixture was stirred at 25° C. for 1 hr. The reaction mixture was poured into H2O (20 mL) and extracted with EtOAc (20 mL×3). The combined organic phases were dried over anhydrous Na2SO4, filtered and concentrated under reduced pressure. After purified by silica gel flash chromatography (Eluent of 0%~5% MeOH in CH2Cl2), 4-((1-(4-(2-(2-aminopyridin-3-yl)-5-(3-methyl-4H-1,2,4-triazol-4-yl)-3H-imidazo[4,5-b]pyridin-3-yl)benzyl)piperidin-4-yl)amino)pyrimidine-2-carbonitrile (Example 588, 71.4 mg, yield: 33% for three steps) was obtained as a yellow solid. MS: m/z=584.4 [M+H]+ 1H NMR (400 MHz, Dimethylsulfoxide-d6) δ 8.43 (d, J=8.4 Hz, 1H), 8.19-7.91 (m, 4H), 7.83 (d, J=8.4 Hz, 1H), 7.52-7.41 (m, 4H), 7.25 (dd, J=7.6, 1.6 Hz, 1H), 7.04 (s, 2H), 6.74-6.60 (m, 1H), 6.41 (dd, J=7.6, 4.8 Hz, 1H), 3.91-3.69 (m, 1H), 3.58 (br s, 2H), 2.83-2.75 (m, 2H), 2.56 (s, 3H), 2.19-2.07 (m, 2H), 1.96-1.80 (m, 2H), 1.54-1.42 (m, 2H).

Example 589: 4-((1-(4-(2-(2-Aminopyridin-3-yl)-5-(3-methyl-1H-1,2,4-triazol-1-yl)-3H-imidazo[4,5-h]pyridin-3-yl)benzyl)piperidin-4-yl)amino)pyrimidine-2-carbonitrile

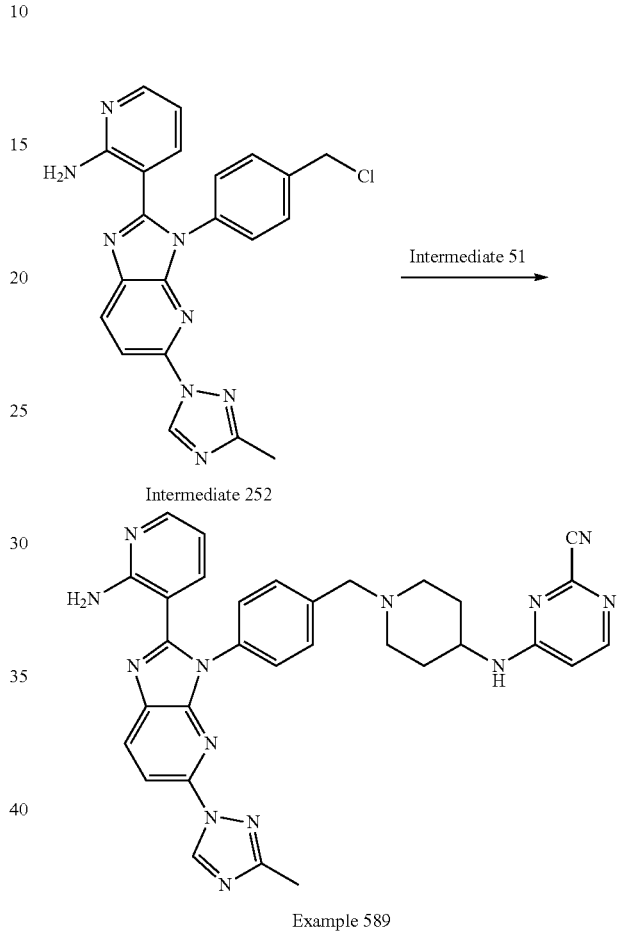

Example 589

To a solution of Intermediate 252 (150 mg, 360 μmol, HCl salt) and Intermediate 51 (73.1 mg, 360 μmol, TFA) in DMF (2 mL) were added K2CO3 (149 mg, 1.08 mmol) and NaI (10.8 mg, 72.0 μmol). The mixture was stirred at 50° C. for 0.5 hr. The reaction mixture was quenched with H2O (50 mL) at 25° C., diluted with CH2Cl2 (50 mL), and extracted with CH2Cl2 (50 mL×2). The combined organic layers were washed with brine (30 mL×3), dried over Na2SO4, filtered and concentrated under reduced pressure. After purified by prep-HPLC (column: Daisogel SP ODS RPS 150×25 mm×5 μm; mobile phase: [water (NH4HCO3)-ACN]; gradient: 30%-60% B over 10 min), 4-((1-(4-(2-(2-aminopyridin-3-yl)-5-(3-methyl-1H-1,2,4-triazol-1-yl)-3H-imidazo[4,5-b]pyridin-3-yl)benzyl)piperidin-4-yl)amino)pyrimidine-2-carbonitrile (Example 589, 59.1 mg, yield: 26% for three steps) was obtained as a light yellow solid. MS: m/z=584.3 [M+H]+. 1H NMR (400 MHz, Dimethylsulfoxide-d6) δ 8.97 (s, 1H), 8.41 (d, J=8.4 Hz, 1H), 8.10-8.05 (m, 2H), 8.02-7.99 (m, 1H), 7.85-7.84 (m, 1H), 7.48-7.42 (m, 4H), 7.17 (dd, J=7.6, 1.2 Hz, 1H), 6.93 (s, 2H), 6.67 (d, J=6.0 Hz, 11H), 6.40 (dd, J=7.6, 4.8 Hz, 1H), 3.86-3.78 (m, 1H), 3.58 (s, 2H), 2.85-2.80 (m, 2H), 2.38 (s, 3H), 2.18-2.12 (m, 2H), 1.93-1.86 (m, 2H), 1.54-1.47 (m, 2H).

Example 590: 4-((1-(4-(2-(2-Aminopyridin-3-yl)-5-(1H-1,2,4-triazol-1-yl)-3H-imidazo[4,5-b]pyridin-3-yl)benzyl)piperidin-4-yl)amino)pyrimidine-2-carbonitrile

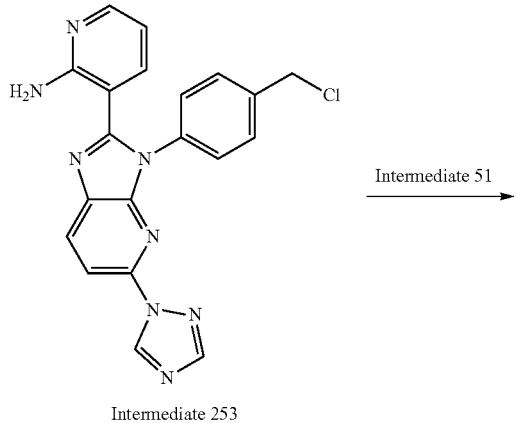

Intermediate 253

→ Intermediate 51

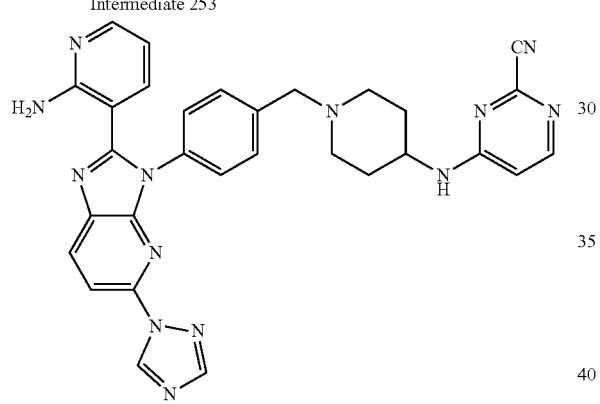

Example 590

To a solution of Intermediate 253 (150 mg, 372 μmol, HCl) and Intermediate 51 (75.7 mg, 372 μmol, TFA) in DMF (3 mL) were added $K_2CO_3$ (154 mg, 1.12 mmol) and NaI (11.2 mg, 74.5 μmol). The mixture was stirred at 50° C. for 0.5 hr. The reaction mixture was quenched with $H_2O$ (50 mL) at 25° C., diluted with $CH_2Cl_2$ (50 mL), and extracted with $CH_2Cl_2$ (50 mL×2). The combined organic layers were washed with brine (30 mL×3), dried over $Na_2SO_4$, filtered and concentrated under reduced pressure. After purified by prep-HPLC (column: Phenomenex C18 150×25 mm×10 μm; mobile phase: [water ($NH_3H_2O$)-ACN]; gradient: 38%-68%, over 11 min), 4-((1-(4-(2-(2-aminopyridin-3-yl)-5-(1H-1,2,4-triazol-1-yl)-3H-imidazo[4,5-b]pyridin-3-yl)benzyl)piperidin-4-yl)amino)pyrimidine-2-carbonitrile (Example 590, 59.1 mg, yield: 38% for three steps) was obtained as a light yellow solid. MS: m/z=570.2 [M+H]$^+$. $^1$H NMR (400 MHz, Dimethylsulfoxide-d$_6$) δ 9.12 (s, 1H), 8.45 (d, J=8.4 Hz, 1H), 8.29 (s, 1H), 8.10-8.04 (m, 2H), 8.02-8.00 (m, 1H), 7.89 (d, J=8.8 Hz, 1H), 7.46-7.44 (m, 4H), 7.20-7.16 (m, 1H), 6.93 (s, 2H), 6.67 (d, J=5.6 Hz, 1H), 6.40 (dd, J=7.6, 4.8 Hz, 1H), 3.88-3.76 (m, 1H), 3.58 (s, 2H), 2.85-2.81 (m, 2H), 2.18-2.12 (m, 2H), 1.89-1.87 (m, 2H), 1.54-1.47 (m, 2H).

Example 591: 4-((1-(4-(2-(2-Aminopyridin-3-yl)-5-(1H-1,2,3-triazol-1-yl)-3H-imidazo[4,5-b]pyridin-3-yl)benzyl)piperidin-4-yl)amino)pyrimidine-2-carbonitrile

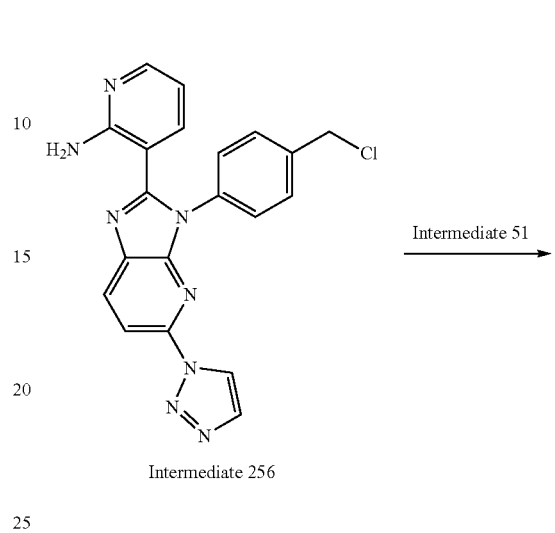

Intermediate 256

→ Intermediate 51

Example 591

To a solution of Intermediate 256 (48.2 mg, 110 μmol, HCl) and Intermediate 51 (34.8 mg, 110 μmol, TFA) in DMF (1 mL) were added $K_2CO_3$ (45.5 mg, 329 μmol) and NaI (16.4 mg, 110 μmol). The mixture was degassed and purged with $N_2$ three times and stirred at 25° C. for 16 hr under $N_2$. The reaction mixture was diluted with $CH_2Cl_2$ (10 mL) and washed with brine (10 mL×3), dried over $Na_2SO_4$, filtered and concentrated under reduced pressure. After purified by prep-TLC ($SiO_2$, $CH_2Cl_2$:MeOH=10:1), 4-((1-(4-(2-(2-aminopyridin-3-yl)-5-(1H-1,2,3-triazol-1-yl)-3H-imidazo[4,5-b]pyridin-3-yl)benzyl)piperidin-4-yl)amino)pyrimidine-2-carbonitrile (Example 591, 8.6 mg, yield 13% 13% for three steps) was obtained as a yellow solid. MS: m/z=570.1 [M+H]$^+$. $^1$H NMR (400 MHz, Methanol-d$_4$) δ 8.59 (s, 1H), 8.41 (d, J=8.8 Hz, 1H), 8.24 (d, J=8.4 Hz, 1H), 8.05-7.96 (m, 2H), 7.86 (s, 1H), 7.57 (d, J=8.4 Hz, 2H), 7.46 (d, J=8.4 Hz, 2H), 7.33 (dd, J=8.0, 2.0 Hz, 1H), 6.64-6.57 (m, 1H), 6.48 (dd, J=7.6, 5.2 Hz, 1H), 4.06-3.89 (m, 1H), 3.70 (s, 2H), 3.04-2.94 (m, 2H), 2.37-2.26 (m, 2H), 2.07-1.98 (m, 2H), 1.66-1.59 (m, 2H).

Example 592: 4-((1-(4-(2-(2-Aminopyridin-3-yl)-5-(2H-1,2,3-triazol-2-yl)-3H-imidazo[4,5-b]pyridin-3-yl)benzyl)piperidin-4-yl)amino)pyrimidine-2-carbonitrile

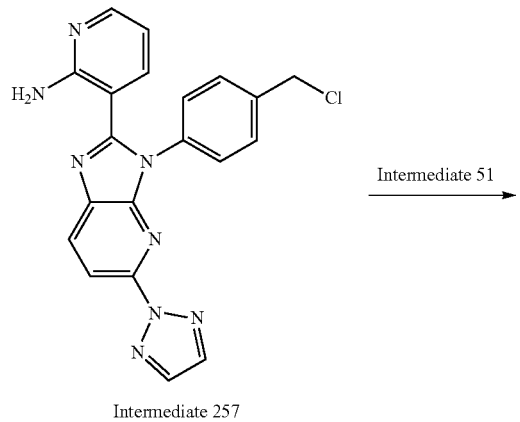

Intermediate 257

→ Intermediate 51

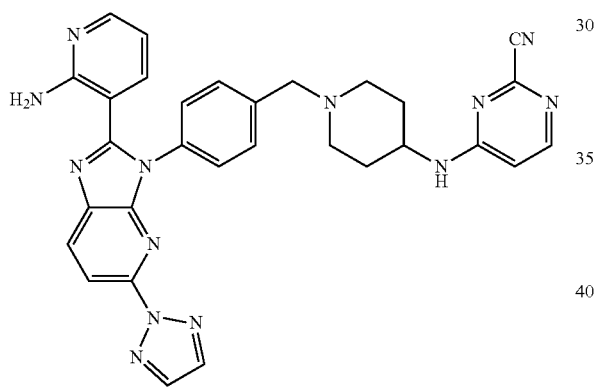

Example 592

To a solution of Intermediate 257 (103 mg, 235 µmol, HCl) and Intermediate 51 (74.4 mg, 235 µmol, TFA) in DMF (1 mL) were added K$_2$CO$_3$ (97.2 mg, 704 µmol) and NaI (35.2 mg, 235 µmol). The mixture was degassed and purged with N$_2$ for 3 times and stirred at 25° C. for 16 hr under N$_2$. The reaction mixture was diluted with CH$_2$Cl$_2$ (10 mL) and washed with brine (10 mL×3), dried over Na$_2$SO$_4$, filtered and concentrated under reduced pressure. After purified by silica gel flash chromatography (MeOH in CH$_2$Cl$_2$=1% to 7%), 4-((1-(4-(2-(2-aminopyridin-3-yl)-5-(2H-1,2,3-triazol-2-yl)-3H-imidazo[4,5-b]pyridin-3-yl)benzyl)piperidin-4-yl)amino)pyrimidine-2-carbonitrile (Example 592, 27.3 mg, yield 18% for three steps) was obtained as a pink solid. MS: m/z=570.2 [M+H]$^+$. $^1$H NMR (400 MHz, Dimethylsulfoxide-d$_6$) δ 8.44 (d, J=8.4 Hz, 1H), 8.13 (s, 2H), 8.11-8.02 (m, 3H), 8.00 (dd, J=4.8, 1.6 Hz, 1H), 7.50-7.42 (m, 4H), 7.19-7.15 (m, 1H), 6.95 (br s, 2H), 6.68 (d, J=5.6 Hz, 1H), 6.38 (dd, J=7.6, 4.8 Hz, 1H), 3.88-3.76 (m, 1H), 3.59 (s, 2H), 2.86-2.79 (m, 2H), 2.21-2.12 (m, 2H), 1.93-1.84 (m, 2H), 1.54-1.45 (m, 2H).

Example 593: 4-((1-(4-(2-(2-Aminopyridin-3-yl)-5-(4-methyl-1H-1,2,3-triazol-1-yl)-3H-imidazo[4,5-b]pyridin-3-yl)benzyl)piperidin-4-yl)amino)pyrimidine-2-carbonitrile

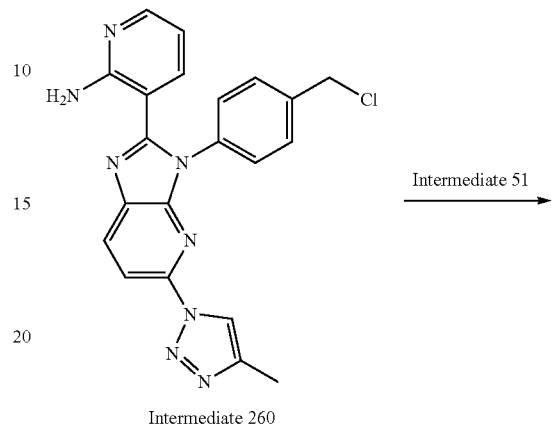

Intermediate 260

→ Intermediate 51

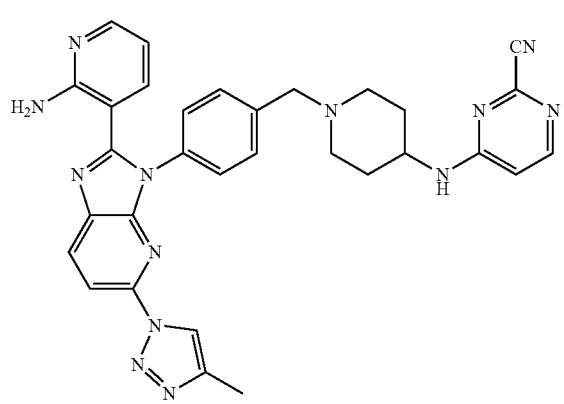

Example 593

To a solution of Intermediate 260 (146 mg, 322 µmol, HCl salt), Intermediate 51 (175 mg, 552 µmol, TFA salt) in DMF (2 mL) were added K$_2$CO$_3$ (223 mg, 1.61 mmol) and NaI (14.5 mg, 96.6 µmol). The mixture was stirred at 25° C. for 16 hr. The reaction mixture was poured into H$_2$O (20 mL), extracted with EtOAc (20 mL×3). The organic phase was dried over anhydrous Na$_2$SO$_4$, filtered and concentrated under reduced pressure. After purified by silica gel flash chromatography (Eluent of 0%~7% MeOH in CH2Cl$_2$), 4-((1-(4-(2-(2-aminopyridin-3-yl)-5-(4-methyl-1H-1,2,3-triazol-1-yl)-3H-imidazo[4,5-b]pyridin-3-yl)benzyl)piperidin-4-yl)amino)pyrimidine-2-carbonitrile (Example 593, 18.3 mg, yield: 10% for three steps) was obtained as a yellow solid. MS: m/z=584.4 [M+H]$^+$ $^1$H NMR (400 MHz, Dimethylsulfoxide-d$_6$) δ 8.55-8.41 (m, 1H), 8.39-8.29 (m, 1H), 8.17-7.96 (m, 4H), 7.54-7.42 (m, 4H), 7.26-7.12 (m, 1H), 6.92 (br s, 2H), 6.75-6.60 (m, 1H), 6.48-6.34 (m, 1H), 3.91-3.74 (m, 1H), 3.58 (s, 2H), 2.89-2.77 (m, 2H), 2.32 (s, 3H), 2.23-2.10 (m, 2H), 1.97-1.81 (m, 2H), 1.60-1.44 (m, 2H).

Example 594: 4-((1-(4-(2-(2-Aminopyridin-3-yl)-5-(oxazol-4-yl)-3H-imidazo[4,5-b]pyridin-3-yl)benzyl)piperidin-4-yl)amino)pyrimidine-2-carbonitrile

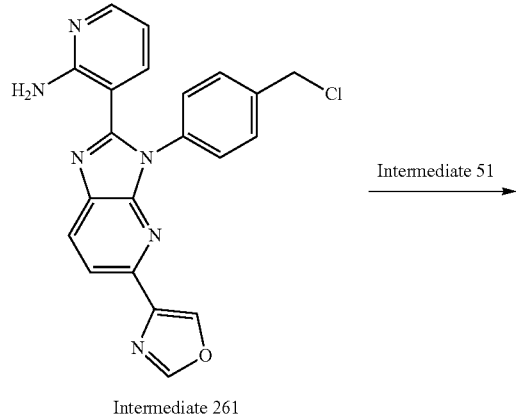

Intermediate 261

→ Intermediate 51

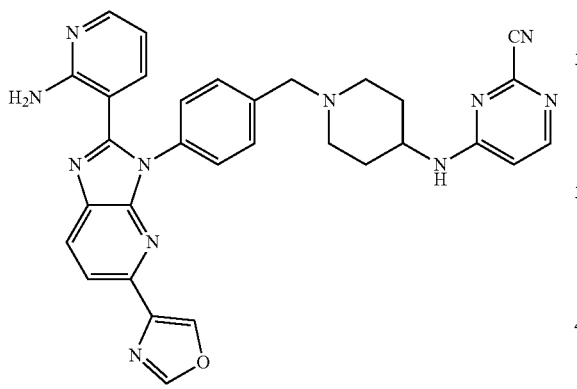

Example 594

To a solution of Intermediate 261 (122 mg, 303 μmol, HCl salt) and Intermediate 51 (96 mg 303 μmol, TFA) in DMF (3 mL) were added $K_2CO_3$ (167 mg, 1.21 mmol) and NaI (22.7 mg, 151 μmol). The mixture was stirred at 25° C. for 16 hr. The reaction mixture was quenched with $H_2O$ (5 mL) at 25° C. and extracted with EtOAc (10 mL×3). The combined organic layers were washed with brine (50 mL×3), dried over $Na_2SO_4$, filtered and concentrated under reduced pressure. After purified by prep-HPLC (column: Phenomenex C18 150×25 mm×10 m; mobile phase: [water ($NH_4HCO_3$)-ACN]; gradient: 26%-56% B over 11 min), 4-((1-(4-(2-(2-aminopyridin-3-yl)-5-(oxazol-4-yl)-3H-imidazo[4,5-b]pyridin-3-yl)benzyl)piperidin-4-yl)amino)pyrimidine-2-carbonitrile (Example 594, 62.6 mg, yield: 35% for three steps) was obtained as a yellow solid. MS: m/z=570.2 [M+H]+. $^1$H NMR (400 MHz, Dimethylsulfoxide-$d_6$) δ 8.49 (s, 1H), 8.45 (s, 1H), 8.27 (d, J=8.0 Hz, 1H), 8.14-8.03 (m, 2H), 7.99 (dd, J=4.8, 1.6 Hz, 1H), 7.92 (d, J=8.4 Hz, 1H), 7.49-7.39 (m, 4H), 7.13 (dd, J=7.6, 1.2 Hz, 1H), 6.98 (br s, 2H), 6.68 (d, J=6.4 Hz, 1H), 6.37 (dd, J=7.6, 4.8 Hz, 1H), 3.95-3.71 (m, 1H), 3.58 (s, 2H), 2.86-2.80 (m, 2H), 2.20-2.12 (m, 2H), 1.97-1.84 (m, 2H), 1.57-1.45 (m, 2H).

Example 595: 4-((1-(4-(2-(2-Aminopyridin-3-yl)-5-(4-fluoropyridin-3-yl)-3H-imidazo[4,5-b]pyridin-3-yl)benzyl)piperidin-4-yl)amino)pyrimidine-2-carbonitrile

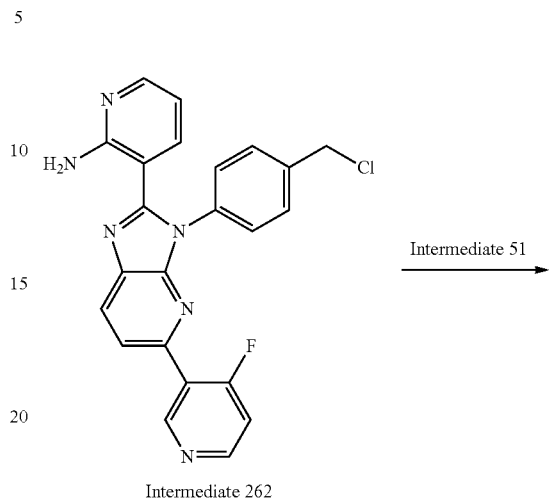

Intermediate 262

→ Intermediate 51

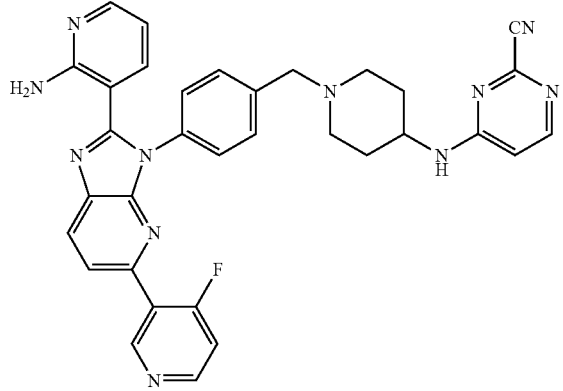

Example 595

To a solution of Intermediate 262 (286 mg, 664 μmol) in DMF (4 mL) were added Intermediate 51 (149 mg, 731 μmol), NaI (19.9 mg, 133 μmol), and $K_2CO_3$ (276 mg, 2.0 mmol). The mixture was stirred at 25° C. for 12 hr under $N_2$. The mixture was diluted with $H_2O$ (6 mL) and extracted with EtOAc (6 mL×3). The combined organic phases was washed with brine (6 mL), dried over anhydrous $Na_2SO_4$, filtered and concentrated. After purified by prep-HPLC (column: Welch Xtimate C18 150×25 mm×5 μm; mobile phase: [water ($NH_4HCO_3$)-ACN]; gradient: 42%-72% B over 7 min), 4-((1-(4-(2-(2-aminopyridin-3-yl)-5-(4-fluoropyridin-3-yl)-3H-imidazo[4,5-b]pyridin-3-yl)benzyl)piperidin-4-yl)amino)pyrimidine-2-carbonitrile (Example 595, 28.2 mg, yield: 6.8% for 3 steps) was obtained as a light yellow solid. MS: m/z=620.2 [M+Na]+. $^1$H NMR (400 MHz, Dimethylsulfoxide-$d_6$) δ 8.98 (d, J=10.8 Hz, 1H), 8.61 (dd, J=7.2, 5.6 Hz, 1H), 8.34 (d, J=8.4 Hz, 1H), 8.12-7.97 (m, 3H), 7.83 (d, J=6.8 Hz, 1H), 7.50-7.42 (m, 5H), 7.18 (d, J=6.4 Hz, 1H), 7.01 (br s, 2H), 6.66 (d, J=6.0 Hz, 1H), 6.39 (dd, J=7.6, 4.8 Hz, 1H), 3.82-3.76 (m, 1H), 3.57 (s, 2H), 2.86-2.75 (m, 2H), 2.21-2.08 (m, 2H), 1.99-1.80 (m, 2H), 1.54-1.44 (m, 2H). $^{19}$F NMR (400 MHz, Dimethylsulfoxide-$d_6$) δ −108.465.

Example 596: 4-((1-(4-(2-(2-Aminopyridin-3-yl)-5-(4-methylpyridin-2-yl)-3H-imidazo[4,5-b]pyridin-3-yl)benzyl)piperidin-4-yl)amino)pyrimidine-2-carbonitrile Example 597: 4-((1-(4-(2-(2-aminopyridin-3-yl)-5-(6-(methoxy-d3)pyridin-3-yl-2-d)-3H-imidazo[4,5-b]pyridin-3-yl)benzyl)piperidin-4-yl)amino)pyrimidine-2-carbonitrile

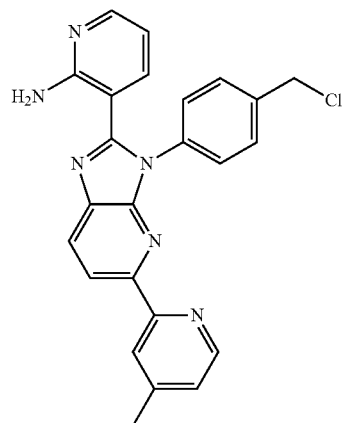

Intermediate 263

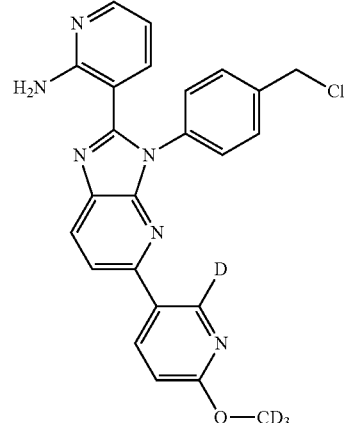

Intermediate 265

Intermediate 51 →

Intermediate 51 →

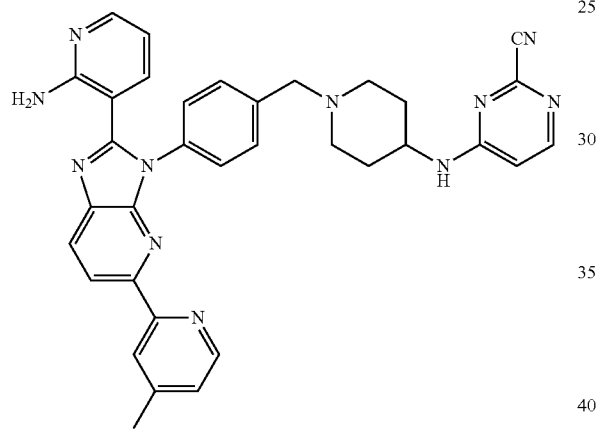

Example 596

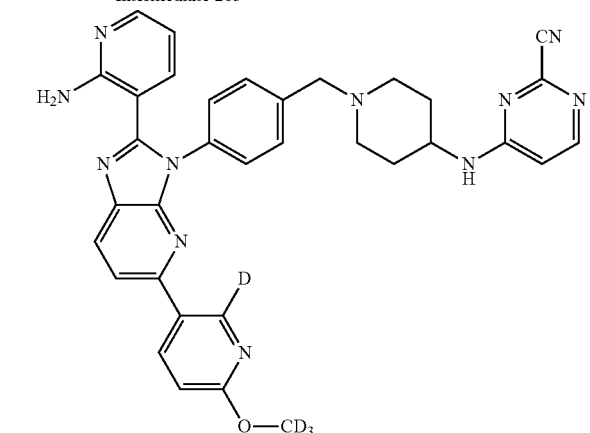

Example 597

To a mixture of Intermediate 263 (261 mg, 611 μmol) and 4-(piperidin-4-ylamino)pyrimidine-2-carbonitrile (137 mg, 672 μmol) in DMF (3 mL) was added DIEA (395 mg, 3.06 mmol). The mixture was stirred at 20° C. for 1 hr. The mixture was diluted with $H_2O$ (50 mL and extracted with EtOAc (50 mL×2). The combined organic layers were washed with brine (50 mL), dried over anhydrous $Na_2SO_4$, filtered and concentrated. After purified by prep-HPLC (column: C18 150×30 mm; mobile phase: [water ($NH_3H_2O$+ $NH_4HCO_3$)-ACN]; gradient. 47%-77% B over 7 min), 4-((1-(4-(2-(2-aminopyridin-3-yl)-5-(4-methylpyridin-2-yl)-3H-imidazo[4,5-b]pyridin-3-yl)benzyl)piperidin-4-yl)amino)pyrimidine-2-carbonitrile (Example 596, 122.7 mg, yield: 33.8% for three steps) was obtained as an off white solid. MS: m/z=616.2 [M+Na]$^+$. $^1$H NMR (400 MHz, Dimethylsulfoxide-$d_6$) δ 8.53 (d, J=4.8 Hz, 1H), 8.46 (d, J=8.4 Hz, 1H), 8.30 (d, J=8.4 Hz, 1H), 8.07 (dd, J=14.0, 6.0 Hz, 2H), 8.02-7.97 (m, 2H), 7.53-7.45 (m, 4H), 7.23 (d, J=4.0 Hz, 1H), 7.17 (dd, J=7.6, 1.6 Hz, 1H), 7.03 (br s, 2H), 6.68 (d, J=6.0 Hz, 1H), 6.38 (dd, J=7.6, 4.8 Hz, 1H), 3.82 (s, 1H), 3.61 (s, 2H), 2.89-2.80 (m, 2H), 2.34 (s, 3H), 2.22-2.11 (m, 2H), 1.94-1.85 (m, 2H), 1.58-1.44 (m, 2H).

To a solution of Intermediate 265 (226 mg, 466 μmol, HCl salt) and Intermediate 51 (145 mg, 466 μmol, TFA) in DMF (2 mL) were added $K_2CO_3$ (322 mg, 2.33 mmol) and NaI (14 mg, 93.3 μmol). The mixture was stirred at 50° C. for 1 hr. The reaction mixture was quenched with $H_2O$ (5 mL) at 25° C. and extracted with $CH_2Cl_2$ (15 mL×2). The combined organic layers were washed with brine (50 mL×3), dried over $Na_2SO_4$, filtered and concentrated under reduced pressure. After purified by prep-HPLC (column: Phenomenex C18 150×25 mm×10 μm; mobile phase: [water ($NH_4HCO_3$)-ACN]; gradient: 35%-65% B over 11 min), 4-((1-(4-(2-(2-aminopyridin-3-yl)-5-(6-(methoxy-d3)pyridin-3-yl-2-d)-3H-imidazo[4,5-b]pyridin-3-yl)benzyl)piperidin-4-yl)amino)pyrimidine-2-carbonitrile (Example 597, 106 mg, yield: 37% for two steps) was obtained as a light yellow lyophilized powder. MS: m/z=613.3 [M+H]$^+$. D %: 3D %=57.4%, 4D %=38.2%. $^1$H NMR (400 MHz, Dimethylsulfoxide-$d_6$) δ 8.85 (s, 1H), 8.30 (dd, J=8.8, 2.8 Hz, 1H), 8.27 (d, J=8.4 Hz, 1H), 8.11-7.95 (m, 4H), 7.50-7.41 (m, 4H), 7.16 (dd, J=7.6, 1.6 Hz, 1H), 7.03 (br s, 2H), 6.96-6.87 (m, 1H), 6.67 (d, J=6.0 Hz, 1H), 6.38 (dd, J=7.6, 4.4 Hz, 1H), 3.90-3.75 (m, 1H), 3.59 (s, 2H), 2.89-2.79 (m, 2H), 2.21-2.10 (m, 2H), 1.95-1.83 (m, 2H), 1.57-1.44 (m, 2H).

Example 598: 4-((1-(4-(2-(2-Aminopyridin-3-yl)-5-(6-(methoxy-d)pyridin-3-yl)-3H-imidazo[4,5-b]pyridin-3-yl)benzyl)piperidin-4-yl)amino)pyrimidine-2-carbonitrile

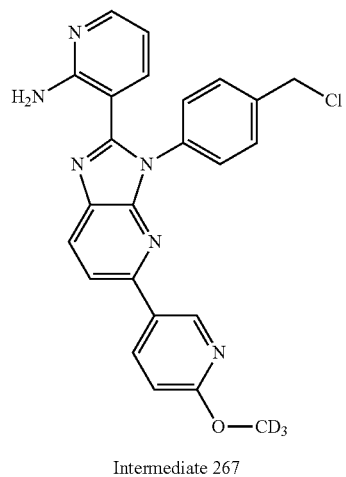

Intermediate 267

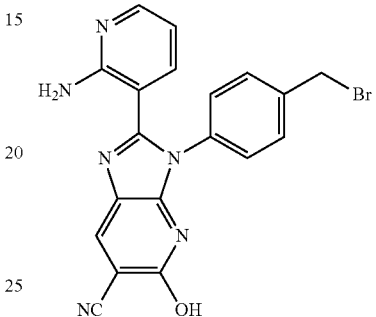

Intermediate 268

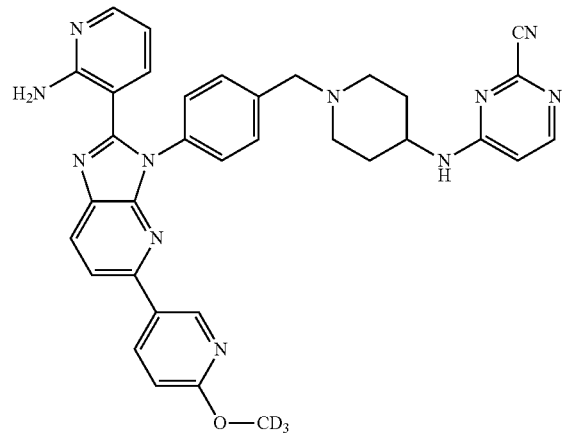

Example 598

To a solution of Intermediate 267 (380 mg, 788 µmol, HCl salt) and Intermediate 51 (250 mg, 788 µmol, TFA) in DMF (5 mL) were added K$_2$CO$_3$ (544 mg, 3.94 mmol) and NaI (11.8 mg, 78.8 µmol). The mixture was stirred at 50° C. for 1 hr. The reaction mixture was quenched with H$_2$O (50 mL) at 25° C. and extracted with CH$_2$Cl$_2$ (50 mL×2). The combined organic layers were washed with brine (50 mL×3), dried over Na$_2$SO$_4$, filtered and concentrated under reduced pressure. After purified by silica gel flash chromatography (Eluent of 1%~5% MeOH in CH$_2$Cl$_2$), 4-((1-(4-(2-(2-aminopyridin-3-yl)-5-(6-(methoxy-d$_3$)pyridin-3-yl)-3H-imidazo[4,5-b]pyridin-3-yl)benzyl)piperidin-4-yl)amino)pyrimidine-2-carbonitrile (Example 598, 104.7 mg, yield: 22% for two steps) was obtained as a brown solid. MS: m/z=613.3 [M+H]$^+$. D %: 3D %=98.9%. $^1$H NMR (400 MHz, Dimethylsulfoxide-d$_6$) δ 8.85 (d, J=2.0 Hz, 1H), 8.35-8.23 (m, 2H), 8.13-7.95 (m, 4H), 7.52-7.40 (m, 4H), 7.17-7.11 (m, 1H), 7.04 (s, 2H), 6.91 (d, J=8.4 Hz, 1H), 6.67 (d, J=6.0 Hz, 1H), 6.38 (dd, J=7.6, 4.8 Hz, 1H), 3.98-3.70 (m, 1H), 3.59 (s, 2H), 2.87-2.78 (m, 2H), 2.21-2.09 (m, 2H), 1.94-1.84 (m, 2H), 1.56-1.46 (m, 2H).

Example 599: 2-(2-Aminopyridin-3-yl)-3-(4-((4-((2-cyanopyrimidin-4-yl)amino)piperidin-1-yl)methyl)phenyl)-5-hydroxy-3H-imidazo[4,5-b]pyridine-6-carbonitrile Example 599

To a solution of Intermediate 268 (350 mg, 830 µmol) and 4-(piperidin-4-ylamino)pyrimidine-2-carbonitrile (203 mg, 997 µmol) in DMF (3 mL) were added K$_2$CO$_3$ (459 mg, 3.3 mmol) and NaI (6.2 mg, 41 µmol). The mixture was stirred at 50° C. for 1 hr. The reaction mixture was quenched with H$_2$O (10 mL) at 25° C. and extracted with CH$_2$Cl$_2$ (15 mL×2). The combined organic layers were washed with brine (50 mL×3), dried over Na$_2$SO$_4$, filtered and concentrated under reduced pressure. After purified by silica gel flash chromatography (Eluent of 0%~10% MeOH in CH$_2$Cl$_2$), 2-(2-aminopyridin-3-yl)-3-(4-((4-((2-cyanopyrimidin-4-yl)amino)piperidin-1-yl)methyl)phenyl)-5-hydroxy-3H-imidazo[4,5-b]pyridine-6-carbonitrile (Example 599, 43.2 mg, yield: 9% for two steps) was obtained as a yellow solid. MS: m/z=544.2 [M+H]$^+$. $^1$H NMR (400 MHz, Dimethylsulfoxide-d$_6$) δ 8.57 (s, 1H), 8.18-8.04 (m, 2H), 7.98-7.92 (m, 1H), 7.52-7.33 (m, 5H), 7.09 (d, J=6.4 Hz, 1H), 6.91 (s, 2H), 6.69 (d, J=6.4 Hz, 1H), 6.34 (dd, J=7.6, 4.8 Hz, 1H), 3.88-3.78 (m, 1H), 3.65-3.59 (m, 2H), 2.86-2.80 (m, 2H), 2.27-2.15 (m, 2H), 1.94-1.85 (m, 2H), 1.56-1.47 (m, 2H).

Example 600: 4-((1-(4-(2-(2-Amino-4-fluoropyridin-3-yl)-5-(5-fluoropyridin-2-yl)-3H-imidazo[4,5-b]pyridin-3-yl)benzyl)piperidin-4-yl)amino)pyrimidine-2-carbonitrile Example 601: 4-((1-(4-(5-(5-Fluoropyridin-2-yl)-2-(pyrimidin-5-yl)-3H-imidazo[4,5-b]pyridin-3-yl)benzyl)piperidin-4-yl)amino)pyrimidine-2-carbonitrile

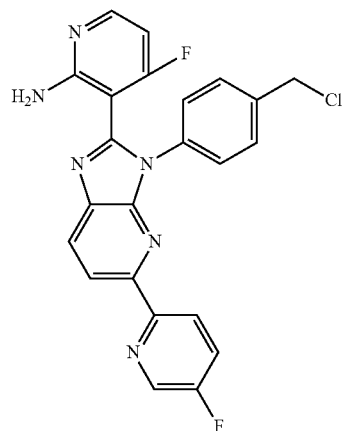

Intermediate 51 →

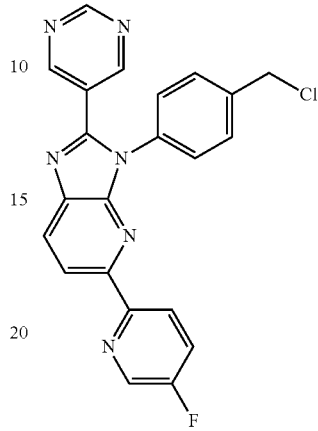

Intermediate 51 →

Intermediate 270

Intermediate 271

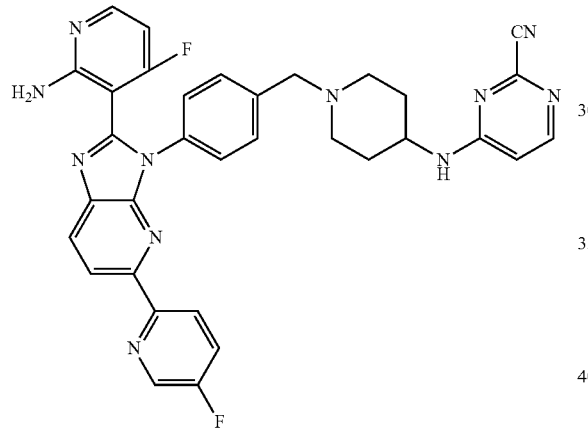

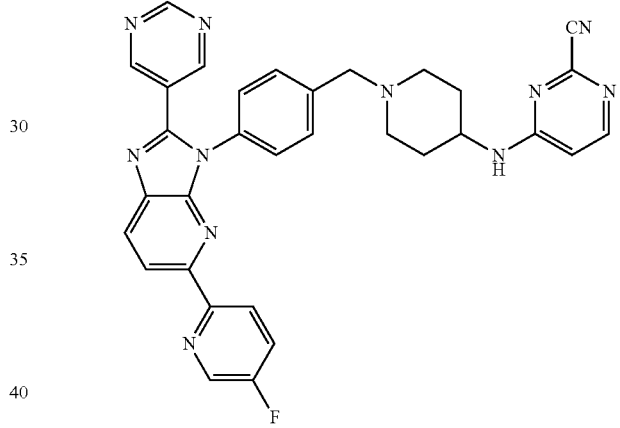

Example 600

Example 601

To a solution of Intermediate 270 (20 mg, 41.2 µmol, HCl salt) and Intermediate 51 (13.1 mg, 41.2 µmol, TFA) in DMF (1 mL) were added $K_2CO_3$ (28.5 mg, 206 µmol) and NaI (618 µg, 4.12 µmol). The mixture was stirred at 50° C. for 1 hr. The reaction mixture was quenched with $H_2O$ (5 mL) at 25° C. and extracted with $CH_2Cl_2$ (15 mL×2). The combined organic layers were washed with brine (50 mL×3), dried over $Na_2SO_4$, filtered and concentrated under reduced pressure. After purified by prep-TLC ($SiO_2$, $CH_2Cl_2$:MeOH=10:1), 4-((1-(4-(2-(2-amino-4-fluoropyridin-3-yl)-5-(5-fluoropyridin-2-yl)-3H-imidazo[4,5-b]pyridin-3-yl)benzyl)piperidin-4-yl)amino)pyrimidine-2-carbonitrile (Example 600, 7.9 mg, yield: 29% for three steps) was obtained as a yellow solid. MS: m/z=616.2 [M+H]$^+$. $^1$H NMR (400 MHz, Methanol-$d_4$) δ 8.56-8.48 (m, 2H), 8.37 (dd, J=8.8, 4.4 Hz, 1H), 8.28 (d, J=8.4 Hz, 1H), 8.08-7.98 (m, 1H), 7.66-7.61 (m, 1H), 7.55-7.47 (m, 4H), 7.35-7.30 (m, 1H), 6.61 (d, J=5.6 Hz, 1H), 6.38 (dd, J=8.8, 6.0 Hz, 1H), 4.05-3.93 (m, 1H), 3.73 (s, 2H), 3.06-2.98 (m, 2H), 2.43-2.31 (m, 2H), 2.10-2.03 (m, 2H), 1.68-1.60 (m, 2H). $^{19}$F NMR (400 MHz, Methanol-$d_4$) δ −102.89, −129.57.

To a solution of Intermediate 271 (150 mg, 360 µmol, HCl) and Intermediate 51 (114 mg, 360 µmol, TFA) in DMF (8 mL) were added $K_2CO_3$ (149 mg, 1.08 mmol) and NaI (10.8 mg, 72.0 µmol). The mixture was stirred at 50° C. for 1 hr. The reaction mixture was quenched with $H_2O$ (50 mL) at 25° C., diluted with $CH_2Cl_2$ (50 mL), and extracted with $CH_2Cl_2$ (50 mL×2). The combined organic layers were washed with brine (30 mL×3), dried over $Na_2SO_4$, filtered and concentrated under reduced pressure. After purified by prep-HPLC (column: Waters xbridge 150×25 mm×10 µm; mobile phase: [water (NH$_4$HCO$_3$)-ACN]; gradient: 35%-65% B over 10 min), 4-((1-(4-(5-(5-fluoropyridin-2-yl)-2-(pyrimidin-5-yl)-3H-imidazo[4,5-h]pyridin-3-yl)benzyl)piperidin-4-yl)amino)pyrimidine-2-carbonitrile (Example 601, 50.9 mg, yield: 24% for three steps) was obtained as a light yellow solid. MS: m/z=584.2 [M+H]$^+$. $^1$H NMR (400 MHz, Dimethylsulfoxide-$d_6$) δ 9.24 (s, 1H), 8.89 (s, 2H), 8.69 (d, J=2.8 Hz, 1H), 8.47-8.43 (m, 2H), 8.28-8.24 (m, 1H), 8.11-8.04 (m, 2H), 7.87-7.82 (m, 1H), 7.60-7.57 (m, 2H), 7.56-7.54 (m, 2H), 6.68 (d, J=5.2 Hz, 1H), 3.89-3.78 (m, 1H), 3.63 (s, 2H), 2.85 (d, J=11.2 Hz, 2H), 2.22-2.16 (m, 2H), 1.95-1.87 (m, 2H), 1.55-1.47 (m, 2H). $^{19}$F NMR (400 MHz, Dimethylsulfoxide-$d_6$) δ=−127.404.

Example 602: 4-((1-(4-(2-(2-Aminopyridin-3-yl)-6-(5-fluoropyridin-2-yl)-1H-benzo[d]imidazol-1-yl)benzyl)piperidin-4-yl)amino)pyrimidine-2-carbonitrile

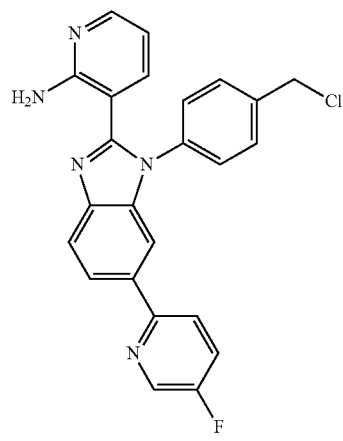

Intermediate 272

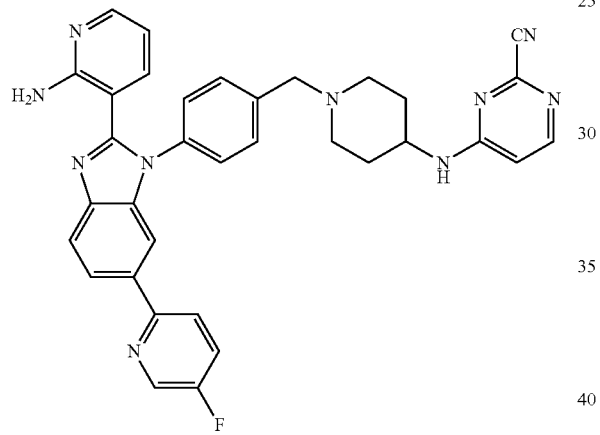

Example 602

To a solution of Intermediate 272 (300 mg, 698 μmol, HCl salt) and Intermediate 51 (221 mg, 698 μmol, TFA) in DMF (5 mL) were added K$_2$CO$_3$ (289 mg, 2.09 mmol) and NaI (20.9 mg, 140 μmol). The mixture was stirred at 50° C. for 1 hr. The reaction mixture was quenched with H$_2$O (50 mL) at 25° C. and extracted with CH$_2$Cl$_2$ (50 mL×3). The combined organic layers were washed with brine (50 mL×3), dried over Na$_2$SO$_4$, filtered and concentrated under reduced pressure. After purified by prep-HPLC (column: Phenomenex C18 150×25 mm×10 μm; mobile phase: [water (NH$_3$H$_2$O)-ACN]; gradient: 38%-68%, over 11 min), 4-((1-(4-(2-(2-aminopyridin-3-yl)-6-(5-fluoropyridin-2-yl)-1H-benzo[d]imidazol-1-yl)benzyl)piperidin-4-yl)amino)pyrimidine-2-carbonitrile (Example 602, 55.0 mg, yield: 13% for two steps) was obtained as a light yellow lyophilized powder. MS: m/z=597.2 [M+H]$^+$. $^1$H NMR (400 MHz, Dimethylsulfoxide-d$_6$) δ 8.60 (d, J=2.8 Hz, 1H), 8.08 (dd, J=8.8, 4.4 Hz, 3H), 8.04-8.01 (m, 1H), 7.98 (dd, J=4.8, 1.8 Hz, 1H), 7.90-7.88 (m, 2H), 7.81-7.76 (m, 1H), 7.54-7.52 (m, 2H), 7.44 (d, J=8.4 Hz, 2H), 7.11-7.08 (m, 3H), 6.70-6.65 (m, 1H), 6.35 (dd, J=7.6, 4.8 Hz, 1H), 3.87-3.77 (m, 1H), 3.61 (s, 2H), 2.84-2.83 (m, 2H), 2.20-2.14 (m, 2H), 1.93-1.87 (m, 2H), 1.55-1.48 (m, 2H). $^{19}$F NMR (400 MHz, Dimethylsulfoxide-d$_6$) δ=−130.25.

Example 603: 4-((1-(4-(2-(2-Aminopyridin-3-yl)-5-(5-fluoropyrimidin-2-yl)-3H-imidazo[4,5-b]pyridin-3-yl)benzyl)piperidin-4-yl)amino)pyrimidine-2-carbonitrile

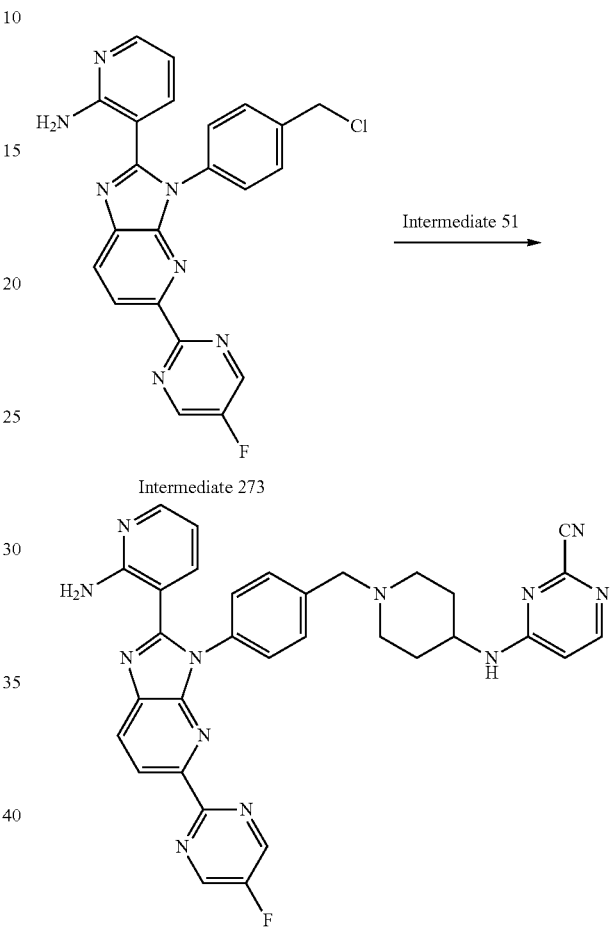

Intermediate 273

Example 603

To a solution of Intermediate 273 (300 mg, 641 μmol, HCl) in DMF (5 mL) were added NaI (9.6 mg, 64 μmol) and K$_2$CO$_3$ (266 mg, 1.92 mmol). The mixture was stirred at 25° C. for 16 hr. The reaction mixture was diluted with H$_2$O (30 mL) and extracted with EtOAc (20 mL×3). The combined organic layers were washed with brine (30 mL), dried over Na$_2$SO$_4$, filtered and concentrated under reduced pressure. After purified by prep-HPLC (column: Phenomenex C18 150×25 mm×10 μm; mobile phase: [water (NH$_3$H$_2$O+ NH$_4$HCO$_3$)-ACN]; gradient: 32%-52% B over 11 min), 4-((1-(4-(2-(2-aminopyridin-3-yl)-5-(5-fluoropyrimidin-2-yl)-3H-imidazo[4,5-b]pyridin-3-yl)benzyl)piperidin-4-yl)amino)pyrimidine-2-carbonitrile (Example 603, 47.1 mg, yield: 12% for three steps) was obtained as a yellow solid. MS: m/z=599.1 [M+H]$^+$. $^1$H NMR (400 MHz, Dimethylsulfoxide-d$_6$) δ 9.00 (s, 2H), 8.43 (d, J=8.4 Hz, 1H), 8.34 (d, J=8.4 Hz, 1H), 8.15-8.02 (m, 2H), 8.02-7.97 (m, 1H), 7.52-7.40 (m, 4H), 7.20-7.10 (m, 1H), 7.00 (br s, 2H), 6.67 (d, J=6.0 Hz, 1H), 6.37 (dd, J=7.6, 4.8 Hz, 1H), 3.89-3.74 (m, 1H), 3.59 (s, 2H), 2.92-2.77 (m, 2H), 2.23-

2.10 (m, 2H), 1.95-1.80 (m, 2H), 1.61-1.42 (m, 2H). $^{19}$F NMR (400 MHz, Dimethysulfoxide-d$_6$) δ −139.07.

Example 604: 4-((1-(4-(2-(2-Aminopyridin-3-yl)-5-(5-methylpyrimidin-2-yl)-3H-imidazo[4,5-b]pyridin-3-yl)benzyl)piperidin-4-yl)amino)pyrimidine-2-carbonitrile

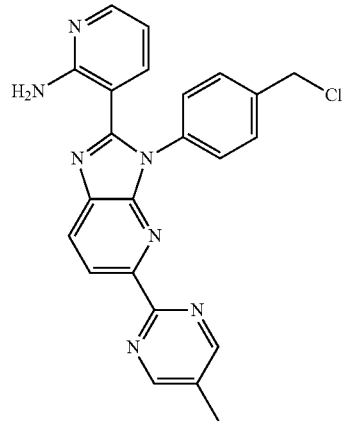

Intermediate 274

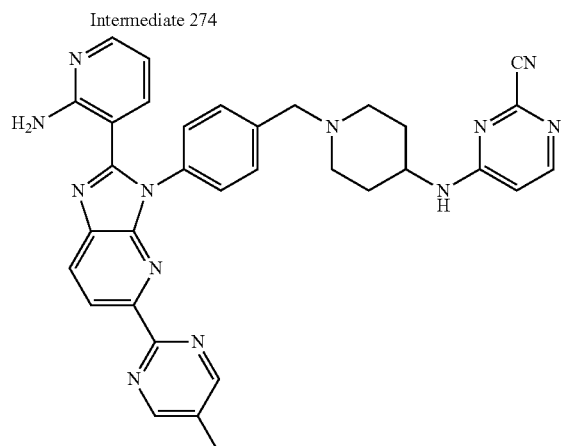

Example 604

To a solution of Intermediate 274 (142 mg, 332 μmol) and Intermediate 51 (126 mg, 398 μmol, TFA) in DMF (2 mL) were added K$_2$CO$_3$ (229 mg, 1.66 mmol) and NaI (14.9 mg, 99.6 μmol). The mixture was stirred at 25° C. for 16 hr. The reaction mixture was poured into H$_2$O (15 mL) and extracted with EtOAc (15 mL×3). The combined organic layers were dried over anhydrous Na$_2$SO$_4$, filtered and concentrated under reduced pressure. After purified by silica gel flash chromatography (Eluent of 0%~5% MeOH in CH$_2$Cl$_2$), 4-((1-(4-(2-(2-aminopyridin-3-yl)-5-(5-methylpyrimidin-2-yl)-3H-imidazo[4,5-b]pyridin-3-yl)benzyl)piperidin-4-yl)amino)pyrimidine-2-carbonitrile (Example 604, 34.9 mg, yield: 18% for three steps) was obtained as a yellow solid. MS: m/z=595.2 [M+H]$^+$. $^1$H NMR (400 MHz, Dimethylsulfoxide-d$_4$) δ 8.84-8.66 (m, 2H), 8.46 (d, J=8.4 Hz, 1H), 8.32 (d, J=8.4 Hz, 1H), 8.19-8.02 (m, 2H), 8.01-7.96 (m, 1H), 7.61-7.28 (m, 4H), 7.22-7.08 (m, 1H), 7.00 (s, 2H), 6.77-6.57 (m, 1H), 6.44-6.30 (m, 1H), 3.89-3.70 (m, 1H), 3.60 (br s, 2H), 2.98-2.69 (m, 2H), 2.32 (s, 3H), 2.25-2.09 (m, 2H), 1.95-1.75 (m, 2H), 1.55-1.43 (m, 2H).

Example 605: 4-((1-(4-(2-(2-Aminopyridin-3-yl)-5-(5-fluoropyrazin-2-yl)-3H-imidazo[4,5-b]pyridin-3-yl)benzyl)piperidin-4-yl)amino)pyrimidine-2-carbonitrile

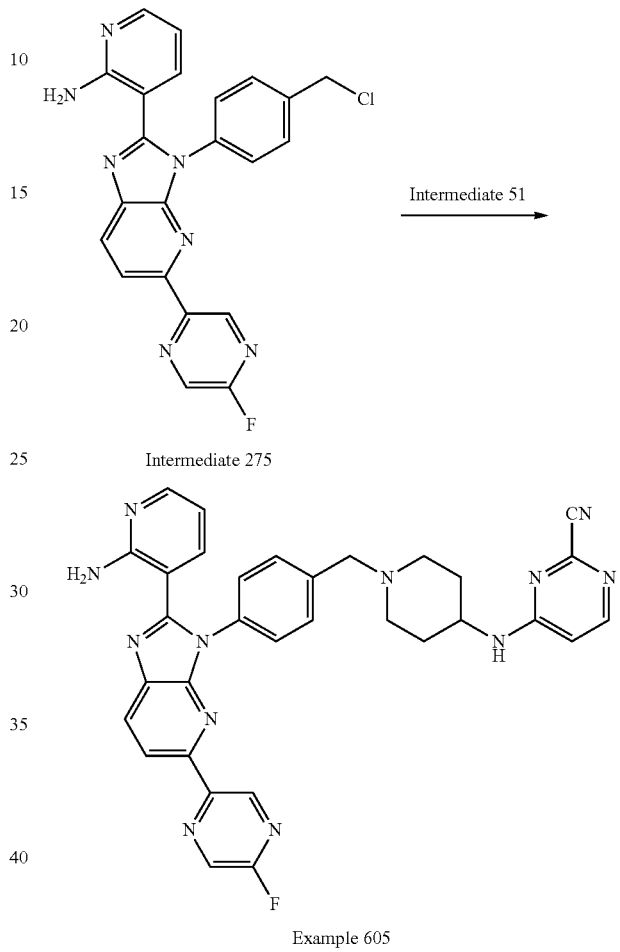

To a solution of Intermediate 275 (146 mg, 338 μmol, HCl salt) and 4-(piperidin-4-ylamino)pyrimidine-2-carbonitrile (118 mg, 372 μmol, TFA) in DMF (2 mL) were added K$_2$CO$_3$ (234 mg, 1.69 mmol) and NaI (15.2 mg, 101 μmol). The mixture was stirred at 25° C. for 1.5 hr. The reaction mixture was poured into H$_2$O (15 mL), extracted with EtOAc (15 mL×3). The combined organic layers were dried over anhydrous Na$_2$SO$_4$, filtered and concentrated under reduced pressure. After purified by prep-HPLC (column: Phenomenex C18 150×25 mm×10 μm; mobile phase: [water (NH$_4$HCO$_3$)-ACN]; gradient: 40%-60% B over 11 min), 4-((1-(4-(2-(2-aminopyridin-3-yl)-5-(5-fluoropyrazin-2-yl)-3H-imidazo[4,5-b]pyridin-3-yl)benzyl)piperidin-4-yl)amino)pyrimidine-2-carbonitrile (Example 605, 11 mg, yield: 5% for two steps) was obtained as a light yellow lyophilized powder. MS: m/z=599.3 [M+H]$^+$. $^1$H NMR (400 MHz, Dimethylsulfoxide-d$_6$) δ 9.04-8.91 (m, 1H), 8.85-8.73 (m, 1H), 8.39 (d, J=8.4 Hz, 1H), 8.32 (d, J=8.4 Hz, 1H), 8.15-7.97 (m, 3H), 7.53-7.47 (m, 4H), 7.16 (dd, J=7.6, 1.6 Hz, 1H), 7.02 (br s, 2H), 6.67 (d, J=6.0 Hz, 1H), 6.40 (dd, J=7.6, 4.8 Hz, 1H), 3.95-3.70 (m, 1H), 3.60 (s, 2H), 2.87-

2.80 (m, 2H), 2.21-2.12 (m, 2H), 1.95-1.84 (m, 2H), 1.57-1.44 (m, 2H). $^{19}$F NMR (400 MHz, Dimethylsulfoxide-d$_6$) δ -82.705.

Example 606: 4-((1-(4-(2-(2-Aminopyridin-3-yl)-5-(6-(fluoromethoxy)pyridin-3-yl)-3H-imidazo[4,5-b]pyridin-3-yl)benzyl)piperidin-4-yl)amino)pyrimidine-2-carbonitrile

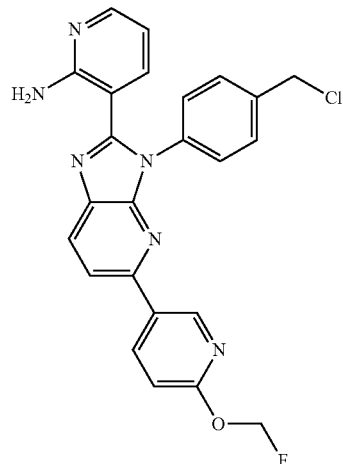

Intermediate 277

→ Intermediate 51

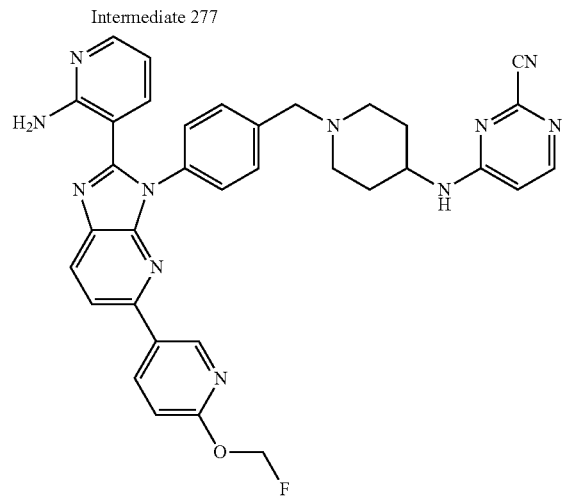

Example 606

To a solution of Intermediate 277 (250 mg, 542 μmol, HCl salt) and Intermediate 51 (172 mg, 542 μmol, TFA) in DMF (3 mL) were added K$_2$CO$_3$ (300 mg, 1.17 mmol) and NaI (40.7 mg, 271 μmol). The mixture was stirred at 25° C. for 16 hr. The reaction mixture was quenched with H$_2$O (5 mL) at 25° C. and extracted with EtOAc (10 mL×3). The combined organic layers were washed with brine (50 mL×3), dried over Na$_2$SO$_4$, filtered and concentrated under reduced pressure. After purified by prep-HPLC (column: Phenomenex C18 150×25 mm×10 μm; mobile phase: [water (NH$_4$HCO$_3$)-ACN]; gradient: 35%-65% B over 11 min), 4-((1-(4-(2-(2-aminopyridin-3-yl)-5-(6-(fluoromethoxy)pyridin-3-yl)-3H-imidazo[4,5-b]pyridin-3-yl)benzyl)piperidin-4-yl)amino)pyrimidine-2-carbonitrile (Example 606, 145.3 mg, yield: 43% for three steps) was obtained as a yellow powder. MS: m/z=628.2 [M+H]j. $^1$H NMR (400 MHz, Dimethylsulfoxide-d$_6$) δ 8.97-8.84 (m, 1H), 8.43 (d, J=8.8 Hz, 1H), 8.30 (d, J=8.4 Hz, 1H), 8.20-7.89 (m, 4H), 7.57-7.36 (m, 4H), 7.22-6.98 (m, 4H), 6.83-6.60 (m, 1H), 6.45-6.32 (m, 1H), 6.24-6.02 (m, 2H), 4.01-3.67 (m, 1H), 3.65-3.59 (s, 2H), 2.90-2.77 (m, 2H), 2.23-2.09 (m, 2H), 1.96-1.80 (m, 2H), 1.57-1.40 (m, 2H). $^{19}$F NMR (400 MHz, Dimethylsulfoxide-d$_6$) δ -154.35.

Example 607: 4-((1-(4-(2-(2-Aminopyridin-3-yl)-5-(1-(fluoromethyl)-6-oxo-1,6-dihydropyridin-3-yl)-3H-imidazo[4,5-b]pyridin-3-yl)benzyl)piperidin-4-yl)amino)pyrimidine-2-carbonitrile

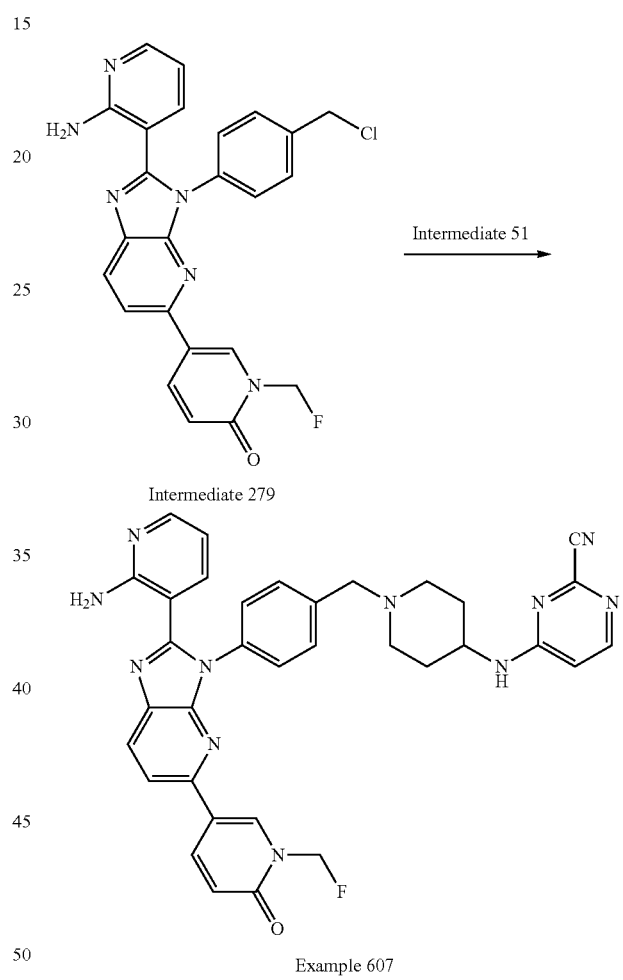

To a solution of Intermediate 279 (458 mg, 921 μmol, HCl salt) and Intermediate 51 (292 mg, 921 μmol) in DMF (3 mL) were added K$_2$CO$_3$ (509 mg, 3.68 mmol) and NaI (69 mg, 460 μmol). The mixture was stirred at 25° C. for 16 hr. The reaction mixture was quenched with H$_2$O (30 mL) at 25° C. and extracted with EtOAc (10 mL×3). The combined organic layers were washed with brine (20 mL×3), dried over Na$_2$SO$_4$, filtered and concentrated under reduced pressure. After purified by prep-HPLC (column: Daisogel SP ODS RPS 150×25 mm×5 μm; mobile phase: [water (NH$_4$HCO$_3$)-ACN]; gradient: 22%-52% B over 11 min), 4-((1-(4-(2-(2-aminopyridin-3-yl)-5-(1-(fluoromethyl)-6-oxo-1,6-dihydropyridin-3-yl)-3H-imidazo[4,5-b]pyridin-3-yl)benzyl)piperidin-4-yl)amino)pyrimidine-2-carbonitrile (Example 607, 291 mg, yield: 49% for three steps) was obtained as a yellow powder. MS: m/z=628.2 [M+H]⁺. ¹H NMR (400 MHz, Dimethylsulfoxide-d₆) δ 8.60 (d, J=2.4 Hz, 1H), 8.27 (d, J=8.4 Hz, 1H), 8.17 (dd, J=9.6, 2.4 Hz, 1H), 8.12-7.96 (m, 3H), 7.86 (d, J=8.4 Hz, 1H), 7.50-7.41 (m, 4H), 7.16-7.11 (m, 1H), 7.02 (s, 2H), 6.68 (d, J=6.4 Hz, 1H), 6.60 (d, J=9.6 Hz, 1H), 6.37 (dd, J=7.6, 4.8 Hz, 1H), 6.03 (d, J=50.8 Hz, 1H), 3.92-3.66 (m, 1H), 3.59 (s, 2H), 2.89-2.78 (m, 2H), 2.21-2.10 (m, 2H), 1.95-1.82 (m, 2H), 1.56-1.44 (m, 2H). ¹⁹F NMR (400 MHz, Dimethylsulfoxide-d₆) δ −172.673.

Example 608: 4-((1-(4-(2-(2-Aminopyridin-3-yl)-5-(2-(methyl-d₃)-2H-1,2,3-triazol-4-yl)-3H-imidazo[4,5-b]pyridin-3-yl)benzyl)piperidin-4-yl)amino)pyrimidine-2-carbonitrile

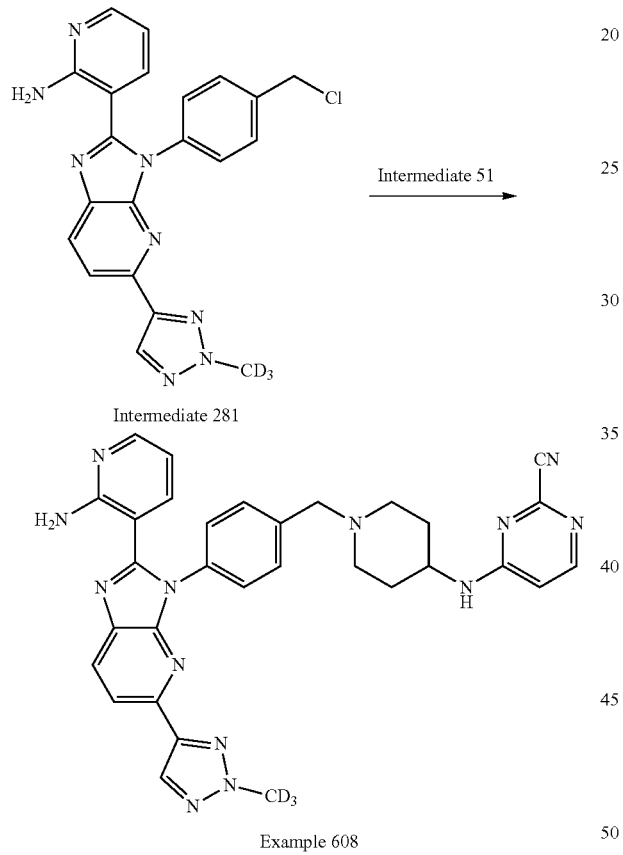

Intermediate 281

Example 608

To a solution of Intermediate 281 (420 mg, 920 μmol, HCl salt) and Intermediate 51 (292 mg, 920 μmol, TFA) in DMF (5 mL) were added K₂CO₃ (636 mg, 4.6 mmol) and NaI (13.8 mg, 92 μmol). The mixture was stirred at 50° C. for 1 hr. The reaction mixture was quenched with H₂O (50 mL) at 25° C. and extracted with CH₂Cl₂ (50 mL×2). The combined organic layers were washed with brine (50 mL×3), dried over Na₂SO₄, filtered and concentrated under reduced pressure. After purified by silica gel flash chromatography (Eluent of 1%~6% MeOH in CH₂Cl₂), 4-((1-(4-(2-(2-aminopyridin-3-yl)-5-(2-(methyl-d₃)-2H-1,2,3-triazol-4-yl)-3H-imidazo[4,5-b]pyridin-3-yl)benzyl)piperidin-4-yl)amino)pyrimidine-2-carbonitrile (Example 608, 301.2 mg, yield: 53% for two steps) was obtained as a green solid. MS: m/z=587.2 [M+H]⁺. ¹H NMR (400 MHz, Dimethylsulfoxide-d₆) δ 8.27 (d, J=8.4 Hz, 1H), 8.09-7.91 (m, 5H), 7.48-7.40 (m, 4H), 7.16-7.08 (m, 1H), 6.93 (s, 2H), 6.67 (d, J=6.0 Hz, 1H), 6.37 (dd, J=7.6, 4.8 Hz, 1H), 3.85-3.77 (m, 1H), 3.58 (s, 2H), 2.86-2.80 (m, 2H), 2.19-2.12 (m, 2H), 1.93-1.84 (m, 2H), 1.53-1.46 (m, 2H).

Example 609: 4-((1-(4-(2-(2-Aminopyridin-3-yl)-5-(2-ethyl-2H-1,2,3-triazol-4-yl)-3H-imidazo[4,5-b]pyridin-3-yl)benzyl)piperidin-4-yl)amino)pyrimidine-2-carbonitrile

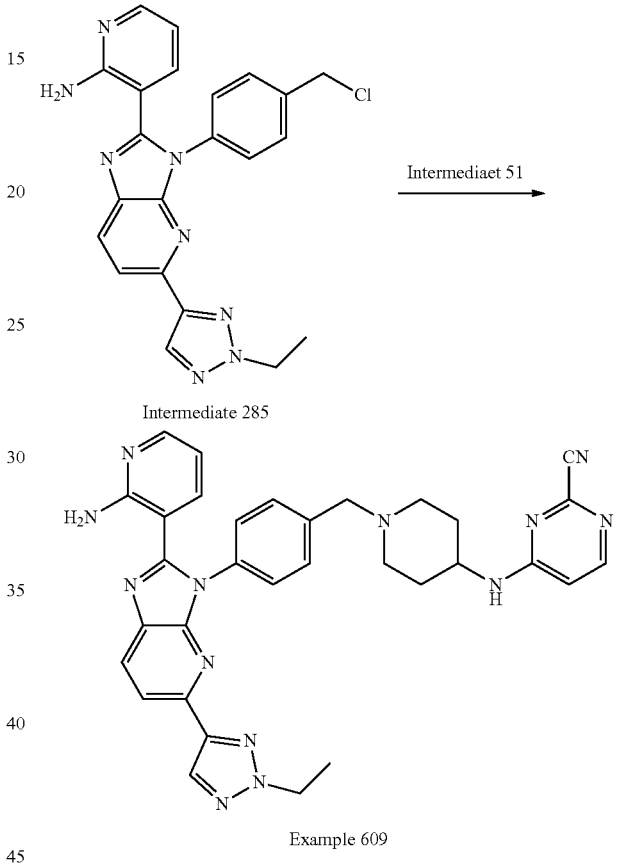

Intermediate 285

Example 609

To a mixture of Intermediate 285 (171 mg, 397 μmol) and Intermediate 51 (88.7 mg, 437 μmol) in DMF (4 mL) were added NaI (11.9 mg, 79.4 μmol) and K₂CO₃ (165 mg, 1.19 mmol). The reaction mixture was stirred at 20° C. for 12 hr. The mixture was diluted with H₂O (20 mL) and extracted with EtOAc (20 mL×2). The combined organic layers were washed with brine (10 mL), dried over anhydrous Na₂SO₄, filtered and concentrated. After purified by prep-HPLC (column: C18 150×30 mm; mobile phase: [water (NH₃H₂O+NH₄HCO₃)-ACN]; gradient: 45%-75% B over 7 min), 4-((1-(4-(2-(2-aminopyridin-3-yl)-5-(2-ethyl-2H-1,2,3-triazol-4-yl)-3H-imidazo[4,5-b]pyridin-3-yl)benzyl)piperidin-4-yl)amino)pyrimidine-2-carbonitrile (Example 609, 66 mg, 110 μmol, yield: 28% for three steps) was obtained as a yellow solid. MS: m/z=620.2 [M+Na]⁺. ¹H NMR (400 MHz, Dimethylsulfoxide-d₆) δ 8.28 (d, J=8.0 Hz, 1H), 8.13-8.04 (m, 3H), 8.02-7.92 (m, 2H), 7.51-7.40 (m, 4H), 7.14 (d, J=6.4 Hz, 1H), 6.98 (s, 2H), 6.68 (d, J=5.6 Hz, 1H), 6.37 (dd, J=7.6, 4.8 Hz, 1H), 4.57-4.46 (m, 2H), 3.89-3.77 (m, 1H), 3.64-3.55 (m, 2H), 2.89-2.77 (m, 2H), 2.22-2.09 (m, 2H), 1.95-1.84 (m, 2H), 1.55-1.44 (m, 5H).

Example 610: 4-((1-(4-(2-(2-Aminopyridin-3-yl)-5-(2-isopropyl-2H-1,2,3-triazol-4-yl)-3H-imidazo[4,5-b]pyridin-3-yl)benzyl)piperidin-4-yl)amino)pyrimidine-2-carbonitrile

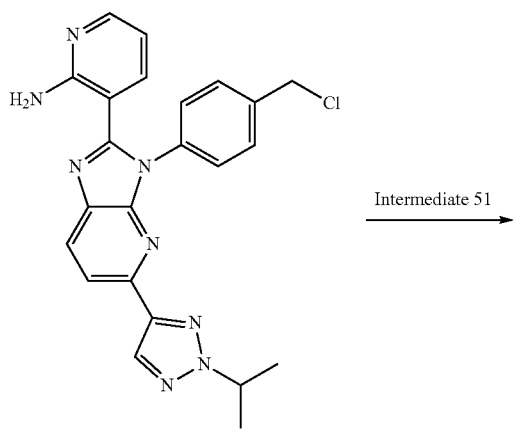

Intermediate 289

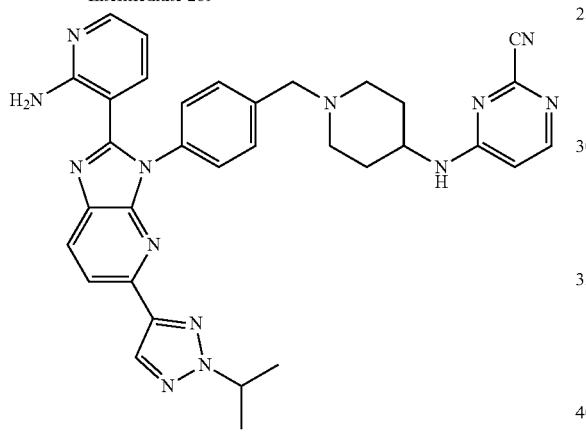

Example 610

To a solution of Intermediate 289 (146 mg, 328 μmol) and 4-(piperidin-4-ylamino)pyrimidine-2-carbonitrile (73.4 mg, 361 μmol) in DMF (5 mL) were added $K_2CO_3$ (136 mg, 984 μmol) and NaI (9.84 mg, 65.6 μmol) at 20° C. The reaction mixture was stirred at 20° C. for 12 hr. The mixture was diluted with $H_2O$ (10 mL) and extracted with EtOAc (10 mL×2). The combined organic layers were washed with brine (10 mL), dried over anhydrous $Na_2SO_4$, filtered and concentrated. After purified by prep-HPLC (column: C18 150×30 mm; mobile phase: [water ($NH_3H_2O+NH_4HCO_3$)-ACN]; gradient: 51%-81% B over 7 min), 4-((1-(4-(2-(2-aminopyridin-3-yl)-5-(2-isopropyl-2H-1,2,3-triazol-4-yl)-3H-imidazo[4,5-b]pyridin-3-yl)benzyl)piperidin-4-yl)amino)pyrimidine-2-carbonitrile (Example 610, 53.3 mg, yield: 26.6% for three steps) was obtained as an off-white solid. MS: m/z=612.3 [M+H]$^+$. $^1$H NMR (400 MHz, Dimethylsulfoxide-$d_6$) δ 8.27 (d, J=8.4 Hz, 1H), 8.15-8.03 (m, 3H), 7.99 (dd, J=4.8, 1.6 Hz, 1H), 7.95 (d, J=8.4 Hz, 1H), 7.50-7.41 (m, 4H), 7.14 (dd, J=7.6, 1.6, Hz, 1H), 7.00 (s, 2H), 6.67 (d, J=6.0 Hz, 1H), 6.37 (dd, J=8.0, 4.8 Hz, 1H), 4.93-4.82 (m, 1H), 3.82-3.81 (m, 1H), 3.59 (s, 2H), 2.87-2.78 (m, 2H), 2.23-2.09 (m, 2H), 1.96-1.78 (m, 2H), 1.58-1.43 (m, 8H).

Example 611: 4-((1-(4-(2-(2-Aminopyridin-3-yl)-5-(1-isopropyl-1H-1,2,3-triazol-4-yl)-3H-imidazo[4,5-b]pyridin-3-yl)benzyl)piperidin-4-yl)amino)pyrimidine-2-carbonitrile

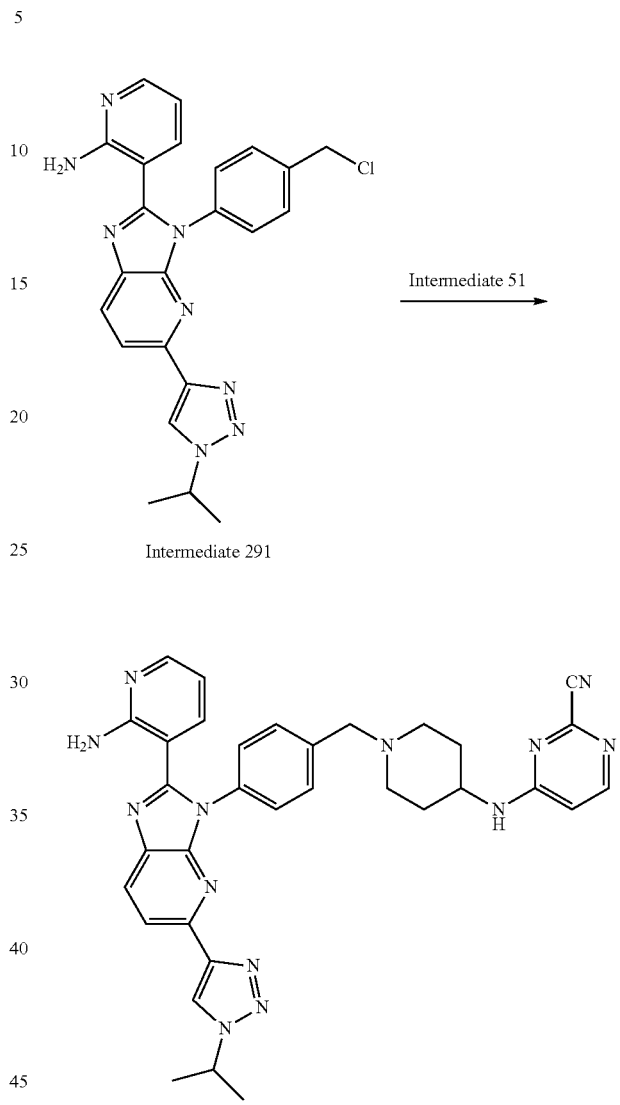

Intermediate 291

Example 611

To a solution of Intermediate 291 (220 mg, 494 μmol, HCl salt) and Intermediate 51 (111 mg, 544 μmol) in DMF (8 mL) were added NaI (14.8 mg, 98.9 μmol) and $K_2CO_3$ (205 mg, 1.48 mmol) at 20° C. The reaction mixture was stirred at 20° C. for 12 hr. The mixture was diluted with $H_2O$ (20 mL) and extracted with EtOAc (20 mL×2). The combined organic layers were washed with brine (20 mL), dried over anhydrous $Na_2SO_4$, filtered and concentrated. After purified by prep-HPLC (column: C18 150×30 mm; mobile phase: [water ($NH_3H_2O+NH_4CO_3$)-ACN]; gradient: 45%-75% B over 7 min), 4-((1-(4-(2-(2-aminopyridin-3-yl)-5-(1-isopropyl-1H-1,2,3-triazol-4-yl)-3H-imidazo[4,5-b]pyridin-3-yl)benzyl)piperidin-4-yl)amino)pyrimidine-2-carbonitrile (Intermediate 611, 119 mg, yield: 39% for three steps) was obtained as an off-white solid. MS: m/z=612.3 [M+H]$^+$. $^1$H NMR (400 MHz, Dimethylsulfoxide-$d_6$) δ 8.42 (s, 1H), 8.28 (d, J=8.4 Hz, 1H), 8.12-8.04 (m, 3H), 7.98 (dd, J=4.8, 1.6 Hz, 1H), 7.49-7.41 (m, 4H), 7.11 (dd, J=7.6, 1.6 Hz, 1H), 6.97 (br s, 2H), 6.68 (d, J=6.0 Hz, 1H), 6.36 (dd, J=7.6, 4.8

Hz, 1H), 4.93-4.82 (m, 1H), 3.87-3.76 (m, 1H), 3.59 (s, 2H), 2.89-2.79 (m, 2H), 2.22-2.11 (m, 2H), 1.94-1.79 (m, 2H), 1.54-1.47 (m, 8H).

Example 612: 4-((1-(4-(2-(2-Aminopyridin-3-yl)-5-(2-methyl-5-(methyl-d₃)-2H-1,2,3-triazol-4-yl)-3H-imidazo[4,5-b]pyridin-3-yl)benzyl)piperidin-4-yl)amino)pyrimidine-2-carbonitrile

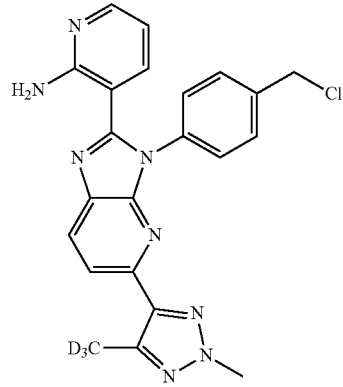

Intermediate 293

→ Intermediate 51

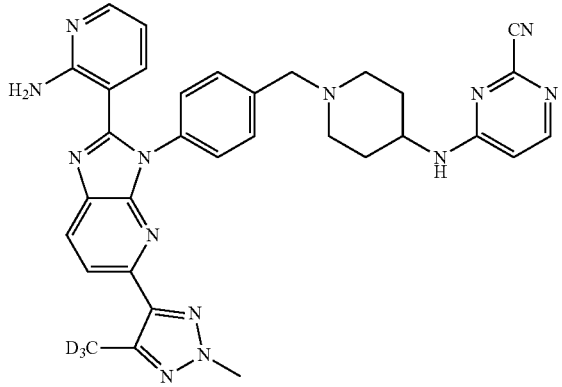

Example 612

To a solution of Intermediate 293 (170 mg, 359 μmol, HCl salt) and Intermediate 51 (114 mg, 359 μmol, TFA salt) in DMF (2 mL) were added K₂CO₃ (199 mg, 1.44 mmol) and NaI (54 mg, 359 μmol). The mixture was degassed and purged with N₂ three times and stirred at 25° C. for 1 hr under N₂. The reaction mixture was filtered and concentrated under reduced pressure. After purified by prep-HPLC (column: Waters xbridge 150×25 mm 10 μm; mobile phase: [water (NH₄HCO₃)-ACN]; gradient: 34%-64% B over 11 min), 4-((1-(4-(2-(2-aminopyridin-3-yl)-5-(2-methyl-5-(methyl-d₃)-2H-1,2,3-triazol-4-yl)-3H-imidazo[4,5-b]pyridin-3-yl)benzyl)piperidin-4-yl)amino)pyrimidine-2-carbonitrile (Example 612, 19.7 mg, yield: 8.9% for three steps) was obtained as a yellow solid. MS: m/z=601.3 [M+H]⁺. D %: 3D %=100%, ¹H NMR (400 MHz, Dimethylsulfoxide-d₆) δ 8.25 (d, J=8.0 Hz, 1H), 8.12-8.03 (m, 2H), 8.02-8.00 (m, 1H), 7.91 (d, J=8.4 Hz, 1H), 7.51-7.40 (m, 4H), 7.25 (dd, J=8.0, 1.2 Hz, 1H), 7.09 (br s, 2H), 6.67 (d, J=6.4 Hz, 1H), 6.41 (dd, J=7.6, 4.8, Hz, 1H), 4.12 (s, 3H), 3.85-3.75 (m, 1H), 3.58 (s, 2H), 3.21-3.09 (m, 2H), 2.83-2.76 (m, 2H), 2.17-2.08 (m, 2H), 1.93-1.83 (m, 2H).

Example 613: 4-((1-(4-(2-(2-Aminopyridin-3-yl)-5-(2H-1,2,3-triazol-4-yl)-3H-imidazo[4,5-b]pyridin-3-yl)benzyl)piperidin-4-yl)amino)pyrimidine-2-carbonitrile

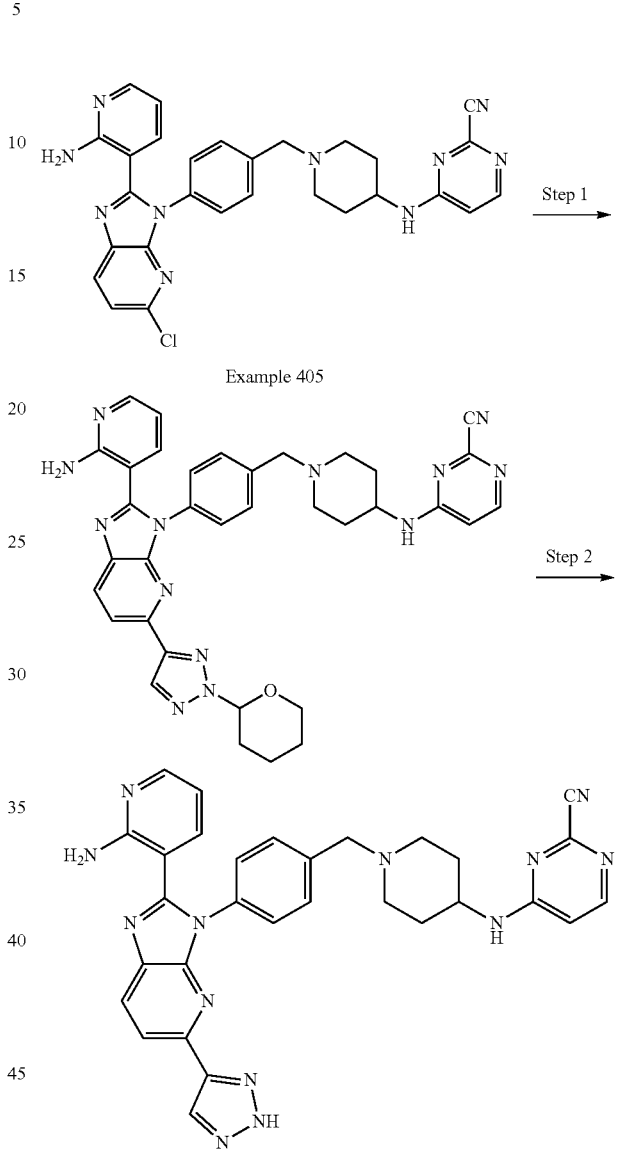

Step 1: 4-((1-(4-(2-(2-Aminopyridin-3-yl)-5-(2-(tetrahydro-2H-pyran-2-yl)-2H-1,2,3-triazol-4-yl)-3H-imidazo[4,5-b]pyridin-3-yl)benzyl)piperidin-4-yl)amino)pyrimidine-2-carbonitrile A mixture of Example 405 (250 mg, 466 μmol), 2-(tetrahydro-2H-pyran-2-yl)-4-(4,4,5,5-tetramethyl-1,3,2-dioxaborolan-2-yl)-2H-1,2,3-triazole (143 mg, 512 μmol), Pd(dppf)Cl₂ (34.1 mg, 46.5 μmol), and Cs₂CO₃ (455 mg, 1.40 mmol) in H₂O (0.5 mL) and 1,4-dioxane (2 mL) was degassed and purged with N₂ three times. The mixture was stirred at 100° C. for 16 hr under N₂ atmosphere. The reaction mixture was poured into H₂O (15 mL) and extracted with EtOAc (15 mL×3). The combined organic layers were dried over anhydrous Na₂SO₄, filtered and concentrated under reduced pressure. 4-((1-(4-(2-(2-Amino-pyridin-3-yl)-5-(2-(tetrahydro-2H-pyran-2-yl)-2H-1,2,3-triazol-4-yl)-3H-imidazo[4,5-b]pyridin-3-yl)benzyl)piperidin-4-yl)amino)pyrimidine-2-carbonitrile (285 mg) was obtained as a brown solid. MS: m/z=654.4 [M+H]+

Step 2: 4-((1-(4-(2-(2-Aminopyridin-3-yl)-5-(2H-1,2,3-triazol-4-yl)-3H-imidazo[4,5-b]pyridin-3-yl)benzyl)piperidin-4-yl)amino)pyrimidine-2-carbonitrile To a solution of 4-((1-(4-(2-(2-aminopyridin-3-yl)-5-(2-(tetrahydro-2H-pyran-2-yl)-2H-1,2,3-triazol-4-yl)-3H-imidazo[4,5-b]pyridin-3-yl)benzyl)piperidin-4-yl)amino)pyrimidine-2-carbonitrile (285 mg, 436 μmol) in CH$_2$Cl$_2$ (4 mL) was added TFA (2 mL). The mixture was stirred at 25° C. for 2 hr. The pH of reaction mixture was adjusted to 8 with aq. Sat. NaHCO$_3$. The mixture was extracted with CH$_2$Cl$_2$ (20 mL×3). The combined organic layers were dried over Na$_2$SO$_4$, filtered and concentrated under reduced pressure. After purified by prep-HPLC (column: Phenomenex C18 150×25 mm×10 μm; mobile phase: [water (NH$_4$HCO$_3$)-ACN]; gradient: 18%-48% B over 11 min), 4-((1-(4-(2-(2-aminopyridin-3-yl)-5-(2H-1,2,3-triazol-4-yl)-3H-imidazo[4,5-b]pyridin-3-yl)benzyl)piperidin-4-yl)amino)pyrimidine-2-carbonitrile (Example 613, 12.2 mg, yield: 5% for two steps) was obtained as an off white solid. MS: m/z=570.3 [M+H]+. $^1$H NMR (400 MHz, Methanol-d$_4$) δ 8.30-8.13 (m, 2H), 8.11-8.05 (m, 1H), 8.04-7.95 (m, 2H), 7.54 (d, J=8.4 Hz, 2H), 7.44 (d, J=8.4 Hz, 2H), 7.30 (dd, J=7.6, 1.6 Hz, 1H), 6.66-6.53 (m, 1H), 6.46 (dd, J=8.0, 5.2 Hz, 1H), 4.07-3.84 (m, 1H), 3.67 (br s, 2H), 3.07-2.88 (m, 2H), 2.38-2.17 (m, 2H), 2.10-1.90 (m, 2H), 1.69-1.57 (m, 2H).

Example 614: 4-((1-(4-(2-(2-Aminopyridin-3-yl)-5-(2,5-dimethyl-2H-1,2,3-triazol-4-yl)-3H-imidazo[4,5-b]pyridin-3-yl)benzyl)piperidin-4-yl)amino)pyrimidine-2-carbonitrile

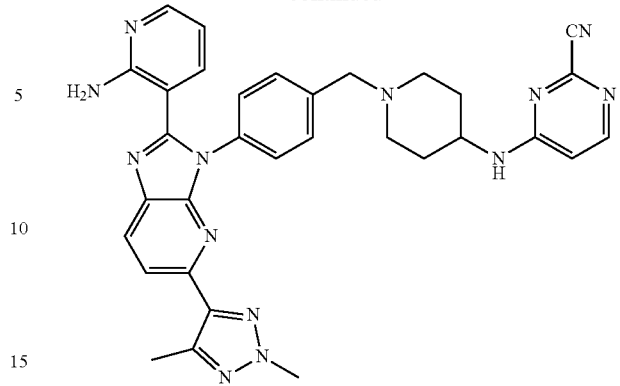

Example 614

To a mixture of Intermediate 294 (230 mg, 534 μmol) and Intermediate 51 (119 mg, 587 mol) in DMF (2 mL) were added NaI (16.0 mg, 106 μmol) and K$_2$CO$_3$ (221 mg, 1.60 mmol), the mixture was stirred at 20° C. for 12 hr. The mixture was diluted with H$_2$O (50 mL) and extracted with EtOAc (30 mL×2). The combined organic layers were washed with brine (30 mL), dried over anhydrous Na$_2$SO$_4$, filtered and concentrated. After purified by prep-HPLC (column: C18 150×30 mm; mobile phase: [water (NH$_3$H$_2$O+ NH$_4$HCO$_3$)-ACN]; gradient: 48%-78% B over 7 min), 4-((1-(4-(2-(2-aminopyridin-3-yl)-5-(2,5-dimethyl-2H-1,2,3-triazol-4-yl)-3H-imidazo[4,5-b]pyridin-3-yl)benzyl)piperidin-4-yl)amino)pyrimidine-2-carbonitrile (Example 614, 78.2 mg, yield: 24% for two steps) was obtained as a white solid. MS: m/z=598.3 [M+H]+. $^1$H NMR (400 MHz, Dimethylsulfoxide-d$_6$) δ 8.25 (d, J=8.4 Hz, 1H), 8.10-8.00 (m, 3H), 7.91 (d, J=8.4 Hz, 1H), 7.49-7.43 (m, 4H), 7.25 (dd, J=8.0, 2.0 Hz, 1H), 7.09 (s, 2H), 6.67 (d, J=5.6 Hz, 1H), 6.41 (dd, J=7.6, 4.8 Hz, 1H), 4.12 (s, 3H), 3.87-3.73 (m, 1H), 3.58 (s, 2H), 2.84-2.75 (m, 2H), 2.34 (s, 3H), 2.18-2.06 (m, 2H), 1.93-1.82 (m, 2H), 1.56-1.42 (m, 2H).

Example 615: 4-((1-(4-(2-(2-Aminopyridin-3-yl)-5-(2-cyclopropyl-2H-1,2,3-triazol-4-yl)-3H-imidazo[4,5-b]pyridin-3-yl)benzyl)piperidin-4-yl)amino)pyrimidine-2-carbonitrile

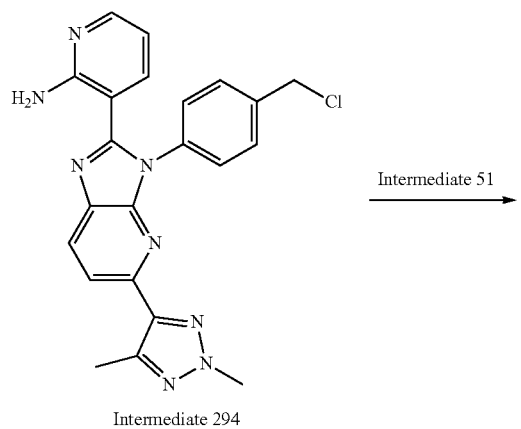

Intermediate 294

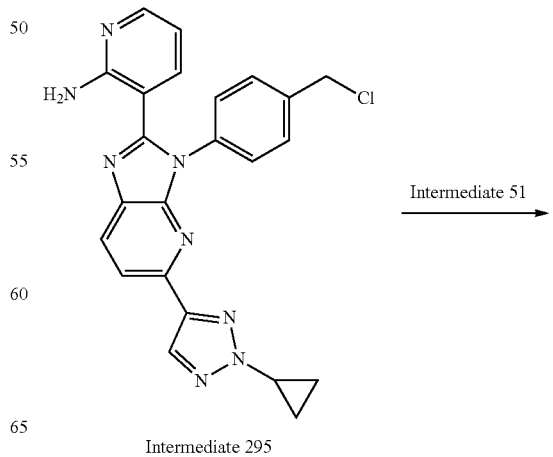

Intermediate 295

1751

-continued

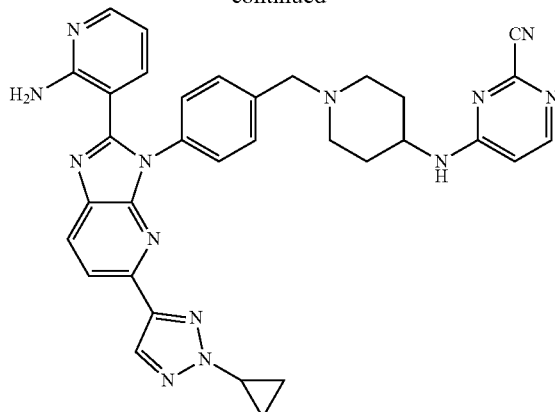

Example 615

To a solution of Intermediate 295 (170 mg, 384 µmol) and Intermediate 51 (86 mg, 422 mol) in DMF (3 mL) were added K$_2$CO$_3$ (159 mg, 1.15 mmol) and NaI (11.5 mg, 76.8 µmol) at 20° C. The reaction mixture was stirred at 20° C. for 12 hr. The reaction mixture was diluted with H$_2$O (20 ml) and extracted with EtOAc (20 mL). The organic layer was separated, dried over anhydrous Na$_2$SO$_4$ and concentrated under reduced pressure. After purified by prep-HPLC (column: Phenomenex C18 80×30 mm×5 µm; mobile phase: [water (NH$_3$H$_2$O+NH$_4$HCO$_3$)-ACN]; gradient: 46%-76% B over 7 min), 4-((1-(4-(2-(2-aminopyridin-3-yl)-5-(2-cyclopropyl-2H-1,2,3-triazol-4-yl)-3H-imidazo[4,5-b]pyridin-3-yl)benzyl)piperidin-4-yl)amino)pyrimidine-2-carbonitrile (Example 615, 68.7 mg, yield: 29% for three steps) was obtained as a yellow solid. MS: m/z=610.4 [M+H]$^+$. $^1$H NMR (400 MHz, Dimethylsulfoxide-d$_6$) δ 8.27 (d, J=8.4 Hz, 1H), 8.13-8.02 (m, 3H), 7.99 (dd, J=4.8, 1.6, Hz, 1H), 7.93 (d, J=8.4 Hz, 1H), 7.49-7.41 (m, 4H), 7.16-7.12 (m, 1H), 6.98 (s, 2H), 6.67 (d, J=6.0 Hz, 1H), 6.37 (dd, J=7.6, 4.8 Hz, 1H), 4.23-4.15 (m, 1H), 3.81-3.79 (m, 1H), 3.58 (s, 2H), 2.87-2.79 (m, 2H), 2.20-2.10 (m, 2H), 1.94-1.83 (m, 2H), 1.56-1.43 (m, 2H), 1.27-1.23 (m, 2H), 1.15-1.09 (m, 2H).

Example 616: 4-((1-(4-(2-(2-Aminopyridin-3-yl)-5-(2-methyl-2H-1,2,3-triazol-4-yl-5-d)-3H-imidazo[4,5-b]pyridin-3-yl)benzyl)piperidin-4-yl)amino)pyrimidine-2-carbonitrile

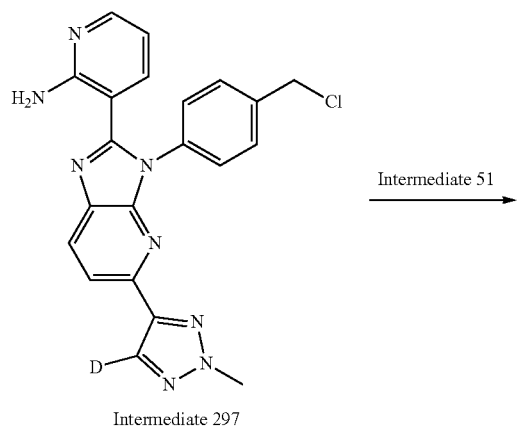

Intermediate 297

1752

-continued

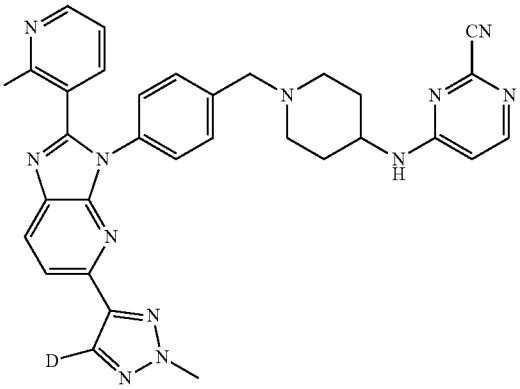

Example 616

To a solution of Intermediate 297 (20 mg, 47.9 µmol) and 4-(piperidin-4-ylamino)pyrimidine-2-carbonitrile (15.2 mg, 47.9 µmol, TFA) in DMF (2 mL) were added K$_2$CO$_3$ (19.8 mg, 144 µmol) and NaI (717 µg, 4.79 µmol). The mixture was stirred at 50° C. for 1 hr. The reaction mixture was quenched with H$_2$O (5 mL) at 25° C. and extracted with CH$_2$Cl$_2$ (15 mL×2). The combined organic layers were washed with brine (50 mL×3), dried over Na$_2$SO$_4$, filtered and concentrated under reduced pressure. After purified by prep-TLC (SiO$_2$, CH$_2$Cl$_2$:MeOH=10:1), 4-((1-(4-(2-(2-aminopyridin-3-yl)-5-(2-methyl-2H-1,2,3-triazol-4-yl-5-d)-3H-imidazo[4,5-b]pyridin-3-yl)benzyl)piperidin-4-yl)amino)pyrimidine-2-carbonitrile (Example 616, 16.6 mg, yield: 58%) was obtained as a yellow solid. MS: m/z=585.2 [M+H]$^+$. D %: 1 D %=96.2%. $^1$H NMR (400 MHz, Methanol-d$_4$) δ 8.17 (d, J=8.0 Hz, 1H), 8.04-7.95 (m, 3H), 7.53 (d, J=8.0 Hz, 2H), 7.42 (d, J=8.0 Hz, 2H), 7.31-7.23 (m, 1H), 6.60 (d, J=5.2 Hz, 1H), 6.45 (dd, J=7.6, 5.2 Hz, 1H), 4.21 (s, 3H), 4.04-3.89 (m, 1H), 3.67 (s, 2H), 3.02-2.92 (m, 2H), 2.38-2.22 (m, 2H), 2.04-1.97 (m, 2H), 1.68-1.56 (m, 2H).

Example 617: 4-((1-(4-(2-(2-Aminopyridin-3-yl)-5-(1-(difluoromethyl)-6-oxo-1,6-dihydropyridin-3-yl)-3H-imidazo[4,5-b]pyridin-3-yl)benzyl)piperidin-4-yl)amino)pyrimidine-2-carbonitrile

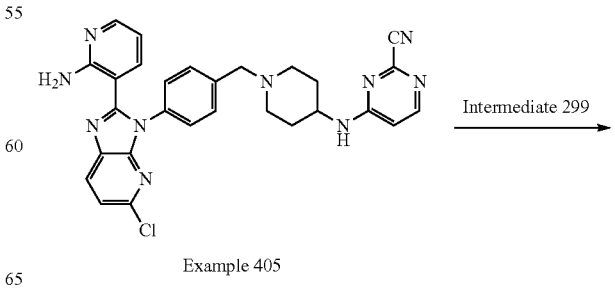

Example 405

-continued

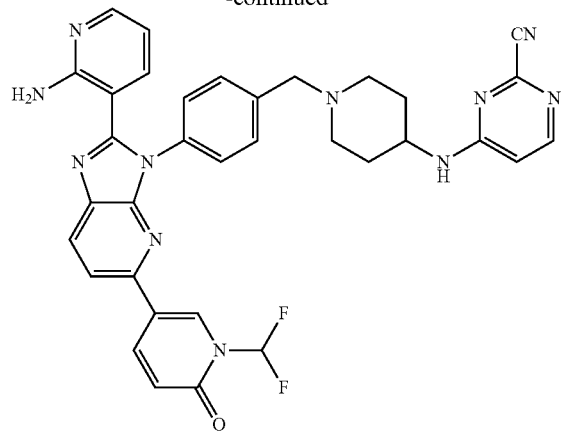

Example 617

A mixture of Example 405 (119 mg, 222 μmol), Intermediate 299 (42 mg, 222 μmol), Cs₂CO₃ (217 mg, 667 μmol), and Pd(dppf)Cl₂ (16.3 mg, 22.2 μmol) in 1,4-dioxane (2 mL) and H₂O (0.4 mL) was degassed and purged with N₂ three times. The mixture was stirred at 80° C. for 2 hr under N₂ atmosphere. The reaction mixture was quenched with H₂O (20 mL) and extracted with CH₂Cl₂ (20 mL×2). The combined organic layers were washed with brine (20 mL), dried over Na₂SO₄, filtered and concentrated under reduced pressure. After purified by prep-HPLC (column: Waters Xbridge 150×25 mm×5 μm; mobile phase: [water (NH₄HCO₃)-ACN]; gradient: 33%-63% B over 12 min), 4-((1-(4-(2-(2-aminopyridin-3-yl)-5-(1-(difluoromethyl)-6-oxo-1,6-dihydropyridin-3-yl)-3H-imidazo[4,5-b]pyridin-3-yl)benzyl)piperidin-4-yl)amino)pyrimidine-2-carbonitrile (Example 617, 71.6 mg, yield: 49% for two steps) was obtained as a yellow lyophilized powder. MS: m/z=646.0 [M+H]⁺. ¹H NMR (400 MHz, Dimethylsulfoxide-d₆) δ 8.38-8.35 (m, 1H), 8.30-8.22 (m, 2H), 8.17-7.97 (m, 4H), 7.97-7.72 (m, 1H), 7.53-7.40 (m, 4H), 7.18-7.14 (m, 1H), 7.06 (s, 2H), 6.75-6.62 (m, 2H), 6.38 (dd, J=7.6, 4.8 Hz, 1H), 3.96-3.75 (m, 1H), 3.59 (s, 2H), 2.90-2.75 (m, 2H), 2.22-2.05 (m, 2H), 1.97-1.77 (m, 2H), 1.58-1.40 (m, 2H). ¹⁹F NMR (400 MHz, Dimethylsulfoxide-d₆) δ −103.343.

Example 618: 4-((1-(4-(2-(2-Aminopyridin-3-yl)-5-(2-(fluoromethyl)-2H-1,2,3-triazol-4-yl)-3H-imidazo[4,5-b]pyridin-3-yl)benzyl)piperidin-4-yl)amino)pyrimidine-2-carbonitrile

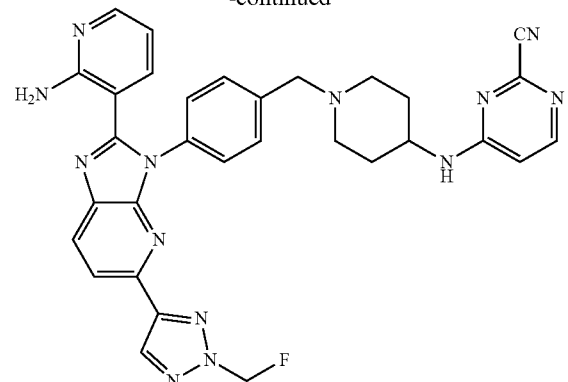

Example 618

To a solution of Intermediate 304 (1.6 g, 3.39 mmol, HCl salt) and Intermediate 51 (1.08 g, 3.39 mmol, TFA) in DMF (30 mL) were added K₂CO₃ (1.41 g, 10.2 mmol) and NaI (35.2 mg, 235 μmol). The mixture was degassed, purged with N₂ three times, and stirred at 50° C. for 1 hr under N₂. The reaction mixture was diluted with CH₂Cl₂ (50 mL), washed with brine (30 mL×4), dried over Na₂SO₄, filtered, and concentrated under reduced pressure. After purified by silica gel flash chromatography (Eluent of 5%~8% MeOH in CH₂Cl₂), 4-((1-(4-(2-(2-aminopyridin-3-yl)-5-(2-(fluoromethyl)-2H-1,2,3-triazol-4-yl)-3H-imidazo[4,5-b]pyridin-3-yl)benzyl)piperidin-4-yl)amino)pyrimidine-2-carbonitrile (Example 618, 1.01 g, yield 47% for three steps) was obtained as a yellow solid. MS: m/z=602.3 [M+H]⁺. ¹H NMR (400 MHz, Dimethylsulfoxide-d₆) δ 8.38-8.31 (m, 2H), 8.11-7.98 (m, 4H), 7.50-7.43 (m, 4H), 7.19-7.13 (m, 1H), 6.97 (br s, 2H), 6.68 (d, J=6.0 Hz, 1H), 6.48 (d, J=51.6 Hz, 2H), 6.38 (dd, J=7.6, 4.8 Hz, 1H), 3.88-3.75 (m, 1H), 3.59 (s, 2H), 2.86-2.81 (m, 2H), 2.20-2.12 (m, 2H), 1.94-1.85 (m, 2H), 1.55-1.45 (m, 2H). ¹⁹F NMR (400 MHz, Dimethylsulfoxide-d₆) δ −166.260.

Example 619: 4-((1-(4-(2-(2-Aminopyridin-3-yl)-5-(1-(fluoromethyl)-1H-1,2,3-triazol-4-yl)-3H-imidazo[4,5-b]pyridin-3-yl)benzyl)piperidin-4-yl)amino)pyrimidine-2-carbonitrile

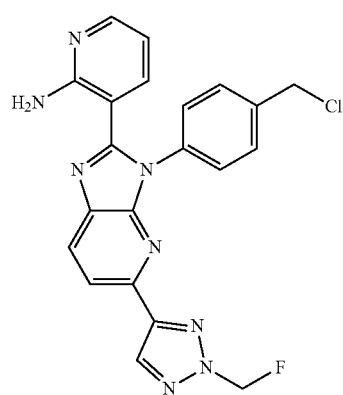

Intermediate 304

⟶ Intermediate 51

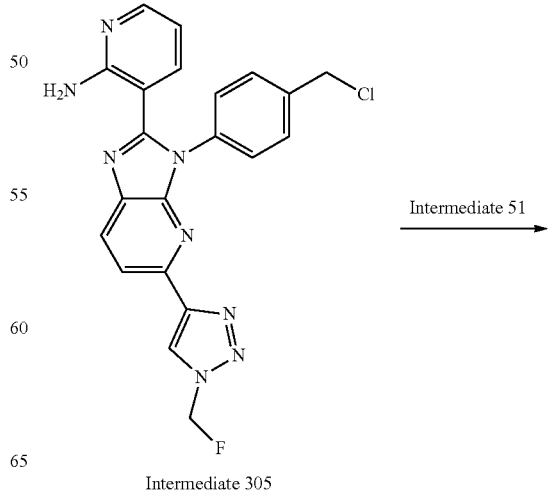

Intermediate 305

⟶ Intermediate 51

-continued

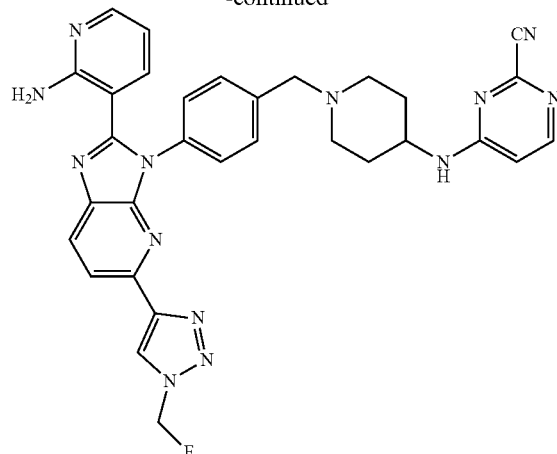

Example 619

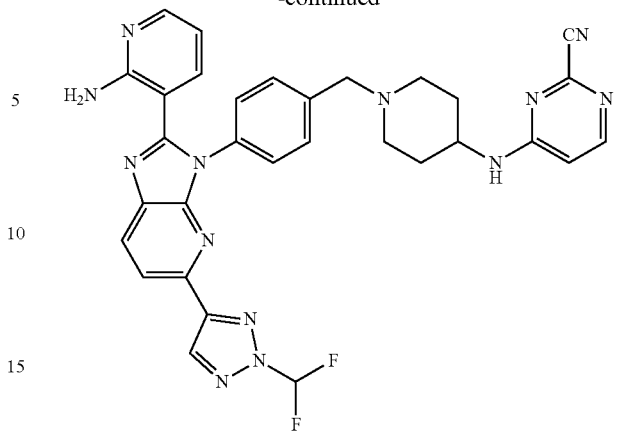

Example 620

To a solution of Intermediate 305 (450 mg, 955 μmol, HCl salt) and Intermediate 51 (304 mg, 955 μmol, TFA) in DMF (30 mL) were added $K_2CO_3$ (396 mg, 2.86 mmol), NaI (28.6 mg, 191 μmol). The mixture was degassed and purged with $N_2$ for 3 times and stirred at 50° C. for 1 hr under $N_2$. The reaction mixture was filtered and concentrated under reduced pressure. After purified by prep-HPLC (column: Daisogel SP ODS RPS 150×25 mm×5 μm; mobile phase: [water ($NH_4HCO_3$)-ACN]; gradient: 25%-55% B over 11 min), 4-((1-(4-(2-(2-aminopyridin-3-yl)-5-(1-(fluoromethyl)-1H-1,2,3-triazol-4-yl)-3H-imidazo[4,5-b]pyridin-3-yl)benzyl)piperidin-4-yl)amino)pyrimidine-2-carbonitrile (Example 619, 175.1 mg, yield 30% for three steps) was obtained as a yellow lyophilized powder. MS: m/z=602.2 $[M+H]^+$. $^1$H NMR (400 MHz, Dimethylsulfoxide-$d_6$) δ 8.79 (s, 1H), 8.32 (d, J=8.4 Hz, 1H), 8.15-8.03 (m, 3H), 7.99 (dd, J=4.8, 1.6 Hz, 1H), 7.52-7.41 (m, 4H), 7.14 (dd, J=7.6, 1.6 Hz, 1H), 6.97 (br s, 2H), 6.68 (d, J=6.0 Hz, 1H), 6.48 (d, J=50.4 Hz, 2H), 6.37 (dd, J=7.6, 4.4 Hz, 1H), 3.84-3.80 (m, 1H), 3.58 (s, 2H), 2.86-2.81 (m, 2H), 2.21-2.10 (m, 2H), 1.92-1.87 (m, 2H), 1.59-1.43 (m, 2H). $^{19}$F NMR (400 MHz, Dimethylsulfoxide-$d_6$) δ −166.65.

Intermediate 620: 4-((1-(4-(2-(2-Aminopyridin-3-yl)-5-(2-(difluoromethyl)-2H-1,2,3-triazol-4-yl)-3H-imidazo[4,5-b]pyridin-3-yl)benzyl)piperidin-4-yl)amino)pyrimidine-2-carbonitrile To a solution of Intermediate 307 (312 mg, 689 μmol, HCl salt) and Intermediate 51 (219 mg, 689 μmol, TFA) in DMF (4 mL) were added $K_2CO_3$ (381 mg, 2.76 mmol) and NaI (51.6 mg, 345 μmol). The mixture was stirred at 50° C. for 1 hr. The reaction mixture was quenched with $H_2O$ (10 mL) at 25° C. and extracted with EtOAc (10 mL×3). The combined organic layers were washed with brine (50 mL×3), dried over $Na_2SO_4$, filtered and concentrated under reduced pressure. After purified by silica gel flash chromatography (Eluent of 0%~5% $CH_2Cl_2$ in MeOH), 4-((1-(4-(2-(2-aminopyridin-3-yl)-5-(2-(difluoromethyl)-2H-1,2,3-triazol-4-yl)-3H-imidazo[4,5-b]pyridin-3-yl)benzyl)piperidin-4-yl)amino)pyrimidine-2-carbonitrile (Example 620, 202.9 mg, yield: 47% for three steps) was obtained as a yellow solid. MS: m/z=620.2 $[M+H]^+$. $^1$H NMR (400 MHz, Dimethylsulfoxide-$d_6$) δ 8.99 (s, 1H), 8.33 (d, J=8.0 Hz, 1H), 8.30-7.90 (m, 5H), 7.52-7.40 (m, 4H), 7.14 (d, J=6.8 Hz, 1H), 6.98 (br s, 2H), 6.68 (d, J=6.0 Hz, 1H), 6.37 (dd, J=7.2, 4.8 Hz, 1H), 3.91-3.72 (m, 1H), 3.58 (s, 2H), 2.91-2.74 (m, 2H), 2.24-2.09 (m, 2H), 1.96-1.78 (m, 2H), 1.57-1.42 (m, 2H). $^{19}$F NMR (400 MHz, Dimethylsulfoxide-$d_6$) δ −96.38.

Example 621: 4-((1-(4-(2-(3-Aminopyrazin-2-yl)-5-(2-(methyl-$d_3$)-2H-1,2,3-triazol-4-yl)-3H-imidazo[4,5-b]pyridin-3-yl)benzyl)piperidin-4-yl)amino)pyrimidine-2-carbonitrile

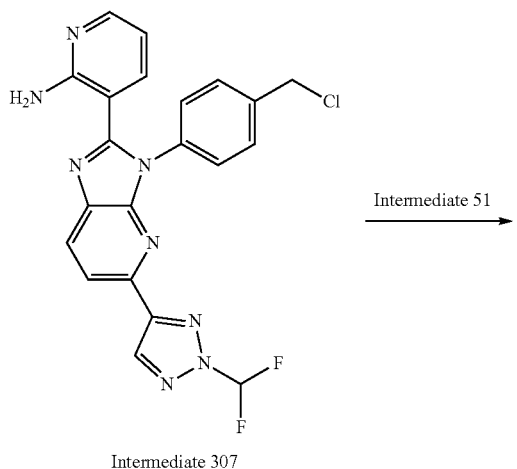

Intermediate 307

→ Intermediate 51

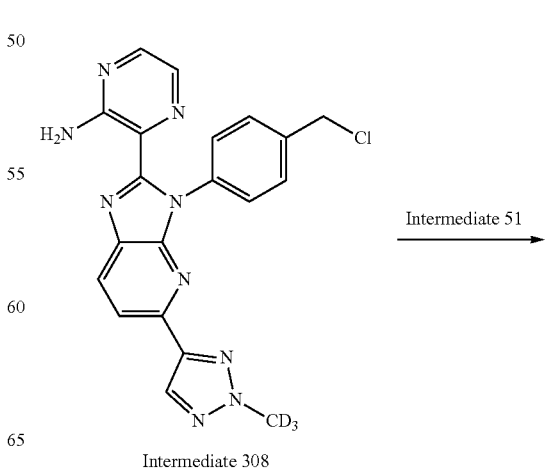

Intermediate 308

→ Intermediate 51

1757
-continued

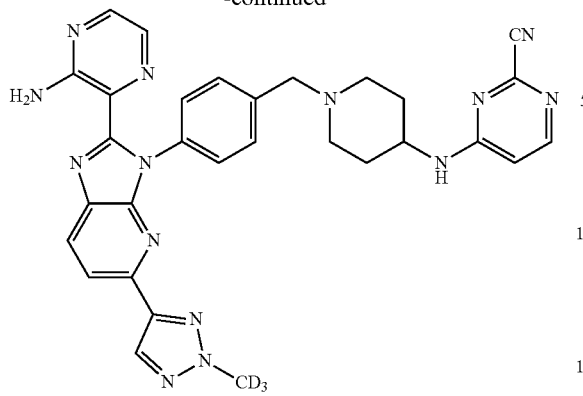

Example 621

To a solution of Intermediate 308 (220 mg, 481 μmol, HCl salt) and Intermediate 51 (153 mg, 481 μmol, TFA) in DMF (3 mL) were added $K_2CO_3$ (332 mg, 2.41 mmol) and NaI (7.21 mg, 48.1 μmol). The mixture was stirred at 50° C. for 1 hr. The reaction mixture was quenched with $H_2O$ (5 mL) at 25° C. and extracted with $CH_2Cl_2$ (15 mL×2). The combined organic layers were washed with brine (50 mL×3), dried over $Na_2SO_4$, filtered and concentrated under reduced pressure. After purified by prep-HPLC (column: Waters Xbridge BEH C18 150×25 mm×5 μm; mobile phase: [water ($NH_4HCO_3$)-ACN]; gradient: 32%-62% B over 10 min), 4-((1-(4-(2-(3-aminopyrazin-2-yl)-5-(2-(methyl-$d_3$)-2H-1,2,3-triazol-4-yl)-3H-imidazo[4,5-b]pyridin-3-yl)benzyl)piperidin-4-yl)amino)pyrimidine-2-carbonitrile (Example 621, 57.8 mg, yield: 20% for two steps) was obtained as a yellow lyophilized powder. MS: m/z=588.1 [M+H]$^+$. D %: 3D %=99.1%. $^1$H NMR (400 MHz, Dimethylsulfoxide-$d_6$) δ 8.35 (d, J=8.4 Hz, 1H), 8.24-7.86 (m, 5H), 7.77 (br s, 2H), 7.51-7.30 (m, 5H), 6.68 (d, J=5.6 Hz, 1H), 3.91-3.77 (m, 1H), 3.59 (s, 2H), 2.91-2.81 (m, 2H), 2.24-2.11 (m, 2H), 2.00-1.79 (m, 2H), 1.59-1.41 (m, 2H).

Example 622: 4-((1-(4-(2-(3-Aminoisoxazol-4-yl)-5-(5-fluoropyridin-2-yl)-3H-imidazo[4,5-b]pyridin-3-yl)benzyl)piperidin-4-yl)amino)pyrimidine-2-carbonitrile

1758
-continued

Example 622

To a solution of Intermediate 310 (58.7 mg, 128 μmol, HCl salt), Intermediate 51 (40.7 mg, 128 μmol, TFA salt) in DMF (1 mL) were added $K_2CO_3$ (70.9 mg, 513 μmol) and NaI (19.2 mg, 128 μmol). The mixture was degassed and purged with $N_2$ for 3 times and stirred at 25° C. for 1 hr under $N_2$. The reaction mixture was quenched with $H_2O$ (10 mL) and extracted with $CH_2Cl_2$ (5 mL×3). The combined organic layers were washed with brine (10 mL×2), dried over $Na_2SO_4$, filtered and concentrated under reduced pressure. After purified by silica gel flash chromatography (Eluent of 0%~9% MeOH in $CH_2Cl_2$), 4-((1-(4-(2-(3-aminoisoxazol-4-yl)-5-(5-fluoropyridin-2-yl)-3H-imidazo[4,5-b]pyridin-3-yl)benzyl)piperidin-4-yl)amino)pyrimidine-2-carbonitrile (Example 622, 22.6 mg, yield: 29% for three steps) was obtained as a yellow powder. MS: m/z=588.4 [M+H]$^+$. $^1$H NMR (400 MHz, Dimethylsulfoxide-$d_6$) δ 8.66 (d, J=2.8 Hz, 1H), 8.41-8.36 (m, 1H), 8.33-8.29 (m, 1H), 8.15 (dd, J=9.2, 4.8 Hz, 1H), 8.12-8.06 (m, 2H), 7.80-7.78 (m, 1H), 7.65-7.59 (m, 4H), 7.52 (s, 1H), 6.71-6.64 (m, 3H), 3.91-3.77 (m, 1H), 3.69 (s, 2H), 2.96-2.88 (m, 2H), 2.28-2.18 (m, 2H), 1.97-1.88 (m, 2H), 1.59-1.50 (m, 2H). $^{19}$F NMR (400 MHz, Dimethylsulfoxide-$d_6$) δ -127.739.

Example 623: 4-((1-(4-(2-(2-Aminopyridin-3-yl)-5-(6-(fluoromethoxy-$d_2$)pyridin-3-yl)-3H-imidazo[4,5-b]pyridin-3-yl)benzyl)piperidin-4-yl)amino)pyrimidine-2-carbonitrile

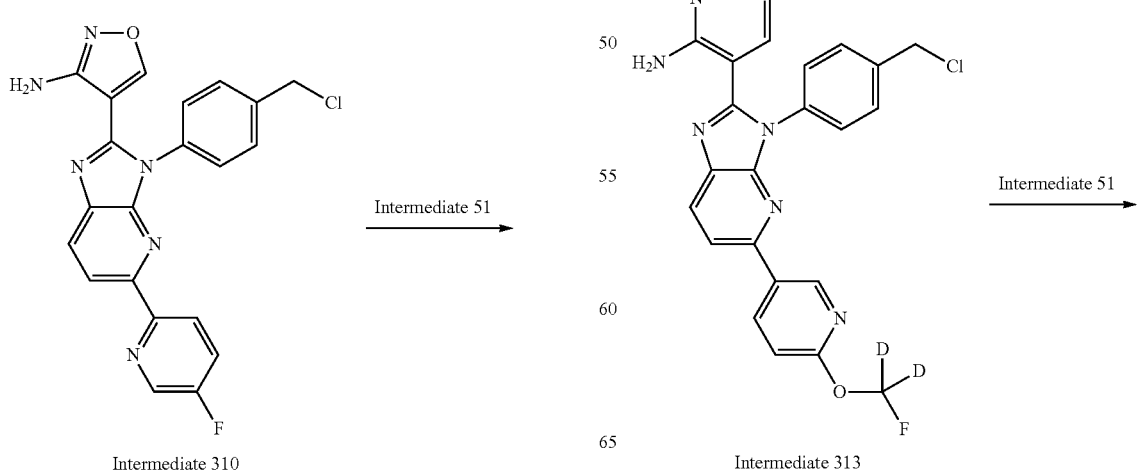

Intermediate 310      Intermediate 313

-continued

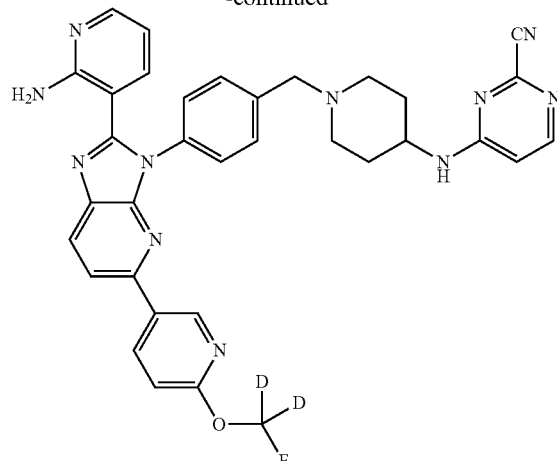

Example 623

To a solution of Intermediate 313 (300 mg, 601 µmol, HCl salt) and Intermediate 51 (191 mg, 601 µmol, TFA) in DMF (6 mL) were added K$_2$CO$_3$ (249 mg, 1.80 mmol) and NaI (18.0 mg, 120 µmol). The mixture was stirred at 50° C. for 1 hr. The reaction mixture was quenched with H$_2$O (10 mL) at 25° C. and extracted with CH$_2$Cl$_2$ (10 mL×3). The combined organic layers were washed with brine (20 mL×3), dried over Na$_2$SO$_4$, filtered and concentrated under reduced pressure. After purified by silica gel flash chromatography (Eluent of 5%~8% MeOH in CH$_2$Cl$_2$) and triturated with EtOAc (10 mL) at 25° C. for 5 min., 4-((1-(4-(2-(2-aminopyridin-3-yl)-5-(6-(fluoromethoxy-d$_2$)pyridin-3-yl)-3H-imidazo[4,5-b]pyridin-3-yl)benzyl)piperidin-4-yl)amino)pyrimidine-2-carbonitrile (Intermediate 623, 86.5 mg, yield: 23% for two steps) was obtained as an off-white solid. MS: m/z=630.2 [M+H]$^+$. D %: 2D %=98.2%. $^1$H NMR (400 MHz, Dimethylsulfoxide-d$_6$) δ 8.90 (d, J=2.4 Hz, 1H), 8.42 (dd, J=8.4, 2.4 Hz, 1H), 8.29 (d, J=8.4 Hz, 1H), 8.09-7.99 (m, 4H), 7.50-7.43 (m, 4H), 7.18-7.13 (m, 1H), 7.09 (d, J=8.8 Hz, 1H), 7.01 (br s, 2H), 6.67 (br d, J=5.2 Hz, 1H), 6.39 (dd, J=7.6, 4.8 Hz, 1H), 3.84-3.79 (m, 1H), 3.59 (br s, 2H), 2.85-2.79 (m, 2H), 2.19-2.11 (m, 2H), 1.93-1.83 (m, 2H), 1.55-1.46 (m, 2H). $^{19}$F NMR (400 MHz, Dimethylsulfoxide-d$_6$) δ −155.547.

Example 624: 4-((1-(4-(2-(2-Aminopyridin-3-yl)-5-(1-(fluoromethyl-d$_2$)-6-oxo-1,6-dihydropyridin-3-yl)-3H-imidazo[4,5-b]pyridin-3-yl)benzyl)piperidin-4-yl)amino)pyrimidine-2-carbonitrile

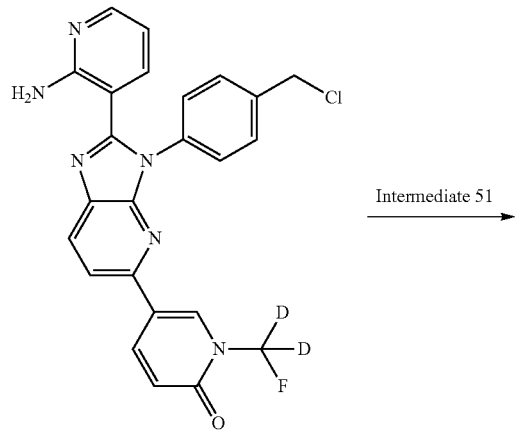

Intermediate 314

-continued

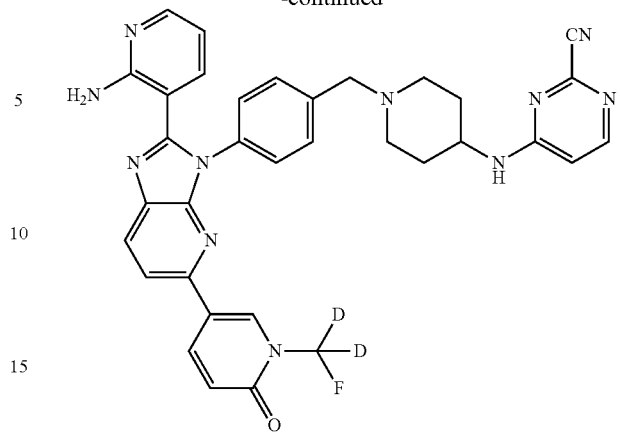

Example 624

To a solution of Intermediate 314 (101 mg, 202 µmol, HCl salt) and Intermediate 51 (64.2 mg, 202 µmol, TFA) in DMF (3 mL) were added K$_2$CO$_3$ (140 mg, 1.01 mmol) and NaI (3.03 mg, 20.2 µmol). The mixture was stirred at 50° C. for 1 hr. The reaction mixture was quenched with H$_2$O (5 mL) at 25° C. and extracted with CH$_2$Cl$_2$ (15 mL×2). The combined organic layers were washed with brine (20 mL×3), dried over Na$_2$SO$_4$, filtered and concentrated under reduced pressure. After purified by silica gel flash chromatography (Eluent of 1%~8% MeOH in CH$_2$Cl$_2$), 4-((1-(4-(2-(2-aminopyridin-3-yl)-5-(1-(fluoromethyl-d$_2$)-6-oxo-1,6-dihydropyridin-3-yl)-3H-imidazo[4,5-b]pyridin-3-yl)benzyl)piperidin-4-yl)amino)pyrimidine-2-carbonitrile (Example 624, 37.1 mg, yield: 28% for two steps) was obtained as a yellow solid. MS: m/z=630.2 [M+H]$^+$. D %: 2D %=98.4%. $^1$H NMR (400 MHz, Dimethylsulfoxide-d$_6$) δ 8.60 (d, J=2.8 Hz, 1H), 8.27 (d, J=8.4 Hz, 1H), 8.18 (dd, J=9.6, 2.4 Hz, 1H), 8.14-8.02 (m, 2H), 8.01-7.96 (m, 1H), 7.86 (d, J=8.4 Hz, 1H), 7.51-7.40 (m, 4H), 7.16-7.10 (m, 1H), 7.02 (br s, 2H), 6.67 (d, J=6.0 Hz, 1H), 6.61 (d, J=9.6 Hz, 1H), 6.37 (dd, J=7.6, 4.8 Hz, 1H), 3.85-3.74 (m, 1H), 3.59 (s, 2H), 2.91-2.75 (m, 2H), 2.18-2.09 (m, 2H), 1.95-1.84 (m, 2H), 1.55-1.44 (m, 2H). $^{19}$F NMR (400 MHz, Dimethylsulfoxide-d$_6$) δ −173.761.

Example 625: 4-((1-(4-(2-(2-Aminopyridin-3-yl)-5-(1-ethyl-1H-1,2,3-triazol-4-yl)-3H-imidazo[4,5-b]pyridin-3-yl)benzyl)piperidin-4-yl)amino)pyrimidine-2-carbonitrile

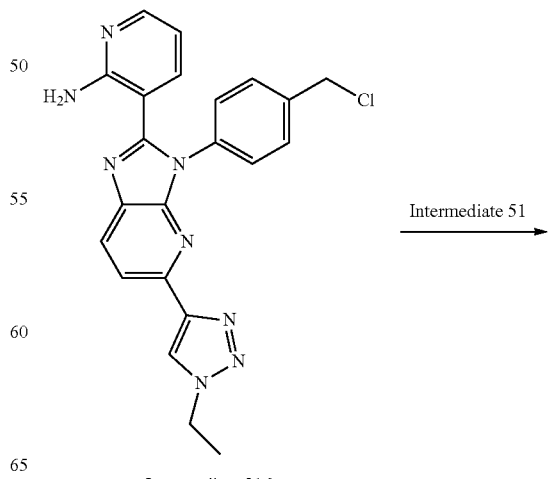

Intermediate 316

1761
-continued

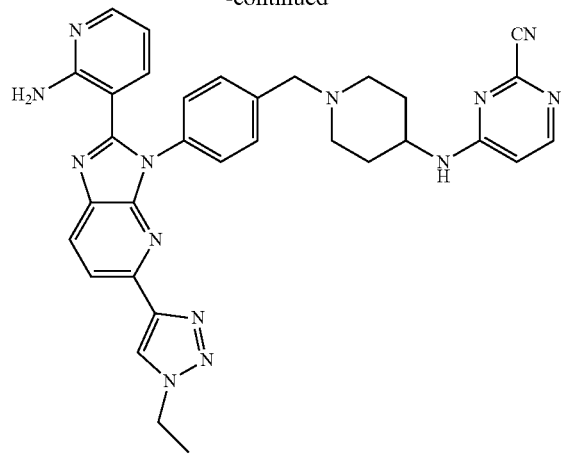

Example 625

To a mixture of Intermediate 316 (110 mg, 255 µmol) and Intermediate 51 (57.1 mg, 280 µmol) in DMF (2 mL) were added $K_2CO_3$ (106 mg, 766 µmol) and NaI (3.83 mg, 25.5 µmol), the mixture was stirred at 20° C. for 12 hr. The mixture was diluted with $H_2O$ (20 mL) and extracted with EtOAc (10 mL×2). The combined organic layers were washed with brine (10 mL), dried over anhydrous $Na_2SO_4$, filtered and concentrated. After purified by prep-HPLC (column: C18 150×30 mm; mobile phase: [water ($NH_3H_2O+ NH_4HCO_3$)-ACN]; gradient: 45%-75% B over 7 min), 4-((1-(4-(2-(2-aminopyridin-3-yl)-5-(1-ethyl-1H-1,2,3-triazol-4-yl)-3H-imidazo[4,5-b]pyridin-3-yl)benzyl)piperidin-4-yl)amino)pyrimidine-2-carbonitrile (Example 625, 48.8 mg, yield: 32%) was obtained as a white solid. MS: m/z=598.2 [M+H]⁺. ¹H NMR (400 MHz, Dimethylsulfoxide-$d_6$) δ 8.41 (s, 1H), 8.27 (d, J=8.4 Hz, 1H), 8.12-8.04 (m, 3H), 7.99 (dd, J=4.8, 1.6 Hz, 1H), 7.50-7.40 (m, 4H), 7.11 (dd, J=8.0, 2.0 Hz, 1H), 6.97 (s, 2H), 6.68 (d, J=6.0 Hz, 1H), 6.36 (dd, J=7.6, 4.8 Hz, 1H), 4.42 (q, J=7.2 Hz, 2H), 3.89-3.77 (m, 1H), 3.59 (s, 2H), 2.93-2.79 (m, 2H), 2.25-2.09 (m, 2H), 1.97-1.84 (m, 2H), 1.54-1.42 (m, 5H).

Example 626: 4-((1-(4-(2-(2-Aminopyridin-3-yl)-5-(2-(cyanomethyl)-2H-1,2,3-triazol-4-yl)-3H-imidazo[4,5-b]pyridin-3-yl)benzyl)piperidin-4-yl)amino)pyrimidine-2-carbonitrile 1762
-continued To a solution of Intermediate 318 (90 mg, 204 µmol) and Intermediate 51 (53.8 mg, 265 µmol) in DMF (1 mL) were added NaI (3.05 mg, 20.4 µmol) and $K_2CO_3$ (84.5 mg, 611 µmol). The mixture was stirred at 25° C. for 12 hr under $N_2$. The reaction mixture was quenched with $H_2O$ 10 mL) at 25° C. and extracted with $CH_2Cl_2$ (10 mL×3). The combined organic layers were washed with brine (20 mL×3), dried over $Na_2SO_4$, filtered and concentrated under reduced pressure. After purified by prep-HPLC (column: Phenomenex C18 80×30 mm×5 µm; mobile phase: [water ($NH_3H_2O+ NH_4HCO_3$)-ACN]; gradient: 45%-75% B over 7 min), 4-((1-(4-(2-(2-aminopyridin-3-yl)-5-(2-(cyanomethyl)-2H-1,2,3-triazol-4-yl)-3H-imidazo[4,5-b]pyridin-3-yl)benzyl)piperidin-4-yl)amino)pyrimidine-2-carbonitrile (Example 626, 21.6 mg, yield: 17% for three steps) was obtained as an off-white solid. MS: m/z=609.4 [M+H]⁺. ¹H NMR (400 MHz, Dimethylsulfoxide-$d_6$) δ 8.32 (d, J=8.4 Hz, 1H), 8.28 (s, 1H), 8.09 (d, J=5.6 Hz, 2H), 8.02-7.95 (m, 2H), 7.51-7.39 (m, 4H), 7.15 (dd, J=7.6, 1.2 Hz, 1H), 6.97 (s, 2H), 6.68 (d, J=6.0 Hz, 1H), 6.38 (dd, J=8.0, 5.2 Hz, 1H), 5.99 (s, 2H), 3.95-3.75 (m, 1H), 3.59 (br s, 2H), 2.97-2.69 (m, 2H), 2.28-2.03 (m, 2H), 2.01-1.82 (m, 2H), 1.59-1.39 (m, 2H).

Example 627: 4-((1-(4-(2-(3-Aminopyrazin-2-yl)-5-(2-(fluoromethyl)-2H-1,2,3-triazol-4-yl)-3H-imidazo[4,5-b]pyridin-3-yl)benzyl)piperidin-4-yl)amino)pyrimidine-2-carbonitrile

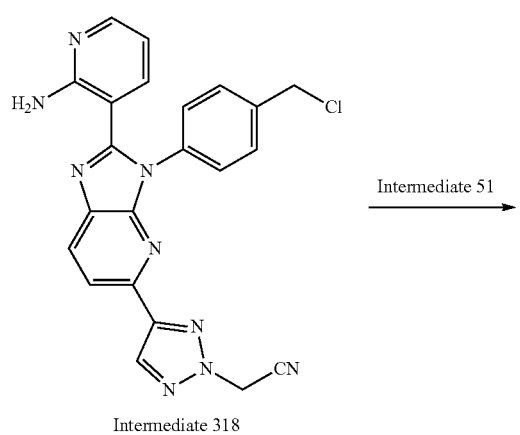

Intermediate 318

→ Intermediate 51

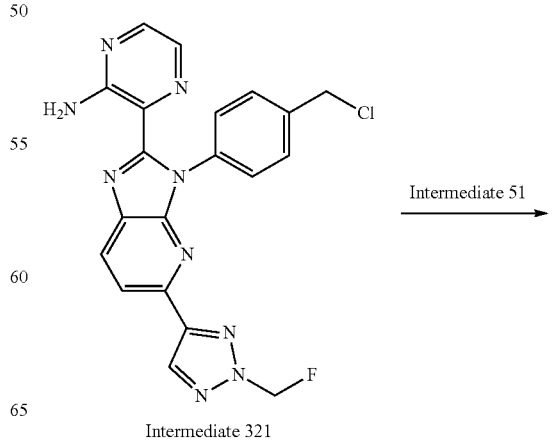

Intermediate 321

→ Intermediate 51

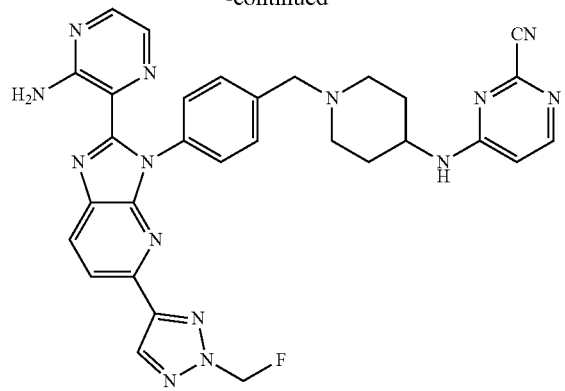

Example 627

To a solution of Intermediate 321 (200 mg, 423 µmol, HCl salt) and Intermediate 51 (135 mg, 423 µmol, TFA) in DMF (3 mL) were added K$_2$CO$_3$ (176 mg, 1.27 mmol) and NaI (12.7 mg, 84.7 µmol). The mixture was degassed and purged with N$_2$ three times and stirred at 50° C. for 1 hr under N$_2$. The reaction mixture was filtered and concentrated under reduced pressure. After purified by prep-HPLC (column: Daisogel SP ODS RPS 150×25 mm×5 µm; mobile phase: [water (NH$_4$HCO$_3$)-ACN]; gradient: 35%-65% B over 11 min), 4-((1-(4-(2-(3-aminopyrazin-2-yl)-5-(2-(fluoromethyl)-2H-1,2,3-triazol-4-yl)-3H-imidazo[4,5-b]pyridin-3-yl)benzyl)piperidin-4-yl)amino)pyrimidine-2-carbonitrile (Example 627, 24.3 mg, yield 9.3% for three steps) was obtained as a gray solid. MS: m/z=603.2 [M+H]$^+$. $^1$H NMR (400 MHz, Dimethylsulfoxide-d$_6$) δ 8.41 (d, J=8.4 Hz, 1H), 8.33 (s, 1H), 8.12-7.99 (m, 4H), 7.77 (br s, 2H), 7.49 (d, J=2.4 Hz, 1H), 7.46-7.41 (m, 2H), 7.40-7.36 (m, 2H), 6.68 (d, J=6.8 Hz, 1H), 6.48 (d, J=51.6 Hz, 2H), 3.87-3.79 (m, 1H), 3.59 (s, 2H), 2.88-2.83 (m, 2H), 2.21-2.14 (m, 2H), 1.96-1.88 (m, 2H), 1.57-1.47 (m, 2H). $^{19}$F NMR (400 MHz, Dimethylsulfoxide-d$_6$) δ -166.381.

Example 628: 4-((1-(4-(2-(3-Aminopyrazin-2-yl)-5-(1-(fluoromethyl)-1H-1,2,3-triazol-4-yl)-3H-imidazo[4,5-b]pyridin-3-yl)benzyl)piperidin-4-yl)amino)pyrimidine-2-carbonitrile Example 628

To a solution of Intermediate 322 (70 mg, 148 µmol, HCl salt) and Intermediate 51 (47.3 mg, 148 µmol, TFA) in DMF (2 mL) were added K$_2$CO$_3$ (61.5 mg, 445 µmol), NaI (4.44 mg, 29.6 µmol). The mixture was degassed and purged with N$_2$ three times and stirred at 50° C. for 1 hr under N$_2$. The reaction mixture was filtered and concentrated under reduced pressure. After purified by prep-HPLC (column: Daisogel SP ODS RPS 150×25 mm×5 µm; mobile phase: [water (NH$_4$HCO$_3$)-ACN]; gradient: 28%-58% B over 11 min), 4-((1-(4-(2-(3-aminopyrazin-2-yl)-5-(1-(fluoromethyl)-1H-1,2,3-triazol-4-yl)-3H-imidazo[4,5-b]pyridin-3-yl)benzyl)piperidin-4-yl)amino)pyrimidine-2-carbonitrile (Example 628, 14.2 mg, yield 15% for three steps) was obtained as a yellow solid. MS: m/z=603.3 [M+H]$^+$. $^1$H NMR (400 MHz, Methanol-d$_4$) δ 8.58 (s, 1H), 8.30 (d, J=8.4 Hz, 1H), 8.19 (d, J=8.4 Hz, 1H), 8.04-7.98 (m, 1H), 7.94 (d, J=2.0 Hz, 1H), 7.52-7.48 (m, 1H), 7.38-7.34 (m, 2H), 6.64-6.58 (m, 1H), 6.38 (d, J=50.8 Hz, 2H), 4.05-3.92 (m, 1H), 3.69 (s, 2H), 3.04-3.00 (m, 2H), 2.35-2.26 (m, 2H), 2.07-2.01 (m, 2H), 1.70-1.60 (m, 2H). $^{19}$F NMR (400 MHz, Methanol-d$_4$) δ -169.788.

Example 629: 4-((1-(4-(2-(3-Aminopyrazin-2-yl)-5-(2-ethyl-2H-1,2,3-triazol-4-yl)-3H-imidazo[4,5-b]pyridin-3-yl)benzyl)piperidin-4-yl)amino)pyrimidine-2-carbonitrile

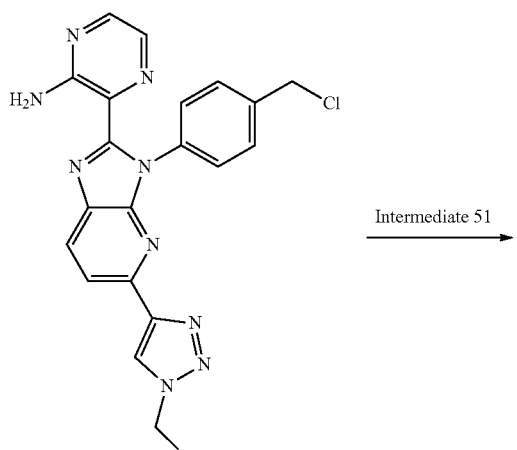

Intermediate 322

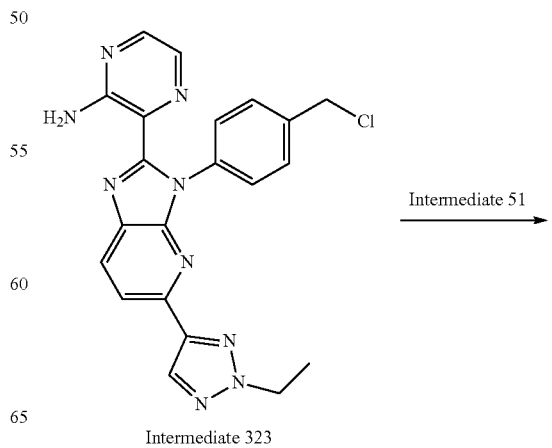

Intermediate 323

1765
-continued

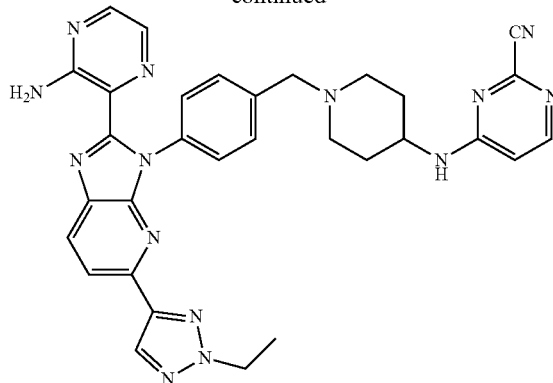

Example 629

To a mixture of Intermediate 323 (190 mg, 440 μmol) and Intermediate 51 (98.4 mg, 484 μmol) in DMF (3 mL) were added NaI (6.59 mg, 44.0 μmol) and $K_2CO_3$ (182 mg, 1.32 mmol). The mixture was stirred at 20° C. for 2 hr. The reaction mixture was quenched with $H_2O$ (50 mL) and extracted with EtOAc (50 mL×2). The combined organic layers were washed with brine (50 mL), dried over anhydrous $Na_2SO_4$, filtered and concentrated. After purified by prep-HPLC (column: C18 150×30 mm; mobile phase: [water ($NH_3H_2O+NH_4HCO_3$)-ACN]; gradient: 48%-78% B over 7 min), 4-((1-(4-(2-(3-aminopyrazin-2-yl)-5-(2-ethyl-2H-1,2,3-triazol-4-yl)-3H-imidazo[4,5-b]pyridin-3-yl)benzyl)piperidin-4-yl)amino)pyrimidine-2-carbonitrile (Example 629, 107 mg, yield: 40% for two steps) was obtained as a yellow solid. MS: m/z=621.1 [M+Na]$^+$. $^1$H NMR (400 MHz, Dimethylsulfoxide-d$_6$) δ 8.33 (d, J=8.4 Hz, 1H), 8.12-7.93 (m, 5H), 7.78 (br s, 2H), 7.47 (d, J=2.4 Hz, 1H), 7.45-7.33 (m, 4H), 6.68 (d, J=6.0 Hz, 1H), 4.50 (q, J=7.2 Hz, 2H), 3.89-3.75 (m, 1H), 3.59 (s, 2H), 2.96-2.80 (m, 2H), 2.24-2.10 (m, 2H), 1.98-1.82 (m, 2H), 1.57-1.41 (m, 5H).

Example 630: 4-((1-(4-(2-(3-Aminopyrazin-2-yl)-5-(2-isopropyl-2H-1,2,3-triazol-4-yl)-3H-imidazo[4,5-b]pyridin-3-yl)benzyl)piperidin-4-yl)amino)pyrimidine-2-carbonitrile

1766
-continued

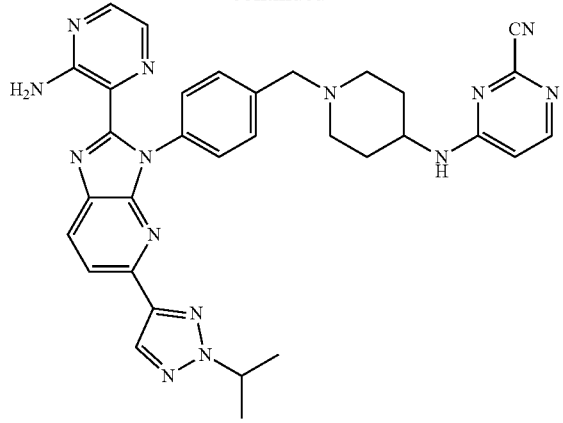

Example 630

To a solution of Intermediate 324 (187 mg, 419 μmol) and Intermediate 51 (93.8 mg, 461 μmol) in DMF (8 mL) were added $K_2CO_3$ (174 mg, 1.26 mmol) and NaI (12.6 mg, 84 μmol) at 20° C. The reaction mixture was stirred at 20° C. for 12 hr. The mixture was diluted with $H_2O$ (20 mL) and extracted with EtOAc (20 mL×2). The combined organic layers were washed with brine (20 mL), dried over anhydrous $Na_2SO_4$, filtered and concentrated. After purified by prep-HPLC (column: Xtimate C18 150×40 mm×10 μm; mobile phase: [water (FA)-ACN]; gradient: 25%-55% B over 7 min), the fractions were concentrated to remove most of MeCN. The product was diluted with $CH_2Cl_2$ (30 mL) and washed with sat. $NaHCO_3$ (30 mL×2). The organic layer was dried over anhydrous $Na_2SO_4$, filtered and concentrated to give 4-((1-(4-(2-(3-aminopyrazin-2-yl)-5-(2-isopropyl-2H-1,2,3-triazol-4-yl)-3H-imidazo[4,5-b]pyridin-3-yl)benzyl)piperidin-4-yl)amino)pyrimidine-2-carbonitrile (Example 630, 61.0 mg, yield: 23.6% for 3 steps) as a yellow solid. MS: m/z=613.3 [M+H]$^+$. $^1$H NMR (400 MHz, Dimethylsulfoxide-d$_6$) δ 8.37-8.32 (m, 1H), 8.12-7.96 (m, 5H), 7.78 (s, 2H), 7.48-7.34 (m, 5H), 6.70-6.64 (m, 1H), 4.91-4.84 (m, 1H), 3.88-3.76 (m, 1H), 3.59 (s, 2H), 2.91-2.80 (m, 2H), 2.20-2.11 (m, 2H), 1.96-1.85 (m, 2H), 1.56-1.48 (m, 8H).

Example 631: 4-((1-(4-(2-(3-Aminopyrazin-2-yl)-5-(2-cyclopropyl-2H-1,2,3-triazol-4-yl)-3H-imidazo[4,5-b]pyridin-3-yl)benzyl)piperidin-4-yl)amino)pyrimidine-2-carbonitrile

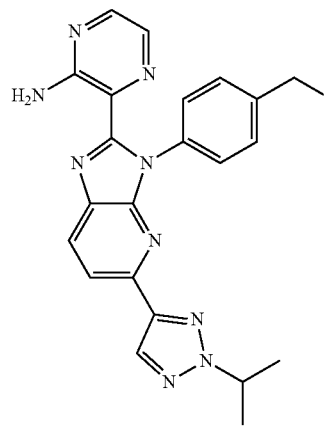

Intermediate 324

→ Intermediate 51

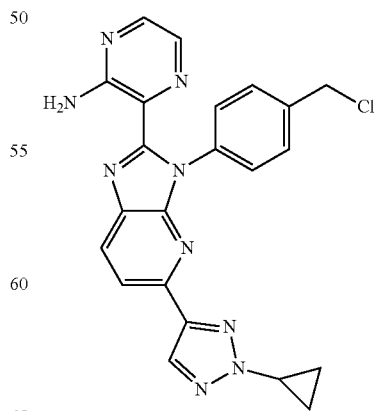

Intermediate 325

→ Intermediate 51

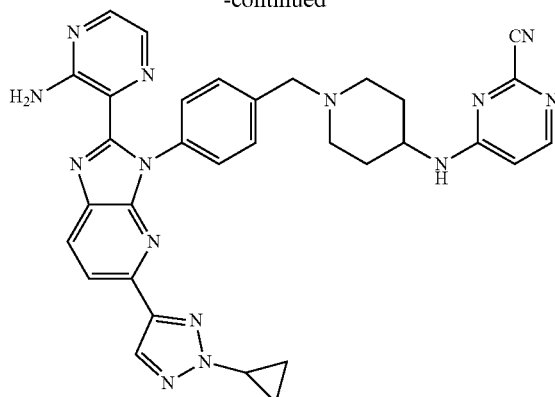

Example 631

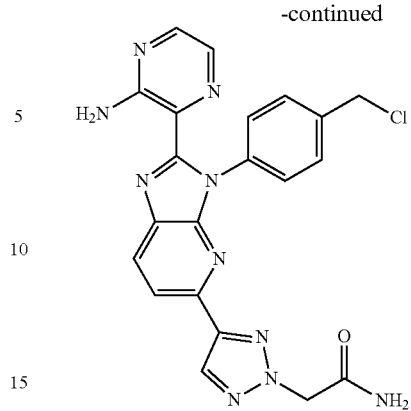

Intermediate 327

To a solution of Intermediate 325 (130 mg, 642 μmol, HCl salt) and Intermediate 51 (130 mg, 642 μmol) in DMF (3 mL) were added NaI (8.02 mg, 53.5 μmol) and $K_2CO_3$ (222 mg, 1.60 mmol). The mixture was stirred at 25° C. for 1 hr. The mixture was diluted with water (10 mL) and extracted with ethyl acetate (10 mL×2). The combined organic layers were dried over anhydrous $Na_2SO_4$, filtered and concentrated. After purified by prep-HPLC (column: C18 150×30 mm; mobile phase: [water ($NH_3H_2O+NH_4HCO_3$)-ACN]; gradient: 55%-85% B over 7 min), 4-((1-(4-(2-(3-aminopyrazin-2-yl)-5-(2-cyclopropyl-2H-1,2,3-triazol-4-yl)-3H-imidazo[4,5-b]pyridin-3-yl)benzyl)piperidin-4-yl)amino)pyrimidine-2-carbonitrile (Example 631, 60.8 mg, yield: 19% for three steps) was obtained as a light yellow solid. MS: m/z=611.1 [M+H]⁺. ¹H NMR (400 MHz, Dimethylsulfoxide-$d_6$) δ 8.35 (d, J=8.0 Hz, 1H), 8.13-8.03 (m, 2H), 8.03-8.00 (m, 2H), 7.97 (d, J=8.0 Hz, 1H), 7.78 (br s, 2H), 7.48 (d, J=2.0 Hz, 1H), 7.43 (d, J=8.4 Hz, 2H), 7.36 (d, J=8.4 Hz, 2H), 6.69 (d, J=6.0 Hz, 1H), 4.27-4.14 (m, 1H), 3.94-3.74 (m, 1H), 3.60 (s, 2H), 2.88-2.82 (m, 2H), 2.24-2.12 (m, 2H), 1.97-1.83 (m, 2H), 1.58-1.43 (m, 2H), 1.27-1.23 (m, 2H), 1.16-1.10 (m, 2H).

Example 632 & 633: 4-((1-(4-(2-(3-Aminopyrazin-2-yl)-5-(2-(cyanomethyl)-2H-1,2,3-triazol-4-yl)-3H-imidazo[4,5-b]pyridin-3-yl)benzyl)piperidin-4-yl)amino)pyrimidine-2-carbonitrile & 2-(4-(2-(3-aminopyrazin-2-yl)-3-(4-((4-((2-cyanopyrimidin-4-yl)amino)piperidin-1-yl)methyl)phenyl)-3H-imidazo[4,5-b]pyridin-5-yl)-2H-1,2,3-triazol-2-yl)acetamide

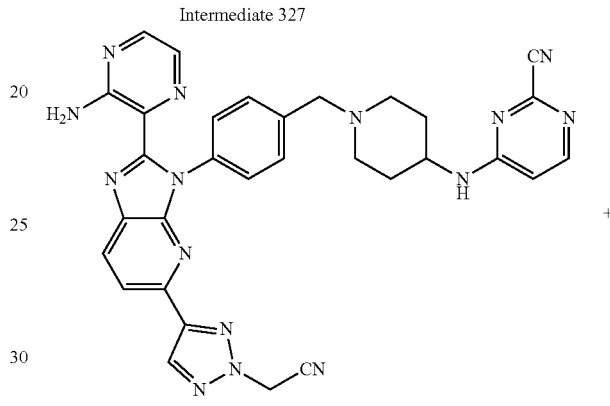

Example 632

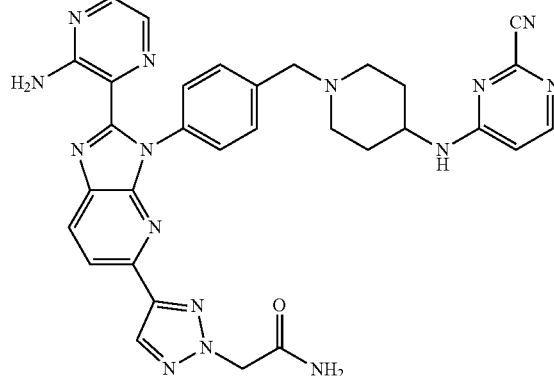

Example 633

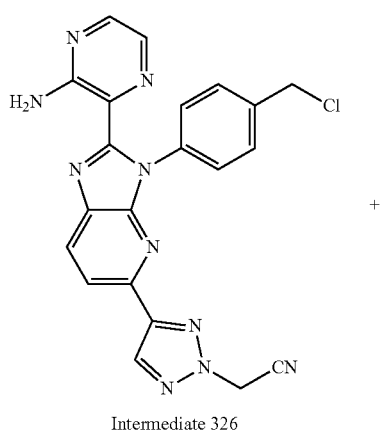

Intermediate 326

To a solution of a mixture of Intermediate 326 and Intermediate 327 (104 mg, 236 μmol, HCl salt) and Intermediate 51 (57.5 mg, 283 μmol) in DMF (2 mL) were added NaI (3.53 mg, 23.6 μmol) and $K_2CO_3$ (97.7 mg, 707 μmol). The mixture was stirred at 50° C. for 1 hr. The mixture was diluted with water (10 mL) and extracted with EtOAc (10 mL×2). The combined organic layers were dried over anhydrous $Na_2SO_4$, filtered and concentrated. After purified by prep-HPLC (column: C18 150×30 mm; mobile phase: [water ($NH_3H_2O+NH_4HCO_3$)-ACN]; gradient. 47%-77% B over 7 min)), 4-((1-(4-(2-(3-aminopyrazin-2-yl)-5-(2-(cyanomethyl)-2H-1,2,3-triazol-4-yl)-3H-imidazo[4,5-b]pyridin-3-yl)benzyl)piperidin-4-yl)amino)pyrimidine-2-carbonitrile (Example 632, 10.6 mg, yield: 7.7% for three steps) was obtained as a light yellow solid. MS: m/z=610.3 [M+H]⁺. ¹H NMR (400 MHz, Dimethylsulfoxide-$d_6$) δ 8.39

(d, J=8.4 Hz, 1H), 8.25 (s, 1H), 8.15-8.03 (m, 2H), 8.03-7.97 (m, 2H), 7.78 (br s, 2H), 7.48 (d, J=2.4 Hz, 1H), 7.46-7.41 (m, 2H), 7.39-7.32 (m, 2H), 6.68 (d, J=6.0 Hz, 1H), 5.99 (s, 2H), 3.89-3.71 (m, 1H), 3.59 (s, 2H), 2.92-2.80 (m, 2H), 2.26-2.10 (m, 2H), 1.97-1.83 (m, 2H), 1.62-1.44 (m, 2H). 2-(4-(2-(3-Aminopyrazin-2-yl)-3-(4-((4-((2-cyanopyrimidin-4-yl)amino)piperidin-1-yl)methyl)phenyl)-3H-imidazo[4,5-b]pyridin-5-yl)-2H-1,2,3-triazol-2-yl)acetamide (Example 633, 27.8 mg, yield: 20% for three steps) was also obtained as a light yellow solid. MS: m/z=628.4 [M+H]$^+$. $^1$H NMR (400 MHz, Dimethylsulfoxide-d$_6$) δ 8.35 (d, J=8.4 Hz, 1H), 8.18-8.02 (m, 3H), 8.01 (d, J=2.4 Hz, 1H), 7.97 (d, J=8.4 Hz, 1H), 7.77 (br s, 2H), 7.67 (s, 1H), 7.48 (d, J=2.4 Hz, 1H), 7.45-7.41 (m, 2H), 7.40-7.34 (m, 3H), 6.68 (d, J=6.4 Hz, 1H), 5.16 (s, 2H), 3.97-3.69 (m, 1H), 3.59 (s, 2H), 2.88-2.83 (m, 2H), 2.23-2.11 (m, 2H), 1.94-1.82 (m, 2H), 1.58-1.45 (m, 2H)

Example 634: 4-((1-(4-(2-(3-Aminopyrazin-2-yl)-5-(2-methyl-2H-1,2,3-triazol-4-yl-5-d)-3H-imidazo[4,5-b]pyridin-3-yl)benzyl)piperidin-4-yl)amino)pyrimidine-2-carbonitrile

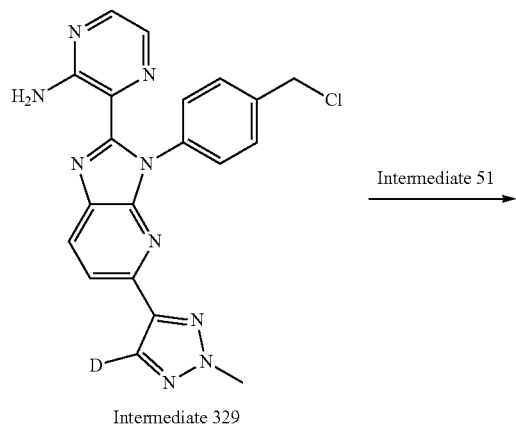

Intermediate 329

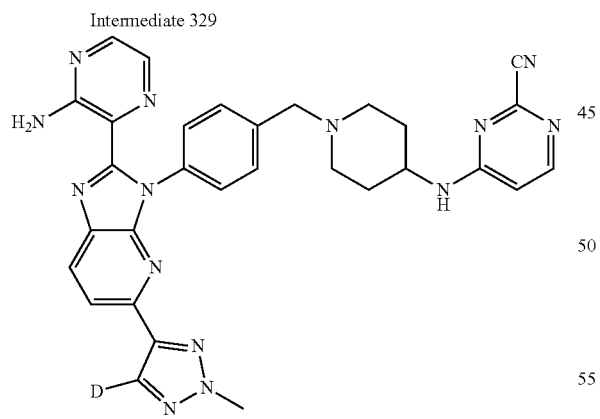

Example 634

To a solution of Intermediate 329 (375 mg, 824 μmol, HCl salt) and Intermediate 51 (261 mg, 824 gmol, TFA) in DMF (5 mL) were added K$_2$CO$_3$ (569 mg, 4.12 mmol) and NaI (12.4 mg, 82.4 μmol). The mixture was stirred at 50° C. for 1 hr. The reaction mixture was quenched with H$_2$O (5 mL) at 25° C. and extracted with CH$_2$Cl$_2$ (15 mL×2). The combined organic layers were washed with brine (50 mL×3), dried over Na$_2$SO$_4$, filtered and concentrated under reduced pressure. After purified by prep-HPLC (column: Daisogel SP ODS RPS 150×25 mm×5 μm; mobile phase: [water (NH$_4$HCO$_3$)-ACN]; gradient: 42%-72% B over 11 min), 4-((1-(4-(2-(3-aminopyrazin-2-yl)-5-(2-methyl-2H-1,2,3-triazol-4-yl-5-d)-3H-imidazo[4,5-b]pyridin-3-yl)benzyl)piperidin-4-yl)amino)pyrimidine-2-carbonitrile (Example 634, 273 mg, yield: 57% for three steps) was obtained as a yellow lyophilized powder. MS: m/z=586.3 [M+H]$^+$. 1D %=98.4%. $^1$H NMR (400 MHz, Dimethylsulfoxide-d$_6$) δ 8.35 (d, J=8.4 Hz, 1H), 8.13-8.05 (m, 2H), 8.02-7.95 (m, 2H), 7.78 (br s, 2H), 7.48 (d, J=2.0 Hz, 1H), 7.45-7.41 (m, 2H), 7.38-7.34 (m, 2H), 6.68 (d, J=6.4 Hz, 1H), 4.21 (s, 3H), 3.89-3.77 (m, 1H), 3.59 (s, 2H), 2.89-2.82 (m, 2H), 2.21-2.12 (m, 2H), 1.96-1.87 (m, 2H), 1.55-1.45 (m, 2H).

Example 635: 4-((1-(4-(2-(3-Aminopyrazin-2-yl)-5-(2,5-dimethyl-2H-1,2,3-triazol-4-yl)-3H-imidazo[4,5-b]pyridin-3-yl)benzyl)piperidin-4-yl)amino)pyrimidine-2-carbonitrile

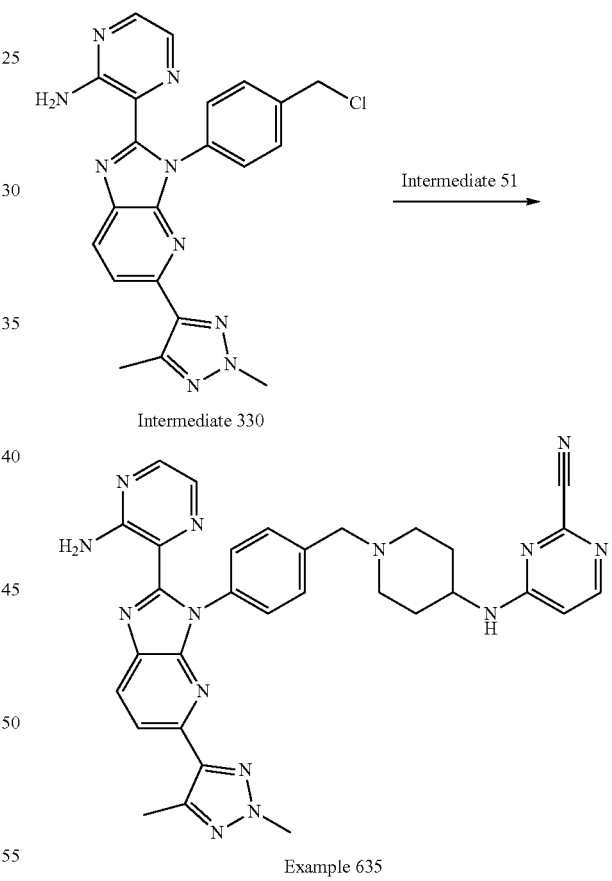

Example 635

To a solution of Intermediate 330 (160 mg, 370 μmol) in DMF (3 mL) were added 4-(piperidin-4-ylamino)pyrimidine-2-carbonitrile (82.8 mg, 408 μmol), K$_2$CO$_3$ (154 mg, 1.11 mmol), NaI (5.55 mg, 37.1 μmol). The mixture was stirred at 25° C. for 12 hr under N$_2$. The mixture was diluted with H$_2$O (20 mL) and extracted with EtOAc (10 mL×3). The combined organic layers were washed with brine (20 mL), dried over anhydrous Na$_2$SO$_4$, filtered and concentrated. After purified by prep-HPLC (column: C18 150×30 mm; mobile phase: [water (NH$_3$H$_2$O+NH$_4$HCO$_3$)-ACN];

gradient: 47%-77% B over 7 min), 4-((1-(4-(2-(3-aminopyrazin-2-yl)-5-(2,5-dimethyl-2H-1,2,3-triazol-4-yl)-3H-imidazo[4,5-b]pyridin-3-yl)benzyl)piperidin-4-yl)amino)pyrimidine-2-carbonitrile (Example 635, 50.2 mg, yield: 22.7% for three steps) was obtained as a light yellow solid. MS: m/z=599.3 [M+H]$^+$. $^1$H NMR (400 MHz, Dimethylsulfoxide-d$_6$) δ 8.30 (br d, J=6.8 Hz, 1H), 8.15-7.98 (m, 3H), 7.98-7.77 (m, 31H), 7.52 (s, 1H), 7.46-7.28 (m, 4H), 6.67 (br s, 11H), 4.11 (s, 3H), 3.87-3.71 (m, 1H), 3.58 (br s, 2H), 2.89-2.73 (m, 2H), 2.27 (s, 3H), 2.17-2.04 (m, 2H), 1.93-1.80 (m, 2H), 1.51-1.48 (m, 2H).

Example 636: 4-((1-(4-(2-(3-Aminopyrazin-2-yl)-5-(6-methoxypyridin-3-yl)-3H-imidazo[4,5-b]pyridin-3-yl)benzyl)piperidin-4-yl)amino)pyrimidine-2-carbonitrile min), 4-((1-(4-(2-(3-aminopyrazin-2-yl)-5-(6-methoxypyridin-3-yl)-3H-imidazo[4,5-b]pyridin-3-yl)benzyl)piperidin-4-yl)amino)pyrimidine-2-carbonitrile (Example 636, 159 mg, yield: 62% for three steps) was obtained as a yellow lyophilized powder. MS: m/z=611.2 [M+H]$^+$. $^1$H NMR (400 MHz, Dimethylsulfoxide-d$_6$) δ 8.84 (d, J=2.4 Hz, 1H), 8.36-8.27 (m, 2H), 8.11-7.98 (m, 4H), 7.82 (br s, 2H), 7.49 (d, J=2.4 Hz, 1H), 7.45-7.36 (m, 4H), 6.91 (d, J=8.8 Hz, 1H), 6.68 (d, J=6.0 Hz, 1H), 3.89 (s, 3H), 3.87-3.77 (m, 1H), 3.60 (s, 2H), 2.91-2.80 (m, 2H), 2.22-2.12 (m, 2H), 1.97-1.83 (m, 2H), 1.60-1.44 (m, 2H).

Example 637: 4-((1-(4-(2-(3-Aminopyrazin-2-yl)-5-(6-(methoxy-d)pyridin-3-yl)-3H-imidazo[4,5-b]pyridin-3-yl)benzyl)piperidin-4-yl)amino)pyrimidine-2-carbonitrile

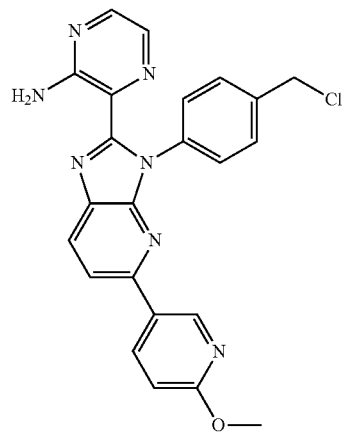

Intermediate 331

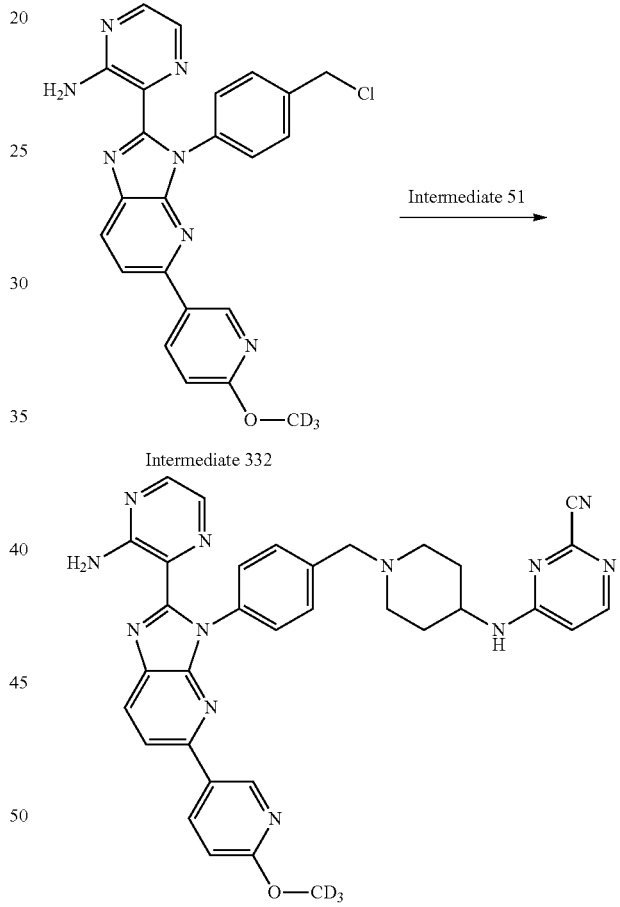

Example 636

Example 637

To a solution of Intermediate 331 (197 mg, 410 μmol, HCl salt) and Intermediate 51 (130 mg, 410 μmol, TFA) in DMF (3 mL) were added K$_2$CO$_3$ (283 mg, 2.05 mmol) and NaI (12.3 mg, 82.0 μmol). The mixture was stirred at 50° C. for 1 hr. The reaction mixture was quenched with H$_2$O (5 mL) at 25° C. and extracted with CH$_2$Cl$_2$ (15 mL×2). The combined organic layers were washed with brine (50 mL×3), dried over Na$_2$SO$_4$, filtered and concentrated under reduced pressure. After purified by prep-HPLC (column: Daisogel SP ODS RPS 150×25 mm×5 μm; mobile phase: [water (NH$_4$HCO$_3$)-ACN]; gradient: 38%-68% B over 11

To a solution of Intermediate 332 (389 mg, 805 μmol, HCl salt) and Intermediate 51 (255 mg, 805 μmol, TFA) in DMF (5 mL) were added K$_2$CO$_3$ (556 mg, 4.02 mmol) and NaI (24.1 mg, 161 μmol). The mixture was stirred at 50° C. for 1 hr. The reaction mixture was quenched with H$_2$O (20 mL) at 25° C. and extracted with CH$_2$Cl$_2$ (50 mL×2). The combined organic layers were washed with brine (50 mL×3), dried over Na$_2$SO$_4$, filtered and concentrated under reduced pressure. After purified by prep-HPLC (column: Daisogel SP ODS RPS 150×25 mm×5 μm; mobile phase: [water (NH$_4$HCO$_3$)-ACN]; gradient: 50%-80% B over 11 min), 4-((1-(4-(2-(3-aminopyrazin-2-yl)-5-(6-(methoxy-d₃)pyridin-3-yl)-3H-imidazo[4,5-b]pyridin-3-yl)benzyl)piperidin-4-yl)amino)pyrimidine-2-carbonitrile (Example 637, 113 mg, yield: 23% for three steps) was obtained as a light yellow lyophilized powder. MS: m/z=614.3 [M+H]⁺. D %: 3D %=100.0%. ¹H NMR (400 MHz, Dimethylsulfoxide-d₆) δ 8.84 (d, J=2.4 Hz, 1H), 8.35-8.26 (m, 2H), 8.10-7.99 (m, 4H), 7.82 (br s, 2H), 7.49 (d, J=2.4 Hz, 1H), 7.44-7.36 (m, 4H), 6.90 (d, J=8.8 Hz, 1H), 6.67 (d, J=6.0 Hz, 1H), 3.88-3.75 (m, 1H), 3.59 (s, 2H), 2.88-2.79 (m, 2H), 2.24-2.13 (m, 2H), 1.97-1.86 (m, 2H), 1.57-1.47 (m, 2H).

Example 638: 4-((1-(4-(2-(3-Aminopyrazin-2-yl)-5-(5-(methoxy-d₃)pyridin-2-yl)-3H-imidazo[4,5-b]pyridin-3-yl)benzyl)piperidin-4-yl)amino)pyrimidine-2-carbonitrile

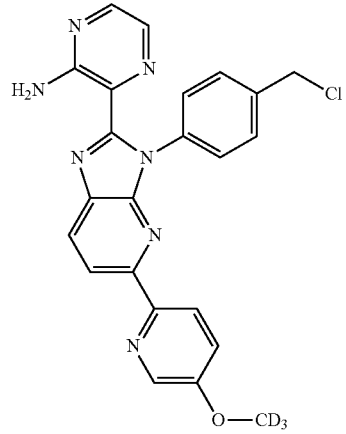

Intermediate 334

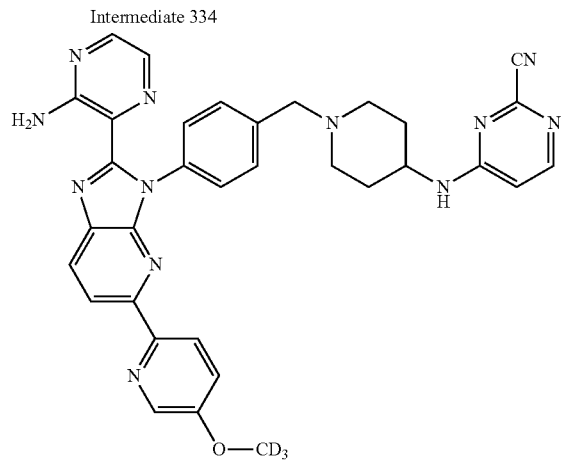

Example 638

To a solution of Intermediate 334 (360 mg, 745 μmol, HCl salt) and Intermediate 51 (236 mg, 745 μmol, TFA) in DMF (5 mL) were added K₂CO₃ (515 mg, 3.72 mmol) and NaI (22.3 mg, 149 μmol). The mixture was stirred at 50° C. for 1 hr. The reaction mixture was quenched with H₂O (5 mL) at 25° C. and extracted with CH₂Cl₂ (15 mL×2). The combined organic layers were washed with brine (50 mL×3), dried over Na₂SO₄, filtered and concentrated under reduced pressure. After purified by prep-HPLC (column: Daisogel SP ODS RPS 150×25 mm×5 μm; mobile phase: [water (NH₄HCO₃)-ACN]; gradient: 38%-68% B over 11 min), 4-((1-(4-(2-(3-aminopyrazin-2-yl)-5-(5-(methoxy-d₃)pyridin-2-yl)-3H-imidazo[4,5-b]pyridin-3-yl)benzyl)piperidin-4-yl)amino)pyrimidine-2-carbonitrile (Example 638, 219 mg, yield: 48% for three steps) was obtained as a yellow lyophilized powder. MS: m/z=614.3 [M+H]⁺. D %: 3D %=97.6%. ¹H NMR (400 MHz, Dimethylsulfoxide-d₆) δ 8.43-8.31 (m, 3H), 8.14-8.05 (m, 3H), 8.01 (d, J=2.0 Hz, 1H), 7.81 (br s, 2H), 7.51-7.47 (m, 2H), 7.46-7.42 (m, 2H), 7.41-7.37 (m, 2H), 6.68 (d, J=6.0 Hz, 1H), 3.95-3.77 (m, 1H), 3.61 (s, 2H), 2.91-2.84 (m, 2H), 2.22-2.12 (m, 2H), 1.96-1.86 (m, 2H), 1.57-1.49 (m, 2H). Example 639: 4-((1-(4-(2-(3-Aminopyrazin-2-yl)-5-(6-(fluoromethoxy)pyridin-3-yl)-3H-imidazo[4,5-b]pyridin-3-yl)benzyl)piperidin-4-yl)amino)pyrimidine-2-carbonitrile

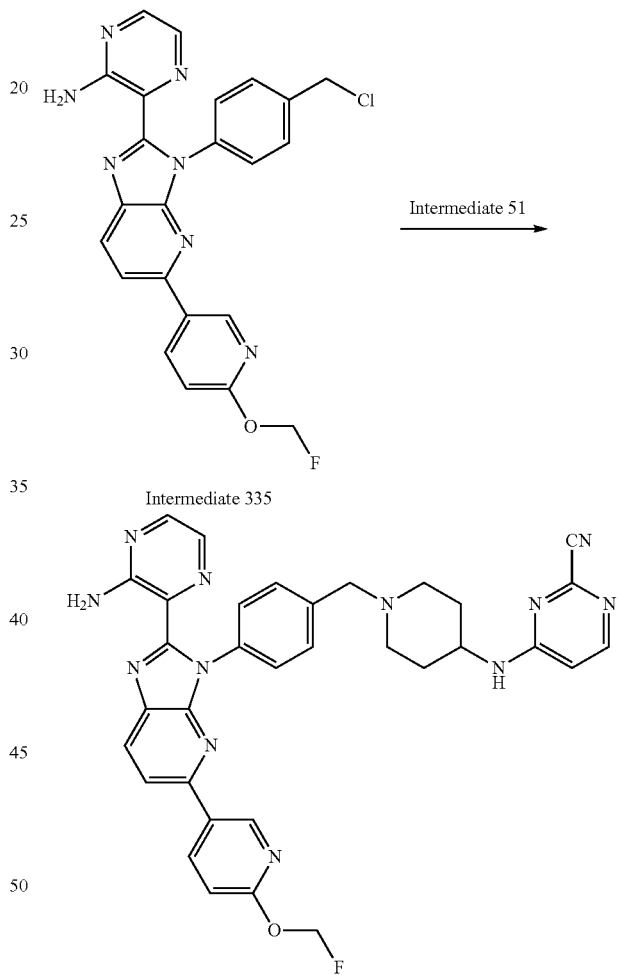

Intermediate 335

Example 639

To a solution of Intermediate 335 (420 mg, 843 μmol, HCl salt), Intermediate 335 (294 mg, 927 μmol, TFA salt) in DMF (2 mL) were added K₂CO₃ (582 mg, 4.21 mmol) and NaI (37.9 mg, 253 μmol). The mixture was stirred at 25° C. for 16 hr. The reaction mixture was quenched with H₂O (20 mL) and extracted with EtOAc (30 mL×3). The combined organic layers were washed with brine (30 mL×3), dried over anhydrous Na₂SO₄, filtered and concentrated under reduced pressure. After purified by silica gel flash chromatography (Eluent of 0%~5% MeOH in CH₂Cl₂), 4-((1-(4-(2-(3-aminopyrazin-2-yl)-5-(6-(fluoromethoxy)pyridin-3- yl)-3H-imidazo[4,5-b]pyridin-3-yl)benzyl)piperidin-4-yl)amino)pyrimidine-2-carbonitrile (Example 639, 269 mg, yield: 51% for three steps) was obtained as a yellow solid. MS: m/z=629.2 [M+H]$^+$. $^1$H NMR (400 MHz, Dimethylsulfoxide-d$_6$) δ 8.90 (d, J=2.0 Hz, 1H), 8.41 (dd, J=8.4, 2.4 Hz, 1H), 8.37 (d, J=8.4 Hz, 1H), 8.15-8.03 (m, 3H), 8.02 (d, J=2.0 Hz, 1H), 7.82 (br s, 2H), 7.49 (d, J=2.4 Hz, 1H), 7.46-7.41 (m, 2H), 7.41-7.36 (m, 2H), 7.09 (d, J=8.8 Hz, 1H), 6.68 (br d, J=6.4 Hz, 1H), 6.12 (d, J=52.8 Hz, 2H), 3.91-3.76 (m, 1H), 3.60 (s, 2H), 2.89-2.82 (m, 2H), 2.22-2.11 (m, 2H), 1.96-1.84 (m, 2H), 1.57-1.45 (m, 2H). $^{19}$F NMR (400 MHz, Dimethysulfoxide-d$_6$) δ −154.386.

Example 640: 4-((1-(4-(2-(3-Aminopyrazin-2-yl)-5-(6-(fluoromethoxy-d$_2$)pyridin-3-yl)-3H-imidazo[4,5-b]pyridin-3-yl)benzyl)piperidin-4-yl)amino)pyrimidine-2-carbonitrile

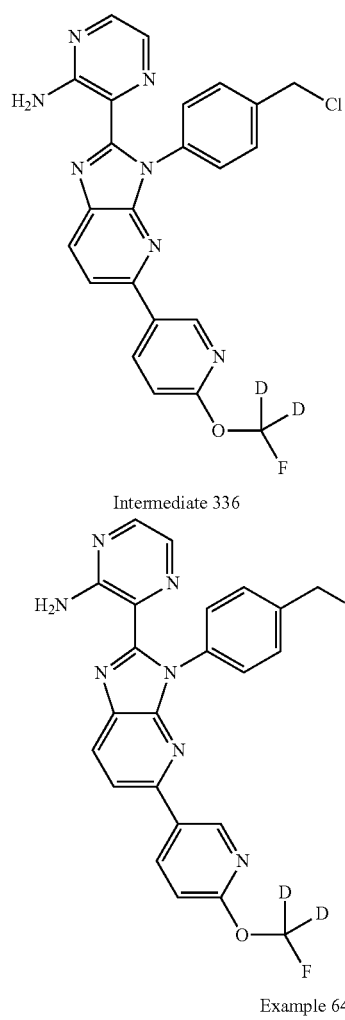

To a solution of Intermediate 336 (207 mg, 414 μmol, HCl salt) and Intermediate 51 (131 mg, 414 μmol, TFA) in DMF (5 mL) were added K$_2$CO$_3$ (172 mg, 1.24 mmol) and NaI (6.2 mg, 41.4 μmol). The mixture was stirred at 50° C. for 1 hr. The reaction mixture was quenched with H$_2$O (30 mL) at 25° C. and extracted with CH$_2$Cl$_2$ (20 mL×2). The combined organic layers were washed with brine (50 mL×3), dried over Na$_2$SO$_4$, filtered and concentrated under reduced pressure. After purified by silica gel flash chromatography (Eluent of 1%~5% MeOH in CH$_2$Cl$_2$) and triturated with EtOAc (10 mL) at 25° C. for 5 min., 4-((1-(4-(2-(3-aminopyrazin-2-yl)-5-(6-(fluoromethoxy-d$_2$)pyridin-3-yl)-3H-imidazo[4,5-b]pyridin-3-yl)benzyl)piperidin-4-yl)amino)pyrimidine-2-carbonitrile (Example 640, 104 mg, yield: 39% for two steps) was obtained as a yellow solid. MS: m/z=631.2 [M+H]$^+$. D %: 2D %=96.6%. $^1$H NMR (400 MHz, Dimethylsulfoxide-d$_6$) δ 8.94-8.86 (m, 1H), 8.44-8.34 (m, 2H), 8.10-8.01 (m, 4H), 7.80 (br s, 2H), 7.51-7.47 (m, 1H), 7.46-7.41 (m, 2H), 7.40-7.36 (m, 2H), 7.09 (d, J=8.4 Hz, 1H), 6.68 (d, J=5.2 Hz, 1H), 3.89-3.77 (m, 1H), 3.60 (s, 2H), 2.88-2.82 (m, 2H), 2.22-2.14 (m, 2H), 1.95-1.87 (m, 2H), 1.56-1.47 (m, 2H). $^{19}$F NMR (400 MHz, Dimethylsulfoxide-d$_6$) δ −155.59.

Example 641: 4-((1-(4-(2-(2-Aminopyridin-3-yl)-5-(6-cyclopropoxypyridin-3-yl)-3H-imidazo[4,5-b]pyridin-3-yl)benzyl)piperidin-4-yl)amino)pyrimidine-2-carbonitrile

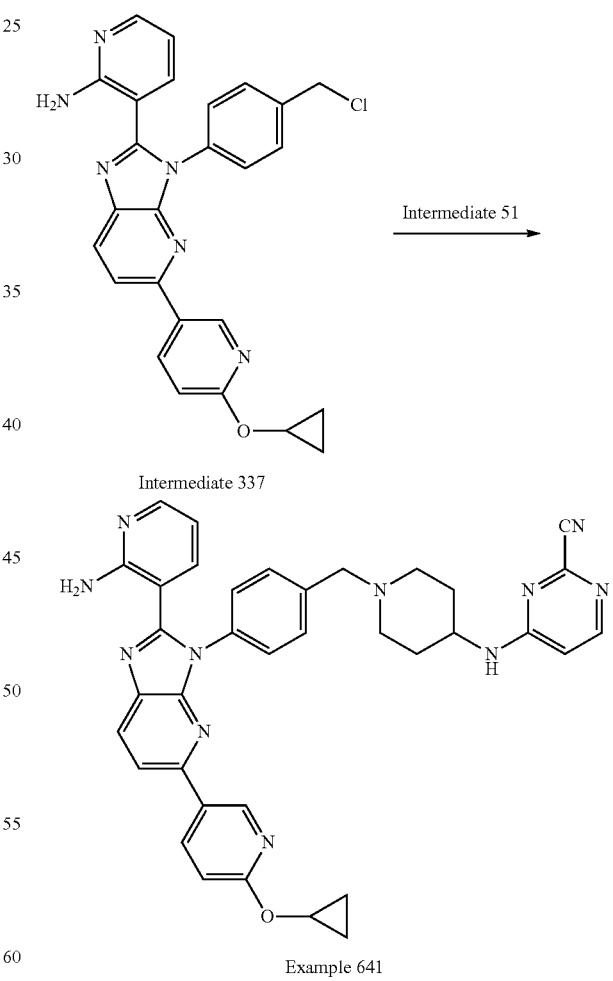

To a mixture of Intermediate 337 (191 mg, 407 μmol) and Intermediate 51 (91.1 mg, 448 gmol) in DMF (4 mL) were added NaI (12.2 mg, 81.5 μmol) and K$_2$CO$_3$ (169 mg, 1.22 mmol). The mixture was stirred at 80° C. for 12 hr. The mixture was diluted with H$_2$O (50 mL) and extracted with EtOAc (50 mL×2). The combined organic layers were washed with brine (50 mL), dried over anhydrous Na$_2$SO$_4$, filtered and concentrated. After purified by silica gel flash chromatography (Methanol in CH$_2$Cl$_2$=0-10%) and prep-HPLC (column: C18 150×30 mm; mobile phase: [water (NH$_3$H$_2$O+NH$_4$HCO$_3$)-ACN]; gradient: 48%-78% B over 7 min), 4-((1-(4-(2-(2-aminopyridin-3-yl)-5-(6-cyclopropoxypyridin-3-yl)-3H-imidazo[4,5-b]pyridin-3-yl)benzyl)piperidin-4-yl)amino)pyrimidine-2-carbonitrile (Example 641, 50.7 mg, yield 20% for 3 steps) was obtained as a white solid. MS: m/z=658.2 [M+Na]$^+$. $^1$H NMR (400 MHz, Dimethylsulfoxide-d$_6$) δ 8.87 (d, J=2.0 Hz, 1H), 8.34-8.24 (m, 2H), 8.12-8.04 (m, 2H), 8.01-7.95 (m, 2H), 7.52-7.43 (m, 4H), 7.16 (d, J=7.2 Hz, 1H), 7.04 (br s, 2H), 6.95 (d, J=8.8 Hz, 1H), 6.67 (d, J=6.4 Hz, 1H), 6.38 (dd, J=7.6, 4.8 Hz, 11H), 4.28-4.19 (m, 11H), 3.90-3.75 (m, 11H), 3.59 (s, 2H), 2.90-2.78 (m, 2H), 2.21-2.11 (m, 2H), 1.94-1.80 (m, 2H), 1.55-1.40 (m, 2H), 0.82-0.73 (m, 2H), 0.70-0.61 (m, 2H).

Example 642: 4-((1-(4-(2-(2-Aminopyridin-3-yl)-5-(6-isopropoxypyridin-3-yl)-3H-imidazo[4,5-b]pyridin-3-yl)benzyl)piperidin-4-yl)amino)pyrimidine-2-carbonitrile 483 μmol) in DMF (3 mL) were added NaI (13.2 mg, 87.9 μmol) and K$_2$CO$_3$ (182 mg, 1.32 mmol), the mixture was stirred at 20° C. for 12 hr. The reaction mixture was quenched with H$_2$O (50 mL) and extracted with EtOAc (30 mL×2). The combined organic layers were washed with brine (20 mL), dried over anhydrous Na$_2$SO$_4$, filtered and concentrated. After purified by silica gel flash chromatography (MeOH in CH$_2$Cl$_2$=0-10%), 4-((1-(4-(2-(2-aminopyridin-3-yl)-5-(6-isopropoxypyridin-3-yl)-3H-imidazo[4,5-b]pyridin-3-yl)benzyl)piperidin-4-yl)amino)pyrimidine-2-carbonitrile (Example 642, 78.7 mg, yield: 28% for three steps) was obtained as a white solid. MS: m/z=660.2 [M+Na]$^+$. $^1$H NMR (400 MHz, Dimethylsulfoxide-d$_6$) δ 8.84 (d, J=2.0 Hz, 1H), 8.32-8.23 (m, 2H), 8.12-8.03 (m, 2H), 8.01-7.92 (m, 2H), 7.52-7.41 (m, 4H), 7.15 (dd, J=7.6, 1.6 Hz, 1H), 7.03 (br s, 2H), 6.82 (d, J=8.8 Hz, 1H), 6.67 (d, J=6.0 Hz, 1H), 6.38 (dd, J=8.0, 4.8 Hz, 1H), 5.32-5.21 (m, 1H), 3.88-3.74 (m, 1H), 3.59 (s, 2H), 2.91-2.76 (m, 2H), 2.21-2.09 (m, 2H), 1.96-1.81 (m, 2H), 1.55-1.43 (m, 2H), 1.33-1.29 (m, 6H).

Example 643: 4-((1-(4-(2-(2-Aminopyridin-3-yl)-5-(6-isopropylpyridin-3-yl)-3H-imidazo[4,5-b]pyridin-3-yl)benzyl)piperidin-4-yl)amino)pyrimidine-2-carbonitrile

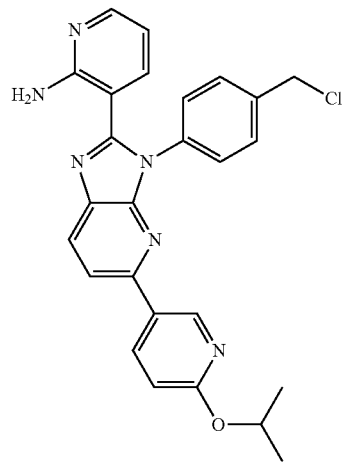

Intermediate 338

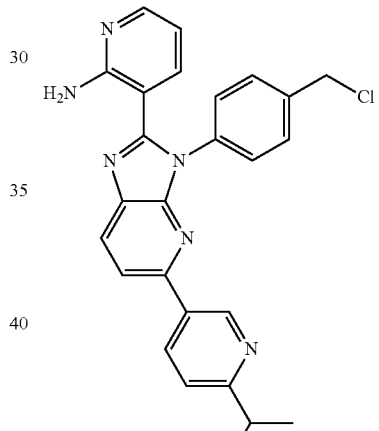

Intermediate 342

Intermediate 51 →

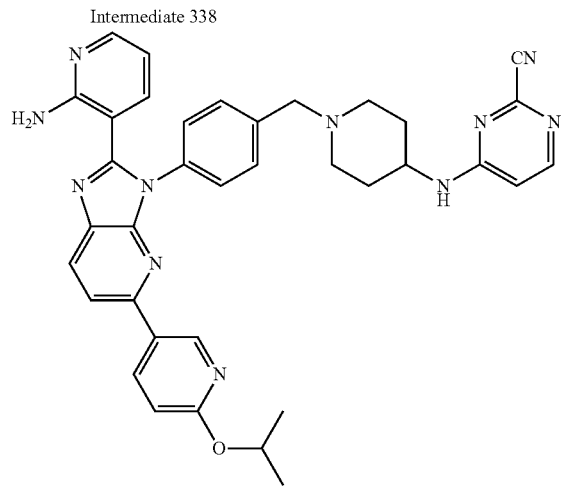

Example 642

Intermediate 51 →

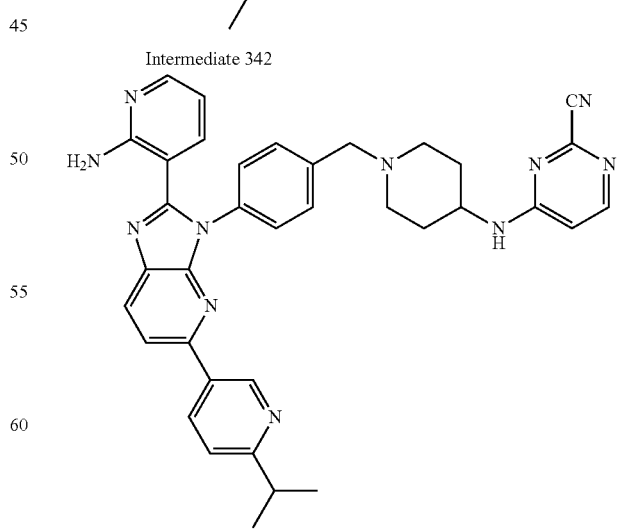

Example 643

To a mixture of Intermediate 338 (207 mg, 440 μmol) and 4-(piperidin-4-ylamino)pyrimidine-2-carbonitrile (98.3 mg, To a solution of Intermediate 342 (186 mg, 409 μmol) and Intermediate 51 (99.7 mg, 491 μmol) in DMF (6 mL) were added K$_2$CO$_3$ (170 mg, 1.23 mmol) and NaI (12.3 mg, 81.8 μmol) at 20° C. The reaction mixture was stirred at 20° C. for 12 hr and 80° C. for 2 hr. The mixture was diluted with H$_2$O (20 mL) and extracted with EtOAc (20 mL×2). The combined organic layers were washed with brine (20 mL), dried over anhydrous Na$_2$SO$_4$, filtered and concentrated. After purified by prep-HPLC (column: C18 150×30 mm; mobile phase: [water (NH$_3$H$_2$O+NH$_4$HCO$_3$)-ACN]; gradient: 56%-86% B over 7 min), 4-((1-(4-(2-(2-aminopyridin-3-yl)-5-(6-isopropylpyridin-3-yl)-3H-imidazo[4,5-b]pyridin-3-yl)benzyl)piperidin-4-yl)amino)pyrimidine-2-carbonitrile (Example 643, 64.2 mg, 99.0 μmol, 24% yield for 3 steps) was obtained as a yellow solid. MS: m/z=622.3 [M+H]$^+$. $^1$H NMR (400 MHz, Dimethylsulfoxide-d$_6$) δ 9.13-9.11 (m, 1H), 8.32-8.25 (m, 2H), 8.13-7.99 (m, 4H), 7.51-7.44 (m, 4H), 7.36 (d, J=8.0 Hz, 1H), 7.17 (dd, J=8.0, 2.0 Hz, 1H), 7.03 (s, 2H), 6.67 (d, J=6.0 Hz, 1H), 6.39 (dd, J=7.6, 4.8 Hz, 1H), 3.82 (br s, 1H), 3.59 (s, 2H), 3.10-3.00 (m, 1H), 2.88-2.79 (m, 2H), 2.22-2.11 (m, 2H), 1.94-1.84 (m, 2H), 1.55-1.44 (m, 2H), 1.24 (d, J=7.2 Hz, 6H).

Example 644: 4-((1-(4-(2-(2-Aminopyridin-3-yl)-5-(5-cyclopropylpyridin-2-yl)-3H-imidazo[4,5-b]pyridin-3-yl)benzyl)piperidin-4-yl)amino)pyrimidine-2-carbonitrile To a solution of Intermediate 343 (238 mg, 525 gmol) in DMF (3 mL) were added Intermediate 51 (128 mg, 631 μmol), K$_2$CO$_3$ (218 mg, 1.58 mmol), and NaI (7.88 mg, 52.5 μmol). The mixture was stirred at 25° C. for 12 hr under N$_2$. The mixture was diluted with H$_2$O (20 mL) and extracted with EtOAc (10 mL×2). The combined organic layers were washed with brine (15 mL), dried over anhydrous Na$_2$SO$_4$, filtered and concentrated. After purified by prep-HPLC (column: Welch Xtimate C18 150×30 mm×5 μm; mobile phase: [water (NH$_4$HCO$_3$)-ACN]; gradient: 57%-87% B over 7 min), 4-((1-(4-(2-(2-aminopyridin-3-yl)-5-(5-cyclopropylpyridin-2-yl)-3H-imidazo[4,5-h]pyridin-3-yl)benzyl)piperidin-4-yl)amino)pyrimidine-2-carbonitrile (Example 644, 99.6 mg, yield: 30.6% for three steps) was obtained as a light yellow solid. MS: m/z=620.3 [M+H]$^+$. $^1$H NMR (400 MHz, Dimethylsulfoxide-d$_6$) δ 8.49 (d, J=2.0 Hz, 1H), 8.42 (d, J=8.4 Hz, 1H), 8.28 (d, J=8.4 Hz, 1H), 8.13-8.03 (m, 3H), 8.00 (dd, J=4.8, 2 Hz, 1H), 7.53-7.43 (m, 5H), 7.16 (dd, J=7.6, 2.4 Hz, 1H), 7.02 (br s, 2H), 6.68 (d, J=6.0 Hz, 1H), 6.38 (dd, J=7.6, 4.8 Hz, 1H), 3.89-3.74 (m, 1H), 3.60 (s, 2H), 2.90-2.76 (m, 2H), 2.23-2.16 (m, 2H), 2.15-1.95 (m, 1H), 1.94-1.84 (m, 2H), 1.59-1.47 (m, 2H), 1.07-1.03 (m, 2H), 0.82-0.77 (m, 2H).

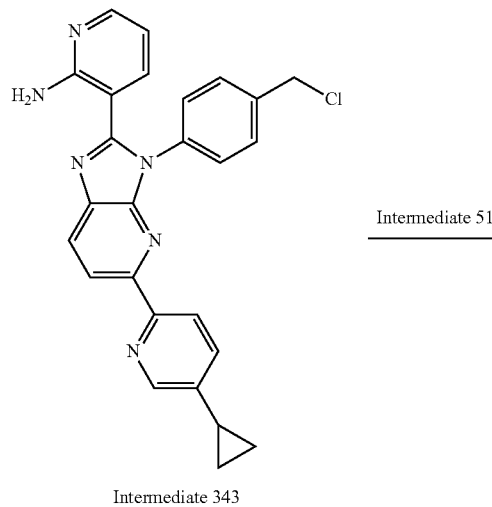

Intermediate 343

→ Intermediate 51

Example 645: 4-((1-(4-(2-(2-Aminopyridin-3-yl)-5-(6-(difluoromethyl)pyridin-3-yl)-3H-imidazo[4,5-b]pyridin-3-yl)benzyl)piperidin-4-yl)amino)pyrimidine-2-carbonitrile

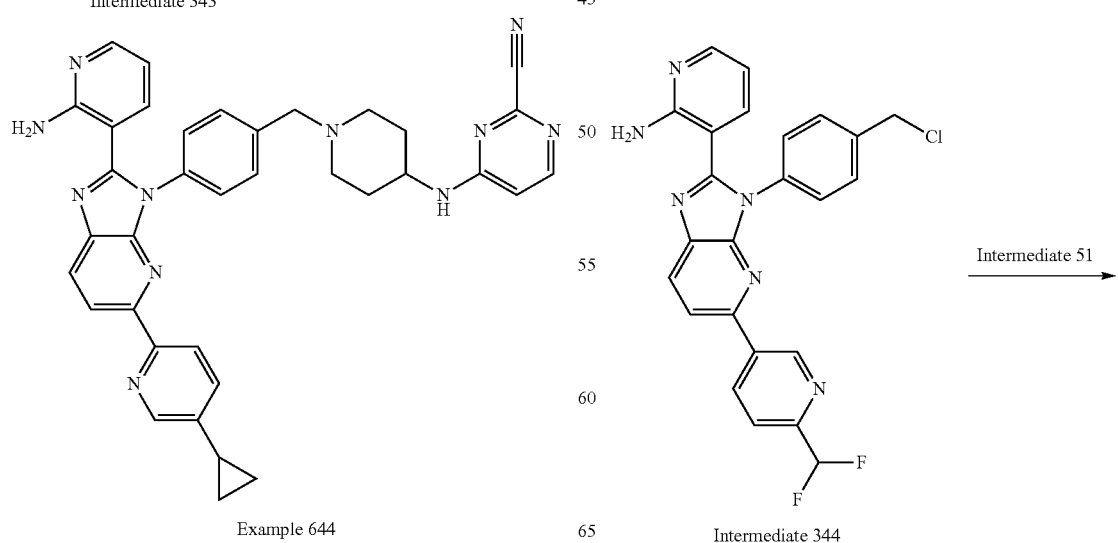

Example 644

Intermediate 344

→ Intermediate 51

-continued

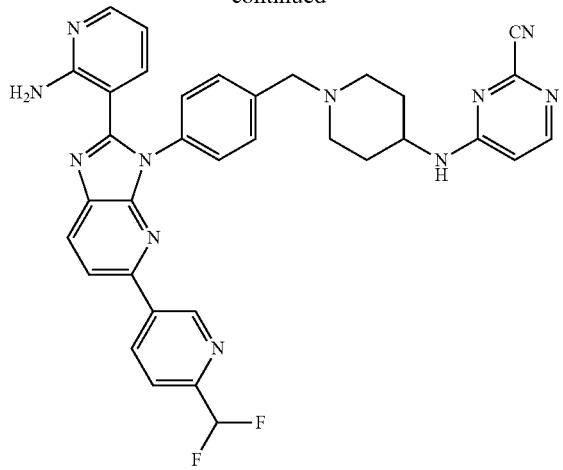

Example 645

To a solution of Intermediate 344 (405 mg, 811 μmol, HCl salt) and Intermediate 51 (260 mg, 820 μmol, TFA salt) in DMF (4 mL) were added $K_2CO_3$ (336 mg, 2.43 mmol) and NaI (12.2 mg, 81.1 μmol). The mixture was stirred at 25° C. for 16 hr. The reaction mixture was quenched with $H_2O$ (20 mL) and extracted with EtOAc (20 mL×3). The combined organic layers were washed with brine (20 mL×2), dried over $Na_2SO_4$, filtered and concentrated under reduced pressure. After purified by silica gel flash chromatography (Eluent of 0%-6% MeOH in $CH_2Cl_2$), 4-((1-(4-(2-(2-aminopyridin-3-yl)-5-(6-(difluoromethyl)pyridin-3-yl)-3H-imidazo[4,5-b]pyridin-3-yl)benzyl)piperidin-4-yl)amino)pyrimidine-2-carbonitrile (Example 645, 227.8 mg, yield: 45% for three steps) was obtained as a brown solid. MS: m/z=630.2 [M+H]$^+$. $^1$H NMR (400 MHz, Dimethylsulfoxide-d$_6$) δ 9.32 (s, 1H), 8.64-8.48 (m, 1H), 8.36 (d, J=8.4 Hz, 1H), 8.15 (d, J=8.4 Hz, 1H), 8.11-8.03 (m, 2H), 8.03-7.99 (m, 1H), 7.80 (d, J=8.0 Hz, 1H), 7.52-7.43 (m, 4H), 7.20-7.13 (m, 1H), 7.14-6.86 (m, 3H), 6.67 (d, J=5.6 Hz, 1H), 6.39 (dd, J=7.6, 4.8 Hz, 1H), 3.89-3.74 (m, 1H), 3.59 (s, 2H), 2.90-2.75 (m, 2H), 2.21-2.10 (m, 2H), 1.98-1.77 (m, 2H), 1.60-1.40 (m, 2H). $^{19}$F NMR (400 MHz, Dimethysulfoxide-d$_6$) δ −115.381.

Example 646: 4-((1-(4-(2-(2-Aminopyridin-3-yl)-5-(6-(trifluoromethyl)pyridin-3-yl)-3H-imidazo[4,5-b]pyridin-3-yl)benzyl)piperidin-4-yl)amino)pyrimidine-2-carbonitrile

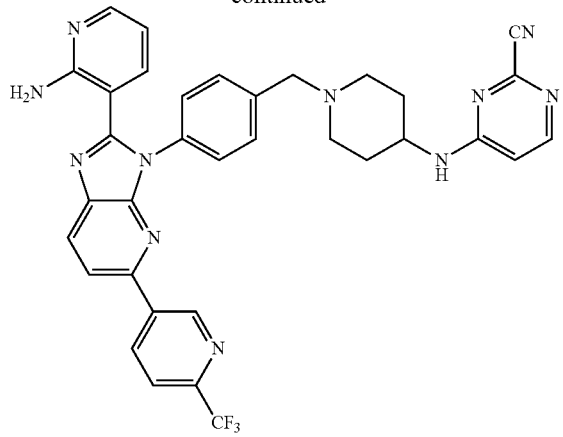

Example 646

To a solution of Intermediate 345 (276 mg, 574 μmol, HCl salt) and Intermediate 51 (200 mg, 631 μmol, TFA salt) in DMF (2 mL) were added $K_2CO_3$ (238 mg, 1.72 mmol) and NaI (8.60 mg, 57.4 μmol). The mixture was stirred at 25° C. for 16 hr. The reaction mixture was quenched with $H_2O$ (20 mL) and extracted with EtOAc (20 mL×3). The combined organic layers were washed with brine (20 mL×2), dried over $Na_2SO_4$, filtered and concentrated under reduced pressure. After purified by silica gel flash chromatography (Eluent of 0%-3% MeOH in $CH_2Cl_2$), 4-((1-(4-(2-(2-aminopyridin-3-yl)-5-(6-(trifluoromethyl)pyridin-3-yl)-3H-imidazo[4,5-b]pyridin-3-yl)benzyl)piperidin-4-yl)amino)pyrimidine-2-carbonitrile (Example 646, 199.8 mg, yield: 54% for three steps) was obtained as a light yellow solid. MS: m/z=648.2 [M+H]$^+$. $^1$H NMR (400 MHz, Methanol-d$_6$) 9.45 (s, 1H), 8.72-8.48 (m, 1H), 8.29 (d, J=8.8 Hz, 1H), 8.10 (d, J=8.4 Hz, 1H), 8.04-7.94 (m, 2H), 7.88 (d, J=8.0 Hz, 1H), 7.57 (d, J=8.4 Hz, 2H), 7.47 (d, J=8.4 Hz, 2H), 7.38-7.28 (m, 1H), 6.67-6.52 (m, 1H), 6.48 (dd, J=7.6, 4.8 Hz, 1H), 4.07-3.88 (m, 1H), 3.67 (s, 2H), 3.05-2.89 (m, 2H), 2.36-2.20 (m, 2H), 2.05-1.98 (m, 2H), 1.59-1.58 (m, 2H). $^{19}$F NMR (400 MHz, Dimethysulfoxide-d$_6$) δ −69.247.

Example 647: 4-((1-(4-(2-(2-Aminopyridin-3-yl)-5-(5-ethylpyridin-2-yl)-3H-imidazo[4,5-b]pyridin-3-yl)benzyl)piperidin-4-yl)amino)pyrimidine-2-carbonitrile

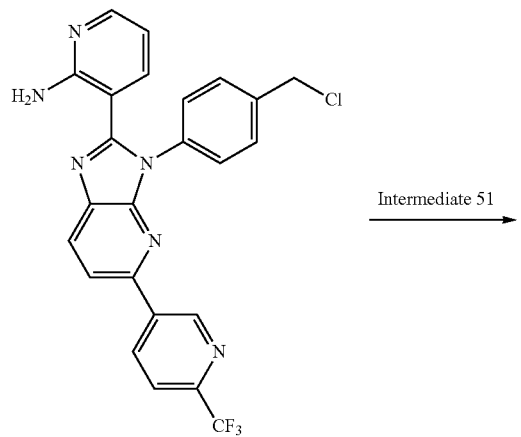

Intermediate 345 →(Intermediate 51)

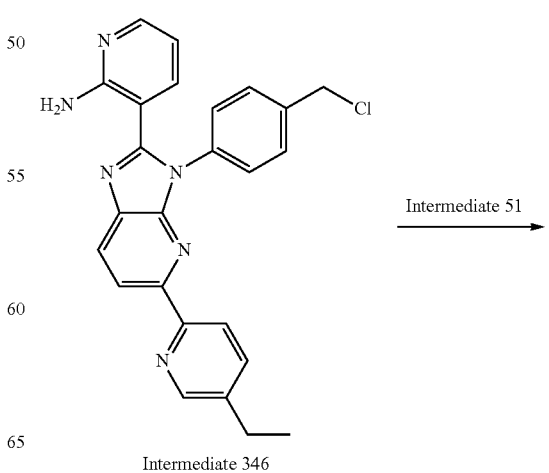

Intermediate 346 →(Intermediate 51)

-continued

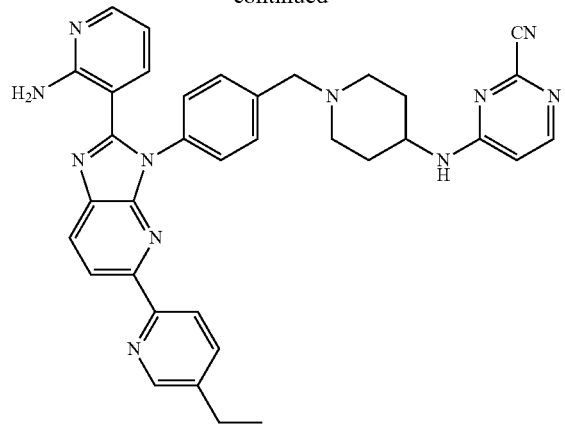

Example 647

To a solution of Intermediate 346 (237 mg, 496 μmol, HCl salt) and Intermediate 51 (158 mg, 496 μmol, TFA salt) in DMF (5 mL) were added K$_2$CO$_3$ (343 mg, 2.48 mmol) and NaI (14.9 mg, 99.3 μmol). The mixture was stirred at 50° C. for 1 hr. The reaction mixture was quenched with H$_2$O (10 mL) at 25° C. and extracted with CH$_2$Cl$_2$ (15 mL×2). The combined organic layers were washed with brine (50 mL×3), dried over Na$_2$SO$_4$, filtered and concentrated under reduced pressure. After purified by prep-HPLC (column: CD07-Daisogel SP-100-8-ODS-PK 150×25×10 μm; mobile phase: [water (NH$_4$HCO$_3$)-ACN]; gradient: 42%-72% B over 10 min), 4-((1-(4-(2-(2-aminopyridin-3-yl)-5-(5-ethylpyridin-2-yl)-3H-imidazo[4,5-b]pyridin-3-yl)benzyl)piperidin-4-yl)amino)pyrimidine-2-carbonitrile (Example 647, 100 mg, yield: 33% for two steps) was obtained as a yellow lyophilized powder. MS: m/z=608.3 [M+H]$^+$. $^1$H NMR (400 MHz, Dimethylsulfoxide-d$_6$) δ 8.53 (d, J=1.6 Hz, 1H), 8.43 (d, J=8.4 Hz, 1H), 8.29 (d, J=8.4 Hz, 1H), 8.14-8.02 (m, 3H), 8.00 (dd, J=4.8, 1.6 Hz, 1H), 7.74 (dd, J=8.0, 1.2 Hz, 1H), 7.53-7.43 (m, 4H), 7.19-7.13 (m, 1H), 7.02 (br s, 2H), 6.68 (d, J=6.0 Hz, 1H), 6.38 (dd, J=7.6, 4.8 Hz, 1H), 3.91-3.74 (m, 1H), 3.60 (s, 2H), 2.89-2.79 (m, 2H), 2.66 (q, J=7.6 Hz, 2H), 2.22-2.12 (m, 2H), 1.94-1.81 (m, 2H), 1.57-1.45 (m, 2H), 1.21 (t, J=7.6 Hz, 3H).

Example 648: 4-((1-(4-(2-(2-Aminopyridin-3-yl)-5-(5-(fluoromethyl)pyridin-2-yl)-3H-imidazo[4,5-b]pyridin-3-yl)benzyl)piperidin-4-yl)amino)pyrimidine-2-carbonitrile

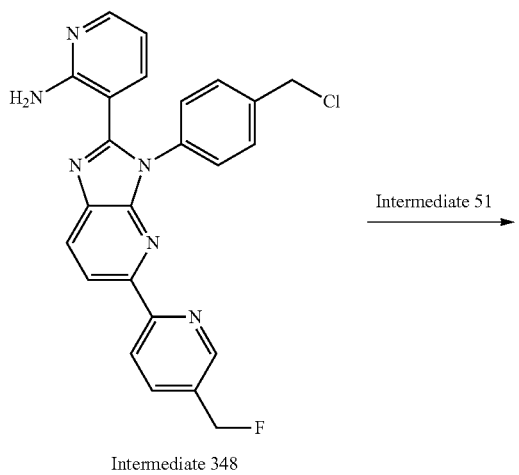

Intermediate 348 → Intermediate 51

-continued

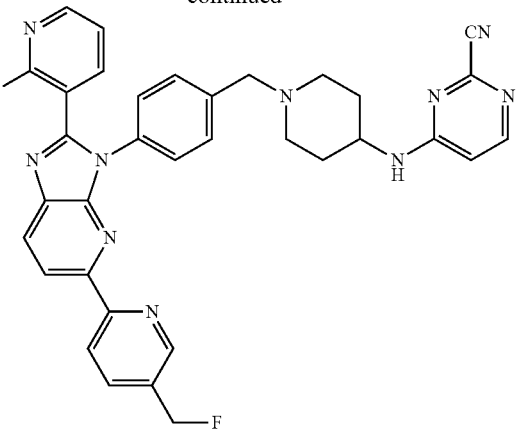

Example 648

To a solution of Intermediate 348 (158 mg, 328 μmol, HCl salt) and Intermediate 51 (104 mg, 328 μmol, TFA) in DMF (5 mL) were added K$_2$CO$_3$ (227 mg, 1.64 mmol) and NaI (9.84 mg, 65.7 μmol). The mixture was stirred at 50° C. for 1 hr. The reaction mixture was quenched with H$_2$O (5 mL) at 25° C. and extracted with CH$_2$Cl$_2$ (15 mL×2). The combined organic layers were washed with brine (50 mL×3), dried over Na$_2$SO$_4$, filtered and concentrated under reduced pressure. After purified by silica gel flash chromatography (Eluent of 0%~6% MeOH in CH$_2$Cl$_2$), 4-((1-(4-(2-(2-aminopyridin-3-yl)-5-(5-(fluoromethyl)pyridin-2-yl)-3H-imidazo[4,5-b]pyridin-3-yl)benzyl)piperidin-4-yl)amino)pyrimidine-2-carbonitrile (Example 648, 116 mg, yield: 52% for three steps) was obtained as a yellow solid. MS: m/z=612.3 [M+H]$^+$. $^1$H NMR (400 MHz, Dimethylsulfoxide-d$_6$) δ 8.73 (s, 1H), 8.49 (d, J=8.4 Hz, 1H), 8.32 (d, J=8.4 Hz, 1H), 8.23 (d, J=8.4 Hz, 1H), 8.13-8.02 (m, 2H), 8.01 (dd, J=4.8, 2.0 Hz, 1H), 7.99-7.94 (m, 1H), 7.52-7.46 (m, 4H), 7.17 (dd, J=7.6, 1.6 Hz, 1H), 7.01 (br s, 2H), 6.68 (d, J=6.0 Hz, 1H), 6.39 (dd, J=7.6, 4.8 Hz, 1H), 5.53 (d, J=47.2 Hz, 2H), 3.93-3.71 (m, 1H), 3.61 (s, 2H), 2.89-2.80 (m, 2H), 2.23-2.13 (m, 2H), 1.95-1.85 (m, 2H), 1.58-1.46 (m, 2H). $^{19}$F NMR (400 MHz, Dimethylsulfoxide-d$_6$) δ −206.809.

1785

Example 649: 4-((1-(4-(2-(2-Aminopyridin-3-yl)-5-(5-(difluoromethyl)pyridin-2-yl)-3H-imidazo[4,5-b]pyridin-3-yl)benzyl)piperidin-4-yl)amino)pyrimidine-2-carbonitrile

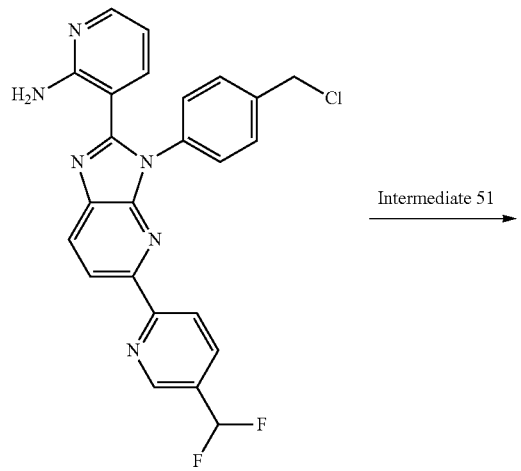

Intermediate 349

Intermediate 51 →

Example 649

To a solution of Intermediate 349 (270 mg, 541 µmol, HCl salt) and Intermediate 51 (172 mg, 541 µmol, TFA salt) in DMF (5 mL) were added $K_2CO_3$ (299 mg, 1.16 mmol) and NaI (41 mg, 270 µmol). The mixture was stirred at 25° C. for 16 hr. The reaction mixture was with $H_2O$ (5 mL) at 25° C. and extracted with EtOAc (10 mL×3). The combined organic layers were washed with brine (10 mL×3), dried over $Na_2SO_4$, filtered and concentrated under reduced pressure. After purified by prep-HPLC (column: CD$_{07}$-Daisogel SP-100-8-ODS-PK 150×25×10 µm; mobile phase: [water ($NH_4HCO_3$)-ACN]; gradient: 38%-68% B over 10 min), 4-((1-(4-(2-(2-aminopyridin-3-yl)-5-(5-(difluoromethyl)pyridin-2-yl)-3H-imidazo[4,5-b]pyridin-3-yl)benzyl)piperidin-4-yl)amino)pyrimidine-2-carbonitrile (Example 649, 170.4 mg, yield: 48% for two steps) was obtained as a yellow powder. MS: m/z=630.3 [M+H]$^+$. $^1$H NMR (400 MHz, Dimethylsulfoxide-d$_6$) δ 8.87 (s, 1H), 8.51 (d, J=8.4 Hz, 1H), 8.37-8.29 (m, 2H), 8.14-8.00 (m, 4H), 7.53-7.46 (m, 4H), 7.35-7.16 (m, 2H), 7.06-7.00 (m, 2H), 6.68 (d, J=6.0 Hz, 1H), 6.39 (dd, J=7.6, 4.8 Hz, 1H), 3.90-3.72 (m, 1H), 3.60 (s, 2H), 2.88-2.80 (m, 2H), 2.22-2.12 (m, 2H), 1.97-1.86 (m, 2H), 1.58-1.47 (m, 2H). $^{19}$F NMR (400 MHz, Dimethylsulfoxide-d$_6$) δ −111.254.

1786

Example 650: 4-((1-(4-(2-(2-Aminopyridin-3-yl)-5-(5-(trifluoromethyl)pyridin-2-yl)-3H-imidazo[4,5-b]pyridin-3-yl)benzyl)piperidin-4-yl)amino)pyrimidine-2-carbonitrile

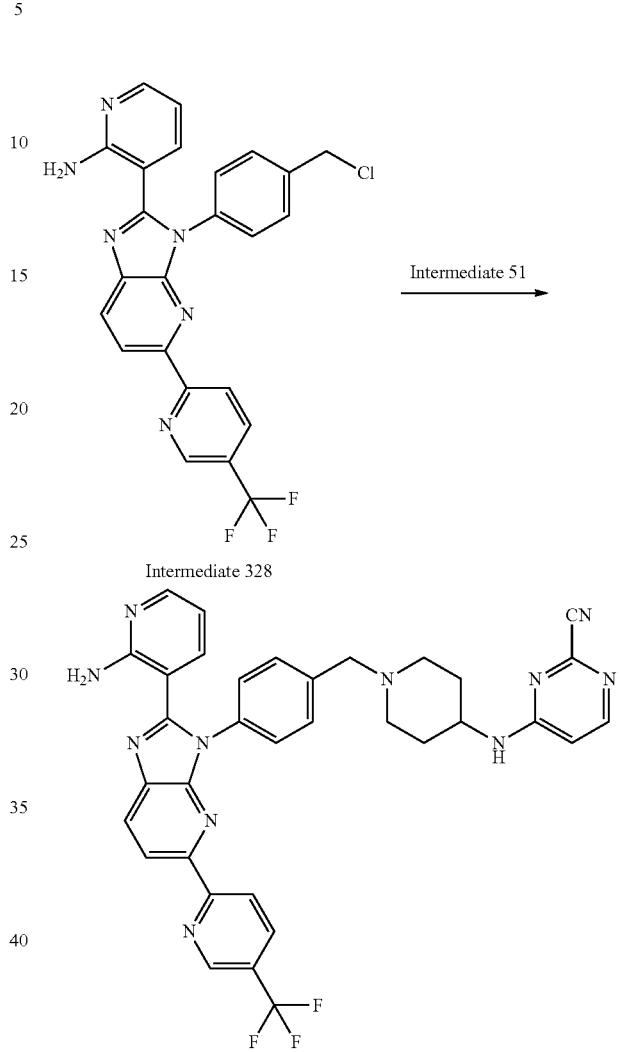

Intermediate 328

Intermediate 51 →

Example 650

To a solution of Intermediate 328 (246 mg, 476 µmol, HCl salt) and Intermediate 51 (151 mg, 476 µmol, TFA salt) in DMF (5 mL) were added $K_2CO_3$ (263 mg, 1.9 mmol) and NaI (36 mg, 238 µmol). The mixture was stirred at 25° C. for 16 hr. The reaction mixture was quenched with $H_2O$ (10 mL) at 25° C. and extracted with EtOAc (10 mL×3). The combined organic layers were washed with brine (10 mL×3), dried over $Na_2SO_4$, filtered and concentrated under reduced pressure. After purified by silica gel flash chromatography (Eluent of 0%~5% MeOH in $CH_2Cl_2$), 4-((1-(4-(2-(2-aminopyridin-3-yl)-5-(5-(trifluoromethyl)pyridin-2-yl)-3H-imidazo[4,5-b]pyridin-3-yl)benzyl)piperidin-4-yl)amino)pyrimidine-2-carbonitrile (Example 650, 166.4 mg, yield: 53% for two steps) was obtained as a light yellow powder. MS: m/z=648.6 [M+H]$^+$. $^1$H NMR (400 MHz, Dimethylsulfoxide-d$_6$) δ 9.06 (s, 1H), 8.53 (d, J=8.4 Hz, 1H), 8.41-8.26 (m, 3H), 8.21-7.97 (m, 3H), 7.57-7.42 (m, 4H), 7.18 (d, J=7.6 Hz, 1H), 7.03 (br s, 2H), 6.68 (d, J=5.6 Hz, 1H), 6.43-6.35 (m, 1H), 3.92-3.72 (m, 1H), 3.60 (s, 2H), 2.90-2.78 (m, 2H), 2.22-2.10 (m, 2H), 1.96-1.83 (m, 2H), 1.57-1.44 (m, 2H). $^{19}$F NMR (400 MHz, Dimethylsulfoxide-d6) δ −60.763.

II. Biological Evaluation

Example 1: NanoBRET Target Engagement (TE) Assay

NanoBRET is a highly specific and validated cell-based technique for assessing target engagement (Vasta et al., 2018, Cell Chem Biol. 25(2):206-214). The NanoBRET™ Target Engagement (TE) Intracellular Kinase Assays are based on the NanoBRET™ System (Promega Corporation), an energy transfer technique designed to measure molecular proximity in living cells. The NanoBRET™ TE Assays measure the apparent affinity of test compounds by competitive displacement of the NanoBRET™ tracer compound, which is a cell permeable molecule engineered to be reversibly bound to a NanoLuc® luciferase-kinase fusion expressed in cells. For compound screening, when a test compound binds to the selected kinase, the BRET signal is attenuated. For kinase inhibitors in particular, intracellular target selectivity is fundamental to pharmacological mechanism and allows the proteins of interest to be in the correct cellular confirmation. Although non-cell-based techniques have been developed to measure kinase binding or enzymatic inhibition with accuracy and precision, such approaches can fail to accurately predict engagement of the full-length target protein in the more complex and biologically relevant cellular context (Knight and Shokat, 2005, Chem. Biol. 12, 621-637; Smyth and Collins, 2009, J. Chem. Biol. 2, 131-151). The NanoBRET assay procedure was used to interrogate the compounds against the full length AKT E17K per manufacturers suggestions. Briefly, HEK-293 cells (ATCC Cat #CRL-1573) were used for transfection purposes using FuGENE HD Transfection Reagent (Promega Cat #E2311). All cells were evaluated for viability prior to transfection and optimization of the transfection was done prior to experimentation. Greater than 95% viability was used for all experiments. Following transfection, cells were washed and resuspended in Opti-MEM. NanoBRET assays were performed in white, 384-well plates (Corning) at a density of 2×10$^5$ cells/well. All example compounds were prepared as concentrated stock solutions in DMSO (Sigma-Aldrich). Compounds are dissolved in DMSO to make 10 mM stock solution. Example compounds were transferred as 40 µL of 10 mM stock solution to a 384 pp-plate (LABCYTE, PP-0200) and diluted in 3-fold, 10-point dilution via transferring 12 µL compound into 24 µL DMSO by Apricot liquid handler. A Labcyte ECHO 550 compound dispenser was used to facilitate compound transfer directly to cells. Cells were equilibrated for 2 hr with energy transfer probes and example compound prior to BRET measurements. The AKTE17K (Promega Cat #NV2421) as well as specific probe (NanoBRET tracer, Promega Cat #N264B) was prepared at a concentration of 20× in tracer dilution buffer (12.5 mM HEPES, 31.25% PEG-400, pH 7.5). For target engagement analysis, the energy transfer probes were added to the cells at concentrations optimized for the target in question (AKT E17K). Following compound incubation, NanoBRET NanoGlo Substrate (Promega Cat #N157D) and Extracellular Nanoluc Inhibitor (Promega Cat #N235C) was added according to the manufacturer's recommended protocol, and luminescence was measured on Envision Reader (Perkin Elmer) Multimode Luminometer equipped with 450 nm BPfilter (donor) and 600 nm LPfilter (acceptor), using 0.5 s integration time. Milli-BRET units (mBU) are calculated by multiplying the raw BRET values by 1000. Apparent tracer affinity values (EC50) were determined using the sigmoidal dose-response (variable slope).

Competitive displacement data were then plotted and data were fit to determine the $EC_{50}$ value for each example compound. Table 4 provides the assay results for select examples. Activity is defined as "+", for $EC_{50}$ between 600-10,000 nanomolar; "++" for $EC_{50}$ between 60-600 nanomolar; "+++" for $EC_{50}$ between 15-60 nanomolar; and "++++", for $EC_{50}$ less than 15 nanomolar.

TABLE 4

| Chemistry Example | Compound Name | MS: [M + H]$^+$ | AKT1 E17K IC50 |
|---|---|---|---|
| 1 | 6-((1-(4-(2-(2-aminopyridin-3-yl)-3H-imidazo[4,5-b]pyridin-3-yl)benzyl)piperidin-4-yl)oxy)nicotinonitrile | 503.1 | + |
| 2 | 6-((1-(4-(2-(2-aminopyridin-3-yl)-5-phenyl-3H-imidazo[4,5-b]pyridin-3-yl)benzyl)piperidin-4-yl)oxy)nicotinonitrile | 579.3 | ++ |
| 3 | 6-((1-(4-(2-(2-aminopyridin-3-yl)-6-phenyl-3H-imidazo[4,5-b]pyridin-3-yl)benzyl)piperidin-4-yl)oxy)nicotinonitrile | 579.1 | + |
| 4 | 6-((1-(4-(2-(2-aminopyridin-3-yl)-3H-imidazo[4,5-b]pyridin-3-yl)benzyl)piperidin-4-yl)oxy)picolinonitrile | 503.3 | + |
| 5 | 2-((1-(4-(2-(2-aminopyridin-3-yl)-3H-imidazo[4,5-b]pyridin-3-yl)benzyl)piperidin-4-yl)oxy)isonicotinonitrile | 503.3 | + |
| 6 | 2-((1-(4-(2-(2-aminopyridin-3-yl)-3H-imidazo[4,5-b]pyridin-3-yl)benzyl)piperidin-4-yl)oxy)nicotinonitrile | 503.4 | + |
| 7 | 6-((1-(4-(2-(2-aminopyridin-3-yl)-5-phenyl-3H-imidazo[4,5-b]pyridin-3-yl)benzyl)piperidin-4-yl)oxy)picolinonitrile | 579.3 | ++ |
| 8 | 2-((1-(4-(2-(2-aminopyridin-3-yl)-5-phenyl-3H-imidazo[4,5-b]pyridin-3-yl)benzyl)piperidin-4-yl)oxy)isonicotinonitrile | 579.1 | + |
| 9 | 2-((1-(4-(2-(2-aminopyridin-3-yl)-5-phenyl-3H-imidazo[4,5-b]pyridin-3-yl)benzyl)piperidin-4-yl)oxy)nicotinonitrile | 579.1 | ++ |
| 10 | 6-((1-(4-(2-(2-aminopyridin-3-yl)-6-phenyl-3H-imidazo[4,5-b]pyridin-3-yl)benzyl)piperidin-4-yl)oxy)picolinonitrile | 579.3 | + |
| 11 | 2-((1-(4-(2-(2-aminopyridin-3-yl)-6-phenyl-3H-imidazo[4,5-b]pyridin-3-yl)benzyl)piperidin-4-yl)oxy)isonicotinonitrile | 579.3 | + |
| 12 | 2-((1-(4-(2-(2-aminopyridin-3-yl)-6-phenyl-3H-imidazo[4,5-b]pyridin-3-yl)benzyl)piperidin-4-yl)oxy)nicotinonitrile | 579.2 | + |
| 13 | 4-(4-(4-(2-(2-aminopyridin-3-yl)-3H-imidazo[4,5-b]pyridin-3-yl)benzyl)piperazin-1-yl)picolinonitrile | 488.1 | + |

TABLE 4-continued

| Chemistry Example | Compound Name | MS: [M + H]+ | AKT1 E17K IC50 |
|---|---|---|---|
| 14 | 5-(4-(4-(2-(2-aminopyridin-3-yl)-3H-imidazo[4,5-b]pyridin-3-yl)benzyl)piperazin-1-yl)picolinonitrile | 488.2 | + |
| 15 | 6-(4-(4-(2-(2-aminopyridin-3-yl)-3H-imidazo[4,5-b]pyridin-3-yl)benzyl)piperazin-1-yl)picolinonitrile | 488.3 | + |
| 16 | 5-(4-(4-(2-(2-aminopyridin-3-yl)-3H-imidazo[4,5-b]pyridin-3-yl)benzyl)piperazin-1-yl)nicotinonitrile | 488.3 | + |
| 17 | 2-(4-(4-(2-(2-aminopyridin-3-yl)-3H-imidazo[4,5-b]pyridin-3-yl)benzyl)piperazin-1-yl)isonicotinonitrile | 488.3 | + |
| 18 | 4-(4-(4-(2-(2-aminopyridin-3-yl)-3H-imidazo[4,5-b]pyridin-3-yl)benzyl)piperazin-1-yl)pyrimidine-2-carbonitrile | 489.4 | ++ |
| 19 | 6-(4-(4-(2-(2-aminopyridin-3-yl)-3H-imidazo[4,5-b]pyridin-3-yl)benzyl)piperazin-1-yl)pyrazine-2-carbonitrile | 489.3 | + |
| 20 | 2-(4-(4-(2-(2-aminopyridin-3-yl)-3H-imidazo[4,5-b]pyridin-3-yl)benzyl)piperazin-1-yl)pyrimidine-4-carbonitrile | 489.3 | + |
| 21 | 6-(4-(4-(2-(2-aminopyridin-3-yl)-3H-imidazo[4,5-b]pyridin-3-yl)benzyl)piperazin-1-yl)pyrimidine-4-carbonitrile | 489.3 | ++ |
| 22 | 6-(4-(4-(2-(2-aminopyridin-3-yl)-3H-imidazo[4,5-b]pyridin-3-yl)benzyl)piperazin-1-yl)pyridazine-4-carbonitrile | 489.1 | + |
| 23 | N-(1-(4-(2-(2-aminopyridin-3-yl)-3H-imidazo[4,5-b]pyridin-3-yl)benzyl)piperidin-4-yl)-2-cyanoisonicotinamide | 530.2 | + |
| 24 | N-(1-(4-(2-(2-aminopyridin-3-yl)-3H-imidazo[4,5-b]pyridin-3-yl)benzyl)piperidin-4-yl)-6-cyanonicotinamide | 530.2 | + |
| 25 | N-(1-(4-(2-(2-aminopyridin-3-yl)-3H-imidazo[4,5-b]pyridin-3-yl)benzyl)piperidin-4-yl)-5-cyanopicolinamide | 530.1 | + |
| 26 | N-(1-(4-(2-(2-aminopyridin-3-yl)-3H-imidazo[4,5-b]pyridin-3-yl)benzyl)piperidin-4-yl)-5-cyanonicotinamide | 530.2 | + |
| 27 | N-(1-(4-(2-(2-aminopyridin-3-yl)-3H-imidazo[4,5-b]pyridin-3-yl)benzyl)piperidin-4-yl)-2-cyanonicotinamide | 530.3 | + |
| 28 | N-(1-(4-(2-(2-aminopyridin-3-yl)-3H-imidazo[4,5-b]pyridin-3-yl)benzyl)piperidin-4-yl)-3-cyanopicolinamide | 529.9 | + |
| 29 | N-(1-(4-(2-(2-aminopyridin-3-yl)-3H-imidazo[4,5-b]pyridin-3-yl)benzyl)piperidin-4-yl)-4-cyanonicotinamide | 530.1 | + |
| 30 | N-(1-(4-(2-(2-aminopyridin-3-yl)-3H-imidazo[4,5-b]pyridin-3-yl)benzyl)piperidin-4-yl)-6-cyanopicolinamide | 530.1 | + |
| 31 | N-(1-(4-(2-(2-aminopyridin-3-yl)-3H-imidazo[4,5-b]pyridin-3-yl)benzyl)piperidin-4-yl)-4-cyanopicolinamide | 530.1 | + |
| 32 | N-(1-(4-(2-(2-aminopyridin-3-yl)-3H-imidazo[4,5-b]pyridin-3-yl)benzyl)piperidin-4-yl)-2-cyanopyrimidine-4-carboxamide | 531.0 | ++ |
| 33 | N-(1-(4-(2-(2-aminopyridin-3-yl)-3H-imidazo[4,5-b]pyridin-3-yl)benzyl)piperidin-4-yl)-6-cyanopyrimidine-4-carboxamide | 531.1 | + |
| 34 | N-(1-(4-(2-(2-aminopyridin-3-yl)-3H-imidazo[4,5-b]pyridin-3-yl)benzyl)piperidin-4-yl)-2-cyanobenzo[d]thiazole-5-carboxamide | 586.2 | ++ |
| 35 | N-(1-(4-(2-(2-aminopyridin-3-yl)-3H-imidazo[4,5-b]pyridin-3-yl)benzyl)piperidin-4-yl)-2-cyano-5-fluorobenzo[d]thiazole-7-carboxamide | 604.3 | ++ |
| 36 | N-(1-(4-(2-(2-aminopyridin-3-yl)-3H-imidazo[4,5-b]pyridin-3-yl)benzyl)piperidin-4-yl)-3-cyanoisonicotinamide | 530.2 | + |
| 37 | N-(3-(2-(2-aminopyridin-3-yl)-3-(4-((4-(2-cyanopyridin-4-yl)piperazin-1-yl)methyl)phenyl)-3H-imidazo[4,5-b]pyridin-5-yl)phenyl)acetamide | 621.2 | +++ |
| 38 | N-(3-(2-(2-aminopyridin-3-yl)-3-(4-((4-(6-cyanopyridin-3-yl)piperazin-1-yl)methyl)phenyl)-3H-imidazo[4,5-b]pyridin-5-yl)phenyl)acetamide | 621.2 | ++ |
| 39 | N-(3-(2-(2-aminopyridin-3-y)-3-(4-(4-(6-cyanopyridin-2-yl)piperazin-1-yl)methyl)phenyl)-3H-imidazo[4,5-b]pyridin-5-yl)phenyl)acetamide | 621.2 | ++ |
| 40 | N-(3-(2-(2-aminopyridin-3-yl)-3-(4-((4-(6-cyanopyrazin-2-yl)piperazin-1-yl)methyl)phenyl)-3H-imidazo[4,5-b]pyridin-5-yl)phenyl)acetamide | 622.2 | ++++ |
| 41 | N-(3-(2-(2-aminopyridin-3-yl)-3-(4-((4-(6-cyanopyrimidin-4-yl)piperazin-1-yl)methyl)phenyl)-3H-imidazo[4,5-b]pyridin-5-yl)phenyl)acetamide | 622.2 | ++++ |
| 42 | N-(3-(2-(2-aminopyridin-3-yl)-3-(4-((4-(2-cyanopyrimidin-5-yl)piperazin-1-yl)methyl)phenyl)-3H-imidazo[4,5-b]pyridin-5-yl)phenyl)acetamide | 622.3 | +++ |
| 43 | N-(3-(2-(2-aminopyridin-3-yl)-3-(4-((4-(6-cyanopyridazin-4-yl)piperazin-1-yl)methyl)phenyl)-3H-imidazo[4,5-b]pyridin-5-yl)phenyl)acetamide | 622.4 | ++ |
| 44 | N-(3-(2-(2-aminopyridin-3-yl)-3-(4-((4-(2-cyanopyrimidin-4-yl)piperazin-1-yl)methyl)phenyl)-3H-imidazo[4,5-b]pyridin-5-yl)phenyl)acetamide | 622.5 | ++++ |
| 45 | N-(3-(2-(2-aminopyridin-3-yl)-3-(4-((4-(5-cyanopyridazin-3-yl)piperazin-1-yl)methyl)phenyl)-3H-imidazo[4,5-b]pyridin-5-yl)phenyl)acetamide | 622.2 | ++ |

TABLE 4-continued

| Chemistry Example | Compound Name | MS: [M + H]+ | AKT1 E17K IC50 |
|---|---|---|---|
| 46 | N-(3-(2-(2-aminopyridin-3-yl)-3-(4-((4-(4-cyanopyrimidin-2-yl)piperazin-1-yl)methyl)phenyl)-3H-imidazo[4,5-b]pyridin-5-yl)phenyl)acetamide | 622.3 | ++++ |
| 47 | 4-((4-(2-(2-aminopyridin-3-yl)-3H-imidazo[4,5-b]pyridin-3-yl)benzyl)amino)pyrimidine-2-carbonitrile | 420.3 | + |
| 48 | 4-((4-(2-(2-aminopyridin-3-yl)-5-phenyl-3H-imidazo[4,5-b]pyridin-3-yl)benzyl)amino)pyrimidine-2-carbonitrile | 496.4 | +++ |
| 49 | 4-(4-(4-(2-(2-aminopyridin-3-yl)-5-phenyl-3H-imidazo[4,5-b]pyridin-3-yl)benzyl)piperazin-1-yl)pyrimidine-2-carbonitrile | 565.4 | ++++ |
| 50 | 6-((4-(2-(2-aminopyridin-3-yl)-3H-imidazo[4,5-b]pyridin-3-yl)benzyl)amino)pyridazine-4-carbonitrile | 420.1 | + |
| 51 | 6-((1-(4-(2-(2-aminopyridin-3-yl)-3H-imidazo[4,5-b]pyridin-3-yl)benzyl)piperidin-4-yl)amino)pyridazine-4-carbonitrile | 503.2 | + |
| 52 | 6-((4-(2-(2-aminopyridin-3-yl)-5-phenyl-3H-imidazo[4,5-b]pyridin-3-yl)benzyl)amino)pyridazine-4-carbonitrile | 496.1 | ++ |
| 53 | 6-(4-(4-(2-(2-aminopyridin-3-yl)-5-phenyl-3H-imidazo[4,5-b]pyridin-3-yl)benzyl)piperazin-1-yl)pyridazine-4-carbonitrile | 565.2 | ++ |
| 54 | 6-((1-(4-(2-(2-aminopyridin-3-yl)-5-phenyl-3H-imidazo[4,5-b]pyridin-3-yl)benzyl)piperidin-4-yl)amino)pyridazine-4-carbonitrile | 579.3 | ++ |
| 55 | N-(1-(4-(2-(2-aminopyridin-3-yl)-5-phenyl-3H-imidazo[4,5-b]pyridin-3-yl)benzyl)piperidin-4-yl)-2-cyanoisonicotinamide | 606.2 | +++ |
| 56 | N-(1-(4-(2-(2-aminopyridin-3-yl)-5-phenyl-3H-imidazo[4,5-b]pyridin-3-yl)benzyl)piperidin-4-yl)-6-cyanopicolinamide | 606.2 | ++++ |
| 57 | N-(1-(4-(2-(2-aminopyridin-3-yl)-5-phenyl-3H-imidazo[4,5-b]pyridin-3-yl)benzyl)piperidin-4-yl)-5-cyanonicotinamide | 606.2 | ++ |
| 58 | N-(1-(4-(2-(2-aminopyridin-3-yl)-5-phenyl-3H-imidazo[4,5-b]pyridin-3-yl)benzyl)piperidin-4-yl)-2-cyanonicotinamide | 606.4 | ++++ |
| 59 | N-(1-(4-(2-(2-aminopyridin-3-yl)-5-phenyl-3H-imidazo[4,5-b]pyridin-3-yl)benzyl)piperidin-4-yl)-3-cyanoisonicotinamide | 606.2 | +++ |
| 60 | N-(1-(4-(2-(2-aminopyridin-3-yl)-5-phenyl-3H-imidazo[4,5-b]pyridin-3-yl)benzyl)piperidin-4-yl)-4-cyanonicotinamide | 606.3 | ++++ |
| 61 | N-(1-(4-(2-(2-aminopyridin-3-yl)-5-phenyl-3H-imidazo[4,5-b]pyridin-3-yl)benzyl)piperidin-4-yl)-3-cyanopicolinamide | 606.1 | ++++ |
| 62 | 4-((1-(4-(2-(2-aminopyridin-3-yl)-3H-imidazo[4,5-b]pyridin-3-yl)benzyl)piperidin-4-yl)amino)picolinonitrile | 502.4 | + |
| 63 | 6-((1-(4-(2-(2-aminopyridin-3-yl)-3H-imidazo[4,5-b]pyridin-3-yl)benzyl)piperidin-4-yl)amino)picolinonitrile | 502.2 | + |
| 64 | 6-((1-(4-(2-(2-aminopyridin-3-yl)-3H-imidazo[4,5-b]pyridin-3-yl)benzyl)piperidin-4-yl)amino)pyrimidine-4-carbonitrile | 503.1 | + |
| 65 | 5-(4-(4-(2-(2-aminopyridin-3-yl)-5-phenyl-3H-imidazo[4,5-b]pyridin-3-yl)benzyl)piperazin-1-yl)nicotinonitrile | 564.1 | ++ |
| 66 | 2-(4-(4-(2-(2-aminopyridin-3-yl)-5-phenyl-3H-imidazo[4,5-b]pyridin-3-yl)benzyl)piperazin-1-yl)isonicotinonitrile | 564.2 | + |
| 67 | 6-(4-(4-(2-(2-aminopyridin-3-yl)-5-phenyl-3H-imidazo[4,5-b]pyridin-3-yl)benzyl)piperazin-1-yl)pyrazine-2-carbonitrile | 565.4 | ++ |
| 68 | 2-(4-(4-(2-(2-aminopyridin-3-yl)-5-phenyl-3H-imidazo[4,5-b]pyridin-3-yl)benzyl)piperazin-1-yl)pyrimidine-4-carbonitrile | 565.2 | ++++ |
| 69 | 6-(4-(4-(2-(2-aminopyridin-3-yl)-3H-imidazo[4,5-b]pyridin-3-yl)benzyl)piperazine-1-carbonyl)picolinonitrile | 516.1 | + |
| 70 | 4-(4-(4-(2-(2-aminopyridin-3-yl)-5-phenyl-3H-imidazo[4,5-b]pyridin-3-yl)benzyl)piperazine-1-carbonyl)pyridazine-3-carbonitrile | 593.3 | ++ |
| 71 | N-(1-(4-(2-(2-aminopyridin-3-yl)-5-phenyl-3H-imidazo[4,5-b]pyridin-3-yl)benzyl)piperidin-4-yl)-3-cyanopyridazine-4-carboxamide | 607.4 | +++ |
| 72 | 4-(4-(4-(2-(2-aminopyridin-3-yl)-5-phenyl-3H-imidazo[4,5-b]pyridin-3-yl)benzyl)piperazine-1-carbonyl)pyrimidine-5-carbonitrile | 593.4 | + |
| 73 | N-(1-(4-(2-(2-aminopyridin-3-yl)-5-phenyl-3H-imidazo[4,5-b]pyridin-3-yl)benzyl)piperidin-4-yl)-5-cyanopyrimidine-4-carboxamide | 607.3 | +++ |
| 74 | 5-((1-(4-(2-(2-aminopyridin-3-yl)-3H-imidazo[4,5-b]pyridin-3-yl)benzyl)piperidin-4-yl)amino)nicotinonitrile | 502.4 | + |
| 75 | 2-((1-(4-(2-(2-aminopyridin-3-yl)-3H-imidazo[4,5-b]pyridin-3-yl)benzyl)piperidin-4-yl)amino)isonicotinonitrile | 502.1 | + |
| 76 | 6-((1-(4-(2-(2-aminopyridin-3-yl)-3H-imidazo[4,5-b]pyridin-3-yl)benzyl)piperidin-4-yl)amino)pyrazine-2-carbonitrile | 503.2 | + |
| 77 | 2-((1-(4-(2-(2-aminopyridin-3-yl)-3H-imidazo[4,5-b]pyridin-3-yl)benzyl)piperidin-4-yl)amino)pyrimidine-4-carbonitrile | 503.3 | ++ |
| 78 | 6-(4-(4-(2-(2-aminopyridin-3-yl)-5-phenyl-3H-imidazo[4,5-b]pyridin-3-yl)benzyl)piperazin-1-yl)pyrimidine-4-carbonitrile | 565.2 | ++++ |
| 79 | 5-(4-(4-(2-(2-aminopyridin-3-yl)-3H-imidazo[4,5-b]pyridin-3-yl)benzyl)piperazine-1-carbonyl)nicotinonitrile | 516.2 | + |
| 80 | 6-(4-(4-(2-(2-aminopyridin-3-yl)-3H-imidazo[4,5-b]pyridin-3-yl)benzyl)piperazine-1-carbonyl)nicotinonitrile | 516.2 | + |

TABLE 4-continued

| Chemistry Example | Compound Name | MS: [M + H]+ | AKT1 E17K IC50 |
|---|---|---|---|
| 81 | N-(1-(4-(2-(2-aminopyridin-3-yl)-5-phenyl-3H-imidazo[4,5-b]pyridin-3-yl)benzyl)piperidin-4-yl)-5-cyanopicolinamide | 606.4 | ++ |
| 82 | 4-(4-(4-(2-(2-aminopyridin-3-yl)-5-phenyl-3H-imidazo[4,5-b]pyridin-3-yl)benzyl)piperazin-1-yl)picolinonitrile | 564.4 | +++ |
| 83 | 6-(4-(4-(2-(2-aminopyridin-3-yl)-5-phenyl-3H-imidazo[4,5-b]pyridin-3-yl)benzyl)piperazin-1-yl)picolinonitrile | 564.3 | ++ |
| 84 | 5-((1-(4-(2-(2-aminopyridin-3-yl)-5-phenyl-3H-imidazo[4,5-b]pyridin-3-yl)benzyl)piperidin-4-yl)amino)picolinonitrile | 578.2 | +++ |
| 85 | 4-((1-(4-(2-(2-aminopyridin-3-yl)-5-phenyl-3H-imidazo[4,5-b]pyridin-3-yl)benzyl)piperidin-4-yl)amino)picolinonitrile | 578.2 | ++++ |
| 86 | 6-((1-(4-(2-(2-aminopyridin-3-yl)-5-phenyl-3H-imidazo[4,5-b]pyridin-3-yl)benzyl)piperidin-4-yl)amino)picolinonitrile | 578.2 | ++ |
| 87 | 2-((1-(4-(2-(2-aminopyridin-3-yl)-5-phenyl-3H-imidazo[4,5-b]pyridin-3-yl)benzyl)piperidin-4-yl)amino)isonicotinonitrile | 578.3 | ++ |
| 88 | 4-((1-(4-(2-(2-aminopyridin-3-yl)-5-phenyl-3H-imidazo[4,5-b]pyridin-3-yl)benzyl)piperidin-4-yl)amino)pyrimidine-2-carbonitrile | 579.4 | ++++ |
| 89 | 6-((1-(4-(2-(2-aminopyridin-3-yl)-5-phenyl-3H-imidazo[4,5-b]pyridin-3-yl)benzyl)piperidin-4-yl)amino)pyrazine-2-carbonitrile | 579.1 | ++++ |
| 90 | 2-((1-(4-(2-(2-aminopyridin-3-yl)-5-phenyl-3H-imidazo[4,5-b]pyridin-3-yl)benzyl)piperidin-4-yl)amino)pyrimidine-4-carbonitrile | 579.1 | ++++ |
| 91 | 6-((1-(4-(2-(2-aminopyridin-3-yl)-5-phenyl-3H-imidazo[4,5-b]pyridin-3-yl)benzyl)piperidin-4-yl)amino)pyrimidine-4-carbonitrile | 579.2 | ++++ |
| 92 | 4-((1-(4-(2-(2-aminopyridin-3-yl)-3H-imidazo[4,5-b]pyridin-3-yl)benzyl)piperidin-4-yl)amino)pyrimidine-2-carbonitrile | 503.3 | +++ |
| 93 | 5-((1-(4-(2-(2-aminopyridin-3-yl)-5-phenyl-3H-imidazo[4,5-b]pyridin-3-yl)benzyl)piperidin-4-yl)amino)nicotinonitrile | 578.4 | ++ |
| 94 | 5-(4-(4-(2-(2-aminopyridin-3-yl)-5-phenyl-3H-imidazo[4,5-b]pyridin-3-yl)benzyl)piperazin-1-yl)picolinonitrile | 564.0 | ++ |
| 95 | 5-((4-(2-(2-aminopyridin-3-yl)-3H-imidazo[4,5-b]pyridin-3-yl)benzyl)amino)pyrimidine-2-carbonitrile | 420.1 | + |
| 96 | 5-((4-(2-(2-aminopyridin-3-yl)-5-phenyl-3H-imidazo[4,5-b]pyridin-3-yl)benzyl)amino)pyrimidine-2-carbonitrile | 496.3 | ++++ |
| 97 | 5-(4-(4-(2-(2-aminopyridin-3-yl)-5-phenyl-3H-imidazo[4,5-b]pyridin-3-yl)benzyl)piperazin-1-yl)pyrimidine-2-carbonitrile | 565.3 | +++ |
| 98 | N-(4-(2-(2-aminopyridin-3-yl)-3H-imidazo[4,5-b]pyridin-3-yl)benzyl)-2-cyanonicotinamide | 447.2 | + |
| 99 | N-(4-(2-(2-aminopyridin-3-yl)-3H-imidazo[4,5-b]pyridin-3-yl)benzyl)-3-cyanoisonicotinamide | 447.0 | + |
| 100 | N-(4-(2-(2-aminopyridin-3-yl)-3H-imidazo[4,5-b]pyridin-3-yl)benzyl)-4-cyanonicotinamide | 447.1 | + |
| 101 | N-(4-(2-(2-aminopyridin-3-yl)-3H-imidazo[4,5-b]pyridin-3-yl)benzyl)-3-cyanopicolinamide | 447.1 | + |
| 102 | 5-(4-(4-(2-(2-aminopyridin-3-yl)-3H-imidazo[4,5-b]pyridin-3-yl)benzyl)piperazine-1-carbonyl)picolinonitrile | 516.2 | + |
| 103 | N-(4-(2-(2-aminopyridin-3-yl)-5-phenyl-3H-imidazo[4,5-b]pyridin-3-yl)benzyl)-2-cyanonicotinamide | 523.2 | + |
| 104 | N-(4-(2-(2-aminopyridin-3-yl)-5-phenyl-3H-imidazo[4,5-b]pyridin-3-yl)benzyl)-3-cyanoisonicotinamide | 523.2 | + |
| 105 | N-(4-(2-(2-aminopyridin-3-yl)-5-phenyl-3H-imidazo[4,5-b]pyridin-3-yl)benzyl)-4-cyanonicotinamide | 523.2 | + |
| 106 | N-(4-(2-(2-aminopyridin-3-yl)-6-phenyl-3H-imidazo[4,5-b]pyridin-3-yl)benzyl)-6-cyanonicotinamide | 523.2 | + |
| 107 | N-(1-(4-(2-(2-aminopyridin-3-yl)-6-phenyl-3H-imidazo[4,5-b]pyridin-3-yl)benzyl)piperidin-4-yl)-2-cyanoisonicotinamide | 606.3 | + |
| 108 | N-(4-(2-(2-aminopyridin-3-yl)-3H-imidazo[4,5-b]pyridin-3-yl)benzyl)-6-cyanopicolinamide | 447.1 | + |
| 109 | 4-(4-(4-(2-(2-aminopyridin-3-yl)-3H-imidazo[4,5-b]pyridin-3-yl)benzyl)piperazine-1-carbonyl)picolinonitrile | 516.3 | + |
| 110 | 2-(4-(4-(2-(2-aminopyridin-3-yl)-3H-imidazo[4,5-b]pyridin-3-yl)benzyl)piperazine-1-carbonyl)nicotinonitrile | 516.0 | + |
| 111 | 5-(4-(4-(2-(2-aminopyridin-3-yl)-6-phenyl-3H-imidazo[4,5-b]pyridin-3-yl)benzyl)piperazine-1-carbonyl)picolinonitrile | 592.1 | + |
| 112 | 5-((4-(2-(2-aminopyridin-3-yl)-5-phenyl-3H-imidazo[4,5-b]pyridin-3-yl)benzyl)amino)pyridazine-3-carbonitrile | 496.2 | +++ |
| 113 | N-(4-(2-(2-aminopyridin-3-yl)-3H-imidazo[4,5-b]pyridin-3-yl)benzyl)-6-cyanopyrimidine-4-carboxamide | 448.2 | + |
| 114 | 6-(4-(4-(2-(2-aminopyridin-3-yl)-3H-imidazo[4,5-b]pyridin-3-yl)benzyl)piperazine-1-carbonyl)pyrimidine-4-carbonitrile | 517.1 | ++ |
| 115 | N-(4-(2-(2-aminopyridin-3-yl)-5-phenyl-3H-imidazo[4,5-b]pyridin-3-yl)benzyl)-6-cyanopyrimidine-4-carboxamide | 523.9 | ++++ |

TABLE 4-continued

| Chemistry Example | Compound Name | MS: [M + H]+ | AKT1 E17K IC50 |
|---|---|---|---|
| 116 | 6-(4-(4-(2-(2-aminopyridin-3-yl)-5-phenyl-3H-imidazo[4,5-b]pyridin-3-yl)benzyl)piperazine-1-carbonyl)pyrimidine-4-carbonitrile | 593.2 | ++++ |
| 117 | N-(1-(4-(2-(2-aminopyridin-3-yl)-5-phenyl-3H-imidazo[4,5-b]pyridin-3-yl)benzyl)piperidin-4-yl)-6-cyanopyrimidine-4-carboxamide | 607.2 | +++ |
| 118 | N-(4-(2-(2-aminopyridin-3-yl)-5-phenyl-3H-imidazo[4,5-b]pyridin-3-yl)benzyl)-3-cyanopicolinamide | 523.3 | + |
| 119 | N-(4-(2-(2-aminopyridin-3-yl)-3H-imidazo[4,5-b]pyridin-3-yl)benzyl)-2-cyanopyrimidine-5-carboxamide | 448.3 | + |
| 120 | N-(4-(2-(2-aminopyridin-3-yl)-5-phenyl-3H-imidazo[4,5-b]pyridin-3-yl)benzyl)-2-cyanopyrimidine-5-carboxamide | 524.3 | ++++ |
| 121 | N-(4-(2-(2-aminopyridin-3-yl)-3H-imidazo[4,5-b]pyridin-3-yl)benzyl)-6-cyanonicotinamide | 447.3 | + |
| 122 | N-(4-(2-(2-aminopyridin-3-yl)-3H-imidazo[4,5-b]pyridin-3-yl)benzyl)-2-cyanoisonicotinamide | 447.1 | + |
| 123 | N-(4-(2-(2-aminopyridin-3-yl)-3H-imidazo[4,5-b]pyridin-3-yl)benzyl)-5-cyanonicotinamide | 447.0 | + |
| 124 | N-(4-(2-(2-aminopyridin-3-yl)-3H-imidazo[4,5-b]pyridin-3-yl)benzyl)-5-cyanopicolinamide | 447.0 | + |
| 125 | N-(4-(2-(2-aminopyridin-3-yl)-5-phenyl-3H-imidazo[4,5-b]pyridin-3-yl)benzyl)-5-cyanonicotinamide | 523.4 | +++ |
| 126 | N-(4-(2-(2-aminopyridin-3-yl)-5-phenyl-3H-imidazo[4,5-b]pyridin-3-yl)benzyl)-5-cyanopicolinamide | 523.4 | + |
| 127 | 4-((4-(2-(2-aminopyridin-3-yl)-3H-imidazo[4,5-b]pyridin-3-yl)benzyl)amino)picolinonitrile | 419.0 | + |
| 128 | 5-((4-(2-(2-aminopyridin-3-yl)-3H-imidazo[4,5-b]pyridin-3-yl)benzyl)amino)picolinonitrile | 419.1 | + |
| 129 | 4-((4-(2-(2-aminopyridin-3-yl)-5-phenyl-3H-imidazo[4,5-b]pyridin-3-yl)benzyl)amino)picolinonitrile | 495.3 | ++ |
| 130 | 6-((4-(2-(2-aminopyridin-3-yl)-3H-imidazo[4,5-b]pyridin-3-yl)benzyl)amino)picolinonitrile | 419.1 | + |
| 131 | 5-((4-(2-(2-aminopyridin-3-yl)-3H-imidazo[4,5-b]pyridin-3-yl)benzyl)amino)nicotinonitrile | 419.1 | + |
| 132 | 2-((4-(2-(2-aminopyridin-3-yl)-3H-imidazo[4,5-b]pyridin-3-yl)benzyl)amino)isonicotinonitrile | 419.1 | + |
| 133 | 6-((4-(2-(2-aminopyridin-3-yl)-3H-imidazo[4,5-b]pyridin-3-yI)benzyl)amino)pyrazine-2-carbonitrile | 420.1 | + |
| 134 | 2-((4-(2-(2-aminopyridin-3-yl)-3H-imidazo[4,5-b]pyridin-3-yl)benzyl)amino)pyrimidine-4-carbonitrile | 420.0 | + |
| 135 | 6-((4-(2-(2-aminopyridin-3-yl)-3H-imidazo[4,5-b]pyridin-3-yl)benzyl)amino)pyrimidine-4-carbonitrile | 420.0 | + |
| 136 | 6-((4-(2-(2-aminopyridin-3-yl)-5-phenyl-3H-imidazo[4,5-b]pyridin-3-yl)benzyl)amino)pyrimidine-4-carbonitrile | 496.1 | +++ |
| 137 | 4-(4-(4-(2-(2-aminopyridin-3-yl)-6-phenyl-3H-imidazo[4,5-b]pyridin-3-yl)benzyl)piperazine-1-carbonyl)picolinonitrile | 592.3 | + |
| 138 | 6-(4-(4-(2-(2-aminopyridin-3-yl)-5-phenyl-3H-imidazo[4,5-b]pyridin-3-yl)benzyl)piperazine-1-carbonyl)picolinonitrile | 592.1 | ++ |
| 139 | 5-14-14-(2-(2-aminopyridin-3-yl)-5-phenyl-3H-imidazo[4,5-b]pyridin-3-yI)benzyl)piperazine-1-carbonyl)nicotinonitrile | 592.4 | + |
| 140 | 2-(4-(4-(2-(2-aminopyridin-3-yl)-5-phenyl-3H-imidazo[4,5-b]pyridin-3-yl)benzyl)piperazine-1-carbonyl)isonicotinonitrile | 592.1 | ++ |
| 141 | 4-(4-(4-(2-(2-aminopyridin-3-yl)-5-phenyl-3H-imidazo[4,5-b]pyridin-3-yl)benzyl)piperazine-1-carbonyl)pyrimidine-2-carbonitrile | 593.1 | ++++ |
| 142 | 6-(4-(4-(2-(2-aminopyridin-3-yl)-5-phenyl-3H-imidazo[4,5-b]pyridin-3-yl)benzyl)piperazine-1-carbonyl)nicotinonitrile | 592.2 | + |
| 143 | 3-(4-(4-(2-(2-aminopyridin-3-yl)-5-phenyl-3H-imidazo[4,5-b]pyridin-3-yl)benzyl)piperazine-1-carbonyl)picolinonitrile | 592.2 | ++ |
| 144 | 4-(4-(4-(2-(2-aminopyridin-3-yl)-5-phenyl-3H-imidazo[4,5-b]pyridin-3-yl)benzyl)piperazine-1-carbonyl)nicotinonitrile | 592.3 | + |
| 145 | 3-(4-(4-(2-(2-aminopyridin-3-yl)-5-phenyl-3H-imidazo[4,5-b]pyridin-3-yl)benzyl)piperazine-1-carbonyl)isonicotinonitrile | 592.2 | + |
| 146 | 2-(4-(4-(2-(2-aminopyridin-3-yl)-5-phenyl-3H-imidazo[4,5-b]pyridin-3-yl)benzyl)piperazine-1-carbonyl)nicotinonitrile | 592.2 | + |
| 147 | N-(4-(2-(2-aminopyridin-3-yl)-3H-imidazo[4,5-b]pyridin-3-yl)benzyl)-4-cyanopicolinamide | 447.3 | + |
| 148 | N-(4-(2-(2-aminopyridin-3-yl)-3H-imidazo[4,5-b]pyridin-3-yl)benzyl)-2-cyanopyrimidine-4-carboxamide | 448.1 | + |
| 149 | 2-(4-(4-(2-(2-aminopyridin-3-yl)-3H-imidazo[4,5-b]pyridin-3-yl)benzyl)piperazine-1-carbonyl)isonicotinonitrile | 516.1 | + |
| 150 | N-(1-(4-(2-(2-aminopyridin-3-yl)-5-phenyl-3H-imidazo[4,5-b]pyridin-3-yl)benzyl)piperidin-4-yl)-4-cyanopicolinamide | 606.1 | ++ |
| 151 | N-(1-(4-(2-(2-aminopyridin-3-yl)-5-phenyl-3H-imidazo[4,5-b]pyridin-3-yl)benzyl)piperidin-4-yl)-2-cyanopyrimidine-4-carboxamide | 607.1 | ++++ |

TABLE 4-continued

| Chemistry Example | Compound Name | MS: [M + H]+ | AKT1 E17K IC50 |
|---|---|---|---|
| 152 | 4-(4-(4-(2-(2-aminopyridin-3-yl)-3H-imidazo[4,5-b]pyridin-3-yl)benzyl)piperazine-1-carbonyl)pyrimidine-2-carbonitrile | 517.2 | ++ |
| 153 | 3-(4-(4-(2-(2-aminopyridin-3-yl)-3H-imidazo[4,5-b]pyridin-3-yl)benzyl)piperazine-1-carbonyl)picolinonitrile | 516.4 | + |
| 154 | 4-(4-(4-(2-(2-aminopyridin-3-yl)-3H-imidazo[4,5-b]pyridin-3-yl)benzyl)piperazine-1-carbonyl)nicotinonitrile | 516.3 | + |
| 155 | 3-(4-(4-(2-(2-aminopyridin-3-yl)-3H-imidazo[4,5-b]pyridin-3-yl)benzyl)piperazine-1-carbonyl)isonicotinonitrile | 516.2 | + |
| 156 | 4-((1-(4-(2-(2-aminopyridin-3-yl)-5-phenyl-3H-imidazo[4,5-b]pyridin-3-yl)benzyl)piperidin-4-yl)(methyl)amino)pyrimidine-2-carbonitrile | 593.4 | +++ |
| 157 | 5-((1-(4-(2-(2-aminopyridin-3-yl)-3H-imidazo[4,5-b]pyridin-3-yl)benzyl)piperidin-4-yl)amino)picolinonitrile | 502.1 | + |
| 158 | 5-((1-(4-(2-(2-aminopyridin-3-yl)-5-phenyl-3H-imidazo[4,5-b]pyridin-3-yl)benzyl)piperidin-4-yl)amino)pyridazine-3-carbonitrile | 579.4 | +++ |
| 159 | 5-(4-(4-(2-(2-aminopyridin-3-yl)-5-phenyl-3H-imidazo[4,5-b]pyridin-3-yl)benzyl)piperazin-1-yl)pyridazine-3-carbonitrile | 565.4 | +++ |
| 160 | N-(4-(2-(2-aminopyridin-3-yl)-5-phenyl-3H-imidazo[4,5-b]pyridin-3-yl)benzyl)-6-cyanonicotinamide | 523.2 | +++ |
| 161 | N-(4-(2-(2-aminopyridin-3-yl)-5-phenyl-3H-imidazo[4,5-b]pyridin-3-yl)benzyl)-2-cyanoisonicotinamide | 523.2 | +++ |
| 162 | N-(4-(2-(2-aminopyridin-3-yl)-5-phenyl-3H-imidazo[4,5-b]pyridin-3-yl)benzyl)-6-cyanopicolinamide | 523.2 | ++ |
| 163 | 3-(4-(4-(2-(2-aminopyridin-3-yl)-5-phenyl-3H-imidazo[4,5-b]pyridin-3-yl)benzyl)piperazine-1-carbonyl)pyrazine-2-carbonitrile | 593.3 | ++ |
| 164 | 3-(4-(4-(2-(2-aminopyridin-3-yl)-3H-imidazo[4,5-b]pyridin-3-yl)benzyl)piperazine-1-carbonyl)pyrazine-2-carbonitrile | 517.3 | + |
| 165 | N-(1-(4-(2-(2-aminopyridin-3-yl)-6-phenyl-3H-imidazo[4,5-b]pyridin-3-yl)benzyl)piperidin-4-yl)-6-cyanonicotinamide | 606.2 | + |
| 166 | 5-(4-(4-(2-(2-aminopyridin-3-yl)-5-phenyl-3H-imidazo[4,5-b]pyridin-3-yl)benzyl)piperazine-1-carbonyl)picolinonitrile | 592.2 | +++ |
| 167 | N-(1-(4-(2-(2-aminopyridin-3-yl)-5-phenyl-3H-imidazo[4,5-b]pyridin-3-yl)benzyl)piperidin-4-yl)-6-cyanonicotinamide | 606.2 | ++ |
| 168 | N-(4-(2-(2-aminopyridin-3-yl)-6-phenyl-3H-imidazo[4,5-b]pyridin-3-yl)benzyl)-6-cyanopicolinamide | 523.2 | + |
| 169 | N-(4-(2-(2-aminopyridin-3-yl)-6-phenyl-3H-imidazo[4,5-b]pyridin-3-yl)benzyl)-2-cyanoisonicotinamide | 523.10 | ++ |
| 170 | N-(4-(2-(2-aminopyridin-3-yl)-5-phenyl-3H-imidazo[4,5-b]pyridin-3-yl)benzyl)-4-cyanopicolinamide | 523.1 | ++ |
| 171 | N-(4-(2-(2-aminopyridin-3-yl)-5-phenyl-3H-imidazo[4,5-b]pyridin-3-yl)benzyl)-2-cyanopyrimidine-4-carboxamide | 524.1 | +++ |
| 172 | 4-(4-(4-(2-(2-aminopyridin-3-yl)-5-phenyl-3H-imidazo[4,5-b]pyridin-3-yl)benzyl)piperazine-1-carbonyl)picolinonitrile | 592.2 | +++ |
| 173 | N-(4-(2-(2-aminopyridin-3-yl)-3H-imidazo[4,5-b]pyridin-3-yl)benzyl)-2-cyano-5-fluorobenzo[d]thiazole-7-carboxamide | 521.0 | ++++ |
| 174 | N-(4-(2-(2-aminopyridin-3-yl)-3H-imidazo[4,5-b]pyridin-3-yl)benzyl)-2-cyano-6-fluorobenzo[d]thiazole-4-carboxamide | 521.1 | +++ |
| 175 | 7-(4-(4-(2-(2-aminopyridin-3-yl)-3H-imidazo[4,5-b]pyridin-3-yl)benzyl)piperazine-1-carbonyl)-5-fluorobenzo[d]thiazole-2-carbonitrile | 590.3 | + |
| 176 | N-(4-(2-(2-aminopyridin-3-yl)-5-phenyl-3H-imidazo[4,5-b]pyridin-3-yl)benzyl)-2-cyano-5-fluorobenzo[d]thiazole-7-carboxamide | 597.1 | +++ |
| 177 | N-(4-(2-(2-aminopyridin-3-yl)-5-phenyl-3H-imidazo[4,5-b]pyridin-3-yl)benzyl)-2-cyano-6-fluorobenzo[d]thiazole-4-carboxamide | 597.3 | ++++ |
| 178 | N-(4-(5-(3-acetamidophenyl)-2-(2-aminopyridin-3-yl)-3H-imidazo[4,5-b]pyridin-3-yl)benzyl)-2-cyano-5-fluorobenzo[d]thiazole-7-carboxamide | 654.2 | ++++ |
| 179 | N-(4-(5-(3-acetamidophenyl)-2-(2-aminopyridin-3-yl)-3H-imidazo[4,5-b]pyridin-3-yl)benzyl)-2-cyano-6-fluorobenzo[d]thiazole-4-carboxamide | 654.4 | +++ |
| 180 | 7-(4-(4-(2-(2-aminopyridin-3-yl)-5-phenyl-3H-imidazo[4,5-b]pyridin-3-yl)benzyl)piperazine-1-carbonyl)-5-fluorobenzo[d]thiazole-2-carbonitrile | 666.4 | +++ |
| 181 | 4-(4-(4-(2-(2-aminopyridin-3-yl)-5-phenyl-3H-imidazo[4,5-b]pyridin-3-yl)benzyl)piperazine-1-carbonyl)-6-fluorobenzo[d]thiazole-2-carbonitrile | 666.1 | +++ |
| 182 | N-(1-(4-(2-(2-aminopyridin-3-yl)-5-phenyl-3H-imidazo[4,5-b]pyridin-3-yl)benzyl)piperidin-4-yl)-2-cyano-5-fluorobenzo[d]thiazole-7-carboxamide | 680.2 | ++ |
| 183 | N-(1-(4-(2-(2-aminopyridin-3-yl)-5-phenyl-3H-imidazo[4,5-b]pyridin-3-yl)benzyl)piperidin-4-yl)-2-cyano-6-fluorobenzo[d]thiazole-4-carboxamide | 680.2 | ++ |

TABLE 4-continued

| Chemistry Example | Compound Name | MS: [M + H]+ | AKT1 E17K IC50 |
|---|---|---|---|
| 184 | 5-(4-(4-(2-(2-aminopyridin-3-yl)-5-phenyl-3H-imidazo[4,5-b]pyridin-3-yl)benzyl)piperazine-1-carbonyl)benzo[d]thiazole-2-carbonitrile | 648.4 | ++++ |
| 185 | N-(1-(4-(2-(2-aminopyridin-3-yl)-5-phenyl-3H-imidazo[4,5-b]pyridin-3-yl)benzyl)piperidin-4-yl)-2-cyanobenzo[d]thiazole-5-carboxamide | 662.5 | ++++ |
| 186 | 6-((4-(2-(2-aminopyridin-3-yl)-5-phenyl-3H-imidazo[4,5-b]pyridin-3-yl)benzyl)amino)picolinonitrile | 495.1 | ++ |
| 187 | 5-((4-(2-(2-aminopyridin-3-yl)-5-phenyl-3H-imidazo[4,5-b]pyridin-3-yl)benzyl)amino)picolinonitrile | 495.1 | ++ |
| 188 | 5-((4-(2-(2-aminopyridin-3-yl)-5-phenyl-3H-imidazo[4,5-b]pyridin-3-yl)benzyl)amino)nicotinonitrile | 495.5 | ++ |
| 189 | 2-((4-(2-(2-aminopyridin-3-yl)-5-phenyl-3H-imidazo[4,5-b]pyridin-3-yl)benzyl)amino)isonicotinonitrile | 495.2 | ++ |
| 190 | 6-((4-(2-(2-aminopyridin-3-yI)-5-phenyl-3H-imidazo[4,5-b]pyridin-3-yl)benzyl)amino)pyrazine-2-carbonitrile | 496.3 | ++ |
| 191 | 2-((4-(2-(2-aminopyridin-3-yl)-5-phenyl-3H-imidazo[4,5-b]pyridin-3-yl)benzyl)amino)pyrimidine-4-carbonitrile | 496.2 | +++ |
| 192 | 4-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile | 593.3 | +++ |
| 193 | 2-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile | 593.5 | ++ |
| 194 | 6-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile | 593.3 | ++ |
| 195 | 4-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile | 593.4 | ++++ |
| 196 | 2-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile | 593.3 | ++ |
| 197 | 6-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile | 593.4 | ++ |
| 198 | 4-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-2-carbonitrile | 591.4 | +++ |
| 199 | 2-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-4-carbonitrile | 591.4 | ++ |
| 200 | 6-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-4-carbonitrile | 591.4 | +++ |
| 201 | 4-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-2-carbonitrile | 605.4 | ++ |
| 202 | 6-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-4-carbonitrile | 605.3 | + |
| 203 | 4-3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-2-carbonitrile | 591.4 | ++ |
| 204 | 2-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-4-carbonitrile | 591.5 | + |
| 205 | 6-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-4-carbonitrile | 591.5 | ++ |
| 206 | (S)-4-(4-(4-(2-(2-aminopyridin-3-yl)-5-phenyl-3H-imidazo[4,5-b]pyridin-3-yl)benzyl)-2-methylpiperazin-1-yl)pyrimidine-2-carbonitrile | 579.4 | +++ |
| 207 | (S)-2-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile | 579.4 | ++ |
| 208 | (S)-6-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile | 579.4 | ++ |
| 209 | 4-((4-(2-(2-aminopyridin-3-yl)-5-phenyl-3H-imidazo[4,5-b]pyridin-3-yl)benzyl)amino)-1,3,5-triazine-2-carbonitrile | 497.2 | ++++ |
| 210 | 4-((4-(2-(2-aminopyridin-3-yl)-5-phenyl-3H-imidazo[4,5-b]pyridin-3-yl)benzyl)amino)-6-hydroxy-1,3,5-triazine-2-carbonitrile | 513.34 | + |

TABLE 4-continued

| Chemistry Example | Compound Name | MS: [M + H]+ | AKT1 E17K IC50 |
|---|---|---|---|
| 211 | 4-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-2-carbonitrile | 591.4 | ++++ |
| 212 | 2-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-4-carbonitrile | 591.3 | ++ |
| 213 | 6-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-4-carbonitrile | 591.3 | +++ |
| 214 | 4-(4-(4-(2-(2-aminopyridin-3-yl)-5-phenyl-3H-imidazo[4,5-b]pyridin-3-yl)benzyl)-1,4-diazepan-1-yl)pyrimidine-2-carbonitrile | 579.2 | +++ |
| 215 | 6-(4-(4-(2-(2-aminopyridin-3-yl)-5-phenyl-3H-imidazo[4,5-b]pyridin-3-yl)benzyl)-1,4-diazepan-1-yl)pyrimidine-4-carbonitrile | 579.3 | ++++ |
| 216 | 4-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-2-carbonitrile | 577.3 | ++++ |
| 217 | 2-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile | 577.4 | +++ |
| 218 | 6-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile | 577.4 | +++ |
| 219 | 4-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-2-carbonitrile | 591.3 | ++++ |
| 220 | 2-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-4-carbonitrile | 591.4 | ++ |
| 221 | 6-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-4-carbonitrile | 591.3 | ++ |
| 222 | 4-((1-((4-(2-(2-aminopyridin-3-yl)-5-phenyl-3H-imidazo[4,5-b]pyridin-3-yl)phenyl)methyl-d2)piperidin-4-ylamino)pyrimidine-2-carbonitrile | 581.3 | ++++ |
| 223 | 4-((1-(4-(2-(2-aminopyridin-3-yl)-5-phenyl-3H-imidazo[4,5-b]pyridin-3-yl)benzyl)piperidin-4-yl)(methyl)amino)-1,3,5-triazine-2-carbonitrile | 594.2 | +++ |
| 224 | (S)-4-((1-(4-(2-(2-aminopyridin-3-yl)-5-phenyl-3H-imidazo[4,5-b]pyridin-3-yl)benzyl)piperidin-3-yl)amino)-1,3,5-triazine-2-carbonitrile | 580.3 | ++++ |
| 225 | (R)-4-(4-(4-(2-(2-aminopyridin-3-yl)-5-phenyl-3H-imidazo[4,5-b]pyridin-3-yl)benzyl)-2-methylpiperazin-1-yl)pyrimidine-2-carbonitrile | 579.3 | ++ |
| 226 | (R)-2-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile | 579.3 | ++ |
| 227 | (R)-6-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile | 579.3 | ++ |
| 228 | 2-(4-(4-(2-(2-aminopyridin-3-yl)-5-phenyl-3H-imidazo[4,5-b]pyridin-3-yl)benzyl)-1,4-diazepan-1-yl)pyrimidine-4-carbonitrile | 579.3 | +++ |
| 229 | N-(3-(4-(2-(2-aminopyridin-3-yl)-5-phenyl-3H-imidazo[4,5-b]pyridin-3-yl)benzyl)-3-azabicyclo[3.2.1]octan-8-yl)-2-cyanopyrimidine-4-carboxamide | 633.3 | +++ |
| 230 | N-(3-(4-(2-(2-aminopyridin-3-yl)-5-phenyl-3H-imidazo[4,5-b]pyridin-3-yl)benzyl)-3-azabicyclo[3.2.1]octan-8-yl)-6-cyanopyrimidine-4-carboxamide | 633.3 | ++ |
| 231 | 2-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-4-carbonitrile | 605.3 | + |
| 232 | 4-((1-(4-(2-(2-aminopyridin-3-yl)-5-phenyl-3H-imidazo[4,5-b]pyridin-3-yl)benzyl)piperidin-4-yl)(methyl-d3)amino)pyrimidine-2-carbonitrile | 596.2 | ++++ |
| 233 | 4-((1-(4-(2-(2-aminopyridin-3-yl)-5-phenyl-3H-imidazo[4,5-b]pyridin-3-yl)benzyl)piperidin-4-yl)(methyl-d3)amino)-1,3,5-triazine-2-carbonitrile | 597.4 | +++ |
| 234 | N-(1-(4-(2-(2-aminopyridin-3-yl)-5-phenyl-3H-imidazo[4,5-b]pyridin-3-yl)benzyl)piperidin-4-yl)-2-cyano-N-(methyl-d3)pyrimidine-4-carboxamide | 624.4 | ++++ |
| 235 | 4-(4-(4-(2-(2-aminopyridin-3-yl)-5-morpholino-3H-imidazo[4,5-b]pyridin-3-yl)benzyl)piperazin-1-yl)pyrimidine-2-carbonitrile | 574.3 | ++ |

TABLE 4-continued

| Chemistry Example | Compound Name | MS: [M + H]+ | AKT1 E17K IC50 |
|---|---|---|---|
| 236 | 2-(4-(4-(2-(2-aminopyridin-3-yl)-5-morpholino-3H-imidazo[4,5-b]pyridin-3-yl)benzyl)piperazin-1-yl)pyrimidine-4-carbonitrile | 574.3 | +++ |
| 237 | 6-(4-(4-(2-(2-aminopyridin-3-yl)-5-morpholino-3H-imidazo[4,5-b]pyridin-3-yl)benzyl)piperazin-1-yl)pyrimidine-4-carbonitrile | 574.2 | +++ |
| 238 | 4-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-2-carbonitrile | 582.2 | +++ |
| 239 | 4-((1-(4-(2-(2-aminopyridin-3-yl)-5-morpholino-3H-imidazo[4,5-b]pyridin-3-yl)benzyl)piperidin-4-yl)amino)pyrimidine-2-carbonitrile | 588.4 | ++++ |
| 240 | 2-((1-(4-(2-(2-aminopyridin-3-yl)-5-morpholino-3H-imidazo[4,5-b]pyridin-3-yl)benzyl)piperidin-4-yl)amino)pyrimidine-4-carbonitrile | 588.3 | +++ |
| 241 | 6-((1-(4-(2-(2-aminopyridin-3-yl)-5-morpholino-3H-imidazo[4,5-b]pyridin-3-yl)benzyl)piperidin-4-yl)amino)pyrimidine-4-carbonitrile | 588.3 | +++ |
| 242 | 4-(4-(4-(2-(2-aminopyridin-3-yl)-5-(4-fluorophenyl)-3H-imidazo[4,5-b]pyridin-3-yl)benzyl)piperazin-1-yl)pyrimidine-2-carbonitrile | 583.3 | +++ |
| 243 | 2-(4-(4-(2-(2-aminopyridin-3-yl)-5-(4-fluorophenyl)-3H-imidazo[4,5-b]pyridin-3-yl)benzyl)piperazin-1-yl)pyrimidine-4-carbonitrile | 583.3 | ++ |
| 244 | N-(4-(2-(2-aminopyridin-3-yl)-3H-imidazo[4,5-b]pyridin-3-yl)benzyl)-2-cyanothiazole-4-carboxamide | 453.0 | + |
| 245 | N-(4-(2-(2-aminopyridin-3-yl)-5-phenyl-3H-imidazo[4,5-b]pyridin-3-yl)benzyl)-2-cyanothiazole-5-carboxamide | 529.2 | ++++ |
| 246 | N-(4-(2-(2-aminopyridin-3-yl)-5-phenyl-3H-imidazo[4,5-b]pyridin-3-yl)benzyl)-2-cyanothiazole-4-carboxamide | 529.2 | +++ |
| 247 | 4-(4-(4-(2-(2-aminopyridin-3-yl)-5-phenyl-3H-imidazo[4,5-b]pyridin-3-yl)benzyl)piperazine-1-carbonyl)thiazole-2-carbonitrile | 598.2 | ++++ |
| 248 | 4-((7-(4-(2-(2-aminopyridin-3-yl)-5-phenyl-3H-imidazo[4,5-b]pyridin-3-yl)benzyl)-7-azaspiro[3.5]nonan-2-yl)amino)-1,3,5-triazine-2-carbonitrile | 620.4 | ++++ |
| 249 | 4-(7-(4-(2-(2-aminopyridin-3-yl)-5-phenyl-3H-imidazo[4,5-b]pyridin-3-yl)benzyl)-2,7-diazaspiro[3.5]nonan-2-yl)-1,3,5-triazine-2-carbonitrile | 606.4 | +++ |
| 250 | 4-(4-(4-(2-(2-aminopyridin-3-yl)-5-phenyl-3H-imidazo[4,5-b]pyridin-3-yl)benzyl)-1,4-diazepan-1-yl)-1,3,5-triazine-2-carbonitrile | 580.3 | +++ |
| 251 | 4-(7-(4-(2-(2-aminopyridin-3-yl)-5-phenyl-3H-imidazo[4,5-b]pyridin-3-yl)benzyl)-2,7-diazaspiro[4.4]nonan-2-y])-1,3,5-triazine-2-carbonitrile | 606.4 | ++++ |
| 252 | 4-(2-(4-(2-(2-aminopyridin-3-yl)-5-phenyl-3H-imidazo[4,5-b]pyridin-3-yl)benzyl)-2,8-diazaspiro[4.5]decan-8-yl)-1,3,5-triazine-2-carbonitrile | 620.3 | +++ |
| 253 | 4-(2-(4-(2-(2-aminopyridin-3-yl)-5-phenyl-3H-imidazo[4,5-b]pyridin-3-yl)benzyl)-2,7-diazaspiro[4.5]decan-7-yl)-1,3,5-triazine-2-carbonitrile | 620.5 | +++ |
| 254 | 4-(9-(4-(2-(2-aminopyridin-3-yl)-5-phenyl-3H-imidazo[4,5-b]pyridin-3-yl)benzyl)-2,9-diazaspiro[5.5]undecan-2-yl)-1,3,5-triazine-2-carbonitrile | 634.3 | ++++ |
| 255 | (R)-4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile | 606.3 | ++++ |
| 256 | 4-((2R,6R)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile | 594.3 | +++ |
| 257 | 4-(5-(4-(2-(2-aminopyridin-3-yl)-5-phenyl-3H-imidazo[4,5-b]pyridin-3-yl)benzyl)-2,5-diazabicyclo[2.2.2]octan-2-yl)-1,3,5-triazine-2-carbonitrile | 592.2 | +++ |
| 258 | 4-(4-(4-(2-(2-aminopyridin-3-yl)-5-cyclopropyl-3H-imidazo[4,5-b]pyridin-3-yl)benzyl)piperazin-1-yl)pyrimidine-2-carbonitrile | 529.3 | ++++ |
| 259 | 4-(4-(4-(2-(2-aminopyridin-3-yl)-5-(2-oxo-1,2-dihydropyridin-3-yl)-3H-imidazo[4,5-b]pyridin-3-yl)benzyl)piperazin-1-yl)pyrimidine-2-carbonitrile | 582.3 | ++++ |
| 260 | 4-(4-(4-(2-(2-aminopyridin-3-yl)-5-(1-methyl-2-oxo-1,2-dihydropyridin-3-yl)-3H-imidazo[4,5-b]pyridin-3-yl)benzyl)piperazin-1-yl)pyrimidine-2-carbonitrile | 596.3 | +++ |
| 261 | 4-((1-(4-(2-(2-aminopyridin-3-yl)-5-(1-methyl-2-oxo-1,2-dihydropyridin-3-yl)-3H-imidazo[4,5-b]pyridin-3-yl)benzyl)piperidin-4-yl)amino)pyrimidine-2-carbonitrile | 610.4 | ++++ |

TABLE 4-continued

| Chemistry Example | Compound Name | MS: [M + H]+ | AKT1 E17K IC50 |
|---|---|---|---|
| 262 | 4-((1-(4-(2-(2-aminopyridin-3-yl)-5-cyclobutyl-3H-imidazo[4,5-b]pyridin-3-yl)benzyl)piperidin-4-yl)amino)pyrimidine-2-carbonitrile | 557.4 | ++++ |
| 263 | 4-((1-(4-(2-(2-aminopyridin-3-yl)-5-(cyclohex-1-en-1-yl)-3H-imidazo[4,5-b]pyridin-3-yl)benzyl)piperidin-4-yl)amino)pyrimidine-2-carbonitrile | 583.4 | +++ |
| 264 | 4-((1-(4-(2-(2-aminopyridin-3-yl)-5-cyclohexyl-3H-imidazo[4,5-b]pyridin-3-yl)benzyl)piperidin-4-yl)amino)pyrimidine-2-carbonitrile | 585.4 | ++++ |
| 265 | 4-((1-(4-(2-(2-aminopyridin-3-yl)-5-(3-cyanophenyl)-3H-imidazo[4,5-b]pyridin-3-yl)benzyl)piperidin-4-yl)amino)pyrimidine-2-carbonitrile | 604.4 | ++++ |
| 266 | 4-((1-(4-(2-(2-aminopyridin-3-yl)-5-(6-oxo-1,6-dihydropyridin-3-yl)-3H-imidazo[4,5-b]pyridin-3-yl)benzyl)piperidin-4-yl)amino)pyrimidine-2-carbonitrile | 596.4 | ++ |
| 267 | 4-((1-(4-(2-(2-aminopyridin-3-yl)-5-(6-oxo-1,6-dihydropyridin-2-yl)-3H-imidazo[4,5-b]pyridin-3-yl)benzyl)piperidin-4-yl)amino)pyrimidine-2-carbonitrile | 596.1 | ++++ |
| 268 | 4-(2-(4-(2-(2-aminopyridin-3-yl)-5-phenyl-3H-imidazo[4,5-b]pyridin-3-yl)benzyl)-2,7-diazaspiro[3.5]nonan-7-yl)-1,3,5-triazine-2-carbonitrile | 606.3 | ++++ |
| 269 | (S)-4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile | 606.4 | ++++ |
| 270 | 4-(3-(4-(2-(2-aminopyridin-3-yl)-5-phenyl-3H-imidazo[4,5-b]pyridin-3-yl)benzyl)-3,8-diazabicyclo[3.2.1]octan-8-yl)-1,3,5-triazine-2-carbonitrile | 592.4 | ++ |
| 271 | 4-(8-(4-(2-(2-aminopyridin-3-yl)-5-phenyl-3H-imidazo[4,5-b]pyridin-3-yl)benzyl)-3,8-diazabicyclo[3.2.1]octan-3-yl)-1,3,5-triazine-2-carbonitrile | 592.4 | +++ |
| 272 | 4-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile | 578.3 | ++++ |
| 273 | (R)-4-(4-(4-(2-(2-aminopyridin-3-yl)-5-phenyl-3H-imidazo[4,5-b]pyridin-3-yl)benzyl)-2-methylpiperazin-1-yl)-1,3,5-triazine-2-carbonitrile | 580.3 | ++++ |
| 274 | (S)-4-(4-(4-(2-(2-aminopyridin-3-yl)-5-phenyl-3H-imidazo[4,5-b]pyridin-3-yl)benzyl)-2-methylpiperazin-1-yl)-1,3,5-triazine-2-carbonitrile | 580.4 | +++ |
| 275 | 4-((2S,6S)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile | 594.4 | ++++ |
| 276 | 4-(7-(4-(2-(2-aminopyridin-3-yl)-5-phenyl-3H-imidazo[4,5-b]pyridin-3-yl)benzyl)-4,7-diazaspiro[2.5]octan-4-yl)-1,3,5-triazine-2-carbonitrile | 592.3 | ++++ |
| 277 | 4-((2R,6S)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile | 594.4 | +++ |
| 278 | 4-((1-(4-(2-(2-aminopyridin-3-yl)-5-phenyl-3H-imidazo[4,5-b]pyridin-3-yl)benzyl)azepan-4-yl)amino)-1,3,5-triazine-2-carbonitrile | 594.4 | +++ |
| 279 | 4-((4-(4-(2-(2-aminopyridin-3-yl)-5-phenyl-3H-imidazo[4,5-b]pyridin-3-yl)benzyl)-1,4-oxazepan-6-yl)amino)-1,3,5-triazine-2-carbonitrile | 596.4 | ++++ |
| 280 | 4-((1-(4-(2-(2-aminopyridin-3-yl)-5-methyl-3H-imidazo[4,5-b]pyridin-3-yl)benzyl)piperidin-4-yl)amino)pyrimidine-2-carbonitrile | 517.2 | ++++ |
| 281 | 4-(4-(4-(2-(2-aminopyridin-3-yl)-5-(2-fluorophenyl)-3H-imidazo[4,5-b]pyridin-3-yl)benzyl)piperazin-1-yl)pyrimidine-2-carbonitrile | 583.3 | ++++ |
| 282 | 2-(4-(4-(2-(2-aminopyridin-3-yl)-5-(2-fluorophenyl)-3H-imidazo[4,5-b]pyridin-3-yl)benzyl)piperazin-1-yl)pyrimidine-4-carbonitrile | 583.3 | +++ |
| 283 | 2-(4-(4-(2-(2-aminopyridin-3-yl)-5-(3-oxo-1,4-diazepan-1-y])-3H-imidazo[4,5-b]pyridin-3-yl)benzyl)piperazin-1-yl)pyrimidine-4-carbonitrile | 601.4 | +++ |
| 284 | 6-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-4-carbonitrile | 601.4 | ++ |
| 285 | 4-(8-(4-(2-(2-aminopyridin-3-yl)-5-morpholino-3H-imidazo[4,5-b]pyridin-3-yl)benzyl)-3,8-diazabicyclo[3.2.1]octan-3-yl)-1,3,5-triazine-2-carbonitrile | 601.5 | ++++ |

TABLE 4-continued

| Chemistry Example | Compound Name | MS: [M + H]+ | AKT1 E17K IC50 |
|---|---|---|---|
| 286 | 4-((1-(4-(2-(2-aminopyridin-3-yl)-5-isopropyl-3H-imidazo[4,5-b]pyridin-3-yl)benzyl)piperidin-4-yl)amino)pyrimidine-2-carbonitrile | 545.2 | ++++ |
| 287 | 4-((1-(4-(2-(2-aminopyridin-3-yl)-5-methoxy-3H-imidazo[4,5-b]pyridin-3-yl)benzyl)piperidin-4-yl)amino)pyrimidine-2-carbonitrile | 533.2 | ++++ |
| 288 | 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxamide | 546.2 | +++ |
| 289 | 2-(2-aminopyridin-3-yl)-3-(4-((4-((2-cyanopyrimidin-4-yl)amino)piperidin-1-yl)methyl)phenyl)-N,N-dimethyl-3H-imidazo[4,5-b]pyridine-5-carboxamide | 574.4 | ++ |
| 290 | 6-(4-(4-(2-(2-aminopyridin-3-yl)-5-cyclopropyl-3H-imidazo[4,5-b]pyridin-3-yl)benzyl)piperazin-1-yl)pyrimidine-4-carbonitrile | 529.4 | +++ |
| 291 | 6-((1-(4-(2-(2-aminopyridin-3-yl)-5-cyclopropyl-3H-imidazo[4,5-b]pyridin-3-yl)benzyl)piperidin-4-yl)amino)pyrimidine-4-carbonitrile | 543.4 | +++ |
| 292 | 4-(4-(4-(2-(2-aminopyridin-3-yl)-5-morpholino-3H-imidazo[4,5-b]pyridin-3-yl)benzyl)piperazin-1-yl)-1,3,5-triazine-2-carbonitrile | 575.4 | ++++ |
| 293 | 4-(4-(4-(2-(2-aminopyridin-3-yl)-5-(2-cyanophenyl)-3H-imidazo[4,5-b]pyridin-3-yl)benzyl)piperazin-1-yl)pyrimidine-2-carbonitrile | 590.2 | ++++ |
| 294 | 4-(4-(4-(2-(2-aminopyridin-3-yl)-5-(4-cyanophenyl)-3H-imidazo[4,5-b]pyridin-3-yl)benzyl)piperazin-1-yl)pyrimidine-2-carbonitrile | 590.3 | +++ |
| 295 | 4-(4-(4-(2-(2-aminopyridin-3-yl)-5-(3-fluorophenyl)-3H-imidazo[4,5-b]pyridin-3-yl)benzyl)piperazin-1-yl)pyrimidine-2-carbonitrile | 583.3 | ++++ |
| 296 | 4-(4-(4-(2-(2-aminopyridin-3-yl)-5-(3-chlorophenyl)-3H-imidazo[4,5-b]pyridin-3-yl)benzyl)piperazin-1-yl)pyrimidine-2-carbonitrile | 599.2 | ++++ |
| 297 | 2-(4-(4-(2-(2-aminopyridin-3-yl)-5-(3-chlorophenyl)-3H-imidazo[4,5-b]pyridin-3-yl)benzyl)piperazin-1-yl)pyrimidine-4-carbonitrile | 599.4 | ++ |
| 298 | 4-((1-(4-(2-(2-aminopyridin-3-yl)-5-cyclopropyl-3H-imidazo[4,5-b]pyridin-3-yl)benzyl)piperidin-4-yl)amino)pyrimidine-2-carbonitrile | 543.3 | ++++ |
| 299 | 4-((1-(4-(2-(2-aminopyridin-3-yl)-5-(tetrahydro-2H-pyran-4-yl)-3H-imidazo[4,5-b]pyridin-3-yl)benzyl)piperidin-4-yl)amino)pyrimidine-2-carbonitrile | 587.2 | ++++ |
| 300 | 4-((1-(4-(2-(2-aminopyridin-3-yl)-5-phenyl-3H-imidazo[4,5-b]pyridin-3-yl)benzyl)azetidin-3-yl)amino)-1,3,5-triazine-2-carbonitrile | 552.4 | +++ |
| 301 | 4-(6-(4-(2-(2-aminopyridin-3-yl)-5-phenyl-3H-imidazo[4,5-b]pyridin-3-yl)benzyl)-2,6-diazaspiro[3.4]octan-2-yl)-1,3,5-triazine-2-carbonitrile | 592.3 | ++++ |
| 302 | 4-(7-(4-(2-(2-aminopyridin-3-yl)-5-phenyl-3H-imidazo[4,5-b]pyridin-3-yl)benzyl)-2,7-diazaspiro[4.4]nonan-2-yl)pyrimidine-2-carbonitrile | 605.3 | ++++ |
| 303 | 4-(6-(4-(2-(2-aminopyridin-3-yl)-5-phenyl-3H-imidazo[4,5-b]pyridin-3-yl)benzyl)-2,6-diazaspiro[3.3]heptan-2-yl)-1,3,5-triazine-2-carbonitrile | 578.3 | ++++ |
| 304 | 4-(4-(4-(2-(2-aminopyridin-3-yl)-5-(2-chlorophenyl)-3H-imidazo[4,5-b]pyridin-3-yl)benzyl)piperazin-1-yl)-1,3,5-triazine-2-carbonitrile | 600.4 | ++++ |
| 305 | 4-((1-(4-(2-(2-aminopyridin-3-yl)-5-(2-chlorophenyl)-3H-imidazo[4,5-b]pyridin-3-yl)benzyl)piperidin-4-yl)amino)pyrimidine-2-carbonitrile | 613.4 | ++++ |
| 306 | 2-((1-(4-(2-(2-aminopyridin-3-yl)-5-(2-chlorophenyl)-3H-imidazo[4,5-b]pyridin-3-yl)benzyl)piperidin-4-yl)amino)pyrimidine-4-carbonitrile | 613.3 | +++ |
| 307 | 6-((1-(4-(2-(2-aminopyridin-3-yl)-5-(2-chlorophenyl)-3H-imidazo[4,5-b]pyridin-3-yl)benzyl)piperidin-4-yl)amino)pyrimidine-4-carbonitrile | 613.4 | ++ |
| 308 | 4-((1-(4-(2-(2-aminopyridin-3-yl)-5-(4-chlorophenyl)-3H-imidazo[4,5-b]pyridin-3-yl)benzyl)piperidin-4-yl)amino)pyrimidine-2-carbonitrile | 613.2 | ++++ |
| 309 | 2-(4-(4-(2-(2-aminopyridin-3-yl)-5-(3-fluorophenyl)-3H-imidazo[4,5-b]pyridin-3-yl)benzyl)piperazin-1-yl)pyrimidine-4-carbonitrile | 583.4 | +++ |
| 310 | 6-(4-(4-(2-(2-aminopyridin-3-yl)-5-(3-fluorophenyl)-3H-imidazo[4,5-b]pyridin-3-yl)benzyl)piperazin-1-yl)pyrimidine-4-carbonitrile | 583.4 | ++++ |

TABLE 4-continued

| Chemistry Example | Compound Name | MS: [M + H]+ | AKT1 E17K IC50 |
|---|---|---|---|
| 311 | 6-((1-(4-(2-(2-aminopyridin-3-yl)-5-(3-fluorophenyl)-3H-imidazo[4,5-b]pyridin-3-yl)benzyl)piperidin-4-yl)amino)pyrimidine-4-carbonitrile | 597.4 | ++++ |
| 312 | 4-(4-(4-(2-(2-aminopyridin-3-yl)-5-(2-fluorophenyl)-3H-imidazo[4,5-b]pyridin-3-yl)benzyl)piperazin-1-yl)-1,3,5-triazine-2-carbonitrile | 584.2 | ++++ |
| 313 | 2-((1-(4-(2-(2-aminopyridin-3-yl)-5-(2-fluorophenyl)-3H-imidazo[4,5-b]pyridin-3-yl)benzyl)piperidin-4-yl)amino)pyrimidine-4-carbonitrile | 597.4 | ++++ |
| 314 | 6-(4-(4-(2-(2-aminopyridin-3-yl)-5-(2-fluorophenyl)-3H-imidazo[4,5-b]pyridin-3-yl)benzyl)piperazin-1-yl)pyrimidine-4-carbonitrile | 583.4 | ++++ |
| 315 | 6-((1-(4-(2-(2-aminopyridin-3-yl)-5-(2-fluorophenyl)-3H-imidazo[4,5-b]pyridin-3-yl)benzyl)piperidin-4-yl)amino)pyrimidine-4-carbonitrile | 597.4 | +++ |
| 316 | 4-((1-(4-(2-(2-aminopyridin-3-yl)-5-(2-fluorophenyl)-3H-imidazo[4,5-b]pyridin-3-yl)benzyl)piperidin-4-yl)amino)pyrimidine-2-carbonitrile | 597.4 | ++++ |
| 317 | 4-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-2-carbonitrile | 601.2 | ++ |
| 318 | 4-((1-(4-(2-(2-aminopyridin-3-yl)-5-(3-oxo-1,4-diazepan-1-yl)-3H-imidazo[4,5-b]pyridin-3-yl)benzyl)piperidin-4-yl)amino)pyrimidine-2-carbonitrile | 615.2 | +++ |
| 319 | 2-(4-(4-(2-(2-aminopyridin-3-yl)-5-(4-cyanophenyl)-3H-imidazo[4,5-b]pyridin-3-yl)benzyl)piperazin-1-yl)pyrimidine-4-carbonitrile | 590.2 | ++ |
| 320 | 4-((1-(4-(2-(2-aminopyridin-3-yl)-5-(4-cyanophenyl)-3H-imidazo[4,5-b]pyridin-3-yl)benzyl)piperidin-4-yl)amino)pyrimidine-2-carbonitrile | 604.2 | ++++ |
| 321 | 2-((1-(4-(2-(2-aminopyridin-3-yl)-5-(4-cyanophenyl)-3H-imidazo[4,5-b]pyridin-3-yl)benzyl)piperidin-4-yl)amino)pyrimidine-4-carbonitrile | 604.4 | ++ |
| 322 | 2-(4-(4-(2-(2-aminopyridin-3-yl)-5-(2-cyanophenyl)-3H-imidazo[4,5-b]pyridin-3-yl)benzyl)piperazin-1-yl)pyrimidine-4-carbonitrile | 590.2 | +++ |
| 323 | 4-((1-(4-(2-(2-aminopyridin-3-yl)-5-(5-oxo-1,4-diazepan-1-yl)-3H-imidazo[4,5-b]pyridin-3-yl)benzyl)piperidin-4-yl)amino)pyrimidine-2-carbonitrile | 615.5 | + |
| 324 | 4-(4-(4-(2-(2-aminopyridin-3-yl)-5-(2-chlorophenyl)-3H-imidazo[4,5-b]pyridin-3-yl)benzyl)piperazin-1-yl)pyrimidine-2-carbonitrile | 599.1 | ++++ |
| 325 | 2-(4-(4-(2-(2-aminopyridin-3-yl)-5-(2-chlorophenyl)-3H-imidazo[4,5-b]pyridin-3-yl)benzyl)piperazin-1-yl)pyrimidine-4-carbonitrile | 599.3 | +++ |
| 326 | 6-(4-(4-(2-(2-aminopyridin-3-yl)-5-(2-chlorophenyl)-3H-imidazo[4,5-b]pyridin-3-yl)benzyl)piperazin-1-yl)pyrimidine-4-carbonitrile | 599.4 | +++ |
| 327 | 5-(4-(4-(2-(2-aminopyridin-3-yl)-5-phenyl-3H-imidazo[4,5-b]pyridin-3-yl)benzyl)piperazine-1-carbonyl)thiazole-2-carbonitrile | 598.3 | ++ |
| 328 | 4-(4-(4-(2-(2-aminopyridin-3-yl)-5-phenyl-3H-imidazo[4,5-b]pyridin-3-yl)benzyl)piperazin-1-yl)-1,3,5-triazine-2-carbonitrile | 566.3 | ++++ |
| 329 | 4-(4-(4-(2-(2-aminopyridin-3-yl)-5-(cyclohex-1-en-1-yl)-3H-imidazo[4,5-b]pyridin-3-yl)benzyl)piperazin-1-yl)pyrimidine-2-carbonitrile | 569.2 | +++ |
| 330 | 4-(4-(4-(2-(2-aminopyridin-3-yl)-5-(3,6-dihydro-2H-pyran-4-yl)-3H-imidazo[4,5-b]pyridin-3-yl)benzyl)piperazin-1-yl)pyrimidine-2-carbonitrile | 571.1 | ++++ |
| 331 | 4-(4-(4-(2-(2-aminopyridin-3-yl)-5-(3-cyanophenyl)-3H-imidazo[4,5-b]pyridin-3-yl)benzyl)piperazin-1-yl)pyrimidine-2-carbonitrile | 590.4 | ++++ |
| 332 | 4-(4-(4-(2-(2-aminopyridin-3-yl)-5-(6-oxo-1,6-dihydropyridin-3-yl)-3H-imidazo[4,5-b]pyridin-3-yl)benzyl)piperazin-1-yl)pyrimidine-2-carbonitrile | 582.2 | + |
| 333 | 2-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-4-carbonitrile | 582.2 | +++ |
| 334 | 6-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-4-carbonitrile | 582.3 | +++ |
| 335 | 4-((1-(4-(2-(2-aminopyridin-3-yl)-5-(2-cyanophenyl)-3H-imidazo[4,5-b]pyridin-3-yl)benzyl)piperidin-4-yl)amino)pyrimidine-2-carbonitrile | 604.3 | ++++ |

TABLE 4-continued

| Chemistry Example | Compound Name | MS: [M + H]+ | AKT1 E17K IC50 |
|---|---|---|---|
| 336 | N-(1-(4-(2-(2-aminopyridin-3-yl)-5-phenyl-3H-imidazo[4,5-b]pyridin-3-yl)benzyl)piperidin-4-yl)-2-cyano-N-methylpyrimidine-4-carboxamide | 621.3 | ++++ |
| 337 | (R)-4-((1-(4-(2-(2-aminopyridin-3-yl)-5-phenyl-3H-imidazo[4,5-b]pyridin-3-yl)benzyl)piperidin-3-yl)amino)-1,3,5-triazine-2-carbonitrile | 580.4 | ++++ |
| 338 | 4-(1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile | 578.3 | +++ |
| 339 | 4-((3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile | 591.2 | +++ |
| 340 | 4-((3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)-1,3,5-triazine-2-carbonitrile | 592.4 | ++++ |
| 341 | 4-((3aR,6aR)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile | 591.4 | ++++ |
| 342 | 4-(4-(4-(2-(2-aminopyridin-3-yl)-5-(4-chlorophenyl)-3H-imidazo[4,5-b]pyridin-3-yl)benzyl)piperazin-1-yl)pyrimidine-2-carbonitrile | 599.4 | +++ |
| 343 | 2-(4-(4-(2-(2-aminopyridin-3-yl)-5-(4-chlorophenyl)-3H-imidazo[4,5-b]pyridin-3-yl)benzyl)piperazin-1-yl)pyrimidine-4-carbonitrile | 599.2 | ++ |
| 344 | 6-(4-(4-(2-(2-aminopyridin-3-yl)-5-(4-chlorophenyl)-3H-imidazo[4,5-b]pyridin-3-yl)benzyl)piperazin-1-yl)pyrimidine-4-carbonitrile | 599.2 | ++ |
| 345 | 4-(4-(4-(2-(2-aminopyridin-3-yl)-5-(4-methyl-5-oxo-1,4-diazepan-1-yl)-3H-imidazo[4,5-b]pyridin-3-yl)benzyl)piperazin-1-yl)pyrimidine-2-carbonitrile | 615.3 | ++ |
| 346 | 4-((1-(4-(2-(2-aminopyridin-3-yl)-5-(4-methyl-5-oxo-1,4-diazepan-1-yl)-3H-imidazo[4,5-b]pyridin-3-yl)benzyl)piperidin-4-yl)amino)pyrimidine-2-carbonitrile | 629.4 | ++ |
| 347 | 2-((1-(4-(2-(2-aminopyridin-3-yl)-5-(3-oxo-1,4-diazepan-1-yl)-3H-imidazo[4,5-b]pyridin-3-yl)benzyl)piperidin-4-yl)amino)pyrimidine-4-carbonitrile | 615.5 | ++ |
| 348 | 4-(4-(4-(2-(2-aminopyridin-3-yl)-5-(1-methyl-6-oxo-1,6-dihydropyridin-3-yl)-3H-imidazo[4,5-b]pyridin-3-yl)benzyl)piperazin-1-yl)pyrimidine-2-carbonitrile | 596.1 | ++ |
| 349 | 4-(4-(4-(2-(2-aminopyridin-3-yl)-5-(1-methyl-2-oxo-1,2-dihydropyridin-4-yl)-3H-imidazo[4,5-b]pyridin-3-yl)benzyl)piperazin-1-yl)pyrimidine-2-carbonitrile | 596.2 | +++ |
| 350 | 2-(4-(4-(2-(2-aminopyridin-3-yl)-5-cyclopropyl-3H-imidazo[4,5-b]pyridin-3-yl)benzyl)piperazin-1-yl)pyrimidine-4-carbonitrile | 529.4 | +++ |
| 351 | 2-((1-(4-(2-(2-aminopyridin-3-yl)-5-cyclopropyl-3H-imidazo[4,5-b]pyridin-3-yl)benzyl)piperidin-4-yl)amino)pyrimidine-4-carbonitrile | 543.4 | +++ |
| 352 | 2-((1-(4-(2-(2-aminopyridin-3-yl)-5-(4-fluorophenyl)-3H-imidazo[4,5-b]pyridin-3-yl)benzyl)piperidin-4-yl)amino)pyrimidine-4-carbonitrile | 597.4 | +++ |
| 353 | 4-((1-(4-(2-(2-aminopyridin-3-yl)-5-(3-chlorophenyl)-3H-imidazo[4,5-b]pyridin-3-yl)benzyl)piperidin-4-yl)amino)pyrimidine-2-carbonitrile | 613.4 | ++ |
| 354 | 2-(4-(4-(2-(2-aminopyridin-3-yl)-5-(1-methyl-6-oxo-1,6-dihydropyridin-3-yl)-3H-imidazo[4,5-b]pyridin-3-yl)benzyl)piperazin-1-yl)pyrimidine-4-carbonitrile | 596.2 | ++ |
| 355 | 4-((1-(4-(2-(2-aminopyridin-3-yl)-5-(1-methyl-6-oxo-1,6-dihydropyridin-3-yl)-3H-imidazo[4,5-b]pyridin-3-yl)benzyl)piperidin-4-yl)amino)pyrimidine-2-carbonitrile | 610.2 | +++ |
| 356 | 2-((1-(4-(2-(2-aminopyridin-3-yl)-5-(1-methyl-6-oxo-1,6-dihydropyridin-3-yl)-3H-imidazo[4,5-b]pyridin-3-yl)benzyl)piperidin-4-yl)amino)pyrimidine-4-carbonitrile | 610.2 | ++ |
| 357 | 4-((1-(4-(2-(2-aminopyridin-3-yl)-5-(3-fluorophenyl)-3H-imidazo[4,5-b]pyridin-3-yl)benzyl)piperidin-4-yl)amino)pyrimidine-2-carbonitrile | 597.5 | +++ |
| 358 | 2-((1-(4-(2-(2-aminopyridin-3-yl)-5-(3-fluorophenyl)-3H-imidazo[4,5-b]pyridin-3-yl)benzyl)piperidin-4-yl)amino)pyrimidine-4-carbonitrile | 597.3 | +++ |
| 359 | 4-((1-(4-(2-(2-aminopyridin-3-yl)-5-(1-methyl-2-oxo-1,2-dihydropyridin-4-yl)-3H-imidazo[4,5-b]pyridin-3-yl)benzyl)piperidin-4-yl)amino)pyrimidine-2-carbonitrile | 610.2 | ++++ |
| 360 | 2-((1-(4-(2-(2-aminopyridin-3-yl)-5-(1-methyl-2-oxo-1,2-dihydropyridin-4-yl)-3H-imidazo[4,5-b]pyridin-3-yl)benzyl)piperidin-4-yl)amino)pyrimidine-4-carbonitrile | 610.1 | ++ |

TABLE 4-continued

| Chemistry Example | Compound Name | MS: [M + H]+ | AKT1 E17K IC50 |
|---|---|---|---|
| 361 | 4-(7-(4-(2-(2-aminopyridin-3-yl)-5-phenyl-3H-imidazo[4,5-b]pyridin-3-yl)benzyl)-2,7-diazaspiro[3.5]nonan-2-yl)pyrimidine-2-carbonitrile | 605.4 | ++++ |
| 362 | 4-((7-(4-(2-(2-aminopyridin-3-yl)-5-phenyl-3H-imidazo[4,5-b]pyridin-3-yl)benzyl)-7-azaspiro[3.5]nonan-2-yl)amino)pyrimidine-2-carbonitrile | 619.4 | ++++ |
| 363 | 4-(8-(4-(2-(2-aminopyridin-3-yl)-5-phenyl-3H-imidazo[4,5-b]pyridin-3-yl)benzyl)-2,8-diazaspiro[4.5]decan-2-yl)-1,3,5-triazine-2-carbonitrile | 620.3 | +++ |
| 364 | 4-(9-(4-(2-(2-aminopyridin-3-yl)-5-phenyl-3H-imidazo[4,5-b]pyridin-3-yl)benzyl)-3,9-diazaspiro[5.5]undecan-3-yl)pyrimidine-2-carbonitrile | 633.5 | +++ |
| 365 | 4-(9-(4-(2-(2-aminopyridin-3-yl)-5-phenyl-3H-imidazo[4,5-b]pyridin-3-yl)benzyl)-3,9-diazaspiro[5.5]undecan-3-yl)-1,3,5-triazine-2-carbonitrile | 634.3 | +++ |
| 366 | 4-(6-(4-(2-(2-aminopyridin-3-yl)-5-phenyl-3H-imidazo[4,5-b]pyridin-3-yl)benzyl)-2,6-diazaspiro[3.3]heptan-2-yl)pyrimidine-2-carbonitrile | 577.3 | ++++ |
| 367 | 4-((3aS,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile | 591.3 | ++++ |
| 368 | 4-(4-(4-(2-(2-aminopyridin-3-yl)-5-(4-fluorophenyl)-3H-imidazo[4,5-b]pyridin-3-yl)benzyl)piperazin-1-yl)-1,3,5-triazine-2-carbonitrile | 584.4 | ++++ |
| 369 | 4-(4-(4-(2-(2-aminopyridin-3-yl)-5-(4-chlorophenyl)-3H-imidazo[4,5-b]pyridin-3-yl)benzyl)piperazin-1-yl)-1,3,5-triazine-2-carbonitrile | 600.4 | +++ |
| 370 | 4-((1-(4-(2-(2-aminopyridin-3-yl)-5-(4-fluorophenyl)-3H-imidazo[4,5-b]pyridin-3-yl)benzyl)piperidin-4-yl)amino)pyrimidine-2-carbonitrile | 597.4 | ++++ |
| 371 | 2-((1-(4-(2-(2-aminopyridin-3-yl)-5-(4-chlorophenyl)-3H-imidazo[4,5-b]pyridin-3-yl)benzyl)piperidin-4-yl)amino)pyrimidine-4-carbonitrile | 613.4 | ++ |
| 372 | 2-((1-(4-(2-(2-aminopyridin-3-yl)-5-(3-chlorophenyl)-3H-imidazo[4,5-b]pyridin-3-yl)benzyl)piperidin-4-yl)amino)pyrimidine-4-carbonitrile | 613.3 | +++ |
| 373 | 6-((1-(4-(2-(2-aminopyridin-3-yl)-5-(3-chlorophenyl)-3H-imidazo[4,5-b]pyridin-3-yl)benzyl)piperidin-4-yl)amino)pyrimidine-4-carbonitrile | 613.4 | +++ |
| 374 | 6-(4-(4-(2-(2-aminopyridin-3-yl)-5-(3-chlorophenyl)-3H-imidazo[4,5-b]pyridin-3-yl)benzyl)piperazin-1-yl)pyrimidine-4-carbonitrile | 599.4 | +++ |
| 375 | 4-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-2-carbonitrile | 577.3 | +++ |
| 376 | 6-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile | 577.3 | ++ |
| 377 | 2-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile | 577.3 | ++ |
| 378 | 4-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile | 593.4 | ++ |
| 379 | 2-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile | 593.2 | + |
| 380 | 6-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile | 593.4 | + |
| 381 | 4-((1-(4-(2-(2-aminopyridin-3-yl)-5-(2-oxo-1,2-dihydropyridin-3-yl)-3H-imidazo[4,5-b]pyridin-3-yl)benzyl)piperidin-4-yl)amino)pyrimidine-2-carbonitrile | 596.3 | ++++ |
| 382 | 4-((1-(4-(2-(2-aminopyridin-3-yl)-5-(4-chlorophenyl)-3H-imidazo[4,5-b]pyridin-3-yl)benzyl)piperidin-4-yl)amino)-1,3,5-triazine-2-carbonitrile | 614.4 | +++ |
| 383 | 4-(4-(4-(2-(2-aminopyridin-3-yl)-5-(4-cyanopyridin-3-yl)-3H-imidazo[4,5-b]pyridin-3-yl)benzyl)piperazin-1-yl)pyrimidine-2-carbonitrile | 591.4 | ++++ |
| 384 | 4-((1-(4-(2-(2-aminopyridin-3-yl)-5-(4-cyanopyridin-3-yl)-3H-imidazo[4,5-b]pyridin-3-yl)benzyl)piperidin-4-yl)amino)pyrimidine-2-carbonitrile | 605.4 | +++ |
| 385 | 4-((1-((4-(2-(2-aminopyridin-3-yl)-3H-imidazo[4,5-b]pyridin-3-yl)phenyl)methyl-d2)piperidin-4-yl)amino)pyrimidine-2-carbonitrile | 505.2 | +++ |

TABLE 4-continued

| Chemistry Example | Compound Name | MS: [M + H]+ | AKT1 E17K IC50 |
|---|---|---|---|
| 386 | 4-(4-(4-(2-(2-aminopyridin-3-yl)-5-(4-methyl-3-oxo-1,4-diazepan-1-yl)-3H-imidazo[4,5-b]pyridin-3-yl)benzyl)piperazin-1-yl)pyrimidine-2-carbonitrile | 615.3 | +++ |
| 387 | 4-((1-(4-(2-(2-aminopyridin-3-yl)-5-(3-oxomorpholino)-3H-imidazo[4,5-b]pyridin-3-yl)benzyl)piperidin-4-yl)amino)pyrimidine-2-carbonitrile | 602.4 | ++ |
| 388 | 4-((1-(4-(2-(2-aminopyridin-3-yl)-5-cyclopentyl-3H-imidazo[4,5-b]pyridin-3-yl)benzyl)piperidin-4-yl)amino)pyrimidine-2-carbonitrile | 571.2 | ++++ |
| 389 | 4-((1-(4-(2-(2-aminopyridin-3-yl)-5-(dimethylamino)-3H-imidazo[4,5-b]pyridin-3-yl)benzyl)piperidin-4-yl)amino)pyrimidine-2-carbonitrile | 546.4 | ++++ |
| 390 | 4-((1-(4-(2-(2-aminopyridin-3-yl)-3H-imidazo[4,5-b]pyridin-3-yl)benzyl)piperidin-4-yl)(methyl)amino)pyrimidine-2-carbonitrile | 517.2 | ++++ |
| 391 | 4-((1-(4-(2-(2-aminopyridin-3-yl)-5-phenyl-3H-imidazo[4,5-b]pyridin-3-yl)benzyl)piperidin-4-yl)amino)-1,3,5-triazine-2-carbonitrile | 580.2 | ++++ |
| 392 | 4-((1-(4-(2-(2-aminopyridin-3-yl)-3H-imidazo[4,5-b]pyridin-3-yl)benzyl)-4-methylpiperidin-4-yl)amino)pyrimidine-2-carbonitrile | 517.2 | ++ |
| 393 | 4-((1-(4-(2-(2-aminopyridin-3-yl)-5-(1-methyl-6-oxo-1,6-dihydropyridin-2-yl)-3H-imidazo[4,5-b]pyridin-3-yl)benzyl)piperidin-4-yl)amino)pyrimidine-2-carbonitrile | 610.5 | + |
| 394 | 4-(4-(4-(2-(2-aminopyridin-3-yl)-5-(1-methyl-6-oxo-1,6-dihydropyridin-2-yl)-3H-imidazo[4,5-b]pyridin-3-yl)benzyl)piperazin-1-yl)pyrimidine-2-carbonitrile | 596.1 | + |
| 395 | 4-((1-(4-(2-(2-aminopyridin-3-yl)-5-(3-methoxyphenyl)-3H-imidazo[4,5-b]pyridin-3-yl)benzyl)piperidin-4-yl)amino)pyrimidine-2-carbonitrile | 609.5 | ++++ |
| 396 | 4-((1-(4-(2-(2-aminopyridin-3-yl)-5-(tert-butyl)-3H-imidazo[4,5-b]pyridin-3-yl)benzyl)piperidin-4-yl)amino)pyrimidine-2-carbonitrile | 559.2 | +++ |
| 397 | 4-((1-(4-(2-(2-aminopyridin-3-yl)-5-ethyl-3H-imidazo[4,5-b]pyridin-3-yl)benzyl)piperidin-4-yl)amino)pyrimidine-2-carbonitrile | 531.2 | ++++ |
| 398 | 2-(2-aminopyridin-3-yl)-3-(4-(4-(2-cyanopyrimidin-4-yl)amino)piperidin-1-yl)methyl)phenyl)-N-methyl-3H-imidazo[4,5-b]pyridine-5-carboxamide | 560.2 | ++++ |
| 399 | 4-(4-(4-(2-(2-aminopyridin-3-yl)-5-(3-cyanopyridin-4-yl)-3H-imidazo[4,5-b]pyridin-3-yl)benzyl)piperazin-1-yl)pyrimidine-2-carbonitrile | 591.3 | +++ |
| 400 | 4-((1-(4-(2-(2-aminopyridin-3-yl)-5-(3-cyanopyridin-4-yl)-3H-imidazo[4,5-b]pyridin-3-yl)benzyl)piperidin-4-yl)amino)pyrimidine-2-carbonitrile | 605.4 | ++++ |
| 401 | 4-((1-(4-(2-(2-aminopyridin-3-yl)-5-fluoro-3H-imidazo[4,5-b]pyridin-3-yl)benzyl)piperidin-4-yl)amino)pyrimidine-2-carbonitrile | 521.4 | +++ |
| 402 | 4-((1-(4-(2-(2-aminopyridin-3-yl)-6-fluoro-3H-imidazo[4,5-b]pyridin-3-yl)benzyl)piperidin-4-yl)amino)pyrimidine-2-carbonitrile | 521.1 | ++++ |
| 403 | 4-((1-(4-(2-(2-aminopyridin-3-yl)-5-(2-oxooxazolidin-3-yl)-3H-imidazo[4,5-b]pyridin-3-yl)benzyl)piperidin-4-yl)amino)pyrimidine-2-carbonitrile | 588.1 | ++++ |
| 404 | 4-((1-(4-(2-(2-aminopyridin-3-yl)-5-(6-fluoropyridin-3-yl)-3H-imidazo[4,5-b]pyridin-3-yl)benzyl)piperidin-4-yl)amino)pyrimidine-2-carbonitrile | 598.4 | ++++ |
| 405 | 4-((1-(4-(2-(2-aminopyridin-3-yl)-5-chloro-3H-imidazo[4,5-b]pyridin-3-yl)benzyl)piperidin-4-yl)amino)pyrimidine-2-carbonitrile | 537.2 | ++++ |
| 406 | 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carbonitrile | 528.3 | ++++ |
| 407 | 4-(4-(4-(2-(2-aminopyridin-3-yl)-5-(3-cyanopyridin-2-yl)-3H-imidazo[4,5-b]pyridin-3-yl)benzyl)piperazin-1-yl)pyrimidine-2-carbonitrile | 591.1 | ++++ |
| 408 | 4-((1-(4-(2-(2-aminopyridin-3-yl)-5-(3-cyanopyridin-2-yl)-3H-imidazo[4,5-b]pyridin-3-yl)benzyl)piperidin-4-yl)amino)pyrimidine-2-carbonitrile | 605.4 | ++++ |
| 409 | 4-((1-(4-(2-(2-aminopyridin-3-yl)-5-(2-cyanopyridin-3-yl)-3H-imidazo[4,5-b]pyridin-3-yl)benzyl)piperidin-4-yl)amino)pyrimidine-2-carbonitrile | 605.4 | ++++ |
| 410 | 4-((1-(4-(2-(2-aminopyridin-3-yl)-5-(trifluoromethyl)-3H-imidazo[4,5-b]pyridin-3-yl)benzyl)piperidin-4-yl)amino)pyrimidine-2-carbonitrile | 571.3 | ++++ |

TABLE 4-continued

| Chemistry Example | Compound Name | MS: [M + H]+ | AKT1 E17K IC50 |
|---|---|---|---|
| 411 | 2-(2-aminopyridin-3-yl)-3-(4-((4-((2-cyanopyrimidin-4-yl)amino)piperidin-1-yl)methyl)phenyl)-3H-imidazo[4,5-b]pyridine-6-carbonitrile | 528.4 | +++ |
| 412 | 4-((1-(4-(2-(2-aminopyridin-3-yl)-5,6-dimethyl-3H-imidazo[4,5-b]pyridin-3-yl)benzyl)piperidin-4-yl)amino)pyrimidine-2-carbonitrile | 531.4 | ++++ |
| 413 | 4-((1-(4-(2-(2-aminopyridin-3-yl)-1H-imidazo[4,5-b]pyrazin-1-yl)benzyl)piperidin-4-yl)amino)pyrimidine-2-carbonitrile | 504.1 | +++ |
| 414 | methyl 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylate | 561.3 | ++++ |
| 415 | 2-(2-aminopyridin-3-yl)-3-(4-((4-(2-cyanopyrimidin-4-yl)amino)piperidin-1-yl)methyl)phenyl)-3H-imidazo[4,5-b]pyridine-5-carboxylic acid | 547.4 | + |
| 416 | 4-((1-(4-(2-(2-aminopyridin-3-yl)-5-(fluoromethoxy)-3H-imidazo[4,5-b]pyridin-3-yl)benzyl)piperidin-4-yl)amino)pyrimidine-2-carbonitrile | 551.1 | ++++ |
| 417 | 4-((1-(4-(2-(2-aminopyridin-3-yl)-5-(tetrahydrofuran-3-yl)-3H-imidazo[4,5-b]pyridin-3-yl)benzyl)piperidin-4-yl)amino)pyrimidine-2-carbonitrile | 573.4 | ++++ |
| 418 | 4-((1-(4-(2-(2-aminopyridin-3-yl)-5-(5-cyanopyridin-2-yl)-3H-imidazo[4,5-b]pyridin-3-yl)benzyl)piperidin-4-yl)amino)pyrimidine-2-carbonitrile | 605.0 | +++ |
| 419 | 4-((1-(4-(2-(2-aminopyridin-3-yl)-5-(6-cyanopyridin-3-yl)-3H-imidazo[4,5-b]pyridin-3-yl)benzyl)piperidin-4-yl)amino)pyrimidine-2-carbonitrile | 605.1 | ++++ |
| 420 | 4-((1-(4-(2-(2-aminopyridin-3-yl)-5-(oxetan-3-yl)-3H-imidazo[4,5-b]pyridin-3-yl)benzyl)piperidin-4-yl)amino)pyrimidine-2-carbonitrile | 559.1 | ++++ |
| 421 | 4-((1-(4-(2-(2-aminopyridin-3-yl)-5-(4-methoxyphenyl)-3H-imidazo[4,5-b]pyridin-3-yl)benzyl)piperidin-4-yl)amino)pyrimidine-2-carbonitrile | 609.2 | ++++ |
| 422 | 4-((1-(4-(2-(2-aminopyridin-3-yl)-5-(2-methoxyphenyl)-3H-imidazo[4,5-b]pyridin-3-yl)benzyl)piperidin-4-yl)amino)pyrimidine-2-carbonitrile | 609.1 | ++++ |
| 423 | 4-((1-(4-(2-(2-aminopyridin-3-yl)-5-(trifluoromethoxy)-3H-imidazo[4,5-b]pyridin-3-yl)benzyl)piperidin-4-yl)amino)pyrimidine-2-carbonitrile | 587.1 | ++ |
| 424 | 4-(4-(4-(2-(2-aminopyridin-3-yl)-5-(2-cyanopyridin-3-yl)-3H-imidazo[4,5-b]pyridin-3-yl)benzyl)piperazin-1-yl)pyrimidine-2-carbonitrile | 591.4 | +++ |
| 425 | 4-((1-(4-(2-(2-aminopyridin-3-yl)-5-isopropoxy-3H-imidazo[4,5-b]pyridin-3-yl)benzyl)piperidin-4-yl)amino)pyrimidine-2-carbonitrile | 561.1 | ++++ |
| 426 | 4-((4-(4-(2-(2-aminopyridin-3-yl)-5-phenyl-3H-imidazo[4,5-b]pyridin-3-yl)benzyl)piperazin-1-yl)amino)pyrimidine-2-carbonitrile | 580.4 | ++++ |
| 427 | 4-((1-(4-(2-(2-aminopyridin-3-yl)-5-(methoxy-d3)-3H-imidazo[4,5-b]pyridin-3-yl)benzyl)piperidin-4-yl)amino)pyrimidine-2-carbonitrile | 536.1 | ++++ |
| 428 | 4-((1-(4-(2-(2-aminopyridin-3-yl)-5-(6-cyanopyridin-2-yl)-3H-imidazo[4,5-b]pyridin-3-yl)benzyl)piperidin-4-yl)amino)pyrimidine-2-carbonitrile | 605.1 | +++ |
| 429 | 4-((1-(4-(2-(2-aminopyridin-3-yl)-5-(2-cyanopyridin-4-yl)-3H-imidazo[4,5-b]pyridin-3-yl)benzyl)piperidin-4-yl)amino)pyrimidine-2-carbonitrile | 605.2 | ++++ |
| 430 | 4-((1-(4-(2-(2-aminopyridin-3-yl)-5-(5-cyanopyridin-3-yl)-3H-imidazo[4,5-b]pyridin-3-yl)benzyl)piperidin-4-yl)amino)pyrimidine-2-carbonitrile | 605.3 | ++++ |
| 431 | 4-((1-(4-(2-(2-aminopyridin-3-yl)-5-(pyridin-3-yl)-3H-imidazo[4,5-b]pyridin-3-yl)benzyl)piperidin-4-yl)amino)pyrimidine-2-carbonitrile | 580.3 | ++++ |
| 432 | 4-(4-(4-(2-(2-aminopyridin-3-yl)-5-(pyridin-3-yl)-3H-imidazo[4,5-b]pyridin-3-yl)benzyl)piperazin-1-yl)pyrimidine-2-carbonitrile | 566.3 | ++++ |
| 433 | 4-((1-(4-(2-(2-aminopyridin-3-yl)-5-(pyridin-4-yl)-3H-imidazo[4,5-b]pyridin-3-yl)benzyl)piperidin-4-yl)amino)pyrimidine-2-carbonitrile | 580.4 | ++++ |
| 434 | 4-((7-(4-(2-(2-aminopyridin-3-yl)-5-morpholino-3H-imidazo[4,5-b]pyridin-3-yl)benzyl)-7-azaspiro[3.5]nonan-2-yl)amino)-1,3,5-triazine-2-carbonitrile | 629.3 | +++ |
| 435 | 4-((1-(4-(2-(2-aminopyridin-3-yl)-5-(methylthio)-3H-imidazo[4,5-b]pyridin-3-yl)benzyl)piperidin-4-yl)amino)pyrimidine-2-carbonitrile | 571.0 [M + Na]+. | ++++ |

TABLE 4-continued

| Chemistry Example | Compound Name | MS: [M + H]+ | AKT1 E17K IC50 |
|---|---|---|---|
| 436 | 4-((1-(4-(2-(2-aminopyridin-3-yl)-5-(methylsulfonyl)-3H-imidazo[4,5-b]pyridin-3-yl)benzyl)piperidin-4-yl)amino)pyrimidine-2-carbonitrile | 581.3 | ++ |
| 437 | 4-((1-(4-(2-(2-aminopyridin-3-yl)-5-(4-methoxypyridin-2-yl)-3H-imidazo[4,5-b]pyridin-3-yl)benzyl)piperidin-4-yl)amino)pyrimidine-2-carbonitrile | 610.2 | ++++ |
| 438 | 4-((1-(4-(2-(2-aminopyridin-3-yl)-5-(1-methyl-1H-1,2,3-triazol-4-yl)-3H-imidazo[4,5-b]pyridin-3-yl)benzyl)piperidin-4-yl)amino)pyrimidine-2-carbonitrile | 584.2 | ++++ |
| 439 | 4-((1-(4-(2-(2-aminopyridin-3-yl)-5-(4-fluoro-3-methoxyphenyl)-3H-imidazo[4,5-b]pyridin-3-yl)benzyl)piperidin-4-yl)amino)pyrimidine-2-carbonitrile | 627.3 | ++++ |
| 440 | N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)acetamide | 636.2 | ++++ |
| 441 | 4-((1-(4-(2-(2-aminopyridin-3-yl)-5-(4-fluorophenyl)-3H-imidazo[4,5-b]pyridin-3-yl)benzyl)piperidin-4-yl)(methyl-d3)amino)pyrimidine-2-carbonitrile | 614.7 | ++++ |
| 442 | 4-((1-((4-(2-(2-aminopyridin-3-yl)-5-(4-fluorophenyl)-3H-imidazo(4,5-b]pyridin-3-yl)phenyl)methyl-d2)piperidin-4-yl)(methyl-d3)amino)pyrimidine-2-carbonitrile | 616.5 | ++++ |
| 443 | 4-((1-(4-(2-(2-aminopyridin-3-yl)-5-(4-fluorophenyl)-3H-imidazo[4,5-b]pyridin-3-yl)benzyl)azetidin-3-yl)amino)pyrimidine-2-carbonitrile | 569.3 | ++++ |
| 444 | 4-((7-(4-(2-(2-aminopyridin-3-yl)-5-(4-fluorophenyl)-3H-imidazo[4,5-b]pyridin-3-yl)benzyl)-7-azaspiro[3.5]nonan-2-yl)amino)pyrimidine-2-carbonitrile | 637.4 | +++ |
| 445 | 4-((2-(4-(2-(2-aminopyridin-3-yl)-5-(4-fluorophenyl)-3H-imidazo[4,5-b]pyridin-3-yl)benzyl)-2-azaspiro[3.3]heptan-6-yl)amino)pyrimidine-2-carbonitrile | 609.3 | ++++ |
| 446 | 4-((2-(4-(2-(2-aminopyridin-3-yl)-5-(4-fluorophenyl)-3H-imidazo[4,5-b]pyridin-3-yl)benzyl)-2-azaspiro[3.5]nonan-7-yl)amino)pyrimidine-2-carbonitrile | 637.4 | +++ |
| 447 | 4-(6-(4-(2-(2-aminopyridin-3-yl)-5-(4-fluorophenyl)-3H-imidazo[4,5-b]pyridin-3-yl)benzyl)-2,6-diazaspiro[3.3]heptan-2-yl)pyrimidine-2-carbonitrile | 595.3 | ++++ |
| 448 | 4-(8-(4-(2-(2-aminopyridin-3-yl)-5-(4-fluorophenyl)-3H-imidazo[4,5-b]pyridin-3-yl)benzyl)-3,8-diazabicyclo[3.2.1]octan-3-yl)pyrimidine-2-carbonitrile | 609.2 | +++ |
| 449 | 4-((3aR,6aS)-5-(4-(2-(2-aminopyridin-3-yl)-5-(4-fluorophenyl)-3H-imidazo[4,5-b]pyridin-3-yl)benzyl)hexahydropyrrolo[3,4-c]pyrrol-2(1H)-yl)pyrimidine-2-carbonitrile | 609.3 | +++ |
| 450 | 4-(3aS,6aS)-5-(4-(2-(2-aminopyridin-3-yl)-5-(4-fluorophenyl)-3H-imidazo[4,5-b]pyridin-3-yl)benzyl)hexahydropyrrolo[3,4-c]pyrrol-2(1H)-yl)pyrimidine-2-carbonitrile | 609.4 | +++ |
| 451 | 4-((1-(4-(2-(2-aminopyridin-3-yl)-5-(4-fluorophenyl)-3H-imidazo[4,5-b]pyridin-3-yl)benzyl)piperidin-4-yl-4-d)amino)pyrimidine-2-carbonitrile | 598.7 | ++++ |
| 452 | 4-((1-(4-(2-(2-aminopyridin-3-yl)-5,6-dimethyl-3H-imidazo[4,5-b]pyridin-3-yl)benzyl)piperidin-4-yl-4-d)amino)pyrimidine-2-carbonitrile | 532.7 | ++++ |
| 453 | 4-((1-(4-(2-(2-aminopyridin-3-yl)-5-(cyclopent-1-en-1-yl)-3H-imidazo[4,5-b]pyridin-3-yl)benzyl)piperidin-4-yl)amino)pyrimidine-2-carbonitrile | 569.3 | ++++ |
| 454 | 4-((1-(4-(2-(2-aminopyridin-3-yl)-5-vinyl-3H-imidazo[4,5-b]pyridin-3-yl)benzyl)piperidin-4-yl)amino)pyrimidine-2-carbonitrile | 529.2 | ++++ |
| 455 | 4-((1-(4-(2-(2-aminopyridin-3-yl)-5,6-dimethyl-3H-imidazo[4,5-b]pyridin-3-yl)benzyl)piperidin-4-yl)(methyl-d3)amino)pyrimidine-2-carbonitrile | 548.3 | ++++ |
| 456 | 4-((1-(4-(2-(2-aminopyridin-3-yl)-5-(5-fluoropyridin-2-yl)-3H-imidazo[4,5-b]pyridin-3-yl)benzyl)piperidin-4-yl)amino)pyrimidine-2-carbonitrile | 598.2 | ++++ |
| 457 | 4-((1-(4-(2-(2-aminopyridin-3-yl)-5-(methylamino)-3H-imidazo[4,5-b]pyridin-3-yl)benzyl)piperidin-4-yl)amino)pyrimidine-2-carbonitrile | 532.2 | +++ |
| 458 | 4-((1-(4-(2-(2-aminopyridin-3-yl)-5-(bis(methyl-d3)amino)-3H-imidazo[4,5-b]pyridin-3-yl)benzyl)piperidin-4-yl)amino)pyrimidine-2-carbonitrile | 552.0 | ++++ |
| 459 | 4-((1-(4-(2-(2-aminopyridin-3-yl)-5-((methyl-d3)amino)-3H-imidazo[4,5-b]pyridin-3-yl)benzyl)piperidin-4-yl)amino)pyrimidine-2-carbonitrile | 535.1 | ++++ |

TABLE 4-continued

| Chemistry Example | Compound Name | MS: [M + H]+ | AKT1 E17K IC50 |
|---|---|---|---|
| 460 | 4-((1-(4-(2-(2-aminopyridin-3-yl)-5-(azetidin-1-yl)-3H-imidazo[4,5-b]pyridin-3-yl)benzyl)piperidin-4-yl)amino)pyrimidine-2-carbonitrile | 558.5 | ++++ |
| 461 | 4-((1-(4-(2-(2-aminopyridin-3-yl)-5-(isoxazol-4-yl)-3H-imidazo[4,5-b]pyridin-3-yl)benzyl)piperidin-4-yl)amino)pyrimidine-2-carbonitrile | 570.3 | ++++ |
| 462 | 4-((1-(4-(2-(2-aminopyridin-3-yl)-5-(oxazol-5-yl)-3H-imidazo[4,5-b]pyridin-3-yl)benzyl)piperidin-4-yl)amino)pyrimidine-2-carbonitrile | 570.2 | ++++ |
| 463 | 4-((1-(4-(2-(2-aminopyridin-3-yl)-5-(5-methylisoxazol-4-yl)-3H-imidazo[4,5-b]pyridin-3-yl)benzyl)piperidin-4-yl)amino)pyrimidine-2-carbonitrile | 584.3 | ++++ |
| 464 | 4-((1-(4-(2-(2-aminopyridin-3-yl)-5-(3-methylisoxazol-4-yl)-3H-imidazo[4,5-b]pyridin-3-yl)benzyl)piperidin-4-yl)amino)pyrimidine-2-carbonitrile | 584.4 | ++++ |
| 465 | 4-((1-(4-(2-(2-aminopyridin-3-yl)-5-(3-methyl-1H-pyrazol-5-yl)-3H-imidazo[4,5-b]pyridin-3-yl)benzyl)piperidin-4-yl)amino)pyrimidine-2-carbonitrile | 583.3 | ++++ |
| 466 | 4-((1-(4-(2-(2-aminopyridin-3-yl)-5-(1-ethyl-1H-pyrazol-4-yl)-3H-imidazo[4,5-b]pyridin-3-yl)benzyl)piperidin-4-yl)amino)pyrimidine-2-carbonitrile | 597.4 | ++++ |
| 467 | 4-((1-(4-(2-(2-aminopyridin-3-yl)-5-(1-methyl-1H-pyrazol-5-yl)-3H-imidazo[4,5-b]pyridin-3-yl)benzyl)piperidin-4-yl)amino)pyrimidine-2-carbonitrile | 583.4 | ++++ |
| 468 | 4-((1-(4-(2-(2-aminopyridin-3-yl)-5-(3-(2-oxopyrrolidin-1-yl)phenyl)-3H-imidazo[4,5-b]pyridin-3-yl)benzyl)piperidin-4-yl)amino)pyrimidine-2-carbonitrile | 662.4 | ++++ |
| 469 | 4-((1-(4-(2-(2-aminopyridin-3-yl)-5-(4-fluoro-2-methoxyphenyl)-3H-imidazo[4,5-b]pyridin-3-yl)benzyl)piperidin-4-yl)amino)pyrimidine-2-carbonitrile | 627.5 | ++++ |
| 470 | 4-((1-(4-(2-(2-aminopyridin-3-yl)-5-(2-(trifluoromethyl)phenyl)-3H-imidazo[4,5-b]pyridin-3-yl)benzyl)piperidin-4-yl)amino)pyrimidine-2-carbonitrile | 647.3 | ++ |
| 471 | 4-((1-(4-(2-(2-aminopyridin-3-yl)-5-(4-(trifluoromethyl)phenyl)-3H-imidazo[4,5-b]pyridin-3-yl)benzyl)piperidin-4-yl)amino)pyrimidine-2-carbonitrile | 647.3 | +++ |
| 472 | 4-((1-(4-(2-(2-aminopyridin-3-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile | 584.3 | ++++ |
| 473 | 4-((1-(4-(2-(2-aminopyridin-3-yl)-5-(3,5-dimethylisoxazol-4-yl)-3H-imidazo[4,5-b]pyridin-3-yl)benzyl)piperidin-4-yl)amino)pyrimidine-2-carbonitrile | 598.4 | ++++ |
| 474 | 4-((1-(4-(2-(2-aminopyridin-3-yl)-5-(1-(difluoromethyl)-1H-pyrazol-4-yl)-3H-imidazo[4,5-b]pyridin-3-yl)benzyl)piperidin-4-yl)amino)pyrimidine-2-carbonitrile | 619.3 | ++++ |
| 475 | 4-((1-(4-(2-(2-aminopyridin-3-yl)-5-(2,4-difluorophenyl)-3H-imidazo[4,5-b]pyridin-3-yl)benzyl)piperidin-4-yl)amino)pyrimidine-2-carbonitrile | 615.3 | ++++ |
| 476 | 4-((1-(4-(2-(2-aminopyridin-3-yl)-5-(6-methoxypyridin-2-yl)-3H-imidazo[4,5-b]pyridin-3-yl)benzyl)piperidin-4-yl)amino)pyrimidine-2-carbonitrile | 610.5 | ++++ |
| 477 | 4-((1-(4-(2-(2-aminopyridin-3-yl)-5-(2-methylpyridin-4-yl)-3H-imidazo[4,5-b]pyridin-3-yl)benzyl)piperidin-4-yl)amino)pyrimidine-2-carbonitrile | 594.3 | ++++ |
| 478 | 4-((1-(4-(2-(2-aminopyridin-3-yl)-5-(5-methylpyridin-3-y])-3H-imidazo[4,5-b]pyridin-3-yl)benzyl)piperidin-4-yl)amino)pyrimidine-2-carbonitrile | 594.4 | ++++ |
| 479 | 4-((1-(4-(2-(2-aminopyridin-3-yl)-5-(1-isopropyl-1H-pyrazol-4-yl)-3H-imidazo[4,5-b]pyridin-3-yl)benzyl)piperidin-4-yl)amino)pyrimidine-2-carbonitrile | 611.3 | ++++ |
| 480 | 4-((1-(4-(2-(2-aminopyridin-3-yl)-5-(isothiazol-4-yl)-3H-imidazo[4,5-b]pyridin-3-yl)benzyl)piperidin-4-yl)amino)pyrimidine-2-carbonitrile | 586.3 | ++++ |
| 481 | 4-((1-(4-(2-(2-aminopyridin-3-yl)-5-(5-cyano-1-methyl-1H-pyrrol-3-yl)-3H-imidazo[4,5-b]pyridin-3-yl)benzyl)piperidin-4-yl)amino)pyrimidine-2-carbonitrile | 607.3 | ++++ |
| 482 | 4-((1-(4-(2-(2-aminopyridin-3-yl)-5-(thiazol-4-yl)-3H-imidazo[4,5-b]pyridin-3-yl)benzyl)piperidin-4-yl)amino)pyrimidine-2-carbonitrile | 608.2 [M + Na]+ | ++++ |
| 483 | 4-((1-(4-(2-(2-aminopyridin-3-yl)-5-(isothiazol-5-yl)-3H-imidazo[4,5-b]pyridin-3-yl)benzyl)piperidin-4-yl)amino)pyrimidine-2-carbonitrile | 586.3 | ++++ |
| 484 | 4-((1-(4-(2-(2-aminopyridin-3-yl)-5-(1,5-dimethyl-1H-pyrazol-4-yl)-3H-imidazo[4,5-b]pyridin-3-yl)benzyl)piperidin-4-yl)amino)pyrimidine-2-carbonitrile | 597.2 | ++++ |

TABLE 4-continued

| Chemistry Example | Compound Name | MS: [M + H]+ | AKT1 E17K IC50 |
|---|---|---|---|
| 485 | 4-((1-(4-(2-(2-aminopyridin-3-yl)-5-bromo-3H-imidazo[4,5-b]pyridin-3-yl)benzyl)piperidin-4-yl)amino)pyrimidine-2-carbonitrile | 581.2, 583.1 | ++++ |
| 486 | 4-((1-((4-(2-(2-aminopyridin-3-yl)-5-bromo-3H-imidazo[4,5-b]pyridin-3-yl)phenyl)methyl-d2)piperidin-4-yl)amino)pyrimidine-2-carbonitrile | 583.2, 585.2 | ++++ |
| 487 | 4-((1-(4-(2-(2-aminopyridin-3-yl)-5-(4-fluorophenyl)-3H-imidazo[4,5-b]pyridin-3-yl)benzyl)piperidin-4-yl)amino)-1,3,5-triazine-2-carbonitrile | 598.3 | ++++ |
| 488 | 4-((1-((4-(2-(2-aminopyridin-3-yl)-5-(4-fluorophenyl)-3H-imidazo[4,5-b]pyridin-3-yl)phenyl)methyl-d2)piperidin-4-yl)(methyl)amino)pyrimidine-2-carbonitrile | 613.4 | ++++ |
| 489 | 4-((1-((4-(2-(2-aminopyridin-3-yl)-5-(4-fluorophenyl)-3H-imidazo[4,5-b]pyridin-3-yl)phenyl)methyl-d2)piperidin-4-yl)amino)pyrimidine-2-carbonitrile | 599.3 | ++++ |
| 490 | 4-(7-(4-(2-(2-aminopyridin-3-yl)-5-(4-fluorophenyl)-3H-imidazo[4,5-b]pyridin-3-yl)benzyl)-2,7-diazaspiro[3.5]nonan-2-yl)pyrimidine-2-carbonitrile | 623.3 | ++++ |
| 491 | 4-(2-(4-(2-(2-aminopyridin-3-yl)-5-(4-fluorophenyl)-3H-imidazo[4,5-b]pyridin-3-yl)benzyl)-2,7-diazaspiro[3.5]nonan-7-yl)pyrimidine-2-carbonitrile | 623.3 | ++++ |
| 492 | 4-((1-(4-(2-(2-aminopyridin-3-yl)-5-(methylsulfinyl)-3H-imidazo[4,5-b]pyridin-3-yl)benzyl)piperidin-4-yl)amino)pyrimidine-2-carbonitrile | 565.2 | ++ |
| 493 | 4-((1-(4-(2-(2-aminopyridin-3-yl)-5,7-dimethyl-3H-imidazo[4,5-b]pyridin-3-yl)benzyl)piperidin-4-yl)amino)pyrimidine-2-carbonitrile | 531.7 | ++++ |
| 494 | 4-((1-(4-(8-(2-aminopyridin-3-yl)-6-hydroxy-9H-purin-9-yl)benzyl)piperidin-4-yl)amino)pyrimidine-2-carbonitrile | 520.1 | + |
| 495 | 4-((1-(4-(2-(2-aminopyridin-3-yl)-5-(pyridin-2-yl)-3H-imidazo[4,5-b]pyridin-3-yl)benzyl)piperidin-4-yl)amino)pyrimidine-2-carbonitrile | 580.3 | ++++ |
| 496 | 4-((1-(4-(2-(2-aminopyridin-3-yl)-5-hydroxy-3H-imidazo[4,5-b]pyridin-3-yl)benzyl)piperidin-4-yl)amino)pyrimidine-2-carbonitrile | 519.2 | +++ |
| 497 | 4-(1-(4-(5-amino-2-(2-aminopyridin-3-yl)-3H-imidazo[4,5-b]pyridin-3-yl)benzyl)piperidin-4-yl)amino)pyrimidine-2-carbonitrile | 518.2 | +++ |
| 498 | 4-((1-(4-(2-(2-aminopyridin-3-yl)-5-(2-chloro-4-fluorophenyl)-3H-imidazo[4,5-b]pyridin-3-yl)benzyl)piperidin-4-yl)amino)pyrimidine-2-carbonitrile | 631.3 | +++ |
| 499 | 4-((1-(4-(2-(2-aminopyridin-3-yl)-5-(4-fluorophenyl)-6-methyl-3H-imidazo[4,5-b]pyridin-3-yl)benzyl)piperidin-4-yl)amino)pyrimidine-2-carbonitrile | 611.4 | ++++ |
| 500 | 2-(2-aminopyridin-3-yl)-1-(4-((4-((2-cyanopyrimidin-4-yl)amino)piperidin-1-yl)methyl)phenyl)-1H-benzo[d]imidazole-6-carbonitrile | 527.4 | ++++ |
| 501 | 2-(2-aminopyridin-3-yl)-1-(4-((4-((2-cyanopyrimidin-4-yl)amino)piperidin-1-yl)methyl)phenyl)-1H-benzo[d]imidazole-5-carbonitrile | 527.1 | +++ |
| 502 | 4-((1-((4-(2-(2-aminopyridin-3-yl)-3H-imidazo[4,5-b]pyridin-3-yl)phenyl)methyl-d2)piperidin-4-yl)(methyl-d3)amino)pyrimidine-2-carbonitrile | 522.3 | +++ |
| 503 | 4-((1-(4-(2-(2-aminopyridin-3-yl)-3H-imidazo[4,5-b]pyridin-3-yl)benzyl)piperidin-4-yl-4-d)amino)pyrimidine-2-carbonitrile | 504.2 | +++ |
| 504 | 4-((1-((4-(2-(2-aminopyridin-3-yl)-5,6-dimethyl-3H-imidazo[4,5-b]pyridin-3-yl)phenyl)methyl-d2)piperidin-4-yl)amino)pyrimidine-2-carbonitrile | 533.2 | ++++ |
| 505 | 4-((1-(4-(8-(2-aminopyridin-3-yl)-9H-purin-9-yl)benzyl)piperidin-4-yl)amino)pyrimidine-2-carbonitrile | 504.1 | ++ |
| 506 | (S)-4-((1-(4-(2-(2-aminopyridin-3-yl)-5-(tetrahydrofuran-3-yl)-3H-imidazo[4,5-b]pyridin-3-yl)benzyl)piperidin-4-yl)amino)pyrimidine-2-carbonitrile | 573.3 | ++++ |
| 507 | (R)-4-((1-(4-(2-(2-aminopyridin-3-yl)-5-(tetrahydrofuran-3-yl)-3H-imidazo[4,5-b]pyridin-3-yl)benzyl)piperidin-4-yl)amino)pyrimidine-2-carbonitrile | 573.2 | ++++ |
| 508 | 4-((1-(4-(2-(2-aminopyridin-3-yl)-5-(hydroxymethyl)-3H-imidazo[4,5-b]pyridin-3-yl)benzyl)piperidin-4-yl)amino)pyrimidine-2-carbonitrile | 533.1 | +++ |
| 509 | 4-((1-(4-(2-(2-aminopyridin-3-yl)-5-(fluoromethyl)-3H-imidazo[4,5-b]pyridin-3-yl)benzyl)piperidin-4-yl)amino)pyrimidine-2-carbonitrile | 535.1 | ++++ |
| 510 | 4-((1-(4-(2-(2-aminopyridin-3-yl)-5-(pyrrolidin-1-yl)-3H-imidazo[4,5-b]pyridin-3-yl)benzyl)piperidin-4-yl)amino)pyrimidine-2-carbonitrile | 572.4 | ++++ |

TABLE 4-continued

| Chemistry Example | Compound Name | MS: [M + H]+ | AKT1 E17K IC50 |
|---|---|---|---|
| 511 | 4-((1-(4-(2-(2-aminopyridin-3-yl)-5-(2-methoxypyridin-4-yl)-3H-imidazo[4,5-b]pyridin-3-yl)benzyl)piperidin-4-yl)amino)pyrimidine-2-carbonitrile | 610.1 | ++++ |
| 512 | 4-((1-(4-(2-(2-aminopyridin-3-yl)-5-(5-methoxypyridin-3-yl)-3H-imidazo[4,5-b]pyridin-3-yl)benzyl)piperidin-4-yl)amino)pyrimidine-2-carbonitrile | 610.3 | ++++ |
| 513 | 4-((1-(4-(2-(2-aminopyridin-3-yl)-5-ethynyl-3H-imidazo[4,5-b]pyridin-3-yl)benzyl)piperidin-4-yl)amino)pyrimidine-2-carbonitrile | 527.2 | ++++ |
| 514 | N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)-N-methylacetamide | 650.1 | ++++ |
| 515 | 4-((1-(4-(2-(2-aminopyridin-3-yl)-5-(3-methoxypyridin-4-yl)-3H-imidazo[4,5-b]pyridin-3-yl)benzyl)piperidin-4-yl)amino)pyrimidine-2-carbonitrile | 610.1 | ++++ |
| 516 | 4-((1-(4-(2-(2-aminopyridin-3-yl)-5-(6-methoxypyridin-3-y])-3H-imidazo[4,5-b]pyridin-3-yl)benzyl)piperidin-4-yl)amino)pyrimidine-2-carbonitrile | 610.2 | ++++ |
| 517 | 4-((1-(4-(5-(3-aminophenyl)-2-(2-aminopyridin-3-yl)-3H-imidazo[4,5-b]pyridin-3-yl)benzyl)piperidin-4-yl)amino)pyrimidine-2-carbonitrile | 594.3 | ++++ |
| 518 | N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)isobutyramide | 664.3 | ++++ |
| 519 | N-(3-(3-(4-((4-((2-cyanopyrimidin-4-yl)amino)piperidin-1-yl)methyl)phenyl)-2-(2-isobutyramidopyridin-3-y])-3H-imidazo[4,5-b]pyridin-5-yl)phenyl)isobutyramide | 734.3 | +++ |
| 520 | methyl (3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)carbamate | 652.2 | ++++ |
| 521 | 4-((1-(4-(2-(2-aminopyridin-3-yl)-5-(3-(dimethylamino)phenyl)-3H-imidazo[4,5-b]pyridin-3-yl)benzyl)piperidin-4-yl)amino)pyrimidine-2-carbonitrile | 622.3 | ++++ |
| 522 | N-(1-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)piperidin-4-yl)-N-metbylacetamide | 733.4 | +++ |
| 523 | 4-((1-(4-(2-(2-aminopyridin-3-yl)-5-(4-fluoro-2-methylphenyl)-3H-imidazo[4,5-b]pyridin-3-yl)benzyl)piperidin-4-yl)amino)pyrimidine-2-carbonitrile | 611.4 | +++ |
| 524 | 2-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)-5-fluorobenzamide | 640.2 | + |
| 525 | 4-((1-(4-(2-(2-aminopyridin-3-yl)-5-(2-cyano-4-fluorophenyl)-3H-imidazo[4,5-b]pyridin-3-yl)benzyl)piperidin-4-yl)amino)pyrimidine-2-carbonitrile | 622.1 | +++ |
| 526 | 4-((1-(4-(2-(2-aminopyridin-3-yl)-5-(4-fluoro-2-(trifluoromethyl)phenyl)-3H-imidazo[4,5-b]pyridin-3-yl)benzyl)piperidin-4-yl)amino)pyrimidine-2-carbonitrile | 665.1 | + |
| 527 | 4-((1-(4-(2-(2-aminopyridin-3-yl)-5-(o-tolyl)-3H-imidazo[4,5-b]pyridin-3-yl)benzyl)piperidin-4-yl)amino)pyrimidine-2-carbonitrile | 593.2 | ++++ |
| 528 | 4-((1-(4-(2-(2-aminopyridin-3-yl)-5-(m-tolyl)-3H-imidazo[4,5-b]pyridin-3-yl)benzyl)piperidin-4-yl)amino)pyrimidine-2-carbonitrile | 593.4 | ++++ |
| 529 | 4-((1-(4-(2-(2-aminopyridin-3-yl)-5-(p-tolyl)-3H-imidazo[4,5-b]pyridin-3-yl)benzyl)piperidin-4-yl)amino)pyrimidine-2-carbonitrile | 593.3 | ++++ |
| 530 | 4-((1-(4-(2-(2-aminopyridin-3-yl)-5-(3-(trifluoromethyl)phenyl)-3H-imidazo[4,5-b]pyridin-3-yl)benzyl)piperidin-4-yl)amino)pyrimidine-2-carbonitrile | 647.3 | +++ |
| 531 | isopropyl 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylate | 589.3 | ++++ |
| 532 | 4-((1-(4-(2-(2-aminopyridin-3-yl)-1H-benzo[d]imidazol-1-yl)benzyl)piperidin-4-yl)amino)pyrimidine-2-carbonitrile | 502.3 | ++ |
| 533 | 4-((1-(4-(2-(2-aminopyridin-3-yl)-1H-imidazo[4,5-b]pyridin-1-yl)benzyl)piperidin-4-yl)amino)pyrimidine-2-carbonitrile | 503.4 | ++ |
| 534 | 4-((1-(4-(2-(2-aminopyridin-3-yl)-5-(6-methylpyridin-3-yl)-3H-imidazo[4,5-b]pyridin-3-yl)benzyl)piperidin-4-yl)amino)pyrimidine-2-carbonitrile | 594.1 | ++++ |
| 535 | 4-((1-(4-(2-(2-aminopyridin-3-yl)-5-(difluoromethoxy)-3H-imidazo[4,5-b]pyridin-3-yl)benzyl)piperidin-4-yl)amino)pyrimidine-2-carbonitrile | 569.3 | ++++ |
| 536 | 4-((1-(4-(2-(2-aminopyridin-3-yl)-5-(4-methoxypyridin-3-yl)-3H-imidazo[4,5-b]pyridin-3-yl)benzyl)piperidin-4-yl)amino)pyrimidine-2-carbonitrile | 610.3 | ++++ |

TABLE 4-continued

| Chemistry Example | Compound Name | MS: [M + H]+ | AKT1 E17K IC50 |
|---|---|---|---|
| 537 | 4-((1-(4-(2-(2-aminopyridin-3-yl)-5-(2-methoxypyridin-3-yl)-3H-imidazo[4,5-b]pyridin-3-yl)benzyl)piperidin-4-yl)amino)pyrimidine-2-carbonitrile | 610.4 | ++++ |
| 538 | 4-((1-(4-(2-(2-aminopyridin-3-yl)-5-(2-hydroxypyridin-3-yl)-3H-imidazo[4,5-b]pyridin-3-yl)benzyl)piperidin-4-yl)amino)pyrimidine-2-carbonitrile | 596.1 | +++ |
| 539 | 4-((1-(4-(2-(2-aminopyridin-3-yl)-5-(1,3-dimethyl-1H-pyrazol-4-yl)-3H-imidazo[4,5-b]pyridin-3-yl)benzyl)piperidin-4-yl)amino)pyrimidine-2-carbonitrile | 597.1 | ++++ |
| 540 | 4-((1-(4-(2-(2-aminopyridin-3-yl)-1H-imidazo[4,5-c]pyridin-1-yl)benzyl)piperidin-4-yl)amino)pyrimidine-2-carbonitrile | 503.2 | ++ |
| 541 | 4-((1-(4-(2-(2-aminopyridin-3-yl)-5-(4-fluorophenyl)-3H-imidazo[4,5-b]pyridin-3-yl)benzyl)piperidin-4-yl)(methyl)amino)pyrimidine-2-carbonitrile | 611.3 | ++++ |
| 542 | 4-((1-(4-(2-(2-aminopyridin-3-yl)-5-(6-(difluoromethoxy)pyridin-3-yl)-3H-imidazo[4,5-b]pyridin-3-yl)benzyl)piperidin-4-yl)amino)pyrimidine-2-carbonitrile | 646.3 | ++++ |
| 543 | 4-((1-(4-(2-(2-aminopyridin-3-yl)-5-(2-(difluoromethoxy)pyridin-4-yl)-3H-imidazo[4,5-b]pyridin-3-yl)benzyl)piperidin-4-yl)amino)pyrimidine-2-carbonitrile | 646.3 | +++ |
| 544 | 4-((1-(4-(2-(2-aminopyridin-3-yl)-5-(4-fluoro-2-hydroxyphenyl)-3H-imidazo[4,5-b]pyridin-3-yl)benzyl)piperidin-4-yl)amino)pyrimidine-2-carbonitrile | 613.2 | ++++ |
| 545 | 4-((1-(4-(2-(2-aminopyridin-3-yl)-5-(4-fluoro-3-hydroxyphenyl)-3H-imidazo[4,5-b]pyridin-3-yl)benzyl)piperidin-4-yl)amino)pyrimidine-2-carbonitrile | 613.2 | ++++ |
| 546 | 4-((1-(4-(2-(2-aminopyridin-3-yl)-5-(1-methyl-1H-imidazol-5-yl)-3H-imidazo[4,5-b]pyridin-3-yl)benzyl)piperidin-4-yl)amino)pyrimidine-2-carbonitrile | 583.3 | ++++ |
| 547 | 4-((1-(4-(2-(2-aminopyridin-3-yl)-5-(5-methylpyridin-2-y])-3H-imidazo[4,5-b]pyridin-3-yl)benzyl)piperidin-4-yl)amino)pyrimidine-2-carbonitrile | 594.3 | ++++ |
| 548 | 4-((1-(4-(2-(2-aminopyridin-3-yl)-5-(4-cyanopyridin-2-yl)-3H-imidazo[4,5-b]pyridin-3-yl)benzyl)piperidin-4-yl)amino)pyrimidine-2-carbonitrile | 605.5 | ++++ |
| 549 | 4-((1-(4-(2-(2-aminopyridin-3-yl)-6-bromo-5-(4-fluorophenyl)-3H-imidazo[4,5-b]pyridin-3-yl)benzyl)piperidin-4-yl)amino)pyrimidine-2-carbonitrile | 675.0, 677.0 | ++++ |
| 550 | 2-(2-aminopyridin-3-yl)-3-(4-((4-((2-cyanopyrimidin-4-yl)amino)piperidin-1-yl)methyl)phenyl)-5-methyl-3H-imidazo[4,5-b]pyridine-6-carbonitrile | 542.2 | ++++ |
| 551 | 4-((1-(4-(2-(2-aminopyridin-3-yl)-5-(3-fluoropyridin-4-yl)-3H-imidazo[4,5-b]pyridin-3-yl)benzyl)piperidin-4-yl)amino)pyrimidine-2-carbonitrile | 598.2 | ++++ |
| 552 | 4-((1-(4-(2-(2-aminopyridin-3-yl)-5-(5-methoxypyridin-2-yl)-3H-imidazo[4,5-b]pyridin-3-yl)benzyl)piperidin-4-yl)amino)pyrimidine-2-carbonitrile | 610.2 | ++++ |
| 553 | 2-(2-aminopyridin-3-yl)-1-(4-((4-((2-cyanopyrimidin-4-ylamino)piperidin-1-yl)methyl)phenyl)-1H-imidazo[4,5-c]pyridine-6-carbonitrile | 528.2 | +++ |
| 554 | 4-((1-(4-(2-(2-aminopyridin-3-yl)-5-(4-methyloxazol-5-yl)-3H-imidazo[4,5-b]pyridin-3-yl)benzyl)piperidin-4-yl)amino)pyrimidine-2-carbonitrile | 584.2 | ++++ |
| 555 | 4-((1-(4-(2-(2-aminopyridin-3-yl)-5-(1-cyclopropyl-1H-pyrazol-4-yl)-3H-imidazo[4,5-b]pyridin-3-yl)benzyl)piperidin-4-yl)amino)pyrimidine-2-carbonitrile | 609.3 | ++++ |
| 556 | 2-(2-aminopyridin-3-yl)-1-(4-((4-((2-cyanopyrimidin-4-yl)amino)piperidin-1-yl)methyl)phenyl)-1H-imidazo[4,5-b]pyrazine-5,6-dicarbonitrile | 554.2 | + |
| 557 | 2-(2-aminopyridin-3-yl)-3-(4-((4-((2-cyanopyrimidin-4-yl)amino)piperidin-1-yl)methyl)phenyl)-5-(4-fluorophenyl)-3H-imidazo[4,5-b]pyridine-6-carbonitrile | 622.2 | ++++ |
| 558 | 4-((1-(4-(2-(2-aminopyridin-3-yl)-5-(2-fluoropyridin-3-yl)-3H-imidazo[4,5-b]pyridin-3-yl)benzyl)piperidin-4-yl)amino)pyrimidine-2-carbonitrile | 598.1 | ++++ |
| 559 | 4-((1-(4-(2-(2-aminopyridin-3-yl)-5-(1-methyl-1H-1,2,4-triazol-3-yl)-3H-imidazo[4,5-b]pyridin-3-yl)benzyl)piperidin-4-yl)amino)pyrimidine-2-carbonitrile | 584.2 | +++ |
| 560 | 4-((1-(4-(2-(2-aminopyridin-3-yl)-5-(5-ethoxypyridin-2-yl)-3H-imidazo[4,5-b]pyridin-3-yl)benzyl)piperidin-4-yl)amino)pyrimidine-2-carbonitrile | 624.3 | ++++ |
| 561 | 4-((1-(4-(2-(2-aminopyridin-3-yl)-5-(2-fluoropyridin-4-yl)-3H-imidazo[4,5-b]pyridin-3-yl)benzyl)piperidin-4-yl)amino)pyrimidine-2-carbonitrile | 598.3 | ++++ |

TABLE 4-continued

| Chemistry Example | Compound Name | MS: [M + H]+ | AKT1 E17K IC50 |
|---|---|---|---|
| 562 | 4-((1-(4-(2-(3-aminopyrazin-2-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile | 585.2 | ++++ |
| 563 | 4-((1-(4-(2-(2-aminopyridin-3-yl)-5-(3-methoxypyridin-2-yl)-3H-imidazo[4,5-b]pyridin-3-yl)benzyl)piperidin-4-yl)amino)pyrimidine-2-carbonitrile | 610.2 | ++++ |
| 564 | 4-((1-(4-(2-(2-aminopyridin-3-yl)-5-(1-methyl-1H-1,2,3-triazol-5-yl)-3H-imidazo[4,5-b]pyridin-3-yl)benzyl)piperidin-4-yl)amino)pyrimidine-2-carbonitrile | 584.2 | +++ |
| 565 | 2-(2-aminopyridin-3-yl)-3-(4-((4-((2-cyanopyrimidin-4-yl)amino)piperidin-1-yl)methyl)phenyl)-6-methyl-3H-imidazo[4,5-b]pyridine-5-carbonitrile | 542.1 | ++++ |
| 566 | 4-((1-(4-(2-(2-aminopyridin-3-yl)-5-(5-methyl-1,3,4-oxadiazol-2-yl)-3H-imidazo[4,5-b]pyridin-3-yl)benzyl)piperidin-4-yl)amino)pyrimidine-2-carbonitrile | 585.2 | +++ |
| 567 | 4-((1-(4-(2-(2-aminopyridin-3-yl)-5-(1-methyl-1H-1,2,4-triazol-5-yl)-3H-imidazo[4,5-b]pyridin-3-yl)benzyl)piperidin-4-yl)amino)pyrimidine-2-carbonitrile | 584.2 | ++++ |
| 568 | 4-((1-(4-(2-(2-aminopyridin-3-yl)-5-(4-methyl-2H-1,2,3-triazol-2-yl)-3H-imidazo[4,5-b]pyridin-3-yl)benzyl)piperidin-4-yl)amino)pyrimidine-2-carbonitrile | 584.2 | ++++ |
| 569 | 4-((1-(4-(2-(2-aminopyridin-3-yl)-5-(4-methyl-4H-1,2,4-triazol-3-yl)-3H-imidazo[4,5-b]pyridin-3-yl)benzyl)piperidin-4-yl)amino)pyrimidine-2-carbonitrile | 584.2 | ++ |
| 570 | 4-((1-(4-(2-(2-aminopyridin-3-yl)-5-(3-fluoropyridin-2-yl)-3H-imidazo[4,5-b]pyridin-3-yl)benzyl)piperidin-4-yl)amino)pyrimidine-2-carbonitrile | 620.1 [M + Na]+ | ++++ |
| 571 | 4-((1-(4-(2-(2-aminopyridin-3-yl)-5-(6-methylpyridin-2-yl)-3H-imidazo[4,5-b]pyridin-3-yl)benzyl)piperidin-4-ylamino)pyrimidine-2-carbonitrile | 616.1 [M + Na]+ | ++++ |
| 572 | 4-((1-(4-(2-(2-aminopyridin-3-yl)-5-(1-(difluoromethyl)-1H-1,2,4-triazol-3-yl)-3H-imidazo[4,5-b]pyridin-3-yl)benzyl)piperidin-4-yl)amino)pyrimidine-2-carbonitrile | 620.1 | ++++ |
| 573 | 4-((1-(4-(2-(4-aminopyrimidin-5-yl)-5-(5-fluoropyridin-2-yl)-3H-imidazo[4,5-b]pyridin-3-yl)benzyl)piperidin-4-yl)amino)pyrimidine-2-carbonitrile | 599.2 | +++ |
| 574 | 4-((1-(4-(2-(3-aminopyrazin-2-yl)-5-(5-fluoropyridin-2-yl)-3H-imidazo[4,5-b]pyridin-3-yl)benzyl)piperidin-4-yl)amino)pyrimidine-2-carbonitrile | 599.0 | ++++ |
| 575 | 4-((1-(4-(5-(5-fluoropyridin-2-yl)-2-(pyridin-3-yl)-3H-imidazo[4,5-b]pyridin-3-yl)benzyl)piperidin-4-yl)amino)pyrimidine-2-carbonitrile | 583.1 | ++ |
| 576 | 4-((1-(4-(2-(2-aminophenyl)-5-(5-fluoropyridin-2-yl)-3H-imidazo[4,5-b]pyridin-3-yl)benzyl)piperidin-4-yl)amino)pyrimidine-2-carbonitrile | 597.2 | +++ |
| 577 | 4-((1-(4-(5-(5-fluoropyridin-2-yl)-2-phenyl-3H-imidazo[4,5-b]pyridin-3-yl)benzyl)piperidin-4-yl)amino)pyrimidine-2-carbonitrile | 582.2 | +++ |
| 578 | 4-((1-(4-(2-(2-aminopyridin-3-yl)-5-(5-(methoxy-d3)pyridin-2-yl)-3H-imidazo[4,5-b]pyridin-3-yl)benzyl)piperidin-4-yl)amino)pyrimidine-2-carbonitrile | 613.2 | ++++ |
| 579 | 4-((1-(4-(2-(2-aminopyridin-3-yl)-5-(5-(difluoromethoxy)pyridin-2-yl)-3H-imidazo[4,5-b]pyridin-3-yl)benzyl)piperidin-4-yl)amino)pyrimidine-2-carbonitrile | 646.3 | ++++ |
| 580 | 4-((1-(4-(2-(2-aminopyridin-3-yl)-5-(5-(fluoromethoxy)pyridin-2-yl)-3H-imidazo[4,5-b]pyridin-3-yl)benzyl)piperidin-4-yl)amino)pyrimidine-2-carbonitrile | 628.2 | ++++ |
| 581 | 4-((1-(4-(2-(2-aminopyridin-3-yl)-5-(5-methoxypyrimidin-2-yl)-3H-imidazo[4,5-b]pyridin-3-yl)benzyl)piperidin-4-yl)amino)pyrimidine-2-carbonitrile | 611.3 | +++ |
| 582 | 4-((1-(4-(2-(2-aminopyridin-3-yl)-5-(5-methylpyrazin-2-yl)-3H-imidazo[4,5-b]pyridin-3-yl)benzyl)piperidin-4-yl)amino)pyrimidine-2-carbonitrile | 595.3 | ++++ |
| 583 | 4-((1-(4-(2-(2-aminopyridin-3-yl)-5-(5-methoxypyrazin-2-yl)-3H-imidazo[4,5-b]pyridin-3-yl)benzyl)piperidin-4-yl)amino)pyrimidine-2-carbonitrile | 611.2 | ++++ |
| 584 | 4-((1-(4-(2-(2-aminopyridin-3-yl)-5-(6-ethoxypyridin-3-yl)-3H-imidazo[4,5-b]pyridin-3-yl)benzyl)piperidin-4-yl)amino)pyrimidine-2-carbonitrile | 624.1 | ++++ |
| 585 | 4-((1-(4-(2-(2-aminopyridin-3-yl)-5-(5-cyclopropoxypyridin-2-yl)-3H-imidazo[4,5-b]pyridin-3-yl)benzyl)piperidin-4-yl)amino)pyrimidine-2-carbonitrile | 658.2 [M + Na]+ | ++++ |
| 586 | 4-((1-(4-(2-(2-aminopyridin-3-yl)-5-(5-isopropoxypyridin-2-yl)-3H-imidazo[4,5-b]pyridin-3-yl)benzyl)piperidin-4-yl)amino)pyrimidine-2-carbonitrile | 638.4 | ++++ |

TABLE 4-continued

| Chemistry Example | Compound Name | MS: [M + H]⁺ | AKT1 E17K IC50 |
|---|---|---|---|
| 587 | 4-((1-(4-(2-(2-aminopyridin-3-yl)-5-(6-cyclopropylpyridin-3-yl)-3H-imidazo[4,5-b]pyridin-3-yl)benzyl)piperidin-4-yl)amino)pyrimidine-2-carbonitrile | 620.3 | ++++ |
| 588 | 4-((1-(4-(2-(2-aminopyridin-3-yl)-5-(3-methyl-4H-1,2,4-triazol-4-yl)-3H-imidazo[4,5-b]pyridin-3-yl)benzyl)piperidin-4-yl)amino)pyrimidine-2-carbonitrile | 584.4 | +++ |
| 589 | 4-((1-(4-(2-(2-aminopyridin-3-yl)-5-(3-methyl-1H-1,2,4-triazol-1-yl)-3H-imidazo[4,5-b]pyridin-3-yl)benzyl)piperidin-4-yl)amino)pyrimidine-2-carbonitrile | 584.3 | +++ |
| 590 | 4-((1-(4-(2-(2-aminopyridin-3-yl)-5-(1H-1,2,4-triazol-1-y])-3H-imidazo[4,5-b]pyridin-3-yl)benzyl)piperidin-4-yl)amino)pyrimidine-2-carbonitrile | 570.2 | ++++ |
| 591 | 4-((1-(4-(2-(2-aminopyridin-3-yl)-5-(1H-1,2,3-triazol-1-yl)-3H-imidazo[4,5-b]pyridin-3-yl)benzyl)piperidin-4-yl)amino)pyrimidine-2-carbonitrile | 570.1 | ++++ |
| 592 | 4-((1-(4-(2-(2-aminopyridin-3-yl)-5-(2H-1,2,3-triazol-2-yl)-3H-imidazo[4,5-b]pyridin-3-yl)benzyl)piperidin-4-yl)amino)pyrimidine-2-carbonitrile | 570.2 | ++++ |
| 593 | 4-((1-(4-(2-(2-aminopyridin-3-yl)-5-(4-methyl-1H-1,2,3-triazol-1-yl)-3H-imidazo[4,5-b]pyridin-3-yl)benzyl)piperidin-4-yl)amino)pyrimidine-2-carbonitrile | 584.4 | ++++ |
| 594 | 4-((1-(4-(2-(2-aminopyridin-3-yl)-5-(oxazol-4-yl)-3H-imidazo[4,5-b]pyridin-3-yl)benzyl)piperidin-4-yl)amino)pyrimidine-2-carbonitrile | 570.2 | ++++ |
| 595 | 4-((1-(4-(2-(2-aminopyridin-3-yl)-5-(4-fluoropyridin-3-yl)-3H-imidazo[4,5-b]pyridin-3-yl)benzyl)piperidin-4-yl)amino)pyrimidine-2-carbonitrile | 620.2 [M + Na]⁺ | ++++ |
| 596 | 4-((1-(4-(2-(2-aminopyridin-3-yl)-5-(4-methylpyridin-2-yl)-3H-imidazo[4,5-b]pyridin-3-yl)benzyl)piperidin-4-yl)amino)pyrimidine-2-carbonitrile | 616.2 [M + Na]⁺ | ++++ |
| 597 | 4-((1-(4-(2-(2-aminopyridin-3-yl)-5-(6-(methoxy-d3)pyridin-3-yl-2-d)-3H-imidazo[4,5-b]pyridin-3-yl)benzyl)piperidin-4-yl)amino)pyrimidine-2-carbonitrile Mixture of 3D (57.4% and 4D (38.2%) | 613.3 | ++++ |
| 598 | 4-((1-(4-(2-(2-aminopyridin-3-yl)-5-(6-(methoxy-d3)pyridin-3-yl)-3H-imidazo[4,5-b]pyridin-3-yl)benzyl)piperidin-4-yl)amino)pyrimidine-2-carbonitrile | 612.72 | ++++ |
| 599 | 2-(2-aminopyridin-3-yl)-3-(4-((4-((2-cyanopyrimidin-4-ylamino)piperidin-1-yl)methyl)phenyl)-5-hydroxy-3H-imidazo[4,5-b]pyridine-6-carbonitrile | 544.2 | + |
| 600 | 4-((1-(4-(2-(2-amino-4-fluoropyridin-3-yl)-5-(5-fluoropyridin-2-yl)-3H-imidazo[4,5-b]pyridin-3-yl)benzyl)piperidin-4-yl)amino)pyrimidine-2-carbonitrile | 616.2 | +++ |
| 601 | 4-((1-(4-(5-(5-fluoropyridin-2-yl)-2-(pyrimidin-5-yl)-3H-imidazo[4,5-b]pyridin-3-yl)benzyl)piperidin-4-yl)amino)pyrimidine-2-carbonitrile | 584.2 | + |
| 602 | 4-((1-(4-(2-(2-aminopyridin-3-yl)-6-(5-fluoropyridin-2-yl)-1H-benzo[d]imidazol-1-yl)benzyl)piperidin-4-yl)amino)pyrimidine-2-carbonitrile | 596.67 | ++++ |
| 603 | 4-((1-(4-(2-(2-aminopyridin-3-yl)-5-(5-fluoropyrimidin-2-y])-3H-imidazo[4,5-b]pyridin-3-yl)benzyl)piperidin-4-yl)amino)pyrimidine-2-carbonitrile | 599.1 | ++++ |
| 604 | 4-((1-(4-(2-(2-aminopyridin-3-yl)-5-(5-methylpyrimidin-2-yl)-3H-imidazo[4,5-b]pyridin-3-yl)benzyl)piperidin-4-yl)amino)pyrimidine-2-carbonitrile | 595.2 | ++++ |
| 605 | 4-((1-(4-(2-(2-aminopyridin-3-yl)-5-(5-fluoropyrazin-2-yl)-3H-imidazo[4,5-b]pyridin-3-yl)benzyl)piperidin-4-yl)amino)pyrimidine-2-carbonitrile | 599.3 | ++++ |
| 606 | 4-((1-(4-(2-(2-aminopyridin-3-yl)-5-(6-(fluoromethoxy)pyridin-3-yl)-3H-imidazo[4,5-b]pyridin-3-yl)benzyl)piperidin-4-yl)amino)pyrimidine-2-carbonitrile | 628.2 | ++++ |
| 607 | 4-((1-(4-(2-(2-aminopyridin-3-yl)-5-(1-(fluoromethyl)-6-oxo-1,6-dihydropyridin-3-yl)-3H-imidazo[4,5-b]pyridin-3-yl)benzyl)piperidin-4-yl)amino)pyrimidine-2-carbonitrile | 628.2 | +++ |
| 608 | 4-((1-(4-(2-(2-aminopyridin-3-yl)-5-(2-(methyl-d3)-2H-1,2,3-triazol-4-yl)-3H-imidazo[4,5-b]pyridin-3-yl)benzyl)piperidin-4-yl)amino)pyrimidine-2-carbonitrile | 587.2 | ++++ |
| 609 | 4-((1-(4-(2-(2-aminopyridin-3-yl)-5-(2-ethyl-2H-1,2,3-triazol-4-yl)-3H-imidazo[4,5-b]pyridin-3-yl)benzyl)piperidin-4-ylamino)pyrimidine-2-carbonitrile | 620.2 [M + Na]⁺ | ++++ |
| 610 | 4-((1-(4-(2-(2-aminopyridin-3-yl)-5-(2-isopropyl-2H-1,2,3-triazol-4-yl)-3H-imidazo[4,5-b]pyridin-3-yl)benzyl)piperidin-4-yl)amino)pyrimidine-2-carbonitrile | 612.3 | ++++ |
| 611 | 4-((1-(4-(2-(2-aminopyridin-3-yl)-5-(1-isopropyl-1H-1,2,3-triazol-4-yl)-3H-imidazo[4,5-b]pyridin-3-yl)benzyl)piperidin-4-yl)amino)pyrimidine-2-carbonitrile | 612.3 | ++++ |

TABLE 4-continued

| Chemistry Example | Compound Name | MS: [M + H]+ | AKT1 E17K IC50 |
|---|---|---|---|
| 612 | 4-((1-(4-(2-(2-aminopyridin-3-yl)-5-(2-methyl-5-(methyl-d3)-2H-1,2,3-triazol-4-yl)-3H-imidazo[4,5-b]pyridin-3-yl)benzyl)piperidin-4-yl)amino)pyrimidine-2-carbonitrile | 600.71 | ++++ |
| 613 | 4-((1-(4-(2-(2-aminopyridin-3-yl)-5-(2H-1,2,3-triazol-4-yl)-3H-imidazo[4,5-b]pyridin-3-yl)benzyl)piperidin-4-yl)amino)pyrimidine-2-carbonitrile | 570.3 | ++++ |
| 614 | 4-((1-(4-(2-(2-aminopyridin-3-yl)-5-(2,5-dimethyl-2H-1,2,3-triazol-4-yl)-3H-imidazo[4,5-b]pyridin-3-yl)benzyl)piperidin-4-yl)amino)pyrimidine-2-carbonitrile | 597.69 | ++++ |
| 615 | 4-((1-(4-(2-(2-aminopyridin-3-yl)-5-(2-cyclopropyl-2H-1,2,3-triazol-4-yl)-3H-imidazo[4,5-b]pyridin-3-yl)benzyl)piperidin-4-yl)amino)pyrimidine-2-carbonitrile | 610.4 | ++++ |
| 616 | 4-((1-(4-(2-(2-aminopyridin-3-yl)-5-(2-methyl-2H-1,2,3-triazol-4-yl-5-d)-3H-imidazo[4,5-b]pyridin-3-yl)benzyl)piperidin-4-yl)amino)pyrimidine-2-carbonitrile | 585.2 | ++++ |
| 617 | 4-((1-(4-(2-(2-aminopyridin-3-yl)-5-(1-(difluoromethyl)-6-oxo-1,6-dihydropyridin-3-yl)-3H-imidazo[4,5-b]pyridin-3-yl)benzyl)piperidin-4-yl)amino)pyrimidine-2-carbonitrile | 646.0 | +++ |
| 618 | 4-((1-(4-(2-(2-aminopyridin-3-yl)-5-(2-(fluoromethyl)-2H-1,2,3-triazol-4-yl)-3H-imidazo[4,5-b]pyridin-3-yl)benzyl)piperidin-4-yl)amino)pyrimidine-2-carbonitrile | 602.3 | ++++ |
| 619 | 4-((1-(4-(2-(2-aminopyridin-3-yl)-5-(1-(fluoromethyl)-1H-1,2,3-triazol-4-yl)-3H-imidazo[4,5-b]pyridin-3-yl)benzyl)piperidin-4-yl)amino)pyrimidine-2-carbonitrile | 602.2 | ++++ |
| 620 | 4-((1-(4-(2-(2-aminopyridin-3-yl)-5-(2-(difluoromethyl)-2H-1,2,3-triazol-4-yl)-3H-imidazo[4,5-b]pyridin-3-yl)benzyl)piperidin-4-yl)amino)pyrimidine-2-carbonitrile | 620.2 | ++++ |
| 621 | 4-((1-(4-(2-(3-aminopyrazin-2-yl)-5-(2-(methyl-d3)-2H-1,2,3-triazol-4-yl)-3H-imidazo[4,5-b]pyridin-3-yl)benzyl)piperidin-4-yl)amino)pyrimidine-2-carbonitrile | 588.1 | ++++ |
| 622 | 4-((1-(4-(2-(3-aminoisoxazol-4-yl)-5-(5-fluoropyridin-2-yl)-3H-imidazo[4,5-b]pyridin-3-yl)benzyl)piperidin-4-yl)amino)pyrimidine-2-carbonitrile | 588.4 | ++ |
| 623 | 4-((1-(4-(2-(2-aminopyridin-3-yl)-5-(6-(fluoromethoxy-d2)pyridin-3-yl)-3H-imidazo[4,5-b]pyridin-3-yl)benzyl)piperidin-4-yl)amino)pyrimidine-2-carbonitrile | 630.2 | ++++ |
| 624 | 4-((1-(4-(2-(2-aminopyridin-3-yl)-5-(1-(fluoromethyl-d2)-6-oxo-1,6-dihydropyridin-3-yl)-3H-imidazo[4,5-b]pyridin-3-yl)benzyl)piperidin-4-yl)amino)pyrimidine-2-carbonitrile | 630.2 | +++ |
| 625 | 4-((1-(4-(2-(2-aminopyridin-3-yl)-5-(1-ethyl-1H-1,2,3-triazol-4-yl)-3H-imidazo[4,5-b]pyridin-3-yl)benzyl)piperidin-4-yl)amino)pyrimidine-2-carbonitrile | 598.2 | ++++ |
| 626 | 4-((1-(4-(2-(2-aminopyridin-3-yl)-5-(2-(cyanomethyl)-2H-1,2,3-triazol-4-yl)-3H-imidazo[4,5-b]pyridin-3-yl)benzyl)piperidin-4-yl)amino)pyrimidine-2-carbonitrile | 609.4 | ++++ |
| 627 | 4-((1-(4-(2-(3-aminopyrazin-2-yl)-5-(2-(fluoromethyl)-2H-1,2,3-triazol-4-yl)-3H-imidazo[4,5-b]pyridin-3-yl)benzyl)piperidin-4-yl)amino)pyrimidine-2-carbonitrile | 603.2 | ++++ |
| 628 | 4-((1-(4-(2-(3-aminopyrazin-2-yl)-5-(1-(fluoromethyl)-1H-1,2,3-triazol-4-yl)-3H-imidazo[4,5-b]pyridin-3-yl)benzyl)piperidin-4-yl)amino)pyrimidine-2-carbonitrile | 603.3 | ++++ |
| 629 | 4-((1-(4-(2-(3-aminopyrazin-2-yl)-5-(2-ethyl-2H-1,2,3-triazol-4-yl)-3H-imidazo[4,5-b]pyridin-3-yl)benzyl)piperidin-4-yl)amino)pyrimidine-2-carbonitrile | 621.1 [M + Na]+ | ++++ |
| 630 | 4-((1-(4-(2-(3-aminopyrazin-2-yl)-5-(2-isopropyl-2H-1,2,3-triazol-4-yl)-3H-imidazo[4,5-b]pyridin-3-yl)benzyl)piperidin-4-yl)amino)pyrimidine-2-carbonitrile | 613.3 | ++++ |
| 631 | 4-((1-(4-(2-(3-aminopyrazin-2-yl)-5-(2-cyclopropyl-2H-1,2,3-triazol-4-yl)-3H-imidazo[4,5-b]pyridin-3-yl)benzyl)piperidin-4-yl)amino)pyrimidine-2-carbonitrile | 611.1 | ++++ |
| 632 | 4-((1-(4-(2-(3-aminopyrazin-2-yl)-5-(2-(cyanomethyl)-2H-1,2,3-triazol-4-yl)-3H-imidazo[4,5-b]pyridin-3-yl)benzyl)piperidin-4-yl)amino)pyrimidine-2-carbonitrile | 610.3 | ++++ |
| 633 | 2-(4-(2-(3-aminopyrazin-2-yl)-3-(4-((4-((2-cyanopyrimidin-4-yl)amino)piperidin-1-yl)methyl)phenyl)-3H-imidazo[4,5-b]pyridin-5-yl)-2H-1,2,3-triazol-2-yl)acetamide | 628.4 | +++ |
| 634 | 4-((1-(4-(2-(3-aminopyrazin-2-yl)-5-(2-methyl-2H-1,2,3-triazol-4-yl-5-d)-3H-imidazo[4,5-b]pyridin-3-yl)benzyl)piperidin-4-yl)amino)pyrimidine-2-carbonitrile | 586.3 | ++++ |
| 635 | 4-((1-(4-(2-(3-aminopyrazin-2-yl)-5-(2,5-dimethyl-2H-1,2,3-triazol-4-yl)-3H-imidazo[4,5-b]pyridin-3-yl)benzyl)piperidin-4-yl)amino)pyrimidine-2-carbonitrile | 599.3 | +++ |
| 636 | 4-((1-(4-(2-(3-aminopyrazin-2-yl)-5-(6-methoxypyridin-3-yl)-3H-imidazo[4,5-b]pyridin-3-yl)benzyl)piperidin-4-yl)amino)pyrimidine-2-carbonitrile | 611.2 | ++++ |

TABLE 4-continued

| Chemistry Example | Compound Name | MS: [M + H]+ | AKT1 E17K IC50 |
|---|---|---|---|
| 637 | 4-((1-(4-(2-(3-aminopyrazin-2-yl)-5-(6-(methoxy-d3)pyridin-3-yl)-3H-imidazo[4,5-b]pyridin-3-yl)benzyl)piperidin-4-yl)amino)pyrimidine-2-carbonitrile | 614.3 | ++++ |
| 638 | 4-((1-(4-(2-(3-aminopyrazin-2-yl)-5-(5-(methoxy-d3)pyridin-2-yl)-3H-imidazo[4,5-b]pyridin-3-yl)benzyl)piperidin-4-yl)amino)pyrimidine-2-carbonitrile | 614.3 | ++++ |
| 639 | 4-((1-(4-(2-(3-aminopyrazin-2-yl)-5-(6-(fluoromethoxy)pyridin-3-yl)-3H-imidazo[4,5-b]pyridin-3-yl)benzyl)piperidin-4-yl)amino)pyrimidine-2-carbonitrile | 629.2 | ++++ |
| 640 | 4-((1-(4-(2-(3-aminopyrazin-2-yl)-5-(6-(fluoromethoxy-d2)pyridin-3-yl)-3H-imidazo[4,5-b]pyridin-3-yl)benzyl)piperidin-4-yl)amino)pyrimidine-2-carbonitrile | 631.2 | ++++ |
| 641 | 4-((1-(4-(2-(2-aminopyridin-3-yl)-5-(6-cyclopropoxypyridin-3-yl)-3H-imidazo[4,5-b]pyridin-3-yl)benzyl)piperidin-4-yl)amino)pyrimidine-2-carbonitrile | 658.2 [M + Na]+ | ++++ |
| 642 | 4-((1-(4-(2-(2-aminopyridin-3-yl)-5-(6-isopropoxypyridin-3-yl)-3H-imidazo[4,5-b]pyridin-3-yl)benzyl)piperidin-4-yl)amino)pyrimidine-2-carbonitrile | 660.2 [M + Na]+ | ++++ |
| 643 | 4-((1-(4-(2-(2-aminopyridin-3-yl)-5-(6-isopropylpyridin-3-yl)-3H-imidazo[4,5-b]pyridin-3-yl)benzyl)piperidin-4-yl)amino)pyrimidine-2-carbonitrile | 622.3 | ++++ |
| 644 | 4-((1-(4-(2-(2-aminopyridin-3-yl)-5-(5-cyclopropylpyridin-2-yl)-3H-imidazo[4,5-b]pyridin-3-yl)benzyl)piperidin-4-yl)amino)pyrimidine-2-carbonitrile | 620.3 | ++++ |
| 645 | 4-((1-(4-(2-(2-aminopyridin-3-yl)-5-(6-(difluoromethyl)pyridin-3-yl)-3H-imidazo[4,5-b]pyridin-3-yl)benzyl)piperidin-4-yl)amino)pyrimidine-2-carbonitrile | 630.2 | ++++ |
| 646 | 4-((1-(4-(2-(2-aminopyridin-3-yl)-5-(6-(trifluoromethyl)pyridin-3-yl)-3H-imidazo[4,5-b]pyridin-3-yl)benzyl)piperidin-4-yl)amino)pyrimidine-2-carbonitrile | 648.2 | ++++ |
| 647 | 4-((1-(4-(2-(2-aminopyridin-3-yl)-5-(5-ethylpyridin-2-yl)-3H-imidazo[4,5-b]pyridin-3-yl)benzyl)piperidin-4-yl)amino)pyrimidine-2-carbonitrile | 608.3 | ++++ |
| 648 | 4-((1-(4-(2-(2-aminopyridin-3-yl)-5-(5-(fluoromethyl)pyridin-2-yl)-3H-imidazo[4,5-b]pyridin-3-yl)benzyl)piperidin-4-yl)amino)pyrimidine-2-carbonitrile | 612.3 | ++++ |
| 649 | 4-((1-(4-(2-(2-aminopyridin-3-yl)-5-(5-(difluoromethyl)pyridin-2-yl)-3H-imidazo[4,5-b]pyridin-3-yl)benzyl)piperidin-4-yl)amino)pyrimidine-2-carbonitrile | 630.3 | ++++ |
| 650 | 4-((1-(4-(2-(2-aminopyridin-3-yl)-5-(5-(trifluoromethyl)pyridin-2-yl)-3H-imidazo[4,5-b]pyridin-3-yl)benzyl)piperidin-4-yl)amino)pyrimidine-2-carbonitrile | 648.6 | +++ |

III. Preparation of Pharmaceutical Dosage Forms

Example 1: Oral Capsule

The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2. Solution for Injection

The active ingredient is a compound of Table 1, or a pharmaceutically acceptable salt or solvate thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

We claim:

1. A compound, or pharmaceutically acceptable salt or solvate thereof, selected from the group consisting of:

- 6-((1-(4-(2-(2-aminopyridin-3-yl)-3H-imidazo[4,5-b]pyridin-3-yl)benzyl)piperidin-4-yl)oxy)nicotinonitrile;
- 6-((1-(4-(2-(2-aminopyridin-3-yl)-5-phenyl-3H-imidazo[4,5-b]pyridin-3-yl)benzyl)piperidin-4-yl)oxy)nicotinonitrile;
- 6-((1-(4-(2-(2-aminopyridin-3-yl)-6-phenyl-3H-imidazo[4,5-b]pyridin-3-yl)benzyl)piperidin-4-yl)oxy)nicotinonitrile;
- 6-((1-(4-(2-(2-aminopyridin-3-yl)-3H-imidazo[4,5-b]pyridin-3-yl)benzyl)piperidin-4-yl)oxy)picolinonitrile;
- 2-((1-(4-(2-(2-aminopyridin-3-yl)-3H-imidazo[4,5-b]pyridin-3-yl)benzyl)piperidin-4-yl)oxy)isonicotinonitrile;
- 2-((1-(4-(2-(2-aminopyridin-3-yl)-3H-imidazo[4,5-b]pyridin-3-yl)benzyl)piperidin-4-yl)oxy)nicotinonitrile;
- 6-((1-(4-(2-(2-aminopyridin-3-yl)-5-phenyl-3H-imidazo[4,5-b]pyridin-3-yl)benzyl)piperidin-4-yl)oxy)picolinonitrile;
- 2-((1-(4-(2-(2-aminopyridin-3-yl)-5-phenyl-3H-imidazo[4,5-b]pyridin-3-yl)benzyl)piperidin-4-yl)oxy)isonicotinonitrile;
- 2-((1-(4-(2-(2-aminopyridin-3-yl)-5-phenyl-3H-imidazo[4,5-b]pyridin-3-yl)benzyl)piperidin-4-yl)oxy)nicotinonitrile;
- 6-((1-(4-(2-(2-aminopyridin-3-yl)-6-phenyl-3H-imidazo[4,5-b]pyridin-3-yl)benzyl)piperidin-4-yl)oxy)picolinonitrile;
- 2-((1-(4-(2-(2-aminopyridin-3-yl)-6-phenyl-3H-imidazo[4,5-b]pyridin-3-yl)benzyl)piperidin-4-yl)oxy)isonicotinonitrile;
- 2-((1-(4-(2-(2-aminopyridin-3-yl)-6-phenyl-3H-imidazo[4,5-b]pyridin-3-yl)benzyl)piperidin-4-yl)oxy)nicotinonitrile;
- 4-(4-(4-(2-(2-aminopyridin-3-yl)-3H-imidazo[4,5-b]pyridin-3-yl)benzyl)piperazin-1-yl)picolinonitrile;
- 5-(4-(4-(2-(2-aminopyridin-3-yl)-3H-imidazo[4,5-b]pyridin-3-yl)benzyl)piperazin-1-yl)picolinonitrile;
- 6-(4-(4-(2-(2-aminopyridin-3-yl)-3H-imidazo[4,5-b]pyridin-3-yl)benzyl)piperazin-1-yl)picolinonitrile;
- 5-(4-(4-(2-(2-aminopyridin-3-yl)-3H-imidazo[4,5-b]pyridin-3-yl)benzyl)piperazin-1-yl)nicotinonitrile;
- 2-(4-(4-(2-(2-aminopyridin-3-yl)-3H-imidazo[4,5-b]pyridin-3-yl)benzyl)piperazin-1-yl)isonicotinonitrile;
- 4-(4-(4-(2-(2-aminopyridin-3-yl)-3H-imidazo[4,5-b]pyridin-3-yl)benzyl)piperazin-1-yl)pyrimidine-2-carbonitrile;
- 6-(4-(4-(2-(2-aminopyridin-3-yl)-3H-imidazo[4,5-b]pyridin-3-yl)benzyl)piperazin-1-yl)pyrazine-2-carbonitrile;
- 2-(4-(4-(2-(2-aminopyridin-3-yl)-3H-imidazo[4,5-b]pyridin-3-yl)benzyl)piperazin-1-yl)pyrimidine-4-carbonitrile;
- 6-(4-(4-(2-(2-aminopyridin-3-yl)-3H-imidazo[4,5-b]pyridin-3-yl)benzyl)piperazin-1-yl)pyrimidine-4-carbonitrile;
- 6-(4-(4-(2-(2-aminopyridin-3-yl)-3H-imidazo[4,5-b]pyridin-3-yl)benzyl)piperazin-1-yl)pyridazine-4-carbonitrile;
- N-(1-(4-(2-(2-aminopyridin-3-yl)-3H-imidazo[4,5-b]pyridin-3-yl)benzyl)piperidin-4-yl)-2-cyanoisonicotinamide;
- N-(1-(4-(2-(2-aminopyridin-3-yl)-3H-imidazo[4,5-b]pyridin-3-yl)benzyl)piperidin-4-yl)-6-cyanonicotinamide;
- N-(1-(4-(2-(2-aminopyridin-3-yl)-3H-imidazo[4,5-b]pyridin-3-yl)benzyl)piperidin-4-yl)-5-cyanopicolinamide;
- N-(1-(4-(2-(2-aminopyridin-3-yl)-3H-imidazo[4,5-b]pyridin-3-yl)benzyl)piperidin-4-yl)-5-cyanonicotinamide;
- N-(1-(4-(2-(2-aminopyridin-3-yl)-3H-imidazo[4,5-b]pyridin-3-yl)benzyl)piperidin-4-yl)-2-cyanonicotinamide;
- N-(1-(4-(2-(2-aminopyridin-3-yl)-3H-imidazo[4,5-b]pyridin-3-yl)benzyl)piperidin-4-yl)-3-cyanopicolinamide;
- N-(1-(4-(2-(2-aminopyridin-3-yl)-3H-imidazo[4,5-b]pyridin-3-yl)benzyl)piperidin-4-yl)-4-cyanonicotinamide;
- N-(1-(4-(2-(2-aminopyridin-3-yl)-3H-imidazo[4,5-b]pyridin-3-yl)benzyl)piperidin-4-yl)-6-cyanopicolinamide;
- N-(1-(4-(2-(2-aminopyridin-3-yl)-3H-imidazo[4,5-b]pyridin-3-yl)benzyl)piperidin-4-yl)-4-cyanopicolinamide;
- N-(1-(4-(2-(2-aminopyridin-3-yl)-3H-imidazo[4,5-b]pyridin-3-yl)benzyl)piperidin-4-yl)-2-cyanopyrimidine-4-carboxamide;
- N-(1-(4-(2-(2-aminopyridin-3-yl)-3H-imidazo[4,5-b]pyridin-3-yl)benzyl)piperidin-4-yl)-6-cyanopyrimidine-4-carboxamide;
- N-(1-(4-(2-(2-aminopyridin-3-yl)-3H-imidazo[4,5-b]pyridin-3-yl)benzyl)piperidin-4-yl)-2-cyanobenzo[d]thiazole-5-carboxamide;
- N-(1-(4-(2-(2-aminopyridin-3-yl)-3H-imidazo[4,5-b]pyridin-3-yl)benzyl)piperidin-4-yl)-2-cyano-5-fluorobenzo[d]thiazole-7-carboxamide;
- N-(1-(4-(2-(2-aminopyridin-3-yl)-3H-imidazo[4,5-b]pyridin-3-yl)benzyl)piperidin-4-yl)-3-cyanoisonicotinamide;
- N-(3-(2-(2-aminopyridin-3-yl)-3-(4-((4-(2-cyanopyridin-4-yl)piperazin-1-yl)methyl)phenyl)-3H-imidazo[4,5-b]pyridin-5-yl)phenyl)acetamide;
- N-(3-(2-(2-aminopyridin-3-yl)-3-(4-((4-(6-cyanopyridin-3-yl)piperazin-1-yl)methyl)phenyl)-3H-imidazo[4,5-b]pyridin-5-yl)phenyl)acetamide;
- N-(3-(2-(2-aminopyridin-3-yl)-3-(4-((4-(6-cyanopyridin-2-yl)piperazin-1-yl)methyl)phenyl)-3H-imidazo[4,5-b]pyridin-5-yl)phenyl)acetamide;
- N-(3-(2-(2-aminopyridin-3-yl)-3-(4-((4-(6-cyanopyrazin-2-yl)piperazin-1-yl)methyl)phenyl)-3H-imidazo[4,5-b]pyridin-5-yl)phenyl)acetamide;
- N-(3-(2-(2-aminopyridin-3-yl)-3-(4-((4-(6-cyanopyrimidin-4-yl)piperazin-1-yl)methyl)phenyl)-3H-imidazo[4,5-b]pyridin-5-yl)phenyl)acetamide;

N-(3-(2-(2-aminopyridin-3-yl)-3-(4-((4-(2-cyanopyrimidin-5-yl)piperazin-1-yl)methyl)phenyl)-3H-imidazo[4,5-b]pyridin-5-yl)phenyl)acetamide;

N-(3-(2-(2-aminopyridin-3-yl)-3-(4-((4-(6-cyanopyridazin-4-yl)piperazin-1-yl)methyl)phenyl)-3H-imidazo[4,5-b]pyridin-5-yl)phenyl)acetamide;

N-(3-(2-(2-aminopyridin-3-yl)-3-(4-((4-(2-cyanopyrimidin-4-yl)piperazin-1-yl)methyl)phenyl)-3H-imidazo[4,5-b]pyridin-5-yl)phenyl)acetamide;

N-(3-(2-(2-aminopyridin-3-yl)-3-(4-((4-(5-cyanopyridazin-3-yl)piperazin-1-yl)methyl)phenyl)-3H-imidazo[4,5-b]pyridin-5-yl)phenyl)acetamide;

N-(3-(2-(2-aminopyridin-3-yl)-3-(4-((4-(4-cyanopyrimidin-2-yl)piperazin-1-yl)methyl)phenyl)-3H-imidazo[4,5-b]pyridin-5-yl)phenyl)acetamide;

4-(4-(4-(2-(2-aminopyridin-3-yl)-5-phenyl-3H-imidazo[4,5-b]pyridin-3-yl)benzyl)piperazin-1-yl)pyrimidine-2-carbonitrile;

6-((1-(4-(2-(2-aminopyridin-3-yl)-3H-imidazo[4,5-b]pyridin-3-yl)benzyl)piperidin-4-yl)amino)pyridazine-4-carbonitrile;

6-(4-(4-(2-(2-aminopyridin-3-yl)-5-phenyl-3H-imidazo[4,5-b]pyridin-3-yl)benzyl)piperazin-1-yl)pyridazine-4-carbonitrile;

6-((1-(4-(2-(2-aminopyridin-3-yl)-5-phenyl-3H-imidazo[4,5-b]pyridin-3-yl)benzyl)piperidin-4-yl)amino)pyridazine-4-carbonitrile;

N-(1-(4-(2-(2-aminopyridin-3-yl)-5-phenyl-3H-imidazo[4,5-b]pyridin-3-yl)benzyl)piperidin-4-yl)-2-cyanoisonicotinamide;

N-(1-(4-(2-(2-aminopyridin-3-yl)-5-phenyl-3H-imidazo[4,5-b]pyridin-3-yl)benzyl)piperidin-4-yl)-6-cyanopicolinamide;

N-(1-(4-(2-(2-aminopyridin-3-yl)-5-phenyl-3H-imidazo[4,5-b]pyridin-3-yl)benzyl)piperidin-4-yl)-5-cyanonicotinamide;

N-(1-(4-(2-(2-aminopyridin-3-yl)-5-phenyl-3H-imidazo[4,5-b]pyridin-3-yl)benzyl)piperidin-4-yl)-2-cyanonicotinamide;

N-(1-(4-(2-(2-aminopyridin-3-yl)-5-phenyl-3H-imidazo[4,5-b]pyridin-3-yl)benzyl)piperidin-4-yl)-3-cyanoisonicotinamide;

N-(1-(4-(2-(2-aminopyridin-3-yl)-5-phenyl-3H-imidazo[4,5-b]pyridin-3-yl)benzyl)piperidin-4-yl)-4-cyanonicotinamide;

N-(1-(4-(2-(2-aminopyridin-3-yl)-5-phenyl-3H-imidazo[4,5-b]pyridin-3-yl)benzyl)piperidin-4-yl)-3-cyanopicolinamide;

4-((1-(4-(2-(2-aminopyridin-3-yl)-3H-imidazo[4,5-b]pyridin-3-yl)benzyl)piperidin-4-yl)amino)picolinonitrile;

6-((1-(4-(2-(2-aminopyridin-3-yl)-3H-imidazo[4,5-b]pyridin-3-yl)benzyl)piperidin-4-yl)amino)picolinonitrile;

6-((1-(4-(2-(2-aminopyridin-3-yl)-3H-imidazo[4,5-b]pyridin-3-yl)benzyl)piperidin-4-yl)amino)pyrimidine-4-carbonitrile;

5-(4-(4-(2-(2-aminopyridin-3-yl)-5-phenyl-3H-imidazo[4,5-b]pyridin-3-yl)benzyl)piperazin-1-yl)nicotinonitrile;

2-(4-(4-(2-(2-aminopyridin-3-yl)-5-phenyl-3H-imidazo[4,5-b]pyridin-3-yl)benzyl)piperazin-1-yl)isonicotinonitrile;

6-(4-(4-(2-(2-aminopyridin-3-yl)-5-phenyl-3H-imidazo[4,5-b]pyridin-3-yl)benzyl)piperazin-1-yl)pyrazine-2-carbonitrile;

2-(4-(4-(2-(2-aminopyridin-3-yl)-5-phenyl-3H-imidazo[4,5-b]pyridin-3-yl)benzyl)piperazin-1-yl)pyrimidine-4-carbonitrile;

6-(4-(4-(2-(2-aminopyridin-3-yl)-3H-imidazo[4,5-b]pyridin-3-yl)benzyl)piperazine-1-carbonyl)picolinonitrile;

4-(4-(4-(2-(2-aminopyridin-3-yl)-5-phenyl-3H-imidazo[4,5-b]pyridin-3-yl)benzyl)piperazine-1-carbonyl)pyridazine-3-carbonitrile;

N-(1-(4-(2-(2-aminopyridin-3-yl)-5-phenyl-3H-imidazo[4,5-b]pyridin-3-yl)benzyl)piperidin-4-yl)-3-cyanopyridazine-4-carboxamide;

4-(4-(4-(2-(2-aminopyridin-3-yl)-5-phenyl-3H-imidazo[4,5-b]pyridin-3-yl)benzyl)piperazine-1-carbonyl)pyrimidine-5-carbonitrile;

N-(1-(4-(2-(2-aminopyridin-3-yl)-5-phenyl-3H-imidazo[4,5-b]pyridin-3-yl)benzyl)piperidin-4-yl)-5-cyanopyrimidine-4-carboxamide;

5-((1-(4-(2-(2-aminopyridin-3-yl)-3H-imidazo[4,5-b]pyridin-3-yl)benzyl)piperidin-4-yl)amino)nicotinonitrile;

2-((1-(4-(2-(2-aminopyridin-3-yl)-3H-imidazo[4,5-b]pyridin-3-yl)benzyl)piperidin-4-yl)amino)isonicotinonitrile;

6-((1-(4-(2-(2-aminopyridin-3-yl)-3H-imidazo[4,5-b]pyridin-3-yl)benzyl)piperidin-4-yl)amino)pyrazine-2-carbonitrile;

2-((1-(4-(2-(2-aminopyridin-3-yl)-3H-imidazo[4,5-b]pyridin-3-yl)benzyl)piperidin-4-yl)amino)pyrimidine-4-carbonitrile;

6-(4-(4-(2-(2-aminopyridin-3-yl)-5-phenyl-3H-imidazo[4,5-b]pyridin-3-yl)benzyl)piperazin-1-yl)pyrimidine-4-carbonitrile;

5-(4-(4-(2-(2-aminopyridin-3-yl)-3H-imidazo[4,5-b]pyridin-3-yl)benzyl)piperazine-1-carbonyl)nicotinonitrile;

6-(4-(4-(2-(2-aminopyridin-3-yl)-3H-imidazo[4,5-b]pyridin-3-yl)benzyl)piperazine-1-carbonyl)nicotinonitrile;

N-(1-(4-(2-(2-aminopyridin-3-yl)-5-phenyl-3H-imidazo[4,5-b]pyridin-3-yl)benzyl)piperidin-4-yl)-5-cyanopicolinamide;

4-(4-(4-(2-(2-aminopyridin-3-yl)-5-phenyl-3H-imidazo[4,5-b]pyridin-3-yl)benzyl)piperazin-1-yl)picolinonitrile;

6-(4-(4-(2-(2-aminopyridin-3-yl)-5-phenyl-3H-imidazo[4,5-b]pyridin-3-yl)benzyl)piperazin-1-yl)picolinonitrile;

5-((1-(4-(2-(2-aminopyridin-3-yl)-5-phenyl-3H-imidazo[4,5-b]pyridin-3-yl)benzyl)piperidin-4-yl)amino)picolinonitrile;

4-((1-(4-(2-(2-aminopyridin-3-yl)-5-phenyl-3H-imidazo[4,5-b]pyridin-3-yl)benzyl)piperidin-4-yl)amino)picolinonitrile;

6-((1-(4-(2-(2-aminopyridin-3-yl)-5-phenyl-3H-imidazo[4,5-b]pyridin-3-yl)benzyl)piperidin-4-yl)amino)picolinonitrile;

2-((1-(4-(2-(2-aminopyridin-3-yl)-5-phenyl-3H-imidazo[4,5-b]pyridin-3-yl)benzyl)piperidin-4-yl)amino)isonicotinonitrile;

4-((1-(4-(2-(2-aminopyridin-3-yl)-5-phenyl-3H-imidazo[4,5-b]pyridin-3-yl)benzyl)piperidin-4-yl)amino)pyrimidine-2-carbonitrile;

6-((1-(4-(2-(2-aminopyridin-3-yl)-5-phenyl-3H-imidazo[4,5-b]pyridin-3-yl)benzyl)piperidin-4-yl)amino)pyrazine-2-carbonitrile;

2-((1-(4-(2-(2-aminopyridin-3-yl)-5-phenyl-3H-imidazo[4,5-b]pyridin-3-yl)benzyl)piperidin-4-yl)amino)pyrimidine-4-carbonitrile;

6-((1-(4-(2-(2-aminopyridin-3-yl)-5-phenyl-3H-imidazo[4,5-b]pyridin-3-yl)benzyl)piperidin-4-yl)amino)pyrimidine-4-carbonitrile;

4-((1-(4-(2-(2-aminopyridin-3-yl)-3H-imidazo[4,5-b]pyridin-3-yl)benzyl)piperidin-4-yl)amino)pyrimidine-2-carbonitrile;

5-((1-(4-(2-(2-aminopyridin-3-yl)-5-phenyl-3H-imidazo[4,5-b]pyridin-3-yl)benzyl)piperidin-4-yl)amino)nicotinonitrile;

5-(4-(4-(2-(2-aminopyridin-3-yl)-5-phenyl-3H-imidazo[4,5-b]pyridin-3-yl)benzyl)piperazin-1-yl)picolinonitrile;

5-(4-(4-(2-(2-aminopyridin-3-yl)-5-phenyl-3H-imidazo[4,5-b]pyridin-3-yl)benzyl)piperazin-1-yl)pyrimidine-2-carbonitrile;

5-(4-(4-(2-(2-aminopyridin-3-yl)-3H-imidazo[4,5-b]pyridin-3-yl)benzyl)piperazine-1-carbonyl)picolinonitrile;

N-(1-(4-(2-(2-aminopyridin-3-yl)-6-phenyl-3H-imidazo[4,5-b]pyridin-3-yl)benzyl)piperidin-4-yl)-2-cyanoisonicotinamide;

4-(4-(4-(2-(2-aminopyridin-3-yl)-3H-imidazo[4,5-b]pyridin-3-yl)benzyl)piperazine-1-carbonyl)picolinonitrile;

2-(4-(4-(2-(2-aminopyridin-3-yl)-3H-imidazo[4,5-b]pyridin-3-yl)benzyl)piperazine-1-carbonyl)nicotinonitrile;

5-(4-(4-(2-(2-aminopyridin-3-yl)-6-phenyl-3H-imidazo[4,5-b]pyridin-3-yl)benzyl)piperazine-1-carbonyl)picolinonitrile;

6-(4-(4-(2-(2-aminopyridin-3-yl)-3H-imidazo[4,5-b]pyridin-3-yl)benzyl)piperazine-1-carbonyl)pyrimidine-4-carbonitrile;

6-(4-(4-(2-(2-aminopyridin-3-yl)-5-phenyl-3H-imidazo[4,5-b]pyridin-3-yl)benzyl)piperazine-1-carbonyl)pyrimidine-4-carbonitrile;

N-(1-(4-(2-(2-aminopyridin-3-yl)-5-phenyl-3H-imidazo[4,5-b]pyridin-3-yl)benzyl)piperidin-4-yl)-6-cyanopyrimidine-4-carboxamide;

4-(4-(4-(2-(2-aminopyridin-3-yl)-6-phenyl-3H-imidazo[4,5-b]pyridin-3-yl)benzyl)piperazine-1-carbonyl)picolinonitrile;

6-(4-(4-(2-(2-aminopyridin-3-yl)-5-phenyl-3H-imidazo[4,5-b]pyridin-3-yl)benzyl)piperazine-1-carbonyl)picolinonitrile;

5-(4-(4-(2-(2-aminopyridin-3-yl)-5-phenyl-3H-imidazo[4,5-b]pyridin-3-yl)benzyl)piperazine-1-carbonyl)nicotinonitrile;

2-(4-(4-(2-(2-aminopyridin-3-yl)-5-phenyl-3H-imidazo[4,5-b]pyridin-3-yl)benzyl)piperazine-1-carbonyl)isonicotinonitrile;

4-(4-(4-(2-(2-aminopyridin-3-yl)-5-phenyl-3H-imidazo[4,5-b]pyridin-3-yl)benzyl)piperazine-1-carbonyl)pyrimidine-2-carbonitrile;

6-(4-(4-(2-(2-aminopyridin-3-yl)-5-phenyl-3H-imidazo[4,5-b]pyridin-3-yl)benzyl)piperazine-1-carbonyl)nicotinonitrile;

3-(4-(4-(2-(2-aminopyridin-3-yl)-5-phenyl-3H-imidazo[4,5-b]pyridin-3-yl)benzyl)piperazine-1-carbonyl)picolinonitrile;

4-(4-(4-(2-(2-aminopyridin-3-yl)-5-phenyl-3H-imidazo[4,5-b]pyridin-3-yl)benzyl)piperazine-1-carbonyl)nicotinonitrile;

3-(4-(4-(2-(2-aminopyridin-3-yl)-5-phenyl-3H-imidazo[4,5-b]pyridin-3-yl)benzyl)piperazine-1-carbonyl)isonicotinonitrile;

2-(4-(4-(2-(2-aminopyridin-3-yl)-5-phenyl-3H-imidazo[4,5-b]pyridin-3-yl)benzyl)piperazine-1-carbonyl)nicotinonitrile;

2-(4-(4-(2-(2-aminopyridin-3-yl)-3H-imidazo[4,5-b]pyridin-3-yl)benzyl)piperazine-1-carbonyl)isonicotinonitrile;

N-(1-(4-(2-(2-aminopyridin-3-yl)-5-phenyl-3H-imidazo[4,5-b]pyridin-3-yl)benzyl)piperidin-4-yl)-4-cyanopicolinamide;

N-(1-(4-(2-(2-aminopyridin-3-yl)-5-phenyl-3H-imidazo[4,5-b]pyridin-3-yl)benzyl)piperidin-4-yl)-2-cyanopyrimidine-4-carboxamide;

4-(4-(4-(2-(2-aminopyridin-3-yl)-3H-imidazo[4,5-b]pyridin-3-yl)benzyl)piperazine-1-carbonyl)pyrimidine-2-carbonitrile;

3-(4-(4-(2-(2-aminopyridin-3-yl)-3H-imidazo[4,5-b]pyridin-3-yl)benzyl)piperazine-1-carbonyl)picolinonitrile;

4-(4-(4-(2-(2-aminopyridin-3-yl)-3H-imidazo[4,5-b]pyridin-3-yl)benzyl)piperazine-1-carbonyl)nicotinonitrile;

3-(4-(4-(2-(2-aminopyridin-3-yl)-3H-imidazo[4,5-b]pyridin-3-yl)benzyl)piperazine-1-carbonyl)isonicotinonitrile;

4-((1-(4-(2-(2-aminopyridin-3-yl)-5-phenyl-3H-imidazo[4,5-b]pyridin-3-yl)benzyl)piperidin-4-yl)(methyl)amino)pyrimidine-2-carbonitrile;

5-((1-(4-(2-(2-aminopyridin-3-yl)-3H-imidazo[4,5-b]pyridin-3-yl)benzyl)piperidin-4-yl)amino)picolinonitrile;

5-((1-(4-(2-(2-aminopyridin-3-yl)-5-phenyl-3H-imidazo[4,5-b]pyridin-3-yl)benzyl)piperidin-4-yl)amino)pyridazine-3-carbonitrile;

5-(4-(4-(2-(2-aminopyridin-3-yl)-5-phenyl-3H-imidazo[4,5-b]pyridin-3-yl)benzyl)piperazin-1-yl)pyridazine-3-carbonitrile;

3-(4-(4-(2-(2-aminopyridin-3-yl)-5-phenyl-3H-imidazo[4,5-b]pyridin-3-yl)benzyl)piperazine-1-carbonyl)pyrazine-2-carbonitrile;

3-(4-(4-(2-(2-aminopyridin-3-yl)-3H-imidazo[4,5-b]pyridin-3-yl)benzyl)piperazine-1-carbonyl)pyrazine-2-carbonitrile;

N-(1-(4-(2-(2-aminopyridin-3-yl)-6-phenyl-3H-imidazo[4,5-b]pyridin-3-yl)benzyl)piperidin-4-yl)-6-cyanonicotinamide;

5-(4-(4-(2-(2-aminopyridin-3-yl)-5-phenyl-3H-imidazo[4,5-b]pyridin-3-yl)benzyl)piperazine-1-carbonyl)picolinonitrile;

N-(1-(4-(2-(2-aminopyridin-3-yl)-5-phenyl-3H-imidazo[4,5-b]pyridin-3-yl)benzyl)piperidin-4-yl)-6-cyanonicotinamide;

4-(4-(4-(2-(2-aminopyridin-3-yl)-5-phenyl-3H-imidazo[4,5-b]pyridin-3-yl)benzyl)piperazine-1-carbonyl)picolinonitrile;

7-(4-(4-(2-(2-aminopyridin-3-yl)-3H-imidazo[4,5-b]pyridin-3-yl)benzyl)piperazine-1-carbonyl)-5-fluorobenzo[d]thiazole-2-carbonitrile;

7-(4-(4-(2-(2-aminopyridin-3-yl)-5-phenyl-3H-imidazo[4,5-b]pyridin-3-yl)benzyl)piperazine-1-carbonyl)-5-fluorobenzo[d]thiazole-2-carbonitrile;

4-(4-(4-(2-(2-aminopyridin-3-yl)-5-phenyl-3H-imidazo[4,5-b]pyridin-3-yl)benzyl)piperazine-1-carbonyl)-6-fluorobenzo[d]thiazole-2-carbonitrile;

N-(1-(4-(2-(2-aminopyridin-3-yl)-5-phenyl-3H-imidazo[4,5-b]pyridin-3-yl)benzyl)piperidin-4-yl)-2-cyano-5-fluorobenzo[d]thiazole-7-carboxamide;

N-(1-(4-(2-(2-aminopyridin-3-yl)-5-phenyl-3H-imidazo[4,5-b]pyridin-3-yl)benzyl)piperidin-4-yl)-2-cyano-6-fluorobenzo[d]thiazole-4-carboxamide;

5-(4-(4-(2-(2-aminopyridin-3-yl)-5-phenyl-3H-imidazo[4,5-b]pyridin-3-yl)benzyl)piperazine-1-carbonyl)benzo[d]thiazole-2-carbonitrile;

N-(1-(4-(2-(2-aminopyridin-3-yl)-5-phenyl-3H-imidazo[4,5-b]pyridin-3-yl)benzyl)piperidin-4-yl)-2-cyanobenzo[d]thiazole-5-carboxamide;

4-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile;

2-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile;

6-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile;

4-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile;

2-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile;

6-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile;

4-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-2-carbonitrile;

2-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-4-carbonitrile;

6-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-4-carbonitrile;

4-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-2-carbonitrile;

6-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-4-carbonitrile;

4-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-2-carbonitrile;

2-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-4-carbonitrile;

6-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-4-carbonitrile;

(S)-4-(4-(4-(2-(2-aminopyridin-3-yl)-5-phenyl-3H-imidazo[4,5-b]pyridin-3-yl)benzyl)-2-methylpiperazin-1-yl)pyrimidine-2-carbonitrile;

(S)-2-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile;

(S)-6-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile;

4-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-2-carbonitrile;

2-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-4-carbonitrile;

6-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-4-carbonitrile;

4-(4-(4-(2-(2-aminopyridin-3-yl)-5-phenyl-3H-imidazo[4,5-b]pyridin-3-yl)benzyl)-1,4-diazepan-1-yl)pyrimidine-2-carbonitrile;

6-(4-(4-(2-(2-aminopyridin-3-yl)-5-phenyl-3H-imidazo[4,5-b]pyridin-3-yl)benzyl)-1,4-diazepan-1-yl)pyrimidine-4-carbonitrile;

4-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-2-carbonitrile;

2-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile;

6-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile;

4-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-2-carbonitrile;

2-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-4-carbonitrile;

6-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-4-carbonitrile;

4-((1-((4-(2-(2-aminopyridin-3-yl)-5-phenyl-3H-imidazo[4,5-b]pyridin-3-yl)phenyl)methyl-d2)piperidin-4-yl)amino)pyrimidine-2-carbonitrile;

4-((1-(4-(2-(2-aminopyridin-3-yl)-5-phenyl-3H-imidazo[4,5-b]pyridin-3-yl)benzyl)piperidin-4-yl)(methyl)amino)-1,3,5-triazine-2-carbonitrile;

(S)-4-((1-(4-(2-(2-aminopyridin-3-yl)-5-phenyl-3H-imidazo[4,5-b]pyridin-3-yl)benzyl)piperidin-3-yl)amino)-1,3,5-triazine-2-carbonitrile;

(R)-4-(4-(4-(2-(2-aminopyridin-3-yl)-5-phenyl-3H-imidazo[4,5-b]pyridin-3-yl)benzyl)-2-methylpiperazin-1-yl)pyrimidine-2-carbonitrile;

(R)-2-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile;

(R)-6-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile;

2-(4-(4-(2-(2-aminopyridin-3-yl)-5-phenyl-3H-imidazo[4,5-b]pyridin-3-yl)benzyl)-1,4-diazepan-1-yl)pyrimidine-4-carbonitrile;

N-(3-(4-(2-(2-aminopyridin-3-yl)-5-phenyl-3H-imidazo[4,5-b]pyridin-3-yl)benzyl)-3-azabicyclo[3.2.1]octan-8-yl)-2-cyanopyrimidine-4-carboxamide;

N-(3-(4-(2-(2-aminopyridin-3-yl)-5-phenyl-3H-imidazo[4,5-b]pyridin-3-yl)benzyl)-3-azabicyclo[3.2.1]octan-8-yl)-6-cyanopyrimidine-4-carboxamide;

2-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-4-carbonitrile;

4-((1-(4-(2-(2-aminopyridin-3-yl)-5-phenyl-3H-imidazo[4,5-b]pyridin-3-yl)benzyl)piperidin-4-yl)(methyl-d3)amino)pyrimidine-2-carbonitrile;

4-((1-(4-(2-(2-aminopyridin-3-yl)-5-phenyl-3H-imidazo[4,5-b]pyridin-3-yl)benzyl)piperidin-4-yl)(methyl-d3)amino)-1,3,5-triazine-2-carbonitrile;

N-(1-(4-(2-(2-aminopyridin-3-yl)-5-phenyl-3H-imidazo[4,5-b]pyridin-3-yl)benzyl)piperidin-4-yl)-2-cyano-N-(methyl-d3)pyrimidine-4-carboxamide;

4-(4-(4-(2-(2-aminopyridin-3-yl)-5-morpholino-3H-imidazo[4,5-b]pyridin-3-yl)benzyl)piperazin-1-yl)pyrimidine-2-carbonitrile;

2-(4-(4-(2-(2-aminopyridin-3-yl)-5-morpholino-3H-imidazo[4,5-b]pyridin-3-yl)benzyl)piperazin-1-yl)pyrimidine-4-carbonitrile;

6-(4-(4-(2-(2-aminopyridin-3-yl)-5-morpholino-3H-imidazo[4,5-b]pyridin-3-yl)benzyl)piperazin-1-yl)pyrimidine-4-carbonitrile;

4-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-morpholino-3H-imidazo[4,5-b]pyridin-3-yl)benzyl)piperidin-4-yl)amino)pyrimidine-2-carbonitrile;

2-((1-(4-(2-(2-aminopyridin-3-yl)-5-morpholino-3H-imidazo[4,5-b]pyridin-3-yl)benzyl)piperidin-4-yl)amino)pyrimidine-4-carbonitrile;

6-((1-(4-(2-(2-aminopyridin-3-yl)-5-morpholino-3H-imidazo[4,5-b]pyridin-3-yl)benzyl)piperidin-4-yl)amino)pyrimidine-4-carbonitrile;

4-(4-(4-(2-(2-aminopyridin-3-yl)-5-(4-fluorophenyl)-3H-imidazo[4,5-b]pyridin-3-yl)benzyl)piperazin-1-yl)pyrimidine-2-carbonitrile;

2-(4-(4-(2-(2-aminopyridin-3-yl)-5-(4-fluorophenyl)-3H-imidazo[4,5-b]pyridin-3-yl)benzyl)piperazin-1-yl)pyrimidine-4-carbonitrile;

4-(4-(4-(2-(2-aminopyridin-3-yl)-5-phenyl-3H-imidazo[4,5-b]pyridin-3-yl)benzyl)piperazine-1-carbonyl)thiazole-2-carbonitrile;

4-((7-(4-(2-(2-aminopyridin-3-yl)-5-phenyl-3H-imidazo[4,5-b]pyridin-3-yl)benzyl)-7-azaspiro[3.5]nonan-2-yl)amino)-1,3,5-triazine-2-carbonitrile;

4-(7-(4-(2-(2-aminopyridin-3-yl)-5-phenyl-3H-imidazo[4,5-b]pyridin-3-yl)benzyl)-2,7-diazaspiro[3.5]nonan-2-yl)-1,3,5-triazine-2-carbonitrile;

4-(4-(4-(2-(2-aminopyridin-3-yl)-5-phenyl-3H-imidazo[4,5-b]pyridin-3-yl)benzyl)-1,4-diazepan-1-yl)-1,3,5-triazine-2-carbonitrile;

4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile;

4-(2-(4-(2-(2-aminopyridin-3-yl)-5-phenyl-3H-imidazo[4,5-b]pyridin-3-yl)benzyl)-2,8-diazaspiro[4.5]decan-8-yl)-1,3,5-triazine-2-carbonitrile;

4-(2-(4-(2-(2-aminopyridin-3-yl)-5-phenyl-3H-imidazo[4,5-b]pyridin-3-yl)benzyl)-2,7-diazaspiro[4.5]decan-7-yl)-1,3,5-triazine-2-carbonitrile;

4-(9-(4-(2-(2-aminopyridin-3-yl)-5-phenyl-3H-imidazo[4,5-b]pyridin-3-yl)benzyl)-2,9-diazaspiro[5.5]undecan-2-yl)-1,3,5-triazine-2-carbonitrile;

(R)-4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile;

4-((2R,6R)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile;

4-(5-(4-(2-(2-aminopyridin-3-yl)-5-phenyl-3H-imidazo[4,5-b]pyridin-3-yl)benzyl)-2,5-diazabicyclo[2.2.2]octan-2-yl)-1,3,5-triazine-2-carbonitrile;

4-(4-(4-(2-(2-aminopyridin-3-yl)-5-cyclopropyl-3H-imidazo[4,5-b]pyridin-3-yl)benzyl)piperazin-1-yl)pyrimidine-2-carbonitrile;

4-(4-(4-(2-(2-aminopyridin-3-yl)-5-(2-oxo-1,2-dihydropyridin-3-yl)-3H-imidazo[4,5-b]pyridin-3-yl)benzyl)piperazin-1-yl)pyrimidine-2-carbonitrile;

4-(4-(4-(2-(2-aminopyridin-3-yl)-5-(1-methyl-2-oxo-1,2-dihydropyridin-3-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(1-methyl-2-oxo-1,2-dihydropyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-cyclobutyl-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(cyclohex-1-en-1-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-cyclohexyl-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-cyanophenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-oxo-1,6-dihydropyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-oxo-1,6-dihydropyridin-2-yl)-3H-imidazo[4,5-b]pyridin-3-yl)benzyl)piperidin-4-yl)amino)pyrimidine-2-carbonitrile;

4-(2-(4-(2-(2-aminopyridin-3-yl)-5-phenyl-3H-imidazo[4,5-b]pyridin-3-yl)benzyl)-2,7-diazaspiro[3.5]nonan-7-yl)-1,3,5-triazine-2-carbonitrile;

(S)-4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile;

4-(3-(4-(2-(2-aminopyridin-3-yl)-5-phenyl-3H-imidazo[4,5-b]pyridin-3-yl)benzyl)-3,8-diazabicyclo[3.2.1]octan-8-yl)-1,3,5-triazine-2-carbonitrile;

4-(8-(4-(2-(2-aminopyridin-3-yl)-5-phenyl-3H-imidazo[4,5-b]pyridin-3-yl)benzyl)-3,8-diazabicyclo[3.2.1]octan-3-yl)-1,3,5-triazine-2-carbonitrile;

4-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile;

(R)-4-(4-(4-(2-(2-aminopyridin-3-yl)-5-phenyl-3H-imidazo[4,5-b]pyridin-3-yl)benzyl)-2-methylpiperazin-1-yl)-1,3,5-triazine-2-carbonitrile;

(S)-4-(4-(4-(2-(2-aminopyridin-3-yl)-5-phenyl-3H-imidazo[4,5-b]pyridin-3-yl)benzyl)-2-methylpiperazin-1-yl)-1,3,5-triazine-2-carbonitrile;

4-((2S,6S)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile;

4-(7-(4-(2-(2-aminopyridin-3-yl)-5-phenyl-3H-imidazo[4,5-b]pyridin-3-yl)benzyl)-4,7-diazaspiro[2.5]octan-4-yl)-1,3,5-triazine-2-carbonitrile;

4-((2R,6S)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile;

4-((1-(4-(2-(2-aminopyridin-3-yl)-5-phenyl-3H-imidazo[4,5-b]pyridin-3-yl)benzyl)azepan-4-yl)amino)-1,3,5-triazine-2-carbonitrile;

4-((4-(4-(2-(2-aminopyridin-3-yl)-5-phenyl-3H-imidazo[4,5-b]pyridin-3-yl)benzyl)-1,4-oxazepan-6-yl)amino)-1,3,5-triazine-2-carbonitrile;

4-((1-(4-(2-(2-aminopyridin-3-yl)-5-methyl-3H-imidazo[4,5-b]pyridin-3-yl)benzyl)piperidin-4-yl)amino)pyrimidine-2-carbonitrile;

4-(4-(4-(2-(2-aminopyridin-3-yl)-5-(2-fluorophenyl)-3H-imidazo[4,5-b]pyridin-3-yl)benzyl)piperazin-1-yl)pyrimidine-2-carbonitrile;

2-(4-(4-(2-(2-aminopyridin-3-yl)-5-(2-fluorophenyl)-3H-imidazo[4,5-b]pyridin-3-yl)benzyl)piperazin-1-yl)pyrimidine-4-carbonitrile;

2-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-4-carbonitrile;

6-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-4-carbonitrile;

4-(8-(4-(2-(2-aminopyridin-3-yl)-5-morpholino-3H-imidazo[4,5-b]pyridin-3-yl)benzyl)-3,8-diazabicyclo[3.2.1]octan-3-yl)-1,3,5-triazine-2-carbonitrile;

4-((1-(4-(2-(2-aminopyridin-3-yl)-5-isopropyl-3H-imidazo[4,5-b]pyridin-3-yl)benzyl)piperidin-4-yl)amino)pyrimidine-2-carbonitrile;

4-((1-(4-(2-(2-aminopyridin-3-yl)-5-methoxy-3H-imidazo[4,5-b]pyridin-3-yl)benzyl)piperidin-4-yl)amino)pyrimidine-2-carbonitrile;

2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxamide;

2-(2-aminopyridin-3-yl)-3-(4-((4-((2-cyanopyrimidin-4-yl)amino)piperidin-1-yl)methyl)phenyl)-N,N-dimethyl-3H-imidazo[4,5-b]pyridine-5-carboxamide;

6-(4-(4-(2-(2-aminopyridin-3-yl)-5-cyclopropyl-3H-imidazo[4,5-b]pyridin-3-yl)benzyl)piperazin-1-yl)pyrimidine-4-carbonitrile;

6-((1-(4-(2-(2-aminopyridin-3-yl)-5-cyclopropyl-3H-imidazo[4,5-b]pyridin-3-yl)benzyl)piperidin-4-yl)amino)pyrimidine-4-carbonitrile;

4-(4-(4-(2-(2-aminopyridin-3-yl)-5-morpholino-3H-imidazo[4,5-b]pyridin-3-yl)benzyl)piperazin-1-yl)-1,3,5-triazine-2-carbonitrile;

4-(4-(4-(2-(2-aminopyridin-3-yl)-5-(2-cyanophenyl)-3H-imidazo[4,5-b]pyridin-3-yl)benzyl)piperazin-1-yl)pyrimidine-2-carbonitrile;

4-(4-(4-(2-(2-aminopyridin-3-yl)-5-(4-cyanophenyl)-3H-imidazo[4,5-b]pyridin-3-yl)benzyl)piperazin-1-yl)pyrimidine-2-carbonitrile;

4-(4-(4-(2-(2-aminopyridin-3-yl)-5-(3-fluorophenyl)-3H-imidazo[4,5-b]pyridin-3-yl)benzyl)piperazin-1-yl)pyrimidine-2-carbonitrile;

4-(4-(4-(2-(2-aminopyridin-3-yl)-5-(3-chlorophenyl)-3H-imidazo[4,5-b]pyridin-3-yl)benzyl)piperazin-1-yl)pyrimidine-2-carbonitrile;

2-(4-(4-(2-(2-aminopyridin-3-yl)-5-(3-chlorophenyl)-3H-imidazo[4,5-b]pyridin-3-yl)benzyl)piperazin-1-yl)pyrimidine-4-carbonitrile;

4-((1-(4-(2-(2-aminopyridin-3-yl)-5-cyclopropyl-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(tetrahydro-2H-pyran-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-phenyl-3H-imidazo[4,5-b]pyridin-3-yl)benzyl)azetidin-3-yl)amino)-1,3,5-triazine-2-carbonitrile;

4-(6-(4-(2-(2-aminopyridin-3-yl)-5-phenyl-3H-imidazo[4,5-b]pyridin-3-yl)benzyl)-2,6-diazaspiro[3.4]octan-2-yl)-1,3,5-triazine-2-carbonitrile;

4-(7-(4-(2-(2-aminopyridin-3-yl)-5-phenyl-3H-imidazo[4,5-b]pyridin-3-yl)benzyl)-2,7-diazaspiro[4.4]nonan-2-yl)pyrimidine-2-carbonitrile;

4-(6-(4-(2-(2-aminopyridin-3-yl)-5-phenyl-3H-imidazo[4,5-b]pyridin-3-yl)benzyl)-2,6-diazaspiro[3.3]heptan-2-yl)-1,3,5-triazine-2-carbonitrile;

4-(4-(4-(2-(2-aminopyridin-3-yl)-5-(2-chlorophenyl)-3H-imidazo[4,5-b]pyridin-3-yl)benzyl)piperazin-1-yl)-1,3,5-triazine-2-carbonitrile;

4-((1-(4-(2-(2-aminopyridin-3-yl)-5-(2-chlorophenyl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(2-chlorophenyl)-3H-imidazo[4,5-b]pyridin-3-yl)benzyl)piperidin-4-yl)amino)pyrimidine-4-carbonitrile;

6-((1-(4-(2-(2-aminopyridin-3-yl)-5-(2-chlorophenyl)-3H-imidazo[4,5-b]pyridin-3-yl)benzyl)piperidin-4-yl)amino)pyrimidine-4-carbonitrile;

4-((1-(4-(2-(2-aminopyridin-3-yl)-5-(4-chlorophenyl)-3H-imidazo[4,5-b]pyridin-3-yl)benzyl)piperidin-4-yl)amino)pyrimidine-2-carbonitrile;

2-(4-(4-(2-(2-aminopyridin-3-yl)-5-(3-fluorophenyl)-3H-imidazo[4,5-b]pyridin-3-yl)benzyl)piperazin-1-yl)pyrimidine-4-carbonitrile;

6-(4-(4-(2-(2-aminopyridin-3-yl)-5-(3-fluorophenyl)-3H-imidazo[4,5-b]pyridin-3-yl)benzyl)piperazin-1-yl)pyrimidine-4-carbonitrile;

6-((1-(4-(2-(2-aminopyridin-3-yl)-5-(3-fluorophenyl)-3H-imidazo[4,5-b]pyridin-3-yl)benzyl)piperidin-4-yl)amino)pyrimidine-4-carbonitrile;

4-(4-(4-(2-(2-aminopyridin-3-yl)-5-(2-fluorophenyl)-3H-imidazo[4,5-b]pyridin-3-yl)benzyl)piperazin-1-yl)-1,3,5-triazine-2-carbonitrile;

2-((1-(4-(2-(2-aminopyridin-3-yl)-5-(2-fluorophenyl)-3H-imidazo[4,5-b]pyridin-3-yl)benzyl)piperidin-4-yl)amino)pyrimidine-4-carbonitrile;

6-(4-(4-(2-(2-aminopyridin-3-yl)-5-(2-fluorophenyl)-3H-imidazo[4,5-b]pyridin-3-yl)benzyl)piperazin-1-yl)pyrimidine-4-carbonitrile;

6-((1-(4-(2-(2-aminopyridin-3-yl)-5-(2-fluorophenyl)-3H-imidazo[4,5-b]pyridin-3-yl)benzyl)piperidin-4-yl)amino)pyrimidine-4-carbonitrile;

4-((1-(4-(2-(2-aminopyridin-3-yl)-5-(2-fluorophenyl)-3H-imidazo[4,5-b]pyridin-3-yl)benzyl)piperidin-4-yl)amino)pyrimidine-2-carbonitrile;

4-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(3-oxo-1,4-diazepan-1-yl)-3H-imidazo[4,5-b]pyridin-3-yl)benzyl)piperidin-4-yl)amino)pyrimidine-2-carbonitrile;

2-(4-(4-(2-(2-aminopyridin-3-yl)-5-(4-cyanophenyl)-3H-imidazo[4,5-b]pyridin-3-yl)benzyl)piperazin-1-yl)pyrimidine-4-carbonitrile;

4-((1-(4-(2-(2-aminopyridin-3-yl)-5-(4-cyanophenyl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(4-cyanophenyl)-3H-imidazo[4,5-b]pyridin-3-yl)benzyl)piperidin-4-yl)amino)pyrimidine-4-carbonitrile;

2-(4-(4-(2-(2-aminopyridin-3-yl)-5-(2-cyanophenyl)-3H-imidazo[4,5-b]pyridin-3-yl)benzyl)piperazin-1-yl)pyrimidine-4-carbonitrile;

4-((1-(4-(2-(2-aminopyridin-3-yl)-5-(5-oxo-1,4-diazepan-1-yl)-3H-imidazo[4,5-b]pyridin-3-yl)benzyl)piperidin-4-yl)amino)pyrimidine-2-carbonitrile;

4-(4-(4-(2-(2-aminopyridin-3-yl)-5-(2-chlorophenyl)-3H-imidazo[4,5-b]pyridin-3-yl)benzyl)piperazin-1-yl)pyrimidine-2-carbonitrile;

2-(4-(4-(2-(2-aminopyridin-3-yl)-5-(2-chlorophenyl)-3H-imidazo[4,5-b]pyridin-3-yl)benzyl)piperazin-1-yl)pyrimidine-4-carbonitrile;

6-(4-(4-(2-(2-aminopyridin-3-yl)-5-(2-chlorophenyl)-3H-imidazo[4,5-b]pyridin-3-yl)benzyl)piperazin-1-yl)pyrimidine-4-carbonitrile;

5-(4-(4-(2-(2-aminopyridin-3-yl)-5-phenyl-3H-imidazo[4,5-b]pyridin-3-yl)benzyl)piperazine-1-carbonyl)thiazole-2-carbonitrile;

4-(4-(4-(2-(2-aminopyridin-3-yl)-5-phenyl-3H-imidazo[4,5-b]pyridin-3-yl)benzyl)piperazin-1-yl)-1,3,5-triazine-2-carbonitrile;

4-(4-(4-(2-(2-aminopyridin-3-yl)-5-(cyclohex-1-en-1-yl)-3H-imidazo[4,5-b]pyridin-3-yl)benzyl)piperazin-1-yl)pyrimidine-2-carbonitrile;

4-(4-(4-(2-(2-aminopyridin-3-yl)-5-(3,6-dihydro-2H-pyran-4-yl)-3H-imidazo[4,5-b]pyridin-3-yl)benzyl)piperazin-1-yl)pyrimidine-2-carbonitrile;

4-(4-(4-(2-(2-aminopyridin-3-yl)-5-(3-cyanophenyl)-3H-imidazo[4,5-b]pyridin-3-yl)benzyl)piperazin-1-yl)pyrimidine-2-carbonitrile;

4-(4-(4-(2-(2-aminopyridin-3-yl)-5-(6-oxo-1,6-dihydropyridin-3-yl)-3H-imidazo[4,5-b]pyridin-3-yl)benzyl)piperazin-1-yl)pyrimidine-2-carbonitrile;

2-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-4-carbonitrile;

6-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-4-carbonitrile;

4-((1-(4-(2-(2-aminopyridin-3-yl)-5-(2-cyanophenyl)-3H-imidazo[4,5-b]pyridin-3-yl)benzyl)piperidin-4-yl)amino)pyrimidine-2-carbonitrile;

N-(1-(4-(2-(2-aminopyridin-3-yl)-5-phenyl-3H-imidazo[4,5-b]pyridin-3-yl)benzyl)piperidin-4-yl)-2-cyano-N-methylpyrimidine-4-carboxamide;

(R)-4-((1-(4-(2-(2-aminopyridin-3-yl)-5-phenyl-3H-imidazo[4,5-b]pyridin-3-yl)benzyl)piperidin-3-yl)amino)-1,3,5-triazine-2-carbonitrile;

4-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile;

4-((3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile;

4-((3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)-1,3,5-triazine-2-carbonitrile;

4-((3aR,6aR)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile;

4-(4-(4-(2-(2-aminopyridin-3-yl)-5-(4-chlorophenyl)-3H-imidazo[4,5-b]pyridin-3-yl)benzyl)piperazin-1-yl)pyrimidine-2-carbonitrile;

2-(4-(4-(2-(2-aminopyridin-3-yl)-5-(4-chlorophenyl)-3H-imidazo[4,5-b]pyridin-3-yl)benzyl)piperazin-1-yl)pyrimidine-4-carbonitrile;

6-(4-(4-(2-(2-aminopyridin-3-yl)-5-(4-chlorophenyl)-3H-imidazo[4,5-b]pyridin-3-yl)benzyl)piperazin-1-yl)pyrimidine-4-carbonitrile;

4-(4-(4-(2-(2-aminopyridin-3-yl)-5-(4-methyl-5-oxo-1,4-diazepan-1-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(4-methyl-5-oxo-1,4-diazepan-1-yl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(3-oxo-1,4-diazepan-1-yl)-3H-imidazo[4,5-b]pyridin-3-yl)benzyl)piperidin-4-yl)amino)pyrimidine-4-carbonitrile;

4-(4-(4-(2-(2-aminopyridin-3-yl)-5-(1-methyl-6-oxo-1,6-dihydropyridin-3-yl)-3H-imidazo[4,5-b]pyridin-3-yl)benzyl)piperazin-1-yl)pyrimidine-2-carbonitrile;

4-(4-(4-(2-(2-aminopyridin-3-yl)-5-(1-methyl-2-oxo-1,2-dihydropyridin-4-yl)-3H-imidazo[4,5-b]pyridin-3-yl)benzyl)piperazin-1-yl)pyrimidine-2-carbonitrile;

2-(4-(4-(2-(2-aminopyridin-3-yl)-5-cyclopropyl-3H-imidazo[4,5-b]pyridin-3-yl)benzyl)piperazin-1-yl)pyrimidine-4-carbonitrile;

2-((1-(4-(2-(2-aminopyridin-3-yl)-5-cyclopropyl-3H-imidazo[4,5-b]pyridin-3-yl)benzyl)piperidin-4-yl)amino)pyrimidine-4-carbonitrile;

2-((1-(4-(2-(2-aminopyridin-3-yl)-5-(4-fluorophenyl)-3H-imidazo[4,5-b]pyridin-3-yl)benzyl)piperidin-4-yl)amino)pyrimidine-4-carbonitrile;

4-((1-(4-(2-(2-aminopyridin-3-yl)-5-(3-chlorophenyl)-3H-imidazo[4,5-b]pyridin-3-yl)benzyl)piperidin-4-yl)amino)pyrimidine-2-carbonitrile;

2-(4-(4-(2-(2-aminopyridin-3-yl)-5-(1-methyl-6-oxo-1,6-dihydropyridin-3-yl)-3H-imidazo[4,5-b]pyridin-3-yl)benzyl)piperazin-1-yl)pyrimidine-4-carbonitrile;

4-((1-(4-(2-(2-aminopyridin-3-yl)-5-(1-methyl-6-oxo-1,6-dihydropyridin-3-yl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(1-methyl-6-oxo-1,6-dihydropyridin-3-yl)-3H-imidazo[4,5-b]pyridin-3-yl)benzyl)piperidin-4-yl)amino)pyrimidine-4-carbonitrile;

4-((1-(4-(2-(2-aminopyridin-3-yl)-5-(3-fluorophenyl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(3-fluorophenyl)-3H-imidazo[4,5-b]pyridin-3-yl)benzyl)piperidin-4-yl)amino)pyrimidine-4-carbonitrile;

4-((1-(4-(2-(2-aminopyridin-3-yl)-5-(1-methyl-2-oxo-1,2-dihydropyridin-4-yl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(1-methyl-2-oxo-1,2-dihydropyridin-4-yl)-3H-imidazo[4,5-b]pyridin-3-yl)benzyl)piperidin-4-yl)amino)pyrimidine-4-carbonitrile;

4-(7-(4-(2-(2-aminopyridin-3-yl)-5-phenyl-3H-imidazo[4,5-b]pyridin-3-yl)benzyl)-2,7-diazaspiro[3.5]nonan-2-yl)pyrimidine-2-carbonitrile;

4-((7-(4-(2-(2-aminopyridin-3-yl)-5-phenyl-3H-imidazo[4,5-b]pyridin-3-yl)benzyl)-7-azaspiro[3.5]nonan-2-yl)amino)pyrimidine-2-carbonitrile;

4-(8-(4-(2-(2-aminopyridin-3-yl)-5-phenyl-3H-imidazo[4,5-b]pyridin-3-yl)benzyl)-2,8-diazaspiro[4.5]decan-2-yl)-1,3,5-triazine-2-carbonitrile;

4-(9-(4-(2-(2-aminopyridin-3-yl)-5-phenyl-3H-imidazo[4,5-b]pyridin-3-yl)benzyl)-3,9-diazaspiro[5.5]undecan-3-yl)pyrimidine-2-carbonitrile;

4-(9-(4-(2-(2-aminopyridin-3-yl)-5-phenyl-3H-imidazo[4,5-b]pyridin-3-yl)benzyl)-3,9-diazaspiro[5.5]undecan-3-yl)-1,3,5-triazine-2-carbonitrile;

4-(6-(4-(2-(2-aminopyridin-3-yl)-5-phenyl-3H-imidazo[4,5-b]pyridin-3-yl)benzyl)-2,6-diazaspiro[3.3]heptan-2-yl)pyrimidine-2-carbonitrile;

4-((3aS,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile;

4-(4-(4-(2-(2-aminopyridin-3-yl)-5-(4-fluorophenyl)-3H-imidazo[4,5-b]pyridin-3-yl)benzyl)piperazin-1-yl)-1,3,5-triazine-2-carbonitrile;

4-(4-(4-(2-(2-aminopyridin-3-yl)-5-(4-chlorophenyl)-3H-imidazo[4,5-b]pyridin-3-yl)benzyl)piperazin-1-yl)-1,3,5-triazine-2-carbonitrile;

4-((1-(4-(2-(2-aminopyridin-3-yl)-5-(4-fluorophenyl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(4-chlorophenyl)-3H-imidazo[4,5-b]pyridin-3-yl)benzyl)piperidin-4-yl)amino)pyrimidine-4-carbonitrile;

2-((1-(4-(2-(2-aminopyridin-3-yl)-5-(3-chlorophenyl)-3H-imidazo[4,5-b]pyridin-3-yl)benzyl)piperidin-4-yl)amino)pyrimidine-4-carbonitrile;

6-((1-(4-(2-(2-aminopyridin-3-yl)-5-(3-chlorophenyl)-3H-imidazo[4,5-b]pyridin-3-yl)benzyl)piperidin-4-yl)amino)pyrimidine-4-carbonitrile;

6-(4-(4-(2-(2-aminopyridin-3-yl)-5-(3-chlorophenyl)-3H-imidazo[4,5-b]pyridin-3-yl)benzyl)piperazin-1-yl)pyrimidine-4-carbonitrile;

4-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-2-carbonitrile;

6-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile;

2-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile;

4-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile;

2-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile;

6-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile;

4-((1-(4-(2-(2-aminopyridin-3-yl)-5-(2-oxo-1,2-dihydropyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-chlorophenyl)-3H-imidazo[4,5-b]pyridin-3-yl)benzyl)piperidin-4-yl)amino)-1,3,5-triazine-2-carbonitrile;

4-(4-(4-(2-(2-aminopyridin-3-yl)-5-(4-cyanopyridin-3-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(4-cyanopyridin-3-yl)-3H-imidazo[4,5-b]pyridin-3-yl)benzyl)piperidin-4-yl)amino)pyrimidine-2-carbonitrile;

4-((1-((4-(2-(2-aminopyridin-3-yl)-3H-imidazo[4,5-b]pyridin-3-yl)phenyl)methyl-d2)piperidin-4-yl)amino)pyrimidine-2-carbonitrile;

4-(4-(4-(2-(2-aminopyridin-3-yl)-5-(4-methyl-3-oxo-1,4-diazepan-1-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(3-oxomorpholino)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-cyclopentyl-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(dimethylamino)-3H-imidazo[4,5-b]pyridin-3-yl)benzyl)piperidin-4-yl)amino)pyrimidine-2-carbonitrile;

4-((1-(4-(2-(2-aminopyridin-3-yl)-3H-imidazo[4,5-b]pyridin-3-yl)benzyl)piperidin-4-yl)(methyl)amino)pyrimidine-2-carbonitrile;

4-((1-(4-(2-(2-aminopyridin-3-yl)-5-phenyl-3H-imidazo[4,5-b]pyridin-3-yl)benzyl)piperidin-4-yl)amino)-1,3,5-triazine-2-carbonitrile;

4-((1-(4-(2-(2-aminopyridin-3-yl)-3H-imidazo[4,5-b]pyridin-3-yl)benzyl)-4-methylpiperidin-4-yl)amino)pyrimidine-2-carbonitrile;

4-((1-(4-(2-(2-aminopyridin-3-yl)-5-(1-methyl-6-oxo-1,6-dihydropyridin-2-yl)-3H-imidazo[4,5-b]pyridin-3-yl)benzyl)piperidin-4-yl)amino)pyrimidine-2-carbonitrile;

4-(4-(4-(2-(2-aminopyridin-3-yl)-5-(1-methyl-6-oxo-1,6-dihydropyridin-2-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(3-methoxyphenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(tert-butyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-ethyl-3H-imidazo[4,5-b]pyridin-3-yl)benzyl)piperidin-4-yl)amino)pyrimidine-2-carbonitrile;

2-(2-aminopyridin-3-yl)-3-(4-((4-((2-cyanopyrimidin-4-yl)amino)piperidin-1-yl)methyl)phenyl)-N-methyl-3H-imidazo[4,5-b]pyridine-5-carboxamide;

4-(4-(4-(2-(2-aminopyridin-3-yl)-5-(3-cyanopyridin-4-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(3-cyanopyridin-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-fluoro-3H-imidazo[4,5-b]pyridin-3-yl)benzyl)piperidin-4-yl)amino)pyrimidine-2-carbonitrile;

4-((1-(4-(2-(2-aminopyridin-3-yl)-6-fluoro-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-oxooxazolidin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-fluoropyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-chloro-3H-imidazo[4,5-b]pyridin-3-yl)benzyl)piperidin-4-yl)amino)pyrimidine-2-carbonitrile;

2-(2-aminopyridin-3-yl)-3-(4-((4-((2-cyanopyrimidin-4-yl)amino)piperidin-1-yl)methyl)phenyl)-3H-imidazo[4,5-b]pyridine-5-carbonitrile;

4-(4-(4-(2-(2-aminopyridin-3-yl)-5-(3-cyanopyridin-2-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(3-cyanopyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-cyanopyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(trifluoromethyl)-3H-imidazo[4,5-b]pyridin-3-yl)benzyl)piperidin-4-yl)amino)pyrimidine-2-carbonitrile;

2-(2-aminopyridin-3-yl)-3-(4-((4-((2-cyanopyrimidin-4-yl)amino)piperidin-1-yl)methyl)phenyl)-3H-imidazo[4,5-b]pyridine-6-carbonitrile;

4-((1-(4-(2-(2-aminopyridin-3-yl)-5,6-dimethyl-3H-imidazo[4,5-b]pyridin-3-yl)benzyl)piperidin-4-yl)amino)pyrimidine-2-carbonitrile;

4-((1-(4-(2-(2-aminopyridin-3-yl)-1H-imidazo[4,5-b]pyrazin-1-yl)benzyl)piperidin-4-yl)amino)pyrimidine-2-carbonitrile;

methyl 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylate;

2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylic acid;

4-((1-(4-(2-(2-aminopyridin-3-yl)-5-(fluoromethoxy)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(tetrahydrofuran-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-cyanopyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-cyanopyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(oxetan-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-methoxyphenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-methoxyphenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(trifluoromethoxy)-3H-imidazo[4,5-b]pyridin-3-yl)benzyl)piperidin-4-yl)amino)pyrimidine-2-carbonitrile;

4-(4-(4-(2-(2-aminopyridin-3-yl)-5-(2-cyanopyridin-3-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-isopropoxy-3H-imidazo[4,5-b]pyridin-3-yl)benzyl)piperidin-4-yl)amino)pyrimidine-2-carbonitrile;

4-((4-(4-(2-(2-aminopyridin-3-yl)-5-phenyl-3H-imidazo[4,5-b]pyridin-3-yl)benzyl)piperazin-1-yl)amino)pyrimidine-2-carbonitrile;

4-((1-(4-(2-(2-aminopyridin-3-yl)-5-(methoxy-d3)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-cyanopyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-cyanopyrimidin-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-cyanopyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(pyridin-3-yl)-3H-imidazo[4,5-b]pyridin-3-yl)benzyl)piperidin-4-yl)amino)pyrimidine-2-carbonitrile;

4-(4-(4-(2-(2-aminopyridin-3-yl)-5-(pyridin-3-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(pyridin-4-yl)-3H-imidazo[4,5-b]pyridin-3-yl)benzyl)piperidin-4-yl)amino)pyrimidine-2-carbonitrile;

4-((7-(4-(2-(2-aminopyridin-3-yl)-5-morpholino-3H-imidazo[4,5-b]pyridin-3-yl)benzyl)-7-azaspiro[3.5]nonan-2-yl)amino)-1,3,5-triazine-2-carbonitrile;

4-((1-(4-(2-(2-aminopyridin-3-yl)-5-(methylthio)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(methylsulfonyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-methoxypyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-methyl-1H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-fluoro-3-methoxyphenyl)-3H-imidazo[4,5-b]pyridin-3-yl)benzyl)piperidin-4-yl)amino)pyrimidine-2-carbonitrile;

N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)acetamide;

4-((1-(4-(2-(2-aminopyridin-3-yl)-5-(4-fluorophenyl)-3H-imidazo[4,5-b]pyridin-3-yl)benzyl)piperidin-4-yl)(methyl-d3)amino)pyrimidine-2-carbonitrile;

4-((1-((4-(2-(2-aminopyridin-3-yl)-5-(4-fluorophenyl)-3H-imidazo[4,5-b]pyridin-3-yl)phenyl)methyl-d2)piperidin-4-yl)(methyl-d3)amino)pyrimidine-2-carbonitrile;

4-((1-(4-(2-(2-aminopyridin-3-yl)-5-(4-fluorophenyl)-3H-imidazo[4,5-b]pyridin-3-yl)benzyl)azetidin-3-yl)amino)pyrimidine-2-carbonitrile;

4-((7-(4-(2-(2-aminopyridin-3-yl)-5-(4-fluorophenyl)-3H-imidazo[4,5-b]pyridin-3-yl)benzyl)-7-azaspiro[3.5]nonan-2-yl)amino)pyrimidine-2-carbonitrile;

4-((2-(4-(2-(2-aminopyridin-3-yl)-5-(4-fluorophenyl)-3H-imidazo[4,5-b]pyridin-3-yl)benzyl)-2-azaspiro[3.3]heptan-6-yl)amino)pyrimidine-2-carbonitrile;

4-((2-(4-(2-(2-aminopyridin-3-yl)-5-(4-fluorophenyl)-3H-imidazo[4,5-b]pyridin-3-yl)benzyl)-2-azaspiro[3.5]nonan-7-yl)amino)pyrimidine-2-carbonitrile;

4-(6-(4-(2-(2-aminopyridin-3-yl)-5-(4-fluorophenyl)-3H-imidazo[4,5-b]pyridin-3-yl)benzyl)-2,6-diazaspiro[3.3]heptan-2-yl)pyrimidine-2-carbonitrile;

4-(8-(4-(2-(2-aminopyridin-3-yl)-5-(4-fluorophenyl)-3H-imidazo[4,5-b]pyridin-3-yl)benzyl)-3,8-diazabicyclo[3.2.1]octan-3-yl)pyrimidine-2-carbonitrile;

4-(3aR,6aS)-5-(4-(2-(2-aminopyridin-3-yl)-5-(4-fluorophenyl)-3H-imidazo[4,5-b]pyridin-3-yl)benzyl)hexahydropyrrolo[3,4-c]pyrrol-2(1H)-yl)pyrimidine-2-carbonitrile;

4-((3aS,6aS)-5-(4-(2-(2-aminopyridin-3-yl)-5-(4-fluorophenyl)-3H-imidazo[4,5-b]pyridin-3-yl)benzyl)hexahydropyrrolo[3,4-c]pyrrol-2(1H)-yl)pyrimidine-2-carbonitrile;

4-((1-(4-(2-(2-aminopyridin-3-yl)-5-(4-fluorophenyl)-3H-imidazo[4,5-b]pyridin-3-yl)benzyl)piperidin-4-yl-4-d)amino)pyrimidine-2-carbonitrile;

4-((1-(4-(2-(2-aminopyridin-3-yl)-5,6-dimethyl-3H-imidazo[4,5-b]pyridin-3-yl)benzyl)piperidin-4-yl-4-d)amino)pyrimidine-2-carbonitrile;

4-((1-(4-(2-(2-aminopyridin-3-yl)-5-(cyclopent-1-en-1-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-vinyl-3H-imidazo[4,5-b]pyridin-3-yl)benzyl)piperidin-4-yl)amino)pyrimidine-2-carbonitrile;

4-((1-(4-(2-(2-aminopyridin-3-yl)-5,6-dimethyl-3H-imidazo[4,5-b]pyridin-3-yl)benzyl)piperidin-4-yl)(methyl-d3)amino)pyrimidine-2-carbonitrile;

4-((1-(4-(2-(2-aminopyridin-3-yl)-5-(5-fluoropyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(methylamino)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(bis(methyl-d3) amino)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-((methyl-d3)amino)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(azetidin-1-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(isoxazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(oxazol-5-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-methylisoxazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-methylisoxazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-methyl-1H-pyrazol-5-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-ethyl-1H-pyrazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-methyl-1H-pyrazol-5-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-(2-oxopyrrolidin-1-yl)phenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-fluoro-2-methoxyphenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-(trifluoromethyl)phenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-(trifluoromethyl)phenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3,5-dimethylisoxazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-(difluoromethyl)-1H-pyrazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2,4-difluorophenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-methoxypyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-methylpyridin-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-methylpyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-isopropyl-1H-pyrazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(isothiazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-cyano-1-methyl-1H-pyrrol-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(thiazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(isothiazol-5-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1,5-dimethyl-1H-pyrazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-bromo-3H-imidazo[4,5-b]pyridin-3-yl)benzyl)piperidin-4-yl)amino)pyrimidine-2-carbonitrile;

4-((1-((4-(2-(2-aminopyridin-3-yl)-5-bromo-3H-imidazo[4,5-b]pyridin-3-yl)phenyl)methyl-d2)piperidin-4-yl)amino)pyrimidine-2-carbonitrile;

4-((1-(4-(2-(2-aminopyridin-3-yl)-5-(4-fluorophenyl)-3H-imidazo[4,5-b]pyridin-3-yl)benzyl)piperidin-4-yl)amino)-1,3,5-triazine-2-carbonitrile;

4-((1-((4-(2-(2-aminopyridin-3-yl)-5-(4-fluorophenyl)-3H-imidazo[4,5-b]pyridin-3-yl)phenyl)methyl-d2)piperidin-4-yl)(methyl)amino)pyrimidine-2-carbonitrile;

4-((1-((4-(2-(2-aminopyridin-3-yl)-5-(4-fluorophenyl)-3H-imidazo[4,5-b]pyridin-3-yl)phenyl)methyl-d2)piperidin-4-yl)amino)pyrimidine-2-carbonitrile;

4-(7-(4-(2-(2-aminopyridin-3-yl)-5-(4-fluorophenyl)-3H-imidazo[4,5-b]pyridin-3-yl)benzyl)-2,7-diazaspiro[3.5]nonan-2-yl)pyrimidine-2-carbonitrile;

4-(2-(4-(2-(2-aminopyridin-3-yl)-5-(4-fluorophenyl)-3H-imidazo[4,5-b]pyridin-3-yl)benzyl)-2,7-diazaspiro[3.5]nonan-7-yl)pyrimidine-2-carbonitrile;

4-((1-(4-(2-(2-aminopyridin-3-yl)-5-(methylsulfinyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5,7-dimethyl-3H-imidazo[4,5-b]pyridin-3-yl)benzyl)piperidin-4-yl)amino)pyrimidine-2-carbonitrile;

4-((1-(4-(8-(2-aminopyridin-3-yl)-6-hydroxy-9H-purin-9-yl)benzyl)piperidin-4-yl)amino)pyrimidine-2-carbonitrile;

4-((1-(4-(2-(2-aminopyridin-3-yl)-5-(pyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-hydroxy-3H-imidazo[4,5-b]pyridin-3-yl)benzyl)piperidin-4-yl)amino)pyrimidine-2-carbonitrile;

4-((1-(4-(5-amino-2-(2-aminopyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-chloro-4-fluorophenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-fluorophenyl)-6-methyl-3H-imidazo[4,5-b]pyridin-3-yl)benzyl)piperidin-4-yl)amino)pyrimidine-2-carbonitrile;

2-(2-aminopyridin-3-yl)-1-(4-((4-((2-cyanopyrimidin-4-yl)amino)piperidin-1-yl)methyl)phenyl)-1H-benzo[d]imidazole-6-carbonitrile;

2-(2-aminopyridin-3-yl)-1-(4-((4-((2-cyanopyrimidin-4-yl)amino)piperidin-1-yl)methyl)phenyl)-1H-benzo[d]imidazole-5-carbonitrile;

4-((1-((4-(2-(2-aminopyridin-3-yl)-3H-imidazo[4,5-b]
pyridin-3-yl)phenyl)methyl-d2)piperidin-4-yl)(methyl-
d3)amino)pyrimidine-2-carbonitrile;
4-((1-(4-(2-(2-aminopyridin-3-yl)-3H-imidazo[4,5-b]
pyridin-3-yl)benzyl)piperidin-4-yl-4-d)amino)pyrimi-
dine-2-carbonitrile;
4-((1-((4-(2-(2-aminopyridin-3-yl)-5,6-dimethyl-3H-imi-
dazo[4,5-b]pyridin-3-yl)phenyl)methyl-d2)piperidin-
4-yl)amino)pyrimidine-2-carbonitrile;
4-((1-(4-(8-(2-aminopyridin-3-yl)-9H-purin-9-yl)benzyl)
piperidin-4-yl)amino)pyrimidine-2-carbonitrile;
(S)-4-((1-(4-(2-(2-aminopyridin-3-yl)-5-(tetrahydro-
furan-3-yl)-3H-imidazo[4,5-b]pyridin-3-yl)benzyl)pi-
peridin-4-yl)amino)pyrimidine-2-carbonitrile;
(R)-4-((1-(4-(2-(2-aminopyridin-3-yl)-5-(tetrahydro-
furan-3-yl)-3H-imidazo[4,5-b]pyridin-3-yl)benzyl)pi-
peridin-4-yl)amino)pyrimidine-2-carbonitrile;
4-((1-(4-(2-(2-aminopyridin-3-yl)-5-(hydroxymethyl)-
3H-imidazo[4,5-b]pyridin-3-yl)benzyl)piperidin-4-yl)
amino)pyrimidine-2-carbonitrile;
4-((1-(4-(2-(2-aminopyridin-3-yl)-5-(fluoromethyl)-3H-
imidazo[4,5-b]pyridin-3-yl)benzyl)piperidin-4-yl)
amino)pyrimidine-2-carbonitrile;
4-((1-(4-(2-(2-aminopyridin-3-yl)-5-(pyrrolidin-1-yl)-
3H-imidazo[4,5-b]pyridin-3-yl)benzyl)piperidin-4-yl)
amino)pyrimidine-2-carbonitrile;
4-((1-(4-(2-(2-aminopyridin-3-yl)-5-(2-methoxypyridin-
4-yl)-3H-imidazo[4,5-b]pyridin-3-yl)benzyl)piperidin-
4-yl)amino)pyrimidine-2-carbonitrile;
4-((1-(4-(2-(2-aminopyridin-3-yl)-5-(5-methoxy pyridin-
3-yl)-3H-imidazo[4,5-b]pyridin-3-yl)benzyl)piperidin-
4-yl)amino)pyrimidine-2-carbonitrile;
4-((1-(4-(2-(2-aminopyridin-3-yl)-5-ethynyl-3H-imidazo
[4,5-b]pyridin-3-yl)benzyl)piperidin-4-yl)amino)py-
rimidine-2-carbonitrile;
N-(3-(2-(2-aminopyridin-3-yl)-3-(4-((4-((2-cyanopyrimi-
din-4-yl)amino)piperidin-1-yl)methyl)phenyl)-3H-imi-
dazo[4,5-b]pyridin-5-yl)phenyl)-N-methylacetamide;
4-((1-(4-(2-(2-aminopyridin-3-yl)-5-(3-methoxypyridin-
4-yl)-3H-imidazo[4,5-b]pyridin-3-yl)benzyl)piperidin-
4-yl)amino)pyrimidine-2-carbonitrile;
4-((1-(4-(2-(2-aminopyridin-3-yl)-5-(6-methoxypyridin-
3-yl)-3H-imidazo[4,5-b]pyridin-3-yl)benzyl)piperidin-
4-yl)amino)pyrimidine-2-carbonitrile;
4-((1-(4-(5-(3-aminophenyl)-2-(2-aminopyridin-3-yl)-
3H-imidazo[4,5-b]pyridin-3-yl)benzyl)piperidin-4-yl)
amino)pyrimidine-2-carbonitrile;
N-(3-(2-(2-aminopyridin-3-yl)-3-(4-((4-((2-cyanopyrimi-
din-4-yl)amino)piperidin-1-yl)methyl)phenyl)-3H-imi-
dazo[4,5-b]pyridin-5-yl)phenyl)isobutyramide;
N-(3-(3-(4-((4-((2-cyanopyrimidin-4-yl)amino)piperidin-
1-yl)methyl)phenyl)-2-(2-isobutyramidopyridin-3-yl)-
3H-imidazo[4,5-b]pyridin-5-yl)phenyl)isobutyramide;
methyl (3-(2-(2-aminopyridin-3-yl)-3-(4-((4-((2-cyano-
pyrimidin-4-yl)amino)piperidin-1-yl)methyl)phenyl)-
3H-imidazo[4,5-b]pyridin-5-yl)phenyl)carbamate;
4-((1-(4-(2-(2-aminopyridin-3-yl)-5-(3-(dimethylamino)
phenyl)-3H-imidazo[4,5-b]pyridin-3-yl)benzyl)piperi-
din-4-yl)amino)pyrimidine-2-carbonitrile;
N-(1-(3-(2-(2-aminopyridin-3-yl)-3-(4-((4-((2-cyanopy-
rimidin-4-yl)amino)piperidin-1-yl)methyl)phenyl)-3H-
imidazo[4,5-b]pyridin-5-yl)phenyl)piperidin-4-yl)-N-
methylacetamide;
4-((1-(4-(2-(2-aminopyridin-3-yl)-5-(4-fluoro-2-meth-
ylphenyl)-3H-imidazo[4,5-b]pyridin-3-yl)benzyl)pip-
eridin-4-yl)amino)pyrimidine-2-carbonitrile;

2-(2-(2-aminopyridin-3-yl)-3-(4-((4-((2-cyanopyrimidin-
4-yl)amino)piperidin-1-yl)methyl)phenyl)-3H-imidazo
[4,5-b]pyridin-5-yl)-5-fluorobenzamide;
4-((1-(4-(2-(2-aminopyridin-3-yl)-5-(2-cyano-4-fluoro-
phenyl)-3H-imidazo[4,5-b]pyridin-3-yl)benzyl)piperi-
din-4-yl)amino)pyrimidine-2-carbonitrile;
4-((1-(4-(2-(2-aminopyridin-3-yl)-5-(4-fluoro-2-(trifluo-
romethyl)phenyl)-3H-imidazo[4,5-b]pyridin-3-yl)ben-
zyl)piperidin-4-yl)amino)pyrimidine-2-carbonitrile;
4-((1-(4-(2-(2-aminopyridin-3-yl)-5-(o-tolyl)-3H-imi-
dazo[4,5-b]pyridin-3-yl)benzyl)piperidin-4-yl)amino)
pyrimidine-2-carbonitrile;
4-((1-(4-(2-(2-aminopyridin-3-yl)-5-(m-tolyl)-3H-imi-
dazo[4,5-b]pyridin-3-yl)benzyl)piperidin-4-yl)amino)
pyrimidine-2-carbonitrile;
4-((1-(4-(2-(2-aminopyridin-3-yl)-5-(p-tolyl)-3H-imi-
dazo[4,5-b]pyridin-3-yl)benzyl)piperidin-4-yl)amino)
pyrimidine-2-carbonitrile;
4-((1-(4-(2-(2-aminopyridin-3-yl)-5-(3-(trifluoromethyl)
phenyl)-3H-imidazo[4,5-b]pyridin-3-yl)benzyl)piperi-
din-4-yl)amino)pyrimidine-2-carbonitrile;
isopropyl 2-(2-aminopyridin-3-yl)-3-(4-((4-((2-cyanopy-
rimidin-4-yl)amino)piperidin-1-yl)methyl)phenyl)-3H-
imidazo[4,5-b]pyridine-5-carboxylate;
4-((1-(4-(2-(2-aminopyridin-3-yl)-1H-benzo[d]imidazol-
1-yl)benzyl)piperidin-4-yl)amino)pyrimidine-2-carbo-
nitrile;
4-((1-(4-(2-(2-aminopyridin-3-yl)-1H-imidazo[4,5-b]
pyridin-1-yl)benzyl)piperidin-4-yl)amino)pyrimidine-
2-carbonitrile;
4-((1-(4-(2-(2-aminopyridin-3-yl)-5-(6-methylpyridin-3-
yl)-3H-imidazo[4,5-b]pyridin-3-yl)benzyl)piperidin-4-
yl)amino)pyrimidine-2-carbonitrile;
4-((1-(4-(2-(2-aminopyridin-3-yl)-5-(difluoromethoxy)-
3H-imidazo[4,5-b]pyridin-3-yl)benzyl)piperidin-4-yl)
amino)pyrimidine-2-carbonitrile;
4-((1-(4-(2-(2-aminopyridin-3-yl)-5-(4-methoxypyridin-
3-yl)-3H-imidazo[4,5-b]pyridin-3-yl)benzyl)piperidin-
4-yl)amino)pyrimidine-2-carbonitrile;
4-((1-(4-(2-(2-aminopyridin-3-yl)-5-(2-methoxypyridin-
3-yl)-3H-imidazo[4,5-b]pyridin-3-yl)benzyl)piperidin-
4-yl)amino)pyrimidine-2-carbonitrile;
4-((1-(4-(2-(2-aminopyridin-3-yl)-5-(2-hydroxypyridin-
3-yl)-3H-imidazo[4,5-b]pyridin-3-yl)benzyl)piperidin-
4-yl)amino)pyrimidine-2-carbonitrile;
4-((1-(4-(2-(2-aminopyridin-3-yl)-5-(1,3-dimethyl-1H-
pyrazol-4-yl)-3H-imidazo[4,5-b]pyridin-3-yl)benzyl)
piperidin-4-yl)amino)pyrimidine-2-carbonitrile;
4-((1-(4-(2-(2-aminopyridin-3-yl)-1H-imidazo[4,5-c]
pyridin-1-yl)benzyl)piperidin-4-yl)amino)pyrimidine-
2-carbonitrile;
4-((1-(4-(2-(2-aminopyridin-3-yl)-5-(4-fluorophenyl)-
3H-imidazo[4,5-b]pyridin-3-yl)benzyl)piperidin-4-yl)
(methyl)amino)pyrimidine-2-carbonitrile;
4-((1-(4-(2-(2-aminopyridin-3-yl)-5-(6-(difluo-
romethoxy)pyridin-3-yl)-3H-imidazo[4,5-b]pyridin-3-
yl)benzyl)piperidin-4-yl)amino)pyrimidine-2-carboni-
trile;
4-((1-(4-(2-(2-aminopyridin-3-yl)-5-(2-(difluo-
romethoxy)pyridin-4-yl)-3H-imidazo[4,5-b]pyridin-3-
yl)benzyl)piperidin-4-yl)amino)pyrimidine-2-carboni-
trile;
4-((1-(4-(2-(2-aminopyridin-3-yl)-5-(4-fluoro-2-hy-
droxyphenyl)-3H-imidazo[4,5-b]pyridin-3-yl)benzyl)
piperidin-4-yl)amino)pyrimidine-2-carbonitrile;

4-((1-(4-(2-(2-aminopyridin-3-yl)-5-(4-fluoro-3-hydroxyphenyl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1-methyl-1H-imidazol-5-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-methylpyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(4-cyanopyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-6-bromo-5-(4-fluorophenyl)-3H-imidazo[4,5-b]pyridin-3-yl)benzyl)piperidin-4-yl)amino)pyrimidine-2-carbonitrile;
2-(2-aminopyridin-3-yl)-3-(4-((4-((2-cyanopyrimidin-4-yl)amino)piperidin-1-yl)methyl)phenyl)-5-methyl-3H-imidazo[4,5-b]pyridine-6-carbonitrile;
4-((1-(4-(2-(2-aminopyridin-3-yl)-5-(3-fluoropyridin-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-methoxypyridin-2-yl)-3H-imidazo[4,5-b]pyridin-3-yl)benzyl)piperidin-4-yl)amino)pyrimidine-2-carbonitrile;
2-(2-aminopyridin-3-yl)-1-(4-((4-((2-cyanopyrimidin-4-yl)amino)piperidin-1-yl)methyl)phenyl)-1H-imidazo[4,5-c]pyridine-6-carbonitrile;
4-((1-(4-(2-(2-aminopyridin-3-yl)-5-(4-methyloxazol-5-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1-cyclopropyl-1H-pyrazol-4-yl)-3H-imidazo[4,5-b]pyridin-3-yl)benzyl)piperidin-4-yl)amino)pyrimidine-2-carbonitrile;
2-(2-aminopyridin-3-yl)-1-(4-((4-((2-cyanopyrimidin-4-yl)amino)piperidin-1-yl)methyl)phenyl)-1H-imidazo[4,5-b]pyrazine-5,6-dicarbonitrile;
2-(2-aminopyridin-3-yl)-3-(4-((4-((2-cyanopyrimidin-4-yl)amino)piperidin-1-yl)methyl)phenyl)-5-(4-fluorophenyl)-3H-imidazo[4,5-b]pyridine-6-carbonitrile;
4-((1-(4-(2-(2-aminopyridin-3-yl)-5-(2-fluoropyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1-methyl-1H-1,2,4-triazol-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-ethoxypyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2-fluoropyridin-4-yl)-3H-imidazo[4,5-b]pyridin-3-yl)benzyl)piperidin-4-yl)amino)pyrimidine-2-carbonitrile;
4-((1-(4-(2-(3-aminopyrazin-2-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(3-methoxypyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(l-methyl-1H-1,2,3-triazol-5-yl)-3H-imidazo[4,5-b]pyridin-3-yl)benzyl)piperidin-4-yl)amino)pyrimidine-2-carbonitrile;
2-(2-aminopyridin-3-yl)-3-(4-((4-((2-cyanopyrimidin-4-yl)amino)piperidin-1-yl)methyl)phenyl)-6-methyl-3H-imidazo[4,5-b]pyridine-5-carbonitrile;
4-((1-(4-(2-(2-aminopyridin-3-yl)-5-(5-methyl-1,3,4-oxadiazol-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1-methyl-1H-1,2,4-triazol-5-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(4-methyl-2H-1,2,3-triazol-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(4-methyl-4H-1,2,4-triazol-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(3-fluoropyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-methylpyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1-(difluoromethyl)-1H-1,2,4-triazol-3-yl)-3H-imidazo[4,5-b]pyridin-3-yl)benzyl)piperidin-4-yl)amino)pyrimidine-2-carbonitrile;
4-((1-(4-(2-(4-aminopyrimidin-5-yl)-5-(5-fluoropyridin-2-yl)-3H-imidazo[4,5-b]pyridin-3-yl)benzyl)piperidin-4-yl)amino)pyrimidine-2-carbonitrile;
4-((1-(4-(2-(3-aminopyrazin-2-yl)-5-(5-fluoropyridin-2-yl)-3H-imidazo[4,5-b]pyridin-3-yl)benzyl)piperidin-4-yl)amino)pyrimidine-2-carbonitrile;
4-((1-(4-(5-(5-fluoropyridin-2-yl)-2-(pyridin-3-yl)-3H-imidazo[4,5-b]pyridin-3-yl)benzyl)piperidin-4-yl)amino)pyrimidine-2-carbonitrile;
4-((1-(4-(2-(2-aminophenyl)-5-(5-fluoropyridin-2-yl)-3H-imidazo[4,5-b]pyridin-3-yl)benzyl)piperidin-4-yl)amino)pyrimidine-2-carbonitrile;
4-((1-(4-(5-(5-fluoropyridin-2-yl)-2-phenyl-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-(methoxy-d3)pyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-(difluoromethoxy)pyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-(fluoromethoxy)pyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-methoxypyrimidin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-methylpyrazin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-methoxypyrazin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-ethoxy pyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-cyclopropoxypyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-isopropoxypyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-cyclopropylpyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-methyl-4H-1,2,4-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(3-methyl-1H-1,2,4-triazol-1-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1H-1,2,4-triazol-1-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1H-1,2,3-triazol-1-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2H-1,2,3-triazol-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(4-methyl-1H-1,2,3-triazol-1-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(oxazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(4-fluoropyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(4-methylpyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-(methoxy-d3)pyridin-3-yl-2-d)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-(methoxy-d3)pyridin-3-yl)-3H-imidazo[4,5-b]pyridin-3-yl)benzyl)piperidin-4-yl)amino)pyrimidine-2-carbonitrile;
2-(2-aminopyridin-3-yl)-3-(4-((4-((2-cyanopyrimidin-4-yl)amino)piperidin-1-yl)methyl)phenyl)-5-hydroxy-3H-imidazo[4,5-b]pyridine-6-carbonitrile;
4-((1-(4-(2-(2-amino-4-fluoropyridin-3-yl)-5-(5-fluoropyridin-2-yl)-3H-imidazo[4,5-b]pyridin-3-yl)benzyl)piperidin-4-yl)amino)pyrimidine-2-carbonitrile;
4-((1-(4-(5-(5-fluoropyridin-2-yl)-2-(pyrimidin-5-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-6-(5-fluoropyridin-2-yl)-1H-benzo[d]imidazol-1-yl)benzyl)piperidin-4-yl)amino)pyrimidine-2-carbonitrile;
4-((1-(4-(2-(2-aminopyridin-3-yl)-5-(5-fluoropyrimidin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-methylpyrimidin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-fluoropyrazin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-(fluoromethoxy)pyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1-(fluoromethyl)-6-oxo-1,6-dihydropyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2-(methyl-d3)-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2-ethyl-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2-isopropyl-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1-isopropyl-1H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2-methyl-5-(methyl-d3)-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2,5-dimethyl-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2-cyclopropyl-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2-methyl-2H-1,2,3-triazol-4-yl-5-d)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1-(difluoromethyl)-6-oxo-1,6-dihydropyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2-(fluoromethyl)-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1-(fluoromethyl)-1H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2-(difluoromethyl)-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(3-aminopyrazin-2-yl)-5-(2-(methyl-d3)-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(3-aminoisoxazol-4-yl)-5-(5-fluoropyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-(fluoromethoxy-d2)pyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1-(fluoromethyl-d2)-6-oxo-1,6-dihydropyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(1-ethyl-1H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2-(cyanomethyl)-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(3-aminopyrazin-2-yl)-5-(2-(fluoromethyl)-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(3-aminopyrazin-2-yl)-5-(1-(fluoromethyl)-1H-1,2,3-triazol-4-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(2-ethyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(2-isopropyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(2-cyclopropyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(2-(cyanomethyl)-2H-1,2,3-triazol-4-yl)-3H-imidazo[4,5-b]pyridin-3-yl)benzyl)piperidin-4-yl)amino)pyrimidine-2-carbonitrile;

2-(4-(2-(3-aminopyrazin-2-yl)-3-(4-((4-((2-cyanopyrimidin-4-yl)amino)piperidin-1-yl)methyl)phenyl)-3H-imidazo[4,5-b]pyridin-5-yl)-2H-1,2,3-triazol-2-yl)acetamide;

4-((1-(4-(2-(3-aminopyrazin-2-yl)-5-(2-methyl-2H-1,2,3-triazol-4-yl-5-d)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(2,5-dimethyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(6-methoxypyridin-3-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(6-(methoxy-d3)pyridin-3-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(5-(methoxy-d3)pyridin-2-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(6-(fluoromethoxy)pyridin-3-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(6-(fluoromethoxy-d2)pyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-cyclopropoxypyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-isopropoxypyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-isopropylpyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-cyclopropylpyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-(difluoromethyl)pyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-(trifluoromethyl)pyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-ethylpyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-(fluoromethyl)pyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-(difluoromethyl)pyridin-2-yl)-3H-imidazo[4,5-b]pyridin-3-yl)benzyl)piperidin-4-yl)amino)pyrimidine-2-carbonitrile; and 4-((1-(4-(2-(2-aminopyridin-3-yl)-5-(5-(trifluoromethyl)pyridin-2-yl)-3H-imidazo[4,5-b]pyridin-3-yl)benzyl)piperidin-4-yl)amino)pyrimidine-2-carbonitrile.

2. The compound of claim 1, or pharmaceutically acceptable salt or solvate thereof, wherein the compound is selected from the group consisting of:

4-((1-(4-(2-(2-aminopyridin-3-yl)-5-phenyl-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-fluorophenyl)-3H-imidazo[4,5-b]pyridin-3-yl)benzyl)piperidin-4-yl)amino)pyrimidine-2-carbonitrile;

2-(2-aminopyridin-3-yl)-3-(4-((4-((2-cyanopyrimidin-4-yl)amino)piperidin-1-yl)methyl)phenyl)-3H-imidazo[4,5-b]pyridine-6-carbonitrile;

4-((1-(4-(2-(2-aminopyridin-3-yl)-5-(5-fluoropyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-methoxypyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-(difluoromethoxy)pyridin-2-yl)-3H-imidazo[4,5-b]pyridin-3-yl)benzyl)piperidin-4-yl)amino)pyrimidine-2-carbonitrile; and 4-((1-(4-(2-(2-aminopyridin-3-yl)-5-(5-cyclopropoxypyridin-2-yl)-3H-imidazo[4,5-b]pyridin-3-yl)benzyl)piperidin-4-yl)amino)pyrimidine-2-carbonitrile.

3. The compound of claim 2, or pharmaceutically acceptable salt or solvate thereof, wherein the compound is 4-((1-(4-(2-(2-aminopyridin-3-yl)-5-phenyl-3H-imidazo[4,5-b]pyridin-3-yl)benzyl)piperidin-4-yl)amino)pyrimidine-2-carbonitrile.

4. The compound of claim 2, or pharmaceutically acceptable salt or solvate thereof, wherein the compound is 4-((1-(4-(2-(2-aminopyridin-3-yl)-5-(4-fluorophenyl)-3H-imidazo[4,5-b]pyridin-3-yl)benzyl)piperidin-4-yl)amino)pyrimidine-2-carbonitrile.

5. The compound of claim 2, or pharmaceutically acceptable salt or solvate thereof, wherein the compound is 2-(2-aminopyridin-3-yl)-3-(4-((4-((2-cyanopyrimidin-4-yl)amino)piperidin-1-yl)methyl)phenyl)-3H-imidazo[4,5-b]pyridine-6-carbonitrile.

6. The compound of claim 2, or pharmaceutically acceptable salt or solvate thereof, wherein the compound is 4-((1-(4-(2-(2-aminopyridin-3-yl)-5-(5-fluoropyridin-2-yl)-3H-imidazo[4,5-b]pyridin-3-yl)benzyl)piperidin-4-yl)amino)pyrimidine-2-carbonitrile.

7. The compound of claim 2, or pharmaceutically acceptable salt or solvate thereof, wherein the compound is 4-((1-(4-(2-(2-aminopyridin-3-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile.

8. The compound of claim 2, or pharmaceutically acceptable salt or solvate thereof, wherein the compound is 4-((1-(4-(2-(2-aminopyridin-3-yl)-5-(6-methoxypyridin-3-yl)-3H-imidazo[4,5-b]pyridin-3-yl)benzyl)piperidin-4-yl)amino)pyrimidine-2-carbonitrile.

9. The compound of claim 2, or pharmaceutically acceptable salt or solvate thereof, wherein the compound is 4-((1-(4-(2-(2-aminopyridin-3-yl)-5-(5-(difluoromethoxy)pyridin-2-yl)-3H-imidazo[4,5-b]pyridin-3-yl)benzyl)piperidin-4-yl)amino)pyrimidine-2-carbonitrile.

10. The compound of claim 2, or pharmaceutically acceptable salt or solvate thereof, wherein the compound is 4-((1-(4-(2-(2-aminopyridin-3-yl)-5-(5-cyclopropoxypyridin-2-yl)-3H-imidazo[4,5-b]pyridin-3-yl)benzyl)piperidin-4-yl)amino)pyrimidine-2-carbonitrile.

11. A pharmaceutical composition comprising at least one pharmaceutically acceptable excipient and a compound, or pharmaceutically acceptable salt or solvate thereof, selected from the group consisting of:

6-((1-(4-(2-(2-aminopyridin-3-yl)-3H-imidazo[4,5-b]pyridin-3-yl)benzyl)piperidin-4-yl)oxy)nicotinonitrile;
6-((1-(4-(2-(2-aminopyridin-3-yl)-5-phenyl-3H-imidazo[4,5-b]pyridin-3-yl)benzyl)piperidin-4-yl)oxy)nicotinonitrile;
6-((1-(4-(2-(2-aminopyridin-3-yl)-6-phenyl-3H-imidazo[4,5-b]pyridin-3-yl)benzyl)piperidin-4-yl)oxy)nicotinonitrile;
6-((1-(4-(2-(2-aminopyridin-3-yl)-3H-imidazo[4,5-b]pyridin-3-yl)benzyl)piperidin-4-yl)oxy)picolinonitrile;
2-((1-(4-(2-(2-aminopyridin-3-yl)-3H-imidazo[4,5-b]pyridin-3-yl)benzyl)piperidin-4-yl)oxy)isonicotinonitrile;
2-((1-(4-(2-(2-aminopyridin-3-yl)-3H-imidazo[4,5-b]pyridin-3-yl)benzyl)piperidin-4-yl)oxy)nicotinonitrile;
6-((1-(4-(2-(2-aminopyridin-3-yl)-5-phenyl-3H-imidazo[4,5-b]pyridin-3-yl)benzyl)piperidin-4-yl)oxy)picolinonitrile;
2-((1-(4-(2-(2-aminopyridin-3-yl)-5-phenyl-3H-imidazo[4,5-b]pyridin-3-yl)benzyl)piperidin-4-yl)oxy)isonicotinonitrile;
2-((1-(4-(2-(2-aminopyridin-3-yl)-5-phenyl-3H-imidazo[4,5-b]pyridin-3-yl)benzyl)piperidin-4-yl)oxy)nicotinonitrile;
6-((1-(4-(2-(2-aminopyridin-3-yl)-6-phenyl-3H-imidazo[4,5-b]pyridin-3-yl)benzyl)piperidin-4-yl)oxy)picolinonitrile;
2-((1-(4-(2-(2-aminopyridin-3-yl)-6-phenyl-3H-imidazo[4,5-b]pyridin-3-yl)benzyl)piperidin-4-yl)oxy)isonicotinonitrile;
2-((1-(4-(2-(2-aminopyridin-3-yl)-6-phenyl-3H-imidazo[4,5-b]pyridin-3-yl)benzyl)piperidin-4-yl)oxy)nicotinonitrile;
4-(4-(4-(2-(2-aminopyridin-3-yl)-3H-imidazo[4,5-b]pyridin-3-yl)benzyl)piperazin-1-yl)picolinonitrile;
5-(4-(4-(2-(2-aminopyridin-3-yl)-3H-imidazo[4,5-b]pyridin-3-yl)benzyl)piperazin-1-yl)picolinonitrile;
6-(4-(4-(2-(2-aminopyridin-3-yl)-3H-imidazo[4,5-b]pyridin-3-yl)benzyl)piperazin-1-yl)picolinonitrile;
5-(4-(4-(2-(2-aminopyridin-3-yl)-3H-imidazo[4,5-b]pyridin-3-yl)benzyl)piperazin-1-yl)nicotinonitrile;
2-(4-(4-(2-(2-aminopyridin-3-yl)-3H-imidazo[4,5-b]pyridin-3-yl)benzyl)piperazin-1-yl)isonicotinonitrile;
4-(4-(4-(2-(2-aminopyridin-3-yl)-3H-imidazo[4,5-b]pyridin-3-yl)benzyl)piperazin-1-yl)pyrimidine-2-carbonitrile;
6-(4-(4-(2-(2-aminopyridin-3-yl)-3H-imidazo[4,5-b]pyridin-3-yl)benzyl)piperazin-1-yl)pyrazine-2-carbonitrile;
2-(4-(4-(2-(2-aminopyridin-3-yl)-3H-imidazo[4,5-b]pyridin-3-yl)benzyl)piperazin-1-yl)pyrimidine-4-carbonitrile;
6-(4-(4-(2-(2-aminopyridin-3-yl)-3H-imidazo[4,5-b]pyridin-3-yl)benzyl)piperazin-1-yl)pyrimidine-4-carbonitrile;
6-(4-(4-(2-(2-aminopyridin-3-yl)-3H-imidazo[4,5-b]pyridin-3-yl)benzyl)piperazin-1-yl)pyridazine-4-carbonitrile;
N-(1-(4-(2-(2-aminopyridin-3-yl)-3H-imidazo[4,5-b]pyridin-3-yl)benzyl)piperidin-4-yl)-2-cyanoisonicotinamide;
N-(1-(4-(2-(2-aminopyridin-3-yl)-3H-imidazo[4,5-b]pyridin-3-yl)benzyl)piperidin-4-yl)-6-cyanonicotinamide;
N-(1-(4-(2-(2-aminopyridin-3-yl)-3H-imidazo[4,5-b]pyridin-3-yl)benzyl)piperidin-4-yl)-5-cyanopicolinamide;
N-(1-(4-(2-(2-aminopyridin-3-yl)-3H-imidazo[4,5-b]pyridin-3-yl)benzyl)piperidin-4-yl)-5-cyanonicotinamide;
N-(1-(4-(2-(2-aminopyridin-3-yl)-3H-imidazo[4,5-b]pyridin-3-yl)benzyl)piperidin-4-yl)-2-cyanonicotinamide;
N-(1-(4-(2-(2-aminopyridin-3-yl)-3H-imidazo[4,5-b]pyridin-3-yl)benzyl)piperidin-4-yl)-3-cyanopicolinamide;
N-(1-(4-(2-(2-aminopyridin-3-yl)-3H-imidazo[4,5-b]pyridin-3-yl)benzyl)piperidin-4-yl)-4-cyanonicotinamide;
N-(1-(4-(2-(2-aminopyridin-3-yl)-3H-imidazo[4,5-b]pyridin-3-yl)benzyl)piperidin-4-yl)-6-cyanopicolinamide;
N-(1-(4-(2-(2-aminopyridin-3-yl)-3H-imidazo[4,5-b]pyridin-3-yl)benzyl)piperidin-4-yl)-4-cyanopicolinamide;
N-(1-(4-(2-(2-aminopyridin-3-yl)-3H-imidazo[4,5-b]pyridin-3-yl)benzyl)piperidin-4-yl)-2-cyanopyrimidine-4-carboxamide;
N-(1-(4-(2-(2-aminopyridin-3-yl)-3H-imidazo[4,5-b]pyridin-3-yl)benzyl)piperidin-4-yl)-6-cyanopyrimidine-4-carboxamide;
N-(1-(4-(2-(2-aminopyridin-3-yl)-3H-imidazo[4,5-b]pyridin-3-yl)benzyl)piperidin-4-yl)-2-cyanobenzo[d]thiazole-5-carboxamide;
N-(1-(4-(2-(2-aminopyridin-3-yl)-3H-imidazo[4,5-b]pyridin-3-yl)benzyl)piperidin-4-yl)-2-cyano-5-fluorobenzo[d]thiazole-7-carboxamide;
N-(1-(4-(2-(2-aminopyridin-3-yl)-3H-imidazo[4,5-b]pyridin-3-yl)benzyl)piperidin-4-yl)-3-cyanoisonicotinamide;
N-(3-(2-(2-aminopyridin-3-yl)-3-(4-((4-(2-cyanopyridin-4-yl)piperazin-1-yl)methyl)phenyl)-3H-imidazo[4,5-b]pyridin-5-yl)phenyl)acetamide;
N-(3-(2-(2-aminopyridin-3-yl)-3-(4-((4-(6-cyanopyridin-3-yl)piperazin-1-yl)methyl)phenyl)-3H-imidazo[4,5-b]pyridin-5-yl)phenyl)acetamide;
N-(3-(2-(2-aminopyridin-3-yl)-3-(4-((4-(6-cyanopyridin-2-yl)piperazin-1-yl)methyl)phenyl)-3H-imidazo[4,5-b]pyridin-5-yl)phenyl)acetamide;
N-(3-(2-(2-aminopyridin-3-yl)-3-(4-((4-(6-cyanopyrazin-2-yl)piperazin-1-yl)methyl)phenyl)-3H-imidazo[4,5-b]pyridin-5-yl)phenyl)acetamide;
N-(3-(2-(2-aminopyridin-3-yl)-3-(4-((4-(6-cyanopyrimidin-4-yl)piperazin-1-yl)methyl)phenyl)-3H-imidazo[4,5-b]pyridin-5-yl)phenyl)acetamide;
N-(3-(2-(2-aminopyridin-3-yl)-3-(4-((4-(2-cyanopyrimidin-5-yl)piperazin-1-yl)methyl)phenyl)-3H-imidazo[4,5-b]pyridin-5-yl)phenyl)acetamide;
N-(3-(2-(2-aminopyridin-3-yl)-3-(4-((4-(6-cyanopyridazin-4-yl)piperazin-1-yl)methyl)phenyl)-3H-imidazo[4,5-b]pyridin-5-yl)phenyl)acetamide;
N-(3-(2-(2-aminopyridin-3-yl)-3-(4-((4-(2-cyanopyrimidin-4-yl)piperazin-1-yl)methyl)phenyl)-3H-imidazo[4,5-b]pyridin-5-yl)phenyl)acetamide;

N-(3-(2-(2-aminopyridin-3-yl)-3-(4-((4-(5-cyano-pyridazin-3-yl)piperazin-1-yl)methyl)phenyl)-3H-imidazo[4,5-b]pyridin-5-yl)phenyl)acetamide;

N-(3-(2-(2-aminopyridin-3-yl)-3-(4-((4-(4-cyanopyrimidin-2-yl)piperazin-1-yl)methyl)phenyl)-3H-imidazo[4,5-b]pyridin-5-yl)phenyl)acetamide;

4-(4-(4-(2-(2-aminopyridin-3-yl)-5-phenyl-3H-imidazo[4,5-b]pyridin-3-yl)benzyl)piperazin-1-yl)pyrimidine-2-carbonitrile;

6-((1-(4-(2-(2-aminopyridin-3-yl)-3H-imidazo[4,5-b]pyridin-3-yl)benzyl)piperidin-4-yl)amino)pyridazine-4-carbonitrile;

6-(4-(4-(2-(2-aminopyridin-3-yl)-5-phenyl-3H-imidazo[4,5-b]pyridin-3-yl)benzyl)piperazin-1-yl)pyridazine-4-carbonitrile;

6-((1-(4-(2-(2-aminopyridin-3-yl)-5-phenyl-3H-imidazo[4,5-b]pyridin-3-yl)benzyl)piperidin-4-yl)amino)pyridazine-4-carbonitrile;

N-(1-(4-(2-(2-aminopyridin-3-yl)-5-phenyl-3H-imidazo[4,5-b]pyridin-3-yl)benzyl)piperidin-4-yl)-2-cyanoisonicotinamide;

N-(1-(4-(2-(2-aminopyridin-3-yl)-5-phenyl-3H-imidazo[4,5-b]pyridin-3-yl)benzyl)piperidin-4-yl)-6-cyanopicolinamide;

N-(1-(4-(2-(2-aminopyridin-3-yl)-5-phenyl-3H-imidazo[4,5-b]pyridin-3-yl)benzyl)piperidin-4-yl)-5-cyanonicotinamide;

N-(1-(4-(2-(2-aminopyridin-3-yl)-5-phenyl-3H-imidazo[4,5-b]pyridin-3-yl)benzyl)piperidin-4-yl)-2-cyanonicotinamide;

N-(1-(4-(2-(2-aminopyridin-3-yl)-5-phenyl-3H-imidazo[4,5-b]pyridin-3-yl)benzyl)piperidin-4-yl)-3-cyanoisonicotinamide;

N-(1-(4-(2-(2-aminopyridin-3-yl)-5-phenyl-3H-imidazo[4,5-b]pyridin-3-yl)benzyl)piperidin-4-yl)-4-cyanonicotinamide;

N-(1-(4-(2-(2-aminopyridin-3-yl)-5-phenyl-3H-imidazo[4,5-b]pyridin-3-yl)benzyl)piperidin-4-yl)-3-cyanopicolinamide;

4-((1-(4-(2-(2-aminopyridin-3-yl)-3H-imidazo[4,5-b]pyridin-3-yl)benzyl)piperidin-4-yl)amino)picolinonitrile;

6-((1-(4-(2-(2-aminopyridin-3-yl)-3H-imidazo[4,5-b]pyridin-3-yl)benzyl)piperidin-4-yl)amino)picolinonitrile;

6-((1-(4-(2-(2-aminopyridin-3-yl)-3H-imidazo[4,5-b]pyridin-3-yl)benzyl)piperidin-4-yl)amino)pyrimidine-4-carbonitrile;

5-(4-(4-(2-(2-aminopyridin-3-yl)-5-phenyl-3H-imidazo[4,5-b]pyridin-3-yl)benzyl)piperazin-1-yl)nicotinonitrile;

2-(4-(4-(2-(2-aminopyridin-3-yl)-5-phenyl-3H-imidazo[4,5-b]pyridin-3-yl)benzyl)piperazin-1-yl)isonicotinonitrile;

6-(4-(4-(2-(2-aminopyridin-3-yl)-5-phenyl-3H-imidazo[4,5-b]pyridin-3-yl)benzyl)piperazin-1-yl)pyrazine-2-carbonitrile;

2-(4-(4-(2-(2-aminopyridin-3-yl)-5-phenyl-3H-imidazo[4,5-b]pyridin-3-yl)benzyl)piperazin-1-yl)pyrimidine-4-carbonitrile;

6-(4-(4-(2-(2-aminopyridin-3-yl)-3H-imidazo[4,5-b]pyridin-3-yl)benzyl)piperazine-1-carbonyl)picolinonitrile;

4-(4-(4-(2-(2-aminopyridin-3-yl)-5-phenyl-3H-imidazo[4,5-b]pyridin-3-yl)benzyl)piperazine-1-carbonyl)pyridazine-3-carbonitrile;

N-(1-(4-(2-(2-aminopyridin-3-yl)-5-phenyl-3H-imidazo[4,5-b]pyridin-3-yl)benzyl)piperidin-4-yl)-3-cyanopyridazine-4-carboxamide;

4-(4-(4-(2-(2-aminopyridin-3-yl)-5-phenyl-3H-imidazo[4,5-b]pyridin-3-yl)benzyl)piperazine-1-carbonyl)pyrimidine-5-carbonitrile;

N-(1-(4-(2-(2-aminopyridin-3-yl)-5-phenyl-3H-imidazo[4,5-b]pyridin-3-yl)benzyl)piperidin-4-yl)-5-cyanopyrimidine-4-carboxamide;

5-((1-(4-(2-(2-aminopyridin-3-yl)-3H-imidazo[4,5-b]pyridin-3-yl)benzyl)piperidin-4-yl)amino)nicotinonitrile;

2-((1-(4-(2-(2-aminopyridin-3-yl)-3H-imidazo[4,5-b]pyridin-3-yl)benzyl)piperidin-4-yl)amino)isonicotinonitrile;

6-((1-(4-(2-(2-aminopyridin-3-yl)-3H-imidazo[4,5-b]pyridin-3-yl)benzyl)piperidin-4-yl)amino)pyrazine-2-carbonitrile;

2-((1-(4-(2-(2-aminopyridin-3-yl)-3H-imidazo[4,5-b]pyridin-3-yl)benzyl)piperidin-4-yl)amino)pyrimidine-4-carbonitrile;

6-(4-(4-(2-(2-aminopyridin-3-yl)-5-phenyl-3H-imidazo[4,5-b]pyridin-3-yl)benzyl)piperazin-1-yl)pyrimidine-4-carbonitrile;

5-(4-(4-(2-(2-aminopyridin-3-yl)-3H-imidazo[4,5-b]pyridin-3-yl)benzyl)piperazine-1-carbonyl)nicotinonitrile;

6-(4-(4-(2-(2-aminopyridin-3-yl)-3H-imidazo[4,5-b]pyridin-3-yl)benzyl)piperazine-1-carbonyl)nicotinonitrile;

N-(1-(4-(2-(2-aminopyridin-3-yl)-5-phenyl-3H-imidazo[4,5-b]pyridin-3-yl)benzyl)piperidin-4-yl)-5-cyanopicolinamide;

4-(4-(4-(2-(2-aminopyridin-3-yl)-5-phenyl-3H-imidazo[4,5-b]pyridin-3-yl)benzyl)piperazin-1-yl)picolinonitrile;

6-(4-(4-(2-(2-aminopyridin-3-yl)-5-phenyl-3H-imidazo[4,5-b]pyridin-3-yl)benzyl)piperazin-1-yl)picolinonitrile;

5-((1-(4-(2-(2-aminopyridin-3-yl)-5-phenyl-3H-imidazo[4,5-b]pyridin-3-yl)benzyl)piperidin-4-yl)amino)picolinonitrile;

4-((1-(4-(2-(2-aminopyridin-3-yl)-5-phenyl-3H-imidazo[4,5-b]pyridin-3-yl)benzyl)piperidin-4-yl)amino)picolinonitrile;

6-((1-(4-(2-(2-aminopyridin-3-yl)-5-phenyl-3H-imidazo[4,5-b]pyridin-3-yl)benzyl)piperidin-4-yl)amino)picolinonitrile;

2-((1-(4-(2-(2-aminopyridin-3-yl)-5-phenyl-3H-imidazo[4,5-b]pyridin-3-yl)benzyl)piperidin-4-yl)amino)isonicotinonitrile;

4-((1-(4-(2-(2-aminopyridin-3-yl)-5-phenyl-3H-imidazo[4,5-b]pyridin-3-yl)benzyl)piperidin-4-yl)amino)pyrimidine-2-carbonitrile;

6-((1-(4-(2-(2-aminopyridin-3-yl)-5-phenyl-3H-imidazo[4,5-b]pyridin-3-yl)benzyl)piperidin-4-yl)amino)pyrazine-2-carbonitrile;

2-((1-(4-(2-(2-aminopyridin-3-yl)-5-phenyl-3H-imidazo[4,5-b]pyridin-3-yl)benzyl)piperidin-4-yl)amino)pyrimidine-4-carbonitrile;

6-((1-(4-(2-(2-aminopyridin-3-yl)-5-phenyl-3H-imidazo[4,5-b]pyridin-3-yl)benzyl)piperidin-4-yl)amino)pyrimidine-4-carbonitrile;

4-((1-(4-(2-(2-aminopyridin-3-yl)-3H-imidazo[4,5-b]pyridin-3-yl)benzyl)piperidin-4-yl)amino)pyrimidine-2-carbonitrile;

5-((1-(4-(2-(2-aminopyridin-3-yl)-5-phenyl-3H-imidazo[4,5-b]pyridin-3-yl)benzyl)piperidin-4-yl)amino)nicotinonitrile;

5-(4-(4-(2-(2-aminopyridin-3-yl)-5-phenyl-3H-imidazo[4,5-b]pyridin-3-yl)benzyl)piperazin-1-yl)picolinonitrile;

5-(4-(4-(2-(2-aminopyridin-3-yl)-5-phenyl-3H-imidazo[4,5-b]pyridin-3-yl)benzyl)piperazin-1-yl)pyrimidine-2-carbonitrile;

5-(4-(4-(2-(2-aminopyridin-3-yl)-3H-imidazo[4,5-b]pyridin-3-yl)benzyl)piperazine-1-carbonyl)picolinonitrile;

N-(1-(4-(2-(2-aminopyridin-3-yl)-6-phenyl-3H-imidazo[4,5-b]pyridin-3-yl)benzyl)piperidin-4-yl)-2-cyanoisonicotinamide;

4-(4-(4-(2-(2-aminopyridin-3-yl)-3H-imidazo[4,5-b]pyridin-3-yl)benzyl)piperazine-1-carbonyl)picolinonitrile;

2-(4-(4-(2-(2-aminopyridin-3-yl)-3H-imidazo[4,5-b]pyridin-3-yl)benzyl)piperazine-1-carbonyl)nicotinonitrile;

5-(4-(4-(2-(2-aminopyridin-3-yl)-6-phenyl-3H-imidazo[4,5-b]pyridin-3-yl)benzyl)piperazine-1-carbonyl)picolinonitrile;

6-(4-(4-(2-(2-aminopyridin-3-yl)-3H-imidazo[4,5-b]pyridin-3-yl)benzyl)piperazine-1-carbonyl)pyrimidine-4-carbonitrile;

6-(4-(4-(2-(2-aminopyridin-3-yl)-5-phenyl-3H-imidazo[4,5-b]pyridin-3-yl)benzyl)piperazine-1-carbonyl)pyrimidine-4-carbonitrile;

N-(1-(4-(2-(2-aminopyridin-3-yl)-5-phenyl-3H-imidazo[4,5-b]pyridin-3-yl)benzyl)piperidin-4-yl)-6-cyanopyrimidine-4-carboxamide;

4-(4-(4-(2-(2-aminopyridin-3-yl)-6-phenyl-3H-imidazo[4,5-b]pyridin-3-yl)benzyl)piperazine-1-carbonyl)picolinonitrile;

6-(4-(4-(2-(2-aminopyridin-3-yl)-5-phenyl-3H-imidazo[4,5-b]pyridin-3-yl)benzyl)piperazine-1-carbonyl)picolinonitrile;

5-(4-(4-(2-(2-aminopyridin-3-yl)-5-phenyl-3H-imidazo[4,5-b]pyridin-3-yl)benzyl)piperazine-1-carbonyl)nicotinonitrile;

2-(4-(4-(2-(2-aminopyridin-3-yl)-5-phenyl-3H-imidazo[4,5-b]pyridin-3-yl)benzyl)piperazine-1-carbonyl)isonicotinonitrile;

4-(4-(4-(2-(2-aminopyridin-3-yl)-5-phenyl-3H-imidazo[4,5-b]pyridin-3-yl)benzyl)piperazine-1-carbonyl)pyrimidine-2-carbonitrile;

6-(4-(4-(2-(2-aminopyridin-3-yl)-5-phenyl-3H-imidazo[4,5-b]pyridin-3-yl)benzyl)piperazine-1-carbonyl)nicotinonitrile;

3-(4-(4-(2-(2-aminopyridin-3-yl)-5-phenyl-3H-imidazo[4,5-b]pyridin-3-yl)benzyl)piperazine-1-carbonyl)picolinonitrile;

4-(4-(4-(2-(2-aminopyridin-3-yl)-5-phenyl-3H-imidazo[4,5-b]pyridin-3-yl)benzyl)piperazine-1-carbonyl)nicotinonitrile;

3-(4-(4-(2-(2-aminopyridin-3-yl)-5-phenyl-3H-imidazo[4,5-b]pyridin-3-yl)benzyl)piperazine-1-carbonyl)isonicotinonitrile;

2-(4-(4-(2-(2-aminopyridin-3-yl)-5-phenyl-3H-imidazo[4,5-b]pyridin-3-yl)benzyl)piperazine-1-carbonyl)nicotinonitrile;

2-(4-(4-(2-(2-aminopyridin-3-yl)-3H-imidazo[4,5-b]pyridin-3-yl)benzyl)piperazine-1-carbonyl)isonicotinonitrile;

N-(1-(4-(2-(2-aminopyridin-3-yl)-5-phenyl-3H-imidazo[4,5-b]pyridin-3-yl)benzyl)piperidin-4-yl)-4-cyanopicolinamide;

N-(1-(4-(2-(2-aminopyridin-3-yl)-5-phenyl-3H-imidazo[4,5-b]pyridin-3-yl)benzyl)piperidin-4-yl)-2-cyanopyrimidine-4-carboxamide;

4-(4-(4-(2-(2-aminopyridin-3-yl)-3H-imidazo[4,5-b]pyridin-3-yl)benzyl)piperazine-1-carbonyl)pyrimidine-2-carbonitrile;

3-(4-(4-(2-(2-aminopyridin-3-yl)-3H-imidazo[4,5-b]pyridin-3-yl)benzyl)piperazine-1-carbonyl)picolinonitrile;

4-(4-(4-(2-(2-aminopyridin-3-yl)-3H-imidazo[4,5-b]pyridin-3-yl)benzyl)piperazine-1-carbonyl)nicotinonitrile;

3-(4-(4-(2-(2-aminopyridin-3-yl)-3H-imidazo[4,5-b]pyridin-3-yl)benzyl)piperazine-1-carbonyl)isonicotinonitrile;

4-((1-(4-(2-(2-aminopyridin-3-yl)-5-phenyl-3H-imidazo[4,5-b]pyridin-3-yl)benzyl)piperidin-4-yl)(methyl)amino)pyrimidine-2-carbonitrile;

5-((1-(4-(2-(2-aminopyridin-3-yl)-3H-imidazo[4,5-b]pyridin-3-yl)benzyl)piperidin-4-yl)amino)picolinonitrile;

5-((1-(4-(2-(2-aminopyridin-3-yl)-5-phenyl-3H-imidazo[4,5-b]pyridin-3-yl)benzyl)piperidin-4-yl)amino)pyridazine-3-carbonitrile;

5-(4-(4-(2-(2-aminopyridin-3-yl)-5-phenyl-3H-imidazo[4,5-b]pyridin-3-yl)benzyl)piperazin-1-yl)pyridazine-3-carbonitrile;

3-(4-(4-(2-(2-aminopyridin-3-yl)-5-phenyl-3H-imidazo[4,5-b]pyridin-3-yl)benzyl)piperazine-1-carbonyl)pyrazine-2-carbonitrile;

3-(4-(4-(2-(2-aminopyridin-3-yl)-3H-imidazo[4,5-b]pyridin-3-yl)benzyl)piperazine-1-carbonyl)pyrazine-2-carbonitrile;

N-(1-(4-(2-(2-aminopyridin-3-yl)-6-phenyl-3H-imidazo[4,5-b]pyridin-3-yl)benzyl)piperidin-4-yl)-6-cyanonicotinamide;

5-(4-(4-(2-(2-aminopyridin-3-yl)-5-phenyl-3H-imidazo[4,5-b]pyridin-3-yl)benzyl)piperazine-1-carbonyl)picolinonitrile;

N-(1-(4-(2-(2-aminopyridin-3-yl)-5-phenyl-3H-imidazo[4,5-b]pyridin-3-yl)benzyl)piperidin-4-yl)-6-cyanonicotinamide;

4-(4-(4-(2-(2-aminopyridin-3-yl)-5-phenyl-3H-imidazo[4,5-b]pyridin-3-yl)benzyl)piperazine-1-carbonyl)picolinonitrile;

7-(4-(4-(2-(2-aminopyridin-3-yl)-3H-imidazo[4,5-b]pyridin-3-yl)benzyl)piperazine-1-carbonyl)-5-fluorobenzo[d]thiazole-2-carbonitrile;

7-(4-(4-(2-(2-aminopyridin-3-yl)-5-phenyl-3H-imidazo[4,5-b]pyridin-3-yl)benzyl)piperazine-1-carbonyl)-5-fluorobenzo[d]thiazole-2-carbonitrile;

4-(4-(4-(2-(2-aminopyridin-3-yl)-5-phenyl-3H-imidazo[4,5-b]pyridin-3-yl)benzyl)piperazine-1-carbonyl)-6-fluorobenzo[d]thiazole-2-carbonitrile;

N-(1-(4-(2-(2-aminopyridin-3-yl)-5-phenyl-3H-imidazo[4,5-b]pyridin-3-yl)benzyl)piperidin-4-yl)-2-cyano-5-fluorobenzo[d]thiazole-7-carboxamide;

N-(1-(4-(2-(2-aminopyridin-3-yl)-5-phenyl-3H-imidazo[4,5-b]pyridin-3-yl)benzyl)piperidin-4-yl)-2-cyano-6-fluorobenzo[d]thiazole-4-carboxamide;

5-(4-(4-(2-(2-aminopyridin-3-yl)-5-phenyl-3H-imidazo[4,5-b]pyridin-3-yl)benzyl)piperazine-1-carbonyl)benzo[d]thiazole-2-carbonitrile;

N-(1-(4-(2-(2-aminopyridin-3-yl)-5-phenyl-3H-imidazo[4,5-b]pyridin-3-yl)benzyl)piperidin-4-yl)-2-cyanobenzo[d]thiazole-5-carboxamide;

4-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile;

2-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile;

6-((2S,6S)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile;

4-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile;

2-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile;

6-((2R,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile;

4-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-2-carbonitrile;

2-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-4-carbonitrile;

6-(7-(4-(2-(2-aminopyridin-3-yl)-5-phenyl-3H-imidazo[4,5-b]pyridin-3-yl)benzyl)-4,7-diazaspiro[2.5]octan-4-yl)pyrimidine-4-carbonitrile;

4-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-2-carbonitrile;

6-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-4-carbonitrile;

4-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-2-carbonitrile;

2-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-4-carbonitrile;

6-(3-(4-(2-(2-aminopyridin-3-yl)-5-phenyl-3H-imidazo[4,5-b]pyridin-3-yl)benzyl)-3,8-diazabicyclo[3.2.1]octan-8-yl)pyrimidine-4-carbonitrile;

(S)-4-(4-(4-(2-(2-aminopyridin-3-yl)-5-phenyl-3H-imidazo[4,5-b]pyridin-3-yl)benzyl)-2-methylpiperazin-1-yl)pyrimidine-2-carbonitrile;

(S)-2-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile;

(S)-6-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile;

4-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-2-carbonitrile;

2-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-4-carbonitrile;

6-(8-(4-(2-(2-aminopyridin-3-yl)-5-phenyl-3H-imidazo[4,5-b]pyridin-3-yl)benzyl)-3,8-diazabicyclo[3.2.1]octan-3-yl)pyrimidine-4-carbonitrile;

4-(4-(4-(2-(2-aminopyridin-3-yl)-5-phenyl-3H-imidazo[4,5-b]pyridin-3-yl)benzyl)-1,4-diazepan-1-yl)pyrimidine-2-carbonitrile;

6-(4-(4-(2-(2-aminopyridin-3-yl)-5-phenyl-3H-imidazo[4,5-b]pyridin-3-yl)benzyl)-1,4-diazepan-1-yl)pyrimidine-4-carbonitrile;

4-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-2-carbonitrile;

2-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile;

6-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile;

4-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-2-carbonitrile;

2-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-4-carbonitrile;

6-(5-(4-(2-(2-aminopyridin-3-yl)-5-phenyl-3H-imidazo[4,5-b]pyridin-3-yl)benzyl)-2,5-diazabicyclo[2.2.2]octan-2-yl)pyrimidine-4-carbonitrile;

4-((1-((4-(2-(2-aminopyridin-3-yl)-5-phenyl-3H-imidazo[4,5-b]pyridin-3-yl)phenyl)methyl-d2)piperidin-4-yl)amino)pyrimidine-2-carbonitrile;

4-((1-(4-(2-(2-aminopyridin-3-yl)-5-phenyl-3H-imidazo[4,5-b]pyridin-3-yl)benzyl)piperidin-4-yl)(methyl)amino)-1,3,5-triazine-2-carbonitrile;

(S)-4-((1-(4-(2-(2-aminopyridin-3-yl)-5-phenyl-3H-imidazo[4,5-b]pyridin-3-yl)benzyl)piperidin-3-yl)amino)-1,3,5-triazine-2-carbonitrile;

(R)-4-(4-(4-(2-(2-aminopyridin-3-yl)-5-phenyl-3H-imidazo[4,5-b]pyridin-3-yl)benzyl)-2-methylpiperazin-1-yl)pyrimidine-2-carbonitrile;

(R)-2-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile;

(R)-6-(4-(4-(2-(2-aminopyridin-3-yl)-5-phenyl-3H-imidazo[4,5-b]pyridin-3-yl)benzyl)-2-methylpiperazin-1-yl)pyrimidine-4-carbonitrile;

2-(4-(4-(2-(2-aminopyridin-3-yl)-5-phenyl-3H-imidazo[4,5-b]pyridin-3-yl)benzyl)-1,4-diazepan-1-yl)pyrimidine-4-carbonitrile;

N-(3-(4-(2-(2-aminopyridin-3-yl)-5-phenyl-3H-imidazo[4,5-b]pyridin-3-yl)benzyl)-3-azabicyclo[3.2.1]octan-8-yl)-2-cyanopyrimidine-4-carboxamide;

N-(3-(4-(2-(2-aminopyridin-3-yl)-5-phenyl-3H-imidazo[4,5-b]pyridin-3-yl)benzyl)-3-azabicyclo[3.2.1]octan-8-yl)-6-cyanopyrimidine-4-carboxamide;

2-((3-(4-(2-(2-aminopyridin-3-yl)-5-phenyl-3H-imidazo[4,5-b]pyridin-3-yl)benzyl)-3-azabicyclo[3.2.1]octan-8-yl)amino)pyrimidine-4-carbonitrile;

4-((1-(4-(2-(2-aminopyridin-3-yl)-5-phenyl-3H-imidazo[4,5-b]pyridin-3-yl)benzyl)piperidin-4-yl)(methyl-d3)amino)pyrimidine-2-carbonitrile;

4-((1-(4-(2-(2-aminopyridin-3-yl)-5-phenyl-3H-imidazo[4,5-b]pyridin-3-yl)benzyl)piperidin-4-yl)(methyl-d3)amino)-1,3,5-triazine-2-carbonitrile;

N-(1-(4-(2-(2-aminopyridin-3-yl)-5-phenyl-3H-imidazo[4,5-b]pyridin-3-yl)benzyl)piperidin-4-yl)-2-cyano-N-(methyl-d3)pyrimidine-4-carboxamide;

4-(4-(4-(2-(2-aminopyridin-3-yl)-5-morpholino-3H-imidazo[4,5-b]pyridin-3-yl)benzyl)piperazin-1-yl)pyrimidine-2-carbonitrile;

2-(4-(4-(2-(2-aminopyridin-3-yl)-5-morpholino-3H-imidazo[4,5-b]pyridin-3-yl)benzyl)piperazin-1-yl)pyrimidine-4-carbonitrile;

6-(4-(4-(2-(2-aminopyridin-3-yl)-5-morpholino-3H-imidazo[4,5-b]pyridin-3-yl)benzyl)piperazin-1-yl)pyrimidine-4-carbonitrile;

4-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-morpholino-3H-imidazo[4,5-b]pyridin-3-yl)benzyl)piperidin-4-yl)amino)pyrimidine-2-carbonitrile;

2-((1-(4-(2-(2-aminopyridin-3-yl)-5-morpholino-3H-imidazo[4,5-b]pyridin-3-yl)benzyl)piperidin-4-yl)amino)pyrimidine-4-carbonitrile;
6-((1-(4-(2-(2-aminopyridin-3-yl)-5-morpholino-3H-imidazo[4,5-b]pyridin-3-yl)benzyl)piperidin-4-yl)amino)pyrimidine-4-carbonitrile;
4-(4-(4-(2-(2-aminopyridin-3-yl)-5-(4-fluorophenyl)-3H-imidazo[4,5-b]pyridin-3-yl)benzyl)piperazin-1-yl)pyrimidine-2-carbonitrile;
2-(4-(4-(2-(2-aminopyridin-3-yl)-5-(4-fluorophenyl)-3H-imidazo[4,5-b]pyridin-3-yl)benzyl)piperazin-1-yl)pyrimidine-4-carbonitrile;
4-(4-(4-(2-(2-aminopyridin-3-yl)-5-phenyl-3H-imidazo[4,5-b]pyridin-3-yl)benzyl)piperazine-1-carbonyl)thiazole-2-carbonitrile;
4-((7-(4-(2-(2-aminopyridin-3-yl)-5-phenyl-3H-imidazo[4,5-b]pyridin-3-yl)benzyl)-7-azaspiro[3.5]nonan-2-yl)amino)-1,3,5-triazine-2-carbonitrile;
4-(7-(4-(2-(2-aminopyridin-3-yl)-5-phenyl-3H-imidazo[4,5-b]pyridin-3-yl)benzyl)-2,7-diazaspiro[3.5]nonan-2-yl)-1,3,5-triazine-2-carbonitrile;
4-(4-(4-(2-(2-aminopyridin-3-yl)-5-phenyl-3H-imidazo[4,5-b]pyridin-3-yl)benzyl)-1,4-diazepan-1-yl)-1,3,5-triazine-2-carbonitrile;
4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile;
4-(2-(4-(2-(2-aminopyridin-3-yl)-5-phenyl-3H-imidazo[4,5-b]pyridin-3-yl)benzyl)-2,8-diazaspiro[4.5]decan-8-yl)-1,3,5-triazine-2-carbonitrile;
4-(2-(4-(2-(2-aminopyridin-3-yl)-5-phenyl-3H-imidazo[4,5-b]pyridin-3-yl)benzyl)-2,7-diazaspiro[4.5]decan-7-yl)-1,3,5-triazine-2-carbonitrile;
4-(9-(4-(2-(2-aminopyridin-3-yl)-5-phenyl-3H-imidazo[4,5-b]pyridin-3-yl)benzyl)-2,9-diazaspiro[5.5]undecan-2-yl)-1,3,5-triazine-2-carbonitrile;
(R)-4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile;
4-((2R,6R)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile;
4-(5-(4-(2-(2-aminopyridin-3-yl)-5-phenyl-3H-imidazo[4,5-b]pyridin-3-yl)benzyl)-2,5-diazabicyclo[2.2.2]octan-2-yl)-1,3,5-triazine-2-carbonitrile;
4-(4-(4-(2-(2-aminopyridin-3-yl)-5-cyclopropyl-3H-imidazo[4,5-b]pyridin-3-yl)benzyl)piperazin-1-yl)pyrimidine-2-carbonitrile;
4-(4-(4-(2-(2-aminopyridin-3-yl)-5-(2-oxo-1,2-dihydropyridin-3-yl)-3H-imidazo[4,5-b]pyridin-3-yl)benzyl)piperazin-1-yl)pyrimidine-2-carbonitrile;
4-(4-(4-(2-(2-aminopyridin-3-yl)-5-(1-methyl-2-oxo-1,2-dihydropyridin-3-yl)-3H-imidazo[4,5-b]pyridin-3-yl)benzyl)piperazin-1-yl)pyrimidine-2-carbonitrile;
4-((1-(4-(2-(2-aminopyridin-3-yl)-5-(1-methyl-2-oxo-1,2-dihydropyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-cyclobutyl-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(cyclohex-1-en-1-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-cyclohexyl-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(3-cyanophenyl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-oxo-1,6-dihydropyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-oxo-1,6-dihydropyridin-2-yl)-3H-imidazo[4,5-b]pyridin-3-yl)benzyl)piperidin-4-yl)amino)pyrimidine-2-carbonitrile;
4-(2-(4-(2-(2-aminopyridin-3-yl)-5-phenyl-3H-imidazo[4,5-b]pyridin-3-yl)benzyl)-2,7-diazaspiro[3.5]nonan-7-yl)-1,3,5-triazine-2-carbonitrile;
(S)-4-(7-(4-(2-(2-aminopyridin-3-yl)-5-phenyl-3H-imidazo[4,5-b]pyridin-3-yl)benzyl)-2,7-diazaspiro[4.4]nonan-2-yl)-1,3,5-triazine-2-carbonitrile;
4-(3-(4-(2-(2-aminopyridin-3-yl)-5-phenyl-3H-imidazo[4,5-b]pyridin-3-yl)benzyl)-3,8-diazabicyclo[3.2.1]octan-8-yl)-1,3,5-triazine-2-carbonitrile;
4-(8-(4-(2-(2-aminopyridin-3-yl)-5-phenyl-3H-imidazo[4,5-b]pyridin-3-yl)benzyl)-3,8-diazabicyclo[3.2.1]octan-3-yl)-1,3,5-triazine-2-carbonitrile;
4-((1R,4R)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile;
(R)-4-(4-(4-(2-(2-aminopyridin-3-yl)-5-phenyl-3H-imidazo[4,5-b]pyridin-3-yl)benzyl)-2-methylpiperazin-1-yl)-1,3,5-triazine-2-carbonitrile;
(S)-4-(4-(4-(2-(2-aminopyridin-3-yl)-5-phenyl-3H-imidazo[4,5-b]pyridin-3-yl)benzyl)-2-methylpiperazin-1-yl)-1,3,5-triazine-2-carbonitrile;
4-((2S,6S)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile;
4-(7-(4-(2-(2-aminopyridin-3-yl)-5-phenyl-3H-imidazo[4,5-b]pyridin-3-yl)benzyl)-4,7-diazaspiro[2.5]octan-4-yl)-1,3,5-triazine-2-carbonitrile;
4-((2R,6S)-4-(4-(2-(2-aminopyridin-3-yl)-5-phenyl-3H-imidazo[4,5-b]pyridin-3-yl)benzyl)-2,6-dimethylpiperazin-1-yl)-1,3,5-triazine-2-carbonitrile;
4-((1-(4-(2-(2-aminopyridin-3-yl)-5-phenyl-3H-imidazo[4,5-b]pyridin-3-yl)benzyl)azepan-4-yl)amino)-1,3,5-triazine-2-carbonitrile;
4-((4-(4-(2-(2-aminopyridin-3-yl)-5-phenyl-3H-imidazo[4,5-b]pyridin-3-yl)benzyl)-1,4-oxazepan-6-yl)amino)-1,3,5-triazine-2-carbonitrile;
4-((1-(4-(2-(2-aminopyridin-3-yl)-5-methyl-3H-imidazo[4,5-b]pyridin-3-yl)benzyl)piperidin-4-yl)amino)pyrimidine-2-carbonitrile;
4-(4-(4-(2-(2-aminopyridin-3-yl)-5-(2-fluorophenyl)-3H-imidazo[4,5-b]pyridin-3-yl)benzyl)piperazin-1-yl)pyrimidine-2-carbonitrile;
2-(4-(4-(2-(2-aminopyridin-3-yl)-5-(2-fluorophenyl)-3H-imidazo[4,5-b]pyridin-3-yl)benzyl)piperazin-1-yl)pyrimidine-4-carbonitrile;
2-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-4-carbonitrile;
6-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-4-carbonitrile;
4-(8-(4-(2-(2-aminopyridin-3-yl)-5-morpholino-3H-imidazo[4,5-b]pyridin-3-yl)benzyl)-3,8-diazabicyclo[3.2.1]octan-3-yl)-1,3,5-triazine-2-carbonitrile;
4-((1-(4-(2-(2-aminopyridin-3-yl)-5-isopropyl-3H-imidazo[4,5-b]pyridin-3-yl)benzyl)piperidin-4-yl)amino)pyrimidine-2-carbonitrile;

4-((1-(4-(2-(2-aminopyridin-3-yl)-5-methoxy-3H-imidazo[4,5-b]pyridin-3-yl)benzyl)piperidin-4-yl)amino)pyrimidine-2-carbonitrile;

2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxamide;

2-(2-aminopyridin-3-yl)-3-(4-((4-((2-cyanopyrimidin-4-yl)amino)piperidin-1-yl)methyl)phenyl)-N,N-dimethyl-3H-imidazo[4,5-b]pyridine-5-carboxamide;

6-(4-(4-(2-(2-aminopyridin-3-yl)-5-cyclopropyl-3H-imidazo[4,5-b]pyridin-3-yl)benzyl)piperazin-1-yl)pyrimidine-4-carbonitrile;

6-((1-(4-(2-(2-aminopyridin-3-yl)-5-cyclopropyl-3H-imidazo[4,5-b]pyridin-3-yl)benzyl)piperidin-4-yl)amino)pyrimidine-4-carbonitrile;

4-(4-(4-(2-(2-aminopyridin-3-yl)-5-morpholino-3H-imidazo[4,5-b]pyridin-3-yl)benzyl)piperazin-1-yl)-1,3,5-triazine-2-carbonitrile;

4-(4-(4-(2-(2-aminopyridin-3-yl)-5-(2-cyanophenyl)-3H-imidazo[4,5-b]pyridin-3-yl)benzyl)piperazin-1-yl)pyrimidine-2-carbonitrile;

4-(4-(4-(2-(2-aminopyridin-3-yl)-5-(4-cyanophenyl)-3H-imidazo[4,5-b]pyridin-3-yl)benzyl)piperazin-1-yl)pyrimidine-2-carbonitrile;

4-(4-(4-(2-(2-aminopyridin-3-yl)-5-(3-fluorophenyl)-3H-imidazo[4,5-b]pyridin-3-yl)benzyl)piperazin-1-yl)pyrimidine-2-carbonitrile;

4-(4-(4-(2-(2-aminopyridin-3-yl)-5-(3-chlorophenyl)-3H-imidazo[4,5-b]pyridin-3-yl)benzyl)piperazin-1-yl)pyrimidine-2-carbonitrile;

2-(4-(4-(2-(2-aminopyridin-3-yl)-5-(3-chlorophenyl)-3H-imidazo[4,5-b]pyridin-3-yl)benzyl)piperazin-1-yl)pyrimidine-4-carbonitrile;

4-((1-(4-(2-(2-aminopyridin-3-yl)-5-cyclopropyl-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(tetrahydro-2H-pyran-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-phenyl-3H-imidazo[4,5-b]pyridin-3-yl)benzyl)azetidin-3-yl)amino)-1,3,5-triazine-2-carbonitrile;

4-(6-(4-(2-(2-aminopyridin-3-yl)-5-phenyl-3H-imidazo[4,5-b]pyridin-3-yl)benzyl)-2,6-diazaspiro[3.4]octan-2-yl)-1,3,5-triazine-2-carbonitrile;

4-(7-(4-(2-(2-aminopyridin-3-yl)-5-phenyl-3H-imidazo[4,5-b]pyridin-3-yl)benzyl)-2,7-diazaspiro[4.4]nonan-2-yl)pyrimidine-2-carbonitrile;

4-(6-(4-(2-(2-aminopyridin-3-yl)-5-phenyl-3H-imidazo[4,5-b]pyridin-3-yl)benzyl)-2,6-diazaspiro[3.3]heptan-2-yl)-1,3,5-triazine-2-carbonitrile;

4-(4-(4-(2-(2-aminopyridin-3-yl)-5-(2-chlorophenyl)-3H-imidazo[4,5-b]pyridin-3-yl)benzyl)piperazin-1-yl)-1,3,5-triazine-2-carbonitrile;

4-((1-(4-(2-(2-aminopyridin-3-yl)-5-(2-chlorophenyl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(2-chlorophenyl)-3H-imidazo[4,5-b]pyridin-3-yl)benzyl)piperidin-4-yl)amino)pyrimidine-4-carbonitrile;

6-((1-(4-(2-(2-aminopyridin-3-yl)-5-(2-chlorophenyl)-3H-imidazo[4,5-b]pyridin-3-yl)benzyl)piperidin-4-yl)amino)pyrimidine-4-carbonitrile;

4-((1-(4-(2-(2-aminopyridin-3-yl)-5-(4-chlorophenyl)-3H-imidazo[4,5-b]pyridin-3-yl)benzyl)piperidin-4-yl)amino)pyrimidine-2-carbonitrile;

2-(4-(4-(2-(2-aminopyridin-3-yl)-5-(3-fluorophenyl)-3H-imidazo[4,5-b]pyridin-3-yl)benzyl)piperazin-1-yl)pyrimidine-4-carbonitrile;

6-(4-(4-(2-(2-aminopyridin-3-yl)-5-(3-fluorophenyl)-3H-imidazo[4,5-b]pyridin-3-yl)benzyl)piperazin-1-yl)pyrimidine-4-carbonitrile;

6-((1-(4-(2-(2-aminopyridin-3-yl)-5-(3-fluorophenyl)-3H-imidazo[4,5-b]pyridin-3-yl)benzyl)piperidin-4-yl)amino)pyrimidine-4-carbonitrile;

4-(4-(4-(2-(2-aminopyridin-3-yl)-5-(2-fluorophenyl)-3H-imidazo[4,5-b]pyridin-3-yl)benzyl)piperazin-1-yl)-1,3,5-triazine-2-carbonitrile;

2-((1-(4-(2-(2-aminopyridin-3-yl)-5-(2-fluorophenyl)-3H-imidazo[4,5-b]pyridin-3-yl)benzyl)piperidin-4-yl)amino)pyrimidine-4-carbonitrile;

6-(4-(4-(2-(2-aminopyridin-3-yl)-5-(2-fluorophenyl)-3H-imidazo[4,5-b]pyridin-3-yl)benzyl)piperazin-1-yl)pyrimidine-4-carbonitrile;

6-((1-(4-(2-(2-aminopyridin-3-yl)-5-(2-fluorophenyl)-3H-imidazo[4,5-b]pyridin-3-yl)benzyl)piperidin-4-yl)amino)pyrimidine-4-carbonitrile;

4-((1-(4-(2-(2-aminopyridin-3-yl)-5-(2-fluorophenyl)-3H-imidazo[4,5-b]pyridin-3-yl)benzyl)piperidin-4-yl)amino)pyrimidine-2-carbonitrile;

4-(4-(4-(2-(2-aminopyridin-3-yl)-5-(3-oxo-1,4-diazepan-1-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(3-oxo-1,4-diazepan-1-yl)-3H-imidazo[4,5-b]pyridin-3-yl)benzyl)piperidin-4-yl)amino)pyrimidine-2-carbonitrile;

2-(4-(4-(2-(2-aminopyridin-3-yl)-5-(4-cyanophenyl)-3H-imidazo[4,5-b]pyridin-3-yl)benzyl)piperazin-1-yl)pyrimidine-4-carbonitrile;

4-((1-(4-(2-(2-aminopyridin-3-yl)-5-(4-cyanophenyl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(4-cyanophenyl)-3H-imidazo[4,5-b]pyridin-3-yl)benzyl)piperidin-4-yl)amino)pyrimidine-2-carbonitrile;

2-(4-(4-(2-(2-aminopyridin-3-yl)-5-(2-cyanophenyl)-3H-imidazo[4,5-b]pyridin-3-yl)benzyl)piperazin-1-yl)pyrimidine-4-carbonitrile;

4-((1-(4-(2-(2-aminopyridin-3-yl)-5-(5-oxo-1,4-diazepan-1-yl)-3H-imidazo[4,5-b]pyridin-3-yl)benzyl)piperidin-4-yl)amino)pyrimidine-2-carbonitrile;

4-(4-(4-(2-(2-aminopyridin-3-yl)-5-(2-chlorophenyl)-3H-imidazo[4,5-b]pyridin-3-yl)benzyl)piperazin-1-yl)pyrimidine-2-carbonitrile;

2-(4-(4-(2-(2-aminopyridin-3-yl)-5-(2-chlorophenyl)-3H-imidazo[4,5-b]pyridin-3-yl)benzyl)piperazin-1-yl)pyrimidine-4-carbonitrile;

6-(4-(4-(2-(2-aminopyridin-3-yl)-5-(2-chlorophenyl)-3H-imidazo[4,5-b]pyridin-3-yl)benzyl)piperazin-1-yl)pyrimidine-4-carbonitrile;

5-(4-(4-(2-(2-aminopyridin-3-yl)-5-phenyl-3H-imidazo[4,5-b]pyridin-3-yl)benzyl)piperazine-1-carbonyl)thiazole-2-carbonitrile;

4-(4-(4-(2-(2-aminopyridin-3-yl)-5-phenyl-3H-imidazo[4,5-b]pyridin-3-yl)benzyl)piperazin-1-yl)-1,3,5-triazine-2-carbonitrile;

4-(4-(4-(2-(2-aminopyridin-3-yl)-5-(cyclohex-1-en-1-yl)-3H-imidazo[4,5-b]pyridin-3-yl)benzyl)piperazin-1-yl)pyrimidine-2-carbonitrile;

4-(4-(4-(2-(2-aminopyridin-3-yl)-5-(3,6-dihydro-2H-pyran-4-yl)-3H-imidazo[4,5-b]pyridin-3-yl)benzyl)piperazin-1-yl)pyrimidine-2-carbonitrile;

4-(4-(4-(2-(2-aminopyridin-3-yl)-5-(3-cyanophenyl)-3H-imidazo[4,5-b]pyridin-3-yl)benzyl)piperazin-1-yl)pyrimidine-2-carbonitrile;

4-(4-(4-(2-(2-aminopyridin-3-yl)-5-(6-oxo-1,6-dihydropyridin-3-yl)-3H-imidazo[4,5-b]pyridin-3-yl)benzyl)piperazin-1-yl)pyrimidine-2-carbonitrile;

2-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-4-carbonitrile;

6-(4-(4-(2-(2-aminopyridin-3-yl)-5-(6-oxo-1,6-dihydropyridin-2-yl)-3H-imidazo[4,5-b]pyridin-3-yl)benzyl)piperazin-1-yl)pyrimidine-4-carbonitrile;

4-((1-(4-(2-(2-aminopyridin-3-yl)-5-(2-cyanophenyl)-3H-imidazo[4,5-b]pyridin-3-yl)benzyl)piperidin-4-yl)amino)pyrimidine-2-carbonitrile;

N-(1-(4-(2-(2-aminopyridin-3-yl)-5-phenyl-3H-imidazo[4,5-b]pyridin-3-yl)benzyl)piperidin-4-yl)-2-cyano-N-methylpyrimidine-4-carboxamide;

(R)-4-((1-(4-(2-(2-aminopyridin-3-yl)-5-phenyl-3H-imidazo[4,5-b]pyridin-3-yl)benzyl)piperidin-3-yl)amino)-1,3,5-triazine-2-carbonitrile;

4-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)-1,3,5-triazine-2-carbonitrile;

4-((3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile;

4-((3aR,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)-1,3,5-triazine-2-carbonitrile;

4-((3aR,6aR)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile;

4-(4-(4-(2-(2-aminopyridin-3-yl)-5-(4-chlorophenyl)-3H-imidazo[4,5-b]pyridin-3-yl)benzyl)piperazin-1-yl)pyrimidine-2-carbonitrile;

2-(4-(4-(2-(2-aminopyridin-3-yl)-5-(4-chlorophenyl)-3H-imidazo[4,5-b]pyridin-3-yl)benzyl)piperazin-1-yl)pyrimidine-4-carbonitrile;

6-(4-(4-(2-(2-aminopyridin-3-yl)-5-(4-chlorophenyl)-3H-imidazo[4,5-b]pyridin-3-yl)benzyl)piperazin-1-yl)pyrimidine-4-carbonitrile;

4-(4-(4-(2-(2-aminopyridin-3-yl)-5-(4-methyl-5-oxo-1,4-diazepan-1-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(4-methyl-5-oxo-1,4-diazepan-1-yl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(3-oxo-1,4-diazepan-1-yl)-3H-imidazo[4,5-b]pyridin-3-yl)benzyl)piperidin-4-yl)amino)pyrimidine-4-carbonitrile;

4-(4-(4-(2-(2-aminopyridin-3-yl)-5-(1-methyl-6-oxo-1,6-dihydropyridin-3-yl)-3H-imidazo[4,5-b]pyridin-3-yl)benzyl)piperazin-1-yl)pyrimidine-2-carbonitrile;

4-(4-(4-(2-(2-aminopyridin-3-yl)-5-(1-methyl-2-oxo-1,2-dihydropyridin-4-yl)-3H-imidazo[4,5-b]pyridin-3-yl)benzyl)piperazin-1-yl)pyrimidine-2-carbonitrile;

2-(4-(4-(2-(2-aminopyridin-3-yl)-5-cyclopropyl-3H-imidazo[4,5-b]pyridin-3-yl)benzyl)piperazin-1-yl)pyrimidine-4-carbonitrile;

2-((1-(4-(2-(2-aminopyridin-3-yl)-5-cyclopropyl-3H-imidazo[4,5-b]pyridin-3-yl)benzyl)piperidin-4-yl)amino)pyrimidine-4-carbonitrile;

2-((1-(4-(2-(2-aminopyridin-3-yl)-5-(4-fluorophenyl)-3H-imidazo[4,5-b]pyridin-3-yl)benzyl)piperidin-4-yl)amino)pyrimidine-4-carbonitrile;

4-((1-(4-(2-(2-aminopyridin-3-yl)-5-(3-chlorophenyl)-3H-imidazo[4,5-b]pyridin-3-yl)benzyl)piperidin-4-yl)amino)pyrimidine-2-carbonitrile;

2-(4-(4-(2-(2-aminopyridin-3-yl)-5-(1-methyl-6-oxo-1,6-dihydropyridin-3-yl)-3H-imidazo[4,5-b]pyridin-3-yl)benzyl)piperazin-1-yl)pyrimidine-4-carbonitrile;

4-((1-(4-(2-(2-aminopyridin-3-yl)-5-(1-methyl-6-oxo-1,6-dihydropyridin-3-yl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(1-methyl-6-oxo-1,6-dihydropyridin-3-yl)-3H-imidazo[4,5-b]pyridin-3-yl)benzyl)piperidin-4-yl)amino)pyrimidine-4-carbonitrile;

4-((1-(4-(2-(2-aminopyridin-3-yl)-5-(3-fluorophenyl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(3-fluorophenyl)-3H-imidazo[4,5-b]pyridin-3-yl)benzyl)piperidin-4-yl)amino)pyrimidine-4-carbonitrile;

4-((1-(4-(2-(2-aminopyridin-3-yl)-5-(1-methyl-2-oxo-1,2-dihydropyridin-4-yl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(1-methyl-2-oxo-1,2-dihydropyridin-4-yl)-3H-imidazo[4,5-b]pyridin-3-yl)benzyl)piperidin-4-yl)amino)pyrimidine-4-carbonitrile;

4-(7-(4-(2-(2-aminopyridin-3-yl)-5-phenyl-3H-imidazo[4,5-b]pyridin-3-yl)benzyl)-2,7-diazaspiro[3.5]nonan-2-yl)pyrimidine-2-carbonitrile;

4-((7-(4-(2-(2-aminopyridin-3-yl)-5-phenyl-3H-imidazo[4,5-b]pyridin-3-yl)benzyl)-7-azaspiro[3.5]nonan-2-yl)amino)pyrimidine-2-carbonitrile;

4-(8-(4-(2-(2-aminopyridin-3-yl)-5-phenyl-3H-imidazo[4,5-b]pyridin-3-yl)benzyl)-2,8-diazaspiro[4.5]decan-2-yl)-1,3,5-triazine-2-carbonitrile;

4-(9-(4-(2-(2-aminopyridin-3-yl)-5-phenyl-3H-imidazo[4,5-b]pyridin-3-yl)benzyl)-3,9-diazaspiro[5.5]undecan-3-yl)pyrimidine-2-carbonitrile;

4-(9-(4-(2-(2-aminopyridin-3-yl)-5-phenyl-3H-imidazo[4,5-b]pyridin-3-yl)benzyl)-3,9-diazaspiro[5.5]undecan-3-yl)-1,3,5-triazine-2-carbonitrile;

4-(6-(4-(2-(2-aminopyridin-3-yl)-5-phenyl-3H-imidazo[4,5-b]pyridin-3-yl)benzyl)-2,6-diazaspiro[3.3]heptan-2-yl)pyrimidine-2-carbonitrile;

4-((3aS,6aS)-5-(4-(2-(2-aminopyridin-3-yl)-5-phenyl-3H-imidazo[4,5-b]pyridin-3-yl)benzyl)hexahydropyrrolo[3,4-c]pyrrol-2(1H)-yl)pyrimidine-2-carbonitrile;

4-(4-(4-(2-(2-aminopyridin-3-yl)-5-(4-fluorophenyl)-3H-imidazo[4,5-b]pyridin-3-yl)benzyl)piperazin-1-yl)-1,3,5-triazine-2-carbonitrile;

4-(4-(4-(2-(2-aminopyridin-3-yl)-5-(4-chlorophenyl)-3H-imidazo[4,5-b]pyridin-3-yl)benzyl)piperazin-1-yl)-1,3,5-triazine-2-carbonitrile;

4-((1-(4-(2-(2-aminopyridin-3-yl)-5-(4-fluorophenyl)-3H-imidazo[4,5-b]pyridin-3-yl)benzyl)piperidin-4-yl)amino)pyrimidine-2-carbonitrile;

2-((1-(4-(2-(2-aminopyridin-3-yl)-5-(4-chlorophenyl)-3H-imidazo[4,5-b]pyridin-3-yl)benzyl)piperidin-4-yl)amino)pyrimidine-4-carbonitrile;

2-((1-(4-(2-(2-aminopyridin-3-yl)-5-(3-chlorophenyl)-3H-imidazo[4,5-b]pyridin-3-yl)benzyl)piperidin-4-yl)amino)pyrimidine-4-carbonitrile;

6-((1-(4-(2-(2-aminopyridin-3-yl)-5-(3-chlorophenyl)-3H-imidazo[4,5-b]pyridin-3-yl)benzyl)piperidin-4-yl)amino)pyrimidine-4-carbonitrile;

6-(4-(4-(2-(2-aminopyridin-3-yl)-5-(3-chlorophenyl)-3H-imidazo[4,5-b]pyridin-3-yl)benzyl)piperazin-1-yl)pyrimidine-4-carbonitrile;

4-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-2-carbonitrile;

6-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile;

2-((1S,4S)-5-(4-(2-(2-aminopyridin-3-yl)-5-phenyl-3H-imidazo[4,5-b]pyridin-3-yl)benzyl)-2,5-diazabicyclo[2.2.1]heptan-2-yl)pyrimidine-4-carbonitrile;

4-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-2-carbonitrile;

2-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile;

6-((2S,6R)-4-(4-(2-(2-aminopyridin-3-yl)-5-phenyl-3H-imidazo[4,5-b]pyridin-3-yl)benzyl)-2,6-dimethylpiperazin-1-yl)pyrimidine-4-carbonitrile;

4-((1-(4-(2-(2-aminopyridin-3-yl)-5-(2-oxo-1,2-dihydropyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-chlorophenyl)-3H-imidazo[4,5-b]pyridin-3-yl)benzyl)piperidin-4-yl)amino)-1,3,5-triazine-2-carbonitrile;

4-(4-(4-(2-(2-aminopyridin-3-yl)-5-(4-cyanopyridin-3-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(4-cyanopyridin-3-yl)-3H-imidazo[4,5-b]pyridin-3-yl)benzyl)piperidin-4-yl)amino)pyrimidine-2-carbonitrile;

4-((1-((4-(2-(2-aminopyridin-3-yl)-3H-imidazo[4,5-b]pyridin-3-yl)phenyl)methyl-d2)piperidin-4-yl)amino)pyrimidine-2-carbonitrile;

4-(4-(4-(2-(2-aminopyridin-3-yl)-5-(4-methyl-3-oxo-1,4-diazepan-1-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(3-oxomorpholino)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-cyclopentyl-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(dimethylamino)-3H-imidazo[4,5-b]pyridin-3-yl)benzyl)piperidin-4-yl)amino)pyrimidine-2-carbonitrile;

4-((1-(4-(2-(2-aminopyridin-3-yl)-3H-imidazo[4,5-b]pyridin-3-yl)benzyl)piperidin-4-yl)(methyl)amino)pyrimidine-2-carbonitrile;

4-((1-(4-(2-(2-aminopyridin-3-yl)-5-phenyl-3H-imidazo[4,5-b]pyridin-3-yl)benzyl)piperidin-4-yl)amino)-1,3,5-triazine-2-carbonitrile;

4-((1-(4-(2-(2-aminopyridin-3-yl)-3H-imidazo[4,5-b]pyridin-3-yl)benzyl)-4-methylpiperidin-4-yl)amino)pyrimidine-2-carbonitrile;

4-((1-(4-(2-(2-aminopyridin-3-yl)-5-(1-methyl-6-oxo-1,6-dihydropyridin-2-yl)-3H-imidazo[4,5-b]pyridin-3-yl)benzyl)piperidin-4-yl)amino)pyrimidine-2-carbonitrile;

4-(4-(4-(2-(2-aminopyridin-3-yl)-5-(1-methyl-6-oxo-1,6-dihydropyridin-2-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(3-methoxyphenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(tert-butyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-ethyl-3H-imidazo[4,5-b]pyridin-3-yl)benzyl)piperidin-4-yl)amino)pyrimidine-2-carbonitrile;

2-(2-aminopyridin-3-yl)-3-(4-((4-((2-cyanopyrimidin-4-yl)amino)piperidin-1-yl)methyl)phenyl)-N-methyl-3H-imidazo[4,5-b]pyridine-5-carboxamide;

4-(4-(4-(2-(2-aminopyridin-3-yl)-5-(3-cyanopyridin-4-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(3-cyanopyridin-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-fluoro-3H-imidazo[4,5-b]pyridin-3-yl)benzyl)piperidin-4-yl)amino)pyrimidine-2-carbonitrile;

4-((1-(4-(2-(2-aminopyridin-3-yl)-6-fluoro-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-oxooxazolidin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-fluoropyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-chloro-3H-imidazo[4,5-b]pyridin-3-yl)benzyl)piperidin-4-yl)amino)pyrimidine-2-carbonitrile;

2-(2-aminopyridin-3-yl)-3-(4-((4-((2-cyanopyrimidin-4-yl)amino)piperidin-1-yl)methyl)phenyl)-3H-imidazo[4,5-b]pyridine-5-carbonitrile;

4-(4-(4-(2-(2-aminopyridin-3-yl)-5-(3-cyanopyridin-2-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(3-cyanopyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-cyanopyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(trifluoromethyl)-3H-imidazo[4,5-b]pyridin-3-yl)benzyl)piperidin-4-yl)amino)pyrimidine-2-carbonitrile;

2-(2-aminopyridin-3-yl)-3-(4-((4-((2-cyanopyrimidin-4-yl)amino)piperidin-1-yl)methyl)phenyl)-3H-imidazo[4,5-b]pyridine-6-carbonitrile;

4-((1-(4-(2-(2-aminopyridin-3-yl)-5,6-dimethyl-3H-imidazo[4,5-b]pyridin-3-yl)benzyl)piperidin-4-yl)amino)pyrimidine-2-carbonitrile;

4-((1-(4-(2-(2-aminopyridin-3-yl)-1H-imidazo[4,5-b]pyrazin-1-yl)benzyl)piperidin-4-yl)amino)pyrimidine-2-carbonitrile;

methyl 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylate;

2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylic acid;

4-((1-(4-(2-(2-aminopyridin-3-yl)-5-(fluoromethoxy)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(tetrahydrofuran-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-cyanopyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-cyanopyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(oxetan-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-methoxyphenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-methoxyphenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(trifluoromethoxy)-3H-imidazo[4,5-b]pyridin-3-yl)benzyl)piperidin-4-yl)amino)pyrimidine-2-carbonitrile;

4-(4-(4-(2-(2-aminopyridin-3-yl)-5-(2-cyanopyridin-3-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-isopropoxy-3H-imidazo[4,5-b]pyridin-3-yl)benzyl)piperidin-4-yl)amino)pyrimidine-2-carbonitrile;

4-((4-(4-(2-(2-aminopyridin-3-yl)-5-phenyl-3H-imidazo[4,5-b]pyridin-3-yl)benzyl)piperazin-1-yl)amino)pyrimidine-2-carbonitrile;

4-((1-(4-(2-(2-aminopyridin-3-yl)-5-(methoxy-d3)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-cyanopyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-cyanopyridin-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-cyanopyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(pyridin-3-yl)-3H-imidazo[4,5-b]pyridin-3-yl)benzyl)piperidin-4-yl)amino)pyrimidine-2-carbonitrile;

4-(4-(4-(2-(2-aminopyridin-3-yl)-5-(pyridin-3-yl)-3H-imidazo[4,5-b]pyridin-3-yl)benzyl)piperazin-1-yl)pyrimidine-2-carbonitrile;

4-((1-(4-(2-(2-aminopyridin-3-yl)-5-(pyridin-4-yl)-3H-imidazo[4,5-b]pyridin-3-yl)benzyl)piperidin-4-yl)amino)pyrimidine-2-carbonitrile;

4-((7-(4-(2-(2-aminopyridin-3-yl)-5-morpholino-3H-imidazo[4,5-b]pyridin-3-yl)benzyl)-7-azaspiro[3.5]nonan-2-yl)amino)-1,3,5-triazine-2-carbonitrile;

4-((1-(4-(2-(2-aminopyridin-3-yl)-5-(methylthio)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(methylsulfonyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-methoxypyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-methyl-1H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-fluoro-3-methoxyphenyl)-3H-imidazo[4,5-b]pyridin-3-yl)benzyl)piperidin-4-yl)amino)pyrimidine-2-carbonitrile;

N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)acetamide;

4-((1-(4-(2-(2-aminopyridin-3-yl)-5-(4-fluorophenyl)-3H-imidazo[4,5-b]pyridin-3-yl)benzyl)piperidin-4-yl)(methyl-d3)amino)pyrimidine-2-carbonitrile;

4-((1-((4-(2-(2-aminopyridin-3-yl)-5-(4-fluorophenyl)-3H-imidazo[4,5-b]pyridin-3-yl)phenyl)methyl-d2)piperidin-4-yl)(methyl-d3)amino)pyrimidine-2-carbonitrile;

4-((1-(4-(2-(2-aminopyridin-3-yl)-5-(4-fluorophenyl)-3H-imidazo[4,5-b]pyridin-3-yl)benzyl)azetidin-3-yl)amino)pyrimidine-2-carbonitrile;

4-((7-(4-(2-(2-aminopyridin-3-yl)-5-(4-fluorophenyl)-3H-imidazo[4,5-b]pyridin-3-yl)benzyl)-7-azaspiro[3.5]nonan-2-yl)amino)pyrimidine-2-carbonitrile;

4-((2-(4-(2-(2-aminopyridin-3-yl)-5-(4-fluorophenyl)-3H-imidazo[4,5-b]pyridin-3-yl)benzyl)-2-azaspiro[3.3]heptan-6-yl)amino)pyrimidine-2-carbonitrile;

4-((2-(4-(2-(2-aminopyridin-3-yl)-5-(4-fluorophenyl)-3H-imidazo[4,5-b]pyridin-3-yl)benzyl)-2-azaspiro[3.5]nonan-7-yl)amino)pyrimidine-2-carbonitrile;

4-(6-(4-(2-(2-aminopyridin-3-yl)-5-(4-fluorophenyl)-3H-imidazo[4,5-b]pyridin-3-yl)benzyl)-2,6-diazaspiro[3.3]heptan-2-yl)pyrimidine-2-carbonitrile;

4-(8-(4-(2-(2-aminopyridin-3-yl)-5-(4-fluorophenyl)-3H-imidazo[4,5-b]pyridin-3-yl)benzyl)-3,8-diazabicyclo[3.2.1]octan-3-yl)pyrimidine-2-carbonitrile;

4-((3aR,6aS)-5-(4-(2-(2-aminopyridin-3-yl)-5-(4-fluorophenyl)-3H-imidazo[4,5-b]pyridin-3-yl)benzyl)hexahydropyrrolo[3,4-c]pyrrol-2(1H)-yl)pyrimidine-2-carbonitrile;

4-((3aS,6aS)-5-(4-(2-(2-aminopyridin-3-yl)-5-(4-fluorophenyl)-3H-imidazo[4,5-b]pyridin-3-yl)benzyl)hexahydropyrrolo[3,4-c]pyrrol-2(1H)-yl)pyrimidine-2-carbonitrile;

4-((1-(4-(2-(2-aminopyridin-3-yl)-5-(4-fluorophenyl)-3H-imidazo[4,5-b]pyridin-3-yl)benzyl)piperidin-4-yl-4-d)amino)pyrimidine-2-carbonitrile;

4-((1-(4-(2-(2-aminopyridin-3-yl)-5,6-dimethyl-3H-imidazo[4,5-b]pyridin-3-yl)benzyl)piperidin-4-yl-4-d)amino)pyrimidine-2-carbonitrile;

4-((1-(4-(2-(2-aminopyridin-3-yl)-5-(cyclopent-1-en-1-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-vinyl-3H-imidazo[4,5-b]pyridin-3-yl)benzyl)piperidin-4-yl)amino)pyrimidine-2-carbonitrile;

4-((1-(4-(2-(2-aminopyridin-3-yl)-5,6-dimethyl-3H-imidazo[4,5-b]pyridin-3-yl)benzyl)piperidin-4-yl)(methyl-d3)amino)pyrimidine-2-carbonitrile;

4-((1-(4-(2-(2-aminopyridin-3-yl)-5-(5-fluoropyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(methylamino)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(bis(methyl-d3)amino)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-((methyl-d3)amino)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(azetidin-1-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(isoxazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(oxazol-5-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-methylisoxazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-methylisoxazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-methyl-1H-pyrazol-5-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-ethyl-1H-pyrazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-methyl-1H-pyrazol-5-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-(2-oxopyrrolidin-1-yl)phenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-fluoro-2-methoxyphenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-(trifluoromethyl)phenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-(trifluoromethyl)phenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3,5-dimethylisoxazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-(difluoromethyl)-1H-pyrazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2,4-difluorophenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-methoxypyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-methylpyridin-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-methylpyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-isopropyl-1H-pyrazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(isothiazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-cyano-1-methyl-1H-pyrrol-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(thiazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(isothiazol-5-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1,5-dimethyl-1H-pyrazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-bromo-3H-imidazo[4,5-b]pyridin-3-yl)benzyl)piperidin-4-yl)amino)pyrimidine-2-carbonitrile;

4-((1-((4-(2-(2-aminopyridin-3-yl)-5-bromo-3H-imidazo[4,5-b]pyridin-3-yl)phenyl)methyl-d2)piperidin-4-yl)amino)pyrimidine-2-carbonitrile;

4-((1-(4-(2-(2-aminopyridin-3-yl)-5-(4-fluorophenyl)-3H-imidazo[4,5-b]pyridin-3-yl)benzyl)piperidin-4-yl)amino)-1,3,5-triazine-2-carbonitrile;

4-((1-((4-(2-(2-aminopyridin-3-yl)-5-(4-fluorophenyl)-3H-imidazo[4,5-b]pyridin-3-yl)phenyl)methyl-d2)piperidin-4-yl)(methyl)amino)pyrimidine-2-carbonitrile;

4-((1-((4-(2-(2-aminopyridin-3-yl)-5-(4-fluorophenyl)-3H-imidazo[4,5-b]pyridin-3-yl)phenyl)methyl-d2)piperidin-4-yl)amino)pyrimidine-2-carbonitrile;

4-(7-(4-(2-(2-aminopyridin-3-yl)-5-(4-fluorophenyl)-3H-imidazo[4,5-b]pyridin-3-yl)benzyl)-2,7-diazaspiro[3.5]nonan-2-yl)pyrimidine-2-carbonitrile;

4-(2-(4-(2-(2-aminopyridin-3-yl)-5-(4-fluorophenyl)-3H-imidazo[4,5-b]pyridin-3-yl)benzyl)-2,7-diazaspiro[3.5]nonan-7-yl)pyrimidine-2-carbonitrile;

4-((1-(4-(2-(2-aminopyridin-3-yl)-5-(methylsulfinyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5,7-dimethyl-3H-imidazo[4,5-b]pyridin-3-yl)benzyl)piperidin-4-yl)amino)pyrimidine-2-carbonitrile;

4-((1-(4-(8-(2-aminopyridin-3-yl)-6-hydroxy-9H-purin-9-yl)benzyl)piperidin-4-yl)amino)pyrimidine-2-carbonitrile;

4-((1-(4-(2-(2-aminopyridin-3-yl)-5-(pyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-hydroxy-3H-imidazo[4,5-b]pyridin-3-yl)benzyl)piperidin-4-yl)amino)pyrimidine-2-carbonitrile;

4-((1-(4-(5-amino-2-(2-aminopyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-chloro-4-fluorophenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-fluorophenyl)-6-methyl-3H-imidazo[4,5-b]pyridin-3-yl)benzyl)piperidin-4-yl)amino)pyrimidine-2-carbonitrile;

2-(2-aminopyridin-3-yl)-1-(4-((4-((2-cyanopyrimidin-4-yl)amino)piperidin-1-yl)methyl)phenyl)-1H-benzo[d]imidazole-6-carbonitrile;

2-(2-aminopyridin-3-yl)-1-(4-((4-((2-cyanopyrimidin-4-yl)amino)piperidin-1-yl)methyl)phenyl)-1H-benzo[d]imidazole-5-carbonitrile;

4-((1-((4-(2-(2-aminopyridin-3-yl)-3H-imidazo[4,5-b]pyridin-3-yl)phenyl)methyl-d2)piperidin-4-yl)(methyl-d3)amino)pyrimidine-2-carbonitrile;

4-((1-(4-(2-(2-aminopyridin-3-yl)-3H-imidazo[4,5-b]pyridin-3-yl)benzyl)piperidin-4-yl-4-d)amino)pyrimidine-2-carbonitrile;

4-((1-((4-(2-(2-aminopyridin-3-yl)-5,6-dimethyl-3H-imidazo[4,5-b]pyridin-3-yl)phenyl)methyl-d2)piperidin-4-yl)amino)pyrimidine-2-carbonitrile;

4-((1-(4-(8-(2-aminopyridin-3-yl)-9H-purin-9-yl)benzyl)piperidin-4-yl)amino)pyrimidine-2-carbonitrile;

(S)-4-((1-(4-(2-(2-aminopyridin-3-yl)-5-(tetrahydrofuran-3-yl)-3H-imidazo[4,5-b]pyridin-3-yl)benzyl)piperidin-4-yl)amino)pyrimidine-2-carbonitrile;

(R)-4-((1-(4-(2-(2-aminopyridin-3-yl)-5-(tetrahydrofuran-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(hydroxymethyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(fluoromethyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(pyrrolidin-1-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-methoxypyridin-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-methoxypyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-ethynyl-3H-imidazo[4,5-b]pyridin-3-yl)benzyl)piperidin-4-yl)amino)pyrimidine-2-carbonitrile;

N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)-N-methylacetamide;

4-((1-(4-(2-(2-aminopyridin-3-yl)-5-(3-methoxypyridin-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-methoxy pyridin-3-yl)-3H-imidazo[4,5-b]pyridin-3-yl)benzyl)piperidin-4-yl)amino)pyrimidine-2-carbonitrile;

4-((1-(4-(5-(3-aminophenyl)-2-(2-aminopyridin-3-yl)-3H-imidazo[4,5-b]pyridin-3-yl)benzyl)piperidin-4-yl)amino)pyrimidine-2-carbonitrile;

N-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)isobutyramide;

N-(3-(3-(4-((4-((2-cyanopyrimidin-4-yl)amino)piperidin-1-yl)methyl)phenyl)-2-(2-isobutyramidopyridin-3-yl)-3H-imidazo[4,5-b]pyridin-5-yl)phenyl)isobutyramide;

methyl (3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)carbamate;

4-((1-(4-(2-(2-aminopyridin-3-yl)-5-(3-(dimethylamino)phenyl)-3H-imidazo[4,5-b]pyridin-3-yl)benzyl)piperidin-4-yl)amino)pyrimidine-2-carbonitrile;

N-(1-(3-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)phenyl)piperidin-4-yl)-N-methylacetamide;

4-((1-(4-(2-(2-aminopyridin-3-yl)-5-(4-fluoro-2-methylphenyl)-3H-imidazo[4,5-b]pyridin-3-yl)benzyl)piperidin-4-yl)amino)pyrimidine-2-carbonitrile;

2-(2-(2-aminopyridin-3-yl)-3-(4-((4-((2-cyanopyrimidin-4-yl)amino)piperidin-1-yl)methyl)phenyl)-3H-imidazo[4,5-b]pyridin-5-yl)-5-fluorobenzamide;

4-((1-(4-(2-(2-aminopyridin-3-yl)-5-(2-cyano-4-fluorophenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-fluoro-2-(trifluoromethyl)phenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(o-tolyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(m-tolyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(p-tolyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-(trifluoromethyl)phenyl)-3H-imidazo[4,5-b]pyridin-3-yl)benzyl)piperidin-4-yl)amino)pyrimidine-2-carbonitrile;

isopropyl 2-(2-aminopyridin-3-yl)-3-(4-((4-((2-cyanopyrimidin-4-yl)amino)piperidin-1-yl)methyl)phenyl)-3H-imidazo[4,5-b]pyridine-5-carboxylate;

4-((1-(4-(2-(2-aminopyridin-3-yl)-1H-benzo[d]imidazol-1-yl)benzyl)piperidin-4-yl)amino)pyrimidine-2-carbonitrile;

4-((1-(4-(2-(2-aminopyridin-3-yl)-1H-imidazo[4,5-b]pyridin-1-yl)benzyl)piperidin-4-yl)amino)pyrimidine-2-carbonitrile;

4-((1-(4-(2-(2-aminopyridin-3-yl)-5-(6-methylpyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(difluoromethoxy)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-methoxypyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-methoxypyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-hydroxypyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1,3-dimethyl-1H-pyrazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-1H-imidazo[4,5-c]pyridin-1-yl)benzyl)piperidin-4-yl)amino)pyrimidine-2-carbonitrile;

4-((1-(4-(2-(2-aminopyridin-3-yl)-5-(4-fluorophenyl)-3H-imidazo[4,5-b]pyridin-3-yl)benzyl)piperidin-4-yl)(methyl)amino)pyrimidine-2-carbonitrile;

4-((1-(4-(2-(2-aminopyridin-3-yl)-5-(6-(difluoromethoxy)pyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-(difluoromethoxy)pyridin-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-fluoro-2-hydroxyphenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-fluoro-3-hydroxyphenyl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-methyl-1H-imidazol-5-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-methylpyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-cyanopyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-6-bromo-5-(4-fluorophenyl)-3H-imidazo[4,5-b]pyridin-3-yl)benzyl)piperidin-4-yl)amino)pyrimidine-2-carbonitrile;

2-(2-aminopyridin-3-yl)-3-(4-((4-((2-cyanopyrimidin-4-yl)amino)piperidin-1-yl)methyl)phenyl)-5-methyl-3H-imidazo[4,5-b]pyridine-6-carbonitrile;

4-((1-(4-(2-(2-aminopyridin-3-yl)-5-(3-fluoropyridin-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-methoxypyridin-2-yl)-3H-imidazo[4,5-b]pyridin-3-yl)benzyl)piperidin-4-yl)amino)pyrimidine-2-carbonitrile;

2-(2-aminopyridin-3-yl)-1-(4-((4-((2-cyanopyrimidin-4-yl)amino)piperidin-1-yl)methyl)phenyl)-1H-imidazo[4,5-c]pyridine-6-carbonitrile;

4-((1-(4-(2-(2-aminopyridin-3-yl)-5-(4-methyloxazol-5-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-cyclopropyl-1H-pyrazol-4-yl)-3H-imidazo[4,5-b]pyridin-3-yl)benzyl)piperidin-4-yl)amino)pyrimidine-2-carbonitrile;

2-(2-aminopyridin-3-yl)-1-(4-((4-((2-cyanopyrimidin-4-yl)amino)piperidin-1-yl)methyl)phenyl)-1H-imidazo[4,5-b]pyrazine-5,6-dicarbonitrile;

2-(2-aminopyridin-3-yl)-3-(4-((4-((2-cyanopyrimidin-4-yl)amino)piperidin-1-yl)methyl)phenyl)-5-(4-fluorophenyl)-3H-imidazo[4,5-b]pyridine-6-carbonitrile;

4-((1-(4-(2-(2-aminopyridin-3-yl)-5-(2-fluoropyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-methyl-1H-1,2,4-triazol-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-ethoxypyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-fluoropyridin-4-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-methoxypyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-methyl-1H-1,2,3-triazol-5-yl)-3H-imidazo[4,5-b]pyridin-3-yl)benzyl)piperidin-4-yl)amino)pyrimidine-2-carbonitrile;

2-(2-aminopyridin-3-yl)-3-(4-((4-((2-cyanopyrimidin-4-yl)amino)piperidin-1-yl)methyl)phenyl)-6-methyl-3H-imidazo[4,5-b]pyridine-5-carbonitrile;

4-((1-(4-(2-(2-aminopyridin-3-yl)-5-(5-methyl-1,3,4-oxadiazol-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-methyl-1H-1,2,4-triazol-5-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-methyl-2H-1,2,3-triazol-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-methyl-4H-1,2,4-triazol-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-fluoropyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-methylpyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-(difluoromethyl)-1H-1,2,4-triazol-3-yl)-3H-imidazo[4,5-b]pyridin-3-yl)benzyl)piperidin-4-yl)amino)pyrimidine-2-carbonitrile;

4-((1-(4-(2-(4-aminopyrimidin-5-yl)-5-(5-fluoropyridin-2-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(5-fluoropyridin-2-yl)-3H-imidazo[4,5-b]pyridin-3-yl)benzyl)piperidin-4-yl)amino)pyrimidine-2-carbonitrile;

4-((1-(4-(5-(5-fluoropyridin-2-yl)-2-(pyridin-3-yl)-3H-imidazo[4,5-b]pyridin-3-yl)benzyl)piperidin-4-yl)amino)pyrimidine-2-carbonitrile;

4-((1-(4-(2-(2-aminophenyl)-5-(5-fluoropyridin-2-yl)-3H-imidazo[4,5-b]pyridin-3-yl)benzyl)piperidin-4-yl)amino)pyrimidine-2-carbonitrile;

4-((1-(4-(5-(5-fluoropyridin-2-yl)-2-phenyl-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-(methoxy-d3)pyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-(difluoromethoxy)pyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-(fluoromethoxy)pyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-methoxypyrimidin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-methylpyrazin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-methoxypyrazin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-ethoxypyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-cyclopropoxypyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-isopropoxypyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-cyclopropylpyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-methyl-4H-1,2,4-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(3-methyl-1H-1,2,4-triazol-1-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1H-1,2,4-triazol-1-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1H-1,2,3-triazol-1-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2H-1,2,3-triazol-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-methyl-1H-1,2,3-triazol-1-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(oxazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-fluoropyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(4-methylpyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-(methoxy-d3)pyridin-3-yl-2-d)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-(methoxy-d3)pyridin-3-yl)-3H-imidazo[4,5-b]pyridin-3-yl)benzyl)piperidin-4-yl)amino)pyrimidine-2-carbonitrile;

2-(2-aminopyridin-3-yl)-3-(4-((4-((2-cyanopyrimidin-4-yl)amino)piperidin-1-yl)methyl)phenyl)-5-hydroxy-3H-imidazo[4,5-b]pyridine-6-carbonitrile;

4-((1-(4-(2-(2-amino-4-fluoropyridin-3-yl)-5-(5-fluoropyridin-2-yl)-3H-imidazo[4,5-b]pyridin-3-yl)benzyl)piperidin-4-yl)amino)pyrimidine-2-carbonitrile;

4-((1-(4-(5-(5-fluoropyridin-2-yl)-2-(pyrimidin-5-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-6-(5-fluoropyridin-2-yl)-1H-benzo[d]imidazol-1-yl)benzyl)piperidin-4-yl)amino)pyrimidine-2-carbonitrile;

4-((1-(4-(2-(2-aminopyridin-3-yl)-5-(5-fluoropyrimidin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-methylpyrimidin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(5-fluoropyrazin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-(fluoromethoxy)pyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-(fluoromethyl)-6-oxo-1,6-dihydropyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-(methyl-d3)-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-ethyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-isopropyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-isopropyl-1H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-methyl-5-(methyl-d3)-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2,5-dimethyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-cyclopropyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-methyl-2H-1,2,3-triazol-4-yl-5-d)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-(difluoromethyl)-6-oxo-1,6-dihydropyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-(fluoromethyl)-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-(fluoromethyl)-1H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-(difluoromethyl)-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(2-(methyl-d3)-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(3-aminoisoxazol-4-yl)-5-(5-fluoropyridin-2-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(6-(fluoromethoxy-d2)pyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-(fluoromethyl-d2)-6-oxo-1,6-dihydropyridin-3-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(1-ethyl-1H-1,2,3-triazol-4-yl)-3H-imidazo[4,5-b]pyridin-3-yl)benzyl)piperidin-4-yl)amino)pyrimidine-2-carbonitrile;

4-((1-(4-(2-(2-aminopyridin-3-yl)-5-(2-(cyanomethyl)-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(2-(fluoromethyl)-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(1-(fluoromethyl)-1H-1,2,3-triazol-4-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(2-ethyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(2-isopropyl-2H-1,2,3-triazol-4-yl)-3H-imidazo[4,5-b]pyridin-3-yl)benzyl)piperidin-4-yl)amino)pyrimidine-2-carbonitrile;

4-((1-(4-(2-(3-aminopyrazin-2-yl)-5-(2-cyclopropyl-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(3-aminopyrazin-2-yl)-5-(2-(cyanomethyl)-2H-1,2,3-triazol-4-yl)-3H-imidazo[4,5-b]pyridin-3-yl)benzyl)piperidin-4-yl)amino)pyrimidine-2-carbonitrile;
2-(4-(2-(3-aminopyrazin-2-yl)-3-(4-((4-((2-cyanopyrimidin-4-yl)amino)piperidin-1-yl)methyl)phenyl)-3H-imidazo[4,5-b]pyridin-5-yl)-2H-1,2,3-triazol-2-yl)acetamide;
4-((1-(4-(2-(3-aminopyrazin-2-yl)-5-(2-methyl-2H-1,2,3-triazol-4-yl-5-d)-3H-imidazo[4,5-b]pyridin-3-yl)benzyl)piperidin-4-yl)amino)pyrimidine-2-carbonitrile;
4-((1-(4-(2-(3-aminopyrazin-2-yl)-5-(2,5-dimethyl-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(3-aminopyrazin-2-yl)-5-(6-methoxy pyridin-3-yl)-3H-imidazo[4,5-b]pyridin-3-yl)benzyl)piperidin-4-yl)amino)pyrimidine-2-carbonitrile;
4-((1-(4-(2-(3-aminopyrazin-2-yl)-5-(6-(methoxy-d3) pyridin-3-yl)-3H-imidazo[4,5-b]pyridin-3-yl)benzyl) piperidin-4-yl)amino)pyrimidine-2-carbonitrile;
4-((1-(4-(2-(3-aminopyrazin-2-yl)-5-(5-(methoxy-d3) pyridin-2-yl)-3H-imidazo[4,5-b]pyridin-3-yl)benzyl) piperidin-4-yl)amino)pyrimidine-2-carbonitrile;
4-((1-(4-(2-(3-aminopyrazin-2-yl)-5-(6-(fluoromethoxy) pyridin-3-yl)-3H-imidazo[4,5-b]pyridin-3-yl)benzyl) piperidin-4-yl)amino)pyrimidine-2-carbonitrile;
4-((1-(4-(2-(3-aminopyrazin-2-yl)-5-(6-(fluoromethoxy-d2)pyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-cyclopropoxypyridin-3-yl)-3H-imidazo[4,5-b]pyridin-3-yl)benzyl) piperidin-4-yl)amino)pyrimidine-2-carbonitrile;
4-((1-(4-(2-(2-aminopyridin-3-yl)-5-(6-isopropoxypyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-isopropylpyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-cyclopropylpyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-(difluoromethyl) pyridin-3-yl)-3H-imidazo[4,5-b]pyridin-3-yl)benzyl) piperidin-4-yl)amino)pyrimidine-2-carbonitrile;
4-((1-(4-(2-(2-aminopyridin-3-yl)-5-(6-(trifluoromethyl) pyridin-3-yl)-3H-imidazo[4,5-b]pyridin-3-yl)benzyl) piperidin-4-yl)amino)pyrimidine-2-carbonitrile;
4-((1-(4-(2-(2-aminopyridin-3-yl)-5-(5-ethylpyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-(fluoromethyl) pyridin-2-yl)-3H-imidazo[4,5-b]pyridin-3-yl)benzyl) piperidin-4-yl)amino)pyrimidine-2-carbonitrile;
4-((1-(4-(2-(2-aminopyridin-3-yl)-5-(5-(difluoromethyl) pyridin-2-yl)-3H-imidazo[4,5-b]pyridin-3-yl)benzyl) piperidin-4-yl)amino)pyrimidine-2-carbonitrile; and
4-((1-(4-(2-(2-aminopyridin-3-yl)-5-(5-(trifluoromethyl) pyridin-2-yl)-3H-imidazo[4,5-b]pyridin-3-yl)benzyl) piperidin-4-yl)amino)pyrimidine-2-carbonitrile.

12. The pharmaceutical composition of claim 11, wherein the compound, or pharmaceutically acceptable salt or solvate thereof, is selected from the group consisting of:

4-((1-(4-(2-(2-aminopyridin-3-yl)-5-phenyl-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(4-fluorophenyl)-3H-imidazo[4,5-b]pyridin-3-yl)benzyl)piperidin-4-yl) amino)pyrimidine-2-carbonitrile;
2-(2-aminopyridin-3-yl)-3-(4-((4-((2-cyanopyrimidin-4-yl)amino)piperidin-1-yl)methyl)phenyl)-3H-imidazo [4,5-b]pyridine-6-carbonitrile;
4-((1-(4-(2-(2-aminopyridin-3-yl)-5-(5-fluoropyridin-2-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(6-methoxypyridin-3-yl)-3H-imidazo[4,5-b]pyridin-3-yl)benzyl)piperidin-4-yl)amino)pyrimidine-2-carbonitrile;
4-((1-(4-(2-(2-aminopyridin-3-yl)-5-(5-(difluoromethoxy)pyridin-2-yl)-3H-imidazo[4,5-b]pyridin-3-yl)benzyl)piperidin-4-yl)amino)pyrimidine-2-carbonitrile; and
4-((1-(4-(2-(2-aminopyridin-3-yl)-5-(5-cyclopropoxypyridin-2-yl)-3H-imidazo[4,5-b]pyridin-3-yl)benzyl) piperidin-4-yl)amino)pyrimidine-2-carbonitrile.

13. The pharmaceutical composition of claim 12, wherein the compound is 4-((1-(4-(2-(2-aminopyridin-3-yl)-5-phenyl-3H-imidazo[4,5-b]pyridin-3-yl)benzyl)piperidin-4-yl) amino)pyrimidine-2-carbonitrile, or a pharmaceutically acceptable salt or solvate thereof.

14. The pharmaceutical composition of claim 12, wherein the compound is 4-((1-(4-(2-(2-aminopyridin-3-yl)-5-(4-fluorophenyl)-3H-imidazo[4,5-b]pyridin-3-yl)benzyl)piperidin-4-yl)amino)pyrimidine-2-carbonitrile, or a pharmaceutically acceptable salt or solvate thereof.

15. The pharmaceutical composition of claim 12, wherein the compound is 2-(2-aminopyridin-3-yl)-3-(4-((4-((2-cyanopyrimidin-4-yl)amino)piperidin-1-yl)methyl)phenyl)-3H-imidazo[4,5-b]pyridine-6-carbonitrile, or a pharmaceutically acceptable salt or solvate thereof.

16. The pharmaceutical composition of claim 12, wherein the compound is 4-((1-(4-(2-(2-aminopyridin-3-yl)-5-(5-fluoropyridin-2-yl)-3H-imidazo[4,5-b]pyridin-3-yl)benzyl) piperidin-4-yl)amino)pyrimidine-2-carbonitrile, or a pharmaceutically acceptable salt or solvate thereof.

17. The pharmaceutical composition of claim 12, wherein the compound is 4-((1-(4-(2-(2-aminopyridin-3-yl)-5-(2-methyl-2H-1,2,3-triazol-4-yl)-3H-imidazo[4,5-b]pyridin-3-yl)benzyl)piperidin-4-yl)amino)pyrimidine-2-carbonitrile, or a pharmaceutically acceptable salt or solvate thereof.

18. The pharmaceutical composition of claim 12, wherein the compound is 4-((1-(4-(2-(2-aminopyridin-3-yl)-5-(6-methoxypyridin-3-yl)-3H-imidazo[4,5-b]pyridin-3-yl)benzyl)piperidin-4-yl)amino)pyrimidine-2-carbonitrile, or a pharmaceutically acceptable salt or solvate thereof.

19. The pharmaceutical composition of claim 12, wherein the compound is 4-((1-(4-(2-(2-aminopyridin-3-yl)-5-(5-(difluoromethoxy)pyridin-2-yl)-3H-imidazo[4,5-b]pyridin-3-yl)benzyl)piperidin-4-yl)amino)pyrimidine-2-carbonitrile, or a pharmaceutically acceptable salt or solvate thereof.

20. The pharmaceutical composition of claim 12, wherein the compound is 4-((1-(4-(2-(2-aminopyridin-3-yl)-5-(5-cyclopropoxypyridin-2-yl)-3H-imidazo[4,5-b]pyridin-3-yl) benzyl)piperidin-4-yl)amino)pyrimidine-2-carbonitrile, or a pharmaceutically acceptable salt or solvate thereof.

* * * * *

```
SEQUENCE LISTING

Sequence total quantity: 1
SEQ ID NO: 1         moltype = AA  length = 480
FEATURE              Location/Qualifiers
source               1..480
                     mol_type = protein
                     organism = Homo sapiens
SEQUENCE: 1
MSDVAIVKEG WLHKRGKYIK TWRPRYFLLK NDGTFIGYKE RPQDVDQREA PLNNFSVAQC   60
QLMKTERPRP NTFIIRCLQW TTVIERTFHV ETPEEREEWT TAIQTVADGL KKQEEEEMDF  120
RSGSPSDNSG AEEMEVSLAK PKHRVTMNEF EYLKLLGKGT FGKVILVKEK ATGRYYAMKI  180
LKKEVIVAKD EVAHTLTENR VLQNSRHPFL TALKYSFQTH DRLCFVMEYA NGGELFFHLS  240
RERVFSEDRA RFYGAEIVSA LDYLHSEKNV VYRDLKLENL MLDKDGHIKI TDFGLCKEGI  300
```

```
KDGATMKTFC GTPEYLAPEV LEDNDYGRAV DWWGLGVVMY EMMCGRLPFY NQDHEKLFEL  360
ILMEEIRFPR TLGPEAKSLL SGLLKKDPKQ RLGGGSEDAK EIMQHRFFAG IVWQHVYEKK  420
LSPPFKPQVT SETDTRYFDE EFTAQMITIT PPDQDDSMEC VDSERRPHFP QFSYSASGTA  480
```